(12) United States Patent
Al-Awar et al.

(10) Patent No.: US 12,264,147 B2
(45) Date of Patent: *Apr. 1, 2025

(54) SUBSTITUTED CARBOXAMIDES AS INHIBITORS OF WDR5 PROTEIN-PROTEIN BINDING

(71) Applicant: Propellon Therapeutics Inc., Toronto (CA)

(72) Inventors: Rima Al-Awar, Toronto (CA); Carlos Armando Zepeda-Velazquez, Mississauga (CA); Gennady Poda, Toronto (CA); Methvin Isaac, Brampton (CA); David Uehling, Toronto (CA); Brian Wilson, Mississauga (CA); Babu Joseph, Oakville (CA); Yong Liu, Oakville (CA); Pandiaraju Subramanian, Oakville (CA); Ahmed Mamai, Mississauga (CA); Michael Prakesch, Toronto (CA); Julia Katheleen Stille, Ottawa (CA)

(73) Assignee: Propellon Therapeutics Inc., Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/738,707

(22) Filed: May 6, 2022

(65) Prior Publication Data

US 2023/0219926 A1    Jul. 13, 2023

Related U.S. Application Data

(63) Continuation of application No. 17/484,534, filed on Sep. 24, 2021, now abandoned, which is a continuation of application No. 16/080,866, filed as application No. PCT/CA2017/050269 on Mar. 1, 2017, now Pat. No. 11,319,299.

(60) Provisional application No. 62/301,673, filed on Mar. 1, 2016.

(51) Int. Cl.
| | | |
|---|---|---|
| *C07C 233/15* | (2006.01) | |
| *A61K 45/06* | (2006.01) | |
| *C07D 401/10* | (2006.01) | |
| *C07D 401/12* | (2006.01) | |
| *C07D 401/14* | (2006.01) | |
| *C07D 403/10* | (2006.01) | |
| *C07D 405/14* | (2006.01) | |
| *C07D 413/14* | (2006.01) | |
| *C07D 417/12* | (2006.01) | |
| *C07D 417/14* | (2006.01) | |
| *A61P 35/02* | (2006.01) | |

(52) U.S. Cl.
CPC .......... *C07D 401/12* (2013.01); *A61K 45/06* (2013.01); *C07D 401/10* (2013.01); *C07D 401/14* (2013.01); *C07D 403/10* (2013.01); *C07D 405/14* (2013.01); *C07D 413/14* (2013.01); *C07D 417/12* (2013.01); *C07D 417/14* (2013.01); *A61P 35/02* (2018.01)

(58) Field of Classification Search
CPC ..................................................... C07C 233/15
USPC ........................................................ 564/123
See application file for complete search history.

(56) References Cited

U.S. PATENT DOCUMENTS

| | | |
|---|---|---|
| 5,981,537 A | 11/1999 | Nugent et al. |
| 6,288,055 B1 | 9/2001 | Natarajan et al. |
| 7,169,791 B2 | 1/2007 | Breitenstein et al. |
| 7,230,001 B1 | 6/2007 | Rudolf et al. |
| 7,312,341 B2 | 12/2007 | Desimone et al. |
| 7,547,804 B2 | 6/2009 | Bajji et al. |
| 7,745,437 B2 | 6/2010 | Ren et al. |
| 7,807,679 B2 | 10/2010 | Cassayre et al. |
| 7,947,696 B2 | 5/2011 | Eggenweiler et al. |
| 8,193,239 B2 | 6/2012 | Ford et al. |
| 8,748,423 B2 | 6/2014 | Hangauer et al. |
| 9,079,866 B2 | 7/2015 | Bacani et al. |
| 10,160,763 B2 | 12/2018 | Fesik et al. |
| 10,501,466 B2 | 12/2019 | Fesik et al. |

(Continued)

FOREIGN PATENT DOCUMENTS

| | | |
|---|---|---|
| CA | 2944959 A1 | 10/2015 |
| CN | 100355751 C | 12/2007 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Mintz, Levin, Cohn, Ferris, Glovsky and Popeo, P.C.

(57) ABSTRACT

The present application is directed to compounds of Formula I:

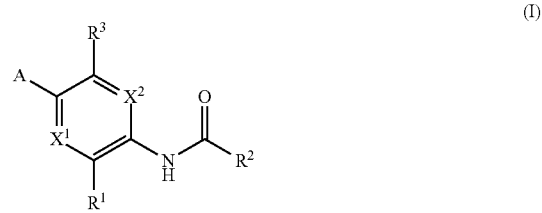

compounds comprising these compounds and their uses, for example as medicaments for the treatment of diseases, disorders or conditions mediated or treatable by inhibition of binding between WDR5 protein and its binding partners.

2 Claims, 1 Drawing Sheet

(56) References Cited

U.S. PATENT DOCUMENTS

| | | |
|---|---|---|
| 2001/0051719 A1 | 12/2001 | Bromidge et al. |
| 2007/0254894 A1 | 11/2007 | Kane et al. |
| 2009/0069327 A1 | 3/2009 | Ding et al. |
| 2009/0105250 A1 | 4/2009 | Sim et al. |
| 2009/0233905 A1 | 9/2009 | Burke et al. |
| 2010/0184765 A1 | 7/2010 | Huang et al. |
| 2012/0208815 A1 | 8/2012 | Burger et al. |
| 2015/0266881 A1 | 9/2015 | Tomita et al. |
| 2016/0311807 A1 | 10/2016 | Treon et al. |
| 2016/0318878 A1 | 11/2016 | Treon et al. |
| 2019/0112290 A1 | 4/2019 | Al-awar et al. |
| 2019/0119264 A1 | 4/2019 | Al-awar et al. |
| 2020/0385371 A1 | 12/2020 | Al-awar et al. |

FOREIGN PATENT DOCUMENTS

| | | | |
|---|---|---|---|
| CN | 101875617 A | 11/2010 | |
| CN | 105175284 A | 12/2015 | |
| CN | 105585565 A | 5/2016 | |
| JP | H0959236 A | 3/1997 | |
| JP | 2010520228 A | 6/2010 | |
| WO | 0172745 A1 | 10/2001 | |
| WO | 0244153 A1 | 6/2002 | |
| WO | 02088101 A2 | 11/2002 | |
| WO | 2006124731 A2 | 11/2006 | |
| WO | 2008106692 A1 | 9/2008 | |
| WO | 2011149874 A2 | 12/2011 | |
| WO | 2011156557 A2 | 12/2011 | |
| WO | 2011159685 A2 | 12/2011 | |
| WO | 2012066065 A1 | 5/2012 | |
| WO | 2014003124 A1 | 1/2014 | |
| WO | 2014048878 A1 | 4/2014 | |
| WO | 2014121055 A2 | 8/2014 | |
| WO | 2016112846 A1 | 7/2016 | |
| WO | 2017147701 A1 | 9/2017 | |
| WO | WO-2017147700 A1 * | 9/2017 | ........... A61K 31/496 |
| WO | 2017221092 A1 | 12/2017 | |
| WO | 2020086857 A1 | 4/2020 | |
| WO | 2021028806 A1 | 2/2021 | |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*

Vippagunta, et al. Advanced Drug Delivery Reviews, 48, 2001, 18.*

Bolshan et al. (2013) "Synthesis, Optimization, and Evaluation of Novel Small Molecules as Antagonists of WDR5-MLL Interaction", ACS Medicinal Chemistry Letters, 4(3):353-357.

Carugo et al. Jun. 2016 "In Vivo Functional Platform Targeting Patient-Derived Xenografts Identifies WDR5- Myc Association as a Critical Determinant of Pancreatic Cancer", Cell Reports, 16(1):133-147.

Cheung et al. (Aug. 2011) "Methylation of an Intronic Region Regulates miR-199a in Testicular Tumor Malignancy", Oncogene., 30(31):3404-3415.

Costa et al. (Jan. 2010) "Reversing HOXA9 Oncogene Activation by PBK Inlribition: Epigenetic Mechanism and Prognostic Significance in Human Glioblastoma", Cancer Research, 70(2):453-462.

Dubuc et al. (Mar. 2013) "Aberrant Patterns of H3K4 and H3K27 Histone Lysine Methylation Occur Across Subgroups in Medulloblastoma", Acta Neuropathologica, 125(3):373-384.

Gallo et al. (Jan. 2013) "A Tumorigenic MLL-homeobox Network in Human Glioblastoma Stem Cells", Cancer Research, 73(1):417-427.

Getlik et al. (2016) "Structure-Based Optimization of a Small Molecule Antagonist of the Interaction between WD Repeat-Containing Protein 5 (WDR5) and Mixed-Lineage Leukemia 1 (MLLJ)", Journal of Medicinal Chemistry, 59(6):2478-2496.

Grebien et al. (2015) "Pharmacological Targeting of the Wdr5-MLL Interaction in C/EBPa N-terminal Leukemia", Nature Chemical Biology, 11(8):571-578(11 pages).

Hackam et al. (2006) "Translation of Research Evidence From Animals to Humans", JAMA, 296(14):1731-1732.

Irizarry et al. (Feb. 2009) "The Human Colon Cancer Methylome Shows Similar Hypo- and Hypermethylation at Conserved Tissue-Specific CpG Island Shores", Nature Genetics, 41(2):178-186.

Karatas et al. (2010) "Analysis of the Binding Mixed Lineage Leukemia 1 (MLLI) and Histone 3 Peptides to WD repeat Domain 5 (WDR%) for the design of Inhibitors of the MLL1-WDR5 Interaction", Journal of Medicinal Chemistry, 53(14):5179-5185.

Karatas et al. (2015) "Structure-based Design Of Conformationally Constrained Cyclic Peptidomimetics To Targetthe MLL1-WDR5 Protein-protein Interaction As Inhibitors Of The MLL1 Methyltransferase Activity", Chinese Chemical Letters, 26:455-458.

Kim et al. (May 2014) "A Role for WDR5 in Integrating Threonine 11 Phosphorylation to Lysine 4 Methylation on Histone H3 During Androgen Signaling and in Prostate Cancer", Molecular Cell, 54(4):613-625.

Li et al. (Aug. 2015) "Pygo2 siRNA Inhibit the Growth and Increase Apoptosis of U251 Cell by Suppressing Histone H3K4 Trimethylation", Journal of Molecular Neuroscience, 56(4):949-955.

Li et al. (2016) "Structure-based Design and Synthesis of Small Molecular Inhibitors Disturbing the Interaction of MLL1-WDR5", European Journal of Medicinal Chemistry, 118:1-8.

Molyneux et al. (Mar. 2012) "Burkitt's lymphoma", Lancet, 379(9822):1234-1244.

Sausen et al. (2015) "Clinical Implications of Genomic Alterations in the Tumour and Circulation of Pancreatic Cancer Patients", Nature Communications, 6:7686(15 pages).

Schneider et al. (2016) "In Vivo RNAi Screening for Pancreatic Cancer Drivers: PILOTing the WDR5-MYC Axis", Trends in Cancer, 2(8):391-392.

Senisterra et al. (2013) "Small-molecule Inhibition of MLL Activity by Disruption of its Interaction with WDR5", Biochemical Journal, 449(1):151-159(13 pages).

Song et al. (2008) "WDR5 Interacts with Mixed Lineage Leukemia (MLL) Protein via the Histone H3-binding Pocket", Journal of Biological Chemistry, 283(50):35258-35264.

Sun et al. (Jul. 2016) "LncRNA GCIncl Promotes Gastric Carcinogenesis and May Act as a Modular Scaffold of WDR5 and KAT2A Complexes to Specify the Histone Modification Pattern", Cancer Discovery, 6(7):784-801.

Thomas et al. (May 2015) "Interaction With WDR5 Promotes Target Gene Recognition And Tumorigenesis By MYC", Molecular Cell, 58(3):440-452.

Wermuth, Camilleg. (1996) "Molecular Variations Based on Isosteric Replacements", Practice of Medicinal Chemistry, 203-237.

Zhao et al. (Dec. 2015) "Expression and Clinical Role of RBQ3 in Gliomas", The Journal of Neurological Science, 359(1-2):177-184.

Zhao et al. (Nov. 2014) "Methylation Of DACT2 Promotes Papillary Thyroid Cancer Metastasis By Activating Wnt Signaling", PLoS One, 9(11):e112336.

Zhou et al. (Feb. 2016) "Pygo2 Functions As A Prognostic Factor For Glioma Due To Its Up-regulation Of H3K4ME3 And Promotion of mLL1/MLL2 Complex Recruitment", Scientific Reports, 6:22066.

* cited by examiner

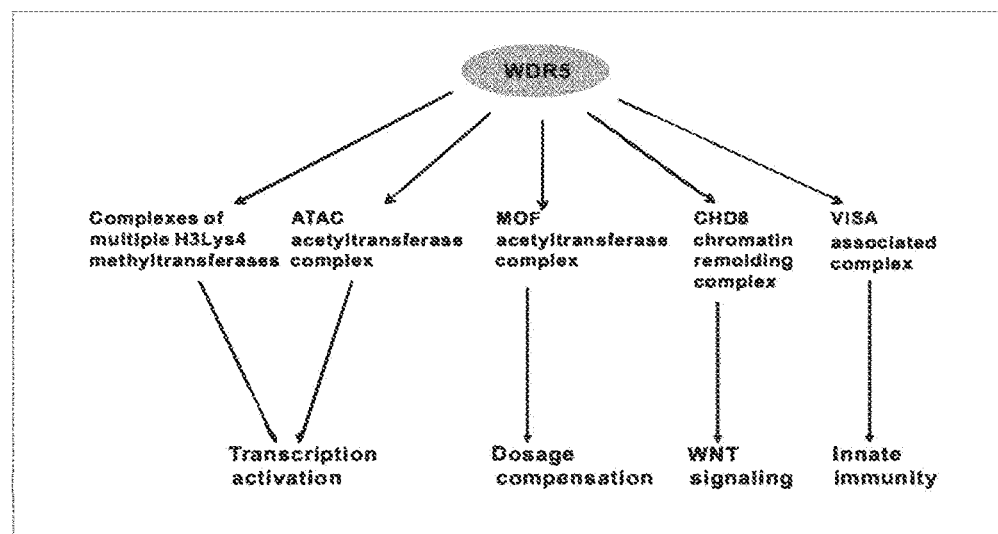

SUBSTITUTED CARBOXAMIDES AS INHIBITORS OF WDR5 PROTEIN-PROTEIN BINDING

CROSS-REFERENCE TO RELATED APPLICATIONS

This application is a continuation of U.S. application Ser. No. 17/484,534, filed Sep. 24, 2021, which is a continuation of U.S. application Ser. No. 16/080,866, filed Aug. 29, 2018, now U.S. Pat. No. 11,319,299, which is a National Stage Application, filed under 35 U.S.C. 371, of International Application No. PCT/CA2017/050269, filed Mar. 1, 2017, which claims priority to, and the benefit of U.S. Provisional Patent Application No. 62/301,673 filed on Mar. 1, 2016, the contents of each of the aforementioned patent applications are incorporated herein by reference in their entireties.

FIELD

The present application relates to compounds, processes for their preparation, compositions comprising them and their use for the treatment of diseases, disorders and conditions mediated by binding between WDR5 and its binding partners including, but not limited to, MLL1.

BACKGROUND

Histones, the most basic units for packing DNA into nucleosomes and covalent modifications of histones, such as methylation, acetylation and phosphorylation, play a central role for regulation of gene transcription [*Nat. Rev. Mol. Cell Biol.* 2001, 2: 422-432; *Cell* 2007, 128: 693-705]. Epigenetics refers to the heritable changes that control how the genome is accessed in different cell types during embryonic development and cellular differentiation [*Genes. Dev.* 2009; 23: 781-3]. This capability permits specialization of function between cells without altering the DNA sequence.

It is now well recognized that misregulation of histone modifications plays a key role in a wide range of human diseases, including but not limited to cancer [*Cell.*, 2007, 10: 693-705; *Nat. Rev. Cancer.*, 2010, 10:457-469]. Mixed Lineage Leukemia 1 (MLL1) protein is a Histone H3 Lysine 4 (H3K4) methyltransferase and is frequently misregulated in a subset of acute leukemias [*Trends Mol. Med.*, 2004, 10: 500-507, *Cell. Stem. Cell.*, 2007, 1:324-337]. MLL1 itself has a weak H3K4 methyltransferase activity but its enzymatic activity is dramatically enhanced when MLL1 is present in a core complex made up of MLL1, WD repeat domain 5 protein (WDR5), Absent, Small, or Homeotic-2-Like (ASH2L) and Retinoblastoma Binding Protein 5 (RbBP5). Recent studies have clearly shown that the binding between MLL1 and WDR5 proteins is optimal for the activity of MLL1 but dispensable for the activity of other MLL family members, including MLL2, MLL3 and MLL4 [*Mol. Cell.*, 2014, 53:247-261]. Hence, blocking the protein-protein binding of MLL1 with WDR5 can specifically inhibit the activity of MLL1 H3K4 methyltransferase activity, and such inhibition has potential for the treatment of human diseases such as a subset of acute leukemias whose development and progression depend upon MLL1 activity.

WDR5 is a common subunit of all six mammalian histone H3K4 methyltransferases [*Dev. Biol.*, 2010,339 (2):240-249]. WDR5 has 334 amino acids and contains seven typical WD40 repeat domains, each approximately 40 amino acids in length [*Nat. Struct. Mol. Biol.*, 2009, 16 (7):678-680]. Structural studies suggest that the WD40 repeats form a seven-bladed propeller fold, with each blade made up of a four-stranded antiparallel sheet. This structural property suggests that WDR5 has many exposed surfaces making it a useful adaptor to interact with other proteins. Further, pulldown assays indicate that WDR5 prefers to bind dimethylated histone H3K4 peptides [*Nat. Struct. Mol. Biol.*, 2009, 16 (7):678-680].

Two recent studies suggested an important role of WDR5 in the MLL1 complex. The WDR5 interacting (WIN) motif, made up of amino acid residues 3762-3773 next to the SET domain in MLL1 protein, was independently discovered to mediate the binding of MLL1 with WDR5 [*J. Biol. Chem.*, 2008, 283(47):32158-32161; *J. Biol. Chem.*, 2008,283(50): 35258-35264]. The crystal structure of the WIN motif peptide with WDR5 shows that the WIN motif, which is the analogue of H3 N-terminal peptide, binds with WDR5 in the central depression of the β-propeller by adopting a 310-helical structure and inserting Arg3765 into the central channel. Hence, the binding between MLL1 and WDR5 is mediated by a well-defined pocket in WDR5 and WIN motif (residues 3762-3773) in MLL1. Previous studies have demonstrated that a 3-residue peptide, i.e. Ac-A-R-A-$NH_2$ ($K_i$ =0.12 mmol/L) has the same binding affinity as the 12-residue WIN peptide ($K_i$ =0.16 mmol/L) to WDR5 [*J. Med. Chem.*, 2010, 53: 5179-5185; *J. Am. Chem. Soc.*, 2013, 135: 669-682].

Because WDR5 is an essential component of the histone methylation, acetylation, and chromatin remodeling complexes, while not wishing to be limited by theory, WDR5 is believed to serve as an adaptor protein for complex assembly. However, it may also contribute to other physiological phenomena. WDR5 is an important component for assembly or stability of the virus-induced signaling adapter (VISA) associated complex, which plays a key role in virus-triggered induction of type I interferons (IFNs) and antiviral innate immune response [*Proc. Natl. Acad. Sci. USA.*, 2010, 107(2):815-820]. Previous studies have demonstrated that VISA is located at the outer membrane of mitochondria. Interestingly, this study revealed that WDR5 was not only localized in the nucleus as believed before, but also abundantly localized in the cytoplasm. Viral infection caused translocation of WDR5 from the nucleus to the mitochondria located VISA complex, where it played a role in the assembly and stability of the VISA complex. These studies demonstrate for the first time a cytoplasmic function for WDR5, specifically in virus-triggered signaling resulting in induction of type I IFNs [*Proc. Natl. Acad. Sci. USA.*, 2010,107 (2):815-820].

(a) MLL1-WDR5 Complex in Leukemogenesis

Leukemia is characterized by an abnormal increase of white blood cells in the blood or bone marrow. Among all types of cancers, the morbidity of leukemia is the highest for patients below 35 years old. Over 70% of infant leukemia patients bear a translocation involving chromosome 11, resulting in the fusion of the MLL1 gene with other genes [*Nat. Rev. Cancer.*, 2007, 7(11):823-833]. MLL1 translocations are also found in approximately 10% of adult acute myeloid leukemia (AML) patients who were previously treated with topoisomerase II inhibitors for other types of cancers [*Nat. Rev. Cancer.*, 2007, 7(11):823-833]

MLL1 is the human homologue of *Saccharomyces cerevisiae* gene Set1 and the *Drosophila* gene Trx. The genes encode an enzyme to catalyze the methylation of H3K4 [*Nat. Rev. Cancer.*, 2007, 7(11):823-833]. Trimethylation of histone 3 at lysine 4 (H3K4) is a hallmark of active gene transcription, and alteration of this process often causes changes in gene expression pattern. MLL1 translocation is also linked to altered transcription of important genes involved in stem cell maintenance and development and, thus, leads to leukemogenesis. The MLL1 gene was first discovered in leukemia patients in 1991 [*Nat. Rev. Cancer.*, 2007, 7(11):823-833]. cDNA of the MLL1 gene contains ~12 kb nucleotides and encodes a peptide over 4000 amino acids in length. In the cell, the premature MLL1 protein is digested by taspase, which results in two peptides: a 300 kDa N-terminal fragment and a 170 kDa C-terminal fragment. The two cleaved peptides form a heterodimer, which is complexed with other components, including WDR5, RBBP5, ASH2L and DPY30. In some leukemia patients, chromosomal translocation results in fusion of ~4.2 kb DNA of the MLL1 N-terminal coding region with some other genes [*Cancer. Cell.*, 2003, 4(3):197-207].

The generation of MLL1 fusion protein is sufficient to induce leukemia, which has been demonstrated in animal models [*Nat. Rev. Cancer.*, 2007, 7(11):823-833]. The mechanisms of MLL1 fusion-mediated leukemia have been studied extensively in the past twenty years. The MLL/SET1 family members are most enzymatically active when part of the "core complex" (WRAD2), comprising the catalytic SET-domain-containing subunits bound to a sub-complex made up of the proteins WDR5, RbBP5, Ash2L and a homodimer of DPY-30. The necessity of MLL/SET1 members to bind WRAD2 for full activity is the basis of a particular drug development strategy, which seeks to disrupt the binding between the MLL/SET1 subunits and WDR5. Recent efforts to pharmacologically target the MLL1 catalytic activity has centered on attempts to disrupt the MLL1-WDR5 binding by means of Win-motif mimicking peptides and small-molecule peptidomimetics [*J. Med. Chem.*, 2010, 53: 5179-5185; *J. Am. Chem. Soc.*, 2013, 135: 669-682; *Mol Cell.*, 2014; 53:247-261]. However, as with most peptide based inhibitors, MLL1-WDR5 peptidic inhibitors exhibit poor cell-based activity and lack oral bioavailability due to poor cell-permeability and peptide chemical liability (e.g. susceptibility to peptidases).

(b) Role of WDR5 in Other Cancers
(i) Bladder Cancer

WDR5 also plays a critical role in embryonic stem cell self-renewal [*Cell.* 2011; 145 (2):183-97] and epithelial-mesenchymal transition [*Mol. Cell.*, 2011; 43(5):811-22]. A recent study found that the protein H2A.Z is overexpressed in bladder cancer and activates oncogenic transcription by recruiting WDR5 and Bromodomain PHD Finger Transcription Factor (BPTF) to its target genes [*Epigenetics. Chromatin.*, 2013; 6 (1):34], suggesting that WDR5 may play a role in bladder cancer, though its expression pattern, role and mechanism in bladder cancer remained unclear. WDR5 is upregulated in bladder cancer tissues compared with normal tissues as determined by immunohistochemistry (IHC), and is correlated with advanced tumor stage and overall survival of bladder cancer patients. A recent study found that WDR5 is overexpressed in prostate cancer tissue compared with normal tissues [*Mol. Cell.*, 2014 May 22; 54 (4):613-25]. Taken together, high expression levels of WDR5 may serve as a novel molecular marker for bladder cancer.

WDR5 silencing reduces cell growth in breast cancer and prostate cancer [*Mol. Cell.*, 2014, 54 (4):613-25; *Cell Rep.*, 2013 5 (2):302-13], but the detailed mechanism and role in vivo is still unknown. Through gain or loss of function, WDR5 was found to promote bladder cancer cell proliferation in vitro and tumor growth in vivo, and that silencing WDR5 mainly induces the G0/G1 phase cell cycle arrest. The cell cycle is regulated by cyclins and cyclin-dependent kinases. Cyclin E1 and Cyclin E2 regulate the G1 to S-phase transition, while Cyclin B1 regulates the G2 to M-phase transition. Moreover, Cyclin E is associated with high-grade, high-stage and invasive bladder cancer [*Cell. Cycle.*, 2012; 11(7):1468-76; *Am. J. Pathol.*, 2000; 157(3):787-94]. UHMK1 (also named KIS) is overexpressed in leukemia and promotes the G1 to S-phase transition [*Leuk. Res.*, 2008; 32 (9):1358-65]. Mechanistically, WDR5 knockdown inhibited cyclin E1, cyclin E2 and UHMK1 leading to G0/G1 phase cell cycle arrest, which might disturb the effect of cyclin B1 downregulation on G2 to M-phase transition. Additional studies showed that knockdown of MLL1, a core component of the MLL/SET1 complexes, suppressed HeLa cell proliferation by reducing the expression of cyclin B and inducing the G2/M phase cell cycle arrest [*Oncogene.* 2013; 32(28): 3359-70]. These data suggest that WDR5 promotes bladder cancer cell proliferation in vitro and in vivo by regulating the cell cycle, but the role and mechanism are not the same as MLL1.

WDR5 is believed to play a role in cancer stem cells (CSCs). CSCs are a small subpopulation of cells in a tumor that can self-renew and differentiate into multiple lineages, and possess strong tumor-initiating capacity. CSCs have been widely identified in a number of malignancies, and the existence of CSCs in bladder cancer was found by Chan et al [*Proc. Natl. Acad. Sci. USA.*, 2009; 106 (33):14016-21]. Several studies have found that sphere culture is an effective way to enrich cancer stem cells [*Cell.* 2007; 131(6):1109-23; *Urol Oncol.* 2012; 30(3):314-8]. It was observed that WDR5 and pluripotency transcription factors were upregulated in UM-UC-3 and T24 spheres. Through gain or loss of function, it was demonstrated that WDR5 promoted UM-UC-3 and T24 cells self-renewal in vitro and upregulated the homeobox protein transcription factor Nanog. Emerging evidence shows that Nanog is overexpressed in poorly differentiated tumors and correlated with poor survival outcome of patients with various types of cancer, including bladder cancer [*Nat. Genet.*, 2008; 40(5):499-507; *Onco. Targets. Ther.*, 2013; 6:1207-20]. Moreover, Nanog plays a role in CSCs self-renewal and targeting. Nanog has shown promising therapeutic potential in several types of cancer [*Cell Stem Cell.* 2011; 9 (1):50-63; *Oncogene.* 2013; 32(37): 4397-405]. WDR5 directly activates Nanog by mediating its promoter H3K4me3 level. Taken together, recent findings suggest that WDR5 plays a role in self-renewal of bladder cancer cells by regulating Nanog.

Further studies have demonstrated that WDR5 silencing increased cell apoptosis and decreased bladder cancer cells resistance to cisplatin. Conversely, overexpression of WDR5 enhanced chemoresistance to cisplatin. Moreover, WDR5 directly regulates important inhibitors of apoptotic proteins, MCL1 [*FEBS Lett.* 2010; 584(14):2981-9; *Sci Rep.* 2014; 4:6098] and BIRC3 [*Expert Opin Ther Targets.* 2009; 13(11):1333-45], by H3K4me3.

In summary, WDR5 is upregulated in bladder cancer, and promotes bladder cancer cell proliferation, self-renewal and chemoresistance via activating a series of oncogenes by H3K4me3. Therefore, WDR5 is a potential biomarker for bladder cancer and a promising target for drug development [*Sci Rep.* 2015; 5: 8293, *Genom Data.* 2015; 5:27-9.].

(ii) Acute Myeloid Leukemia (AML)

The CEBPA gene is mutated in 9% of patients with acute myeloid leukemia (AML). Selective expression of a short (30-kDa) CCAAT-enhancer binding protein-α (C/EBPα) translational isoform, termed p30, represents the most common type of CEBPA mutation in AML. The molecular mechanisms underlying p30-mediated transformation remain incompletely understood. Recent studies have shown that C/EBPα p30, but not the normal p42 isoform, preferentially interacts with WDR5, a key component of SET/MLL (SET-domain/mixed-lineage leukemia) histone-methyltransferase complexes. Accordingly, p30-bound genomic regions are enriched for MLL-dependent H3K4me3 marks. The p30-dependent increase in self-renewal and inhibition of myeloid differentiation required WDR5, as downregulation of the latter inhibited proliferation and restored differentiation in p30-dependent AML models. Small-molecule inhibitors of WDR5-MLL binding selectively inhibited proliferation and induced differentiation in p30-expressing human AML cells revealing the mechanism of p30-dependent transformation and establish the p30 cofactor WDR5 as a therapeutic target in CEBPA-mutant AML [*Nat Chem Biol.* 2015; 11(8):571-8].

(iii) MYCN-Amplified Neuroblastoma

MYCN gene amplification in neuroblastoma drives a gene expression program that correlates strongly with aggressive disease. Mechanistically, trimethylation of histone H3 lysine 4 (H3K4) at target gene promoters is a prerequisite for this transcriptional program to be enacted. WDR5 is a histone H3K4 presenter that has been found to have an essential role in H3K4 trimethylation. For this reason, in this study, the relationship between WDR5-mediated H3K4 trimethylation and N-Myc transcriptional programs in neuroblastoma cells was investigated. N-Myc upregulated WDR5 expression in neuroblastoma cells. Gene expression analysis revealed that WDR5 target genes included those with MYC-binding elements at promoters such as MDM2. WDR5 was shown to form a protein complex at the MDM2 promoter with N-Myc, but not p53, leading to histone H3K4 trimethylation and activation of MDM2 transcription [*Cancer Res* 2015; 75(23); 5143-54]. RNAi-mediated attenuation of WDR5 upregulated expression of wild-type but not mutant p53, an effect associated with growth inhibition and apoptosis. Similarly, a small-molecule antagonist of WDR5 reduced N-Myc/WDR5 complex formation, N-Myc target gene expression, and cell growth in neuroblastoma cells. In MYCN-transgenic mice, WDR5 was overexpressed in precancerous ganglion and neuroblastoma cells compared with normal ganglion cells. Clinically, elevated levels of WDR5 in neuroblastoma specimens were an independent predictor of poor overall survival. Overall, these results identify WDR5 as a relevant cofactor for N-Myc-regulated transcriptional activation and tumorogenesis and as a novel therapeutic target for MYCN-amplified neuroblastomas [*Cancer Res* 2015; 75(23); 5143-54, *Mol Cell.* 2015; 58(3):440-52.].

SUMMARY

The structural features as described in the background suggest that the WDR5-MLL binding is a desirable drug target. Hence, agents that bind to the WDR5 protein and compete for binding with WDR5-interacting partners can reverse the transcriptional activities of WDR5 containing complexes. Considering the challenges generally associated with inhibiting protein-protein interactions, along with the current need to treat WDR5-driven tumor types such as leukemia and bladder cancers, complementary approaches including virtual screening, focused library screening and traditional structure activity relationship (SAR) studies were conducted. These studies led to the identification of compounds which inhibit the WDR5 protein-protein binding. In addition, structure-activity relationship studies demonstrated that specific chemical features contribute to longer residence times for the binding of these compounds with WDR5. Studies indicate that longer residence times can be designed into WDR5 inhibitors and contribute to the ligand-induced anti-proliferative effects observed in hematologic and solid tumors.

A novel class of compounds of Formula (I) have been prepared that show potent disruption of WDR5-MLL1 protein-protein binding and therefore have utility in the treatment of cancers and other WDR5-mediated diseases, disorders and conditions.

Therefore, in one aspect, the present application includes a compound of Formula (I) or a pharmaceutically acceptable salt and/or solvate thereof:

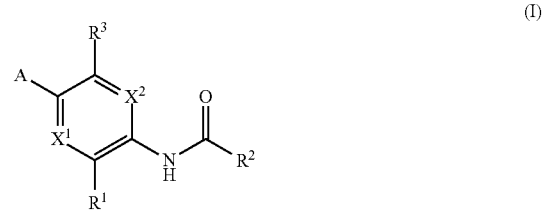

wherein:

$R^1$ is a heterocycloalkyl that is unsubstituted or substituted with one or more substituents selected from halo, $C_{1-6}$alkyl, $C_{1-6}$fluoroalkyl, $C_{3-10}$-cycloalkyl, $OR^4$, $SR^4$, $NR^5R^6$, $C_{1-6}$alkyleneOR$^4$, $C_{1-6}$alkyleneSR$^4$ and $C_{1-6}$alkyleneNR$^5R^6$, provided that $R^1$ comprises at least one basic nitrogen atom;

$R^2$ is selected from $C_{6-10}$aryl and heteroaryl, and $R^2$ is unsubstituted or substituted with one or more substituents selected from halo, $C_{1-6}$alkyl, $C_{1-6}$fluoroalkyl, =O, =S, $OR^7$, $SR^7$ and $NR^8R^9$;

$R^3$ is selected from $C_{6-10}$aryl, heteroaryl and heterocycloalkyl, and $R^3$ is unsubstituted or substituted with one or more substituents selected from halo, CN, $C_{1-6}$alkyl, $C_{1-6}$fluoroalkyl, =O, =S, $OR^{10}$, $SR^{10}$, $SO_2R^{10}$, $NR^{11}R^{12}$, $R^{13}$, $C_{1-6}$alkyleneR$^{13}$, $C_{1-6}$alkenyleneR$^{13}$, $OC_{1-6}$alkyleneR$^{13}$, $SC_{1-6}$alkyleneR$^{13}$, $C_{1-6}$alkyleneNR$^{11}R^{12}$, $C_{1-6}$alkyleneOR$^{10}$, $C_{1-6}$alkyleneSR$^{10}$, $OC_{1-6}$alkyleneNR$^{11}R^{12}$, $SC_{1-6}$alkyleneNR$^{11}R^{12}$, $OC_{1-6}$alkyleneOR$^{10}$, $SC_{1-6}$alkyleneOR$^{10}$, $OC_{1-6}$alkyleneSR$^{10}$, $SC_{1-6}$alkyleneSR$^{10}$, $C(O)OR^{10}$, $C(S)OR^{10}$, $C(S)NR^{11}R^{12}$ and $C(O)NR^{11}R^{12}$;

$R^4$ is selected from H, $C_{1-6}$alkyl $C_{1-6}$fluoroalkyl, $C(O)C_{1-6}$alkyl and $C(O)C_{1-6}$fluoroalkyl;

$R^5$ and $R^6$ are independently selected from H, $C_{1-6}$alkyl, $C_{1-6}$fluoroalkyl, heterocycloalkyl, $C(O)C_{1-6}$alkyl, $C(O)C_{1-6}$fluoroalkyl, $C(O)OC_{1-6}$alkyl, $C(O)NHC_{1-6}$alkyl, $SO_2C_{1-6}$alkyl, $SO_2HNC_{1-6}$alkyl, $C_{1-6}$alkyleneOC$_{1-6}$alkyl, $C_{1-6}$alkyleneC$_{6-10}$aryl, $C_{1-6}$alkyleneheteroaryl, $C_{1-6}$alkyleneheterocycloalkyl and $C_{1-6}$alkyleneC$_{3-6}$cycloalkyl, or $R^5$ and $R^6$ together with the nitrogen atom to which they are attached form a 3-10 membered heterocycle that is unsubstituted or substituted with one or more substituents selected from halo, CN, OH, $C_{1-6}$alkyl $OC_{1-6}$alkyl, $C_{1-6}$fluoroalkyl, $OC_{1-6}$fluoroalkyl, $C(O)C_{1-6}$alkyl, $C(O)C_{1-6}$fluoroalkyl, $C(O)C_{1-6}$alkyl, $C(O)NHC_{1-6}$alkyl, $SO_2C_{1-6}$alkyl, $SO_2HNC_{1-6}$alkyl, $C_{1-6}$alkyleneOC$_{1-6}$alkyl, $C_{1-6}$alkyleneC$_{6-10}$aryl, $C_{1-6}$alkyleneheteroaryl, $C_{1-6}$alkyleneheterocycloalkyl and $C_{1-6}$alkyleneC$_{3-6}$cycloalkyl;

$R^7$ is selected from H, $C_{1-6}$alkyl, $C_{1-6}$fluoroalkyl, $C(O)C_{1-6}$fluoroalkyl and $C(O)C_{1-6}$alkyl;

$R^8$ and $R^9$ are independently selected from H, $C_{1-6}$alkyl, $C_{1-6}$fluoroalkyl, $C(O)C_{1-6}$fluoroalkyl and $C(O)C_{1-6}$alkyl, or $R^8$ and $R^9$ together with the nitrogen atom to which they are attached form a 3-10 membered heterocycle that is unsubstituted or substituted with one or more substituents selected from halo, OH, CN, $C_{1-6}$alkyl $OC_{1-6}$alkyl, $C_{1-6}$fluoroalkyl and $OC_{1-6}$fluoroalkyl;

$R^{10}$ is selected from H, $C_{1-6}$alkyl, $C_{1-6}$fluoroalkyl, C(O)$C_{1-6}$alkyl, C(O)$C_{1-6}$fluoroalkyl, $C_{3-10}$cycloalkyl, heterocycloalkyl, $C_{6-10}$aryl, heteroaryl, $C_{1-6}$alkylene$C_{3-10}$cycloalkyl, $C_{1-6}$alkylene$C_{6-10}$aryl, $C_{1-6}$alkyleneheteroaryl and $C_{1-6}$alkyleneheterocycloalkyl, and is unsubstituted or substituted with one or more substituents selected from halo, CN, $OR^{14}$, $SR^{14}$, $NR^{15}R^{16}$, $C_{1-6}$alkyl, C(O)$R^{14}$, C(O)$OR^{14}$, C(O)$NR^{15}R^{16}$, S(O)$C_{1-6}$alkyl, $SO_2C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$ alkyleneheteroaryl, $C_{1-6}$alkyleneheterocycloalkyl, $C_{1-6}$alkylene$R^{14}$, $C_{1-6}$alkylene$OR^{14}$, $C_{1-6}$alkylene$SR^{14}$ and $C_{1-6}$alkylene$NR^{15}R^{16}$;

$R^{11}$ and $R^{12}$ are each independently selected from H, $C_{1-10}$alkyl, $C_{1-10}$fluoroalkyl, C(O)$C_{1-6}$alkyl, C(O)$C_{1-6}$fluoroalkyl, C(O)$C_{6-10}$aryl, C(O)$C_{3-10}$cycloalkyl, C(O)heteroaryl, C(O)heterocycloalkyl, C(O)$OC_{1-6}$alkyl, C(O)$OC_{1-6}$fluoroalkyl, C(O)$OC_{6-10}$aryl, C(O)$OC_{3-10}$cycloalkyl, C(O)Oheteroaryl, C(O)Oheterocycloalkyl, C(O)$NHC_{1-6}$alkyl, C(O)$NHC_{1-6}$fluoroalkyl, C(O)$NHC_{6-10}$aryl, C(O)$NHC_{3-10}$cycloalkyl, C(O)NHheteroaryl, C(O)NHheterocycloalkyl, $SO_2C_{1-6}$alkyl, $SO_2C_{1-6}$fluoroalkyl, $SO_2C_{6-10}$aryl, $SO_2C_{3-10}$cycloalkyl, $SO_2$heteroaryl, $SO_2$heterocycloalkyl, $C_{3-10}$cycloalkyl, heterocycloalkyl, heteroaryl, $C_{6-10}$aryl, $C_{1-6}$alkylene$C_{3-10}$cycloalkyl, $C_{1-6}$alkylene$C_{6-10}$aryl, $C_{1-6}$alkyleneheteroaryl and $C_{1-6}$alkyleneheterocycloalkyl, and each of $R^{11}$ and $R^{12}$ are independently unsubstituted or substituted with one or more substituents selected from halo, CN, $OR^{14}$, $SR^{14}$, $NR^{15}R^{16}$, $C_{1-6}$alkyl, C(O)$R^{14}$, C(O)$OR^{14}$, C(O)$NR^{15}R^{16}$, S(O)$C_{1-6}$alkyl, $SO_2C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkylene$R^{14}$, $C_{1-6}$alkylene$OR^{14}$, $C_{1-6}$alkylene$SR^{14}$ and $C_{1-6}$alkylene$NR^{15}R^{16}$, or $R^{11}$ and $R^{12}$ together with the nitrogen atom to which they are attached form a 3-10 membered heterocycle that is unsubstituted or substituted with one or more substituents independently selected from halo, CN, $OR^{14}$, $SR^{14}$, $NR^{15}R^{16}$, $C_{1-6}$alkyl, C(O)$R^{14}$, C(O)$OR^{14}$, C(O)$NR^{15}R^{16}$, S(O)$C_{1-6}$alkyl, $SO_2C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkylene$R^{14}$, $C_{1-6}$alkylene$OR^{14}$, $C_{1-6}$alkylene$SR^{14}$ and $C_{1-6}$alkylene$NR^{15}R^{16}$;

$R^{13}$ is selected from C(O)$C_{1-6}$alkyl, C(O)$C_{1-6}$fluoroalkyl, C(O)$C_{6-10}$aryl, C(O)$C_{3-10}$cycloalkyl, C(O)heteroaryl, C(O)heterocycloalkyl, $C_{3-10}$cycloalkyl, heterocycloalkyl, heteroaryl and $C_{6-10}$aryl, and $R^{13}$ is unsubstituted or substituted with one or more substituents independently selected from halo, CN, $OR^{14}$, $SR^{14}$, $NR^{15}R^{16}$, $C_{1-6}$alkyl, C(O)$R^{14}$, C(O)$OR^{14}$, C(O)$NR^{15}R^{16}$, S(O)$C_{1-6}$alkyl, $SO_2C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$ alkyleneheteroaryl, $C_{1-6}$ alkyleneheterocycloalkyl, $C_{1-6}$alkylene$R^{14}$, $C_{1-6}$alkylene$OR^{14}$, $C_{1-6}$alkylene$SR^{14}$ and $C_{1-6}$alkylene$NR^{15}R^{16}$, $R^{14}$ is selected from H, $C_{1-6}$alkyl, $C_{1-6}$fluoroalkyl, C(O)$C_{1-6}$alkyl, C(O)$C_{1-6}$fluoroalkyl, $C_{3-10}$cycloalkyl, heterocycloalkyl, $C_{6-10}$aryl, $C_{1-6}$alkylene$C_{6-10}$aryl, $C_{1-6}$alkylene$C_{3-10}$cycloalkyl and $C_{1-6}$alkyleneheterocycloalkyl, and $R^{14}$ is unsubstituted or substituted with one or more substituents selected from halo, CN, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, N($C_{1-6}$alkyl)($C_{1-6}$alkyl), C(O)$C_{1-6}$alkyl, C(O)$C_{1-6}$fluoroalkyl, C(O)OH, C(O)$OC_{1-6}$alkyl, C(O)$NH_2$, C(O)$NHC_{1-6}$alkyl, C(O)N($C_{1-6}$alkyl)($C_{1-6}$alkyl), $SO_2C_{1-6}$alkyl, S(O)$C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkylene$OC_{1-6}$alkyl, $C_{1-6}$alkyleneSH, $C_{1-6}$alkylene$SC_{1-6}$alkyl, $C_{1-6}$alkylene$NH_2$, $C_{1-6}$alkylene$NHC_{1-6}$alkyl and $C_{1-6}$alkyleneN($C_{1-6}$alkyl)($C_{1-6}$alkyl);

$R^{15}$ and $R^{16}$ are each independently selected from H, $C_{1-6}$alkyl, $C_{1-6}$fluoroalkyl, C(O)$C_{1-6}$alkyl, C(O)$C_{1-6}$fluoroalkyl, $C_{3-10}$-cycloalkyl, heterocycloalkyl, $C_{6-10}$aryl, $C_{1-6}$alkylene$C_{6-10}$aryl, $C_{1-6}$alkylene$C_{3-10}$cycloalkyl and $C_{1-6}$alkyleneheterocycloalkyl and each of $R^{15}$ and $R^{16}$ is unsubstituted or substituted with one or more substituents independently selected from halo, CN, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_1$-6alkyl, N($C_{1-6}$alkyl)($C_{1-6}$alkyl), C(O)$C_{1-6}$alkyl, C(O)$C_{1-6}$fluoroalkyl, C(O)OH, C(O)$OC_{1-6}$alkyl, C(O)$NH_2$, C(O)$NHC_1$-6alkyl, C(O)N($C_{1-6}$alkyl)($C_{1-6}$alkyl), $SO_2C_{1-6}$alkyl, S(O)$C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkylene$OC_{1-6}$alkyl, $C_{1-6}$alkyleneSH, $C_{1-6}$alkylene$SC_{1-6}$alkyl, $C_{1-6}$alkylene$NH_2$, $C_{1-6}$alkylene$NHC_{1-6}$alkyl and $C_{1-6}$alkyleneN($C_{1-6}$alkyl)($C_{1-6}$alkyl), or $R^{15}$ and $R^{16}$ together with the nitrogen atom to which they are attached form a 3-10 membered heterocycle that is unsubstituted or substituted with one or more substituents selected from halo, CN, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, N($C_{1-6}$alkyl)($C_{1-6}$alkyl), C(O)$C_{1-6}$alkyl, C(O)$C_{1-6}$fluoroalkyl, C(O)OH, C(O)$OC_{1-6}$alkyl, C(O)$NH_2$, C(O)$NHC_{1-6}$alkyl, C(O)N($C_{1-6}$alkyl)($C_{1-6}$alkyl), $SO_2C_{1-6}$alkyl, S(O)$C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$-cycloalkyl, $C_{1-6}$alkyleneheteroaryl, $C_{1-6}$alkyleneheterocycloalkyl, $C_{1-6}$alkyleneOH, $C_{1-6}$alkylene$OC_{1-6}$alkyl, $C_{1-6}$alkyleneSH, $C_{1-6}$ alkylene $SC_{1-6}$alkyl, $C_{1-6}$alkylene$NH_2$, $C_{1-6}$alkylene$NHC_{1-6}$alkyl and $C_{1-6}$alkyleneN($C_{1-6}$alkyl)($C_{1-6}$alkyl);

$X^1$ and $X^2$ are each independently selected from $CR^{17}$ and N;

$R^{17}$ is selected from H, F, $C_{1-6}$alkyl and $C_{1-6}$fluoroalkyl;

A is F, and all alkyl and alkylene groups are optionally fluorosubstituted.

In another aspect, the present application includes a composition comprising one or more compounds of the application and a carrier.

In another aspect, the present application includes a method for inhibition of binding of WDR5 to its binding partners in a cell, either in a biological sample or in a patient, comprising administering an effective amount of one or more compounds of the application to the cell.

The present application also includes a method of treating a disease, disorder or condition that is mediated or treatable by inhibition of binding between WDR5 protein and its binding partners comprising administering a therapeutically effective amount of one or more compounds of the application to a subject in need thereof. In an embodiment of the present application, the disease, disorder or condition mediated or treatable by inhibition of binding between WDR5 protein and its binding partners is cancer.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1 illustrates WDR5 as an adaptor protein in multiple complexes and related biological processes.

DETAILED DESCRIPTION (a) Definitions

Unless otherwise indicated, the definitions and embodiments described in this and other sections are intended to be applicable to all embodiments and aspects of the present application herein described for which they are suitable as would be understood by a person skilled in the art.

The term "compound of the application" or "compound of the present application" and the like as used herein refers to a compound of Formula I, including compounds of Ia, Ib, Ic and Id, and pharmaceutically acceptable salts and/or solvates thereof.

The term "composition of the application" or "composition of the present application" and the like as used herein refers to a composition, such a pharmaceutical composition, comprising one or more compounds of Formula I, including compounds of Formula Ia, Ib, Ic and/or Id or pharmaceutically acceptable salts and/or solvates thereof.

The term "and/or" as used herein means that the listed items are present, or used, individually or in combination. In effect, this term means that "at least one of" or "one or more" of the listed items is used or present. The term "and/or" with respect to pharmaceutically acceptable salts and/or solvates thereof means that the compounds of the application exist as individual salts and hydrates, as well as a combination of, for example, a salt of a solvate of a compound of the application.

As used in the present application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art.

In embodiments of the present application, the compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having an alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomeric forms which the compounds form, as well as mixtures thereof, are included within the scope of the present application.

The compounds of the present application may further exist in varying polymorphic forms and it is contemplated that any polymorphs, or mixtures thereof, which form are included within the scope of the present application.

The present description refers to a number of chemical terms and abbreviations used by those skilled in the art. Nevertheless, definitions of selected terms are provided for clarity and consistency.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 100% of the starting material or substrate is converted to product.

The term "basic nitrogen" as used herein refers to a nitrogen atom that has a lone pair of electrons available to participate in an interaction with a hydrogen atom. In an embodiment, the interaction is a hydrogen bond, an ionic bond or a covalent bond. In general, the basic nitrogen atom will be either a primary, secondary or tertiary alkyl amine nitrogen atom, either in a linear, branched or cyclic group. In some embodiments, the pKa of the conjugate acid of the basic nitrogen atom will be greater than about 8-10.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-10}$alkyl means an alkyl group having 1, 2, 3, 4, 5, 6, 7, 8, 9 or 10 carbon atoms.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{2-6}$alkylene means an alkylene group having 2, 3, 4, 5 or 6 carbon atoms.

The term "alkenyl" as used herein, whether it is used alone or as part of another group, means straight or branched chain, unsaturated alkyl groups containing at least one double bond. The number of carbon atoms that are possible in the referenced alkylene group are indicated by the prefix "$C_{n1-n2}$". For example, the term $C_{2-6}$alkenyl means an alkenyl group having 2, 3, 4, 5 or 6 carbon atoms and at least one double bond.

The term "fluoroalkyl" as used herein refers to an alkyl group wherein one or more, including all of the hydrogen atoms are replaced by a fluorine atom. In an embodiment, the fluoroalkyl comprises at least one —$CHF_2$ group. In another embodiment, the fluoroalkyl comprises at least one —$CF_3$ group.

The term "fluorosubstituted" as used herein refers to a chemical group wherein one or more, including all of the hydrogen atoms, are replaced by a fluorine atom.

The term "cycloalkyl," as used herein, whether it is used alone or as part of another group, means a saturated carbocyclic group containing a number of carbon atoms and one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The term "aryl" as used herein, whether it is used alone or as part of another group, refers to cyclic groups containing from 6 to 20 carbon atoms and at least one aromatic ring. In an embodiment of the application, the aryl group contains from 6, 9 or 10 carbon atoms, such as phenyl, indanyl or naphthyl.

The term "heterocycloalkyl" as used herein, whether it is used alone or as part of another group, refers to cyclic groups containing 3 to 20 atoms, suitably 3 to 10 atoms, and at least one non-aromatic, ring in which one or more of the atoms are a heteromoiety selected from O, S, S(O), $SO_2$, N, NH and $NC_{1-6}$alkyl, suitably O, S, N, NH and $NC_{1-6}$alkyl. Heterocycloalkyl groups are either saturated or unsaturated (i.e. contain one or more double bonds) and contain one or more than one ring (i.e. are polycyclic). When a heterocycloalkyl group contains more than one ring, the rings may be fused, bridged, spirofused or linked by a bond. When a heterocycloalkyl group contains the prefix $C_{n1-n2}$ this prefix indicates the number of carbon atoms in the corresponding carbocyclic group, in which one or more, suitably 1 to 5, of the ring atoms is replaced with a heteromoiety as defined above.

A first ring group being "fused" with a second ring group means the first ring and the second ring share at least two atoms there between.

The term "heteroaryl" as used herein refers to cyclic groups containing from 5 to 20 atoms, suitably 5 to 10 atoms, at least one aromatic ring and at least one a heteromoiety selected from O, S, S(O), $SO_2$, N, NH and $NC_{1-6}$alkyl, suitably O, S, N, NH and $NC_{1-6}$alkyl. Heteroaryl groups contain one or more than one ring (i.e. are polycyclic). When a heteroaryl group contains more than one ring, the rings may be fused, bridged, spirofused or linked by a bond. When a heteroaryl group contains the prefix $C_{n1-n2}$ this prefix indicates the number of carbon atoms in the corresponding carbocyclic group, in which one or more, suitably 1 to 5, of the ring atoms is replaced with a heteromoiety as defined above.

The term "available", as in "available hydrogen atoms" or "available atoms" refers to atoms that would be known to a person skilled in the art to be capable of replacement by a substituent.

The terms "halo" or "halogen" as used herein, whether it is used alone or as part of another group, refers to a halogen atom and includes fluoro, chloro, bromo and iodo.

The term "amine" or "amino," as used herein, whether it is used alone or as part of another group, refers to groups of the general formula NRR', wherein R and R' are each independently selected from hydrogen and an alkyl group, such as $C_{1-6}$alkyl.

The term "atm" as used herein refers to atmosphere.

The term "MS" as used herein refers to mass spectrometry.

The term "aq." as used herein refers to aqueous.

DCM as used herein refers to dichloromethane.

DIPEA as used herein refers to N,N-diisopropyl ethylamine

DMF as used herein refers to dimethylformamide.

DMSO as used herein refers to dimethylsulfoxide.

EtOAc as used herein refers to ethyl acetate.

HATU as used herein refers to 1-[Bis(dimethylamino)methylene]-1H-1,2,3-triazolo[4,5-b]pyridinium 3-oxid hexafluorophosphate.

MeOH as used herein refers to methanol.

MeCN as used herein refers to acetonitrile.

HCl as used herein refers to hydrochloric acid.

TFA as used herein refers to trifluoroacetic acid.

TBAF as used herein refers to tetra-n-butylammonium fluoride.

CsF as used herein is cesium fluoride.

μwave as used herein refers to a microwave reaction vessel.

SnAr as used herein represents nucleophilic aromatic substitution.

LCMS as used herein refers to liquid chromatography-mass spectrometry.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas).

The term "subject" as used herein includes all members of the animal kingdom including mammals, and suitably refers to humans. Thus the methods of the present application are applicable to both human therapy and veterinary applications. In an embodiment, the subject is a mammal. In another embodiment, the subject is human.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with, the treatment of subjects.

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. [See, for example, S. M. Berge, et al., "Pharmaceutical Salts," *J. Pharm. Sci.* 1977, 66, 1-19]. The selection of the appropriate salt may be useful, for example, so that an ester functionality, if any, elsewhere in a compound is not hydrolyzed. The selection criteria for the appropriate salt will be known to one skilled in the art.

The term "solvate" as used herein means a compound, or a salt or prodrug of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

The term "treating" or "treatment" as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early cancer can be treated to prevent progression, or alternatively a subject in remission can be treated with a compound or composition of the application to prevent recurrence. Treatment methods comprise administering to a subject a therapeutically effective amount of one or more of the compounds of the application and optionally consist of a single administration, or alternatively comprise a series of administrations. For example, the compounds of the application are administered at least once a week. However, in another embodiment, the compounds are administered to the subject from about one time per two weeks, three weeks or one month. In another embodiment, the compounds are administered about one time per week to about once daily. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compounds of the application, and/or a combination thereof. It will also be appreciated that the effective dosage of the compound used for the treatment may increase or decrease over the course of a particular treatment regime.

Changes in dosage may result and become apparent by standard diagnostic assays known in the art. In some instances, chronic administration is required. For example, the compounds are administered to the subject in an amount and for duration sufficient to treat the subject.

"Palliating" a disease, disorder or condition means that the extent and/or undesirable clinical manifestations of a disease, disorder or condition are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition or manifesting a symptom associated with a disease, disorder or condition.

The "disease", "disorder" or "condition" as used herein refers to a disease, disorder or condition mediated or treatable by inhibition of binding between WDR5 protein and its binding partners, in particular MLL1, and in particular using a WDR5 protein inhibitor, such as a compound of the application herein described.

The term "mediated or treatable by inhibition of binding between WDR5 protein and its binding partners" as used herein means that the disease, disorder or condition to be treated is affected by, modulated by and/or has some biological basis, either direct or indirect, that includes WDR5 binding, in particular, increased WDR5 binding, to its binding partners, such as MLL1. Such biological basis includes, for example, WDR5 and/or MLL1 gene overexpression or WDR5 and/or MLL1 protein over-accumulation or overexpression of proteins that are products of or precursors to WDR5-mediated and/or MLL1 gene expression. In a refined context, "mediated or treatable by inhibition of binding between WDR5 protein and its binding partners" refers to an effect mediated through inhibition of binding between WDR5 and MLL1. In a broader context, "mediated or treatable by inhibition of binding between WDR5 protein and its binding partners" can include the large number of diseases that are caused by aberrant methylation of histone 3 lysine 4 (H3K4) residues, as results from aberrant WDR5 and/or MLL1 activity. As used herein, WDR5 refers to the protein identified as GenBank Accession number NM_017588 [*J. Biol. Chem.* 2001, 276 (49), 46515-46522] and isoforms that include this sequence, and shorter versions. Similarly, the other WDR5 proteins are characterized and described in any of the protein databases. As used herein, MLL1 refers to the protein identified as GenBank Accession number NM_005933 [*Proc. Natl. Acad. Sci. U.S.A.* 1991, 88 (23), 10735-10739; *DNA Cell Biol.* 1995, 14 (6), 475-483] and isoforms that include this sequence, and shorter versions. Similarly, the other MLL1 proteins are characterized and described in any of the protein databases.

The term "binding" as used herein refers to any interaction between two entities, such as two proteins, that leads to a functional effect.

As used herein, the term "effective amount" or "therapeutically effective amount" means an amount of one or more compounds of the application that is effective, at dosages and for periods of time necessary to achieve the desired result. For example in the context of treating a disease, disorder or condition mediated or treatable by inhibition of binding between WDR5 protein and its binding partners, an effective amount is an amount that, for example, increases said inhibition compared to the inhibition without administration of the one or more compounds. In an embodiment, effective amounts vary according to factors such as the disease state, age, sex and/or weight of the subject. In a further embodiment, the amount of a given compound or compounds that will correspond to an effective amount will vary depending upon factors, such as the given drug(s) or compound(s), the pharmaceutical formulation, the route of administration, the type of condition, disease or disorder, the identity of the subject being treated, and the like, but can nevertheless be routinely determined by one skilled in the art.

The term "administered" as used herein means administration of a therapeutically effective amount of one or more compounds or compositions of the application to a cell, tissue, organ or subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder. Neoplasms can be benign (such as uterine fibroids and melanocytic nevi), potentially malignant (such as carcinoma in situ) or malignant (i.e. cancer). Exemplary neoplastic disorders include the so-called solid tumours and liquid tumours, including but not limited to carcinoma, sarcoma, metastatic disorders (e.g., tumors arising from the prostate), hematopoietic neoplastic disorders, (e.g., leukemias, lymphomas, myeloma and other malignant plasma cell disorders), metastatic tumors and other cancers.

The term "cancer" as used herein refers to cellular-proliferative disease states.

(b) Compounds and Compositions of the Application

The present application includes a compound of Formula (I) or a pharmaceutically acceptable salt and/or solvate thereof:

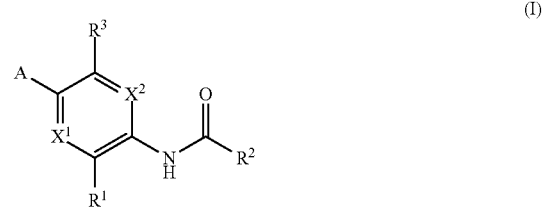

wherein:
R$^1$ is a heterocycloalkyl that is unsubstituted or substituted with one or more substituents selected from halo, C$_{1-6}$alkyl, C$_{1-6}$fluoroalkyl, C$_{3-10}$-cycloalkyl, OR$^4$, SR$^4$, NR$^5$R$^6$, C$_{1-6}$alkyleneOR$^4$, C$_{1-6}$alkyleneSR$^4$ and C$_{1-6}$alkyleneNR$^5$R$^6$, provided that R$^1$ comprises at least one basic nitrogen atom;
R$^2$ is selected from C$_{6-10}$aryl and heteroaryl, and R$^2$ is unsubstituted or substituted with one or more substituents selected from halo, C$_{1-6}$alkyl, C$_{1-6}$fluoroalkyl, =O, =S, OR$^7$, SR$^7$ and NR$^8$R$^9$;
R$^3$ is selected from C$_{6-10}$aryl, heteroaryl and heterocycloalkyl, and R$^3$ is unsubstituted or substituted with one or more substituents selected from halo, CN, C$_{1-6}$alkyl, C$_{1-6}$fluoroalkyl, =O, =S, OR$^{10}$, SR$^{10}$, SO$_2$R$^{10}$, $NR^{11}R^{12}$, $R^{13}$, $C_{1-6}$alkylene$R^{13}$, $C_{1-6}$alkenylene$R^{13}$, $OC_{1-6}$alkylene$R^{13}$, $SC_{1-6}$alkylene$R^{13}$, $C_{1-6}$alkylene$NR^{11}R^{12}$, $C_{1-6}$alkyleneOR$^{10}$, $C_{1-6}$alkyleneSR$^{10}$, $OC_{1-6}$alkylene$NR^{11}R^{12}$, $SC_{1-6}$alkylene$NR^{11}R^{12}$, $OC_{1-6}$alkyleneOR$^{10}$, $SC_{1-6}$alkyleneOR$^{10}$, $OC_{1-6}$alkyleneSR$^{10}$, $SC_{1-6}$alkyleneSR$^{10}$, $C(O)OR^{10}$, $C(S)OR^{10}$, $C(S)NR^{11}R^{12}$ and $C(O)NR^{11}R^{12}$, $R^4$ is selected from H, $C_{1-6}$alkyl $C_{1-6}$fluoroalkyl, $C(O)C_{1-6}$alkyl and $C(O)C_{1-6}$fluoroalkyl;

$R^5$ and $R^6$ are independently selected from H, $C_{1-6}$alkyl, $C_{1-6}$fluoroalkyl, heterocycloalkyl, $C(O)C_{1-6}$alkyl, $C(O)C_{1-6}$fluoroalkyl, $C(O)OC_{1-6}$alkyl, $C(O)NHC_{1-6}$alkyl, $SO_2C_{1-6}$alkyl, $SO_2HNC_{1-6}$alkyl, $C_{1-6}$alkyleneOC$_{1-6}$alkyl, $C_{1-6}$alkyleneC$_{6-10}$aryl, $C_{1-6}$alkyleneheteroaryl, $C_{1-6}$alkyleneheterocycloalkyl and $C_{1-6}$alkyleneC$_{3-6}$cycloalkyl, or $R^5$ and $R^6$ together with the nitrogen atom to which they are attached form a 3-10 membered heterocycle that is unsubstituted or substituted with one or more substituents selected from halo, CN, OH, $C_{1-6}$alkyl OC$_{1-6}$alkyl, $C_{1-6}$fluoroalkyl, OC$_{1-6}$fluoroalkyl, $C(O)C_{1-6}$alkyl, $C(O)C_{1-6}$fluoroalkyl, $C(O)C_{1-6}$alkyl, $C(O)NHC_{1-6}$alkyl, $SO_2C_{1-6}$alkyl, $SO_2HNC_{1-6}$alkyl, $C_{1-6}$alkyleneOC$_{1-6}$alkyl, $C_{1-6}$alkyleneC$_{6-10}$aryl, $C_{1-6}$alkyleneheteroaryl, $C_{1-6}$alkyleneheterocycloalkyl and $C_{1-6}$alkyleneC$_{3-6}$cycloalkyl;

$R^7$ is selected from H, $C_{1-6}$alkyl, $C_{1-6}$fluoroalkyl, $C(O)C_{1-6}$fluoroalkyl and $C(O)C_{1-6}$alkyl;

$R^8$ and $R^9$ are independently selected from H, $C_{1-6}$alkyl, $C_{1-6}$fluoroalkyl, $C(O)C_{1-6}$fluoroalkyl and $C(O)C_{1-6}$alkyl, or $R^8$ and $R^9$ together with the nitrogen atom to which they are attached form a 3-10 membered heterocycle that is unsubstituted or substituted with one or more substituents selected from halo, OH, CN, $C_{1-6}$alkyl OC$_{1-6}$alkyl, $C_{1-6}$fluoroalkyl and OC$_{1-6}$fluoroalkyl;

$R^{10}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, heteroaryl, $C_{1-6}$alkylene$C_{3-10}$cycloalkyl, $C_{1-6}$alkyleneC$_{6-10}$aryl, $C_{1-6}$alkyleneheteroaryl and $C_{1-6}$alkyleneheterocycloalkyl, and is unsubstituted or substituted with one or more substituents selected from halo, CN, OR$^{14}$, SR$^{14}$, NR$^{15}$R$^{16}$, $C_{1-6}$alkyl, $C(O)R^{14}$, $C(O)OR^{14}$, $C(O)NR^{15}R^{16}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl $C_{1-6}$alkyleneC$_{3-10}$cycloalkyl $C_{1-6}$alkyleneheteroaryl, $C_{1-6}$alkyleneheterocycloalkyl, $C_{1-6}$alkylene$R^{14}$, $C_{1-6}$alkyleneOR$^{14}$, $C_{1-6}$alkyleneSR$^{14}$ and $C_{1-6}$alkyleneNR$^{15}$R$^{16}$;

$R^{11}$ and $R^{12}$ are each independently selected from H, $C_{1-10}$alkyl $C_{1-10}$fluoroalkyl, $C(O)C_{1-6}$alkyl, $C(O)C_{1-6}$fluoroalkyl, $C(O)C_{6-10}$aryl, $C(O)C_{3-10}$cycloalkyl, $C(O)$heteroaryl, $C(O)$heterocycloalkyl, $C(O)OC_{1-6}$alkyl, $C(O)OC_{1-6}$fluoroalkyl, $C(O)OC_{6-10}$aryl, $C(O)OC_{3-10}$cycloalkyl, $C(O)O$heteroaryl, $C(O)O$heterocycloalkyl, $C(O)NHC_{1-6}$alkyl, $C(O)NHC_{1-6}$fluoroalkyl, $C(O)NHC_{6-10}$aryl, $C(O)NHC_{3-10}$cycloalkyl, $C(O)NH$heteroaryl, $C(O)NH$heterocycloalkyl, $SO_2C_{1-6}$alkyl, $SO_2C_{1-6}$fluoroalkyl, $SO_2C_{6-10}$aryl, $SO_2C_{3-10}$cycloalkyl, $SO_2$heteroaryl, $SO_2$heterocycloalkyl, $C_{3-10}$cycloalkyl, heterocycloalkyl, heteroaryl, $C_{6-10}$aryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and each of $R^{11}$ and $R^{12}$ are independently unsubstituted or substituted with one or more substituents selected from halo, CN, OR$^{14}$, SR$^{14}$, NR$^{15}$R$^{16}$, $C_{1-6}$alkyl, $C(O)R^{14}$, $C(O)OR^{14}$, $C(O)NR^{15}R^{16}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkylene$R^{14}$, $C_{1-6}$alkyleneOR$^{14}$, $C_{1-6}$alkyleneSR$^{14}$ and $C_{1-6}$alkyleneNR$^{15}$R$^{16}$ or $R^{11}$ and $R^{12}$ together with the nitrogen atom to which they are attached form a 3-10 membered heterocycle that is unsubstituted or substituted with one or more substituents independently selected from halo, CN, OR$^{14}$, SR$^{14}$, NR$^{15}$R$^{16}$, $C_{1-6}$alkyl, $C(O)R^{14}$, $C(O)OR^{14}$, $C(O)NR^{15}R^{16}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$-cycloalkyl, $C_{1-6}$alkyleneheteroaryl, $C_{1-6}$alkylene$R^{14}$, $C_{1-6}$alkyleneOR$^{14}$, $C_{1-6}$alkyleneSR$^{14}$ and $C_{1-6}$alkyleneNR$^{15}$R$^{16}$;

$R^{13}$ is selected from $C(O)C_{1-6}$alkyl, $C(O)C_{1-6}$fluoroalkyl, $C(O)C_{6-10}$aryl, $C(O)C_{3-10}$cycloalkyl, $C(O)$heteroaryl, $C(O)$heterocycloalkyl, $C_{3-10}$cycloalkyl, heterocycloalkyl, heteroaryl and $C_{6-10}$aryl, and $R^{13}$ is unsubstituted or substituted with one or more substituents independently selected from halo, CN, OR$^{14}$, SR$^{14}$, NR$^{15}$R$^{16}$, $C_{1-6}$alkyl, $C(O)R^{14}$, $C(O)OR^{14}$, $C(O)NR^{15}R^{16}$, $S(O)C_{1-6}$alkyl, $SO_2C_{1-6}$alkyl, $C_{6-10}$aryl, heteroaryl, $C_{3-10}$-cycloalkyl, heterocycloalkyl, $C_{1-6}$alkyleneC$_{6-10}$aryl, $C_{1-6}$alkyleneC$_{3-10}$-cycloalkyl, $C_{1-6}$ alkyleneheteroaryl, $C_{1-6}$ alkyleneheterocycloalkyl, $C_{1-6}$alkylene$R^{14}$, $C_{1-6}$alkyleneOR$^{14}$, $C_{1-6}$alkyleneSR$^{14}$ and $C_{1-6}$alkyleneNR$^{15}$R$^{16}$;

$R^{14}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl, and $R^{14}$ is unsubstituted or substituted with one or more substituents selected from halo, CN, $C_{1-6}$alkyl, $C_{1-6}$fluoroalkyl, OH, SH, OC$_{1-6}$alkyl, OC$_{1-6}$fluoroalkyl, SC$_{1-6}$alkyl, SC$_{1-6}$fluoroalkyl, NH$_2$, NHC$_{1-6}$alkyl, N(C$_{1-6}$alkyl)(C$_{1-6}$alkyl), $C(O)C_{1-6}$alkyl, $C(O)C_{1-6}$fluoroalkyl, $C(O)$OH, $C(O)OC_{1-6}$alkyl, $C(O)NH_2$, $C(O)NHC_{1-6}$alkyl, $C(O)N(C_{1-6}$alkyl)(C$_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$-cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl); $R^{15}$ and $R^{16}$ are each independently selected from H, $C_{1-6}$alkyl, $C_{1-6}$fluoroalkyl, $C(O)C_{1-6}$alkyl, $C(O)C_{1-6}$fluoroalkyl, $C_{3-10}$-cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl and each of $R^{15}$ and $R^{16}$ is unsubstituted or substituted with one or more substituents independently selected from halo, CN, $C_{1-6}$alkyl, $C_{1-6}$fluoroalkyl, OH, SH, OC$_{1-6}$alkyl, OC$_{1-6}$fluoroalkyl, SC$_{1-6}$alkyl, SC$_{1-6}$fluoroalkyl, NH$_2$, NHC$_{1-6}$alkyl, N(C$_{1-6}$alkyl)(C$_{1-6}$alkyl), $C(O)C_{1-6}$alkyl, $C(O)C_{1-6}$fluoroalkyl, $C(O)$OH, $C(O)OC_{1-6}$alkyl, $C(O)NH_2$, $C(O)NHC_{1-6}$alkyl, $C(O)N(C_{1-6}$alkyl)(C$_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneS$C_{1-6}$alkyl, $C_{1-6}$alkyleneNH$_2$, $C_{1-6}$alkyleneNH$C_{1-6}$alkyl and $C_{1-6}$alkyleneN($C_{1-6}$alkyl)($C_{1-6}$alkyl), or $R^{15}$ and $R^{16}$ together with the nitrogen atom to which they are attached form a 3-10 membered heterocycle that is unsubstituted or substituted with one or more substituents selected from halo, CN, $C_{1-6}$alkyl, $C_{1-6}$fluoroalkyl, OH, SH, O$C_{1-6}$alkyl, O$C_{1}$-6fluoroalkyl, S$C_{1-6}$alkyl, S$C_{1-6}$fluoroalkyl, NH$_2$, NH$C_{1-6}$alkyl, N($C_{1-6}$alkyl)($C_{1-6}$alkyl), C(O)$C_{1-6}$alkyl, C(O)$C_{1-6}$fluoroalkyl, C(O)OH, C(O)O$C_{1-6}$alkyl, C(O)NH$_2$, C(O)NH$C_{1-6}$alkyl, C(O)N($C_{1-6}$alkyl)($C_{1-6}$alkyl), SO$_2$$C_{1-6}$alkyl, S(O)$C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneO$C_{1-6}$alkyl, $C_{1-6}$alkyleneSH, $C_{1-6}$ alkyleneS$C_{1-6}$alkyl, $C_{1-6}$alkyleneNH$_2$, $C_{1-6}$alkyleneNH$C_{1-6}$alkyl and $C_{1-6}$alkyleneN($C_{1-6}$alkyl)($C_{1-6}$alkyl); $X^1$ and $X^2$ are each independently selected from CR$^{17}$ and N;

$R^{17}$ is selected from H, F, $C_{1-6}$alkyl and $C_{1-6}$fluoroalkyl;

A is F, and all alkyl and alkylene groups are optionally fluorosubstituted.

The present application also includes a compound of Formula (I) or a pharmaceutically acceptable salt and/or solvate thereof:

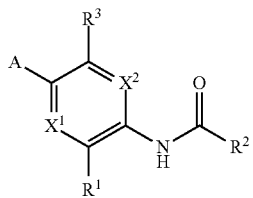

(I)

wherein:

$R^1$ is a heterocycloalkyl that is unsubstituted or substituted with one or more substituents selected from halo, $C_{1-6}$alkyl, $C_{1-6}$fluoroalkyl, OR$^4$, SR$^4$, NR$^5$R$^6$, $C_{1-6}$alkyleneOR$^4$, $C_{1-6}$alkyleneSR$^4$ and $C_{1-6}$alkyleneNR$^5$R$^6$, provided that $R^1$ comprises at least one basic nitrogen atom;

$R^2$ is selected from $C_{6-10}$aryl and heteroaryl, and $R^2$ is unsubstituted or substituted with one or more substituents selected from halo, $C_{1-6}$alkyl, $C_{1-6}$fluoroalkyl, =O, =S, OR$^7$, SR$^7$ and NR$^8$R$^9$;

$R^3$ is selected from $C_{6-10}$aryl, heteroaryl and heterocycloalkyl, and $R^3$ is unsubstituted or substituted with one or more substituents selected from halo, CN, $C_{1-6}$alkyl, $C_{1-6}$fluoroalkyl, OR$^{10}$, SR$^{10}$NR$^{11}$R$^{12}$, R$^{13}$, $C_{1-6}$alkyleneR$^{13}$, O$C_{1-6}$alkyleneR$^{13}$, S$C_{1-6}$alkyleneR$^{13}$, $C_{1-6}$alkyleneNR$^{11}$R$^{12}$, $C_{1-6}$ alkyleneOR$^{10}$, $C_{1-6}$alkyleneSR$^{10}$, O$C_{1-6}$alkyleneNR$^{11}$R$^{12}$, S$C_{1-6}$alkyleneNR$^{11}$R$^{12}$, O$C_{1-6}$alkyleneOR$^{10}$, S$C_{1-6}$alkyleneOR$^{10}$, O$C_{1-6}$alkyleneSR$^{10}$, S$C_{1-6}$alkyleneSR$^{10}$, C(O)OR$^{10}$, C(S)OR$^{10}$, C(S)NR$^{11}$R$^{12}$ and C(O)NR$^{11}$R$^{12}$;

$R^4$ is selected from H, $C_{1-6}$alkyl $C_{1-6}$fluoroalkyl, C(O)$C_{1-6}$alkyl and C(O)$C_{1-6}$fluoroalkyl;

$R^5$ and $R^6$ are independently selected from H, $C_{1-6}$alkyl, $C_{1-6}$fluoroalkyl, heterocycloalkyl, C(O)$C_{1-6}$alkyl and C(O)$C_{1-6}$fluoroalkyl, or $R^5$ and $R^6$ together with the nitrogen atom to which they are attached form a 3-10 membered heterocycle that is unsubstituted or substituted with one or more substituents selected from halo, OH, $C_{1-6}$alkyl O$C_{1-6}$alkyl, $C_{1-6}$fluoroalkyl, O$C_{1-6}$fluoroalkyl, C(O)$C_{1-6}$alkyl and C(O)$C_{1-6}$fluoroalkyl;

$R^7$ is selected from H, $C_{1-6}$alkyl, $C_{1-6}$fluoroalkyl, C(O)$C_{1-6}$fluoroalkyl and C(O)$C_{1-6}$alkyl;

$R^8$ and $R^9$ are independently selected from H, $C_{1-6}$alkyl, $C_{1-6}$fluoroalkyl, C(O)$C_{1-6}$fluoroalkyl and C(O)$C_{1-6}$alkyl, or $R^8$ and $R^9$ together with the nitrogen atom to which they are attached form a 3-10 membered heterocycle that is unsubstituted or substituted with one or more substituents selected from halo, OH, $C_{1-6}$alkyl O$C_{1-6}$alkyl, $C_{1-6}$fluoroalkyl and O$C_{1-6}$fluoroalkyl;

$R^{10}$ is selected from H, $C_{1-6}$alkyl, $C_{1-6}$fluoroalkyl, C(O)$C_{1-6}$alkyl, C(O)$C_{1-6}$fluoroalkyl, $C_{3-10}$-cycloalkyl, heterocycloalkyl, $C_{6-10}$aryl, heteroaryl, $C_{1-6}$alkylene$C_{3-10}$-cycloalkyl, $C_{1-6}$alkylene$C_{6-10}$aryl, $C_{1-6}$alkyleneheteroaryl and $C_{1-6}$alkyleneheterocycloalkyl, and is unsubstituted or substituted with one or more substituents selected from halo, OR$^{14}$, SR$^{14}$, NR$^{15}$R$^{16}$, $C_{1-6}$alkyl, C(O)R$^{14}$, C(O)OR$^{14}$, C(O)NR$^{15}$R$^{16}$, S(O)$C_{1-6}$alkyl, SO$_2$$C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$-cycloalkyl, $C_{1-6}$alkyleneheteroaryl, $C_{1-6}$alkyleneheterocycloalkyl, $C_{1-6}$alkyleneR$^{14}$, $C_{1-6}$alkyleneOR$^{14}$, $C_{1-6}$alkyleneSR$^{14}$ and $C_{1-6}$alkyleneNR$^{15}$R$^{16}$;

$R^{11}$ and $R^{12}$ are each independently selected from H, $C_{1-10}$alkyl $C_{1-10}$fluoroalkyl, C(O)$C_{1-6}$alkyl, C(O)$C_{1-6}$fluoroalkyl, $C_{3-10}$cycloalkyl, heterocycloalkyl, heteroaryl, $C_{6-10}$aryl, $C_{1-6}$alkylene$C_{3-10}$cycloalkyl, $C_{1-6}$alkylene$C_{6-10}$aryl, $C_{1-6}$alkyleneheteroaryl and $C_{1-6}$alkyleneheterocycloalkyl, and each of $R^{11}$ and $R^{12}$ are independently unsubstituted or substituted with one or more substituents selected from halo, OR$^{14}$, SR$^{14}$, NR$^{15}$R$^{16}$, $C_{1-6}$alkyl, C(O)R$^{14}$, C(O)OR$^{14}$, C(O)NR$^{15}$R$^{16}$, S(O)$C_{1-6}$alkyl, SO$_2$$C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneR$^{14}$, $C_{1-6}$alkyleneOR$^{14}$, $C_{1-6}$alkyleneSR$^{14}$ and $C_{1-6}$alkyleneNR$^{15}$R$^{16}$ or RH and $R^{12}$ together with the nitrogen atom to which they are attached form a 3-10 membered heterocycle that is unsubstituted or substituted with one or more substituents independently selected from halo, OR$^{14}$SR$^{14}$, NR$^{15}$R$^{16}$, $C_{1-6}$alkyl, C(O)R$^{14}$, C(O)OR$^{14}$, C(O)NR$^{15}$R$^{16}$, S(O)$C_{1-6}$alkyl, SO$_2$$C_{1-6}$alkyl, $C_{6-10}$aryl, heteroaryl, $C_{3-10}$-cycloalkyl, heterocycloalkyl, $C_{1-6}$alkylene$C_{6-10}$aryl, $C_{1-6}$alkylene$C_{3-10}$-cycloalkyl, $C_{1-6}$alkyleneheteroaryl, $C_{1-6}$alkyleneR$^{14}$, $C_{1-6}$alkyleneOR$^{14}$, $C_{1-6}$alkyleneSR$^{14}$ and $C_{1-6}$alkyleneNR$^{15}$R$^{16}$;

$R^{13}$ is selected from C(O)$C_{1-6}$alkyl, C(O)$C_{1-6}$fluoroalkyl, $C_{3-10}$-cycloalkyl, heterocycloalkyl, heteroaryl and $C_{6-10}$aryl, and $R^{13}$ is unsubstituted or substituted with one or more substituents independently selected from halo, OR$^{14}$, SR$^{14}$, NR$^{15}$R$^{16}$, $C_{1-6}$alkyl, C(O)R$^{14}$, C(O)OR$^{14}$, C(O)NR$^{15}$R$^{16}$, S(O)$C_{1-6}$alkyl, SO$_2$$C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneR$^{14}$, $C_{1-6}$alkyleneOR$^{14}$, $C_{1-6}$alkyleneSR$^{14}$ and $C_{1-6}$alkyleneNR$^{15}$R$^{16}$, $R^{14}$ is selected from H, $C_{1-6}$alkyl, $C_{1-6}$fluoroalkyl, C(O)$C_{1-6}$alkyl, C(O)$C_{1-6}$fluoroalkyl, $C_{3-10}$cycloalkyl, heterocycloalkyl, $C_{6-10}$aryl, $C_{1-6}$alkylene$C_{6-10}$aryl, $C_{1-6}$alkylene$C_{3-10}$cycloalkyl and C₁₋₆alkyleneheterocycloalkyl, and R¹⁴ is unsubstituted or substituted with one or more substituents selected from halo, C₁₋₆alkyl, C₁₋₆fluoroalkyl, OH, SH, OC₁₋₆alkyl, OC₁₋₆fluoroalkyl, SC₁₋₆alkyl, SC₁₋₆fluoroalkyl, NH₂, NHC₁₋₆alkyl, N(C₁₋₆alkyl)(C₁₋₆alkyl), C(O)C₁₋₆alkyl, C(O)C₁₋₆fluoroalkyl, C(O)OH, C(O)OC₁₋₆alkyl, C(O)NH₂, C(O)NHC₁₋₆alkyl, C(O)N(C₁₋₆alkyl)(C₁₋₆alkyl), SO₂C₁₋₆alkyl, S(O)C₁₋₆alkyl, C₆₋₁₀aryl, heteroaryl, C₃₋₁₀cycloalkyl, heterocycloalkyl, C₁₋₆alkyleneC₆₋₁₀aryl, C₁₋₆alkyleneC₃₋₁₀cycloalkyl, C₁₋₆alkyleneheteroaryl, C₁₋₆alkyleneheterocycloalkyl, C₁₋₆alkyleneOH, C₁₋₆alkyleneOC₁₋₆alkyl, C₁₋₆alkyleneSH, C₁₋₆alkyleneSC₁₋₆alkyl, C₁₋₆alkyleneNH₂, C₁₋₆alkyleneNHC₁₋₆alkyl and C₁₋₆alkyleneN(C₁₋₆alkyl)(C₁₋₆alkyl); R¹⁵ and R¹⁶ are each independently selected from H, C₁₋₆alkyl, C₁₋₆fluoroalkyl, C(O)C₁₋₆alkyl, C(O)C₁₋₆fluoroalkyl, C₃₋₁₀cycloalkyl, heterocycloalkyl, C₆₋₁₀aryl, C₁₋₆alkyleneC₆₋₁₀ aryl, C₁₋₆alkyleneC₃₋₁₀cycloalkyl and C₁₋₆alkyleneheterocycloalkyl and each of R¹⁵ and R¹⁶ is unsubstituted or substituted with one or more substituents independently selected from halo, C₁₋₆alkyl, C₁₋₆fluoroalkyl, OH, SH, OC₁₋₆alkyl, OC₁₋₆fluoroalkyl, SC₁₋₆alkyl, SC₁₋₆fluoroalkyl, NH₂, NHC₁₋₆alkyl, N(C₁₋₆alkyl)(C₁₋₆alkyl), C(O)C₁₋₆alkyl, C(O)C₁₋₆fluoroalkyl, C(O)OH, C(O)OC₁₋₆alkyl, C(O)NH₂, C(O)NHC₁₋₆alkyl, C(O)N(C₁₋₆alkyl)(C₁₋₆alkyl), SO₂C₁₋₆alkyl, S(O)C₁₋₆alkyl, C₆₋₁₀aryl, heteroaryl, C₃₋₁₀cycloalkyl, heterocycloalkyl, C₁₋₆alkyleneC₆₋₁₀aryl, C₁₋₆alkyleneC₃₋₁₀cycloalkyl, C₁₋₆alkyleneheteroaryl, C₁₋₆alkyleneheterocycloalkyl, C₁₋₆alkyleneOH, C₁₋₆alkyleneOC₁₋₆alkyl, C₁₋₆alkyleneSH, C₁₋₆alkyleneSC₁₋₆alkyl, C₁₋₆alkyleneNH₂, C₁₋₆alkyleneNHC₁₋₆alkyl and C₁₋₆alkyleneN(C₁₋₆alkyl)(C₁₋₆alkyl), or R¹⁵ and R¹⁶ together with the nitrogen atom to which they are attached form a 3-10 membered heterocycle that is unsubstituted or substituted with one or more substituents selected from halo, C₁₋₆alkyl, C₁₋₆fluoroalkyl, OH, SH, OC₁₋₆alkyl, OC₁₋₆fluoroalkyl, SC₁₋₆alkyl, SC₁₋₆fluoroalkyl, NH₂, NHC₁₋₆alkyl, N(C₁₋₆alkyl)(C₁₋₆alkyl), C(O)C₁₋₆alkyl, C(O)C₁₋₆fluoroalkyl, C(O)OH, C(O)OC₁₋₆alkyl, C(O)NH₂, C(O)NHC₁₋₆alkyl, C(O)N(C₁₋₆alkyl)(C₁₋₆alkyl), SO₂C₁₋₆alkyl, S(O)C₁₋₆alkyl, C₆₋₁₀aryl, heteroaryl, C₃₋₁₀cycloalkyl, heterocycloalkyl, C₁₋₆alkyleneC₆₋₁₀aryl, C₁₋₆alkylene C₃₋₁₀ cycloalkyl, C₁₋₆alkyleneheteroaryl, C₁₋₆alkyleneheterocycloalkyl, C₁₋₆alkyleneOH, C₁₋₆alkyleneOC₁₋₆alkyl, C₁₋₆alkyleneSH, C₁₋₆alkyleneSC₁₋₆alkyl, C₁₋₆alkyleneNH₂, C₁₋₆alkyleneNHC₁₋₆alkyl and C₁₋₆alkyleneN(C₁₋₆alkyl)(C₁₋₆alkyl);

X¹ and X² are each independently selected from CR¹⁷ and N;

R¹⁷ is selected from H, C₁₋₆alkyl and C₁₋₆fluoroalkyl;

A is F; and all alkyl and alkylene groups are optionally fluorosubstituted.

In some embodiments, R¹ is a heterocycloalkyl that is unsubstituted or substituted with one, two or three substituents selected from halo, C₁₋₆alkyl, C₁₋₆fluoroalkyl, NR⁵R⁶ and C₁₋₆alkyleneNR⁵R⁶, provided that R¹ comprises at least one basic nitrogen atom. In some embodiments, R¹ is a heterocycloalkyl that is substituted with one or two substituents selected from halo, C₁₋₆alkyl and NR⁵R⁶, provided that R¹ comprises at least one basic nitrogen atom. In some embodiments, R¹ is a heterocycloalkyl that is substituted with one or two substituents selected from C₁₋₆alkyl and NR⁵R⁶, provided that R¹ comprises at least one basic nitrogen atom. In some embodiments, R¹ is a C₅₋₆heterocyclalkyl comprising one or two nitrogen atoms at least one of which is basic.

In some embodiments, R¹ is selected from:

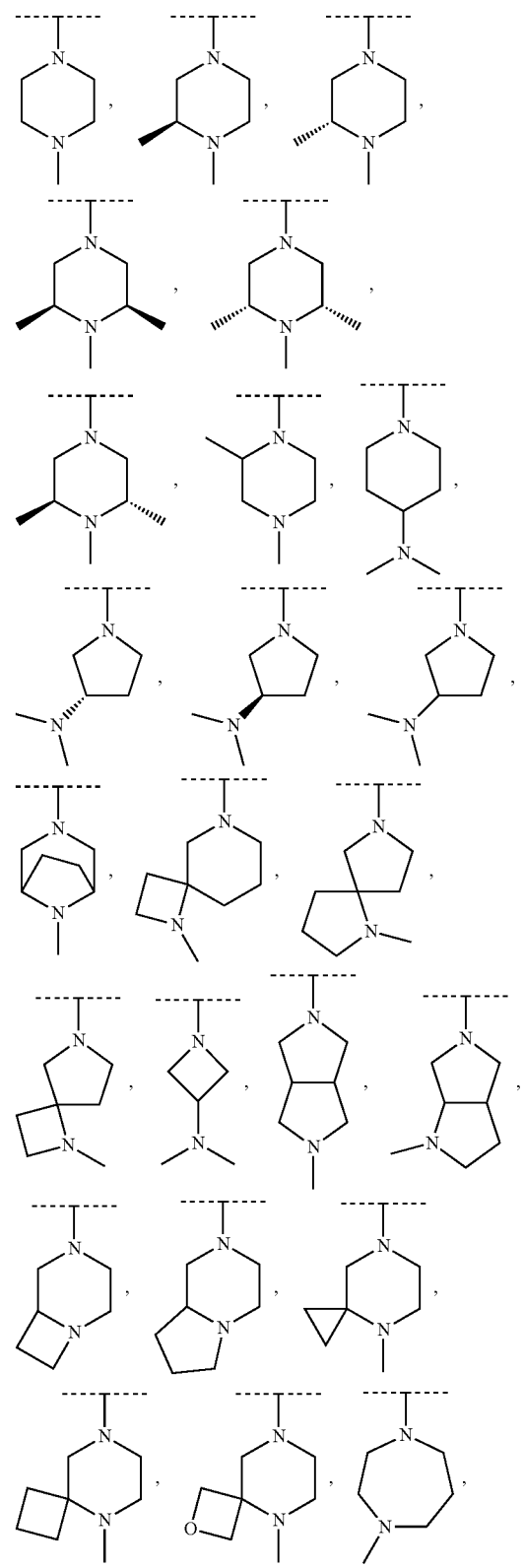

-continued

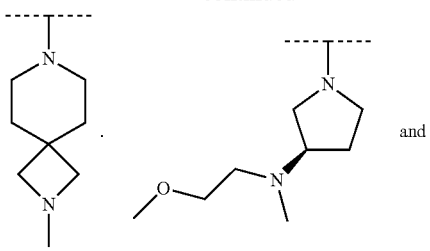

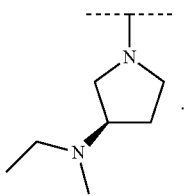

In some embodiments, R¹ is selected from:

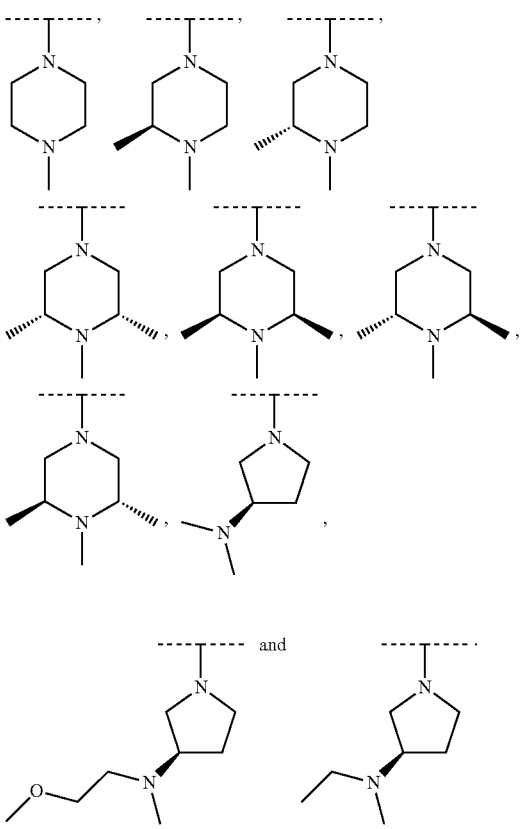

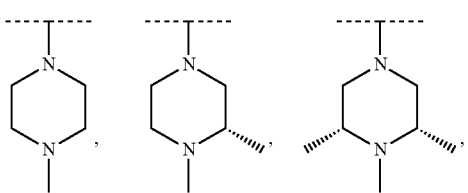

In some embodiments, R¹ is selected from:

-continued

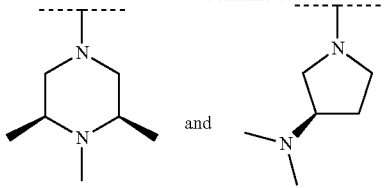

In some embodiments, R¹ is selected from:

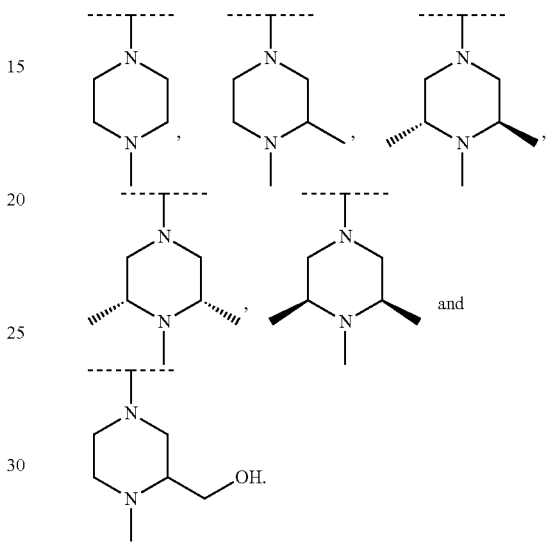

In some embodiments, R¹ is selected from:

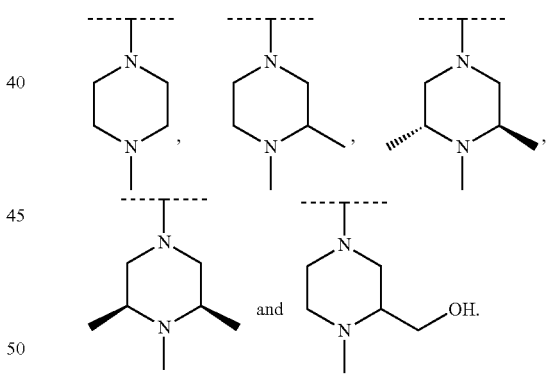

R¹ is selected from:

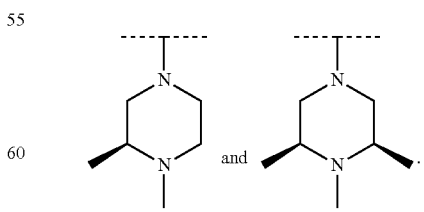

In some embodiments, R² is selected from $C_{6-10}$aryl and heteroaryl, and R² is unsubstituted or substituted with one, two or three substituents selected from halo, $C_{1-6}$alkyl, $C_{1-6}$fluoroalkyl, =O, OR⁷, SR⁷ and NR⁸R⁹. In some embodiments, $R^2$ is selected from $C_{6-10}$aryl and heteroaryl, and $R^2$ is unsubstituted or substituted with one, two or three substituents selected from halo, $C_{1-6}$alkyl, $C_{1-6}$fluoroalkyl, =O and $NR^8R^9$. In some embodiments, $R^2$ is selected from $C_{6-10}$aryl and heteroaryl, and $R^2$ is unsubstituted or substituted with one or two substituents selected from halo, $C_{1-6}$alkyl, $C_{1-6}$fluoroalkyl and =O. In some embodiments, $R^2$ is selected from phenyl and $C_{1-6}$-heteroaryl, and $R^2$ is substituted with one to three substituents selected from F, $CF_2H$, $CF_3$ and =O.

In some embodiments, $R^2$ is selected from:

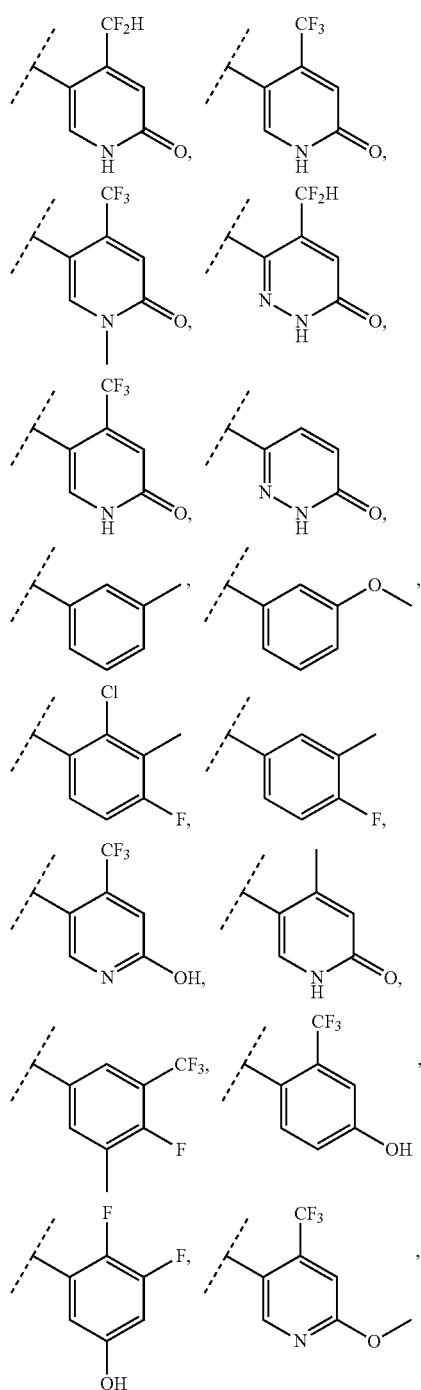

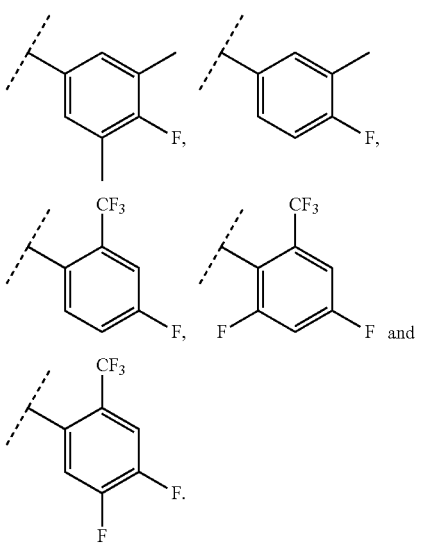

In some embodiments, $R^2$ is selected from

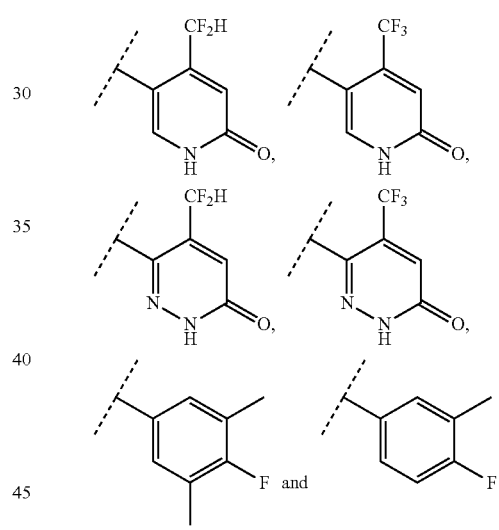

or a tautomer thereof.

In some embodiments, $R^2$ is selected from:

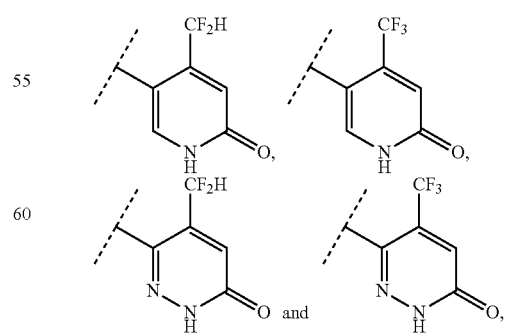

or a tautomer thereof.

In an embodiment, the tautomer of the R² group is

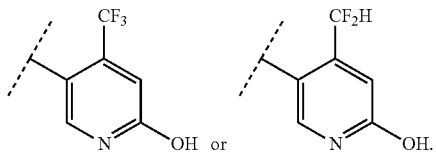

In some embodiments, R² is selected from:

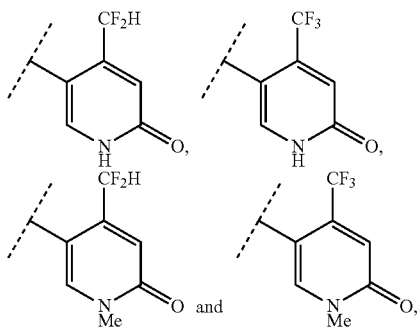

or a tautomer thereof.
In some embodiments, R² is selected from:

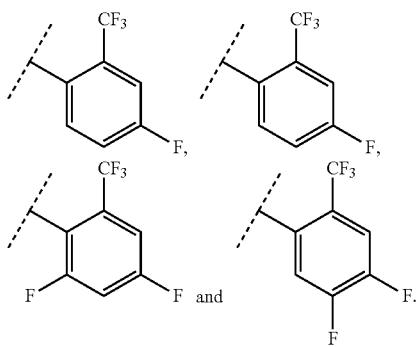

In some embodiments, R² is

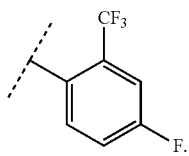

In some embodiments, R³ is selected from $C_{6-10}$aryl, heteroaryl and heterocycloalkyl, and R³ is substituted with one, two or three substituents selected from halo, CN, $C_{1-6}$alkyl, $C_{1-6}$fluoroalkyl, $OR^{10}$, $NR^{11}R^{12}$, $R^{13}$, $C_{1-6}$alkyleneR$^{13}$, $OC_{1-6}$ alkyleneR$^{13}$, $C_{1-6}$alkyleneNR$^{11}R^{12}$, $C_{1-6}$alkyleneOR$^{10}$, $OC_{1-6}$alkyleneNR$^{11}R^{12}$, $OC_{1-6}$alkyleneOR$^{10}$, $C(O)OR^{10}$ and $C(O)NR^{11}R^{12}$. In some embodiments, R³ is selected from $C_{6-10}$aryl, heteroaryl and heterocycloalkyl, and R³ is substituted with one or two substituents selected from halo, CN, $C_{1-6}$alkyl, $C_{1-6}$fluoroalkyl, $OR^{10}$, $NR^{11}R^{12}$, $R^{13}$, $C_{1-6}$alkyleneR$^{13}$, $OC_{1-6}$alkyleneR$^{13}$, $C_{1-6}$alkyleneNR$^{11}R^{12}$, $C_{1-6}$alkyleneOR$^{10}$, $OC_{1-6}$alkyleneNR$^{11}R^{12}$ and $OC_{1-6}$alkyleneOR$^{10}$. In some embodiments, R³ is selected from $C_{6-10}$aryl, heteroaryl and heterocycloalkyl, and R³ is unsubstituted or substituted with one or two substituents selected from halo, CN, $C_{1-6}$alkyl, $OR^{10}$, $NR^{11}R^{12}$, $R^{13}$ and $OC_{1-6}$alkyleneR$^{13}$. In some embodiments, R³ is heteroaryl, and R³ is substituted with one substituent selected from halo, CN, $C_{1-6}$alkyl, $OR^{10}$, $NR^{11}R^{12}$, $R^{13}$ and $OC_{1-6}$alkyleneR$^{13}$. In some embodiments, R³ is heteroaryl, and R³ is substituted with one substituent selected from $R^{13}$. In some embodiments, R³ is phenyl. In some embodiments, R³ is selected from monocyclic $C_{5-6}$heterocycloalkyl and monocyclic $C_{5-6}$ heteroaryl. In some embodiments, R³ is selected from phenyl, pyrimidinyl, pyridinyl, dihydropyridine, dihydropyrrolyl, aziridinyl, oxiranyl, furanyl, thienyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. In some embodiments, R³ is selected from phenyl, pyridinyl, pyrimidinyl and dihydropyridinyl.

In some embodiments, R⁵ and R⁶ are independently selected from H, $C_{1-6}$alkyl and heterocycloalkyl. In some embodiments, R⁵ and R⁶ are independently selected from H and $C_{1-6}$alkyl. In some embodiments, R⁵ and R⁶ together with the nitrogen atom to which they are attached form a 3-10 membered heterocycle that is unsubstituted or substituted with one, two or three substituents selected from halo and $C_{1-6}$alkyl. In some embodiments, R⁵ and R⁶ together with the nitrogen atom to which they are attached form a 3-10 membered heterocycle that is unsubstituted. In some embodiments, $R^{10}$ is selected from H, $C_{1-6}$alkyl, $C_{1-6}$fluoroalkyl, $C(O)C_{1-6}$alkyl, $C_{3-10}$cycloalkyl, heterocycloalkyl, $C_{6-10}$aryl, heteroaryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl. In some embodiments, $R^{10}$ is selected from H, $C_{1-6}$alkyl, $C_{1-6}$fluoroalkyl, $C_{3-10}$cycloalkyl, heterocycloalkyl, $C_{1-6}$alkyleneC$_{3-10}$cycloalkyl and $C_{1-6}$alkyleneheterocycloalkyl. In some embodiments, $R^{10}$ is selected from H, $C_{1-6}$alkyl, $C_{1-6}$fluoroalkyl, heterocycloalkyl and $C_{1-6}$alkyleneC$_{3-10}$cycloalkyl. In some embodiments, $R^{10}$ is selected from $C_{1-6}$alkyl and $C_{1-6}$fluoroalkyl. In some embodiments, $R^{10}$ is an unsubstituted or substituted monocyclic heterocycloalkyl selected from dihydropyridinyl, pyridinyl, pyrimidinyl, aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl In some embodiments, $R^{10}$ is morpholinyl.

In some embodiments, $R^{11}$ and $R^{12}$ are each independently selected from H, $C_{1-10}$alkyl, $C_{1-10}$fluoroalkyl, $C(O)C_{1-6}$alkyl, $C_{3-10}$cycloalkyl, heterocycloalkyl, heteroaryl, $C_{6-10}$aryl, $C_{1-6}$alkyleneC$_{3-10}$cycloalkyl, $C_{1-6}$alkylene $C_{6-10}$aryl, $C_{1-6}$ alkyleneheteroaryl and $C_{1-6}$alkyleneheterocycloalkyl. In some embodiments, $R^{1}$ and $R^{12}$ are each independently selected from H, $C_{1-10}$alkyl, $C_{3-10}$cycloalkyl, heterocycloalkyl, $C_{1-6}$alkylene$C_{3-10}$cycloalkyl and $C_{1-6}$alkyleneheterocycloalkyl. In some embodiments, $R^{11}$ and $R^{12}$ are each independently selected from H, $C_{1-10}$alkyl and $C_{3-10}$cycloalkyl. In some embodiments, $R^{11}$ and $R^{12}$ together with the nitrogen atom to which they are attached form a 3-10 membered heterocycle that is unsubstituted.

In some embodiments, $R^{13}$ is selected from C(O)$C_{1-6}$alkyl, $C_{3-10}$cycloalkyl, heterocycloalkyl, heteroaryl and $C_{6-10}$aryl. In some embodiments, $R^{13}$ is selected from $C_{3-10}$cycloalkyl and heterocycloalkyl. In some embodiments, $R^{13}$ is heterocycloalkyl. In some embodiments, $R^{13}$ is an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. In some embodiments, $R^{13}$ is morpholinyl.

In some embodiments, $X^1$ and $X^2$ are each independently selected from $CR^{17}$ and N, in which $R^{17}$ is selected from H and $C_{1-6}$alkyl. In some embodiments, both of $X^1$ and $X^2$ are $CR^{17}$, in which $R^{17}$ is H. In some embodiments, one of $X^1$ and $X^2$ is $CR^{17}$ and the other of $X^1$ and $X^2$ is N, in which $R^{17}$ is H.

In some embodiments, the compound of Formula I is selected from:

4-fluoro-N-[4-fluoro-2-(4-methylpiperazin-1-yl)-5-[3-(morpholin-4-ylmethyl)phenyl]phenyl]-3,5-dimethylbenzamide;

N-[4-fluoro-2-(4-methylpiperazin-1-yl)-5-[3-(morpholin-4-ylmethyl)phenyl]phenyl]-6-oxo-4-(trifluoromethyl)-1H-pyridine-3-carboxamide;

N-[4-fluoro-2-(4-methylpiperazin-1-yl)-5-(2-morpholin-4-ylpyrimidin-5-yl)phenyl]-6-oxo-4-(trifluoromethyl)-1H-pyridine-3-carboxamide;

N-[4-fluoro-2-(4-methylpiperazin-1-yl)-5-(6-morpholin-4-ylpyridin-3-yl)phenyl]-6-oxo-4-(trifluoromethyl)-1H-pyridine-3-carboxamide;

N-[5-(1,3-benzodioxol-5-yl)-4-fluoro-2-(4-methylpiperazin-1-yl)phenyl]-6-oxo-4-(trifluoromethyl)-1H-pyridine-3-carboxamide;

N-[2-[(3R)-3,4-dimethylpiperazin-1-yl]-4-fluoro-5-(2-morpholin-4-ylpyrimidin-5-yl)phenyl]-6-oxo-4-(trifluoromethyl)-1H-pyridine-3-carboxamide;

N-[2-[(3S)-3,4-dimethylpiperazin-1-yl]-4-fluoro-5-(2-morpholin-4-ylpyrimidin-5-yl)phenyl]-6-oxo-4-(trifluoromethyl)-1H-pyridine-3-carboxamide;

N-[4-fluoro-5-(2-morpholin-4-ylpyrimidin-5-yl)-2-[(3R,5S)-3,4,5-trimethylpiperazin-1-yl]phenyl]-6-oxo-4-(trifluoromethyl)-1H-pyridine-3-carboxamide;

N-[4-fluoro-2-(4-methylpiperazin-1-yl)-5-(2-pyrrolidin-1-ylpyrimidin-5-yl)phenyl]-6-oxo-4-(trifluoromethyl)-1H-pyridine-3-carboxamide;

N-[5-[2-(cyclopropylamino)pyrimidin-5-yl]-4-fluoro-2-(4-methylpiperazin-1-yl)phenyl]-6-oxo-4-(trifluoromethyl)-1H-pyridine-3-carboxamide;

N-[5-[2-(cyclohexylamino)pyrimidin-5-yl]-4-fluoro-2-(4-methylpiperazin-1-yl)phenyl]-6-oxo-4-(trifluoromethyl)-1H-pyridine-3-carboxamide;

N-[5-(2-ethoxypyrimidin-5-yl)-4-fluoro-2-(4-methylpiperazin-1-yl)phenyl]-6-oxo-4-(trifluoromethyl)-1H-pyridine-3-carboxamide;

N-[4-fluoro-2-(4-methylpiperazin-1-yl)-5-(2-methylpyrimidin-5-yl)phenyl]-6-oxo-4-(trifluoromethyl)-1H-pyridine-3-carboxamide;

N-[5-[6-(cyclohexylamino)pyridin-3-yl]-4-fluoro-2-(4-methylpiperazin-1-yl)phenyl]-6-oxo-4-(trifluoromethyl)-1H-pyridine-3-carboxamide;

N-[4-fluoro-5-(2-hydroxypyrimidin-5-yl)-2-(4-methylpiperazin-1-yl)phenyl]-6-oxo-4-(trifluoromethyl)-1H-pyridine-3-carboxamide;

N-[5-(2-cyanopyrimidin-5-yl)-4-fluoro-2-(4-methylpiperazin-1-yl)phenyl]-6-oxo-4-(trifluoromethyl)-1H-pyridine-3-carboxamide;

N-[4-fluoro-2-(4-methylpiperazin-1-yl)-5-[2-(2,2,2-trifluoroethoxy)pyrimidin-5-yl]phenyl]-6-oxo-4-(trifluoromethyl)-1H-pyridine-3-carboxamide;

N-[4-fluoro-2-(4-methylpiperazin-1-yl)-5-pyrimidin-5-ylphenyl]-6-oxo-4-(trifluoromethyl)-1H-pyridine-3-carboxamide;

N-[5-(2,4-dimethoxypyrimidin-5-yl)-4-fluoro-2-(4-methylpiperazin-1-yl)phenyl]-6-oxo-4-(trifluoromethyl)-1H-pyridine-3-carboxamide;

4-(difluoromethyl)-N-[4-fluoro-2-(4-methylpiperazin-1-yl)-5-(2-morpholin-4-ylpyrimidin-5-yl)phenyl]-6-oxo-1H-pyridine-3-carboxamide;

N-[2-[3-(dimethylamino)pyrrolidin-1-yl]-4-fluoro-5-(2-morpholin-4-ylpyrimidin-5-yl)phenyl]-6-oxo-4-(trifluoromethyl)-1H-pyridine-3-carboxamide;

N-[5-(3,6-dihydro-2H-pyran-4-yl)-4-fluoro-2-(4-methylpiperazin-1-yl)phenyl]-6-oxo-4-(trifluoromethyl)-1H-pyridine-3-carboxamide;

N-[4-fluoro-2-(4-methylpiperazin-1-yl)-5-(1,2,3,6-tetrahydropyridin-4-yl)phenyl]-6-oxo-4-(trifluoromethyl)-1H-pyridine-3-carboxamide;

4-fluoro-N-[4-fluoro-5-(2-morpholin-4-ylpyrimidin-5-yl)-2-[(3R,5S)-3,4,5-trimethylpiperazin-1-yl]phenyl]-3-methylbenzamide;

6-acetamido-N-[4-fluoro-5-(2-morpholin-4-ylpyrimidin-5-yl)-2-[(3R,5S)-3,4,5-trimethylpiperazin-1-yl]phenyl]-4-(trifluoromethyl)pyridine-3-carboxamide;

4-fluoro-N-[4-fluoro-5-(2-morpholin-4-ylpyrimidin-5-yl)-2-[(3R,5S)-3,4,5-trimethylpiperazin-1-yl]phenyl]-3,5-dimethylbenzamide;

N-[4-fluoro-5-(4-morpholin-4-ylphenyl)-2-[(3R,5S)-3,4,5-trimethylpiperazin-1-yl]phenyl]-6-oxo-4-(trifluoromethyl)-1H-pyridine-3-carboxamide;

N-[4-fluoro-2-(4-methylpiperazin-1-yl)-5-[6-(oxan-4-yloxy)pyridin-3-yl]phenyl]-6-oxo-4-(trifluoromethyl)-1H-pyridine-3-carboxamide;

N-[5-(2-cyanopyrimidin-5-yl)-4-fluoro-2-[(3S,5R)-3,4,5-trimethylpiperazin-1-yl]phenyl]-6-oxo-4-(trifluoromethyl)-1H-pyridine-3-carboxamide;

N-[4-fluoro-5-(6-morpholin-4-ylpyridin-3-yl)-2-[(3S,5R)-3,4,5-trimethylpiperazin-1-yl]phenyl]-6-oxo-4-(trifluoromethyl)-1H-pyridine-3-carboxamide;

N-[4-fluoro-5-(2-methylpyrimidin-5-yl)-2-[(3S,5R)-3,4,5-trimethylpiperazin-1-yl]phenyl]-6-oxo-4-(trifluoromethyl)-1H-pyridine-3-carboxamide;

4-(difluoromethyl)-N-[4-fluoro-5-(2-morpholin-4-ylpyrimidin-5-yl)-2-[(3S,5R)-3,4,5-trimethylpiperazin-1-yl]phenyl]-6-oxo-1H-pyridine-3-carboxamide;

N-[4-fluoro-5-pyridin-3-yl-2-[(3R,5S)-3,4,5-trimethylpiperazin-1-yl]phenyl]-6-oxo-4-(trifluoromethyl)-1H-pyridine-3-carboxamide;

N-[4-fluoro-5-pyridin-4-yl-2-[(3R,5S)-3,4,5-trimethylpiperazin-1-yl]phenyl]-6-oxo-4-(trifluoromethyl)-1H-pyridine-3-carboxamide;

N-[2-[(3R)-3-(dimethylamino)pyrrolidin-1-yl]-4-fluoro-5-(2-morpholin-4-ylpyrimidin-5-yl)phenyl]-6-oxo-4-(trifluoromethyl)-1H-pyridine-3-carboxamide;

N-[2-[(3S)-3-(dimethylamino)pyrrolidin-1-yl]-4-fluoro-5-(2-morpholin-4-ylpyrimidin-5-yl)phenyl]-6-oxo-4-(trifluoromethyl)-1H-pyridine-3-carboxamide;

N-[5-[6-(cyclopropylmethoxy)pyridin-3-yl]-4-fluoro-2-[(3S,5R)-3,4,5-trimethylpiperazin-1-yl]phenyl]-6-oxo-4-(trifluoromethyl)-1H-pyridine-3-carboxamide;

N-[5-[2-(dimethylamino)pyrimidin-5-yl]-4-fluoro-2-(4-methylpiperazin-1-yl)phenyl]-6-oxo-4-(trifluoromethyl)-1H-pyridine-3-carboxamide;

N-[4-fluoro-2-(4-methylpiperazin-1-yl)-5-[6-(morpholin-4-ylmethyl)pyridin-3-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,5S)-3,4,5-trimethylpiperazin-1-yl]phenyl]-3-(trifluoromethyl)-1H-pyrazole-4-carboxamide;

N-(2',6-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide;

N-(3'-((cyclopentylamino)methyl)-6-fluoro-4-(4-methylpiperazin-1-yl)-[1,1'-biphenyl]-3-yl)-6-oxo-4-(trifluoromethyl)-1,6-dihydropyridine-3-carboxamide;

N-(4-(3,4-dimethylpiperazin-1-yl)-6-fluoro-3'-(morpholinomethyl)-[1,1'-biphenyl]-3-yl)-6-oxo-4-(trifluoromethyl)-1,6-dihydropyridine-3-carboxamide;

N-(4-fluoro-2-(4-methylpiperazin-1-yl)-5-(2-morpholinopyridin-4-yl)phenyl)-6-oxo-4-(trifluoromethyl)-1,6-dihydropyridine-3-carboxamide;

N-(4-fluoro-2-(4-methylpiperazin-1-yl)-5-(5-(morpholinomethyl)pyridin-3-yl)phenyl)-6-oxo-4-(trifluoromethyl)-1,6-dihydropyridine-3-carboxamide;

N-(4-fluoro-2-(4-methylpiperazin-1-yl)-5-(5-(((tetrahydro-2H-pyran-4-yl)amino)methyl)pyridin-3-yl)phenyl)-6-oxo-4-(trifluoromethyl)-1,6-dihydropyridine-3-carboxamide;

(R)—N-(4-fluoro-2-(4-methylpiperazin-1-yl)-5-(5-(((tetrahydrofuran-3-yl)amino)methyl)pyridin-3-yl)phenyl)-6-oxo-4-(trifluoromethyl)-1,6-dihydropyridine-3-carboxamide;

(R)—N-(4-(3,4-dimethylpiperazin-1-yl)-6-fluoro-3'-(morpholinomethyl)-[1,1'-biphenyl]-3-yl)-6-oxo-4-(trifluoromethyl)-1,6-dihydropyridine-3-carboxamide;

(S)—N-(4-(3,4-dimethylpiperazin-1-yl)-6-fluoro-3'-(morpholinomethyl)-[1,1'-biphenyl]-3-yl)-6-oxo-4-(trifluoromethyl)-1,6-dihydropyridine-3-carboxamide;

N-(6-fluoro-3'-(morpholinomethyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide;

N-(4-(3-(dimethylamino)pyrrolidin-1-yl)-6-fluoro-3'-(morpholinomethyl)-[1,1'-biphenyl]-3-yl)-6-oxo-4-(trifluoromethyl)-1,6-dihydropyridine-3-carboxamide;

N-[4-fluoro-2-(4-methylpiperazin-1-yl)-5-(2-morpholin-4-ylpyridin-4-yl)phenyl]-6-oxo-4-(trifluoromethyl)-1H-pyridine-3-carboxamide;

2-(difluoromethyl)-N-(5-(2-((2S,6R)-2,6-dimethylmorpholino)pyrimidin-5-yl)-2-((S)-3,4-dimethylpiperazin-1-yl)-4-fluorophenyl)-4-fluorobenzamide;

N-[5-(1,3-benzodioxol-5-yl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(6-acetamidopyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,5S)-3,4,5-trimethylpiperazin-1-yl]phenyl]-4-methoxy-6-oxo-1H-pyridine-3-carboxamide;

N-[5-[2-(cyclopropylmethoxy)pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[2-[(cyclohexylamino)methyl]phenyl]-4-fluoro-2-[(3R,5S)-3,4,5-trimethylpiperazin-1-yl]phenyl]-6-oxo-4-(trifluoromethyl)-1H-pyridine-3-carboxamide;

N-[5-(3-chloro-4-morpholin-4-ylphenyl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(3,4-dihydro-2H-1,5-benzodioxepin-7-yl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(2,3-dihydro-1,4-benzodioxin-6-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(4-methyl-2,3-dihydro-1,4-benzoxazin-7-yl)-2-[(3R,5S)-3,4,5-trimethylpiperazin-1-yl]phenyl]-6-oxo-4-(trifluoromethyl)-1H-pyridine-3-carboxamide;

N-[5-(2-acetamidopyrimidin-5-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(1-phenyl-3,6-dihydro-2H-pyridin-4-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,5S)-3,4,5-trimethylpiperazin-1-yl]phenyl]benzamide;

4-fluoro-N-[4-fluoro-5-(2-morpholin-4-ylpyrimidin-5-yl)-2-[(3R,5S)-3,4,5-trimethylpiperazin-1-yl]phenyl]-3-methoxybenzamide;

3,5-dichloro-N-[4-fluoro-5-(2-morpholin-4-ylpyrimidin-5-yl)-2-[(3R,5S)-3,4,5-trimethylpiperazin-1-yl]phenyl]benzamide;

N-[4-fluoro-5-(2-morpholin-4-ylpyrimidin-5-yl)-2-[(3R,5S)-3,4,5-trimethylpiperazin-1-yl]phenyl]-6-oxo-4-(trifluoromethyl)-1H-pyridazine-3-carboxamide;

N-[4-fluoro-5-(2-morpholin-4-ylpyrimidin-5-yl)-2-[(3R)-3,4-dimethylpiperazin-1-yl]phenyl]benzamide;

N-[4-fluoro-5-(2-morpholin-4-ylpyrimidin-5-yl)-2-[(3R)-3,4-dimethylpiperazin-1-yl]phenyl]furan-2-carboxamide;

N-[4-fluoro-5-(2-morpholin-4-ylpyrimidin-5-yl)-2-[(3R)-3,4-dimethylpiperazin-1-yl]phenyl]pyridine-3-carboxamide;

N-[4-fluoro-5-(2-morpholin-4-ylpyridin-4-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-[6-(2-methoxyethoxy)pyridin-3-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-(3-morpholin-4-ylphenyl)-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,5S)-3,4,5-trimethylpiperazin-1-yl]phenyl]-2-methoxybenzamide;

2-chloro-4-fluoro-N-[4-fluoro-5-(2-morpholin-4-ylpyrimidin-5-yl)-2-[(3R,5S)-3,4,5-trimethylpiperazin-1-yl]phenyl]benzamide;

5-fluoro-N-[4-fluoro-5-(2-morpholin-4-ylpyrimidin-5-yl)-2-[(3R,5S)-3,4,5-trimethylpiperazin-1-yl]phenyl]-2-(trifluoromethyl)benzamide;

N-[4-fluoro-5-(2-morpholin-4-ylpyrimidin-5-yl)-2-[(3R,5S)-3,4,5-trimethylpiperazin-1-yl]phenyl]-3-methoxybenzamide;

N-[4-fluoro-5-[4-(2-methoxyethoxy)phenyl]-2-[(3R,5S)-3,4,5-trimethylpiperazin-1-yl]phenyl]-6-oxo-4-(trifluoromethyl)-1H-pyridine-3-carboxamide;

N-[5-[5-chloro-6-(2-methylpropoxy)pyridin-3-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[3-chloro-4-(cyclopropylmethoxy)phenyl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,5S)-3,4,5-trimethylpiperazin-1-yl]phenyl]-1-methyl-6-oxo-4-(trifluoromethyl)pyridine-3-carboxamide;

N-[5-(3,6-dihydro-2H-pyran-4-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-2-[(3R,5S)-3,4,5-trimethylpiperazin-1-yl]-5-(1,2,3,6-tetrahydropyridin-4-yl)phenyl]-6-oxo-4-(trifluoromethyl)-1H-pyridine-3-carboxamide;

N-[4-fluoro-5-(2-morpholin-4-ylpyrimidin-5-yl)-2-[(3R)-3,4-dimethylpiperazin-1-yl]phenyl]-3-(trifluoromethyl)-1H-pyrazole-4-carboxamide;

4-fluoro-N-[4-fluoro-5-(2-morpholin-4-ylpyrimidin-5-yl)-2-[(3R)-3,4-dimethylpiperazin-1-yl]phenyl]-3,5-dimethylbenzamide;

N-[5-(3-chloro-5-cyano-4-hydroxyphenyl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(5-cyano-6-phenylmethoxypyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(4-cyanophenyl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[6-(oxan-4-yloxy)pyridin-3-yl]-2-[(3R,5S)-3,4,5-trimethylpiperazin-1-yl]phenyl]-6-oxo-4-(trifluoromethyl)-1H-pyridine-3-carboxamide;

N-[5-(3-cyanophenyl)-4-fluoro-2-[(3R,5S)-3,4,5-trimethylpiperazin-1-yl]phenyl]-6-oxo-4-(trifluoromethyl)-1H-pyridine-3-carboxamide;

N-[5-[2-(dimethylamino)pyrimidin-5-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-(5,6-dimethoxypyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,5S)-3,4,5-trimethylpiperazin-1-yl]phenyl]-1,3-benzodioxole-4-carboxamide;

N-[4-fluoro-5-(2-morpholin-4-ylpyrimidin-5-yl)-2-[(3R,5S)-3,4,5-trimethylpiperazin-1-yl]phenyl]-4-methoxybenzamide;

4-fluoro-N-[4-fluoro-5-(2-morpholin-4-ylpyrimidin-5-yl)-2-[(3R,5S)-3,4,5-trimethylpiperazin-1-yl]phenyl]benzamide;

N-[4-fluoro-5-(3-fluoro-5-morpholin-4-ylphenyl)-2-[(3R,5S)-3,4,5-trimethylpiperazin-1-yl]phenyl]-6-oxo-4-(trifluoromethyl)-1H-pyridine-3-carboxamide;

2-chloro-N-[4-fluoro-5-(2-morpholin-4-ylpyrimidin-5-yl)-2-[(3R,5S)-3,4,5-trimethylpiperazin-1-yl]phenyl]benzamide;

2-fluoro-N-[4-fluoro-5-(2-morpholin-4-ylpyrimidin-5-yl)-2-[(3R,5S)-3,4,5-trimethylpiperazin-1-yl]phenyl]-3-methoxybenzamide;

3,4-difluoro-N-[4-fluoro-5-(2-morpholin-4-ylpyrimidin-5-yl)-2-[(3R,5S)-3,4,5-trimethylpiperazin-1-yl]phenyl]benzamide;

N-[4-fluoro-5-(4-methoxyphenyl)-2-[(3R,5S)-3,4,5-trimethylpiperazin-1-yl]phenyl]-6-oxo-4-(trifluoromethyl)-1H-pyridine-3-carboxamide;

N-[5-[4-(cyclopropylmethoxy)phenyl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(4-pyrrolidin-1-ylphenyl)-2-[(3R,5S)-3,4,5-trimethylpiperazin-1-yl]phenyl]-6-oxo-4-(trifluoromethyl)-1H-pyridine-3-carboxamide;

3-acetamido-N-[4-fluoro-5-(2-morpholin-4-ylpyrimidin-5-yl)-2-[(3R,5S)-3,4,5-trimethylpiperazin-1-yl]phenyl]benzamide;

N-[4-fluoro-5-(2-morpholin-4-ylpyrimidin-5-yl)-2-[(3R)-3,4-dimethylpiperazin-1-yl]phenyl]-1-methylindazole-3-carboxamide;

N-[4-fluoro-5-(4-morpholin-4-ylphenyl)-2-[(3R)-3,4-dimethylpiperazin-1-yl]phenyl]-1-methylindazole-3-carboxamide;

N-[4-fluoro-5-[3-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[3-[(4-fluoropiperidin-1-yl)methyl]phenyl]-2-[(3R,5S)-3,4,5-trimethylpiperazin-1-yl]phenyl]-6-oxo-4-(trifluoromethyl)-1H-pyridine-3-carboxamide;

N-[2-(3,4,6,7,9,9a-hexahydro-1H-pyrazino[2,1-c][1,4]oxazin-8-yl)-4-fluoro-5-(2-morpholin-4-ylpyrimidin-5-yl)phenyl]-6-oxo-4-(trifluoromethyl)-1H-pyridine-3-carboxamide;

N-[4-fluoro-5-(2-morpholin-4-ylpyrimidin-5-yl)-2-[(3R)-3,4-dimethylpiperazin-1-yl]phenyl]-1-methylpyrazole-4-carboxamide;

N-[4-fluoro-5-(4-morpholin-4-ylphenyl)-2-[(3R)-3,4-dimethylpiperazin-1-yl]phenyl]-1-methylpyrazole-4-carboxamide;

N-[5-(5-cyano-6-hydroxypyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(3-fluoro-4-morpholin-4-ylphenyl)-2-[(3R,5S)-3,4,5-trimethylpiperazin-1-yl]phenyl]-6-oxo-4-(trifluoromethyl)-1H-pyridine-3-carboxamide;

N-[5-[3-(cyclopropylmethoxy)phenyl]-4-fluoro-2-[(3R,5S)-3,4,5-trimethylpiperazin-1-yl]phenyl]-6-oxo-4-(trifluoromethyl)-1H-pyridine-3-carboxamide;

3-(dimethylamino)-N-[4-fluoro-5-(2-morpholin-4-ylpyrimidin-5-yl)-2-[(3R,5S)-3,4,5-trimethylpiperazin-1-yl]phenyl]benzamide;

N-[4-fluoro-5-(2-morpholin-4-ylpyrimidin-5-yl)-2-[(3R,5S)-3,4,5-trimethylpiperazin-1-yl]phenyl]-1,3-oxazole-4-carboxamide;

N-[4-fluoro-5-(2-morpholin-4-ylpyrimidin-5-yl)-2-[(3R)-3,4-dimethylpiperazin-1-yl]phenyl]-1-methyl-6-oxo-4-(trifluoromethyl)pyridine-3-carboxamide;

N-[4-fluoro-5-(4-morpholin-4-ylphenyl)-2-[(3R)-3,4-dimethylpiperazin-1-yl]phenyl]-1-methyl-6-oxo-4-(trifluoromethyl)pyridine-3-carboxamide;

N-[4-fluoro-5-(2-propan-2-yloxypyrimidin-5-yl)-2-[(3R,5S)-3,4,5-trimethylpiperazin-1-yl]phenyl]-6-oxo-4-(trifluoromethyl)-1H-pyridine-3-carboxamide;

N-[5-(6-cyanopyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(6-cyano-5-methylpyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(2-cyanopyridin-4-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[2-methoxy-6-(trifluoromethyl)pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-methoxy-6-methylpyridin-4-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-[6-methoxy-5-(trifluoromethyl)pyridin-3-yl]-2-[(3R,5S)-3,4,5-trimethylpiperazin-1-yl]phenyl]-6-oxo-4-(trifluoromethyl)-1H-pyridine-3-carboxamide;

4-cyano-N-[4-fluoro-5-(2-morpholin-4-ylpyrimidin-5-yl)-2-[(3R,5S)-3,4,5-trimethylpiperazin-1-yl]phenyl]-6-methoxypyridine-3-carboxamide;

3-chloro-N-[4-fluoro-5-(2-morpholin-4-ylpyrimidin-5-yl)-2-[(3R,5S)-3,4,5-trimethylpiperazin-1-yl]phenyl]benzamide;

2,6-dichloro-N-[4-fluoro-5-(2-morpholin-4-ylpyrimidin-5-yl)-2-[(3R,5S)-3,4,5-trimethylpiperazin-1-yl]phenyl]benzamide;

3-chloro-2-fluoro-N-[4-fluoro-5-(2-morpholin-4-ylpyrimidin-5-yl)-2-[(3R,5S)-3,4,5-trimethylpiperazin-1-yl]phenyl]benzamide;

N-[4-fluoro-5-(2-morpholin-4-ylpyrimidin-5-yl)-2-[(3R,5S)-3,4,5-trimethylpiperazin-1-yl]phenyl]-2-(trifluoromethyl)benzamide;

N-[5-[6-(dimethylamino)pyridin-3-yl]-4-fluoro-2-[(3R,5S)-3,4,5-trimethylpiperazin-1-yl]phenyl]-6-oxo-4-(trifluoromethyl)-1H-pyridine-3-carboxamide;

tert-butyl 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

N-[4-fluoro-2-[(3R,5S)-3,4,5-trimethylpiperazin-1-yl]-5-[4-(trifluoromethyl)phenyl]phenyl]-6-oxo-4-(trifluoromethyl)-1H-pyridine-3-carboxamide;

N-[4-fluoro-2-[(3R,5S)-3,4,5-trimethylpiperazin-1-yl]-5-[4-(trifluoromethoxy)phenyl]phenyl]-6-oxo-4-(trifluoromethyl)-1H-pyridine-3-carboxamide;

N-[4-fluoro-5-phenyl-2-[(3R,5S)-3,4,5-trimethylpiperazin-1-yl]phenyl]-6-oxo-4-(trifluoromethyl)-1H-pyridine-3-carboxamide;

N-[5-(4-chlorophenyl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[(4-methoxyphenyl)methyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-(6-methylpyridazin-4-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(2-methylpropyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[5-[1-(cyclopropylmethyl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-2-[(3R,5S)-3,4,5-trimethylpiperazin-1-yl]-5-[1-(3,3,3-trifluoropropyl)-3,6-dihydro-2H-pyridin-4-yl]phenyl]-6-oxo-4-(trifluoromethyl)-1H-pyridine-3-carboxamide;

N-[4-fluoro-5-[1-[(4-fluorophenyl)methyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(pyridin-3-ylmethyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-2-[(3R,5S)-3,4,5-trimethylpiperazin-1-yl]-5-[1-(thiophen-3-ylmethyl)-3,6-dihydro-2H-pyridin-4-yl]phenyl]-6-oxo-4-(trifluoromethyl)-1H-pyridine-3-carboxamide;

N-[5-[5-(cyclopropylmethoxy)pyridin-3-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(6-hydroxypyridin-3-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-piperazin-1-ylpyrimidin-5-yl)-2-[(3R,5S)-3,4,5-trimethylpiperazin-1-yl]phenyl]-6-oxo-4-(trifluoromethyl)-1H-pyridine-3-carboxamide;

3-chloro-5-fluoro-N-[4-fluoro-5-(2-morpholin-4-ylpyrimidin-5-yl)-2-[(3R,5S)-3,4,5-trimethylpiperazin-1-yl]phenyl]benzamide;

3,5-difluoro-N-[4-fluoro-5-(2-morpholin-4-ylpyrimidin-5-yl)-2-[(3R,5S)-3,4,5-trimethylpiperazin-1-yl]phenyl]benzamide;

N-[4-fluoro-5-[2-[(2R,6S)-2,6-dimethylmorpholin-4-yl]pyrimidin-5-yl]-2-[(3S,5R)-3,4,5-trimethylpiperazin-1-yl]phenyl]-6-oxo-4-(trifluoromethyl)-1H-pyridine-3-carboxamide;

N-[4-fluoro-2-[(3R,5S)-3,4,5-trimethylpiperazin-1-yl]-5-[1-(1,3-thiazol-2-ylmethyl)-3,6-dihydro-2H-pyridin-4-yl]phenyl]-6-oxo-4-(trifluoromethyl)-1H-pyridine-3-carboxamide;

N-[4-fluoro-5-[1-[(2-methyl-1,3-oxazol-5-yl)methyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[(1-methylpyrazol-4-yl)methyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[(4-morpholin-4-ylphenyl)methyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[[4-(4-methylpiperazin-1-yl)phenyl]methyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(oxan-4-ylmethyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

3,5-dichloro-N-[4-fluoro-5-(2-morpholin-4-ylpyrimidin-5-yl)-2-[(3R)-3-(dimethylamino)pyrrolidin-1-yl]phenyl]benzamide;

3,5-dichloro-N-[4-fluoro-5-(4-morpholin-4-ylphenyl)-2-[(3R)-3-(dimethylamino)pyrrolidin-1-yl]phenyl]benzamide;

N-[5-(5-cyano-6-morpholin-4-ylpyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(5-methyl-6-morpholin-4-ylpyridin-3-yl)-2-[(3R,5S)-3,4,5-trimethylpiperazin-1-yl]phenyl]-6-oxo-4-(trifluoromethyl)-1H-pyridine-3-carboxamide;

N-[5-(2,3-dihydro-1H-pyrrolo[2,3-b]pyridin-5-yl)-4-fluoro-2-[(3R,5S)-3,4,5-trimethylpiperazin-1-yl]phenyl]-6-oxo-4-(tnfluoromethyl)-1H-pyridine-3-carboxamide;

N-[4-fluoro-2-[(3R,5S)-3,4,5-trimethylpiperazin-1-yl]-5-[5-(trifluoromethyl)pyridin-3-yl]phenyl]-6-oxo-4-(trifluoromethyl)-1H-pyridine-3-carboxamide;

N-[5-[5-(tert-butylcarbamoyl)pyridin-3-yl]-4-fluoro-2-[(3R,5S)-3,4,5-trimethylpiperazin-1-yl]phenyl]-6-oxo-4-(trifluoromethyl)-1H-pyridine-3-carboxamide;

3-chloro-N-[4-fluoro-5-(2-morpholin-4-ylpyrimidin-5-yl)-2-[(3R,5S)-3,4,5-trimethylpiperazin-1-yl]phenyl]-5-(trifluoromethyl)benzamide;

3-fluoro-N-[4-fluoro-5-(2-morpholin-4-ylpyrimidin-5-yl)-2-[(3R,5S)-3,4,5-trimethylpiperazin-1-yl]phenyl]-5-(trifluoromethyl)benzamide;

N-[4-fluoro-5-(4-morpholin-4-ylphenyl)-2-[(3R)-3-(dimethylamino)pyrrolidin-1-yl]phenyl]-1H-pyrazole-4-carboxamide;

N-[4-fluoro-5-(5-methylpyridin-3-yl)-2-[(3R,5S)-3,4,5-trimethylpiperazin-1-yl]phenyl]-6-oxo-4-(trifluoromethyl)-1H-pyridine-3-carboxamide;

N-[5-(5-carbamoylpyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-2-[(3R,5S)-3,4,5-trimethylpiperazin-1-yl]-5-[5-(trifluoromethyl)pyridin-3-yl]phenyl]-1-methyl-6-oxo-4-(trifluoromethyl)pyridine-3-carboxamide;

N-[4-fluoro-5-(2-morpholin-4-ylpyrimidin-5-yl)-2-[(3R)-3,4-dimethylpiperazin-1-yl]phenyl]-4-methyl-1,3-thiazole-2-carboxamide;

2-[(dimethylamino)methyl]-N-[4-fluoro-5-(2-morpholin-4-ylpyrimidin-5-yl)-2-[(3R)-3,4-dimethylpiperazin-1-yl]phenyl]-1,3-thiazole-4-carboxamide;

4-chloro-N-[4-fluoro-5-(2-morpholin-4-ylpyrimidin-5-yl)-2-[(3R)-3,4-dimethylpiperazin-1-yl]phenyl]-1H-pyrazole-3-carboxamide;

N-[4-fluoro-5-(2-morpholin-4-ylpyrimidin-5-yl)-2-[(3R)-3-(dimethylamino)pyrrolidin-1-yl]phenyl]-1-methyl-6-oxo-4-(trifluoromethyl)pyridine-3-carboxamide;

N-[4-fluoro-5-(2-morpholin-4-ylpyrimidin-5-yl)-2-[(3R)-3-(dimethylamino)pyrrolidin-1-yl]phenyl]-3-(trifluoromethyl)-1H-pyrazole-4-carboxamide;

N-[4-fluoro-5-(2-morpholin-4-ylpyrimidin-5-yl)-2-[(3R,5S)-3,4,5-trimethylpiperazin-1-yl]phenyl]-3-(trifluoromethyl)benzamide;

N-[4-fluoro-5-(2-morpholin-4-ylpyrimidin-5-yl)-2-[(3R,5S)-3,4,5-trimethylpiperazin-1-yl]phenyl]-4-(trifluoromethyl)pyrimidine-5-carboxamide;

N-[4-fluoro-5-(2-morpholin-4-ylpyrimidin-5-yl)-2-[(3R,5S)-3,4,5-trimethylpiperazin-1-yl]phenyl]-4-(trifluoromethyl)-1,3-thiazole-5-carboxamide;

2-fluoro-N-[4-fluoro-5-(2-morpholin-4-ylpyrimidin-5-yl)-2-[(3R,5S)-3,4,5-trimethylpiperazin-1-yl]phenyl]-5-(trifluoromethyl)benzamide;

3-fluoro-N-[4-fluoro-5-(2-morpholin-4-ylpyrimidin-5-yl)-2-[(3R,5S)-3,4,5-trimethylpiperazin-1-yl]phenyl]-5-methoxybenzamide;

3,5-dichloro-N-[4-fluoro-5-(4-morpholin-4-ylphenyl)-2-[(3R,5S)-3,4,5-trimethylpiperazin-1-yl]phenyl]benzamide;

N-[4-fluoro-5-(2-morpholin-4-ylpyrimidin-5-yl)-2-[(3R),3,4-dimethylpiperazin-1-yl]phenyl]-1-methylpyrazole-3-carboxamide;

N-[4-fluoro-5-(2-morpholin-4-ylpyrimidin-5-yl)-2-[(3R),3,4-dimethylpiperazin-1-yl]phenyl]-1H-pyrazole-3-carboxamide;

N-[4-fluoro-5-(2-morpholin-4-ylpyrimidin-5-yl)-2-[(3R),3,4-dimethylpiperazin-1-yl]phenyl]-2-methyl-1,3-thiazole-4-carboxamide;

N-[4-fluoro-5-(2-morpholin-4-ylpyrimidin-5-yl)-2-[(3R),3,4-dimethylpiperazin-1-yl]phenyl]-2-methyl-1,3-thiazole-5-carboxamide;

N-[5-(6-acetamidopyridin-3-yl)-4-fluoro-2-[(3R),3,4-dimethylpiperazin-1-yl]phenyl]-6-oxo-4-(trifluoromethyl)-1H-pyridine-3-carboxamide;

N-[5-(2-cyanopyrimidin-5-yl)-4-fluoro-2-[(3R),3,4-dimethylpiperazin-1-yl]phenyl]-6-oxo-4-(trifluoromethyl)-1H-pyridine-3-carboxamide;

N-[5-[6-(cyclopropylmethoxy)pyridin-3-yl]-4-fluoro-2-[(3R)-3,4-dimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R),3,4-dimethylpiperazin-1-yl]phenyl]-2-methyl-4-(trifluoromethyl)-1,3-thiazole-5-carboxamide;

3,5-dichloro-N-[4-fluoro-5-(2-morpholin-4-ylpyrimidin-5-yl)-2-[(3R)-3,4-dimethylpiperazin-1-yl]phenyl]benzamide;

N-[4-fluoro-5-(3-fluoro-4-morpholin-4-ylphenyl)-2-[(3R)-3,4-dimethylpiperazin-1-yl]phenyl]-6-oxo-4-(trifluoromethyl)-1H-pyridine-3-carboxamide;

N-[4-fluoro-5-[2-[(2R,6S)-2,6-dimethylmorpholin-4-yl]pyrimidin-5-yl]-2-[(3R)-3,4-dimethylpiperazin-1-yl]phenyl]-6-oxo-4-(trifluoromethyl)-1H-pyridine-3-carboxamide;

4-fluoro-N-[4-fluoro-5-[2-(4-methyl-1,4-diazepan-1-yl)pyrimidin-5-yl]-2-[(3R,5S)-3,4,5-trimethylpiperazin-1-yl]phenyl]-2-(trifluoromethyl)benzamide;

N-[4-fluoro-5-(4-morpholin-4-ylphenyl)-2-[(3R,5S)-3,4,5-trimethylpiperazin-1-yl]phenyl]-1-methyl-6-oxo-4-(trifluoromethyl)pyridine-3-carboxamide;

N-[5-(5-cyanopyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(5-chloropyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(2-cyclohexyloxypyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[2-(4-methoxyphenyl)acetyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[6-(2-methoxyethoxy)pyridin-3-yl]-2-[(3R,5S)-3,4,5-trimethylpiperazin-1-yl]phenyl]-1-methyl-6-oxo-4-(trifluoromethyl)pyridine-3-carboxamide;

N-[4-fluoro-5-(2-pyrrolidin-1-ylpyrimidin-5-yl)-2-[(3R,5S)-3,4,5-trimethylpiperazin-1-yl]phenyl]-1-methyl-6-oxo-4-(trifluoromethyl)pyridine-3-carboxamide;

N-[4-fluoro-5-(2-morpholin-4-ylpyrimidin-5-yl)-2-[(3R,5S)-3,4,5-trimethylpiperazin-1-yl]phenyl]-3-(trifluoromethyl)thiophene-2-carboxamide;

3,5-dichloro-4-fluoro-N-[4-fluoro-5-(2-morpholin-4-ylpyrimidin-5-yl)-2-[(3R,5S)-3,4,5-trimethylpiperazin-1-yl]phenyl]benzamide;

2,3-dichloro-N-[4-fluoro-5-(2-morpholin-4-ylpyrimidin-5-yl)-2-[(3R,5S)-3,4,5-trimethylpiperazin-1-yl]phenyl]benzamide;

N-[4-fluoro-5-[3-[[methyl(oxetan-3-yl)amino]methyl]phenyl]-2-[(3R)-3,4-dimethylpiperazin-1-yl]phenyl]-6-oxo-4-(trifluoromethyl)-1H-pyridine-3-carboxamide;

N-[5-(5-ethoxypyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-5-(2-morpholin-4-ylpyrimidin-5-yl)-2-[(3R)-3,4-dimethylpiperazin-1-yl]phenyl]-1-methyl-6-oxopyridine-3-carboxamide;

N-[5-(6-acetamidopyridin-3-yl)-4-fluoro-2-[(3R)-3,4-dimethylpiperazin-1-yl]phenyl]-4-(difluoromethyl)-1-methyl-6-oxopyridine-3-carboxamide;

N-[5-(2-cyanopyrimidin-5-yl)-4-fluoro-2-[(3R)-3,4-dimethylpiperazin-1-yl]phenyl]-4-(difluoromethyl)-1-methyl-6-oxopyridine-3-carboxamide;

N-[5-[6-(dimethylamino)pyridin-3-yl]-4-fluoro-2-[(3R)-3,4-dimethylpiperazin-1-yl]phenyl]-6-oxo-4-(trifluoromethyl)-1H-pyridine-3-carboxamide;

N-[5-[5-cyano-6-(dimethylamino)pyridin-3-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[6-(dimethylamino)-5-fluoropyridin-3-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-(5-chloro-6-morpholin-4-ylpyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(2,3-dihydro-[1,4]dioxino[2,3-b]pyridin-7-yl)-4-fluoro-2-[(3R,5S)-3,4,5-trimethylpiperazin-1-yl]phenyl]-6-oxo-4-(trifluoromethyl)-1H-pyridine-3-carboxamide;

2-(difluoromethyl)-N-(2-((S)-3,4-dimethylpiperazin-1-yl)-4-fluoro-5-(2-((S)-2-methylmorpholino)pyrimidin-5-yl)phenyl)-4-fluorobenzamide;

N-[4-fluoro-5-(2-morpholin-4-ylpyrimidin-5-yl)-2-(3,3,4-trimethylpiperazin-1-yl)phenyl]-6-oxo-4-(trifluoromethyl)-1H-pyridine-3-carboxamide;

N-[4-fluoro-5-(2-morpholin-4-ylpyridin-4-yl)-2-[(3R,5S)-3,4,5-trimethylpiperazin-1-yl]phenyl]-1-methyl-6-oxo-4-(trifluoromethyl)pyridine-3-carboxamide;

N-[4-fluoro-5-(4-pyrrolidin-1-ylphenyl)-2-[(3R,5S)-3,4,5-trimethylpiperazin-1-yl]phenyl]-1-methyl-6-oxo-4-(trifluoromethyl)pyridine-3-carboxamide;

N-[5-[4-(cyclopropylmethoxy)phenyl]-4-fluoro-2-[(3R,5S)-3,4,5-trimethylpiperazin-1-yl]phenyl]-1-methyl-6-oxo-4-(trifluoromethyl)pyridine-3-carboxamide;

2,3-difluoro-N-[4-fluoro-5-(2-morpholin-4-ylpyrimidin-5-yl)-2-[(3R,5S)-3,4,5-trimethylpiperazin-1-yl]phenyl]benzamide;

2-chloro-4-fluoro-N-[4-fluoro-5-(2-morpholin-4-ylpyrimidin-5-yl)-2-[(3R)-3,4-dimethylpiperazin-1-yl]phenyl]benzamide;

N-[5-(1-cyclopentyl-3,6-dihydro-2H-pyridin-4-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[1-(4-methoxyphenyl)ethyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[5-(1-butan-2-yl-3,6-dihydro-2H-pyridin-4-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(6-morpholin-4-ylpyridin-3-yl)-2-[(3R)-3-(dimethylamino)pyrrolidin-1-yl]phenyl]-6-oxo-4-(trifluoromethyl)-1H-pyridine-3-carboxamide;

N-[4-fluoro-5-[1-(oxetan-3-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-piperidin-4-yl-2-[(3R,5S)-3,4,5-trimethylpiperazin-1-yl]phenyl]-6-oxo-4-(trifluoromethyl)-1H-pyridine-3-carboxamide;

N-[4-fluoro-5-(6-hydroxypyridin-3-yl)-2-[(3R)-3-(dimethylamino)pyrrolidin-1-yl]phenyl]-6-oxo-4-(trifluoromethyl)-1H-pyridine-3-carboxamide;

N-[5-[6-(cyclopropylmethoxy)pyridin-3-yl]-4-fluoro-2-[(3R)-3-(dimethylamino)pyrrolidin-1-yl]phenyl]-6-oxo-4-(trifluoromethyl)-1H-pyridine-3-carboxamide;

N-[4-fluoro-5-(6-morpholin-4-ylpyridin-3-yl)-2-[(3R)-3,4-dimethylpiperazin-1-yl]phenyl]-6-oxo-4-(trifluoromethyl)-1H-pyridine-3-carboxamide;

N-[4-fluoro-5-(2-propan-2-yloxypyrimidin-5-yl)-2-[(3R)-3,4-dimethylpiperazin-1-yl]phenyl]-6-oxo-4-(trifluoromethyl)-1H-pyridine-3-carboxamide;

N-[5-(2,3-dihydro-[1,4]dioxino[2,3-b]pyridin-7-yl)-4-fluoro-2-[(3R)-3,4-dimethylpiperazin-1-yl]phenyl]-6-oxo-4-(trifluoromethyl)-1H-pyridine-3-carboxamide;

N-[4-fluoro-5-[1-(1-methylpiperidin-4-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[5-[1-(2,2-dimethylpropanoyl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[1-(2,2-dimethylpropanoyl)piperidin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(1-pyrimidin-2-yl-3,6-dihydro-2H-pyridin-4-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-[2-[(2R,6S)-2,6-dimethylmorpholin-4-yl]pyrimidin-5-yl]-2-[(3S,5R)-3,4,5-trimethylpiperazin-1-yl]phenyl]-1-methyl-6-oxo-4-(trifluoromethyl)pyridine-3-carboxamide;

N-[4-fluoro-5-(3-fluoro-4-morpholin-4-ylphenyl)-2-[(3R,5S)-3,4,5-trimethylpiperazin-1-yl]phenyl]-1-methyl-6-oxo-4-(trifluoromethyl)pyridine-3-carboxamide;

4-fluoro-N-[4-fluoro-5-(2-morpholin-4-ylpyrimidin-5-yl)-2-[(3R,5S)-3,4,5-trimethylpiperazin-1-yl]phenyl]-2-(trifluoromethyl)benzamide;

N-[4-fluoro-5-(1-methylsulfonyl-2,5-dihydropyrrol-3-yl)-2-[(3R,5S)-3,4,5-trimethylpiperazin-1-yl]phenyl]-6-oxo-4-(trifluoromethyl)-1H-pyridine-3-carboxamide;

3,5-dichloro-N-[5-[6-(cyclopropylmethoxy)pyridin-3-yl]-4-fluoro-2-[(3R,5S)-3,4,5-trimethylpiperazin-1-yl]phenyl]benzamide;

2-chloro-N-[5-[6-(cyclopropylmethoxy)pyridin-3-yl]-4-fluoro-2-[(3R,5S)-3,4,5-trimethylpiperazin-1-yl]phenyl]-4-fluorobenzamide;

N-[5-(1-acetyl-3,6-dihydro-2H-pyridin-4-yl)-4-fluoro-2-[(3R,5S)-3,4,5-trimethylpiperazin-1-yl]phenyl]-6-oxo-4-(trifluoromethyl)-1H-pyridine-3-carboxamide;

ethyl 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

2-methylpropyl 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

N-[5-[1-(3,3-dimethylbutanoyl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[1-(3,3-dimethylbutanoyl)piperidin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(6-fluoropyridin-3-yl)-2-[(3R,5S)-3,4,5-trimethylpiperazin-1-yl]phenyl]-6-oxo-4-(trifluoromethyl)-1H-pyridine-3-carboxamide;

N-[2-[4-(dimethylamino)piperidin-1-yl]-4-fluoro-5-(2-morpholin-4-ylpyrimidin-5-yl)phenyl]-6-oxo-4-(trifluoromethyl)-1H-pyridine-3-carboxamide;

N-[2-[4-[2-(dimethylamino)ethyl]piperazin-1-yl]-4-fluoro-5-(2-morpholin-4-ylpyrimidin-5-yl)phenyl]-6-oxo-4-(trifluoromethyl)-1H-pyridine-3-carboxamide;

N-[2-[2-[(dimethylamino)methyl]morpholin-4-yl]-4-fluoro-5-(2-morpholin-4-ylpyrimidin-5-yl)phenyl]-6-oxo-4-(trifluoromethyl)-1H-pyridine-3-carboxamide;

N-[4-fluoro-5-(6-pyrrolidin-1-ylpyridin-3-yl)-2-[(3R,5S)-3,4,5-trimethylpiperazin-1-yl]phenyl]-6-oxo-4-(trifluoromethyl)-1H-pyridine-3-carboxamide;

N-[5-(5-cyano-6-pyrrolidin-1-ylpyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(2,2-difluoro-1,3-benzodioxol-5-yl)-4-fluoro-2-[(3R,5S)-3,4,5-trimethylpiperazin-1-yl]phenyl]-6-oxo-4-(trifluoromethyl)-1H-pyridine-3-carboxamide;

3-chloro-4-fluoro-N-[4-fluoro-5-(2-morpholin-4-ylpyrimidin-5-yl)-2-[(3R,5S)-3,4,5-trimethylpiperazin-1-yl]phenyl]benzamide;

3-chloro-N-[4-fluoro-5-(2-morpholin-4-ylpyrimidin-5-yl)-2-[(3R,5S)-3,4,5-trimethylpiperazin-1-yl]phenyl]-5-methoxybenzamide;

3-chloro-2,4-difluoro-N-[4-fluoro-5-(2-morpholin-4-ylpyrimidin-5-yl)-2-[(3R,5S)-3,4,5-trimethylpiperazin-1-yl]phenyl]benzamide;

N-[4-fluoro-5-(1-methyl-3,6-dihydro-2H-pyridin-4-yl)-2-[(3R,5S)-3,4,5-trimethylpiperazin-1-yl]phenyl]-6-oxo-4-(trifluoromethyl)-1H-pyridine-3-carboxamide;

N-[4-fluoro-2-(8-methyl-3,8-diazabicyclo[3.2.1]octan-3-yl)-5-(2-morpholin-4-ylpyrimidin-5-yl)phenyl]-6-oxo-4-(trifluoromethyl)-1H-pyridine-3-carboxamide;

N-[5-(6-cyano-4-methylpyridin-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(1-pyridin-2-yl-3,6-dihydro-2H-pyridin-4-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(5-methylpyrimidin-2-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[6-[(2R,6S)-2,6-dimethylmorpholin-4-yl]pyridin-3-yl]-2-[(3S,5R)-3,4,5-trimethylpiperazin-1-yl]phenyl]-6-oxo-4-(trifluoromethyl)-1H-pyridine-3-carboxamide;

N-[4-fluoro-5-[2-[(2R,6S)-2,6-dimethylmorpholin-4-yl]pyrimidin-5-yl]-2-[(3R)-3,4-dimethylpiperazin-1-yl]phenyl]-1-methyl-6-oxo-4-(trifluoromethyl)pyridine-3-carboxamide;

N-[4-fluoro-5-[1-(6-methoxypyrimidin-4-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[5-[1-(5-chloropyrimidin-2-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

ethyl 2-[4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridin-1-yl]pyrimidine-4-carboxylate;

N-[4-fluoro-2-[3-(methylamino)pyrrolidin-1-yl]-5-(2-morpholin-4-ylpyrimidin-5-yl)phenyl]-6-oxo-4-(trifluoromethyl)-1H-pyridine-3-carboxamide;

N-[2-[3-[(dimethylamino)methyl]pyrrolidin-1-yl]-4-fluoro-5-(2-morpholin-4-ylpyrimidin-5-yl)phenyl]-6-oxo-4-(trifluoromethyl)-1H-pyridine-3-carboxamide;

N-[4-fluoro-5-[2-(4-methylpiperazin-1-yl)pyrimidin-5-yl]-2-[(3R)-3,4-dimethylpiperazin-1-yl]phenyl]-1-methyl-6-oxo-4-(trifluoromethyl)pyridine-3-carboxamide;

N-[4-fluoro-5-(2-morpholin-4-ylpyrimidin-5-yl)-2-[(3R,5S)-3,4,5-trimethylpiperazin-1-yl]phenyl]-3-hydroxy-5-(trifluoromethyl)benzamide;

N-[4-fluoro-5-(2-morpholin-4-ylpyrimidin-5-yl)-2-[(3R,5S)-3,4,5-trimethylpiperazin-1-yl]phenyl]-3-hydroxybenzamide;

N-[4-fluoro-5-(2-morpholin-4-ylpyrimidin-5-yl)-2-[(3R,5S)-3,4,5-trimethylpiperazin-1-yl]phenyl]-3-hydroxyquinoline-4-carboxamide;

N-[4-fluoro-5-(2-morpholin-4-ylpyrimidin-5-yl)-2-[(3R)-3-(dimethylamino)pyrrolidin-1-yl]phenyl]-1-methyl-3-(trifluoromethyl)pyrazole-4-carboxamide;

N-[4-fluoro-5-(2-morpholin-4-ylpyrimidin-5-yl)-2-[(3R)-3,4-dimethylpiperazin-1-yl]phenyl]-1-methyl-3-(trifluoromethyl)pyrazole-4-carboxamide;

N-[5-[1-(dimethylcarbamoyl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(pyrrolidine-1-carbonyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(4-methylpiperazine-1-carbonyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

phenyl 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

N-[4-fluoro-5-[1-[(2R,6S)-2,6-dimethyloxan-4-yl]-3,6-dihydro-2H-pyridin-4-yl]-2-[(3S,5R)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,5S)-3,4,5-trimethylpiperazin-1-yl]phenyl]-4-hydroxy-2-(trifluoromethyl)benzamide;

2,3-difluoro-N-[4-fluoro-5-(2-morpholin-4-ylpyrimidin-5-yl)-2-[(3R,5S)-3,4,5-trimethylpiperazin-1-yl]phenyl]-5-hydroxybenzamide;

N-[5-[2-(cyclobutylmethoxy)pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[2-(2,2-dimethylpropoxy)pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[2-(diethylamino)pyrimidin-5-yl]-4-fluoro-2-[(3R,5S)-3,4,5-trimethylpiperazin-1-yl]phenyl]-6-oxo-4-(trifluoromethyl)-1H-pyridine-3-carboxamide;

3-fluoro-N-[4-fluoro-5-(2-morpholin-4-ylpyrimidin-5-yl)-2-[(3R,5S)-3,4,5-trimethylpiperazin-1-yl]phenyl]-2-(trifluoromethyl)benzamide;

3,4,5-trifluoro-N-[4-fluoro-5-(2-morpholin-4-ylpyrimidin-5-yl)-2-[(3R,5S)-3,4,5-trimethylpiperazin-1-yl]phenyl]benzamide;

2-fluoro-N-[4-fluoro-5-(2-morpholin-4-ylpyrimidin-5-yl)-2-[(3R,5S)-3,4,5-trimethylpiperazin-1-yl]phenyl]-6-(trifluoromethyl)benzamide;

4-fluoro-N-[4-fluoro-5-(2-morpholin-4-ylpyrimidin-5-yl)-2-[(3R)-3,4-dimethylpiperazin-1-yl]phenyl]-2-(trifluoromethyl)benzamide;

4-fluoro-N-[4-fluoro-5-(2-morpholin-4-ylpyrimidin-5-yl)-2-[(3R)-3,4-dimethylpiperazin-1-yl]phenyl]-2-(trifluoromethyl)benzamide;

3,5-dichloro-N-[4-fluoro-2-[3-(methylamino)pyrrolidin-1-yl]-5-(2-morpholin-4-ylpyrimidin-5-yl)phenyl]benzamide;

N-[4-fluoro-5-[6-(4-methylpiperazin-1-yl)pyridin-3-yl]-2-[(3R)-3,4-dimethylpiperazin-1-yl]phenyl]-1-methyl-6-oxo-4-(trifluoromethyl)pyridine-3-carboxamide;

N-[4-fluoro-5-[4-(4-methylpiperazin-1-yl)phenyl]-2-[(3R)-3,4-dimethylpiperazin-1-yl]phenyl]-1-methyl-6-oxo-4-(trifluoromethyl)pyridine-3-carboxamide;

N-[4-fluoro-2-[3-[methyl(propyl)amino]pyrrolidin-1-yl]-5-(2-morpholin-4-ylpyrimidin-5-yl)phenyl]-6-oxo-4-(trifluoromethyl)-1H-pyridine-3-carboxamide;

3,5-dichloro-N-[4-fluoro-2-[3-[methyl(propyl)amino]pyrrolidin-1-yl]-5-(2-morpholin-4-ylpyrimidin-5-yl)phenyl]benzamide;

N-[5-[1-[2-(dimethylamino)acetyl]-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

4-[4-[5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]pyrimidin-2-yl]piperazin-1-yl]-4-oxobutanoic acid;

N-[4-fluoro-5-(2-morpholin-4-ylpyrimidin-5-yl)-2-[(3R,4R)-3-(dimethylamino)-4-fluoropyrrolidin-1-yl]phenyl]-1-methyl-6-oxo-4-(trifluoromethyl)pyridine-3-carboxamide;

N-[5-[6-(cyclopropylmethoxy)pyridin-3-yl]-4-fluoro-2-[(3R,4R)-3-(dimethylamino)-4-fluoropyrrolidin-1-yl]phenyl]-1-methyl-6-oxo-4-(trifluoromethyl)pyridine-3-carboxamide;

N-[4-fluoro-2-morpholin-4-yl-5-(2-piperazin-1-ylpyrimidin-5-yl)phenyl]-6-oxo-4-(trifluoromethyl)-1H-pyridine-3-carboxamide;

N-[4-fluoro-5-(2-morpholin-4-ylpyrimidin-5-yl)-2-[(3R,4R)-3-(dimethylamino)-4-fluoropyrrolidin-1-yl]phenyl]-6-oxo-4-(trifluoromethyl)-1H-pyridine-3-carboxamide;

N-[5-[6-(cyclopropylmethoxy)pyridin-3-yl]-4-fluoro-2-[(3R,4R)-3-(dimethylamino)-4-fluoropyrrolidin-1-yl]phenyl]-6-oxo-4-(trifluoromethyl)-1H-pyridine-3-carboxamide;

N-[4-fluoro-5-(6-hydroxypyridin-3-yl)-2-[(3R,4R)-3-(dimethylamino)-4-fluoropyrrolidin-1-yl]phenyl]-6-oxo-4-(trifluoromethyl)-1H-pyridine-3-carboxamide;

tert-butyl 4-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-3,6-dihydro-2H-pyridine-1-carboxylate;

N-[5-[6-(cyclopropylmethoxy)pyridin-3-yl]-4-fluoro-2-[(3R,5S)-3,4,5-trimethylpiperazin-1-yl]phenyl]-4-(difluoromethyl)-6-oxo-1H-pyridine-3-carboxamide;

1-ethyl-N-[4-fluoro-5-(2-morpholin-4-ylpyrimidin-5-yl)-2-[(3R,5S)-3,4,5-trimethylpiperazin-1-yl]phenyl]-6-oxo-4-(trifluoromethyl)pyridine-3-carboxamide;

4-fluoro-N-[4-fluoro-5-[2-(4-methylpiperazin-1-yl)pyrimidin-5-yl]-2-[(3R)-3,4-dimethylpiperazin-1-yl]phenyl]-2-(trifluoromethyl)benzamide;

4-fluoro-N-[4-fluoro-5-[6-(4-methylpiperazin-1-yl)pyridin-3-yl]-2-[(3R)-3,4-dimethylpiperazin-1-yl]phenyl]-2-(trifluoromethyl)benzamide;

2,3-dichloro-N-[4-fluoro-5-(2-morpholin-4-ylpyrimidin-5-yl)-2-[(3R)-3,4-dimethylpiperazin-1-yl]phenyl]benzamide;

N-[4-fluoro-2-[(3R)-3,4-dimethylpiperazin-1-yl]-5-[2-(2,2,6,6-tetramethylmorpholin-4-yl)pyrimidin-5-yl]phenyl]-6-oxo-4-(trifluoromethyl)-1H-pyridine-3-carboxamide;

N-[4-fluoro-2-[(3R,5S)-3,4,5-trimethylpiperazin-1-yl]-5-[2-(2,2,6,6-tetramethylmorpholin-4-yl)pyrimidin-5-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,5S)-3,4,5-trimethylpiperazin-1-yl]phenyl]-5-(trifluoromethyl)-1H-pyrazole-3-carboxamide;

tert-butyl 5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

tert-butyl 3-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-2,5-dihydropyrrole-1-carboxylate;

tert-butyl 3-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-8-azabicyclo[3.2.1]oct-2-ene-8-carboxylate;

tert-butyl 5-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-3,6-dihydro-2H-pyridine-1-carboxylate;

tert-butyl 3-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-2,5-dihydropyrrole-1-carboxylate;

tert-butyl 3-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-8-azabicyclo[3.2.1]oct-2-ene-8-carboxylate;

N-[4-fluoro-2-[(3R,5S)-3,4,5-trimethylpiperazin-1-yl]-5-(1,2,3,6-tetrahydropyridin-5-yl)phenyl]-6-oxo-4-(trifluoromethyl)-1H-pyridine-3-carboxamide;

N-[5-(2,5-dihydro-1H-pyrrol-3-yl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(8-azabicyclo[3.2.1]oct-2-en-3-yl)-4-fluoro-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-5-(6-morpholin-4-ylpyridin-3-yl)-2-[(3R)-3,4-dimethylpiperazin-1-yl]phenyl]-6-oxo-1H-pyridine-3-carboxamide;

N-[5-(2-butan-2-yloxypyridin-4-yl)-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,4R)-3-(dimethylamino)-4-methoxypyrrolidin-1-yl]phenyl]-6-oxo-4-(trifluoromethyl)-1H-pyridine-3-carboxamide;

N-[4-fluoro-5-(1-pyrimidin-2-yl-3,6-dihydro-2H-pyridin-5-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-(1-pyrimidin-2-yl-2,5-dihydropyrrol-3-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-(8-pyrimidin-2-yl-8-azabicyclo[3.2.1]oct-2-en-3-yl)-2-[(3R,5S)-3,4,5-trimethylpiperazin-1-yl]phenyl]-6-oxo-4-(trifluoromethyl)-1H-pyridine-3-carboxamide;

N-[4-fluoro-2-[(3R)-3,4-dimethylpiperazin-1-yl]-5-[2-[(3R)-3-methylmorpholin-4-yl]pyrimidin-5-yl]phenyl]-6-oxo-4-(trifluoromethyl)-1H-pyridine-3-carboxamide;

N-[4-fluoro-5-[2-[(3R)-3-methylmorpholin-4-yl]pyrimidin-5-yl]-2-[(3S,5R)-3,4,5-trimethylpiperazin-1-yl]phenyl]-6-oxo-4-(trifluoromethyl)-1H-pyridine-3-carboxamide;

N-[4-fluoro-5-(2-morpholin-4-yl-1,4,5,6-tetrahydropyrimidin-5-yl)-2-[(3R,5S)-3,4,5-trimethylpiperazin-1-yl]phenyl]-6-oxo-4-(trifluoromethyl)-1H-pyridine-3-carboxamide;

N-[4-fluoro-2-[(3S)-3,4-dimethylpiperazin-1-yl]-5-[2-[(2R)-2-methylmorpholin-4-yl]pyrimidin-5-yl]phenyl]-6-oxo-4-(trifluoromethyl)-1H-pyridine-3-carboxamide;

N-[4-fluoro-5-[6-[(2R,6S)-2,6-dimethylmorpholin-4-yl]pyridin-3-yl]-2-[(3R)-3,4-dimethylpiperazin-1-yl]phenyl]-6-oxo-4-(trifluoromethyl)-1H-pyridine-3-carboxamide;

4-(difluoromethyl)-N-[4-fluoro-5-(2-morpholin-4-ylpyrimidin-5-yl)-2-[(3R,5S)-3,4,5-trimethylpiperazin-1-yl]phenyl]-1-methyl-6-oxopyridine-3-carboxamide;

N-[4-fluoro-5-(2-morpholin-4-ylpyrimidin-5-yl)-2-[(1R,4R)-5-methyl-2,5-diazabicyclo[2.2.1]heptan-2-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,4R)-3-[ethyl(methyl)amino]-4-fluoropyrrolidin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R)-3-[ethyl(methyl)amino]pyrrolidin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,4R)-3-[ethyl(methyl)amino]-4-fluoropyrrolidin-1-yl]phenyl]-1-methyl-6-oxo-4-(trifluoromethyl)pyridine-3-carboxamide;

N-[4-fluoro-2-[(3R)-3,4-dimethylpiperazin-1-yl]-5-[2-[(2R)-2-propan-2-ylmorpholin-4-yl]pyrimidin-5-yl]phenyl]-6-oxo-4-(trifluoromethyl)-1H-pyridine-3-carboxamide;

N-[4-fluoro-5-[2-[(2R)-2-propan-2-ylmorpholin-4-yl]pyrimidin-5-yl]-2-[(3S,5R)-3,4,5-trimethylpiperazin-1-yl]phenyl]-6-oxo-4-(trifluoromethyl)-1H-pyridine-3-carboxamide;

N-[5-[2-(2,2-dimethylmorpholin-4-yl)pyrimidin-5-yl]-4-fluoro-2-[(3R)-3,4-dimethylpiperazin-1-yl]phenyl]-6-oxo-4-(trifluoromethyl)-1H-pyridine-3-carboxamide;

N-[5-[2-(2,2-dimethylmorpholin-4-yl)pyrimidin-5-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,5S)-3,4,5-trimethylpiperazin-1-yl]phenyl]-7-(trifluoromethyl)-[1,2,4]triazolo[4,3-a]pyridine-6-carboxamide;

N-[5-[2-(7-azabicyclo[2.2.1]heptan-7-yl)pyrimidin-5-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,5R)-3,4,5-trimethylpiperazin-1-yl]phenyl]-6-oxo-4-(trifluoromethyl)-1H-pyridine-3-carboxamide;

N-[4-fluoro-5-(3-fluoro-4-morpholin-4-ylphenyl)-2-[(3R,5R)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,5R)-3,4,5-trimethylpiperazin-1-yl]phenyl]-6-oxo-4-(trifluoromethyl)-1H-pyridine-3-carboxamide;

N-[4-fluoro-5-[2-[(2R,6S)-2,6-dimethylmorpholin-4-yl]pyrimidin-5-yl]-2-[(3R,5R)-3,4,5-trimethylpiperazin-1-yl]phenyl]-6-oxo-4-(trifluoromethyl)-1H-pyridine-3-carboxamide;

N-[4-fluoro-5-(3-fluoro-4-morpholin-4-ylphenyl)-2-[(3R,5R)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,4R)-3-[ethyl(methyl)amino]-4-methoxypyrrolidin-1-yl]phenyl]-6-oxo-4-(trifluoromethyl)-1H-pyridine-3-carboxamide;

N-[5-[6-(cyclopropylmethoxy)pyridin-3-yl]-4-fluoro-2-[(3R,5R)-3,4,5-trimethylpiperazin-1-yl]phenyl]-6-oxo-4-(trifluoromethyl)-1H-pyridine-3-carboxamide;

N-[4-fluoro-5-[2-[(2R,6S)-2,6-dimethylmorpholin-4-yl]pyrimidin-5-yl]-2-[(3S,5S)-3,4,5-trimethylpiperazin-1-yl]phenyl]-6-oxo-4-(trifluoromethyl)-1H-pyridine-3-carboxamide;

N-[5-[6-(cyclopropylmethoxy)pyridin-3-yl]-4-fluoro-2-[(3R,5R)-3,4,5-trimethylpiperazin-1-yl]phenyl]-6-oxo-4-(trifluoromethyl)-1H-pyridine-3-carboxamide;

N-[4-fluoro-5-[2-[methyl-[(3R)-oxolan-3-yl]amino]pyrimidin-5-yl]-2-[(3R)-3,4-dimethylpiperazin-1-yl]phenyl]-6-oxo-4-(trifluoromethyl)-1H-pyridine-3-carboxamide;

N-[4-fluoro-5-[2-[methyl-[(3R)-oxolan-3-yl]amino]pyrimidin-5-yl]-2-[(3S,5R)-3,4,5-trimethylpiperazin-1-yl]phenyl]-6-oxo-4-(trifluoromethyl)-1H-pyridine-3-carboxamide;

4-fluoro-N-[4-fluoro-5-(2-morpholin-4-ylpyrimidin-5-yl)-2-[(3R,5S)-3,5-dimethylpiperazin-1-yl]phenyl]-2-(trifluoromethyl)benzamide;

N-[4-fluoro-5-[1-(6-methoxypyrimidin-4-yl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(5-methoxypyrimidin-2-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(5-fluoropyrimidin-2-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[5-[1-(4,6-dimethylpyrimidin-2-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(5-formylpyrimidin-2-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[2-[methyl(oxan-4-yl)amino]pyrimidin-5-yl]-2-[(3R)-3,4-dimethylpiperazin-1-yl]phenyl]-6-oxo-4-(trifluoromethyl)-1H-pyridine-3-carboxamide;

N-[4-fluoro-5-[2-[methyl(oxan-4-yl)amino]pyrimidin-5-yl]-2-[(3R,5S)-3,4,5-trimethylpiperazin-1-yl]phenyl]-6-oxo-4-(trifluoromethyl)-1H-pyridine-3-carboxamide;

N-[5-[1-(dimethylcarbamoyl)-3,6-dihydro-2H-pyridin-5-yl]-4-fluoro-2-[(3R,5S)-3,4,5-trimethylpiperazin-1-yl]phenyl]-6-oxo-4-(trifluoromethyl)-1H-pyridine-3-carboxamide;

ethyl 5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

N-[4-fluoro-5-[1-(pyrrolidine-1-carbonyl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(5-methoxypyrimidin-2-yl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(5-methylpyrimidin-2-yl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(5-fluoropyrimidin-2-yl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-4-yl)-2-[(3R,5S)-3,4,5-trimethylpiperazin-1-yl]phenyl]-6-oxo-4-(trifluoromethyl)-1H-pyridine-3-carboxamide;

4-fluoro-N-[4-fluoro-5-[2-(4-methylpiperazin-1-yl)pyrimidin-5-yl]-2-[(3R,5S)-3,4,5-trimethylpiperazin-1-yl]phenyl]-2-(trifluoromethyl)benzamide;

N-[5-[2-(dimethylamino)pyrimidin-5-yl]-4-fluoro-2-[(3R,5S)-3,4,5-trimethylpiperazin-1-yl]phenyl]-4-fluoro-2-(trifluoromethyl)benzamide;

4-fluoro-N-[4-fluoro-2-[(3R,5S)-3,4,5-trimethylpiperazin-1-yl]-5-[2-[(3R,5S)-3,4,5-trimethylpiperazin-1-yl]pyrimidin-5-yl]phenyl]-2-(trifluoromethyl)benzamide;

4-fluoro-N-[4-fluoro-5-[2-(4-methylpiperazin-1-yl)pyrimidin-5-yl]-2-[(3R,5R)-3,4,5-trimethylpiperazin-1-yl]phenyl]-2-(trifluoromethyl)benzamide;

4-(difluoromethyl)-N-[4-fluoro-5-[2-[(2R,6S)-2,6-dimethylmorpholin-4-yl]pyrimidin-5-yl]-2-[(3R)-3,4-dimethylpiperazin-1-yl]phenyl]-1-methyl-6-oxopyridine-3-carboxamide;

N-[4-fluoro-5-(6-morpholin-4-ylpyridazin-3-yl)-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-5-[2-[(2R,6S)-2,6-dimethylmorpholin-4-yl]pyrimidin-5-yl]-2-[(3S,5R)-3,4,5-trimethylpiperazin-1-yl]phenyl]-6-oxo-1H-pyridine-3-carboxamide;

4-(difluoromethyl)-N-[4-fluoro-5-[2-[(2R)-2-methylmorpholin-4-yl]pyrimidin-5-yl]-2-[(3R,5S)-3,4,5-trimethylpiperazin-1-yl]phenyl]-6-oxo-1H-pyridine-3-carboxamide;

4-fluoro-N-[4-fluoro-5-(2-morpholin-4-ylpyrimidin-5-yl)-2-[(3R,5R)-3,4,5-trimethylpiperazin-1-yl]phenyl]-2-(trifluoromethyl)benzamide;

N-[4-fluoro-5-[2-[(2R)-2-methylmorpholin-4-yl]pyrimidin-5-yl]-2-[(3R,5S)-3,4,5-trimethylpiperazin-1-yl]phenyl]-6-oxo-4-(trifluoromethyl)-1H-pyridine-3-carboxamide;

N-[4-fluoro-2-[(3R)-3,4-dimethylpiperazin-1-yl]-5-[2-[(2R)-2-methylmorpholin-4-yl]pyrimidin-5-yl]phenyl]-6-oxo-4-(trifluoromethyl)-1H-pyridine-3-carboxamide;

N-[4-fluoro-5-[2-[(2R)-2-methylmorpholin-4-yl]pyrimidin-5-yl]-2-[(3S,5R)-3,4,5-trimethylpiperazin-1-yl]phenyl]-6-oxo-4-(trifluoromethyl)-1H-pyridine-3-carboxamide;

N-[4-fluoro-5-(1-pyrimidin-2-yl-3,6-dihydro-2H-pyridin-5-yl)-2-[(3R,5S)-3,4,5-trimethylpiperazin-1-yl]phenyl]-1-methyl-6-oxo-4-(trifluoromethyl)pyridine-3-carboxamide;

N-[4-fluoro-5-[4-[(4-fluorophenyl)methyl]piperazin-1-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-(4-pyrimidin-2-ylpiperazin-1-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[5-(hydroxymethyl)pyrimidin-2-yl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-5-[2-[(2R,6S)-2,6-dimethylmorpholin-4-yl]pyrimidin-5-yl]-2-[(3S)-3,4-dimethylpiperazin-1-yl]phenyl]-6-oxo-1H-pyridine-3-carboxamide;

4-(difluoromethyl)-N-[4-fluoro-2-[(3S)-3,4-dimethylpiperazin-1-yl]-5-[2-[(2R)-2-methylmorpholin-4-yl]pyrimidin-5-yl]phenyl]-6-oxo-1H-pyridine-3-carboxamide;

4-(difluoromethyl)-N-[4-fluoro-5-[2-[(2R)-2-methylmorpholin-4-yl]pyrimidin-5-yl]-2-[(3S,5R)-3,4,5-trimethylpiperazin-1-yl]phenyl]-6-oxo-1H-pyridine-3-carboxamide;

4-(difluoromethyl)-N-[4-fluoro-2-[(3R)-3,4-dimethylpiperazin-1-yl]-5-[2-[(2R)-2-methylmorpholin-4-yl]pyrimidin-5-yl]phenyl]-6-oxo-1H-pyridine-3-carboxamide;

N-[4-fluoro-5-(2-methylsulfonylpyrimidin-4-yl)-2-[(3R,5S)-3,4,5-trimethylpiperazin-1-yl]phenyl]-6-oxo-4-(trifluoromethyl)-1H-pyridine-3-carboxamide;

4-fluoro-N-[4-fluoro-5-[2-(4-methyl-1,4-diazepan-1-yl)pyrimidin-5-yl]-2-[(3R)-3,4-dimethylpiperazin-1-yl]phenyl]-2-(trifluoromethyl)benzamide;

4-fluoro-N-[4-fluoro-5-(2-piperazin-1-ylpyrimidin-5-yl)-2-[(3R)-3,4-dimethylpiperazin-1-yl]phenyl]-2-(trifluoromethyl)benzamide;

4-fluoro-N-[4-fluoro-5-(6-morpholin-4-ylpyridin-3-yl)-2-[(3R)-3,4-dimethylpiperazin-1-yl]phenyl]-2-(trifluoromethyl)benzamide;

4-(difluoromethyl)-N-[4-fluoro-5-[6-(oxan-4-yloxy)pyridin-3-yl]-2-[(3R)-3,4-dimethylpiperazin-1-yl]phenyl]-6-oxo-1H-pyridine-3-carboxamide;

N-[5-[1-(5-cyanopyrimidin-2-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[1-[5-[(dimethylamino)methyl]pyrimidin-2-yl]-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[5-(morpholin-4-ylmethyl)pyrimidin-2-yl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[5-[(4-methylpiperazin-1-yl)methyl]pyrimidin-2-yl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

2-methylpropyl 5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

N-[4-fluoro-5-[1-(5-formylpyrimidin-2-yl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-5-(2-morpholin-4-ylpyrimidin-5-yl)-2-[(3R)-3,4-dimethylpiperazin-1-yl]phenyl]-6-oxo-1H-pyridine-3-carboxamide;

N-[5-[6-(cyclopropylmethoxy)pyridin-3-yl]-4-fluoro-2-[(3R)-3,4-dimethylpiperazin-1-yl]phenyl]-4-(difluoromethyl)-6-oxo-1H-pyridine-3-carboxamide;

4-(difluoromethyl)-N-[4-fluoro-5-(6-morpholin-4-ylpyridin-3-yl)-2-[(3R,5S)-3,4,5-trimethylpiperazin-1-yl]phenyl]-6-oxo-1H-pyridine-3-carboxamide;

N-[4-fluoro-5-[1-[5-(hydroxymethyl)pyrimidin-2-yl]-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide;

N-[5-[1-[5-[(dimethylamino)methyl]pyrimidin-2-yl]-3,6-dihydro-2H-pyridin-5-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[5-(morpholin-4-ylmethyl)pyrimidin-2-yl]-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[5-[(4-methylpiperazin-1-yl)methyl]pyrimidin-2-yl]-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide;

N-[4-fluoro-2-[(3S)-3-(dimethylamino)pyrrolidin-1-yl]-5-[2-[(2R,6S)-2,6-dimethylmorpholin-4-yl]pyrimidin-5-yl]phenyl]-6-oxo-4-(trifluoromethyl)-1H-pyridine-3-carboxamide;

N-[4-fluoro-5-[2-[(2R,6S)-2,6-dimethylmorpholin-4-yl]pyrimidin-5-yl]-2-[(3S)-3-[ethyl(methyl)amino]pyrrolidin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R)-3-(diethylamino)pyrrolidin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R)-3-[methyl(propan-2-yl)amino]pyrrolidin-1-yl]phenyl]-6-oxo-4-(trifluoromethyl)-1H-pyridine-3-carboxamide;

N-[4-fluoro-5-[6-[(2R,6S)-2,6-dimethylmorpholin-4-yl]pyridin-3-yl]-2-[(3R)-3,4-dimethylpiperazin-1-yl]phenyl]-1-methyl-6-oxo-4-(trifluoromethyl)pyridine-3-carboxamide;

N-[4-fluoro-5-[6-[(2R,6S)-2,6-dimethylmorpholin-4-yl]pyridin-3-yl]-2-[(3S,5R)-3,4,5-trimethylpiperazin-1-yl]phenyl]-1-methyl-6-oxo-4-(trifluoromethyl)pyridine-3-carboxamide;

4-fluoro-N-[4-fluoro-5-[6-[(2R,6S)-2,6-dimethylmorpholin-4-yl]pyridin-3-yl]-2-[(3R)-3,4-dimethylpiperazin-1-yl]phenyl]-2-(trifluoromethyl)benzamide;

N-[4-fluoro-5-[2-(4-hydroxy-4-methylpiperidin-1-yl)pyrimidin-5-yl]-2-[(3R)-3,4-dimethylpiperazin-1-yl]phenyl]-6-oxo-4-(trifluoromethyl)-1H-pyridine-3-carboxamide;

N-[4-fluoro-5-[2-(4-hydroxy-4-methylpiperidin-1-yl)pyrimidin-5-yl]-2-[(3R,5S)-3,4,5-trimethylpiperazin-1-yl]phenyl]-6-oxo-4-(trifluoromethyl)-1H-pyridine-3-carboxamide;

N-[4-fluoro-2-[(3S)-3-(dimethylamino)pyrrolidin-1-yl]-5-[2-[(2R,6S)-2,6-dimethylmorpholin-4-yl]pyrimidin-5-yl]phenyl]-1-methyl-6-oxo-4-(trifluoromethyl)pyridine-3-carboxamide;

N-[4-fluoro-5-[2-[(2R,6S)-2,6-dimethylmorpholin-4-yl]pyrimidin-5-yl]-2-[(3S)-3-[ethyl(methyl)amino]pyrrolidin-1-yl]phenyl]-1-methyl-6-oxo-4-(trifluoromethyl)pyridine-3-carboxamide;

N-[4-fluoro-5-(2-morpholin-4-ylpyrimidin-5-yl)-2-[(3R)-3-(diethylamino)pyrrolidin-1-yl]phenyl]-1-methyl-6-oxo-4-(trifluoromethyl)pyridine-3-carboxamide;

N-[4-fluoro-5-(2-morpholin-4-ylpyrimidin-5-yl)-2-[(3R)-3-[methyl(propan-2-yl)amino]pyrrolidin-1-yl]phenyl]-1-methyl-6-oxo-4-(trifluoromethyl)pyridine-3-carboxamide;

4-fluoro-N-[4-fluoro-5-[2-[(2R,6S)-2,6-dimethylmorpholin-4-yl]pyrimidin-5-yl]-2-[(3R)-3,4-dimethylpiperazin-1-yl]phenyl]-2-(trifluoromethyl)benzamide;

4-fluoro-N-[4-fluoro-5-[2-[(2R,6S)-2,6-dimethylmorpholin-4-yl]pyrimidin-5-yl]-2-[(3S,5R)-3,4,5-trimethylpiperazin-1-yl]phenyl]-2-(trifluoromethyl)benzamide;

4-fluoro-N-[4-fluoro-5-[6-[(2R,6S)-2,6-dimethylmorpholin-4-yl]pyridin-3-yl]-2-[(3S,5R)-3,4,5-trimethylpiperazin-1-yl]phenyl]-2-(trifluoromethyl)benzamide;

N-[4-fluoro-2-[(3R)-3,4-dimethylpiperazin-1-yl]-5-[6-[(2R)-2-methylmorpholin-4-yl]pyridin-3-yl]phenyl]-6-oxo-4-(trifluoromethyl)-1H-pyridine-3-carboxamide;

N-[4-fluoro-5-[6-[(2R)-2-methylmorpholin-4-yl]pyridin-3-yl]-2-[(3S,5R)-3,4,5-trimethylpiperazin-1-yl]phenyl]-6-oxo-4-(trifluoromethyl)-1H-pyridine-3-carboxamide;

N-[5-[2-(4-cyclopropylpiperazin-1-yl)pyrimidin-5-yl]-4-fluoro-2-[(3R)-3,4-dimethylpiperazin-1-yl]phenyl]-4-fluoro-2-(trifluoromethyl)benzamide;

4-(difluoromethyl)-N-[4-fluoro-5-(3-fluoro-4-morpholin-4-ylphenyl)-2-[(3R,5S)-3,4,5-trimethylpiperazin-1-yl]phenyl]-6-oxo-1H-pyridine-3-carboxamide;

N-[4-fluoro-5-[1-(5-methoxypyrimidin-2-yl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(6-methoxypyrimidin-4-yl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(5-methylpyrimidin-2-yl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(5-fluoropyrimidin-2-yl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(pyrrolidine-1-carbonyl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(pyrazine-2-carbonyl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide;

2-methylpropyl 3-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-2,5-dihydropyrrole-1-carboxylate;

N-[4-fluoro-5-[1-(5-formylpyrimidin-2-yl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-(1-methylpyrazol-4-yl)-2-[(3R,5S)-3,4,5-trimethylpiperazin-1-yl]phenyl]-6-oxo-4-(trifluoromethyl)-1H-pyridine-3-carboxamide;

N-[5-(4-cyano-1,3-thiazol-2-yl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(5-cyano-1,3-thiazol-2-yl)-4-fluoro-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-5-(3-fluoro-4-morpholin-4-ylphenyl)-2-[(3R)-3,4-dimethylpiperazin-1-yl]phenyl]-6-oxo-1H-pyridine-3-carboxamide;

4-(difluoromethyl)-N-[4-fluoro-5-(3-fluoro-4-morpholin-4-ylphenyl)-2-[(3R,5S)-3,4,5-trimethylpiperazin-1-yl]phenyl]-1-methyl-6-oxopyridine-3-carboxamide;

N-[4-fluoro-2-[(3R)-3,4-dimethylpiperazin-1-yl]-5-[2-[(2R)-2-methylmorpholin-4-yl]pyrimidin-5-yl]phenyl]-1-methyl-6-oxo-4-(trifluoromethyl)pyridine-3-carboxamide;

N-[4-fluoro-5-[2-[(2R)-2-methylmorpholin-4-yl]pyrimidin-5-yl]-2-[(3S,5R)-3,4,5-trimethylpiperazin-1-yl]phenyl]-1-methyl-6-oxo-4-(trifluoromethyl)pyridine-3-carboxamide;

4-fluoro-N-[4-fluoro-2-[(3R)-3,4-dimethylpiperazin-1-yl]-5-[2-[(2R)-2-methylmorpholin-4-yl]pyrimidin-5-yl]phenyl]-2-(trifluoromethyl)benzamide;

4-fluoro-N-[4-fluoro-5-[2-[(2R)-2-methylmorpholin-4-yl]pyrimidin-5-yl]-2-[(3S,5R)-3,4,5-trimethylpiperazin-1-yl]phenyl]-2-(trifluoromethyl)benzamide;

N-[5-[2-(4-cyclopropylpiperazin-1-yl)pyrimidin-5-yl]-4-fluoro-2-[(3R,5S)-3,4,5-trimethylpiperazin-1-yl]phenyl]-4-fluoro-2-(trifluoromethyl)benzamide;

N-[5-[2-(4-cyclopropylpiperazin-1-yl)pyrimidin-5-yl]-4-fluoro-2-[(3R)-3,4-dimethylpiperazin-1-yl]phenyl]-1-methyl-6-oxo-4-(trifluoromethyl)pyridine-3-carboxamide;

4-fluoro-N-[4-fluoro-2-[(3S)-3,4-dimethylpiperazin-1-yl]-5-[2-[(2R)-2-methylmorpholin-4-yl]pyrimidin-5-yl]phenyl]-2-(trifluoromethyl)benzamide;

N-[5-[1-[5-[(dimethylamino)methyl]pyrimidin-2-yl]-2,5-dihydropyrrol-3-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[5-(morpholin-4-ylmethyl)pyrimidin-2-yl]-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-[5-[(4-methylpiperazin-1-yl)methyl]pyrimidin-2-yl]-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-2-[(3S)-3,4-dimethylpiperazin-1-yl]-5-[2-[(2R)-2-methylmorpholin-4-yl]pyrimidin-5-yl]phenyl]-1-methyl-6-oxopyridine-3-carboxamide;

4-(difluoromethyl)-N-[4-fluoro-5-[2-[(2R)-2-methylmorpholin-4-yl]pyrimidin-5-yl]-2-[(3R,5S)-3,4,5-trimethylpiperazin-1-yl]phenyl]-1-methyl-6-oxopyridine-3-carboxamide;

4-(difluoromethyl)-N-[4-fluoro-5-[2-[(2R,6S)-2,6-dimethylmorpholin-4-yl]pyrimidin-5-yl]-2-[(3R,5S)-3,4,5-trimethylpiperazin-1-yl]phenyl]-1-methyl-6-oxopyridine-3-carboxamide N-[4-fluoro-5-(2-morpholin-4-ylpyrimidin-5-yl)-2-[(3aR,6aR)-2,3,3a,4,6,6a-hexahydro-1H-pyrrolo[2,3-c]pyrrol-5-yl]phenyl]-6-oxo-4-(trifluoromethyl)-1H-pyridine-3-carboxamide;

N-[4-fluoro-5-(2-piperazin-1-ylpyrimidin-5-yl)-2-[(3R)-3,4-dimethylpiperazin-1-yl]phenyl]-1-methyl-6-oxo-4-(trifluoromethyl)pyridine-3-carboxamide;

4-fluoro-N-[4-fluoro-5-[2-(4-propan-2-ylpiperazin-1-yl)pyrimidin-5-yl]-2-[(3R)-3,4-dimethylpiperazin-1-yl]phenyl]-2-(trifluoromethyl)benzamide;

4-fluoro-N-[4-fluoro-5-[2-(4-propan-2-ylpiperazin-1-yl)pyrimidin-5-yl]-2-[(3R,5S)-3,4,5-trimethylpiperazin-1-yl]phenyl]-2-(trifluoromethyl)benzamide;

N-[4-fluoro-5-[2-(4-propan-2-ylpiperazin-1-yl)pyrimidin-5-yl]-2-[(3R)-3,4-dimethylpiperazin-1-yl]phenyl]-1-methyl-6-oxo-4-(trifluoromethyl)pyridine-3-carboxamide;

N-[4-fluoro-2-[(3S)-3,4-dimethylpiperazin-1-yl]-5-[2-[(3R)-3-methylmorpholin-4-yl]pyrimidin-5-yl]phenyl]-6-oxo-4-(trifluoromethyl)-1H-pyridine-3-carboxamide;

N-[4-fluoro-5-[2-[(3R)-3-methylmorpholin-4-yl]pyrimidin-5-yl]-2-[(3R,5S)-3,4,5-trimethylpiperazin-1-yl]phenyl]-6-oxo-4-(trifluoromethyl)-1H-pyridine-3-carboxamide;

(1-methylcyclobutyl) 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

(1-methylcyclobutyl) 5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

(1-methylcyclobutyl) 3-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-2,5-dihydropyrrole-1-carboxylate;

N-[4-fluoro-5-(6-morpholin-4-ylpyridin-2-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-(6-morpholin-4-ylpyrazin-2-yl)-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-5-[2-[(3R)-3-methylmorpholin-4-yl]pyrimidin-5-yl]-2-[(3S,5R)-3,4,5-trimethylpiperazin-1-yl]phenyl]-1-methyl-6-oxopyridine-3-carboxamide;

N-[4-fluoro-5-(2-morpholin-4-ylpyrimidin-5-yl)-2-[(3aR,6aR)-1-propyl-2,3,3a,4,6,6a-hexahydropyrrolo[2,3-c]pyrrol-5-yl]phenyl]-6-oxo-4-(trifluoromethyl)-1H-pyridine-3-carboxamide;

N-[4-fluoro-5-(2-morpholin-4-ylpyrimidin-5-yl)-2-[(3aR,6aR)-1-methyl-2,3,3a,4,6,6a-hexahydropyrrolo[2,3-c]pyrrol-5-yl]phenyl]-6-oxo-4-(trifluoromethyl)-1H-pyridine-3-carboxamide;

4-(difluoromethyl)-N-[4-fluoro-5-(3-fluoro-4-morpholin-4-ylphenyl)-2-[(3R)-3,4-dimethylpiperazin-1-yl]phenyl]-1-methyl-6-oxopyridine-3-carboxamide;

N-[4-fluoro-5-(2-morpholin-4-ylpyrimidin-5-yl)-2-[(3R,5S)-3,4,4,5-tetramethylpiperazin-4-ium-1-yl]phenyl]-6-oxo-4-(trifluoromethyl)-1H-pyridine-3-carboxamide;

4-(difluoromethyl)-N-[4-fluoro-2-[(3R)-3,4-dimethylpiperazin-1-yl]-5-[2-[(2R)-2-methylmorpholin-4-yl]pyrimidin-5-yl]phenyl]-1-methyl-6-oxopyridine-3-carboxamide;

4-(difluoromethyl)-N-[4-fluoro-5-[2-[(2R)-2-methylmorpholin-4-yl]pyrimidin-5-yl]-2-[(3S,5R)-3,4,5-trimethylpiperazin-1-yl]phenyl]-1-methyl-6-oxopyridine-3-carboxamide;

N-(cyclopropylmethyl)-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-1,3-thiazole-4-carboxamide;

N-(cyclopropylmethyl)-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-N-methyl-1,3-thiazole-4-carboxamide;

N-cyclohexyl-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-1,3-thiazole-4-carboxamide;

N-cyclohexyl-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-N-methyl-1,3-thiazole-4-carboxamide;

N-[4-fluoro-5-[4-(morpholine-4-carbonyl)-1,3-thiazol-2-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[4-(4-methylpiperazine-1-carbonyl)-1,3-thiazol-2-yl]-2-[(3R,5S)-3,4,5-trimethylpiperazin-1-yl]phenyl]-6-oxo-4-(trifluoromethyl)-1H-pyridine-3-carboxamide;

(3-methyloxetan-3-yl) 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

(3-methyloxetan-3-yl) 5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

(3-methyloxetan-3-yl) 3-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-2,5-dihydropyrrole-1-carboxylate;

N-[4-fluoro-5-[5-(morpholin-4-ylmethyl)thiophen-2-yl]-2-[(3R,5S)-3,4,5-trimethylpiperazin-1-yl]phenyl]-6-oxo-4-(trifluoromethyl)-1H-pyridine-3-carboxamide;

N-[4-fluoro-2-[(3R,5S)-3,4,5-trimethylpiperazin-1-yl]-5-thiophen-2-ylphenyl]-6-oxo-4-(trifluoromethyl)-1H-pyridine-3-carboxamide;

N-[4-fluoro-2-[(3R,5S)-3,4,5-trimethylpiperazin-1-yl]-5-thiophen-3-ylphenyl]-6-oxo-4-(trifluoromethyl)-1H-pyridine-3-carboxamide;

N-[4-fluoro-5-[5-(morpholin-4-ylmethyl)thiophen-3-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R)-3,4-dimethylpiperazin-1-yl]phenyl]-6-oxo-5-(trifluoromethyl)-1H-pyridine-3-carboxamide;

N-(cyclopropylmethyl)-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-1,3-thiazole-5-carboxamide;

N-(cyclopropylmethyl)-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-N-methyl-1,3-thiazole-5-carboxamide;

N-cyclohexyl-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-1,3-thiazole-5-carboxamide;

N-cyclohexyl-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-N-methyl-1,3-thiazole-5-carboxamide;

N-[4-fluoro-5-[5-(morpholine-4-carbonyl)-1,3-thiazol-2-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[5-(4-methylpiperazine-1-carbonyl)-1,3-thiazol-2-yl]-2-[(3R,5S)-3,4,5-trimethylpiperazin-1-yl]phenyl]-6-oxo-4-(trifluoromethyl)-1H-pyridine-3-carboxamide;

5-amino-4-fluoro-N-[4-fluoro-5-(2-morpholin-4-ylpyrimidin-5-yl)-2-[(3R,5S)-3,4,5-trimethylpiperazin-1-yl]phenyl]-2-(trifluoromethyl)benzamide;

N-[5-[1-(6-cyclopropylpyridazin-3-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[1-(6-ethylpyridazin-3-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[6-(oxan-4-yloxy)pyridin-3-yl]-2-[(3R,5S)-3,4,5-trimethylpiperazin-1-yl]phenyl]-6-methoxy-4-(trifluoromethyl)pyridine-3-carboxamide;

N-[4-fluoro-5-(2-morpholin-4-ylpyrimidin-5-yl)-2-[(3R,5S)-3,4,5-trimethylpiperazin-1-yl]phenyl]-6-methoxy-4-(trifluoromethyl)pyridine-3-carboxamide;

4-(difluoromethyl)-N-[4-fluoro-2-[(3R)-3,4-dimethylpiperazin-1-yl]-5-[6-[(2R)-2-methylmorpholin-4-yl]pyridin-3-yl]phenyl]-6-oxo-1H-pyridine-3-carboxamide;

4-(difluoromethyl)-N-[4-fluoro-5-[6-[(2R)-2-methylmorpholin-4-yl]pyridin-3-yl]-2-[(3R,5S)-3,4,5-trimethylpiperazin-1-yl]phenyl]-6-oxo-1H-pyridine-3-carboxamide;

4-(difluoromethyl)-N-[4-fluoro-2-[(3S)-3,4-dimethylpiperazin-1-yl]-5-[6-[(2R)-2-methylmorpholin-4-yl]pyridin-3-yl]phenyl]-6-oxo-1H-pyridine-3-carboxamide;

4-(difluoromethyl)-N-[4-fluoro-5-[6-[(2R)-2-methylmorpholin-4-yl]pyridin-3-yl]-2-[(3S,5R)-3,4,5-trimethylpiperazin-1-yl]phenyl]-6-oxo-1H-pyridine-3-carboxamide;

4-(difluoromethyl)-N-[4-fluoro-5-[6-[(2R,6S)-2,6-dimethylmorpholin-4-yl]pyridin-3-yl]-2-[(3R,5S)-3,4,5-trimethylpiperazin-1-yl]phenyl]-6-oxo-1H-pyridine-3-carboxamide;

5-amino-4-fluoro-N-[4-fluoro-5-(2-morpholin-4-ylpyrimidin-5-yl)-2-[(3R)-3,4-dimethylpiperazin-1-yl]phenyl]-2-(trifluoromethyl)benzamide;

N-[4-fluoro-5-(2-morpholin-4-ylpyrimidin-5-yl)-2-[(3aR,6aR)-1-ethyl-2,3,3a,4,6,6a-hexahydropyrrolo[2,3-c]pyrrol-5-yl]phenyl]-6-oxo-4-(trifluoromethyl)-1H-pyridine-3-carboxamide;

4-(difluoromethyl)-N-[4-fluoro-5-[6-[(2R,6S)-2,6-dimethylmorpholin-4-yl]pyridin-3-yl]-2-[(3S)-3,4-dimethylpiperazin-1-yl]phenyl]-6-oxo-1H-pyridine-3-carboxamide;

4-(difluoromethyl)-N-[4-fluoro-5-[6-[(2R,6S)-2,6-dimethylmorpholin-4-yl]pyridin-3-yl]-2-[(3S)-3,4-dimethylpiperazin-1-yl]phenyl]-1-methyl-6-oxopyridine-3-carboxamide;

4-(difluoromethyl)-N-[4-fluoro-2-[(3S)-3,4-dimethylpiperazin-1-yl]-5-[6-[(2R)-2-methylmorpholin-4-yl]pyridin-3-yl]phenyl]-1-methyl-6-oxopyridine-3-carboxamide;

4-(difluoromethyl)-N-[4-fluoro-5-[6-[(2R)-2-methylmorpholin-4-yl]pyridin-3-yl]-2-[(3S,5R)-3,4,5-trimethylpiperazin-1-yl]phenyl]-1-methyl-6-oxopyridine-3-carboxamide;

4-(difluoromethyl)-N-[4-fluoro-5-[6-[(2R,6S)-2,6-dimethylmorpholin-4-yl]pyridin-3-yl]-2-[(3R,5S)-3,4,5-trimethylpiperazin-1-yl]phenyl]-1-methyl-6-oxopyridine-3-carboxamide;

4-(difluoromethyl)-N-[4-fluoro-2-[(3R)-3,4-dimethylpiperazin-1-yl]-5-[6-[(2R)-2-methylmorpholin-4-yl]pyridin-3-yl]phenyl]-1-methyl-6-oxopyridine-3-carboxamide;

N-[4-fluoro-5-(2-morpholin-4-ylpyrimidin-5-yl)-2-[(3R)-3-[methyl(2,2,2-trifluoroethyl)amino]pyrrolidin-1-yl]phenyl]-6-oxo-4-(trifluoromethyl)-1H-pyridine-3-carboxamide;

4-(difluoromethyl)-N-[4-fluoro-5-[2-[(3R)-3-methylmorpholin-4-yl]pyrimidin-5-yl]-2-[(3S,5R)-3,4,5-trimethylpiperazin-1-yl]phenyl]-6-oxo-1H-pyridine-3-carboxamide;

N-[5-[6-(cyclopropylmethoxy)pyridin-3-yl]-4-fluoro-2-[(3R)-3,4-dimethylpiperazin-1-yl]phenyl]-1-methyl-6-oxo-4-(trifluoromethyl)pyridine-3-carboxamide;

N-(cyclopropylmethyl)-4-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-1,3-thiazole-2-carboxamide;

N-(cyclopropylmethyl)-4-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-N-methyl-1,3-thiazole-2-carboxamide;

N-cyclohexyl-4-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-1,3-thiazole-2-carboxamide;

N-cyclohexyl-4-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-N-methyl-1,3-thiazole-2-carboxamide;

N-[4-fluoro-5-[2-(morpholine-4-carbonyl)-1,3-thiazol-4-yl]-2-[(3R,5S)-3,4,5-trimethylpiperazin-1-yl]phenyl]-1-methyl-6-oxo-4-(trifluoromethyl)pyridine-3-carboxamide;

N-[4-fluoro-5-[2-(4-methylpiperazine-1-carbonyl)-1,3-thiazol-4-yl]-2-[(3R,5S)-3,4,5-trimethylpiperazin-1-yl]phenyl]-1-methyl-6-oxo-4-(trifluoromethyl)pyridine-3-carboxamide;

4-fluoro-N-[4-fluoro-5-(4-piperazin-1-ylphenyl)-2-[(3R)-3,4-dimethylpiperazin-1-yl]phenyl]-2-(trifluoromethyl)benzamide;

4-fluoro-N-[4-fluoro-5-(6-piperazin-1-ylpyridin-3-yl)-2-[(3R)-3,4-dimethylpiperazin-1-yl]phenyl]-2-(trifluoromethyl)benzamide;

N-(cyclopropylmethyl)-4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-1,3-thiazole-2-carboxamide;

N-(cyclopropylmethyl)-4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-N-methyl-1,3-thiazole-2-carboxamide;

N-cyclohexyl-4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-1,3-thiazole-2-carboxamide;

N-cyclohexyl-4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-N-methyl-1,3-thiazole-2-carboxamide;

N-[4-fluoro-5-[2-(morpholine-4-carbonyl)-1,3-thiazol-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[2-(4-methylpiperazine-1-carbonyl)-1,3-thiazol-4-yl]-2-[(3R,5S)-3,4,5-trimethylpiperazin-1-yl]phenyl]-6-oxo-4-(trifluoromethyl)-1H-pyridine-3-carboxamide;

N-[5-[2-(cyclohexylamino)pyrimidin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[2-(methylamino)pyrimidin-4-yl]-2-[(3R,5S)-3,4,5-trimethylpiperazin-1-yl]phenyl]-6-oxo-4-(trifluoromethyl)-1H-pyridine-3-carboxamide;

N-[5-(2-cyanopyrimidin-4-yl)-4-fluoro-2-[(3R,5S)-3,4,5-trimethylpiperazin-1-yl]phenyl]-6-oxo-4-(trifluoromethyl)-1H-pyridine-3-carboxamide;

N-[5-[2-(dimethylamino)pyrimidin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-2-[4-(methylamino)piperidin-1-yl]-5-(2-morpholin-4-ylpyrimidin-5-yl)phenyl]-6-oxo-4-(trifluoromethyl)-1H-pyridine-3-carboxamide;

4-(difluoromethyl)-N-[4-fluoro-5-[6-[(2R)-2-methylmorpholin-4-yl]pyridin-3-yl]-2-[(3R,5S)-3,4,5-trimethylpiperazin-1-yl]phenyl]-1-methyl-6-oxopyridine-3-carboxamide;

N-[5-[6-(cyclopropylmethoxy)pyridin-3-yl]-4-fluoro-2-[(3R)-3,4-dimethylpiperazin-1-yl]phenyl]-4-(difluoromethyl)-1-methyl-6-oxopyridine-3-carboxamide;

N-[4-fluoro-2-[(3S)-3,4-dimethylpiperazin-1-yl]-5-[2-[(2R)-2-methylmorpholin-4-yl]pyrimidin-5-yl]phenyl]-1-methyl-6-oxo-4-(trifluoromethyl)pyridine-3-carboxamide;

4-fluoro-N-[4-fluoro-5-[2-[(2R)-2-methylmorpholin-4-yl]pyrimidin-5-yl]-2-[(3R,5S)-3,4,5-trimethylpiperazin-1-yl]phenyl]-2-(trifluoromethyl)benzamide;

4-fluoro-N-[4-fluoro-5-(2-piperazin-1-ylpyrimidin-5-yl)-2-[(3R,5S)-3,4,5-trimethylpiperazin-1-yl]phenyl]-2-(trifluoromethyl)benzamide;

4-fluoro-N-[4-fluoro-5-(6-morpholin-4-ylpyridin-3-yl)-2-[(3R,5S)-3,4,5-trimethylpiperazin-1-yl]phenyl]-2-(trifluoromethyl)benzamide;

N-[4-fluoro-5-(6-piperazin-1-ylpyridin-3-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-(4-piperazin-1-ylphenyl)-2-[(3R,5S)-3,4,5-trimethylpiperazin-1-yl]phenyl]-6-oxo-4-(trifluoromethyl)-1H-pyridine-3-carboxamide;

N-[5-(3-carbamoyl-4-fluorophenyl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(4-carbamoyl-3-fluorophenyl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(3-carbamoyl-4-fluorophenyl)-4-fluoro-2-[(3R,5S)-3,4,5-trimethylpiperazin-1-yl]phenyl]-4-(difluoromethyl)-6-oxo-1H-pyridine-3-carboxamide;

N-[5-(4-carbamoyl-3-fluorophenyl)-4-fluoro-2-[(3R,5S)-3,4,5-trimethylpiperazin-1-yl]phenyl]-4-(difluoromethyl)-6-oxo-1H-pyridine-3-carboxamide;

2-fluoro-5-[2-fluoro-5-[[4-fluoro-2-(trifluoromethyl)benzoyl]amino]-4-[(3R)-3,4-dimethylpiperazin-1-yl]phenyl]benzamide;

2-fluoro-4-[2-fluoro-5-[[4-fluoro-2-(trifluoromethyl)benzoyl]amino]-4-[(3R)-3,4-dimethylpiperazin-1-yl]phenyl]benzamide;

2-fluoro-5-[2-fluoro-5-[[4-fluoro-2-(trifluoromethyl)benzoyl]amino]-4-[(3R,5S)-3,4,5-trimethylpiperazin-1-yl]phenyl]benzamide;

N-[5-[2-(4-tert-butylpiperazin-1-yl)pyrimidin-5-yl]-4-fluoro-2-[(3R)-3,4-dimethylpiperazin-1-yl]phenyl]-4-fluoro-2-(trifluoromethyl)benzamide;

N-[5-[2-(2,2-dimethylmorpholin-4-yl)pyrimidin-5-yl]-4-fluoro-2-[(3R)-3,4-dimethylpiperazin-1-yl]phenyl]-4-fluoro-2-(trifluoromethyl)benzamide;

N-[5-[2-(2,2-dimethylmorpholin-4-yl)pyrimidin-5-yl]-4-fluoro-2-[(3R,5S)-3,4,5-trimethylpiperazin-1-yl]phenyl]-4-fluoro-2-(trifluoromethyl)benzamide;

N-[5-[2-[4-(cyclopropylmethyl)piperazin-1-yl]pyrimidin-5-yl]-4-fluoro-2-[(3R)-3,4-dimethylpiperazin-1-yl]phenyl]-4-fluoro-2-(trifluoromethyl)benzamide;

N-[2-(4-cyclopropylpiperazin-1-yl)-4-fluoro-5-(2-morpholin-4-ylpyrimidin-5-yl)phenyl]-6-oxo-4-(trifluoromethyl)-1H-pyridine-3-carboxamide;

N-[4-fluoro-5-(5-fluoro-6-oxo-1H-pyridin-3-yl)-2-[(3R,5S)-3,4,5-trimethylpiperazin-1-yl]phenyl]-6-oxo-4-(trifluoromethyl)-1H-pyridine-3-carboxamide;

benzyl N-[5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]pyridin-3-yl]carbamate;

N-[4-fluoro-5-(5-fluoro-1-methyl-6-oxopyridin-3-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(4-methoxybenzoyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-oxo-1,3-dihydropyrrolo[2,3-b]pyridin-5-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-(1-methyl-2-oxopyridin-4-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-(1-methyl-6-oxopyridin-3-yl)-2-[(3R,5S)-3,4,5-trimethylpiperazin-1-yl]phenyl]-6-oxo-4-(trifluoromethyl)-1H-pyridine-3-carboxamide;

N-[5-[1-(cyclohexanecarbonyl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

tert-butyl N-[1-[2-[(3,5-dichlorobenzoyl)amino]-5-fluoro-4-(2-morpholin-4-ylpyrimidin-5-yl)phenyl]pyrrolidin-3-yl]-N-methylcarbamate;

3,5-dichloro-N-[4-fluoro-2-[3-[3-methoxypropyl(methyl)amino]pyrrolidin-1-yl]-5-(2-morpholin-4-ylpyrimidin-5-yl)phenyl]benzamide;

N-[4-fluoro-2-[3-[3-methoxypropyl(methyl)amino]pyrrolidin-1-yl]-5-(2-morpholin-4-ylpyrimidin-5-yl)phenyl]-6-oxo-4-(trifluoromethyl)-1H-pyridine-3-carboxamide;

N-[4-fluoro-5-[1-(pyrazine-2-carbonyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R)-3-[methyl(methylsulfonyl)amino]pyrrolidin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R)-3-[methyl(methylsulfonyl)amino]pyrrolidin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,4R)-3-methoxy-4-[2-methoxyethyl(methyl)amino]pyrrolidin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,4R)-3-fluoro-4-[2-methoxyethyl(methyl)amino]pyrrolidin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R)-3-[2-methoxyethyl(methyl)amino]pyrrolidin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R,4R)-3-fluoro-4-[2-methoxyethyl(methyl)amino]pyrrolidin-1-yl]phenyl]-1-methyl-6-oxo-4-(trifluoromethyl)pyridine-3-carboxamide;

N-[4-fluoro-5-(2-morpholin-4-ylpyrimidin-5-yl)-2-[(3R)-3-[2-methoxyethyl(methyl)amino]pyrrolidin-1-yl]phenyl]-1-methyl-6-oxo-4-(trifluoromethyl)pyridine-3-carboxamide;

N-[4-fluoro-5-(6-methylsulfonylpyridin-3-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-[2-(methanesulfonamido)pyrimidin-5-yl]-2-[(3R,5S)-3,4,5-trimethylpiperazin-1-yl]phenyl]-6-oxo-4-(trifluoromethyl)-1H-pyridine-3-carboxamide;

N-[5-[1-(5-cyanopyrimidin-2-yl)-3,6-dihydro-2H-pyridin-5-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(1-methylsulfonyl-3,6-dihydro-2H-pyridin-5-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-(1-methylsulfonyl-3,6-dihydro-2H-pyridin-4-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R)-3-[cyclopropylmethyl(methyl)amino]pyrrolidin-1-yl]phenyl]-6-oxo-4-(trifluoromethyl)-1H-pyridine-3-carboxamide;

N-[4-fluoro-5-(2-morpholin-4-ylpyrimidin-5-yl)-2-[(3R)-3-[cyclopropylmethyl(methyl)amino]pyrrolidin-1-yl]phenyl]-1-methyl-6-oxo-4-(trifluoromethyl)pyridine-3-carboxamide;

N-[5-[1-(5-cyanopyrimidin-2-yl)-2,5-dihydropyrrol-3-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-(3-carbamoyl-4-fluorophenyl)-4-fluoro-2-[(3R,5S)-3,4,5-trimethylpiperazin-1-yl]phenyl]-1-methyl-6-oxo-4-(trifluoromethyl)pyridine-3-carboxamide;

N-[5-(4-carbamoyl-3-fluorophenyl)-4-fluoro-2-[(3R,5S)-3,4,5-trimethylpiperazin-1-yl]phenyl]-1-methyl-6-oxo-4-(trifluoromethyl)pyridine-3-carboxamide;

N-[5-(3-carbamoyl-4-fluorophenyl)-4-fluoro-2-[(3R,5S)-3,4,5-trimethylpiperazin-1-yl]phenyl]-4-(difluoromethyl)-1-methyl-6-oxopyridine-3-carboxamide;

N-[5-(4-carbamoyl-3-fluorophenyl)-4-fluoro-2-[(3R,5S)-3,4,5-trimethylpiperazin-1-yl]phenyl]-4-(difluoromethyl)-1-methyl-6-oxopyridine-3-carboxamide;

N-[4-fluoro-2-[(3R)-3,4-dimethylpiperazin-1-yl]-5-[2-[(2R)-2-methylmorpholin-4-yl]pyrimidin-4-yl]phenyl]-6-oxo-4-(trifluoromethyl)-1H-pyridine-3-carboxamide;

N-[4-fluoro-5-[2-[(2R)-2-methylmorpholin-4-yl]pyrimidin-4-yl]-2-[(3S,5R)-3,4,5-trimethylpiperazin-1-yl]phenyl]-6-oxo-4-(trifluoromethyl)-1H-pyridine-3-carboxamide;

N-[5-(4-carbamoyl-3-fluorophenyl)-4-fluoro-2-[(3R)-3,4-dimethylpiperazin-1-yl]phenyl]-4-(difluoromethyl)-6-oxo-1H-pyridine-3-carboxamide;

N-[5-(3-carbamoyl-4-fluorophenyl)-4-fluoro-2-[(3R)-3,4-dimethylpiperazin-1-yl]phenyl]-4-(difluoromethyl)-6-oxo-1H-pyridine-3-carboxamide;

4-(difluoromethyl)-N-[4-fluoro-5-[3-fluoro-4-(methylcarbamoyl)phenyl]-2-[(3R)-3,4-dimethylpiperazin-1-yl]phenyl]-6-oxo-1H-pyridine-3-carboxamide;

4-(difluoromethyl)-N-[4-fluoro-5-[4-fluoro-3-(methylcarbamoyl)phenyl]-2-[(3R)-3,4-dimethylpiperazin-1-yl]phenyl]-6-oxo-1H-pyridine-3-carboxamide;

N-[4-fluoro-5-(4-morpholin-4-ylpyrimidin-2-yl)-2-[(3R)-3,4-dimethylpiperazin-1-yl]phenyl]-6-oxo-4-(trifluoromethyl)-1H-pyridine-3-carboxamide;

propan-2-yl 3-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-2,5-dihydropyrrole-1-carboxylate;

propan-2-yl 5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

propan-2-yl 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate;

N-[4-fluoro-5-[3-fluoro-4-(methylcarbamoyl)phenyl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[4-fluoro-3-(methylcarbamoyl)phenyl]-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-5-[3-fluoro-4-(methylcarbamoyl)phenyl]-2-[(3R,5S)-3,4,5-trimethylpiperazin-1-yl]phenyl]-6-oxo-1H-pyridine-3-carboxamide;

4-(difluoromethyl)-N-[4-fluoro-5-[4-fluoro-3-(methylcarbamoyl)phenyl]-2-[(3R,5S)-3,4,5-trimethylpiperazin-1-yl]phenyl]-6-oxo-1H-pyridine-3-carboxamide;

4-(difluoromethyl)-N-[4-fluoro-2-[(3R)-3,4-dimethylpiperazin-1-yl]-5-[2-[(3R)-3-methylmorpholin-4-yl]pyrimidin-5-yl]phenyl]-1-methyl-6-oxopyridine-3-carboxamide;

N-[4-fluoro-2-[(3R)-3,4-dimethylpiperazin-1-yl]-5-[2-[(3R)-3-methylmorpholin-4-yl]pyrimidin-5-yl]phenyl]-1-methyl-6-oxo-4-(trifluoromethyl)pyridine-3-carboxamide;

N-[4-fluoro-5-(6-fluoropyridin-2-yl)-2-[(3R)-3,4-dimethylpiperazin-1-yl]phenyl]-6-oxo-4-(trifluoromethyl)-1H-pyridine-3-carboxamide;

N-[4-fluoro-2-[(3R)-3,4-dimethylpiperazin-1-yl]-5-[6-(trifluoromethyl)pyridin-2-yl]phenyl]-6-oxo-4-(trifluoromethyl)-1H-pyridine-3-carboxamide;

4-fluoro-N-[4-fluoro-5-[2-[(2R)-2-methylmorpholin-4-yl]pyrimidin-5-yl]-2-[(3S,5R)-3,4,5-trimethylpiperazin-1-yl]phenyl]-3,5-dimethylbenzamide;

4-(Difluoromethyl)-N-(4-fluoro-5-(1-(pyrrolidine-1-carbonyl)-2,5-dihydro-1H-pyrrol-3-yl)-2-((3S,5R)-3,4,5-trimethylpiperazin-1-yl)phenyl)-6-oxo-1,6-dihydropyridine-3-carboxamide;

4-fluoro-N-[4-fluoro-5-[2-(4-hydroxy-4-methylpiperidin-1-yl)pyrimidin-5-yl]-2-[(3R)-3,4-dimethylpiperazin-1-yl]phenyl]-2-(trifluoromethyl)benzamide;

4-fluoro-N-[4-fluoro-5-(2-morpholin-4-ylpyrimidin-4-yl)-2-[(3R)-3,4-dimethylpiperazin-1-yl]phenyl]-2-(trifluoromethyl)benzamide;

N-[5-[1-(5-cyano-1,3-thiazol-2-yl)-3,6-dihydro-2H-pyridin-5-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-yl-1,3-thiazol-4-yl)-2-[(3R,5S)-3,4,5-trimethylpiperazin-1-yl]phenyl]-6-oxo-4-(trifluoromethyl)-1H-pyridine-3-carboxamide;

N-[4-fluoro-5-(2-morpholin-4-yl-1,3-thiazol-4-yl)-2-[(3R)-3,4-dimethylpiperazin-1-yl]phenyl]-6-oxo-4-(trifluoromethyl)-1H-pyridine-3-carboxamide;

N-[4-fluoro-5-(2-morpholin-4-yl-1,3-thiazol-5-yl)-2-[(3R)-3,4-dimethylpiperazin-1-yl]phenyl]-6-oxo-4-(trifluoromethyl)-1H-pyridine-3-carboxamide;

N-[4-fluoro-5-(2-morpholin-4-yl-1,3-thiazol-5-yl)-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-5-(2-morpholin-4-yl-1,3-thiazol-4-yl)-2-[(3R)-3,4-dimethylpiperazin-1-yl]phenyl]-1-methyl-6-oxopyridine-3-carboxamide;

4-(difluoromethyl)-N-[4-fluoro-5-(2-morpholin-4-yl-1,3-thiazol-5-yl)-2-[(3R)-3,4-dimethylpiperazin-1-yl]phenyl]-1-methyl-6-oxopyridine-3-carboxamide;

4-(difluoromethyl)-N-[4-fluoro-5-(2-morpholin-4-yl-1,3-thiazol-4-yl)-2-[(3R,5S)-3,4,5-trimethylpiperazin-1-yl]phenyl]-1-methyl-6-oxopyridine-3-carboxamide;

4-(difluoromethyl)-N-[4-fluoro-5-(2-morpholin-4-yl-1,3-thiazol-5-yl)-2-[(3R,5S)-3,4,5-trimethylpiperazin-1-yl]phenyl]-1-methyl-6-oxopyridine-3-carboxamide;

2,4-difluoro-5-[2-fluoro-5-[[4-fluoro-2-(trifluoromethyl)benzoyl]amino]-4-[(3R,5S)-3,4,5-trimethylpiperazin-1-yl]phenyl]-N-(2,4,4-trimethylpentan-2-yl)benzamide;

2,4-difluoro-5-[2-fluoro-5-[[4-fluoro-2-(trifluoromethyl)benzoyl]amino]-4-[(3R)-3,4-dimethylpiperazin-1-yl]phenyl]-N-(2,4,4-trimethylpentan-2-yl)benzamide;

N-[5-[2,4-difluoro-5-(2,4,4-trimethylpentan-2-ylcarbamoyl)phenyl]-4-fluoro-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[5-[2,4-difluoro-5-(2,4,4-trimethylpentan-2-ylcarbamoyl)phenyl]-4-fluoro-2-[(3R,5S)-3,4,5-trimethylpiperazin-1-yl]phenyl]-6-oxo-1H-pyridine-3-carboxamide;

4-(difluoromethyl)-N-[4-fluoro-2-[(3R)-3,4-dimethylpiperazin-1-yl]-5-[2-[(3R)-3-methylmorpholin-4-yl]pyrimidin-5-yl]phenyl]-6-oxo-1H-pyridine-3-carboxamide (S)-4-(Sifluoromethyl)-N-(2-(3,4-dimethylpiperazin-1-yl)-4-fluoro-5-(1-(pyrrolidine-1-carbonyl)-2,5-dihydro-1H-pyrrol-3-yl)phenyl)-6-oxo-1,6-dihydropyridine-3-carboxamide;

1-Methylcyclobutyl 3-(5-(4-(difluoromethyl)-6-oxo-1,6-dihydropyridine-3-carboxamido)-2-fluoro-4-((3S,5R)-3,4,5-trimethylpiperazin-1-yl)phenyl)-2,5-dihydro-1H-pyrrole-1-carboxylate;

1-Methylcyclobutyl (S)-3-(5-(4-(difluoromethyl)-6-oxo-1,6-dihydropyridine-3-carboxamido)-4-(3,4-dimethylpiperazin-1-yl)-2-fluorophenyl)-2,5-dihydro-H-pyrrole-1-carboxylate;

N-[5-(5-carbamoyl-2,4-difluorophenyl)-4-fluoro-2-[(3R,5S)-3,4,5-trimethylpiperazin-1-yl]phenyl]-6-oxo-4-(trifluoromethyl)-1H-pyridine-3-carboxamide;

N-[5-(5-carbamoyl-2,4-difluorophenyl)-4-fluoro-2-[(3R,5S)-3,4,5-trimethylpiperazin-1-yl]phenyl]-4-(difluoromethyl)-6-oxo-1H-pyridine-3-carboxamide;

2,4-difluoro-5-[2-fluoro-5-[[4-fluoro-2-(trifluoromethyl)benzoyl]amino]-4-[(3R,5S)-3,4,5-trimethylpiperazin-1-yl]phenyl]benzamide;

2,4-difluoro-5-[2-fluoro-5-[[4-fluoro-2-(trifluoromethyl)benzoyl]amino]-4-[(3R)-3,4-dimethylpiperazin-1-yl]phenyl]benzamide;

4-fluoro-N-[4-fluoro-5-[2-(4-hydroxy-4-methylpiperidin-1-yl)pyrimidin-5-yl]-2-[(3R,5S)-3,4,5-trimethylpiperazin-1-yl]phenyl]-2-(trifluoromethyl)benzamide;

3,3-Difluorocyclobutyl 3-(5-(4-(difluoromethyl)-6-oxo-1,6-dihydropyridine-3-carboxamido)-2-fluoro-4-((3S,5R)-3,4,5-trimethylpiperazin-1-yl)phenyl)-2,5-dihydro-1H-pyrrole-1-carboxylate;

3,3-Difluorocyclobutyl (S)-3-(5-(4-(difluoromethyl)-6-oxo-1,6-dihydropyridine-3-carboxamido)-4-(3,4-dimethylpiperazin-1-yl)-2-fluorophenyl)-2,5-dihydro-1H-pyrrole-1-carboxylate;

(S)—N-(5-(1-(2-cyanopyrimidin-5-yl)-1,2,3,6-tetrahydropyridin-4-yl)-2-(3,4-dimethylpiperazin-1-yl)-4-fluorophenyl)-4-(difluoromethyl)-6-oxo-1,6-dihydropyridine-3-carboxamide;

N-[4-fluoro-5-[2-[(2R)-2-methylmorpholin-4-yl]pyrimidin-5-yl]-2-[(3R,5S)-3,4,5-trimethylpiperazin-1-yl]phenyl]-1-methyl-6-oxo-4-(trifluoromethyl)pyridine-3-carboxamide;

N-[4-fluoro-5-[2-(4-hydroxy-4-methylpiperidin-1-yl)pyrimidin-5-yl]-2-[(3R,5S)-3,4,5-trimethylpiperazin-1-yl]phenyl]-1-methyl-6-oxo-4-(trifluoromethyl)pyridine-3-carboxamide;

N-[5-[1-(4-cyano-1,3-thiazol-2-yl)-3,6-dihydro-2H-pyridin-5-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(1,3-oxazol-2-yl)-3,6-dihydro-2H-pyridin-5-yl]-2-[(3R,5S)-3,4,5-trimethylpiperazin-1-yl]phenyl]-

6-oxo-4-(trifluoromethyl)-1H-pyridine-3-carboxamide
4-(difluoromethyl)-N-[4-fluoro-5-(1-pyrimidin-2-yl-3,6-dihydro-2H-pyridin-5-yl)-2-[(3R,5S)-3,4,5-trimethylpiperazin-1-yl]phenyl]-6-oxo-1H-pyridine-3-carboxamide;
4-(difluoromethyl)-N-[4-fluoro-5-[1-(5-methoxypyrimidin-2-yl)-3,6-dihydro-2H-pyridin-5-yl]-2-[(3R,5S)-3,4,5-trimethylpiperazin-1-yl]phenyl]-6-oxo-1H-pyridine-3-carboxamide;
4-(difluoromethyl)-N-[4-fluoro-5-[1-(5-formylpyrimidin-2-yl)-3,6-dihydro-2H-pyridin-4-yl]-2-[(3R,5S)-3,4,5-trimethylpiperazin-1-yl]phenyl]-6-oxo-TH-pyridine-3-carboxamide;
4-(difluoromethyl)-N-[4-fluoro-5-[1-(6-methoxypyrimidin-4-yl)-3,6-dihydro-2H-pyridin-4-yl]-2-[(3R,5S)-3,4,5-trimethylpiperazin-1-yl]phenyl]-6-oxo-1H-pyridine-3-carboxamide;
ethyl 5-[5-[[4-(difluoromethyl)-6-oxo-1H-pyridine-3-carbonyl]amino]-2-fluoro-4-[(3R,5S)-3,4,5-trimethylpiperazin-1-yl]phenyl]-3,6-dihydro-2H-pyridine-1-carboxylate; 4-fluoro-N-[4-fluoro-5-(1-pyrimidin-2-yl-3,6-dihydro-2H-pyridin-5-yl)-2-[(3R)-3,4-dimethylpiperazin-1-yl]phenyl]-2-(trifluoromethyl)benzamide;
4-fluoro-N-[4-fluoro-5-[1-(5-formylpyrimidin-2-yl)-3,6-dihydro-2H-pyridin-5-yl]-2-[(3R)-3,4-dimethylpiperazin-1-yl]phenyl]-2-(trifluoromethyl)benzamide;
(1-methylcyclobutyl) 4-[5-[[4-(difluoromethyl)-6-oxo-1H-pyridine-3-carbonyl]amino]-2-fluoro-4-[(3R,5S)-3,4,5-trimethylpiperazin-1-yl]phenyl]-3,6-dihydro-2H-pyridine-1-carboxylate;
N-[5-(4-carbamoyl-3-fluorophenyl)-4-fluoro-2-[(3R)-3,4-dimethylpiperazin-1-yl]phenyl]-4-(difluoromethyl)-1-methyl-6-oxopyridine-3-carboxamide;
4-(difluoromethyl)-N-[4-fluoro-5-[3-fluoro-4-(methylcarbamoyl)phenyl]-2-[(3R)-3,4-dimethylpiperazin-1-yl]phenyl]-1-methyl-6-oxopyridine-3-carboxamide;
2-(difluoromethyl)-4-fluoro-N-[4-fluoro-5-(2-morpholin-4-ylpyrimidin-5-yl)-2-[(3R)-3,4-dimethylpiperazin-1-yl]phenyl]benzamide;
2-(difluoromethyl)-4-fluoro-N-[4-fluoro-5-(2-morpholin-4-ylpyrimidin-4-yl)-2-[(3R)-3,4-dimethylpiperazin-1-yl]phenyl]benzamide;
2,6-difluoro-4-[2-fluoro-5-[[4-fluoro-2-(trifluoromethyl)benzoyl]amino]-4-[(3R,5S)-3,4,5-trimethylpiperazin-1-yl]phenyl]benzamide;
2,6-difluoro-4-[2-fluoro-5-[[4-fluoro-2-(trifluoromethyl)benzoyl]amino]-4-[(3R)-3,4-dimethylpiperazin-1-yl]phenyl]benzamide;
N-[5-(4-carbamoyl-3,5-difluorophenyl)-4-fluoro-2-[(3R,5S)-3,4,5-trimethylpiperazin-1-yl]phenyl]-6-oxo-4-(trifluoromethyl)-1H-pyridine-3-carboxamide;
N-[5-(4-carbamoyl-3,5-difluorophenyl)-4-fluoro-2-[(3R,5S)-3,4,5-trimethylpiperazin-1-yl]phenyl]-4-(difluoromethyl)-6-oxo-1H-pyridine-3-carboxamide;
4-fluoro-N-[4-fluoro-2-[(3R)-3,4-dimethylpiperazin-1-yl]-5-[2-[(3R)-3-methylmorpholin-4-yl]pyrimidin-5-yl]phenyl]-2-(trifluoromethyl)benzamide;
N-[4-fluoro-5-[2-(4-propan-2-ylpiperazin-1-yl)pyrimidin-5-yl]-2-[(3R,5S)-3,4,5-trimethylpiperazin-1-yl]phenyl]-1-methyl-6-oxo-4-(trifluoromethyl)pyridine-3-carboxamide;
N-[5-[2-(2,2-dimethylmorpholin-4-yl)pyrimidin-5-yl]-4-fluoro-2-[(3R,5S)-3,4,5-trimethylpiperazin-1-yl]phenyl]-1-methyl-6-oxo-4-(trifluoromethyl)pyridine-3-carboxamide;
N-[4-fluoro-5-(2-morpholin-4-ylpyrimidin-4-yl)-2-[(3R)-3,4-dimethylpiperazin-1-yl]phenyl]-1-methyl-6-oxo-4-(trifluoromethyl)pyridine-3-carboxamide;
4-(difluoromethyl)-N-[4-fluoro-5-(2-morpholin-4-ylpyrimidin-4-yl)-2-[(3R)-3,4-dimethylpiperazin-1-yl]phenyl]-1-methyl-6-oxopyridine-3-carboxamide;
2,3-difluoro-4-[2-fluoro-5-[[4-fluoro-2-(trifluoromethyl)benzoyl]amino]-4-[(3R,5S)-3,4,5-trimethylpiperazin-1-yl]phenyl]-N-(2,4,4-trimethylpentan-2-yl)benzamide;
2,3-difluoro-4-[2-fluoro-5-[[4-fluoro-2-(trifluoromethyl)benzoyl]amino]-4-[(3R)-3,4-dimethylpiperazin-1-yl]phenyl]-N-(2,4,4-trimethylpentan-2-yl)benzamide;
2,3-difluoro-4-[2-fluoro-5-[[4-fluoro-2-(trifluoromethyl)benzoyl]amino]-4-[(3R,5S)-3,4,5-trimethylpiperazin-1-yl]phenyl]benzamide;
2,3-difluoro-4-[2-fluoro-5-[[4-fluoro-2-(trifluoromethyl)benzoyl]amino]-4-[(3R)-3,4-dimethylpiperazin-1-yl]phenyl]benzamide;
N-[5-[2,3-difluoro-4-(2,4,4-trimethylpentan-2-ylcarbamoyl)phenyl]-4-fluoro-2-[(3R,5S)-3,4,5-trimethylpiperazin-1-yl]phenyl]-6-oxo-4-(trifluoromethyl)-1H-pyridine-3-carboxamide;
N-[5-(4-carbamoyl-2,3-difluorophenyl)-4-fluoro-2-[(3R,5S)-3,4,5-trimethylpiperazin-1-yl]phenyl]-6-oxo-4-(trifluoromethyl)-1H-pyridine-3-carboxamide;
N-[4-fluoro-5-(6-morpholin-4-ylpyridin-2-yl)-2-[(3R)-3,4-dimethylpiperazin-1-yl]phenyl]-1-methyl-6-oxo-4-(trifluoromethyl)pyridine-3-carboxamide;
4-(difluoromethyl)-N-[4-fluoro-5-(6-morpholin-4-ylpyridin-2-yl)-2-[(3R)-3,4-dimethylpiperazin-1-yl]phenyl]-1-methyl-6-oxopyridine-3-carboxamide;
4-fluoro-N-[4-fluoro-5-(6-morpholin-4-ylpyridin-2-yl)-2-[(3R)-3,4-dimethylpiperazin-1-yl]phenyl]-2-(trifluoromethyl)benzamide;
propan-2-yl 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-2,3,6,7-tetrahydroazepine-1-carboxylate;
N-[4-fluoro-5-(1-methylbenzimidazol-5-yl)-2-[(3R,5S)-3,4,5-trimethylpiperazin-1-yl]phenyl]-6-oxo-4-(trifluoromethyl)-1H-pyridine-3-carboxamide;
N-[4-fluoro-5-(3-methylbenzimidazol-5-yl)-2-[(3R,5S)-3,4,5-trimethylpiperazin-1-yl]phenyl]-6-oxo-4-(trifluoromethyl)-1H-pyridine-3-carboxamide;
N-[5-(1,3-benzothiazol-4-yl)-4-fluoro-2-[(3R,5S)-3,4,5-trimethylpiperazin-1-yl]phenyl]-6-oxo-4-(trifluoromethyl)-1H-pyridine-3-carboxamide;
N-[5-(1,3-benzothiazol-5-yl)-4-fluoro-2-[(3R,5S)-3,4,5-trimethylpiperazin-1-yl]phenyl]-6-oxo-4-(trifluoromethyl)-1H-pyridine-3-carboxamide;
N-[5-(1,3-benzothiazol-6-yl)-4-fluoro-2-[(3R,5S)-3,4,5-trimethylpiperazin-1-yl]phenyl]-6-oxo-4-(trifluoromethyl)-1H-pyridine-3-carboxamide;
4-(difluoromethyl)-N-[4-fluoro-5-(1-methylbenzimidazol-5-yl)-2-[(3R,5S)-3,4,5-trimethylpiperazin-1-yl]phenyl]-1-methyl-6-oxopyridine-3-carboxamide;
4-(difluoromethyl)-N-[4-fluoro-5-(3-methylbenzimidazol-5-yl)-2-[(3R,5S)-3,4,5-trimethylpiperazin-1-yl]phenyl]-1-methyl-6-oxopyridine-3-carboxamide;
N-[5-(1,3-benzothiazol-4-yl)-4-fluoro-2-[(3R,5S)-3,4,5-trimethylpiperazin-1-yl]phenyl]-4-(difluoromethyl)-1-methyl-6-oxopyridine-3-carboxamide;
N-[5-(1,3-benzothiazol-5-yl)-4-fluoro-2-[(3R,5S)-3,4,5-trimethylpiperazin-1-yl]phenyl]-4-(difluoromethyl)-1-methyl-6-oxopyridine-3-carboxamide;

N-[5-(1,3-benzothiazol-6-yl)-4-fluoro-2-[(3R,5S)-3,4,5-trimethylpiperazin-1-yl]phenyl]-4-(difluoromethyl)-1-methyl-6-oxopyridine-3-carboxamide;

N-[5-[1-(5-cyano-1,3-thiazol-2-yl)-3,6-dihydro-2H-pyridin-4-yl]-4-fluoro-2-[(3R,5S)-3,4,5-trimethylpiperazin-1-yl]phenyl]-4-(difluoromethyl)-6-oxo-1H-pyridine-3-carboxamide;

N-[5-[1-(5-cyano-1,3-thiazol-2-yl)-3,6-dihydro-2H-pyridin-4-yl]-4-fluoro-2-[(3R)-3,4-dimethylpiperazin-1-yl]phenyl]-4-(difluoromethyl)-6-oxo-1H-pyridine-3-carboxamide;

N-[5-[1-(5-cyano-1,3-thiazol-2-yl)-3,6-dihydro-2H-pyridin-5-yl]-4-fluoro-2-[(3R,5S)-3,4,5-trimethylpiperazin-1-yl]phenyl]-4-(difluoromethyl)-6-oxo-1H-pyridine-3-carboxamide;

N-[5-[1-(5-cyano-1,3-thiazol-2-yl)-3,6-dihydro-2H-pyridin-5-yl]-4-fluoro-2-[(3R)-3,4-dimethylpiperazin-1-yl]phenyl]-4-(difluoromethyl)-6-oxo-1H-pyridine-3-carboxamide;

N-[5-[1-(5-cyano-1,3-thiazol-2-yl)-3,6-dihydro-2H-pyridin-5-yl]-4-fluoro-2-[(3R)-3,4-dimethylpiperazin-1-yl]phenyl]-4-fluoro-2-(trifluoromethyl)benzamide;

N-[5-[1-(5-cyano-1,3-thiazol-2-yl)-3,6-dihydro-2H-pyridin-4-yl]-4-fluoro-2-[(3R)-3,4-dimethylpiperazin-1-yl]phenyl]-4-fluoro-2-(trifluoromethyl)benzamide;

N-[4-fluoro-5-[2-[(2R)-2-methylmorpholin-4-yl]pyrimidin-4-yl]-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-5-(2-morpholin-4-ylpyrimidin-4-yl)-2-[(3R,5S)-3,4,5-trimethylpiperazin-1-yl]phenyl]-6-oxo-1H-pyridine-3-carboxamide;

N-[4-fluoro-5-(2-morpholin-4-ylpyrimidin-4-yl)-2-[(3R,5S)-3,4,5-trimethylpiperazin-1-yl]phenyl]-1-methyl-6-oxo-4-(trifluoromethyl)pyridine-3-carboxamide;

N-[4-fluoro-5-[2-[(2R)-2-methylmorpholin-4-yl]pyrimidin-4-yl]-2-[(3S,5R)-3,4,5-trimethylpiperazin-1-yl]phenyl]-1-methyl-6-oxo-4-(trifluoromethyl)pyridine-3-carboxamide;

N-[4-fluoro-5-[2-(oxan-4-yloxy)pyrimidin-4-yl]-2-[(3R,5S)-3,4,5-trimethylpiperazin-1-yl]phenyl]-6-oxo-4-(trifluoromethyl)-1H-pyridine-3-carboxamide;

N-[5-[1-(5-cyano-1,3-thiazol-2-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[2-[(2R,6S)-2,6-dimethylmorpholin-4-yl]pyrimidin-4-yl]-2-[(3S,5R)-3,4,5-trimethylpiperazin-1-yl]phenyl]-6-oxo-4-(trifluoromethyl)-1H-pyridine-3-carboxamide;

N-[4-fluoro-5-[2-[(2R,6S)-2,6-dimethylmorpholin-4-yl]pyrimidin-4-yl]-2-[(3R)-3,4-dimethylpiperazin-1-yl]phenyl]-6-oxo-4-(trifluoromethyl)-1H-pyridine-3-carboxamide;

(1-methylcyclobutyl) 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-2,3,6,7-tetrahydroazepine-1-carboxylate;

N-[5-[1-(5-cyano-1,3-thiazol-2-yl)-2,3,6,7-tetrahydroazepin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[1-(2-cyanopyrimidin-4-yl)-3,6-dihydro-2H-pyridin-5-yl]-4-fluoro-2-[(3R,5S)-3,4,5-trimethylpiperazin-1-yl]phenyl]-6-oxo-4-(trifluoromethyl)-1H-pyridine-3-carboxamide;

(3,3-difluorocyclobutyl) 4-[5-[[4-(difluoromethyl)-6-oxo-1H-pyridine-3-carbonyl]amino]-2-fluoro-4-[(3R,5S)-3,4,5-trimethylpiperazin-1-yl]phenyl]-3,6-dihydro-2H-pyridine-1-carboxylate;

(3,3-difluorocyclobutyl) 4-[5-[[4-(difluoromethyl)-6-oxo-1H-pyridine-3-carbonyl]amino]-2-fluoro-4-[(3R)-3,4-dimethylpiperazin-1-yl]phenyl]-3,6-dihydro-2H-pyridine-1-carboxylate;

(3,3-difluorocyclobutyl) 5-[5-[[4-(difluoromethyl)-6-oxo-1H-pyridine-3-carbonyl]amino]-2-fluoro-4-[(3R,5S)-3,4,5-trimethylpiperazin-1-yl]phenyl]-3,6-dihydro-2H-pyridine-1-carboxylate;

(3,3-difluorocyclobutyl) 5-[5-[[4-(difluoromethyl)-6-oxo-1H-pyridine-3-carbonyl]amino]-2-fluoro-4-[(3R)-3,4-dimethylpiperazin-1-yl]phenyl]-3,6-dihydro-2H-pyridine-1-carboxylate;

(3,3-difluorocyclobutyl) 5-[2-fluoro-5-[[4-fluoro-2-(trifluoromethyl)benzoyl]amino]-4-[(3R)-3,4-dimethylpiperazin-1-yl]phenyl]-3,6-dihydro-2H-pyridine-1-carboxylate;

(3,3-difluorocyclobutyl) 4-[2-fluoro-5-[[4-fluoro-2-(trifluoromethyl)benzoyl]amino]-4-[(3R)-3,4-dimethylpiperazin-1-yl]phenyl]-3,6-dihydro-2H-pyridine-1-carboxylate;

N-[5-[1-(2-cyanopyrimidin-4-yl)-3,6-dihydro-2H-pyridin-4-yl]-4-fluoro-2-[(3R)-3,4-dimethylpiperazin-1-yl]phenyl]-4-(difluoromethyl)-6-oxo-1H-pyridine-3-carboxamide;

N-[5-[1-(2-cyanopyrimidin-4-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[4-(cyclohexylcarbamoyl)-3,5-difluorophenyl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[4-[(2,2-dimethylcyclohexyl)carbamoyl]-3,5-difluorophenyl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[4-(cyclopropylmethylcarbamoyl)-3,5-difluorophenyl]-4-fluoro-2-[(3R,5S)-3,4,5-trimethylpiperazin-1-yl]phenyl]-6-oxo-4-(trifluoromethyl)-1H-pyridine-3-carboxamide;

N-[4-fluoro-5-[2-(morpholin-4-ylmethyl)-1,3-thiazol-4-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[1-(2-morpholin-4-ylethyl)pyrazol-4-yl]-2-[(3R)-3,4-dimethylpiperazin-1-yl]phenyl]-6-oxo-4-(trifluoromethyl)-1H-pyridine-3-carboxamide;

4-(difluoromethyl)-N-[4-fluoro-5-[1-(2-morpholin-4-ylethyl)pyrazol-4-yl]-2-[(3R)-3,4-dimethylpiperazin-1-yl]phenyl]-1-methyl-6-oxopyridine-3-carboxamide;

N-[4-fluoro-5-[1-(2-morpholin-4-ylethyl)pyrazol-4-yl]-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-5-[1-(2-morpholin-4-ylethyl)pyrazol-4-yl]-2-[(3R,5S)-3,4,5-trimethylpiperazin-1-yl]phenyl]-1-methyl-6-oxopyridine-3-carboxamide;

N-[4-fluoro-5-(2-morpholin-4-ylpyrimidin-4-yl)-2-[(3R)-3,4-dimethylpiperazin-1-yl]phenyl]-6-oxo-4-(trifluoromethyl)-1H-pyridine-3-carboxamide;

N-[4-fluoro-5-(6-morpholin-4-ylpyridin-2-yl)-2-[(3R)-3,4-dimethylpiperazin-1-yl]phenyl]-6-oxo-4-(trifluoromethyl)-1H-pyridine-3-carboxamide;

4-(difluoromethyl)-N-[4-fluoro-5-(2-morpholin-4-ylpyrimidin-4-yl)-2-[(3R)-3,4-dimethylpiperazin-1-yl]phenyl]-6-oxo-1H-pyridine-3-carboxamide;

4-(difluoromethyl)-N-[4-fluoro-5-(6-morpholin-4-ylpyridin-2-yl)-2-[(3R)-3,4-dimethylpiperazin-1-yl]phenyl]-6-oxo-1H-pyridine-3-carboxamide;

2-(difluoromethyl)-4-fluoro-N-[4-fluoro-5-(2-morpholin-4-ylpyrimidin-5-yl)-2-[(3R,5S)-3,4,5-trimethylpiperazin-1-yl]phenyl]benzamide;

propan-2-yl 4-[5-[[4-(difluoromethyl)-6-oxo-1H-pyridine-3-carbonyl]amino]-2-fluoro-4-[(3R,5S)-3,4,5-trimethylpiperazin-1-yl]phenyl]-2,3,6,7-tetrahydroazepine-1-carboxylate;

propan-2-yl 4-[5-[[4-(difluoromethyl)-6-oxo-1H-pyridine-3-carbonyl]amino]-2-fluoro-4-[(3R)-3,4-dimethylpiperazin-1-yl]phenyl]-3,6-dihydro-2H-pyridine-1-carboxylate;

propan-2-yl 5-[5-[[4-(difluoromethyl)-6-oxo-1H-pyridine-3-carbonyl]amino]-2-fluoro-4-[(3R,5S)-3,4,5-trimethylpiperazin-1-yl]phenyl]-3,6-dihydro-2H-pyridine-1-carboxylate;

propan-2-yl 5-[5-[[4-(difluoromethyl)-6-oxo-1H-pyridine-3-carbonyl]amino]-2-fluoro-4-[(3R)-3,4-dimethylpiperazin-1-yl]phenyl]-3,6-dihydro-2H-pyridine-1-carboxylate;

propan-2-yl 4-[2-fluoro-5-[[4-fluoro-2-(trifluoromethyl)benzoyl]amino]-4-[(3R)-3,4-dimethylpiperazin-1-yl]phenyl]-3,6-dihydro-2H-pyridine-1-carboxylate;

propan-2-yl 5-[2-fluoro-5-[[4-fluoro-2-(trifluoromethyl)benzoyl]amino]-4-[(3R)-3,4-dimethylpiperazin-1-yl]phenyl]-3,6-dihydro-2H-pyridine-1-carboxylate;

(1-methylcyclobutyl) 4-[5-[[4-(difluoromethyl)-6-oxo-1H-pyridine-3-carbonyl]amino]-2-fluoro-4-[(3R,5S)-3,4,5-trimethylpiperazin-1-yl]phenyl]-2,3,6,7-tetrahydroazepine-1-carboxylate;

(3,3-difluorocyclobutyl) 4-[5-[[4-(difluoromethyl)-6-oxo-TH-pyridine-3-carbonyl]amino]-2-fluoro-4-[(3R,5S)-3,4,5-trimethylpiperazin-1-yl]phenyl]-2,3,6,7-tetrahydroazepine-1-carboxylate;

N-[5-[1-(5-cyano-1,3-thiazol-2-yl)-2,3,6,7-tetrahydroazepin-4-yl]-4-fluoro-2-[(3R,5S)-3,4,5-trimethylpiperazin-1-yl]phenyl]-4-(difluoromethyl)-6-oxo-1H-pyridine-3-carboxamide;

N-[5-[4-(cyclohexylcarbamoyl)-3-fluorophenyl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[4-[cyclopropylmethyl(methyl)carbamoyl]-3-fluorophenyl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[4-[(4,4-difluorocyclohexyl)carbamoyl]-3-fluorophenyl]-4-fluoro-2-[(3R,5S)-3,4,5-trimethylpiperazin-1-yl]phenyl]-6-oxo-4-(trifluoromethyl)-1H-pyridine-3-carboxamide;

N-[5-[4-(cyclopropylmethylcarbamoyl)-3-fluorophenyl]-4-fluoro-2-[(3R,5S)-3,4,5-trimethylpiperazin-1-yl]phenyl]-6-oxo-4-(trifluoromethyl)-1H-pyridine-3-carboxamide;

4-fluoro-N-[4-fluoro-2-[(3R)-3,4-dimethylpiperazin-1-yl]-5-[2-[(2R)-2-methylmorpholin-4-yl]pyrimidin-4-yl]phenyl]-2-(trifluoromethyl)benzamide;

4-fluoro-N-[4-fluoro-2-[(3S)-3,4-dimethylpiperazin-1-yl]-5-[2-[(3R)-3-methylmorpholin-4-yl]pyrimidin-5-yl]phenyl]-2-(trifluoromethyl)benzamide;

4-fluoro-N-[4-fluoro-2-[(3S)-3,4-dimethylpiperazin-1-yl]-5-[2-[(2R)-2-methylmorpholin-4-yl]pyrimidin-4-yl]phenyl]-2-(trifluoromethyl)benzamide;

4-fluoro-N-[4-fluoro-5-[2-[(2R,6S)-2,6-dimethylmorpholin-4-yl]pyrimidin-4-yl]-2-[(3R)-3,4-dimethylpiperazin-1-yl]phenyl]-2-(trifluoromethyl)benzamide;

N-[5-[1-(2-cyanopyrimidin-4-yl)-3,6-dihydro-2H-pyridin-5-yl]-4-fluoro-2-[(3R)-3,4-dimethylpiperazin-1-yl]phenyl]-4-(difluoromethyl)-6-oxo-1H-pyridine-3-carboxamide;

4-(difluoromethyl)-N-[4-fluoro-5-[4-(morpholin-4-ylmethyl)-1,3-thiazol-2-yl]-2-[(3R,5S)-3,4,5-trimethylpiperazin-1-yl]phenyl]-1-methyl-6-oxopyridine-3-carboxamide;

N-[4-fluoro-5-(6-piperazin-1-ylpyridin-2-yl)-2-[(3R)-3,4-dimethylpiperazin-1-yl]phenyl]-6-oxo-4-(trifluoromethyl)-1H-pyridine-3-carboxamide;

N-[4-fluoro-5-[2-[(2R,6S)-2,6-dimethylmorpholin-4-yl]pyrimidin-4-yl]-2-[(3R,5S)-3,4,5-trimethylpiperazin-1-yl]phenyl]-1-methyl-6-oxo-4-(trifluoromethyl)pyridine-3-carboxamide;

4-(difluoromethyl)-N-[4-fluoro-5-[2-[(2R,6S)-2,6-dimethylmorpholin-4-yl]pyrimidin-4-yl]-2-[(3S,5R)-3,4,5-trimethylpiperazin-1-yl]phenyl]-6-oxo-1H-pyridine-3-carboxamide;

4-(difluoromethyl)-N-[4-fluoro-5-[2-[(2R,6S)-2,6-dimethylmorpholin-4-yl]pyrimidin-4-yl]-2-[(3R,5S)-3,4,5-trimethylpiperazin-1-yl]phenyl]-1-methyl-6-oxopyridine-3-carboxamide;

4-(difluoromethyl)-N-[4-fluoro-5-(2-morpholin-4-ylpyrimidin-4-yl)-2-[(3R,5S)-3,4,5-trimethylpiperazin-1-yl]phenyl]-1-methyl-6-oxopyridine-3-carboxamide;

N-[5-[4-[(2,2-dimethylcyclohexyl)carbamoyl]-3-fluorophenyl]-4-fluoro-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[4-fluoro-5-[5-(morpholin-4-ylmethyl)-1,3-thiazol-2-yl]-2-[(3R,5S)-3,4,5-trimethylpiperazin-1-yl]phenyl]-1-methyl-6-oxopyridine-3-carboxamide;

4-(difluoromethyl)-N-[4-fluoro-5-[2-(morpholin-4-ylmethyl)-1,3-thiazol-4-yl]-2-[(3R,5S)-3,4,5-trimethylpiperazin-1-yl]phenyl]-1-methyl-6-oxopyridine-3-carboxamide;

N-[4-fluoro-5-[4-(morpholin-4-ylmethyl)-1,3-thiazol-2-yl]-2-[(3R,5S)-3,4,5-trimethylpiperazin-1-yl]phenyl]-6-oxo-4-(trifluoromethyl)-1H-pyridine-3-carboxamide;

N-[4-fluoro-5-[5-(morpholin-4-ylmethyl)-1,3-thiazol-2-yl]-2-[(3R,5S)-3,4,5-trimethylpiperazin-1-yl]phenyl]-6-oxo-4-(tnfluoromethyl)-1H-pyridine-3-carboxamide;

2-(difluoromethyl)-N-(5-(2-((2S,6R)-2,6-dimethylmorpholino)pyrimidin-5-yl)-4-fluoro-2-((3S,5R)-3,4,5-trimethylpiperazin-1-yl)phenyl)-4-fluorobenzamide;

2-(difluoromethyl)-4-fluoro-N-(4-fluoro-5-(2-((S)-2-methylmorpholino)pyrimidin-5-yl)-2-((3S,5R)-3,4,5-trimethylpiperazin-1-yl)phenyl)benzamide; and 2-(difluoromethyl)-4-fluoro-N-(4-fluoro-5-(2-((R)-2-methylmorpholino)pyrimidin-5-yl)-2-((3S,5R)-3,4,5-trimethylpiperazin-1-yl)phenyl)benzamide, 3-(difluoromethyl)-N-(5-(2-((2S,6R)-2,6-dimethylmorpholino)pyrimidin-5-yl)-4-fluoro-2-((3S,5R)-3,4,5-trimethylpiperazin-1-yl)phenyl)-5-fluoropicolinamide;

3-(difluoromethyl)-5-fluoro-N-(4-fluoro-5-(2-morpholinopyrimidin-5-yl)-2-((3S,5R)-3,4,5-trimethylpiperazin-1-yl)phenyl)picolinamide;

(S)-3-(difluoromethyl)-N-(2-(3,4-dimethylpiperazin-1-yl)-4-fluoro-5-(2-morpholinopyrimidin-4-yl)phenyl)-5-fluoropicolinamide;

3-(difluoromethyl)-5-fluoro-N-(4-fluoro-5-(2-((R)-2-methylmorpholino)pyrimidin-4-yl)-2-((3S,5R)-3,4,5-trimethylpiperazin-1-yl)phenyl)picolinamide;

3-(difluoromethyl)-N-(5-(2-((2S,6R)-2,6-dimethylmorpholino)pyrimidin-4-yl)-4-fluoro-2-((3S,5R)-3,4,5-trimethylpiperazin-1-yl)phenyl)-5-fluoropicolinamide;

N-(4'-(cyclohexyl(methyl)carbamoyl)-3',5',6-trifluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(4'-(cyclopentyl(methyl)carbamoyl)-3',5',6-trifluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

6-oxo-N-(3',5',6-trifluoro-4'-(((R)-tetrahydrofuran-3-yl)carbamoyl)-4-((3S,5R)-3,4,5-trimethylpiperazin-1-yl)-[1,1'-biphenyl]-3-yl)-4-(trifluoromethyl)-1,6-dihydropyridine-3-carboxamide;

3-(difluoromethyl)-N-(5-(2-((2S,6R)-2,6-dimethylmorpholino)pyrimidin-5-yl)-4-fluoro-2-((3S,5R)-3,4,5-trimethylpiperazin-1-yl)phenyl)-5-fluoropicolinamide; and 3-(difluoromethyl)-5-fluoro-N-(4-fluoro-5-(2-morpholinopyrimidin-5-yl)-2-((3S,5R)-3,4,5-trimethylpiperazin-1-yl)phenyl)picolinamide;

or a pharmaceutically acceptable salt and/or solvate thereof.

In some embodiments, the compound of Formula I is selected from:

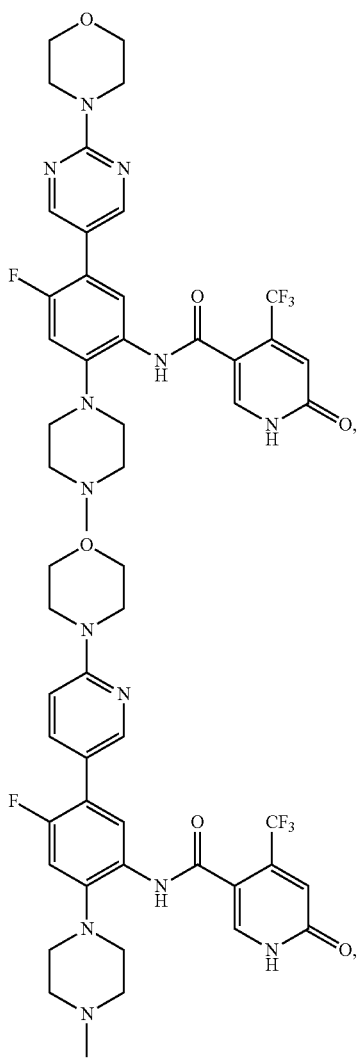

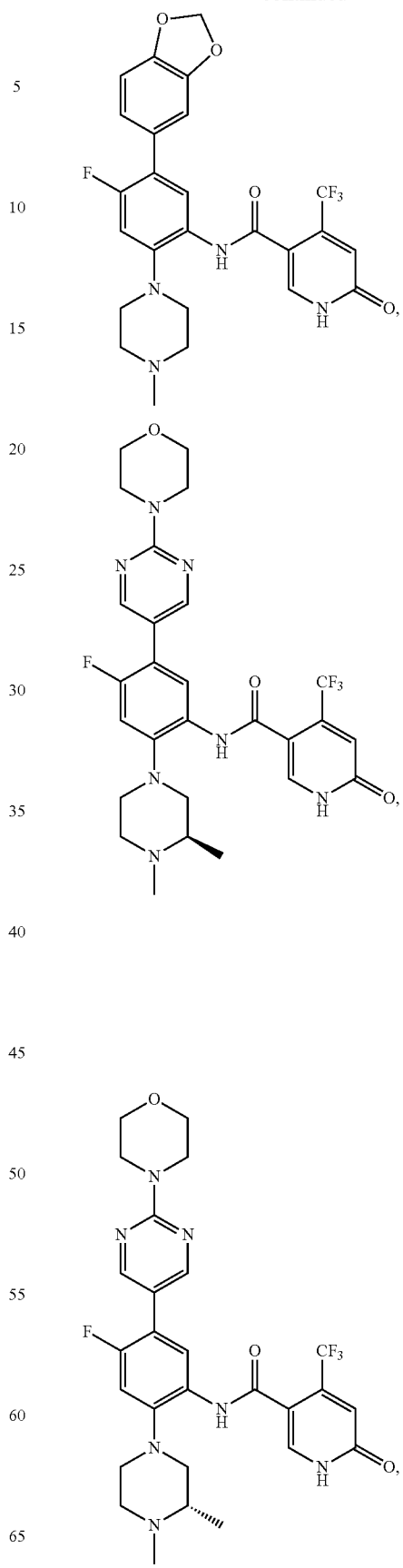

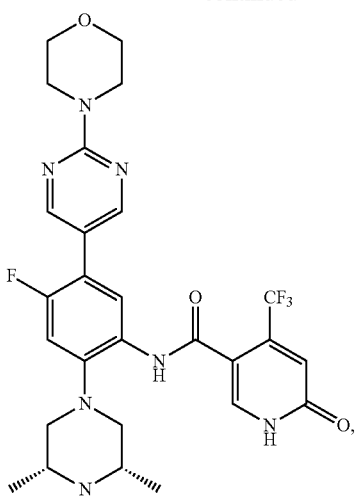
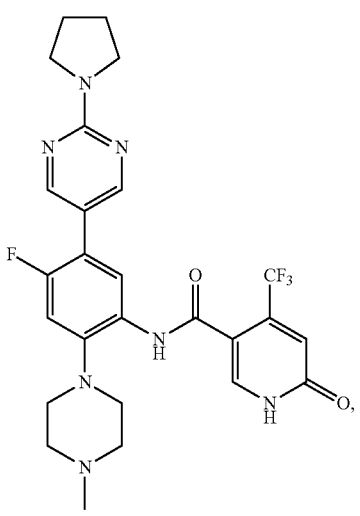
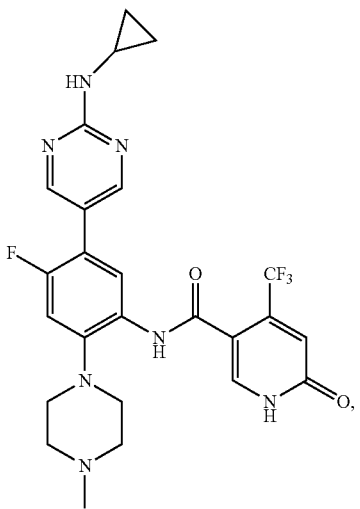
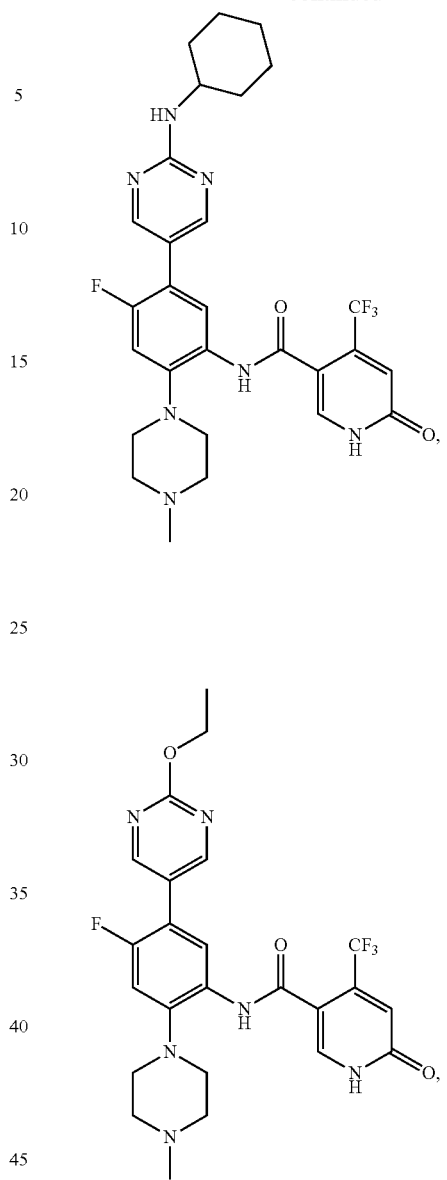
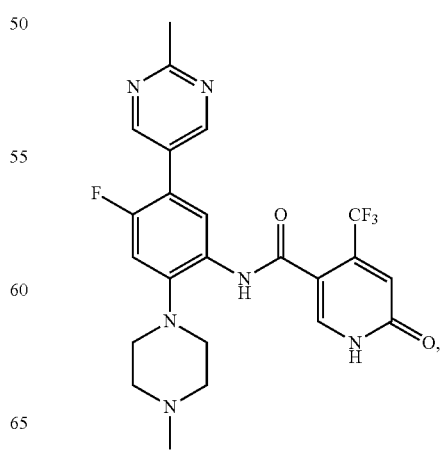

71
-continued
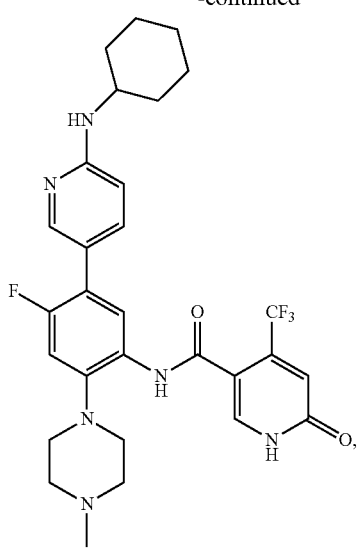
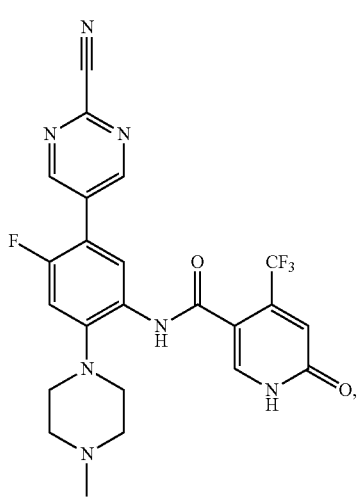
72
-continued
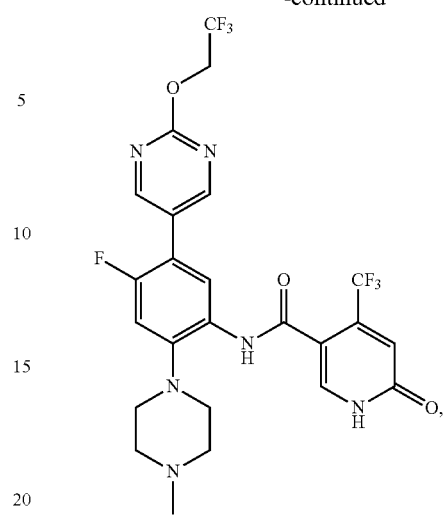
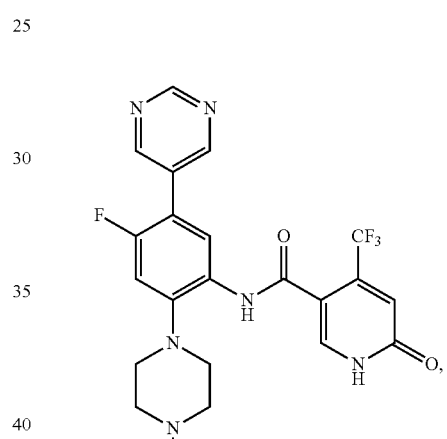
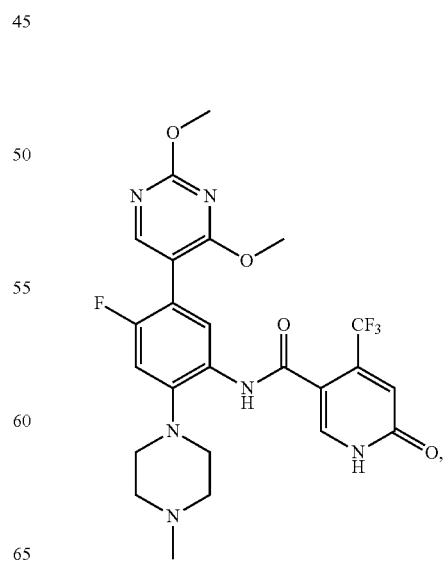

73
-continued
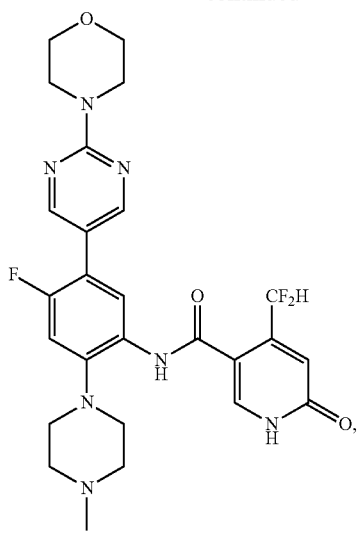
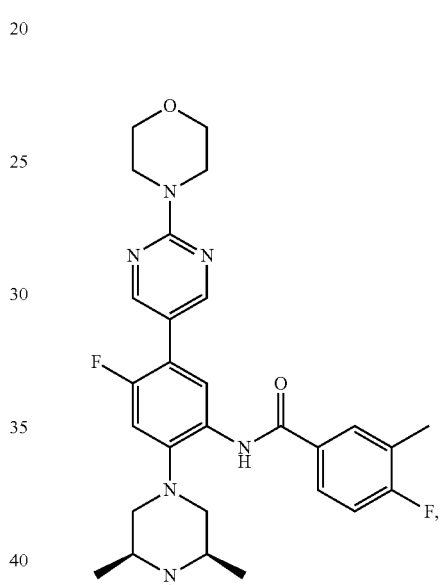
74
-continued
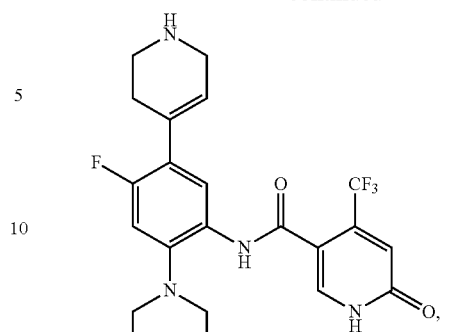
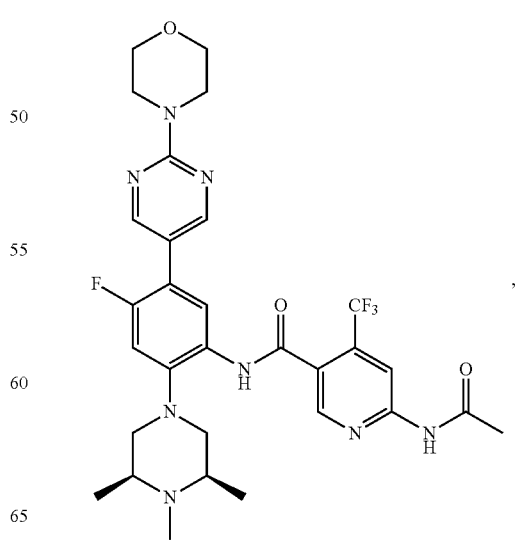

75
-continued
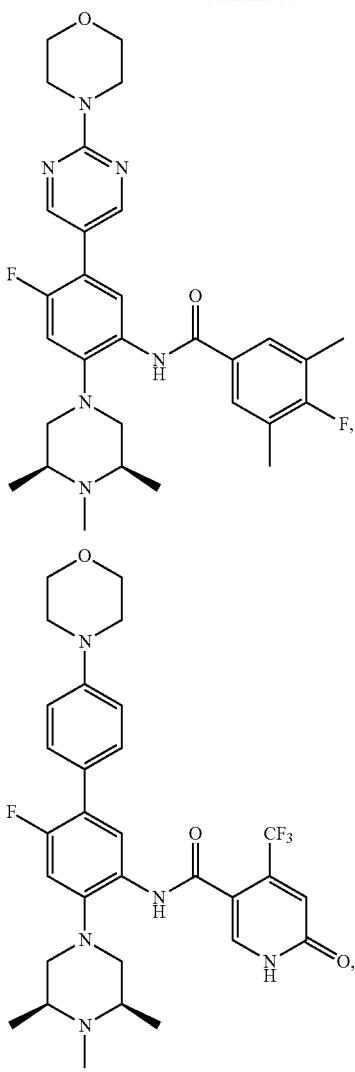
76
-continued
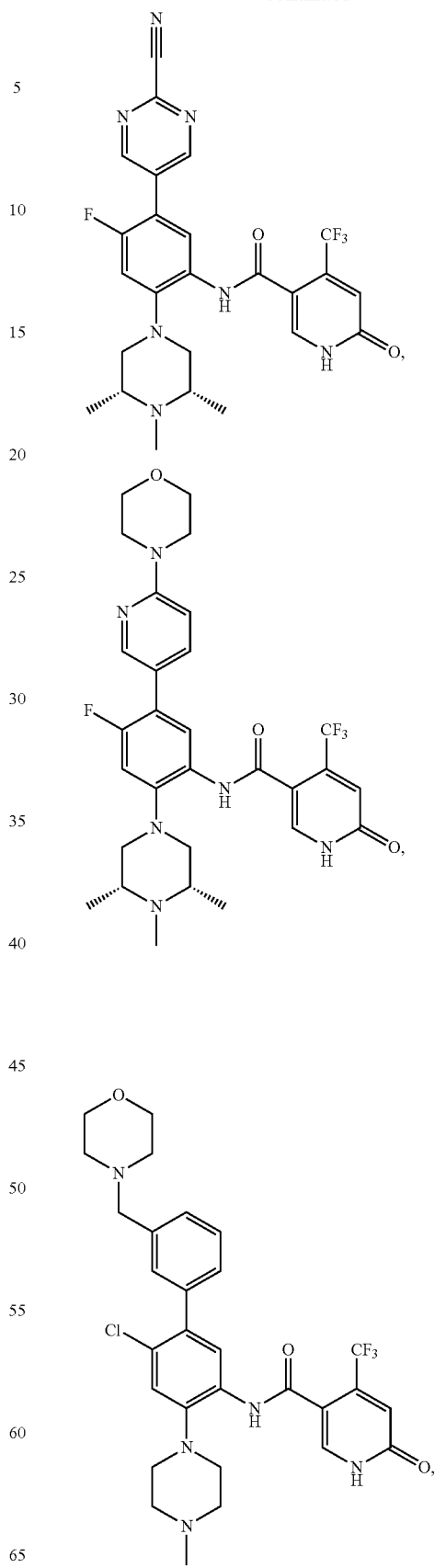

77
-continued
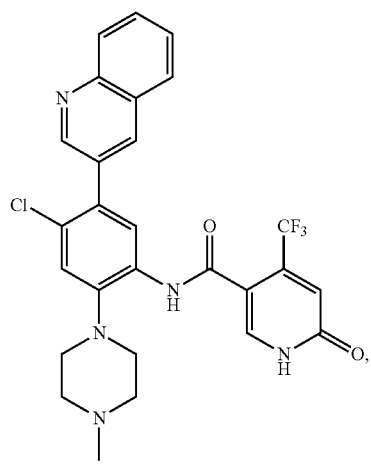
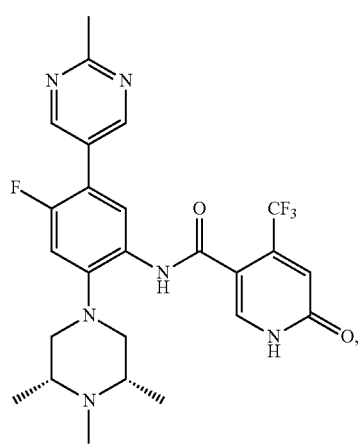
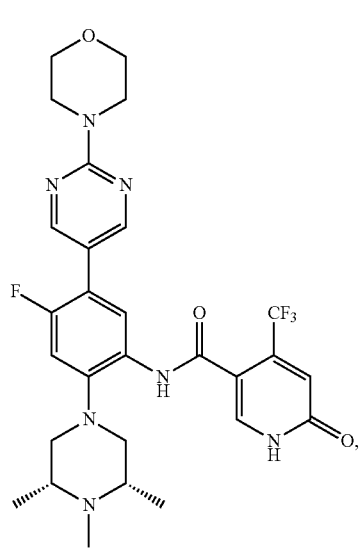
78
-continued
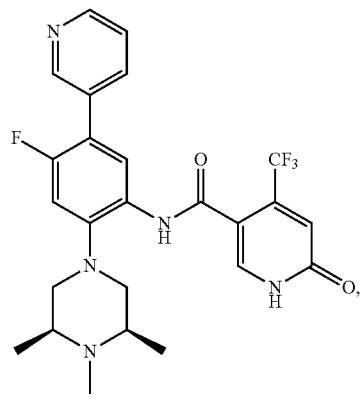

79
-continued
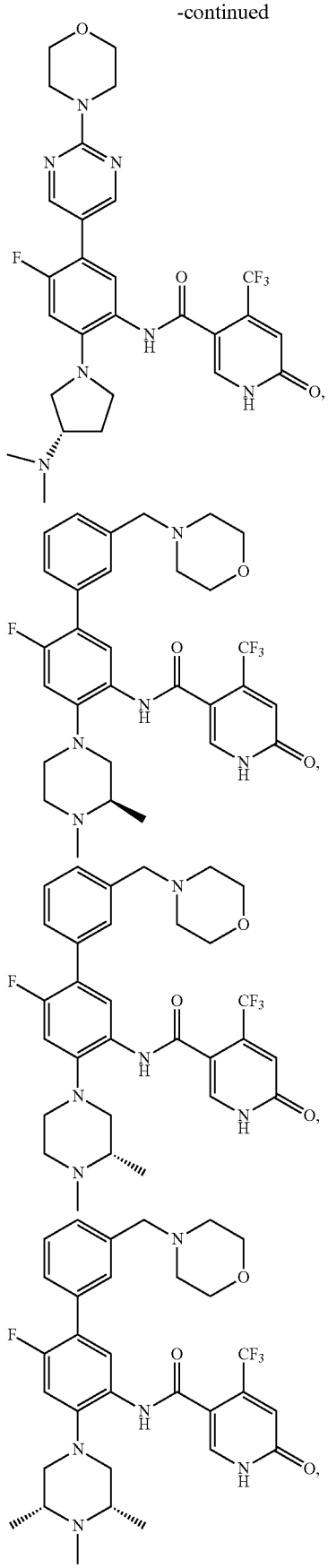
80
-continued
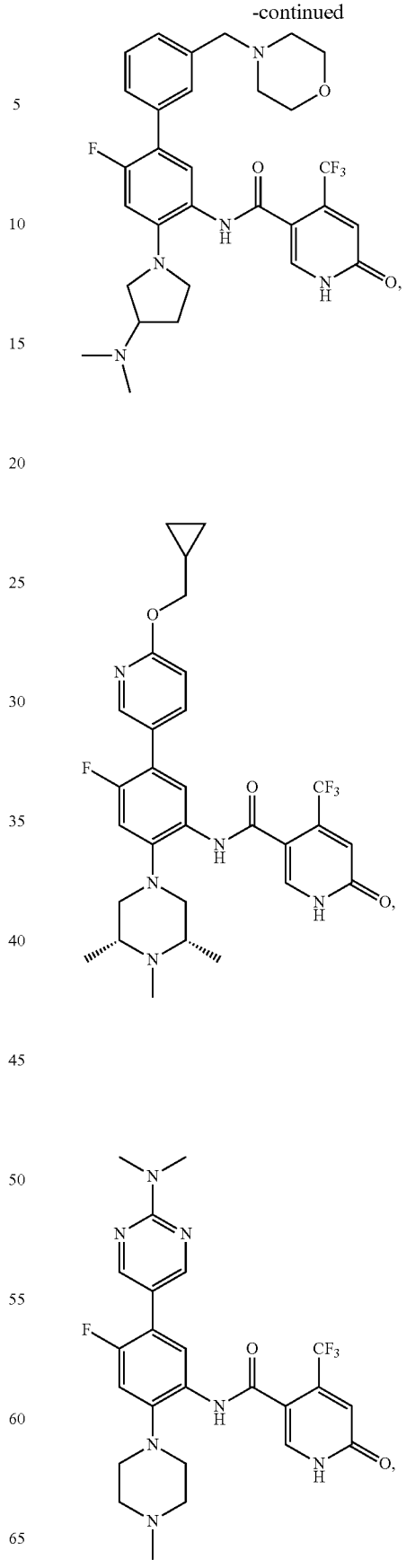

81
-continued
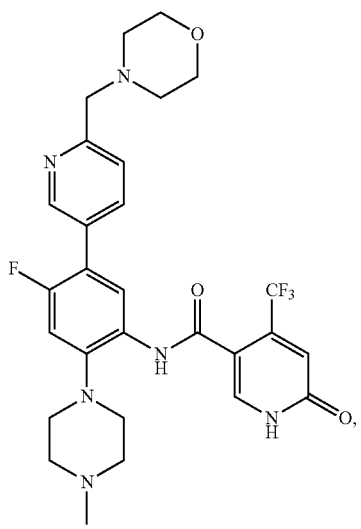
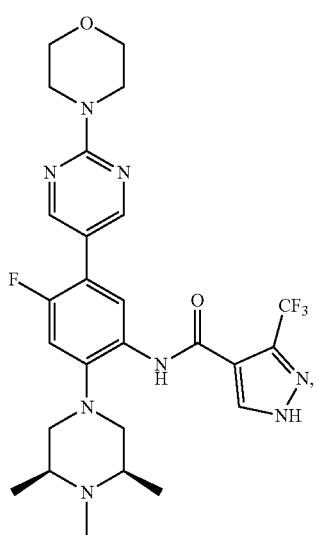
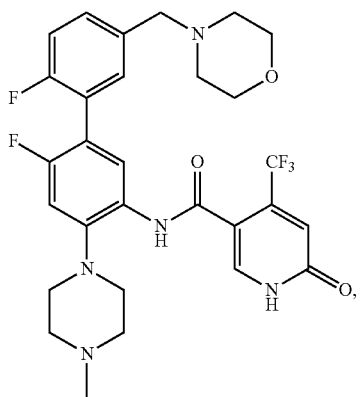
82
-continued
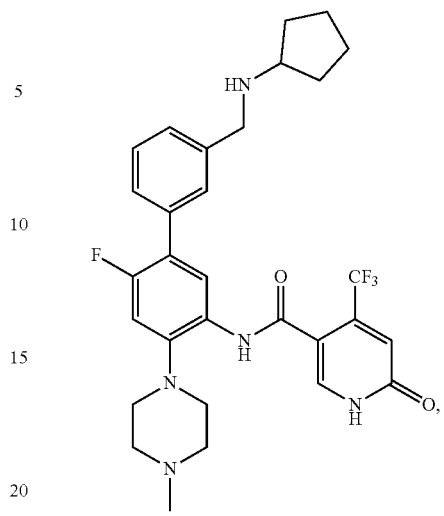
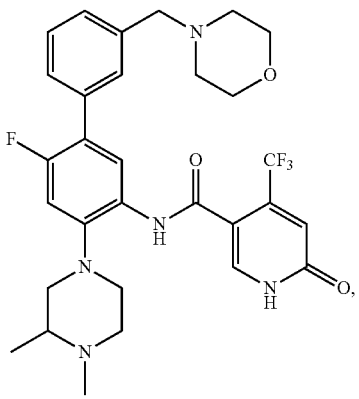
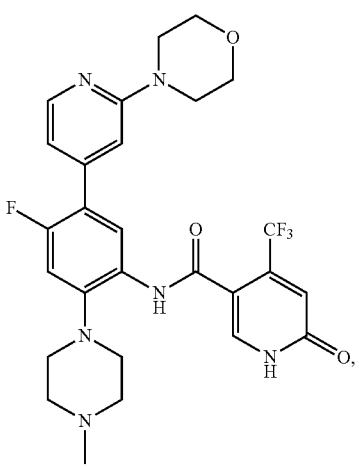

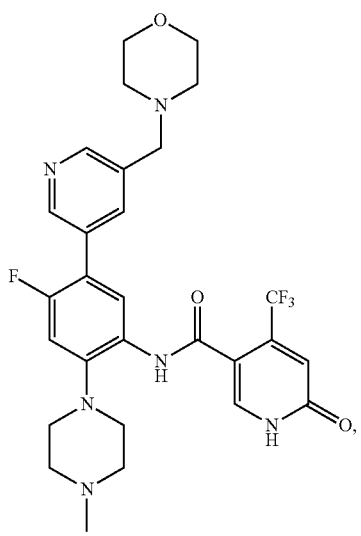
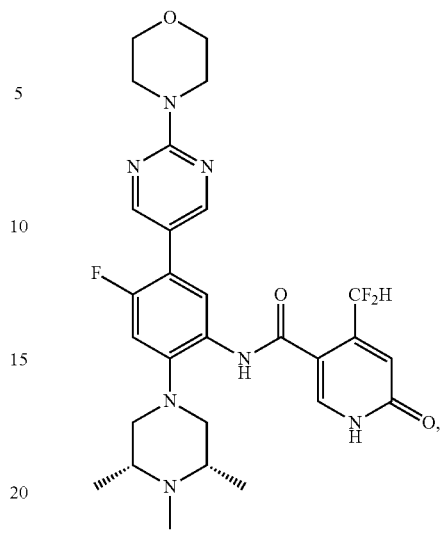
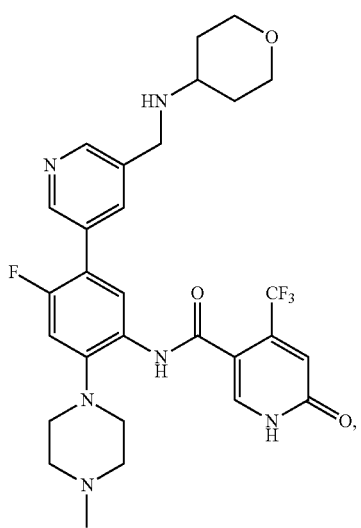
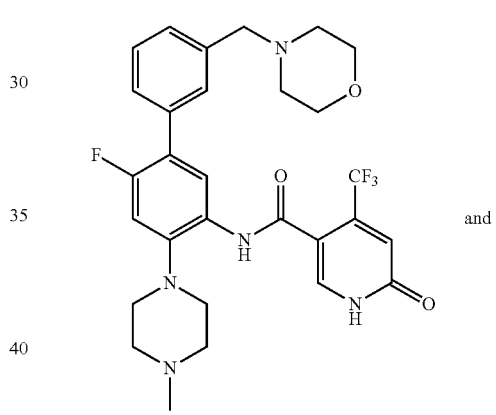
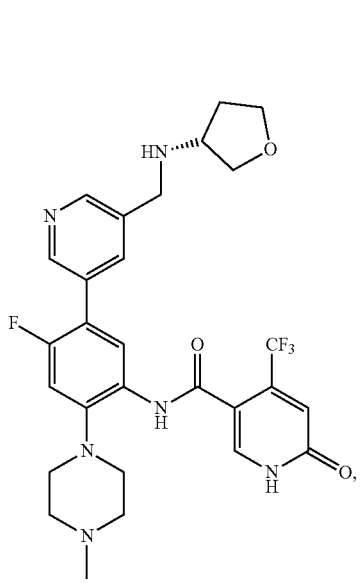
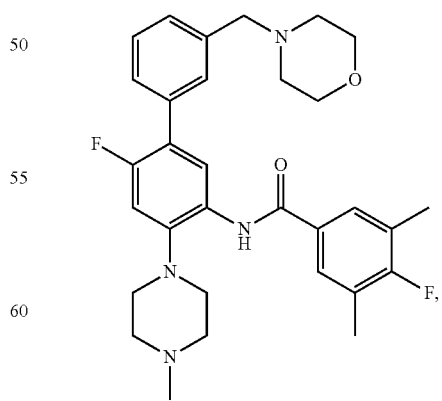
or a pharmaceutically acceptable salt and/or solvate thereof.

In some embodiments, the compound of Formula I is selected from:
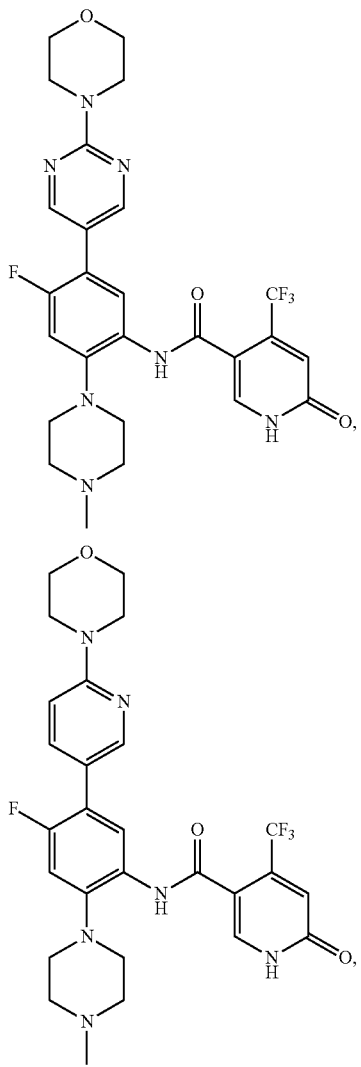
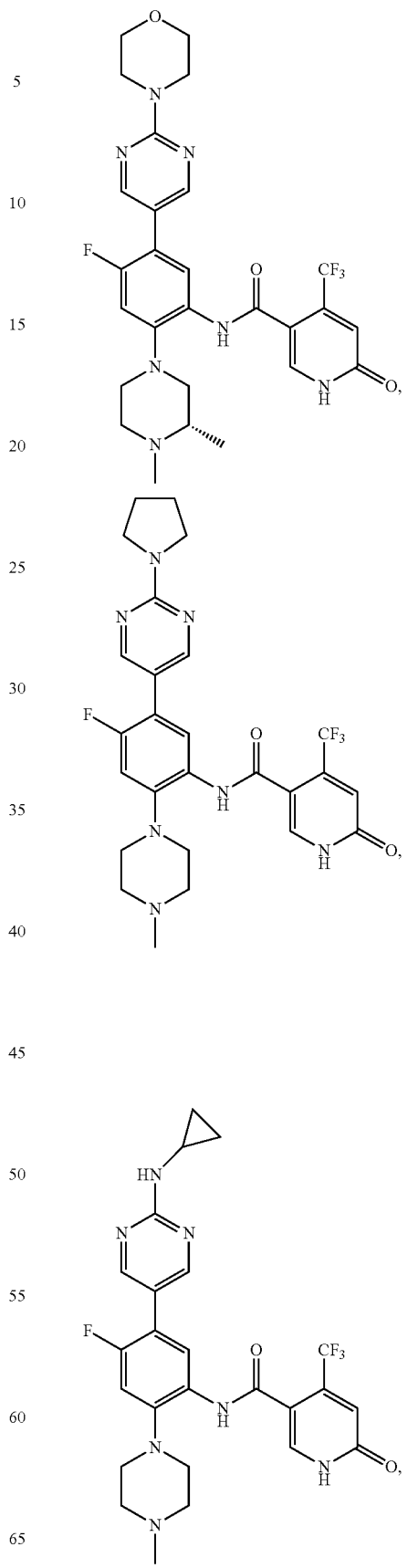

87
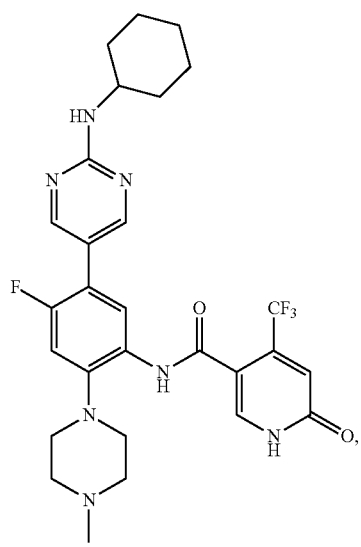
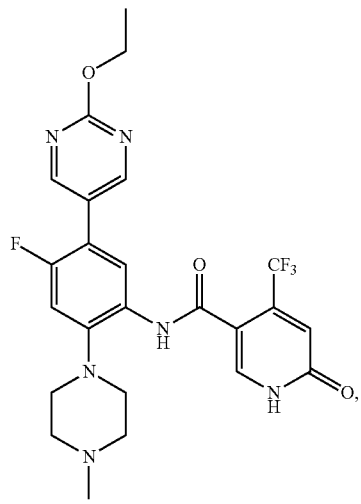
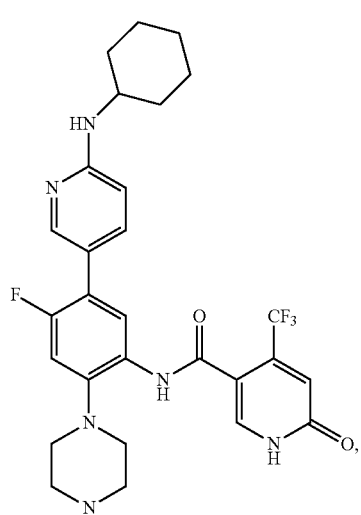
88
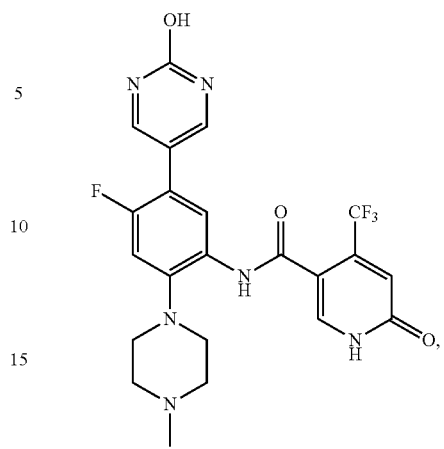
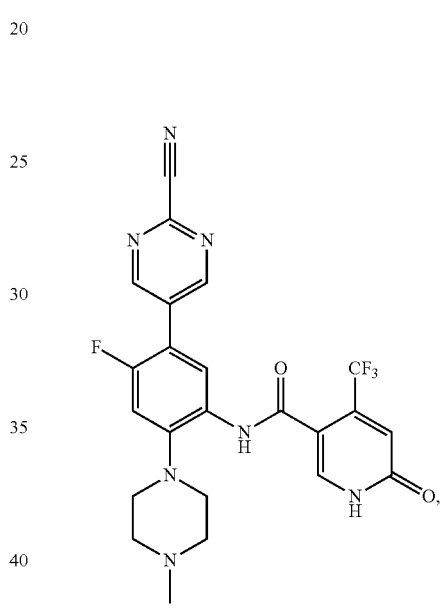
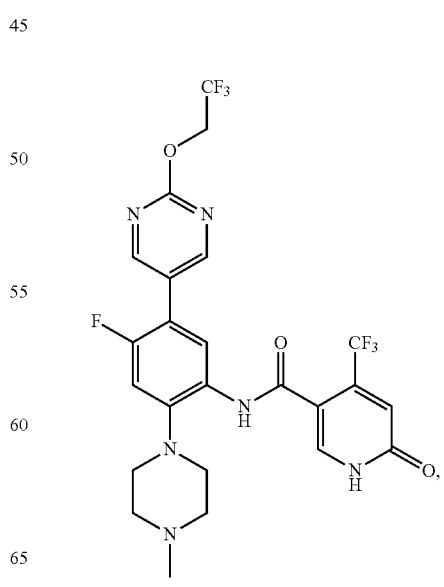

89
-continued
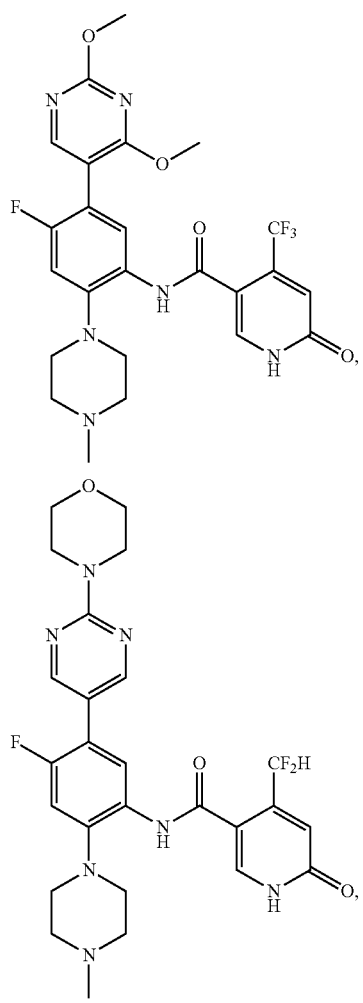
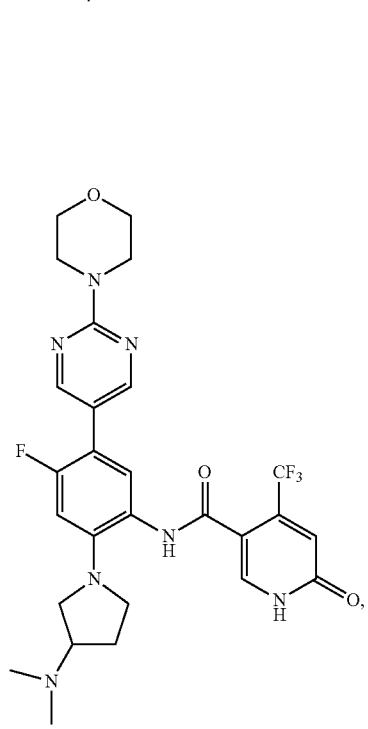
90
-continued
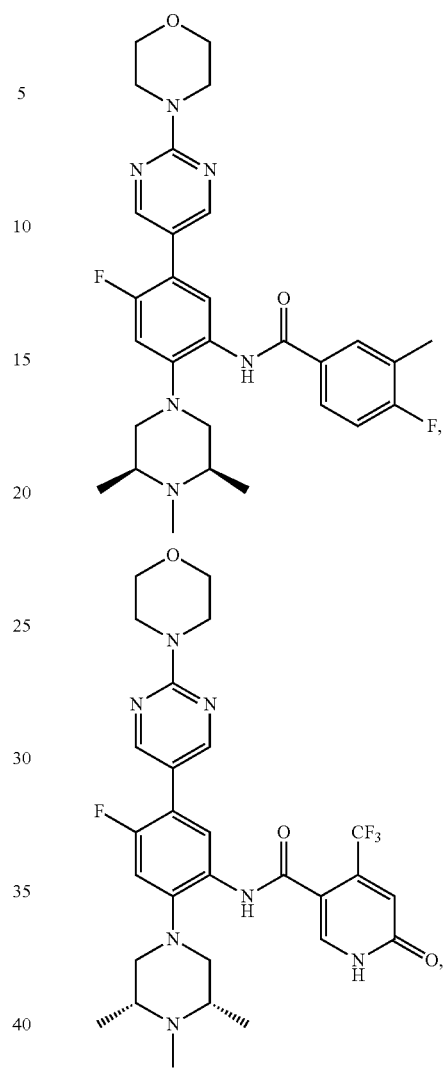
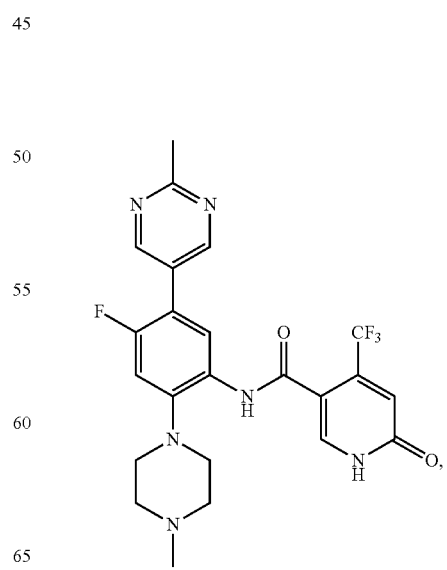

91
-continued
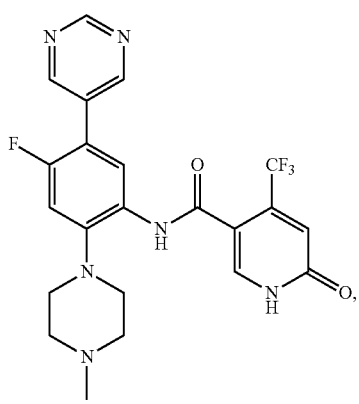
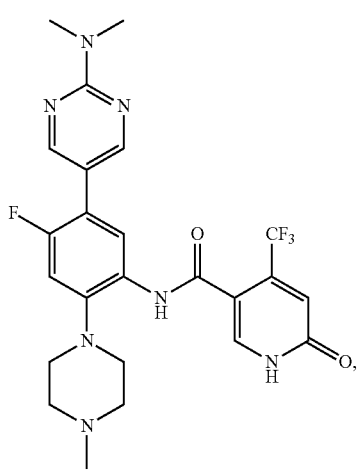
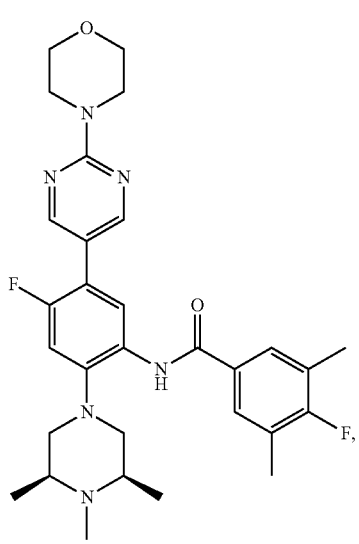
92
-continued
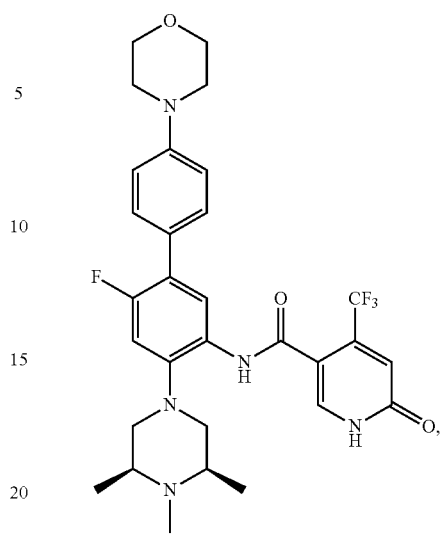
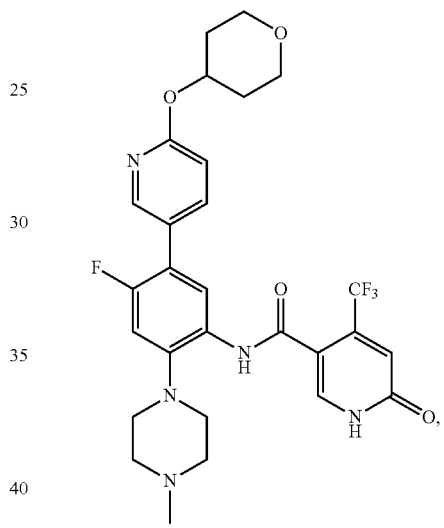
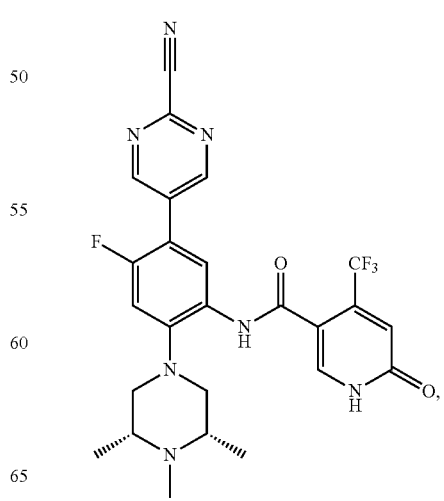

93
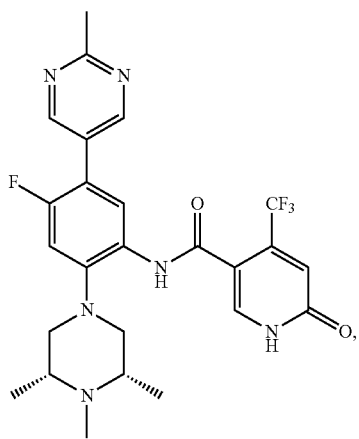
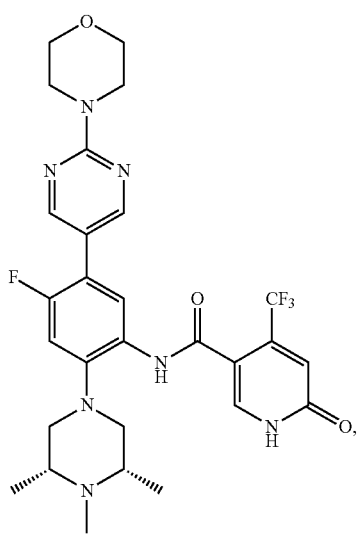
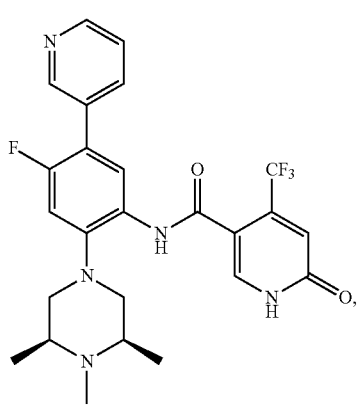
94
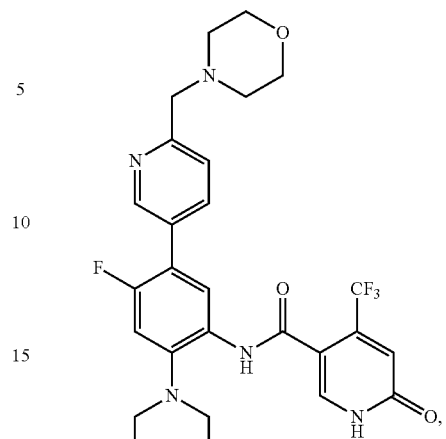
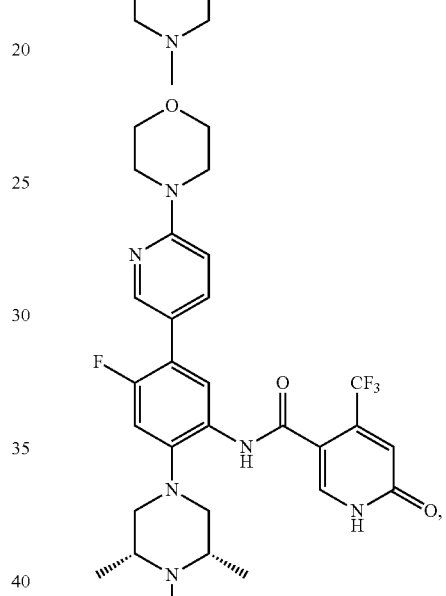
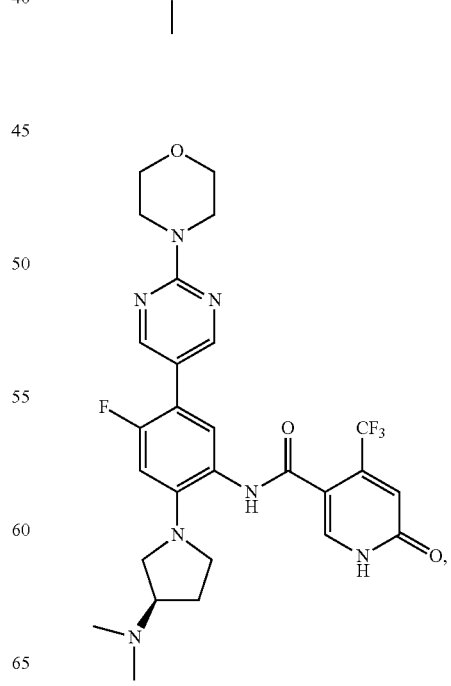

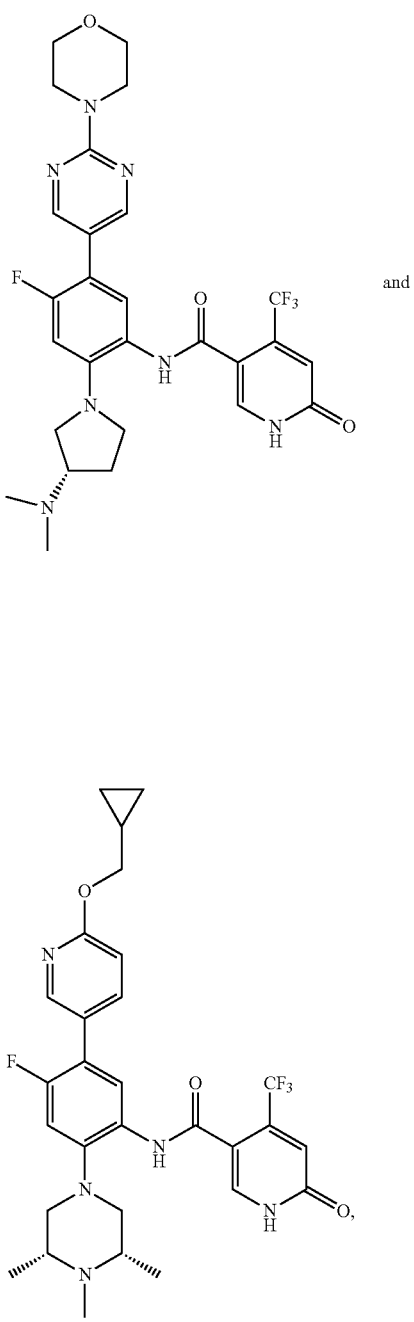

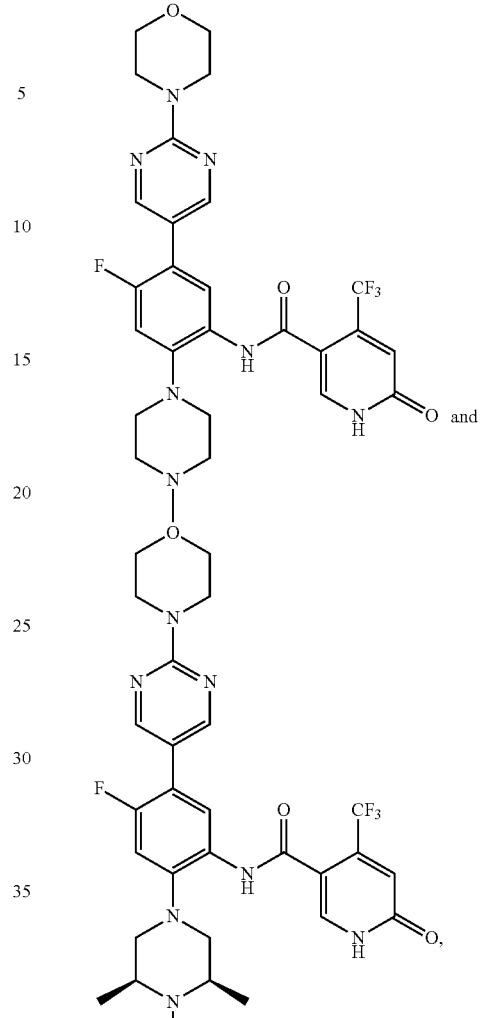

or a pharmaceutically acceptable salt and/or solvate thereof.

In some embodiments, the compound of Formula I is selected from, a pharmaceutically acceptable salt and/or solvate thereof:

The present application also includes a compound of Formula (Ia) or a pharmaceutically acceptable salt and/or solvate thereof:

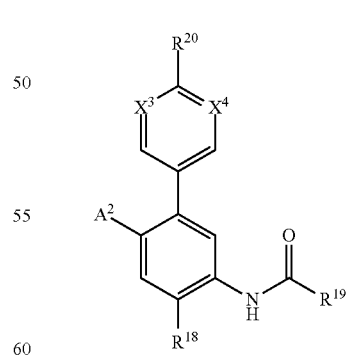

(Ia)

wherein:
$R^{18}$ is a heterocycloalkyl that is unsubstituted or substituted with one or more substituents selected from halo, $C_{1-6}$alkyl, $C_{1-6}$fluoroalkyl, $C_{3-10}$cycloalkyl, $OR^{21}$, $SR^{21}$, $NR^{22}R^{23}$, $C_{1-6}$alkyleneOR$^{21}$, $C_{1-6}$alkyleneSR$^{21}$ and $C_{1-6}$alkyleneNR$^{22}R^{23}$, provided that $R^{18}$ comprises at least one basic nitrogen atom;

$R^{19}$ is selected from $C_{6-10}$aryl and heteroaryl, and $R^{19}$ is unsubstituted or substituted with one or more substituents selected from halo, $C_{1-6}$alkyl, $C_{1-6}$fluoroalkyl, =O, =S, $OR^{24}$, $SR^{24}$ and $NR^{25}R^{26}$;

$R^{20}$ is selected from H, halo, CN, $C_{1-6}$alkyl, $C_{1-6}$fluoroalkyl, $OR^{27}$, $SR^{27}$, $SO_2R^{27}$, $NR^{28}R^{29}$, $R^{30}$, $C_{1-6}$alkylene$R^{30}$, $C_{1-6}$alkenylene$R^{30}$, $OC_{1-6}$alkylene$R^{30}$, $SC_{1-6}$alkylene$R^{30}$, $C_{1-6}$alkyleneNR$^{28}R^{29}$, $C_{1-6}$alkyleneOR$^{27}$, $C_{1-6}$alkyleneSR$^{27}$, $OC_{1-6}$alkyleneNR$^{28}R^{29}$, $SC_{1-6}$alkyleneNR$^{28}R^{29}$, $OC_{1-6}$alkyleneOR$^{27}$, $SC_{1-6}$alkyleneOR$^{27}$, $OC_{1-6}$alkyleneSR$^{27}$, $SC_{1-6}$alkyleneSR$^{27}$, $C(O)OR^{27}$, $C(S)OR^{27}$, $C(S)NR^{28}R^{29}$ and $C(O)NR^{28}R^{29}$;

$R^{21}$ is selected from H, $C_{1-6}$alkyl $C_{1-6}$fluoroalkyl, $C(O)C_{1-6}$alkyl and $C(O)C_{1-6}$fluoroalkyl;

$R^{22}$ and $R^{23}$ are independently selected from H, $C_{1-6}$alkyl, $C_{1-6}$fluoroalkyl, heterocycloalkyl, $C(O)C_{1-6}$alkyl, $C(O)C_{1-6}$fluoroalkyl, $C(O)OC_{1-6}$alkyl, $C(O)NHC_{1-6}$alkyl, $SO_2C_{1-6}$alkyl, $SO_2HNC_{1-6}$alkyl, $C_{1-6}$alkyleneOC$_{1-6}$alkyl, $C_{1-6}$alkyleneC$_{6-10}$aryl, $C_{1-6}$alkyleneheteroaryl, $C_{1-6}$alkyleneheterocycloalkyl and $C_{1-6}$alkyleneC$_{3-6}$cycloalkyl, or $R^{22}$ and $R^{23}$ together with the nitrogen atom to which they are attached form a 3-10 membered heterocycle that is unsubstituted or substituted with one or more substituents selected from halo, CN, OH, $C_{1-6}$alkyl $OC_{1-6}$alkyl, $C_{1-6}$fluoroalkyl, $OC_{1-6}$fluoroalkyl, $C(O)C_{1-6}$alkyl, $C(O)C_{1-6}$fluoroalkyl, $C(O)C_{1-6}$alkyl, $C(O)NHC_{1-6}$alkyl, $SO_2C_{1-6}$alkyl, $SO_2HNC_{1-6}$alkyl, $C_{1-6}$alkyleneOC$_{1-6}$alkyl, $C_{1-6}$alkyleneC$_{6-10}$aryl, $C_{1-6}$alkyleneheteroaryl, $C_{1-6}$alkyleneheterocycloalkyl and $C_{1-6}$alkyleneC$_{3-6}$cycloalkyl;

$R^{24}$ is selected from H, $C_{1-6}$alkyl, $C_{1-6}$fluoroalkyl and $C(O)C_{1-6}$alkyl;

$R^{25}$ and $R^{26}$ are independently selected from H, $C_{1-6}$alkyl, $C_{1-6}$fluoroalkyl and $C(O)C_{1-6}$alkyl, or $R^{25}$ and $R^{26}$ together with the nitrogen atom to which they are attached form a 3-10 membered heterocycle that is unsubstituted or substituted with one or more substituents selected from halo, OH, CN, $C_{1-6}$alkyl $OC_{1-6}$alkyl, $C_{1-6}$fluoroalkyl and $OC_{1-6}$fluoroalkyl;

$R^{27}$ is selected from H, $C_{1-6}$alkyl, $C_{1-6}$fluoroalkyl, $C(O)C_{1-6}$alkyl, $C_{3-10}$cycloalkyl, heterocycloalkyl, $C_{6-10}$aryl, heteroaryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and is unsubstituted or substituted with one or more substituents selected from halo, $OR^{31}$, $SR^{31}$, $NR^{32}R^{33}$, $C_{1-6}$alkyl, $C(O)R^{31}$, $C(O)OR^{31}$, $C(O)NR^{32}R^{33}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{31}$, $C_{1-6}$alkyleneOR$^{31}$, $C_{1-6}$alkyleneSR$^{31}$ and $C_{1-6}$alkyleneNR$^{32}R^{33}$;

$R^{28}$ and $R^{29}$ are each independently selected from H, $C_{1-10}$alkyl, $C_{1-10}$fluoroalkyl, $C(O)C_{1-6}$alkyl, $C(O)C_{6-10}$aryl, $C(O)C_{3-10}$cycloalkyl, $C(O)$heteroaryl, $C(O)$heterocycloalkyl, $C(O)OC_{1-6}$alkyl, $C(O)OC_{1-6}$fluoroalkyl, $C(O)OC_{6-10}$aryl, $C(O)OC_{3-10}$cycloalkyl, $C(O)O$heteroaryl, $C(O)O$heterocycloalkyl, $C(O)NHC_{1-6}$alkyl, $C(O)NHC_{1-6}$fluoroalkyl, $C(O)NHC_{6-10}$aryl, $C(O)NHC_{3-10}$cycloalkyl, $C(O)NH$heteroaryl, $C(O)NH$heterocycloalkyl, $SO_2C_{1-6}$alkyl, $SO_2C_{1-6}$fluoroalkyl, $SO_2C_{6-10}$aryl, $SO_2C_{3-10}$cycloalkyl, $SO_2$heteroaryl, $SO_2$heterocycloalkyl, $C_{3-10}$cycloalkyl, heterocycloalkyl, heteroaryl, $C_{6-10}$aryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and each of $R^{28}$ and $R^{29}$ are independently unsubstituted or substituted with one or more substituents selected from halo, CN, $OR^{31}$, $SR^{31}$, $NR^{32}R^{33}$, $C_{1-6}$alkyl, $C(O)R^{31}$, $C(O)OR^{31}$, $C(O)NR^{32}R^{33}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{31}$, $C_{1-6}$alkyleneOR$^{31}$, $C_{1-6}$alkyleneSR$^{31}$ and $C_{1-6}$alkyleneNR$^{32}R^{33}$, or $R^{28}$ and $R^{29}$ together with the nitrogen atom to which they are attached form a 3-10 membered heterocycle that is unsubstituted or substituted with one or more substituents independently selected from halo, CN, $OR^{31}$, $SR^{31}$, $NR^{32}R^{33}$, $C_{1-6}$alkyl, $C(O)R^{31}$, $C(O)OR^{31}$, $C(O)NR^{32}R^{33}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneR$^{31}$, $C_{1-6}$alkyleneOR$^{31}$, $C_{1-6}$alkyleneSR$^{31}$ and $C_{1-6}$alkyleneNR$^{32}R^{33}$;

$R^{30}$ is selected from $C(O)C_{1-6}$alkyl, $C(O)C_{1-6}$fluoroalkyl, $C(O)C_{6-10}$aryl, $C(O)C_{3-10}$cycloalkyl, $C(O)$heteroaryl, $C(O)$heterocycloalkyl, $C_{3-10}$cycloalkyl, heterocycloalkyl, heteroaryl and $C_{6-10}$aryl, and $R^{30}$ is unsubstituted or substituted with one or more substituents independently selected from halo, CN, $OR^{31}$, $SR^{31}$, $NR^{32}R^{33}$, $C_{1-6}$alkyl, $C(O)R^{31}$, $C(O)OR^{31}$, $C(O)NR^{32}R^{33}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{31}$, $C_{1-6}$alkyleneOR$^{31}$, $C_{1-6}$alkyleneSR$^{31}$ and $C_{1-6}$alkyleneNR$^{32}R^{33}$, $R^{31}$ is selected from H, $C_{1-6}$alkyl, $C_{1-6}$fluoroalkyl, $C(O)C_{1-6}$alkyl, $C_{3-10}$cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl, and $R^{31}$ is unsubstituted or substituted with one or more substituents selected from halo, CN, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl)($C_{1-6}$alkyl), $C(O)C_{1-6}$alkyl, $C(O)OH$, $C(O)OC_{1-6}$alkyl, $C(O)NH_2$, $C(O)NHC_{1-6}$alkyl, $C(O)N(C_{1-6}$alkyl)($C_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)($C_{1-6}$alkyl);

$R^{32}$ and $R^{33}$ are each independently selected from H, $C_{1-6}$alkyl, $C_{1-6}$fluoroalkyl, $C(O)C_{1-6}$alkyl, $C_{3-10}$cycloalkyl, heterocycloalkyl, $C_6$-10aryl, $C_{1-6}$alkylene $C_{6-10}$aryl, $C_{1-6}$alkyleneC$_{3-10}$cycloalkyl and $C_{1-6}$alkyleneheterocycloalkyl and each of $R^{15}$ and $R^{16}$ is unsubstituted or substituted with one or more substituents independently selected from halo, CN, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl)($C_{1-6}$alkyl), $C(O)C_{1-6}$alkyl, $C(O)OH$, $C(O)OC_{1-6}$alkyl, $C(O)NH_2$, $C(O)NHC_{1-6}$alkyl, $C(O)N(C_{1-6}$alkyl)($C_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl), or $R^{32}$ and $R^{33}$ together with the nitrogen atom to which they are attached form a 3-10 membered heterocycle that is unsubstituted or substituted with one or more substituents selected from halo, CN, $C_{1-6}$alkyl, $C_{1-6}$fluoroalkyl, OH, SH, OC$_{1-6}$alkyl, OC$_{1-6}$fluoroalkyl, SC$_{1-6}$alkyl, SC$_{1-6}$fluoroalkyl, NH$_2$, NHC$_{1-6}$alkyl, N(C$_{1-6}$alkyl)(C$_{1-6}$alkyl), C(O)C$_{1-6}$alkyl, C(O)OH, C(O)OC$_{1-6}$alkyl, C(O)NH$_2$, C(O)NHC$_{1-6}$alkyl, C(O)N(C$_{1-6}$alkyl)(C$_{1-6}$alkyl), SO$_2$C$_{1-6}$alkyl, S(O)C$_{1-6}$alkyl, C$_{6-10}$aryl, heteroaryl, C$_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl); $X^3$ and $X^4$ are each independently selected from CR$^{34}$ and N;

$R^{34}$ is selected from H, $C_{1-6}$alkyl and $C_{1-6}$fluoroalkyl;

$A^2$ is F; and alkyl and alkylene groups are optionally fluorosubstituted.

The present application also includes a compound of Formula (Ia) or a pharmaceutically acceptable salt and/or solvate thereof:

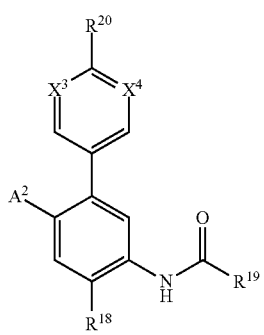

(Ia)

wherein:

$R^{18}$ is a heterocycloalkyl that is unsubstituted or substituted with one or more substituents selected from halo, $C_{1-6}$alkyl, $C_{1-6}$fluoroalkyl, OR$^{21}$, SR$^{21}$, NR$^{22}$R$^{23}$, $C_{1-6}$alkyleneOR$^{21}$, $C_{1-6}$alkyleneSR$^{21}$ and $C_{1-6}$alkyleneNR$^{22}$R$^{23}$, provided that $R^1$ comprises at least one basic nitrogen atom;

$R^{19}$ is selected from C$_{6-10}$aryl and heteroaryl, and $R^{19}$ is unsubstituted or substituted with one or more substituents selected from halo, $C_{1-6}$alkyl, $C_{1-6}$fluoroalkyl, =O, =S, OR$^{24}$, SR$^{24}$ and NR$^{25}$R$^{26}$;

$R^{20}$ is selected from H, halo, CN, $C_{1-6}$alkyl, $C_{1-6}$fluoroalkyl, OR$^{27}$, SR$^{27}$, NR$^{28}$R$^{29}$, R$^{30}$, $C_{1-6}$alkyleneR$^{30}$, OC$_{1-6}$alkyleneR$^{30}$, SC$_{1-6}$alkyleneR$^{30}$, $C_{1-6}$alkyleneNR$^{28}$R$^{29}$, $C_{1-6}$alkyleneOR$^{27}$, $C_{1-6}$alkyleneSR$^{27}$, OC$_{1-6}$alkyleneNR$^{28}$R$^{29}$, SC$_{1-6}$alkyleneNR$^{28}$R$^{29}$, OC$_{1-6}$alkyleneOR$^{27}$, SC$_{1-6}$alkyleneOR$^{27}$, OC$_{1-6}$alkyleneSR$^{27}$, SC$_{1-6}$alkyleneSR$^{27}$, C(O)OR$^{27}$, C(S)OR$^{27}$, C(S)NR$^{28}$R$^{29}$ and C(O)NR$^{28}$R$^{29}$;

$R^{21}$ is selected from H, $C_{1-6}$alkyl $C_{1-6}$fluoroalkyl, C(O)C$_{1-6}$alkyl and C(O)C$_{1-6}$fluoroalkyl;

$R^{22}$ and $R^{23}$ are independently selected from H, $C_{1-6}$alkyl, $C_{1-6}$fluoroalkyl, heterocycloalkyl, C(O)C$_{1-6}$alkyl and C(O)C$_{1-6}$fluoroalkyl, or $R^{22}$ and $R^{23}$ together with the nitrogen atom to which they are attached form a 3-10 membered heterocycle that is unsubstituted or substituted with one or more substituents selected from halo, OH, $C_{1-6}$alkyl OC$_{1-6}$alkyl, $C_{1-6}$fluoroalkyl, OC$_{1-6}$fluoroalkyl, C(O)C$_{1-6}$alkyl and C(O)C$_{1-6}$fluoroalkyl;

$R^{24}$ is selected from H, $C_{1-6}$alkyl, $C_{1-6}$fluoroalkyl and C(O)C$_{1-6}$alkyl;

$R^{25}$ and $R^{26}$ are independently selected from H, $C_{1-6}$alkyl, $C_{1-6}$fluoroalkyl and C(O)C$_{1-6}$alkyl, or $R^{25}$ and $R^{26}$ together with the nitrogen atom to which they are attached form a 3-10 membered heterocycle that is unsubstituted or substituted with one or more substituents selected from halo, OH, $C_{1-6}$alkyl OC$_{1-6}$alkyl, $C_{1-6}$fluoroalkyl and OC$_{1-6}$fluoroalkyl;

$R^{27}$ is selected from H, $C_{1-6}$alkyl, $C_{1-6}$fluoroalkyl, C(O)C$_{1-6}$alkyl, C$_{3-10}$cycloalkyl, heterocycloalkyl, C$_{6-10}$aryl, heteroaryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and is unsubstituted or substituted with one or more substituents selected from halo, OR$^{31}$, SR$^{31}$, NR$^{32}$R$^{33}$, $C_{1-6}$alkyl, C(O)R$^{31}$, C(O)OR$^{31}$, C(O)NR$^{32}$R$^{33}$, S(O)C$_{1-6}$alkyl, SO$_2$C$_{1-6}$alkyl, C$_{6-10}$aryl, heteroaryl, C$_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{31}$, $C_{1-6}$alkyleneOR$^{31}$, $C_{1-6}$alkyleneSR$^{31}$ and $C_{1-6}$alkyleneNR$^{32}$R$^{33}$;

$R^{28}$ and $R^{29}$ are each independently selected from H, $C_{1-10}$alkyl, $C_{1-10}$fluoroalkyl, C(O)C$_{1-6}$alkyl, C$_{3-10}$cycloalkyl, heterocycloalkyl, heteroaryl, C$_{6-10}$aryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and each of $R^{28}$ and $R^{29}$ are independently unsubstituted or substituted with one or more substituents selected from halo, OR$^{31}$, SR$^{31}$, NR$^{32}$R$^{33}$, $C_{1-6}$alkyl, C(O)R$^{31}$, C(O)OR$^{31}$, C(O)NR$^{32}$R$^{33}$, S(O)C$_{1-6}$alkyl, SO$_2$C$_{1-6}$alkyl, C$_{6-10}$aryl, heteroaryl, C$_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{31}$, $C_{1-6}$alkyleneOR$^{31}$, $C_{1-6}$alkyleneSR$^{31}$ and $C_{1-6}$alkyleneNR$^{32}$R$^{33}$, or $R^{28}$ and $R^{29}$ together with the nitrogen atom to which they are attached form a 3-10 membered heterocycle that is unsubstituted or substituted with one or more substituents independently selected from halo, OR$^{31}$, SR$^{31}$, NR$^{32}$R$^{33}$, $C_{1-6}$alkyl, C(O)R$^{31}$, C(O)OR$^{31}$, C(O)NR$^{32}$R$^{33}$, S(O)C$_{1-6}$alkyl, SO$_2$C$_{1-6}$alkyl, C$_{6-10}$aryl, heteroaryl, C$_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneR$^{31}$, $C_{1-6}$alkyleneOR$^{31}$, $C_{1-6}$alkyleneSR$^{31}$ and $C_{1-6}$alkyleneNR$^{32}$R$^{33}$;

$R^{30}$ is selected from C(O)C$_{1-6}$alkyl, C$_{3-10}$cycloalkyl, heterocycloalkyl, heteroaryl and C$_{6-10}$aryl, and $R^{30}$ is unsubstituted or substituted with one or more substituents independently selected from halo, OR$^{31}$, SR$^{31}$, NR$^{32}$R$^{33}$, $C_{1-6}$alkyl, C(O)R$^{31}$, C(O)OR$^{31}$, C(O)NR$^{32}$R$^{33}$, S(O)C$_{1-6}$alkyl, SO$_2$C$_{1-6}$alkyl, C$_{6-10}$aryl, heteroaryl, C$_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{31}$, $C_{1-6}$alkyleneOR$^{31}$, $C_{1-6}$alkyleneSR$^{31}$ and $C_{1-6}$alkyleneNR$^{32}$R$^{33}$;

$R^{31}$ is selected from H, $C_{1-6}$alkyl, $C_{1-6}$fluoroalkyl, C(O)C$_{1-6}$alkyl, C$_{3-10}$cycloalkyl, heterocycloalkyl, C$_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl, and $R^{31}$ is unsubstituted or substituted with one or more substituents selected from halo, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl$)(C_{1-6}$alkyl$)$, $C(O)C_{1-6}$alkyl, $C(O)OH$, $C(O)OC_{1-6}$alkyl, $C(O)NH_2$, $C(O)NHC_{1-6}$alkyl, $C(O)N(C_{1-6}$alkyl$)(C_{1-6}$alkyl$)$, $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl);

$R^{32}$ and $R^{33}$ are each independently selected from H, $C_{1-6}$alkyl, $C_{1-6}$fluoroalkyl, $C(O)C_{1-6}$alkyl, $C_{3-10}$cycloalkyl, heterocycloalkyl, $C_{6-10}$aryl, $C_{1-6}$alkylene$C_{6-10}$aryl, $C_{1-6}$alkylene$C_{3-10}$cycloalkyl and $C_{1-6}$alkyleneheterocycloalkyl and each of $R^{15}$ and $R^{16}$ is unsubstituted or substituted with one or more substituents independently selected from halo, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl$)(C_{1-6}$alkyl$)$, $C(O)C_{1-6}$alkyl, $C(O)OH$, $C(O)OC_{1-6}$alkyl, $C(O)NH_2$, $C(O)NHC_{1-6}$alkyl, $C(O)N(C_{1-6}$alkyl$)(C_{1-6}$alkyl$)$, $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl), or $R^{32}$ and $R^{33}$ together with the nitrogen atom to which they are attached form a 3-10 membered heterocycle that is unsubstituted or substituted with one or more substituents selected from halo, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl$)(C_{1-6}$alkyl$)$, $C(O)C_{1-6}$alkyl, $C(O)OH$, $C(O)OC_{1-6}$alkyl, $C(O)NH_2$, $C(O)NHC_{1-6}$alkyl, $C(O)N(C_{1-6}$alkyl$)(C_{1-6}$alkyl$)$, $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl);

$X^3$ and $X^4$ are each independently selected from $CR^{34}$ and N;

$R^{34}$ is selected from H, $C_{1-6}$alkyl and $C_{1-6}$fluoroalkyl;

$A^2$ is F; and alkyl and alkylene groups are optionally fluorosubstituted.

In some embodiments, $R^{18}$ is a heterocycloalkyl that is unsubstituted or substituted with one, two or three substituents selected from halo, $C_{1-6}$alkyl, $C_{1-6}$fluoroalkyl, $NR^{22}R^{23}$ and $C_{1-6}$alkyleneNR$^{22}$R$^{23}$, provided that $R^{18}$ comprises at least one basic nitrogen atom. In some embodiments, $R^{18}$ is a heterocycloalkyl that is substituted with one or two substituents selected from halo, $C_{1-6}$alkyl and $NR^{22}R^{23}$, provided that $R^{18}$ comprises at least one basic nitrogen atom. In some embodiments, $R^{18}$ is a heterocycloalkyl that is substituted with one, two or three substituents selected from $C_{1-6}$alkyl and $NR^{22}R^{23}$, provided that $R^{18}$ comprises at least one basic nitrogen atom. In some embodiments, $R^{18}$ is a $C_{5-6}$heterocyclalkyl comprising one or two nitrogen atoms at least one of which is basic.

In some embodiments, $R^{18}$ is selected from:

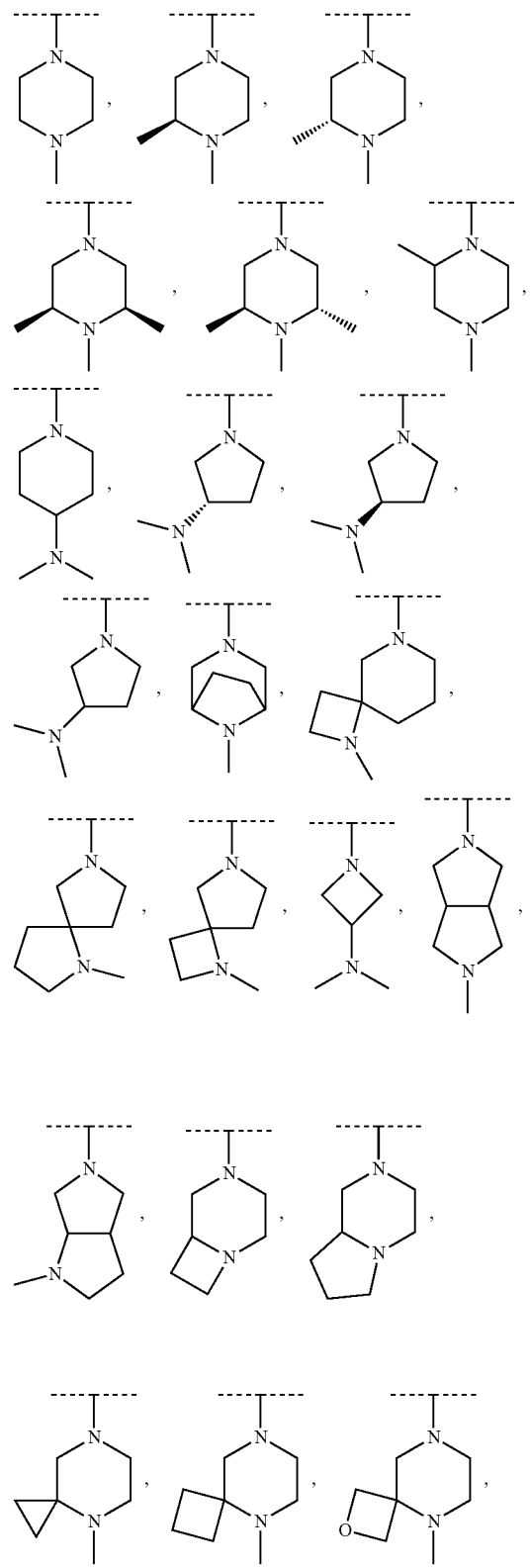

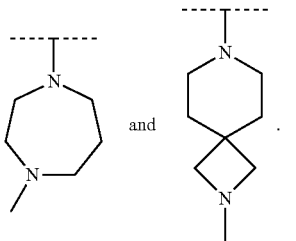

In some embodiments, $R^{18}$ is selected from:

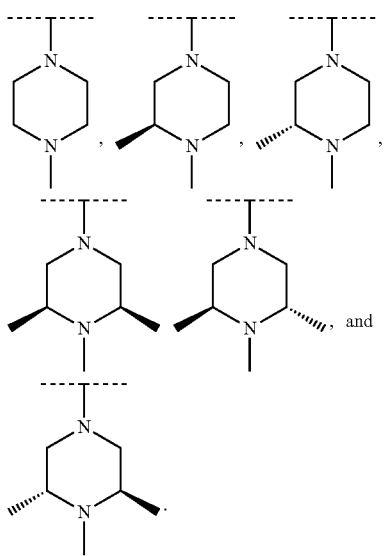

In some embodiments, $R^{18}$ is selected from:

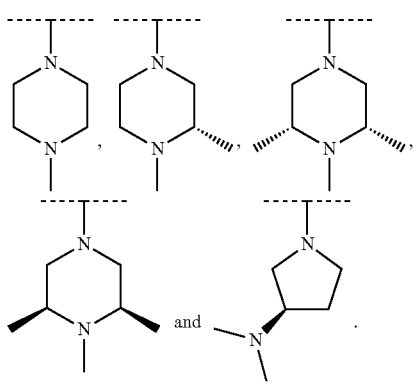

$R^{18}$ is selected from:

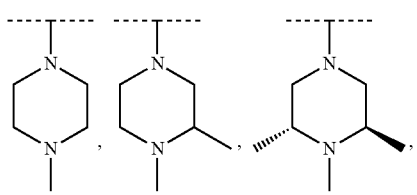

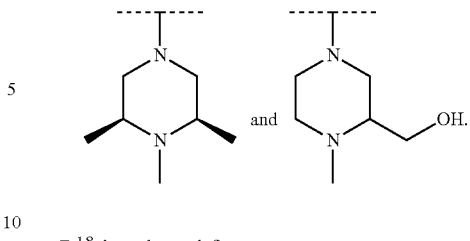

$R^{18}$ is selected from:

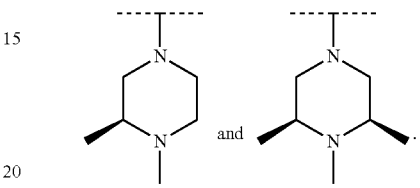

In some embodiments, $R^{19}$ is selected from $C_{6-10}$aryl and heteroaryl, and $R^{19}$ is unsubstituted or substituted with one, two or three substituents selected from halo, $C_{1-6}$alkyl, $C_{1-6}$fluoroalkyl, =O, $OR^{24}$, $SR^{24}$ and $NR^{25}R^{26}$. In some embodiments, $R^{19}$ is selected from $C_{6-10}$aryl and heteroaryl, and $R^{19}$ is unsubstituted or substituted with one, two or three substituents selected from halo, $C_{1-6}$alkyl, $C_{1-6}$fluoroalkyl, =O and $NR^{25}R^{26}$. In some embodiments, $R^{19}$ is selected from $C_{6-10}$aryl and heteroaryl, and $R^{19}$ is unsubstituted or substituted with one or two substituents selected from halo, $C_{1-6}$alkyl, $C_{1-6}$fluoroalkyl and =O. In some embodiments, $R^{19}$ is selected from phenyl and $C_{1-6}$-heteroaryl, and $R^{19}$ is substituted with one to three substituents selected from F, $CF_2H$, $CF_3$ and =O.

In some embodiments, $R^{19}$ is:

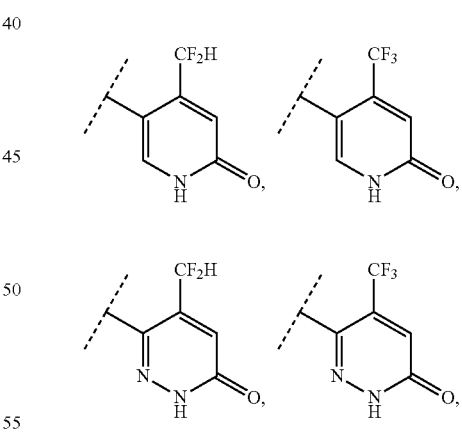

or a tautomer thereof. The tautomer of this $R^{19}$ group is

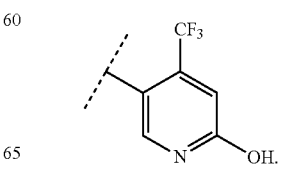

In some embodiments, $R^{19}$ is selected from:

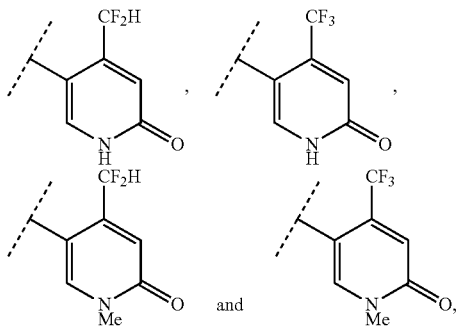

or a tautomer thereof.
In some embodiments, $R^{19}$ is

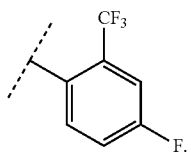

In some embodiments, $R^{20}$ is selected from H, halo, CN, $C_{1-6}$alkyl, $C_{1-6}$fluoroalkyl, $OR^{27}$, $NR^{28}R^{29}$, $R^{30}$, $C_{1-6}$alkylene$R^{30}$, $OC_{1-6}$alkylene$R^{30}$, $C_{1-6}$alkyleneNR$^{28}$R$^{29}$, $C_{1-6}$alkyleneOR$^{27}$, $OC_{1-6}$alkyleneNR$^{28}$R$^{29}$, $OC_{1-6}$alkyleneOR$^{27}$, $C(O)OR^{27}$ and $C(O)NR^{28}R^{29}$. In some embodiments, $R^{20}$ is selected from H, halo, CN, $C_{1-6}$alkyl, $C_{1-6}$fluoroalkyl, $OR^{27}$, $NR^{28}R^{29}$, $R^{30}$, $C_{1-6}$alkylene$R^{30}$, $OC_{1-6}$alkylene$R^{30}$, $C_{1-6}$alkyleneNR$^{28}$R$^{29}$, $C_{1-6}$alkyleneOR$^{27}$, $OC_{1-6}$alkyleneNR$^{28}$R$^{29}$ and $OC_{1-6}$alkyleneOR$^{27}$. In some embodiments, $R^{20}$ is selected from H, CN, $C_{1-6}$alkyl, $OR^{27}$, $NR^{28}R^{29}$, $R^{30}$, $C_{1-6}$alkylene$R^{30}$ and $OC_{1-6}$alkylene$R^{30}$. In some embodiments, wherein $R^{20}$ is selected from $C_{1-6}$alkyl and $R^{30}$.

In some embodiments, $R^{22}$ and $R^{23}$ are independently selected from H, $C_{1-6}$alkyl and heterocycloalkyl. In some embodiments, $R^{22}$ and $R^{23}$ are independently selected from H and $C_{1-6}$alkyl.

In some embodiments, $R^{22}$ and $R^{23}$ together with the nitrogen atom to which they are attached form a 3-10 membered heterocycle that is unsubstituted or substituted with one or two substituents selected from halo and $C_{1-6}$alkyl. In some embodiments, $R^{22}$ and $R^{23}$ together with the nitrogen atom to which they are attached form a 3-10 membered heterocycle that is unsubstituted.

In some embodiments, $R^{27}$ is selected from H, $C_{1-6}$alkyl, $C_{1-6}$fluoroalkyl, $C(O)C_{1-6}$alkyl, $C_{3-10}$cycloalkyl, heterocycloalkyl, $C_{6-10}$aryl, heteroaryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl. In some embodiments, $R^{27}$ is selected from H, $C_{1-6}$alkyl, $C_{1-6}$fluoroalkyl, $C_{3-10}$cycloalkyl, heterocycloalkyl, $C_{1-6}$alkyleneC$_{3-10}$cycloalkyl and $C_{1-6}$alkyleneheterocycloalkyl. In some embodiments, $R^{27}$ is selected from H, $C_{1-6}$alkyl, $C_{1-6}$fluoroalkyl, heterocycloalkyl and $C_{1-6}$alkyleneC$_{3-10}$cycloalkyl. In some embodiments, $R^{27}$ is selected from $C_{1-6}$alkyl, $C_{1-6}$fluoroalkyl and heterocycloalkyl. In some embodiments, $R^{27}$ is an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In some embodiments, $R^{28}$ and $R^{29}$ are each independently selected from H, $C_{1-10}$alkyl, $C_{1-10}$fluoroalkyl, $C(O)C_{1-6}$alkyl, $C_{3-10}$cycloalkyl, heterocycloalkyl, heteroaryl, $C_{6-10}$aryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl. In some embodiments, $R^{28}$ and $R^{29}$ are each independently selected from H, $C_{1-10}$alkyl, $C_{3-10}$cycloalkyl, heterocycloalkyl, $C_{1-6}$alkyleneC$_{3-10}$cycloalkyl and $C_{1-6}$alkyleneheterocycloalkyl. In some embodiments, $R^{28}$ and $R^{29}$ are each independently selected from H, $C_{1-10}$alkyl and $C_{3-10}$cycloalkyl.

In some embodiments, $R^{28}$ and $R^{29}$ together with the nitrogen atom to which they are attached form a 3-10 membered heterocycle that is unsubstituted.

In some embodiments, $R^{30}$ is selected from $C(O)C_{1-6}$alkyl, $C_{3-10}$cycloalkyl, heterocycloalkyl, heteroaryl and $C_{6-10}$aryl. In some embodiments, $R^{30}$ is selected from $C_{3-10}$cycloalkyl and heterocycloalkyl. In some embodiments, $R^{30}$ is heterocycloalkyl. In some embodiments $R^{30}$ is an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-TH-azepinyl, homopiperazinyl, 1,3-dioxepanyl, 4,7-dihydro-1,3-dioxepinyl, and hexamethylene oxidyl.

In some embodiments, $X^3$ and $X^4$ are each independently selected from $CR^{34}$ and N, in which $R^{34}$ is selected from H and $C_{1-6}$alkyl. In some embodiments, $X^3$ and $X^4$ are $CR^{34}$, in which $R^{34}$ is H. In some embodiments, $X^1$ and $X^2$ is $CR^{34}$ and the other of $X^1$ and $X^2$ is N, in which $R^{34}$ is H. In some embodiments, both of $X^3$ and $X^4$ are N.

The present application also include a compound of Formula (Ib) or a pharmaceutically acceptable salt and/or solvate thereof:

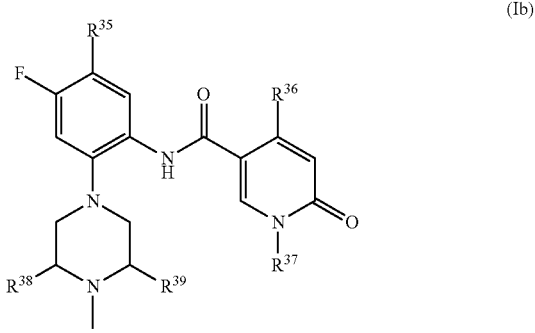

(Ib)

wherein:
$R^{35}$ is selected from phenyl, $C_{5-6}$heteroaryl and $C_{5-6}$heterocycloalkyl, and $R^{35}$ is substituted with one substituents selected from halo, CN, $C_{1-6}$alkyl, $C_{1-6}$fluoroalkyl, =O, =S, $OR^{40}$, $SR^{40}$, $SO_2R^{40}$, $NR^{41}R^{42}$, $R^{43}$, $C_{1-6}$alkyleneR$^{43}$, C$_{1-6}$alkenyleneR$^{43}$, OC$_{1-6}$alkyleneR$^{43}$, SC$_{1-6}$alkyleneR$^{43}$, C$_{1-6}$alkyleneNR$^{41}$R$^{42}$, C$_{1-6}$alkyleneOR$^{40}$, C$_{1-6}$alkyleneSR$^{40}$, OC$_{1-6}$alkyleneNR$^{41}$R$^{42}$, SC$_{1-6}$alkyleneNR$^{41}$R$^{42}$, OC$_{1-6}$alkyleneOR$^{40}$, SC$_{1-6}$alkyleneOR$^{40}$, OC$_{1-6}$alkyleneSR$^{40}$, SC$_{1-6}$alkyleneSR$^{40}$, C(O)OR$^{40}$, C(S)OR$^{40}$, C(S)NR$^{41}$R$^{42}$ and C(O)NR$^{41}$R$^{42}$;

R$^{36}$ is selected from CF$_2$H and CF$_3$;

R$^{37}$ is selected from H and CH$_3$;

R$^{38}$ and R$^{39}$ are independently selected from H and CH$_3$

R$^{40}$ is selected from H, C$_{1-6}$alkyl, C$_{1-6}$fluoroalkyl, C(O)C$_{1-6}$alkyl, C(O)C$_{1-6}$fluoroalkyl, C$_{3-10}$cycloalkyl, heterocycloalkyl, C$_{6-10}$aryl, heteroaryl, C$_{1-6}$alkyleneC$_{3-10}$cycloalkyl, C$_{1-6}$alkyleneC$_{6-10}$aryl, C$_{1-6}$alkyleneheteroaryl and C$_{1-6}$alkyleneheterocycloalkyl, and is unsubstituted or substituted with one to three substituents selected from halo, CN, OR$^{44}$, SR$^{44}$, NR$^{45}$R$^{46}$, C$_{1-6}$alkyl, C(O)R$^{44}$, C(O)OR$^{44}$, C(O)NR$^{45}$R$^{46}$, S(O)C$_{1-6}$alkyl, SO$_2$C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneR$^{44}$, C$_{1-6}$alkyleneOR$^{44}$, C$_{1-6}$alkyleneSR$^{44}$ and C$_{1-6}$alkyleneNR$^{45}$R$^{46}$; R$^{41}$ and R$^{42}$ are each independently selected from H, C$_{1-10}$alkyl, C$_{1-10}$fluoroalkyl, C(O)C$_{1-6}$alkyl, C(O)C$_{1-6}$fluoroalkyl, C(O)C$_{6-10}$aryl, C(O)C$_{3-10}$cycloalkyl, C(O)heteroaryl, C(O)heterocycloalkyl, C(O)OC$_{1-6}$alkyl, C(O)OC$_{1-6}$fluoroalkyl, C(O)OC$_{6-10}$aryl, C(O)OC$_{3-10}$cycloalkyl, C(O)Oheteroaryl, C(O)Oheterocycloalkyl, C(O)NHC$_{1-6}$alkyl, C(O)NHC$_{1-6}$fluoroalkyl, C(O)NHC$_{6-10}$aryl, C(O)NHC$_{3-10}$cycloalkyl, C(O)NHheteroaryl, C(O)NHheterocycloalkyl, SO$_2$C$_{1-6}$alkyl, SO$_2$C$_{1-6}$fluoroalkyl, SO$_2$C$_{6-10}$aryl, SO$_2$C$_{3-10}$cycloalkyl, SO$_2$heteroaryl, SO$_2$heterocycloalkyl, C$_{3-10}$cycloalkyl, heterocycloalkyl, heteroaryl, C$_{6-10}$aryl, C$_{1-6}$alkyleneC$_{3-10}$cycloalkyl, C$_{1-6}$alkyleneC$_{6-10}$aryl, C$_{1-6}$alkyleneheteroaryl and C$_{1-6}$alkyleneheterocycloalkyl, and each of R$^{41}$ and R$^{42}$ are independently unsubstituted or substituted with one to three substituents selected from halo, CN, OR$^{44}$, SR$^{44}$, NR$^{45}$R$^{46}$, C$_{1-6}$alkyl, C(O)R$^{44}$, C(O)OR$^{44}$, C(O)NR$^{45}$R$^{46}$, S(O)C$_{1-6}$alkyl, SO$_2$C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneR$^{44}$, C$_{1-6}$alkyleneOR$^{44}$, C$_{1-6}$alkyleneSR$^{44}$ and C$_{1-6}$alkyleneNR$^{45}$R$^{46}$, or R$^{41}$ and R$^{42}$ together with the nitrogen atom to which they are attached form a 3-6 membered heterocycle that is unsubstituted or substituted with one to three substituents independently selected from halo, CN, OR$^{44}$, SR$^{44}$, NR$^{45}$R$^{46}$, C$_{1-6}$alkyl, C(O)R$^{44}$, C(O)OR$^{44}$, C(O)NR$^{45}$R$^{46}$, S(O)C$_{1-6}$alkyl, SO$_2$C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneR$^{44}$, C$_{1-6}$alkyleneOR$^{44}$, C$_{1-6}$alkyleneSR$^{44}$ and C$_{1-6}$alkyleneNR$^{45}$R$^{46}$;

R$^{43}$ is selected from C(O)C$_{1-6}$alkyl, C(O)C$_{1-6}$fluoroalkyl, C(O)C$_{6-10}$aryl, C(O)C$_{3-10}$cycloalkyl, C(O)heteroaryl, C(O)heterocycloalkyl, C$_{3-10}$cycloalkyl, heterocycloalkyl, heteroaryl and C$_{6-10}$aryl, and R$^{43}$ is unsubstituted or substituted with one to three substituents independently selected from halo, CN, OR$^{44}$, SR$^{44}$, NR$^{45}$R$^{46}$, C$_{1-6}$alkyl, C(O)R$^{44}$, C(O)OR$^{44}$, C(O)NR$^{45}$R$^{46}$, S(O)C$_{1-6}$alkyl, SO$_2$C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneR$^{44}$, C$_{1-6}$alkyleneOR$^{44}$, C$_{1-6}$alkyleneSR$^{44}$ and C$_{1-6}$alkyleneNR$^{45}$R$^{46}$.

R$^{44}$ is selected from H, C$_{1-6}$alkyl, C$_{1-6}$fluoroalkyl, C(O)C$_{1-6}$alkyl, C(O)C$_{1-6}$fluoroalkyl, C$_{3-10}$cycloalkyl, heterocycloalkyl, C$_{6-10}$aryl, C$_{1-6}$alkyleneC$_{6-10}$aryl, C$_{1-6}$alkyleneC$_{3-10}$cycloalkyl and C$_{1-6}$alkyleneheterocycloalkyl, and R$^{44}$ is unsubstituted or substituted with one to three substituents selected from halo, CN, C$_{1-6}$alkyl, C$_{1-6}$fluoroalkyl, OH, SH, OC$_{1-6}$alkyl, OC$_{1-6}$fluoroalkyl, SC$_{1-6}$alkyl, SC$_{1-6}$fluoroalkyl, NH$_2$, NHC$_{1-6}$alkyl, N(C$_{1-6}$alkyl)(C$_{1-6}$alkyl), C(O)C$_{1-6}$alkyl, C(O)C$_{1-6}$fluoroalkyl, C(O)OH, C(O)OC$_{1-6}$alkyl, C(O)NH$_2$, C(O)NHC$_{1-6}$alkyl, C(O)N(C$_{1-6}$alkyl)(C$_{1-6}$alkyl), SO$_2$C$_{1-6}$alkyl, S(O)C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneOH, C$_{1-6}$alkyleneOC$_{1-6}$alkyl, C$_{1-6}$alkyleneSH, C$_{1-6}$alkyleneSC$_{1-6}$alkyl, C$_{1-6}$alkyleneNH$_2$, C$_{1-6}$alkyleneNHC$_{1-6}$alkyl and C$_{1-6}$alkyleneN(C$_{1-6}$alkyl)(C$_{1-6}$alkyl); R$^{45}$ and R$^{46}$ are each independently selected from H, C$_{1-6}$alkyl, C$_{1-6}$fluoroalkyl, C(O)C$_{1-6}$alkyl, C(O)C$_{1-6}$fluoroalkyl, C$_{3-10}$cycloalkyl, heterocycloalkyl, C$_{6-10}$aryl, C$_{1-6}$alkyleneC$_{6-10}$aryl, C$_{1-6}$alkyleneC$_{3-10}$cycloalkyl and C$_{1-6}$alkyleneheterocycloalkyl and each of R$^{45}$ and R$^{46}$ is unsubstituted or substituted with one to three substituents independently selected from halo, CN, C$_{1-6}$alkyl, C$_{1-6}$fluoroalkyl, OH, SH, OC$_{1-6}$alkyl, OC$_{1-6}$fluoroalkyl, SC$_{1-6}$alkyl, SC$_{1-6}$fluoroalkyl, NH$_2$, NHC$_{1-6}$alkyl, N(C$_{1-6}$alkyl)(C$_{1-6}$alkyl), C(O)C$_{1-6}$alkyl, C(O)C$_{1-6}$fluoroalkyl, C(O)OH, C(O)OC$_{1-6}$alkyl, C(O)NH$_2$, C(O)NHC$_{1-6}$alkyl, C(O)N(C$_{1-6}$alkyl)(C$_{1-6}$alkyl), SO$_2$C$_{1-6}$alkyl, S(O)C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneOH, C$_{1-6}$alkyleneOC$_{1-6}$alkyl, C$_{1-6}$alkyleneSH, C$_{1-6}$alkyleneSC$_{1-6}$alkyl, C$_{1-6}$alkyleneNH$_2$, C$_{1-6}$alkyleneNHC$_{1-6}$alkyl and C$_{1-6}$alkyleneN(C$_{1-6}$alkyl)(C$_{1-6}$alkyl), or R$^{45}$ and R$^{46}$ together with the nitrogen atom to which they are attached form a 3-6 membered heterocycle that is unsubstituted or substituted with one to three substituents selected from halo, CN, C$_{1-6}$alkyl, C$_{1-6}$fluoroalkyl, OH, SH, OC$_{1-6}$alkyl, OC$_{1-6}$fluoroalkyl, SC$_{1-6}$alkyl, SC$_{1-6}$fluoroalkyl, NH$_2$, NHC$_{1-6}$alkyl, N(C$_{1-6}$alkyl)(C$_{1-6}$alkyl), C(O)C$_{1-6}$alkyl, C(O)C$_{1-6}$fluoroalkyl, C(O)OH, C(O)OC$_{1-6}$alkyl, C(O)NH$_2$, C(O)NHC$_{1-6}$alkyl, C(O)N(C$_{1-6}$alkyl)(C$_{1-6}$alkyl), SO$_2$C$_{1-6}$alkyl, S(O)C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneOH, C$_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN($C_{1-6}$alkyl)($C_{1-6}$alkyl).

In some embodiments, $R^{35}$ is selected from phenyl, pyrimidinyl, pyridinyl, dihydropyridine, pyrrolyl and dihydropyrrolyl, each of which is substituted with one substituent selected from halo, CN, $C_{1-6}$alkyl, $C_{1-6}$fluoroalkyl, =O, =S, OR$^{40}$, SR$^{40}$, SO$_2$R$^{40}$, NR$^{41}$R$^{42}$, R$^{43}$, $C_{1-6}$alkyleneR$^{43}$, $C_{1-6}$alkenyleneR$^{43}$, OC$_{1-6}$alkyleneR$^{43}$, SC$_{1-6}$alkyleneR$^{43}$, $C_{1-6}$alkyleneNR$^{41}$R$^{42}$, $C_{1-6}$alkyleneOR$^{40}$, $C_{1-6}$alkyleneSR$^{40}$, OC$_{1-6}$alkyleneNR$^{41}$R$^{42}$, SC$_{1-6}$alkyleneNR$^{41}$R$^{42}$, OC$_{1-6}$alkyleneOR$^{40}$, SC$_{1-6}$alkyleneOR$^{40}$, OC$_{1-6}$alkyleneSR$^{40}$, SC$_{1-6}$alkyleneSR$^{40}$, C(O)OR$^{40}$, C(S)OR$^{40}$, C(S)NR$^{41}$R$^{42}$ and C(O)NR$^{41}$R$^{42}$ In some embodiments, $R^{35}$ is substituted with one substituent selected from $C_{1-6}$alkyl, $C_{1-6}$fluoroalkyl, OR$^{40}$, NR$^{41}$R$^{42}$, R$^{43}$, $C_{1-6}$alkyleneR$^{43}$, OC$_{1-6}$alkyleneR$^{43}$, $C_{1-6}$alkyleneNR$^{41}$R$^{42}$, $C_{1-6}$alkyleneOR$^{40}$, OC$_{1-6}$alkyleneNR$^{41}$R$^{42}$, OC$_{1-6}$alkyleneOR$^{40}$, C(O)OR$^{40}$ and C(O)NR$^{41}$R$^{42}$.

In some embodiments, $R^{35}$ is substituted with R$^{43}$ or $C_{1-6}$alkyleneR$^{43}$ wherein R$^{43}$ is selected from $C_{5-6}$cycloalkyl, $C_{5-6}$heterocycloalkyl, $C_{5-6}$heteroaryl and phenyl, and R$^{43}$ is unsubstituted or substituted with one to three substituents independently selected from halo and $C_{1-6}$alkyl. In some embodiments, R$^{43}$ is $C_{1-6}$-heterocycloalkyl. In some embodiments, R$^{43}$ is selected from piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. In some embodiments, R$^{43}$ is morpholinyl, optionally substituted with one or two Me.

In some embodiments, $R^{35}$ is selected from:

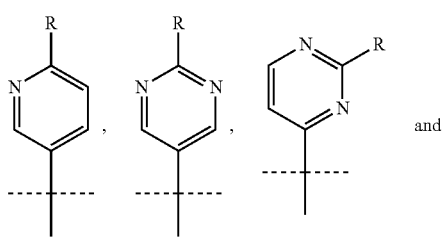

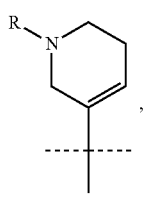

wherein R is the substituent.

In some embodiments, the compound of Formula Ib is selected from:

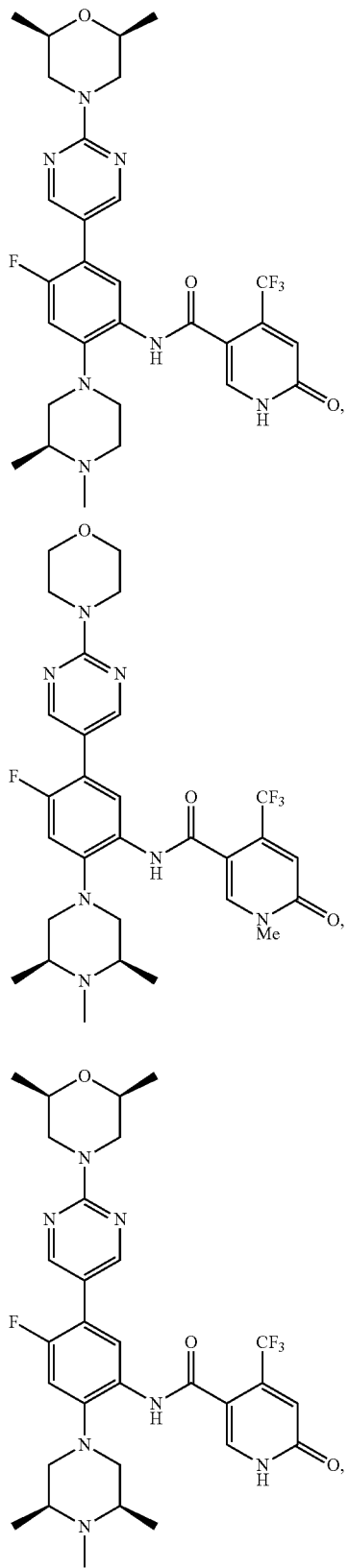

111
-continued
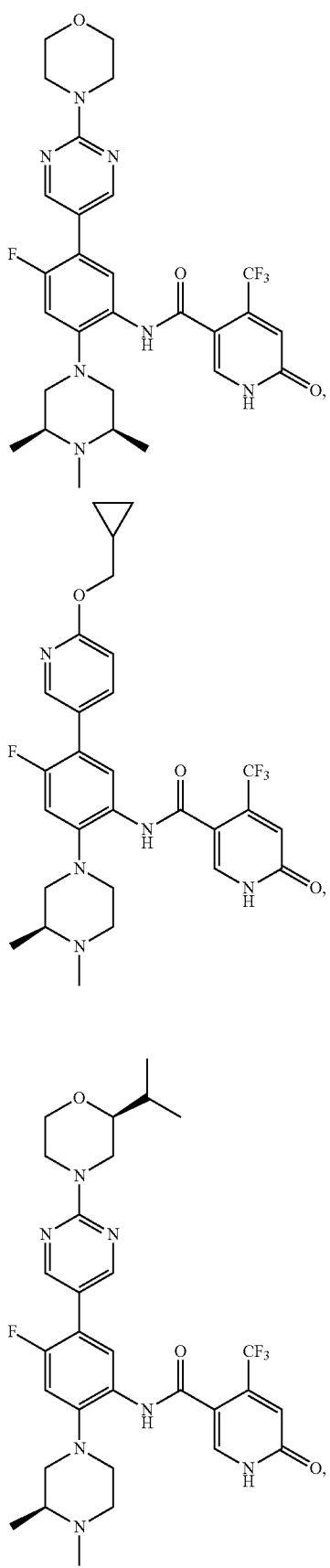
112
-continued
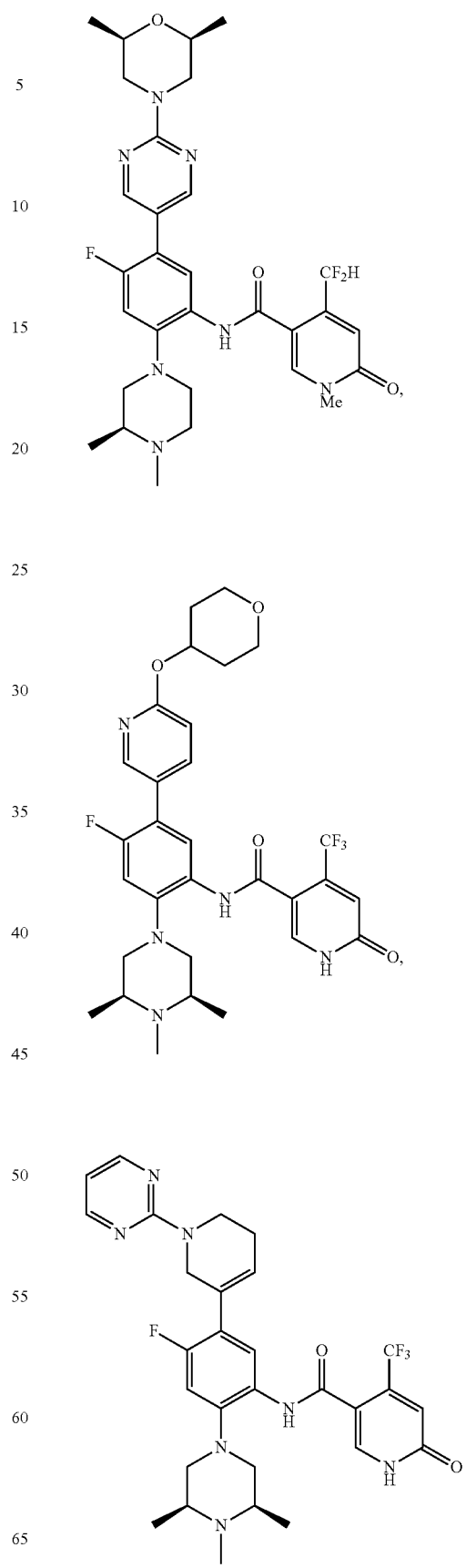

113
-continued
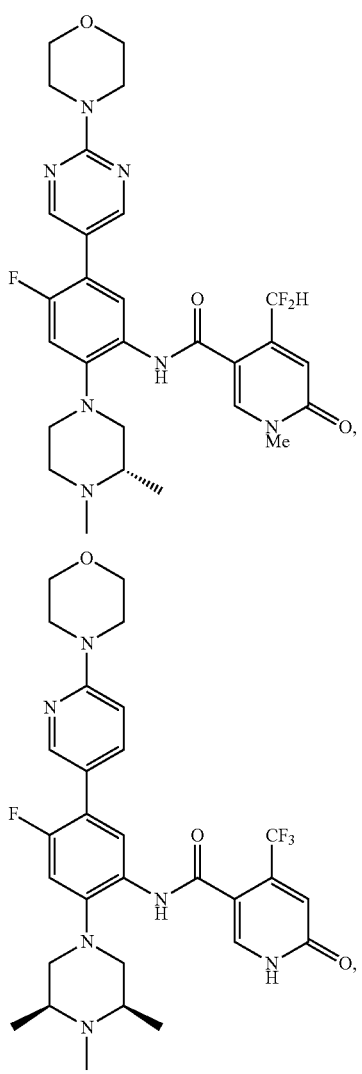
114
-continued
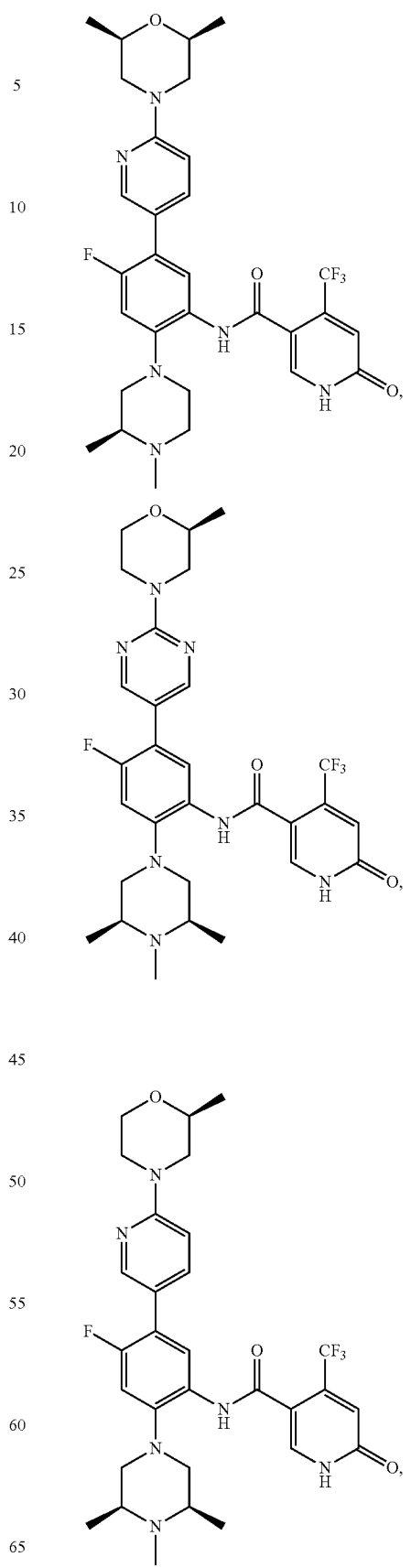

115
-continued
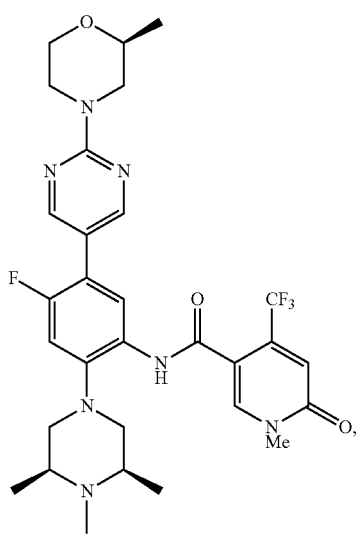
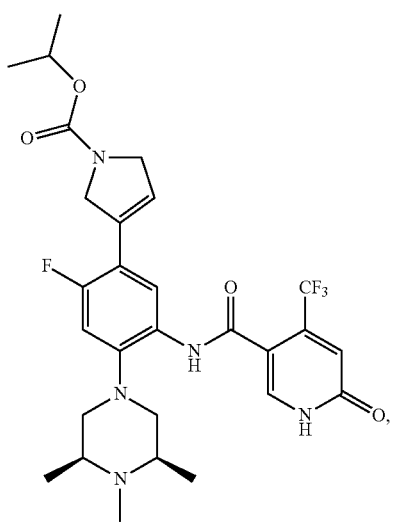
116
-continued
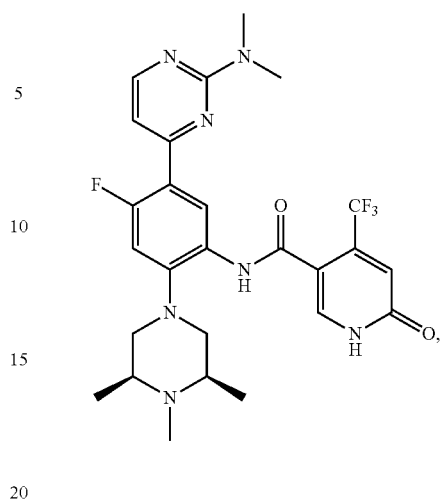
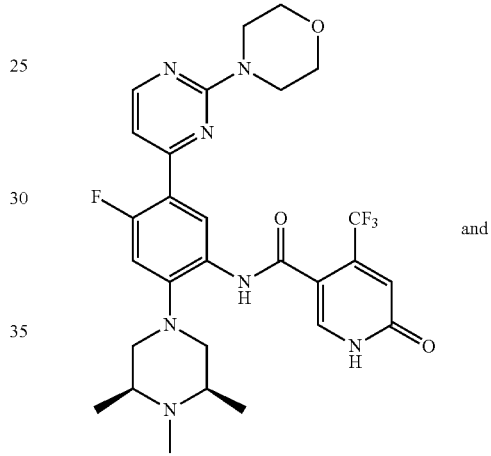
and
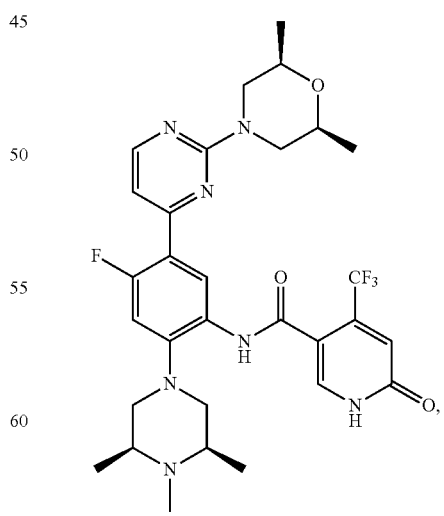
or a pharmaceutically acceptable salt and/or solvate thereof.

The present application also include a compound of Formula (Ic) or a pharmaceutically acceptable salt and/or solvate thereof:

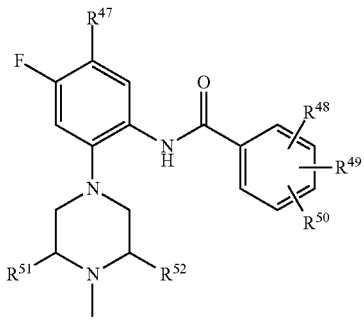

(Ic)

wherein:

$R^{47}$ is selected from phenyl, $C_{5-6}$heteroaryl and $C_{5-6}$heterocycloalkyl, and $R^{47}$ is substituted with one substituents selected from halo, CN, $C_{1-6}$alkyl, $C_{1-6}$fluoroalkyl, =O, =S, $OR^{53}$, $SR^{53}$, $SO_2R^{53}$, $NR^{54}R^{55}$, $R^{56}$, $C_{1-6}$alkylene$R^{56}$, $C_{1-6}$alkenylene$R^{56}$, $OC_{1-6}$alkylene$R^{56}$, $SC_{1-6}$alkylene$R^{56}$, $C_{1-6}$alkylene$NR^{54}R^{55}$, $C_{1-6}$alkyleneOR$^{53}$, $C_{1-6}$ alkyleneSR$^{53}$, $OC_{1-6}$alkylene$NR^{54}R^{55}$, $SC_{1-6}$alkylene$NR^{54}R^{55}$, $OC_{1-6}$alkyleneOR$^{53}$, $SC_{1-6}$alkyleneOR$^{53}$, $OC_{1-6}$alkyleneSR$^{53}$, $SC_{1-6}$alkyleneSR$^{53}$, $C(O)OR^{53}$, $C(S)OR^{53}$, $C(S)NR^{54}R^{55}$ and $C(O)NR^{54}R^{55}$;

$R^{48}$, $R^{49}$ and $R^{50}$ are independently selected from H, F, $CF_3$ and $CF_2H$, provided that at least one of $R^{48}$, $R^{49}$ and $R^{50}$ is not H;

$R^{51}$ and $R^{52}$ are independently selected from H and $CH_3$ $R^{53}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, heteroaryl, $C_{1-6}$alkylene$C_{3-10}$cycloalkyl, $C_{1-6}$alkylene$C_{6-10}$aryl, $C_{1-6}$alkyleneheteroaryl and $C_{1-6}$alkyleneheterocycloalkyl, and is unsubstituted or substituted with one to three substituents selected from;

$R^{54}$ and $R^{55}$ are each independently selected from H, $C_{1-10}$alkyl, $C_{1-10}$fluoroalkyl, $C(O)C_{1-6}$alkyl, $C(O)C_{1-6}$fluoroalkyl, $C(O)C_{6-10}$aryl, $C(O)C_{3-10}$cycloalkyl, $C(O)$heteroaryl, $C(O)$heterocycloalkyl, $C(O)OC_{1-6}$alkyl, $C(O)OC_{1-6}$fluoroalkyl, $C(O)OC_{6-10}$aryl, $C(O)OC_{3-10}$cycloalkyl, $C(O)O$heteroaryl, $C(O)O$heterocycloalkyl, $C(O)NHC_{1-6}$alkyl, $C(O)NHC_{1-6}$fluoroalkyl, $C(O)NHC_{6-10}$aryl, $C(O)NHC_{3-10}$cycloalkyl, $C(O)NH$heteroaryl, $C(O)NH$heterocycloalkyl, $SO_2C_{1-6}$alkyl, $SO_2C_{1-6}$fluoroalkyl, $SO_2C_{6-10}$aryl, $SO_2C_{3-10}$cycloalkyl, $SO_2$heteroaryl, $SO_2$heterocycloalkyl, $C_{3-10}$cycloalkyl, heterocycloalkyl, heteroaryl, $C_{6-10}$aryl, $C_{1-6}$alkylene$C_{3-10}$cycloalkyl, $C_{1-6}$alkylene$C_{6-10}$aryl, $C_{1-6}$alkyleneheteroaryl and $C_{1-6}$alkyleneheterocycloalkyl, and each of $R^{54}$ and $R^{55}$ are independently unsubstituted or substituted with one to three substituents selected from halo, CN, $OR^{57}$, $SR^{57}$, $NR^{58}R^{58}$, $C_{1-6}$alkyl, $C(O)R^{57}$, $C(O)OR^{57}$, $C(O)NR^{58}R^{59}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkylene$C_{1-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkylene$R^{57}$, $C_{1-6}$alkyleneOR$^{57}$, $C_{1-6}$alkyleneSR$^{57}$ and $C_{1-6}$alkyleneNR$^{58}R^{59}$, or $R^{54}$ and $R^{55}$ together with the nitrogen atom to which they are attached form a 3-6 membered heterocycle that is unsubstituted or substituted with one to three substituents independently selected from halo, CN, $OR^{57}$, $SR^{57}$, $NR^{58}R^{58}$, $C_{1-6}$alkyl, $C(O)R^{57}$, $C(O)OR^{57}$, $C(O)NR^{58}R^{59}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkylene$C_{1-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkylene$R^{57}$, $C_{1-6}$alkyleneOR$^{57}$, $C_{1-6}$alkyleneSR$^{57}$ and $C_{1-6}$alkyleneNR$^{58}R^{59}$;

$R^{56}$ is selected from $C(O)C_{1-6}$alkyl, $C(O)C_{1-6}$fluoroalkyl, $C(O)C_{6-10}$aryl, $C(O)C_{3-10}$cycloalkyl, $C(O)$heteroaryl, $C(O)$heterocycloalkyl, $C_{3-10}$cycloalkyl, heterocycloalkyl, heteroaryl and $C_{6-10}$aryl, and $R^{56}$ is unsubstituted or substituted with one to three substituents independently selected halo, CN, $OR^{57}$, $SR^{57}$, $NR^{58}R^{58}$, $C_{1-6}$alkyl, $C(O)R^{57}$, $C(O)OR^{57}$, $C(O)NR^{58}R^{59}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkylene$R^{57}$, $C_{1-6}$alkyleneOR$^{57}$, $C_{1-6}$alkyleneSR$^{57}$ and $C_{1-6}$alkyleneNR$^{51}R^{59}$;

$R^{57}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, $C_{1-6}$alkylene$C_{6-10}$aryl, $C_{1-6}$alkylene$C_{3-10}$cycloalkyl and $C_{1-6}$alkyleneheterocycloalkyl, and $R^{57}$ is unsubstituted or substituted with one to three substituents selected from halo, CN, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl$)(C_{1-6}$alkyl$)$, $C(O)C_{1-6}$alkyl, $C(O)C_{1-6}$fluoroalkyl, $C(O)OH$, $C(O)OC_{1-6}$alkyl, $C(O)NH_2$, $C(O)NHC_{1-6}$alkyl, $C(O)N(C_{1-6}$alkyl$)(C_{1-6}$alkyl$)$, $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN$(C_{1-6}$alkyl$)(C_{1-6}$alkyl$)$; $R^{58}$ and $R^{59}$ are each independently selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, $C_{1-6}$alkylene$C_{6-10}$aryl, $C_{1-6}$alkylene$C_{3-10}$cycloalkyl and $C_{1-6}$alkyleneheterocycloalkyl and each of $R^{58}$ and $R^{59}$ is unsubstituted or substituted with one to three substituents independently selected from halo, CN, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl$)(C_{1-6}$ alkyl$)$, $C(O)C_{1-6}$alkyl, $C(O)C_{1-6}$fluoroalkyl, $C(O)OH$, $C(O)OC_{1-6}$alkyl, $C(O)NH_2$, $C(O)NHC_{1-6}$alkyl, $C(O)N(C_{1-6}$alkyl$)(C_{1-6}$alkyl$)$, $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$ alkyleneNHC$_{1-6}$alkyl and $C_{1-6}$alkyleneN$(C_{1-6}$alkyl$)(C_{1-6}$alkyl$)$, or $R^{58}$ and $R^{59}$ together with the nitrogen atom to which they are attached form a 3-6 membered heterocycle that is unsubstituted or substituted with one to three substituents selected from halo, CN, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl)$(C_{1-6}$alkyl), $C(O)C_{1-6}$alkyl, $C(O)C_{1-6}$fluoroalkyl, $C(O)OH$, $C(O)OC_{1-6}$alkyl, $C(O)NH_2$, $C(O)NHC_{1-6}$alkyl, $C(O)N(C_{1-6}$alkyl)$(C_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl).

In some embodiments, $R^{47}$ is selected from phenyl, pyrimidinyl, pyridinyl, dihydropyridine, pyrrolyl and dihydropyrrolyl, each of which is substituted with one substituent selected from halo, CN, $C_{1-6}$alkyl, $C_{1-6}$fluoroalkyl, =O, =S, $OR^{53}$, $SR^{53}$, $SO_2R^{53}$, $NR^{54}R^{55}$, $R^{56}$, $C_{1-6}$alkylene$R^{56}$, $C_{1-6}$alkenylene$R^{56}$, $OC_{1-6}$alkylene$R^{56}$, $SC_{1-6}$alkylene$R^{56}$, $C_{1-6}$alkyleneNR$^{54}R^{55}$, $C_{1-6}$alkyleneOR$^{53}$, $C_{1-6}$alkyleneSR$^{53}$, $OC_{1-6}$alkyleneNR$^{54}R^{55}$, $SC_{1-6}$alkyleneNR$^{45}R^{55}$, $OC_{1-6}$alkyleneOR$^3$, $SC_{1-6}$alkyleneOR$^3$, $OC_{1-6}$alkyleneSR$^{53}$, $SC_{1-6}$alkyleneSR$^{53}$, $C(O)OR^{53}$, $C(S)OR^{53}$, $C(S)NR^{54}R^{55}$ and $C(O)NR^{54}R^{55}$.

In some embodiments, $R^{47}$ is substituted with one substituent selected from $C_{1-6}$alkyl, $C_{1-6}$fluoroalkyl, $OR^{53}$, $NR^{54}R^{55}$, $R^{56}$, $C_{1-6}$alkylene$R^{56}$, $OC_{1-6}$alkylene$R^{56}$, $C_{1-6}$alkyleneNR$^{54}R^{55}$, $C_{1-6}$alkyleneOR$^{53}$, $OC_{1-6}$alkyleneNR$^{54}R^{55}$, $OC_{1-6}$alkyleneOR$^{53}$, $C(O)OR^{53}$ and $C(O)NR^{54}R^{55}$.

In some embodiments, $R^{47}$ is substituted with $R^{56}$ or $C_{1-6}$alkylene$R^{56}$ wherein $R^{56}$ is selected from $C_{5-6}$cycloalkyl, $C_{5-6}$heterocycloalkyl, $C_{5-6}$heteroaryl and phenyl, and $R^{56}$ is unsubstituted or substituted with one to three substituents independently selected from halo and $C_{1-6}$alkyl. In some embodiments, $R^{56}$ is $C_{1-6}$-heterocycloalkyl. In some embodiments, $R^{56}$ is selected from piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. In some embodiments, $R^{56}$ is morpholinyl, optionally substituted with one or two Me.

In some embodiments, $R^{47}$ is selected from:

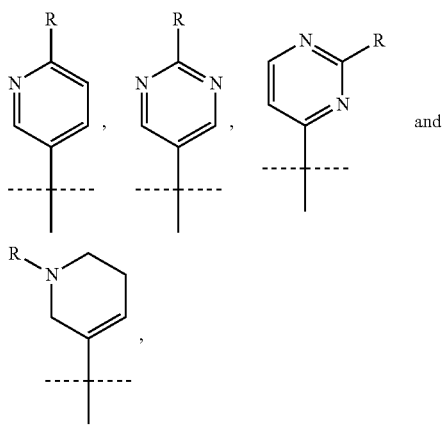

wherein R is the substituent.

In some embodiments, $R^{48}$, $R^{49}$ and $R^{50}$ are located on the phenyl ring as follows:

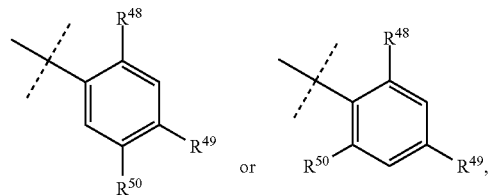

wherein $R^{48}$ is selected from $CF_3$ and $CF_2H$ and $R^{49}$ and $R^{50}$ are independently selected from H and F. In some embodiments, both $R^{49}$ and $R^{50}$ are F. In some embodiments, $R^{49}$ is F and $R^{50}$ is H.

In some embodiments the compound of Formula Ic is selected from:

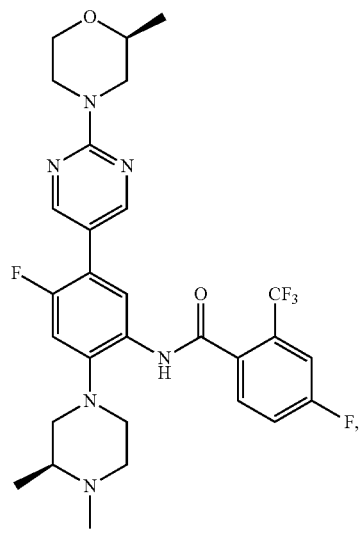

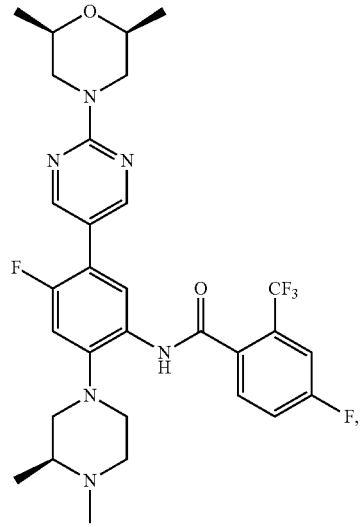

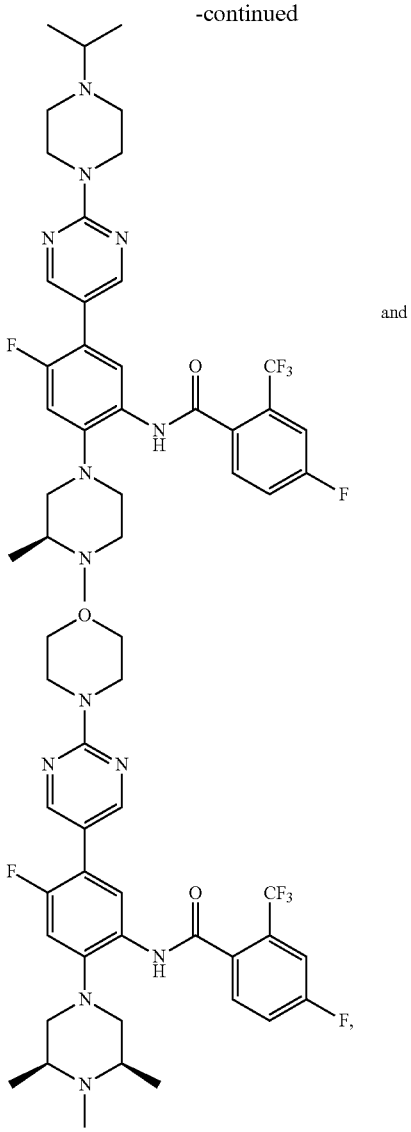

or a pharmaceutically acceptable salt and/or solvate thereof.

The compounds of the present application are suitably formulated in a conventional manner into compositions using one or more carriers. Accordingly, the present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier. In embodiments of the application the pharmaceutical compositions are used in the treatment of nay of the diseases, disorders or conditions described herein.

The compounds of the application are administered to a subject in a variety of forms depending on the selected route of administration, as will be understood by those skilled in the art. For example, a compound of the application is administered by oral, inhalation, parenteral, buccal, sublingual, nasal, rectal, vaginal, patch, pump, topical or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Parenteral administration includes systemic delivery routes other than the gastrointestinal (GI) tract, and includes, for example intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

In some embodiments, a compound of the application is orally administered, for example, with an inert diluent or with an assimilable edible carrier, or it is enclosed in hard or soft shell gelatin capsules, or it is compressed into tablets, or it is incorporated directly with the food of the diet. In some embodiments, the compound is incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). In embodiments, the tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for example as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of phospholipids, such as cholesterol, stearylamine or phosphatidylcholines. For oral administration in a capsule form, useful carriers or diluents include lactose and dried corn starch.

In some embodiments, liquid preparations for oral administration take the form of, for example, solutions, syrups or suspensions, or they are suitably presented as a dry product for constitution with water or other suitable vehicle before use. When aqueous suspensions and/or emulsions are administered orally, the compound of the application is suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of the application and use the lyophilizates obtained, for example, for the preparation of products for injection.

In some embodiments, a compound of the application is administered parenterally. For example, solutions of a compound of the application are prepared in water suitably mixed with a surfactant such as hydroxypropylcellulose. In some embodiments, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared, and the pH's of the solutions are suitably adjusted and buffered. For intravenous use, the total concentration of solutes should be controlled to render the preparation isotonic. For ocular administration, ointments or droppable liquids are delivered, for example, by ocular delivery systems known to the art such as applicators or eye droppers. In some embodiment, such compositions include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

In some embodiments, a compound of the application is formulated for parenteral administration by injection, including using conventional catheterization techniques or infusion. Formulations for injection are, for example, presented in unit dosage form, e.g., in ampoules or in multi-dose containers, with an added preservative. In some embodiments, the compositions take such forms as sterile suspensions, solutions or emulsions in oily or aqueous vehicles, and contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

In some embodiments, compositions for nasal administration are conveniently formulated as aerosols, drops, gels and powders. For intranasal administration or administration by inhalation, the compounds of the application are conveniently delivered in the form of a solution, dry powder formulation or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. In some embodiments, the pressurized container or nebulizer contains a solution or suspension of the active compound. Capsules and cartridges (made, for example, from gelatin) for use in an inhaler or insufflator are, for example, formulated containing a powder mix of a compound of the application and a suitable powder base such as lactose or starch. The aerosol dosage forms can also take the form of a pump-atomizer.

Compositions suitable for buccal or sublingual administration include tablets, lozenges, and pastilles, wherein a compound of the application is formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: *Remington's Pharmaceutical Sciences,* 16th Ed., Mack Publishing, Easton, PA, 1980, pp. 1530-1533 for further discussion of suppository dosage forms.

In some embodiments a compound of the application is coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, in some embodiments, a compound of the application is coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

A compound of the application including pharmaceutically acceptable salts and/or solvates thereof is suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient, and from about 1 wt % to about 99.95 wt % or about 30 wt % to about 99.90 wt % of a pharmaceutically acceptable carrier, all percentages by weight being based on the total composition.

A compound of the application is either used alone or in combination with other known agents useful for treating diseases, disorders or conditions that are mediated or treatable by inhibition of binding between WDR5 protein and its binding partners, and those that are treatable with a WDR5 inhibitor, such as the compounds disclosed herein. When used in combination with other agents useful in treating diseases, disorders or conditions mediated or treatable by inhibition of binding between WDR5 protein and its binding partners, it is an embodiment that a compound of the application is administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In an embodiment, a compound of the present application is administered with another therapeutic agent simultaneously or sequentially in separate unit dosage forms or together in a single unit dosage form. Accordingly, the present application provides a single unit dosage form comprising one or more compounds of the application, an additional therapeutic agent, and a pharmaceutically acceptable carrier.

The dosage of a compound of the application varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. In some embodiments, a compound of the application is administered initially in a suitable dosage that is adjusted as required, depending on the clinical response. Dosages will generally be selected to maintain a serum level of the compound of the application from about 0.01 µg/cc to about 1000 µg/cc, or about 0.1 µg/cc to about 100 µg/cc. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg will be administered. For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. For administration in suppository form, a representative amount is from about 0.1 mg/kg to about 10 mg/kg or about 0.1 mg/kg to about 1 mg/kg. In an embodiment of the application, compositions are formulated for oral administration and the one or more compounds are suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. In embodiments of the application the one or more compounds of the application are administered in a single daily, weekly or monthly dose or the total daily dose is divided into two, three or four daily doses.

In the above, the term "a compound" also includes embodiments wherein one or more compounds are referenced.

(c) Methods and Uses of the Application (i) Therapeutic Methods and Uses

The compounds of the application have been shown to be inhibitors of the binding of WDR5 to MLL1.

Accordingly, the present application includes a method for inhibition of binding of WDR5 to its binding partners in a cell, either in a biological sample or in a patient, comprising administering an effective amount of one or more compounds of the application to the cell. The application also includes a use of one or more compounds of the application for inhibition of binding of WDR5 to its binding partners in a cell as well as a use of one or more compounds of the application for the preparation of a medicament for inhibition of binding of WDR5 to its binding partners in a cell. The application further includes one or more compounds of the application for use to inhibit binding of WDR5 to its binding partners in a cell.

It is an embodiment of the present application, in all aspects, that the binding partner for WDR5 is MLL1, or a portion thereof. In some embodiments, the binding partner for WDR5 is the WDR5 interacting (WIN) motif, consisting of amino acid residues 3762-3773 next to the SET domain in the MLL1 protein, [J. Biol. Chem., 2008, 283(47):32158-32161; J. Biol. Chem., 2008,283(50):35258-35264].

As the compounds of the application have been shown to be capable of inhibiting the binding of WDR5 to its binding partners, the compounds of the application are useful for treating diseases, disorders or conditions mediated or treatable by inhibition of binding between WDR5 protein and its binding partners. Therefore the compounds of the present application are useful as medicaments. Accordingly, the present application includes a compound of the application for use as a medicament.

The present application also includes a method of treating a disease, disorder or condition that is mediated or treatable by inhibition of binding between WDR5 protein and its binding partners comprising administering a therapeutically effective amount of one or more compounds of the application to a subject in need thereof.

The present application also includes a use of one or more compounds of the application for treating a disease, disorder or condition mediated or treatable by inhibition of binding between WDR5 protein and its binding partners as well as a use of one or more compounds of the application for the preparation of a medicament for treating of a disease, disorder or condition mediated or treatable by inhibition of binding between WDR5 protein and its binding partners. The application further includes one or more compounds of the application for use in treating a disease, disorder or condition mediated or treatable by inhibition of binding between WDR5 protein and its binding partners.

In an embodiment, the disease, disorder or condition mediated or treatable by inhibition of binding between WDR5 protein and its binding partners is a neoplastic disorder. Accordingly, the present application also includes a method of treating a neoplastic disorder comprising administering a therapeutically effective amount of one or more compounds of the application to a subject in need thereof. The present application also includes a use of one or more compounds of the application for treatment of a neoplastic disorder as well as a use of one or more compounds of the application for the preparation of a medicament for treatment of a neoplastic disorder. The application further includes one or more compounds of the application for use in treating a neoplastic disorder. In an embodiment, the treatment is in an amount effective to ameliorate at least one symptom of the neoplastic disorder, for example, reduced cell proliferation or reduced tumor mass, among others, in a subject in need of such treatment.

In another embodiment of the present application, the disease, disorder or condition mediated or treatable by inhibition of binding between WDR5 protein and its binding partners is cancer. Accordingly, the present application also includes a method of treating cancer comprising administering a therapeutically effective amount of one or more compounds of the application to a subject in need thereof. The present application also includes a use of one or more compounds of the application for treatment of cancer as well as a use of one or more compounds of the application for the preparation of a medicament for treatment of cancer. The application further includes one or more compounds of the application for use in treating cancer. In an embodiment, the compound is administered for the prevention of cancer in a subject such as a mammal having a predisposition for cancer.

In an embodiment, the cancer is selected from, but not limited to: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated in accordance with the methods described herein.

In an embodiment, the cancer is selected from solid cancer and leukemias. In another embodiment, the cancer is selected from leukaemia, lymphoma, non-Hodgkin's lymphoma, Burkitt lymphoma, MLL-fusion lymphoma, primary effusion leukemia and multiple myeloma. In a further embodiment of the present application, the cancer is selected from leukemia, melanoma, lung cancer, bladder cancer, colon cancer, brain cancer, ovarian cancer, breast cancer, prostate cancer, neuroblastoma and kidney cancer. In a further embodiment, the cancer is selected from leukemia, bladder cancer, prostate cancer, brain cancer and neuroblastoma. In a further embodiment, the cancer is selected from bladder cancer, acute myeloid leukemia (AML), gliomas, glioblastomas and MYCN-amplified neuroblastoma.

In an embodiment, the disease, disorder or condition mediated or treatable by inhibition of binding between WDR5 protein and its binding partners is a disease, disorder or condition associated with an uncontrolled and/or abnormal cellular activity affected directly or indirectly by a binding of WDR5 to its binding partners. In another embodiment, the uncontrolled and/or abnormal cellular activity that is affected directly or indirectly by binding of WDR5 to its binding partners is proliferative activity in a cell. Accordingly, the application also includes a method of inhibiting proliferative activity in a cell, comprising administering an effective amount of one or more compounds of the application to the cell. The present application also includes a use of one or more compounds of the application for inhibition of proliferative activity in a cell as well as a use of one or more compounds of the application for the preparation of a medicament for inhibition of proliferative activity in a cell. The application further includes one or more compounds of the application for use in inhibiting proliferative activity in a cell.

The present application also includes a method of inhibiting uncontrolled and/or abnormal cellular activities mediated directly or indirectly by binding of WDR5 to its binding partners in a cell, either in a biological sample or in a subject, comprising administering an effective amount of one or more compounds of the application to the cell. The application also includes a use of one or more compounds of the application for inhibition of uncontrolled and/or abnormal cellular activities mediated directly or indirectly by binding of WDR5 to its binding partners in a cell as well as a use of one or more compounds of the application for the preparation of a medicament for inhibition of uncontrolled and/or abnormal cellular activities mediated directly or indirectly binding of WDR5 to its binding partners in a cell. The application further includes one or more compounds of the application for use in inhibiting uncontrolled and/or abnormal cellular activities mediated directly or indirectly by binding of WDR5 to its binding partners in a cell.

In further embodiments, the present application also includes a method of treating a disease, disorder or condition that is mediated or treatable by inhibition of binding between WDR5 protein and its binding partners comprising administering a therapeutically effective amount of one or more compounds of the application in combination with another known agent useful for treatment of a disease, disorder or condition mediated or treatable by inhibition of binding between WDR5 protein and its binding partners to a subject in need thereof. The present application also includes a use of one or more compounds of the application in combination with a known agent useful for treatment of a disease, disorder or condition mediated or treatable by inhibition of binding between WDR5 protein and its binding partners, for treatment of a disease, disorder or condition mediated or treatable by inhibition of binding between WDR5 protein and its binding partners.

In a further embodiment, the disease, disorder or condition mediated or treatable by inhibition of binding between WDR5 protein and its binding partners is cancer and the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors, immunotherapy, hormonal therapy and anti-angiogenic therapies.

(d) Methods of Preparing the Compounds of the Application

Scheme 1 illustrates one embodiment of a route to compounds of the application in which Suzuki or related coupling is performed on compounds (A) to afford intermediates (B). Subsequent coupling of (B) with a carboxylic acid or appropriate or acid halide provides compounds of the application.

Scheme 1

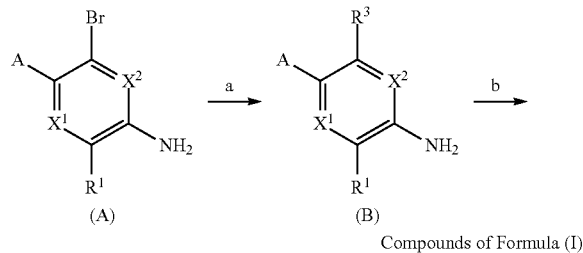

Compounds of Formula (I)

a) R³B(OH)₂ or boronate ester, Pd(Amphos)Cl₂, K₃PO₄, dioxane/H₂O, μwave, 110° C.; b) R²C(O)OH, coupling agent or R²C(O)X, wherein X is a halide, amine.

In an alternate embodiment, compounds of Formula (I) are prepared by first coupling the carboxylic acid or acyl halides with aniline (A) followed by Suzuki or related coupling (Scheme 2).

Scheme 2

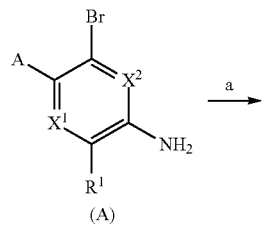

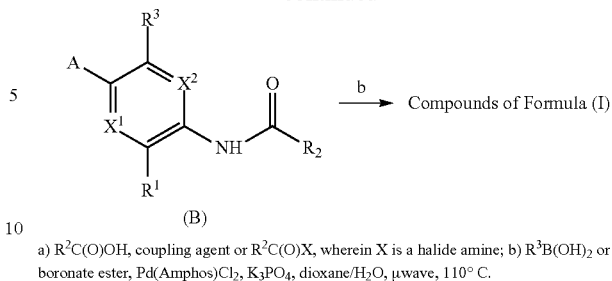

a) R²C(O)OH, coupling agent or R²C(O)X, wherein X is a halide amine; b) R³B(OH)₂ or boronate ester, Pd(Amphos)Cl₂, K₃PO₄, dioxane/H₂O, μwave, 110° C.

In some embodiments of the application, compounds of Formula (I) are prepared from the nitroaryl or nitroheteroaryl compounds D (Q=Cl or Br; Z=F or Br). Nucleophilic aromatic substitution with, for example, various piperazines or amines provide intermediate E. In some embodiments, reduction of E under reductive conditions by various means, including catalytic hydrogenation and dissolving metal reductions both in their various forms [see House, H. O., Modern Synthetic Reactions, Second Edition, W. A. Benjamin, Inc., Menlo Park, California, publication (1972)]affords compounds F. Coupling of F with boronic acids or esters, for example under the Suzuki conditions [*Tetrahedron* 2002, 58: 9633-9695; *Organic Letters* 2006, 8(9), 1787-1789] affords intermediate G. Related coupling reactions for the conversion of F to G or H to Formula I as described in Scheme 3 include the Heck (olefin) [*J. Am. Chem. Soc.* 1974 96(4):1133-1136]; Stille (organostannane) [*Synthesis* 1992 803-815]; Sonogashira (acetylene) [*Tetrahedron Lett* 1975 16(50):4467-4470] and Negishi (organozinc) [*Aldrichimica Acta.*, 2005,38(3):71-78] coupling reactions.

Scheme 3

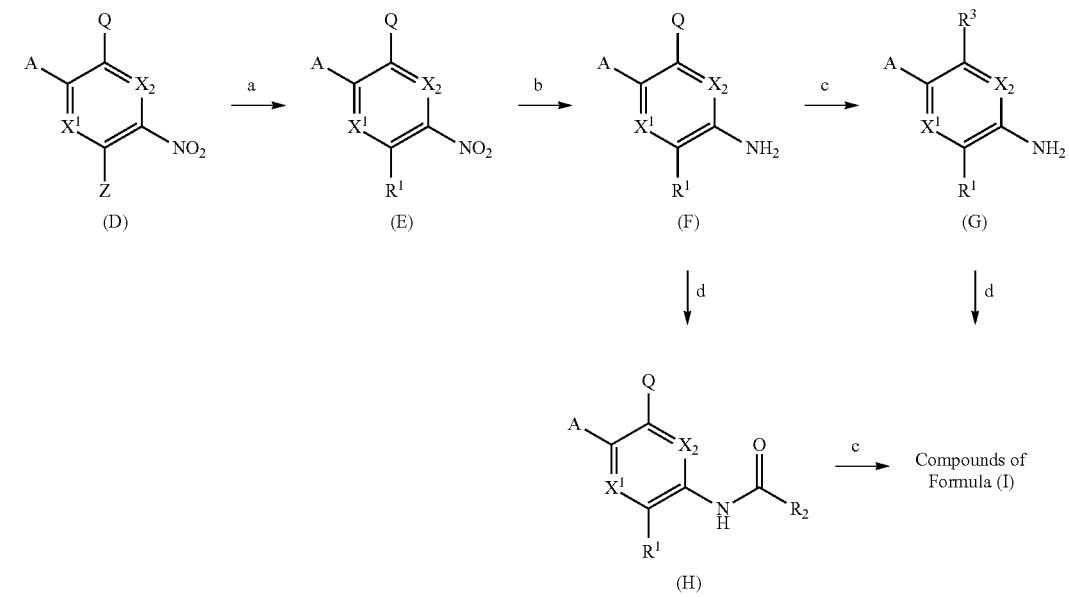

a) piperazine or amine, base; b) Zn or Fe, alcohol solvent; c) R³B(OH)₂ or boronate ester, Pd(Amphos)Cl₂, K₃PO₄, dioxane/H₂O, μwave, 110° C.; d) R²C(O)OH, coupling agent or R²C(O)X, where X is a halide, amine.

In some embodiments compounds of Formula (I) are prepared by treatment of compounds of Formula F with amines (e.g. piperazines) to afford the intermediate K (Scheme 4). In some embodiments, bromination of K with N-bromosuccinmide provides the versatile intermediate L which is transformed into Formula (I) according to Scheme 3.

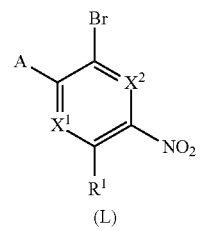

(L)

a) piperazine or amines, base; b) N-bromosuccinimide.

In some embodiments of the application, compounds of Formula (I) wherein $R^2$=2-chloro-4-trifluoromethylpyridine or trifluoromethylpyrimidone are prepared as shown in Scheme 5. Therefore, in some embodiments, acylation of compounds G (prepared, for example, via Scheme 3) with the 6-chloro-4-(trifluoromethyl)nicotinic acid chloride (generated in situ from the corresponding acid and $SOCl_2$] gives amide M. Hydrolysis of M with sodium acetate in acetic acid under microwave conditions provides pyridone N. Coupling of N with boronic acids or esters, for example, under the Suzuki conditions deliver compounds of Formula (Ib). Alternatively, in some embodiments, the Suzuki coupled intermediate O is acylated with the 6-chloro-4-(trifluoromethyl)nicotinic acid chloride to give Id which is subsequently hydrolysed to compounds Ib (Scheme 5).

Scheme 4

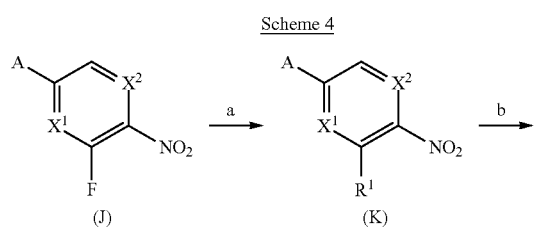

Scheme 5

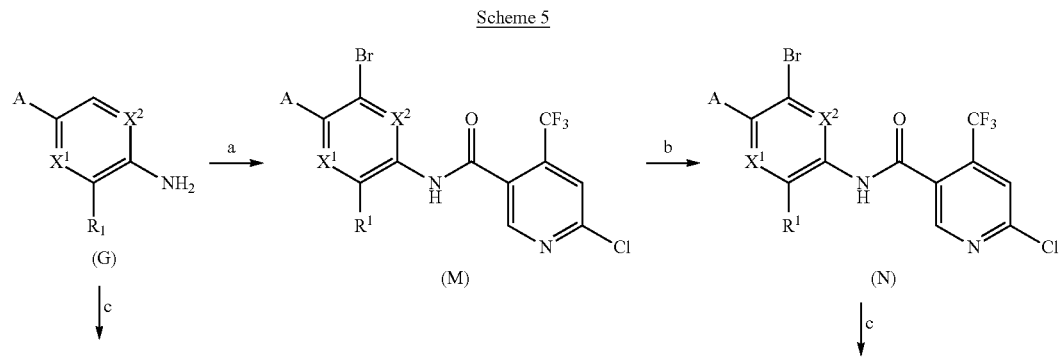

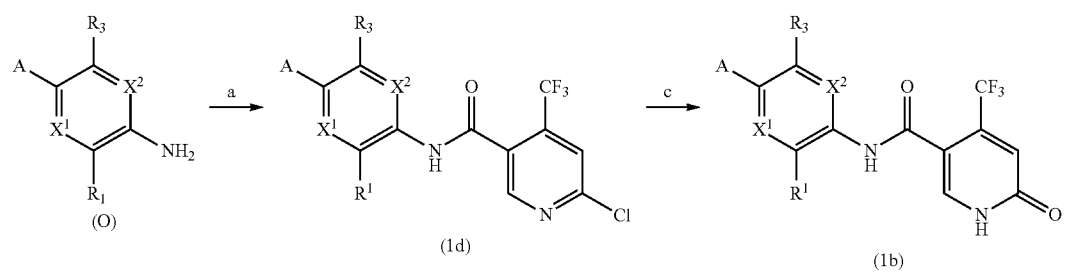

a) $R^2C(O)OH$, coupling agent or $R^2C(O)X$, X is a halide amine; b) NaOAc, AcOH, μwave, 160° C.; c) $R^3B(OH)_2$ or boronate ester, Pd(Amphos)Cl$_2$, K$_3$PO$_4$, dioxane/H$_2$O, μwave, 110° C..

Scheme 6 illustrates another embodiment for the preparation of compounds of Formula (Ib), wherein $R^2$ in the compounds of Formula I is trifluoromethyl pyrimidone. In some embodiments, acylation of aniline G with the 6-methoxy-4-(trifluoromethyl)nicotinic acid [$R^a$=Me] or 4-(trifluoromethyl)-6-(2-(trimethylsilyl)ethoxy)nicotinic acid [$R^a$=—CH$_2$CH$_2$TMS] (generated from the corresponding acid and the alcohol, for example, as in Scheme 7) gives amide Q. In some embodiments, the amide Q is then transformed into the boronate ester R. In some embodiments, the Suzuki coupling of R to a variety halides affords intermediates S. In some embodiments, subsequent deprotection of S provides compounds of the present application (Formula Ib). In some embodiments, compounds of Formula Ib are prepared via Suzuki coupling to Q followed by deprotection (Scheme 6).

Throughout the synthetic methods and processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994). Tech-

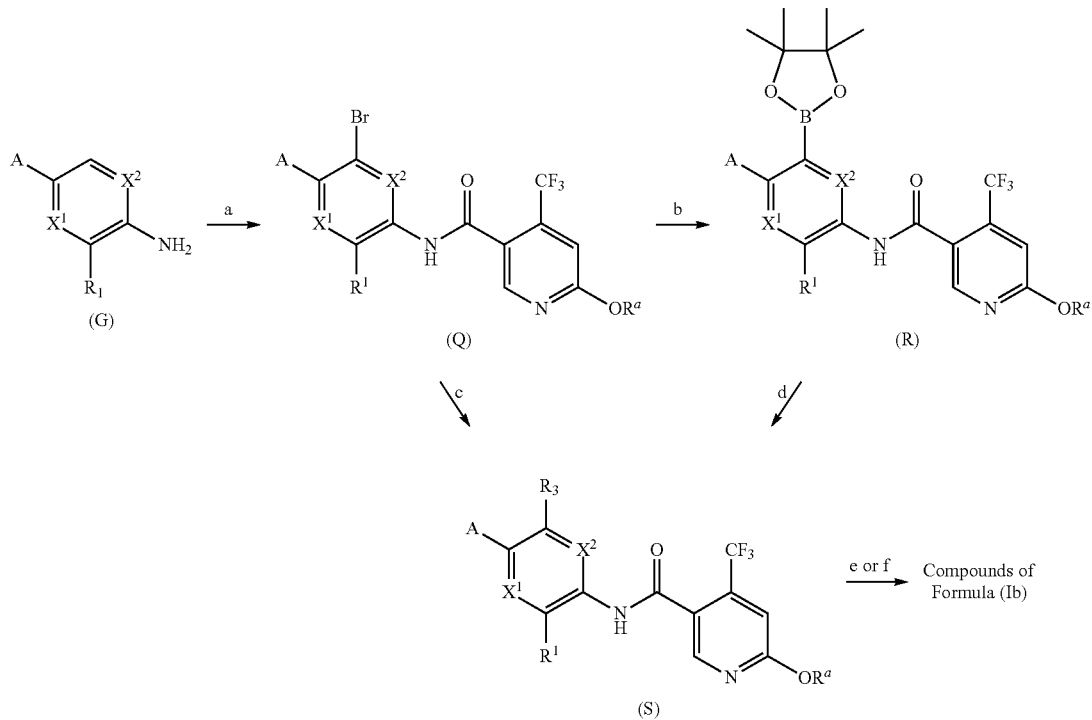

Scheme 6 a) $R^2C(O)OH$, coupling agent; b) bipinacolatodiboron, Pd (dppf)$_2$Cl$_2$, NaOAc, dioxane, 110° C.; c) $R^3B(OH)_2$ or boronate ester, Pd(Amphos)Cl$_2$, K$_3$PO$_4$, dioxane/H$_2$O, μwave, 110° C.; d) $R^3$-halide or triflate, Pd(Amphos)Cl$_2$, K$_3$PO$_4$, dioxane/H$_2$O, μwave, 110° C.; e) HCl or TFA; f) CsF or TBAF.

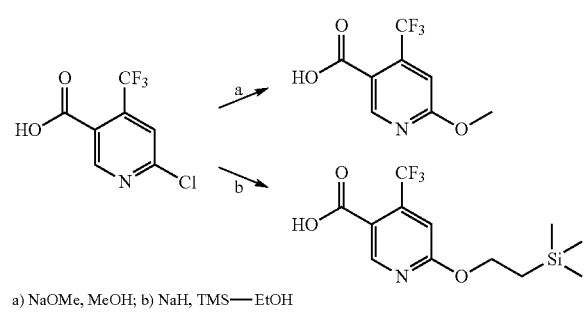

Scheme 7 a) NaOMe, MeOH; b) NaH, TMS—EtOH niques for purification of intermediates and final products include, for example, straight and reversed phase chromatography on column or rotating plate, recrystallisation, distillation and liquid-liquid or solid-liquid extraction, which will be readily understood by one skilled in the art.

EXAMPLES

The following non-limiting examples are illustrative of the present application:

(a) General Methods

Exemplary compounds of the application were synthesized using the methods described herein, or other methods, which are known in the art. Unless otherwise noted, reagents and solvents were obtained from commercial suppliers (e.g. Aldrich, Enamine, Combiblock, Bepharm, and J&W PharmLab).

The compounds and/or intermediates were characterized by high performance liquid chromatography (HPLC) using a Waters ACQUITY UPLC system with a SQ (single quadrupole) MS and a photodiode array (PDA) detector (Milford, MA). The analytical columns were reversed phase Acqity UPLC BEH C18 (2.1×50 mm, 1.7 µm). A gradient elution was used (flow 0.4 mL/min), typically starting with mobile phase 0.1% formic acid in water (solvent A) and 0.1% formic acid in acetonitrile (solvent B). A gradient starting at 95% solvent A going to 5% in 1.8 min., holding for 0.5 min., going back to 95% in 0.5 min. and equilibrating the column for 0.5 min. Compounds were detected by ultraviolet light (UV) absorption at either 220 or 254 nm. HPLC solvents were from Burdick and Jackson (Muskegan, MI), or Fisher Scientific (Pittsburgh, PA).

In some instances, purity was assessed by thin layer chromatography (TLC) using glass or plastic backed silica gel plates, such as, for example, Baker-Flex Silica Gel IB2-F flexible sheets. TLC results were readily detected visually under ultraviolet light, or by employing well-known iodine vapor and other various staining techniques.

The compounds and/or intermediates were characterized by LCMS. General conditions were as follows. Low and High resolution Mass spectra were acquired on LC/MS systems using electrospray ionization methods from a range of instruments of the following configurations: Low resolution—Waters ACQUITY UPLC system with a SQ (single quadrupole) MS; Waters ACQUITY UPLC H-Class system with a 3100 (single quadrupole) MS. High resolution—Waters ACQUITY UPLC II system equipped with a Synapt Xevo QTof and Waters ACQUITY UPLC II system equipped with a Synapt G2S QTof mass spectrometer with an atmospheric pressure ionization source. [M+H] refers to the protonated molecular ion of the chemical species.

Nuclear magnetic resonance (NMR) analysis was performed on a Bruker 500 MHz NMR spectrometer using ICON-NMR, under TopSpin program control. Spectra were measured at 298K, unless indicated otherwise and were referenced relative to the solvent chemical shift.

(b) Synthesis of Compounds

The following compounds were prepared using one or more of the synthetic methods disclosed in Schemes 1 to 7:

Example 1: Synthesis of 4-fluoro-N-[4-fluoro-2-(4-methylpiperazin-1-yl)-5-[3-(morpholin-4-ylmethyl)phenyl]phenyl]-3,5-dimethylbenzamide

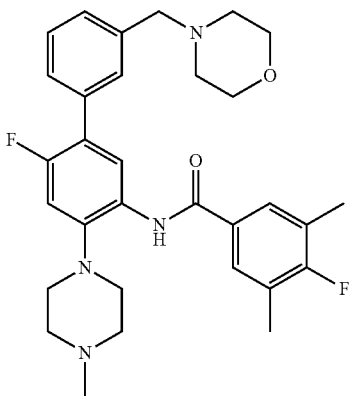 [SMILES: Cc1cc(C(=O)Nc2cc(-c3cccc(CN4CCOCC4)c3)c(F)cc2N2CCN(C)CC2)cc(C)c1F]

Step 1: Synthesis of 1-(4-chloro-5-fluoro-2-nitrophenyl)-4-methylpiperazine

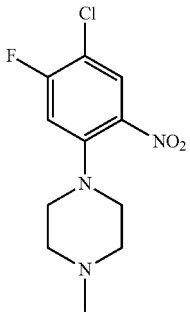 [SMILES: CN1CCN(c2cc(F)c(Cl)cc2[N+](=O)[O-])CC1]

A microwave vial was charged with 1-bromo-4-chloro-5-fluoro-2-nitrobenzene (0.50 g, 1.965 mmol), palladium(II) acetate (0.044 g, 0.197 mmol), 4,5-bis(diphenylphosphino)-9,9-dimethylxanthene, 97% (0.114 g, 0.197 mmol) and cesium carbonate (0.960 g, 2.95 mmol). The vial was capped, evacuated and backfilled with nitrogen. Toluene (volume: 25 ml) and 1-methylpiperazine (0.196 ml, 1.769 mmol) were added via syringe and the reaction vial was evacuated and backfilled with nitrogen. The reaction was warmed to 40° C. overnight. LCMS indicated about 75% conversion and ~3:1 for the desired product versus the nucleophilic aromatic substitution (SNAr) displacement of the ArF. The reaction was transferred to a round bottom flask with DCM and then concentrated onto celite. Purification by flash chromatography [0-10% MeOH/DCM+1% NH$_4$OH; 100 g column] afforded an inseparable mixture of the two products 1-(4-chloro-5-fluoro-2-nitrophenyl)-4-methylpiperazine (0.428 g, 1.095 mmol, 55.7% yield) and 1-(5-bromo-2-chloro-4-nitrophenyl)-4-methylpiperazine. The mixture was used directly in the next step. LCMS [M+H]$^+$ 274 g/mol.

Step 2: Synthesis of 4-((2'-fluoro-4'-(4-methylpiperazin-1-yl)-5'-nitro-[1,1'-biphenyl]-3-yl)methyl)morpholine

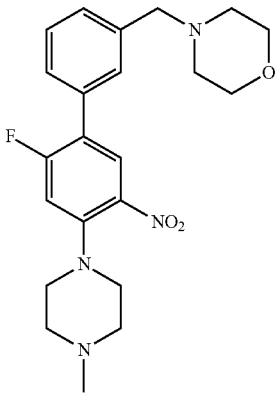

A vial was charged with the mixture obtained in 1-(4-chloro-5-fluoro-2-nitrophenyl)-4-methylpiperazine,3-(4-morpholinomethyl)phenylboronic acid pinacol ester (0.498 g, 1.642 mmol), XPhos Pd G2 (0.017 g, 0.022 mmol), and XPhos (10.44 mg, 0.022 mmol). The vial was sealed with a cap and septum, evacuated and backfilled with nitrogen. 1,4-Dioxane (volume: 10 ml) and a 2M aq. solution of sodium carbonate monohydrate (ACS) (2.74 ml, 5.47 mmol) were added via syringe and the vial was evacuated and backfilled with nitrogen an additional time. The reaction was heated at 90° C. in an aluminum block overnight. LCMS indicated complete consumption of the starting material(s). The peak at 1.56 minutes ionized for the mass of the target product. The reaction was cooled to room temperature and concentrated onto celite. Purification by silica gel flash chromatography [1-10% MeOH/DCM+1% NH$_4$OH;] afforded the desired 4-((2'-fluoro-4'-(4-methylpiperazin-1-yl)-5'-nitro-[1,1'-biphenyl]-3-yl)methyl)morpholine (0.248 g, 0.598 mmol, 54.7% yield) as a yellow oil. LCMS [M+H]$^+$ 415 g/mol.

Step 3: Synthesis of 6-fluoro-4-(4-methylpiperazin-1-yl)-3'-(morpholinomethyl)-[1,1'-biphenyl]-3-amine

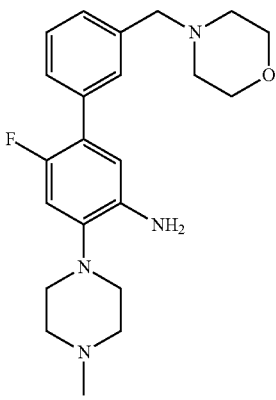

A solution of 4-((2'-fluoro-4'-(4-methylpiperazin-1-yl)-5'-nitro-[1,1'-biphenyl]-3-yl)methyl)morpholine (0.248 g, 0.598 mmol) in MeOH (volume: 10 ml) was hydrogenated in the presence of platinum(IV) oxide (0.014 g, 0.060 mmol) at 1 atm (balloon) of H$_2$ (g). After 18 h (overnight), LCMS indicated formation of two polar peaks, both indicating the desired product by MS. Celite was added to the reaction and the mixture was filtered eluting with MeOH. The filtrate was then concentrated onto celite and purified by silica gel flash chromatography [1-10% MeOH/DCM+1% NH$_4$OH] to afford 6-fluoro-4-(4-methylpiperazin-1-yl)-3'-(morpholinomethyl)-[1,1'-biphenyl]-3-amine (0.130 g, 0.338 mmol, 56.5% yield) as a blue foam that was >90% the desired product by NMR and LCMS. LCMS [M+H]$^+$ 385 g/mol.

Step 4: Synthesis of 4-fluoro-N-[4-fluoro-2-(4-methylpiperazin-1-yl)-5-[3-(morpholin-4-ylmethyl)phenyl]phenyl]-3,5-dimethylbenzamide

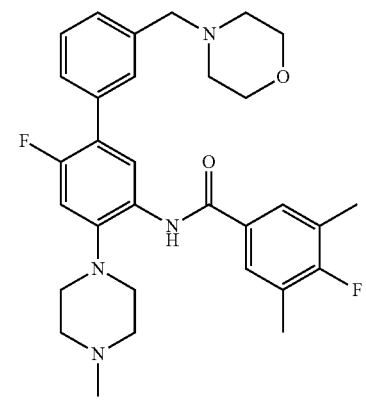 [SMILES: Cc1cc(C(=O)Nc2cc(-c3cccc(CN4CCOCC4)c3)c(F)cc2N2CCN(C)CC2)cc(C)c1F]

4-Fluoro-3,5-dimethylbenzoic acid (0.016 g, 0.094 mmol) was activated with HATU (0.045 g, 0.117 mmol) and DIPEA (0.020 ml, 0.117 mmol) in N,N-dimethylformamide (DMF) (volume: 1 ml, ratio: 1.000) at room temperature. After 5 minutes, the solution was added to a solution of 6-fluoro-4-(4-methylpiperazin-1-yl)-3'-(morpholinomethyl)-[1,1'-biphenyl]-3-amine (0.030 g, 0.078 mmol) in DMF (volume: 1 ml, ratio: 1.000) at room temperature. The reaction was warmed briefly (at 50° C. for 1 h and then at 70° C. for 1 h). The reaction was then stirred at room temperature overnight and then concentrated onto celite. The intermediate was purified by silica gel flash chromatography (reverse phase) on the Biotage [5-95% MeCN/Water; 30 g C18 column] to afford 4-fluoro-N-(6-fluoro-4-(4-methylpiperazin-1-yl)-3'-(morpholinomethyl)-[1,1'-biphenyl]-3-yl)-3,5-dimethylbenzamide (0.009 g, 0.017 mmol, 21.57% yield) as a clear film that was pure by LCMS and NMR. $^1$H NMR (500 MHz, DMSO-d$_6$) δ=9.49 (s, 1H), 8.02 (d, J=8.6 Hz, 1H), 7.73 (d, J=6.8 Hz, 2H), 7.47-7.41 (m, 3H), 7.34 (d, J=6.8 Hz, 1H), 7.19 (d, J=12.2 Hz, 1H), 3.60-3.57 (m, 4H), 3.54 (s, 2H), 2.97-2.93 (m, 4H), 2.38 (br. s, 4H), 2.32 (s, 6H), 2.24 (s, 3H). LCMS [M+H]$^+$ 535 g/mol.

Example 2: Synthesis of 4-fluoro-N-[4-fluoro-2-(4-methylpiperazin-1-yl)-5-[3-(morpholin-4-ylmethyl)phenyl]phenyl]-3,5-dimethylbenzamide

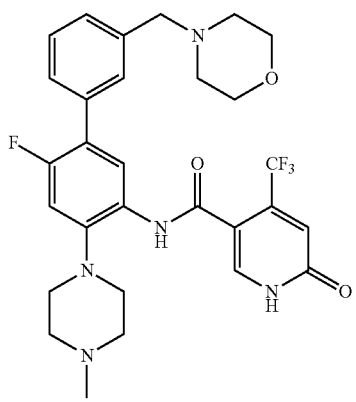

Diethyl chlorophosphate (0.045 ml, 0.312 mmol) was added to a solution of 6-hydroxy-4-(trifluoromethyl)nicotinic acid (0.065 g, 0.312 mmol) in pyridine, anhydrous (0.945 ml, 11.70 mmol) at room temperature under nitrogen. After stirring for 1 h, this solution was added to a vial containing 6-fluoro-4-(4-methylpiperazin-1-yl)-3'-(morpholinomethyl)-[1,1'-biphenyl]-3-amine (step 3 from (a): 0.030 g, 0.078 mmol) under nitrogen and the reaction was heated to 70° C. for 3 hours. The pyridine was removed under reduced pressure and LCMS of the residue (dissolved in DCM, MeCN and MeOH) indicated complete conversion to the desired product. The mixture was loaded onto celite purified by flash chromatography [0.5-10% DCM/MeOH+ 1% NH$_4$OH] to methylpiperazin-1-yl)-3'-(morpholinomethyl)-[1,1'-biphenyl]-3-yl)-6-oxo-4-(trifluoromethyl)-1,6-dihydropyridine-3-carboxamide (0.024 g, 0.042 mmol, 53.6% yield) as a clear film. $^1$H NMR (500 MHz, DMSO-d$_6$) δ=9.53 (s, 1H), 7.94 (s, 1H), 7.76 (d, J=8.4 Hz, 1H), 7.46-7.42 (m, 2H), 7.40-7.38 (m, 1H), 7.32 (d, J=7.3 Hz, 1H), 7.08 (d, J=12.5 Hz, 1H), 6.81 (s, 1H), 3.60-3.57 (m, 4H), 3.53 (s, 2H), 2.93 (br. s., 4H), 2.38 (br. s., 4H), 2.24 (s, 3H); LCMS [M+H]$^+$ 574 g/mol.

In a like manner, the following additional compounds of the application were prepared using schemes 1-7 and the yields disclosed are for the final synthetic step to afford the compounds of the present application:

Example 3: N-(4-fluoro-2-(4-methylpiperazin-1-yl)-5-(2-morpholinopyrimidin-5-yl)phenyl)-6-oxo-4-(trifluoromethyl)-1,6-dihydropyridine-3-carboxamide

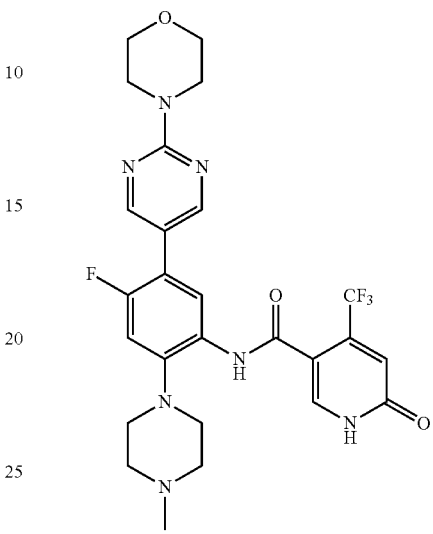

Step 1. N-(5-bromo-4-fluoro-2-(4-methylpiperazin-1-yl)phenyl)-6-oxo-4-(trifluoromethyl)-1,6-dihydropyridine-3-carboxamide

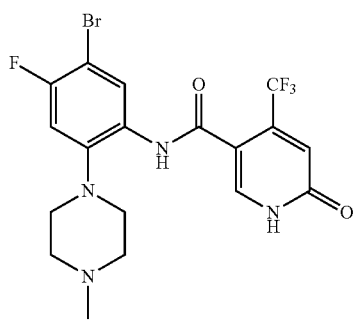 [SMILES: CN1CCN(c2cc(F)c(Br)cc2NC(=O)c2c[nH]c(=O)cc2C(F)(F)F)CC1]

In a 10 ml microwave vial to a suspension of 6-hydroxy-4-(trifluoromethyl)nicotinic acid (719 mg, 3.47 mmol) in anhydrous pyridine (4210 µl, 52.1 mmol) was slowly added diethyl chlorophosphate (514 µl, 3.56 mmol) at RT in an atmosphere of N$_2$. The reaction mixture was stirred at RT for 2 h. The suspension turned into a solution and then into a suspension again. To this mixture, 5-bromo-4-fluoro-2-(4-methylpiperazin-1-yl)aniline (250 mg, 0.868 mmol) was added and the reaction was heated at 70° C. for 3 h. After completion of the reaction, pyridine was removed in vacuo and the residue partitioned between ethyl acetate (3 mL) and saturated sodium bicarbonate solution (3 mL). The suspension was stirred for 10 min. The organic layer was separated, and dried over anhydrous Na$_2$SO$_4$. The solvent was evaporated in vacuo yielding the crude product that was purified by flash column chromatography on silica gel (0-100%, 89% CH$_2$Cl$_2$, 10% MeOH, 1% NH$_4$Ac/CH$_2$Cl$_2$) to afford the desired compound. LCMS C8 [M+1]$^+$=459.4

Step 2: N-(5-bromo-4-fluoro-2-(4-methylpiperazin-1-yl)phenyl)-6-oxo-4-(trifluoromethyl)-1,6-dihydropyridine-3-carboxamide

Example 4: N-(4-fluoro-2-(4-methylpiperazin-1-yl)-5-(6-morpholinopyridin-3-yl)phenyl)-6-oxo-4-(trifluoromethyl)-1,6-dihydropyridine-3-carboxamide

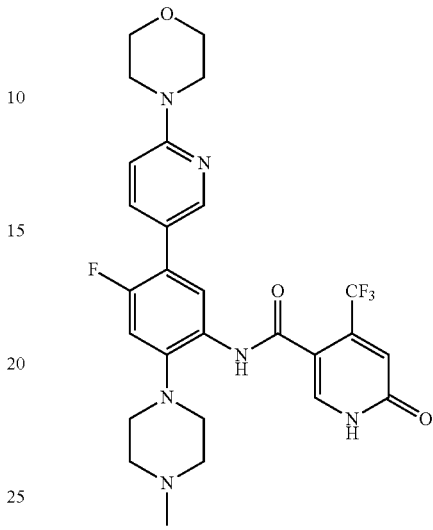

The title compound was prepared in 78% yield similar to the sequence described above for the preparation of Example 3 except using 4-[5-(4,4,5,5-tetramethyl-[1,3,2]dioxaborolan-2-yl)-pyridin-2-yl]-morpholine in place of 2-(4-morpholino)pyrimidine-5-boronic acid pinacol ester to provide the title compound in 78% yield. 1H NMR (500 MHz, MeOD) δ 8.32 (s, 1H), 7.97 (s, 1H), 7.91 (d, J=8.3 Hz, 1H), 7.79 (d, J=8.8 Hz, 1H), 7.09 (d, J=12.0 Hz, 1H), 6.92 (s, 1H), 6.91 (d, J=9.1 Hz, 1H), 3.83-3.80 (m, 4H), 3.55-3.52 (m, 4H), 3.03 (s, 4H), 2.76 (s, 4H), 2.45 (s, 3H); LCMS [M+H]$^+$ 561.6.

Example 5: N-(5-(benzo[d][1,3]dioxol-5-yl)-4-fluoro-2-(4-methylpiperazin-1-yl)phenyl)-6-oxo-4-(trifluoromethyl)-1,6-dihydropyridine-3-carboxamide

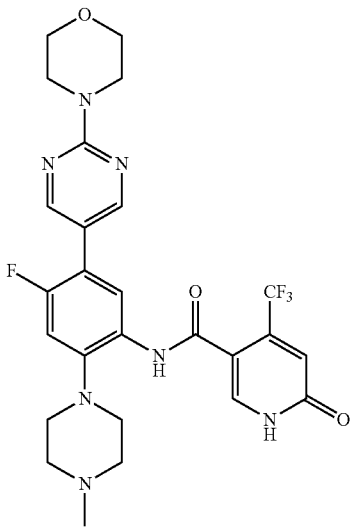

In a 5 mL microwave vial N-(5-bromo-4-fluoro-2-(4-methylpiperazin-1-yl)phenyl)-6-oxo-4-(trifluoromethyl)-1,6-dihydropyridine-3-carboxamide (29.67 mg, 0.062 mmol), 2-(4-morpholino)pyrimidine-5-boronic acid pinacol ester (54.3 mg, 0.187 mmol), sodium carbonate, anhydrous (65.9 mg, 0.622 mmol), XPhos (5.93 mg, 0.012 mmol) and XPhos Pd G2 (9.78 mg, 0.012 mmol) were dissolved in water (1166 μl) and 1,4-dioxane (1943 μl) to give a white suspension. The suspension was stirred for 5 min, degassed, purged with N$_2$, and microwaved for 60 min at 120° C. The solvent was evaporated and 15 ml of CH$_2$Cl$_2$ were added. The suspension was sonicated and extracted from water. The solvent was evaporated in vacuo yielding the crude product that was purified by flash column chromatography on silica gel (0-100%, 89% CH$_2$Cl$_2$, 10% MeOH, 1% NH$_4$Ac/CH$_2$Cl$_2$) to afford the desired compound in 61% yield. $^1$H NMR (500 MHz, MeOD) δ 8.55 (s, 2H), 7.97 (s, 1H), 7.91 (d, J=8.2 Hz, 1H), 7.11 (d, J=12.0 Hz, 1H), 6.92 (s, 1H), 3.86-3.82 (m, 4H), 3.78-3.74 (m, 4H), 3.01 (s, 4H), 2.66 (s, 4H), 2.37 (s, 3H); LCMS [M+H]$^+$ 562.7.

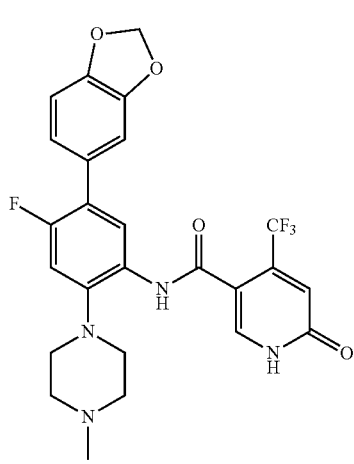

This example was prepared similar to the sequence described above for the preparation of Example 3 using 3,4-methylenedioxyphenylboronic acid in place of 2-(4- morpholino)pyrimidine-5-boronic acid pinacol ester to provide the title compound in 70% yield. ¹H NMR (500 MHz, MeOD) δ 7.96 (s, 1H), 7.88 (d, J=8.3 Hz, 1H), 7.06 (d, J=12.0 Hz, 1H), 7.02 (d, J=7.1 Hz, 2H), 6.92 (s, 1H), 6.90 (d, J=8.6 Hz, 1H), 5.99 (s, 2H), 3.02 (t, J=4.9 Hz, 4H), 2.73 (s, 4H), 2.43 (s, J=13.2 Hz, 3H); LCMS [M+H]⁺ 519.5.

Example 6: (R)—N-(2-(3,4-dimethylpiperazin-1-yl)-4-fluoro-5-(2-morpholinopyrimidin-5-yl)phenyl)-6-oxo-4-(trifluoromethyl)-1,6-dihydropyridine-3-carboxamide

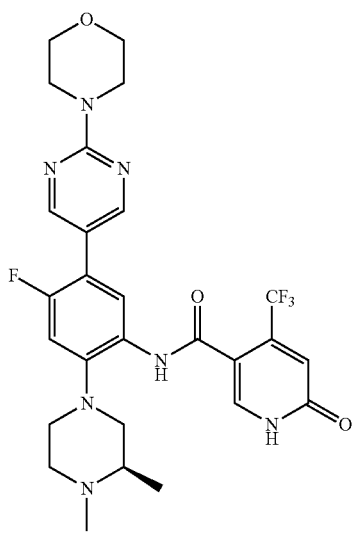

Example 7: (S)—N-(2-(3,4-dimethylpiperazin-1-yl)-4-fluoro-5-(2-morpholinopyrimidin-5-yl)phenyl)-6-oxo-4-(trifluoromethyl)-1,6-dihydropyridine-3-carboxamide

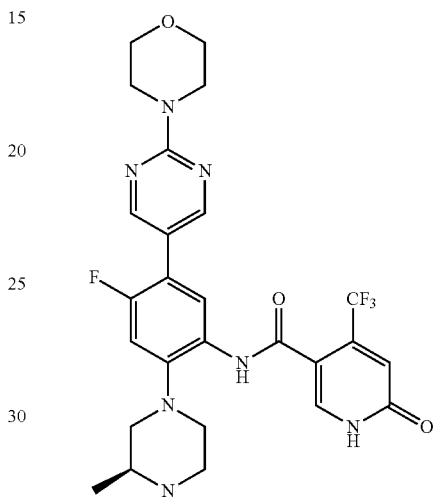

The title compound was prepared using (R)-4-(4-chloro-5-fluoro-2-nitrophenyl)-1,2-dimethylpiperazine and 2-(4-morpholino)pyrimidine-5-boronic acid pinacol ester to give the (R)-4-(5-(4-(3,4-dimethylpiperazin-1-yl)-2-fluoro-5-nitrophenyl)pyrimidin-2-yl)morpholine intermediate, which was reduced to the corresponding amine using standard methods. Diethyl chlorophosphate (4 equiv.) was added to a solution of 6-hydroxy-4-(trifluoromethyl)nicotinic acid (4 equiv.) in pyridine at room temperature under N₂. After stirring for 1 h, the solution of activated acid was added to a vial containing (R)-4-(5-(4-(3,4-dimethylpiperazin-1-yl)-2-fluoro-5-aminophenyl)pyrimidin-2-yl)morpholine (1 equiv.) under nitrogen and the reaction was heated to 70° C. for 3 h. The reaction mixture was concentrated onto celite and subjected to flash chromatography [0.5-10% DCM/MeOH+1% NH₄OH] to afford the title compound in 19% yield. ¹H NMR (500 MHz, DMSO-d₆) δ=9.43 (br. s., 1H), 8.53 (s, 2H), 7.96 (s, 1H), 7.78 (d, J=8.4 Hz, 1H), 7.08 (d, J=12.2 Hz, 1H), 6.70 (s, 1H), 3.77-3.73 (m, 4H), 3.70-3.66 (m, 4H), 3.08-2.95 (m, 2H), 2.88-2.72 (m, 2H), 2.41 (t, J=10.6 Hz, 1H), 2.35-2.30 (m, 1H), 2.25-2.18 (m, 4H), 0.97 (d, J=6.1 Hz, 3H); LCMS [M+H]⁺ 576.

The title compound was prepared using (S)-4-(4-chloro-5-fluoro-2-nitrophenyl)-1,2-dimethylpiperazine and 2-(4-morpholino)pyrimidine-5-boronic acid pinacol ester to give the (S)-4-(5-(4-(3,4-dimethylpiperazin-1-yl)-2-fluoro-5-nitrophenyl)pyrimidin-2-yl)morpholine intermediate, which was reduced to the corresponding amine using standard methods. Diethyl chlorophosphate (4 equiv.) was added to a solution of 6-hydroxy-4-(trifluoromethyl)nicotinic acid (4 equiv.) in pyridine at room temperature under N₂. After stirring for 1 h, the solution of activated acid was added to a vial containing (S)-4-(5-(4-(3,4-dimethylpiperazin-1-yl)-2-fluoro-5-aminophenyl)pyrimidin-2-yl)morpholine (1 equivalent) under nitrogen and the reaction was heated to 70° C. for 3 h. The reaction mixture was concentrated onto celite and subjected to flash chromatography [0.5-10% DCM/MeOH+1% NH₄OH] to afford the title compound in 15% yield. ¹H NMR (500 MHz, DMSO-d₆) δ=9.45 (br. s., 1H), 8.53 (s, 2H), 7.95 (s, 1H), 7.78 (d, J=8.6 Hz, 1H), 7.08 (d, J=12.2 Hz, 1H), 6.72 (br. s., 1H), 3.77-3.74 (m, 4H), 3.69-3.66 (m, 4H), 3.00 (dd, J=11.0, 17.4 Hz, 2H), 2.87-2.72 (m, 2H), 2.44-2.30 (m, 3H), 2.21 (s, 4H), 0.97 (d, J=6.1 Hz, 3H); LCMS [M+H]⁺ 576.4.

Example 8: N-(4-fluoro-5-(2-morpholinopyrimidin-5-yl)-2-((3R,5S)-3,4,5-trimethylpiperazin-1-yl)phenyl)-6-oxo-4-(trifluoromethyl)-1,6-dihydropyridine-3-carboxamide

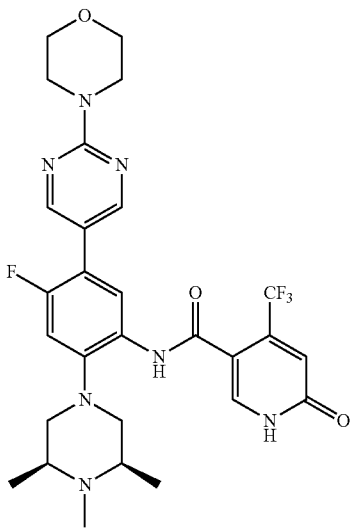

Step 1: (2S,6R)-4-(4-bromo-5-fluoro-2-nitrophenyl)-1,2,6-trimethylpiperazine

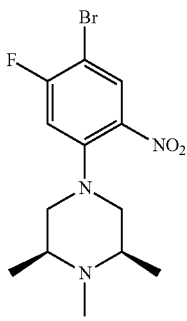 [SMILES: C[C@@H]1CN(c2cc(F)c(Br)cc2[N+](=O)[O-])C[C@H](C)N1C]

To a suspension of K$_2$CO$_3$ (0.456 g, 3.30 mmol) in toluene (10 mL) was added 1-bromo-2,4-difluoro-5-nitrobenzene (1.497 g, 6.29 mmol) and the reaction mixture was heated at 50° C. for 2 min before a solution of (2R,6S)-1,2,6-trimethylpiperazine (0.806 g, 6.29 mmol) in toluene (3 mL) was slowly added over 3 min. The resulting mixture was stirred at 50° C. for 1 h. After adding water (20 mL), it was extracted with EtOAc (30 mL×2) and the combined extracts were concentrated and dried under vacuum to give a dark orange red oil which solidified to a yellow solid (2.166 g, 100% yield). LCMS [M+H]$^+$=348.3.

Step 2: 4-(5-(2-fluoro-5-nitro-4-((3S,5R)-3,4,5-trimethylpiperazin-1-yl)phenyl)pyrimidin-2-yl)morpholine

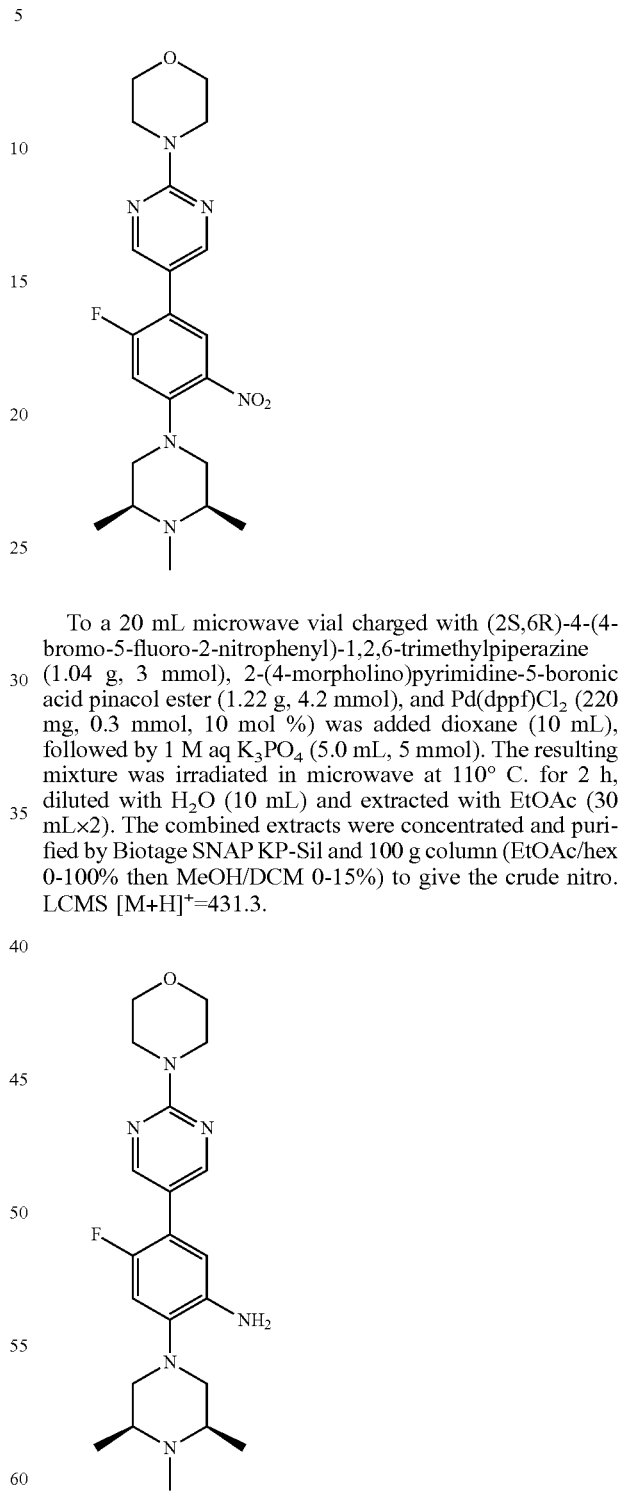

To a 20 mL microwave vial charged with (2S,6R)-4-(4-bromo-5-fluoro-2-nitrophenyl)-1,2,6-trimethylpiperazine (1.04 g, 3 mmol), 2-(4-morpholino)pyrimidine-5-boronic acid pinacol ester (1.22 g, 4.2 mmol), and Pd(dppf)Cl$_2$ (220 mg, 0.3 mmol, 10 mol %) was added dioxane (10 mL), followed by 1 M aq K$_3$PO$_4$ (5.0 mL, 5 mmol). The resulting mixture was irradiated in microwave at 110° C. for 2 h, diluted with H$_2$O (10 mL) and extracted with EtOAc (30 mL×2). The combined extracts were concentrated and purified by Biotage SNAP KP-Sil and 100 g column (EtOAc/hex 0-100% then MeOH/DCM 0-15%) to give the crude nitro. LCMS [M+H]$^+$=431.3.

Step 3: 4-fluoro-5-(2-morpholinopyrimidin-5-yl)-2-((3S,5R)-3,4,5-trimethylpiperazin-1-yl)aniline To a solution of 4-(5-(2-fluoro-5-nitro-4-((3S,5R)-3,4,5-trimethylpiperazin-1-yl)phenyl)pyrimidin-2-yl)morpholine (1.081 g) in 1:1 MeOH/THF (30 mL) at ambient temperature was added a suspension of Raney-Nickel (129 mg, 0.5 mmol) in MeOH (2 mL), followed by hydrazine monohydrate (0.44 mL, 9 mmol) dropwise over 1 min. After addition, the reaction mixture was stirred at rt for 15 min. Additional MeOH (5 mL) and THF (5 mL) was added and the mixture was heated at 60° C. Additional Raney-Nickel (129 mg, 0.5 mmol) in MeOH (2 mL) was added, followed by hydrazine monohydrate (0.44 mL, 9 mmol). The reaction mixture was heated at 60° C. for 30 min. The mixture was allowed to cool, passed through celite and rinsed with MeOH (30 mL×2) and DCM (20 mL). The filtrate was concentrated to about 30 mL of volume. The resulting precipitate was collected by suction filtration to give the title compound as a grey solid. LC-MS [MH]$^+$401.3.

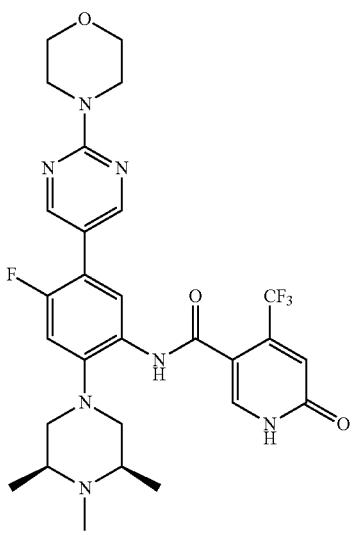

Step 4: N-(4-fluoro-5-(2-morpholinopyrimidin-5-yl)-2-((3R,5S)-3,4,5-trimethylpiperazin-1-yl)phenyl)-6-oxo-4-(trifluoromethyl)-1,6-dihydropyridine-3-carboxamide To a 25 mL round bottomed flask charged with 6-chloro-4-(trifluoromethyl)nicotinic acid (406 mg, 1.8 mmol) was added thionyl chloride (2.18 mL, 30 mmol). The resulting suspension was heated at 80° C. for 1 h. The mixture was evaporated to give a light yellow oil which was treated with DCM (10 mL), 4-fluoro-5-(2-morpholinopyrimidin-5-yl)-2-((3S,5R)-3,4,5-trimethylpiperazin-1-yl)aniline (601 mg, 1.5 mmol) and Et3N (0.63 mL, 4.5 mmol). The resulting mixture was stirred at ambient temperature for 1 h. After quenching with sat. aq NaHCO$_3$ (20 mL), the mixture was extracted with DCM (30 mL×2) and the combined extracts were evaporated and dried to give the chloro intermediate as a light brown foam. The resulting chloropyridine intermediate was taken up in HOAc/H$_2$O (10 mL/3 mL) and NaOAc (246 mg, 3 mmol) was added in a 20 mL microwave vial. The mixture was irradiated in a microwave apparatus at 160° C. for 6 h. LCMS showed completion of the reaction. After removal of HOAc using a Rotovap at (bath heated to 60° C.), the residue was diluted with DCM (30 mL), basified with sat. NaHCO$_3$ (20 mL) and extracted with DCM (50 mL×2). The combined extracts were concentrated and purified by Biotage SNAP KP-Sil using a 50 g column. Fractions showing clean product were combined concentrated and dried to give the title compound as an off-white solid (460 mg, 51% yield). $^1$H NMR (500 MHz, MeOD-d$_4$) δ=8.58-8.55 (m, 2H), 7.98 (s, 1H), 7.91 (d, J=8.2 Hz, 1H), 7.10 (d, J=12.1 Hz, 1H), 6.93 (s, 1H), 3.89-3.82 (m, 4H), 3.81-3.75 (m, 4H), 3.08 (d, J=11.2 Hz, 2H), 2.67-2.52 (m, 4H), 2.39 (s, 3H), 1.18 (d, J=6.1 Hz, 6H); $^{19}$F NMR (471 MHz, METHANOL-d4) δ=−63.80, −120.73; LCMS [MH]$^+$590.32.

Example 9: N-(4-fluoro-2-(4-methylpiperazin-1-yl)-5-(2-(pyrrolidin-1-yl)pyrimidin-5-yl)phenyl)-6-oxo-4-(trifluoromethyl)-1,6-dihydropyridine-3-carboxamide

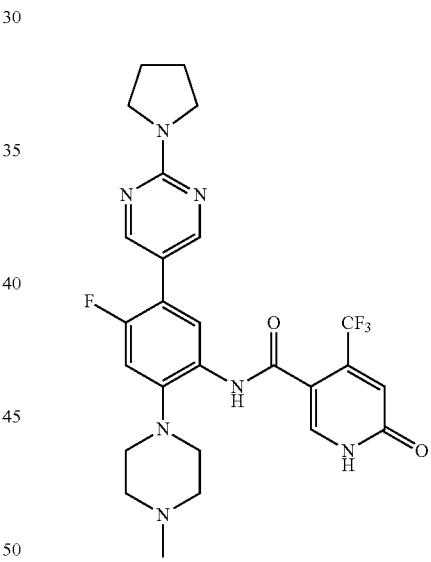

The title compound was prepared similar to the sequence described above for the preparation of Example 3 using 2-(pyrrolidin-1-yl)pyrimidine-5-boronic acid pinacol ester in place of 2-(4-morpholino)pyrimidine-5-boronic acid pinacol ester to give the title compound in 66% yield. $^1$H NMR (500 MHz, MeOD) δ 8.51 (s, 2H), 7.97 (s, 1H), 7.90 (d, J=8.1 Hz, 1H), 7.11 (d, J=12.0 Hz, 1H), 6.92 (s, 1H), 3.60 (t, J=6.7 Hz, 4H), 3.02 (t, J=5.0 Hz, 4H), 2.69 (s, J=2.2 Hz, 4H), 2.40 (s, 3H), 2.05-2.03 (m, 4H); LCMS [M+H]$^+$ 546.38.

Example 10: N-(5-(2-(cyclopropylamino)pyrimidin-5-yl)-4-fluoro-2-(4-methylpiperazin-1-yl)phenyl)-6-oxo-4-(trifluoromethyl)-1,6-dihydropyridine-3-carboxamide

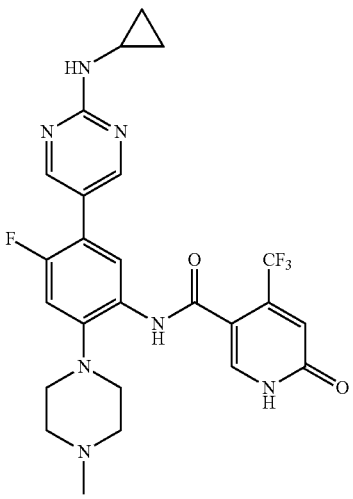 [SMILES: CN1CCN(c2cc(F)c(-c3cnc(NC4CC4)nc3)cc2NC(=O)c2c[nH]c(=O)cc2C(F)(F)F)CC1]

The title compound was prepared in 33% yield similar to the sequence described above for the preparation of Example 3 using 2-cyclopropylaminopyrimidine-5-boronic acid, pinacol ester in place of 2-(4-morpholino)pyrimidine-5-boronic acid pinacol ester. $^1$H NMR (500 MHz, MeOD-d$_4$) δ 8.47 (s, 2H), 8.03 (s, 1H), 7.90 (d, J=8.2 Hz, 1H), 7.18 (d, J=11.7 Hz, 1H), 6.93 (s, 1H), 3.22 (s, 4H), 2.91 (s, 3H), 1.32 (dd, J=9.0, 6.1 Hz, 4H); LCMS [M+H]$^+$ 532.5.

Example 11: N-(5-(2-(cyclohexylamino)pyrimidin-5-yl)-4-fluoro-2-(4-methylpiperazin-1-yl)phenyl)-6-oxo-4-(trifluoromethyl)-1,6-dihydropyridine-3-carboxamide

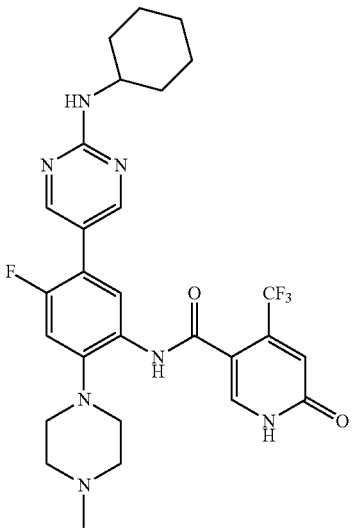

The title compound was prepared in 29% yield similar to the sequence described above for the preparation of Example 3 using 2-(cyclohexylamino)pyrimidine-5-boronic acid, pinacol ester in place of 2-(4-morpholino)pyrimidine-5-boronic acid pinacol ester. $^1$H NMR (500 MHz, MeOD) δ 8.45 (s, 2H), 7.97 (s, 1H), 7.88 (d, J=8.1 Hz, 1H), 7.11 (d, J=11.9 Hz, 1H), 6.92 (s, 1H), 3.86-3.75 (m, 1H), 3.01 (s, 4H), 2.69 (s, 4H), 2.39 (s, 3H), 2.02 (dd, J=11.9, 2.2 Hz, 2H), 1.80 (dd, J=10.5, 2.8 Hz, 2H), 1.68 (d, J=12.9 Hz, 2H), 1.43 (d, J=12.8 Hz, 2H), 1.31 (d, J=13.4 Hz, 2H); LCMS [M+H]$^+$ 574.4.

Example 12: N-(5-(2-ethoxypyrimidin-5-yl)-4-fluoro-2-(4-methylpiperazin-1-yl)phenyl)-6-oxo-4-(trifluoromethyl)-1,6-dihydropyridine-3-carboxamide

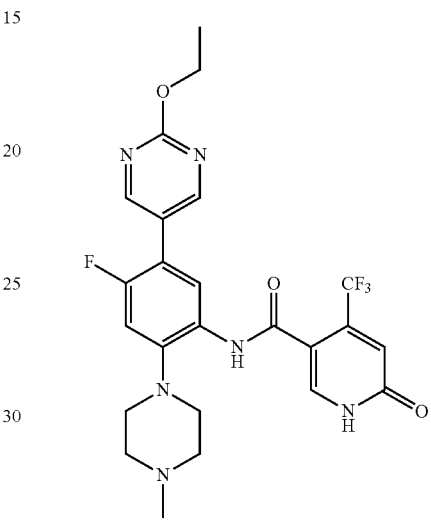

The title compound was prepared in 68% yield similar to the sequence described above for the preparation of Example 3 using 2-ethoxypyrimidine-5-boronic acid in place of 2-(4-morpholino)pyrimidine-5-boronic acid pinacol ester. $^1$H NMR (500 MHz, MeOD) δ 8.74 (s, 2H), 7.98 (s, 1H), 7.95 (d, J=8.2 Hz, 1H), 7.15 (d, J=12.0 Hz, 1H), 6.92 (s, 1H), 4.50 (q, J=7.1 Hz, 2H), 3.03 (s, 4H), 2.68 (s, 4H), 2.39 (s, 3H), 1.44 (t, J=7.1 Hz, 3H); LCMS [M+H]$^+$ 520.9.

Example 13: N-(4-fluoro-2-(4-methylpiperazin-1-yl)-5-(2-methylpyrimidin-5-yl)phenyl)-6-oxo-4-(trifluoromethyl)-1,6-dihydropyridine-3-carboxamide

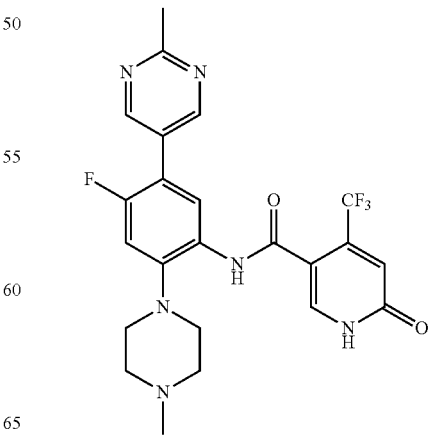

The title compound was prepared in 50% yield similar to the sequence described above for the preparation of Example 3 using 2-methylpyrimidin-5-ylboronic acid pinacol ester in place of 2-(4-morpholino)pyrimidine-5-boronic acid pinacol ester. $^1$H NMR (500 MHz, MeOD-d$_4$) δ 8.89 (s, 2H), 7.98 (d, J=7.9 Hz, 1H), 7.98 (s, 1H), 7.17 (d, J=12.1 Hz, 1H), 6.93 (s, 1H), 3.06 (t, J=4.2 Hz, 4H), 2.75 (s, 3H), 2.72 (s, 4H), 2.41 (s, 3H); LCMS [M+H]$^+$ 491.2.

Example 14: N-(5-(6-(cyclohexylamino)pyridin-3-yl)-4-fluoro-2-(4-methylpiperazin-1-yl)phenyl)-6-oxo-4-(trifluoromethyl)-1,6-dihydropyridine-3-carboxamide

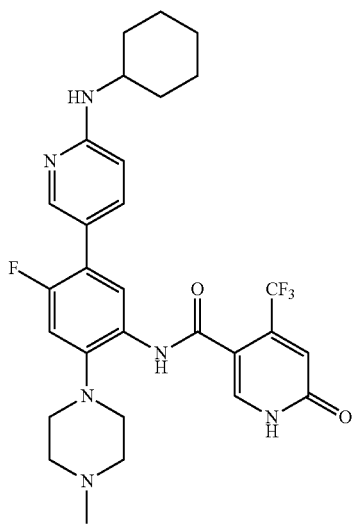 [SMILES: CN1CCN(c2cc(F)c(-c3ccc(NC4CCCCC4)nc3)cc2NC(=O)c2c[nH]c(=O)cc2C(F)(F)F)CC1]

The title compound was prepared in 99% yield similar to the sequence described above for the preparation of Example 3 using 6-(cyclohexylamino)pyridine-3-boronic acid pinacol ester in place of 2-(4-morpholino)pyrimidine-5-boronic acid pinacol ester. $^1$H NMR (500 MHz, MeOD-d$_4$) (major rotamer) δ 8.11 (s, 1H), 7.97 (s, 1H), 7.88 (d, J=8.2 Hz, 1H), 7.62 (d, J=8.9 Hz, 1H), 7.08 (d, J=12.0 Hz, 1H), 6.92 (s, 1H), 6.59 (d, J=8.8 Hz, 1H), 3.71-3.63 (m, 1H), 3.03 (s, 4H), 2.77 (s, 4H), 2.46 (s, 3H), 2.03 (dd, J=12.4, 2.7 Hz, 2H), 1.82-1.77 (m, 2H), 1.45 (td, J=12.4, 3.3 Hz, 2H), 1.32-1.22 (m, 4H); LCMS [M+H]$^+$ 573.4 g/mol.

Example 15: N-(4-fluoro-5-(2-hydroxypyrimidin-5-yl)-2-(4-methylpiperazin-1-yl)phenyl)-6-oxo-4-(trifluoromethyl)-1,6-dihydropyridine-3-carboxamide

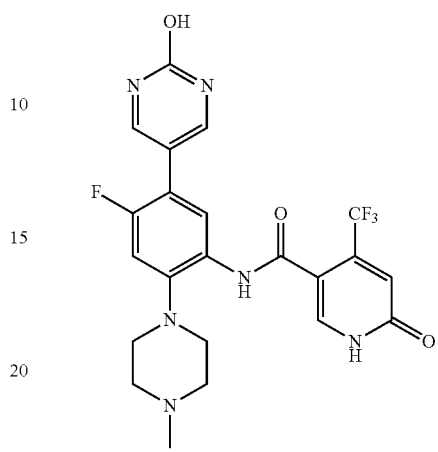

The title compound was isolated in 4% yield as a side product from the chromatographic purification of Example 12. $^1$H NMR (500 MHz, MeOD-d$_4$) δ 8.53 (s, 2H), 7.99 (s, 1H), 7.91 (d, J=8.3 Hz, 1H), 7.17 (d, J=12.0 Hz, 1H), 6.93 (s, 1H), 3.11 (s, 4H), 3.03 (s, 4H), 2.66 (s, 3H); LCMS [M+H]$^+$ 493.3.

Example 16: N-(5-(2-cyanopyrimidin-5-yl)-4-fluoro-2-(4-methylpiperazin-1-yl)phenyl)-6-oxo-4-(trifluoromethyl)-1,6-dihydropyridine-3-carboxamide

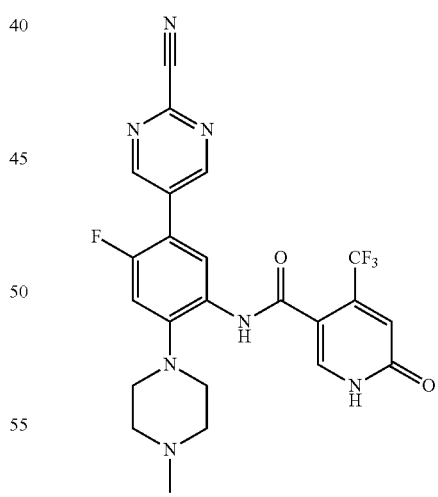

The title compound was prepared in 41% yield similar to the sequence described above for the preparation of Example 3 using 2-cyanopyrimidine-5-boronic acid pinacol ester in place of 2-(4-morpholino)pyrimidine-5-boronic acid pinacol ester. $^1$H NMR (500 MHz, MeOD-d$_4$) δ 9.14 (s, 2H), 8.05 (d, J=8.2 Hz, 1H), 7.98 (s, 1H), 7.20 (d, J=12.3 Hz, 1H), 6.93 (s, 1H), 3.11-3.07 (m, 4H), 2.74 (s, 4H), 2.43 (s, 3H); LCMS [M+H]$^+$ 501.8 g/mol.

Example 17: N-(4-fluoro-2-(4-methylpiperazin-1-yl)-5-(2-(2,2,2-trifluoroethoxy)pyrimidin-5-yl)phenyl)-6-oxo-4-(trifluoromethyl)-1,6-dihydropyridine-3-carboxamide

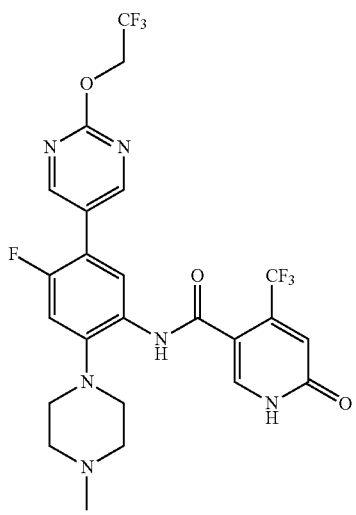 [SMILES: CN1CCN(c2cc(F)c(-c3cnc(OCC(F)(F)F)nc3)cc2NC(=O)c2c[nH]c(=O)cc2C(F)(F)F)CC1]

The title compound was prepared in 81% yield similar to the sequence described above for the preparation of Example 3 using 2-(2,2,2-trifluoroethoxy)pyrimidine-5-boronic acid, pinacol ester in place of 2-(4-morpholino)pyrimidine-5-boronic acid pinacol ester. $^1$H NMR (500 MHz, MeOD-d$_4$) δ 8.82 (s, 2H), 7.97 (s, 1H), 7.97 (d, J=8.1 Hz, 1H), 7.17 (d, J=12.0 Hz, 1H), 6.92 (s, 1H), 5.01 (q, J=8.6 Hz, 2H), 3.06-3.02 (m, 4H), 2.70 (s, 4H), 2.40 (s, 3H); LCMS [M+H]$^+$ 574.8.

Example 18: N-(4-fluoro-2-(4-methylpiperazin-1-yl)-5-(pyrimidin-5-yl)phenyl)-6-oxo-4-(trifluoromethyl)-1,6-dihydropyridine-3-carboxamide

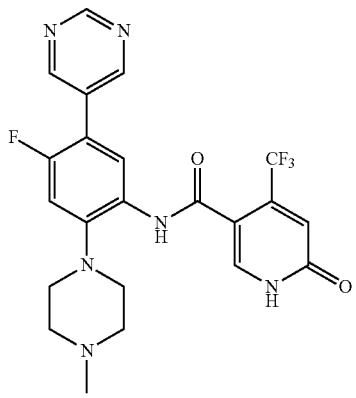 [SMILES: CN1CCN(c2cc(F)c(-c3cncnc3)cc2NC(=O)c2c[nH]c(=O)cc2C(F)(F)F)CC1]

The title compound was prepared in 78% yield similar to the sequence described above for the preparation of Example 3 using 5-pyrimidine boronic acid pinacol ester in place of 2-(4-morpholino)pyrimidine-5-boronic acid pinacol ester. $^1$H NMR (500 MHz, MeOD-d$_4$) δ 9.15 (s, 1H), 9.00 (s, 2H), 8.01 (d, J=8.2 Hz, 1H), 7.98 (s, 1H), 7.18 (d, J=12.1 Hz, 1H), 6.92 (s, 1H), 3.06 (t, J=4.4 Hz, 4H), 2.69 (s, 4H), 2.40 (s, 3H); LCMS [M+H]$^+$ 476.9.

Example 19: N-(5-(2,4-dimethoxypyrimidin-5-yl)-4-fluoro-2-(4-methylpiperazin-1-yl)phenyl)-6-oxo-4-(trifluoromethyl)-1,6-dihydropyridine-3-carboxamide

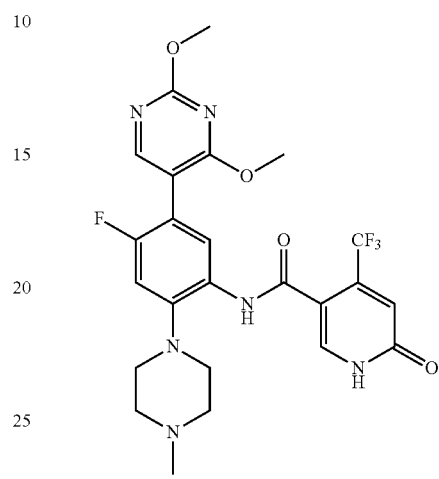

The title compound was prepared in 73% yield similar to the sequence described above for the preparation of Example 3 using 2,4-dimethoxypyrimidine-5-boronic acid, pinacol ester in place of 2-(4-morpholino)pyrimidine-5-boronic acid pinacol ester. $^1$H NMR (500 MHz, MeOD-d$_4$) δ 8.22 (s, 1H), 7.95 (s, 1H), 7.80 (d, J=7.7 Hz, 1H), 7.08 (d, J=11.2 Hz, 1H), 6.92 (s, 1H), 4.05 (s, 3H), 4.02 (s, 3H), 3.03 (s, 4H), 2.71 (s, 4H), 2.41 (s, 3H); LCMS [M+H]$^+$ 537.3.

Example 20: 4-(difluoromethyl)-N-(4-fluoro-2-(4-methylpiperazin-1-yl)-5-(2-morpholinopyrimidin-5-yl)phenyl)-6-oxo-1,6-dihydropyridine-3-carboxamide

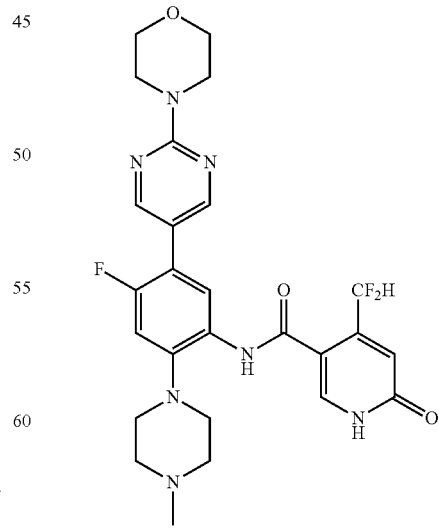

In a 5 ml microwave vessel to a suspension of 4-(difluoromethyl)-6-hydroxynicotinic acid (60.9 mg, 0.322 mmol)

in anhydrous pyridine (391 µl, 4.83 mmol) was added slowly diethyl chlorophosphate (47.7 µl, 0.330 mmol) at RT in an atmosphere of nitrogen. The reaction mixture was stirred for 2 h. The suspension turned homogeneous and then a precipitate formed. To this mixture, 4-fluoro-2-(4-methylpiperazin-1-yl)-5-(2-morpholinopyrimidin-5-yl)aniline (30 mg, 0.081 mmol) was added and the reaction was heated at 70° C. for 3 h. After completion, the pyridine was removed in vacuo and the residue partitioned between EtOAc (3 mL) and saturated aqueous NaHCO₃ (3 mL). The suspension was stirred for 10 min. The organic layer was separated, and dried over anhydrous Na₂SO₄. The solvent was evaporated in vacuo yielding the crude product. The solvent was evaporated in vacuo yielding the crude product that was purified by flash column chromatography on silica gel (0-100%, 89% DCM, 10% MeOH, 1% NH₄Ac/DCM) to afford the desired compound in 72% yield. ¹H NMR (500 MHz, MeOD-d₄) δ 8.55 (d, J=1.1 Hz, 2H), 8.03 (s, 1H), 7.84 (d, J=8.3 Hz, 1H), 7.30 (t, J=55.0 Hz, 1H), 7.10 (d, J=12.1 Hz, 1H), 6.81 (s, 1H), 3.85-3.82 (m, 4H), 3.77-3.75 (m, 4H), 3.02 (s, 4H), 2.67 (s, 4H), 2.38 (s, 3H); LCMS [M+H]⁺ 544.4.

Example 21: N-[2-[3-(dimethylamino)pyrrolidin-1-yl]-4-fluoro-5-(2-morpholin-4-ylpyrimidin-5-yl)phenyl]-6-oxo-4-(trifluoromethyl)-1H-pyridine-3-carboxamide

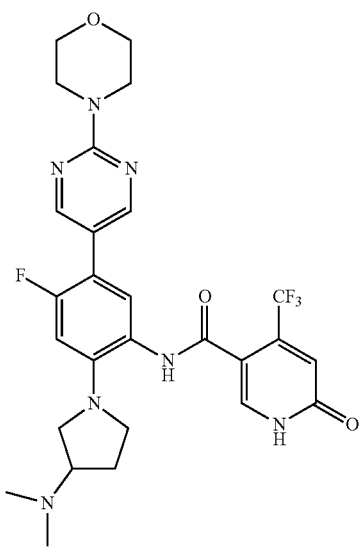

Step 1: 1-(5-fluoro-2-nitrophenyl)-N,N-dimethylpyrrolidin-3-amine

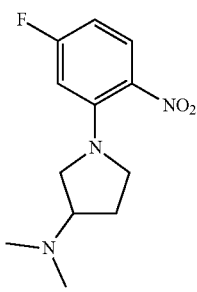 [SMILES: CN(C)C1CCN(c2cc(F)ccc2[N+](=O)[O-])C1]

A suspension of 3-(dimethylamino)pyrrolidine (0.40 mL, 3.1 mmol) and K₂CO₃ (0.22 g, 1.6 mmol) in toluene (4 mL) was warmed to 45° C. After 10 minutes 2,4-difluoro-1-nitrobenzene (0.35 mL, 3.1 mmol) was added dropwise. The reaction was maintained at 45° C. for 1 h. The reaction was concentrated onto celite and flash chromatography [0.5-10% MeOH/DCM+1% NH₄OH] afforded 1-(5-fluoro-2-nitrophenyl)-N,N-dimethylpyrrolidin-3-amine (0.33 g, 41%). LCMS [M+H]⁺: 254.0.

Step 2: 1-(4-bromo-5-fluoro-2-nitrophenyl)-N,N-dimethylpyrrolidin-3-amine

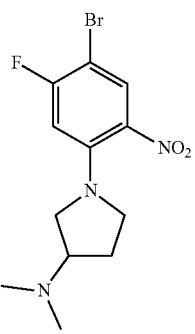 [SMILES: CN(C)C1CCN(c2cc(F)c(Br)cc2[N+](=O)[O-])C1]

A solution of 1-(5-fluoro-2-nitrophenyl)-N,N-dimethylpyrrolidin-3-amine (0.325 g, 1.3 mmol) and NBS (0.22 g, 1.3 mmol) in acetic acid (10 mL) was heated at 105° C. for 2 h. The reaction was cooled to room temperature and poured into water. The mixture was carefully neutralised with Na₂CO₃ (2M Aq.) and the resultant was extracted exhaustively with DCM. The combined extracts were dried over magnesium sulfate, filtered and concentrated to dryness. Flash chromatography [1-10% DCM/MeOH+1% NH₄OH] afforded the title compound (0.184 g, 43%). LCMS [M+H]⁺: 332.2.

Step 3: 1-(5-fluoro-4-(2-morpholinopyrimidin-5-yl)-2-nitrophenyl)-N,N-dimethylpyrrolidin-3-amine

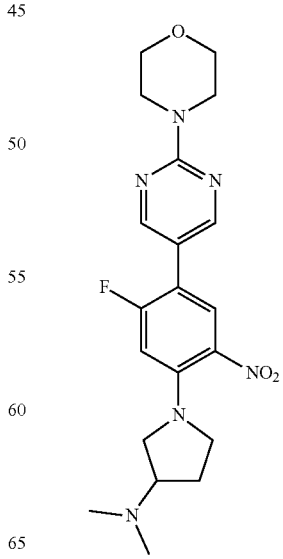

A 30 mL vial was charged with a mixture of 1-(4-bromo-5-fluoro-2-nitrophenyl)-N,N-dimethylpyrrolidin-3-amine (0.092 g, 0.277 mmol), 2-(4-Morpholino)pyrimidine-5-boronic acid pinacol ester (0.113 g, 0.388 mmol), XPhos Pd G2 (4.36 mg, 5.54 µmol) and XPhos (2.64 mg, 5.54 µmol). The vial was sealed with a cap/septum, evacuated and backfilled with nitrogen. 1,4-Dioxane (4 ml) and 2M Aq sodium carbonate (0.692 ml, 1.385 mmol) were added via syringe and the vial was evacuated and backfilled an additional time. The reaction was heated in an aluminum block overnight at 95° C. LCMS [BJW-5015-0054-01; more polar method] indicated clean conversion to the desired product. The reaction mixture was loaded onto celite and purified by flash [0.5-10% MeOH/DCM+1% NH$_4$OH] to afford 1-(5-fluoro-4-(2-morpholinopyrimidin-5-yl)-2-nitrophenyl)-N,N-dimethylpyrrolidin-3-amine (0.271 mmol, 98% yield) as a yellow film that was >95% pure by LCMS. LCMS [M+H]$^+$: 417.3.

Step 4. 1-(2-amino-5-fluoro-4-(2-morpholinopyrimidin-5-yl)phenyl)-N,N-dimethylpyrrolidin-3-amine

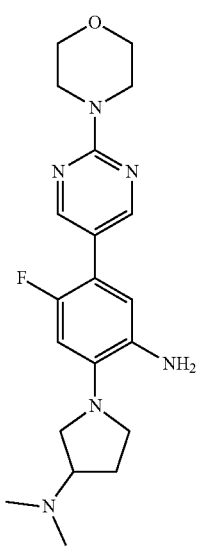 [SMILES: CN(C)C1CCN(c2cc(F)c(-c3cnc(N4CCOCC4)nc3)cc2N)C1]

A mixture of 1-(5-fluoro-4-(2-morpholinopyrimidin-5-yl)-2-nitrophenyl)-N,N-dimethylpyrrolidin-3-amine (0.113 g, 0.271 mmol), iron (0.076 g, 1.357 mmol) and acetic acid (3 ml) was heated to 85° C. for 1 h. The reaction mixture was cooled, diluted with DCM, and decanted by pipette to a round bottom flask. LCMS indicated complete consumption of the starting nitro compound. Concentration onto celite followed by flash [0.1-10% MeOH/DCM+1% NH$_4$OH] afforded 1-(2-amino-5-fluoro-4-(2-morpholinopyrimidin-5-yl)phenyl)-N,N-dimethylpyrrolidin-3-amine (0.204 mmol, 75% yield) [BJW-5015-0056-02] as a yellow foam that was ~92% pure by LCMS. LCMS [M+H]$^+$=387.3

Step 5: N-[2-[3-(dimethylamino)pyrrolidin-1-yl]-4-fluoro-5-(2-morpholin-4-ylpyrimidin-5-yl)phenyl]-6-oxo-4-(trifluoromethyl)-1H-pyridine-3-carboxamide

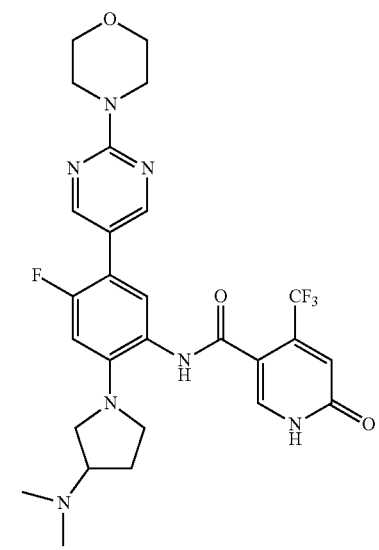 [SMILES: CN(C)C1CCN(c2cc(F)c(-c3cnc(N4CCOCC4)nc3)cc2NC(=O)c2c[nH]c(=O)cc2C(F)(F)F)C1]

Diethyl chlorophosphate (0.118 ml, 0.818 mmol) was added to a stirring solution of 6-hydroxy-4-(trifluoromethyl) nicotinic acid (0.169 g, 0.818 mmol) in pyridine (Py) (2 ml) at room temperature. After stirring for 45 minutes the solution of activated acid was added to a stirring solution of 1-(2-amino-5-fluoro-4-(2-morpholinopyrimidin-5-yl)phenyl)-N,N-dimethylpyrrolidin-3-amine (0.079 g, 0.204 mmol) also in pyridine (2 ml) at room temperature. The reaction was heated to 75° C. for ~5 h. LCMS indicated complete conversion to the desired product along with the excess nicotinic acid. The reaction was concentrated onto celite and purified by flash RP on the biotage [5-95% MeCN/water—no modifier] to afford N-(2-(3-(dimethylamino)pyrrolidin-1-yl)-4-fluoro-5-(2-morpholinopyrimidin-5-yl)phenyl)-6-oxo-4-(trifluoromethyl)-1,6-dihydropyridine-3-carboxamide (0.064 mmol, 32% yield) as a tan solid. $^1$H-NMR (500 MHz, DMSO-d6) δ=12.56 (br. s., 1H), 9.82 (s, 1H), 8.51 (s, 2H), 7.96 (br. s., 1H), 7.32 (d, J=7.5 Hz, 1H), 6.81 (s, 1H), 6.67 (d, J=13.3 Hz, 1H), 3.76-3.67 (m, 8H), 3.41-3.38 (m, 2H), 3.26-3.22 (m, J=8.6, 8.6 Hz, 1H), 2.64 (br. s., 2H), 2.19-2.13 (m, 6H), 2.07 (br. s., 1H), 1.74-1.67 (m, 1H); LCMS [M+H]$^+$ 576.5.

Example 22: N-[5-(3,6-dihydro-2H-pyran-4-yl)-4-fluoro-2-(4-methylpiperazin-1-yl)phenyl]-6-oxo-4-(trifluoromethyl)-1H-pyridine-3-carboxamide

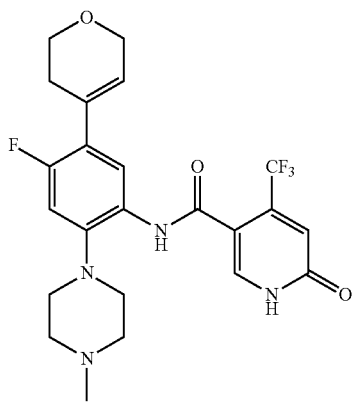 [SMILES: CN1CCN(c2cc(F)c(C3=CCOCC3)cc2NC(=O)c2c[nH]c(=O)cc2C(F)(F)F)CC1]

Step 1: N-(5-bromo-4-fluoro-2-(4-methylpiperazin-1-yl)phenyl)-4-(trifluoromethyl)-6-(2-(trimethylsilyl)ethoxy)nicotinamide

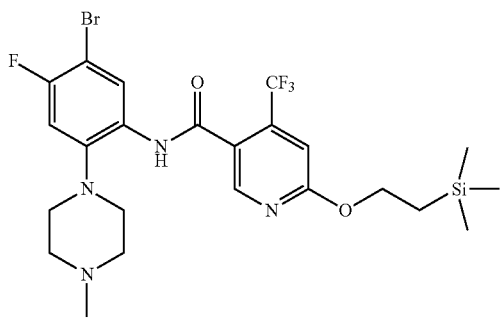 [SMILES: CN1CCN(c2cc(F)c(Br)cc2NC(=O)c2cnc(OCC[Si](C)(C)C)cc2C(F)(F)F)CC1]

To a solution of 4-(trifluoromethyl)-6-(2-(trimethylsilyl)ethoxy)nicotinic acid (800 mg, 2.60 mmol) in pyridine (6.0 mL) was added slowly diethyl chlorophosphate (0.384 ml, 2.65 mmol) at rt in an atmosphere of argon, and the reaction mixture was stirred at rt for about 1 h. The clear solution became cloudy/suspension. To this was then added 5-bromo-4-fluoro-2-(4-methylpiperazin-1-yl)aniline (150 mg, 0.521 mmol) in one lot, and the reaction mixture was heated to 90° C. under argon atmosphere. The reaction was complete in 2 h. A mixture of the desired product along with the excess 4-(trifluoromethyl)-6-(2-(trimethylsilyl)ethoxy)nicotinic acid was observed. The reaction mixture was concentrated to dryness and the residue was co-evaporated twice with toluene to remove the residual pyridine. The residue was taken up in DCM and adsorbed onto celite and purified on Isco column (24 g), to afford the title compound as a beige solid (237 mg). LCMS [M+H]$^+$=577.6

Step 2. N-(5-(3,6-dihydro-2H-pyran-4-yl)-4-fluoro-2-(4-methylpiperazin-1-yl)phenyl)-4-(trifluoromethyl)-6-(2-(trimethylsilyl)ethoxy)nicotinamide

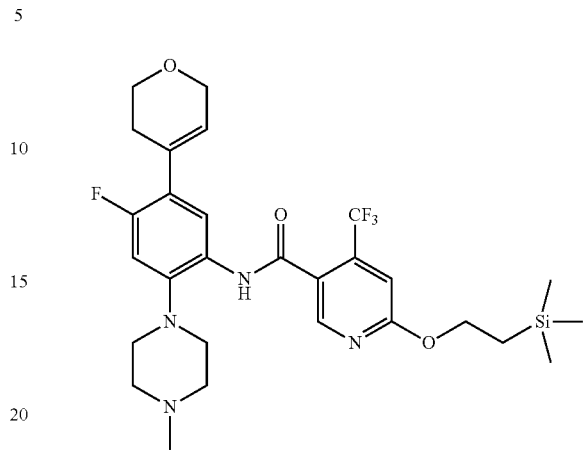

N-(5-bromo-4-fluoro-2-(4-methylpiperazin-1-yl)phenyl)-4-(trifluoromethyl)-6-(2-(trimethylsilyl)ethoxy)nicotinamide (35 mg, 0.061 mmol) and 3,6-dihydro-2H-pyran-4-boronic acid, pinacol ester (17.83 mg, 0.085 mmol) were mixed in 1,4-dioxane (2 ml). Potassium phosphate tribasic reagent grade, >=98% (25.7 mg, 0.121 mmol) was added as a solution in 0.5 ml water and the vial was flushed with nitrogen. Bis(di-tert-butyl(4-dimethylaminophenyl)phosphine)dichloropalladium(II) (4.29 mg, 6.06 µmol) was added, the vial was sealed, and the mixture heated in a microwave reactor to 110° C. for 30 minutes. The crude mixture was concentrated onto celite and purified on Isco (4G) column, eluting with DCM containing 0-2% methanol. The product containing fractions were combined and concentrated to afford the title compound as a pale yellow glassy solid (34 mg). LCMS [M+H]$^+$=581.4.

Step 3: N-(5-(3,6-dihydro-2H-pyran-4-yl)-4-fluoro-2-(4-methylpiperazin-1-yl)phenyl)-4-(trifluoromethyl)-6-(2-(trimethylsilyl)ethoxy)nicotinamide

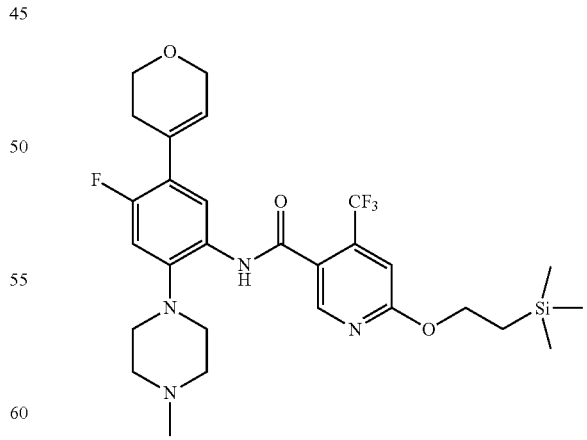

TFA (1 ml) was added to a solution of the N-(5-(3,6-dihydro-2H-pyran-4-yl)-4-fluoro-2-(4-methylpiperazin-1-yl)phenyl)-2-(trifluoromethyl)-4-(2-(trimethylsilyl)ethoxy)benzamide in DCM (2 ml) at RT and the reaction mixture was stirred at RT. LCMS showed completion of the reaction after 0.5 h. The mixture was concentrated to dryness, and the residue was triturated with diethylether. The solid was filtered and dried under high vacuum to obtain the desired product as a beige solid (22 mg). $^1$H NMR (500 MHz, MeOD-d$_4$) δ=8.02 (s, 1H), 7.84-7.74 (m, 1H), 7.06 (d, J=12.2 Hz, 1H), 6.98-6.93 (m, 1H), 6.11 (br. s., 1H), 4.31 (q, J=2.7 Hz, 2H), 3.92 (t, J=5.4 Hz, 2H), 3.61 (d, J=11.4 Hz, 2H), 3.29-3.21 (m, 2H), 2.97 (s, 3H), 2.72-2.64 (m, 4H), 2.72-2.64 (m, 4H), 2.51 (br. s., 2H). LCMS [M+H]$^+$ 481

Example 23: N-[4-fluoro-2-(4-methylpiperazin-1-yl)-5-(1,2,3,6-tetrahydropyridin-4-yl)phenyl]-6-oxo-4-(trifluoromethyl)-1H-pyridine-3-carboxamide

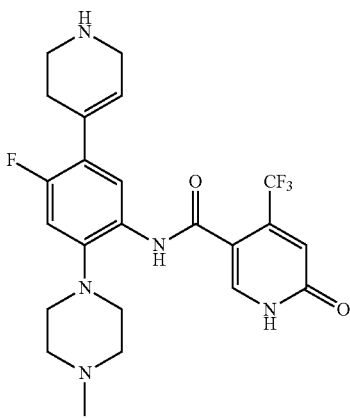 [SMILES: CN1CCN(c2cc(F)c(C3=CCNCC3)cc2NC(=O)c2c[nH]c(=O)cc2C(F)(F)F)CC1]

Step 1: tert-butyl 4-(2-fluoro-4-(4-methylpiperazin-1-yl)-5-(4-(trifluoromethyl)-6-(2-(trimethylsilyl)ethoxy)nicotinamido)phenyl)-3,6-dihydropyridine-1(2H)-carboxylate

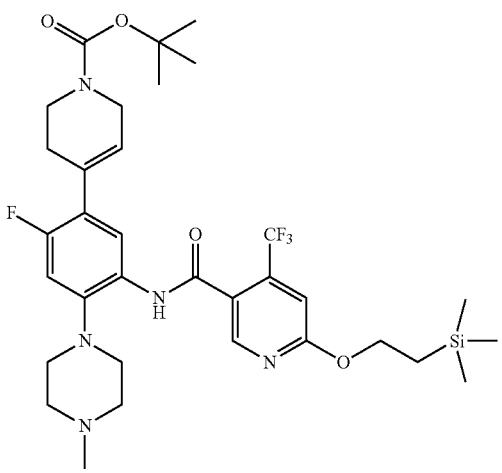 [SMILES: CN1CCN(c2cc(F)c(C3=CCN(C(=O)OC(C)(C)C)CC3)cc2NC(=O)c2cnc(OCC[Si](C)(C)C)cc2C(F)(F)F)CC1]

N-(5-Bromo-4-fluoro-2-(4-methylpiperazin-1-yl)phenyl)-4-(trifluoromethyl)-6-(2-(trimethylsilyl)ethoxy)nicotinamide (35 mg, 0.061 mmol) and tert-butyl-4-(4,4,5,5-tetramethyl-1,3,2-dioxaborolan-2-yl)-1,2,3,6-tetrahydropyridine-1-carboxylate (26.2 mg, 0.085 mmol) were mixed in 1,4-dioxane (1.5 ml). Potassium phosphate tribasic reagent grade, >=98% (25.7 mg, 0.121 mmol) was added as a solution in 0.5 ml water and the vial was flushed with nitrogen. Bis(di-tert-butyl(4-dimethylaminophenyl)phosphine)dichloropalladium(II) (4.29 mg, 6.06 µmol) was added, the vial was sealed, and the mixture heated in a microwave reactor to 110° C. for 30 minutes. The crude mixture was concentrated onto celite and purified on silica gel chromatography, eluting with hexanes containing 0-50% ethylacetate. The product containing fractions were combined and concentrated to afford the title compound as a white foam (27 mg). LCMS [M+H]$^+$=681.2.

Step 2: N-[4-fluoro-2-(4-methylpiperazin-1-yl)-5-(1,2,3,6-tetrahydropyridin-4-yl)phenyl]-6-oxo-4-(trifluoromethyl)-1H-pyridine-3-carboxamide

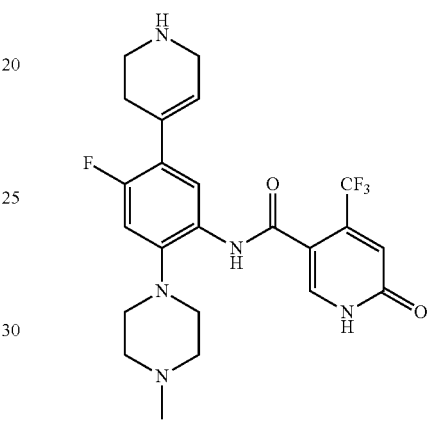

TFA (1 ml) was added to a solution of the starting material in DCM (2 ml) at RT and the reaction mixture was stirred at RT. LCMS showed completion of the reaction after 0.5 h. The reaction mixture was concentrated to dryness, and the residue was triturated with diethylether. The solid was filtered and dried under high vacuum to obtain the desired product as a pale yellow solid (29 mg, 93% yield). $^1$H-NMR (500 MHz, METHANOL-d4) δ=8.01 (s, 1H), 7.87 (d, J=7.9 Hz, 1H), 7.11 (d, J=12.1 Hz, 1H), 6.95 (s, 1H), 6.09 (br. s., 1H), 3.89 (d, J=2.4 Hz, 2H), 3.62 (d, J=11.4 Hz, 2H), 3.48 (t, J=6.1 Hz, 2H), 3.40-3.34 (m, 2H), 3.31-3.22 (m, 2H), 3.17-3.07 (m, 2H), 2.97 (s, 3H), 2.80 (br. s., 2H). LCMS [M+H]$^+$=480

Example 24: N-[4-fluoro-2-(4-methylpiperazin-1-yl)phenyl]-6-oxo-4-(trifluoromethyl)-1H-pyridine-3-carboxamide (Comparative Example)

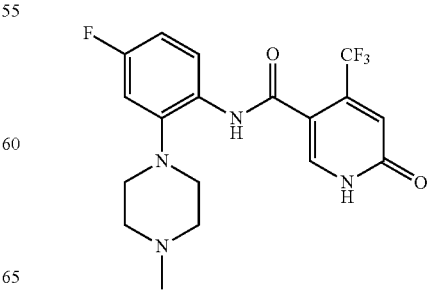

Step 1: N-(4-fluoro-2-(4-methylpiperazin-1-yl)phenyl)-4-(trifluoromethyl)-6-(2-(trimethylsilyl)ethoxy)nicotinamide

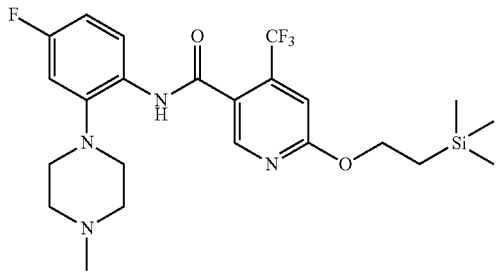 [SMILES: CN1CCN(c2cc(F)ccc2NC(=O)c2cnc(OCC[Si](C)(C)C)cc2C(F)(F)F)CC1]

N-(5-bromo-4-fluoro-2-(4-methylpiperazin-1-yl)phenyl)-4-(trifluoromethyl)-6-(2-(trimethylsilyl)ethoxy)nicotinamide (35 mg, 0.061 mmol) and 1-methyl-1,2,3,6-tetrahydropyridine-4-boronic acid pinacol ester (18.93 mg, 0.085 mmol) were mixed in 1,4-dioxane (1.5 ml). Potassium phosphate tribasic reagent grade, >=98% (25.7 mg, 0.121 mmol) was added as a solution in 0.5 ml water and the vial was flushed with nitrogen. Bis(di-tert-butyl(4-dimethylaminophenyl)phosphine)dichloropalladium(II) (4.29 mg, 6.06 µmol) was added, the vial was sealed, and the mixture heated in a microwave reactor to 110° C. for 30 minutes. The crude mixture was concentrated onto celite and purified on Isco (4G) column, eluting with hexanes containing 0-60% EA. The product containing fractions were combined and concentrated to afford the title compound as a pale yellow foam (13.5 mg, 44.7% yield). LCMS [M+H]$^+$=499.6.

Step 2: N-[4-fluoro-2-(4-methylpiperazin-1-yl)phenyl]-6-oxo-4-(trifluoromethyl)-1H-pyridine-3-carboxamide

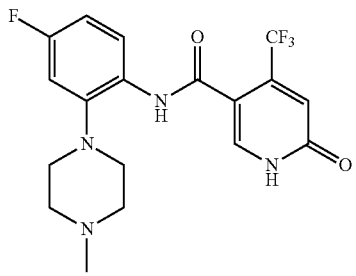

TFA (1 mL) was added to a solution of the starting material in DCM (2 ml) at RT and the reaction mixture was stirred at RT. LCMS showed completion of the reaction after 1.5 h. The reaction mixture was concentrated to dryness, and the residue was triturated with diethyl ether. The solid was filtered and dried under high vacuum to obtain the desired product as a pale yellow solid. (10 mg, 65% yield). $^1$H-NMR (500 MHz, METHANOL-d4) δ=7.89 (s, 1H), 7.70 (dd, J=6.0, 8.8 Hz, 1H), 6.97 (dd, J=2.8, 10.0 Hz, 1H), 6.88 (dt, J=2.8, 8.4 Hz, 1H), 6.83 (s, 1H), 3.50 (d, J=11.1 Hz, 2H), 3.21-3.18 (m, 2H), 3.17-3.09 (m, 2H), 3.02-2.93 (m, 2H), 2.86 (s, 3H); LCMS [M+H]$^+$ 399.

Example 25: 4-fluoro-N-[4-fluoro-5-(2-morpholin-4-ylpyrimidin-5-yl)-2-[(3R,5S)-3,4,5-trimethylpiperazin-1-yl]phenyl]-3-methylbenzamide

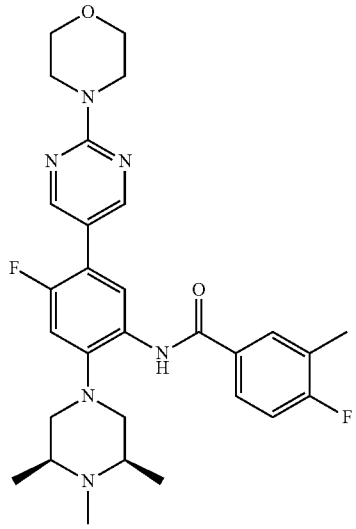 [SMILES: Cc1cc(C(=O)Nc2cc(-c3cnc(N4CCOCC4)nc3)c(F)cc2N2C[C@@H](C)N(C)[C@@H](C)C2)ccc1F]

To a 25 mL RBF charged with 4-fluoro-3-methylbenzoic acid (46 mg, 0.3 mmol) was added thionyl chloride (0.364 mL, 5 mmol). The resulting suspension was heated at 80° C. for 1 h. It was evaporated to give a light yellow oil which was treated with DCM (3 mL), 4-fluoro-5-(2-morpholinopyrimidin-5-yl)-2-((3S,5R)-3,4,5-trimethylpiperazin-1-yl)aniline (40 mg, 0.1 mmol, obtained from Step 3, Example 8 above) followed by Et$_3$N (0.042 mL, 0.3 mmol). The resulting dark red mixture was stirred at rt 1 h, quenched with sat. aq NaHCO$_3$ (10 mL) and extracted with DCM (20 mL×2). The combined extracts were concentrated and purified by flash chromatography (gradient: EtOAc/hex 0-100% then MeOH/DCM 0-5%) to give the title compound as a beige solid (43.1 mg, 80%). $^1$H-NMR (500 MHz, CHLOROFORM-d) δ 9.18 (s, 1H), 8.65 (d, J=8.2 Hz, 1H), 8.59 (s, 2H), 7.82 (dd, J=1.8, 7.1 Hz, 1H), 7.78-7.69 (m, 1H), 7.17 (t, J=8.8 Hz, 1H), 7.02 (d, J=11.2 Hz, 1H), 3.92-3.85 (m, 4H), 3.85-3.78 (m, 4H), 2.92 (d, J=11.0 Hz, 2H), 2.70 (t, J=10.9 Hz, 2H), 2.46-2.37 (m, 8H), 1.18 (d, J=1.0 Hz, 6H); LC-MS [M+H]$^+$ 537.43.

Example 26: N-[4-fluoro-2-[(3R,5S)-3,4,5-trimethylpiperazin-1-yl]phenyl]-6-oxo-4-(trifluoromethyl)-1H-pyridine-3-carboxamide (Comparative Example)

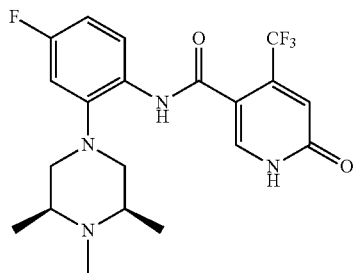 [SMILES: C[C@@H]1CN(c2cc(F)ccc2NC(=O)c2c[nH]c(=O)cc2C(F)(F)F)C[C@H](C)N1C]

Step 1: cis-4-(5-fluoro-2-nitrophenyl)-1,2,6-trimethylpiperazine

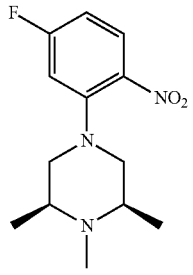 [SMILES: C[C@@H]1CN(c2cc(F)ccc2[N+](=O)[O-])C[C@H](C)N1C]

A suspension of cis-1,2,6-trimethylpiperazine (0.40 g, 3.1 mmol) and potassium carbonate (0.26 g, 1.9 mmol) in toluene (4 mL) was warmed to 45° C. After 10 minutes 2,4-difluoro-1-nitrobenzene (0.35 mL, 3.1 mmol) was added dropwise. The reaction was stirred at 45° C. for 1 h and then cooled to room temperature. The reaction mixture was partitioned between DCM and water and the layers were separated. The aqueous layer was extracted with DCM and the combined organic extracts were dried over magnesium sulfate. After removal of the inorganics by filtration the filtrate was concentrated onto celite and purified by flash chromatography [0.5-10% MeOH/DCM+1% NH$_4$OH] to afford cis-4-(5-fluoro-2-nitrophenyl)-1,2,6-trimethylpiperazine (0.71 g, 85%). LCMS [M+H]$^+$: 268.2.

Step 2: cis-4-fluoro-2-(3,4,5-trimethylpiperazin-1-yl)aniline

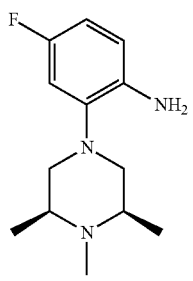 [SMILES: C[C@@H]1CN(c2cc(F)ccc2N)C[C@H](C)N1C]

A solution of cis-4-(5-fluoro-2-nitrophenyl)-1,2,6-trimethylpiperazine (0.155 g, 0.58 mmol) in methanol (5 mL) was hydrogenated in the presence of platinum(IV) oxide (0.013 g, 0.058 mmol) at 1 atm of H$_2$ (g). After 6 h the reaction mixture was concentrated onto celite and purified by flash chromatography [0.5-10% MeOH/DCM+1% NH$_4$OH] to afford cis-4-fluoro-2-(3,4,5-trimethylpiperazin-1-yl)aniline (0.11 g, 82%). LCMS [M+H]$^+$: 238.1.

Step 3: cis-N-(4-fluoro-2-(3,4,5-trimethylpiperazin-1-yl)phenyl)-6-oxo-4-(trifluoromethyl)-1,6-dihydropyridine-3-carboxamide

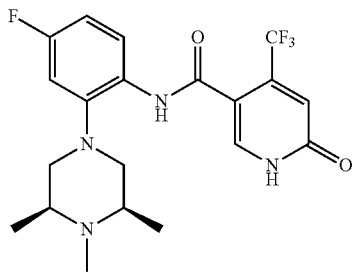 [SMILES: C[C@@H]1CN(c2cc(F)ccc2NC(=O)c2c[nH]c(=O)cc2C(F)(F)F)C[C@H](C)N1C]

A suspension of 6-chloro-4-(trifluoromethyl)nicotinic acid (0.057 g, 0.25 mmol) and thionyl chloride (0.8 mL, 10 mmol) was heated at 80° C. for 1 h. The reaction mixture was concentrated to dryness to afford the acid chloride which was suspended in anhydrous dichloromethane (5 mL) and treated with cis-4-fluoro-2-(3,4,5-trimethylpiperazin-1-yl)aniline (0.050 g, 0.2 mmol) and triethylamine (0.09 mL, 0.6 mmol) at room temperature. After 1 h the reaction was quenched with sat. aq NaHCO$_3$ (10 mL) and extracted into DCM. The combined extracts were concentrated and the residue was dried under reduced pressure to afford cis-6-chloro-N-(4-fluoro-2-(3,4,5-trimethylpiperazin-1-yl)phenyl)-4-(trifluoromethyl)nicotinamide. The resulting chloropyridine intermediate was taken up in HOAc/H$_2$O (7 mL/2 mL) and sodium acetate (0.035 g, 0.42 mmol) was added. The mixture was irradiated in a microwave apparatus at 160° C. for 4 h. The reaction mixture was concentrated onto celite and purified by flash chromatography [0.5-10% MeOH/DCM+1% NH$_4$OH] to afford the title compound cis-N-(4-fluoro-2-(3,4,5-trimethylpiperazin-1-yl)phenyl)-6-oxo-4-(trifluoromethyl)-1,6-dihydropyridine-3-carboxamide (0.063 g, 67%). $^1$H-NMR (500 MHz, DMSO-d6) δ=12.44 (br. s., 1H), 9.41 (s, 1H), 7.88 (s, 1H), 7.64 (dd, J=6.6, 8.4 Hz, 1H), 6.99-6.86 (m, 2H), 6.81 (s, 1H), 2.97 (d, J=11.0 Hz, 2H), 2.43 (t, J=10.9 Hz, 2H), 2.37-2.30 (m, 2H), 2.19 (s, 3H), 1.00 (d, J=6.1 Hz, 6H); LCMS [M+H]$^+$ 427.1

Example 27: 6-acetamido-N-[4-fluoro-5-(2-morpholin-4-ylpyrimidin-5-yl)-2-[(3R,5S)-3,4,5-trimethylpiperazin-1-yl]phenyl]-4-(trifluoromethyl)pyridine-3-carboxamide

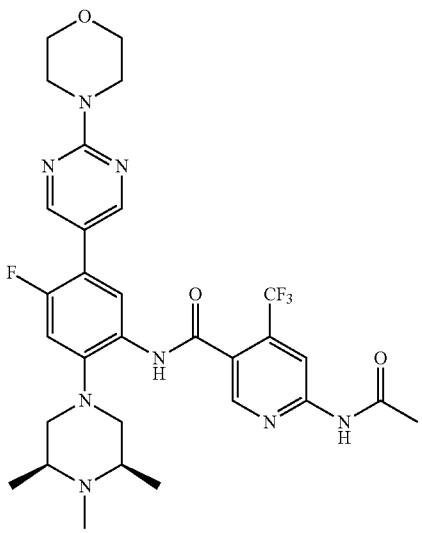 [SMILES: CC(=O)Nc1cc(C(F)(F)F)c(C(=O)Nc2cc(-c3cnc(N4CCOCC4)nc3)c(F)cc2N2C[C@@H](C)N(C)[C@@H](C)C2)cn1]

To a 5 mL microwave vial charged with 6-chloro-N-(4-fluoro-5-(2-morpholinopyrimidin-5-yl)-2-((3S,5R)-3,4,5-trimethylpiperazin-1-yl)phenyl)-4-(trifluoromethyl)nicotinamide (60.7 mg, 0.1 mmol, prepared using the procedure described in the synthesis of Example 8), acetamide (30 mg, 0.5 mmol), Pd$_2$(dba)$_3$ (9.2 mg, 0.01 mmol, 10 mol %), xantphos (12 mg, 0.02 mmol, 20 mol %) and K$_2$CO$_3$ (41 mg, 0.3 mmol) was added dioxane (3 mL). The resulting mixture was irradiated in microwave at 140° C. for 2 h. After passing through microfilter, the filtrate was concentrated, purified by flash chromatography (gradient: EtOAc/hex 0-100% then MeOH/DCM 0-5%), reversed phase C18 column (gradient: CH$_3$CN (0.1% TFA)/H$_2$O 5-90%), porapak column and triturated with MeOH (2 mL) to give the title compound as a white solid (24.6 mg, 38% yield). $^1$H-NMR (500 MHz, CDCl$_3$) δ 8.74 (s, 1H), 8.68-8.56 (m, 5H), 8.15 (s, 1H), 7.04 (d, J=11.1 Hz, 1H), 3.93-3.86 (m, 4H), 3.84-3.79 (m, 4H), 3.52 (d, J=4.6 Hz, 1H), 2.84 (d, J=11.0 Hz, 2H), 2.64 (t, J=10.9 Hz, 2H), 2.35-2.25 (m, 8H), 1.13 (d, J=6.2 Hz, 6H); LC-MS [M+H]$^+$ 631.3.

Example 28: 4-fluoro-N-[4-fluoro-5-(2-morpholin-4-ylpyrimidin-5-yl)-2-[(3R,5S)-3,4,5-trimethylpiperazin-1-yl]phenyl]-3,5-dimethylbenzamide

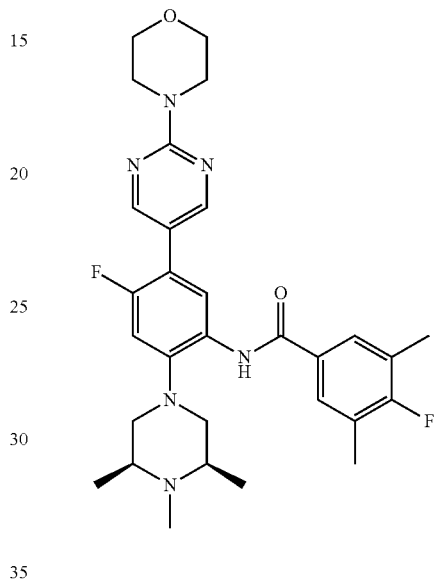

To a 25 mL RBF charged with 4-fluoro-3,5-dimethylbenzoic acid (50 mg, 0.3 mmol) was added thionyl chloride (0.364 mL, 5 mmol). The resulting suspension was heated at 80° C. for 1 h. It was evaporated to give a light yellow oil which was treated with DCM (3 mL), 4-fluoro-5-(2-morpholinopyrimidin-5-yl)-2-((3S,5R)-3,4,5-trimethylpiperazin-1-yl)aniline (40 mg, 0.1 mmol, obtained from the procedure used to produce Example 8 above) followed by Et$_3$N (0.042 mL, 0.3 mmol). The resulting dark red mixture was stirred at rt for 1 h. After quenching with sat. NaHCO$_3$ (10 mL), it was extracted with DCM (20 mL×2). The combined extracts were concentrated, loaded onto celite, dried and purified using Biotage SNAP KP-Sil 50 g (gradient: EtOAc/hex 0-100% then MeOH/DCM 0-8%). Fractions showing pure product were combined, concentrated, triturated with MeOH (3 mL), suction filtered and rinsed with MeOH (0.5 mL) to give a white solid. The filter cake was dried under vacuum to give a pale beige solid (4.6028-4.5767 g=26.1 mg, yield 47% based on 99.70% purity). $^1$H NMR (500 MHz, CDCl$_3$) δ=9.19 (s, 1H), 8.65 (d, J=8.3 Hz, 1H), 8.60 (s, 2H), 7.62 (d, J=6.7 Hz, 2H), 7.02 (d, J=11.2 Hz, 1H), 3.93-3.86 (m, 4H), 3.85-3.79 (m, 4H), 2.94 (d, J=11.0 Hz, 2H), 2.71 (t, J=10.9 Hz, 2H), 2.51-2.41 (m, 2H), 2.41-2.35 (m, 9H), 1.19 (d, J=6.2 Hz, 6H); LC-MS [M+H]$^+$ 551.3.

Example 29: N-[4-fluoro-5-(4-morpholin-4-ylphenyl)-2-[(3R,5S)-3,4,5-trimethylpiperazin-1-yl]phenyl]-6-oxo-4-(trifluoromethyl)-1H-pyridine-3-carboxamide

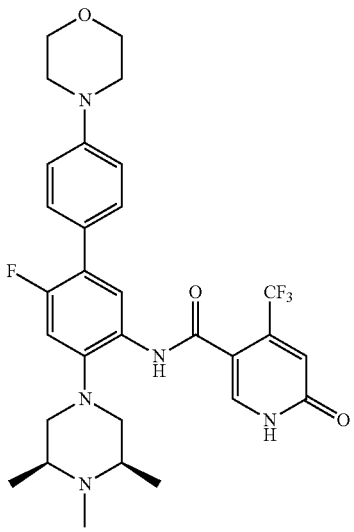

Step 1: 5-bromo-4-fluoro-2-((3R,5S)-3,4,5-trimethylpiperazin-1-yl)aniline

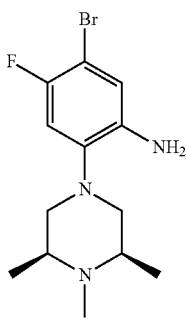

The (2S,6R)-4-(4-bromo-5-fluoro-2-nitrophenyl)-1,2,6-trimethylpiperazine obtained from Example 8, Step 1 (2.16 g) was dissolved in MeOH (30 mL) and to it was added a suspension of Raney-Nickel, 2800 (269 mg, 3.14 mmol) in MeOH (5 mL), followed by hydrazine monohydrate (0.912 mL, 18.86 mmol). The reaction was exothermic. After completion of the addition, the resulting mixture was stirred at rt for 30 min. It was then heated to 50° C. and treated with additional hydrazine monohydrate (0.61 mL, 12.57 mmol), followed by Raney-Nickel, 2800 (0.162 g, 1.886 mmol). The resulting mixture was heated at 50° C. for 1 h. The reaction mixture was filtered and the filtrate was concentrated and purified by Biotage SNAP KP-Sil 50 g (gradient: MeOH/DCM 0-15%) to give, after concentration of fractions showing product, 975 mg of the aniline product as a light brown solid. LCMS [M+H]$^+$ 318.3.

Step 2: N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide To a 25 mL RBF charged with 6-chloro-4-(trifluoromethyl)nicotinic acid (271 mg, 1.2 mmol) was added thionyl chloride (3.64 mL, 50 mmol). The resulting suspension was heated at 80° C. for 1 h, then cooled and evaporated with a rotary evaporator to give a light yellow oil which was treated with DCM (10 mL), 5-bromo-4-fluoro-2-((3S,5R)-3,4,5-trimethylpiperazin-1-yl)aniline (316 mg, 1 mmol) and Et$_3$N (0.42 mL, 3 mmol). The resulting mixture was stirred for 16 h at ambient temperature. The mixture was quenched with sat. aq NaHCO$_3$ (10 mL), extracted with DCM (30 mL×2) and the combined extracts were evaporated and dried to give a light brown solid. A mixture of this solid, NaOAc (164 mg, 2 mmol) in HOAc/H$_2$O (7 mL/2 mL) in a 20 mL microwave vial was heated at 160° C. for 4 h. Solvents were removed using a rotary evaporator at 60° C. and the residue was treated with sat. NaHCO$_3$ (20 mL) and extracted with DCM (60 mL+30 mL). The extracts were concentrated and purified by Biotage SNAP KP-Sil 50 g (gradient: EtOAc/hex 0-100% then MeOH/DCM 0-20%). Fractions containing product were concentrated and dried under vacuum to give a light beige solid (304 mg). LCMS [M+H]$^+$=505.38.

Step 4: N-(6-fluoro-4'-morpholino-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

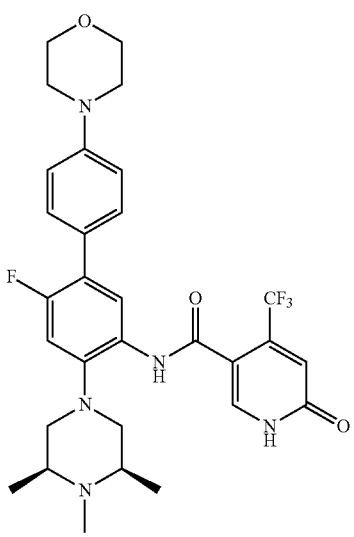

To a 5 mL microwave vial charged with N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol), 4-(morpholino)phenylboronic acid (41.4 mg, 0.2 mmol), and Pd(dppf)Cl$_2$ (14.6 mg, 0.02 mmol, 20 mol %) was added dioxane (3 mL), followed by 1 M aq K$_3$PO$_4$ (0.5 mL, 0.5 mmol). The resulting mixture was irradiated in microwave at 110° C. for 2 h. LCMS showed completion of the reaction. The crude reaction mixture was loaded onto celite, dried and purified using Biotage SNAP KP-Sil 25 g (gradient: EtOAc/hex 0-100% then MeOH/DCM 0-30%). Fractions showing impure product were concentrated, loaded onto celite, and repurified by Biotage SNAP C18 30 g (gradient: CH$_3$CN (0.1% TFA)/H$_2$O 5-30%). Fractions showing product were combined, passed through porapak 6 cc, concentrated and dried to give the title compound as an off white solid (24.6 mg, 40% yield). $^1$H-NMR (500 MHz, MeOD-d$_4$) δ 7.96 (s, 1H), 7.92 (d, J=7.9 Hz, 1H), 7.47 (d, J=8.4 Hz, 2H), 7.07-7.00 (m, 3H), 6.92 (s, 1H), 3.91-3.81 (m, 4H), 3.25-3.17 (m, 4H), 3.05 (d, J=11.1 Hz, 2H), 2.67-2.52 (m, 4H), 2.39 (s, 3H), 1.18 (d, J=6.0 Hz, 6H); LC-MS [M+H]$^+$ 588.36.

Example 30: N-[4-fluoro-2-(4-methylpiperazin-1-yl)-5-[6-(oxan-4-yloxy)pyridin-3-yl]phenyl]-6-oxo-4-(trifluoromethyl)-1H-pyridine-3-carboxamide

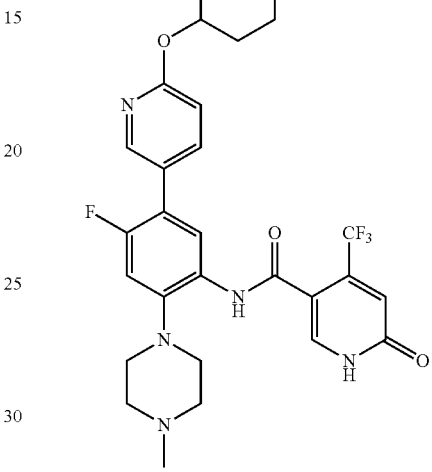

To a 5 mL microwave vial charged with N-(5-bromo-4-fluoro-2-(4-methylpiperazin-1-yl)phenyl)-6-oxo-4-(trifluoromethyl)-1,6-dihydropyridine-3-carboxamide (30.08 mg, 0.063 mmol), 2-(tetrahydropyran-4-yloxy)-5-(4,4,5,5-tetramethyl-1,3,2-dioxaborolan-2-yl)pyridine (57.7 mg, 0.189 mmol), sodium carbonate, anhydrous (66.8 mg, 0.630 mmol) and XPhos (6.01 mg, 0.013 mmol), XPhos Pd G2 (9.92 mg, 0.013 mmol) was added water (1970 µl)/1,4-dioxane (1182 µl) to give a white suspension. The resultant mixture was stirred for 5 min, degassed, purged with N$_2$, and microwaved for 60 min at 120° C. The solvent (dioxane) was evaporated and 15 ml of DCM were added. The suspension was sonicated and the organic phase was removed and concentrated (3×). The resulting crude black oil was purified using a Biotage column, (100-0%, CH2Cl2: 10% MeOH in DCM+NH$_4$Ac; in 10 min and isocratic for 5 min [new isolera 2.3] using KP-SIL 10 g column. Collected at 0% of the DCM) to yield the final product. The product was freeze dried for 2 days to yield 26.0 mg (68% yield) of the desired target compound. $^1$H-NMR NMR (500 MHz, MeOD) δ 8.29 (s, 1H), 7.97 (s, 1H), 7.92 (d, J=8.2 Hz, 1H), 7.87 (d, J=8.6 Hz, 1H), 7.12 (d, J=11.9 Hz, 1H), 6.93 (s, 1H), 6.87 (d, J=8.6 Hz, 1H), 5.26 (tt, J=8.4, 4.0 Hz, 1H), 3.98 (dt, J=9.4, 4.5 Hz, 2H), 3.63 (ddd, J=11.8, 9.1, 2.9 Hz, 2H), 3.05 (s, 4H), 2.80 (s, 4H), 2.48 (s, 3H), 2.13-2.06 (m, 2H), 1.82-1.74 (m, 2H); LCMS [M+H]$^+$=576.3.

Example 31: N-[5-(2-cyanopyrimidin-5-yl)-4-fluoro-2-[(3S,5R)-3,4,5-trimethylpiperazin-1-yl]phenyl]-6-oxo-4-(trifluoromethyl)-1H-pyridine-3-carboxamide

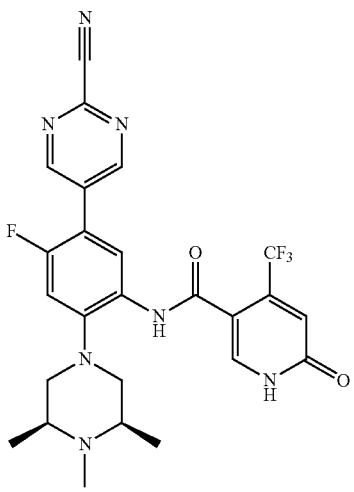 [SMILES: C[C@@H]1CN(c2cc(F)c(-c3cnc(C#N)nc3)cc2NC(=O)c2c[nH]c(=O)cc2C(F)(F)F)C[C@H](C)N1C]

Step 1: N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide

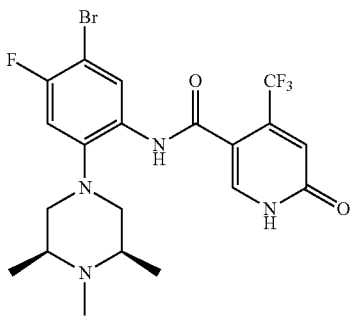 [SMILES: C[C@@H]1CN(c2cc(F)c(Br)cc2NC(=O)c2c[nH]c(=O)cc2C(F)(F)F)C[C@H](C)N1C]

In a 10 mL microwave vial to a suspension of 6-hydroxy-4-(trifluoromethyl)nicotinic acid (1048 mg, 5.06 mmol) in pyridine, anhydrous (6139 µl, 76 mmol) was added slowly diethyl chlorophosphate (749 µl, 5.19 mmol) at RT in an atmosphere of nitrogen. The reaction mixture was stirred at rt for 2 h. The suspension turned into a solution and then into a suspension again. To this, 5-bromo-4-fluoro-2-((3S,5R)-3,4,5-trimethylpiperazin-1-yl)aniline (400 mg, 1.265 mmol) was added and the reaction was heated at 70° C. for 3 h. After completion, pyridine was removed in vacuo and the residue partitioned between dichloromethane (3 mL) and saturated sodium bicarbonate solution (3 mL). The suspension was stirred for 10 min. The organic layer was separated, and dried over anhydrous $Na_2SO_4$. The solvent was evaporated in vacuo yielding the crude product which was purified by flash column chromatography on silica gel (0-100%, 89% $CH_2Cl_2$, 10% MeOH, 1% $NH_4Ac/CH_2Cl_2$) to afford the title compound (192 mg, 30%). $^1H$ NMR (500 MHz, MeOD) δ 8.10 (d, J=7.4 Hz, 1H), 7.92 (s, 1H), 7.09 (d, J=10.1 Hz, 1H), 6.90 (s, 1H), 3.00 (d, J=11.0 Hz, 2H), 2.57 (t, J=11.0 Hz, 2H), 2.54-2.49 (m, 2H), 2.35 (s, 3H), 1.14 (d, J=6.0 Hz, 6H); LCMS $[M+1]^+$=505.00.

Step 2: N-[5-(2-cyanopyrimidin-5-yl)-4-fluoro-2-[(3S,5R)-3,4,5-trimethylpiperazin-1-yl]phenyl]-6-oxo-4-(trifluoromethyl)-1H-pyridine-3-carboxamide

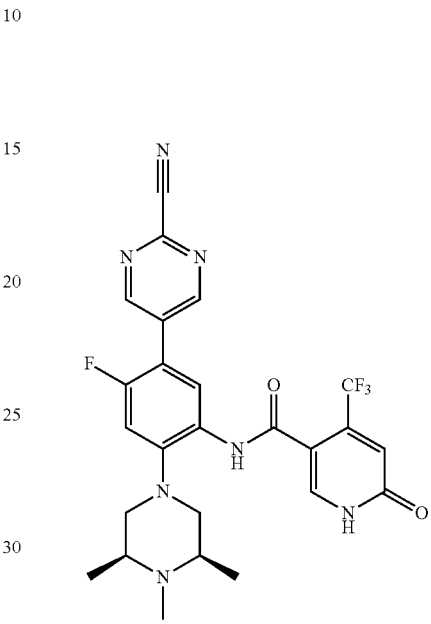

To a 5 mL microwave vial charged with N-(5-bromo-4-fluoro-2-((3R,5S)-3,4,5-trimethylpiperazin-1-yl)phenyl)-6-oxo-4-(trifluoromethyl)-1,6-dihydropyridine-3-carboxamide (29.85 mg, 0.059 mmol), prepared according to the method described in Example 29), 2-cyanopyrimidine-5-boronic acid pinacol ester (40.9 mg, 0.177 mmol), sodium carbonate, anhydrous (62.6 mg, 0.591 mmol) and XPhos (5.63 mg, 0.012 mmol), XPhos Pd G2 (9.30 mg, 0.012 mmol) was added in water (1846 µl)/1,4-dioxane (1108 µl) to give a white suspension that was stirred for 5 min, degassed, purged with $N_2$, and microwaved for 60 min at 120° C. The solvent was evaporated and 15 ml of DCM was added. The suspension was sonicated and the organic phase was removed and concentrated (3×). The crude black oil was purified using a Biotage column, (100-0%, $CH_2Cl_2$: 10% MeOH in $CH_2Cl_2+NH_4Ac$; in 10 min and isocratic for 5 min using KP-SIL 10 g column. Collected at 0% of the $CH_2Cl_2$) to yield an impure product. The product was freeze dried for 2 days to yield the crude product that was purified via preparatory HPLC. The fractions were evaporated and the concentrate was slowly passed through a ionic exchange column Rxn CX 6 cc with MeOH and $NH_4OH$. The product was lyophilized to yield 8.1 mg (26% yield) of the title compound. $^1H$-NMR (500 MHz, MeOD) δ 9.14 (s, 2H), 8.04 (d, J=8.2 Hz, 1H), 7.96 (s, 1H), 7.16 (d, J=12.4 Hz, 1H), 6.92 (s, 1H), 3.15 (d, J=11.6 Hz, 2H), 2.65 (t, J=11.2 Hz, 2H), 2.61-2.54 (m, 2H), 2.39 (s, 3H), 2.03 (s, 1H), 1.17 (d, J=6.1 Hz, 6H); LCMS $[M+H]^+$ 530.

Example 32: N-[4-fluoro-5-(6-morpholin-4-ylpyridin-3-yl)-2-[(3S,5R)-3,4,5-trimethylpiperazin-1-yl]phenyl]-6-oxo-4-(triluoromethyl)-1H-pyridine-3-carboxamide

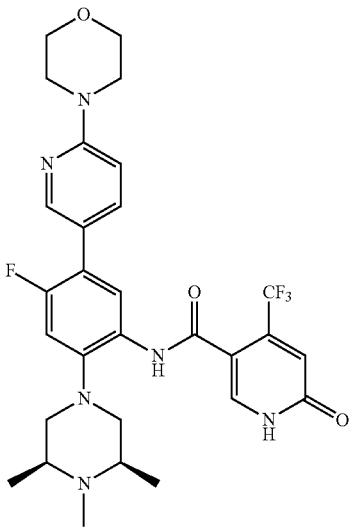

A procedure was used similar to that used for Example 31 above using N-(5-bromo-4-fluoro-2-((3R,5S)-3,4,5-trimethylpiperazin-1-yl)phenyl)-6-oxo-4-(trifluoromethyl)-1,6-dihydropyridine-3-carboxamide (28.89 mg, 0.057 mmol), 4-[5-(4,4,5,5-tetramethyl-[1,3,2]dioxaborolan-2-yl)-pyridin-2-yl]-morpholine (49.8 mg, 0.172 mmol), sodium carbonate, anhydrous (60.6 mg, 0.572 mmol) and XPhos (5.45 mg, 0.011 mmol), XPhos Pd G2 (9.00 mg, 0.011 mmol) to give 33.7 mg (82% yield) of the title compound. $^{1}$H-NMR (500 MHz, MeOD-d$_{4}$) δ 8.32 (s, 1H), 7.96 (s, 1H), 7.90 (d, J=8.3 Hz, 1H), 7.78 (d, J=9.8 Hz, 1H), 7.08 (d, J=12.0 Hz, 1H), 6.92 (s, 1H), 6.91 (d, J=9.0 Hz, 1H), 3.83-3.80 (m, 4H), 3.56-3.53 (m, 4H), 3.13 (d, J=11.6 Hz, 2H), 2.80 (s, 2H), 2.70 (t, J=11.3 Hz, 2H), 2.53 (s, 3H), 1.23 (d, J=6.2 Hz, 6H); LCMS [M+H]$^{+}$ 589.

Example 33: N-[4-fluoro-5-(2-methylpyrimidin-5-yl)-2-[(3S,5R)-3,4,5-trimethylpiperazin-1-yl]phenyl]-6-oxo-4-(trifluoromethyl)-1H-pyridine-3-carboxamide

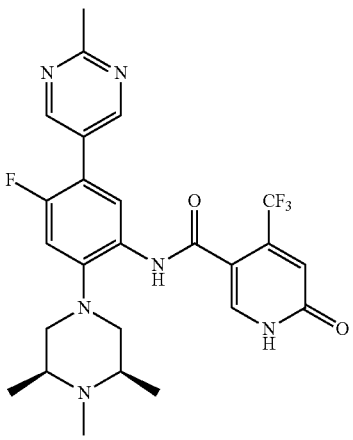 [SMILES: Cc1ncc(-c2cc(NC(=O)c3c[nH]c(=O)cc3C(F)(F)F)c(N3C[C@@H](C)N(C)[C@@H](C)C3)cc2F)cn1]

A procedure was used similar to that used for Example 31 above with N-(5-bromo-4-fluoro-2-((3R,5S)-3,4,5-trimethylpiperazin-1-yl)phenyl)-6-oxo-4-(trifluoromethyl)-1,6-dihydropyridine-3-carboxamide (28.40 mg, 0.056 mmol), 2-methylpyrimidin-5-ylboronic acid pinacol ester (37.1 mg, 0.169 mmol), sodium carbonate, anhydrous (59.6 mg, 0.562 mmol) and XPhos (5.36 mg, 0.011 mmol), XPhos Pd G2 (8.84 mg, 0.011 mmol) gave 17.3 mg (59% yield) of the title compound. $^{1}$H-NMR (500 MHz, MeOD) δ 8.89 (s, 2H), 7.97 (d, J=9.3 Hz, 1H), 7.96 (s, 1H), 7.14 (d, J=12.1 Hz, 1H), 6.92 (s, 1H), 3.11 (d, J=11.1 Hz, 2H), 2.74 (s, 3H), 2.67-2.56 (m, 4H), 2.40 (s, 3H), 1.17 (d, J=6.0 Hz, 6H); LCMS [M+H]$^{+}$ 519.

Example 34: 4-(difluoromethyl)-N-[4-fluoro-5-(2-morpholin-4-ylpyrimidin-5-yl)-2-[(3S,5R)-3,4,5-trimethylpiperazin-1-yl]phenyl]-6-oxo-1H-pyridine-3-carboxamide

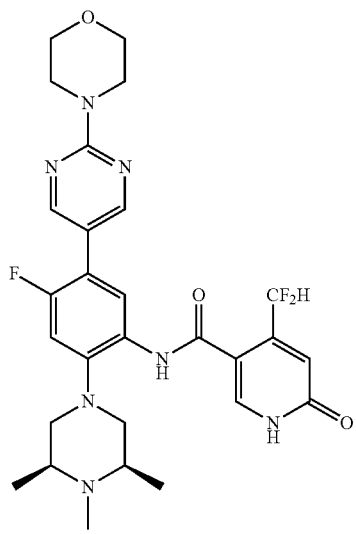

Step 1: methyl 4-formyl-6-methoxynicotinate

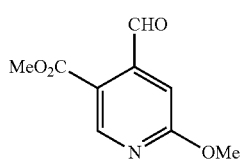 [SMILES: COC(=O)c1cnc(OC)cc1C=O]

To a solution of the commercially available 5-bromo-2-methoxyisonicotinaldehyde (5.0 g, 23.2 mmol, 1 eq) in MeOH was added triethylamine (12 eq), Pd (dppf)Cl$_{2}$ (0.1 eq) at 70° C. under 50 psi of CO gas in a steel bomb for 16 h. Subsequent reaction work-up and flash column chromatography on silica-gel afforded 1.8 g (39% yield) of the desired compound, methyl 4-formyl-6-methoxynicotinate; LCMS [M+H]$^{+}$ 196.

Step 2: methyl 4-(difluoromethyl)-6-methoxynicotinate

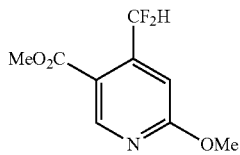 [SMILES: COC(=O)c1cnc(OC)cc1C(F)F]

To a solution of the methyl 4-formyl-6-methoxynicotinate (1.8 g, 9.2 mmol, 1 eq) in DCM was added DAST fluoride (4 eq) at −78° C. and the mixture was maintained at RT for 16 h. TLC analysis indicated formation of less polar spot. Subsequent reaction work-up and flash column chromatography on silica-gel afforded 1.3 g (65% yield) of the desired intermediate, methyl 4-(difluoromethyl)-6-methoxynicotinate; LCMS [M+H]$^+$ 218.

Step 3: methyl 4-(difluoromethyl)-6-oxo-1,6-dihydropyridine-3-carboxylate

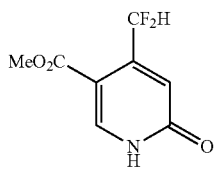

A solution of the methyl 4-(difluoromethyl)-6-methoxynicotinate (2.5 g, 11.5 mmol, 1 eq) and NaI (3 eq) in acetonitrile was treated with TMS-chloride (3 eq) at RT. The resulting mixture was heated to 90° C. for 3 h. TLC analysis indicated formation of polar spot. Reaction work-up and trituration with ether gave 1.7 g (73% yield) of the intermediate, methyl 4-(difluoromethyl)-6-oxo-1,6-dihydropyridine-3-carboxylate; LCMS [M+H]$^+$ 204.

Step 4: 4-(difluoromethyl)-6-oxo-1,6-dihydropyridine-3-carboxylic acid

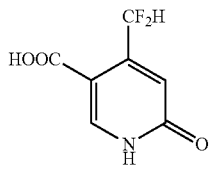 [SMILES: O=C(O)c1c[nH]c(=O)cc1C(F)F]

A solution of the methyl 4-(difluoromethyl)-6-oxo-1,6-dihydropyridine-3-carboxylate (1.7 g, 8.3 mmol, 1 eq) in MeOH:THF:Water (3:2:1) was treated with LiOH·H$_2$O (4.5 eq) at RT and heated to 75° C. for 16 h. TLC analysis indicated consumption of the starting material. Removal of the organic solvent under vacuum followed by neutralization to acidic pH gave 1.15 g (73% yield) of the desired acid, 4-(difluoromethyl)-6-oxo-1,6-dihydropyridine-3-carboxylic acid as a white solid; LCMS [M+H]$^+$ 190.

Step 5: 4-(difluoromethyl)-N-[4-fluoro-5-(2-morpholin-4-ylpyrimidin-5-yl)-2-[(3S,5R)-3,4,5-trimethylpiperazin-1-yl]phenyl]-6-oxo-1H-pyridine-3-carboxamide

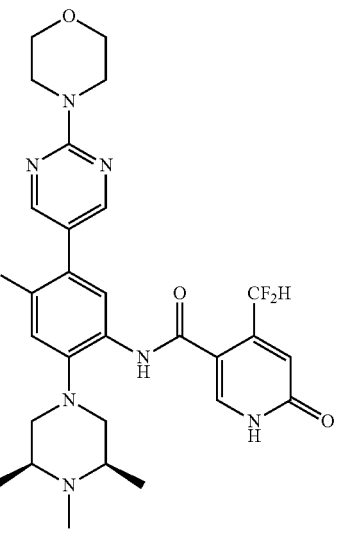

In a 10 ml microwave vial to a suspension of 4-(difluoromethyl)-6-oxo-1,6-dihydropyridine-3-carboxylic acid (37.2 mg, 0.197 mmol) in anhydrous pyridine (239 µl, 2.95 mmol) was added slowly diethyl chlorophosphate (29.1 µl, 0.202 mmol) at ambient temperature in an atmosphere of nitrogen. The reaction mixture was stirred at rt for 2 h. To this mixture then was added 4-fluoro-5-(2-morpholinopyrimidin-5-yl)-2-((3S,5R)-3,4,5-trimethylpiperazin-1-yl)aniline (obtained from Example 8, Step 3) and the reaction was heated at 70° C. for 3 h. After completion, pyridine was removed in vacuo and the residue partitioned between ethyl acetate (3 mL) and saturated sodium bicarbonate solution (3 mL). The suspension was stirred for 10 min. The organic layer was separated, and dried over anhydrous Na$_2$SO$_4$. The solvent was evaporated in vacuo yielding the crude product. Purification was performed via Biotage column, (100-0%, DCM: 10% MeOH in DCM+NH$_4$Ac; in 10 min and isocratic for 5 min [new isolera 2.3] using KP-SIL 10 g column) to yield the product that was lyophilized for 1 day to obtain after further purification using prep HPLC 15.7 mg (55% yield) of the title compound. $^1$H-NMR (500 MHz, MeOD) δ 8.54 (d, J=1.1 Hz, 2H), 8.01 (s, 1H), 7.80 (d, J=8.3 Hz, 1H), 7.31 (t, J=55.1 Hz, 3H) 7.06 (d, J=12.1 Hz, 1H), 6.81 (s, 1H), 3.86-3.81 (m, 4H), 3.78-3.74 (m, 4H), 3.07 (d, J=11.2 Hz, 2H), 2.60 (t, J=11.1 Hz, 2H), 2.54 (d, J=6.2 Hz, 2H), 2.37 (s, 3H), 1.15 (d, J=6.1 Hz, 6H); LCMS [M+H]$^+$ 572.

Example 35: N-[4-fluoro-5-pyridin-3-yl-2-[(3R,5S)-3,4,5-trimethylpiperazin-1-yl]phenyl]-6-oxo-4-(trifluoromethyl)-1H-pyridine-3-carboxamide

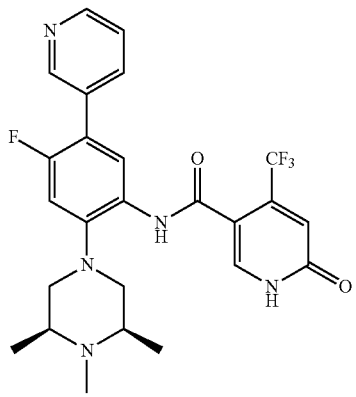

The title compound (23.2 mg, 56%) was prepared according to a procedure similar to Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (40.4 mg, 0.08 mmol) and 3-pyridinylboronic acid (20 mg, 0.16 mmol). $^1$H-NMR (500 MHz, METHANOL-d4) δ 8.75 (s, 1H), 8.55 (d, J=5.2 Hz, 1H), 8.06 (d, J=7.9 Hz, 1H), 7.98 (s, 1H), 7.98 (d, J=7.2 Hz, 2H), 7.56 (dd, J=5.0, 8.0 Hz, 1H), 7.13 (d, J=12.1 Hz, 1H), 6.93 (s, 1H), 3.12 (d, J=11.4 Hz, 2H), 2.68-2.62 (m, 2H), 2.61-2.52 (m, 2H), 2.40 (s, 3H), 1.19 (d, J=6.1 Hz, 6H); LC-MS [M+H]$^+$ 504.25.

Example 36: N-[4-fluoro-5-pyridin-4-yl-2-[(3R,5S)-3,4,5-trimethylpiperazin-1-yl]phenyl]-6-oxo-4-(trifluoromethyl)-1H-pyridine-3-carboxamide

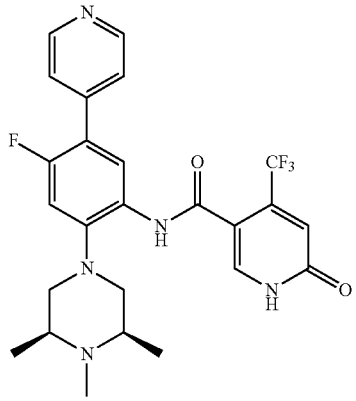

The title compound (24.0 mg, 58% yield) was prepared according to a procedure similar to Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (40.4 mg, 0.08 mmol) and 4-pyridylboronic acid (20 mg, 0.16 mmol). $^1$H-NMR (500 MHz, METHANOL-d4) δ 8.62 (d, J=5.3 Hz, 2H), 8.04 (d, J=8.2 Hz, 1H), 7.98 (s, 1H), 7.67 (d, J=4.9 Hz, 2H), 7.12 (d, J=12.5 Hz, 1H), 6.93 (s, 1H), 3.14 (d, J=11.4 Hz, 2H), 2.69-2.61 (m, 2H), 2.61-2.52 (m, 2H), 2.39 (s, 3H), 1.19 (d, J=6.1 Hz, 6H); LC-MS [M+H]$^+$ 504.25.

Example 37: N-[2-[(3R)-3-(dimethylamino)pyrrolidin-1-yl]-4-fluoro-5-(2-morpholin-4-ylpyrimidin-5-yl)phenyl]-6-oxo-4-(trifluoromethyl)-1H-pyridine-3-carboxamide

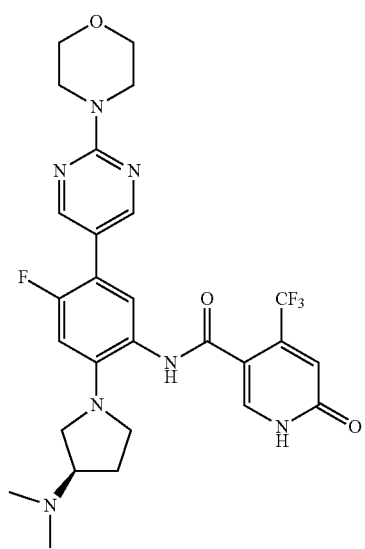 [SMILES: CN(C)[C@@H]1CCN(c2cc(F)c(-c3cnc(N4CCOCC4)nc3)cc2NC(=O)c2c[nH]c(=O)cc2C(F)(F)F)C1]

The title compound was prepared similar to the sequence described above for the preparation of Example 21 above using (R)-(+)-3-(dimethylamino)pyrrolidine in place of racemic 3-(dimethylamino)pyrrolidine in Step 1 to give the title compound (31 mg, 22% yield for the last step). $^1$H NMR (500 MHz, DMSO-d6) δ=12.56 (br. s., 1H), 9.82 (s, 1H), 8.51 (s, 2H), 7.96 (br. s., 1H), 7.32 (d, J=7.5 Hz, 1H), 6.81 (s, 1H), 6.67 (d, J=13.3 Hz, 1H), 3.76-3.67 (m, 8H), 3.41-3.38 (m, 2H), 3.26-3.22 (m, J=8.6, 8.6 Hz, 1H), 2.64 (br. s., 2H), 2.19-2.13 (m, 6H), 2.07 (br. s., 1H), 1.74-1.67 (m, 1H); LCMS [M+H]$^+$ 576.3.

Example 38: N-[2-[(3S)-3-(dimethylamino)pyrrolidin-1-yl]-4-fluoro-5-(2-morpholin-4-ylpyrimidin-5-yl)phenyl]-6-oxo-4-(trifluoromethyl)-1H-pyridine-3-carboxamide

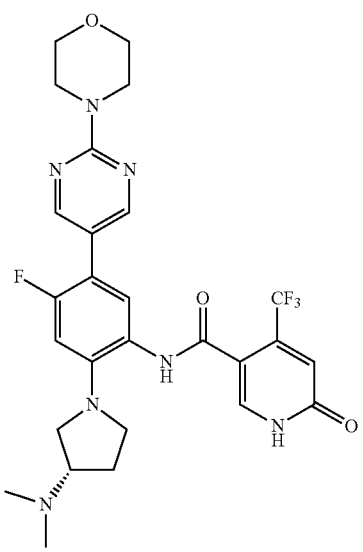

The title compound was prepared similar to the sequence described above for the preparation of Example 21 using (S)-(−)-3-(dimethylamino)pyrrolidine in place of racemic 3-(dimethylamino)pyrrolidine in Step 1 to give 28 mg (23% yield) of the title compound for the last step. $^{1}$H-NMR (500 MHz, DMSO-d6) δ=12.56 (br. s., 1H), 9.82 (s, 1H), 8.51 (s, 2H), 7.96 (br. s., 1H), 7.32 (d, J=7.5 Hz, 1H), 6.81 (s, 1H), 6.67 (d, J=13.3 Hz, 1H), 3.76-3.67 (m, 8H), 3.41-3.38 (m, 2H), 3.26-3.22 (m, J=8.6, 8.6 Hz, 1H), 2.64 (br. s., 2H), 2.19-2.13 (m, 6H), 2.07 (br. s., 1H), 1.74-1.67 (m, 1H); LCMS [M+H]$^{+}$ 576.1.

Example 39: N-[5-[6-(cyclopropylmethoxy)pyridin-3-yl]-4-fluoro-2-[(3S,5R)-3,4,5-trimethylpiperazin-1-yl]phenyl]-6-oxo-4-(trifluoromethyl)-1H-pyridine-3-carboxamide

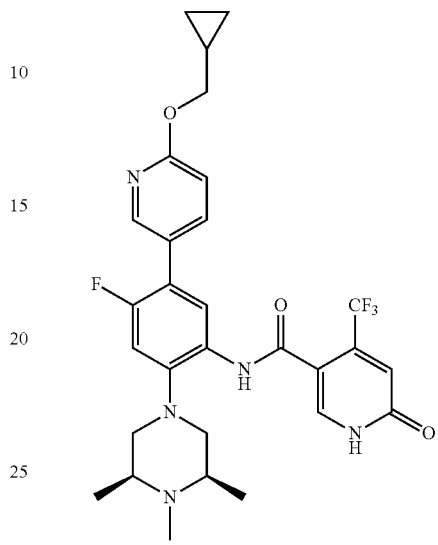

Step 1: 1-bromo-2,4-difluoro-5-nitrobenzene

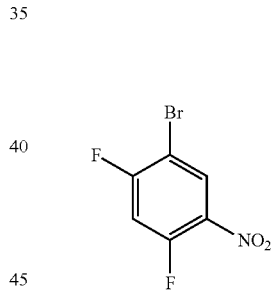

To a suspension of 1-bromo-2,4-difluorobenzene (10 g, 52.1 mmol, 1.0 eq) in cold H$_2$SO$_4$ (37.9 mL) was added Conc. HNO$_3$ (33.3 mL) in a dropwise manner keeping the internal temp 20° C., stirred for 10 min at 0° C. then, the reaction mixture was poured into a mixture of diethyl ether (250 mL) and ice water (250 mL) with vigorous stirring. The organic layer was separated and the aqueous layer was again extracted with Et$_2$O (250 mL). The combined organic layer was washed with Satd. sodium bicarbonate (2×200 mL) followed by satd. brine (2×200 mL) solution. The separated organic layer was dried over Na$_2$SO$_4$ and concentrated under reduced pressure to give crude product which was purified by column chromatography (SiO$_2$, 100-200 mesh) using 15% EtOAc in pet ether as an eluent to give 1-bromo-2,4-difluoro-5-nitrobenzene (52 g, 72% yield) as a yellow color liquid. LCMS: M+H]+ 272.23.

Step 2: (2S,6R)-4-(4-bromo-5-fluoro-2-nitrophenyl)-1,2,6-trimethylpiperazine

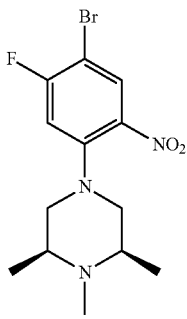

To a solution of 1-bromo-2,4-difluoro-5-nitrobenzene (2.71 g, 21.1 mmol, 1 eq) in ethanol (100 mL) was added TEA (3.49 mL, 25.2 mmol, 1.19 eq) under argon for 20 mins then followed by addition of (2S,6R)-1,2,6-trimethylpiperazine (5.0 g, 21.1 mmol, 1.7 eq) at RT under argon atmosphere and heated to 85° C. for 16 h. TLC analysis indicated formation of polar spot. Then, the reaction mixture was cooled to RT, solvent was evaporated under reduced pressure, the crude product was poured on ice-water (300 mL), and extracted with EtOAc (2×100 mL). The combined organic layers were dried over $Na_2SO_4$ and concentrated under reduced pressure to give crude product which was purified by combiflash column chromatography using 3% methanol in DCM as an eluent to afford 1-bromo-2,4-difluoro-5-nitrobenzene (5.2 g, 70%) as a pale yellow color liquid. LCMS: [M+H]+ 348.15.

Step 3: 5-bromo-4-fluoro-2-((3S,5R)-3,4,5-trimethylpiperazin-1-yl)aniline

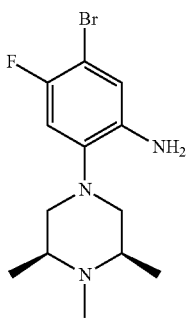

To a solution of 1-bromo-2,4-difluoro-5-nitrobenzene (2.5 g, 7.2 mmol, 1 eq) in ethanol:water (30 mL:10 mL) was added $NH_4Cl$ (0.95 g, 57.97 mmol, 4+4 eq) followed by iron powder (3.24 g, 57.9 mmol, 4+4 eq) at RT under argon atmosphere and heated to 80° C. for 16 h. TLC analysis indicated formation of polar spot. Then, the reaction mixture was cooled to RT, filtered through a celite bed washed with methanol, and the filtrate was concentrated under reduced pressure to give crude product which was purified by neutral alumina column chromatography using 100% DCM as an eluent to afford 5-bromo-4-fluoro-2-((3S,5R)-3,4,5-trimethylpiperazin-1-yl)aniline (1.3 g, 59.1%) as an off white solid. LCMS: [M+H]+ 316.13.

Step 4: 6-chloro-4-(trifluoromethyl)nicotinic acid

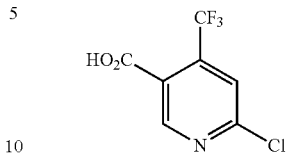

To a solution of butyl magnesium chloride (27.8 mL, 47.2 mmol, 0.7 eq, 1.7 M in THF) in THF was added butyl lithium (30.0 mL, 74.3 mmol, 1.1 eq, 2.5M in hexane) at 0° C. and the reaction mixture was stirred for 10 min, then diluted with THF (80 mL) and cooled to −78° C. Then, 5-bromo-2-chloro-4-(trifluoromethyl)pyridine (17.5 g, 67.5 mmol, 1 eqm procedure described in Example 93) in THF (30 mL) was added and the reaction mixture was stirred for 1 h at same temperature, before being poured onto crushed dry ice then slowly allowed to warm to RT for 16 h. TLC indicated polar spot and the reaction mixture was concentrated and acidified with 2N HCl (80 mL) and extracted with EtOAc (2×500 mL). The organic layer was separated, dried with sodium sulfate and concentrated under reduced pressure to give crude residue. The crude compound was recrystallized from n-pentane (30 mL) and dried using high vacuum to give 6-chloro-4-(trifluoromethyl)nicotinic acid (10 g, 66.6%) as an off white solid compound. LCMS: [M+H]+ 224.05.

Step 5: methyl 6-chloro-4-(trifluoromethyl)nicotinate

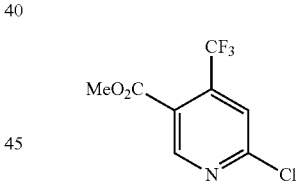

To a solution of 6-chloro-4-(trifluoromethyl)nicotinic acid (16.6 g, 75.1 mmol, 1 eq) in acetone (160 mL), potassium carbonate (15.55 g, 112.6 mmol, 1.5 eq) and dimethylsulphate (8.21 mL, 97.6 mmol, 1.3 eq) was added at 0° C. and the reaction mixture was allowed to come to RT and stirred for 2 h. TLC analysis indicated formation of a non-polar spot. The reaction mixture was concentrated under reduced pressure and gave crude residue. The crude compound was dissolved in EtOAc (500 mL) and washed with brine (2×200 mL) and water (2×200 mL). The separated organic layer was dried over $Na_2SO_4$ and concentrated under reduced pressure to result in crude product; which was purified by column chromatography (silica gel 100-200 mesh) using as an eluent 0-2% EtOAc in petroleum ether to give methyl 6-chloro-4-(trifluoromethyl)nicotinate (13 g, 72.22%) as a liquid compound. LCMS: [M+H]+ 240.08.

Step 6: methyl 4-(trifluoromethyl)-6-(2-(trimethylsilyl)ethoxy)nicotinate

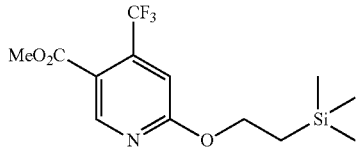 [SMILES: COC(=O)c1cnc(OCC[Si](C)(C)C)cc1C(F)(F)F]

To a suspension of methyl 6-chloro-4-(trifluoromethyl) nicotinate (12.7 g, 53.1 mmol, 1 eq) in toluene (120 mL), TMS-ethanol (4.71 mL, 53.1 mmol, 1 eq), cesium carbonate (51.8 g, 159.4 mmol, 3 eq) and BINAP (3.571 g, 5.3 mmol, 0.1 eq) were degassed with for 15 min and Pd(OAc)$_2$ (0.95 g, 4.2 mmol, 0.08 eq) was added then the reaction mixture was heated to 120° C. for 2 h. TLC analysis indicated formation of a non-polar spot. The reaction mixture was diluted with EtOAc (500 mL), filtered with a celite pad and concentrated under reduced pressure to result in crude product which was purified by column chromatography (silica gel 100-200 mesh) using 5% EtOAc in petroleum ether as an eluent to afford the desired compound (9.0 g, 65%) as a pale yellow color liquid. LCMS: [M+H]$^+$: 294.15.

Step 7: 4-(trifluoromethyl)-6-(2-(trimethylsilyl)ethoxy)nicotinic acid

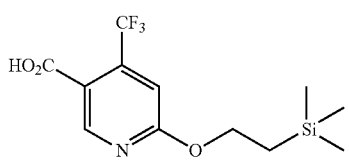 [SMILES: C[Si](C)(C)CCOc1cc(C(F)(F)F)c(C(=O)O)cn1]

To a solution of methyl 4-(trifluoromethyl)-6-(2-(trimethylsilyl)ethoxy)nicotinate (20 g, 62.3 mmol, 1 eq) in THF:MeOH:H$_2$O (60 mL: 40 mL: 20 mL), lithium hydroxide monohydrate (10 g, 249.2 mmol, 4 eq) was added and the reaction mixture was stirred at RT for 16 h. TLC analysis indicated polar spot. The reaction was concentrated under reduced pressure and gave crude compound. The crude compound was acidified with 2N HCl (20 mL), then the obtained precipitate was filtered off and washed with diethyl ether (50 mL) and dried under high vacuum to give the desired compound 4-(trifluoromethyl)-6-(2-(trimethylsilyl)ethoxy)nicotinic acid (9.2 g, 48.40%) as an off white solid. LCMS: [M+H]$^+$ 306.20.

Step 8: N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide

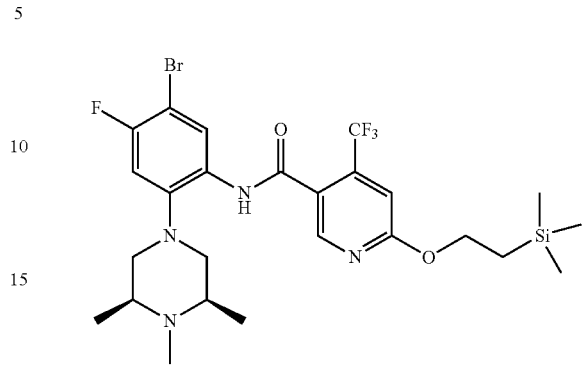

To a solution of 4-(trifluoromethyl)-6-(2-(trimethylsilyl)ethoxy)nicotinic acid (6.0 g, 19.5 mmol, 1.0 eq) in dry DMF (70 mL), HATU (11.13 g, 29.3 mmol, 1.5 eq) and DIPEA (6.6 mL, 39.0 mmol, 2.0 eq) were added at RT and the reaction mixture was stirred for 10 min. Then 5-bromo-4-fluoro-2-((3S,5R)-3,4,5-trimethylpiperazin-1-yl)aniline (5.8 g, 19.5 mmol, 1.0 eq) was added and the reaction mixture was stirred for 48 h. TLC analysis indicated formation of a non-polar spot. The reaction mixture was diluted with EtOAc (2×500 mL) and washed with cold water (2×500 mL) & Brine (2×200 mL), The separated organic layers were combined, dried over Na$_2$SO$_4$ and concentrated under reduced pressure to give crude product which was purified by column chromatography (Neutral Al$_2$O$_3$) using as an eluent 10%-20% EtOAc in petroleum ether to give the title compound (5.2 g, 45%) as an off white solid. LCMS: [M+H]$^+$: 604.8.

Step 9: N-(5-(6-(cyclopropylmethoxy)pyridin-3-yl)-4-fluoro-2-((3S,5R)-3,4,5-trimethylpiperazin-1-yl)phenyl)-4-(trifluoromethyl)-6-(2-(trimethylsilyl)ethoxy)nicotinamide

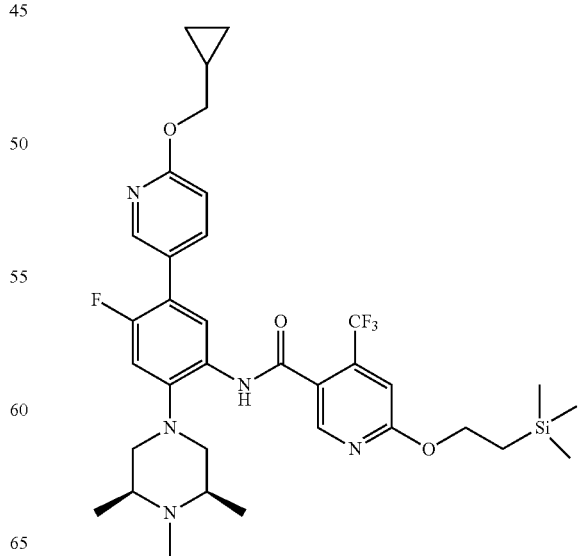

To a 20 mL microwave vial charged with N-(5-bromo-4-fluoro-2-((3R,5S)-3,4,5-trimethylpiperazin-1-yl)phenyl)-4-(trifluoromethyl)-6-(2-(trimethylsilyl)ethoxy)nicotinamide (0.532 g, 0.879 mmol), 2-(cyclopropylmethoxy)-5-(4,4,5,5-tetramethyl-1,3,2-dioxaborolan-2-yl)pyridine (0.363 g, 1.318 mmol), bis(di-tert-butyl(4-dimethylaminophenyl)phosphine)dichloropalladium(II) (0.062 g, 0.088 mmol) and potassium phosphate tribasic reagent grade, >98% (0.373 g, 1.757 mmol) was added water (1.464 ml)/1,4-dioxane (13.18 ml) to give a white suspension that was stirred for 5 min, degassed, purged with $N_2$, and microwaved for 60 min at 110° C. The reaction was monitored by LCMS, which indicated that the reaction was complete. The solvent (dioxane) was evaporated and 15 ml of DCM were added. The suspension was sonicated and the organic phase was removed and concentrated (3×). The crude brown oil was purified using a Biotage column, (100-0%, $CH_2Cl_2$: 10% MeOH in $CH_2Cl_2+NH_4Ac$; in 10 min and isocratic for 5 min using KP-SIL 50 g column. Collected at 10% of the $CH_2Cl_2$) to yield the intermediate product. The fractions were evaporated and the resulting product was lyophilized to give 295 mg (49.4% yield) of the target silylated intermediate. LCMS [M–H]–=672.1.

Step 10: N-(5-(6-(cyclopropylmethoxy)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide

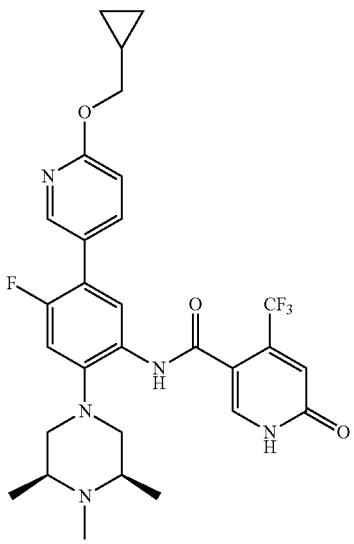 [SMILES: C[C@@H]1CN(c2cc(F)c(-c3ccc(OCC4CC4)nc3)cc2NC(=O)c2c[nH]c(=O)cc2C(F)(F)F)C[C@H](C)N1C]

To a solution of N-(5-(6-(cyclopropylmethoxy)pyridin-3-yl)-4-fluoro-2-((3R,5S)-3,4,5-trimethylpiperazin-1-yl)phenyl)-4-(trifluoromethyl)-6-(2-(trimethylsilyl)ethoxy)nicotinamide (135.26 mg, 0.201 mmol) in dry DMF (401 µL) was added CsF (91 mg, 0.602 mmol) and heated at 60° C. for 1 h. The reaction was monitored by LCMS which indicated that the reaction was complete. The mixture was diluted with water and extracted with ethyl acetate (3×20 ml). The combined organic layer was washed with water, brine solution, concentrated under reduce pressure and freeze dried for 2 days to yield the title compound (0.182 mmol, 91% yield). $^1$H-NMR (500 MHz, MeOD) δ 8.27 (s, 1H), 7.95 (s, 1H), 7.90 (d, J=8.2 Hz, 1H), 7.86 (dd, J=8.6, 0.9 Hz, 1H), 7.09 (d, J=12.0 Hz, 1H), 6.92 (s, 1H), 6.88 (d, J=8.7 Hz, 1H), 4.15 (d, J=7.1 Hz, 2H), 3.11 (d, J=9.5 Hz, 2H), 2.75-2.62 (m, 4H), 2.46 (s, 3H), 1.35-1.25 (m, 1H), 1.20 (d, J=5.6 Hz, 6H), 0.64-0.58 (m, 2H), 0.39-0.34 (m, 2H); LCMS [M+H]+ 574.

Example 40: N-[5-[2-(dimethylamino)pyrimidin-5-yl]-4-fluoro-2-(4-methylpiperazin-1-yl)phenyl]-6-oxo-4-(trifluoromethyl)-1H-pyridine-3-carboxamide

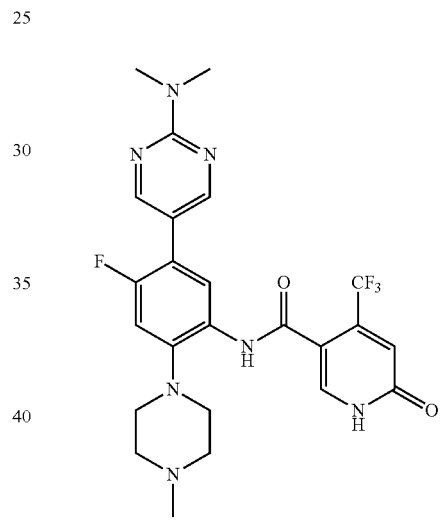

A procedure similar to that employed in Example 3, Step 2 using N-(5-bromo-4-fluoro-2-(4-methylpiperazin-1-yl)phenyl)-6-oxo-4-(trifluoromethyl)-1,6-dihydropyridine-3-carboxamide (30.53 mg, 0.064 mmol), N,N-dimethyl-5-(4,4,5,5-tetramethyl-1,3,2-dioxaborolan-2-yl)pyrimidin-2-amine (47.8 mg, 0.192 mmol), anhydrous sodium carbonate (67.8 mg, 0.640 mmol), XPhos (6.10 mg, 0.013 mmol), and XPhos Pd G2 (10.07 mg, 0.013 mmol) gave 27.4 mg (78% yield) of the title compound as a white powder. $^1$HNMR (500 MHz, MeOD) δ 8.41 (d, J=1.1 Hz, 2H), 7.87 (s, 1H), 7.80 (d, J=8.2 Hz, 1H), 7.01 (d, J=12.0 Hz, 1H), 6.82 (s, 1H), 3.12 (s, 6H), 2.92 (s, 4H), 2.62 (s, 4H), 2.32 (s, 3H); LCMS [M+H]+ 520.

Example 41: N-[4-fluoro-2-(4-methylpiperazin-1-yl)-5-[6-(morpholin-4-ylmethyl)pyridin-3-yl]phenyl]-6-oxo-4-(trifluoromethyl)-1H-pyridine-3-carboxamide

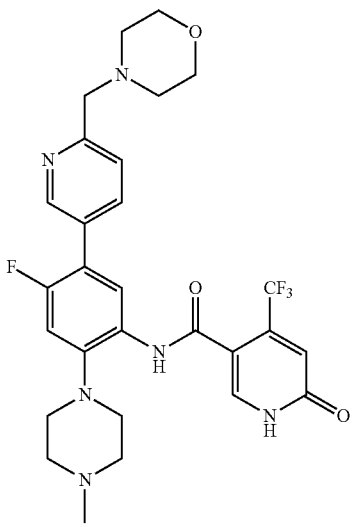

A procedure similar to that of Example 3 using N-(5-bromo-4-fluoro-2-(4-methylpiperazin-1-yl)phenyl)-6-oxo-4-(trifluoromethyl)-1,6-dihydropyridine-3-carboxamide (30.77 mg, 0.064 mmol) and 6-(morpholinomethyl)pyridin-3-ylboronic acid (42.9 mg, 0.193 mmol) afforded 22.5 mg (55.9% yield) of the title compound. $^1$H-NMR (500 MHz, MeOD) δ 8.73 (s, 1H), 8.04 (d, J=8.4 Hz, 1H), 8.01 (s, 1H), 8.00 (d, J=8.2 Hz, 1H), 7.65 (d, J=8.1 Hz, 1H), 7.21 (d, J=11.8 Hz, 1H), 6.94 (s, 1H), 3.93 (s, 2H), 3.78 (s, 4H), 3.21 (s, 4H), 2.84 (s, 3H), 2.76 (s, 4H); LCMS [M+H]+ 575.

Example 42: N-[4-fluoro-5-(2-morpholin-4-ylpyrimidin-5-yl)-2-[(3R,5S)-3,4,5-trimethylpiperazin-1-yl]phenyl]-3-(trifluoromethyl)-1H-pyrazole-4-carboxamide

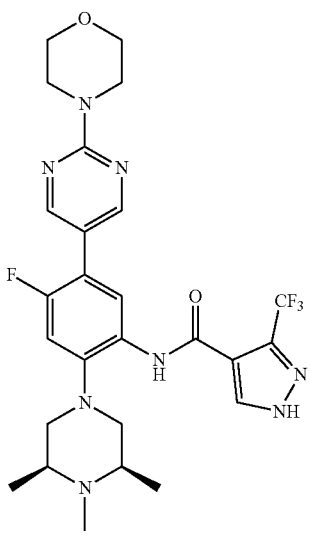

The title compound was prepared according to a method similar to that used in Example 34 above using 3-(trifluoromethyl)pyrazole-4-carboxylic acid (27 mg, 0.15 mmol) and 4-fluoro-5-(2-morpholinopyrimidin-5-yl)-2-((3S,5R)-3,4,5-trimethylpiperazin-1-yl)aniline (20 mg, 0.05 mmol) to give 18.1 mg (62% yield) of the product as a white solid. $^1$H NMR (500 MHz, METHANOL-d4) δ 8.58 (s, 2H), 8.39 (br. s., 1H), 7.98 (d, J=8.2 Hz, 1H), 7.11 (d, J=12.0 Hz, 1H), 3.89-3.83 (m, 4H), 3.80-3.75 (m, 4H), 3.04 (d, J=11.4 Hz, 2H), 2.63 (t, J=11.2 Hz, 2H), 2.55-2.46 (m, 2H), 2.37 (s, 3H), 1.15 (d, J=6.2 Hz, 6H); LC-MS [M+H]+=569.39.

Example 43: N-(2',6-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide

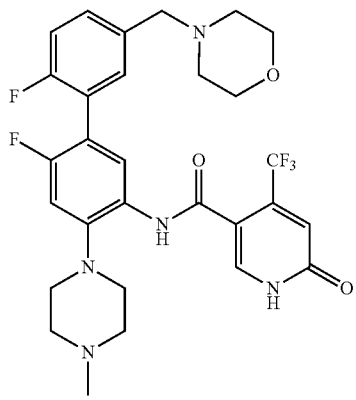

A procedure similar to that of Example 3 using N-(5-bromo-4-fluoro-2-(4-methylpiperazin-1-yl)phenyl)-6-oxo-4-(trifluoromethyl)-1,6-dihydropyridine-3-carboxamide (29.41 mg, 0.062 mmol), 4-(4-fluoro-3-(4,4,5,5-tetramethyl-1,3,2-dioxaborolan-2-yl)benzyl)morpholine (59.4 mg, 0.185 mmol), sodium carbonate, anhydrous (65.3 mg, 0.616 mmol), XPhos (5.88 mg, 0.012 mmol), and XPhos Pd G2 (9.70 mg, 0.012 mmol) afforded 30.6 mg (81% yield) of the title compound as a white solid. $^1$H NMR (500 MHz, MeOD) δ 7.95 (s, 1H), 7.85 (d, J=7.6 Hz, 1H), 7.40 (dd, J=9.2, 6.1 Hz, 2H), 7.18-7.14 (m, 1H), 7.09 (d, J=11.2 Hz, 1H), 6.92 (s, 1H), 3.74-3.66 (m, 4H), 3.57 (s, 2H), 3.04 (s, 4H), 2.68 (s, 4H), 2.49 (s, 4H), 2.39 (s, 3H)); LCMS [M+H]+ 592 g/mol.

Example 44: N-(3'-((cyclopentylamino)methyl)-6-fluoro-4-(4-methylpiperazin-1-yl)-[1,1'-biphenyl]-3-yl)-6-oxo-4-(trifluoromethyl)-1,6-dihydropyridine-3-carboxamide

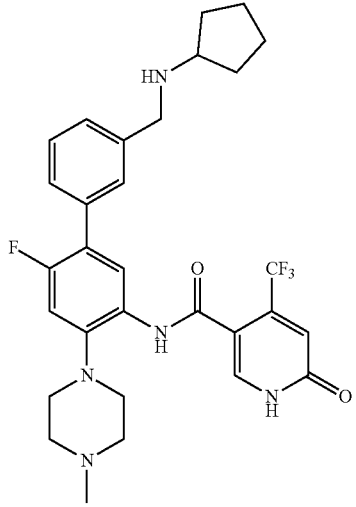 [SMILES: CN1CCN(c2cc(F)c(-c3cccc(CNC4CCCC4)c3)cc2NC(=O)c2c[nH]c(=O)cc2C(F)(F)F)CC1]

A procedure was employed similar that to described in Example 3 using N-(5-bromo-4-fluoro-2-(4-methylpiperazin-1-yl)phenyl)-6-oxo-4-(trifluoromethyl)-1,6-dihydropyridine-3-carboxamide (30.51 mg, 0.064 mmol), 3-(N-cyclopentylaminomethyl)phenylboronic acid, pinacol ester, HCl (64.8 mg, 0.192 mmol), anhydrous sodium carbonate, (67.8 mg, 0.639 mmol), XPhos (6.10 mg, 0.013 mmol), and XPhos Pd G2 (10.06 mg, 0.013 mmol) to give 0.68 mg (1.7% yield) of the title compound. $^1$H NMR (500 MHz, MeOD) δ 8.08 (s, 1H), 8.00 (d, J=7.9 Hz, 1H), 7.62 (s, 1H), 7.57 (d, J=7.6 Hz, 1H), 7.49 (t, J=7.7 Hz, 1H), 7.43 (d, J=7.6 Hz, 1H), 7.10 (d, J=12.0 Hz, 1H), 6.79 (d, J=6.4 Hz, 1H), 4.05 (s, 2H), 3.38 (p, J=7.3 Hz, 1H), 3.04-2.99 (m, 4H), 2.65 (s, 4H), 2.36 (s, 3H), 2.06 (dt, J=12.5, 7.0 Hz, 2H), 1.81-1.75 (m, 2H), 1.65-1.54 (m, 4H); LCMS [M+H]$^+$=562.7.

Example 45: N-(4-(3,4-dimethylpiperazin-1-yl)-6-fluoro-3'-(morpholinomethyl)-[1,1'-biphenyl]-3-yl)-6-oxo-4-(trifluoromethyl)-1,6-dihydropyridine-3-carboxamide

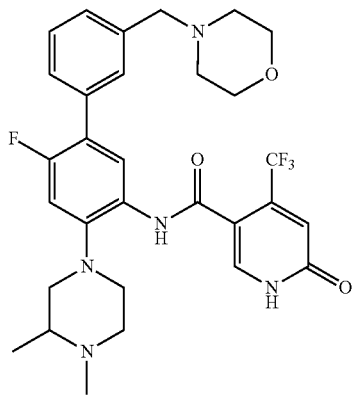

Step 1: 4-(4-chloro-5-fluoro-2-nitrophenyl)-1,2-dimethylpiperazine

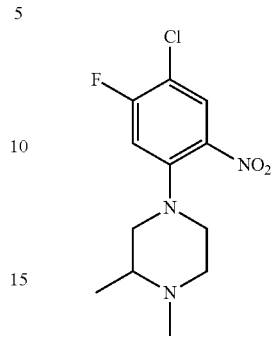

A microwave vial was charged with 1-bromo-4-chloro-5-fluoro-2-nitrobenzene (0.50 g, 2.0 mmol), 1,2-dimethylpiperazine (0.39 g, 2.1 mmol), palladium acetate (0.044 g, 0.20 mmol), 4,5-bis(diphenylphosphino)-9,9-dimethylxanthene (0.11 g, 0.20 mmol) and cesium carbonate (2.1 g, 6.4 mmol). The vial was capped, evacuated and backfilled with nitrogen. Toluene (25 mL) was added via syringe and the reaction vial was evacuated and backfilled with nitrogen an additional time. The reaction was warmed to 50° C. overnight. The reaction mixture was concentrated onto celite and purified by flash chromatography [0-10% MeOH/DCM+1% NH$_4$OH] to afford an inseparable mixture of the desired Buchwald product [4-(4-chloro-5-fluoro-2-nitrophenyl)-1,2-dimethylpiperazine] along with undesired by-product [4-(5-bromo-2-chloro-4-nitrophenyl)-1,2-dimethylpiperazine]. This mixture was carried forward to the next step where the corresponding products were separable by flash chromatography. LCMS [M+H]$^+$=288.3.

Step 2: 4-((4'-(3,4-dimethylpiperazin-1-yl)-2'-fluoro-5'-nitro-[1,1'-biphenyl]-3-yl)methyl)morpholine

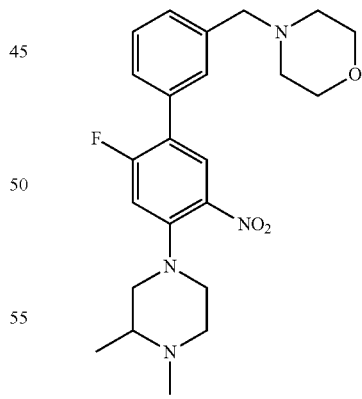

A vial was charged with the mixture obtained in Step 1 (0.22 g), 3-(4-morpholinomethyl)phenylboronic acid pinacol ester (0.16 g, 0.52 mmol), XPhos Pd G2 (0.006 g, 0.007 mmol) and XPhos (0.004 g, 0.007 mmol). The vial was sealed with a septum cap and evacuated and backfilled with nitrogen. 1,4-Dioxane (4 mL) and a 2M aq. solution of sodium carbonate (0.90 mL, 1.7 mmol) were added via syringe. The vial was evacuated and backfilled an additional time before being heated at 100° C. in an aluminum block overnight. The reaction was cooled to room temperature and concentrated directly onto celite. Flash chromatography [0.5-5% MeOH/DCM+1% NH₄OH] afforded the desired 4-((4'-(3,4-dimethylpiperazin-1-yl)-2'-fluoro-5'-nitro-[1,1'-biphenyl]-3-yl)methyl)morpholine (0.18 g, 62%). LCMS [M+H]⁺: 429.7.

Step 3: 4-(3,4-dimethylpiperazin-1-yl)-6-fluoro-3'-(morpholinomethyl)-[1,1'-biphenyl]-3-amine

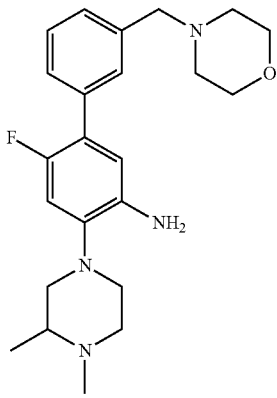 [SMILES: CC1CN(c2cc(F)c(-c3cccc(CN4CCOCC4)c3)cc2N)CCN1C]

A mixture of 4-((4'-(3,4-dimethylpiperazin-1-yl)-2'-fluoro-5'-nitro-[1,1'-biphenyl]-3-yl)methyl)morpholine (0.18 g, 0.43 mmol), iron (0.12 g, 2.2 mmol) and acetic acid (4 mL) was heated to 80° C. for 1 h. The reaction mixture was cooled to room temperature, diluted with DCM and the liquids were decanted by pipette. Concentration onto celite followed by flash chromatography [0.5-10% MeOH/DCM+1% NH₄OH] afforded 4-(3,4-dimethylpiperazin-1-yl)-6-fluoro-3'-(morpholinomethyl)-[1,1'-biphenyl]-3-amine (0.32 mmol, 75%). LCMS [M+H]⁺: 399.7.

Step 4: N-(4-(3,4-dimethylpiperazin-1-yl)-6-fluoro-3'-(morpholinomethyl)-[1,1'-biphenyl]-3-yl)-6-oxo-4-(trifluoromethyl)-1,6-dihydropyridine-3-carboxamide

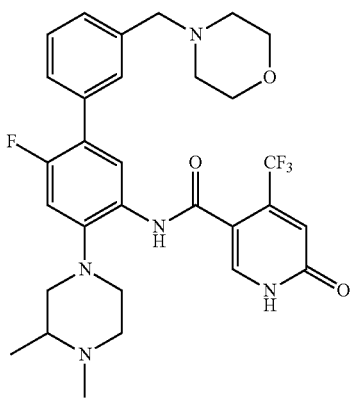

Diethyl chlorophosphate (0.186 ml, 1.285 mmol) was added to a stirring solution of 6-hydroxy-4-(trifluoromethyl) nicotinic acid (0.266 g, 1.285 mmol) in pyridine (3 ml) at room temperature. After stirring for 1 h the solution of activated acid was added to a stirring solution of 4-(3,4-dimethylpiperazin-1-yl)-6-fluoro-3'-(morpholinomethyl)-[1,1'-biphenyl]-3-amine (0.128 g, 0.321 mmol) also in pyridine (3 ml) at room temperature. The reaction was heated to 75° C. overnight. LCMS indicated the presence of the desired product along with the excess nicotinic acid. The reaction was concentrated onto celite and purified by RP flash on the Biotage [5-95% MeCN/water] to afford 135 mg of crude product that was not of sufficient purity by NMR and LCMS. The mixture was loaded onto celite and purified by silica gel chromatography [1-25% MeOH/DCM+1% NH₄OH] to afford the title compound (106 mg, 53.4% yield) as a colorless solid after lyophilization. ¹H NMR (500 MHz, DMSO-d6) δ 9.52 (s, 1H), 7.94 (s, 1H), 7.75 (d, J=8.44 Hz, 1H), 7.29-7.47 (m, 4H), 7.06 (d, J=12.47 Hz, 1H), 6.81 (s, 1H), 3.58 (t, J=4.40 Hz, 4H), 3.53 (s, 2H), 2.99-3.09 (m, 2H), 2.80-2.87 (m, 1H), 2.74-2.80 (m, 1H), 2.32-2.46 (m, 6H), 2.23-2.27 (m, 1H), 0.99 (d, J=6.24 Hz, 3H); LCMS [M+H]⁺ 574 g/mol.

Example 46: N-(4-fluoro-2-(4-methylpiperazin-1-yl)-5-(2-morpholinopyridin-4-yl)phenyl)-6-oxo-4-(trifluoromethyl)-1,6-dihydropyridine-3-carboxamide

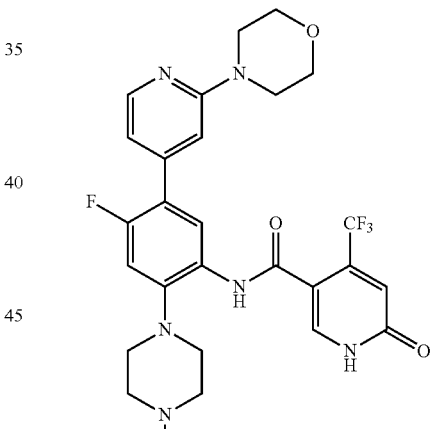

A procedure employed similar to that of Example 3 using N-(5-bromo-4-fluoro-2-(4-methylpiperazin-1-yl)phenyl)-6-oxo-4-(trifluoromethyl)-1,6-dihydropyridine-3-carboxamide (29.10 mg, 0.061 mmol), 2-morpholinopyridine-4-boronic acid, pinacol ester (53.1 mg, 0.183 mmol) gave 17.4 mg (50.7% yield) of the target compound as a white powder. ¹H NMR (500 MHz, MeOD) δ 8.16 (d, J=5.4 Hz, 1H), 7.97 (s, 1H), 7.94 (d, J=8.1 Hz, 1H), 7.10 (d, J=12.2 Hz, 1H), 6.96 (s, 1H), 6.92 (s, 1H), 6.91 (d, J=5.1 Hz, 1H), 3.84-3.80 (m, 4H), 3.54-3.50 (m, 4H), 3.03 (t, J=4.9 Hz, 4H), 2.68 (s, J=2.0 Hz, 4H), 2.39 (s, 3H); LCMS [M+H]⁺ 561 g/mol.

Example 47: N-(4-fluoro-2-(4-methylpiperazin-1-yl)-5-(5-(morpholinomethyl)pyridin-3-yl)phenyl)-6-oxo-4-(trifluoromethyl)-1,6-dihydropyridine-3-carboxamide Example 48: N-(4-fluoro-2-(4-methylpiperazin-1-yl)-5-(5-((((tetrahydro-2H-pyran-4-yl)amino)methyl)pyridin-3-yl)phenyl)-6-oxo-4-(trifluoromethyl)-1,6-dihydropyridine-3-carboxamide

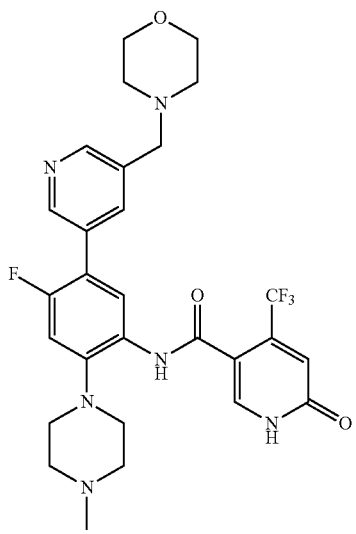

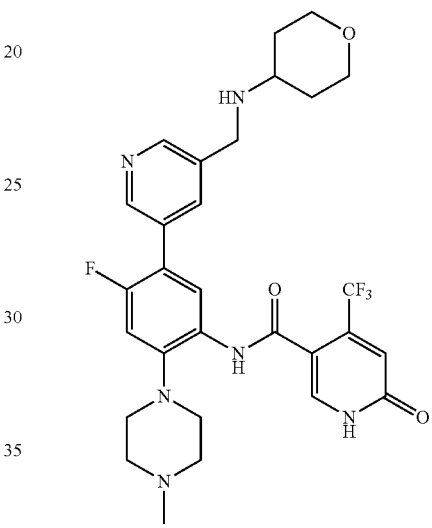

A procedure employed similar to that of Example 29 above using N-(5-bromo-4-fluoro-2-(4-methylpiperazin-1-yl)phenyl)-6-oxo-4-(trifluoromethyl)-1,6-dihydropyridine-3-carboxamide (19.4 mg, 0.041 mmol) and 4-((5-(4,4,5,5-tetramethyl-1,3,2-dioxaborolan-2-yl)pyridin-3-yl)methyl)morpholine (37.1 mg, 0.122 mmol) gave 15.5 mg (64.4% yield) of the title compound as pale yellow powder. $^1$H NMR (500 MHz, CD3CN-D2O) δ 8.74 (s, 1H), 8.57 (s, 1H), 8.12 (d, J=8.2 Hz, 1H), 8.04 (s, 1H), 7.89 (s, 1H), 7.21 (d, J=11.8 Hz, 1H), 6.91 (s, 1H), 3.99 (s, 2H), 3.74 (s, 4H), 3.40 (s, 4H), 3.17 (s, 4H), 2.84 (s, 3H), 2.83 (s, 4H). LCMS [M+H]$^+$ 575 g/mol.

A procedure was employed similar to that of Example 3 using N-(5-bromo-2-(4-methylpiperazin-1-yl)phenyl)-6-oxo-4-(trifluoromethyl)-1,6-dihydropyridine-3-carboxamide (30.52 mg, 0.066 mmol) and 4-((6-fluoro-5-(4,4,5,5-tetramethyl-1,3,2-dioxaborolan-2-yl)pyridin-3-yl)methyl)morpholine (64.2 mg, 0.199 mmol) to give 11.9 mg (30.1% yield) of the title compound. $^1$H NMR (500 MHz, MeOD) δ 8.67 (t, J=2.1 Hz, 1H), 8.56 (d, J=2.2 Hz, 1H), 8.07 (t, J=2.6 Hz, 1H), 8.00 (d, J=8.3 Hz, 1H), 7.98 (s, 1H), 7.15 (d, J=12.0 Hz, 1H), 6.92 (s, 1H), 3.99 (s, 2H), 3.98-3.95 (m, 2H), 3.42 (td, J=12.0, 2.2 Hz, 2H), 3.06-3.02 (m, 4H), 2.85 (ddd, J=15.2, 9.4, 4.2 Hz, 1H), 2.67 (s, J=2.7 Hz, 4H), 2.38 (s, 3H), 1.95 (ddd, J=6.6, 4.2, 2.0 Hz, 2H), 1.50 (ddd, J=24.2, 12.2, 4.6 Hz, 2H); LCMS [M+H]$^+$ 589 g/mol.

Example 49: (R)—N-(4-fluoro-2-(4-methylpiperazin-1-yl)-5-(5-(((tetrahydrofuran-3-yl)amino)methyl)pyridin-3-yl)phenyl)-6-oxo-4-(trifluoromethyl)-1,6-dihydropyridine-3-carboxamide

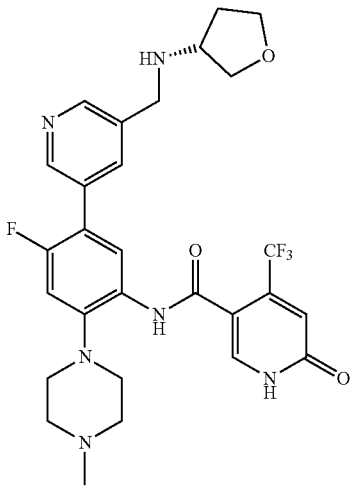

A procedure was employed similar to that of Example 3 using N-(5-bromo-4-fluoro-2-(4-methylpiperazin-1-yl)phenyl)-6-oxo-4-(trifluoromethyl)-1,6-dihydropyridine-3-carboxamide (20.46 mg, 0.043 mmol) and (R)—N-((5-(4,4,5,5-tetramethyl-1,3,2-dioxaborolan-2-yl)pyridin-3-yl)methyl)tetrahydrofuran-3-amine (39.1 mg, 0.129 mmol) to give the title compound (16.0 mg) in 60.5% yield. $^1$H NMR (500 MHz, MeOD) δ 8.85 (s, 1H), 8.72 (d, J=2.0 Hz, 1H), 8.23 (t, J=2.3 Hz, 1H), 8.07 (d, J=8.1 Hz, 1H), 8.05 (s, 1H), 7.26 (d, J=11.8 Hz, 1H), 6.94 (s, 1H), 4.39 (d, J=2.4 Hz, 2H), 4.11-4.06 (m, 2H), 4.02 (ddd, J=11.0, 6.9, 2.5 Hz, 1H), 3.87 (dd, J=10.9, 5.7 Hz, 1H), 3.76 (dt, J=15.5, 8.4 Hz, 1H), 2.94 (s, 3H), 2.45 (dtd, J=13.4, 8.1, 5.0 Hz, 1H), 2.13 (dtd, J=11.3, 7.6, 3.3 Hz, 1H); LCMS [M+H]$^+$ 575 g/mol.

Example 50: (R)—N-(4-(3,4-dimethylpiperazin-1-yl)-6-fluoro-3'-(morpholinomethyl)-[1,1'-biphenyl]-3-yl)-6-oxo-4-(trifluoromethyl)-1,6-dihydropyridine-3-carboxamide

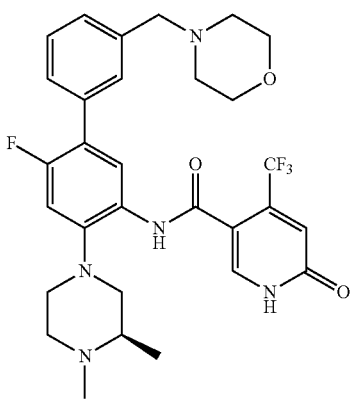

Step 1: (R)-4-(4-chloro-5-fluoro-2-nitrophenyl)-1,2-dimethylpiperazine

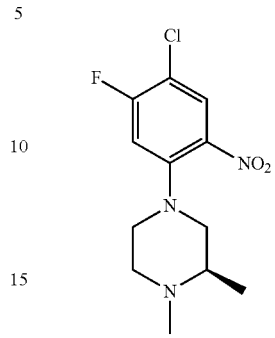

A vial was charged with 1-bromo-4-chloro-5-fluoro-2-nitrobenzene (1.0 g, 3.93 mmol), (R)-1,2-dimethyl-piperazine dihydrochloride (0.772 g, 4.13 mmol), palladium(II) acetate (0.088 g, 0.393 mmol), Xantphos (0.227 g, 0.393 mmol) and cesium carbonate (5.12 g, 15.72 mmol). The vial was sealed with a septum and evacuated and back-filled with nitrogen. Toluene (15 ml) was added and the vial was evacuated and back-filled again. The reaction was warmed to 50° C. After 7.5 h total reaction time, LCMS indicated the complete consumption of the starting material. The reaction mixture was transferred to a round bottom flask with DCM and then concentrated onto celite. Flash [0.5-10% MeOH/DCM+1% NH$_4$OH] afforded 490 mg (41.2% yield) of the title compound. LCMS [M+H]+=288.3

Step 2: (R)-4-((4'-(3,4-dimethylpiperazin-1-yl)-2'-fluoro-5'-nitro-[1,1'-biphenyl]-3-yl)methyl)morpholine

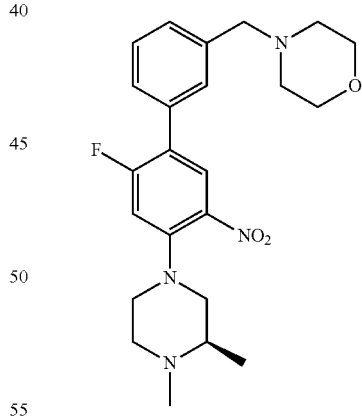

A 30 mL vial was charged with a mixture of (R)-4-(4-chloro-5-fluoro-2-nitrophenyl)-1,2-dimethylpiperazine (0.050 g, 0.174 mmol), 3-(4-morpholinomethyl)phenylboronic acid pinacol ester (0.074 g, 0.243 mmol), XPhos Pd G2 (2.73 mg, 3.48 µmol) and XPhos (1.657 mg, 3.48 µmol). The vial was sealed with a cap/septum, evacuated and backfilled with nitrogen. 1,4-Dioxane (2 ml) and 2M Aq sodium carbonate (0.434 ml, 0.869 mmol) were added via syringe and the vial was evacuated and backfilled an additional time. The reaction was heated in an aluminum block overnight at 100° C. LCMS indicated very clean conversion to the desired product. The reaction mixture was loaded onto celite and purified by flash chromatography [0.1-5% MeOH/DCM+1% NH₄OH] to afford the product (0.152 mmol, 87% yield) as a yellow film.

Step 3: (R)-4-(3,4-dimethylpiperazin-1-yl)-6-fluoro-3'-(morpholinomethyl)-[1,1'-biphenyl]-3-amine

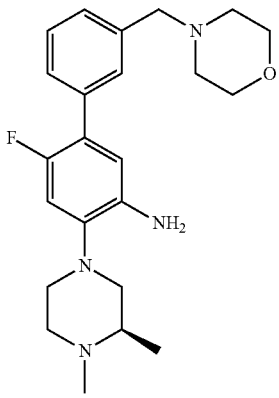 [SMILES: C[C@@H]1CN(c2cc(F)c(-c3cccc(CN4CCOCC4)c3)cc2N)CCN1C]

A mixture of (R)-4-((4'-(3,4-dimethylpiperazin-1-yl)-2'-fluoro-5'-nitro-[1,1'-biphenyl]-3-yl)methyl)morpholine (0.065 g, 0.152 mmol), iron (0.042 g, 0.758 mmol) and acetic acid (2 ml) was heated to 80° C. for 1 h. The heating block was turned off and the reaction was stirred at room temperature overnight. The reaction mixture was diluted with DCM and decanted by pipette to a round bottom flask. LCMS indicated complete conversion to the desired product. Concentration onto celite followed by flash [0.1-10% MeOH/DCM+1% NH₄OH] afforded the product (0.123 mmol, 81% yield) as a brown film that was pure by LCMS. LCMS [M+H]+=399.5.

Step 4: (R)—N-(4-(3,4-dimethylpiperazin-1-yl)-6-fluoro-3'-(morpholinomethyl)-[1,1'-biphenyl]-3-yl)-6-oxo-4-(trifluoromethyl)-1,6-dihydropyridine-3-carboxamide

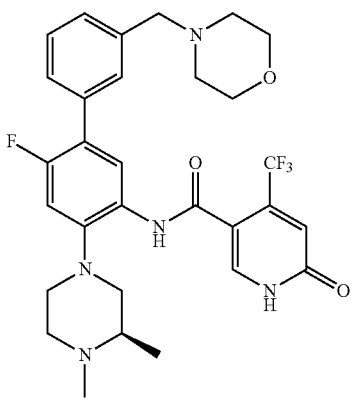

Diethyl chlorophosphate (0.071 ml, 0.492 mmol) was added to a stirring solution of 6-hydroxy-4-(trifluoromethyl) nicotinic acid (0.102 g, 0.492 mmol) in pyridine (1.5 ml) at room temperature. After stirring for 30 minutes the solution of activated acid was added to a stirring solution of (R)-4-(3,4-dimethylpiperazin-1-yl)-6-fluoro-3'-(morpholinomethyl)-[1,1'-biphenyl]-3-amine (0.049 g, 0.123 mmol) also in pyridine (1.5 ml) at room temperature. The reaction was heated to 75° C. for ~3 h. The reaction was concentrated onto celite and purified by flash [1-25% MeOH/DCM+1% NH₄OH] to afford crude product that was ~92% pure [254 nm]. This material was loaded onto celite and repurified on the biotage [5-95% MeCN/water—no modifier] to afford the title compound (0.022 mmol, 17.99% yield) as a tan solid that was pure by LCMS. ¹H NMR (500 MHz, DMSO-d₆) δ=9.41 (br. s., 1H), 7.97 (s, 1H), 7.80 (d, J=8.7 Hz, 1H), 7.47-7.29 (m, 5H), 7.06 (d, J=12.5 Hz, 1H), 6.69 (br. s., 1H), 3.57 (t, J=4.3 Hz, 4H), 3.52 (s, 2H), 3.07-2.97 (m, 2H), 2.86-2.74 (m, 2H), 2.45-2.40 (m, 2H), 2.39-2.34 (m, 5H), 2.21 (s, 3H), 0.98 (d, J=6.2 Hz, 3H); LCMS [M+H]⁺ 574 g/mol.

Example 51: (S)—N-(4-(3,4-dimethylpiperazin-1-yl)-6-fluoro-3'-(morpholinomethyl)-[1,1'-biphenyl]-3-yl)-6-oxo-4-(trifluoromethyl)-1,6-dihydropyridine-3-carboxamide

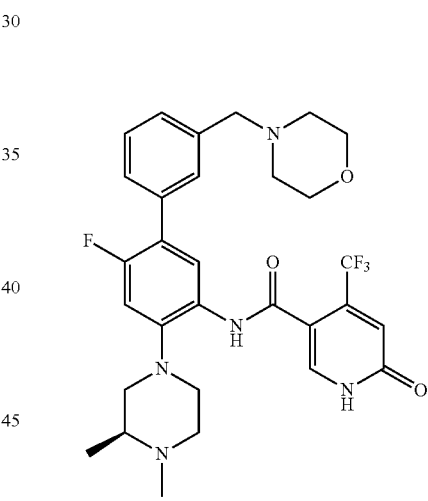

The title compound was prepared similar to the sequence described above for the preparation of Example 50 above using (S)-1,2-dimethyl-piperazine hydrochloride in place of racemic 1,2-dimethyl-piperazine in Step 1, to give 19.0 mg (28% yield) of the title compound in the last step. ¹H NMR (500 MHz, DMSO-d₆) δ=9.44 (s, 1H), 7.96 (s, 1H), 7.78 (d, J=8.6 Hz, 1H), 7.47-7.28 (m, 4H), 7.06 (d, J=12.5 Hz, 1H), 6.73 (s, 1H), 3.57 (t, J=4.3 Hz, 4H), 3.52 (s, 2H), 3.07-2.98 (m, 2H), 2.86-2.74 (m, 2H), 2.45-2.33 (m, 6H), 2.26-2.19 (m, 4H), 0.98 (d, J=6.1 Hz, 3H); LCMS [M+H]+: 588.4.

Example 52: N-(6-fluoro-3'-(morpholinomethyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide

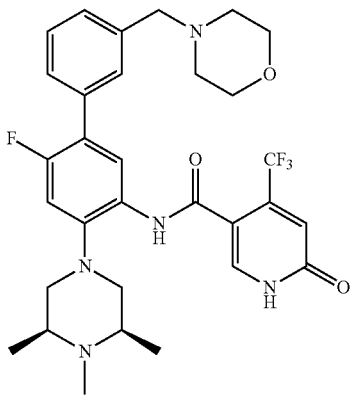 [SMILES: C[C@@H]1CN(c2cc(F)c(-c3cccc(CN4CCOCC4)c3)cc2NC(=O)c2c[nH]c(=O)cc2C(F)(F)F)C[C@H](C)N1C]

The sequence described above for the preparation of Example 50 using cis-1,2,6-trimethyl-piperazine in place of racemic 1,2-dimethyl-piperazine was used to give 7 mg (21% yield) of the title compound in the final step. $^1$H NMR (500 MHz, DMSO-$d_6$) δ=9.30 (br. s., 1H), 8.01 (s, 1H), 7.84 (d, J=8.6 Hz, 1H), 7.48-7.28 (m, 4H), 7.04 (d, J=12.3 Hz, 1H), 6.55 (br. s., 1H), 3.57 (t, J=4.3 Hz, 4H), 3.52 (s, 2H), 3.01 (d, J=10.9 Hz, 2H), 2.40-2.31 (m, 7H), 2.20 (s, 3H), 1.02 (d, J=6.1 Hz, 6H); LCMS [M+H]$^+$=602.4.

Example 53: N-(4-(3-(dimethylamino)pyrrolidin-1-yl)-6-fluoro-3'-(morpholinomethyl)-[1,1'-biphenyl]-3-yl)-6-oxo-4-(trifluoromethyl)-1,6-dihydropyridine-3-carboxamide

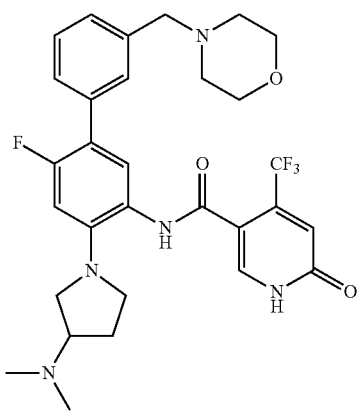 [SMILES: CN(C)C1CCN(c2cc(F)c(-c3cccc(CN4CCOCC4)c3)cc2NC(=O)c2c[nH]c(=O)cc2C(F)(F)F)C1]

Step 1: 1-(2-fluoro-3'-(morpholinomethyl)-5-nitro-[1,1'-biphenyl]-4-yl)-N,N-dimethylpyrrolidin-3-amine

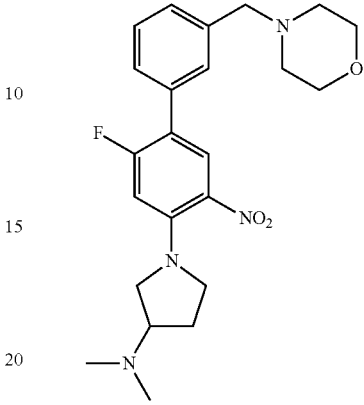

A vial was charged with a mixture of 1-(4-bromo-5-fluoro-2-nitrophenyl)-N,N-dimethylpyrrolidin-3-amine (0.092 g, 0.28 mmol, prepared as described in Example 21 above), 3-(4-morpholinomethyl)phenylboronic acid pinacol ester (0.12 g, 0.39 mmol), XPhos Pd G2 (0.0044 g, 0.005 mmol) and XPhos (0.0026 g, 0.005 mmol). The vial was sealed with a septum cap and evacuated and backfilled with nitrogen. 1,4-Dioxane (4 mL) and 2M Aq sodium carbonate (0.70 mL, 1.4 mmol) were added via syringe. The vial was evacuated and backfilled an additional time before being heated at 95° C. overnight. The reaction was cooled to room temperature and concentrated directly onto celite. Flash chromatography [0.5-10% MeOH/DCM+1% NH$_4$OH] afforded 1-(2-fluoro-3'-(morpholinomethyl)-5-nitro-[1,1'-biphenyl]-4-yl)-N,N-dimethylpyrrolidin-3-amine (0.110 g, 86%). LCMS [M+H]+: 429.5.

Step 2: 1-(5-amino-2-fluoro-3'-(morpholinomethyl)-[1,1'-biphenyl]-4-yl)-N,N-dimethylpyrrolidin-3-amine

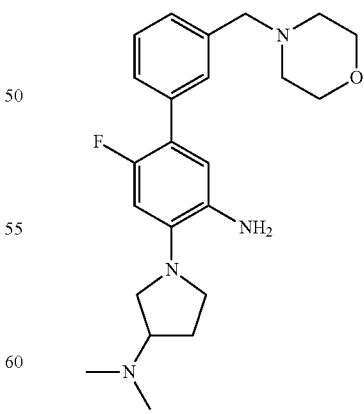

A mixture of 1-(2-fluoro-3'-(morpholinomethyl)-5-nitro-[1,1'-biphenyl]-4-yl)-N,N-dimethylpyrrolidin-3-amine (0.11 g, 0.26 mmol), iron (0.070 g, 1.3 mmol) and acetic acid (3 mL) was heated to 85° C. for 1 h. The reaction mixture was Step 3: N-(4-(3-(dimethylamino)pyrrolidin-1-yl)-6-fluoro-3'-(morpholinomethyl)-[1,1'-biphenyl]-3-yl)-6-oxo-4-(trifluoromethyl)-1,6-dihydropyridine-3-carboxamide

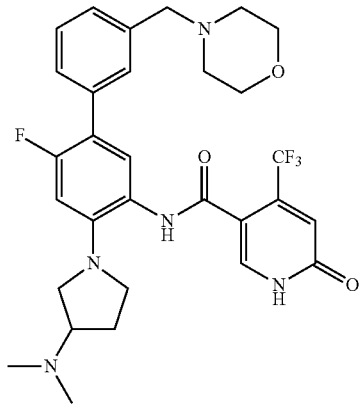 [SMILES: CN(C)C1CCN(c2cc(F)c(-c3cccc(CN4CCOCC4)c3)cc2NC(=O)c2c[nH]c(=O)cc2C(F)(F)F)C1]

Diethyl chlorophosphate (0.090 mL, 0.61 mmol) was added to a stirring solution of 6-hydroxy-4-(trifluoromethyl) nicotinic acid (0.130 g, 0.61 mmol) in pyridine (2 mL) at room temperature. After stirring for 45 minutes the solution of activated acid was added to a stirring solution of 1-(5-amino-2-fluoro-3'-(morpholinomethyl)-[1,1'-biphenyl]-4-yl)-N,N-dimethylpyrrolidin-3-amine (0.061 g, 0.15 mmol) also in pyridine (2 mL) at room temperature. The reaction was heated to 75° C. for 5 h. The reaction mixture was concentrated onto celite and reverse phase chromatography [5-95% MeCN/water; C18 column] afforded the title compound (28.0 mg, 30% yield). $^1$H-NMR (500 MHz, DMSO-d6) δ 12.57 (br. s., 1H), 9.82 (d, J=5.14 Hz, 1H), 7.97 (br. s., 1H), 7.34-7.43 (m, 3H), 7.22-7.33 (m, 2H), 6.80 (d, J=5.38 Hz, 1H), 6.66 (dd, J=5.99, 14.31 Hz, 1H), 3.58 (br. s., 4H), 3.51 (d, J=5.87 Hz, 2H), 3.40-3.42 (m, 2H), 3.26 (m, 1H), 2.64 (br. s., 1H), 2.38 (br. s., 4H), 2.12-2.22 (m, 7H), 2.09 (d, J=3.79 Hz, 1H), 1.71 (d, J=7.70 Hz, 1H); LCMS [M+H]+=588.5.

Example 54: N-(6-chloro-4-(4-methylpiperazin-1-yl)-3'-(morpholinomethyl)-[1,1'-biphenyl]-3-yl)-6-oxo-4-(trifluoromethyl)-1,6-dihydropyridine-3-carboxamide (Comparative Example)

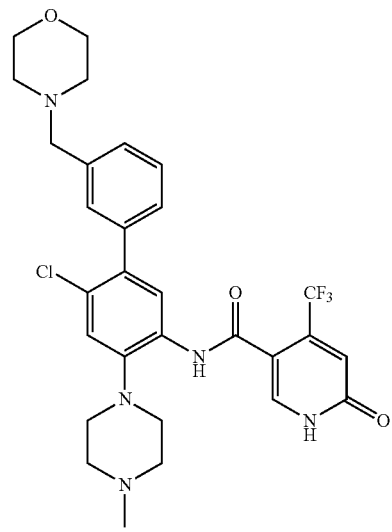 [SMILES: CN1CCN(c2cc(Cl)c(-c3cccc(CN4CCOCC4)c3)cc2NC(=O)c2c[nH]c(=O)cc2C(F)(F)F)CC1]

To a 2 ml microwave vial containing a suspension of 6-hydroxy-4-(trifluoromethyl)nicotinic acid (103 mg, 0.499 mmol) in pyridine, anhydrous (603 μl, 7.48 mmol) was added slowly diethyl chlorophosphate (72.1 μl, 0.499 mmol) at rt in an atmosphere of nitrogen. The reaction mixture was stirred at rt for 1 h. To this mixture was added 6-chloro-4-(4-methylpiperazin-1-yl)-3'-(morpholinomethyl)-[1,1'-biphenyl]-3-amine (50 mg, 0.125 mmol, prepared in a similar manner to examples hereinabove) and the reaction was heated at 70° C. for 2 h. After completion, pyridine was removed in vacuo and the residue partitioned between ethyl acetate (3 mL) and saturated sodium bicarbonate solution (3 mL). The suspension was stirred for 10 min. The organic layer was separated, and dried over anhydrous Na$_2$SO$_4$. The solvent was evaporated in vacuo yielding the crude product. Purification was performed via preparative HPLC to yield the title compound (10.4 mg, 12% yield). $^1$H NMR (500 MHz, MeOD) δ 8.47 (s, 1H), 7.96 (s, 1H), 7.95 (s, 1H), 7.45 (s, 1H), 7.42 (d, J=7.4 Hz, 1H), 7.38 (d, J=5.6 Hz, 2H), 7.36 (s, 1H), 6.92 (s, 1H), 3.72-3.70 (m, 4H), 3.64 (s, 2H), 3.05 (t, J=4.4 Hz, 4H), 2.80 (s, 4H), 2.54 (s, 4H), 2.48 (s, 3H); LCMS [M+H]+ 591 g/mol.

Example 55: N-[4-methoxy-5-(2-morpholin-4-ylpyrimidin-5-yl)-2-[(3R,5S)-3,4,5-trimethylpiperazin-1-yl]phenyl]-6-oxo-4-(trifluoromethyl)-1H-pyridine-3-carboxamide Comparative Example

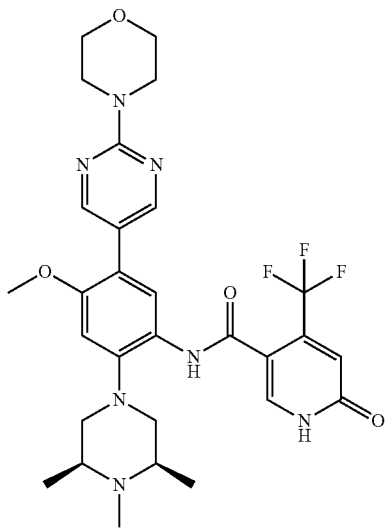 [SMILES: COc1cc(N2C[C@@H](C)N(C)[C@@H](C)C2)c(NC(=O)c2c[nH]c(=O)cc2C(F)(F)F)cc1-c1cnc(N2CCOCC2)nc1]

Step 1: cis-4-(4-bromo-5-methoxy-2-nitrophenyl)-1,2,6-trimethylpiperazine

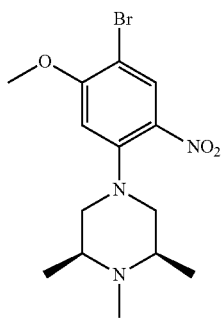 [SMILES: COc1cc(N2C[C@@H](C)N(C)[C@@H](C)C2)c([N+](=O)[O-])cc1Br]

A solution of 1-bromo-4-fluoro-2-methoxy-5-nitrobenzene (0.250 g, 1.0 mmol) in PhMe (1 mL) was slowly added to a rapidly stirring mixture of cis-1,2,6-trimethylpiperazine (0.13 g, 1.0 mmol) and K$_2$CO$_3$ (0.070 g, 0.50 mmol) in PhMe (2 mL) at 45° C. After 2 h the heat was turned off and the reaction was allowed to stir at room temperature for 18 h. The reaction mixture was concentrated onto celite and purification by flash chromatography [0.5-10% MeOH/DCM+0.5% NH$_4$OH] afforded cis-4-(4-bromo-5-methoxy-2-nitrophenyl)-1,2,6-trimethylpiperazine (0.33 g, 92%). LCMS [M+H]+: 358.3.

Step 2: 4-(5-(2-methoxy-5-nitro-4-(cis-3,4,5-trimethylpiperazin-1-yl)phenyl)pyrimidin-2-yl)morpholine

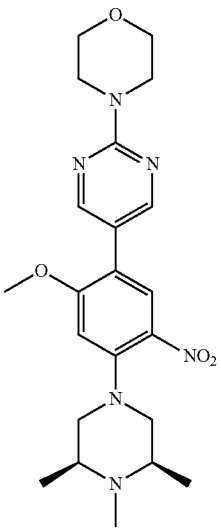

A reaction vial was charged with a mixture of cis-4-(4-bromo-5-methoxy-2-nitrophenyl)-1,2,6-trimethylpiperazine (0.11 g, 0.31 mmol), 2-(4-morpholino)pyrimidine-5-boronic acid pinacol ester (0.098 g, 0.34 mmol), XPhos Pd G2 (5 mg, 6 μmol) and XPhos (3 mg, 6 μmol). The vial was sealed with a septum, evacuated and backfilled with nitrogen. 1,4-Dioxane (3 mL) and 2 M aqueous sodium carbonate (0.5 mL) were added via syringe and the vial was evacuated and backfilled an additional time. The reaction was heated to 90° C. in an aluminum block for 18 h. After cooling to room temperature the reaction mixture was concentrated onto celite and purified by flash chromatography [0.5-10% MeOH/DCM+0.5% NH$_4$OH] to afford 4-(5-(2-methoxy-5-nitro-4-(cis-3,4,5-trimethylpiperazin-1-yl)phenyl)pyrimidin-2-yl)morpholine (0.14 g, 100%). LCMS [M+H]+: 443.3.

Step 3: 4-methoxy-5-(2-morpholinopyrimidin-5-yl)-2-(cis-3,4,5-trimethylpiperazin-1-yl)aniline

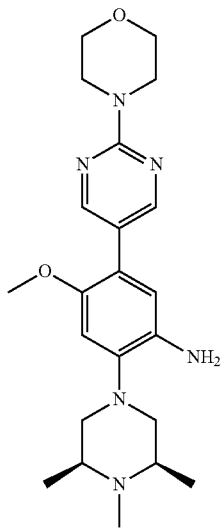 [SMILES: COc1cc(N2C[C@@H](C)N(C)[C@@H](C)C2)c([N+](=O)[O-])cc1-c1cnc(N2CCOCC2)nc1]

A mixture of 4-(5-(2-methoxy-5-nitro-4-(cis-3,4,5-trimethylpiperazin-1-yl)phenyl)pyrimidin-2-yl)morpholine (0.14 g, 0.31 mmol), SnCl₂ (0.24 g, 1.2 mmol) and EtOH (5 mL) was heated to 75° C. for 1 h. The heat was turned off and the reaction was allowed to stir at room temperature overnight. The reaction mixture was concentrated onto celite and purified by flash chromatography [0.5-10% MeOH/DCM+1% NH₄OH] to afford 4-methoxy-5-(2-morpholinopyrimidin-5-yl)-2-(cis-3,4,5-trimethylpiperazin-1-yl)aniline (0.11 g, 83%). LCMS [M+H]+: 413.6.

Step 4: N-(4-methoxy-5-(2-morpholinopyrimidin-5-yl)-2-(cis-3,4,5-trimethylpiperazin-1-yl)phenyl)-6-oxo-4-(trifluoromethyl)-1,6-dihydropyridine-3-carboxamide

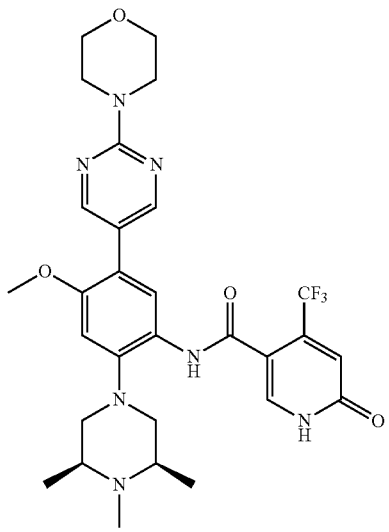 [SMILES: COc1cc(N2C[C@@H](C)N(C)[C@@H](C)C2)c(NC(=O)c2c[nH]c(=O)cc2C(F)(F)F)cc1-c1cnc(N2CCOCC2)nc1]

4-(trifluoromethyl)-6-(2-(trimethylsilyl)ethoxy)nicotinic acid (0.056 g, 0.18 mmol) was activated with HATU (0.069 g, 0.18 mmol) and N,N-diisopropylethylamine (0.03 mL, 0.18 mmol) in DMF (0.5 mL) at room temperature. The solution of activated acid was added to a solution of 4-methoxy-5-(2-morpholinopyrimidin-5-yl)-2-(cis-3,4,5-trimethylpiperazin-1-yl)aniline (0.050 g, 0.12 mmol) in DMF (1 mL) and the reaction was heated to 55° C. for 18 h. After cooling to room temperature the reaction mixture was concentrated onto celite and purified by flash chromatography [0.5-7.5% MeOH/DCM+0.5% NH₄OH]. The silyl protected amide was dissolved in DCM (2 mL) and treated with TFA (1 mL) at room temperature. After stirring for 2 h the volatiles were removed under a stream of air and the title compound was isolated by a catch and release protocol using a SCX2 silica cartridge to afford the title compound (0.067 g, 92%). $^1$H NMR (500 MHz, DMSO-d6) δ=9.37 (s, 1H), 8.47 (s, 2H), 7.90 (s, 1H), 7.57 (s, 1H), 6.85-6.74 (m, 2H), 3.81 (s, 3H), 3.75-3.72 (m, 4H), 3.70-3.66 (m, 4H), 3.00 (br d, J=10.9 Hz, 3H), 2.47-2.43 (m, 1H), 2.38-2.30 (m, 2H), 2.21 (s, 3H), 1.02 (d, J=6.1 Hz, 6H); LCMS [M+H]+: 602.5.

Example 56: N-(2-(4-methylpiperazin-1-yl)-5-(2-morpholinopyrimidin-5-yl)phenyl)-6-oxo-4-(trifluoromethyl)-1,6-dihydropyridine-3-carboxamide (Comparative Example)

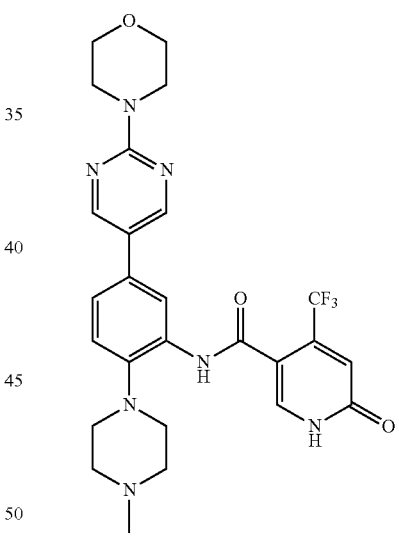

The procedure followed was similar to that used for Example 3 above using N-(5-bromo-2-(4-methylpiperazin-1-yl)phenyl)-6-oxo-4-(trifluoromethyl)-1,6-dihydropyridine-3-carboxamide (51.9 mg, 0.108 mmol) and 2-(4-morpholino)pyrimidine-5-boronic acid pinacol ester (95 mg, 0.325 mmol) to afford the title compound (39.5 mg, 55% yield) as a white solid. 1H NMR (500 MHz, DMSO) δ 9.45 (s, 1H), 8.63 (s, 2H), 8.01 (d, J=2.0 Hz, 1H), 7.98 (s, 1H), 7.42 (dd, J=8.3, 2.2 Hz, 1H), 7.25 (d, J=8.3 Hz, 1H), 6.80 (s, 1H), 3.74 (q, J=4.5 Hz, 4H), 3.68 (q, J=4.5 Hz, 4H), 2.87 (t, J=4.4 Hz, 4H), 2.47 (s, 4H), 2.22 (s, 3H); LCMS [M+H]+ 544.

Example 57: N-[2-(4-methylpiperazin-1-yl)-5-[3-(morpholin-4-ylmethyl)phenyl]phenyl]-6-oxo-4-(trifluoromethyl)-1H-pyridine-3-carboxamide (Comparative Example)

Example 58: N-(5-(2-morpholinopyrimidin-5-yl)-2-((3R,5S)-3,4,5-trimethylpiperazin-1-yl)phenyl)-6-oxo-4-(trifluoromethyl)-1,6-dihydropyridine-3-carboxamide Comparative Example

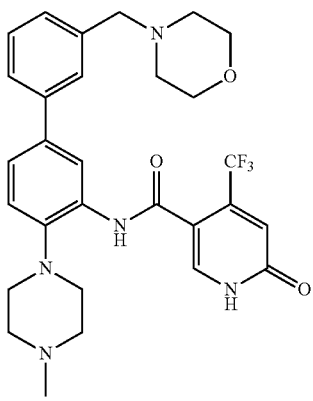

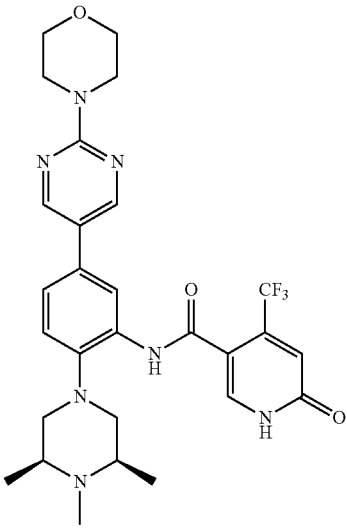 [SMILES: C[C@@H]1CN(c2ccc(-c3cnc(N4CCOCC4)nc3)cc2NC(=O)c2c[nH]c(=O)cc2C(F)(F)F)C[C@H](C)N1C]

6-Hydroxy-4-(trifluoromethyl)nicotinic acid (69.2 mg, 0.327 mmol) was dissolved/suspended in $SOCl_2$ (1 mL) and stirred at 70° C. for 2 h. The $SOCl_2$ was removed under reduced pressure (h/v 1 h). The residue was dissolved in DCM and 4-(4-methylpiperazin-1-yl)-3'-(morpholinomethyl)-[1,1'-biphenyl]-3-amine (100 mg, 0.273 mmol, prepared using methods similar to those described for Example 29) was added in one portion before pyridine (28.7 μl, 0.355 mmol) was added. The reaction mixture was stirred for 3d, diluted with sat. aq. sodium bicarbonate solution and extracted with DCM (3×5 mL). The combined organic phases were loaded on silica gel and subjected to purification via Biotage (25 g column, MeOH/DCM 0-30%, 30 CV) to give the title compound (15 mg, 8.91% yield). $^1$H-NMR (500 MHz, MeOD) δ 8.77 (d, J=2.0 Hz, 1H), 8.26 (d, J=2.0 Hz, 1H), 8.08 (dd, J=8.1, 2.3 Hz, 1H), 8.02 (s, 1H), 7.63 (d, J=8.2 Hz, 1H), 7.55 (dd, J=8.3, 2.1 Hz, 1H), 7.42 (t, J=4.2 Hz, 1H), 6.94 (s, 1H), 3.79 (s, 2H), 3.75-3.73 (m, 4H), 3.15 (s, 4H), 2.72 (s, 4H), 2.63 (s, 3H); LCMS [M+H]+ 557.

N-(5-bromo-2-((3S,5R)-3,4,5-trimethylpiperazin-1-yl)phenyl)-6-oxo-4-(trifluoromethyl)-1,6-dihydropyridine-3-carboxamide (39 mg, 0.08 mmol) and 2-(4-morpholino)pyrimidine-5-boronic acid pinacol ester (35 mg, 0.12 mmol) were employed in a procedure similar to Step 3, Example 31 to give the title compound as a beige solid (13.0 mg, 28% yield). $^1$H-NMR (500 MHz, METHANOL-d4) δ 8.64 (s, 2H), 8.17 (s, 1H), 8.00 (s, 1H), 7.42 (d, J=8.0 Hz, 1H), 7.33 (d, J=8.2 Hz, 1H), 6.92 (s, 1H), 3.87-3.81 (m, 4H), 3.81-3.75 (m, 4H), 3.00 (d, J=11.4 Hz, 2H), 2.67 (t, J=11.1 Hz, 2H), 2.59-2.47 (m, 2H), 2.39 (s, 3H), 1.18 (d, J=6.2 Hz, 6H); LC-MS [M+H]+ 572.26.

Example 59: N-[5-(2-morpholin-4-ylpyrimidin-5-yl)-2-[rac-(3R,5S)-3,4,5-trimethylpiperazin-1-yl]-4-(trifluoromethyl)phenyl]-6-oxo-4-(trifluoromethyl)-1H-pyridine-3-carboxamide

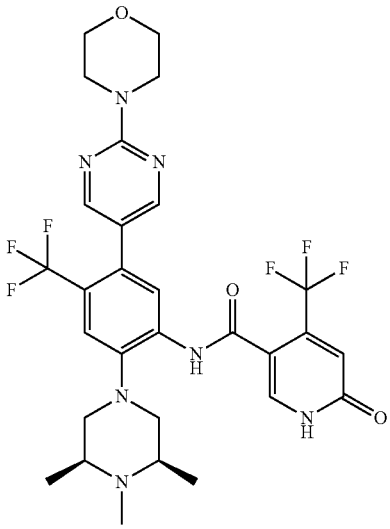 [SMILES: C[C@@H]1CN(c2cc(C(F)(F)F)c(-c3cnc(N4CCOCC4)nc3)cc2NC(=O)c2c[nH]c(=O)cc2C(F)(F)F)C[C@H](C)N1C]

Step 1: (2S,6R)-1,2,6-trimethyl-4-(2-nitro-5-(trifluoromethyl)phenyl)piperazine

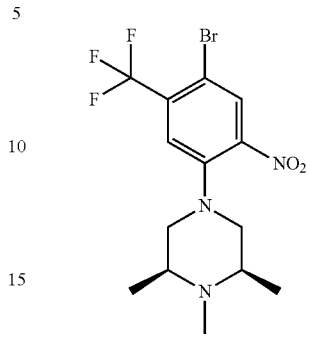

To a solution of 3-fluoro-4-nitrobenzotrifluoride (1 g, 4.78 mmol) in DMSO (2 ml) was added (2R,6S)-1,2,6-trimethylpiperazine (0.644 g, 5.02 mmol) and diisopropylethylamine (0.9 ml, 5.25 mmol). Slight exothermicity was observed. The resulting dark red solution was stirred at RT for 1 h. Only traces of the starting material were observed. The reaction mixture was diluted with water (30 ml) and extracted with EtOAc (3×25 ml). The combined organic phase was washed with water, and brine, dried over Na$_2$SO$_4$ and concentrated to obtain an orange oil as the desired product. (1.481 g, 98%). After standing overnight, the oil became an orange solid. This was taken to the next step without any purification. LCMS [M+H]$^+$ 318.4.

Step 2: (2S,6R)-4-(4-bromo-2-nitro-5-(trifluoromethyl)phenyl)-1,2,6-trimethylpiperazine

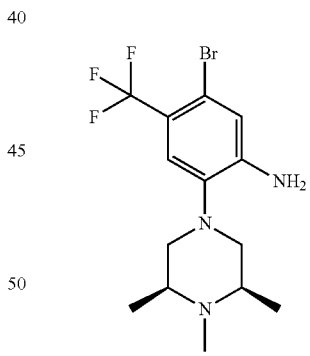

To a solution of (2S,6R)-1,2,6-trimethyl-4-(2-nitro-5-(trifluoromethyl)phenyl)piperazine (1.150 g, 3.62 mmol) in acetic acid (10 ml) was added bromine (0.467 ml, 9.06 mmol). Slight exothermicity was observed. The resulting dark red solution was stirred at 80° C. for 4 h. 52% conversion was observed. 0.2 ml bromine and 3 ml acetic acid were added and the reaction mixture was heated overnight at 80° C. for 22 h. A small amount of starting material was observed. The mixture was allowed to cool to RT, concentrated, the residue was taken up in DCM, neutralized with Satd. NaHCO$_3$ soln., washed with brine, dried over Na$_2$SO$_4$ and concentrated to obtain the crude product. It was purified on a 40 g Isco column, eluting with DCM containing 0-2% MeOH, to yield the desired product as a light brown solid (378 mg, 26%). LCMS [M+H]+ 396.5

Step 3: 5-bromo-4-(trifluoromethyl)-2-((3S,5R)-3,4,5-trimethylpiperazin-1-yl)aniline To a solution of (2S,6R)-4-(4-bromo-2-nitro-5-(trifluoromethyl)phenyl)-1,2,6-trimethylpiperazine (345 mg, 0.871 mmol) in acetic acid (4 ml), was added iron powder, 99% (243 mg, 4.35 mmol). The resulting dark brown solution was stirred at 80° C. The reaction mixture became a slurry and the conversion was complete in 12 min. The mixture was allowed to cool to RT, concentrated, the residue was taken up in DCM, neutralized with Satd. NaHCO$_3$ soln., washed with brine, dried over Na$_2$SO$_4$ and concentrated to afford the crude product. It was purified on reverse phase Isco column (15.5), eluting with water containing 0-80% CH$_3$CN to collect the title compound as a yellow solid (300 mg, 94%). LCMS [M+H]+ 366.5

Step 4: N-(5-bromo-4-(trifluoromethyl)-2-((3S,5R)-3,4,5-trimethylpiperazin-1-yl)phenyl)-6-oxo-4-(trifluoromethyl)-1,6-dihydropyridine-3-carboxamide

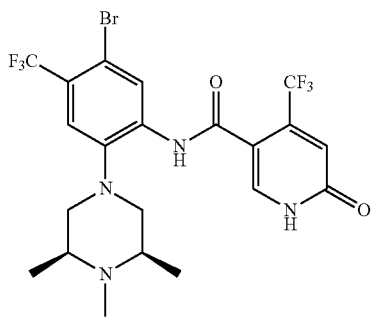 [SMILES: C[C@@H]1CN(c2cc(C(F)(F)F)c(Br)cc2NC(=O)c2c[nH]c(=O)cc2C(F)(F)F)C[C@H](C)N1C]

To a 10 mL RBF charged with 6-chloro-4-(trifluoromethyl)nicotinic acid (115 mg, 0.512 mmol), was added thionyl chloride (894 µl, 12.29 mmol). The resulting suspension was heated at 80° C. for 1 h. It was evaporated to give a light yellow oil which was taken up in DCM (3 mL). 5-bromo-4-(trifluoromethyl)-2-((3S,5R)-3,4,5-trimethylpiperazin-1-yl)aniline (150 mg, 0.410 mmol) and triethylamine (171 µl, 1.229 mmol) were added and the resulting mixture was stirred at RT for 1 h. After basifying with sat. NaHCO$_3$ (5 mL), it was extracted with DCM (5×2 mL). The extracts were combined and concentrated to obtain the crude as a pale brown waxy solid. The reaction was combined with HOAc/H$_2$O (3.6 mL/1.2 mL) in a 5 mL microwave vial and was heated in the microwave at 160° C. for 5 h Solvents were removed on a rotovap at 60° C. and the residue was treated with sat. NaHCO$_3$ (30 mL). It was extracted with DCM (2×45 ml). The extracts were combined, dried over Na$_2$SO$_4$, concentrated onto celite and purified on silica gel column (12 G), eluting with DCM containing 0-5% MeOH. The desired product was obtained as a light purple coloured solid (131 mg, 58%). LCMS [M+H]+ 555.1

Step 5: N-[5-(2-morpholin-4-ylpyrimidin-5-yl)-2-[(3R,5S)-3,4,5-trimethylpiperazin-1-yl]-4-(trifluoromethyl)phenyl]-6-oxo-4-(trifluoromethyl)-1H-pyridine-3-carboxamide

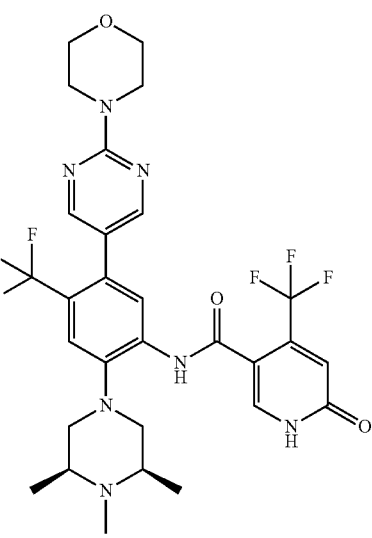

N-(5-bromo-4-(trifluoromethyl)-2-((3S,5R)-3,4,5-trimethylpiperazin-1-yl)phenyl)-6-oxo-4-(trifluoromethyl)-1,6-dihydropyridine-3-carboxamide (50 mg, 0.09 mmol), 2-(4-morpholino)pyrimidine-5-boronic acid pinacol ester (37 mg, 0.126 mmol), XPhos Pd G2 (14 mg, 0.018 mmol), Xphos (9 mg, 0.018 mmol) and sodium carbonate, anhydrous (95 mg, 0.9 mmol) were taken in a microwave vial. 1,4-Dioxane (4 ml) and water (1 ml) were added and stirred for 5 min. The white suspension was purged with argon and the reaction mixture was heated in the microwave for 60 min at 110° C. The mixture was concentrated onto celite and purified on preparative column, eluting with water/acetonitrile gradient to isolate the title compound as a white solid (10.5 mg, 17%). $^1$H NMR (500 MHz, METHANOL-d4) δ=8.30 (s, 2H), 8.05 (s, 1H), 7.99 (br. s., 1H), 7.62 (s, 1H), 7.01-6.84 (m, 1H), 3.87-3.82 (m, 4H), 3.79-3.75 (m, 4H), 3.15 (d, J=11.7 Hz, 2H), 3.02 (br. s., 2H), 2.90-2.81 (m, 2H), 2.66-2.64 (m, 3H), 1.29 (d, J=6.2 Hz, 6H); LCMS [M+H]+ 640.7.

Example 60: N-[4-fluoro-2-(4-methylpiperazin-1-yl)-5-(2-morpholin-4-ylpyridin-4-yl)phenyl]-6-oxo-4-(trifluoromethyl)-1H-pyridine-3-carboxamide

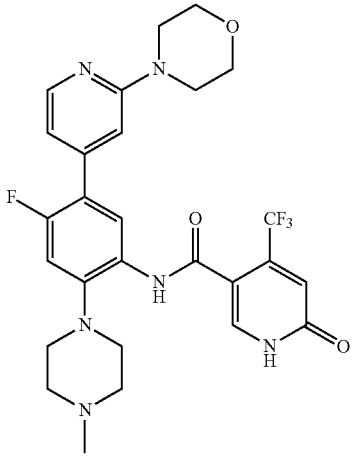

The title compound was prepared similar to the sequence described for the preparation of Example 3 using 2-morpholinopyridine-4-boronic acid, pinacol ester. $^1$H NMR (500 MHz, MeOD) δ 8.16 (d, J=5.4 Hz, 1H), 7.97 (s, 1H), 7.94 (d, J=8.1 Hz, 1H), 7.10 (d, J=12.2 Hz, 1H), 6.96 (s, 1H), 6.92 (s, 1H), 6.91 (d, J=5.1 Hz, 1H), 3.84-3.80 (m, 4H), 3.54-3.50 (m, 4H), 3.03 (t, J=4.9 Hz, 4H), 2.68 (s, J=2.0 Hz, 4H), 2.39 (s, 3H); LCMS [M+1]+=561.4.

Example 61: N-[4-methyl-5-(2-morpholin-4-ylpyrimidin-5-yl)-2-[rac-(3R 5S)-3,4,5-trimethylpiperazin-1-yl]phenyl]-6-oxo-4-(trifluoromethyl)-1H-pyridine-3-carboxamide

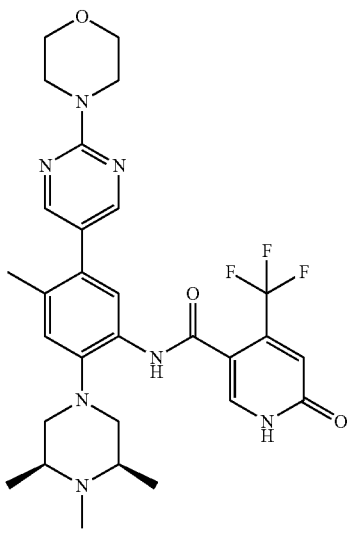 [SMILES: Cc1cc(N2C[C@@H](C)N(C)[C@@H](C)C2)c(NC(=O)c2c[nH]c(=O)cc2C(F)(F)F)cc1-c1cnc(N2CCOCC2)nc1]

Step 1: 5-bromo-4-methyl-2-((3S,5R)-3,4,5-trimethylpiperazin-1-yl)aniline

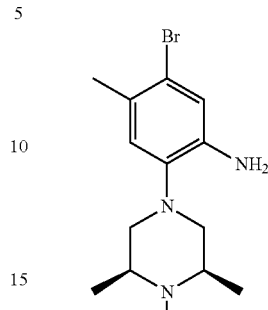

To a solution of 1-bromo-4-fluoro-2-methyl-5-nitrobenzene (2.34 g, 10 mmol) in DMSO (5 mL) was added (2S,6R)-1,2,6-trimethylpiperazine (1.35 g, 10.5 mmol). The resulting dark red mixture was stirred at 80° C. for 1.5 h. Orange precipitates formed upon cooling. The reaction mixture was diluted with H$_2$O (60 mL), basified with 1 M aq NaOH (10 mL, 10 mmol) and extracted with EtOAc (60 mL+30 mL). The combined extracts were concentrated and dried under vacuum to give the NO$_2$ intermediate as a dark orange solid (3.36 g). LCMS [M+H]$^+$ 342.2. To a solution of the above dark orange solid (3.36 g) and hydrazine monohydrate (1.46 mL, 30 mmol) in MeOH (45 mL) at 60° C. was added a suspension of Raney-Nickel (0.214 g, 2.5 mmol) in MeOH (5 mL) portionwise over 5 min. After addition, the reaction mixture was heated at 60° C. for 30 min. The reaction turned from dark orange red to light brown. It was passed through celite, and rinsed with MeOH (20 mL×2). The combined filtrate was concentrated to give a light brown oil which was purified by flash chromatography (gradient: EtOAc/hex 0-100% then MeOH/DCM 0-5%) to give the title compound as a pink solid (2.349 g, 74%). LCMS [M+H]$^+$ 312.1.

Step 2: N-(5-bromo-4-methyl-2-((3S,5R)-3,4,5-trimethylpiperazin-1-yl)phenyl)-6-oxo-4-(trifluoromethyl)-1,6-dihydropyridine-3-carboxamide

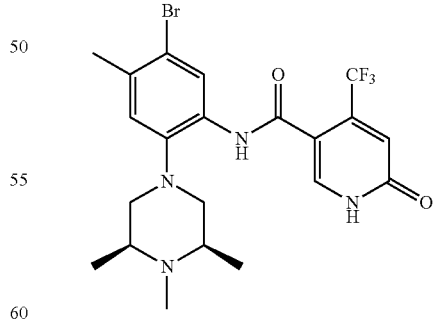

To a 25 mL RBF charged with 6-chloro-4-(trifluoromethyl)nicotinic acid (542 mg, 2.4 mmol) was added thionyl chloride (4.37 mL, 60 mmol). The resulting suspension was heated at 80° C. for 1 h. It was evaporated to give a light yellow oil which was treated with DCM (15 mL), 5-bromo-4-methyl-2-((3S,5R)-3,4,5-trimethylpiperazin-1-yl)aniline (625 mg, 2 mmol) and Et$_3$N (0.84 mL, 6 mmol). The resulting mixture was stirred at rt for 1 h. After basifying with sat. NaHCO$_3$ (30 mL), it was extracted with DCM (30 mL×2). The combined extracts were concentrated to give a beige solid. LCMS [M+H]$^+$ 519.1. A mixture of the above solid, NaOAc (328 mg, 4 mmol) in HOAc/H$_2$O (10 mL/3 mL) in a 20 mL microwave vial was microwaved at 160° C. for 5 h. Solvents were removed and the residue was treated with sat. NaHCO$_3$ (30 mL) and extracted with DCM (60 mL+30 mL). The combined extracts were concentrated and purified by flash chromatography (gradient: EtOAc/hex 0-100% then MeOH/DCM 0-15%) and triturated with MeOH (10 mL) to give the title compound as a pale yellow solid (761 mg, 71%). LCMS [M+H]$^+$ 501.2.

Step 3: N-(4-methyl-5-(2-morpholinopyrimidin-5-yl)-2-((3S,5R)-3,4,5-trimethylpiperazin-1-yl)phenyl)-6-oxo-4-(trifluoromethyl)-1,6-dihydropyridine-3-carboxamide

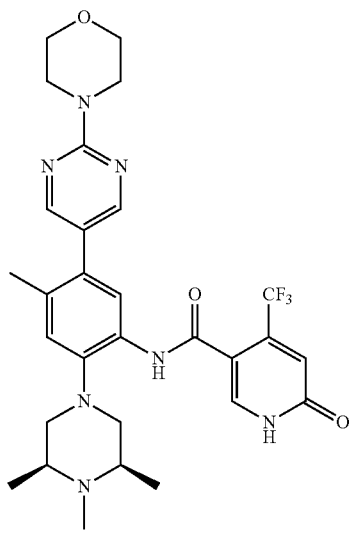

The title compound (white solid, 26.4 mg, 45%) was prepared according to a procedure similar to the last step of Example 29 using N-(5-bromo-4-methyl-2-((3S,5R)-3,4,5-trimethylpiperazin-1-yl)phenyl)-6-oxo-4-(trifluoromethyl)-1,6-dihydropyridine-3-carboxamide (50 mg, 0.1 mmol) and 2-(4-morpholino)pyrimidine-5-boronic acid pinacol ester (58 mg, 0.2 mmol). $^1$H NMR (500 MHz, METHANOL-d4) δ=8.37 (s, 2H), 7.96 (s, 1H), 7.74 (s, 1H), 7.16 (s, 1H), 6.91 (s, 1H), 3.86-3.76 (m, 8H), 3.01 (d, J=11.4 Hz, 2H), 2.71-2.62 (m, 2H), 2.61-2.53 (m, 2H), 2.40 (s, 3H), 2.30 (s, 3H), 1.18 (d, J=1.0 Hz, 6H); LCMS [M+H]$^+$ 586.3.

Example 62: 2-(difluoromethyl)-N-(5-(2-((2S,6R)-2,6-dimethylmorpholino)pyrimidin-5-yl)-2-((S)-3,4-dimethylpiperazin-1-yl)-4-fluorophenyl)-4-fluorobenzamide

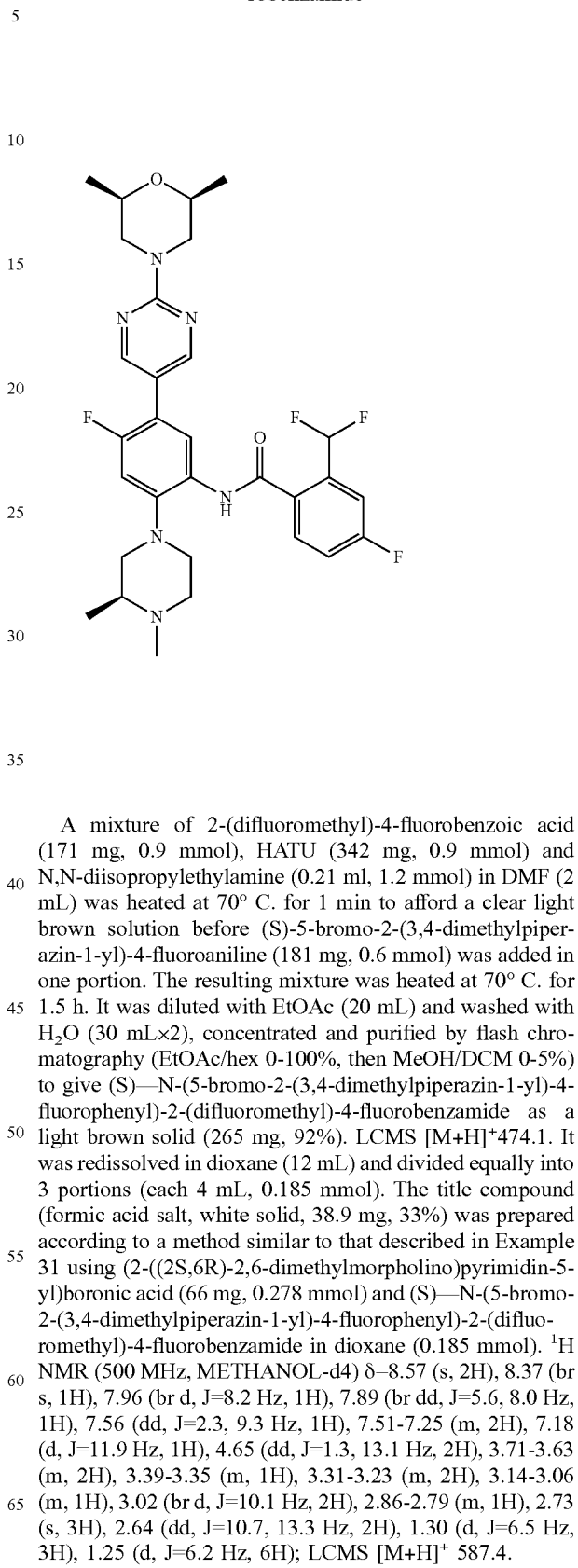

A mixture of 2-(difluoromethyl)-4-fluorobenzoic acid (171 mg, 0.9 mmol), HATU (342 mg, 0.9 mmol) and N,N-diisopropylethylamine (0.21 ml, 1.2 mmol) in DMF (2 mL) was heated at 70° C. for 1 min to afford a clear light brown solution before (S)-5-bromo-2-(3,4-dimethylpiperazin-1-yl)-4-fluoroaniline (181 mg, 0.6 mmol) was added in one portion. The resulting mixture was heated at 70° C. for 1.5 h. It was diluted with EtOAc (20 mL) and washed with H$_2$O (30 mL×2), concentrated and purified by flash chromatography (EtOAc/hex 0-100%, then MeOH/DCM 0-5%) to give (S)—N-(5-bromo-2-(3,4-dimethylpiperazin-1-yl)-4-fluorophenyl)-2-(difluoromethyl)-4-fluorobenzamide as a light brown solid (265 mg, 92%). LCMS [M+H]$^+$474.1. It was redissolved in dioxane (12 mL) and divided equally into 3 portions (each 4 mL, 0.185 mmol). The title compound (formic acid salt, white solid, 38.9 mg, 33%) was prepared according to a method similar to that described in Example 31 using (2-((2S,6R)-2,6-dimethylmorpholino)pyrimidin-5-yl)boronic acid (66 mg, 0.278 mmol) and (S)—N-(5-bromo-2-(3,4-dimethylpiperazin-1-yl)-4-fluorophenyl)-2-(difluoromethyl)-4-fluorobenzamide in dioxane (0.185 mmol). $^1$H NMR (500 MHz, METHANOL-d4) δ=8.57 (s, 2H), 8.37 (br s, 1H), 7.96 (br d, J=8.2 Hz, 1H), 7.89 (br dd, J=5.6, 8.0 Hz, 1H), 7.56 (dd, J=2.3, 9.3 Hz, 1H), 7.51-7.25 (m, 2H), 7.18 (d, J=11.9 Hz, 1H), 4.65 (dd, J=1.3, 13.1 Hz, 2H), 3.71-3.63 (m, 2H), 3.39-3.35 (m, 1H), 3.31-3.23 (m, 2H), 3.14-3.06 (m, 1H), 3.02 (br d, J=10.1 Hz, 2H), 2.86-2.79 (m, 1H), 2.73 (s, 3H), 2.64 (dd, J=10.7, 13.3 Hz, 2H), 1.30 (d, J=6.5 Hz, 3H), 1.25 (d, J=6.2 Hz, 6H); LCMS [M+H]$^+$ 587.4.

Example 63: N-[5-(1,3-benzodioxol-5-yl)-4-fluoro-2-[(3R,5S)-3,4,5-trimethylpiperazin-1-yl]phenyl]-6-oxo-4-(trifluoromethyl)-1H-pyridine-3-carboxamide

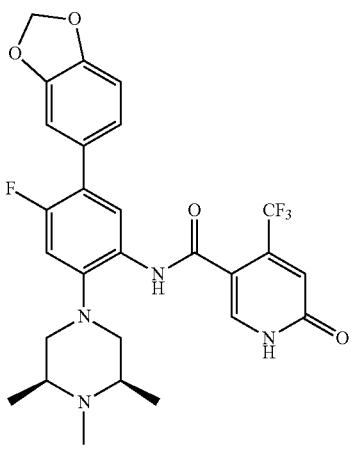 [SMILES: C[C@@H]1CN(c2cc(F)c(-c3ccc4c(c3)OCO4)cc2NC(=O)c2c[nH]c(=O)cc2C(F)(F)F)C[C@H](C)N1C]

The title compound was prepared similar to the sequence described above for the preparation of Example 31 using 3,4-methylenedioxyphenylboronic acid. $^1$H NMR (500 MHz, MeOD) δ 7.94 (s, 1H), 7.86 (d, J=8.2 Hz, 1H), 7.03 (t, J=5.8 Hz, 3H), 6.92 (s, 1H), 6.90 (d, J=8.7 Hz, 1H), 5.99 (s, 2H), 3.07 (d, J=8.4 Hz, 2H), 2.63 (d, J=7.3 Hz, 4H), 2.42 (s, 3H), 1.18 (d, J=5.4 Hz, 6H); LCMS [M+1]+=547.21.

Example 64: N-[5-(6-acetamidopyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

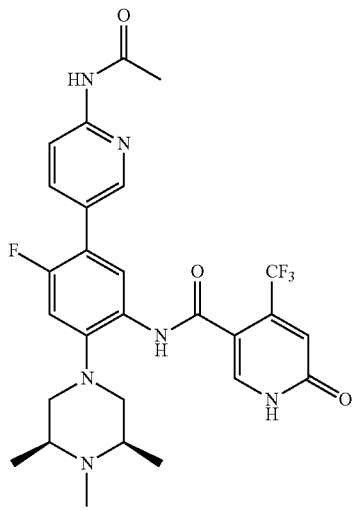 [SMILES: CC(=O)Nc1ccc(-c2cc(NC(=O)c3c[nH]c(=O)cc3C(F)(F)F)c(N3C[C@@H](C)N(C)[C@@H](C)C3)cc2F)cn1]

The title compound was prepared similar to the sequence described above for the preparation of Example 31 using 2-acetamidopyridine-5-boronic acid, pinacol ester in as the boronic ester coupling partner. $^1$H NMR (500 MHz, MeOD) δ 8.47 (s, 1H), 8.18 (d, J=8.6 Hz, 1H), 7.96-7.92 (m, 3H), 7.09 (d, J=12.1 Hz, 1H), 6.92 (s, 1H), 3.09 (d, J=10.5 Hz, 2H), 2.67-2.59 (m, 4H), 2.41 (s, 3H), 2.20 (s, 3H), 1.18 (d, J=5.8 Hz, 6H); LCMS [M+1]+=561.28.

Example 65: N-[4-fluoro-5-(2-morpholin-4-ylpyrimidin-5-yl)-2-[(3R,5S)-3,4,5-trimethylpiperazin-1-yl]phenyl]-4-methoxy-6-oxo-1H-pyridine-3-carboxamide

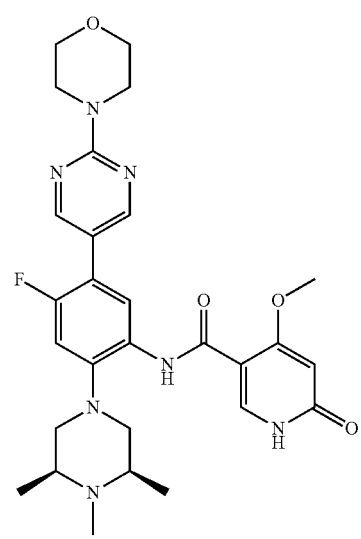 [SMILES: COc1cc(=O)[nH]cc1C(=O)Nc1cc(-c2cnc(N3CCOCC3)nc2)c(F)cc1N1C[C@@H](C)N(C)[C@@H](C)C1]

In a 5 ml microwave vial to a suspension of 4-methoxy-6-oxo-1,6-dihydropyridine-3-carboxylic acid (50.7 mg, 0.300 mmol) in pyridine, anhydrous (364 μl, 4.49 mmol) was added slowly diethyl chlorophosphate (44.4 μl, 0.307 mmol) at rt in an atmosphere of nitrogen. The reaction mixture was stirred at rt for 2 h. To this was added 4-fluoro-5-(2-morpholinopyrimidin-5-yl)-2-((3R,5S)-3,4,5-trimethylpiperazin-1-yl)aniline (30 mg, 0.075 mmol, preparation described in Example 8) and the reaction was heated at 70° C. for 3 h. The pyridine was removed in vacuo and the residue partitioned between ethyl acetate (3 mL) and saturated sodium bicarbonate solution (3 mL). The suspension was stirred for 10 min. The organic layer was separated, dried over anhydrous Na$_2$SO$_4$, and solvent was evaporated in vacuo. The crude product was purified by silica gel chromatography to obtain the title compound (15 mg, 36% yield) as a brown solid. $^1$H NMR (500 MHz, MeOD) δ 8.55 (d, J=1.1 Hz, 4H), 8.49 (d, J=1.2 Hz, 14H), 8.31 (s, 2H), 7.12 (d, J=11.9 Hz, 2H), 6.84 (dd, J=9.9, 5.9 Hz, 15H), 6.08 (d, J=4.6 Hz, 2H), 4.14 (s, 6H), 3.86-3.80 (m, 43H), 3.76 (dd, J=9.0, 4.1 Hz, 43H), 3.19 (s, 7H), 3.02 (d, J=10.7 Hz, 5H), 2.84 (s, 11H), 2.65-2.60 (m, 9H), 2.61-2.51 (m, 42H), 2.43 (s, 7H), 1.25 (d, J=6.0 Hz, 42H); LCMS [M+1]+=552.3.

Example 66: N-[5-[2-(cyclopropylmethoxy)pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

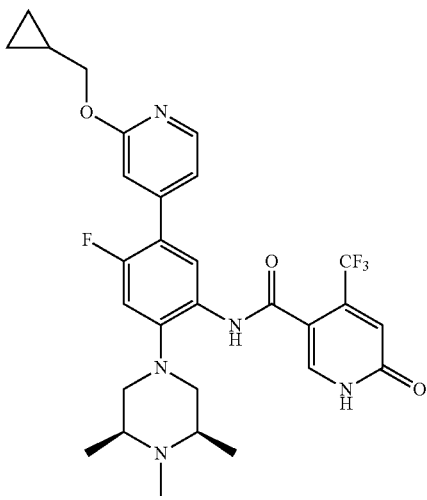 [SMILES: C[C@@H]1CN(c2cc(F)c(-c3ccnc(OCC4CC4)c3)cc2NC(=O)c2c[nH]c(=O)cc2C(F)(F)F)C[C@H](C)N1C]

The title compound was prepared similar to the sequence described above for the preparation of Example 31 using 2-(cyclopropylmethoxy)-4-(4,4,5,5-tetramethyl-1,3,2-dioxaborolan-2-yl)pyridine as the boronic ester coupling partner. $^1$H NMR (500 MHz, MeOD) δ 8.14 (d, J=5.4 Hz, 1H), 7.97 (d, J=9.2 Hz, 1H), 7.96 (s, 1H), 7.13 (d, J=5.4 Hz, 1H), 7.07 (d, J=12.3 Hz, 1H), 6.97 (s, 1H), 6.91 (s, 1H), 4.14 (d, J=7.1 Hz, 2H), 3.10 (d, J=11.3 Hz, 2H), 2.62 (t, J=11.2 Hz, 2H), 2.54 (ddd, J=10.3, 6.9, 4.1 Hz, 2H), 2.37 (s, 3H), 1.35-1.25 (m, 1H), 1.16 (d, J=6.2 Hz, 6H), 0.61 (q, J=5.9 Hz, 2H), 0.37 (q, J=4.7 Hz, 2H); LCMS [M+1]+=574.22.

Example 67: N-[5-[2-[(cyclohexylamino)methyl]phenyl]-4-fluoro-2-[(3R,5S)-3,4,5-trimethylpiperazin-1-yl]phenyl]-6-oxo-4-(trifluoromethyl)-1H-pyridine-3-carboxamide

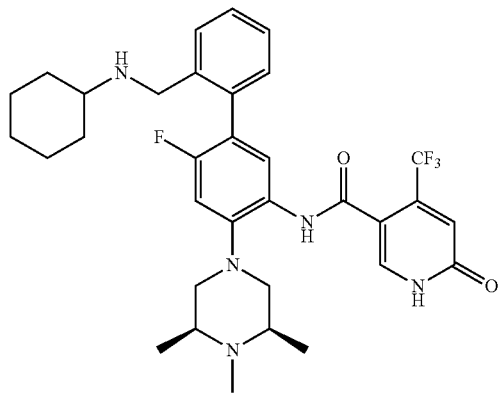 [SMILES: C[C@@H]1CN(c2cc(F)c(-c3ccccc3CNC3CCCCC3)cc2NC(=O)c2c[nH]c(=O)cc2C(F)(F)F)C[C@H](C)N1C]

Step 1: N-(6-fluoro-2'-formyl-4-((3S,5R)-3,4,5-trimethylpiperazin-1-yl)-[1,1'-biphenyl]-3-yl)-6-methoxy-4-(trifluoromethyl)nicotinamide


N-(5-bromo-4-fluoro-2-((3S,5R)-3,4,5-trimethylpiperazin-1-yl)phenyl)-6-methoxy-4-(trifluoromethyl)nicotinamide (125 mg, 0.241 mmol), 2-formylphenylboronic acid (50.5 mg, 0.337 mmol), sodium carbonate, anhydrous (255 mg, 2.407 mmol), XPhos Pd G2 (37.9 mg, 0.048 mg) and Xphos (22.95 mg, 0.048 mmol) were mixed in a microwave vial. Water (3 ml) and 1,4-dioxane (3 ml) were added and stirred for 5 min. The white suspension was purged with argon and the reaction mixture was heated in the microwave for 30 min at 110° C. The reaction mixture was concentrated onto celite and purified on Isco (4G) column, eluting with DCM containing 0-2% MeOH to obtain the desired product as an off white foam. (124 mg, 90%). LCMS [M+H]+ 545.4

Step 2: N-(2'-((cyclohexylamino)methyl)-6-fluoro-4-((3S,5R)-3,4,5-trimethylpiperazin-1-yl)-[1,1'-biphenyl]-3-yl)-6-methoxy-4-(trifluoromethyl)nicotinamide

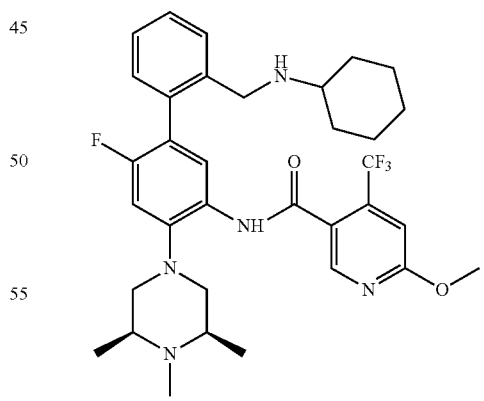

N-(6-fluoro-2'-formyl-4-((3S,5R)-3,4,5-trimethylpiperazin-1-yl)-[1,1'-biphenyl]-3-yl)-6-methoxy-4-(trifluoromethyl)nicotinamide (70 mg, 0.122 mmol), N-(6-fluoro-2'-formyl-4-((3S,5R)-3,4,5-trimethylpiperazin-1-yl)-[1,1'-biphenyl]-3-yl)-6-methoxy-4-(trifluoromethyl)nicotinamide (70 mg, 0.122 mmol) and acetic acid, glacial, 99.8% (0.028 ml, 0.488 mmol) were mixed in anhydrous DCE. A cloudy Step 3: N-(2'-((cyclohexylamino)methyl)-6-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide hydrochloride salt

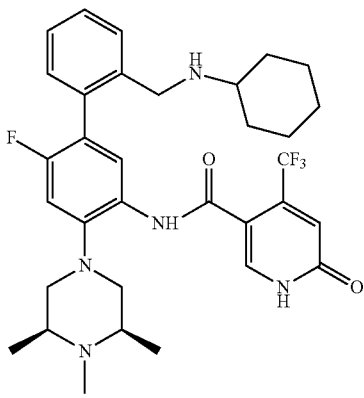 [SMILES: C[C@@H]1CN(c2cc(F)c(-c3ccccc3CNC3CCCCC3)cc2NC(=O)c2c[nH]c(=O)cc2C(F)(F)F)C[C@H](C)N1C]

To a solution of N-(2'-((cyclohexylamino)methyl)-6-fluoro-4-((3S,5R)-3,4,5-trimethylpiperazin-1-yl)-[1,1'-biphenyl]-3-yl)-6-methoxy-4-(trifluoromethyl)nicotinamide (48 mg, 0.076 mmol) in methanol (1.5. ml) was added concentrated HCl (1.0 ml) and the reaction mixture was heated at 80° C. The reaction was complete after 2.5 h. The reaction mixture was allowed to cool to RT, concentrated to dryness, co-evaporated with MeOH first and then with DCM to yield the desired product as an off white solid (30 mg, 51%). $^1$H NMR (500 MHz, METHANOL-d4) δ=8.02-7.88 (m, 1H), 7.72-7.65 (m, 1H), 7.63-7.59 (m, 1H), 7.50-7.43 (m, 2H), 7.36-7.30 (m, 1H), 7.16 (d, J=10.8 Hz, 1H), 6.82 (s, 1H), 4.30-4.02 (m, 2H), 3.60-3.50 (m, 2H), 3.33-3.25 (m, 2H), 3.00-2.88 (m, 5H), 1.89-1.78 (m, 2H), 1.69 (br. s., 2H), 1.56 (d, J=12.6 Hz, 1H), 1.44-1.31 (m, 6H), 1.23-1.15 (m, 5H), 1.12-1.04 (m, 1H), 1.12-1.04 (m, 1H); LCMS [M+H]+=614.6.

Example 68: N-[5-(3-chloro-4-morpholin-4-ylphenyl)-4-fluoro-2-[(3R 5S)-3,4,5-trimethylpiperazin-1-yl]phenyl]-6-oxo-4-(trifluoromethyl)-1H-pyridine-3-carboxamide

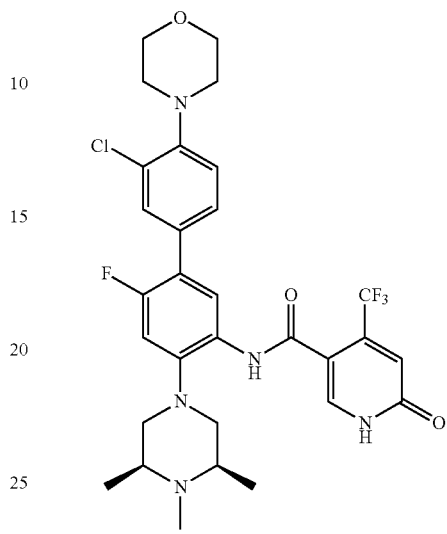

The title compound (light brown solid, 50.7 mg, 80%) was prepared in a manner similar to Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol, example 31) and 3-chloro-4-(4-morpholinyl)benzeneboronic acid pinacol ester (65 mg, 0.2 mmol). $^1$H NMR (500 MHz, METHANOL-d4) δ=7.97 (s, 1H), 7.91 (d, J=8.2 Hz, 1H), 7.59 (s, 1H), 7.48 (d, J=8.2 Hz, 1H), 7.22 (d, J=8.1 Hz, 1H), 7.06 (d, J=12.1 Hz, 1H), 6.92 (s, 1H), 3.92-3.85 (m, 4H), 3.15-3.05 (m, 6H), 2.68-2.52 (m, 4H), 2.39 (s, 3H), 1.18 (d, J=6.1 Hz, 6H); LCMS [M+H]$^+$ 622.1.

Example 69: N-[5-(3,4-dihydro-2H-1,5-benzodioxepin-7-yl)-4-fluoro-2-[(3R,5S)-3,4,5-trimethylpiperazin-1-yl]phenyl]-6-oxo-4-(trifluoromethyl)-1H-pyridine-3-carboxamide

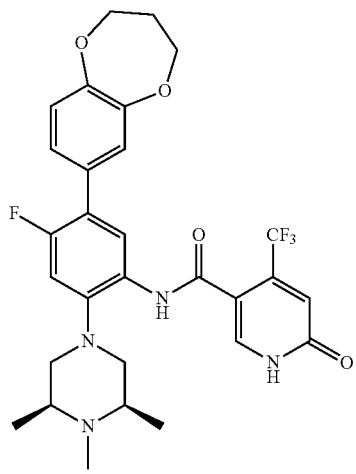 [SMILES: C[C@@H]1CN(c2cc(F)c(-c3ccc4c(c3)OCCCO4)cc2NC(=O)c2c[nH]c(=O)cc2C(F)(F)F)C[C@H](C)N1C]

The title compound (light beige solid, 44.6 mg, 77%) was prepared in a manner similar to Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 3,4-dihydro-2H-1,5-benzodioxepin-7-ylboronic acid (38.8 mg, 0.2 mmol). $^1$H NMR (500 MHz, METHANOL-d4) δ=7.96 (s, 1H), 7.89 (d, J=8.3 Hz, 1H), 7.19-7.15 (m, 1H), 7.13 (d, J=8.1 Hz, 1H), 7.06-7.00 (m, 2H), 6.92 (s, 1H), 4.25-4.19 (m, 4H), 3.06 (d, J=11.1 Hz, 2H), 2.67-2.52 (m, 4H), 2.39 (s, 3H), 2.23-2.17 (m, 2H), 1.18 (d, J=6.1 Hz, 6H); LCMS [M+H]$^+$=575.3.

Example 70: N-[5-(2,3-dihydro-1,4-benzodioxin-6-yl)-4-fluoro-2-[(3R,5S)-3,4,5-trimethylpiperazin-1-yl]phenyl]-6-oxo-4-(trifluoromethyl)-1H-pyridine-3-carboxamide

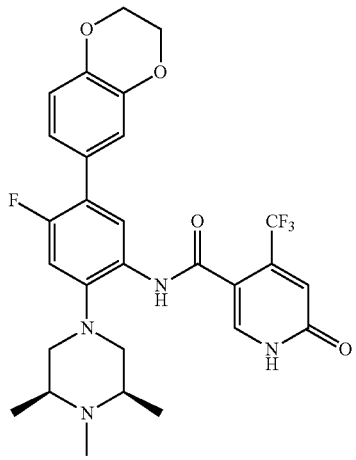

The title compound (off white solid, 43.7 mg, 78%) was prepared in a manner similar to Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 2,3-dihydro-1,4-benzodioxin-6-ylboronic acid (36 mg, 0.2 mmol). $^1$H NMR (500 MHz, METHANOL-d4) δ=7.96 (s, 1H), 7.88 (d, J=8.3 Hz, 1H), 7.07-6.98 (m, 3H), 6.95-6.87 (m, 2H), 4.29 (s, 4H), 3.06 (d, J=11.2 Hz, 2H), 2.66-2.52 (m, 4H), 2.39 (s, 3H), 1.18 (d, J=6.1 Hz, 6H); LCMS [M+H]$^+$=561.2.

Example 71: N-[4-fluoro-5-(4-methyl-2,3-dihydro-1,4-benzoxazin-7-yl)-2-[(3R,5S)-3,4,5-trimethylpiperazin-1-yl]phenyl]-6-oxo-4-(trifluoromethyl)-1H-pyridine-3-carboxamide

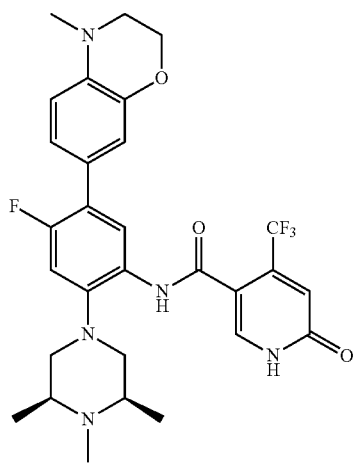

The title compound (pale beige solid, 28.9 mg, 50%) was prepared in a manner similar to Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 4-methyl-7-(4,4,5,5-tetramethyl-1,3,2-dioxaborolan-2-yl)-3,4-dihydro-2H-1,4-benzoxazine (55 mg, 0.2 mmol). $^1$H NMR (500 MHz, METHANOL-d4) δ=7.96 (s, 1H), 7.88 (d, J=8.3 Hz, 1H), 7.03 (d, J=8.4 Hz, 1H), 7.00 (d, J=12.2 Hz, 1H), 6.94-6.92 (m, 1H), 6.92 (s, 1H), 6.77 (d, J=8.4 Hz, 1H), 4.33-4.28 (m, 2H), 3.32-3.28 (m, 2H), 3.04 (d, J=11.1 Hz, 2H), 2.93 (s, 3H), 2.66-2.47 (m, 4H), 2.39 (s, 3H), 1.18 (d, J=6.1 Hz, 6H); LCMS [M+H]$^+$ 574.4.

Example 72: N-[5-(2-acetamidopyrimidin-5-yl)-4-fluoro-2-[(3R,5S)-3,4,5-trimethylpiperazin-1-yl]phenyl]-6-oxo-4-(trifluoromethyl)-1H-pyridine-3-carboxamide

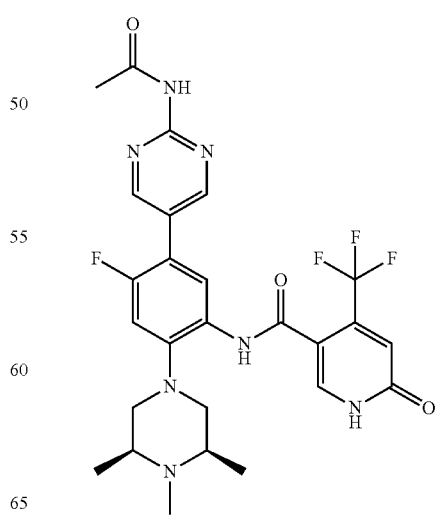

The title compound was prepared in a manner similar to Example 31 using N-(5-(4,4,5,5-tetramethyl-1,3,2-dioxaborolan-2-yl)pyrimidin-2-yl)acetamide in place of 2-cyanopyrimidine-5-boronic acid pinacol ester. ¹H NMR (500 MHz, MeOD) δ 8.81 (s, 2H), 7.98 (s, 1H), 7.96 (d, J=4.7 Hz, 1H), 7.15 (d, J=12.0 Hz, 1H), 6.93 (s, 1H), 3.16 (d, J=7.0 Hz, 2H), 2.80 (s, 2H), 2.71 (t, J=11.1 Hz, 3H), 2.52 (s, 3H), 2.28 (s, 3H), 1.23 (d, J=5.9 Hz, 6H); LCMS [M+1]+=562.2.

Example 73: N-[4-fluoro-5-(1-phenyl-3,6-dihydro-2H-pyridin-4-yl)-2-[(3R,5S)-3,4,5-trimethylpiperazin-1-yl]phenyl]-6-oxo-4-(trifluoromethyl)-1H-pyridine-3-carboxamide

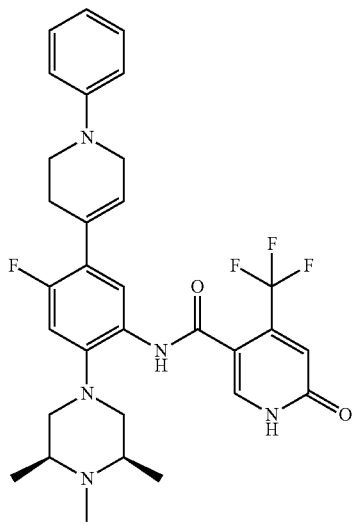

The procedure was similar to Example 39 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (60 mg, 0.099 mmol) and 1,2,3,6-tetrahydro-1-phenyl-4-(4,4,5,5-tetramethyl-1,3,2-dioxaborolan-2-yl)-pyridine (39.6 mg, 0.139 mmol) to give, after deprotection of the silyloxy intermediate, 20 mg (74% yield) of the title compound as a pale yellow orange powder. ¹H NMR (500 MHz, METHANOL-d4) δ=8.04-7.98 (m, 1H), 7.86 (d, J=7.9 Hz, 1H), 7.34 (t, J=8.0 Hz, 2H), 7.15 (d, J=8.2 Hz, 2H), 7.08 (d, J=12.1 Hz, 1H), 7.01-6.94 (m, 2H), 6.20 (br. s., 1H), 4.00-3.93 (m, 2H), 3.62-3.57 (m, 2H), 3.55-3.48 (m, 2H), 3.37 (br. s., 2H), 3.00 (s, 3H), 2.92 (t, J=12.3 Hz, 2H), 2.74 (br. s., 2H), 1.49-1.42 (m, 6H); LCMS [M+H]+ 584.6.

Example 74: N-[4-fluoro-5-(2-morpholin-4-ylpyrimidin-5-yl)-2-[(3R,5S)-3,4,5-trimethylpiperazin-1-yl]phenyl]benzamide

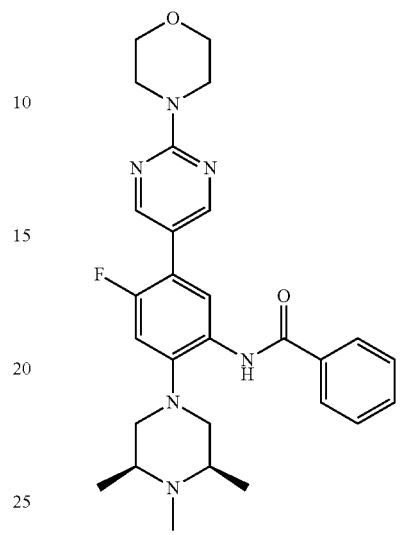

The title compound (pale beige solid, 25.3 mg, 50%) was prepared in a manner similar to Example 34 using 4-fluoro-5-(2-morpholinopyrimidin-5-yl)-2-((3S,5R)-3,4,5-trimethylpiperazin-1-yl)aniline (40 mg, 0.1 mmol) and benzoyl chloride (17 L, 0.15 mmol). ¹H NMR (500 MHz, CHLOROFORM-d) δ=9.25 (s, 1H), 8.69 (d, J=8.2 Hz, 1H), 8.60 (d, J=1.2 Hz, 2H), 7.94 (d, J=7.1 Hz, 2H), 7.64-7.54 (m, 3H), 7.03 (d, J=11.4 Hz, 1H), 3.93-3.86 (m, 4H), 3.85-3.79 (m, 4H), 2.93 (d, J=10.9 Hz, 2H), 2.70 (t, J=10.9 Hz, 2H), 2.50-2.41 (m, 2H), 2.39 (s, 3H), 1.18 (d, J=6.2 Hz, 6H); LCMS [M+H]+ 505.4.

Example 75: 4-fluoro-N-[4-fluoro-5-(2-morpholin-4-ylpyrimidin-5-yl)-2-[(3R,5S)-3,4,5-trimethylpiperazin-1-yl]phenyl]-3-methoxybenzamide

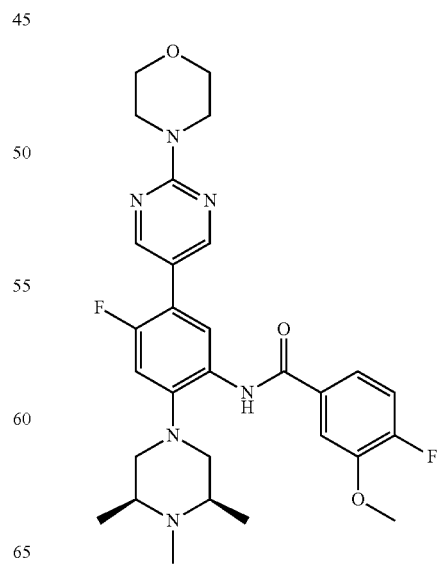

The title compound (beige solid, 4.6 mg, 8%) was prepared in a manner similar to Example 34 using 4-fluoro-3-methoxybenzoic acid (34 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). ¹H NMR (500 MHz, CHLOROFORM-d) δ=9.14 (s, 1H), 8.57 (d, J=8.3 Hz, 1H), 8.51 (d, J=1.1 Hz, 2H), 7.58 (dd, J=2.0, 8.1 Hz, 1H), 7.31 (t, J=5.8 Hz, 1H), 7.14 (dd, J=8.4, 10.5 Hz, 1H), 6.94 (d, J=11.2 Hz, 1H), 3.93 (s, 3H), 3.83-3.78 (m, 4H), 3.74-3.71 (m, 4H), 2.82 (d, J=10.9 Hz, 2H), 2.61 (t, J=10.9 Hz, 2H), 2.36-2.30 (m, 2H), 2.29 (s, 3H), 1.08 (d, J=6.2 Hz, 6H); LCMS [M+H]⁺ 553.3.

Example 76: 3,5-dichloro-N-[4-fluoro-5-(2-morpholin-4-ylpyrimidin-5-yl)-2-[(3R,5S)-3,4,5-trimethylpiperazin-1-yl]phenyl]benzamide

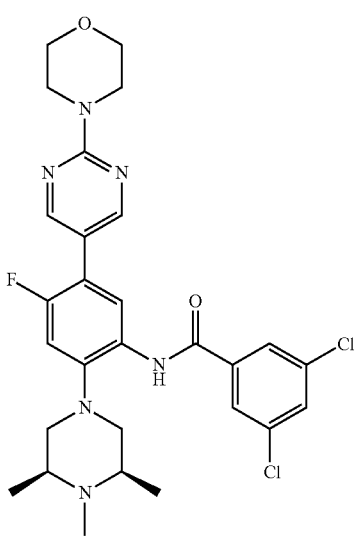 [SMILES: C[C@@H]1CN(c2cc(F)c(-c3cnc(N4CCOCC4)nc3)cc2NC(=O)c2cc(Cl)cc(Cl)c2)C[C@H](C)N1C]

The title compound (beige solid, 32.4 mg, 55%) was prepared in a manner similar to Example 34 using 3,5-dichlorobenzoic acid (38 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). ¹H NMR (500 MHz, CHLOROFORM-d) δ=9.20 (s, 1H), 8.52 (d, J=8.2 Hz, 1H), 8.50 (d, J=1.2 Hz, 2H), 7.71 (s, 2H), 7.50 (s, 1H), 6.95 (d, J=11.2 Hz, 1H), 3.84-3.78 (m, 4H), 3.75-3.69 (m, 4H), 2.82 (d, J=11.0 Hz, 2H), 2.63 (t, J=10.9 Hz, 2H), 2.42-2.34 (m, 2H), 2.31 (s, 3H), 1.11 (d, J=6.2 Hz, 6H); LCMS [M+H]⁺ 573.2.

Example 77: N-[4-fluoro-5-(2-morpholin-4-ylpyrimidin-5-yl)-2-[(3R,5S)-3,4,5-trimethylpiperazin-1-yl]phenyl]-6-oxo-4-(triluoromethyl)-1H-pyridazine-3-carboxamide

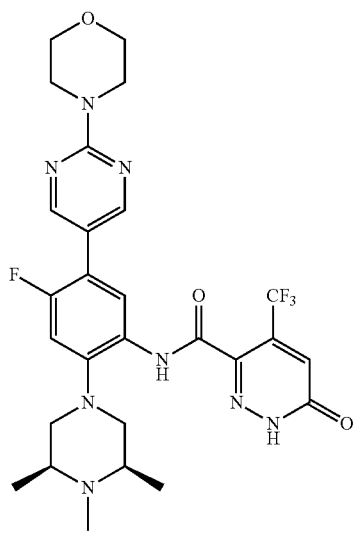

Step 1: ethyl 2-diazo-4,4,4-trifluoro-3-oxobutanoate

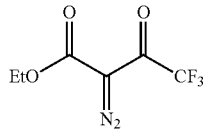

To a solution of ethyl 2-diazoacetate (50 g, 438 mmol, 1 eq) in DCM (500 mL) was added dropwise a solution of TFAA (70 mL, 482 mmol, 1.1 eq, in DCM) at 0° C. under argon, then the reaction mixture was continued for 2 h. TLC analysis indicated formation of polar spot. The reaction mixture was neutralized with sat NaHCO₃ solution and extracted with DCM (3×300 mL). The combined organic layer was washed with Cu₂SO₄ solution and dried over Na₂SO₄, then concentrated to give ethyl 2-diazo-4,4,4-trifluoro-3-oxobutanoate (50 g, 55%) as a green oil. TLC: EtOAc Pet ether (2:8); R_f: 0.4.

Step 2: 5-ethyl 1-methyl (Z)-4-diazo-3-(trifluoromethyl)pent-2-enedioate

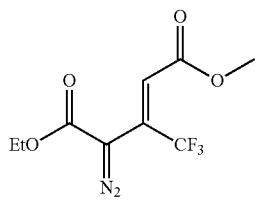

To a stirred solution of methyl 2-(triphenyl-15-phosphaneylidene)acetate (52.56 g, 157 mmol, 1.5 eq) in diethyl ether (308 mL) was added ethyl 2-diazo-4,4,4-trifluoro-3-oxobutanoate (22 g, 104 mmol, 1 eq) at 10° C. under argon atmosphere, then the reaction mixture was stirred at RT for 24 h. TLC analysis indicated formation of polar spot. The reaction mixture was filtered and washed with diethyl ether then the filtrate was concentrated to crude compound. The crude compound was purified by column chromatography (silica gel, 100-200 mesh) using 0-10% diethyl ether in pentane as eluent to afford 5-ethyl 1-methyl (Z)-4-diazo-3-(trifluoromethyl)pent-2-enedioate (19 g, 68.19%) as yellow oil. TLC system: diethyl ether:pentane (3:7); R$_f$: 0.4.

Step 3: ethyl 6-methoxy-4-(trifluoromethyl)pyridazine-3-carboxylate

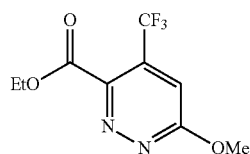

To a stirred solution of 5-ethyl 1-methyl (Z)-4-diazo-3-(trifluoromethyl)pent-2-enedioate (19 g, 71.42 mmol, 1 eq) in diethyl ether (190 mL) was portion wise added TPP (22.4 g, 85.71 mmol, 1.2 eq) at 10° C. then allowed to remain at RT for 16 h. TLC analysis indicated formation of polar spot. The reaction mixture was filtered then the filtrate was concentrated to crude residue. The crude residue was purified by column chromatography (silica gel, 230-400 mesh) using 0-20% acetone in pet ether as eluent to afford ethyl 6-methoxy-4-(trifluoromethyl)pyridazine-3-carboxylate (5 g, 28.90%) as yellow oil. LCMS: [M+H]+ 251.14.

Step 4: ethyl 6-oxo-4-(trifluoromethyl)-1,6-dihydropyridazine-3-carboxylate

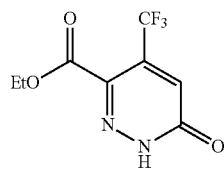

To a stirred solution of 6-methoxy-4-(trifluoromethyl)pyridazine-3-carboxylate (4.5 g, 18 mmol, 1 eq) in ACN (80 mL) was added NaI (8.1 g, 54 mmol, 3 eq) and TMS-Cl (5.86 g, 54 mmol, 3 eq) at RT under argon atmosphere, then the reaction mixture was heated to 80° C. for 2 h. TLC analysis indicated formation of polar spot. The reaction mixture was concentrated to crude residue, which was diluted with water and extracted with EtOAc (3×100 mL). The combined organic layer was dried over Na$_2$SO$_4$ then concentrated to crude compound. The crude compound was purified by column chromatography (silica gel, 100-200 mesh) using 0-5% MeOH in DCM as eluent to afford (3.2 g, 76.20%) as pale yellow solid. LCMS: [M+H]+ 237.04.

Step 5: 6-oxo-4-(trifluoromethyl)-1,6-dihydropyridazine-3-carboxylic acid

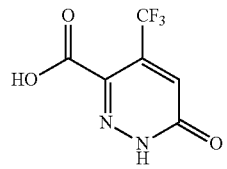 [SMILES: O=C(O)c1n[nH]c(=O)cc1C(F)(F)F]

To a solution of ethyl 6-oxo-4-(trifluoromethyl)-1,6-dihydropyridazine-3-carboxylate (205 mg, 0.923 mmol) in THF (923 µl) was added lithium hydroxide monohydrate (77 mg, 1.846 mmol) dissolved in water (923 µl), and the mixture was stirred for 1 h at room temperature. The reaction was concentrated, adjusted to a pH of 3, and extracted with DCM. The compound was not soluble in DCM. Purification was carried out using an anion exchange column to give the title compound (150 mg, 78% yield). LCMS [M−H] 206.98.

Step 6: N-[4-fluoro-5-(2-morpholin-4-ylpyrimidin-5-yl)-2-[(3R,5S)-3,4,5-trimethylpiperazin-1-yl]phenyl]-6-oxo-4-(triluoromethyl)-1H-pyridazine-3-carboxamide

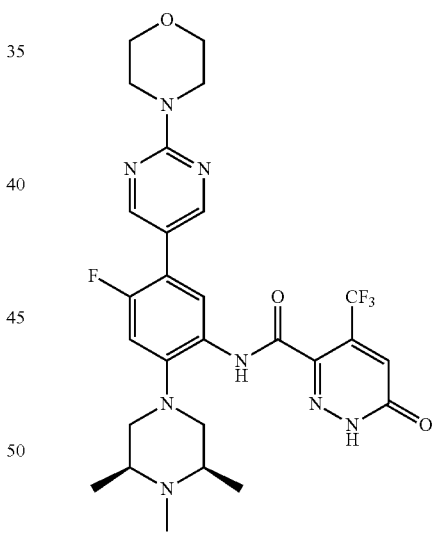

The title compound was prepared similar to the sequence described above for the preparation of Example 34 using 6-oxo-4-(trifluoromethyl)-1,6-dihydropyridazine-3-carboxylic acid in place of 1-methyl-6-oxo-4-(trifluoromethyl)-1,6-dihydropyridine-3-carboxylic acid. $^1$H NMR (500 MHz, MeOD) δ 8.57 (d, J=1.1 Hz, 2H), 8.28 (d, J=8.2 Hz, 1H), 7.34 (s, 1H), 7.12 (d, J=11.9 Hz, 1H), 3.86-3.83 (m, 4H), 3.78-3.75 (m, 4H), 3.08 (d, J=11.5 Hz, 2H), 2.80 (s, 2H), 2.67 (t, J=11.2 Hz, 2H), 2.50 (s, 3H), 1.21 (d, J=6.3 Hz, 6H); LCMS [M+1]+=591.4.

Example 78: N-[4-fluoro-5-(2-morpholin-4-ylpyrimidin-5-yl)-2-[(3R)-3,4-dimethylpiperazin-1-yl]phenyl]benzamide

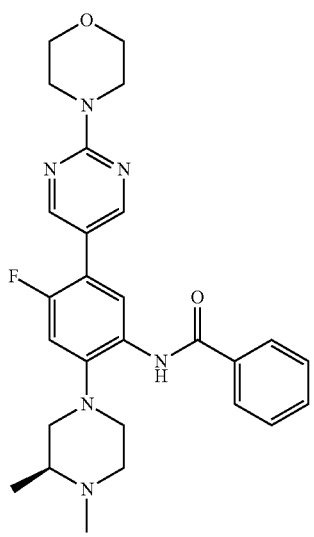

Step 1: (S)-4-(4-bromo-5-fluoro-2-nitrophenyl)-1,2-dimethylpiperazine

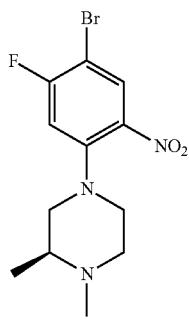 [SMILES: C[C@H]1CN(c2cc(F)c(Br)cc2[N+](=O)[O-])CCN1C]

A solution of 1-bromo-2,4-difluoro-5-nitrobenzene (3.85 mL, 30.5 mmol) in toluene (10 mL) was added dropwise to a rapidly stirring mixture of (S)-1,2-dimethylpiperazine dihydrochloride (5.70 g, 30.5 mmol) and potassium carbonate (10.5 g, 76 mmol) in toluene (70 mL) at room temperature. After stirring for 20 minutes the reaction was warmed to 45° C. for 30 minutes. After the reaction was cooled to room temperature the reaction mixture was partitioned between water (100 mL) and ethyl acetate (100 mL). The layers were separated and the aqueous layer was extracted with additional ethyl acetate. The combined organic extracts were dried over magnesium sulfate and after removal of the inorganics by filtration the filtrate was concentrated onto celite. Purification by flash chromatography [1-10% MeOH/DCM+0.5% NH$_4$OH] afforded (S)-4-(4-bromo-5-fluoro-2-nitrophenyl)-1,2-dimethylpiperazine (7.41 g, 73%). LCMS [M+H]+: 332.1.

Step 2: (S)-4-(5-(4-(3,4-dimethylpiperazin-1-yl)-2-fluoro-5-nitrophenyl)pyrimidin-2-yl)morpholine A 100 mL round bottomed flask was charged with a mixture of (S)-4-(4-bromo-5-fluoro-2-nitrophenyl)-1,2-dimethylpiperazine (1.60 g, 4.8 mmol), 2-(4-morpholino)pyrimidine-5-boronic acid pinacol ester (1.50 g, 5.2 mmol), XPhos Pd G2 (0.075 g, 0.10 mmol) and XPhos (0.045 g, 0.10 mmol). The flask was sealed with a septum, evacuated and backfilled with nitrogen. 1,4-dioxane (40 mL) and 2 M aqueous sodium carbonate (12 mL) were added via syringe and the flask was evacuated and backfilled an additional time. The reaction was heated to 90° C. for 3 h in an oil bath. After cooling to room temperature the reaction was partitioned between DCM and water. The layers were separated and the aqueous layer was extracted with additional DCM. The combined organic extracts were dried over magnesium sulfate and after removal of the inorganics by filtration the filtrate was concentrated onto celite. Purification by flash chromatography [0.5-10% MeOH/DCM+1% NH$_4$OH] afforded (S)-4-(5-(4-(3,4-dimethylpiperazin-1-yl)-2-fluoro-5-nitrophenyl)pyrimidin-2-yl)morpholine (2.0 g, >95%). LCMS [M+H]+: 417.2.

Step 3: Preparation of (S)-2-(3,4-dimethylpiperazin-1-yl)-4-fluoro-5-(2-morpholinopyrimidin-5-yl)aniline

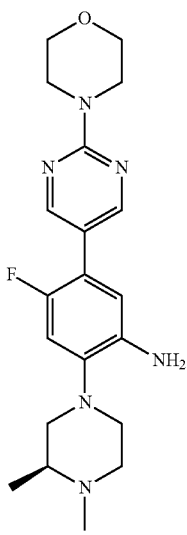 [SMILES: C[C@H]1CN(c2cc(F)c(-c3cnc(N4CCOCC4)nc3)cc2[N+](=O)[O-])CCN1C]

A mixture of (S)-4-(5-(4-(3,4-dimethylpiperazin-1-yl)-2-fluoro-5-nitrophenyl)pyrimidin-2-yl)morpholine (2.0 g, 5.0 mmol), iron powder (1.1 g, 20 mmol) and acetic acid (25 mL) was heated to 80° C. for 90 minutes. After cooling to room temperature the reaction was transferred to a large Erlenmeyer flask and diluted with DCM (250 mL). The acetic acid was carefully neutralised by the addition of aqueous sodium bicarbonate. The whole was transferred to a separatory funnel and the layers were separated. The aqueous layer was extracted with additional DCM. The combined organic extracts were dried over magnesium sulfate and after removal of the inorganics by filtration, the filtrate was concentrated onto celite. Purification by flash chromatography [0.5-10% DCM/MeOH+0.5% NH$_4$OH] afforded (S)-2-(3,4-dimethylpiperazin-1-yl)-4-fluoro-5-(2-morpholinopyrimidin-5-yl)aniline (1.34 g, 70%). LCMS [M+H]+: 387.3.

Step 4: Preparation of (S)—N-(2-(3,4-dimethylpiperazin-1-yl)-4-fluoro-5-(2-morpholinopyrimidin-5-yl)phenyl)benzamide

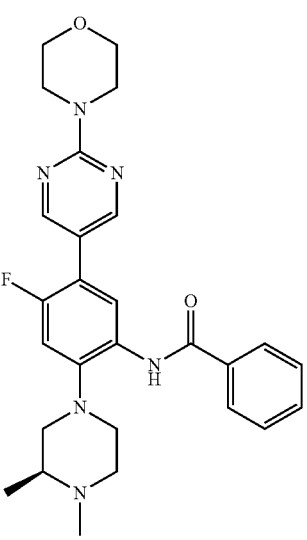

Benzoyl chloride (0.010 mL, 0.10 mmol) was added dropwise to a stirring solution of (S)-2-(3,4-dimethylpiperazin-1-yl)-4-fluoro-5-(2-morpholinopyrimidin-5-yl)aniline (0.025 g, 0.065 mmol) and triethylamine (0.026 mL, 0.19 mmol) in DCM (3 mL) at room temperature. After stirring for 2 h at room temperature the reaction was concentrated onto celite and purified by flash chromatography [0.5-10% MeOH/DCM+0.5% NH$_4$OH] to afford the title compound (S)—N-(2-(3,4-dimethylpiperazin-1-yl)-4-fluoro-5-(2-morpholinopyrimidin-5-yl)phenyl)benzamide (0.028 g, 88%). $^1$H NMR (500 MHz, DMSO-d6) δ=9.57 (s, 1H), 8.57 (s, 2H), 8.04-7.93 (m, 3H), 7.67-7.53 (m, 3H), 7.18 (d, J=12.1 Hz, 1H), 3.79-3.75 (m, 4H), 3.71-3.67 (m, 4H), 3.06-2.98 (m, 2H), 2.91-2.78 (m, 4H), 2.22 (br. s., 4H), 0.97 (d, J=6.0 Hz, 3H); LCMS [M+H]+: 491.4.

Example 79: N-[4-fluoro-5-(2-morpholin-4-ylpyrimidin-5-yl)-2-[(3R)-3,4-dimethylpiperazin-1-yl]phenyl]furan-2-carboxamide

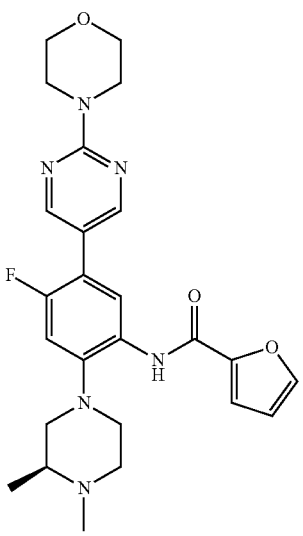

The title compound was prepared similar to the sequence described above for the preparation of Example 78 using 2-furoyl chloride in place of benzoyl chloride in Step 4. $^1$H NMR (500 MHz, DMSO-d6) δ=9.37 (s, 1H), 8.55 (s, 2H), 8.20 (d, J=8.6 Hz, 1H), 7.99 (s, 1H), 7.30 (d, J=3.4 Hz, 1H), 7.24 (d, J=12.0 Hz, 1H), 6.74 (dd, J=1.7, 3.5 Hz, 1H), 3.79-3.75 (m, 4H), 3.72-3.66 (m, 4H), 3.00-2.82 (m, 5H), 2.27 (br. s., 4H), 1.02 (d, J=6.2 Hz, 3H); LCMS [M+H]+: 481.3.

Example 80: N-[4-fluoro-5-(2-morpholin-4-ylpyrimidin-5-yl)-2-[(3R)-3,4-dimethylpiperazin-1-yl]phenyl]pyridine-3-carboxamide

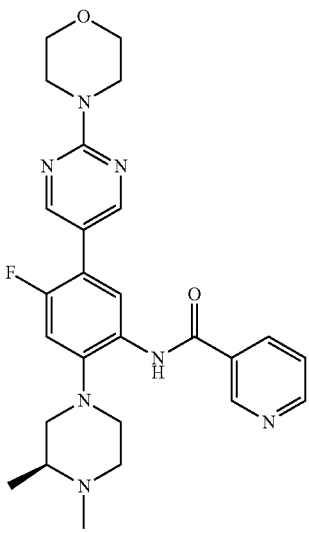

The title compound was prepared similar to the sequence described above for the preparation of Example 78 using nicotinoyl chloride hydrochloride in place of benzoyl chloride in Step 4. $^1$H NMR (500 MHz, DMSO-d6) δ 9.82 (s, 1H), 9.13 (br. s., 1H), 8.78 (d, J=4.52 Hz, 1H), 8.57 (d, J=1.10 Hz, 2H), 8.30 (d, J=8.19 Hz, 1H), 7.89 (d, J=8.31 Hz, 1H), 7.61 (dd, J=4.89, 7.83 Hz, 1H), 7.15 (d, J=11.86 Hz, 1H), 3.75-3.80 (m, 4H), 3.67-3.71 (m, 4H), 3.05 (br. s., 2H), 2.75-2.91 (m, 2H), 2.21 (br. s., 4H), 0.98 (br. s., 3H); LCMS [M+H]+: 492.4.

Example 81: N-[4-chloro-5-(2-morpholin-4-ylpyrimidin-5-yl)-2-[(3R)-3,4-dimethylpiperazin-1-yl]phenyl]-6-oxo-4-(trifluoromethyl)-1H-pyridine-3-carboxamide

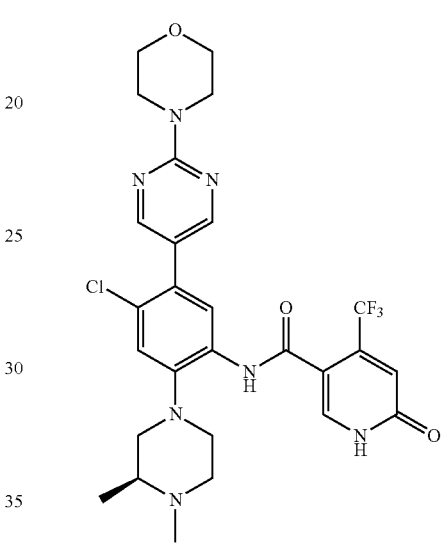

Step 1: (S)-4-(4-bromo-5-chloro-2-nitrophenyl)-1,2-dimethylpiperazine

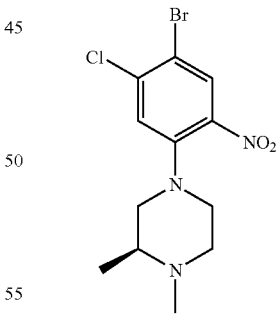

A solution of 1-bromo-2-chloro-4-fluoro-5-nitrobenzene (1.0 g, 3.9 mmol) in toluene (2 mL) was added dropwise to a rapidly stirring mixture of (S)-1,2-dimethylpiperazine dihydrochloride (0.73 g, 3.9 mmol) and potassium carbonate (1.4 g, 9.8 mmol) in toluene (10 mL) at room temperature. After stirring for 20 minutes at room temperature the reaction was warmed to 45° C. for 18 h. After the reaction was cooled to room temperature the reaction mixture was partitioned between water (50 mL) and ethyl acetate (50 mL). The layers were separated and the aqueous layer was extracted with additional ethyl acetate. The combined organic extracts were dried over magnesium sulfate and after removal of the inorganics by filtration the filtrate was concentrated onto celite. Purification by flash chromatography [1-10% MeOH/DCM+0.5% NH₄OH] afforded (S)-4-(4-bromo-5-chloro-2-nitrophenyl)-1,2-dimethylpiperazine (0.66 g, 48%). LCMS [M+H]+: 348.0.

Step 2: (S)-4-(5-(2-chloro-4-(3,4-dimethylpiperazin-1-yl)-5-nitrophenyl)pyrimidin-2-yl)morpholine

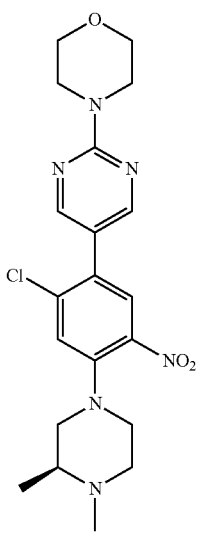 [SMILES: C[C@H]1CN(c2cc(Cl)c(-c3cnc(N4CCOCC4)nc3)cc2N)CCN1C]

A vial was charged with (S)-4-(4-bromo-5-chloro-2-nitrophenyl)-1,2-dimethylpiperazine (0.40 g, 1.1 mmol), 2-(4-morpholino)pyrimidine-5-boronic acid pinacol ester (0.37 g, 1.3 mmol) and tetrakis(triphenylphosphine)palladium(0) (0.13 g, 0.11 mmol). The vial was sealed with a septum, evacuated and backfilled with nitrogen. 1,4-Dioxane (7 mL) and 2 M aqueous sodium carbonate (3 mL) were added via syringe and the vial was evacuated and backfilled an additional time. The reaction was heated to 100° C. for 3 h. After cooling to room temperature the reaction mixture was concentrated onto celite and flash chromatography [0.5-10% MeOH/DCM+0.5% NH₄OH] afforded (S)-4-(5-(2-chloro-4-(3,4-dimethylpiperazin-1-yl)-5-nitrophenyl)pyrimidin-2-yl)morpholine (0.28 g, 56%). LCMS [M+H]+: 433.2.

Step 3: (S)-4-chloro-2-(3,4-dimethylpiperazin-1-yl)-5-(2-morpholinopyrimidin-5-yl)aniline

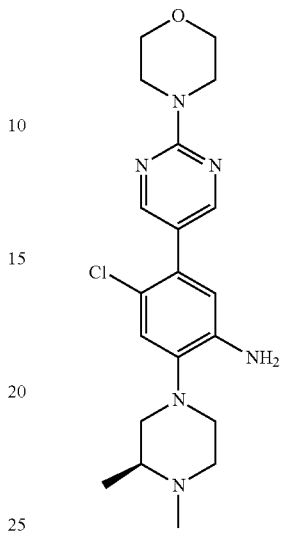

A mixture of (S)-4-(5-(2-chloro-4-(3,4-dimethylpiperazin-1-yl)-5-nitrophenyl)pyrimidin-2-yl)morpholine (0.12 g, 0.28 mmol), iron powder (0.080 g, 1.4 mmol), hydrochloric acid (0.12 mL, 1.4 mmol), MeOH (5 mL) and water (1 mL) was heated to 85° C. for 1 h. After cooling to room temperature the reaction was diluted with MeOH and filtered through celite, eluting with additional MeOH. The filtrate was concentrated onto celite and flash chromatography [0.5-10% MeOH/DCM+1% NH₄OH] afforded (S)-4-chloro-2-(3,4-dimethylpiperazin-1-yl)-5-(2-morpholinopyrimidin-5-yl)aniline (0.046 g, 41%). LCMS [M+H]+: 403.3.

Step 4: (S)—N-(4-chloro-2-(3,4-dimethylpiperazin-1-yl)-5-(2-morpholinopyrimidin-5-yl)phenyl)-6-oxo-4-(trifluoromethyl)-1,6-dihydropyridine-3-carboxamide

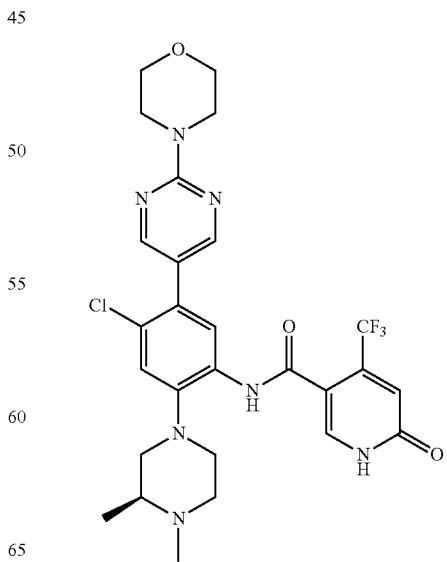

A suspension of 6-chloro-4-(trifluoromethyl)nicotinic acid (0.030 g, 0.13 mmol) and thionyl chloride (0.32 mL, 4.5 mmol) was heated at 80° C. for 1 h. The reaction mixture was concentrated to dryness to afford the acid chloride which was suspended in anhydrous DCM (2 mL) and treated with a solution of (S)-4-chloro-2-(3,4-dimethylpiperazin-1-yl)-5-(2-morpholinopyrimidin-5-yl)aniline (0.045 g, 0.11 mmol) and triethylamine (0.05 mL, 0.3 mmol) in DCM (2 mL) at room temperature. After stirring for 18 h at room temperature the reaction mixture was quenched with a saturated aqueous NaHCO₃ solution (10 mL) and extracted with DCM. The combined organic extracts were dried over magnesium sulfate and after removal of the inorganics by filtration the filtrate was concentrated onto celite. Purification by flash chromatography [0.5-10% MeOH/DCM+0.5% NH₄OH] afforded (S)-6-chloro-N-(4-chloro-2-(3,4-dimethylpiperazin-1-yl)-5-(2-morpholinopyrimidin-5-yl)phenyl)-4-(trifluoromethyl)nicotinamide. A mixture of the prepared amide and sodium acetate (0.018 g, 0.22 mmol) in HOAc/H₂O (4 mL/1 mL) was irradiated at 160° C. for 4 h. The reaction mixture was concentrated onto celite and purified by flash chromatography [0.5-10% MeOH/DCM+0.5% NH₄OH] to afford the title compound (S)—N-(4-chloro-2-(3,4-dimethylpiperazin-1-yl)-5-(2-morpholinopyrimidin-5-yl)phenyl)-6-oxo-4-(trifluoromethyl)-1,6-dihydropyridine-3-carboxamide (0.019 g, 29%). ¹H NMR (500 MHz, DMSO-d6) δ=12.58 (br. s., 1H), 9.55 (s, 1H), 8.46 (s, 2H), 8.24 (br. s., 1H), 7.93 (br. s., 1H), 7.80 (s, 1H), 7.28 (s, 1H), 6.88-6.79 (m, 2H), 6.64 (s, 1H), 3.78-3.75 (m, 4H), 3.70-3.68 (m, 4H), 3.06-2.99 (m, 3H), 2.84 (d, J=11.0 Hz, 3H), 2.25 (br. s., 2H), 1.00 (d, J=6.0 Hz, 3H); LCMS [M+H]+: 592.4.

Example 82: N-[4-chloro-5-(2-morpholin-4-ylpyrimidin-5-yl)-2-[(3R,5S)-3,4,5-trimethylpiperazin-1-yl]phenyl]-6-oxo-4-(trifluoromethyl)-1H-pyridine-3-carboxamide

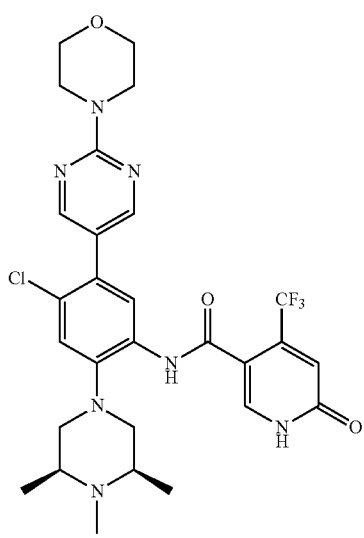 [SMILES: C[C@@H]1CN(c2cc(Cl)c(-c3cnc(N4CCOCC4)nc3)cc2NC(=O)c2c[nH]c(=O)cc2C(F)(F)F)C[C@H](C)N1C]

The title compound was prepared similar to the sequence described above for the preparation of Example 81 using cis-1,2,6-trimethylpiperazine in place of (S)-1,2-dimethylpiperazine dihydrochloride in Step 1. ¹H N-MR (500 MHz, DMSO-d6) δ=12.60 (br. s., 1H), 9.56 (s, 1H), 8.46 (s, 2H), 7.91 (s, 1H), 7.79 (s, 1H), 7.25 (s, 1H), 6.82 (s, 1H), 3.79-3.74 (m, 5H), 3.73-3.66 (m, 5H), 3.01 (d, J=10.6 Hz, 3H), 2.42-2.35 (m, 2H), 2.22 (br. s., 3H), 1.02 (d, J=5.9 Hz, 6H); LCMS [M+H]+: 606.3.

Example 83: N-[4-fluoro-5-(2-morpholin-4-ylpyridin-4-yl)-2-[(3R,5S)-3,4,5-trimethylpiperazin-1-yl]phenyl]-6-oxo-4-(trifluoromethyl)-1H-pyridine-3-carboxamide

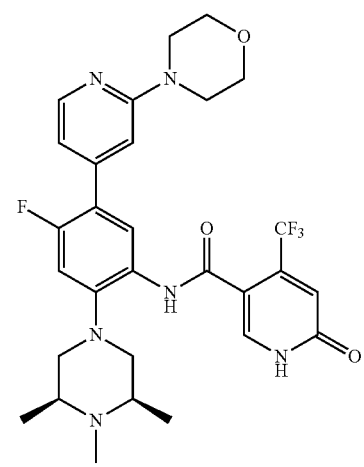 [SMILES: C[C@@H]1CN(c2cc(F)c(-c3ccnc(N4CCOCC4)c3)cc2NC(=O)c2c[nH]c(=O)cc2C(F)(F)F)C[C@H](C)N1C]

The title compound (pale yellow solid, 23.6 mg, 39%) was prepared similar to the procedure of Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 2-morpholinopyridine-4-boronic acid, pinacol ester (58 mg, 0.2 mmol). ¹H NMR (500 MHz, METHANOL-d4) δ=8.18 (d, J=5.3 Hz, 1H), 7.98 (s, 1H), 7.95 (d, J=7.8 Hz, 1H), 7.08 (d, J=12.2 Hz, 1H), 6.97 (s, 1H), 6.95-6.90 (m, 2H), 3.86-3.80 (m, 4H), 3.58-3.49 (m, 4H), 3.11 (d, J=11.2 Hz, 2H), 2.64 (t, J=11.2 Hz, 2H), 2.60-2.53 (m, 2H), 2.39 (s, 3H), 1.18 (d, J=6.1 Hz, 6H); LCMS [M+H]+ 589.4.

Example 84: N-[4-fluoro-5-[6-(2-methoxyethoxy)pyridin-3-yl]-2-[(3R,5S)-3,4,5-trimethylpiperazin-1-yl]phenyl]-6-oxo-4-(triluoromethyl)-1H-pyridine-3-carboxamide Example 85: N-[4-fluoro-5-(3-morpholin-4-ylphenyl)-2-[(3R,5S)-3,4,5-trimethylpiperazin-1-yl]phenyl]-6-oxo-4-(trifluoromethyl)-1H-pyridine-3-carboxamide

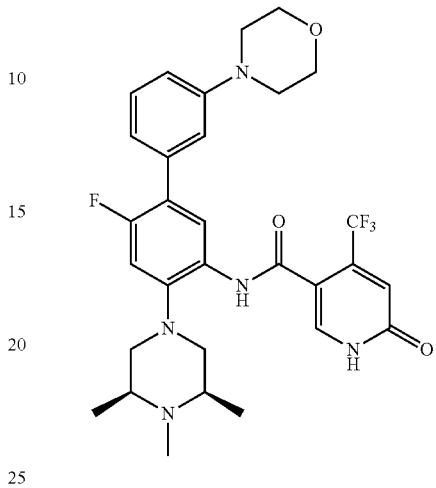

The title compound (46.0 mg, 77%) was prepared similar to the procedure of Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 4-[3-(4,4,5,5-tetramethyl-1,3,2-dioxaborolan-2-yl)phenyl]morpholine (58 mg, 0.2 mmol). $^1$H NMR (500 MHz, METHANOL-d4) δ=7.97 (s, 1H), 7.90 (d, J=7.9 Hz, 1H), 7.34 (t, J=7.9 Hz, 1H), 7.13 (s, 1H), 7.07-7.02 (m, 2H), 7.00 (d, J=8.3 Hz, 1H), 6.92 (s, 1H), 3.86 (d, J=3.1 Hz, 4H), 3.25-3.17 (m, 4H), 3.07 (d, J=11.1 Hz, 2H), 2.67-2.51 (m, 4H), 2.39 (s, 3H), 1.18 (d, J=6.1 Hz, 6H); LCMS [M+H]$^+$ 588.4.

Example 86: N-[4-fluoro-5-(2-morpholin-4-ylpyrimidin-5-yl)-2-[(3R,5S)-3,4,5-trimethylpiperazin-1-yl]phenyl]-2-methoxybenzamide

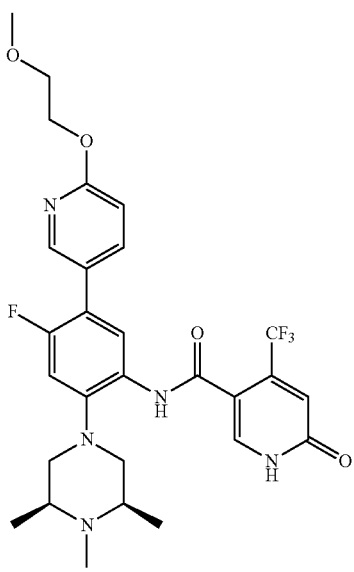

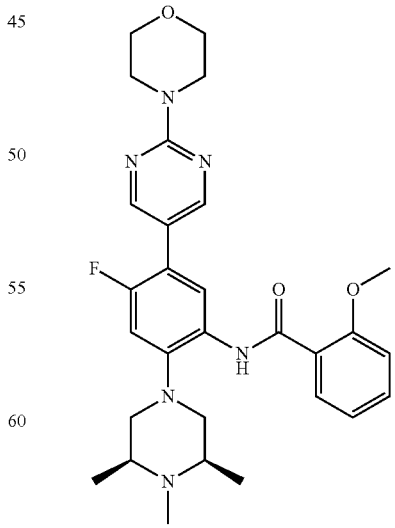

The title compound (pale yellow solid, 41.2 mg, 68%) was prepared similar to the procedure of Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 2-(2-methoxyethoxy)-5-(4,4,5,5-tetramethyl-1,3,2-dioxaborolan-2-yl)pyridine (56 mg, 0.2 mmol). $^1$H NMR (500 MHz, METHANOL-d4) δ=8.31 (s, 1H), 7.97 (s, 1H), 7.92 (d, J=8.2 Hz, 1H), 7.89 (d, J=8.7 Hz, 1H), 7.09 (d, J=11.8 Hz, 1H), 6.93 (s, 1H), 6.92 (d, J=7.6 Hz, 2H), 4.51-4.44 (m, 2H), 3.79 (dd, J=4.1, 5.1 Hz, 2H), 3.44 (s, 3H), 3.08 (d, J=11.1 Hz, 2H), 2.67-2.54 (m, 4H), 2.40 (s, 3H), 1.18 (d, J=6.1 Hz, 6H); LCMS [M+H]$^+$ 578.4.

The title compound (beige solid, 48.1 mg, 86%) was prepared by a procedure similar to that of Example 34 using 4-fluoro-5-(2-morpholinopyrimidin-5-yl)-2-((3S,5R)-3,4,5-trimethylpiperazin-1-yl)aniline (40 mg, 0.1 mmol) and 2-methoxybenzoyl chloride (22 μL, 0.15 mmol). $^1$H NMR (500 MHz, CHLOROFORM-d) δ=10.41 (s, 1H), 8.66 (d, J=8.4 Hz, 1H), 8.59 (s, 2H), 8.33 (d, J=7.8 Hz, 1H), 7.55 (t, J=7.8 Hz, 1H), 7.18 (t, J=7.5 Hz, 1H), 7.09 (d, J=8.3 Hz, 1H), 6.97 (d, J=11.6 Hz, 1H), 4.12 (s, 3H), 3.92-3.85 (m, 4H), 3.85-3.78 (m, 4H), 3.03-2.96 (m, 2H), 2.63 (t, J=11.0 Hz, 2H), 2.51-2.42 (m, 2H), 2.37 (s, 3H), 1.14 (d, J=6.1 Hz, 6H); LCMS [M+H]$^+$ 535.4.

Example 87: 2-chloro-4-fluoro-N-[4-fluoro-5-(2-morpholin-4-ylpyrimidin-5-yl)-2-[(3R,5S)-3,4,5-trimethylpiperazin-1-yl]phenyl]benzamide

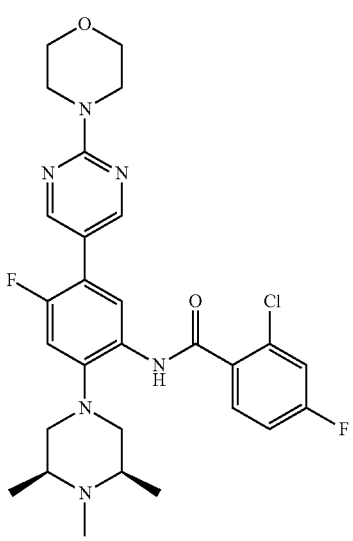 [SMILES: C[C@@H]1CN(c2cc(F)c(-c3cnc(N4CCOCC4)nc3)cc2NC(=O)c2ccc(F)cc2Cl)C[C@H](C)N1C]

The title compound (off-white solid, 42.7 mg, 75%) was prepared by a procedure similar to that of Example 34 using 4-fluoro-5-(2-morpholinopyrimidin-5-yl)-2-((3S,5R)-3,4,5-trimethylpiperazin-1-yl)aniline (40 mg, 0.1 mmol) and 2-chloro-4-fluorobenzoylchloride (20 μL, 0.15 mmol). $^1$H NMR (500 MHz, CHLOROFORM-d) δ=9.22 (s, 1H), 8.69 (d, J=8.3 Hz, 1H), 8.59 (s, 2H), 7.86 (dd, J=6.1, 8.7 Hz, 1H), 7.26 (dd, J=2.4, 8.4 Hz, 1H), 7.16 (t, J=8.2 Hz, 1H), 7.04 (d, J=11.2 Hz, 1H), 3.92-3.86 (m, 4H), 3.85-3.78 (m, 4H), 2.92-2.86 (m, 2H), 2.66 (t, J=10.9 Hz, 2H), 2.42-2.32 (m, 5H), 1.14 (d, J=6.2 Hz, 6H); LCMS [M+H]$^+$ 557.4.

Example 88: 5-fluoro-N-[4-fluoro-5-(2-morpholin-4-ylpyrimidin-5-yl)-2-[(3R,5S)-3,4,5-trimethylpiperazin-1-yl]phenyl]-2-(trifluoromethyl)benzamide

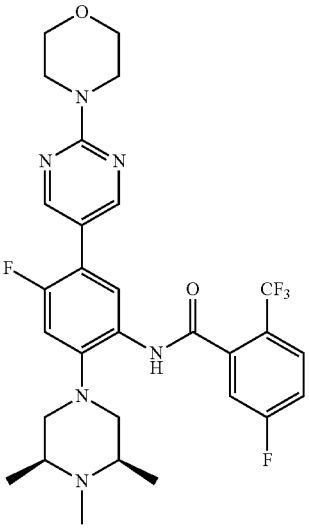

The title compound (beige solid, 53.4 mg, 87%) was prepared by a procedure similar to that of Example 34 using 4-fluoro-5-(2-morpholinopyrimidin-5-yl)-2-((3S,5R)-3,4,5-trimethylpiperazin-1-yl)aniline (40 mg, 0.1 mmol) and 5-fluoro-2-(trifluoromethyl)benzoyl chloride (23 μL, 0.15 mmol). $^1$H NMR (500 MHz, CHLOROFORM-d) δ=8.64-8.53 (m, 4H), 7.83 (dd, J=5.0, 8.7 Hz, 1H), 7.38-7.30 (m, 2H), 7.03 (d, J=11.2 Hz, 1H), 3.93-3.87 (m, 4H), 3.85-3.78 (m, 4H), 2.85 (d, J=10.9 Hz, 2H), 2.64 (t, J=10.9 Hz, 2H), 2.32-2.21 (m, 5H), 1.13 (d, J=6.2 Hz, 6H); LCMS [M+H]$^+$ 591.4.

Example 89: N-[4-fluoro-5-(2-morpholin-4-ylpyrimidin-5-yl)-2-[(3R,5S)-3,4,5-trimethylpiperazin-1-yl]phenyl]-3-methoxybenzamide

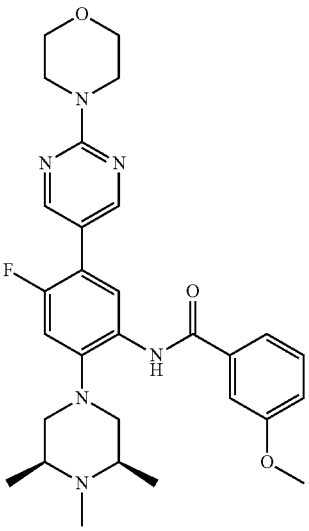

The title compound (yellow solid, 39.3 mg, 72%) was prepared by a procedure similar to that of Example 34 using 4-fluoro-5-(2-morpholinopyrimidin-5-yl)-2-((3S,5R)-3,4,5-trimethylpiperazin-1-yl)aniline (40 mg, 0.1 mmol) and 3-methoxybenzoyl chloride (21 μL, 0.15 mmol). $^1$H NMR (500 MHz, CHLOROFORM-d) δ=9.25 (s, 1H), 8.69 (d, J=8.3 Hz, 1H), 8.60 (s, 2H), 7.54-7.52 (m, 1H), 7.47-7.44 (m, 1H), 7.17-7.12 (m, 1H), 7.03 (d, J=11.2 Hz, 1H), 3.93 (s, 3H), 3.91-3.87 (m, 4H), 3.82 (d, J=1.0 Hz, 4H), 2.92 (d, J=11.0 Hz, 2H), 2.71 (t, J=11.0 Hz, 2H), 2.52-2.42 (m, 2H), 2.39 (s, 3H), 1.18 (d, J=6.2 Hz, 6H); LCMS [M+H]$^+$ 535.4.

Example 90: N-[4-fluoro-5-[4-(2-methoxyethoxy)phenyl]-2-[(3R,5S)-3,4,5-trimethylpiperazin-1-yl]phenyl]-6-oxo-4-(trifluoromethyl)-JH-pyridine-3-carboxamide

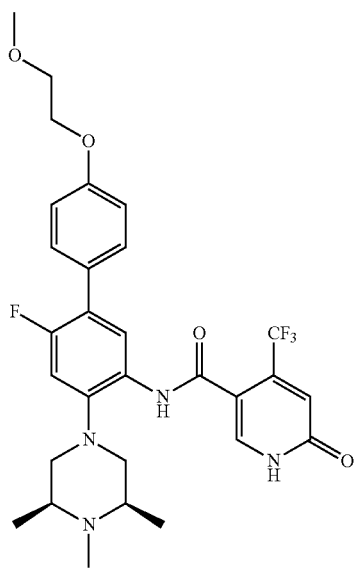

The title compound (grey solid, 37.6 mg, 63%) was prepared by a procedure similar to that of Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 4-(2-methoxyethoxy)phenylboronic acid (39 mg, 0.2 mmol). $^1$H NMR (500 MHz, METHANOL-d4) δ=7.97 (s, 1H), 7.91 (d, J=8.2 Hz, 1H), 7.49 (d, J=7.6 Hz, 2H), 7.07-7.01 (m, 3H), 6.92 (s, 1H), 4.18 (dd, J=3.8, 5.4 Hz, 2H), 3.82-3.76 (m, 2H), 3.46 (s, 3H), 3.07 (d, J=11.0 Hz, 2H), 2.68-2.53 (m, 4H), 2.39 (s, 3H), 1.18 (d, J=6.0 Hz, 6H); LCMS [M+H]$^+$ 577.4.

Example 91: N-[5-[5-chloro-6-(2-methylpropoxy)pyridin-3-yl]-4-fluoro-2-[(3R,5S)-3,4,5-trimethylpiperazin-1-yl]phenyl]-6-oxo-4-(trifluoromethyl)-1H-pyridine-3-carboxamide

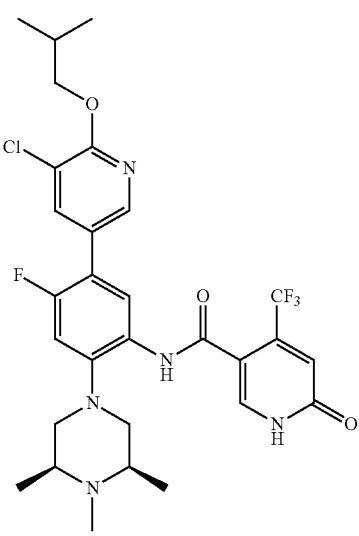 [SMILES: CC(C)COc1ncc(-c2cc(NC(=O)c3c[nH]c(=O)cc3C(F)(F)F)c(N3C[C@@H](C)N(C)[C@@H](C)C3)cc2F)cc1Cl]

The title compound (light brown solid, 48.1 mg, 77%) was prepared by a procedure similar to that of Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 3-chloro-2-isobutoxypyridine-5-boronic acid (46 mg, 0.2 mmol). $^1$H NMR (500 MHz, METHANOL-d4) δ=8.24 (s, 1H), 7.97 (d, J=7.8 Hz, 2H), 7.92 (d, J=8.3 Hz, 1H), 7.10 (d, J=12.1 Hz, 1H), 6.93 (s, 1H), 4.21 (d, J=6.6 Hz, 2H), 3.09 (d, J=11.2 Hz, 2H), 2.68-2.60 (m, 2H), 2.60-2.53 (m, 2H), 2.39 (s, 3H), 2.15 (td, J=6.7, 13.4 Hz, 1H), 1.18 (d, J=6.1 Hz, 6H), 1.08 (d, J=6.7 Hz, 6H); LCMS [M+H]$^+$ 610.3.

Example 92: N-[5-[3-chloro-4-(cyclopropylmethoxy)phenyl]-4-fluoro-2-[(3R,5S)-3,4,5-trimethylpiperazin-1-yl]phenyl]-6-oxo-4-(trifluoromethyl)-1H-pyridine-3-carboxamide

Example 93: N-[4-fluoro-5-(2-morpholin-4-ylpyrimidin-5-yl)-2-[(3R,5S)-3,4,5-trimethylpiperazin-1-yl]phenyl]-1-methyl-6-oxo-4-(trifluoromethyl)pyridine-3-carboxamide

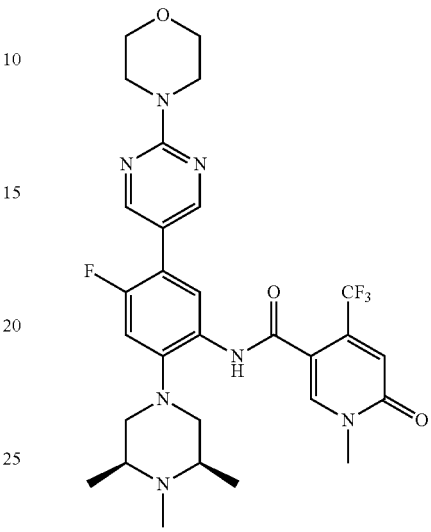

Step 1: 5-bromo-2-chloro-4-iodopyridine

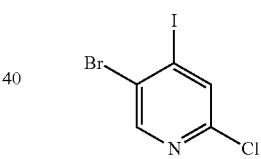

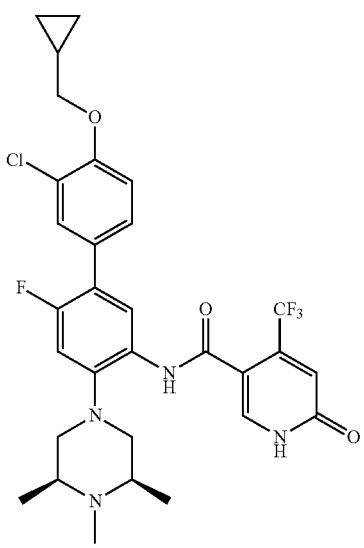 [SMILES: C[C@@H]1CN(c2cc(F)c(-c3ccc(OCC4CC4)c(Cl)c3)cc2NC(=O)c2c[nH]c(=O)cc2C(F)(F)F)C[C@H](C)N1C]

The title compound (light brown solid, 26.9 mg, 43%) was prepared by a procedure similar to that of Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and (3-chloro-4-(cyclopropylmethoxy)phenyl)boronic acid (45.3 mg, 0.2 mmol). $^1$H NMR (500 MHz, METHANOL-d4) δ=7.97 (s, 1H), 7.90 (d, J=8.3 Hz, 1H), 7.58 (s, 1H), 7.45 (d, J=8.7 Hz, 1H), 7.13 (d, J=8.6 Hz, 1H), 7.06 (d, J=12.1 Hz, 1H), 6.93 (s, 1H), 3.98 (d, J=6.8 Hz, 2H), 3.07 (d, J=11.1 Hz, 2H), 2.67-2.53 (m, 4H), 2.40 (s, 3H), 1.38-1.30 (m, 1H), 1.18 (d, J=6.0 Hz, 6H), 0.70-0.64 (m, 2H), 0.46-0.41 (m, 2H); LCMS [M+H]$^+$ 607.3.

A stirred solution of DIPA (4.02 mL, 28.8 mmol, 1.1 eq) in dry THF (50 mL) was cooled to −78° C. and n-BuLi (10.47 mL, 26.18 mmol, 1.0 eq, 2.5M in hexane) was added dropwise under an argon atmosphere. Then, the reaction mixture was stirred for 30 min. at the same temp., followed by the addition of a solution of 2-chloro-5-bromopyridine (5.0 g, 26.178 mmol, 1.0 eq) in dry THF (50 mL) and stirred for 1 h at the same temp. Then, a solution of iodine (6.64 g, 26.178 mmol, 1.0 eq) in THF (50 mL) was added dropwise at −78° C. After completion of addition the reaction mixture was allowed to warm to RT over 4 h. The reaction progress was monitored by TLC. The reaction mixture was quenched with a saturated aqueous solution of sodium thiosulfate, and extracted with EtOAc (3×100 mL). The combined organic layer was dried over Na$_2$SO$_4$ and concentrated under reduced pressure to obtain the crude compound. The crude compound was recrystallized from ethanol (20 mL) to give the title compound (5 g, 60.3%) as an off white solid. LCMS: [M+H]+ 317.86.

Step 2:
5-bromo-2-chloro-4-(trifluoromethyl)pyridine

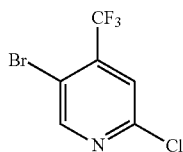

To a stirred solution of 5-bromo-2-chloro-4-iodopyridine (20.0 g, 63.09 mmol, 1.0 eq) in DMF (200 mL), methyl 2,2-difluoro-2-(fluorosulfonyl)acetate (16.15 mL, 126.18 mmol, 2.0 eq) and CuI (24.02 g, 126.18 mmol, 2.0 eq) were added at RT under argon atmosphere and the reaction mixture was heated to 100° C. for 6 h. TLC analysis indicated a non-polar spot. The reaction mixture was diluted with water (200 mL) and filtered off and washed with n-pentane (1 L) and cold water (3 L). The separated organic layer was dried over sodium sulfate and concentrated under reduced pressure at 30° C. The crude compound was purified by column chromatography (Silica gel, 100-200 mesh) using 5% EtOAc in pet ether as an eluent to afford the title compound (9.0 g, 55.2%) as a liquid compound. TLC: 5% EtOAc in pet ether; $R_f$: 0.7

Step 3:
5-bromo-2-methoxy-4-(trifluoromethyl)pyridine

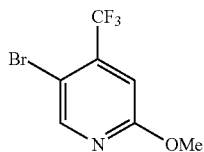 [SMILES: COc1cc(C(F)(F)F)c(Br)cn1]

To a solution of 5-bromo-2-chloro-4-(trifluoromethyl)pyridine (24.0 g, 93.02 mmol, 1.0 eq) in methanol (200 mL), was added 30% NaOMe (33.08 mL, 186.04 mmol, 2.0 eq). Then, the reaction mixture was heated at 70° C. for 6 h. TLC analysis indicated formation of a non-polar spot. The reaction mixture was diluted with water and extracted with EtOAc (3×200 mL). The separated organic layer was dried over sodium sulfate and concentrated under reduced pressure at 30° C. The crude compound was purified by column chromatography (silica gel, 100-200 mesh) using 5% EtOAc in pet ether as an eluent to give 5-bromo-2-methoxy-4-(trifluoromethyl)pyridine (15 g, 63.47%) as an off white solid. TLC: 5% EtOAc in pet ether; $R_f$: 0.8.

Step 4: 6-methoxy-4-(trifluoromethyl)nicotinic acid

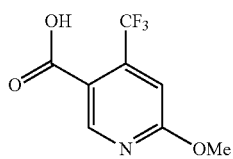 [SMILES: COc1cc(C(F)(F)F)c(C(=O)O)cn1]

A solution of n-butyl magnesium chloride (20% in THF; 27.8 mL, 27.79 mmol, 1.2 eq) was added to a solution of n-butyl lithium (2.5M in hexane; 23.16 mL, 92.64 mmol, 4 eq) under argon atm. After 10 min, the reaction mixture was diluted with dry THF (80 mL) and cooled to −78° C. A solution of 5-bromo-2-methoxy-4-(trifluoromethyl)pyridine (6 g, 23.16 mmol, 1.0 eq) in dry THF (30 mL) was added to the above reaction mixture at −78° C. and stirred for 1 h at the same temperature. Then, crushed dry ice was added at −78° C. After addition, the reaction mixture was allowed to remain at RT for 16 h. TLC analysis indicated formation of polar spot. The reaction mixture was concentrated under reduced pressure and acidified with 2N aq. HCl (20 mL), then the obtained solid was filtered off and washed with n-pentane to give 6-methoxy-4-(trifluoromethyl)nicotinic acid (3.5 g, 67.3%) as an off white solid compound. LCMS: [M+H]+ 221.99, M+H.

Step 5: methyl 6-methoxy-4-(trifluoromethyl)nicotinate

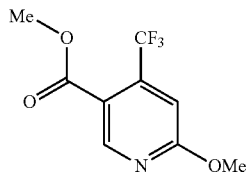 [SMILES: COC(=O)c1cnc(OC)cc1C(F)(F)F]

To a stirred solution of 6-methoxy-4-(trifluoromethyl)nicotinic acid (22 g, 99.5 mmol, 1.0 eq) in acetone (160 mL) was added $K_2CO_3$ (20.5 g, 149.25 mmol, 1.5 eq) followed by the dropwise addition of dimethylsulphate (16.3 g, 129.4 mmol, 1.3 eq) at 0° C. and the reaction mixture was allowed to remain at RT over 2 h. TLC analysis indicated formation of a non-polar spot. The reaction mixture was concentrated under reduced pressure to crude residue, which was redissolved in EtOAc (500 mL) and washed with water and brine. The separated organic layer was dried over $Na_2SO_4$ and concentrated under reduced pressure to give crude compound. The crude compound was purified by column chromatography (silica gel, 100-200 mesh) using 0-2% EtOAc in pet ether as an eluent to afford methyl 6-methoxy-4-(trifluoromethyl)nicotinate (19 g, 81.5%) as a white solid. [M+H]+ 236.37.

Step 6: methyl 6-oxo-4-(trifluoromethyl)-1,6-dihydropyridine-3-carboxylate

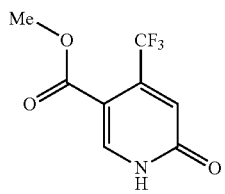

To a stirred solution of methyl 6-methoxy-4-(trifluoromethyl)nicotinate (3 g, 12.76 mmol, 1.0 eq) in ACN (30 mL) was added TMS-Cl (4.54 g, 38.28 mmol, 3.0 eq) and NaI (5.7 g, 38.28 mmol, 3.0 eq) at RT under argon atm. Then, the reaction mixture was heated to reflux for 3 h. TLC analysis indicated formation of polar spot. Then, the reaction mixture was diluted with water (500 mL) and extracted with EtOAc (3×100 mL). The combined organic layer was dried over Na₂SO₄ and concentrated under reduced pressure to give crude compound. The crude compound was purified by column chromatography (silica gel, 100-200 mesh) using 0-5% EtOAc in pet ether as eluent to afford methyl 6-oxo-4-(trifluoromethyl)-1,6-dihydropyridine-3-carboxylate (1.2 g, 42.8%) as an off-white solid. LCMS: [M+H]+ 221.96.

Step 7: methyl 1-methyl-6-oxo-4-(trifluoromethyl)-1,6-dihydropyridine-3-carboxylate

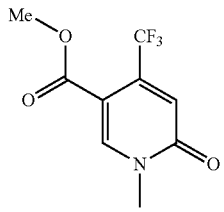

To a stirred solution of methyl 6-oxo-4-(trifluoromethyl)-1,6-dihydropyridine-3-carboxylate (13.0 g, 58.82 mmol, 1.0 eq) in DMF (130 mL) was added methyl iodide (4.3 mL, 70.58 mmol, 1.2 eq) and cesium carbonate (28.6 g, 88.2 mmol, 1.5 eq) at RT under argon atmosphere. Then, the reaction mixture was stirred at RT for 1 h. TLC analysis indicated formation of a non-polar spot. The reaction mixture was diluted with cold water (1 L) and extracted with EtOAc (3×150 mL). The combined organic layer was dried over Na₂SO₄ and concentrated under reduced pressure to crude compound. The crude compound was purified by column chromatography (silica gel, 100-200 mesh) using 0-30% EtOAc in pet ether as eluent to give methyl 1-methyl-6-oxo-4-(trifluoromethyl)-1,6-dihydropyridine-3-carboxylate (10 g, 72.4% yield) as off-white solid. LCMS: 99.26% with [M+H]+ 235.98.

Step 8: 1-methyl-6-oxo-4-(trifluoromethyl)-1,6-dihydropyridine-3-carboxylic acid

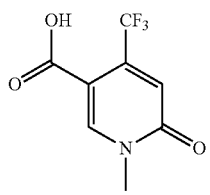

To a stirred solution of methyl 1-methyl-6-oxo-4-(trifluoromethyl)-1,6-dihydropyridine-3-carboxylate (9.0 g, 38.29 mmol, 1.0 eq) in THF:MeOH:H₂O (220 mL, 3:1:2) was added LiOH·H₂O (4.7 g, 114.8 mmol, 3.0 eq) at RT and the reaction mixture was stirred at RT for 16 h. TLC analysis indicated formation of polar spot. The reaction mixture was concentrated under reduced pressure to crude product. The crude product was acidified with aqueous 2N HCl (20 mL), the resulting precipitate was filtered off and washed with diethyl to give 1-methyl-6-oxo-4-(trifluoromethyl)-1,6-dihydropyridine-3-carboxylic acid (6.0 g, 71.42%) as an off white solid. LCMS: [M+H]+ 221.95.

Step 9: N-[4-fluoro-5-(2-morpholin-4-ylpyrimidin-5-yl)-2-[(3R,5S)-3,4,5-trimethylpiperazin-1-yl]phenyl]-1-methyl-6-oxo-4-(trifluoromethyl)pyridine-3-carboxamide In a 5 ml microwave vial to a suspension of 1-methyl-6-oxo-4-(trifluoromethyl)-1,6-dihydropyridine-3-carboxylic acid (59.6 mg, 0.270 mmol) in pyridine, anhydrous (327 μl, 4.04 mmol) was added slowly diethyl chlorophosphate (59.4 μl, 0.411 mmol) at RT in an atmosphere of nitrogen. The reaction mixture was stirred at rt for 2 h. The suspension turned brown. To this, 4-fluoro-5-(2-morpholinopyrimidin-5-yl)-2-((3R,5S)-3,4,5-trimethylpiperazin-1-yl)aniline (27 mg, 0.067 mmol) was added and the reaction was heated at 70° C. for 16 h. After completion, pyridine was removed in vacuo and the residue partitioned between ethyl acetate (3 mL) and saturated sodium bicarbonate solution (3 mL). The suspension was stirred for 10 min. The organic layer was separated, and dried over anhydrous Na₂SO₄. The solvent was evaporated in vacuo yielding the crude product which was purified by flash column chromatography on silica gel (0-100%, 89% CH₂Cl₂, 10% MeOH, 1% NH₄Ac/CH₂Cl₂) to afford the desired compound. ¹H NMR (500 MHz, MeOD) δ 8.55 (d, J=1.1 Hz, 2H), 8.24 (s, 1H), 7.90 (d, J=8.3 Hz, 1H), 7.08 (d, J=12.1 Hz, 1H), 6.94 (s, 1H), 3.85-3.82 (m, 4H), 3.78-3.75 (m, 4H), 3.64 (s, 3H), 3.04 (d, J=11.3 Hz, 2H), 2.60 (t, J=11.2 Hz, 2H), 2.50 (dd, J=8.3, 5.9 Hz, 2H), 2.34 (s, 3H), 1.15 (d, J=6.2 Hz, 6H); LCMS [M+1]+=604.24.

Example 94: N-[5-(3,6-dihydro-2H-pyran-4-yl)-4-fluoro-2-[(3R,5S)-3,4,5-trimethylpiperazin-1-yl]phenyl]-6-oxo-4-(trifluoromethyl)-1H-pyridine-3-carboxamide

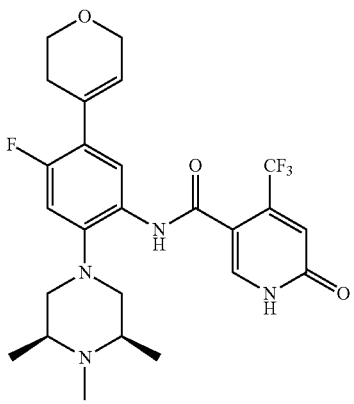

The procedure followed was similar to Example 39 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) and 3,6-dihydro-2H-pyran-4-boronic acid, pinacol ester (24.28 mg, 0.116 mmol) followed by deprotection of the intermediate to afford after purification 16 mg (63% for final step) of the title compound as a beige solid. $^1$H NMR (500 MHz, METHANOL-d4) δ=7.94 (s, 1H), 7.78 (d, J=8.1 Hz, 1H), 6.96 (d, J=12.6 Hz, 1H), 6.94-6.89 (m, 1H), 6.08 (br. s., 1H), 4.39-4.20 (m, 2H), 3.99-3.82 (m, 2H), 3.03 (d, J=10.6 Hz, 2H), 2.65-2.47 (m, 6H), 2.39 (s, 3H), 1.17 (d, J=5.9 Hz, 6H); LCMS [M+H]+ 509.7

Example 95: N-[4-fluoro-2-[(3R,5S)-3,4,5-trimethylpiperazin-1-yl]-5-(1,2,3,6-tetrahydropyridin-4-yl)phenyl]-6-oxo-4-(trifluoromethyl)-1H-pyridine-3-carboxamide

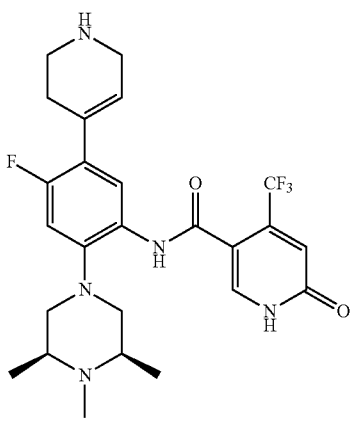

The product was obtained after TFA deprotection of the intermediate resulting from a reaction between N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) and tert-butyl-4-(4,4,5,5-tetramethyl-1,3,2-dioxaborolan-2-yl)-1,2,3,6-tetrahydropyridine-1-carboxylate (35.7 mg, 0.116 mmol) using a method similar to that in Example 39 to give, after deprotection, the title compound in 94% yield for the final step. $^1$H NMR (500 MHz, METHANOL-d4) δ=8.06 (s, 1H), 7.82 (d, J=8.1 Hz, 1H), 6.96 (d, J=12.5 Hz, 1H), 6.80 (s, 1H), 6.05 (br. s., 1H), 3.66 (d, J=2.7 Hz, 2H), 3.24 (t, J=5.8 Hz, 2H), 3.02 (d, J=11.1 Hz, 2H), 2.65-2.47 (m, 6H), 2.36 (s, 3H), 1.16 (d, J=6.1 Hz, 6H); LCMS [M+H]+ 508.6

Example 96: N-[4-fluoro-5-(2-morpholin-4-ylpyrimidin-5-yl)-2-[(3R)-3,4-dimethylpiperazin-1-yl]phenyl]-3-(trifluoromethyl)-1H-pyrazole-4-carboxamide

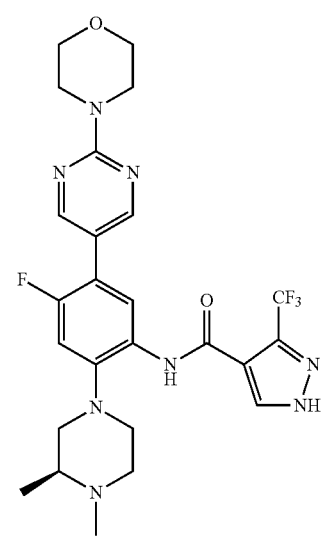 [SMILES: C[C@H]1CN(c2cc(F)c(-c3cnc(N4CCOCC4)nc3)cc2NC(=O)c2c[nH]nc2C(F)(F)F)CCN1C]

The title compound (white solid, 18.1 mg, 62%) was prepared according to a procedure similar to that used in Example 34 with 3-(trifluoromethyl)pyrazole-4-carboxylic acid (27 mg, 0.15 mmol) and (S)-2-(3,4-dimethylpiperazin-1-yl)-4-fluoro-5-(2-morpholinopyrimidin-5-yl)aniline (20 mg, 0.05 mmol). $^1$H NMR (500 MHz, METHANOL-d4) δ=8.58 (s, 2H), 8.39 (br. s., 1H), 7.98 (d, J=8.2 Hz, 1H), 7.11 (d, J=12.0 Hz, 1H), 3.89-3.83 (m, 4H), 3.80-3.75 (m, 4H), 3.04 (d, J=11.4 Hz, 2H), 2.63 (t, J=11.2 Hz, 2H), 2.55-2.46 (m, 2H), 2.37 (s, 3H), 1.15 (d, J=6.2 Hz, 6H); LCMS [M+H]+ 563.4.

Example 97: 4-fluoro-N-[4-fluoro-5-(2-morpholin-4-ylpyrimidin-5-yl)-2-[(3R)-3,4-dimethylpiperazin-1-yl]phenyl]-3,5-dimethylbenzamide

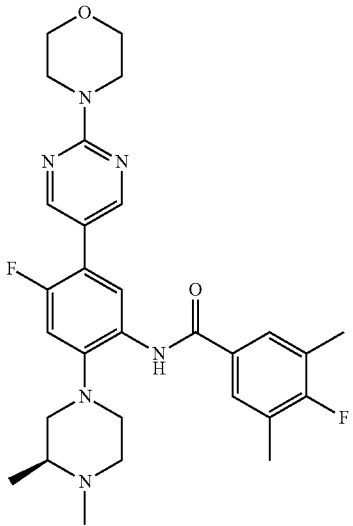 [SMILES: Cc1cc(C(=O)Nc2cc(-c3cnc(N4CCOCC4)nc3)c(F)cc2N2CCN(C)[C@@H](C)C2)cc(C)c1F]

The title compound (pale beige solid, 26.1 mg, 47%) was prepared according to a procedure similar to Example 78 using 4-fluoro-3,5-dimethylbenzoic acid (50 mg, 0.3 mmol) and (S)-2-(3,4-dimethylpiperazin-1-yl)-4-fluoro-5-(2-morpholinopyrimidin-5-yl)aniline (40 mg, 0.1 mmol). $^1$H NMR (500 MHz, CHLOROFORM-d) δ=9.19 (s, 1H), 8.65 (d, J=8.3 Hz, 1H), 8.60 (s, 2H), 7.62 (d, J=6.7 Hz, 2H), 7.02 (d, J=11.2 Hz, 1H), 3.93-3.86 (m, 4H), 3.85-3.79 (m, 4H), 2.94 (d, J=11.0 Hz, 2H), 2.71 (t, J=10.9 Hz, 2H), 2.51-2.41 (m, 2H), 2.41-2.35 (m, 9H), 1.19 (d, J=6.2 Hz, 6H); LCMS [M+H]$^+$ 551.3.

Example 98: N-[5-(3-chloro-5-cyano-4-hydroxyphenyl)-4-fluoro-2-[(3R,5S)-3,4,5-trimethylpiperazin-1-yl]phenyl]-6-oxo-4-(trifluoromethyl)-1H-pyridine-3-carboxamide

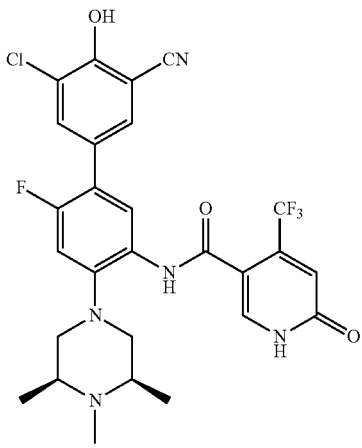 [SMILES: C[C@@H]1CN(c2cc(F)c(-c3cc(Cl)c(O)c(C#N)c3)cc2NC(=O)c2c[nH]c(=O)cc2C(F)(F)F)C[C@H](C)N1C]

The procedure used was similar to that of Example 31 using N-(5-bromo-4-fluoro-2-((3S,5R)-3,4,5-trimethylpiperazin-1-yl)phenyl)-4-(trifluoromethyl)-6-(2-(trimethylsi-lyl)ethoxy)nicotinamide (50 mg, 0.083 mmol) and 3-chloro-5-(4,4,5,5-tetramethyl-1,3,2-dioxaborolan-2-yl)-2-(2-(trimethylsilyl)ethoxy)benzonitrile (43.9 mg, 0.116 mmol) followed by deprotection of the resulting intermediate using TFA to give the title compound as a tan solid. $^1$H NMR (500 MHz, DMSO-d6) δ=12.55 (br. s., 1H), 9.45 (s, 1H), 8.16 (s, 1H), 7.94 (s, 1H), 7.67 (d, J=8.8 Hz, 1H), 7.39 (br. s., 1H), 7.22 (br. s, 1H), 6.95 (d, J=12.8 Hz, 1H), 6.81 (s, 1H), 3.02 (d, J=8.7 Hz, 2H), 2.50-2.44 (m, 4H), 2.27 (br. s., 3H), 1.04 (d, J=5.0 Hz, 6H); LCMS [M+H]+ 578.6

Example 99: N-[5-(5-cyano-6-phenylmethoxypyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

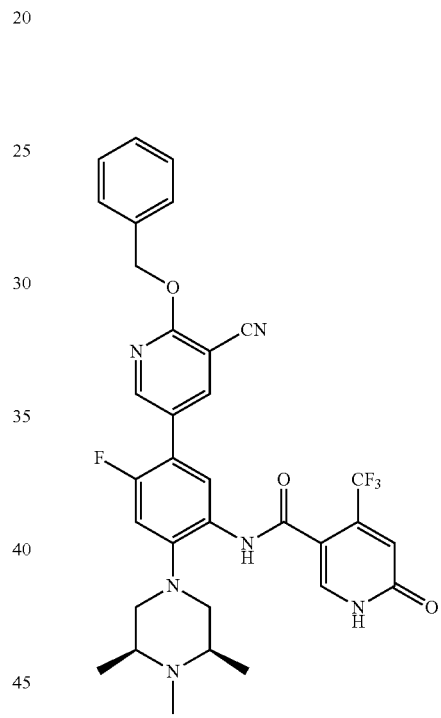

The procedure used was similar to that of Example 31 using N-(5-bromo-4-fluoro-2-((3S,5R)-3,4,5-trimethylpiperazin-1-yl)phenyl)-4-(trifluoromethyl)-6-(2-(trimethylsi-lyl)ethoxy)nicotinamide (300 mg, 0.495 mmol) and 2-(benzyloxy)-5-(trimethylstannyl)nicotinonitrile (222 mg, 0.595 mmol) to give, after deprotection with TFA, 66 mg (20% yield) of the title compound. $^1$H NMR (500 MHz, METHANOL-d4) δ=8.61 (s, 1H), 8.32 (d, J=1.5 Hz, 1H), 8.05 (br. s., 1H), 7.98 (d, J=8.1 Hz, 1H), 7.53 (d, J=7.3 Hz, 2H), 7.41 (t, J=7.4 Hz, 2H), 7.38-7.32 (m, 1H), 7.24 (d, J=11.2 Hz, 1H), 6.95 (s, 1H), 5.69-5.56 (m, 2H), 3.69-3.49 (m, 2H), 3.48-3.36 (m, 2H), 3.11-2.92 (m, 5H), 1.46 (br. s., 6H); LCMS [M+H]+ 635.7.

Example 100: N-[5-(4-cyanophenyl)-4-fluoro-2-[(3R,5S)-3,4,5-trimethylpiperazin-1-yl]phenyl]-6-oxo-4-(trifluoromethyl)-1H-pyridine-3-carboxamide

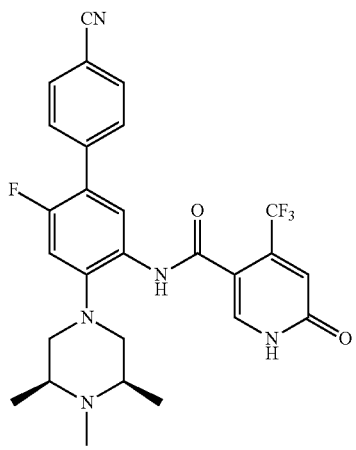

In a 5 mL microwave vial N-(5-bromo-4-fluoro-2-((3R,5S)-3,4,5-trimethylpiperazin-1-yl)phenyl)-4-(trifluoromethyl)-6-(2-(trimethylsilyl)ethoxy)nicotinamide (52.13 mg, 0.086 mmol), 4-cyanophenylboronic acid (18.97 mg, 0.129 mmol), bis(di-tert-butyl(4-dimethylaminophenyl)phosphine)dichloropalladium (II) (6.10 mg, 8.61 µmol) and potassium phosphate tribasic reagent grade (36.5 mg, 0.172 mmol) were dissolved in water (172 µl)/1,4-dioxane (1550 µl) (9:1 mixture) to give a white suspension. The suspension was stirred for 5 min, degassed, purged with $N_2$, and microwaved for 60 min at 120° C. The solvent was evaporated and 15 mL of $CH_2Cl_2$ were added. The suspension was sonicated and extracted from water (15 mL). The solvent was evaporated in vacuo yielding the crude product which was purified by flash column chromatography on silica gel (0-100%, 89% $CH_2Cl_2$, 10% MeOH, 1% $NH_4Ac/CH_2Cl_2$) to afford the protected intermediate. The product was dissolved in 2 mL of DCM and trifluoroacetic acid (132 µl, 1.722 mmol) was added. The purple solution was stirred for 1 h and the solvent was evaporated. The residue was purified using a cation exchange column eluting with MeOH: $NH_4OH$. The residue was freeze dried for 2 days to afford the title compound. $^1$H NMR (500 MHz, MeOD) δ 7.96 (d, J=6.7 Hz, 2H), 7.81 (d, J=8.4 Hz, 2H), 7.74 (d, J=7.4 Hz, 2H), 7.09 (d, J=12.3 Hz, 1H), 6.91 (s, 1H), 3.10 (d, J=11.3 Hz, 2H), 2.63 (t, J=11.2 Hz, 2H), 2.55 (dt, J=6.0, 5.1 Hz, 2H), 2.37 (s, 3H), 1.16 (d, J=6.2 Hz, 6H); $^{19}$F NMR (471 MHz, MeOD) δ -63.78 (s), -120.23 (s); LCMS [M+1]+=528.17.

Example 101: N-[4-fluoro-5-[6-(oxan-4-yloxy)pyridin-3-yl]-2-[(3R,5S)-3,4,5-trimethylpiperazin-1-yl]phenyl]-6-oxo-4-(trifluoromethyl)-1H-pyridine-3-carboxamide

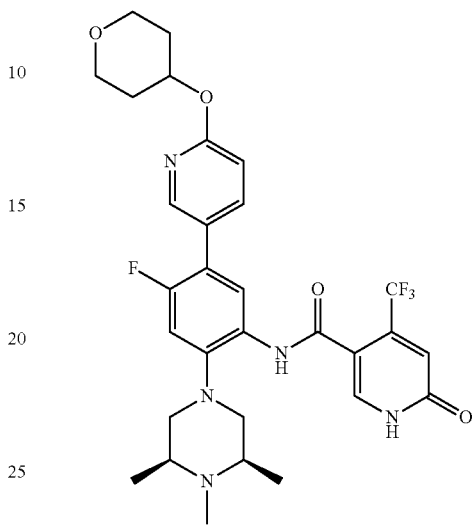

The title compound was prepared similar to the sequence described above for the preparation of Example 100 using 2-(tetrahydropyran-4-yloxy)-5-(4,4,5,5-tetramethyl-1,3,2-dioxaborolan-2-yl)pyridine as the borolane starting material. $^1$H NMR (500 MHz, MeOD) δ 8.29 (s, 1H), 7.96 (s, 1H), 7.90 (d, J=8.3 Hz, 1H), 7.86 (d, J=9.6 Hz, 1H), 7.07 (d, J=12.0 Hz, 1H), 6.90 (s, 1H), 6.87 (d, J=8.7 Hz, 1H), 5.25 (tt, J=8.4, 4.0 Hz, 1H), 4.01-3.94 (m, 2H), 3.63 (ddd, J=11.8, 9.1, 2.9 Hz, 2H), 3.06 (d, J=11.2 Hz, 2H), 2.61 (t, J=11.1 Hz, 2H), 2.54 (s, 2H), 2.13-2.06 (m, 2H), 1.83-1.73 (m, 2H), 1.16 (d, J=6.2 Hz, 6H); LCMS [M+1]+=604.39.

Example 102: N-[5-(3-cyanophenyl)-4-fluoro-2-[(3R,5S)-3,4,5-trimethylpiperazin-1-yl]phenyl]-6-oxo-4-(trifluoromethyl)-1H-pyridine-3-carboxamide

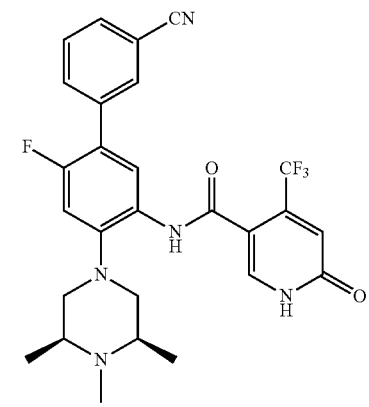

The title compound was prepared similar to the sequence described above for the preparation of Example 100 using 3-cyanophenylboronic acid. $^1$H NMR (500 MHz, MeOD) δ 7.96 (s, 1H), 7.93 (d, J=8.8 Hz, 2H), 7.87 (d, J=7.9 Hz, 1H), 7.73 (d, J=7.8 Hz, 1H), 7.64 (t, J=7.8 Hz, 1H), 7.09 (d, J=12.2 Hz, 1H), 6.91 (s, 1H), 3.09 (d, J=11.3 Hz, 2H), 2.63 (t, J=11.1 Hz, 2H), 2.55 (s, 2H), 2.37 (s, 3H), 1.16 (d, J=6.2 Hz, 6H); LCMS [M+1]+=528.32.

Example 103: N-[5-[2-(dimethylamino)pyrimidin-5-yl]-4-fluoro-2-[(3R,5S)-3,4,5-trimethylpiperazin-1-yl]phenyl]-6-oxo-4-(trifluoromethyl)-1H-pyridine-3-carboxamide

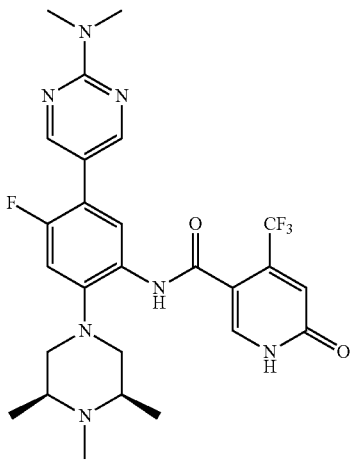

The title compound was prepared according a method similar to that used for the preparation of Example 100 using N,N-dimethyl-5-(4,4,5,5-tetramethyl-1,3,2-dioxaborolan-2-yl)pyrimidin-2-amine. $^1$H NMR (500 MHz, MeOD) δ 8.51 (d, J=1.1 Hz, 2H), 7.97 (s, 1H), 7.89 (d, J=8.2 Hz, 1H), 7.07 (d, J=12.1 Hz, 1H), 6.90 (s, 1H), 3.22 (s, 6H), 3.05 (d, J=11.2 Hz, 2H), 2.61 (t, J=11.2 Hz, 2H), 2.53 (d, J=6.0 Hz, 2H), 2.36 (s, 3H), 1.16 (d, J=6.2 Hz, 6H); LCMS [M+1]+=548.34.

Example 104: N-[5-(5,6-dimethoxypyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

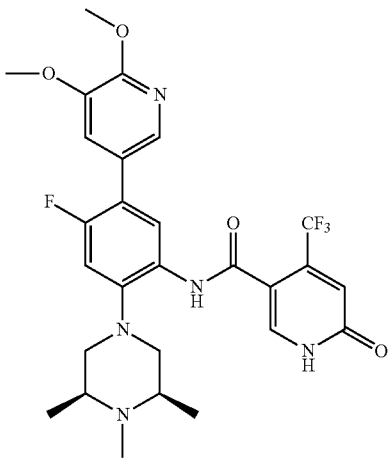 [SMILES: COc1cc(-c2cc(NC(=O)c3c[nH]c(=O)cc3C(F)(F)F)c(N3C[C@@H](C)N(C)[C@@H](C)C3)cc2F)cnc1OC]

The title compound was prepared according a method similar to that used for the preparation of Example 100 with (5,6-dimethoxypyridin-3-yl)boronic acid in place of 4-cyanophenylboronic acid. $^1$H NMR (500 MHz, MeOD) δ 7.97 (s, 1H), 7.90 (d, J=8.1 Hz, 1H), 7.85 (s, 1H), 7.40 (s, 1H), 7.07 (d, J=12.1 Hz, 1H), 6.91 (s, 1H), 3.99 (s, 3H), 3.90 (s, 3H), 3.06 (d, J=11.3 Hz, 2H), 2.62 (t, J=11.1 Hz, 2H), 2.54 (s, 2H), 2.37 (s, 3H), 1.16 (d, J=6.2 Hz, 6H). $^{19}$F NMR (471 MHz, MeOD) δ −63.76 (s), −120.32 (s); LCMS HSS [M+1]+=564.29.

Example 105: N-[4-fluoro-5-(2-morpholin-4-ylpyrimidin-5-yl)-2-[(3R,5S)-3,4,5-trimethylpiperazin-1-yl]phenyl]-1,3-benzodioxole-4-carboxamide

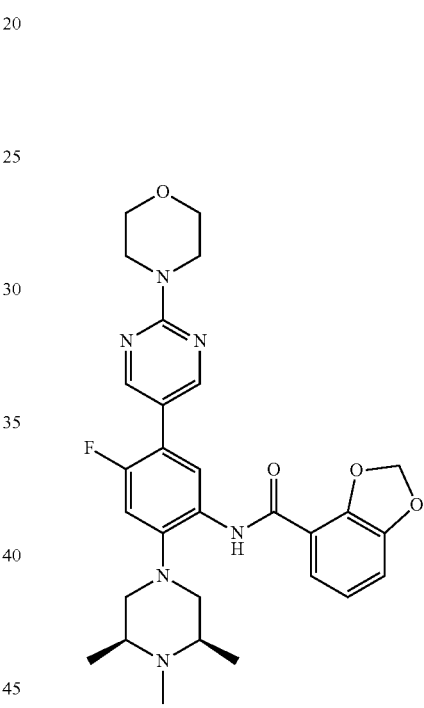

The title compound (light beige solid, 39.9 mg, 71%) was prepared according to a method similar to that used for Example 34 using 1,3-benzodioxole-4-carboxylic acid (33 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.86 (s, 1H), 8.77 (d, J=8.4 Hz, 1H), 8.60 (s, 2H), 7.70 (dd, J=2.4, 7.0 Hz, 1H), 7.08-7.00 (m, 3H), 6.22 (s, 2H), 3.92-3.85 (m, 4H), 3.84-3.79 (m, 4H), 2.96-2.89 (m, 2H), 2.66 (t, J=10.9 Hz, 2H), 2.45-2.37 (m, 5H), 1.17 (d, J=6.2 Hz, 6H); LCMS [M+H]+ 549.2.

Example 106: N-[4-fluoro-5-(2-morpholin-4-ylpyrimidin-5-yl)-2-[(3R,5S)-3,4,5-trimethylpiperazin-1-yl]phenyl]-4-methoxybenzamide

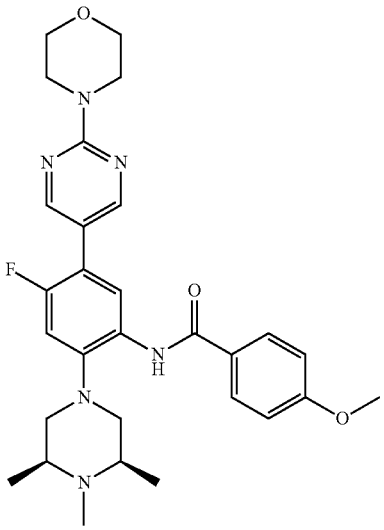

The title compound (beige solid, 52.4 mg, 96%) was prepared through a procedure similar to that of Example 34 using 4-fluoro-5-(2-morpholinopyrimidin-5-yl)-2-((3S,5R)-3,4,5-trimethylpiperazin-1-yl)aniline (40 mg, 0.1 mmol) and 4-methoxybenzoyl chloride (20 µL, 0.15 mmol). $^1$H NMR (500 MHz, CHLOROFORM-d) δ=9.15 (s, 1H), 8.67 (d, J=8.3 Hz, 1H), 8.60 (d, J=1.2 Hz, 2H), 7.92 (d, J=8.2 Hz, 1H), 7.90 (s, 1H), 7.04 (d, J=8.8 Hz, 2H), 7.02 (d, J=11.4 Hz, 1H), 3.93 (s, 3H), 3.91-3.87 (m, 4H), 3.84-3.80 (m, 4H), 2.93 (d, J=11.0 Hz, 2H), 2.69 (t, J=11.0 Hz, 2H), 2.46 (dt, J=3.1, 6.6 Hz, 2H), 2.39 (s, 3H), 1.18 (d, J=6.2 Hz, 6H); LCMS [M+H]$^+$ 535.3.

Example 107: 4-fluoro-N-[4-fluoro-5-(2-morpholin-4-ylpyrimidin-5-yl)-2-[(3R,5S)-3,4,5-trimethylpiperazin-1-yl]phenyl]benzamide

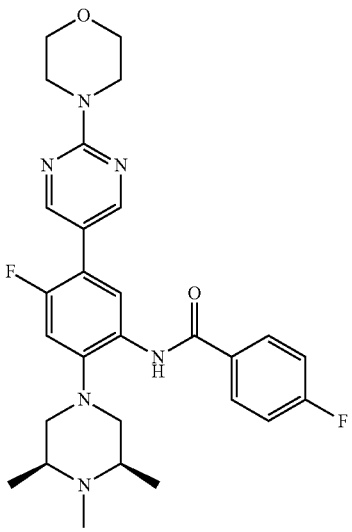

The title compound (light beige solid, 49.0 mg, 93%) was prepared using a procedure similar to Example 34 using 4-fluoro-5-(2-morpholinopyrimidin-5-yl)-2-((3S,5R)-3,4,5-trimethylpiperazin-1-yl)aniline (40 mg, 0.1 mmol) and 4-fluorobenzoyl chloride (18 µL, 0.15 mmol). $^1$H NMR (500 MHz, CHLOROFORM-d) δ=9.19 (s, 1H), 8.65 (d, J=8.2 Hz, 1H), 8.59 (s, 2H), 7.95 (t, J=6.6 Hz, 2H), 7.27-7.22 (m, 2H), 7.03 (d, J=11.2 Hz, 1H), 3.93-3.85 (m, 4H), 3.85-3.78 (m, 4H), 2.92 (d, J=11.0 Hz, 2H), 2.70 (t, J=11.0 Hz, 2H), 2.49-2.37 (m, 5H), 1.18 (d, J=6.2 Hz, 6H); LCMS [M+H]$^+$ 523.4.

Example 108: N-[4-fluoro-5-(3-fluoro-5-morpholin-4-ylphenyl)-2-[(3R,5S)-3,4,5-trimethylpiperazin-1-yl]phenyl]-6-oxo-4-(trifluoromethyl)-1H-pyridine-3-carboxamide

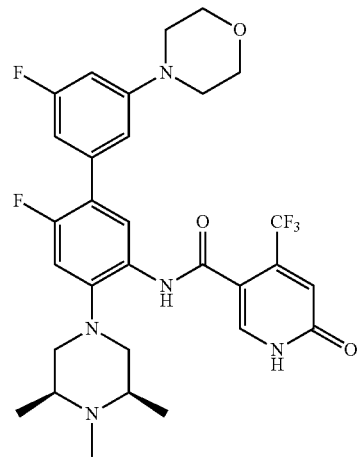

The title compound (brown solid, 28.3 mg, 45%) was prepared through a procedure similar to that of Example 100 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 3-fluoro-5-morpholinophenylboronic acid (45 mg, 0.2 mmol). $^1$H NMR (500 MHz, METHANOL-d4) δ=7.97 (s, 1H), 7.90 (d, J=8.3 Hz, 1H), 7.58 (s, 1H), 7.45 (d, J=8.7 Hz, 1H), 7.13 (d, J=8.6 Hz, 1H), 7.06 (d, J=12.1 Hz, 1H), 6.93 (s, 1H), 3.98 (d, J=6.8 Hz, 2H), 3.07 (d, J=11.1 Hz, 2H), 2.67-2.53 (m, 4H), 2.40 (s, 3H), 1.38-1.30 (m, 1H), 1.18 (d, J=6.0 Hz, 6H), 0.70-0.64 (m, 2H), 0.46-0.41 (m, 2H); LCMS [M+H]$^+$ 607.3.

Example 109: 2-chloro-N-[4-fluoro-5-(2-morpholin-4-ylpyrimidin-5-yl)-2-[(3R,5S)-3,4,5-trimethylpiperazin-1-yl]phenyl]benzamide

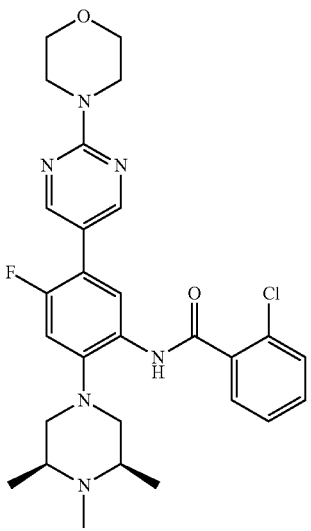

The title compound (beige solid, 38.2 mg, 70%) was prepared through a procedure similar to that of Example 34 using 4-fluoro-5-(2-morpholinopyrimidin-5-yl)-2-((3S,5R)-3,4,5-trimethylpiperazin-1-yl)aniline (40 mg, 0.1 mmol) and 2-chlorobenzoyl chloride (19 μL, 0.15 mmol). $^1$H NMR (500 MHz, CHLOROFORM-d) δ=9.15 (s, 1H), 8.71 (d, J=8.3 Hz, 1H), 8.61 (s, 2H), 7.81 (dd, J=1.8, 7.5 Hz, 1H), 7.54-7.41 (m, 3H), 7.04 (d, J=11.4 Hz, 1H), 3.93-3.86 (m, 4H), 3.84-3.78 (m, 4H), 2.94-2.88 (m, 2H), 2.66 (t, J=10.9 Hz, 2H), 2.43-2.30 (m, 5H), 1.14 (d, J=6.2 Hz, 6H); LCMS [M+H]$^+$ 539.4.

Example 110: 2-fluoro-N-[4-fluoro-5-(2-morpholin-4-ylpyrimidin-5-yl)-2-[(3R,5S)-3,4,5-trimethylpiperazin-1-yl]phenyl]-3-methoxybenzamide

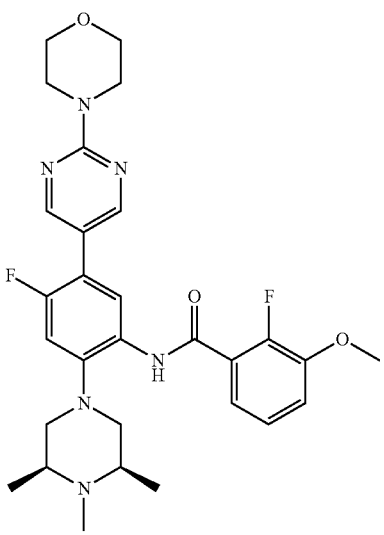

The title compound (light beige solid, 46.7 mg, 84%) was prepared through a procedure similar to that of Example 34 using 4-fluoro-5-(2-morpholinopyrimidin-5-yl)-2-((3S,5R)-3,4,5-trimethylpiperazin-1-yl)aniline (40 mg, 0.1 mmol) and 2-fluoro-3-methoxybenzoyl chloride (28 mg, 0.15 mmol). $^1$H NMR (500 MHz, CHLOROFORM-d) δ=9.73 (d, J=12.7 Hz, 1H), 8.74 (d, J=8.3 Hz, 1H), 8.60 (s, 2H), 7.73 (t, J=7.2 Hz, 1H), 7.26 (t, J=8.4 Hz, 1H), 7.18 (t, J=8.0 Hz, 1H), 7.04 (d, J=11.4 Hz, 1H), 3.98 (s, 3H), 3.92-3.86 (m, 4H), 3.85-3.78 (m, 4H), 2.92 (d, J=10.9 Hz, 2H), 2.67 (t, J=10.8 Hz, 2H), 2.54 (br. s., 2H), 2.40 (s, 3H), 1.17 (d, J=6.1 Hz, 6H); LCMS [M+H]$^+$ 553.5.

Example 111: 3,4-difluoro-N-[4-fluoro-5-(2-morpholin-4-ylpyrimidin-5-yl)-2-[(3R,5S)-3,4,5-trimethylpiperazin-1-yl]phenyl]benzamide

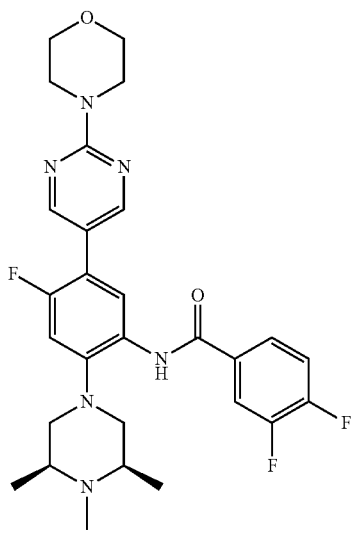

The title compound (beige solid, 37.5 mg, 67%) was prepared through a procedure similar to that of Example 34 using 4-fluoro-5-(2-morpholinopyrimidin-5-yl)-2-((3S,5R)-3,4,5-trimethylpiperazin-1-yl)aniline (40 mg, 0.1 mmol) and 3,4-difluorobenzoyl chloride (19 μL, 0.15 mmol). $^1$H NMR (500 MHz, CHLOROFORM-d) δ=9.73 (d, J=12.7 Hz, 1H), 8.74 (d, J=8.3 Hz, 1H), 8.60 (s, 2H), 7.73 (t, J=7.2 Hz, 1H), 7.26 (t, J=8.4 Hz, 1H), 7.18 (t, J=8.0 Hz, 1H), 7.04 (d, J=11.4 Hz, 1H), 3.98 (s, 3H), 3.92-3.86 (m, 4H), 3.85-3.78 (m, 4H), 2.92 (d, J=10.9 Hz, 2H), 2.67 (t, J=10.8 Hz, 2H), 2.54 k(br. s., 2H), 2.40 (s, 3H), 1.17 (d, J=6.1 Hz, 6H); LCMS [M+H]$^+$ 541.3.

Example 112: N-[4-fluoro-5-(4-methoxyphenyl)-2-[(3R,5S)-3,4,5-trimethylpiperazin-1-yl]phenyl]-6-oxo-4-(trifluoromethyl)-1H-pyridine-3-carboxamide

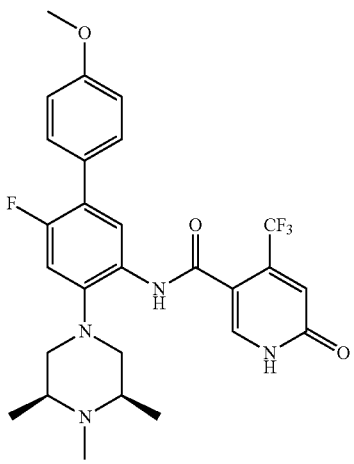

The title compound (grey solid, 42.7 mg, 79%) was prepared according to a procedure similar to that of Example 100 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 4-methoxyphenylboronic acid (30 mg, 0.2 mmol). $^1$H NMR (500 MHz, METHANOL-d4) δ=7.96 (s, 1H), 7.91 (d, J=8.3 Hz, 1H), 7.49 (d, J=7.5 Hz, 2H), 7.04 (d, J=12.2 Hz, 1H), 7.01 (d, J=8.8 Hz, 2H), 6.93 (s, 1H), 3.85 (s, 3H), 3.07 (d, J=11.0 Hz, 2H), 2.68-2.54 (m, 4H), 2.40 (s, 3H), 1.19 (d, J=6.1 Hz, 6H); LCMS [M+H]$^+$ 533.4.

Example 113: N-[5-[4-(cyclopropylmethoxy)phenyl]-4-fluoro-2-[(3R,5S)-3,4,5-trimethylpiperazin-1-yl]phenyl]-6-oxo-4-(trifluoromethyl)-JH-pyridine-3-carboxamide

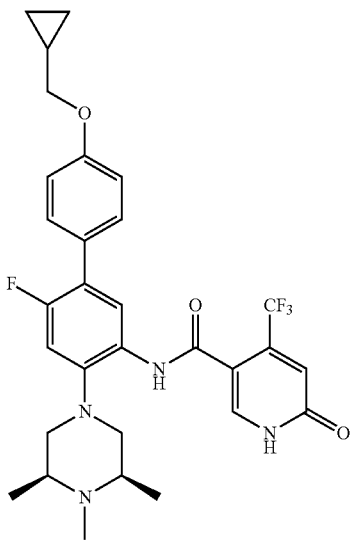

The title compound (grey solid, 47.5 mg, 81%) was prepared according to a procedure similar to that of Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 4-(cyclopropylmethoxy)phenylboronic acid (38 mg, 0.2 mmol). $^1$H NMR (500 MHz, METHANOL-d4) δ=7.96 (s, 1H), 7.91 (d, J=8.2 Hz, 1H), 7.47 (d, J=7.6 Hz, 2H), 7.04 (d, J=12.1 Hz, 1H), 7.00 (d, J=8.8 Hz, 2H), 6.93 (s, 1H), 3.88 (d, J=6.8 Hz, 2H), 3.07 (d, J=10.6 Hz, 2H), 2.68-2.55 (m, 4H), 2.40 (s, 3H), 1.33-1.25 (m, 1H), 1.18 (d, J=6.0 Hz, 6H), 0.68-0.61 (m, 2H), 0.42-0.35 (m, 2H); LCMS [M+H]$^+$ 573.3.

Example 114: N-[4-fluoro-5-(4-pyrrolidin-1-ylphenyl)-2-[(3R,5S)-3,4,5-trimethylpiperazin-1-yl]phenyl]-6-oxo-4-(trifluoromethyl)-1H-pyridine-3-carboxamide

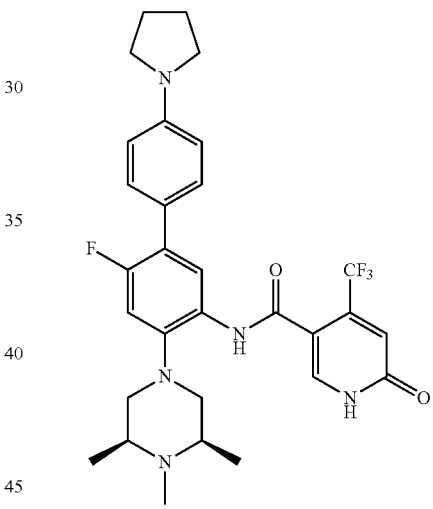

The title compound (brown solid, 43.2 mg, 74%) was prepared according to a procedure similar to that of Example 100 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 1-[4-(4,4,5,5-tetramethyl-1,3,2-dioxaborolan-2-yl)phenyl]pyrrolidine (55 mg, 0.2 mmol). $^1$H NMR (500 MHz, METHANOL-d4) δ=7.95 (s, 1H), 7.90 (d, J=8.3 Hz, 1H), 7.41 (d, J=7.7 Hz, 2H), 7.00 (d, J=12.2 Hz, 1H), 6.92 (s, 1H), 6.65 (d, J=8.7 Hz, 2H), 3.04 (d, J=11.0 Hz, 2H), 2.66-2.52 (m, 4H), 2.40 (s, 3H), 2.09-2.01 (m, 4H), 1.18 (d, J=6.0 Hz, 6H); LCMS [M+H]$^+$ 572.4.

Example 115: 3-acetamido-N-[4-fluoro-5-(2-morpholin-4-ylpyrimidin-5-yl)-2-[(3R,5S)-3,4,5-trimethylpiperazin-1-yl]phenyl]benzamide

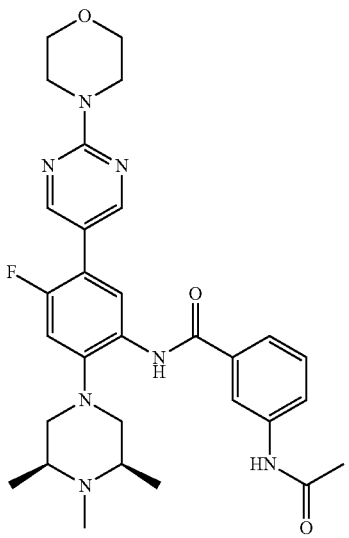 [SMILES: CC(=O)Nc1cccc(C(=O)Nc2cc(-c3cnc(N4CCOCC4)nc3)c(F)cc2N2C[C@@H](C)N(C)[C@@H](C)C2)c1]

The title compound (off-white solid, 41.9 mg, 70%) was prepared according to a procedure similar to that of Example 34 using 3-acetylaminobenzoic acid (36 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.20 (s, 1H), 8.57 (d, J=8.2 Hz, 1H), 8.50 (s, 2H), 8.05 (br. s., 1H), 7.71 (d, J=8.2 Hz, 1H), 7.56 (d, J=7.7 Hz, 1H), 7.42 (t, J=7.9 Hz, 1H), 7.23 (br. s., 1H), 6.94 (d, J=11.1 Hz, 1H), 3.83-3.77 (m, 4H), 3.75-3.69 (m, 4H), 2.83 (d, J=11.0 Hz, 2H), 2.59 (t, J=10.8 Hz, 2H), 2.46 (br. s., 2H), 2.30 (s, 3H), 2.16 (s, 3H), 1.07 (d, J=6.1 Hz, 6H); LCMS [M+H]$^+$ 562.4.

Example 116: N-[4-fluoro-5-(2-morpholin-4-ylpyrimidin-5-yl)-2-[(3R)-3,4-dimethylpiperazin-1-yl]phenyl]-1-methylindazole-3-carboxamide

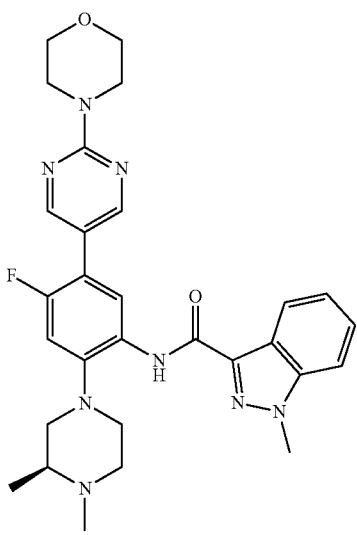 [SMILES: C[C@H]1CN(c2cc(F)c(-c3cnc(N4CCOCC4)nc3)cc2NC(=O)c2nn(C)c3ccccc23)CCN1C]

The title compound was prepared similar to the sequence described above for the preparation of Example 78 using 1-methyl-1H-indazole-3-carbonylchloride in place of benzoyl chloride in Step 4. $^1$H NMR (500 MHz, DMSO-d6) δ=9.94 (s, 1H), 8.59 (s, 2H), 8.54 (d, J=8.6 Hz, 1H), 8.24 (d, J=8.2 Hz, 1H), 7.82 (d, J=8.6 Hz, 1H), 7.54 (t, J=7.6 Hz, 1H), 7.37 (t, J=7.5 Hz, 1H), 7.29 (d, J=11.7 Hz, 1H), 4.22 (s, 3H), 3.80-3.77 (m, 4H), 3.72-3.69 (m, 4H), 3.02-2.89 (m, 4H), 2.66-2.57 (m, 2H), 2.32 (s, 3H), 1.06 (d, J=6.2 Hz, 3H); LCMS [M+H]+: 545.3.

Example 117: N-[4-fluoro-5-(4-morpholin-4-ylphenyl)-2-[(3R)-3,4-dimethylpiperazin-1-yl]phenyl]-1-methylindazole-3-carboxamide

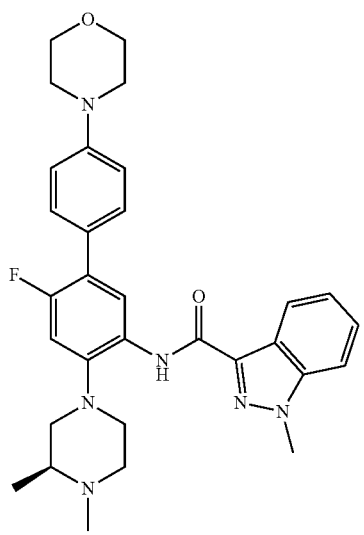 [SMILES: C[C@H]1CN(c2cc(F)c(-c3ccc(N4CCOCC4)cc3)cc2NC(=O)c2nn(C)c3ccccc23)CCN1C]

The title compound was prepared similar to the sequence described above for the preparation of Example 116 using 4-(morpholino)phenylboronic acid in place of 2-(4-morpholino)pyrimidine-5-boronic acid pinacol ester in Step 2. $^1$H NMR (500 MHz, DMSO-d6) δ=9.94 (s, 1H), 8.56 (d, J=8.6 Hz, 1H), 8.25 (d, J=8.2 Hz, 1H), 7.82 (d, J=8.7 Hz, 1H), 7.54 (t, J=7.7 Hz, 1H), 7.45 (br d, J=7.7 Hz, 2H), 7.37 (t, J=7.5 Hz, 1H), 7.22 (d, J=12.1 Hz, 1H), 7.08 (d, J=8.8 Hz, 2H), 4.21 (s, 3H), 3.80-3.75 (m, 4H), 3.21-3.17 (m, 4H), 3.00-2.89 (m, 5H), 2.67-2.58 (m, 4H), 2.32 (s, 3H), 1.07 (d, J=6.1 Hz, 3H); LCMS [M+H]+: 543.4.

Example 118: N-[4-fluoro-5-[3-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide

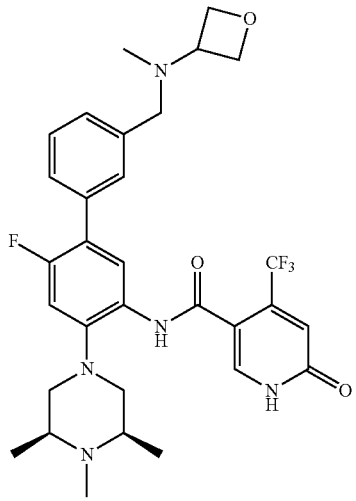 [SMILES: C[C@@H]1CN(c2cc(F)c(-c3cccc(CN(C)C4COC4)c3)cc2NC(=O)c2c[nH]c(=O)cc2C(F)(F)F)C[C@H](C)N1C]

Step 1: N-(6-fluoro-3'-formyl-4-((3S,5R)-3,4,5-trimethylpiperazin-1-yl)-[1,1'-biphenyl]-3-yl)-4-(trifluoromethyl)-6-(2-(trimethylsilyl)ethoxy)nicotinamide

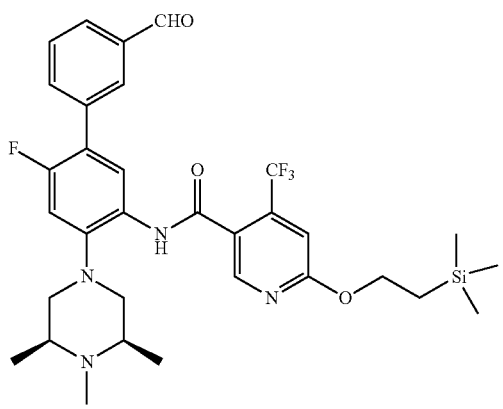 [SMILES: C[C@@H]1CN(c2cc(F)c(-c3cccc(C=O)c3)cc2NC(=O)c2cnc(OCC[Si](C)(C)C)cc2C(F)(F)F)C[C@H](C)N1C]

A procedure similar to that of Example 100 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (130 mg, 0.215 mmol) and 3-formylphenylboronic acid (45.1 mg, 0.301 mmol) afforded the title compound (84 mg, 62% yield). LCMS [M+H]+: 631.8.

Step 2: N-(6-fluoro-3'-((methyl(oxetan-3-yl)amino)methyl)-4-((3S,5R)-3,4,5-trimethylpiperazin-1-yl)-[1,1'-biphenyl]-3-yl)-4-(trifluoromethyl)-6-(2-(trimethylsilyl)ethoxy)nicotinamide

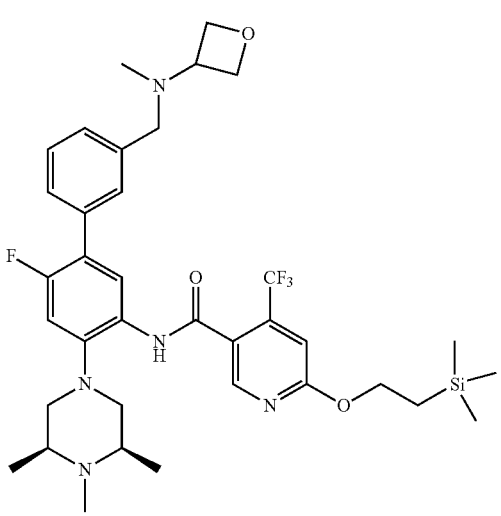 [SMILES: C[C@@H]1CN(c2cc(F)c(-c3cccc(CN(C)C4COC4)c3)cc2NC(=O)c2cnc(OCC[Si](C)(C)C)cc2C(F)(F)F)C[C@H](C)N1C]

N-(6-fluoro-3'-formyl-4-((3S,5R)-3,4,5-trimethylpiperazin-1-yl)-[1,1'-biphenyl]-3-yl)-4-(trifluoromethyl)-6-(2-(trimethylsilyl)ethoxy)nicotinamide (40 mg, 0.063 mmol), N-methyl-3-oxetanamine (11.05 mg, 0.127 mmol) and acetic acid, glacial, 99.8% (15.23 mg, 0.254 mmol) were mixed in anhydrous DCE. A cloudy solution was obtained. After 5-10 min, sodium triacetoxyborohydride (40.3 mg, 0.190 mmol) was added and the reaction mixture was stirred at RT. There was no difference observed between 7.5 h and overnight at RT. A small amount of the starting material (approx. 5%) of the starting material was observed along with the desired product. The reaction mixture was quenched with sat aq NaHCO₃ solution (basic). The organic phase was separated, the aqueous phase was extracted with DCM (×2), then the combined organic phase was washed with brine, dried over Na₂SO₄ and concentrated to obtain the crude product. It was purified on reverse phase isco column (5.5G), eluting with water containing 0-60% acetonitrile. The appropriate fractions were combined and concentrated to afford the desired product as a white foam (31 mg, 70% yield). LCMS [M+H]+=700.6.

Step 3: N-(6-fluoro-3'-((methyl(oxetan-3-yl)amino) methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide, trifluoroacetic acid salt Example 119: N-[4-fluoro-5-[3-[(4-fluoropiperidin-1-yl)methyl]phenyl]-2-[(3R,5S)-3,4,5-trimethylpiperazin-1-yl]phenyl]-6-oxo-4-(trifluoromethyl)-1H-pyridine-3-carboxamide

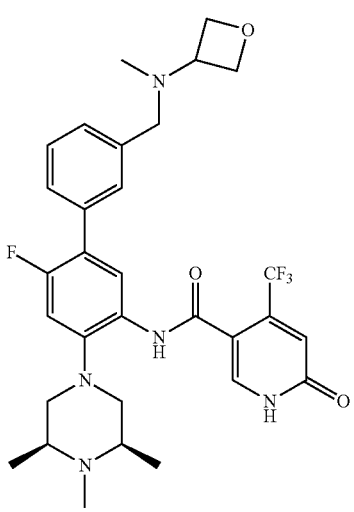 [SMILES: C[C@@H]1CN(c2cc(F)c(-c3cccc(CN(C)C4COC4)c3)cc2NC(=O)c2c[nH]c(=O)cc2C(F)(F)F)C[C@H](C)N1C]

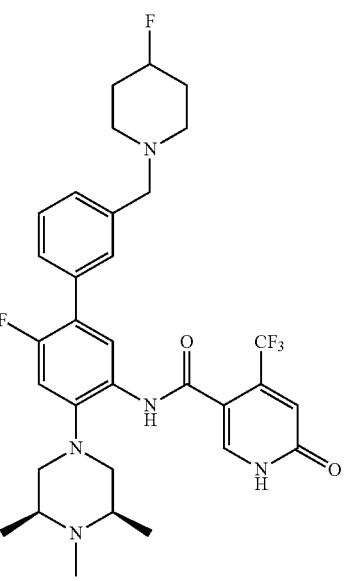

The product of the foregoing procedure was dissolved in DCM (2 mL) and TFA (0.5 ml) was added. The reaction mixture was stirred at RT. LCMS showed completion of the reaction after 8 min. The reaction mixture was concentrated to dryness, and the residue was triturated with ether to collect the title compound as a white powder. (32 mg, 82% yield). $^1$H NMR (500 MHz, METHANOL-d4) δ=7.94 (t, J=3.9 Hz, 2H), 7.65 (s, 1H), 7.65 (d, J=8.1 Hz, 2H), 7.55 (t, J=7.6 Hz, 1H), 7.48 (d, J=7.6 Hz, 1H), 7.14 (d, J=11.7 Hz, 1H), 6.87 (s, 1H), 4.74-4.66 (m, 2H), 4.65-4.53 (m, 2H), 4.52-4.46 (m, 1H), 4.31 (s, 2H), 3.52-3.44 (m, 2H), 3.29 (br s, 2H), 2.83-2.83 (m, 1H), 2.99-2.80 (m, 4H), 2.74 (s, 3H), 1.38 (d, J=6.4 Hz, 6H); LCMS [M+H]+ 602.

A sequence similar to that of Example 118 was used with 4-fluoropiperidine as the amine in the reductive amination step to provide 26 mg (70% yield) of the title compound as the TFA salt. $^1$H NMR (500 MHz, METHANOL-d4) δ=7.97-7.91 (m, 2H), 7.69-7.63 (m, 2H), 7.55 (t, J=7.6 Hz, 1H), 7.51-7.46 (m, 1H), 7.13 (d, J=11.7 Hz, 1H), 6.87 (s, 1H), 4.37 (s, 2H), 3.58-3.26 (m, 9H), 3.00-2.81 (m, 5H), 2.38-2.12 (m, 2H), 2.06-1.85 (m, 2H), 1.44-1.32 (m, 6H). LCMS [M+H]+ 618.7.

Example 120: N-[2-(3,4,6,7,9,9a-hexahydro-JH-pyrazino[2,1-c][1,4]oxazin-8-yl)-4-fluoro-5-(2-morpholin-4-ylpyrimidin-5-yl)phenyl]-6-oxo-4-(trifluoromethyl)-1H-pyridine-3-carboxamide

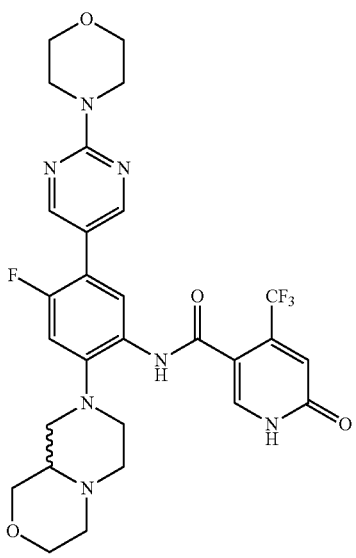 [SMILES: O=C(Nc1cc(-c2cnc(N3CCOCC3)nc2)c(F)cc1N1CCN2CCOCC2C1)c1c[nH]c(=O)cc1C(F)(F)F]

Step 1: 8-(4-bromo-5-fluoro-2-nitrophenyl)octahydropyrazino[2,1-c][1,4]oxazine

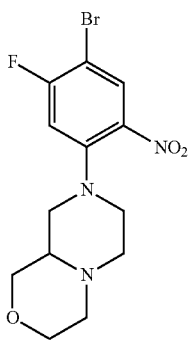 [SMILES: O=[N+]([O-])c1cc(Br)c(F)cc1N1CCN2CCOCC2C1]

A suspension of octahydropyrazino[2,1-c][1,4]oxazine (612 mg, 4.30 mmol) and Potassium carbonate (ACS) (297 mg, 2.152 mmol) in toluene (10 ml) was stirred for 5 minutes at room temperature. Then a solution of 1-bromo-2,4-difluoro-5-nitrobenzene (1024 mg, 4.30 mmol) in toluene (1 ml) was added dropwise from a pipette (2 ml of toluene were used to rinse the vial) and the reaction was stirred at 50° C. for 3 h 30 min. Then the reaction mixture was partitioned into water and DCM and the product was extracted by DCM (3×20 mL). The organic phase was dried over MgSO$_4$ and after filtration and solvents removal, the crude material was dry loaded and purified by Flash chromatography [0-10% MeOH/DCM] to afford the desired 8-(4-bromo-5-fluoro-2-nitrophenyl)octahydropyrazino[2,1-c][1,4]oxazine (1.3361 g, 3.67 mmol, 85% yield) as an orange powder. LCMS [M+H]$^+$: 360.2.

Step 2: 8-(5-fluoro-4-(2-morpholinopyrimidin-5-yl)-2-nitrophenyl)octahydropyrazino[2,1-c][1,4]oxazine

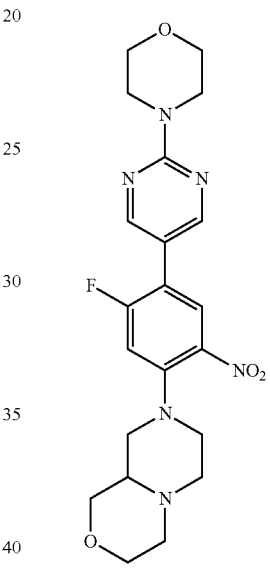

A 30 mL vial was charged with a mixture of 8-(4-bromo-5-fluoro-2-nitrophenyl)octahydropyrazino[2,1-c][1,4]oxazine (112 mg, 0.311 mmol), 2-(4-morpholino)pyrimidine-5-boronic acid pinacol ester (127 mg, 0.435 mmol), XPhos Pd G2 (4.89 mg, 6.22 µmol) and XPhos (2.96 mg, 6.22 µmol). Then sodium carbonate solution (2 molar) (0.777 ml, 1.555 mmol) was added via syringe and the vial was flushed with argon. The reaction was stirred at 90° C. for 2 hours then the reaction mixture was partitioned into water and DCM and the product was extracted by DCM (3×20 mL). The organic phase was dried over MgSO$_4$ and after filtration and solvents removal, the crude material was dry loaded and purified by flash chromatography [0-10% MeOH/DCM] to afford the desired 8-(5-fluoro-4-(2-morpholinopyrimidin-5-yl)-2-nitrophenyl)octahydropyrazino[2,1-c][1,4]oxazine (143.6 mg, 0.291 mmol, 94% yield) as a brown oil. LCMS [M+H]+ 444.9.

Step 3: 4-fluoro-2-(hexahydropyrazino[2,1-c][1,4]oxazin-8(H)-yl)-5-(2-morpholinopyrimidin-5-yl)aniline

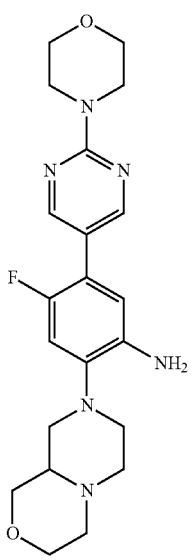 [SMILES: O=[N+]([O-])c1cc(-c2cnc(N3CCOCC3)nc2)c(F)cc1N1CCN2CCOCC2C1]

To a solution of 8-(5-fluoro-4-(2-morpholinopyrimidin-5-yl)-2-nitrophenyl)octahydropyrazino[2,1-c][1,4]oxazine (143.6 mg, 0.323 mmol) in a mixture of MeOH (5 ml) and water (1 ml) was added zinc dust (106 mg, 1.615 mmol) followed by 4 drops of hydrochloric acid (ACS) (11.78 mg, 0.323 mmol). The reaction mixture was stirred at 90° C. for 40 minutes then the crude mixture was filtered through a pad of celite using methanol to elute the product. Then the filtrate was concentrated under vacuum and the crude mixture was dry loaded and purified by Flash chromatography [0-10% MeOH/DCM] to afford the desired 4-fluoro-2-(hexahydropyrazino[2,1-c][1,4]oxazin-8(1H)-yl)-5-(2-morpholinopyrimidin-5-yl)aniline (53.2 mg, 0.128 mmol, 39.7% yield) as a yellow oil. LCMS [M+H]+ 415.1.

Step 4: N-(4-fluoro-2-(hexahydropyrazino[2,1-c][1,4]oxazin-8(H)-yl)-5-(2-morpholinopyrimidin-5-yl)phenyl)-4-(trifluoromethyl)-6-(2-(trimethylsilyl)ethoxy)nicotinamide

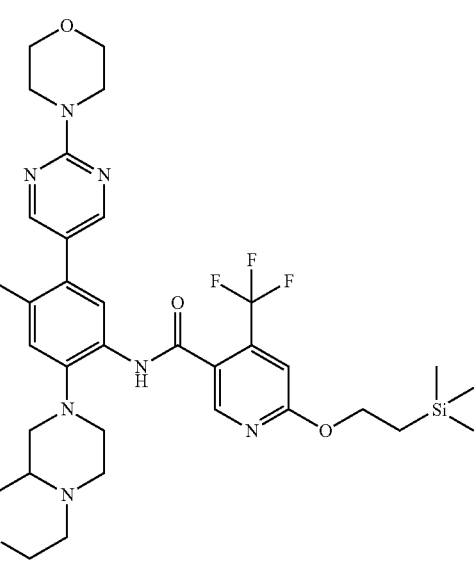

To a solution of 4-(trifluoromethyl)-6-(2-(trimethylsilyl)ethoxy)nicotinic acid (51.3 mg, 0.167 mmol) in N,N-dimethylformamide (DMF) (5 mL) were added HATU (98 mg, 0.257 mmol) and N,N-diisopropylethylamine (0.133 ml, 0.770 mmol). The reaction mixture was stirred for 5 minutes before adding a solution of 4-fluoro-2-(hexahydropyrazino[2,1-c][1,4]oxazin-8(1H)-yl)-5-(2-morpholinopyrimidin-5-yl)aniline (53.2 mg, 0.128 mmol) in 1 mL of DMF (use of 2×1 mL of DMF to rinse). Then the reaction mixture was stirred at room temperature overnight. The crude material was dry loaded and purified by flash chromatography [4-100% water/ACN] to afford the desired N-(4-fluoro-2-(hexahydropyrazino[2,1-c][1,4]oxazin-8(1H)-yl)-5-(2-morpholinopyrimidin-5-yl)phenyl)-4-(trifluoromethyl)-6-(2-(trimethylsilyl)ethoxy)nicotinamide (12.7 mg, 0.018 mmol, 13.92% yield) as a tan solid. LCMS [M+H]+ 704.3.

Step 5: N-(4-fluoro-2-(hexahydropyrazino[2,1-c][1,4]oxazin-8(1H)-yl)-5-(2-morpholinopyrimidin-5-yl)phenyl)-6-oxo-4-(trifluoromethyl)-1,6-dihydropyridine-3-carboxamide (TFA salt)

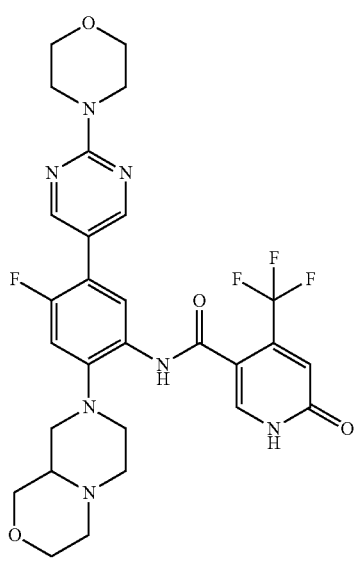 [SMILES: O=C(Nc1cc(-c2cnc(N3CCOCC3)nc2)c(F)cc1N1CCN2CCOCC2C1)c1c[nH]c(=O)cc1C(F)(F)F]

To a solution of N-(4-fluoro-2-(hexahydropyrazino[2,1-c][1,4]oxazin-8(1H)-yl)-5-(2-morpholinopyrimidin-5-yl)phenyl)-4-(trifluoromethyl)-6-(2-(trimethylsilyl)ethoxy)nicotinamide (12.7 mg, 0.018 mmol) in DCM (3 ml) was added trifluoroacetic acid (2 ml, 26.1 mmol). The reaction mixture was stirred at 60° C. for 3 hours then the TFA and solvent were removed under vacuum to give the desired N-(4-fluoro-2-(hexahydropyrazino[2,1-c][1,4]oxazin-8(1H)-yl)-5-(2-morpholinopyrimidin-5-yl)phenyl)-6-oxo-4-(trifluoromethyl)-1,6-dihydropyridine-3-carboxamide TFA salt (15.3 mg, 0.014 mmol, 76% yield) as a light brown powder. $^1$H NMR (500 MHz, DMSO-d6) δ=9.62 (s, 1H), 8.54 (s, 2H), 8.02 (s, 1H), 7.92 (d, J=8.31 Hz, 1H), 7.24 (d, J=11.74 Hz, 1H), 6.85 (s, 1H), 4.05 (br d, J=10.88 Hz, 1H), 3.96 (br d, J=11.13 Hz, 1H), 3.80-3.74 (m, 6H), 3.71-3.65 (m, 6H), 3.59-3.44 (m, 3H), 3.36 (br d, J=11.49 Hz, 1H), 3.29 (br d, J=11.98 Hz, 2H), 3.23-3.06 (m, 2H), 2.85 (br t, J=11.68 Hz, 1H); LCMS [M+H]+ 604.31.

Example 121: N-[4-fluoro-5-(2-morpholin-4-ylpyrimidin-5-yl)-2-[(3R)-3,4-dimethylpiperazin-1-yl]phenyl]-1-methylpyrazole-4-carboxamide

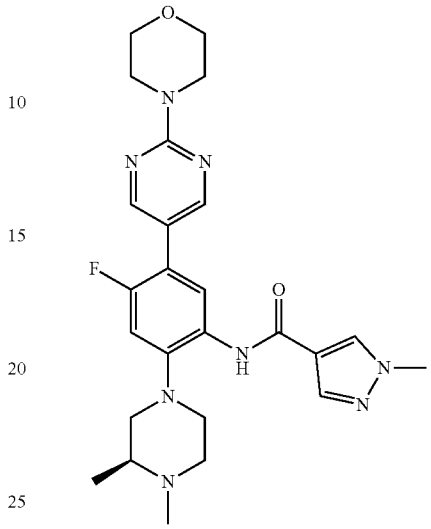

The title compound was prepared similar to the procedure described above for the preparation of Example 78 using 1-methyl-1H-pyrazole-4-carboxylic acid in place of 3-(trifluoromethyl)pyrazole-4-carboxylic acid for Step 4. $^1$H NMR (500 MHz, DMSO-d6) δ=9.07 (s, 1H), 8.55 (d, J=1.0 Hz, 2H), 8.30 (s, 1H), 7.98 (s, 1H), 7.86 (d, J=8.6 Hz, 1H), 7.11 (d, J=12.2 Hz, 1H), 3.91 (s, 3H), 3.77-3.75 (m, 4H), 3.70-3.67 (m, 4H), 3.06-2.94 (m, 2H), 2.85-2.75 (m, 2H), 2.36 (dd, J=2.3, 10.6 Hz, 1H), 2.30-2.20 (m, 4H), 0.97 (d, J=6.2 Hz, 3H); LCMS [M+H]+: 495.3.

Example 122: N-[4-fluoro-5-(4-morpholin-4-ylphenyl)-2-[(3R)-3,4-dimethylpiperazin-1-yl]phenyl]-1-methylpyrazole-4-carboxamide

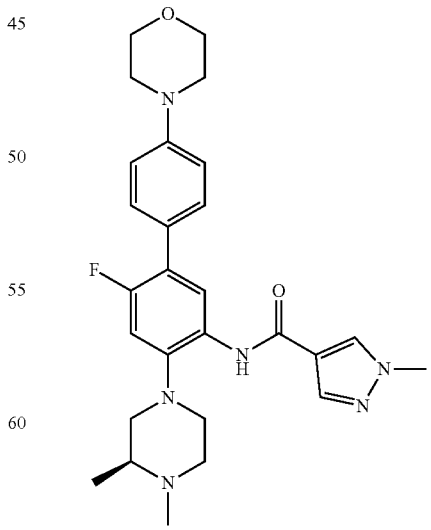

The title compound was prepared similar to the sequence described above for the preparation of Example 78 using 4-(morpholino)phenylboronic acid in place of 2-(4-morpholino)pyrimidine-5-boronic acid pinacol ester in Step 2. ¹H NMR (500 MHz, DMSO-d6) δ=9.01 (s, 1H), 8.29 (s, 1H), 7.97 (s, 1H), 7.88 (d, J=8.7 Hz, 1H), 7.43-7.37 (m, 2H), 7.09-7.00 (m, 3H), 3.91 (s, 3H), 3.79-3.74 (m, 4H), 3.19-3.15 (m, 4H), 3.03-2.92 (m, 2H), 2.85-2.76 (m, 2H), 2.40-2.35 (m, 1H), 2.31-2.21 (m, 4H), 0.98 (d, J=6.2 Hz, 3H); LCMS [M+H]+: 493.4.

Example 123: N-[5-(5-cyano-6-hydroxypyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

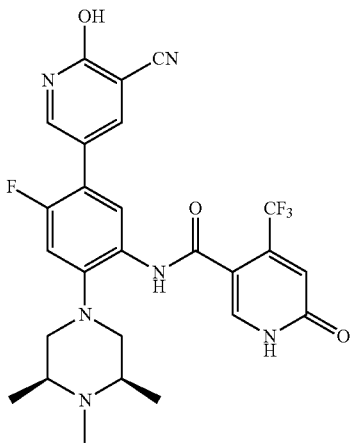

Step 1: N-(5-(6-(benzyloxy)-5-cyanopyridin-3-yl)-4-fluoro-2-((3S,5R)-3,4,5-trimethylpiperazin-1-yl)phenyl)-4-(trifluoromethyl)-6-(2-(trimethylsilyl)ethoxy)nicotinamide

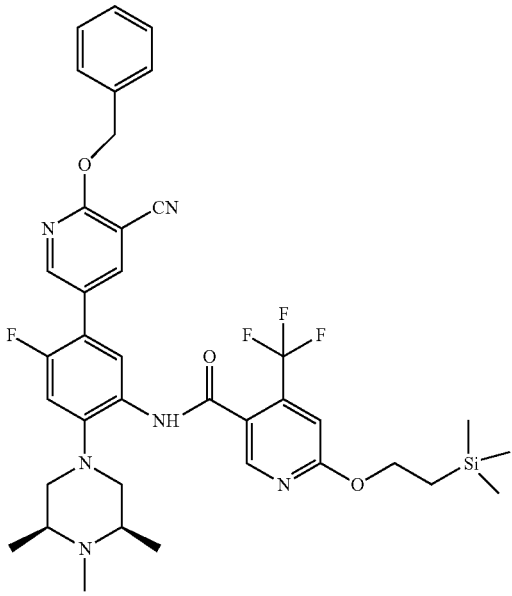 [SMILES: C[C@@H]1CN(c2cc(F)c(-c3cnc(OCc4ccccc4)c(C#N)c3)cc2NC(=O)c2cnc(OCC[Si](C)(C)C)cc2C(F)(F)F)C[C@H](C)N1C]

To a solution of N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (300 mg, 0.495 mmol) and 2-(benzyloxy)-5-(trimethylstannyl)nicotinonitrile (222 mg, 0.595 mmol) in dry DMF (2 ml) at RT under N₂, was added CsF (151 mg, 0.991 mmol), copper(I) iodide (9.44 mg, 0.050 mmol) and tetrakis(triphenylphosphine)palladium(0) polymer bound (573 mg, 0.495 mmol). The reaction mixture was stirred overnight at 60° C. The major product was the deprotected one. The mixture was concentrated to dryness, partitioned between EtOAc and satd. aq citric acid solution. The organic phase was separated, and the aqueous phase was extracted with EtOAc (3×). The combined organic phase was washed with sodium bicarbonate solution (8 ml), dried over Na₂SO₄ and concentrated to obtain the crude product which was adsorbed on celite and purified on isco (12 g), eluting with DCM containing 0-10% MeOH. The deprotected product was isolated as a beige solid (66 mg, 20%). LCMS [M+H]+ 635.7

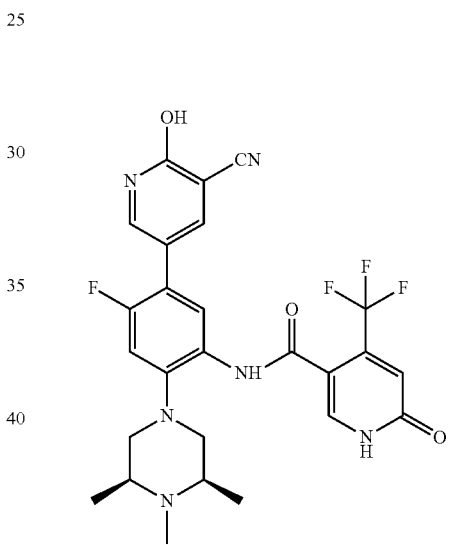

N-(5-(6-(benzyloxy)-5-cyanopyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (20 mg) was dissolved in MeOH and subjected to hydrogenolysis at 45° C. in an H-cube. The reaction was complete in 1 h. The solution was concentrated and purified on a preparatory column, eluting with water/acetonitrile gradient. The desired product was isolated as a white solid. (5 mg, 26%). ¹H NMR (500 MHz, METHANOL-d4)) δ ppm 1.24-1.30 (m, 6H) 2.68-2.87 (m, 5H) 3.13-3.19 (m, 2H) 3.22-3.32 (m, 2H) 6.83 (br s, 1H) 7.07 (br d, J=11.86 Hz, 1H) 7.79 (d, J=8.31 Hz, 1H) 7.87 (br s, 1H) 7.91 (s, 1H) 8.24 (br s, 1H). LCMS [M+H]+ 545.7

Example 124: N-[4-fluoro-5-(3-fluoro-4-morpholin-4-ylphenyl)-2-[(3R,5S)-3,4,5-trimethylpiperazin-1-yl]phenyl]-6-oxo-4-(trifluoromethyl)-1H-pyridine-3-carboxamide

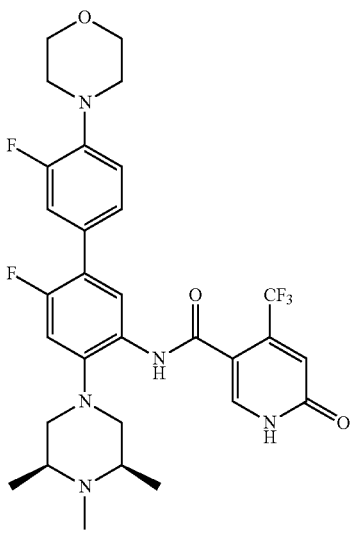

The title compound (brown solid, 37.4 mg, 61%) was prepared by a procedure similar to Example 100 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 3-fluoro-4-morpholinophenylboronic acid (45 mg, 0.2 mmol). $^1$H NMR (500 MHz, METHANOL-d4) δ=7.97 (s, 1H), 7.92 (d, J=8.3 Hz, 1H), 7.33 (d, J=8.7 Hz, 1H), 7.30 (d, J=14.2 Hz, 1H), 7.12 (t, J=8.7 Hz, 1H), 7.05 (d, J=12.4 Hz, 1H), 6.93 (s, 1H), 3.92-3.83 (m, 4H), 3.18-3.11 (m, 4H), 3.08 (br d, J=10.9 Hz, 2H), 2.69-2.54 (m, 4H), 2.40 (s, 3H), 1.19 (d, J=6.0 Hz, 6H); LCMS [M+H]$^+$ 606.3.

Example 125: N-[5-[3-(cyclopropylmethoxy)phenyl]-4-fluoro-2-[(3R,5S)-3,4,5-trimethylpiperazin-1-yl]phenyl]-6-oxo-4-(trifluoromethyl)-1H-pyridine-3-carboxamide

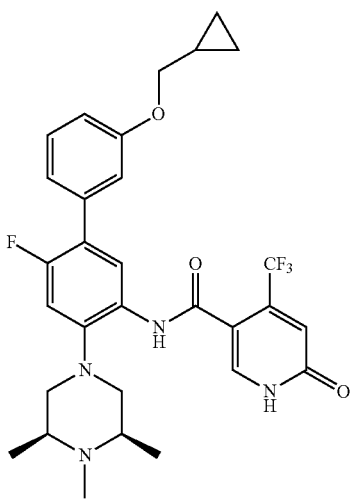

The title compound (light brown solid, 47.3 mg, 82%) was prepared according to a procedure similar to Example 100 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 3-(cyclopropylmethoxy)phenylboronic acid (38 mg, 0.2 mmol). $^1$H NMR (500 MHz, METHANOL-d4) δ=7.97 (s, 1H), 7.92 (d, J=8.2 Hz, 1H), 7.34 (t, J=8.0 Hz, 1H), 7.11 (d, J=7.7 Hz, 1H), 7.09 (s, 1H), 7.05 (d, J=12.0 Hz, 1H), 6.92 (s, 1H), 6.93 (d, J=6.6 Hz, 2H), 3.88 (d, J=6.8 Hz, 2H), 3.08 (br d, J=11.1 Hz, 2H), 2.68-2.54 (m, 4H), 2.40 (s, 3H), 1.33-1.24 (m, 1H), 1.19 (d, J=6.0 Hz, 6H), 0.67-0.61 (m, 2H), 0.42-0.35 (m, 2H); LCMS [M+H]$^+$ 573.4.

Example 126: 3-(dimethylamino)-N-[4-fluoro-5-(2-morpholin-4-ylpyrimidin-5-yl)-2-[(3R,5S)-3,4,5-trimethylpiperazin-1-yl]phenyl]benzamide

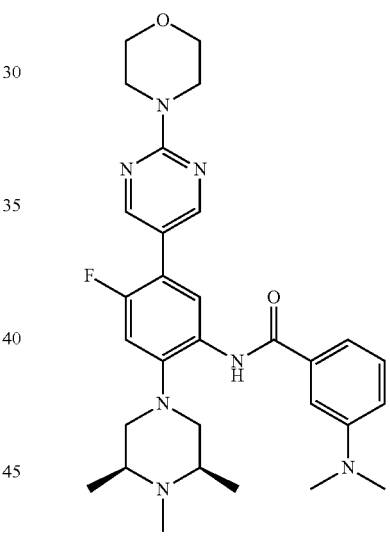

The title compound (light pink solid, 30.8 mg, 55%) was prepared according to a procedure similar to Example 34 using 3-(dimethylamino)benzoic acid (33 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, METHANOL-d4) δ=8.56 (s, 2H), 8.21 (d, J=8.3 Hz, 1H), 7.38 (t, J=8.0 Hz, 1H), 7.29 (s, 1H), 7.22 (d, J=7.6 Hz, 1H), 7.11 (d, J=11.9 Hz, 1H), 7.01 (dd, J=2.4, 8.3 Hz, 1H), 3.88-3.83 (m, 4H), 3.80-3.76 (m, 4H), 3.05 (s, 7H), 2.64 (t, J=11.1 Hz, 2H), 2.56-2.48 (m, 2H), 2.37 (s, 3H), 1.15 (d, J=6.2 Hz, 6H); LCMS [M+H]$^+$ 548.3.

Example 127: N-[4-fluoro-5-(2-morpholin-4-ylpyrimidin-5-yl)-2-[(3R,5S)-3,4,5-trimethylpiperazin-1-yl]phenyl]-1,3-oxazole-4-carboxamide

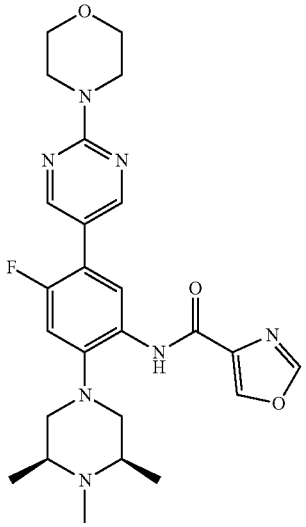

The title compound (light beige solid, 30.7 mg, 61%) was prepared according to a procedure similar to that of Example 34 using oxazole-4-carboxylic acid (23 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.78 (s, 1H), 8.61 (d, J=8.3 Hz, 1H), 8.58 (d, J=1.2 Hz, 2H), 8.35 (s, 1H), 7.97 (s, 1H), 7.28 (s, 1H), 6.98 (d, J=11.4 Hz, 1H), 3.92-3.85 (m, 4H), 3.84-3.79 (m, 4H), 2.96 (d, J=9.7 Hz, 2H), 2.72-2.58 (m, 4H), 2.41 (s, 3H), 1.17 (d, J=5.5 Hz, 6H); LCMS [M+H]$^+$ 496.4.

Example 128: N-[4-fluoro-5-(2-morpholin-4-ylpyrimidin-5-yl)-2-[(3R)-3,4-dimethylpiperazin-1-yl]phenyl]-1-methyl-6-oxo-4-(trifluoromethyl)pyridine-3-carboxamide

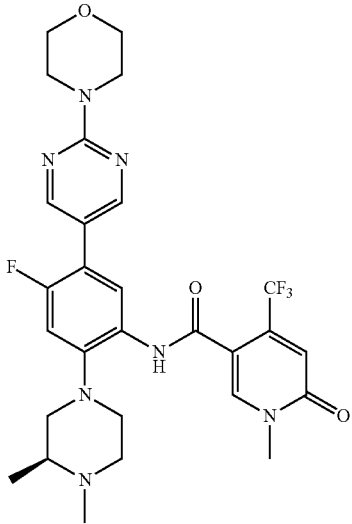 [SMILES: C[C@H]1CN(c2cc(F)c(-c3cnc(N4CCOCC4)nc3)cc2NC(=O)c2cn(C)c(=O)cc2C(F)(F)F)CCN1C]

Step 2: N-[4-fluoro-5-(2-morpholin-4-ylpyrimidin-5-yl)-2-[(3R)-3,4-dimethylpiperazin-1-yl]phenyl]-1-methyl-6-oxo-4-(trifluoromethyl)pyridine-3-carboxamide

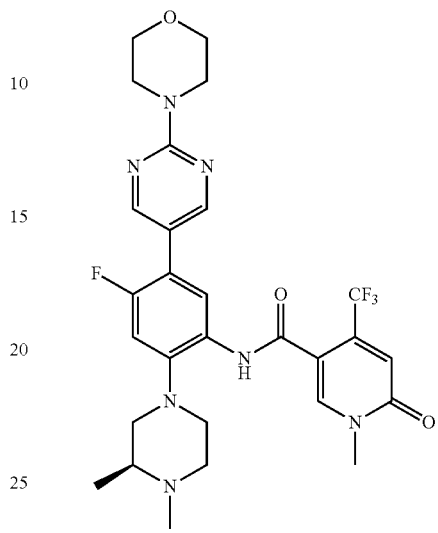

The title compound was prepared according to a procedure similar to Example 78 using 1-methyl-6-oxo-4-(trifluoromethyl)-1,6-dihydropyridine-3-carboxylic acid (obtained as described in Example 93, Step 8) as the acylating agent. $^1$H NMR (500 MHz, DMSO-d6) δ=9.40 (s, 1H), 8.45 (s, 2H), 8.23 (s, 1H), 7.67 (d, J=8.7 Hz, 1H), 7.02 (d, J=12.2 Hz, 1H), 6.80 (s, 1H), 3.71-3.66 (m, 4H), 3.63-3.59 (m, 4H), 3.46 (s, 3H), 3.01-2.91 (m, 2H), 2.78-2.66 (m, 2H), 2.35-2.27 (m, 2H), 2.20-2.09 (m, 4H), 0.90 (d, J=6.2 Hz, 3H); LCMS [M+H]+: 590.3.

Example 129: N-[4-fluoro-5-(4-morpholin-4-ylphenyl)-2-[(3R)-3,4-dimethylpiperazin-1-yl]phenyl]-1-methyl-6-oxo-4-(trifluoromethyl)pyridine-3-carboxamide

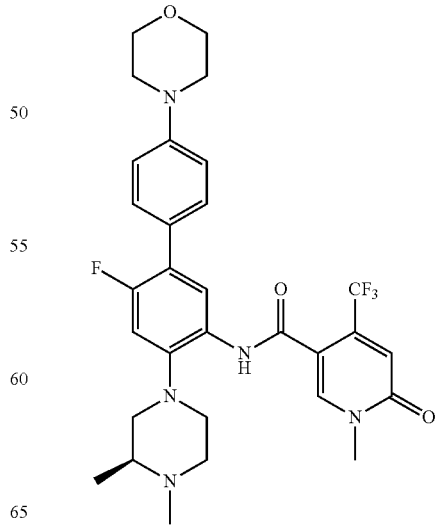

The title compound was prepared similar to the sequence described above for the preparation of Example 128 using (S)-4-(3,4-dimethylpiperazin-1-yl)-6-fluoro-4'-morpholino-[1,1'-biphenyl]-3-amine which was derived from a sequence using 4-(morpholino)phenylboronic acid in place of 2-(4-morpholino)pyrimidine-5-boronic acid pinacol ester in Step 2 of Example 78. $^1$H NMR (500 MHz, DMSO-d6) δ=9.34 (s, 1H), 8.24 (s, 1H), 7.68 (d, J=8.8 Hz, 1H), 7.31 (br s, 1H), 7.30 (br s, 1H), 7.00-6.94 (m, 3H), 6.80 (s, 1H), 3.70-3.67 (m, 4H), 3.45 (s, 3H), 3.11-3.07 (m, 4H), 2.98-2.90 (m, 2H), 2.79-2.66 (m, 2H), 2.36-2.27 (m, 3H), 2.18-2.11 (m, 4H), 0.91 (d, J=6.2 Hz, 3H); LCMS [M+H]+: 588.4.

Example 130: N-[4-fluoro-5-(2-propan-2-yloxypyrimidin-5-yl)-2-[(3R,5S)-3,4,5-trimethylpiperazin-1-yl]phenyl]-6-oxo-4-(trifluoromethyl)-1H-pyridine-3-carboxamide

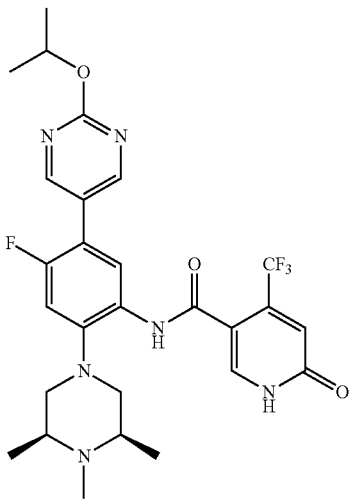 [SMILES: CC(C)Oc1ncc(-c2cc(NC(=O)c3c[nH]c(=O)cc3C(F)(F)F)c(N3C[C@@H](C)N(C)[C@@H](C)C3)cc2F)cn1]

The title compound was prepared similar to the sequence described above for the preparation of Example 100 using (2-isopropoxypyrimidin-5-yl)boronic acid in place of 4-cyanophenylboronic acid. $^1$H NMR (500 MHz, MeOD) δ 8.73 (s, 2H), 7.97 (s, 1H), 7.94 (d, J=8.2 Hz, 1H), 7.11 (d, J=12.0 Hz, 1H), 6.90 (s, 1H), 5.37 (dt, J=12.3, 6.1 Hz, 1H), 3.08 (d, J=11.3 Hz, 2H), 2.62 (t, J=11.1 Hz, 2H), 2.54 (d, J=6.1 Hz, 2H), 2.36 (s, 3H), 1.41 (d, J=6.2 Hz, 6H), 1.16 (d, J=6.2 Hz, 6H); LCMS [M+1]+=563.39.

Example 131: N-[5-(6-cyanopyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

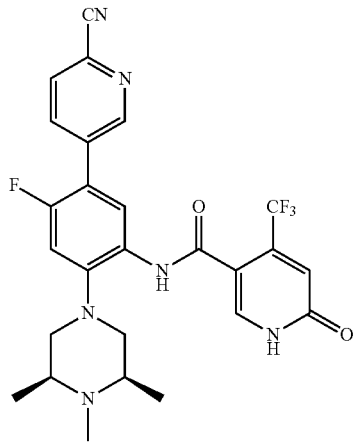

The title compound was prepared similar to the sequence described above for the preparation of Example 100 using 2-cyanopyridine-5-boronic acid pinacol ester. $^1$H NMR (500 MHz, MeOD) δ 8.91 (s, 1H), 8.19 (d, J=9.2 Hz, 1H), 8.00 (d, J=8.2 Hz, 1H), 7.96 (t, J=4.0 Hz, 2H), 7.13 (d, J=12.3 Hz, 1H), 6.91 (s, 1H), 3.12 (d, J=11.4 Hz, 2H), 2.64 (t, J=11.2 Hz, 2H), 2.55 (dd, J=13.2, 7.0 Hz, 2H), 2.37 (s, 3H), 1.16 (d, J=6.2 Hz, 6H); LCMS [M+1]+=529.38.

Example 132: N-[5-(6-cyano-5-methylpyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

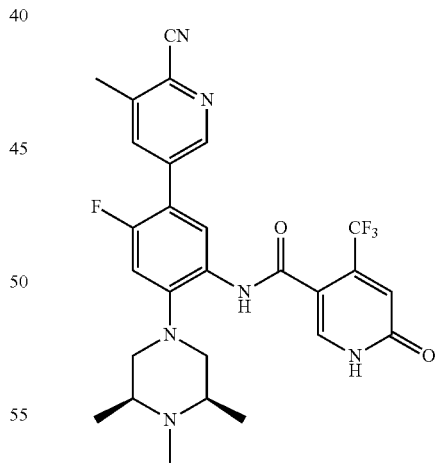

The title compound was prepared similar to the sequence described above for the preparation of Example 100 using 2-cyano-3-methylpyridine-5-boronic acid, pinacol ester. $^1$H NMR (500 MHz, MeOD) δ 8.72 (s, 1H), 8.07 (s, 1H), 7.98 (d, J=8.2 Hz, 1H), 7.97 (s, 1H), 7.12 (d, J=12.3 Hz, 1H), 6.91 (s, 1H), 3.12 (d, J=11.4 Hz, 2H), 2.64 (d, J=10.9 Hz, 2H), 2.62 (s, 3H), 2.54 (dd, J=9.0, 5.2 Hz, 2H), 2.37 (s, 3H), 1.16 (d, J=6.2 Hz, 6H); $^{19}$F NMR (471 MHz, MeOD) δ −63.75 (s), −119.92 (s); LCMS HSS [M+1]+=543.30.

Example 133: N-[5-(2-cyanopyridin-4-yl)-4-fluoro-2-[(3R,5S)-3,4,5-trimethylpiperazin-1-yl]phenyl]-6-oxo-4-(trifluoromethyl)-1H-pyridine-3-carboxamide

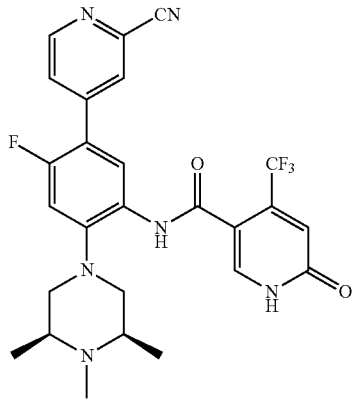 [SMILES: C[C@@H]1CN(c2cc(F)c(-c3ccnc(C#N)c3)cc2NC(=O)c2c[nH]c(=O)cc2C(F)(F)F)C[C@H](C)N1C]

The title compound was prepared similar to the sequence described above for the preparation of Example 100 using 2-cyanopyridine-4-boronic acid pinacol ester in place of 4-cyanophenylboronic acid. $^1$H NMR (500 MHz, MeOD) δ 8.75 (d, J=5.3 Hz, 1H), 8.12 (s, 1H), 8.03 (d, J=8.2 Hz, 1H), 7.98 (s, 1H), 7.88 (d, J=5.2 Hz, 1H), 7.12 (d, J=12.6 Hz, 1H), 6.91 (s, 1H), 3.14 (d, J=11.7 Hz, 2H), 2.63 (t, J=11.2 Hz, 2H), 2.58-2.50 (m, 2H), 2.36 (s, 3H), 1.16 (d, J=6.2 Hz, 6H); LCMS [M+1]+=529.38.

Example 134: N-[4-fluoro-5-[2-methoxy-6-(trifluoromethyl)pyridin-4-yl]-2-[(3R,5S)-3,4,5-trimethylpiperazin-1-yl]phenyl]-6-oxo-4-(trifluoromethyl)-1H-pyridine-3-carboxamide

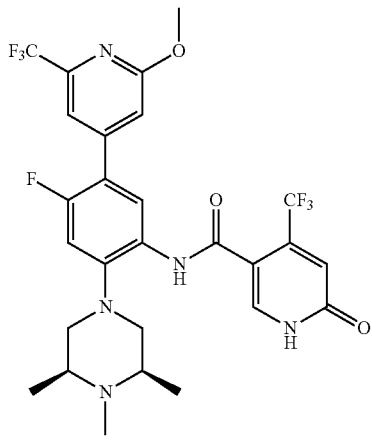 [SMILES: COc1cc(-c2cc(NC(=O)c3c[nH]c(=O)cc3C(F)(F)F)c(N3C[C@@H](C)N(C)[C@@H](C)C3)cc2F)cc(C(F)(F)F)n1]

The title compound was prepared similar to the sequence described above for the preparation of Example 100 using 2-methoxy-6-trifluoromethylpyridine-4-boronic acid. $^1$H NMR (500 MHz, MeOD) δ 7.97 (s, 2H), 7.53 (s, 1H), 7.19 (s, 1H), 7.10 (d, J=12.5 Hz, 1H), 6.91 (s, 1H), 4.01 (s, 3H), 3.12 (d, J=11.5 Hz, 2H), 2.63 (t, J=11.2 Hz, 2H), 2.58-2.52 (m, 2H), 2.37 (s, 3H), 1.16 (d, J=6.1 Hz, 6H); LCMS [M+1]+=602.06.

Example 135: N-[4-fluoro-5-(2-methoxy-6-methylpyridin-4-yl)-2-[(3R,5S)-3,4,5-trimethylpiperazin-1-yl]phenyl]-6-oxo-4-(trifluoromethyl)-1H-pyridine-3-carboxamide

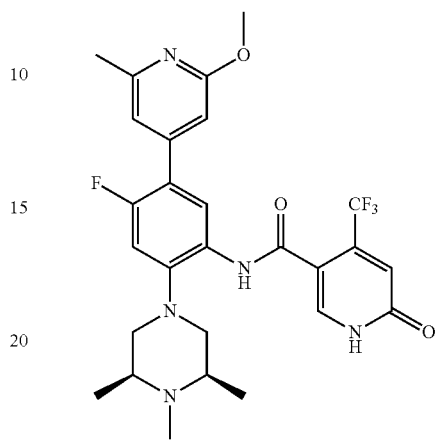

The title compound was prepared similar to the sequence described above for the preparation of Example 100 using 6-methoxy-2-picoline-4-boronic acid, pinacol ester. $^1$H NMR (500 MHz, MeOD) δ 7.95 (s, 2H), 7.07 (d, J=12.2 Hz, 1H), 7.00 (s, 1H), 6.92 (s, 1H), 6.76 (s, 1H), 3.93 (s, 3H), 3.12 (d, J=8.1 Hz, 2H), 2.65 (d, J=7.1 Hz, 4H), 2.48 (s, 3H), 1.19 (d, J=5.5 Hz, 6H); LCMS [M+1]+=548.04.

Example 136: N-[4-fluoro-5-[6-methoxy-5-(trifluoromethyl)pyridin-3-yl]-2-[(3R,5S)-3,4,5-trimethylpiperazin-1-yl]phenyl]-6-oxo-4-(trifluoromethyl)-1H-pyridine-3-carboxamide

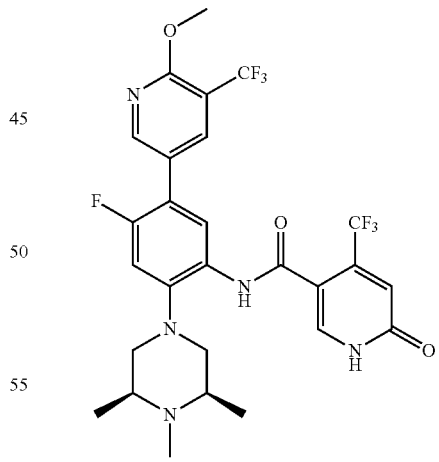

The title compound was prepared similar to the sequence described above for the preparation of Example 31 using 2-methoxy-3-(trifluoromethyl)pyridine-5-boronic acid. $^1$H NMR (500 MHz, MeOD) δ 8.54 (s, 1H), 8.14 (s, 1H), 7.97 (s, 1H), 7.92 (d, J=8.3 Hz, 1H), 7.10 (d, J=12.1 Hz, 1H), 6.91 (s, 1H), 4.08 (s, 3H), 3.08 (d, J=11.3 Hz, 2H), 2.62 (t, J=11.1 Hz, 2H), 2.55 (dd, J=8.1, 6.1 Hz, 2H), 2.37 (s, 3H), 1.16 (d, J=6.2 Hz, 6H); LCMS [M+1]+=602.3.

Example 137: 4-cyano-N-[4-fluoro-5-(2-morpholin-4-ylpyrimidin-5-yl)-2-[(3R,5S)-3,4,5-trimethylpiperazin-1-yl]phenyl]-6-methoxypyridine-3-carboxamide

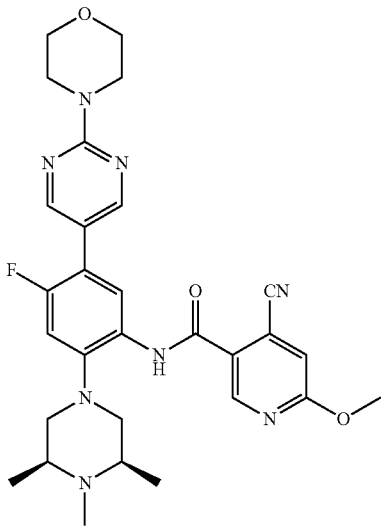 [SMILES: COc1cc(C#N)c(C(=O)Nc2cc(-c3cnc(N4CCOCC4)nc3)c(F)cc2N2C[C@@H](C)N(C)[C@@H](C)C2)cn1]

Step 1: 5-bromo-4-iodo-2-methoxypyridine

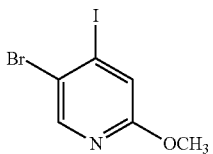

A solution of DIPA (14.8 mL, 117.6 mmol, and 1.1 eq) in dry THF (150 mL) was cooled to −78° C., and n-BuLi (42 mL, 106.95 mmol, 1 eq, 2.5 M) was added dropwise. Then, the reaction mixture was stirred for 30 min, 5-bromo-2-methoxypyridine (20.0 g, 106.95 mmol, 1.0 eq) in dry THF (115 mL) was added dropwise, then the reaction mixture was stirred at −78° C. for 1 h. The reaction mixture was quenched with iodine (27.6 g, 106.95 mmol, and 1 eq) in THF (80 mL) added dropwise and the reaction mixture was stirred for 16 h. TLC analysis indicated a non-polar spot. The reaction was quenched with sodium thiosulfate solution (500 mL), extracted with EtOAc (1000 mL) and the separated organic layers were combined and dried over $Na_2SO_4$. Concentration under reduced pressure gave crude compound; which was recrystallized from ethanol (120 mL) to give 5-bromo-4-iodo-2-methoxypyridine (12 g, 35.9%) as an off white solid. LCMS: [M+H]+ 315.83.

Step 2: 5-bromo-2-methoxyisonicotinonitrile

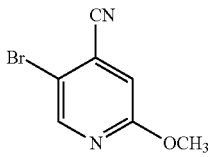

To a suspension of 5-bromo-4-iodo-2-methoxypyridine (10 g, 31.85 mmol, 1 eq) in DMF (100 mL) was added CuCN (5.7 g, 63.7 mmol, 2.0 eq). The reaction mixture was heated at 100° C. for 16 h. TLC analysis indicated polar spot. The reaction mixture was diluted with water (200 mL) and filtered off and washed with EtOAc (500 mL) and cold water (300 lt). The organic layer was separated, dried over sodium sulfate and concentrated under reduced pressure at 30° C. This was purified by column chromatography using silica (100-200 mesh) eluting with 5% EtOAc in pet ether to give 5-bromo-2-methoxyisonicotinonitrile (4 g, 59.7% yield) as a solid compound. GCMS: [M+H]+ 213.

Step 3: methyl 4-cyano-6-methoxynicotinate

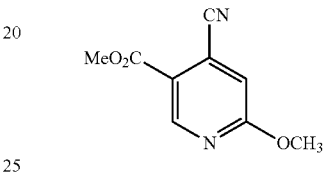

To a stirred solution of 5-bromo-2-methoxyisonicotinonitrile (4 g, 18.86 mmol, 1 eq) in MeOH (33 mL) was added TEA (33 mL, 226.32 mmol, 12 eq) and $Pd_2(dppf)Cl_2 \cdot DCM$ (1.5 g, 1.89 mmol, 0.1 eq) at RT and the reaction mixture was de-gassed with argon for 5 min. Then the reaction mixture was heated to 90° C. for 16 h under CO gas (250 psi) in a sealed bomb. TLC analysis indicated formation of polar spot. The reaction mixture was filtered through a celite pad then the filtrate was concentrated to crude compound. The crude compound was purified by column chromatography (silica gel, 100-2000 mesh) using 20% EtOAc in Pet ether as eluent to afford methyl 4-cyano-6-methoxynicotinate (2 g, 55.5% yield) as solid. LCMS: [M+H] 193.0.

Step 4: 4-cyano-6-methoxynicotinic acid

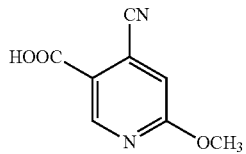

To a suspension of methyl 4-cyano-6-methoxynicotinate (2 g, 10.36 mmol, 1 eq) in THF:MeOH:$H_2O$ (9 mL: 3 mL: 6 mL) (33 mL), lithium hydroxide monohydrate (248 mg, 249.2 mmol, 4.0 eq) was added. The reaction mixture was stirred at RT for 16 h. TLC analysis of indication of polar spot. The reaction was concentrated under reduced pressure gave crude compound. This was acidified with 2N HCl (20 mL), precipitate was formed and filtered off and washed with diethyl ether (50 mL) and filtered off and dried on vacuum to give 4-cyano-6-methoxynicotinic acid (0.9 mg, 48.6% yield) as an off white solid compound. LCMS: [M+]H+ 177.17.

Step 5: 4-cyano-N-[4-fluoro-5-(2-morpholin-4-ylpyrimidin-5-yl)-2-[(3R,5S)-3,4,5-trimethylpiperazin-1-yl]phenyl]-6-methoxypyridine-3-carboxamide

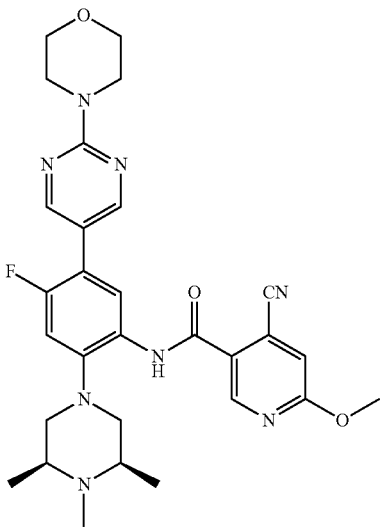 [SMILES: COc1cc(C#N)c(C(=O)Nc2cc(-c3cnc(N4CCOCC4)nc3)c(F)cc2N2C[C@@H](C)N(C)[C@@H](C)C2)cn1]

The title compound was prepared in a manner similar to the preparation of Example 34 using 4-cyano-6-methoxynicotinic acid in place of 1-methyl-6-oxo-4-(trifluoromethyl)-1,6-dihydropyridine-3-carboxylic acid. $^1$H NMR (500 MHz, MeOD) δ 8.76 (d, J=10.2 Hz, 1H), 8.56 (s, 2H), 7.50 (s, 1H), 7.46 (dd, J=12.0, 8.2 Hz, 1H), 7.14 (t, J=12.6 Hz, 1H), 4.10 (d, J=1.4 Hz, 3H), 3.82 (dd, J=6.4, 2.9 Hz, 4H), 3.77-3.73 (m, 4H), 2.89 (d, J=12.1 Hz, 1H), 2.67 (t, J=11.0 Hz, 1H), 2.64 (dt, J=30.5, 11.2 Hz, 2H), 2.57-2.51 (m, 1H), 2.57-2.44 (m, 2H), 2.20 (s, 3H), 1.04 (dd, J=22.7, 6.3 Hz, 6H); Major rotamer reported; LCMS [M+1]$^+$=561.43.

Example 138: 3-chloro-N-[4-fluoro-5-(2-morpholin-4-ylpyrimidin-5-yl)-2-[(3R,5S)-3,4,5-trimethylpiperazin-1-yl]phenyl]benzamide

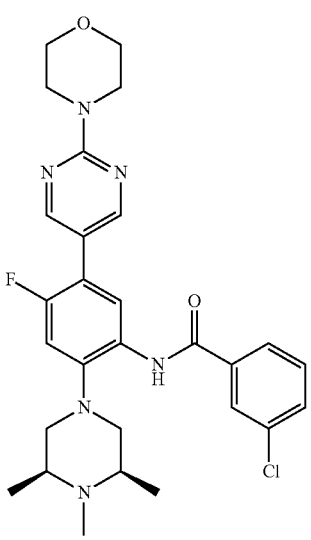

The title compound (beige solid, 32.4 mg, 55%) was prepared according to a procedure similar to Example 34 using 3,5-dichlorobenzoic acid (38 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.20 (s, 1H), 8.52 (d, J=8.2 Hz, 1H), 8.50 (d, J=1.2 Hz, 2H), 7.71 (s, 2H), 7.50 (s, 1H), 6.95 (d, J=11.2 Hz, 1H), 3.84-3.78 (m, 4H), 3.75-3.69 (m, 4H), 2.82 (d, J=11.0 Hz, 2H), 2.63 (t, J=10.9 Hz, 2H), 2.42-2.34 (m, 2H), 2.31 (s, 3H), 1.11 (d, J=6.2 Hz, 6H); LCMS [M+H]$^+$ 573.2.

Example 139: 2,6-dichloro-N-[4-fluoro-5-(2-morpholin-4-ylpyrimidin-5-yl)-2-[(3R,5S)-3,4,5-trimethylpiperazin-1-yl]phenyl]benzamide

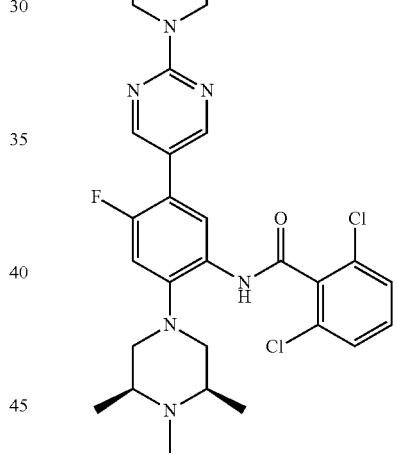

The title compound (beige solid, 32.4 mg, 55%) was prepared according to a procedure similar to Example 34 using 3,5-dichlorobenzoic acid (38 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.20 (s, 1H), 8.52 (d, J=8.2 Hz, 1H), 8.50 (d, J=1.2 Hz, 2H), 7.71 (s, 2H), 7.50 (s, 1H), 6.95 (d, J=11.2 Hz, 1H), 3.84-3.78 (m, 4H), 3.75-3.69 (m, 4H), 2.82 (d, J=11.0 Hz, 2H), 2.63 (t, J=10.9 Hz, 2H), 2.42-2.34 (m, 2H), 2.31 (s, 3H), 1.11 (d, J=6.2 Hz, 6H); LCMS [M+H]$^+$ 573.2.

Example 140: 3-chloro-2-fluoro-N-[4-fluoro-5-(2-morpholin-4-ylpyrimidin-5-yl)-2-[(3R,5S)-3,4,5-trimethylpiperazin-1-yl]phenyl]benzamide

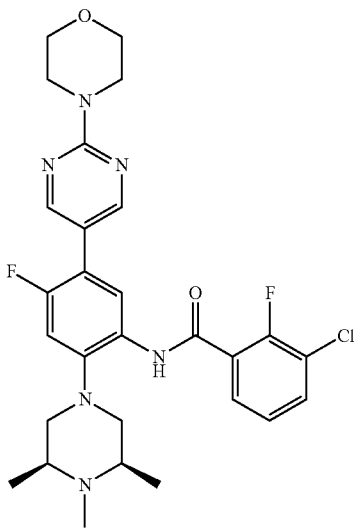

The title compound (light yellow solid, 46.9 mg, 82%) was prepared by a procedure similar to Example 34 using 3-chloro-2-fluorobenzoic acid (35 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.78 (d, J=12.5 Hz, 1H), 8.71 (d, J=8.3 Hz, 1H), 8.58 (s, 2H), 8.08 (t, J=7.3 Hz, 1H), 7.61 (t, J=7.5 Hz, 1H), 7.29 (t, J=7.6 Hz, 1H), 7.04 (d, J=11.4 Hz, 1H), 3.91-3.84 (m, 4H), 3.83-3.78 (m, 4H), 2.89 (t, J=7.0 Hz, 2H), 2.67 (t, J=10.9 Hz, 2H), 2.56-2.47 (m, 2H), 2.38 (s, 3H), 1.16 (d, J=6.2 Hz, 6H); LCMS [M+H]$^+$ 557.3.

Example 141: N-[4-fluoro-5-(2-morpholin-4-ylpyrimidin-5-yl)-2-[(3R,5S)-3,4,5-trimethylpiperazin-1-yl]phenyl]-2-(trifluoromethyl)benzamide

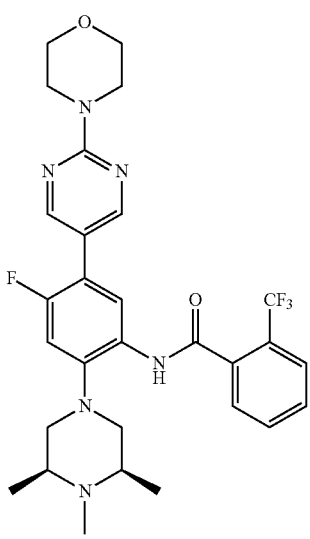

The title compound (beige solid, 51.7 mg, 89%) was prepared by a procedure similar to Example 34 using 4-fluoro-5-(2-morpholinopyrimidin-5-yl)-2-((3S,5R)-3,4,5-trimethylpiperazin-1-yl)aniline (40 mg, 0.1 mmol) and 2-(trifluoromethyl)benzoyl chloride (22 μL, 0.15 mmol). $^1$H NMR (500 MHz, CHLOROFORM-d) δ=8.62-8.53 (m, 4H), 7.80 (d, J=7.6 Hz, 1H), 7.69 (t, J=7.6 Hz, 1H), 7.64 (t, J=6.8 Hz, 2H), 7.00 (d, J=11.2 Hz, 1H), 3.92-3.84 (m, 4H), 3.84-3.76 (m, 4H), 2.85 (d, J=11.0 Hz, 2H), 2.62 (t, J=10.9 Hz, 2H), 2.31-2.17 (m, 5H), 1.11 (d, J=6.2 Hz, 6H); LCMS [M+H]$^+$ 573.4.

Example 142: N-[5-[6-(dimethylamino)pyridin-3-yl]-4-fluoro-2-[(3R 5S)-3,4,5-trimethylpiperazin-1-yl]phenyl]-6-oxo-4-(trifluoromethyl)-1H-pyridine-3-carboxamide

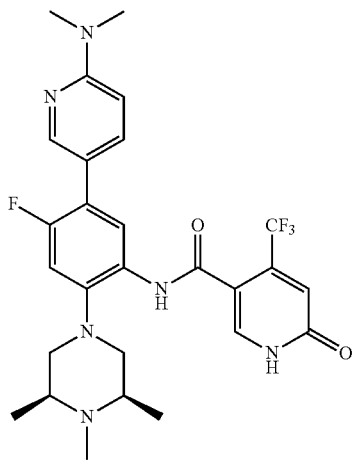

The title compound was prepared similar to the sequence described above for the preparation of Example 31 using 6-(dimethylamino)pyridine-3-boronic acid pinacol ester. $^1$H NMR (500 MHz, MeOD) δ 8.25 (s, 1H), 7.95 (s, 1H), 7.89 (d, J=8.3 Hz, 1H), 7.74 (dd, J=9.0, 0.8 Hz, 1H), 7.04 (d, J=12.2 Hz, 1H), 6.91 (s, 1H), 6.75 (d, J=8.9 Hz, 1H), 3.12 (s, 6H), 3.04 (d, J=11.2 Hz, 2H), 2.61 (t, J=11.1 Hz, 2H), 2.57-2.50 (m, 2H), 2.37 (s, 3H), 1.16 (d, J=6.1 Hz, 6H); LCMS [M+1]$^+$=547.28.

Example 143: tert-butyl 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate

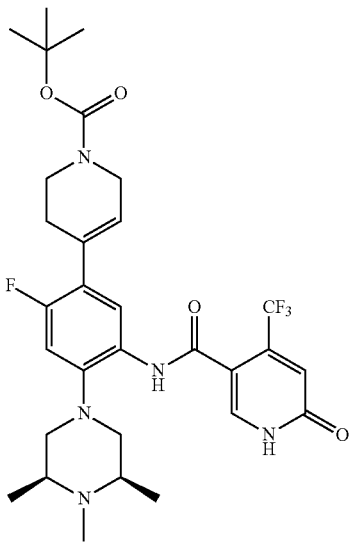

Step 1: tert-butyl 4-(2-fluoro-5-(4-(trifluoromethyl)-6-(2-(trimethylsilyl)ethoxy)nicotinamido)-4-((3S,5R)-3,4,5-trimethylpiperazin-1-yl)phenyl)-3,6-dihydropyridine-1(2H)-carboxylate

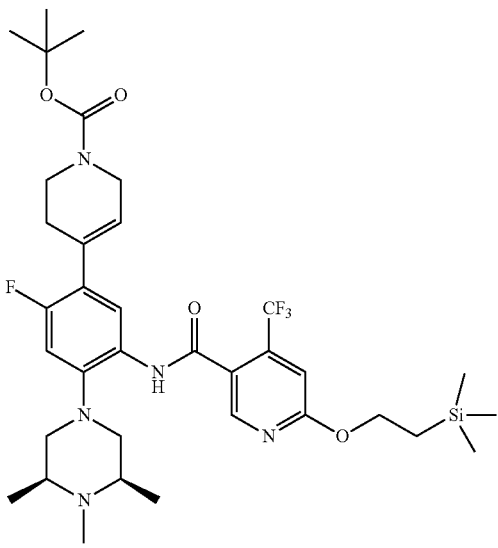 [SMILES: C[C@@H]1CN(c2cc(F)c(C3=CCN(C(=O)OC(C)(C)C)CC3)cc2NC(=O)c2cnc(OCC[Si](C)(C)C)cc2C(F)(F)F)C[C@H](C)N1C]

A procedure similar to Example 39 was employed using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (250 mg, 0.413 mmol), tert-butyl-4-(4,4,5,5-tetramethyl-1,3,2-dioxaborolan-2-yl)-1,2,3,6-tetrahydropyridine-1-carboxylate (191 mg, 0.619 mmol to give the title compound. LCMS [M+H]=708.7.

Step 2: tert-butyl 4-(2-fluoro-5-(4-(trifluoromethyl)-6-(2-(trimethylsilyl)ethoxy)nicotinamido)-4-((3S,5R)-3,4,5-trimethylpiperazin-1-yl)phenyl)-3,6-dihydropyridine-1 (2H)-carboxylate

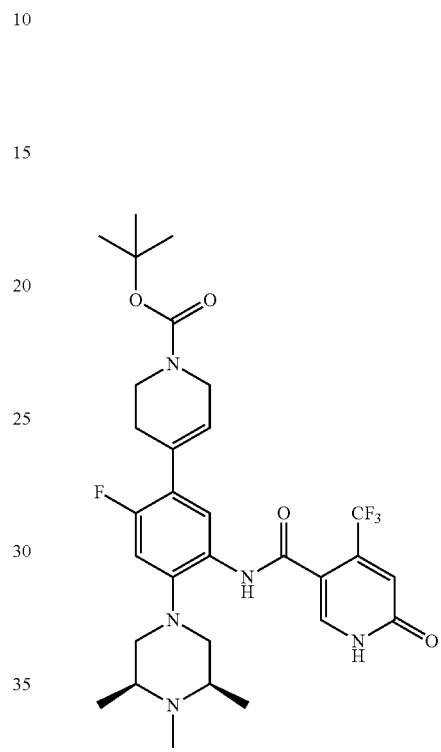

TFA (0.6 ml) was added to a solution of tert-butyl 4-(2-fluoro-5-(4-(trifluoromethyl)-6-(2-(trimethylsilyl)ethoxy)nicotinamido)-4-((3S,5R)-3,4,5-trimethylpiperazin-1-yl)phenyl)-3,6-dihydropyridine-1(2H)-carboxylate in DCM (20 ml) at RT and the reaction mixture was stirred at RT. LCMS after 10 min showed completion of the reaction. The reaction mixture was concentrated to dryness (bath temperature <25° C.), the residue was dissolved in MeOH and passed through a cation exchange resin cartridge (Porapak Rxn CX 60 cc) to collect the title compound as an off white powder. (706 mg, 91%). $^1$H NMR (500 MHz, METHANOL-d4) δ=8.01-7.93 (m, 1H), 7.84-7.73 (m, 1H), 7.01-6.93 (m, 1H), 6.92-6.86 (m, 1H), 6.10-5.93 (m, 1H), 4.17-4.02 (m, 2H), 3.71-3.58 (m, 2H), 3.06-2.99 (m, 2H), 2.65-2.49 (m, 6H), 2.43-2.36 (m, 3H), 1.62-1.43 (m, 9H), 1.17 (br d, J=5.7 Hz, 6H); LCMS [M+H]+ 608.6

Example 144: N-[4-fluoro-2-[(3R,5S)-3,4,5-trimethylpiperazin-1-yl]-5-[4-(trifluoromethyl)phenyl]phenyl]-6-oxo-4-(trifluoromethyl)-1H-pyridine-3-carboxamide

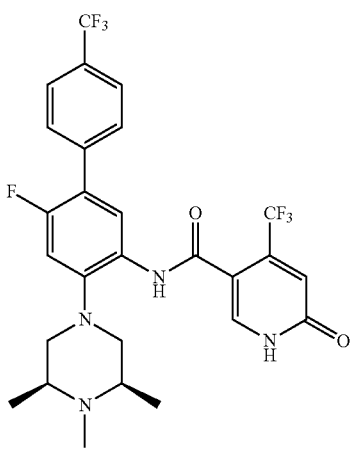

The title compound (tan solid, 43.8 mg, 75%) was prepared using a procedure similar to that of Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 4-(trifluoromethyl)phenylboronic acid (38 mg, 0.2 mmol). $^1$H NMR (500 MHz, CHLOROFORM-d) δ=8.66 (s, 1H), 8.50 (d, J=8.1 Hz, 1H), 7.88 (s, 1H), 7.70 (s, 4H), 7.04 (d, J=11.6 Hz, 1H), 7.01 (s, 1H), 2.85 (br d, J=11.0 Hz, 2H), 2.68 (br t, J=10.9 Hz, 2H), 2.41-2.27 (m, 5H), 1.15 (d, J=6.2 Hz, 6H); LCMS [M+H]$^+$ 571.1.

Example 145: N-[4-fluoro-2-[(3R,5S)-3,4,5-trimethylpiperazin-1-yl]-5-[4-(trifluoromethoxy)phenyl]phenyl]-6-oxo-4-(trifluoromethyl)-1H-pyridine-3-carboxamide

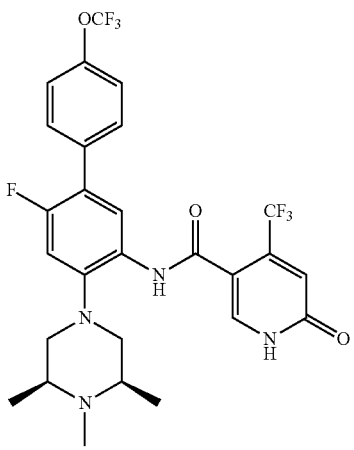

The title compound (light solid, 37.6 mg, 64%) was prepared by a procedure similar to Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 4-(trifluoromethoxy)phenylboronic acid (41 mg, 0.2 mmol). $^1$H NMR (500 MHz, CHLOROFORM-d) δ=8.67 (s, 1H), 8.47 (d, J=8.2 Hz, 1H), 7.86 (s, 1H), 7.60 (d, J=7.8 Hz, 2H), 7.29 (br d, J=8.4 Hz, 2H), 7.05-6.99 (m, 2H), 2.84 (br d, J=10.9 Hz, 2H), 2.67 (br t, J=10.9 Hz, 2H), 2.40-2.29 (m, 5H), 1.15 (d, J=6.1 Hz, 6H); LCMS [M+H]$^+$ 587.2.

Example 146: N-[4-fluoro-5-phenyl-2-[(3R,5S)-3,4,5-trimethylpiperazin-1-yl]phenyl]-6-oxo-4-(trifluoromethyl)-1H-pyridine-3-carboxamide

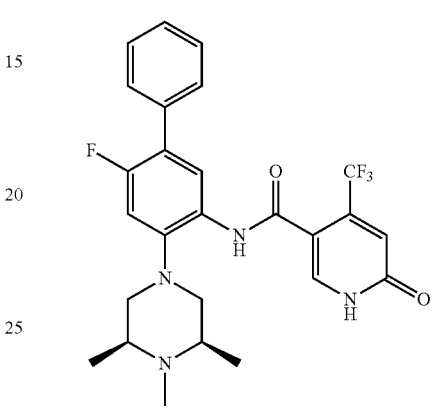

The title compound (grey solid, 29.4 mg, 56%) was prepared by a procedure similar to Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and phenylboronic acid (24 mg, 0.2 mmol). $^1$H NMR (500 MHz, CHLOROFORM-d) δ=8.67 (s, 1H), 8.48 (d, J=8.1 Hz, 1H), 7.87 (s, 1H), 7.58 (d, J=8.1 Hz, 2H), 7.44 (t, J=7.6 Hz, 2H), 7.39-7.34 (m, 1H), 7.04-6.98 (m, 2H), 2.85 (br d, J=10.9 Hz, 2H), 2.67 (br t, J=10.9 Hz, 2H), 2.42-2.29 (m, 5H), 1.15 (d, J=6.2 Hz, 6H); LCMS [M+H]$^+$ 503.2.

Example 147: N-[5-(4-chlorophenyl)-4-fluoro-2-[(3R,5S)-3,4,5-trimethylpiperazin-1-yl]phenyl]-6-oxo-4-(trifluoromethyl)-1H-pyridine-3-carboxamide

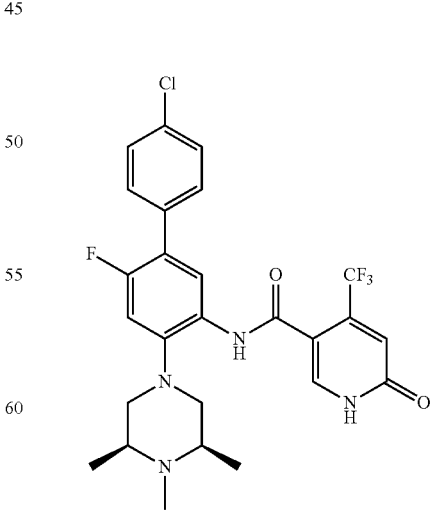

The title compound (grey solid, 31.5 mg, 57%) was prepared in a manner similar to Example 31 using N-(5- bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 4-chlorophenylboronic acid (31 mg, 0.2 mmol). $^1$H NMR (500 MHz, CHLOROFORM-d) δ=8.66 (s, 1H), 8.46 (d, J=8.1 Hz, 1H), 7.87 (s, 1H), 7.51 (d, J=7.7 Hz, 2H), 7.44-7.39 (m, 2H), 7.04-6.98 (m, 2H), 2.84 (br d, J=11.0 Hz, 2H), 2.67 (br t, J=10.8 Hz, 2H), 2.40-2.30 (m, 5H), 1.15 (d, J=6.2 Hz, 6H); LCMS [M+H]$^+$ 537.3.

Example 148: N-[4-fluoro-5-[1-[(4-methoxyphenyl)methyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

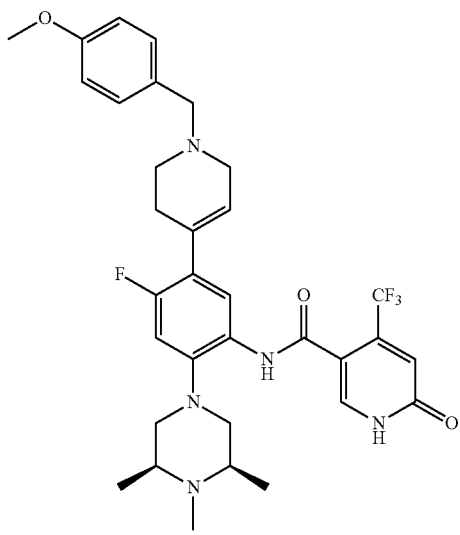 [SMILES: COc1ccc(CN2CC=C(c3cc(NC(=O)c4c[nH]c(=O)cc4C(F)(F)F)c(N4C[C@@H](C)N(C)[C@@H](C)C4)cc3F)CC2)cc1]

N-(4-Fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (15 mg, 0.030 mmol), 4-methoxybenzaldehyde (8.05 mg, 0.059 mmol) and acetic acid, glacial, 99.8% (7.10 mg, 0.118 mmol) were mixed in anhydrous DCE. A cloudy solution was obtained. After 5-10 min, sodium triacetoxyborohydride (18.79 mg, 0.089 mmol) was added and the reaction mixture was stirred at RT for 18 h. LCMS showed complete disappearance of the starting material and formation of the desired product. The reaction was quenched with sat aq NaHCO$_3$ solution (basic). The organic phase was separated, the aqueous phase was extracted with DCM (2×), then the combined organic phase was washed with brine, dried over Na$_2$SO$_4$ and concentrated to obtain the crude product. It was purified on isco column (4 G), eluting with DCM containing 0-8% DCM. The appropriate fractions were combined and concentrated to afford the title compound as a white foam (11 mg, 56%). $^1$H NMR (500 MHz, METHANOL-d4) δ=7.97-7.89 (m, 1H), 7.81-7.70 (m, 1H), 7.35-7.27 (m, 2H), 6.98-6.83 (m, 4H), 6.03-5.95 (m, 1H), 3.83-3.76 (m, 3H), 3.69-3.62 (m, 2H), 3.25-3.17 (m, 2H), 3.05-2.95 (m, 2H), 2.84-2.73 (m, 2H), 2.61-2.48 (m, 6H), 2.35 (s, 3H), 1.17-1.12 (m, 6H); LCMS [M+H]+ 628.4

Example 149: N-[4-fluoro-5-(6-methylpyridazin-4-yl)-2-[(3R,5S)-3,4,5-trimethylpiperazin-1-yl]phenyl]-6-oxo-4-(trifluoromethyl)-1H-pyridine-3-carboxamide

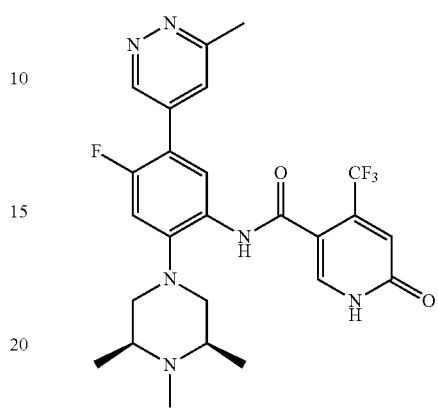

N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) and 3-methylpyridazine-5-boronic acid, pinacol ester (25.4 mg, 0.116 mmol) using a procedure similar to Example 39 afforded the silyl ether intermediate, which was deprotected using TFA and isolated to give the title compound in 61% yield. $^1$H NMR (500 MHz, METHANOL-d4) δ=9.32-9.20 (m, 1H), 8.12-8.03 (m, 1H), 8.01-7.95 (m, 1H), 7.86-7.80 (m, 1H), 7.23-7.10 (m, 1H), 6.98-6.88 (m, 1H), 3.21-3.12 (m, 2H), 2.78-2.74 (m, 3H), 2.72-2.61 (m, 4H), 2.49-2.38 (m, 3H), 1.20 (br d, J=4.6 Hz, 6H); LCMS [M+H]+ 519.5

Example 150: N-[4-fluoro-5-[1-(2-methylpropyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

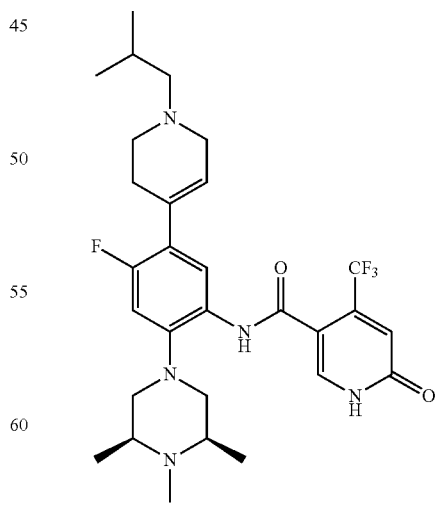

A procedure similar to Example 148 was used with N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide and isobutyraldehyde to give the desired product. ¹H NMR (500 MHz, METHANOL-d4) δ=7.87-7.76 (m, 1H), 7.74-7.62 (m, 1H), 6.87-6.81 (m, 1H), 6.81-6.77 (m, 1H), 5.96-5.84 (m, 1H), 3.29-3.22 (m, 2H), 2.95-2.86 (m, 2H), 2.80-2.71 (m, 2H), 2.56-2.50 (m, 2H), 2.50-2.45 (m, 2H), 2.45-2.37 (m, 2H), 2.37-2.30 (m, 2H), 2.29-2.23 (m, 3H), 1.94-1.83 (m, 1H), 1.08-1.01 (m, 6H), 0.91-0.86 (m, 6H); LCMS [M+H]+ 564.4

Example 151: N-[5-[1-(cyclopropylmethyl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

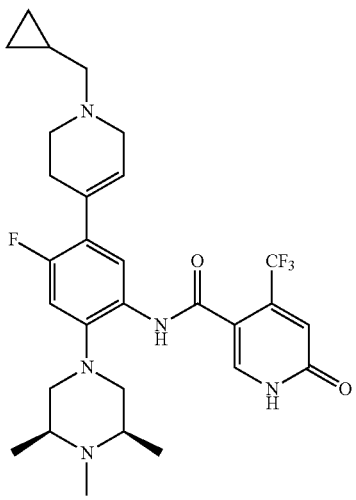 [SMILES: C[C@@H]1CN(c2cc(F)c(C3=CCN(CC4CC4)CC3)cc2NC(=O)c2c[nH]c(=O)cc2C(F)(F)F)C[C@H](C)N1C]

A procedure similar to Example 148 was used with cyclopropylbutyraldehyde to give the title compound in 77% yield. ¹H NMR (500 MHz, METHANOL-d4) δ=7.96-7.90 (m, 1H), 7.88-7.82 (m, 1H), 7.04-6.97 (m, 1H), 6.96-6.91 (m, 1H), 6.11-6.03 (m, 1H), 3.86-3.74 (m, 2H), 3.40-3.35 (m, 2H), 3.11-3.02 (m, 2H), 2.98-2.90 (m, 2H), 2.86-2.77 (m, 2H), 2.69-2.57 (m, 4H), 2.48-2.38 (m, 3H), 1.22-1.17 (m, 6H), 1.16-1.09 (m, 1H), 0.78-0.73 (m, 2H), 0.44-0.37 (m, 2H); LCMS [M+H]+ 562.5

Example 152: N-[4-fluoro-2-[(3R,5S)-3,4,5-trimethylpiperazin-1-yl]-5-[1-(3,3,3-trifluoropropyl)-3,6-dihydro-2H-pyridin-4-yl]phenyl]-6-oxo-4-(trifluoromethyl)-1H-pyridine-3-carboxamide

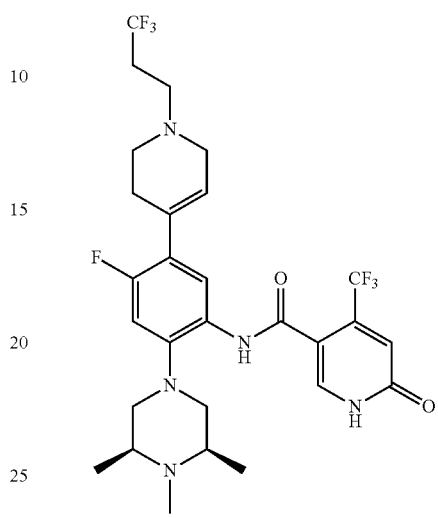

A procedure similar to that used for Example 148 was employed using 4,4,4-trifluorobutanal to give the title compound in 83% yield. ¹H NMR (500 MHz, METHANOL-d4) δ=7.97-7.91 (m, 1H), 7.83-7.73 (m, 1H), 6.98-6.93 (m, 1H), 6.93-6.91 (m, 1H), 6.06-5.98 (m, 1H), 3.27-3.22 (m, 2H), 3.07-3.01 (m, 2H), 2.83-2.75 (m, 4H), 2.63-2.49 (m, 8H), 2.40-2.37 (m, 3H), 1.19-1.15 (m, 6H); LCMS [M+H]+ 604.5

Example 153: N-[4-fluoro-5-[1-[(4-fluorophenyl)methyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

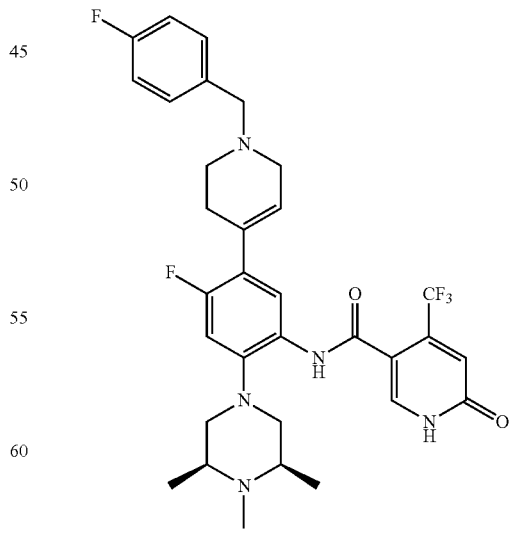

A procedure similar to that used for Example 148 with 4-fluorobenzaldehyde gave the title compound in 73% yield. ¹H NMR (500 MHz, METHANOL-d4) δ=7.97-7.90 (m, 1H), 7.83-7.73 (m, 1H), 7.49-7.37 (m, 2H), 7.15-7.05 (m, 2H), 6.99-6.88 (m, 2H), 6.05-5.96 (m, 1H), 3.73-3.67 (m, 2H), 3.25-3.19 (m, 2H), 3.08-2.99 (m, 2H), 2.81-2.75 (m, 2H), 2.63-2.53 (m, 6H), 2.42-2.37 (m, 3H), 1.21-1.16 (m, 6H); LCMS [M+H]+ 616.6.

Example 154: N-[4-fluoro-5-[1-(pyridin-3-ylmethyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

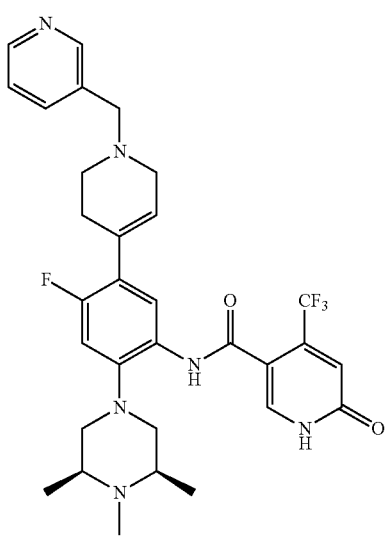 [SMILES: C[C@@H]1CN(c2cc(F)c(C3=CCN(Cc4cccnc4)CC3)cc2NC(=O)c2c[nH]c(=O)cc2C(F)(F)F)C[C@H](C)N1C]

A procedure similar to Example 148 using nicotinaldehyde afforded the title compound in 38% yield. ¹H NMR (500 MHz, METHANOL-d4) δ=8.49-8.45 (m, 1H), 8.40-8.33 (m, 1H), 7.84-7.77 (m, 2H), 7.70-7.60 (m, 1H), 7.37-7.33 (m, 1H), 6.86-6.78 (m, 2H), 5.94-5.86 (m, 1H), 3.67-3.60 (m, 2H), 3.13-3.08 (m, 2H), 2.96-2.87 (m, 2H), 2.69-2.63 (m, 2H), 2.54-2.45 (m, 6H), 2.32-2.28 (m, 3H), 1.08-1.05 (m, 6H); LCMS [M+H]+ 599.5

Example 155: N-[4-fluoro-2-[(3R,5S)-3,4,5-trimethylpiperazin-1-yl]-5-[1-(thiophen-3-ylmethyl)-3,6-dihydro-2H-pyridin-4-yl]phenyl]-6-oxo-4-(trifluoromethyl)-1H-pyridine-3-carboxamide

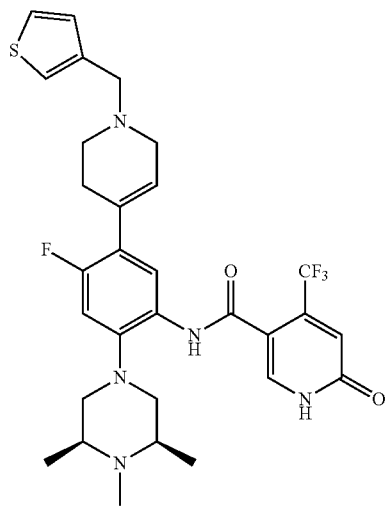 [SMILES: C[C@@H]1CN(c2cc(F)c(C3=CCN(Cc4ccsc4)CC3)cc2NC(=O)c2c[nH]c(=O)cc2C(F)(F)F)C[C@H](C)N1C]

A procedure similar to Example 148 using thiophene-3-carbaldehyde afforded the title compound in 73% yield. ¹H NMR (500 MHz, METHANOL-d4) δ=7.99-7.90 (m, 1H), 7.83-7.73 (m, 1H), 7.42 (dd, J=3.1, 4.6 Hz, 1H), 7.39-7.32 (m, 1H), 7.23-7.15 (m, 1H), 6.99-6.86 (m, 2H), 6.08-5.95 (m, 1H), 3.82-3.71 (m, 2H), 3.28-3.20 (m, 2H), 3.02 (br d, J=10.9 Hz, 2H), 2.85-2.74 (m, 2H), 2.63-2.50 (m, 6H), 2.41-2.35 (m, 3H), 1.20-1.14 (m, 6H); LCMS [M+H]+ 604.5

Example 156: N-[5-[5-(cyclopropylmethoxy)pyridin-3-yl]-4-fluoro-2-[(3R,5S)-3,4,5-trimethylpiperazin-1-yl]phenyl]-6-oxo-4-(trifluoromethyl)-1H-pyridine-3-carboxamide

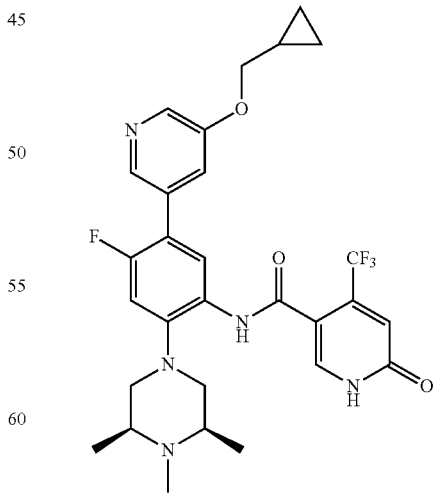

A procedure similar to Example 39 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide Example 157: N-[4-fluoro-5-(6-hydroxypyridin-3-yl)-2-[(3R,5S)-3,4,5-trimethylpiperazin-1-yl]phenyl]-6-oxo-4-(trifluoromethyl)-1H-pyridine-3-carboxamide and 3-(cyclopropylmethoxy)-5-(4,4,5,5-tetramethyl-1,3,2-dioxaborolan-2-yl)pyridine afforded the silyoxy intermediate which was deprotected using TFA to give the title compound in 71% yield for the last step. ¹H NMR (500 MHz, METHANOL-d4) δ=8.22-8.17 (m, 1H), 8.16-8.08 (m, 1H), 7.93-7.88 (m, 1H), 7.87-7.80 (m, 1H), 7.50-7.44 (m, 1H), 7.10-7.00 (m, 1H), 6.86-6.79 (m, 1H), 3.90-3.83 (m, 2H), 3.16-3.08 (m, 2H), 3.01-2.81 (m, 2H), 2.73-2.65 (m, 2H), 2.63-2.43 (m, 3H), 1.23-1.18 (m, 7H), 0.59-0.52 (m, 2H), 0.33-0.27 (m, 2H); LCMS [M+H]+ 574.6

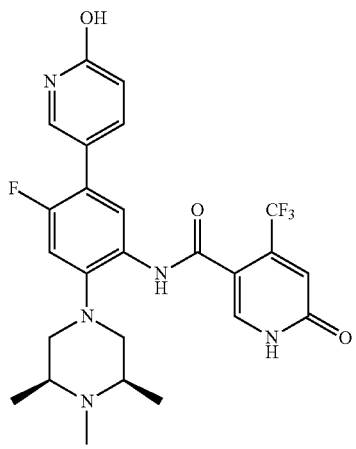 [SMILES: C[C@@H]1CN(c2cc(F)c(-c3ccc(O)nc3)cc2NC(=O)c2c[nH]c(=O)cc2C(F)(F)F)C[C@H](C)N1C]

The title compound was prepared similar to the sequence described above for the preparation of Example 31 using 2-(cyclopropylmethoxy)-5-(4,4,5,5-tetramethyl-1,3,2-dioxaborolan-2-yl)pyridine. This compound was isolated during the purification step as a side product. ¹H NMR (500 MHz, DMSO) δ 9.50 (s, 1H), 7.91 (s, 1H), 7.69 (d, J=8.7 Hz, 1H), 7.60 (d, J=9.6 Hz, 1H), 7.49 (s, 1H), 7.00 (d, J=12.6 Hz, 1H), 6.80 (s, 1H), 6.44 (d, J=9.5 Hz, 1H), 3.00 (d, J=10.9 Hz, 2H), 2.44 (t, J=11.0 Hz, 2H), 2.36-2.31 (m, 2H), 2.19 (s, 3H), 1.00 (d, J=6.1 Hz, 6H); ¹⁹F NMR (471 MHz, DMSO) δ −61.34 (s), −119.33 (s); LCMS HSS [M+1]+=520.35. Major rotamer reported Example 158: N-[4-fluoro-5-(2-piperazin-1-ylpyrimidin-5-yl)-2-[(3R,5S)-3,4,5-trimethylpiperazin-1-yl]phenyl]-6-oxo-4-(trifluoromethyl)-H-pyridine-3-carboxamide

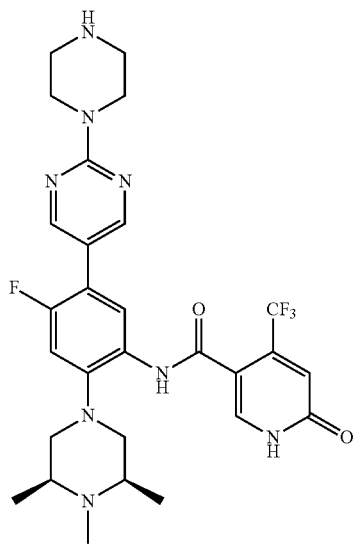

The title compound was prepared similar to the sequence described above for the preparation of Example 31 using 2-(4-boc-piperazino)pyrimidine-5-boronic acid pinacol ester and deprotecting the intermediate Boc-protected piperidine with TFA. ¹H NMR (500 MHz, MeOD) δ 8.56 (d, J=0.9 Hz, 2H), 7.97 (s, 1H), 7.90 (d, J=8.2 Hz, 1H), 7.08 (d, J=12.1 Hz, 1H), 6.89 (s, 1H), 3.97-3.92 (m, 4H), 3.07-3.02 (m, J=10.8, 5.6 Hz, 6H), 2.61 (t, J=11.1 Hz, 2H), 2.57-2.48 (m, 2H), 2.36 (s, 3H), 1.16 (d, J=6.1 Hz, 6H); LCMS HSS [M+1]+=589.34.

Example 159: 3-chloro-5-fluoro-N-[4-fluoro-5-(2-morpholin-4-ylpyrimidin-5-yl)-2-[(3R,5S)-3,4,5-trimethylpiperazin-1-yl]phenyl]benzamide

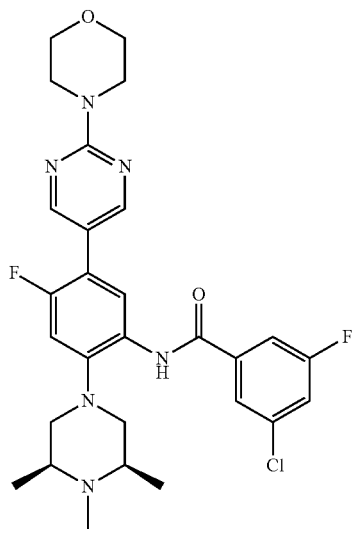 [SMILES: C[C@@H]1CN(c2cc(F)c(-c3cnc(N4CCOCC4)nc3)cc2NC(=O)c2cc(F)cc(Cl)c2)C[C@H](C)N1C]

The title compound (beige solid, 42.5 mg, 74%) was prepared by a procedure similar to Example 34 using 3-chloro-5-fluorobenzoic acid (35 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.26 (s, 1H), 8.60 (d, J=8.1 Hz, 1H), 8.57 (d, J=1.1 Hz, 2H), 7.68 (s, 1H), 7.54 (td, J=1.8, 8.7 Hz, 1H), 7.32 (td, J=2.1, 8.0 Hz, 1H), 7.03 (d, J=11.2 Hz, 1H), 3.92-3.85 (m, 4H), 3.83-3.78 (m, 4H), 2.90 (br d, J=11.0 Hz, 2H), 2.71 (br t, J=10.9 Hz, 2H), 2.49-2.41 (m, 2H), 2.38 (s, 3H), 1.18 (d, J=6.2 Hz, 6H); LCMS [M+H]$^+$ 557.4.

Example 160: 3,5-difluoro-N-[4-fluoro-5-(2-morpholin-4-ylpyrimidin-5-yl)-2-[(3R,5S)-3,4,5-trimethylpiperazin-1-yl]phenyl]benzamide

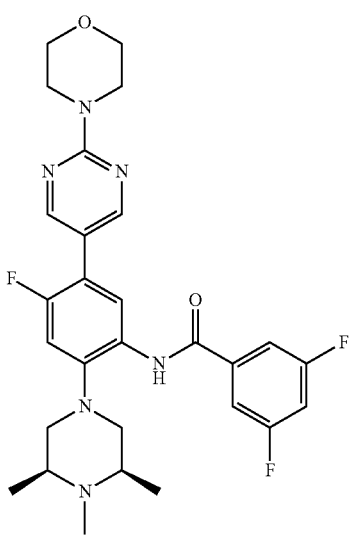 [SMILES: C[C@@H]1CN(c2cc(F)c(-c3cnc(N4CCOCC4)nc3)cc2NC(=O)c2cc(F)cc(F)c2)C[C@H](C)N1C]

Example 161: N-[4-fluoro-5-[2-[(2R,6S)-2,6-dimethylmorpholin-4-yl]pyrimidin-5-yl]-2-[(3S,5R)-3,4,5-trimethylpiperazin-1-yl]phenyl]-6-oxo-4-(trifluoromethyl)-1H-pyridine-3-carboxamide

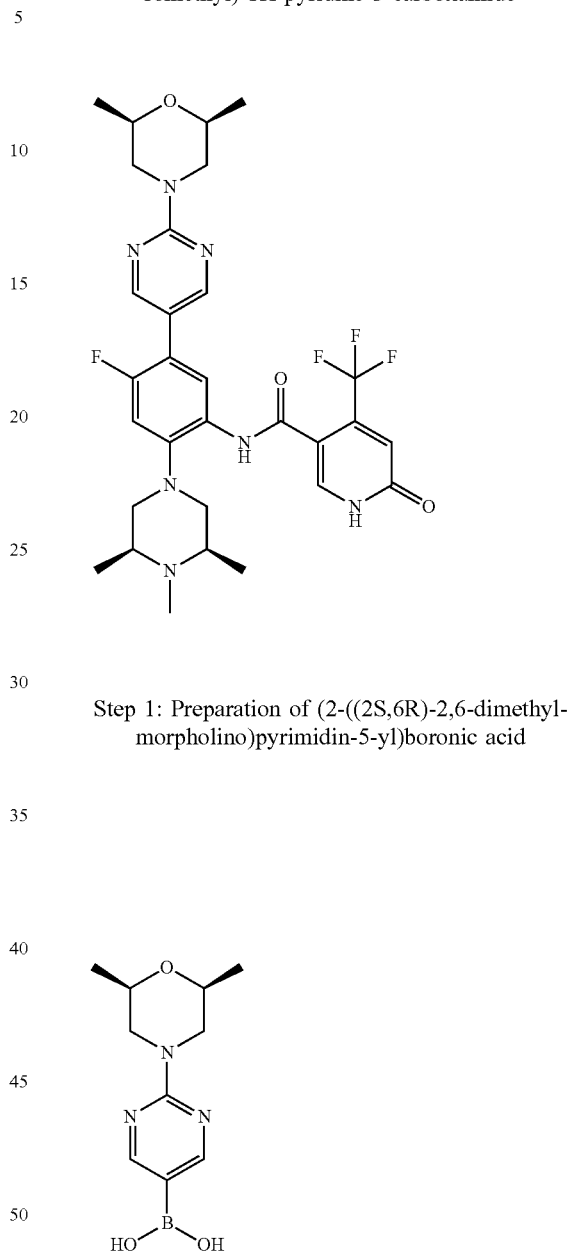

Step 1: Preparation of (2-((2S,6R)-2,6-dimethylmorpholino)pyrimidin-5-yl)boronic acid The title compound (beige solid, 41.5 mg, 74%) was prepared by a procedure similar to Example 34 using 3,5-difluorobenzoic acid (32 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.23 (s, 1H), 8.61 (d, J=8.1 Hz, 1H), 8.57 (d, J=1.0 Hz, 2H), 7.46-7.40 (m, 2H), 7.08-7.00 (m, 2H), 3.92-3.85 (m, 4H), 3.83-3.78 (m, 4H), 2.89 (br d, J=11.0 Hz, 2H), 2.70 (t, J=10.9 Hz, 2H), 2.46-2.40 (m, 2H), 2.38 (s, 3H), 1.17 (d, J=6.2 Hz, 6H); LCMS [M+H]$^+$ 541.4.

To a mixture of 2-chloropyrimidine-5-boronic acid (1.584 g, 10 mmol) and cis-2,6-dimethylmorpholine (1.29 mL, 10.5 mmol) in EtOH (5 mL) was added triethylamine (1.54 mL, 11 mmol). The resulting suspension was stirred at 60° C. for 1 h. Solvents were removed and the residue oil solidified to a crystalline pale yellow solid. It was triturated with H$_2$O (20 mL), suction filtered, rinsed with H$_2$O (20 mL), air dried and dried under vacuum to give the title compound as a pale yellow solid (827 mg, 35%). LCMS [M+H]$^+$ 238.14.

313

Step 2: Preparation of N-(5-(2-((2S,6R)-2,6-dimethylmorpholino)pyrimidin-5-yl)-4-fluoro-2-((3S,5R)-3,4,5-trimethylpiperazin-1-yl)phenyl)-6-oxo-4-(trifluoromethyl)-1,6-dihydropyridine-3-carboxamide

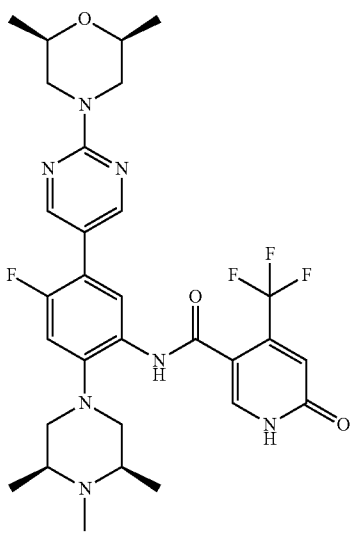

The title compound (brown solid, 39.1 mg, 60%) was prepared by a procedure similar to Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and (2-((2S,6R)-2,6-dimethylmorpholino)pyrimidin-5-yl)boronic acid (47 mg, 0.2 mmol). $^1$H NMR (500 MHz, METHANOL-d4) δ=8.54 (s, 2H), 7.98 (s, 1H), 7.90 (d, J=8.2 Hz, 1H), 7.09 (d, J=12.0 Hz, 1H), 6.93 (s, 1H), 4.64 (dd, J=1.3, 13.1 Hz, 2H), 3.67 (ddd, J=2.3, 6.3, 10.5 Hz, 2H), 3.07 (br d, J=11.0 Hz, 2H), 2.66-2.55 (m, 6H), 2.40 (s, 3H), 1.25 (d, J=6.1 Hz, 6H), 1.18 (d, J=6.2 Hz, 6H); LCMS [M+H]$^+$ 618.4.

314

Example 162: N-[4-fluoro-2-[(3R,5S)-3,4,5-trimethylpiperazin-1-yl]-5-[1-(1,3-thiazol-2-ylmethyl)-3,6-dihydro-2H-pyridin-4-yl]phenyl]-6-oxo-4-(trifluoromethyl)-1H-pyridine-3-carboxamide

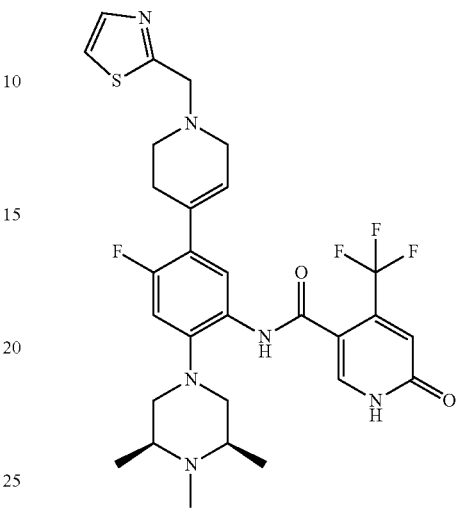

The procedure was similar to Example 148 using thiazole-2-carbaldehyde and N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide to give the title compound in 81% yield. $^1$H NMR (500 MHz, METHANOL-d4) δ=7.97-7.91 (m, 1H), 7.83-7.73 (m, 2H), 7.62-7.57 (m, 1H), 6.99-6.90 (m, 2H), 6.06-5.97 (m, 1H), 4.07-4.02 (m, 2H), 3.37-3.34 (m, 2H), 3.07-2.99 (m, 2H), 2.88-2.81 (m, 2H), 2.63-2.53 (m, 6H), 2.39 (s, 3H), 1.19-1.14 (m, 6H); LCMS [M+H]+ 605.4

Example 163: N-[4-fluoro-5-[1-[(2-methyl-1,3-oxazol-5-yl)methyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

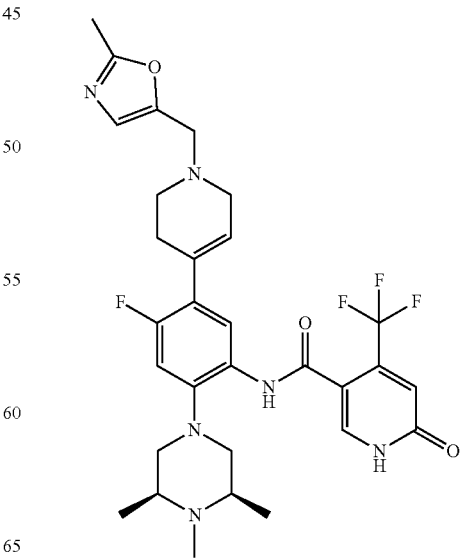

The procedure was similar to Example 148 using 2-methyloxazole-5-carbaldehyde and N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide to give the title compound in 35% yield. $^1$H NMR (500 MHz, METHANOL-d4) δ=7.96-7.91 (m, 1H), 7.82-7.74 (m, 1H), 6.99-6.97 (m, 1H), 6.96-6.93 (m, 1H), 6.93-6.91 (m, 1H), 6.05-5.99 (m, 1H), 3.80-3.75 (m, 2H), 3.28-3.21 (m, 2H), 3.06-2.99 (m, 2H), 2.81 (t, J=5.7 Hz, 2H), 2.62-2.53 (m, 6H), 2.49-2.45 (m, 3H), 2.41-2.38 (m, 3H), 1.19-1.16 (m, 6H); LCMS [M+H]+ 603.5

Example 164: N-[4-fluoro-5-[1-[(I-methylpyrazol-4-yl)methyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

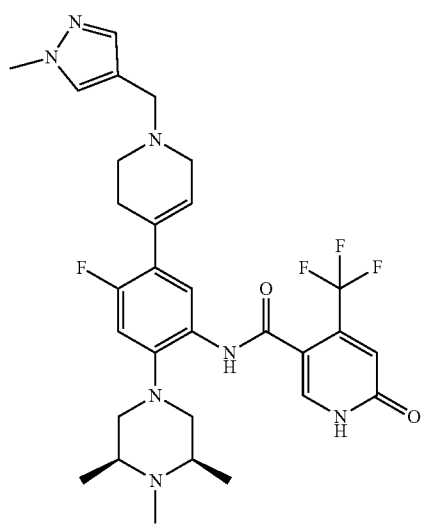 [SMILES: C[C@@H]1CN(c2cc(F)c(C3=CCN(Cc4cnn(C)c4)CC3)cc2NC(=O)c2c[nH]c(=O)cc2C(F)(F)F)C[C@H](C)N1C]

The procedure was similar to Example 148 using 1-methyl-1H-pyrazole-4-carbaldehyde and N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide to give the title compound in 68% yield. $^1$H NMR (500 MHz, METHANOL-d4) δ=7.94 (s, 1H), 7.77 (br d, J=8.1 Hz, 1H), 7.62 (s, 1H), 7.50 (s, 1H), 6.96-6.92 (m, 1H), 6.91 (s, 1H), 6.02 (br s, 1H), 3.90 (s, 3H), 3.64 (s, 2H), 3.26-3.20 (m, 2H), 3.05-2.98 (m, 2H), 2.83-2.76 (m, 2H), 2.62-2.50 (m, 6H), 2.37 (s, 3H), 1.16 (d, J=6.0 Hz, 6H); LCMS [M+H]+ 602.5.

Example 165: N-[4-fluoro-5-[1-[(4-morpholin-4-ylphenyl)methyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

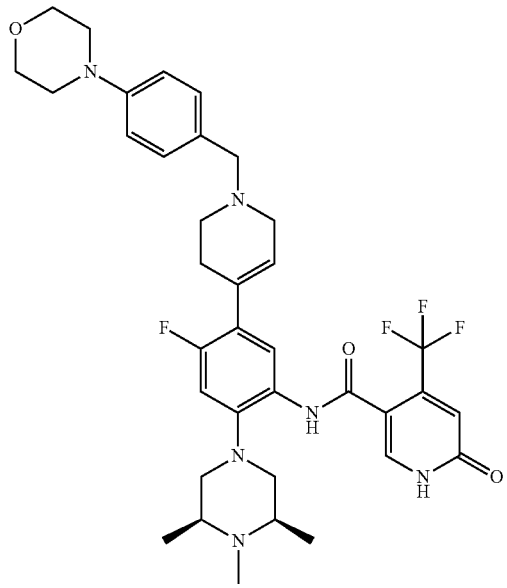 [SMILES: C[C@@H]1CN(c2cc(F)c(C3=CCN(Cc4ccc(N5CCOCC5)cc4)CC3)cc2NC(=O)c2c[nH]c(=O)cc2C(F)(F)F)C[C@H](C)N1C]

The procedure was similar to Example 148 using 4-morpholinobenzaldehyde and N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide to give the title compound in 45% yield. $^1$H NMR (500 MHz, METHANOL-d4) δ=7.98-7.91 (m, 1H), 7.83-7.74 (m, 1H), 7.35-7.26 (m, 2H), 7.01-6.97 (m, 2H), 6.96-6.92 (m, 1H), 6.91-6.89 (m, 1H), 6.11-5.92 (m, 1H), 3.87-3.83 (m, 4H), 3.69-3.63 (m, 2H), 3.27-3.21 (m, 2H), 3.19-3.15 (m, 4H), 3.05-2.98 (m, 2H), 2.83-2.76 (m, 2H), 2.62-2.50 (m, 6H), 2.39-2.36 (m, 3H), 1.18-1.14 (m, 6H); LCMS [M+H]+ 683.5

317

Example 166: N-[4-fluoro-5-[1-[[4-(4-methylpiperazin-1-yl)phenyl]methyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

318

Example 167: N-[4-fluoro-5-[1-(oxan-4-ylmethyl)-3,6-dihydro-2H-pyridin-4-yl]-2-[(3R,5S)-3,4,5-trimethylpiperazin-1-yl]phenyl]-6-oxo-4-(trifluoromethyl)-JH-pyridine-3-carboxamide

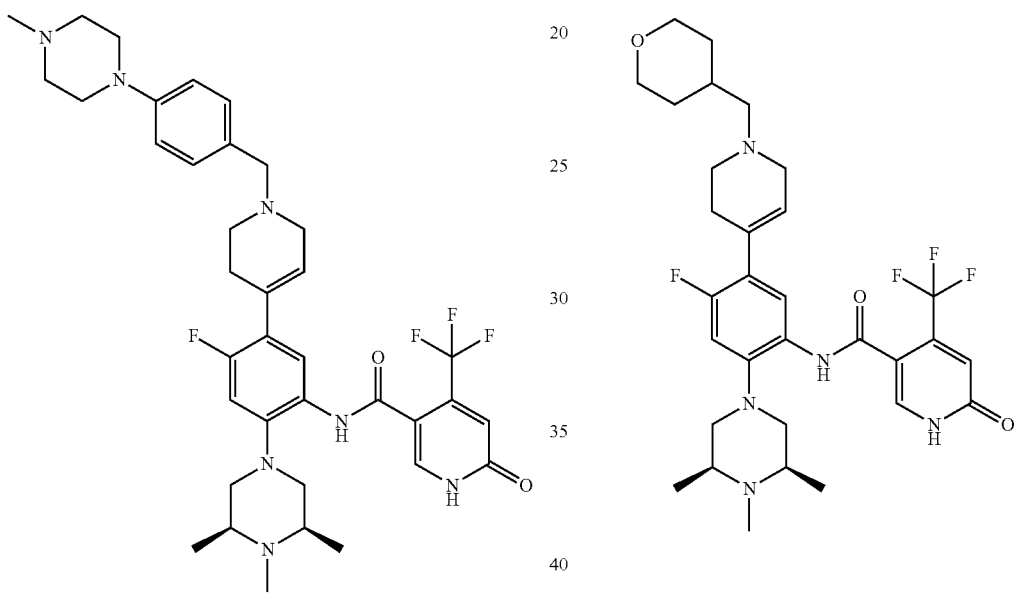

The procedure was similar to Example 148 using 4-(4-methylpiperazin-1-yl)benzaldehyde and N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide to give the title compound in 22% yield. $^1$H NMR (500 MHz, METHANOL-d4) δ=8.01-7.89 (m, 1H), 7.82-7.72 (m, 1H), 7.34-7.27 (m, 2H), 7.02-6.98 (m, 2H), 6.96-6.92 (m, 1H), 6.92-6.88 (m, 1H), 6.07-5.94 (m, 1H), 3.73-3.66 (m, 2H), 3.28-3.22 (m, 6H), 3.06-2.98 (m, 2H), 2.85-2.78 (m, 2H), 2.70-2.65 (m, 4H), 2.62-2.50 (m, 6H), 2.38 (d, J=8.9 Hz, 6H), 1.18-1.14 (m, 6H); LCMS [M+H]+ 696.5

The procedure was similar to Example 148 using tetrahydro-2H-pyran-4-carbaldehyde and N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide to give the title compound in 88% yield. $^1$H NMR (500 MHz, METHANOL-d4) δ=7.98-7.90 (m, 1H), 7.85-7.74 (m, 1H), 6.98-6.93 (m, 1H), 6.93-6.89 (m, 1H), 6.08-5.95 (m, 1H), 4.00-3.93 (m, 2H), 3.51-3.43 (m, 2H), 3.28-3.22 (m, 2H), 3.07-2.98 (m, 2H), 2.84-2.77 (m, 2H), 2.65-2.52 (m, 6H), 2.46-2.42 (m, 2H), 2.40-2.36 (m, 3H), 2.02-1.90 (m, 1H), 1.79-1.73 (m, 2H), 1.34-1.30 (m, 2H), 1.18-1.15 (m, 6H); LCMS [M+H]+ 606.5.

Example 168: 3,5-dichloro-N-[4-fluoro-5-(2-morpholin-4-ylpyrimidin-5-yl)-2-[(3R)-3-(dimethylamino)pyrrolidin-1-yl]phenyl]benzamide

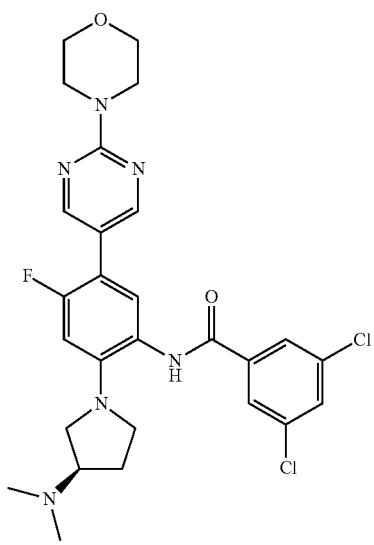 [SMILES: CN(C)[C@@H]1CCN(c2cc(F)c(-c3cnc(N4CCOCC4)nc3)cc2NC(=O)c2cc(Cl)cc(Cl)c2)C1]

Step 1: Preparation of (R)-1-(4-bromo-5-fluoro-2-nitrophenyl)-N,N-dimethylpyrrolidin-3-amine

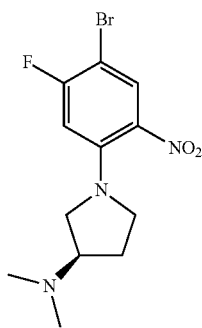 [SMILES: CN(C)[C@@H]1CCN(c2cc(F)c(Br)cc2[N+](=O)[O-])C1]

A solution of 1-bromo-2,4-difluoro-5-nitrobenzene (2.7 mL, 21 mmol) in toluene (5 mL) was added dropwise to a rapidly stirring mixture of (3R)-(+)-3-(dimethylamino)pyrrolidine (2.4 g, 21 mmol) and potassium carbonate (1.4 g, 10 mmol) in toluene (50 mL) at room temperature. After stirring for 20 minutes the reaction was warmed to 45° C. for 30 minutes. After the reaction was cooled to room temperature the reaction mixture was partitioned between water (100 mL) and ethyl acetate (100 mL). The layers were separated and the aqueous layer was extracted with additional ethyl acetate. The combined organic extracts were dried over magnesium sulfate and after removal of the inorganics by filtration the filtrate was concentrated onto celite. Purification by flash chromatography [1-10% MeOH/DCM+0.5% NH$_4$OH] afforded (R)-1-(4-bromo-5-fluoro-2-nitrophenyl)-N,N-dimethylpyrrolidin-3-amine (6.4 g, 91%). LCMS [M+H]+: 332.1.

Step 2: Preparation of (R)-1-(5-fluoro-4-(2-morpholinopyrimidin-5-yl)-2-nitrophenyl)-N,N-dimethylpyrrolidin-3-amine

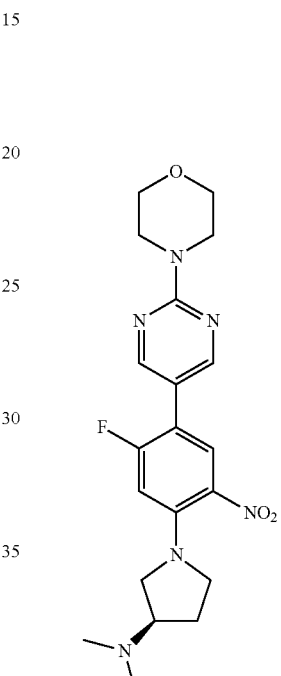

A vial was charged with (R)-1-(4-bromo-5-fluoro-2-nitrophenyl)-N,N-dimethylpyrrolidin-3-amine (0.50 g, 1.50 mmol), 2-(4-morpholino)pyrimidine-5-boronic acid pinacol ester (0.48 g, 1.66 mmol) and tetrakis(triphenylphosphine)palladium(0) (0.17 g, 0.15 mmol). The vial was sealed with a septum, evacuated and backfilled with nitrogen. 1,4-Dioxane (12 mL) and 2 M aqueous sodium carbonate (4 mL) were added via syringe and the vial was evacuated and backfilled an additional time. The reaction was heated to 85° C. for 3 h. After cooling to room temperature the reaction mixture was concentrated onto celite and flash chromatography [0.5-10% MeOH/DCM+0.5% NH$_4$OH] afforded (R)-1-(5-fluoro-4-(2-morpholinopyrimidin-5-yl)-2-nitrophenyl)-N,N-dimethylpyrrolidin-3-amine (0.61 g, 97%). LCMS [M+H]+: 417.3.

Step 3: Preparation of (R)-1-(2-amino-5-fluoro-4-(2-morpholinopyrimidin-5-yl)phenyl)-N,N-dimethylpyrrolidin-3-amine

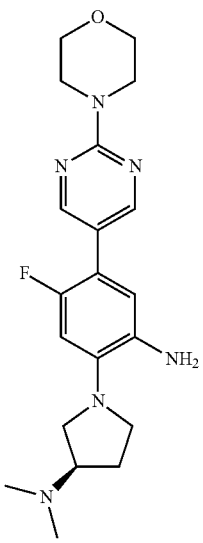 [SMILES: CN(C)[C@@H]1CCN(c2cc(F)c(-c3cnc(N4CCOCC4)nc3)cc2N)C1]

A mixture of (R)-1-(5-fluoro-4-(2-morpholinopyrimidin-5-yl)-2-nitrophenyl)-N,N-dimethylpyrrolidin-3-amine (0.61 g, 1.5 mmol) and tin(II) chloride (0.93 g, 4.9 mmol) in ethanol (12 mL) was heated to 75° C. for 1 h. The reaction mixture was concentrated onto celite and purification by flash chromatography [0.5-10% MeOH/DCM+0.5% NH$_4$OH] afforded (R)-1-(2-amino-5-fluoro-4-(2-morpholinopyrimidin-5-yl)phenyl)-N,N-dimethylpyrrolidin-3-amine (0.54 g, 90%). LCMS [M+H]+: 387.2.

Step 4: Preparation of (R)-3,5-dichloro-N-(2-(3-(dimethylamino)pyrrolidin-1-yl)-4-fluoro-5-(2-morpholinopyrimidin-5-yl)phenyl)benzamide

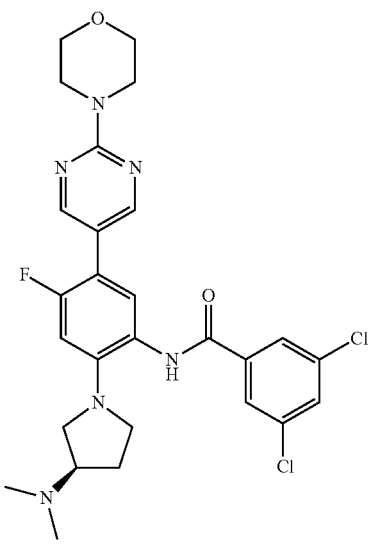 [SMILES: CN(C)[C@@H]1CCN(c2cc(F)c(-c3cnc(N4CCOCC4)nc3)cc2NC(=O)c2cc(Cl)cc(Cl)c2)C1]

To a solution of 3,5-dichlorobenzoic acid (0.025 g, 0.13 mmol) in DCM (1 mL) was added propylphosphonic anhydride (50% solution) (0.08 mL, 0.13 mmol) and triethylamine (0.03 mL, 0.19 mmol). After mixing the clear solution was transferred by pipette to a suspension of (R)-1-(2-amino-5-fluoro-4-(2-morpholinopyrimidin-5-yl)phenyl)-N,N-dimethylpyrrolidin-3-amine (0.025 g, 0.07 mmol) in DCM (1 mL) at room temperature. After stirring for 18 h at room temperature the reaction was concentrated onto celite and purified by flash chromatography [0.5-10% MeOH/DCM+0.5% NH$_4$OH] to afford the title compound (R)-3,5-dichloro-N-(2-(3-(dimethylamino)pyrrolidin-1-yl)-4-fluoro-5-(2-morpholinopyrimidin-5-yl)phenyl)benzamide (0.021 g, 55%). $^1$H NMR (500 MHz, DMSO-d6) δ=10.17 (s, 1H), 8.52 (s, 2H), 7.99 (d, J=1.8 Hz, 2H), 7.89 (t, J=1.8 Hz, 1H), 7.31 (d, J=8.8 Hz, 1H), 6.67 (d, J=14.1 Hz, 1H), 3.75-3.72 (m, 4H), 3.70-3.66 (m, 4H), 3.44-3.40 (m, 1H), 3.19 (t, J=8.7 Hz, 1H), 2.65-2.61 (m, 1H), 2.13-2.05 (m, 7H), 1.71-1.62 (m, 1H); LCMS [M+H]+: 559.3.

Example 169: 3,5-dichloro-N-[4-fluoro-5-(4-morpholin-4-ylphenyl)-2-[(3R)-3-(dimethylamino)pyrrolidin-1-yl]phenyl]benzamide

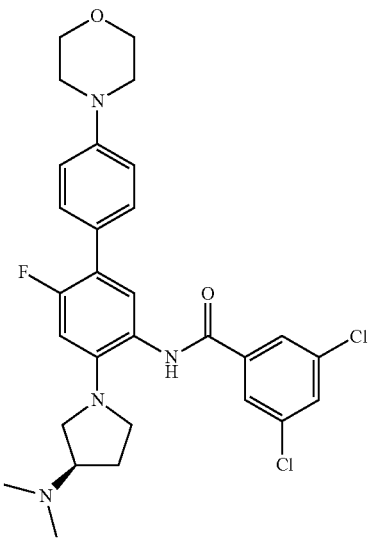 [SMILES: CN(C)[C@@H]1CCN(c2cc(F)c(-c3ccc(N4CCOCC4)cc3)cc2NC(=O)c2cc(Cl)cc(Cl)c2)C1]

The title compound was prepared similar to the sequence described above for the preparation of Example 168 using 4-(morpholino)phenylboronic acid in place of 2-(4-morpholino)pyrimidine-5-boronic acid pinacol ester in Step 2. $^1$H NMR (500 MHz, DMSO-d6) δ=10.13 (s, 1H), 7.99 (s, 2H), 7.89 (s, 1H), 7.37 (br d, J=8.3 Hz, 2H), 7.23 (d, J=8.8 Hz, 1H), 7.00 (d, J=8.8 Hz, 2H), 6.81 (br s, 1H), 6.68-6.56 (m, 2H), 3.78-3.73 (m, 4H), 3.41-3.39 (m, 2H), 3.19 (br t, J=8.9 Hz, 1H), 3.16-3.12 (m, 4H), 2.13-2.05 (m, 9H), 1.72-1.62 (m, 1H); LCMS [M+H]+: 557.3.

Example 170: N-[5-(5-cyano-6-morpholin-4-ylpyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

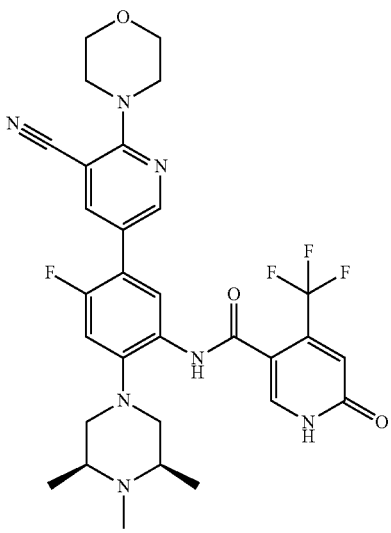 [SMILES: C[C@@H]1CN(c2cc(F)c(-c3cnc(N4CCOCC4)c(C#N)c3)cc2NC(=O)c2c[nH]c(=O)cc2C(F)(F)F)C[C@H](C)N1C]

The title compound was prepared according a procedure similar to Example 31 using 3-cyano-2-morpholinopyridine-5-boronic acid, pinacol ester. ¹H NMR (500 MHz, MeOD) δ 8.57 (s, 1H), 8.15 (d, J=2.2 Hz, 1H), 7.96 (s, 1H), 7.91 (d, J=8.3 Hz, 1H), 7.09 (d, J=12.2 Hz, 1H), 6.91 (s, 1H), 3.85-3.82 (m, 4H), 3.76-3.73 (m, 4H), 3.07 (d, J=11.2 Hz, 2H), 2.62 (t, J=11.1 Hz, 2H), 2.55 (dt, J=6.4, 4.2 Hz, 2H), 2.37 (s, 3H), 1.16 (d, J=6.1 Hz, 6H); LCMS [M+1]+=614.39.

Example 171: N-[4-fluoro-5-(5-methyl-6-morpholin-4-ylpyridin-3-yl)-2-[(3R,5S)-3,4,5-trimethylpiperazin-1-yl]phenyl]-6-oxo-4-(trifluoromethyl)-1H-pyridine-3-carboxamide

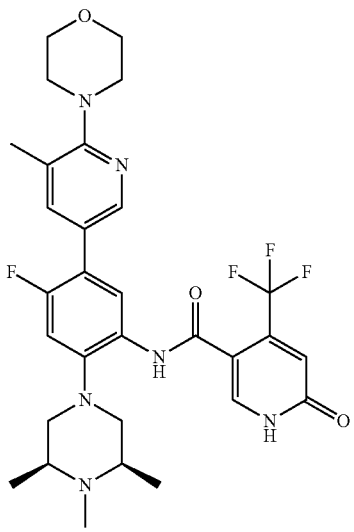

The title compound was prepared using a procedure similar to Example 31 using 4-(3-methyl-5-(4,4,5,5-tetramethyl-1,3,2-dioxaborolan-2-yl)pyridin-2-yl)morpholine. ¹H NMR (500 MHz, MeOD) δ 8.27 (s, 1H), 7.96 (s, 1H), 7.91 (d, J=8.2 Hz, 1H), 7.74 (s, 1H), 7.07 (d, J=12.1 Hz, 1H), 6.91 (s, 1H), 3.87-3.84 (m, 4H), 3.20-3.17 (m, 4H), 3.07 (d, J=11.2 Hz, 2H), 2.62 (t, J=11.1 Hz, 2H), 2.55 (ddd, J=10.4, 6.2, 3.1 Hz, 2H), 2.37 (s, 6H), 1.16 (d, J=6.1 Hz, 6H); ¹⁹F NMR (471 MHz, MeOD) δ -63.78, -120.54; LCMS HSS [M+1]+=603.26.

Example 172: N-[5-(2,3-dihydro-1H-pyrrolo[2,3-b]pyridin-5-yl)-4-fluoro-2-[(3R,5S)-3,4,5-trimethylpiperazin-1-yl]phenyl]-6-oxo-4-(trifluoromethyl)-1H-pyridine-3-carboxamide

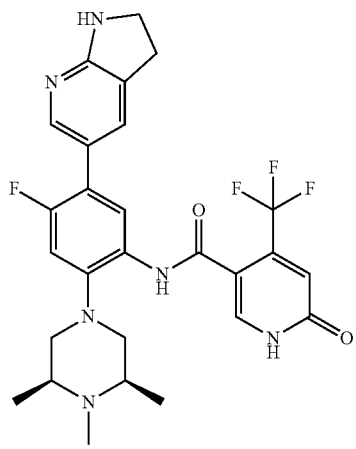 [SMILES: C[C@@H]1CN(c2cc(F)c(-c3cnc4c(c3)CCN4)cc2NC(=O)c2c[nH]c(=O)cc2C(F)(F)F)C[C@H](C)N1C]

The title compound was prepared by a procedure similar to Example 31 using 2,3-dihydropyrrolo[2,3-b]pyridine-5-boronic acid, pinacol ester. ¹H NMR (500 MHz, MeOD) δ 7.95 (s, 1H), 7.85 (d, J=8.3 Hz, 1H), 7.83 (s, 1H), 7.50 (s, 1H), 7.03 (d, J=12.1 Hz, 1H), 6.90 (s, 1H), 3.65 (t, J=8.5 Hz, 2H), 3.12 (t, J=8.4 Hz, 2H), 3.04 (d, J=10.9 Hz, 2H), 2.60 (t, J=11.1 Hz, 2H), 2.54 (ddd, J=9.8, 7.5, 2.5 Hz, 2H), 2.37 (s, 3H), 1.16 (d, J=6.1 Hz, 6H); ¹⁹F NMR (471 MHz, MeOD) δ -63.78 (s), -120.60 (s); LCMS HSS [M+1]+=545.33.

Example 173: N-[4-fluoro-2-[(3R 5S)-3,4,5-trimeth-ylpiperazin-1-yl]-5-[5-(trifluoromethyl)pyridin-3-yl]phenyl]-6-oxo-4-(trifluoromethyl)-1H-pyridine-3-carboxamide

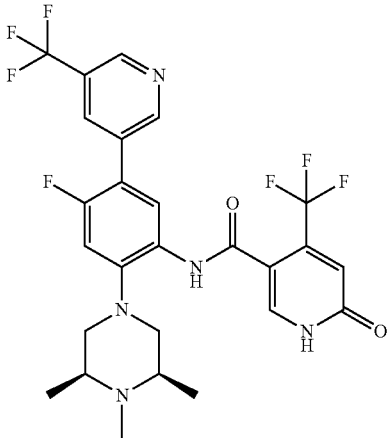

The procedure followed was similar to that used in Example 39 to give, after deprotection of the silyloxy intermediate, the title compound in 91% yield. $^1$H NMR (500 MHz, METHANOL-d4) δ=9.07-9.00 (m, 1H), 8.94-8.86 (m, 1H), 8.37-8.32 (m, 1H), 8.03-7.96 (m, 2H), 7.20-7.12 (m, 1H), 6.97-6.91 (m, 1H), 3.17-3.11 (m, 2H), 2.70-2.63 (m, 2H), 2.62-2.54 (m, 2H), 2.42-2.37 (m, 3H), 1.22-1.16 (m, 6H); LCMS [M+H]+ 572.5.

Example 174: N-[5-[5-(tert-butylcarbamoyl)pyridin-3-yl]-4-fluoro-2-[(3R,5S)-3,4,5-trimethylpiperazin-1-yl]phenyl]-6-oxo-4-(triluoromethyl)-1H-pyridine-3-carboxamide

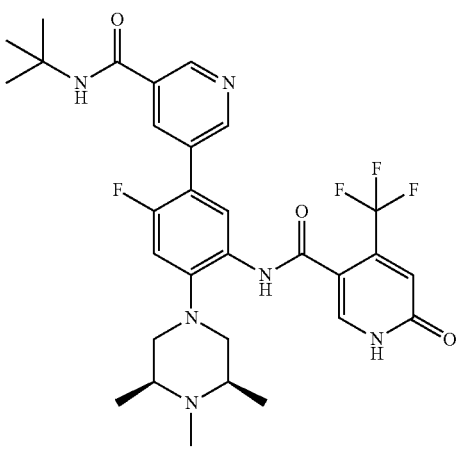 [SMILES: C[C@@H]1CN(c2cc(F)c(-c3cncc(C(=O)NC(C)(C)C)c3)cc2NC(=O)c2c[nH]c(=O)cc2C(F)(F)F)C[C@H](C)N1C]

The procedure followed was similar to that used in Example 39 to give, after deprotection of the silyloxy intermediate, the title compound in 84% yield. $^1$H NMR (500 MHz, METHANOL-d4) δ=8.90-8.81 (m, 2H), 8.35-8.30 (m, 1H), 8.04-7.93 (m, 2H), 7.18-7.08 (m, 2H), 6.96-6.87 (m, 1H), 3.16-3.05 (m, 2H), 2.70-2.61 (m, 2H), 2.61-2.52 (m, 2H), 2.41-2.35 (m, 3H), 1.51-1.47 (m, 9H), 1.21-1.15 (m, 6H); LCMS [M+H]+ 603.7

Example 175: 3-chloro-N-[4-fluoro-5-(2-morpholin-4-ylpyrimidin-5-yl)-2-[(3R,5S)-3,4,5-trimethylpiperazin-1-yl]phenyl]-5-(trifluoromethyl)benzamide

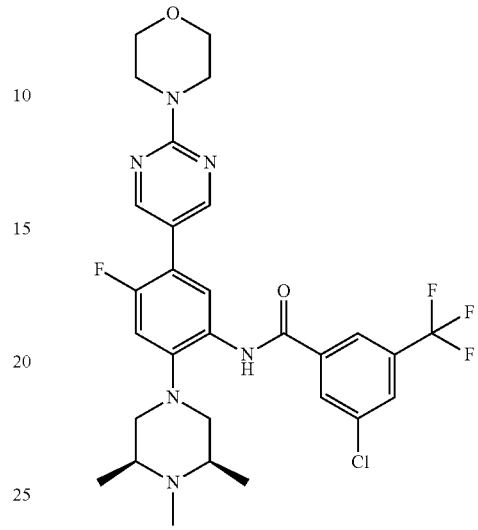

The title compound (beige solid, 36.8 mg, 59%) was prepared using a procedure similar that of Example 34 using 3-chloro-5-(trifluoromethyl)benzoic acid (45 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.45 (s, 1H), 8.65 (d, J=8.2 Hz, 1H), 8.60 (d, J=0.7 Hz, 2H), 8.17 (s, 1H), 8.03 (s, 1H), 7.85 (s, 1H), 7.06 (d, J=11.1 Hz, 1H), 3.94-3.86 (m, 4H), 3.86-3.79 (m, 4H), 2.92 (br d, J=11.1 Hz, 2H), 2.74 (br t, J=10.9 Hz, 2H), 2.52-2.42 (m, 2H), 2.39 (s, 3H), 1.20 (d, J=6.2 Hz, 6H); LCMS [M+H]$^+$ 607.3.

Example 176: 3-fluoro-N-[4-fluoro-5-(2-morpholin-4-ylpyrimidin-5-yl)-2-[(3R,5S)-3,4,5-trimethylpiperazin-1-yl]phenyl]-5-(trifluoromethyl)benzamide

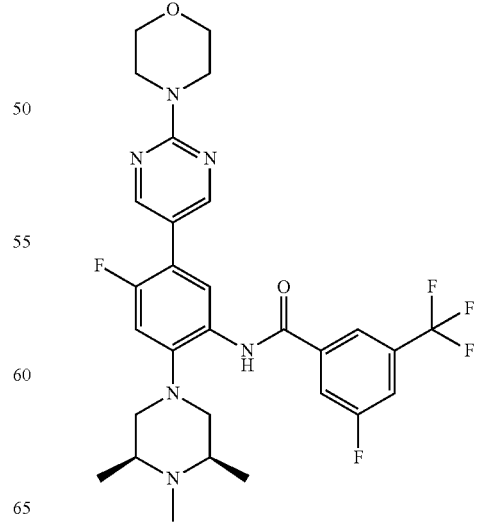

The title compound (beige solid, 38.4 mg, 63%) was prepared by a procedure similar to Example 34 using 3-fluoro-5-trifluoromethylbenzoic acid (42 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.44 (s, 1H), 8.66-8.63 (m, 1H), 8.58 (d, J=1.5 Hz, 2H), 7.94-7.88 (m, 2H), 7.56 (br d, J=7.7 Hz, 1H), 7.04 (d, J=11.1 Hz, 1H), 3.91-3.86 (m, 4H), 3.82-3.78 (m, 4H), 2.90 (br d, J=11.0 Hz, 2H), 2.72 (t, J=11.0 Hz, 2H), 2.47-2.40 (m, 2H), 2.37 (s, 3H), 1.18 (d, J=6.1 Hz, 6H); LCMS [M+H]$^+$ 591.4.

Example 177: N-[4-fluoro-5-(4-morpholin-4-ylphenyl)-2-[(3R)-3-(dimethylamino)pyrrolidin-1-yl]phenyl]-1H-pyrazole-4-carboxamide

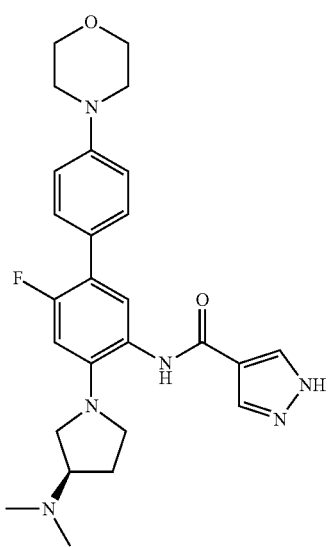 [SMILES: CN(C)[C@@H]1CCN(c2cc(F)c(-c3ccc(N4CCOCC4)cc3)cc2NC(=O)c2cn[nH]c2)C1]

The title compound was prepared similar to the sequence described above for the preparation of Example 168 using 1H-pyrazole-4-carboxylic acid in place of 3,5-dichlorobenzoic acid in Step 4. $^1$H NMR (500 MHz, DMSO-d6) δ=13.21 (br s, 1H), 9.47 (s, 1H), 8.38-8.25 (m, 1H), 8.15-7.97 (m, 1H), 7.36 (d, J=7.9 Hz, 2H), 7.17 (d, J=9.0 Hz, 1H), 7.00 (d, J=8.9 Hz, 2H), 6.81 (s, 1H), 6.66-6.59 (m, 2H), 3.78-3.73 (m, 4H), 3.23 (t, J=8.7 Hz, 1H), 3.16-3.12 (m, 4H), 2.63-2.59 (m, 1H), 2.12 (s, 3H), 2.11-2.02 (m, 7H), 1.73-1.61 (m, 1H), 1.57-1.46 (m, 1H); LCMS [M+H]+: 479.3.

Example 178: N-[4-fluoro-5-(5-methylpyridin-3-yl)-2-[(3R,5S)-3,4,5-trimethylpiperazin-1-yl]phenyl]-6-oxo-4-(trifluoromethyl)-1H-pyridine-3-carboxamide

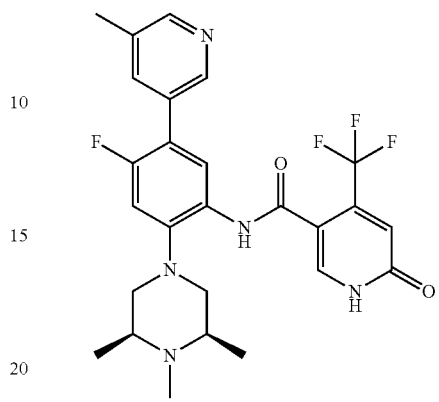

The procedure used was similar to Example 39 to give, after deprotection of the silyloxy intermediate, the title compound in 91% yield. $^1$H NMR (500 MHz, METHANOL-d4) δ=9.07-9.00 (m, 1H), 8.94-8.86 (m, 1H), 8.37-8.32 (m, 1H), 8.03-7.96 (m, 2H), 7.20-7.12 (m, 1H), 6.97-6.91 (m, 1H), 3.17-3.11 (m, 2H), 2.70-2.63 (m, 2H), 2.62-2.54 (m, 2H), 2.42-2.37 (m, 3H), 1.22-1.16 (m, 6H); LCMS [M+H]+ 572.5.

Example 179: N-[5-(5-carbamoylpyridin-3-yl)-4-fluoro-2-[(3R,5S)-3,4,5-trimethylpiperazin-1-yl]phenyl]-6-oxo-4-(trifluoromethyl)-H-pyridine-3-carboxamide

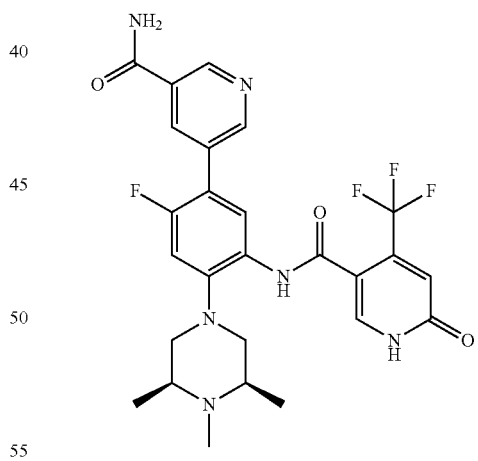

TFA (2 ml) was added to a solution of N-(5-(5-(tert-butylcarbamoyl)pyridin-3-yl)-4-fluoro-2-((3S,5R)-3,4,5-trimethylpiperazin-1-yl)phenyl)-4-(trifluoromethyl)-6-(2-(trimethylsilyl)ethoxy)nicotinamide (Example 174) in DCM (2 ml) at RT and the mixture was heated at 50° C. for 30 min. The reaction mixture was concentrated and heated with methylsulfonic acid (10 eq) in toluene at 100° C. Complete disappearance of the intermediate and formation of the desired product was observed after 30 min. The reaction mixture was concentrated to dryness, the residue was dissolved in MeOH and passed through a cation exchange resin cartridge (Isolute SCX-2 500 mg, 6 ml) to collect the title compound as a beige powder (6.5 mg, 27%). $^1$H NMR (500 MHz, METHANOL-d4) δ=8.95-8.88 (m, 1H), 8.83-8.74 (m, 1H), 8.38-8.32 (m, 1H), 7.93-7.83 (m, 2H), 7.09-7.01 (m, 1H), 6.86-6.79 (m, 1H), 3.10-2.99 (m, 2H), 2.66-2.54 (m, 4H), 2.42-2.30 (m, 3H), 1.15-1.07 (m, 6H); $^{19}$F NMR (471 MHz, METHANOL-d4) δ=−63.78 (s, 1F), −120.49 (s, 1F)

Example 180: N-[4-fluoro-2-[(3R,5S)-3,4,5-trimethylpiperazin-1-yl]-5-[5-(trifluoromethyl)pyridin-3-yl]phenyl]-1-methyl-6-oxo-4-(trifluoromethyl)pyridine-3-carboxamide

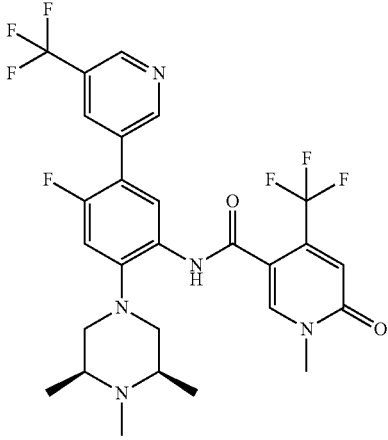 [SMILES: C[C@@H]1CN(c2cc(F)c(-c3cncc(C(F)(F)F)c3)cc2NC(=O)c2cn(C)c(=O)cc2C(F)(F)F)C[C@H](C)N1C]

Cesium carbonate (8.55 mg, 0.026 mmol) was added to a solution of N-(4-fluoro-5-(5-(trifluoromethyl)pyridin-3-yl)-2-((3S,5R)-3,4,5-trimethylpiperazin-1-yl)phenyl)-6-oxo-4-(trifluoromethyl)-1,6-dihydropyridine-3-carboxamide (Example 173, 15 mg, 0.026 mmol) and iodomethane (2.451 μl, 0.039 mmol) in DMF (1. ml) at RT. The reaction mixture was continuously stirred at RT. After 10 min, complete conversion was observed. One minor less polar peak with the same mass was observed. While not wishing to be limited by theory, it could be the O-methylated by-product. Mass (600) corresponding to the dimethyl substituted by-product was also observed in trace amounts. The mixture was diluted with DCM (4 ml) and washed with water (6 ml). The aqueous phase was extracted with DCM (2×5 ml) and the combined organic phase was washed with water, and brine, then dried with Na$_2$SO$_4$ and concentrated onto celite. Purification by flash column chromatography on Isco (4G) column, eluting with DCM containing 0-3% MeOH afforded the title compound as a white solid. (6 mg, 37% yield). $^1$H NMR (500 MHz, METHANOL-d4) δ=8.97-8.87 (m, 1H), 8.83-8.73 (m, 1H), 8.25-8.19 (m, 1H), 8.19-8.14 (m, 1H), 7.93-7.84 (m, 1H), 7.11-7.03 (m, 1H), 6.88-6.80 (m, 1H), 3.58-3.54 (m, 3H), 3.09-2.99 (m, 2H), 2.62-2.45 (m, 4H), 2.37-2.27 (m, 3H), 1.12-1.07 (m, 6H); LCMS [M+H]+ 586.4.

Example 181: N-[4-fluoro-5-(2-morpholin-4-ylpyrimidin-5-yl)-2-[(3R)-3,4-dimethylpiperazin-1-yl]phenyl]-4-methyl-1,3-thiazole-2-carboxamide

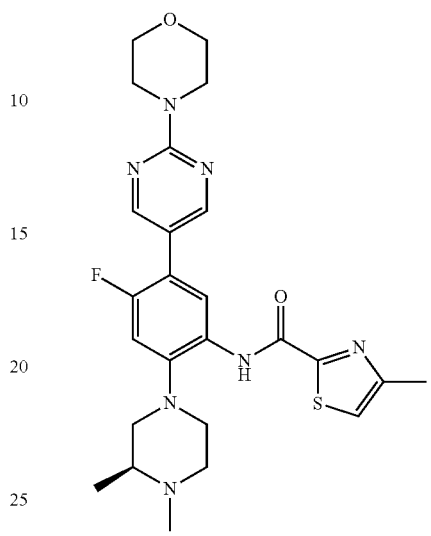

The title compound was prepared similar to the procedure described above for the preparation of Example 78 using 4-methylthiazole-2-carboxylic acid in place of 6-chloro-4-(trifluoromethyl)nicotinic acid. $^1$H NMR (500 MHz, DMSO-d6) δ=10.19 (s, 1H), 8.56 (s, 2H), 8.38 (d, J=8.3 Hz, 1H), 7.76 (s, 1H), 7.31 (d, J=11.7 Hz, 1H), 3.80-3.75 (m, 4H), 3.71-3.67 (m, 4H), 2.98-2.86 (m, 5H), 2.59 (br d, J=9.5 Hz, 3H), 2.28 (s, 3H), 1.04 (d, J=6.2 Hz, 3H); LCMS [M+H]+: 512.4.

Example 182: 2-[(dimethylamino)methyl]-N-[4-fluoro-5-(2-morpholin-4-ylpyrimidin-5-yl)-2-[(3R)-3,4-dimethylpiperazin-1-yl]phenyl]-1,3-thiazole-4-carboxamide

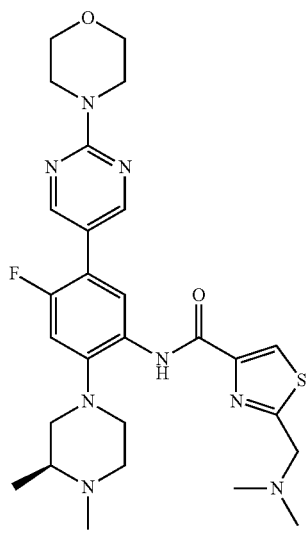 [SMILES: C[C@H]1CN(c2cc(F)c(-c3cnc(N4CCOCC4)nc3)cc2NC(=O)c2csc(CN(C)C)n2)CCN1C]

The title compound was prepared similar to the procedure described above for the preparation of Example 78 using 2-[(dimethylamino)methyl]-1,3-thiazole-4-carboxylic acid in place of 6-chloro-4-(trifluoromethyl)nicotinic acid. ¹H NMR (500 MHz, DMSO-d6) δ=10.24 (s, 1H), 8.56 (s, 2H), 8.49 (br d, J=8.2 Hz, 1H), 8.45 (s, 1H), 7.28 (br d, J=11.7 Hz, 1H), 3.90-3.81 (m, 2H), 3.77 (br d, J=4.2 Hz, 4H), 3.70 (br d, J=4.4 Hz, 4H), 2.94-2.86 (m, 4H), 2.34-2.28 (m, 8H), 1.02 (br d, J=6.0 Hz, 3H); LCMS [M+H]+: 555.4.

Example 183: 4-chloro-N-[4-fluoro-5-(2-morpholin-4-ylpyrimidin-5-yl)-2-[(3R)-3,4-dimethylpiperazin-1-yl]phenyl]-1H-pyrazole-3-carboxamide

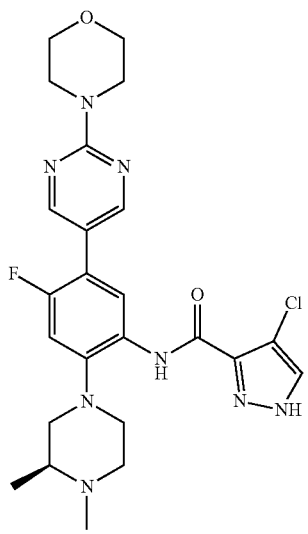 [SMILES: C[C@H]1CN(c2cc(F)c(-c3cnc(N4CCOCC4)nc3)cc2NC(=O)c2n[nH]cc2Cl)CCN1C]

The title compound was prepared similar to the procedure described above for the preparation of Example 78 using 4-chloro-1H-pyrazole-3-carboxylic acid in place of 3,5-dichlorobenzoic acid. ¹H NMR (500 MHz, DMSO-d6) δ=9.63 (s, 1H), 8.49 (d, J=1.0 Hz, 2H), 8.37 (d, J=8.4 Hz, 1H), 8.05 (br s, 1H), 7.18 (d, J=11.7 Hz, 1H), 3.71-3.68 (m, 4H), 3.63-3.60 (m, 4H), 2.89-2.75 (m, 4H), 2.40-2.34 (m, 2H), 2.28-2.23 (m, 1H), 2.19 (s, 3H), 0.94 (d, J=6.1 Hz, 3H); LCMS [M+H]+: 515.2.

Example 184: N-[4-fluoro-5-(2-morpholin-4-ylpyrimidin-5-yl)-2-[(3R)-3-(dimethylamino)pyrrolidin-1-yl]phenyl]-1-methyl-6-oxo-4-(trifluoromethyl)pyridine-3-carboxamide

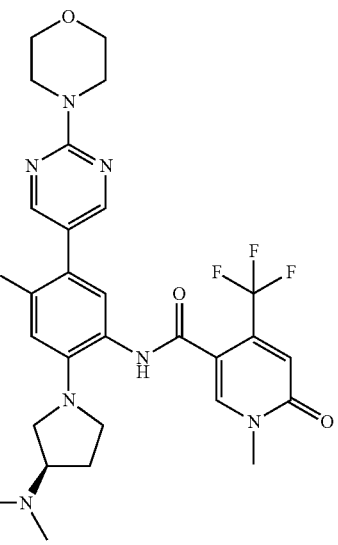

1-Methyl-6-oxo-4-(trifluoromethyl)-1,6-dihydropyridine-3-carboxylic acid (29 mg, 0.13 mmol) was activated with HATU (49 mg, 0.13 mmol) and N,N-diisopropylethylamine (0.023 mL, 0.13 mmol) in DMF (0.5 mL) at room temperature. This solution of activated acid was added to a stirring solution of (R)-1-(2-amino-5-fluoro-4-(2-morpholinopyrimidin-5-yl)phenyl)-N,N-dimethylpyrrolidin-3-amine (25 mg, 0.065 mmol) [Example 168, Step C] in DMF (1 mL) at room temperature. The reaction was warmed to 40° C. for 1 h and then to 55° C. for an additional 1 h. An additional portion of activated acid was prepared and added to the reaction mixture and the reaction was heated at 55° C. overnight. The reaction mixture was concentrated onto celite and purified by flash chromatography [1-10% MeOH/DCM+1% NH₄OH] followed by reverse phase chromatography [5-95% MeCN/water; C18 column] to afford (R)—N-(2-(3-(dimethylamino)pyrrolidin-1-yl)-4-fluoro-5-(2-morpholinopyrimidin-5-yl)phenyl)-1-methyl-6-oxo-4-(trifluoromethyl)-1,6-dihydropyridine-3-carboxamide (0.020 g, 52%). ¹H NMR (500 MHz, DMSO-d6) δ=13.95 (br. s., 1H), 9.29 (br. s., 1H), 8.59 (br. s., 1H), 8.55 (s, 2H), 7.82 (d, J=8.4 Hz, 1H), 7.14 (d, J=12.0 Hz, 1H), 3.78-3.75 (m, 4H), 3.70-3.67 (m, 4H), 3.01 (br. s., 2H), 2.88 (br. s, 2H), 2.23 (br. s., 3H), 1.00 (br. s, 3H); LCMS [M+H]+: 590.5.

Example 185: N-[4-fluoro-5-(2-morpholin-4-ylpyrimidin-5-yl)-2-[(3R)-3-(dimethylamino)pyrrolidin-1-yl]phenyl]-3-(trifluoromethyl)-1H-pyrazole-4-carboxamide

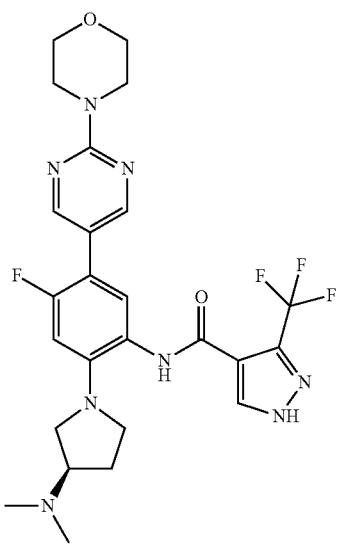 [SMILES: CN(C)[C@@H]1CCN(c2cc(F)c(-c3cnc(N4CCOCC4)nc3)cc2NC(=O)c2c[nH]nc2C(F)(F)F)C1]

The title compound was prepared similar to the procedure described above for the preparation of Example 184 using 3-(trifluoromethyl)pyrazole-4-carboxylic acid in place of 1-methyl-6-oxo-4-(trifluoromethyl)-1,6-dihydropyridine-3-carboxylic acid. $^1$H NMR (500 MHz, DMSO-d6) δ=9.60 (s, 1H), 8.46 (s, 1H), 8.44 (s, 2H), 7.17 (d, J=8.7 Hz, 1H), 6.60 (d, J=14.1 Hz, 1H), 3.68-3.64 (m, 4H), 3.62-3.59 (m, 4H), 3.30 (br dd, J=3.2, 6.7 Hz, 4H), 3.14 (t, J=8.8 Hz, 1H), 2.55-2.49 (m, 4H), 2.02 (s, 6H), 2.00-1.95 (m, 1H), 1.64-1.55 (m, 1H); LCMS [M+H]+: 549.4.

Example 186: N-[4-fluoro-5-(2-morpholin-4-ylpyrimidin-5-yl)-2-[(3R,5S)-3,4,5-trimethylpiperazin-1-yl]phenyl]-3-(trifluoromethyl)benzamide

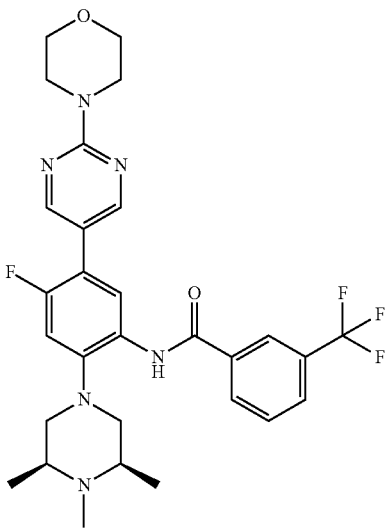 [SMILES: C[C@@H]1CN(c2cc(F)c(-c3cnc(N4CCOCC4)nc3)cc2NC(=O)c2cccc(C(F)(F)F)c2)C[C@H](C)N1C]

The title compound (beige solid, 51.0 mg, 87%) was prepared by a procedure similar to Example 34 using 3-(trifluoromethyl)benzoic acid (38 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.41 (s, 1H), 8.67 (d, J=8.2 Hz, 1H), 8.58 (d, J=1.2 Hz, 2H), 8.18 (d, J=7.8 Hz, 1H), 8.14 (s, 1H), 7.86 (d, J=7.8 Hz, 1H), 7.70 (t, J=7.8 Hz, 1H), 7.03 (d, J=11.2 Hz, 1H), 3.91-3.85 (m, 4H), 3.83-3.77 (m, 4H), 2.91 (br d, J=11.0 Hz, 2H), 2.71 (t, J=11.0 Hz, 2H), 2.49-2.40 (m, 2H), 2.37 (s, 3H), 1.17 (d, J=6.2 Hz, 6H); LCMS [M+H]$^+$ 573.3.

Example 187: N-[4-fluoro-5-(2-morpholin-4-ylpyrimidin-5-yl)-2-[(3R,5S)-3,4,5-trimethylpiperazin-1-yl]phenyl]-4-(trifluoromethyl)pyrimidine-5-carboxamide

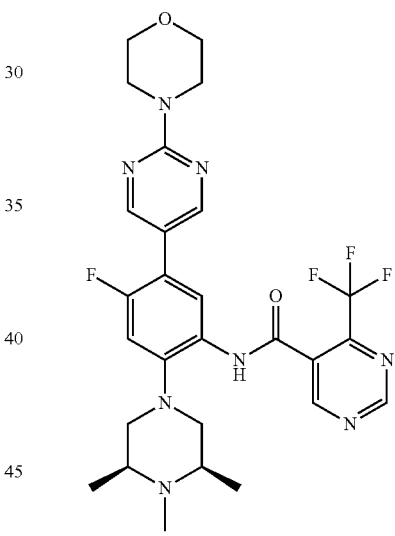

The title compound (beige solid, 39.0 mg, 65%) was prepared through a procedure similar to Example 34 using 4-trifluoromethyl-pyrimidine-5-carboxylic acid (38 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.50 (s, 1H), 9.15 (s, 1H), 8.83 (s, 1H), 8.61-8.54 (m, 3H), 7.06 (d, J=11.1 Hz, 1H), 3.90-3.85 (m, 4H), 3.83-3.78 (m, 4H), 2.81 (br d, J=10.9 Hz, 2H), 2.65 (br t, J=10.8 Hz, 2H), 2.33-2.21 (m, 5H), 1.12 (d, J=6.2 Hz, 6H); LCMS [M+H]$^+$ 575.4.

Example 188: N-[4-fluoro-5-(2-morpholin-4-ylpyrimidin-5-yl)-2-[(3R,5S)-3,4,5-trimethylpiperazin-1-yl]phenyl]-4-(trifluoromethyl)-1,3-thiazole-5-carboxamide

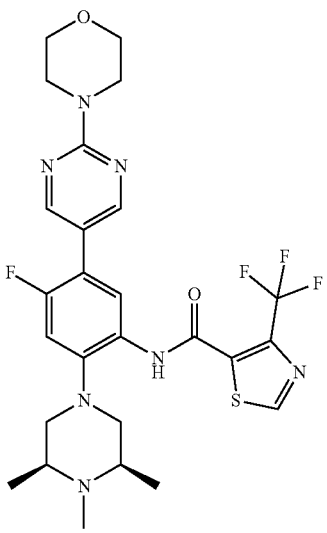 [SMILES: C[C@@H]1CN(c2cc(F)c(-c3cnc(N4CCOCC4)nc3)cc2NC(=O)c2scnc2C(F)(F)F)C[C@H](C)N1C]

The title compound (beige solid, 42.3 mg, 72%) was prepared by a procedure similar to Example 34 using 4-(trifluoromethyl)-1,3-thiazole-5-carboxylic acid (39 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFODR-d) δ=9.19 (br s, 1H), 8.94 (s, 1H), 8.60-8.54 (m, 3H), 7.07 (d, J=11.1 Hz, 1H), 3.92-3.84 (m, 4H), 3.83-3.77 (m, 4H), 2.82 (br d, J=10.8 Hz, 2H), 2.66 (br t, J=10.8 Hz, 2H), 2.43-2.30 (m, 5H), 1.14 (d, J=6.2 Hz, 6H); LCMS [M+H]$^+$ 580.3.

Example 189: 2-fluoro-N-[4-fluoro-5-(2-morpholin-4-ylpyrimidin-5-yl)-2-[(3R,5S)-3,4,5-trimethylpiperazin-1-yl]phenyl]-5-(trifluoromethyl)benzamide

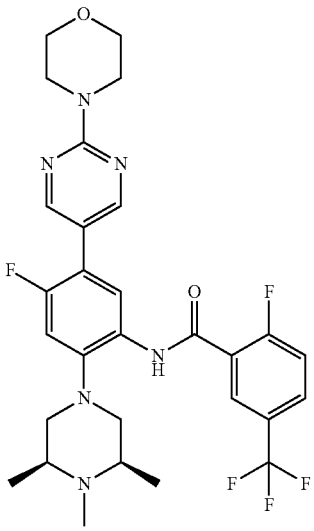 [SMILES: C[C@@H]1CN(c2cc(F)c(-c3cnc(N4CCOCC4)nc3)cc2NC(=O)c2cc(C(F)(F)F)ccc2F)C[C@H](C)N1C]

The title compound (pale beige solid, 53.6 mg, 89%) was prepared by a procedure similar to Example 34 using 2-fluoro-5-(trifluoromethyl)benzoic acid (42 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.84 (br d, J=12.7 Hz, 1H), 8.73 (d, J=8.3 Hz, 1H), 8.59 (d, J=1.1 Hz, 2H), 8.54 (dd, J=2.0, 6.9 Hz, 1H), 7.86-7.80 (m, 1H), 7.38 (dd, J=8.9, 10.9 Hz, 1H), 7.05 (d, J=11.2 Hz, 1H), 3.91-3.86 (m, 4H), 3.83-3.77 (m, 4H), 2.89 (br d, J=10.8 Hz, 2H), 2.67 (br t, J=10.8 Hz, 2H), 2.53-2.45 (m, 2H), 2.38 (s, 3H), 1.16 (d, J=6.1 Hz, 6H); LCMS [M+H]$^+$ 591.4.

Example 190: 3-fluoro-N-[4-fluoro-5-(2-morpholin-4-ylpyrimidin-5-yl)-2-[(3R,5S)-3,4,5-trimethylpiperazin-1-yl]phenyl]-5-methoxybenzamide

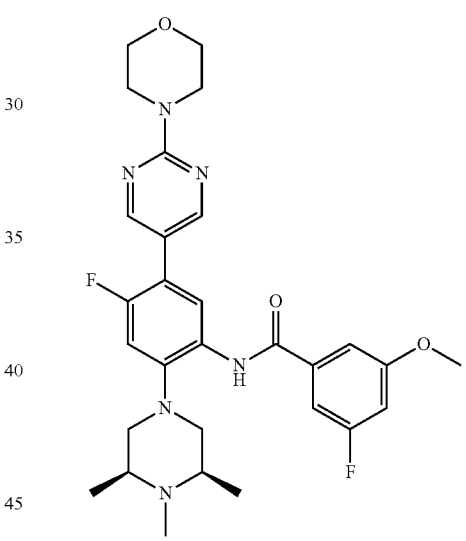

The title compound (beige solid, 48.4 mg, 87%) was prepared by a procedure similar to Example 34 using 3-fluoro-5-methoxybenzoic acid (34 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.20 (s, 1H), 8.63 (d, J=8.2 Hz, 1H), 8.57 (s, 2H), 7.28 (br s, 1H), 7.16 (br d, J=8.7 Hz, 1H), 7.01 (d, J=11.2 Hz, 1H), 6.83 (td, J=2.1, 10.1 Hz, 1H), 3.90 (s, 3H), 3.89-3.85 (m, 4H), 3.82-3.78 (m, 4H), 2.90 (br d, J=11.0 Hz, 2H), 2.68 (t, J=10.9 Hz, 2H), 2.49-2.39 (m, 2H), 2.37 (s, 3H), 1.16 (d, J=6.2 Hz, 6H); LCMS [M+H]$^+$ 553.4.

Example 191: 3,5-dichloro-N-[4-fluoro-5-(4-morpholin-4-ylphenyl)-2-[(3R,5S)-3,4,5-trimethylpiperazin-1-yl]phenyl]benzamide

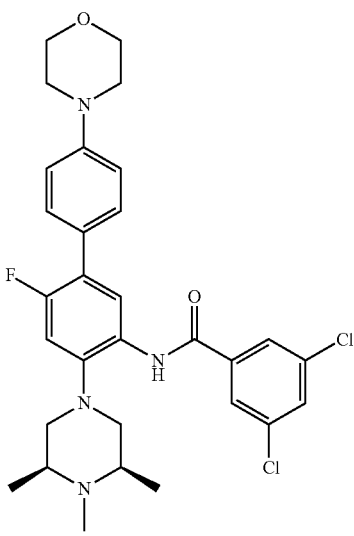 [SMILES: C[C@@H]1CN(c2cc(F)c(-c3ccc(N4CCOCC4)cc3)cc2NC(=O)c2cc(Cl)cc(Cl)c2)C[C@H](C)N1C]

The title compound (pale beige solid, 43.1 mg, 75%) was prepared by a procedure similar to Example 34 using 3,5-dichlorobenzoic acid (38 mg, 0.2 mmol) substituting 4-fluoro-5-(2-morpholinopyrimidin-5-yl)-2-((3S,5R)-3,4,5-trimethylpiperazin-1-yl)aniline as the aniline (40 mg, 0.1 mmol). $^1$H NMR (500 MHz, CHLOROFORM-d) δ=9.30 (s, 1H), 8.63 (d, J=8.3 Hz, 1H), 7.80 (d, J=1.7 Hz, 2H), 7.59-7.51 (m, 3H), 7.02-6.94 (m, 3H), 3.93-3.85 (m, 4H), 3.28-3.18 (m, 4H), 2.90 (br d, J=11.0 Hz, 2H), 2.71 (t, J=10.9 Hz, 2H), 2.52-2.41 (m, 2H), 2.38 (s, 3H), 1.18 (d, J=6.2 Hz, 6H); LCMS [M+H]$^+$ 571.3.

Example 192: N-[4-fluoro-5-(2-morpholin-4-ylpyrimidin-5-yl)-2-[(3R)-3,4-dimethylpiperazin-1-yl]phenyl]-1-methylpyrazole-3-carboxamide

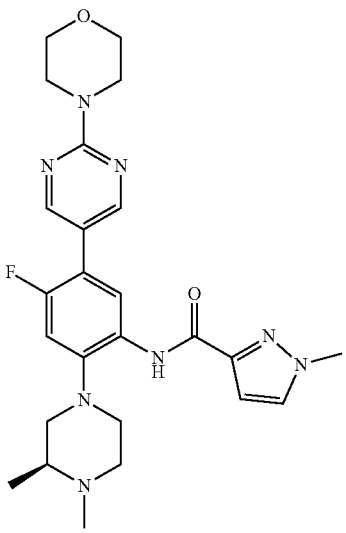

The title compound was prepared similar to the procedure described for the preparation of Example 78 using 1-methyl-1H-pyrazole-3-carboxylic acid as the acylating agent. $^1$H NMR (500 MHz, DMSO-d6) δ=9.75 (br s, 1H), 8.55 (br s, 2H), 8.47-8.41 (m, 1H), 7.90 (br s, 1H), 7.30-7.21 (m, 1H), 6.77 (br s, 1H), 3.97 (br s, 3H), 3.79-3.75 (m, 4H), 3.71-3.68 (m, 4H), 2.91 (br s, 5H), 2.29 (br s, 3H), 1.04 (br s, 3H); LCMS [M+H]+: 495.4.

Example 193: N-[4-fluoro-5-(2-morpholin-4-ylpyrimidin-5-yl)-2-[(3R)-3,4-dimethylpiperazin-1-yl]phenyl]-1H-pyrazole-3-carboxamide

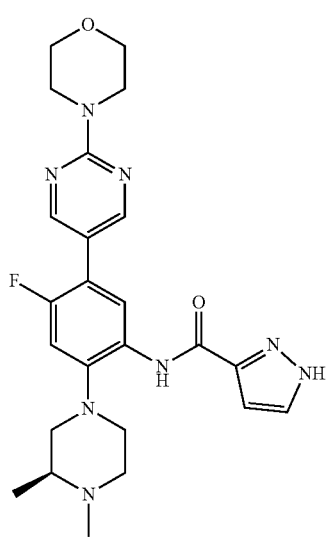 [SMILES: C[C@H]1CN(c2cc(F)c(-c3cnc(N4CCOCC4)nc3)cc2NC(=O)c2cc[nH]n2)CCN1C]

The title compound was prepared similar to the procedure described above for the preparation of Example 78 using 1H-pyrazole-3-carboxylic acid in place of 3-(trifluoromethyl)pyrazole-4-carboxylic acid. $^1$H NMR (500 MHz, DMSO-d6) δ=13.70-13.36 (m, 1H), 9.72 (br s, 1H), 8.56 (br s, 2H), 8.48 (br d, J=4.0 Hz, 1H), 7.93 (br s, 1H), 7.25 (br d, J=11.1 Hz, 1H), 6.80 (br s, 1H), 3.80-3.76 (m, 4H), 3.71-3.67 (m, 4H), 2.97-2.85 (m, 5H), 2.28 (br s, 3H), 1.03 (br s, 3H); LCMS [M+H]+: 481.4.

Example 194: N-[4-fluoro-5-(2-morpholin-4-ylpyrimidin-5-yl)-2-[(3R)-3,4-dimethylpiperazin-1-yl]phenyl]-2-methyl-1,3-thiazole-4-carboxamide

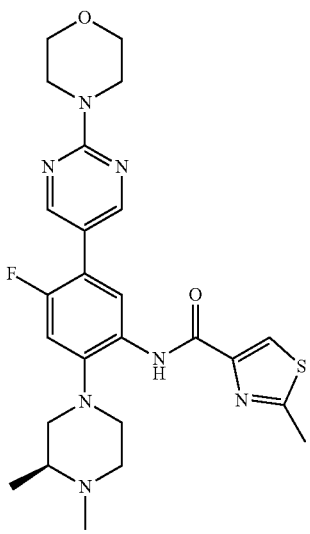

The title compound was prepared similar to the procedure described for Example 78 using 2-methyl-1,3-thiazole-4-carboxylic acid hydrochloride as the carboxylic acid acylating agent. $^1$H NMR (500 MHz, DMSO-d6) δ=10.27 (s, 1H), 8.56 (s, 2H), 8.50 (d, J=8.6 Hz, 1H), 8.32 (s, 1H), 7.28 (d, J=11.6 Hz, 1H), 3.79-3.76 (m, 4H), 3.71-3.68 (m, 4H), 2.95-2.87 (m, 4H), 2.78 (s, 3H), 2.56 (br d, J=11.1 Hz, 4H), 2.29 (s, 3H), 1.04 (d, J=6.2 Hz, 3H); LCMS [M+H]+: 512.2.

Example 195: N-[4-fluoro-5-(2-morpholin-4-ylpyrimidin-5-yl)-2-[(3R)-3,4-dimethylpiperazin-1-yl]phenyl]-2-methyl-1,3-thiazole-5-carboxamide

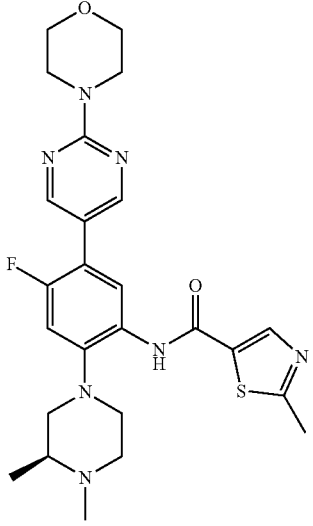 [SMILES: Cc1ncc(C(=O)Nc2cc(-c3cnc(N4CCOCC4)nc3)c(F)cc2N2CCN(C)[C@@H](C)C2)s1]

The title compound was prepared similar to the procedure described above for the preparation of Example 78 using 2-methyl-1,3-thiazole-5-carboxylic acid as acylating agent. $^1$H NMR (500 MHz, DMSO-d6) δ=9.59 (s, 1H), 8.48 (s, 2H), 8.31 (br s, 1H), 7.69 (d, J=8.6 Hz, 1H), 7.03 (d, J=12.3 Hz, 1H), 3.70-3.67 (m, 4H), 3.62-3.59 (m, 4H), 2.99-2.90 (m, 2H), 2.79-2.68 (m, 2H), 2.64 (s, 3H), 2.27-2.21 (m, 1H), 2.13 (s, 3H), 0.89 (d, J=6.2 Hz, 3H); LCMS [M+H]+: 512.2.

Example 196: N-[5-(6-acetamidopyridin-3-yl)-4-fluoro-2-[(3R)-3,4-dimethylpiperazin-1-yl]phenyl]-6-oxo-4-(trifluoromethyl)-1H-pyridine-3-carboxamide

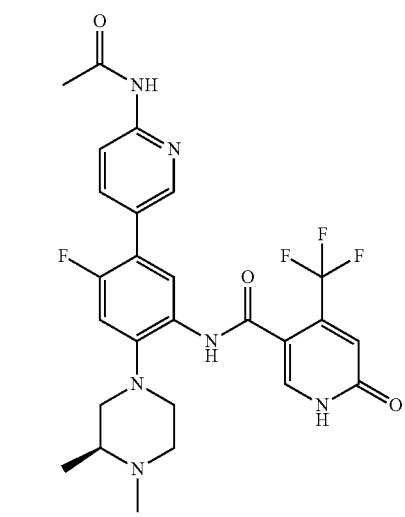 [SMILES: CC(=O)Nc1ccc(-c2cc(NC(=O)c3c[nH]c(=O)cc3C(F)(F)F)c(N3CCN(C)[C@@H](C)C3)cc2F)cn1]

Step 1: tert-butyl (S)-3-methylpiperazine-1-carboxylate

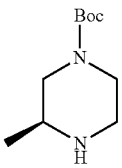

To a stirred solution of 2-methyl piperazine (10 g, 100 mmol, 1 eq) in ethanol (200 mL) was added DIPEA (43.5 mL, 250 mmol, and the reaction mixture stirred for 10 min. To this Boc anhydride (21.8 mL, 100 mmol, 1 eq) was added at 0° C. and the resulting reaction mixture was stirred at room temperature overnight. The progress of reaction was monitored by TLC, which indicated formation of nonpolar spot. The reaction mixture was concentrated and dissolved in DCM (200 mL) then washed with water (2×80 mL) followed by brine solution. The combined organic layer was dried over Na$_2$SO$_4$ and concentrated under reduced pressure to afford crude tert-butyl (S)-3-methylpiperazine-1-carboxylate (20 g, crude yield 100%) as a yellow liquid. TLC: MeOH:DCM (0.5:9.5); R$_f$=0.3.

Step 2: tert-butyl (S)-3,4-dimethylpiperazine-1-carboxylate

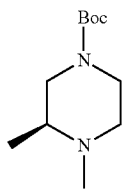

To a stirred solution of tert-butyl (S)-3-methylpiperazine-1-carboxylate (50 g, 250 mmol, 1 eq) in DCM:AcOH (10:3, 500 mL) was added 37% HCHO (40.5 mL, 500 mmol, 2 eq) at 0° C. and the resulting reaction mixture was stirred at room temperature for 3 h. NaCNBH₃ (31.5 g, 500 mmol, 2 eq) was added portion wise at 0° C. and the resulting reaction mixture was stirred at room temperature for 2 h. The progress of reaction was monitored with TLC, which indicated formation of nonpolar spot. The reaction mixture was basified with sat. aq, NaHCO₃ solution and extracted with DCM (2×150 mL). The combined organic layer was washed with water, followed by brine solution and dried over Na₂SO₄ then concentrated under reduced pressure to afford tert-butyl (S)-3,4-dimethylpiperazine-1-carboxylate (55 g, crude) as colorless liquid. TLC system: MeOH:DCM (1:9); R$_f$: 0.4.

Step 3: (S)-1,2-dimethylpiperazine

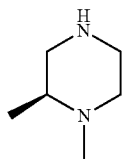

To a stirred solution of tert-butyl (S)-3,4-dimethylpiperazine-1-carboxylate (50 g, 233 mol, 1 eq) in DCM (500 mL) was added TFA (156 mL, 2097.3 mmol, 9 eq) at 0° C. and the resulting reaction mixture was stirred at room temperature for 16 h. The progress of reaction was monitored with TLC, which indicated formation of polar spot. The reaction mixture was evaporated under reduced pressure to crude residue, which was basified with NH₃ in THF and excess THF then was concentrated under reduced pressure, followed by dilution with DCM (150 mL) and filtration. The filtrate was concentrated under reduced pressure to afford crude (S)-1,2-dimethylpiperazine (55 g, crude) as a colorless liquid. TLC system: MeOH:DCM (1:5); R$_f$:0.1.

Step 4: 1-bromo-2,4-difluoro-5-nitrobenzene

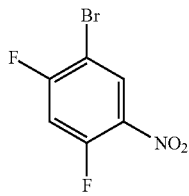 [SMILES: O=[N+]([O-])c1cc(Br)c(F)cc1F]

To a stirred suspension of 1-bromo-2,4-difluorobenzene (50 g, 259 mmol, 1 eq) in cold H2SO₄ (187.6 mL) was added conc. HNO₃ (165.5 mL) in a dropwise manner keeping the internal temp 20° C. then stirred for 10 min. at 0° C. Then the reaction mixture was poured into a mixture of diethyl ether (250 mL) and ice water (250 mL) with vigorous stirring. The organic layer was separated and the aqueous layer was again extracted with Et₂O (250 mL). The combined organic layer was washed with sat. sodium bicarbonate (2×200 mL) followed by sat. brine (2×200 mL) solution. The separated organic layer was dried over Na₂SO₄ and concentrated under reduced pressure to give crude product which was purified by column chromatography (silica gel, 100-200 mesh) using 0-15% EtOAc in pet ether as an eluent to afford 1-bromo-2,4-difluoro-5-nitrobenzene (52 g, 72%) as a yellow color liquid. TLC System: EtOAc:pet ether (3:7); R$_f$: 0.4

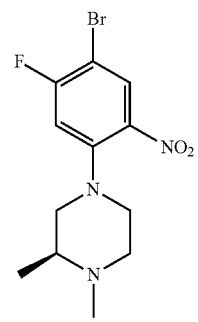 [SMILES: C[C@H]1CN(c2cc(F)c(Br)cc2[N+](=O)[O-])CCN1C]

Step 5: (S)-4-(4-bromo-5-fluoro-2-nitrophenyl)-1,2-dimethylpiperazine

To a stirred solution of (S)-1,2-dimethylpiperazine (45 g, 190.6 mmol, 1 eq) in EtOH (450 mL) was added TEA (106.9 mL, 762.7 mmol, 4 eq) under argon for 20 min., then followed by addition of 1-bromo-2,4-difluoro-5-nitrobenzene (47.8 g, 286.0 mmol, 1.5 eq) at RT under argon atm and heated to 85° C. for 16 h. TLC analysis indicated formation of less polar spot, then the reaction mixture was cooled to RT and solvent was evaporated under reduced pressure to give crude product, which was purified by column chromatography (silica gel, 100-200 mesh) using 0-30% EtOAc in pet ether as an eluent to afford (S)-4-(4-bromo-5-fluoro-2-nitrophenyl)-1,2-dimethylpiperazine (42 g, 92%) as a yellow solid. LCMS: [M+H]+ 332.0.

Step 6: (S)-5-bromo-2-(3,4-dimethylpiperazin-1-yl)-4-fluoroaniline

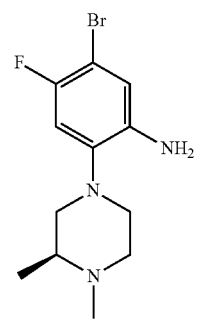

To a stirred solution of (S)-4-(4-bromo-5-fluoro-2-nitrophenyl)-1,2-dimethylpiperazine (32 g, 96.67 mmol, 1 eq) in EtOH:water (1:1, 640 mL) was added NH₄Cl (31 g, 96.67 mmol, 6 eq) followed by Fe powder (32.3 g, 96.67 mmol, 6 eq) at RT under argon atm., and heated to 80° C. for 16 h. TLC analysis indicated formation of polar spot, then the reaction mixture was cooled to RT then filtered through a celite pad and washed with MeOH (2×100 mL). The filtrate was concentrated under reduced pressure to crude product. The crude compound was purified by column chromatography (neutral alumina) using 100% DCM as an eluent affording (S)-5-bromo-2-(3,4-dimethylpiperazin-1-yl)-4-fluoroaniline (10.5 g, 48% yield) as pale yellow semi-solid. LCMS: [M+H]+ 302.17.

Step 7: (S)—N-(5-bromo-2-(3,4-dimethylpiperazin-1-yl)-4-fluorophenyl)-4-(trifluoromethyl)-6-(2-(trimethylsilyl)ethoxy)nicotinamide

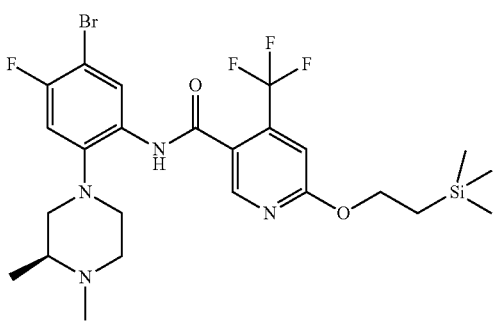 [SMILES: C[C@H]1CN(c2cc(F)c(Br)cc2NC(=O)c2cnc(OCC[Si](C)(C)C)cc2C(F)(F)F)CCN1C]

Propylphosphonic anhydride solution (2.81 ml, 4.71 mmol) was added dropwise to a mixture of (S)-5-bromo-2-(3,4-dimethylpiperazin-1-yl)-4-fluoroaniline (0.890 g, 2.95 mmol) and pyridine (0.949 ml, 11.78 mmol) in dry tetrahydrofuran (THF) (14.73 ml) under N₂ at RT. After 1.5 h of stirring, a pale yellow solution was obtained. Then (S)-5-bromo-2-(3,4-dimethylpiperazin-1-yl)-4-fluoroaniline (0.890 g, 2.95 mmol) was added as a solid and the reaction mixture was heated at 50° C. The crude product was allowed to cool to RT, THF was removed and the residue was partitioned between ethyl acetate (25 mL) and sodium bicarbonate sat solution (25 mL). The organic phase was separated and the aqueous phase was extracted with additional ethyl acetate (25 mL). The solvent was evaporated in vacuo yielding the crude product that was purified by flash column chromatography on silica gel (0-100%, 89% CH₂Cl₂, 10% MeOH, 1% NH₄Ac/CH₂Cl₂) to afford the desired compound (1.36 g, 89%). LCMS [M+1]⁺=591.22 g/mol.

Step 8: N-[5-(6-acetamidopyridin-3-yl)-4-fluoro-2-[(3R)-3,4-dimethylpiperazin-1-yl]phenyl]-6-oxo-4-(trifluoromethyl)-1H-pyridine-3-carboxamide

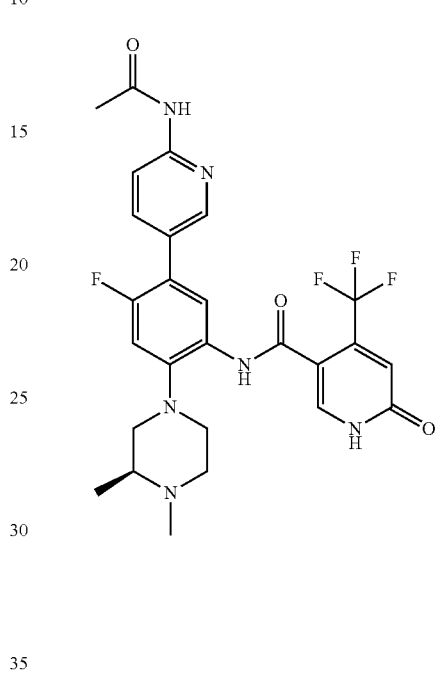

In a 5 mL microwave vial 2-acetamidopyridine-5-boronic acid, pinacol ester (0.034 g, 0.131 mmol), (S)—N-(5-bromo-2-(3,4-dimethylpiperazin-1-yl)-4-fluorophenyl)-4-(trifluoromethyl)-6-(2-(trimethylsilyl)ethoxy)nicotinamide (0.05183 g, 0.088 mmol), bis(di-tert-butyl(4-dimethylaminophenyl)phosphine)dichloropalladium(II) (6.20 mg, 8.76 µmol) and potassium phosphate tribasic reagent grade (0.037 g, 0.175 mmol) were dissolved in water (0.175 ml)/1,4-dioxane (1.577 ml) (9:1 mixture) to give a white suspension. The suspension was stirred for 5 min, degassed, purged with N₂, and microwaved for 60 min at 110° C. The solvent was evaporated and 15 mL of CH₂Cl₂ were added. The suspension was sonicated and extracted from water (15 mL). The solvent was evaporated in vacuo yielding the crude product that was purified by flash column chromatography on silica gel (0-100%, 89% CH₂Cl₂, 10% MeOH, 1% NH₄Ac/CH₂Cl₂) to afford the protected intermediate. The product was dissolved in 2 mL of DCM and trifluoroacetic acid (0.101 ml, 1.314 mmol) was added. The purple solution was stirred for 1 h and the solvent was evaporated. The residue was purified using a cation exchange column eluting with MeOH:NH₄OH. ¹H NMR (500 MHz, MeOD-d4) δ 8.37 (s, 1H), 8.08 (d, J=8.6 Hz, 1H), 7.87 (s, 1H), 7.84 (d, J=7.7 Hz, 2H), 7.00 (d, J=12.1 Hz, 1H), 6.81 (s, 1H), 3.02 (dq, J=11.6, 2.0 Hz, 1H), 2.97 (dt, J=11.6, 2.2 Hz, 1H), 2.87-2.80 (m, 2H), 2.50-2.42 (m, 2H), 2.32 (ddd, J=9.4, 6.4, 2.7 Hz, 1H), 2.27 (s, 3H), 2.10 (s, 3H), 1.03 (d, J=6.3 Hz, 3H); LCMS [M+1]+=547.28.

Example 197: N-[5-(2-cyanopyrimidin-5-yl)-4-fluoro-2-[(3R)-3,4-dimethylpiperazin-1-yl]phenyl]-6-oxo-4-(trifluoromethyl)-1H-pyridine-3-carboxamide

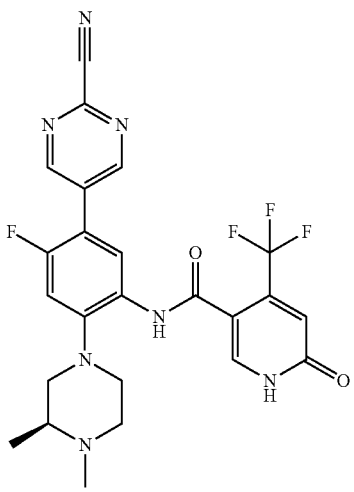

The title compound was prepared similar to the sequence described above for the preparation of Example 196 using 2-cyanopyrimidine-5-boronic acid pinacol ester in place of 2-acetamidopyridine-5-boronic acid, pinacol ester. $^1$H NMR (500 MHz, MeOD) δ 9.14 (d, J=0.7 Hz, 2H), 8.05 (d, J=8.1 Hz, 1H), 7.97 (s, 1H), 7.18 (d, J=12.2 Hz, 1H), 6.92 (s, J=4.4 Hz, 1H), 3.21-3.17 (m, 1H), 3.14 (dt, J=12.0, 2.7 Hz, 1H), 2.98-2.91 (m, 2H), 2.61-2.52 (m, 2H), 2.42 (ddd, J=9.6, 6.3, 2.9 Hz, 1H), 1.13 (d, J=6.4 Hz, 3H); LCMS [M+1]+=516.29.

Example 198: N-[5-[6-(cyclopropylmethoxy)pyridin-3-yl]-4-fluoro-2-[(3R)-3,4-dimethylpiperazin-1-yl]phenyl]-6-oxo-4-(trifluoromethyl)-1H-pyridine-3-carboxamide

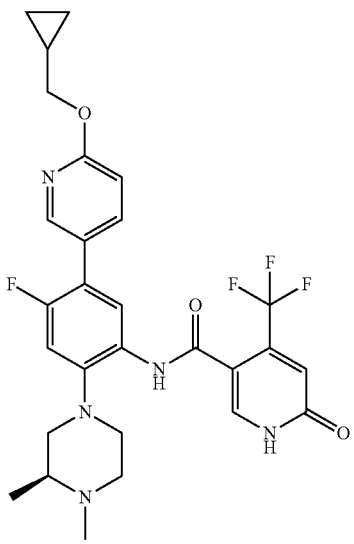

The title compound was prepared similar to the sequence described above for the preparation of Example 196 using 2-cyanopyrimidine-5-boronic acid pinacol ester in place of 2-acetamidopyridine-5-boronic acid, pinacol ester. $^1$H NMR (500 MHz, MeOD) δ 8.17 (s, 1H), 7.86 (s, 1H), 7.81 (d, J=8.2 Hz, 1H), 7.76 (dq, J=8.7, 0.8 Hz, 1H), 6.99 (d, J=12.0 Hz, 1H), 6.82 (s, 1H), 6.78 (d, J=8.6 Hz, 1H), 4.05 (d, J=7.1 Hz, 2H), 3.01 (dq, J 11.3, 2.0 Hz, 1H), 2.96 (dt, J=11.4, 2.1 Hz, 1H), 2.87-2.82 (m, 2H), 2.49-2.42 (m, 2H), 2.33 (ddd, J=9.6, 6.5, 3.0 Hz, 1H), 2.28 (s, 2H), 1.21 (ddd, J=12.9, 7.7, 4.1 Hz, 1H), 1.03 (d, J=6.3 Hz, 3H), 0.53-0.49 (m, 2H), 0.27 (q, J=4.7 Hz, 2H); LCMS [M+1]+=560.30.

Example 199: N-[4-fluoro-5-(2-morpholin-4-ylpyrimidin-5-yl)-2-[(3R)-3,4-dimethylpiperazin-1-yl]phenyl]-2-methyl-4-(trifluoromethyl)-1,3-thiazole-5-carboxamide The title compound was prepared according to a procedure similar to Example 78 using 2-methyl-4-(trifluoromethyl)-1,3-thiazole-5-carbonyl chloride as acylating agent. $^1$H NMR (500 MHz, DMSO-d6) δ=9.96 (s, 1H), 8.46 (s, 2H), 7.70 (br d, J=7.0 Hz, 1H), 7.05 (br d, J=11.5 Hz, 1H), 3.71-3.67 (m, 4H), 3.63-3.59 (m, 4H), 2.98-2.86 (m, 2H), 2.81-2.67 (m, 5H), 2.36 (br t, J=10.5 Hz, 1H), 2.31-2.24 (m, 1H), 2.19-2.12 (m, 4H), 0.93 (d, J=6.1 Hz, 3H); LCMS [M+H]+: 580.2.

Example 200: 3,5-dichloro-N-[4-fluoro-5-(2-morpholin-4-ylpyrimidin-5-yl)-2-[(3R)-3,4-dimethylpiperazin-1-yl]phenyl]benzamide

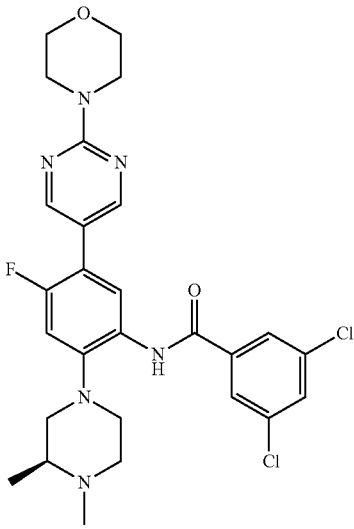 [SMILES: C[C@H]1CN(c2cc(F)c(-c3cnc(N4CCOCC4)nc3)cc2NC(=O)c2cc(Cl)cc(Cl)c2)CCN1C]

The title compound was prepared using a procedure similar to Example 78 with 3,5-dichlorobenzoic acid as acylating agent. $^1$H NMR (500 MHz, DMSO-d6) δ=9.79 (s, 1H), 8.49 (d, J=1.1 Hz, 2H), 7.92-7.80 (m, 3H), 7.73 (d, J=8.6 Hz, 1H), 7.05 (d, J=12.3 Hz, 1H), 3.71-3.66 (m, 4H), 3.63-3.59 (m, 5H), 2.96 (br t, J=9.0 Hz, 2H), 2.82-2.66 (m, 2H), 2.20 (dt, J=2.8, 11.0 Hz, 1H), 2.16-2.07 (m, 4H), 0.90 (d, J=6.4 Hz, 3H); LCMS [M+H]+: 559.1.

Example 201: N-[4-fluoro-5-(3-fluoro-4-morpholin-4-ylphenyl)-2-[(3R)-3,4-dimethylpiperazin-1-yl]phenyl]-6-oxo-4-(trifluoromethyl)-1H-pyridine-3-carboxamide

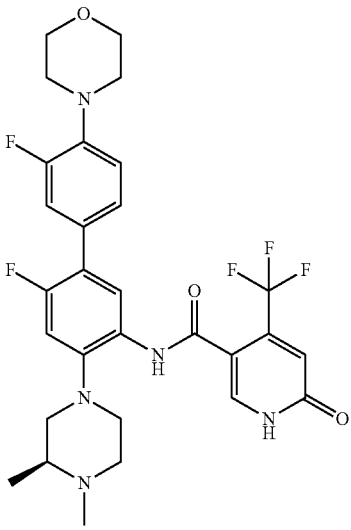

The title compound (brown solid, 37.4 mg, 61%) was prepared through a procedure similar to that of Example 40 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and 3-fluoro-4-morpholinophenylboronic acid (45 mg, 0.2 mmol). $^1$H NMR (500 MHz, METHANOL-d4) δ=7.97 (s, 1H), 7.92 (d, J=8.3 Hz, 1H), 7.33 (d, J=8.7 Hz, 1H), 7.30 (d, J=14.2 Hz, 1H), 7.12 (t, J=8.7 Hz, 1H), 7.05 (d, J=12.4 Hz, 1H), 6.93 (s, 1H), 3.92-3.83 (m, 4H), 3.18-3.11 (m, 4H), 3.08 (br d, J=10.9 Hz, 2H), 2.69-2.54 (m, 4H), 2.40 (s, 3H), 1.19 (d, J=6.0 Hz, 6H); LCMS [M+H]+ 606.3.

Example 202: N-[4-fluoro-5-[2-[(2R,6S)-2,6-dimethylmorpholin-4-yl]pyrimidin-5-yl]-2-[(3R)-3,4-dimethylpiperazin-1-yl]phenyl]-6-oxo-4-(trifluoromethyl)-1H-pyridine-3-carboxamide

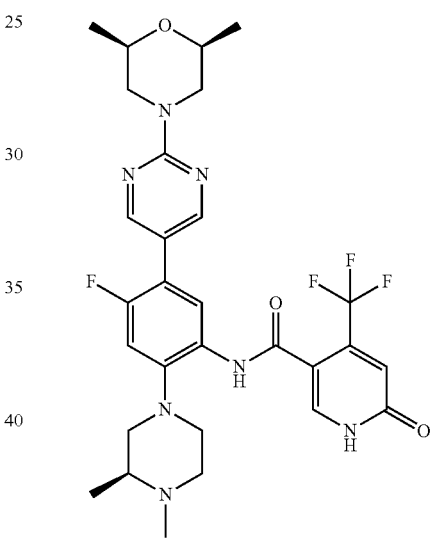

The title compound (light brown solid, 48.3 mg, 77%) was prepared in a manner similar to that described in Example 40 using (S)—N-(5-bromo-2-(3,4-dimethylpiperazin-1-yl)-4-fluorophenyl)-6-oxo-4-(trifluoromethyl)-1,6-dihydropyridine-3-carboxamide (49.1 mg, 0.1 mmol) and (2-((2S,6R)-2,6-dimethylmorpholino)pyrimidin-5-yl)boronic acid (47 mg, 0.2 mmol). $^1$H NMR (500 MHz, CHLOROFORM-d) δ=8.71 (s, 1H), 8.57 (d, J=1.0 Hz, 2H), 8.47 (d, J=8.2 Hz, 1H), 7.89 (s, 1H), 7.06 (d, J=11.1 Hz, 1H), 7.02 (s, 1H), 4.64 (dd, J=1.5, 13.2 Hz, 2H), 3.69 (ddd, J=2.4, 6.3, 10.5 Hz, 2H), 3.02-2.87 (m, 3H), 2.83 (br d, J=11.1 Hz, 1H), 2.68 (dd, J=10.6, 13.2 Hz, 2H), 2.61 (br t, J=10.6 Hz, 1H), 2.42-2.32 (m, 4H), 2.28-2.18 (m, 1H), 1.30 (d, J=6.2 Hz, 6H), 1.11 (d, J=6.2 Hz, 3H); LCMS [M+H]+ 604.3.

Example 203: 4-fluoro-N-[4-fluoro-5-[2-(4-methyl-1,4-diazepan-1-yl)pyrimidin-5-yl]-2-[(3R,5S)-3,4,5-trimethylpiperazin-1-yl]phenyl]-2-(trifluoromethyl)benzamide

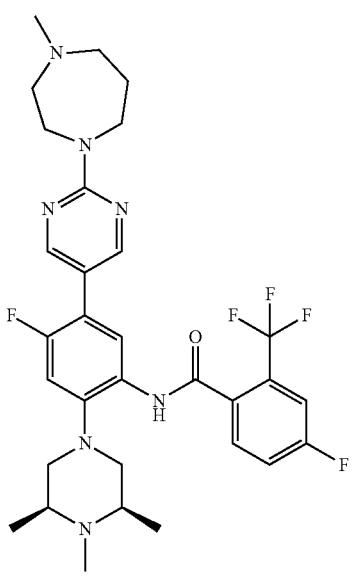 [SMILES: C[C@@H]1CN(c2cc(F)c(-c3cnc(N4CCCN(C)CC4)nc3)cc2NC(=O)c2ccc(F)cc2C(F)(F)F)C[C@H](C)N1C]

To a mixture of 2-chloropyrimidine-5-boronic acid (48 mg, 0.3 mmol) and 1-methylhomopiperazine (0.039 mL, 0.315 mmol) in EtOH (2 mL) was added triethylamine (0.070 mL, 0.5 mmol). The resulting mixture was stirred at 75° C. for 1.5 h. Solvents were removed to give crude (2-(4-methyl-1,4-diazepan-1-yl)pyrimidin-5-yl)boronic acid as a yellow oil. LCMS [M+H]$^+$ 237.4. The title compound (off white solid, 31.4 mg, 50%) was prepared using a procedure similar to that of Example 29 using crude (2-(4-methyl-1,4-diazepan-1-yl)pyrimidin-5-yl)boronic acid (0.3 mmol) and N-(5-bromo-4-fluoro-2-((3S,5R)-3,4,5-trimethylpiperazin-1-yl)phenyl)-4-fluoro-2-(trifluoromethyl)benzamide (50.5 mg, 0.1 mmol). $^1$H NMR (500 MHz, CHLOROFORM-d) δ=8.60-8.52 (m, 4H), 7.66 (dd, J=5.3, 8.4 Hz, 1H), 7.50 (dd, J=2.4, 8.8 Hz, 1H), 7.38 (dt, J=2.3, 8.1 Hz, 1H), 7.00 (d, J=11.1 Hz, 1H), 4.02-3.95 (m, 2H), 3.87 (t, J=6.4 Hz, 2H), 2.83 (br d, J=11.0 Hz, 2H), 2.76-2.69 (m, 2H), 2.65-2.56 (m, 4H), 2.40 (s, 3H), 2.30-2.18 (m, 5H), 2.08-2.00 (m, 2H), 1.10 (d, J=6.2 Hz, 6H); LCMS [M+H]$^+$ 618.6.

Example 204: N-[4-fluoro-5-(4-morpholin-4-ylphenyl)-2-[(3R,5S)-3,4,5-trimethylpiperazin-1-yl]phenyl]-1-methyl-6-oxo-4-(trifluoromethyl)pyridine-3-carboxamide

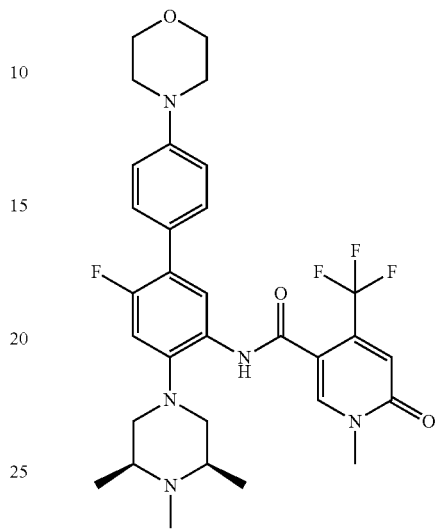

Step 1: Preparation of 6-fluoro-4'-morpholino-4-((3S,5R)-3,4,5-trimethylpiperazin-1-yl)-[1,1'-biphenyl]-3-amine

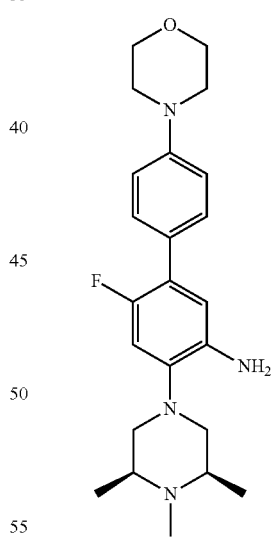

To a 20 mL microwave vial charged with 5-bromo-4-fluoro-2-((3S,5R)-3,4,5-trimethylpiperazin-1-yl)aniline (1.265 g mg, 4 mmol), 4-(morpholino)phenylboronic acid (1.242 g, 6.0 mmol), and Pd(dppf)Cl$_2$ (220 mg, 0.3 mmol, 7.5 mol %) was added dioxane (12 mL), followed by 1 M aq K$_3$PO$_4$ (6 mL, 6 mmol). The resulting mixture was irradiated in a microwave at 110° C. for 2 h. After quenching with sat. brine (20 mL), it was extracted with EtOAc (30 mL×2). The combined extracts were concentrated and purified by Biotage SNAP KP-Sil 50 g (gradient: EtOAc/hex 0-100% then MeOH/DCM 0-8%). Fractions showing product gave light brownish clear needle crystals (1.320 g, yield 82%) of the desired product. LCMS[M+H]+ 399.3.

Step 2: N-(6-fluoro-4'-morpholino-4-((3S,5R)-3,4,5-trimethylpiperazin-1-yl)-[1,1'-biphenyl]-3-yl)-1-methyl-6-oxo-4-(trifluoromethyl)-1,6-dihydropyridine-3-carboxamide

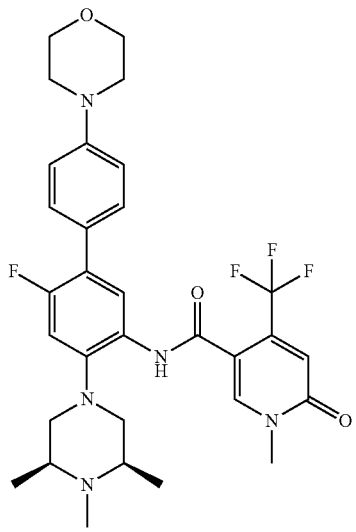

The title compound (yellow solid, 19.9 mg, 32%) was prepared through a procedure similar to Example 34 using 1-methyl-6-oxo-4-(trifluoromethyl)-1,6-dihydropyridine-3-carboxylic acid (44 mg, 0.2 mmol) and 6-fluoro-4'-morpholino-4-((3S,5R)-3,4,5-trimethylpiperazin-1-yl)-[1,1'-biphenyl]-3-amine (40 mg, 0.1 mmol). $^{1}$H NMR (500 MHz, CHLOROFORM-d) δ=8.71 (s, 1H), 8.48 (d, J=8.3 Hz, 1H), 7.87 (s, 1H), 7.52 (d, J=7.5 Hz, 2H), 7.02-6.94 (m, 4H), 3.92-3.85 (m, 4H), 3.64 (s, 3H), 3.26-3.19 (m, 4H), 2.81 (br d, J=11.0 Hz, 2H), 2.65 (br t, J=10.8 Hz, 2H), 2.33 (s, 5H), 1.13 (d, J=6.2 Hz, 6H); LCMS [M+H]+ 602.4.

Example 205: N-[5-(5-cyanopyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

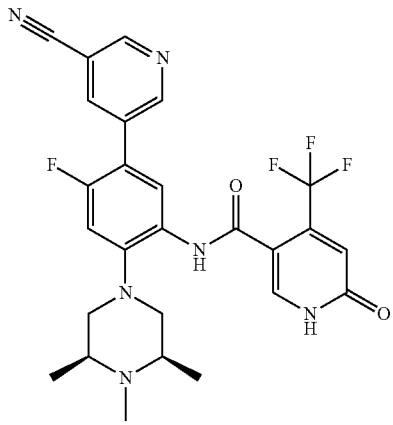 [SMILES: C[C@@H]1CN(c2cc(F)c(-c3cncc(C#N)c3)cc2NC(=O)c2c[nH]c(=O)cc2C(F)(F)F)C[C@H](C)N1C]

The title compound was prepared using a procedure similar to that described in Example 39 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol), 3-cyanopyridine-5-boronic acid pinacol ester (19.00 mg, 0.083 mmol) and [1,1'-Bis(diphenylphosphino)ferrocene]dichloropalladium(II) (12.10 mg, 0.017 mmol) to give, after deprotection of the silyoxy intermediate, 25.5 mg (94% yield for the last step) of the title compound. $^{1}$H NMR (500 MHz, METHANOL-d4) δ=9.15-8.83 (m, 2H), 8.52-8.30 (m, 1H), 8.14-7.90 (m, 2H), 7.27-7.08 (m, 1H), 7.02-6.85 (m, 1H), 3.20-3.10 (m, 2H), 2.77-2.57 (m, 4H), 2.50-2.37 (m, 3H), 1.26-1.15 (m, 6H); LCMS [M+H]+ 529.2

Example 206: N-[5-(5-chloropyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

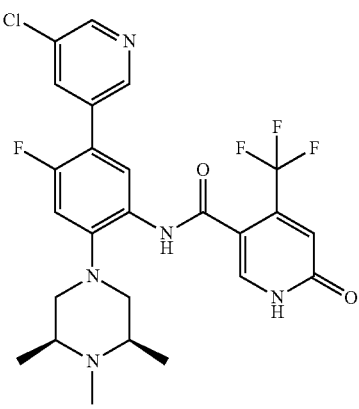 [SMILES: C[C@@H]1CN(c2cc(F)c(-c3cncc(Cl)c3)cc2NC(=O)c2c[nH]c(=O)cc2C(F)(F)F)C[C@H](C)N1C]

A procedure similar to that of Example 39 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol), 3-chloropyridine-5-boronic acid (19.49 mg, 0.124 mmol) to give the silyoxy intermediate which was deprotected using TFA and purified by standard methods to give the title compound in 89% yield. $^{1}$H NMR (500 MHz, METHANOL-d4) δ=8.73-8.65 (m, 1H), 8.61-8.52 (m, 1H), 8.15-8.07 (m, 1H), 8.01-7.94 (m, 2H), 7.21-7.09 (m, 1H), 6.96-6.91 (m, 1H), 3.20-3.08 (m, 2H), 2.71-2.62 (m, 4H), 2.47-2.40 (m, 3H), 1.20 (br d, J=4.9 Hz, 6H); LCMS [M+H]+ 538.2.

Example 207: N-[5-(2-cyclohexyloxypyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

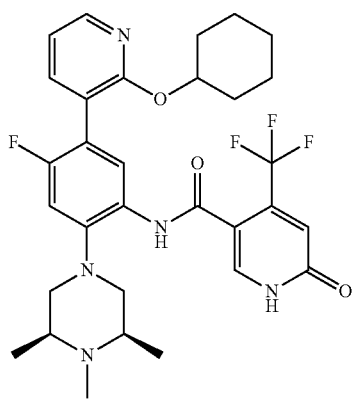

A procedure similar to that of Example 39 employing N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) and 2-cyclohexyloxypyridine-3-boronic acid, pinacol ester (37.6 mg, 0.124 mmol) was used. Deprotection of the N-(5-(2-(cyclohexyloxy)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide intermediate with TFA and purification by standard procedures gave the title compound in 97% yield for the last step. $^1$H NMR (500 MHz, METHANOL-d4) δ=8.20-8.07 (m, 1H), 8.03-7.80 (m, 2H), 7.74-7.62 (m, 1H), 7.14-6.97 (m, 2H), 6.96-6.89 (m, 1H), 5.19-5.05 (m, 1H), 3.17-3.04 (m, 2H), 2.75-2.57 (m, 4H), 2.52-2.35 (m, 3H), 2.00-1.89 (m, 2H), 1.79-1.68 (m, 2H), 1.62-1.51 (m, 3H), 1.49-1.40 (m, 2H), 1.38-1.28 (m, 2H), 1.27-1.14 (m, 6H); LCMS [M+H]+ 602.5

Example 208: N-[4-fluoro-5-[1-[2-(4-methoxyphenyl)acetyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

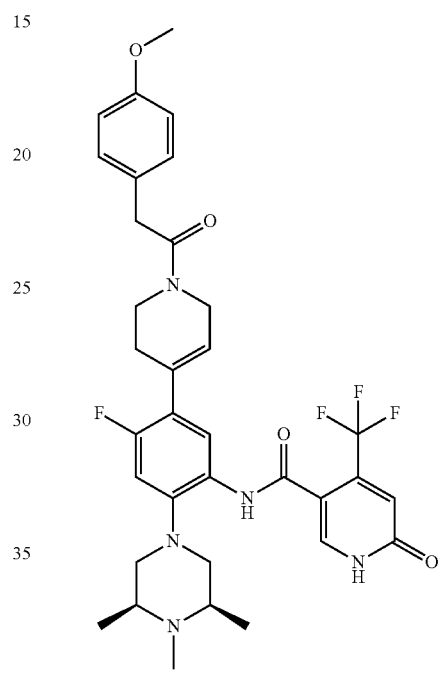

To N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol obtained from Example 148) and N,N-diisopropylethylamine (0.021 ml, 0.118 mmol) in DCM (3 ml) at RT was added 4-methoxyphenylacetyl chloride (9.75 μl, 0.065 mmol). The milky reaction mixture became a clear solution. It was stirred at RT. Complete disappearance of the starting material and formation of the desired product was observed after 20 min at rt. The reaction was worked up at this point and purified using standard methods to give the title compound (31.5 mg, 77% yield). $^1$H NMR (500 MHz, METHANOL-d4) δ=7.89-7.77 (m, 1H), 7.66-7.55 (m, 1H), 7.15-7.01 (m, 2H), 6.88-6.75 (m, 4H), 5.96-5.75 (m, 1H), 4.19-4.09 (m, 2H), 3.72-3.59 (m, 7H), 2.97-2.85 (m, 2H), 2.54-2.39 (m, 5H), 2.30-2.23 (m, 4H), 1.09-1.03 (m, 6H); LCMS [M+H]+ 656.6.

Example 209: N-[4-fluoro-5-[6-(2-methoxyethoxy)pyridin-3-yl]-2-[(3R,5S)-3,4,5-trimethylpiperazin-1-yl]phenyl]-1-methyl-6-oxo-4-(trifluoromethyl)pyridine-3-carboxamide

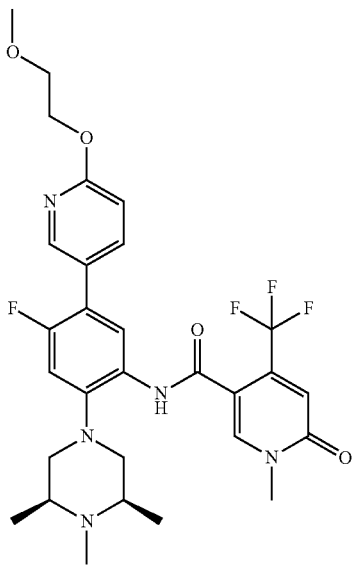

Step 1: Preparation of N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide

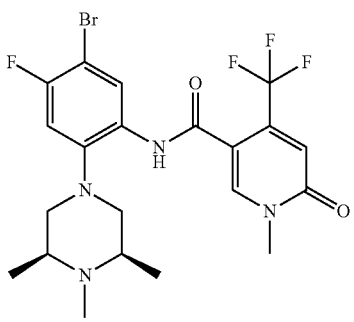 [SMILES: C[C@@H]1CN(c2cc(F)c(Br)cc2NC(=O)c2cn(C)c(=O)cc2C(F)(F)F)C[C@H](C)N1C]

To a solution of N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (505 mg, 1 mmol) in DMF (10 mL) was added cesium carbonate (326 mg, 1 mmol). After stirring at rt for 10 min, iodomethane (68 µL, 1.1 mmol) was added. The resulting mixture was stirred at rt for 30 min. then H$_2$O (50 mL) was added slowly with stirring and an abundance of white precipitate formed. After stirring at rt for 10 min, it was filtered and washed with H$_2$O (10 mL), then dried to give the title compound as a light beige solid (417 mg, 78%). LCMS [M+H]$^+$ 519.2.

Step 2: N-(4-fluoro-5-(6-(2-methoxyethoxy)pyridin-3-yl)-2-((3S,5R)-3,4,5-trimethylpiperazin-1-yl)phenyl)-1-methyl-6-oxo-4-(trifluoromethyl)-1,6-dihydropyridine-3-carboxamide

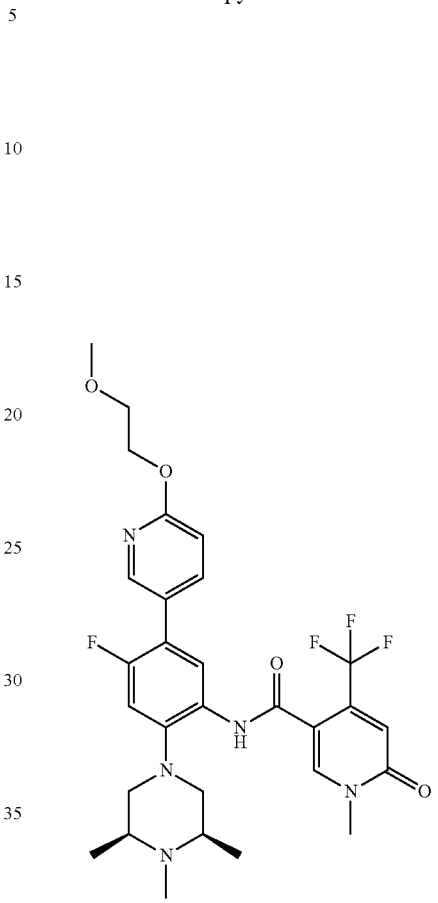

The title compound (grey solid, 41.2 mg, 67%) was prepared similar to the Suzuki coupling procedure described in Example 31 using N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (51.9 mg, 0.1 mmol) and 2-(2-methoxyethoxy)-5-(4,4,5,5-tetramethyl-1,3,2-dioxaborolan-2-yl)pyridine (56 mg, 0.2 mmol). $^1$H NMR (500 MHz, CHLOROFORM-d) δ=8.71 (s, 1H), 8.47 (d, J=8.2 Hz, 1H), 8.35 (s, 1H), 7.87 (s, 1H), 7.78 (br d, J=8.7 Hz, 1H), 7.02 (d, J=10.4 Hz, 1H), 6.97 (s, 1H), 6.88 (d, J=8.7 Hz, 1H), 4.57-4.49 (m, 2H), 3.81-3.74 (m, 2H), 3.64 (s, 3H), 3.46 (s, 3H), 2.81 (br d, J=11.0 Hz, 2H), 2.64 (br t, J=10.8 Hz, 2H), 2.37-2.27 (m, 5H), 1.13 (d, J=6.2 Hz, 6H); LCMS [M+H]$^+$ 592.4.

Example 210: N-[4-fluoro-5-(2-pyrrolidin-1-ylpyrimidin-5-yl)-2-[(3R,5S)-3,4,5-trimethylpiperazin-1-yl]phenyl]-1-methyl-6-oxo-4-(trifluoromethyl)pyridine-3-carboxamide

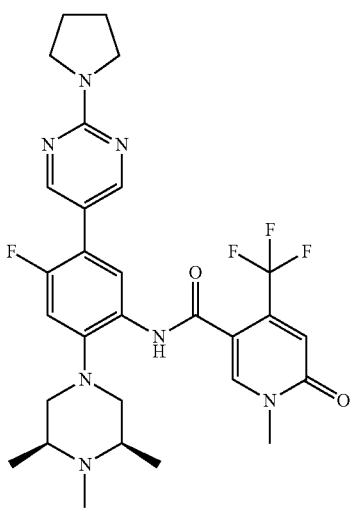

The title compound (grey solid, 50.6 mg, 84%) was prepared using a procedure similar to Example 29 with N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (51.9 mg, 0.1 mmol) and 2-(pyrrolidin-1-yl)pyrimidine-5-boronic acid pinacol ester (55 mg, 0.2 mmol). $^1$H NMR (500 MHz, CHLOROFORM-d) δ=8.72 (s, 1H), 8.54 (s, 2H), 8.45 (d, J=8.1 Hz, 1H), 7.88 (s, 1H), 7.01 (d, J=10.5 Hz, 1H), 6.97 (s, 1H), 3.68-3.60 (m, 7H), 2.80 (br d, J=10.9 Hz, 2H), 2.63 (br t, J=10.8 Hz, 2H), 2.37-2.26 (m, 5H), 2.08-1.99 (m, 4H), 1.13 (d, J=6.2 Hz, 6H); LCMS [M+H]$^+$ 588.4.

Example 211: N-[4-fluoro-5-(2-morpholin-4-ylpyrimidin-5-yl)-2-[(3R,5S)-3,4,5-trimethylpiperazin-1-yl]phenyl]-3-(trifluoromethyl)thiophene-2-carboxamide

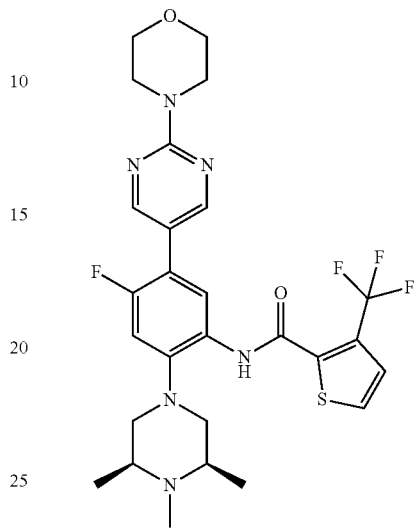

The title compound (beige solid, 36.1 mg, 62%) was prepared similar to Example 34 using 4-(trifluoromethyl)-1,3-thiazole-5-carboxylic acid (39 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.13 (s, 1H), 8.58 (d, J=8.3 Hz, 1H), 8.56 (d, J=1.2 Hz, 2H), 7.54 (d, J=5.1 Hz, 1H), 7.36 (d, J=5.3 Hz, 1H), 7.04 (d, J=11.2 Hz, 1H), 3.90-3.83 (m, 4H), 3.83-3.76 (m, 4H), 2.85 (br d, J=10.8 Hz, 2H), 2.65 (t, J=10.9 Hz, 2H), 2.46-2.37 (m, 2H), 2.34 (s, 3H), 1.14 (d, J=6.2 Hz, 6H); LCMS [M+H]$^+$ 579.3.

Example 212: 3,5-dichloro-4-fluoro-N-[4-fluoro-5-(2-morpholin-4-ylpyrimidin-5-yl)-2-[(3R,5S)-3,4,5-trimethylpiperazin-1-yl]phenyl]benzamide

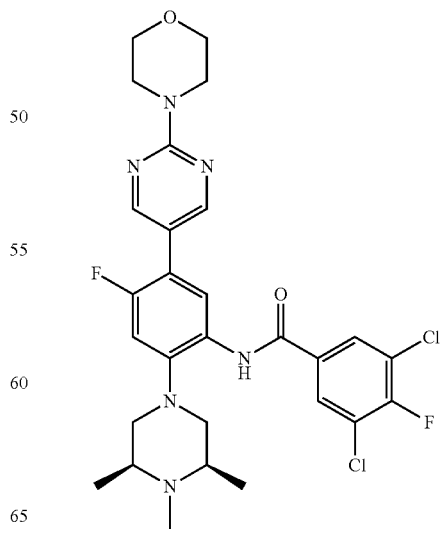

The title compound (beige solid, 49.8 mg, 83%) was prepared in a manner similar to that described in Example 34 using 3,5-dichloro-4-fluorobenzoic acid (42 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.25 (s, 1H), 8.58-8.54 (m, 3H), 7.88 (d, J=6.0 Hz, 2H), 7.02 (d, J=11.1 Hz, 1H), 3.91-3.85 (m, 4H), 3.82-3.78 (m, 4H), 2.89 (br d, J=11.0 Hz, 2H), 2.71 (t, J=10.9 Hz, 2H), 2.47-2.40 (m, 2H), 2.38 (s, 3H), 1.18 (d, J=6.2 Hz, 6H); LCMS [M+H]$^+$ 591.3.

Example 213: 2,3-dichloro-N-[4-fluoro-5-(2-morpholin-4-ylpyrimidin-5-yl)-2-[(3R,5S)-3,4,5-trimethylpiperazin-1-yl]phenyl]benzamide

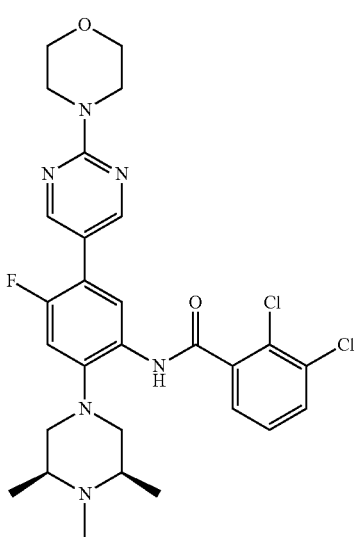

The title compound (beige solid, 45.5 mg, 77%) was prepared by a procedure similar to that of Example 34 using 2,3-dichlorobenzoic acid (38 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=8.91 (s, 1H), 8.63 (d, J=8.2 Hz, 1H), 8.58 (s, 2H), 7.60 (dd, J=8.0, 9.1 Hz, 1H), 7.61 (dd, J=7.9, 12.2 Hz, 1H), 7.36 (t, J=7.8 Hz, 1H), 7.01 (d, J=11.2 Hz, 1H), 3.91-3.85 (m, 4H), 3.82-3.78 (m, 4H), 2.88 (br d, J=11.0 Hz, 2H), 2.64 (t, J=10.9 Hz, 2H), 2.39-2.29 (m, 5H), 1.13 (d, J=6.2 Hz, 6H); LCMS [M+H]$^+$ 573.3.

Example 214: N-[4-fluoro-5-[3-[[methyl(oxetan-3-yl)amino]methyl]phenyl]-2-[(3R)-3,4-dimethylpiperazin-1-yl]phenyl]-6-oxo-4-(trifluoromethyl)-1H-pyridine-3-carboxamide

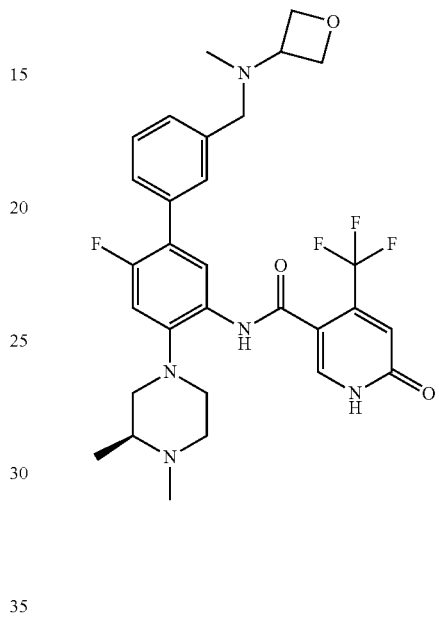

(S)—N-(4-(3,4-dimethylpiperazin-1-yl)-6-fluoro-3'-formyl-[1,1'-biphenyl]-3-yl)-6-oxo-4-(trifluoromethyl)-1,6-dihydropyridine-3-carboxamide (116 mg, 0.225 mmol), (S)—N-(4-(3,4-dimethylpiperazin-1-yl)-6-fluoro-3'-formyl-[1,1'-biphenyl]-3-yl)-6-oxo-4-(trifluoromethyl)-1,6-dihydropyridine-3-carboxamide (116 mg, 0.225 mmol) and acetic acid, glacial, 99.8% (53.9 mg, 0.898 mmol) were mixed in anhydrous DCE. A cloudy solution was obtained. After 5-10 min, Sodium triacetoxyborohydride (143 mg, 0.674 mmol) was added and the reaction mixture was stirred at RT overnight. LCMS showed complete disappearance of the starting material and formation of the desired product. The reaction mixture was quenched with sat aq NaHCO$_3$ solution. The organic phase was separated, the aqueous phase was extracted with DCM, the combined organic phase was washed with brine, then dried over Na$_2$SO$_4$ and concentrated to obtain the crude. The product was purified using silica gel chromatography (4 G column), eluting with DCM containing 0-6% DCM. The appropriate fractions were combined and concentrated to afford the desired product as a white foam (71 mg, 510% yield). $^1$H NMR (500 MHz, METHANOL-d4) δ=8.25-8.19 (m, 1H), 7.95-7.87 (m, 1H), 7.86-7.79 (m, 1H), 7.44-7.41 (m, 1H), 7.40-7.37 (m, 1H), 7.37-7.32 (m, 1H), 7.29-7.24 (m, 1H), 7.07-7.01 (m, 1H), 6.86-6.81 (m, 1H), 4.56-4.51 (m, 2H), 4.50-4.45 (m, 2H), 3.70-3.58 (m, 1H), 3.47-3.39 (m, 2H), 3.31-3.25 (m, 1H), 3.18-3.10 (m, 2H), 3.04-2.91 (m, 3H), 2.78-2.68 (m, 1H), 2.68-2.58 (m, 3H), 2.09-1.98 (m, 3H), 1.24-1.21 (m, 3H); LCMS [M+H]+ 588.

Example 215: N-[5-(5-ethoxypyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

Example 216: 4-(difluoromethyl)-N-[4-fluoro-5-(2-morpholin-4-ylpyrimidin-5-yl)-2-[(3R)-3,4-dimethylpiperazin-1-yl]phenyl]-1-methyl-6-oxopyridine-3-carboxamide

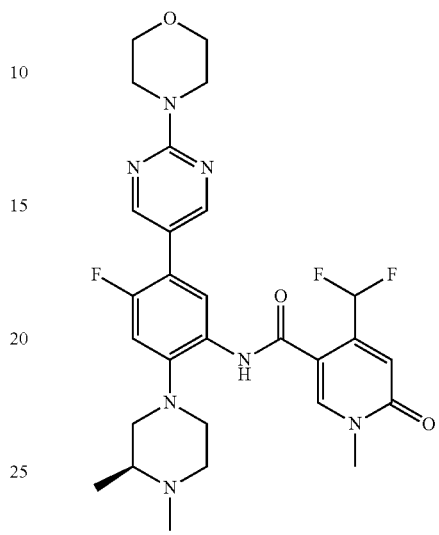

The title compound was prepared similar to the procedure described above for the preparation of Example 78 using 1-methyl-6-oxo-4-(trifluoromethyl)-1,6-dihydropyridine-3-carboxylic acid as the acylating agent. $^1$H NMR (500 MHz, DMSO-d6) δ=9.40 (s, 1H), 8.45 (s, 2H), 8.23 (s, 1H), 7.67 (d, J=8.7 Hz, 1H), 7.02 (d, J=12.2 Hz, 1H), 6.80 (s, 1H), 3.71-3.66 (m, 4H), 3.63-3.59 (m, 4H), 3.46 (s, 3H), 3.01-2.91 (m, 2H), 2.78-2.66 (m, 2H), 2.35-2.27 (m, 2H), 2.20-2.09 (m, 4H), 0.90 (d, J=6.2 Hz, 3H); LCMS [M+H]+: 590.3.

Example 217: N-[5-(6-acetamidopyridin-3-yl)-4-fluoro-2-[(3R)-3,4-dimethylpiperazin-1-yl]phenyl]-4-(difluoromethyl)-1-methyl-6-oxopyridine-3-carboxamide

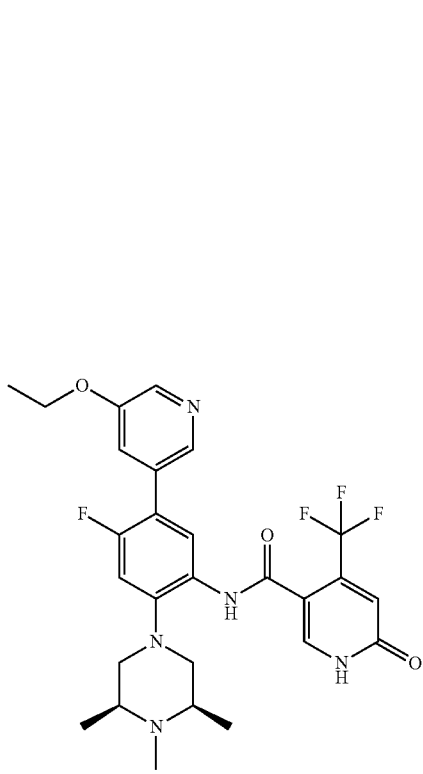 [SMILES: CCOc1cncc(-c2cc(NC(=O)c3c[nH]c(=O)cc3C(F)(F)F)c(N3C[C@@H](C)N(C)[C@@H](C)C3)cc2F)c1]

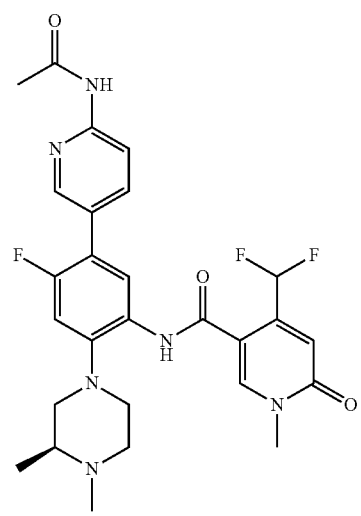 [SMILES: CC(=O)Nc1ccc(-c2cc(NC(=O)c3cn(C)c(=O)cc3C(F)F)c(N3CCN(C)[C@@H](C)C3)cc2F)cn1]

The procedure was similar to Example 39 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (30 mg, 0.050 mmol), 3-(Cyclopropylmethoxy)-5-(4,4,5,5-tetramethyl-1,3,2-dioxaborolan-2-yl)pyridine (27.3 mg, 0.099 mmol) to give the intermediate N-(5-(5-(cyclopropylmethoxy)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide which was deprotected by TFA and purified by standard methods to give the title compound (5.0 mg, Yield=710% for the last step). $^1$H NMR (500 MHz, METHANOL-d4) δ=8.22-8.17 (m, 1H), 8.16-8.08 (m, 1H), 7.93-7.88 (m, 1H), 7.87-7.80 (m, 1H), 7.50-7.44 (m, 1H), 7.10-7.00 (m, 1H), 6.86-6.79 (m, 1H), 3.90-3.83 (m, 2H), 3.16-3.08 (m, 2H), 3.01-2.81 (m, 2H), 2.73-2.65 (m, 2H), 2.63-2.43 (m, 3H), 1.23-1.18 (m, 7H), 0.59-0.52 (m, 2H), 0.33-0.27 (m, 2H); LCMS [M+H]+ 574.6.

Step 1: 5-bromo-2-methoxyisonicotinaldehyde

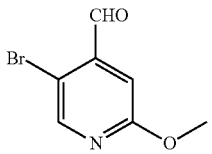

To a solution of DiPA (30.6 mL, 212.76 mmol, 2 eq) in dry THF (100 mL) was added n-BuLi (2.5M in n-hexane, 84.8 mL, 212.76 mmol, 2 eq) at −78° C. and allowed to warm up to −30° C. over 30 min. To freshly prepared LDA was added a solution of 5-bromo-2-methoxypyridine Exact Mass: 186.96 (2×20 g, 106.38 mmol, 1 eq) in dry THF (400 mL) at −78° C. under an argon atm and maintained for 1 h at the same temperature before being quenched with DMF (15.7 mL, 212.76 mmol, 2 eq) added dropwise and stirred at the same temperature for 10 mins. TLC analysis indicated formation of polar spots. Then, the reaction mixture was quenched with sat·NH$_4$Cl (150 mL) and extracted with EtOAc (2×200 ml) and washed with water and brine. The combined organic layers were dried over Na$_2$SO$_4$ and concentrated under reduced pressure to give crude product of 5-bromo-2-methoxypyridine. TLC: 10% EtOAc in pet ether; R$_f$: 0.6

Step 2: methyl 4-formyl-6-methoxynicotinate

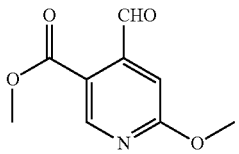

To a stirred solution of 5-bromo-2-methoxypyridine (2×20 g, 93.45 mmol, 1 eq) in methanol (200 mL) was added TEA (65.27 ml, 462.27 mmol, 5 eq) at RT in a steel bomb degassed with argon for 10 mins, then Pd$_2$(dppf)Cl$_2$DCM (2.28 g, 2.8 mmol, 0.03 eq) was added and the reaction mixture heated to 70° C. under 250 Psi (CO gas) for 16 h. TLC analysis indicated formation of polar spots. The reaction mixture was filtered through a celite bed washed with methanol; then the filtrate was evaporated under reduced pressure. The crude compound was purified by silica gel column chromatography (230-400 mesh) using 0-5% EtOAc in pet ether as an eluent to give methyl 4-formyl-6-methoxynicotinate (8.2 g, 43.9%) as an off white solid. TLC system: 20% EtOAc in pet ether; R$_f$: 0.6.

Step 3: methyl 4-(difluoromethyl)-6-methoxynicotinate

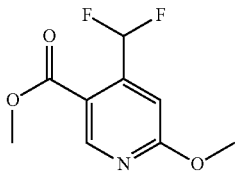

To a stirred solution of methyl 4-formyl-6-methoxynicotinate (2×8 g, 41.0 mmol, 1 eq) in DCM (80 mL) was added DAST (10.8 mL, 81.98 mmol, 2 eq) at −78° C. under argon then slowly warmed to RT and stirred for 16 h. TLC analysis indicated formation of less polar spots. The reaction mixture was cooled to 0° C., quenched with satd. aq·NaHCO$_3$ solution, extracted with DCM (2×200 ml), and washed with water (2×100 mL) and brine (2×100 mL). The combined organic layers were dried over Na$_2$SO$_4$ and concentrated under reduced pressure to give crude product of methyl 4-(difluoromethyl)-6-methoxynicotinate (8 g, crude) as an off white solid. The crude product was used without further purification. TLC: 20% EtOAc in pet ether; R$_f$: 0.7

Step 4: methyl 4-(difluoromethyl)-6-oxo-1,6-dihydropyridine-3-carboxylate

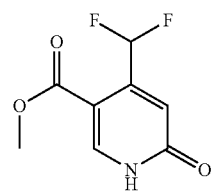

To a stirred solution of methyl 4-(difluoromethyl)-6-methoxynicotinate (16 g, 73.7 mmol, 1 eq) in ACN (160 mL) was added NaI (33.13 g, 22.1 mmol, 2 eq) followed by TMS-Cl (28.1 mL, 22.1 mmol, 3 eq) dropwise at rt under argon then slowly warmed to 80° C. and stirred for 2 h. TLC analysis indicated formation of polar spots. The reaction mixture was cooled to rt and poured into ice water. Isolation of the product gave methyl 4-(difluoromethyl)-6-oxo-1,6-dihydropyridine-3-carboxylate (14 g, 78.6%) as an off white solid. The crude product was used without further purification. TLC: 70% EtOAc in pet ether; R$_f$: 0.3

Step 5: methyl 4-(difluoromethyl)-1-methyl-6-oxo-1,6-dihydropyridine-3-carboxylate

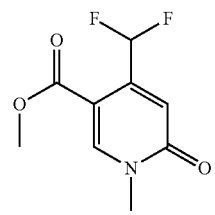

To a stirred solution of methyl 4-(difluoromethyl)-6-oxo-1,6-dihydropyridine-3-carboxylate (14 g, 68.96 mmol, 1 eq) in DMF (140 mL) was added Cs$_2$CO$_3$ (33.62 g, 103.44 mmol, 1.5 eq) followed by CH$_3$I (4.16 mL, 82.69 mmol, 1.2 eq) dropwise at RT under argon then stirred for 1 h. TLC analysis indicated formation of less polar spots. The reaction mixture was at rt poured into ice water. The solids were collected by suction filtration and dried under vacuum to give methyl 4-(difluoromethyl)-1-methyl-6-oxo-1,6-dihydropyridine-3-carboxylate (13 g, 87.2%) as an off white solid. The crude product was used without further purification. TLC: 5% EtOAc in pet ether; R$_f$: 0.6

Step 6: 4-(difluoromethyl)-1-methyl-6-oxo-1,6-dihydropyridine-3-carboxylic acid

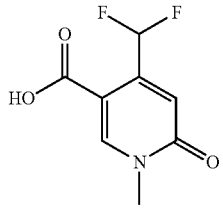

To a stirred solution of methyl 4-(difluoromethyl)-1-methyl-6-oxo-1,6-dihydropyridine-3-carboxylate (13 g, 59.9 mmol, 1 eq) in MeOH:THF:H$_2$O (50 mL: 50 mL: 30 mL) was added LiOH (5.02 g, 119.81 mmol, 2 eq) at RT stirred for 16 h. TLC analysis indicated formation of polar spot. The solvent was evaporated under reduced pressure, the reaction mixture was cooled to 0° C., acidified with 2N HCl, extracted with EtOAc (2×200 mL) and washed with water (2×100 mL) and brine (2×100 mL). Combined organic layers were dried over Na$_2$SO$_4$ and concentrated under reduced pressure to give crude product. The crude product was washed with n-pentane to obtain pure 4-(difluoromethyl)-1-methyl-6-oxo-1,6-dihydropyridine-3-carboxylic acid (10 g, 82.6%) as an off white solid. LCMS: [M+H]+: 203.95:

Step 7: (S)—N-(5-bromo-2-(3,4-dimethylpiperazin-1-yl)-4-fluorophenyl)-4-(difluoromethyl)-1-methyl-6-oxo-1,6-dihydropyridine-3-carboxamide

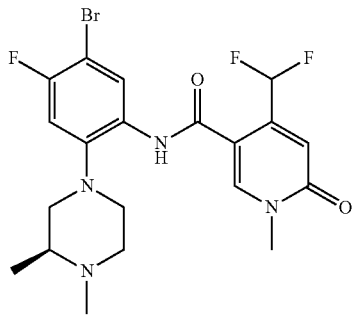 [SMILES: C[C@H]1CN(c2cc(F)c(Br)cc2NC(=O)c2cn(C)c(=O)cc2C(F)F)CCN1C]

To a stirred solution of 4-(difluoromethyl)-1-methyl-6-oxo-1,6-dihydropyridine-3-carboxylic acid (8 g, 39.40 mmol, 1 eq) in DMF (80 mL) under argon atm was added DIPEA (21.7 mL, 118.2 mmol, 3 eq), HATU (44.9 g, 118.2 mmol, 3 eq) and then (S)-5-bromo-2-(3,4-dimethylpiperazin-1-yl)-4-fluoroaniline (11.94 g, 39.4 mmol, 1 eq, preparation described in Example 196) at 0° C. and then was stirred for 16 h. TLC analysis indicated formation of nonpolar spots. The reaction mixture was diluted with ice water (200 mL) and extracted with EtOAc (2×500 mL). The organic layer was washed with brine and dried over Na$_2$SO$_4$ and concentrated under reduced pressure to give crude product. The crude product was purified by column chromatography (neutral alumina) using 0-5% MeOH in EtOAc as an eluent to afford (S)—N-(5-bromo-2-(3,4-dimethylpiperazin-1-yl)-4-fluorophenyl)-4-(difluoromethyl)-1-methyl-6-oxo-1,6-dihydropyridine-3-carboxamide (5.5 g, 50%) as a pale brown solid; LCMS: [M+H]+ 487.25.

Step 8: N-[5-(6-acetamidopyridin-3-yl)-4-fluoro-2-[(3R)-3,4-dimethylpiperazin-1-yl]phenyl]-4-(difluoromethyl)-1-methyl-6-oxopyridine-3-carboxamide

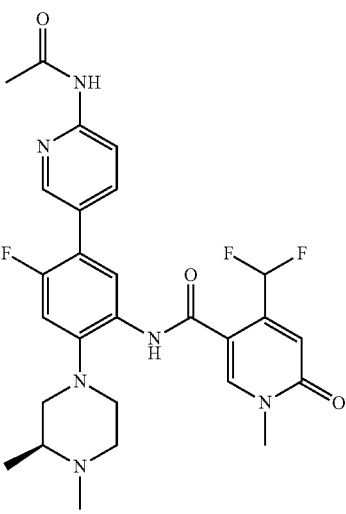

The title compound was prepared through a procedure similar to that described in the final step of Example 100 using 2-acetamidopyridine-5-boronic acid, pinacol ester and (S)-4-(difluoromethyl)-N-(2-(3,4-dimethylpiperazin-1-yl)-4-fluoro-5-(2-morpholinopyrimidin-5-yl)phenyl)-1-methyl-6-oxo-1,6-dihydropyridine-3-carboxamide to give the title compound which was purified using standard methods. $^1$H NMR (500 MHz, MeOD) δ 8.47 (s, 1H), 8.30 (s, 1H), 8.17 (d, J=8.6 Hz, 1H), 7.95 (d, J=9.6 Hz, 1H), 7.83 (d, J=8.3 Hz, 1H), 7.28 (t, J=55.1 Hz, 1H), 7.09 (d, J=12.1 Hz, 1H), 6.82 (s, 1H), 3.65 (s, 3H), 3.14 (dd, J=11.7, 2.2 Hz, 1H), 3.08 (d, J=11.6 Hz, 1H), 2.93 (ddd, J=11.6, 10.0, 2.4 Hz, 2H), 2.52 (ddd, J=14.1, 13.6, 6.3 Hz, 2H), 2.41-2.36 (m, 1H), 2.35 (s, 3H), 2.20 (s, 3H), 1.11 (d, J=6.3 Hz, 3H); LCMS [M+1]+=543.30.

Example 218: N-[5-(2-cyanopyrimidin-5-yl)-4-fluoro-2-[(3R)-3,4-dimethylpiperazin-1-yl]phenyl]-4-(difluoromethyl)-1-methyl-6-oxopyridine-3-carboxamide

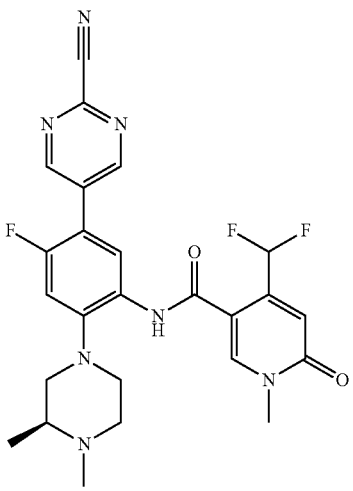 [SMILES: C[C@H]1CN(c2cc(F)c(-c3cnc(C#N)nc3)cc2NC(=O)c2cn(C)c(=O)cc2C(F)F)CCN1C]

The title compound was prepared using a procedure similar to Example 217 using 2-cyanopyrimidine-5-boronic acid pinacol ester and (S)—N-(5-bromo-2-(3,4-dimethylpiperazin-1-yl)-4-fluorophenyl)-4-(difluoromethyl)-1-methyl-6-oxo-1,6-dihydropyridine-3-carboxamide in the final step. $^1$H NMR (500 MHz, MeOD) δ 9.04 (s, 2H), 8.19 (s, 1H), 7.85 (d, J=8.2 Hz, 1H), 7.25 (d, J=55.0 Hz, 1H), 7.07 (d, J=12.6 Hz, 1H), 6.72 (s, 1H), 3.55 (s, 3H), 3.11 (dq, J=11.6, 2.2 Hz, 1H), 3.05 (dt, J=11.9, 2.4 Hz, 1H), 2.86 (t, J=11.6 Hz, 1H), 2.82 (dt, J=11.5, 2.1 Hz, 1H), 2.50-2.45 (m, 1H), 2.42 (td, J=11.4, 2.9 Hz, 1H), 2.31-2.27 (m, 1H), 2.25 (s, 3H), 1.01 (d, J=6.3 Hz, 3H); LCMS [M+1]+=512.30.

Example 219: N-[5-[6-(dimethylamino)pyridin-3-yl]-4-fluoro-2-[(3R)-3,4-dimethylpiperazin-1-yl]phenyl]-6-oxo-4-(trifluoromethyl)-1H-pyridine-3-carboxamide

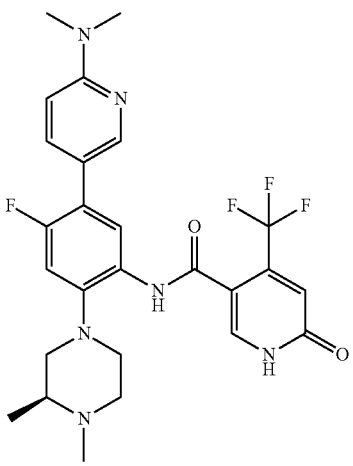

The title compound was prepared similar to the sequence described above for the preparation of Example 196 using 6-(dimethylamino)pyridine-3-boronic acid pinacol ester in place of 2-acetamidopyridine-5-boronic acid, pinacol ester. $^1$H NMR (500 MHz, MeOD) δ 8.25 (s, 1H), 7.96 (s, 1H), 7.90 (d, J=8.3 Hz, 1H), 7.74 (d, J=9.0 Hz, 1H), 7.06 (d, J=12.1 Hz, 1H), 6.91 (s, 1H), 6.75 (d, J=9.0 Hz, 1H), 3.12 (s, 6H), 3.09 (dq, J=11.3, 1.9 Hz, 1H), 3.04 (dt, J=11.5 Hz, 1H), 2.97-2.90 (m, 2H), 2.55 (ddd, J=11.4, 10.3, 3.9 Hz, 2H), 2.44-2.40 (m, 1H), 2.38 (s, 3H), 1.13 (d, J=6.3 Hz, 3H); LCMS [M+1]+=533.29.

Example 220: N-[5-[5-cyano-6-(dimethylamino)pyridin-3-yl]-4-fluoro-2-[(3R 5S)-3,4,5-trimethylpiperazin-1-yl]phenyl]-6-oxo-4-(trifluoromethyl)-1H-pyridine-3-carboxamide

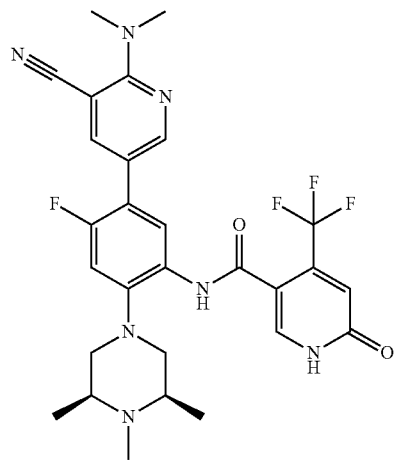 [SMILES: C[C@@H]1CN(c2cc(F)c(-c3cnc(N(C)C)c(C#N)c3)cc2NC(=O)c2c[nH]c(=O)cc2C(F)(F)F)C[C@H](C)N1C]

The procedure was similar to Example 39 using 3-cyano-2-(N,N-dimethylamino)pyridine-5-boronic acid, pinacol ester (0.034 g, 0.125 mmol), N-(5-bromo-4-fluoro-2-((3R,5S)-3,4,5-trimethylpiperazin-1-yl)phenyl)-4-(trifluoromethyl)-6-(2-(trimethylsilyl)ethoxy)nicotinamide (0.05033 g, 0.083 mmol) to give, after deprotection of the silyloxy coupled product 38.3 mg (77% yield) the title compound. $^1$H NMR (500 MHz, MeOD) δ 8.49 (s, 1H), 8.04 (d, J=1.8 Hz, 1H), 7.96 (s, 1H), 7.89 (d, J=8.3 Hz, 1H), 7.07 (d, J=12.2 Hz, 1H), 6.91 (s, 1H), 3.33 (s, 6H), 3.06 (d, J=11.2 Hz, 2H), 2.61 (t, J=11.1 Hz, 2H), 2.57-2.51 (m, 2H), 2.37 (s, 3H), 1.16 (d, J=6.1 Hz, 6H); LCMS [M+1]+=572.34.

369

Example 221: N-[5-[6-(dimethylamino)-5-fluoro-pyridin-3-yl]-4-fluoro-2-[(3R,5S)-3,4,5-trimethylpiperazin-1-yl]phenyl]-6-oxo-4-(trifluoromethyl)-1H-pyridine-3-carboxamide

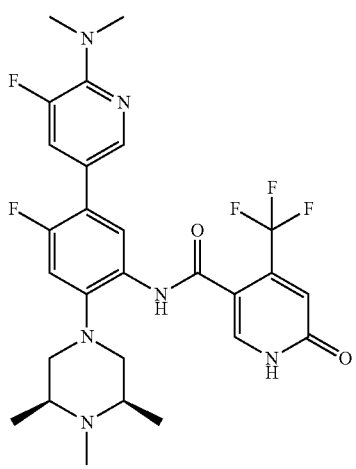 [SMILES: C[C@@H]1CN(c2cc(F)c(-c3cnc(N(C)C)c(F)c3)cc2NC(=O)c2c[nH]c(=O)cc2C(F)(F)F)C[C@H](C)N1C]

The title compound was prepared by a procedure similar to that of Example 39 using 2-(N,N-dimethylamino)-3-fluoropyridine-5-boronic acid pinacol ester hydrochloride (0.039 g, 0.129 mmol), N-(5-bromo-4-fluoro-2-((3R,5S)-3,4,5-trimethylpiperazin-1-yl)phenyl)-4-(trifluoromethyl)-6-(2-(trimethylsilyl)ethoxy)nicotinamide (0.05214 g, 0.086 mmol) to give the title compound (14 mg, 29% yield). $^1$H NMR (500 MHz, MeOD) δ 8.12 (s, 1H), 7.96 (s, 1H), 7.90 (d, J=8.2 Hz, 1H), 7.55 (d, J=14.9 Hz, 1H), 7.06 (d, J=12.2 Hz, 1H), 6.91 (s, 1H), 3.13 (d, J=2.0 Hz, 6H), 3.06 (d, J=11.1 Hz, 2H), 2.61 (t, J=11.1 Hz, 2H), 2.56 (dt, J=9.8, 6.5 Hz, 2H), 2.38 (s, 3H), 1.16 (d, J=6.1 Hz, 6H); $^{19}$F NMR (471 MHz, MeOD) δ −63.79 (s), −120.46 (s), −131.66 (s); LCMS [M+1]+=565.34.

370

Example 222: N-[5-(5-chloro-6-morpholin-4-ylpyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

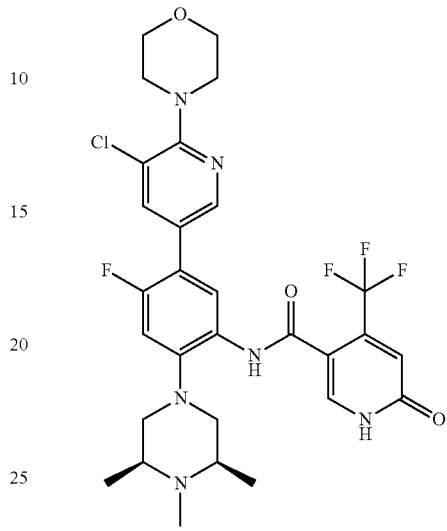

The title compound was prepared similar to the sequence described above for the preparation of Example 39 using 5-chloro-6-morpholinopyridin-3-ylboronic acid (0.032 g, 0.130 mmol), N-(5-bromo-4-fluoro-2-((3R,5S)-3,4,5-trimethylpiperazin-1-yl)phenyl)-4-(trifluoromethyl)-6-(2-(trimethylsilyl)ethoxy)nicotinamide (0.05251 g, 0.087 mmol) to give the title compound (14 mg, 26% yield). $^1$H NMR (500 MHz, MeOD) δ 8.37 (s, 1H), 7.96 (s, 1H), 7.93 (s, 1H), 7.91 (d, J=8.2 Hz, 1H), 7.08 (d, J=12.1 Hz, 1H), 6.91 (s, 1H), 3.87-3.84 (m, 4H), 3.41-3.39 (m, 4H), 3.07 (d, J=11.2 Hz, 2H), 2.62 (t, J=11.1 Hz, 2H), 2.55 (dd, J=12.6, 6.7 Hz, 2H), 2.37 (s, 3H), 1.16 (d, J=6.1 Hz, 6H); LCMS [M+1]+=623.27.

Example 223: N-[5-(2,3-dihydro-[1,4]dioxino[2,3-b]pyridin-7-yl)-4-fluoro-2-[(3R,5S)-3,4,5-trimethylpiperazin-1-yl]phenyl]-6-oxo-4-(trifluoromethyl)-1H-pyridine-3-carboxamide

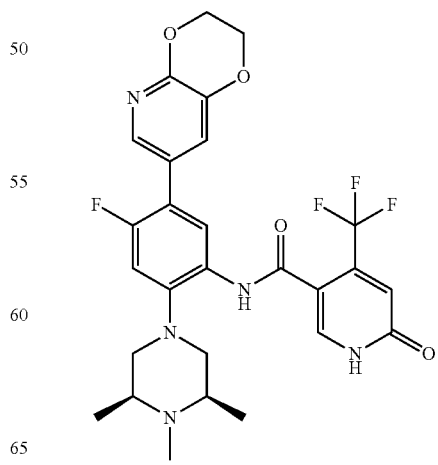

The procedure used was similar to Example 39 except using 7-(4,4,5,5-tetramethyl-1,3,2-dioxaborolan-2-yl)-2,3-dihydro-[1,4]dioxino[2,3-b]pyridine (0.033 g, 0.125 mmol) and N-(5-bromo-4-fluoro-2-((3R,5S)-3,4,5-trimethylpiperazin-1-yl)phenyl)-4-(trifluoromethyl)-6-(2-(trimethylsilyl)ethoxy)nicotinamide (0.05027 g, 0.083 mmol) to give after deprotection of the silyloxy coupled intermediate the title compound (41 mg, 85% yield). $^1$H NMR (500 MHz, MeOD) δ 7.95 (s, 1H), 7.89 (d, J=7.6 Hz, 2H), 7.50 (s, 1H), 7.07 (d, J=12.1 Hz, 1H), 6.91 (s, 1H), 4.49 (dd, J=5.0, 3.1 Hz, 2H), 4.33 (dd, J=5.0, 3.1 Hz, 2H), 3.07 (d, J=11.2 Hz, 2H), 2.62 (t, J=11.1 Hz, 2H), 2.56 (dt, J=9.6, 6.2 Hz, 2H), 2.37 (s, 3H), 1.16 (d, J=6.1 Hz, 6H); LCMS [M+H]+=562.26.

Example 224: 2-(difluoromethyl)-N-(2-((S)-3,4-dimethylpiperazin-1-yl)-4-fluoro-5-(2-((S)-2-methylmorpholino)pyrimidin-5-yl)phenyl)-4-fluorobenzamide

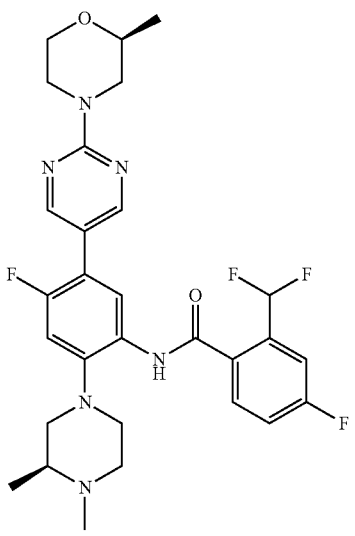 [SMILES: C[C@H]1CN(c2ncc(-c3cc(NC(=O)c4ccc(F)cc4C(F)F)c(N4CCN(C)[C@@H](C)C4)cc3F)cn2)CCO1]

The title compound (formic acid salt, white solid, 46.9 mg, 41%) was prepared according to a procedure similar to Example 31 using crude (S)-(2-(2-methylmorpholino)pyrimidin-5-yl)boronic acid (0.555 mmol+0.278 mmol) and (S)—N-(5-bromo-2-(3,4-dimethylpiperazin-1-yl)-4-fluorophenyl)-2-(difluoromethyl)-4-fluorobenzamide (prepared as described in Example 62) in dioxane (0.185 mmol). $^1$H NMR (500 MHz, METHANOL-d4) δ=8.57 (br s, 2H), 8.36 (br dd, J=1.7, 2.8 Hz, 1H), 7.96 (br d, J=8.1 Hz, 1H), 7.93-7.87 (m, 1H), 7.56 (br d, J=9.3 Hz, 1H), 7.50-7.26 (m, 2H), 7.19 (d, J=11.9 Hz, 1H), 4.65-4.54 (m, 2H), 3.99 (br d, J=11.6 Hz, 1H), 3.68-3.58 (m, 2H), 3.48-3.38 (m, 1H), 3.31-3.25 (m, 2H), 3.22-3.04 (m, 4H), 2.94-2.83 (m, 1H), 2.82-2.71 (m, 4H), 1.37-1.30 (m, 3H), 1.25 (d, J=6.1 Hz, 3H); LCMS [M+H]+ 573.3

Example 225: N-[4-fluoro-5-(2-morpholin-4-ylpyrimidin-5-yl)-2-(3,3,4-trimethylpiperazin-1-yl)phenyl]-6-oxo-4-(trifluoromethyl)-1H-pyridine-3-carboxamide

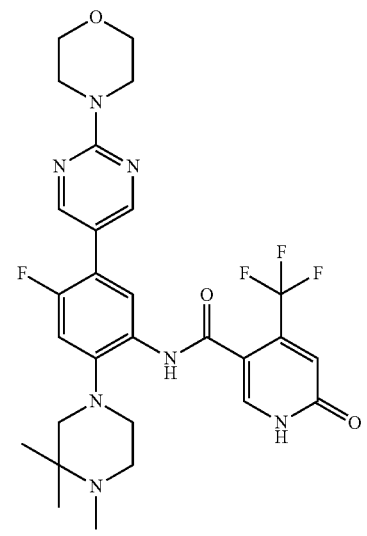

Step 1: Preparation of 5-bromo-4-fluoro-2-(3,3,4-trimethylpiperazin-1-yl)aniline

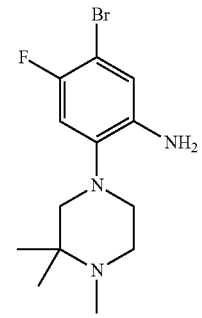 [SMILES: CN1CCN(c2cc(F)c(Br)cc2N)CC1(C)C]

To a suspension of K$_2$CO$_3$ (566 mg, 4.09 mmol, 0.525 equiv.) in toluene (20 mL) was added 1,2,2-trimethyl-piperazine (1.00 g, 7.8 mmol), followed by dropwise addition of a solution of 1-bromo-2,4-difluoro-5-nitrobenzene (0.98 mL, 7.8 mmol) in toluene (3 mL) over 2 min. The resulting mixture was stirred at rt for 30 min, then 45° C. for 1.5 h resulting in an abundance of yellow precipitate. After diluting with H$_2$O (20 mL) to dissolve the insoluble salts, it was extracted with EtOAc (20 mL×2). The combined extracts were concentrated and dried under vacuum to give the nitro intermediate as an orange red oil. LCMS [M+H]+ 346.2. To a solution of the above orange oil in MeOH (30 mL) was added a suspension of Raney-Nickel (334 mg, 3.9 mmol) in MeOH (5 mL), followed by hydrazine monohydrate (1.14 mL, 23.4 mmol) dropwise over 2 min. After addition, the reaction mixture was stirred at rt for 30 min. Additional Raney-Nickel (334 mg, 3.9 mmol) in MeOH (5 mL) and hydrazine monohydrate (1.14 mL, 23.4 mmol) were added, followed by THF (15 mL) to make a clear solution. The resulting mixture was heated at 60° C. for 30 min. Additional THF (10 mL) and hydrazine monohydrate (0.38 mL, 7.8 mmol) were added and it was heated at 60° C. for 30 min. After filtration, the filtrate was concentrated to give a dark brown liquid which was purified by flash chromatography (gradient: EtOAc/hex 0-100% then MeOH/DCM 0-10%) to give the title compound as a beige solid (1.796 g, 68%). LCMS [M+H]$^+$ 316.2.

Step 2: Preparation of N-(5-bromo-4-fluoro-2-(3,3,4-trimethylpiperazin-1-yl)phenyl)-6-oxo-4-(trifluoromethyl)-1,6-dihydropyridine-3-carboxamide

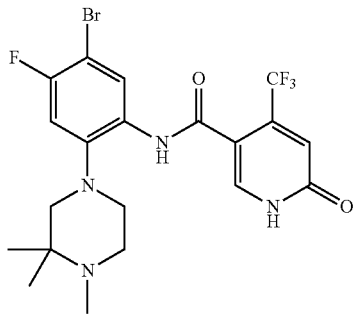 [SMILES: CN1CCN(c2cc(F)c(Br)cc2NC(=O)c2c[nH]c(=O)cc2C(F)(F)F)CC1(C)C]

The title compound (beige solid, 1.303 g, 70%) was prepared by a method similar to that of Example 29 Step 3 using 5-bromo-4-fluoro-2-(3,3,4-trimethylpiperazin-1-yl)aniline. LCMS [M+H]$^+$ 505.2.

Step 3: Preparation of N-(4-fluoro-5-(2-morpholinopyrimidin-5-yl)-2-(3,3,4-trimethylpiperazin-1-yl)phenyl)-6-oxo-4-(trifluoromethyl)-1,6-dihydropyridine-3-carboxamide

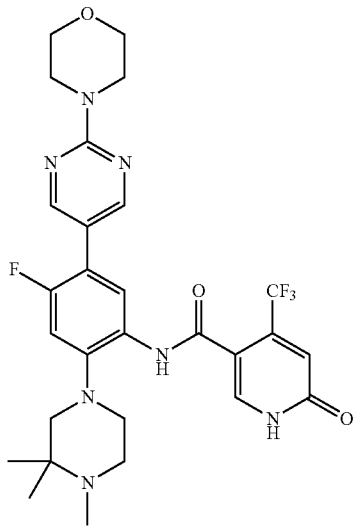 [SMILES: CN1CCN(c2cc(F)c(-c3cnc(N4CCOCC4)nc3)cc2NC(=O)c2c[nH]c(=O)cc2C(F)(F)F)CC1(C)C]

The title compound (white solid, 36.3 mg, 61%) was prepared using a procedure similar to the final step of Example 31 using N-(5-bromo-4-fluoro-2-(3,3,4-trimethylpiperazin-1-yl)phenyl)-6-oxo-4-(trifluoromethyl)-1,6-dihydropyridine-3-carboxamide (50.5 mg, 0.1 mmol) and 2-(4-morpholino)pyrimidine-5-boronic acid pinacol ester (58 mg, 0.2 mmol). $^1$H NMR (500 MHz, METHANOL-d4) δ=8.56 (s, 2H), 8.09 (s, 1H), 7.91 (br d, J=8.2 Hz, 1H), 7.13 (d, J=12.1 Hz, 1H), 6.93 (s, 1H), 3.88-3.82 (m, 4H), 3.80-3.74 (m, 4H), 3.10-2.99 (m, 2H), 2.85-2.75 (m, 2H), 2.70 (s, 2H), 2.33 (s, 3H), 1.13 (s, 6H); LCMS [M+H]$^+$ 590.3.

Example 226: N-[4-fluoro-5-(2-morpholin-4-ylpyridin-4-yl)-2-[(3R,5S)-3,4,5-trimethylpiperazin-1-yl]phenyl]-1-methyl-6-oxo-4-(trifluoromethyl)pyridine-3-carboxamide

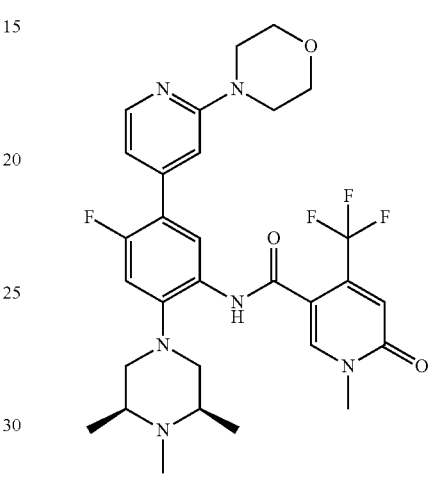

Step 1: N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide

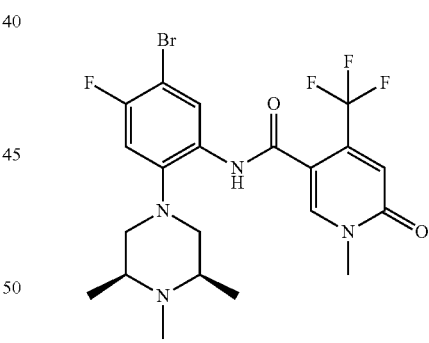

To a stirred solution of 1-methyl-6-oxo-4-(trifluoromethyl)-1,6-dihydropyridine-3-carboxylic acid (2.1 g, 9.50 mmol, 1 eq, from Example 93) in DMF (30 mL) was added HATU (10.83 g, 28.50 mmol, 3 eq) at 0° C. under argon atmosphere followed by DIPEA (5.2 mL, 28.50 mmol, 3 eq) and stirred for 15 min at the same temp. Then, 5-bromo-4-fluoro-2-((3S,5R)-3,4,5-trimethylpiperazin-1-yl)aniline (2.99 g, 9.50 mmol, 1 eq) was added at 0° C. and allowed to remain at RT over 32 h. TLC analysis indicated formation of polar spot. The reaction mixture was diluted with water (300 mL) and extracted with DCM (3×100 mL). The organic layer was washed with water (2×200 mL) and dried over Na$_2$SO$_4$ and concentrated under reduced pressure to give crude product. Crude product was purified by column chromatography (Neutral Alumina) using 0-30% EtOAc in Methanol as an eluent and gave (1.5 g, 30.48%) as an off white solid. LCMS: [M+H]+ 221.95.

Step 2: N-[4-fluoro-5-(2-morpholin-4-ylpyridin-4-yl)-2-[(3R,5S)-3,4,5-trimethylpiperazin-1-yl]phenyl]-1-methyl-6-oxo-4-(trifluoromethyl)pyridine-3-carboxamide

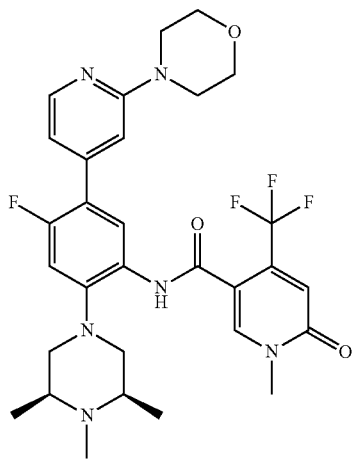

The title compound (white solid, 21.2 mg, 35%) was prepared according to a procedure similar to that of Example 31 using N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (51.9 mg, 0.1 mmol) and 2-morpholinopyridine-4-boronic acid, pinacol ester (58 mg, 0.2 mmol). $^1$H NMR (500 MHz, CHLOROFORM-d) δ=8.68 (s, 1H), 8.51 (d, J=8.1 Hz, 1H), 8.25 (d, J=5.1 Hz, 1H), 7.88 (s, 1H), 7.01 (d, J=11.4 Hz, 1H), 6.99-6.97 (m, 1H), 6.88 (d, J=5.1 Hz, 1H), 6.80 (s, 1H), 3.89-3.82 (m, 4H), 3.65 (s, 3H), 3.59-3.53 (m, 4H), 2.82 (br d, J=10.9 Hz, 2H), 2.64 (br t, J=10.9 Hz, 2H), 2.37-2.27 (m, 5H), 1.14 (d, J=6.2 Hz, 6H); LCMS [M+H]$^+$ 603.4.

Example 227: N-[4-fluoro-5-(4-pyrrolidin-1-ylphenyl)-2-[(3R,5S)-3,4,5-trimethylpiperazin-1-yl]phenyl]-1-methyl-6-oxo-4-(trifluoromethyl)pyridine-3-carboxamide

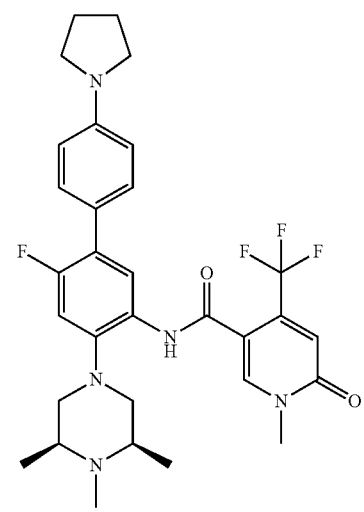

The title compound (yellow solid, 37.5 mg, 64%) was prepared by a procedure similar to that of Example 29 using N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (51.9 mg, 0.1 mmol) and 1-[4-(4,4,5,5-tetramethyl-1,3,2-dioxaborolan-2-yl)phenyl] pyrrolidine (55 mg, 0.2 mmol). $^1$H NMR (500 MHz, CHLOROFORM-d) δ=8.72 (s, 1H), 8.48 (d, J=8.3 Hz, 1H), 7.86 (s, 1H), 7.48 (br d, J=7.5 Hz, 2H), 7.01-6.94 (m, 2H), 6.62 (d, J=8.7 Hz, 2H), 3.64 (s, 3H), 3.34 (br t, J=6.4 Hz, 4H), 2.81 (br d, J=11.0 Hz, 2H), 2.64 (br t, J=10.9 Hz, 2H), 2.36-2.27 (m, 5H), 2.07-1.99 (m, 4H), 1.13 (d, J=6.1 Hz, 6H); LCMS [M+H]$^+$ 586.3.

Example 228: N-[5-[4-(cyclopropylmethoxy)phenyl]-4-fluoro-2-[(3R,5S)-3,4,5-trimethylpiperazin-1-yl]phenyl]-1-methyl-6-oxo-4-(trifluoromethyl)pyridine-3-carboxamide

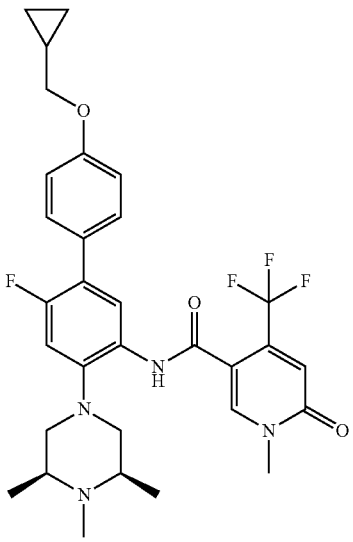

The title compound (white solid, 37.0 mg, 63%) was prepared in a manner similar to Example 31 using N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (51.9 mg, 0.1 mmol) and 4-(cyclopropylmethoxy)phenylboronic acid (38 mg, 0.2 mmol). $^1$H NMR (500 MHz, CHLOROFORM-d) δ=8.71 (s, 1H), 8.47 (d, J=8.3 Hz, 1H), 7.86 (s, 1H), 7.51 (d, J=7.6 Hz, 2H), 7.01-6.95 (m, 4H), 3.85 (d, J=6.8 Hz, 2H), 3.64 (s, 3H), 2.81 (br d, J=10.9 Hz, 2H), 2.64 (t, J=10.9 Hz, 2H), 2.35-2.28 (m, 5H), 1.35-1.25 (m, 1H), 1.13 (d, J=6.2 Hz, 6H), 0.70-0.63 (m, 2H), 0.40-0.35 (m, 2H); LCMS [M+H]$^+$ 587.4.

Example 229: 2,3-difluoro-N-[4-fluoro-5-(2-morpholin-4-ylpyrimidin-5-yl)-2-[(3R,5S)-3,4,5-trimethylpiperazin-1-yl]phenyl]benzamide The title compound (white solid, 37.0 mg, 63%) was prepared through a procedure similar to that of Example 31 using N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (51.9 mg, 0.1 mmol) and 4-(cyclopropylmethoxy)phenylboronic acid (38 mg, 0.2 mmol). $^1$H NMR (500 MHz, CHLOROFORM-d) δ=8.71 (s, 1H), 8.47 (d, J=8.3 Hz, 1H), 7.86 (s, 1H), 7.51 (d, J=7.6 Hz, 2H), 7.01-6.95 (m, 4H), 3.85 (d, J=6.8 Hz, 2H), 3.64 (s, 3H), 2.81 (br d, J=10.9 Hz, 2H), 2.64 (t, J=10.9 Hz, 2H), 2.35-2.28 (m, 5H), 1.35-1.25 (m, 1H), 1.13 (d, J=6.2 Hz, 6H), 0.70-0.63 (m, 2H), 0.40-0.35 (m, 2H); LCMS [M+H]$^+$ 587.4.

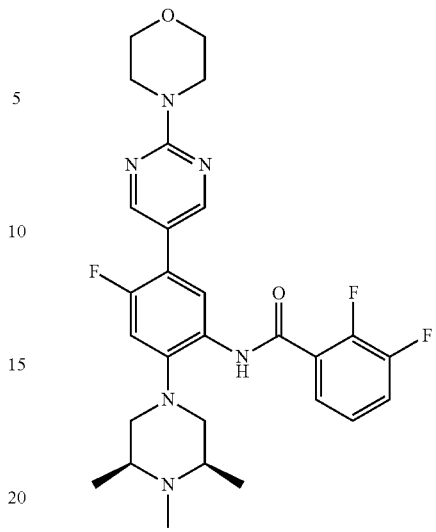

The title compound (light beige solid, 46.8 mg, 84%) was prepared in a procedure similar to that of Example 34 using 4-fluoro-5-(2-morpholinopyrimidin-5-yl)-2-((3S,5R)-3,4,5-trimethylpiperazin-1-yl)aniline (40 mg, 0.1 mmol) and 2,3-difluorobenzoyl chloride (19 μL, 0.15 mmol). $^1$H NMR (500 MHz, CHLOROFORM-d) δ=9.74 (br d, J=12.1 Hz, 1H), 8.72 (d, J=8.2 Hz, 1H), 8.58 (s, 2H), 7.95 (t, J=7.2 Hz, 1H), 7.43-7.36 (m, 1H), 7.31-7.26 (m, 1H), 7.04 (d, J=11.4 Hz, 1H), 3.90-3.86 (m, 4H), 3.82-3.79 (m, 4H), 2.89 (br d, J=10.9 Hz, 2H), 2.67 (t, J=10.8 Hz, 2H), 2.55-2.46 (m, 2H), 2.38 (s, 3H), 1.16 (d, J=6.2 Hz, 6H); LCMS [M+H]$^+$ 541.3.

Example 230: 2-chloro-4-fluoro-N-[4-fluoro-5-(2-morpholin-4-ylpyrimidin-5-yl)-2-[(3R)-3,4-dimethylpiperazin-1-yl]phenyl]benzamide

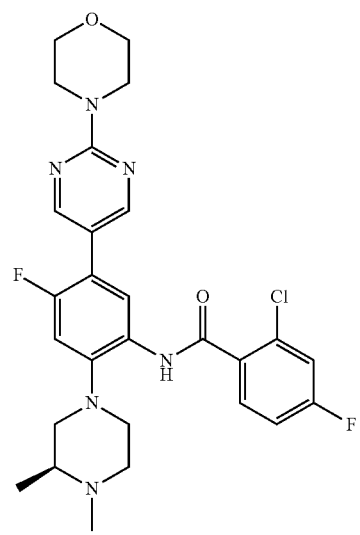 [SMILES: C[C@H]1CN(c2cc(F)c(-c3cnc(N4CCOCC4)nc3)cc2NC(=O)c2ccc(F)cc2Cl)CCN1C]

The title compound (light beige solid, 23.6 mg, 70%) was prepared by a procedure similar to that of Example 78 using (S)-2-(3,4-dimethylpiperazin-1-yl)-4-fluoro-5-(2-morpholinopyrimidin-5-yl)aniline (23 mg, 0.06 mmol) and 2-chloro-4-fluorobenzoylchloride (12 μL, 0.09 mmol). $^1$H NMR (500 MHz, CHLOROFORM-d) δ=9.20 (s, 1H), 8.68 (d, J=8.2 Hz, 1H), 8.59 (s, 2H), 7.85 (dd, J=6.0, 8.7 Hz, 1H), 7.25 (dd, J=2.4, 8.3 Hz, 1H), 7.15 (t, J=8.2 Hz, 1H), 7.04 (d, J=11.2 Hz, 1H), 3.91-3.86 (m, 4H), 3.82-3.78 (m, 4H), 3.01-2.85 (m, 4H), 2.60 (t, J=10.6 Hz, 1H), 2.42 (dt, J=3.2, 11.0 Hz, 1H), 2.35 (s, 3H), 2.26 (br s, 1H), 1.09 (d, J=6.2 Hz, 3H); LCMS [M+H]+ 543.4.

Example 231: N-[5-(I-cyclopentyl-3,6-dihydro-2H-pyridin-4-yl)-4-fluoro-2-[(3R,5S)-3,4,5-trimethylpiperazin-1-yl]phenyl]-6-oxo-4-(trifluoromethyl)-1H-pyridine-3-carboxamide

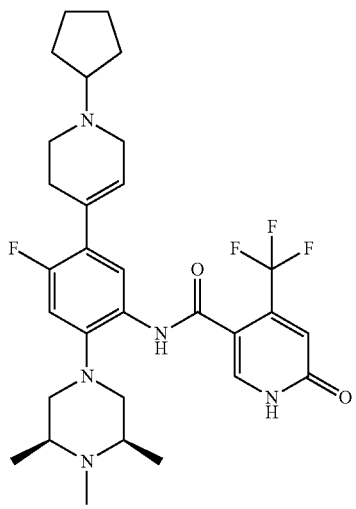

The procedure used was similar to Example 148 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (34 mg, 0.057 mmol) and cyclopentanone (7.59 µl, 0.085 mmol) to give, after isolation of the product combined and concentrated to afford the title compound as a yellow powder (28 mg, 77% yield) of the title compound. $^1$H NMR (500 MHz, METHANOL-d4) δ=8.02-7.93 (m, 1H), 7.84-7.75 (m, 1H), 6.98-6.92 (m, 1H), 6.91-6.87 (m, 1H), 6.09-5.99 (m, 1H), 3.43-3.38 (m, 2H), 3.07-2.99 (m, 2H), 2.97-2.90 (m, 2H), 2.89-2.81 (m, 1H), 2.68-2.62 (m, 2H), 2.62-2.56 (m, 2H), 2.56-2.49 (m, 2H), 2.39-2.36 (m, 3H), 2.09-2.01 (m, 2H), 1.83-1.75 (m, 2H), 1.71-1.63 (m, 2H), 1.61-1.52 (m, 2H), 1.18-1.15 (m, 6H); LCMS [M+H]+ 576.5

Example 232: N-[4-fluoro-5-[1-[1-(4-methoxyphenyl)ethyl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

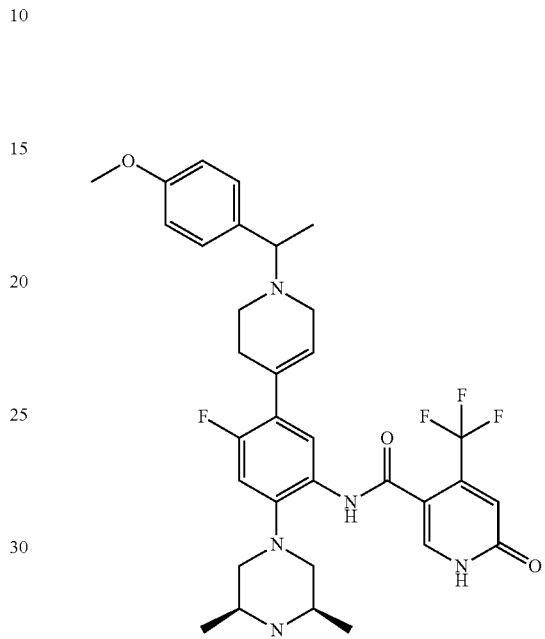

The procedure used was similar to that of Example 148 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (40 mg, 0.067 mmol), 4'-methoxyacetophenone 99% (15.09 mg, 0.100 mmol) and Titanium(IV) isopropoxide (0.060 ml, 0.201 mmol) which were mixed in anhydrous THF. The reaction mixture was heated at 75° C. for 6 h. The reaction mixture was then cooled to RT and EtOH (2 ml) and sodium borohydride (10.14 mg, 0.268 mmol) were added in sequence. The mixture was then allowed to stir at room temperature for 16 h. The workup and isolation using standard methods provided the title compound (7 mg, 14% yield). $^1$H NMR (500 MHz, METHANOL-d4) δ=7.94-7.84 (m, 1H), 7.77-7.68 (m, 1H), 7.43-7.31 (m, 2H), 7.04-6.92 (m, 3H), 6.85-6.78 (m, 1H), 5.98-5.87 (m, 1H), 4.46-4.36 (m, 1H), 3.86-3.76 (m, 1H), 3.76-3.72 (m, 3H), 3.71-3.63 (m, 1H), 3.47-3.26 (m, 4H), 3.19-3.12 (m, 2H), 2.89-2.81 (m, 2H), 2.80-2.77 (m, 3H), 2.76-2.69 (m, 2H), 1.73-1.65 (m, 3H), 1.30 (d, J=6.4 Hz, 6H); LCMS [M+H]+ 642.6

Example 233: N-[5-(I-butan-2-yl-3,6-dihydro-2H-pyridin-4-yl)-4-fluoro-2-[(3R,5S)-3,4,5-trimethylpiperazin-1-yl]phenyl]-6-oxo-4-(trifluoromethyl)-1H-pyridine-3-carboxamide

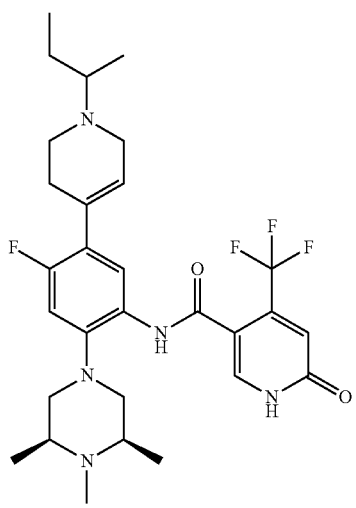

The procedure was similar to Example 148 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) and 2-butanone (7.94 µl, 0.089 mmol) to give the title compound (9 mg, 24% yield). $^1$H NMR (500 MHz, METHANOL-d4) δ=8.83-8.30 (m, 2H), 7.93 (br s, 1H), 7.90-7.80 (m, 1H), 7.03 (br d, J=12.3 Hz, 1H), 6.94 (br s, 1H), 6.09 (br s, 1H), 3.90 (br s, 2H), 3.58-3.41 (m, 3H), 3.15-3.05 (m, 2H), 2.95-2.84 (m, 2H), 2.83-2.73 (m, 2H), 2.72-2.63 (m, 2H), 2.51 (s, 3H), 2.02-1.88 (m, 1H), 1.73-1.61 (m, 1H), 1.44-1.38 (m, 3H), 1.28-1.21 (m, 6H), 1.13-1.05 (m, 3H); LCMS [M+H]+ 564.5

Example 234: N-[4-fluoro-5-(6-morpholin-4-ylpyridin-3-yl)-2-[(3R)-3-(dimethylamino)pyrrolidin-1-yl]phenyl]-6-oxo-4-(trifluoromethyl)-1H-pyridine-3-carboxamide

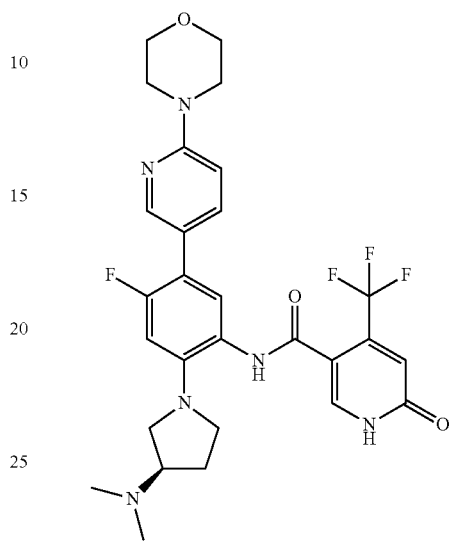

Step 1: (R)-1-(2-amino-4-bromo-5-fluorophenyl)-N,N-dimethylpyrrolidin-3-amine

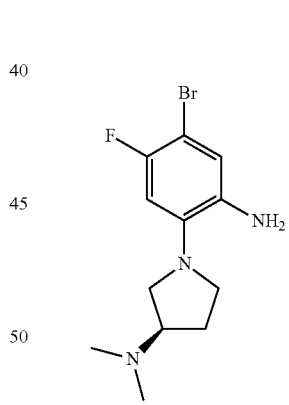

A mixture of (R)-1-(4-bromo-5-fluoro-2-nitrophenyl)-N,N-dimethylpyrrolidin-3-amine (0.65 g, 2.0 mmol) and SnCl$_2$ (0.93 g, 4.9 mmol) in EtOH (8 mL) was heated to 75° C. 4 h. After cooling to room temperature the reaction mixture was concentrated onto celite. Purification by flash chromatography [1-20% MeOH/DCM] afforded (R)-1-(2-amino-4-bromo-5-fluorophenyl)-N,N-dimethylpyrrolidin-3-amine (0.61 g, 95%). LCMS [M+H]+: 302.3.

Step 2: (R)—N-(5-bromo-2-(3-(dimethylamino)pyrrolidin-1-yl)-4-fluorophenyl)-4-(trifluoromethyl)-6-(2-(trimethylsilyl)ethoxy)nicotinamide

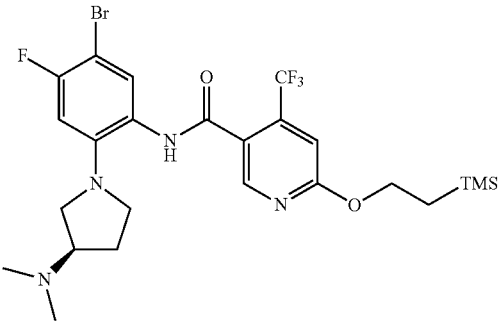 [SMILES: CN(C)[C@@H]1CCN(c2cc(F)c(Br)cc2NC(=O)c2cnc(OCC[Si](C)(C)C)cc2C(F)(F)F)C1]

4-(Trifluoromethyl)-6-(2-(trimethylsilyl)ethoxy)nicotinic acid (0.30 g, 0.99 mmol) was activated with HATU (0.38 g, 0.99 mmol) and N,N-diisopropylethylamine (0.36 mL, 2.1 mmol) in DMF (1 mL) at room temperature. The solution of activated acid was added to a solution of (R)-1-(2-amino-4-bromo-5-fluorophenyl)-N,N-dimethylpyrrolidin-3-amine (0.250 g, 0.827 mmol) in DMF (3 mL) and the reaction was heated to 55° C. for 18 h. After cooling to room temperature the reaction was partitioned between H₂O and DCM. The layers were separated and the aqueous layer was extracted with an additional portion of DCM. The combined organics were washed with water, 1N NaOH (Aq.), brine and dried over magnesium sulfate. After removal of the inorganics by filtration the filtrate was concentrated onto celite. Purification by flash chromatography [0-5% MeOH/DCM] afforded (R)—N-(5-bromo-2-(3-(dimethylamino)pyrrolidin-1-yl)-4-fluorophenyl)-4-(trifluoromethyl)-6-(2-(trimethylsilyl)ethoxy)nicotinamide (0.12 g, 24%). LCMS [M+H]+: 591.2.

Step 3: (R)—N-(2-(3-(dimethylamino)pyrrolidin-1-yl)-4-fluoro-5-(6-morpholinopyridin-3-yl)phenyl)-6-oxo-4-(trifluoromethyl)-1,6-dihydropyridine-3-carboxamide

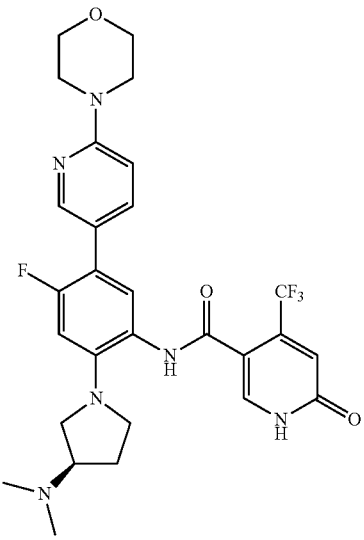 [SMILES: CN(C)[C@@H]1CCN(c2cc(F)c(-c3ccc(N4CCOCC4)nc3)cc2NC(=O)c2c[nH]c(=O)cc2C(F)(F)F)C1]

A microwave vial was charged with (R)—N-(5-bromo-2-(3-(dimethylamino)pyrrolidin-1-yl)-4-fluorophenyl)-4-(trifluoromethyl)-6-(2-(trimethylsilyl)ethoxy)nicotinamide (0.058 g, 0.098 mmol), 4-[5-(4,4,5,5-tetramethyl-[1,3,2]dioxaborolan-2-yl)-pyridin-2-yl]-morpholine (0.043 g, 0.15 mmol), bis(di-tert-butyl(4-dimethylaminophenyl)phosphine)dichloropalladium(II) (0.007 g, 0.01 mmol) and K₃PO₄ (0.042 g, 0.20 mmol). The vial was sealed with a septum cap and evacuated and backfilled with nitrogen. 1,4-Dioxane (1.5 mL) and H₂O (0.15 mL) were added via syringe and the vial was evacuated and backfilled with nitrogen an additional time. The reaction was irradiated to 110° C. for 1.5 h. The reaction mixture was concentrated onto celite and purification by flash chromatography [0.5-10% MeOH/DCM+0.5% NH₄OH] afforded the silyl protected biaryl as a clear amber film. The silyl protected product of the Suzuki coupling was dissolved in DCM (2 mL) and treated with trifluoroacetic acid (0.75 mL) at room temperature. After stirring for 1 h at room temperature the volatiles were removed in vacuo and the pure product was isolated by a catch and release protocol using a PoraPak Rxn CX ion exchange cartridge. Lyophilization afforded the title compound (R)—N-(2-(3-(dimethylamino)pyrrolidin-1-yl)-4-fluoro-5-(6-morpholinopyridin-3-yl)phenyl)-6-oxo-4-trifluoromethyl)-1,6-dihydropyridine-3-carboxamide (0.017 g, 30%). ¹H NMR (500 MHz, DMSO-d6) δ=9.71 (s, 1H), 8.18 (s, 1H), 7.89 (br s, 1H), 7.59 (br d, J=9.7 Hz, 1H), 7.21 (br d, J=8.8 Hz, 1H), 6.84 (d, J=8.9 Hz, 1H), 6.71 (s, 1H), 6.58 (d, J=14.2 Hz, 1H), 3.66-3.62 (m, 4H), 3.42-3.38 (m, 4H), 3.34-3.30 (m, 2H), 3.17 (br d, J=8.4 Hz, 1H), 2.08 (s, 6H), 2.03-1.96 (m, 1H), 1.63 (quin, J=9.9 Hz, 1H); LCMS [M+H]+: 575.3.

Example 235: N-[4-fluoro-5-[1-(oxetan-3-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

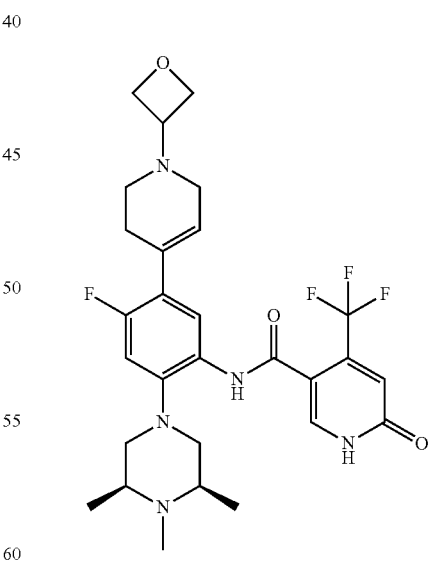

The procedure used was similar to that of Example 148 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (33 mg, 0.055 mmol), and oxetan-3-one (4.18 mg, 0.058 mmol) to give after workup the title compound (31 mg, 95% yield).

¹H NMR (500 MHz, METHANOL-d4) δ=7.93 (s, 1H), 7.79 (br d, J=7.9 Hz, 1H), 6.97-6.94 (m, 1H), 6.92 (s, 1H), 6.03 (br s, 1H), 4.78-4.67 (m, 4H), 3.70 (t, J=6.5 Hz, 1H), 3.16-3.08 (m, 2H), 3.04 (br d, J=9.8 Hz, 2H), 2.65-2.55 (m, 8H), 2.40 (s, 3H), 1.21-1.16 (m, 6H); LCMS [M+H]+ 564.6

Example 236: N-[4-fluoro-5-piperidin-4-yl-2-[(3R,5S)-3,4,5-trimethylpiperazin-1-yl]phenyl]-6-oxo-4-(trifluoromethyl)-1H-pyridine-3-carboxamide

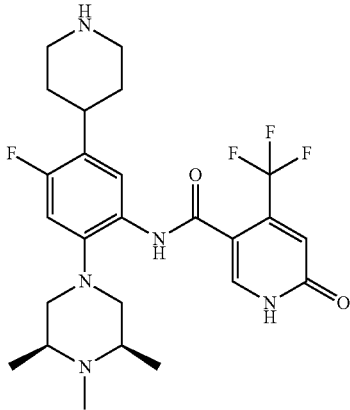

Step 1: tert-butyl 4-(2-fluoro-5-(4-(trifluoromethyl)-6-(2-(trimethylsilyl)ethoxy)nicotinamido)-4-((3S,5R)-3,4,5-trimethylpiperazin-1-yl)phenyl)piperidine-1-carboxylate

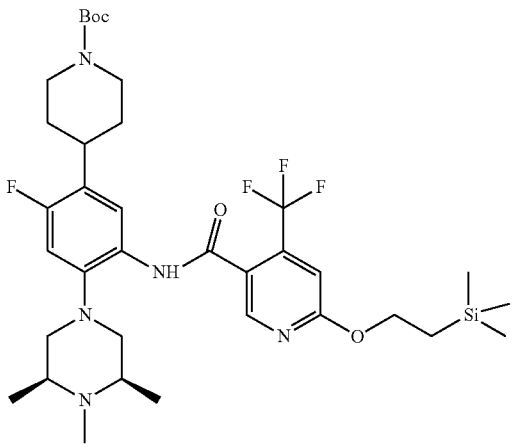 [SMILES: C[C@@H]1CN(c2cc(F)c(C3CCN(C(=O)OC(C)(C)C)CC3)cc2NC(=O)c2cnc(OCC[Si](C)(C)C)cc2C(F)(F)F)C[C@H](C)N1C]

A solution of tert-butyl 4-(2-fluoro-5-(4-(trifluoromethyl)-6-(2 (trimethylsilyl) ethoxy) nicotinamido)-4-((3S,5R)-3,4,5-trimethylpiperazin-1-yl)phenyl)-5,6-dihydropyridine-1(2H)-carboxylate (310 mg, 0.438 mmol) in MeOH was subjected to hydrogenation using palladium on carbon, 10% catalyst cartridge at RT, under 1 atm. pressure, on an H-cube. The mixture was concentrated to dryness to afford a white foam (301 mg, 97%). ¹H NMR (500 MHz, METHANOL-d4) δ=8.47-8.35 (m, 1H), 7.77-7.66 (m, 1H), 7.07-6.99 (m, 1H), 6.89-6.78 (m, 1H), 4.51-4.42 (m, 2H), 4.18-4.07 (m, 2H), 2.97-2.90 (m, 1H), 2.89-2.85 (m, 2H), 2.84-2.67 (m, 2H), 2.52-2.42 (m, 2H), 2.40-2.31 (m, 2H), 2.26-2.20 (m, 3H), 1.77-1.66 (m, 2H), 1.62-1.51 (m, 2H), 1.40-1.37 (m, 9H), 1.11-1.07 (m, 2H), 1.05-1.02 (m, 6H), 0.05-0.04 (m, 9H); LCMS [M+H]+ 710.6.

Step 2: N-(4-fluoro-5-(piperidin-4-yl)-2-((3S,5R)-3,4,5-trimethylpiperazin-1-yl)phenyl)-6-oxo-4-(trifluoromethyl)-1,6-dihydropyridine-3-carboxamide

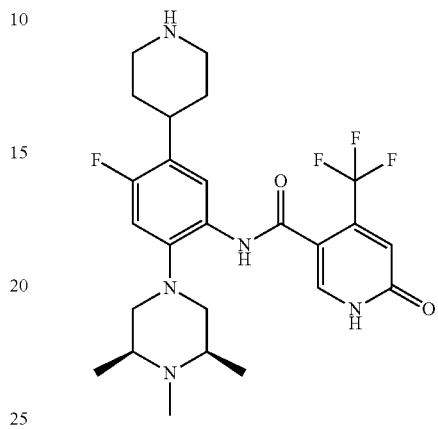

TFA (2 ml) was added to a solution of tert-butyl 4-(2-fluoro-5-(4-(trifluoromethyl)-6-(2-(trimethylsilyl)ethoxy)nicotinamido)-4-((3S,5R)-3,4,5-trimethylpiperazin-1-yl)phenyl)piperidine-1-carboxylate in DCM (6 ml) at RT and the reaction mixture was stirred at RT for 10 min. The mixture was concentrated to dryness, then the residue was dissolved in MeOH and passed through a cation exchange resin cartridge (Porapak Rxn CX 20 cc). The desired product as a free base was isolated as an off white powder. (210 mg, 94%). ¹H NMR (500 MHz, METHANOL-d4) δ=8.10 (s, 1H), 7.86 (br d, J=7.7 Hz, 1H), 7.00-6.94 (m, 1H), 6.78-6.72 (m, 1H), 3.44-3.39 (m, 2H), 3.21-3.11 (m, 1H), 3.09-3.01 (m, 2H), 3.01-2.95 (m, 2H), 2.60-2.54 (m, 2H), 2.53-2.47 (m, 2H), 2.39-2.34 (m, 3H), 2.04-1.98 (m, 2H), 1.96-1.86 (m, 2H), 1.15 (d, J=6.1 Hz, 6H); LCMS [M+H]+ 510.5.

Example 237: N-[4-fluoro-5-(6-hydroxypyridin-3-yl)-2-[(3R)-3-(dimethylamino)pyrrolidin-1-yl]phenyl]-6-oxo-4-(trifluoromethyl)-1H-pyridine-3-carboxamide

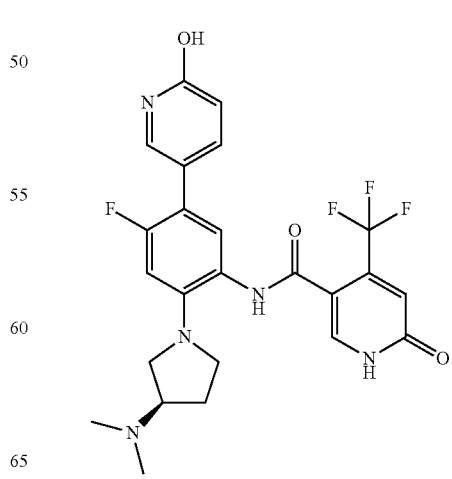

Examples 237 and 238 were isolated from a single reaction performed using a procedure similar to Example 234 Step 3 using 2-(cyclopropylmethoxy)-5-(4,4,5,5-tetramethyl-1,3,2-dioxaborolan-2-yl)pyridine in place of 4-[5-(4,4,5,5-tetramethyl-[1,3,2]dioxaborolan-2-yl)-pyridin-2-yl]-morpholine and separating the two products by chromatography. $^1$H NMR (500 MHz, DMSO-d6) δ=11.81-11.62 (m, 1H), 9.66 (br s, 1H), 8.00 (br s, 1H), 7.61-7.55 (m, 1H), 7.42 (br s, 1H), 7.21 (br d, J=8.9 Hz, 1H), 6.68-6.59 (m, J=14.2 Hz, 2H), 6.41 (d, J=9.5 Hz, 1H), 3.24-3.19 (m, 1H), 2.14 (s, 6H), 2.09-2.03 (m, 1H), 1.73-1.64 (m, 1H), 1.23 (s, 1H); LCMS [M+H]+: 506.2

Example 238: N-[5-[6-(cyclopropylmethoxy)pyridin-3-yl]-4-fluoro-2-[(3R)-3-(dimethylamino)pyrrolidin-1-yl]phenyl]-6-oxo-4-(trifluoromethyl)-1H-pyridine-3-carboxamide Example 239: N-[4-fluoro-5-(6-morpholin-4-ylpyridin-3-yl)-2-[(3R)-3,4-dimethylpiperazin-1-yl]phenyl]-6-oxo-4-(trifluoromethyl)-1H-pyridine-3-carboxamide

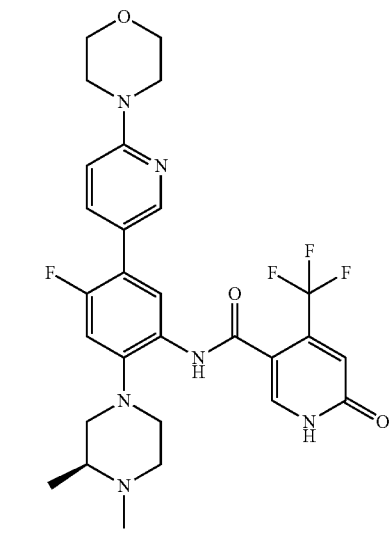

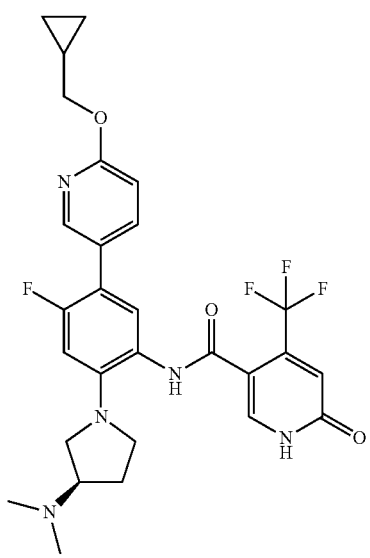 [SMILES: CN(C)[C@@H]1CCN(c2cc(F)c(-c3ccc(OCC4CC4)nc3)cc2NC(=O)c2c[nH]c(=O)cc2C(F)(F)F)C1]

$^1$H NMR (500 MHz, DMSO-d6) δ=12.54 (br s, 1H), 9.77 (br s, 1H), 8.22 (s, 1H), 7.97 (br s, 1H), 7.78 (br d, J=8.2 Hz, 1H), 7.29 (br d, J=8.7 Hz, 1H), 6.89 (d, J=8.6 Hz, 1H), 6.74 (br s, 1H), 6.66 (d, J=14.2 Hz, 1H), 4.12 (d, J=7.1 Hz, 2H), 3.42-3.37 (m, 4H), 3.26-3.21 (m, 1H), 2.15 (s, 6H), 2.09-2.03 (m, 1H), 1.74-1.64 (m, 1H), 1.29-1.22 (m, 1H), 0.58-0.53 (m, 2H), 0.36-0.31 (m, 2H); LCMS [M+H]+: 560.3.

The procedure used was similar that used in the last step of Example 196 using 4-[5-(4,4,5,5-tetramethyl-[1,3,2]dioxaborolan-2-yl)-pyridin-2-yl]-morpholine (0.040 g, 0.138 mmol), (S)—N-(5-bromo-2-(3,4-dimethylpiperazin-1-yl)-4-fluorophenyl)-4-(trifluoromethyl)-6-(2-(trimethylsilyl)ethoxy)nicotinamide (0.05432 g, 0.092 mmol) to give 18 mg (34% yield) of the title compound. $^1$H NMR (500 MHz, MeOD) δ 8.31 (s, 1H), 7.96 (s, 1H), 7.91 (d, J=8.2 Hz, 1H), 7.78 (d, J=8.8 Hz, 1H), 7.08 (d, J=12.1 Hz, 1H), 6.91 (s, 1H), 6.90 (d, J=8.1 Hz, 1H), 3.83-3.79 (m, 4H), 3.55-3.52 (m, 4H), 3.11 (d, J=11.7 Hz, 1H), 3.06 (d, J=11.4 Hz, 1H), 2.96 (dd, J=20.2, 10.7 Hz, 2H), 2.60 (dd, J=21.9, 11.5 Hz, 2H), 2.50 (s, 1H), 2.42 (s, 3H), 1.15 (d, J=6.2 Hz, 3H); LCMS [M+1]+=575.42.

Example 240: N-[4-fluoro-5-(2-propan-2-yloxypyrimidin-5-yl)-2-[(3R)-3,4-dimethylpiperazin-1-yl]phenyl]-6-oxo-4-(trifluoromethyl)-1H-pyridine-3-carboxamide

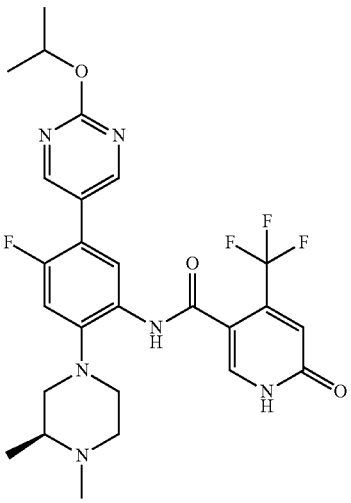

The title compound (18 mg, 38% yield) was prepared similar to the sequence described above for the preparation of Example 196 using (2-isopropoxypyrimidin-5-yl)boronic acid (0.024 g, 0.130 mmol), (S)—N-(5-bromo-2-(3,4-dimethylpiperazin-1-yl)-4-fluorophenyl)-4-(trifluoromethyl)-6-(2-(trimethylsilyl)ethoxy)nicotinamide (0.05144 g, 0.087 mmol). $^1$H NMR (500 MHz, MeOD) δ 8.73 (s, 2H), 7.97 (s, 1H), 7.95 (d, J=8.2 Hz, 1H), 7.14 (d, J=12.0 Hz, 1H), 6.91 (s, 1H), 5.37 (sep, J=6.2 Hz, 1H), 3.11 (dd, J=26.9, 10.8 Hz, 2H), 2.96 (t, J=8.9 Hz, 2H), 2.59 (t, J=10.7 Hz, 2H), 2.47 (s, 1H), 2.40 (s, 3H), 1.14 (d, J=6.0 Hz, 3H); LCMS [M+1]+=549.09.

Example 241: N-[5-(2,3-dihydro-[1,4]dioxino[2,3-b]pyridin-7-yl)-4-fluoro-2-[(3R)-3,4-dimethylpiperazin-1-yl]phenyl]-6-oxo-4-(trifluoromethyl)-1H-pyridine-3-carboxamide

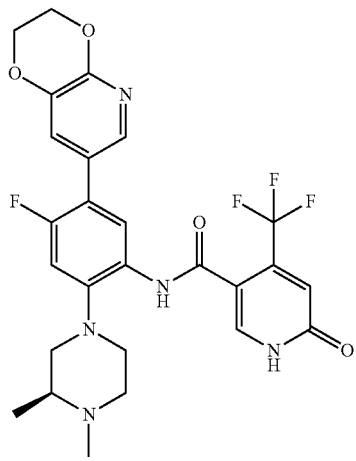 [SMILES: C[C@H]1CN(c2cc(F)c(-c3cnc4c(c3)OCCO4)cc2NC(=O)c2c[nH]c(=O)cc2C(F)(F)F)CCN1C]

The title compound (22.5 mg, 45% yield) was prepared similar to the sequence described above for the preparation of Example 196 using 7-(4,4,5,5-tetramethyl-1,3,2-dioxaborolan-2-yl)-2,3-dihydro-[1,4]dioxino[2,3-b]pyridine (0.035 g, 0.132 mmol), (S)—N-(5-bromo-2-(3,4-dimethylpiperazin-1-yl)-4-fluorophenyl)-4-(trifluoromethyl)-6-(2-(trimethylsilyl)ethoxy)nicotinamide (0.05200 g, 0.088 mmol). $^1$H NMR (500 MHz, MeOD) δ 7.97 (s, 1H), 7.92-7.89 (m, 2H), 7.49 (s, 1H), 7.09 (d, J=12.1 Hz, 1H), 6.91 (s, 1H), 4.49 (dd, J=5.0, 3.1 Hz, 2H), 4.33 (dd, J=4.9, 3.1 Hz, 2H), 3.13 (d, J=11.7 Hz, 1H), 3.08 (d, J=11.5 Hz, 1H), 2.97 (dd, J=19.7, 10.3 Hz, 2H), 2.61 (dd, J=21.5, 11.1 Hz, 2H), 2.51 (s, 1H), 2.42 (s, 3H), 1.15 (d, J=6.2 Hz, 3H); LCMS HSS [M+1]+=548.26.

Example 242: N-[4-fluoro-5-[1-(1-methylpiperidin-4-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

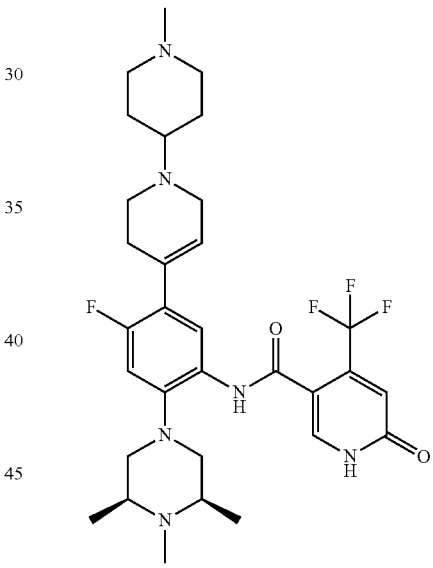

A procedure similar to that of Example 148 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (40 mg, 0.067 mmol), N-methyl-4-piperidone 97% (0.012 ml, 0.100 mmol) gave the title compound (14 mg, 31% yield). $^1$H NMR (500 MHz, METHANOL-d4) δ=7.86-7.79 (m, 1H), 7.71-7.61 (m, 1H), 6.85-6.80 (m, 1H), 6.80-6.77 (m, 1H), 5.99-5.86 (m, 1H), 3.29-3.25 (m, 2H), 3.07-3.01 (m, 2H), 2.93-2.86 (m, 2H), 2.82-2.75 (m, 2H), 2.53-2.40 (m, 7H), 2.38-2.31 (m, 3H), 2.30-2.23 (m, 5H), 1.99-1.89 (m, 2H), 1.67-1.58 (m, 2H), 1.07-1.03 (m, 6H); LCMS [M+H]+ 605.5.

Example 243: N-[5-[1-(2,2-dimethylpropanoyl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

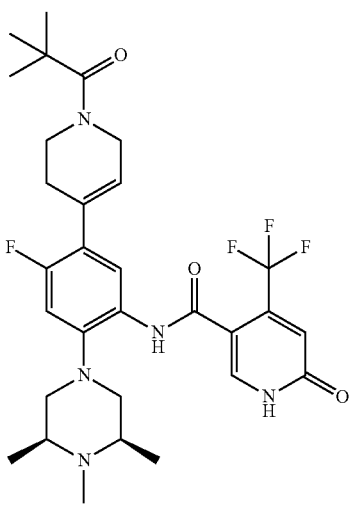

To a solution of N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (27 mg, 0.053 mmol) and N,N-diisopropylethylamine (10.66 μl, 0.061 mmol) in DCM (3 ml) at RT was added trimethylacetyl chloride (6.87 μl, 0.056 mmol). After 10 min, the reaction mixture was quenched with water (2 ml), worked up and the crude product purified to provide the title compound (15 mg, 45% yield). $^1$H NMR (500 MHz, METHANOL-d4) δ=7.94 (s, 1H), 7.78 (br d, J=8.2 Hz, 1H), 6.99-6.95 (m, 1H), 6.94-6.91 (m, 1H), 6.05 (br s, 1H), 4.28 (br s, 2H), 3.88 (t, J=5.6 Hz, 2H), 3.04 (br d, J=10.3 Hz, 2H), 2.64-2.55 (m, 6H), 2.42-2.38 (m, 3H), 1.35-1.33 (m, 9H), 1.19-1.16 (m, 6H); LCMS [M+H]+ 592.6

Example 244: N-[5-[1-(2,2-dimethylpropanoyl)piperidin-4-yl]-4-fluoro-2-[(3R,5S)-3,4,5-trimethylpiperazin-1-yl]phenyl]-6-oxo-4-(triluoromethyl)-1H-pyridine-3-carboxamide

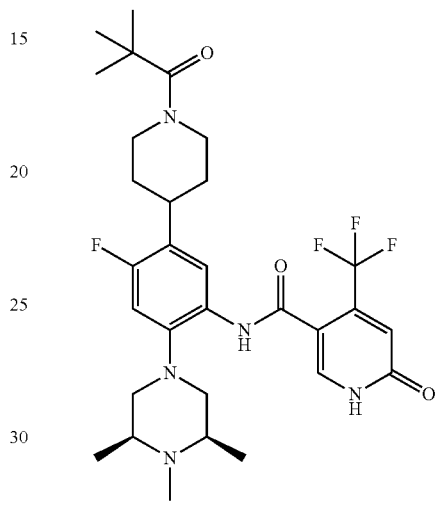

To a solution of N-(4-fluoro-5-(piperidin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and N,N-diisopropylethylamine (9.83 μl, 0.056 mmol) in DCM (3 ml) at RT was added trimethylacetyl chloride (6.34 μl, 0.052 mmol). The mixture became a clear solution. It was stirred at RT. Complete disappearance of the starting material and formation of the desired product was observed after 4 min at rt. The reaction was quenched with water (2 ml) after 10 min. The organic phase was separated, the aqueous phase was extracted with DCM (2 ml), and the combined organic phase was washed with, saturated NaHCO$_3$ soln., brine, then dried over Na$_2$SO$_4$ and concentrated onto celite. It was then purified by sgc (4 g column), eluting with DCM containing 0-8% MeOH. The desired fractions were combined and concentrated to afford the title compound as a white powder (26 mg, 85% yield). $^1$H NMR (500 MHz, METHANOL-d4) δ=7.98-7.93 (m, 1H), 7.80-7.72 (m, 1H), 6.99-6.94 (m, 1H), 6.94-6.91 (m, 1H), 4.66-4.55 (m, 2H), 3.23-3.11 (m, 1H), 3.06-2.91 (m, 4H), 2.63-2.51 (m, 4H), 2.43-2.37 (m, 3H), 1.96-1.88 (m, 2H), 1.74-1.65 (m, 2H), 1.35-1.32 (m, 10H), 1.18-1.15 (m, 6H); LCMS [M+H]+ 594.7.

393

Example 245: N-[4-fluoro-5-(1-pyrimidin-2-yl-3,6-dihydro-2H-pyridin-4-yl)-2-[(3R,5S)-3,4,5-trimethylpiperazin-1-yl]phenyl]-6-oxo-4-(trifluoromethyl)-1H-pyridine-3-carboxamide

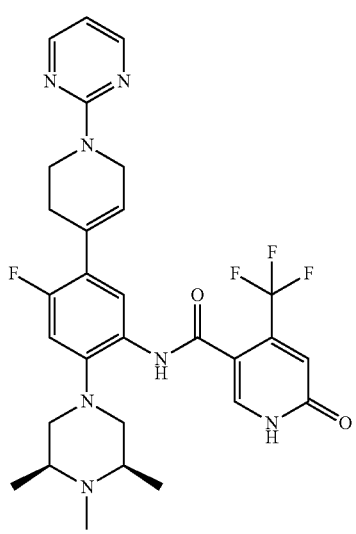

To a solution of N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) and 2-bromopyrimidine 95% (10.34 mg, 0.065 mmol) in ethanol (3 ml) at RT was added N,N-diisopropylethylamine (0.021 ml, 0.118 mmol). The reaction mixture was heated at 80° C. Complete disappearance of the starting material and formation of the desired product were observed after 4 min. The organic phase was separated, the aqueous phase was extracted with DCM (2 ml), the combined organic phase was washed with saturated NaHCO$_3$ soln., brine, then dried over Na$_2$SO$_4$ and concentrated onto celite. It was purified by sgc (4 g column), eluting with DCM containing 0-6% MeOH. The desired fractions were combined and concentrated to afford the title compound as an off white powder (26 mg, 71%). $^1$H NMR (500 MHz, METHANOL-d4) δ=8.43-8.31 (m, 2H), 7.95 (s, 1H), 7.80 (br d, J=8.1 Hz, 1H), 6.98-6.94 (m, 1H), 6.92 (s, 1H), 6.63 (t, J=4.8 Hz, 1H), 6.13 (br s, 1H), 4.37 (br d, J=2.8 Hz, 2H), 4.06 (t, J=5.6 Hz, 2H), 3.03 (br d, J=10.9 Hz, 2H), 2.62-2.52 (m, 6H), 2.38 (s, 3H), 1.17 (d, J=6.0 Hz, 6H), 1.00 (d, J=6.6 Hz, 1H); LCMS [M+H]+ 586.

394

Example 246: N-[4-fluoro-5-[2-[(2R,6S)-2,6-dimethylmorpholin-4-yl]pyrimidin-5-yl]-2-[(3S,5R)-3,4,5-trimethylpiperazin-1-yl]phenyl]-1-methyl-6-oxo-4-(trifluoromethyl)pyridine-3-carboxamide

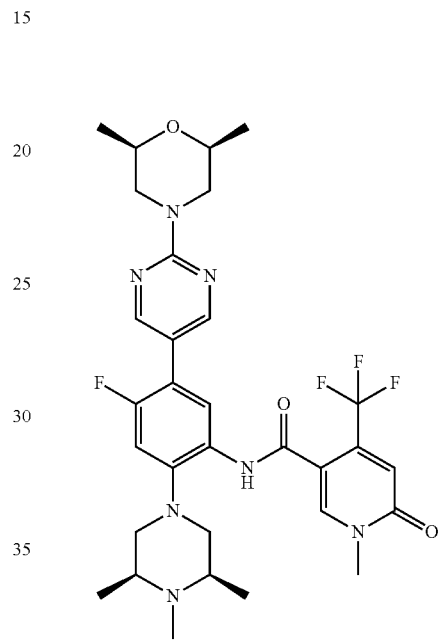

The title compound (pale beige solid, 37.1 mg, 73%) was prepared by a procedure similar to Example 226 using N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (42 mg, 0.08 mmol) and (2-((2S,6R)-2,6-dimethylmorpholino)pyrimidin-5-yl)boronic acid (38 mg, 0.16 mmol). $^1$H NMR (500 MHz, CHLOROFORM-d) δ=8.73 (s, 1H), 8.54 (s, 2H), 8.46 (d, J=8.2 Hz, 1H), 7.87 (s, 1H), 7.02 (d, J=10.4 Hz, 1H), 6.97 (s, 1H), 4.62 (dd, J=1.3, 13.0 Hz, 2H), 3.73-3.63 (m, 5H), 2.80 (br d, J=10.9 Hz, 2H), 2.70-2.59 (m, 4H), 2.37-2.26 (m, 5H), 1.28 (d, J=6.2 Hz, 6H), 1.13 (d, J=6.2 Hz, 6H); LCMS [M+H]+ 632.5.

Example 247: N-[4-fluoro-5-(3-fluoro-4-morpholin-4-ylphenyl)-2-[(3R,5S)-3,4,5-trimethylpiperazin-1-yl]phenyl]-1-methyl-6-oxo-4-(trifluoromethyl)pyridine-3-carboxamide

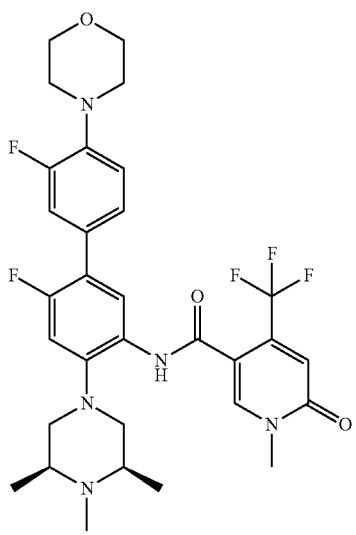

The title compound (pale beige solid, 35.8 mg, 72%) was prepared by a procedure similar to Example 226 using N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (42 mg, 0.08 mmol) and 3-fluoro-4-morpholinophenylboronic acid (36 mg, 0.16 mmol). $^1$H NMR (500 MHz, CHLOROFORM-d) δ=8.70 (s, 1H), 8.48 (d, J=8.3 Hz, 1H), 7.87 (s, 1H), 7.32 (s, 1H), 7.30 (d, J=7.7 Hz, 1H), 7.02-6.96 (m, 3H), 3.93-3.87 (m, 4H), 3.65 (s, 3H), 3.18-3.11 (m, 4H), 2.82 (br d, J=11.0 Hz, 2H), 2.64 (br t, J=10.8 Hz, 2H), 2.37-2.27 (m, 5H), 1.13 (d, J=6.2 Hz, 6H); LCMS [M+H]$^+$ 620.4.

Example 248: 4-fluoro-N-[4-fluoro-5-(2-morpholin-4-ylpyrimidin-5-yl)-2-[(3R,5S)-3,4,5-trimethylpiperazin-1-yl]phenyl]-2-(trifluoromethyl)benzamide

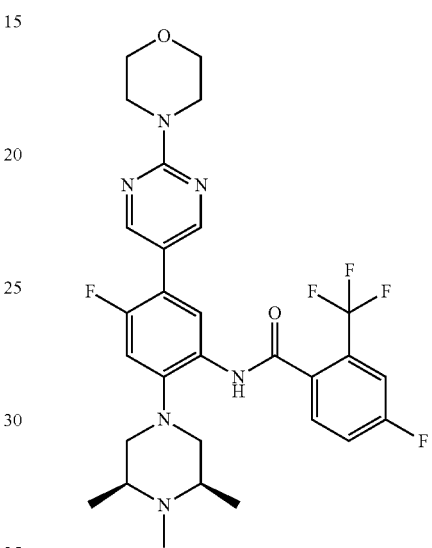

To a solution of 4-fluoro-5-(2-morpholinopyrimidin-5-yl)-2-((3S,5R)-3,4,5-trimethylpiperazin-1-yl)aniline (40 mg, 0.1 mmol) in dioxane (2 mL) was added 4-fluoro-2-(trifluoromethyl)benzoyl chloride (17 μL, 0.11 mmol). The mixture was heated at 110° C. for 30 min, and Et$_3$N (0.028 mL, 0.2 mmol) was added and the resulting mixture was heated at 110° C. for 10 min. Additional dioxane (3 mL) was added and the mixture was heated at 110° C. for 30 min. After quenching with sat. NaHCO$_3$ (3 mL), the reaction was extracted with DCM (5 mL) and the organic layer was loaded on Biotage samplet and purified by flash chromatography (gradient: EtOAc/hex 0-100% then MeOH/DCM 0-10%) to give the title compound as a brown solid (23.9 mg, 39%). $^1$H NMR (500 MHz, CHLOROFORM-d) δ=8.62-8.54 (m, 4H), 7.66 (dd, J=5.3, 8.3 Hz, 1H), 7.50 (dd, J=2.3, 8.8 Hz, 1H), 7.39 (dt, J=2.2, 8.1 Hz, 1H), 7.01 (d, J=11.2 Hz, 1H), 3.90-3.86 (m, 4H), 3.82-3.78 (m, 4H), 2.84 (br d, J=11.1 Hz, 2H), 2.72-2.56 (m, 2H), 2.38-2.20 (m, 5H), 1.12 (br d, J=5.6 Hz, 6H); LCMS [M+H]$^+$ 591.4.

Example 249: N-[4-fluoro-5-(1-methylsulfonyl-2,5-dihydropyrrol-3-yl)-2-[(3R,5S)-3,4,5-trimethylpiperazin-1-yl]phenyl]-6-oxo-4-(trifluoromethyl)-1H-pyridine-3-carboxamide

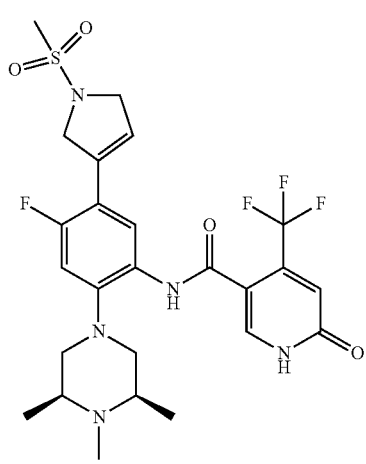 [SMILES: C[C@@H]1CN(c2cc(F)c(C3=CCN(S(C)(=O)=O)C3)cc2NC(=O)c2c[nH]c(=O)cc2C(F)(F)F)C[C@H](C)N1C]

To a mixture of N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (25 mg, 0.051 mmol) and N,N-diisopropylethylamine (0.018 ml, 0.101 mmol) in DCM (3 ml) at RT, was added methanesulfonyl chloride (3.92 µl, 0.051 mmol). It was stirred at RT. Formation of the desired product along with some di-substituted by-product and starting material was observed even after 20 min at rt. No change between 20 min and 45 min was observed. Therefore, 0.5 eq of methanesulfonyl chloride was added stirring at RT continued. The mixture was quenched with MeOH and concentrated onto celite, then purified by sgc eluting with DCM containing 0-6% MeOH and 0-0.6% $NH_{40}H$. The desired fractions were combined and concentrated to afford the title compound as a white powder (16 mg, 53% yield). $^1$H NMR (500 MHz, METHANOL-d4) δ=7.89-7.81 (m, 1H), 7.73-7.62 (m, 1H), 6.94-6.85 (m, 1H), 6.83-6.76 (m, 1H), 6.27-6.19 (m, 1H), 4.50-4.40 (m, 2H), 4.30-4.19 (m, 2H), 3.00-2.90 (m, 2H), 2.87-2.79 (m, 3H), 2.54-2.38 (m, 4H), 2.30-2.22 (m, 3H), 1.10-1.02 (m, 6H); LCMS [M+H]+ 572.4.

Example 250: 3,5-dichloro-N-[5-[6-(cyclopropylmethoxy)pyridin-3-yl]-4-fluoro-2-[(3R,5S)-3,4,5-trimethylpiperazin-1-yl]phenyl]benzamide

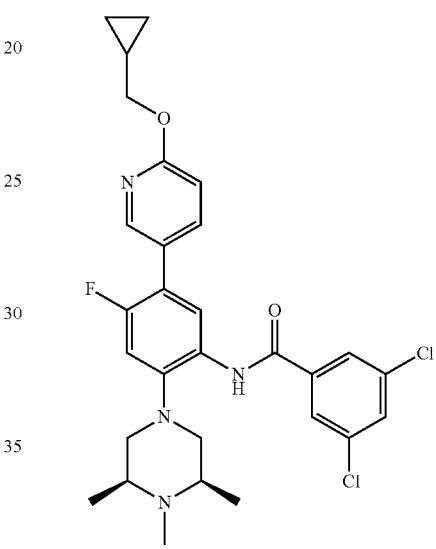

The title compound (off white solid, 23.0 mg, 40%) was prepared according to a sequence similar to that described hereinabove using 5-(6-(cyclopropylmethoxy)pyridin-3-yl)-4-fluoro-2-((3S,5R)-3,4,5-trimethylpiperazin-1-yl)aniline (38.4 mg, 0.1 mmol) and 3,5-dichlorobenzoyl chloride (21 µL, 0.15 mmol). $^1$H NMR (500 MHz, CHLOROFORM-d) δ=9.27 (s, 1H), 8.61 (d, J=8.2 Hz, 1H), 8.37 (s, 1H), 7.83-7.77 (m, 3H), 7.57 (s, 1H), 7.02 (d, J=11.1 Hz, 1H), 6.85 (d, J=8.6 Hz, 1H), 4.19 (d, J=7.1 Hz, 2H), 2.91 (br d, J=11.1 Hz, 2H), 2.73 (t, J=10.9 Hz, 2H), 2.52-2.42 (m, 2H), 2.39 (s, 3H), 1.37-1.28 (m, 1H), 1.19 (d, J=6.2 Hz, 6H), 0.67-0.61 (m, 2H), 0.41-0.36 (m, 2H); LCMS [M+H]+ 557.4.

Example 251: 2-chloro-N-[5-[6-(cyclopropyl-methoxy)pyridin-3-yl]-4-fluoro-2-[(3R,5S)-3,4,5-trimethylpiperazin-1-yl]phenyl]-4-fluorobenzamide

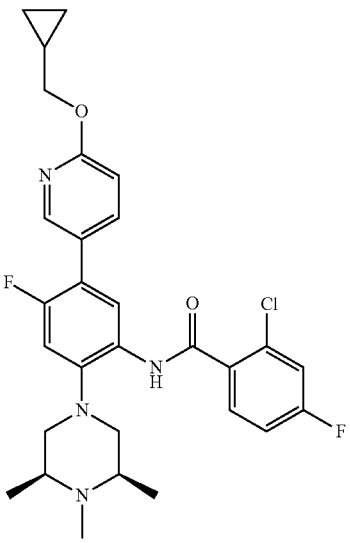 [SMILES: C[C@@H]1CN(c2cc(F)c(-c3ccc(OCC4CC4)nc3)cc2NC(=O)c2ccc(F)cc2Cl)C[C@H](C)N1C]

The title compound (white solid, 44.4 mg, 810%) was prepared in a sequence similar that described hereinabove using 5-(6-(cyclopropylmethoxy)pyridin-3-yl)-4-fluoro-2-((3S,5R)-3,4,5-trimethylpiperazin-1-yl)aniline (38.4 mg, 0.1 mmol) and 2-chloro-4-fluorobenzoylchloride (20 μL, 0.15 mmol). $^1$H NMR (500 MHz, CHLOROFORM-d) δ=9.20 (s, 1H), 8.68 (d, J=8.3 Hz, 1H), 8.37 (s, 1H), 7.85 (t, J=7.5 Hz, 1H), 7.80 (d, J=8.4 Hz, 1H), 7.24 (dd, J=2.4, 8.4 Hz, 1H), 7.14 (t, J=8.1 Hz, 1H), 7.02 (d, J=11.2 Hz, 1H), 6.85 (d, J=8.6 Hz, 1H), 4.19 (d, J=7.2 Hz, 2H), 2.88 (br d, J=11.0 Hz, 2H), 2.65 (t, J=10.9 Hz, 2H), 2.42-2.31 (m, 5H), 1.37-1.28 (m, 1H), 1.13 (d, J=6.2 Hz, 6H), 0.67-0.61 (m, 2H), 0.40-0.35 (m, 2H); LCMS [M+H]$^+$ 541.2.

Example 252: N-[5-(1-acetyl-3,6-dihydro-2H-pyridin-4-yl)-4-fluoro-2-[(3R,5S)-3,4,5-trimethylpiperazin-1-yl]phenyl]-6-oxo-4-(trifluoromethyl)-1H-pyridine-3-carboxamide

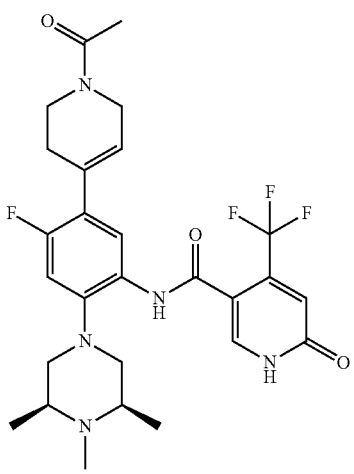

To a solution of N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) and N,N-diisopropylethylamine (0.021 ml, 0.118 mmol) in DCM (3 mL) at RT, was added 4-methoxybenzoyl chloride, 99% (8.55 μl, 0.062 mmol). The reaction mixture was stirred at RT. Complete disappearance of the starting material and formation of the desired product was observed after 4 min. The reaction was quenched with water (2 ml) after 10 min. The organic phase was separated, the aqueous phase was extracted with DCM (2 ml), the combined organic phase was washed with satd. NaHCO$_3$ soln., brine, then dried over Na$_2$SO$_4$ and concentrated onto celite. It was then purified on Isco column (4 g), eluting with DCM containing 0-8% MeOH. The desired fractions were combined and concentrated to afford the title compound as a white powder (23 mg, 58%) $^{19}$F NMR (471 MHz, METHANOL-d4) δ=−63.83 (s, 1F), −117.61 (s, 1F); LCMS [M+H]+ 642.5

Example 253: ethyl 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate

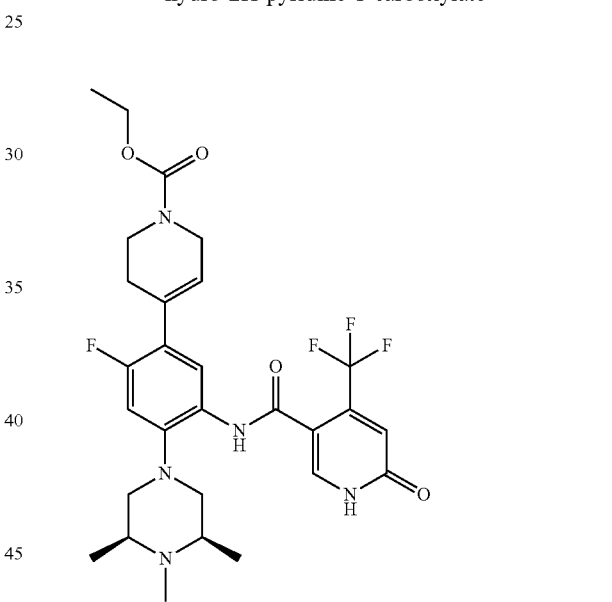

To a solution of N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (50 mg, 0.099 mmol) and N,N-diisopropylethylamine (0.034 ml, 0.197 mmol) in dichloromethane (DCM) (3 ml) at RT was added ethyl chloroformate (0.011 ml, 0.118 mmol). The milky reaction mixture became a clear solution. It was stirred at RT. Complete disappearance of the starting material and formation of the desired product was observed after 20 min at RT. The reaction was quenched with water (2 mL), the organic phase was separated, the aqueous phase was extracted with DCM (2×2 ml), the combined organic phase was washed with brine, then dried over Na$_2$SO$_4$ and concentrated onto celite. It was purified on Isco column (4 g), eluting with DCM containing 0-6% MeOH to collect the title compound as a white powder (44 mg, 73%). $^1$H NMR (500 MHz, METHANOL-d4) δ=7.94 (s, 1H), 7.77 (br d, J=8.1 Hz, 1H), 6.98-6.94 (m, 1H), 6.92 (s, 1H), 6.00 (br s, 1H), 4.21-4.16 (m, 2H), 4.16-4.07 (m, 2H), 3.68 (br s, 2H), 3.03 (br d, J=10.5 Hz, 2H), 2.63-2.50 (m, 6H), 2.39 (s, 3H), 1.33-1.30 (m, 3H), 1.20-1.15 (m, 6H), 0.94-0.94 (m, 1H); LCMS [M+H]+ 580.46

Example 254: 2-methylpropyl 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate

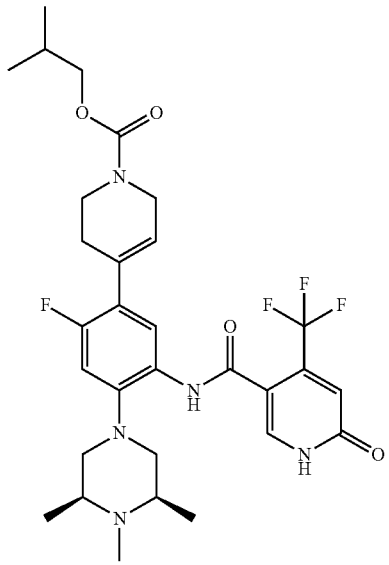 [SMILES: CC(C)COC(=O)N1CC=C(c2cc(NC(=O)c3c[nH]c(=O)cc3C(F)(F)F)c(N3C[C@@H](C)N(C)[C@@H](C)C3)cc2F)CC1]

The procedure used was similar to that of Example 253 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) and isobutyl chloroformate (7.73 µl, 0.059 mmol) to give, after workup and purification, the title compound as a white powder (25.5 mg, 67% yield). ¹H NMR (500 MHz, METHANOL-d4) δ=7.94-7.87 (m, 1H), 7.78-7.68 (m, 1H), 6.94-6.90 (m, 1H), 6.90-6.87 (m, 1H), 6.04-5.89 (m, 1H), 4.19-4.06 (m, 2H), 3.92-3.87 (m, 2H), 3.73-3.60 (m, 2H), 3.02-2.97 (m, 2H), 2.58-2.46 (m, 6H), 2.37-2.33 (m, 3H), 2.01-1.89 (m, 1H), 1.15-1.11 (m, 6H), 0.98-0.94 (m, 6H), 0.85-0.85 (m, 1H); LCMS [M+H]+ 608.45

Example 255: N-[5-[1-(3,3-dimethylbutanoyl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

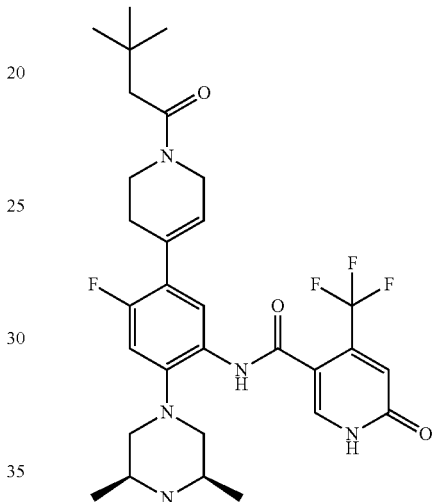

The procedure used was similar to Example 253 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (29.5 mg, 0.058 mmol) and N,N-diisopropylethylamine (0.013 ml, 0.073 mmol) and 3,3-dimethylbutyryl chloride (8.48 µl, 0.061 mmol). The workup and purification provided the title compound as a white powder (25 mg, 68% yield). ¹H NMR (500 MHz, METHANOL-d4) δ=7.99-7.91 (m, 1H), 7.84-7.71 (m, 1H), 6.98-6.94 (m, 1H), 6.94-6.90 (m, 1H), 6.08-5.97 (m, 1H), 4.34-4.27 (m, 1H), 4.26-4.20 (m, 1H), 3.87-3.78 (m, 2H), 3.08-3.01 (m, 2H), 2.64-2.51 (m, 6H), 2.45-2.40 (m, 2H), 2.39-2.37 (m, 3H), 1.19-1.15 (m, 6H), 1.11-1.07 (m, 9H); LCMS [M+H]+ 606.5

Example 256: N-[5-[1-(3,3-dimethylbutanoyl)piperidin-4-yl]-4-fluoro-2-[(3R,5S)-3,4,5-trimethylpiperazin-1-yl]phenyl]-6-oxo-4-(trifluoromethyl)-1H-pyridine-3-carboxamide

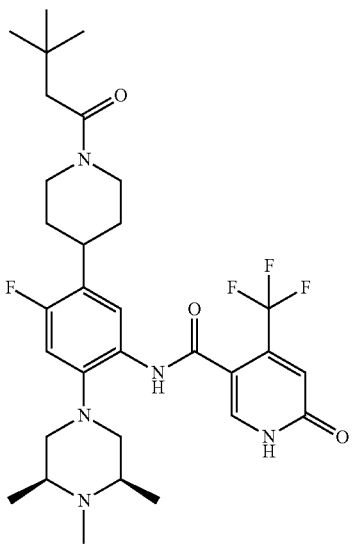 [SMILES: C[C@@H]1CN(c2cc(F)c(C3CCN(C(=O)CC(C)(C)C)CC3)cc2NC(=O)c2c[nH]c(=O)cc2C(F)(F)F)C[C@H](C)N1C]

To a mixture of N-(4-fluoro-5-(piperidin-4-yl)-2-((3S,5R)-3,4,5-trimethylpiperazin-1-yl)phenyl)-6-oxo-4-(trifluoromethyl)-1,6-dihydropyridine-3-carboxamide (26.5 mg, 0.052 mmol) and N,N-diisopropylethylamine (0.011 ml, 0.065 mmol) in DCM (3 ml) at RT was added 3,3-dimethylbutyryl chloride (7.59 µl, 0.055 mmol). A workup and purification provided the title compound as a white powder (26 mg, 74% yield). $^1$H NMR (500 MHz, METHANOL-d4) δ=8.00-7.90 (m, 1H), 7.81-7.70 (m, 1H), 6.99-6.94 (m, 1H), 6.94-6.90 (m, 1H), 4.82-4.73 (m, 1H), 4.28-4.19 (m, 1H), 3.29-3.21 (m, 1H), 3.17-3.09 (m, 1H), 3.02-2.94 (m, 2H), 2.77-2.69 (m, 1H), 2.63-2.51 (m, 4H), 2.49-2.44 (m, 1H), 2.40-2.37 (m, 3H), 2.36-2.29 (m, 1H), 1.95-1.86 (m, 2H), 1.78-1.70 (m, 1H), 1.69-1.62 (m, 1H), 1.18-1.14 (m, 6H), 1.08 (s, 9H); LCMS [M+H]+ 608.45

Example 257: N-[4-fluoro-5-(6-fluoropyridin-3-yl)-2-[(3R,5S)-3,4,5-trimethylpiperazin-1-yl]phenyl]-6-oxo-4-(trifluoromethyl)-1H-pyridine-3-carboxamide

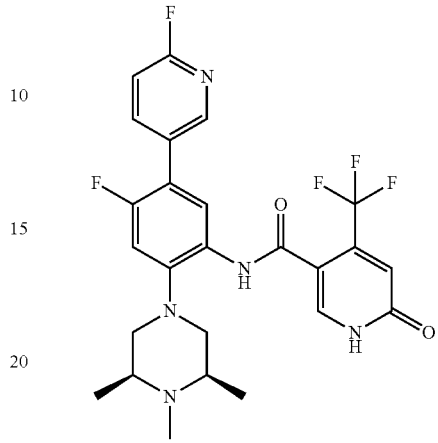

The title compound was prepared similar to the procedure described above for the final coupling and deprotection steps in the preparation of Example 31 using 6-fluoropyridine-3-boronic acid pinacol ester. $^1$H NMR (500 MHz, DMSO-d6) δ=12.81-12.30 (m, 1H), 9.59 (s, 1H), 8.36 (s, 1H), 8.16-8.06 (m, 1H), 7.92 (s, 1H), 7.78 (d, J=8.6 Hz, 1H), 7.32 (dd, J=2.7, 8.6 Hz, 1H), 7.08 (d, J=12.5 Hz, 1H), 6.81 (s, 1H), 3.06 (br d, J=11.0 Hz, 2H), 2.49-2.43 (m, 2H), 2.20 (s, 3H), 1.01 (d, J=6.0 Hz, 6H); LCMS [M+H]+: 522.5.

Example 258: N-[2-[4-(dimethylamino)piperidin-1-yl]-4-fluoro-5-(2-morpholin-4-ylpyrimidin-5-yl)phenyl]-6-oxo-4-(trifluoromethyl)-1H-pyridine-3-carboxamide

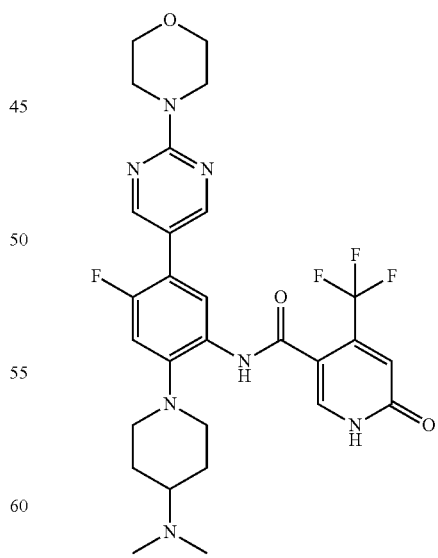

The title compound was prepared similar to the sequence described above for the preparation of Example 234 using 4-(dimethylamino)piperidine in place of (R)—N-ethyl-N-methylpyrrolidin-3-amine in Step 1. $^1$H NMR (500 MHz, DMSO-d6) δ=9.55 (s, 1H), 8.52 (s, 2H), 7.90 (s, 1H), 7.78 (d, J=8.4 Hz, 1H), 7.07 (d, J=12.3 Hz, 1H), 6.81 (s, 1H), 3.78-3.74 (m, 4H), 3.69-3.66 (m, 4H), 3.19 (br d, J=11.6 Hz, 2H), 2.67-2.58 (m, 3H), 2.24 (br s, 6H), 1.87-1.76 (m, 2H), 1.58 (br dd, J=3.1, 11.7 Hz, 2H); LCMS [M+H]+: 590.5.

Example 259: N-[2-[4-[2-(dimethylamino)ethyl]piperazin-1-yl]-4-fluoro-5-(2-morpholin-4-ylpyrimidin-5-yl)phenyl]-6-oxo-4-(trifluoromethyl)-1H-pyridine-3-carboxamide

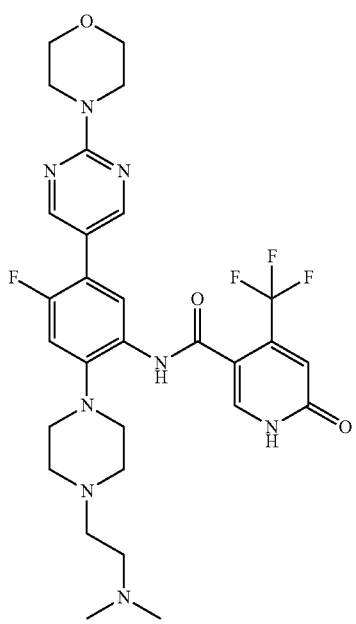 [SMILES: CN(C)CCN1CCN(c2cc(F)c(-c3cnc(N4CCOCC4)nc3)cc2NC(=O)c2c[nH]c(=O)cc2C(F)(F)F)CC1]

The title compound was prepared similar to the procedure described above for the preparation of Example 234 using 1-(2-dimethylaminoethyl)piperazine in place of (R)—N-ethyl-N-methylpyrrolidin-3-amine in Step 1. $^1$H NMR (500 MHz, DMSO-d6) δ=9.54 (s, 1H), 8.53 (d, J=1.0 Hz, 2H), 7.92 (s, 1H), 7.75 (d, J=8.7 Hz, 1H), 7.09 (d, J=12.2 Hz, 1H), 6.81 (s, 1H), 3.78-3.73 (m, 4H), 3.70-3.65 (m, 4H), 2.90 (br s, 4H), 2.60-2.54 (m, 4H), 2.48-2.39 (m, 4H), 2.21 (br s, 6H); LCMS [M+H]+: 619.5.

Example 260: N-[2-[2-[(dimethylamino)methyl]morpholin-4-yl]-4-fluoro-5-(2-morpholin-4-ylpyrimidin-5-yl)phenyl]-6-oxo-4-(trifluoromethyl)-1H-pyridine-3-carboxamide

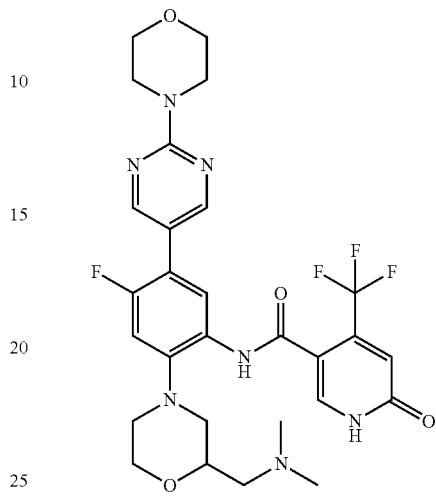

The title compound was prepared similar to the sequence described above for the preparation of Example 234 using dimethyl-morpholin-2-ylmethyl-amine in place of (R)—N-ethyl-N-methylpyrrolidin-3-amine in Step 1. $^1$H NMR (500 MHz, DMSO-d6) δ=9.58 (s, 1H), 8.53 (d, J=0.9 Hz, 2H), 7.95 (s, 1H), 7.77 (d, J=8.4 Hz, 1H), 7.10 (d, J=12.1 Hz, 1H), 6.81 (s, 1H), 3.85 (br d, J=11.4 Hz, 1H), 3.77-3.74 (m, 4H), 3.73-3.70 (m, 1H), 3.69-3.67 (m, 4H), 3.08 (br d, J=11.4 Hz, 1H), 2.99 (br d, J=11.7 Hz, 1H), 2.77 (dt, J=2.6, 11.4 Hz, 1H), 2.63 (br d, J=1.7 Hz, 1H), 2.48 (br d, J=1.6 Hz, 1H), 2.36 (br d, J=1.8 Hz, 1H), 2.13 (br s, 6H); LCMS [M+H]+: 606.4.

Example 261: N-[4-fluoro-5-(6-pyrrolidin-1-ylpyridin-3-yl)-2-[(3R,5S)-3,4,5-trimethylpiperazin-1-yl]phenyl]-6-oxo-4-(trifluoromethyl)-1H-pyridine-3-carboxamide

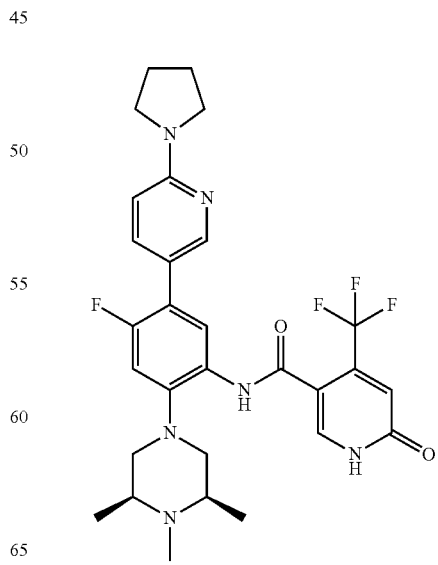

The title compound was prepared similar to the sequence described above for the preparation of Example 100 using 6-(pyrrolidin-1-yl)pyridine-3-boronic acid, pinacol ester (34.0 mg, 0.124 mmol) and N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) to give the title compound (37 mg, 79%). $^1$H NMR (500 MHz, DMSO-d6) δ=12.66-12.44 (m, 1H), 9.49 (s, 1H), 8.20 (s, 1H), 7.91 (s, 1H), 7.76-7.69 (m, 1H), 7.61 (br d, J=8.7 Hz, 1H), 7.00 (br d, J=12.5 Hz, 1H), 6.81 (s, 1H), 6.54 (d, J=8.8 Hz, 1H), 3.41 (br s, 6H), 3.06-2.97 (m, 1H), 2.44 (br d, J=9.3 Hz, 1H), 2.36 (br dd, J=1.8, 3.5 Hz, 1H), 1.99-1.89 (m, 5H), 1.14 (d, J=13.2 Hz, 2H), 1.01 (br d, J=5.0 Hz, 6H); LCMS [M+H]+: 573.5.

Example 262: N-[5-(5-cyano-6-pyrrolidin-1-ylpyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

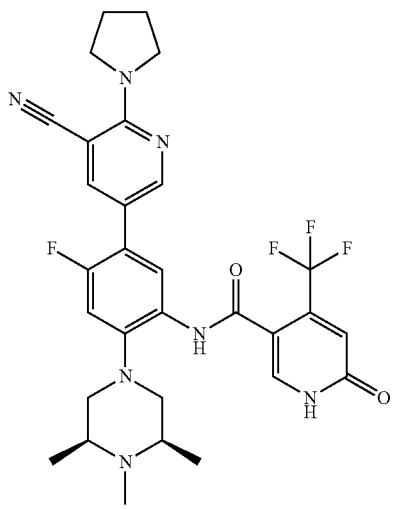 [SMILES: C[C@@H]1CN(c2cc(F)c(-c3cnc(N4CCCC4)c(C#N)c3)cc2NC(=O)c2c[nH]c(=O)cc2C(F)(F)F)C[C@H](C)N1C]

The title compound was prepared similar to the sequence described for the preparation of Example 100 using 3-cyano-2-pyrrolidinopyridine-5-boronic acid, pinacol ester (37.1 mg, 0.124 mmol) and N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) to give the title compound (32 mg 64% yield). $^1$H NMR (500 MHz, DMSO-d6) δ=12.66-12.49 (m, 1H), 9.55 (s, 1H), 8.46 (d, J=1.7 Hz, 1H), 8.02 (d, J=2.2 Hz, 1H), 7.91 (s, 1H), 7.74 (d, J=8.4 Hz, 1H), 7.02 (d, J=12.5 Hz, 1H), 6.81 (s, 1H), 3.71 (br t, J=6.5 Hz, 5H), 3.02 (br d, J=11.2 Hz, 2H), 2.47-2.40 (m, 2H), 2.38-2.28 (m, 2H), 2.19 (br s, 3H), 1.95 (td, J=3.4, 6.3 Hz, 5H), 1.00 (br d, J=6.0 Hz, 6H); LCMS [M+H]+: 598.5.

Example 263: N-[5-(2,2-difluoro-1,3-benzodioxol-5-yl)-4-fluoro-2-[(3R,5S)-3,4,5-trimethylpiperazin-1-yl]phenyl]-6-oxo-4-(trifluoromethyl)-1H-pyridine-3-carboxamide

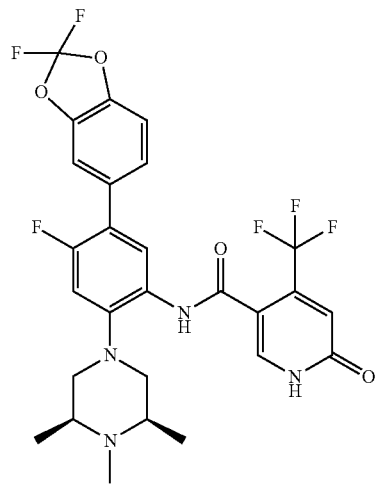 [SMILES: C[C@@H]1CN(c2cc(F)c(-c3ccc4c(c3)OC(F)(F)O4)cc2NC(=O)c2c[nH]c(=O)cc2C(F)(F)F)C[C@H](C)N1C]

The title compound was prepared similar to the sequence described above for the preparation of Example 100 using 2,2-difluoro-benzo[1,3]dioxole-5-boronic acid (25.01 mg, 0.124 mmol) and N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) to give the title compound (40.2 mg, 80% yield). $^1$H NMR (500 MHz, DMSO-d6) δ=12.77-12.43 (m, 1H), 9.55 (s, 1H), 7.91 (s, 1H), 7.75 (d, J=8.7 Hz, 1H), 7.59-7.46 (m, 2H), 7.31 (d, J=8.6 Hz, 1H), 7.04 (d, J=12.5 Hz, 1H), 6.80 (s, 1H), 3.04 (br d, J=10.9 Hz, 2H), 2.48-2.43 (m, 2H), 2.38-2.31 (m, 2H), 2.19 (s, 3H), 1.01 (d, J=6.1 Hz, 6H); LCMS [M+H]+: 583.0.

Example 264: 3-chloro-4-fluoro-N-[4-fluoro-5-(2-morpholin-4-ylpyrimidin-5-yl)-2-[(3R,5S)-3,4,5-trimethylpiperazin-1-yl]phenyl]benzamide

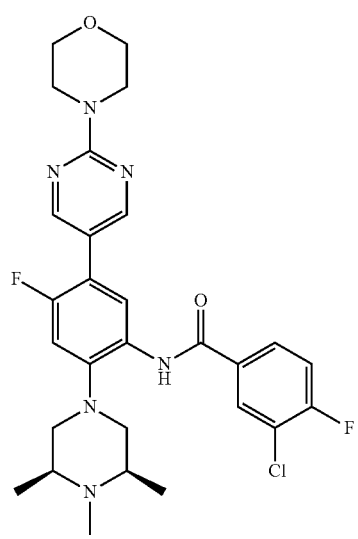

The title compound (beige solid, 49.8 mg, 83%) was prepared by a procedure similar to that of Example 34 using 3,5-dichloro-4-fluorobenzoic acid (42 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.25 (s, 1H), 8.58-8.54 (m, 3H), 7.88 (d, J=6.0 Hz, 2H), 7.02 (d, J=11.1 Hz, 1H), 3.91-3.85 (m, 4H), 3.82-3.78 (m, 4H), 2.89 (br d, J=11.0 Hz, 2H), 2.71 (t, J=10.9 Hz, 2H), 2.47-2.40 (m, 2H), 2.38 (s, 3H), 1.18 (d, J=6.2 Hz, 6H); LCMS [M+H]$^+$ 591.3.

Example 265: 3-chloro-N-[4-fluoro-5-(2-morpholin-4-ylpyrimidin-5-yl)-2-[(3R,5S)-3,4,5-trimethylpiperazin-1-yl]phenyl]-5-methoxybenzamide Example 266: 3-chloro-2,4-difluoro-N-[4-fluoro-5-(2-morpholin-4-ylpyrimidin-5-yl)-2-[(3R,5S)-3,4,5-trimethylpiperazin-1-yl]phenyl]benzamide

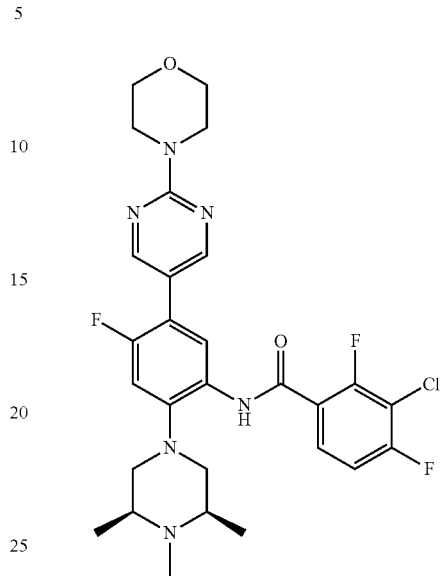

The title compound (off-white solid, 46.6 mg, 79%) was prepared by a procedure similar to that of Example 34 using 3-chloro-2,4-difluorobenzoic acid (39 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.78 (br d, J=12.5 Hz, 1H), 8.70 (d, J=8.2 Hz, 1H), 8.58 (s, 2H), 8.14 (q, J=7.7 Hz, 1H), 7.19 (br t, J=8.1 Hz, 1H), 7.04 (d, J=11.1 Hz, 1H), 3.87 (br d, J=3.8 Hz, 4H), 3.81 (br d, J=4.4 Hz, 4H), 2.88 (br d, J=11.1 Hz, 2H), 2.68 (br t, J=10.8 Hz, 2H), 2.55-2.45 (m, 2H), 2.38 (s, 3H), 1.16 (d, J=6.1 Hz, 6H); LCMS [M+H]$^+$ 575.4.

Example 267: N-[4-fluoro-5-(1-methyl-3,6-dihydro-2H-pyridin-4-yl)-2-[(3R,5S)-3,4,5-trimethylpiperazin-1-yl]phenyl]-6-oxo-4-(trifluoromethyl)-1H-pyridine-3-carboxamide

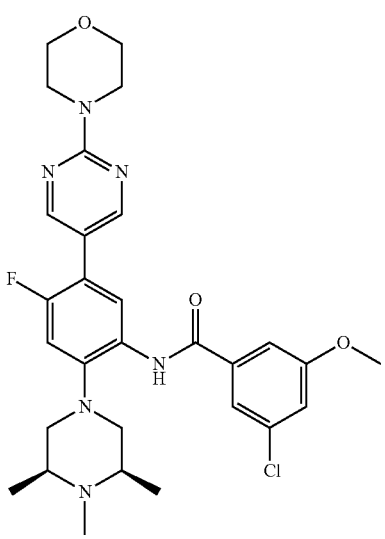

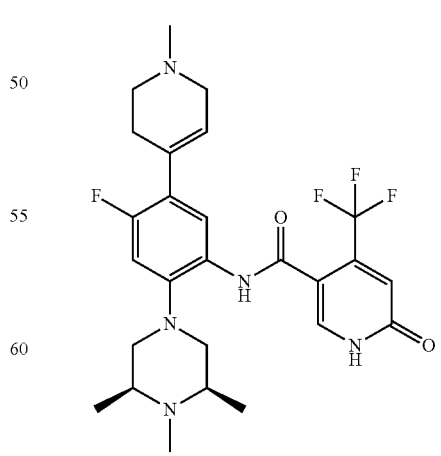

The title compound (white solid, 42.2 mg, 76%) was prepared by a procedure similar to Example 34 using 3-chloro-5-methoxybenzoic acid (37 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.24 (s, 1H), 8.62 (d, J=8.3 Hz, 1H), 8.57 (s, 2H), 7.42 (s, 1H), 7.39 (s, 1H), 7.10 (t, J=2.0 Hz, 1H), 7.01 (d, J=11.2 Hz, 1H), 3.90 (s, 3H), 3.89-3.86 (m, 4H), 3.82-3.78 (m, 4H), 2.91 (br d, J=11.1 Hz, 2H), 2.69 (t, J=11.0 Hz, 2H), 2.52-2.41 (m, 2H), 2.38 (s, 3H), 1.17 (d, J=6.2 Hz, 6H); LCMS [M+H]$^+$ 569.3.

The procedure followed was similar to Example 148 using N-(4-fluoro-5-(1,2,3,6-tetrahydropyridin-4-yl)-2-

((3S,5R)-3,4,5-trimethylpiperazin-1-yl)phenyl)-6-oxo-4-(trifluoromethyl)-1,6-dihydropyridine-3-carboxamide (30 mg, 0.059 mmol) and paraformaldehyde (3.55 mg, 0.118 mmol) to give, after workup and purification, 3.5 mg (10% yield) of the title compound. $^1$H NMR (500 MHz, METHANOL-d4) δ=7.90-7.85 (m, 1H), 7.72-7.64 (m, 1H), 6.86-6.79 (m, 1H), 6.78-6.72 (m, 1H), 5.93-5.88 (m, 1H), 3.11-3.06 (m, 2H), 2.93-2.87 (m, 2H), 2.68-2.61 (m, 2H), 2.52-2.49 (m, 2H), 2.48-2.43 (m, 2H), 2.42-2.37 (m, 2H), 2.34-2.30 (m, 3H), 2.26-2.23 (m, 3H), 1.04 (br d, J=6.0 Hz, 6H); LCMS [M+H]+ 522.46.

Example 268: N-[4-fluoro-2-(8-methyl-3,8-diazabicyclo[3.2.1]octan-3-yl)-5-(2-morpholin-4-ylpyrimidin-5-yl)phenyl]-6-oxo-4-(trifluoromethyl)-1H-pyridine-3-carboxamide

Example 269: N-[5-(6-cyano-4-methylpyridin-3-yl)-4-fluoro-2-[(3R,5S)-3,4,5-trimethylpiperazin-1-yl]phenyl]-6-oxo-4-(trifluoromethyl)-1H-pyridine-3-carboxamide

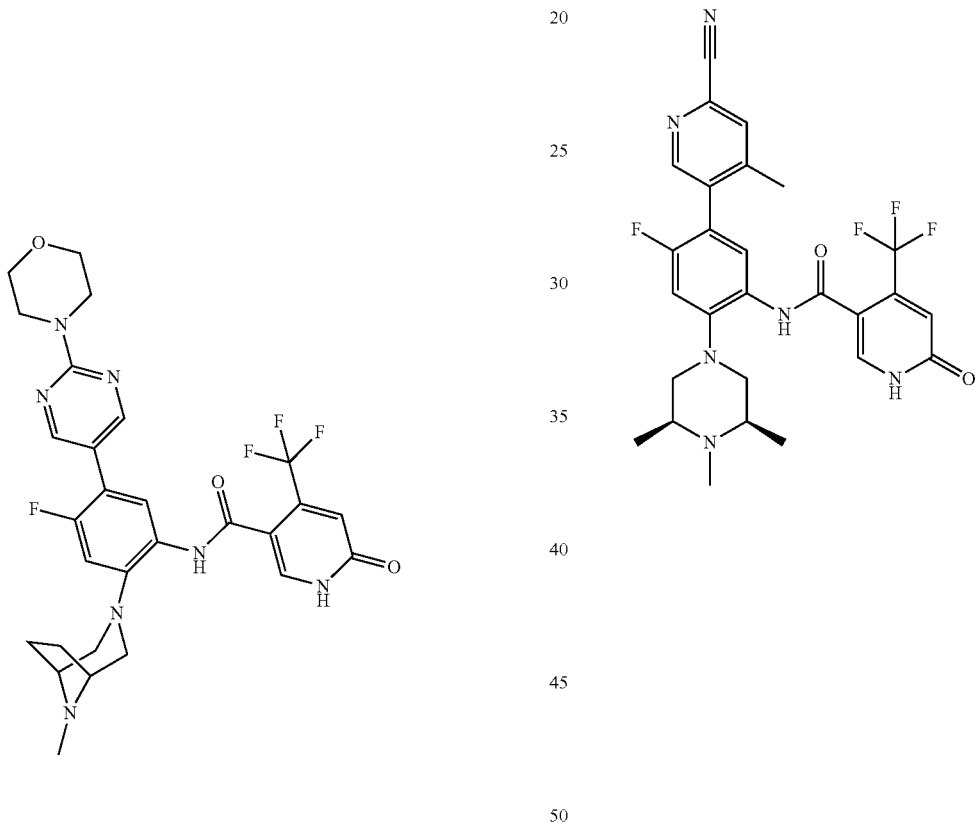

The title compound was prepared similar to the procedure described above for the preparation of Example 234 using 8-methyl-3,8-diazabicyclo[3.2.1]octane dihydrochloride in place of (R)—N-ethyl-N-methylpyrrolidin-3-amine in Step 3. $^1$H NMR (500 MHz, DMSO-d6) δ=9.42 (s, 1H), 8.53 (s, 2H), 8.07 (s, 1H), 7.66 (br d, J=8.4 Hz, 1H), 7.07 (d, J=12.5 Hz, 1H), 6.83 (s, 1H), 3.78-3.73 (m, 4H), 3.70-3.65 (m, 4H), 3.13 (br s, H), 2.96-2.81 (m, 4H), 2.22 (s, 3H), 1.95-1.82 (m, 2H), 1.75 (br d, J=7.1 Hz, 2H); LCMS [M+H]+: 588.4.

The title compound was prepared similar to the sequence described above for the preparation of Example 100 using 4-methyl-5-(tetramethyl-1,3,2-dioxaborolan-2-yl)pyridine-2-carbonitrile (30.2 mg, 0.124 mmol) and N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) to give the title compound (41.2 mg, 92% yield). $^1$H NMR (500 MHz, DMSO-d6) δ=9.59 (s, 1H), 8.55 (s, 1H), 8.08 (s, 1H), 7.90 (s, 1H), 7.65 (br d, J=8.1 Hz, 1H), 7.11 (d, J=11.7 Hz, 1H), 6.80 (s, 1H), 3.10 (br d, J=10.8 Hz, 2H), 2.96 (s, 2H), 2.27 (s, 3H), 2.22 (br s, 3H), 1.14 (d, J=13.2 Hz, 4H), 1.02 (br d, J=5.9 Hz, 6H); LCMS [M+H]+: 543.2.

Example 270: N-[4-fluoro-5-(1-pyridin-2-yl-3,6-dihydro-2H-pyridin-4-yl)-2-[(3R 5S)-3,4,5-trimethylpiperazin-1-yl]phenyl]-6-oxo-4-(trifluoromethyl)-1H-pyridine-3-carboxamide

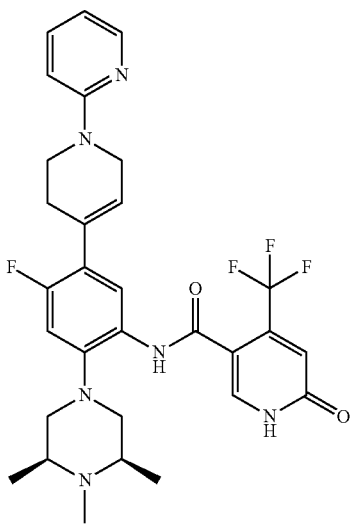 [SMILES: C[C@@H]1CN(c2cc(F)c(C3=CCN(c4ccccn4)CC3)cc2NC(=O)c2c[nH]c(=O)cc2C(F)(F)F)C[C@H](C)N1C]

Example 271: N-[4-fluoro-5-[1-(5-methylpyrimidin-2-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

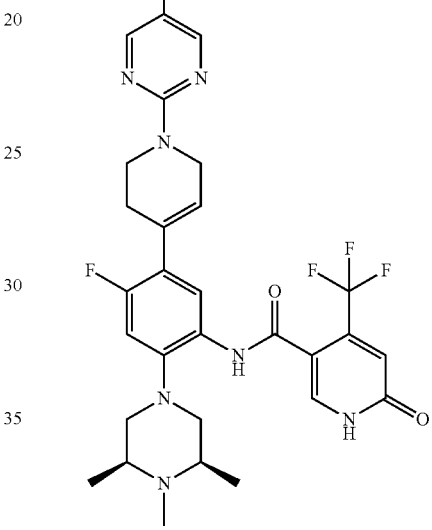

Copper (I) iodide (1.013 mg, 5.32 µmol) was added to a mixture of 2-chloropyridine 99% (6.50 µl, 0.069 mmol), N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (27 mg, 0.053 mmol) and N,N-diisopropylethylamine (0.028 ml, 0.160 mmol) in ethylene glycol (1.5 ml). The mixture was heated in a microwave reactor at 180° C. for 1 h. The mixture was quenched and worked up in a similar manner to Example 148 to provide the title compound as a yellow powder (8.5 mg, 26%). $^1$H NMR (500 MHz, METHANOL-d4) δ=7.99 (dd, J=1.2, 4.9 Hz, 1H), 7.85-7.82 (m, 1H), 7.73-7.67 (m, 1H), 7.51-7.45 (m, 1H), 6.87-6.83 (m, 1H), 6.82-6.79 (m, 1H), 6.76-6.71 (m, 1H), 6.60-6.52 (m, 1H), 6.08-6.01 (m, 1H), 4.04-3.99 (m, 2H), 3.75-3.70 (m, 2H), 2.95-2.90 (m, 2H), 2.55-2.43 (m, 6H), 2.29-2.27 (m, 3H), 1.06 (d, J=5.9 Hz, 6H); LCMS [M+H]+ 585.5.

In a small reaction vessel N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (26 mg, 0.051 mmol) and 2-chloro-5-methylpyrimidine (7.57 mg, 0.059 mmol) in ethanol (3 ml) were combined at ambient temperature, and N,N-diisopropylethylamine (0.018 ml, 0.102 mmol) was added. The mixture was heated for 3 h at 150° C., and the standard workup and purification provided (12 mg (36% yield) of the title compound. $^1$H NMR (500 MHz, METHANOL-d4) δ=8.31-8.19 (m, 2H), 7.94 (s, 1H), 7.85-7.72 (m, 1H), 6.98-6.94 (m, 1H), 6.92 (s, 1H), 6.12 (br s, 1H), 4.33 (br d, J=2.7 Hz, 2H), 4.01 (t, J=5.6 Hz, 2H), 3.04 (br d, J=10.5 Hz, 2H), 2.64-2.54 (m, 6H), 2.39 (s, 3H), 2.17 (s, 3H), 1.20-1.16 (m, 6H); LCMS [M+H]+ 600.4

415

Example 272: N-[4-fluoro-5-[6-[(2R,6S)-2,6-dimethylmorpholin-4-yl]pyridin-3-yl]-2-[(3S,5R)-3,4,5-trimethylpiperazin-1-yl]phenyl]-6-oxo-4-(trifluoromethyl)-1H-pyridine-3-carboxamide

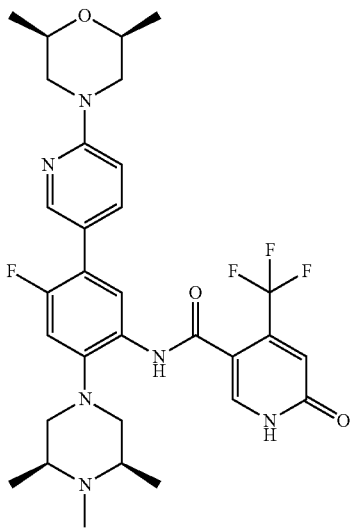

Step 1: (2S,6R)-2,6-dimethyl-4-(5-(4,4,5,5-tetramethyl-1,3,2-dioxaborolan-2-yl)pyridin-2-yl)morpholine

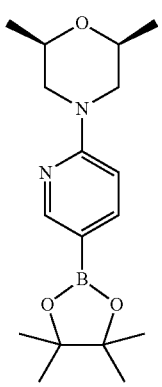

To a 20 mL microwave vial charged with 2-chloro-5-(4,4,5,5-tetramethyl-1,3,2-dioxaborolan-2-yl)pyridine (0.968 g, 4 mmol), cis-2,6-dimethylmorpholine (0.54 mL, 4.4 mmol) and Hunig base (1.39 mL, 8 mmol) was added NMP (2 mL). The resulting solution was heated at 140° C. for 2 h. After removing Hunig base, the mixture was purified by flash chromatography (gradient: EtOAc/hex 0-100%) to give the title compound as a crystalline beige solid (485 mg, yield 38%). LCMS for boronic acid [M+H]⁺ 237.2.

416

Step 2: N-(5-(6-((2S,6R)-2,6-dimethylmorpholino)pyridin-3-yl)-4-fluoro-2-((3S,5R)-3,4,5-trimethylpiperazin-1-yl)phenyl)-6-oxo-4-(trifluoromethyl)-1,6-dihydropyridine-3-carboxamide

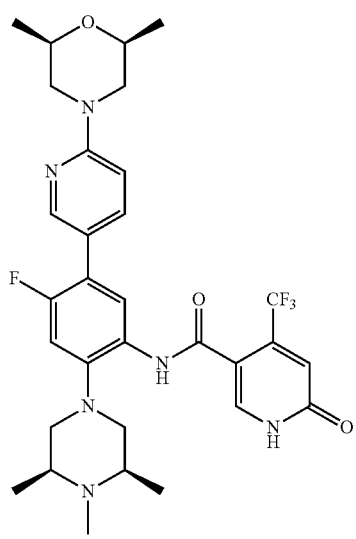

The title compound (off-white solid, 34.2 mg, 54%) was prepared by a procedure similar to that described in Example 31 using N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol) and (2S,6R)-2,6-dimethyl-4-(5-(4,4,5,5-tetramethyl-1,3,2-dioxaborolan-2-yl)pyridin-2-yl)morpholine (63 mg, 0.2 mmol). ¹H NMR (500 MHz, METHANOL-d4) δ=8.31 (s, 1H), 7.97 (s, 1H), 7.92 (br d, J=8.3 Hz, 1H), 7.78 (br d, J=9.2 Hz, 1H), 7.07 (d, J=12.1 Hz, 1H), 6.95-6.89 (m, 2H), 4.16 (br d, J=11.6 Hz, 2H), 3.74 (ddd, J=2.3, 6.3, 10.3 Hz, 2H), 3.07 (br d, J=10.4 Hz, 2H), 2.68-2.57 (m, 4H), 2.53 (dd, J=10.8, 12.6 Hz, 2H), 2.41 (s, 3H), 1.26 (d, J=6.2 Hz, 6H), 1.19 (br d, J=5.6 Hz, 6H); LCMS [M+H]⁺ 617.5.

Example 273: N-[4-fluoro-5-[2-[(2R,6S)-2,6-dimethylmorpholin-4-yl]pyrimidin-5-yl]-2-[(3R)-3,4-dimethylpiperazin-1-yl]phenyl]-1-methyl-6-oxo-4-(trifluoromethyl)pyridine-3-carboxamide

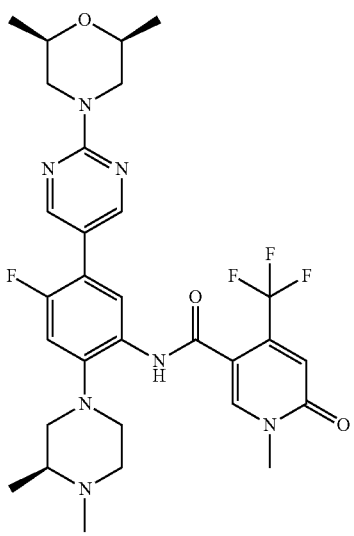

Step 1: (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide

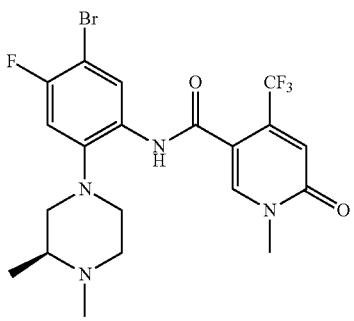 [SMILES: C[C@H]1CN(c2cc(F)c(Br)cc2NC(=O)c2cn(C)c(=O)cc2C(F)(F)F)CCN1C]

To a stirred solution of 1-methyl-6-oxo-4-(trifluoromethyl)-1,6-dihydropyridine-3-carboxylic acid (5 g, 22.62 mmol, 1 eq) in DMF (50 mL) was added HATU (25.79 g, 67.87 mmol, 3 eq) at 0° C. under argon atmosphere followed by DIPEA (11.82 mL, 67.87 mmol, 3 eq) and stirred for 15 min at the same temperature. Then, (S)-5-bromo-2-(3,4-dimethylpiperazin-1-yl)-4-fluoroaniline (2.99 g, 24.88 mmol, 1.1 eq) was added at 0° C. and the reaction mixture was allowed to remain at RT over 48 h. TLC analysis indicated formation of polar spot. The reaction mixture was diluted with water (300 mL) and extracted with EtOAc (3×100 mL). The organic layer was washed with ice water (2×200 mL) and dried over $Na_2SO_4$ then concentrated under reduced pressure to give crude product. Crude product was purified by column chromatography (Neutral Alumina) using 0-60% EtOAc in petroleum ether as an eluent to provide (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (4 g, 35%) as an off white solid. LCMS $[M+H]^+$ 505.23.

Step 2: N-(4-fluoro-5-(6-(2-methoxyethoxy)pyridin-3-yl)-2-((3S,5R)-3,4,5-trimethylpiperazin-1-yl)phenyl)-1-methyl-6-oxo-4-(trifluoromethyl)-1,6-dihydropyridine-3-carboxamide

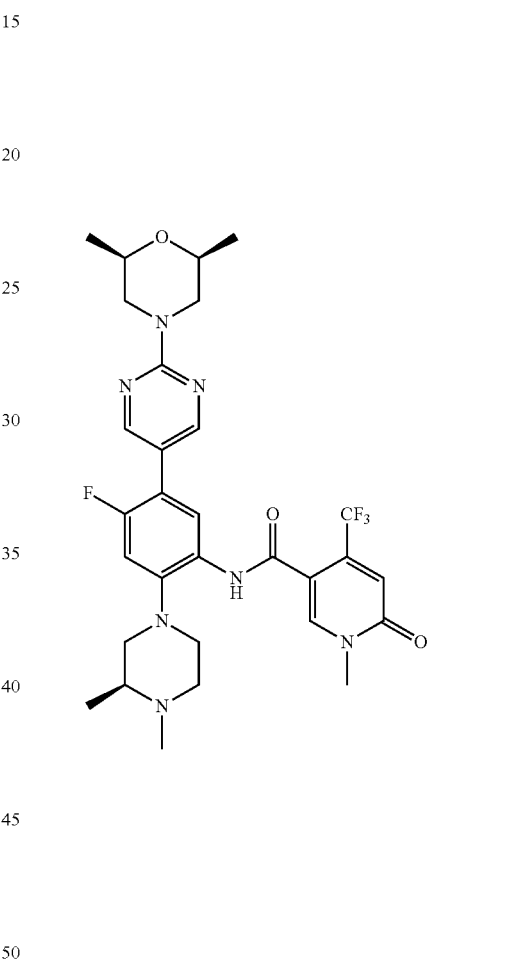

The title compound (white solid, 47.4 mg, 77%) was prepared by a procedure similar to that of Example 31 using (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (50.5 mg, 0.1 mmol) and (2-((2S, 6R)-2,6-dimethylmorpholino)pyrimidin-5-yl)boronic acid (47 mg, 0.2 mmol). $^1$H NMR (500 MHz, CHLOROFORM-d) δ=8.74 (br s, 1H), 8.54 (s, 2H), 8.46 (br d, J=7.8 Hz, 1H), 7.88 (s, 1H), 7.03 (d, J=11.1 Hz, 1H), 6.97 (s, 1H), 4.65-4.58 (m, 2H), 3.72-3.63 (m, 5H), 3.02-2.84 (m, 3H), 2.80 (br d, J=10.9 Hz, 1H), 2.70-2.54 (m, 3H), 2.43-2.28 (m, 4H), 2.20 (br s, 1H), 1.28 (d, J=6.2 Hz, 6H), 1.09 (br d, J=6.1 Hz, 3H); LCMS $[M+H]^+$ 618.4.

Example 274: N-[4-fluoro-5-[1-(6-methoxypyrimidin-4-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

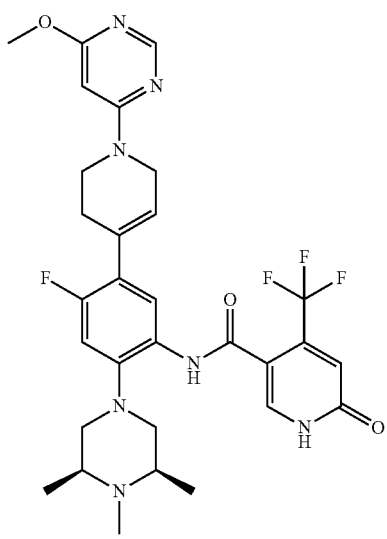 [SMILES: COc1cc(N2CC=C(c3cc(NC(=O)c4c[nH]c(=O)cc4C(F)(F)F)c(N4C[C@@H](C)N(C)[C@@H](C)C4)cc3F)CC2)ncn1]

To a microwave vial charged with N-(4-fluoro-5-(1,2,3,6-tetrahydropyridin-4-yl)-2-((3 S, 5R)-3,4,5-trimethylpiperazin-1-yl)phenyl)-6-oxo-4-(trifluoromethyl)-1,6-dihydropyridine-3-carboxamide (25.5 mg, 0.050 mmol) and 4-iodo-6-methoxy pyrimidine (13.64 mg, 0.058 mmol) in ethanol (3 ml) at RT, was added N,N-diisopropylethylamine (0.018 ml, 0.100 mmol). The mixture was heated at 130° C. for 3 h. The reaction was worked up and the product was purified by sgc to afford the title compound (19 mg, 58% yield). $^1$H NMR (500 MHz, METHANOL-d4) δ=8.26-8.21 (m, 1H), 7.98-7.93 (m, 1H), 7.85-7.76 (m, 1H), 6.99-6.94 (m, 1H), 6.94-6.90 (m, 1H), 6.12 (br s, 1H), 6.04 (s, 1H), 4.26-4.16 (m, 2H), 4.00-3.88 (m, 5H), 3.03 (br d, J=11.0 Hz, 2H), 2.65-2.52 (m, 6H), 2.38 (s, 3H), 1.19-1.15 (m, 6H); LCMS [M+H]+ 616.6

Example 275: N-[5-[1-(5-chloropyrimidin-2-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

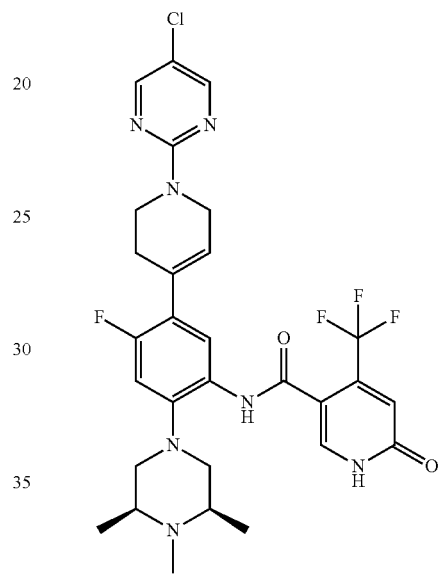

To a microwave vial charged with N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25.5 mg, 0.050 mmol) and 2,5-dichloropyrimidine (8.61 mg, 0.058 mmol) in ethanol (3 ml) at RT, was added N,N-diisopropylethylamine (0.018 ml, 0.100 mmol). The mixture was heated at 90° C. for 2 h. 95% conversion to the desired product was observed after 2 h. Standard workup and purification yielded the title compound (23 mg, 69% yield). $^1$H NMR (500 MHz, METHANOL-d4) δ=8.25-8.18 (m, 2H), 7.87-7.79 (m, 1H), 7.73-7.62 (m, 1H), 6.87-6.82 (m, 1H), 6.81-6.78 (m, 1H), 6.04-5.96 (m, 1H), 4.30-4.22 (m, 2H), 3.97-3.90 (m, 2H), 2.96-2.89 (m, 2H), 2.52-2.40 (m, 6H), 2.28-2.25 (m, 3H), 1.07-1.03 (m, 6H); LCMS [M+H]+ 620.

Example 276: ethyl 2-[4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridin-1-yl]pyrimidine-4-carboxylate

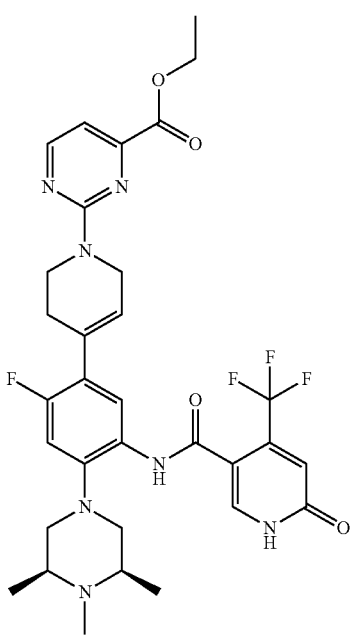 [SMILES: CCOC(=O)c1ccnc(N2CC=C(c3cc(NC(=O)c4c[nH]c(=O)cc4C(F)(F)F)c(N4C[C@@H](C)N(C)[C@@H](C)C4)cc3F)CC2)n1]

A small microwave flask was charged with N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25. mg, 0.049 mmol) and methyl 2-chloropyrimidine-4-carboxylate (9.78 mg, 0.057 mmol) in ethanol (3 ml) at RT, followed by N,N-diisopropylethylamine (0.017 ml, 0.099 mmol). The mixture was heated at 90° C. for 72 h. A standard workup and purification yielded the title compound (16 mg, 47% yield). $^1$H NMR (500 MHz, METHANOL-d4) δ=8.61-8.57 (m, 1H), 8.06-7.95 (m, 1H), 7.87-7.77 (m, 1H), 7.22-7.14 (m, 1H), 7.09-7.01 (m, 1H), 6.99-6.90 (m, 1H), 6.21-6.11 (m, 1H), 4.49-4.40 (m, 4H), 4.17-4.10 (m, 2H), 3.24-3.10 (m, 4H), 2.86-2.78 (m, 2H), 2.78-2.70 (m, 3H), 2.66-2.59 (m, 2H), 1.45-1.40 (m, 3H), 1.36-1.32 (m, 6H); LCMS [M+H]+ 658.4.

Example 277: N-[4-fluoro-2-[3-(methylamino)pyrrolidin-1-yl]-5-(2-morpholin-4-ylpyrimidin-5-yl)phenyl]-6-oxo-4-(trifluoromethyl)-1H-pyridine-3-carboxamide

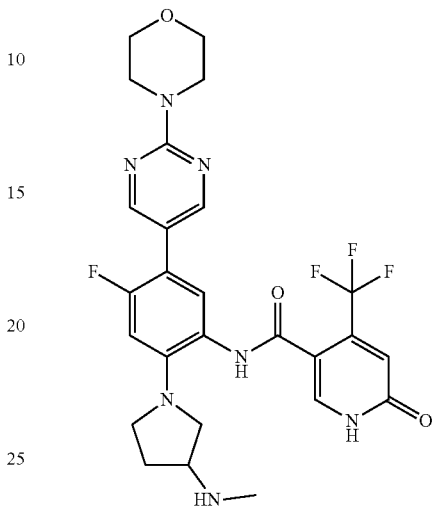

Step 1: tert-butyl (1-(4-bromo-5-fluoro-2-nitrophenyl)pyrrolidin-3-yl)(methyl)carbamate

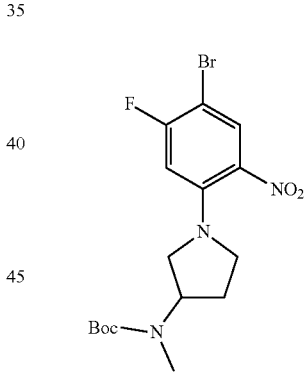

A suspension of 3-N-boc-3-(methylamino)pyrrolidine (1.33 g, 6.64 mmol) and K2CO₃ (0.459 g, 3.32 mmol) in toluene (10 ml) was stirred for 5 min at room temperature. Then a solution of 1-bromo-2,4-difluoro-5-nitrobenzene (1.580 g, 6.64 mmol) in toluene (1 ml) was added dropwise from a pipette (2 ml of toluene were used to rinse the vial) and the reaction was stirred at 50° C. for 3 h 30 min. Then the reaction mixture was partitioned into water and DCM and the product was extracted by DCM (3×20 mL). The organic phase was dried over MgSO₄ and after filtration and solvents removal, the crude material was dry loaded and purified by flash chromatography [0-10% MeOH/DCM] to afford the desired tert-butyl (1-(4-bromo-5-fluoro-2-nitrophenyl)pyrrolidin-3-yl)(methyl)carbamate (2.17 g, 5.19 mmol, 78% yield) as an orange oil. LCMS [M+H]+ 418.2.

Step 2: tert-butyl (1-(5-fluoro-4-(2-morpholinopyrimidin-5-yl)-2-nitrophenyl)pyrrolidin-3-yl)(methyl)carbamate

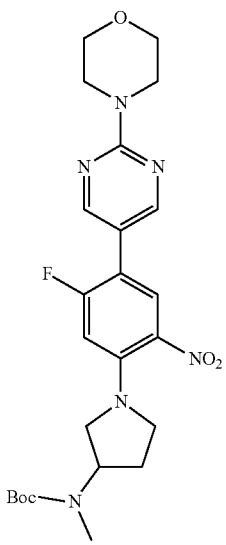 [SMILES: CN(C(=O)OC(C)(C)C)C1CCN(c2cc(F)c(-c3cnc(N4CCOCC4)nc3)cc2[N+](=O)[O-])C1]

A 100 mL RBF was charged with a mixture of tert-butyl (1-(4-bromo-5-fluoro-2-nitrophenyl)pyrrolidin-3-yl)(methyl)carbamate (2.17 g, 5.19 mmol), XPhos (0.049 g, 0.104 mmol), XPhos (0.049 g, 0.104 mmol) and XPhos (0.049 g, 0.104 mmol). Then 1,4-dioxane (50 ml) and sodium carbonate solution (2 M) (2.75 mL) were added via syringe and the vial was flushed with argon. The reaction was stirred at 90° C. overnight. Then the reaction mixture was partitioned into water and DCM and the product was extracted by DCM (3×50 mL). The organic phase was dried over MgSO₄ and after filtration and solvents removal, the crude material was dry loaded and purified by Flash chromatography [0-10% MeOH/DCM] to afford the desired tert-butyl (1-(5-fluoro-4-(2-morpholinopyrimidin-5-yl)-2-nitrophenyl)pyrrolidin-3-yl)(methyl)carbamate (1.21 g, 2.415 mmol, 46.6% yield) as a dark orange oil. LCMS [M+H]+ 503.4.

Step 3: tert-butyl (1-(2-amino-5-fluoro-4-(2-morpholinopyrimidin-5-yl)phenyl)pyrrolidin-3-yl)(methyl)carbamate

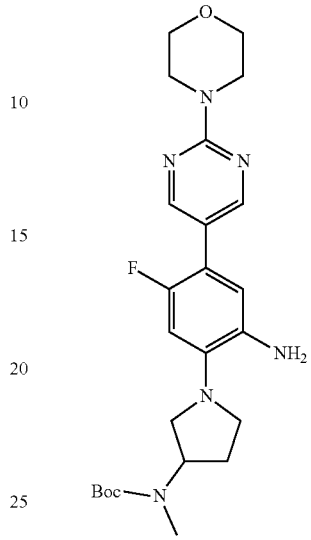

A mixture of tert-butyl (1-(5-fluoro-4-(2-morpholinopyrimidin-5-yl)-2-nitrophenyl)pyrrolidin-3-yl)(methyl)carbamate (1.8598 g, 3.70 mmol) and tin(II) chloride, 98% (2.105 g, 11.10 mmol) in a mixture of EtOH (10 ml) and MeOH (10 ml) was heated to 90° C. for 3 h. Then the reaction mixture was concentrated onto celite and purified by flash [0.5-10% MeOH/DCM] to afford the tert-butyl (1-(2-amino-5-fluoro-4-(2-morpholinopyrimidin-5-yl)phenyl)pyrrolidin-3-yl)(methyl)carbamate (0.94 g, 1.990 mmol, 53.8% yield) as a yellow solid. LCMS [M+H]+ 473.2.

Step 4: tert-butyl (1-(5-fluoro-4-(2-morpholinopyrimidin-5-yl)-2-(4-(trifluoromethyl)-6-(2-(trimethylsilyl)ethoxy)nicotinamido)phenyl)pyrrolidin-3-yl)(methyl)carbamate

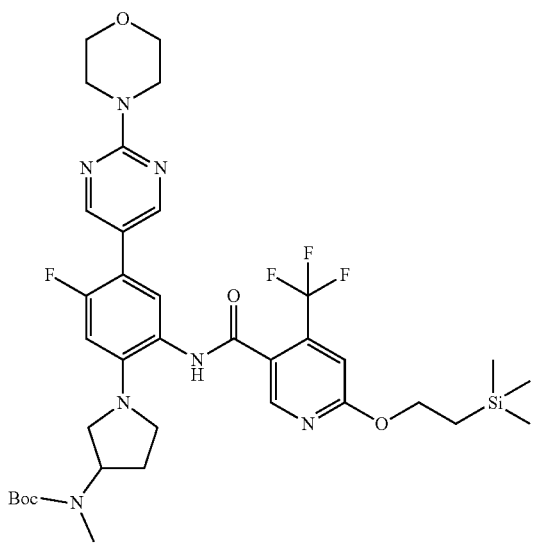 [SMILES: CN(C(=O)OC(C)(C)C)C1CCN(c2cc(F)c(-c3cnc(N4CCOCC4)nc3)cc2NC(=O)c2cnc(OCC[Si](C)(C)C)cc2C(F)(F)F)C1]

Propylphosphonic anhydride solution (0.189 ml, 0.317 mmol) was added dropwise to a mixture of 4-(trifluoromethyl)-6-(2-(trimethylsilyl)ethoxy)nicotinic acid (72 mg, 0.234 mmol) and pyridine (5.24 ml, 65.1 mmol) in DCM (2 ml) under N₂ atmosphere at room temperature. After 15 minutes of stirring at 50° C. a solution of tert-butyl (1-(2-amino-5-fluoro-4-(2-morpholinopyrimidin-5-yl)phenyl)pyrrolidin-3-yl)(methyl)carbamate (100 mg, 0.212 mmol) in 2 mL of DCM was added and the reaction mixture was heated at 50° C. overnight. The reaction mixture was then concentrated onto celite and purified by flash chromatography [0-10% MeOH/DCM] to afford the tert-butyl (1-(5-fluoro-4-(2-morpholinopyrimidin-5-yl)-2-(4-(trifluoromethyl)-6-(2-(trimethylsilyl)ethoxy)nicotinamido)phenyl)pyrrolidin-3-yl)(methyl)carbamate (161 mg, 0.211 mmol, 100% yield) as an off-white powder. LCMS [M+H]+ 762.5.

Step 5: N-(4-fluoro-2-(3-(methylamino)pyrrolidin-1-yl)-5-(2-morpholinopyrimidin-5-yl)phenyl)-6-oxo-4-(trifluoromethyl)-1,6-dihydropyridine-3-carboxamide

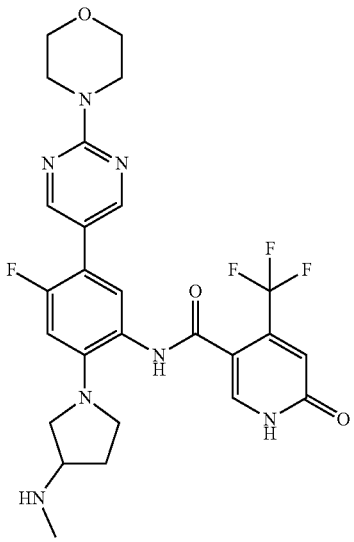 [SMILES: CNC1CCN(c2cc(F)c(-c3cnc(N4CCOCC4)nc3)cc2NC(=O)c2c[nH]c(=O)cc2C(F)(F)F)C1]

To a solution of tert-butyl (1-(5-fluoro-4-(2-morpholinopyrimidin-5-yl)-2-(4-(trifluoromethyl)-6-(2-(trimethylsilyl)ethoxy)nicotinamido)phenyl)pyrrolidin-3-yl)(methyl)carbamate (161 mg, 0.211 mmol) in DCM (3 ml) was added trifluoroacetic acid (2 ml, 26.1 mmol). The reaction mixture was stirred at 60° C. for 50 minutes. Then the TFA and solvent were removed under vacuum and the crude material was purified by flash chromatography [0-40% DCM/MeOH] to afford the N-(4-fluoro-2-(3-(methylamino)pyrrolidin-1-yl)-5-(2-morpholinopyrimidin-5-yl)phenyl)-6-oxo-4-(trifluoromethyl)-1,6-dihydropyridine-3-carboxamide (6.4 mg, 0.011 mmol, 5.39% yield) as a white powder (yield for 2 steps). ¹H NMR (500 MHz, DMSO-d6) δ=9.79 (br s, 1H), 8.49 (s, 2H), 7.98 (br s, 1H), 7.29 (br d, J=8.6 Hz, 1H), 6.75 (s, 1H), 6.62 (d, J=14.1 Hz, 1H), 3.75-3.71 (m, 4H), 3.69-3.65 (m, 4H), 3.46 (br dd, J=5.6, 9.2 Hz, 1H), 3.41-3.38 (m, 1H), 3.18-3.13 (m, 1H), 3.10 (br dd, J=4.5, 9.7 Hz, 1H), 2.26 (s, 3H), 2.03-1.94 (m, 1H), 1.76-1.66 (m, 1H), 1.23 (s, 1H); LCMS [M+H]+ 562.3.

Example 278: N-[2-[3-[(dimethylamino)methyl]pyrrolidin-1-yl]-4-fluoro-5-(2-morpholin-4-ylpyrimidin-5-yl)phenyl]-6-oxo-4-(trifluoromethyl)-1H-pyridine-3-carboxamide

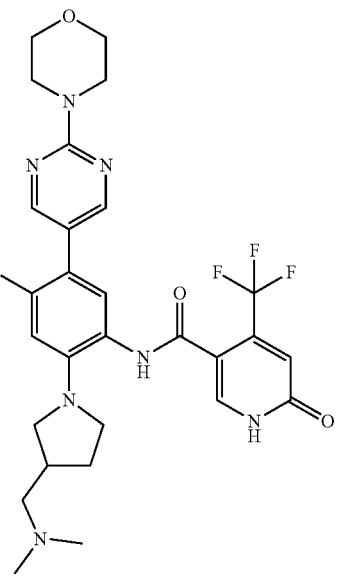

The title compound was prepared similar to the procedure described above for the preparation of Example 234 using N,N-dimethyl(3-pyrrolidinyl)methanamine in place of (R)—N-ethyl-N-methylpyrrolidin-3-amine in Step 1. ¹H NMR (500 MHz, DMSO-d6) δ=9.81 (s, 1H), 8.50 (s, 2H), 7.95 (s, 1H), 7.29 (d, J=8.8 Hz, 1H), 6.80 (s, 1H), 6.62 (d, J=14.1 Hz, 1H), 3.76-3.70 (m, 4H), 3.69-3.65 (m, 4H), 3.10 (br dd, J=7.1, 9.3 Hz, 1H), 2.44-2.33 (m, 1H), 2.24 (br s, 2H), 2.16 (br s, 6H), 1.98 (qd, J=6.0, 11.8 Hz, 1H), 1.64-1.52 (m, 1H); LCMS [M+H]+: 590.4.

Example 279: N-[4-fluoro-5-[2-(4-methylpiperazin-1-yl)pyrimidin-5-yl]-2-[(3R)-3,4-dimethylpiperazin-1-yl]phenyl]-1-methyl-6-oxo-4-(trifluoromethyl)pyridine-3-carboxamide

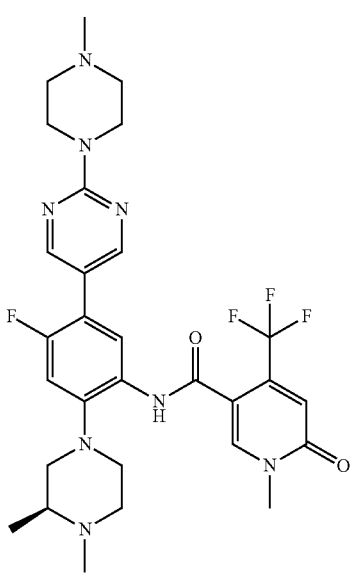 [SMILES: C[C@H]1CN(c2cc(F)c(-c3cnc(N4CCN(C)CC4)nc3)cc2NC(=O)c2cn(C)c(=O)cc2C(F)(F)F)CCN1C]

The title compound (light beige solid, 44.2 mg, 72%) was prepared by a procedure similar to Example 273 using (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (50.5 mg, 0.1 mmol) and 2-(4-methylpiperazin-1-yl)pyrimidine-5-boronic acid pinacol ester (61 mg, 0.2 mmol). $^1$H NMR (500 MHz, METHANOL-d4) δ=8.57-8.53 (m, 2H), 8.26 (s, 1H), 7.92 (d, J=8.3 Hz, 1H), 7.11 (br d, J=10.9 Hz, 1H), 6.95 (s, 1H), 3.97-3.85 (m, 4H), 3.66 (s, 3H), 3.14-3.03 (m, 2H), 3.00-2.87 (m, 2H), 2.61-2.49 (m, 6H), 2.43-2.34 (m, 7H), 1.13 (d, J=6.1 Hz, 3H); LCMS [M+H]$^+$ 603.4.

Example 280: N-[4-fluoro-5-(2-morpholin-4-ylpyrimidin-5-yl)-2-[(3R,5S)-3,4,5-trimethylpiperazin-1-yl]phenyl]-3-hydroxy-5-(trifluoromethyl)benzamide

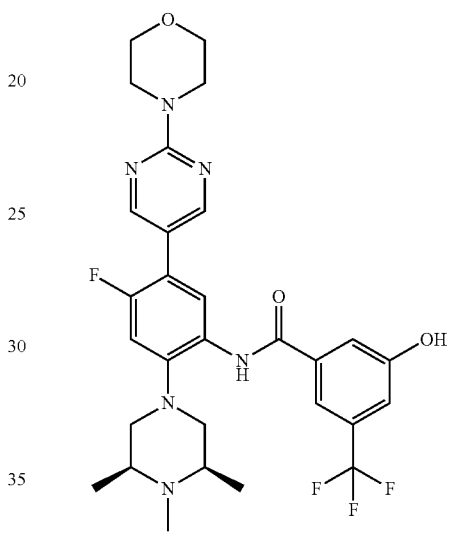

To a 25 mL RBF was charged with 3-hydroxy-5-(trifluoromethyl)benzoic acid (41 mg, 0.2 mmol) was added thionyl chloride (0.364 mL, 5 mmol). The resulting suspension was heated at 80° C. for 1 h (very insoluble, turned clear in about 15 min). The solvents were evaporated to give a light yellow oil which was treated with DCM (5 mL), 4-fluoro-5-(2-morpholinopyrimidin-5-yl)-2-((3S,5R)-3,4,5-trimethylpiperazin-1-yl)aniline (40 mg, 0.1 mmol) and Et$_3$N (42 μL, 0.3 mmol). The resulting dark brown suspension was stirred at rt for 30 min and purified by flash chromatography and prep-HPLC to give the title compound as a beige solid (formic acid salt, 2.6 mg, 4%). $^1$H NMR (500 MHz, METHANOL-d4) δ=8.58 (s, 2H), 8.50 (br s, 1H), 8.09 (d, J=8.2 Hz, 1H), 7.68 (s, 1H), 7.61 (s, 1H), 7.29 (s, 1H), 7.14 (d, J=11.9 Hz, 1H), 3.88-3.83 (m, 4H), 3.80-3.76 (m, 4H), 3.17 (br d, J=10.6 Hz, 2H), 2.83-2.71 (m, 4H), 2.53 (s, 3H), 1.24 (d, J=5.9 Hz, 6H); LCMS [M+H]$^+$ 589.4.

Example 281: N-[4-fluoro-5-(2-morpholin-4-ylpyrimidin-5-yl)-2-[(3R,5S)-3,4,5-trimethylpiperazin-1-yl]phenyl]-3-hydroxybenzamide

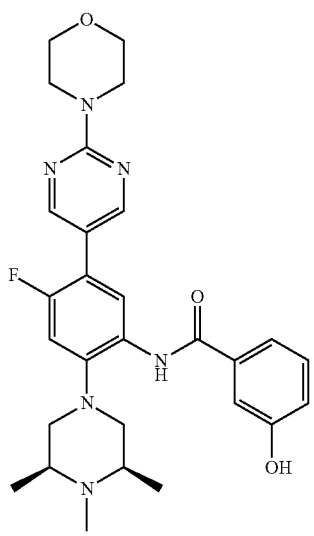 [SMILES: C[C@@H]1CN(c2cc(F)c(-c3cnc(N4CCOCC4)nc3)cc2NC(=O)c2cccc(O)c2)C[C@H](C)N1C]

To a solution of N-(4-fluoro-5-(2-morpholinopyrimidin-5-yl)-2-((3S,5R)-3,4,5-trimethylpiperazin-1-yl)phenyl)-3-methoxybenzamide (21.4 mg, 0.04 mmol) in DCM (1 mL) at 0° C. was added boron tribromide solution (1.0 M in methylene chloride, 0.2 mL, 0.2 mmol). The mixture was stirred at rt for 3 h, quenched with H₂O (20 mL), sat. NaHCO₃ (15 mL) and extracted with DCM (30 mL×2). The combined DCM extracts were concentrated and purified by prep-HPLC to give the title compound as off-white solid (6.6 mg, 31%). ¹H NMR (500 MHz, METHANOL-d4) δ=8.58 (s, 2H), 8.07 (d, J=8.2 Hz, 1H), 7.44-7.36 (m, 3H), 7.16 (d, J=11.9 Hz, 1H), 7.06 (br d, J=7.7 Hz, 1H), 3.89-3.82 (m, 4H), 3.81-3.75 (m, 4H), 3.23 (br d, J=11.6 Hz, 2H), 3.00 (br s, 2H), 2.88-2.74 (m, 2H), 2.65 (s, 3H), 1.28 (d, J=6.2 Hz, 6H); LCMS [M+H]⁺ 521.4.

Example 282: N-[4-fluoro-5-(2-morpholin-4-ylpyrimidin-5-yl)-2-[(3R,5S)-3,4,5-trimethylpiperazin-1-yl]phenyl]-3-hydroxyquinoline-4-carboxamide

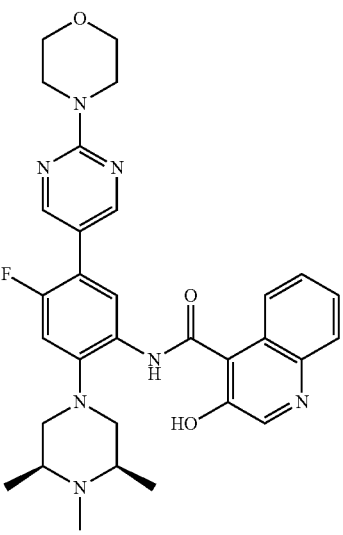 [SMILES: C[C@@H]1CN(c2cc(F)c(-c3cnc(N4CCOCC4)nc3)cc2NC(=O)c2c(O)cnc3ccccc23)C[C@H](C)N1C]

A mixture of 4-fluoro-5-(2-morpholinopyrimidin-5-yl)-2-((3S,5R)-3,4,5-trimethylpiperazin-1-yl)aniline (80 mg, 0.2 mmol), 3-hydroxyquinoline-4-carboxylic acid (76 mg, 0.4 mmol) and DCC (103 mg, 0.5 mmol) in DCM (6 mL) in a 30 mL vial was sealed and heated at 45° C. for 18 h. It was loaded directly onto Biotage samplet and purified by flash chromatography (gradient: EtOAc/hex 0-100% then MeOH/DCM 0-20%) to give the title compound as a dark yellow solid (85.6 mg, 74%). ¹H NMR (500 MHz, METHANOL-d4) δ=9.21 (br d, J=8.7 Hz, 1H), 8.63 (s, 2H), 8.56 (d, J=8.4 Hz, 1H), 8.53 (s, 1H), 7.81 (d, J=8.1 Hz, 1H), 7.46 (t, J=7.8 Hz, 1H), 7.33 (t, J=7.5 Hz, 1H), 7.07 (d, J=12.0 Hz, 1H), 3.89-3.83 (m, 4H), 3.81-3.76 (m, 4H), 3.44-3.35 (m, 2H), 3.31-3.25 (m, 2H), 2.79-2.68 (m, 5H), 1.28 (d, J=6.5 Hz, 6H); LCMS [M+H]⁺ 572.5.

Example 283: N-[4-fluoro-5-(2-morpholin-4-ylpyrimidin-5-yl)-2-[(3R)-3-(dimethylamino)pyrrolidin-1-yl]phenyl]-1-methyl-3-(triluoromethyl)pyrazole-4-carboxamide Example 284: N-[4-fluoro-5-(2-morpholin-4-ylpyrimidin-5-yl)-2-[(3R)-3,4-dimethylpiperazin-1-yl]phenyl]-1-methyl-3-(trifluoromethyl)pyrazole-4-carboxamide

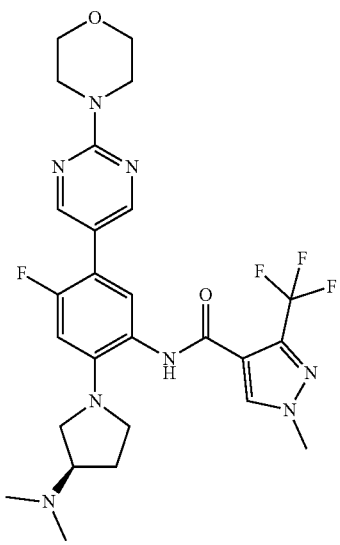 [SMILES: CN(C)[C@@H]1CCN(c2cc(F)c(-c3cnc(N4CCOCC4)nc3)cc2NC(=O)c2cn(C)nc2C(F)(F)F)C1]

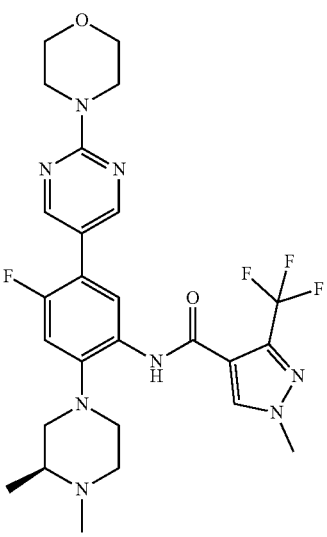 [SMILES: C[C@H]1CN(c2cc(F)c(-c3cnc(N4CCOCC4)nc3)cc2NC(=O)c2cn(C)nc2C(F)(F)F)CCN1C]

1-Methyl-3-(trifluoromethyl)-1H-pyrazole-4-carboxylic acid (0.038 g, 0.194 mmol) was activated in DMF (1 ml) with HATU (0.074 g, 0.194 mmol) and N,N-diisopropylethylamine (0.034 ml, 0.194 mmol). The solution of activated acid was then added to a stirring solution of (R)-1-(2-amino-5-fluoro-4-(2-morpholinopyrimidin-5-yl)phenyl)-N,N-dimethylpyrrolidin-3-amine (0.050 g, 0.129 mmol) in N,N-dimethylformamide (DMF) (1 ml) at room temperature. The reaction was warmed to 50° C. then heated at 60° C. overnight. Workup and purification using standard methods afforded the title compound (0.071 mmol, 55.0% yield) as a tan solid. $^1$H NMR (500 MHz, DMSO-d6) δ=9.29 (s, 1H), 8.55 (d, J=0.7 Hz, 2H), 8.49 (s, 1H), 7.79 (d, J=8.4 Hz, 1H), 7.13 (d, J=12.2 Hz, 1H), 4.01 (s, 3H), 3.78-3.73 (m, 4H), 3.72-3.65 (m, 4H), 3.05-2.98 (m, 1H), 2.95 (br d, J=10.9 Hz, 1H), 2.88-2.79 (m, 1H), 2.78-2.72 (m, 1H), 2.66-2.63 (m, 1H), 2.45 (br d, J=10.5 Hz, 1H), 2.37 (br d, J=1.6 Hz, 1H), 2.34-2.27 (m, 1H), 2.25-2.16 (m, 4H), 0.96 (d, J=6.2 Hz, 3H); LCMS [M+H]+: 563.4.

1-Methyl-3-(trifluoromethyl)-1H-pyrazole-4-carboxylic acid (0.038 g, 0.194 mmol) was activated in DMF (1 mL) with HATU (0.074 g, 0.194 mmol) and N,N-diisopropylethylamine (0.034 ml, 0.194 mmol). The solution of activated acid was then added to a stirring solution of (S)-2-(3,4-dimethylpiperazin-1-yl)-4-fluoro-5-(2-morpholinopyrimidin-5-yl)aniline (0.050 g, 0.129 mmol) in DMF (1 ml) at room temperature. The reaction was warmed to 50° C. and monitored by LCMS [230 pm—start heating]. After heating at 60° C. overnight, workup and purification afforded the title compound (27 mg, 37% yield). $^1$H NMR (500 MHz, DMSO-d6) δ=9.72 (s, 1H), 8.51 (s, 2H), 8.47 (s, 1H), 7.21 (d, J=8.8 Hz, 1H), 6.67 (d, J=13.8 Hz, 1H), 3.99 (s, 3H), 3.75-3.72 (m, 4H), 3.70-3.66 (m, 4H), 3.40-3.35 (m, 3H), 3.21 (t, J=8.8 Hz, 1H), 2.11 (s, 6H), 2.09-2.03 (m, 1H), 1.68 (quin, J=10.0 Hz, 1H); LCMS [M+H]+: 563.5.

Example 285: N-[5-[1-(dimethylcarbamoyl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

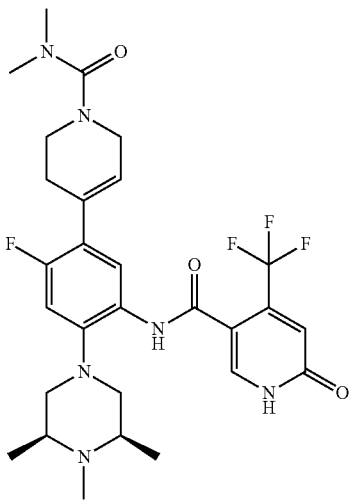

The procedure used was similar to that of Example 253 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and dimethylcarbamoyl chloride (4.76 µl, 0.052 mmol) to give after workup and purification the title compound (24 mg, 75% yield). $^1$H NMR (500 MHz, METHANOL-d4) δ=7.99-7.90 (m, 1H), 7.82-7.73 (m, 1H), 6.99-6.94 (m, 1H), 6.93-6.90 (m, 1H), 6.06-5.97 (m, 1H), 4.01-3.92 (m, 2H), 3.50-3.46 (m, 2H), 3.06-2.99 (m, 2H), 2.93-2.87 (m, 6H), 2.65-2.52 (m, 6H), 2.43-2.36 (m, 3H), 1.21-1.15 (m, 6H); LCMS [M+H]+ 579.3.

Example 286: N-[4-fluoro-5-[1-(pyrrolidine-1-carbonyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

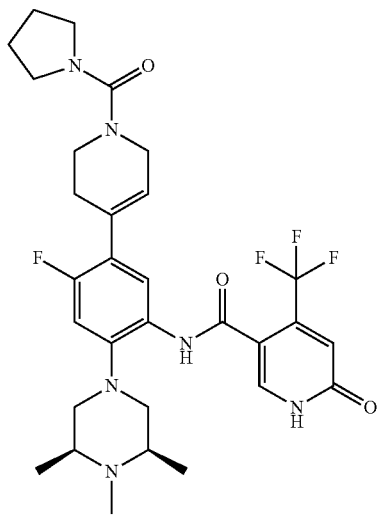 [SMILES: C[C@@H]1CN(c2cc(F)c(C3=CCN(C(=O)N4CCCC4)CC3)cc2NC(=O)c2c[nH]c(=O)cc2C(F)(F)F)C[C@H](C)N1C]

The procedure was similar to Example 253 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and 1-pyrrolidinecarbonyl chloride (5.71 µl, 0.052 mmol) to give, after workup and purification, the title compound (19 mg, 61% yield). $^1$H NMR (500 MHz, METHANOL-d4) δ=7.98-7.91 (m, 1H), 7.84-7.73 (m, 1H), 6.98-6.93 (m, 1H), 6.93-6.91 (m, 1H), 6.06-5.97 (m, 1H), 4.04-3.96 (m, 2H), 3.57-3.50 (m, 2H), 3.46-3.41 (m, 4H), 3.09-2.96 (m, 2H), 2.63-2.50 (m, 6H), 2.43-2.35 (m, 3H), 1.93-1.85 (m, 4H), 1.19-1.15 (m, 6H); LCMS [M+H]+ 605.4.

Example 287: N-[4-fluoro-5-[1-(4-methylpiperazine-1-carbonyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

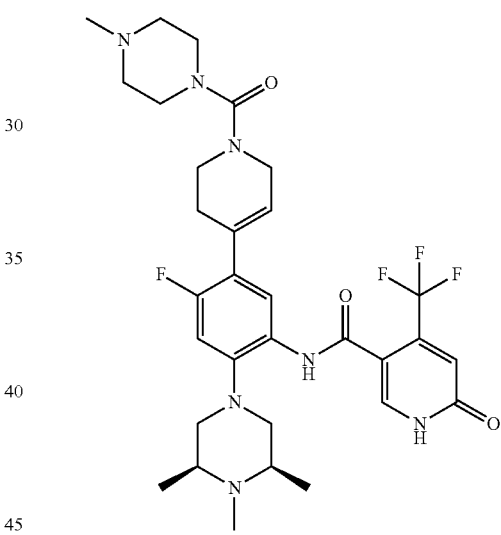

The procedure employed was similar to that of Example 253 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and 4-methyl-1-piperazinecarbonyl chloride hydrochloride (10.30 mg, 0.052 mmol) to give, after workup and purification, the title compound as a white powder (24 mg, 73% yield). $^1$H NMR (500 MHz, METHANOL-d4) δ=7.98-7.90 (m, 1H), 7.83-7.72 (m, 1H), 6.99-6.93 (m, 1H), 6.93-6.91 (m, 1H), 6.04-5.97 (m, 1H), 4.03-3.97 (m, 2H), 3.54-3.49 (m, 2H), 3.38-3.35 (m, 4H), 3.06-2.99 (m, 2H), 2.64-2.53 (m, 6H), 2.53-2.47 (m, 4H), 2.41-2.37 (m, 3H), 2.37-2.33 (m, 3H), 1.17 (d, J=5.9 Hz, 6H); LCMS [M+H]+ 634.7.

435

Example 288: phenyl 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate

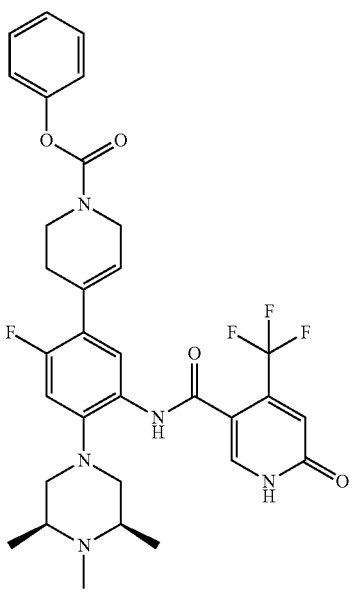 [SMILES: C[C@@H]1CN(c2cc(F)c(C3=CCN(C(=O)Oc4ccccc4)CC3)cc2NC(=O)c2c[nH]c(=O)cc2C(F)(F)F)C[C@H](C)N1C]

The procedure was similar to that of Example 253 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and phenyl chloroformate (6.51 µl, 0.052 mmol) to give, after standard workup and purification, the title compound (23 mg, 71% yield). $^1$H NMR (500 MHz, METHANOL-d4) δ=7.99-7.93 (m, 1H), 7.86-7.78 (m, 1H), 7.45-7.37 (m, 2H), 7.29-7.22 (m, 1H), 7.21-7.11 (m, 2H), 7.03-6.95 (m, 1H), 6.95-6.90 (m, 1H), 6.12-6.03 (m, 1H), 4.45-4.17 (m, 2H), 3.98-3.74 (m, 2H), 3.08-3.01 (m, 2H), 2.71-2.52 (m, 6H), 2.43-2.36 (m, 3H), 1.21-1.16 (m, 6H); LCMS [M+H]+ 628.3.

436

Example 289: N-[4-fluoro-5-[1-[(2R,6S)-2,6-dimethyloxan-4-yl]-3,6-dihydro-2H-pyridin-4-yl]-2-[(3S,5R)-3,4,5-trimethylpiperazin-1-yl]phenyl]-6-oxo-4-(trifluoromethyl)-1H-pyridine-3-carboxamide

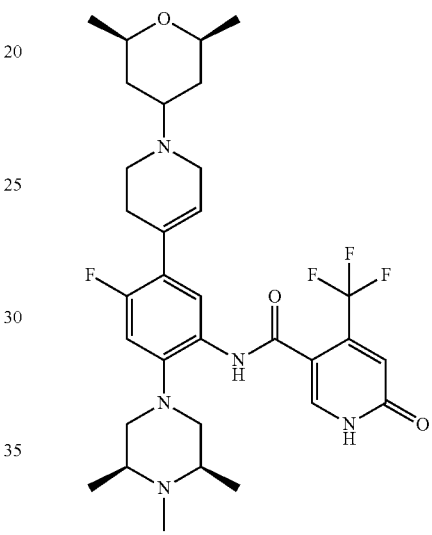

The procedure followed was similar to that of Example 148 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) and cis-2,6-dimethyloxan-4-one (15.15 mg, 0.118 mmol) to give, after workup and purification, the title compound (16 mg, 40% yield). $^1$H NMR (500 MHz, METHANOL-d4) δ=8.02-7.94 (m, 1H), 7.91-7.82 (m, 1H), 7.15-7.04 (m, 1H), 6.99-6.91 (m, 1H), 6.15-6.03 (m, 1H), 3.98-3.87 (m, 2H), 3.66-3.46 (m, 4H), 3.27-3.16 (m, 4H), 2.88-2.88 (m, 1H), 2.92-2.81 (m, 3H), 2.80-2.66 (m, 4H), 2.22-2.11 (m, 2H), 1.42-1.33 (m, 8H), 1.30-1.19 (m, 6H); LCMS [M+H]+ 620.6

Example 290: N-[4-fluoro-5-(2-morpholin-4-ylpyrimidin-5-yl)-2-[(3R,5S)-3,4,5-trimethylpiperazin-1-yl]phenyl]-4-hydroxy-2-(trifluoromethyl)benzamide

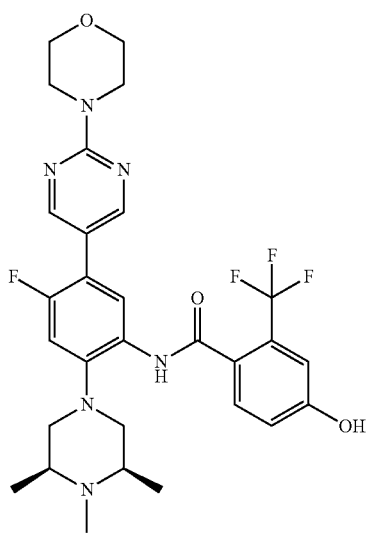 [SMILES: C[C@@H]1CN(c2cc(F)c(-c3cnc(N4CCOCC4)nc3)cc2NC(=O)c2ccc(O)cc2C(F)(F)F)C[C@H](C)N1C]

A mixture of 4-fluoro-5-(2-morpholinopyrimidin-5-yl)-2-((3S,5R)-3,4,5-trimethylpiperazin-1-yl)aniline (80 mg, 0.2 mmol), 4-hydroxy-2-(trifluoromethyl)benzoic acid (82 mg, 0.4 mmol) and DCC (103 mg, 0.5 mmol) in DCM (5 mL) in a 30 mL vial was sealed and heated d at 45° C. for 18 h. It was purified by flash chromatography and prep-HPLC to give the title compound as a beige solid (TFA salt, 23.9 mg, 17%). $^1$H NMR (500 MHz, METHANOL-d4) δ=8.56 (s, 2H), 8.32 (br s, 1H), 8.03 (d, J=8.2 Hz, 1H), 7.59 (br d, J=8.4 Hz, 1H), 7.23-7.18 (m, 2H), 7.14 (br d, J=8.3 Hz, 1H), 3.87-3.82 (m, 4H), 3.80-3.74 (m, 4H), 3.57-3.43 (m, 2H), 3.33-3.28 (m, 2H), 3.01 (br t, J=12.1 Hz, 2H), 2.93 (s, 3H), 1.43 (d, J=6.4 Hz, 6H); LCMS [M+H]$^+$ 589.4.

Example 291: 2,3-difluoro-N-[4-fluoro-5-(2-morpholin-4-ylpyrimidin-5-yl)-2-[(3R,5S)-3,4,5-trimethylpiperazin-1-yl]phenyl]-5-hydroxybenzamide

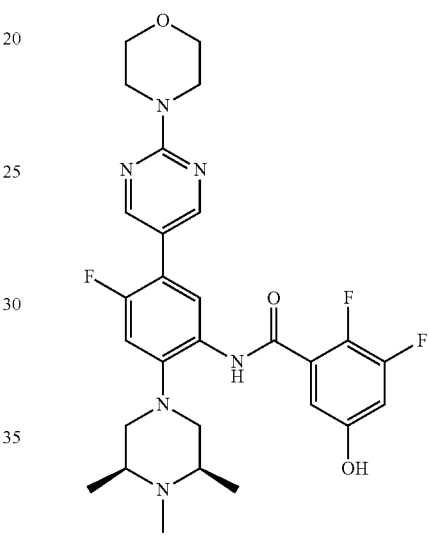

A mixture of 4-fluoro-5-(2-morpholinopyrimidin-5-yl)-2-((3S,5R)-3,4,5-trimethylpiperazin-1-yl)aniline (80 mg, 0.2 mmol), 2,3-difluoro-5-hydroxybenzoic acid (70 mg, 0.4 mmol) and DCC (103 mg, 0.5 mmol) in DCM (5 mL) in a 30 mL vial was sealed and heated at 45° C. overnight (18 h). It was purified by flash chromatography and prep-HPLC to give the title compound as a light purple solid (TFA salt, 15.7 mg, 12%). $^1$H NMR (500 MHz, METHANOL-d4) δ=8.59 (s, 2H), 8.31 (d, J=8.3 Hz, 1H), 7.36 (q, J=9.5 Hz, 1H), 7.25 (br d, J=11.6 Hz, 1H), 6.81 (d, J=8.7 Hz, 1H), 3.92-3.85 (m, 4H), 3.82-3.75 (m, 4H), 3.58-3.43 (m, 2H), 3.39 (br d, J=12.8 Hz, 2H), 3.02-2.90 (m, 5H), 1.45 (d, J=6.5 Hz, 6H); LCMS [M+H]$^+$ 557.3.

Example 292: N-[5-[2-(cyclobutylmethoxy)pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

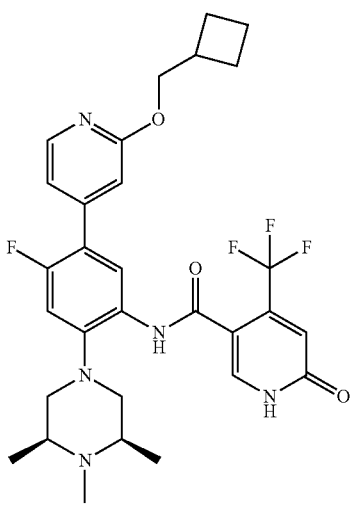

The title compound was prepared similar to the sequence described above for the preparation of Example 100 using 2-(cyclobutylmethoxy)-4-(4,4,5,5-tetramethyl-1,3,2-dioxaborolan-2-yl)pyridine (33.7 mg, 0.116 mmol), N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (47 mg, 0.078 mmol) to give the title compound (34.6 mg, 76% yield). $^1$H NMR (500 MHz, DMSO-d6) δ=9.59 (s, 1H), 8.21 (d, J=5.3 Hz, 1H), 7.93 (s, 1H), 7.82 (d, J=8.4 Hz, 1H), 7.11 (d, J=5.4 Hz, 1H), 7.03 (d, J=12.8 Hz, 1H), 6.88 (s, 1H), 6.81 (s, 1H), 4.27 (d, J=6.8 Hz, 2H), 3.09 (br d, J=10.9 Hz, 2H), 2.70-2.68 (m, 1H), 2.73 (td, J=7.4, 14.7 Hz, 1H), 2.36 (br s, 2H), 2.20 (br s, 3H), 2.12-2.01 (m, 2H), 1.97-1.74 (m, 4H), 1.01 (br d, J=5.9 Hz, 6H); LCMS [M+H]+: 588.6.

Example 293: N-[5-[2-(2,2-dimethylpropoxy)pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

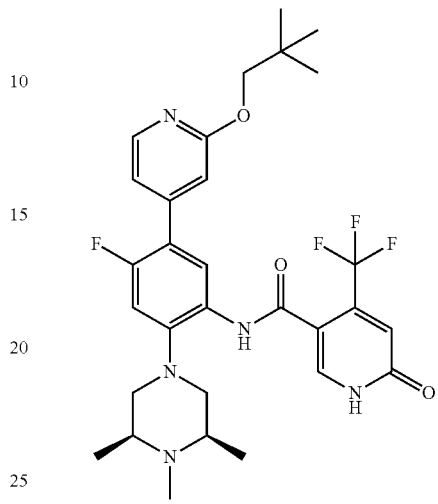

The title compound was prepared by a procedure similar to the sequence described for Example 100 using 2-(neopentyloxy)-4-(4,4,5,5-tetramethyl-1,3,2-dioxaborolan-2-yl)pyridine (36.1 mg, 0.124 mmol) and N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) to give the title compound (21.1 mg, 43% yield). $^1$H NMR (500 MHz, DMSO-d6) δ=9.59 (s, 1H), 8.20 (d, J=5.4 Hz, 1H), 7.94 (s, 1H), 7.82 (d, J=8.4 Hz, 1H), 7.11 (br d, J=5.4 Hz, 1H), 7.04 (d, J=12.8 Hz, 1H), 6.89 (s, 1H), 6.81 (s, 1H), 3.99 (s, 2H), 3.09 (br d, J=10.9 Hz, 2H), 2.48 (br s, 1H), 2.36 (br d, J=1.7 Hz, 2H), 2.20 (br s, 3H), 1.01 (br s, 6H), 1.00 (s, 9H); LCMS [M+H]+: 590.6.

Example 294: N-[5-[2-(diethylamino)pyrimidin-5-yl]-4-fluoro-2-[(3R,5S)-3,4,5-trimethylpiperazin-1-yl]phenyl]-6-oxo-4-(trifluoromethyl)-1H-pyridine-3-carboxamide

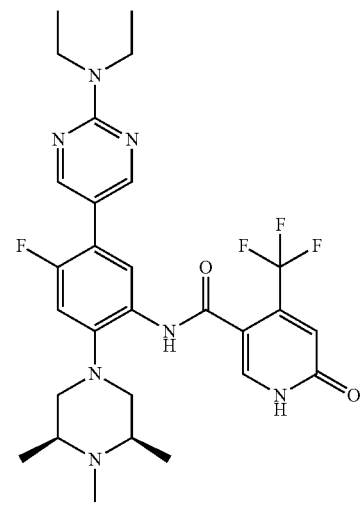 [SMILES: CCN(CC)c1ncc(-c2cc(NC(=O)c3c[nH]c(=O)cc3C(F)(F)F)c(N3C[C@@H](C)N(C)[C@@H](C)C3)cc2F)cn1]

The title compound was prepared similar to the sequence described above for the preparation of Example 100 using 2-diethylaminopyrimidine-5-boronic acid, pinacol ester (34.3 mg, 0.124 mmol) and N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) to give the title compound (33.5 mg, 71% yield). $^1$H NMR (500 MHz, DMSO-d6) δ=9.52 (s, 1H), 8.46 (s, 2H), 7.90 (s, 1H), 7.73 (d, J=8.7 Hz, 1H), 7.03 (d, J=12.2 Hz, 1H), 6.81 (s, 1H), 3.62 (q, J=7.0 Hz, 4H), 3.01 (br d, J=11.0 Hz, 2H), 2.46 (br t, J=11.0 Hz, 2H), 2.35 (br d, J=6.1 Hz, 2H), 2.19 (s, 3H), 1.14 (t, J=7.0 Hz, 6H), 1.00 (d, J=6.1 Hz, 6H); LCMS [M+H]+: 576.6.

Example 295: 3-fluoro-N-[4-fluoro-5-(2-morpholin-4-ylpyrimidin-5-yl)-2-[(3R,5S)-3,4,5-trimethylpiperazin-1-yl]phenyl]-2-(trifluoromethyl)benzamide

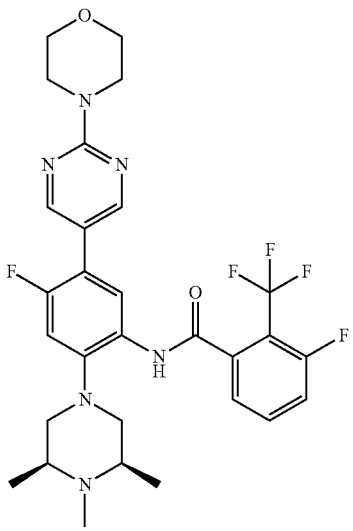 [SMILES: C[C@@H]1CN(c2cc(F)c(-c3cnc(N4CCOCC4)nc3)cc2NC(=O)c2cccc(F)c2C(F)(F)F)C[C@H](C)N1C]

The title compound (beige solid, 49.3 mg, 82%) was prepared by a procedure similar to that of Example 34 using 4-fluoro-5-(2-morpholinopyrimidin-5-yl)-2-((3S,5R)-3,4,5-trimethylpiperazin-1-yl)aniline (40 mg, 0.1 mmol) in DCM (3 mL) and 3-fluoro-2-(trifluoromethyl)benzoyl chloride (23 μL, 0.15 mmol). $^1$H NMR (500 MHz, CHLOROFORM-d) δ=8.58 (s, 2H), 8.51 (d, J=8.2 Hz, 1H), 8.42 (s, 1H), 7.67 (dt, J=5.0, 7.9 Hz, 1H), 7.39-7.33 (m, 2H), 7.00 (d, J=11.2 Hz, 1H), 3.91-3.84 (m, 4H), 3.83-3.78 (m, 4H), 2.85 (br d, J=11.1 Hz, 2H), 2.62 (br t, J=10.8 Hz, 2H), 2.32-2.18 (m, 5H), 1.12 (d, J=6.2 Hz, 6H); LCMS [M+H]$^+$ 591.5.

Example 296: 3,4,5-trifluoro-N-[4-fluoro-5-(2-morpholin-4-ylpyrimidin-5-yl)-2-[(3R,5S)-3,4,5-trimethylpiperazin-1-yl]phenyl]benzamide

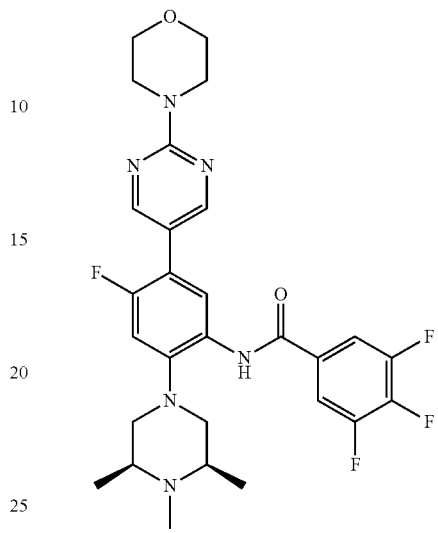

The title compound (tan solid, 38.3 mg, 67%) was prepared by a procedure similar to that of Example 34 using 3,4,5-trifluorobenzoic acid (35 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.20 (s, 1H), 8.60-8.54 (m, 3H), 7.56 (t, J=7.0 Hz, 2H), 7.03 (d, J=11.1 Hz, 1H), 3.91-3.84 (m, 4H), 3.84-3.77 (m, 4H), 2.87 (br d, J=11.0 Hz, 2H), 2.70 (t, J=10.9 Hz, 2H), 2.47-2.36 (m, 5H), 1.17 (d, J=6.2 Hz, 6H); LCMS [M+H]$^+$ 559.5.

Example 297: 2-fluoro-N-[4-fluoro-5-(2-morpholin-4-ylpyrimidin-5-yl)-2-[(3R,5S)-3,4,5-trimethylpiperazin-1-yl]phenyl]-6-(trifluoromethyl)benzamide

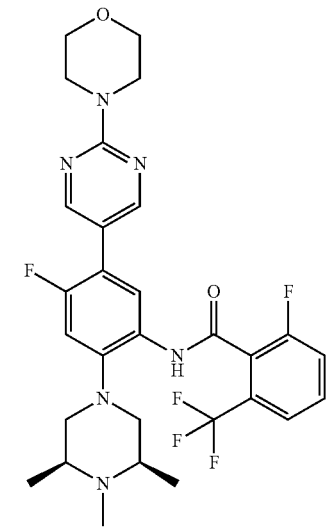

The title compound (off-white solid, 43.0 mg, 72%) was prepared by a procedure similar to Example 34 using 4-fluoro-5-(2-morpholinopyrimidin-5-yl)-2-((3S,5R)-3,4,5-trimethylpiperazin-1-yl)aniline (40 mg, 0.1 mmol) and 2-fluoro-6-(trifluoromethyl)benzoyl chloride (23 µL, 0.15 mmol). $^1$H NMR (500 MHz, CHLOROFORM-d) δ=8.58 (s, 2H), 8.50 (d, J=8.2 Hz, 1H), 8.44 (s, 1H), 7.63-7.57 (m, 2H), 7.46-7.40 (m, 1H), 6.98 (d, J=11.4 Hz, 1H), 3.91-3.84 (m, 4H), 3.82-3.77 (m, 4H), 2.90 (br d, J=11.1 Hz, 2H), 2.61 (br t, J=10.8 Hz, 2H), 2.33-2.23 (m, 5H), 1.12 (d, J=6.2 Hz, 6H); LCMS [M+H]$^+$ 591.5.

Example 298: 4-fluoro-N-[4-fluoro-5-(2-morpholin-4-ylpyrimidin-5-yl)-2-[(3R)-3,4-dimethylpiperazin-1-yl]phenyl]-2-(trifluoromethyl)benzamide

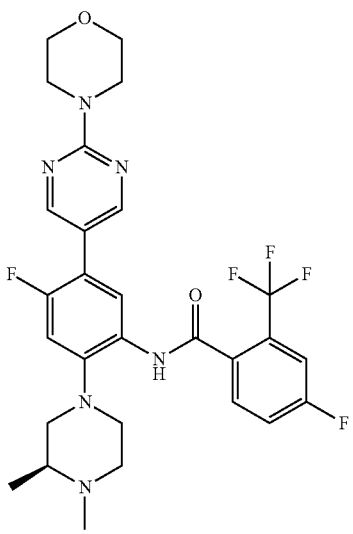 [SMILES: C[C@H]1CN(c2cc(F)c(-c3cnc(N4CCOCC4)nc3)cc2NC(=O)c2ccc(F)cc2C(F)(F)F)CCN1C]

The title compound (formic acid salt, pale beige solid, 34.8 mg, 56%) was prepared by a procedure similar to that of Example 29 using (S)—N-(5-bromo-2-(3,4-dimethylpiperazin-1-yl)-4-fluorophenyl)-4-fluoro-2-(trifluoromethyl)benzamide (51 mg, 0.104 mmol) and 2-(4-morpholino)pyrimidine-5-boronic acid pinacol ester (58 mg, 0.2 mmol). $^1$H NMR (500 MHz, METHANOL-d4) δ=8.58 (s, 2H), 8.36 (br s, 1H), 8.05 (d, J=8.2 Hz, 1H), 7.83 (dd, J=5.4, 8.4 Hz, 1H), 7.67 (dd, J=2.0, 9.0 Hz, 1H), 7.58 (t, J=8.3 Hz, 1H), 7.20 (d, J=11.9 Hz, 1H), 3.89-3.83 (m, 4H), 3.80-3.76 (m, 4H), 3.48-3.39 (m, 1H), 3.31-3.24 (m, 2H), 3.21-3.07 (m, 3H), 2.93-2.84 (m, 1H), 2.83-2.77 (m, 3H), 1.38-1.32 (m, 3H); LCMS [M+H]$^+$ 577.5.

Example 299: 4-fluoro-N-[4-fluoro-5-(2-morpholin-4-ylpyrimidin-5-yl)-2-[(3R)-3,4-dimethylpiperazin-1-yl]phenyl]-2-(trifluoromethyl)benzamide

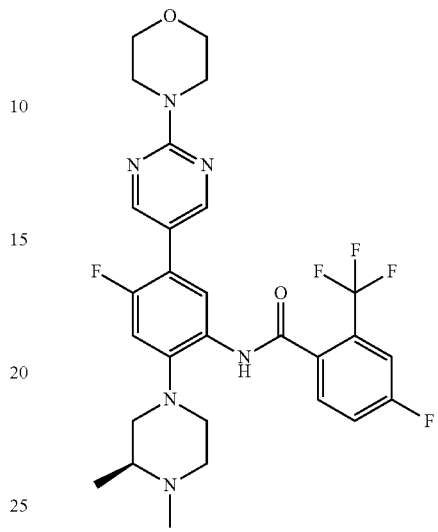

The title compound (formic acid salt, pale beige solid, 34.8 mg, 56%) was prepared through a procedure similar to Example 31 using (S)—N-(5-bromo-2-(3,4-dimethylpiperazin-1-yl)-4-fluorophenyl)-4-fluoro-2-(trifluoromethyl)benzamide (51 mg, 0.104 mmol) and 2-(4-morpholino)pyrimidine-5-boronic acid pinacol ester (58 mg, 0.2 mmol). $^1$H NMR (500 MHz, METHANOL-d4) δ=8.58 (s, 2H), 8.36 (br s, 1H), 8.05 (d, J=8.2 Hz, 1H), 7.83 (dd, J=5.4, 8.4 Hz, 1H), 7.67 (dd, J=2.0, 9.0 Hz, 1H), 7.58 (t, J=8.3 Hz, 1H), 7.20 (d, J=11.9 Hz, 1H), 3.89-3.83 (m, 4H), 3.80-3.76 (m, 4H), 3.48-3.39 (m, 1H), 3.31-3.24 (m, 2H), 3.21-3.07 (m, 3H), 2.93-2.84 (m, 1H), 2.83-2.77 (m, 3H), 1.38-1.32 (m, 3H); LCMS [M+H]$^+$ 577.5.

Example 300: 3,5-dichloro-N-[4-fluoro-2-[3-(methylamino)pyrrolidin-1-yl]-5-(2-morpholin-4-ylpyrimidin-5-yl)phenyl]benzamide

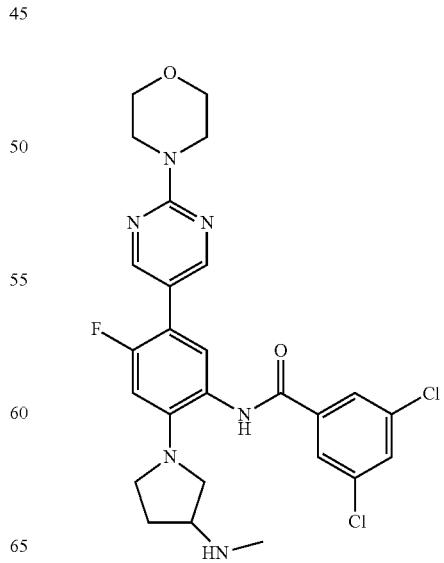

Step 1: tert-butyl (1-(2-amino-5-fluoro-4-(2-morpholinopyrimidin-5-yl)phenyl)pyrrolidin-3-yl)(methyl)carbamate

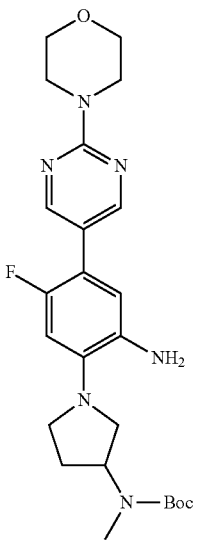

A mixture of tert-butyl (1-(5-fluoro-4-(2-morpholinopyrimidin-5-yl)-2-nitrophenyl)pyrrolidin-3-yl)(methyl)carbamate (1.8598 g, 3.70 mmol, prepared as shown hereinabove in Example 277) and tin(II) chloride, 98% (2.105 g, 11.10 mmol) in a mixture of ethanol (EtOH) (10 ml) and methanol (MeOH) (10 ml) was heated to 90° C. for 3 hours. Then the reaction mixture was concentrated onto celite and purified by flash chromatography [0-30% MeOH/DCM] to afford the tert-butyl (1-(2-amino-5-fluoro-4-(2-morpholinopyrimidin-5-yl)phenyl)pyrrolidin-3-yl)(methyl)carbamate (0.94 g, 1.990 mmol, 53.8% yield) as a yellow powder. LCMS [M+H]+ 473.2.

Step 2: tert-butyl (1-(2-(3,5-dichlorobenzamido)-5-fluoro-4-(2-morpholinopyrimidin-5-yl)phenyl)pyrrolidin-3-yl)(methyl)carbamate

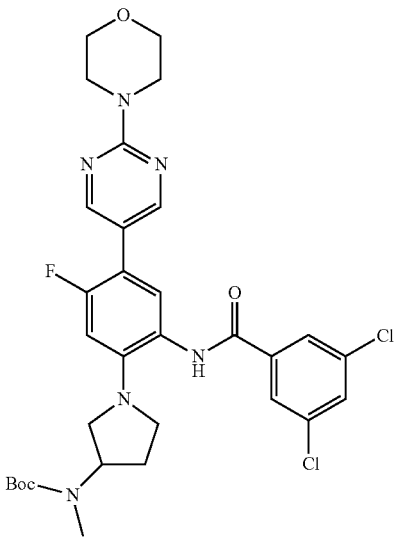 [SMILES: CN(C(=O)OC(C)(C)C)C1CCN(c2cc(F)c(-c3cnc(N4CCOCC4)nc3)cc2NC(=O)c2cc(Cl)cc(Cl)c2)C1]

To a solution of tert-butyl (1-(2-amino-5-fluoro-4-(2-morpholinopyrimidin-5-yl)phenyl)pyrrolidin-3-yl)(methyl)carbamate (211 mg, 0.446 mmol) and triethylamine (0.187 ml, 1.339 mmol) in DCM (40 ml) was added 3,5-dichlorobenzoyl chloride (94 mg, 0.446 mmol). Then the reaction mixture was stirred at room temperature for 2 hours. Then the crude material was dry loaded and purified by Flash chromatography [0-10% DCM/MeOH] to afford the desired tert-butyl (1-(2-(3,5-dichlorobenzamido)-5-fluoro-4-(2-morpholinopyrimidin-5-yl)phenyl)pyrrolidin-3-yl)(methyl)carbamate (288 mg, 0.424 mmol, 95% yield) as a yellow solid. $^1$H NMR (500 MHz, DMSO-d6) δ=10.16 (s, 1H), 8.52 (s, 2H), 7.95-8.02 (m, 2H), 7.88 (s, 1H), 7.34 (d, J=8.80 Hz, 1H), 6.72 (d, J=13.94 Hz, 1H), 5.75 (s, 1H), 4.55 (br. s., 1H), 3.71-3.75 (m, 5H), 3.65-3.68 (m, 4H), 3.35-3.41 (m, 2H), 3.25-3.30 (m, 2H), 2.69 (s, 3H), 1.92-2.07 (m, 2H), 1.35 (s, 9H); LCMS [M+H]+ 645.2.

Step 3: 3,5-dichloro-N-(4-fluoro-2-(3-(methylamino)pyrrolidin-1-yl)-5-(2-morpholinopyrimidin-5-yl)phenyl)benzamide, 2Trifluoroacetic Acid, 2CF3COOH

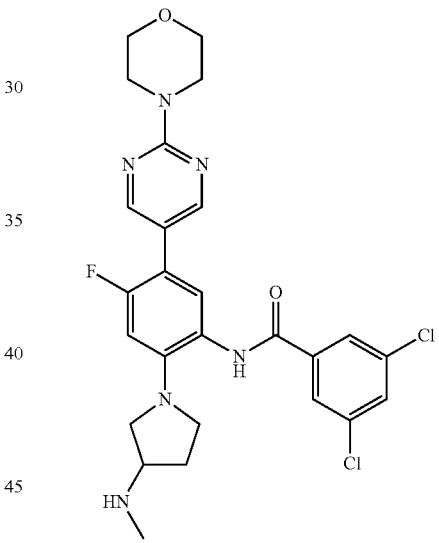

To a solution of tert-butyl (1-(2-(3,5-dichlorobenzamido)-5-fluoro-4-(2-morpholinopyrimidin-5-yl)phenyl)pyrrolidin-3-yl)(methyl)carbamate (288 mg, 0.446 mmol) in DCM (3 mL) was added trifluoroacetic acid (2 ml, 26.1 mmol). The reaction mixture was stirred at 24° C. for 1 hour. Then the TFA and solvent were removed under vacuum and the crude material was purified by flash chromatography [0-20% DCM/MeOH] to afford the 3,5-dichloro-N-(4-fluoro-2-(3-(methylamino)pyrrolidin-1-yl)-5-(2-morpholinopyrimidin-5-yl)phenyl)benzamide (TFA salt), (77.4 mg, 0.095 mmol, 21.31% yield) as a light brown powder. $^1$H NMR (500 MHz, DMSO-d6) δ=10.18 (s, 1H), 8.73 (br. s., 2H), 8.53 (s, 2H), 7.97-8.04 (m, 2H), 7.89 (s, 1H), 7.39 (d, J=8.80 Hz, 1H), 6.76 (d, J=13.82 Hz, 1H), 3.78 (d, J=5.38 Hz, 1H), 3.71-3.75 (m, 4H), 3.65-3.69 (m, 4H), 3.62 (dd, J=6.85, 10.76 Hz, 1H), 3.43-3.49 (m, 2H), 3.39 (dd, J=5.07, 10.70 Hz, 2H), 3.31-3.37 (m, 2H), 3.17 (s, 2H), 2.58 (br. s., 3H), 2.22-2.31 (m, 1H), 1.98-2.07 (m, 1H); LCMS [M+H]+ 545.3.

Example 301: N-[4-fluoro-5-[6-(4-methylpiperazin-1-yl)pyridin-3-yl]-2-[(3R)-3,4-dimethylpiperazin-1-yl]phenyl]-1-methyl-6-oxo-4-(trifluoromethyl)pyridine-3-carboxamide

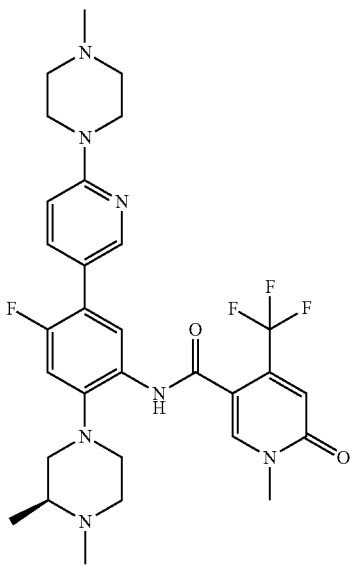

The title compound (white solid, 36.9 mg, 61%) was prepared by a procedure similar to Example 273 using (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (50.5 mg, 0.1 mmol) and 2-(4-methylpiperazin-1-yl)pyridine-5-boronic acid, pinacol ester (61 mg, 0.2 mmol). $^1$H NMR (500 MHz, METHANOL-d4) δ=8.27 (s, 1H), 8.17 (d, J=5.3 Hz, 1H), 7.95 (d, J=7.9 Hz, 1H), 7.10 (d, J=12.1 Hz, 1H), 6.99 (s, 1H), 6.95 (br s, 1H), 6.90 (br d, J=4.6 Hz, 1H), 3.66 (s, 3H), 3.65-3.59 (m, 4H), 3.19-3.06 (m, 2H), 3.00-2.88 (m, 2H), 2.66-2.51 (m, 6H), 2.44-2.34 (m, 7H), 1.13 (d, J=6.2 Hz, 3H); LCMS [M+H]$^+$ 602.4.

Example 302: N-[4-fluoro-5-[4-(4-methylpiperazin-1-yl)phenyl]-2-[(3R)-3,4-dimethylpiperazin-1-yl]phenyl]-1-methyl-6-oxo-4-(trifluoromethyl)pyridine-3-carboxamide

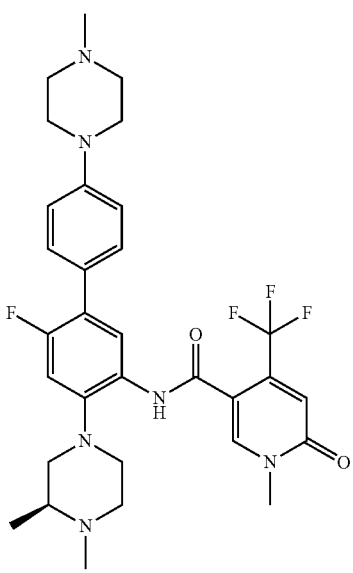

The title compound (light brown solid, 38.6 mg, 63%) was prepared by a procedure similar to Example 273 using (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (50.5 mg, 0.1 mmol) and [4-(4-methylpiperazin-1-yl)phenyl]boronic acid, pinacol ester (60 mg, 0.2 mmol). $^1$H NMR (500 MHz, METHANOL-d4) δ=8.25 (br s, 1H), 7.93 (br d, J=8.2 Hz, 1H), 7.47 (br d, J=7.8 Hz, 2H), 7.08-7.03 (m, 3H), 6.95 (s, 1H), 3.66 (s, 3H), 3.31-3.26 (m, 4H), 3.12-3.01 (m, 2H), 2.98-2.89 (m, 2H), 2.69-2.62 (m, 4H), 2.59-2.49 (m, 2H), 2.43-2.35 (m, 7H), 1.13 (d, J=6.4 Hz, 3H); LCMS [M+H]$^+$ 601.5.

449

Example 303: N-[4-fluoro-2-[3-[methyl(propyl)amino]pyrrolidin-1-yl]-5-(2-morpholin-4-ylpyrimidin-5-yl)phenyl]-6-oxo-4-(trifluoromethyl)-1H-pyridine-3-carboxamide

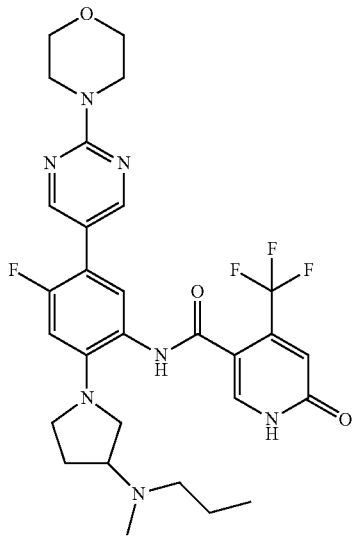 [SMILES: CCCN(C)C1CCN(c2cc(F)c(-c3cnc(N4CCOCC4)nc3)cc2NC(=O)c2c[nH]c(=O)cc2C(F)(F)F)C1]

To a solution of N-(4-fluoro-2-(3-(methylamino)pyrrolidin-1-yl)-5-(2-morpholinopyrimidin-5-yl)phenyl)-6-oxo-4-(trifluoromethyl)-1,6-dihydropyridine-3-carboxamide (39 mg, 0.069 mmol) and propionaldehyde (17.7 mg, 0.305 mmol) in 1,2-dichloroethane (DCE) (3 ml) was added acetic acid (33 mg, 0.550 mmol) and the reaction mixture was stirred at room temperature for 15 minutes. Then sodium triacetoxyborohydride (53.0 mg, 0.250 mmol) was added and the reaction mixture was stirred at room temperature for an additional 20 minutes. Then a saturated solution of NaHCO$_3$ (3 mL) was added and the product was extracted using DCM (3×20 mL). The organic phase was dried over MgSO$_4$ and after filtration and solvents removal, the crude material was dry loaded and purified by flash chromatography [0-30% MeOH/DCM] to afford the N-(4-fluoro-2-(3-(methyl(propyl)amino)pyrrolidin-1-yl)-5-(2-morpholinopyrimidin-5-yl)phenyl)-6-oxo-4-(trifluoromethyl)-1,6-dihydropyridine-3-carboxamide-TFA (42.0 mg, 0.056 mmol, 80% yield) as an off-white powder. $^1$H NMR (500 MHz, DMSO-d6) δ=9.80 (s, 1H), 8.50 (s, 2H), 7.98 (s, 1H), 7.31 (d, J=8.56 Hz, 1H), 6.77 (s, 1H), 6.66 (d, J=14.06 Hz, 1H), 3.71-3.75 (m, 4H), 3.65-3.69 (m, 4H), 3.22-3.28 (m, 4H), 2.85-2.92 (m, 1H), 2.26 (q, J=6.77 Hz, 2H), 2.13 (s, 3H), 2.07 (d, J=6.72 Hz, 1H), 1.64-1.74 (m, 1H), 1.34-1.43 (m, 2H), 0.79 (t, J=7.34 Hz, 3H); LCMS [M+H]+ 604.5.

450

Example 304: 3,5-dichloro-N-[4-fluoro-2-[3-[methyl(propyl)amino]pyrrolidin-1-yl]-5-(2-morpholin-4-ylpyrimidin-5-yl)phenyl]benzamide

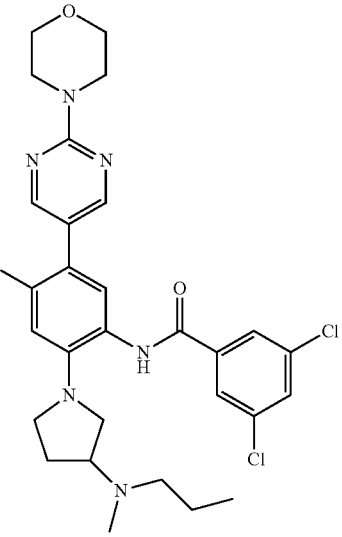

Step 1: tert-butyl (1-(2-(3,5-dichlorobenzamido)-5-fluoro-4-(2-morpholinopyrimidin-5-yl)phenyl)pyrrolidin-3-yl)(methyl)carbamate

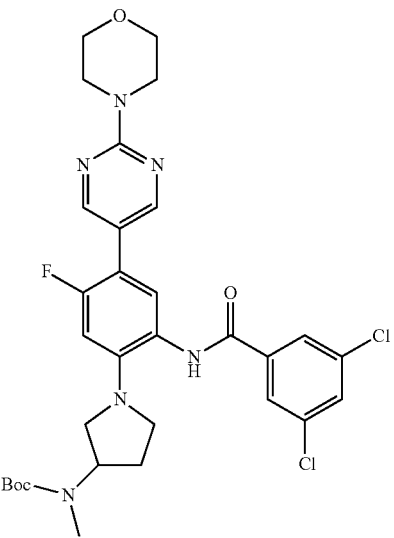

To a solution of tert-butyl (1-(2-amino-5-fluoro-4-(2-morpholinopyrimidin-5-yl)phenyl)pyrrolidin-3-yl)(methyl)carbamate (211 mg, 0.446 mmol, preparation described in Example 277) and triethylamine (0.187 ml, 1.339 mmol) in DCM (40 ml) was added 3,5-dichlorobenzoyl chloride (94 mg, 0.446 mmol). Then the reaction mixture was stirred at room temperature for 2 hours. Then the crude material was dry loaded and purified by Flash chromatography [0-10% DCM/MeOH] to afford the desired tert-butyl (1-(2-(3,5-dichlorobenzamido)-5-fluoro-4-(2-morpholinopyrimidin-5-yl)phenyl)pyrrolidin-3-yl)(methyl)carbamate (288 mg, 0.424 mmol, 95% yield) as a yellow solid. $^1$H NMR (500 MHz, DMSO-d6) δ=10.16 (s, 1H), 8.52 (s, 2H), 7.95-8.02 (m, 2H), 7.88 (s, 1H), 7.34 (d, J=8.80 Hz, 1H), 6.72 (d, J=13.94 Hz, 1H), 5.75 (s, 1H), 4.55 (br. s., 1H), 3.71-3.75 (m, 5H), 3.65-3.68 (m, 4H), 3.35-3.41 (m, 2H), 3.25-3.30 (m, 2H), 2.69 (s, 3H), 1.92-2.07 (m, 2H), 1.35 (s, 9H); LCMS [M+H]+ 645.2.

Step 2: 3,5-dichloro-N-(4-fluoro-2-(3-(methylamino)pyrrolidin-1-yl)-5-(2-morpholinopyrimidin-5-yl)phenyl)benzamide-TFA salt

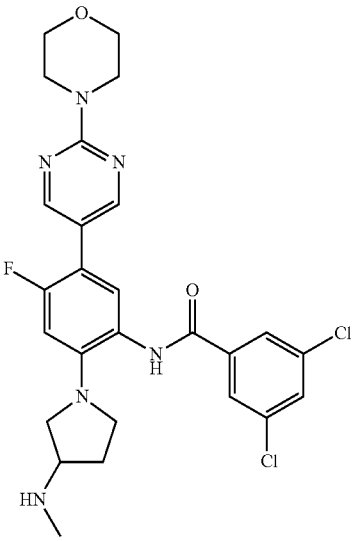 [SMILES: CNC1CCN(c2cc(F)c(-c3cnc(N4CCOCC4)nc3)cc2NC(=O)c2cc(Cl)cc(Cl)c2)C1]

To a solution of tert-butyl (1-(2-(3,5-dichlorobenzamido)-5-fluoro-4-(2-morpholinopyrimidin-5-yl)phenyl)pyrrolidin-3-yl)(methyl)carbamate (288 mg, 0.446 mmol) in dichloromethane (DCM) (3 ml) was added trifluoroacetic acid (2 ml, 26.1 mmol). The reaction mixture was stirred at 24° C. for 1 hour. Then the TFA and solvent were removed under vacuum and the crude material was purified by Flash chromatography [0-20% DCM/MeOH] to afford the 3,5-dichloro-N-(4-fluoro-2-(3-(methylamino)pyrrolidin-1-yl)-5-(2-morpholinopyrimidin-5-yl)phenyl)benzamide-2TFA, (77.4 mg, 0.095 mmol, 21.31% yield) as a light brown powder. $^1$H NMR (500 MHz, DMSO-d6) δ=10.18 (s, 1H), 8.73 (br. s., 2H), 8.53 (s, 2H), 7.97-8.04 (m, 2H), 7.89 (s, 1H), 7.39 (d, J=8.80 Hz, 1H), 6.76 (d, J=13.82 Hz, 1H), 3.78 (d, J=5.38 Hz, 1H), 3.71-3.75 (m, 4H), 3.65-3.69 (m, 4H), 3.62 (dd, J=6.85, 10.76 Hz, 1H), 3.43-3.49 (m, 2H), 3.39 (dd, J=5.07, 10.70 Hz, 2H), 3.31-3.37 (m, 2H), 3.17 (s, 2H), 2.58 (br. s., 3H), 2.22-2.31 (m, 1H), 1.98-2.07 (m, 1H); LCMS [M+H]+ 545.3.

Step 3: 3,5-dichloro-N-(4-fluoro-2-(3-(methyl(propyl)amino)pyrrolidin-1-yl)-5-(2-morpholinopyrimidin-5-yl)phenyl)benzamide

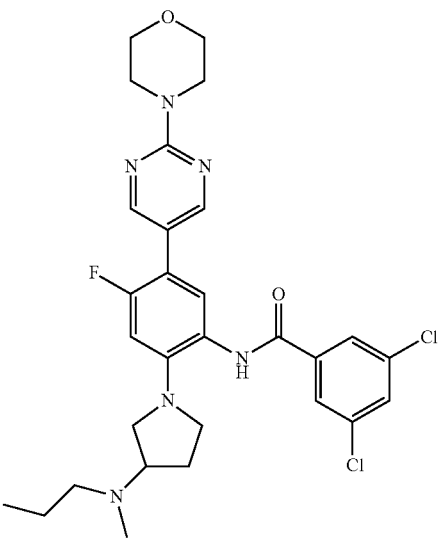 [SMILES: CCCN(C)C1CCN(c2cc(F)c(-c3cnc(N4CCOCC4)nc3)cc2NC(=O)c2cc(Cl)cc(Cl)c2)C1]

To a solution of 3,5-dichloro-N-(4-fluoro-2-(3-(methylamino)pyrrolidin-1-yl)-5-(2-morpholinopyrimidin-5-yl) phenyl)benzamide (35 mg, 0.064 mmol) and propionaldehyde (3.73 mg, 0.064 mmol) in 1,2-dichloroethane (DCE) (3 ml) was added acetic acid (23 mg, 0.383 mmol) and the reaction mixture was stirred at room temperature for 15 minutes. Then sodium triacetoxyborohydride (50 mg, 0.236 mmol) was added and the reaction mixture was stirred at room temperature for an hour. Then a saturated solution of NaHCO$_3$ (3 mL) was added and the product was extracted using DCM (3×20 mL). The organic phase was dried over MgSO$_4$ and after filtration and solvents removal, the crude material was dry loaded and purified by Flash chromatography [0-10% MeOH/DCM] to afford the 3,5-dichloro-N-(4-fluoro-2-(3-(methyl(propyl)amino)pyrrolidin-1-yl)-5-(2-morpholinopyrimidin-5-yl)phenyl)benzamide (25.0 mg, 0.040 mmol, 63.0% yield) as a slightly yellow powder. $^1$H NMR (500 MHz, DMSO-d6) δ=10.17 (s, 1H), 8.51 (s, 2H), 7.99 (s, 1H), 7.98 (s, 1H), 7.85-7.92 (m, 1H), 7.30 (d, J=8.80 Hz, 1H), 6.66 (d, J=14.06 Hz, 1H), 3.70-3.79 (m, 5H), 3.65-3.70 (m, 5H), 3.35-3.44 (m, 2H), 3.18-3.29 (m, 2H), 2.86 (br. s., 1H), 2.13-2.25 (m, 2H), 2.05-2.13 (m, 4H), 1.91 (s, 1H), 1.60-1.72 (m, 1H), 1.26-1.50 (m, 3H), 0.73-0.93 (m, 1H), 0.70 (t, J=7.27 Hz, 3H); LCMS [M+H]+ 587.4.

Example 305: N-[5-[1-[2-(dimethylamino)acetyl]-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

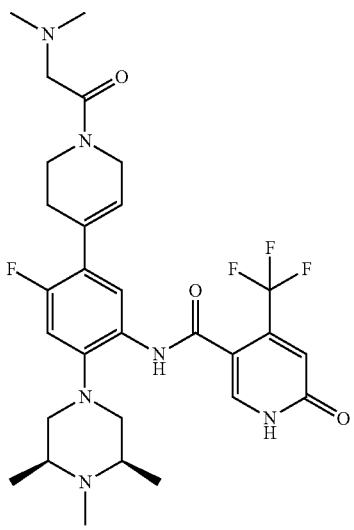

The procedure followed was similar to Example 253 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) and 2-(dimethylamino)acetyl chloride hydrochloride (12.09 mg, 0.065 mmol) to give the title compound (21.5 mg, 55% yield). $^1$H NMR (500 MHz, METHANOL-d4) δ=7.99-7.93 (m, 1H), 7.84-7.75 (m, 1H), 7.01-6.94 (m, 1H), 6.91 (s, 1H), 6.09-5.98 (m, 1H), 4.31-4.18 (m, 2H), 3.84-3.72 (m, 2H), 3.50-3.45 (m, 2H), 3.07-2.98 (m, 2H), 2.65-2.50 (m, 6H), 2.49-2.41 (m, 6H), 2.40-2.36 (m, 3H), 1.18-1.14 (m, 6H); LCMS [M+H]+ 593.

Example 306: 4-[4-[5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]pyrimidin-2-yl]piperazin-1-yl]-4-oxobutanoic acid

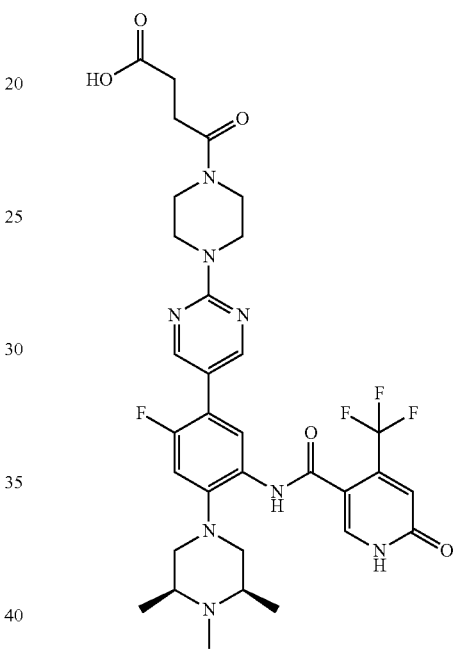

N-(4-fluoro-5-(2-(piperazin-1-yl)pyrimidin-5-yl)-2-((3S,5R)-3,4,5-trimethylpiperazin-1-yl)phenyl)-6-oxo-4-(trifluoromethyl)-1,6-dihydropyridine-3-carboxamide (15.32 mg, 0.026 mmol) and succinic anhydride (5.21 mg, 0.052 mmol) were dissolved in N,N-diisopropylethylamine (4.53 µL, 0.026 mmol) and tetrahydrofuran (THF) (521 µL). The suspension was stirred overnight, and the residue was purified using a cation exchange column eluting with MeOH:NH$_4$OH. $^1$H NMR (500 MHz, MeOD) δ 8.55 (s, 2H), 7.97 (s, 1H), 7.90 (d, J=8.2 Hz, 1H), 7.10 (d, J=12.0 Hz, 1H), 6.91 (s, 1H), 3.97-3.93 (m, 2H), 3.89-3.85 (m, 2H), 3.67 (d, J=9.7 Hz, 4H), 3.09 (d, J=8.9 Hz, 2H), 2.70 (dt, J=10.4, 7.1 Hz, 6H), 2.58 (t, J=6.9 Hz, 2H), 2.45 (s, 3H), 1.20 (d, J=5.5 Hz, 6H); LCMS HSS [M+1]+=689.40.

Example 307: N-[4-fluoro-5-(2-morpholin-4-ylpyrimidin-5-yl)-2-[(3R,4R)-3-(dimethylamino)-4-fluoropyrrolidin-1-yl]phenyl]-1-methyl-6-oxo-4-(trifluoromethyl)pyridine-3-carboxamide

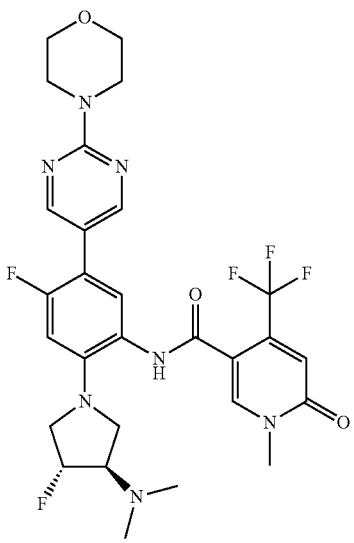 [SMILES: CN(C)[C@@H]1CN(c2cc(F)c(-c3cnc(N4CCOCC4)nc3)cc2NC(=O)c2cn(C)c(=O)cc2C(F)(F)F)C[C@H]1F]

Step 1: trans-tert-butyl-3-(dimethylamino)-4-hydroxypyrrolidine-1-carboxylate

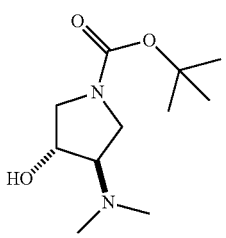 [SMILES: CN(C)[C@@H]1CN(C(=O)OC(C)(C)C)C[C@H]1O]

A solution of tert-butyl 6-oxa-3-azabicyclo[3.1.0]hexane-3-carboxylate (0.42 mL, 2.7 mmol) and dimethylamine (2.0 M THF, 6.0 mL, 12 mmol) in a sealed vial was heated at 90° C. for 40 h in an aluminum reaction block. After cooling to room temperature the reaction mixture was concentrated onto celite and purification by flash chromatography [1-10% MeOH/DCM+0.5% NH$_4$OH] afforded trans-tert-butyl-3-(dimethylamino)-4-hydroxypyrrolidine-1-carboxylate (1.6 g, 64%). $^1$H NMR (500 MHz, DMSO-d6) δ=5.08 (d, J=4.9 Hz, 1H), 4.10 (br s, 1H), 3.49-3.37 (m, 3H), 3.18-3.10 (m, 1H), 3.05-2.97 (m, 1H), 2.18 (s, 6H), 1.39 (s, 9H).

Step 2: trans-tert-butyl-3-(dimethylamino)-4-fluoropyrrolidine-1-carboxylate

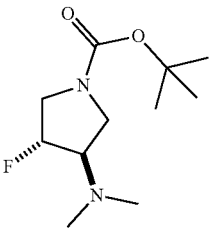 [SMILES: CN(C)[C@@H]1CN(C(=O)OC(C)(C)C)C[C@H]1F]

(Diethylamino)sulfur trifluoride (0.40 mL, 3.0 mmol) was added dropwise to a stirring solution of trans-tert-butyl-3-(dimethylamino)-4-hydroxypyrrolidine-1-carboxylate (0.50 g, 2.2 mmol) in DCM (10 mL) at −78° C. The reaction was allowed to warm to room temperature overnight. The reaction mixture was concentrated onto celite and purification by flash chromatography [0-3% DCM/MeOH+0.5% NH$_4$OH] afforded trans-tert-butyl-3-(dimethylamino)-4-fluoropyrrolidine-1-carboxylate (0.39 g, 78%). $^1$H NMR (500 MHz, DMSO-d6) δ=5.27-5.12 (m, 1H), 3.67-3.55 (m, 1H), 3.48 (dd, J=6.8, 11.5 Hz, 1H), 3.42-3.35 (m, 1H), 3.27 (br s, 1H), 2.90 (br s, 1H), 2.19 (s, 6H), 1.41 (s, 9H).

Step 3: Trans-4-fluoro-N,N-dimethylpyrrolidin-3-amine

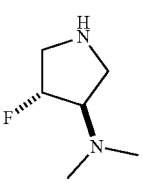

Trifluoroacetic acid (1.3 mL, 17 mmol) was added to a solution of trans-tert-butyl-3-(dimethylamino)-4-fluoropyrrolidine-1-carboxylate (0.39 g, 1.7 mmol) in DCM (3 mL) at room temperature. After stirring for 3 h the volatiles were removed under a stream of air and the pure product was isolated by a catch and release protocol using an SCX-2 silica cartridge. Trans-4-fluoro-N,N-dimethylpyrrolidin-3-amine (0.12 g, 54%). $^1$H NMR (500 MHz, DMSO-d6) δ=5.08-4.90 (m, 1H), 3.09 (dd, J=7.1, 10.8 Hz, 1H), 3.02-2.80 (m, 2H), 2.59 (dt, J=2.0, 7.5 Hz, 1H), 2.45 (dd, J=8.0, 10.8 Hz, 1H), 2.17 (s, 6H).

Step 4: Trans-1-(4-bromo-5-fluoro-2-nitrophenyl)-4-fluoro-N,N-dimethylpyrrolidin-3-amine

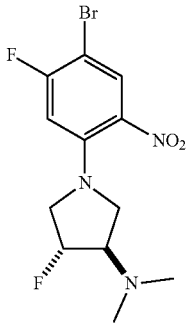 [SMILES: CN(C)[C@@H]1CN(c2cc(F)c(Br)cc2[N+](=O)[O-])C[C@H]1F]

A solution of 1-bromo-2,4-difluoro-5-nitrobenzene (0.225 g, 0.945 mmol) in PhMe (1 mL) was slowly added to a rapidly stirring mixture of trans-4-fluoro-N,N-dimethylpyrrolidin-3-amine (0.13 g, 0.95 mmol) and K₂CO₃ (0.065 g, 0.47 mmol) in PhMe (2 mL) at room temperature. After stirring for 15 minutes the reaction was warmed to 45° C. for 5 h. The reaction was cooled to room temperature and partitioned between H₂O (50 mL) and EtOAc (50 mL). The layers were separated and the aqueous layer was extracted with an additional portion of EtOAc. The combined organic extracts were concentrated onto celite and purification by flash chromatography [1-10% MeOH/DCM+0.5% NH₄OH] afforded trans-1-(4-bromo-5-fluoro-2-nitrophenyl)-4-fluoro-N,N-dimethylpyrrolidin-3-amine (0.25 g, 76%). LCMS [M+H]+: 350.3.

Step 5: trans-4-fluoro-1-(5-fluoro-4-(2-morpholinopyrimidin-5-yl)-2-nitrophenyl)-N,N-dimethylpyrrolidin-3-amine

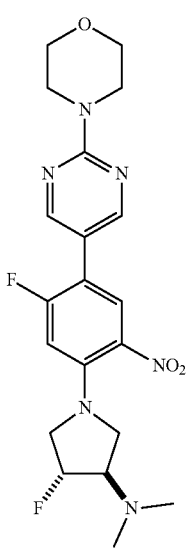 [SMILES: CN(C)[C@@H]1CN(c2cc(F)c(-c3cnc(N4CCOCC4)nc3)cc2[N+](=O)[O-])C[C@H]1F]

A 30 mL vial was charged with a mixture of trans-1-(4-bromo-5-fluoro-2-nitrophenyl)-4-fluoro-N,N-dimethylpyrrolidin-3-amine (0.13 g, 0.36 mmol), 2-(4-morpholino)pyrimidine-5-boronic acid pinacol ester (0.12 g, 0.39 mmol), XPhos Pd G2 (6 mg, 7 µmol) and XPhos (4 mg, 7 µmol). The vial was sealed with a septum, evacuated and backfilled with nitrogen. 1,4-Dioxane (3 mL) and aqueous sodium carbonate (2 M, 0.6 mL) were added via syringe and the vial was evacuated and backfilled an additional time. The reaction was heated to 90° C. in an aluminum block for 18 h. After cooling to room temperature the reaction mixture was concentrated onto celite and purification by flash chromatography [0.5-10% MeOH/DCM+0.5% NH₄OH] afforded the product (0.16 g, 95%). LCMS [M+H]+: 435.4.

Step 6: trans-1-(2-amino-5-fluoro-4-(2-morpholinopyrimidin-5-yl)phenyl)-4-fluoro-N,N-dimethylpyrrolidin-3-amine

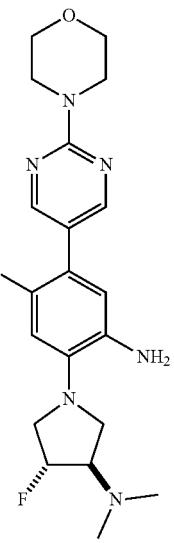

A mixture of trans-4-fluoro-1-(5-fluoro-4-(2-morpholinopyrimidin-5-yl)-2-nitrophenyl)-N,N-dimethylpyrrolidin-3-amine (0.17 g, 0.38 mmol) and SnCl₂ (0.22 g, 1.2 mmol) in EtOH (6 mL) was heated to 75° C. for 5 h. After cooling to room temperature the reaction was concentrated onto celite and purification by flash chromatography [0.5-10% MeOH/DCM+0.5% NH₄OH] afforded trans-1-(2-amino-5-fluoro-4-(2-morpholinopyrimidin-5-yl)phenyl)-4-fluoro-N,N-dimethylpyrrolidin-3-amine (0.13 g, 83%). LCMS [M+H]+: 405.4.

459

Step 7: trans-N-(2-(3-(dimethylamino)-4-fluoropyr-rolidin-1-yl)-4-fluoro-5-(2-morpholinopyrimidin-5-yl)phenyl)-1-methyl-6-oxo-4-(trifluoromethyl)-1,6-dihydropyridine-3-carboxamide

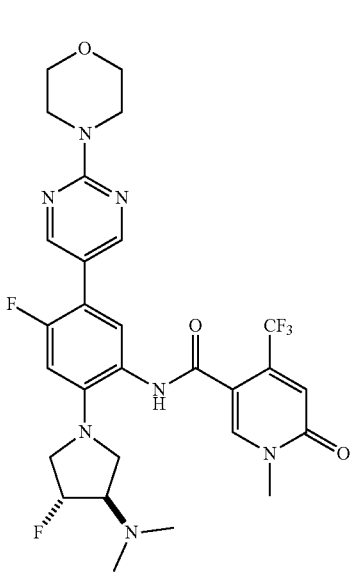 [SMILES: CN(C)[C@@H]1CN(c2cc(F)c(-c3cnc(N4CCOCC4)nc3)cc2NC(=O)c2cn(C)c(=O)cc2C(F)(F)F)C[C@H]1F]

1-Methyl-6-oxo-4-(trifluoromethyl)-1,6-dihydropyridine-3-carboxylic acid (0.050 g, 0.22 mmol) was activated with HATU (0.085 g, 0.22 mmol) and N,N-diisopropylethylamine (0.04 mL, 0.22 mmol) in DMF (1 mL) at room temperature. The solution of activated acid was added to a solution of trans-1-(2-amino-5-fluoro-4-(2-morpholinopyrimidin-5-yl)phenyl)-4-fluoro-N,N-dimethylpyrrolidin-3-amine (0.060 g, 0.15 mmol) in DMF (1 mL) and the reaction was heated to 55° C. for 18 h. After cooling to room temperature the reaction mixture was concentrated onto celite and purified by flash chromatography [0.5-10% MeOH/DCM+0.5% NH₄OH]. Further purification by a catch and release protocol using an SCX-2 silica cartridge afforded the title compound trans-N-(2-(3-(dimethylamino)-4-fluoropyrrolidin-1-yl)-4-fluoro-5-(2-morpholinopyrimidin-5-yl)phenyl)-1-methyl-6-oxo-4-(trifluoromethyl)-1,6-dihydropyridine-3-carboxamide (0.055 g, 61%). LCMS [M+H]+: 608.5.

460

Example 308: trans-N-(5-(6-(cyclopropylmethoxy)pyridin-3-yl)-2-(3-(dimethylamino)-4-fluoropyrrolidin-1-yl)-4-fluorophenyl)-1-methyl-6-oxo-4-(trifluoromethyl)-1,6-dihydropyridine-3-carboxamide

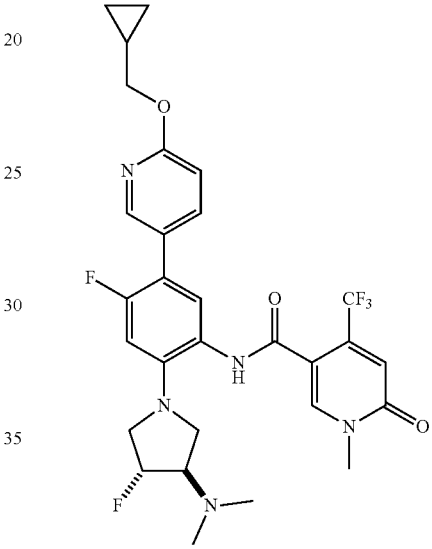

The title compound (76 mg, 53% yield) was prepared from (3R,4S)-1-(2-amino-4-(6-(cyclopropylmethoxy)pyridin-3-yl)-5-fluorophenyl)-4-fluoro-N,N-dimethylpyrrolidin-3-amine (50 mg, 0.129 mmol) and 1-methyl-6-oxo-4-(trifluoromethyl)-1,6-dihydropyridine-3-carboxylic acid (42.7 mg, 0.193 mmol) according to methods similar to Example 34. $^1$H NMR (500 MHz, DMSO-d6) δ=9.85 (s, 1H), 8.37 (s, 1H), 8.24 (s, 1H), 7.80 (br d, J=7.7 Hz, 1H), 7.38 (d, J=8.6 Hz, 1H), 6.93 (d, J=8.9 Hz, 1H), 6.89-6.82 (m, 2H), 5.31-5.14 (m, 1H), 4.14 (d, J=7.1 Hz, 2H), 3.63-3.58 (m, 2H), 3.54 (s, 3H), 3.16 (br dd, J=6.6, 10.0 Hz, 1H), 2.98-2.89 (m, 1H), 2.22 (s, 6H), 0.59-0.54 (m, 2H), 0.34 (q, J=4.8 Hz, 2H); LCMS [M+H]+: 592.5.

Example 309: N-[4-fluoro-2-morpholin-4-yl-5-(2-piperazin-1-ylpyrimidin-5-yl)phenyl]-6-oxo-4-(trifluoromethyl)-1H-pyridine-3-carboxamide

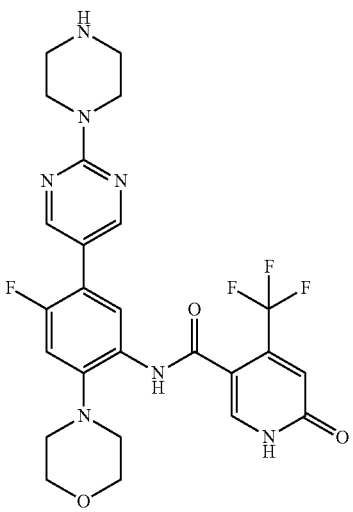 [SMILES: O=C(Nc1cc(-c2cnc(N3CCNCC3)nc2)c(F)cc1N1CCOCC1)c1c[nH]c(=O)cc1C(F)(F)F]

Step 1: tert-butyl 4-(5-(5-amino-2-fluoro-4-morpholinophenyl)pyrimidin-2-yl)piperazine-1-carboxylate

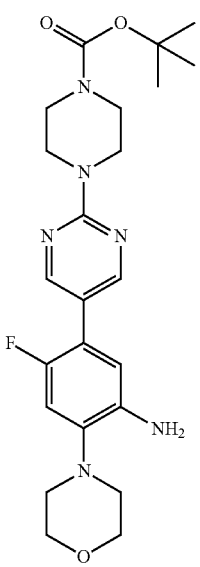 [SMILES: CC(C)(C)OC(=O)N1CCN(c2ncc(-c3cc(N)c(N4CCOCC4)cc3F)cn2)CC1]

To a 5 mL microwave vial charged with 5-bromo-4-fluoro-2-(morpholin-4-yl)aniline (190 mg, 0.691 mmol), 2-(4-boc-piperazino)pyrimidine-5-boronic acid pinacol ester (323 mg, 0.829 mmol), bis(di-tert-butyl(4-dimethylaminophenyl)phosphine)dichloropalladium(II) (48.9 mg, 0.069 mmol) and potassium phosphate tribasic (0.440 g, 2.072 mmol) was added 1,4-dioxane (12 mL)/water (1.3 mL) (9.1 mixture) to give a white suspension. The suspension was stirred for 5 min, degassed, purged with $N_2$, and microwaved for 60 min at 110° C. The solvent was evaporated and 15 mL of $CH_2Cl_2$ were added. The suspension was sonicated and extracted from water (15 mL). The solvent was evaporated in vacuo yielding the crude product that was purified by flash column chromatography on silica gel (0-100%, 89% $CH_2Cl_2$, 10% MeOH, 1% $NH_4Ac/CH_2Cl_2$). The compound was freeze dried for 2 days to afford the title reagent. $^1$H NMR (500 MHz, MeOD) δ 8.49 (d, J=1.0 Hz, 2H), 6.87 (d, J=12.1 Hz, 1H), 6.83 (d, J=7.9 Hz, 1H), 3.85 (dd, J=10.0, 7.1 Hz, 8H), 3.52 (s, 4H), 2.94-2.90 (m, 4H), 1.49 (s, 9H); LCMS [M+1]$^+$=459.40.

Step 2: N-(4-fluoro-2-morpholino-5-(2-(piperazin-1-yl)pyrimidin-5-yl)phenyl)-6-oxo-4-(trifluoromethyl)-1,6-dihydropyridine-3-carboxamide

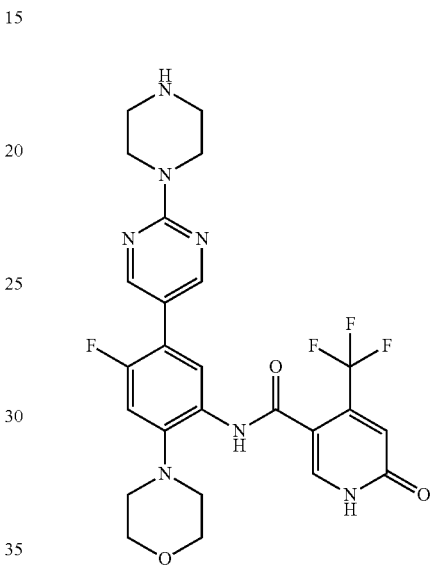

In a 5 mL microwave vial to a suspension of 6-hydroxy-4-(trifluoromethyl)nicotinic acid (145 mg, 0.698 mmol) in pyridine, anhydrous (847 μl, 10.47 mmol) was added slowly diethyl chlorophosphate (103 μl, 0.715 mmol at RT in an atmosphere of nitrogen. The reaction mixture was stirred at rt for 2 hours. The suspension turned into a solution and then into a suspension again. To this, tert-butyl 4-(5-(5-amino-2-fluoro-4-morpholinophenyl)pyrimidin-2-yl)piperazine-1-carboxylate (80 mg, 0.174 mmol) was added and the reaction was heated at 70° C. for 3 h. After completion, pyridine was removed in vacuo and the residue partitioned between ethyl acetate (3 mL) and saturated sodium bicarbonate solution (3 mL). The suspension was stirred for 10 min. The organic layer was separated, and dried over anhydrous $Na_2SO_4$. The solvent was evaporated in vacuo yielding the crude product. The solvent was evaporated in vacuo yielding the crude product that was purified by flash column chromatography on silica gel (0-100%, 89% $CH_2Cl_2$, 10% MeOH, 1% $NH_4Ac/CH_2Cl_2$) to afford the silyloxy intermediate. The product was dissolved in 2 mL of dichloromethane and trifluoroacetic acid (398 mg, 3.49 mmol) was added. The purple solution was stirred for 1 hour and the solvent was evaporated. The residue was purified using a cation exchange column eluting with MeOH:$NH_4OH$ and freeze dried for 2 days to afford the title compound. $^1$H NMR (500 MHz, MeOD) δ 8.55 (d, J=0.9 Hz, 2H), 8.00 (s, 1H), 7.92 (d, J=8.2 Hz, 1H), 7.12 (d, J=12.1 Hz, 1H), 6.88 (s, 1H), 3.92-3.88 (m, 4H), 3.85-3.81 (m, 4H), 2.96 (dd, J=9.8, 5.2 Hz, 8H); LCMS [M+1]$^+$=548.41.

Example 310: N-[4-fluoro-5-(2-morpholin-4-ylpyrimidin-5-yl)-2-[(3R,4R)-3-(dimethylamino)-4-fluoropyrrolidin-1-yl]phenyl]-6-oxo-4-(trifluoromethyl)-1H-pyridine-3-carboxamide

Example 311: N-[5-[6-(cyclopropylmethoxy)pyridin-3-yl]-4-fluoro-2-[(3R,4R)-3-(dimethylamino)-4-fluoropyrrolidin-1-yl]phenyl]-6-oxo-4-(trifluoromethyl)-1H-pyridine-3-carboxamide

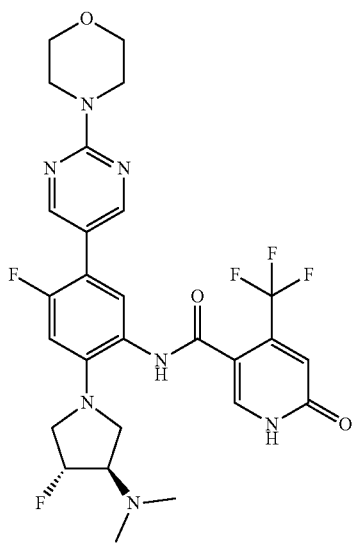 [SMILES: CN(C)[C@@H]1CN(c2cc(F)c(-c3cnc(N4CCOCC4)nc3)cc2NC(=O)c2c[nH]c(=O)cc2C(F)(F)F)C[C@H]1F]

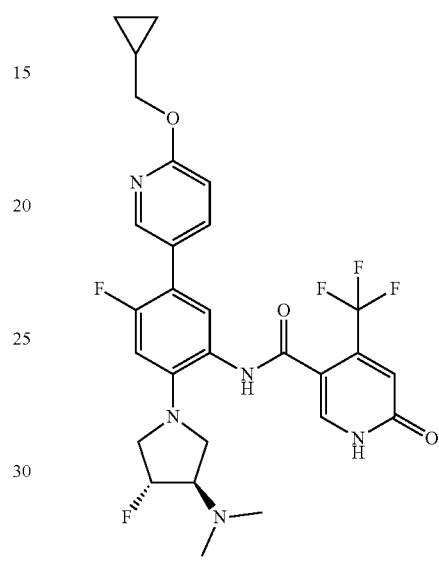

4-(Trifluoromethyl)-6-(2-(trimethylsilyl)ethoxy)nicotinic acid (0.068 g, 0.22 mmol) was activated with HATU (0.085 g, 0.22 mmol) and N,N-diisopropylethylamine (0.04 mL, 0.22 mmol) in DMF (1 mL) at room temperature. The solution of activated acid was added to a solution of trans-1-(2-amino-5-fluoro-4-(2-morpholinopyrimidin-5-yl)phenyl)-4-fluoro-N,N-dimethylpyrrolidin-3-amine (0.060 g, 0.15 mmol, from Example 307) in DMF (1 mL) and the reaction was heated to 55° C. for 18 h. After cooling to room temperature the reaction mixture was concentrated onto celite and purified by flash chromatography [0.5-10% MeOH/DCM+0.5% NH$_4$OH]. The silyl protected amide was dissolved in DCM (2 mL) and treated with trifluoroacetic acid (2 mL) at room temperature. After stirring for 3 h the volatiles were removed under a stream of air and the residue was concentrated onto celite. Reverse phase chromatography [5-95% MeCN/H$_2$O+10 mM NH$_4$HCO$_3$] followed by lyophilization afforded trans-N-(2-(3-(dimethylamino)-4-fluoropyrrolidin-1-yl)-4-fluoro-5-(2-morpholinopyrimidin-5-yl)phenyl)-6-oxo-4-(trifluoromethyl)-1,6-dihydropyridine-3-carboxamide (0.040 g, 45%). $^1$H NMR (500 MHz, DMSO-d6) δ=9.81 (br s, 1H), 8.52 (s, 2H), 8.01 (br s, 1H), 7.40 (d, J=8.8 Hz, 1H), 6.82 (d, J=13.6 Hz, 1H), 6.75 (br s, 1H), 5.30-5.14 (m, 1H), 3.76-3.73 (m, 4H), 3.70-3.67 (m, 4H), 3.62-3.53 (m, 4H), 3.19-3.14 (m, 1H), 2.97-2.88 (m, 1H), 2.22 (s, 6H); LCMS [M+H]+: 594.5.

4-(Trifluoromethyl)-6-(2-(trimethylsilyl)ethoxy)nicotinic acid (0.060 g, 0.19 mmol) was activated with HATU (0.073 g, 0.19 mmol) and N,N-diisopropylethylamine (0.04 mL, 0.19 mmol) in DMF (1 mL) at room temperature. The solution of activated acid was added to a solution of trans-1-(2-amino-4-(6-(cyclopropylmethoxy)pyridin-3-yl)-5-fluorophenyl)-4-fluoro-N,N-dimethylpyrrolidin-3-amine (0.050 g, 0.13 mmol) in DMF (1 mL) and the reaction was heated to 55° C. for 18 h. After cooling to room temperature the reaction mixture was concentrated onto celite and purified by flash chromatography [0.5-10% MeOH/DCM+0.5% NH$_4$OH]. The silyl protected amide was dissolved in DCM (2 mL) and treated with trifluoroacetic acid (2 mL) at room temperature. After stirring for 3 h the volatiles were removed under a stream of air and the residue was concentrated onto celite. Reverse phase chromatography [5-95% MeCN/H$_2$O+ 10 mM NH$_4$HCO$_3$] afforded 18 mg (27% yield) of the title compound. $^1$H NMR (500 MHz, DMSO-d6) δ=9.81 (br s, 1H), 8.24 (s, 1H), 8.01 (br s, 1H), 7.81 (br d, J=9.5 Hz, 1H), 7.40 (br d, J=8.7 Hz, 1H), 6.92 (d, J=8.7 Hz, 1H), 6.82 (d, J=13.7 Hz, 1H), 6.75 (br s, 1H), 5.30-5.15 (m, 1H), 4.13 (d, J=7.1 Hz, 2H), 3.63-3.53 (m, 4H), 3.17 (dd, J=6.3, 10.2 Hz, 1H), 2.97-2.87 (m, 1H), 2.22 (s, 6H), 1.30-1.23 (m, 1H), 0.59-0.53 (m, 2H), 0.36-0.32 (m, 2H); LCMS [M+H]+: 578.5.

Example 312: N-[4-fluoro-5-(6-hydroxypyridin-3-yl)-2-[(3R 4R)-3-(dimethylamino)-4-fluoropyrrolidin-1-yl]phenyl]-6-oxo-4-(trifluoromethyl)-1H-pyridine-3-carboxamide

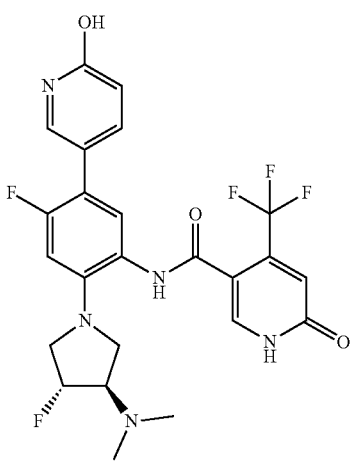

The reverse phase chromatography from Example 311 afforded 17 mg (23% yield) of the title compound. $^1$H NMR (500 MHz, DMSO-d6) δ=11.92-11.65 (m, 1H), 9.77 (br s, 1H), 8.01 (br s, 1H), 7.61 (br d, J=9.0 Hz, 1H), 7.46 (br s, 1H), 7.34 (d, J=8.8 Hz, 1H), 6.85-6.71 (m, 2H), 6.44 (d, J=9.5 Hz, 1H), 5.33-5.10 (m, 1H), 3.61-3.53 (m, 5H), 3.13 (dd, J=6.7, 10.0 Hz, 1H), 2.97-2.85 (m, 1H), 2.21 (s, 6H); LCMS [M+H]+: 524.3.

Example 313: tert-butyl 4-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-3,6-dihydro-2H-pyridine-1-carboxylate

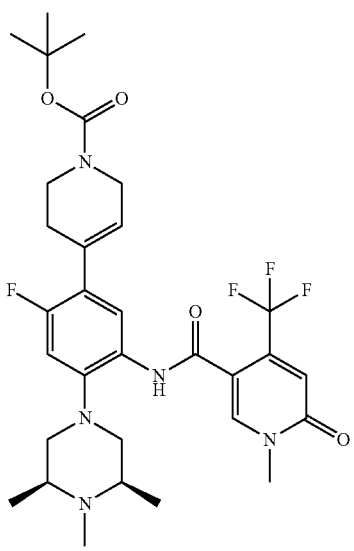 [SMILES: C[C@@H]1CN(c2cc(F)c(C3=CCN(C(=O)OC(C)(C)C)CC3)cc2NC(=O)c2cn(C)c(=O)cc2C(F)(F)F)C[C@H](C)N1C]

Iodomethane (1.178 μl, 0.019 mmol) was added to a solution of tert-butyl 4-(2-fluoro-5-(6-oxo-4-(trifluoromethyl)-1,6-dihydropyridine-3-carboxamido)-4-((3S,5R)-3,4,5-trimethylpiperazin-1-yl)phenyl)-3,6-dihydropyridine-1 (2H)-carboxylate (10 mg, 0.016 mmol) and cesium carbonate (5.36 mg, 0.016 mmol) in DMF (1. ml) at RT to give the title compound (8 mg, 74% yield). $^1$H NMR (500 MHz, METHANOL-d4) δ=8.15-8.07 (m, 1H), 7.71-7.63 (m, 1H), 6.90-6.82 (m, 2H), 5.95-5.83 (m, 1H), 4.02-3.94 (m, 2H), 3.58-3.49 (m, 5H), 2.94-2.88 (m, 2H), 2.52-2.38 (m, 6H), 2.28-2.24 (m, 3H), 1.42-1.39 (m, 9H), 1.06-1.03 (m, 6H); LCMS [M+H]+ 622.5.

Example 314: N-[5-[6-(cyclopropylmethoxy)pyridin-3-yl]-4-fluoro-2-[(3R,5S)-3,4,5-trimethylpiperazin-1-yl]phenyl]-4-(difluoromethyl)-6-oxo-1H-pyridine-3-carboxamide

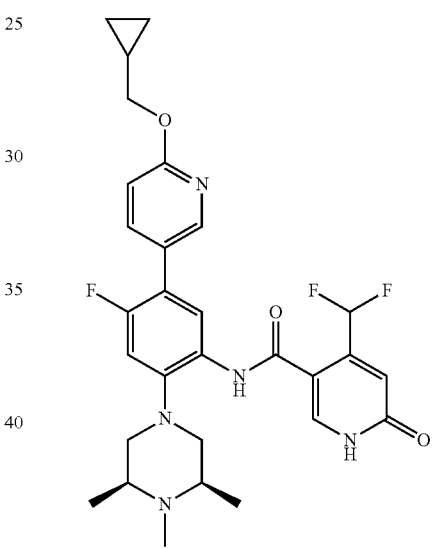

The title compound (19 mg, 46% yield) was obtained from 4-(difluoromethyl)-6-oxo-1,6-dihydropyridine-3-carboxylic acid (59.0 mg, 0.312 mmol) and 5-(6-(cyclopropylmethoxy)pyridin-3-yl)-4-fluoro-2-((3S,5R)-3,4,5-trimethylpiperazin-1-yl)aniline (30 mg, 0.078 mmol). $^1$H NMR (500 MHz, MeOD) δ 8.27 (s, 1H), 8.01 (s, 1H), 7.86 (dd, J=8.7, 0.8 Hz, 1H), 7.81 (d, J=8.3 Hz, 1H), 7.31 (t, J=55.1 Hz, 1H), 7.05 (d, J=12.1 Hz, 1H), 6.87 (d, J=8.6 Hz, 1H), 6.81 (s, 1H), 4.15 (d, J=7.1 Hz, 2H), 3.07 (d, J=11.3 Hz, 2H), 2.60 (t, J=11.1 Hz, 2H), 2.55-2.47 (m, 2H), 2.36 (s, 3H), 1.34-1.25 (m, 1H), 1.15 (d, J=6.2 Hz, 6H), 0.64-0.58 (m, 2H), 0.36 (q, J=4.7 Hz, 2H); LCMS [M+1]+=556.5.

Example 315: 1-ethyl-N-[4-fluoro-5-(2-morpholin-4-ylpyrimidin-5-yl)-2-[(3R,5S)-3,4,5-trimethylpiperazin-1-yl]phenyl]-6-oxo-4-(trifluoromethyl)pyridine-3-carboxamide Example 316: 4-fluoro-N-[4-fluoro-5-[2-(4-methylpiperazin-1-yl)pyrimidin-5-yl]-2-[(3R)-3,4-dimethylpiperazin-1-yl]phenyl]-2-(trifluoromethyl)benzamide

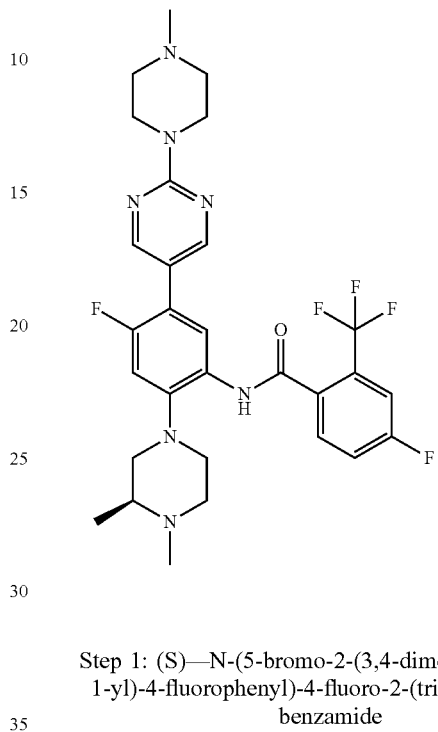

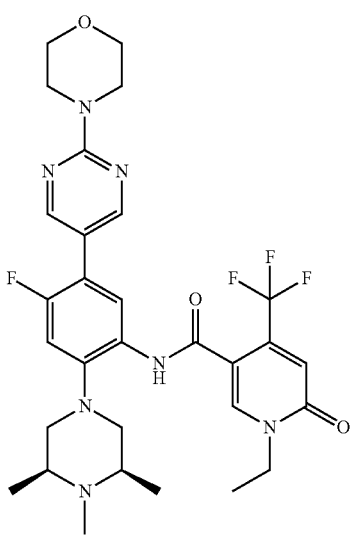 [SMILES: CCn1cc(C(=O)Nc2cc(-c3cnc(N4CCOCC4)nc3)c(F)cc2N2C[C@@H](C)N(C)[C@@H](C)C2)c(C(F)(F)F)cc1=O]

Step 1: (S)—N-(5-bromo-2-(3,4-dimethylpiperazin-1-yl)-4-fluorophenyl)-4-fluoro-2-(trifluoromethyl)benzamide

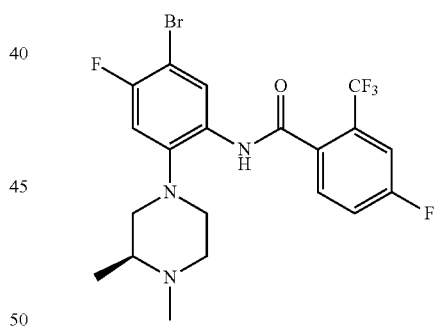

Cesium carbonate (25.5 mg, 0.078 mmol) was added to a solution of N-(4-fluoro-5-(2-morpholinopyrimidin-5-yl)-2-((3S,5R)-3,4,5-trimethylpiperazin-1-yl)phenyl)-6-oxo-4-(trifluoromethyl)-1,6-dihydropyridine-3-carboxamide (46.06 mg, 0.078 mmol) and iodoethane (7.19 µl, 0.090 mmol) in DMF (1562 µl) at RT. The reaction mixture was stirred at RT overnight. The solvent was evaporated in vacuo yielding the crude product then purification was performed by flash column chromatography on silica gel (0-100%, 89% CH$_2$Cl$_2$, 10% MeOH, 1% NH$_4$Ac/CH$_2$Cl$_2$) to afford the desired compound. $^1$H NMR (500 MHz, MeOD) δ 8.55 (s, 2H), 8.23 (s, 1H), 7.93 (d, J=8.2 Hz, 1H), 7.09 (d, J=12.1 Hz, 1H), 6.93 (s, 1H), 4.11 (q, J=7.2 Hz, 2H), 3.85-3.82 (m, 4H), 3.78-3.75 (m, 4H), 3.06 (d, J=11.4 Hz, 2H), 2.61 (t, J=11.2 Hz, 2H), 2.54-2.47 (m, 2H), 2.34 (s, 3H), 1.42 (t, J=7.2 Hz, 3H), 1.15 (d, J=6.2 Hz, 6H); LCMS HSS [M+1]$^+$=618.61.

To a solution of 4-fluoro-2-(trifluoromethyl)benzoyl chloride (0.61 mL, 4 mmol) in DCM (15 mL) at rt was added Et$_3$N (1.12 mL, 8 mmol). After addition, the resulting mixture was stirred at rt for 5 min and a solution of (S)-5-bromo-2-(3,4-dimethylpiperazin-1-yl)-4-fluoroaniline (604 mg, 2 mmol) in DCM (10 mL) was added. The resulting dark orange solution was stirred at rt for 2 h. After quenching with sat. NaHCO$_3$ (15 mL) and stirring for 2 min at rt, it was extracted with DCM (20 mL×2). The combined extracts were combined, and concentrated to give a light beige solid. Purification by flash chromatography (gradient: EtOAc/hex 0-100%) gave the title compound as a light yellow solid (822 mg, 82%). LCMS [M+H]$^+$ 492.4.

Step 2: Preparation of (S)—N-(2-(3,4-dimethylpiperazin-1-yl)-4-fluoro-5-(2-(4-methylpiperazin-1-yl)pyrimidin-5-yl)phenyl)-4-fluoro-2-(trifluoromethyl)benzamide

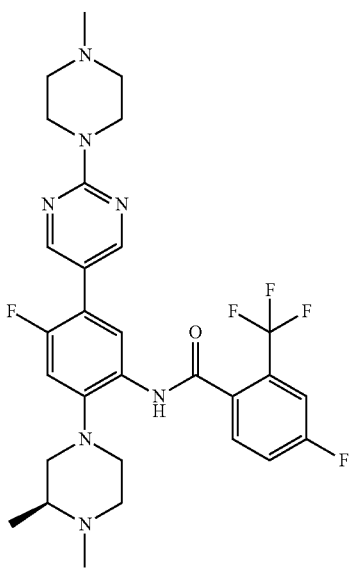 [SMILES: C[C@H]1CN(c2cc(F)c(-c3cnc(N4CCN(C)CC4)nc3)cc2NC(=O)c2ccc(F)cc2C(F)(F)F)CCN1C]

The title compound (beige solid, 15.9 mg, 26%) was prepared according to a procedure similar to the last step of Example 31 using (S)—N-(5-bromo-2-(3,4-dimethylpiperazin-1-yl)-4-fluorophenyl)-4-fluoro-2-(trifluoromethyl)benzamide (53 mg, 0.1 mmol) and 2-(4-methylpiperazin-1-yl)pyrimidine-5-boronic acid pinacol ester (61 mg, 0.2 mmol). $^1$H NMR (500 MHz, CHLOROFORM-d) δ=8.61-8.54 (m, 4H), 7.67 (dd, J=5.3, 8.4 Hz, 1H), 7.50 (dd, J=2.4, 8.7 Hz, 1H), 7.38 (dt, J=2.3, 8.1 Hz, 1H), 7.02 (d, J=11.2 Hz, 1H), 3.97-3.87 (m, 4H), 2.97-2.81 (m, 4H), 2.56 (t, J=10.5 Hz, 1H), 2.50 (t, J=5.1 Hz, 4H), 2.36 (s, 3H), 2.32-2.25 (m, 4H), 2.12 (br s, 1H), 1.05 (d, J=6.2 Hz, 3H); LCMS [M+H]$^+$ 590.3.

Example 317: 4-fluoro-N-[4-fluoro-5-[6-(4-methylpiperazin-1-yl)pyridin-3-yl]-2-[(3R)-3,4-dimethylpiperazin-1-yl]phenyl]-2-(trifluoromethyl)benzamide

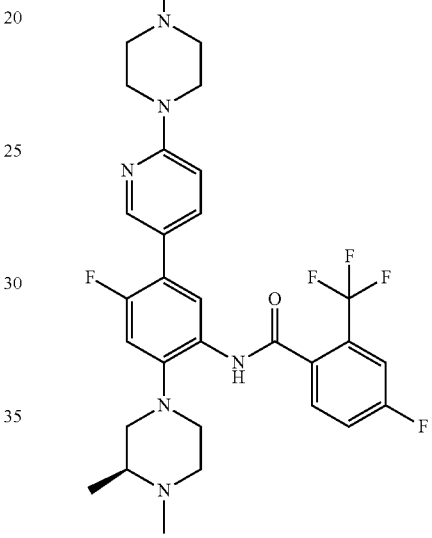

The title compound (beige solid, 6.6 mg, 11%) was prepared through a method similar to Example 31 using (S)—N-(5-bromo-2-(3,4-dimethylpiperazin-1-yl)-4-fluorophenyl)-4-fluoro-2-(trifluoromethyl)benzamide (53 mg, 0.1 mmol) and 2-(4-methylpiperazin-1-yl)pyridine-5-boronic acid, pinacol ester (61 mg, 0.2 mmol). $^1$H NMR (500 MHz, CHLOROFORM-d) δ=8.62 (d, J=7.9 Hz, 1H), 8.56 (s, 1H), 8.24 (d, J=5.1 Hz, 1H), 7.67 (dd, J=5.3, 8.4 Hz, 1H), 7.51 (dd, J=2.3, 8.8 Hz, 1H), 7.39 (t, J=8.0 Hz, 1H), 7.01 (d, J=11.2 Hz, 1H), 6.88-6.83 (m, 2H), 3.67-3.59 (m, 4H), 2.99-2.82 (m, 4H), 2.61-2.52 (m, 5H), 2.36 (s, 3H), 2.32-2.26 (m, 4H), 2.13 (br s, 1H), 1.06 (d, J=6.2 Hz, 3H); LCMS [M+H]$^+$ 589.5.

Example 318: 2,3-dichloro-N-[4-fluoro-5-(2-morpholin-4-ylpyrimidin-5-yl)-2-[(3R)-3,4-dimethylpiperazin-1-yl]phenyl]benzamide

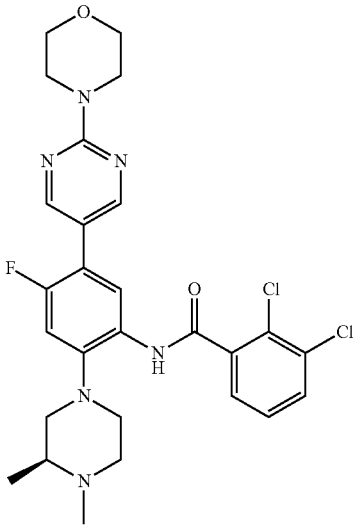 [SMILES: C[C@H]1CN(c2cc(F)c(-c3cnc(N4CCOCC4)nc3)cc2NC(=O)c2cccc(Cl)c2Cl)CCN1C]

The title compound (beige solid, 45.5 mg, 77%) was prepared through a method similar to Example 78 using 2,3-dichlorobenzoic acid (38 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=8.91 (s, 1H), 8.63 (d, J=8.2 Hz, 1H), 8.58 (s, 2H), 7.60 (dd, J=8.0, 9.1 Hz, 1H), 7.61 (dd, J=7.9, 12.2 Hz, 1H), 7.36 (t, J=7.8 Hz, 1H), 7.01 (d, J=11.2 Hz, 1H), 3.91-3.85 (m, 4H), 3.82-3.78 (m, 4H), 2.88 (br d, J=11.0 Hz, 2H), 2.64 (t, J=10.9 Hz, 2H), 2.39-2.29 (m, 5H), 1.13 (d, J=6.2 Hz, 6H); LCMS [M+H]$^+$ 573.3.

Example 319: N-[4-fluoro-2-[(3R)-3,4-dimethylpiperazin-1-yl]-5-[2-(2,2,6,6-tetramethylmorpholin-4-yl)pyrimidin-5-yl]phenyl]-6-oxo-4-(trifluoromethyl)-1H-pyridine-3-carboxamide

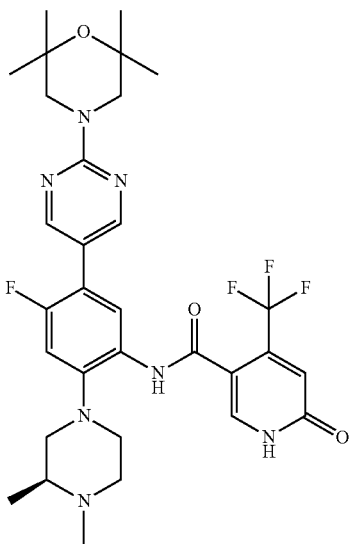 [SMILES: C[C@H]1CN(c2cc(F)c(-c3cnc(N4CC(C)(C)OC(C)(C)C4)nc3)cc2NC(=O)c2c[nH]c(=O)cc2C(F)(F)F)CCN1C]

To a mixture of 2-chloropyrimidine-5-boronic acid (31.7 mg, 0.2 mmol) and 2,2,6,6-tetramethylmorpholine (30.1 mg, 0.21 mmol) in EtOH (1 mL) was added triethylamine (0.042 mL, 0.3 mmol). The resulting suspension was stirred at 70° C. for 1 h. Solvents were removed to give the crude (2-(2,2,6,6-tetramethylmorpholino)pyrimidin-5-yl)boronic acid intermediate as colorless crystals. LCMS [M+H]$^+$ 266.3. The title compound (white solid, 40.7 mg, 64%) was prepared through methods similar to those described in Example 40 using the above boronic acid (0.2 mmol) and (S)—N-(5-bromo-2-(3,4-dimethylpiperazin-1-yl)-4-fluorophenyl)-6-oxo-4-(trifluoromethyl)-1,6-dihydropyridine-3-carboxamide (49.1 mg, 0.1 mmol). $^1$H NMR (500 MHz, CHLOROFORM-d) δ=8.71 (br s, 1H), 8.54 (s, 2H), 8.47 (br d, J=8.1 Hz, 1H), 7.87 (s, 1H), 7.04 (d, J=11.1 Hz, 1H), 7.01 (s, 1H), 3.72 (s, 4H), 3.02-2.87 (m, 3H), 2.83 (br d, J=10.8 Hz, 1H), 2.60 (br t, J=10.3 Hz, 1H), 2.35 (br s, 4H), 2.22 (br s, 1H), 1.29 (s, 12H), 1.10 (br d, J=5.9 Hz, 3H); LCMS [M+H]$^+$ 632.5.

Example 320: N-[4-fluoro-2-[(3R,5S)-3,4,5-trimethylpiperazin-1-yl]-5-[2-(2,2,6,6-tetramethylmorpholin-4-yl)pyrimidin-5-yl]phenyl]-6-oxo-4-(trifluoromethyl)-1H-pyridine-3-carboxamide

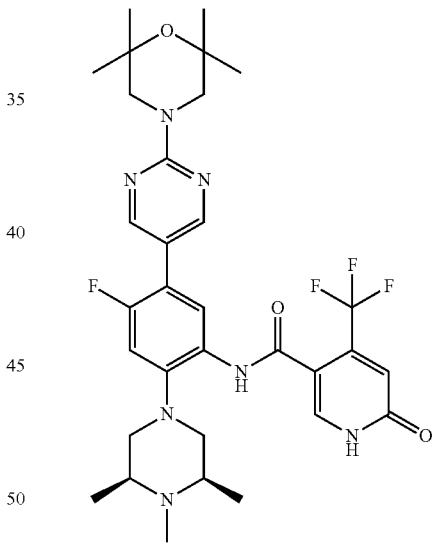

The title compound (white solid, 32.3 mg, 49%) was prepared by methods similar to those described in Example 31 using crude (2-(2,2,6,6-tetramethylmorpholino)pyrimidin-5-yl)boronic acid (0.2 mmol) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, CHLOROFORM-d) δ=8.70 (br s, 1H), 8.54 (s, 2H), 8.45 (d, J=8.1 Hz, 1H), 7.87 (s, 1H), 7.05-6.97 (m, 2H), 3.72 (s, 4H), 2.82 (br d, J=10.8 Hz, 2H), 2.66 (br t, J=10.8 Hz, 2H), 2.40-2.26 (m, 5H), 1.29 (s, 12H), 1.14 (d, J=6.0 Hz, 6H); LCMS [M+H]$^+$ 646.5.

Example 321: N-[4-fluoro-5-(2-morpholin-4-ylpyrimidin-5-yl)-2-[(3R,5S)-3,4,5-trimethylpiperazin-1-yl]phenyl]-5-(trifluoromethyl)-1H-pyrazole-3-carboxamide

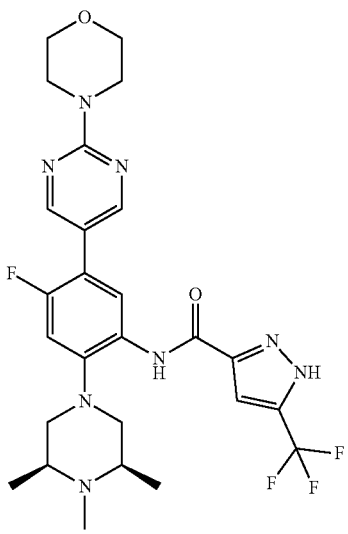

The title compound (white solid, 48.8 mg, 86%) was prepared by methods similar to Example 34 using 5-(trifluoromethyl)-1H-pyrazole-3-carboxylic acid (27 mg, 0.15 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=9.37 (s, 1H), 8.61 (d, J=1.0 Hz, 2H), 8.58 (d, J=8.2 Hz, 1H), 7.05 (d, J=11.2 Hz, 1H), 7.01 (s, 1H), 3.93-3.87 (m, 4H), 3.84-3.80 (m, 4H), 2.91 (br d, J=11.0 Hz, 2H), 2.74 (t, J=10.9 Hz, 2H), 2.55-2.46 (m, 2H), 2.42 (s, 3H), 1.18 (d, J=6.2 Hz, 6H); LCMS [M+H]$^+$ 563.5.

Example 322: tert-butyl 5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate

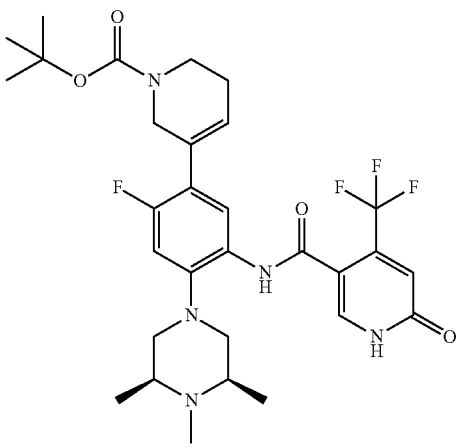 [SMILES: C[C@@H]1CN(c2cc(F)c(C3=CCCN(C(=O)OC(C)(C)C)C3)cc2NC(=O)c2c[nH]c(=O)cc2C(F)(F)F)C[C@H](C)N1C]

The procedure followed was similar to Example 100 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (400 mg, 0.661 mmol) and 1-boc-5,6-dihydro-2H-pyridine-3-boronic acid, pinacol ester (306 mg, 0.991 mmol) to give, after deprotection of the silyloxy intermediate tert-butyl 5-(2-fluoro-5-(6-oxo-4-(trifluoromethyl)-1,6-dihydropyridine-3-carboxamido)-4-((3S,5R)-3,4,5-trimethylpiperazin-1-yl)phenyl)-3,6-dihydropyridine-1 (2H)-carboxylate and purification, the title compound. (33 mg, 73% yield). $^1$H NMR (500 MHz, METHANOL-d4) δ=7.86-7.80 (m, 1H), 7.69-7.60 (m, 1H), 6.89-6.82 (m, 1H), 6.82-6.77 (m, 1H), 6.02-5.95 (m, 1H), 4.15-4.06 (m, 2H), 3.54-3.42 (m, 2H), 2.95-2.89 (m, 2H), 2.54-2.40 (m, 4H), 2.28-2.25 (m, 3H), 2.24-2.19 (m, 2H), 1.40-1.37 (m, 9H), 1.05 (d, J=6.0 Hz, 6H); LCMS [M+H]+ 608.4

Example 323: tert-butyl 3-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-2,5-dihydropyrrole-1-carboxylate

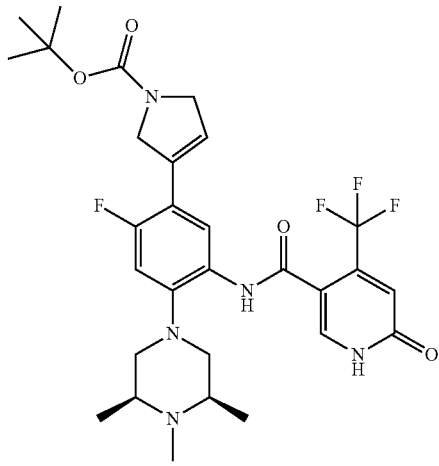 [SMILES: C[C@@H]1CN(c2cc(F)c(C3=CCN(C(=O)OC(C)(C)C)C3)cc2NC(=O)c2c[nH]c(=O)cc2C(F)(F)F)C[C@H](C)N1C]

A procedure similar to that used in Example 100 with N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (400 mg, 0.661 mmol) and tert-butyl 3-(4,4,5,5-tetramethyl-1,3,2-dioxaborolan-2-yl)-2,5-dihydropyrrole-1-carboxylate (292 mg, 0.991 mmol) gave the silyloxypyridyl intermediate that was deprotected and purified to give the title compound (42.5 mg, 94% yield on last step). $^1$H NMR (500 MHz, METHANOL-d4) δ=7.90-7.84 (m, 1H), 7.74-7.61 (m, 1H), 6.96-6.88 (m, 1H), 6.85-6.79 (m, 1H), 6.28-6.19 (m, 1H), 4.44-4.35 (m, 2H), 4.24-4.15 (m, 2H), 3.04-2.96 (m, 2H), 2.66-2.52 (m, 4H), 2.40-2.31 (m, 3H), 1.44-1.39 (m, 9H), 1.13-1.09 (m, 6H); LCMS [M+H]+ 594.6.

Example 324: tert-butyl 3-[2-fluoro-5-[[6-oxo-4-(trifluoromethyl)-H-pyridine-3-carbonyl]amino]-4-[(3R,5S)-3,4,5-trimethylpiperazin-1-yl]phenyl]-8-azabicyclo[3.2.1]oct-2-ene-8-carboxylate

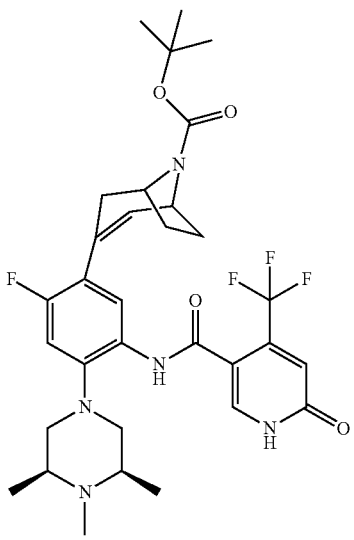 [SMILES: C[C@@H]1CN(c2cc(F)c(C3=CC4CCC(C3)N4C(=O)OC(C)(C)C)cc2NC(=O)c2c[nH]c(=O)cc2C(F)(F)F)C[C@H](C)N1C]

A similar sequence to that of Example 100 starting from N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (400 mg, 0.661 mmol), 8-Boc-8-azabicyclo[3.2.1]oct-3-ene-3-boronic acid pinacol ester (332 mg, 0.991 mmol) gave, after deprotection of the silyloxy intermediate and purification using standard methods, the title compound (33 mg, 73% yield for last step). $^1$H NMR (500 MHz, METHANOL-d4) δ=7.87-7.81 (m, 1H), 7.66-7.56 (m, 1H), 6.87-6.79 (m, 2H), 6.25-6.18 (m, 1H), 4.40-4.27 (m, 2H), 3.04-2.95 (m, 1H), 2.95-2.88 (m, 2H), 2.53-2.43 (m, 4H), 2.31-2.27 (m, 3H), 2.19-2.10 (m, 2H), 1.99-1.89 (m, 2H), 1.78-1.69 (m, 1H), 1.41-1.36 (m, 9H), 1.08-1.04 (m, 6H); LCMS [M+H]+ 594.6.

Example 325: tert-butyl 5-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-3,6-dihydro-2H-pyridine-1-carboxylate

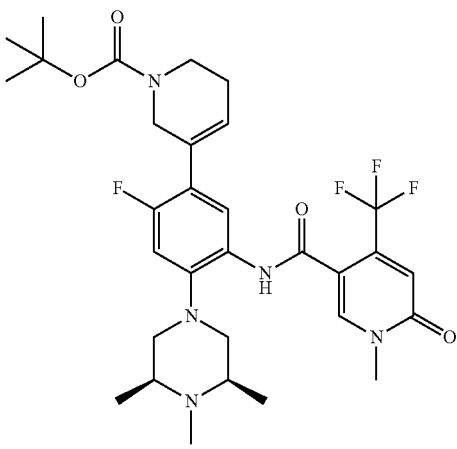 [SMILES: C[C@@H]1CN(c2cc(F)c(C3=CCCN(C(=O)OC(C)(C)C)C3)cc2NC(=O)c2cn(C)c(=O)cc2C(F)(F)F)C[C@H](C)N1C]

Iodomethane (2.83 μl, 0.045 mmol) was added to a solution of tert-butyl 5-(2-fluoro-5-(6-oxo-4-(trifluoromethyl)-1,6-dihydropyridine-3-carboxamido)-4-((3S,5R)-3,4,5-trimethylpiperazin-1-yl)phenyl)-3,6-dihydropyridine-1(2H)-carboxylate (24 mg, 0.039 mmol) and cesium carbonate (12.87 mg, 0.039 mmol) in DMF (1. ml) at RT. The mixture was stirred at RT. After 15 min, the mixture was quenched, worked up and purified using standard methods to give the title compound (15.5 mg, 60% yield). $^1$H NMR (500 MHz, METHANOL-d4) δ=8.14-8.06 (m, 1H), 7.70-7.61 (m, 1H), 6.89-6.81 (m, 2H), 6.04-5.94 (m, 1H), 4.14-4.08 (m, 2H), 3.56-3.53 (m, 3H), 3.51-3.43 (m, 2H), 2.94-2.88 (m, 2H), 2.51-2.44 (m, 2H), 2.43-2.35 (m, 2H), 2.24-2.19 (m, 5H), 1.40-1.37 (m, 9H), 1.04 (d, J=6.2 Hz, 6H); LCMS [M+H]+ 622.5.

Example 326: tert-butyl 3-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-2,5-dihydropyrrole-1-carboxylate

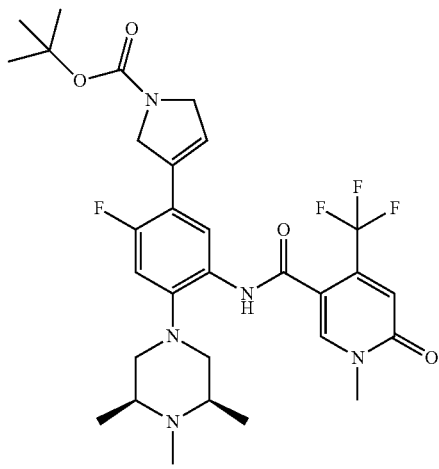 [SMILES: C[C@@H]1CN(c2cc(F)c(C3=CCN(C(=O)OC(C)(C)C)C3)cc2NC(=O)c2cn(C)c(=O)cc2C(F)(F)F)C[C@H](C)N1C]

A similar procedure To Example 325 using iodomethane (3.86 μl, 0.062 mmol), tert-butyl 3-(2-fluoro-5-(6-oxo-4-(trifluoromethyl)-1,6-dihydropyridine-3-carboxamido)-4-((3S,5R)-3,4,5-trimethylpiperazin-1-yl)phenyl)-2,5-dihydro-1H-pyrrole-1-carboxylate (32 mg, 0.054 mmol) and cesium carbonate (17.56 mg, 0.054 mmol) gave the title compound (23.5 mg, 68% yield). $^1$H NMR (500 MHz, METHANOL-d4) δ=8.18-8.09 (m, 1H), 7.76-7.60 (m, 1H), 6.94-6.87 (m, 1H), 6.85-6.80 (m, 1H), 6.28-6.18 (m, 1H), 4.43-4.35 (m, 2H), 4.23-4.14 (m, 2H), 3.58-3.52 (m, 3H), 2.98-2.89 (m, 2H), 2.52-2.44 (m, 2H), 2.43-2.35 (m, 2H), 2.26-2.21 (m, 3H), 1.41 (d, J=5.4 Hz, 9H), 1.05-1.01 (m, 6H); LCMS [M+H]+ 608.4.

Example 327: tert-butyl 3-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-8-azabicyclo[3.2.1]oct-2-ene-8-carboxylate

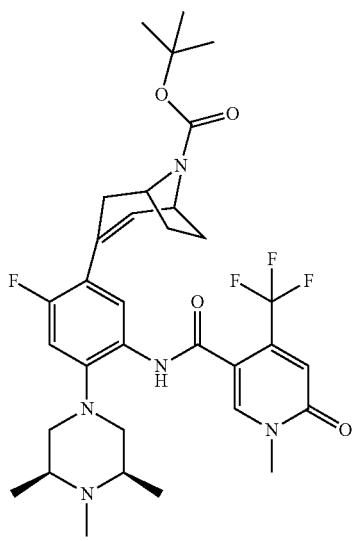 [SMILES: C[C@@H]1CN(c2cc(F)c(C3=CC4CCC(C3)N4C(=O)OC(C)(C)C)cc2NC(=O)c2cn(C)c(=O)cc2C(F)(F)F)C[C@H](C)N1C]

A similar procedure to Example 325 using iodomethane (2.82 μl, 0.045 mmol), tert-butyl 3-(2-fluoro-5-(6-oxo-4-(trifluoromethyl)-1,6-dihydropyridine-3-carboxamido)-4-((3S,5R)-3,4,5-trimethylpiperazin-1-yl)phenyl)-8-azabicyclo[3.2.1]oct-2-ene-8-carboxylate (25 mg, 0.039 mmol) and cesium carbonate (12.85 mg, 0.039 mmol) gave the title compound (17 mg, 58% yield). $^1$H NMR (500 MHz, METHANOL-d4) δ=8.13-8.08 (m, 1H), 7.64-7.56 (m, 1H), 6.85-6.78 (m, 2H), 6.23-6.17 (m, 1H), 4.37-4.26 (m, 2H), 3.55-3.52 (m, 3H), 3.01-2.94 (m, 1H), 2.91-2.86 (m, 2H), 2.49-2.42 (m, 2H), 2.40-2.34 (m, 2H), 2.24-2.21 (m, 3H), 2.18-2.08 (m, 2H), 1.97-1.89 (m, 2H), 1.77-1.67 (m, 1H), 1.40-1.36 (m, 9H), 1.04-1.01 (m, 6H); LCMS [M+H]+ 648.5.

Example 328: N-[4-fluoro-2-[(3R,5S)-3,4,5-trimethylpiperazin-1-yl]-5-(1,2,3,6-tetrahydropyridin-5-yl)phenyl]-6-oxo-4-(trifluoromethyl)-1H-pyridine-3-carboxamide

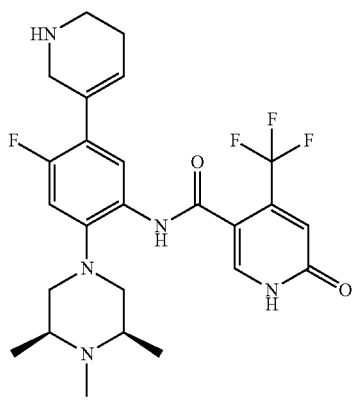

A procedure similar to that of Example 100 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (400 mg, 0.661 mmol) and 1-boc-5,6-dihydro-2H-pyridine-3-boronic acid, pinacol ester (306 mg, 0.991 mmol) gave, after deprotection of the silyloxy intermediate, (33 mg, 73% yield) of the title compound. $^1$H NMR (500 MHz, METHANOL-d4) δ=7.86-7.80 (m, 1H), 7.69-7.60 (m, 1H), 6.89-6.82 (m, 1H), 6.82-6.77 (m, 1H), 6.02-5.95 (m, 1H), 4.15-4.06 (m, 2H), 3.54-3.42 (m, 2H), 2.95-2.89 (m, 2H), 2.54-2.40 (m, 4H), 2.28-2.25 (m, 3H), 2.24-2.19 (m, 2H), 1.40-1.37 (m, 9H), 1.05 (d, J=6.0 Hz, 6H); LCMS [M+H]+ 608.4

Example 329: N-[5-(2,5-dihydro-1H-pyrrol-3-yl)-4-fluoro-2-[(3R,5S)-3,4,5-trimethylpiperazin-1-yl]phenyl]-6-oxo-4-(trifluoromethyl)-1H-pyridine-3-carboxamide

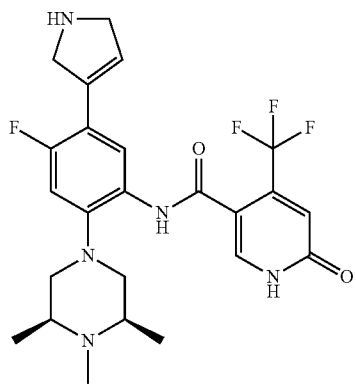 [SMILES: C[C@@H]1CN(c2cc(F)c(C3=CCNC3)cc2NC(=O)c2c[nH]c(=O)cc2C(F)(F)F)C[C@H](C)N1C]

A procedure similar to that of Example 100 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (400 mg, 0.661 mmol) and tert-butyl 3-(4,4,5,5-tetramethyl-1,3,2-dioxaborolan-2-yl)-2,5-dihydropyrrole-1-carboxylate (292 mg, 0.991 mmol) gave, after deprotection of the N-Boc silyloxy pyridine intermediate, the title compound (255 mg, 95% yield on last step). $^1$H NMR (500 MHz, METHANOL-d4) δ=8.09-8.02 (m, 1H), 7.91-7.79 (m, 1H), 7.07-6.97 (m, 1H), 6.86-6.77 (m, 1H), 6.45-6.36 (m, 1H), 4.29-4.21 (m, 2H), 4.09-4.01 (m, 2H), 3.10-3.01 (m, 2H), 2.65-2.56 (m, 2H), 2.55-2.48 (m, 2H), 2.38-2.34 (m, 3H), 1.18-1.13 (m, 6H); $^{19}$F NMR (471 MHz, METHANOL-d4) δ=−63.45 (s, 1F), −115.19 (s, 1F).

Example 330: N-[5-(8-azabicyclo[3.2.1]oct-2-en-3-yl)-4-fluoro-2-[(3R,5S)-3,4,5-trimethylpiperazin-1-yl]phenyl]-6-oxo-4-(trifluoromethyl)-1H-pyridine-3-carboxamide

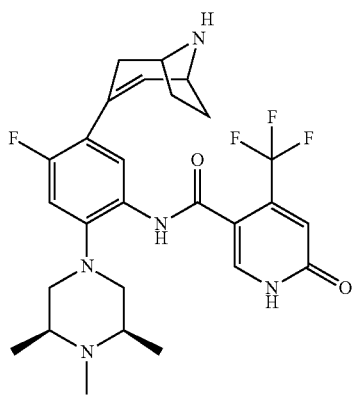

The procedure followed was similar to Example 100 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (400 mg, 0.661 mmol) and 8-Boc-8-azabicyclo[3.2.1]oct-3-ene-3-boronic acid pinacol ester (332 mg, 0.991 mmol) to give, after deprotection of the silyloxy coupled intermediate, the title compound as an off white powder. (33 mg, 73%). $^1$H NMR (500 MHz, METHANOL-d4) δ=8.12-8.07 (m, 1H), 7.86-7.75 (m, 1H), 7.00-6.93 (m, 1H), 6.78-6.72 (m, 1H), 6.39-6.30 (m, 1H), 4.19-4.07 (m, 1H), 3.15-3.06 (m, 1H), 3.05-2.99 (m, 2H), 2.61-2.54 (m, 2H), 2.53-2.47 (m, 3H), 2.38-2.35 (m, 3H), 2.32-2.23 (m, 2H), 2.16-2.05 (m, 1H), 2.00-1.94 (m, 1H), 1.17-1.14 (m, 6H); LCMS [M+H]+ 534.6

Example 331: 4-(difluoromethyl)-N-[4-fluoro-5-(6-morpholin-4-ylpyridin-3-yl)-2-[(3R)-3,4-dimethylpiperazin-1-yl]phenyl]-6-oxo-1H-pyridine-3-carboxamide

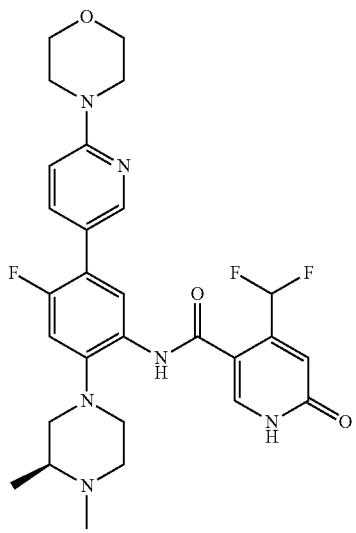 [SMILES: C[C@H]1CN(c2cc(F)c(-c3ccc(N4CCOCC4)nc3)cc2NC(=O)c2c[nH]c(=O)cc2C(F)F)CCN1C]

In a 10 ml microwave vial to a suspension of 4-(difluoromethyl)-6-oxo-1,6-dihydropyridine-3-carboxylic acid (78 mg, 0.415 mmol) in pyridine, anhydrous (504 μl, 6.23 mmol) was added slowly diethyl chlorophosphate (61.5 μl, 0.425 mmol) at rt in an atmosphere of nitrogen. The reaction mixture was stirred at rt for 2 h. The suspension turned into a solution and then into a suspension again. The suspension turned yellow white. To this, (S)-2-(3,4-dimethylpiperazin-1-yl)-4-fluoro-5-(6-morpholinopyridin-3-yl)aniline (40 mg, 0.104 mmol) was added and the reaction was heated at 70° C. for 16 h to give, after workup and purification (58 mg, 93% yield) of the title compound. $^1$H NMR (500 MHz, MeOD) δ 8.21 (s, 1H), 7.94 (s, 1H), 7.75 (d, J=8.3 Hz, 1H), 7.68 (d, J=9.1 Hz, 1H), 7.20 (t, J=55.1 Hz, 1H), 6.97 (d, J=12.1 Hz, 1H), 6.79 (d, J=8.9 Hz, 1H), 6.68 (s, 1H), 3.72-3.69 (m, 4H), 3.45-3.41 (m, 4H), 3.04 (d, J=11.1 Hz, 1H), 2.98 (d, J=8.9 Hz, 1H), 2.91-2.86 (m, 1H), 2.79 (s, 1H), 2.52 (s, 2H), 2.37 (s, 3H), 1.07 (s, 3H); LCMS [M+1]+=557.52.

Example 332: N-[5-(2-butan-2-yloxypyridin-4-yl)-4-fluoro-2-[(3R,5S)-3,4,5-trimethylpiperazin-1-yl]phenyl]-6-oxo-4-(trifluoromethyl)-1H-pyridine-3-carboxamide

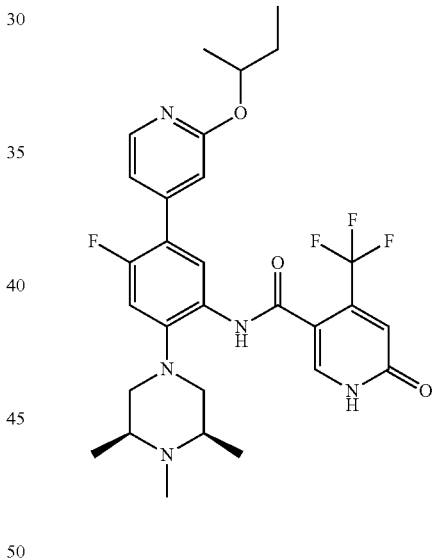

The title compound was prepared similar to the sequence described above for the preparation of Example 100 using 2-(sec-butoxy)-4-(4,4,5,5-tetramethyl-1,3,2-dioxaborolan-2-yl)pyridine (34.3 mg, 0.124 mmol) and N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) to give the title compound (31.5 mg, 66% yield). $^1$H NMR (500 MHz, DMSO-d6) δ=9.58 (s, 1H), 8.20 (d, J=5.3 Hz, 1H), 7.93 (s, 1H), 7.82 (d, J=8.4 Hz, 1H), 7.07 (d, J=5.3 Hz, 1H), 7.03 (d, J=12.8 Hz, 1H), 6.83 (s, 1H), 6.81 (s, 1H), 5.13 (q, J=6.2 Hz, 1H), 3.09 (br d, J=11.1 Hz, 2H), 2.49-2.45 (m, 1H), 2.36 (br s, 2H), 2.20 (s, 3H), 1.77-1.56 (m, 2H), 1.27 (d, J=6.1 Hz, 3H), 1.01 (br d, J=6.0 Hz, 6H), 0.92 (t, J=7.4 Hz, 3H); LCMS [M+H]+: 576.6.

Example 333: N-[4-fluoro-5-(2-morpholin-4-ylpyrimidin-5-yl)-2-[(3R,4R)-3-(dimethylamino)-4-methoxypyrrolidin-1-yl]phenyl]-6-oxo-4-(trifluoromethyl)-1H-pyridine-3-carboxamide

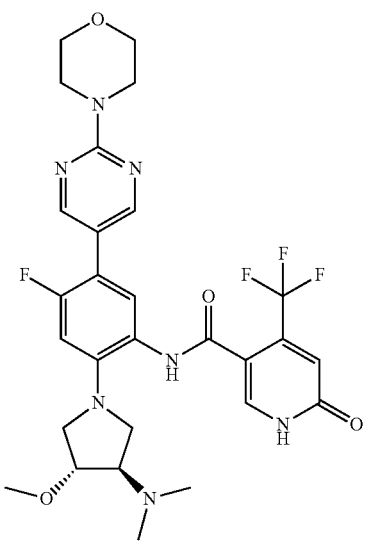 [SMILES: CO[C@@H]1CN(c2cc(F)c(-c3cnc(N4CCOCC4)nc3)cc2NC(=O)c2c[nH]c(=O)cc2C(F)(F)F)C[C@H]1N(C)C]

The title compound was prepared in a manner similar to the sequence described above for the preparation of Example 307. $^1$H NMR (500 MHz, DMSO-d6) δ=9.81 (s, 1H), 8.51 (s, 2H), 7.96 (s, 1H), 7.36 (br d, J=8.7 Hz, 1H), 6.80 (s, 1H), 6.75 (d, J=13.8 Hz, 1H), 3.87 (br d, J=5.4 Hz, 1H), 3.77-3.71 (m, 4H), 3.69-3.65 (m, 4H), 3.52-3.42 (m, 2H), 3.25 (s, 3H), 3.19 (br dd, J=5.9, 10.1 Hz, 1H), 2.75 (br d, J=4.8 Hz, 1H), 2.19 (s, 6H); LCMS [M+H]+: 606.5.

Example 334: N-[4-fluoro-5-(1-pyrimidin-2-yl-3,6-dihydro-2H-pyridin-5-yl)-2-[(3R,5S)-3,4,5-trimethylpiperazin-1-yl]phenyl]-6-oxo-4-(trifluoromethyl)-1H-pyridine-3-carboxamide

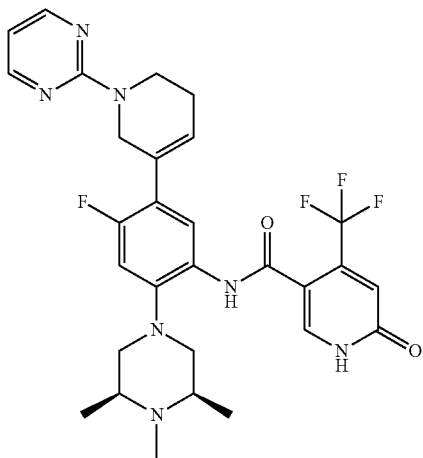 [SMILES: C[C@@H]1CN(c2cc(F)c(C3=CCCN(c4ncccn4)C3)cc2NC(=O)c2c[nH]c(=O)cc2C(F)(F)F)C[C@H](C)N1C]

To N-(4-Fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (35 mg, 0.069 mmol) and 2-bromopyrimidine 95% (12.06 mg, 0.076 mmol) in ethanol (3 ml) at RT was added N,N-diisopropylethylamine (0.024 ml, 0.138 mmol). The mixture was heated at 85-90° C. for 7 h. Workup and purification gave the title compound (38 mg, 88% yield). $^1$H NMR (500 MHz, METHANOL-d4) δ=8.40-8.31 (m, 2H), 8.00-7.92 (m, 1H), 7.86-7.74 (m, 1H), 7.04-6.96 (m, 1H), 6.94-6.89 (m, 1H), 6.66-6.59 (m, 1H), 6.21-6.12 (m, 1H), 4.59-4.51 (m, 2H), 4.05-3.98 (m, 2H), 3.09-3.01 (m, 2H), 2.65-2.52 (m, 4H), 2.45-2.37 (m, 5H), 1.20-1.16 (m, 6H); LCMS [M+H]+ 586.7

Example 335: N-[4-fluoro-5-(I-pyrimidin-2-yl-2,5-dihydropyrrol-3-yl)-2-[(3R,5S)-3,4,5-trimethylpiperazin-1-yl]phenyl]-6-oxo-4-(trifluoromethyl)-1H-pyridine-3-carboxamide

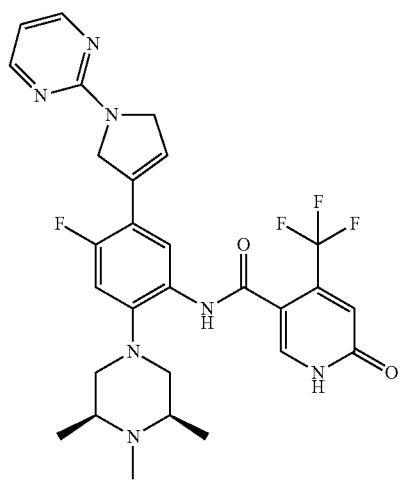 [SMILES: C[C@@H]1CN(c2cc(F)c(C3=CCN(c4ncccn4)C3)cc2NC(=O)c2c[nH]c(=O)cc2C(F)(F)F)C[C@H](C)N1C]

A procedure similar to Example 334 using N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (35 mg, 0.071 mmol) and 2-bromopyrimidine 95% (12.40 mg, 0.078 mmol) gave, after purification and workup, the title compound (5.5 mg, 12% yield). $^1$H NMR (500 MHz, METHANOL-d4) δ=8.31-8.25 (m, 2H), 7.90-7.83 (m, 1H), 7.82-7.75 (m, 1H), 6.96-6.90 (m, 1H), 6.85-6.81 (m, 1H), 6.61-6.54 (m, 1H), 6.43-6.36 (m, 1H), 4.67-4.60 (m, 2H), 4.50-4.41 (m, 3H), 3.00-2.94 (m, 2H), 2.55-2.44 (m, 4H), 2.30-2.27 (m, 3H), 1.09-1.05 (m, 6H); LCMS [M+H]+ 572.6.

Example 336: N-[4-fluoro-5-(8-pyrimidin-2-yl-8-azabicyclo[3.2.1]oct-2-en-3-yl)-2-[(3R,5S)-3,4,5-trimethylpiperazin-1-yl]phenyl]-6-oxo-4-(trifluoromethyl)-1H-pyridine-3-carboxamide Example 337: N-[4-fluoro-2-[(3R)-3,4-dimethylpiperazin-1-yl]-5-[2-[(3R)-3-methylmorpholin-4-yl]pyrimidin-5-yl]phenyl]-6-oxo-4-(trifluoromethyl)-1H-pyridine-3-carboxamide

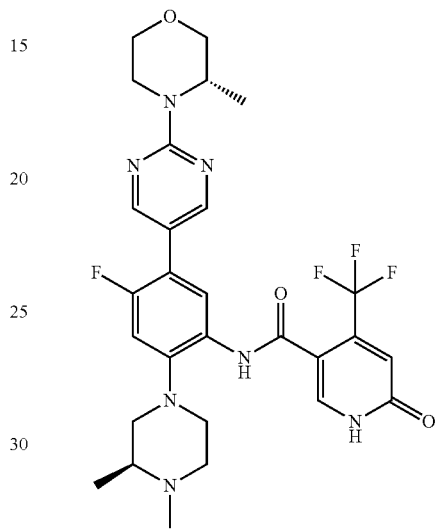

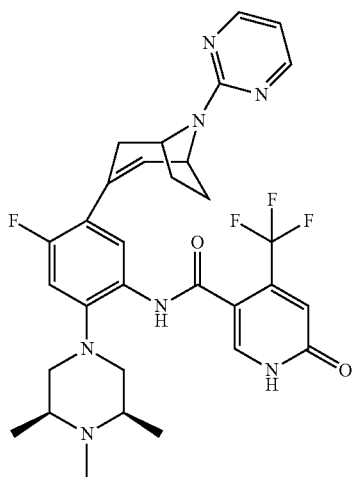 [SMILES: C[C@@H]1CN(c2cc(F)c(C3=CC4CCC(C3)N4c3ncccn3)cc2NC(=O)c2c[nH]c(=O)cc2C(F)(F)F)C[C@H](C)N1C]

A procedure similar to Example 334 using N-(5-(8-azabicyclo[3.2.1]oct-2-en-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (35 mg, 0.066 mmol) and 2-bromopyrimidine 95% (11.5 mg, 0.072 mmol) gave the title compound (31 mg, 74% yield). ¹H NMR (500 MHz, METHANOL-d4) δ=8.40-8.34 (m, 2H), 7.96-7.91 (m, 1H), 7.68-7.59 (m, 1H), 6.93-6.87 (m, 2H), 6.69-6.64 (m, 1H), 6.47-6.42 (m, 1H), 5.00-4.95 (m, 1H), 4.91-4.89 (m, 1H), 3.18-3.10 (m, 1H), 3.02-2.96 (m, 2H), 2.60-2.49 (m, 4H), 2.40-2.33 (m, 4H), 2.31-2.24 (m, 1H), 2.20-2.11 (m, 2H), 2.02-1.93 (m, 1H), 1.14 (d, J=6.0 Hz, 6H); LCMS [M+H]+ 612.7.

To a mixture of 2-chloropyrimidine-5-boronic acid (31.7 mg, 0.2 mmol) and (S)-3-methylmorpholine (0.042 mL, 0.21 mmol) in EtOH (2 mL) was added triethylamine (0.042 mL, 0.3 mmol). The resulting mixture was stirred at 70° C. for 80 min. Solvents were removed to give a light yellow oil. (S)-3-methylmorpholine (0.042 mL, 0.21 mmol) was added to the above oil, followed by triethylamine (0.042 mL, 0.3 mmol) and EtOH (2 mL). The resulting mixture was heated at 70° C. overnight for 18 h. Solvents were removed to give the crude (S)-(2-(3-methylmorpholino)pyrimidin-5-yl)boronic acid as a yellow oil. LCMS [M+H]+ 224.2. The title compound (off-white solid, 24.5 mg, 41%) was prepared by a procedure similar to Example 40 using the boronic acid and (S)—N-(5-bromo-2-(3,4-dimethylpiperazin-1-yl)-4-fluorophenyl)-6-oxo-4-(trifluoromethyl)-1,6-dihydropyridine-3-carboxamide (49.1 mg, 0.1 mmol). ¹H NMR (500 MHz, CHLOROFORM-d) δ=8.71 (br s, 1H), 8.56 (br s, 2H), 8.51-8.38 (m, 1H), 7.89 (s, 1H), 7.04 (br d, J=11.0 Hz, 1H), 7.00 (br d, J=9.4 Hz, 1H), 4.81-4.71 (m, 1H), 4.40 (br d, J=13.3 Hz, 1H), 4.01 (br d, J=11.0 Hz, 1H), 3.84-3.77 (m, 1H), 3.77-3.70 (m, 1H), 3.58 (br t, J=10.8 Hz, 1H), 3.38-3.26 (m, 1H), 3.04-2.86 (m, 3H), 2.83 (br d, J=9.5 Hz, 1H), 2.61 (br s, 1H), 2.50-2.13 (m, 5H), 1.38-1.30 (m, 3H), 1.16-1.06 (m, 3H); LCMS [M+H]+ 590.6.

Example 338: N-[4-fluoro-5-[2-[(3R)-3-methylmorpholin-4-yl]pyrimidin-5-yl]-2-[(3S,5R)-3,4,5-trimethylpiperazin-1-yl]phenyl]-6-oxo-4-(trifluoromethyl)-1H-pyridine-3-carboxamide

Example 339: N-[4-fluoro-5-(2-morpholin-4-yl-1,4,5,6-tetrahydropyrimidin-5-yl)-2-[(3R,5S)-3,4,5-trimethylpiperazin-1-yl]phenyl]-6-oxo-4-(trifluoromethyl)-1H-pyridine-3-carboxamide

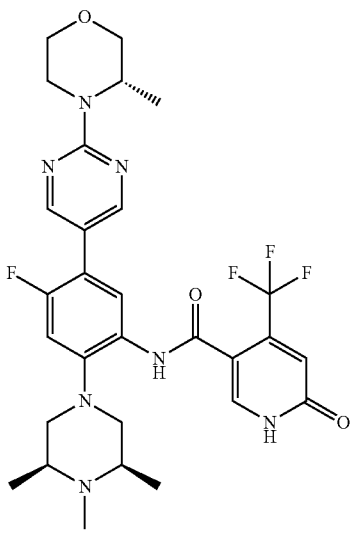 [SMILES: C[C@@H]1CN(c2cc(F)c(-c3cnc(N4CCOC[C@@H]4C)nc3)cc2NC(=O)c2c[nH]c(=O)cc2C(F)(F)F)C[C@H](C)N1C]

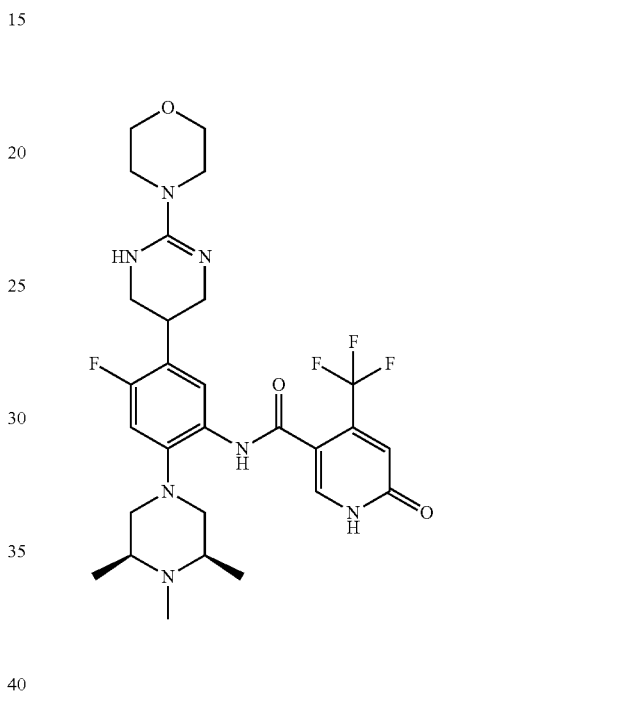

The title compound (light beige solid, 14.4 mg, 23%) was prepared in a manner similar to Example 31 using crude (S)-(2-(3-methylmorpholino)pyrimidin-5-yl)boronic acid (0.2 mmol) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, CHLOROFORM-d) δ=8.71 (br s, 1H), 8.57 (s, 2H), 8.47 (br d, J=8.1 Hz, 1H), 7.86 (br s, 1H), 7.06-6.98 (m, 2H), 4.81-4.75 (m, 1H), 4.42 (br d, J=13.4 Hz, 1H), 4.03 (dd, J=3.4, 11.2 Hz, 1H), 3.82 (d, J=11.4 Hz, 1H), 3.75 (dd, J=2.7, 11.4 Hz, 1H), 3.60 (dt, J=2.9, 11.8 Hz, 1H), 3.34 (dt, J=3.8, 13.0 Hz, 1H), 2.83 (br d, J=10.4 Hz, 2H), 2.75-2.61 (m, 2H), 2.41-2.27 (m, 5H), 1.36 (d, J=6.7 Hz, 3H), 1.16 (br d, J=5.6 Hz, 6H); LCMS [M+H]$^+$ 604.5.

A solution of N-(4-fluoro-5-(2-morpholinopyrimidin-5-yl)-2-((3R,5S)-3,4,5-trimethylpiperazin-1-yl)phenyl)-6-oxo-4-(trifluoromethyl)-1,6-dihydropyridine-3-carboxamide (75 mg, 0.127 mmol) and sodium borohydride (289 mg, 7.63 mmol) in MeOH (5 ml) and water (0.5 ml) was agitated at 70° C. for 2.5 days. It was then quenched with sat. aq. NH$_4$Cl followed by MeOH. A standard workup and purification provided N-(4-fluoro-5-(2-morpholino-1,4,5,6-tetrahydropyrimidin-5-yl)-2-((3R,5S)-3,4,5-trimethylpiperazin-1-yl)phenyl)-6-oxo-4-(trifluoromethyl)-1,6-dihydropyridine-3-carboxamide-HCl, as a white powder. $^1$H NMR (500 MHz, DMSO-d$_6$) δ 12.92-12.48 (m, 1H), 9.68-9.40 (m, 1H), 8.74-8.51 (m, 2H), 8.15 (s, 1H), 7.91 (br s, 1H), 7.74-7.48 (m, 1H), 7.02 (br d, J=11.9 Hz, 1H), 6.82 (s, 1H), 3.74-3.61 (m, 5H), 3.60-3.51 (m, 3H), 3.44-3.39 (m, 8H), 3.10-2.91 (m, 3H), 2.35-2.25 (m, 2H), 1.14-0.98 (m, 6H); LCMS (MH$^+$)=594.7.

Example 340: N-[4-fluoro-2-[(3S)-3,4-dimethylpiperazin-1-yl]-5-[2-[(2R)-2-methylmorpholin-4-yl]pyrimidin-5-yl]phenyl]-6-oxo-4-(trifluoromethyl)-1H-pyridine-3-carboxamide

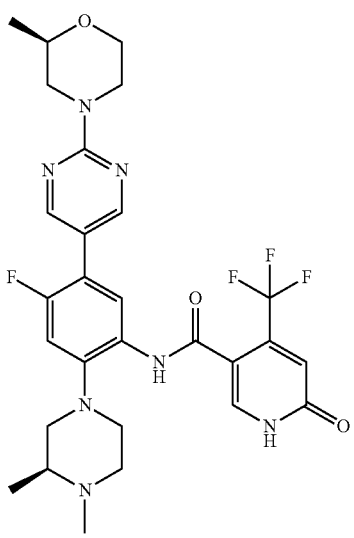 [SMILES: C[C@@H]1CN(c2ncc(-c3cc(NC(=O)c4c[nH]c(=O)cc4C(F)(F)F)c(N4CCN(C)[C@@H](C)C4)cc3F)cn2)CCO1]

To a mixture of 2-chloropyrimidine-5-boronic acid (32 mg, 0.2 mmol) and (R)-2-methyl-morpholine, hydrochloride (29 mg, 0.21 mmol) in EtOH (2 mL) was added triethylamine (0.070 mL, 0.5 mmol). The resulting mixture was stirred at 70° C. for 1.5 h. Solvents were removed to give the crude (R)-(2-(2-methylmorpholino)pyrimidin-5-yl)boronic acid as a pale yellow solid. LCMS [M+H]$^+$ 224.2. The title compound (pale beige solid, 34.2 mg, 55%) was prepared through a procedure similar to the last step of Example 273 using this boronic acid (0.2 mmol) and (S)—N-(5-bromo-2-(3,4-dimethylpiperazin-1-yl)-4-fluorophenyl)-6-oxo-4-(trifluoromethyl)-1,6-dihydropyridine-3-carboxamide (49.1 mg, 0.1 mmol). $^1$H NMR (500 MHz, CHLOROFORM-d) δ=8.70 (br s, 1H), 8.55 (s, 2H), 8.45 (br d, J=5.6 Hz, 1H), 7.89 (s, 1H), 7.04 (d, J=11.2 Hz, 1H), 7.01-6.99 (m, 1H), 4.64-4.53 (m, 2H), 4.01 (br d, J=11.2 Hz, 1H), 3.67-3.58 (m, 2H), 3.15-3.05 (m, 1H), 3.01-2.86 (m, 3H), 2.85-2.70 (m, 2H), 2.60 (br t, J=10.3 Hz, 1H), 2.42-2.29 (m, 4H), 2.29-2.15 (m, 1H), 1.30-1.25 (m, 3H), 1.10 (br d, J=6.0 Hz, 3H); LCMS [M+H]$^+$ 590.6.

Example 341: N-[4-fluoro-5-[6-[(2R,6S)-2,6-dimethylmorpholin-4-yl]pyridin-3-yl]-2-[(3R)-3,4-dimethylpiperazin-1-yl]phenyl]-6-oxo-4-(trifluoromethyl)-1H-pyridine-3-carboxamide

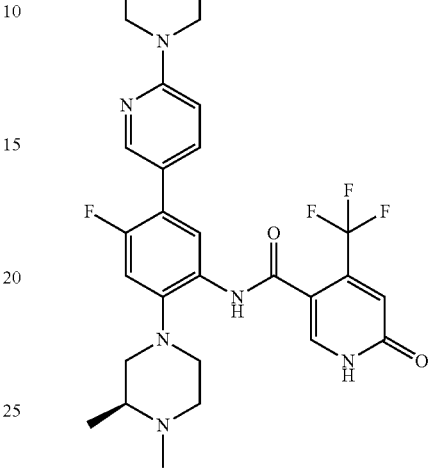

Step 1: (2S,6R)-2,6-dimethyl-4-(5-(4,4,5,5-tetramethyl-1,3,2-dioxaborolan-2-yl)pyridin-2-yl)morpholine

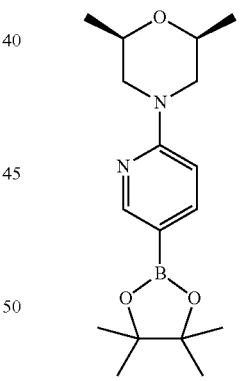

To a 20 mL microwave vial charged with 2-chloro-5-(4,4,5,5-tetramethyl-1,3,2-dioxaborolan-2-yl)pyridine (0.968 g, 4 mmol), cis-2,6-dimethylmorpholine (0.54 mL, 4.4 mmol) and Hunig base (1.39 mL, 8 mmol) was added NMP (2 mL). The resulting solution was heated at 140° C. for 2 h. After removing the amine base, the mixture was loaded onto Biotage samplet and purified by flash chromatography (gradient: EtOAc/hex 0-100%) to give the title compound as a crystalline beige solid (485 mg, 38%). LCMS [M+H]$^+$ 237.2.

Step 2: N-(4-fluoro-5-(2-((S)-3-methylmorpholino)pyrimidin-5-yl)-2-((3S,5R)-3,4,5-trimethylpiperazin-1-yl)phenyl)-6-oxo-4-(trifluoromethyl)-1,6-dihydropyridine-3-carboxamide

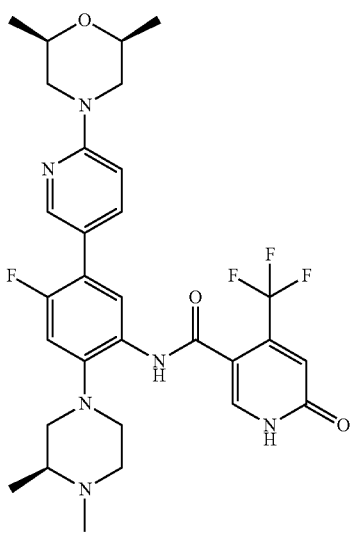

The title compound (light brown solid, 27.0 mg, 44%) was prepared by a procedure similar to that of the last step of Example 39 using (S)—N-(5-bromo-2-(3,4-dimethylpiperazin-1-yl)-4-fluorophenyl)-6-oxo-4-(trifluoromethyl)-1,6-dihydropyridine-3-carboxamide (49 mg, 0.1 mmol) and (2S,6R)-2,6-dimethyl-4-(5-(4,4,5,5-tetramethyl-1,3,2-dioxaborolan-2-yl)pyridin-2-yl)morpholine (63 mg, 0.2 mmol). $^1$H NMR (500 MHz, CHLOROFORM-d) δ=8.72 (br s, 1H), 8.51-8.42 (m, 2H), 7.93-7.84 (m, 1H), 7.74 (br d, J=8.3 Hz, 1H), 7.08-6.97 (m, 2H), 6.71 (br d, J=8.7 Hz, 1H), 4.13 (br d, J=12.5 Hz, 2H), 3.85-3.69 (m, 2H), 3.05-2.88 (m, 3H), 2.84 (br d, J=10.6 Hz, 1H), 2.68-2.54 (m, 3H), 2.50-2.31 (m, 4H), 2.30-2.14 (m, 1H), 1.31 (dd, J=1.9, 6.1 Hz, 6H), 1.11 (br d, J=5.7 Hz, 3H); LCMS [M+H]$^+$ 603.6.

Example 342: 4-(difluoromethyl)-N-[4-fluoro-5-(2-morpholin-4-ylpyrimidin-5-yl)-2-[(3R,5S)-3,4,5-trimethylpiperazin-1-yl]phenyl]-1-methyl-6-oxopyridine-3-carboxamide

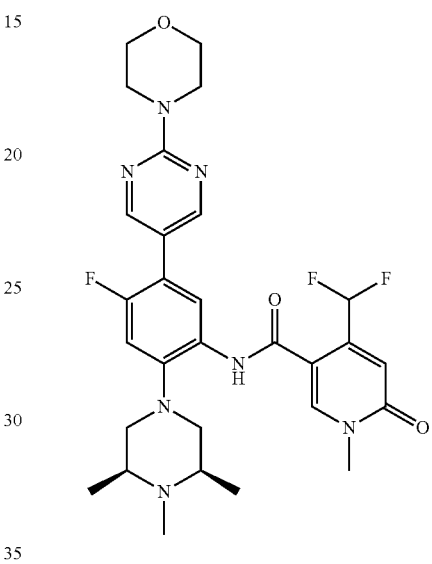

4-(Difluoromethyl)-1-methyl-6-oxo-1,6-dihydropyridine-3-carboxylic acid (0.023 g, 0.11 mmol) was activated with HATU (0.043 g, 0.11 mmol) and N,N-diisopropylethylamine (0.02 mL, 0.11 mmol) in DMF (0.5 mL) at room temperature. The solution of activated acid was added to a solution of 4-fluoro-5-(2-morpholinopyrimidin-5-yl)-2-(cis-3,4,5-trimethylpiperazin-1-yl)aniline (0.030 g, 0.075 mmol) DMF (0.5 mL) and the reaction was heated to 55° C. for 18 h. After cooling to room temperature the reaction mixture was concentrated onto celite and purified by flash chromatography [0.5-10% MeOH/DCM+0.5% NH$_4$OH]. The product containing fractions were combined and re-concentrated onto celite. Reverse phase chromatography [5-95% MeCN/H$_2$O] afforded 4-(difluoromethyl)-N-(4-fluoro-5-(2-morpholinopyrimidin-5-yl)-2-(cis-3,4,5-trimethylpiperazin-1-yl)phenyl)-1-methyl-6-oxo-1,6-dihydropyridine-3-carboxamide (0.012 g, 27%). $^1$H NMR (500 MHz, DMSO-d6) δ=9.50 (s, 1H), 8.52 (s, 2H), 8.34 (s, 1H), 7.67 (d, J=8.6 Hz, 1H), 7.50-7.18 (m, 1H), 7.05 (d, J=12.3 Hz, 1H), 6.64 (s, 1H), 3.76-3.74 (m, 4H), 3.69-3.66 (m, 4H), 3.52 (s, 3H), 3.03 (br d, J=10.8 Hz, 3H), 2.37-2.30 (m, 3H), 2.18 (s, 3H), 1.00 (d, J=6.1 Hz, 6H); LCMS [M+H]+: 586.6.

Example 343: N-[4-fluoro-5-(2-morpholin-4-ylpyrimidin-5-yl)-2-[(R,4R)-5-methyl-2,5-diazabicyclo[2.2.1]heptan-2-yl]phenyl]-6-oxo-4-(trifluoromethyl)-1H-pyridine-3-carboxamide Example 344: N-[4-fluoro-5-(2-morpholin-4-ylpyrimidin-5-yl)-2-[(3R,4R)-3-[ethyl(methyl)amino]-4-fluoropyrrolidin-1-yl]phenyl]-6-oxo-4-(trifluoromethyl)-1H-pyridine-3-carboxamide

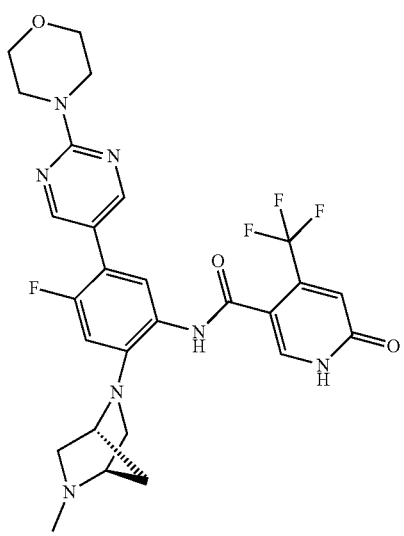 [SMILES: CN1C[C@H]2C[C@@H]1CN2c1cc(F)c(-c2cnc(N3CCOCC3)nc2)cc1NC(=O)c1c[nH]c(=O)cc1C(F)(F)F]

The title compound was prepared similar to the sequence described above for the preparation of Example 234 using (1R,4R)-2-methyl-2,5-diazabicyclo[2.2.1]heptane dihydrobromide in place of (R)—N-ethyl-N-methylpyrrolidin-3-amine in Step 1. $^1$H NMR (500 MHz, DMSO-d6) δ=9.71 (s, 1H), 8.50 (s, 2H), 7.96 (s, 1H), 7.31 (d, J=8.8 Hz, 1H), 6.79 (s, 1H), 6.68 (d, J=13.9 Hz, 1H), 4.23 (s, 1H), 3.75-3.71 (m, 4H), 3.70-3.65 (m, 4H), 3.44 (br d, J=7.9 Hz, 1H), 3.23 (br d, J=9.3 Hz, 1H), 2.79-2.73 (m, 1H), 2.72-2.66 (m, 1H), 2.25 (s, 3H), 1.82 (br d, J=9.0 Hz, 1H), 1.65 (br d, J=9.0 Hz, 1H); LCMS [M+H]+: 574.4.

The title compound was prepared similar to the procedure described above for the preparation of Example 307 using N-ethylmethylamine in place of dimethylamine in Step 1. $^1$H NMR (500 MHz, DMSO-d6) δ=9.78 (br d, J=2.8 Hz, 1H), 8.53 (s, 2H), 8.01 (br s, 1H), 7.41 (d, J=8.8 Hz, 1H), 6.82 (d, J=13.6 Hz, 1H), 6.77-6.68 (m, 1H), 5.32-5.13 (m, 1H), 3.77-3.73 (m, 4H), 3.70-3.67 (m, 4H), 3.63-3.56 (m, 2H), 3.55-3.52 (m, 1H), 3.30 (s, 3H), 3.19-3.13 (m, 2H), 2.56-2.54 (m, 2H), 2.20 (s, 3H), 0.98 (t, J=7.1 Hz, 3H); LCMS [M+H]+: 608.4.

Example 345: N-[4-fluoro-5-(2-morpholin-4-ylpyrimidin-5-yl)-2-[(3R)-3-[ethyl(methyl)amino]pyrrolidin-1-yl]phenyl]-6-oxo-4-(trifluoromethyl)-1H-pyridine-3-carboxamide

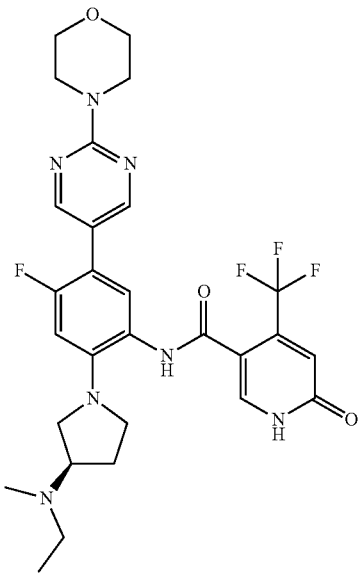 [SMILES: CCN(C)[C@@H]1CCN(c2cc(F)c(-c3cnc(N4CCOCC4)nc3)cc2NC(=O)c2c[nH]c(=O)cc2C(F)(F)F)C1]

Step 1: tert-butyl (R)-3-(ethyl(methyl)amino)pyrrolidine-1-carboxylate

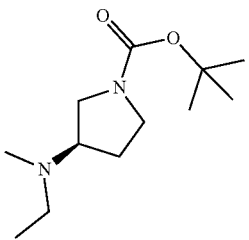 [SMILES: CCN(C)[C@@H]1CCN(C(=O)OC(C)(C)C)C1]

A mixture of (S)-1-Boc-3-methanesulfonyloxy-pyrrolidine (0.50 g, 1.9 mmol), N-ethylmethylamine (0.40 mL, 4.7 mmol) and N,N-diisopropylethylamine (0.82 mL, 4.7 mmol) was heated to 70° C. in a sealed tube for 40 h. After cooling to room temperature the reaction mixture was concentrated onto celite and purified by flash chromatography [0-5% MeOH/DCM+0.5% NH$_4$OH] to afford tert-butyl (R)-3-(ethyl(methyl)amino)pyrrolidine-1-carboxylate (0.20 g, 47%). $^1$H NMR (500 MHz, DMSO-d6) δ=3.51-3.43 (m, 1H), 3.39-3.36 (m, 1H), 3.22-3.09 (m, 1H), 2.97-2.79 (m, 2H), 2.47-2.33 (m, 2H), 2.12 (s, 3H), 1.98 (br dd, J=6.4, 10.8 Hz, 1H), 1.72-1.56 (m, 1H), 1.39 (s, 9H), 0.96 (t, J=7.1 Hz, 3H).

Step 2: (R)—N-ethyl-N-methylpyrrolidin-3-amine

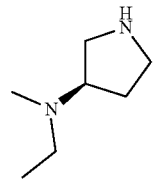

A solution of tert-butyl (R)-3-(ethyl(methyl)amino)pyrrolidine-1-carboxylate (0.20 g, 0.89 mmol) in DCM (4 mL) was treated with TFA (1.4 mL, 18 mmol) at room temperature. After stirring for 2 h the volatiles were removed under a stream of air and the product was isolated by a catch and release protocol using a SCX2 silica cartridge to afford (R)—N-ethyl-N-methylpyrrolidin-3-amine (0.12 g, 100%). $^1$H NMR (500 MHz, DMSO-d6) δ=2.91 (dd, J=7.1, 10.4 Hz, 1H), 2.85-2.66 (m, 3H), 2.46 (dd, J=7.6, 10.4 Hz, 1H), 2.43-2.29 (m, 2H), 2.09 (s, 3H), 1.77 (dtd, J=5.0, 7.4, 12.2 Hz, 1H), 1.45 (qd, J=8.0, 12.1 Hz, 1H), 0.96 (t, J=7.2 Hz, 3H).

Step 3: (R)-1-(4-bromo-5-fluoro-2-nitrophenyl)-N-ethyl-N-methylpyrrolidin-3-amine

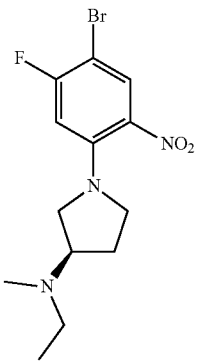 [SMILES: CCN(C)[C@@H]1CCN(c2cc(F)c(Br)cc2[N+](=O)[O-])C1]

A solution of 1-bromo-2,4-difluoro-5-nitrobenzene (0.22 g, 0.95 mmol) in PhMe (1 mL) was slowly added to a rapidly stirring mixture of (R)—N-ethyl-N-methylpyrrolidin-3-amine (0.12 g, 0.95 mmol) and K$_2$CO$_3$ (0.065 g, 0.47 mmol) in PhMe (2 mL) at 45° C. After 4 h the heat was turned off and the reaction was allowed to stir at room temperature for 18 h. The reaction mixture was concentrated onto celite and purification by flash chromatography [0.5-10% MeOH/DCM+0.5% NH$_4$OH] afforded (R)-1-(4-bromo-5-fluoro-2-nitrophenyl)-N-ethyl-N-methylpyrrolidin-3-amine (0.22 g, 66%). LCMS [M+H]$^+$: 346.3.

Step 4: (R)—N-ethyl-1-(5-fluoro-4-(2-morpholinopyrimidin-5-yl)-2-nitrophenyl)-N-methylpyrrolidin-3-amine

Step 5: (R)-1-(2-amino-5-fluoro-4-(2-morpholinopyrimidin-5-yl)phenyl)-N-ethyl-N-methylpyrrolidin-3-amine

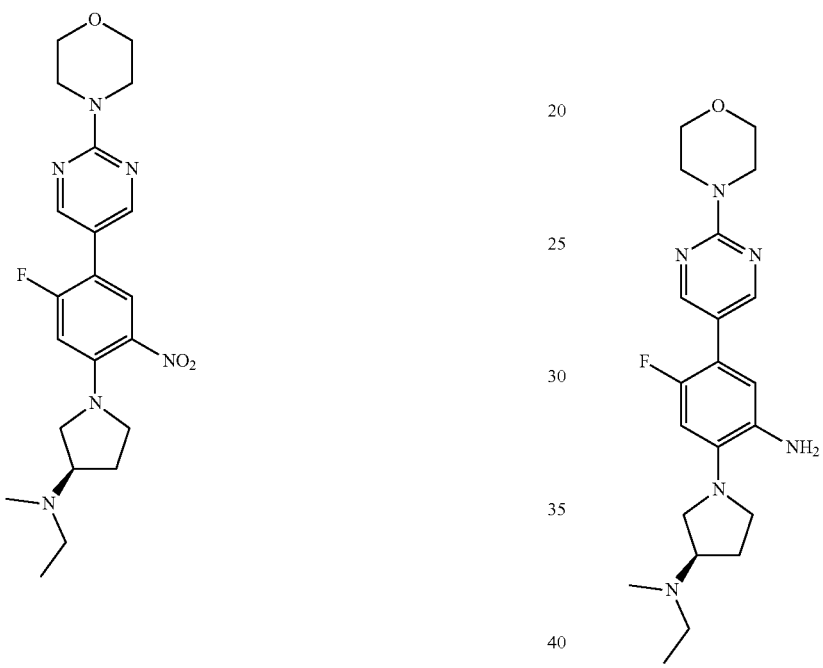

A reaction vial was charged with a mixture of (R)-1-(4-bromo-5-fluoro-2-nitrophenyl)-N-ethyl-N-methylpyrrolidin-3-amine (0.11 g, 0.32 mmol), 2-(4-morpholino)pyrimidine-5-boronic acid pinacol ester (0.10 g, 0.35 mmol), XPhos Pd G2 (5.0 mg, 6.4 μmol) and XPhos (3.0 mg, 6.4 μmol). The vial was sealed with a septum, evacuated and backfilled with nitrogen. 1,4-Dioxane (3 mL) and 2 M aqueous sodium carbonate (0.6 mL) were added via syringe and the vial was evacuated and backfilled an additional time. The reaction was heated to 90° C. in an aluminum block overnight. After cooling to room temperature the reaction mixture was concentrated onto celite and purified by flash chromatography [0.5-10% MeOH/DCM+0.5% NH$_4$OH] to afford (R)—N-ethyl-1-(5-fluoro-4-(2-morpholinopyrimidin-5-yl)-2-nitrophenyl)-N-methylpyrrolidin-3-amine (0.11 g, 78%). LCMS [M+H]+. 431.4.

A mixture of (R)—N-ethyl-1-(5-fluoro-4-(2-morpholinopyrimidin-5-yl)-2-nitrophenyl)-N-methylpyrrolidin-3-amine (0.10 g, 0.25 mmol), SnCl$_2$ (0.24 g, 1.2 mmol) and EtOH (5 mL) was heated to 75° C. for 1 h. The heat was turned off and the reaction was allowed to stir at room temperature for 18 h. The reaction mixture was concentrated onto celite and purification by flash chromatography [0.5-10% MeOH/DCM+1% NH$_4$OH] afforded (R)-1-(2-amino-5-fluoro-4-(2-morpholinopyrimidin-5-yl)phenyl)-N-ethyl-N-methylpyrrolidin-3-amine (0.084 g, 84%). LCMS [M+H]+: 401.3.

497

Step 6: (R)—N-(2-(3-(ethyl(methyl)amino)pyrrolidin-1-yl)-4-fluoro-5-(2-morpholinopyrimidin-5-yl)phenyl)-6-oxo-4-(trifluoromethyl)-1,6-dihydropyridine-3-carboxamide

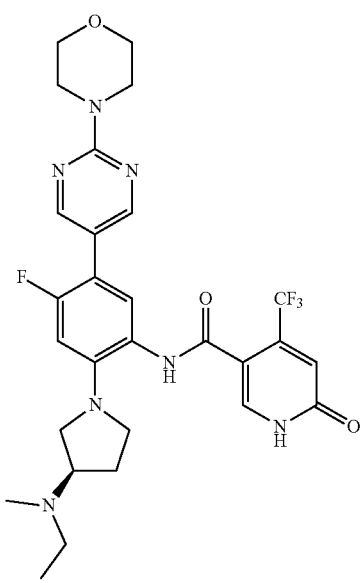 [SMILES: CCN(C)[C@@H]1CCN(c2cc(F)c(-c3cnc(N4CCOCC4)nc3)cc2NC(=O)c2c[nH]c(=O)cc2C(F)(F)F)C1]

4-(Trifluoromethyl)-6-(2-(trimethylsilyl)ethoxy)nicotinic acid (0.046 g, 0.15 mmol) was activated with HATU (0.057 g, 0.15 mmol) and N,N-diisopropylethylamine (0.03 mL, 0.15 mmol) in DMF (0.5 mL) at room temperature. The solution of activated acid was added to a solution of (R)-1-(2-amino-5-fluoro-4-(2-morpholinopyrimidin-5-yl)phenyl)-N-ethyl-N-methylpyrrolidin-3-amine (0.040 g, 0.10 mmol) in DMF (1 mL) and the reaction was heated to 55° C. for 18 h. After cooling to room temperature the reaction mixture was concentrated onto celite and purified by flash chromatography [0.5-10% MeOH/DCM+0.5% NH$_4$OH]. The silyl protected amide was dissolved in DCM (2 mL) and treated with TFA (1 mL) at room temperature. After stirring for 2 h the volatiles were removed under a stream of air and the title compound was isolated by a catch and release protocol using a SCX2 silica cartridge to afford (R)—N-(2-(3-(ethyl(methyl)amino)pyrrolidin-1-yl)-4-fluoro-5-(2-morpholinopyrimidin-5-yl)phenyl)-6-oxo-4-(trifluoromethyl)-1,6-dihydropyridine-3-carboxamide (0.042 g, 71%). $^1$H NMR (500 MHz, DMSO-d6) δ=9.80 (s, 1H), 8.51 (s, 2H), 7.96 (s, 1H), 7.32 (br d, J=8.6 Hz, 1H), 6.80 (s, 1H), 6.67 (d, J=13.9 Hz, 1H), 3.76-3.72 (m, 4H), 3.70-3.66 (m, 4H), 3.38 (br d, J=8.9 Hz, 4H), 3.27-3.22 (m, 1H), 2.90 (br t, J=7.9 Hz, 1H), 2.42 (td, J=6.4, 13.0 Hz, 2H), 2.14 (s, 3H), 2.12-2.06 (m, 1H), 1.75-1.65 (m, 1H), 0.99-0.94 (m, 6H); LCMS [M+H]+: 590.5.

498

Example 346: N-[4-fluoro-5-(2-morpholin-4-ylpyrimidin-5-yl)-2-[(3R,4R)-3-[ethyl(methyl)amino]-4-fluoropyrrolidin-1-yl]phenyl]-1-methyl-6-oxo-4-(trifluoromethyl)pyridine-3-carboxamide

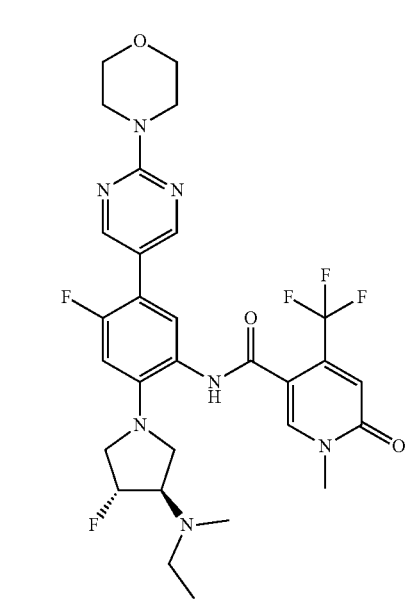 [SMILES: CCN(C)[C@@H]1CN(c2cc(F)c(-c3cnc(N4CCOCC4)nc3)cc2NC(=O)c2cn(C)c(=O)cc2C(F)(F)F)C[C@H]1F]

The title compound was prepared similar to the procedure described above for the preparation of Example 344 using 1-methyl-6-oxo-4-(trifluoromethyl)-1,6-dihydropyridine-3-carboxylic acid in place of 4-(trifluoromethyl)-6-(2-(trimethylsilyl)ethoxy)nicotinic acid in Step 7. $^1$H NMR (500 MHz, DMSO-d6) δ=9.84 (s, 1H), 8.52 (s, 2H), 8.36 (s, 1H), 7.39 (d, J=8.6 Hz, 1H), 6.89-6.82 (m, 2H), 5.32-5.12 (m, 1H), 3.77-3.74 (m, 4H), 3.69-3.67 (m, 4H), 3.64-3.59 (m, 2H), 3.58-3.51 (m, 6H), 3.19-3.11 (m, 2H), 2.20 (s, 3H), 0.98 (t, J=7.0 Hz, 3H); LCMS [M+H]+: 622.6.

Example 347: N-[4-fluoro-2-[(3R)-3,4-dimethylpiperazin-1-yl]-5-[2-[(2R)-2-propan-2-ylmorpholin-4-yl]pyrimidin-5-yl]phenyl]-6-oxo-4-(trifluoromethyl)-1H-pyridine-3-carboxamide

Example 348: N-[4-fluoro-5-[2-[(2R)-2-propan-2-ylmorpholin-4-yl]pyrimidin-5-yl]-2-[(3S,5R)-3,4,5-trimethylpiperazin-1-yl]phenyl]-6-oxo-4-(trifluoromethyl)-1H-pyridine-3-carboxamide

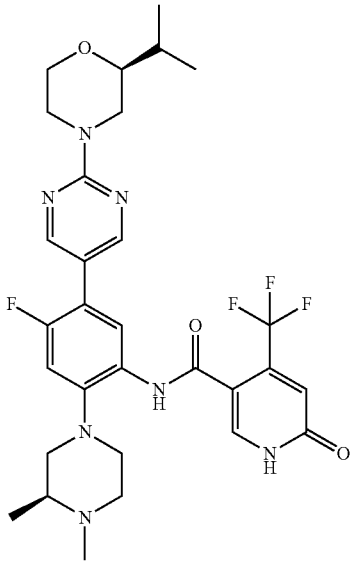 [SMILES: CC(C)[C@H]1CN(c2ncc(-c3cc(NC(=O)c4c[nH]c(=O)cc4C(F)(F)F)c(N4CCN(C)[C@@H](C)C4)cc3F)cn2)CCO1]

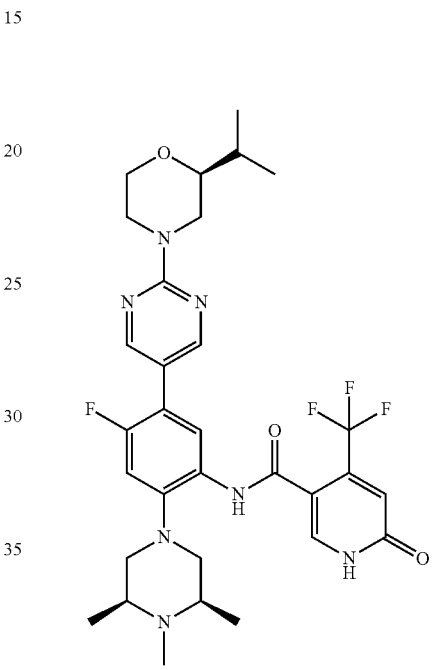

To a mixture of 2-chloropyrimidine-5-boronic acid (32 mg, 0.2 mmol) and (S)-2-isopropylmorpholine (27 mg, 0.21 mmol) in EtOH (2 mL) was added triethylamine (0.070 mL, 0.5 mmol). The resulting mixture was stirred at 75° C. for 1.5 h. Solvents were removed to give the crude (S)-(2-(2-isopropylmorpholino)pyrimidin-5-yl)boronic acid as a pale yellow solid. LCMS [M+H]$^+$ 252.3. The title compound (pale beige solid, 34.2 mg, 55%) was prepared by a method similar to the last step of Example 31 using this boronic acid (0.2 mmol) and (S)—N-(5-bromo-2-(3,4-dimethylpiperazin-1-yl)-4-fluorophenyl)-6-oxo-4-(trifluoromethyl)-1,6-dihydropyridine-3-carboxamide (49.1 mg, 0.1 mmol). $^1$H NMR (500 MHz, CHLOROFORM-d) δ=8.72 (br s, 1H), 8.57 (s, 2H), 8.47 (br d, J=8.1 Hz, 1H), 7.88 (br s, 1H), 7.06 (d, J=11.1 Hz, 1H), 7.02 (br s, 1H), 4.69 (br d, J=13.1 Hz, 1H), 4.57 (br d, J=13.3 Hz, 1H), 4.05 (dd, J=2.6, 11.4 Hz, 1H), 3.64 (dt, J=2.6, 11.6 Hz, 1H), 3.22-3.07 (m, 2H), 3.03-2.80 (m, 5H), 2.61 (br t, J=10.4 Hz, 1H), 2.44-2.30 (m, 4H), 2.23 (br s, 1H), 1.83 (qd, J=6.8, 13.5 Hz, 1H), 1.12 (br d, J=6.0 Hz, 3H), 1.06 (d, J=6.7 Hz, 3H), 1.04 (d, J=6.8 Hz, 3H); LCMS [M+H]$^+$ 618.6.

The title compound (beige solid, 30.8 mg, 49%) was prepared by a procedure similar to the last step of Example 31 using crude (S)-(2-(2-isopropylmorpholino)pyrimidin-5-yl)boronic acid (0.2 mmol) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, CHLOROFORM-d) δ=8.69 (br s, 1H), 8.56 (s, 2H), 8.45 (br d, J=7.9 Hz, 1H), 7.86 (s, 1H), 7.06-6.97 (m, 2H), 4.67 (br d, J=13.0 Hz, 1H), 4.56 (br d, J=13.2 Hz, 1H), 4.03 (dd, J=2.5, 11.4 Hz, 1H), 3.62 (dt, J=2.6, 11.6 Hz, 1H), 3.22-3.04 (m, 2H), 2.89-2.76 (m, 3H), 2.73-2.58 (m, 2H), 2.41-2.25 (m, 5H), 1.81 (qd, J=6.8, 13.5 Hz, 1H), 1.14 (br d, J=5.7 Hz, 6H), 1.04 (d, J=6.8 Hz, 3H), 1.02 (d, J=6.8 Hz, 3H); LCMS [M+H]$^+$ 632.6.

Example 349: N-[5-[2-(2,2-dimethylmorpholin-4-yl)pyrimidin-5-yl]-4-fluoro-2-[(3R)-3,4-dimethylpiperazin-1-yl]phenyl]-6-oxo-4-(trifluoromethyl)-1H-pyridine-3-carboxamide

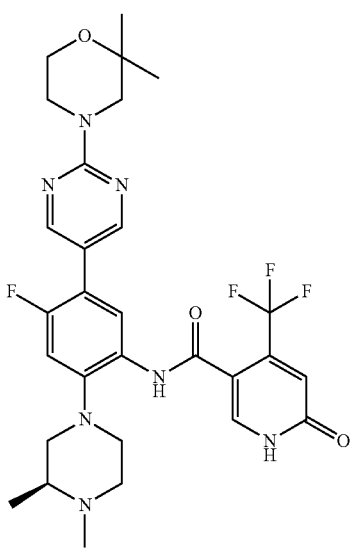

To a mixture of 2-chloropyrimidine-5-boronic acid (32 mg, 0.2 mmol) and 2,2-dimethylmorpholine (24 mg, 0.21 mmol) in EtOH (2 mL) was added triethylamine (0.070 mL, 0.5 mmol). The resulting mixture was stirred at 75° C. for 1.5 h. Solvents were removed to give the crude (2-(2,2-dimethylmorpholino)pyrimidin-5-yl)boronic acid as a pale yellow solid. LCMS [M+H]$^+$ 238.2. The title compound (beige solid, 36.6 mg, 60%) was prepared by a procedure similar to the last step of Example 31 using this boronic acid (0.2 mmol) and (S)—N-(5-bromo-2-(3,4-dimethylpiperazin-1-yl)-4-fluorophenyl)-6-oxo-4-(trifluoromethyl)-1,6-dihydropyridine-3-carboxamide (49.1 mg, 0.1 mmol). $^1$H NMR (500 MHz, CHLOROFORM-d) δ=8.70 (s, 1H), 8.54 (s, 2H), 8.45 (br d, J=8.1 Hz, 1H), 7.88 (s, 1H), 7.04 (d, J=11.1 Hz, 1H), 7.00 (br s, 1H), 3.89-3.80 (m, 4H), 3.71 (s, 2H), 3.02-2.87 (m, 3H), 2.82 (br d, J=10.9 Hz, 1H), 2.86-2.77 (m, 1H), 2.60 (br t, J=10.4 Hz, 1H), 2.42-2.30 (m, 4H), 2.23 (br s, 1H), 1.28 (s, 6H), 1.10 (br d, J=6.1 Hz, 3H); LCMS [M+H]$^+$ 604.5.

Example 350: N-[5-[2-(2,2-dimethylmorpholin-4-yl)pyrimidin-5-yl]-4-fluoro-2-[(3R,5S)-3,4,5-trimethylpiperazin-1-yl]phenyl]-6-oxo-4-(trifluoromethyl)-1H-pyridine-3-carboxamide

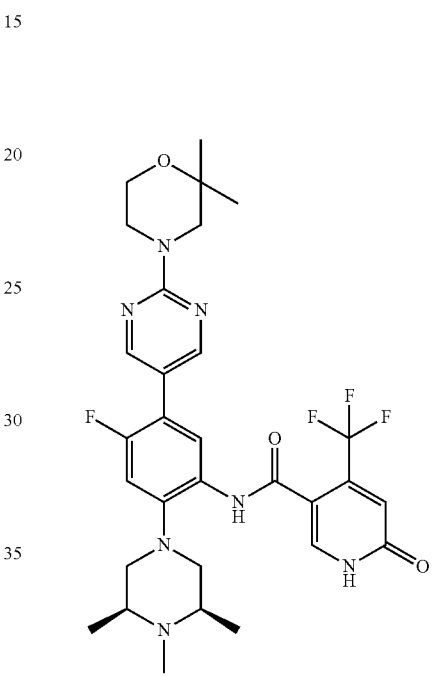

The title compound (beige solid, 36.6 mg, 58%) was prepared by a procedure similar to that of described in the last step of Example 31 using crude (2-(2,2-dimethylmorpholino)pyrimidin-5-yl)boronic acid (0.2 mmol) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, CHLOROFORM-d) δ=8.71 (br s, 1H), 8.55 (s, 2H), 8.46 (br d, J=8.1 Hz, 1H), 7.90-7.85 (m, 1H), 7.07-7.00 (m, 2H), 3.90-3.82 (m, 4H), 3.72 (s, 2H), 2.83 (br d, J=10.9 Hz, 2H), 2.67 (br t, J=10.8 Hz, 2H), 2.41-2.27 (m, 5H), 1.30 (s, 6H), 1.15 (br d, J=6.1 Hz, 6H); LCMS [M+H]$^+$ 618.6.

Example 351: N-[4-fluoro-5-(2-morpholin-4-ylpyrimidin-5-yl)-2-[(3R,5S)-3,4,5-trimethylpiperazin-1-yl]phenyl]-7-(trifluoromethyl)-[1,2,4]triazolo[4,3-a]pyridine-6-carboxamide

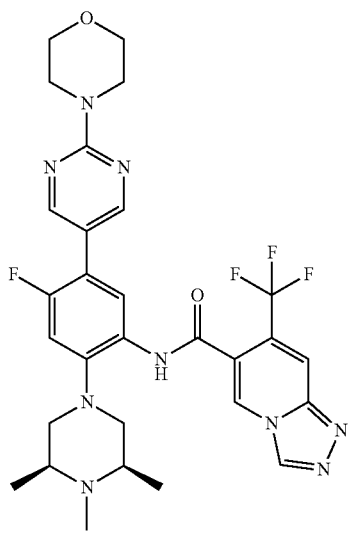 [SMILES: C[C@@H]1CN(c2cc(F)c(-c3cnc(N4CCOCC4)nc3)cc2NC(=O)c2cn3cnnc3cc2C(F)(F)F)C[C@H](C)N1C]

The title compound (yellow solid, 49.7 mg, 77%) was prepared by a procedure similar to that of Example 331 using 7-(trifluoromethyl)-[1,2,4]triazolo[4,3-a]pyridine-6-carboxylic acid (46 mg, 0.2 mmol) and 4-fluoro-5-(2-morpholinopyrimidin-5-yl)-2-((3S,5R)-3,4,5-trimethylpiperazin-1-yl)aniline (40 mg, 0.1 mmol). $^1$H NMR (500 MHz, CHLOROFORM-d) δ=13.44 (br d, J=13.4 Hz, 1H), 8.60 (d, J=13.7 Hz, 1H), 8.54 (s, 2H), 8.36 (s, 1H), 7.32 (s, 1H), 7.25 (d, J=7.1 Hz, 1H), 7.12 (d, J=11.1 Hz, 1H), 3.96-3.89 (m, 4H), 3.85-3.79 (m, 4H), 2.99 (br d, J=10.8 Hz, 2H), 2.82 (br s, 2H), 2.78-2.64 (m, 2H), 2.43 (br s, 3H), 1.17 (br d, J=5.9 Hz, 6H); LCMS [M+H]$^+$ 614.6.

Example 352: N-[5-[2-(7-azabicyclo[2.2.1]heptan-7-yl)pyrimidin-5-yl]-4-fluoro-2-[(3R,5S)-3,4,5-trimethylpiperazin-1-yl]phenyl]-6-oxo-4-(trifluoromethyl)-1H-pyridine-3-carboxamide

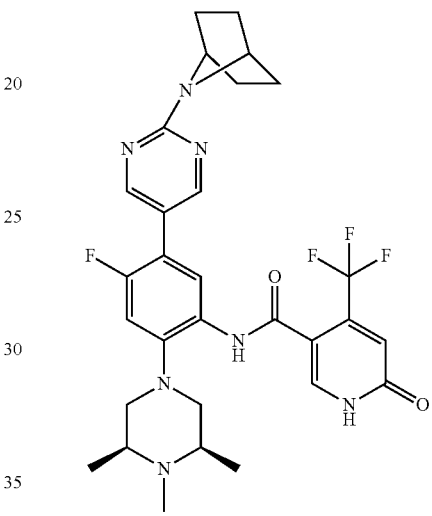

To a mixture of 2-chloropyrimidine-5-boronic acid (32 mg, 0.2 mmol) and 7-azabicyclo[2.2.1]heptane hydrochloride (28 mg, 0.21 mmol) in EtOH (2 mL) was added triethylamine (0.070 mL, 0.5 mmol). The resulting mixture was stirred at 75° C. 4 h. Solvents were removed to give the crude (2-(7-azabicyclo[2.2.1]heptan-7-yl)pyrimidin-5-yl)boronic acid as a light yellow solid. LCMS [M+H]$^+$ 220.3. The title compound (beige solid, 6.5 mg, 11%) was prepared by a procedure similar to that of Example 100 using the boronic acid (0.2 mmol) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, CHLOROFORM-d) δ=8.69 (br s, 1H), 8.54 (s, 2H), 8.43 (br d, J=6.8 Hz, 1H), 7.86 (br s, 1H), 7.05-6.94 (m, 2H), 4.74 (br s, 2H), 2.88-2.76 (m, 2H), 2.65 (br s, 2H), 2.40-2.26 (m, 4H), 1.91-1.79 (m, 5H), 1.53 (br d, J=7.1 Hz, 4H), 1.14 (br s, 6H); LCMS [M+H]$^+$ 600.6.

505

Example 353: N-[4-fluoro-5-(2-morpholin-4-ylpyrimidin-5-yl)-2-[(3R,5R)-3,4,5-trimethylpiperazin-1-yl]phenyl]-6-oxo-4-(trifluoromethyl)-1H-pyridine-3-carboxamide

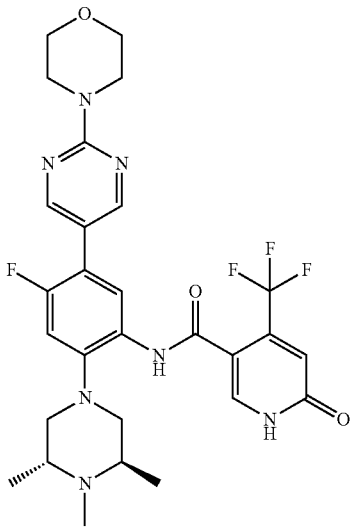 [SMILES: C[C@@H]1CN(c2cc(F)c(-c3cnc(N4CCOCC4)nc3)cc2NC(=O)c2c[nH]c(=O)cc2C(F)(F)F)C[C@@H](C)N1C]

Step 1: (2R,6R)-4-(4-bromo-5-fluoro-2-nitrophenyl)-1,2,6-trimethylpiperazine

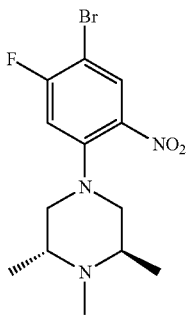 [SMILES: C[C@@H]1CN(c2cc(F)c(Br)cc2[N+](=O)[O-])C[C@@H](C)N1C]

To a stirred solution of (2R,6R)-1,2,6-trimethylpiperazine (4 g, 32.9 mmol, 1.3 eq) in ethanol (20 mL) was added TEA (5.23 mL, 37.5 mmol, 1.5 eq) at RT under argon atmosphere. After 30 min, 1-bromo-2,4-difluoro-5-nitrobenzene (preparation shown in Example 196 Step 4) was added (6 g, 25.0 mmol, 1 eq) at RT. Then the reaction mixture was heated to 85° C. for 16 h. TLC analysis indicated formation of polar spot. The reaction mixture was concentrated under reduced pressure gave crude product. The crude product was purified by column chromatography (silica gel 230-400 mesh) using 1-1.5% methanol in DCM as an eluent afforded (2R,6R)-4-(4-bromo-5-fluoro-2-nitrophenyl)-1,2,6-trimethylpiperazine (2.8 g, 32.2% yield) as yellow liquid. LCMS: [M+H]+ 345.85.

506

Step 2: 5-bromo-4-fluoro-2-((3R,5R)-3,4,5-trimethylpiperazin-1-yl)aniline

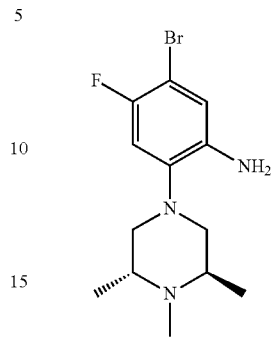

To a stirred solution of (2R,6R)-4-(4-bromo-5-fluoro-2-nitrophenyl)-1,2,6-trimethylpiperazine (0.82 g, 8.0 mmol, 1 eq) in ethanol:water (90 mL: 5 mL), was added NH₄Cl (1.29 g, 24.2 mmol, 3 eq) and Fe powder (1.35 g, 24.2 mmol, 3 eq) at RT and the resulting reaction mixture was heated at 80° C. for 16 h. The reaction was monitored by TLC, which indicated formation of polar spot. Then, the reaction mixture was cooled to RT and filtered through a celite bed; celite bed was washed with EtOAc (200 mL), and the filtrates were concentrated under reduced pressure to give crude product. The crude product was purified by column chromatography (neutral alumina) using DCM as an eluent to give 5-bromo-4-fluoro-2-((3R,5R)-3,4,5-trimethylpiperazin-1-yl)aniline (750 mg, 30% yield) as brown liquid. LCMS: [M+H]+ 316.1.

Step 3: N-(5-bromo-4-fluoro-2-((3R,5R)-3,4,5-trimethylpiperazin-1-yl)phenyl)-4-(trifluoromethyl)-6-(2-(trimethylsilyl)ethoxy)nicotinamide

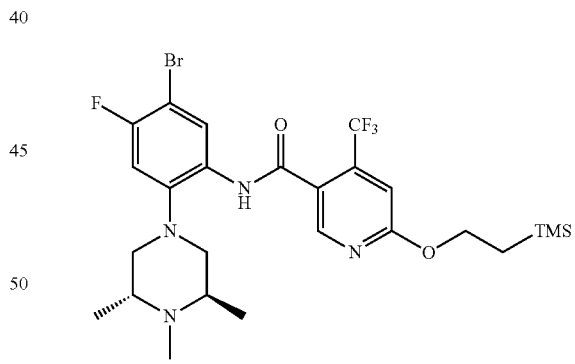

4-(Trifluoromethyl)-6-(2-(trimethylsilyl)ethoxy)nicotinic acid (0.22 g, 0.71 mmol) and propylphosphonic anhydride solution (0.7 mL, 2.4 mmol) were added to a suspension of 5-bromo-4-fluoro-2-((3R,5R)-3,4,5-trimethylpiperazin-1-yl)aniline (0.15 g, 0.47 mmol) in THF (4 mL). A solution of 4-methylmorpholine (0.10 mL, 0.95 mmol) in THF (1 mL) was added dropwise and the reaction mixture was stirred overnight at room temperature. The volatiles were removed in vacuo and the residue was partitioned between EtOAc and water. The layers were separated and the aqueous layer was extracted with an additional portion of EtOAc. The combined organics were washed with water, aqueous 1 N NaOH, and a saturated brine solution. After drying over magnesium sulfate, the inorganics were removed by filtration and the filtrate was concentrated to dryness. The residue was purified by flash chromatography [0.5-10% MeOH/DCM+0.5% NH₄OH] to afford N-(5-bromo-4-fluoro-2-((3R,5R)-3,4,5-trimethylpiperazin-1-yl)phenyl)-4-(trifluoromethyl)-6-(2-(trimethylsilyl)ethoxy)nicotinamide (0.12 g, 41%). LCMS [M+H]+: 605.3.

Step 4: N-(4-fluoro-5-(2-morpholinopyrimidin-5-yl)-2-((3R,5R)-3,4,5-trimethylpiperazin-1-yl)phenyl)-6-oxo-4-(trifluoromethyl)-1,6-dihydropyridine-3-carboxamide

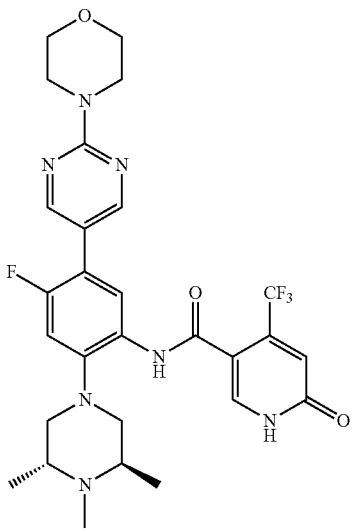 [SMILES: C[C@@H]1CN(c2cc(F)c(-c3cnc(N4CCOCC4)nc3)cc2NC(=O)c2c[nH]c(=O)cc2C(F)(F)F)C[C@@H](C)N1C]

A reaction vial was charged with 2-(4-morpholino)pyrimidine-5-boronic acid pinacol ester (0.017 g, 0.057 mmol), XPhos Pd G2 (0.00075 g, 0.96 μmol) and XPhos (0.00046 g, 0.96 μmol). The vial was sealed with a septum and evacuated and backfilled with nitrogen. A solution of N-(5-bromo-4-fluoro-2-((3R,5R)-3,4,5-trimethylpiperazin-1-yl)phenyl)-4-(trifluoromethyl)-6-(2-(trimethylsilyl)ethoxy)nicotinamide (0.029 g, 0.048 mmol) in 1,4-dioxane (0.8 mL) was added via syringe, followed by aqueous sodium carbonate (0.084 mL, 2 M) and the vial was evacuated and backfilled an additional time. The reaction was heated to 80° C. for 18 h. The reaction mixture was partitioned between DCM and water and the layers were separated. The aqueous layer was extracted with an additional portion of DCM and the combined organics were dried over magnesium sulfate. After removal of the inorganics by filtration the filtrate was concentrated to dryness and the residue was purified by flash chromatography [0.5-10% MeOH/DCM+0.5% NH₄OH] to afford the silyl protected intermediate which was dissolved in DCM (2 mL) and treated with TFA (0.2 mL) at room temperature. After stirring for 1 h the volatiles were removed in vacuo and the title compound was isolated using a catch and release protocol with a PoraPak Rxn CX ion exchange column to afford the title compound N-(4-fluoro-5-(2-morpholinopyrimidin-5-yl)-2-((3R,5R)-3,4,5-trimethylpiperazin-1-yl)phenyl)-6-oxo-4-(trifluoromethyl)-1,6-dihydropyridine-3-carboxamide (0.014 g, 51%). ¹H NMR (500 MHz, DMSO-d6) δ=9.30 (s, 1H), 8.53 (s, 2H), 8.03 (s, 1H), 7.74 (d, J=8.6 Hz, 1H), 7.07 (d, J=12.3 Hz, 1H), 6.80 (s, 1H), 3.79-3.72 (m, 4H), 3.70-3.65 (m, 4H), 2.90 (br d, J=9.3 Hz, 2H), 2.84-2.77 (m, 2H), 2.64 (br dd, J=6.2, 10.8 Hz, 2H), 2.20 (s, 3H), 0.97 (d, J=6.4 Hz, 6H); LCMS [M+H]+: 590.6.

Example 354: N-[4-fluoro-5-(3-fluoro-4-morpholin-4-ylphenyl)-2-[(3R,5R)-3,4,5-trimethylpiperazin-1-yl]phenyl]-6-oxo-4-(trifluoromethyl)-1H-pyridine-3-carboxamide

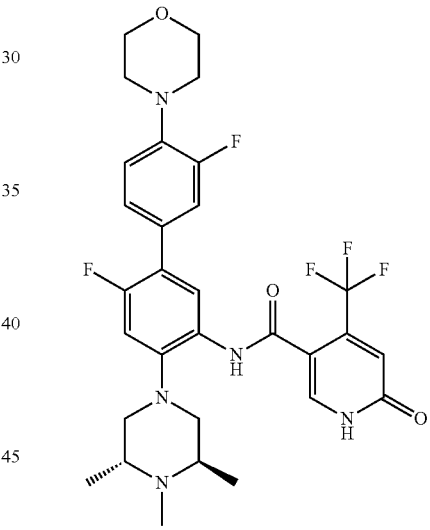

The title compound was prepared similar to the procedure described above for the preparation of Example 353 using 3-fluoro-4-morpholinophenylboronic acid in place of 2-(4-morpholino)pyrimidine-5-boronic acid pinacol ester in Step 3. ¹H NMR (500 MHz, DMSO-d6) δ=9.29 (s, 1H), 8.03 (s, 1H), 7.75 (br d, J=8.7 Hz, 1H), 7.33-7.23 (m, 2H), 7.19-7.11 (m, 1H), 7.03 (d, J=12.7 Hz, 1H), 6.81 (s, 1H), 3.80-3.73 (m, 4H), 3.11-3.02 (m, 4H), 2.95-2.88 (m, 2H), 2.84-2.78 (m, 2H), 2.64 (br dd, J=6.1, 10.8 Hz, 2H), 2.21 (s, 3H), 0.97 (d, J=6.4 Hz, 6H); LCMS [M+H]+: 606.6.

Example 355: N-[4-fluoro-5-(2-morpholin-4-ylpyrimidin-5-yl)-2-[(3R,5R)-3,4,5-trimethylpiperazin-1-yl]phenyl]-6-oxo-4-(trifluoromethyl)-1H-pyridine-3-carboxamide

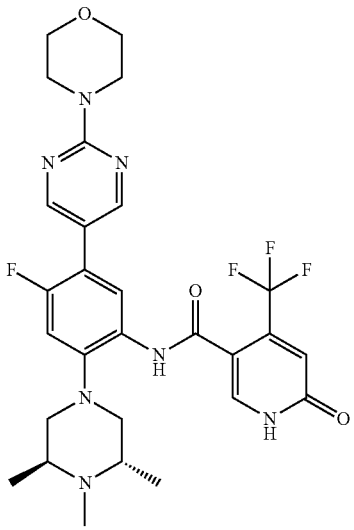 [SMILES: C[C@H]1CN(c2cc(F)c(-c3cnc(N4CCOCC4)nc3)cc2NC(=O)c2c[nH]c(=O)cc2C(F)(F)F)C[C@H](C)N1C]

Step 1: (R)-1-(benzylamino)propan-2-ol

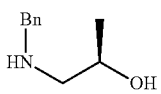

To a solution of (R)-1-aminopropan-2-ol (50 g, 792.8 mmol, 1 eq) in THF (1680 mL) was added benzaldehyde (84 g, 799.9 mmol, 1.2 eq), MgSO₄ (41 g) under argon atmosphere. The reaction mixture was stirred at room temperature for 4 h. The reaction was filtered and concentrated to obtain the crude intermediate, which was diluted with ethanol, NaBH₄ (8.4 g, 220.0 mmol, 0.33 eq) was added portion wise at 10° C. and stirred for 2 h at RT. Then, NaBH₄ (8.4 g, 220.0 mmol, 0.33 eq) was added portion wise at 10° C. and stirred for 72 h at RT. The reaction was monitored by TLC, and TLC analysis indicated formation of nonpolar spot. The reaction mixture was concentrated under reduced pressure to give crude product. The crude product was diluted with ethyl acetate then extracted with 2N aq. HCl (3×100 mL). The Aq. layer was neutralized (pH 7) with sat. NaHCO₃ solution, extracted with DCM (4×100 mL) followed by washing with brine solution (100 mL), drying over Na₂SO₄ and concentrating under reduced pressure to provide crude (R)-1-(benzylamino)propan-2-ol (110 g, 100% yield) as a colourless liquid. TLC: 5% MeOH:DCM; $R_f$: 0.4

Step 2: tert-butyl ((S)-1-(benzyl((R)-2-hydroxypropyl)amino)-1-oxopropan-2-yl)carbamate

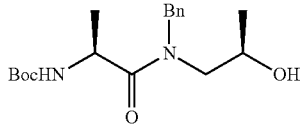 [SMILES: C[C@H](NC(=O)OC(C)(C)C)C(=O)N(Cc1ccccc1)C[C@@H](C)O]

To a stirred solution of (tert-butoxycarbonyl)-L-alanine (45 g, 272.7 mmol, 1 eq) in DCM (800 mL) was added CDI (44 g, 272.7 mmol, 1 eq) at 10° C. under argon atmosphere. The reaction mixture was stirred for 2 h at RT. (R)-1-(Benzylamino)propan-2-ol (45 g, 272.7 mmol, 1 eq) in DCM (100 mL) was added slowly at 10° C. and stirred for 16 h at RT. The reaction was monitored by TLC, and TLC analysis indicated formation of less polar spot. The reaction mixture was concentrated under reduced pressure to give crude compound. The crude compound was purified by column chromatography using 100-200 silica gel as stationary phase and ethyl acetate in pet ether as mobile phase to afford pure tert-butyl ((S)-1-(benzyl((R)-2-hydroxypropyl)amino)-1-oxopropan-2-yl)carbamate (75 g, 81.8% yield) as colour less liquid. LCMS: [M+H]+ 337.0.

Step 3: (S)-2-amino-N-benzyl-N—((R)-2-hydroxypropyl)propanamide

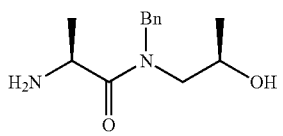 [SMILES: C[C@H](N)C(=O)N(Cc1ccccc1)C[C@@H](C)O]

To a solution of tert-butyl ((S)-1-(benzyl((R)-2-hydroxypropyl)amino)-1-oxopropan-2-yl)carbamate (55 g, 163.6 mmol, 1 eq) in DCM (550 mL) was added TFA (250 mL, 3272.0 mmol, 20 eq) at 0° C. under argon atmosphere. The reaction mixture was stirred for 1 h at RT. TLC analysis indicated formation of polar spot. The reaction mixture was concentrated under reduced pressure to give crude compound. The residue was diluted with DCM (250 mL), washed with sat. NaHCO₃ solution (200 mL) and the aqueous layer was extracted with DCM (200 mL). The combined organic layer was washed with water (2×150 mL) followed by brine solution (100 mL), dried over Na₂SO₄ and concentrated under reduced pressure to afford crude (S)-2-amino-N-benzyl-N—((R)-2-hydroxypropyl)propanamide (25 g, crude yield) as colorless liquid. LCMS: [M+H]+ 237.0.

Step 4: (R)-1-(((S)-2-aminopropyl)(benzyl)amino)propan-2-ol

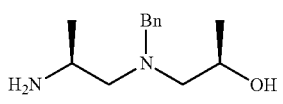

A stirred solution of (S)-2-amino-N-benzyl-N—((R)-2-hydroxypropyl)propanamide (21 g, 89.0 mmol, 1 eq) in THF (400 mL) was cooled to 0° C. and BH₃·DMS (10M) (25.5 mL, 254.5 mmol, 2.86 eq) was added dropwise at 0° C. under argon atmosphere. Then, the reaction mixture was allowed to stir at RT for 16 h. After cooling to 0° C., the reaction mixture was quenched with HCl (20%, 490 mL). The reaction was basified with KOH (5N, 164 mL) and KOH (310.8 g, 37.2 eq), and the mixture was heated at reflux for 24 h. Then MeOH (100 mL) was added at rt then refluxed for 72 h. The reaction was monitored by TLC, and TLC analysis indicated formation of less polar spot. The reaction mixture was cooled to room temperature, and concentrated to remove organic solvents. The aqueous layer was extracted with DCM (250 mL). The combined organic layer was washed with brine (100 mL), dried over Na₂SO₄ and concentrated under reduced pressure to obtain the crude product, which was purified by column by using neutral alumina as stationary phase and 0-5% MeOH in DCM as mobile phase to afford (R)-1-(((S)-2-aminopropyl)(benzyl)amino)propan-2-ol (14 g, 70.80% yield) as pale green liquid. LCMS: [M+1] 223.11.

Step 5: (3S,5S)-1-benzyl-3,5-dimethylpiperazine

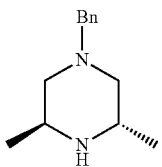

To a stirred solution of (R)-1-(((S)-2-aminopropyl)(benzyl)amino)propan-2-ol (4 g, 18.0 mmol, 1 eq) in THF (160 mL) was added TPP (9.45 g, 36.03 mmol, 2 eq) at 0° C. After stirring for 10 min, DIAD (7.3 mL, 36.03 mmol, 2 eq) was added at 0° C. The reaction mixture was stirred for 16 h at room temperature. TLC analysis indicated formation of less polar spot. The reaction mixture was concentrated to give crude residue, which was purified by column by using neutral alumina as stationary phase and 0-5% MeOH in DCM as mobile phase to give (3S,5S)-1-benzyl-3,5-dimethylpiperazine (14 g, 41.7% yield) as pale brown liquid. LCMS: [M+1]+ 205.06.

Step 6: (2S,6S)-4-benzyl-1,2,6-trimethylpiperazine

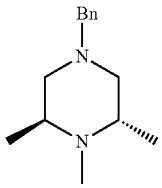

A solution of (3S,5S)-1-benzyl-3,5-dimethylpiperazine (3.5 g, 17.15 mmol, 1 eq) in DCM:AcOH (35 mL:15 mL. 5 mL) was cooled to 0° C. and 37% HCHO soln. (2.8 mL, 34.31 mmol, 2 eq) was added dropwise at 0° C. under argon atmosphere. Then, the reaction mixture was allowed to react at RT for 3 h. The reaction mixture was cooled to 0° C. and NaCNBH₃ 2.1 g, 34.31 mol, 2 eq) was added slowly at 0° C. and allowed to react at RT for 2 h. The reaction was monitored by TLC, and TLC analysis indicated formation of less polar spot. The reaction was basified with sat. NaHCO₃ and extracted with DCM (2×250 ml). The combined organic layer was washed with water (150 mL) and brine solution (100 mL), dried over Na₂SO₄ then concentrated under reduced pressure to give crude compound. The crude compound was purified by silica gel chromatography (silica gel 230-400 mesh) using 2-5% MeOH in DCM as an eluent to afford (2S,6S)-4-benzyl-1,2,6-trimethylpiperazine (3 g, 81.1% yield) as brown liquid. LCMS: [M+H]+ 219.11.

Step 7: (2S,6S)-1,2,6-trimethylpiperazine

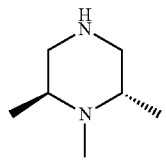

To a stirred solution of (2S,6S)-4-benzyl-1,2,6-trimethylpiperazine (4.6 g, 21.1 mmol, 1 eq) in methanol (146 mL) was added Pd(OH)₂ (20% wt on carbon, 820 mg) and HCl (4M in dioxane, 1 mL). Then the reaction mixture was purged with nitrogen for 15 min, and then hydrogenated under par shaker for 18 h. TLC analysis indicated formation of polar spot. The reaction mixture was filtered through celite, and washed with methanol and DCM. The filtrate was concentrated under reduced pressure to afford (2S,6S)-1,2,6-trimethylpiperazine (3 g, 45% crude yield) as a pale yellow liquid. LCMS: [M+H]+ 347.96.

Step 8: (2S,6S)-4-(4-bromo-5-fluoro-2-nitrophenyl)-1,2,6-trimethylpiperazine

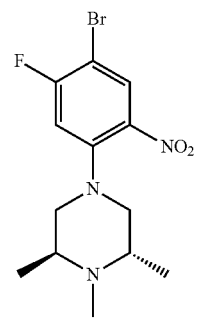 [SMILES: C[C@H]1CN(c2cc(F)c(Br)cc2[N+](=O)[O-])C[C@H](C)N1C]

To a solution of (2S,6S)-4-benzyl-1,2,6-trimethylpiperazine (3 g, 13.4 mmol, 1.3 eq) in ethanol (90 mL) was added TEA (2 mL, 15.449 mmol, 1.5 eq) at RT under argon atmosphere, then after 30 min, 1-bromo-2,4-difluoro-5-nitrobenzene (4.5 mL, 10.299 mmol, 1 eq) was added at RT. Then the reaction mass was heated to 85° C. for 16 h. The reaction was monitored by TLC, and TLC analysis indicated formation of polar spot. The reaction mixture was concentrated under reduced pressure to give crude product. The crude product was purified by column chromatography (silica gel 230-400 mesh) using 3% methanol in DCM as an eluent to give (2S,6S)-4-(4-bromo-5-fluoro-2-nitrophenyl)-1,2,6-trimethylpiperazine (3 g, 46.8% yield) as yellow liquid. LCMS: [M+H]+ 347.96.

Step 9: 5-bromo-4-fluoro-2-((3S,5S)-3,4,5-trimethylpiperazin-1-yl)aniline

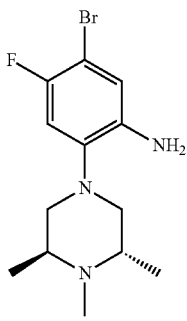 [SMILES: C[C@H]1CN(c2cc(F)c(Br)cc2N)C[C@H](C)N1C]

A round bottomed flask was charged with (2S,6S)-4-(4-bromo-5-fluoro-2-nitrophenyl)-1,2,6-trimethylpiperazine (3.5 g, 10.14 mmol, 1 eq), NH$_4$Cl (3.25 g, 60.86 mmol, 6 eq) and Fe powder (3.4 g, 60.9 mmol, 6 eq) and covered with ethanol:water (60 mL: 10 mL) at RT. The resulting suspension was then heated to 80° C. for 16 h. The reaction was monitored by TLC, and TLC analysis indicated formation of a polar spot. Then, the reaction mixture was cooled to RT and filtered through a celite bed; celite bed was washed with EtOAc (200 mL), then the filtrates were concentrated under reduced pressure to give crude product. The crude product was purified by column chromatography (neutral alumina) using DCM as an eluent to give 5-bromo-4-fluoro-2-((3S,5S)-3,4,5-trimethylpiperazin-1-yl)aniline (1.4 g, 41.1% yield) as brown semisolid. LCMS: [M+H]+: 318.0.

Step 10: N-[4-fluoro-5-(2-morpholin-4-ylpyrimidin-5-yl)-2-[(3R,5R)-3,4,5-trimethylpiperazin-1-yl]phenyl]-6-oxo-4-(trifluoromethyl)-1H-pyridine-3-carboxamide

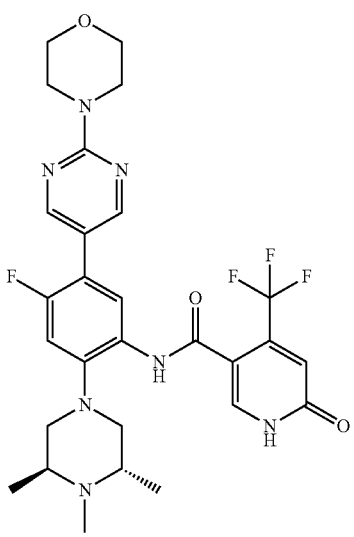 [SMILES: C[C@H]1CN(c2cc(F)c(-c3cnc(N4CCOCC4)nc3)cc2NC(=O)c2c[nH]c(=O)cc2C(F)(F)F)C[C@H](C)N1C]

The title compound was prepare similar to the sequence described above for the preparation of Example 353 using 5-bromo-4-fluoro-2-((3S,5S)-3,4,5-trimethylpiperazin-1-yl)aniline in place of 5-bromo-4-fluoro-2-((3R,5R)-3,4,5-trimethylpiperazin-1-yl)aniline in Step 3. $^1$H NMR (500 MHz, DMSO-d6) δ=9.30 (s, 1H), 8.53 (d, J=0.6 Hz, 2H), 8.03 (s, 1H), 7.74 (d, J=8.6 Hz, 1H), 7.07 (d, J=12.3 Hz, 1H), 6.80 (s, 1H), 3.78-3.72 (m, 4H), 3.71-3.65 (m, 4H), 2.90 (br d, J=9.0 Hz, 2H), 2.81 (dt, J=3.1, 6.1 Hz, 2H), 2.64 (br dd, J=6.2, 10.8 Hz, 2H), 2.20 (s, 3H), 0.97 (d, J=6.4 Hz, 6H); LCMS [M+H]+: 590.6.

Example 356: N-[4-fluoro-5-[2-[(2R,6S)-2,6-dimethylmorpholin-4-yl]pyrimidin-5-yl]-2-[(3R,5R)-3,4,5-trimethylpiperazin-1-yl]phenyl]-6-oxo-4-(trifluoromethyl)-1H-pyridine-3-carboxamide

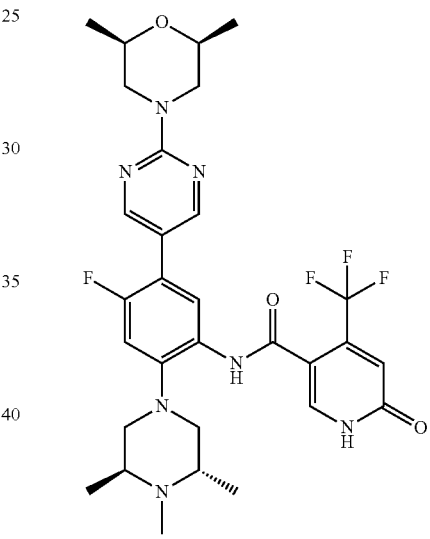

The title compound was prepared similar to the sequence described above for the preparation of Example 355 using (2-(cis-2,6-dimethylmorpholino)pyrimidin-5-yl)boronic acid in place of 2-(4-morpholino)pyrimidine-5-boronic acid pinacol ester in the final step. $^1$H NMR (500 MHz, DMSO-d6) δ=9.29 (s, 1H), 8.51 (s, 2H), 8.03 (s, 1H), 7.73 (d, J=8.6 Hz, 1H), 7.07 (d, J=12.3 Hz, 1H), 6.80 (s, 1H), 4.60-4.46 (m, 2H), 3.63-3.51 (m, 2H), 2.90 (br d, J=8.1 Hz, 2H), 2.84-2.78 (m, 2H), 2.63 (br dd, J=6.2, 10.8 Hz, 2H), 2.58 (dd, J=10.8, 13.0 Hz, 2H), 2.20 (s, 3H), 1.16 (d, J=6.1 Hz, 6H), 0.97 (d, J=6.4 Hz, 6H); LCMS [M+H]+: 618.5.

515

Example 357: N-[4-fluoro-5-(3-fluoro-4-morpholin-4-ylphenyl)-2-[(3R,5R)-3,4,5-trimethylpiperazin-1-yl]phenyl]-6-oxo-4-(trifluoromethyl)-1H-pyridine-3-carboxamide

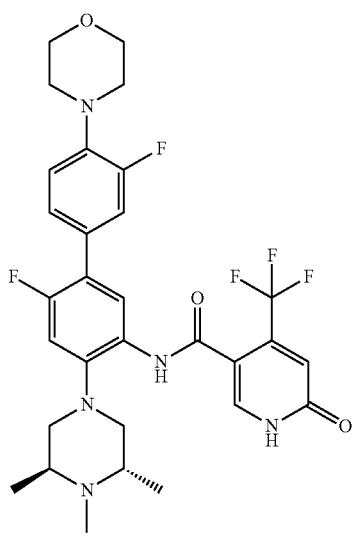 [SMILES: C[C@H]1CN(c2cc(F)c(-c3ccc(N4CCOCC4)c(F)c3)cc2NC(=O)c2c[nH]c(=O)cc2C(F)(F)F)C[C@H](C)N1C]

The title compound was prepared similar to the sequence described above for the preparation of Example 355 using 3-fluoro-4-morpholinophenylboronic acid in place of 2-(4-morpholino)pyrimidine-5-boronic acid pinacol ester in the final step. $^1$H NMR (500 MHz, DMSO-d6) δ=9.28 (s, 1H), 8.04 (s, 1H), 7.75 (br d, J=8.4 Hz, 1H), 7.36-7.23 (m, 2H), 7.17-7.09 (m, 1H), 7.04 (d, J=12.7 Hz, 1H), 6.81 (s, 1H), 3.80-3.72 (m, 4H), 3.10-3.03 (m, 4H), 2.91 (br d, J=8.8 Hz, 2H), 2.86-2.78 (m, 2H), 2.64 (br dd, J=6.1, 10.8 Hz, 2H), 2.20 (s, 3H), 0.97 (d, J=6.4 Hz, 6H); LCMS [M+H]+: 606.6.

516

Example 358: N-[4-fluoro-5-(2-morpholin-4-ylpyrimidin-5-yl)-2-[(3R,4R)-3-[ethyl(methyl)amino]-4-methoxypyrrolidin-1-yl]phenyl]-6-oxo-4-(trifluoromethyl)-1H-pyridine-3-carboxamide

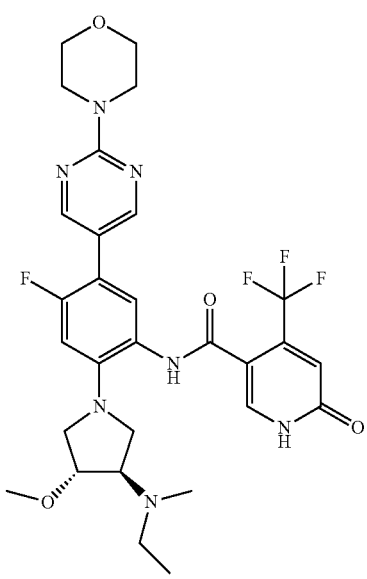 [SMILES: CCN(C)[C@@H]1CN(c2cc(F)c(-c3cnc(N4CCOCC4)nc3)cc2NC(=O)c2c[nH]c(=O)cc2C(F)(F)F)C[C@H]1OC]

The title compound was prepared similar to the procedure described above for the preparation of Example 307 using N-ethylmethylamine in place of N-(2-methoxyethyl)methylamine in Step 1. $^1$H NMR (500 MHz, DMSO-d6) δ=9.78 (s, 1H), 8.51 (s, 2H), 7.98 (s, 1H), 7.36 (d, J=8.8 Hz, 1H), 6.77 (s, 1H), 6.74 (d, J=13.8 Hz, 1H), 3.91-3.84 (m, 1H), 3.78-3.71 (m, 4H), 3.70-3.63 (m, 4H), 3.51-3.42 (m, 2H), 3.25 (s, 3H), 3.18 (br dd, J=6.4, 10.0 Hz, 1H), 3.05-2.97 (m, 1H), 2.48-2.40 (m, 1H), 2.17 (s, 3H), 0.95 (t, J=7.1 Hz, 3H); LCMS [M+H]+: 620.6.

517

Example 359: N-[5-[6-(cyclopropylmethoxy)pyridin-3-yl]-4-fluoro-2-[(3R,5R)-3,4,5-trimethylpiperazin-1-yl]phenyl]-6-oxo-4-(trifluoromethyl)-1H-pyridine-3-carboxamide

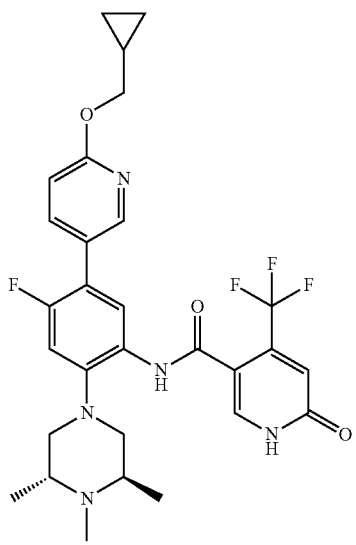 [SMILES: C[C@@H]1CN(c2cc(F)c(-c3ccc(OCC4CC4)nc3)cc2NC(=O)c2c[nH]c(=O)cc2C(F)(F)F)C[C@@H](C)N1C]

The title compound was prepared similar to the procedure described above for the preparation of Example 353 using 2-(cyclopropylmethoxy)-5-(4,4,5,5-tetramethyl-1,3,2-dioxaborolan-2-yl)pyridine in place of 2-(4-morpholino)pyrimidine-5-boronic acid pinacol ester in Step 3. $^1$H NMR (500 MHz, DMSO-d6) δ=8.91 (s, 1H), 8.25 (s, 1H), 8.18 (s, 1H), 7.94 (d, J=8.7 Hz, 1H), 7.86-7.77 (m, 1H), 7.11 (d, J=12.2 Hz, 1H), 6.92 (d, J=8.6 Hz, 1H), 6.28 (s, 1H), 4.13 (d, J=7.2 Hz, 2H), 2.91 (br d, J=8.6 Hz, 2H), 2.86-2.78 (m, 2H), 2.61 (br dd, J=6.2, 10.9 Hz, 2H), 2.21 (s, 3H), 1.32-1.21 (m, 1H), 0.97 (d, J=6.4 Hz, 6H), 0.59-0.52 (m, 2H), 0.37-0.30 (m, 2H); LCMS [M+H]+: 574.6.

518

Example 360: N-[4-fluoro-5-[2-[(2R,6S)-2,6-dimethylmorpholin-4-yl]pyrimidin-5-yl]-2-[(3S,5S)-3,4,5-trimethylpiperazin-1-yl]phenyl]-6-oxo-4-(trifluoromethyl)-1H-pyridine-3-carboxamide

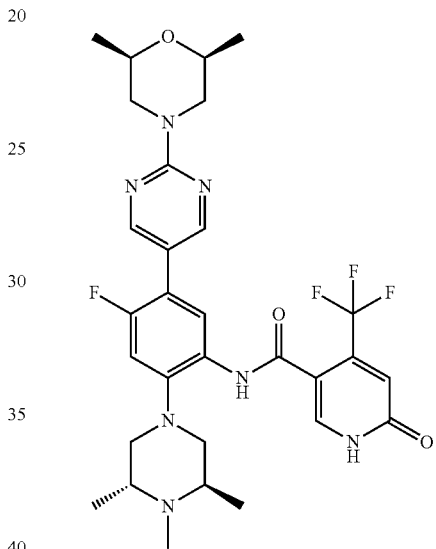

The title compound was prepared similar to the procedure described above for the preparation of Example 353 using (2-(cis-2,6-dimethylmorpholino)pyrimidin-5-yl)boronic acid in place of 2-(4-morpholino)pyrimidine-5-boronic acid pinacol ester in Step 3. $^1$H NMR (500 MHz, DMSO-d6) δ=9.28 (s, 1H), 8.51 (s, 2H), 8.04 (s, 1H), 7.74 (d, J=8.6 Hz, 1H), 7.07 (d, J=12.3 Hz, 1H), 6.78 (s, 1H), 4.59-4.48 (m, 2H), 3.57 (ddd, J=2.3, 6.3, 10.3 Hz, 2H), 2.94-2.88 (m, 2H), 2.81 (dt, J=3.0, 6.1 Hz, 2H), 2.63 (br dd, J=6.2, 10.8 Hz, 2H), 2.58 (dd, J=10.8, 13.1 Hz, 2H), 2.20 (s, 3H), 1.16 (d, J=6.2 Hz, 6H), 0.97 (d, J=6.4 Hz, 6H); LCMS [M+H]+: 618.6.

Example 361: N-[5-[6-(cyclopropylmethoxy)pyridin-3-yl]-4-fluoro-2-[(3R,5R)-3,4,5-trimethylpiperazin-1-yl]phenyl]-6-oxo-4-(triluoromethyl)-1H-pyridine-3-carboxamide

Example 362: N-[4-fluoro-5-[2-[methyl-[(3R)-oxolan-3-yl]amino]pyrimidin-5-yl]-2-[(3R)-3,4-dimethylpiperazin-1-yl]phenyl]-6-oxo-4-(trifluoromethyl)-1H-pyridine-3-carboxamide

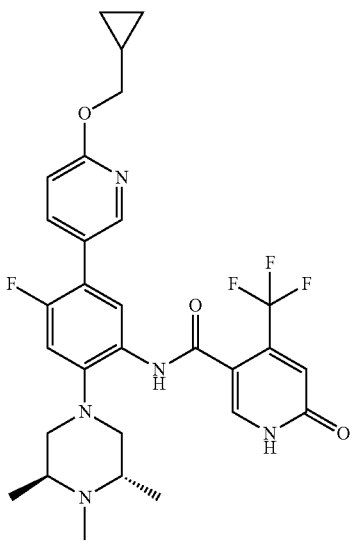 [SMILES: C[C@H]1CN(c2cc(F)c(-c3ccc(OCC4CC4)nc3)cc2NC(=O)c2c[nH]c(=O)cc2C(F)(F)F)C[C@H](C)N1C]

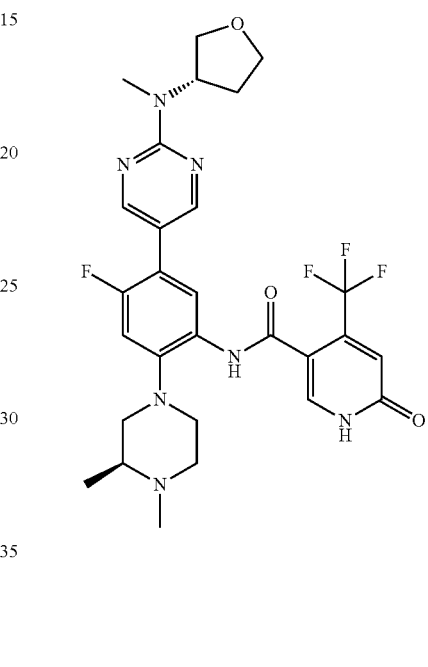

The title compound was prepared similar to the sequence described above for the preparation of Example 355 using 2-(cyclopropylmethoxy)-5-(4,4,5,5-tetramethyl-1,3,2-dioxaborolan-2-yl)pyridine in place of 2-(4-morpholino)pyrimidine-5-boronic acid pinacol ester in the final step of the sequence. $^1$H NMR (500 MHz, DMSO-d6) δ=9.02 (s, 1H), 8.25 (s, 1H), 8.14 (s, 1H), 7.90 (d, J=8.6 Hz, 1H), 7.82 (dd, J=1.2, 8.6 Hz, 1H), 7.10 (d, J=12.2 Hz, 1H), 6.93 (d, J=8.6 Hz, 1H), 6.42 (s, 1H), 4.14 (d, J=7.2 Hz, 2H), 2.94-2.89 (m, 2H), 2.87-2.80 (m, 2H), 2.62 (br dd, J=6.2, 10.9 Hz, 2H), 2.21 (s, 3H), 1.32-1.21 (m, 1H), 0.97 (d, J=6.4 Hz, 6H), 0.59-0.53 (m, 2H), 0.37-0.31 (m, 2H); LCMS [M+H]+: 574.5.

To a mixture of 2-chloropyrimidine-5-boronic acid (32 mg, 0.2 mmol) and (S)-methyl-(tetrahydro-furan-3-yl)-amine hydrochloride (29 mg, 0.21 mmol) in EtOH (2 mL) was added triethylamine (0.070 mL, 0.5 mmol). The resulting mixture was stirred at 75° C. for 5 h. Solvents were removed to give crude (S)-(2-(methyl(tetrahydrofuran-3-yl)amino)pyrimidin-5-yl)boronic acid as a light yellow semi-solid. LCMS [M+H]$^+$ 224.2. The title compound (light beige solid, 8.3 mg, 14%) was prepared by a procedure similar to that of the last step of Example 273 using crude (S)-(2-(methyl(tetrahydrofuran-3-yl)amino)pyrimidin-5-yl)boronic acid (0.2 mmol) and (S)—N-(5-bromo-2-(3,4-dimethylpiperazin-1-yl)-4-fluorophenyl)-6-oxo-4-(trifluoromethyl)-1,6-dihydropyridine-3-carboxamide (49.1 mg, 0.1 mmol). $^1$H NMR (500 MHz, CHLOROFORM-d) δ=8.72 (br s, 1H), 8.57 (s, 2H), 8.47 (br d, J=8.1 Hz, 1H), 7.88 (s, 1H), 7.05 (br d, J=11.0 Hz, 1H), 7.02 (s, 1H), 5.69-5.63 (m, 1H), 4.13 (dt, J=4.7, 8.5 Hz, 1H), 3.94-3.87 (m, 2H), 3.79 (q, J=8.1 Hz, 1H), 3.16 (s, 3H), 3.03-2.88 (m, 3H), 2.83 (br d, J=10.9 Hz, 1H), 2.61 (br t, J=10.3 Hz, 1H), 2.43-2.29 (m, 5H), 2.23 (br s, 1H), 2.06-1.97 (m, 1H), 1.12 (br d, J=5.9 Hz, 3H); LCMS [M+H]$^+$ 590.6.

Example 363: N-[4-fluoro-5-[2-[methyl-[(3R)-oxolan-3-yl]amino]pyrimidin-5-yl]-2-[(3S,5R)-3,4,5-trimethylpiperazin-1-yl]phenyl]-6-oxo-4-(trifluoromethyl)-1H-pyridine-3-carboxamide

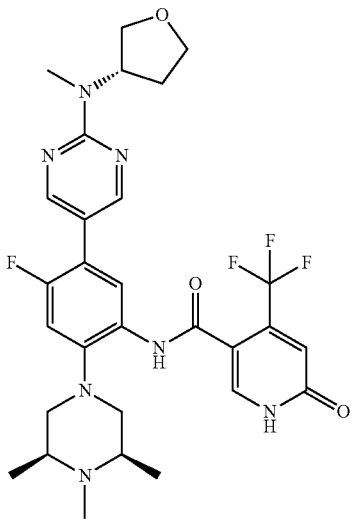 [SMILES: C[C@@H]1CN(c2cc(F)c(-c3cnc(N(C)[C@H]4CCOC4)nc3)cc2NC(=O)c2c[nH]c(=O)cc2C(F)(F)F)C[C@H](C)N1C]

The title compound (beige solid, 5.3 mg, 9%) was prepared by a procedure similar to that of Example 29 using crude (S)-(2-(methyl(tetrahydrofuran-3-yl)amino)pyrimidin-5-yl)boronic acid (0.2 mmol) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, CHLOROFORM-d) δ=8.70 (br s, 1H), 8.55 (s, 2H), 8.45 (br d, J=7.6 Hz, 1H), 7.83 (s, 1H), 7.06-6.96 (m, 2H), 5.68-5.60 (m, 1H), 4.11 (dt, J=4.6, 8.4 Hz, 1H), 3.92-3.85 (m, 2H), 3.78 (q, J=8.0 Hz, 1H), 3.15 (s, 3H), 2.86-2.75 (m, 2H), 2.65 (br t, J=9.2 Hz, 2H), 2.39-2.16 (m, 6H), 2.04-1.94 (m, 1H), 1.14 (d, J=4.8 Hz, 6H); LCMS [M+H]$^+$ 604.6.

Example 364: 4-fluoro-N-[4-fluoro-5-(2-morpholin-4-ylpyrimidin-5-yl)-2-[(3R,5S)-3,5-dimethylpiperazin-1-yl]phenyl]-2-(trifluoromethyl)benzamide

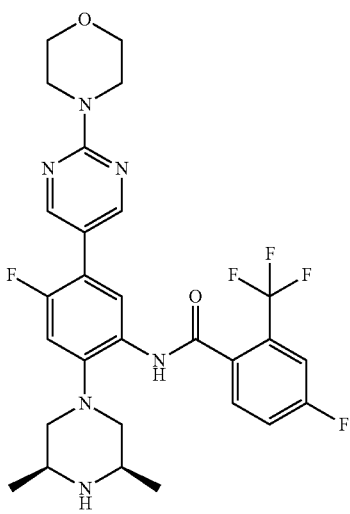 [SMILES: C[C@@H]1CN(c2cc(F)c(-c3cnc(N4CCOCC4)nc3)cc2NC(=O)c2ccc(F)cc2C(F)(F)F)C[C@H](C)N1]

Step 1: tert-butyl (2S,6R)-4-(2-amino-4-bromo-5-fluorophenyl)-2,6-dimethylpiperazine-1-carboxylate

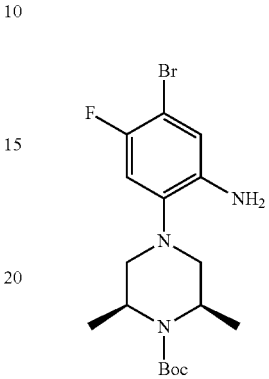

To a suspension of K$_2$CO$_3$ (366 mg, 2.65 mmol, 0.525 equiv.) in toluene (20 mL) was added cis-2,6-dimethylpiperazine (577 mg, 5.05 mmol), followed by dropwise addition of 1-bromo-2,4-difluoro-5-nitrobenzene (0.63 mL, 5 mmol) over 1 min. The resulting mixture was stirred at 45° C. overnight. After diluting with H$_2$O (20 mL) to dissolve the insoluble salts, it was extracted with EtOAc (40 mL×2). The combined extracts were concentrated and dried under vacuum to give the nitro intermediate (3S,5R)-1-(4-bromo-5-fluoro-2-nitrophenyl)-3,5-dimethylpiperazine as an orange solid. LCMS [M+H]$^+$ 332.3. To a solution of the this intermediate in THF (30 mL) was added di-tert-butyl dicarbonate (1.309 g, 6 mmol). The resulting mixture was stirred at rt for 1.5 h. DMAP (73 mg, 0.6 mmol) was added and the resulting mixture was stirred at rt for 1 h. Additional di-tert-butyl dicarbonate (1.309 g, 6 mmol) was added and the resulting mixture was stirred over the weekend at rt. Solvents were removed and the residue was purified by flash chromatography (gradient: EtOAc/hex 0-30%) to give tert-butyl (2S,6R)-4-(4-bromo-5-fluoro-2-nitrophenyl)-2,6-dimethylpiperazine-1-carboxylate as pale yellow crystals (0.946 g). To a solution of the above pale yellow crystal in MeOH (30 mL) was added a suspension of Raney-Nickel (214 mg, 2.5 mmol) in MeOH (5 mL), followed by addition of hydrazine monohydrate (0.73 mL, 15 mmol) over 2 min. After addition, the resulting mixture was stirred at rt for 5 min then heated at 60° C. for 45 min. After filtering and rinsing with MeOH (10 mL), the filtrate was concentrated and purified by flash chromatography (gradient: EtOAc/hex 0-30%) to give tert-butyl (2S,6R)-4-(2-amino-4-bromo-5-fluorophenyl)-2,6-dimethylpiperazine-1-carboxylate as a beige solid (385 mg, 19% yield over 3 steps). LCMS [M+H]$^+$ 402.4.

Step 2: Preparation of tert-butyl (2S,6R)-4-(4-bromo-5-fluoro-2-(4-fluoro-2-(trifluoromethyl)benzamido)phenyl)-2,6-dimethylpiperazine-1-carboxylate

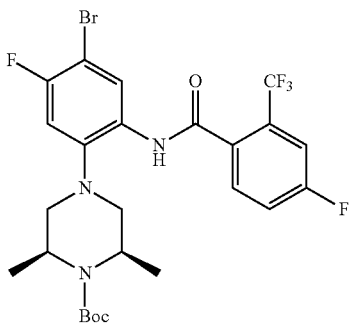 [SMILES: C[C@@H]1CN(c2cc(F)c(Br)cc2NC(=O)c2ccc(F)cc2C(F)(F)F)C[C@H](C)N1C(=O)OC(C)(C)C]

To a solution of 4-fluoro-2-(trifluoromethyl)benzoyl chloride (0.29 mL, 1.914 mmol) in DCM (10 mL) at rt was added Et₃N (0.534 mL, 3.83 mmol). After addition, the resulting mixture was stirred at rt for 5 min, before a solution of (2S,6R)-tert-butyl 4-(2-amino-4-bromo-5-fluorophenyl)-2,6-dimethylpiperaine-1-carboxylate (385 mg, 0.957 mmol) in DCM (5 mL) was added. The resulting mixture was stirred at rt overnight. After quenching with sat. NaHCO₃ (15 mL) and stirring for 10 min at rt, it was extracted with DCM (15 mL×2). The combined extracts were combined and concentrated to give a light yellow solid. It was triturated with DCM/MeOH (2 mL/8 mL), filtered and dried to give a white solid (463 mg). LCMS [M+H]⁺ 592.4.

Step 3: N-(2-((3S,5R)-3,5-dimethylpiperazin-1-yl)-4-fluoro-5-(2-morpholinopyrimidin-5-yl)phenyl)-4-fluoro-2-(trifluoromethyl)benzamide

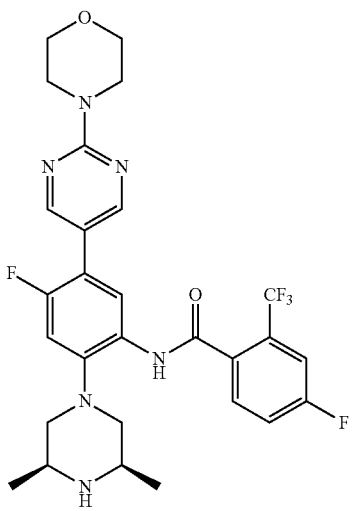 [SMILES: C[C@@H]1CN(c2cc(F)c(-c3cnc(N4CCOCC4)nc3)cc2NC(=O)c2ccc(F)cc2C(F)(F)F)C[C@H](C)N1]

tert-Butyl(2S,6R)-4-(5-fluoro-2-(4-fluoro-2-(trifluoromethyl)benzamido)-4-(2-morpholinopyrimidin-5-yl)phenyl)-2,6-dimethylpiperazine-1-carboxylate (444 mg) was prepared according to a method similar to that used in the final step of Example 29 using 2-(4-morpholino)pyrimidine-5-boronic acid pinacol ester (466 mg, 1.6 mmol) and (2S,6R)-tert-butyl 4-(4-bromo-5-fluoro-2-(4-fluoro-2-(trifluoromethyl)benzamido)phenyl)-2,6-dimethylpiperazine-1-carboxylate (453 mg, 0.765 mmol). LCMS [M+H]⁺ 677.6. The above solid (444 mg) was redissolved in DCM (10 mL) and treated with TFA (1.2 mL). The resulting mixture was stirred at rt for 4 h and basified with 1 M NaHCO₃ (15 mL). After stirring at rt for 2 min, it was separated and the aqueous was extracted with DCM (15 mL). The combined DCM extracts were concentrated and dried to give a light brown oil which was purified by flash chromatography (gradient: EtOAc/hex 0-100% then MeOH/DCM 0-20%) to give the title compound as a white solid (263.7 mg, 45% over 2 steps). ¹H NMR (500 MHz, CHLOROFORM-d) δ=8.60 (s, 1H, NH), 8.58 (s, 2H), 8.56 (d, J=8.2 Hz, 1H), 7.66 (dd, J=5.3, 8.3 Hz, 1H), 7.49 (dd, J=2.3, 8.8 Hz, 1H), 7.37 (t, J=8.0 Hz, 1H), 7.00 (d, J=11.2 Hz, 1H), 3.91-3.85 (m, 4H), 3.82-3.78 (m, 4H), 2.94-2.82 (m, 4H), 2.36 (br t, J=10.5 Hz, 2H), 1.08 (d, J=6.2 Hz, 6H); LCMS [M+H]⁺ 577.5.

Example 365: N-[4-fluoro-5-[1-(6-methoxypyrimidin-4-yl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide

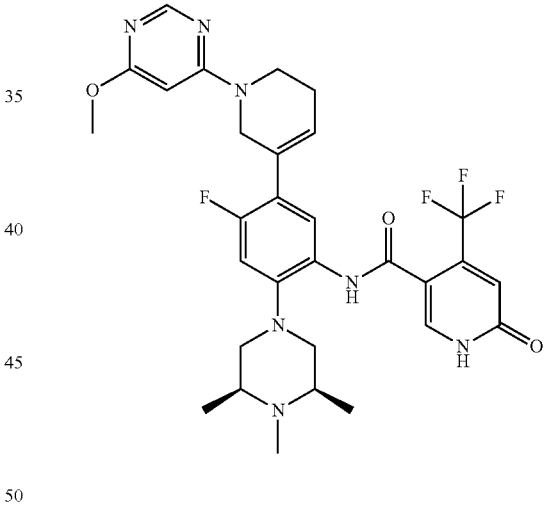

The procedure followed was similar to Example 270 using N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (26 mg, 0.051 mmol) and 4-Iodo-6-methoxypyrimidine (13.90 mg, 0.059 mmol) to give the title compound (22 mg, 66% yield). ¹H NMR (500 MHz, METHANOL-d4) δ=8.14-8.06 (m, 1H), 7.87-7.81 (m, 1H), 7.72-7.63 (m, 1H), 6.92-6.85 (m, 1H), 6.83-6.77 (m, 1H), 6.10-6.02 (m, 1H), 5.96-5.92 (m, 1H), 4.30-4.21 (m, 2H), 3.82-3.78 (m, 3H), 3.77-3.72 (m, 2H), 2.97-2.90 (m, 2H), 2.52-2.46 (m, 2H), 2.46-2.39 (m, 2H), 2.35-2.29 (m, 2H), 2.27 (s, 3H), 1.07-1.02 (m, 6H); LCMS [M+H]+ 616.6.

Example 366: N-[4-fluoro-5-[1-(5-methoxypyrimidin-2-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

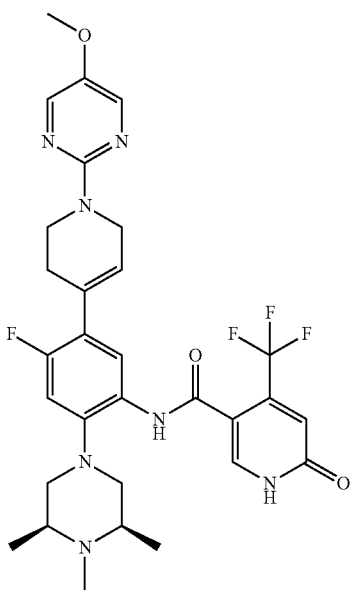 [SMILES: COc1cnc(N2CC=C(c3cc(NC(=O)c4c[nH]c(=O)cc4C(F)(F)F)c(N4C[C@@H](C)N(C)[C@@H](C)C4)cc3F)CC2)nc1]

The procedure followed was similar to Example 270 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (38 mg, 0.075 mmol) and 2-bromo-5-methoxypyrimidine (16.98 mg, 0.090 mmol) in 2-propanol (2.5 ml). The standard workup and purification provided the title compound as a tan coloured powder (24 mg, 50% yield). $^1$H NMR (500 MHz, METHANOL-d4) δ=8.22-8.16 (m, 2H), 7.98-7.93 (m, 1H), 7.84-7.76 (m, 1H), 6.99-6.94 (m, 1H), 6.94-6.91 (m, 1H), 6.16-6.10 (m, 1H), 4.32-4.28 (m, 2H), 4.01-3.96 (m, 2H), 3.86-3.83 (m, 3H), 3.06-3.00 (m, 2H), 2.63-2.57 (m, 4H), 2.56-2.50 (m, 2H), 2.39-2.38 (m, 3H), 1.18-1.16 (m, 6H); LCMS [M+H]+ 616.7

Example 367: N-[4-fluoro-5-[1-(5-fluoropyrimidin-2-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

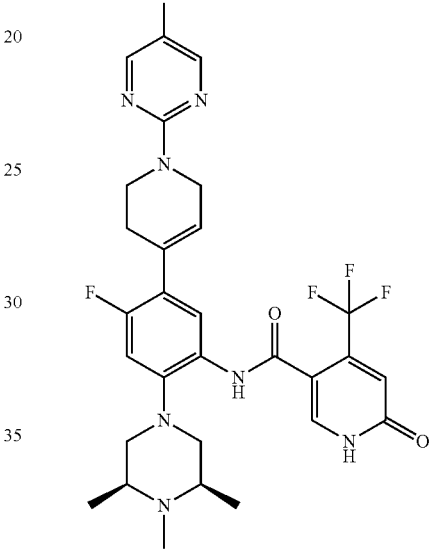

The procedure followed was similar to Example 270 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (32 mg, 0.063 mmol) and 2-bromo-5-fluoropyrimidine (13.39 mg, 0.076 mmol) in 2-propanol (2.5 ml). Workup and purification provided the title compound as a tan coloured powder (28 mg, 70% yield). $^1$H NMR (500 MHz, METHANOL-d4) δ=8.37-8.28 (m, 2H), 7.98-7.92 (m, 1H), 7.85-7.74 (m, 1H), 6.98-6.94 (m, 1H), 6.93-6.90 (m, 1H), 6.17-6.07 (m, 1H), 4.37-4.33 (m, 2H), 4.03 (t, J=5.6 Hz, 2H), 3.05-2.99 (m, 2H), 2.63-2.57 (m, 4H), 2.56-2.49 (m, 2H), 2.39-2.36 (m, 3H), 1.19-1.16 (m, 6H); LCMS [M+H]+ 604.6.

Example 368: N-[5-[1-(4,6-dimethylpyrimidin-2-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

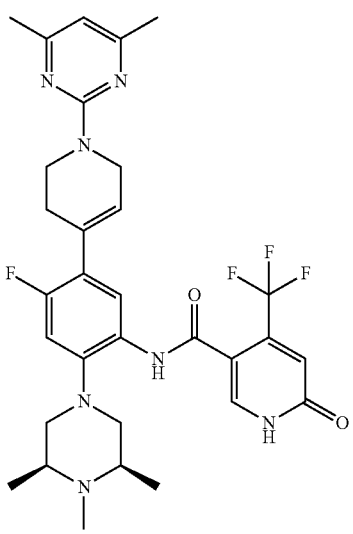 [SMILES: Cc1cc(C)nc(N2CC=C(c3cc(NC(=O)c4c[nH]c(=O)cc4C(F)(F)F)c(N4C[C@@H](C)N(C)[C@@H](C)C4)cc3F)CC2)n1]

A procedure similar to that of Example 270 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) and 2-bromo-4,6-dimethylpyrimidine (13.27 mg, 0.071 mmol) gave the title compound (28 mg, 73% yield). $^1$H NMR (500 MHz, METHANOL-d4) δ=7.99-7.92 (m, 1H), 7.83-7.75 (m, 1H), 6.98-6.94 (m, 1H), 6.93-6.90 (m, 1H), 6.46-6.39 (m, 1H), 6.16-6.08 (m, 1H), 4.41-4.37 (m, 2H), 4.09-4.03 (m, 2H), 3.07-3.00 (m, 2H), 2.63-2.52 (m, 6H), 2.39-2.37 (m, 3H), 2.33-2.30 (m, 6H), 1.17 (d, J=6.0 Hz, 6H); LCMS [M+H]+ 614.7.

Example 369: N-[4-fluoro-5-[1-(5-formylpyrimidin-2-yl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

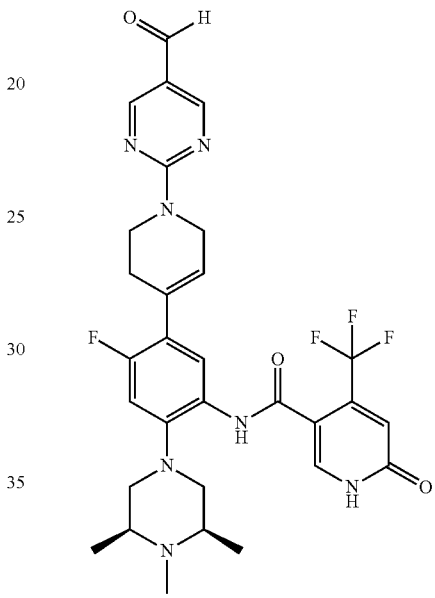

The procedure followed was similar to Example 270 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (50 mg, 0.099 mmol) and 2-bromo-pyrimidine-5-carbaldehyde (22.11 mg, 0.118 mmol) to give the title compound as a beige powder (24 mg, 38% yield). $^1$H NMR (500 MHz, METHANOL-d4) δ=9.82-9.72 (m, 1H), 8.87-8.76 (m, 2H), 7.99-7.92 (m, 1H), 7.85-7.77 (m, 1H), 6.99-6.94 (m, 1H), 6.93-6.90 (m, 1H), 6.19-6.10 (m, 1H), 4.58-4.52 (m, 2H), 4.28-4.19 (m, 2H), 3.08-3.01 (m, 2H), 2.68-2.63 (m, 2H), 2.63-2.57 (m, 2H), 2.56-2.48 (m, 2H), 2.39-2.36 (m, 3H), 1.18-1.15 (m, 6H); LCMS [M+H]+ 614.7.

Example 370: N-[4-fluoro-5-[2-[methyl(oxan-4-yl)amino]pyrimidin-5-yl]-2-[(3R)-3,4-dimethylpiperazin-1-yl]phenyl]-6-oxo-4-(trifluoromethyl)-1H-pyridine-3-carboxamide

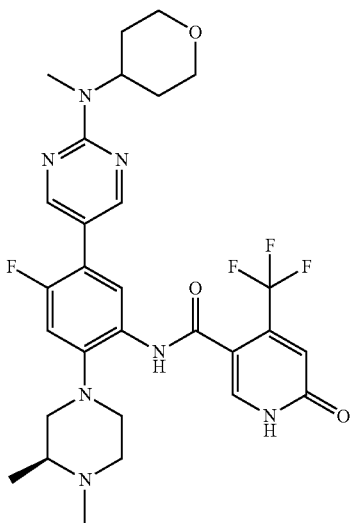 [SMILES: C[C@H]1CN(c2cc(F)c(-c3cnc(N(C)C4CCOCC4)nc3)cc2NC(=O)c2c[nH]c(=O)cc2C(F)(F)F)CCN1C]

To a mixture of 2-chloropyrimidine-5-boronic acid (32 mg, 0.2 mmol) and N-methyl-N-tetrahydro-2H-pyran-4-ylamine (26 μL, 0.21 mmol) in EtOH (2 mL) was added triethylamine (0.070 mL, 0.5 mmol). The resulting mixture was stirred at 75° C. for 5 h. Solvents were removed to give crude (2-(methyl(tetrahydro-2H-pyran-4-yl)amino)pyrimidin-5-yl)boronic acid as a light yellow solid. LCMS [M+H]$^+$ 238.2. The title compound (white solid, 5.4 mg, 9%) was prepared similar to Example 29 using crude (2-(methyl(tetrahydro-2H-pyran-4-yl)amino)pyrimidin-5-yl)boronic acid (0.2 mmol) and (S)—N-(5-bromo-2-(3,4-dimethylpiperazin-1-yl)-4-fluorophenyl)-6-oxo-4-(trifluoromethyl)-1,6-dihydropyridine-3-carboxamide (49.1 mg, 0.1 mmol). $^1$H NMR (500 MHz, CHLOROFORM-d) δ=8.73 (br s, 1H), 8.57 (s, 2H), 8.52-8.40 (m, 1H), 7.87 (br s, 1H), 7.11-6.91 (m, 2H), 4.98 (br t, J=11.9 Hz, 1H), 4.11 (br dd, J=4.0, 11.4 Hz, 2H), 3.61 (br t, J=11.6 Hz, 2H), 3.11 (s, 3H), 3.05-2.82 (m, 4H), 2.70-2.55 (m, 1H), 2.38 (br s, 3H), 2.30-2.16 (m, 1H), 1.94 (dq, J=4.4, 12.2 Hz, 2H), 1.70 (br d, J=11.5 Hz, 2H), 1.13 (br s, 3H); LCMS [M+H]$^+$ 604.5.

Example 371: N-[4-fluoro-5-[2-[methyl(oxan-4-yl)amino]pyrimidin-5-yl]-2-[(3R,5S)-3,4,5-trimethylpiperazin-1-yl]phenyl]-6-oxo-4-(trifluoromethyl)-1H-pyridine-3-carboxamide

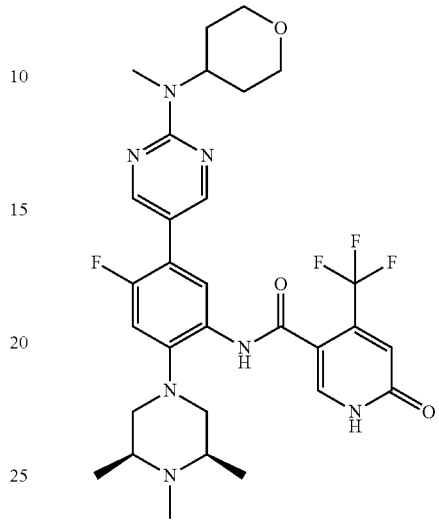

The title compound (white solid, 4.6 mg, 7%) was prepared similar to Example 31 using crude (2-(methyl(tetrahydro-2H-pyran-4-yl)amino)pyrimidin-5-yl)boronic acid (0.2 mmol) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, CHLOROFORM-d) δ=8.72 (br s, 1H), 8.57 (br s, 2H), 8.46 (br s, 1H), 7.86 (br s, 1H), 7.03 (br d, J=11.0 Hz, 2H), 4.97 (br t, J=11.7 Hz, 1H), 4.11 (br dd, J=3.6, 11.2 Hz, 2H), 3.61 (br t, J=11.5 Hz, 2H), 3.11 (s, 3H), 2.91-2.78 (m, 2H), 2.76-2.58 (m, 2H), 2.35 (br s, 4H), 1.94 (dq, J=4.0, 12.0 Hz, 3H), 1.70 (br d, J=11.5 Hz, 4H), 1.17 (br s, 6H); LCMS [M+H]$^+$ 618.6.

Example 372: N-[5-[1-(dimethylcarbamoyl)-3,6-dihydro-2H-pyridin-5-yl]-4-fluoro-2-[(3R,5S)-3,4,5-trimethylpiperazin-1-yl]phenyl]-6-oxo-4-(trifluoromethyl)-1H-pyridine-3-carboxamide

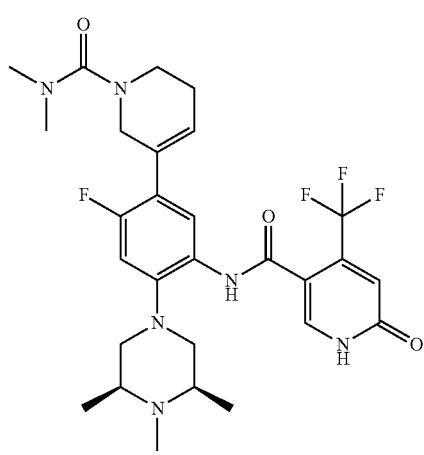 [SMILES: C[C@@H]1CN(c2cc(F)c(C3=CCCN(C(=O)N(C)C)C3)cc2NC(=O)c2c[nH]c(=O)cc2C(F)(F)F)C[C@H](C)N1C]

To a mixture of N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and N,N-diisopropylethylamine (0.017 ml, 0.099 mmol) in DCM (3 ml) at RT, was added dimethylcarbamoyl chloride (5.67 µl, 0.062 mmol). After stirring overnight, additional dimethylcarbamoyl chloride (0.5 eq) was added and the mixture was stirred for an additional 1.5 h. The reaction was quenched with water, and standard workup and purification gave the title compound as a white powder (24 mg, 80% yield). $^1$H NMR (500 MHz, METHANOL-d4) δ=7.98-7.90 (m, 1H), 7.81-7.71 (m, 1H), 7.00-6.94 (m, 1H), 6.94-6.90 (m, 1H), 6.16-6.03 (m, 1H), 4.11-4.03 (m, 2H), 3.45-3.41 (m, 2H), 3.07-3.01 (m, 2H), 2.93-2.88 (m, 6H), 2.63-2.57 (m, 2H), 2.57-2.50 (m, 2H), 2.44-2.39 (m, 2H), 2.39-2.36 (m, 3H), 1.18-1.15 (m, 6H); LCMS [M+H]+ 579.6.

Example 373: ethyl 5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate

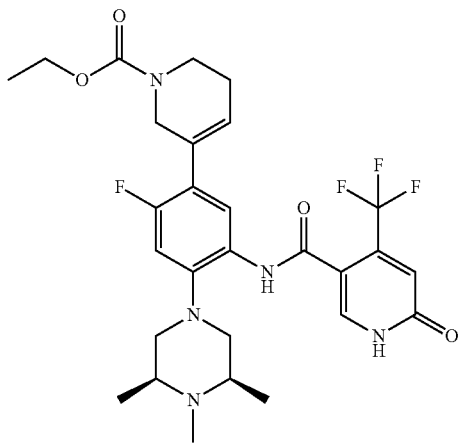 [SMILES: CCOC(=O)N1CCC=C(c2cc(NC(=O)c3c[nH]c(=O)cc3C(F)(F)F)c(N3C[C@@H](C)N(C)[C@@H](C)C3)cc2F)C1]

This example was prepared using a procedure similar to Example 39 from N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (400 mg, 0.661 mmol) and 1-Boc-5,6-dihydro-2H-pyridine-3-boronic acid, pinacol ester (306 mg, 0.991 mmol) followed by deprotection of a portion (50 mg, 0.071 mmol) of the resulting tert-butyl 5-(2-fluoro-5-(4-(trifluoromethyl)-6-(2-(trimethylsilyl)ethoxy)nicotinamido)-4-((3S,5R)-3,4,5-trimethylpiperazin-1-yl)phenyl)-3,6-dihydropyridine-1(2H)-carboxylate intermediate by stirring in a solution of TFA in DCM (5 ml) at room temperature for 45 min. Standard workup and purification gave the title compound (33 mg, 73% yield). $^1$H NMR (500 MHz, METHANOL-d4) δ=7.86-7.80 (m, 1H), 7.69-7.60 (m, 1H), 6.89-6.82 (m, 1H), 6.82-6.77 (m, 1H), 6.02-5.95 (m, 1H), 4.15-4.06 (m, 2H), 3.54-3.42 (m, 2H), 2.95-2.89 (m, 2H), 2.54-2.40 (m, 4H), 2.28-2.25 (m, 3H), 2.24-2.19 (m, 2H), 1.40-1.37 (m, 9H), 1.05 (d, J=6.0 Hz, 6H); LCMS [M+H]+ 608.4

Example 374: N-[4-fluoro-5-[1-(pyrrolidine-1-carbonyl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide

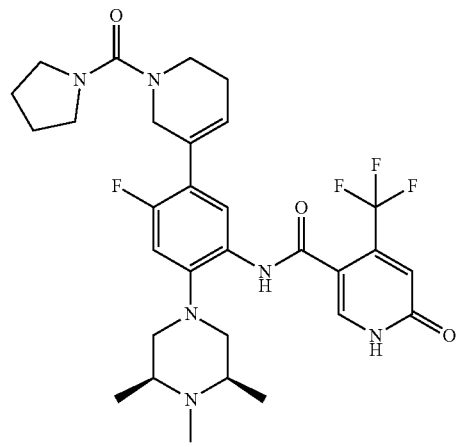 [SMILES: C[C@@H]1CN(c2cc(F)c(C3=CCCN(C(=O)N4CCCC4)C3)cc2NC(=O)c2c[nH]c(=O)cc2C(F)(F)F)C[C@H](C)N1C]

The procedure followed was similar to that of Example 253 using N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) N,N-diisopropylethylamine (0.017 ml, 0.099 mmol), and 1-pyrrolidinecarbonyl chloride (5.71 µl, 0.052 mmol) in DCM (3 mL) at RT to give the title compound (24 mg, 77% yield). $^1$H NMR (500 MHz, METHANOL-d4) δ=7.98-7.89 (m, 1H), 7.80-7.71 (m, 1H), 6.99-6.94 (m, 1H), 6.93-6.89 (m, 1H), 6.16-6.05 (m, 1H), 4.15-4.05 (m, 2H), 3.51-3.41 (m, 6H), 3.07-2.96 (m, 2H), 2.64-2.50 (m, 4H), 2.43-2.33 (m, 5H), 1.93-1.83 (m, 4H), 1.18-1.11 (m, 6H); LCMS [M+H]+ 605.7.

Example 375: N-[4-fluoro-5-[1-(5-methoxypyrimidin-2-yl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide

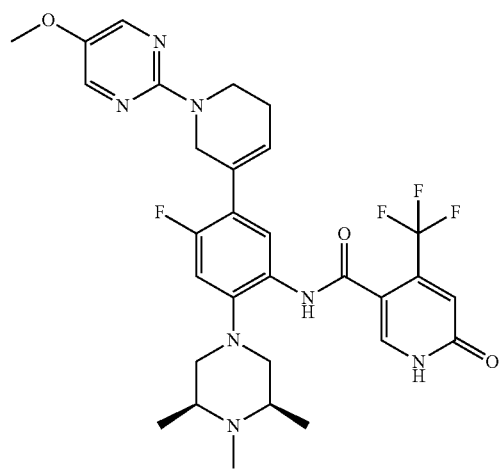 [SMILES: COc1cnc(N2CCC=C(c3cc(NC(=O)c4c[nH]c(=O)cc4C(F)(F)F)c(N4C[C@@H](C)N(C)[C@@H](C)C4)cc3F)C2)nc1]

The procedure followed was similar to Example 270 using N-(4-fluoro-5-(1,2,5,6-tetrahydropyridin-3-yl)-2-

((3S,5R)-3,4,5-trimethylpiperazin-1-yl)phenyl)-6-oxo-4-(trifluoromethyl)-1,6-dihydropyridine-3-carboxamide (25 mg, 0.049 mmol) and 2-bromo-5-methoxypyrimidine (13.03 mg, 0.069 mmol) to afford, after workup and purification, the title compound (19 mg, 61% yield). $^1$H NMR (500 MHz, METHANOL-d4) δ 8.16 (s, 2H), 7.96 (s, 1H), 7.80 (d, J=7.82 Hz, 1H), 6.98 (d, J=12.10 Hz, 1H), 6.92 (s, 1H), 6.13 (br. s, 1H), 4.46 (br. s., 2H), 3.93 (t, J=5.62 Hz, 2H), 3.83 (s, 3H), 3.04 (d, J=11.13 Hz, 2H), 2.58-2.64 (m, 2H), 2.55 (d, J=5.62 Hz, 2H), 2.37-2.44 (m, 5H), 1.17 (d, J=5.99 Hz, 6H); LCMS [M+H]+ 616.7.

Example 376: N-[4-fluoro-5-[1-(5-methylpyrimidin-2-yl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide

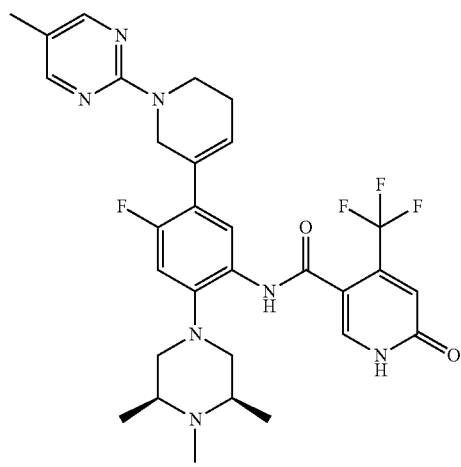 [SMILES: Cc1cnc(N2CCC=C(c3cc(NC(=O)c4c[nH]c(=O)cc4C(F)(F)F)c(N4C[C@@H](C)N(C)[C@@H](C)C4)cc3F)C2)nc1]

The procedure followed was similar to Example 270 using N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and 2-chloro-5-methylpyrimidine (8.87 mg, 0.069 mmol) to give, after workup and purification, the title compound (22 mg, 70% yield). $^1$H NMR (500 MHz, METHANOL-d4) δ 8.22 (s, 2H), 7.96 (s, 1H), 7.80 (d, J=7.95 Hz, 1H), 6.98 (d, J=12.23 Hz, 1H), 6.92 (s, 1H), 6.15 (br. s, 1H), 4.49 (br. s., 2H), 3.96 (t, J=5.75 Hz, 2H), 3.04 (d, J=11.13 Hz, 2H), 2.58-2.65 (m, 2H), 2.49-2.56 (m, 2H), 2.55 (d, J=4.77 Hz, 2H), 2.41 (d, J=3.30 Hz, 2H), 2.38 (s, 3H), 2.16 (s, 3H), 1.17 (d, J=6.11 Hz, 6H); LCMS [M+H]+ 600.7.

Example 377: N-[4-fluoro-5-[1-(5-fluoropyrimidin-2-yl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide

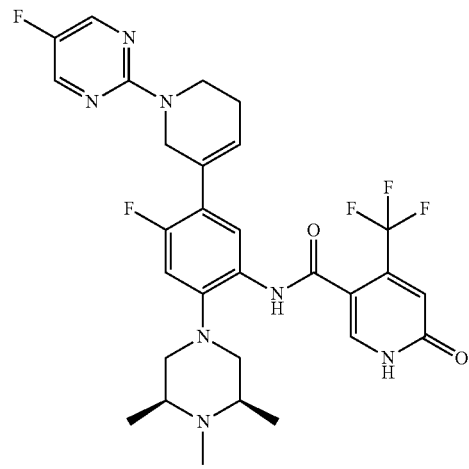 [SMILES: C[C@@H]1CN(c2cc(F)c(C3=CCCN(c4ncc(F)cn4)C3)cc2NC(=O)c2c[nH]c(=O)cc2C(F)(F)F)C[C@H](C)N1C]

The procedure followed was similar to Example 270 using N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and 2-bromo-5-fluoropyrimidine (10.46 mg, 0.059 mmol) to give, after workup and purification, the title compound (23 mg, 74% yield). $^1$H NMR (500 MHz, METHANOL-d4) δ 8.28-8.36 (m, 2H), 7.96 (s, 1H), 7.79 (d, J=7.95 Hz, 1H), 6.98 (d, J=12.23 Hz, 1H), 6.92 (s, 1H), 6.15 (br. s., 1H), 4.51 (br. s., 2H), 3.98 (t, J=5.75 Hz, 2H), 3.04 (d, J=11.13 Hz, 2H), 2.58-2.66 (m, 2H), 2.49-2.57 (m, 2H), 2.41 (d, J=3.67 Hz, 2H), 2.38 (s, 3H), 1.17 (d, J=6.11 Hz, 6H); LCMS [M+H]+ 604.5.

Example 378: N-[4-fluoro-5-(2-morpholin-4-ylpyrimidin-4-yl)-2-[(3R,5S)-3,4,5-trimethylpiperazin-1-yl]phenyl]-6-oxo-4-(trifluoromethyl)-1H-pyridine-3-carboxamide

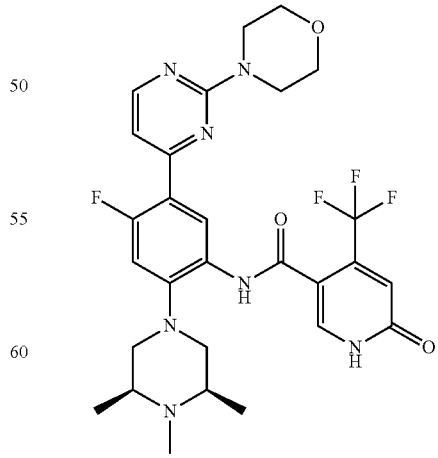

The title compound was prepared similar to the sequence described above for the preparation of Example 39 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) and 4-[5-(4,4,5,5-Tetramethyl-[1,3,2]dioxaborolan-2-yl)-pyridin-2-yl]-morpholine to give, after deprotection of the N-(4-fluoro-5-(6-morpholinopyridin-3-yl)-2-((3S,5R)-3,4,5-trimethylpiperazin-1-yl)phenyl)-4-(trifluoromethyl)-6-(2-(trimethylsilyl)ethoxy)nicotinamide intermediate, the title compound (48.6 mg, 44% yield). $^1$H NMR (500 MHz, MeOD) δ 8.58 (d, J=8.3 Hz, 1H), 8.37 (d, J=5.2 Hz, 1H), 7.92 (s, 1H), 7.13 (dd, J=5.0, 1.6 Hz, 1H), 7.01 (d, J=13.2 Hz, 1H), 6.92 (s, 1H), 3.84 (d, J=5.0 Hz, 4H), 3.77-3.75 (m, 4H), 3.16 (d, J=10.4 Hz, 2H), 2.64 (dd, J=23.5, 12.5 Hz, 4H), 2.40 (s, 3H), 1.18 (d, J=5.9 Hz, 6H); LCMS HSS [M+1]$^+$=590.55.

Example 379: 4-fluoro-N-[4-fluoro-5-[2-(4-methylpiperazin-1-yl)pyrimidin-5-yl]-2-[(3R,5S)-3,4,5-trimethylpiperazin-1-yl]phenyl]-2-(trifluoromethyl)benzamide phenyl)-4-fluoro-2-(trifluoromethyl)benzamide as a pale beige solid (417 mg, 39%). LCMS [M+H]$^+$ 506.4. The title compound (white solid, 41.2 mg, 68%) was prepared by a procedure similar to examples hereinabove using 2-(4-methylpiperazin-1-yl)pyrimidine-5-boronic acid pinacol ester (60.8 mg, 0.2 mmol) and N-(5-bromo-4-fluoro-2-((3S,5R)-3,4,5-trimethylpiperazin-1-yl)phenyl)-4-fluoro-2-(trifluoromethyl)benzamide (50.6 mg, 0.1 mmol). $^1$H NMR (500 MHz, CHLOROFORM-d) δ=8.60-8.53 (m, 4H), 7.66 (dd, J=5.3, 8.4 Hz, 1H), 7.50 (dd, J=2.3, 8.7 Hz, 1H), 7.38 (t, J=8.0 Hz, 1H), 7.00 (d, J=11.2 Hz, 1H), 3.96-3.87 (m, 4H), 2.82 (br d, J=11.0 Hz, 2H), 2.62 (t, J=10.9 Hz, 2H), 2.50 (t, J=5.1 Hz, 4H), 2.36 (s, 3H), 2.27 (s, 3H), 2.26-2.19 (m, 2H), 1.10 (d, J=6.2 Hz, 6H); LCMS [M+H]$^+$ 604.6.

Example 380: N-[5-[2-(dimethylamino)pyrimidin-5-yl]-4-fluoro-2-[(3R,5S)-3,4,5-trimethylpiperazin-1-yl]phenyl]-4-fluoro-2-(trifluoromethyl)benzamide

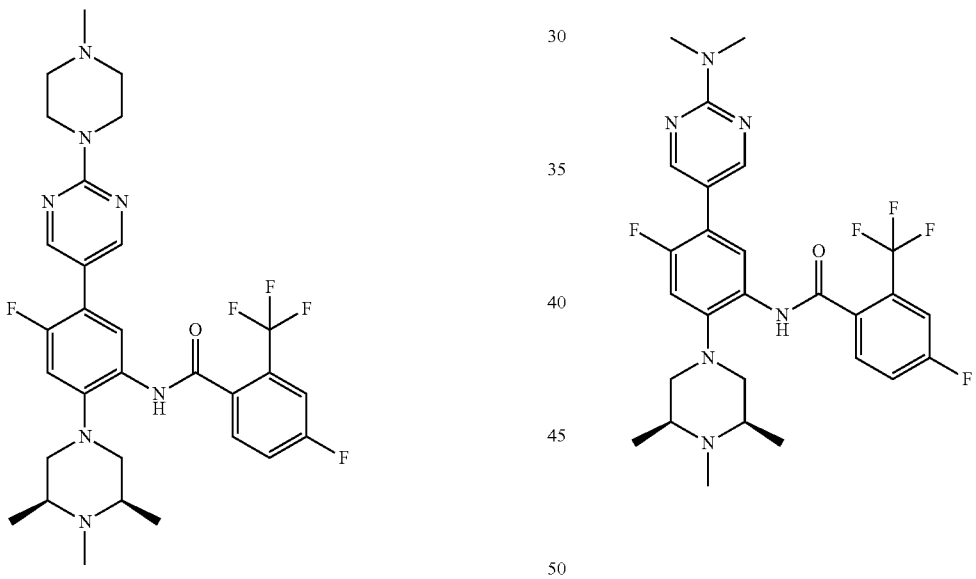

To a solution of 4-fluoro-2-(trifluoromethyl)benzoyl chloride (0.61 mL, 4 mmol) in DCM (15 mL) at rt was added Et$_3$N (1.12 mL, 8 mmol). After addition, the resulting mixture was stirred at rt for 5 min, before a solution of 5-bromo-4-fluoro-2-((3S,5R)-3,4,5-trimethylpiperazin-1-yl)aniline (632 mg, 2 mmol) in DCM (10 mL) was added. The resulting mixture was stirred at rt for 2 h. After basic workup with sat. NaHCO$_3$, it was purified by flash chromatography (gradient: EtOAc/hex 0-100%) to give N-(5-bromo-4-fluoro-2-((3S,5R)-3,4,5-trimethylpiperazin-1-yl)

The title compound (pale beige solid, 44.9 mg, 81%) was prepared through a procedure similar to Example 31 using N,N-dimethyl-5-(4,4,5,5-tetramethyl-1,3,2-dioxaborolan-2-yl)pyrimidin-2-amine (50 mg, 0.2 mmol) and N-(5-bromo-4-fluoro-2-((3S,5R)-3,4,5-trimethylpiperazin-1-yl)phenyl)-4-fluoro-2-(trifluoromethyl)benzamide (50.6 mg, 0.1 mmol). $^1$H NMR (500 MHz, CHLOROFORM-d) δ=8.62-8.51 (m, 4H), 7.66 (dd, J=5.3, 8.4 Hz, 1H), 7.49 (dd, J=2.3, 8.8 Hz, 1H), 7.38 (dt, J=2.3, 8.1 Hz, 1H), 7.00 (d, J=11.2 Hz, 1H), 3.25 (s, 6H), 2.82 (br d, J=11.0 Hz, 2H), 2.62 (br t, J=10.8 Hz, 2H), 2.28 (s, 3H), 2.25-2.17 (m, 2H), 1.11 (d, J=6.1 Hz, 6H); LCMS [M+H]$^+$ 549.5.

Example 381: 4-fluoro-N-[4-fluoro-2-[(3R,5S)-3,4,5-trimethylpiperazin-1-yl]-5-[2-[(3R,5S)-3,4,5-trimethylpiperazin-1-yl]pyrimidin-5-yl]phenyl]-2-(trifluoromethyl)benzamide

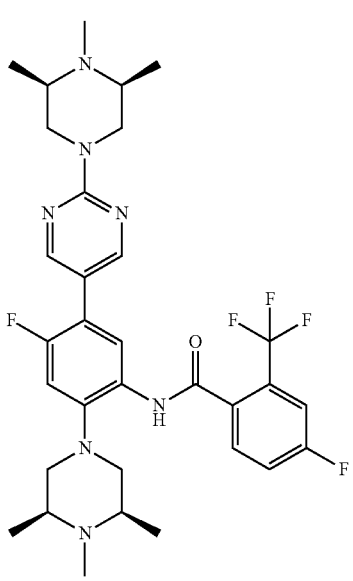 [SMILES: C[C@@H]1CN(c2ncc(-c3cc(NC(=O)c4ccc(F)cc4C(F)(F)F)c(N4C[C@@H](C)N(C)[C@@H](C)C4)cc3F)cn2)C[C@H](C)N1C]

To a mixture of 2-chloropyrimidine-5-boronic acid (48 mg, 0.3 mmol) and (2R,6S)-1,2,6-trimethylpiperazine (40 mg, 0.315 mmol) in EtOH (2 mL) was added triethylamine (0.07 mL, 0.5 mmol). The resulting mixture was stirred at 80° C. for 1 h. Solvents were removed to give crude (2-((3S,5R)-3,4,5-trimethylpiperazin-1-yl)pyrimidin-5-yl) boronic acid as a pale yellow oil (semi-solid). The title compound (light brown solid, 35.3 mg, 55%) was prepared similar to the procedure of Example 31 using crude (2-((3S,5R)-3,4,5-trimethylpiperazin-1-yl)pyrimidin-5-yl)boronic acid (0.3 mmol) and N-(5-bromo-4-fluoro-2-((3S,5R)-3,4,5-trimethylpiperazin-1-yl)phenyl)-4-fluoro-2-(trifluoromethyl)benzamide (50.6 mg, 0.1 mmol). $^1$H NMR (500 MHz, CHLOROFORM-d) δ=8.60-8.52 (m, 4H), 7.66 (dd, J=5.3, 8.4 Hz, 1H), 7.50 (dd, J=2.4, 8.8 Hz, 1H), 7.38 (dt, J=2.3, 8.1 Hz, 1H), 7.00 (d, J=11.2 Hz, 1H), 4.65-4.59 (m, 2H), 2.87-2.76 (m, 4H), 2.62 (t, J=11.0 Hz, 2H), 2.32 (s, 3H), 2.29-2.19 (m, 7H), 1.21 (d, J=6.1 Hz, 6H), 1.10 (d, J=6.2 Hz, 6H); LCMS [M+H]$^+$ 632.7.

Example 382: 4-fluoro-N-[4-fluoro-5-[2-(4-methylpiperazin-1-yl)pyrimidin-5-yl]-2-[(3R,5R)-3,4,5-trimethylpiperazin-1-yl]phenyl]-2-(trifluoromethyl)benzamide

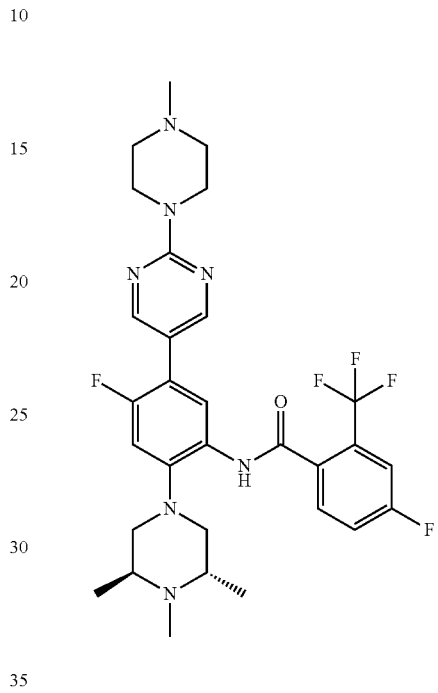

To a solution of 4-fluoro-2-(trifluoromethyl)benzoyl chloride (0.30 mL, 2 mmol) in DCM (9 mL) at rt was added Et$_3$N (0.56 mL, 4 mmol). After addition, the resulting mixture was stirred at rt for 5 min, before a solution of 5-bromo-4-fluoro-2-((3S,5S)-3,4,5-trimethylpiperazin-1-yl)aniline (316 mg, 1 mmol, prepared in a similar manner to examples hereinabove) in DCM (1 mL) was added. The resulting mixture was stirred at rt for 1 h. After quenching with sat. NaHCO$_3$ (5 mL) and stirring for 5 min at rt, the DCM layer was loaded onto samplet and purified by flash chromatography (gradient: EtOAc/hex 0-100% then MeOH/DCM 0-10%) to give N-(5-bromo-4-fluoro-2-((3S,5S)-3,4,5-trimethylpiperazin-1-yl)phenyl)-4-fluoro-2-(trifluoromethyl)benzamide as a pale beige solid (424 mg, 84%). LCMS [M+H]$^+$ 506.4. The title compound (white solid, 46.3 mg, 77%) was prepared using a procedure similar to Example 31 using 2-(4-methylpiperazin-1-yl)pyrimidine-5-boronic acid pinacol ester (61 mg, 0.2 mmol) and N-(5-bromo-4-fluoro-2-((3S,5S)-3,4,5-trimethylpiperazin-1-yl)phenyl)-4-fluoro-2-(trifluoromethyl)benzamide (51 mg, 0.1 mmol). $^1$H NMR (500 MHz, CHLOROFORM-d) δ=8.62 (s, 1H), 8.56 (s, 2H), 8.53 (d, J=8.2 Hz, 1H), 7.67 (dd, J=5.3, 8.4 Hz, 1H), 7.49 (dd, J=2.3, 8.7 Hz, 1H), 7.36 (t, J=8.1 Hz, 1H), 7.00 (d, J=11.2 Hz, 1H), 3.96-3.87 (m, 4H), 2.94-2.78 (m, 4H), 2.66 (br dd, J=5.9, 10.6 Hz, 2H), 2.50 (t, J=5.0 Hz, 4H), 2.36 (s, 3H), 2.29 (s, 3H), 0.93 (br d, J=6.2 Hz, 6H); LCMS [M+H]$^+$ 604.5.

539

Example 383: 4-(difluoromethyl)-N-[4-fluoro-5-[2-[(2R,6S)-2,6-dimethylmorpholin-4-yl]pyrimidin-5-yl]-2-[(3R)-3,4-dimethylpiperazin-1-yl]phenyl]-1-methyl-6-oxopyridine-3-carboxamide

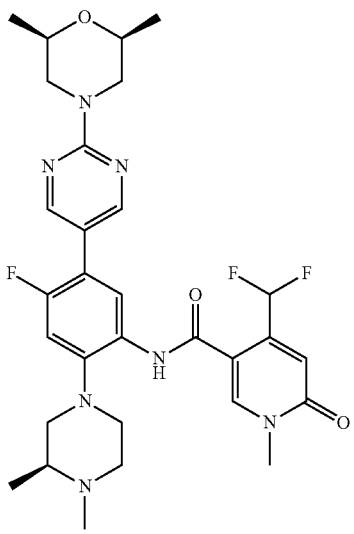

Step 1: (S)—N-(5-bromo-2-(3,4-dimethylpiperazin-1-yl)-4-fluorophenyl)-4-(difluoromethyl)-1-methyl-6-oxo-1,6-dihydropyridine-3-carboxamide

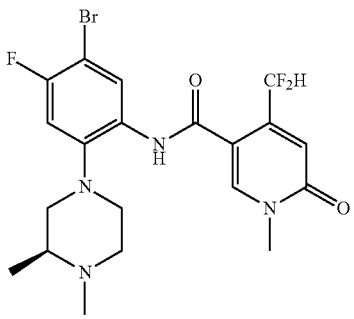

To a stirred solution of 4-(difluoromethyl)-1-methyl-6-oxo-1,6-dihydropyridine-3-carboxylic acid (8 g, 39.40 mmol, 1 eq, prepared in Example 217 Step 6) in DMF (80 mL) was added DIPEA (21.7 mL, 118.2 mmol, 3 eq), HATU (44.9 g, 118.2 mmol, 3 eq) and then (S)-5-bromo-2-(3,4-dimethylpiperazin-1-yl)-4-fluoroaniline (11.94 g, 39.4 mmol, 1 eq) was added at 0° C. under argon atm, and the mixture was stirred for 16 h. TLC analysis indicated formation of nonpolar spots. The reaction mixture was diluted with ice water (200 mL) and extracted with EtOAc (2×500 mL). The organic layer was washed with brine and dried over Na$_2$SO$_4$ and concentrated under reduced pressure to give crude product. The crude product was purified by column chromatography (neutral alumina) using 0-5% MeOH in EtOAc as an eluent to give (S)—N-(5-bromo-2-(3,4-dimethylpiperazin-1-yl)-4-fluorophenyl)-4-(difluoromethyl)-1-methyl-6-oxo-1,6-dihydropyridine-3-carboxamide (5.5 g, 50%) as a pale brown solid. LCMS: [M+H]+ 487.25.

540

Step 2: 4-(difluoromethyl)-N-[4-fluoro-5-[2-[(2R,6S)-2,6-dimethylmorpholin-4-yl]pyrimidin-5-yl]-2-[(3R)-3,4-dimethylpiperazin-1-yl]phenyl]-1-methyl-6-oxopyridine-3-carboxamide

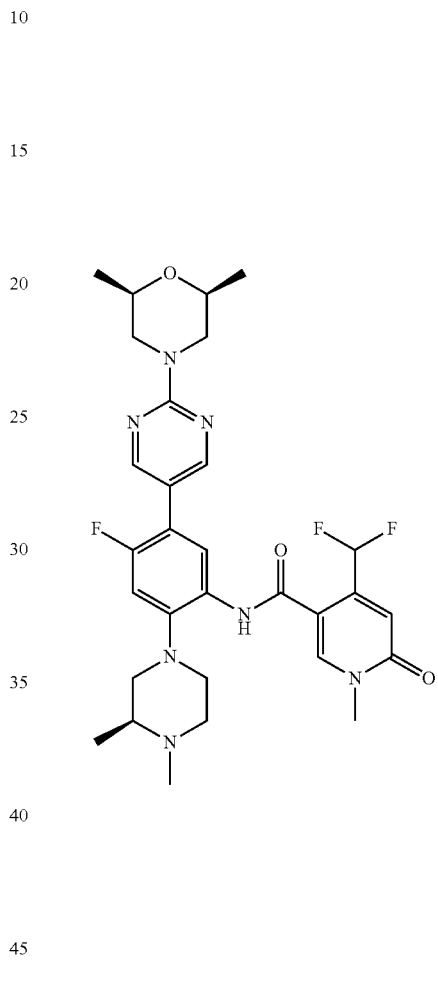

The title compound was prepared according to a procedure similar to that described in Example 31 using (S)—N-(5-bromo-2-(3,4-dimethylpiperazin-1-yl)-4-fluorophenyl)-4-(difluoromethyl)-1-methyl-6-oxo-1,6-dihydropyridine-3-carboxamide (25 mg, 0.051 mmol) and (2-((2S,6R)-2,6-dimethylmorpholino)pyrimidin-5-yl)boronic acid (18.24 mg, 0.077 mmol). $^1$H NMR (500 MHz, DMSO-d6) δ=9.48 (s, 1H), 8.51 (s, 2H), 8.36 (s, 1H), 7.68 (br d, J=8.6 Hz, 1H), 7.50-7.17 (m, 1H), 7.09 (br d, J=12.0 Hz, 1H), 6.65 (s, 1H), 4.54 (br d, J=11.7 Hz, 2H), 3.57 (ddd, J=2.3, 6.3, 10.3 Hz, 2H), 3.52 (s, 3H), 3.10-2.96 (m, 2H), 2.88-2.71 (m, 2H), 2.58 (dd, J=10.8, 13.0 Hz, 2H), 2.22 (br s, 2H), 1.20-1.11 (m, 1H), 1.16 (d, J=6.1 Hz, 5H), 0.98 (br s, 3H); LCMS [M+H]+: 600.6.

Example 384: N-[4-fluoro-5-(6-morpholin-4-ylpyridazin-3-yl)-2-[(3R,5S)-3,4,5-trimethylpiperazin-1-yl]phenyl]-6-oxo-4-(trifluoromethyl)-1H-pyridine-3-carboxamide

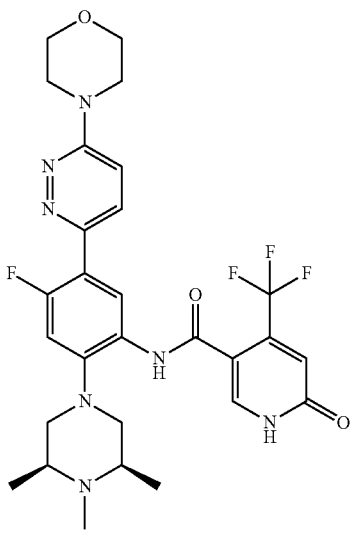

Step 1: N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy)nicotinamide

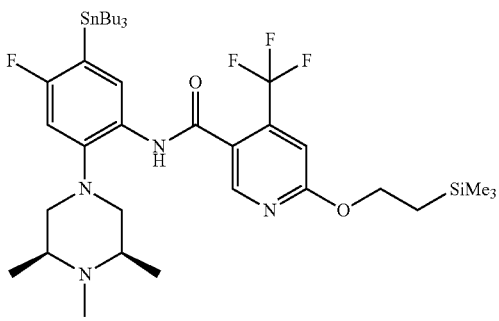

A stirred solution of N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (10 g, 17.01 mmol, 1 eq, from Example 39) in toluene (60 mL) was degassed with argon for 15 min, then hexabutylditin (17.3 mL, 34.1 mmol, 2 eq) was added, followed by Pd$_2$(dppf)$_2$Cl$_2$·DCM (1.39 g, 1.706 mmol, 0.1 eq) and after that heated to reflux under argon atmosphere for 24 h. TLC analysis indicated formation of less polar spots. The reaction mixture was filtered through celite bed washed with EtOAc; and the filtrate was evaporated under reduced pressure. The resulting crude product was purified by column chromatography (neutral alumina) using 0-5% EtOAc in pet ether as an eluent and resulted in N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy)nicotinamide (5.2 g, 36.6% yield) as a pale yellow solid. $^1$H NMR (500 MHz, MeOD) δ 8.49 (s, 1H), 7.92-7.81 (m, 1H), 7.13 (s, 1H), 6.90 (d, J=7.5 Hz, 1H), 4.58-4.54 (m, 2H), 3.10 (d, J=8.0 Hz, 2H), 2.64 (d, J=5.8 Hz, 4H), 2.43 (s, 3H), 1.65 (d, J=7.7 Hz, 3H), 1.57 (dd, J=15.6, 8.0 Hz, 6H), 1.42-1.32 (m, 10H), 1.20 (s, 11H), 1.16-1.10 (m, 6H), 0.90 (t, J=7.4 Hz, 9H), 0.11 (s, 9H); LCMS C18 [M+1]$^+$=817.75.

Step 2: N-[4-fluoro-5-(6-morpholin-4-ylpyridazin-3-yl)-2-[(3R,5S)-3,4,5-trimethylpiperazin-1-yl]phenyl]-6-oxo-4-(trifluoromethyl)-1H-pyridine-3-carboxamide

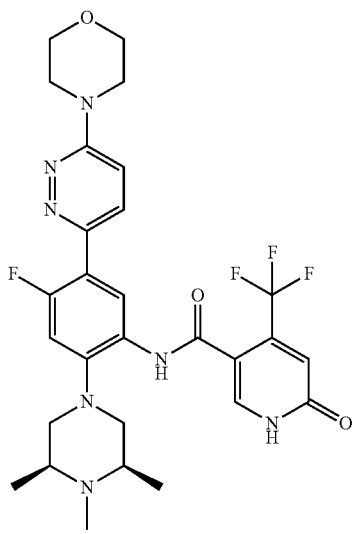

In N-methyl-2-pyrrolidinone (NMP) (247 μl) was dissolved N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy)nicotinamide (100.9 mg, 0.124 mmol). To the solution was added 4-(6-bromopyridazin-3-yl)morpholine (33.2 mg, 0.136 mmol), lithium chloride (15.73 mg, 0.371 mmol) and bis(triphenylphosphine)palladium(II) dichloride (4.78 mg, 6.80 μmol) at room temperature and then it was microwaved at the temperature of 120° C. for 2 hours. Standard workup and purification gave the title compound (2.1 mg, 3% yield). $^1$H NMR (500 MHz, MeOD) δ 8.29 (d, J=7.2 Hz, 1H), 8.02 (s, 1H), 7.78 (d, J=7.8 Hz, 1H), 7.33 (d, J=9.7 Hz, 1H), 7.11 (d, J=12.2 Hz, 1H), 6.89 (s, 1H), 3.83 (s, 4H), 3.65 (s, 4H), 2.90 (s, 2H), 2.78 (s, 2H), 2.58 (s, 2H), 1.94 (s, 3H), 1.29 (s, 6H); $^{19}$F NMR (471 MHz, MeOD) δ −63.67 (s), −119.73 (s); LCMS HSS [M+1]$^+$ =590.55.

Example 385: 4-(difluoromethyl)-N-[4-fluoro-5-[2-[(2R,6S)-2,6-dimethylmorpholin-4-yl]pyrimidin-5-yl]-2-[(3S,5R)-3,4,5-trimethylpiperazin-1-yl]phenyl]-6-oxo-1H-pyridine-3-carboxamide

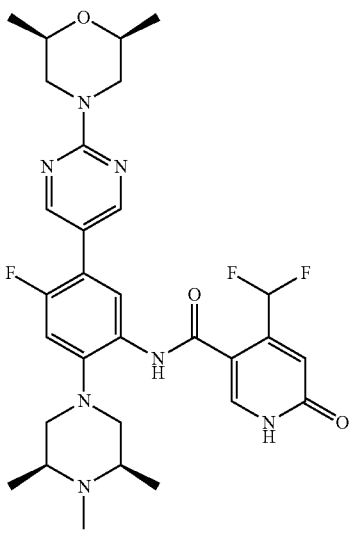

Step 1:
5-bromo-2-(2-(trimethylsilyl)ethoxy)pyridine

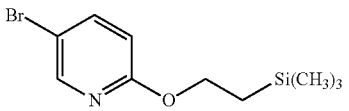

To a stirred solution of TMS ethanol (16.23 ml, 194.8 mmol, 1.5 eq) in dry THF (500 ml) was added NaH (4.68 g, 195.0 mmol, 1.5 eq) at 0° C. under argon. The mixture was stirred for 30 min and 5-bromo-2-chloropyridine (25 g, 130.2 mmol, 1 eq) in dry THF (125 ml) at the same temperature was added. The mixture was then slowly warmed to reflux for 24 h, and TLC analysis indicated formation of less polar spot along with 10% of starting material. Then, the reaction mixture cooled to RT was poured into ice water, extracted with EtOAc (2×500 ml) and washed with water (2×250 ml), and brine (2×250 ml). The organic layers were combined and dried over Na$_2$SO$_4$ and concentrated under reduced pressure to give crude product. Crude product was purified by silica gel chromatography (260-400 mesh) using 100% pet ether as an eluent to give 5-bromo-2-(2-(trimethylsilyl)ethoxy)pyridine (22 g, 64%) as a pale yellow liquid. TLC: 10% EtOAc in Pet Ether; R$_f$: 0.8.

Step 2: 5-bromo-2-(2-(trimethylsilyl)ethoxy)isonicotinaldehyde

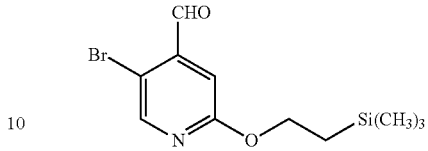

To a solution of DiPA (5.76 ml, 57.0 mmol, 1.5 eq) in dry THF (30 ml) was added n-BuLi (2.5M in n-hexane, 15.2 ml, 38.09 mmol, 1.3 eq) at −78° C. and then allowed to warm to −30° C. over 30 min. To freshly prepared LDA was added a solution of 5-bromo-2-(2-(trimethylsilyl)ethoxy)pyridine (8 g, 29.3 mmol, 1 eq) in dry THF (200 ml) at −78° C. under argon atm and was maintained for 1 h at the same temperature. Then it was quenched with DMF (2.38 g, 32.23 mmol, 1.1 eq) added dropwise and stirred at the same temperature for 10 min. TLC analysis indicated formation of polar spots. Then, the reaction mixture was quenched with sat. NH$_4$Cl (50 ml) and extracted with EtOAc (4×200 ml) then washed with water and brine. The combined organic layer was dried with Na$_2$SO$_4$ and concentrated under reduced pressure to give crude 5-bromo-2-(2-(trimethylsilyl)ethoxy)isonicotinaldehyde (7.8 g, 88.6%) as a pale yellow liquid. The crude product was used without further purification. TLC: 5% EtOAc in pet ether; R$_f$: 0.6

Step 3: methyl 4-formyl-6-(2-(trimethylsilyl)ethoxy)nicotinate

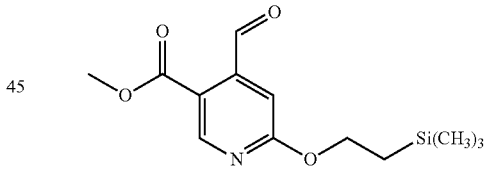

To a stirred solution of 5-bromo-2-(2-(trimethylsilyl)ethoxy)isonicotinaldehyde (7.8 g, 25.91 mmol, 1 eq) in methanol (80 ml) was added TEA (36.35 ml, 259.1 mmol, 10 eq) at RT in a steel bomb degassed with argon for 10 min, then Pd$_2$(dppf)Cl$_2$DCM (2.11 g, 2.59 mmol, 0.1 eq) was added and the mixture was then heated to 70° C. under 250 Psi (CO gas) for 16 h. TLC analysis indicated formation of polar spots. The reaction mixture was filtered through celite bed washed with methanol; and the filtrate was evaporated under reduced pressure. The crude compound was purified by flash chromatography using 5% EtOAc in pet ether as an eluent to afford methyl 4-formyl-6-(2-(trimethylsilyl)ethoxy)nicotinate (3.1 g, 39.7%) as a pale yellow liquid. TLC: 5% EtOAc in pet ether; R$_f$: 0.5.

Step 4: methyl 4-(difluoromethyl)-6-(2-(trimethylsilyl)ethoxy)nicotinate

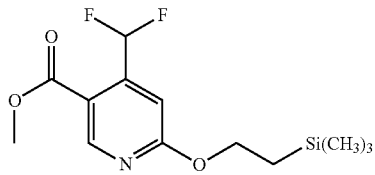

To a stirred solution of methyl 4-formyl-6-(2-(trimethylsilyl)ethoxy)nicotinate (6.1 g, 21.7 mmol, 1 eq) in DCM (60 ml) was added DAST (5.24 g, 32.56 mmol, 1.5 eq) at −78° C. under argon then slowly warmed to RT and stirred for 16 h. TLC analysis indicated formation of less polar spots. The reaction mixture was cooled to 0° C. quenched with Satd. NaHCO$_3$ solution, extracted with DCM (2×200 ml) washed with water (2×100 ml) and brine (2×100 ml). Combined organic layer was dried with Na$_2$SO$_4$ and concentrated under reduced pressure to give crude product methyl 4-(difluoromethyl)-6-(2-(trimethylsilyl)ethoxy)nicotinate (6 g, 92.87%) as a pale yellow color liquid. The crude product was used without further purification. TLC: 5% EtOAc in pet ether; R$_f$: 0.6.

Step 5: 4-(difluoromethyl)-6-(2-(trimethylsilyl)ethoxy)nicotinic acid

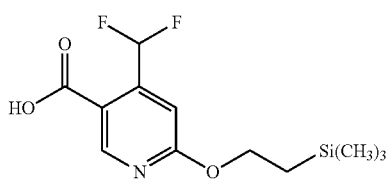

To a stirred solution of methyl 4-(difluoromethyl)-6-(2-(trimethylsilyl)ethoxy)nicotinate (6 g, 19.8 mmol, 1 eq) in MeOH:THF:H$_2$O (30:30:10 ml) was added LiOH (1.66 g, 39.6 mmol, 2 eq) at RT and was stirred for 16 h. TLC analysis indicated formation of polar spot. The solvent was evaporated under reduced pressure, the reaction mixture was cooled to 0° C., acidified with 2N HCl, extracted with EtOAc (2×100 ml), and washed with water (2×50 ml) and brine (2×50 ml). Combined organic layers were dried over Na$_2$SO$_4$ and concentrated under reduced pressure to give crude product. The crude product was washed with pentane to obtain pure 4-(difluoromethyl)-6-(2-(trimethylsilyl)ethoxy)nicotinic acid (4.5 g, 78.7%) as an off white solid. TLC: 5% MeOH in DCM; R$_f$: 0.1.

Step 6: N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide

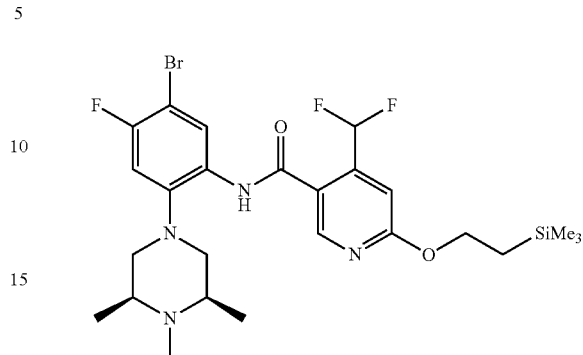

To a stirred solution of 4-(difluoromethyl)-6-(2-(trimethylsilyl)ethoxy)nicotinic acid (15 g, 47.61 mmol, 1 eq) in DMF (300 mL) was added DIPEA (25.7 mL, 142.8 mmol, 3 eq), HATU (54.27 g, 142.8 mmol, 3 eq) and then 5-bromo-4-fluoro-2-((3S,5R)-3,4,5-trimethylpiperazin-1-yl)aniline (14.3 g, 47.61 mmol, 1 eq) added at 0° C. under argon atm, and after that stirred for 16 h. TLC analysis indicated formation of nonpolar spots. The reaction mixture was diluted with ice water (200 mL) and extracted with EtOAc (2×500 mL). The organic layer was washed with brine and dried over Na$_2$SO$_4$ and concentrated under reduced pressure to give crude product. The crude product was purified by column chromatography (neutral alumina) using 0-5% EtOAc in pet ether as an eluent to result in N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (10 g, 66% yield) as an off white solid. LCMS: [M+H]+ 587.34.

Step 7: 4-(difluoromethyl)-N-[4-fluoro-5-[2-[(2R,6S)-2,6-dimethylmorpholin-4-yl]pyrimidin-5-yl]-2-[(3S,5R)-3,4,5-trimethylpiperazin-1-yl]phenyl]-6-oxo-1H-pyridine-3-carboxamide

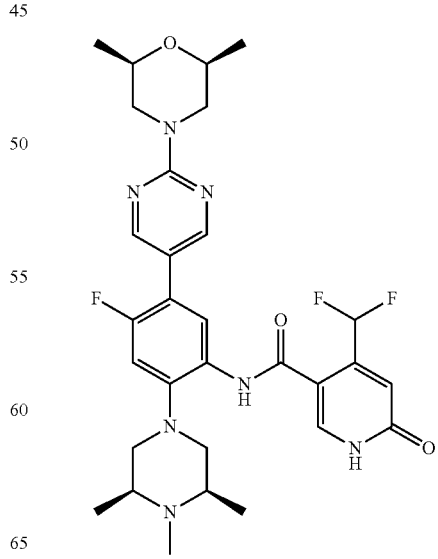

A microwave vial was charged with N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (25 mg, 0.043 mmol) and (2-((2S,6R)-2,6-dimethylmorpholino)pyrimidin-5-yl)boronic acid (15.13 mg, 0.064 mmol), potassium phosphate tribasic reagent grade, >=98% (27.1 mg, 0.128 mmol) and bis(di-tert-butyl(4-dimethylaminophenyl)phosphine)dichloropalladium(II) (3.01 mg, 4.25 μmol). The vial was sealed and evacuated and backfilled with nitrogen (×3). 1,4-Dioxane (0.9 ml) and water (0.100 ml) were added, the vial was evacuated and backfilled with nitrogen and heated with microwave at 110° C. for 2 hours. Aqueous workup [water/DCM] was performed then it was dried over magnesium sulfate and purified by flash chromatography [0.5-10% MeOH/DCM+0.5% NH₄OH; collect at 290 nm] to afford the 4-(difluoromethyl)-N-(5-(2-((2S,6R)-2,6-dimethylmorpholino)pyrimidin-5-yl)-4-fluoro-2-((3S,5R)-3,4,5-trimethylpiperazin-1-yl)phenyl)-6-(2-(trimethylsilyl)ethoxy)nicotinamide intermediate as a clear pale yellow film. This material was dissolved in DCM (2 mL) and treated with TFA (0.163 ml, 2.127 mmol) at room temperature. After 1 hour, LCMS indicated clean deprotection to the desired product. The volatiles were removed in vacuo and the residue cleaned with a catch and release on a PoraPak Rxn CX ion exchange column followed by lyophilization to afford the title compound as a white powder (0.029 mmol, 67.8% yield). ¹H NMR (500 MHz, DMSO-d6) δ=9.51 (s, 1H), 8.44 (d, J=0.7 Hz, 2H), 7.92 (s, 1H), 7.59 (d, J=8.7 Hz, 1H), 7.44-7.12 (m, 1H), 6.96 (d, J=12.3 Hz, 1H), 6.53 (s, 1H), 4.47 (br d, J=11.6 Hz, 2H), 3.50 (ddd, J=2.3, 6.2, 10.4 Hz, 2H), 2.96 (br d, J=10.9 Hz, 2H), 2.51 (dd, J=10.8, 13.1 Hz, 2H), 2.39 (br t, J=11.0 Hz, 2H), 2.25 (br s, 2H), 2.12 (s, 3H), 1.09 (d, J=6.1 Hz, 6H), 0.93 (d, J=6.1 Hz, 6H); LCMS [M+H]+: 600.6.

Example 386: 4-(difluoromethyl)-N-[4-fluoro-5-[2-[(2R)-2-methylmorpholin-4-yl]pyrimidin-5-yl]-2-[(3R,5S)-3,4,5-trimethylpiperazin-1-yl]phenyl]-6-oxo-1H-pyridine-3-carboxamide

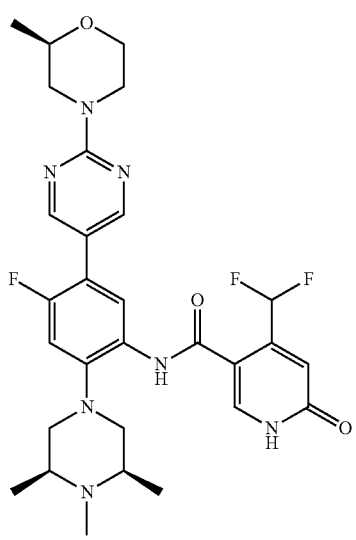

The procedure used was similar to Example 385 using N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (25 mg, 0.043 mmol) and (R)-(2-(2-methylmorpholino)pyrimidin-5-yl)boronic acid (17.08 mg, 0.077 mmol) to give after workup and purification the title compound (7.2 mg, 29% yield) as a white powder. ¹H NMR (500 MHz, DMSO-d6) δ=12.34 (br d, J=1.6 Hz, 1H), 9.52 (s, 1H), 8.45 (s, 2H), 7.92 (s, 1H), 7.60 (br d, J=5.5 Hz, 1H), 7.44-7.14 (m, 1H), 7.03-6.92 (m, 1H), 6.53 (s, 1H), 4.45 (br d, J=13.0 Hz, 1H), 4.38 (br d, J=13.2 Hz, 1H), 3.84 (dd, J=2.6, 11.5 Hz, 1H), 3.50-3.40 (m, 2H), 3.01-2.89 (m, 3H), 2.61 (dd, J=10.4, 13.1 Hz, 1H), 2.25 (br s, 1H), 2.12 (br s, 3H), 1.09 (d, J=6.2 Hz, 3H), 0.94 (br s, 6H); LCMS [M+H]+: 586.6.

Example 387: 4-fluoro-N-[4-fluoro-5-(2-morpholin-4-ylpyrimidin-5-yl)-2-[(3R,5R)-3,4,5-trimethylpiperazin-1-yl]phenyl]-2-(trifluoromethyl)benzamide

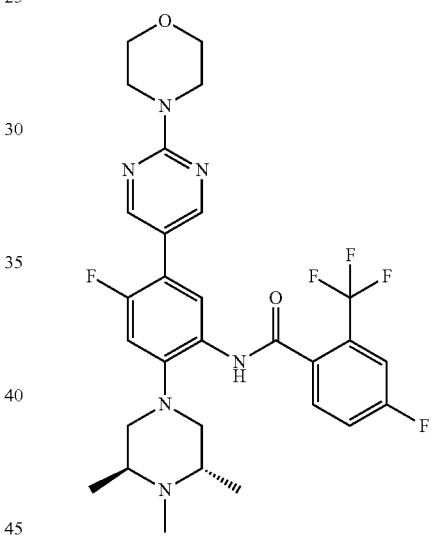

The title compound (white solid, 44.2 mg, 74%) was prepared by a procedure similar to that of Example 31 using 2-(4-morpholino)pyrimidine-5-boronic acid pinacol ester (58 mg, 0.2 mmol) and N-(5-bromo-4-fluoro-2-((3S,5S)-3,4,5-trimethylpiperazin-1-yl)phenyl)-4-fluoro-2-(trifluoromethyl)benzamide (51 mg, 0.1 mmol). ¹H NMR (500 MHz, CHLOROFORM-d) δ=8.63 (s, 1H), 8.58 (s, 2H), 8.55-8.52 (m, 1H), 7.67 (dd, J=5.3, 8.3 Hz, 1H), 7.49 (dd, J=2.3, 8.7 Hz, 1H), 7.36 (t, J=7.9 Hz, 1H), 7.01 (d, J=11.2 Hz, 1H), 3.90-3.85 (m, 4H), 3.82-3.77 (m, 4H), 2.95-2.80 (m, 4H), 2.66 (br dd, J=5.9, 10.4 Hz, 2H), 2.30 (s, 3H), 0.93 (br d, J=6.1 Hz, 6H); LCMS [M+H]⁺ 591.5.

Example 388: N-[4-fluoro-5-[2-[(2R)-2-methylmorpholin-4-yl]pyrimidin-5-yl]-2-[(3R,5S)-3,4,5-trimethylpiperazin-1-yl]phenyl]-6-oxo-4-(trifluoromethyl)-1H-pyridine-3-carboxamide

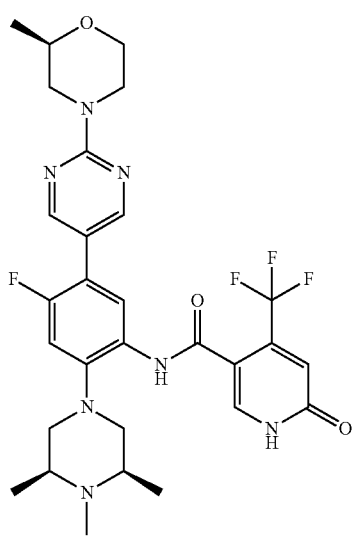

To a mixture of 2-chloropyrimidine-5-boronic acid (48 mg, 0.3 mmol) and (R)-2-methyl-morpholine, hydrochloride (43 mg, 0.315 mmol) in EtOH (3 mL) was added triethylamine (0.105 mL, 0.75 mmol). The resulting mixture was stirred at 80° C. for 1 h. Solvents were removed to give crude (R)-(2-(2-methylmorpholino)pyrimidin-5-yl)boronic acid as a pale yellow solid. LCMS [M+H]$^+$ 224.3. The title compound (pale beige solid, 18.0 mg, 29%) was prepared in a similar manner to Example 31 using crude (R)-(2-(2-methylmorpholino)pyrimidin-5-yl)boronic acid (0.3 mmol) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, CHLOROFORM-d) δ=8.70 (br s, 1H), 8.55 (s, 2H), 8.44 (br d, J=8.1 Hz, 1H), 7.87 (s, 1H), 7.06-6.97 (m, 2H), 4.64-4.54 (m, 2H), 4.01 (dd, J=2.6, 11.6 Hz, 1H), 3.70-3.60 (m, 2H), 3.15-3.04 (m, 1H), 2.82 (br d, J=10.8 Hz, 2H), 2.75 (dd, J=10.5, 13.1 Hz, 1H), 2.66 (br t, J=10.5 Hz, 2H), 2.42-2.24 (m, 5H), 1.27 (d, J=6.2 Hz, 3H), 1.14 (br d, J=5.7 Hz, 6H); LCMS [M+H]$^+$ 604.5.

Example 389: N-[4-fluoro-2-[(3R)-3,4-dimethylpiperazin-1-yl]-5-[2-[(2R)-2-methylmorpholin-4-yl]pyrimidin-5-yl]phenyl]-6-oxo-4-(trifluoromethyl)-1H-pyridine-3-carboxamide

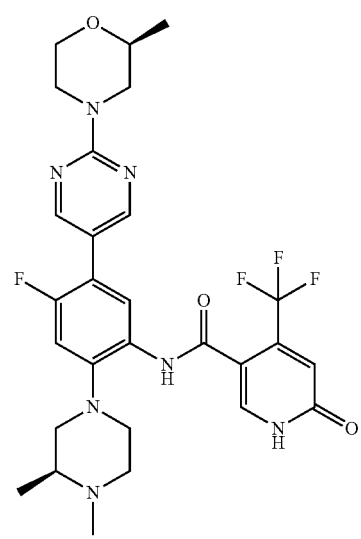

To a mixture of 2-chloropyrimidine-5-boronic acid (48 mg, 0.3 mmol) and (S)-2-methylmorpholine (33 mg, 0.33 mmol) in EtOH (3 mL) was added triethylamine (0.070 mL, 0.5 mmol). The resulting mixture was stirred at 80° C. for 1 h. Solvents were removed to give crude (S)-(2-(2-methylmorpholino)pyrimidin-5-yl)boronic acid as a yellow solid. LCMS [M+H]$^+$ 224.1. The title compound (pale beige solid, 30.2 mg, 51%) was prepared in a manner similar to the final step of Example 31 using crude (S)-(2-(2-methylmorpholino)pyrimidin-5-yl)boronic acid (0.3 mmol) and (S)—N-(5-bromo-2-(3,4-dimethylpiperazin-1-yl)-4-fluorophenyl)-6-oxo-4-(trifluoromethyl)-1,6-dihydropyridine-3-carboxamide (49.1 mg, 0.1 mmol). $^1$H NMR (500 MHz, CHLOROFORM-d) δ=8.70 (s, 1H), 8.55 (s, 2H), 8.45 (br d, J=8.1 Hz, 1H), 7.89 (s, 1H), 7.04 (d, J=11.1 Hz, 1H), 7.00 (s, 1H), 4.64-4.53 (m, 2H), 4.01 (dd, J=2.5, 11.6 Hz, 1H), 3.71-3.58 (m, 2H), 3.15-3.06 (m, 1H), 3.01-2.86 (m, 3H), 2.82 (br d, J=10.9 Hz, 1H), 2.75 (dd, J=10.6, 13.0 Hz, 1H), 2.60 (br t, J=10.5 Hz, 1H), 2.43-2.30 (m, 4H), 2.22 (br s, 1H), 1.27 (d, J=6.2 Hz, 3H), 1.10 (br d, J=6.1 Hz, 3H); LCMS [M+H]$^+$590.6.

Example 390: N-[4-fluoro-5-[2-[(2R)-2-methylmorpholin-4-yl]pyrimidin-5-yl]-2-[(3S,5R)-3,4,5-trimethylpiperazin-1-yl]phenyl]-6-oxo-4-(trifluoromethyl)-1H-pyridine-3-carboxamide

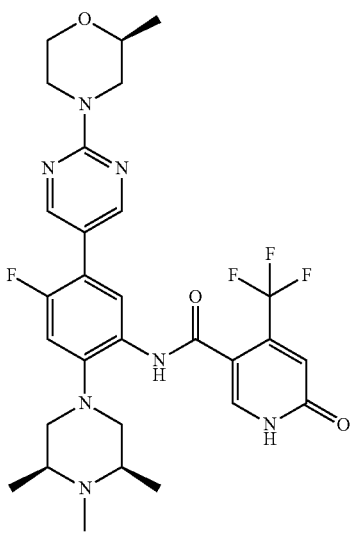

The title compound (pale beige solid, 35.5 mg, 58%) was prepared through a procedure similar to that of Example 31 using crude (S)-(2-(2-methylmorpholino)pyrimidin-5-yl)boronic acid (0.3 mmol) and (S)—N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, CHLOROFORM-d) δ=8.69 (s, 1H), 8.55 (s, 2H), 8.44 (br d, J=8.1 Hz, 1H), 7.88 (s, 1H), 7.05-6.98 (m, 2H), 4.64-4.54 (m, 2H), 4.01 (dd, J=2.7, 11.5 Hz, 1H), 3.70-3.59 (m, 2H), 3.10 (dt, J=3.4, 12.6 Hz, 1H), 2.82 (br d, J=11.0 Hz, 2H), 2.75 (dd, J=10.5, 13.1 Hz, 1H), 2.65 (br t, J=10.9 Hz, 2H), 2.39-2.27 (m, 5H), 1.27 (d, J=6.2 Hz, 3H), 1.14 (d, J=6.1 Hz, 6H); LCMS [M+H]$^+$ 604.6.

Example 391: N-[4-fluoro-5-(1-pyrimidin-2-yl-3,6-dihydro-2H-pyridin-5-yl)-2-[(3R,5S)-3,4,5-trimethylpiperazin-1-yl]phenyl]-1-methyl-6-oxo-4-(trifluoromethyl)pyridine-3-carboxamide

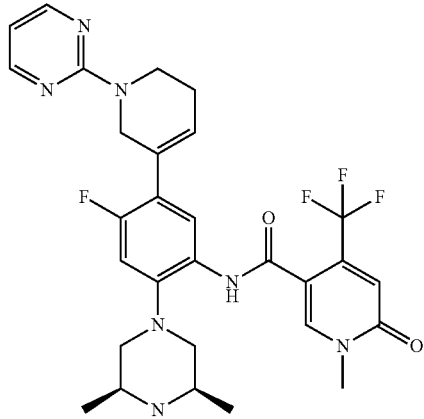

Cesium carbonate (6.68 mg, 0.020 mmol) was added to a solution of N-(4-fluoro-5-(1-(pyrimidin-2-yl)-1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (12 mg, 0.020 mmol) and MeI (1.467 μl, 0.024 mmol) in DMF (1 ml) at RT. The reaction mixture was continuously stirred at RT. Complete conversion to the desired product was observed after 18 min. The mixture was diluted with DCM (1 ml) and mixed with water (2 ml). The aqueous phase was extracted with DCM (2×1 ml), the combined organic phase was washed with water (1 ml×5), brine, dried over Na$_2$SO$_4$ and concentrated. The crude was purified on Isco column, eluting with DCM containing 0-2% MeOH and 0-0.2% NH$_4$OH to afford the title compound as a white solid. (5.3 mg, 40%). $^1$H NMR (500 MHz, METHANOL-d4) δ=8.26-8.23 (m, 2H), 8.16-8.08 (m, 1H), 7.73-7.67 (m, 1H), 6.90-6.85 (m, 1H), 6.84-6.82 (m, 1H), 6.54-6.47 (m, 1H), 6.11-6.02 (m, 1H), 4.46-4.40 (m, 2H), 3.92-3.87 (m, 2H), 3.58-3.52 (m, 3H), 2.99-2.85 (m, 2H), 2.53-2.44 (m, 2H), 2.44-2.37 (m, 2H), 2.33-2.29 (m, 2H), 2.27-2.20 (m, 3H), 1.07-1.03 (m, 6H); LCMS [M+H]+ 600.8.

Example 392: N-[4-fluoro-5-[4-[(4-fluorophenyl)methyl]piperazin-1-yl]-2-[(3R,5S)-3,4,5-trimethylpiperazin-1-yl]phenyl]-6-oxo-4-(trifluoromethyl)-1H-pyridine-3-carboxamide

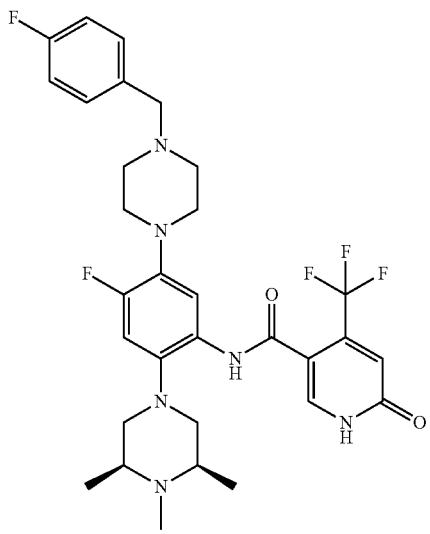 [SMILES: C[C@@H]1CN(c2cc(F)c(N3CCN(Cc4ccc(F)cc4)CC3)cc2NC(=O)c2c[nH]c(=O)cc2C(F)(F)F)C[C@H](C)N1C]

2,2'-Bis(diphenylphosphino)-1,1'-binaphthalene (15.4 mg, 0.025 mmol), N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (100 mg, 0.165 mmol), palladium(II) acetate (2.2 mg, 0.001 mmol), 1-(4-fluorobenzyl)piperazine (35.3 mg, 0.182 mmol) and $CsCO_3$ (215 mg, 0.661 mmol) were mixed in 1,4-dioxane (3 ml) and the vial was flushed with nitrogen. The reaction mixture was heated in an oil bath at 110° C. for 16 h. The mixture was further heated at 135° C. for 5 h. The reaction mixture was filtered through celite, the filter cake was washed with DCM, the combined filtrate was concentrated onto celite and purified by silica gel chromatography to give N-(4-fluoro-5-(4-(4-fluorobenzyl)piperazin-1-yl)-2-((3S,5R)-3,4,5-trimethylpiperazin-1-yl)phenyl)-4-(trifluoromethyl)-6-(2-(trimethylsilyl)ethoxy)nicotinamide, which was dissolved in DCM (1.5 mL). TFA (0.5 ml) was added and the mixture was stirred at room temperature for 10 min. Concentration and passing through a cation exchange resin cartridge (Isolute SCX-2 6 ml), and eluting with 3% $NH_3$ in MeOH afforded after removal of solvents the title compound as the free base (11.5 mg, 93%). $^1$H NMR (500 MHz, METHANOL-d4) δ=7.92-7.87 (m, 1H), 7.58-7.50 (m, 1H), 7.36-7.30 (m, 2H), 7.02-6.93 (m, 3H), 6.81-6.77 (m, 1H), 3.66-3.57 (m, 2H), 3.08-3.02 (m, 4H), 2.93-2.88 (m, 2H), 2.85-2.73 (m, 2H), 2.71-2.64 (m, 4H), 2.63-2.57 (m, 2H), 2.53-2.47 (m, 3H), 1.15 (br d, J=6.0 Hz, 6H); LCMS [M+H]+ 619.8.

Example 393: N-[4-fluoro-5-(4-pyrimidin-2-ylpiperazin-1-yl)-2-[(3R,5S)-3,4,5-trimethylpiperazin-1-yl]phenyl]-6-oxo-4-(triluoromethyl)-1H-pyridine-3-carboxamide

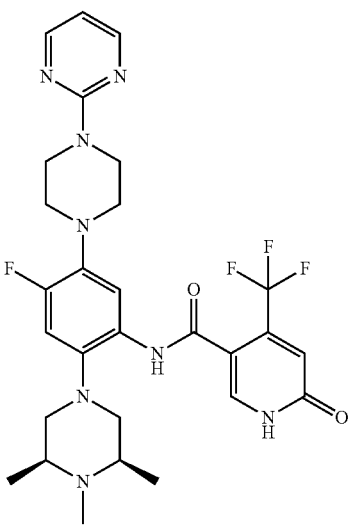 [SMILES: C[C@@H]1CN(c2cc(F)c(N3CCN(c4ncccn4)CC3)cc2NC(=O)c2c[nH]c(=O)cc2C(F)(F)F)C[C@H](C)N1C]

The procedure used was similar to that of Example 392 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (100 mg, 0.165 mmol) and 1-(2-pyrimidyl)piperazine (54.2 mg, 0.330 mmol) to give, after deprotection of the silyoxypyridyl intermediate, the title compound as an off white powder (50 mg, 99% yield). $^1$H NMR (500 MHz, METHANOL-d4) δ=8.37-8.31 (m, 2H), 7.99-7.93 (m, 1H), 7.72-7.64 (m, 1H), 7.09-7.01 (m, 1H), 6.92-6.85 (m, 1H), 6.64-6.56 (m, 1H), 3.98-3.92 (m, 4H), 3.14-3.08 (m, 4H), 2.99-2.91 (m, 2H), 2.79-2.69 (m, 2H), 2.67-2.61 (m, 2H), 2.52-2.44 (m, 3H), 1.22-1.17 (m, 6H); LCMS [M+H]+ 589.6.

Example 394: N-[4-fluoro-5-[1-[5-(hydroxymethyl)pyrimidin-2-yl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

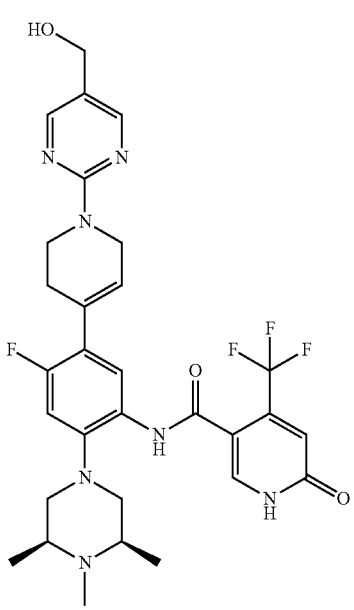

Sodium borohydride (7.71 mg, 0.204 mmol) was added to a solution of N-(4-fluoro-5-(1-(5-formylpyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.041 mmol) in methanol (3 ml) and water (0.5 ml) at RT. The reaction was complete in 5 min. The mixture was concentrated, taken up in EtOAc, quenched with $NH_4Cl$ solution, the organic phase was separated, the aqueous phase was extracted with EtOAc (5×3 ml), dried over $Na_2SO_4$, concentrated onto celite and purified on Isco (4G), eluting with DCM containing 0-4% MeOH and 0-0.4% $NH_4OH$. The desired product was isolated as an orange red powder (24 mg, 91%). $^1H$ NMR (500 MHz, METHANOL-d4) δ=8.29-8.22 (m, 2H), 7.87-7.82 (m, 1H), 7.72-7.64 (m, 1H), 6.92-6.86 (m, 1H), 6.84-6.80 (m, 1H), 6.06-5.98 (m, 1H), 4.39-4.35 (m, 2H), 4.29-4.24 (m, 2H), 3.97-3.93 (m, 2H), 3.04-2.98 (m, 2H), 2.82-2.69 (m, 2H), 2.63-2.55 (m, 2H), 2.52-2.44 (m, 5H), 1.15-1.12 (m, 6H); LCMS [M+H]+ 616.7

Example 395: 4-(difluoromethyl)-N-[4-fluoro-5-[2-[(2R,6S)-2,6-dimethylmorpholin-4-yl]pyrimidin-5-yl]-2-[(3S)-3,4-dimethylpiperazin-1-yl]phenyl]-6-oxo-1H-pyridine-3-carboxamide

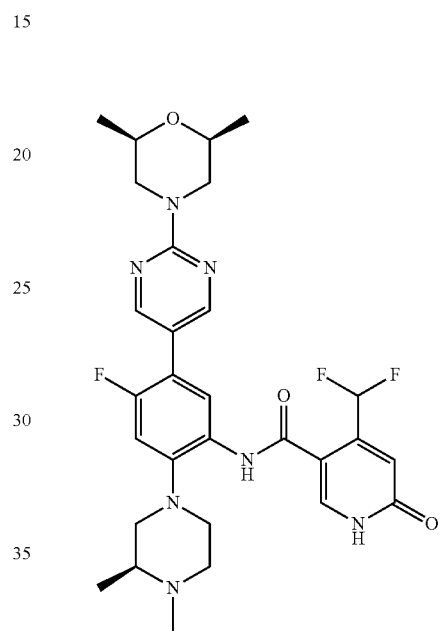

The title compound (pale beige solid, 35.5 mg, 58%) was prepared by a procedure similar to that of Example 383 using crude (S)-(2-(2-methylmorpholino)pyrimidin-5-yl)boronic acid (0.3 mmol) and (S)—N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1H$ NMR (500 MHz, CHLOROFORM-d) δ=8.69 (s, 1H), 8.55 (s, 2H), 8.44 (br d, J=8.1 Hz, 1H), 7.88 (s, 1H), 7.05-6.98 (m, 2H), 4.64-4.54 (m, 2H), 4.01 (dd, J=2.7, 11.5 Hz, 1H), 3.70-3.59 (m, 2H), 3.10 (dt, J=3.4, 12.6 Hz, 1H), 2.82 (br d, J=11.0 Hz, 2H), 2.75 (dd, J=10.5, 13.1 Hz, 1H), 2.65 (br t, J=10.9 Hz, 2H), 2.39-2.27 (m, 5H), 1.27 (d, J=6.2 Hz, 3H), 1.14 (d, J=6.1 Hz, 6H); LCMS [M+H]+ 604.6.

Example 396: 4-(difluoromethyl)-N-[4-fluoro-2-[(3S)-3,4-dimethylpiperazin-1-yl]-5-[2-[(2R)-2-methylmorpholin-4-yl]pyrimidin-5-yl]phenyl]-6-oxo-1H-pyridine-3-carboxamide

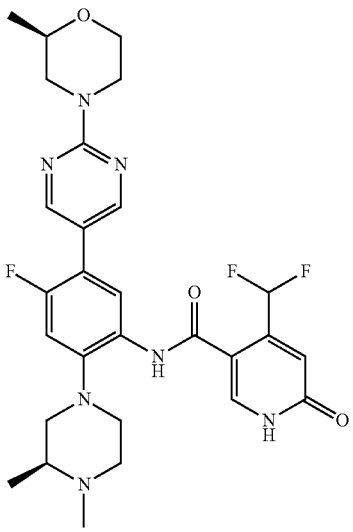

Step 1: (S)—N-(5-bromo-2-(3,4-dimethylpiperazin-1-yl)-4-fluorophenyl)-4-(difluoromethyl)-6-(2-(trimethylsilyl)ethoxy)nicotinamide

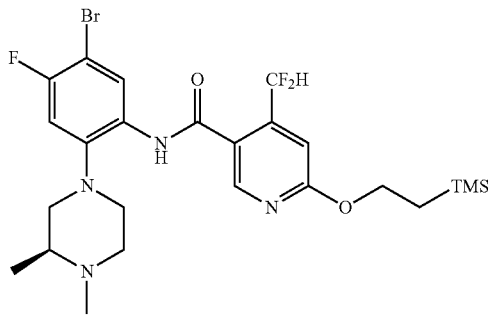 [SMILES: C[C@H]1CN(c2cc(F)c(Br)cc2NC(=O)c2cnc(OCC[Si](C)(C)C)cc2C(F)F)CCN1C]

To a stirred solution of 4-(difluoromethyl)-6-(2-(trimethylsilyl)ethoxy)nicotinic acid (10 g, 34.59 mmol, 1 eq) in DMF (100 mL) was added DIPEA (18.6 mL, 103.8 mmol, 3 eq), HATU (39.4 g, 103.8 mmol, 3 eq) and then (S)-5-bromo-2-(3,4-dimethylpiperazin-1-yl)-4-fluoroaniline (10.4 g, 34.59 mmol, 1 eq) was added at 0° C. under argon atm, and after that stirred for 16 h. TLC analysis indicated formation of nonpolar spots. The reaction mixture was diluted with ice water (200 mL) and extracted with EtOAc (2×500 mL). The organic layer was washed with brine and dried over Na₂SO₄ and concentrated under reduced pressure to give crude product. The crude product was purified by column chromatography (neutral alumina) using 0-5% EtOAc in pet ether as an eluent to give (S)—N-(5-bromo-2-(3,4-dimethylpiperazin-1-yl)-4-fluorophenyl)-4-(difluoromethyl)-6-(2-(trimethylsilyl)ethoxy)nicotinamide (5 g, 30% yield) as an off white solid. LCMS: [M+H]+ 573.04.

Step 2: 4-(difluoromethyl)-N-[4-fluoro-2-[(3S)-3,4-dimethylpiperazin-1-yl]-5-[2-[(2R)-2-methylmorpholin-4-yl]pyrimidin-5-yl]phenyl]-6-oxo-1H-pyridine-3-carboxamide

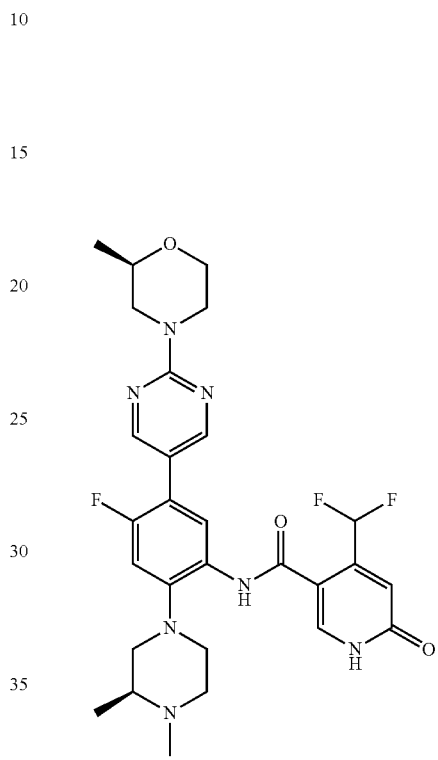

The procedure followed was similar to that used in Example 39 using (S)—N-(5-bromo-2-(3,4-dimethylpiperazin-1-yl)-4-fluorophenyl)-4-(difluoromethyl)-6-(2-(trimethylsilyl)ethoxy)nicotinamide (25 mg, 0.044 mmol) and (R)-(2-(2-methylmorpholino)pyrimidin-5-yl)boronic acid (17.50 mg, 0.078 mmol to give the title compound (11 mg, 44.1% yield) as a white powder. ¹H NMR (500 MHz, DMSO-d6) δ=12.37 (br s, 1H), 9.55 (s, 1H), 8.52 (s, 2H), 8.00 (s, 1H), 7.69 (d, J=8.6 Hz, 1H), 7.48-7.21 (m, 1H), 7.06 (d, J=12.5 Hz, 1H), 6.59 (s, 1H), 4.57-4.40 (m, 2H), 3.91 (dd, J=2.4, 11.5 Hz, 1H), 3.57-3.49 (m, 2H), 3.06-2.96 (m, 3H), 2.85-2.74 (m, 2H), 2.67 (dd, J=10.5, 13.1 Hz, 1H), 2.42 (t, J=10.6 Hz, 1H), 2.35-2.28 (m, 1H), 2.20 (s, 4H), 1.16 (d, J=6.2 Hz, 3H), 0.97 (d, J=6.2 Hz, 3H); LCMS [M+H]+: 572.6.

Example 397: 4-(difluoromethyl)-N-[4-fluoro-5-[2-[(2R)-2-methylmorpholin-4-yl]pyrimidin-5-yl]-2-[(3S,5R)-3,4,5-trimethylpiperazin-1-yl]phenyl]-6-oxo-1H-pyridine-3-carboxamide

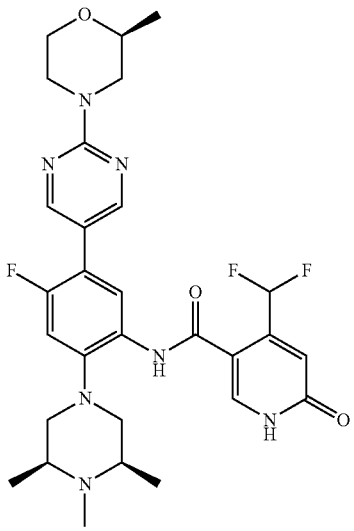

Step 1: N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide

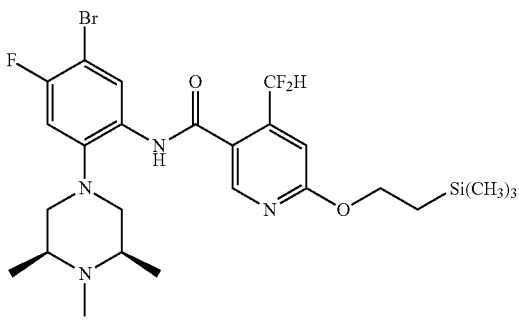

To a stirred solution of 4-(difluoromethyl)-6-(2-(trimethylsilyl)ethoxy)nicotinic acid (15 g, 47.61 mmol, 1 eq, from Example 385 Step 5) in DMF (300 mL) was added DIPEA (25.7 mL, 142.83 mmol, 3 eq), HATU (54.27 g, 142.83 mmol, 3 eq) and then 5-bromo-4-fluoro-2-((3R,5S)-3,4,5-trimethylpiperazin-1-yl)aniline (14.3 g, 47.61 mmol, 1 eq) was added at 0° C. under argon atm, and after that stirred for 16 h. TLC analysis indicated formation of nonpolar spots. The reaction mixture was diluted with ice water (200 mL) and extracted with EtOAc (2×500 mL). The organic layer was washed with brine and dried over $Na_2SO_4$ and concentrated under reduced pressure to give crude product. The crude product was purified by column chromatography (neutral alumina) using 0-5% EtOAc in pet ether as an eluent afforded N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (10 g, 66% yield) as an off white solid. LCMS: [M+H]+ 587.34.

Step 2: 4-(difluoromethyl)-N-[4-fluoro-5-[2-[(2R)-2-methylmorpholin-4-yl]pyrimidin-5-yl]-2-[(3S,5R)-3,4,5-trimethylpiperazin-1-yl]phenyl]-6-oxo-1H-pyridine-3-carboxamide

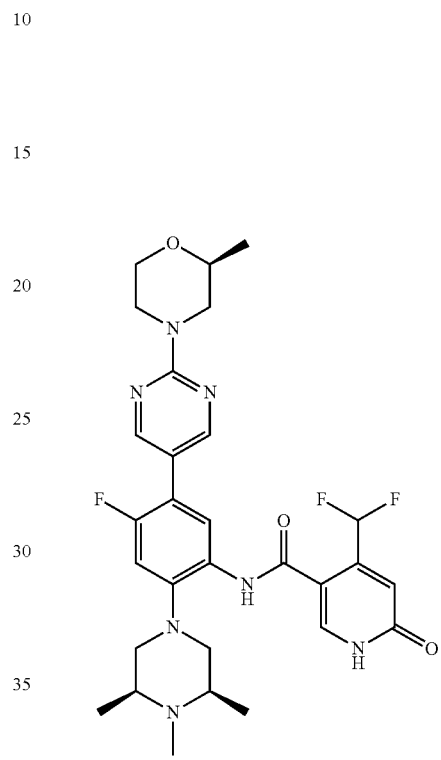

The title compound (9 mg, 36% yield) was prepared by a procedure similar to Example 39 using N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (25 mg, 0.043 mmol), (S)-(2-(2-methylmorpholino)pyrimidin-5-yl)boronic acid (18.98 mg, 0.085 mmol). $^1$H NMR (500 MHz, DMSO-d6) δ=12.40 (br d, J=2.3 Hz, 1H), 9.59 (s, 1H), 8.52 (d, J=0.7 Hz, 2H), 7.99 (br s, 1H), 7.67 (br d, J=8.4 Hz, 1H), 7.49-7.20 (m, 1H), 7.04 (br d, J=12.3 Hz, 1H), 6.60 (s, 1H), 4.55-4.41 (m, 2H), 3.91 (dd, J=2.3, 11.3 Hz, 1H), 3.54-3.48 (m, 2H), 3.06-2.98 (m, 3H), 2.68 (dd, J=10.5, 13.1 Hz, 1H), 2.47-2.42 (m, 2H), 2.32 (br s, 2H), 2.22-2.16 (m, 3H), 1.16 (d, J=6.1 Hz, 3H), 1.00 (br d, J=5.0 Hz, 6H); $^{19}$F NMR (471 MHz, DMSO-d6) δ=−118.73 (br s, 1F), −119.35 (br s, 1F). LCMS [M+H]+ 604.6.

Example 398: 4-(difluoromethyl)-N-[4-fluoro-2-[(3R)-3,4-dimethylpiperazin-1-yl]-5-[2-[(2R)-2-methylmorpholin-4-yl]pyrimidin-5-yl]phenyl]-6-oxo-1H-pyridine-3-carboxamide

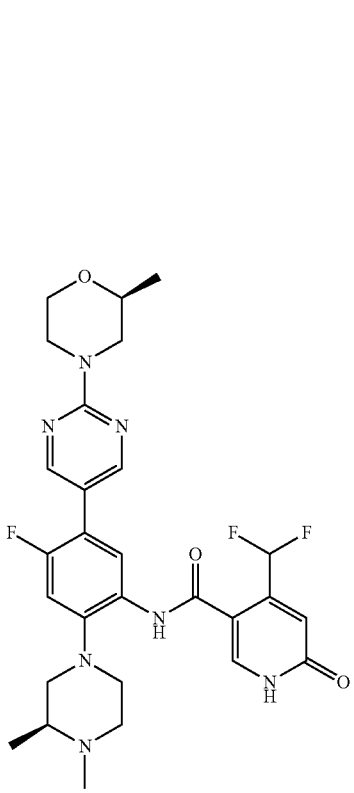

The title compound was prepared by procedure similar to that of Example 39 using (S)—N-(5-bromo-2-(3,4-dimethylpiperazin-1-yl)-4-fluorophenyl)-4-(difluoromethyl)-6-(2-(trimethylsilyl)ethoxy)nicotinamide (25 mg, 0.044 mmol) and (S)-(2-(2-methylmorpholino)pyrimidin-5-yl)boronic acid (19.44 mg, 0.087 mmol) to give the title compound (11.7 mg, 47.0% yield) as a white powder. $^1$H NMR (500 MHz, DMSO-d6) δ=12.38 (br s, 1H), 9.53 (s, 1H), 8.52 (d, J=0.7 Hz, 2H), 8.01 (s, 1H), 7.69 (d, J=8.7 Hz, 1H), 7.49-7.20 (m, 1H), 7.06 (d, J=12.5 Hz, 1H), 6.57 (s, 1H), 4.53-4.42 (m, 2H), 3.91 (dd, J=2.9, 11.3 Hz, 1H), 3.53-3.48 (m, 2H), 3.03-2.97 (m, 2H), 2.81-2.74 (m, 2H), 2.67 (dd, J=10.5, 13.1 Hz, 1H), 2.44-2.39 (m, 1H), 2.34-2.28 (m, 1H), 2.22-2.18 (m, 5H), 1.16 (d, J=6.2 Hz, 3H), 0.97 (d, J=6.1 Hz, 3H); LCMS [M+H]+: 572.6.

Example 399: N-[4-fluoro-5-(2-methylsulfonylpyrimidin-4-yl)-2-[(3R,5S)-3,4,5-trimethylpiperazin-1-yl]phenyl]-6-oxo-4-(trifluoromethyl)-1H-pyridine-3-carboxamide

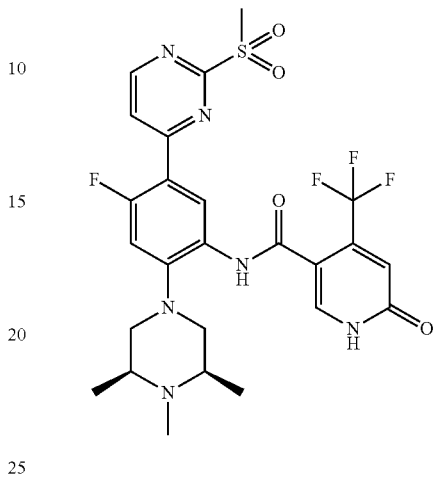

The title compound (4.5 mg, 6% yield) was prepared in a manner similar to that of Example 384 using N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy)nicotinamide (106 mg, 0.130 mmol) and 4-bromo-2-(methylsulfonyl)pyrimidine (30.8 mg, 0.130 mmol). $^1$H NMR (500 MHz, MeOD) δ 8.99 (d, J=5.4 Hz, 1H), 8.63 (d, J=8.3 Hz, 1H), 8.15 (d, J=5.2 Hz, 1H), 7.98 (s, 1H), 7.09 (d, J=13.6 Hz, 1H), 6.93 (s, 1H), 3.44 (s, 3H), 3.25 (d, J=11.7 Hz, 2H), 2.68 (t, J=11.4 Hz, 2H), 2.59 (s, 2H), 2.40 (s, 3H), 1.18 (d, J=6.2 Hz, 6H); LCMS [M+1]$^+$=583.5.

Example 400: 4-fluoro-N-[4-fluoro-5-[2-(4-methyl-1,4-diazepan-1-yl)pyrimidin-5-yl]-2-[(3R)-3,4-dimethylpiperazin-1-yl]phenyl]-2-(trifluoromethyl)benzamide

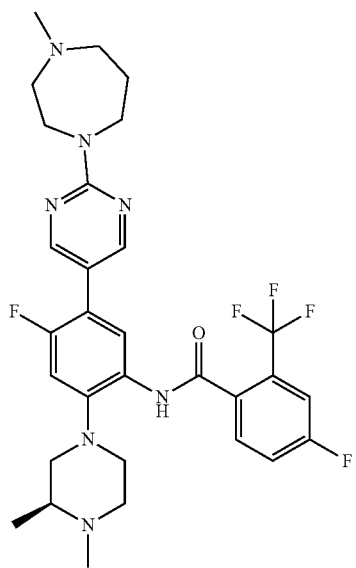

Step 1: Preparation of (S)—N-(5-bromo-2-(3,4-dimethylpiperazin-1-yl)-4-fluorophenyl)-4-fluoro-2-(trifluoromethyl)benzamide

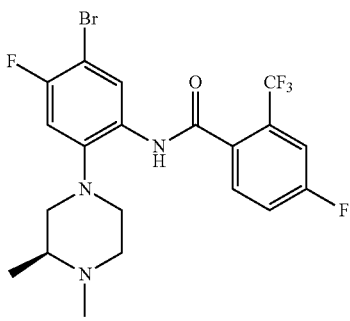 [SMILES: C[C@H]1CN(c2cc(F)c(Br)cc2NC(=O)c2ccc(F)cc2C(F)(F)F)CCN1C]

To a solution of 4-fluoro-2-trifluoromethyl)benzoyl chloride (0.61 mL, 4 mmol) in DCM (15 mL) at rt was added Et$_3$N (1.12 mL, 8 mmol). After addition, the resulting mixture was stirred at rt for 5 min, before a solution of (S)-5-bromo-2-(3,4-dimethylpiperazin-1-yl)-4-fluoroaniline (604 mg, 2 mmol) in DCM (10 mL) was added in 1 min. The resulting dark orange solution was stirred at rt for 2 h. After quenching with sat. NaHCO$_3$ (15 mL) and stirring for 2 min at rt, the mixture was extracted with DCM (20×2 mL). The extracts were combined, and concentrated to give a light beige solid. It was loaded onto samplet with DCM/MeOH and purified by flash chromatography (gradient: EtOAc/hex 0-100%) to give the title compound as a light yellow solid (822 mg, 82%). LCMS [M+H]$^+$ 492.4.

Step 2: 4-fluoro-N-[4-fluoro-5-[2-(4-methyl-1,4-diazepan-1-yl)pyrimidin-5-yl]-2-[(3R)-3,4-dimethylpiperazin-1-yl]phenyl]-2-(trifluoromethyl)benzamide

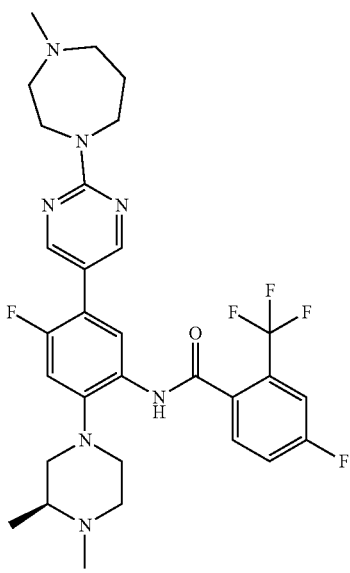 [SMILES: C[C@H]1CN(c2cc(F)c(-c3cnc(N4CCCN(C)CC4)nc3)cc2NC(=O)c2ccc(F)cc2C(F)(F)F)CCN1C]

The title compound (white solid, 30.5 mg, 51%) was prepared by a procedure similar to Example 31 using crude (2-(4-methyl-1,4-diazepan-1-yl)pyrimidin-5-yl)boronic acid (0.3 mmol) and (S)—N-(5-bromo-2-(3,4-dimethylpiperazin-1-yl)-4-fluorophenyl)-4-fluoro-2-(trifluoromethyl)benzamide (49.2 mg, 0.1 mmol). $^1$H NMR (500 MHz, CHLOROFORM-d) δ=8.63-8.52 (m, 4H), 7.66 (dd, J=5.3, 8.4 Hz, 1H), 7.49 (dd, J=2.3, 8.8 Hz, 1H), 7.38 (dt, J=2.3, 8.1 Hz, 1H), 7.01 (d, J=11.2 Hz, 1H), 4.04-3.94 (m, 2H), 3.87 (t, J=6.3 Hz, 2H), 2.98-2.80 (m, 4H), 2.76-2.69 (m, 2H), 2.63-2.52 (m, 3H), 2.40 (s, 3H), 2.33-2.24 (m, 4H), 2.12 (br s, 1H), 2.04 (quin, J=5.8 Hz, 2H), 1.05 (d, J=6.2 Hz, 3H); LCMS [M+H]$^+$ 604.6.

Example 401: 4-fluoro-N-[4-fluoro-5-(2-piperazin-1-ylpyrimidin-5-yl)-2-[(3R)-3,4-dimethylpiperazin-1-yl]phenyl]-2-(trifluoromethyl)benzamide

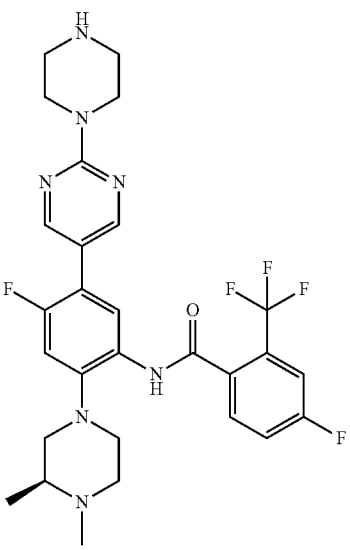

The title compound (beige solid, 15.9 mg, 26%) was prepared according to a procedure similar to that of Example 400 using (S)—N-(5-bromo-2-(3,4-dimethylpiperazin-1-yl)-4-fluorophenyl)-4-fluoro-2-(trifluoromethyl)benzamide (53 mg, 0.1 mmol) and 2-(4-methylpiperazin-1-yl)pyrimidine-5-boronic acid pinacol ester (61 mg, 0.2 mmol). $^1$H NMR (500 MHz, CHLOROFORM-d) δ=8.61-8.54 (m, 4H), 7.67 (dd, J=5.3, 8.4 Hz, 1H), 7.50 (dd, J=2.4, 8.7 Hz, 1H), 7.38 (dt, J=2.3, 8.1 Hz, 1H), 7.02 (d, J=11.2 Hz, 1H), 3.97-3.87 (m, 4H), 2.97-2.81 (m, 4H), 2.56 (t, J=10.5 Hz, 1H), 2.50 (t, J=5.1 Hz, 4H), 2.36 (s, 3H), 2.32-2.25 (m, 4H), 2.12 (br s, 1H), 1.05 (d, J=6.2 Hz, 3H); LCMS [M+H]$^+$ 590.3.

Example 402: 4-fluoro-N-[4-fluoro-5-(6-morpholin-4-ylpyridin-3-yl)-2-[(3R)-3,4-dimethylpiperazin-1-yl]phenyl]-2-(trifluoromethyl)benzamide

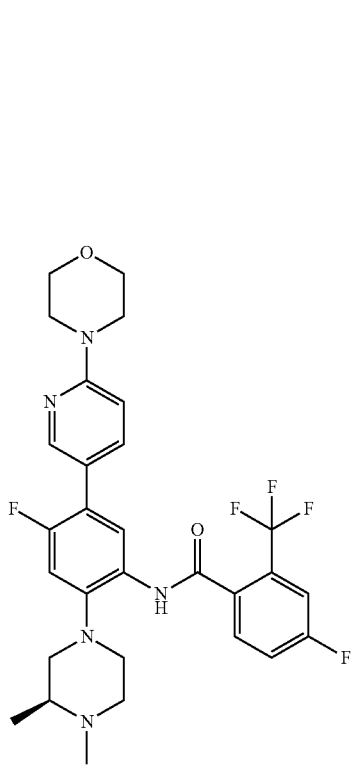

The title compound (pale beige solid, 38.7 mg, 63%) was prepared by a method similar to that of Example 400 using 4-[5-(4,4,5,5-tetramethyl-[1,3,2]dioxaborolan-2-yl)-pyridin-2-yl]-morpholine (60 mg, 0.2 mmol) and (S)—N-(5-bromo-2-(3,4-dimethylpiperazin-1-yl)-4-fluorophenyl)-4-fluoro-2-(trifluoromethyl)benzamide (51 mg, 0.104 mmol). $^1$H NMR (500 MHz, CHLOROFORM-d) δ=8.60 (s, 1H), 8.58 (d, J=8.2 Hz, 1H), 8.48 (s, 1H), 7.76 (br d, J=8.7 Hz, 1H), 7.67 (dd, J=5.3, 8.4 Hz, 1H), 7.50 (dd, J=2.3, 8.8 Hz, 1H), 7.38 (dt, J=2.3, 8.1 Hz, 1H), 7.01 (d, J=11.4 Hz, 1H), 6.71 (d, J=8.9 Hz, 1H), 3.88-3.82 (m, 4H), 3.61-3.55 (m, 4H), 2.99-2.81 (m, 4H), 2.57 (br t, J=10.5 Hz, 1H), 2.39-2.24 (m, 4H), 2.20-2.07 (m, 1H), 1.06 (d, J=6.2 Hz, 3H); LCMS [M+H]$^+$ 576.5.

Example 403: 4-(difluoromethyl)-N-[4-fluoro-5-[6-(oxan-4-yloxy)pyridin-3-yl]-2-[(3R)-3,4-dimethylpiperazin-1-yl]phenyl]-6-oxo-1H-pyridine-3-carboxamide

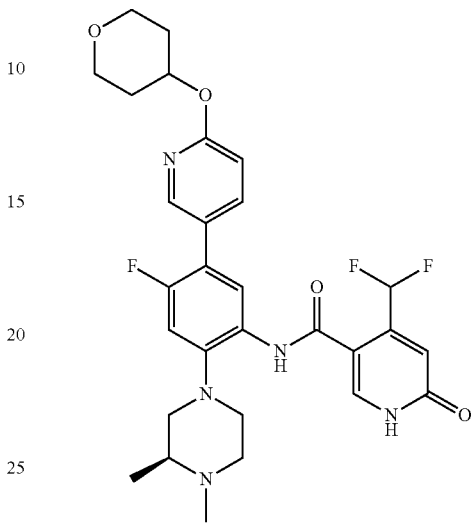

In a 5 mL microwave vial (S)—N-(5-bromo-2-(3,4-dimethylpiperazin-1-yl)-4-fluorophenyl)-4-(difluoromethyl)-6-(2-(trimethylsilyl)ethoxy)nicotinamide (35 mg, 0.061 mmol), 2-(tetrahydropyran-4-yloxy)-5-(4,4,5,5-tetramethyl-1,3,2-dioxaborolan-2-yl)pyridine (27.9 mg, 0.092 mmol), bis(di-tert-butyl(4-dimethylaminophenyl)phosphine)dichloropalladium(II) (4.32 mg, 6.10 μmol) and potassium phosphate tribasic reagent grade (0.026 g, 0.122 mmol) were dissolved in 1,4-dioxane (1.098 mL)/water (0.122 mL) (9:1 mixture) to give a white suspension. The suspension was stirred for 5 min, degassed, purged with N$_2$, and microwaved for 60 min at 110° C. The solvent was evaporated and 15 mL of CH$_2$Cl$_2$ were added. The suspension was sonicated and extracted from water (15 mL). The solvent was evaporated in vacuo yielding the crude product that was purified by flash column chromatography on silica gel (0-100%, 89% CH$_2$Cl$_2$, 10% MeOH, 1% NH$_4$Ac/CH$_2$Cl$_2$) to afford the protected compound. The product was dissolved in 2 mL of dichloromethane and trifluoroacetic acid (70 μl, 0.915 mmol) was added. The purple solution was stirred for 1 hour and the solvent was evaporated. The residue was purified using a cation exchange column eluting with MeOH:NH$_4$OH and freeze dried for 2 days to afford the title compound. $^1$H NMR (500 MHz, MeOD) δ 8.28 (s, 1H), 8.02 (s, 1H), 7.85 (t, J=9.9 Hz, 2H), 7.30 (t, J=55.1 Hz, 1H), 7.08 (d, J=12.1 Hz, 1H), 6.86 (d, J=8.6 Hz, 1H), 6.80 (s, 1H), 5.25 (tt, J=8.2, 3.9 Hz, 1H), 3.98 (dt, J=9.7, 4.5 Hz, 2H), 3.63 (ddd, J=11.8, 9.3, 2.8 Hz, 2H), 3.10 (dd, J=26.7, 11.0 Hz, 2H), 2.94 (t, J=10.1 Hz, 2H), 2.57 (t, J=10.7 Hz, 2H), 2.44 (s, 1H), 2.39 (s, 3H), 2.13-2.06 (m, 2H), 1.81-1.74 (m, 2H), 1.13 (d, J=5.9 Hz, 3H); LCMS [M+1]$^+$=572.56.

Example 404: N-[5-[1-(5-cyanopyrimidin-2-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

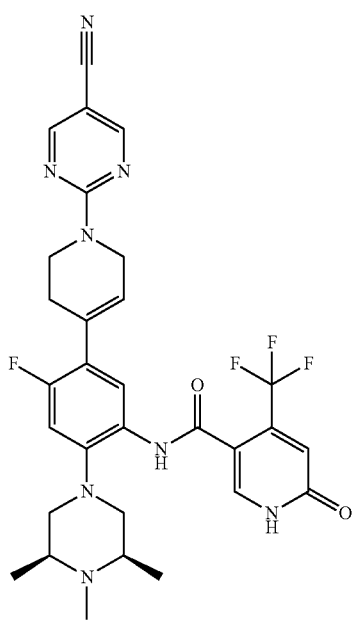

The procedure used was similar to that of Example 270 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) 2-bromo-5-cyanopyrimidine (13.05 mg, 0.071 mmol) to give the title compound (21 mg, 55% yield). $^1$H NMR (500 MHz, METHANOL-d4) δ=8.59-8.47 (m, 2H), 7.87-7.78 (m, 1H), 7.74-7.63 (m, 1H), 6.88-6.83 (m, 1H), 6.82-6.79 (m, 1H), 6.06-5.94 (m, 1H), 4.42-4.35 (m, 2H), 4.09-4.02 (m, 2H), 2.96-2.88 (m, 2H), 2.54-2.41 (m, 6H), 2.30-2.25 (m, 3H), 1.07-1.04 (m, 6H); LCMS [M+H]+ 611.7

Example 405: N-[5-[1-[5-[(dimethylamino)methyl]pyrimidin-2-yl]-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

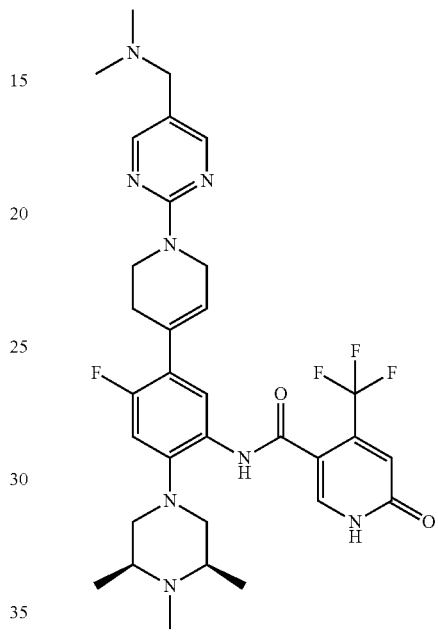

N-(4-Fluoro-5-(1-(5-formylpyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.041 mmol), dimethylamine, 2.0M in THF (0.041 ml, 0.081 mmol) and acetic acid, glacial, 99.8% (9.79 mg, 0.163 mmol) were mixed in anhydrous DCE. A cloudy solution was obtained. After 5 min, sodium triacetoxyborohydride (25.9 mg, 0.122 mmol) was added and the reaction mixture was stirred at ambient temperature for 16 h. The reaction was quenched with sat aq NaHCO$_3$ solution (basic). The organic (org) phase was separated, the aqueous (aq) phase was extracted with DCM (×2), the combined org phase was washed with brine, dried over Na$_2$SO$_4$ and concentrated to afford the crude product. It was purified by silica gel chromatography (4 G), eluting with DCM containing 0-7% MeOH and 0-0.7% NH$_{40}$H to collect the title compound as a white foam (24 mg, 87%). $^1$H NMR (500 MHz, METHANOL-d4) δ=8.37-8.30 (m, 2H), 7.98-7.93 (m, 1H), 7.84-7.75 (m, 1H), 7.00-6.94 (m, 1H), 6.94-6.89 (m, 1H), 6.17-6.09 (m, 1H), 4.42-4.35 (m, 2H), 4.11-4.04 (m, 2H), 3.48-3.42 (m, 2H), 3.07-2.99 (m, 2H), 2.63-2.52 (m, 6H), 2.39-2.36 (m, 3H), 2.34-2.30 (m, 6H), 1.18-1.14 (m, 6H); LCMS [M+H]+ 643.8.

Example 406: N-[4-fluoro-5-[1-[5-(morpholin-4-ylmethyl)pyrimidin-2-yl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

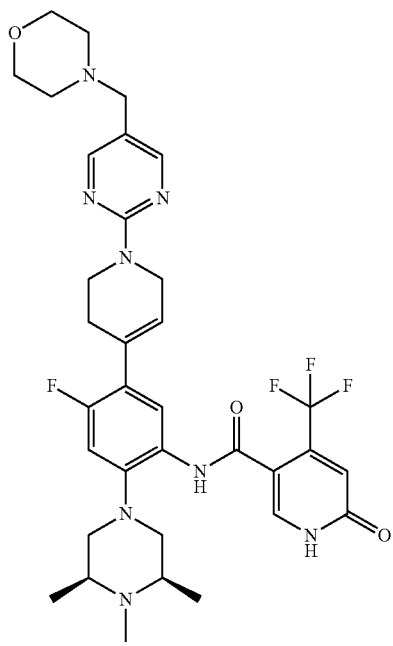 [SMILES: C[C@@H]1CN(c2cc(F)c(C3=CCN(c4ncc(CN5CCOCC5)cn4)CC3)cc2NC(=O)c2c[nH]c(=O)cc2C(F)(F)F)C[C@H](C)N1C]

The procedure followed was similar to Example 405 using N-(4-fluoro-5-(1-(5-formylpyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.041 mmol) and morpholine (5.32 mg, 0.061 mmol) to give the title compound (28 mg, 95% yield). $^1$H NMR (500 MHz, METHANOL-d4) δ=8.37-8.31 (m, 2H), 7.98-7.92 (m, 1H), 7.84-7.76 (m, 1H), 7.00-6.94 (m, 1H), 6.93-6.89 (m, 1H), 6.17-6.09 (m, 1H), 4.42-4.35 (m, 2H), 4.06 (t, J=5.6 Hz, 2H), 3.72-3.68 (m, 4H), 3.44-3.40 (m, 2H), 3.07-2.99 (m, 2H), 2.64-2.53 (m, 6H), 2.51-2.44 (m, 4H), 2.41-2.37 (m, 3H), 1.19-1.15 (m, 6H); LCMS [M+H]+ 685.7

Example 407: N-[4-fluoro-5-[1-[5-[(4-methylpiperazin-1-yl)methyl]pyrimidin-2-yl]-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

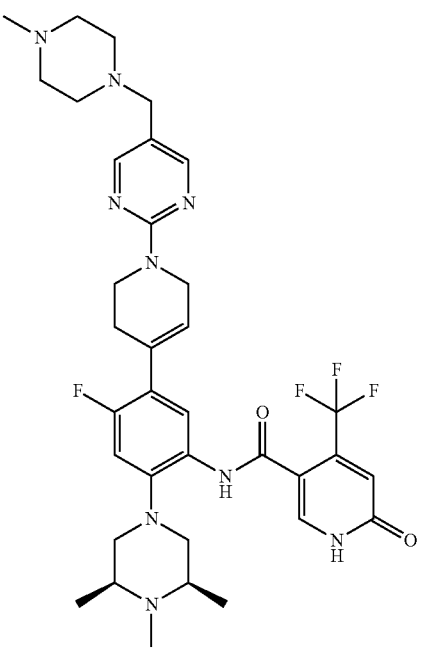 [SMILES: C[C@@H]1CN(c2cc(F)c(C3=CCN(c4ncc(CN5CCN(C)CC5)cn4)CC3)cc2NC(=O)c2c[nH]c(=O)cc2C(F)(F)F)C[C@H](C)N1C]

The procedure followed was similar to Example 405 using N-(4-fluoro-5-(1-(5-formylpyrimidin-2-yl)-1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.041 mmol), 1-methylpiperazine (6.12 mg, 0.061 mmol) to give the title compound (27.5 mg, 92% yield). $^1$H NMR (500 MHz, METHANOL-d4) δ=8.36-8.29 (m, 2H), 7.99-7.94 (m, 1H), 7.84-7.75 (m, 1H), 7.00-6.94 (m, 1H), 6.93-6.88 (m, 1H), 6.17-6.08 (m, 1H), 4.42-4.34 (m, 2H), 4.10-4.03 (m, 2H), 3.44 (s, 2H), 3.03 (br d, J=11.0 Hz, 2H), 2.64-2.56 (m, 6H), 2.55-2.47 (m, 4H), 2.40-2.37 (m, 3H), 2.34-2.30 (m, 3H), 1.16 (d, J=6.1 Hz, 6H); LCMS [M+H]+ 698.8.

Example 408: 2-methylpropyl 5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate

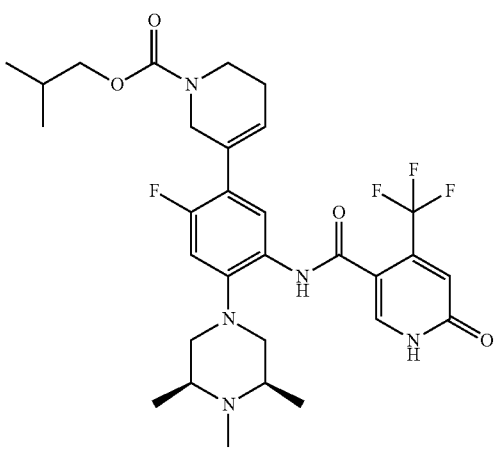 [SMILES: CC(C)COC(=O)N1CCC=C(c2cc(NC(=O)c3c[nH]c(=O)cc3C(F)(F)F)c(N3C[C@@H](C)N(C)[C@@H](C)C3)cc2F)C1]

The procedure followed was similar to Example 253 using N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and isobutyl chloroformate (7.08 µl, 0.054 mmol) to give the title compound (25 mg, 79% yield). $^1$H NMR (500 MHz, METHANOL-d4) δ=7.98-7.93 (m, 1H), 7.82-7.73 (m, 1H), 7.01-6.95 (m, 1H), 6.93-6.88 (m, 1H), 6.14-6.08 (m, 1H), 4.34-4.23 (m, 2H), 3.95-3.89 (m, 2H), 3.70-3.60 (m, 2H), 3.08-3.00 (m, 2H), 2.64-2.51 (m, 4H), 2.40-2.34 (m, 5H), 2.04-1.92 (m, 1H), 1.19-1.15 (m, 6H), 1.01-0.96 (m, 6H).

Example 409: N-[4-fluoro-5-[1-(5-formylpyrimidin-2-yl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide

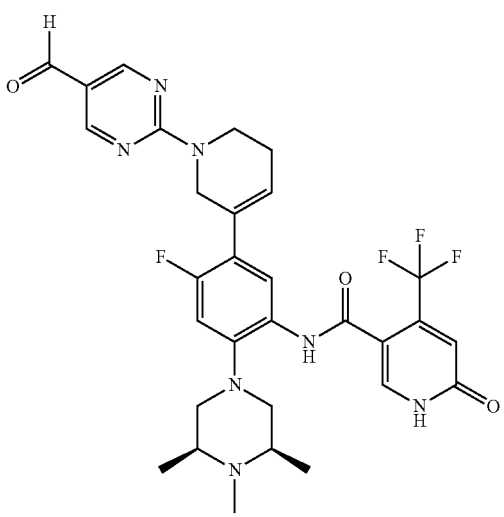 [SMILES: C[C@@H]1CN(c2cc(F)c(C3=CCCN(c4ncc(C=O)cn4)C3)cc2NC(=O)c2c[nH]c(=O)cc2C(F)(F)F)C[C@H](C)N1C]

The procedure used was similar to that of Example 270 using N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (225 mg, 0.443 mmol) and 2-Bromo-pyrimidine-5-carbaldehyde (99 mg, 0.532 mmol) to give the title compound (196 mg, 68% yield). $^1$H NMR (500 MHz, METHANOL-d4) δ=9.81-9.70 (m, 1H), 8.86-8.76 (m, 2H), 8.01-7.92 (m, 1H), 7.86-7.77 (m, 1H), 7.04-6.98 (m, 1H), 6.95-6.88 (m, 1H), 6.25-6.15 (m, 1H), 4.77-4.69 (m, 2H), 4.21-4.13 (m, 2H), 3.10-3.02 (m, 2H), 2.66-2.53 (m, 4H), 2.51-2.43 (m, 2H), 2.41-2.36 (m, 3H), 1.20-1.16 (m, 6H); LCMS [M+H]+ 614.7.

Example 410: 4-(difluoromethyl)-N-[4-fluoro-5-(2-morpholin-4-ylpyrimidin-5-yl)-2-[(3R)-3,4-dimethylpiperazin-1-yl]phenyl]-6-oxo-1H-pyridine-3-carboxamide

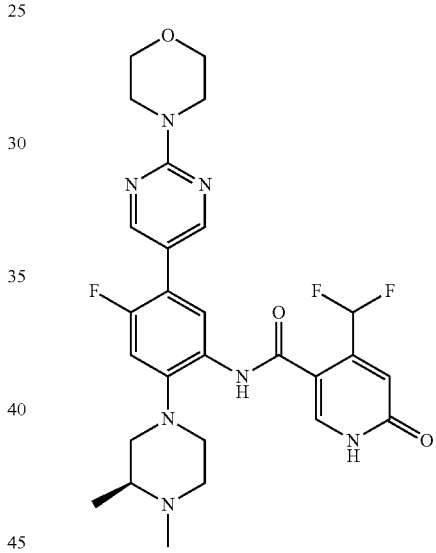

The title compound was prepared according to a sequence similar to Example 39 using 2-(4-morpholino)pyrimidine-5-boronic acid pinacol ester (41.1 mg, 0.141 mmol) and (S)—N-(5-bromo-2-(3,4-dimethylpiperazin-1-yl)-4-fluorophenyl)-4-(difluoromethyl)-6-(2-(trimethylsilyl)ethoxy)nicotinamide (54 mg, 0.094 mmol) to give the title compound (43.6 mg, 81% yield). $^1$H NMR (500 MHz, MeOD) δ 8.54 (s, 2H), 8.02 (s, 1H), 7.82 (d, J=8.3 Hz, 1H), 7.31 (t, J=55.1 Hz, 1H), 7.08 (d, J=12.1 Hz, 1H), 6.81 (s, 1H), 3.85-3.81 (m, 4H), 3.77-3.74 (m, 4H), 3.11 (d, J=11.2 Hz, 1H), 3.06 (d, J=11.5 Hz, 1H), 2.93 (t, J=10.0 Hz, 2H), 2.59-2.52 (m, 2H), 2.41 (d, J=7.5 Hz, 1H), 2.37 (s, 3H), 1.12 (d, J=6.3 Hz, 3H); $^{19}$F NMR (471 MHz, MeOD) δ −120.63 (s), −120.73−−122.51 (m); LCMS [M+1]$^+$=558.65.

Example 411: N-[5-[6-(cyclopropylmethoxy)pyridin-3-yl]-4-fluoro-2-[(3R)-3,4-dimethylpiperazin-1-yl]phenyl]-4-(difluoromethyl)-6-oxo-1H-pyridine-3-carboxamide

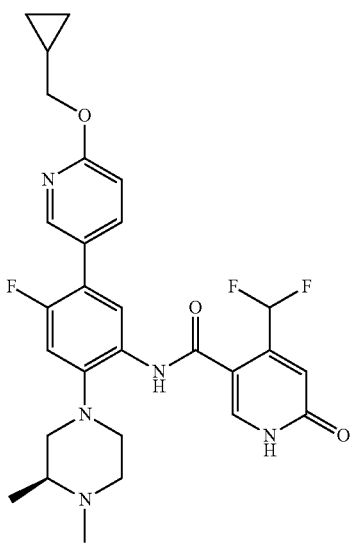 [SMILES: C[C@H]1CN(c2cc(F)c(-c3ccc(OCC4CC4)nc3)cc2NC(=O)c2c[nH]c(=O)cc2C(F)F)CCN1C]

The title compound was prepared using by procedures similar to Example 39 using 2-(cyclopropylmethoxy)-5-(4,4,5,5-tetramethyl-1,3,2-dioxaborolan-2-yl)pyridine (36.5 mg, 0.133 mmol) and (S)—N-(5-bromo-2-(3,4-dimethylpiperazin-1-yl)-4-fluorophenyl)-4-(difluoromethyl)-6-(2-(trimethylsilyl)ethoxy)nicotinamide (50.8 mg, 0.089 mmol) to give the title compound (47.9 mg, 75% yield). $^1$H NMR (500 MHz, MeOD) δ 8.27 (s, 1H), 8.02 (s, 1H), 7.86 (d, J=8.7 Hz, 1H), 7.83 (d, J=8.3 Hz, 1H), 7.30 (t, J=55.1 Hz, 1H), 7.07 (d, J=12.1 Hz, 1H), 6.87 (d, J=8.6 Hz, 1H), 6.80 (s, 1H), 4.15 (d, J=7.1 Hz, 2H), 3.10 (dd, J=26.1, 10.9 Hz, 2H), 2.94 (t, J=10.5 Hz, 2H), 2.57 (t, J=10.9 Hz, 2H), 2.45 (s, 1H), 2.39 (s, 3H), 1.30 (ddd, J=11.9, 7.4, 3.7 Hz, 1H), 1.13 (d, J=6.3 Hz, 3H), 0.64-0.59 (m, 2H), 0.36 (q, J=4.7 Hz, 2H); $^{19}$F NMR (471 MHz, MeOD) δ −120.63 (s), −121.62 (q, J=292.8 Hz); LCMS [M+1]$^+$=542.54.

Example 412: 4-(difluoromethyl)-N-[4-fluoro-5-(6-morpholin-4-ylpyridin-3-yl)-2-[(3R,5S)-3,4,5-trimethylpiperazin-1-yl]phenyl]-6-oxo-1H-pyridine-3-carboxamide

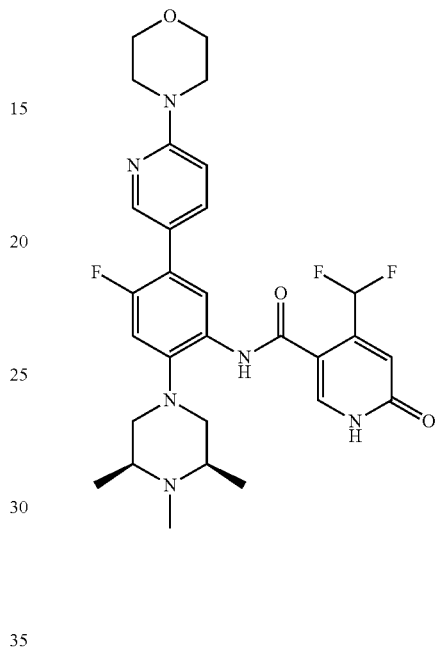

In a 5 mL microwave vial 4-[5-(4,4,5,5-tetramethyl-[1,3,2]dioxaborolan-2-yl)-pyridin-2-yl]-morpholine (36.9 mg, 0.127 mmol), N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (49.9 mg, 0.085 mmol), bis(di-tert-butyl(4-dimethylaminophenyl)phosphine)dichloropalladium(II) (6.01 mg, 8.49 μmol) and potassium phosphate tribasic reagent grade (0.036 g, 0.170 mmol) were dissolved in 1,4-dioxane (1.527 mL)/water (0.170 mL) (9:1 mixture) to give a white suspension. The suspension was stirred for 5 min, degassed, purged with N$_2$, and microwaved for 60 min at 110° C. The solvent was evaporated and 15 mL of CH$_2$Cl$_2$ were added. The suspension was sonicated and extracted from water (15 mL). The solvent was evaporated in vacuo yielding the crude product that was purified by flash column chromatography on silica gel (0-100%, 89% CH$_2$Cl$_2$, 10% MeOH, 1% NH$_4$Ac/CH$_2$Cl$_2$) to afford the protected intermediate. The product was dissolved in 2 mL of dichloromethane and trifluoroacetic acid (97 μl, 1.273 mmol) was added. The solution was stirred for 1 hour and the solvent was evaporated. The residue was purified using a cation exchange column eluting with MeOH:NH$_4$OH and freeze dried for 2 days to afford the title compound. $^1$H NMR (500 MHz, MeOD) δ 8.31 (s, 1H), 8.01 (s, 1H), 7.81 (d, J=8.3 Hz, 1H), 7.78 (d, J=8.7 Hz, 1H), 7.31 (t, J=55.1 Hz, 1H), 7.04 (d, J=12.2 Hz, 1H), 6.90 (d, J=8.9 Hz, 1H), 6.80 (s, 1H), 3.82-3.80 (m, 4H), 3.55-3.51 (m, 4H), 3.06 (d, J=11.0 Hz, 2H), 2.61 (t, J=11.0 Hz, 2H), 2.55 (d, J=5.0 Hz, 2H), 2.37 (s, 3H), 1.16 (d, J=6.0 Hz, 6H); LCMS [M+1]$^+$=569.40.

Example 413: N-[4-fluoro-5-[1-[5-(hydroxymethyl)pyrimidin-2-yl]-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide

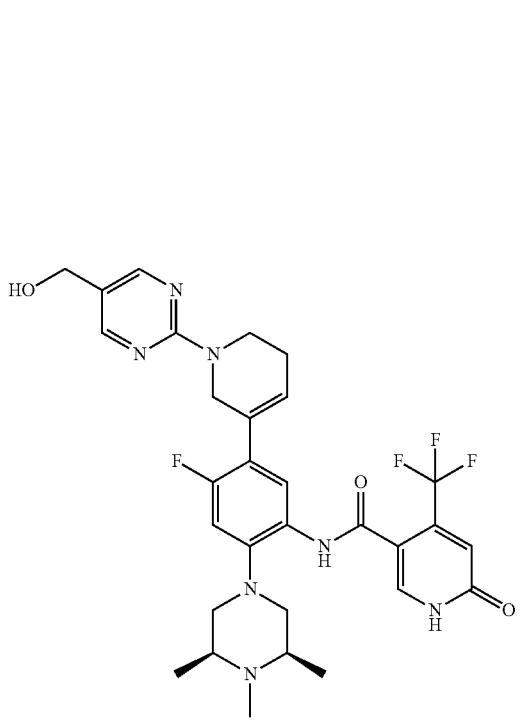 [SMILES: C[C@@H]1CN(c2cc(F)c(C3=CCCN(c4ncc(CO)cn4)C3)cc2NC(=O)c2c[nH]c(=O)cc2C(F)(F)F)C[C@H](C)N1C]

To a mixture of N-(4-fluoro-5-(1-(5-formylpyrimidin-2-yl)-1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.041 mmol) in MeOH (3 ml) and water (0.5 ml) at ambient temperature was added sodium borohydride (7.71 mg, 0.204 mmol). The reaction was stirred at RT for 5 min, quenched with NH$_4$Cl solution, MeOH was removed, and the aq phase was extracted with chloroform/IPA 4:1 solution (4×2 ml). The combined org phase was dried over Na$_2$SO$_4$, concentrated onto celite and purified using sgc (4 g column), eluting with DCM containing 0-8% MeOH and 0-0.8% NH$_4$OH. The desired product was isolated as an orange red powder (20 mg, 76% yield). $^1$H NMR (500 MHz, METHANOL-d4) δ=8.29-8.22 (m, 2H), 7.87-7.80 (m, 1H), 7.73-7.61 (m, 1H), 6.90-6.84 (m, 1H), 6.82-6.76 (m, 1H), 6.08-5.99 (m, 1H), 4.46-4.41 (m, 2H), 4.38-4.33 (m, 2H), 3.94-3.86 (m, 2H), 2.97-2.89 (m, 2H), 2.55-2.40 (m, 4H), 2.33-2.25 (m, 5H), 1.08-1.03 (m, 6H); LCMS [M+H]+ 616.7

Example 414: N-[5-[1-[5-[(dimethylamino)methyl]pyrimidin-2-yl]-3,6-dihydro-2H-pyridin-5-yl]-4-fluoro-2-[(3R,5S)-3,4,5-trimethylpiperazin-1-yl]phenyl]-6-oxo-4-(trifluoromethyl)-1H-pyridine-3-carboxamide

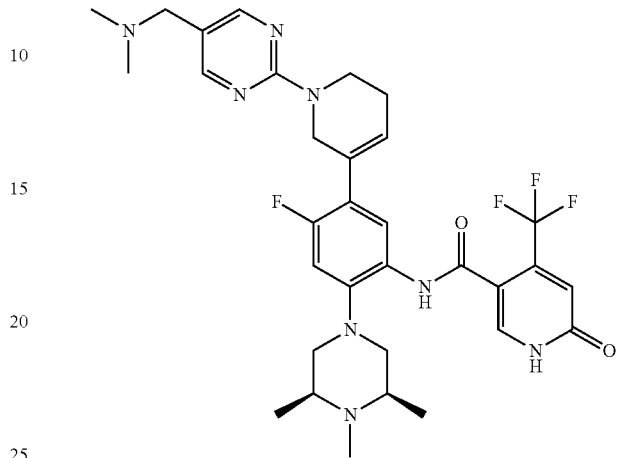

The procedure followed was similar to Example 405 using N-(4-fluoro-5-(1-(5-formylpyrimidin-2-yl)-1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.041 mmol) and dimethylamine (2.0M in THF, 0.041 ml, 0.081 mmol), to afford the title compound (24.5 mg, 89% yield). $^1$H NMR (500 MHz, METHANOL-d4) δ 8.17-8.24 (m, 2H), 7.85 (s, 1H), 7.68 (d, J=7.95 Hz, 1H), 6.86 (d, J=12.23 Hz, 1H), 6.79 (s, 1H), 6.04 (br. s., 1H), 4.44 (br. s., 2H), 3.90 (t, J=5.75 Hz, 2H), 3.30 (s, 2H), 2.92 (d, J=11.13 Hz, 2H), 2.46-2.53 (m, 2H), 2.38-2.44 (m, 2H), 2.30 (d, J=3.55 Hz, 2H), 2.25 (s, 3H), 2.18 (s, 6H), 1.05 (d, J=6.11 Hz, 6H); LCMS [M+H]+ 643.8.

Example 415: N-[4-fluoro-5-[1-[5-(morpholin-4-ylmethyl)pyrimidin-2-yl]-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide

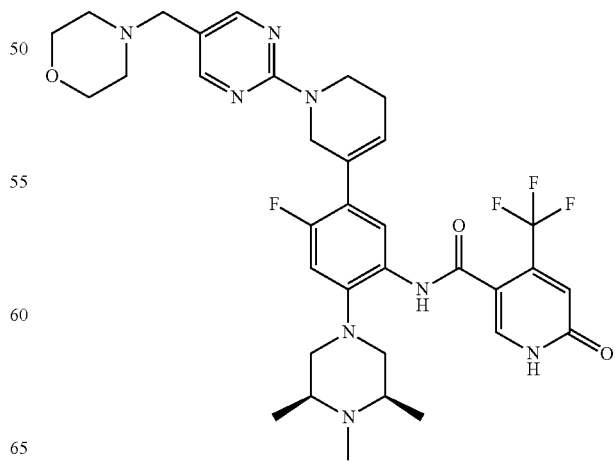

The procedure followed was similar to Example 405 using N-(4-fluoro-5-(1-(5-formylpyrimidin-2-yl)-1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.041 mmol) and morpholine (7.10 mg, 0.081 mmol) to give the title compound (20 mg, 68% yield). $^1$H NMR (500 MHz, METHANOL-d4) δ 8.30 (s, 2H), 7.94 (s, 1H), 7.78 (d, J=7.95 Hz, 1H), 6.96 (d, J=12.23 Hz, 1H), 6.90 (s, 1H), 6.14 (br. s., 1H), 4.53 (br. s., 2H), 3.99 (t, J=5.75 Hz, 2H), 3.68 (t, J=4.46 Hz, 4H), 3.39 (s, 2H), 3.02 (d, J=11.13 Hz, 2H), 2.56-2.63 (m, 2H), 2.49-2.55 (m, 2H), 2.46 (br. s., 4H), 2.39 (d, J=3.42 Hz, 2H), 2.36 (s, 3H), 1.15 (d, J=6.11 Hz, 6H); LCMS [M+H]+ 685.9.

Example 416: N-[4-fluoro-5-[1-[5-[(4-methylpiperazin-1-yl)methyl]pyrimidin-2-yl]-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide

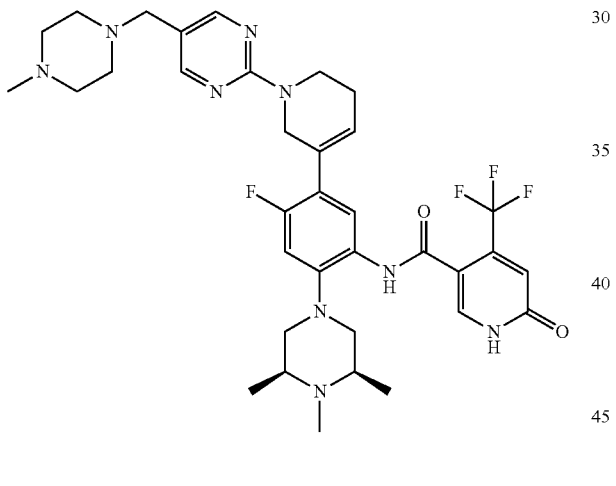

A procedure similar to that used in Example 405 with N-(4-fluoro-5-(1-(5-formylpyrimidin-2-yl)-1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.041 mmol) and 1-methylpiperazine (4.08 mg, 0.041 mmol) gave the title compound (24 mg, 80% yield). $^1$H NMR (500 MHz, METHANOL-d4) δ=8.22-8.16 (m, 2H), 7.88-7.83 (m, 1H), 7.72-7.64 (m, 1H), 6.90-6.84 (m, 1H), 6.82-6.77 (m, 1H), 6.07-6.00 (m, 1H), 4.47-4.41 (m, 2H), 3.92-3.88 (m, 2H), 3.33-3.29 (m, 2H), 2.96-2.89 (m, 2H), 2.64-2.45 (m, 5H), 2.45-2.38 (m, 5H), 2.37-2.27 (m, 4H), 2.26-2.24 (m, 3H), 2.21-2.19 (m, 3H), 2.12-2.12 (m, 1H), 1.05 (d, J=6.1 Hz, 6H); LCMS [M+H]+ 698.8

Example 417: N-[4-fluoro-2-[(3S)-3-(dimethylamino)pyrrolidin-1-yl]-5-[2-[(2R,6S)-2,6-dimethylmorpholin-4-yl]pyrimidin-5-yl]phenyl]-6-oxo-4-(trifluoromethyl)-JH-pyridine-3-carboxamide

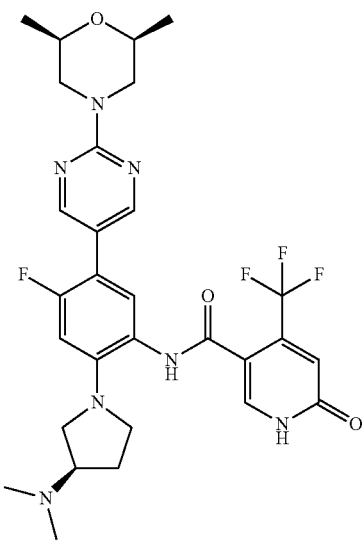 [SMILES: C[C@@H]1CN(c2ncc(-c3cc(NC(=O)c4c[nH]c(=O)cc4C(F)(F)F)c(N4CC[C@@H](N(C)C)C4)cc3F)cn2)C[C@H](C)O1]

Step 1: (R)-1-(4-bromo-5-fluoro-2-nitrophenyl)-N,N-dimethylpyrrolidin-3-amine

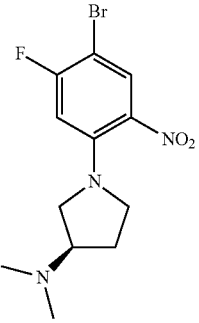 [SMILES: CN(C)[C@@H]1CCN(c2cc(F)c(Br)cc2[N+](=O)[O-])C1]

A solution of 1-bromo-2,4-difluoro-5-nitrobenzene (2.7 mL, 21 mmol) in toluene (5 mL) was added dropwise to a rapidly stirring mixture of (3R)-(+)-3-(dimethylamino)pyrrolidine (2.4 g, 21 mmol) and potassium carbonate (1.4 g, 10 mmol) in toluene (50 mL) at room temperature. After stirring for 20 minutes the reaction was warmed to 45° C. for 30 minutes. After the reaction was cooled to room temperature the reaction mixture was partitioned between water (100 mL) and ethyl acetate (100 mL). The layers were separated and the aqueous layer was extracted with additional ethyl acetate. The combined organic extracts were dried over magnesium sulfate and after removal of the inorganics by filtration the filtrate was concentrated onto celite. Purification by flash chromatography [1-10% MeOH/DCM+0.5% NH$_4$OH] afforded (R)-1-(4-bromo-5-fluoro-2-nitrophenyl)-N,N-dimethylpyrrolidin-3-amine (6.4 g, 91%). LCMS [M+H]+: 332.1.

Step 2: (R)-1-(4-(2-(cis-2,6-dimethylmorpholino)pyrimidin-5-yl)-5-fluoro-2-nitrophenyl)-N,N-dimethylpyrrolidin-3-amine

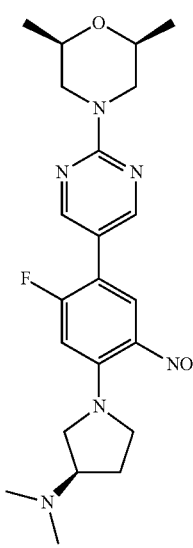

A vial was charged with a mixture of (R)-1-(4-bromo-5-fluoro-2-nitrophenyl)-N,N-dimethylpyrrolidin-3-amine (0.050 g, 0.15 mmol), (2-(cis-2,6-dimethylmorpholino)pyrimidin-5-yl)boronic acid (0.050 g, 0.21 mmol), XPhos Pd G2 (2 mg, 3.0 µmol) and XPhos (1.5 mg, 3.0 µmol). The vial was sealed with a septum, evacuated and backfilled with nitrogen. 1,4-Dioxane (3 mL) and 2 M aqueous sodium carbonate (0.4 mL) were added via syringe and the vial was evacuated and backfilled an additional time. The reaction was heated to 95° C. in an aluminum block for 18 h. After cooling to room temperature the reaction mixture was concentrated onto celite and purified by flash chromatography [0.5-9.5% MeOH/DCM+0.5% NH₄OH] to afford (R)-1-(4-(2-(cis-2,6-dimethylmorpholino)pyrimidin-5-yl)-5-fluoro-2-nitrophenyl)-N,N-dimethylpyrrolidin-3-amine (0.066 g, 99%). LCMS [M+H]+: 445.6.

Step 3: (R)-1-(2-amino-4-(2-(cis-2,6-dimethylmorpholino)pyrimidin-5-yl)-5-fluorophenyl)-N,N-dimethylpyrrolidin-3-amine

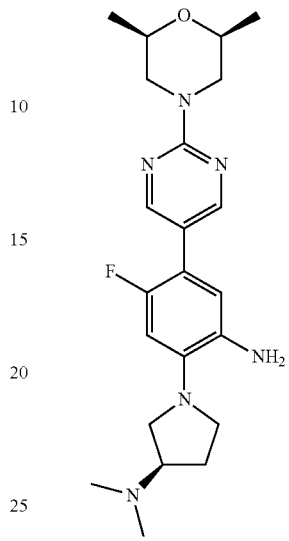

A mixture of (R)-1-(4-(2-(cis-2,6-dimethylmorpholino)pyrimidin-5-yl)-5-fluoro-2-nitrophenyl)-N,N-dimethylpyrrolidin-3-amine (0.066 g, 0.15 mmol) and tin(II) chloride (0.11 g, 0.60 mmol in EtOH (5 mL) was heated to 75° C. for 1 h. The reaction mixture was concentrated onto celite and purification by flash chromatography [0.5-10% MeOH/DCM+0.5% NH₄OH] afforded (R)-1-(2-amino-4-(2-(cis-2,6-dimethylmorpholino)pyrimidin-5-yl)-5-fluorophenyl)-N,N-dimethylpyrrolidin-3-amine (0.050 g, 81%). LCMS [M+H]+: 415.5.

Step 4: N-(2-((R)-3-(dimethylamino)pyrrolidin-1-yl)-5-(2-(cis-2,6-dimethylmorpholino)pyrimidin-5-yl)-4-fluorophenyl)-6-oxo-4-(trifluoromethyl)-1,6-dihydropyridine-3-carboxamide

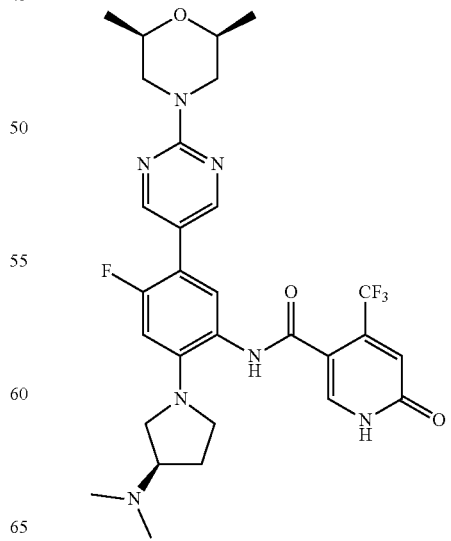

4-(Trifluoromethyl)-6-(2-(trimethylsilyl)ethoxy)nicotinic acid (0.028 g, 0.090 mmol) was activated with HATU (0.035 g, 0.090 mmol) and N,N-diisopropylethylamine (0.02 mL, 0.090 mmol) in DMF (0.5 mL) at room temperature. The solution of activated acid was added to a solution of (R)-1-(2-amino-4-(2-(cis-2,6-dimethylmorpholino)pyrimidin-5-yl)-5-fluorophenyl)-N,N-dimethylpyrrolidin-3-amine (0.025 g, 0.060 mmol) in DMF (1 mL) and the reaction was heated to 55° C. for 18 h. After cooling to room temperature the reaction mixture was concentrated onto celite and purified by flash chromatography [0.5-7.5% MeOH/DCM+0.5% NH₄OH]. The silyl protected amide was dissolved in DCM (2 mL) and treated with TFA (1 mL) at room temperature. After stirring for 2 h the volatiles were removed under a stream of air and the title compound was isolated by a catch and release protocol using a SCX2 silica cartridge to afford the title compound (0.019 g, 52%). $^1$H NMR (500 MHz, DMSO-d6) δ=12.53 (br s, 1H), 9.81 (s, 1H), 8.48 (s, 2H), 7.95 (br s, 1H), 7.29 (br d, J=8.8 Hz, 1H), 6.80 (s, 1H), 6.66 (br d, J=14.2 Hz, 1H), 4.52 (br d, J=12.6 Hz, 2H), 3.60-3.53 (m, 4H), 2.60-2.53 (m, 4H), 2.15 (s, 6H), 2.11-2.00 (m, 1H), 1.69 (quin, J=9.9 Hz, 1H), 1.16 (br d, J=6.1 Hz, 6H), 1.09-0.97 (m, 1H); LCMS [M+H]+: 604.6.

Example 418: N-[4-fluoro-5-[2-[(2R,6S)-2,6-dimethylmorpholin-4-yl]pyrimidin-5-yl]-2-[(3S)-3-[ethyl(methyl)amino]pyrrolidin-1-yl]phenyl]-6-oxo-4-(trifluoromethyl)-1H-pyridine-3-carboxamide

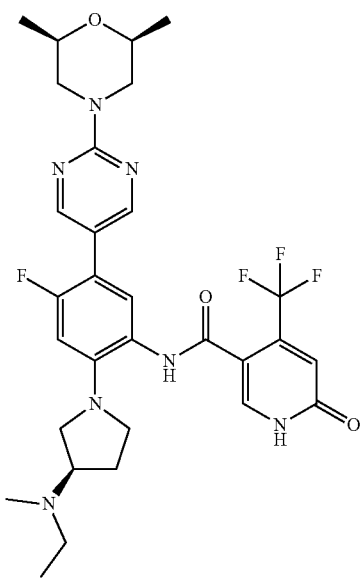 [SMILES: CCN(C)[C@@H]1CCN(c2cc(F)c(-c3cnc(N4C[C@@H](C)O[C@@H](C)C4)nc3)cc2NC(=O)c2c[nH]c(=O)cc2C(F)(F)F)C1]

The title compound was prepared similar to the procedure described above for the preparation of Example 417 using (R)—N-ethyl-N-methylpyrrolidin-3-amine in place of (3R)-(+)-3-(dimethylamino)pyrrolidine in Step 1. $^1$H NMR (500 MHz, DMSO-d6) δ=12.53 (br s, 1H), 9.79 (s, 1H), 8.48 (s, 2H), 7.94 (br s, 1H), 7.30 (br d, J=8.8 Hz, 1H), 6.80 (s, 1H), 6.66 (d, J=13.9 Hz, 1H), 4.52 (br d, J=12.7 Hz, 2H), 3.60-3.53 (m, 2H), 3.40-3.36 (m, J=9.2 Hz, 3H), 3.26-3.20 (m, 2H), 2.89 (br d, J=5.1 Hz, 1H), 2.60-2.53 (m, 3H), 2.45-2.38 (m, 2H), 2.14 (s, 3H), 2.11-2.04 (m, 1H), 1.74-1.64 (m, 1H), 1.16 (d, J=6.1 Hz, 6H), 0.95 (br t, J=7.0 Hz, 3H); LCMS [M+H]+: 618.5.

Example 419: N-[4-fluoro-5-(2-morpholin-4-ylpyrimidin-5-yl)-2-[(3R)-3-(diethylamino)pyrrolidin-1-yl]phenyl]-6-oxo-4-(trifluoromethyl)-1H-pyridine-3-carboxamide

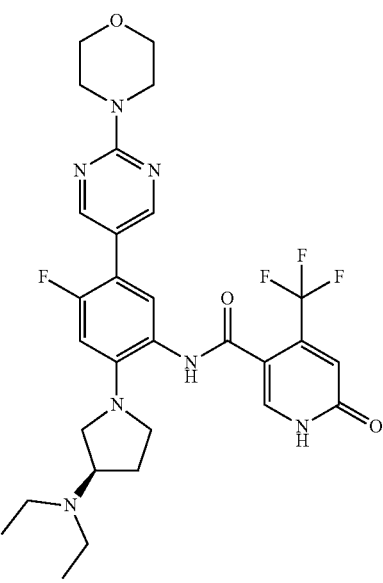 [SMILES: CCN(CC)[C@@H]1CCN(c2cc(F)c(-c3cnc(N4CCOCC4)nc3)cc2NC(=O)c2c[nH]c(=O)cc2C(F)(F)F)C1]

The title compound was prepared similar to the procedure described above for the preparation of Example 417 using diethylamine in place of N-ethylmethylamine in Step 1 and (2-morpholinopyrimidin-5-yl)boronic acid in Step 2. $^1$H NMR (500 MHz, DMSO-d6) δ=12.44 (br s, 1H), 9.78 (s, 1H), 8.50 (s, 2H), 7.95 (br s, 1H), 7.31 (br d, J=8.6 Hz, 1H), 6.79 (s, 1H), 6.66 (d, J=13.9 Hz, 1H), 3.75-3.72 (m, 4H), 3.69-3.66 (m, 4H), 3.37-3.35 (m, 3H), 3.25-3.18 (m, 2H), 2.58-2.52 (m, 5H), 2.10-2.03 (m, 1H), 1.73-1.64 (m, 1H), 0.99 (br d, J=6.2 Hz, 3H), 0.91 (t, J=7.0 Hz, 6H); LCMS [M+H]+: 604.5.

583

Example 420: N-[4-fluoro-5-(2-morpholin-4-ylpyrimidin-5-yl)-2-[(3R)-3-[methyl(propan-2-yl)amino]pyrrolidin-1-yl]phenyl]-6-oxo-4-(trifluoromethyl)-1H-pyridine-3-carboxamide

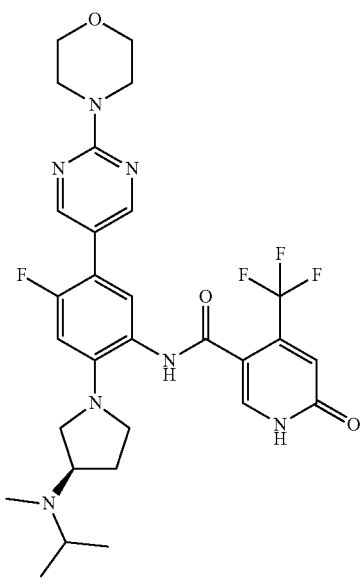 [SMILES: CC(C)N(C)[C@@H]1CCN(c2cc(F)c(-c3cnc(N4CCOCC4)nc3)cc2NC(=O)c2c[nH]c(=O)cc2C(F)(F)F)C1]

The title compound was prepared similar to the procedure described above for the preparation of Example 417 using N-isopropyl-N-methylamine in place of N-ethylmethylamine in Step 1 and (2-morpholinopyrimidin-5-yl)boronic acid in Step 2. $^1$H NMR (500 MHz, DMSO-d6) δ=9.79 (s, 1H), 8.50 (s, 2H), 7.94 (br s, 1H), 7.30 (br d, J=8.8 Hz, 1H), 6.79 (s, 1H), 6.66 (d, J=14.1 Hz, 1H), 3.75-3.71 (m, 4H), 3.70-3.66 (m, 4H), 3.41-3.35 (m, 3H), 3.25-3.20 (m, 1H), 3.09-3.01 (m, 2H), 2.95-2.88 (m, 1H), 2.05 (s, 3H), 1.71-1.62 (m, 1H), 0.98 (br d, J=6.5 Hz, 6H); LCMS [M+H]+: 604.5.

584

Example 421: N-[4-fluoro-5-[6-[(2R,6S)-2,6-dimethylmorpholin-4-yl]pyridin-3-yl]-2-[(3R)-3,4-dimethylpiperazin-1-yl]phenyl]-1-methyl-6-oxo-4-(trifluoromethyl)pyridine-3-carboxamide

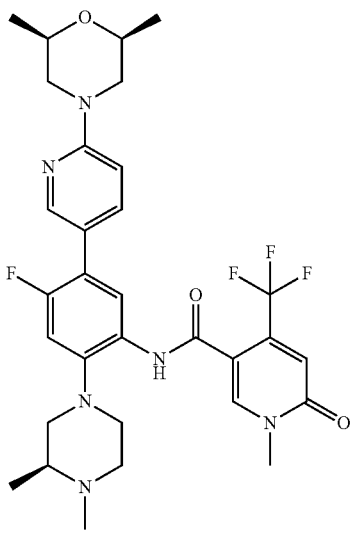

The title compound (white solid, 26.0 mg, 42%) was prepared by a procedure similar to Example 209 using (2S,6R)-2,6-dimethyl-4-(5-(4,4,5,5-tetramethyl-1,3,2-dioxaborolan-2-yl)pyridin-2-yl)morpholine (47 mg, 0.15 mmol) and (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (50.4 mg, 0.1 mmol). $^1$H NMR (500 MHz, METHANOL-d4) δ=8.32 (s, 1H), 8.26 (s, 1H), 7.93 (d, J=8.3 Hz, 1H), 7.79 (br d, J=9.0 Hz, 1H), 7.09 (d, J=12.1 Hz, 1H), 6.95 (s, 1H), 6.92 (d, J=8.6 Hz, 1H), 4.16 (br d, J=12.6 Hz, 2H), 3.78-3.70 (m, 2H), 3.67 (s, 3H), 3.15-3.04 (m, 2H), 2.96 (br t, J=10.2 Hz, 2H), 2.63-2.51 (m, 4H), 2.49-2.43 (m, 1H), 2.40 (br s, 3H), 1.27 (d, J=6.2 Hz, 6H), 1.15 (d, J=6.2 Hz, 3H); LCMS [M+H]$^+$ 617.6.

Example 422: N-[4-fluoro-5-[6-[(2R,6S)-2,6-dimethylmorpholin-4-yl]pyridin-3-yl]-2-[(3S,5R)-3,4,5-trimethylpiperazin-1-yl]phenyl]-1-methyl-6-oxo-4-(trifluoromethyl)pyridine-3-carboxamide

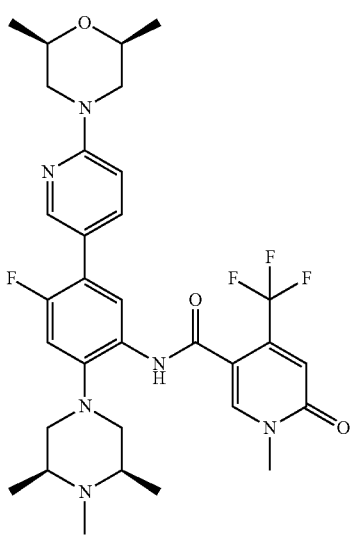

The title compound (white solid, 26.4 mg, 42%) was prepared through a procedure similar to Example 209 using (2S,6R)-2,6-dimethyl-4-(5-(4,4,5,5-tetramethyl-1,3,2-dioxaborolan-2-yl)pyridin-2-yl)morpholine (47 mg, 0.15 mmol) and N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (51.8 mg, 0.1 mmol). $^1$H NMR (500 MHz, METHANOL-d4) δ=8.31 (s, 1H), 8.26 (s, 1H), 7.93 (d, J=8.3 Hz, 1H), 7.79 (br d, J=8.8 Hz, 1H), 7.09 (d, J=12.0 Hz, 1H), 6.95 (s, 1H), 6.92 (d, J=8.7 Hz, 1H), 4.16 (br d, J=12.1 Hz, 2H), 3.78-3.70 (m, 2H), 3.66 (s, 3H), 3.09 (br d, J=8.4 Hz, 2H), 2.73-2.51 (m, 6H), 2.44 (br s, 3H), 1.27 (d, J=6.2 Hz, 6H), 1.21 (br s, 6H); LCMS [M+H]$^+$ 631.6.

Example 423: 4-fluoro-N-[4-fluoro-5-[6-[(2R,6S)-2,6-dimethylmorpholin-4-yl]pyridin-3-yl]-2-[(3R)-3,4-dimethylpiperazin-1-yl]phenyl]-2-(trifluoromethyl)benzamide

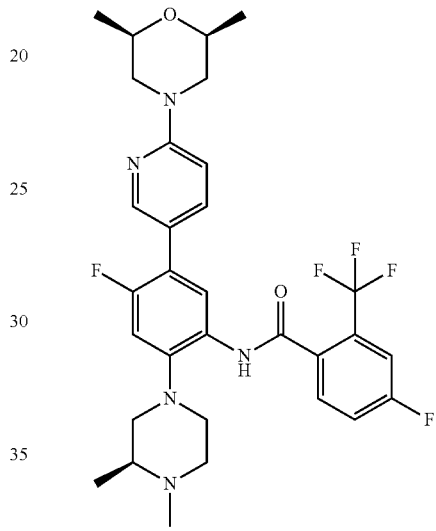

The title compound (formic acid salt, off white solid, 43.0 mg, 66%) was prepared by a method similar to that of Example 400 using (2S,6R)-2,6-dimethyl-4-(5-(4,4,5,5-tetramethyl-1,3,2-dioxaborolan-2-yl)pyridin-2-yl)morpholine (47 mg, 0.15 mmol) and (S)—N-(5-bromo-2-(3,4-dimethylpiperazin-1-yl)-4-fluorophenyl)-4-fluoro-2-(trifluoromethyl)benzamide (49.2 mg, 0.1 mmol). $^1$H NMR (500 MHz, METHANOL-d4) δ=8.52-8.35 (m, 1H), 8.33 (s, 1H), 8.05 (d, J=8.1 Hz, 1H), 7.84-7.77 (m, 2H), 7.67 (br d, J=8.9 Hz, 1H), 7.58 (br t, J=7.9 Hz, 1H), 7.18 (br d, J=11.7 Hz, 1H), 6.93 (d, J=8.2 Hz, 1H), 4.17 (br d, J=12.7 Hz, 2H), 3.78-3.70 (m, 2H), 3.51-3.41 (m, 1H), 3.41-3.35 (m, 1H), 3.31-3.08 (m, 5H), 2.94-2.77 (m, 4H), 2.55 (br t, J=11.6 Hz, 2H), 1.40-1.32 (m, 3H), 1.27 (br d, J=6.2 Hz, 6H); LCMS [M+H]$^+$ 604.6.

Example 424: N-[4-fluoro-5-[2-(4-hydroxy-4-methylpiperidin-1-yl)pyrimidin-5-yl]-2-[(3R)-3,4-dimethylpiperazin-1-yl]phenyl]-6-oxo-4-(trifluoromethyl)-1H-pyridine-3-carboxamide

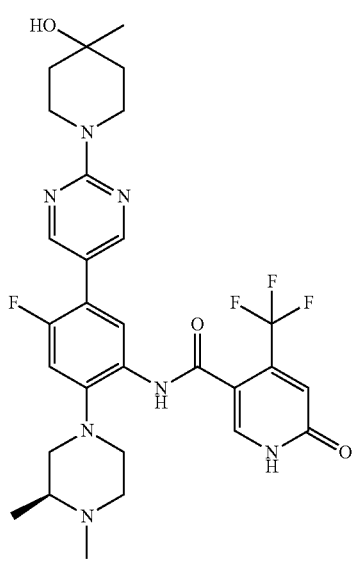 [SMILES: C[C@H]1CN(c2cc(F)c(-c3cnc(N4CCC(C)(O)CC4)nc3)cc2NC(=O)c2c[nH]c(=O)cc2C(F)(F)F)CCN1C]

To a mixture of 2-chloropyrimidine-5-boronic acid (48 mg, 0.3 mmol) and 4-methylpiperidin-4-ol (36 mg, 0.315 mmol) in EtOH (2 mL) was added triethylamine (0.070 mL, 0.5 mmol). The resulting mixture was stirred at 80° C. for 1 h and solvents were removed to give crude (2-(4-hydroxy-4-methylpiperidin-1-yl)pyrimidin-5-yl)boronic acid as a yellow solid. LCMS [M+H]$^+$ 238.4. The title compound (light beige solid, 34.7 mg, 57%) was prepared according to a method similar to Example 40 using crude (2-(4-hydroxy-4-methylpiperidin-1-yl)pyrimidin-5-yl)boronic acid (0.3 mmol) and (S)—N-(5-bromo-2-(3,4-dimethylpiperazin-1-yl)-4-fluorophenyl)-6-oxo-4-(trifluoromethyl)-1,6-dihydropyridine-3-carboxamide (49 mg, 0.1 mmol). $^1$H NMR (500 MHz, METHANOL-d4) δ=8.51 (s, 2H), 7.99 (s, 1H), 7.91 (br d, J=8.2 Hz, 1H), 7.10 (d, J=12.1 Hz, 1H), 6.93 (s, 1H), 4.29 (td, J=4.0, 13.2 Hz, 2H), 3.63-3.53 (m, 2H), 3.14-3.03 (m, 2H), 2.99-2.91 (m, 2H), 2.61-2.52 (m, 2H), 2.47-2.42 (m, 1H), 2.39 (s, 3H), 1.71-1.58 (m, 4H), 1.28 (s, 3H), 1.14 (d, J=6.2 Hz, 3H); LCMS [M+H]$^+$ 604.5.

Example 425: N-[4-fluoro-5-[2-(4-hydroxy-4-methylpiperidin-1-yl)pyrimidin-5-yl]-2-[(3R,5S)-3,4,5-trimethylpiperazin-1-yl]phenyl]-6-oxo-4-(trifluoromethyl)-1H-pyridine-3-carboxamide

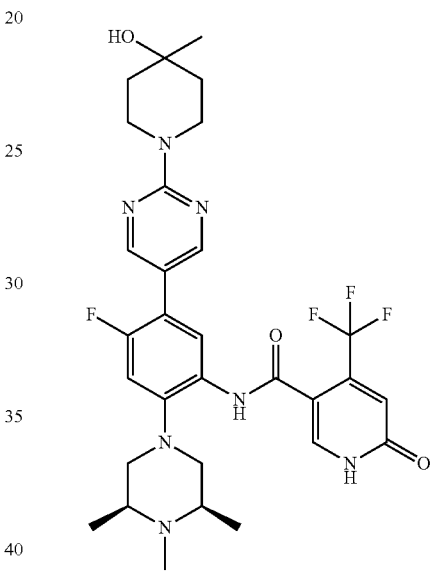

The title compound (light beige solid, 29.2 mg, 47%) was prepared by a procedure similar to Example 31 using crude (2-(4-hydroxy-4-methylpiperidin-1-yl)pyrimidin-5-yl)boronic acid (0.3 mmol) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (51 mg, 0.1 mmol). $^1$H NMR (500 MHz, METHANOL-d4) δ=8.51 (s, 2H), 7.98 (s, 1H), 7.90 (d, J=8.2 Hz, 1H), 7.09 (d, J=12.1 Hz, 1H), 6.93 (s, 1H), 4.29 (td, J=4.2, 13.3 Hz, 2H), 3.58 (ddd, J=3.5, 10.3, 13.3 Hz, 2H), 3.07 (br d, J=11.0 Hz, 2H), 2.67-2.53 (m, 4H), 2.40 (s, 3H), 1.70-1.58 (m, 4H), 1.28 (s, 3H), 1.18 (d, J=6.0 Hz, 6H); LCMS [M+H]$^+$ 618.5.

589

Example 426: N-[4-fluoro-2-[(3S)-3-(dimethyl-amino)pyrrolidin-1-yl]-5-[2-[(2R,6S)-2,6-dimethyl-morpholin-4-yl]pyrimidin-5-yl]phenyl]-1-methyl-6-oxo-4-(trifluoromethyl)pyridine-3-carboxamide

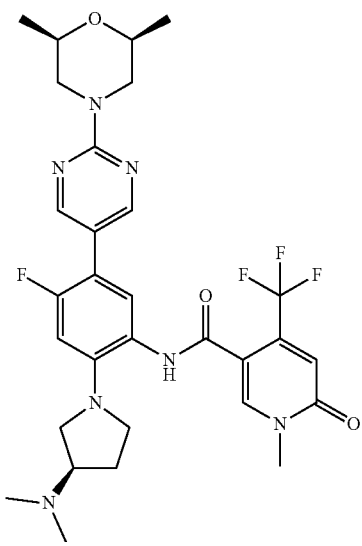 [SMILES: C[C@@H]1CN(c2ncc(-c3cc(NC(=O)c4cn(C)c(=O)cc4C(F)(F)F)c(N4CC[C@@H](N(C)C)C4)cc3F)cn2)C[C@H](C)O1]

The title compound was prepared similar to the procedure described above for the preparation of Example 417 Step 4 using (R)-1-(2-amino-4-(2-((2S,6R)-2,6-dimethylmorpholino)pyrimidin-5-yl)-5-fluorophenyl)-N,N-dimethylpyrrolidin-3-amine (25 mg, 0.060 mmol) and [1-methyl-6-oxo-4-(trifluoromethyl)-1,6-dihydropyridine-3-carboxylic acid (20.00 mg, 0.090 mmol) to give the title compound (37.3 mg, 34% yield). $^1$H NMR (500 MHz, DMSO-d6) δ=9.79 (s, 1H), 8.47 (s, 2H), 8.33 (s, 1H), 7.28 (d, J=8.8 Hz, 1H), 6.86 (s, 1H), 6.69 (d, J=13.8 Hz, 1H), 4.52 (br d, J=12.0 Hz, 2H), 3.60-3.52 (m, 7H), 3.25-3.19 (m, 2H), 2.67-2.56 (m, 7H), 2.14 (s, 6H), 2.10-2.03 (m, 1H), 1.75-1.65 (m, 1H), 1.16 (d, J=6.2 Hz, 6H); LCMS [M+H]+: 618.5.

590

Example 427: N-[4-fluoro-5-[2-[(2R,6S)-2,6-dimethylmorpholin-4-yl]pyrimidin-5-yl]-2-[(3S)-3-[ethyl(methyl)amino]pyrrolidin-1-yl]phenyl]-1-methyl-6-oxo-4-(trifluoromethyl)pyridine-3-carboxamide

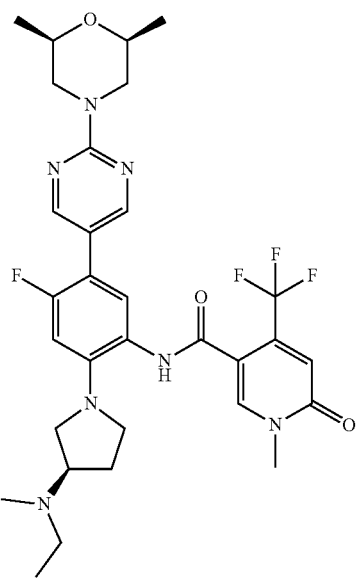 [SMILES: CCN(C)[C@@H]1CCN(c2cc(F)c(-c3cnc(N4C[C@@H](C)O[C@@H](C)C4)nc3)cc2NC(=O)c2cn(C)c(=O)cc2C(F)(F)F)C1]

The title compound was prepared similar to the procedure described above for the preparation of Example 417 using 1-methyl-6-oxo-4-(trifluoromethyl)-1,6-dihydropyridine-3-carboxylic acid in place of 4-(trifluoromethyl)-6-(2-(trimethylsilyl)ethoxy)nicotinic acid in Step 4. $^1$H NMR (500 MHz, DMSO-d6) δ=9.78 (s, 1H), 8.47 (s, 2H), 8.32 (s, 1H), 7.28 (d, J=8.7 Hz, 1H), 6.86 (s, 1H), 6.69 (d, J=13.9 Hz, 1H), 4.52 (br d, J=11.7 Hz, 2H), 3.59-3.52 (m, 5H), 3.42-3.36 (m, 4H), 3.27-3.20 (m, 1H), 2.93-2.84 (m, 1H), 2.60-2.53 (m, 3H), 2.44-2.38 (m, 2H), 2.13 (s, 3H), 2.11-2.05 (m, 1H), 1.73-1.65 (m, 1H), 1.16 (d, J=6.2 Hz, 6H), 0.95 (t, J=7.1 Hz, 3H); LCMS [M+H]+: 632.6.

Example 428: N-[4-fluoro-5-(2-morpholin-4-ylpyrimidin-5-yl)-2-[(3R)-3-(diethylamino)pyrrolidin-1-yl]phenyl]-1-methyl-6-oxo-4-(trifluoromethyl)pyridine-3-carboxamide

Example 429: N-[4-fluoro-5-(2-morpholin-4-ylpyrimidin-5-yl)-2-[(3R)-3-[methyl(propan-2-yl)amino]pyrrolidin-1-yl]phenyl]-1-methyl-6-oxo-4-(trifluoromethyl)pyridine-3-carboxamide

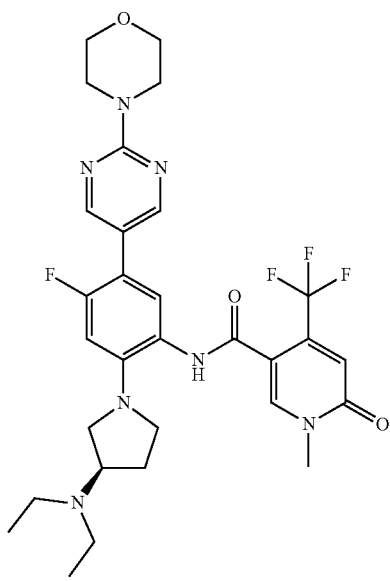 [SMILES: CCN(CC)[C@@H]1CCN(c2cc(F)c(-c3cnc(N4CCOCC4)nc3)cc2NC(=O)c2cn(C)c(=O)cc2C(F)(F)F)C1]

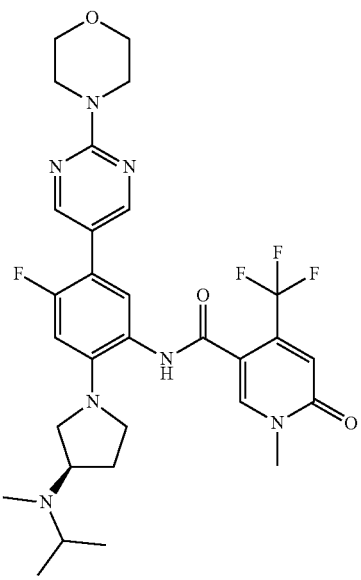 [SMILES: CC(C)N(C)[C@@H]1CCN(c2cc(F)c(-c3cnc(N4CCOCC4)nc3)cc2NC(=O)c2cn(C)c(=O)cc2C(F)(F)F)C1]

The title compound was prepared according to a sequence similar to the preparation of Example 417 using (R)-1-(2-amino-5-fluoro-4-(2-morpholinopyrimidin-5-yl)phenyl)-N,N-diethylpyrrolidin-3-amine (19 mg, 0.046 mmol) that was dissolved in N,N-Dimethylformamide (DMF) (1 ml) and treated with a solution of activated acid [1-methyl-6-oxo-4-(trifluoromethyl)-1,6-dihydropyridine-3-carboxylic acid (15.20 mg, 0.069 mmol) to give the title compound (28.3 mg, 35% yield for final step). $^1$H NMR (500 MHz, DMSO-d6) δ=9.76 (s, 1H), 8.49 (s, 2H), 8.33 (s, 1H), 7.29 (d, J=8.7 Hz, 1H), 6.86 (s, 1H), 6.68 (d, J=13.8 Hz, 1H), 3.75-3.72 (m, 4H), 3.70-3.65 (m, 4H), 3.54 (s, 3H), 3.40-3.35 (m, 4H), 3.25-3.17 (m, 2H), 2.57-2.52 (m, 5H), 2.11-2.03 (m, 1H), 1.73-1.64 (m, 1H), 0.91 (t, J=7.0 Hz, 6H); LCMS [M+H]+: 618.5.

The title compound was prepared according to a sequence similar to Example 417 using (R)-1-(2-amino-5-fluoro-4-(2-morpholinopyrimidin-5-yl)phenyl)-N-isopropyl-N-methylpyrrolidin-3-amine (18 mg, 0.043 mmol) that was dissolved in DMF and [1-methyl-6-oxo-4-(trifluoromethyl)-1,6-dihydropyridine-3-carboxylic acid (9.60 mg, 0.043 mmol) in the final step to give the title compound (26.8 mg, 49% yield). $^1$H NMR (500 MHz, DMSO-d6) δ=9.78 (s, 1H), 8.49 (s, 2H), 8.32 (s, 1H), 7.28 (d, J=8.9 Hz, 1H), 6.86 (s, 1H), 6.68 (d, J=13.9 Hz, 1H), 3.75-3.72 (m, 4H), 3.69-3.66 (m, 4H), 3.54 (s, 3H), 3.26-3.20 (m, 2H), 3.12-3.01 (m, 1H), 2.97-2.87 (m, 1H), 2.12-2.03 (m, 4H), 1.71-1.62 (m, 1H), 0.92 (br d, J=6.1 Hz, 6H); LCMS [M+H]+: 618.6.

Example 430: 4-fluoro-N-[4-fluoro-5-[2-[(2R,6S)-2,6-dimethylmorpholin-4-yl]pyrimidin-5-yl]-2-[(3R)-3,4-dimethylpiperazin-1-yl]phenyl]-2-(trifluoromethyl)benzamide

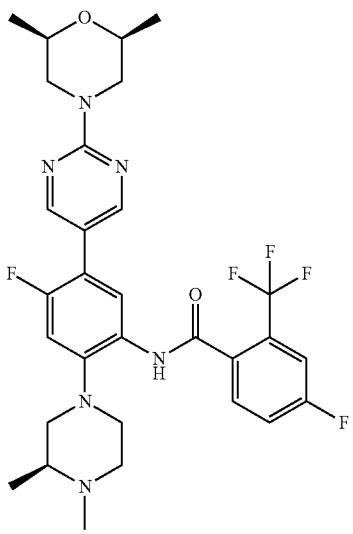

The title compound (formic acid salt, white solid, 36.2 mg, 55%) was prepared according to a procedure similar to that used in Example 400 using (2-((2S,6R)-2,6-dimethylmorpholino)pyrimidin-5-yl)boronic acid (36 mg, 0.15 mmol) and (S)—N-(5-bromo-2-(3,4-dimethylpiperazin-1-yl)-4-fluorophenyl)-4-fluoro-2-(trifluoromethyl)benzamide (49 mg, 0.1 mmol). $^1$H NMR (500 MHz, METHANOL-d4) δ=8.57 (s, 2H), 8.37 (br s, 1H), 8.04 (d, J=8.2 Hz, 1H), 7.82 (dd, J=5.4, 8.4 Hz, 1H), 7.68 (dd, J=2.2, 9.0 Hz, 1H), 7.58 (dt, J=2.3, 8.3 Hz, 1H), 7.20 (d, J=11.9 Hz, 1H), 4.68-4.63 (m, 2H), 3.71-3.64 (m, 2H), 3.43-3.37 (m, 1H), 3.31-3.22 (m, 2H), 3.16-3.04 (m, 3H), 2.91-2.80 (m, 1H), 2.79-2.75 (m, 3H), 2.68-2.60 (m, 2H), 1.33 (br d, J=6.4 Hz, 3H), 1.26 (d, J=6.2 Hz, 6H); LCMS [M+H]$^+$ 605.5.

Example 431: 4-fluoro-N-[4-fluoro-5-[2-[(2R,6S)-2,6-dimethylmorpholin-4-yl]pyrimidin-5-yl]-2-[(3S,5R)-3,4,5-trimethylpiperazin-1-yl]phenyl]-2-(trifluoromethyl)benzamide

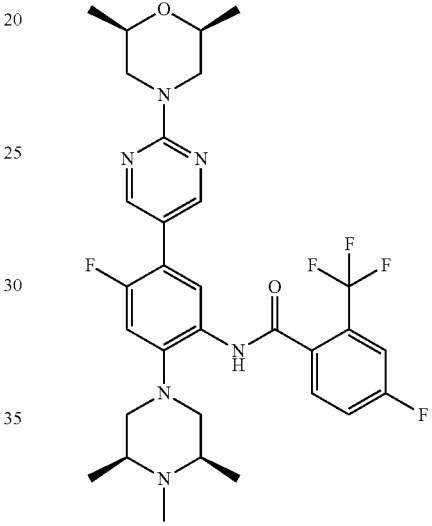

The title compound (formic acid salt, white solid, 36.5 mg, 39%) was prepared by a procedure similar to Example 400 using (2-((2S,6R)-2,6-dimethylmorpholino)pyrimidin-5-yl)boronic acid (36 mg, 0.15 mmol) and N-(5-bromo-4-fluoro-2-((3S,5R)-3,4,5-trimethylpiperazin-1-yl)phenyl)-4-fluoro-2-(trifluoromethyl)benzamide (51 mg, 0.1 mmol). $^1$H NMR (500 MHz, METHANOL-d4) δ=8.56 (s, 2H), 8.42 (br s, 1H), 8.05 (d, J=8.2 Hz, 1H), 7.81 (dd, J=5.3, 8.4 Hz, 1H), 7.68 (br d, J=8.9 Hz, 1H), 7.58 (br t, J=8.1 Hz, 1H), 7.20 (br d, J=11.9 Hz, 1H), 4.65 (br d, J=13.2 Hz, 2H), 3.67 (br dd, J=6.4, 7.9 Hz, 2H), 3.26 (br d, J=13.0 Hz, 4H), 2.94-2.82 (m, 2H), 2.77 (br d, J=9.4 Hz, 3H), 2.68-2.60 (m, 2H), 1.37 (br d, J=4.5 Hz, 6H), 1.25 (d, J=6.2 Hz, 6H); LCMS [M+H]$^+$ 619.5.

Example 432: 4-fluoro-N-[4-fluoro-5-[6-[(2R,6S)-2,6-dimethylmorpholin-4-yl]pyridin-3-yl]-2-[(3S,5R)-3,4,5-trimethylpiperazin-1-yl]phenyl]-2-(trifluoromethyl)benzamide

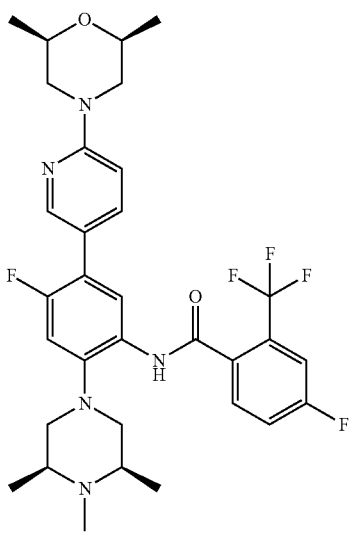 [SMILES: C[C@@H]1CN(c2ccc(-c3cc(NC(=O)c4ccc(F)cc4C(F)(F)F)c(N4C[C@@H](C)N(C)[C@@H](C)C4)cc3F)cn2)C[C@H](C)O1]

The title compound (white solid, 35.8 mg, 56%) was prepared by a procedure similar to Example 400 using (2S,6R)-2,6-dimethyl-4-(5-(4,4,5,5-tetramethyl-1,3,2-dioxaborolan-2-yl)pyridin-2-yl)morpholine (47 mg, 0.15 mmol) and N-(5-bromo-4-fluoro-2-((3S,5R)-3,4,5-trimethylpiperazin-1-yl)phenyl)-4-fluoro-2-(trifluoromethyl)benzamide (51 mg, 0.1 mmol). $^1$H NMR (500 MHz, METHANOL-d4) δ=8.33 (s, 1H), 8.03 (d, J=8.3 Hz, 1H), 7.82-7.75 (m, 2H), 7.66 (dd, J=2.3, 9.1 Hz, 1H), 7.57 (dt, J=2.3, 8.3 Hz, 1H), 7.08 (d, J=12.0 Hz, 1H), 6.93 (d, J=9.0 Hz, 1H), 4.17 (br d, J=11.6 Hz, 2H), 3.78-3.71 (m, 2H), 3.06 (br d, J=11.4 Hz, 2H), 2.63 (br t, J=11.1 Hz, 2H), 2.58-2.43 (m, 4H), 2.35 (br s, 3H), 1.27 (d, J=6.2 Hz, 6H), 1.17 (d, J=6.2 Hz, 6H); LCMS [M+H]$^+$ 618.5.

Example 433: N-[4-fluoro-2-[(3R)-3,4-dimethylpiperazin-1-yl]-5-[6-[(2R)-2-methylmorpholin-4-yl]pyridin-3-yl]phenyl]-6-oxo-4-(trifluoromethyl)-1H-pyridine-3-carboxamide

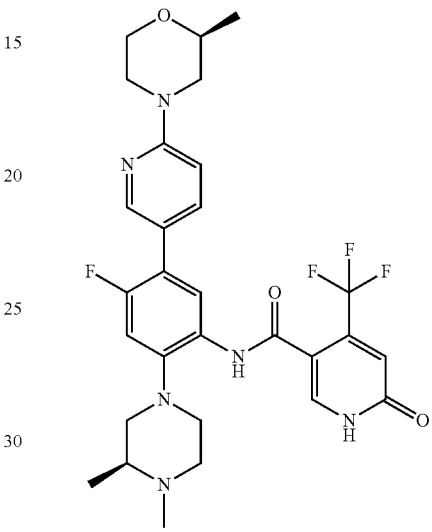

To a 5 mL microwave vial charged with 2-chloro-5-(4,4,5,5-tetramethyl-1,3,2-dioxaborolan-2-yl)pyridine (479 mg, 2 mmol), (S)-2-methylmorpholine (223 mg, 2.2 mmol) and Hunig base (0.70 mL, 4 mmol) was added NMP (1 mL). The resulting solution was heated at 140° C. for 2 h and purified by flash chromatography twice (gradient: EtOAc/hex 0-100% and EtOAc/hex 0-50% respectively) to give (S)-2-methyl-4-(5-(4,4,5,5-tetramethyl-1,3,2-dioxaborolan-2-yl)pyridin-2-yl)morpholine as a crystalline light beige solid (102 mg). LCMS for boronic acid [M+H]$^+$ 223.2. The title compound (pale beige solid, 21.1 mg, 34%) was prepared by a method similar to Example 400 using (S)-2-methyl-4-(5-(4,4,5,5-tetramethyl-1,3,2-dioxaborolan-2-yl)pyridin-2-yl)morpholine (50 mg) and (S)—N-(5-bromo-2-(3,4-dimethylpiperazin-1-yl)-4-fluorophenyl)-6-oxo-4-(trifluoromethyl)-1,6-dihydropyridine-3-carboxamide (49.1 mg, 0.1 mmol). $^1$H NMR (500 MHz, METHANOL-d4) δ=8.32 (s, 1H), 7.98 (s, 1H), 7.93 (br d, J=8.3 Hz, 1H), 7.79 (br d, J=8.9 Hz, 1H), 7.09 (d, J=12.1 Hz, 1H), 6.95-6.90 (m, 2H), 4.16 (br d, J=12.7 Hz, 1H), 4.10-3.99 (m, 2H), 3.76-3.66 (m, 2H), 3.16-3.03 (m, 2H), 3.02-2.90 (m, 3H), 2.67-2.53 (m, 3H), 2.47 (br s, 1H), 2.44-2.38 (m, 3H), 1.26 (d, J=6.2 Hz, 3H), 1.15 (br d, J=6.2 Hz, 3H); LCMS [M+H]$^+$ 589.5.

Example 434: N-[4-fluoro-5-[6-[(2R)-2-methylmorpholin-4-yl]pyridin-3-yl]-2-[(3S,5R)-3,4,5-trimethylpiperazin-1-yl]phenyl]-6-oxo-4-(trifluoromethyl)-1H-pyridine-3-carboxamide

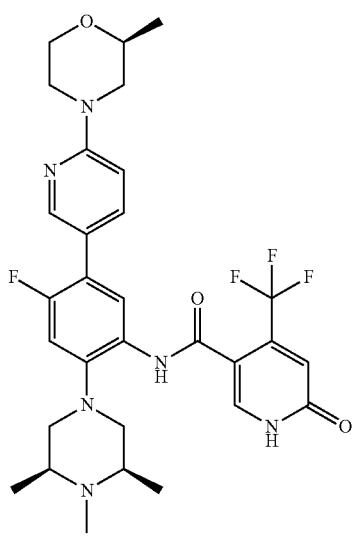 [SMILES: C[C@@H]1CN(c2cc(F)c(-c3ccc(N4CCO[C@@H](C)C4)nc3)cc2NC(=O)c2c[nH]c(=O)cc2C(F)(F)F)C[C@H](C)N1C]

The title compound (pale beige solid, 26.5 mg, 40%) was prepared by a procedure similar to Example 400 using (S)-2-methyl-4-(5-(4,4,5,5-tetramethyl-1,3,2-dioxaborolan-2-yl)pyridin-2-yl)morpholine (50 mg, 80% purity, 0.16 mmol) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, METHANOL-d4) δ=8.32 (s, 1H), 7.97 (s, 1H), 7.92 (br d, J=8.4 Hz, 1H), 7.79 (br d, J=8.8 Hz, 1H), 7.07 (d, J=12.1 Hz, 1H), 6.95-6.90 (m, 2H), 4.16 (br d, J=12.7 Hz, 1H), 4.10-3.99 (m, 2H), 3.75-3.66 (m, 2H), 3.07 (br d, J=10.5 Hz, 2H), 2.96 (dt, J=3.4, 12.3 Hz, 1H), 2.70-2.56 (m, 5H), 2.41 (s, 3H), 1.26 (d, J=6.2 Hz, 3H), 1.19 (d, J=5.7 Hz, 6H); LCMS [M+H]$^+$ 603.6.

Example 435: N-[5-[2-(4-cyclopropylpiperazin-1-yl)pyrimidin-5-yl]-4-fluoro-2-[(3R)-3,4-dimethylpiperazin-1-yl]phenyl]-4-fluoro-2-(trifluoromethyl)benzamide

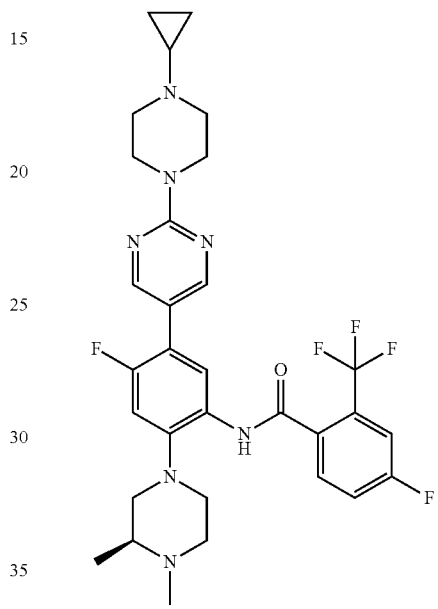

To a mixture of 2-chloropyrimidine-5-boronic acid (633 mg, 4 mmol) and 1-cyclopropylpiperazine (0.56 mL, 4.4 mmol) in EtOH (8 mL) was added triethylamine (0.84 mL, 6 mmol). The resulting mixture was stirred at 75° C. for 1 h, concentrated and dried to give crude (2-(4-cyclopropylpiperazin-1-yl)pyrimidin-5-yl)boronic acid as a beige solid (1.319 g, 75% purity assuming full conversion). LCMS [M+H]$^+$ 249.2. The title compound (beige solid, 15.9 mg, 25%) was prepared according to a procedure similar to Example 40 using crude (2-(4-cyclopropylpiperazin-1-yl)pyrimidin-5-yl)boronic acid (0.27 mmol) and (S)—N-(5-bromo-2-(3,4-dimethylpiperazin-1-yl)-4-fluorophenyl)-4-fluoro-2-(trifluoromethyl)benzamide (57 mg, 86% purity, 0.1 mmol). $^1$H NMR (500 MHz, METHANOL-d4) δ=8.56 (s, 2H), 8.03 (d, J=8.2 Hz, 1H), 7.80 (dd, J=5.3, 8.4 Hz, 1H), 7.66 (dd, J=2.3, 9.0 Hz, 1H), 7.57 (dt, J=2.3, 8.3 Hz, 1H), 7.13 (d, J=12.0 Hz, 1H), 3.91-3.84 (m, 4H), 3.16-3.04 (m, 2H), 2.99-2.88 (m, 2H), 2.77-2.70 (m, 4H), 2.58 (t, J=10.8 Hz, 1H), 2.49 (dt, J=2.6, 11.5 Hz, 1H), 2.39-2.32 (m, 4H), 1.76-1.72 (m, 1H), 1.13 (d, J=6.2 Hz, 3H), 0.60-0.48 (m, 4H); LCMS [M+H]$^+$ found 616.6.

Example 436: 4-(difluoromethyl)-N-[4-fluoro-5-(3-fluoro-4-morpholin-4-ylphenyl)-2-[(3R,5S)-3,4,5-trimethylpiperazin-1-yl]phenyl]-6-oxo-1H-pyridine-3-carboxamide

Example 437: N-[4-fluoro-5-[1-(5-methoxypyrimidin-2-yl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide

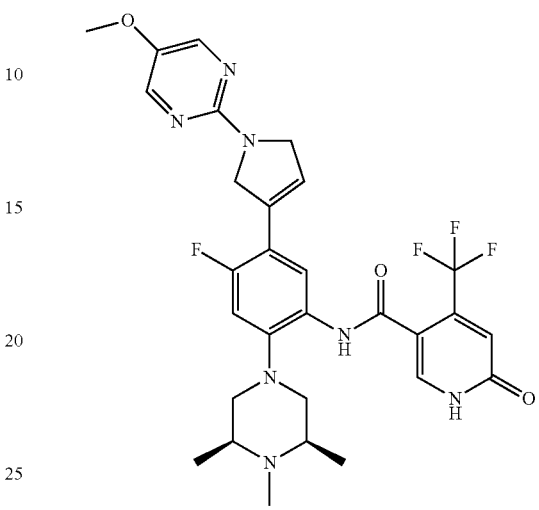

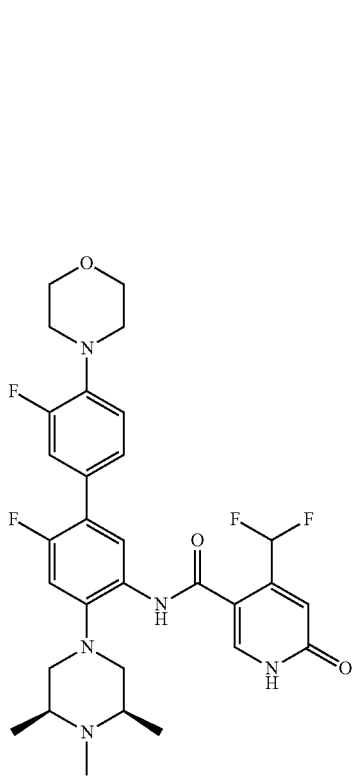

The procedure used was similar to Example 270 using N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (20 mg, 0.041 mmol) and 2-bromo-5-methoxypyrimidine (10.72 mg, 0.057 mmol) to give the title compound (13.5 mg, 53% yield). $^1$H NMR (500 MHz, METHANOL-d4) δ 8.04-8.11 (m, 2H), 7.86 (s, 1H), 7.77 (d, J=8.07 Hz, 1H), 6.91 (d, J=12.96 Hz, 1H), 6.80 (s, 1H), 6.37 (br. s., 1H), 4.53-4.62 (m, 2H), 4.38 (br. s., 2H), 3.73 (s, 3H), 2.94 (d, J=11.37 Hz, 2H), 2.46-2.53 (m, 2H), 2.37-2.44 (m, 2H), 2.37-2.44 (m, 2H), 2.25 (s, 3H), 1.05 (d, J=6.11 Hz, 6H); LCMS [M+H]+ 602.7.

Example 438: N-[4-fluoro-5-[1-(6-methoxypyrimidin-4-yl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide

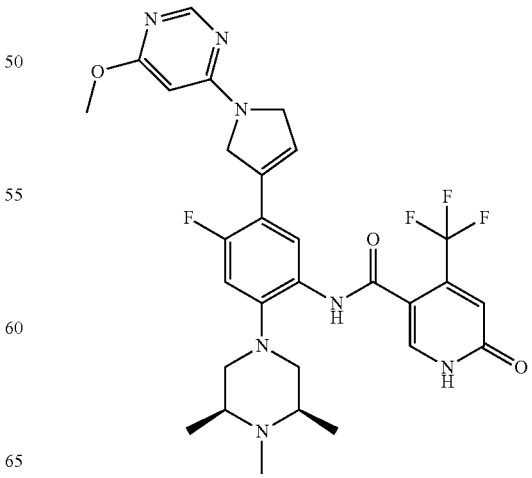

A sequence similar to Example 397 using N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (92.3 mg, 0.157 mmol) and 3-fluoro-4-morpholinophenylboronic acid (42.4 mg, 0.189 mmol) was employed to give, after deprotection of the N-(3',6-difluoro-4'-morpholino-4-((3S,5R)-3,4,5-trimethylpiperazin-1-yl)-[1,1'-biphenyl]-3-yl)-4-(difluoromethyl)-6-(2-(trimethylsilyl)ethoxy)nicotinamide intermediate, (108 mg, 0.157 mmol) the title compound (13.6 mg, 14.15% yield) as a white powder. $^1$H NMR (500 MHz, DMSO-d6) δ=12.39 (br. s., 1H), 9.56 (s, 1H), 7.99 (s, 1H), 7.69 (d, J=8.68 Hz, 1H), 7.21-7.49 (m, 2H), 7.09-7.16 (m, 1H), 7.00 (d, J=12.72 Hz, 1H), 6.59 (s, 1H), 3.71-3.81 (m, 4H), 3.00-3.09 (m, 6H), 2.48 (br. s., 1H), 2.33 (d, J=6.60 Hz, 2H), 2.19 (s, 3H), 1.00 (d, J=6.11 Hz, 6H); LCMS [M+H]+ 588.5.

The procedure used was similar to Example 270 using N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (20 mg, 0.041 mmol) and 4-iodo-6-Methoxy pyrimidine (13.39 mg, 0.057 mmol) to give the title compound (19 mg, 74% yield). $^1$H NMR (500 MHz, METHANOL-d4) δ 8.19-8.28 (m, 1H), 7.99 (s, 1H), 7.89 (d, J=7.95 Hz, 1H), 7.04 (d, J=12.96 Hz, 1H), 6.93 (s, 1H), 6.49 (br. s., 1H), 5.86 (br. s., 1H), 4.26-4.72 (m, 4H), 3.93 (s, 3H), 3.07 (d, J=11.25 Hz, 2H), 2.58-2.65 (m, 2H), 2.55 (d, J=6.11 Hz, 2H), 2.38 (s, 3H), 1.17 (d, J=5.99 Hz, 6H); LCMS [M+H]+ 602.7.

Example 439: N-[4-fluoro-5-[1-(5-methylpyrimidin-2-yl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide

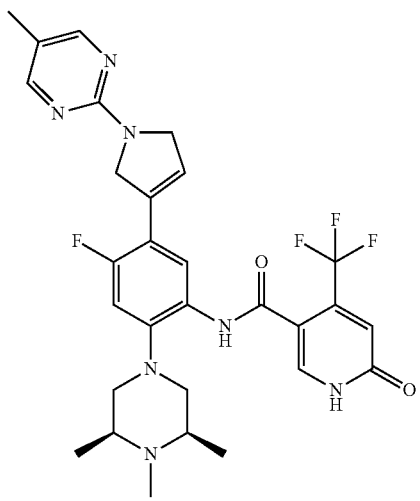 [SMILES: Cc1cnc(N2CC=C(c3cc(NC(=O)c4c[nH]c(=O)cc4C(F)(F)F)c(N4C[C@@H](C)N(C)[C@@H](C)C4)cc3F)C2)nc1]

A procedure similar to Example 270 was employed using N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (20 mg, 0.041 mmol) and 2-Chloro-5-methylpyrimidine (7.29 mg, 0.057 mmol) to give the title compound (16.5 mg, 63% yield). $^1$H NMR (500 MHz, METHANOL-d4) δ 8.26 (s, 2H), 8.04 (s, 1H), 7.91 (d, J=7.95 Hz, 1H), 7.03 (d, J=12.96 Hz, 1H), 6.87 (s, 1H), 6.48-6.53 (m, 1H), 6.50 (br. s., 1H), 4.72 (br. s., 2H), 4.52 (br. s., 2H), 3.07 (d, J=11.25 Hz, 2H), 2.58-2.65 (m, 2H), 2.53 (d, J=6.36 Hz, 2H), 2.37 (s, 3H), 2.19 (s, 3H), 1.16-1.18 (m, 6H), 1.17 (d, J=6.11 Hz, 6H); LCMS [M+H]+ 586.7

Example 440: N-[4-fluoro-5-[1-(5-fluoropyrimidin-2-yl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide

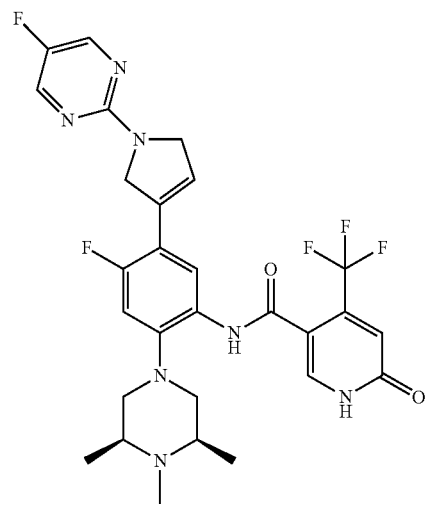 [SMILES: C[C@@H]1CN(c2cc(F)c(C3=CCN(c4ncc(F)cn4)C3)cc2NC(=O)c2c[nH]c(=O)cc2C(F)(F)F)C[C@H](C)N1C]

A procedure similar to that of Example 270 was employed using N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (20 mg, 0.041 mmol) and 2-Bromo-5-fluoropyrimidine (7.17 mg, 0.041 mmol) to give the title compound (17.5 mg, 70% yield). $^1$H NMR (500 MHz, METHANOL-d4) δ=8.40-8.31 (m, 2H), 8.04-7.97 (m, 1H), 7.94-7.85 (m, 1H), 7.08-7.00 (m, 1H), 6.95-6.88 (m, 1H), 6.53-6.46 (m, 1H), 5.51 (s, 1H), 4.75-4.68 (m, 2H), 4.56-4.48 (m, 2H), 3.12-3.03 (m, 2H), 2.66-2.58 (m, 2H), 2.56-2.49 (m, 2H), 2.41-2.36 (m, 3H), 1.19-1.15 (m, 6H); LCMS [M+H]+ 590.7.

Example 441: N-[4-fluoro-5-[1-(pyrrolidine-1-carbonyl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide

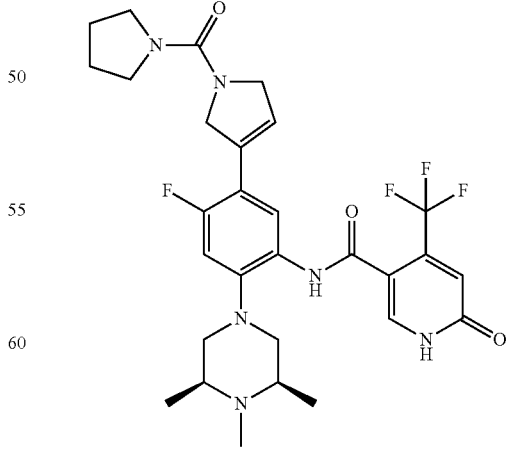

The procedure followed was similar to Example 253 using N-(5-(2,5-dihydro-1H-pyrrol-3-yl)-4-fluoro-2-((3S, 5R)-3,4,5-trimethylpiperazin-1-yl)phenyl)-6-oxo-4-(trifluoromethyl)-1,6-dihydropyridine-3-carboxamide (24 mg, 0.049 mmol) and 1-pyrrolidinecarbonyl chloride (5.37 µl, 0.049 mmol) to give the title compound (22 mg, 73% yield). ¹H NMR (500 MHz, METHANOL-d4) δ=8.03-7.93 (m, 1H), 7.87-7.76 (m, 1H), 7.06-6.98 (m, 1H), 6.94-6.87 (m, 1H), 6.41-6.30 (m, 1H), 4.71-4.62 (m, 2H), 4.51-4.43 (m, 2H), 3.54-3.47 (m, 4H), 3.10-3.02 (m, 2H), 2.64-2.57 (m, 2H), 2.56-2.49 (m, 2H), 1.97-1.88 (m, 4H), 1.20-1.15 (m, 6H); LCMS [M+H]+ 591.7.

Example 442: N-[4-fluoro-5-[1-(pyrazine-2-carbonyl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide

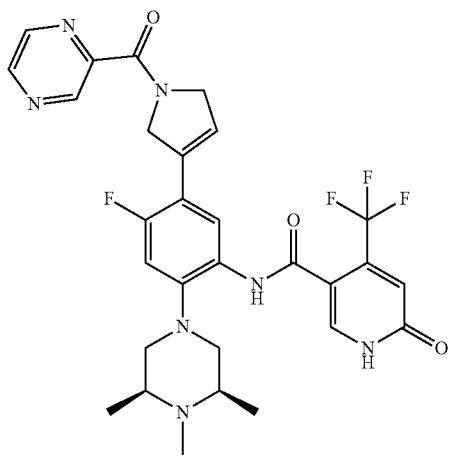 [SMILES: C[C@@H]1CN(c2cc(F)c(C3=CCN(C(=O)c4cnccn4)C3)cc2NC(=O)c2c[nH]c(=O)cc2C(F)(F)F)C[C@H](C)N1C]

The procedure followed was similar to Example 253 using N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (25 mg, 0.051 mmol) and pyrazine-2-carbonyl chloride (10.83 mg, 0.076 mmol) to give the title compound (11 mg, 34% yield). ¹H NMR (500 MHz, METHANOL-d4) δ=9.17-9.09 (m, 1H), 8.78-8.70 (m, 2H), 8.02-7.94 (m, 1H), 7.93-7.75 (m, 1H), 7.09-6.99 (m, 1H), 6.96-6.91 (m, 1H), 6.50-6.36 (m, 1H), 5.14-5.07 (m, 1H), 4.72-4.65 (m, 1H), 3.13-3.03 (m, 2H), 2.65-2.52 (m, 4H), 2.41-2.36 (m, 3H), 1.17 (t, J=6.5 Hz, 6H); LCMS [M+H]+ 600.6.

Example 443: 2-methylpropyl 3-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-2,5-dihydropyrrole-1-carboxylate

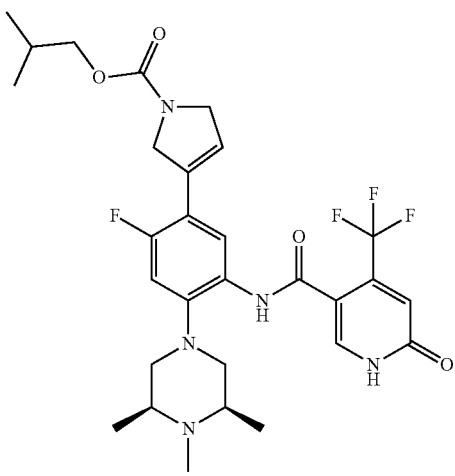 [SMILES: CC(C)COC(=O)N1CC=C(c2cc(NC(=O)c3c[nH]c(=O)cc3C(F)(F)F)c(N3C[C@@H](C)N(C)[C@@H](C)C3)cc2F)C1]

The procedure employed was similar to Example 253 using N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (25 mg, 0.051 mmol) and isobutyl chloroformate (6.62 µl, 0.051 mmol) to give the title compound (25 mg, 79% yield). ¹H NMR (500 MHz, METHANOL-d4) δ=8.01-7.93 (m, 1H), 7.87-7.77 (m, 1H), 7.05-6.98 (m, 1H), 6.95-6.90 (m, 1H), 6.42-6.32 (m, 1H), 4.63-4.53 (m, 2H), 4.43-4.31 (m, 2H), 3.94 (t, J=7.2 Hz, 2H), 3.10-3.03 (m, 2H), 2.65-2.58 (m, 2H), 2.58-2.49 (m, 2H), 2.08-1.92 (m, 1H), 1.21-1.15 (m, 6H), 1.05-0.97 (m, 6H); LCMS [M+H]+ 594.4

Example 444: N-[4-fluoro-5-[1-(5-formylpyrimidin-2-yl)-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide

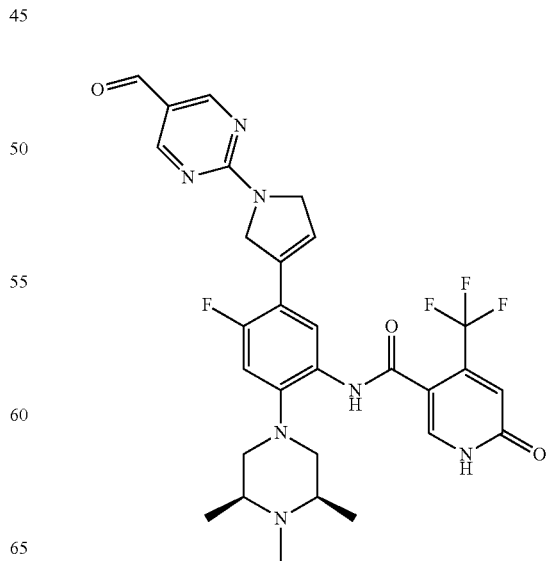

The procedure followed was similar to Example 270 using N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (200 mg, 0.405 mmol) and 2-bromo-pyrimidine-5-carbaldehyde (91 mg, 0.486 mmol) to give the title compound (212 mg, 83% yield). ¹H NMR (500 MHz, METHANOL-d4) δ=12.85-12.28 (m, 1H), 9.88-9.77 (m, 1H), 9.57-9.46 (m, 1H), 8.93-8.84 (m, 2H), 8.03-7.91 (m, 1H), 7.73 (br d, J=8.3 Hz, 1H), 7.06-6.96 (m, 1H), 6.87-6.78 (m, 1H), 6.51-6.43 (m, 1H), 4.82-4.72 (m, 2H), 4.64-4.56 (m, 2H), 3.10-3.01 (m, 2H), 2.48-2.42 (m, 2H), 2.39-2.30 (m, 2H), 2.23-2.17 (m, 3H), 1.01 (d, J=6.1 Hz, 6H); LCMS [M+H]+ 600.6.

Example 445: N-[4-fluoro-5-(1-methylpyrazol-4-yl)-2-[(3R,5S)-3,4,5-trimethylpiperazin-1-yl]phenyl]-6-oxo-4-(trifluoromethyl)-1H-pyridine-3-carboxamide

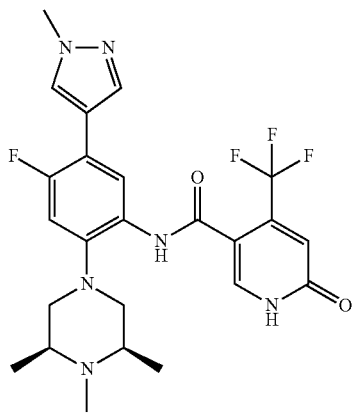 [SMILES: C[C@@H]1CN(c2cc(F)c(-c3cnn(C)c3)cc2NC(=O)c2c[nH]c(=O)cc2C(F)(F)F)C[C@H](C)N1C]

Step 1: cis-4-(4-Bromo-5-fluoro-2-nitrophenyl)-1,2,6-trimethylpiperazine

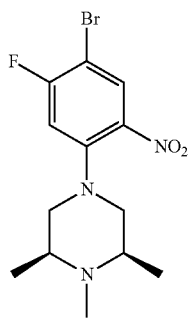

A solution of 1-bromo-2,4-difluoro-5-nitrobenzene (5.0 g, 21 mmol) in toluene (5 mL) was added dropwise to a rapidly stirring mixture of cis-1,2,6-trimethylpiperazine (2.7 g, 21 mmol) and potassium carbonate (1.4 g, 10 mmol) in toluene (50 mL) at room temperature. After stirring for 20 minutes the reaction was warmed to 45° C. for 30 minutes. After the reaction was cooled to room temperature the reaction mixture was partitioned between water (100 mL) and ethyl acetate (100 mL). The layers were separated and the aqueous layer was extracted with additional ethyl acetate. The combined organic extracts were dried over magnesium sulfate and after removal of the inorganics by filtration the filtrate was concentrated onto celite. Purification by flash chromatography [1-10% MeOH/DCM+0.5% NH₄OH] afforded cis-4-(4-bromo-5-fluoro-2-nitrophenyl)-1,2,6-trimethylpiperazine (6.8 g, 93% yield). LCMS [M+H]+: 346.3.

Step 2: cis-4-(5-fluoro-2-nitro-4-(4,4,5,5-tetramethyl-1,3,2-dioxaborolan-2-yl)phenyl)-1,2,6-trimethylpiperazine

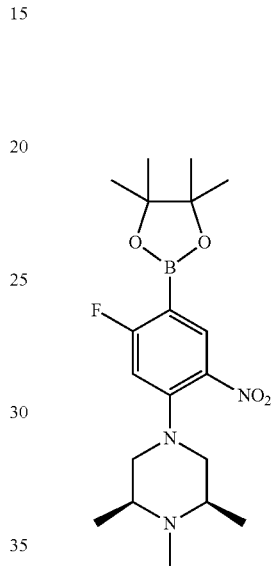

Two reaction vials containing magnetic stir bars were charged with cis-4-(4-bromo-5-fluoro-2-nitrophenyl)-1,2,6-trimethylpiperazine (0.55 g, 1.6 mmol), bis(pinacolato)diboron (0.73 g, 2.9 mmol), potassium acetate (0.44 g, 4.5 mmol) and [1,1'-bis(diphenylphosphino)ferrocene]dichloropalladium(II) (0.12 g, 0.16 mmol). The vials were sealed with septa. After evacuating and back filling the vials with nitrogen gas 1,4-dioxane (10 mL) and DMSO (0.2 mL) were added via syringe and the reaction vials were evacuated and back filled an additional time. The reaction vials were heated to 100° C. for 3 h. After cooling to room temperature the reaction mixtures were combined and passed through a pad of celite eluting with DCM. The filtrate was concentrated to near dryness and purified by flash chromatography [0.5-9.5% MeOH/DCM+0.5% NH₄OH] to afford cis-4-(5-fluoro-2-nitro-4-(4,4,5,5-tetramethyl-1,3,2-dioxaborolan-2-yl)phenyl)-1,2,6-trimethylpiperazine (0.95 g, 76%). ¹H NMR (500 MHz, DMSO-d6) δ=8.06 (d, J=6.4 Hz, 1H), 7.02 (d, J=12.0 Hz, 1H), 3.14 (br d, J=12.6 Hz, 2H), 2.72 (br t, J=11.6 Hz, 2H), 2.28-2.22 (m, 2H), 2.19 (s, 3H), 1.29 (s, 12H), 1.01 (d, J=6.1 Hz, 6H).

Step 3: cis-4-(5-Fluoro-4-(1-methyl-1H-pyrazol-4-yl)-2-nitrophenyl)-1,2,6-trimethylpiperazine

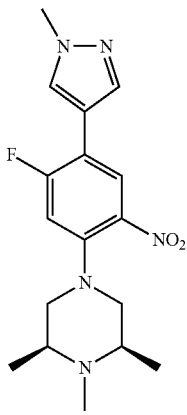 [SMILES: C[C@@H]1CN(c2cc(F)c(-c3cnn(C)c3)cc2[N+](=O)[O-])C[C@H](C)N1C]

A 30 mL vial was charged with a mixture of cis-4-(5-fluoro-2-nitro-4-(4,4,5,5-tetramethyl-1,3,2-dioxaborolan-2-yl)phenyl)-1,2,6-trimethylpiperazine (0.045 g, 0.11 mmol), 4-bromo-1-methyl-TH-pyrazole (0.020 g, 0.13 mmol), XPhos Pd G2 (1.8 mg, 2.3 µmol) and XPhos (1.1 mg, 2.3 µmol). The vial was sealed with a septum and evacuated and backfilled with nitrogen. 1,4-Dioxane (3 mL) and 2 M aqueous sodium carbonate (0.5 mL) were added via syringe and the vial was evacuated and backfilled an additional time. The reaction was heated to 95° C. for 20 h. After cooling to room temperature the reaction mixture was concentrated onto celite and purified by flash chromatography [0.5-9.5% MeOH/DCM+0.5% NH₄OH] to afford cis-4-(5-fluoro-4-(1-methyl-1H-pyrazol-4-yl)-2-nitrophenyl)-1,2,6-trimethylpiperazine (0.014 g, 35%). LCMS [M+H]+: 348.1.

Step 4: 4-fluoro-5-(1-methyl-1H-pyrazol-4-yl)-2-(cis-3,4,5-trimethylpiperazin-1-yl)aniline

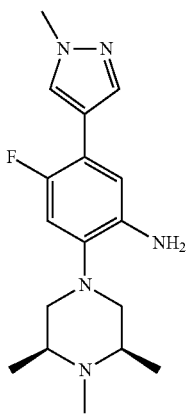 [SMILES: C[C@@H]1CN(c2cc(F)c(-c3cnn(C)c3)cc2N)C[C@H](C)N1C]

A solution of cis-4-(5-fluoro-4-(1-methyl-1H-pyrazol-4-yl)-2-nitrophenyl)-1,2,6-trimethylpiperazine (0.014 g, 0.04 mmol) and tin(II) chloride (0.030 g, 0.14 mmol) in a mixture of EtOH (3 mL) and MeOH (1 mL) was heated to 65° C. for 4 h. After cooling to room temperature the reaction mixture was concentrated onto celite and purified by flash chromatography [0.5-10% MeOH/DCM+0.5% NH₄OH] to afford 4-fluoro-5-(1-methyl-1H-pyrazol-4-yl)-2-(cis-3,4,5-trimethylpiperazin-1-yl)aniline (0.009 g, 70%). LCMS [M+H]+: 318.5.

Step 5: N-(4-fluoro-5-(1-methyl-1H-pyrazol-4-yl)-2-(cis-3,4,5-trimethylpiperazin-1-yl)phenyl)-6-oxo-4-(trifluoromethyl)-1,6-dihydropyridine-3-carboxamide 4-(trifluoromethyl)-6-(2-(trimethylsilyl)ethoxy)nicotinic acid (0.017 g, 0.057 mmol) was activated with HATU (0.022 g, 0.057 mmol) and N,N-diisopropylethylamine (10 µl, 0.057 mmol) in DMF (0.5 mL) at room temperature. The solution of activated acid was added to a solution of 4-fluoro-5-(1-methyl-1H-pyrazol-4-yl)-2-(cis-3,4,5-trimethylpiperazin-1-yl)aniline (0.009 g, 0.030 mmol) in DMF (0.5 mL) and the reaction was heated to 50° C. for 18 h. After cooling to room temperature the reaction mixture was concentrated onto celite and purified by flash chromatography [0.5-10% MeOH/DCM+0.5% NH₄OH]. The silyl protected amide was dissolved in DCM (2 mL) and treated with TFA (0.5 mL) at room temperature. After stirring for 2 h the volatiles were removed under a stream of air and the title compound was isolated with a catch and release protocol using a SCX2 silica cartridge to afford the title compound N-(4-fluoro-5-(1-methyl-1H-pyrazol-4-yl)-2-(cis-3,4,5-trimethylpiperazin-1-yl)phenyl)-6-oxo-4-(trifluoromethyl)-1,6-dihydropyridine-3-carboxamide (0.011 g, 77%). $^1$H NMR (500 MHz, DMSO-d6) δ=12.56 (br s, 1H), 9.45 (s, 1H), 8.05 (s, 1H), 7.94 (s, 1H), 7.86 (d, J=8.3 Hz, 1H), 7.74 (s, 1H), 6.99 (d, J=12.6 Hz, 1H), 6.80 (s, 1H), 3.89 (s, 3H), 2.98 (br d, J=10.9 Hz, 2H), 2.44 (br t, J=10.9 Hz, 2H), 2.36-2.28 (m, 2H), 2.19 (s, 3H), 1.00 (d, J=6.1 Hz, 6H); LCMS [M+H]+: 507.6.

Example 446: N-[5-(4-cyano-1,3-thiazol-2-yl)-4-fluoro-2-[(3R,5S)-3,4,5-trimethylpiperazin-1-yl]phenyl]-6-oxo-4-(trifluoromethyl)-1H-pyridine-3-carboxamide

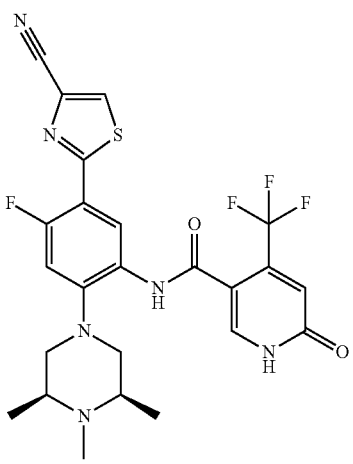 [SMILES: C[C@@H]1CN(c2cc(F)c(-c3nc(C#N)cs3)cc2NC(=O)c2c[nH]c(=O)cc2C(F)(F)F)C[C@H](C)N1C]

The title compound was prepared similar to the procedure described above for the preparation of Example 445 using 2-bromo-4-cyanothiazole in place of 4-bromo-1-methyl-1H-pyrazole in Step 3. $^1$H NMR (500 MHz, DMSO-d6) δ=9.68 (s, 1H), 8.95 (s, 1H), 8.39 (d, J=8.1 Hz, 1H), 7.97 (s, 1H), 7.13 (d, J=13.3 Hz, 1H), 6.82 (s, 1H), 3.18 (br d, J=11.6 Hz, 2H), 2.38-2.33 (m, 2H), 2.20 (s, 3H), 1.01 (br d, J=6.0 Hz, 6H); LCMS [M+H]+: 535.5.

Example 447: N-[5-(5-cyano-1,3-thiazol-2-yl)-4-fluoro-2-[(3R 5S)-3,4,5-trimethylpiperazin-1-yl]phenyl]-6-oxo-4-(trifluoromethyl)-1H-pyridine-3-carboxamide

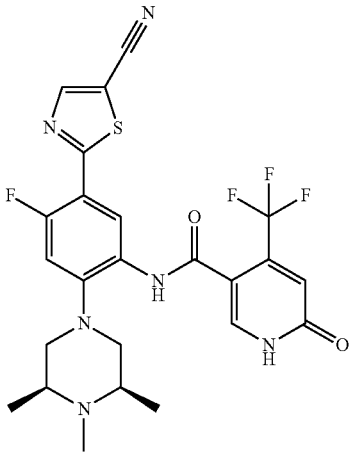 [SMILES: C[C@@H]1CN(c2cc(F)c(-c3ncc(C#N)s3)cc2NC(=O)c2c[nH]c(=O)cc2C(F)(F)F)C[C@H](C)N1C]

The title compound was prepared similar to the procedure described above for the preparation of Example 445 using 2-bromo-5-cyanothiazole in place of 4-bromo-1-methyl-1H-pyrazole in Step 3. $^1$H NMR (500 MHz, DMSO-d6) δ=9.71 (s, 1H), 8.79 (d, J=2.1 Hz, 1H), 8.48 (d, J=8.2 Hz, 1H), 7.94 (s, 1H), 7.16 (d, J=13.3 Hz, 1H), 6.83 (s, 1H), 3.22 (br d, J=11.4 Hz, 3H), 2.37 (br s, 3H), 2.20 (s, 3H), 1.02 (d, J=6.1 Hz, 6H); LCMS [M+H]+: 535.5.

Example 448: 4-(difluoromethyl)-N-[4-fluoro-5-(3-fluoro-4-morpholin-4-ylphenyl)-2-[(3R)-3,4-dimethylpiperazin-1-yl]phenyl]-6-oxo-1H-pyridine-3-carboxamide

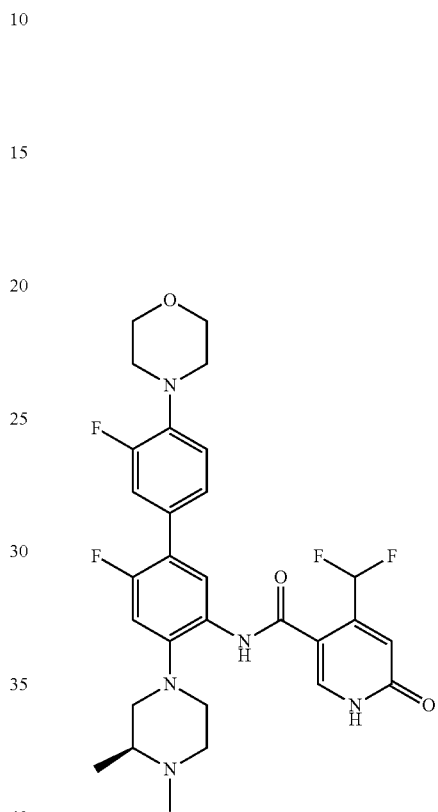

The procedure followed was similar to Example 396 using (S)—N-(5-bromo-2-(3,4-dimethylpiperazin-1-yl)-4-fluorophenyl)-4-(difluoromethyl)-6-(2-(trimethylsilyl)ethoxy)nicotinamide (96 mg, 0.167 mmol) and 3-fluoro-4-morpholinophenylboronic acid (111 mg, 0.493 mmol) to give, after deprotection of the intermediate (S)-4-(difluoromethyl)-N-(4-(3,4-dimethylpiperazin-1-yl)-3',6-difluoro-4'-morpholino-[1,1'-biphenyl]-3-yl)-6-(2-(trimethylsilyl)ethoxy)nicotinamide the title compound (69.0 mg, 0.118 mmol, 70.3% yield) as a white powder. $^1$H NMR (500 MHz, DMSO-d6) δ=12.35 (br. s., 1H), 9.54 (s, 1H), 8.00 (s, 1H), 7.71 (d, J=8.68 Hz, 1H), 7.21-7.48 (m, 3H), 7.09-7.16 (m, 1H), 7.04 (d, J=12.72 Hz, 1H), 6.59 (s, 1H), 3.73-3.79 (m, 4H), 2.99-3.09 (m, 6H), 2.72-2.89 (m, 2H), 2.40-2.47 (m, 1H), 2.29-2.39 (m, 1H), 2.23 (br. s., 3H), 0.98 (d, J=5.62 Hz, 3H); LCMS [M+H]+ 574.5.

Example 449: 4-(difluoromethyl)-N-[4-fluoro-5-(3-fluoro-4-morpholin-4-ylphenyl)-2-[(3R,5S)-3,4,5-trimethylpiperazin-1-yl]phenyl]-1-methyl-6-oxopyridine-3-carboxamide

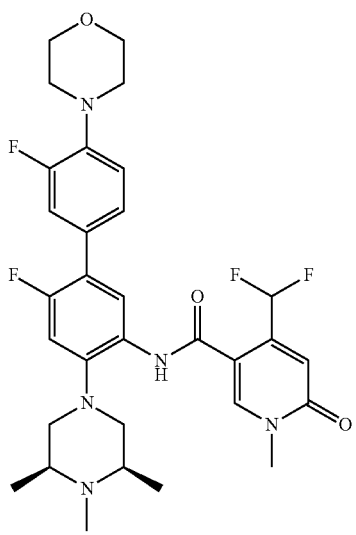

To a mixture of N-(3',6-difluoro-4'-morpholino-4-((3S,5R)-3,4,5-trimethylpiperazin-1-yl)-[1,1'-biphenyl]-3-yl)-4-(difluoromethyl)-6-oxo-1,6-dihydropyridine-3-carboxamide (70 mg, 0.095 mmol) and cesium carbonate (46.6 mg, 0.143 mmol) in N,N-dimethylformamide (4 ml) was added iodomethane (10 μl, 0.161 mmol) at room temperature. The reaction mixture was stirred for 15 minutes at room temperature and followed by LCMS. Successive portions of 10 and 5 μL of MeI were added at 15 min intervals and the reaction was worked up and the product was purified to give the title compound (0.022 mmol, 22.71% yield) as an off-white powder. $^1$H NMR (500 MHz, DMSO-d6) δ 9.47 (s, 1H), 8.32-8.35 (m, 1H), 7.69 (d, J=8.56 Hz, 1H), 7.20-7.48 (m, 3H), 7.13 (t, J=7.30 Hz, 1H), 7.02 (d, J=12.47 Hz, 1H), 6.64 (s, 1H), 3.72-3.80 (m, 4H), 3.47-3.55 (m, 3H), 3.35 (d, J=2.69 Hz, 1H), 2.97-3.10 (m, 6H), 2.45 (br. s., 1H), 2.36 (br. s., 2H), 2.19 (br. s., 3H), 1.01 (d, J=5.62 Hz, 6H). LCMS [M+H]+ 602.5.

Example 450: N-[4-fluoro-2-[(3R)-3,4-dimethylpiperazin-1-yl]-5-[2-[(2R)-2-methylmorpholin-4-yl]pyrimidin-5-yl]phenyl]-1-methyl-6-oxo-4-(trifluoromethyl)pyridine-3-carboxamide

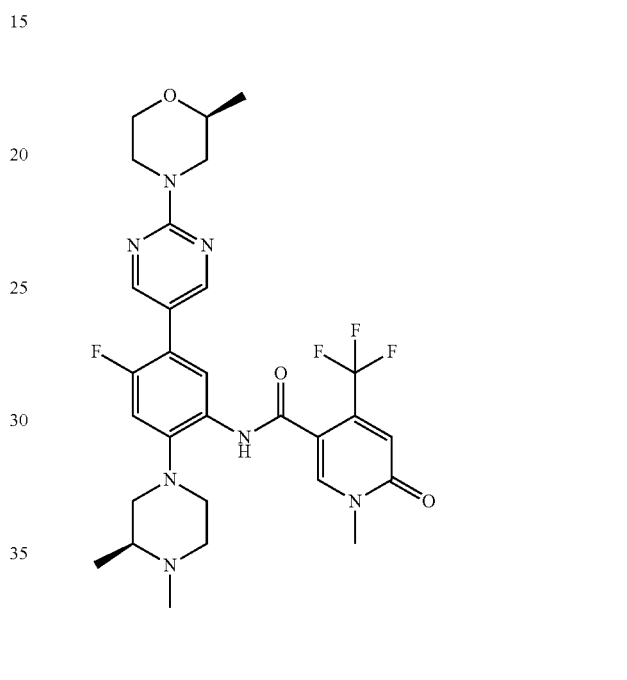

The title compound (light beige solid, 31.6 mg, 52%) was prepared in a manner similar to Example 31 using crude (S)-(2-(2-methylmorpholino)pyrimidin-5-yl)boronic acid (0.2 mmol) and (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (50.5 mg, 0.1 mmol). $^1$H NMR (500 MHz, METHANOL-d4) δ=8.56 (s, 2H), 8.27 (s, 1H), 7.92 (d, J=8.3 Hz, 1H), 7.12 (d, J=12.1 Hz, 1H), 6.95 (s, 1H), 4.65-4.54 (m, 2H), 4.01-3.96 (m, 1H), 3.69-3.59 (m, 5H), 3.15-3.04 (m, 3H), 3.01-2.89 (m, 2H), 2.77-2.70 (m, 1H), 2.64-2.50 (m, 2H), 2.43 (br s, 1H), 2.38 (s, 3H), 1.25 (d, J=6.2 Hz, 3H), 1.14 (d, J=6.4 Hz, 3H); LCMS [M+H]+ 604.5.

Example 451: N-[4-fluoro-5-[2-[(2R)-2-methylmorpholin-4-yl]pyrimidin-5-yl]-2-[(3S,5R)-3,4,5-trimethylpiperazin-1-yl]phenyl]-1-methyl-6-oxo-4-(trifluoromethyl)pyridine-3-carboxamide Example 452: 4-fluoro-N-[4-fluoro-2-[(3R)-3,4-dimethylpiperazin-1-yl]-5-[2-[(2R)-2-methylmorpholin-4-yl]pyrimidin-5-yl]phenyl]-2-(trifluoromethyl)benzamide

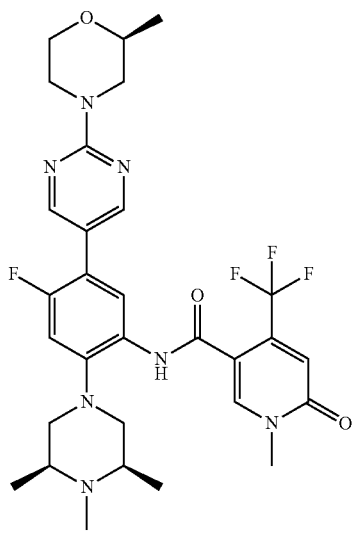 [SMILES: C[C@@H]1CN(c2cc(F)c(-c3cnc(N4CCO[C@@H](C)C4)nc3)cc2NC(=O)c2cn(C)c(=O)cc2C(F)(F)F)C[C@H](C)N1C]

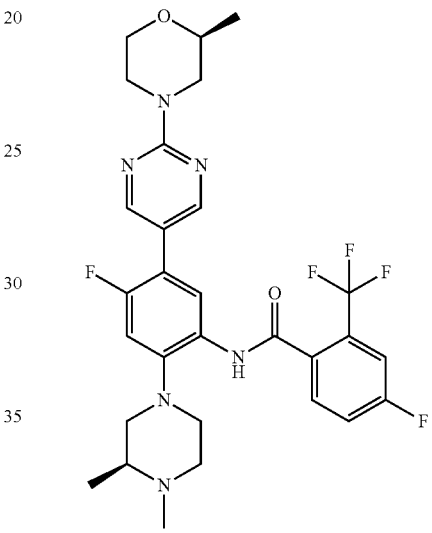

The title compound (off white solid, 12.9 mg, 21%) was prepared in a manner similar to Example 31 using crude (S)-(2-(2-methylmorpholino)pyrimidin-5-yl)boronic acid (0.2 mmol) and N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (52 mg, 0.1 mmol). $^1$H NMR (500 MHz, METHANOL-d4) δ=8.55 (s, 2H), 8.26 (s, 1H), 7.91 (d, J=8.3 Hz, 1H), 7.11 (d, J=12.0 Hz, 1H), 6.94 (s, 1H), 4.64-4.52 (m, 2H), 3.98 (dd, J=2.6, 11.4 Hz, 1H), 3.68-3.58 (m, 5H), 3.12-3.03 (m, 3H), 2.76-2.54 (m, 5H), 2.41 (br s, 3H), 1.26-1.23 (m, 3H), 1.19 (br d, J=4.3 Hz, 6H); LCMS [M+H]$^+$ 618.5.

The title compound (formic acid salt, beige solid, 28.1 mg, 43%) was prepared using a similar procedure to Example 400 using crude (S)-(2-(2-methylmorpholino)pyrimidin-5-yl)boronic acid (0.2 mmol) and (S)—N-(5-bromo-2-(3,4-dimethylpiperazin-1-yl)-4-fluorophenyl)-4-fluoro-2-(trifluoromethyl)benzamide (49 mg, 0.1 mmol). $^1$H NMR (500 MHz, METHANOL-d4) δ=8.55 (s, 2H), 8.40 (br s, 1H), 8.03 (d, J=8.3 Hz, 1H), 7.80 (dd, J=5.3, 8.3 Hz, 1H), 7.65 (dd, J=1.7, 8.9 Hz, 1H), 7.56 (t, J=8.2 Hz, 1H), 7.17 (d, J=11.9 Hz, 1H), 4.63-4.52 (m, 2H), 3.97 (br dd, J=2.3, 11.5 Hz, 1H), 3.66-3.57 (m, 2H), 3.35 (br d, J=11.0 Hz, 1H), 3.27-3.18 (m, 2H), 3.15-2.98 (m, 4H), 2.84 (br d, J=10.8 Hz, 1H), 2.76-2.68 (m, 4H), 1.30 (br d, J=6.1 Hz, 3H), 1.23 (d, J=6.1 Hz, 3H); LCMS [M+H]$^+$ 591.5.

Example 453: 4-fluoro-N-[4-fluoro-5-[2-[(2R)-2-methylmorpholin-4-yl]pyrimidin-5-yl]-2-[(3S,5R)-3,4,5-trimethylpiperazin-1-yl]phenyl]-2-(trifluoromethyl)benzamide

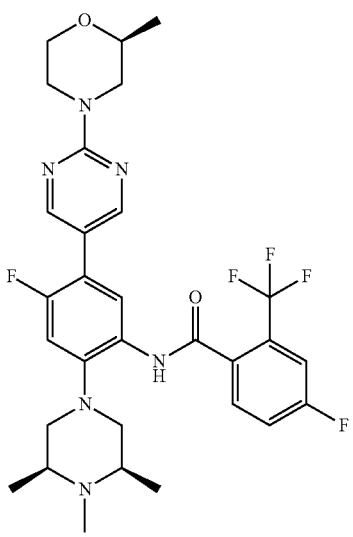 [SMILES: C[C@@H]1CN(c2cc(F)c(-c3cnc(N4CCO[C@@H](C)C4)nc3)cc2NC(=O)c2ccc(F)cc2C(F)(F)F)C[C@H](C)N1C]

The title compound (formic acid salt, beige solid, 35.8 mg, 54%) was prepared according to a procedure similar to Example 400 using crude (S)-(2-(2-methylmorpholino)pyrimidin-5-yl)boronic acid (0.2 mmol) and N-(5-bromo-4-fluoro-2-((3S,5R)-3,4,5-trimethylpiperazin-1-yl)phenyl)-4-fluoro-2-(trifluoromethyl)benzamide (51 mg, 0.1 mmol). $^1$H NMR (500 MHz, METHANOL-d4) δ=8.55 (s, 2H), 8.46 (br s, 1H), 8.03 (d, J=8.2 Hz, 1H), 7.78 (dd, J=5.4, 8.3 Hz, 1H), 7.65 (br d, J=8.9 Hz, 1H), 7.56 (br t, J=8.1 Hz, 1H), 7.16 (d, J=11.9 Hz, 1H), 4.65-4.52 (m, 2H), 3.99-3.94 (m, 1H), 3.67-3.56 (m, 2H), 3.18 (br s, 2H), 3.12-2.96 (m, 3H), 2.87-2.76 (m, 2H), 2.75-2.68 (m, 1H), 2.66 (s, 3H), 1.30 (br d, J=5.7 Hz, 6H), 1.23 (d, J=6.2 Hz, 3H); LCMS [M+H]$^+$ 605.5.

Example 454: N-[5-[2-(4-cyclopropylpiperazin-1-yl)pyrimidin-5-yl]-4-fluoro-2-[(3R,5S)-3,4,5-trimethylpiperazin-1-yl]phenyl]-4-fluoro-2-(trifluoromethyl)benzamide

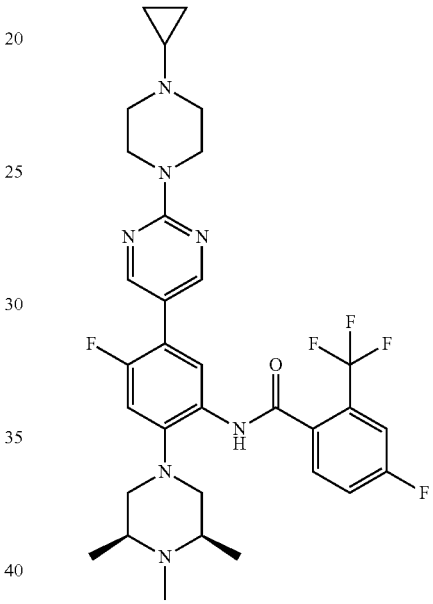

The title compound (beige solid, 4.2 mg, 7%) was prepared according a procedure similar to Example 400 using crude (2-(4-cyclopropylpiperazin-1-yl)pyrimidin-5-yl)boronic acid (0.27 mmol) and N-(5-bromo-4-fluoro-2-((3S,5R)-3,4,5-trimethylpiperazin-1-yl)phenyl)-4-fluoro-2-(trifluoromethyl)benzamide (57 mg, 89% purity, 0.1 mmol). $^1$H NMR (500 MHz, METHANOL-d4) δ=8.56 (s, 2H), 8.03 (d, J=8.3 Hz, 1H), 7.78 (dd, J=5.3, 8.5 Hz, 1H), 7.66 (dd, J=2.2, 9.2 Hz, 1H), 7.58 (t, J=8.3 Hz, 1H), 7.11 (d, J=12.0 Hz, 1H), 3.91-3.84 (m, 4H), 3.07 (br d, J=11.4 Hz, 2H), 2.74 (t, J=5.1 Hz, 4H), 2.63 (t, J=11.2 Hz, 2H), 2.52-2.43 (m, 2H), 2.34 (s, 3H), 1.76-1.72 (m, 1H), 1.17 (d, J=6.2 Hz, 6H), 0.58-0.49 (m, 4H); LCMS [M+H]$^+$ 630.6.

Example 455: N-[5-[2-(4-cyclopropylpiperazin-1-yl)pyrimidin-5-yl]-4-fluoro-2-[(3R)-3,4-dimethylpiperazin-1-yl]phenyl]-1-methyl-6-oxo-4-(trifluoromethyl)pyridine-3-carboxamide Example 456: 4-fluoro-N-[4-fluoro-2-[(3S)-3,4-dimethylpiperazin-1-yl]-5-[2-[(2R)-2-methylmorpholin-4-yl]pyrimidin-5-yl]phenyl]-2-(trifluoroethyl)benzamide

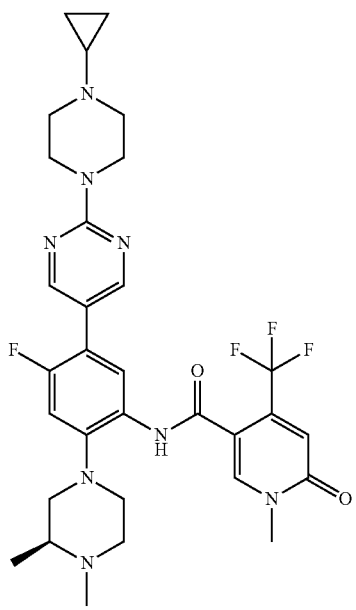 [SMILES: C[C@H]1CN(c2cc(F)c(-c3cnc(N4CCN(C5CC5)CC4)nc3)cc2NC(=O)c2cn(C)c(=O)cc2C(F)(F)F)CCN1C]

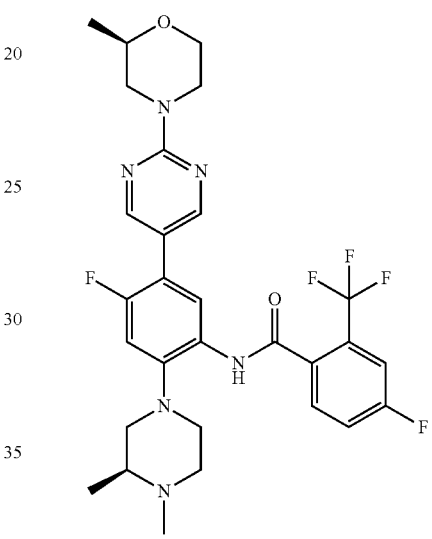

The title compound (light beige solid, 28.3 mg, 44%) was prepared according to a procedure similar to Example 400 using crude (2-(4-cyclopropylpiperazin-1-yl)pyrimidin-5-yl)boronic acid (0.27 mmol) and (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (49 mg, 0.1 mmol). $^1$H NMR (500 MHz, METHANOL-d4) δ=8.54 (s, 2H), 8.27 (s, 1H), 7.92 (d, J=8.2 Hz, 1H), 7.12 (d, J=12.0 Hz, 1H), 6.95 (s, 1H), 3.86 (br s, 4H), 3.66 (s, 3H), 3.15-3.03 (m, 2H), 3.00-2.89 (m, 2H), 2.78-2.69 (m, 4H), 2.62-2.51 (m, 2H), 2.43 (br s, 1H), 2.38 (s, 3H), 1.74 (br d, J=3.9 Hz, 1H), 1.14 (d, J=6.2 Hz, 3H), 0.58-0.53 (m, 2H), 0.53-0.49 (m, 2H); LCMS [M+H]$^+$ 629.6.

The title compound (formic acid salt, beige solid, 25.0 mg, 38%) was prepared according to a procedure similar to Example 400 using crude (R)-(2-(2-methylmorpholino)pyrimidin-5-yl)boronic acid (0.2 mmol) and (S)—N-(5-bromo-2-(3,4-dimethylpiperazin-1-yl)-4-fluoro-2-(trifluoromethyl)benzamide (49 mg, 0.1 mmol). $^1$H NMR (500 MHz, METHANOL-d4) δ=8.57 (s, 2H), 8.03 (d, J=8.3 Hz, 1H), 7.79 (dd, J=5.4, 8.4 Hz, 1H), 7.66 (dd, J=2.3, 9.0 Hz, 1H), 7.57 (dt, J=2.3, 8.3 Hz, 1H), 7.13 (d, J=12.0 Hz, 1H), 4.65-4.54 (m, 2H), 3.99 (dd, J=2.5, 11.6 Hz, 1H), 3.68-3.59 (m, 2H), 3.15-3.01 (m, 3H), 2.99-2.88 (m, 2H), 2.74 (dd, J=10.5, 13.2 Hz, 1H), 2.57 (t, J=10.8 Hz, 1H), 2.52-2.44 (m, 1H), 2.37-2.31 (m, 4H), 1.25 (d, J=6.2 Hz, 3H), 1.13 (d, J=6.2 Hz, 3H); LCMS [M+H]$^+$ 591.5.

Example 457: N-[5-[1-[5-[(dimethylamino)methyl]
pyrimidin-2-yl]-2,5-dihydropyrrol-3-yl]-4-fluoro-2-
[(3R,5S)-3,4,5-trimethylpiperazin-1-yl]phenyl]-6-
oxo-4-(trifluoromethyl)-1H-pyridine-3-carboxamide Example 458: N-[4-fluoro-5-[1-[5-(morpholin-4-
ylmethyl)pyrimidin-2-yl]-2,5-dihydropyrrol-3-yl]-2-
[(3R,5S)-3,4,5-trimethylpiperazin-1-yl]phenyl]-6-
oxo-4-(trifluoromethyl)-1H-pyridine-3-carboxamide

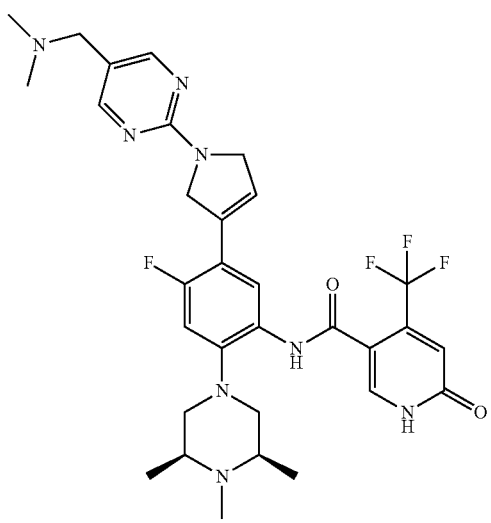 [SMILES: C[C@@H]1CN(c2cc(F)c(C3=CCN(c4ncc(CN(C)C)cn4)C3)cc2NC(=O)c2c[nH]c(=O)cc2C(F)(F)F)C[C@H](C)N1C]

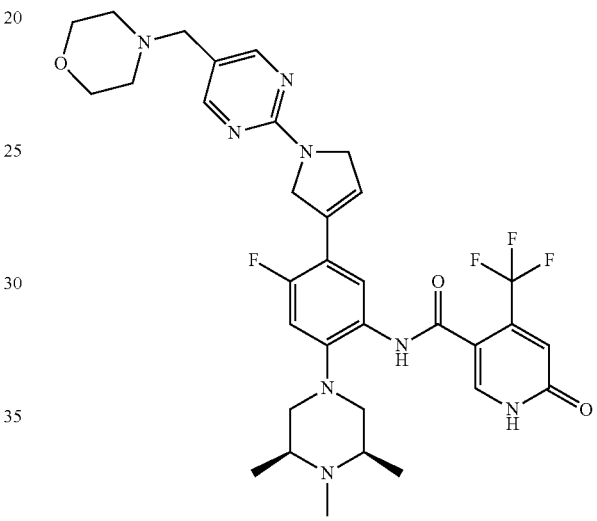

The procedure followed was similar to Example 148 using N-(4-fluoro-5-(1-(5-formylpyrimidin-2-yl)-2,5-dihydro-1H-pyrrol-3-yl)-2-((3S,5R)-3,4,5-trimethylpiperazin-1-yl)phenyl)-6-oxo-4-(trifluoromethyl)-1,6-dihydropyridine-3-carboxamide (30 mg, 0.050 mmol) and dimethylamine, 2.0M in THF (0.050 ml, 0.100 mmol) to give the title compound (23 mg, 70% yield). $^1$H NMR (500 MHz, METHANOL-d4) δ=8.40-8.34 (m, 2H), 8.04-7.97 (m, 1H), 7.95-7.85 (m, 1H), 7.08-7.00 (m, 1H), 6.95-6.89 (m, 1H), 6.55-6.46 (m, 1H), 4.76-4.72 (m, 2H), 4.57-4.53 (m, 2H), 3.46-3.42 (m, 2H), 3.11-3.05 (m, 2H), 2.65-2.58 (m, 2H), 2.56-2.48 (m, 2H), 2.40-2.36 (m, 3H), 2.33-2.28 (m, 6H), 1.17 (d, J=6.1 Hz, 6H); LCMS [M+H]+ 629.8.

The procedure employed was similar to that of Example 148 using N-(4-fluoro-5-(1-(5-formylpyrimidin-2-yl)-2,5-dihydro-1H-pyrrol-3-yl)-2-((3S,5R)-3,4,5-trimethylpiperazin-1-yl)phenyl)-6-oxo-4-(trifluoromethyl)-1,6-dihydropyridine-3-carboxamide (30 mg, 0.050 mmol) and morpholine (8.72 mg, 0.100 mmol) to give the title compound (10 mg, 28% yield). $^1$H NMR (500 MHz, METHANOL-d4) δ=8.41-8.32 (m, 2H), 8.03-7.98 (m, 1H), 7.94-7.86 (m, 1H), 7.08-7.00 (m, 1H), 6.95-6.89 (m, 1H), 6.55-6.47 (m, 1H), 4.76-4.71 (m, 2H), 4.57-4.51 (m, 2H), 3.75-3.68 (m, 4H), 3.46-3.42 (m, 2H), 3.12-3.04 (m, 2H), 2.66-2.59 (m, 2H), 2.57-2.52 (m, 2H), 2.51-2.44 (m, 4H), 2.41-2.37 (m, 3H), 1.19-1.15 (m, 6H); LCMS [M+H]+ 671.8.

Example 459: N-[4-fluoro-5-[1-[5-[(4-methylpiperazin-1-yl)methyl]pyrimidin-2-yl]-2,5-dihydropyrrol-3-yl]-2-[(3R,5S)-3,4,5-trimethylpiperazin-1-yl]phenyl]-6-oxo-4-(trifluoromethyl)-1H-pyridine-3-carboxamide Example 460: 4-(difluoromethyl)-N-[4-fluoro-2-[(3S)-3,4-dimethylpiperazin-1-yl]-5-[2-[(2R)-2-methylmorpholin-4-yl]pyrimidin-5-yl]phenyl]-1-methyl-6-oxopyridine-3-carboxamide

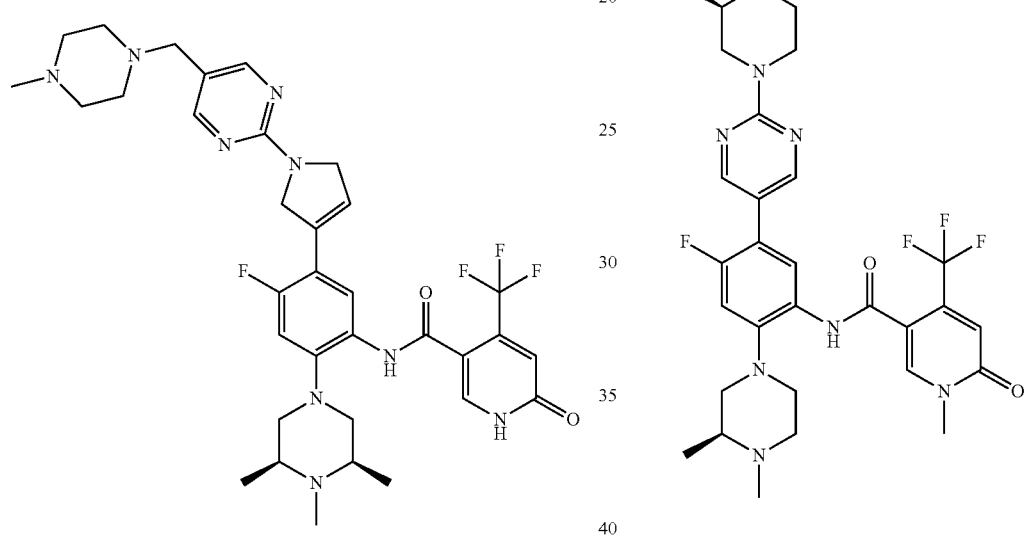

The procedure followed was similar to Example 148 using N-(4-fluoro-5-(1-(5-formylpyrimidin-2-yl)-2,5-dihydro-1H-pyrrol-3-yl)-2-((3S,5R)-3,4,5-trimethylpiperazin-1-yl)phenyl)-6-oxo-4-(trifluoromethyl)-1,6-dihydropyridine-3-carboxamide (30 mg, 0.050 mmol) and 1-methylpiperazine (10.02 mg, 0.100 mmol) to give the title compound (25 mg, 69% yield). $^1$H NMR (500 MHz, METHANOL-d4) δ=8.38-8.32 (m, 2H), 8.02-7.97 (m, 1H), 7.95-7.87 (m, 1H), 7.07-7.01 (m, 1H), 6.95-6.88 (m, 1H), 6.54-6.47 (m, 1H), 4.78-4.71 (m, 2H), 4.58-4.51 (m, 2H), 3.49-3.44 (m, 2H), 3.12-3.03 (m, 2H), 2.80-2.40 (m, 12H), 2.38-2.35 (m, 3H), 2.34-2.29 (m, 3H), 1.19-1.15 (m, 6H); LCMS [M+H]+ 584.6.

The title compound (8.1 mg, 33.7% yield) was prepared according to a procedure similar to that described for Example 383 using (S)—N-(5-bromo-2-(3,4-dimethylpiperazin-1-yl)-4-fluorophenyl)-4-(difluoromethyl)-1-methyl-6-oxo-1,6-dihydropyridine-3-carboxamide (20 mg, 0.041 mmol) and (R)-(2-(2-methylmorpholino)pyrimidin-5-yl)boronic acid (45.8 mg, 0.205 mmol). $^1$H NMR (500 MHz, DMSO-d6) δ=9.47 (s, 1H), 8.52 (s, 2H), 8.36 (s, 1H), 7.68 (d, J=8.4 Hz, 1H), 7.47-7.18 (m, 1H), 7.08 (d, J=12.2 Hz, 1H), 6.65 (s, 1H), 4.52 (br d, J=13.1 Hz, 1H), 4.44 (br d, J=13.2 Hz, 1H), 3.91 (br dd, J=2.4, 11.4 Hz, 1H), 3.52 (s, 4H), 3.08-2.95 (m, 3H), 2.86-2.79 (m, 1H), 2.76 (br d, J=11.0 Hz, 1H), 2.67 (dd, J=10.5, 13.0 Hz, 1H), 2.42 (br t, J=10.5 Hz, 1H), 2.38-2.29 (m, 1H), 2.20 (s, 3H), 1.16 (d, J=6.2 Hz, 3H), 0.97 (d, J=6.2 Hz, 3H); LCMS [M+H]+: 586.6.

623

Example 461: 4-(difluoromethyl)-N-[4-fluoro-5-[2-[(2R)-2-methylmorpholin-4-yl]pyrimidin-5-yl]-2-[(3R,5S)-3,4,5-trimethylpiperazin-1-yl]phenyl]-1-methyl-6-oxopyridine-3-carboxamide

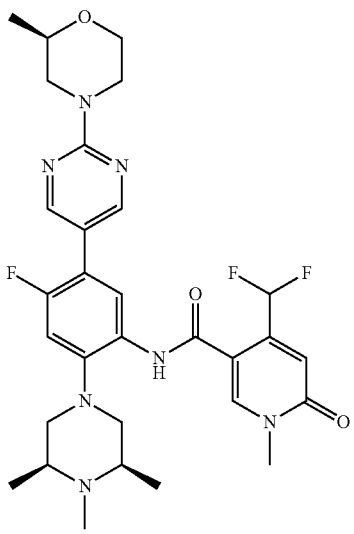

Step 1: N-(5-bromo-4-fluoro-2-((3S,5R)-3,4,5-trimethylpiperazin-1-yl)phenyl)-4-(difluoromethyl)-1-methyl-6-oxo-1,6-dihydropyridine-3-carboxamide

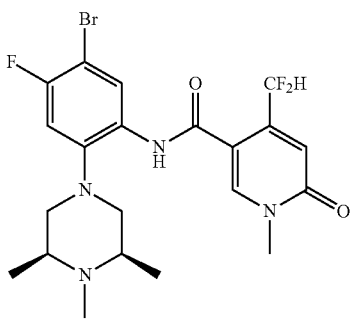

To a stirred solution of 4-(difluoromethyl)-1-methyl-6-oxo-1,6-dihydropyridine-3-carboxylic acid (4 g, 19.7 mmol, 1 eq, from Example 34, Step 4) in DMF (40 mL) was added DIPEA (9.9 mL, 59.0 mmol, 3 eq), HATU (22.4 g, 59.1 mmol, 3 eq) and then 5-bromo-4-fluoro-2-((3S,5R)-3,4,5-trimethylpiperazin-1-yl)aniline (6.2 g, 19.7 mmol, 1 eq) was dropwise added at 0° C.-rt for 16 h. TLC analysis indicated formation of polar spots. The reaction mixture was diluted with ice water (100 mL) and extracted with EtOAc (2×100 mL). The organic layer was washed with brine and dried over $Na_2SO_4$ and concentrated under reduced pressure to give crude product. The crude product was purified by column chromatography (neutral alumina) using 0-5% MeOH in DCM as an eluent to afford (2.5 g, 30%) as a pale brown solid. LCMS: [M+H]+ 501.07.

624

Step 2: 4-(difluoromethyl)-N-[4-fluoro-5-[2-[(2R)-2-methylmorpholin-4-yl]pyrimidin-5-yl]-2-[(3R,5S)-3,4,5-trimethylpiperazin-1-yl]phenyl]-1-methyl-6-oxopyridine-3-carboxamide

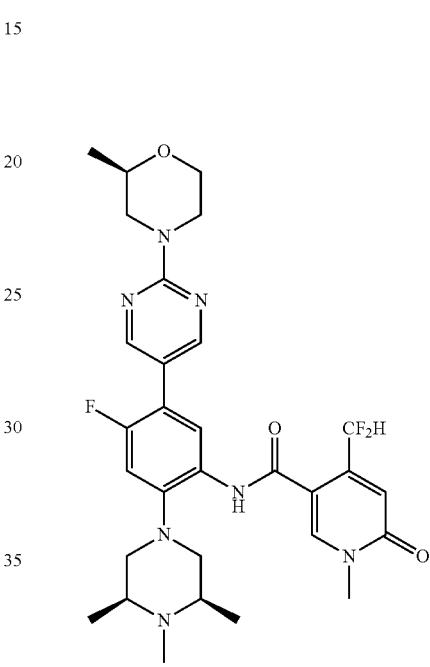

The title compound (11.0 mg, 46% yield) was prepared according to a procedure similar to that described for Example 31 using N-(5-bromo-4-fluoro-2-((3S,5R)-3,4,5-trimethylpiperazin-1-yl)phenyl)-4-(difluoromethyl)-1-methyl-6-oxo-1,6-dihydropyridine-3-carboxamide (20 mg, 0.040 mmol), (R)-(2-(2-methylmorpholino)pyrimidin-5-yl) boronic acid (35.6 mg, 0.160 mmol). $^1$H NMR (500 MHz, DMSO-d6) δ=9.51 (br s, 1H), 8.52 (s, 2H), 8.35 (s, 1H), 7.67 (d, J=8.6 Hz, 1H), 7.51-7.21 (m, 1H), 7.06 (d, J=12.3 Hz, 1H), 6.65 (s, 1H), 4.52 (br d, J=13.0 Hz, 1H), 4.45 (br d, J=13.0 Hz, 1H), 3.92 (dd, J=2.4, 11.7 Hz, 1H), 3.53 (s, 3H), 3.04 (br d, J=11.4 Hz, 2H), 3.01-2.96 (m, 1H), 2.72-2.64 (m, 1H), 2.48-2.43 (m, 2H), 2.37-2.31 (m, 2H), 2.19 (s, 3H), 1.17 (d, J=6.1 Hz, 3H), 1.01 (d, J=6.0 Hz, 6H); LCMS [M+H]+: 600.6.

Example 462: 4-(difluoromethyl)-N-[4-fluoro-5-[2-[(2R,6S)-2,6-dimethylmorpholin-4-yl]pyrimidin-5-yl]-2-[(3R,5S)-3,4,5-trimethylpiperazin-1-yl]phenyl]-1-methyl-6-oxopyridine-3-carboxamide

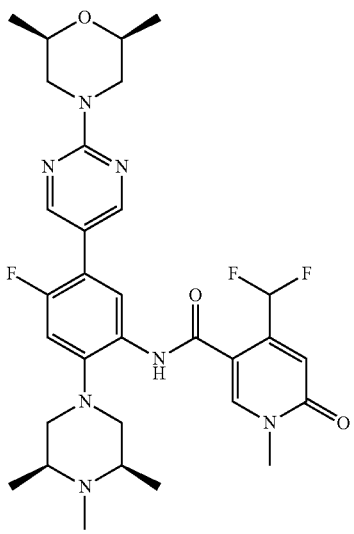

The title compound (4.8 mg, 20% yield) was prepared according to a procedure similar to that of Example 31 using N-(5-bromo-4-fluoro-2-((3S,5R)-3,4,5-trimethylpiperazin-1-yl)phenyl)-4-(difluoromethyl)-1-methyl-6-oxo-1,6-dihydropyridine-3-carboxamide (20 mg, 0.040 mmol), (2S,6R)-2,6-dimethyl-4-(5-(4,4,5,5-tetramethyl-1,3,2-dioxaborolan-2-yl)pyrimidin-2-yl)morpholine (19.10 mg, 0.060 mmol). $^1$H NMR (500 MHz, DMSO-d6) δ=9.40 (s, 1H), 8.28 (s, 1H), 8.18 (br s, 1H), 7.64-7.56 (m, 2H), 7.44-7.12 (m, 1H), 6.96 (br d, J=12.3 Hz, 1H), 6.88 (br d, J=8.8 Hz, 1H), 6.57 (s, 1H), 4.12 (br d, J=12.3 Hz, 2H), 3.61-3.51 (m, 2H), 3.45 (s, 3H), 2.95 (br d, J=10.9 Hz, 2H), 2.28 (br d, J=7.6 Hz, 2H), 2.11 (s, 3H), 1.10 (br d, J=6.1 Hz, 6H), 0.93 (br d, J=6.0 Hz, 6H); LCMS [M+H]+: 613.6.

Example 463: N-[4-fluoro-5-(2-morpholin-4-ylpyrimidin-5-yl)-2-[(3aR,6aR)-2,3,3a,4,6,6a-hexahydro-1H-pyrrolo[2,3-c]pyrrol-5-yl]phenyl]-6-oxo-4-(trifluoromethyl)-1H-pyridine-3-carboxamide

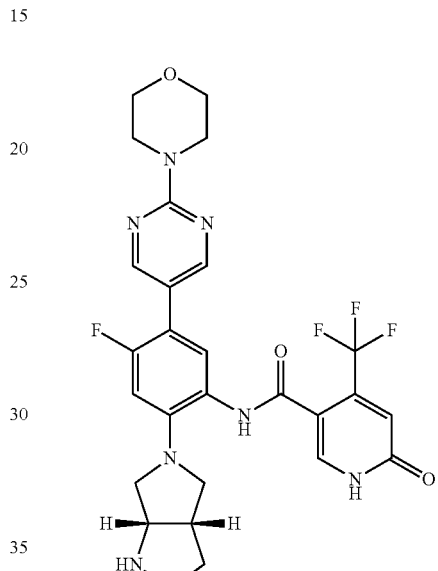

The title compound (22.5 mg, 1.219% yield) was obtained as an off-white powder from tert-butyl (3aS,6aS)-5-(2-amino-5-fluoro-4-(2-morpholinopyrimidin-5-yl)phenyl) hexahydropyrrolo[3,4-b]pyrrole-1(2H)-carboxylate (1.31 g, 2.70 mmol) and 4-(trifluoromethyl)-6-(2-(trimethylsilyl) ethoxy)nicotinic acid (0.96 g, 3.12 mmol) followed by TFA deprotection of the silyloxypyridine intermediate using a procedure similar to that described for the final step of Example 39. The tert-butyl (3aS,6aS)-5-(2-amino-5-fluoro-4-(2-morpholinopyrimidin-5-yl)phenyl)hexahydropyrrolo[3,4-b]pyrrole-1(2H)-carboxylate was obtained from a route starting with 1-Boc-3as-6as-octahydropyrrolo-3-4-b-pyrrole and 1-bromo-2,4-difluoro-5-nitrobenzene through a route similar to that described in Example 34. $^1$H NMR (500 MHz, DMSO-d6) δ=9.70 (br. s., 1H), 8.51 (s, 2H), 8.06 (s, 1H), 7.50 (d, J=8.68 Hz, 1H), 6.82 (d, J=13.20 Hz, 1H), 6.74 (s, 1H), 3.74 (d, J=5.01 Hz, 7H), 3.68 (d, J=4.89 Hz, 7H), 3.17-3.29 (m, 9H), 3.09 (d, J=9.05 Hz, 2H), 2.97 (dd, J=4.46, 9.72 Hz, 2H), 2.88 (dd, J=6.60, 10.39 Hz, 2H), 2.68-2.81 (m, 3H), 1.82 (dd, J=7.64, 12.17 Hz, 1H), 1.48-1.58 (m, 1H); LCMS [M+H]+ 574.5.

Example 464: N-[4-fluoro-5-(2-piperazin-1-ylpyrimidin-5-yl)-2-[(3R)-3,4-dimethylpiperazin-1-yl]phenyl]-1-methyl-6-oxo-4-(trifluoromethyl)pyridine-3-carboxamide

Example 465: 4-fluoro-N-[4-fluoro-5-[2-(4-propan-2-ylpiperazin-1-yl)pyrimidin-5-yl]-2-[(3R)-3,4-dimethylpiperazin-1-yl]phenyl]-2-(trifluoromethyl)benzamide

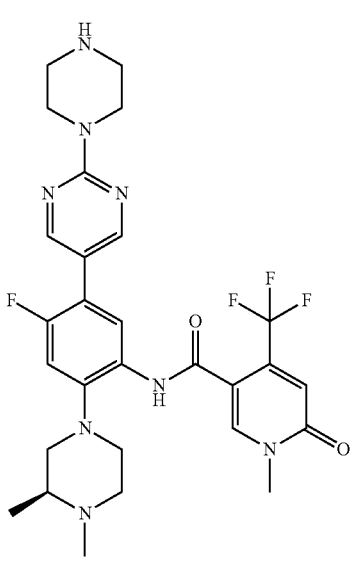

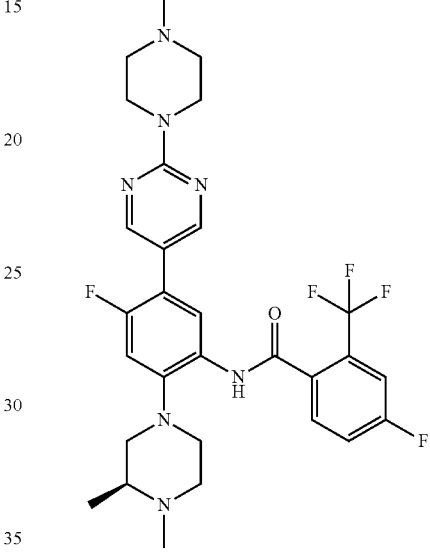

Intermediate tert-butyl (S)-4-(5-(4-(3,4-dimethylpiperazin-1-yl)-2-fluoro-5-(1-methyl-6-oxo-4-(trifluoromethyl)-1,6-dihydropyridine-3-carboxamido)phenyl)pyrimidin-2-yl)piperazine-1-carboxylate (brown solid) was prepared according to a procedure similar to that of Example 31 using 2-(4-Boc-piperazino)pyrimidine-5-boronic acid pinacol ester (234 mg, 0.6 mmol) and (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (202 mg, 0.4 mmol). LCMS [M+H]$^+$689.6. Followed by deprotection using TFA (1.2 mL) in DCM (20 mL) and removal of the solvents, the residue was passed through porapak (20 cc, rinsed with DCM/2 M NH$_3$/MeOH), purified by prep-HPLC and Biotage Isolute SCX-2 column to give the title compound as a light yellow solid (117.4 mg, 49% over 2 steps). $^1$H NMR (500 MHz, METHANOL-d4) δ=8.55 (s, 2H), 8.27 (s, 1H), 7.92 (d, J=8.2 Hz, 1H), 7.12 (d, J=12.1 Hz, 1H), 6.95 (s, 1H), 3.91-3.83 (m, 4H), 3.67 (s, 3H), 3.14-3.03 (m, 2H), 2.99-2.89 (m, 6H), 2.60-2.49 (m, 2H), 2.44-2.34 (m, 4H), 1.13 (d, J=6.2 Hz, 3H); LCMS [M+H]$^+$ 589.6.

To a mixture of 2-chloropyrimidine-5-boronic acid (633 mg, 4 mmol) and 1-isopropylpiperazine (0.57 mL, 4.4 mmol) in EtOH (8 mL) was added triethylamine (0.84 mL, 6 mmol). The resulting mixture (a cloudy suspension, never observed to clear) was stirred at 75° C. for 1 h. Solvents were removed and the residue was dried under high vacuum to give crude (2-(4-isopropylpiperazin-1-yl)pyrimidin-5-yl)boronic acid as a beige solid (1.272 g, 79% purity assuming full conversion). LCMS [M+H]$^+$ found 251.4. The title compound (light beige solid, 34.1 mg, 54%) was prepared by a procedure similar to Example 400 using crude (2-(4-isopropylpiperazin-1-yl)pyrimidin-5-yl)boronic acid (0.27 mmol) and (S)—N-(5-bromo-2-(3,4-dimethylpiperazin-1-yl)-4-fluorophenyl)-4-fluoro-2-(trifluoromethyl)benzamide (57 mg, 86% purity, 0.1 mmol). $^1$H NMR (500 MHz, METHANOL-d4) δ=8.56 (s, 2H), 8.03 (d, J=8.2 Hz, 1H), 7.80 (dd, J=5.3, 8.4 Hz, 1H), 7.66 (dd, J=2.1, 9.0 Hz, 1H), 7.57 (t, J=8.3 Hz, 1H), 7.13 (d, J=12.0 Hz, 1H), 3.91 (br s, 4H), 3.14-3.03 (m, 2H), 3.00-2.88 (m, 2H), 2.83-2.73 (m, 1H), 2.67 (br t, J=4.7 Hz, 4H), 2.58 (br t, J=10.8 Hz, 1H), 2.52-2.41 (m, 1H), 2.39-2.31 (m, 4H), 1.18-1.11 (m, 9H); LCMS [M+H]$^+$ 618.6.

Example 466: 4-fluoro-N-[4-fluoro-5-[2-(4-propan-2-ylpiperazin-1-yl)pyrimidin-5-yl]-2-[(3R,5S)-3,4,5-trimethylpiperazin-1-yl]phenyl]-2-(trifluoromethyl)benzamide

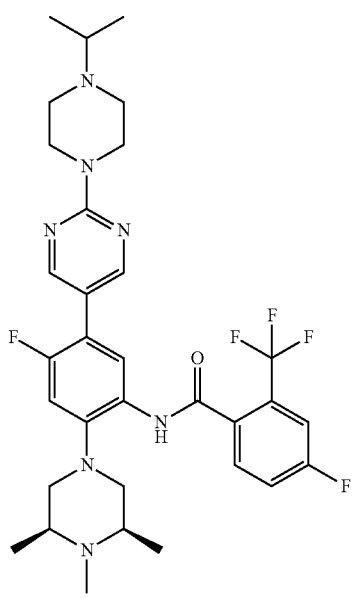

The title compound (pale beige solid, 34.3 mg, 54%) was prepared by a procedure similar to that of Example 31 using crude (2-(4-isopropylpiperazin-1-yl)pyrimidin-5-yl)boronic acid (0.27 mmol) and (N-(5-bromo-4-fluoro-2-((3S,5R)-3,4,5-trimethylpiperazin-1-yl)phenyl)-4-fluoro-2-(trifluoromethyl)benzamide (57 mg, 89% purity, 0.1 mmol). $^1$H NMR (500 MHz, METHANOL-d4) δ=8.56 (s, 2H), 8.03 (d, J=8.3 Hz, 1H), 7.78 (dd, J=5.3, 8.4 Hz, 1H), 7.66 (dd, J=2.2, 9.0 Hz, 1H), 7.57 (dt, J=2.2, 8.2 Hz, 1H), 7.11 (d, J=12.0 Hz, 1H), 3.91 (br s, 4H), 3.06 (br d, J=11.4 Hz, 2H), 2.84-2.74 (m, 1H), 2.72-2.60 (m, 6H), 2.47 (br s, 2H), 2.38-2.31 (m, 3H), 1.17 (br d, J=6.4 Hz, 6H), 1.15 (br d, J=6.5 Hz, 6H); LCMS [M+H]$^+$ 632.7.

Example 467: N-[4-fluoro-5-[2-(4-propan-2-ylpiperazin-1-yl)pyrimidin-5-yl]-2-[(3R)-3,4-dimethylpiperazin-1-yl]phenyl]-1-methyl-6-oxo-4-(trifluoromethyl)pyridine-3-carboxamide

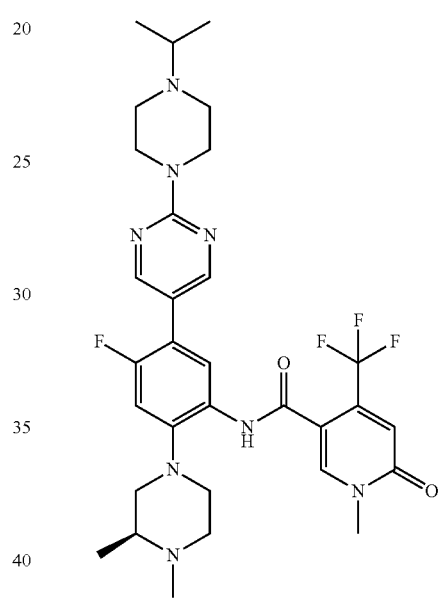

The title compound (beige solid, 25.4 mg, 40%) was prepared according to a procedure similar to that of Example 31 using crude (2-(4-isopropylpiperazin-1-yl)pyrimidin-5-yl)boronic acid (0.27 mmol) and (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (50.5 mg, 89% purity, 0.1 mmol). $^1$H NMR (500 MHz, METHANOL-d4) δ=8.55 (s, 2H), 8.27 (s, 1H), 7.92 (d, J=8.3 Hz, 1H), 7.12 (d, J=12.1 Hz, 1H), 6.95 (s, 1H), 3.91 (br s, 4H), 3.67 (s, 3H), 3.15-3.03 (m, 2H), 2.99-2.87 (m, 2H), 2.85-2.75 (m, 1H), 2.68 (br s, 4H), 2.61-2.50 (m, 2H), 2.45-2.34 (m, 4H), 1.18-1.11 (m, 9H); LCMS [M+H]$^+$ 631.6.

Example 468: N-[4-fluoro-2-[(3S)-3,4-dimethylpiperazin-1-yl]-5-[2-[(3R)-3-methylmorpholin-4-yl]pyrimidin-5-yl]phenyl]-6-oxo-4-(trifluoromethyl)-1H-pyridine-3-carboxamide

Example 469: N-[4-fluoro-5-[2-[(3R)-3-methylmorpholin-4-yl]pyrimidin-5-yl]-2-[(3R,5S)-3,4,5-trimethylpiperazin-1-yl]phenyl]-6-oxo-4-(trifluoromethyl)-1H-pyridine-3-carboxamide

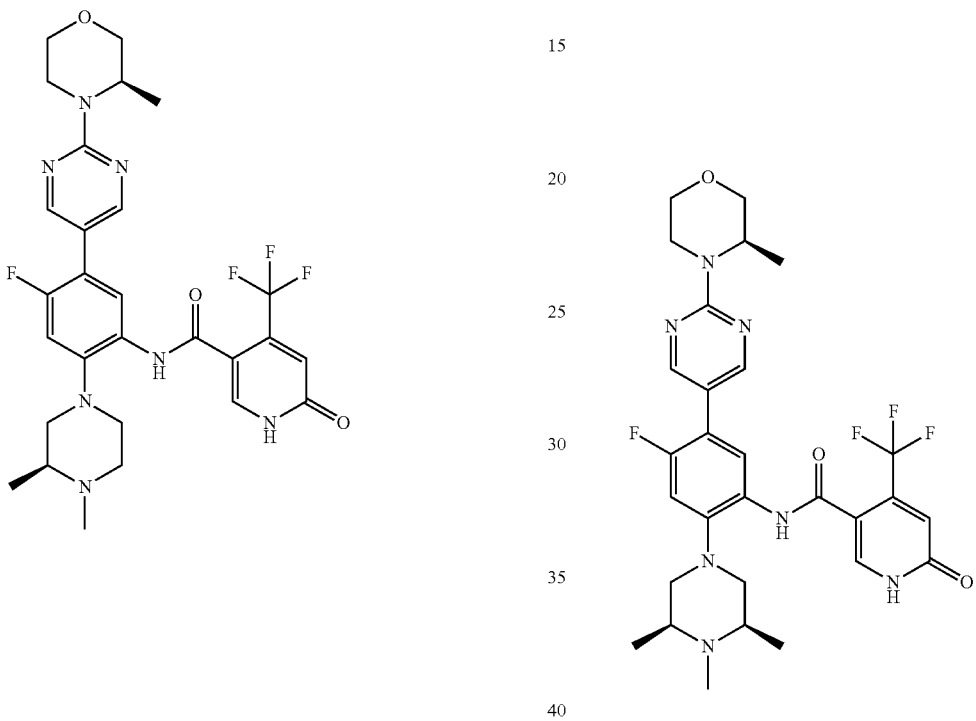

To a mixture of 2-chloropyrimidine-5-boronic acid (633 mg, 4 mmol) and (R)-3-methylmorpholine (0.55 mL, 4.8 mmol) in EtOH (8 mL) was added triethylamine (0.84 mL, 6 mmol). The resulting mixture was stirred for 1 h at 75° C. for 5 h. Solvents were removed to give a dark orange oil that was dried under high vacuum to give crude (R)-(2-(3-methylmorpholino)pyrimidin-5-yl)boronic acid as a yellow foam (953 mg, 84% purity assuming 90% conversion based on LCMS). LCMS [M+H]$^+$ 224.3. The title compound (beige solid, 6.3 mg, 10%) was prepared by a procedure similar to that used in Example 31 using crude (R)-(2-(3-methylmorpholino)pyrimidin-5-yl)boronic acid (0.3 mmol×2) and (S)—N-(5-bromo-2-(3,4-dimethylpiperazin-1-yl)-4-fluorophenyl)-6-oxo-4-(trifluoromethyl)-1,6-dihydropyridine-3-carboxamide (49.1 mg, 0.1 mmol). $^1$H NMR (500 MHz, METHANOL-d4) δ=8.55 (s, 2H), 8.01 (s, 1H), 7.93 (br d, J=8.2 Hz, 1H), 7.13 (br d, J=11.7 Hz, 1H), 6.90 (s, 1H), 4.75 (br d, J=5.3 Hz, 1H), 4.38 (br d, J=12.6 Hz, 1H), 4.02-3.96 (m, 1H), 3.80 (br d, J=11.5 Hz, 1H), 3.76-3.69 (m, 1H), 3.63-3.53 (m, 1H), 3.21-2.63 (m, 8H), 2.54 (br s, 3H), 1.31 (d, J=6.7 Hz, 3H), 1.21 (br s, 3H); LCMS [M+H]$^+$ 590.6.

The title compound (light beige solid, 6.4 mg, 10%) was prepared according to a procedure similar to that described in Example 31 using crude (R)-(2-(3-methylmorpholino)pyrimidin-5-yl)boronic acid (0.3 mmol×2) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, METHANOL-d4) δ=8.56 (s, 2H), 8.00 (s, 1H), 7.92 (br d, J=8.1 Hz, 1H), 7.12 (br d, J=11.9 Hz, 1H), 6.91 (s, 1H), 4.79-4.72 (m, 1H), 4.41-4.36 (m, 1H), 4.00 (br dd, J=3.5, 11.3 Hz, 1H), 3.81 (d, J=11.5 Hz, 1H), 3.73 (dd, J=2.9, 11.6 Hz, 1H), 3.57 (dt, J=2.9, 11.9 Hz, 1H), 3.12 (br d, J=11.0 Hz, 2H), 2.95-2.68 (m, 4H), 2.52 (br s, 3H), 1.32 (d, J=6.7 Hz, 3H), 1.24 (d, J=4.8 Hz, 6H); LCMS [M+H]$^+$ 604.5.

Example 470: (1-methylcyclobutyl) 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate Example 471: (1-methylcyclobutyl) 5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate

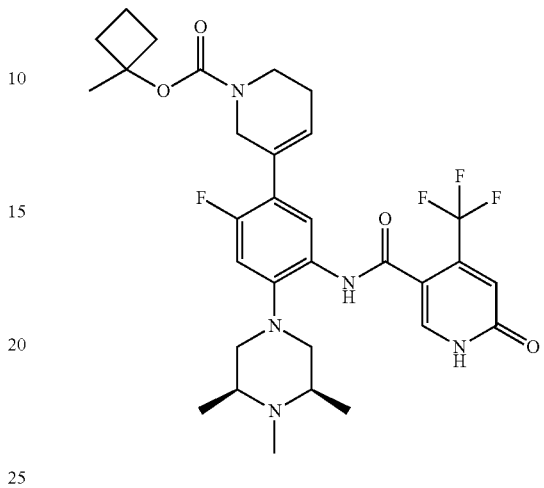

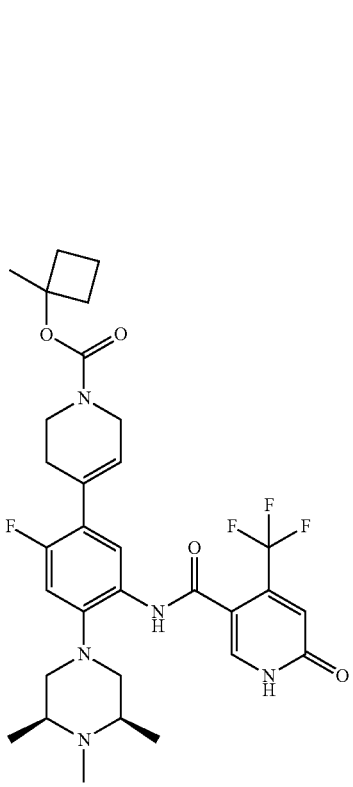 [SMILES: C[C@@H]1CN(c2cc(F)c(C3=CCN(C(=O)OC4(C)CCC4)CC3)cc2NC(=O)c2c[nH]c(=O)cc2C(F)(F)F)C[C@H](C)N1C]

The procedure followed was similar to Example 470 using N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (35 mg, 0.069 mmol) and 1-methylcyclobutyl (4-nitrophenyl) carbonate (21.66 mg, 0.069 mmol) to give the title compound (19 mg, 41% yield). $^1$H NMR (500 MHz, METHANOL-d4) δ=7.87-7.80 (m, 1H), 7.70-7.59 (m, 1H), 6.88-6.82 (m, 1H), 6.81-6.77 (m, 1H), 6.03-5.96 (m, 1H), 4.17-4.06 (m, 2H), 3.56-3.42 (m, 2H), 2.96-2.89 (m, 2H), 2.53-2.39 (m, 4H), 2.29-2.20 (m, 7H), 2.07-1.98 (m, 2H), 1.76-1.67 (m, 1H), 1.65-1.55 (m, 1H), 1.50-1.42 (m, 3H), 1.05 (d, J=6.0 Hz, 6H); LCMS [M+H]+ 620.8.

Example 472: (1-methylcyclobutyl) 3-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-2,5-dihydropyrrole-1-carboxylate

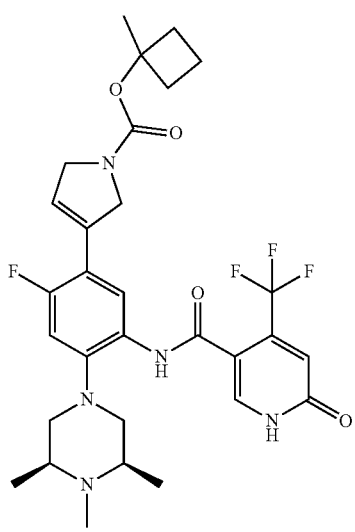

The procedure followed was similar to that described in Example 253 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (35 mg, 0.069 mmol) in dichloromethane (DCM) (3 ml) was added triethylamine (0.019 ml, 0.138 mmol) and a solution of 1-methylcyclobutyl (4-nitrophenyl) carbonate (22 mg, 0.070 mmol, prepared as described in J Med. Chem. 2016, 59 (18), pp 8345-8368) to give the title compound (18 mg, 38% yield). $^1$H NMR (500 MHz, METHANOL-d4) δ=7.87-7.80 (m, 1H), 7.70-7.61 (m, 1H), 6.87-6.82 (m, 1H), 6.81-6.77 (m, 1H), 5.92-5.83 (m, 1H), 4.04-3.92 (m, 2H), 3.61-3.47 (m, 2H), 2.94-2.89 (m, 2H), 2.51-2.39 (m, 6H), 2.31-2.23 (m, 5H), 2.08-2.00 (m, 2H), 1.78-1.69 (m, 1H), 1.65-1.56 (m, 1H), 1.50-1.45 (m, 3H), 1.07-1.03 (m, 6H); LCMS [M+H]+ 620.7.

The procedure followed was similar to Example 470 using N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (30 mg, 0.061 mmol) and 1-methylcyclobutyl (4-nitrophenyl) carbonate (19.09 mg, 0.061 mmol) to give the title compound (27 mg, 70% yield). $^1$H NMR (500 MHz, METHANOL-d4) δ=7.89-7.81 (m, 1H), 7.74-7.62 (m, 1H), 6.94-6.85 (m, 1H), 6.83-6.77 (m, 1H), 6.29-6.18 (m, 1H), 4.47-4.34 (m, 2H), 4.27-4.13 (m, 2H), 2.99-2.89 (m, 2H), 2.53-2.38 (m, 4H), 2.34-2.22 (m, 5H), 2.10-2.00 (m, 2H), 1.79-1.68 (m, 1H), 1.66-1.56 (m, 1H), 1.49 (d, J=3.8 Hz, 3H), 1.08-1.00 (m, 6H); LCMS [M+H]+ 606.7.

Example 473: N-[4-fluoro-5-(6-morpholin-4-ylpyridin-2-yl)-2-[(3R,5S)-3,4,5-trimethylpiperazin-1-yl]phenyl]-6-oxo-4-(trifluoromethyl)-1H-pyridine-3-carboxamide

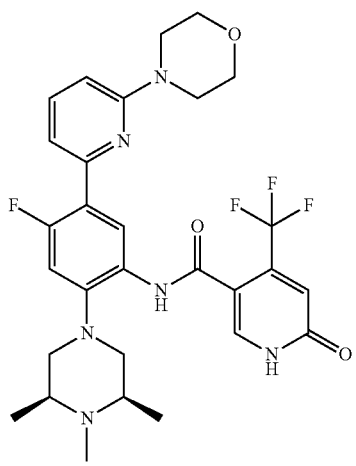

The procedure followed was similar to Example 384 using N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy)nicotinamide (103 mg, 0.126 mmol) and 4-(6-bromopyridin-2-yl)morpholine (33.8 mg, 0.139 mmol) to give the title compound (74.3 mg, 28% yield). $^1$H NMR (500 MHz, MeOD) δ 8.51 (d, J=8.3 Hz, 1H), 7.91 (s, 1H), 7.61 (t, J=8.0 Hz, 1H), 7.21 (dd, J=7.4, 1.2 Hz, 1H), 6.99 (d, J=12.9 Hz, 1H), 6.92 (s, 1H), 6.75 (d, J=8.5 Hz, 1H), 3.83-3.80 (m, 4H), 3.58-3.56 (m, 4H), 3.11 (d, J=10.4 Hz, 2H), 2.67-2.59 (m, 4H), 2.40 (s, 3H), 1.18 (d, J=5.7 Hz, 6H); LCMS [M+1]$^+$=587.46.

Example 474: N-[4-fluoro-5-(6-morpholin-4-ylpyrazin-2-yl)-2-[(3R,5S)-3,4,5-trimethylpiperazin-1-yl]phenyl]-6-oxo-4-(trifluoromethyl)-1H-pyridine-3-carboxamide

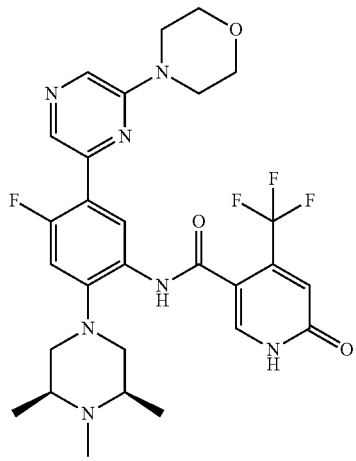

The title compound (74.4 mg, 38.3 mg) was prepared similar to the sequence described above for the preparation of Example 384 using N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy)nicotinamide (103 mg, 0.126 mmol) and 4-(6-bromopyrazin-2-yl)morpholine (33.9 mg, 0.139 mmol). $^1$H NMR (500 MHz, MeOD) δ 8.51 (d, J=8.0 Hz, 1H), 8.33 (d, J=2.1 Hz, 1H), 8.13 (s, 1H), 7.93 (s, 1H), 7.04 (d, J=13.0 Hz, 1H), 6.91 (s, 1H), 3.84-3.81 (m, 4H), 3.69-3.66 (m, 4H), 3.14 (d, J=11.4 Hz, 2H), 2.63 (t, J=11.1 Hz, 2H), 2.56 (d, J=6.4 Hz, 2H), 2.37 (s, 3H), 1.17 (d, J=6.1 Hz, 6H); $^{19}$F NMR (471 MHz, MeOD) δ −63.75 (s), −116.22 (s); LCMS [M+1]$^+$=588.44.

Example 475: 4-(difluoromethyl)-N-[4-fluoro-5-[2-[(3R)-3-methylmorpholin-4-yl]pyrimidin-5-yl]-2-[(3S,5R)-3,4,5-trimethylpiperazin-1-yl]phenyl]-1-methyl-6-oxopyridine-3-carboxamide

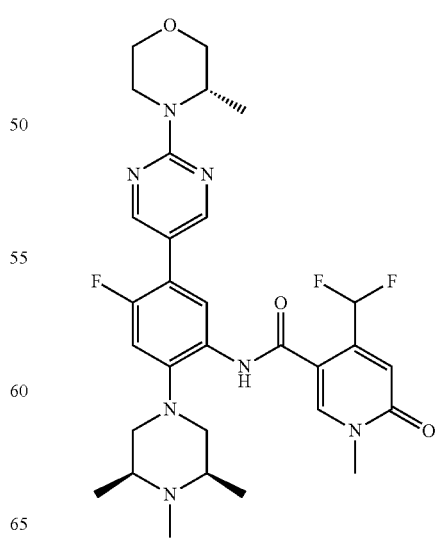

The title compound (10.6 mg, 44.6% yield) was prepared according to a procedure similar to that described in Example 31 using N-(5-bromo-4-fluoro-2-((3S,5R)-3,4,5-trimethylpiperazin-1-yl)phenyl)-4-(difluoromethyl)-1-methyl-6-oxo-1,6-dihydropyridine-3-carboxamide (20 mg, 0.040 mmol) and (S)-(2-(3-methylmorpholino)pyrimidin-5-yl)boronic acid (35.6 mg, 0.160 mmol). $^1$H NMR (500 MHz, DMSO-d6) δ=9.50 (br s, 1H), 8.52 (s, 2H), 8.34 (s, 1H), 7.67 (d, J=8.6 Hz, 1H), 7.50-7.18 (m, 1H), 7.05 (d, J=12.2 Hz, 1H), 6.64 (s, 1H), 4.65 (br dd, J=2.3, 6.7 Hz, 1H), 4.33-4.24 (m, 1H), 3.93 (br dd, J=3.1, 11.2 Hz, 1H), 3.73 (d, J=11.4 Hz, 1H), 3.60 (dd, J=2.9, 11.4 Hz, 1H), 3.52 (s, 3H), 3.44 (dt, J=2.8, 11.8 Hz, 1H), 3.19 (dt, J=3.7, 13.0 Hz, 1H), 3.03 (br d, J=11.0 Hz, 2H), 2.48-2.43 (m, 2H), 2.39-2.30 (m, 2H), 2.18 (s, 3H), 1.21 (d, J=6.7 Hz, 3H), 1.00 (d, J=6.1 Hz, 6H); LCMS [M+H]+: 600.5.

Example 476: N-[4-fluoro-5-(2-morpholin-4-ylpyrimidin-5-yl)-2-[(3aR,6aR)-1-propyl-2,3,3a,4,6,6a-hexahydropyrrolo[2,3-c]pyrrol-5-yl]phenyl]-6-oxo-4-(trifluoromethyl)-1H-pyridine-3-carboxamide

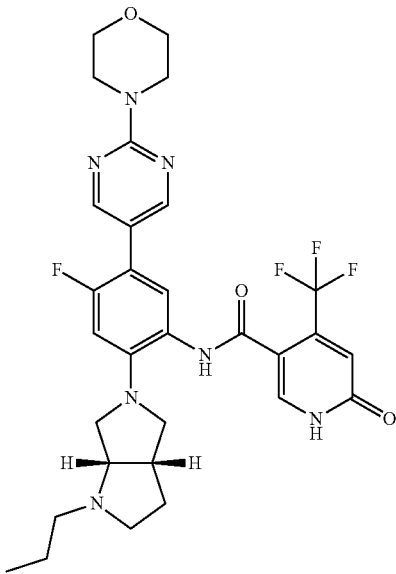 [SMILES: CCCN1CC[C@H]2CN(c3cc(F)c(-c4cnc(N5CCOCC5)nc4)cc3NC(=O)c3c[nH]c(=O)cc3C(F)(F)F)C[C@H]21]

To a solution of N-(4-fluoro-2-(hexahydropyrrolo[3,4-b]pyrrol-5(1H)-yl)-5-(2-morpholinopyrimidin-5-yl)phenyl)-6-oxo-4-(trifluoromethyl)-1,6-dihydropyridine-3-carboxamide-TFA (70 mg, 0.064 mmol, obtained from Example 463) in 1,2-dichloroethane (DCE) (3 ml) was added propionaldehyde (19.4 mg, 0.334 mmol) and acetic acid (36 mg, 0.599 mmol) at room temperature. The reaction mixture was stirred for 15 minutes and then sodium triacetoxyborohydride (54.0 mg, 0.255 mmol) was added. After 90 min the reaction mixture was poured into 20 mL of a saturated solution of NaHCO$_3$. The product was extracted using DCM (3×30 mL). The organic phase was dried over MgSO$_4$ and after filtration and solvent removal the crude material was dry loaded and purified by Flash chromatography [0-30% MeOH/DCM] to afford the N-(4-fluoro-5-(2-morpholinopyrimidin-5-yl)-2-(1-propylhexahydropyrrolo[3,4-b]pyrrol-5(1H)-yl)phenyl)-6-oxo-4-(trifluoromethyl)-1,6-dihydropyridine-3-carboxamide (10.7 mg, 0.016 mmol, 25.6% yield) as a white powder. $^1$H NMR (500 MHz, DMSO-d6) δ=12.58 (br. s., 1H), 9.63 (br. s., 1H), 8.51 (s, 2H), 8.02 (br. s., 1H), 7.53 (d, J=7.83 Hz, 1H), 6.76-6.88 (m, 2H), 3.72-3.78 (m, 5H), 3.65-3.70 (m, 5H), 3.19 (br. s., 1H), 3.11 (br. s., 1H), 2.92-3.07 (m, 3H), 2.74 (d, J=9.78 Hz, 1H), 2.43 (br. s., 1H), 2.36 (br. s., 1H), 2.19 (br. s., 2H), 1.98 (br. s., 1H), 1.61 (br. s., 1H), 1.35 (br. s., 1H), 1.23 (br. s., 1H), 0.81-0.96 (m, 1H), 0.77 (t, J=7.09 Hz, 3H); LCMS [M+H]+ 616.6.

Example 477: N-[4-fluoro-5-(2-morpholin-4-ylpyrimidin-5-yl)-2-[(3aR,6aR)-1-methyl-2,3,3a,4,6,6a-hexahydropyrrolo[2,3-c]pyrrol-5-yl]phenyl]-6-oxo-4-(trifluoromethyl)-1H-pyridine-3-carboxamide

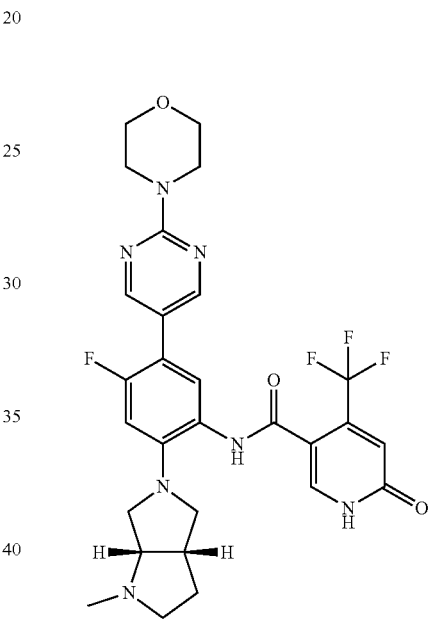

A similar procedure was used as for Example 476 with N-(4-fluoro-2-(hexahydropyrrolo[3,4-b]pyrrol-5(1H)-yl)-5-(2-morpholinopyrimidin-5-yl)phenyl)-6-oxo-4-(trifluoromethyl)-1,6-dihydropyridine-3-carboxamide-TFA (87 mg, 0.079 mmol) and formaldehyde solution, 37% weight in water (36 mg, 0.444 mmol) to afford the title compound (21.2 mg, 0.034 mmol, 42.8% yield) as a white powder. $^1$H NMR (500 MHz, DMSO-d6) δ=12.56 (br. s., 1H), 9.69 (s, 1H), 8.51 (s, 2H), 8.01 (s, 1H), 7.50 (d, J=8.68 Hz, 1H), 6.76-6.83 (m, 2H), 3.71-3.76 (m, 5H), 3.65-3.69 (m, 5H), 3.34-3.40 (m, 2H), 3.19-3.29 (m, 3H), 3.10 (dd, J=4.59, 9.48 Hz, 1H), 3.04 (dd, J=4.83, 10.33 Hz, 1H), 2.94 (t, J=7.58 Hz, 1H), 2.71-2.82 (m, 2H), 2.61-2.68 (m, 1H), 2.32 (s, 1H), 2.15-2.24 (m, 4H), 1.93-2.01 (m, 1H), 1.53-1.63 (m, 1H); LCMS [M+H]+ 588.5.

Example 478: 4-(difluoromethyl)-N-[4-fluoro-5-(3-fluoro-4-morpholin-4-ylphenyl)-2-[(3R)-3,4-dimethylpiperazin-1-yl]phenyl]-1-methyl-6-oxopyridine-3-carboxamide

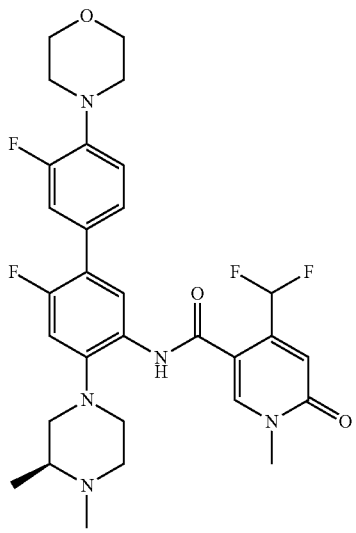 [SMILES: C[C@H]1CN(c2cc(F)c(-c3ccc(N4CCOCC4)c(F)c3)cc2NC(=O)c2cn(C)c(=O)cc2C(F)F)CCN1C]

To a suspension of (S)-4-(difluoromethyl)-N-(4-(3,4-dimethylpiperazin-1-yl)-3',6-difluoro-4'-morpholino-[1,1'-biphenyl]-3-yl)-6-oxo-1,6-dihydropyridine-3-carboxamide (39 mg, 0.068 mmol) and cesium carbonate (24.37 mg, 0.075 mmol) in N,N-dimethylformamide (3 ml) was added MeI (4.66 µl, 0.075 mmol) at room temperature. The reaction mixture was stirred for 90 min at room temperature. Then the reaction mixture was poured into water and the product was extracted by DCM (3×20 mL). The organic phase was dried over MgSO$_4$ and after filtration and solvent removal the crude material was dissolved in MeOH and passed through a PoraPak Rxn CX (20 cc-2 g) cartridge in a catch and elute method. The cartridge was washed with MeOH (20 mL) and the solution of product in MeOH was added onto the cartridge. The cartridge was rinsed with MeOH (2×20 mL) and the product was released with a solution of 10 mL (NH$_3$ in MeOH at 7N) in 10 mL of MeOH to afford the free base of (S)-4-(difluoromethyl)-N-(4-(3,4-dimethylpiperazin-1-yl)-3',6-difluoro-4'-morpholino-[1,1'-biphenyl]-3-yl)-1-methyl-6-oxo-1,6-dihydropyridine-3-carboxamide (32.4 mg, 0.052 mmol, 76% yield) as a white powder. $^1$H NMR (500 MHz, DMSO-d6) δ=9.46 (s, 1H), 8.35 (s, 1H), 7.70 (d, J=8.80 Hz, 1H), 7.21-7.34 (m, 3H), 7.09-7.17 (m, 1H), 7.05 (d, J=12.72 Hz, 1H), 6.64 (s, 1H), 3.73-3.79 (m, 4H), 3.52 (s, 3H), 3.00-3.10 (m, 6H), 2.72-2.89 (m, 2H), 2.43 (t, J=10.27 Hz, 1H), 2.35 (d, J=6.36 Hz, 1H), 2.21 (br. s., 4H), 0.98 (d, J=6.36 Hz, 3H); LCMS [M+H]+ 588.4.

Example 479: N-[4-fluoro-5-(2-morpholin-4-ylpyrimidin-5-yl)-2-[(3R,5S)-3,4,4,5-tetramethylpiperazin-4-ium-1-yl]phenyl]-6-oxo-4-(trifluoromethyl)-1H-pyridine-3-carboxamide

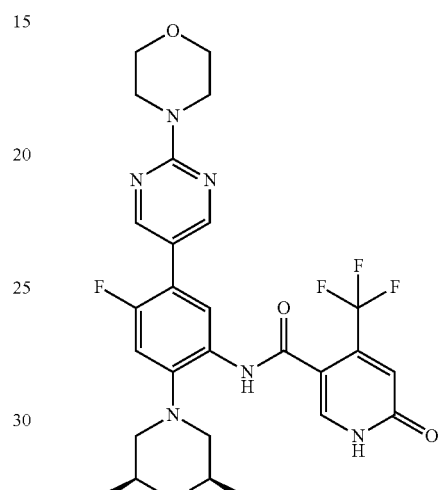

To a suspension of N-(4-fluoro-5-(2-morpholinopyrimidin-5-yl)-2-((3R,5S)-3,4,5-trimethylpiperazin-1-yl)phenyl)-6-oxo-4-(trifluoromethyl)-1,6-dihydropyridine-3-carboxamide (60 mg, 0.102 mmol) in acetonitrile (3 ml) was added iodomethane (8.24 µl, 0.132 mmol) at room temperature. The reaction mixture was stirred for 15 minutes at room temperature and then DCM (3.00 mL) was added to dissolve all the product. After 30 minutes, MeI (60 µl, 0.961 mmol) was added at room temperature and stirred for overnight. The solvents were removed under vacuum and the product was triturated in Et$_2$O. After filtration the pale yellow powder gave the (2R,6S)-4-(5-fluoro-4-(2-morpholinopyrimidin-5-yl)-2-(6-oxo-4-(trifluoromethyl)-1,6-dihydropyridine-3-carboxamido)phenyl)-1,1,2,6-tetramethylpiperazin-1-ium, Iodide, I-[BC] (61.2 mg, 0.079 mmol, 77% yield). $^1$H NMR (500 MHz, DMSO-d6) δ=12.60 (br. s., 1H), 9.54 (s, 1H), 8.54 (s, 2H), 7.99 (d, J=8.56 Hz, 2H), 7.33 (d, J=11.98 Hz, 1H), 6.84 (s, 1H), 3.82-3.90 (m, 2H), 3.74-3.78 (m, 5H), 3.66-3.70 (m, 5H), 3.14-3.27 (m, 5H), 3.11 (s, 3H), 2.88 (s, 3H), 1.34 (d, J=6.60 Hz, 7H); LCMS [M]+604.5.

Example 480: 4-(difluoromethyl)-N-[4-fluoro-2-[(3R)-3,4-dimethylpiperazin-1-yl]-5-[2-[(2R)-2-methylmorpholin-4-yl]pyrimidin-5-yl]phenyl]-1-methyl-6-oxopyridine-3-carboxamide Example 481: 4-(difluoromethyl)-N-[4-fluoro-5-[2-[(2R)-2-methylmorpholin-4-yl]pyrimidin-5-yl]-2-[(3S,5R)-3,4,5-trimethylpiperazin-1-yl]phenyl]-1-methyl-6-oxopyridine-3-carboxamide

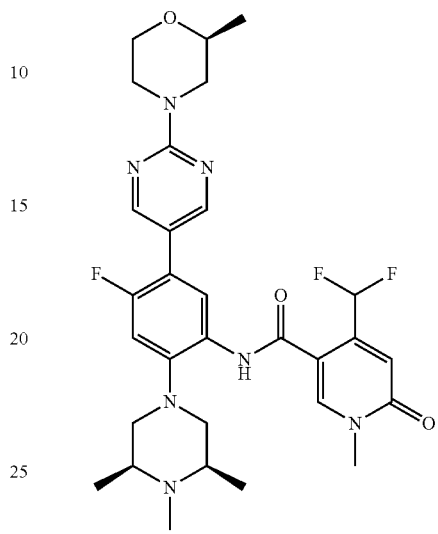

The title compound (off white solid, 12.9 mg, 21%) was prepared using a procedure similar to that in Example 29 using crude (S)-(2-(2-methylmorpholino)pyrimidin-5-yl)boronic acid (0.2 mmol) and N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (52 mg, 0.1 mmol). $^1$H NMR (500 MHz, METHANOL-d4) δ=8.55 (s, 2H), 8.26 (s, 1H), 7.91 (d, J=8.3 Hz, 1H), 7.11 (d, J=12.0 Hz, 1H), 6.94 (s, 1H), 4.64-4.52 (m, 2H), 3.98 (dd, J=2.6, 11.4 Hz, 1H), 3.68-3.58 (m, 5H), 3.12-3.03 (m, 3H), 2.76-2.54 (m, 5H), 2.41 (br s, 3H), 1.26-1.23 (m, 3H), 1.19 (br d, J=4.3 Hz, 6H); LCMS [M+H]$^+$ 618.5.

Example 482: N-(cyclopropylmethyl)-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-1,3-thiazole-4-carboxamide

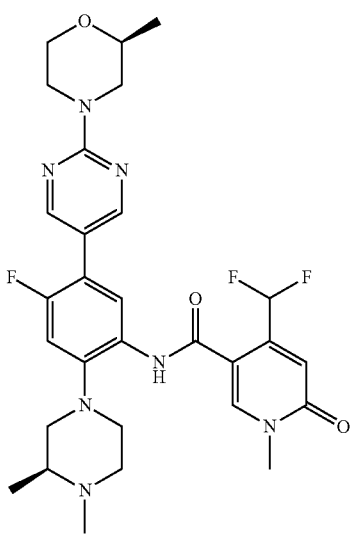 [SMILES: C[C@H]1CN(c2ncc(-c3cc(NC(=O)c4cn(C)c(=O)cc4C(F)F)c(N4CCN(C)[C@@H](C)C4)cc3F)cn2)CCO1]

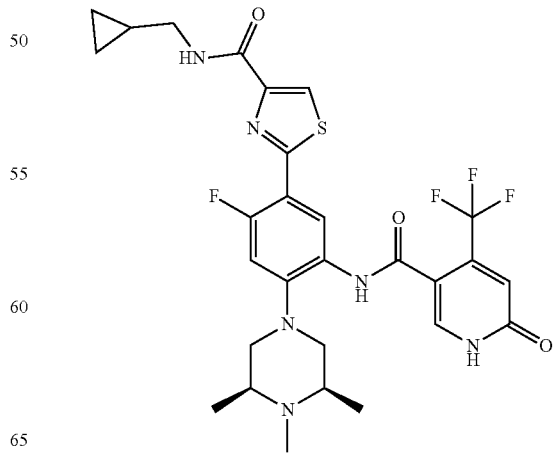

The title compound (light beige solid, 31.6 mg, 52%) was prepared by a procedure similar to that of Example 40 using crude (S)-(2-(2-methylmorpholino)pyrimidin-5-yl)boronic acid (0.2 mmol) and (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (50.5 mg, 0.1 mmol). $^1$H NMR (500 MHz, METHANOL-d4) δ=8.56 (s, 2H), 8.27 (s, 1H), 7.92 (d, J=8.3 Hz, 1H), 7.12 (d, J=12.1 Hz, 1H), 6.95 (s, 1H), 4.65-4.54 (m, 2H), 4.01-3.96 (m, 1H), 3.69-3.59 (m, 5H), 3.15-3.04 (m, 3H), 3.01-2.89 (m, 2H), 2.77-2.70 (m, 1H), 2.64-2.50 (m, 2H), 2.43 (br s, 1H), 2.38 (s, 3H), 1.25 (d, J=6.2 Hz, 3H), 1.14 (d, J=6.4 Hz, 3H); LCMS [M+H]$^+$ 604.5.

Step 1: 2-bromo-N-(cyclopropylmethyl)thiazole-4-carboxamide

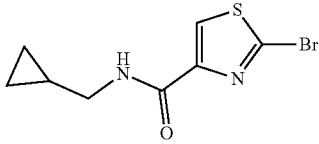 [SMILES: O=C(NCC1CC1)c1csc(Br)n1]

2-Bromo-4-thiazolecarboxylic acid (0.10 g, 0.48 mmol) was activated with HATU (0.27 g, 0.72 mmol) and N,N-diisopropylethylamine (0.13 mL, 0.72 mmol) in DMF (1 mL) at room temperature. The solution of activated acid was added to a stirring solution of aminomethylcyclopropane (0.06 mL, 0.72 mmol) in DMF (1 mL) at room temperature. After stirring at room temperature for 18 h the DMF was removed under reduced pressure. The residue was partitioned between DCM (5 mL) and saturated aqueous NaHCO₃ (5 mL). The decanted organic layer was concentrated onto celite and purified by flash chromatography [EtOAc/hexanes] to afford 2-bromo-N-(cyclopropylmethyl)thiazole-4-carboxamide (0.10 g, 82%). LCMS [M+H]⁺: 261.2.

Step 2: N-(cyclopropylmethyl)-2-(2-fluoro-5-nitro-4-(cis-3,4,5-trimethylpiperazin-1-yl)phenyl)thiazole-4-carboxamide

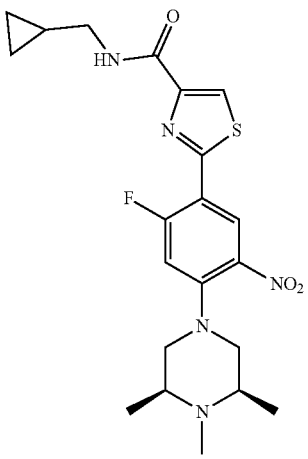 [SMILES: C[C@@H]1CN(c2cc(F)c(-c3nc(C(=O)NCC4CC4)cs3)cc2[N+](=O)[O-])C[C@H](C)N1C]

A reaction vial was charged with a mixture of cis-4-(5-fluoro-2-nitro-4-(4,4,5,5-tetramethyl-1,3,2-dioxaborolan-2-yl)phenyl)-1,2,6-trimethylpiperazine (0.050 g, 0.13 mmol), 2-bromo-N-(cyclopropylmethyl)thiazole-4-carboxamide (0.040 g, 0.14 mmol) and tetrakis(triphenylphosphine)palladium(0) (0.015 g, 0.013 mmol). The vial was sealed with a septum then evacuated and backfilled with nitrogen. 1,4-Dioxane (3 mL) and 2 M aqueous sodium carbonate (1.0 mL) were added via syringe and the vial was evacuated and backfilled an additional time. The reaction was heated in an aluminum block at 95° C. for 5 h. After cooling to room temperature the reaction mixture was concentrated onto celite and purified by flash chromatography [0.5-9.5% MeOH/DCM+0.5% NH₄OH] to afford N-(cyclopropylmethyl)-2-(2-fluoro-5-nitro-4-(cis-3,4,5-trimethylpiperazin-1-yl)phenyl)thiazole-4-carboxamide (0.026 g, 45%). LCMS [M+H]+: 448.4.

Step 3: 2-(5-amino-2-fluoro-4-(cis-3,4,5-trimethylpiperazin-1-yl)phenyl)-N-(cyclopropylmethyl)thiazole-4-carboxamide

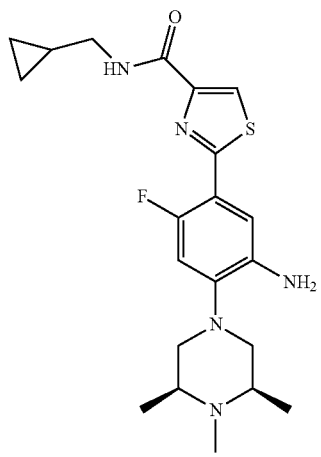 [SMILES: C[C@@H]1CN(c2cc(F)c(-c3nc(C(=O)NCC4CC4)cs3)cc2N)C[C@H](C)N1C]

A solution of N-(cyclopropylmethyl)-2-(2-fluoro-5-nitro-4-(cis-3,4,5-trimethylpiperazin-1-yl)phenyl)thiazole-4-carboxamide (0.026 g, 0.058 mmol) and tin(II) chloride (0.033 g, 0.17 mmol) in a mixture of EtOH (3 mL) and MeOH (1 mL) was heated to 75° C. for 3 h. After cooling to room temperature the reaction mixture was concentrated onto celite and purified by flash [0.5-10% MeOH/DCM+0.5% NH₄OH] to afford 2-(5-amino-2-fluoro-4-(cis-3,4,5-trimethylpiperazin-1-yl)phenyl)-N-(cyclopropylmethyl)thiazole-4-carboxamide (0.017 g, 70%). LCMS [M+H]+: 418.4.

Step 4: N-(cyclopropylmethyl)-2-(2-fluoro-5-(6-oxo-4-(trifluoromethyl)-1,6-dihydropyridine-3-carboxamido)-4-(cis-3,4,5-trimethylpiperazin-1-yl)phenyl)thiazole-4-carboxamide

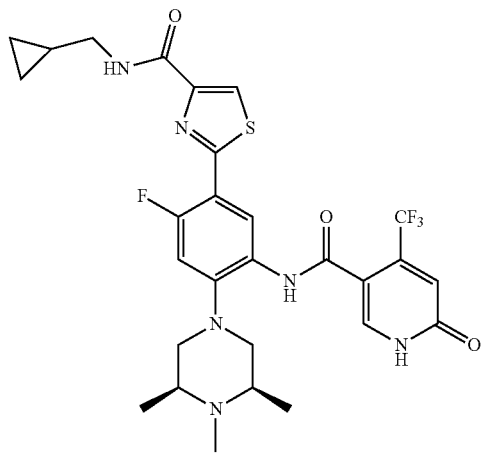 [SMILES: C[C@@H]1CN(c2cc(F)c(-c3nc(C(=O)NCC4CC4)cs3)cc2NC(=O)c2c[nH]c(=O)cc2C(F)(F)F)C[C@H](C)N1C]

4-(Trifluoromethyl)-6-(2-(trimethylsilyl)ethoxy)nicotinic acid (0.025 g, 0.081 mmol) was activated with HATU (0.031 g, 0.081 mmol) and N,N-diisopropylethylamine (0.014 mL, 0.081 mmol) in DMF (0.5 mL) at room temperature. The solution of activated acid was added to a solution of 2-(5-amino-2-fluoro-4-(cis-3,4,5-trimethylpiperazin-1-yl)phenyl)-N-(cyclopropylmethyl)thiazole-4-carboxamide (0.017 g, 0.041 mmol) in DMF (0.5 mL) and the reaction was heated to 50° C. for 18 h. After cooling to room temperature the reaction mixture was concentrated onto celite and purified by flash chromatography [0.5-10% MeOH/DCM+0.5% NH₄OH]. The silyloxy protected pyridine intermediate was dissolved in DCM (2 mL) and treated with TFA (0.7 mL) at room temperature. After stirring for 18 h the volatiles were removed under a stream of air and the product was isolated with a catch and release protocol using a SCX2 silica cartridge. The product was further purified by reverse phase chromatography [5-95% MeCN/10 mM NH₄HCO₃] to afford the title compound N-(cyclopropylmethyl)-2-(2-fluoro-5-(6-oxo-4-(trifluoromethyl)-1,6-dihydropyridine-3-carboxamido)-4-(cis-3,4,5-trimethylpiperazin-1-yl)phenyl)thiazole-4-carboxamide (0.008 g, 32%). ¹H NMR (500 MHz, DMSO-d6) δ=12.56 (br s, 1H), 9.71 (s, 1H), 8.44 (br t, J=5.9 Hz, 1H), 8.37-8.28 (m, 2H), 8.00 (s, 1H), 7.10 (d, J=13.1 Hz, 1H), 6.83 (s, 1H), 3.22-3.12 (m, 6H), 2.34 (br d, J=6.0 Hz, 2H), 2.19 (s, 3H), 1.10-1.04 (m, 1H), 1.01 (br d, J=5.9 Hz, 6H), 0.46-0.41 (m, 2H), 0.29-0.23 (m, 2H); LCMS [M+H]+: 607.3.

Example 483: N-(cyclopropylmethyl)-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-N-methyl-1,3-thiazole-4-carboxamide

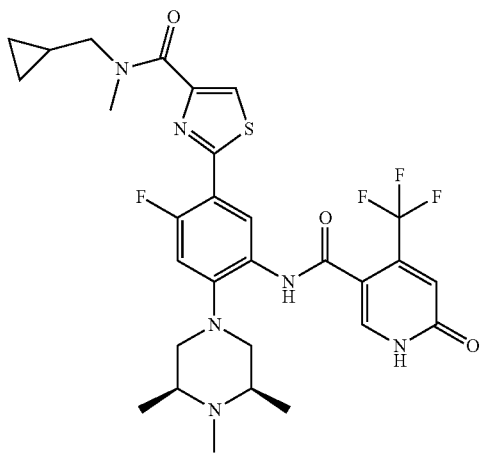 [SMILES: C[C@@H]1CN(c2cc(F)c(-c3nc(C(=O)N(C)CC4CC4)cs3)cc2NC(=O)c2c[nH]c(=O)cc2C(F)(F)F)C[C@H](C)N1C]

The title compound was prepared similar to the procedure described above for the preparation of Example 482 using 1-cyclopropyl-N-methylmethanamine in place of aminomethylcyclopropane in Step 1. ¹H NMR (500 MHz, DMSO-d6) δ=9.67-9.59 (m, 1H), 8.42-8.33 (m, 1H), 8.14 (s, 1H), 7.97-7.85 (m, 1H), 7.11 (br d, J=12.7 Hz, 1H), 6.81 (s, 1H), 3.19-3.11 (m, 4H), 3.07 (s, 3H), 2.39-2.32 (m, 2H), 2.19 (s, 3H), 1.17-1.10 (m, 1H), 1.00 (br d, J=6.7 Hz, 6H), 0.53-0.41 (m, 2H), 0.29 (br s, 1H), 0.19-0.10 (m, 1H); LCMS [M+H]⁺: 621.5.

Example 484: N-Cyclohexyl-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-1,3-thiazole-4-carboxamide

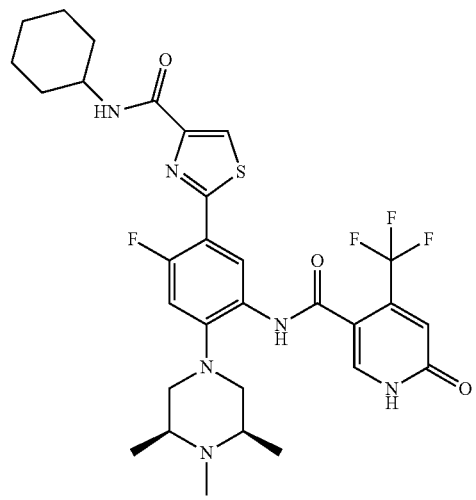 [SMILES: C[C@@H]1CN(c2cc(F)c(-c3nc(C(=O)NC4CCCCC4)cs3)cc2NC(=O)c2c[nH]c(=O)cc2C(F)(F)F)C[C@H](C)N1C]

The title compound was prepared similar to the procedure described above for the preparation of Example 482 using cyclohexylamine in place of aminomethylcyclopropane in Step 1. ¹H NMR (500 MHz, DMSO-d6) δ=12.60 (br s, 1H), 9.71 (s, 1H), 8.36-8.28 (m, 2H), 8.00-7.94 (m, 2H), 7.09 (d, J=13.3 Hz, 1H), 6.83 (s, 1H), 3.85-3.71 (m, 2H), 3.16 (br d, J=11.1 Hz, 2H), 2.33 (br s, 2H), 2.19 (s, 3H), 1.86-1.79 (m, 2H), 1.71 (br d, J=12.5 Hz, 2H), 1.59 (br d, J=13.2 Hz, 1H), 1.44-1.26 (m, 5H), 1.20-1.10 (m, 3H), 1.01 (d, J=6.0 Hz, 6H); LCMS [M+H]+: 635.5.

Example 485: N-cyclohexyl-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-N-methyl-1,3-thiazole-4-carboxamide

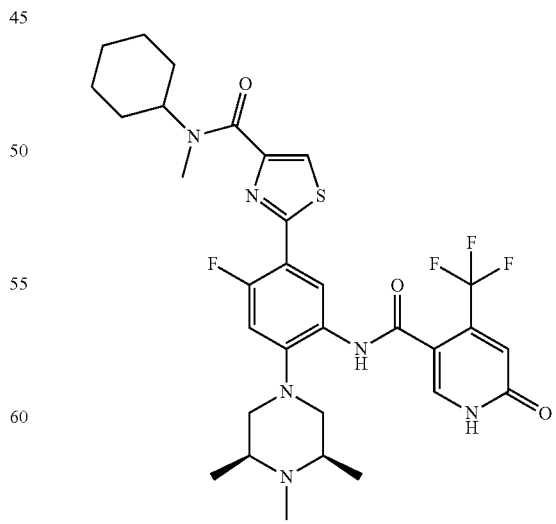

The title compound was prepared similar to the procedure described above for the preparation of Example 482 using N-methylcyclohexylamine in place of aminomethylcyclopropane in Step 1. ¹H NMR (500 MHz, DMSO-d6) δ=9.64 (br s, 1H), 8.43-8.31 (m, 1H), 8.17-8.08 (m, 1H), 7.99-7.92 (m, 1H), 7.87 (br s, 1H), 7.17-6.99 (m, 1H), 6.82 (s, 1H), 4.40-4.28 (m, 1H), 4.00-3.86 (m, 1H), 3.15 (br d, J=10.8 Hz, 3H), 2.89 (s, 3H), 2.36 (br d, J=1.6 Hz, 3H), 2.20 (s, 3H), 1.78 (br d, J=8.8 Hz, 3H), 1.73-1.62 (m, 4H), 1.62-1.51 (m, 3H), 1.02 (br d, J=5.7 Hz, 6H); LCMS [M+H]+: 649.5.

Example 486: N-[4-fluoro-5-[4-(morpholine-4-carbonyl)-1,3-thiazol-2-yl]-2-[(3R,5S)-3,4,5-trimethylpiperazin-1-yl]phenyl]-6-oxo-4-(trifluoromethyl)-1H-pyridine-3-carboxamide

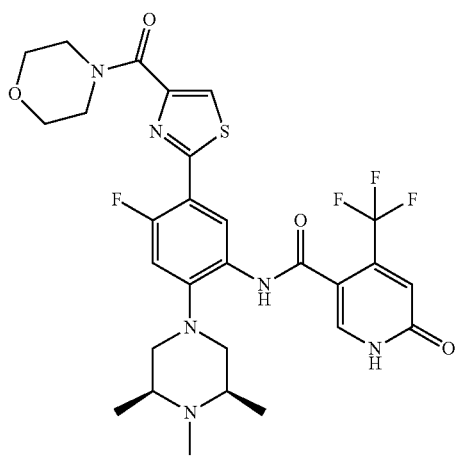 [SMILES: C[C@@H]1CN(c2cc(F)c(-c3nc(C(=O)N4CCOCC4)cs3)cc2NC(=O)c2c[nH]c(=O)cc2C(F)(F)F)C[C@H](C)N1C]

The title compound was prepared similar to the procedure described above for the preparation of Example 482 using morpholine in place of aminomethylcyclopropane in Step 1. ¹H NMR (500 MHz, DMSO-d6) δ=9.64 (s, 1H), 8.40 (d, J=8.2 Hz, 1H), 8.21 (s, 1H), 7.90 (s, 1H), 7.10 (d, J=13.2 Hz, 1H), 6.81 (s, 1H), 3.74-3.64 (m, 8H), 3.14 (br d, J=11.0 Hz, 3H), 2.36 (br t, J=6.8 Hz, 3H), 2.20 (s, 3H), 1.02 (d, J=6.2 Hz, 6H); LCMS [M+H]+: 623.4.

Example 487: N-[4-fluoro-5-[4-(4-methylpiperazine-1-carbonyl)-1,3-thiazol-2-yl]-2-[(3R,5S)-3,4,5-trimethylpiperazin-1-yl]phenyl]-6-oxo-4-(trifluoromethyl)-1H-pyridine-3-carboxamide

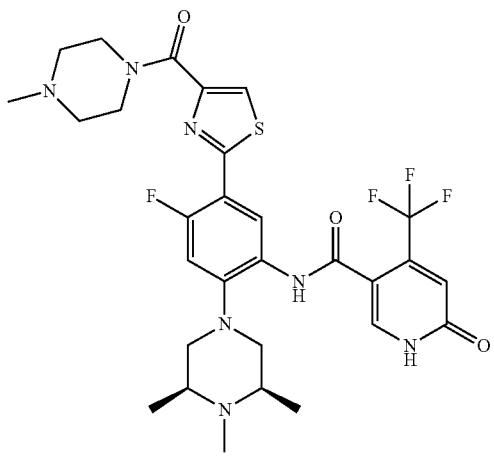 [SMILES: C[C@@H]1CN(c2cc(F)c(-c3nc(C(=O)N4CCN(C)CC4)cs3)cc2NC(=O)c2c[nH]c(=O)cc2C(F)(F)F)C[C@H](C)N1C]

The title compound was prepared similar to the procedure described above for the preparation of Example 482 using 1-methylpiperazine in place of aminomethylcyclopropane in Step 1. ¹H NMR (500 MHz, DMSO-d6) δ=9.65 (s, 1H), 8.41 (d, J=8.1 Hz, 1H), 8.17 (s, 1H), 7.88 (s, 1H), 7.10 (d, J=13.1 Hz, 1H), 6.81 (s, 1H), 3.66 (br s, 4H), 3.14 (br d, J=11.0 Hz, 2H), 2.37 (br s, 5H), 2.20 (br s, 6H), 1.02 (d, J=6.1 Hz, 6H); LCMS [M+H]+: 636.5.

Example 488: (3-methyloxetan-3-yl) 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate

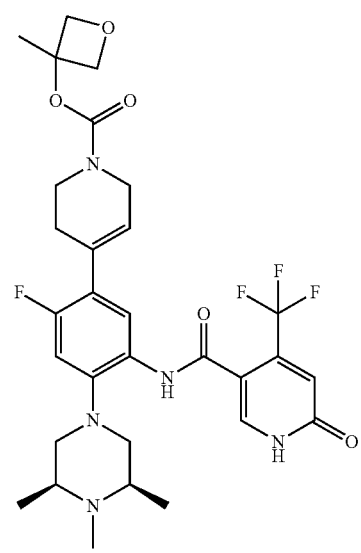 [SMILES: C[C@@H]1CN(c2cc(F)c(C3=CCN(C(=O)OC4(C)COC4)CC3)cc2NC(=O)c2c[nH]c(=O)cc2C(F)(F)F)C[C@H](C)N1C]

The procedure followed was similar to that of Example 472 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (35 mg, 0.069 mmol) and 3-methyloxetan-3-yl (4-nitrophenyl) carbonate (20.08 mg, 0.079 mmol) to give the title compound (29 mg, 64% yield). ¹H NMR (500 MHz, METHANOL-d4) δ=7.85-7.81 (m, 1H), 7.70-7.61 (m, 1H), 6.88-6.82 (m, 1H), 6.81-6.76 (m, 1H), 5.94-5.85 (m, 1H), 4.72-4.67 (m, 2H), 4.42-4.37 (m, 2H), 4.10-3.93 (m, 2H), 3.65-3.49 (m, 2H), 2.95-2.89 (m, 2H), 2.49-2.39 (m, 6H), 2.28-2.24 (m, 3H), 1.66-1.62 (m, 3H), 1.05 (d, J=6.0 Hz, 6H); LCMS [M+H]+ 622.5.

Example 489: (3-methyloxetan-3-yl) 5-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-3,6-dihydro-2H-pyridine-1-carboxylate

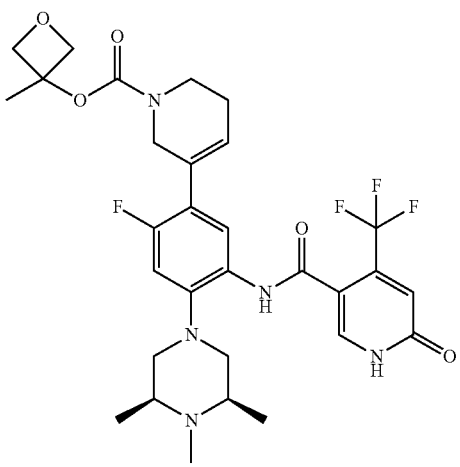 [SMILES: C[C@@H]1CN(c2cc(F)c(C3=CCCN(C(=O)OC4(C)COC4)C3)cc2NC(=O)c2c[nH]c(=O)cc2C(F)(F)F)C[C@H](C)N1C]

The procedure followed was similar to Example 472 using N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) 3-methyloxetan-3-yl (4-nitrophenyl) carbonate (17.96 mg, 0.071 mmol) to give the title compound (23 mg, 60% yield). $^1$H NMR (500 MHz, METHANOL-d4) δ=7.88-7.80 (m, 1H), 7.70-7.59 (m, 1H), 6.89-6.82 (m, 1H), 6.82-6.76 (m, 1H), 6.05-5.96 (m, 1H), 4.72-4.66 (m, 2H), 4.41-4.36 (m, 2H), 4.20-4.10 (m, 2H), 3.57-3.46 (m, 2H), 2.95-2.89 (m, 2H), 2.53-2.39 (m, 4H), 2.28-2.23 (m, 5H), 1.65-1.61 (m, 3H), 1.05 (d, J=6.0 Hz, 6H); LCMS [M+H]+ 622.7.

Example 490: (3-methyloxetan-3-yl) 3-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-2,5-dihydropyrrole-1-carboxylate

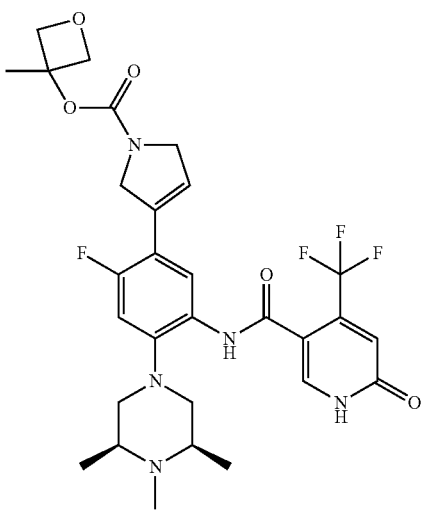 [SMILES: C[C@@H]1CN(c2cc(F)c(C3=CCN(C(=O)OC4(C)COC4)C3)cc2NC(=O)c2c[nH]c(=O)cc2C(F)(F)F)C[C@H](C)N1C]

The procedure followed was similar to Example 472 using N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (34 mg, 0.069 mmol) and 3-methyloxetan-3-yl (4-nitrophenyl) carbonate (20.93 mg, 0.083 mmol) to give the title compound (29 mg, 66% yield). $^1$H NMR (500 MHz, METHANOL-d4) δ=7.89-7.82 (m, 1H), 7.75-7.65 (m, 1H), 6.93-6.87 (m, 1H), 6.83-6.78 (m, 1H), 6.28-6.21 (m, 1H), 4.75-4.69 (m, 2H), 4.51-4.36 (m, 4H), 4.32-4.19 (m, 2H), 2.98-2.90 (m, 2H), 2.53-2.45 (m, 2H), 2.45-2.36 (m, 2H), 2.29-2.24 (m, 3H), 1.68-1.61 (m, 3H), 1.07-1.02 (m, 6H); LCMS [M+H]+ 608.6

Example 491: N-[4-fluoro-5-[5-(morpholin-4-ylmethyl)thiophen-2-yl]-2-[(3R,5S)-3,4,5-trimethylpiperazin-1-yl]phenyl]-6-oxo-4-(trifluoromethyl)-1H-pyridine-3-carboxamide The title compound (62.5 mg, 54% yield) was prepared by a method similar to that of Example 39 using N-(5-bromo-4-fluoro-2-((3R,5S)-3,4,5-trimethylpiperazin-1-yl)phenyl)-4-(trifluoromethyl)-6-(2-(trimethylsilyl)ethoxy)nicotinamide (62.27 mg, 0.103 mmol) and 5-((morpholino)methyl)-2-thiopheneboronic acid pinacol ester (47.7 mg, 0.154 mmol). $^1$H NMR (500 MHz, MeOD) δ 8.14 (d, J=8.1 Hz, 1H), 7.95 (s, 1H), 7.30 (d, J=3.3 Hz, 1H), 7.04 (d, J=12.5 Hz, 1H), 6.98 (d, J=3.5 Hz, 1H), 6.91 (s, 1H), 3.75 (s, 2H), 3.72-3.70 (m, 4H), 3.05 (d, J=11.2 Hz, 2H), 2.61 (t, J=11.1 Hz, 2H), 2.53 (s, 6H), 2.37 (s, 3H), 1.16 (d, J=6.1 Hz, 6H); LCMS [M+1]$^+$=608.45.

Example 492: N-[4-fluoro-2-[(3R,5S)-3,4,5-trimethylpiperazin-1-yl]-5-thiophen-2-ylphenyl]-6-oxo-4-(trifluoromethyl)-1H-pyridine-3-carboxamide

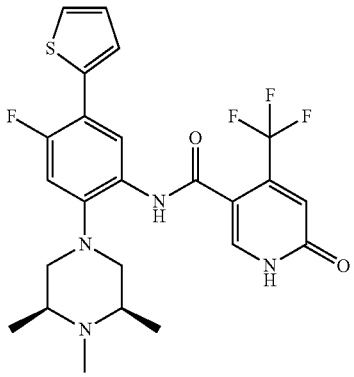

The title compound (50.7 mg, 32% yield) was prepared using a similar procedure to Example 39 using N-(5-bromo-4-fluoro-2-((3R,5S)-3,4,5-trimethylpiperazin-1-yl)phenyl)-4-(trifluoromethyl)-6-(2-(trimethylsilyl)ethoxy)nicotinamide (60.4 mg, 0.100 mmol) and thiophene-2-boronic acid (19.2 mg, 0.150 mmol). $^1$H NMR (500 MHz, MeOD) δ 8.16 (d, J=8.1 Hz, 1H), 7.96 (s, 1H), 7.45 (d, J=4.8 Hz, 2H), 7.12 (t, J=4.3 Hz, 1H), 7.05 (d, J=12.5 Hz, 1H), 6.91 (s, 1H), 3.05 (d, J=11.3 Hz, 2H), 2.61 (t, J=11.1 Hz, 2H), 2.54 (d, J=6.3 Hz, 2H), 2.37 (s, 3H), 1.16 (d, J=6.1 Hz, 6H); LCMS [M+1]$^+$=509.14.

Example 493: N-[4-fluoro-2-[(3R,5S)-3,4,5-trimethylpiperazin-1-yl]-5-thiophen-3-ylphenyl]-6-oxo-4-(trifluoromethyl)-1H-pyridine-3-carboxamide

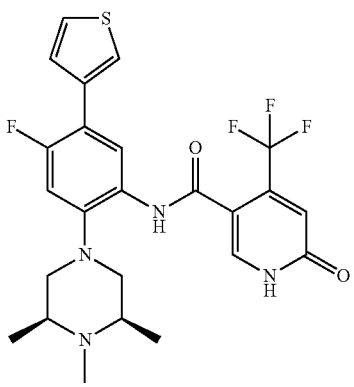

The title compound (52.1 mg, 29% yield) was prepared by a similar procedure to that of Example 39 using N-(5-bromo-4-fluoro-2-((3R,5S)-3,4,5-trimethylpiperazin-1-yl)phenyl)-4-(trifluoromethyl)-6-(2-(trimethylsilyl)ethoxy)nicotinamide (62 mg, 0.102 mmol) and 3-thienylboronic acid (19.65 mg, 0.154 mmol). $^1$H NMR (500 MHz, MeOD) δ 8.08 (d, J=8.2 Hz, 1H), 7.96 (s, 1H), 7.68-7.65 (m, 1H), 7.49 (dd, J=5.0, 3.0 Hz, 1H), 7.43 (d, J=5.1 Hz, 1H), 7.04 (d, J=12.4 Hz, 1H), 6.91 (s, 1H), 3.06 (d, J=10.2 Hz, 2H), 2.65-2.57 (m, 4H), 2.40 (s, 3H), 1.17 (d, J=5.7 Hz, 6H); LCMS [M+1]$^+$=509.29.

Example 494: N-[4-fluoro-5-[5-(morpholin-4-ylmethyl)thiophen-3-yl]-2-[(3R,5S)-3,4,5-trimethylpiperazin-1-yl]phenyl]-6-oxo-4-(trifluoromethyl)-1H-pyridine-3-carboxamide

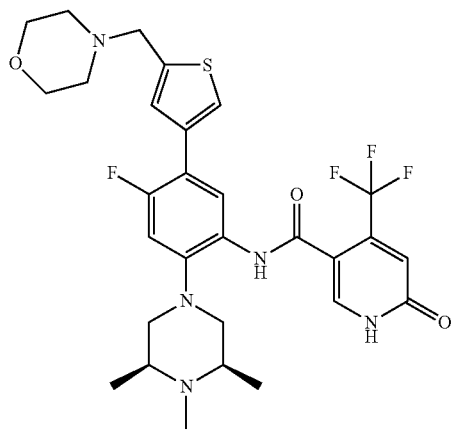 [SMILES: C[C@@H]1CN(c2cc(F)c(-c3csc(CN4CCOCC4)c3)cc2NC(=O)c2c[nH]c(=O)cc2C(F)(F)F)C[C@H](C)N1C]

The title compound (61.6 mg, 23% yield) was prepared by a similar procedure to that described in Example 39 using N-(5-bromo-4-fluoro-2-((3R,5S)-3,4,5-trimethylpiperazin-1-yl)phenyl)-4-(trifluoromethyl)-6-(2-(trimethylsilyl)ethoxy)nicotinamide (61.40 mg, 0.101 mmol) and 2-(morpholin-4-ylmethyl)thiophene-4-boronic acid, pinacol ester (47.0 mg, 0.152 mmol). $^1$H NMR (500 MHz, MeOD) δ 8.06 (d, J=8.0 Hz, 1H), 7.96 (s, 1H), 7.59 (s, 1H), 7.32 (s, 1H), 7.03 (d, J=12.5 Hz, 1H), 6.91 (s, 1H), 3.77 (s, 2H), 3.72-3.70 (m, 4H), 3.05 (d, J=11.1 Hz, 2H), 2.64-2.59 (m, 2H), 2.54 (s, 6H), 2.38 (s, 3H), 1.16 (d, J=5.9 Hz, 6H); LCMS HSS [M+1]$^+$=608.45.

Example 495: N-[4-fluoro-5-(2-morpholin-4-ylpyrimidin-5-yl)-2-[(3R)-3,4-dimethylpiperazin-1-yl]phenyl]-6-oxo-5-(trifluoromethyl)-1H-pyridine-3-carboxamide

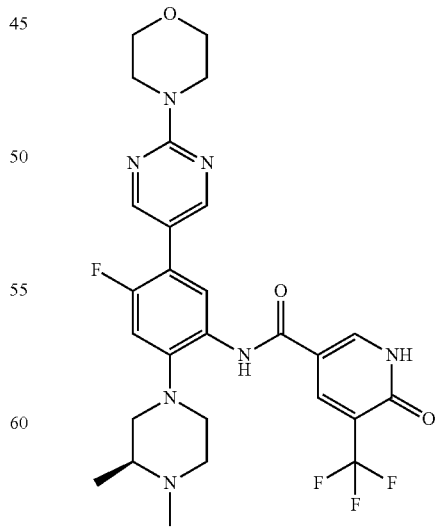

In a 5 mL microwave vial to a suspension of 6-oxo-5-(trifluoromethyl)-1,6-dihydropyridine-3-carboxylic acid (114 mg, 0.553 mmol) in pyridine, anhydrous (671 µl, 8.29 mmol) was added slowly diethyl chlorophosphate (90 µl, 0.622 mmol) at RT in an atmosphere of nitrogen. The reaction mixture was stirred at rt for 2 h. The suspension turned into a solution and then into a suspension again. To this mixture (S)-2-(3,4-dimethylpiperazin-1-yl)-4-fluoro-5-(2-morpholinopyrimidin-5-yl)aniline (53.4 mg, 0.138 mmol) was added and the reaction was heated at 70° C. for 3 h. After completion, pyridine was removed in vacuo and the residue partitioned between dichloromethane (3 mL) and saturated sodium bicarbonate solution (3 mL). The suspension was stirred for 10 min. The organic layer was separated, and dried over anhydrous $Na_2SO_4$. The solvent was evaporated in vacuo yielding the crude product which was purified by flash column chromatography on silica gel (0-100%, 89% $CH_2Cl_2$, 10% MeOH, 1% $NH_4Ac/CH_2Cl_2$) to afford the title compound.

Example 496: N-(cyclopropylmethyl)-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-1,3-thiazole-5-carboxamide

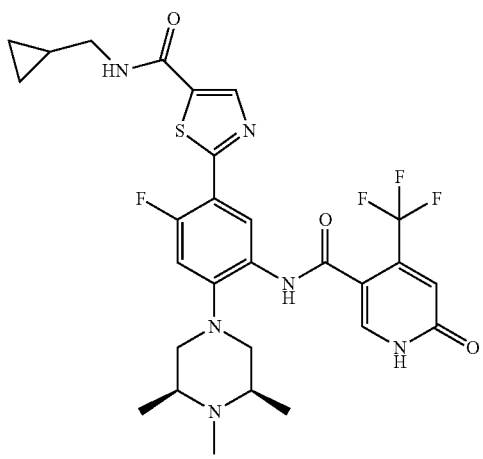 [SMILES: C[C@@H]1CN(c2cc(F)c(-c3ncc(C(=O)NCC4CC4)s3)cc2NC(=O)c2c[nH]c(=O)cc2C(F)(F)F)C[C@H](C)N1C]

The title compound was prepared similar to the procedure described for the preparation of Example 482 using 2-bromo-5-thiazolecarboxylic acid in place of 2-bromo-4-thiazolecarboxylic acid in Step 1. $^1$H NMR (500 MHz, DMSO-d6) δ=9.50 (br s, 1H), 8.84 (t, J=5.6 Hz, 1H), 8.55-8.47 (m, 2H), 7.99 (s, 1H), 7.12 (d, J=13.2 Hz, 1H), 6.67 (br s, 1H), 3.17-3.10 (m, 5H), 2.39-2.30 (m, 3H), 2.19 (s, 3H), 1.01 (d, J=6.1 Hz, 6H), 0.49-0.43 (m, 2H), 0.24 (q, J=4.6 Hz, 2H); LCMS [M+H]+: 607.5.

Example 497: N-(cyclopropylmethyl)-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-N-methyl-1,3-thiazole-5-carboxamide

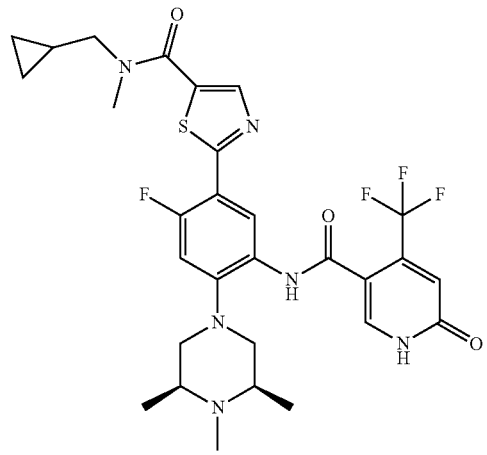 [SMILES: C[C@@H]1CN(c2cc(F)c(-c3ncc(C(=O)N(C)CC4CC4)s3)cc2NC(=O)c2c[nH]c(=O)cc2C(F)(F)F)C[C@H](C)N1C]

The title compound was prepared similar to the procedure described above for the preparation of Example 482 using 1-cyclopropyl-N-methylmethanamine in place of aminomethylcyclopropane in Step 1. $^1$H NMR (500 MHz, DMSO-d6) δ=9.53-9.43 (m, 1H), 8.53 (d, J=8.2 Hz, 1H), 8.39-8.18 (m, 1H), 7.98 (s, 1H), 7.12 (d, J=13.2 Hz, 1H), 6.65 (br s, 1H), 6.56 (s, 1H), 3.15 (br d, J=11.4 Hz, 5H), 2.41-2.33 (m, 3H), 2.21 (s, 3H), 1.11-1.06 (m, 1H), 1.03 (d, J=6.1 Hz, 6H), 0.55-0.49 (m, 2H), 0.32-0.22 (m, 2H); LCMS [M+H]+: 621.4.

Example 498: N-cyclohexyl-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-1,3-thiazole-5-carboxamide

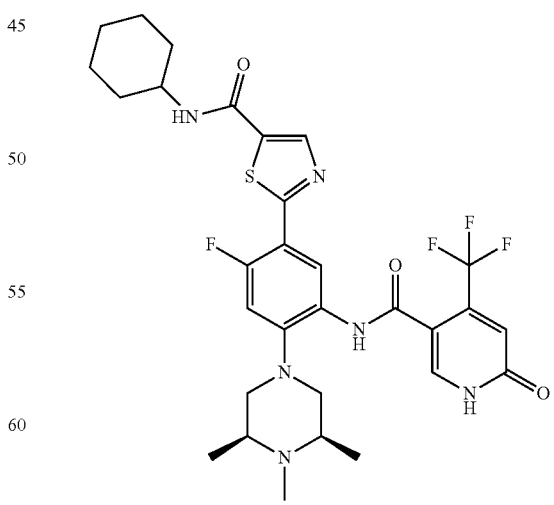

The title compound was prepared similar to the procedure described above for the preparation of Example 482 using cyclohexylamine in place of aminomethylcyclopropane in Step 1. ¹H NMR (500 MHz, DMSO-d6) δ=12.54 (br s, 1H), 9.61 (s, 1H), 8.52-8.41 (m, 3H), 7.95 (s, 1H), 7.11 (d, J=13.2 Hz, 1H), 6.79 (s, 1H), 3.14 (br d, J=11.6 Hz, 2H), 2.39-2.31 (m, 2H), 2.19 (s, 3H), 1.85 (br s, 2H), 1.80-1.71 (m, 2H), 1.61 (br d, J=11.1 Hz, 1H), 1.30 (br t, J=9.5 Hz, 4H), 1.01 (d, J=6.1 Hz, 6H); LCMS [M+H]+: 635.5.

Example 499: N-cyclohexyl-2-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-N-methyl-1,3-thiazole-5-carboxamide

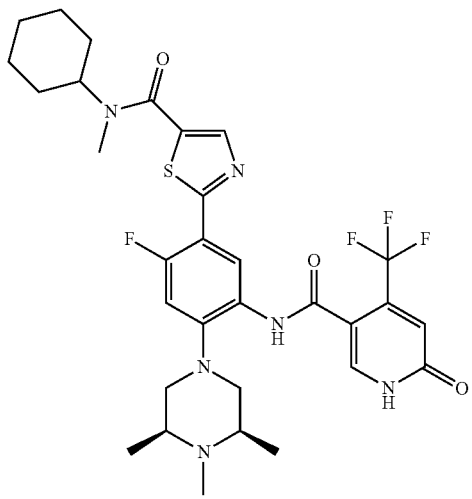 [SMILES: C[C@@H]1CN(c2cc(F)c(-c3ncc(C(=O)N(C)C4CCCCC4)s3)cc2NC(=O)c2c[nH]c(=O)cc2C(F)(F)F)C[C@H](C)N1C]

The title compound was prepared similar to the procedure described above for the preparation of Example 482 using N-methylcyclohexylamine in place of aminomethylcyclopropane in Step 1. ¹H NMR (500 MHz, DMSO-d6) δ=12.49 (br s, 1H), 9.56 (s, 1H), 8.41 (d, J=7.9 Hz, 1H), 8.15 (br s, 1H), 7.85 (s, 1H), 7.04 (d, J=13.1 Hz, 1H), 6.74 (s, 1H), 3.09 (br d, J=11.6 Hz, 2H), 3.03-2.90 (m, 2H), 2.29 (br t, J=7.9 Hz, 3H), 2.13 (s, 3H), 1.76-1.68 (m, 2H), 1.62 (br s, 2H), 1.52 (br s, 3H), 1.29-1.18 (m, 2H), 1.10-1.03 (m, 1H), 0.95 (d, J=6.1 Hz, 6H); LCMS [M+H]+: 649.4.

Example 500: N-[4-fluoro-5-[5-(morpholine-4-carbonyl)-1,3-thiazol-2-yl]-2-[(3R,5S)-3,4,5-trimethylpiperazin-1-yl]phenyl]-6-oxo-4-(trifluoromethyl)-1H-pyridine-3-carboxamide

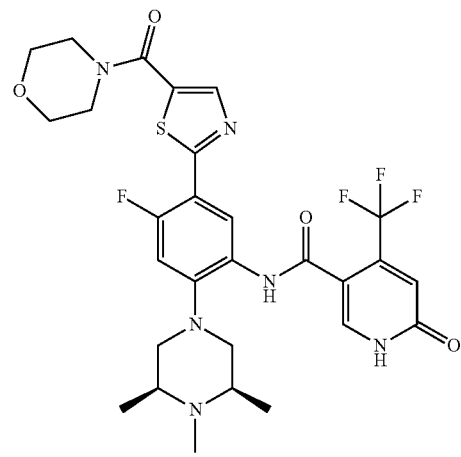 [SMILES: C[C@@H]1CN(c2cc(F)c(-c3ncc(C(=O)N4CCOCC4)s3)cc2NC(=O)c2c[nH]c(=O)cc2C(F)(F)F)C[C@H](C)N1C]

The title compound was prepared similar to the procedure described for the preparation of Example 482 using morpholine in place of aminomethylcyclopropane in Step 1. ¹H NMR (500 MHz, DMSO-d6) δ=12.54 (br s, 1H), 9.63 (s, 1H), 8.46 (d, J=8.1 Hz, 1H), 8.23 (d, J=2.2 Hz, 1H), 7.92 (s, 1H), 7.11 (d, J=13.1 Hz, 1H), 6.80 (s, 1H), 3.70-3.63 (m, 9H), 3.16 (br d, J=11.6 Hz, 2H), 2.38-2.31 (m, 2H), 2.20 (s, 3H), 1.01 (d, J=6.1 Hz, 6H); LCMS [M+H]+: 623.4.

Example 501: N-[4-fluoro-5-[5-(4-methylpiperazine-1-carbonyl)-1,3-thiazol-2-yl]-2-[(3R,5S)-3,4,5-trimethylpiperazin-1-yl]phenyl]-6-oxo-4-(trifluoromethyl)-1H-pyridine-3-carboxamide

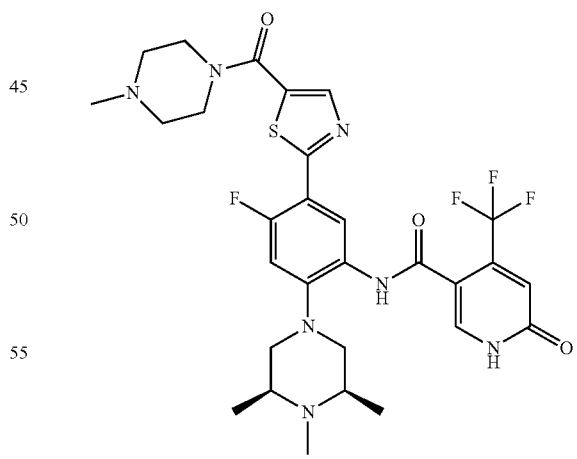

The title compound was prepared similar to the procedure described above for the preparation of Example 482 using 1-methylpiperazine in place of aminomethylcyclopropane in Step 1. ¹H NMR (500 MHz, DMSO-d6) δ=12.59 (br s, 1H), 9.52 (br s, 1H), 8.51 (d, J=8.1 Hz, 1H), 8.21 (d, J=2.2 Hz, 1H), 7.97 (s, 1H), 7.12 (d, J=13.0 Hz, 1H), 6.69 (br d, J=1.0 Hz, 1H), 3.67 (br s, 4H), 3.15 (br d, J=11.2 Hz, 2H), 2.40-2.33 (m, 7H), 2.22 (s, 3H), 2.21 (s, 3H), 1.02 (d, J=6.1 Hz, 6H); LCMS [M+H]+: 636.5.

Example 502: 5-amino-4-fluoro-N-[4-fluoro-5-(2-morpholin-4-ylpyrimidin-5-yl)-2-[(3R,5S)-3,4,5-trimethylpiperazin-1-yl]phenyl]-2-(trifluoromethyl)benzamide

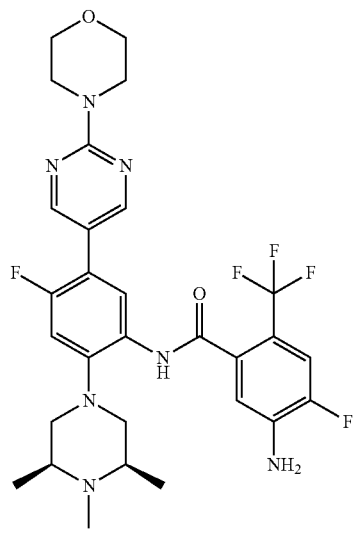 [SMILES: C[C@@H]1CN(c2cc(F)c(-c3cnc(N4CCOCC4)nc3)cc2NC(=O)c2cc(N)c(F)cc2C(F)(F)F)C[C@H](C)N1C]

Step 1: 4-Fluoro-5-nitro-2-(trifluoromethyl)benzoic acid

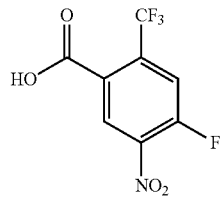

To a solution of 4-fluoro-2-(trifluoromethyl)benzoic acid (0.50 g, 2.4 mmol) in sulphuric acid (4 mL) at 0° C. was added fuming nitric acid (0.11 mL 2.6 mmol). The reaction was warmed to room temperature and stirred for 18 h. An additional equivalent of fuming nitric acid (0.11 mL, 2.6 mmol) was added to the reaction mixture and the reaction was warmed to 45° C. for 4 hours. After cooling to room temperature the mixture was added dropwise to water (25 mL) at 0° C. The mixture was transferred to a separatory funnel and extracted with EtOAc. The combined organics were dried over magnesium sulfate and after removal of the inorganics by filtration the filtrate was concentrated onto celite. Purification by flash chromatography [0.5-10% MeOH/DCM+0.5% NH$_4$OH] afforded 4-fluoro-5-nitro-2-(trifluoromethyl)benzoic acid (0.12 g, 19%). LCMS [M−H]−: 252.0.

Step 2: 4-Fluoro-N-(4-fluoro-5-(2-morpholinopyrimidin-5-yl)-2-(cis-3,4,5-trimethylpiperazin-1-yl)phenyl)-5-nitro-2-(trifluoromethyl)benzamide Thionyl chloride (0.18 mL, 2.5 mmol) was added to a vial containing 4-fluoro-5-nitro-2-(trifluoromethyl)benzoic acid (0.020 g, 0.075 mmol). The resulting suspension was heated at 80° C. for 30 minutes. The reaction mixture was concentrated to dryness and then quickly dried under reduced pressure to afford the crude acid chloride which was used immediately. A solution of 4-fluoro-5-(2-morpholinopyrimidin-5-yl)-2-(cis-3,4,5-trimethylpiperazin-1-yl)aniline (0.020 g, 0.050 mmol) and N,N-diisopropylethylamine (0.030 mL, 0.15 mmol) in DCM (1 mL) at room temperature was treated with a solution of acid chloride prepared above in DCM (1 mL). The reaction was stirred at room temperature for 18 h. The reaction mixture was concentrated directly onto celite and purified by flash chromatography [0.5-10% MeOH/DCM+0.5% NH$_4$OH] to afford 4-fluoro-N-(4-fluoro-5-(2-morpholinopyrimidin-5-yl)-2-(cis-3,4,5-trimethylpiperazin-1-yl)phenyl)-5-nitro-2-(trifluoromethyl)benzamide (0.014 g, 45%). $^1$H NMR (500 MHz, CHLOROFORM-d) δ=8.76 (s, 1H), 8.58 (s, 2H), 8.53 (d, J=8.1 Hz, 1H), 8.36 (d, J=6.8 Hz, 1H), 7.78 (d, J=10.1 Hz, 1H), 7.04 (d, J=11.1 Hz, 1H), 3.90-3.87 (m, 4H), 3.82-3.79 (m, 4H), 2.84 (br d, J=11.1 Hz, 2H), 2.66 (br t, J=10.8 Hz, 2H), 1.26 (s, 3H), 1.14 (d, J=6.2 Hz, 6H).

Step 3: 5-amino-4-fluoro-N-(4-fluoro-5-(2-morpholinopyrimidin-5-yl)-2-(cis-3,4,5-trimethylpiperazin-1-yl)phenyl)-2-(trifluoromethyl)benzamide

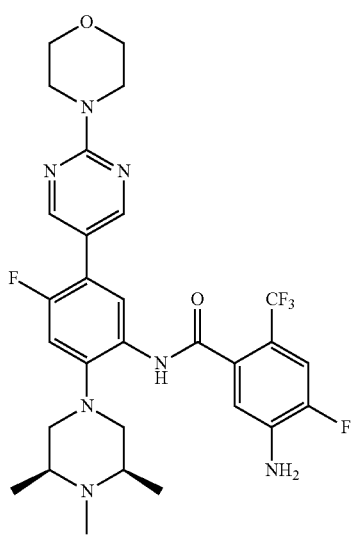 [SMILES: C[C@@H]1CN(c2cc(F)c(-c3cnc(N4CCOCC4)nc3)cc2NC(=O)c2cc(N)c(F)cc2C(F)(F)F)C[C@H](C)N1C]

A mixture of 4-fluoro-N-(4-fluoro-5-(2-morpholinopyrimidin-5-yl)-2-(cis-3,4,5-trimethylpiperazin-1-yl)phenyl)-5-nitro-2-(trifluoromethyl)benzamide (0.014 g, 0.022 mmol) and tin chloride (0.012 g, 0.066 mmol) in EtOH (2 mL) was heated to 75° C. for 1 h. After cooling to room temperature the reaction mixture was concentrated onto celite and purification by flash chromatography [0.5-10% MeOH/DCM+0.5% NH$_4$OH] afforded the title compound 5-amino-4-fluoro-N-(4-fluoro-5-(2-morpholinopyrimidin-5-yl)-2-(cis-3,4,5-trimethylpiperazin-1-yl)phenyl)-2-(trifluoromethyl) benzamide (0.009 g, 69%). $^1$H NMR (500 MHz, METHANOL-d4) δ=8.55 (d, J=0.9 Hz, 2H), 8.06 (d, J=8.3 Hz, 1H), 7.37 (d, J=11.7 Hz, 1H), 7.10 (d, J=12.0 Hz, 1H), 7.01 (d, J=8.3 Hz, 1H), 3.87-3.81 (m, 4H), 3.79-3.74 (m, 4H), 3.00 (br d, J=11.4 Hz, 2H), 2.60 (t, J=11.2 Hz, 2H), 2.43 (dt, J=3.2, 6.6 Hz, 2H), 2.32 (s, 3H), 1.14 (d, J=6.2 Hz, 6H); LCMS [M+H]+: 606.4.

Example 503: N-[5-[1-(6-cyclopropylpyridazin-3-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

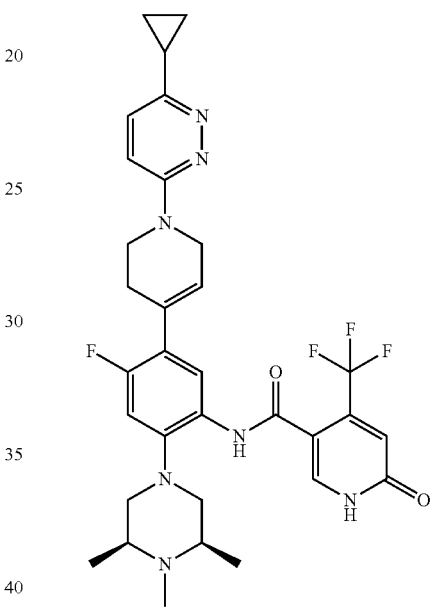

The procedure was similar to that of Example 270 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) and 3-bromo-6-cyclopropyl-pyridazine hydrobromide (23.17 mg, 0.083 mmol) to give the title compound (5 mg, 11% yield). $^1$H NMR (500 MHz, METHANOL-d4) δ=7.86-7.81 (m, 1H), 7.74-7.65 (m, 1H), 7.15-7.05 (m, 2H), 6.88-6.82 (m, 1H), 6.81-6.78 (m, 1H), 6.08-6.01 (m, 1H), 4.13-4.02 (m, 2H), 3.85-3.68 (m, 2H), 2.94-2.89 (m, 2H), 2.57-2.42 (m, 6H), 2.29-2.26 (m, 3H), 2.05-1.97 (m, 1H), 1.07-1.04 (m, 6H), 0.96-0.88 (m, 2H), 0.85-0.80 (m, 2H); LCMS [M+H]+ 626.7.

Example 504: N-[5-[1-(6-ethylpyridazin-3-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

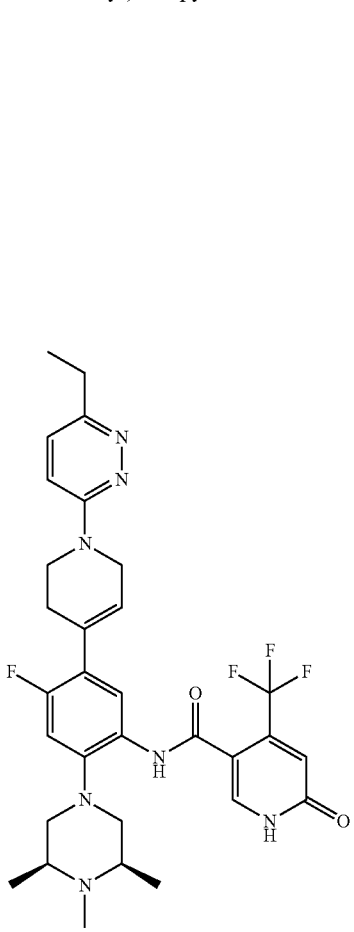

The procedure was similar to that of Example 372 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) and 3-bromo-6-ethyl-pyridazine hydrobromide (22.17 mg, 0.083 mmol) to give the title compound (4 mg, 9% yield). $^1$H NMR (500 MHz, METHANOL-d4) δ=7.84-7.81 (m, 1H), 7.74-7.67 (m, 1H), 7.30-7.24 (m, 1H), 7.19-7.13 (m, 1H), 6.89-6.83 (m, 1H), 6.82-6.80 (m, 1H), 6.09-6.02 (m, 1H), 4.13-4.10 (m, 2H), 3.84-3.74 (m, 2H), 2.95-2.91 (m, 2H), 2.75-2.70 (m, 2H), 2.57-2.46 (m, 6H), 2.28-2.27 (m, 3H), 1.20-1.17 (m, 3H), 1.07-1.05 (m, 6H); LCMS [M+H]+ 614.6.

Example 505: N-[4-fluoro-5-[6-(oxan-4-yloxy)pyridin-3-yl]-2-[(3R,5S)-3,4,5-trimethylpiperazin-1-yl]phenyl]-6-methoxy-4-(trifluoromethyl)pyridine-3-carboxamide

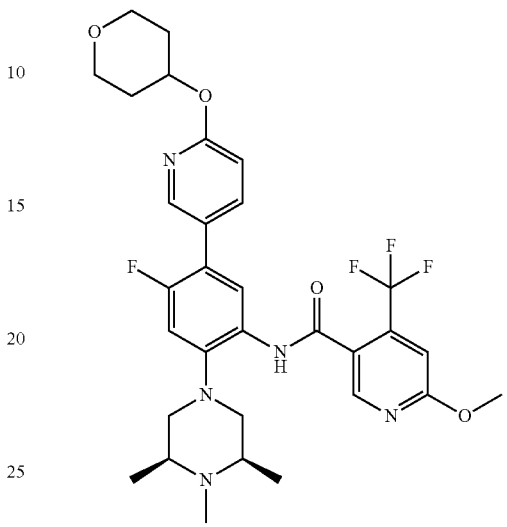

Step 1: 6-methoxy-4-(trifluoromethyl)nicotinic acid

A mixture of 6-chloro-4-(trifluoromethyl)nicotinic acid (4 g, 17.73 mmol) and sodium methoxide (95%, powder) (15.13 g, 266 mmol) in MeOH (40 mL) was heated at reflux under nitrogen in a RB flask. The reaction was complete after 5 h. The mixture was cooled to rt and quenched with satd. citric acid solution. The mixture was concentrated to remove most of the methanol and then extracted with EtOAc (1×200 ml and the 1×100 ml). The combined org phase was dried over Na$_2$SO$_4$ and concentrated to afford the desired product as a white solid. (4.18 g, 95% purity, quantitative yield). $^1$H NMR (500 MHz, DMSO-d6) δ=8.79 (s, 1H), 7.28 (s, 1H), 3.99 (s, 3H).

Step 2: N-(5-bromo-4-fluoro-2-((3S,5R)-3,4,5-trimethylpiperazin-1-yl)phenyl)-6-methoxy-4-(trifluoromethyl)nicotinamide

Step 3: N-(4-fluoro-5-(6-((tetrahydro-2H-pyran-4-yl)oxy)pyridin-3-yl)-2-((3S,5R)-3,4,5-trimethylpiperazin-1-yl)phenyl)-6-methoxy-4-(trifluoromethyl)nicotinamide

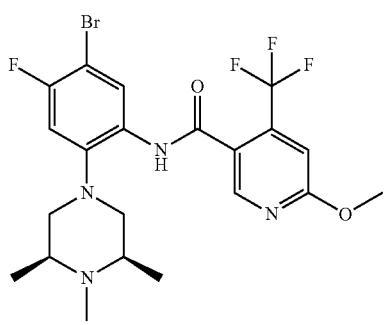 [SMILES: COc1cc(C(F)(F)F)c(C(=O)Nc2cc(Br)c(F)cc2N2C[C@@H](C)N(C)[C@@H](C)C2)cn1]

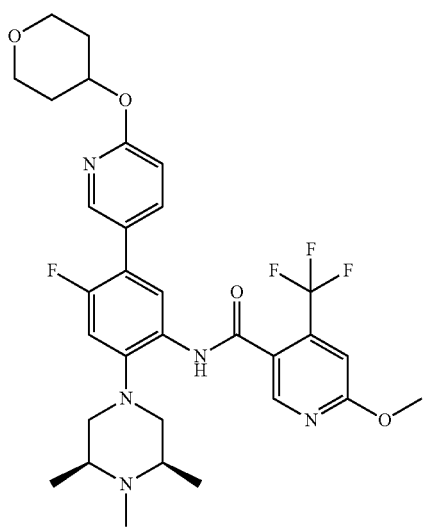 [SMILES: COc1cc(C(F)(F)F)c(C(=O)Nc2cc(-c3ccc(OC4CCOCC4)nc3)c(F)cc2N2C[C@@H](C)N(C)[C@@H](C)C2)cn1]

Propylphosphonic anhydride solution (1.412 ml, 2.372 mmol) was added dropwise to a mixture of 6-methoxy-4-(trifluoromethyl)nicotinic acid (265 mg, 1.138 mmol) and pyridine (0.306 ml, 3.79 mmol) in dry THF (6 ml) under $N_2$ at RT. A dark wine red-coloured solution was obtained. After 1.25 h of stirring at RT, 5-bromo-4-fluoro-2-((3S,5R)-3,4,5-trimethylpiperazin-1-yl)aniline (300 mg, 0.949 mmol) was added as a solution in 1.5 ml THF and the reaction mixture was heated at 50° C. for 16 h. Complete disappearance of the aniline was observed along with the starting acid (20% excess acid was used) and the desired product. The mixture was allowed to cool to RT, THF was removed on a Rotovap, the residue was taken up in DCM (25 ml) and water (25 ml). The org phase was separated and the aq phase was extracted with DCM (2×15 ml). The combined org phase was washed with NaOH (1N, 2×20 ml) solution to remove the excess starting material (acid), then with water (20 ml), and brine (20 ml), dried over $Na_2SO_4$ and concentrated to afford the desired product as light brown solid (250 mg). LCMS shows the purity of the crude as 96%. $^1$H NMR (500 MHz, METHANOL-d4) δ=8.42 (s, 1H), 8.07 (d, J=7.5 Hz, 1H), 7.11 (s, 1H), 7.01 (d, J=10.0 Hz, 1H), 3.95 (s, 3H), 2.94 (d, J=10.5 Hz, 2H), 2.54-2.44 (m, 4H), 2.28 (s, 3H), 1.07 (d, J=5.9 Hz, 6H).

The procedure followed was similar to that of Example 39 using N-(5-bromo-4-fluoro-2-((3S,5R)-3,4,5-trimethylpiperazin-1-yl)phenyl)-6-methoxy-4-(trifluoromethyl)nicotinamide (40 mg, 0.077 mmol) and 2-(tetrahydropyran-4-yloxy)-5-(4,4,5,5-tetramethyl-1,3,2-dioxaborolan-2-yl)pyridine (35.3 mg, 0.116 mmol) to afford the title compound (29 mg, 58% yield). $^1$H NMR (500 MHz, METHANOL-d4) δ=8.48-8.40 (m, 1H), 8.23-8.15 (m, 1H), 7.91-7.83 (m, 1H), 7.81-7.74 (m, 1H), 7.15-7.08 (m, 1H), 7.03-6.95 (m, 1H), 6.82-6.74 (m, 1H), 5.23-5.10 (m, 1H), 4.00-3.94 (m, 3H), 3.92-3.84 (m, 2H), 3.58-3.50 (m, 2H), 3.03-2.95 (m, 2H), 2.59-2.49 (m, 2H), 2.48-2.38 (m, 2H), 2.30-2.24 (m, 3H), 2.04-1.96 (m, 2H), 1.73-1.65 (m, 2H), 1.07 (d, J=6.2 Hz, 6H); LCMS [M+H]+ 618.7

Example 506: N-[4-fluoro-5-(2-morpholin-4-ylpyrimidin-5-yl)-2-[(3R,5S)-3,4,5-trimethylpiperazin-1-yl]phenyl]-6-methoxy-4-(trifluoromethyl)pyridine-3-carboxamide Example 507: 4-(difluoromethyl)-N-[4-fluoro-2-[(3R)-3,4-dimethylpiperazin-1-yl]-5-[6-[(2R)-2-methylmorpholin-4-yl]pyridin-3-yl]phenyl]-6-oxo-1H-pyridine-3-carboxamide

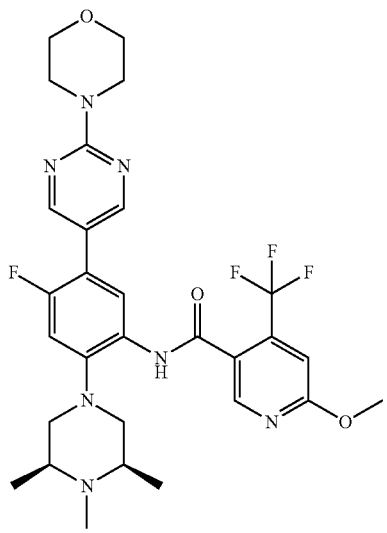

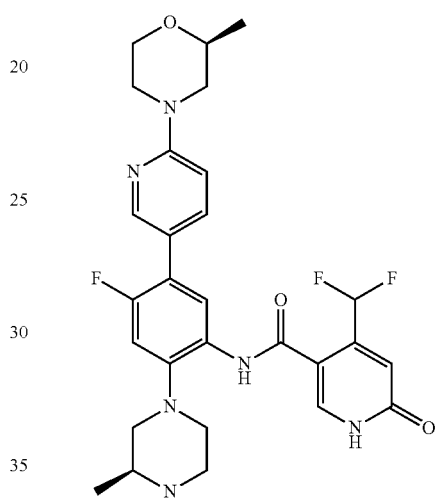

The procedure followed was similar to Example 505, Step 3 using N-(5-bromo-4-fluoro-2-((3S,5R)-3,4,5-trimethylpiperazin-1-yl)phenyl)-6-methoxy-4-(trifluoromethyl)nicotinamide (40 mg, 0.077 mmol), 2-(4-morpholino)pyrimidine-5-boronic acid pinacol ester (33.6 mg, 0.116 mmol) to give the title compound. $^1$H NMR (500 MHz, METHANOL-d4) δ=8.48-8.41 (m, 3H), 7.91-7.83 (m, 1H), 7.14-7.08 (m, 1H), 7.00-6.93 (m, 1H), 4.00-3.92 (m, 3H), 3.76-3.71 (m, 4H), 3.69-3.63 (m, 4H), 2.98-2.91 (m, 2H), 2.54-2.47 (m, 2H), 2.44-2.34 (m, 2H), 2.27-2.22 (m, 3H), 1.05 (d, J=6.1 Hz, 6H); LCMS [M+H]+ 604.4.

The procedure followed was similar to that used for Example 39 using (S)—N-(5-bromo-2-(3,4-dimethylpiperazin-1-yl)-4-fluorophenyl)-4-(difluoromethyl)-6-(2-(trimethylsilyl)ethoxy)nicotinamide (100.7 mg, 0.176 mmol) and (S)-2-methyl-4-(5-(4,4,5,5-tetramethyl-1,3,2-dioxaborolan-2-yl)pyridin-2-yl)morpholine (112 mg, 0.368 mmol) to afford, after TFA deprotection of the silyloxy intermediate, the title compound (64.8 mg, 0.111 mmol, 63.3% yield) as a white powder. $^1$H NMR (500 MHz, DMSO-d6) δ=12.02 (br. s, 1H), 9.51 (s, 1H), 8.27 (s, 1H), 8.00 (s, 1H), 7.66-7.72 (m, 2H), 7.34 (t, J=54.00 Hz, 1H), 7.04 (d, J=12.47 Hz, 1H), 6.94 (d, J=8.80 Hz, 1H), 6.57 (s, 1H), 4.18 (d, J=12.47 Hz, 1H), 4.08 (d, J=12.84 Hz, 1H), 3.92 (dd, J=2.51, 11.43 Hz, 1H), 3.51-3.62 (m, 2H), 3.00 (dd, J=11.07, 19.13 Hz, 2H), 2.73-2.89 (m, 3H), 2.54 (s, 1H), 2.42 (t, J=10.51 Hz, 1H), 2.27-2.37 (m, 1H), 2.17-2.24 (m, 4H), 1.17 (d, J=6.24 Hz, 3H), 0.97 (d, J=6.24 Hz, 3H); LCMS [M]+571.4.

Example 508: 4-(difluoromethyl)-N-[4-fluoro-5-[6-[(2R)-2-methylmorpholin-4-yl]pyridin-3-yl]-2-[(3R,5S)-3,4,5-trimethylpiperazin-1-yl]phenyl]-6-oxo-1H-pyridine-3-carboxamide

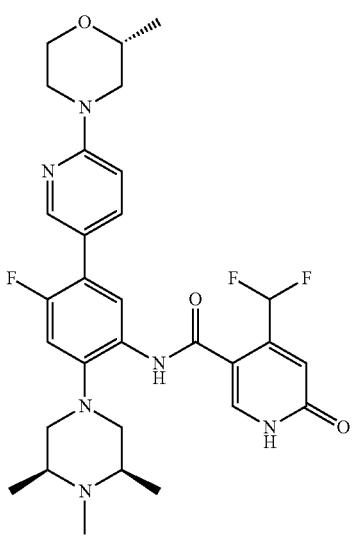 [SMILES: C[C@@H]1CN(c2ccc(-c3cc(NC(=O)c4c[nH]c(=O)cc4C(F)F)c(N4C[C@@H](C)N(C)[C@@H](C)C4)cc3F)cn2)CCO1]

The procedure followed was similar to that for Example 39 using N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (100.4 mg, 0.171 mmol) and (R)-2-methyl-4-(5-(4,4,5,5-tetramethyl-1,3,2-dioxaborolan-2-yl)pyridin-2-yl)morpholine (107.3 mg, 0.353 mmol) to afford, after deprotection of the silyloxy intermediate, the title compound (55.7 mg, 54.7% yield) as a white powder. $^1$H NMR (500 MHz, DMSO-d6) δ=12.07 (br. s, 1H), 9.54 (s, 1H), 8.26 (s, 1H), 8.00 (s, 1H), 7.65-7.70 (m, 2H), 7.35 (t, J=54.90 Hz, 1H), 7.01 (d, J=12.59 Hz, 1H), 6.94 (d, J=8.93 Hz, 1H), 6.58 (s, 1H), 4.18 (d, J=12.72 Hz, 1H), 4.08 (d, J=12.84 Hz, 1H), 3.92 (dd, J=2.38, 11.43 Hz, 1H), 3.51-3.60 (m, 2H), 3.01 (d, J=10.88 Hz, 2H), 2.84 (dt, J=3.42, 12.35 Hz, 1H), 2.54 (s, 1H), 2.45 (t, J=11.00 Hz, 2H), 2.28-2.37 (m, 2H), 2.19 (s, 3H), 1.17 (d, J=6.24 Hz, 3H), 1.00 (d, J=6.11 Hz, 6H); LCMS [M]+585.5.

Example 509: 4-(difluoromethyl)-N-[4-fluoro-2-[(3S)-3,4-dimethylpiperazin-1-yl]-5-[6-[(2R)-2-methylmorpholin-4-yl]pyridin-3-yl]phenyl]-6-oxo-1H-pyridine-3-carboxamide

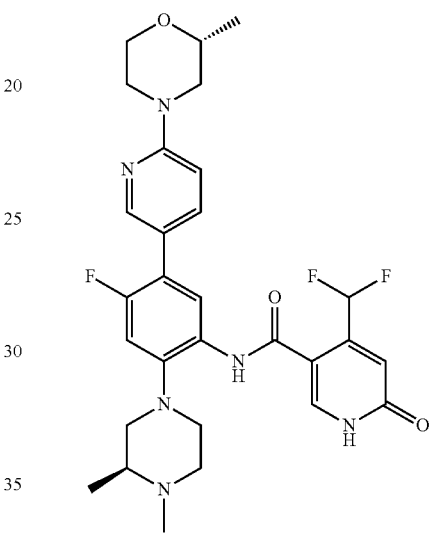

The procedure followed was similar to that described in Example 39 using (S)—N-(5-bromo-2-(3,4-dimethylpiperazin-1-yl)-4-fluorophenyl)-4-(difluoromethyl)-6-(2-(trimethylsilyl)ethoxy)nicotinamide (101.4 mg, 0.177 mmol, from Example 396) and (R)-2-methyl-4-(5-(4,4,5,5-tetramethyl-1,3,2-dioxaborolan-2-yl)pyridin-2-yl)morpholine (109.6 mg, 0.360 mmol) to give, after deprotection of the silyloxy intermediate, the title compound (63.3 mg, 60.3% yield) as a white powder. $^1$H NMR (500 MHz, DMSO-d6) δ=12.09 (br. s, 1H), 9.52 (s, 1H), 8.27 (s, 1H), 8.00 (s, 1H), 7.68 (d, J=8.68 Hz, 2H), 7.34 (t, J=56.50 Hz, 1H), 7.04 (d, J=12.47 Hz, 1H), 6.94 (d, J=8.93 Hz, 1H), 6.58 (s, 1H), 4.18 (d, J=12.47 Hz, 1H), 4.08 (d, J=12.84 Hz, 1H), 3.92 (dd, J=2.51, 11.55 Hz, 1H), 3.51-3.61 (m, 2H), 3.01 (dd, J=11.00, 19.56 Hz, 2H), 2.72-2.88 (m, 3H), 2.52-2.54 (m, 1H), 2.41 (t, J=10.51 Hz, 1H), 2.28-2.37 (m, 1H), 2.21 (s, 4H), 2.19-2.25 (m, 4H), 1.17 (d, J=6.11 Hz, 3H), 0.97 (d, J=6.24 Hz, 3H); LCMS [M]+571.5.

Example 510: 4-(difluoromethyl)-N-[4-fluoro-5-[6-[(2R)-2-methylmorpholin-4-yl]pyridin-3-yl]-2-[(3S,5R)-3,4,5-trimethylpiperazin-1-yl]phenyl]-6-oxo-1H-pyridine-3-carboxamide Example 511: 4-(difluoromethyl)-N-[4-fluoro-5-[6-[(2R,6S)-2,6-dimethylmorpholin-4-yl]pyridin-3-yl]-2-[(3R,5S)-3,4,5-trimethylpiperazin-1-yl]phenyl]-6-oxo-1H-pyridine-3-carboxamide

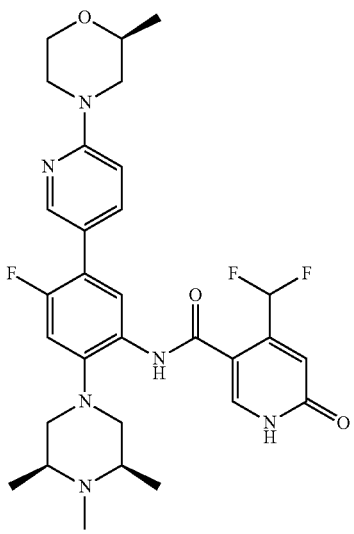 [SMILES: C[C@@H]1CN(c2cc(F)c(-c3ccc(N4CCO[C@@H](C)C4)nc3)cc2NC(=O)c2c[nH]c(=O)cc2C(F)F)C[C@H](C)N1C]

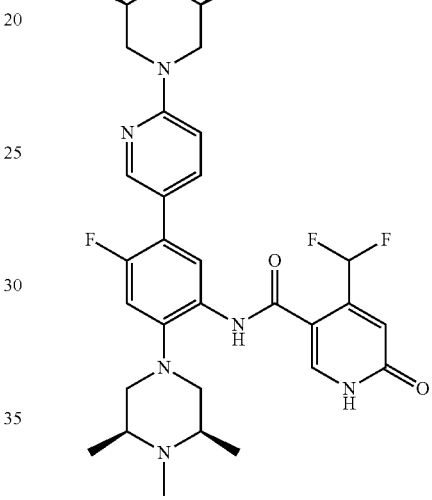

The procedure followed was similar to Example 39 using N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (104.6 mg, 0.178 mmol) and (S)-2-methyl-4-(5-(4,4,5,5-tetramethyl-1,3,2-dioxaborolan-2-yl)pyridin-2-yl)morpholine (109.7 mg, 0.361 mmol) to afford, after deprotection of the silyloxy intermediate with TFA, the title compound (57.6 mg, 54.2% yield) as a white powder. $^1$H NMR (500 MHz, DMSO-d6) δ=11.91 (br. s, 1H), 9.54 (s, 1H), 8.26 (s, 1H), 7.99 (s, 1H), 7.64-7.71 (m, 2H), 7.35 (t, J=54.30 Hz, 1H), 7.01 (d, J=12.47 Hz, 1H), 6.94 (d, J=8.93 Hz, 1H), 6.58 (s, 1H), 4.18 (d, J=12.59 Hz, 1H), 4.08 (d, J=12.84 Hz, 1H), 3.92 (dd, J=2.45, 11.49 Hz, 1H), 3.51-3.62 (m, 2H), 3.01 (d, J=10.76 Hz, 2H), 2.84 (dt, J=3.55, 12.35 Hz, 1H), 2.51-2.54 (m, 1H), 2.45 (t, J=11.00 Hz, 2H), 2.27-2.38 (m, 2H), 2.19 (s, 3H), 1.17 (d, J=6.24 Hz, 3H), 1.00 (d, J=6.24 Hz, 6H); LCMS [M]+585.5.

The procedure followed was similar to Example 39 using N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (100.1 mg, 0.170 mmol) and (2S,6R)-2,6-dimethyl-4-(5-(4,4,5,5-tetramethyl-1,3,2-dioxaborolan-2-yl)pyridin-2-yl)morpholine (109.7 mg, 0.345 mmol) to afford, after deprotection of the silyoxy intermediate, the title compound (53 mg, 51.0% yield) as a white powder. $^1$H NMR (500 MHz, DMSO-d6) δ=12.14 (br. s, 1H), 9.52 (s, 1H), 8.25 (s, 1H), 8.01 (s, 1H), 7.68 (d, J=8.56 Hz, 2H), 7.35 (t, J=56.70 Hz, 1H), 7.01 (d, J=12.47 Hz, 1H), 6.94 (d, J=8.93 Hz, 1H), 6.56 (s, 1H), 4.19 (d, J=11.49 Hz, 2H), 3.61 (ddd, J=2.38, 6.30, 10.39 Hz, 2H), 3.01 (d, J=11.00 Hz, 2H), 2.40-2.48 (m, 4H), 2.32 (d, J=6.36 Hz, 2H), 2.19 (s, 3H), 1.16 (d, J=6.24 Hz, 6H), 1.00 (d, J=6.24 Hz, 6H); LCMS [M]+599.4.

Example 512: 5-amino-4-fluoro-N-[4-fluoro-5-(2-morpholin-4-ylpyrimidin-5-yl)-2-[(3R)-3,4-dimethylpiperazin-1-yl]phenyl]-2-(trifluoromethyl)benzamide

Example 513: N-[4-fluoro-5-(2-morpholin-4-ylpyrimidin-5-yl)-2-[(3aR,6aR)-1-ethyl-2,3,3a,4,6,6a-hexahydropyrrolo[2,3-c]pyrrol-5-yl]phenyl]-6-oxo-4-(trifluoromethyl)-1H-pyridine-3-carboxamide

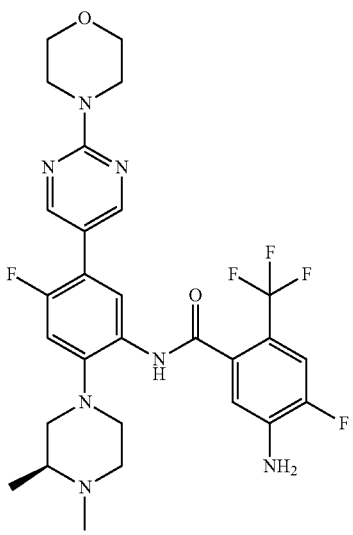 [SMILES: C[C@H]1CN(c2cc(F)c(-c3cnc(N4CCOCC4)nc3)cc2NC(=O)c2cc(N)c(F)cc2C(F)(F)F)CCN1C]

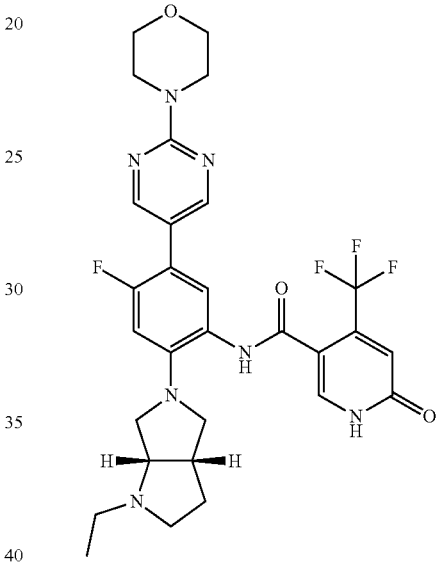

The title compound was prepared similar to the procedure described above for the preparation of Example 502 using (S)-2-(3,4-dimethylpiperazin-1-yl)-4-fluoro-5-(2-morpholinopyrimidin-5-yl)aniline in place of 4-fluoro-5-(2-morpholinopyrimidin-5-yl)-2-(cis-3,4,5-trimethylpiperazin-1-yl)aniline in Step 2. ¹H NMR (500 MHz, METHANOL-d4) δ=8.55 (d, J=1.0 Hz, 2H), 8.06 (d, J=8.3 Hz, 1H), 7.37 (d, J=11.9 Hz, 1H), 7.12 (d, J=12.0 Hz, 1H), 7.01 (d, J=8.4 Hz, 1H), 3.87-3.82 (m, 4H), 3.79-3.74 (m, 4H), 3.07 (br dd, J=2.2, 11.7 Hz, 1H), 3.00 (br d, J=11.5 Hz, 1H), 2.96-2.85 (m, 2H), 2.56 (t, J=10.8 Hz, 1H), 2.45 (dt, J=2.9, 11.5 Hz, 1H), 2.33 (s, 3H), 1.10 (d, J=6.2 Hz, 3H); LCMS [M+H]+: 592.4.

The procedure followed was similar to that of Example 476 using N-(4-fluoro-2-(hexahydropyrrolo[3,4-b]pyrrol-5(1H)-yl)-5-(2-morpholinopyrimidin-5-yl)phenyl)-6-oxo-4-(trifluoromethyl)-1,6-dihydropyridine-3-carboxamide-TFA (70 mg, 0.064 mmol) and propionaldehyde (19.4 mg, 0.334 mmol) to afford the title compound (10.7 mg, 0.016 mmol, 25.6% yield) as a white powder. ¹H NMR (500 MHz, DMSO-d6) δ=12.58 (br. s., 1H), 9.63 (br. s., 1H), 8.51 (s, 2H), 8.02 (br. s., 1H), 7.53 (d, J=7.83 Hz, 1H), 6.76-6.88 (m, 2H), 3.72-3.78 (m, 5H), 3.65-3.70 (m, 5H), 3.19 (br. s., 1H), 3.11 (br. s., 1H), 2.92-3.07 (m, 3H), 2.74 (d, J=9.78 Hz, 1H), 2.43 (br. s., 1H), 2.36 (br. s., 1H), 2.19 (br. s., 2H), 1.98 (br. s., 1H), 1.61 (br. s., 1H), 1.35 (br. s., 1H), 1.23 (br. s., 1H), 0.81-0.96 (m, 1H), 0.77 (t, J=7.09 Hz, 3H); LCMS [M+H]+ 616.6.

Example 514: 4-(difluoromethyl)-N-[4-fluoro-5-[6-[(2R,6S)-2,6-dimethylmorpholin-4-yl]pyridin-3-yl]-2-[(3S)-3,4-dimethylpiperazin-1-yl]phenyl]-6-oxo-1H-pyridine-3-carboxamide

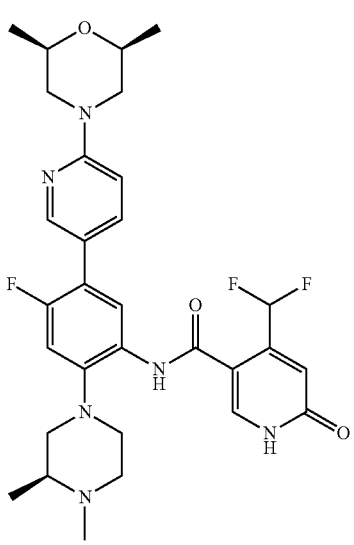 [SMILES: C[C@@H]1CN(c2ccc(-c3cc(NC(=O)c4c[nH]c(=O)cc4C(F)F)c(N4CCN(C)[C@@H](C)C4)cc3F)cn2)C[C@H](C)O1]

The procedure followed was similar to that of Example 39 using (S)—N-(5-bromo-2-(3,4-dimethylpiperazin-1-yl)-4-fluorophenyl)-4-(difluoromethyl)-6-(2-(trimethylsilyl)ethoxy)nicotinamide (97 mg, 0.169 mmol) and (2S,6R)-2,6-dimethyl-4-(5-(4,4,5,5-tetramethyl-1,3,2-dioxaborolan-2-yl)pyridin-2-yl)morpholine (112 mg, 0.352 mmol) to afford, after deprotection of the silyloxy intermediate with TFA, the title compound (43.2 mg, 0.069 mmol, 40.6% yield) as a white powder. $^1$H NMR (500 MHz, DMSO-d6) δ=12.35 (bs, 1H), 9.53 (s, 1H), 8.26 (s, 1H), 8.00 (s, 1H), 7.67 (d, J=8.68 Hz, 2H), 7.34 (t, J=56.50 Hz, 1H), 7.04 (d, J=12.47 Hz, 1H), 6.94 (d, J=8.93 Hz, 1H), 6.59 (s, 1H), 4.19 (d, J=11.49 Hz, 2H), 3.61 (ddd, J=2.20, 6.30, 10.33 Hz, 2H), 3.00 (dd, J=11.07, 19.75 Hz, 2H), 2.71-2.85 (m, 2H), 2.38-2.47 (m, 3H), 2.28-2.37 (m, 1H), 2.22-2.19 (m, 1H), 2.21 (s, 3H), 1.16 (d, J=6.11 Hz, 6H), 0.97 (d, J=6.24 Hz, 3H); LCMS [M]+585.5.

Example 515: 4-(difluoromethyl)-N-[4-fluoro-5-[6-[(2R,6S)-2,6-dimethylmorpholin-4-yl]pyridin-3-yl]-2-[(3S)-3,4-dimethylpiperazin-1-yl]phenyl]-1-methyl-6-oxopyridine-3-carboxamide

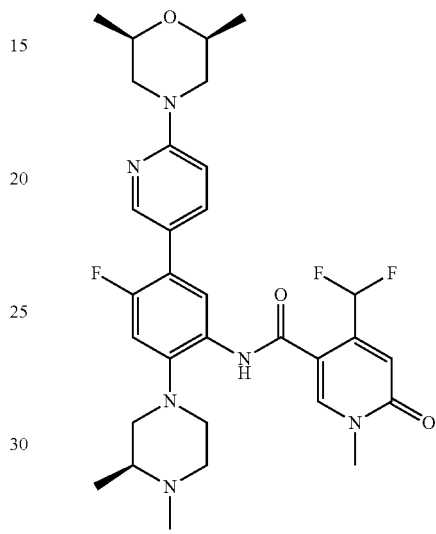

To a suspension of 4-(difluoromethyl)-N-(5-(6-((2S,6R)-2,6-dimethylmorpholino)pyridin-3-yl)-2-((S)-3,4-dimethylpiperazin-1-yl)-4-fluorophenyl)-6-oxo-1,6-dihydropyridine-3-carboxamide (22.6 mg, 0.039 mmol) and cesium carbonate (13.85 mg, 0.043 mmol) in DMF (3 ml) was added MeI (2.65 μl, 0.043 mmol) at room temperature and the reaction mixture was stirred for 1 h 00 at room temperature. The reaction mixture was poured into water and the product was extracted by DCM. The organic phase was dried over MgSO$_4$ and after filtration and solvent removal the crude material was dissolved in MeOH and passed through a PoraPak Rxn CX (20 cc-2 g) cartridge in a catch and elute method. The cartridge was washed with MeOH, then the solution of product in MeOH was added onto the cartridge. The cartridge was rinsed with MeOH (2×20 mL) and then with a solution of 10 mL (NH$_3$ in MeOH at 7N) in 40 mL of MeOH to release the free base of the title compound (22.6 mg, 0.035 mmol, 90% yield) as an off-white powder. $^1$H NMR (500 MHz, DMSO-d6) δ=9.45 (s, 1H), 8.36 (s, 1H), 8.25 (s, 1H), 7.67 (d, J=8.68 Hz, 2H), 7.33 (t, J=55.40 Hz, 1H), 7.05 (d, J=12.47 Hz, 1H), 6.94 (d, J=8.93 Hz, 1H), 6.64 (s, 1H), 4.19 (d, J=11.49 Hz, 2H), 3.61 (ddd, J=2.26, 6.33, 10.24 Hz, 2H), 3.52 (s, 3H), 2.97-3.08 (m, 2H), 2.73-2.86 (m, 2H), 2.38-2.47 (m, 3H), 2.30-2.38 (m, 1H), 2.18-2.27 (m, 1H+3H), 1.17 (d, J=6.24 Hz, 6H), 0.97 (d, J=6.24 Hz, 3H); LCMS [M]+599.4.

Example 516: 4-(difluoromethyl)-N-[4-fluoro-2-[(3S)-3,4-dimethylpiperazin-1-yl]-5-[6-[(2R)-2-methylmorpholin-4-yl]pyridin-3-yl]phenyl]-1-methyl-6-oxopyridine-3-carboxamide

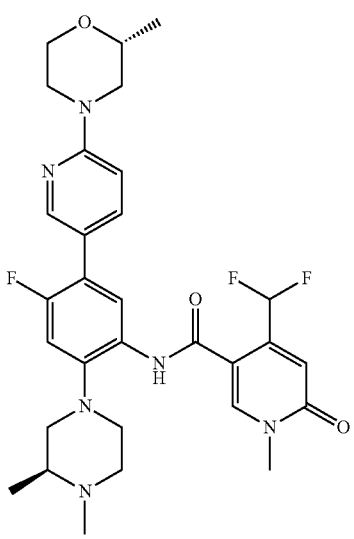 [SMILES: C[C@@H]1CN(c2ccc(-c3cc(NC(=O)c4cn(C)c(=O)cc4C(F)F)c(N4CCN(C)[C@@H](C)C4)cc3F)cn2)CCO1]

The procedure followed was similar to Example 515 using 4-(difluoromethyl)-N-(2-((S)-3,4-dimethylpiperazin-1-yl)-4-fluoro-5-(6-((R)-2-methylmorpholino)pyridin-3-yl)phenyl)-6-oxo-1,6-dihydropyridine-3-carboxamide (39.7 mg, 0.070 mmol) to afford the title compound (39.2 mg, 0.064 mmol, 92% yield) as a white powder. $^1$H NMR (500 MHz, DMSO-d6) δ=9.45 (s, 1H), 8.36 (s, 1H), 8.26 (s, 1H), 7.67 (d, J=8.56 Hz, 2H), 7.33 (t, J=55.10 Hz, 1H), 7.06 (d, J=12.47 Hz, 1H), 6.94 (d, J=8.80 Hz, 1H), 6.64 (s, 1H), 4.18 (d, J=12.47 Hz, 1H), 4.08 (d, J=13.20 Hz, 1H), 3.92 (dd, J=2.63, 11.31 Hz, 1H), 3.55 (d, J=2.57 Hz, 2H), 3.52 (s, 3H), 2.97-3.08 (m, 2H), 2.84 (br. s., 3H), 2.42 (br. s., 1H), 2.36 (br. s., 1H), 2.21 (br. s., 4H), 1.17 (d, J=6.24 Hz, 3H), 0.98 (d, J=5.99 Hz, 3H); LCMS [M]+585.5.

Example 517: 4-(Difluoromethyl)-N-[4-fluoro-5-[6-[(2R)-2-methylmorpholin-4-yl]pyridin-3-yl]-2-[(3S,5R)-3,4,5-trimethylpiperazin-1-yl]phenyl]-1-methyl-6-oxopyridine-3-carboxamide

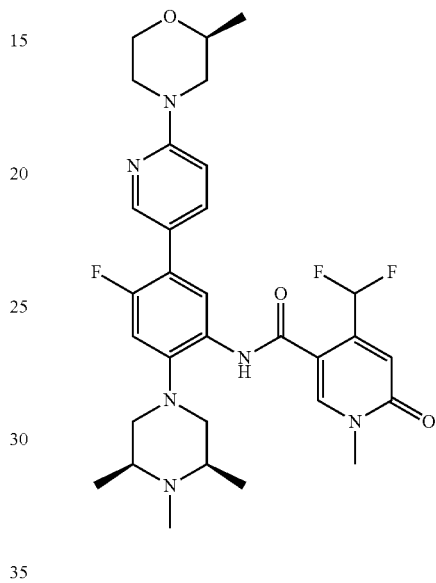

To a suspension of 4-(difluoromethyl)-N-(4-fluoro-5-(6-((S)-2-methylmorpholino)pyridin-3-yl)-2-((3S,5R)-3,4,5-trimethylpiperazin-1-yl)phenyl)-6-oxo-1,6-dihydropyridine-3-carboxamide (35.2 mg, 0.060 mmol) and cesium carbonate (21.58 mg, 0.066 mmol) in DMF (6 mL) was added iodomethane (4.12 μl, 0.066 mmol) at room temperature and stirred for 1 hour. Then the reaction mixture was poured into water and the product was extracted by DCM. The organic phase was dried over MgSO$_4$ and after filtration and solvent removal the crude material was triturated with Et$_2$O. After removing the Et$_2$O under vacuum, the desired 4-(difluoromethyl)-N-(4-fluoro-5-(6-((S)-2-methylmorpholino)pyridin-3-yl)-2-((3S,5R)-3,4,5-trimethylpiperazin-1-yl)phenyl)-1-methyl-6-oxo-1,6-dihydropyridine-3-carboxamide (35.5 mg, 0.056 mmol, 94% yield) was obtained as a white powder. $^1$H NMR (500 MHz, DMSO-d6) δ=9.47 (s, 1H), 8.35 (s, 1H), 8.26 (s, 1H), 7.64-7.70 (m, 2H), 7.33 (t, J=56.50 Hz, 1H), 7.03 (d, J=12.59 Hz, 1H), 6.94 (d, J=8.93 Hz, 1H), 6.64 (s, 1H), 4.18 (d, J=12.72 Hz, 1H), 4.08 (d, J=12.84 Hz, 1H), 3.92 (dd, J=2.32, 11.37 Hz, 1H), 3.56 (dd, J=2.51, 11.07 Hz, 2H), 3.49-3.54 (m, 3H), 3.02 (d, J=11.00 Hz, 2H), 2.84 (dt, J=3.42, 12.29 Hz, 1H), 2.51-2.54 (m, 1H), 2.46 (s, 2H), 2.28-2.38 (m, 2H), 2.18 (s, 4H), 1.17 (d, J=6.11 Hz, 3H), 1.00 (d, J=6.11 Hz, 7H); LCMS [M]+ 599.4.

Example 518: 4-(difluoromethyl)-N-[4-fluoro-5-[6-[(2R,6S)-2,6-dimethylmorpholin-4-yl]pyridin-3-yl]-2-[(3R,5S)-3,4,5-trimethylpiperazin-1-yl]phenyl]-1-methyl-6-oxopyridine-3-carboxamide

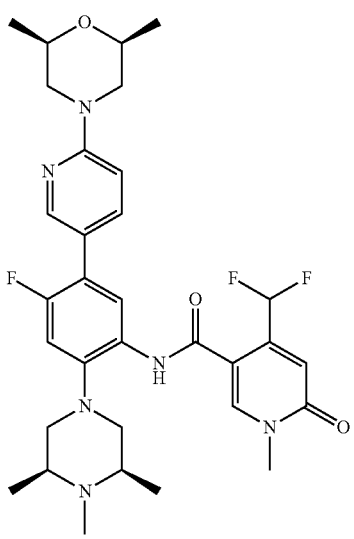 [SMILES: C[C@@H]1CN(c2ccc(-c3cc(NC(=O)c4cn(C)c(=O)cc4C(F)F)c(N4C[C@@H](C)N(C)[C@@H](C)C4)cc3F)cn2)C[C@H](C)O1]

The title compound (white solid, 26.4 mg, 42%) was prepared using (2S,6R)-2,6-dimethyl-4-(5-(4,4,5,5-tetramethyl-1,3,2-dioxaborolan-2-yl)pyridin-2-yl)morpholine (47 mg, 0.15 mmol) and N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (51.8 mg, 0.1 mmol). $^1$H NMR (500 MHz, METHANOL-d4) δ=8.31 (s, 1H), 8.26 (s, 1H), 7.93 (d, J=8.3 Hz, 1H), 7.79 (br d, J=8.8 Hz, 1H), 7.09 (d, J=12.0 Hz, 1H), 6.95 (s, 1H), 6.92 (d, J=8.7 Hz, 1H), 4.16 (br d, J=12.1 Hz, 2H), 3.78-3.70 (m, 2H), 3.66 (s, 3H), 3.09 (br d, J=8.4 Hz, 2H), 2.73-2.51 (m, 6H), 2.44 (br s, 3H), 1.27 (d, J=6.2 Hz, 6H), 1.21 (br s, 6H); LCMS [M+H]$^+$ 631.6.

Example 519: 4-(difluoromethyl)-N-[4-fluoro-2-[(3R)-3,4-dimethylpiperazin-1-yl]-5-[6-[(2R)-2-methylmorpholin-4-yl]pyridin-3-yl]phenyl]-1-methyl-6-oxopyridine-3-carboxamide

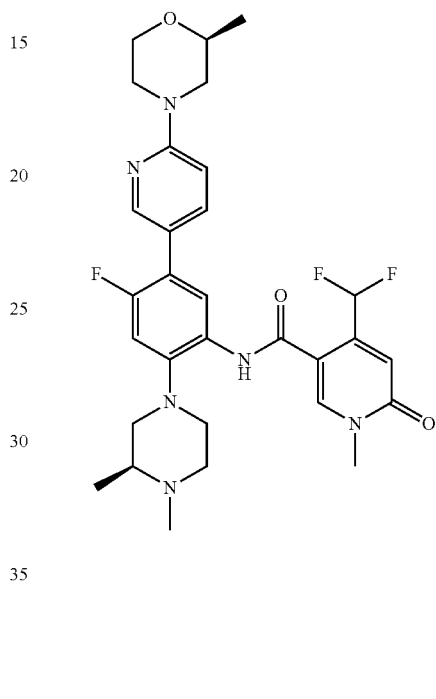

To a suspension of 4-(difluoromethyl)-N-(2-((S)-3,4-dimethylpiperazin-1-yl)-4-fluoro-5-(6-((S)-2-methylmorpholino)pyridin-3-yl)phenyl)-6-oxo-1,6-dihydropyridine-3-carboxamide (43.4 mg, 0.076 mmol) and cesium carbonate (27.3 mg, 0.084 mmol) in N,N-dimethylformamide (6 ml) was added MeI (5.21 µl, 0.084 mmol) at room temperature. The reaction mixture was stirred for 1 hour at room temperature. The reaction mixture was poured into water and the product was extracted by DCM. The organic phase was dried over MgSO$_4$ and after filtration and solvent removal the crude material was triturated with Et$_2$O. After removing the Et$_2$O under vacuum, the desired 4-(difluoromethyl)-N-(2-((S)-3,4-dimethylpiperazin-1-yl)-4-fluoro-5-(6-((S)-2-methylmorpholino)pyridin-3-yl)phenyl)-1-methyl-6-oxo-1,6-dihydropyridine-3-carboxamide (45.7 mg, 0.074 mmol, 98% yield) was obtained as a white powder. $^1$H NMR (500 MHz, DMSO-d6) δ=9.45 (s, 1H), 8.36 (s, 1H), 8.26 (s, 1H), 7.66-7.71 (m, 1H), 7.67 (d, J=8.68 Hz, 2H), 7.33 (t, J=56.10 Hz, 1H), 7.06 (d, J=12.35 Hz, 1H), 6.94 (d, J=8.93 Hz, 1H), 6.64 (s, 1H), 4.18 (d, J=12.84 Hz, 1H), 4.08 (d, J=12.59 Hz, 1H), 3.92 (dd, J=2.51, 11.55 Hz, 1H), 3.56 (dd, J=2.32, 11.00 Hz, 2H), 3.49-3.53 (m, 3H), 2.96-3.09 (m, 2H), 2.74-2.88 (m, 3H), 2.41 (d, J=10.88 Hz, 1H), 2.34 (br. s., 1H), 2.20 (s, 4H), 1.17 (d, J=6.24 Hz, 3H), 0.97 (d, J=6.24 Hz, 3H); LCMS [M]+585.4.

Example 520: N-[4-fluoro-5-(2-morpholin-4-ylpyrimidin-5-yl)-2-[(3R)-3-[methyl(2,2,2-trifluoroethyl)amino]pyrrolidin-1-yl]phenyl]-6-oxo-4-(trifluoromethyl)-1H-pyridine-3-carboxamide

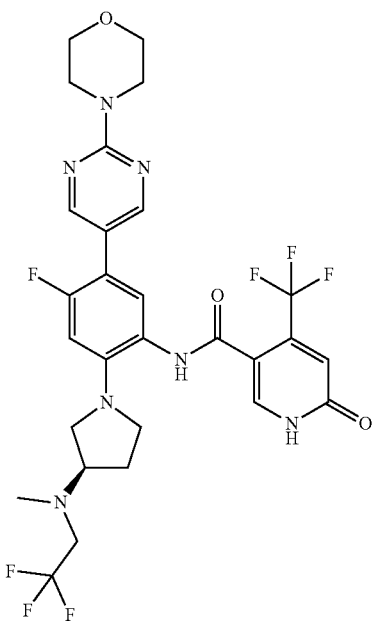 [SMILES: CN(CC(F)(F)F)[C@@H]1CCN(c2cc(F)c(-c3cnc(N4CCOCC4)nc3)cc2NC(=O)c2c[nH]c(=O)cc2C(F)(F)F)C1]

Step 1: tert-butyl (R)-3-(methyl(2,2,2-trifluoroethyl)amino)pyrrolidine-1-carboxylate

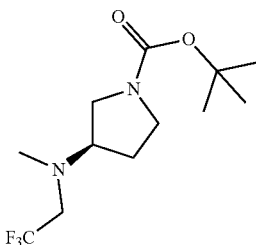

Trifluoroacetic acid (0.30 mL, 3.7 mmol) was activated with HATU (1.4 g, 3.7 mmol) and N,N-diisopropylethylamine (0.65 mL, 3.7 mmol) in DMF (3 mL) at room temperature. After stirring for 10 minutes the solution of activated acid was added to a vial containing a solution of (R)-3-(methylamino)pyrrolidine-1-carboxylic acid tert-butyl ester (0.50 g, 2.5 mmol) in DMF (3 mL) at room temperature. The reaction was allowed to stir at room temperature for 2 h. The solvent was removed in vacuo and the residue was partitioned between DCM and saturated aqueous NaHCO₃. The layers were separated and the organics were dried over magnesium sulfate. After removing the inorganics by filtration the filtrate was concentrated to dryness and the residue was purified by flash chromatography [25-75% EtOAc/hexanes]. The resultant trifluoroacetamide was dissolved in THF (12 mL) and cooled to 0° C. A solution of borane dimethyl sulfide complex (3.3 mL, 2 M THF) was added and the ice bath was removed. The reaction mixture was heated to 60° C. for 4 h. After cooling to room temperature the reaction was carefully quenched with a saturated aqueous NaHCO₃ solution and then diluted with DCM and water. The layers were separated and the aqueous layer was extracted with an additional portion of DCM. The combined organic layers were dried over magnesium sulfate. After removal of the inorganics by filtration the filtrate was concentrated onto celite. Flash chromatography [0-30% EtOAc/hexanes] afforded tert-butyl (R)-3-(methyl(2,2,2-trifluoroethyl)amino)pyrrolidine-1-carboxylate (0.54 g, 77% yield). $^1$H NMR (500 MHz, DMSO-d6) δ=3.46 (q, J=8.7 Hz, 1H), 3.39-3.31 (m, 2H), 3.27-3.09 (m, 4H), 3.03-2.87 (m, 1H), 2.36 (s, 3H), 1.98 (br s, 1H), 1.77-1.62 (m, 1H), 1.39 (s, 9H).

Step 2: (R)-1-(4-bromo-5-fluoro-2-nitrophenyl)-N-methyl-N-(2,2,2-trifluoroethyl)pyrrolidin-3-amine

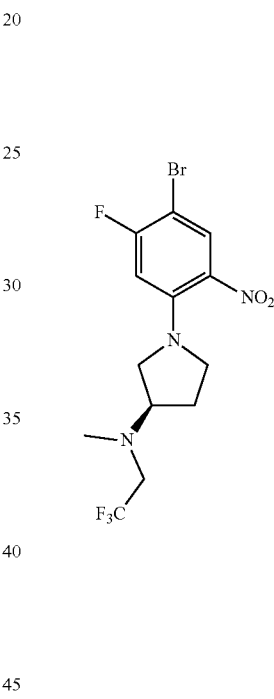

A solution of tert-butyl (R)-3-(methyl(2,2,2-trifluoroethyl)amino)pyrrolidine-1-carboxylate (0.54 g, 1.93 mmol) in DCM (5 mL) was treated with TFA (3.0 mL) at room temperature. After stirring overnight at room temperature the volatiles were removed under a stream of air. The TFA salt of the deprotected amine was suspended in toluene (3 mL) and potassium carbonate (0.40 g, 2.9 mmol) was added carefully in portions. A solution of 1-bromo-2,4-difluoro-5-nitrobenzene (0.46 g, 1.93 mmol) in toluene (3 mL) was added dropwise and the reaction was warmed to 50° C. After 3 h the reaction mixture was cooled to room temperature and partitioned between water and EtOAc. The layers were separated and the aqueous layer was extracted with an additional portion of EtOAc. The combined extracts were dried over magnesium sulfate and after removal of the inorganics by filtration the filtrate was concentrated onto celite. Purification by flash chromatography [10-50% EtOAc/hexanes] afforded (R)-1-(4-bromo-5-fluoro-2-nitrophenyl)-N-methyl-N-(2,2,2-trifluoroethyl)pyrrolidin-3-amine (0.40 g, 52%). LCMS [M+H]⁺: 400.2.

Step 3: (R)-1-(2-amino-4-bromo-5-fluorophenyl)-N-methyl-N-(2,2,2-trifluoroethyl)pyrrolidin-3-amine

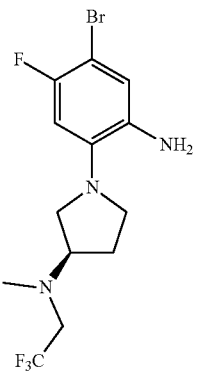 [SMILES: CN(CC(F)(F)F)[C@@H]1CCN(c2cc(F)c(Br)cc2N)C1]

Tin chloride (0.57 g, 3.00 mmol) was added to a solution of (R)-1-(4-bromo-5-fluoro-2-nitrophenyl)-N-methyl-N-(2,2,2-trifluoroethyl)pyrrolidin-3-amine (0.40 g, 1.000 mmol) in EtOH (8 mL) and the reaction was heated to 80° C. for 1 h. After cooling to room temperature the reaction mixture was concentrated directly onto celite and purified by flash chromatography[0.5-10% MeOH/DCM+0.5% NH$_4$OH] to afford (R)-1-(2-amino-4-bromo-5-fluorophenyl)-N-methyl-N-(2,2,2-trifluoroethyl)pyrrolidin-3-amine (0.34 g, 91%). LCMS [M+H]$^+$: 370.1.

Step 4: (R)—N-(5-bromo-4-fluoro-2-(3-(methyl(2,2,2-trifluoroethyl)amino)pyrrolidin-1-yl)phenyl)-4-(trifluoromethyl)-6-(2-(trimethylsilyl)ethoxy)nicotinamide

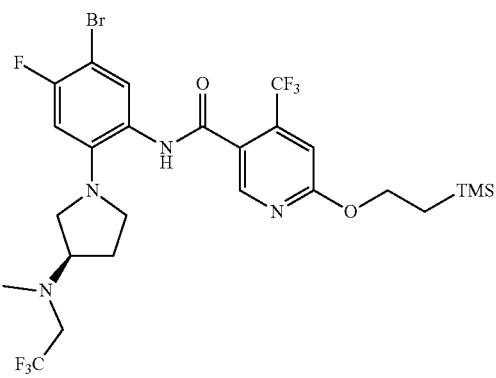 [SMILES: CN(CC(F)(F)F)[C@@H]1CCN(c2cc(F)c(Br)cc2NC(=O)c2cnc(OCC[Si](C)(C)C)cc2C(F)(F)F)C1]

4-(Trifluoromethyl)-6-(2-(trimethylsilyl)ethoxy)nicotinic acid (0.19 g, 0.61 mmol) was activated with HATU (0.23 g, 0.61 mmol) and N,N-diisopropylethylamine (0.11 mL, 0.61 mmol) in DMF (3 mL) at room temperature. After agitating for 5 minutes the solution of activated acid was added dropwise to a stirring solution of (R)-1-(2-amino-4-bromo-5-fluorophenyl)-N-methyl-N-(2,2,2-trifluoroethyl)pyrrolidin-3-amine (0.15 g, 0.41 mmol) in DMF (3 mL) and the reaction warmed to 40° C. for 18 h. The reaction mixture was concentrated onto celite and purified by flash chromatography [0.5-5% MeOH/DCM+0.5% NH$_4$OH] to afford (R)—N-(5-bromo-4-fluoro-2-(3-(methyl(2,2,2-trifluoroethyl)amino)pyrrolidin-1-yl)phenyl)-4-(trifluoromethyl)-6-(2-(trimethylsilyl)ethoxy)nicotinamide (0.22 g, 82%). LCMS [M+H]+: 659.2.

Step 5: (R)—N-(4-fluoro-2-(3-(methyl(2,2,2-trifluoroethyl)amino)pyrrolidin-1-yl)-5-(2-morpholinopyrimidin-5-yl)phenyl)-6-oxo-4-(trifluoromethyl)-1,6-dihydropyridine-3-carboxamide

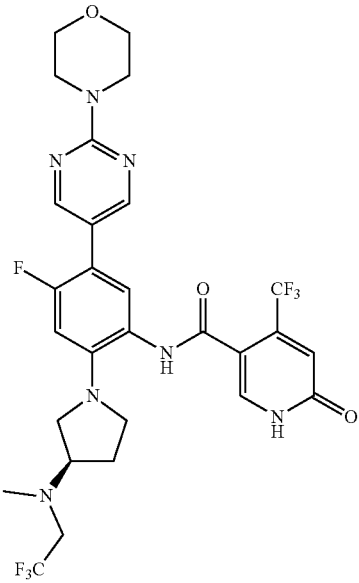 [SMILES: CN(CC(F)(F)F)[C@@H]1CCN(c2cc(F)c(-c3cnc(N4CCOCC4)nc3)cc2NC(=O)c2c[nH]c(=O)cc2C(F)(F)F)C1]

A vial was charged with 2-(4-morpholino)pyrimidine-5-boronic acid pinacol ester (0.044 g, 0.15 mmol), (R)—N-(5-bromo-4-fluoro-2-(3-(methyl(2,2,2-trifluoroethyl)amino)pyrrolidin-1-yl)phenyl)-4-(trifluoromethyl)-6-(2-(trimethylsilyl)ethoxy)nicotinamide (0.050 g, 0.076 mmol), XPhos Pd G2 (0.0012 g, 1.5 μmol) and XPhos (0.0007 g, 1.5 μmol). The vial was sealed and evacuated and backfilled with nitrogen. 1,4-Dioxane (1.3 mL) and aqueous sodium carbonate, (0.15 mL, 0.27 mmol) were added via syringe and the vial evacuated and backfilled an additional time. The reaction was heated to 90° C. for 18 h. After cooling to room temperature the reaction mixture was concentrated onto celite and purified by flash chromatography [0.5-10% MeOH/DCM+0.5% NH$_4$OH] to afford the silyl protected amide. The intermediate product was dissolved in DCM (2 mL) and treated with TFA (0.30 mL). After stirring for 1 h the volatiles were removed in vacuo and the product was isolated with a catch and release protocol using a PoraPak RXN CX ion exchange column to afford the title compound (R)—N-(4-fluoro-2-(3-(methyl(2,2,2-trifluoroethyl)amino)pyrrolidin-1-yl)-5-(2-morpholinopyrimidin-5-yl)phenyl)-6-oxo-4-(trifluoromethyl)-1,6-dihydropyridine-3-carboxamide (0.020 g, 41%). $^1$H NMR (500 MHz, DMSO-d6) δ=12.57 (br s, 1H), 9.79 (s, 1H), 8.50 (s, 2H), 7.96 (br s, 1H), 7.35 (d, J=8.8 Hz, 1H), 6.79 (s, 1H), 6.68 (d, J=13.8 Hz, 1H), 3.73 (br d, J=4.9 Hz, 4H), 3.68 (br d, J=4.8 Hz, 4H), 3.29-3.08 (m, 4H), 2.38 (s, 3H), 2.11 (br dd, J=5.5, 10.8 Hz, 1H), 1.79-1.67 (m, 1H); LCMS [M+H]+: 644.3.

Example 521: 4-(difluoromethyl)-N-[4-fluoro-5-[2-[(3R)-3-methylmorpholin-4-yl]pyrimidin-5-yl]-2-[(3S,5R)-3,4,5-trimethylpiperazin-1-yl]phenyl]-6-oxo-1H-pyridine-3-carboxamide

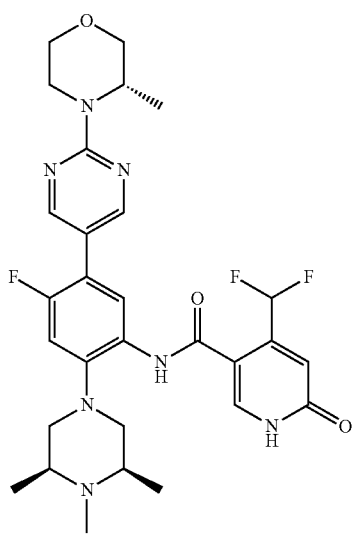 [SMILES: C[C@@H]1CN(c2cc(F)c(-c3cnc(N4CCOC[C@@H]4C)nc3)cc2NC(=O)c2c[nH]c(=O)cc2C(F)F)C[C@H](C)N1C]

The title compound (light beige solid, 14.4 mg, 23%) was prepared from (S)-(2-(3-methylmorpholino)pyrimidin-5-yl)boronic acid (0.2 mmol) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, CHLOROFORM-d) δ=8.71 (br s, 1H), 8.57 (s, 2H), 8.47 (br d, J=8.1 Hz, 1H), 7.86 (br s, 1H), 7.06-6.98 (m, 2H), 4.81-4.75 (m, 1H), 4.42 (br d, J=13.4 Hz, 1H), 4.03 (dd, J=3.4, 11.2 Hz, 1H), 3.82 (d, J=11.4 Hz, 1H), 3.75 (dd, J=2.7, 11.4 Hz, 1H), 3.60 (dt, J=2.9, 11.8 Hz, 1H), 3.34 (dt, J=3.8, 13.0 Hz, 1H), 2.83 (br d, J=10.4 Hz, 2H), 2.75-2.61 (m, 2H), 2.41-2.27 (m, 5H), 1.36 (d, J=6.7 Hz, 3H), 1.16 (br d, J=5.6 Hz, 6H); LCMS [M+H]$^+$ 604.5.

Example 522: N-[5-[6-(cyclopropylmethoxy)pyridin-3-yl]-4-fluoro-2-[(3R)-3,4-dimethylpiperazin-1-yl]phenyl]-1-methyl-6-oxo-4-(trifluoromethyl)pyridine-3-carboxamide

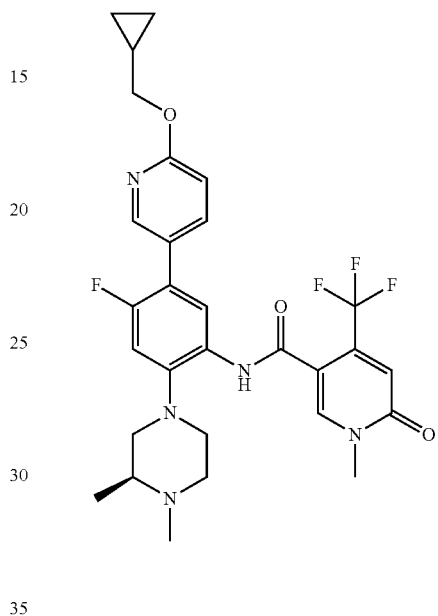

A 30 mL vial was charged with a mixture of (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (30 mg, 0.059 mmol) and 2-(cyclopropylmethoxy)-5-(4,4,5,5-tetramethyl-1,3,2-dioxaborolan-2-yl)pyridine (37.1 mg, 0.135 mmol). Then 1,4-dioxane (5 ml) and a solution of potassium phosphate tribasic (25.2 mg, 0.119 mmol) in water (0.5 ml) were added via syringe and the vial was flushed with argon for 10 minutes. Then bis(di-tert-butyl(4-dimethylaminophenyl)phosphine)dichloropalladium(II) (6.31 mg, 8.91 μmol) was added and the reaction was stirred at 110° C. under microwave for 1.5 hours. The solvent was removed under vacuum and the crude material was concentrated onto celite and purified by Flash chromatography [0-30% MeOH/DCM] to afford the desired (S)—N-(5-(6-(cyclopropylmethoxy)pyridin-3-yl)-2-(3,4-dimethylpiperazin-1-yl)-4-fluorophenyl)-1-methyl-6-oxo-4-(trifluoromethyl)-1,6-dihydropyridine-3-carboxamide (28.4 mg, 0.049 mmol, 82% yield) as a white powder. $^1$H NMR (500 MHz, DMSO-d6) δ=9.46 (s, 1H), 8.31 (s, 1H), 8.25 (s, 1H), 7.81 (d, J=9.78 Hz, 1H), 7.76 (d, J=8.44 Hz, 1H), 7.09 (d, J=12.35 Hz, 1H), 6.94 (d, J=8.68 Hz, 1H), 6.87 (s, 1H), 4.14 (d, J=7.21 Hz, 2H), 3.52 (s, 3H), 2.98-3.09 (m, 2H), 2.83 (br. s., 1H), 2.72-2.79 (m, 1H), 2.42 (t, J=10.45 Hz, 1H), 2.31-2.38 (m, 1H), 2.18-2.29 (m, 4H), 1.23 (s, 2H), 0.98 (d, J=6.24 Hz, 3H), 0.56 (dd, J=1.59, 8.07 Hz, 2H), 0.34 (d, J=4.89 Hz, 2H); LCMS [M+H]+ 574.4.

Example 523: N-(cyclopropylmethyl)-4-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-1,3-thiazole-2-carboxamide Example 524: N-(cyclopropylmethyl)-4-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-N-methyl-1,3-thiazole-2-carboxamide

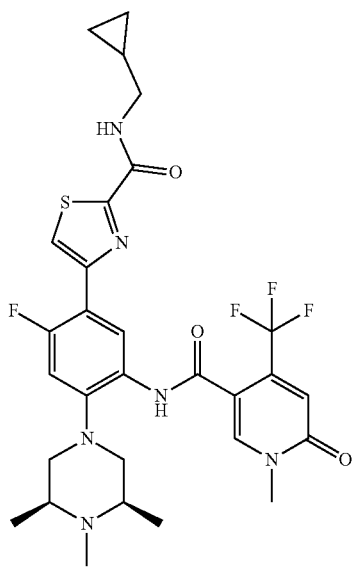

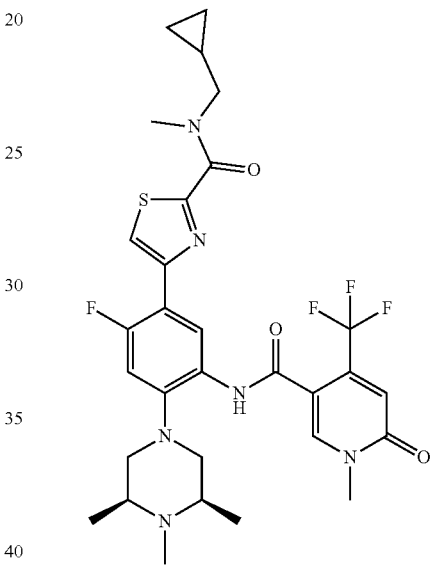

The title compound was prepared using 1-methyl-6-oxo-4-(trifluoromethyl)-1,6-dihydropyridine-3-carboxylic acid and 4-(5-amino-2-fluoro-4-((3S,5R)-3,4,5-trimethylpiperazin-1-yl)phenyl)-N-(cyclopropylmethyl)thiazole-2-carboxamide according to a procedure similar to Example 34. $^1$H NMR (500 MHz, DMSO-d6) δ=9.55 (s, 1H), 8.86 (t, J=6.1 Hz, 1H), 8.40 (s, 1H), 8.23 (d, J=8.3 Hz, 1H), 8.15 (d, J=2.1 Hz, 1H), 7.07 (d, J=13.1 Hz, 1H), 6.89 (s, 1H), 3.55 (s, 3H), 3.17 (t, J=6.5 Hz, 2H), 3.08 (br d, J=11.0 Hz, 2H), 2.38-2.30 (m, 2H), 2.18 (s, 3H), 1.12-1.05 (m, 1H), 1.00 (d, J=6.1 Hz, 6H), 0.48-0.40 (m, 2H), 0.31-0.22 (m, 2H); LCMS [M+H]+: 621.1.

The title compound was prepared using procedures similar to Example 482 using 1-methyl-6-oxo-4-(trifluoromethyl)-1,6-dihydropyridine-3-carboxylic acid and 4-(5-amino-2-fluoro-4-((3S,5R)-3,4,5-trimethylpiperazin-1-yl)phenyl)-N-(cyclopropylmethyl)-N-methylthiazole-2-carboxamide. $^1$H NMR (500 MHz, DMSO-d6) δ=9.46-9.37 (m, 1H), 8.32-8.20 (m, 2H), 8.07 (s, 1H), 7.05-6.97 (m, 1H), 6.81 (s, 1H), 3.89 (br d, J=6.8 Hz, 1H), 3.52 (s, 3H), 3.33 (br d, J=7.0 Hz, 1H), 3.05 (s, 2H), 3.00 (br d, J=11.0 Hz, 2H), 2.33-2.27 (m, 2H), 2.12 (s, 3H), 1.19-1.12 (m, 1H), 0.95 (br d, J=5.9 Hz, 6H), 0.48-0.34 (m, 2H), 0.28-0.16 (m, 2H); LCMS [M+H]+: 635.1.

Example 525: N-cyclohexyl-4-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-1,3-thiazole-2-carboxamide Example 526: N-cyclohexyl-4-[2-fluoro-5-[[1-methyl-6-oxo-4-(trifluoromethyl)pyridine-3-carbonyl]amino]-4-[(3R,5S)-3,4,5-trimethylpiperazin-1-yl]phenyl]-N-methyl-1,3-thiazole-2-carboxamide

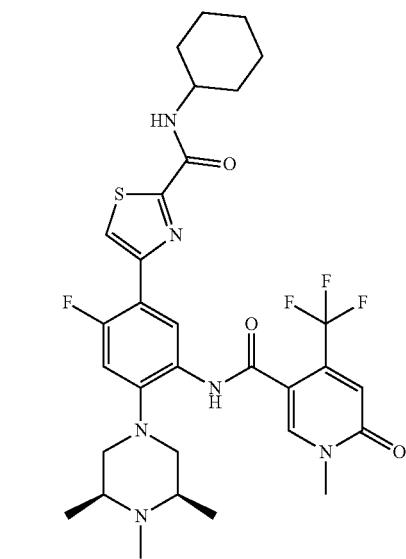

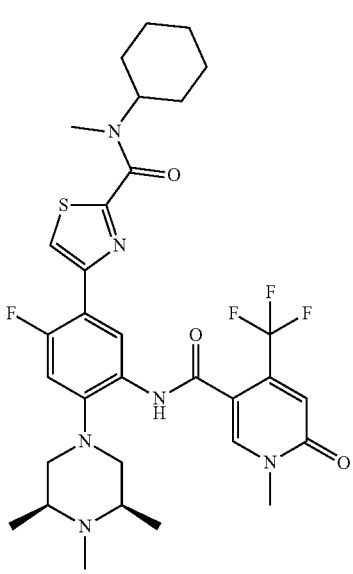 [SMILES: C[C@@H]1CN(c2cc(F)c(-c3csc(C(=O)N(C)C4CCCCC4)n3)cc2NC(=O)c2cn(C)c(=O)cc2C(F)(F)F)C[C@H](C)N1C]

The title compound was prepared by procedures similar to Example 482 using 1-methyl-6-oxo-4-(trifluoromethyl)-1,6-dihydropyridine-3-carboxylic acid and 4-(5-amino-2-fluoro-4-((3S,5R)-3,4,5-trimethylpiperazin-1-yl)phenyl)-N-cyclohexylthiazole-2-carboxamide. $^1$H NMR (500 MHz, DMSO-d6) δ=9.55 (s, 1H), 8.48 (d, J=8.3 Hz, 1H), 8.39 (s, 1H), 8.20 (d, J=8.4 Hz, 1H), 8.14 (d, J=2.1 Hz, 1H), 7.06 (d, J=13.1 Hz, 1H), 6.89 (s, 1H), 3.55 (s, 3H), 3.08 (br d, J=11.2 Hz, 2H), 2.39-2.30 (m, 2H), 2.18 (s, 3H), 1.87-1.78 (m, 2H), 1.73 (br d, J=13.2 Hz, 2H), 1.64-1.56 (m, 1H), 1.45 (dq, J=3.1, 12.0 Hz, 2H), 1.36-1.23 (m, 2H), 1.00 (d, J=6.1 Hz, 6H); LCMS [M+H]+: 649.2.

The title compound was prepared according to a procedure similar to that of Example 482 using 1-methyl-6-oxo-4-(trifluoromethyl)-1,6-dihydropyridine-3-carboxylic acid and 4-(5-amino-2-fluoro-4-((3S,5R)-3,4,5-trimethylpiperazin-1-yl)phenyl)-N-cyclohexyl-N-methylthiazole-2-carboxamide. $^1$H NMR (500 MHz, DMSO-d6) δ=9.49 (br s, 1H), 8.39-8.29 (m, 2H), 8.13 (s, 1H), 7.15-7.04 (m, 1H), 6.88 (s, 1H), 3.53 (s, 3H), 3.09 (br d, J=10.6 Hz, 2H), 2.37 (br t, J=6.9 Hz, 2H), 2.19 (s, 3H), 1.78 (br d, J=10.9 Hz, 2H), 1.70-1.55 (m, 4H), 1.38 (br d, J=9.8 Hz, 3H), 1.02 (br d, J=6.0 Hz, 6H); LCMS [M+H]+: 663.4.

689

Example 527: N-[4-fluoro-5-[2-(morpholine-4-carbonyl)-1,3-thiazol-4-yl]-2-[(3R,5S)-3,4,5-trimethylpiperazin-1-yl]phenyl]-1-methyl-6-oxo-4-(trifluoromethyl)pyridine-3-carboxamide

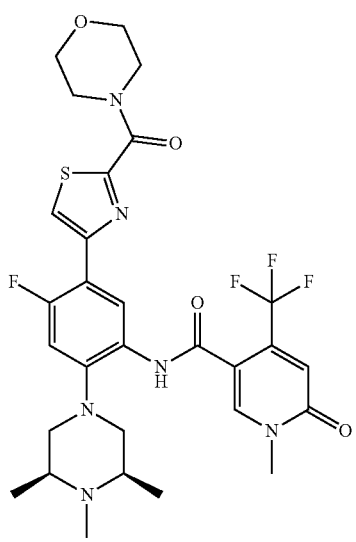 [SMILES: C[C@@H]1CN(c2cc(F)c(-c3csc(C(=O)N4CCOCC4)n3)cc2NC(=O)c2cn(C)c(=O)cc2C(F)(F)F)C[C@H](C)N1C]

The title compound was prepared according to a procedure similar to that described above for the preparation of Example 482 using 1-methyl-6-oxo-4-(trifluoromethyl)-1,6-dihydropyridine-3-carboxylic acid in place of 4-(trifluoromethyl)-6-(2-(trimethylsilyl)ethoxy)nicotinic acid and (4-(5-amino-2-fluoro-4-((3S,5R)-3,4,5-trimethylpiperazin-1-yl)phenyl)thiazol-2-yl)(morpholino)methanone. $^1$H NMR (500 MHz, DMSO-d6) δ=9.50 (s, 1H), 8.39 (d, J=8.3 Hz, 1H), 8.25 (s, 1H), 8.16 (d, J=2.0 Hz, 1H), 7.08 (d, J=13.0 Hz, 1H), 6.89 (s, 1H), 4.36 (br s, 2H), 3.70 (br s, 6H), 3.53 (s, 3H), 3.09 (br d, J=11.0 Hz, 2H), 2.43-2.34 (m, 3H), 2.20 (s, 3H), 1.03 (d, J=6.1 Hz, 6H); LCMS [M+H]+: 637.3.

690

Example 528: N-[4-fluoro-5-[2-(4-methylpiperazine-1-carbonyl)-1,3-thiazol-4-yl]-2-[(3R,5S)-3,4,5-trimethylpiperazin-1-yl]phenyl]-1-methyl-6-oxo-4-(trifluoromethyl)pyridine-3-carboxamide

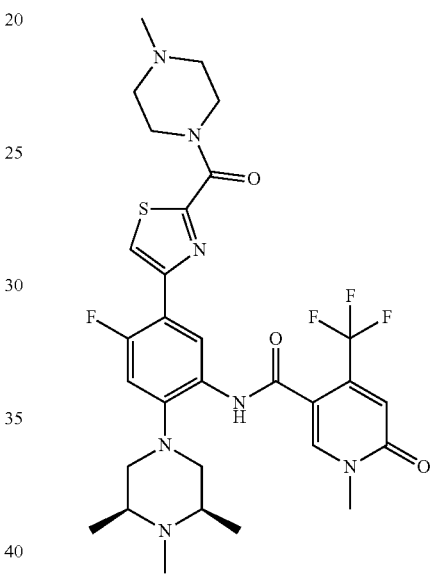

The title compound was prepared according to a procedure similar to that described above for the preparation of Example 482 using 1-methyl-6-oxo-4-(trifluoromethyl)-1,6-dihydropyridine-3-carboxylic acid and (4-(5-amino-2-fluoro-4-((3S,5R)-3,4,5-trimethylpiperazin-1-yl)phenyl)thiazol-2-yl)(4-methylpiperazin-1-yl)methanone. $^1$H NMR (500 MHz, DMSO-d6) δ=9.49 (s, 1H), 8.41 (d, J=8.3 Hz, 1H), 8.23 (s, 1H), 8.14 (d, J=2.0 Hz, 1H), 7.07 (d, J=13.0 Hz, 1H), 6.89 (s, 1H), 4.29 (br s, 2H), 3.68 (br s, 2H), 3.52 (s, 3H), 3.08 (br d, J=11.1 Hz, 2H), 2.42 (br s, 5H), 2.20 (s, 3H), 2.20 (s, 3H), 1.03 (d, J=6.0 Hz, 6H); LCMS [M+H]+: 650.3.

Example 529: 4-fluoro-N-[4-fluoro-5-(4-piperazin-1-ylphenyl)-2-[(3R)-3,4-dimethylpiperazin-1-yl]phenyl]-2-(trifluoromethyl)benzamide

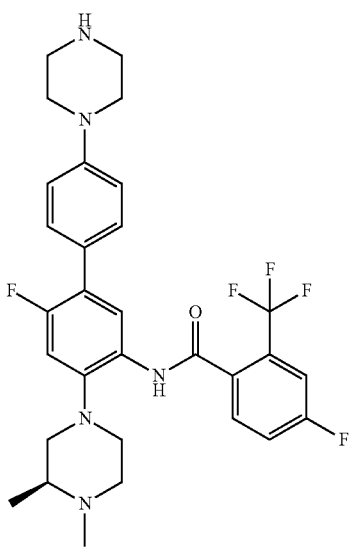 [SMILES: C[C@H]1CN(c2cc(F)c(-c3ccc(N4CCNCC4)cc3)cc2NC(=O)c2ccc(F)cc2C(F)(F)F)CCN1C]

To a solution of tert-butyl (S)-4-(4'-(3,4-dimethylpiperazin-1-yl)-2'-fluoro-5'-(4-fluoro-2-(trifluoromethyl)benzamido)-[1,1'-biphenyl]-4-yl)piperazine-1-carboxylate (68.4 mg, 0.102 mmol, prepared by similar methods to Example 400) in DCM (3 ml) was added trifluoroacetic acid (3 ml, 39.2 mmol). The reaction mixture was stirred at 24° C. for 30 minutes. Workup and purification gave the title compound (58.1 mg, 0.096 mmol, 95% yield) as a white powder. $^1$H NMR (500 MHz, DMSO-d6) δ=9.60 (s, 1H), 7.75-7.83 (m, 3H), 7.69-7.74 (m, 1H), 7.44 (d, J=8.80 Hz, 1H), 7.36 (d, J=7.95 Hz, 2H), 7.00-7.07 (m, 3H), 6.88-6.97 (m, 1H), 3.09-3.14 (m, 4H), 3.09-3.14 (m, 4H), 2.98-3.08 (m, 4H), 2.84-2.89 (m, 6H), 2.74-2.81 (m, 1H), 2.43 (t, J=10.51 Hz, 1H), 2.27-2.34 (m, 1H), 2.19 (s, 4H), 0.98 (d, J=6.24 Hz, 3H); LCMS [M+H]+ 574.4.

Example 530: 4-fluoro-N-[4-fluoro-5-(6-piperazin-1-ylpyridin-3-yl)-2-[(3R)-3,4-dimethylpiperazin-1-yl]phenyl]-2-(trifluoromethyl)benzamide To a solution of tert-butyl (S)-4-(5-(4-(3,4-dimethylpiperazin-1-yl)-2-fluoro-5-(4-fluoro-2-(trifluoromethyl)benzamido)phenyl)pyridin-2-yl)piperazine-1-carboxylate (69.9 mg, 0.104 mmol, prepared by similar methods as those in Example 400) in DCM (3 ml) was added TFA (3 ml, 39.2 mmol). The reaction mixture was stirred at 24° C. for 30 min. Standard workup and purification gave the title compound (47.7 mg, 0.081 mmol, 79% yield) as a white powder. $^1$H NMR (500 MHz, DMSO-d6) δ=9.63 (s, 1H), 8.25 (s, 1H), 7.75-7.83 (m, 3H), 7.72 (dt, J=1.96, 8.30 Hz, 1H), 7.65 (d, J=8.80 Hz, 1H), 7.07 (d, J=12.35 Hz, 1H), 6.90 (d, J=8.93 Hz, 1H), 3.43-3.48 (m, 4H), 3.02 (dd, J=10.94, 18.28 Hz, 2H), 2.72-2.86 (m, 7H), 2.43 (t, J=10.51 Hz, 1H), 2.27-2.34 (m, 1H), 2.19 (s, 4H), 0.98 (d, J=6.24 Hz, 3H); LCMS [M+H]+ 575.4.

Example 531: N-(cyclopropylmethyl)-4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-1,3-thiazole-2-carboxamide

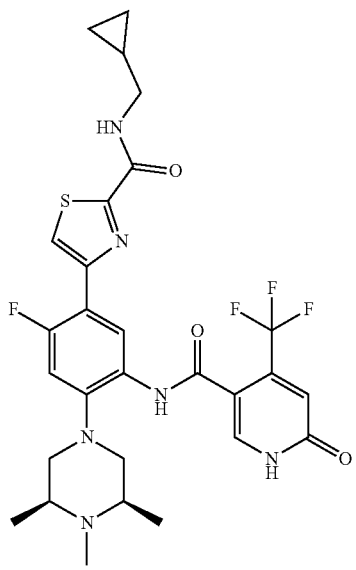

The title compound was prepared in a manner similar to Example 482 from 4-(trifluoromethyl)-6-(2-(trimethylsilyl)ethoxy)nicotinic acid and 4-(5-amino-2-fluoro-4-((3S,5R)-3,4,5-trimethylpiperazin-1-yl)phenyl)-N-(cyclopropylmethyl)thiazole-2-carboxamide. $^1$H NMR (500 MHz, DMSO-d6) δ=9.54 (s, 1H), 8.86 (t, J=6.0 Hz, 1H), 8.20 (d, J=8.6 Hz, 1H), 8.14 (d, J=2.1 Hz, 1H), 8.01 (s, 1H), 7.06 (d, J=13.1 Hz, 1H), 6.75 (s, 1H), 3.17 (t, J=6.5 Hz, 3H), 3.08 (br d, J=11.1 Hz, 2H), 2.37-2.27 (m, 3H), 2.19 (s, 3H), 1.24 (s, 1H), 1.01 (d, J=6.1 Hz, 6H), 0.47-0.42 (m, 2H), 0.29-0.24 (m, 2H); LCMS [M+H]+: 607.0.

Example 532: N-(cyclopropylmethyl)-4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-N-methyl-1,3-thiazole-2-carboxamide

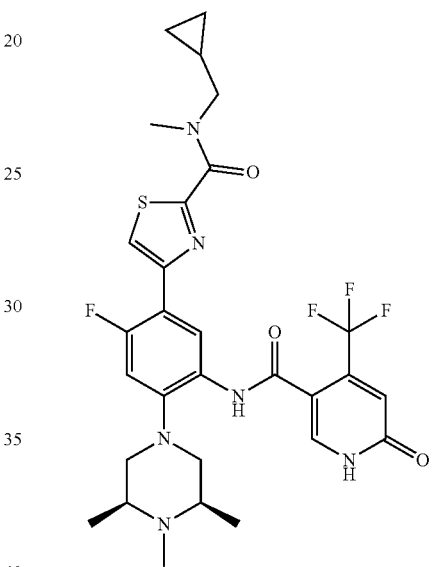

The title compound was prepared according to a procedure similar to Example 482 using 4-(5-amino-2-fluoro-4-((3S,5R)-3,4,5-trimethylpiperazin-1-yl)phenyl)-N-(cyclopropylmethyl)-N-methylthiazole-2-carboxamide and 4-(trifluoromethyl)-6-(2-(trimethylsilyl)ethoxy)nicotinic acid. $^1$H NMR (500 MHz, DMSO-d6) δ=9.43-9.32 (m, 1H), 8.32-8.23 (m, 1H), 8.06 (d, J=1.8 Hz, 1H), 7.86 (br s, 1H), 7.04-6.93 (m, 1H), 6.62 (br s, 1H), 3.90 (d, J=7.0 Hz, 1H), 3.53 (s, 1H), 3.34 (br d, J=6.8 Hz, 1H), 3.05 (s, 2H), 3.00 (br d, J=10.1 Hz, 2H), 2.31-2.25 (m, 2H), 2.13 (s, 3H), 1.17 (s, 1H), 0.95 (d, J=6.1 Hz, 6H), 0.46-0.35 (m, 2H), 0.27-0.17 (m, 2H); LCMS [M+H]+: 621.6.

Example 533: N-cyclohexyl-4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-1,3-thiazole-2-carboxamide Example 534: N-cyclohexyl-4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-N-methyl-1,3-thiazole-2-carboxamide

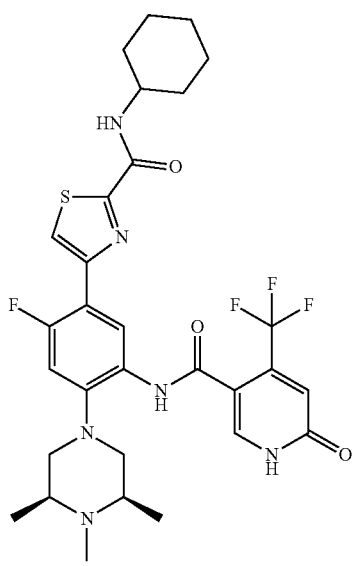

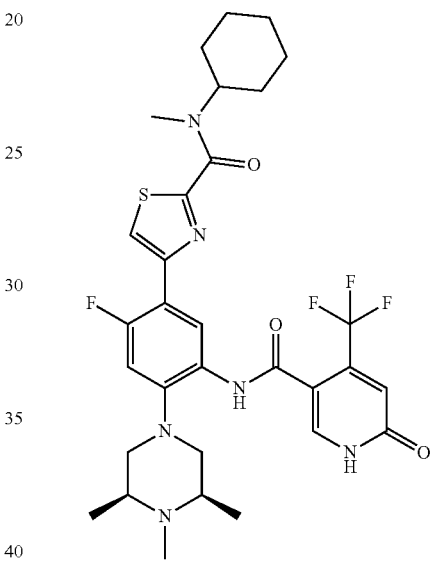

The title compound was prepared according to a procedure similar to Example 482 from 4-(5-amino-2-fluoro-4-((3S,5R)-3,4,5-trimethylpiperazin-1-yl)phenyl)-N-cyclohexylthiazole-2-carboxamide and 4-(trifluoromethyl)-6-(2-(trimethylsilyl)ethoxy)nicotinic acid. $^1$H NMR (500 MHz, DMSO-d6) δ=9.41 (br s, 1H), 8.41 (d, J=8.6 Hz, 1H), 8.12 (d, J=8.4 Hz, 1H), 8.05 (d, J=2.1 Hz, 1H), 7.96 (s, 1H), 6.97 (d, J=13.1 Hz, 1H), 6.61 (br s, 1H), 3.70 (dtd, J=3.7, 7.7, 15.1 Hz, 1H), 3.00 (br d, J=10.9 Hz, 3H), 2.29-2.21 (m, 2H), 2.12 (s, 3H), 1.79-1.72 (m, 2H), 1.66 (br d, J=13.0 Hz, 2H), 1.58-1.50 (m, 1H), 1.44-1.33 (m, 2H), 1.29-1.15 (m, 4H), 1.10-1.03 (m, 1H), 0.93 (d, J=6.1 Hz, 6H); LCMS [M+H]+: 635.2.

The title compound was prepared according to a procedure similar to Example 482 from 4-(5-amino-2-fluoro-4-((3S,5R)-3,4,5-trimethylpiperazin-1-yl)phenyl)-N-cyclohexyl-N-methylthiazole-2-carboxamide and 4-(trifluoromethyl)-6-(2-(trimethylsilyl)ethoxy)nicotinic acid. $^1$H NMR (500 MHz, DMSO-d6) δ=9.52 (s, 1H), 8.34-8.25 (m, 1H), 8.13 (s, 1H), 7.95-7.86 (m, 1H), 7.12-7.02 (m, 1H), 6.76 (s, 1H), 5.23-5.09 (m, 1H), 4.40-4.29 (m, 1H), 3.39 (s, 1H), 3.08 (br d, J=10.9 Hz, 2H), 2.94 (s, 2H), 2.36 (br dd, J=3.4, 6.7 Hz, 2H), 2.20 (s, 3H), 1.79 (br d, J=10.9 Hz, 2H), 1.73-1.54 (m, 5H), 1.46-1.29 (m, 3H), 1.24 (s, 1H), 1.02 (d, J=6.1 Hz, 6H); LCMS [M+H]+: 649.4.

Example 535: N-[4-fluoro-5-[2-(morpholine-4-carbonyl)-1,3-thiazol-4-yl]-2-[(3R,5S)-3,4,5-trimethylpiperazin-1-yl]phenyl]-6-oxo-4-(trifluoromethyl)-1H-pyridine-3-carboxamide

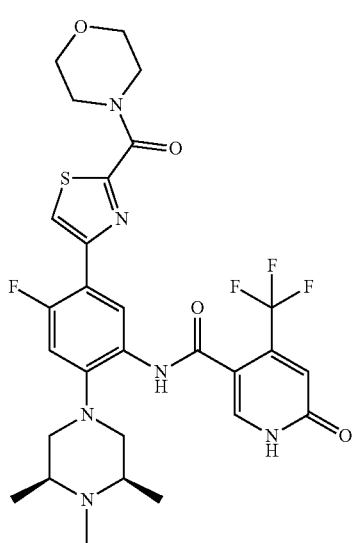

The title compound was prepared according to a procedure similar to the preparation of Example 482 from (4-(5-amino-2-fluoro-4-((3S,5R)-3,4,5-trimethylpiperazin-1-yl)phenyl)thiazol-2-yl)(morpholino)methanone and 4-(trifluoromethyl)-6-(2-(trimethylsilyl)ethoxy)nicotinic acid. $^1$H NMR (500 MHz, DMSO-d6) δ=12.65-12.42 (m, 1H), 9.55 (s, 1H), 8.36 (d, J=8.4 Hz, 1H), 8.15 (d, J=2.1 Hz, 1H), 7.86 (s, 1H), 7.06 (d, J=13.1 Hz, 1H), 6.79 (s, 1H), 4.39 (br s, 2H), 3.71 (br s, 6H), 3.09 (br d, J=10.9 Hz, 2H), 2.41-2.33 (m, 2H), 2.21 (s, 3H), 1.03 (d, J=6.1 Hz, 6H); LCMS [M+H]+: 623.5.

Example 536: N-[4-fluoro-5-[2-(4-methylpiperazine-1-carbonyl)-1,3-thiazol-4-yl]-2-[(3R,5S)-3,4,5-trimethylpiperazin-1-yl]phenyl]-6-oxo-4-(trifluoromethyl)-1H-pyridine-3-carboxamide The title compound was prepared by a procedure similar to the preparation of Example 482 from (4-(5-amino-2-fluoro-4-((3S,5R)-3,4,5-trimethylpiperazin-1-yl)phenyl)thiazol-2-yl)(4-methylpiperazin-1-yl)methanone and 4-(trifluoromethyl)-6-(2-(trimethylsilyl)ethoxy)nicotinic acid. $^1$H NMR (500 MHz, DMSO-d6) δ=9.50 (br s, 1H), 8.40 (br d, J=8.3 Hz, 1H), 8.14 (d, J=1.6 Hz, 1H), 7.87 (s, 1H), 7.07 (d, J=13.0 Hz, 1H), 6.73 (br s, 1H), 4.32 (br s, 2H), 3.69 (br s, 2H), 3.08 (br d, J=11.0 Hz, 2H), 2.43 (br s, 4H), 2.38 (br d, J=6.6 Hz, 2H), 2.22 (br s, 6H), 1.04 (d, J=6.0 Hz, 7H); LCMS [M+H]+: 636.5.

Example 537: N-[5-[2-(cyclohexylamino)pyrimidin-4-yl]-4-fluoro-2-[(3R,5S)-3,4,5-trimethylpiperazin-1-yl]phenyl]-6-oxo-4-(triluoromethyl)-1H-pyridine-3-carboxamide

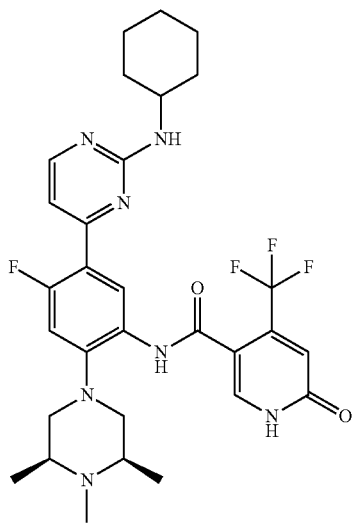

In N,N-Dimethylformamide (520 µl) was dissolved N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy)nicotinamide (106 mg, 0.130 mmol, preparation described in Example 384). To the solution was added (4-bromopyrimidin-2-yl)cyclohexylamine (33.3 mg, 0.130 mmol), LiCl (16.53 mg, 0.390 mmol) and bis(triphenylphosphine)palladium(II) dichloride (5.02 mg, 7.15 µmol) at room temperature and then it was microwaved at the temperature of 120° C. for 3 hours. The reaction mixture was quenched with water and then extracted with DCM. The organic layer, thus separated, was concentrated and purified by column chromatography. Purification was performed via Biotage column, (100-0%, CH$_2$Cl$_2$: 10% MeOH in CH$_2$Cl$_2$+NH$_4$Ac; in 10 min and isocratic for 5 min [new isolera 2.3] using KP-SIL 10 g column. Collected 20% of the CH2Cl$_2$) to yield the pure product that was lyophilized for 1 day. There were several impurities present so it was decided to purify via prep-HPLC after the deprotection. The product was dissolved in 2 mL of DCM and trifluoroacetic acid (995 µl, 12.99 mmol) was added. The purple solution was stirred for 1 h and the solvent was evaporated. The product was purified by prep HPLC to give the title compound (4.3 mg, 6% yield). $^1$H NMR (500 MHz, MeOD) δ 8.56 (s, 1H), 8.24 (d, J=5.3 Hz, 1H), 7.91 (s, 1H), 7.06-6.99 (m, 2H), 6.92 (s, 1H), 3.86 (s, 1H), 3.15 (s, 1H), 2.68-2.54 (m, 4H), 2.40 (s, 3H), 2.04 (d, J=9.9 Hz, 2H), 1.78 (d, J=13.6 Hz, 2H), 1.66 (d, J=13.0 Hz, 1H), 1.46 (dd, J=25.1, 12.5 Hz, 2H), 1.34-1.24 (m, 3H), 1.18 (d, J=5.6 Hz, 6H); LCMS [M+1]$^+$=602.7.

Example 538: N-[4-fluoro-5-[2-(methylamino)pyrimidin-4-yl]-2-[(3R,5S)-3,4,5-trimethylpiperazin-1-yl]phenyl]-6-oxo-4-(trifluoromethyl)-1H-pyridine-3-carboxamide

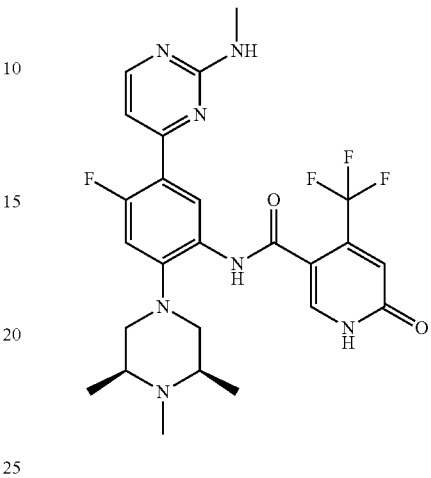

The title compound was prepared similar to the sequence described above for the preparation of Example 537 using 4-bromo-N-methylpyrimidin-2-amine and N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy)nicotinamide. $^1$H NMR (500 MHz, MeOD) δ 8.53 (s, 1H), 8.27 (d, J=5.2 Hz, 1H), 7.94 (s, 1H), 7.06 (dd, J=5.1, 1.7 Hz, 1H), 7.03 (d, J=13.1 Hz, 1H), 6.92 (s, 1H), 3.19 (s, 2H), 2.98 (s, 3H), 2.69 (s, 2H), 2.45 (s, 2H), 1.20 (s, 6H); LCMS [M+1]$^+$=534.6.

Example 539: N-[5-(2-cyanopyrimidin-4-yl)-4-fluoro-2-[(3S,5S)-3,4,5-trimethylpiperazin-1-yl]phenyl]-6-oxo-4-(trifluoromethyl)-1H-pyridine-3-carboxamide

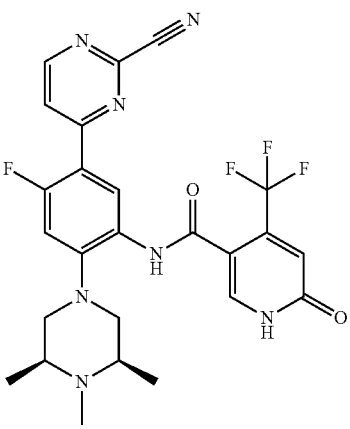 [SMILES: C[C@@H]1CN(c2cc(F)c(-c3ccnc(C#N)n3)cc2NC(=O)c2c[nH]c(=O)cc2C(F)(F)F)C[C@H](C)N1C]

The title compound was prepared similar to the sequence described above for the preparation of Example 537 using 4-bromopyrimidine-2-carbonitrile and N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy)nicotinamide. $^1$H NMR (500 MHz, DMSO) δ 9.72 (s, 1H), 9.00 (d, J=5.5 Hz, 1H), 8.28 (d, J=8.2 Hz, 1H), 8.13 (d, J=5.0 Hz, 1H), 7.08 (d, J=13.9 Hz, 1H), 6.82 (s, 1H), 3.23 (d, J=10.9 Hz, 2H), 2.55 (d, J=11.1 Hz, 2H), 2.34 (s, 2H), 2.19 (s, 4H), 1.01 (d, J=5.9 Hz, 6H); $^{19}$F NMR (471 MHz, DMSO) δ −61.26 (s), −114.60 (s); LCMS HSS [M+1]$^+$=530.5.

Example 540: N-[5-[2-(dimethylamino)pyrimidin-4-yl]-4-fluoro-2-[(3R,5S)-3,4,5-trimethylpiperazin-1-yl]phenyl]-6-oxo-4-(trifluoromethyl)-1H-pyridine-3-carboxamide

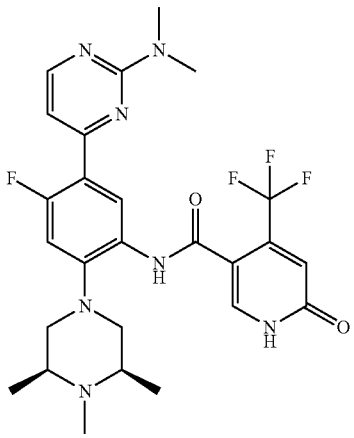 [SMILES: C[C@@H]1CN(c2cc(F)c(-c3ccnc(N(C)C)n3)cc2NC(=O)c2c[nH]c(=O)cc2C(F)(F)F)C[C@H](C)N1C]

The title compound was prepared similar to the sequence described above for the preparation of Example 537 using 4-bromo-N,N-dimethylpyrimidin-2-amine and N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy) nicotinamide. $^1$H NMR (500 MHz, MeOD) δ 8.60 (d, J=8.1 Hz, 1H), 8.32 (d, J=5.3 Hz, 1H), 7.93 (s, 1H), 7.05 (dd, J=5.2, 2.0 Hz, 1H), 7.00 (d, J=13.2 Hz, 1H), 6.91 (s, 1H), 3.23 (s, 6H), 3.16 (d, J=11.2 Hz, 2H), 2.63 (t, J=11.2 Hz, 2H), 2.56 (d, J=6.2 Hz, 2H), 2.37 (s, 3H), 1.17 (d, J=6.2 Hz, 6H); LCMS [M+1]$^+$=590.6.

Example 541: N-[4-fluoro-2-[4-(methylamino)piperidin-1-yl]-5-(2-morpholin-4-ylpyrimidin-5-yl)phenyl]-6-oxo-4-(trifluoromethyl)-1H-pyridine-3-carboxamide

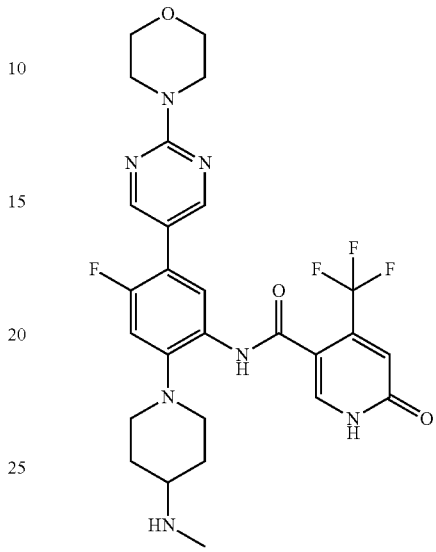

Step 1: tert-butyl (1-(5-fluoro-4-(2-morpholinopyrimidin-5-yl)-2-(4-(trifluoromethyl)-6-(2-(trimethylsilyl)ethoxy)nicotinamido)phenyl)piperidin-4-yl)(methyl)carbamate

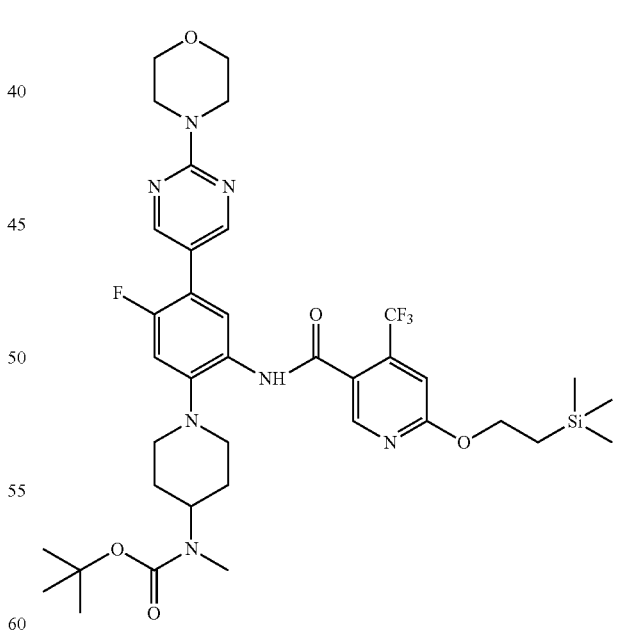

To a solution of tert-butyl (1-(2-amino-5-fluoro-4-(2-morpholinopyrimidin-5-yl)phenyl)piperidin-4-yl)(methyl)carbamate, (0.623 g, 1.280 mmol, prepared from a 3 step procedure similar to Examples hereinabove starting from tert-butyl methyl(piperidin-4-yl)carbamate and 1-bromo-2,4-difluoro-5-nitrobenzene), 4-(trifluoromethyl)-6-(2-(trimethylsilyl)ethoxy)nicotinic acid (0.512 g, 1.664 mmol) in ethyl acetate (EtOAc) (15 ml) was added 4-methylmorpholine (0.422 ml, 3.84 mmol) at 0° C. The reaction mixture was stirred for 15 minutes before adding propylphosphonic anhydride solution (2.287 ml, 3.84 mmol) dropwise. The reaction mixture was further stirred at 0° C. for 1 hour and at room temperature for an extra 5 hours. A standard workup and purification with silica gel chromatography afforded the title compound (1.08 g, 84% yield). LCMS [M+H]+=776.5.

Step 2: N-[4-fluoro-2-[4-(methylamino)piperidin-1-yl]-5-(2-morpholin-4-ylpyrimidin-5-yl)phenyl]-6-oxo-4-(trifluoromethyl)-1H-pyridine-3-carboxamide

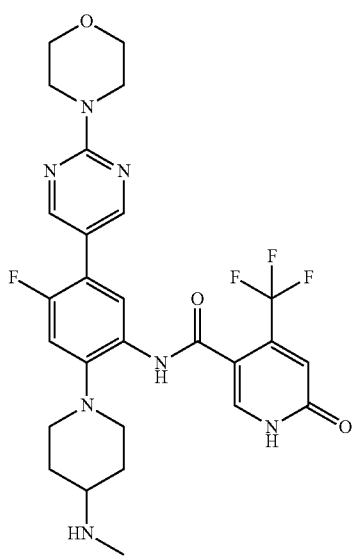 [SMILES: CNC1CCN(c2cc(F)c(-c3cnc(N4CCOCC4)nc3)cc2NC(=O)c2c[nH]c(=O)cc2C(F)(F)F)CC1]

To a solution of tert-butyl (1-(5-fluoro-4-(2-morpholinopyrimidin-5-yl)-2-(4-(trifluoromethyl)-6-(2-(trimethylsilyl)ethoxy)nicotinamido)phenyl)piperidin-4-yl)(methyl)carbamate (1.0756 g, 1.081 mmol) in DCM (3 mL) was added TFA (3 ml, 39.2 mmol). The reaction mixture was stirred at 24° C. for 30 minutes. The TFA and solvent were removed under vacuum and the product was purified by Flash chromatography [0-30% MeOH/DCM] to afford the TFA salt of N-(4-fluoro-2-(4-(methylamino)piperidin-1-yl)-5-(2-morpholinopyrimidin-5-yl)phenyl)-6-oxo-4-(trifluoromethyl)-1,6-dihydropyridine-3-carboxamide. The product was dissolved in MeOH and passed through a PoraPak Rxn CX (20 cc-2 g) cartridge in a catch and elute method. The cartridge was washed with MeOH, then the solution of product in MeOH was added onto the cartridge. The cartridge was rinsed with MeOH (2×20 mL) and then with a solution of 10 mL (NH₃ in MeOH at 7N) in 40 mL of MeOH to release the free base of the title compound (228.9 mg, 0.338 mmol, 31.3% yield) as a white powder. $^1$H NMR (500 MHz, DMSO-d6) δ=9.43 (s, 1H), 8.52 (d, J=0.86 Hz, 2H), 7.95 (s, 1H), 7.81 (d, J=8.56 Hz, 1H), 7.09 (d, J=12.35 Hz, 1H), 6.73 (s, 1H), 3.74-3.78 (m, 4H), 3.65-3.70 (m, 4H), 3.11 (d, J=11.74 Hz, 2H), 2.66 (t, J=11.19 Hz, 2H), 2.42-2.48 (m, 1H), 2.31 (s, 3H), 1.88 (d, J=14.55 Hz, 2H), 1.44 (d, J=10.15 Hz, 2H); LCMS [M+H]+ 576.5.

Example 542: 4-(difluoromethyl)-N-[4-fluoro-5-[6-[(2R)-2-methylmorpholin-4-yl]pyridin-3-yl]-2-[(3R,5S)-3,4,5-trimethylpiperazin-1-yl]phenyl]-1-methyl-6-oxopyridine-3-carboxamide

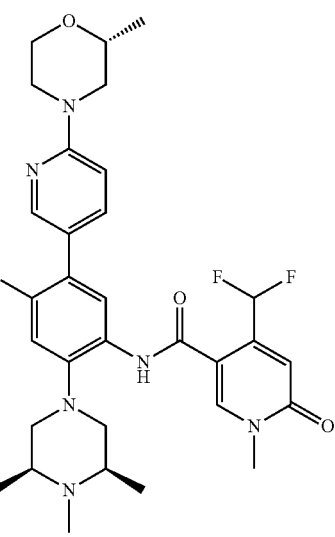

To a suspension of 4-(difluoromethyl)-N-(4-fluoro-5-(6-((R)-2-methylmorpholino)pyridin-3-yl)-2-((3S,5R)-3,4,5-trimethylpiperazin-1-yl)phenyl)-6-oxo-1,6-dihydropyridine-3-carboxamide (41.8 mg, 0.071 mmol) and cesium carbonate (25.6 mg, 0.079 mmol) in N,N-dimethylformamide (4 ml) was added iodomethane (4.90 µl, 0.079 mmol) at room temperature and the reaction mixture was stirred for 2 hours. Then the reaction mixture was poured into water and the product was extracted by DCM. The organic phase was dried over MgSO₄. After filtration and evaporation of the solvent, the product was dissolved in MeOH and passed through a PoraPak Rxn CX (20 cc-2 g) cartridge in a catch and elute method. The cartridge was washed with MeOH, then the solution of product in MeOH was added onto the cartridge. The cartridge was rinsed with MeOH (2×20 mL) and then with a solution of 10 mL (NH₃ in MeOH at 7N) in 40 mL of MeOH to release the free base of 4-(difluoromethyl)-N-(4-fluoro-5-(6-((R)-2-methylmorpholino)pyridin-3-yl)-2-((3S,5R)-3,4,5-trimethylpiperazin-1-yl)phenyl)-1-methyl-6-oxo-1,6-dihydropyridine-3-carboxamide (36.2 mg, 80% yield) as an off-white powder. $^1$H NMR (500 MHz, DMSO-d6) δ=9.46 (s, 1H), 8.35 (s, 1H), 8.26 (s, 1H), 7.64-7.70 (m, 2H), 7.33 (t, J=54.50 Hz, 1H), 7.03 (d, J=12.47 Hz, 1H), 6.94 (d, J=8.93 Hz, 1H), 6.64 (s, 1H), 4.18 (d, J=12.47 Hz, 1H), 4.08 (d, J=12.84 Hz, 1H), 3.92 (dd, J=2.45, 11.49 Hz, 1H), 3.56 (dd, J=2.51, 11.07 Hz, 2H), 3.52 (s, 3H), 3.02 (d, J=10.88 Hz, 2H), 2.84 (dt, J=3.42, 12.35 Hz, 1H), 2.35 (d, J=6.24 Hz, 2H), 2.19 (s, 3H), 1.17 (d, J=6.24 Hz, 4H), 1.00 (d, J=6.11 Hz, 6H); LCMS [M]+ 599.6.

705

Example 543: N-[5-[6-(cyclopropylmethoxy)pyridin-3-yl]-4-fluoro-2-[(3R)-3,4-dimethylpiperazin-1-yl]phenyl]-4-(difluoromethyl)-1-methyl-6-oxopyridine-3-carboxamide

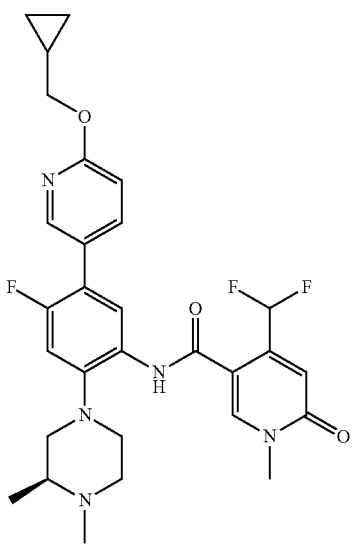

The procedure followed was similar to Example 217 using (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (30 mg, 0.059 mmol) and 2-(cyclopropylmethoxy)-5-(4,4,5,5-tetramethyl-1,3,2-dioxaborolan-2-yl)pyridine (37.1 mg, 0.135 mmol) to afford the title compound (28.4 mg, 0.049 mmol, 82% yield) as a white powder. $^1$H NMR (500 MHz, DMSO-d6) δ=9.46 (s, 1H), 8.31 (s, 1H), 8.25 (s, 1H), 7.81 (d, J=9.78 Hz, 1H), 7.76 (d, J=8.44 Hz, 1H), 7.09 (d, J=12.35 Hz, 1H), 6.94 (d, J=8.68 Hz, 1H), 6.87 (s, 1H), 4.14 (d, J=7.21 Hz, 2H), 3.52 (s, 3H), 2.98-3.09 (m, 2H), 2.83 (br. s., 1H), 2.72-2.79 (m, 1H), 2.42 (t, J=10.45 Hz, 1H), 2.31-2.38 (m, 1H), 2.18-2.29 (m, 4H), 1.23 (s, 2H), 0.98 (d, J=6.24 Hz, 3H), 0.56 (dd, J=1.59, 8.07 Hz, 2H), 0.34 (d, J=4.89 Hz, 2H); LCMS [M+H]+ 574.4.

706

Example 544: N-[4-fluoro-2-[(3S)-3,4-dimethylpiperazin-1-yl]-5-[2-[(2R)-2-methylmorpholin-4-yl]pyrimidin-5-yl]phenyl]-1-methyl-6-oxo-4-(trifluoromethyl)pyridine-3-carboxamide

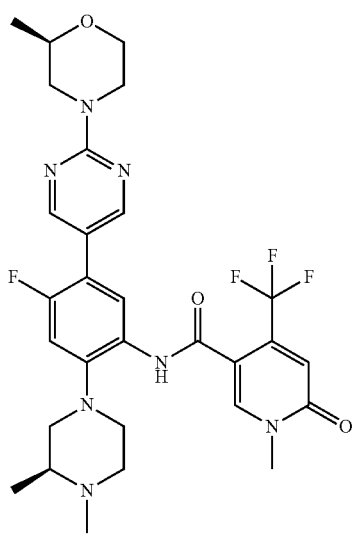 [SMILES: C[C@@H]1CN(c2ncc(-c3cc(NC(=O)c4cn(C)c(=O)cc4C(F)(F)F)c(N4CCN(C)[C@@H](C)C4)cc3F)cn2)CCO1]

The title compound (off white solid, 16.4 mg, 35%) was prepared by a procedure similar to Example 100 using crude (R)-(2-(2-methylmorpholino)pyrimidin-5-yl)boronic acid (0.15 mmol×2) and (S)—N-(5-bromo-2-(3,4-dimethylpiperazin-1-yl)-4-fluorophenyl)-1-methyl-6-oxo-4-(trifluoromethyl)-1,6-dihydropyridine-3-carboxamide (38 mg, 0.075 mmol). $^1$H NMR (500 MHz, METHANOL-d4) δ=8.56 (s, 2H), 8.27 (s, 1H), 7.91 (d, J=8.2 Hz, 1H), 7.12 (d, J=12.1 Hz, 1H), 6.95 (s, 1H), 4.65-4.54 (m, 2H), 3.99 (dd, J=2.5, 11.6 Hz, 1H), 3.67 (s, 3H), 3.65-3.59 (m, 2H), 3.17-3.03 (m, 3H), 3.02-2.87 (m, 2H), 2.73 (dd, J=10.5, 13.3 Hz, 1H), 2.59 (br t, J=10.6 Hz, 2H), 2.47 (br s, 1H), 2.41 (br s, 3H), 1.25 (d, J=6.2 Hz, 3H), 1.15 (br d, J=6.1 Hz, 3H); LCMS [M+H]+ 604.4.

Example 545: 4-fluoro-N-[4-fluoro-5-[2-[(2R)-2-methylmorpholin-4-yl]pyrimidin-5-yl]-2-[(3R,5S)-3,4,5-trimethylpiperazin-1-yl]phenyl]-2-(trifluoromethyl)benzamide

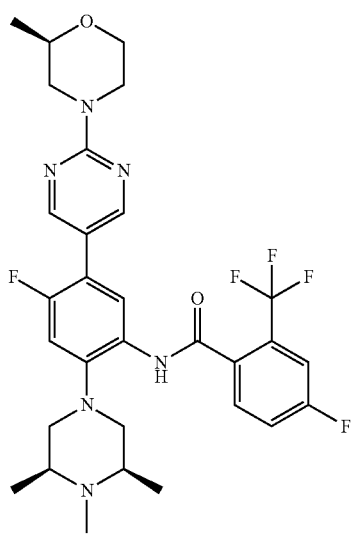

The title compound (formic acid salt, off white solid, 44.0 mg, 67%) was prepared by a procedure similar to Example 31 using crude (R)-(2-(2-methylmorpholino)pyrimidin-5-yl)boronic acid (0.3 mmol) and N-(5-bromo-4-fluoro-2-((3S,5R)-3,4,5-trimethylpiperazin-1-yl)phenyl)-4-fluoro-2-(trifluoromethyl)benzamide (57 mg, 89% purity, 0.1 mmol). $^1$H NMR (500 MHz, METHANOL-d4) δ=8.57 (s, 2H), 8.44 (br s, 1H), 8.06 (d, J=8.2 Hz, 1H), 7.81 (dd, J=5.3, 8.4 Hz, 1H), 7.67 (dd, J=2.2, 9.0 Hz, 1H), 7.58 (dt, J=2.3, 8.3 Hz, 1H), 7.20 (d, J=11.7 Hz, 1H), 4.66-4.55 (m, 2H), 3.99 (dd, J=3.1, 11.5 Hz, 1H), 3.68-3.59 (m, 2H), 3.30-3.19 (m, 4H), 3.18-3.05 (m, 1H), 2.97-2.86 (m, 2H), 2.82-2.77 (m, 3H), 2.74 (dd, J=10.5, 13.1 Hz, 1H), 1.37 (dd, J=1.5, 6.1 Hz, 6H), 1.25 (d, J=6.2 Hz, 3H); LCMS [M+H]$^+$ 605.4.

Example 546: 4-fluoro-N-[4-fluoro-5-(2-piperazin-1-ylpyrimidin-5-yl)-2-[(3R,5S)-3,4,5-trimethylpiperazin-1-yl]phenyl]-2-(trifluoromethyl)benzamide

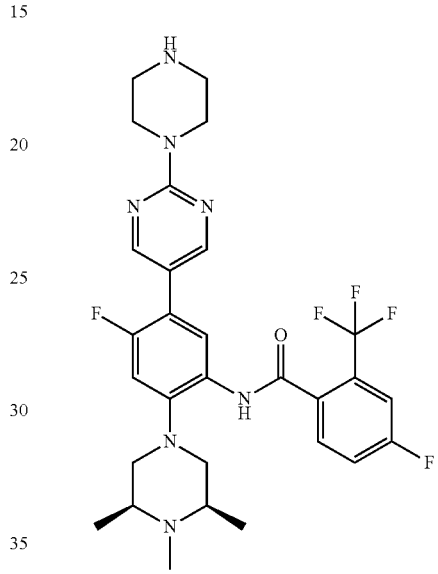

Intermediate tert-butyl 4-(5-(2-fluoro-5-(4-fluoro-2-(trifluoromethyl)benzamido)-4-((3R,5S)-3,4,5-trimethylpiperazin-1-yl)phenyl)pyrimidin-2-yl)piperazine-1-carboxylate (dark brown solid) was prepared by a procedure similar to Example 400 using 2-(4-Boc-piperazino)pyrimidine-5-boronic acid pinacol ester (78 mg, 0.2 mmol) and N-(5-bromo-4-fluoro-2-((3S,5R)-3,4,5-trimethylpiperazin-1-yl)phenyl)-4-fluoro-2-(trifluoromethyl)benzamide (57 mg, 89% purity, 0.1 mmol). LCMS [M+H]$^+$ 690.4. The solid was redissolved in DCM (5 mL) and treated with TFA (0.31 mL). The resulting mixture was stirred at rt overnight. After removal of the solvents, the residue was purified by prep-HPLC and Biotage Isolute SCX-2 column to give the title compound as a beige solid (49.0 mg, 81% over 2 steps). $^1$H NMR (500 MHz, METHANOL-d4) δ=8.56 (s, 2H), 8.02 (d, J=8.2 Hz, 1H), 7.78 (dd, J=5.3, 8.4 Hz, 1H), 7.66 (dd, J=2.3, 9.0 Hz, 1H), 7.57 (dt, J=2.2, 8.2 Hz, 1H), 7.11 (d, J=12.0 Hz, 1H), 3.88 (br s, 4H), 3.06 (br d, J=11.2 Hz, 2H), 2.93 (br s, 4H), 2.62 (br t, J=11.2 Hz, 2H), 2.51-2.41 (m, 2H), 2.34 (s, 3H), 1.16 (d, J=6.2 Hz, 6H); LCMS [M+H]$^+$ 590.4.

Example 547: 4-fluoro-N-[4-fluoro-5-(6-morpholin-4-ylpyridin-3-yl)-2-[(3R,5S)-3,4,5-trimethylpiperazin-1-yl]phenyl]-2-(trifluoromethyl)benzamide Example 548: N-[4-fluoro-5-[2-[(2R)-2-propan-2-ylmorpholin-4-yl]pyrimidin-5-yl]-2-[(3S,5R)-3,4,5-trimethylpiperazin-1-yl]phenyl]-6-oxo-4-(trifluoromethyl)-1H-pyridine-3-carboxamide

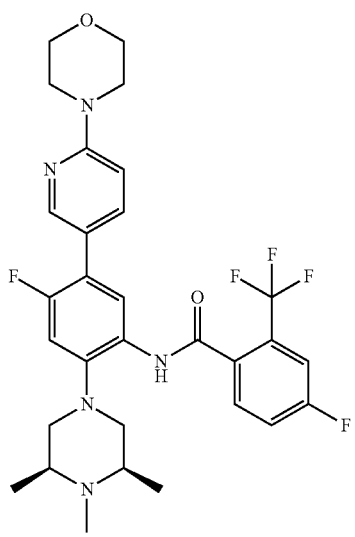

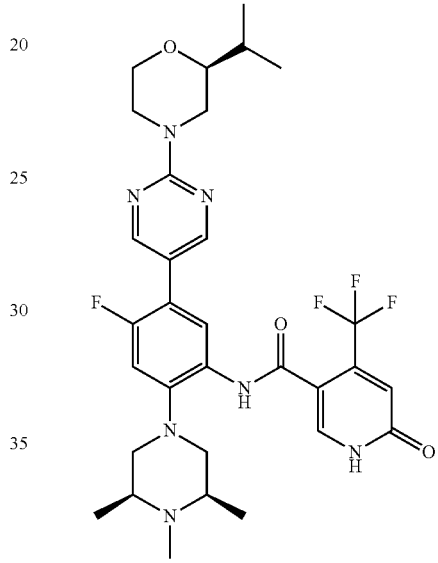

The title compound (formic acid salt, pale beige solid, 57.1 mg, 88%) was prepared by a procedure similar to Example 400 using 4-[5-(4,4,5,5-tetramethyl-[1,3,2]dioxaborolan-2-yl)-pyridin-2-yl]-morpholine (58 mg, 0.2 mmol) and N-(5-bromo-4-fluoro-2-((3S,5R)-3,4,5-trimethylpiperazin-1-yl)phenyl)-4-fluoro-2-(trifluoromethyl)benzamide (57 mg, 89% purity, 0.1 mmol). $^1$H NMR (500 MHz, METHANOL-d4) δ=8.42 (br s, 1H), 8.35 (s, 1H), 8.07 (d, J=8.2 Hz, 1H), 7.85-7.77 (m, 2H), 7.67 (br d, J=8.8 Hz, 1H), 7.58 (br t, J=7.9 Hz, 1H), 7.20 (d, J=11.9 Hz, 1H), 6.94 (br d, J=8.9 Hz, 1H), 3.87-3.78 (m, 4H), 3.56 (br s, 4H), 3.42 (br s, 2H), 3.30 (br d, J=12.8 Hz, 2H), 3.00 (br d, J=10.5 Hz, 2H), 2.89 (s, 3H), 1.42 (br d, J=6.2 Hz, 6H); LCMS [M+H]$^+$ 590.4.

The title compound (beige solid, 30.8 mg, 49%) was prepared by a procedure similar to Example 29 using crude (S)-(2-(2-isopropylmorpholino)pyrimidin-5-yl)boronic acid (0.2 mmol) and N-(5-bromo-4-fluoro-2-((3S,5R)-3,4,5-trimethylpiperazin-1-yl)phenyl)-6-oxo-4-(trifluoromethyl)-1,6-dihydropyridine-3-carboxamide (50.5 mg, 0.1 mmol). $^1$H NMR (500 MHz, CHLOROFORM-d) δ=8.69 (br s, 1H), 8.56 (s, 2H), 8.45 (br d, J=7.9 Hz, 1H), 7.86 (s, 1H), 7.06-6.97 (m, 2H), 4.67 (br d, J=13.0 Hz, 1H), 4.56 (br d, J=13.2 Hz, 1H), 4.03 (dd, J=2.5, 11.4 Hz, 1H), 3.62 (dt, J=2.6, 11.6 Hz, 1H), 3.22-3.04 (m, 2H), 2.89-2.76 (m, 3H), 2.73-2.58 (m, 2H), 2.41-2.25 (m, 5H), 1.81 (qd, J=6.8, 13.5 Hz, 1H), 1.14 (br d, J=5.7 Hz, 6H), 1.04 (d, J=6.8 Hz, 3H), 1.02 (d, J=6.8 Hz, 3H); LCMS [M+H]$^+$ 632.6.

Example 549: N-[4-fluoro-5-(4-piperazin-1-ylphenyl)-2-[(3R,5S)-3,4,5-trimethylpiperazin-1-yl]phenyl]-6-oxo-4-(trifluoromethyl)-1H-pyridine-3-carboxamide

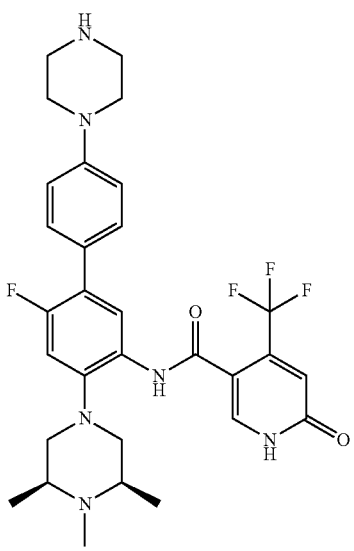

The procedure followed was similar to Example 39 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (207 mg, 0.342 mmol) and tert-butyl 4-[4-(4,4,5,5-tetramethyl-1,3,2-dioxaborolan-2-yl)phenyl]tetrahydro-1(2H)-pyrazinecarboxylate (211 mg, 0.543 mmol) to afford the intermediate tert-butyl 4-(2'-fluoro-5'-(4-(trifluoromethyl)-6-(2-(trimethylsilyl)ethoxy)nicotinamido)-4'-((3S,5R)-3,4,5-trimethylpiperazin-1-yl)-[1,1'-biphenyl]-4-yl)piperazine-1-carboxylate which was deprotected using TFA and DCM according to procedures hereinabove to provide the title compound (18.2 mg, 66.3% yield) as a white powder. $^1$H NMR (500 MHz, DMSO-d6) δ=9.44 (s, 1H), 7.92 (s, 1H), 7.75 (d, J=8.56 Hz, 1H), 7.35 (d, J=7.83 Hz, 2H), 6.96-7.03 (m, 3H), 6.78 (s, 1H), 3.08-3.14 (m, 4H), 3.00 (d, J=10.88 Hz, 2H), 2.83-2.89 (m, 4H), 2.45 (t, J=10.94 Hz, 2H), 2.30-2.38 (m, 2H), 2.19 (s, 3H), 1.01 (d, J=6.11 Hz, 6H); LCMS [M+H]+ 587.4.

Example 550: N-[5-(3-carbamoyl-4-fluorophenyl)-4-fluoro-2-[(3R,5S)-3,4,5-trimethylpiperazin-1-yl]phenyl]-6-oxo-4-(trifluoromethyl)-1H-pyridine-3-carboxamide

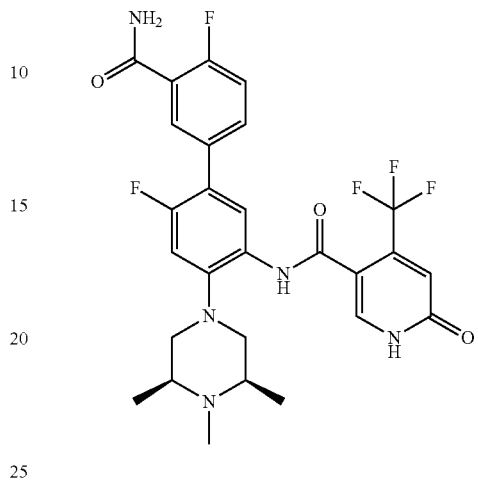

The title compound was prepared using a procedure similar to that used in Example 100 using 3-carbamoyl-4-fluorophenylboronic acid to afford the title compound (TFA salt) as a white solid (43 mg, 0.060 mmol, 98% yield). $^1$H NMR (500 MHz, METHANOL-d4) δ=7.85 (s, 1H), 7.85-7.82 (m, 1H), 7.80 (d, J=8.2 Hz, 1H), 7.60-7.50 (m, 1H), 7.18 (dd, J=8.7, 10.6 Hz, 1H), 7.02 (d, J=11.7 Hz, 1H), 6.79-6.74 (m, 1H), 3.39-3.30 (m, 2H), 3.24 (br d, J=13.1 Hz, 2H), 2.84 (s, 3H), 2.81-2.73 (m, 2H), 1.29 (d, J=6.5 Hz, 6H); LCMS [M+H]+ 564.

Example 551: N-[5-(4-carbamoyl-3-fluorophenyl)-4-fluoro-2-[(3R,5S)-3,4,5-trimethylpiperazin-1-yl]phenyl]-6-oxo-4-(trifluoromethyl)-1H-pyridine-3-carboxamide

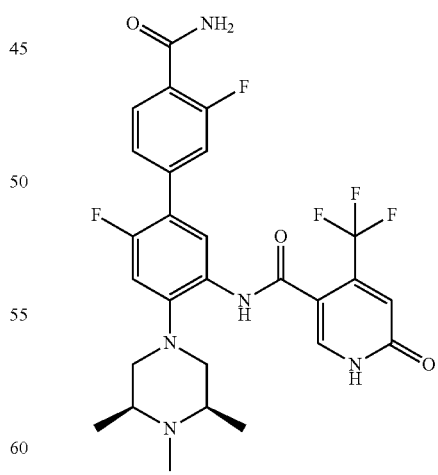

The procedure followed was similar to Example 100 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (62 mg, 0.102 mmol) and 4-carbamoyl-3-fluorophenylboronic acid, 96% (28.1 mg, 0.154 mmol) afforded, after deprotection of the intermediate, the title compound as a white solid (53 mg, 99% yield for last step). $^1$H NMR (500 MHz, METHANOL-d4) δ=7.92 (s, 1H), 7.90 (d, J=8.1 Hz, 1H), 7.81 (t, J=7.9 Hz, 1H), 7.39 (d, J=8.1 Hz, 1H), 7.34 (d, J=12.2 Hz, 1H), 7.09 (d, J=11.9 Hz, 1H), 6.85-6.82 (m, 1H), 3.45-3.37 (m, 2H), 3.31 (br d, J=13.1 Hz, 2H), 2.89 (s, 3H), 2.88-2.79 (m, 2H), 1.35 (d, J=6.4 Hz, 6H); LCMS [M+H]$^+$ 564.

Example 552: N-[5-(3-carbamoyl-4-fluorophenyl)-4-fluoro-2-[(3R,5S)-3,4,5-trimethylpiperazin-1-yl]phenyl]-4-(difluoromethyl)-6-oxo-1H-pyridine-3-carboxamide

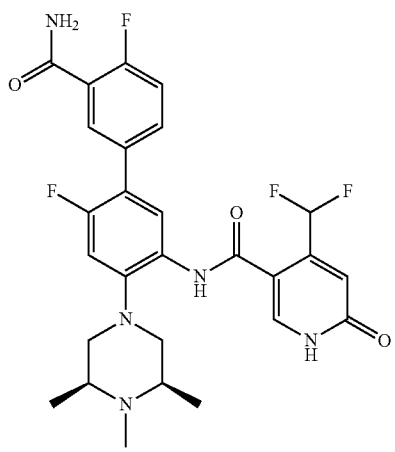

A procedure similar to Example 100 using N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (60 mg, 0.102 mmol, preparation shown in Example 397) and 3-carbamoyl-4-fluorophenylboronic acid, 97% (28.0 mg, 0.153 mmol) gave, after deprotection of the silyloxy intermediate, the title compound (TFA salt) as a white solid (61 mg, 0.075 mmol, 95% yield). $^1$H NMR (500 MHz, METHANOL-d4) δ=7.96 (s, 1H), 7.89 (br d, J=6.0 Hz, 1H), 7.70 (d, J=8.2 Hz, 1H), 7.66-7.61 (m, 1H), 7.32-7.08 (m, 2H), 7.05 (d, J=11.7 Hz, 1H), 6.72-6.67 (m, 1H), 3.42-3.34 (m, 2H), 3.31 (br d, J=13.3 Hz, 2H), 2.88 (s, 3H), 2.86-2.78 (m, 2H), 1.34 (d, J=6.4 Hz, 6H); LCMS [M+H]$^+$ 546.

Example 553: N-[5-(4-carbamoyl-3-fluorophenyl)-4-fluoro-2-[(3R,5S)-3,4,5-trimethylpiperazin-1-yl]phenyl]-4-(difluoromethyl)-6-oxo-1H-pyridine-3-carboxamide

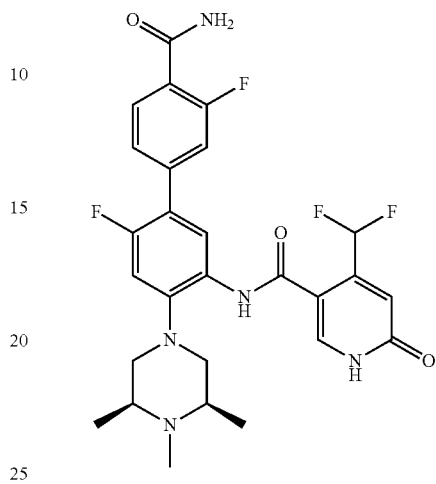

The title compound was prepared by a procedure similar to Example 100 using N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (60 mg, 0.102 mmol) and 4-carbamoyl-3-fluorophenylboronic acid, 96% (28.0 mg, 0.153 mmol). Deprotection with TFA gave the product (TFA salt) as an off-white solid (66.8 mg, 0.082 mmol, 95% yield). $^1$H NMR (500 MHz, METHANOL-d4) δ=7.99 (s, 1H), 7.82 (t, J=8.0 Hz, 1H), 7.76 (d, J=8.1 Hz, 1H), 7.40 (d, J=8.2 Hz, 1H), 7.37-7.11 (m, 2H), 7.08 (d, J=12.0 Hz, 1H), 6.72 (s, 1H), 3.45-3.37 (m, 2H), 3.34 (br d, J=13.3 Hz, 2H), 2.91 (s, 3H), 2.89-2.83 (m, 2H), 1.36 (d, J=6.4 Hz, 6H); LCMS [M+H]$^+$ 546.

Example 554: 2-fluoro-5-[2-fluoro-5-[[4-fluoro-2-(trifluoromethyl)benzoyl]amino]-4-[(3R)-3,4-dimethylpiperazin-1-yl]phenyl]benzamide

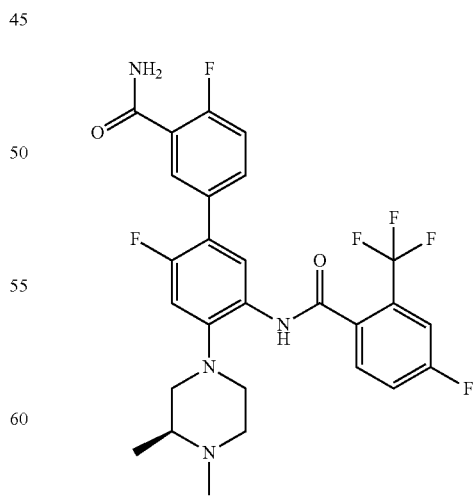

A procedure similar to Example 400 using (S)—N-(5-bromo-2-(3,4-dimethylpiperazin-1-yl)-4-fluorophenyl)-4-fluoro-2-(trifluoromethyl)benzamide (62 mg, 0.126 mmol)

and 3-carbamoyl-4-fluorophenylboronic acid, 97% (34.6 mg, 0.189 mmol) gave the title compound which was isolated as a very light yellow foamy powder (45.7 mg, 0.079 mmol, 62.6% yield). $^1$H NMR (500 MHz, METHANOL-d4) δ=8.07 (d, J=8.2 Hz, 1H), 8.02 (br d, J=6.1 Hz, 1H), 7.79 (dd, J=5.4, 8.4 Hz, 1H), 7.77-7.71 (m, 1H), 7.66 (dd, J=2.3, 9.0 Hz, 1H), 7.60-7.53 (m, 1H), 7.34 (dd, J=8.7, 10.6 Hz, 1H), 7.13 (d, J=12.0 Hz, 1H), 3.14 (br dd, J=1.9, 11.4 Hz, 1H), 3.10-3.04 (m, 1H), 3.00-2.95 (m, 1H), 2.92 (br d, J=13.8 Hz, 1H), 2.59 (t, J=10.9 Hz, 1H), 2.49 (dt, J=2.6, 11.2 Hz, 1H), 2.35 (s, 3H), 1.13 (d, J=6.4 Hz, 3H); LCMS [M+H]$^+$ 551.

Example 555: 2-fluoro-4-[2-fluoro-5-[[4-fluoro-2-(trifluoromethyl)benzoyl]amino]-4-[(3R)-3,4-dimethylpiperazin-1-yl]phenyl]benzamide

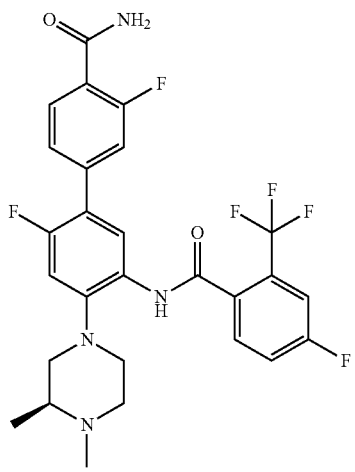

A procedure similar to Example 400 using (S)—N-(5-bromo-2-(3,4-dimethylpiperazin-1-yl)-4-fluorophenyl)-4-fluoro-2-(trifluoromethyl)benzamide (62 mg, 0.126 mmol) and 4-carbamoyl-3-fluorophenylboronic acid, 96% (34.6 mg, 0.189 mmol) provided the title compound as an off-white foamy powder (41 mg, 0.071 mmol, 56.2% yield). $^1$H NMR (500 MHz, METHANOL-d4) δ=8.09 (d, J=8.2 Hz, 1H), 7.93 (t, J=8.0 Hz, 1H), 7.82-7.76 (m, 1H), 7.66 (dd, J=2.2, 9.0 Hz, 1H), 7.57 (dt, J=2.3, 8.3 Hz, 1H), 7.52 (br d, J=8.2 Hz, 1H), 7.47 (br d, J=12.3 Hz, 1H), 7.14 (d, J=12.2 Hz, 1H), 3.16 (br dd, J=1.7, 11.4 Hz, 1H), 3.11 (br d, J=11.6 Hz, 1H), 3.01-2.96 (m, 1H), 2.95-2.90 (m, 1H), 2.59 (t, J=10.9 Hz, 1H), 2.49 (dt, J=2.7, 11.2 Hz, 1H), 2.37 (br d, J=2.9 Hz, 1H), 2.35 (s, 3H), 1.14 (d, J=6.4 Hz, 3H); LCMS [M+H]$^+$ 551.

Example 556: 2-fluoro-5-[2-fluoro-5-[[4-fluoro-2-(trifluoromethyl)benzoyl]amino]-4-[(3R,5S)-3,4,5-trimethylpiperazin-1-yl]phenyl]benzamide

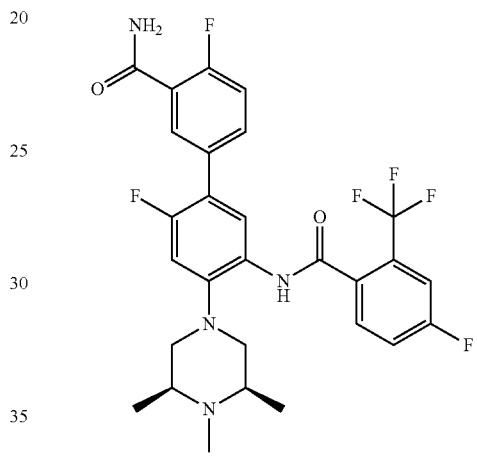

A procedure similar to Example 100 using N-(5-bromo-4-fluoro-2-((3S,5R)-3,4,5-trimethylpiperazin-1-yl)phenyl)-4-fluoro-2-(trifluoromethyl)benzamide (31 mg, 0.061 mmol) and 3-carbamoyl-4-fluorophenylboronic acid, 97% (16.80 mg, 0.092 mmol) provided the title compound which was isolated as a white fluffy powder (25.9 mg, 0.044 mmol, 71.2% yield). $^1$H NMR (500 MHz, METHANOL-d4) δ=7.94 (d, J=8.2 Hz, 1H), 7.91-7.88 (m, 1H), 7.69-7.60 (m, 2H), 7.54 (dd, J=2.3, 9.0 Hz, 1H), 7.45 (dt, J=2.4, 8.3 Hz, 1H), 7.23 (dd, J=8.6, 10.7 Hz, 1H), 7.02-6.94 (m, 1H), 2.97 (br d, J=11.4 Hz, 2H), 2.52 (t, J=11.2 Hz, 2H), 2.39-2.30 (m, 2H), 2.22 (s, 3H), 1.05 (d, J=6.4 Hz, 6H); LCMS [M+H]$^+$ 565.

Example 557: N-[5-[2-(4-tert-butylpiperazin-1-yl)pyrimidin-5-yl]-4-fluoro-2-[(3R)-3,4-dimethylpiperazin-1-yl]phenyl]-4-fluoro-2-(trifluoromethyl)benzamide

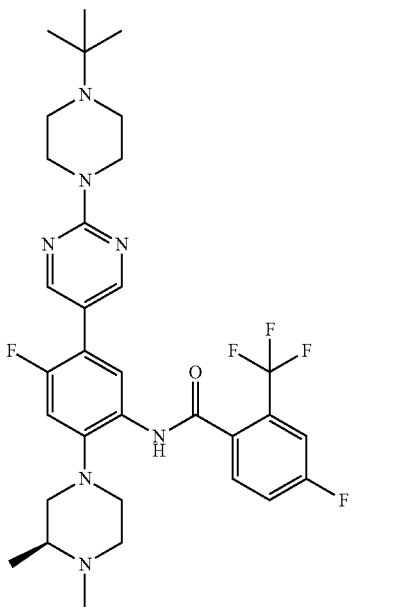 [SMILES: C[C@H]1CN(c2cc(F)c(-c3cnc(N4CCN(C(C)(C)C)CC4)nc3)cc2NC(=O)c2ccc(F)cc2C(F)(F)F)CCN1C]

To a mixture of 2-chloropyrimidine-5-boronic acid (633 mg, 4 mmol) and 1-tert-butylpiperazine (0.64 mL, 4.4 mmol) in EtOH (8 mL) was added triethylamine (0.84 mL, 6 mmol). The resulting mixture was stirred at 75° C. for 1 h. Solvents were removed and the residue was dried under high vacuum to give crude (2-(4-(tert-butyl)piperazin-1-yl)pyrimidin-5-yl)boronic acid as a light beige solid (1.361 g, 77% purity assuming full conversion). LCMS [M+H]$^+$ 265.32. The title compound (di-formic acid salt, light brown solid, 56.7 mg, 78%) was prepared using a procedure similar to Example 400 using crude (2-(4-(tert-butyl)piperazin-1-yl)pyrimidin-5-yl)boronic acid (0.3 mmol) and (S)—N-(5-bromo-2-(3,4-dimethylpiperazin-1-yl)-4-fluorophenyl)-4-fluoro-2-(trifluoromethyl)benzamide (57 mg, 86% purity, 0.1 mmol). $^1$H NMR (500 MHz, METHANOL-d4) δ=8.64 (s, 2H), 8.43 (br s, 2H), 8.07 (d, J=8.2 Hz, 1H), 7.82 (dd, J=5.3, 8.4 Hz, 1H), 7.67 (dd, J=2.0, 9.0 Hz, 1H), 7.58 (dt, J=2.1, 8.2 Hz, 1H), 7.22 (d, J=11.7 Hz, 1H), 4.21 (br s, 4H), 3.48-3.36 (m, 5H), 3.26 (br t, J=9.0 Hz, 2H), 3.21-3.03 (m, 3H), 2.96-2.84 (m, 1H), 2.81-2.73 (m, 3H), 1.47 (s, 9H), 1.34 (br d, J=6.5 Hz, 3H); LCMS [M+H]$^+$ 632.4.

Example 558: N-[5-[2-(2,2-dimethylmorpholin-4-yl)pyrimidin-5-yl]-4-fluoro-2-[(3R)-3,4-dimethylpiperazin-1-yl]phenyl]-4-fluoro-2-(trifluoromethyl)benzamide

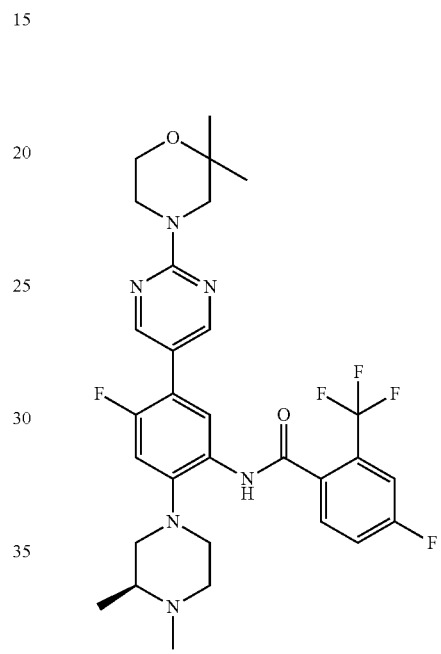

The title compound (formic acid salt, off white solid, 35.1 mg, 54%) was prepared according to a procedure similar to Example 400 using crude (2-(2,2-dimethylmorpholino)pyrimidin-5-yl)boronic acid (0.3 mmol) and (S)—N-(5-bromo-2-(3,4-dimethylpiperazin-1-yl)-4-fluorophenyl)-4-fluoro-2-(trifluoromethyl)benzamide (57 mg, 86% purity, 0.1 mmol). $^1$H NMR (500 MHz, METHANOL-d4) δ=8.53 (s, 2H), 8.42 (br s, 1H), 8.03 (br d, J=8.2 Hz, 1H), 7.80 (dd, J=5.3, 8.4 Hz, 1H), 7.67-7.62 (m, 1H), 7.56 (br t, J=8.2 Hz, 1H), 7.18 (d, J=11.9 Hz, 1H), 3.82 (br dd, J=4.2, 15.8 Hz, 4H), 3.71 (s, 2H), 3.48-3.38 (m, 1H), 3.28-3.22 (m, 2H), 3.21-3.05 (m, 3H), 2.90 (br s, 1H), 2.80 (br s, 3H), 1.38-1.30 (m, 3H), 1.24 (s, 6H); LCMS [M+H]$^+$ 605.3.

Example 559: N-[5-[2-(2,2-dimethylmorpholin-4-yl)pyrimidin-5-yl]-4-fluoro-2-[(3R,5S)-3,4,5-trimethylpiperazin-1-yl]phenyl]-4-fluoro-2-(trifluoromethyl)benzamide

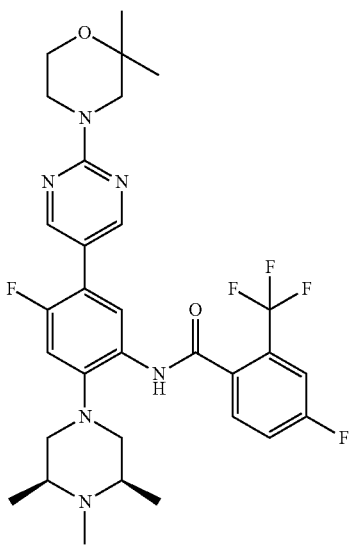

The title compound (formic acid salt, beige solid, 26.4 mg, 40%) was prepared by a procedure similar to Example 400 using crude (2-(2,2-dimethylmorpholino)pyrimidin-5-yl)boronic acid (0.3 mmol) and (N-(5-bromo-4-fluoro-2-((3S,5R)-3,4,5-trimethylpiperazin-1-yl)phenyl)-4-fluoro-2-(trifluoromethyl)benzamide (57 mg, 89% purity, 0.1 mmol). $^1$H NMR (500 MHz, METHANOL-d4) δ=8.54 (s, 2H), 8.36 (br s, 1H), 8.04 (d, J=8.2 Hz, 1H), 7.80 (dd, J=5.3, 8.5 Hz, 1H), 7.66 (dd, J=2.1, 9.0 Hz, 1H), 7.57 (dt, J=2.2, 8.3 Hz, 1H), 7.19 (d, J=11.9 Hz, 1H), 3.88-3.77 (m, 4H), 3.72 (s, 2H), 3.30-3.24 (m, 4H), 2.97-2.85 (m, 2H), 2.81 (br s, 3H), 1.37 (br d, J=6.2 Hz, 6H), 1.25 (s, 6H); LCMS [M+H]$^+$ 619.4.

Example 560: N-[5-[2-[4-(cyclopropylmethyl)piperazin-1-yl]pyrimidin-5-yl]-4-fluoro-2-[(3R)-3,4-dimethylpiperazin-1-yl]phenyl]-4-fluoro-2-(trifluoromethyl)benzamide

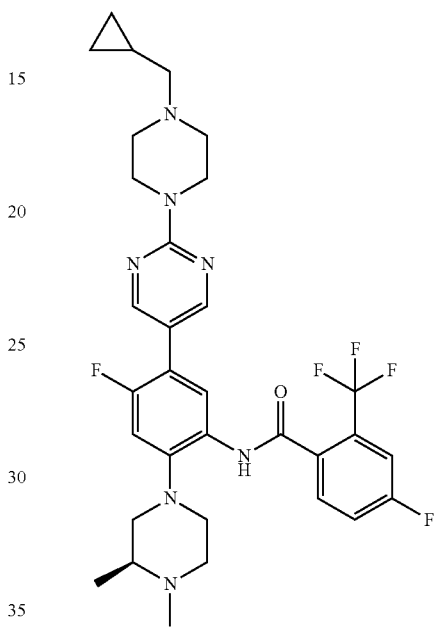

To a mixture of 2-chloropyrimidine-5-boronic acid (633 mg, 4 mmol) and 1-(cyclopropylmethyl)piperazine (0.62 mL, 4.4 mmol) in EtOH (8 mL) was added triethylamine (0.84 mL, 6 mmol). The resulting mixture was stirred at 75° C. for 1 h. Solvents were removed and the residue was dried under high vacuum to give crude (2-(4-(cyclopropylmethyl)piperazin-1-yl)pyrimidin-5-yl)boronic acid as a yellow solid (1.458 g, 72% purity assuming full conversion). LCMS [M+H]$^+$ 263.4. The title compound (di-formic acid salt, beige solid, 45.9 mg, 63%) was prepared by a procedure similar to Example 40 using crude (2-(4-(cyclopropylmethyl)piperazin-1-yl)pyrimidin-5-yl)boronic acid (0.3 mmol) and (S)—N-(5-bromo-2-(3,4-dimethylpiperazin-1-yl)-4-fluorophenyl)-4-fluoro-2-(trifluoromethyl)benzamide (57 mg, 86% purity, 0.1 mmol). $^1$H NMR (500 MHz, METHANOL-d4) δ=8.62 (s, 2H), 8.46 (br s, 2H), 8.05 (d, J=8.1 Hz, 1H), 7.81 (dd, J=5.4, 8.2 Hz, 1H), 7.65 (d, J=8.6 Hz, 1H), 7.57 (t, J=8.2 Hz, 1H), 7.21 (d, J=11.7 Hz, 1H), 4.19 (br s, 4H), 3.56-3.44 (m, 1H), 3.41-3.34 (m, 4H), 3.30-3.25 (m, 3H), 3.23-3.14 (m, 2H), 3.04 (br d, J=6.6 Hz, 3H), 2.97 (br d, J=10.5 Hz, 1H), 2.83 (br s, 3H), 1.43-1.32 (m, 3H), 1.16 (br s, 1H), 0.81-0.73 (m, 2H), 0.47-0.40 (m, 2H); LCMS [M+H]$^+$ 630.4.

Example 561: N-[2-(4-cyclopropylpiperazin-1-yl)-4-fluoro-5-(2-morpholin-4-ylpyrimidin-5-yl)phenyl]-6-oxo-4-(trifluoromethyl)-1H-pyridine-3-carboxamide

Example 562: N-[4-fluoro-5-(5-fluoro-6-oxo-1H-pyridin-3-yl)-2-[(3R,5S)-3,4,5-trimethylpiperazin-1-yl]phenyl]-6-oxo-4-(triluoromethyl)-1H-pyridine-3-carboxamide

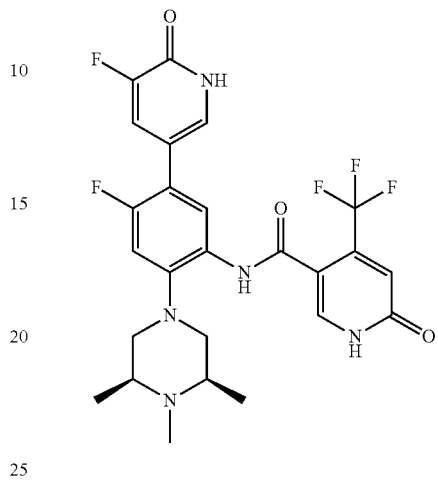

A procedure similar to Example 39 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) and (5-fluoro-6-oxo-1,6-dihydropyridin-3-yl)boronic acid gave the title compound (19 mg, 74% yield). $^1$H NMR (500 MHz, METHANOL-d4) δ=8.03-7.94 (m, 1H), 7.91-7.84 (m, 1H), 7.75-7.65 (m, 1H), 7.55-7.49 (m, 1H), 7.15-7.06 (m, 1H), 6.99-6.91 (m, 1H), 3.15-3.04 (m, 2H), 2.73-2.60 (m, 4H), 2.50-2.40 (m, 3H), 1.25-1.16 (m, 6H); LCMS [M+H]+ 538.5

Example 563: benzyl N-[5-[2-fluoro-5-[[6-oxo-4-(trifluoromethyl)-1H-pyridine-3-carbonyl]amino]-4-[(3R 5S)-3,4,5-trimethylpiperazin-1-yl]phenyl]pyridin-3-yl]carbamate

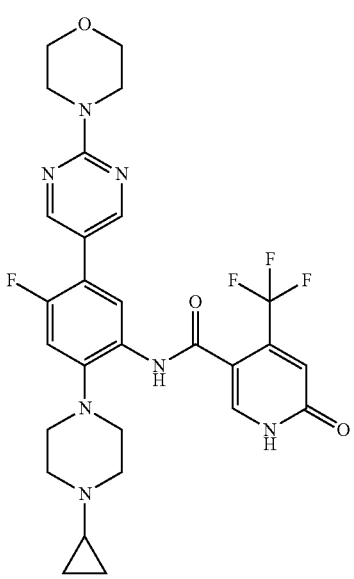 [SMILES: O=C(Nc1cc(-c2cnc(N3CCOCC3)nc2)c(F)cc1N1CCN(C2CC2)CC1)c1c[nH]c(=O)cc1C(F)(F)F]

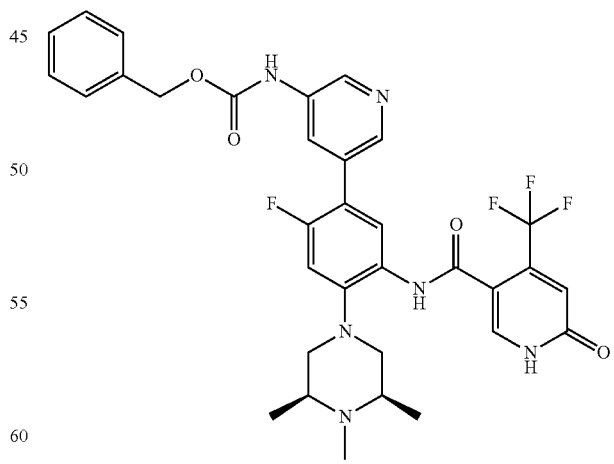

Through a sequence similar to Example 541 using 4-(trifluoromethyl)-6-(2-(trimethylsilyl)ethoxy)nicotinic acid (65.3 mg, 0.212 mmol) and 2-(4-cyclopropylpiperazin-1-yl)-4-fluoro-5-(2-morpholinopyrimidin-5-yl)aniline (65.1 mg, 0.163 mmol) and deprotection of the N-(2-(4-cyclopropylpiperazin-1-yl)-4-fluoro-5-(2-morpholinopyrimidin-5-yl)phenyl)-4-(trifluoromethyl)-6-(2-(trimethylsilyl)ethoxy)nicotinamide intermediate, the title compound TFA salt (24.0 mg, 95% yield in last step) was isolated as a light brown powder. $^1$H NMR (500 MHz, DMSO-d6) δ=9.65 (s, 1H), 8.54 (s, 2H), 7.99 (br s, 1H), 7.88 (d, J=8.31 Hz, 1H), 7.21 (d, J=11.98 Hz, 1H), 6.84 (s, 1H), 3.78-3.74 (m, 4H), 3.70-3.66 (m, 4H), 3.57 (br s, 2H), 3.34 (br s, 4H), 2.99 (br s, 2H), 2.89 (br s, 1H), 0.99 (br s, 2H), 0.85 (br d, J=5.01 Hz, 2H); LCMS [M+H]+ 588.4.

The sequence followed was similar to Example 39 starting with N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (70 mg, 0.116 mmol) and 5-(benzyloxycarbonylamino)pyridine-3-boronic acid, pinacol ester (61.4 mg, 0.173 mmol) to give the title compound (14 mg, 61% yield). ¹H NMR (500 MHz, METHANOL-d4) δ=8.83-8.57 (m, 1H), 8.53-8.32 (m, 1H), 8.29-8.11 (m, 1H), 8.08-7.87 (m, 2H), 7.51-7.31 (m, 5H), 7.20-7.04 (m, 1H), 7.02-6.85 (m, 1H), 5.35-5.17 (m, 2H), 3.19-3.00 (m, 2H), 2.84-2.51 (m, 4H), 2.50-2.26 (m, 3H), 1.31-1.04 (m, 6H); LCMS [M+H]+ 653.4.

Example 564: N-[4-fluoro-5-(5-fluoro-1-methyl-6-oxopyridin-3-yl)-2-[(3R 5S)-3,4,5-trimethylpiperazin-1-yl]phenyl]-6-oxo-4-(trifluoromethyl)-1H-pyridine-3-carboxamide

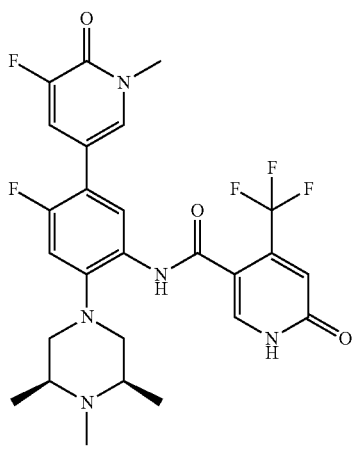 [SMILES: C[C@@H]1CN(c2cc(F)c(-c3cc(F)c(=O)n(C)c3)cc2NC(=O)c2c[nH]c(=O)cc2C(F)(F)F)C[C@H](C)N1C]

N-(4-Fluoro-5-(5-fluoro-1-methyl-6-oxo-1,6-dihydropyridin-3-yl)-2-((3S,5R)-3,4,5-trimethylpiperazin-1-yl)phenyl)-4-(trifluoromethyl)-6-(2-(trimethylsilyl)ethoxy)nicotinamide, obtained as the intermediate in the preparation of Example 562, was treated with cesium carbonate (18.90 mg, 0.058 mmol) and iodomethane (5.42 μl, 0.087 mmol) in DMF (1.5 ml) at RT. Purification of N-(4-fluoro-5-(5-fluoro-1-methyl-6-oxo-1,6-dihydropyridin-3-yl)-2-((3S,5R)-3,4,5-trimethylpiperazin-1-yl)phenyl)-4-(trifluoromethyl)-6-(2-(trimethylsilyl)ethoxy)nicotinamide and deprotection using standard conditions provided the title compound (9 mg, 44% yield). ¹H NMR (500 MHz, METHANOL-d4) δ=7.97 (s, 1H), 7.87 (d, J=8.3 Hz, 1H), 7.77 (s, 1H), 7.62 (br d, J=10.6 Hz, 1H), 7.10 (d, J=12.1 Hz, 1H), 6.92 (s, 1H), 3.74-3.66 (m, 3H), 3.19-3.12 (m, 2H), 2.92 (br s, 2H), 2.77-2.70 (m, 2H), 2.59 (br s, 3H), 1.29-1.23 (m, 6H); LCMS [M+H]+ 552.5.

Example 565: N-[4-fluoro-5-[1-(4-methoxybenzoyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

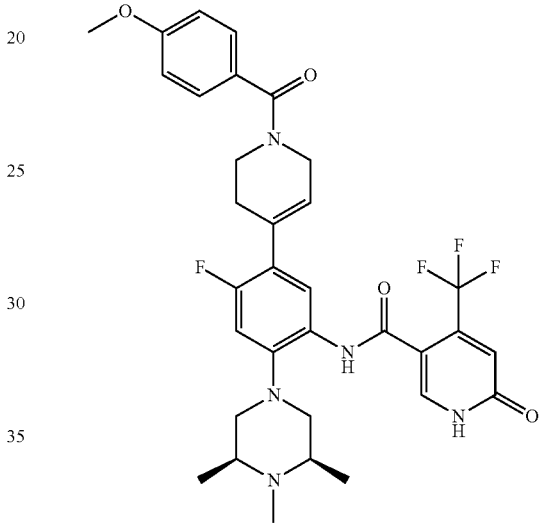

The procedure followed was similar to Example 253 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) and 4-methoxybenzoyl chloride, 99% (8.55 μl, 0.062 mmol) to give the title compound as a white powder (23 mg, 58%). ¹H NMR (500 MHz, METHANOL-d4) δ=7.91-7.78 (m, 1H), 7.76-7.59 (m, 1H), 7.42-7.27 (m, 2H), 6.96-6.89 (m, 2H), 6.89-6.84 (m, 1H), 6.83-6.79 (m, 1H), 6.12-5.64 (m, 1H), 4.32-3.99 (m, 2H), 3.98-3.67 (m, 4H), 3.66-3.52 (m, 1H), 3.00-2.87 (m, 2H), 2.65-2.42 (m, 6H), 2.37-2.27 (m, 3H), 1.08 (br d, J=4.9 Hz, 6H); LCMS [M+H]+ 642.5

Example 566: N-[4-fluoro-5-(2-oxo-1,3-dihydropyrrolo[2,3-b]pyridin-5-yl)-2-[(3R,5S)-3,4,5-trimethylpiperazin-1-yl]phenyl]-6-oxo-4-(trifluoromethyl)-1H-pyridine-3-carboxamide

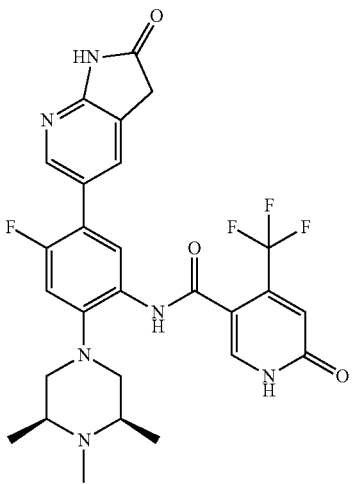 [SMILES: C[C@@H]1CN(c2cc(F)c(-c3cnc4c(c3)CC(=O)N4)cc2NC(=O)c2c[nH]c(=O)cc2C(F)(F)F)C[C@H](C)N1C]

A sequence similar to Example 39 using 5-(4,4,5,5-tetramethyl-1,3,2-dioxaborolan-2-yl)-1 h-pyrrolo[2,3-b]pyridin-2(3 h)-one (0.034 g, 0.129 mmol) and N-(5-bromo-4-fluoro-2-((3R,5S)-3,4,5-trimethylpiperazin-1-yl)phenyl)-4-(trifluoromethyl)-6-(2-(trimethylsilyl)ethoxy) nicotinamide (0.05216 g, 0.086 mmol) gave the title compound (16 mg, 32% yield). $^1$H NMR (500 MHz, DMSO) δ 11.92 (s, 1H), 10.33 (s, 1H), 8.97 (s, 1H), 8.72 (s, 1H), 8.57 (d, J=8.5 Hz, 1H), 8.48 (s, 1H), 8.38 (t, J=8.1 Hz, 1H), 7.85 (d, J=12.4 Hz, 1H), 7.61 (s, 1H), 7.58 (d, J=7.4 Hz, 1H), 4.44 (s, 2H), 3.84 (d, J=10.8 Hz, 2H), 3.77 (s, 2H), 3.17 (s, 3H), 3.00 (s, 3H), 1.95 (d, J=13.2 Hz, 8H), 1.82 (d, J=6.1 Hz, 6H); $^{19}$F NMR (471 MHz, DMSO) δ −61.35 (s), −119.83 (s); LCMS HSS [M+1]+=559.32. Major rotamer reported

Example 567: N-[4-fluoro-5-(1-methyl-2-oxopyridin-4-yl)-2-[(3R,5S)-3,4,5-trimethylpiperazin-1-yl]phenyl]-6-oxo-4-(trifluoromethyl)-1H-pyridine-3-carboxamide

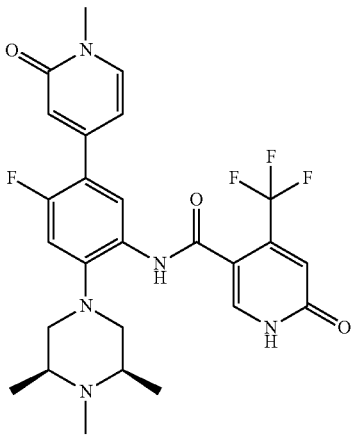 [SMILES: C[C@@H]1CN(c2cc(F)c(-c3ccn(C)c(=O)c3)cc2NC(=O)c2c[nH]c(=O)cc2C(F)(F)F)C[C@H](C)N1C]

A procedure similar to Example 39 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (40 mg, 0.066 mmol) and 1-methyl-2-oxo-1,2-dihydropyridin-4-ylboronic acid pinacol ester (23.29 mg, 0.099 mmol) gave the title compound (28 mg, 90% yield for last step). $^1$H NMR (500 MHz, METHANOL-d4) δ=7.97 (s, 1H), 7.97 (d, J=6.0 Hz, 2H), 7.73 (d, J=7.1 Hz, 1H), 7.09 (d, J=12.5 Hz, 1H), 6.93 (s, 1H), 6.77 (s, 1H), 6.64 (br d, J=7.0 Hz, 1H), 3.62 (s, 3H), 3.14 (br d, J=11.1 Hz, 2H), 2.70-2.63 (m, 2H), 2.62-2.54 (m, 2H), 2.40 (s, 3H), 1.21-1.17 (m, 6H); LCMS [M+H]+ 534.2.

Example 568: N-[4-fluoro-5-(I-methyl-6-oxopyridin-3-yl)-2-[(3R,5S)-3,4,5-trimethylpiperazin-1-yl]phenyl]-6-oxo-4-(trifluoromethyl)-1H-pyridine-3-carboxamide

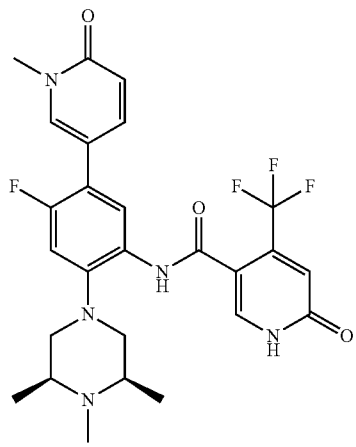 [SMILES: C[C@@H]1CN(c2cc(F)c(-c3ccc(=O)n(C)c3)cc2NC(=O)c2c[nH]c(=O)cc2C(F)(F)F)C[C@H](C)N1C]

The title compound (30 mg, 97% for final step) was prepared through a procedure similar to that of Example 100 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (40 mg, 0.066 mmol) and 1-methyl-1H-pyridin-2-one-5-boronic acid, pinacol ester (23.3 mg, 0.099 mmol). $^1$H NMR (500 MHz, METHANOL-d4) δ=7.97 (s, 1H), 7.94 (s, 1H), 7.89 (d, J=8.4 Hz, 1H), 7.79 (br d, J=9.4 Hz, 1H), 7.09 (d, J=12.1 Hz, 1H), 6.93 (s, 1H), 6.65 (d, J=9.3 Hz, 1H), 3.67 (s, 3H), 3.07 (br d, J=11.0 Hz, 2H), 2.67-2.54 (m, 4H), 2.40 (s, 3H), 1.21-1.16 (m, 6H) LCMS [M+H]+ 534.5.

Example 569: N-[5-[1-(cyclohexanecarbonyl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

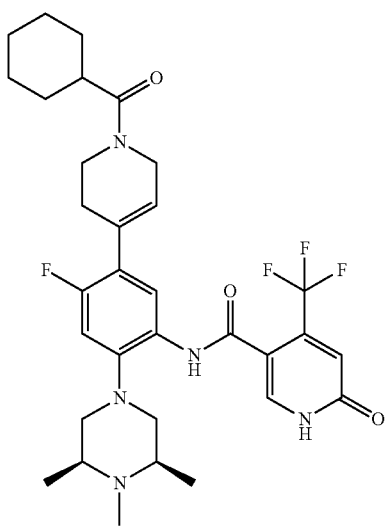 [SMILES: C[C@@H]1CN(c2cc(F)c(C3=CCN(C(=O)C4CCCCC4)CC3)cc2NC(=O)c2c[nH]c(=O)cc2C(F)(F)F)C[C@H](C)N1C]

A procedure similar to that of Example 253 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and cyclohexanecarbonyl chloride (7.03 μl, 0.052 mmol) gave the title compound. (23 mg, 72% yield). $^1$H NMR (500 MHz, METHANOL-d4) δ=7.98-7.92 (m, 1H), 7.82-7.74 (m, 1H), 6.99-6.94 (m, 1H), 6.93-6.89 (m, 1H), 6.09-5.99 (m, 1H), 4.33-4.18 (m, 2H), 3.84-3.78 (m, 2H), 3.07-3.00 (m, 2H), 2.80-2.66 (m, 1H), 2.63-2.50 (m, 6H), 2.39-2.37 (m, 3H), 1.85-1.74 (m, 5H), 1.54-1.36 (m, 5H), 1.18-1.15 (m, 6H), −0.71-0.73 (m, 1H); LCMS [M+H]+ 618.5.

Example 570: tert-butyl N-[1-[2-[(3,5-dichlorobenzoyl)amino]-5-fluoro-4-(2-morpholin-4-ylpyrimidin-5-yl)phenyl]pyrrolidin-3-yl]-N-methylcarbamate

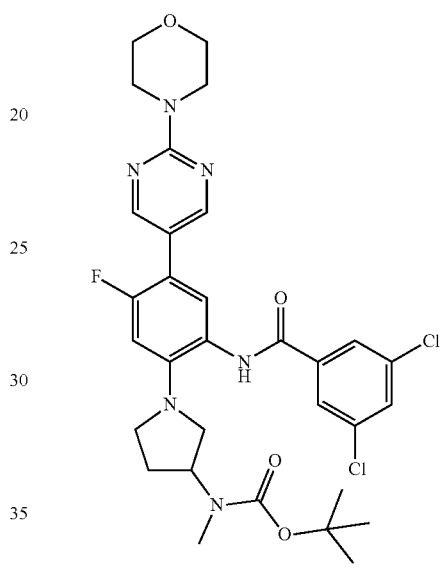

To a solution of tert-butyl (1-(2-amino-5-fluoro-4-(2-morpholinopyrimidin-5-yl)phenyl)pyrrolidin-3-yl)(methyl)carbamate (211 mg, 0.446 mmol, prepared using a sequence similar to Example 541) and triethylamine (0.187 ml, 1.339 mmol) in DCM (40 ml) was added 3,5-dichlorobenzoyl chloride (94 mg, 0.446 mmol). Then the reaction mixture was stirred at room temperature for 2 hours. Then the crude material was dry loaded and purified by chromatography [0-10% DCM/MeOH] to afford the desired tert-butyl (1-(2-(3,5-dichlorobenzamido)-5-fluoro-4-(2-morpholinopyrimidin-5-yl)phenyl)pyrrolidin-3-yl)(methyl)carbamate (288 mg, 0.424 mmol, 95% yield) as a yellow solid. $^1$H NMR (500 MHz, DMSO-d6) δ=10.16 (s, 1H), 8.52 (s, 2H), 7.95-8.02 (m, 2H), 7.88 (s, 1H), 7.34 (d, J=8.80 Hz, 1H), 6.72 (d, J=13.94 Hz, 1H), 5.75 (s, 1H), 4.55 (br. s., 1H), 3.71-3.75 (m, 5H), 3.65-3.68 (m, 4H), 3.35-3.41 (m, 2H), 3.25-3.30 (m, 2H), 2.69 (s, 3H), 1.92-2.07 (m, 2H), 1.35 (s, 9H); LCMS [M+H]+ 645.2.

Example 571: 3,5-dichloro-N-[4-fluoro-2-[3-[3-methoxypropyl(methyl)amino]pyrrolidin-1-yl]-5-(2-morpholin-4-ylpyrimidin-5-yl)phenyl]benzamide

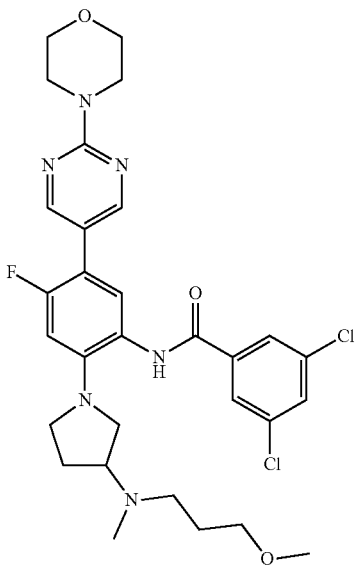 [SMILES: COCCCN(C)C1CCN(c2cc(F)c(-c3cnc(N4CCOCC4)nc3)cc2NC(=O)c2cc(Cl)cc(Cl)c2)C1]

Example 572: N-[4-fluoro-2-[3-[3-methoxypropyl(methyl)amino]pyrrolidin-1-yl]-5-(2-morpholin-4-ylpyrimidin-5-yl)phenyl]-6-oxo-4-(trifluoromethyl)-1H-pyridine-3-carboxamide

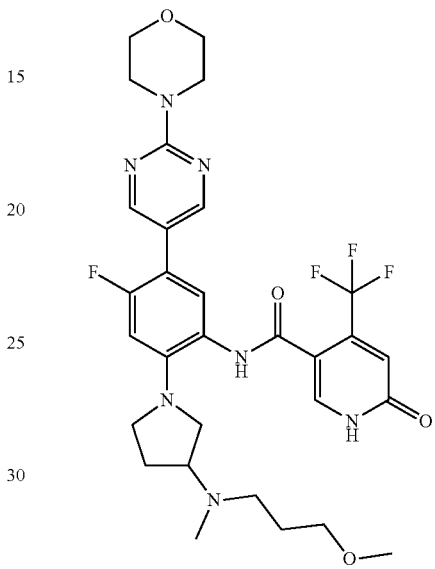

To a solution of 3,5-dichloro-N-(4-fluoro-2-(3-(methylamino)pyrrolidin-1-yl)-5-(2-morpholinopyrimidin-5-yl)phenyl)benzamide (35 mg, 0.064 mmol, prepared by procedures described hereinabove) and 3-methoxypropanal (11 mg, 0.125 mmol) in 1,2-dichloroethane (3 ml) was added acetic acid (23 mg, 0.383 mmol) and the reaction mixture was stirred at room temperature for 15 minutes. Then sodium triacetoxyborohydride (50 mg, 0.236 mmol) was added and the reaction mixture was stirred at room temperature for 1 h 30 min. Then a saturated solution of NaHCO$_3$ (3 mL) was added and the product was extracted using DCM (3×20 mL). The organic phase was dried over MgSO$_4$ and after filtration and solvents removal, the crude material was dry loaded and purified by Flash chromatography [0-10% MeOH/DCM] to afford the 3,5-dichloro-N-(4-fluoro-2-(3-((3-methoxypropyl)(methyl)amino)pyrrolidin-1-yl)-5-(2-morpholinopyrimidin-5-yl)phenyl)benzamide (20.1 mg, 0.031 mmol, 48.2% yield) as a yellow powder. $^1$H NMR (500 MHz, DMSO-d6) δ=10.16 (s, 1H), 8.51 (s, 2H), 7.99 (d, J=1.71 Hz, 2H), 7.89 (s, 1H), 7.30 (d, J=8.80 Hz, 1H), 6.65 (d, J=14.06 Hz, 1H), 3.71-3.75 (m, 4H), 3.65-3.69 (m, 4H), 3.41 (t, J=8.19 Hz, 1H), 3.34-3.37 (m, 1H), 3.27-3.30 (m, 1H), 3.16-3.25 (m, 3H), 3.15 (s, 3H), 2.84-2.91 (m, 1H), 2.19-2.37 (m, 2H), 2.10 (s, 3H), 2.03-2.08 (m, 1H), 1.60-1.70 (m, 1H), 1.55 (quin, J=6.82 Hz, 2H); LCMS [M+H]$^+$ 617.3.

To a solution of N-(4-fluoro-2-(3-(methylamino)pyrrolidin-1-yl)-5-(2-morpholinopyrimidin-5-yl)phenyl)-6-oxo-4-(trifluoromethyl)-1,6-dihydropyridine-3-carboxamide (42 mg, 0.075 mmol) and 3-methoxypropanal (20 mg, 0.227 mmol) in 1,2-dichloroethane (DCE) (3 ml) was added acetic acid (33 mg, 0.550 mmol) and the reaction mixture was stirred at room temperature for 15 minutes. Then sodium triacetoxyborohydride (57.1 mg, 0.269 mmol) was added and the reaction mixture was stirred at room temperature for an additional 20 minutes. Then a saturated solution of NaHCO$_3$ (3 mL) was added and the product was extracted with DCM (3×20 mL). The organic phase was dried over MgSO$_4$ and after filtration and solvents removal, the crude material was dry loaded and purified by Flash chromatography [0-30% MeOH/DCM] to afford the N-(4-fluoro-2-(3-((3-methoxypropyl)(methyl)amino)pyrrolidin-1-yl)-5-(2-morpholinopyrimidin-5-yl)phenyl)-6-oxo-4-(trifluoromethyl)-1,6-dihydropyridine-3-carboxamide TFA salt (17.6 mg, 0.022 mmol, 29.9% yield) as an off-white powder. $^1$H NMR (500 MHz, DMSO-d6) δ=11.99 (br. s., 2H), 9.80 (s, J=7.01, 7.01 Hz, 1H), 8.50 (s, 2H), 7.97 (s, 1H), 7.31 (d, J=8.68 Hz, 1H), 6.79 (s, 1H), 6.65 (d, J=14.06 Hz, 1H), 3.71-3.76 (m, 4H), 3.65-3.70 (m, 4H), 3.38 (br. s., 2H), 3.20-3.29 (m, 4H), 3.17 (s, 3H), 2.85-2.95 (m, 1H), 2.29-2.43 (m, 2H), 2.14 (s, 3H), 2.07 (d, J=3.91 Hz, 1H), 1.65-1.74 (m, 1H), 1.61 (t, J=6.72 Hz, 2H); LCMS [M+H]+ 634.4.

Example 573: N-[4-fluoro-5-[1-(pyrazine-2-carbonyl)-3,6-dihydro-2H-pyridin-4-yl]-2-[(3R,5S)-3,4,5-trimethylpiperazin-1-yl]phenyl]-6-oxo-4-(trifluoromethyl)-1H-pyridine-3-carboxamide

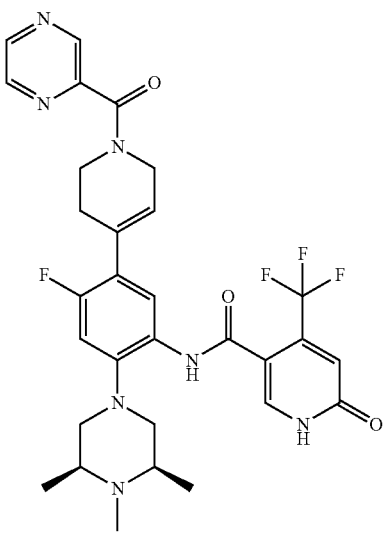 [SMILES: C[C@@H]1CN(c2cc(F)c(C3=CCN(C(=O)c4cnccn4)CC3)cc2NC(=O)c2c[nH]c(=O)cc2C(F)(F)F)C[C@H](C)N1C]

The procedure followed was similar to that of Example 253 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and pyrazine-2-carbonyl chloride (7.37 mg, 0.052 mmol) to afford the title compound (11 mg, 35% yield). $^1$H NMR (500 MHz, METHANOL-d4) δ=8.96-8.89 (m, 1H), 8.76-8.72 (m, 1H), 8.71-8.68 (m, 1H), 7.99-7.91 (m, 1H), 7.85-7.76 (m, 1H), 7.01-6.95 (m, 1H), 6.94-6.91 (m, 1H), 6.16-5.92 (m, 1H), 4.45-4.41 (m, 1H), 4.33-4.30 (m, 1H), 4.10-4.10 (m, 1H), 4.06-4.02 (m, 1H), 3.77 (t, J=5.6 Hz, 1H), 3.07-3.01 (m, 2H), 2.71-2.65 (m, 2H), 2.63-2.53 (m, 4H), 2.40-2.37 (m, 3H), 1.19-1.16 (m, 6H); LCMS [M+H]+ 614.4.

Example 574: N-[4-fluoro-5-(2-morpholin-4-ylpyrimidin-5-yl)-2-[(3R)-3-[methyl(methylsulfonyl)amino]pyrrolidin-1-yl]phenyl]-6-oxo-4-(trifluoromethyl)-1H-pyridine-3-carboxamide

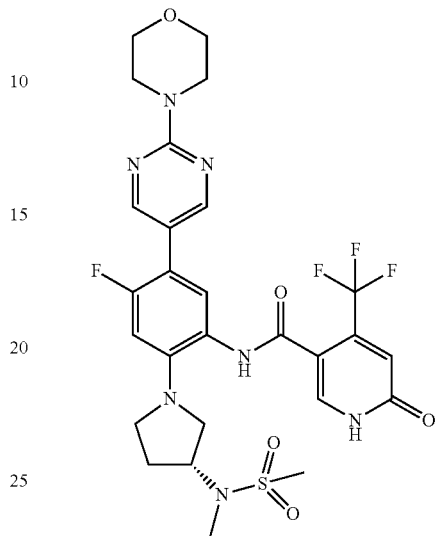

The title compound was prepared similar to the procedure described above for the preparation of Example 417 using (R)—N-methyl-N-(pyrrolidin-3-yl)methanesulfonamide in place of (R)—N-ethyl-N-methylpyrrolidin-3-amine in Step 3. $^1$H NMR (500 MHz, DMSO-d6) δ=9.80 (s, 1H), 8.51 (s, 2H), 7.98 (br s, 1H), 7.38 (br d, J=8.6 Hz, 1H), 6.79 (s, 1H), 6.74 (br d, J=13.6 Hz, 1H), 4.45-4.34 (m, 1H), 3.73 (br d, J=4.2 Hz, 4H), 3.68 (br d, J=3.9 Hz, 4H), 3.39 (br d, J=5.0 Hz, 4H), 2.92 (s, 3H), 2.75 (s, 3H), 2.12 (br d, J=6.8 Hz, 1H), 2.07-1.97 (m, 1H); LCMS [M+H]+: 640.4.

Example 575: N-[4-fluoro-5-(2-morpholin-4-ylpyrimidin-5-yl)-2-[(3S)-3-[methyl(methylsulfonyl)amino]pyrrolidin-1-yl]phenyl]-6-oxo-4-(trifluoromethyl)-1H-pyridine-3-carboxamide

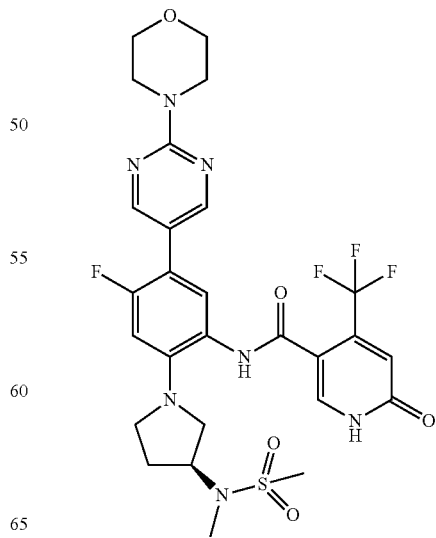

The title compound was prepared similar to the procedure described above for the preparation of Example 417 using (S)—N-methyl-N-(pyrrolidin-3-yl)methanesulfonamide in place of (R)—N-ethyl-N-methylpyrrolidin-3-amine in Step 3. $^1$H NMR (500 MHz, DMSO-d6) δ=9.73 (s, 1H), 8.44 (s, 2H), 7.92 (br s, 1H), 7.31 (d, J=8.7 Hz, 1H), 6.75-6.61 (m, 2H), 4.33 (br t, J=7.9 Hz, 1H), 3.67 (br d, J=4.9 Hz, 4H), 3.62-3.59 (m, 4H), 3.36-3.29 (m, 4H), 2.85 (s, 3H), 2.68 (s, 3H), 2.12-2.02 (m, 1H), 1.99-1.90 (m, 1H); LCMS [M+H]+: 640.5.

Example 576: N-[4-fluoro-5-(2-morpholin-4-ylpyrimidin-5-yl)-2-[(3R,4R)-3-methoxy-4-[2-methoxyethyl(methyl)amino]pyrrolidin-1-yl]phenyl]-6-oxo-4-(trifluoromethyl)-1H-pyridine-3-carboxamide

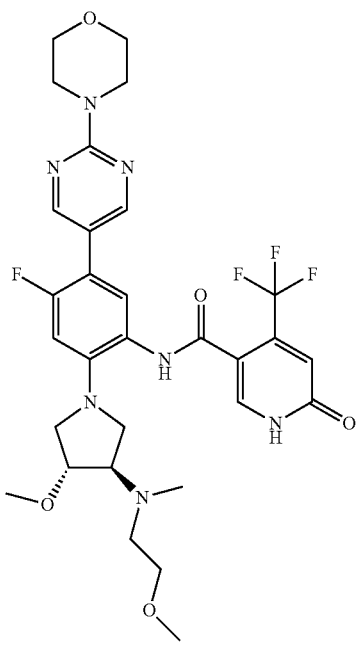 [SMILES: COCCN(C)[C@@H]1CN(c2cc(F)c(-c3cnc(N4CCOCC4)nc3)cc2NC(=O)c2c[nH]c(=O)cc2C(F)(F)F)C[C@H]1OC]

Step 1: tert-butyl trans-3-hydroxy-4-((2-methoxyethyl)(methyl)amino)pyrrolidine-1-carboxylate

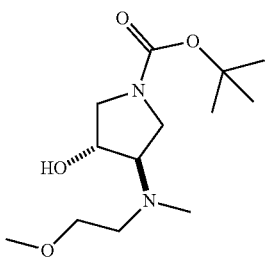 [SMILES: COCCN(C)[C@@H]1CN(C(=O)OC(C)(C)C)C[C@H]1O]

A solution of tert-butyl 6-oxa-3-azabicyclo[3.1.0]hexane-3-carboxylate (0.84 mL, 5.4 mmol) and N-(2-methoxyethyl)methylamine (0.59 mL, 10.8 mmol) in a sealed microwave vial was stirred at 60° C. for 48 h. Flash column chromatography [0.5-10% MeOH/DCM+0.5% NH$_4$OH] afforded tert-butyl trans-3-hydroxy-4-((2-methoxyethyl)(methyl)amino)pyrrolidine-1-carboxylate (1.48 g, 100%). $^1$H NMR (500 MHz, DMSO-d6) δ=5.08 (br d, J=2.9 Hz, 1H), 4.09 (br s, 1H), 3.48-3.36 (m, 4H), 3.23 (s, 3H), 3.12 (dt, J=5.7, 11.6 Hz, 1H), 3.05-2.94 (m, 1H), 2.85 (br dd, J=6.1, 14.5 Hz, 1H), 2.71-2.63 (m, 1H), 2.57-2.53 (m, 1H), 2.22 (s, 3H), 1.39 (s, 9H).

Step 2: tert-butyl trans-3-methoxy-4-((2-methoxyethyl)(methyl)amino)pyrrolidine-1-carboxylate

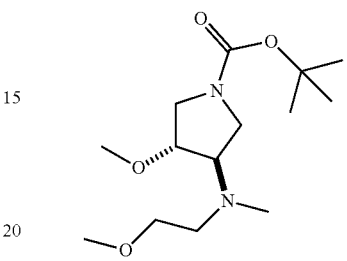

To a solution of tert-butyl trans-3-hydroxy-4-((2-methoxyethyl)(methyl)amino)pyrrolidine-1-carboxylate (0.26 g, 0.95 mmol) in THF (10 mL) at 0° C. was added sodium hydride (60%, 0.055 g, 1.42 mmol) and the reaction mixture was allowed to stir at 0° C. for 10 min. Iodomethane (0.08 mL, 1.23 mmol) was added and the resulting mixture was allowed to stir at room temperature for 18 h. The reaction mixture was quenched with saturated aqueous NH$_4$Cl and extracted with EtOAc. The combined organic extracts were washed with saturated aqueous brine and dried over magnesium sulfate. After removal of the inorganics by filtration the filtrate was concentrated to dryness to afford tert-butyl trans-3-methoxy-4-((2-methoxyethyl)(methyl)amino)pyrrolidine-1-carboxylate (0.089 g, 32%) that was used in the next step without further purification.

Step 3: trans-1-(4-bromo-5-fluoro-2-nitrophenyl)-4-methoxy-N-(2-methoxyethyl)-N-methylpyrrolidin-3-amine

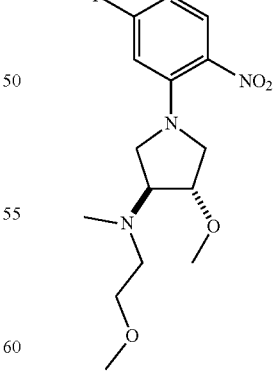

To a solution of tert-butyl trans-3-methoxy-4-((2-methoxyethyl)(methyl)amino)pyrrolidine-1-carboxylate (0.14 g, 0.48 mmol) in DCM (5 mL) was added TFA (0.19 mL, 2.4 mmol). The reaction mixture was stirred at room temperature for 1 h. The reaction mixture was concentrated under reduced pressure and the residue was dissolved in toluene (1 mL). The solution of deprotected amine was added dropwise to a rapidly stirring mixture of 1-bromo-2,4-difluoro-5-nitrobenzene (0.120 g, 0.48 mmol), potassium carbonate (0.033 g, 0.24 mmol) and N,N-diisopropylethylamine (0.085 mL, 0.48 mmol) in toluene (2 mL) at room temperature. After stirring for 20 minutes at room temperature the reaction mixture was heated to 45° C. for 18 h. The reaction mixture was partitioned between water and ethyl acetate. The layers were separated and the aqueous layer was extracted with an additional portion of ethyl acetate. The combined organic extracts were dried over magnesium sulfate. After removal of the inorganics by filtration the filtrate was concentrated to dryness and the residue was purified by flash chromatography [1-10% MeOH/DCM+0.5% NH$_4$OH] to afford trans-1-(4-bromo-5-fluoro-2-nitrophenyl)-4-methoxy-N-(2-methoxyethyl)-N-methylpyrrolidin-3-amine (0.034 g, 17%). $^1$H NMR (500 MHz, METHANOL-d4) δ=8.01 (d, J=7.3 Hz, 1H), 6.94 (d, J=11.9 Hz, 1H), 4.05 (q, J=4.8 Hz, 1H), 3.54 (dd, J=5.9, 10.8 Hz, 1H), 3.52-3.47 (m, 2H), 3.44-3.39 (m, 1H), 3.37 (s, 3H), 3.33 (s, 3H), 3.29-3.23 (m, 2H), 3.11 (dd, J=4.5, 10.9 Hz, 1H), 2.82-2.74 (m, 1H), 2.73-2.65 (m, 1H), 2.35 (s, 3H).

Step 4: trans-1-(5-fluoro-4-(2-morpholinopyrimidin-5-yl)-2-nitrophenyl)-4-methoxy-N-(2-methoxyethyl)-N-methylpyrrolidin-3-amine

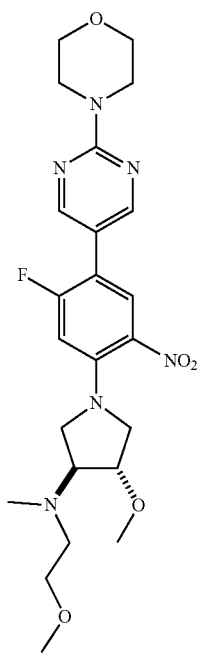 [SMILES: COCCN(C)[C@H]1CN(c2cc(F)c(-c3cnc(N4CCOCC4)nc3)cc2[N+](=O)[O-])C[C@@H]1OC]

A microwave vial was charged with 2-(4-morpholino)pyrimidine-5-boronic acid pinacol ester (0.037 g, 0.13 mmol), potassium phosphate (0.053 g, 0.25 mmol) and bis(di-tert-butyl(4-dimethylaminophenyl)phosphine)dichloropalladium(II) (0.006 g, 8.4 μmol). The vial was sealed with a septum and then evacuated and backfilled with nitrogen. A solution of trans-1-(4-bromo-5-fluoro-2-nitrophenyl)-4-methoxy-N-(2-methoxyethyl)-N-methylpyrrolidin-3-amine (0.034 g, 0.084 mmol) in 1,4-dioxane (4.4 mL) was added via syringe followed by water (0.5 mL). The reaction was irradiated to a temperature of 110° C. for 40 min. The reaction mixture was partitioned between water and DCM. The layers were separated and the aqueous layer was extracted with an additional portion of DCM. The combined organic extracts were dried over magnesium sulfate. After removal of the inorganics by filtration the filtrate was concentrated to dryness and the residue was purified by flash chromatography [0.5-7.5% MeOH/DCM+0.5% NH$_4$OH] to afford trans-1-(5-fluoro-4-(2-morpholinopyrimidin-5-yl)-2-nitrophenyl)-4-methoxy-N-(2-methoxyethyl)-N-methylpyrrolidin-3-amine (0.043 g, 100%). LCMS [M+H]+: 491.5.

Step 5: trans-1-(2-amino-5-fluoro-4-(2-morpholinopyrimidin-5-yl)phenyl)-4-methoxy-N-(2-methoxyethyl)-N-methylpyrrolidin-3-amine

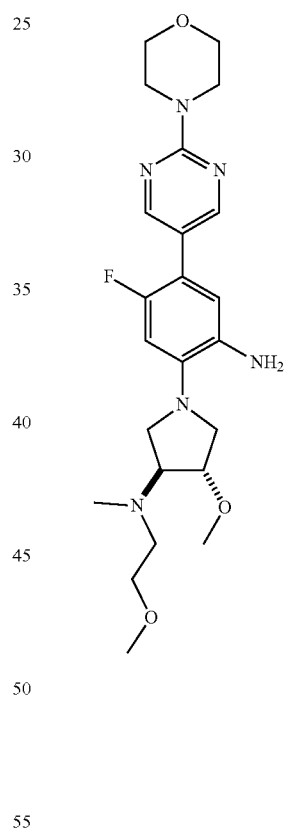

A mixture of trans-1-(5-fluoro-4-(2-morpholinopyrimidin-5-yl)-2-nitrophenyl)-4-methoxy-N-(2-methoxyethyl)-N-methylpyrrolidin-3-amine (0.040 g, 0.082 mmol) and tin(II) chloride (0.046 g, 0.25 mmol) in EtOH (5 mL) was heated to 70° C. for 18 h. The reaction mixture was concentrated onto celite and purified by flash chromatography [0.5-10% MeOH/DCM+0.5% NH$_4$OH] to afford trans-1-(2-amino-5-fluoro-4-(2-morpholinopyrimidin-5-yl)phenyl)-4-methoxy-N-(2-methoxyethyl)-N-methylpyrrolidin-3-amine (0.023 g, 61%). LCMS [M+H]+: 461.5.

Step 6: N-(4-fluoro-2-(trans-3-methoxy-4-((2-methoxyethyl)(methyl)amino)pyrrolidin-1-yl)-5-(2-morpholinopyrimidin-5-yl)phenyl)-6-oxo-4-(trifluoromethyl)-1,6-dihydropyridine-3-carboxamide

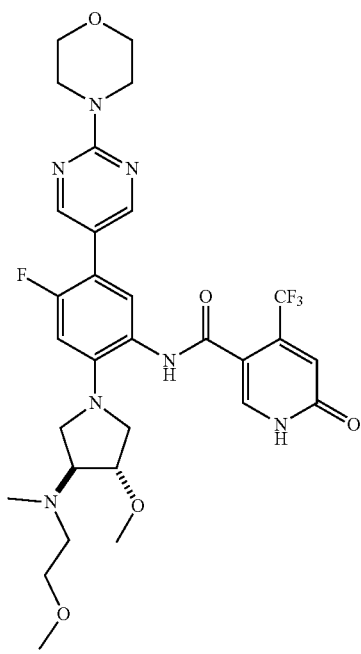 [SMILES: COCCN(C)[C@H]1CN(c2cc(F)c(-c3cnc(N4CCOCC4)nc3)cc2NC(=O)c2c[nH]c(=O)cc2C(F)(F)F)C[C@@H]1OC]

4-(Trifluoromethyl)-6-(2-(trimethylsilyl)ethoxy)nicotinic acid (0.022 g, 0.072 mmol) and propylphosphonic anhydride solution (0.15 mL, 0.48 mmol) were added to a suspension of trans-1-(2-amino-5-fluoro-4-(2-morpholinopyrimidin-5-yl)phenyl)-4-methoxy-N-(2-methoxyethyl)-N-methylpyrrolidin-3-amine (0.022 g, 0.048 mmol) in THF (0.8 mL) at room temperature. A solution of 4-methylmorpholine (0.013 mL, 0.12 mmol) in THF (0.2 mL) was added dropwise and the reaction was allowed to stir at room temperature for 4 h. The reaction mixture was partitioned between water and DCM. The layers were separated and the aqueous layer was extracted with an additional portion of DCM. The combined organic layers were washed with water, 1 N aqueous NaOH, a saturated brine solution and then dried over magnesium sulfate. After removal of the inorganics by filtration the filtrate was concentrated to dryness and the residue was purified by flash chromatography [0.5-10% MeOH/DCM+ 0.5% NH$_4$OH]. The silyl protected amide was dissolved in DCM (2 mL) and treated with TFA (0.2 mL) at room temperature. After stirring for 1 h the volatiles were removed in vacuo and the title compound was isolated using a catch and release protocol with a PoraPak Rxn CX ion exchange column to afford the title compound N-(4-fluoro-2-((3S,4S)-3-methoxy-4-((2-methoxyethyl)(methyl)amino)pyrrolidin-1-yl)-5-(2-morpholinopyrimidin-5-yl)phenyl)-6-oxo-4-(trifluoromethyl)-1,6-dihydropyridine-3-carboxamide (6.0 mg, 21% yield). $^1$H NMR (500 MHz, DMSO-d6) δ=9.80 (s, 1H), 8.51 (s, 2H), 7.97 (br s, 1H), 7.36 (br d, J=8.8 Hz, 1H), 6.81 (s, 1H), 6.75 (d, J=13.8 Hz, 1H), 3.87 (q, J=4.7 Hz, 1H), 3.77-3.71 (m, 4H), 3.70-3.64 (m, 4H), 3.50 (dd, J=6.2, 10.5 Hz, 1H), 3.44 (br dd, J=7.4, 10.0 Hz, 1H), 3.38 (br t, J=6.0 Hz, 2H), 3.26 (s, 3H), 3.21 (s, 3H), 3.10-3.04 (m, 1H), 2.68-2.61 (m, 1H), 2.58-2.53 (m, 1H), 2.23 (s, 3H); LCMS [M+H]+: 650.6.

Example 577: N-[4-fluoro-5-(2-morpholin-4-ylpyrimidin-5-yl)-2-[(3R,4R)-3-fluoro-4-[2-methoxyethyl(methyl)amino]pyrrolidin-1-yl]phenyl]-6-oxo-4-(trifluoromethyl)-1H-pyridine-3-carboxamide

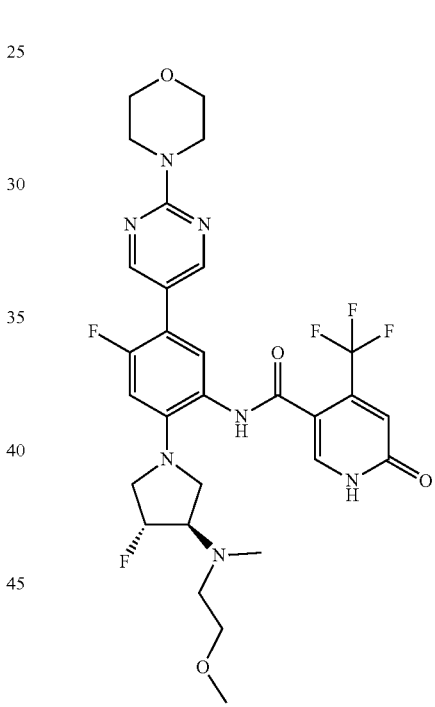

The title compound was prepared similar to the procedure described above for the preparation of Example 307 using N-(2-methoxyethyl)methylamine in place of dimethylamine in Step 1. $^1$H NMR (500 MHz, DMSO-d6) δ=9.83 (s, 1H), 8.53 (s, 2H), 8.00 (br s, 1H), 7.41 (br d, J=8.9 Hz, 1H), 6.85-6.77 (m, 2H), 5.34-5.14 (m, 1H), 3.76-3.73 (m, 5H), 3.70-3.67 (m, 5H), 3.63-3.58 (m, 2H), 3.53 (br d, J=4.2 Hz, 1H), 3.43-3.39 (m, 3H), 3.28-3.25 (m, 2H), 3.22 (s, 3H), 3.16 (br dd, J=6.9, 9.7 Hz, 2H), 2.26 (s, 3H); LCMS [M+H]+: 638.5.

Example 578: N-[4-fluoro-5-(2-morpholin-4-ylpyrimidin-5-yl)-2-[(3R)-3-[2-methoxyethyl(methyl)amino]pyrrolidin-1-yl]phenyl]-6-oxo-4-(trifluoromethyl)-1H-pyridine-3-carboxamide Example 579: N-[4-fluoro-5-(2-morpholin-4-ylpyrimidin-5-yl)-2-[(3R,4R)-3-fluoro-4-[2-methoxyethyl(methyl)amino]pyrrolidin-1-yl]phenyl]-1-methyl-6-oxo-4-(trifluoromethyl)pyridine-3-carboxamide

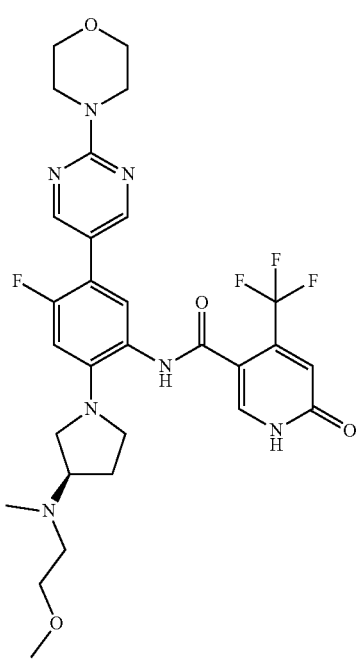 [SMILES: COCCN(C)[C@@H]1CCN(c2cc(F)c(-c3cnc(N4CCOCC4)nc3)cc2NC(=O)c2c[nH]c(=O)cc2C(F)(F)F)C1]

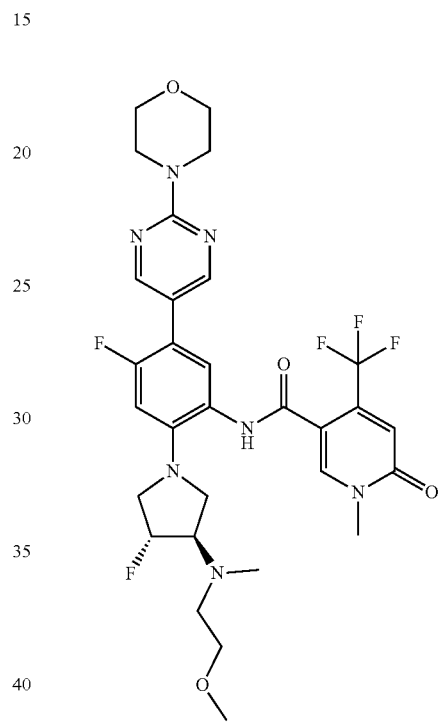

(R)-1-(2-Amino-5-fluoro-4-(2-morpholinopyrimidin-5-yl)phenyl)-N-(2-methoxyethyl)-N-methylpyrrolidin-3-amine (50 mg, 0.116 mmol, prepared by a route similar to that described in Example 541) was dissolved in N,N-dimethylformamide (DMF) (1 ml) and treated with a solution of activated acid [4-(trifluoromethyl)-6-(2-(trimethylsilyl)ethoxy)nicotinic acid (53.5 mg, 0.174 mmol), HATU (66.2 mg, 0.174 mmol) and N,N-diisopropylethylamine (0.030 ml, 0.174 mmol) in N,N-dimethylformamide (DMF) (0.5 ml)] at room temperature. After stirring for 30 minutes at room temperature, the standard workup and purification provided the title compound (0.065 mmol, 55.6% yield) as a yellow solid. $^1$H NMR (500 MHz, DMSO-d6) δ=9.77 (s, 1H), 8.51 (s, 2H), 8.00-7.94 (m, 1H), 7.31 (d, J=8.6 Hz, 1H), 6.76 (br s, 1H), 6.67 (d, J=13.9 Hz, 1H), 3.75-3.72 (m, 4H), 3.70-3.66 (m, 4H), 3.40-3.37 (m, 4H), 3.27-3.22 (m, 2H), 3.21 (s, 3H), 3.03-2.94 (m, 1H), 2.20 (s, 3H), 2.11-2.06 (m, 2H), 1.70 (quin, J=10.0 Hz, 1H); LCMS [M+H]+: 620.6.

The title compound (47 mg, 57% yield) was from cis (3R,4S)-1-(2-amino-5-fluoro-4-(2-morpholinopyrimidin-5-yl)phenyl)-4-fluoro-N-(2-methoxyethyl)-N-methylpyrrolidin-3-amine (50 mg, 0.111 mmol) and [1-methyl-6-oxo-4-(trifluoromethyl)-1,6-dihydropyridine-3-carboxylic acid (37.0 mg, 0.167 mmol) using procedures similar to those described hereinabove. $^1$H NMR (500 MHz, DMSO-d6) δ=9.84 (s, 1H), 8.52 (s, 2H), 8.36 (s, 1H), 7.39 (d, J=8.8 Hz, 1H), 6.91-6.81 (m, 2H), 5.32-5.12 (m, 1H), 3.77-3.74 (m, 4H), 3.70-3.67 (m, 4H), 3.64-3.57 (m, 2H), 3.56-3.52 (m, 4H), 3.43-3.39 (m, 2H), 3.28-3.24 (m, 1H), 3.22 (s, 3H), 3.15 (dd, J=6.7, 10.0 Hz, 1H), 2.64 (br t, J=5.9 Hz, 1H), 2.59 (br t, J=5.9 Hz, 1H), 2.26 (s, 3H); LCMS [M+H]+: 652.5.

Example 580: N-[4-fluoro-5-(2-morpholin-4-ylpyrimidin-5-yl)-2-[(3R)-3-[2-methoxyethyl(methyl)amino]pyrrolidin-1-yl]phenyl]-1-methyl-6-oxo-4-(trifluoromethyl)pyridine-3-carboxamide Example 581: N-[4-fluoro-5-(6-methylsulfonylpyridin-3-yl)-2-[(3R,5S)-3,4,5-trimethylpiperazin-1-yl]phenyl]-6-oxo-4-(trifluoromethyl)-1H-pyridine-3-carboxamide

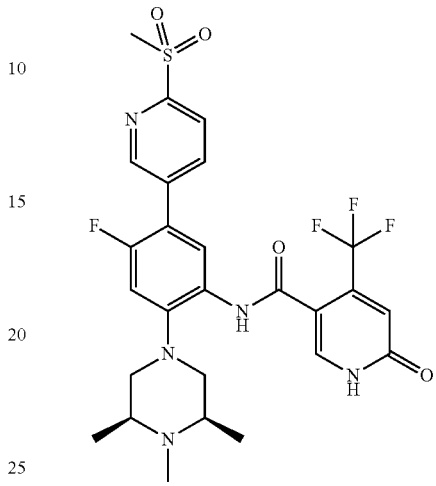

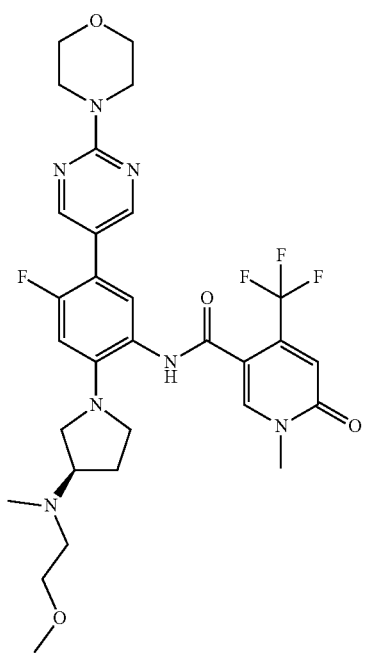 [SMILES: COCCN(C)[C@@H]1CCN(c2cc(F)c(-c3cnc(N4CCOCC4)nc3)cc2NC(=O)c2cn(C)c(=O)cc2C(F)(F)F)C1]

The title compound was prepared by methods similar to those described in Example 39 using 2-(methylsulfonyl)-5-(4,4,5,5-tetramethyl-1,3,2-dioxaborolan-2-yl)pyridine. $^1$H NMR (500 MHz, DMSO-d6) δ=9.64 (s, 1H), 8.92 (s, 1H), 8.26 (dd, J=1.2, 8.3 Hz, 1H), 8.15 (d, J=8.2 Hz, 1H), 7.93 (s, 1H), 7.87 (d, J=8.4 Hz, 1H), 7.12 (d, J=12.6 Hz, 1H), 6.81 (s, 1H), 3.11 (br d, J=11.0 Hz, 2H), 2.37 (br s, 2H), 2.21 (br s, 3H), 1.02 (d, J=6.1 Hz, 6H); LCMS [M+H]+: 582.1.

Example 582: N-[4-fluoro-5-[2-(methanesulfonamido)pyrimidin-5-yl]-2-[(3R,5S)-3,4,5-trimethylpiperazin-1-yl]phenyl]-6-oxo-4-(trifluoromethyl)-1H-pyridine-3-carboxamide

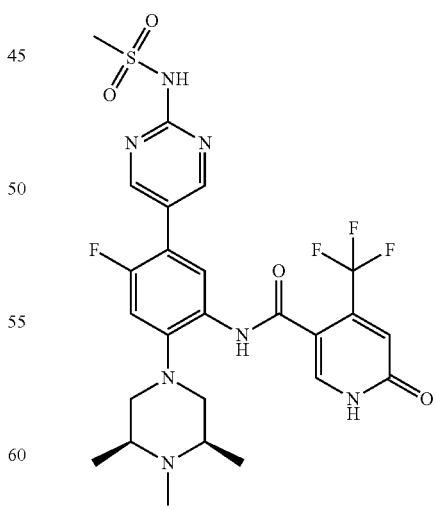

The title compound (46 mg, 53% yield) was prepared from (R)-1-(2-amino-5-fluoro-4-(2-morpholinopyrimidin-5-yl)phenyl)-N-(2-methoxyethyl)-N-methylpyrrolidin-3-amine (50 mg, 0.116 mmol) and [1-methyl-6-oxo-4-(trifluoromethyl)-1,6-dihydropyridine-3-carboxylic acid (38.5 mg, 0.174 mmol) according to procedures similar to those described hereinabove. $^1$H NMR (500 MHz, DMSO-d6) δ=9.79 (s, 1H), 8.50 (s, 2H), 8.33 (s, 1H), 7.30 (d, J=8.7 Hz, 1H), 6.87 (s, 1H), 6.70 (d, J=13.8 Hz, 1H), 3.76-3.73 (m, 4H), 3.70-3.67 (m, 4H), 3.55 (s, 3H), 3.40-3.37 (m, 5H), 3.24 (br d, J=7.2 Hz, 1H), 3.20 (s, 3H), 3.02-2.95 (m, 1H), 2.20 (s, 3H), 2.12-2.05 (m, 1H), 1.70 (quin, J=9.8 Hz, 1H); LCMS [M+H]+: 634.6.

The title compound was prepared in a manner similar to the preparation of Example 39, from 2-(methylsulfonylamino)pyrimidine-5-boronic acid pinacol ester. $^1$H NMR (500 MHz, DMSO-d6) δ=12.69-12.34 (m, 1H), 9.54 (s, 1H), 8.69 (s, 2H), 7.85 (br s, 1H), 7.75 (br d, J=8.2 Hz, 1H), 7.04 (br d, J=12.2 Hz, 1H), 6.75 (s, 1H), 3.33 (s, 3H), 3.03 (br d, J=7.6 Hz, 2H), 2.25-2.17 (m, 2H), 1.17 (br s, 2H), 0.98 (br s, 6H); LCMS [M+H]+: 598.4.

Example 583: N-[5-[1-(5-cyanopyrimidin-2-yl)-3,6-dihydro-2H-pyridin-5-yl]-4-fluoro-2-[(3R,5S)-3,4,5-trimethylpiperazin-1-yl]phenyl]-6-oxo-4-(trifluoromethyl)-1H-pyridine-3-carboxamide

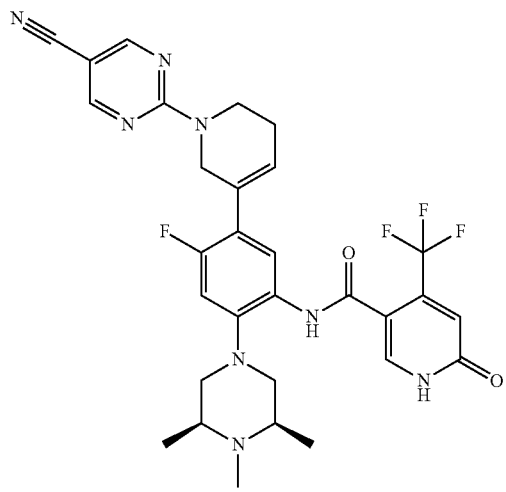 [SMILES: C[C@@H]1CN(c2cc(F)c(C3=CCCN(c4ncc(C#N)cn4)C3)cc2NC(=O)c2c[nH]c(=O)cc2C(F)(F)F)C[C@H](C)N1C]

The procedure used was similar to that of Example 270 using N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) and 2-Bromo-5-cyanopyrimidine (13.05 mg, 0.071 mmol) to give the title compound (27 mg, 71% yield). $^1$H NMR (500 MHz, METHANOL-d4) δ=8.59-8.44 (m, 2H), 7.88-7.81 (m, 1H), 7.72-7.63 (m, 1H), 6.92-6.84 (m, 1H), 6.83-6.79 (m, 1H), 6.14-5.97 (m, 1H), 4.59-4.53 (m, 2H), 4.03-3.98 (m, 2H), 2.96-2.89 (m, 2H), 2.52-2.41 (m, 4H), 2.34-2.29 (m, 2H), 2.28-2.25 (m, 3H), 1.07-1.04 (m, 6H); LCMS [M+H]+ 611.5.

Example 584: N-[4-fluoro-5-(I-methylsulfonyl-3,6-dihydro-2H-pyridin-5-yl)-2-[(3R,5S)-3,4,5-trimethylpiperazin-1-yl]phenyl]-6-oxo-4-(trifluoromethyl)-1H-pyridine-3-carboxamide

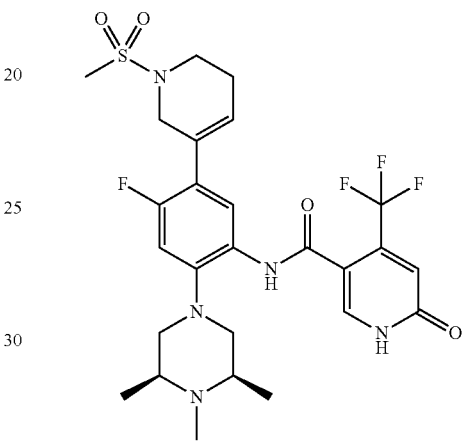

To a solution of N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and N,N-diisopropylethylamine (0.017 ml, 0.099 mmol) in DCM (3 ml) at RT was added methanesulfonyl chloride (4.00 µl, 0.052 mmol). The mixture was stirred at room temperature for 5 min and quenched with MeOH, concentrated onto celite. It was purified on Isco column (4 g), eluting with DCM containing 0-6% MeOH and 0-0.6% NH$_4$OH. The desired fractions were combined and concentrated to afford the title compound as a white powder (15 mg, 49%). $^1$H NMR (500 MHz, METHANOL-d4) δ=7.86-7.81 (m, 1H), 7.68-7.62 (m, 1H), 6.90-6.84 (m, 1H), 6.83-6.78 (m, 1H), 6.05-5.97 (m, 1H), 3.98-3.95 (m, 2H), 3.35 (t, J=5.9 Hz, 2H), 2.97-2.89 (m, 2H), 2.84-2.80 (m, 3H), 2.51-2.46 (m, 2H), 2.45-2.39 (m, 2H), 2.38-2.32 (m, 2H), 2.29-2.25 (m, 3H), 1.05 (d, J=6.0 Hz, 6H); LCMS [M+H]+ 686.7.

745

Example 585: N-[4-fluoro-5-(I-methylsulfonyl-3,6-dihydro-2H-pyridin-4-yl)-2-[(3R,5S)-3,4,5-trimethylpiperazin-1-yl]phenyl]-6-oxo-4-(trifluoromethyl)-1H-pyridine-3-carboxamide

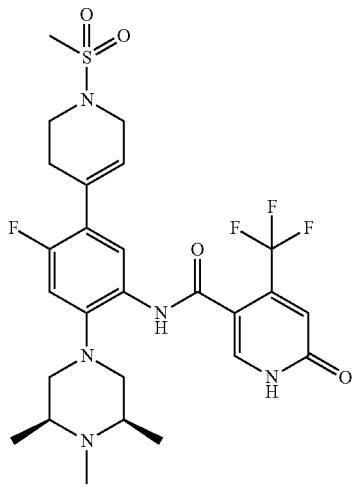 [SMILES: C[C@@H]1CN(c2cc(F)c(C3=CCN(S(C)(=O)=O)CC3)cc2NC(=O)c2c[nH]c(=O)cc2C(F)(F)F)C[C@H](C)N1C]

The procedure was similar to that used in Example 584 from N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (34 mg, 0.067 mmol) to give the title compound (17.5 mg, 42% yield). $^1$H NMR (500 MHz, METHANOL-d4) δ=7.99-7.93 (m, 1H), 7.83-7.75 (m, 1H), 7.00-6.95 (m, 1H), 6.94-6.90 (m, 1H), 6.09-6.01 (m, 1H), 4.00-3.94 (m, 2H), 3.53-3.48 (m, 2H), 3.06-3.01 (m, 2H), 2.95-2.92 (m, 3H), 2.67-2.62 (m, 2H), 2.62-2.57 (m, 2H), 2.56-2.50 (m, 2H), 2.41-2.36 (m, 3H), 1.19-1.16 (m, 6H); LCMS [M+H]+ 686.7.

746

Example 586: N-[4-fluoro-5-(2-morpholin-4-ylpyrimidin-5-yl)-2-[(3R)-3-[cyclopropylmethyl(methyl)amino]pyrrolidin-1-yl]phenyl]-6-oxo-4-(trifluoromethyl)-1H-pyridine-3-carboxamide

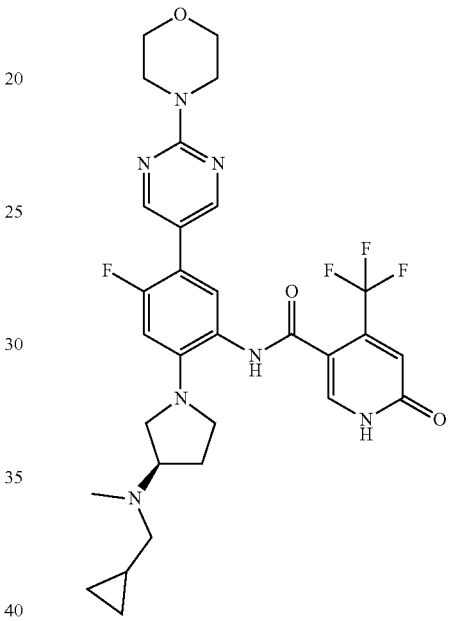

The title compound (17 mg, 59% yield) was prepared according to procedures similar to Examples hereinabove from (R)-1-(2-amino-5-fluoro-4-(2-morpholinopyrimidin-5-yl)phenyl)-N-(cyclopropylmethyl)-N-methylpyrrolidin-3-amine (20 mg, 0.047 mmol) and [4-(trifluoromethyl)-6-(2-(trimethylsilyl)ethoxy)nicotinic acid (21.62 mg, 0.070 mmol) and deprotection of the intermediate using TFA. $^1$H NMR (500 MHz, DMSO-d6) δ=12.48 (br s, 1H), 9.79 (s, 1H), 8.50 (s, 2H), 7.96 (br s, 1H), 7.31 (br d, J=8.7 Hz, 1H), 6.80 (s, 1H), 6.66 (d, J=13.8 Hz, 1H), 3.75-3.71 (m, 4H), 3.68-3.65 (m, 4H), 3.38-3.35 (m, 3H), 3.27-3.22 (m, 2H), 2.98-2.90 (m, 1H), 2.25 (s, 3H), 2.23-2.19 (m, 2H), 2.10-2.04 (m, 1H), 1.75-1.64 (m, 1H), 0.99 (br d, J=5.7 Hz, 2H), 0.85-0.78 (m, 1H), 0.43 (br d, J=7.9 Hz, 2H), 0.02 (br d, J=4.5 Hz, 2H); LCMS [M+H]+: 616.5.

Example 587: N-[4-fluoro-5-(2-morpholin-4-ylpyrimidin-5-yl)-2-[(3R)-3-[cyclopropylmethyl(methyl)amino]pyrrolidin-1-yl]phenyl]-1-methyl-6-oxo-4-(trifluoromethyl)pyridine-3-carboxamide

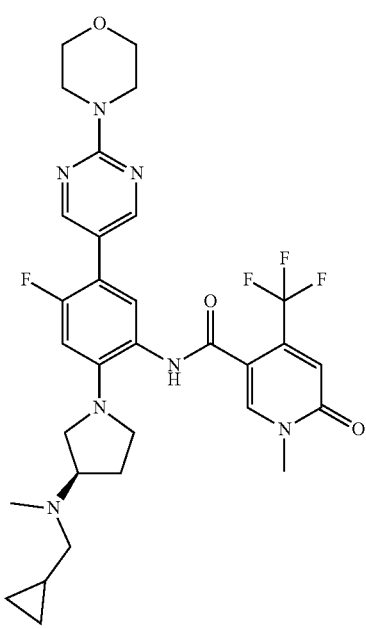 [SMILES: CN(CC1CC1)[C@@H]1CCN(c2cc(F)c(-c3cnc(N4CCOCC4)nc3)cc2NC(=O)c2cn(C)c(=O)cc2C(F)(F)F)C1]

The title compound was prepared from (R)-1-(2-amino-5-fluoro-4-(2-morpholinopyrimidin-5-yl)phenyl)-N-(cyclopropylmethyl)-N-methylpyrrolidin-3-amine (20 mg, 0.047 mmol) and 1-methyl-6-oxo-4-(trifluoromethyl)-1,6-dihydropyridine-3-carboxylic acid (15.55 mg, 0.070 mmol) followed by deprotection by procedures similar to those described hereinabove. $^1$H NMR (500 MHz, DMSO-d6) δ=9.78 (s, 1H), 8.49 (s, 2H), 8.34 (s, 1H), 7.29 (d, J=8.7 Hz, 1H), 6.86 (s, 1H), 6.69 (d, J=13.8 Hz, 1H), 3.75-3.72 (m, 4H), 3.69-3.65 (m, 4H), 3.54 (s, 3H), 3.41-3.34 (m, 5H), 3.29-3.21 (m, 2H), 2.98-2.89 (m, 1H), 2.24 (s, 3H), 2.21 (br d, J=6.4 Hz, 2H), 2.11-2.04 (m, 1H), 1.74-1.65 (m, 1H), 0.84-0.76 (m, 1H), 0.43 (br d, J=7.8 Hz, 2H), 0.02 (br d, J=4.5 Hz, 2H); LCMS [M+H]+: 630.6.

Example 588: N-[5-[1-(5-cyanopyrimidin-2-yl)-2,5-dihydropyrrol-3-yl]-4-fluoro-2-[(3R,5S)-3,4,5-trimethylpiperazin-1-yl]phenyl]-6-oxo-4-(trifluoromethyl)-1H-pyridine-3-carboxamide

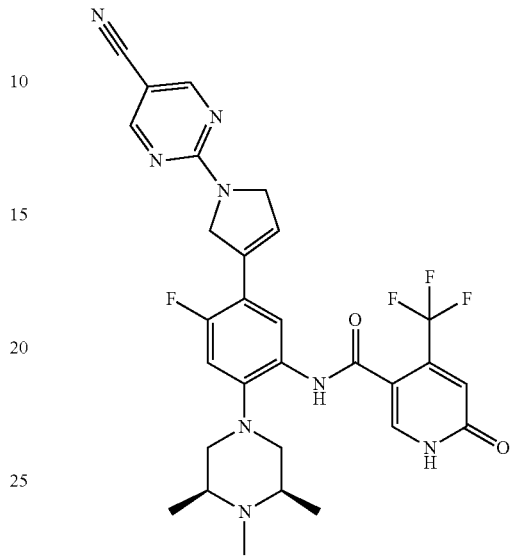

A procedure similar to that of Example 270 using N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (20 mg, 0.041 mmol) and 2-bromo-5-cyanopyrimidine (8.95 mg, 0.049 mmol) gave the title compound (10 mg, 39% yield). $^1$H NMR (500 MHz, METHANOL-d4) δ=9.53-9.42 (m, 1H), 8.90-8.79 (m, 2H), 8.03-7.92 (m, 1H), 7.81-7.70 (m, 1H), 7.07-6.97 (m, 1H), 6.82-6.72 (m, 1H), 6.49-6.40 (m, 1H), 4.75-4.67 (m, 2H), 4.58-4.51 (m, 2H), 3.08-3.01 (m, 2H), 2.47-2.41 (m, 2H), 2.36-2.28 (m, 2H), 2.19 (s, 3H), 1.03-0.98 (m, 6H); LCMS [M+H]+ 597.6.

Example 589: N-[5-(3-carbamoyl-4-fluorophenyl)-4-fluoro-2-[(3R,5S)-3,4,5-trimethylpiperazin-1-yl]phenyl]-1-methyl-6-oxo-4-(trifluoromethyl)pyridine-3-carboxamide

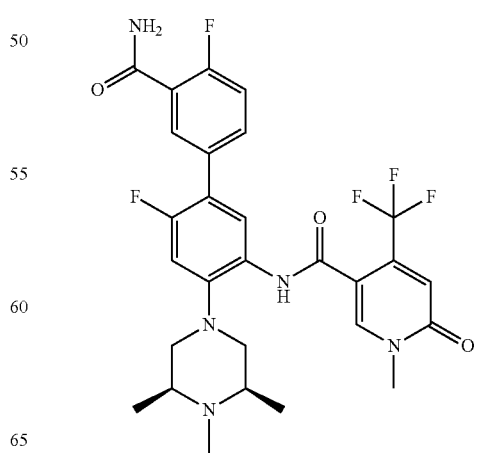

The procedure was similar to that of Example 400 using N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (50 mg, 0.096 mmol, from Example 226, Step 1) and 3-carbamoyl-4-fluorophenylboronic acid, 97% (26.4 mg, 0.144 mmol). The title compound was isolated as a white fluffy powder (27 mg, 0.044 mmol, 46.1% yield). $^1$H NMR (500 MHz, METHANOL-d4) δ=8.14 (s, 1H), 7.88 (br d, J=5.9 Hz, 1H), 7.83 (d, J=8.3 Hz, 1H), 7.65-7.54 (m, 1H), 7.21 (dd, J=8.7, 10.6 Hz, 1H), 6.97 (d, J=12.0 Hz, 1H), 6.85-6.80 (m, 1H), 3.54 (s, 3H), 2.95 (br d, J=11.4 Hz, 2H), 2.56-2.45 (m, 2H), 2.44-2.35 (m, 2H), 2.24 (s, 3H), 1.05 (d, J=6.2 Hz, 6H); LCMS [M+H]$^+$ 578.

Example 590: N-[5-(4-carbamoyl-3-fluorophenyl)-4-fluoro-2-[(3R,5S)-3,4,5-trimethylpiperazin-1-yl]phenyl]-1-methyl-6-oxo-4-(trifluoromethyl)pyridine-3-carboxamide

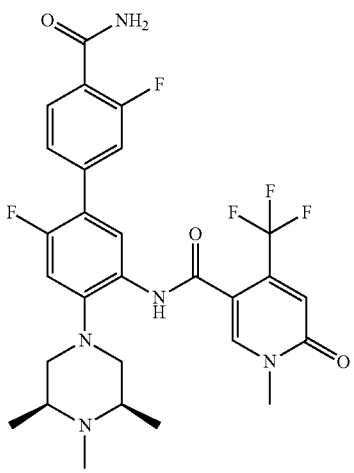 [SMILES: C[C@@H]1CN(c2cc(F)c(-c3ccc(C(N)=O)c(F)c3)cc2NC(=O)c2cn(C)c(=O)cc2C(F)(F)F)C[C@H](C)N1C]

The sequence used was similar to Example 400 using N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (50 mg, 0.096 mmol) and 4-carbamoyl-3-fluorophenylboronic acid, 96% (26.4 mg, 0.144 mmol). The title compound was isolated as a white fluffy powder (26 mg, 0.043 mmol, 44.4% yield). $^1$H NMR (500 MHz, METHANOL-d4) δ=8.14 (s, 1H), 7.87 (d, J=8.3 Hz, 1H), 7.80 (t, J=8.0 Hz, 1H), 7.39 (d, J=8.2 Hz, 1H), 7.34 (d, J=12.5 Hz, 1H), 6.99 (d, J=12.2 Hz, 1H), 6.86-6.81 (m, 1H), 3.54 (s, 3H), 2.98 (br d, J=11.4 Hz, 2H), 2.52 (t, J=11.2 Hz, 2H), 2.46-2.34 (m, 2H), 2.24 (s, 3H), 1.05 (d, J=6.2 Hz, 6H); LCMS [M+H]$^+$ 578.

Example 591: N-[5-(3-carbamoyl-4-fluorophenyl)-4-fluoro-2-[(3R,5S)-3,4,5-trimethylpiperazin-1-yl]phenyl]-4-(difluoromethyl)-1-methyl-6-oxopyridine-3-carboxamide

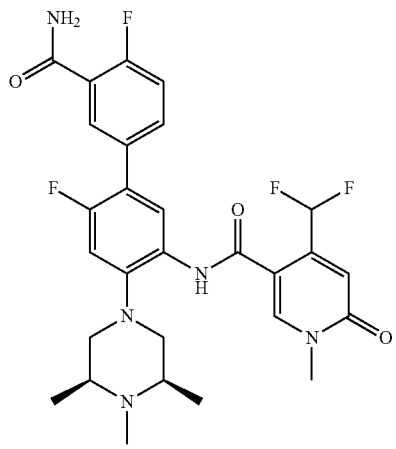 [SMILES: C[C@@H]1CN(c2cc(F)c(-c3ccc(F)c(C(N)=O)c3)cc2NC(=O)c2cn(C)c(=O)cc2C(F)F)C[C@H](C)N1C]

The procedure was similar to Example 400 using N-(5-bromo-4-fluoro-2-((3S,5R)-3,4,5-trimethylpiperazin-1-yl)phenyl)-4-(difluoromethyl)-1-methyl-6-oxo-1,6-dihydropyridine-3-carboxamide (50 mg, 0.100 mmol, preparation described in Example 461) and 3-carbamoyl-4-fluorophenylboronic acid, 97% (27.4 mg, 0.150 mmol). The title compound was isolated as an off-white fluffy powder (15.9 mg, 0.027 mmol, 27.1% yield). $^1$H NMR (500 MHz, METHANOL-d4) δ=8.20 (s, 1H), 7.91-7.85 (m, 1H), 7.71 (d, J=8.3 Hz, 1H), 7.65-7.59 (m, 1H), 7.32-7.05 (m, 2H), 6.98 (d, J=12.1 Hz, 1H), 6.74-6.68 (m, 1H), 3.54 (s, 3H), 3.05 (br d, J=10.6 Hz, 2H), 2.68-2.52 (m, 4H), 2.37 (s, 3H), 1.11 (d, J=5.7 Hz, 6H); LCMS [M+H]$^+$ 560.

Example 592: N-[5-(4-carbamoyl-3-fluorophenyl)-4-fluoro-2-[(3R,5S)-3,4,5-trimethylpiperazin-1-yl]phenyl]-4-(difluoromethyl)-1-methyl-6-oxopyridine-3-carboxamide

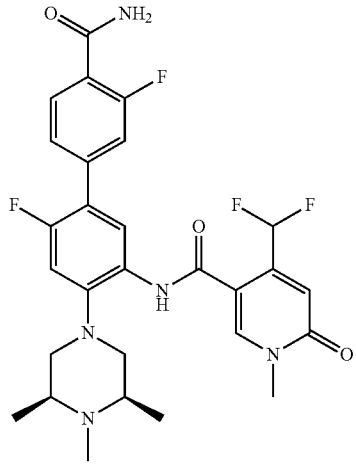 [SMILES: C[C@@H]1CN(c2cc(F)c(-c3ccc(C(N)=O)c(F)c3)cc2NC(=O)c2cn(C)c(=O)cc2C(F)F)C[C@H](C)N1C]

The title compound (11.9 mg, 20.3% yield). was prepared by a procedure similar to Example 400 using N-(5-bromo- 4-fluoro-2-((3S,5R)-3,4,5-trimethylpiperazin-1-yl)phenyl)-4-(difluoromethyl)-1-methyl-6-oxo-1,6-dihydropyridine-3-carboxamide (50 mg, 0.100 mmol) and 4-carbamoyl-3-fluorophenylboronic acid, 96% (27.4 mg, 0.150 mmol). $^1$H NMR (500 MHz, METHANOL-d4) δ=8.27 (s, 1H), 8.22 (s, 1H), 7.81 (t, J=7.9 Hz, 1H), 7.74 (d, J=8.2 Hz, 1H), 7.31-7.08 (m, 1H), 7.03 (d, J=12.2 Hz, 1H), 6.75-6.68 (m, 1H), 3.55 (s, 3H), 3.17 (br d, J=12.3 Hz, 2H), 2.73-2.65 (m, 2H), 2.57 (s, 3H), 1.20 (d, J=6.4 Hz, 6H); LCMS [M+H]$^+$ 560.

Example 593: N-[4-fluoro-2-[(3R)-3,4-dimethylpiperazin-1-yl]-5-[2-[(2R)-2-methylmorpholin-4-yl]pyrimidin-4-yl]phenyl]-6-oxo-4-(trifluoromethyl)-1H-pyridine-3-carboxamide

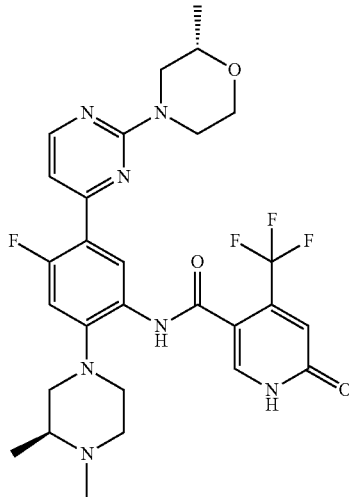 [SMILES: C[C@H]1CN(c2nccc(-c3cc(NC(=O)c4c[nH]c(=O)cc4C(F)(F)F)c(N4CCN(C)[C@@H](C)C4)cc3F)n2)CCO1]

Step 1: (S)—N-(5-bromo-2-(3,4-dimethylpiperazin-1-yl)-4-fluorophenyl)-4-(trifluoromethyl)-6-(2-(trimethylsilyl)ethoxy)nicotinamide

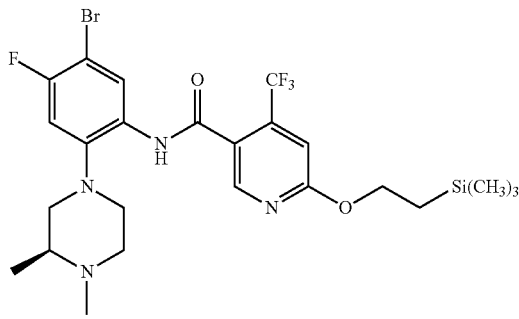

To a stirred solution of 4-(trifluoromethyl)-6-(2-(trimethylsilyl)ethoxy)nicotinic acid (5 g, 16.28 mmol, 1 eq, preparation described in Example 39) in DMF (50 mL) was added DIPEA (6 mL, 32.57 mmol, 2 eq), HATU (44.9 g, 12.37 mmol, 2 eq) and then (S)-5-bromo-2-(3,4-dimethylpiperazin-1-yl)-4l-fluoroaniline (4.6 g, 16.28 mmol, leg) was added at 0° C. under argon atm, and after that stirred for 16 h. TLC analysis indicated formation of nonpolar spots. The reaction mixture was diluted with ice water (200 mL) and extracted with EtOAc (2×500 mL). The organic layer was washed with brine and dried over Na$_2$SO$_4$ and concentrated under reduced pressure to give crude product. The crude product was purified by column chromatography (neutral alumina) using 0-5 EtOAc in pet ether as an eluent to give (S)—N-(5-bromo-2-(3,4-dimethylpiperazin-1-yl)-4-fluorophenyl)-4-(trifluoromethyl)-6-(2-(trimethylsilyl)ethoxy)nicotinamide (4 g, 41.6%) as a pale yellow solid. TLC: 5% MeOH in DCM; R$_f$: 0.5

Step 2: (S)—N-(2-(3,4-dimethylpiperazin-1-yl)-4-fluoro-5-(tributylstannyl)phenyl)-4-(trifluoromethy)-6-(2-(trimethylsilyl)ethoxy)nicotinamide

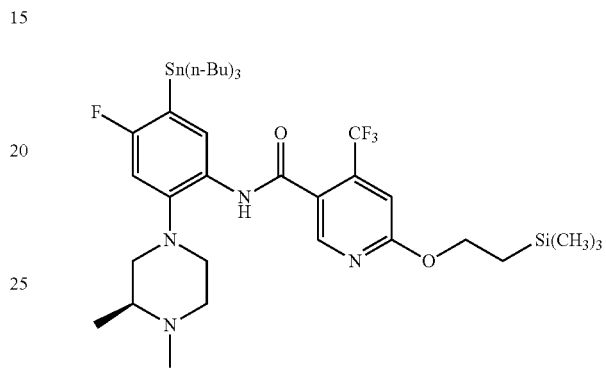

A stirred solution of (S)—N-(5-bromo-2-(3,4-dimethylpiperazin-1-yl)-4-fluorophenyl)-4-(trifluoromethyl)-6-(2-(trimethylsilyl)ethoxy)nicotinamide (4 g, 6.77 mmol, 1 eq) in toluene (40 mL) was degassed with argon for 15 mins, then hexabutylditin (6.89 mL, 13.5 mmol, 2 eq) was added, followed by Pd$_2$(dppf)$_2$C$_{1-2}$ (0.55 g, 0.67 mmol, 0.1 eq) and after that the reaction mixture was heated to reflux under argon atmosphere for 16 h. TLC analysis indicated formation of less polar spots. The reaction mixture was filtered through celite bed washed with EtOAc; the filtrate was evaporated under reduced pressure. The crude compound was purified by column chromatography (neutral alumina) using 0-30% EtOAc in pet ether as an eluent to afford (S)—N-(2-(3,4-dimethylpiperazin-1-yl)-4-fluoro-5-(tributylstannyl)phenyl)-4-(trifluoromethyl)-6-(2-(trimethylsilyl)ethoxy)nicotinamide (2.8 g, 51%) as a pale yellow liquid. LCMS: [M+H]+ 803.16.

Step 3: (S)-2-chloro-N-(2-hydroxypropyl)acetamide

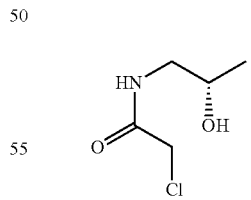

A solution of (S)-1-aminopropan-2-ol (25 g, 332.8 mmol, 1 eq) in THF (500 mL) was cooled to −10° C. and a solution of K$_2$CO$_3$ (137.98 g, 998.5 mmol, 3 eq) was added in H$_2$O (250 mL, 10V) followed by chloro acetyl chloride (28.25 mL, 366.2 mmol, 1.1 eq). The reaction mixture was stirred at the same temperature for 1 h. The reaction was monitored by TLC, and TLC analysis indicated formation of nonpolar spot. The reaction mixture was diluted with ethyl acetate (300 mL) and layers were separated. The aqueous layer was extracted with ethyl acetate (2×200 mL), the combined organic layer was dried over Na₂SO₄ and concentrated under reduced pressure to afford (S)-2-chloro-N-(2-hydroxypropyl)acetamide (29 g, 57.66% yield) as colourless oil. LCMS: [M+H]+ 152.31.

Step 4: (S)-6-methylmorpholin-3-one

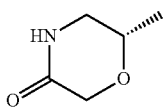

A solution of (S)-2-chloro-N-(2-hydroxypropyl)acetamide (29 g, 192.05 mmol, 1 eq) in DCM (580 mL) was cooled to 0° C. and a solution of t-BuOK (86.18 g, 768.2 mmol, 4 eq) in IPA (580 mL, 20V) was added. The reaction mixture was stirred at the same temperature for 1 h. The reaction was monitored by TLC, and TLC analysis indicated formation of nonpolar spot. The reaction mixture was neutralised (pH 7) with 2N HCl, and concentrated under reduced pressure. 5% methanol in DCM (250 mL) was added to the residue, and the mixture stirred for 30 min. It was filtered through celite, washed with 5% methanol:DCM, filtrate was concentrated under reduced pressure to give crude product which was filtered through a column of neutral alumina with 5% methanol in DCM as an eluent to afford (S)-6-methylmorpholin-3-one (14 g, 63.4% yield) as a white solid. LCMS: [M+H]+ 116.34.

Step 5: (S)-2-methylmorpholine

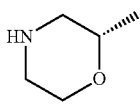

A solution of (S)-6-methylmorpholin-3-one (14 g, 121.7 mmol, 1 eq) in THF (280 mL, 20V) was cooled to 0° C. and LAH (13.8 g, 365.2 mmol, 3 eq) was added slowly portion wise under argon atmosphere. Then, the reaction mixture was allowed to RT for 16 h. The reaction was monitored by TLC, and TLC analysis indicated formation of polar spot. The reaction mixture was quenched with H₂O (14 mL), 2N NaOH (28 mL) followed by H₂O (7 mL) and the resulting precipitate was stirred at room temperature for 1 h. The mixture was filtered through celite, washed with ethyl acetate and the filtrate was concentrated under reduced pressure to afford (S)-2-methylmorpholine (10 g, 81.3% yield) as white solid. LCMS (ELSD): [M+H]+ 102.24.

Step 6: (S)-2-(2-methylmorpholinopyrimidin-4-ol

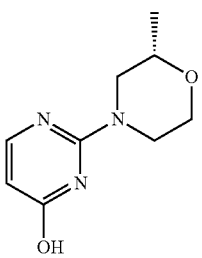

To a suspension of (S)-2-methylmorpholine (5 g, 49.29 mmol, 2 eq) was added 2-(methylthio)pyrimidin-4-ol (3.5 g, 24.64 mmol, 1 eq) at RT, and the resulting suspension was heated at 150° C. for 2 h. The reaction was monitored by TLC, and TLC analysis indicated formation of spot. The reaction mixture was concentrated under reduced pressure to give crude compound. The crude compound was purified by column chromatography (silica gel 100-200 mesh) using 5% methanol:ethyl acetate as an eluent to give (S)-2-(2-methylmorpholino)pyrimidin-4-ol (2.5 g, 52% yield) as pale yellow liquid. LCMS: [M+H]+ 196.03.

Step 7: (S)-4-(4-bromopyrimidin-2-yl)-2-methylmorpholine

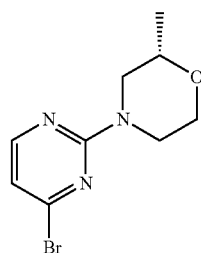

To a suspension of (S)-2-(2-methylmorpholino)pyrimidin-4-ol (5 g, 25.64 mmol, 1 eq) in ACN (50 mL) was added POBr₃ (9.5 g, 33.3 mmol, 1.3 eq) at RT and heated to 80° C. for 3 h. The reaction was monitored by TLC, and TLC analysis indicated formation of nonpolar spot. Then, the reaction mixture was diluted with ethyl acetate (200 mL) and washed with H₂O (2×100 mL). The combined organic layer was dried over Na₂SO₄ and concentrated under reduced pressure to give crude product. The crude product was purified by column chromatography (silica gel 100-200 mesh) using 2% methanol:ethyl acetate as an eluent afforded (S)-4-(4-bromopyrimidin-2-yl)-2-methylmorpholine (3 g, 45.59% yield) as pale yellow solid. LCMS: [M+H]+ 258.14.

Step 8: N-[4-fluoro-2-[(3R)-3,4-dimethylpiperazin-1-yl]-5-[2-[(2R)-2-methylmorpholin-4-yl]pyrimidin-4-yl]phenyl]-6-oxo-4-(trifluoromethyl)-1H-pyridine-3-carboxamide

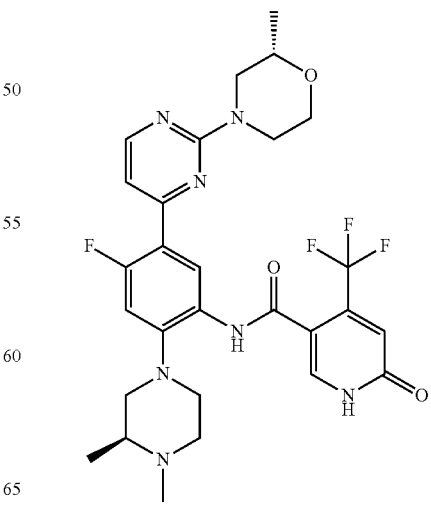

The procedure followed was similar to Example 384 using (S)—N-(2-(3,4-dimethylpiperazin-1-yl)-4-fluoro-5-(tributylstannyl)phenyl)-4-(trifluoromethyl)-6-(2-(trimethylsilyl)ethoxy)nicotinamide (108 mg, 0.135 mmol). The solution was added with (S)-4-(4-bromopyrimidin-2-yl)-2-methylmorpholine (38.3 mg, 0.148 mmol) to give the title compound (16.6 mg, 21% yield). $^1$H NMR (500 MHz, MeOD) δ 8.61 (d, J=8.1 Hz, 1H), 8.37 (d, J=5.2 Hz, 1H), 7.92 (s, 1H), 7.12 (dd, J=4.9, 1.5 Hz, 1H), 7.02 (d, J=13.2 Hz, 1H), 6.92 (s, 1H), 4.65 (d, J=13.1 Hz, 1H), 4.58 (d, J=12.5 Hz, 1H), 3.96 (dd, J=11.4, 2.3 Hz, 1H), 3.64 (td, J=11.9, 2.5 Hz, 2H), 3.22 (d, J=10.9 Hz, 1H), 3.14 (s, 1H), 3.05 (td, J=13.4, 3.5 Hz, 1H), 2.96 (t, J=10.1 Hz, 2H), 2.70 (dd, J=13.1, 10.5 Hz, 1H), 2.60 (t, J=10.8 Hz, 2H), 2.47 (s, 1H), 2.40 (s, 3H), 1.23 (d, J=6.2 Hz, 3H), 1.15 (d, J=6.2 Hz, 3H); $^{19}$F NMR (471 MHz, MeOD) δ −63.79, −115.96; LCMS [M+1]$^+$=590.35.

Example 594: N-[4-fluoro-5-[2-[(2R)-2-methylmorpholin-4-yl]pyrimidin-4-yl]-2-[(3S,5R)-3,4,5-trimethylpiperazin-1-yl]phenyl]-6-oxo-4-(trifluoromethyl)-1H-pyridine-3-carboxamide

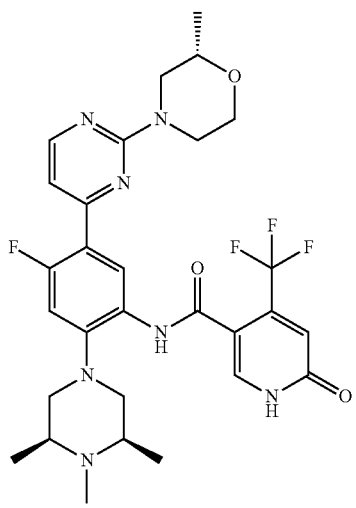

The procedure followed was similar to Example 384 using N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy)nicotinamide (102 mg, 0.125 mmol, preparation described in Example 384, Step 1) and (S)-4-(4-bromopyrimidin-2-yl)-2-methylmorpholine (35.5 mg, 0.138 mmol) to give the title compound (29.4 mg, 37% yield). $^1$H NMR (500 MHz, MeOD) δ 8.60 (d, J=8.1 Hz, 1H), 8.36 (d, J=5.2 Hz, 1H), 7.90 (s, 1H), 7.12 (d, J=3.5 Hz, 1H), 7.00 (d, J=13.2 Hz, 1H), 6.92 (s, 1H), 4.65 (d, J=12.9 Hz, 1H), 4.58 (d, J=13.0 Hz, 1H), 3.96 (dd, J=11.3, 2.2 Hz, 1H), 3.67-3.58 (m, 2H), 3.16 (d, J=10.9 Hz, 2H), 3.04 (td, J=13.2, 3.2 Hz, 1H), 2.70 (dd, J=13.2, 10.6 Hz, 1H), 2.67-2.62 (m, 2H), 2.59 (s, 2H), 2.40 (s, 3H), 1.23 (d, J=6.2 Hz, 3H), 1.18 (d, J=5.8 Hz, 6H); LCMS [M+1]$^+$=604.34.

Example 595: N-[5-(4-carbamoyl-3-fluorophenyl)-4-fluoro-2-[(3R)-3,4-dimethylpiperazin-1-yl]phenyl]-4-(difluoromethyl)-6-oxo-1H-pyridine-3-carboxamide

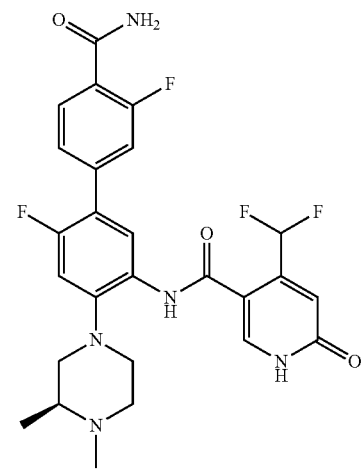 [SMILES: C[C@H]1CN(c2cc(F)c(-c3ccc(C(N)=O)c(F)c3)cc2NC(=O)c2c[nH]c(=O)cc2C(F)F)CCN1C]

A procedure similar to Example 100 using 4-carbamoyl-3-fluorophenylboronic acid, 96% (23.92 mg, 0.131 mmol) and (S)—N-(5-bromo-2-(3,4-dimethylpiperazin-1-yl)-4-fluorophenyl)-4-(difluoromethyl)-6-(2-(trimethylsilyl)ethoxy)nicotinamide (50 mg, 0.087 mmol) gave the title compound (TFA salt) as a white powder (42 mg, 100% yield for last step). $^1$H NMR (500 MHz, METHANOL-d4) δ=7.97 (s, 1H), 7.81 (t, J=8.0 Hz, 1H), 7.74 (d, J=8.2 Hz, 1H), 7.32-7.09 (m, 1H), 7.07 (br d, J=12.1 Hz, 1H), 6.73-6.66 (m, 1H), 3.53 (br d, J=12.2 Hz, 1H), 3.37-3.28 (m, 3H), 3.05-2.98 (m, 1H), 2.88 (s, 3H), 2.83-2.73 (m, 1H), 1.31 (br d, J=6.4 Hz, 3H); LCMS [M+H]$^+$ 532.

Example 596: N-[5-(3-carbamoyl-4-fluorophenyl)-4-fluoro-2-[(3R)-3,4-dimethylpiperazin-1-yl]phenyl]-4-(diluoromethyl)-6-oxo-1H-pyridine-3-carboxamide

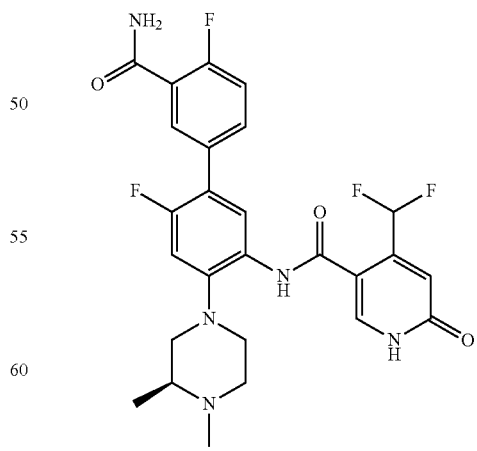

A procedure similar to Example 100 using 3-carbamoyl-4-fluorophenylboronic acid, 97% (15.95 mg, 0.087 mmol) and (S)—N-(5-bromo-2-(3,4-dimethylpiperazin-1-yl)-4- fluorophenyl)-4-(difluoromethyl)-6-(2-(trimethylsilyl) ethoxy)nicotinamide (50 mg, 0.087 mmol) gave the title compound (TFA salt) as a white powder (50 mg, 0100% yield). ¹H NMR (500 MHz, METHANOL-d4) δ=7.97 (s, 1H), 7.92-7.87 (m, 1H), 7.70 (d, J=8.2 Hz, 1H), 7.66-7.60 (m, 1H), 7.31-7.08 (m, 2H), 7.06 (d, J=11.9 Hz, 1H), 6.70 (s, 1H), 3.53 (br d, J=12.2 Hz, 1H), 3.31 (br d, J=11.9 Hz, 3H), 3.05-2.98 (m, 1H), 2.88 (s, 3H), 2.82-2.72 (m, 1H), 1.31 (br d, J=6.2 Hz, 3H); LCMS [M+H]⁺ 532.

Example 597: 4-(difluoromethyl)-N-[4-fluoro-5-[3-fluoro-4-(methylcarbamoyl)phenyl]-2-[(3R)-3,4-dimethylpiperazin-1-yl]phenyl]-6-oxo-1H-pyridine-3-carboxamide

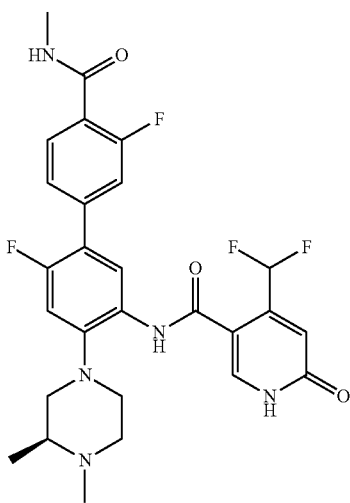 [SMILES: CNC(=O)c1ccc(-c2cc(NC(=O)c3c[nH]c(=O)cc3C(F)F)c(N3CCN(C)[C@@H](C)C3)cc2F)cc1F]

A procedure similar to Example 100 using 3-fluoro-4-(methylcarbamoyl)phenylboronic acid (25.8 mg, 0.131 mmol) and (S)—N-(5-bromo-2-(3,4-dimethylpiperazin-1-yl)-4-fluorophenyl)-4-(difluoromethyl)-6-(2-(trimethylsilyl) ethoxy)nicotinamide (50 mg, 0.087 mmol) gave the title compound (TFA salt) as a white powder (59 mg, 0.072 mmol, 97% yield). ¹H NMR (500 MHz, METHANOL-d4) δ=8.09 (s, 1H), 7.87-7.82 (m, 2H), 7.50 (d, J=8.1 Hz, 1H), 7.46-7.20 (m, 2H), 7.18 (d, J=12.0 Hz, 1H), 6.84-6.80 (m, 1H), 3.65 (br d, J=12.2 Hz, 1H), 3.43 (br d, J=12.0 Hz, 3H), 3.20-3.10 (m, 1H), 2.99 (s, 3H), 2.97 (s, 3H), 2.95-2.88 (m, 1H), 1.43 (d, J=6.2 Hz, 3H); LCMS [M+H]⁺ 546.

Example 598: 4-(difluoromethyl)-N-[4-fluoro-5-[4-fluoro-3-(methylcarbamoyl)phenyl]-2-[(3R)-3,4-dimethylpiperazin-1-yl]phenyl]-6-oxo-1H-pyridine-3-carboxamide

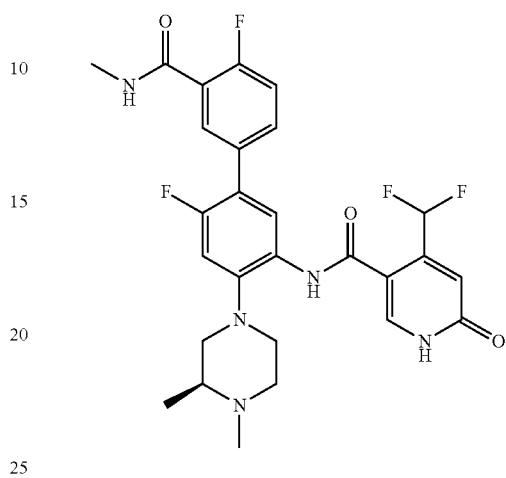

A procedure similar to Example 100 using N-methyl-5-borono-2-fluorobenzamide (25.8 mg, 0.131 mmol) and (S)—N-(5-bromo-2-(3,4-dimethylpiperazin-1-yl)-4-fluorophenyl)-4-(difluoromethyl)-6-(2-(trimethylsilyl)ethoxy) nicotinamide (50 mg, 0.087 mmol) gave the title compound (TFA salt) as a white powder (53 mg, 100% yield for last step). ¹H NMR (500 MHz, METHANOL-d4) δ=7.97 (s, 1H), 7.82 (br d, J=6.6 Hz, 1H), 7.70 (d, J=8.2 Hz, 1H), 7.61 (br dd, J=3.4, 7.6 Hz, 1H), 7.32-7.08 (m, 2H), 7.06 (br d, J=11.7 Hz, 1H), 6.72-6.67 (m, 1H), 3.53 (br d, J=12.3 Hz, 1H), 3.30 (br d, J=12.0 Hz, 3H), 3.09-2.96 (m, 1H), 2.87 (s, 3H), 2.85 (s, 3H), 2.82-2.73 (m, 1H), 1.31 (d, J=6.4 Hz, 3H); LCMS [M+H]⁺ 546.

Example 599: N-[4-fluoro-5-(4-morpholin-4-ylpyrimidin-2-yl)-2-[(3R)-3,4-dimethylpiperazin-1-yl]phenyl]-6-oxo-4-(trifluoromethyl)-1H-pyridine-3-carboxamide

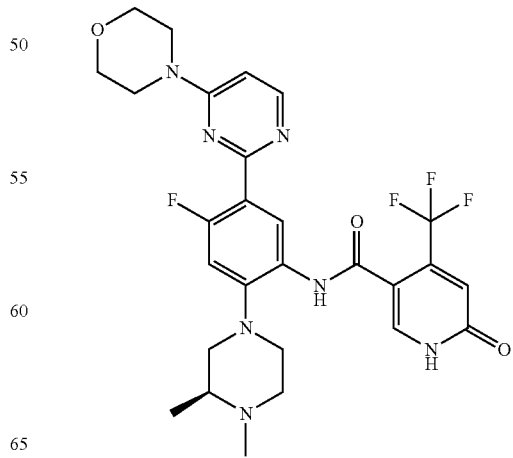

Step 1: (S)-2-(3,4-dimethylpiperazin-1-yl)-4-fluoro-5-(4,4,5,5-tetramethyl-1,3,2-dioxaborolan-2-yl)aniline

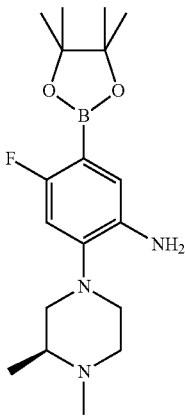 [SMILES: C[C@H]1CN(c2cc(F)c(B3OC(C)(C)C(C)(C)O3)cc2N)CCN1C]

A suspension of potassium acetate (0.601 g, 6.12 mmol), bis(pinacolato)diboron (0.745 g, 2.040 mmol) in dioxane (12 ml) was degassed with $N_2$ for 10 min, then treated with PdCb(dppf) (0.050 g, 0.061 mmol). The reaction was sparged with $N_2$ for an additional 10 min. The mixture was heated to 80° C. overnight, then allowed to cool to rt. The reaction was quenched with $H_2O$ and diluted with EtOAc. Layers were separated. The aqueous phase was extracted with EtOAc (3×). The combined organic phases were washed with $H_2O$ (3×), dried over $Na_2SO_4$, filtered, and concentrated to afford a black residue. The crude material was dissolved in a minimal amount of $CH_2Cl_2$ and chromatographed. Purification of the crude material by silica gel chromatography gave (S)-2-(3,4-dimethylpiperazin-1-yl)-4-fluoro-5-(4,4,5,5-tetramethyl-1,3,2-dioxaborolan-2-yl)aniline (0.656 g, 80% yield) as a brown residue.

Step 2: (S)-2-(3,4-dimethylpiperazin-1-yl)-5-(4-morpholinopyrimidin-2-yl)aniline

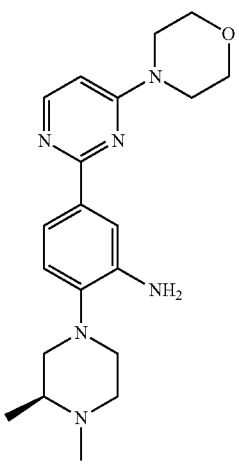 [SMILES: C[C@H]1CN(c2ccc(-c3nccc(N4CCOCC4)n3)cc2N)CCN1C]

To a microwave vial charged with (S)-2-(3,4-dimethylpiperazin-1-yl)-4-fluoro-5-(4,4,5,5-tetramethyl-1,3,2-dioxaborolan-2-yl)aniline (0.143, 0.410 mmol), 4-(2-bromopyrimidin-4-yl)morpholine (0.150 g, 0.615 mmol), $K_3PO_4$ (0.174 g, 0.819 mmol) was added dioxane (2 ml) and water (2 ml) and the vial was flushed with nitrogen. Bis(di-tert-butyl(4-dimethylaminophenyl)phosphine)dichloropalladium(II) (0.0087 g, 0.030 mmol) was added, the vial was sealed, and the mixture heated in a microwave reactor to 110° C. for 30 minutes. The crude mixture was concentrated onto celite and purified using reverse phase silca gel column chromatography (Water:AcCN gradient 0-100%). The product was dried under vacuum to give the title compound as a brown solid (0.097 g, 61%); LCMS $[M+H]^+$ 387

Step 3: (S)—N-(2-(3,4-dimethylpiperazin-1-yl)-5-(4-morpholinopyrimidin-2-yl)phenyl)-4-(trifluoromethyl)-6-(2-(trimethylsilyl)ethoxy)nicotinamide

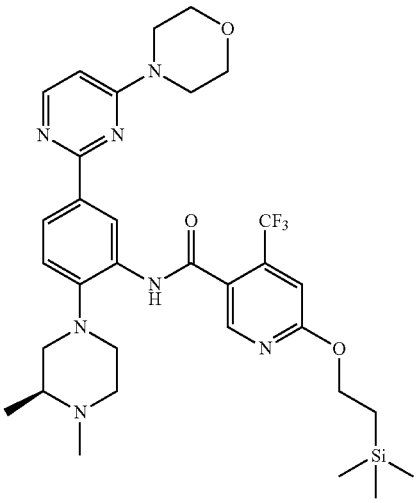

4-(Trifluoromethyl)-6-(2-(trimethylsilyl)ethoxy)nicotinic acid, (72 mg, 0.233 mmol), HATU (89 mg, 0.233 mmol) and DIEA (0.081 ml, 0.466 mmol) were combined in DMF (3.0 mL). After 30 min, (S)-2-(3,4-dimethylpiperazin-1-yl)-4-fluoro-5-(4-morpholinopyrimidin-2-yl)aniline (45 mg, 0.116 mmol) was added and the reaction was heated to 60° C. overnight. The reaction was concentrated onto celite then purified by reverse phase silica gel chromatography using a gradient of Water/AcCN from 0 to 100% to provide the desired product along with an impurity (70 mg, 89%) as a light brown oil; LCMS $[M+H]^+$ 676.

Step 4: N-[4-fluoro-5-(4-morpholin-4-ylpyrimidin-2-yl)-2-[(3R)-3,4-dimethylpiperazin-1-yl]phenyl]-6-oxo-4-(trifluoromethyl)-1H-pyridine-3-carboxamide

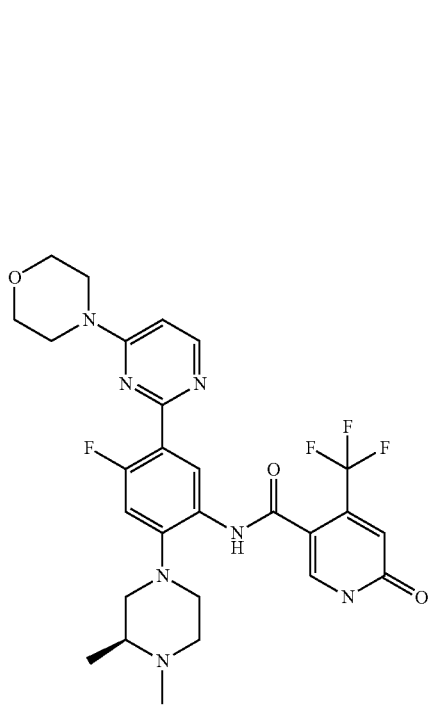 [SMILES: C[C@H]1CN(c2cc(F)c(-c3nccc(N4CCOCC4)n3)cc2NC(=O)c2c[nH]c(=O)cc2C(F)(F)F)CCN1C]

To a vial of (S)—N-(2-(3,4-dimethylpiperazin-1-yl)-4-fluoro-5-(4-morpholinopyrimidin-2-yl)phenyl)-4-(trifluoromethyl)-6-(2-(trimethylsilyl)ethoxy)nicotinamide (70 mg, 0.104 mmol, 1 equiv.) was added TFA/CH$_2$Cl$_2$ (2 ml of a 1:1 mixture). The reaction mixture was stirred at 22° C. for 1 h (Judged complete by LCMS). The solvent was removed in vacuo and the residue was triturated with ether to afford 51 mg title compound (RF=0.98 min) as a beige solid along with an impurity (RF 1.12 min). The material was then further purified by preparatory HPLC (0.1% Formic Acid in water/AcCN as eluent) to afford 18 mg (27% yield) of the title product as a beige solid. $^1$H NMR (500 MHz, METHANOL-d4) δ=8.39 (br d, J=7.9 Hz, 2H), 8.27 (d, J=6.2 Hz, 1H), 8.06-7.94 (m, 1H), 7.08 (d, J=12.2 Hz, 1H), 6.95 (s, 1H), 6.73 (d, J=6.4 Hz, 1H), 3.83-3.72 (m, 8H), 3.31-3.19 (m, 3H), 3.07 (s, 1H), 2.90 (br d, J=9.7 Hz, 2H), 2.77 (br d, J=11.6 Hz, 1H), 2.65 (s, 3H), 1.28 (d, J=6.4 Hz, 3H); LCMS [M+H]$^+$ 576

Example 600: Propan-2-yl 3-[2-fluoro-5-[[6-oxo-4-(trifluoromethyl)-1H-pyridine-3-carbonyl]amino]-4-[(3R 5S)-3,4,5-trimethylpiperazin-1-yl]phenyl]-2,5-dihydropyrrole-1-carboxylate

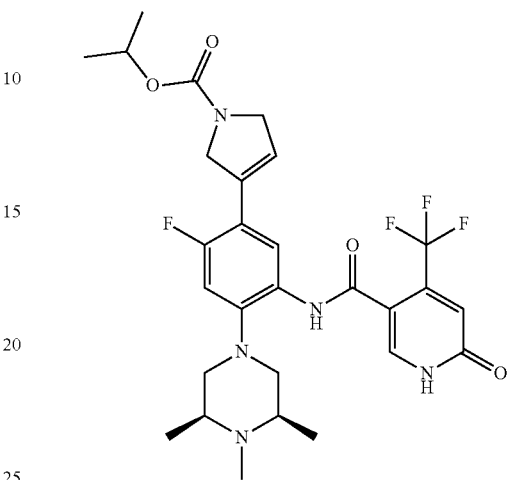

The procedure followed was similar to Example 372 using N-(5-(2,5-dihydro-1H-pyrrol-3-yl)-4-fluoro-2-((3S,5R)-3,4,5-trimethylpiperazin-1-yl)phenyl)-6-oxo-4-(trifluoromethyl)-1,6-dihydropyridine-3-carboxamide (30 mg, 0.061 mmol) and isopropyl chloroformate (0.061 ml, 0.061 mmol) to give the title compound (24 mg, 65% yield). $^1$H NMR (500 MHz, METHANOL-d4) δ=7.90-7.80 (m, 1H), 7.76-7.63 (m, 1H), 6.94-6.86 (m, 1H), 6.85-6.73 (m, 1H), 6.29-6.16 (m, 1H), 4.87-4.81 (m, 1H), 4.47-4.37 (m, 2H), 4.26-4.20 (m, 2H), 2.99-2.90 (m, 2H), 2.53-2.45 (m, 2H), 2.45-2.38 (m, 2H), 2.28-2.22 (m, 3H), 1.23-1.18 (m, 6H), 1.04 (br d, J=5.9 Hz, 6H); LCMS [M+H]+ 580.2

Example 601: propan-2-yl 5-[2-fluoro-5-[[6-oxo-4-(trifluoromethyl)-1H-pyridine-3-carbonyl]amino]-4-[(3R 5S)-3,4,5-trimethylpiperazin-1-yl]phenyl]-3,6-dihydro-2H-pyridine-1-carboxylate

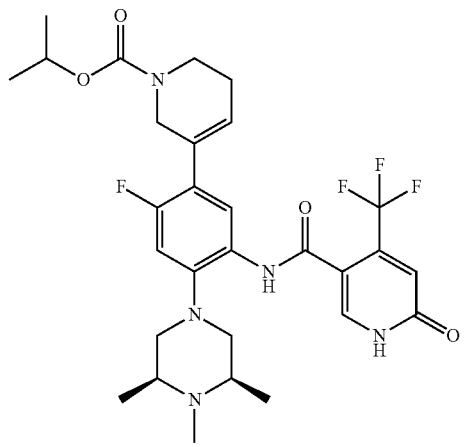

The procedure followed was similar to Example 372 using N-(4-fluoro-5-(1,2,5,6-tetrahydropyridin-3-yl)-2-((3S,5R)-3,4,5-trimethylpiperazin-1-yl)phenyl)-6-oxo-4-

(trifluoromethyl)-1,6-dihydropyridine-3-carboxamide (30 mg, 0.059 mmol) and isopropyl chloroformate (0.059 ml, 0.059 mmol) to give the title compound (27 mg, 73% yield). $^1$H NMR (500 MHz, METHANOL-d4) δ=7.87-7.80 (m, 1H), 7.69-7.60 (m, 1H), 6.89-6.83 (m, 1H), 6.82-6.77 (m, 1H), 6.03-5.96 (m, 1H), 4.86-4.80 (m, 1H), 4.18-4.10 (m, 2H), 3.56-3.47 (m, 2H), 2.91 (br d, J=11.1 Hz, 2H), 2.52-2.45 (m, 2H), 2.44-2.37 (m, 2H), 2.27-2.21 (m, 5H), 1.17 (br d, J=6.1 Hz, 6H), 1.05 (d, J=6.1 Hz, 6H); LCMS [M+H]+ 594.6.

Example 602: propan-2-yl 4-[2-fluoro-5-[[6-oxo-4-(trifluoromethyl)-1H-pyridine-3-carbonyl]amino]-4-[(3R 5S)-3,4,5-trimethylpiperazin-1-yl]phenyl]-3,6-dihydro-2H-pyridine-1-carboxylate

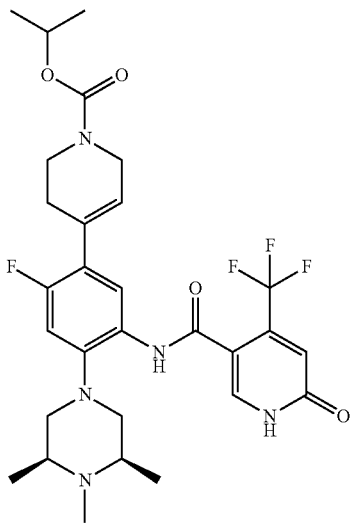

The procedure was similar to Example 372 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.059 mmol) and isopropyl chloroformate (0.059 ml, 0.059 mmol) to give the title compound (28 mg, 76% yield). $^1$H NMR (500 MHz, METHANOL-d4) δ=7.88-7.80 (m, 1H), 7.70-7.61 (m, 1H), 6.87-6.81 (m, 1H), 6.80-6.76 (m, 1H), 5.95-5.82 (m, 1H), 4.85-4.80 (m, 1H), 4.03-3.97 (m, 2H), 3.58-3.53 (m, 2H), 2.93-2.87 (m, 2H), 2.50-2.44 (m, 2H), 2.42-2.36 (m, 4H), 2.27-2.23 (m, 3H), 1.20-1.17 (m, 6H), 1.04 (d, J=6.0 Hz, 6H); LCMS [M+H]+ 594.2

Example 603: N-[4-fluoro-5-[3-fluoro-4-(methylcarbamoyl)phenyl]-2-[(3R 5S)-3,4,5-trimethylpiperazin-1-yl]phenyl]-6-oxo-4-(trifluoromethyl)-1H-pyridine-3-carboxamide

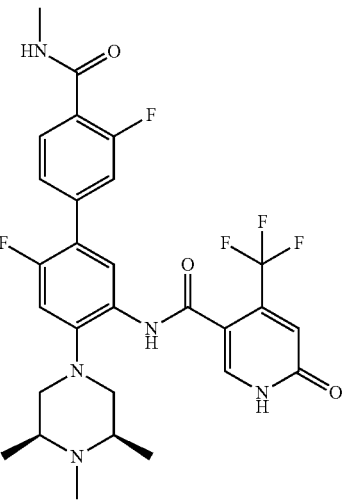

A procedure similar to Example 100 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (54 mg, 0.089 mmol) and 3-fluoro-4-(methylcarbamoyl)phenylboronic acid (26.3 mg, 0.134 mmol) gave the title compound (TFA salt) as a white fluffy powder (58.8 mg, 0.069 mmol, 89% yield). $^1$H NMR (500 MHz, METHANOL-d4) δ=7.91 (s, 1H), 7.88 (d, J=8.2 Hz, 1H), 7.73 (t, J=7.9 Hz, 1H), 7.37 (d, J=8.2 Hz, 1H), 7.32 (d, J=12.1 Hz, 1H), 7.07 (d, J=11.9 Hz, 1H), 6.84-6.79 (m, 1H), 3.46-3.35 (m, 2H), 3.29 (br d, J=13.1 Hz, 2H), 2.88 (s, 2H), 2.87-2.80 (m, 5H), 1.34 (d, J=6.5 Hz, 6H); LCMS [M+H]$^+$ 578.

Example 604: N-[4-fluoro-5-[4-fluoro-3-(methylcarbamoyl)phenyl]-2-[(3R 5S)-3,4,5-trimethylpiperazin-1-yl]phenyl]-6-oxo-4-(trifluoromethyl)-1H-pyridine-3-carboxamide

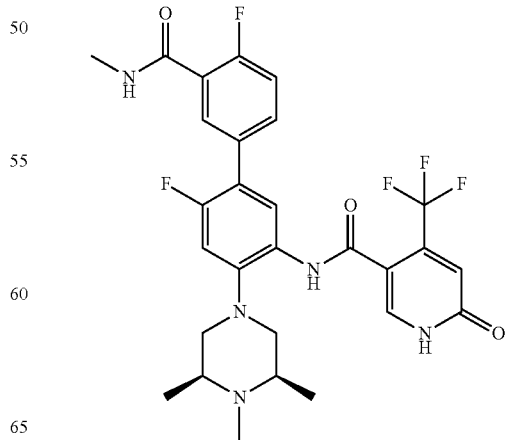

The procedure followed was similar to Example 100 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (50 mg, 0.083 mmol) and N-methyl-5-borono-2-fluorobenzamide (24.40 mg, 0.124 mmol) to give the title compound (TFA salt) as an off-white fluffy powder (53.7 mg, 0.074 mmol, 99% yield). $^1$H NMR (500 MHz, METHANOL-d4) δ=7.93 (s, 1H), 7.87 (d, J=8.2 Hz, 1H), 7.84 (dd, J=1.1, 6.7 Hz, 1H), 7.65-7.57 (m, 1H), 7.24 (dd, J=8.7, 10.5 Hz, 1H), 7.09 (d, J=11.7 Hz, 1H), 6.87-6.83 (m, 1H), 3.48-3.38 (m, 2H), 3.31 (br d, J=13.1 Hz, 2H), 2.91 (s, 3H), 2.89-2.82 (m, 5H), 1.36 (d, J=6.5 Hz, 6H); LCMS [M+H]$^+$ 578.

Example 605: 4-(difluoromethyl)-N-[4-fluoro-5-[3-fluoro-4-(methylcarbamoyl)phenyl]-2-[(3R,5S)-3,4,5-trimethylpiperazin-1-yl]phenyl]-6-oxo-1H-pyridine-3-carboxamide

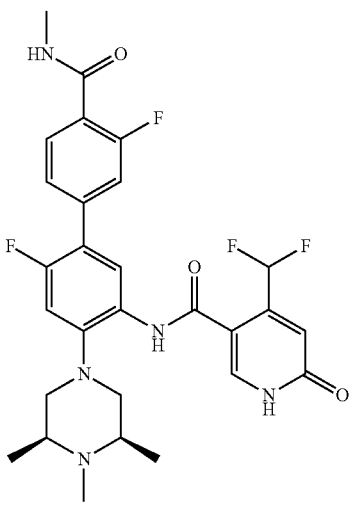 [SMILES: CNC(=O)c1ccc(-c2cc(NC(=O)c3c[nH]c(=O)cc3C(F)F)c(N3C[C@@H](C)N(C)[C@@H](C)C3)cc2F)cc1F]

The procedure was similar to Example 100 using 3-fluoro-4-(methylcarbamoyl)phenylboronic acid (25.1 mg, 0.128 mmol) and N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (50 mg, 0.085 mmol) to give the title compound (TFA salt) as an off-white fluffy powder (50.7 mg, 0.061 mmol, 87% yield). $^1$H NMR (500 MHz, METHANOL-d4) δ=7.95 (s, 1H), 7.76-7.65 (m, 2H), 7.37 (d, J=8.1 Hz, 1H), 7.33-7.08 (m, 2H), 7.05 (d, J=12.0 Hz, 1H), 6.69 (s, 1H), 3.42-3.34 (m, 2H), 3.31 (br d, J=13.3 Hz, 2H), 2.87 (s, 3H), 2.85-2.79 (m, 5H), 1.33 (d, J=6.5 Hz, 6H); LCMS [M+H]$^+$ 560.

Example 606: 4-(difluoromethyl)-N-[4-fluoro-5-[4-fluoro-3-(methylcarbamoyl)phenyl]-2-[(3R,5S)-3,4,5-trimethylpiperazin-1-yl]phenyl]-6-oxo-1H-pyridine-3-carboxamide

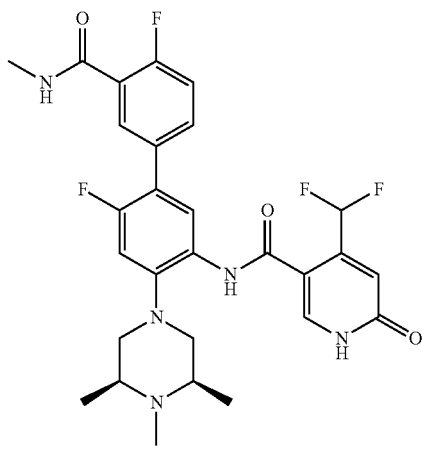 [SMILES: CNC(=O)c1cc(-c2cc(NC(=O)c3c[nH]c(=O)cc3C(F)F)c(N3C[C@@H](C)N(C)[C@@H](C)C3)cc2F)ccc1F]

The procedure was similar to Example 100 using N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (50 mg, 0.085 mmol) and N-methyl-5-borono-2-fluorobenzamide (25.1 mg, 0.128 mmol) to give the title compound (TFA salt) as a white powder (42.1 mg, 87% yield). $^1$H NMR (500 MHz, METHANOL-d4) δ=7.96 (s, 1H), 7.81 (dd, J=1.2, 6.7 Hz, 1H), 7.70 (d, J=8.2 Hz, 1H), 7.63-7.56 (m, 1H), 7.32-7.09 (m, 2H), 7.05 (d, J=11.7 Hz, 1H), 6.72-6.67 (m, 1H), 3.43-3.34 (m, 2H), 3.31 (br d, J=13.2 Hz, 2H), 2.88 (s, 3H), 2.86-2.78 (m, 5H), 1.33 (d, J=6.5 Hz, 6H); LCMS [M+H]$^+$ 560.

Example 607: 4-(difluoromethyl)-N-[4-fluoro-2-[(3R)-3,4-dimethylpiperazin-1-yl]-5-[2-[(3R)-3-methylmorpholin-4-yl]pyrimidin-5-yl]phenyl]-1-methyl-6-oxopyridine-3-carboxamide

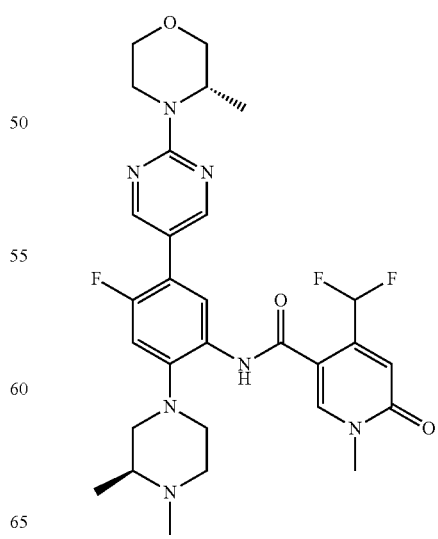

A procedure similar to that of Example 31 using (S)-4-(5-fluoro-2-nitro-4-(4,4,5,5-tetramethyl-1,3,2-dioxaborolan-2-yl)phenyl)-1,2-dimethylpiperazine and 4-(difluoromethyl)-1-methyl-6-oxo-1,6-dihydropyridine-3-carboxylic acid gave the title compound. ¹H NMR (500 MHz, DMSO-d6) δ=9.48 (s, 1H), 8.53 (d, J=0.9 Hz, 2H), 8.36 (s, 1H), 7.69 (d, J=8.6 Hz, 1H), 7.49-7.17 (m, 1H), 7.09 (d, J=12.3 Hz, 1H), 6.65 (s, 1H), 4.65 (br dd, J=2.8, 6.8 Hz, 1H), 4.29 (dd, J=2.4, 13.5 Hz, 1H), 3.93 (dd, J=3.5, 11.3 Hz, 1H), 3.73 (d, J=11.4 Hz, 1H), 3.60 (dd, J=3.1, 11.4 Hz, 1H), 3.52 (s, 3H), 3.44 (dt, J=3.0, 11.8 Hz, 1H), 3.19 (dt, J=3.8, 13.0 Hz, 1H), 3.09-2.98 (m, 2H), 2.87-2.74 (m, 2H), 2.43 (br t, J=10.5 Hz, 1H), 2.36 (br t, J=9.9 Hz, 1H), 2.21 (s, 3H), 1.21 (d, J=6.7 Hz, 3H), 0.98 (d, J=6.2 Hz, 3H); LCMS [M+H]+: 586.2.

Example 608: N-[4-fluoro-2-[(3R)-3,4-dimethylpiperazin-1-yl]-5-[2-[(3R)-3-methylmorpholin-4-yl]pyrimidin-5-yl]phenyl]-1-methyl-6-oxo-4-(trifluoromethyl)pyridine-3-carboxamide

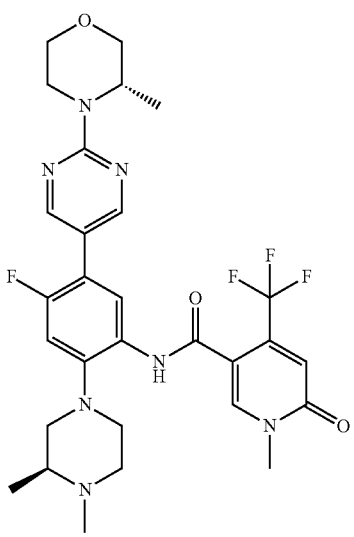

The procedure used was similar to Example 31 using 1-methyl-6-oxo-4-(trifluoromethyl)-1,6-dihydropyridine-3-carboxylic acid and (S)-4-(5-fluoro-2-nitro-4-(4,4,5,5-tetramethyl-1,3,2-dioxaborolan-2-yl)phenyl)-1,2-dimethylpiperazine. ¹H NMR (500 MHz, DMSO-d6) δ=9.46 (s, 1H), 8.52 (d, J=0.7 Hz, 2H), 8.30 (s, 1H), 7.76 (d, J=8.4 Hz, 1H), 7.10 (d, J=12.2 Hz, 1H), 6.87 (s, 1H), 4.65 (br dd, J=2.8, 6.7 Hz, 1H), 4.29 (dd, J=2.3, 13.6 Hz, 1H), 3.93 (dd, J=3.5, 11.3 Hz, 1H), 3.73 (d, J=11.2 Hz, 1H), 3.60 (dd, J=3.1, 11.4 Hz, 1H), 3.44 (dt, J=3.1, 11.9 Hz, 1H), 3.19 (dt, J=3.9, 13.0 Hz, 1H), 3.02 (br t, J=13.3 Hz, 2H), 2.90-2.74 (m, 2H), 2.46-2.34 (m, 2H), 2.25-2.19 (m, 3H), 1.21 (d, J=6.7 Hz, 3H), 0.98 (br d, J=6.0 Hz, 3H); LCMS [M+H]+: 604.3.

Example 609: N-[4-fluoro-5-(6-fluoropyridin-2-yl)-2-[(3R)-3,4-dimethylpiperazin-1-yl]phenyl]-6-oxo-4-(trifluoromethyl)-1H-pyridine-3-carboxamide

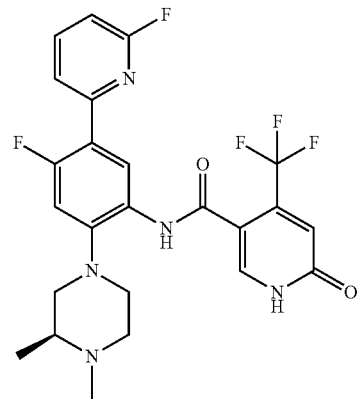

A procedure similar to Example 384 using (S)—N-(2-(3,4-dimethylpiperazin-1-yl)-4-fluoro-5-(tributylstannyl)phenyl)-4-(trifluoromethyl)-6-(2-(trimethylsilyl)ethoxy)nicotinamide (107 mg, 0.133 mmol) and 2-bromo-6-trifluoromethylpyridine (33.2 mg, 0.147 mmol), gave the title compound (15.3 mg, 210% yield). ¹H NMR (500 MHz, MeOD) δ 8.38 (d, J=8.1 Hz, 1H), 8.09-8.04 (m, 2H), 7.99 (s, 1H), 7.73 (d, J=7.0 Hz, 1H), 7.09 (d, J=12.8 Hz, 1H), 6.91 (s, 1H), 3.23-3.15 (m, 2H), 3.00 (t, J=10.6 Hz, 2H), 2.64 (s, 2H), 2.54 (s, 1H), 2.44 (s, 3H), 1.16 (d, J=4.7 Hz, 3H); LCMS [M+1]⁺=558.07.

Example 610: N-[4-fluoro-2-[(3R)-3,4-dimethylpiperazin-1-yl]-5-[6-(trifluoromethyl)pyridin-2-yl]phenyl]-6-oxo-4-(trifluoromethyl)-1H-pyridine-3-carboxamide

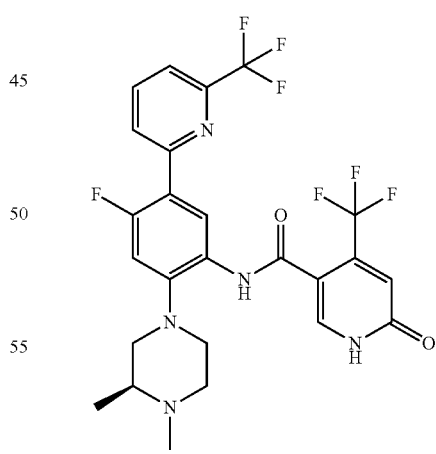

A procedure similar to that of Example 384 using (S)—N-(2-(3,4-dimethylpiperazin-1-yl)-4-fluoro-5-(tributylstannyl)phenyl)-4-(trifluoromethyl)-6-(2-(trimethylsilyl)ethoxy)nicotinamide (109 mg, 0.136 mmol) and 2-bromo-6-fluoropyridine (26.3 mg, 0.150 mmol) gave the title compound (9 mg, 13% yield). ¹H NMR (500 MHz, MeOD) δ 8.35 (d, J=8.2 Hz, 1H), 8.02-7.95 (m, 2H), 7.74 (d, J=7.8

Hz, 1H), 7.06 (d, J=12.9 Hz, 1H), 7.00 (dd, J=8.2, 2.5 Hz, 1H), 6.91 (s, 1H), 3.15 (dd, J=26.8, 11.1 Hz, 2H), 2.95 (t, J=10.9 Hz, 2H), 2.62-2.51 (m, 2H), 2.43 (s, 1H), 2.38 (s, 3H), 1.13 (d, J=6.1 Hz, 3H); LCMS [M+1]$^+$=508.26.

Example 611: 4-fluoro-N-[4-fluoro-5-[2-[(2R)-2-methylmorpholin-4-yl]pyrimidin-5-yl]-2-[(3S,5R)-3,4,5-trimethylpiperazin-1-yl]phenyl]-3,5-dimethyl-benzamide

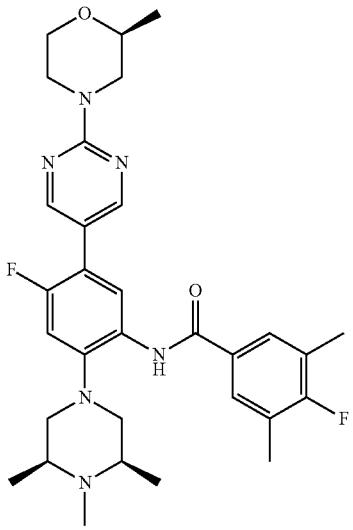 [SMILES: Cc1cc(C(=O)Nc2cc(-c3cnc(N4CCO[C@@H](C)C4)nc3)c(F)cc2N2C[C@@H](C)N(C)[C@@H](C)C2)cc(C)c1F]

A mixture of 4-fluoro-3,5-dimethylbenzoic acid (757 mg, 4.5 mmol), HATU (1.711 g, 4.5 mmol) and N,N-diisopropylethylamine (0.784 ml, 4.5 mmol) in DMF (6 mL) was heated at 60° C. for 5 min to afford a clear colorless solution before 5-bromo-4-fluoro-2-((3S,5R)-3,4,5-trimethylpiperazin-1-yl)aniline (0.949 g, 3 mmol) was added in one portion. The resulting mixture was heated at 60° C. for 4.5 h and 80° C. for 2 h. DMF was removed to give a brown solid which was partitioned between DCM (50 mL) and sat. NaHCO$_3$ (30 mL) and H$_2$O (15 mL) then separated. The aq layer was extracted with DCM (30 mL) and the combined extracts were concentrated to give a brown solid. It was purified by flash chromatography (gradient: EtOAc/hex 0-100% then MeOH/DCM 0-5%) to give N-(5-bromo-4-fluoro-2-((3S,5R)-3,4,5-trimethylpiperazin-1-yl)phenyl)-4-fluoro-3,5-dimethylbenzamide as a light pink crystalline solid (608 mg, 37.6% yield based on 86.5% purity). LCMS [M+H]$^+$ 466.1. The title compound (formic acid salt, white solid, 22.0 mg, 36%) was prepared by a procedure similar to Example 29 using crude (S)-(2-(2-methylmorpholino)pyrimidin-5-yl)boronic acid (0.2 mmol) and N-(5-bromo-4-fluoro-2-((3S,5R)-3,4,5-trimethylpiperazin-1-yl)phenyl)-4-fluoro-3,5-dimethylbenzamide (54 mg, 86.5% purity, 0.1 mmol). $^1$H NMR (500 MHz, METHANOL-d4) δ=8.57 (s, 2H), 8.46 (br s, 1H), 8.02 (d, J=8.3 Hz, 1H), 7.70 (d, J=6.7 Hz, 2H), 7.13 (d, J=12.0 Hz, 1H), 4.65-4.55 (m, 2H), 3.99 (dd, J=2.4, 11.5 Hz, 1H), 3.68-3.60 (m, 2H), 3.20 (br d, J=11.5 Hz, 2H), 3.08 (ddd, J=3.5, 12.0, 13.3 Hz, 1H), 2.88-2.71 (m, 5H), 2.57 (s, 3H), 2.37 (d, J=1.8 Hz, 6H), 1.25 (d, J=6.2 Hz, 9H); LCMS [M+H]$^+$ 565.4.

Example 612: 4-(Difluoromethyl)-N-(4-fluoro-5-(1-(pyrrolidine-1-carbonyl)-2,5-dihydro-1H-pyrrol-3-yl)-2-((3S,5R)-3,4,5-trimethylpiperazin-1-yl)phenyl)-6-oxo-1,6-dihydropyridine-3-carboxamide

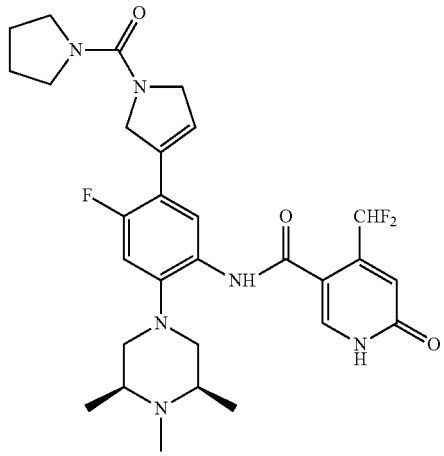 [SMILES: C[C@@H]1CN(c2cc(F)c(C3=CCN(C(=O)N4CCCC4)C3)cc2NC(=O)c2c[nH]c(=O)cc2C(F)F)C[C@H](C)N1C]

The procedure was similar to Example 253 using 1-pyrrolidinecarbonyl chloride (5.81 μl, 0.053 mmol) and 4-(difluoromethyl)-N-(5-(2,5-dihydro-1H-pyrrol-3-yl)-4-fluoro-2-((3S,5R)-3,4,5-trimethylpiperazin-1-yl)phenyl)-6-oxo-1,6-dihydropyridine-3-carboxamide (25 mg, (0.053 mmol) to give the title compound (27.5 mg, 87% yield). $^1$H NMR (500 MHz, METHANOL-d46=8.05-8.00 (m, 1H), 7.76-7.68 (m, 1H), 7.44-7.19 (m, 1H), 7.03-6.95 (m, 1H), 6.84-6.78 (m, 1H), 6.38-6.31 (m, 1H), 4.69-4.60 (m, 2H), 4.50-4.41 (m, 2H), 3.54-3.44 (m, 4H), 3.12-3.02 (m, 2H), 2.63-2.55 (m, 2H), 2.54-2.46 (m, 2H), 2.39-2.33 (m, 3H), 1.99-1.88 (m, 4H), 1.20-1.10 (m, 6H); LCMS [M+H]+ 573.6.

Example 613: 4-fluoro-N-[4-fluoro-5-[2-(4-hydroxy-4-methylpiperidin-1-yl)pyrimidin-5-yl]-2-[(3R)-3,4-dimethylpiperazin-1-yl]phenyl]-2-(trifluoromethyl)benzamide

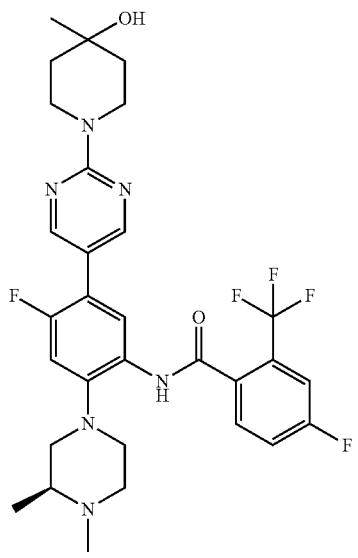 [SMILES: C[C@H]1CN(c2cc(F)c(-c3cnc(N4CCC(C)(O)CC4)nc3)cc2NC(=O)c2ccc(F)cc2C(F)(F)F)CCN1C]

The title compound (formic acid salt, pale beige solid, 26.0 mg, 40%) was prepared by a procedure similar to Example 400 using crude (2-(4-hydroxy-4-methylpiperidin-1-yl)pyrimidin-5-yl)boronic acid (0.3 mmol) and (S)—N-(5-bromo-2-(3,4-dimethylpiperazin-1-yl)-4-fluorophenyl)-4-fluoro-2-(trifluoromethyl)benzamide (57 mg, 86% purity, 0.1 mmol). $^1$H NMR (500 MHz, METHANOL-d4) δ=8.53 (s, 2H), 8.39 (br s, 1H), 8.04 (d, J=8.2 Hz, 1H), 7.82 (dd, J=5.3, 8.4 Hz, 1H), 7.67 (br d, J=8.9 Hz, 1H), 7.58 (br t, J=7.6 Hz, 1H), 7.19 (d, J=11.7 Hz, 1H), 4.31 (br d, J=13.2 Hz, 2H), 3.64-3.54 (m, 2H), 3.45-3.36 (m, 1H), 3.25 (br d, J=9.7 Hz, 2H), 3.12 (br s, 3H), 2.93-2.82 (m, 1H), 2.81-2.73 (m, 3H), 1.70-1.59 (m, 4H), 1.37-1.31 (m, 3H), 1.31-1.27 (m, 3H); LCMS [M+H]$^+$ 605.3.

Example 614: 4-fluoro-N-[4-fluoro-5-(2-morpholin-4-ylpyrimidin-4-yl)-2-[(3R)-3,4-dimethylpiperazin-1-yl]phenyl]-2-(trifluoromethyl)benzamide

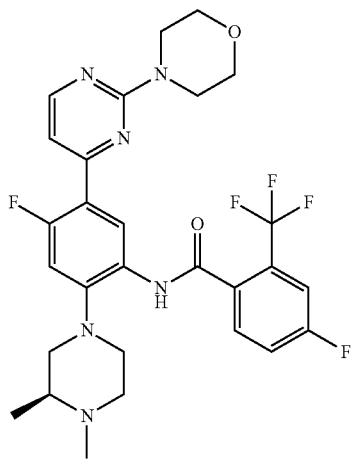

To a solution of 4-fluoro-2-(trifluoromethyl)benzoyl chloride (0.045 mL, 0.3 mmol) in DCM (3 mL) at rt was added Et$_3$N (0.084 mL, 0.6 mmol). After addition, the resulting mixture was stirred at rt for 5 min, before a solution of (S)-2-(3,4-dimethylpiperazin-1-yl)-4-fluoro-5-(2-morpholinopyrimidin-4-yl)aniline (38.6 mg, 0.1 mmol) in DCM (2 mL) was added. The resulting mixture was stirred overnight at room temperature LC-MS then additional 4-fluoro-2-(trifluoromethyl)benzoyl chloride (0.045 mL, 0.3 mmol) in DCM (2 mL) and Et$_3$N (0.084 mL, 0.6 mmol) was added. After addition, the resulting mixture was stirred at rt for 1.5 h and the reaction was judged complete by LCMS. Standard workup and purification by flash chromatography (gradient: EtOAc/hex 0-100% then MeOH/DCM 0-10%, later 1% NH$_3$ in MeOH/DCM 20%) and prep-HPLC gave the title compound (formic acid salt, light brown solid, 7.5 mg, 12%). $^1$H NMR (500 MHz, METHANOL-d4) δ=8.73 (d, J=8.2 Hz, 1H), 8.44 (br s, 1H), 8.41 (d, J=5.3 Hz, 1H), 7.77 (dd, J=5.4, 8.3 Hz, 1H), 7.68 (dd, J=2.3, 9.0 Hz, 1H), 7.58 (dt, J=2.0, 8.2 Hz, 1H), 7.17 (dd, J=1.7, 5.1 Hz, 1H), 7.08 (d, J=13.1 Hz, 1H), 3.90-3.86 (m, 4H), 3.81-3.77 (m, 4H), 3.30-3.23 (m, 2H), 3.20-3.13 (m, 1H), 3.05 (br t, J=11.0 Hz, 1H), 2.82-2.69 (m, 3H), 2.55 (s, 3H), 1.24 (br d, J=5.5 Hz, 3H); LCMS [M+H]$^+$ 577.3.

Example 615: N-[5-[1-(5-cyano-1,3-thiazol-2-yl)-3,6-dihydro-2H-pyridin-5-yl]-4-fluoro-2-[(3R,5S)-3,4,5-trimethylpiperazin-1-yl]phenyl]-6-oxo-4-(trifluoromethyl)-1H-pyridine-3-carboxamide

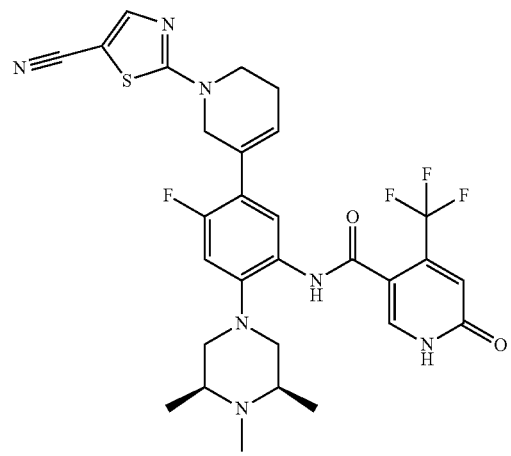 [SMILES: C[C@@H]1CN(c2cc(F)c(C3=CCCN(c4ncc(C#N)s4)C3)cc2NC(=O)c2c[nH]c(=O)cc2C(F)(F)F)C[C@H](C)N1C]

The procedure followed was similar to that of Example 270 using N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and 2-bromo-5-cyanothiazole (9.31 mg, 0.049 mmol) to afford the title compound (24 mg, 75% yield). $^1$H NMR (500 MHz, METHANOL-d4) δ=7.87-7.80 (m, 1H), 7.73-7.70 (m, 1H), 7.70-7.66 (m, 1H), 6.93-6.85 (m, 1H), 6.82-6.77 (m, 1H), 6.12-6.05 (m, 1H), 4.30-4.23 (m, 2H), 3.74-3.66 (m, 2H), 2.97-2.89 (m, 2H), 2.52-2.46 (m, 2H), 2.45-2.38 (m, 4H), 2.29-2.25 (m, 3H), 1.08-1.03 (m, 6H); LCMS [M+H]+ 616.6

Example 616: N-[4-fluoro-5-(2-morpholin-4-yl-1,3-thiazol-4-yl)-2-[(3R,5S)-3,4,5-trimethylpiperazin-1-yl]phenyl]-6-oxo-4-(trifluoromethyl)-1H-pyridine-3-carboxamide

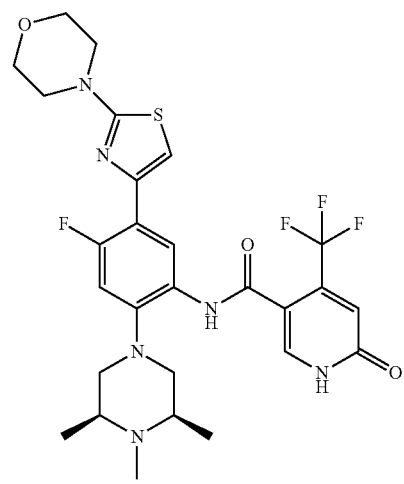 [SMILES: C[C@@H]1CN(c2cc(F)c(-c3csc(N4CCOCC4)n3)cc2NC(=O)c2c[nH]c(=O)cc2C(F)(F)F)C[C@H](C)N1C]

Step 1: 2-(2,4-difluoro-5-nitrophenyl)-6-methyl-1,3,6,2-dioxazaborocane-4,8-dione

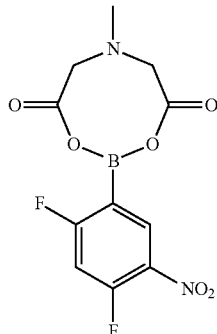

A mixture of 2,4-difluoro-5-nitrophenylboronic acid (4.5 g, 22 mmol) and methyliminodiacetic acid (3.6 g, 24 mmol) in DMF (36 mL) was heated to 85° C. for 18 h under nitrogen. The DMF was removed in vacuo and the waxy yellow solid was dried under reduced pressure overnight to afford 2-(2,4-difluoro-5-nitrophenyl)-6-methyl-1,3,6,2-dioxazaborocane-4,8-dione (7 g, quantitative yield) that did not require purification. LCMS [M−H]−: 313.2.

Step 2: 2-(2-fluoro-5-nitro-4-(cis-3,4,5-trimethylpiperazin-1-yl)phenyl)-6-methyl-1,3,6,2-dioxazaborocane-4,8-dione

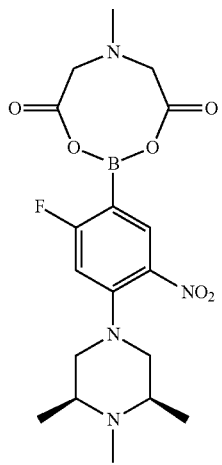

A solution of cis-1,2,6-trimethylpiperazine (0.42 g, 3.4 mmol) in anhydrous toluene (4 mL) was added to a mixture of 2-(2,4-difluoro-5-nitrophenyl)-6-methyl-1,3,6,2-dioxazaborocane-4,8-dione (1.0 g, 3.2 mmol) and potassium carbonate (0.22 g, 1.6 mmol) in anhydrous toluene (3 mL) and anhydrous DMSO (1.0 mL). The reaction mixture was heated to 50° C. for 1.5 h. After cooling to room temperature the organic liquid phase was decanted from the inorganics and filtered through a short pad of celite qualitatively rinsing the reaction vial and celite with a solution of DCM and MeOH. Concentration of the filtrate to dryness and drying under reduced pressure overnight afforded the desired product 2-(2-fluoro-5-nitro-4-(cis-3,4,5-trimethylpiperazin-1-yl)phenyl)-6-methyl-1,3,6,2-dioxazaborocane-4,8-dione (1.5 g, quantitative yield) as a viscous amber oil that was used without further purification. LCMS [M+H]+: 423.3.

Step 3: 4-(4-(2-fluoro-5-nitro-4-(cis-3,4,5-trimethylpiperazin-1-yl)phenyl)thiazol-2-yl)morpholine

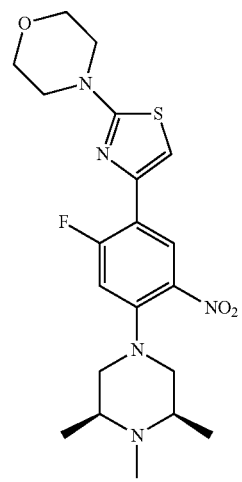 [SMILES: C[C@@H]1CN(c2cc(F)c(-c3csc(N4CCOCC4)n3)cc2[N+](=O)[O-])C[C@H](C)N1C]

A reaction vial was charged with a mixture of 2-(2-fluoro-5-nitro-4-(cis-3,4,5-trimethylpiperazin-1-yl)phenyl)-6-methyl-1,3,6,2-dioxazaborocane-4,8-dione (0.060 g, 0.14 mmol), 4-(4-bromothiazol-2-yl)morpholine (0.042 g, 0.17 mmol) and tetrakis(triphenylphosphine)palladium(0) (0.016 g, 0.014 mmol). The vial was sealed with a septum and evacuated and backfilled with nitrogen. 1,4-Dioxane (4 mL) and 2 M aqueous sodium carbonate (0.9 mL) were added via syringe and the vial was evacuated and backfilled an additional time. The reaction was heated to 90° C. for 3 h. After cooling to room temperature the reaction mixture was concentrated onto celite and purified by flash chromatography [0.5-9.5% MeOH/DCM+0.5% NH4OH] to afford 4-(4-(2-fluoro-5-nitro-4-(cis-3,4,5-trimethylpiperazin-1-yl)phenyl)thiazol-2-yl)morpholine (0.051 g, 82%). LCMS [M+H]+: 436.3.

Step 4: 4-fluoro-5-(2-morpholinothiazol-4-yl)-2-(cis-3,4,5-trimethylpiperazin-1-yl)aniline

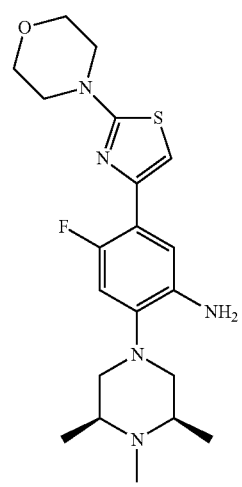 [SMILES: C[C@@H]1CN(c2cc(F)c(-c3csc(N4CCOCC4)n3)cc2N)C[C@H](C)N1C]

A mixture of 4-(4-(2-fluoro-5-nitro-4-(cis-3,4,5-trimethylpiperazin-1-yl)phenyl)thiazol-2-yl)morpholine (0.051 g, 0.12 mmol) and tin(II) chloride (0.070 g, 0.35 mmol) in MeOH (1.5 mL) and EtOH (1.5 mL) was heated to 50° C. for 1 h. After cooling to room temperature the reaction mixture was concentrated onto celite and purified by flash chromatography [0.5-9.5% MeOH/DCM+0.5% NH$_4$OH] to afford 4-fluoro-5-(2-morpholinothiazol-4-yl)-2-(cis-3,4,5-trimethylpiperazin-1-yl)aniline (0.080 g, quantitative yield). LCMS [M+H]+: 406.3.

Step 5: N-(4-fluoro-5-(2-morpholinothiazol-4-yl)-2-(cis-3,4,5-trimethylpiperazin-1-yl)phenyl)-6-oxo-4-(trifluoromethyl)-1,6-dihydropyridine-3-carboxamide

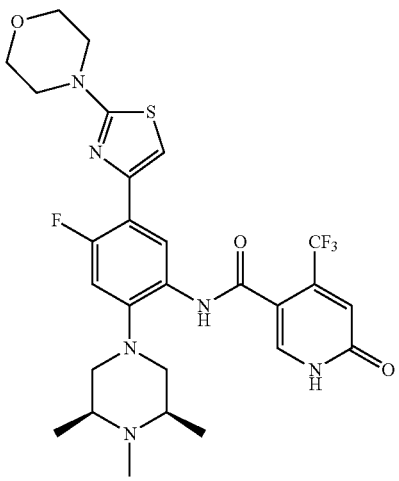 [SMILES: C[C@@H]1CN(c2cc(F)c(-c3csc(N4CCOCC4)n3)cc2NC(=O)c2c[nH]c(=O)cc2C(F)(F)F)C[C@H](C)N1C]

4-(Trifluoromethyl)-6-(2-(trimethylsilyl)ethoxy)nicotinic acid (0.031 g, 0.10 mmol) was activated with HATU (0.040 g, 0.10 mmol) and N,N-diisopropylethylamine (0.017 mL, 0.10 mmol) in DMF (1 mL) at room temperature. The solution of activated acid was added to a solution of 4-fluoro-5-(2-morpholinothiazol-4-yl)-2-(cis-3,4,5-trimethylpiperazin-1-yl)aniline (0.024 g, 0.060 mmol) in DMF (1 mL) and the reaction was heated to 50° C. for 18 h. After cooling to room temperature the reaction mixture was concentrated onto celite and purified by flash chromatography [0.5-9.5% MeOH/DCM+0.5% NH$_4$OH]. The silyl protected amide was dissolved in DCM (1 mL) and treated with TFA (0.5 mL) at room temperature. After stirring for 4 h the volatiles were removed under a stream of air and the title compound was isolated with a catch and release protocol using a SCX2 silica cartridge to afford the title compound N-(4-fluoro-5-(2-morpholinothiazol-4-yl)-2-(cis-3,4,5-trimethylpiperazin-1-yl)phenyl)-6-oxo-4-(trifluoromethyl)-1,6-dihydropyridine-3-carboxamide (0.016 g, 46%). $^1$H NMR (500 MHz, DMSO-d6) δ=12.71-12.39 (m, 1H), 9.49 (s, 1H), 8.18 (br d, J=6.0 Hz, 1H), 7.94 (br s, 1H), 7.12 (d, J=2.0 Hz, 1H), 7.03-6.93 (m, 1H), 6.81 (s, 1H), 6.84-6.78 (m, 1H), 3.75-3.71 (m, 4H), 3.64-3.54 (m, 1H), 3.43-3.40 (m, 4H), 3.15-3.02 (m, 3H), 2.33-2.18 (m, 3H), 1.04 (br s, 6H); LCMS [M+H]+: 595.2.

Example 617: N-[4-fluoro-5-(2-morpholin-4-yl-1,3-thiazol-4-yl)-2-[(3R)-3,4-dimethylpiperazin-1-yl]phenyl]-6-oxo-4-(trifluoromethyl)-1H-pyridine-3-carboxamide

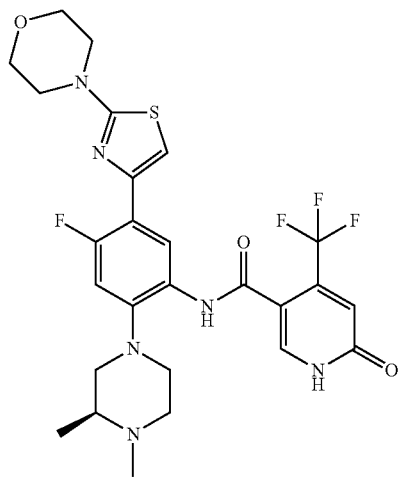 [SMILES: C[C@H]1CN(c2cc(F)c(-c3csc(N4CCOCC4)n3)cc2NC(=O)c2c[nH]c(=O)cc2C(F)(F)F)CCN1C]

The title compound was prepared similar to the procedure described above for the preparation of Example 616 using (S)-1,2-dimethylpiperazine dihydrochloride in place of cis-1,2,6-trimethylpiperazine in Step 2. $^1$H NMR (500 MHz, DMSO-d6) δ=9.47 (s, 1H), 8.17 (br d, J=8.2 Hz, 1H), 7.95 (s, 1H), 7.13 (d, J=2.1 Hz, 1H), 7.00 (d, J=13.2 Hz, 1H), 6.81 (s, 1H), 3.77-3.71 (m, 4H), 3.44-3.41 (m, 4H), 3.02 (br dd, J=11.2, 19.3 Hz, 2H), 2.84-2.73 (m, 3H), 2.41 (br t, J=10.5 Hz, 1H), 2.35-2.29 (m, 1H), 2.21 (s, 3H), 0.97 (d, J=6.2 Hz, 3H); LCMS [M+H]+: 581.2.

Example 618: N-[4-fluoro-5-(2-morpholin-4-yl-1,3-thiazol-5-yl)-2-[(3R)-3,4-dimethylpiperazin-1-yl]phenyl]-6-oxo-4-(trifluoromethyl)-1H-pyridine-3-carboxamide

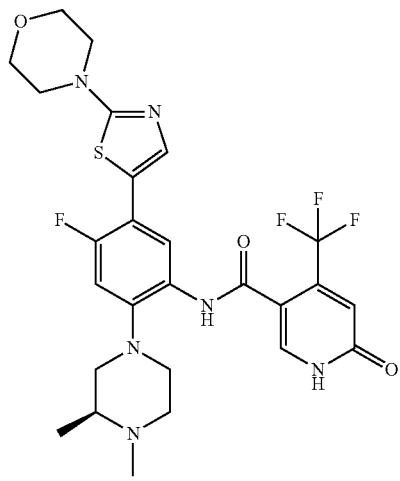 [SMILES: C[C@H]1CN(c2cc(F)c(-c3cnc(N4CCOCC4)s3)cc2NC(=O)c2c[nH]c(=O)cc2C(F)(F)F)CCN1C]

The title compound was prepared similar to the procedure described above for the preparation of Example 616 using (S)-1,2-dimethylpiperazine dihydrochloride in place of cis- 1,2,6-trimethylpiperazine in Step 2 and using 4-(5-bromothiazol-2-yl)morpholine in Step 3. ¹H NMR (500 MHz, DMSO-d6) δ=9.48 (s, 1H), 7.95 (s, 1H), 7.81 (d, J=8.3 Hz, 1H), 7.51 (s, 1H), 7.05 (d, J=13.0 Hz, 1H), 6.82 (s, 1H), 3.75-3.70 (m, 4H), 3.46-3.42 (m, 4H), 3.03-2.95 (m, 2H), 2.82-2.72 (m, 3H), 2.43-2.29 (m, 3H), 2.21 (s, 3H), 0.97 (d, J=6.2 Hz, 3H); LCMS [M+H]+: 581.3.

Example 619: N-[4-fluoro-5-(2-morpholin-4-yl-1,3-thiazol-5-yl)-2-[(3R,5S)-3,4,5-trimethylpiperazin-1-yl]phenyl]-6-oxo-4-(trifluoromethyl)-1H-pyridine-3-carboxamide

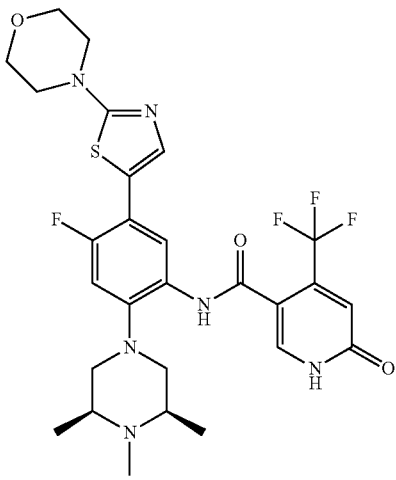 [SMILES: C[C@@H]1CN(c2cc(F)c(-c3cnc(N4CCOCC4)s3)cc2NC(=O)c2c[nH]c(=O)cc2C(F)(F)F)C[C@H](C)N1C]

The title compound was prepared similar to the procedure described above for the preparation of Example 616 using 4-(5-bromothiazol-2-yl)morpholine in place of 4-(4-bromothiazol-2-yl)morpholine in Step 3. ¹H NMR (500 MHz, DMSO-d6) δ=9.50 (s, 1H), 7.94 (s, 1H), 7.81 (d, J=8.3 Hz, 1H), 7.50 (s, 1H), 7.03 (d, J=12.8 Hz, 1H), 6.82 (s, 1H), 3.74-3.71 (m, 4H), 3.46-3.40 (m, 4H), 3.00 (br d, J=11.2 Hz, 2H), 2.44 (br t, J=11.1 Hz, 2H), 2.39-2.30 (m, 2H), 2.19 (s, 3H), 1.00 (d, J=6.0 Hz, 6H); LCMS [M+H]+: 595.3.

Example 620: 4-(difluoromethyl)-N-[4-fluoro-5-(2-morpholin-4-yl-1,3-thiazol-4-yl)-2-[(3R)-3,4-dimethylpiperazin-1-yl]phenyl]-1-methyl-6-oxopyridine-3-carboxamide

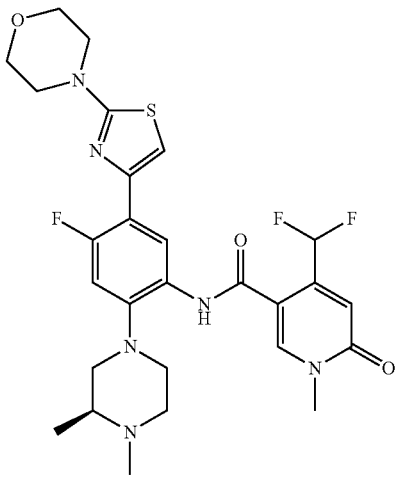 [SMILES: C[C@H]1CN(c2cc(F)c(-c3csc(N4CCOCC4)n3)cc2NC(=O)c2cn(C)c(=O)cc2C(F)F)CCN1C]

The title compound was prepared similar to the procedure described above for the preparation of Example 617 using 4-(difluoromethyl)-1-methyl-6-oxo-1,6-dihydropyridine-3-carboxylic acid in place of 4-(trifluoromethyl)-6-(2-(trimethylsilyl)ethoxy)nicotinic acid in Step 5. ¹H NMR (500 MHz, DMSO-d6) δ=9.44 (s, 1H), 8.43 (s, 1H), 8.09 (d, J=8.4 Hz, 1H), 7.46-7.21 (m, 1H), 7.13 (d, J=2.0 Hz, 1H), 6.99 (d, J=13.3 Hz, 1H), 6.63 (s, 1H), 3.75-3.71 (m, 4H), 3.52 (s, 3H), 3.44-3.39 (m, 4H), 3.07-2.98 (m, 2H), 2.84-2.71 (m, 3H), 2.43-2.35 (m, 2H), 2.34-2.27 (m, 1H), 2.18 (s, 3H), 0.95 (d, J=6.2 Hz, 3H); LCMS [M+H]+: 577.3.

Example 621: 4-(difluoromethyl)-N-[4-fluoro-5-(2-morpholin-4-yl-1,3-thiazol-5-yl)-2-[(3R)-3,4-dimethylpiperazin-1-yl]phenyl]-1-methyl-6-oxopyridine-3-carboxamide

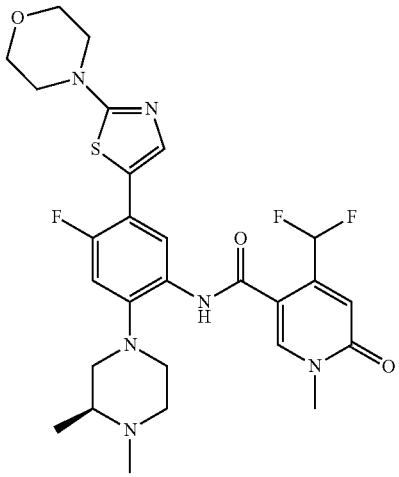 [SMILES: C[C@H]1CN(c2cc(F)c(-c3cnc(N4CCOCC4)s3)cc2NC(=O)c2cn(C)c(=O)cc2C(F)F)CCN1C]

The title compound was prepared similar to the procedure described above for the preparation of Example 618 using 4-(difluoromethyl)-1-methyl-6-oxo-1,6-dihydropyridine-3-carboxylic acid in place of 4-(trifluoromethyl)-6-(2-(trimethylsilyl)ethoxy)nicotinic acid in Step 5. $^1$H NMR (500 MHz, DMSO-d6) δ=9.44 (s, 1H), 8.38 (s, 1H), 7.73 (d, J=8.3 Hz, 1H), 7.51 (s, 1H), 7.46-7.21 (m, 1H), 7.06 (d, J=12.8 Hz, 1H), 6.64 (s, 1H), 3.74-3.70 (m, 4H), 3.52 (s, 3H), 3.45-3.41 (m, 4H), 3.06-2.93 (m, 3H), 2.85-2.71 (m, 3H), 2.42-2.28 (m, 3H), 2.19 (s, 3H), 0.96 (d, J=6.2 Hz, 3H); LCMS [M+H]+: 577.1.

Example 622: 4-(difluoromethyl)-N-[4-fluoro-5-(2-morpholin-4-yl-1,3-thiazol-4-yl)-2-[(3R,5S)-3,4,5-trimethylpiperazin-1-yl]phenyl]-1-methyl-6-oxopyridine-3-carboxamide

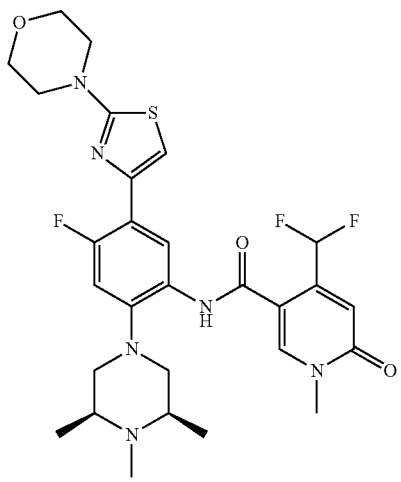 [SMILES: C[C@@H]1CN(c2cc(F)c(-c3csc(N4CCOCC4)n3)cc2NC(=O)c2cn(C)c(=O)cc2C(F)F)C[C@H](C)N1C]

The title compound was prepared similar to the procedure described above for the preparation of Example 616 using 4-(difluoromethyl)-1-methyl-6-oxo-1,6-dihydropyridine-3-carboxylic acid in place of 4-(trifluoromethyl)-6-(2-(trimethylsilyl)ethoxy)nicotinic acid in Step 5. $^1$H NMR (500 MHz, DMSO-d6) δ=9.46 (s, 1H), 8.43 (s, 1H), 8.08 (d, J=8.4 Hz, 1H), 7.48-7.21 (m, 1H), 7.12 (d, J=2.3 Hz, 1H), 6.97 (d, J=13.3 Hz, 1H), 6.63 (s, 1H), 3.76-3.70 (m, 4H), 3.51 (s, 3H), 3.45-3.38 (m, 4H), 3.04 (br d, J=11.1 Hz, 2H), 2.44 (br t, J=11.0 Hz, 2H), 2.30 (dt, J=3.1, 6.6 Hz, 2H), 2.16 (s, 3H), 0.98 (d, J=6.1 Hz, 6H); LCMS [M+H]+: 591.4.

Example 623: 4-(difluoromethyl)-N-[4-fluoro-5-(2-morpholin-4-yl-1,3-thiazol-5-yl)-2-[(3R,5S)-3,4,5-trimethylpiperazin-1-yl]phenyl]-1-methyl-6-oxopyridine-3-carboxamide

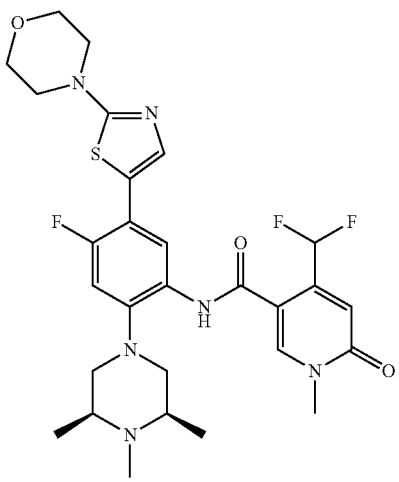 [SMILES: C[C@@H]1CN(c2cc(F)c(-c3cnc(N4CCOCC4)s3)cc2NC(=O)c2cn(C)c(=O)cc2C(F)F)C[C@H](C)N1C]

The title compound was prepared similar to the procedure described above for the preparation of Example 619 using 4-(difluoromethyl)-1-methyl-6-oxo-1,6-dihydropyridine-3-carboxylic acid in place of 4-(trifluoromethyl)-6-(2-(trimethylsilyl)ethoxy)nicotinic acid in Step 5. $^1$H NMR (500 MHz, DMSO-d6) δ=9.46 (s, 1H), 8.36 (s, 1H), 7.71 (d, J=8.3 Hz, 1H), 7.50 (s, 1H), 7.46-7.20 (m, 1H), 7.02 (d, J=12.8 Hz, 1H), 6.64 (s, 1H), 3.73-3.70 (m, 4H), 3.51 (s, 3H), 3.45-3.41 (m, 4H), 3.00 (br d, J=10.9 Hz, 2H), 2.47-2.41 (m, 2H), 2.34-2.29 (m, 2H), 2.17 (s, 3H), 0.98 (d, J=6.1 Hz, 6H); LCMS [M+H]+: 591.3.

Example 624: 2,4-difluoro-5-[2-fluoro-5-[[4-fluoro-2-(trifluoromethyl)benzoyl]amino]-4-[(3R,5S)-3,4,5-trimethylpiperazin-1-yl]phenyl]-N-(2,4,4-trimethylpentan-2-yl)benzamide A procedure similar to that of Example 100 using 2,4-difluoro-5-(4,4,5,5-tetramethyl-1,3,2-dioxaborolan-2-yl)-N-(2,4,4-trimethylpentan-2-yl)benzamide (50.0 mg, 0.126 mmol) and N-(5-bromo-4-fluoro-2-((3S,5R)-3,4,5-trimethylpiperazin-1-yl)phenyl)-4-fluoro-2-(trifluoromethyl)benzamide (40 mg, 0.079 mmol) afforded the title compound as an off-white fluffy powder (39 mg, 0.053 mmol, 67.5% yield). $^1$H NMR (500 MHz, METHANOL-d4) δ=7.84 (d, J=7.7 Hz, 1H), 7.75-7.51 (m, 4H), 7.45 (dt, J=2.3, 8.3 Hz, 1H), 7.07 (t, J=10.0 Hz, 1H), 6.99 (d, J=11.2 Hz, 1H), 3.00 (br d, J=11.4 Hz, 2H), 2.54 (br t, J=11.1 Hz, 2H), 2.42 (br s, 2H), 2.26 (br s, 3H), 1.82 (s, 2H), 1.38 (s, 6H), 1.07 (d, J=6.1 Hz, 6H), 0.94 (s, 9H); LCMS [M+H]$^+$ 695.

Example 625: 2,4-difluoro-5-[2-fluoro-5-[[4-fluoro-2-(trifluoromethyl)benzoyl]amino]-4-[(3R)-3,4-dimethylpiperazin-1-yl]phenyl]-N-(2,4,4-trimethylpentan-2-yl)benzamide

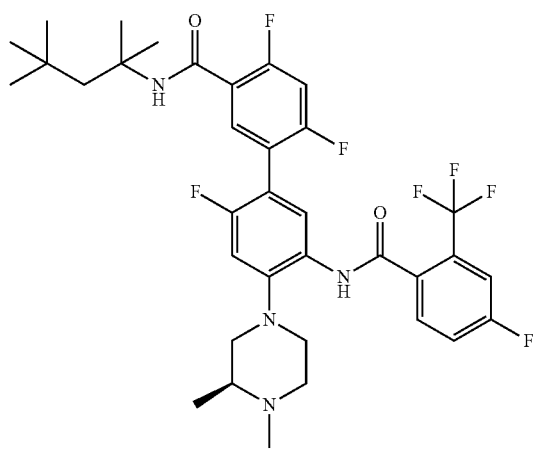 [SMILES: C[C@H]1CN(c2cc(F)c(-c3cc(C(=O)NC(C)(C)CC(C)(C)C)c(F)cc3F)cc2NC(=O)c2ccc(F)cc2C(F)(F)F)CCN1C]

A procedure similar to Example 100 using 2,4-difluoro-5-(4,4,5,5-tetramethyl-1,3,2-dioxaborolan-2-yl)-N-(2,4,4-trimethylpentan-2-yl)benzamide (51.4 mg, 0.130 mmol), potassium phosphate tribasic reagent grade, >=98% (51.7 mg, 0.244 mmol) and (S)—N-(5-bromo-2-(3,4-dimethylpiperazin-1-yl)-4-fluorophenyl)-4-fluoro-2-(trifluoromethyl)benzamide (40 mg, 0.081 mmol) afforded the title compound as an off-white fluffy powder (33 mg, 0.046 mmol, 56.7% yield). $^1$H NMR (500 MHz, METHANOL-d4) δ=7.84 (d, J=7.8 Hz, 1H), 7.76-7.58 (m, 2H), 7.57-7.51 (m, 2H), 7.45 (dt, J=2.4, 8.3 Hz, 1H), 7.07 (t, J=10.0 Hz, 1H), 7.03-6.99 (m, 1H), 3.09-3.04 (m, 1H), 3.01 (br d, J=11.7 Hz, 1H), 2.90-2.83 (m, 2H), 2.51 (br t, J=10.9 Hz, 1H), 2.45 (br s, 1H), 2.37-2.31 (m, 1H), 2.29 (br s, 3H), 1.83 (s, 2H), 1.39 (s, 6H), 1.04 (d, J=6.2 Hz, 3H), 0.95 (s, 9H); LCMS [M+H]$^+$ 681.

Example 626: N-[5-[2,4-difluoro-5-(2,4,4-trimethylpentan-2-ylcarbamoyl)phenyl]-4-fluoro-2-[(3R,5S)-3,4,5-trimethylpiperazin-1-yl]phenyl]-6-oxo-4-(trifluoromethyl)-1H-pyridine-3-carboxamide

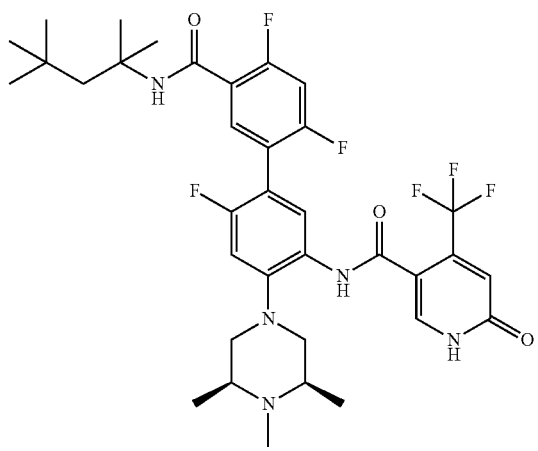 [SMILES: C[C@@H]1CN(c2cc(F)c(-c3cc(C(=O)NC(C)(C)CC(C)(C)C)c(F)cc3F)cc2NC(=O)c2c[nH]c(=O)cc2C(F)(F)F)C[C@H](C)N1C]

A sequence similar to Example 100 using 2,4-difluoro-5-(4,4,5,5-tetramethyl-1,3,2-dioxaborolan-2-yl)-N-(2,4,4-trimethylpentan-2-yl)benzamide (41.8 mg, 0.106 mmol) and N-(5-bromo-4-fluoro-2-((3S,5R)-3,4,5-trimethylpiperazin-1-yl)phenyl)-6-(2-(trimethylsilyl)ethoxy)nicotinamide (40 mg, 0.066 mmol) afforded the title compound (TFA salt) as a white fluffy powder (12.7 mg, 0.013 mmol, 94% yield). $^1$H NMR (500 MHz, METHANOL-d4) δ=7.92 (s, 1H), 7.79 (d, J=7.6 Hz, 1H), 7.73 (br s, 1H), 7.58 (t, J=8.0 Hz, 1H), 7.14-7.05 (m, 2H), 6.87-6.82 (m, 1H), 3.47-3.38 (m, 2H), 3.33 (br d, J=13.1 Hz, 2H), 2.91 (s, 3H), 2.89-2.80 (m, 2H), 1.85 (s, 2H), 1.40 (s, 6H), 1.37 (d, J=6.5 Hz, 6H), 0.96 (s, 9H); LCMS [M+H]$^+$ 694.

Example 627: 4-(difluoromethyl)-N-[5-[2,4-difluoro-5-(2,4,4-trimethylpentan-2-ylcarbamoyl)phenyl]-4-fluoro-2-[(3R,5S)-3,4,5-trimethylpiperazin-1-yl]phenyl]-6-oxo-1H-pyridine-3-carboxamide

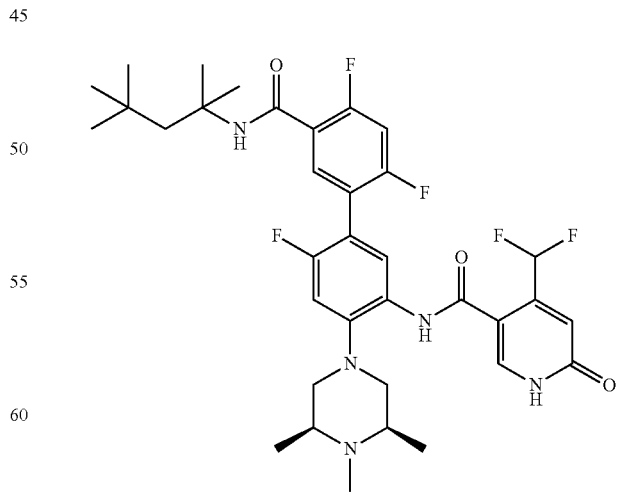

A procedure similar to Example 100 using 2,4-difluoro-5-(4,4,5,5-tetramethyl-1,3,2-dioxaborolan-2-yl)-N-(2,4,4-trimethylpentan-2-yl)benzamide (43.1 mg, 0.109 mmol) and N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (40 mg, 0.068 mmol). The title compound (TFA salt) was collected as a white fluffy powder (13 mg, 0.015 mmol, 100% yield). $^1$H NMR (500 MHz, METHANOL-d4) δ=7.95 (s, 1H), 7.69 (br d, J=2.2 Hz, 1H), 7.61 (d, J=7.6 Hz, 1H), 7.56 (t, J=7.9 Hz, 1H), 7.32-7.10 (m, 1H), 7.09-7.04 (m, 2H), 6.72-6.66 (m, 1H), 3.42-3.36 (m, 2H), 3.35-3.31 (m, 2H), 2.89 (s, 3H), 2.85-2.79 (m, 2H), 1.83 (s, 2H), 1.38 (s, 6H), 1.34 (d, J=6.4 Hz, 6H), 0.94 (s, 9H); LCMS [M+H]$^+$ 676.

Example 628: 4-(difluoromethyl)-N-[4-fluoro-2-[(3R)-3,4-dimethylpiperazin-1-yl]-5-[2-[(3R)-3-methylmorpholin-4-yl]pyrimidin-5-yl]phenyl]-6-oxo-1H-pyridine-3-carboxamide

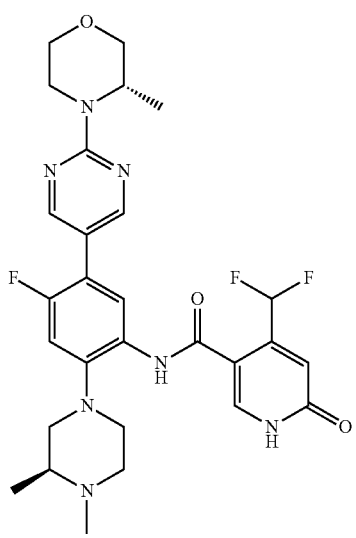 [SMILES: C[C@H]1CN(c2cc(F)c(-c3cnc(N4CCOC[C@@H]4C)nc3)cc2NC(=O)c2c[nH]c(=O)cc2C(F)F)CCN1C]

The title compound was prepared according to a procedure similar to that of Example 39 using (S)-3-methyl-4-(5-(4,4,5,5-tetramethyl-1,3,2-dioxaborolan-2-yl)pyrimidin-2-yl)morpholine and (S)—N-(5-bromo-2-(3,4-dimethylpiperazin-1-yl)-4-fluorophenyl)-4-(difluoromethyl)-6-(2-(trimethylsilyl)ethoxy)nicotinamide. $^1$H NMR (500 MHz, METHANOL-d4) δ=8.54 (d, J=1.0 Hz, 2H), 8.03 (s, 1H), 7.82 (d, J=8.3 Hz, 1H), 7.46-7.18 (m, 1H), 7.08 (d, J=12.1 Hz, 1H), 6.81 (s, 1H), 4.74 (br dd, J=2.8, 6.7 Hz, 1H), 4.37 (dd, J=2.6, 13.8 Hz, 1H), 3.98 (dd, J=3.6, 11.3 Hz, 1H), 3.84-3.76 (m, 1H), 3.75-3.68 (m, 1H), 3.56 (dt, J=3.1, 11.9 Hz, 1H), 3.15-3.03 (m, 2H), 2.98-2.87 (m, 2H), 2.61-2.49 (m, 2H), 2.44-2.38 (m, 1H), 2.37 (s, 3H), 1.30 (d, J=6.8 Hz, 3H), 1.12 (d, J=6.2 Hz, 3H); LCMS [M+H]+: 572.4.

Example 629: (S)-4-(Sifluoromethyl)-N-(2-(3,4-dimethylpiperazin-1-yl)-4-fluoro-5-(1-(pyrrolidine-1-carbonyl)-2,5-dihydro-1H-pyrrol-3-yl)phenyl)-6-oxo-1,6-dihydropyridine-3-carboxamide

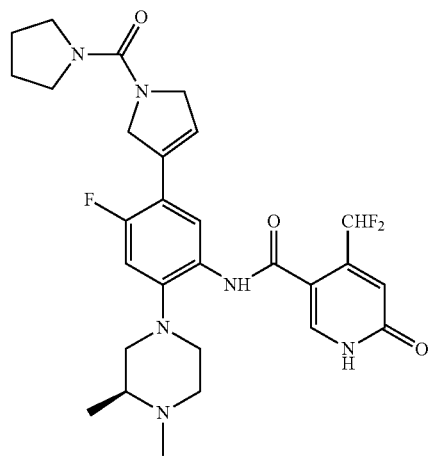 [SMILES: C[C@H]1CN(c2cc(F)c(C3=CCN(C(=O)N4CCCC4)C3)cc2NC(=O)c2c[nH]c(=O)cc2C(F)F)CCN1C]

The procedure followed was similar to Example 253 using (S)-4-(difluoromethyl)-N-(5-(2,5-dihydro-1H-pyrrol-3-yl)-2-(3,4-dimethylpiperazin-1-yl)-4-fluorophenyl)-6-oxo-1,6-dihydropyridine-3-carboxamide (25 mg, 0.054 mmol) and 1-pyrrolidinecarbonyl chloride (5.99 μl, 0.054 mmol) to give the title compound (25 mg, 78% yield). $^1$H NMR (500 MHz, METHANOL-d4 δ=8.07-8.01 (m, 1H), 7.78-7.70 (m, 1H), 7.44-7.19 (m, 1H), 7.05-6.97 (m, 1H), 6.84-6.78 (m, 1H), 6.38-6.31 (m, 1H), 4.70-4.58 (m, 2H), 4.51-4.39 (m, 2H), 3.55-3.43 (m, 4H), 3.15-3.02 (m, 2H), 2.97-2.87 (m, 2H), 2.58-2.48 (m, 2H), 2.42-2.34 (m, 4H), 1.97-1.87 (m, 4H), 1.11 (d, J=6.2 Hz, 3H); LCMS [M+H]+ 559.5.

Example 630: 1-Methylcyclobutyl 3-(5-(4-(difluoromethyl)-6-oxo-1,6-dihydropyridine-3-carboxamido)-2-fluoro-4-((3S,5R)-3,4,5-trimethylpiperazin-1-yl)phenyl)-2,5-dihydro-1H-pyrrole-1-carboxylate

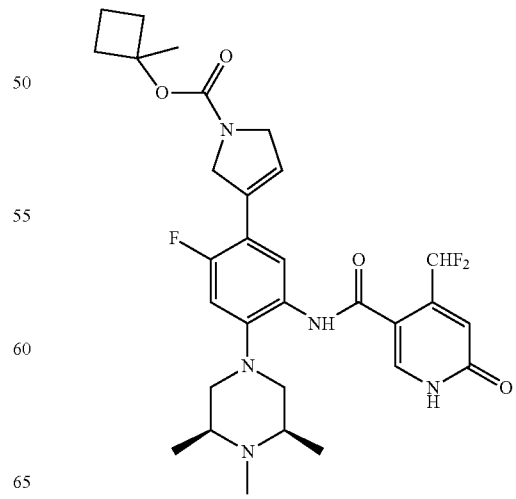

The procedure used was similar to Example 253 using 4-(difluoromethyl)-N-(5-(2,5-dihydro-1H-pyrrol-3-yl)-4-fluoro-2-((3S,5R)-3,4,5-trimethylpiperazin-1-yl)phenyl)-6-oxo-1,6-dihydropyridine-3-carboxamide (25 mg, 0.053 mmol), and 1-methylcyclobutyl (4-nitrophenyl) carbonate (18.16 mg, 0.058 mmol) to give the title compound (22 mg, 68% yield). $^1$H NMR (500 MHz, METHANOL-d4 δ=8.06-7.99 (m, 1H), 7.75-7.66 (m, 1H), 7.45-7.19 (m, 1H), 7.03-6.94 (m, 1H), 6.84-6.77 (m, 1H), 6.39-6.30 (m, 1H), 4.57-4.46 (m, 2H), 4.38-4.26 (m, 2H), 3.12-3.03 (m, 2H), 2.63-2.56 (m, 2H), 2.55-2.47 (m, 2H), 2.45-2.35 (m, 5H), 2.21-2.12 (m, 2H), 1.91-1.81 (m, 1H), 1.78-1.67 (m, 1H), 1.61 (d, J=3.4 Hz, 3H), 1.18-1.13 (m, 6H); LCMS [M+H]+ 588.6.

Example 631: 1-Methylcyclobutyl (S)-3-(5-(4-(difluoromethyl)-6-oxo-1,6-dihydropyridine-3-carboxamido)-4-(3,4-dimethylpiperazin-1-yl)-2-fluorophenyl)-2,5-dihydro-1H-pyrrole-1-carboxylate

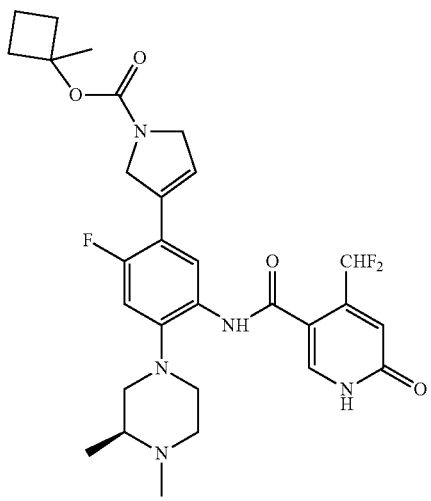 [SMILES: C[C@H]1CN(c2cc(F)c(C3=CCN(C(=O)OC4(C)CCC4)C3)cc2NC(=O)c2c[nH]c(=O)cc2C(F)F)CCN1C]

The procedure followed was similar to Example 253 using (S)-4-(difluoromethyl)-N-(5-(2,5-dihydro-1H-pyrrol-3-yl)-2-(3,4-dimethylpiperazin-1-yl)-4-fluorophenyl)-6-oxo-1,6-dihydropyridine-3-carboxamide (25 mg, 0.054 mmol) and 1-methylcyclobutyl (4-nitrophenyl) carbonate (18.71 mg, 0.060 mmol) to afford the title compound (18 mg, 55% yield). $^1$H NMR (500 MHz, METHANOL-d4 δ=8.07-8.00 (m, 1H), 7.78-7.68 (m, 1H), 7.45-7.20 (m, 1H), 7.05-6.97 (m, 1H), 6.85-6.79 (m, 1H), 6.39-6.30 (m, 1H), 4.59-4.47 (m, 2H), 4.38-4.27 (m, 2H), 3.16-3.03 (m, 2H), 2.97-2.87 (m, 2H), 2.59-2.49 (m, 2H), 2.45-2.35 (m, 6H), 2.23-2.12 (m, 2H), 1.91-1.81 (m, 1H), 1.78-1.68 (m, 1H), 1.65-1.58 (m, 3H), 1.15-1.09 (m, 3H); LCMS [M+H]+ 574.5.

Example 632: N-[5-(5-carbamoyl-2,4-difluorophenyl)-4-fluoro-2-[(3R,5S)-3,4,5-trimethylpiperazin-1-yl]phenyl]-6-oxo-4-(trifluoromethyl)-1H-pyridine-3-carboxamide

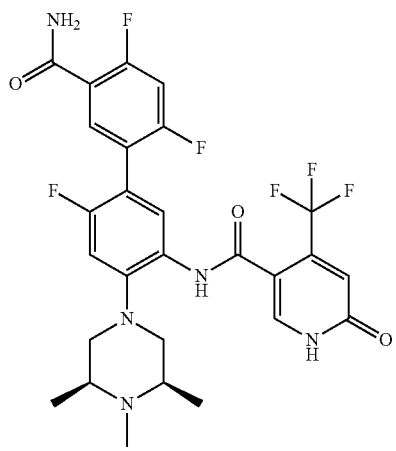 [SMILES: C[C@@H]1CN(c2cc(F)c(-c3cc(C(N)=O)c(F)cc3F)cc2NC(=O)c2c[nH]c(=O)cc2C(F)(F)F)C[C@H](C)N1C]

A procedure similar to that of Example 100 using 2,4-difluoro-5-(4,4,5,5-tetramethyl-1,3,2-dioxaborolan-2-yl)-N-(2,4,4-trimethylpentan-2-yl)benzamide (41.8 mg, 0.106 mmol) and N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (40 mg, 0.066 mmol) gave the title compound (TFA salt) as an off-white fluffy powder (32 mg, 96% yield). $^1$H NMR (500 MHz, METHANOL-d4) δ=7.90 (s, 1H), 7.82 (t, J=8.2 Hz, 1H), 7.78 (d, J=7.6 Hz, 1H), 7.14 (t, J=10.2 Hz, 1H), 7.09 (d, J=10.9 Hz, 1H), 6.84-6.79 (m, 1H), 3.41 (ddd, J=2.9, 6.8, 10.2 Hz, 2H), 3.31 (br d, J=13.2 Hz, 2H), 2.89 (s, 3H), 2.88-2.81 (m, 2H), 1.35 (d, J=6.5 Hz, 6H); LCMS [M+H]$^+$ 582.

Example 633: N-[5-(5-carbamoyl-2,4-difluorophenyl)-4-fluoro-2-[(3R,5S)-3,4,5-trimethylpiperazin-1-yl]phenyl]-4-(difluoromethyl)-6-oxo-1H-pyridine-3-carboxamide

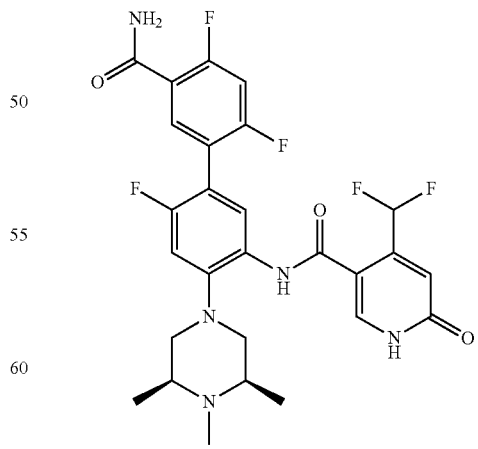

A procedure similar to Example 100 using 2,4-difluoro-5-(4,4,5,5-tetramethyl-1,3,2-dioxaborolan-2-yl)-N-(2,4,4-trimethylpentan-2-yl)benzamide (43.1 mg, 0.109 mmol) and N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (40 mg, 0.068 mmol) afforded the title compound (TFA salt) as an off-white fluffy powder (35 mg, 0.042 mmol, 93% yield). $^1$H NMR (500 MHz, DMSO-d6) δ=7.03 (s, 1H), 6.89 (t, J=8.2 Hz, 1H), 6.70 (d, J=7.6 Hz, 1H), 6.39-6.16 (m, 2H), 6.14 (d, J=11.0 Hz, 1H), 5.79-5.76 (m, 1H), 2.50-2.43 (m, 2H), 2.41 (br d, J=14.1 Hz, 2H), 1.96 (s, 3H), 1.91 (br t, J=12.0 Hz, 2H), 0.41 (d, J=6.4 Hz, 6H); LCMS [M+H]$^+$ 564.

Example 634: 2,4-difluoro-5-[2-fluoro-5-[[4-fluoro-2-(trifluoromethyl)benzoyl]amino]-4-[(3R,5S)-3,4,5-trimethylpiperazin-1-yl]phenyl]benzamide

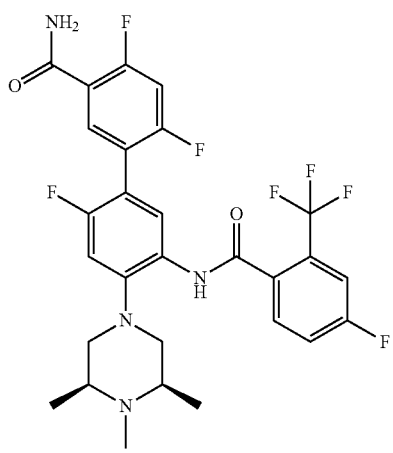 [SMILES: C[C@@H]1CN(c2cc(F)c(-c3cc(C(N)=O)c(F)cc3F)cc2NC(=O)c2ccc(F)cc2C(F)(F)F)C[C@H](C)N1C]

A procedure similar to Example 100 was followed using 2,4-difluoro-5-(4,4,5,5-tetramethyl-1,3,2-dioxaborolan-2-yl)-N-(2,4,4-trimethylpentan-2-yl)benzamide (50.0 mg, 0.126 mmol) and N-(5-bromo-4-fluoro-2-((3S,5R)-3,4,5-trimethylpiperazin-1-yl)phenyl)-4-fluoro-2-(trifluoromethyl)benzamide (40 mg, 0.079 mmol). The title compound (TFA salt) was collected as an off-white fluffy powder (40 mg, 0.047 mmol, 93% yield). $^1$H NMR (500 MHz, METHANOL-d4) δ=7.90 (d, J=7.7 Hz, 1H), 7.83 (t, J=8.1 Hz, 1H), 7.69 (dd, J=5.3, 8.4 Hz, 1H), 7.58-7.53 (m, 1H), 7.46 (dt, J=2.1, 8.3 Hz, 1H), 7.15 (t, J=10.2 Hz, 1H), 7.11 (d, J=11.0 Hz, 1H), 3.44-3.35 (m, 2H), 3.33 (br d, J=13.4 Hz, 2H), 2.90-2.81 (m, 5H), 1.35 (d, J=6.5 Hz, 6H); LCMS [M+H]$^+$ 583.

Example 635: 2,4-difluoro-5-[2-fluoro-5-[[4-fluoro-2-(trifluoromethyl)benzoyl]amino]-4-[(3R)-3,4-dimethylpiperazin-1-yl]phenyl]benzamide

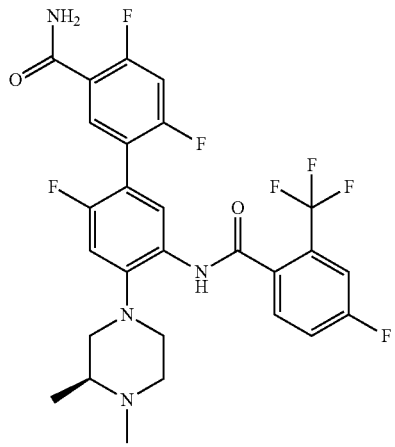 [SMILES: C[C@H]1CN(c2cc(F)c(-c3cc(C(N)=O)c(F)cc3F)cc2NC(=O)c2ccc(F)cc2C(F)(F)F)CCN1C]

A coupling procedure similar to that of Example 100 using 2,4-difluoro-5-(4,4,5,5-tetramethyl-1,3,2-dioxaborolan-2-yl)-N-(2,4,4-trimethylpentan-2-yl)benzamide (51.4 mg, 0.130 mmol) and (S)—N-(5-bromo-2-(3,4-dimethylpiperazin-1-yl)-4-fluorophenyl)-4-fluoro-2-(trifluoromethyl)benzamide (40 mg, 0.081 mmol) afforded the title compound (TFA salt) as an off-white fluffy powder (28 mg, 87% yield). $^1$H NMR (500 MHz, METHANOL-d4) δ=7.89 (d, J=7.6 Hz, 1H), 7.83 (t, J=8.1 Hz, 1H), 7.70 (br dd, J=5.3, 8.3 Hz, 1H), 7.58-7.53 (m, 1H), 7.46 (dt, J=2.0, 8.2 Hz, 1H), 7.15 (t, J=10.3 Hz, 1H), 7.11 (d, J=11.0 Hz, 1H), 3.55 (br d, J=12.2 Hz, 1H), 3.36-3.28 (m, 3H), 3.09-2.99 (m, 1H), 2.87 (s, 3H), 2.86-2.79 (m, 2H), 1.33 (d, J=6.4 Hz, 3H); LCMS [M+H]$^+$ 569.

Example 636: 4-Fluoro-N-[4-fluoro-5-[2-(4-hydroxy-4-methylpiperidin-1-yl)pyrimidin-5-yl]-2-[(3R,5S)-3,4,5-trimethylpiperazin-1-yl]phenyl]-2-(trifluoromethyl)benzamide

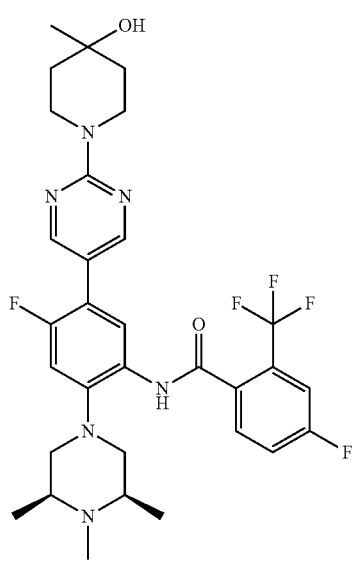

The title compound (formic acid salt, pale beige solid, 24.5 mg, 37%) was prepared by a procedure similar to that of Example 39 using crude (2-(4-hydroxy-4-methylpiperidin-1-yl)pyrimidin-5-yl)boronic acid (0.3 mmol) and N-(5-bromo-4-fluoro-2-((3S,5R)-3,4,5-trimethylpiperazin-1-yl)phenyl)-4-fluoro-2-(trifluoromethyl)benzamide (57 mg, 89% purity, 0.1 mmol). $^1$H NMR (500 MHz, METHANOL-d4) δ=8.53 (s, 2H), 8.40 (br s, 1H), 8.05 (d, J=8.2 Hz, 1H), 7.81 (dd, J=5.3, 8.4 Hz, 1H), 7.67 (dd, J=1.9, 9.1 Hz, 1H), 7.59 (t, J=8.2 Hz, 1H), 7.18 (d, J=11.7 Hz, 1H), 4.31 (td, J=4.0, 13.3 Hz, 2H), 3.63-3.55 (m, 2H), 3.25 (br d, J=12.5 Hz, 2H), 3.21-3.11 (m, 2H), 2.91-2.81 (m, 2H), 2.75 (br s, 3H), 1.70-1.59 (m, 4H), 1.35 (br d, J=6.1 Hz, 6H), 1.29 (s, 3H); LCMS [M+H]$^+$ 619.5.

Example 637: 3,3-Difluorocyclobutyl 3-(5-(4-(difluoromethyl)-6-oxo-1,6-dihydropyridine-3-carboxamido)-2-fluoro-4-((3S,5R)-3,4,5-trimethylpiperazin-1-yl)phenyl)-2,5-dihydro-1H-pyrrole-1-carboxylate

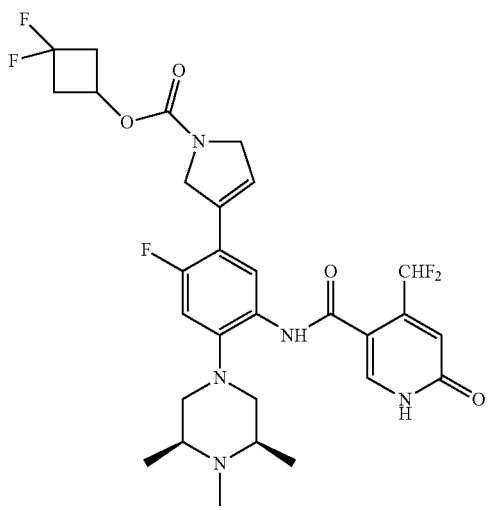 [SMILES: C[C@@H]1CN(c2cc(F)c(C3=CCN(C(=O)OC4CC(F)(F)C4)C3)cc2NC(=O)c2c[nH]c(=O)cc2C(F)F)C[C@H](C)N1C]

A procedure similar to Example 253 using 4-(difluoromethyl)-N-(5-(2,5-dihydro-1H-pyrrol-3-yl)-4-fluoro-2-((3S,5R)-3,4,5-trimethylpiperazin-1-yl)phenyl)-6-oxo-1,6-dihydropyridine-3-carboxamide (25 mg, 0.053 mmol, in turn prepared from the intermediate in Step 1, Example 397 using procedures similar to Example 100) and 3,3-difluorocyclobutyl (4-nitrophenyl) carbonate (15.80 mg, 0.058 mmol) gave the title compound (25 mg, 74% yield). $^1$H NMR (500 MHz, METHANOL-d4 6=8.06-7.98 (m, 1H), 7.76-7.66 (m, 1H), 7.44-7.19 (m, 1H), 7.04-6.94 (m, 1H), 6.83-6.76 (m, 1H), 6.40-6.28 (m, 1H), 4.99-4.91 (m, 1H), 4.62-4.50 (m, 2H), 4.43-4.30 (m, 2H), 3.12-2.98 (m, 4H), 2.83-2.67 (m, 2H), 2.64-2.56 (m, 2H), 2.55-2.47 (m, 2H), 2.41-2.34 (m, 3H), 1.15 (d, J=6.1 Hz, 6H); LCMS [M+H]+ 610.4.

Example 638: 3,3-Difluorocyclobutyl (S)-3-(5-(4-(difluoromethyl)-6-oxo-1,6-dihydropyridine-3-carboxamido)-4-(3,4-dimethylpiperazin-1-yl)-2-fluorophenyl)-2,5-dihydro-1H-pyrrole-1-carboxylate

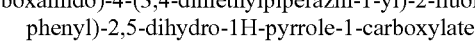

The procedure followed was similar to Example 253 using (S)-4-(difluoromethyl)-N-(5-(2,5-dihydro-1H-pyrrol-3-yl)-2-(3,4-dimethylpiperazin-1-yl)-4-fluorophenyl)-6-oxo-1,6-dihydropyridine-3-carboxamide (25 mg, 0.054 mmol, prepared from the intermediate 1, Example 396 from a couple procedure similar to that described in Example 100) and 3,3-difluorocyclobutyl (4-nitrophenyl) carbonate (16.28 mg, 0.060 mmol) to give the title compound (25 mg, 74% yield). $^1$H NMR (500 MHz, METHANOL-d4 6=8.07-8.00 (m, 1H), 7.78-7.67 (m, 1H), 7.45-7.19 (m, 1H), 7.06-6.97 (m, 1H), 6.86-6.79 (m, 1H), 6.41-6.31 (m, 1H), 5.00-4.92 (m, 1H), 4.63-4.52 (m, 2H), 4.44-4.32 (m, 2H), 3.16-3.01 (m, 4H), 2.96-2.88 (m, 2H), 2.83-2.68 (m, 2H), 2.58-2.48 (m, 2H), 2.44-2.33 (m, 4H), 1.12 (d, J=6.2 Hz, 3H); LCMS [M+H]+ 596.4.

Example 639: (S)—N-(5-(1-(2-cyanopyrimidin-5-yl)-1,2,3,6-tetrahydropyridin-4-yl)-2-(3,4-dimethylpiperazin-1-yl)-4-fluorophenyl)-4-(difluoromethyl)-6-oxo-1,6-dihydropyridine-3-carboxamide Example 640: N-[4-fluoro-5-[2-[(2R)-2-methylmorpholin-4-yl]pyrimidin-5-yl]-2-[(3R,5S)-3,4,5-trimethylpiperazin-1-yl]phenyl]-1-methyl-6-oxo-4-(trifluoromethyl)pyridine-3-carboxamide

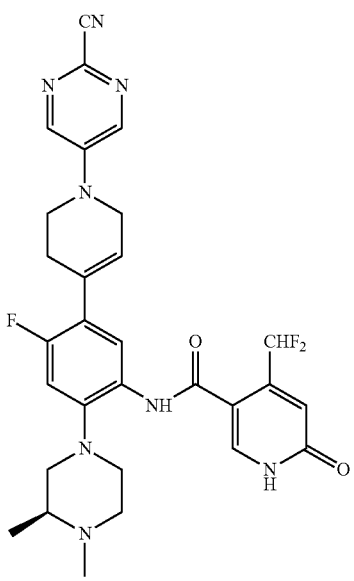 [SMILES: C[C@H]1CN(c2cc(F)c(C3=CCN(c4cnc(C#N)nc4)CC3)cc2NC(=O)c2c[nH]c(=O)cc2C(F)F)CCN1C]

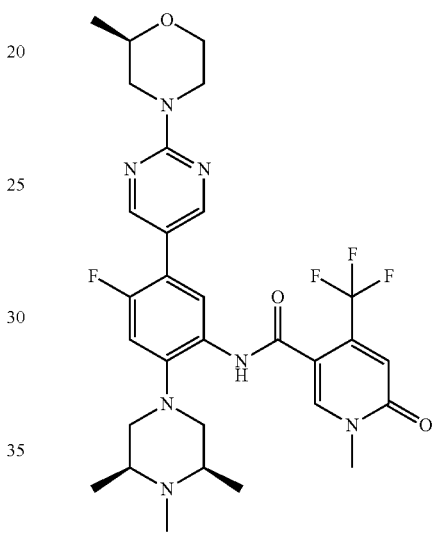

The procedure was similar to that of Example 270 using 5-bromo-2-cyanopyrimidine (14.51 mg, 0.079 mmol) and (S)-4-(difluoromethyl)-N-(2-(3,4-dimethylpiperazin-1-yl)-4-fluoro-5-(1,2,3,6-tetrahydropyridin-4-yl)phenyl)-6-oxo-1,6-dihydropyridine-3-carboxamide (30 mg, 0.063 mmol, prepared using similar methods to those described in the Example 638) to afford the title compound as an off white solid (8 mg). $^1$H NMR (500 MHz, METHANOL-d4 δ=9.61-9.41 (m, 1H), 8.71-8.46 (m, 2H), 8.38-8.13 (m, 1H), 8.09-7.91 (m, 1H), 7.65-7.52 (m, 1H), 7.50-7.16 (m, 1H), 7.06-6.86 (m, 1H), 6.67-6.51 (m, 1H), 6.13-5.98 (m, 1H), 4.16-4.07 (m, 2H), 3.74 (t, J=5.6 Hz, 2H), 3.04-2.93 (m, 2H), 2.84-2.71 (m, 2H), 2.62-2.55 (m, 2H), 2.42-2.36 (m, 1H), 2.36-2.28 (m, 1H), 2.24-2.17 (m, 4H), 1.00-0.93 (m, 3H); LCMS [M+H]+ 579.5

The title compound (formic acid salt, light beige solid, 31.4 mg, 47%) was prepared according a procedure similar to Example 31 using crude (R)-(2-(2-methylmorpholino)pyrimidin-5-yl)boronic acid (0.3 mmol) and N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (52 mg, 0.1 mmol). $^1$H NMR (500 MHz, METHANOL-d4) δ=8.56 (s, 2H), 8.53-8.33 (m, 1H), 8.30 (s, 1H), 7.93 (d, J=8.2 Hz, 1H), 7.17 (d, J=11.9 Hz, 1H), 6.96 (s, 1H), 4.65-4.55 (m, 2H), 3.99 (dd, J=2.6, 11.5 Hz, 1H), 3.71-3.58 (m, 5H), 3.26-3.05 (m, 5H), 2.90-2.80 (m, 2H), 2.77-2.70 (m, 4H), 1.34 (br d, J=5.3 Hz, 6H), 1.25 (d, J=6.2 Hz, 3H); LCMS [M+H]+ 618.3.

Example 641: N-[4-fluoro-5-[2-(4-hydroxy-4-methylpiperidin-1-yl)pyrimidin-5-yl]-2-[(3R,5S)-3,4,5-trimethylpiperazin-1-yl]phenyl]-1-methyl-6-oxo-4-(trifluoromethyl)pyridine-3-carboxamide

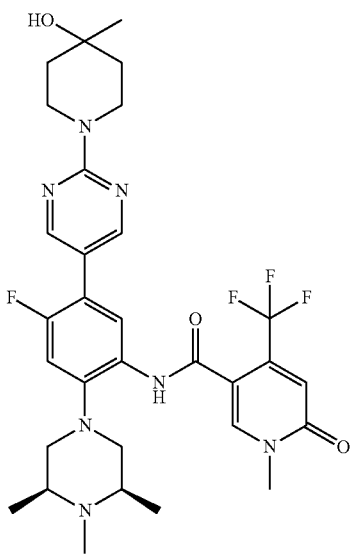 [SMILES: C[C@@H]1CN(c2cc(F)c(-c3cnc(N4CCC(C)(O)CC4)nc3)cc2NC(=O)c2cn(C)c(=O)cc2C(F)(F)F)C[C@H](C)N1C]

The title compound (formic acid salt, pale beige solid, 27.6 mg, 40%) was prepared according to a procedure similar to Example 31 using crude (2-(4-hydroxy-4-methylpiperidin-1-yl)pyrimidin-5-yl)boronic acid (0.3 mmol) and N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (52 mg, 0.1 mmol). $^1$H NMR (500 MHz, METHANOL-d4) δ=8.52 (s, 2H), 8.41 (br s, 1H), 8.31 (s, 1H), 7.91 (d, J=8.2 Hz, 1H), 7.18 (d, J=11.7 Hz, 1H), 6.96 (s, 1H), 4.34-4.27 (m, 2H), 3.67 (s, 3H), 3.63-3.53 (m, 2H), 3.31-3.21 (m, 4H), 2.89 (br d, J=11.2 Hz, 2H), 2.80 (br d, J=6.1 Hz, 3H), 2.68 (s, 1H), 1.70-1.58 (m, 4H), 1.37 (br d, J=6.0 Hz, 6H), 1.29 (s, 3H); LCMS [M+H]$^+$ 632.5.

Example 642: N-[5-[1-(4-cyano-1,3-thiazol-2-yl)-3,6-dihydro-2H-pyridin-5-yl]-4-fluoro-2-[(3R,5S)-3,4,5-trimethylpiperazin-1-yl]phenyl]-6-oxo-4-(trifluoromethyl)-1H-pyridine-3-carboxamide

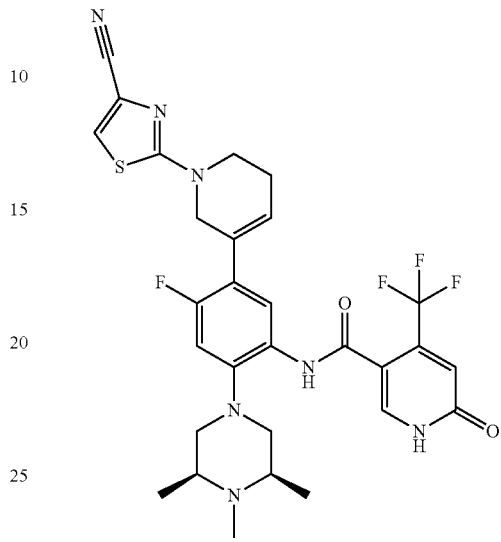

A procedure similar to Example 270 using N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and 2-bromo-4-cyanothiazole (9.31 mg, 0.049 mmol) afforded the title compound (19 mg, 60% yield). $^1$H NMR (500 MHz, METHANOL-d4) δ=7.87-7.81 (m, 1H), 7.74-7.64 (m, 1H), 7.55-7.47 (m, 1H), 6.91-6.85 (m, 1H), 6.83-6.77 (m, 1H), 6.12-6.04 (m, 1H), 4.22-4.16 (m, 2H), 3.68-3.61 (m, 2H), 2.97-2.89 (m, 2H), 2.53-2.47 (m, 2H), 2.47-2.42 (m, 2H), 2.41-2.36 (m, 2H), 2.29-2.24 (m, 3H), 1.08-1.02 (m, 6H); LCMS [M+H]+ 616.5.

Example 643: N-[4-fluoro-5-[1-(1,3-oxazol-2-yl)-3,6-dihydro-2H-pyridin-5-yl]-2-[(3R,5S)-3,4,5-trimethylpiperazin-1-yl]phenyl]-6-oxo-4-(trifluoromethyl)-1H-pyridine-3-carboxamide

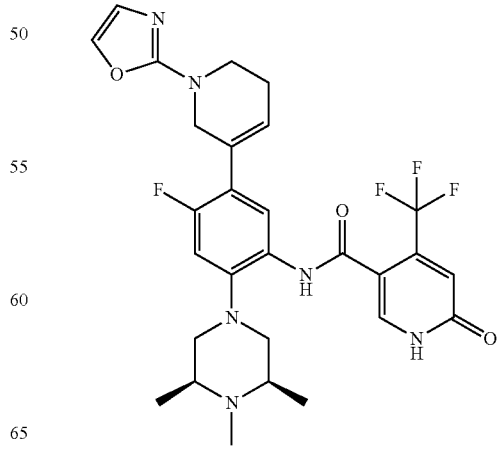

A procedure similar to Example 270 using N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol), 2-iodooxazole (9.60 mg, 0.049 mmol) afforded the title compound (6 mg, 20% yield). $^1$H NMR (500 MHz, METHANOL-d4) δ=7.88-7.82 (m, 1H), 7.71-7.64 (m, 1H), 7.35-7.28 (m, 1H), 6.89-6.83 (m, 1H), 6.80-6.77 (m, 1H), 6.77-6.70 (m, 1H), 6.07-6.01 (m, 1H), 4.23-4.15 (m, 2H), 3.62-3.55 (m, 2H), 2.96-2.88 (m, 2H), 2.52-2.46 (m, 2H), 2.45-2.39 (m, 2H), 2.37-2.30 (m, 2H), 2.28-2.25 (m, 3H), 1.06-1.03 (m, 6H); LCMS [M+H]+ 575.5

Example 644: 4-(difluoromethyl)-N-[4-fluoro-5-(1-pyrimidin-2-yl-3,6-dihydro-2H-pyridin-5-yl)-2-[(3R,5S)-3,4,5-trimethylpiperazin-1-yl]phenyl]-6-oxo-1H-pyridine-3-carboxamide Example 645: 4-(difluoromethyl)-N-[4-fluoro-5-[1-(5-methoxypyrimidin-2-yl)-3,6-dihydro-2H-pyridin-5-yl]-2-[(3R,5S)-3,4,5-trimethylpiperazin-1-yl]phenyl]-6-oxo-1H-pyridine-3-carboxamide

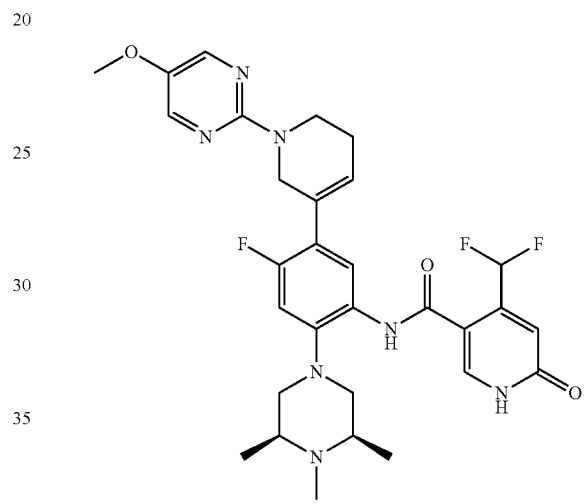

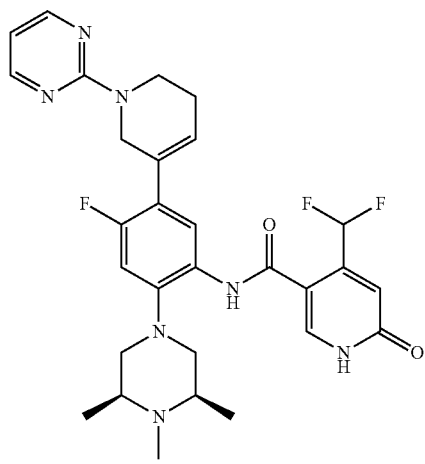 [SMILES: C[C@@H]1CN(c2cc(F)c(C3=CCCN(c4ncccn4)C3)cc2NC(=O)c2c[nH]c(=O)cc2C(F)F)C[C@H](C)N1C]

A procedure similar to Example 270 using 4-(difluoromethyl)-N-(4-fluoro-5-(1,2,5,6-tetrahydropyridin-3-yl)-2-((3S,5R)-3,4,5-trimethylpiperazin-1-yl)phenyl)-6-oxo-1,6-dihydropyridine-3-carboxamide (30 mg, 0.061 mmol) and 2-bromopyrimidine 95% (12.18 mg, 0.077 mmol) afforded the title compound (29 mg, 79% yield). $^1$H NMR (500 MHz, METHANOL-d4) δ=8.28-8.18 (m, 2H), 7.94-7.86 (m, 1H), 7.63-7.55 (m, 1H), 7.35-7.08 (m, 1H), 6.89-6.81 (m, 1H), 6.74-6.68 (m, 1H), 6.52-6.46 (m, 1H), 6.09-6.00 (m, 1H), 4.45-4.39 (m, 2H), 3.91-3.85 (m, 2H), 2.97-2.91 (m, 2H), 2.52-2.44 (m, 2H), 2.43-2.37 (m, 2H), 2.33-2.28 (m, 2H), 2.26-2.23 (m, 3H), 1.06-1.02 (m, 6H); LCMS [M+H]+ 568.6.

A procedure similar to that of Example 270 using 4-(difluoromethyl)-N-(4-fluoro-5-(1,2,5,6-tetrahydropyridin-3-yl)-2-((3S,5R)-3,4,5-trimethylpiperazin-1-yl)phenyl)-6-oxo-1,6-dihydropyridine-3-carboxamide (30 mg, 0.061 mmol) and 2-bromo-5-methoxypyrimidine (16.22 mg, 0.086 mmol) afforded the title compound (24 mg, 62% yield). $^1$H NMR (500 MHz, METHANOL-d4) δ=8.11-7.99 (m, 2H), 7.94-7.84 (m, 1H), 7.62-7.53 (m, 1H), 7.34-7.07 (m, 1H), 6.88-6.80 (m, 1H), 6.72-6.66 (m, 1H), 6.06-5.96 (m, 1H), 4.39-4.29 (m, 2H), 3.83-3.79 (m, 2H), 3.77-3.67 (m, 3H), 2.97-2.91 (m, 2H), 2.51-2.44 (m, 2H), 2.43-2.36 (m, 2H), 2.31-2.26 (m, 2H), 2.26-2.23 (m, 3H), 1.06-1.03 (m, 6H); LCMS [M+H]+ 598.5.

Example 646: 4-(difluoromethyl)-N-[4-fluoro-5-[1-(5-formylpyrimidin-2-yl)-3,6-dihydro-2H-pyridin-4-yl]-2-[(3R,5S)-3,4,5-trimethylpiperazin-1-yl]phenyl]-6-oxo-1H-pyridine-3-carboxamide

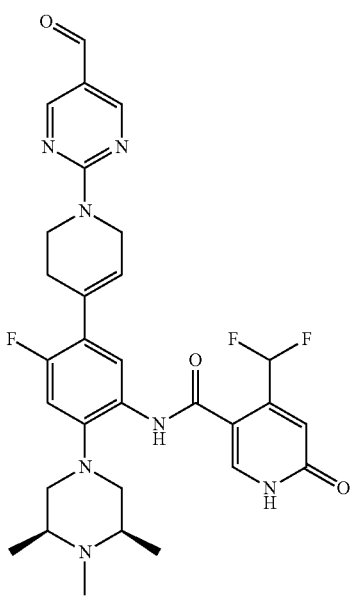 [SMILES: C[C@@H]1CN(c2cc(F)c(C3=CCN(c4ncc(C=O)cn4)CC3)cc2NC(=O)c2c[nH]c(=O)cc2C(F)F)C[C@H](C)N1C]

The procedure followed was similar to that of Example 270 using 4-(difluoromethyl)-N-(4-fluoro-5-(1,2,3,6-tetrahydropyridin-4-yl)-2-((3S,5R)-3,4,5-trimethylpiperazin-1-yl)phenyl)-6-oxo-1,6-dihydropyridine-3-carboxamide (40 mg, 0.082 mmol) and 2-bromo-pyrimidine-5-carbaldehyde (19.86 mg, 0.106 mmol) to afford the title compound (32.5 mg, 63% yield). $^1$H NMR (500 MHz, METHANOL-d4) δ=9.70-9.54 (m, 1H), 8.75-8.61 (m, 2H), 7.93-7.82 (m, 1H), 7.63-7.55 (m, 1H), 7.33-7.06 (m, 1H), 6.88-6.77 (m, 1H), 6.73-6.64 (m, 1H), 6.04-5.92 (m, 1H), 4.49-4.37 (m, 2H), 4.14-4.03 (m, 2H), 2.96-2.88 (m, 2H), 2.54-2.49 (m, 2H), 2.49-2.43 (m, 2H), 2.43-2.36 (m, 2H), 2.27-2.22 (m, 3H), 1.03 (d, J=6.1 Hz, 6H); LCMS [M+H]+ 596.5.

Example 647: 4-(difluoromethyl)-N-[4-fluoro-5-[1-(6-methoxypyrimidin-4-yl)-3,6-dihydro-2H-pyridin-4-yl]-2-[(3R,5S)-3,4,5-trimethylpiperazin-1-yl]phenyl]-6-oxo-1H-pyridine-3-carboxamide

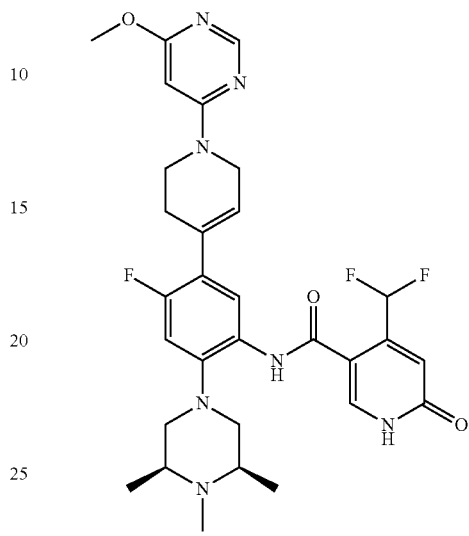

A procedure similar to Example 270 using 4-(difluoromethyl)-N-(4-fluoro-5-(1,2,3,6-tetrahydropyridin-4-yl)-2-((3S,5R)-3,4,5-trimethylpiperazin-1-yl)phenyl)-6-oxo-1,6-dihydropyridine-3-carboxamide (30 mg, 0.061 mmol) and 4-iodo-6-methoxypyrimidine (18.80 mg, 0.080 mmol) gave the title compound (28 mg, 73% yield). $^1$H NMR (500 MHz, METHANOL-d4) δ=8.15-8.06 (m, 1H), 7.92-7.85 (m, 1H), 7.64-7.55 (m, 1H), 7.32-7.07 (m, 1H), 6.82 (d, J=12.5 Hz, 1H), 6.72-6.66 (m, 1H), 6.04-5.96 (m, 1H), 5.94-5.87 (m, 1H), 4.11-4.00 (m, 2H), 3.84-3.74 (m, 5H), 2.95-2.89 (m, 2H), 2.53-2.43 (m, 4H), 2.43-2.36 (m, 2H), 2.25 (s, 3H), 1.04 (d, J=6.0 Hz, 6H); LCMS [M+H]+ 598.5.

Example 648: Ethyl 5-[5-[[4-(difluoromethyl)-6-oxo-1H-pyridine-3-carbonyl]amino]-2-fluoro-4-[(3R,5S)-3,4,5-trimethylpiperazin-1-yl]phenyl]-3,6-dihydro-2H-pyridine-1-carboxylate

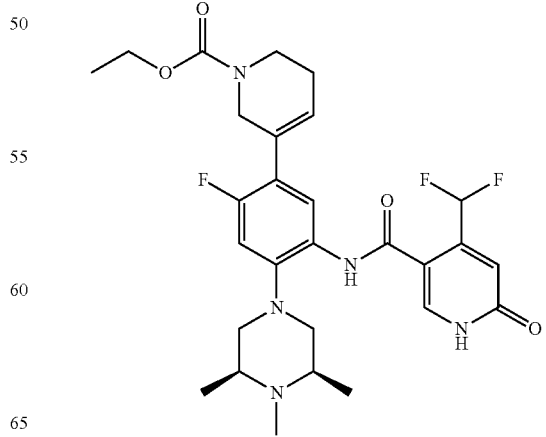

799

The procedure followed was similar to Example 253 using 4-(difluoromethyl)-N-(4-fluoro-5-(1,2,5,6-tetrahydropyridin-3-yl)-2-((3S,5R)-3,4,5-trimethylpiperazin-1-yl)phenyl)-6-oxo-1,6-dihydropyridine-3-carboxamide (30 mg, 0.061 mmol) and ethyl chloroformate (5.83 μl, 0.061 mmol) to give the title compound (29 mg, 80% yield). $^1$H NMR (500 MHz, METHANOL-d4) δ=7.93-7.83 (m, 1H), 7.60-7.50 (m, 1H), 7.34-7.06 (m, 1H), 6.88-6.78 (m, 1H), 6.73-6.63 (m, 1H), 6.03-5.92 (m, 1H), 4.21-4.10 (m, 2H), 4.09-4.01 (m, 2H), 3.57-3.45 (m, 2H), 2.96-2.88 (m, 2H), 2.50-2.43 (m, 2H), 2.43-2.36 (m, 2H), 2.27-2.20 (m, 5H), 1.21-1.16 (m, 3H), 1.07-1.01 (m, 6H); LCMS [M+H]+ 562.5.

Example 649: 4-fluoro-N-[4-fluoro-5-(1-pyrimidin-2-yl-3,6-dihydro-2H-pyridin-5-yl)-2-[(3R)-3,4-dimethylpiperazin-1-yl]phenyl]-2-(trifluoromethyl)benzamide Example 650: 4-fluoro-N-[4-fluoro-5-[1-(5-formylpyrimidin-2-yl)-3,6-dihydro-2H-pyridin-5-yl]-2-[(3R)-3,4-dimethylpiperazin-1-yl]phenyl]-2-(trifluoromethyl)benzamide

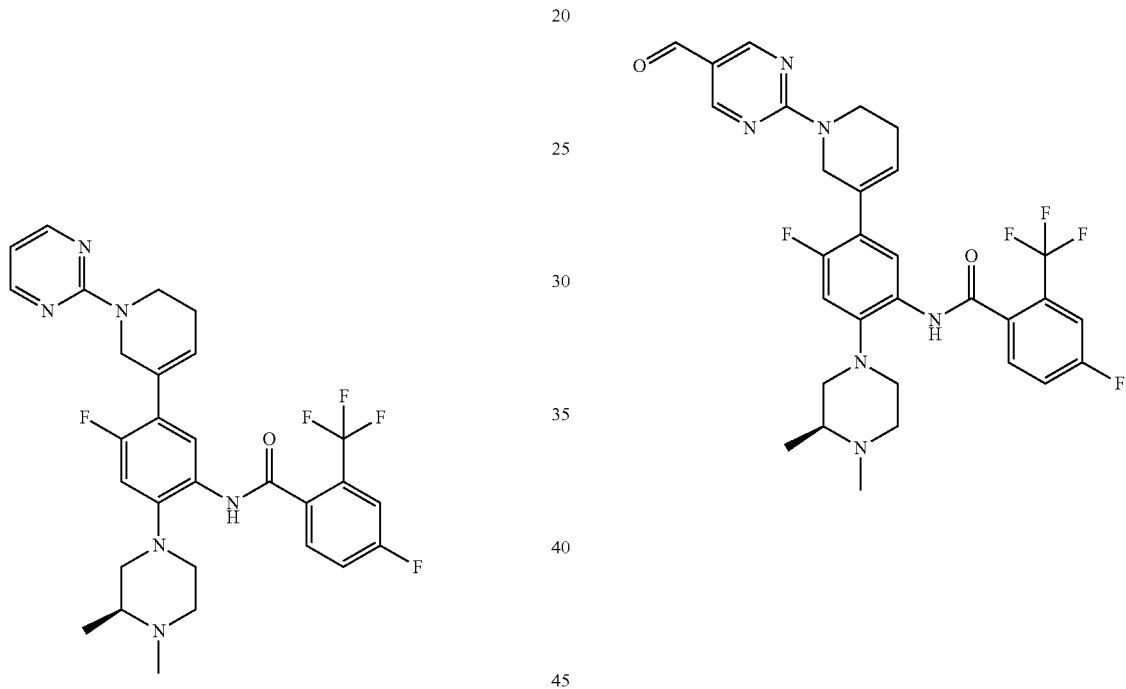

The procedure followed was similar to that of Example 270 using (S)—N-(2-(3,4-dimethylpiperazin-1-yl)-4-fluoro-5-(1,2,5,6-tetrahydropyridin-3-yl)phenyl)-4-fluoro-2-(trifluoromethyl)benzamide (30 mg, 0.061 mmol) and 2-bromopyrimidine 95% (12.06 mg, 0.076 mmol) to afford the title compound (26 mg, 71% yield). $^1$H NMR (500 MHz, METHANOL-d4) δ=8.41-8.30 (m, 2H), 7.97-7.89 (m, 1H), 7.82-7.74 (m, 1H), 7.69-7.62 (m, 1H), 7.60-7.51 (m, 1H), 7.07-6.96 (m, 1H), 6.61 (t, J=4.8 Hz, 1H), 6.21-6.10 (m, 1H), 4.63-4.49 (m, 2H), 4.07-3.96 (m, 2H), 3.13-3.01 (m, 2H), 2.97-2.86 (m, 2H), 2.60-2.51 (m, 1H), 2.50-2.44 (m, 1H), 2.44-2.40 (m, 2H), 2.37-2.29 (m, 4H), 1.12 (d, J=6.2 Hz, 3H); LCMS [M+H]+ 573.5.

The procedure followed was similar to Example 270 using (S)—N-(2-(3,4-dimethylpiperazin-1-yl)-4-fluoro-5-(1,2,5,6-tetrahydropyridin-3-yl)phenyl)-4-fluoro-2-(trifluoromethyl)benzamide (35 mg, 0.071 mmol) and 2-bromopyrimidine-5-carbaldehyde (17.21 mg, 0.092 mmol) to give the title compound (33 mg, 74% yield). $^1$H NMR (500 MHz, METHANOL-d4) δ=9.80-9.73 (m, 1H), 8.87-8.76 (m, 2H), 7.98-7.89 (m, 1H), 7.81-7.74 (m, 1H), 7.69-7.62 (m, 1H), 7.60-7.53 (m, 1H), 7.08-6.98 (m, 1H), 6.23-6.16 (m, 1H), 4.78-4.72 (m, 2H), 4.23-4.15 (m, 2H), 3.13-3.00 (m, 2H), 2.98-2.88 (m, 2H), 2.60-2.51 (m, 1H), 2.50-2.42 (m, 3H), 2.37-2.31 (m, 4H), 1.14-1.10 (m, 3H); LCMS [M+H]+ 601.5.

801

Example 651: (1-methylcyclobutyl) 4-[5-[[4-(difluoromethyl)-6-oxo-1H-pyridine-3-carbonyl]amino]-2-fluoro-4-[(3R 5S)-3,4,5-trimethylpiperazin-1-yl]phenyl]-3,6-dihydro-2H-pyridine-1-carboxylate

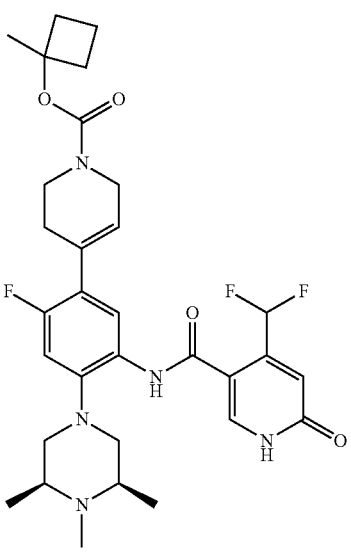 [SMILES: C[C@@H]1CN(c2cc(F)c(C3=CCN(C(=O)OC4(C)CCC4)CC3)cc2NC(=O)c2c[nH]c(=O)cc2C(F)F)C[C@H](C)N1C]

The procedure followed was similar to Example 253 using 4-(difluoromethyl)-N-(4-fluoro-5-(1,2,3,6-tetrahydropyridin-4-yl)-2-((3S,5R)-3,4,5-trimethylpiperazin-1-yl)phenyl)-6-oxo-1,6-dihydropyridine-3-carboxamide (25 mg, 0.051 mmol) and 1-methylcyclobutyl (4-nitrophenyl) carbonate (22 mg, 0.070 mmol) to give the title compound (16.5 mg, 37% yield). $^1$H NMR (500 MHz, METHANOL-d4) δ=7.92-7.85 (m, 1H), 7.59-7.52 (m, 1H), 7.32-7.06 (m, 1H), 6.87-6.77 (m, 1H), 6.72-6.67 (m, 1H), 5.93-5.80 (m, 1H), 4.06-3.89 (m, 2H), 3.61-3.46 (m, 2H), 3.21 (td, J=1.6, 3.2 Hz, 8H), 2.96-2.87 (m, 2H), 2.50-2.43 (m, 2H), 2.42-2.36 (m, 4H), 2.30-2.22 (m, 5H), 2.08-1.99 (m, 2H), 1.79-1.68 (m, 1H), 1.65-1.55 (m, 1H), 1.51-1.41 (m, 3H), 1.06-1.02 (m, 6H); LCMS [M+H]+ 602.6.

802

Example 652: N-[5-(4-carbamoyl-3-fluorophenyl)-4-fluoro-2-[(3R)-3,4-dimethylpiperazin-1-yl]phenyl]-4-(difluoromethyl)-1-methyl-6-oxopyridine-3-carboxamide

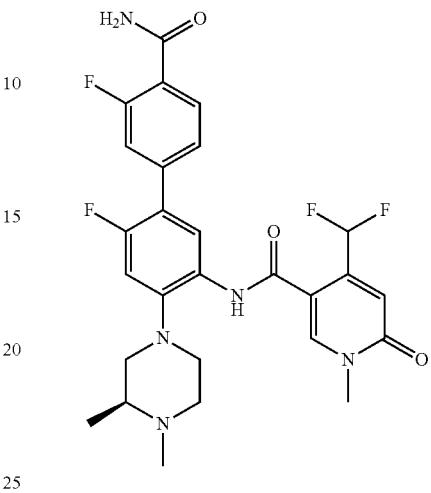

The procedure followed was similar to Example 100 using 4-carbamoyl-3-fluorophenylboronic acid, 96% (22.52 mg, 0.123 mmol) and (S)—N-(5-bromo-2-(3,4-dimethylpiperazin-1-yl)-4-fluorophenyl)-4-(difluoromethyl)-1-methyl-6-oxo-1,6-dihydropyridine-3-carboxamide (40 mg, 0.082 mmol, from Example 461 Step 1) to afford the title compound as a white fluffy powder (8.4 mg, 17.8% yield). $^1$H NMR (500 MHz, METHANOL-d4) δ=8.23 (s, 1H), 7.81 (t, J=8.0 Hz, 1H), 7.74 (d, J=8.2 Hz, 1H), 7.39 (d, J=8.1 Hz, 1H), 7.34 (d, J=12.3 Hz, 1H), 7.30-7.07 (m, 1H), 7.03 (d, J=12.2 Hz, 1H), 6.74-6.67 (m, 1H), 3.55 (s, 3H), 3.17-3.09 (m, 3H), 2.98-2.90 (m, 1H), 2.83-2.74 (m, 2H), 2.68-2.60 (m, 1H), 2.53 (s, 3H), 1.15 (d, J=6.4 Hz, 3H); LCMS [M+H]+ 546.

Example 653: 4-(difluoromethyl)-N-[4-fluoro-5-[3-fluoro-4-(methylcarbamoyl)phenyl]-2-[(3R)-3,4-dimethylpiperazin-1-yl]phenyl]-1-methyl-6-oxopyridine-3-carboxamide

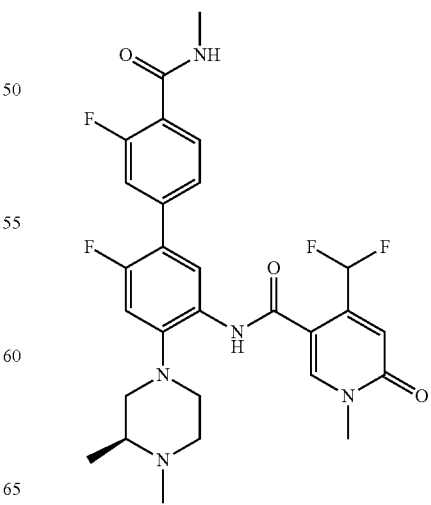

The procedure followed was similar to that of Example 100 using 3-fluoro-4-(methylcarbamoyl)phenylboronic acid (24.25 mg, 0.123 mmol) and (S)—N-(5-bromo-2-(3,4-dimethylpiperazin-1-yl)-4-fluorophenyl)-4-(difluoromethyl)-1-methyl-6-oxo-1,6-dihydropyridine-3-carboxamide (40 mg, 0.082 mmol). The title compound was isolated as a beige fluffy powder (34.8 mg, 72.0% yield). $^1$H NMR (500 MHz, METHANOL-d4) δ=8.19 (s, 1H), 7.75 (d, J=8.3 Hz, 1H), 7.72 (t, J=7.9 Hz, 1H), 7.38 (d, J=8.1 Hz, 1H), 7.32 (d, J=12.2 Hz, 1H), 7.30-7.06 (m, 1H), 6.98 (d, J=12.3 Hz, 1H), 6.73-6.69 (m, 1H), 3.55 (s, 3H), 3.05 (br dd, J=2.0, 11.5 Hz, 1H), 3.00 (dd, J=2.3, 11.7 Hz, 1H), 2.88-2.79 (m, 5H), 2.56 (s, 1H), 2.49-2.38 (m, 2H), 2.33-2.27 (m, 1H), 2.26 (s, 3H), 1.02 (d, J=6.4 Hz, 3H); LCMS [M+H]$^+$ 560.

Example 654: 2-(difluoromethyl)-4-fluoro-N-[4-fluoro-5-(2-morpholin-4-ylpyrimidin-5-yl)-2-[(3R)-3,4-dimethylpiperazin-1-yl]phenyl]benzamide

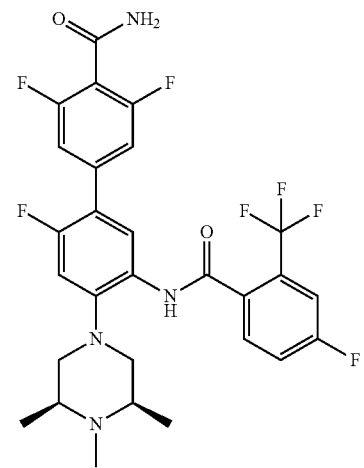 [SMILES: C[C@@H]1CN(c2cc(F)c(-c3cc(F)c(C(N)=O)c(F)c3)cc2NC(=O)c2ccc(F)cc2C(F)(F)F)C[C@H](C)N1C]

The title compound (formic acid salt, light brown solid, 48.2 mg, 39%) was prepared in a manner similar to the sequence described above for the preparation of Example 331 using (S)-2-(3,4-dimethylpiperazin-1-yl)-4-fluoro-5-(2-morpholinopyrimidin-5-yl)aniline (77 mg, 0.2 mmol) and 2-(difluoromethyl)-4-fluorobenzoic acid (prepared as described in Angew. Chem. Int. Ed. 2014, 53, 5955-5958). $^1$H NMR (500 MHz, METHANOL-d4) δ=8.55 (s, 2H), 8.36 (s, 1H), 7.95 (br d, J=8.1 Hz, 1H), 7.88 (br dd, J=5.4, 8.0 Hz, 1H), 7.54 (dd, J=2.4, 9.2 Hz, 1H), 7.48-7.23 (m, 2H), 7.17 (d, J=12.0 Hz, 1H), 3.87-3.81 (m, 4H), 3.79-3.72 (m, 4H), 3.39 (br d, J=10.8 Hz, 1H), 3.30-3.23 (m, 2H), 3.17-3.03 (m, 3H), 2.86 (br dd, J=10.1, 12.6 Hz, 1H), 2.76 (s, 3H), 1.31 (d, J=6.5 Hz, 3H); LCMS [M+H]$^+$ 559.4.

Example 655: 2-(difluoromethyl)-4-fluoro-N-[4-fluoro-5-(2-morpholin-4-ylpyrimidin-4-yl)-2-[(3R)-3,4-dimethylpiperazin-1-yl]phenyl]benzamide

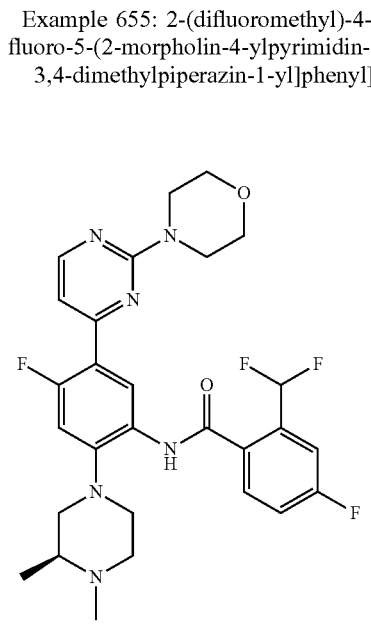

The title compound (formic acid salt, light brown solid, 34.3 mg, 28%) was prepared in a manner similar to the procedure described for the preparation of Example 331 using (S)-2-(3,4-dimethylpiperazin-1-yl)-4-fluoro-5-(2-morpholinopyrimidin-4-yl)aniline (84 mg, 91.6% purity, 0.2 mmol) and 2-(difluoromethyl)-4-fluorobenzoic acid. $^1$H NMR (500 MHz, METHANOL-d4) δ=8.57 (br d, J=7.9 Hz, 1H), 8.38 (d, J=5.3 Hz, 1H), 8.33 (br s, 1H), 7.92-7.81 (m, 1H), 7.54 (dd, J=2.3, 9.3 Hz, 1H), 7.48-7.22 (m, 2H), 7.16-7.07 (m, 2H), 3.89-3.80 (m, 4H), 3.80-3.71 (m, 4H), 3.40-3.32 (m, 3H), 3.18-3.01 (m, 3H), 2.86 (br dd, J=10.2, 12.5 Hz, 1H), 2.75 (s, 3H), 1.30 (d, J=6.4 Hz, 3H); LCMS [M+H]$^+$ 559.3.

Example 656: 2,6-difluoro-4-[2-fluoro-5-[[4-fluoro-2-(trifluoromethyl)benzoyl]amino]-4-[(3R,5S)-3,4,5-trimethylpiperazin-1-yl]phenyl]benzamide A coupling procedure similar to that in Example 100 using 4-(aminocarbonyl)-3,5-difluorophenylboronic acid (23.81 mg, 0.119 mmol) and N-(5-bromo-4-fluoro-2-((3S, 5R)-3,4,5-trimethylpiperazin-1-yl)phenyl)-4-fluoro-2-(trifluoromethyl)benzamide (40 mg, 0.079 mmol) afforded the title compound as a beige fluffy powder (25 mg, 0.041 mmol, 51.6% yield). $^1$H NMR (500 MHz, METHANOL-d4) δ=7.94 (d, J=8.2 Hz, 1H), 7.66 (dd, J=5.3, 8.4 Hz, 1H), 7.55 (dd, J=2.3, 9.0 Hz, 1H), 7.46 (dt, J=2.3, 8.3 Hz, 1H), 7.18 (d, J=8.6 Hz, 2H), 7.03-6.96 (m, 1H), 2.99 (br d, J=11.4 Hz, 2H), 2.52 (t, J=11.2 Hz, 2H), 2.40-2.30 (m, 2H), 2.22 (s, 3H), 1.05 (d, J=6.2 Hz, 6H); LCMS [M+H]$^+$ 583.

Example 657: 2,6-difluoro-4-[2-fluoro-5-[[4-fluoro-2-(trifluoromethyl)benzoyl]amino]-4-[(3R)-3,4-dimethylpiperazin-1-yl]phenyl]benzamide

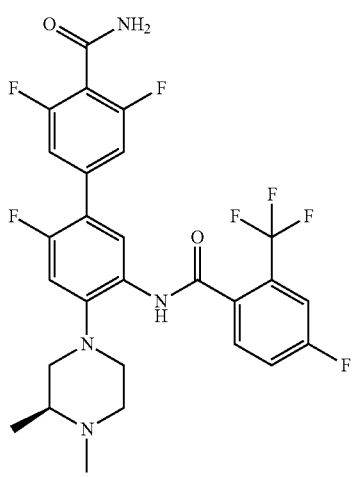 [SMILES: C[C@H]1CN(c2cc(F)c(-c3cc(F)c(C(N)=O)c(F)c3)cc2NC(=O)c2ccc(F)cc2C(F)(F)F)CCN1C]

A procedure followed similar to that of Example 100 using (S)—N-(5-bromo-2-(3,4-dimethylpiperazin-1-yl)-4-fluorophenyl)-4-fluoro-2-(trifluoromethyl)benzamide (40 mg, 0.081 mmol) and 4-(aminocarbonyl)-3,5-difluorophenylboronic acid (24.49 mg, 0.122 mmol) gave the title compound as a light yellow fluffy powder (31 mg, 0.052 mmol, 63.8% yield). $^1$H NMR (500 MHz, METHANOL-d4) δ=7.94 (d, J=8.2 Hz, 1H), 7.68 (dd, J=5.3, 8.4 Hz, 1H), 7.55 (dd, J=2.4, 9.0 Hz, 1H), 7.46 (dt, J=2.4, 8.3 Hz, 1H), 7.18 (d, J=8.6 Hz, 2H), 7.02 (d, J=12.3 Hz, 1H), 3.05 (br dd, J=2.2, 11.5 Hz, 1H), 3.01-2.96 (m, 1H), 2.87-2.83 (m, 1H), 2.83-2.77 (m, 1H), 2.47 (t, J=10.9 Hz, 1H), 2.37 (dt, J=2.8, 11.2 Hz, 1H), 2.23 (s, 3H), 1.01 (d, J=6.4 Hz, 3H); LCMS [M+H]$^+$ 569.

Example 658: N-[5-(4-carbamoyl-3,5-difluorophenyl)-4-fluoro-2-[(3R,5S)-3,4,5-trimethylpiperazin-1-yl]phenyl]-6-oxo-4-(trifluoromethyl)-1H-pyridine-3-carboxamide

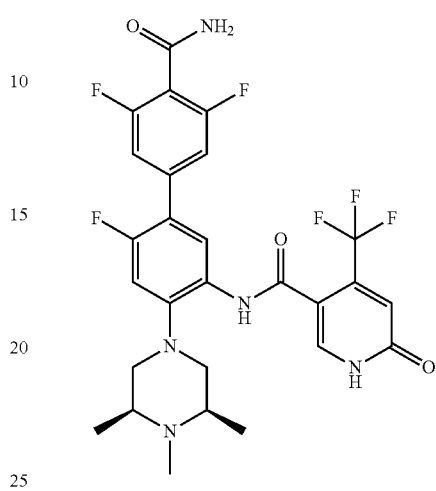

A procedure similar to that of Example 100 using 4-(aminocarbonyl)-3,5-difluorophenylboronic acid (19.91 mg, 0.099 mmol) and N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (40 mg, 0.066 mmol) afforded the title compound (TFA salt) as an off-white fluffy powder (34 mg, 0.040 mmol, 85% yield). $^1$H NMR (500 MHz, METHANOL-d4) δ=7.92 (s, 1H), 7.86 (d, J=8.2 Hz, 1H), 7.17 (d, J=8.6 Hz, 2H), 7.08 (d, J=12.0 Hz, 1H), 6.85-6.81 (m, 1H), 3.46-3.36 (m, 2H), 3.30 (br d, J=13.2 Hz, 2H), 2.89 (s, 3H), 2.88-2.81 (m, 2H), 1.34 (d, J=6.4 Hz, 6H); LCMS [M+H]$^+$ 582.

Example 659: N-[5-(4-carbamoyl-3,5-difluorophenyl)-4-fluoro-2-[(3R,5S)-3,4,5-trimethylpiperazin-1-yl]phenyl]-4-(difluoromethyl)-6-oxo-1H-pyridine-3-carboxamide

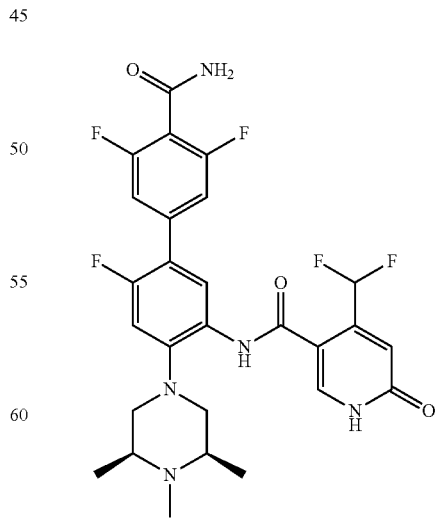

A procedure similar to that of Example 100 using N-(5-bromo-4-fluoro-2-((3S,5R)-3,4,5-trimethylpiperazin-1-yl)

phenyl)-4-(difluoromethyl)-6-(2-(trimethylsilyl)ethoxy) nicotinamide (40 mg, 0.068 mmol) and 4-(aminocarbonyl)-3,5-difluorophenylboronic acid (20.52 mg, 0.102 mmol) afforded the title compound (TFA salt) as an off-white fluffy powder (40 mg, 0.048 mmol, 91% yield). $^1$H NMR (500 MHz, METHANOL-d4) δ=7.97 (s, 1H), 7.71 (d, J=8.2 Hz, 1H), 7.34-7.09 (m, 3H), 7.06 (d, J=12.1 Hz, 1H), 6.72-6.67 (m, 1H), 3.43-3.35 (m, 2H), 3.32 (br d, J=13.4 Hz, 2H), 2.88 (s, 3H), 2.86-2.79 (m, 2H), 1.33 (d, J=6.5 Hz, 6H); LCMS [M+H]$^+$ 564.

Example 660: 4-fluoro-N-[4-fluoro-2-[(3R)-3,4-dimethylpiperazin-1-yl]-5-[2-[(2R)-2-methylmorpholin-4-yl]pyrimidin-4-yl]phenyl]-2-(trifluoromethyl)benzamide

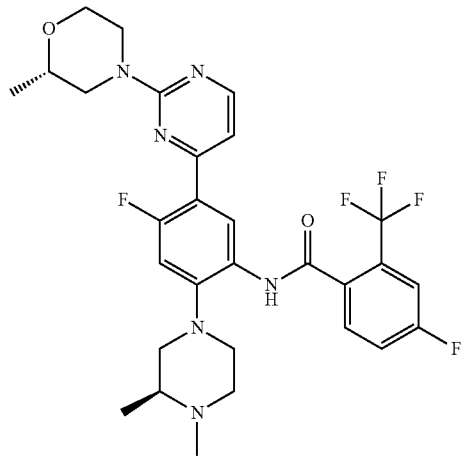 [SMILES: C[C@H]1CN(c2nccc(-c3cc(NC(=O)c4ccc(F)cc4C(F)(F)F)c(N4CCN(C)[C@@H](C)C4)cc3F)n2)CCO1]

To a 20 mL microwave vial charged with (S)—N-(5-bromo-2-(3,4-dimethylpiperazin-1-yl)-4-fluorophenyl)-4-fluoro-2-(trifluoromethyl)benzamide (572 mg, 86% purity, 1 mmol), bis(pinacolato)diboron (508 mg, 2 mmol), Pd(dppf)Cl$_2$ (37 mg, 0.05 mmol) and KOAc (294 mg, 3 mmol) was added dioxane (10 mL) and the resulting mixture was heated at 110° C. in microwave for 6 h. The crude (S)—N-(2-(3,4-dimethylpiperazin-1-yl)-4-fluoro-5-(4,4,5,5-tetramethyl-1,3,2-dioxaborolan-2-yl)phenyl)-4-fluoro-2-(trifluoromethyl)benzamide was diluted with dioxane to a total volume of 20 mL and it was divided equally into 5 portions (each 4 mL, 0.2 mmol) for reactions with various substrates. To a mixture of the above crude ((S)—N-(2-(3,4-dimethylpiperazin-1-yl)-4-fluoro-5-(4,4,5,5-tetramethyl-1,3,2-dioxaborolan-2-yl)phenyl)-4-fluoro-2-(trifluoromethyl)benzamide in dioxane (0.2 mmol assuming full conversion) and (S)-4-(4-bromopyrimidin-2-yl)-2-methylmorpholine (62 mg, 0.24 mmol) was added bis(di-tert-butyl(4-dimethylaminophenyl)phosphine)dichloropalladium(II) (14 mg, 0.02 mmol) and 1 M K$_3$PO$_4$ (0.6 mL, 0.6 mmol). The resulting mixture was heated in microwave at 110° C. for 2 h. After diluting with brine (5 mL), it was extracted with EtOAc (15 mL×2). The combined extracts were concentrated and purified by flash chromatography (gradient: EtOAc/hex 0-100% then MeOH/DCM 0-10%), prep-HPLC and Biotage SCX-2 column to give a white solid. It was redissolved in MeOH (10 mL), treated with 2 drops of HCO$_2$H, evaporated and dried to give the title compound as a pale beige solid (formic acid salt, 71.6 mg, 56% over two steps). $^1$H NMR (500 MHz, METHANOL-d4) δ=8.74 (d, J=8.3 Hz, 1H), 8.47-8.41 (m, 1H), 8.40 (d, J=5.3 Hz, 1H), 7.77 (dd, J=5.3, 8.4 Hz, 1H), 7.68 (dd, J=2.2, 9.0 Hz, 1H), 7.58 (dt, J=2.3, 8.3 Hz, 1H), 7.16 (dd, J=1.7, 5.1 Hz, 1H), 7.09 (d, J=13.1 Hz, 1H), 4.68 (br d, J=13.1 Hz, 1H), 4.61 (br d, J=13.4 Hz, 1H), 3.98 (dd, J=2.4, 11.5 Hz, 1H), 3.69-3.60 (m, 2H), 3.39-3.26 (m, 3H), 3.14-3.03 (m, 2H), 2.99-2.89 (m, 2H), 2.87-2.77 (m, 1H), 2.73 (dd, J=10.5, 13.1 Hz, 1H), 2.69-2.65 (m, 3H), 1.30 (d, J=6.4 Hz, 3H), 1.25 (d, J=6.2 Hz, 3H); LCMS [M+H]$^+$ 591.3.

Example 661: N-[4-fluoro-5-[2-(4-propan-2-ylpiperazin-1-yl)pyrimidin-5-yl]-2-[(3R,5S)-3,4,5-trimethylpiperazin-1-yl]phenyl]-1-methyl-6-oxo-4-(trifluoromethyl)pyridine-3-carboxamide

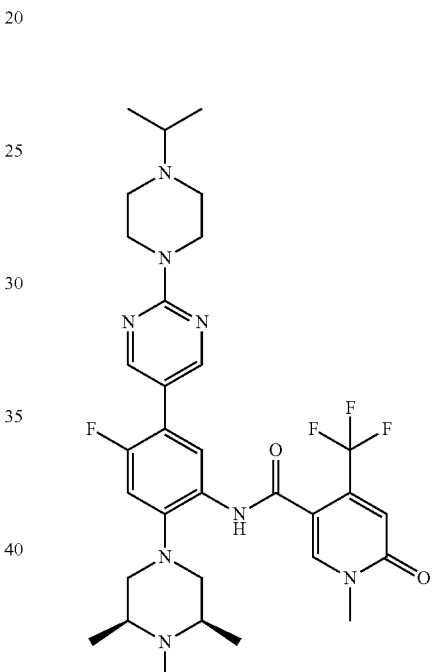

The title compound (di-formic acid salt, light beige solid, 42.4 mg, 57%) was prepared according to a procedure similar to Example 31 using crude (2-(4-isopropylpiperazin-1-yl)pyrimidin-5-yl)boronic acid (0.3 mmol) and N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (52 mg, 0.1 mmol). $^1$H NMR (500 MHz, METHANOL-d4) δ=8.61 (s, 2H), 8.50 (br s, 1H), 8.46 (br s, 1H), 8.28 (br s, 1H), 7.94 (d, J=8.2 Hz, 1H), 7.16 (br d, J=11.9 Hz, 1H), 6.96 (s, 1H), 4.12 (br s, 4H), 3.67 (s, 3H), 3.17 (br s, 6H), 3.06-2.89 (m, 2H), 2.79 (br d, J=11.5 Hz, 2H), 2.65-2.57 (m, 3H), 1.34 (d, J=6.6 Hz, 6H), 1.31-1.26 (m, 6H); LCMS [M+H]$^+$ 645.4.

Example 662: N-[5-[2-(2,2-dimethylmorpholin-4-yl)pyrimidin-5-yl]-4-fluoro-2-[(3R,5S)-3,4,5-trimethylpiperazin-1-yl]phenyl]-1-methyl-6-oxo-4-(trifluoromethyl)pyridine-3-carboxamide

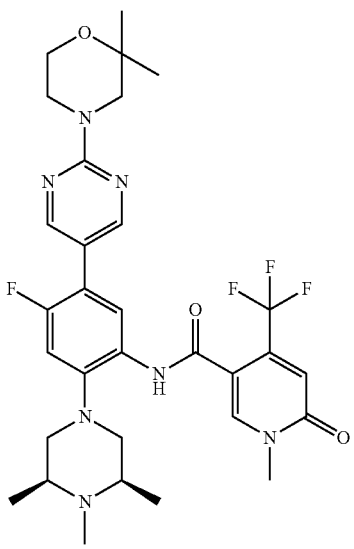 [SMILES: C[C@@H]1CN(c2cc(F)c(-c3cnc(N4CCOC(C)(C)C4)nc3)cc2NC(=O)c2cn(C)c(=O)cc2C(F)(F)F)C[C@H](C)N1C]

The title compound (formic acid salt, light beige solid, 32.9 mg, 48%) was prepared according to a procedure similar to Example 31 using crude (2-(2,2-dimethylmorpholino)pyrimidin-5-yl)boronic acid (0.3 mmol) and N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (52 mg, 0.1 mmol). $^1$H NMR (500 MHz, METHANOL-d4) δ=8.58-8.53 (m, 2H), 8.45 (br s, 1H), 8.29 (s, 1H), 7.92 (d, J=8.3 Hz, 1H), 7.16 (d, J=11.9 Hz, 1H), 6.96 (s, 1H), 3.89-3.80 (m, 4H), 3.74 (s, 2H), 3.67 (s, 3H), 3.20 (br d, J=12.0 Hz, 2H), 3.00 (br s, 2H), 2.85-2.74 (m, 2H), 2.65 (s, 3H), 1.30 (d, J=6.4 Hz, 6H), 1.27 (s, 6H); LCMS [M+H]$^+$ 632.4.

Example 663: N-[4-fluoro-5-(2-morpholin-4-ylpyrimidin-4-yl)-2-[(3R)-3,4-dimethylpiperazin-1-yl]phenyl]-1-methyl-6-oxo-4-(trifluoromethyl)pyridine-3-carboxamide

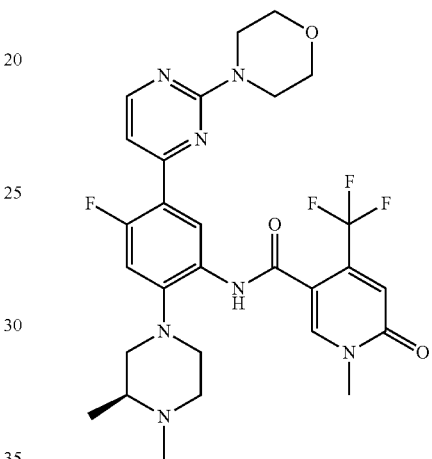

A mixture of 1-methyl-6-oxo-4-(trifluoromethyl)-1,6-dihydropyridine-3-carboxylic acid (44 mg, 0.2 mmol), HATU (76 g, 0.2 mmol) and N,N-diisopropylethylamine (0.052 ml, 0.3 mmol) in DMF (2 mL) was heated at 60° C. for 5 min to afford a clear colorless solution before (S)-2-(3,4-dimethylpiperazin-1-yl)-4-fluoro-5-(2-morpholinopyrimidin-4-yl)aniline (39 mg, 0.1 mmol) was added in one portion. The resulting mixture was heated at 60° C. overnight. Solvents were removed and the residue was purified by prep-HPLC and Biotage SCX-2 column to give the title compound as a light brown solid (34.8 mg, 58%). $^1$H NMR (500 MHz, METHANOL-d4) δ=8.60 (d, J=8.2 Hz, 1H), 8.39 (d, J=5.3 Hz, 1H), 8.25 (s, 1H), 7.15 (dd, J=1.8, 5.1 Hz, 1H), 7.05 (d, J=13.2 Hz, 1H), 6.96 (s, 1H), 3.89-3.84 (m, 4H), 3.80-3.76 (m, 4H), 3.66 (s, 3H), 3.24-3.13 (m, 2H), 3.01-2.91 (m, 2H), 2.64-2.51 (m, 2H), 2.43 (br s, 1H), 2.38 (s, 3H), 1.14 (d, J=6.2 Hz, 3H); LCMS [M+H]$^+$ 590.4.

Example 664: 4-(difluoromethyl)-N-[4-fluoro-5-(2-morpholin-4-ylpyrimidin-4-yl)-2-[(3R)-3,4-dimethylpiperazin-1-yl]phenyl]-1-methyl-6-oxopyridine-3-carboxamide

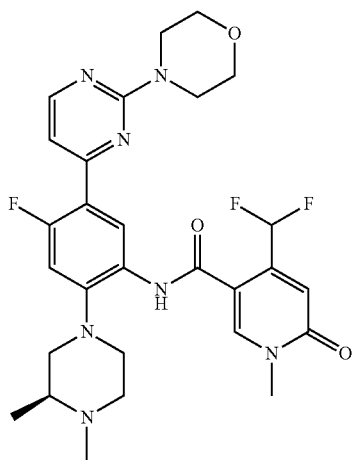

A mixture of 4-(difluoromethyl)-1-methyl-6-oxo-1,6-dihydropyridine-3-carboxylic acid (41 mg, 0.2 mmol), HATU (76 g, 0.2 mmol) and N,N-diisopropylethylamine (0.052 ml, 0.3 mmol) in DMF (2 mL) was heated at 60° C. for 5 min to afford a clear colorless solution before (S)-2-(3,4-dimethylpiperazin-1-yl)-4-fluoro-5-(2-morpholinopyrimidin-4-yl)aniline (39 mg, 0.1 mmol) was added in one portion. The resulting mixture was heated at 60° C. overnight. Solvents were removed and the residue was purified by prep-HPLC and Biotage SCX-2 column to give the title compound as a brown solid (25.2 mg, 43%). $^1$H NMR (500 MHz, METHANOL-d4) δ=8.43 (d, J=8.2 Hz, 1H), 8.40-8.37 (m, 1H), 8.31 (s, 1H), 7.28 (t, J=55.0 Hz, 1H), 7.13 (dd, J=1.7, 5.0 Hz, 1H), 7.03 (d, J=13.2 Hz, 1H), 6.82 (s, 1H), 3.88-3.83 (m, 4H), 3.79-3.73 (m, 4H), 3.64 (s, 3H), 3.26-3.13 (m, 2H), 3.01-2.90 (m, 2H), 2.62-2.50 (m, 2H), 2.46-2.35 (m, 4H), 1.13 (d, J=6.2 Hz, 3H); LCMS [M+H]$^+$ 572.4.

Example 665: 2,3-difluoro-4-[2-fluoro-5-[[4-fluoro-2-(trifluoromethyl)benzoyl]amino]-4-[(3R,5S)-3,4,5-trimethylpiperazin-1-yl]phenyl]-N-(2,4,4-trimethylpentan-2-yl)benzamide

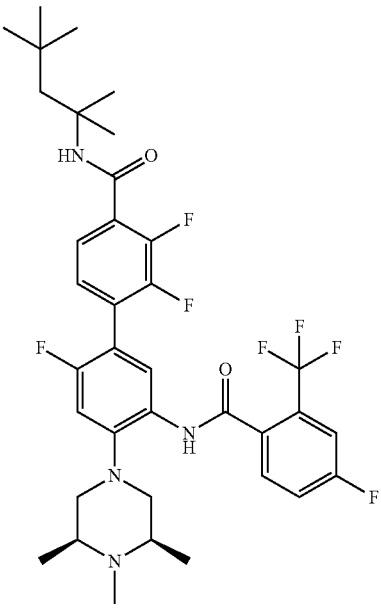 [SMILES: C[C@@H]1CN(c2cc(F)c(-c3ccc(C(=O)NC(C)(C)CC(C)(C)C)c(F)c3F)cc2NC(=O)c2ccc(F)cc2C(F)(F)F)C[C@H](C)N1C]

A coupling procedure similar to Example 100 using 2,3-difluoro-4-(4,4,5,5-tetramethyl-1,3,2-dioxaborolan-2-yl)-N-(2,4,4-trimethylpentan-2-yl)benzamide (68.4 mg, 0.173 mmol) and N-(5-bromo-4-fluoro-2-((3S,5R)-3,4,5-trimethylpiperazin-1-yl)phenyl)-4-fluoro-2-(trifluoromethyl)benzamide (51.5 mg, 0.102 mmol) afforded the title compound as an off-white fluffy powder (59 mg, 79% yield). $^1$H NMR (500 MHz, METHANOL-d4) δ=7.86 (d, J=7.7 Hz, 1H), 7.65 (dd, J=5.3, 8.4 Hz, 1H), 7.54 (dd, J=2.3, 9.0 Hz, 1H), 7.45 (dt, J=2.3, 8.3 Hz, 1H), 7.31 (br t, J=7.0 Hz, 1H), 7.22-7.17 (m, 1H), 7.02 (d, J=11.2 Hz, 1H), 3.05 (br d, J=9.7 Hz, 2H), 2.59 (br s, 4H), 2.34 (br s, 3H), 1.84 (s, 2H), 1.39 (s, 6H), 1.11 (br s, 6H), 0.96 (s, 9H); LCMS [M+H]$^+$ 695.

813

Example 666: 2,3-difluoro-4-[2-fluoro-5-[[4-fluoro-2-(trifluoromethyl)benzoyl]amino]-4-[(3R)-3,4-dimethylpiperazin-1-yl]phenyl]-N-(2,4,4-trimethylpentan-2-yl)benzamide

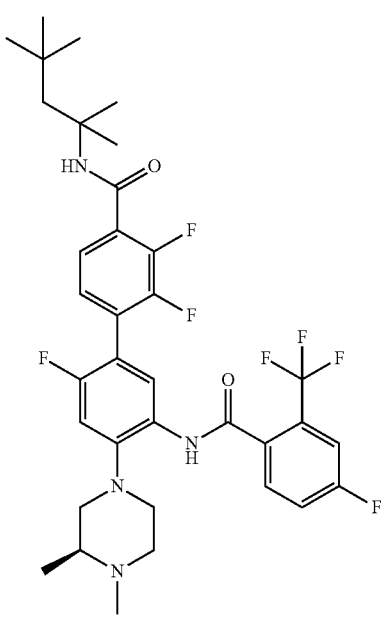 [SMILES: C[C@H]1CN(c2cc(F)c(-c3ccc(C(=O)NC(C)(C)CC(C)(C)C)c(F)c3F)cc2NC(=O)c2ccc(F)cc2C(F)(F)F)CCN1C]

A coupling procedure similar to Example 100 using 2,3-difluoro-4-(4,4,5,5-tetramethyl-1,3,2-dioxaborolan-2-yl)-N-(2,4,4-trimethylpentan-2-yl)benzamide (70.3 mg, 0.178 mmol) and (S)—N-(5-bromo-2-(3,4-dimethylpiperazin-1-yl)-4-fluorophenyl)-4-fluoro-2-(trifluoromethyl)benzamide (51.5 mg, 0.105 mmol) afforded the title compound as a beige fluffy powder (52 mg, 69.4% yield). $^1$H NMR (500 MHz, METHANOL-d4) δ=7.86 (d, J=7.6 Hz, 1H), 7.66 (dd, J=5.3, 8.5 Hz, 1H), 7.54 (dd, J=2.4, 9.0 Hz, 1H), 7.45 (dt, J=2.3, 8.3 Hz, 1H), 7.31 (br t, J=7.0 Hz, 1H), 7.23-7.18 (m, 1H), 7.04 (d, J=11.2 Hz, 1H), 3.09 (br d, J=12.1 Hz, 1H), 3.04 (br d, J=11.6 Hz, 1H), 2.94-2.84 (m, 2H), 2.57-2.47 (m, 2H), 2.46-2.37 (m, 1H), 2.32 (br s, 3H), 1.85 (s, 2H), 1.40 (s, 6H), 1.06 (br d, J=6.1 Hz, 3H), 0.97 (s, 9H); LCMS [M+H]$^+$ 681.

814

Example 667: 2,3-difluoro-4-[2-fluoro-5-[[4-fluoro-2-(trifluoromethyl)benzoyl]amino]-4-[(3R,5S)-3,4,5-trimethylpiperazin-1-yl]phenyl]benzamide

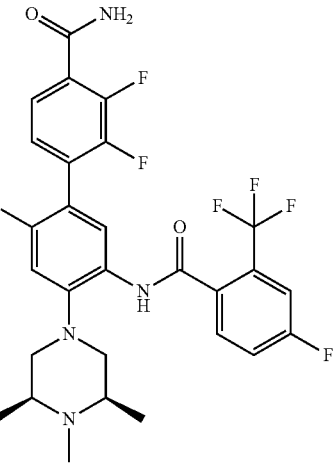

A coupling procedure similar to Example 100 using 2,3-difluoro-4-(4,4,5,5-tetramethyl-1,3,2-dioxaborolan-2-yl)-N-(2,4,4-trimethylpentan-2-yl)benzamide (68.4 mg, 0.173 mmol) and N-(5-bromo-4-fluoro-2-((3S,5R)-3,4,5-trimethylpiperazin-1-yl)phenyl)-4-fluoro-2-(trifluoromethyl)benzamide (51.5 mg, 0.102 mmol) followed by deprotection afforded the title compound (TFA salt) which was isolated as a beige fluffy powder (60 mg, 0.068 mmol, 91% yield). $^1$H NMR (500 MHz, METHANOL-d4) δ=8.05 (d, J=7.6 Hz, 1H), 7.81 (dd, J=5.3, 8.4 Hz, 1H), 7.70-7.65 (m, 2H), 7.58 (dt, J=2.3, 8.3 Hz, 1H), 7.36 (br t, J=7.0 Hz, 1H), 7.25 (d, J=10.9 Hz, 1H), 3.56-3.49 (m, 2H), 3.46 (br d, J=13.0 Hz, 2H), 3.03-2.96 (m, 5H), 1.48 (d, J=6.5 Hz, 6H); LCMS [M+H]$^+$ 583.

Example 668: 2,3-difluoro-4-[2-fluoro-5-[[4-fluoro-2-(trifluoromethyl)benzoyl]amino]-4-[(3R)-3,4-dimethylpiperazin-1-yl]phenyl]benzamide

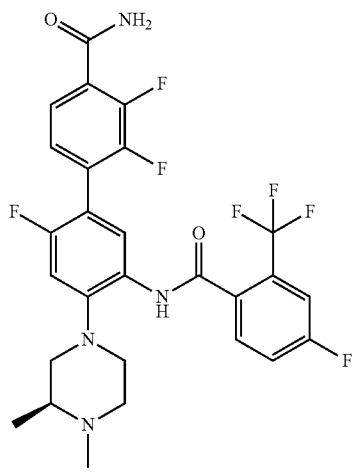 [SMILES: C[C@H]1CN(c2cc(F)c(-c3ccc(C(N)=O)c(F)c3F)cc2NC(=O)c2ccc(F)cc2C(F)(F)F)CCN1C]

A coupling procedure similar to Example 100 using 2,3-difluoro-4-(4,4,5,5-tetramethyl-1,3,2-dioxaborolan-2- yl)-N-(2,4,4-trimethylpentan-2-yl)benzamide (70.3 mg, 0.178 mmol) and (S)—N-(5-bromo-2-(3,4-dimethylpiperazin-1-yl)-4-fluorophenyl)-4-fluoro-2-(trifluoromethyl)benzamide (51.5 mg, 0.105 mmol) followed by acidic deprotection afforded the title compound (TFA salt) as a beige fluffy powder (55 mg, 93% yield). $^1$H NMR (500 MHz, METHANOL-d4) δ=8.04 (d, J=7.6 Hz, 1H), 7.82 (br dd, J=5.4, 8.2 Hz, 1H), 7.71-7.64 (m, 2H), 7.58 (dt, J=2.1, 8.3 Hz, 1H), 7.37 (br t, J=6.9 Hz, 1H), 7.25 (d, J=10.9 Hz, 1H), 3.67 (br d, J=12.3 Hz, 1H), 3.44 (br s, 3H), 3.21-3.12 (m, 1H), 3.00 (s, 3H), 2.99-2.92 (m, 2H), 1.45 (br d, J=6.2 Hz, 3H); LCMS [M+H]$^+$ 569.

Example 669: N-[5-[2,3-difluoro-4-(2,4,4-trimethylpentan-2-ylcarbamoyl)phenyl]-4-fluoro-2-[(3R,5S)-3,4,5-trimethylpiperazin-1-yl]phenyl]-6-oxo-4-(trifluoromethyl)-1H-pyridine-3-carboxamide

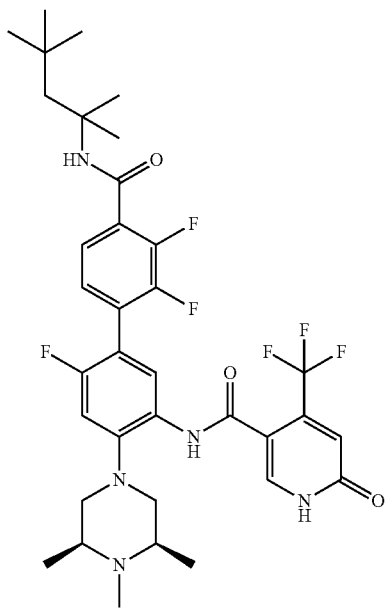 [SMILES: C[C@@H]1CN(c2cc(F)c(-c3ccc(C(=O)NC(C)(C)CC(C)(C)C)c(F)c3F)cc2NC(=O)c2c[nH]c(=O)cc2C(F)(F)F)C[C@H](C)N1C]

A coupling procedure similar to that in Example 100 using 2,3-difluoro-4-(4,4,5,5-tetramethyl-1,3,2-dioxaborolan-2-yl)-N-(2,4,4-trimethylpentan-2-yl)benzamide (69.7 mg, 0.176 mmol) and 2,3-difluoro-4-(4,4,5,5-tetramethyl-1,3,2-dioxaborolan-2-yl)-N-(2,4,4-trimethylpentan-2-yl)benzamide (69.7 mg, 0.176 mmol) afforded the title compound (TFA salt) as a white fluffy powder (17 mg, 0.020 mmol, 93% yield). $^1$H NMR (500 MHz, METHANOL-d4) δ=7.92 (s, 1H), 7.86 (s, 1H), 7.81 (d, J=7.5 Hz, 1H), 7.34 (t, J=6.7 Hz, 1H), 7.23-7.18 (m, 1H), 7.12 (d, J=11.0 Hz, 1H), 6.87-6.83 (m, 1H), 3.48-3.39 (m, 2H), 3.34 (br d, J=13.2 Hz, 2H), 2.92 (s, 3H), 2.90-2.84 (m, 2H), 1.87 (s, 2H), 1.42 (s, 6H), 1.37 (d, J=6.5 Hz, 6H), 0.98 (s, 9H); LCMS [M+H]$^+$ 694.

Example 670: N-[5-(4-carbamoyl-2,3-difluorophenyl)-4-fluoro-2-[(3R,5S)-3,4,5-trimethylpiperazin-1-yl]phenyl]-6-oxo-4-(trifluoromethyl)-1H-pyridine-3-carboxamide

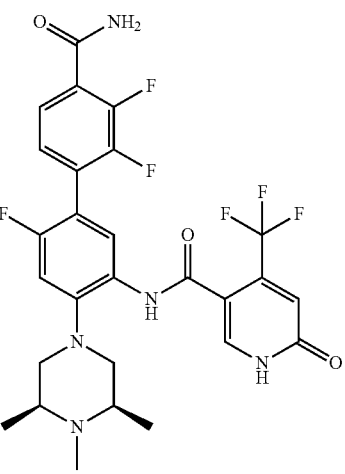 [SMILES: C[C@@H]1CN(c2cc(F)c(-c3ccc(C(N)=O)c(F)c3F)cc2NC(=O)c2c[nH]c(=O)cc2C(F)(F)F)C[C@H](C)N1C]

A coupling procedure similar to that in Example 100 using 2,3-difluoro-4-(4,4,5,5-tetramethyl-1,3,2-dioxaborolan-2-yl)-N-(2,4,4-trimethylpentan-2-yl)benzamide (69.7 mg, 0.176 mmol) and 2,3-difluoro-4-(4,4,5,5-tetramethyl-1,3,2-dioxaborolan-2-yl)-N-(2,4,4-trimethylpentan-2-yl)benzamide (69.7 mg, 0.176 mmol) afforded the title compound (TFA salt) which was isolated as a beige fluffy powder (50 mg, 0.059 mmol, 90% yield). $^1$H NMR (500 MHz, METHANOL-d4) δ=7.89 (s, 1H), 7.80 (d, J=7.5 Hz, 1H), 7.55-7.50 (m, 1H), 7.22 (t, J=6.8 Hz, 1H), 7.10 (d, J=11.0 Hz, 1H), 6.85-6.80 (m, 1H), 3.46-3.36 (m, 2H), 3.31 (br d, J=13.2 Hz, 2H), 2.89 (s, 3H), 2.88-2.82 (m, 2H), 1.34 (d, J=6.5 Hz, 6H); LCMS [M+H]$^+$ 582.

Example 671: N-[4-fluoro-5-(6-morpholin-4-ylpyridin-2-yl)-2-[(3R)-3,4-dimethylpiperazin-1-yl]phenyl]-1-methyl-6-oxo-4-(trifluoromethyl)pyridine-3-carboxamide

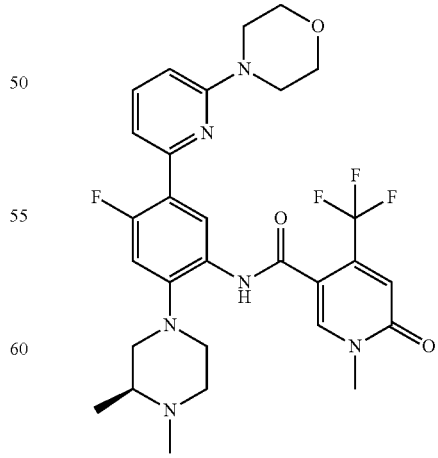

To a 20 mL microwave vial charged with (S)-5-bromo-2-(3,4-dimethylpiperazin-1-yl)-4-fluoroaniline (907 mg, 3 mmol), bis(pinacolato)diboron (1.524 g, 6 mmol), Pd(dppf)Cl₂ (110 mg, 0.15 mmol) and KOAc (883 mg, 9 mmol) was added dioxane (12 mL) and the resulting mixture was heated at 110° C. in microwave for 7 h. The crude product (S)-2-(3,4-dimethylpiperazin-1-yl)-4-fluoro-5-(4,4,5,5-tetramethyl-1,3,2-dioxaborolan-2-yl)aniline in dioxane was split into 2 equal volumes and used directly for subsequent Suzuki couplings. To a mixture of crude (S)-2-(3,4-dimethylpiperazin-1-yl)-4-fluoro-5-(4,4,5,5-tetramethyl-1,3,2-dioxaborolan-2-yl)aniline in dioxane (1.5 mmol assuming full conversion) and 4-(6-bromopyridin-2-yl)morpholine (438 mg, 1.8 mmol) was added bis(di-tert-butyl(4-dimethylaminophenyl)phosphine)dichloropalladium(II) (53 mg, 0.075 mmol) and 1 M K₃PO₄ (3 mL, 3 mmol). The resulting mixture was heated in microwave at 110° C. for 2 h. After diluting with brine (5 mL), it was extracted with EtOAc (15 mL×2). The combined extracts were concentrated and purified by flash chromatography (gradient: EtOAc/hex 0-100% then MeOH/DCM 0-10%) to give (S)-2-(3,4-dimethylpiperazin-1-yl)-4-fluoro-5-(6-morpholinopyridin-2-yl)aniline as a brown foam (403 mg, 61% yield over two steps based on 87.44% purity). LCMS [M+H]⁺ 386.4. A mixture of 1-methyl-6-oxo-4-(trifluoromethyl)-1,6-dihydropyridine-3-carboxylic acid (44 mg, 0.2 mmol), HATU (76 mg, 0.2 mmol) and N,N-diisopropylethylamine (0.052 ml, 0.3 mmol) in DMF (1 mL) was heated at 60° C. for 5 min to afford a clear colorless solution before a solution of (S)-2-(3,4-dimethylpiperazin-1-yl)-4-fluoro-5-(6-morpholinopyridin-2-yl)aniline (44 mg, 87.44% purity, 0.1 mmol) in DMF (1 mL) was added in one portion. The resulting mixture was heated at 60° C. overnight. Solvent were removed and the residue was purified by prep-HPLC and Biotage SCX-2 column to give the title compound as a beige solid (27.1 mg, 45%). ¹H NMR (500 MHz, METHANOL-d4) δ=8.53 (d, J=8.3 Hz, 1H), 8.23 (s, 1H), 7.63 (t, J=7.9 Hz, 1H), 7.23 (dd, J=1.7, 7.5 Hz, 1H), 7.03 (d, J=13.0 Hz, 1H), 6.95 (s, 1H), 6.77 (d, J=8.4 Hz, 1H), 3.86-3.80 (m, 4H), 3.66 (s, 3H), 3.62-3.55 (m, 4H), 3.18-3.06 (m, 2H), 2.99-2.90 (m, 2H), 2.61-2.50 (m, 2H), 2.44-2.34 (m, 4H), 1.14 (d, J=6.4 Hz, 3H); LCMS [M+H]⁺ 589.4.

Example 672: 4-(difluoromethyl)-N-[4-fluoro-5-(6-morpholin-4-ylpyridin-2-yl)-2-[(3R)-3,4-dimethylpiperazin-1-yl]phenyl]-1-methyl-6-oxopyridine-3-carboxamide

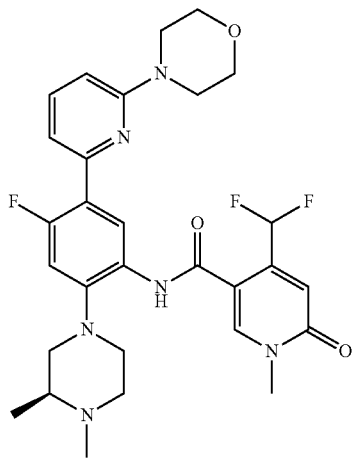

A mixture of 4-(difluoromethyl)-1-methyl-6-oxo-1,6-dihydropyridine-3-carboxylic acid (41 mg, 0.2 mmol), HATU (76 mg, 0.2 mmol) and N,N-diisopropylethylamine (0.052 ml, 0.3 mmol) in DMF (1 mL) was heated at 60° C. for 5 min to afford a clear colorless solution before a solution of (S)-2-(3,4-dimethylpiperazin-1-yl)-4-fluoro-5-(6-morpholinopyridin-2-yl)aniline (44 mg, 87.44% purity, 0.1 mmol) in DMF (1 mL) was added in one portion. The resulting mixture was heated at 60° C. overnight. Solvent were removed and the residue was purified by prep-HPLC and Biotage SCX-2 column to give the title compound as a brown solid (20.5 mg, 35%). ¹H NMR (500 MHz, METHANOL-d4) δ=8.38-8.33 (m, J=8.3 Hz, 1H), 8.31 (s, 1H), 7.63 (t, J=8.0 Hz, 1H), 7.41-7.17 (m, 2H), 7.01 (d, J=12.8 Hz, 1H), 6.82 (s, 1H), 6.79-6.75 (m, J=8.4 Hz, 1H), 3.83-3.78 (m, 4H), 3.64 (s, 3H), 3.60-3.54 (m, 4H), 3.20-3.08 (m, 2H), 2.99-2.87 (m, 2H), 2.60-2.48 (m, 2H), 2.45-2.34 (m, 4H), 1.13 (d, J=6.2 Hz, 3H); LCMS [M+H]⁺ 571.3.

Example 673: 4-fluoro-N-[4-fluoro-5-(6-morpholin-4-ylpyridin-2-yl)-2-[(3R)-3,4-dimethylpiperazin-1-yl]phenyl]-2-(trifluoromethyl)benzamide

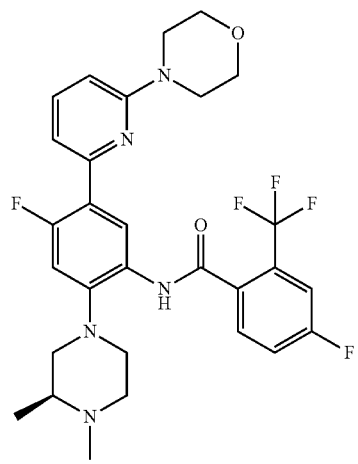 [SMILES: C[C@H]1CN(c2cc(F)c(-c3cccc(N4CCOCC4)n3)cc2NC(=O)c2ccc(F)cc2C(F)(F)F)CCN1C]

To a solution of 4-fluoro-2-(trifluoromethyl)benzoyl chloride (0.045 mL, 0.3 mmol) in DCM (3 mL) at rt was added Et₃N (0.084 mL, 0.6 mmol). After addition, the resulting mixture was stirred at rt for 5 min, before a solution of (S)-2-(3,4-dimethylpiperazin-1-yl)-4-fluoro-5-(6-morpholinopyridin-2-yl)aniline (44 mg, 87.44% purity, 0.1 mmol) in DCM (2 mL) was added. The resulting mixture was stirred for 18 h at rt. Solvent were removed and the residue was purified by prep-HPLC to give the title compound as a brown solid (formic acid salt, 19.8 mg, 31%). ¹H NMR (500 MHz, METHANOL-d4) δ=8.70-8.65 (m, J=8.3 Hz, 1H), 8.34 (br s, 1H), 7.79 (dd, J=5.3, 8.3 Hz, 1H), 7.71-7.55 (m, 3H), 7.26 (br d, J=6.4 Hz, 1H), 7.10 (d, J=12.6 Hz, 1H), 6.82-6.77 (m, J=8.4 Hz, 1H), 3.89-3.80 (m, 4H), 3.64-3.57 (m, 4H), 3.42 (br d, J=10.9 Hz, 1H), 3.37-3.34 (m, 1H), 3.31-3.29 (m, 1H), 3.17-3.04 (m, 3H), 2.91-2.83 (m, 1H), 2.79 (s, 3H), 1.35 (d, J=6.4 Hz, 3H); LCMS [M+H]⁺ 576.2.

Example 674: Propan-2-yl 4-[2-fluoro-5-[[6-oxo-4-(trifluoromethyl)-1H-pyridine-3-carbonyl]amino]-4-[(3R 5S)-3,4,5-trimethylpiperazin-1-yl]phenyl]-2,3,6,7-tetrahydroazepine-1-carboxylate

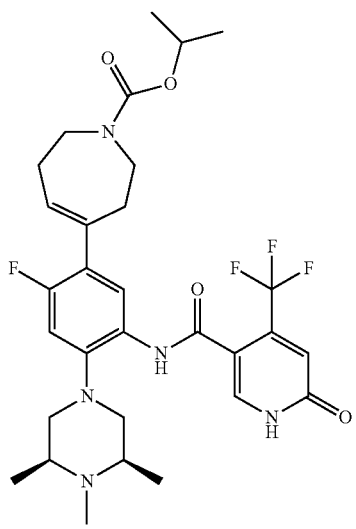 [SMILES: CC(C)OC(=O)N1CCC=C(c2cc(NC(=O)c3c[nH]c(=O)cc3C(F)(F)F)c(N3C[C@@H](C)N(C)[C@@H](C)C3)cc2F)CC1]

To a solution of N-(4-fluoro-5-(2,3,6,7-tetrahydro-1H-azepin-4-yl)-2-((3S,5R)-3,4,5-trimethylpiperazin-1-yl)phenyl)-6-oxo-4-(trifluoromethyl)-1,6-dihydropyridine-3-carboxamide (32 mg, 0.061 mmol, prepared in a similar manner to Example 372 using tert-Butyl 4-(4,4,5,5-tetramethyl-1,3,2-dioxaborolan-2-yl)-2,3,6,7-tetrahydro-1H-azepine-1-carboxylate and N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide) and NN-diisopropylethylamine (0.021 ml, 0.123 mmol) in DCM (3 ml) was added isopropyl chloroformate (0.031 ml, 0.031 mmol in 0.5 ml of DCM. After 5 min, LCMS showed reaction completion. The reaction mixture was diluted with water and DCM. The organic layer was separated. The aqueous layer was extracted several times with DCM. The combined organic layers were dried over $Na_2SO_4$, concentrated down, loaded onto celite and dried. It was then purified by reverse phase Isco (C18 13.3 g cartridge, eluent: 10%, 10-100%, then 100% AcCN/water). The title compound was lyophilized from water/acetonitrile and collected as a white fluffy powder (25 mg, 0.039 mmol, 63.7% yield). $^1$H NMR (500 MHz, METHANOL-d4) δ=7.92 (br d, J=7.1 Hz, 1H), 7.71-7.63 (m, 1H), 6.96-6.91 (m, 2H), 6.02-5.94 (m, 1H), 4.09 (br dd, J=4.8, 14.4 Hz, 2H), 3.70 (t, J=5.9 Hz, 2H), 3.68-3.58 (m, 1H), 3.03 (br d, J=7.9 Hz, 2H), 2.65-2.55 (m, 6H), 2.41 (s, 3H), 1.97-1.86 (m, 2H), 1.32-1.25 (m, 7H), 1.18 (br d, J=5.3 Hz, 6H); LCMS [M+H]$^+$ 608.

Example 675: N-[4-fluoro-5-(I-methylbenzimidazol-5-yl)-2-[(3R,5S)-3,4,5-trimethylpiperazin-1-yl]phenyl]-6-oxo-4-(trifluoromethyl)-1H-pyridine-3-carboxamide

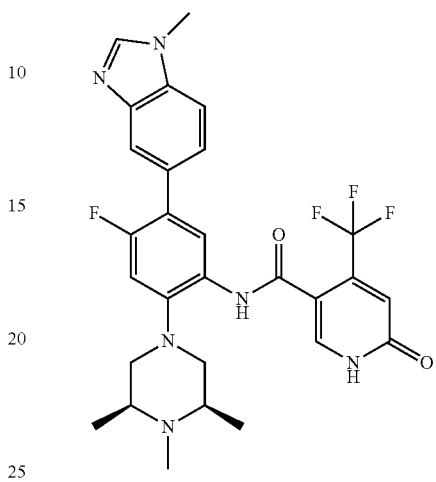

The title compound was prepared similar to the procedure described above for the preparation of Example 616 using 5-bromo-1-methyl-1H-benzo[d]imidazole in place of 4-(4-bromothiazol-2-yl)morpholine in Step 3. $^1$H NMR (500 MHz, DMSO-d6) δ=12.52 (br s, 1H), 9.51 (s, 1H), 8.24 (s, 1H), 7.94 (s, 1H), 7.84 (br d, J=8.6 Hz, 1H), 7.75 (s, 1H), 7.67 (d, J=8.4 Hz, 1H), 7.41 (br d, J=8.4 Hz, 1H), 7.04 (d, J=12.5 Hz, 1H), 6.81 (s, 1H), 3.88 (s, 3H), 3.05 (br d, J=10.9 Hz, 2H), 2.40-2.34 (m, 2H), 2.21 (s, 3H), 1.03 (d, J=6.1 Hz, 6H); LCMS [M+H]+: 557.2.

Example 676: N-[4-fluoro-5-(3-methylbenzimidazol-5-yl)-2-[(3R 5S)-3,4,5-trimethylpiperazin-1-yl]phenyl]-6-oxo-4-(trifluoromethyl)-1H-pyridine-3-carboxamide

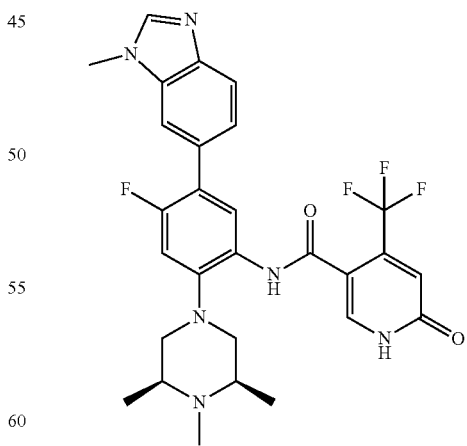

The title compound was prepared similar to the procedure described above for the preparation of Example 616 using 6-bromo-1-methyl-1H-benzo[d]imidazole in place of 4-(4-bromothiazol-2-yl)morpholine in Step 3. $^1$H NMR (500 MHz, DMSO-d6) δ=12.55 (br s, 1H), 9.51 (s, 1H), 8.23 (s, 1H), 7.95 (br s, 1H), 7.83 (br d, J=8.3 Hz, 1H), 7.73 (br d, J=8.3 Hz, 1H), 7.66 (s, 1H), 7.34 (br d, J=8.4 Hz, 1H), 7.06 (br d, J=12.2 Hz, 1H), 6.79 (s, 1H), 3.88 (s, 3H), 3.05 (br d, J=10.6 Hz, 3H), 2.37 (br d, J=7.5 Hz, 3H), 2.21 (s, 3H), 1.03 (br d, J=6.0 Hz, 6H); LCMS [M+H]+: 557.1.

Example 677: N-[5-(1,3-benzothiazol-4-yl)-4-fluoro-2-[(3R,5S)-3,4,5-trimethylpiperazin-1-yl]phenyl]-6-oxo-4-(trifluoromethyl)-1H-pyridine-3-carboxamide

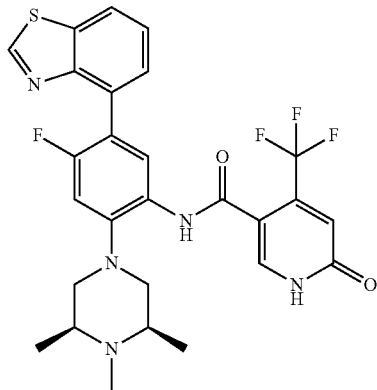 [SMILES: C[C@@H]1CN(c2cc(F)c(-c3cccc4scnc34)cc2NC(=O)c2c[nH]c(=O)cc2C(F)(F)F)C[C@H](C)N1C]

The title compound was prepared similar to the procedure described above for the preparation of Example 616 using 4-bromo-1,3-benzothiazole in place of 4-(4-bromothiazol-2-yl)morpholine in Step 3. $^1$H NMR (500 MHz, DMSO-d6) δ=12.52 (br s, 1H), 9.53 (br d, J=3.2 Hz, 1H), 9.39-9.34 (m, 1H), 8.23 (dd, J=3.2, 7.5 Hz, 1H), 7.91 (br s, 1H), 7.87-7.79 (m, 1H), 7.62-7.56 (m, 1H), 7.54-7.48 (m, 1H), 7.06 (br dd, J=3.8, 11.4 Hz, 1H), 6.80 (br d, J=3.2 Hz, 1H), 3.08 (br d, J=9.5 Hz, 3H), 2.39 (br s, 3H), 2.23 (br s, 3H), 1.04 (br d, J=5.9 Hz, 6H); LCMS [M+H]+: 560.2.

Example 678: N-[5-(1,3-benzothiazol-5-yl)-4-fluoro-2-[(3R,5S)-3,4,5-trimethylpiperazin-1-yl]phenyl]-6-oxo-4-(trifluoromethyl)-1H-pyridine-3-carboxamide

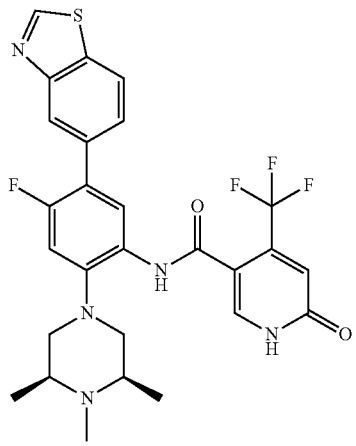 [SMILES: C[C@@H]1CN(c2cc(F)c(-c3ccc4scnc4c3)cc2NC(=O)c2c[nH]c(=O)cc2C(F)(F)F)C[C@H](C)N1C]

The title compound was prepared similar to the procedure described above for the preparation of Example 616 using 5-bromobenzothiazole in place of 4-(4-bromothiazol-2-yl)morpholine in Step 3. $^1$H NMR (500 MHz, DMSO-d6) δ=12.45 (br s, 1H), 9.56 (s, 1H), 9.47 (s, 1H), 8.28 (d, J=8.4 Hz, 1H), 8.19 (s, 1H), 7.95 (s, 1H), 7.89 (br d, J=8.6 Hz, 1H), 7.63 (br d, J=8.2 Hz, 1H), 7.08 (d, J=12.6 Hz, 1H), 6.81 (s, 1H), 3.08 (br d, J=11.0 Hz, 3H), 2.38 (br d, J=7.0 Hz, 3H), 2.21 (s, 3H), 1.03 (d, J=6.1 Hz, 6H); LCMS [M+H]+: 560.2.

Example 679: N-[5-(1,3-benzothiazol-6-yl)-4-fluoro-2-[(3R,5S)-3,4,5-trimethylpiperazin-1-yl]phenyl]-6-oxo-4-(trifluoromethyl)-1H-pyridine-3-carboxamide

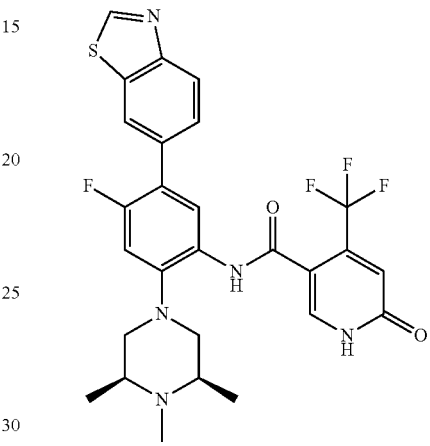

The title compound was prepared similar to the procedure described above for the preparation of Example 616 using 5-bromobenzothiazole in place of 4-(4-bromothiazol-2-yl)morpholine in Step 3. $^1$H NMR (500 MHz, DMSO-d6) δ=12.43 (br s, 1H), 9.55 (s, 1H), 9.44 (s, 1H), 8.32 (s, 1H), 8.18 (d, J=8.6 Hz, 1H), 7.94 (s, 1H), 7.87 (br d, J=8.4 Hz, 1H), 7.67 (br d, J=8.6 Hz, 1H), 7.08 (d, J=12.5 Hz, 1H), 6.81 (s, 1H), 3.07 (br d, J=11.2 Hz, 3H), 2.42-2.32 (m, 3H), 2.21 (s, 3H), 1.03 (br d, J=6.0 Hz, 6H); LCMS [M+H]+: 560.3.

Example 680: 4-(difluoromethyl)-N-[4-fluoro-5-(1-methylbenzimidazol-5-yl)-2-[(3R,5S)-3,4,5-trimethylpiperazin-1-yl]phenyl]-1-methyl-6-oxopyridine-3-carboxamide

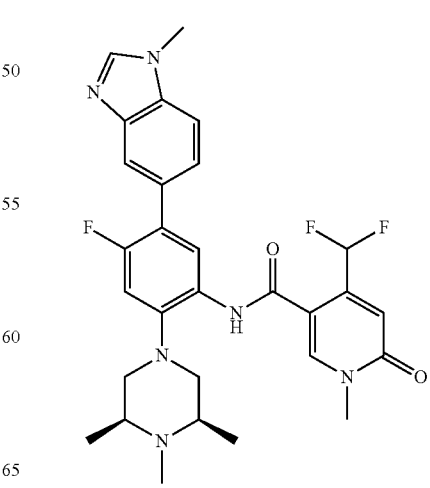

The title compound was prepared from 4-(trifluoromethyl)-6-(2-(trimethylsilyl)ethoxy)nicotinic acid (0.017 g, 0.054 mmol) and 4-fluoro-5-(1-methyl-1H-benzo[d]imidazol-5-yl)-2-((3S,5R)-3,4,5-trimethylpiperazin-1-yl)aniline (0.010 g, 0.027 mmol) the latter reagent which was prepared by a route similar to Example 616 using 2-(2-fluoro-5-nitro-4-((3S,5R)-3,4,5-trimethylpiperazin-1-yl)phenyl)-6-methyl-1,3,6,2-dioxazaborocane-4,8-dione and 5-bromo-1-methyl-1H-benzo[d]imidazole. $^1$H NMR (500 MHz, DMSO-d6) δ=9.49 (s, 1H), 8.37 (s, 1H), 8.24 (s, 1H), 7.79-7.73 (m, 2H), 7.67 (d, J=8.4 Hz, 1H), 7.48-7.23 (m, 2H), 7.05 (d, J=12.5 Hz, 1H), 6.65 (s, 1H), 3.88 (s, 3H), 3.53 (s, 3H), 3.06 (br d, J=11.0 Hz, 3H), 2.42-2.32 (m, 3H), 2.20 (s, 3H), 1.02 (d, J=6.1 Hz, 6H); LCMS [M+H]+: 553.3.

Example 681: 4-(difluoromethyl)-N-[4-fluoro-5-(3-methylbenzimidazol-5-yl)-2-[(3R 5S)-3,4,5-trimethylpiperazin-1-yl]phenyl]-1-methyl-6-oxopyridine-3-carboxamide

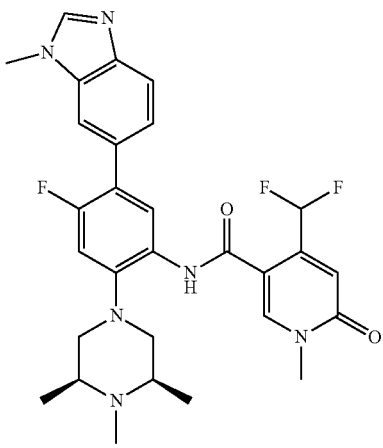 [SMILES: C[C@@H]1CN(c2cc(F)c(-c3ccc4ncn(C)c4c3)cc2NC(=O)c2cn(C)c(=O)cc2C(F)F)C[C@H](C)N1C]

The title compound (13 mg, 79% yield) was prepared according to a procedure similar to that described above for the preparation of Example 616 using 4-(difluoromethyl)-1-methyl-6-oxo-1,6-dihydropyridine-3-carboxylic acid (0.012 g, 0.060 mmol) and 4-fluoro-5-(1-methyl-1H-benzo[d]imidazol-6-yl)-2-((3S,5R)-3,4,5-trimethylpiperazin-1-yl)aniline (0.011 g, 0.030 mmol) in the final step. The latter reagent was prepared according to a route similar to Example 616 starting from 2-(2-fluoro-5-nitro-4-((3S,5R)-3,4,5-trimethylpiperazin-1-yl)phenyl)-6-methyl-1,3,6,2-dioxazaborocane-4,8-dione (0.075 g, 0.178 mmol), 6-bromo-1-methyl-1H-benzo[d]imidazole (0.056 g, 0.266 mmol) and tetrakis(triphenylphosphine)palladium(0) (0.021 g, 0.018 mmol). $^1$H NMR (500 MHz, DMSO-d6) δ=9.50 (s, 1H), 8.38 (s, 1H), 8.23 (s, 1H), 7.74 (t, J=8.7 Hz, 2H), 7.66 (s, 1H), 7.47-7.23 (m, 2H), 7.06 (d, J=12.5 Hz, 1H), 6.65 (s, 1H), 3.88 (s, 3H), 3.53 (s, 3H), 3.06 (br d, J=10.9 Hz, 2H), 2.36 (td, J=3.4, 6.7 Hz, 3H), 2.20 (s, 3H), 1.02 (d, J=6.1 Hz, 6H); LCMS [M+H]+: 553.1.

Example 682: N-[5-(1,3-benzothiazol-4-yl)-4-fluoro-2-[(3R,5S)-3,4,5-trimethylpiperazin-1-yl]phenyl]-4-(difluoromethyl)-1-methyl-6-oxopyridine-3-carboxamide

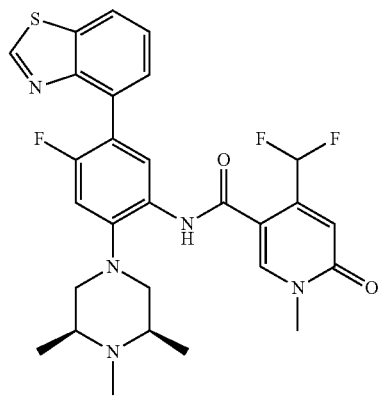 [SMILES: C[C@@H]1CN(c2cc(F)c(-c3cccc4scnc34)cc2NC(=O)c2cn(C)c(=O)cc2C(F)F)C[C@H](C)N1C]

The title compound was prepared similar to the procedure described above for the preparation of Example 677 using 4-(difluoromethyl)-1-methyl-6-oxo-1,6-dihydropyridine-3-carboxylic acid in place of 4-(trifluoromethyl)-6-(2-(trimethylsilyl)ethoxy)nicotinic acid in Step 5. $^1$H NMR (500 MHz, DMSO-d6) δ=9.49 (s, 1H), 9.37 (s, 1H), 8.36 (s, 1H), 8.22 (d, J=8.1 Hz, 1H), 7.76 (d, J=7.9 Hz, 1H), 7.57 (d, J=7.9 Hz, 1H), 7.51 (br d, J=7.3 Hz, 1H), 7.43-7.18 (m, 1H), 7.07 (d, J=11.6 Hz, 1H), 6.63 (s, 1H), 3.51 (s, 3H), 3.08 (br d, J=11.1 Hz, 2H), 2.38 (br d, J=6.4 Hz, 3H), 2.20 (s, 3H), 1.02 (d, J=6.0 Hz, 6H); LCMS [M+H]+: 556.3.

Example 683: N-[5-(1,3-benzothiazol-5-yl)-4-fluoro-2-[(3R,5S)-3,4,5-trimethylpiperazin-1-yl]phenyl]-4-(difluoromethyl)-1-methyl-6-oxopyridine-3-carboxamide

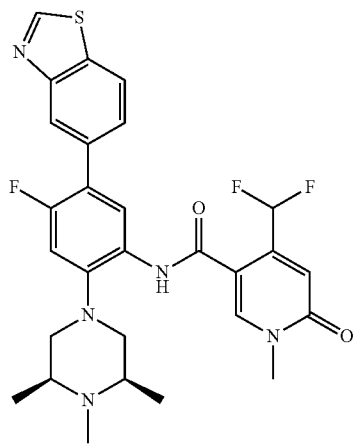 [SMILES: C[C@@H]1CN(c2cc(F)c(-c3ccc4scnc4c3)cc2NC(=O)c2cn(C)c(=O)cc2C(F)F)C[C@H](C)N1C]

The title compound was prepared similar to the procedure described above for the preparation of Example 678 using 4-(difluoromethyl)-1-methyl-6-oxo-1,6-dihydropyridine-3-carboxylic acid in place of 4-(trifluoromethyl)-6-(2-(trimethylsilyl)ethoxy)nicotinic acid in Step 5. $^1$H NMR (500 MHz, DMSO-d6) δ=9.45 (s, 1H), 9.39 (s, 1H), 8.30 (s, 1H), 8.20 (d, J=8.3 Hz, 1H), 8.11 (s, 1H), 7.75 (d, J=8.4 Hz, 1H), 7.56 (br d, J=8.7 Hz, 1H), 7.40-7.15 (m, 1H), 7.02 (d, J=12.6 Hz, 1H), 6.58 (s, 1H), 3.45 (s, 3H), 3.02 (br d, J=11.4 Hz, 2H), 2.30 (br d, J=6.5 Hz, 3H), 2.13 (s, 3H), 0.95 (d, J=6.1 Hz, 6H); LCMS [M+H]+: 556.3.

Example 684: N-[5-(1,3-benzothiazol-6-yl)-4-fluoro-2-[(3R,5S)-3,4,5-trimethylpiperazin-1-yl]phenyl]-4-(difluoromethyl)-1-methyl-6-oxopyridine-3-carboxamide

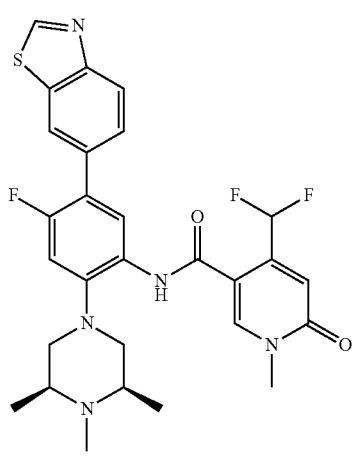

The title compound was prepared similar to the procedure described above for the preparation of Example 679 using 4-(difluoromethyl)-1-methyl-6-oxo-1,6-dihydropyridine-3-carboxylic acid in place of 4-(trifluoromethyl)-6-(2-(trimethylsilyl)ethoxy)nicotinic acid in Step 5. $^1$H NMR (500 MHz, DMSO-d6) δ=9.48 (s, 1H), 9.42 (s, 1H), 8.36 (s, 1H), 8.31 (s, 1H), 8.17 (d, J=8.6 Hz, 1H), 7.80 (br d, J=8.4 Hz, 1H), 7.66 (br d, J=8.3 Hz, 1H), 7.46-7.21 (m, 1H), 7.09 (br d, J=12.5 Hz, 1H), 6.65 (s, 1H), 3.52 (s, 3H), 3.08 (br d, J=10.8 Hz, 2H), 2.37 (br d, J=6.1 Hz, 2H), 2.20 (s, 3H), 1.02 (br d, J=6.1 Hz, 6H); LCMS [M+H]+: 556.1.

Example 685: N-[5-[1-(5-cyano-1,3-thiazol-2-yl)-3,6-dihydro-2H-pyridin-4-yl]-4-fluoro-2-[(3R,5S)-3,4,5-trimethylpiperazin-1-yl]phenyl]-4-(difluoromethyl)-6-oxo-1H-pyridine-3-carboxamide

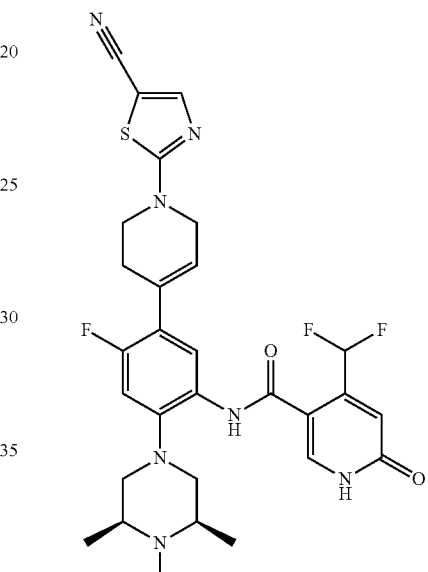

The procedure used was similar to Example 270 using 4-(difluoromethyl)-N-(4-fluoro-5-(1,2,3,6-tetrahydropyridin-4-yl)-2-((3S,5R)-3,4,5-trimethylpiperazin-1-yl)phenyl)-6-oxo-1,6-dihydropyridine-3-carboxamide (25 mg, 0.051 mmol) and 2-bromo-5-cyanothiazole (9.65 mg, 0.051 mmol) to afford the title compound (22 mg, 69% yield). $^1$H NMR (500 MHz, METHANOL-d4) δ 7.89 (s, 1H), 7.71-7.76 (m, 1H), 7.57-7.63 (m, 1H), 7.08-7.33 (m, 1H), 6.84 (d, J=12.47 Hz, 1H), 6.70 (s, 1H), 5.98 (br. s., 1H), 4.10 (d, J=2.69 Hz, 2H), 3.76 (t, J=5.75 Hz, 2H), 2.90-2.95 (m, 2H), 2.93 (d, J=11.25 Hz, 2H), 2.58 (br. s., 2H), 2.44-2.50 (m, 2H), 2.35-2.42 (m, 2H), 2.25 (s, 3H), 1.04 (d, J=6.11 Hz, 6H); LCMS [M+H]+ 598.5.

Example 686: N-[5-[1-(5-cyano-1,3-thiazol-2-yl)-3,6-dihydro-2H-pyridin-4-yl]-4-fluoro-2-[(3R)-3,4-dimethylpiperazin-1-yl]phenyl]-4-(difluoromethyl)-6-oxo-1H-pyridine-3-carboxamide

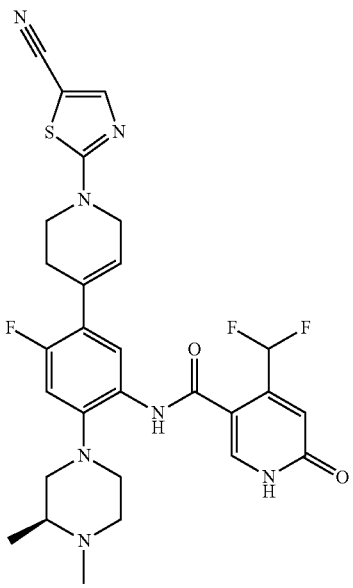 [SMILES: C[C@H]1CN(c2cc(F)c(C3=CCN(c4ncc(C#N)s4)CC3)cc2NC(=O)c2c[nH]c(=O)cc2C(F)F)CCN1C]

The procedure followed was similar to Example 270 using (S)-4-(difluoromethyl)-N-(2-(3,4-dimethylpiperazin-1-yl)-4-fluoro-5-(1,2,3,6-tetrahydropyridin-4-yl)phenyl)-6-oxo-1,6-dihydropyridine-3-carboxamide (25 mg, 0.053 mmol) and 2-bromo-5-cyanothiazole (9.94 mg, 0.053 mmol) to afford the title compound (23.5 mg, 73% yield). $^1$H NMR (500 MHz, METHANOL-d4) δ=7.92-7.88 (m, 1H), 7.77-7.71 (m, 1H), 7.65-7.59 (m, 1H), 7.32-7.07 (m, 1H), 6.90-6.84 (m, 1H), 6.73-6.69 (m, 1H), 6.02-5.95 (m, 1H), 4.13-4.07 (m, 2H), 3.80-3.74 (m, 2H), 3.02-2.89 (m, 2H), 2.83-2.76 (m, 2H), 2.62-2.56 (m, 2H), 2.46-2.37 (m, 2H), 2.31-2.24 (m, 4H), 1.03-0.98 (m, 3H); LCMS [M+H]+ 584.5.

Example 687: N-[5-[1-(5-cyano-1,3-thiazol-2-yl)-3,6-dihydro-2H-pyridin-5-yl]-4-fluoro-2-[(3R,5S)-3,4,5-trimethylpiperazin-1-yl]phenyl]-4-(difluoromethyl)-6-oxo-1H-pyridine-3-carboxamide

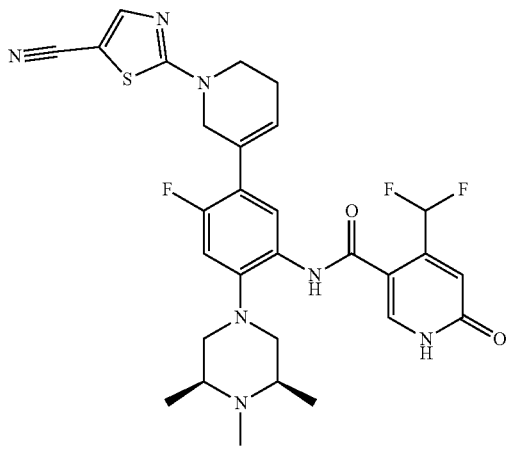 [SMILES: C[C@@H]1CN(c2cc(F)c(C3=CCCN(c4ncc(C#N)s4)C3)cc2NC(=O)c2c[nH]c(=O)cc2C(F)F)C[C@H](C)N1C]

The procedure followed was similar to Example 270 using 4-(difluoromethyl)-N-(4-fluoro-5-(1,2,5,6-tetrahydropyridin-3-yl)-2-((3S,5R)-3,4,5-trimethylpiperazin-1-yl)phenyl)-6-oxo-1,6-dihydropyridine-3-carboxamide (25 mg, 0.051 mmol) and 2-bromo-5-cyanothiazole (9.65 mg, 0.051 mmol) to give the title compound (22 mg, 69% yield). $^1$H NMR (500 MHz, METHANOL-d4) δ 7.89 (s, 1H), 7.69-7.73 (m, 1H), 7.69-7.73 (m, 1H), 7.60 (d, J=8.07 Hz, 1H), 7.08-7.33 (m, 1H), 6.84-6.88 (m, 1H), 6.70 (s, 1H), 6.06-6.11 (m, 1H), 6.06-6.11 (m, 1H), 4.25 (d, J=1.59 Hz, 2H), 3.67-3.72 (m, 2H), 3.67-3.72 (m, 2H), 2.94 (d, J=11.25 Hz, 2H), 2.45-2.51 (m, 2H), 2.37-2.42 (m, 4H), 2.25 (s, 3H), 1.02-1.05 (m, 6H), 1.04 (d, J=6.11 Hz, 6H); LCMS [M+H]+ 598.6.

Example 688: N-[5-[1-(5-cyano-1,3-thiazol-2-yl)-3,6-dihydro-2H-pyridin-5-yl]-4-fluoro-2-[(3R)-3,4-dimethylpiperazin-1-yl]phenyl]-4-(difluoromethyl)-6-oxo-1H-pyridine-3-carboxamide

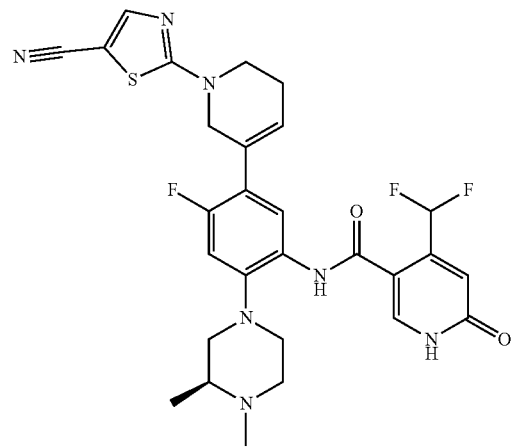 [SMILES: C[C@H]1CN(c2cc(F)c(C3=CCCN(c4ncc(C#N)s4)C3)cc2NC(=O)c2c[nH]c(=O)cc2C(F)F)CCN1C]

The procedure followed was similar to Example 270 using (S)-4-(difluoromethyl)-N-(2-(3,4-dimethylpiperazin-1-yl)-4-fluoro-5-(1,2,5,6-tetrahydropyridin-3-yl)phenyl)-6-oxo-1,6-dihydropyridine-3-carboxamide (25 mg, 0.053 mmol), 2-bromo-5-cyanothiazole (9.94 mg, 0.053 mmol) to afford the title compound (15 mg, 46% yield). $^1$H NMR (500 MHz, METHANOL-d4) δ=7.94-7.87 (m, 1H), 7.75-7.68 (m, 1H), 7.65-7.57 (m, 1H), 7.32-7.07 (m, 1H), 6.92-6.86 (m, 1H), 6.73-6.67 (m, 1H), 6.14-6.06 (m, 1H), 4.30-4.24 (m, 2H), 3.73-3.68 (m, 2H), 3.02-2.96 (m, 1H), 2.95-2.90 (m, 1H), 2.85-2.78 (m, 2H), 2.45-2.38 (m, 4H), 2.31-2.24 (m, 4H), 1.03-0.99 (m, 3H); LCMS [M+H]+ 584.4.

Example 689: N-[5-[1-(5-cyano-1,3-thiazol-2-yl)-3,6-dihydro-2H-pyridin-5-yl]-4-fluoro-2-[(3R)-3,4-dimethylpiperazin-1-yl]phenyl]-4-fluoro-2-(trifluoromethyl)benzamide

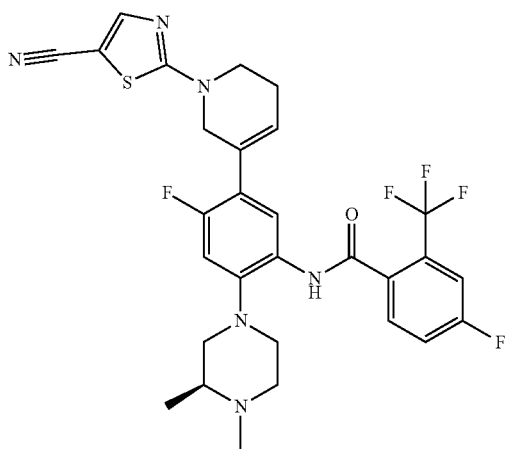 [SMILES: C[C@H]1CN(c2cc(F)c(C3=CCCN(c4ncc(C#N)s4)C3)cc2NC(=O)c2ccc(F)cc2C(F)(F)F)CCN1C]

The procedure followed was similar to Example 270 using (S)—N-(2-(3,4-dimethylpiperazin-1-yl)-4-fluoro-5-(1,2,5,6-tetrahydropyridin-3-yl)phenyl)-4-fluoro-2-(trifluoromethyl)benzamide (25 mg, 0.051 mmol) and 2-bromo-5-cyanothiazole (9.56 mg, 0.051 mmol) to afford the title compound (26.5 mg, 83% yield). $^1$H NMR (500 MHz, METHANOL-d4) δ=7.84-7.78 (m, 1H), 7.74-7.69 (m, 1H), 7.68-7.62 (m, 1H), 7.56-7.51 (m, 1H), 7.48-7.42 (m, 1H), 6.95-6.88 (m, 1H), 6.13-6.07 (m, 1H), 4.27 (br s, 2H), 3.78-3.68 (m, 2H), 3.02-2.94 (m, 1H), 2.94-2.89 (m, 1H), 2.85-2.75 (m, 2H), 2.47-2.39 (m, 3H), 2.39-2.32 (m, 1H), 2.25-2.19 (m, 4H), 1.03-0.98 (m, 3H); LCMS [M+H]+ 603.5.

Example 690: N-[5-[1-(5-cyano-1,3-thiazol-2-yl)-3,6-dihydro-2H-pyridin-4-yl]-4-fluoro-2-[(3R)-3,4-dimethylpiperazin-1-yl]phenyl]-4-fluoro-2-(trifluoromethyl)benzamide

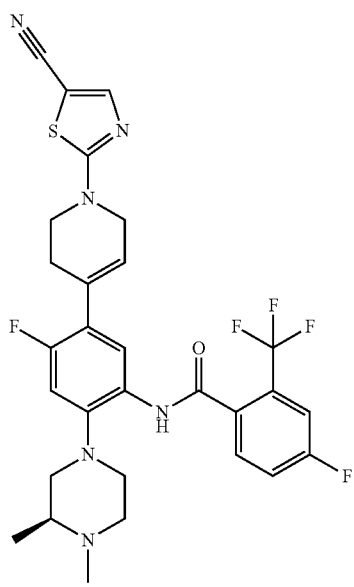 [SMILES: C[C@H]1CN(c2cc(F)c(C3=CCN(c4ncc(C#N)s4)CC3)cc2NC(=O)c2ccc(F)cc2C(F)(F)F)CCN1C]

The procedure used was similar to Example 270 using (S)—N-(2-(3,4-dimethylpiperazin-1-yl)-4-fluoro-5-(1,2,3,6-tetrahydropyridin-4-yl)phenyl)-4-fluoro-2-(trifluoromethyl)benzamide (25 mg, 0.051 mmol, prepared using procedures similar to those described hereinabove) and 2-bromo-5-cyanothiazole (9.56 mg, 0.051 mmol) to give the title compound (22 mg, 69% yield). $^1$H NMR (500 MHz, METHANOL-d4) δ=7.84-7.79 (m, 1H), 7.77-7.71 (m, 1H), 7.68-7.62 (m, 1H), 7.56-7.52 (m, 1H), 7.48-7.41 (m, 1H), 6.93-6.85 (m, 1H), 6.03-5.97 (m, 1H), 4.16-4.07 (m, 2H), 3.84-3.74 (m, 2H), 2.99-2.94 (m, 1H), 2.94-2.88 (m, 1H), 2.84-2.77 (m, 2H), 2.64-2.56 (m, 2H), 2.47-2.39 (m, 1H), 2.38-2.30 (m, 1H), 2.26-2.19 (m, 4H), 1.03-0.98 (m, 3H); LCMS [M+H]+ 603.5

Example 691: N-[4-fluoro-5-[2-[(2R)-2-methylmorpholin-4-yl]pyrimidin-4-yl]-2-[(3R,5S)-3,4,5-trimethylpiperazin-1-yl]phenyl]-6-oxo-4-(trifluoromethyl)-1H-pyridine-3-carboxamide

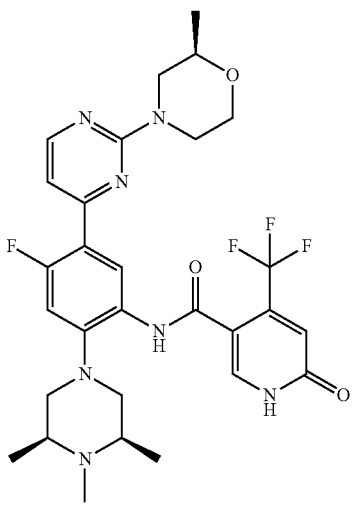 [SMILES: C[C@@H]1CN(c2nccc(-c3cc(NC(=O)c4c[nH]c(=O)cc4C(F)(F)F)c(N4C[C@@H](C)N(C)[C@@H](C)C4)cc3F)n2)CCO1]

The title compound (21.7 mg, 26% yield) was prepared using N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy)nicotinamide (102 mg, 0.125 mmol) and (R)-4-(4-bromopyrimidin-2-yl)-2-methylmorpholine (35.5 mg, 0.138 mmol) by a procedure similar to that described in Example 384. $^1$H NMR (500 MHz, MeOD) δ 8.60 (d, J=8.1 Hz, 1H), 8.36 (d, J=5.2 Hz, 1H), 7.90 (s, 1H), 7.12 (dd, J=5.2, 1.7 Hz, 1H), 7.00 (d, J=13.2 Hz, 1H), 6.92 (s, 1H), 4.65 (d, J=13.1 Hz, 1H), 4.59 (d, J=13.2 Hz, 1H), 3.97 (dd, J=11.5, 2.5 Hz, 1H), 3.66-3.60 (m, 2H), 3.16 (d, J=11.2 Hz, 2H), 3.08-3.02 (m, 1H), 2.70 (dd, J=13.2, 10.4 Hz, 1H), 2.66-2.61 (m, J=11.2 Hz, 2H), 2.59-2.53 (m, 2H), 2.38 (s, 3H), 1.24 (d, J=6.2 Hz, 3H), 1.17 (d, J=6.1 Hz, 6H); LCMS HSS [M+1]$^+$=604.34.

Example 692: 4-(difluoromethyl)-N-[4-fluoro-5-(2-morpholin-4-ylpyrimidin-4-yl)-2-[(3R,5S)-3,4,5-trimethylpiperazin-1-yl]phenyl]-6-oxo-1H-pyridine-3-carboxamide

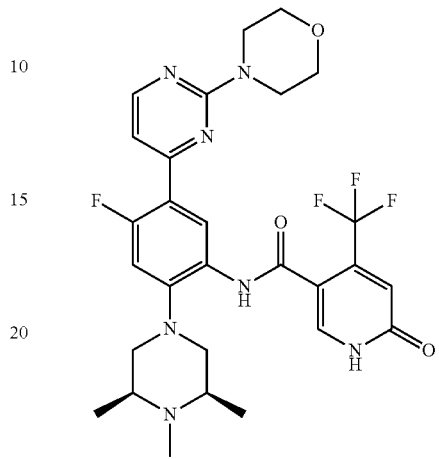

Step 1: 4-(difluoromethyl)-N-(4-fluoro-5-(tributylstannyl)-2-((3S,5R)-3,4,5-trimethylpiperazin-1-yl)phenyl)-6-(2-(trimethylsilyl)ethoxy)nicotinamide

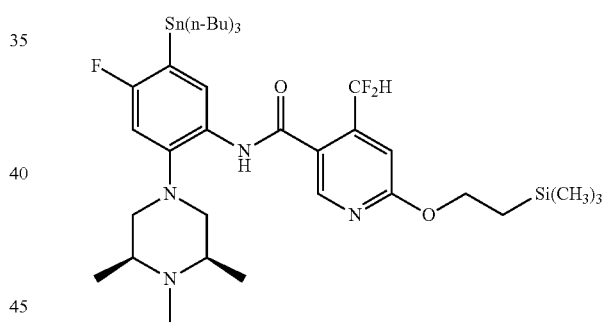

The title compound was prepared similar to the sequence described above for the preparation of Example 384, Step 1 using a stirred solution of N-(5-bromo-4-fluoro-2-((3S,5R)-3,4,5-trimethylpiperazin-1-yl)phenyl)-4-(difluoromethyl)-6-(2-(trimethylsilyl)ethoxy)nicotinamide (10 g, 17.1 mmol, 1 eq) in toluene (60 mL) degassed with argon for 15 min, then adding hexabutylditin (17.3 mL, 34.12 mmol, 2 eq), followed by Pd$_2$(dppf)$_2$Cl$_2$·DCM (1.39 g, 1.71 mmol, 0.1 eq) after that heating to reflux under argon atmosphere for 24 h. TLC analysis indicated formation of less polar spots. The reaction mixture was filtered through celite bed washed with EtOAc; and the filtrate was evaporated under reduced pressure. The crude compound was purified by column chromatography (neutral alumina) using 0-5% EtOAc in pet ether as an eluent to afford 4-(difluoromethyl)-N-(4-fluoro-5-(tributylstannyl)-2-((3S,5R)-3,4,5-trimethylpiperazin-1-yl)phenyl)-6-(2-(trimethylsilyl)ethoxy)nicotinamide (5.2 g, 36.6% yield) as a pale yellow Solid. TLC: 50% EtoAC in petether; R$_f$: 0.5.

Step 2: 4-(difluoromethyl)-N-(4-fluoro-5-(2-morpholinopyrimidin-4-yl)-2-((3S,5R)-3,4,5-trimethylpiperazin-1-yl)phenyl)-6-(2-(trimethylsilyl)ethoxy) nicotinamide

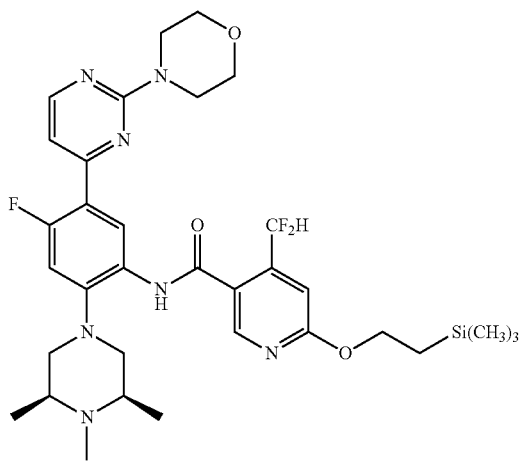

In N,N-dimethylformamide (DMF) (537 µl) was dissolved 4-(difluoromethyl)-N-(4-fluoro-5-(tributylstannyl)-2-((3S,5R)-3,4,5-trimethylpiperazin-1-yl)phenyl)-6-(2-(trimethylsilyl)ethoxy)nicotinamide (107 mg, 0.134 mmol). To the solution was added 4-(4-bromopyrimidin-2-yl)morpholine (36.0 mg, 0.148 mmol), lithium chloride (17.06 mg, 0.402 mmol) and bis(triphenylphosphine)palladium(II) dichloride (5.18 mg, 7.38 µmol) at room temperature and then it was microwaved at the temperature of 120° C. for 3 hours. To the reaction mixture was added water and then extracted with dichloromethane. The organic layer was separated, concentrated and purified by column chromatography on silica gel (0-100%, 89% CH$_2$Cl$_2$, 10% MeOH, 1% NH$_4$Ac/CH$_2$Cl$_2$) to afford the title compound. LCMS [M+1]$^+$=672.43.

Step 3: 4-(difluoromethyl)-N-(4-fluoro-5-(2-morpholinopyrimidin-4-yl)-2-((3S,5R)-3,4,5-trimethylpiperazin-1-yl)phenyl)-6-oxo-1,6-dihydropyridine-3-carboxamide

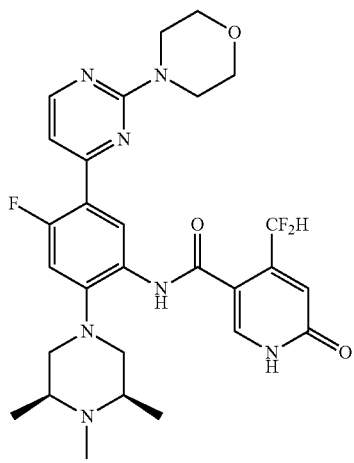 [SMILES: C[C@@H]1CN(c2cc(F)c(-c3ccnc(N4CCOCC4)n3)cc2NC(=O)c2c[nH]c(=O)cc2C(F)F)C[C@H](C)N1C]

The product was dissolved in 2 mL of DCM and TFA (1027 µl, 13.41 mmol) was added. The purple solution was stirred for 1 h and the solvent was evaporated. The residue was purified by a cation exchange column eluting with MeOH:NH$_4$OH and freeze dried for 2 days to afford the product as a white powder. $^1$H NMR (500 MHz, MeOD) δ 8.43 (d, J=8.2 Hz, 1H), 8.37 (d, J=5.2 Hz, 1H), 8.01 (s, TH), 7.31 (t, J=55.1 Hz, TH), 7.12 (dd, J=5.2, 1.9 Hz, TH), 6.99 (d, J=13.2 Hz, TH), 6.81 (s, 1H), 3.85-3.82 (m, 4H), 3.77-3.74 (m, 4H), 3.16 (d, J=11.5 Hz, 2H), 2.62 (t, J=11.2 Hz, 2H), 2.52 (s, 2H), 2.36 (s, 3H), 1.15 (d, J=6.2 Hz, 6H); $^{19}$F NMR (471 MHz, MeOD) δ −115.98 (s), −121.71 (s); LCMS [M+1]$^+$=572.44.

Example 693: N-[4-fluoro-5-(2-morpholin-4-ylpyrimidin-4-yl)-2-[(3R,5S)-3,4,5-trimethylpiperazin-1-yl]phenyl]-1-methyl-6-oxo-4-(trifluoromethyl)pyridine-3-carboxamide

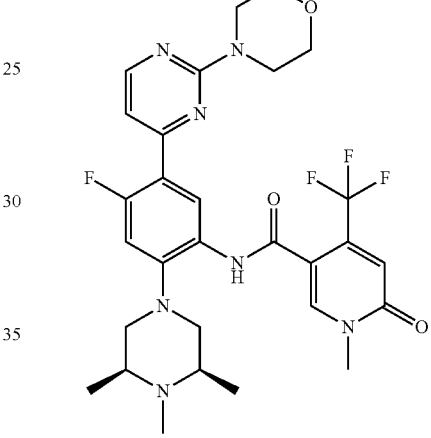

Step 1: 4-(difluoromethyl)-N-(4-fluoro-5-(tributylstannyl)-2-((3S,5R)-3,4,5-trimethylpiperazin-1-yl) phenyl)-6-(2-(trimethylsilyl)ethoxy)nicotinamide

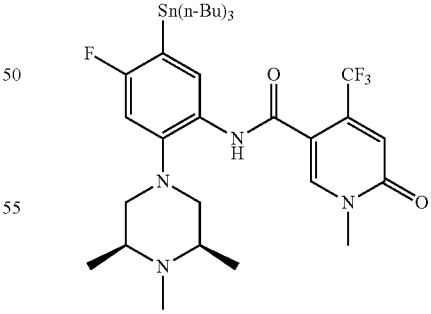

To a stirred solution of N-(5-bromo-4-fluoro-2-((3S,5R)-3,4,5-trimethylpiperazin-1-yl)phenyl)-1-methyl-6-oxo-4-(trifluoromethyl)-1,6-dihydropyridine-3-carboxamide (2 g, 3.86 mmol, 1 eq, procedure described in Example 226) in toluene (70 mL) degassed with argon for 15 min, then hexabutylditin (4.47 g, 7.72 mmol, 2 eq) was added, followed by Pd$_2$(dppf)$_2$Cl$_2$ (315 mg, 0.386 mmol, 0.1 eq) and after that heated to reflux under argon atmosphere for 24 h. TLC analysis indicated formation of less polar spots. The reaction mixture was filtered through celite bed washed with EtOAc; and the filtrate was evaporated under reduced pressure. The crude compound was purified by column chromatography (Basic alumina) using 0-5% MeOH in DCM as an eluent to afford 4-(difluoromethyl)-N-(4-fluoro-5-(tributylstannyl)-2-((3S,5R)-3,4,5-trimethylpiperazin-1-yl)phenyl)-6-(2-(trimethylsilyl)ethoxy)nicotinamide (1.4 g, 50%) as a pale yellow solid. LCMS [M+1]$^+$=731.4.

Step 2: N-(4-fluoro-5-(2-morpholinopyrimidin-4-yl)-2-((3S,5R)-3,4,5-trimethylpiperazin-1-yl)phenyl)-1-methyl-6-oxo-4-(trifluoromethyl)-1,6-dihydropyridine-3-carboxamide

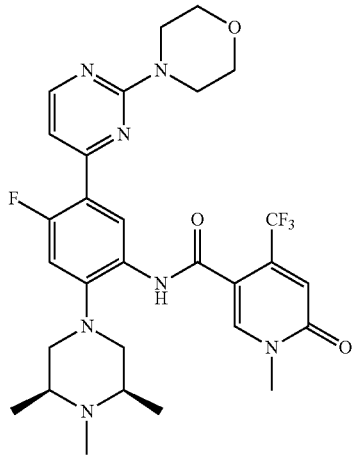

In N,N-dimethylformamide (DMF) (592 µl) was dissolved N-(4-fluoro-5-(tributylstannyl)-2-((3S,5R)-3,4,5-trimethylpiperazin-1-yl)phenyl)-1-methyl-6-oxo-4-(trifluoromethyl)-1,6-dihydropyridine-3-carboxamide (108 mg, 0.148 mmol). To the solution was added 4-(4-bromopyrimidin-2-yl)morpholine (39.8 mg, 0.163 mmol), lithium chloride (18.83 mg, 0.444 mmol) and bis(triphenylphosphine)palladium(II) dichloride (5.72 mg, 8.14 µmol) at room temperature and then it was microwaved at the temperature of 120° C. for 3 hours. To the reaction mixture was added water and then extracted with dichloromethane. The organic layer was separated, concentrated and purified by column chromatography on silica gel (0-100%, 89% CH$_2$Cl$_2$, 10% MeOH, 1% NH$_4$Ac/CH$_2$Cl$_2$) the fractions were concentrated and freeze dried for 2 days to afford the product as a white powder. $^1$H NMR (500 MHz, MeOD) δ 8.58 (d, J=8.2 Hz, 1H), 8.37 (d, J=5.2 Hz, 1H), 8.22 (s, 1H), 7.13 (dd, J=5.2, 2.0 Hz, 1H), 7.01 (d, J=13.2 Hz, 1H), 6.94 (s, 1H), 3.86-3.83 (m, 4H), 3.77-3.75 (m, 4H), 3.64 (s, 3H), 3.13 (d, J=11.6 Hz, 2H), 2.62 (t, J=11.3 Hz, 2H), 2.53-2.48 (m, 2H), 2.34 (s, 3H), 1.15 (d, J=6.3 Hz, 6H); LCMS HSS [M+1]+=604.34.

Example 694: N-[4-fluoro-5-[2-[(2R)-2-methylmorpholin-4-yl]pyrimidin-4-yl]-2-[(3S,5R)-3,4,5-trimethylpiperazin-1-yl]phenyl]-1-methyl-6-oxo-4-(trifluoromethyl)pyridine-3-carboxamide

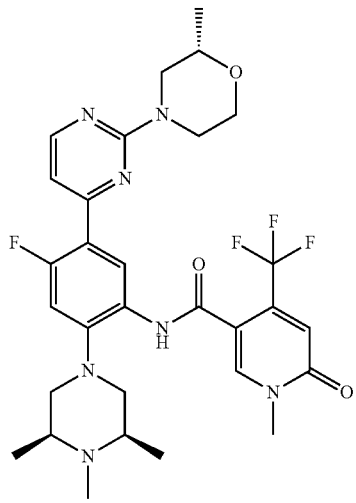 [SMILES: C[C@@H]1CN(c2cc(F)c(-c3ccnc(N4CCO[C@@H](C)C4)n3)cc2NC(=O)c2cn(C)c(=O)cc2C(F)(F)F)C[C@H](C)N1C]

The title compound was prepared similar to the sequence described above for the preparation of Example 693 using (S)-4-(4-bromopyrimidin-2-yl)-2-methylmorpholine in place of 4-(4-bromopyrimidin-2-yl)morpholine. $^1$H NMR (500 MHz, MeOD) δ 8.61 (d, J=8.2 Hz, 1H), 8.37 (d, J=5.2 Hz, 1H), 8.20 (s, 1H), 7.12 (dd, J=5.2, 1.9 Hz, 1H), 7.01 (d, J=13.2 Hz, 1H), 6.94 (s, 1H), 4.65 (d, J=13.2 Hz, 1H), 4.59 (d, J=13.4 Hz, 1H), 3.96 (dd, J=11.5, 2.5 Hz, 1H), 3.64 (s, 3H), 3.62-3.59 (m, 1H), 3.14 (d, J=11.5 Hz, 2H), 3.07-3.01 (m, 1H), 2.70 (dd, J=13.2, 10.4 Hz, 1H), 2.63 (t, J=11.2 Hz, 2H), 2.52 (ddd, J=10.1, 7.6, 4.5 Hz, 2H), 2.35 (s, 3H), 1.23 (d, J=6.2 Hz, 3H), 1.16 (d, J=6.2 Hz, 6H); LCMS [M+1]$^+$=618.34.

Example 695: N-[4-fluoro-5-[2-(oxan-4-yloxy)pyrimidin-4-yl]-2-[(3R,5S)-3,4,5-trimethylpiperazin-1-yl]phenyl]-6-oxo-4-(trifluoromethyl)-1H-pyridine-3-carboxamide

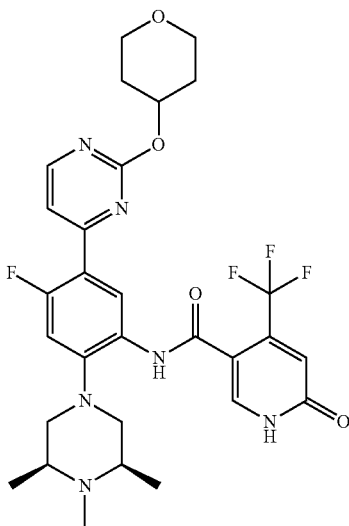 [SMILES: C[C@@H]1CN(c2cc(F)c(-c3ccnc(OC4CCOCC4)n3)cc2NC(=O)c2c[nH]c(=O)cc2C(F)(F)F)C[C@H](C)N1C]

Step 1: 4-bromo-2-(methylthio)pyrimidine

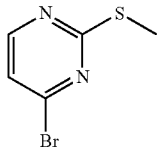

To a stirred solution of 2-(methylthio)pyrimidin-4(3H)-one (5 g, 35.21 mmol, 1 eq) in ACN (100 mL) was added POBr$_3$ (12.1 g, 42.3 mmol, 1.2 eq) at RT, then the reaction mixture was heated to 80° C. for 5 h. Monitored by TLC, the reaction mixture was cooled to RT and quenched in ice cold water then extracted with EtOAc (2×100 mL). The combined organic layer was dried over Na$_2$SO$_4$ and concentrated to crude compound. The crude compound was purified by column chromatography (silica gel, 100-200 mesh) using 0-10% EtOAc in pet ether as eluent to afford 4-bromo-2-(methylthio)pyrimidine (6 g, 83%) as off-white solid. LCMS: [M+H]+ 204.9.

Step 2: 4-bromo-2-(methylsulfonyl)pyrimidine

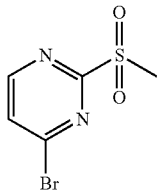

To stirred 30% H$_2$O$_2$ (6 g, 29.4 mmol, 1 eq) was added ammonium molybdate tetrahydrate (1.09 g, 0.88 mmol, 0.03 eq) at 0° C. portion wise then stirred for 20 min., and then a solution of 4-bromo-2-(methylthio)pyrimidine (6 g, 29.41 mmol, 1 eq) slowly added at 0° C. then allowed to RT for 3 h. Monitored by TLC, the reaction mixture was concentrated to crude residue, which was diluted with cold water then extracted with DCM (3×100 mL). The combined organic layer was washed with 5% H$_2$SO$_4$ solution and water then dried over Na$_2$SO$_4$ and concentrated to crude compound. The crude compound was purified by column chromatography (silica gel, 100-200 mesh) using 0-40% EtOAc in pet ether as eluent to afford 4-bromo-2-(methylsulfonyl)pyrimidine (6 g, 86%) as off-white solid. LCMS: [M+H]+ 238.84.

Step 3: 4-bromo-2-((tetrahydro-2H-pyran-4-yl)oxy)pyrimidine

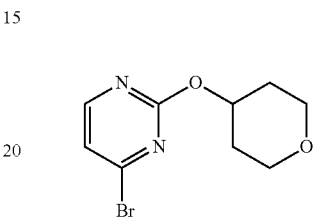

To a stirred solution of tetrahydro-2H-pyran-4-ol (1.66 mL, 16.31 mmol, 1.1 eq) in THF was added K-tOBu (17.79 mL, 17.79 mmol, 1.2 eq, 1M in THF) at 0° C. and continued for 20 min., then the reaction mixture was cooled to −78° C. and to it was added slowly a solution of 4-bromo-2-(methylsulfonyl)pyrimidine (3.5 g, 14.83 mmol, 1 eq, in 50 mL of THF) and continued at −78° C. for 3 h. After monitoring by TLC, the reaction mixture was diluted with diethyl ether (200 mL) and washed with water. The organic layer was dried over Na$_2$SO$_4$ and concentrated to crude compound. The crude compound was purified by column chromatography (silica gel, 100-200 mesh) using 0-20% EtOAc in pet ether as eluent to afford 4-bromo-2-((tetrahydro-2H-pyran-4-yl)oxy)pyrimidine (3.2 g, 83%) as white solid. LC-MS: [M+H]+ 259.09.

Step 4: N-[4-fluoro-5-[2-(oxan-4-yloxy)pyrimidin-4-yl]-2-[(3R,5S)-3,4,5-trimethylpiperazin-1-yl]phenyl]-6-oxo-4-(trifluoromethyl)-1H-pyridine-3-carboxamide

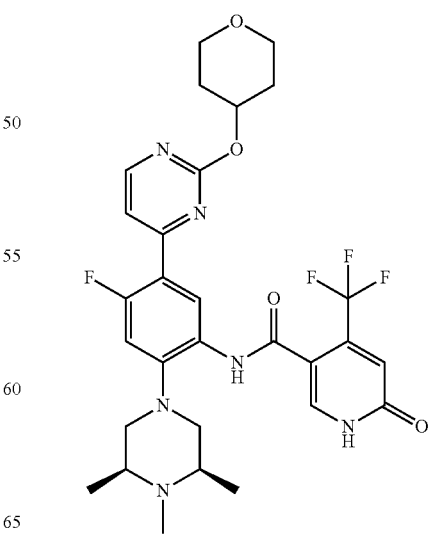

The title compound (10.2 mg, 12.3% yield) was prepared similar to the coupling procedure described above for the preparation of Example 384 using N-(4-fluoro-5-(tributyl-stannyl)-2-((3S,5R)-3,4,5-trimethylpiperazin-1-yl)phenyl)-4-(trifluoromethyl)-6-(2-(trimethylsilyl)ethoxy)nicotinamide (108 mg, 0.132 mmol) and 4-bromo-2-((tetrahydro-2H-pyran-4-yl)oxy)pyrimidine (37.7 mg, 0.146 mmol). $^1$H NMR (500 MHz, MeOD) δ 8.72 (d, J=8.3 Hz, 1H), 8.57 (d, J=5.4 Hz, 1H), 7.92 (s, J=4.6 Hz, 1H), 7.56 (dd, J=4.1 Hz, 1H), 7.06 (d, J=13.3 Hz, 1H), 6.93 (s, 1H), 5.35 (ddd, J=13.0, 8.7, 4.2 Hz, 1H), 4.00 (dt, J=12.0, 4.4 Hz, 2H), 3.67 (ddd, J=12.0, 9.3, 2.9 Hz, 2H), 3.17 (dt, J=3.4, 1.6 Hz, 2H), 2.65 (t, J=11.4 Hz, 2H), 2.58-2.54 (m, 2H), 2.37 (s, 3H), 2.21-2.16 (m, 2H), 1.88-1.81 (m, 2H), 1.17 (d, J=6.4 Hz, 6H); LCMS [M+1]$^+$=605.39.

Example 696: N-[5-[1-(5-cyano-1,3-thiazol-2-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

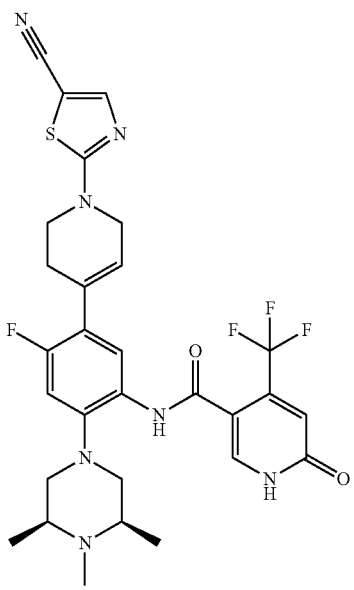

A procedure similar to Example 270 using N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) and 2-bromo-5-cyanothiazole (9.31 mg, 0.049 mmol) afforded the title compound (10.5 mg, 33% yield). $^1$H NMR (500 MHz, METHANOL-d4) δ=7.86-7.82 (m, 1H), 7.77-7.72 (m, 1H), 7.72-7.64 (m, 1H), 6.89-6.83 (m, 1H), 6.82-6.78 (m, 1H), 6.03-5.96 (m, 1H), 4.13-4.08 (m, 2H), 3.82-3.71 (m, 2H), 2.97-2.87 (m, 2H), 2.64-2.54 (m, 2H), 2.52-2.39 (m, 4H), 2.30-2.24 (m, 3H), 1.08-1.03 (m, 6H); LCMS [M+H]+ 616.4.

Example 697: N-[4-fluoro-5-[2-[(2R,6S)-2,6-dimethylmorpholin-4-yl]pyrimidin-4-yl]-2-[(3S,5R)-3,4,5-trimethylpiperazin-1-yl]phenyl]-6-oxo-4-(trifluoromethyl)-1H-pyridine-3-carboxamide

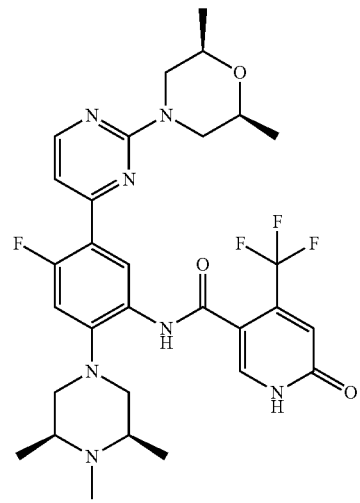

Step 1: 2-((2S,6R)-2,6-dimethylmorpholino)pyrimidin-4(3H)-one

To 2-methylthio-4-pyrimidone (0.6 g, 4.22 mmol) was added cis-2,6-dimethylmorpholine (0.650 mL, 5.28 mmol). The mixture was heated to 145° C. for 2 hours in the microwave, then cooled to room temperature. The solid was crystallized from ethanol. The white needles were washed with EtOH and collected by centrifugation at 4000 RPM. The product was freeze dried for 2 days to afford 2-((2S,6R)-2,6-dimethylmorpholino)pyrimidin-4(3H)-one (308 mg, 35% yield) as a white powder. $^1$H NMR (500 MHz, MeOD) δ 7.63 (d, J=3.5 Hz, 1H), 5.77 (d, J=6.7 Hz, 1H), 4.18 (d, J=13.0 Hz, 2H), 3.64 (dqd, J=12.5, 6.2, 2.4 Hz, 2H), 2.62 (dd, J=13.2, 10.7 Hz, 2H), 1.21 (d, J=6.2 Hz, 6H); LCMS C18 [M+1]$^+$=210.0.

Step 2: (2S,6R)-4-(4-bromopyrimidin-2-yl)-2,6-dimethylmorpholine

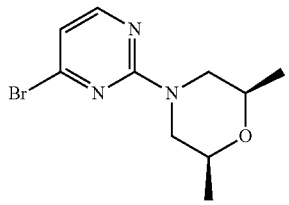

A mixture of 2-((2S,6R)-2,6-dimethylmorpholino)pyrimidin-4(3H)-one (108 mg, 0.516 mmol) and phosphorus(V) oxybromide (192 mg, 0.671 mmol) in acetonitrile (5161 µl) was heated at 82° C. for 1 hour. The reaction was cooled to room temperature, concentrated, and poured over ice. The resulting mixture was neutralized with a saturated solution of NaHCO$_3$, and then extracted with methylene chloride. The organic phase was concentrated and purified by flash column chromatography on silica gel (0-100%, 89% CH$_2$Cl$_2$, 10% MeOH, 1% NH$_4$Ac/CH$_2$Cl$_2$) to afford (2S, 6R)-4-(4-bromopyrimidin-2-yl)-2,6-dimethylmorpholine (106 mg, 74% yield). $^1$H NMR (500 MHz, MeOD) δ 8.07 (d, J=5.1 Hz, 1H), 6.75 (d, J=5.1 Hz, 1H), 4.52 (dd, J=13.2, 1.2 Hz, 2H), 3.60 (dqd, J=12.5, 6.2, 2.4 Hz, 2H), 2.56 (dd, J=13.3, 10.7 Hz, 2H), 1.21 (d, J=6.2 Hz, 6H); LCMS HSS [M+1]$^+$=271.77.

Step 3: N-(5-(2-((2S,6R)-2,6-dimethylmorpholino)pyrimidin-4-yl)-4-fluoro-2-((3S,5R)-3,4,5-trimethylpiperazin-1-yl)phenyl)-4-(trifluoromethyl)-6-(2-(trimethylsilyl)ethoxy)nicotinamide

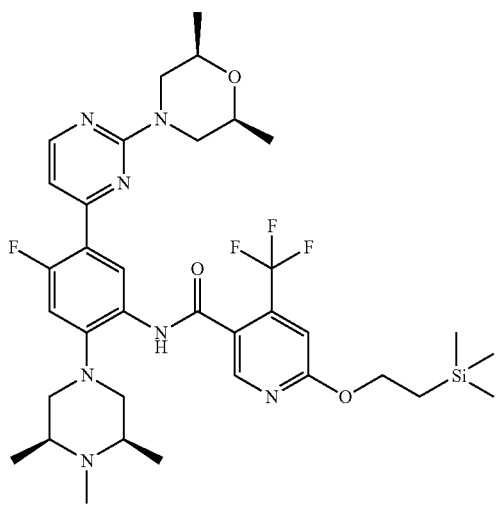 [SMILES: C[C@@H]1CN(c2nccc(-c3cc(NC(=O)c4cnc(OCC[Si](C)(C)C)cc4C(F)(F)F)c(N4C[C@@H](C)N(C)[C@@H](C)C4)cc3F)n2)C[C@H](C)O1]

In N,N-dimethylformamide (DMF) (539 µl) was dissolved N-(4-fluoro-5-(tributylstannyl)-2-((3S,5R)-3,4,5-trimethylpiperazin-1-yl)phenyl)-4-(trifluoromethyl)-6-(2-(trimethylsilyl)ethoxy)nicotinamide (110 mg, 0.135 mmol). To the solution was added (2S,6R)-4-(4-bromopyrimidin-2-yl)-2,6-dimethylmorpholine (40.4 mg, 0.148 mmol), lithium chloride (17.15 mg, 0.405 mmol) and bis(triphenylphosphine)palladium(II) dichloride (5.21 mg, 7.42 µmol) at room temperature and then it was microwaved at the temperature of 120° C. for 3 hours. To the reaction mixture was added water and then it was extracted with dichloromethane. The organic layer was separated, concentrated and purified by column chromatography on silica gel (0-100%, 89% CH$_2$Cl$_2$, 10% MeOH, 1% NH$_4$Ac/CH$_2$Cl$_2$) to afford N-(5-(2-((2S,6R)-2,6-dimethylmorpholino)pyrimidin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide. LCMS [M+1]$^+$=718.26.

Step 4: N-[4-fluoro-5-[2-[(2R,6S)-2,6-dimethylmorpholin-4-yl]pyrimidin-4-yl]-2-[(3S,5R)-3,4,5-trimethylpiperazin-1-yl]phenyl]-6-oxo-4-(trifluoromethyl)-1H-pyridine-3-carboxamide

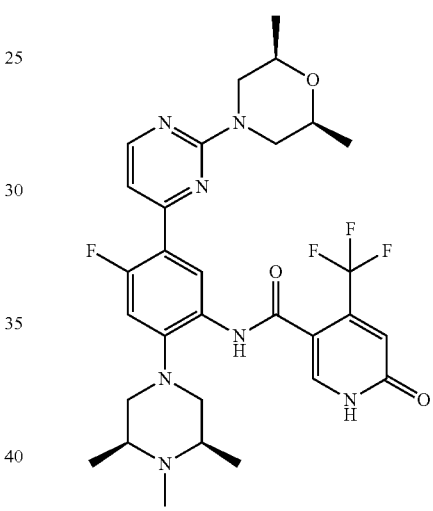

The product was dissolved in 2 mL of DCM and TFA (1033 µl, 13.49 mmol) was added. The purple solution was stirred for 1 h and the solvent was evaporated. The residue was purified using a preparative HPLC followed by a cation exchange column eluting with MeOH:NH$_4$OH and freeze dried for 2 days to afford N-(5-(2-((2S,6R)-2,6-dimethylmorpholino)pyrimidin-4-yl)-4-fluoro-2-((3S,5R)-3,4,5-trimethylpiperazin-1-yl)phenyl)-6-oxo-4-(trifluoromethyl)-1,6-dihydropyridine-3-carboxamide (19 mg, 23% yield) as a white powder. $^1$H NMR (500 MHz, MeOD) δ 8.53 (d, J=8.2 Hz, 1H), 8.26 (d, J=5.2 Hz, 1H), 7.78 (s, 1H), 7.01 (dd, J=5.2, 1.7 Hz, 1H), 6.90 (d, J=13.2 Hz, 1H), 6.82 (s, 1H), 4.57 (d, J=12.8 Hz, 2H), 3.56 (ddd, J=10.4, 6.3, 2.4 Hz, 2H), 3.06 (d, J=11.2 Hz, 2H), 2.56-2.45 (m, 6H), 2.28 (s, 3H), 1.14 (d, J=6.2 Hz, 6H), 1.08 (d, J=6.1 Hz, 6H); 19F NMR (471 MHz, MeOD) δ −63.66 (s), −115.74 (s); LCMS [M+1]$^+$=618.34.

Example 698: N-[4-fluoro-5-[2-[(2R,6S)-2,6-dimethylmorpholin-4-yl]pyrimidin-4-yl]-2-[(3R)-3,4-dimethylpiperazin-1-yl]phenyl]-6-oxo-4-(trifluoromethyl)-1H-pyridine-3-carboxamide

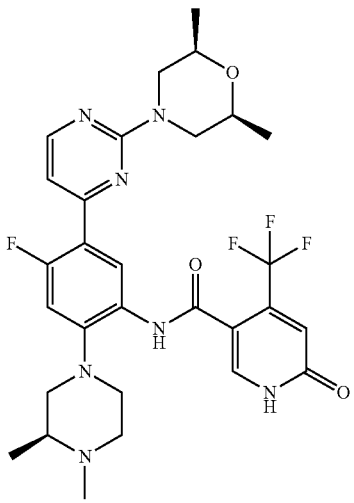 [SMILES: C[C@@H]1CN(c2nccc(-c3cc(NC(=O)c4c[nH]c(=O)cc4C(F)(F)F)c(N4CCN(C)[C@@H](C)C4)cc3F)n2)C[C@H](C)O1]

Step 1: (S)—N-(2-(3,4-dimethylpiperazin-1-yl)-4-fluoro-5-(tributylstannyl)phenyl)-4-(trifluoromethyl)-6-(2-(trimethylsilyl)ethoxy)nicotinamide

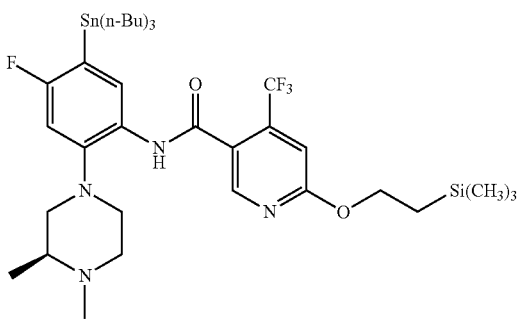

A stirred solution of (S)—N-(5-bromo-2-(3,4-dimethylpiperazin-1-yl)-4-fluorophenyl)-4-(trifluoromethyl)-6-(2-(trimethylsilyl)ethoxy)nicotinamide (4 g, 6.77 mmol, 1 eq) in toluene (40 mL) was degassed with argon for 15 mins, then hexabutylditin (6.89 mL, 13.5 mmol, 2 eq) was added, followed by Pd$_2$(dppf)$_2$Cl$_2$ (0.55 g, 0.67 mmol, 0.1 eq) and after that heated to reflux under argon atmosphere for 16 h. TLC analysis indicated formation of less polar spots. The reaction mixture was filtered through celite bed washed with EtOAc; the filtrate was evaporated under reduced pressure. The crude compound was purified by column chromatography (neutral alumina) using 0-30% EtOAc in pet ether as an eluent to afford (S)—N-(2-(3,4-dimethylpiperazin-1-yl)-4-fluoro-5-(tributylstannyl)phenyl)-4-(trifluoromethyl)-6-(2-(trimethylsilyl)ethoxy)nicotinamide (2.8 g, 51%) as a pale yellow liquid. LCMS: [M+H]+ 803.16.

Step 2: N-(5-(2-((2S,6R)-2,6-dimethylmorpholino)pyrimidin-4-yl)-2-((S)-3,4-dimethylpiperazin-1-yl)-4-fluorophenyl)-6-oxo-4-(trifluoromethyl)-1,6-dihydropyridine-3-carboxamide

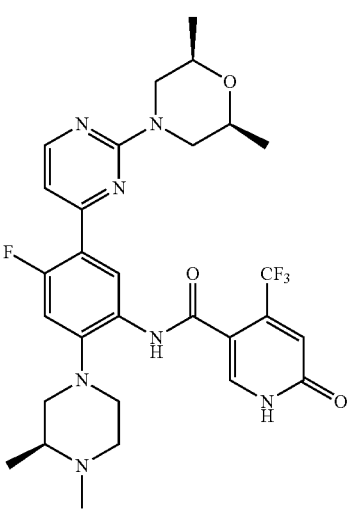 [SMILES: C[C@@H]1CN(c2nccc(-c3cc(NC(=O)c4c[nH]c(=O)cc4C(F)(F)F)c(N4CCN(C)[C@@H](C)C4)cc3F)n2)C[C@H](C)O1]

The title compound (10.1 mg, 12% yield) was prepared similar to the sequence described above for the preparation of Example 697 using (S)—N-(2-(3,4-dimethylpiperazin-1-yl)-4-fluoro-5-(tributylstannyl)phenyl)-4-(trifluoromethyl)-6-(2-(trimethylsilyl)ethoxy)nicotinamide (115 mg, 0.143 mmol) and (2S,6R)-4-(4-bromopyrimidin-2-yl)-2,6-dimethylmorpholine (42.9 mg, 0.158 mmol). $^1$H NMR (500 MHz, MeOD) δ 8.63 (d, J=8.2 Hz, 1H), 8.36 (d, J=5.2 Hz, 1H), 7.90 (s, 1H), 7.11 (dd, J=5.2, 1.7 Hz, 1H), 7.02 (d, J=13.2 Hz, 1H), 6.92 (s, 1H), 4.67 (d, J=13.0 Hz, 2H), 3.66 (ddd, J=10.3, 6.2, 2.3 Hz, 2H), 3.21 (d, J=11.0 Hz, 1H), 3.15 (d, J=12.4 Hz, 1H), 2.96 (t, J=10.2 Hz, 2H), 2.63-2.57 (m, 4H), 2.45 (s, 1H), 2.39 (s, 3H), 1.24 (d, J=6.2 Hz, 6H), 1.15 (d, J=6.3 Hz, 3H); $^{19}$F NMR (471 MHz, MeOD) δ−63.74 (s), −115.95 (s); LCMS HSS [M+1]$^+$=604.27.

845

Example 699: (1-methylcyclobutyl) 4-[2-fluoro-5-[[6-oxo-4-(trifluoromethyl)-1H-pyridine-3-carbonyl]amino]-4-[(3R,5S)-3,4,5-trimethylpiperazin-1-yl]phenyl]-2,3,6,7-tetrahydroazepine-1-carboxylate

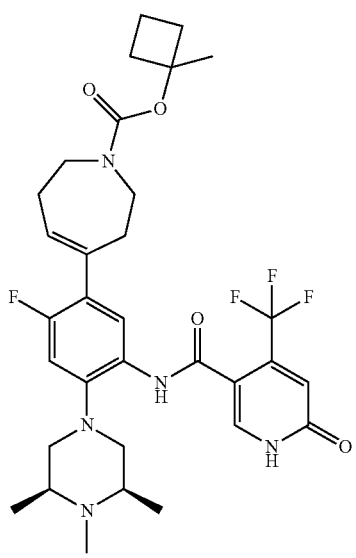 [SMILES: C[C@@H]1CN(c2cc(F)c(C3=CCCN(C(=O)OC4(C)CCC4)CC3)cc2NC(=O)c2c[nH]c(=O)cc2C(F)(F)F)C[C@H](C)N1C]

To a solution of N-(4-fluoro-5-(2,3,6,7-tetrahydro-1H-azepin-4-yl)-2-((3S,5R)-3,4,5-trimethylpiperazin-1-yl)phenyl)-6-oxo-4-(trifluoromethyl)-1,6-dihydropyridine-3-carboxamide (30.6 mg, 0.059 mmol) and 1-methylcyclobutyl (4-nitrophenyl) carbonate (15.48 mg, 0.062 mmol) in DCM (3 ml) was added pyridine (0.019 ml, 0.235 mmol). The reaction mixture was heated at 90° C. for 1 h. It was cooled down and concentrated onto celite. The crude was purified on Isco (4 g silica column, eluting with DCM containing 0-5% MeOH and 0-0.5% NH$_4$OH). The desired product was lyophilized from water/acetonitrile to afford the title compound as a white fluffy powder (18 mg, 0.027 mmol, 46.0% yield). $^1$H NMR (500 MHz, METHANOL-d4) δ=7.91 (br d, J=3.9 Hz, 1H), 7.70-7.59 (m, 1H), 6.95-6.87 (m, 2H), 6.00-5.88 (m, 1H), 4.04 (br s, 2H), 3.69-3.61 (m, 2H), 3.61-3.52 (m, 1H), 3.00 (br d, J=10.9 Hz, 2H), 2.61 (br d, J=5.7 Hz, 2H), 2.56 (br d, J=11.2 Hz, 2H), 2.52-2.41 (m, 2H), 2.36 (s, 3H), 2.34-2.25 (m, 2H), 2.17-2.04 (m, 2H), 1.92 (br d, J=5.7 Hz, 1H), 1.81 (br dd, J=2.2, 5.1 Hz, 1H), 1.75-1.62 (m, 1H), 1.59-1.53 (m, 3H), 1.15 (d, J=5.9 Hz, 6H); LCMS 634.

846

Example 700: N-[5-[1-(5-cyano-1,3-thiazol-2-yl)-2,3,6,7-tetrahydroazepin-4-yl]-4-fluoro-2-[(3R,5S)-3,4,5-trimethylpiperazin-1-yl]phenyl]-6-oxo-4-(trifluoromethyl)-1H-pyridine-3-carboxamide

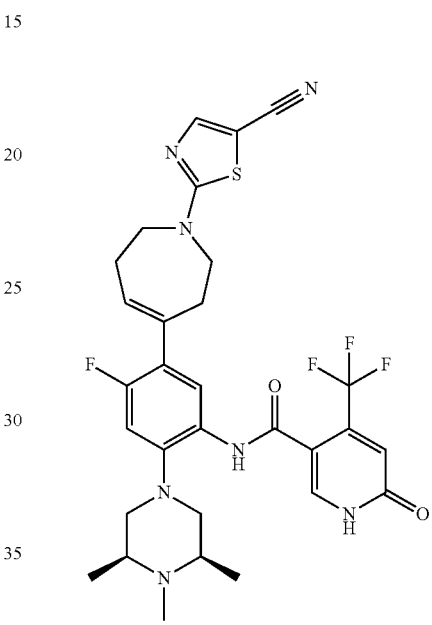

A procedure similar to Example 270 using N-(4-fluoro-5-(2,3,6,7-tetrahydro-1H-azepin-4-yl)-2-((3S,5R)-3,4,5-trimethylpiperazin-1-yl)phenyl)-6-oxo-4-(trifluoromethyl)-1,6-dihydropyridine-3-carboxamide (30 mg, 0.058 mmol) and 2-bromo-5-cyanothiazole (10.87 mg, 0.058 mmol) afforded the title compound as a white fluffy powder (23 mg, 0.035 mmol, 60.3% yield). $^1$H NMR (500 MHz, METHANOL-d4) δ=7.81 (s, 1H), 7.68 (s, 1H), 7.55 (br d, J=8.1 Hz, 1H), 6.85-6.79 (m, 2H), 6.02-5.95 (m, 1H), 4.24 (br d, J=5.1 Hz, 2H), 3.81 (br t, J=5.4 Hz, 3H), 2.89 (br d, J=11.0 Hz, 3H), 2.59-2.53 (m, 3H), 2.45 (br d, J=11.4 Hz, 3H), 2.41 (br d, J=4.5 Hz, 2H), 2.25 (s, 4H), 2.02-1.95 (m, 2H), 1.04 (d, J=6.0 Hz, 6H); LCMS [M+H]$^+$ 630.

Example 701: N-[5-[1-(2-cyanopyrimidin-4-yl)-3,6-dihydro-2H-pyridin-5-yl]-4-fluoro-2-[(3R,5S)-3,4,5-trimethylpiperazin-1-yl]phenyl]-6-oxo-4-(trifluoromethyl)-1H-pyridine-3-carboxamide

Example 702 (3,3-difluorocyclobutyl) 4-[5-[[4-(difluoromethyl)-6-oxo-1H-pyridine-3-carbonyl]amino]-2-fluoro-4-[(3R,5S)-3,4,5-trimethylpiperazin-1-yl]phenyl]-3,6-dihydro-2H-pyridine-1-carboxylate

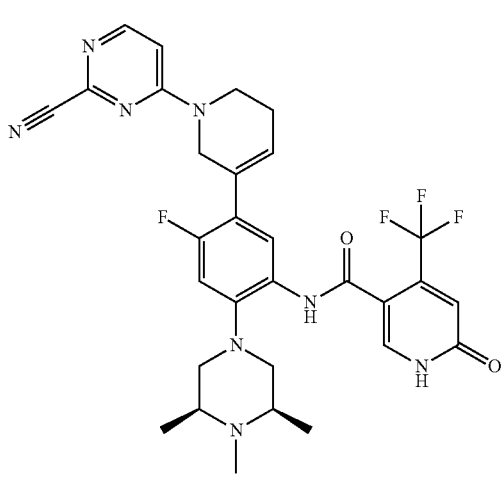 [SMILES: C[C@@H]1CN(c2cc(F)c(C3=CCCN(c4ccnc(C#N)n4)C3)cc2NC(=O)c2c[nH]c(=O)cc2C(F)(F)F)C[C@H](C)N1C]

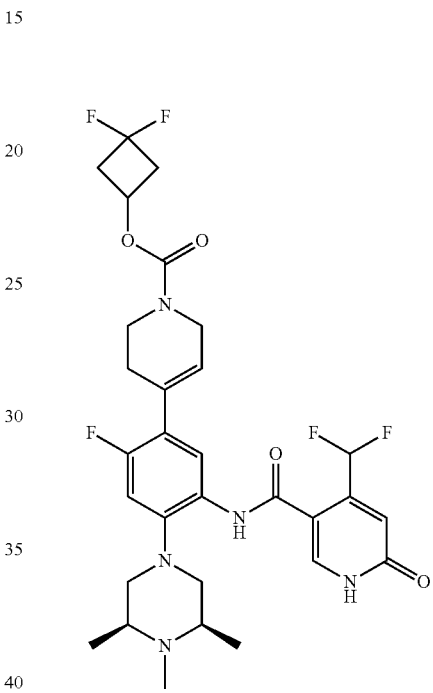

A mixture of cesium carbonate (32.1 mg, 0.099 mmol), 4-bromopyrimidine-2-carbonitrile (9.97 mg, 0.054 mmol), and N-(4-fluoro-5-(1,2,5,6-tetrahydropyridin-3-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) in NMP was heated in an oil bath at 85° C. for 0.5-5 h. The reaction mixture was concentrated to dryness, partitioned between DCM and water, the org phase was separated, aq phase was extracted with DCM (2×), the combined org phase was washed with brine, dried over $Na_2SO_4$ and concentrated to afford a brown residue which was concentrated onto celite and purified on Isco (4 g) column, eluting with DCM containing 0-5% MeOH and 0-0.5% $NH_4OH$. The desired product was isolated as an off white solid (10 mg, 32%) $^1H$ NMR (500 MHz, METHANOL-d4) δ=8.12-8.07 (m, 1H), 7.87-7.82 (m, 1H), 7.71-7.64 (m, 1H), 6.93-6.85 (m, 2H), 6.82-6.78 (m, 1H), 6.14-6.04 (m, 1H), 4.50-4.18 (m, 2H), 3.97-3.69 (m, 2H), 3.00-2.91 (m, 2H), 2.52-2.46 (m, 2H), 2.46-2.40 (m, 2H), 2.38-2.33 (m, 2H), 2.28-2.25 (m, 3H), 1.07-1.04 (m, 6H), 0.04-0.02 (m, 1H); LCMS [M+H]+ 611.5.

The procedure followed was similar to Example 253 using 4-(difluoromethyl)-N-(4-fluoro-5-(1,2,3,6-tetrahydropyridin-4-yl)-2-((3S,5R)-3,4,5-trimethylpiperazin-1-yl)phenyl)-6-oxo-1,6-dihydropyridine-3-carboxamide (25 mg, 0.051 mmol) and 3,3-difluorocyclobutyl-(4-nitrophenyl) carbonate (15.35 mg, 0.056 mmol) to give the title compound (21 mg, 63% yield). $^1H$ NMR (500 MHz, METHANOL-d4) δ 7.85-7.91 (m, 1H), 7.56 (d, J=8.19 Hz, 1H), 7.07-7.32 (m, 1H), 6.81 (d, J=12.47 Hz, 1H), 6.69 (s, 1H), 5.88 (br. s., 1H), 4.78-4.84 (m, 1H), 3.95-4.08 (m, 2H), 3.51-3.62 (m, 2H), 2.88-2.97 (m, 4H), 2.55-2.67 (m, 2H), 2.55-2.67 (m, 2H), 2.36-2.48 (m, 6H), 2.24 (s, 3H), 1.03 (d, J=5.99 Hz, 6H); LCMS [M+H]+ 624.5.

Example 703: (3,3-difluorocyclobutyl) 4-[5-[[4-(difluoromethyl)-6-oxo-1H-pyridine-3-carbonyl]amino]-2-fluoro-4-[(3R)-3,4-dimethylpiperazin-1-yl]phenyl]-3,6-dihydro-2H-pyridine-1-carboxylate

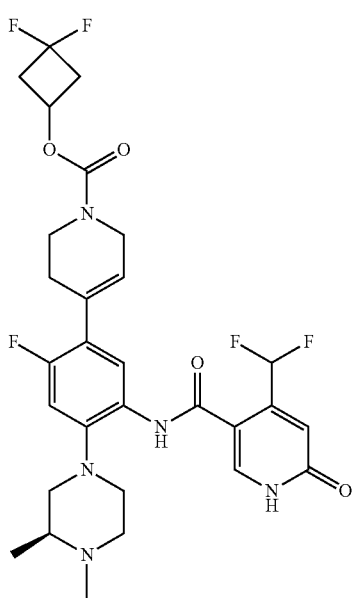 [SMILES: C[C@H]1CN(c2cc(F)c(C3=CCN(C(=O)OC4CC(F)(F)C4)CC3)cc2NC(=O)c2c[nH]c(=O)cc2C(F)F)CCN1C]

The procedure was similar to that of Example 253 using (S)-4-(difluoromethyl)-N-(2-(3,4-dimethylpiperazin-1-yl)-4-fluoro-5-(1,2,3,6-tetrahydropyridin-4-yl)phenyl)-6-oxo-1,6-dihydropyridine-3-carboxamide (25 mg, 0.053 mmol) and 3,3-difluorocyclobutyl (4-nitrophenyl) carbonate (15.80 mg, 0.058 mmol) to give the title compound (26 mg, 77% yield). $^1$H NMR (500 MHz, METHANOL-d4) δ 7.86-7.92 (m, 1H), 7.57 (d, J=8.19 Hz, 1H), 7.07-7.31 (m, 1H), 6.84 (d, J=12.47 Hz, 1H), 6.70 (s, 1H), 5.88 (br. s., 1H), 4.79-4.86 (m, 1H), 3.95-4.10 (m, 2H), 3.51-3.63 (m, 2H), 2.88-2.99 (m, 4H), 2.75-2.83 (m, 2H), 2.54-2.68 (m, 2H), 2.37-2.45 (m, 4H), 2.22-2.29 (m, 4H), 1.00 (d, J=6.36 Hz, 3H); LCMS [M+H]+ 610.5.

Example 704: (3,3-difluorocyclobutyl) 5-[5-[[4-(difluoromethyl)-6-oxo-1H-pyridine-3-carbonyl]amino]-2-fluoro-4-[(3R,5S)-3,4,5-trimethylpiperazin-1-yl]phenyl]-3,6-dihydro-2H-pyridine-1-carboxylate

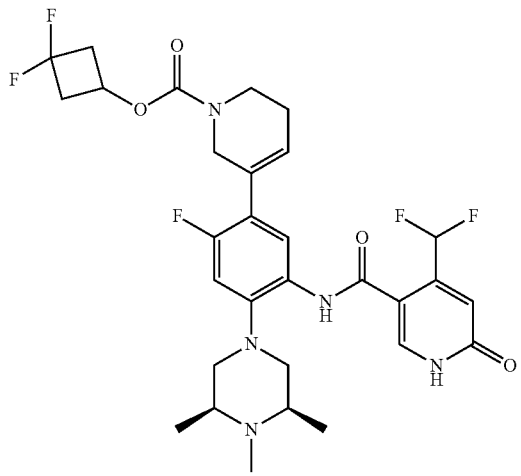 [SMILES: C[C@@H]1CN(c2cc(F)c(C3=CCCN(C(=O)OC4CC(F)(F)C4)C3)cc2NC(=O)c2c[nH]c(=O)cc2C(F)F)C[C@H](C)N1C]

The procedure followed was similar to Example 253 using 4-(difluoromethyl)-N-(4-fluoro-5-(1,2,5,6-tetrahydropyridin-3-yl)-2-((3S,5R)-3,4,5-trimethylpiperazin-1-yl)phenyl)-6-oxo-1,6-dihydropyridine-3-carboxamide (25 mg, 0.051 mmol) and 3,3-difluorocyclobutyl (4-nitrophenyl) carbonate (15.35 mg, 0.056 mmol) to give the title compound (26 mg, 77% yield). $^1$H NMR (500 MHz, METHANOL-d4) δ 7.88 (s, 1H), 7.55 (d, J=8.07 Hz, 1H), 7.07-7.32 (m, 1H), 6.84 (d, J=12.35 Hz, 1H), 6.70 (s, 1H), 5.99 (br. s., 1H), 4.78-4.84 (m, 1H), 4.15 (d, J=17.12 Hz, 2H), 3.52 (d, J=19.81 Hz, 2H), 2.93 (d, J=11.13 Hz, 4H), 2.60 (d, J=6.36 Hz, 2H), 2.43-2.50 (m, 2H), 2.35-2.43 (m, 2H), 2.25 (s, 5H), 1.04 (d, J=5.99 Hz, 6H); LCMS [M+H]+ 624.

Example 705: (3,3-difluorocyclobutyl) 5-[5-[[4-(difluoromethyl)-6-oxo-1H-pyridine-3-carbonyl]amino]-2-fluoro-4-[(3R)-3,4-dimethylpiperazin-1-yl]phenyl]-3,6-dihydro-2H-pyridine-1-carboxylate

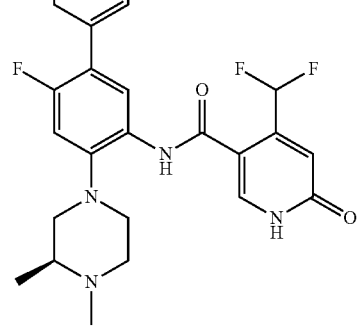

The procedure followed was similar to that of Example 253 using (S)-4-(difluoromethyl)-N-(2-(3,4-dimethylpiperazin-1-yl)-4-fluoro-5-(1,2,5,6-tetrahydropyridin-3-yl)phenyl)-6-oxo-1,6-dihydropyridine-3-carboxamide (25 mg, 0.053 mmol) and 3,3-difluorocyclobutyl (4-nitrophenyl) carbonate (15.80 mg, 0.058 mmol) to give the title compound (23 mg, 68% yield). ¹H NMR (500 MHz, METHANOL-d4) δ 11.86-11.88 (m, 1H), 7.86-7.92 (m, 1H), 7.57 (d, J=8.07 Hz, 1H), 7.07-7.32 (m, 1H), 7.07-7.32 (m, 1H), 7.07-7.32 (m, 1H), 6.86 (d, J=12.23 Hz, 1H), 6.70 (s, 1H), 5.99 (br. s., 1H), 4.78-4.85 (m, 1H), 4.15 (d, J=17.36 Hz, 2H), 3.53 (d, J=19.68 Hz, 2H), 2.88-3.00 (m, 4H), 2.76-2.83 (m, 2H), 2.60 (d, J=5.50 Hz, 2H), 2.37-2.44 (m, 2H), 2.23-2.31 (m, 6H), 1.00 (d, J=6.24 Hz, 3H); LCMS [M+H]+ 610.5.

Example 706: (3,3-difluorocyclobutyl) 5-[2-fluoro-5-[[4-fluoro-2-(trifluoromethyl)benzoyl]amino]-4-[(3R)-3,4-dimethylpiperazin-1-yl]phenyl]-3,6-dihydro-2H-pyridine-1-carboxylate

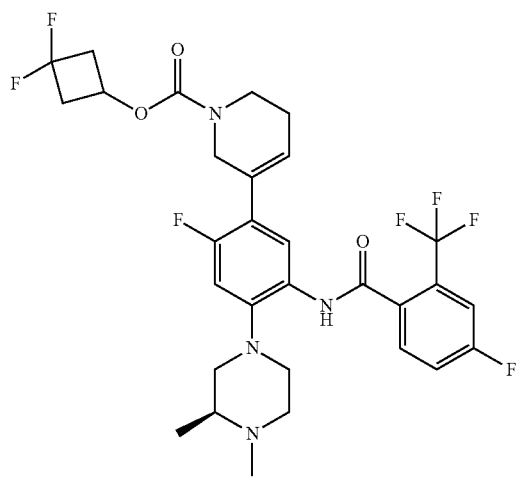 [SMILES: C[C@H]1CN(c2cc(F)c(C3=CCCN(C(=O)OC4CC(F)(F)C4)C3)cc2NC(=O)c2ccc(F)cc2C(F)(F)F)CCN1C]

The procedure was similar to Example 253 using (S)—N-(2-(3,4-dimethylpiperazin-1-yl)-4-fluoro-5-(1,2,5,6-tetrahydropyridin-3-yl)phenyl)-4-fluoro-2-(trifluoromethyl)benzamide (25 mg, 0.051 mmol) and 3,3-difluorocyclobutyl (4-nitrophenyl) carbonate (15.19 mg, 0.056 mmol) to give the title compound (22.5 mg, 67% yield). ¹H NMR (500 MHz, METHANOL-d4) δ=7.79-7.73 (m, 1H), 7.67-7.62 (m, 1H), 7.56-7.52 (m, 1H), 7.47-7.42 (m, 1H), 6.93-6.86 (m, 1H), 6.05-5.99 (m, 1H), 4.85-4.78 (m, 1H), 4.23-4.13 (m, 2H), 3.58-3.48 (m, 2H), 2.99-2.88 (m, 4H), 2.84-2.77 (m, 2H), 2.66-2.54 (m, 2H), 2.47-2.39 (m, 1H), 2.38-2.32 (m, 1H), 2.29-2.20 (m, 6H), 1.02-0.99 (m, 3H); LCMS [M+H]+ 629.4.

Example 707: (3,3-difluorocyclobutyl) 4-[2-fluoro-5-[[4-fluoro-2-(trifluoromethyl)benzoyl]amino]-4-[(3R)-3,4-dimethylpiperazin-1-yl]phenyl]-3,6-dihydro-2H-pyridine-1-carboxylate

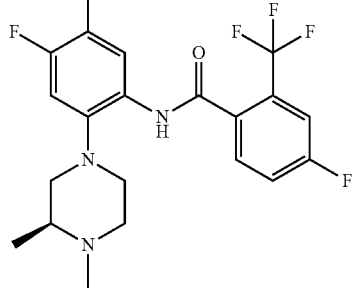

The procedure followed was similar to that of Example 253 using (S)—N-(2-(3,4-dimethylpiperazin-1-yl)-4-fluoro-5-(1,2,3,6-tetrahydropyridin-4-yl)phenyl)-4-fluoro-2-(trifluoromethyl)benzamide (25 mg, 0.051 mmol) and 3,3-difluorocyclobutyl (4-nitrophenyl) carbonate (15.19 mg, 0.056 mmol) to afford the title compound (17 mg, 51% yield). ¹H NMR (500 MHz, METHANOL-d4) δ 7.77 (d, J=8.07 Hz, 1H), 7.64 (dd, J=5.32, 8.50 Hz, 1H), 7.54 (dd, J=2.38, 9.11 Hz, 1H), 7.45 (dt, J=2.38, 8.28 Hz, 1H), 6.87 (d, J=12.35 Hz, 1H), 5.90 (br. s., 1H), 4.79-4.85 (m, 1H), 3.98-4.09 (m, 2H), 3.54-3.63 (m, 2H), 2.88-2.98 (m, 4H), 2.76-2.82 (m, 2H), 2.56-2.67 (m, 2H), 2.39-2.47 (m, 3H), 2.31-2.37 (m, 1H), 2.19-2.25 (m, 4H), 0.99 (d, J=6.36 Hz, 3H); LCMS [M+H]+ 629.5.

Example 708: N-[5-[1-(2-cyanopyrimidin-4-yl)-3,6-dihydro-2H-pyridin-4-yl]-4-fluoro-2-[(3R)-3,4-dimethylpiperazin-1-yl]phenyl]-4-(difluoromethyl)-6-oxo-1H-pyridine-3-carboxamide

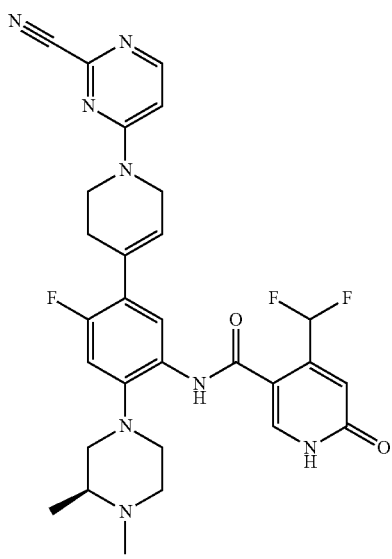 [SMILES: C[C@H]1CN(c2cc(F)c(C3=CCN(c4ccnc(C#N)n4)CC3)cc2NC(=O)c2c[nH]c(=O)cc2C(F)F)CCN1C]

Example 709: N-[5-[1-(2-cyanopyrimidin-4-yl)-3,6-dihydro-2H-pyridin-4-yl]-4-fluoro-2-[(3R,5S)-3,4,5-trimethylpiperazin-1-yl]phenyl]-6-oxo-4-(trifluoromethyl)-1H-pyridine-3-carboxamide

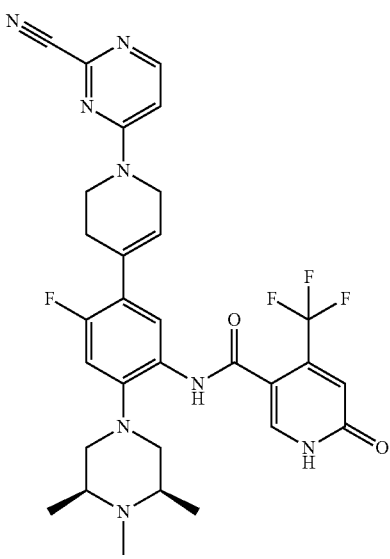 [SMILES: C[C@@H]1CN(c2cc(F)c(C3=CCN(c4ccnc(C#N)n4)CC3)cc2NC(=O)c2c[nH]c(=O)cc2C(F)(F)F)C[C@H](C)N1C]

The procedure followed was similar to that of Example 270 using cesium carbonate (34.3 mg, 0.105 mmol), 4-bromopyrimidine-2-carbonitrile (10.64 mg, 0.058 mmol) and (S)-4-(difluoromethyl)-N-(2-(3,4-dimethylpiperazin-1-yl)-4-fluoro-5-(1,2,3,6-tetrahydropyridin-4-yl)phenyl)-6-oxo-1,6-dihydropyridine-3-carboxamide (25 mg, 0.053 mmol) in NMP to give the title compound (5.5 mg, 17% yield). $^1$H NMR (500 MHz, METHANOL-d4) δ=8.35-8.19 (m, 1H), 8.15-8.08 (m, 1H), 7.98-7.90 (m, 1H), 7.62-7.53 (m, 1H), 7.31-7.06 (m, 1H), 6.95-6.81 (m, 2H), 6.72-6.68 (m, 1H), 6.06-5.99 (m, 1H), 4.31-4.03 (m, 2H), 4.01-3.72 (m, 2H), 3.28-3.23 (m, 1H), 3.15-3.07 (m, 2H), 3.01-2.89 (m, 3H), 2.72-2.61 (m, 4H), 2.54 (br s, 2H), 1.21-1.19 (m, 3H); LCMS [M+H]+ 579.5.

The procedure followed was similar to Example 270 using cesium carbonate (32.1 mg, 0.099 mmol), 4-bromopyrimidine-2-carbonitrile (9.97 mg, 0.054 mmol) and N-(4-fluoro-5-(1,2,3,6-tetrahydropyridin-4-yl)-2-((3S,5R)-3,4,5-trimethylpiperazin-1-yl)phenyl)-6-oxo-4-(trifluoromethyl)-1,6-dihydropyridine-3-carboxamide (25 mg, 0.049 mmol) in NMP to give the title compound (6 mg, 19% yield). $^1$H NMR (500 MHz, METHANOL-d4) δ=8.14-8.09 (m, 1H), 7.89-7.83 (m, 1H), 7.75-7.69 (m, 1H), 6.95-6.90 (m, 1H), 6.89-6.79 (m, 2H), 6.08-5.99 (m, 1H), 4.31-4.05 (m, 2H), 4.00-3.73 (m, 2H), 3.08-3.03 (m, 2H), 3.01-2.88 (m, 2H), 2.70-2.63 (m, 2H), 2.58-2.53 (m, 5H), 1.20-1.18 (m, 6H); LCMS [M+H]+ 611.4.

Example 710: N-[5-[4-(cyclohexylcarbamoyl)-3,5-difluorophenyl]-4-fluoro-2-[(3R,5S)-3,4,5-trimethylpiperazin-1-yl]phenyl]-6-oxo-4-(trifluoromethyl)-1H-pyridine-3-carboxamide

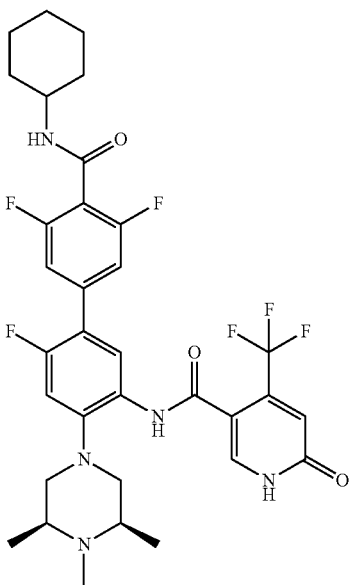

Step 1: 2',3,5-trifluoro-5'-(6-oxo-4-(trifluoromethyl)-1,6-dihydropyridine-3-carboxamido)-4'-((3S,5R)-3,4,5-trimethylpiperazin-1-yl)-[1,1'-biphenyl]-4-carboxylic acid

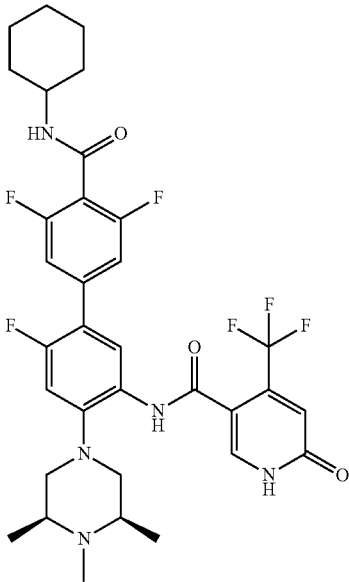 [SMILES: C[C@@H]1CN(c2cc(F)c(-c3cc(F)c(C(=O)NC4CCCCC4)c(F)c3)cc2NC(=O)c2c[nH]c(=O)cc2C(F)(F)F)C[C@H](C)N1C]

N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (300 mg, 0.495 mmol), 3,5-difluoro-4-carboxyphenylboronic acid (200 mg, 0.991 mmol) and potassium phosphate tribasic reagent grade, >=98% (158 mg, 0.743 mmol) were mixed in 1,4-dioxane (10 ml). Water was added and the vial was flushed with nitrogen. The reaction mixture was heated in a microwave reactor to 1 h at 100° C. The reaction mixture was cooled to RT, partitioned between DCM and water, and neutralized with citric acid (1N, 0.8 ml, PH 5~6). The aq phase was extracted several times with DCM/i-PrOH/CHCl₃. The compound formed a suspension. Some brine and some water were added to break up the suspension. The milky organic layer was evaporated as is without drying. The crude product was suspended in DCM (5 ml), and TFA (2 ml) was added. The suspension was stirred at rt for 30 min upon which LCMS showed completion. The solvents were evaporated off and the residue was taken up in MeOH and passed through a cation exchange resin cartridge (2 g porapak, 20 cc capacity) prewashed with MeOH, it was eluted with MeOH then 3% NH₄OH in MeOH. The fractions containing all the product were concentrated down. The residue was taken in some acetonitrile, some water was added. It was then lyophilized to afford the product as a light yellow fluffy powder. LCMS [M+H]+ 583.2.

Step 2: N-[5-[4-(cyclohexylcarbamoyl)-3,5-difluorophenyl]-4-fluoro-2-[(3R,5S)-3,4,5-trimethylpiperazin-1-yl]phenyl]-6-oxo-4-(trifluoromethyl)-1H-pyridine-3-carboxamide

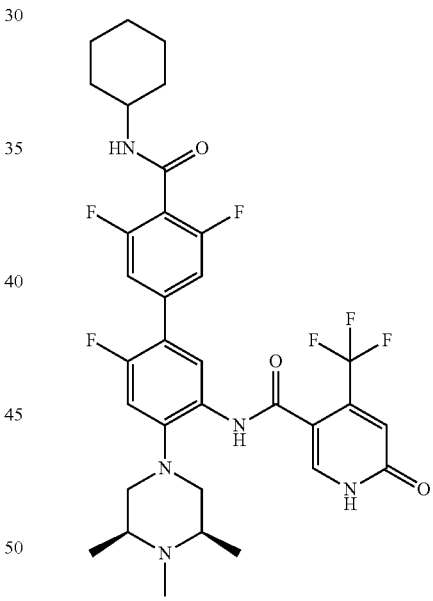

HATU (29.4 mg, 0.077 mmol), cyclohexylamine (7.66 mg, 0.077 mmol) and 2',3,5-trifluoro-5'-(6-oxo-4-(trifluoromethyl)-1,6-dihydropyridine-3-carboxamido)-4'-((3S,5R)-3,4,5-trimethylpiperazin-1-yl)-[1,1'-biphenyl]-4-carboxylic acid (30 mg, 0.052 mmol) were charged into a 30 ml vial. N,N-dimethylformamide (1.5 ml) was added then the mixture was stirred at rt for 5 min upon which N,N-diisopropylethylamine (0.036 ml, 0.206 mmol) was added. The mixture was stirred at ambient temperature for 30 min and the reaction was stopped. It was purified by reverse phase Isco (C18 13.3 g column; eluent:10%, 10-70%, then 70% AcCN/water) to give the title compound after lyophilization as a white fluffy powder (6.7 mg, 9.59 μmol, 18.6% yield). ¹H NMR (500 MHz, METHANOL-d4)

δ=7.88 (s, 1H), 7.83 (d, J=8.2 Hz, 1H), 7.16 (d, J=8.4 Hz, 2H), 6.97 (d, J=12.3 Hz, 1H), 6.82-6.77 (m, 1H), 3.82-3.72 (m, 1H), 2.99 (br d, J=11.2 Hz, 2H), 2.89 (s, 1H), 2.54-2.49 (m, 2H), 2.47-2.39 (m, 2H), 2.26 (s, 3H), 1.92-1.84 (m, 2H), 1.75-1.66 (m, 2H), 1.62-1.54 (m, 1H), 1.38-1.28 (m, 2H), 1.27-1.10 (m, 4H), 1.06 (d, J=6.1 Hz, 6H); LCMS [M+H]+ 664.

Example 711: N-[5-[4-[(2,2-dimethylcyclohexyl)carbamoyl]-3,5-difluorophenyl]-4-fluoro-2-[(3R,5S)-3,4,5-trimethylpiperazin-1-yl]phenyl]-6-oxo-4-(trifluoromethyl)-1H-pyridine-3-carboxamide

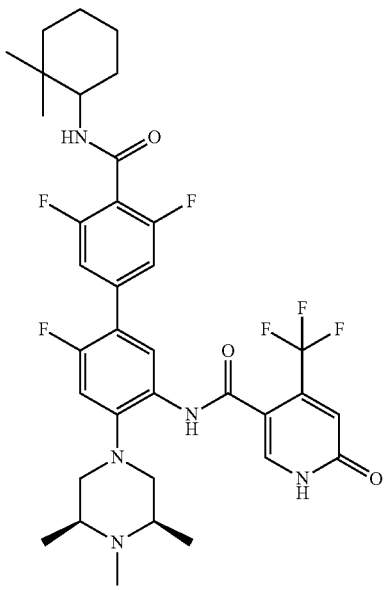 [SMILES: C[C@@H]1CN(c2cc(F)c(-c3cc(F)c(C(=O)NC4CCCCC4(C)C)c(F)c3)cc2NC(=O)c2c[nH]c(=O)cc2C(F)(F)F)C[C@H](C)N1C]

Example 712: N-[5-[4-(cyclopropylmethylcarbamoyl)-3,5-difluorophenyl]-4-fluoro-2-[(3R,5S)-3,4,5-trimethylpiperazin-1-yl]phenyl]-6-oxo-4-(trifluoromethyl)-1H-pyridine-3-carboxamide

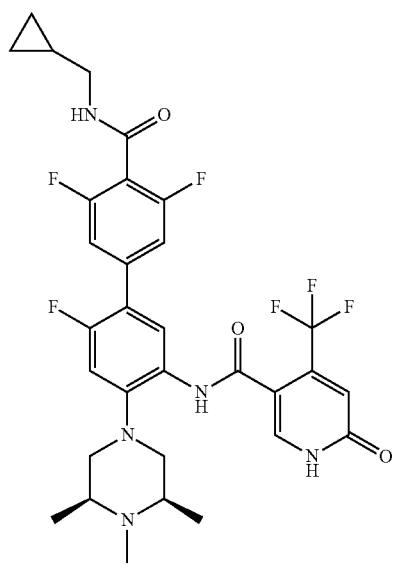 [SMILES: C[C@@H]1CN(c2cc(F)c(-c3cc(F)c(C(=O)NCC4CC4)c(F)c3)cc2NC(=O)c2c[nH]c(=O)cc2C(F)(F)F)C[C@H](C)N1C]

Example 711 was prepared by a similar procedure to that of Example 710 using 2,2-dimethylcyclohexanamine (10.16 mg, 0.080 mmol) and 2',3,5-trifluoro-5'-(6-oxo-4-(trifluoromethyl)-1,6-dihydropyridine-3-carboxamido)-4'-((3S,5R)-3,4,5-trimethylpiperazin-1-yl)-[1,1'-biphenyl]-4-carboxylic acid (31 mg, 0.053 mmol) to give the title compound as a white fluffy powder (3 mg, 4.08 μmol, 7.7% yield). $^1$H NMR (500 MHz, METHANOL-d4) δ=7.98 (s, 1H), 7.85 (d, J=8.2 Hz, 1H), 7.17 (br d, J=8.3 Hz, 2H), 6.97 (d, J=12.3 Hz, 1H), 6.71-6.66 (m, 1H), 3.79 (dd, J=4.1, 11.4 Hz, 1H), 2.99 (br d, J=11.5 Hz, 3H), 2.87 (br d, J=11.4 Hz, 1H), 2.54-2.48 (m, 2H), 2.45-2.37 (m, 2H), 2.25 (s, 3H), 1.73-1.66 (m, 1H), 1.61-1.55 (m, 1H), 1.51-1.40 (m, 4H), 1.39-1.23 (m, 4H), 1.05 (d, J=6.2 Hz, 6H), 0.93 (s, 3H), 0.84 (s, 3H); LCMS [M+H]+ 692.

Example 712 was prepared by a similar procedure to that of Example 710 using aminomethylcyclopropane (5.49 mg, 0.077 mmol) and 2',3,5-trifluoro-5'-(6-oxo-4-(trifluoromethyl)-1,6-dihydropyridine-3-carboxamido)-4'-((3S,5R)-3,4,5-trimethylpiperazin-1-yl)-[1,1'-biphenyl]-4-carboxylic acid (30 mg, 0.052 mmol) to give the title compound as a white fluffy powder (5.7 mg, 8.52 μmol, 16.54% yield). $^1$H NMR (500 MHz, METHANOL-d4) δ=7.91 (s, 1H), 7.84 (br d, J=8.2 Hz, 1H), 7.18 (br d, J=8.6 Hz, 2H), 6.98 (d, J=12.3 Hz, 1H), 6.79-6.72 (m, 1H), 2.99 (br d, J=11.2 Hz, 2H), 2.55-2.48 (m, 2H), 2.47-2.37 (m, 2H), 2.26 (s, 3H), 1.06 (d, J=6.2 Hz, 6H), 0.99 (ddd, J=5.1, 7.2, 12.0 Hz, 1H), 0.47-0.43 (m, 2H), 0.20 (q, J=4.9 Hz, 2H); LCMS [M+H]+ 636.

Example 713: N-[4-fluoro-5-[2-(morpholin-4-ylmethyl)-1,3-thiazol-4-yl]-2-[(3R,5S)-3,4,5-trimethylpiperazin-1-yl]phenyl]-6-oxo-4-(trifluoromethyl)-1H-pyridine-3-carboxamide

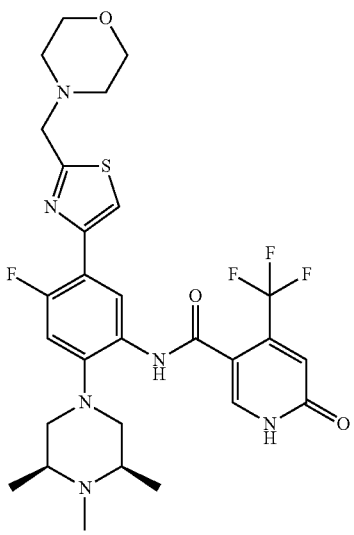 [SMILES: C[C@@H]1CN(c2cc(F)c(-c3csc(CN4CCOCC4)n3)cc2NC(=O)c2c[nH]c(=O)cc2C(F)(F)F)C[C@H](C)N1C]

The title compound was prepared using a sequence similar to that used for the preparation of Example 482 from 4-(trifluoromethyl)-6-(2-(trimethylsilyl)ethoxy)nicotinic acid (16.48 mg, 0.054 mmol), HATU (20.39 mg, 0.054 mmol) and 4-fluoro-5-(2-(morpholinomethyl)thiazol-4-yl)-2-((3S,5R)-3,4,5-trimethylpiperazin-1-yl)aniline (15 mg, 0.036 mmol) to afford the title compound (6.2 mg, 29% yield). $^1$H NMR (500 MHz, DMSO-d6) δ=12.81-12.20 (m, 1H), 9.49 (s, 1H), 8.30 (d, J=8.3 Hz, 1H), 7.95 (s, 1H), 7.82 (d, J=2.3 Hz, 1H), 7.02 (d, J=13.1 Hz, 1H), 6.79 (s, 1H), 3.88 (s, 2H), 3.65-3.58 (m, 4H), 3.03 (br d, J=11.0 Hz, 2H), 2.54 (br s, 4H), 2.48-2.43 (m, 2H), 2.37-2.31 (m, 2H), 2.19 (s, 3H), 1.00 (d, J=6.0 Hz, 6H); LCMS [M+H]+: 609.2.

Example 714: N-[4-fluoro-5-[1-(2-morpholin-4-ylethyl)pyrazol-4-yl]-2-[(3R)-3,4-dimethylpiperazin-1-yl]phenyl]-6-oxo-4-(trifluoromethyl)-1H-pyridine-3-carboxamide

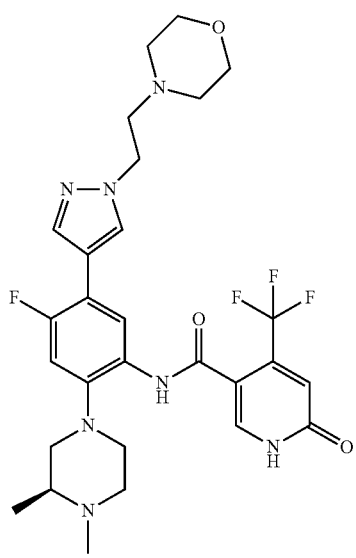 [SMILES: C[C@H]1CN(c2cc(F)c(-c3cnn(CCN4CCOCC4)c3)cc2NC(=O)c2c[nH]c(=O)cc2C(F)(F)F)CCN1C]

The title compound (13 mg, 26% yield) was prepared in a manner similar to that described in Example 39 from (S)—N-(5-bromo-2-(3,4-dimethylpiperazin-1-yl)-4-fluorophenyl)-4-(trifluoromethyl)-6-(2-(trimethylsilyl)ethoxy) nicotinamide (0.050 g, 0.085 mmol) and 1-(2-morpholinoethyl)-1H-pyrazole-4-boronic acid, pinacol ester (0.031 g, 0.101 mmol). $^1$H NMR (500 MHz, DMSO-d6) δ=12.53 (br s, 1H), 9.44 (s, 1H), 8.11 (s, 1H), 7.95 (s, 1H), 7.87 (d, J=8.3 Hz, 1H), 7.76 (s, 1H), 7.02 (d, J=12.7 Hz, 1H), 6.81 (s, 1H), 4.28 (t, J=6.5 Hz, 2H), 3.55 (t, J=4.5 Hz, 4H), 3.02-2.94 (m, 2H), 2.81-2.71 (m, 4H), 2.42 (br s, 4H), 2.40-2.29 (m, 3H), 2.21 (s, 3H), 0.97 (d, J=6.2 Hz, 3H); LCMS [M+H]+: 592.4.

Example 715: 4-(difluoromethyl)-N-[4-fluoro-5-[1-(2-morpholin-4-ylethyl)pyrazol-4-yl]-2-[(3R)-3,4-dimethylpiperazin-1-yl]phenyl]-1-methyl-6-oxopyridine-3-carboxamide

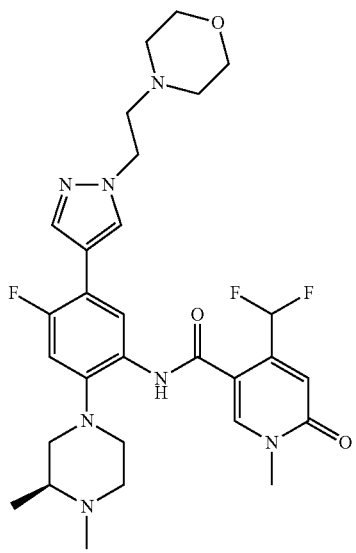 [SMILES: C[C@H]1CN(c2cc(F)c(-c3cnn(CCN4CCOCC4)c3)cc2NC(=O)c2cn(C)c(=O)cc2C(F)F)CCN1C]

The title compound was prepared according to a procedure similar to that described in the preparation of Example 217 using (S)—N-(5-bromo-2-(3,4-dimethylpiperazin-1-yl)-4-fluorophenyl)-4-(difluoromethyl)-1-methyl-6-oxo-1,6-dihydropyridine-3-carboxamide (0.050 g, 0.103 mmol) and 1-(2-morpholinoethyl)-1H-pyrazole-4-boronic acid, pinacol ester (0.038 g, 0.123 mmol). $^1$H NMR (500 MHz, DMSO-d6) δ=9.42 (s, 1H), 8.40 (s, 1H), 8.12 (d, J=1.2 Hz, 1H), 7.87 (s, 1H), 7.80 (d, J=8.3 Hz, 1H), 7.76 (s, 1H), 7.48-7.23 (m, 1H), 7.03 (d, J=12.6 Hz, 1H), 6.66 (s, 1H), 4.28 (t, J=6.5 Hz, 2H), 4.20 (t, J=6.6 Hz, 1H), 3.56-3.53 (m, 8H), 3.03-2.94 (m, 2H), 2.83-2.69 (m, 5H), 2.44-2.39 (m, 7H), 2.32 (dt, J=2.7, 10.9 Hz, 1H), 2.20 (s, 4H), 0.97 (d, J=6.2 Hz, 3H); LCMS [M+H]+: 588.2.

Example 716: N-[4-fluoro-5-[1-(2-morpholin-4-ylethyl)pyrazol-4-yl]-2-[(3R,5S)-3,4,5-trimethylpiperazin-1-yl]phenyl]-6-oxo-4-(triluoromethyl)-1H-pyridine-3-carboxamide

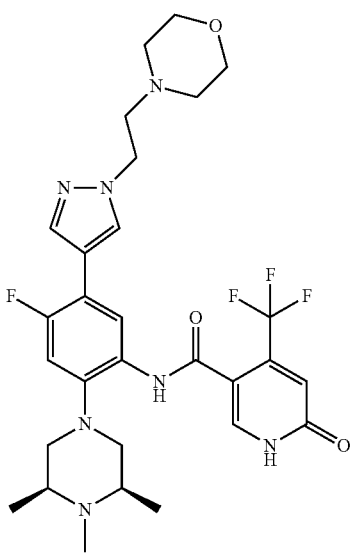 [SMILES: C[C@@H]1CN(c2cc(F)c(-c3cnn(CCN4CCOCC4)c3)cc2NC(=O)c2c[nH]c(=O)cc2C(F)(F)F)C[C@H](C)N1C]

The title compound (19 mg, 38% yield) was prepared in a manner similar to that described in Example 39 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (0.050 g, 0.083 mmol) and 1-(2-morpholinoethyl)-1H-pyrazole-4-boronic acid, pinacol ester (0.030 g, 0.099 mmol). 1H NMR (500 MHz, DMSO-d6) δ=12.55 (br s, 1H), 9.46 (s, 1H), 8.11 (d, J=1.0 Hz, 1H), 7.94 (s, 1H), 7.86 (d, J=8.2 Hz, 1H), 7.75 (s, 1H), 6.99 (d, J=12.6 Hz, 1H), 6.81 (s, 1H), 4.28 (t, J=6.5 Hz, 2H), 3.55 (t, J=4.5 Hz, 4H), 2.98 (br d, J=10.9 Hz, 2H), 2.73 (t, J=6.5 Hz, 2H), 2.44-2.39 (m, 5H), 2.35-2.29 (m, 2H), 2.19 (s, 3H), 1.00 (d, J=6.1 Hz, 6H); LCMS [M+H]+: 606.4.

Example 717: 4-(difluoromethyl)-N-[4-fluoro-5-[1-(2-morpholin-4-ylethyl)pyrazol-4-yl]-2-[(3R,5S)-3,4,5-trimethylpiperazin-1-yl]phenyl]-1-methyl-6-oxopyridine-3-carboxamide

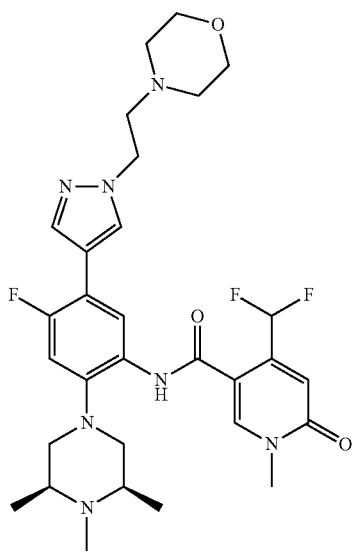 [SMILES: C[C@@H]1CN(c2cc(F)c(-c3cnn(CCN4CCOCC4)c3)cc2NC(=O)c2cn(C)c(=O)cc2C(F)F)C[C@H](C)N1C]

The title compound (33 mg, 55% yield) was prepared by a procedure similar to that of Example 461 using N-(5-bromo-4-fluoro-2-((3S,5R)-3,4,5-trimethylpiperazin-1-yl)phenyl)-4-(difluoromethyl)-1-methyl-6-oxo-1,6-dihydropyridine-3-carboxamide (0.050 g, 0.100 mmol) and 1-(2-morpholinoethyl)-1H-pyrazole-4-boronic acid, pinacol ester (0.037 g, 0.120 mmol). $^1$H NMR (500 MHz, DMSO-d6) δ=9.44 (s, 1H), 8.39 (s, 1H), 8.12 (d, J=1.1 Hz, 1H), 7.87 (s, 2H), 7.79 (d, J=8.4 Hz, 1H), 7.76 (s, 1H), 7.49-7.24 (m, 1H), 7.00 (d, J=12.7 Hz, 1H), 6.66 (s, 1H), 4.28 (t, J=6.6 Hz, 2H), 3.57-3.52 (m, 8H), 3.00 (br d, J=10.9 Hz, 2H), 2.75-2.68 (m, 5H), 2.41 (br d, J=3.4 Hz, 6H), 2.18 (s, 3H), 1.00 (d, J=6.1 Hz, 6H); LCMS [M+H]+: 602.5.

Example 718: N-[4-fluoro-5-(2-morpholin-4-ylpyrimidin-4-yl)-2-[(3R)-3,4-dimethylpiperazin-1-yl]phenyl]-6-oxo-4-(trifluoromethyl)-1H-pyridine-3-carboxamide

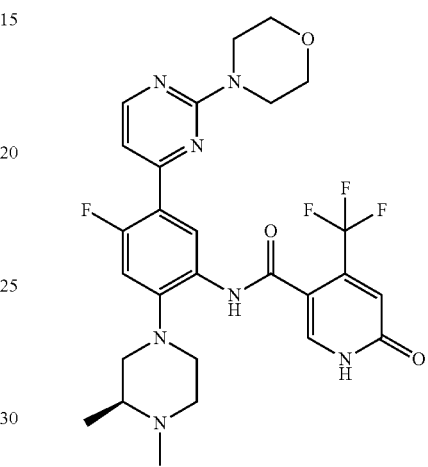

To a 5 mL microwave vial charged with (S)—N-(2-(3,4-dimethylpiperazin-1-yl)-4-fluoro-5-(tributylstannyl)phenyl)-4-(trifluoromethyl)-6-(2-(trimethylsilyl)ethoxy)nicotinamide (120 mg, 0.15 mmol), 4-(4-bromopyrimidin-2-yl)morpholine (44 mg, 0.18 mmol), LiCl (19 mg, 0.45 mmol) and bis(triphenylphosphine)palladium(II) dichloride (10.5 mg, 0.15 mmol, 10 mol %) was added DMF (1.5 mL). The resulting mixture was irradiated in microwave at 120° C. for 3 h. It was diluted with MeOH (20 mL), passed through SCX-2 column (2 g, 15 cc) and dried to give crude (S)—N-(2-(3,4-dimethylpiperazin-1-yl)-4-fluoro-5-(2-morpholinopyrimidin-4-yl)phenyl)-4-(trifluoromethyl)-6-(2-(trimethylsilyl)ethoxy)nicotinamide as a light brown solid. LCMS [M+H]+ 676.4. The above intermediate was redissolved in 2 mL of DCM and treated with TFA (0.92 mL, 12 mmol). The resulting mixture was stirred at rt for 2 h. The volatiles were removed and the residue purified by prep-HPLC and Biotage SCX-2 column to give the title compound as a light beige solid (12.8 mg, 15%). $^1$H NMR (500 MHz, METHANOL-d4) δ=8.60 (br d, J=8.1 Hz, 1H), 8.39 (d, J=5.1 Hz, 1H), 7.95 (s, 1H), 7.15 (dd, J=1.8, 5.1 Hz, 1H), 7.04 (d, J=13.2 Hz, 1H), 6.94 (s, 1H), 3.91-3.83 (m, 4H), 3.81-3.75 (m, 4H), 3.26-3.13 (m, 2H), 3.03-2.91 (m, 2H), 2.65-2.54 (m, 2H), 2.50-2.43 (m, 1H), 2.40 (s, 3H), 1.16 (d, J=6.2 Hz, 3H); LCMS [M+H]+ 576.3.

Example 719: N-[4-fluoro-5-(6-morpholin-4-ylpyridin-2-yl)-2-[(3R)-3,4-dimethylpiperazin-1-yl]phenyl]-6-oxo-4-(trifluoromethyl)-1H-pyridine-3-carboxamide

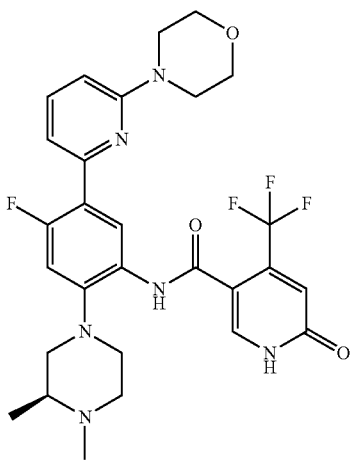 [SMILES: C[C@H]1CN(c2cc(F)c(-c3cccc(N4CCOCC4)n3)cc2NC(=O)c2c[nH]c(=O)cc2C(F)(F)F)CCN1C]

The title compound (light beige solid, 18.5 mg, 21%) was prepared similar to the 2-step sequence described above for the preparation of Example 718 using 4-(6-bromopyridin-2-yl)morpholine and (S)—N-(2-(3,4-dimethylpiperazin-1-yl)-4-fluoro-5-(tributylstannyl)phenyl)-4-(trifluoromethyl)-6-(2-(trimethylsilyl)ethoxy)nicotinamide. $^1$H NMR (500 MHz, METHANOL-d4) δ=8.53 (br d, J=8.1 Hz, 1H), 7.94 (s, 1H), 7.63 (t, J=7.9 Hz, 1H), 7.23 (dd, J=1.5, 7.5 Hz, 1H), 7.02 (d, J=13.0 Hz, 1H), 6.94 (s, 1H), 6.77 (d, J=8.3 Hz, 1H), 3.87-3.80 (m, 4H), 3.64-3.54 (m, 4H), 3.20-3.10 (m, 2H), 3.00-2.93 (m, 2H), 2.62-2.53 (m, 2H), 2.48-2.43 (m, 1H), 2.40 (s, 3H), 1.16 (d, J=6.2 Hz, 3H); LCMS [M+H]$^+$ 575.3.

Example 720: 4-(difluoromethyl)-N-[4-fluoro-5-(2-morpholin-4-ylpyrimidin-4-yl)-2-[(3R)-3,4-dimethylpiperazin-1-yl]phenyl]-6-oxo-1H-pyridine-3-carboxamide

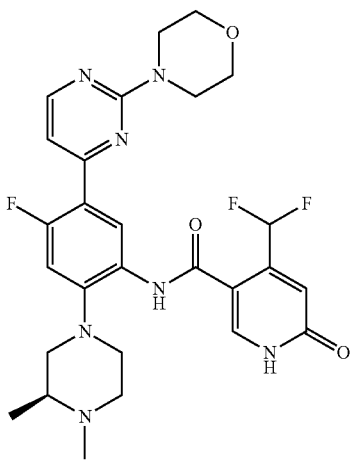

The title compound (light beige solid, 18.2 mg, 16%) was prepared similar to the 2-step sequence described above for the preparation of Example 718 using (S)-4-(difluoromethyl)-N-(2-(3,4-dimethylpiperazin-1-yl)-4-fluoro-5-(tributylstannyl)phenyl)-6-(2-(trimethylsilyl)ethoxy)nicotinamide (157 mg, 0.2 mmol) in place of (S)—N-(2-(3,4-dimethylpiperazin-1-yl)-4-fluoro-5-(tributylstannyl)phenyl)-4-(trifluoromethyl)-6-(2-(trimethylsilyl)ethoxy)nicotinamide. $^1$H NMR (500 MHz, METHANOL-d4) δ=8.46 (d, J=8.3 Hz, 1H), 8.39 (d, J=5.3 Hz, 1H), 8.03 (s, 1H), 7.32 (t, J=55.0 Hz, 1H), 7.13 (dd, J=1.8, 5.1 Hz, 1H), 7.03 (d, J=13.2 Hz, 1H), 6.82 (s, 1H), 3.89-3.83 (m, 4H), 3.80-3.75 (m, 4H), 3.24-3.14 (m, 2H), 3.02-2.89 (m, 2H), 2.63-2.50 (m, 2H), 2.46-2.35 (m, 4H), 1.13 (d, J=6.4 Hz, 3H); LCMS [M+H]$^+$ 558.3.

Example 721: 4-(difluoromethyl)-N-[4-fluoro-5-(6-morpholin-4-ylpyridin-2-yl)-2-[(3R)-3,4-dimethylpiperazin-1-yl]phenyl]-6-oxo-1H-pyridine-3-carboxamide

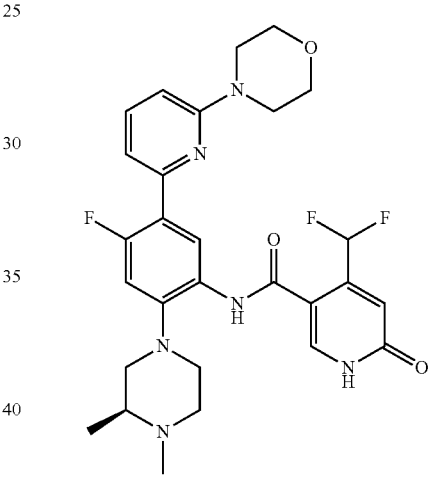

The title compound (off white solid, 8.0 mg, 7%) was prepared similar to the 2-step sequence described above for the preparation of Example 718 using (S)-4-(difluoromethyl)-N-(2-(3,4-dimethylpiperazin-1-yl)-4-fluoro-5-(tributylstannyl)phenyl)-6-(2-(trimethylsilyl)ethoxy)nicotinamide (157 mg, 0.2 mmol) and 4-(6-bromopyridin-2-yl)morpholine (58 mg, 0.24 mmol) in place of (S)—N-(2-(3,4-dimethylpiperazin-1-yl)-4-fluoro-5-(tributylstannyl)phenyl)-4-(trifluoromethyl)-6-(2-(trimethylsilyl)ethoxy)nicotinamide and 4-(4-bromopyrimidin-2-yl)morpholine. $^1$H NMR (500 MHz, METHANOL-d4) δ=8.39 (d, J=8.3 Hz, 1H), 8.02 (s, 1H), 7.63 (t, J=8.0 Hz, 1H), 7.44-7.20 (m, 2H), 7.01 (d, J=13.0 Hz, 1H), 6.83 (s, 1H), 6.77 (d, J=8.6 Hz, 1H), 3.86-3.78 (m, 4H), 3.63-3.55 (m, 4H), 3.21-3.10 (m, 2H), 3.03-2.92 (m, 2H), 2.59 (br t, J=10.8 Hz, 2H), 2.47 (br s, 1H), 2.41 (s, 3H), 1.15 (d, J=6.2 Hz, 3H); LCMS [M+H]$^+$ 557.3.

Example 722: 2-(difluoromethyl)-4-fluoro-N-[4-fluoro-5-(2-morpholin-4-ylpyrimidin-5-yl)-2-[(3R,5S)-3,4,5-trimethylpiperazin-1-yl]phenyl]benzamide

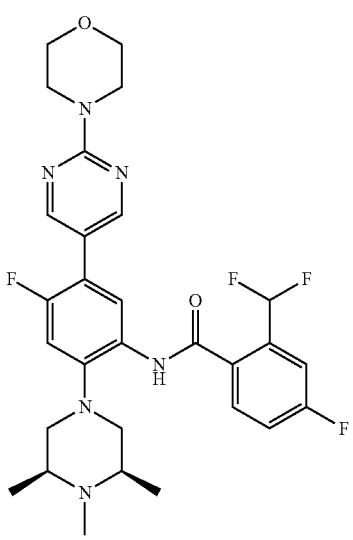 [SMILES: C[C@@H]1CN(c2cc(F)c(-c3cnc(N4CCOCC4)nc3)cc2NC(=O)c2ccc(F)cc2C(F)F)C[C@H](C)N1C]

A mixture of 2-(difluoromethyl)-4-fluorobenzoic acid (76 mg, 0.4 mmol), HATU (152 mg, 0.4 mmol) and N,N-diisopropylethylamine (0.11 ml, 0.6 mmol) in DMF (2 mL) was heated at 60° C. for 5 min to afford a clear colorless solution before 4-fluoro-5-(2-morpholinopyrimidin-5-yl)-2-((3S,5R)-3,4,5-trimethylpiperazin-1-yl)aniline (80 mg, 0.2 mmol) was added in one portion. The resulting mixture was heated at 60° C. for 1 h. Solvent were removed and the residue was purified by prep-HPLC and Biotage SCX-2 column to give a light beige solid. It was suspended in MeOH (10 mL), treated with HCO$_2$H (0.05 mL, filtered and the filtrate was concentrated and dried to give the title compound as a light brown solid (formic acid salt, 35.4 mg, 28%). $^1$H NMR (500 MHz, METHANOL-d4) δ=8.58 (s, 2H), 8.41 (s, 1H), 7.97 (br d, J=8.1 Hz, 1H), 7.88 (br dd, J=5.6, 7.8 Hz, 1H), 7.56 (dd, J=2.3, 9.3 Hz, 1H), 7.51-7.25 (m, 2H), 7.17 (d, J=11.9 Hz, 1H), 3.90-3.82 (m, 4H), 3.82-3.75 (m, 4H), 3.25 (br d, J=12.2 Hz, 2H), 3.11-2.95 (m, 2H), 2.87-2.77 (m, 2H), 2.68 (s, 3H), 1.31 (d, J=6.4 Hz, 6H); LCMS [M+H]$^+$ 573.3.

Example 723: propan-2-yl 4-[5-[[4-(difluoromethyl)-6-oxo-1H-pyridine-3-carbonyl]amino]-2-fluoro-4-[(3R,5S)-3,4,5-trimethylpiperazin-1-yl]phenyl]-2,3,6,7-tetrahydroazepine-1-carboxylate

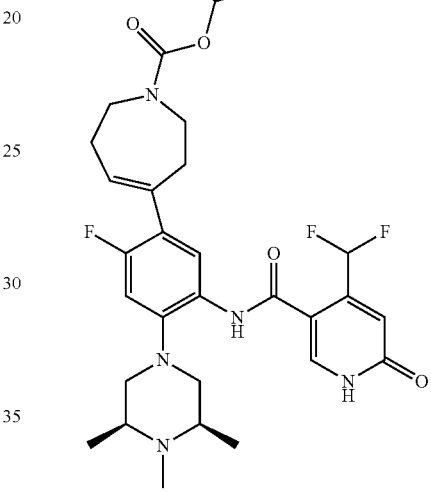

The procedure followed was similar to that of Example 253 using 4-(difluoromethyl)-N-(4-fluoro-5-(2,3,6,7-tetrahydro-1H-azepin-4-yl)-2-((3S,5R)-3,4,5-trimethylpiperazin-1-yl)phenyl)-6-oxo-1,6-dihydropyridine-3-carboxamide (30 mg, 0.060 mmol) and isopropyl chloroformate (0.060 ml, 0.060 mmol) to afford the title compound as a white fluffy powder (24 mg, 0.039 mmol, 64.9% yield). $^1$H NMR (500 MHz, METHANOL-d4) δ=7.90-7.84 (m, 1H), 7.49-7.42 (m, 1H), 7.34-7.05 (m, 1H), 6.80 (d, J=11.9 Hz, 1H), 6.70 (s, 1H), 5.93-5.72 (m, 1H), 3.96 (br dd, J=5.0, 13.8 Hz, 1H), 3.58 (t, J=6.0 Hz, 1H), 3.56-3.46 (m, 1H), 2.90 (br d, J=11.1 Hz, 2H), 2.58-2.49 (m, 2H), 2.48-2.42 (m, 2H), 2.39 (br d, J=6.5 Hz, 3H), 2.24 (s, 3H), 1.84-1.76 (m, 1H), 1.16 (br t, J=5.2 Hz, 6H), 1.03 (d, J=6.0 Hz, 6H); LCMS [M+H]$^+$ 590.

Example 724: propan-2-yl 4-[5-[[4-(difluoromethyl)-6-oxo-1H-pyridine-3-carbonyl]amino]-2-fluoro-4-[(3R)-3,4-dimethylpiperazin-1-yl]phenyl]-3,6-dihydro-2H-pyridine-1-carboxylate

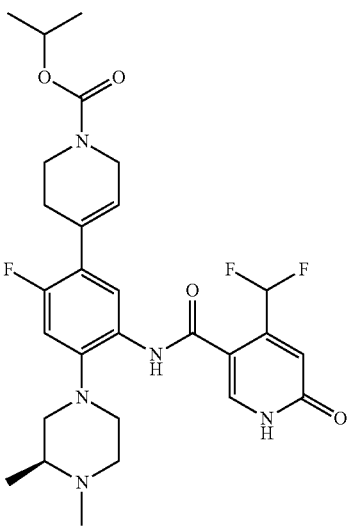 [SMILES: CC(C)OC(=O)N1CC=C(c2cc(NC(=O)c3c[nH]c(=O)cc3C(F)F)c(N3CCN(C)[C@@H](C)C3)cc2F)CC1]

The procedure followed was similar to Example 253 using (S)-4-(difluoromethyl)-N-(2-(3,4-dimethylpiperazin-1-yl)-4-fluoro-5-(1,2,3,6-tetrahydropyridin-4-yl)phenyl)-6-oxo-1,6-dihydropyridine-3-carboxamide (25 mg, 0.053 mmol) and isopropyl chloroformate (0.045 ml, 0.045 mmol) to give the title compound (20.5 mg, 66% yield). $^1$H NMR (500 MHz, METHANOL-d46 7.86-7.93 (m, 1H), 7.89 (s, 1H), 7.54-7.60 (m, 1H), 7.07-7.31 (m, 1H), 6.80-6.87 (m, 1H), 6.70 (s, 1H), 5.88 (br. s., 1H), 4.80-4.86 (m, 1H), 4.00 (br. s., 2H), 3.55 (br. s., 2H), 2.93-3.00 (m, 1H), 2.88-2.93 (m, 1H), 2.75-2.83 (m, 2H), 2.36-2.44 (m, 4H), 2.22-2.31 (m, 4H), 1.18 (d, J=6.24 Hz, 6H), 1.00 (d, J=6.36 Hz, 3H); LCMS [M+H]+ 562.5.

Example 725: propan-2-yl 5-[5-[[4-(difluoromethyl)-6-oxo-1H-pyridine-3-carbonyl]amino]-2-fluoro-4-[(3R 5S)-3,4,5-trimethylpiperazin-1-yl]phenyl]-3,6-dihydro-2H-pyridine-1-carboxylate

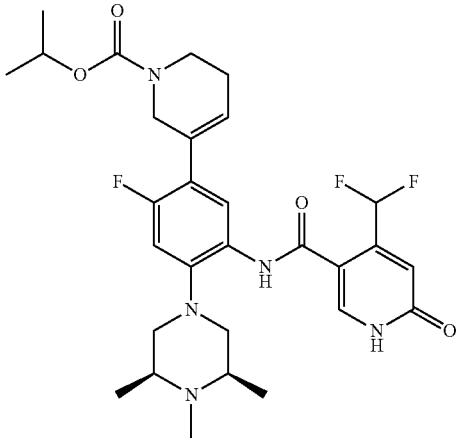 [SMILES: CC(C)OC(=O)N1CCC=C(c2cc(NC(=O)c3c[nH]c(=O)cc3C(F)F)c(N3C[C@@H](C)N(C)[C@@H](C)C3)cc2F)C1]

The procedure was similar to that of Example 253 using 4-(difluoromethyl)-N-(4-fluoro-5-(1,2,5,6-tetrahydropyridin-3-yl)-2-((3S,5R)-3,4,5-trimethylpiperazin-1-yl)phenyl)-6-oxo-1,6-dihydropyridine-3-carboxamide (25 mg, 0.051 mmol) and isopropyl chloroformate (0.049 ml, 0.049 mmol) to give the title compound (23 mg, 74% yield). $^1$H NMR (500 MHz, METHANOL-d4) δ 7.89 (s, 1H), 7.55 (d, J=7.95 Hz, 1H), 7.07-7.32 (m, 1H), 6.83 (d, J=12.23 Hz, 1H), 6.69 (s, 1H), 5.98 (br. s., 1H), 4.79-4.85 (m, 1H), 4.13 (br. s., 2H), 3.50 (br. s., 2H), 2.93 (d, J=11.25 Hz, 2H), 2.43-2.50 (m, 2H), 2.36-2.42 (m, 2H), 2.24 (s, 3H), 2.19-2.23 (m, 2H), 1.15-1.18 (m, 6H), 1.15-1.18 (m, 6H), 1.17 (d, J=6.24 Hz, 6H), 1.03 (d, J=6.11 Hz, 6H); LCMS [M+H]+ 576.5.

Example 726: propan-2-yl 5-[5-[[4-(difluoromethyl)-6-oxo-1H-pyridine-3-carbonyl]amino]-2-fluoro-4-[(3R)-3,4-dimethylpiperazin-1-yl]phenyl]-3,6-dihydro-2H-pyridine-1-carboxylate

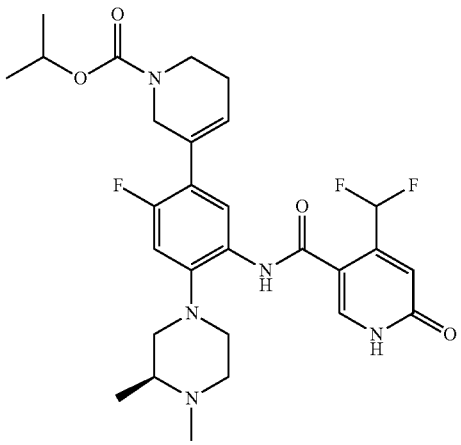 [SMILES: CC(C)OC(=O)N1CCC=C(c2cc(NC(=O)c3c[nH]c(=O)cc3C(F)F)c(N3CCN(C)[C@@H](C)C3)cc2F)C1]

The procedure used was similar to Example 253 using (S)-4-(difluoromethyl)-N-(2-(3,4-dimethylpiperazin-1-yl)-4-fluoro-5-(1,2,5,6-tetrahydropyridin-3-yl)phenyl)-6-oxo-1,6-dihydropyridine-3-carboxamide (25 mg, 0.053 mmol) and isopropyl chloroformate (0.050 mL, 0.050 mmol) to give the title compound (25.5 mg, 82% yield). $^1$H NMR (500 MHz, METHANOL-d4) δ 7.90 (s, 1H), 7.57 (d, J=7.95 Hz, 1H), 7.07-7.32 (m, 1H), 6.85 (d, J=12.35 Hz, 1H), 6.70 (s, 1H), 5.98 (br. s., 1H), 4.78-4.85 (m, 1H), 4.13 (br. s., 2H), 3.50 (br. s., 2H), 2.95-3.01 (m, 1H), 2.92 (d, J=11.49 Hz, 1H), 2.75-2.83 (m, 2H), 2.37-2.45 (m, 2H), 2.20-2.31 (m, 6H), 1.13-1.19 (m, 6H), 1.00 (d, J=6.24 Hz, 3H); LCMS [M+H]+ 562.5.

Example 727: propan-2-yl 4-[2-fluoro-5-[[4-fluoro-2-(trifluoromethyl)benzoyl]amino]-4-[(3R)-3,4-dimethylpiperazin-1-yl]phenyl]-3,6-dihydro-2H-pyridine-1-carboxylate

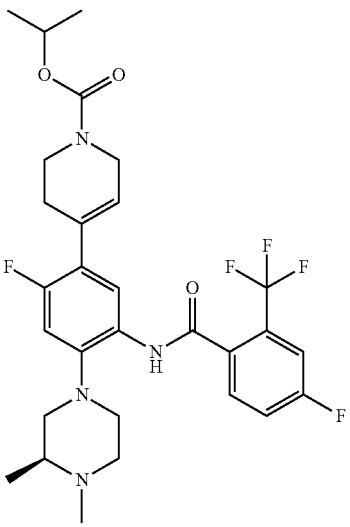 [SMILES: CC(C)OC(=O)N1CC=C(c2cc(NC(=O)c3ccc(F)cc3C(F)(F)F)c(N3CCN(C)[C@@H](C)C3)cc2F)CC1]

The procedure was similar to Example 253 using (S)—N-(2-(3,4-dimethylpiperazin-1-yl)-4-fluoro-5-(1,2,3,6-tetrahydropyridin-4-yl)phenyl)-4-fluoro-2-(trifluoromethyl)benzamide (25 mg, 0.051 mmol) and isopropyl chloroformate (0.048 ml, 0.048 mmol) to give the title compound (21 mg, 68% yield). ¹H NMR (500 MHz, METHANOL-d4) δ 7.73-7.80 (m, 1H), 7.64 (dd, J=5.32, 8.38 Hz, 1H), 7.53 (dd, J=2.32, 9.05 Hz, 1H), 7.44 (dt, J=2.32, 8.25 Hz, 1H), 6.80-6.93 (m, 1H), 5.82-5.96 (m, 1H), 4.79-4.87 (m, 1H), 4.01 (br. s., 2H), 3.56 (br. s., 2H), 2.92-2.99 (m, 1H), 2.89 (d, J=11.49 Hz, 1H), 2.76-2.83 (m, 2H), 2.38-2.51 (m, 3H), 2.29-2.37 (m, 1H), 2.19-2.26 (m, 4H), 1.16-1.20 (m, 6H), 1.18 (d, J=6.24 Hz, 6H), 0.99 (d, J=6.36 Hz, 3H); LCMS [M+H]+ 581.6.

Example 728: propan-2-yl 5-[2-fluoro-5-[[4-fluoro-2-(trifluoromethyl)benzoyl]amino]-4-[(3R)-3,4-dimethylpiperazin-1-yl]phenyl]-3,6-dihydro-2H-pyridine-1-carboxylate

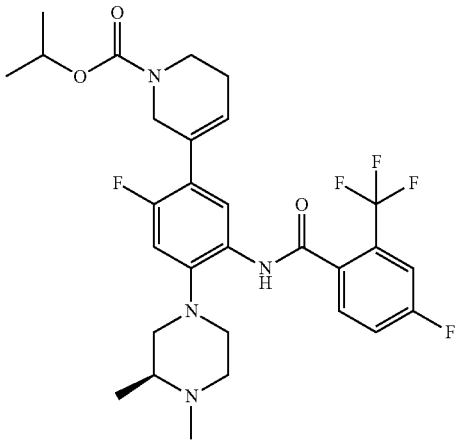 [SMILES: CC(C)OC(=O)N1CCC=C(c2cc(NC(=O)c3ccc(F)cc3C(F)(F)F)c(N3CCN(C)[C@@H](C)C3)cc2F)C1]

The procedure was similar to that of Example 253 using (S)—N-(2-(3,4-dimethylpiperazin-1-yl)-4-fluoro-5-(1,2,5,6-tetrahydropyridin-3-yl)phenyl)-4-fluoro-2-(trifluoromethyl)benzamide (25 mg, 0.051 mmol) and isopropyl chloroformate (0.048 mL, 0.048 mmol) to give the title compound (22 mg, 71% yield). ¹H NMR (500 MHz, METHANOL-d4) δ 7.85-7.92 (m, 1H), 7.76 (dd, J=5.38, 8.44 Hz, 1H), 7.65 (dd, J=2.32, 9.05 Hz, 1H), 7.57 (dt, J=2.32, 8.31 Hz, 1H), 7.00 (d, J=12.23 Hz, 1H), 6.12 (br. s., 1H), 4.90-4.97 (m, 1H), 4.27 (d, J=1.59 Hz, 2H), 3.64 (br. s., 2H), 3.06-3.13 (m, 1H), 3.03 (d, J=11.49 Hz, 1H), 2.87-2.96 (m, 2H), 2.55 (t, J=10.82 Hz, 1H), 2.43-2.51 (m, 1H), 2.30-2.40 (m, 6H), 1.28-1.32 (m, 6H), 1.12 (d, J=6.36 Hz, 3H); LCMS [M+H]+ 581.5.

Example 729: (1-methylcyclobutyl) 4-[5-[[4-(difluoromethyl)-6-oxo-1H-pyridine-3-carbonyl]amino]-2-fluoro-4-[(3R,5S)-3,4,5-trimethylpiperazin-1-yl]phenyl]-2,3,6,7-tetrahydroazepine-1-carboxylate

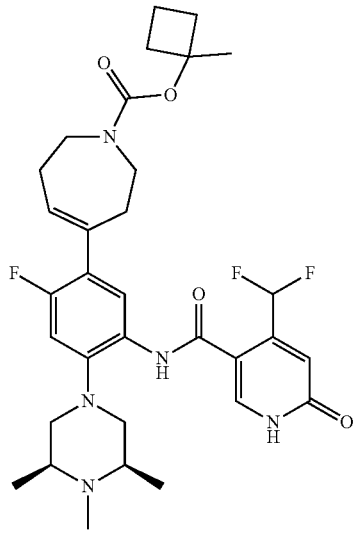 [SMILES: C[C@@H]1CN(c2cc(F)c(C3=CCCN(C(=O)OC4(C)CCC4)CC3)cc2NC(=O)c2c[nH]c(=O)cc2C(F)F)C[C@H](C)N1C]

The procedure used was similar to that of Example 253 using 4-(difluoromethyl)-N-(4-fluoro-5-(2,3,6,7-tetrahydro-1H-azepin-4-yl)-2-((3S,5R)-3,4,5-trimethylpiperazin-1-yl)phenyl)-6-oxo-1,6-dihydropyridine-3-carboxamide (30 mg, 0.060 mmol) and 1-methylcyclobutyl (4-nitrophenyl) carbonate (15.72 mg, 0.063 mmol) to afford the title compound a white fluffy powder (29 mg, 0.045 mmol, 75% yield). ¹H NMR (500 MHz, METHANOL-d4) δ=7.88 (s, 1H), 7.51-7.43 (m, 1H), 7.32-7.07 (m, 1H), 6.80 (br dd, J=3.3, 11.9 Hz, 1H), 6.70 (s, 1H), 5.92-5.78 (m, 1H), 3.93 (br s, 1H), 3.59-3.50 (m, 2H), 3.50-3.40 (m, 1H), 2.90 (br d, J=11.1 Hz, 2H), 2.58-2.49 (m, 2H), 2.48-2.43 (m, 2H), 2.42-2.33 (m, 3H), 2.28-2.18 (m, 5H), 2.06-1.98 (m, 2H), 1.81 (br d, J=5.1 Hz, 1H), 1.76-1.66 (m, 1H), 1.63-1.52 (m, 1H), 1.49-1.43 (m, 3H), 1.03 (d, J=6.1 Hz, 6H); LCMS [M+H]+ 616.

Example 730: (3,3-difluorocyclobutyl) 4-[5-[[4-(difluoromethyl)-6-oxo-1H-pyridine-3-carbonyl]amino]-2-fluoro-4-[(3R,5S)-3,4,5-trimethylpiperazin-1-yl]phenyl]-2,3,6,7-tetrahydroazepine-1-carboxylate

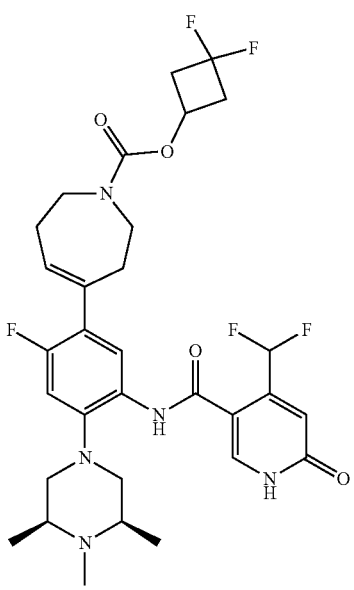 [SMILES: C[C@@H]1CN(c2cc(F)c(C3=CCCN(C(=O)OC4CC(F)(F)C4)CC3)cc2NC(=O)c2c[nH]c(=O)cc2C(F)F)C[C@H](C)N1C]

A procedure similar to that of Example 253 using 4-(difluoromethyl)-N-(4-fluoro-5-(2,3,6,7-tetrahydro-1H-azepin-4-yl)-2-((3S,5R)-3,4,5-trimethylpiperazin-1-yl)phenyl)-6-oxo-1,6-dihydropyridine-3-carboxamide (30 mg, 0.060 mmol) and 3,3-difluorocyclobutyl (4-nitrophenyl) carbonate (17.90 mg, 0.066 mmol) afforded the title compound was collected as a white fluffy powder (26 mg, 65.0% yield). $^1$H NMR (500 MHz, METHANOL-d4) δ=7.88 (br s, 1H), 7.51-7.41 (m, 1H), 7.31-7.07 (m, 1H), 6.80 (br d, J=11.9 Hz, 1H), 6.70 (s, 1H), 5.93-5.79 (m, 1H), 3.98 (d, J=5.3 Hz, 1H), 3.60 (td, J=5.9, 15.2 Hz, 2H), 3.56-3.46 (m, 1H), 2.97-2.83 (m, 4H), 2.62-2.50 (m, 4H), 2.48-2.42 (m, 2H), 2.39 (br d, J=6.2 Hz, 2H), 2.24 (s, 3H), 1.86-1.78 (m, 1H), 1.03 (d, J=6.1 Hz, 6H); LCMS [M+H]$^+$ 638.

Example 731: N-[5-[1-(5-cyano-1,3-thiazol-2-yl)-2,3,6,7-tetrahydroazepin-4-yl]-4-fluoro-2-[(3R,5S)-3,4,5-trimethylpiperazin-1-yl]phenyl]-4-(difluoromethyl)-6-oxo-1H-pyridine-3-carboxamide

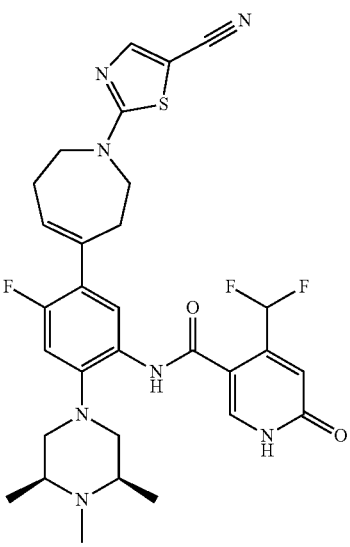 [SMILES: C[C@@H]1CN(c2cc(F)c(C3=CCCN(c4ncc(C#N)s4)CC3)cc2NC(=O)c2c[nH]c(=O)cc2C(F)F)C[C@H](C)N1C]

A procedure similar to that of Example 270 using 4-(difluoromethyl)-N-(4-fluoro-5-(2,3,6,7-tetrahydro-1H-azepin-4-yl)-2-((3S,5R)-3,4,5-trimethylpiperazin-1-yl)phenyl)-6-oxo-1,6-dihydropyridine-3-carboxamide (30 mg, 0.060 mmol) and 2-bromo-5-cyanothiazole (11.26 mg, 0.060 mmol) afforded the title compound was collected as a white fluffy powder (32 mg, 0.050 mmol, 83% yield). $^1$H NMR (500 MHz, METHANOL-d4) δ=7.88 (s, 1H), 7.73-7.65 (m, 1H), 7.50-7.43 (m, 1H), 7.31-7.05 (m, 1H), 6.83-6.75 (m, 1H), 6.69 (s, 1H), 6.02-5.80 (m, 1H), 4.24 (br d, J=5.1 Hz, 1H), 3.85-3.71 (m, 3H), 2.90 (br d, J=11.1 Hz, 2H), 2.58-2.51 (m, 2H), 2.48-2.41 (m, 2H), 2.41-2.32 (m, 2H), 2.25-2.22 (m, 3H), 2.01-1.94 (m, 1H), 1.05-0.99 (m, 6H); LCMS [M+H]$^+$ 612.

Example 732: N-[5-[4-(cyclohexylcarbamoyl)-3-fluorophenyl]-4-fluoro-2-[(3R,5S)-3,4,5-trimethylpiperazin-1-yl]phenyl]-6-oxo-4-(trifluoromethyl)-1H-pyridine-3-carboxamide

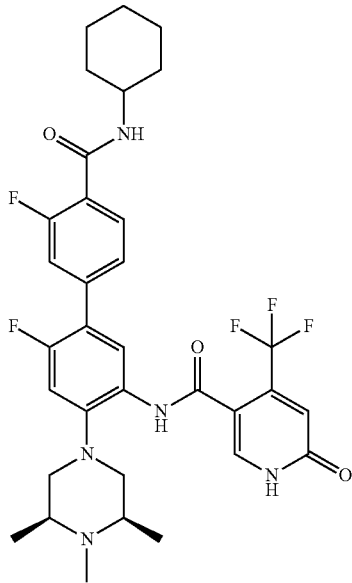 [SMILES: C[C@@H]1CN(c2cc(F)c(-c3ccc(C(=O)NC4CCCCC4)c(F)c3)cc2NC(=O)c2c[nH]c(=O)cc2C(F)(F)F)C[C@H](C)N1C]

Step 1: 2',3-difluoro-5'-(6-oxo-4-(trifluoromethyl)-1,6-dihydropyridine-3-carboxamido)-4'-((3S,5R)-3,4,5-trimethylpiperazin-1-yl)-[1,1'-biphenyl]-4-carboxylic acid

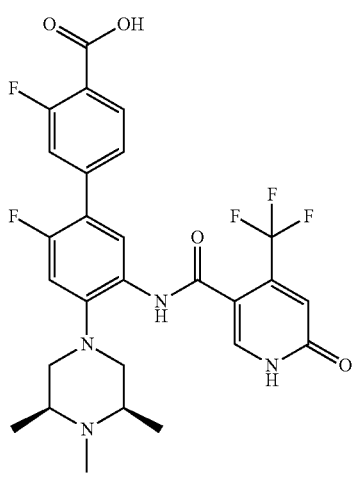 [SMILES: C[C@@H]1CN(c2cc(F)c(-c3ccc(C(=O)O)c(F)c3)cc2NC(=O)c2c[nH]c(=O)cc2C(F)(F)F)C[C@H](C)N1C]

The procedure followed was similar to Example 100 using N-(5-bromo-4-fluoro-2-((3S,5R)-3,4,5-trimethylpiperazin-1-yl)phenyl)-4-(trifluoromethyl)-6-(2-(trimethylsilyl)ethoxy)nicotinamide (300 mg, 0.495 mmol), 4-carboxy-3-fluorophenylboronic acid (137 mg, 0.743 mmol) to give, after deprotection of the silyloxy pyridyl intermediate, the title compound (193 mg, 88% yield) as a pale yellow powder. LCMS: [M+H]+ 565.2.

Step 2: N-[5-[4-(cyclohexylcarbamoyl)-3-fluorophenyl]-4-fluoro-2-[(3R 5S)-3,4,5-trimethylpiperazin-1-yl]phenyl]-6-oxo-4-(triluoromethyl)-1H-pyridine-3-carboxamide

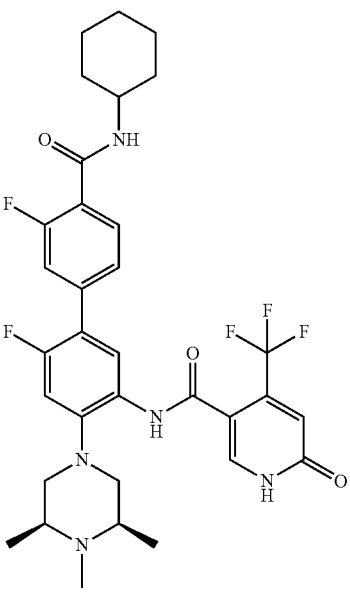 [SMILES: C[C@@H]1CN(c2cc(F)c(-c3ccc(C(=O)NC4CCCCC4)c(F)c3)cc2NC(=O)c2c[nH]c(=O)cc2C(F)(F)F)C[C@H](C)N1C]

A 30 mL vial was charged with HATU (30.3 mg, 0.080 mmol) and cyclohexylamine (7.91 mg, 0.080 mmol). A stock solution of 2',3-difluoro-5'-(6-oxo-4-(trifluoromethyl)-1,6-dihydropyridine-3-carboxamido)-4'-((3S,5R)-3,4,5-trimethylpiperazin-1-yl)-[1,1'-biphenyl]-4-carboxylic acid (30 mg, 0.053 mmol) in N,N-dimethylformamide (2 ml) was added. The mixture was stirred at rt for 5 min upon which N,N-diisopropylethylamine (0.037 ml, 0.213 mmol) was added via a syringe. The mixture was stirred at rt for 30 min, LCMS showed completion. The crude product was adsorbed on celite and dried and purified by reverse phase flash column chromatography (C18 13.3 g column, eluent: 10%, 10-70%, then 70% AcCN/water). The product fractions were concentrated under vacuum and lyophilized to afford the title compound as a white powder (4 mg, 5.89 μmol, 11.1% yield). $^1$H NMR (500 MHz, METHANOL-d4) δ=7.88-7.81 (m, 2H), 7.63 (t, J=7.8 Hz, 1H), 7.37 (d, J=8.1 Hz, 1H), 7.31 (d, J=12.0 Hz, 1H), 6.98 (d, J=12.2 Hz, 1H), 6.83-6.78 (m, 1H), 3.85-3.75 (m, 1H), 3.00 (br d, J=11.2 Hz, 2H), 2.56-2.50 (m, 2H), 2.47 (br d, J=5.0 Hz, 2H), 2.28 (s, 3H), 1.92-1.85 (m, 2H), 1.75-1.68 (m, 2H), 1.62-1.53 (m, 1H), 1.39-1.12 (m, 6H), 1.07 (d, J=6.1 Hz, 6H); LCMS [M+H]+ 646.

Example 733: N-[5-[4-[cyclopropylmethyl(methyl)carbamoyl]-3-fluorophenyl]-4-fluoro-2-[(3R,5S)-3,4,5-trimethylpiperazin-1-yl]phenyl]-6-oxo-4-(trifluoromethyl)-1H-pyridine-3-carboxamide

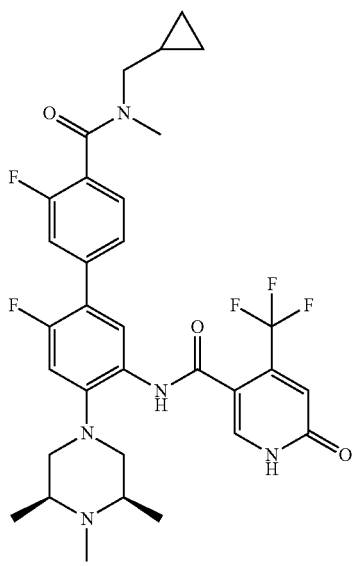 [SMILES: C[C@@H]1CN(c2cc(F)c(-c3ccc(C(=O)N(C)CC4CC4)c(F)c3)cc2NC(=O)c2c[nH]c(=O)cc2C(F)(F)F)C[C@H](C)N1C]

A procedure similar to Example 732 using 1-cyclopropyl-N-methylmethanamine (6.79 mg, 0.080 mmol) and 2',3-difluoro-5'-(6-oxo-4-(trifluoromethyl)-1,6-dihydropyridine-3-carboxamido)-4'-((3S,5R)-3,4,5-trimethylpiperazin-1-yl)-[1,1'-biphenyl]-4-carboxylic acid (30 mg, 0.053 mmol) in Step 2 afforded the title compound as a white fluffy powder (4 mg, 6.02 µmol, 11.3% yield). $^1$H NMR (500 MHz, METHANOL-d4) δ=7.86-7.81 (m, 2H), 7.39-7.35 (m, 1H), 7.33 (br d, J=8.1 Hz, 1H), 7.30 (dd, J=1.5, 7.6 Hz, 1H), 6.96 (d, J=12.2 Hz, 1H), 6.79-6.76 (m, 1H), 3.36 (d, J=7.1 Hz, 1H), 3.08 (s, 2H), 3.06-3.02 (m, 1H), 2.96 (br d, J=11.2 Hz, 2H), 2.94-2.89 (m, 2H), 2.53-2.46 (m, 2H), 2.45-2.36 (m, 2H), 2.24 (s, 3H), 1.04 (d, J=6.1 Hz, 6H), 0.90-0.80 (m, 1H), 0.50-0.46 (m, 1H), 0.44-0.39 (m, 1H), 0.27-0.22 (m, 1H), 0.02--0.04 (m, 1H); LCMS [M+H]$^+$ 632.

Example 734: N-[5-[4-[(4,4-difluorocyclohexyl)carbamoyl]-3-fluorophenyl]-4-fluoro-2-[(3R,5S)-3,4,5-trimethylpiperazin-1-yl]phenyl]-6-oxo-4-(trifluoromethyl)-1H-pyridine-3-carboxamide

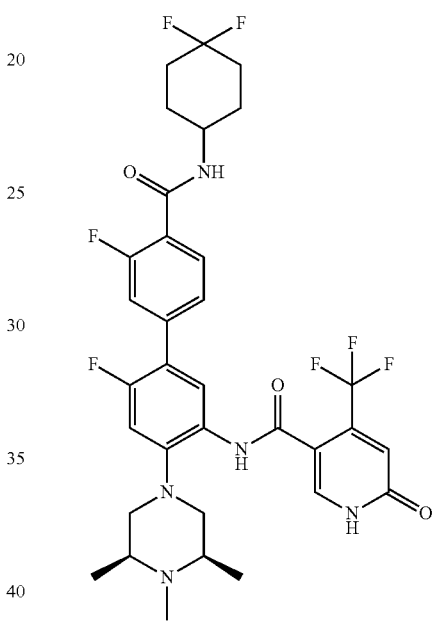

The procedure followed was similar to Example 732 using 4,4-difluorocyclohexylamine hydrochloride (13.68 mg, 0.080 mmol) and 2',3-difluoro-5'-(6-oxo-4-(trifluoromethyl)-1,6-dihydropyridine-3-carboxamido)-4'-((3S,5R)-3,4,5-trimethylpiperazin-1-yl)-[1,1'-biphenyl]-4-carboxylic acid (30 mg, 0.053 mmol) in Step 2 to afford the title compound as an off-white fluffy powder (25.8 mg, 63.4% yield). $^1$H NMR (500 MHz, METHANOL-d4) δ=8.36-8.25 (m, 1H), 7.89-7.85 (m, 2H), 7.63 (t, J=7.8 Hz, 1H), 7.37 (d, J=8.1 Hz, 1H), 7.32 (d, J=11.7 Hz, 1H), 7.02 (d, J=12.1 Hz, 1H), 6.84-6.80 (m, 1H), 3.96 (br t, J=10.4 Hz, 1H), 3.14-3.05 (m, 2H), 2.88-2.75 (m, 2H), 2.69-2.61 (m, 2H), 2.49 (s, 3H), 2.07-1.90 (m, 5H), 1.90-1.77 (m, 2H), 1.68-1.58 (m, 2H), 1.16 (d, J=6.4 Hz, 6H); LCMS [M+H]$^+$ 682.

Example 735: N-[5-[4-(cyclopropylmethylcarbamoyl)-3-fluorophenyl]-4-fluoro-2-[(3R,5S)-3,4,5-trimethylpiperazin-1-yl]phenyl]-6-oxo-4-(trifluoromethyl)-1H-pyridine-3-carboxamide

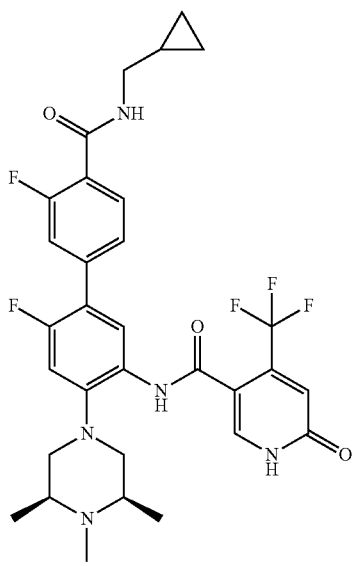

A similar procedure to that of Example 732 using aminomethylcyclopropane (5.67 mg, 0.080 mmol) and 2',3-difluoro-5'-(6-oxo-4-(trifluoromethyl)-1,6-dihydropyridine-3-carboxamido)-4'-((3S,5R)-3,4,5-trimethylpiperazin-1-yl)-[1,1'-biphenyl]-4-carboxylic acid (30 mg, 0.053 mmol) in Step 2 afforded the title compound as a white fluffy powder (1 mg, 2.4% yield). $^1$H NMR (500 MHz, METHANOL-d4) δ=7.88-7.83 (m, 2H), 7.69 (t, J=7.9 Hz, 1H), 7.38 (d, J=8.1 Hz, 1H), 7.33 (br d, J=12.1 Hz, 1H), 6.98 (d, J=12.2 Hz, 1H), 6.83-6.78 (m, 1H), 3.00 (br d, J=11.1 Hz, 2H), 2.57-2.51 (m, 2H), 2.48 (br d, J=6.0 Hz, 2H), 2.28 (s, 3H), 1.07 (d, J=6.1 Hz, 6H), 1.04-0.97 (m, 1H), 0.47-0.42 (m, 2H), 0.23-0.17 (m, 2H); LCMS [M+H]$^+$ 618.

Example 736: 4-fluoro-N-[4-fluoro-2-[(3R)-3,4-dimethylpiperazin-1-yl]-5-[2-[(3R)-3-methylmorpholin-4-yl]pyrimidin-5-yl]phenyl]-2-(trifluoromethyl)benzamide

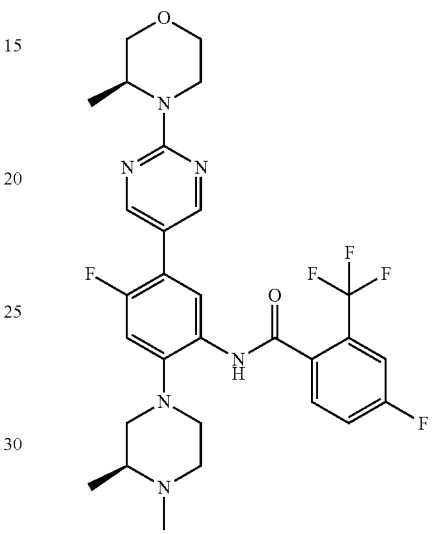

To a 20 mL microwave vial charged with 5-bromo-2-chloropyrimidine (967 mg, 5 mmol) and (S)-3-methylmorpholine (0.62 mL, 5.5 mmol) was added EtOH (5 mL), followed by Et$_3$N (1.40 mL, 10 mmol). The resulting mixture was heated in microwave at 120° C. for 1 h. Solvents were removed and the residue was dried to give the crude (S)-4-(5-bromopyrimidin-2-yl)-3-methylmorpholine as a light brown oil (1.152 g, 87%). LCMS [M+H]$^+$ 258.2. The title compound (formic acid salt, light yellow solid, 50.4 mg, 94% calcd. NMR purity, 37%) was prepared according to the second step described for the preparation of Example 660 using (S)-4-(5-bromopyrimidin-2-yl)-3-methylmorpholine in place of (S)-4-(4-bromopyrimidin-2-yl)-2-methylmorpholine. $^1$H NMR (500 MHz, METHANOL-d4) δ=8.56 (s, 2H), 8.39 (br s, 1H), 8.03 (d, J=8.2 Hz, 1H), 7.80 (dd, J=5.3, 8.4 Hz, 1H), 7.65 (dd, J=2.4, 9.0 Hz, 1H), 7.56 (dt, J=2.5, 8.2 Hz, 1H), 7.17 (d, J=11.9 Hz, 1H), 4.78-4.72 (m, 1H), 4.38 (dd, J=2.6, 13.6 Hz, 1H), 3.98 (dd, J=3.7, 11.4 Hz, 1H), 3.79 (d, J=11.4 Hz, 1H), 3.71 (dd, J=3.1, 11.4 Hz, 1H), 3.56 (dt, J=3.1, 11.9 Hz, 1H), 3.38-3.32 (m, 2H), 3.28-3.20 (m, 2H), 3.13-3.04 (m, 1H), 3.01 (br d, J=9.2 Hz, 2H), 2.82 (dd, J=10.4, 12.5 Hz, 1H), 2.71 (s, 3H), 1.34-1.28 (m, 6H); LCMS [M+H]$^+$ 591.3.

Example 737: 4-fluoro-N-[4-fluoro-2-[(3S)-3,4-dimethylpiperazin-1-yl]-5-[2-[(3R)-3-methylmorpholin-4-yl]pyrimidin-5-yl]phenyl]-2-(trifluoromethyl)benzamide Example 738: 4-fluoro-N-[4-fluoro-2-[(3S)-3,4-dimethylpiperazin-1-yl]-5-[2-[(2R)-2-methylmorpholin-4-yl]pyrimidin-4-yl]phenyl]-2-(trifluoromethyl)benzamide

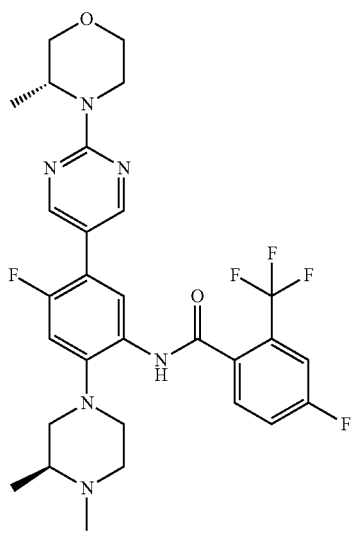 [SMILES: C[C@@H]1COCCN1c1ncc(-c2cc(NC(=O)c3ccc(F)cc3C(F)(F)F)c(N3CCN(C)[C@@H](C)C3)cc2F)cn1]

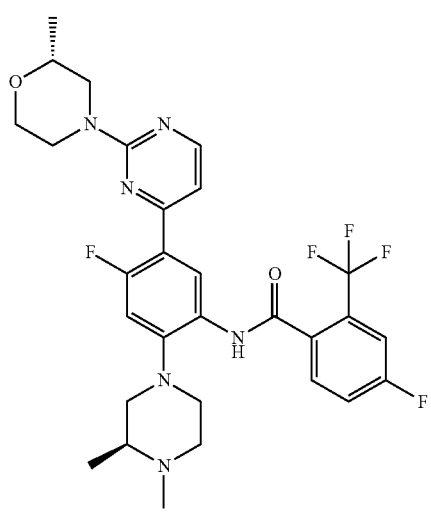 [SMILES: C[C@@H]1CN(c2nccc(-c3cc(NC(=O)c4ccc(F)cc4C(F)(F)F)c(N4CCN(C)[C@@H](C)C4)cc3F)n2)CCO1]

To a 20 mL microwave vial charged with 5-bromo-2-chloropyrimidine (967 mg, 5 mmol) and (R)-3-methylmorpholine (0.62 mL, 5.5 mmol) was added EtOH (5 mL), followed by Et$_3$N (1.40 mL, 10 mmol). The resulting mixture was heated in microwave at 120° C. for 1 h. Solvents were removed and the residue was dried to give crude (R)-4-(5-bromopyrimidin-2-yl)-3-methylmorpholine as a light brown oil (1.003 g, 74%). LCMS [M+H]$^+$ 258.2. The title compound (formic acid salt, light yellow solid, 36.5 mg, 89% calcd. NMR purity, 26%) was prepared according to the second step described above for the preparation of Example 736 using crude (R)-4-(5-bromopyrimidin-2-yl)-3-methylmorpholine in place of (S)-4-(5-bromopyrimidin-2-yl)-3-methylmorpholine. $^1$H NMR (500 MHz, METHANOL-d4) δ=8.57 (s, 2H), 8.46 (br s, 1H), 8.05 (d, J=8.3 Hz, 1H), 7.82 (dd, J=5.3, 8.5 Hz, 1H), 7.67 (dd, J=2.4, 9.0 Hz, 1H), 7.58 (dt, J=2.5, 8.2 Hz, 1H), 7.18 (d, J=11.9 Hz, 1H), 4.80-4.72 (m, 1H), 4.40 (dd, J=2.6, 13.6 Hz, 1H), 4.00 (dd, J=3.6, 11.3 Hz, 1H), 3.81 (d, J=11.5 Hz, 1H), 3.73 (dd, J=3.1, 11.5 Hz, 1H), 3.58 (dt, J=3.0, 11.9 Hz, 1H), 3.36-3.34 (m, 1H), 3.28-3.17 (m, 3H), 3.07 (br t, J=10.9 Hz, 1H), 2.94-2.84 (m, 2H), 2.81-2.74 (m, 1H), 2.64 (s, 3H), 1.34-1.31 (m, 3H), 1.27 (d, J=6.4 Hz, 3H); LCMS [M+H]$^+$ 591.3.

The title compound (formic acid salt, pale beige solid, 68.8 mg, 53%) was prepared according to the second step described above for the preparation of Example 736 using (R)-4-(4-bromopyrimidin-2-yl)-2-methylmorpholine in place of (S)-4-(5-bromopyrimidin-2-yl)-3-methylmorpholine. $^1$H NMR (500 MHz, METHANOL-d4) δ=8.74 (d, J=8.2 Hz, 1H), 8.41 (s, 1H), 8.39 (s, 1H), 7.77 (dd, J=5.3, 8.4 Hz, 1H), 7.68 (dd, J=2.2, 9.0 Hz, 1H), 7.58 (dt, J=2.2, 8.3 Hz, 1H), 7.16 (d, J=5.8 Hz, 1H), 7.12-7.08 (m, 1H), 4.68 (br d, J=13.1 Hz, 1H), 4.61 (br d, J=13.3 Hz, 1H), 3.98 (dd, J=2.3, 11.5 Hz, 1H), 3.71-3.59 (m, 2H), 3.40-3.34 (m, 2H), 3.17-2.97 (m, 4H), 2.92-2.81 (m, 1H), 2.77-2.67 (m, 4H), 1.33 (d, J=6.4 Hz, 3H), 1.25 (d, J=6.2 Hz, 3H); LCMS [M+H]$^+$ 591.3.

Example 739: 4-fluoro-N-[4-fluoro-5-[2-[(2R,6S)-2,6-dimethylmorpholin-4-yl]pyrimidin-4-yl]-2-[(3R)-3,4-dimethylpiperazin-1-yl]phenyl]-2-(trifluoromethyl)benzamide

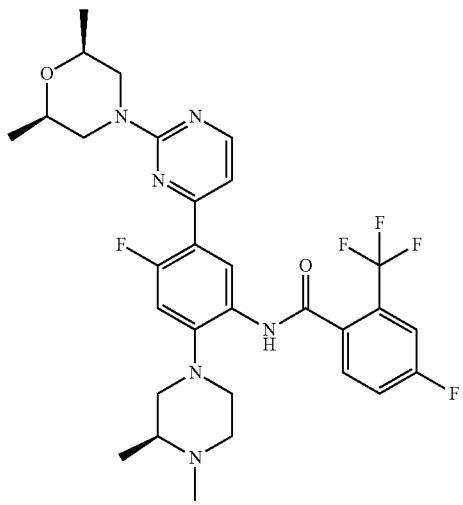 [SMILES: C[C@@H]1CN(c2nccc(-c3cc(NC(=O)c4ccc(F)cc4C(F)(F)F)c(N4CCN(C)[C@@H](C)C4)cc3F)n2)C[C@H](C)O1]

The title compound (formic acid salt, pale beige solid, 74.3 mg, 57%) was prepared according to the second step described above for the preparation of example 736 using (2S,6R)-4-(4-bromopyrimidin-2-yl)-2,6-dimethylmorpholine in place of (S)-4-(5-bromopyrimidin-2-yl)-3-methylmorpholine. $^1$H NMR (500 MHz, METHANOL-d4) δ=8.73 (d, J=8.3 Hz, 1H), 8.45 (br s, 1H), 8.38 (d, J=5.1 Hz, 1H), 7.75 (dd, J=5.3, 8.3 Hz, 1H), 7.67 (dd, J=2.1, 9.0 Hz, 1H), 7.58 (dt, J=2.1, 8.2 Hz, 1H), 7.15 (d, J=5.9 Hz, 1H), 7.08 (d, J=13.1 Hz, 1H), 4.74-4.64 (m, 2H), 3.74-3.62 (m, 2H), 3.39-3.23 (m, 3H), 3.13-3.02 (m, 1H), 2.96-2.85 (m, 2H), 2.85-2.75 (m, 1H), 2.69-2.58 (m, 5H), 1.29 (d, J=6.2 Hz, 3H), 1.26 (d, J=6.2 Hz, 6H); LCMS [M+H]$^+$ 605.3.

Example 740: N-[5-[1-(2-cyanopyrimidin-4-yl)-3,6-dihydro-2H-pyridin-5-yl]-4-fluoro-2-[(3R)-3,4-dimethylpiperazin-1-yl]phenyl]-4-(difluoromethyl)-6-oxo-1H-pyridine-3-carboxamide

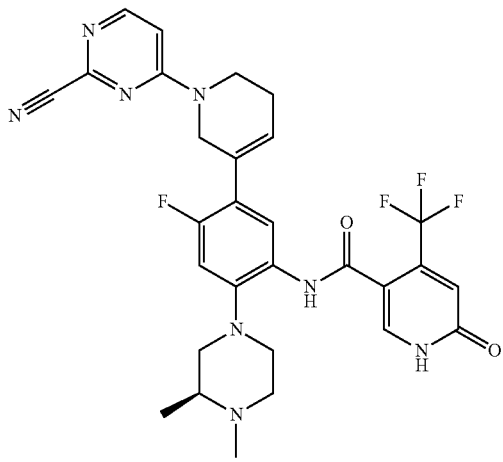 [SMILES: C[C@H]1CN(c2cc(F)c(C3=CCCN(c4ccnc(C#N)n4)C3)cc2NC(=O)c2c[nH]c(=O)cc2C(F)(F)F)CCN1C]

The procedure followed was similar to Example 270 using 4-bromopyrimidine-2-carbonitrile (10.64 mg, 0.058 mmol) and (S)-4-(difluoromethyl)-N-(2-(3,4-dimethylpiperazin-1-yl)-4-fluoro-5-(1,2,5,6-tetrahydropyridin-3-yl)phenyl)-6-oxo-1,6-dihydropyridine-3-carboxamide (25 mg, 0.053 mmol) to afford the title compound (17 mg, 53% yield). $^1$H NMR (500 MHz, METHANOL-d4) δ=8.13-8.05 (m, 1H), 7.93-7.87 (m, 1H), 7.64-7.57 (m, 1H), 7.33-7.08 (m, 1H), 6.92-6.83 (m, 2H), 6.74-6.67 (m, 1H), 6.13-6.05 (m, 1H), 4.52-4.16 (m, 2H), 3.98-3.66 (m, 2H), 3.03-2.96 (m, 1H), 2.96-2.90 (m, 1H), 2.84-2.77 (m, 2H), 2.46-2.39 (m, 2H), 2.38-2.33 (m, 2H), 2.32-2.25 (m, 4H), 1.03-0.99 (m, 3H); LCMS [M+H]$^+$ 579.5.

Example 741: 4-(difluoromethyl)-N-[4-fluoro-5-[4-(morpholin-4-ylmethyl)-1,3-thiazol-2-yl]-2-[(3R,5S)-3,4,5-trimethylpiperazin-1-yl]phenyl]-1-methyl-6-oxopyridine-3-carboxamide

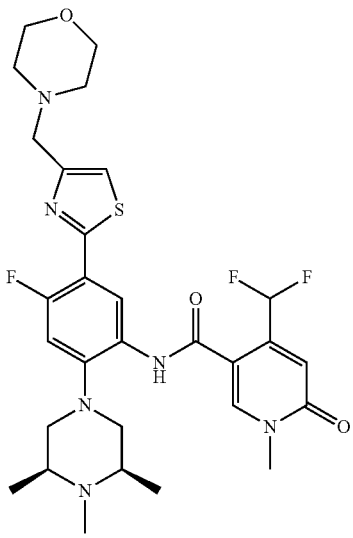 [SMILES: C[C@@H]1CN(c2cc(F)c(-c3nc(CN4CCOCC4)cs3)cc2NC(=O)c2cn(C)c(=O)cc2C(F)F)C[C@H](C)N1C]

Step 1: 4-((2-bromothiazol-4-yl)methyl)morpholine

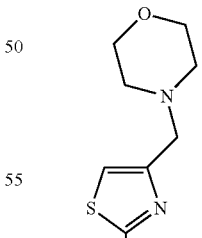

2-Bromo-thiazole-4-carbaldehyde (0.15 g, 0.781 mmol), morpholine (0.14 mL, 1.6 mmol) and acetic acid (0.18 mL, 3.1 mmol) were mixed in anhydrous DCE (8 mL). After 5 min, sodium triacetoxyborohydride (0.50 g, 2.3 mmol) was added and the reaction mixture was allowed to stir at room temperature for 18 h. The reaction was quenched with saturated aqueous sodium bicarbonate and extracted with DCM. The combined organic extracts were washed with a saturated brine solution and dried over magnesium sulfate. After removal of the inorganics by filtration the filtrate was concentrated in vacuo to afford 4-((2-bromothiazol-4-yl)methyl)morpholine (0.18 g, 47%). LCMS [M+H]+: 263.1.

Step 2: 4-((2-(2-fluoro-5-nitro-4-(cis-3,4,5-trimethylpiperazin-1-yl)phenyl)thiazol-4-yl)methyl)morpholine

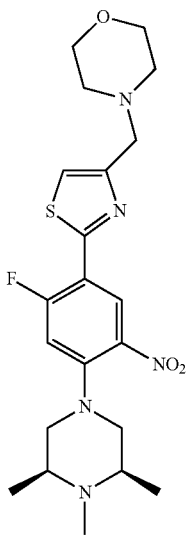 [SMILES: C[C@@H]1CN(c2cc(F)c(-c3nc(CN4CCOCC4)cs3)cc2[N+](=O)[O-])C[C@H](C)N1C]

A reaction vial was charged with a mixture of 2-(2-fluoro-5-nitro-4-(cis-3,4,5-trimethylpiperazin-1-yl)phenyl)-6-methyl-1,3,6,2-dioxazaborocane-4,8-dione (0.075 g, 0.18 mmol), 6-bromo-1-methyl-1H-benzo[d]imidazole (0.056 g, 0.27 mmol) and tetrakis(triphenylphosphine)palladium(0) (0.021 g, 0.018 mmol). The vial was sealed with a septum and evacuated and backfilled with nitrogen. 1,4-dioxane (5 mL) and 2 M aqueous sodium carbonate (0.5 mL) were added via syringe and the vial was evacuated and backfilled an additional time. The reaction was heated to 90° C. for 18 h. After cooling to room temperature the reaction mixture was concentrated onto celite and purified by flash chromatography [0-10% MeOH/DCM+0.1% NH₄OH] to afford 4-((2-(2-fluoro-5-nitro-4-(cis-3,4,5-trimethylpiperazin-1-yl)phenyl)thiazol-4-yl)methyl)morpholine (0.090 g, 84%). LCMS [M+H]+: 450.2.

Step 3: 4-fluoro-5-(4-(morpholinomethyl)thiazol-2-yl)-2-(cis-3,4,5-trimethylpiperazin-1-yl)aniline

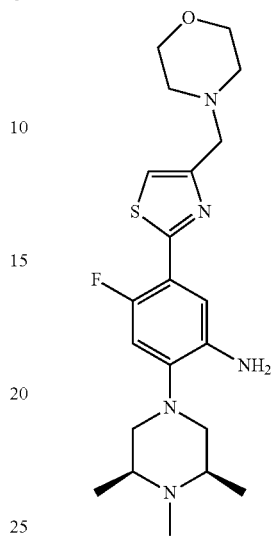

A mixture of 4-((2-(2-fluoro-5-nitro-4-(cis-3,4,5-trimethylpiperazin-1-yl)phenyl)thiazol-4-yl)methyl)morpholine (0.090 g, 0.20 mmol) and tin chloride (0.11 g, 0.60 mmol) in EtOH (4 mL) was heated to 80° C. for 3 h. After cooling to room temperature the reaction mixture was concentrated onto celite and purified by flash [0.5-10% MeOH/DCM+0.5% NH₄OH] to afford 4-fluoro-5-(4-(morpholinomethyl)thiazol-2-yl)-2-(cis-3,4,5-trimethylpiperazin-1-yl)aniline (0.039 g, 46%). LCMS [M+H]+: 420.4.

Step 4: 4-(difluoromethyl)-N-(4-fluoro-5-(4-(morpholinomethyl)thiazol-2-yl)-2-(cis-3,4,5-trimethylpiperazin-1-yl)phenyl)-1-methyl-6-oxo-1,6-dihydropyridine-3-carboxamide

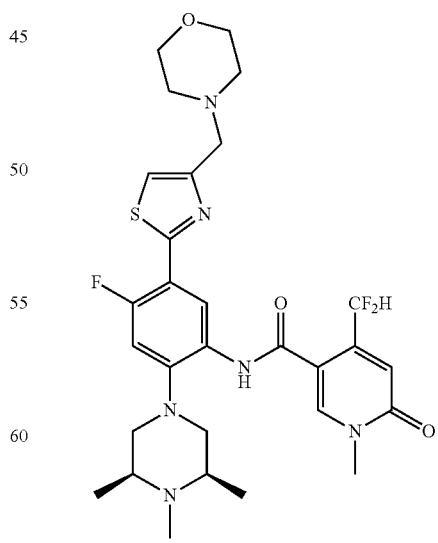

4-(Difluoromethyl)-1-methyl-6-oxo-1,6-dihydropyridine-3-carboxylic acid (0.014 g, 0.068 mmol) was activated with HATU (0.026 g, 0.068 mmol) and N,N-diisopropylethylamine (0.012 mL, 0.068 mmol) in DMF (1 mL). After agitating for 5 min the solution of activated acid was added dropwise to a stirring solution of 4-fluoro-5-(4-(morpholinomethyl)thiazol-2-yl)-2-(cis-3,4,5-trimethylpiperazin-1-yl)aniline (0.019 g, 0.045 mmol) in DMF (1 mL) and the reaction warmed to 40° C. for 18 h. The reaction mixture was loaded onto celite and purified by flash chromatography [0.5-10% MeOH/DCM+0.5% NH$_4$OH]. The product containing fractions were combined and concentrated onto celite and repurified by reverse phase chromatography [5-95% MeCN/10 mM NH$_4$HCO$_3$] to afford the title compound 4-(difluoromethyl)-N-(4-fluoro-5-(4-(morpholinomethyl)thiazol-2-yl)-2-(cis-3,4,5-trimethylpiperazin-1-yl)phenyl)-1-methyl-6-oxo-1,6-dihydropyridine-3-carboxamide (0.0089 g, 32%). $^1$H NMR (500 MHz, DMSO-d6) δ=9.60 (s, 1H), 8.43 (s, 1H), 8.26 (d, J=8.2 Hz, 1H), 7.58 (s, 1H), 7.49-7.20 (m, 1H), 7.08 (d, J=13.2 Hz, 1H), 6.64 (s, 1H), 3.64 (s, 2H), 3.58 (t, J=4.5 Hz, 4H), 3.52 (s, 3H), 3.13 (br d, J=11.4 Hz, 2H), 2.47 (s, 1H), 2.44 (br s, 3H), 2.38-2.28 (m, 2H), 2.18 (s, 3H), 1.00 (d, J=6.1 Hz, 6H); LCMS [M+H]+: 605.3.

Example 742: N-[4-fluoro-5-(6-piperazin-1-ylpyridin-2-yl)-2-[(3R)-3,4-dimethylpiperazin-1-yl]phenyl]-6-oxo-4-(trifluoromethyl)-1H-pyridine-3-carboxamide

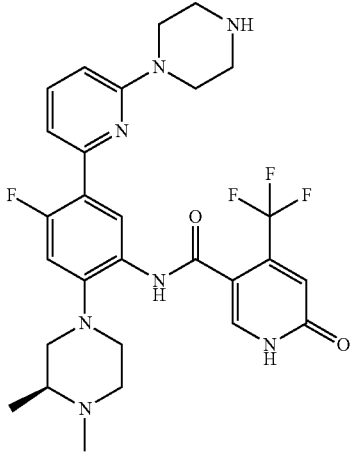

The title compound was prepared similar to the sequence described for the preparation of Example 698 using 4-Boc-1-(6-bromo-2-pyridyl)piperazine in place of (2S,6R)-4-(4-bromopyrimidin-2-yl)-2,6-dimethylmorpholine. $^1$H NMR (500 MHz, MeOD) δ 8.55 (d, J=8.6 Hz, 1H), 7.99 (s, 1H), 7.62 (t, J=8.0 Hz, 1H), 7.22 (dd, J=7.5, 2.1 Hz, 1H), 7.00 (d, J=12.9 Hz, 1H), 6.84 (s, 1H), 6.79 (d, J=8.3 Hz, 1H), 3.68 (dd, J=6.2, 4.3 Hz, 4H), 3.16-3.12 (m, 1H), 3.10 (dt, J=11.7, 2.7 Hz, 1H), 3.07-3.04 (m, 4H), 2.94 (td, J=10.6, 2.8 Hz, 2H), 2.58-2.52 (m, 2H), 2.42-2.38 (m, 1H), 2.36 (s, 3H), 1.13 (d, J=6.4 Hz, 3H); LCMS [M+1]$^+$=574.32.

Example 743: N-[4-fluoro-5-[2-[(2R,6S)-2,6-dimethylmorpholin-4-yl]pyrimidin-4-yl]-2-[(3R,5S)-3,4,5-trimethylpiperazin-1-yl]phenyl]-1-methyl-6-oxo-4-(trifluoromethyl)pyridine-3-carboxamide

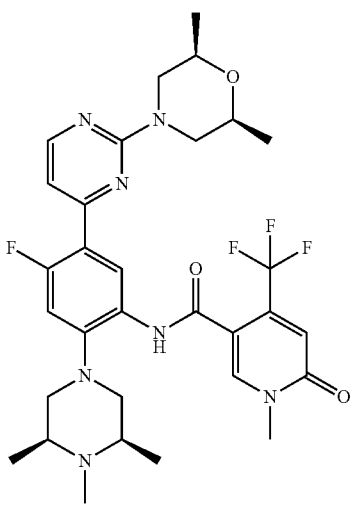

The title compound (25 mg, 26% yield) was prepared similar to the sequence described above for the preparation of Example 693 from N-(4-fluoro-5-(tributylstannyl)-2-((3S,5R)-3,4,5-trimethylpiperazin-1-yl)phenyl)-1-methyl-6-oxo-4-(trifluoromethyl)-1,6-dihydropyridine-3-carboxamide (113 mg, 0.155 mmol) and (2R,6S)-4-(4-bromopyrimidin-2-yl)-2,6-dimethylmorpholine (46.4 mg, 0.170 mmol). $^1$H NMR (500 MHz, MeOD) δ 8.64 (d, J=8.2 Hz, 1H), 8.36 (d, J=5.2 Hz, 1H), 8.18 (s, 1H), 7.11 (dd, J=5.2, 1.9 Hz, 1H), 7.02 (d, J=13.2 Hz, 1H), 6.94 (s, 1H), 4.68 (d, J=12.9 Hz, 2H), 3.70-3.65 (m, 2H), 3.64 (s, 3H), 3.14 (d, J=11.5 Hz, 2H), 2.65-2.58 (m, J=13.4, 11.0 Hz, 4H), 2.53 (s, 2H), 2.36 (s, 3H), 1.24 (d, J=6.2 Hz, 6H), 1.17 (d, J=6.2 Hz, 6H); LCMS HSS [M+1]$^+$=632.41.

Example 744: 4-(difluoromethyl)-N-[4-fluoro-5-[2-[(2R,6S)-2,6-dimethylmorpholin-4-yl]pyrimidin-4-yl]-2-[(3S,5R)-3,4,5-trimethylpiperazin-1-yl]phenyl]-6-oxo-1H-pyridine-3-carboxamide

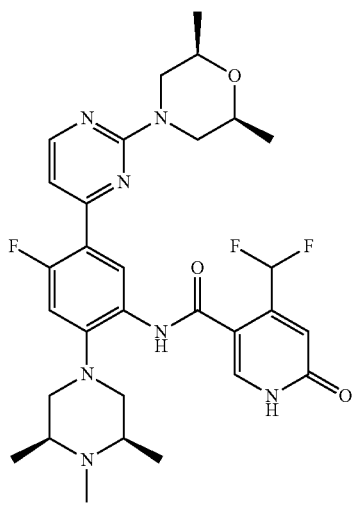

The title compound (26.2 mg, 29% yield) was prepared similar to the sequence described above for the preparation of Example 692 using 4-(difluoromethyl)-N-(4-fluoro-5-(tributylstannyl)-2-((3S,5R)-3,4,5-trimethylpiperazin-1-yl)phenyl)-6-(2-(trimethylsilyl)ethoxy)nicotinamide (111 mg, 0.139 mmol) and (2R,6S)-4-(4-bromopyrimidin-2-yl)-2,6-dimethylmorpholine (41.7 mg, 0.153 mmol). $^1$H NMR (500 MHz, MeOD) δ 8.50 (d, J=8.2 Hz, 1H), 8.35 (d, J=5.2 Hz, 1H), 7.98 (s, 1H), 7.32 (t, J=55.1 Hz, 1H), 7.10 (dd, J=5.2, 1.9 Hz, 1H), 6.99 (d, J=13.2 Hz, 1H), 6.81 (s, 1H), 4.67 (d, J=12.4 Hz, 2H), 3.66 (ddd, J=10.5, 6.3, 2.4 Hz, 2H), 3.16 (d, J=11.3 Hz, 2H), 2.61 (dt, J=13.1, 9.3 Hz, 4H), 2.55-2.50 (m, 2H), 2.36 (s, 3H), 1.23 (d, J=6.2 Hz, 6H), 1.16 (d, J=6.2 Hz, 6H); LCMS [M+1]$^+$=600.35.

Example 745: 4-(difluoromethyl)-N-[4-fluoro-5-[2-[(2R,6S)-2,6-dimethylmorpholin-4-yl]pyrimidin-4-yl]-2-[(3R,5S)-3,4,5-trimethylpiperazin-1-yl]phenyl]-1-methyl-6-oxopyridine-3-carboxamide

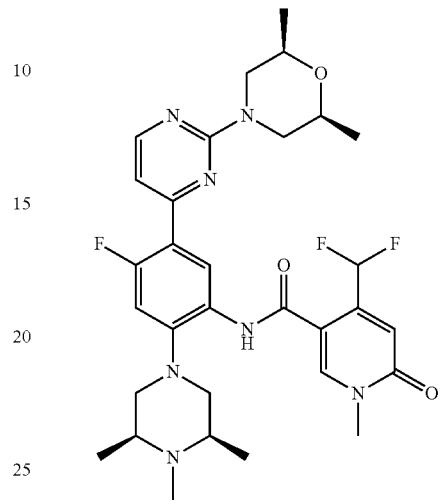

Step 1: 4-(difluoromethyl)-N-(4-fluoro-5-(tributylstannyl)-2-((3S,5R)-3,4,5-trimethylpiperazin-1-yl)phenyl)-1-methyl-6-oxo-1,6-dihydropyridine-3-carboxamide

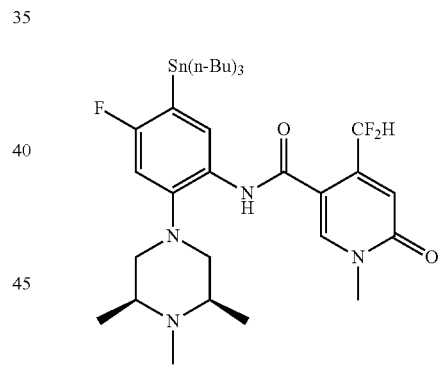

To a stirred solution of N-(5-bromo-4-fluoro-2-((3S,5R)-3,4,5-trimethylpiperazin-1-yl)phenyl)-4-(difluoromethyl)-1-methyl-6-oxo-1,6-dihydropyridine-3-carboxamide (6 g, 12.0 mmol, 1 eq, prepared as described in Example 416) in toluene:DMF (60:5 mL) degassed with argon for 15 min, then hexabutylditin (12.22 mL, 24.0 mmol, 2 eq) was added, followed by Pd$_2$(dppf)$_2$C$_{1-2}$ (0.97 g, 1.2 mmol, 0.1 eq) and after that heated to reflux under argon atmosphere for 24 h. TLC analysis indicated formation of less polar spots. The reaction mixture was filtered through celite bed washed with EtOAc; the filtrate was evaporated under reduced pressure. The crude compound was purified by column chromatography (neutral alumina) using 0-50% EtOAc in pet ether as an eluent to afford 4-(difluoromethyl)-N-(4-fluoro-5-(tributylstannyl)-2-((3S,5R)-3,4,5-trimethylpiperazin-1-yl)phenyl)-1-methyl-6-oxo-1,6-dihydropyridine-3-carboxamide (4.3 g, 50%) as an off white solid. LCMS: [M+H]+ 713.46.

Step 2: 4-(difluoromethyl)-N-(5-(2-((2S,6R)-2,6-dimethylmorpholino)pyrimidin-4-yl)-4-fluoro-2-((3S,5R)-3,4,5-trimethylpiperazin-1-yl)phenyl)-1-methyl-6-oxo-1,6-dihydropyridine-3-carboxamide Example 746: 4-(difluoromethyl)-N-[4-fluoro-5-(2-morpholin-4-ylpyrimidin-4-yl)-2-[(3R,5S)-3,4,5-trimethylpiperazin-1-yl]phenyl]-1-methyl-6-oxopyridine-3-carboxamide

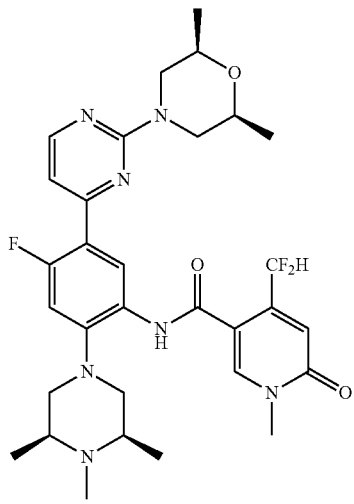

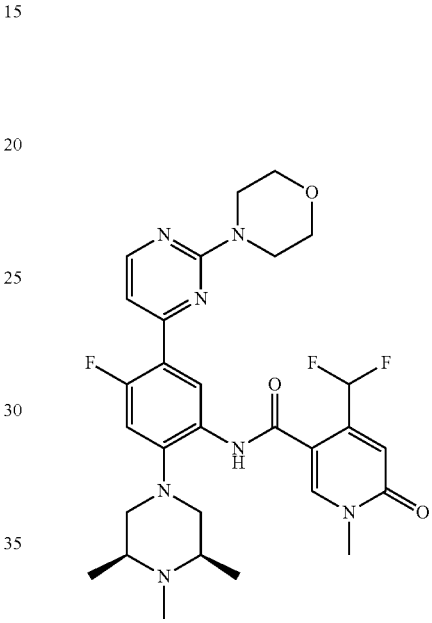

In N,N-dimethylformamide (DMF) (635 µl) was dissolved 4-(difluoromethyl)-N-(4-fluoro-5-(tributylstannyl)-2-((3S,5R)-3,4,5-trimethylpiperazin-1-yl)phenyl)-1-methyl-6-oxo-1,6-dihydropyridine-3-carboxamide (113 mg, 0.159 mmol). To the solution was added (2R,6S)-4-(4-bromopyrimidin-2-yl)-2,6-dimethylmorpholine (47.5 mg, 0.175 mmol), lithium chloride (20.20 mg, 0.476 mmol) and bis(triphenylphosphine)palladium(II) dichloride (6.13 mg, 8.74 µmol) at room temperature and then it was microwaved at the temperature of 120° C. for 3 hours. To the reaction mixture was added water and then it was extracted with DCM. The organic layer was separated, concentrated and purified by column chromatography on silica gel (0-100%, 89% $CH_2Cl_2$, 10% MeOH, 1% $NH_4Ac/CH_2Cl_2$) the fractions were concentrated and freeze dried for 2 days to afford the product as a white powder. $^1$H NMR (500 MHz, MeOD) δ 8.47 (d, J=8.1 Hz, 1H), 8.35 (d, J=5.4 Hz, 1H), 8.26 (s, 1H), 7.29 (t, J=55.2 Hz, 1H), 7.09 (dd, J=5.1, 2.2 Hz, 1H), 7.00 (d, J=13.2 Hz, 1H), 6.82 (s, 1H), 4.66 (dd, J=13.4, 2.2 Hz, 2H), 3.66 (ddd, J=6.8, 5.3, 2.4 Hz, 2H), 3.64 (s, 3H), 3.16 (d, J=11.7 Hz, 2H), 2.64-2.57 (m, 4H), 2.50 (ddd, J=10.8, 6.7, 3.4 Hz, 2H), 2.35 (s, 3H), 1.23 (d, J=6.1 Hz, 6H), 1.15 (d, J=6.1 Hz, 6H); LCMS [M+1]$^+$=614.35.

The title compound (19.7 mg, 22% yield) was prepared similar to the sequence described above for the preparation of Example 745 using 4-(difluoromethyl)-N-(4-fluoro-5-(tributylstannyl)-2-((3S,5R)-3,4,5-trimethylpiperazin-1-yl)phenyl)-1-methyl-6-oxo-1,6-dihydropyridine-3-carboxamide (111 mg, 0.156 mmol) and 4-(4-bromopyrimidin-2-yl)morpholine (38.1 mg, 0.156 mmol). $^1$H NMR (500 MHz, MeOD) δ 8.41 (d, J=8.2 Hz, 1H), 8.37 (d, J=5.2 Hz, 1H), 8.29 (s, 1H), 7.28 (t, J=55.2 Hz, 1H), 7.12 (dd, J=5.2, 2.0 Hz, 1H), 6.99 (d, J=13.3 Hz, 1H), 6.81 (s, 1H), 3.84-3.82 (m, 4H), 3.76-3.74 (m, 4H), 3.63 (s, 3H), 3.16 (d, J=11.8 Hz, 2H), 2.61 (t, J=11.2 Hz, 2H), 2.50 (s, 2H), 2.34 (s, 3H), 1.14 (d, J=6.2 Hz, 6H); LCMS [M+1]$^+$=586.36.

Example 747: N-[5-[4-[(2,2-dimethylcyclohexyl)carbamoyl]-3-fluorophenyl]-4-fluoro-2-[(3R,5S)-3,4,5-trimethylpiperazin-1-yl]phenyl]-6-oxo-4-(trifluoromethyl)-1H-pyridine-3-carboxamide

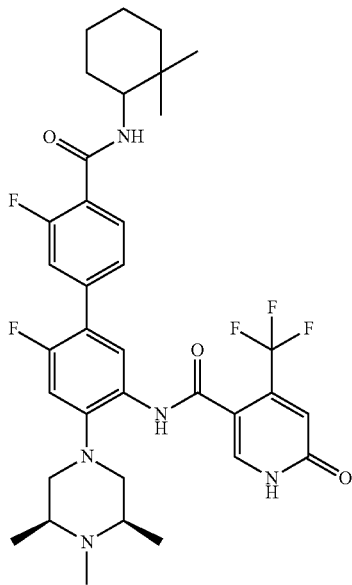 [SMILES: C[C@@H]1CN(c2cc(F)c(-c3ccc(C(=O)NC4CCCCC4(C)C)c(F)c3)cc2NC(=O)c2c[nH]c(=O)cc2C(F)(F)F)C[C@H](C)N1C]

A procedure similar to that of Example 732 using 2,2-dimethylcyclohexanamine (10.14 mg, 0.080 mmol) and 2',3-difluoro-5'-(6-oxo-4-(trifluoromethyl)-1,6-dihydropyridine-3-carboxamido)-4'-((3S,5R)-3,4,5-trimethylpiperazin-1-yl)-[1,1'-biphenyl]-4-carboxylic acid (30 mg, 0.053 mmol) afforded the title compound as an off-white fluffy powder (15.4 mg, 38.2% yield). $^1$H NMR (500 MHz, METHANOL-d4) δ=7.89-7.81 (m, 3H), 7.64 (t, J=7.9 Hz, 1H), 7.38 (d, J=8.1 Hz, 1H), 7.33 (d, J=11.9 Hz, 1H), 7.01 (d, J=12.1 Hz, 1H), 6.83 (s, 1H), 3.85-3.77 (m, 1H), 3.06 (br d, J=11.9 Hz, 2H), 2.67 (br s, 2H), 2.63-2.57 (m, 2H), 2.41 (s, 3H), 1.72-1.64 (m, 1H), 1.62-1.56 (m, 1H), 1.52-1.41 (m, 3H), 1.40-1.23 (m, 3H), 1.13 (d, J=6.1 Hz, 6H), 0.91 (s, 3H), 0.87 (s, 3H); LCMS [M+H]$^+$ 674.

Example 748: 4-(difluoromethyl)-N-[4-fluoro-5-[5-(morpholin-4-ylmethyl)-1,3-thiazol-2-yl]-2-[(3R,5S)-3,4,5-trimethylpiperazin-1-yl]phenyl]-1-methyl-6-oxopyridine-3-carboxamide

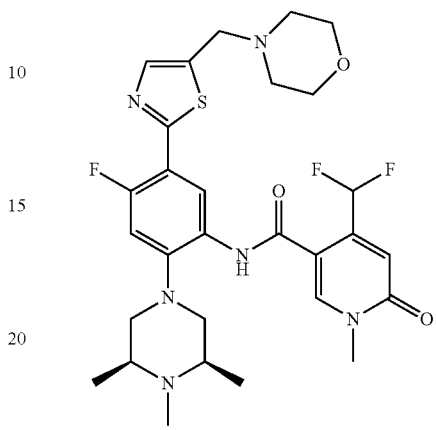

The title compound was prepared similar to the procedure described above for the preparation of Example 741 using 2-bromo-5-formylthiazole in place of 2-bromo-thiazole-4-carbaldehyde in Step 1. $^1$H NMR (500 MHz, DMSO-d6) δ=9.57 (s, 1H), 8.38 (s, 1H), 8.32 (br d, J=8.1 Hz, 1H), 7.78 (s, 1H), 7.53-7.19 (m, 1H), 7.09 (br d, J=12.7 Hz, 1H), 6.64 (s, 1H), 3.78 (s, 2H), 3.58 (br t, J=4.3 Hz, 4H), 3.52 (s, 3H), 3.14 (br d, J=9.9 Hz, 2H), 2.42 (br s, 4H), 2.38-2.27 (m, 2H), 2.18 (br s, 3H), 1.01 (br s, 6H); LCMS [M+H]+: 605.1.

Example 749: 4-(difluoromethyl)-N-[4-fluoro-5-[2-(morpholin-4-ylmethyl)-1,3-thiazol-4-yl]-2-[(3R,5S)-3,4,5-trimethylpiperazin-1-yl]phenyl]-1-methyl-6-oxopyridine-3-carboxamide

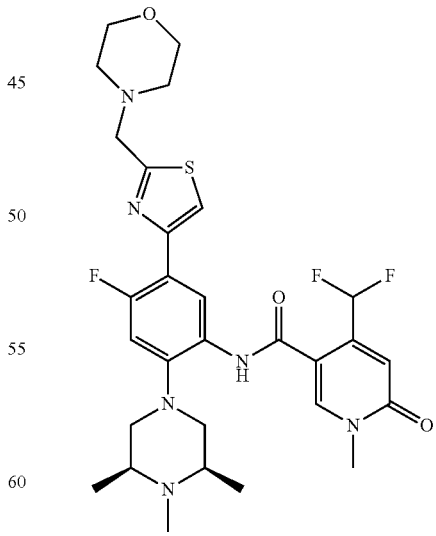

The title compound was prepared similar to the procedure described above for the preparation of Example 741 using 4-bromo-2-formylthiazole in place of 2-bromo-thiazole-4-carbaldehyde in Step 1. $^1$H NMR (500 MHz, DMSO-d6)

δ=9.49 (s, 1H), 8.42 (s, 1H), 8.21 (d, J=8.3 Hz, 1H), 7.83 (d, J=2.3 Hz, 1H), 7.51-7.19 (m, 1H), 7.02 (d, J=13.2 Hz, 1H), 6.64 (s, 1H), 3.87 (s, 2H), 3.65-3.58 (m, 4H), 3.52 (s, 3H), 3.06 (br d, J=11.1 Hz, 2H), 2.53 (br s, 4H), 2.46-2.46 (m, 1H), 2.47-2.42 (m, 1H), 2.35-2.28 (m, 2H), 2.18 (s, 3H), 0.99 (d, J=6.0 Hz, 6H); LCMS [M+H]+: 605.3.

Example 750: N-[4-fluoro-5-[4-(morpholin-4-ylmethyl)-1,3-thiazol-2-yl]-2-[(3R,5S)-3,4,5-trimethylpiperazin-1-yl]phenyl]-6-oxo-4-(trifluoromethyl)-1H-pyridine-3-carboxamide

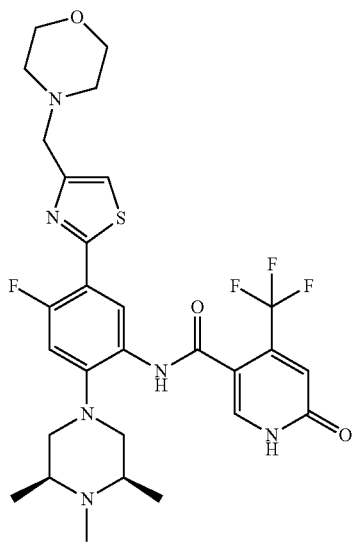 [SMILES: C[C@@H]1CN(c2cc(F)c(-c3nc(CN4CCOCC4)cs3)cc2NC(=O)c2c[nH]c(=O)cc2C(F)(F)F)C[C@H](C)N1C]

The title compound was prepared similar to the procedure described above for the preparation of Example 741 using 4-(trifluoromethyl)-6-(2-(trimethylsilyl)ethoxy)nicotinic acid in place of 4-(difluoromethyl)-1-methyl-6-oxo-1,6-dihydropyridine-3-carboxylic acid in Step 4. $^1$H NMR (500 MHz, DMSO-d6) δ=9.60 (s, 1H), 8.35 (d, J=8.1 Hz, 1H), 7.97 (s, 1H), 7.58 (s, 1H), 7.07 (d, J=13.1 Hz, 1H), 6.81 (s, 1H), 3.65 (s, 2H), 3.58 (t, J=4.5 Hz, 4H), 3.11 (br d, J=11.4 Hz, 2H), 2.48 (br s, 1H), 2.45 (br d, J=4.9 Hz, 4H), 2.39-2.31 (m, 2H), 2.19 (s, 3H), 1.00 (d, J=6.1 Hz, 6H); LCMS [M+H]+: 609.3.

Example 751: N-[4-fluoro-5-[5-(morpholin-4-ylmethyl)-1,3-thiazol-2-yl]-2-[(3R,5S)-3,4,5-trimethylpiperazin-1-yl]phenyl]-6-oxo-4-(trifluoromethyl)-1H-pyridine-3-carboxamide

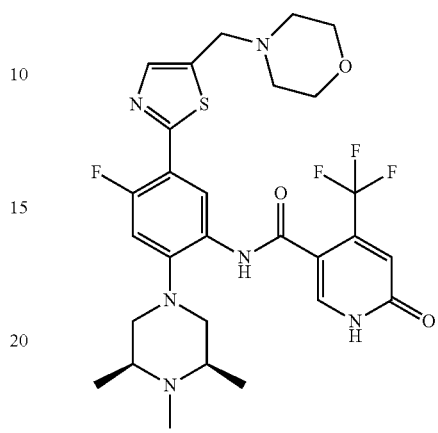

The title compound was prepared similar to the procedure described above for the preparation of Example 748 using 4-(trifluoromethyl)-6-(2-(trimethylsilyl)ethoxy)nicotinic acid in place of 4-(difluoromethyl)-1-methyl-6-oxo-1,6-dihydropyridine-3-carboxylic acid in Step 4. $^1$H NMR (500 MHz, DMSO-d6) δ=12.77-12.17 (m, 1H), 9.55 (s, 1H), 8.42 (d, J=8.2 Hz, 1H), 7.93 (s, 1H), 7.79 (s, 1H), 7.07 (d, J=13.1 Hz, 1H), 6.78 (s, 1H), 3.78 (s, 2H), 3.58 (br t, J=4.3 Hz, 4H), 3.11 (br d, J=11.1 Hz, 2H), 2.49-2.46 (m, 2H), 2.42 (br s, 4H), 2.39-2.31 (m, 2H), 2.19 (s, 3H), 1.01 (d, J=6.1 Hz, 6H); LCMS [M+H]+: 609.2.

Example 752: 2-(difluoromethyl)-N-(5-(2-((2S,6R)-2,6-dimethylmorpholino)pyrimidin-5-yl)-4-fluoro-2-((3S,5R)-3,4,5-trimethylpiperazin-1-yl)phenyl)-4-fluorobenzamide

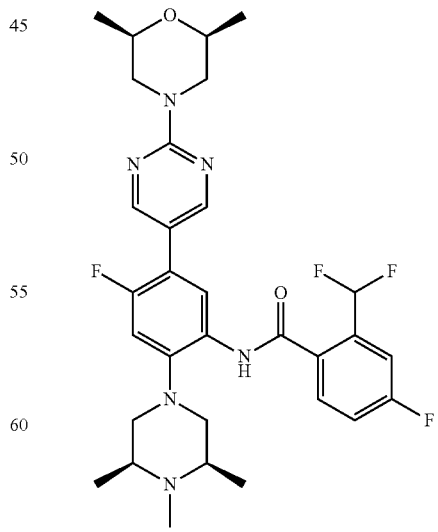

A mixture of 2-(difluoromethyl)-4-fluorobenzoic acid (171 mg, 0.9 mmol), HATU (342 mg, 0.9 mmol) and N,N-diisopropylethylamine (0.21 ml, 1.2 mmol) in DMF (2 mL) was heated at 70° C. for 1 min to afford a clear solution before 5-bromo-4-fluoro-2-((3S,5R)-3,4,5-trimethylpiperazin-1-yl)aniline (190 mg, 0.6 mmol) was added in one portion. The resulting mixture was heated at 70° C. for 2 h. It was diluted with EtOAc (20 mL) and washed with H$_2$O (30 mL×2), concentrated and purified by flash chromatography (EtOAc/hex 0-100%, then MeOH/DCM 0-5%) to give crude N-(5-bromo-4-fluoro-2-((3S,5R)-3,4,5-trimethylpiperazin-1-yl)phenyl)-2-(difluoromethyl)-4-fluorobenzamide as a dark brown (416 mg, 70% assuming full conversion). LCMS [M+H]$^+$ 488.0. It was redissolved in dioxane (12 mL) and divided equally into 3 portions (each 4 mL, 0.2 mmol). The title compound (formic acid salt, white solid, 26.7 mg, 21%) was prepared according to a procedure similar to Example 31 using (2-((2S,6R)-2,6-dimethylmorpholino)pyrimidin-5-yl)boronic acid (71 mg, 0.3 mmol) and crude N-(5-bromo-4-fluoro-2-((3S,5R)-3,4,5-trimethylpiperazin-1-yl)phenyl)-2-(difluoromethyl)-4-fluorobenzamide in dioxane (0.2 mmol). $^1$H NMR (500 MHz, METHANOL-d4) δ=8.54 (br s, 2H), 8.35 (br s, 1H), 7.95 (br d, J=8.1 Hz, 1H), 7.90-7.83 (m, 1H), 7.54 (br d, J=9.2 Hz, 1H), 7.48-7.24 (m, 2H), 7.19 (d, J=11.9 Hz, 1H), 4.63 (br d, J=13.0 Hz, 2H), 3.68-3.61 (m, 2H), 3.42-3.33 (m, 2H), 3.30-3.24 (m, 2H), 2.94 (br d, J=10.8 Hz, 2H), 2.84 (br s, 3H), 2.65-2.57 (m, 2H), 1.38 (br d, J=6.2 Hz, 6H), 1.23 (br d, J=6.1 Hz, 6H); LCMS [M+H]$^+$ 601.4.

Example 753: 2-(difluoromethyl)-4-fluoro-N-(4-fluoro-5-(2-((S)-2-methylmorpholino)pyrimidin-5-yl)-2-((3S,5R)-3,4,5-trimethylpiperazin-1-yl)phenyl)benzamide

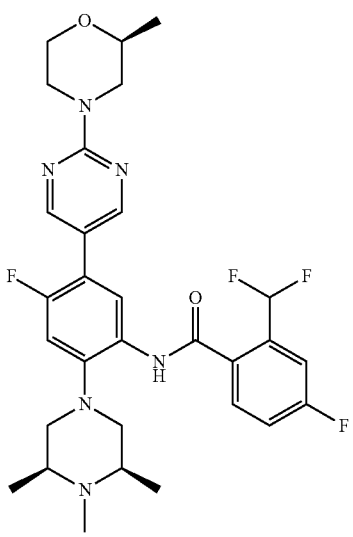 [SMILES: C[C@@H]1CN(c2cc(F)c(-c3cnc(N4CCO[C@@H](C)C4)nc3)cc2NC(=O)c2ccc(F)cc2C(F)F)C[C@H](C)N1C]

The title compound (formic acid salt, white solid, 36.5 mg, 29%) was prepared by a procedure similar to Example 31 using crude (S)-(2-(2-methylmorpholino)pyrimidin-5-yl)boronic acid (0.6 mmol) and crude N-(5-bromo-4-fluoro-2-((3S,5R)-3,4,5-trimethylpiperazin-1-yl)phenyl)-2-(difluoromethyl)-4-fluorobenzamide (preparation described in Example 752) in dioxane (0.2 mmol). $^1$H NMR (500 MHz, METHANOL-d4) δ=8.57 (s, 2H), 8.37 (br s, 1H), 7.97 (br d, J=8.2 Hz, 1H), 7.91-7.82 (m, 1H), 7.56 (dd, J=2.1, 9.2 Hz, 1H), 7.50-7.26 (m, 2H), 7.20 (d, J=11.9 Hz, 1H), 4.65-4.52 (m, 2H), 3.99 (dd, J=2.6, 11.5 Hz, 1H), 3.67-3.57 (m, 2H), 3.32-3.24 (m, 4H), 3.13-3.02 (m, 1H), 2.93 (br t, J=12.3 Hz, 2H), 2.83 (s, 3H), 2.74 (dd, J=10.5, 13.2 Hz, 1H), 1.38 (d, J=6.4 Hz, 6H), 1.25 (d, J=6.2 Hz, 3H); LCMS [M+H]$^+$ 587.3.

Example 754: 2-(difluoromethyl)-4-fluoro-N-(4-fluoro-5-(2-((R)-2-methylmorpholino)pyrimidin-5-yl)-2-((3S,5R)-3,4,5-trimethylpiperazin-1-yl)phenyl)benzamide

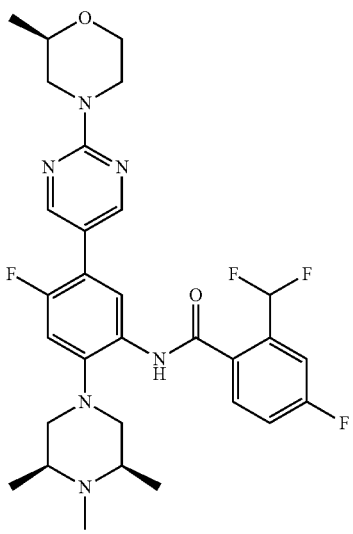 [SMILES: C[C@@H]1CN(c2ncc(-c3cc(NC(=O)c4ccc(F)cc4C(F)F)c(N4C[C@@H](C)N(C)[C@@H](C)C4)cc3F)cn2)CCO1]

The title compound (formic acid salt, white solid, 12.3 mg, 89% calcd. NMR purity, 9%) was prepared according to a procedure similar to Example 31 using crude (R)-(2-(2-methylmorpholino)pyrimidin-5-yl)boronic acid (0.6 mmol+ 0.3 mmol) and crude N-(5-bromo-4-fluoro-2-((3S,5R)-3,4,5-trimethylpiperazin-1-yl)phenyl)-2-(difluoromethyl)-4-fluorobenzamide in dioxane (0.2 mmol). $^1$H NMR (500 MHz, METHANOL-d4) δ=8.57 (s, 2H), 8.42 (br s, 1H), 7.97 (br d, J=8.1 Hz, 1H), 7.88 (br dd, J=5.5, 7.9 Hz, 1H), 7.56 (dd, J=2.4, 9.3 Hz, 1H), 7.51-7.26 (m, 2H), 7.18 (d, J=12.0 Hz, 1H), 4.66-4.55 (m, 2H), 3.99 (dd, J=2.4, 11.6 Hz, 1H), 3.69-3.58 (m, 2H), 3.27 (br d, J=12.3 Hz, 2H), 3.15-3.03 (m, 3H), 2.84 (br t, J=11.8 Hz, 2H), 2.77-2.68 (m, 4H), 1.33 (d, J=6.4 Hz, 6H), 1.25 (d, J=6.2 Hz, 3H); LCMS [M+H]$^+$ 587.4.

Example 755: 3-(difluoromethyl)-N-(5-(2-((2S,6R)-2,6-dimethylmorpholino)pyrimidin-5-yl)-4-fluoro-2-((3S,5R)-3,4,5-trimethylpiperazin-1-yl)phenyl)-5-fluoropicolinamide

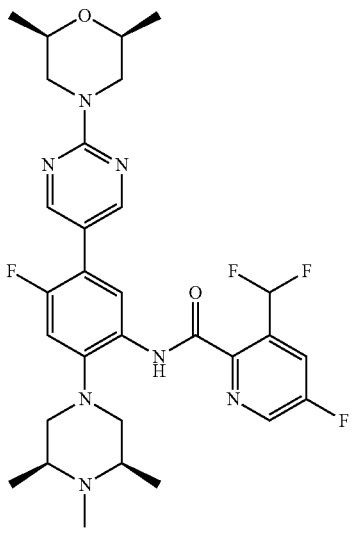 [SMILES: C[C@@H]1CN(c2ncc(-c3cc(NC(=O)c4ncc(F)cc4C(F)F)c(N4C[C@@H](C)N(C)[C@@H](C)C4)cc3F)cn2)C[C@H](C)O1]

The title compound was collected as a yellow fluffy powder (41.5 mg, 0.066 mmol, 69.7% yield). ¹HNMR (500 MHz, METHANOL-d4) δ=8.78 (br s, 1H), 8.58 (s, 2H), 8.55 (br d, J=8.2 Hz, 1H), 8.17 (br d, J=8.3 Hz, 1H), 8.14-7.90 (m, 1H), 7.14 (br d, J=11.7 Hz, 1H), 4.66 (br d, J=13.0 Hz, 2H), 3.74-3.63 (m, 2H), 3.06 (br d, J=8.9 Hz, 2H), 2.76-2.63 (m, 6H), 2.46 (s, 3H), 1.26 (br d, J=6.1 Hz, 6H), 1.19 (br d, J=5.0 Hz, 6H); LCMS [M+H]⁺ 602.

Example 756: 3-(difluoromethyl)-5-fluoro-N-(4-fluoro-5-(2-morpholinopyrimidin-5-yl)-2-((3S,5R)-3,4,5-trimethylpiperazin-1-yl)phenyl)picolinamide

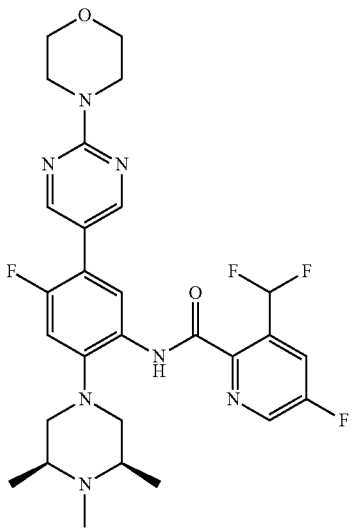 [SMILES: C[C@@H]1CN(c2cc(F)c(-c3cnc(N4CCOCC4)nc3)cc2NC(=O)c2ncc(F)cc2C(F)F)C[C@H](C)N1C]

The title compound was collected as a tan fluffy powder (36 mg, 0.058 mmol, 70.6% yield). ¹H NMR (500 MHz, METHANOL-d4) δ=8.66 (d, J=2.6 Hz, 1H), 8.47 (d, J=1.1 Hz, 2H), 8.42 (d, J=8.3 Hz, 1H), 8.04 (dd, J=2.4, 8.9 Hz, 1H), 8.01-7.78 (m, 1H), 7.05-6.98 (m, 1H), 3.77-3.72 (m, 4H), 3.69-3.62 (m, 4H), 2.96-2.91 (m, 2H), 2.62-2.52 (m, 4H), 2.34 (s, 3H), 1.07 (d, J=5.7 Hz, 6H); LCMS [M+H]⁺ 574.

Example 757: (S)-3-(difluoromethyl)-N-(2-(3,4-dimethylpiperazin-1-yl)-4-fluoro-5-(2-morpholinopyrimidin-4-yl)phenyl)-5-fluoropicolinamide

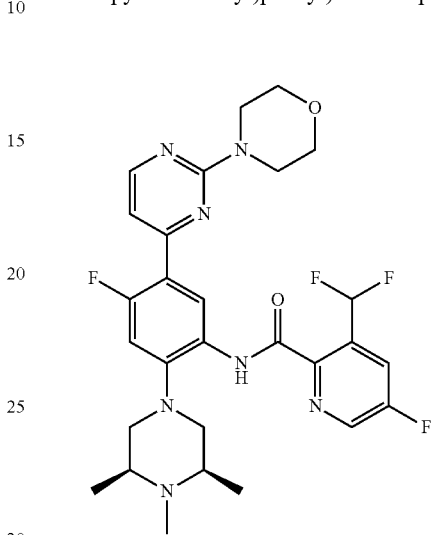

The title compound was collected as a beige fluffy powder (25 mg, 0.042 mmol, 40.6% yield). ¹H NMR (500 MHz, METHANOL-d4) δ=9.04 (d, J=8.2 Hz, 1H), 8.67 (d, J=2.6 Hz, 1H), 8.29 (d, J=5.3 Hz, 1H), 8.05 (dd, J=2.5, 8.9 Hz, 1H), 8.02-7.79 (m, 1H), 7.03-6.98 (m, 2H), 3.81-3.78 (m, 4H), 3.71-3.68 (m, 4H), 3.05-2.99 (m, 2H), 2.92-2.86 (m, 2H), 2.60-2.42 (m, 4H), 2.33 (s, 3H), 1.04 (d, J=6.1 Hz, 3H); LCMS [M+H]⁺ 560.

Example 758: 3-(difluoromethyl)-5-fluoro-N-(4-fluoro-5-(2-((R)-2-methylmorpholino)pyrimidin-4-yl)-2-((3S,5R)-3,4,5-trimethylpiperazin-1-yl)phenyl)picolinamide

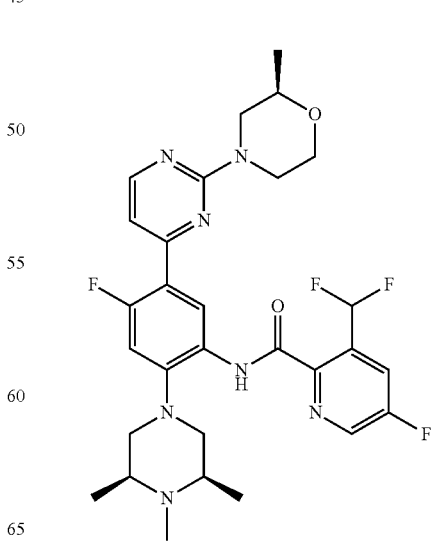

901

The title compound was collected as a tan fluffy powder (56 mg, 0.091 mmol, 63.1% yield). $^1$H NMR (500 MHz, METHANOL-d4) δ=9.14 (d, J=8.3 Hz, 1H), 8.63 (d, J=2.6 Hz, 1H), 8.26 (d, J=5.1 Hz, 1H), 8.03 (dd, J=2.4, 8.8 Hz, 1H), 8.00-7.76 (m, 1H), 7.01 (dd, J=1.9, 5.2 Hz, 1H), 6.93 (d, J=12.8 Hz, 1H), 4.64 (br d, J=13.0 Hz, 1H), 4.50 (br d, J=13.3 Hz, 1H), 3.88 (dd, J=2.6, 11.5 Hz, 1H), 3.59-3.51 (m, 2H), 3.02-2.96 (m, 3H), 2.63 (dd, J=10.5, 13.2 Hz, 1H), 2.59-2.51 (m, 4H), 2.33 (s, 3H), 1.17 (d, J=6.2 Hz, 3H), 1.06 (d, J=5.6 Hz, 6H); LCMS [M+H]$^+$ 588.

Example 759: 3-(difluoromethyl)-N-(5-(2-((2S,6R)-2,6-dimethylmorpholino)pyrimidin-4-yl)-4-fluoro-2-((3S,5R)-3,4,5-trimethylpiperazin-1-yl)phenyl)-5-fluoropicolinamide The title compound was collected as a dark beige fluffy powder (39 mg, 0.062 mmol, 42.9% yield). $^1$H NMR (500 MHz, METHANOL-d4) δ=9.24 (br d, J=8.1 Hz, 1H), 8.65 (br s, 1H), 8.26 (br d, J=4.9 Hz, 1H), 8.04 (br d, J=7.9 Hz, 1H), 8.01-7.77 (m, 1H), 7.02 (br d, J=3.8 Hz, 1H), 6.95 (br d, J=12.8 Hz, 1H), 4.64 (br d, J=12.8 Hz, 2H), 3.59 (br s, 2H), 3.02 (br d, J=9.4 Hz, 2H), 2.62-2.52 (m, 7H), 2.34 (s, 3H), 1.17 (br d, J=6.0 Hz, 6H), 1.07 (br d, J=5.0 Hz, 6H); LCMS [M+H]$^+$ 602.

902

Example 760: N-(4'-(cyclohexyl(methyl)carbamoyl)-3',5',6-trifluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

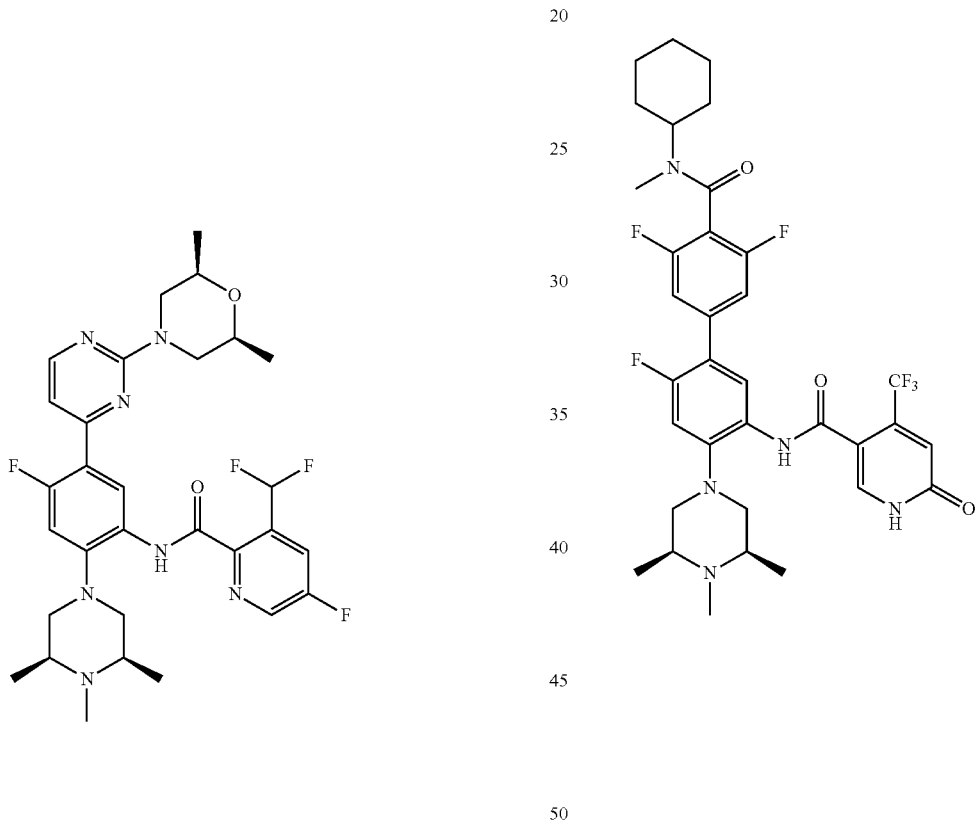

The title compound was collected as an off-white fluffy powder (13.9 mg, 0.019 mmol, 29.1% yield). 1H NMR (500 MHz, METHANOL-d4) δ=7.88-7.82 (m, 2H), 7.22 (dd, J=8.6, 11.4 Hz, 2H), 6.99 (dd, J=4.3, 12.4 Hz, 1H), 6.83-6.79 (m, 1H), 4.39 (tt, J=3.7, 12.0 Hz, 1H), 3.00 (br d, J=11.1 Hz, 2H), 2.94 (s, 2H), 2.78 (s, 1H), 2.56-2.50 (m, 2H), 2.48-2.39 (m, 2H), 2.27 (s, 3H), 1.80 (br d, J=13.3 Hz, 1H), 1.75-1.67 (m, 2H), 1.64-1.56 (m, 3H), 1.51 (dt, J=3.1, 12.3 Hz, 2H), 1.42-1.32 (m, 1H), 1.06 (d, J=6.1 Hz, 6H); LCMS [M+H]$^+$ 678.

903

Example 761: N-(4'-(cyclopentyl(methyl)carbamoyl)-3',5',6-trifluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

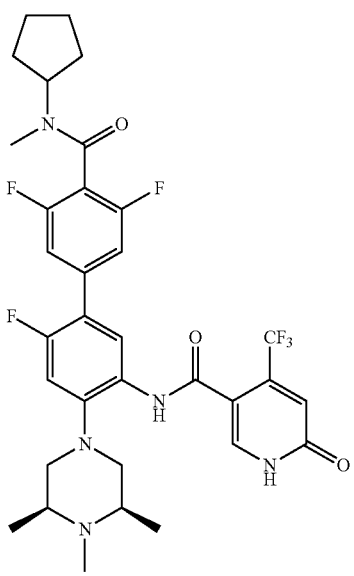 [SMILES: C[C@@H]1CN(c2cc(F)c(-c3cc(F)c(C(=O)N(C)C4CCCC4)c(F)c3)cc2NC(=O)c2c[nH]c(=O)cc2C(F)(F)F)C[C@H](C)N1C]

The title compound was collected as an off-white fluffy powder (19.7 mg, 0.028 mmol, 54.8% yield). $^1$H NMR (500 MHz, METHANOL-d4) δ=7.86 (s, 1H), 7.85-7.83 (m, 1H), 7.22 (br d, J=8.3 Hz, 2H), 7.00 (d, J=12.3 Hz, 1H), 6.84-6.81 (m, 1H), 3.96 (quin, J=7.8 Hz, 1H), 3.05-2.97 (m, 2H), 2.94 (s, 2H), 2.79 (s, 1H), 2.61-2.49 (m, 4H), 2.33 (s, 3H), 1.91-1.83 (m, 1H), 1.78-1.69 (m, 2H), 1.68-1.56 (m, 4H), 1.43 (br s, 1H), 1.09 (br d, J=5.5 Hz, 6H); LCMS [M+H]$^+$ 664.

904

Example 762: 6-oxo-N-(3',5',6-trifluoro-4'-(((R)-tetrahydrofuran-3-yl)carbamoyl)-4-((3S,5R)-3,4,5-trimethylpiperazin-1-yl)-[1,1'-biphenyl]-3-yl)-4-(trifluoromethyl)-1,6-dihydropyridine-3-carboxamide

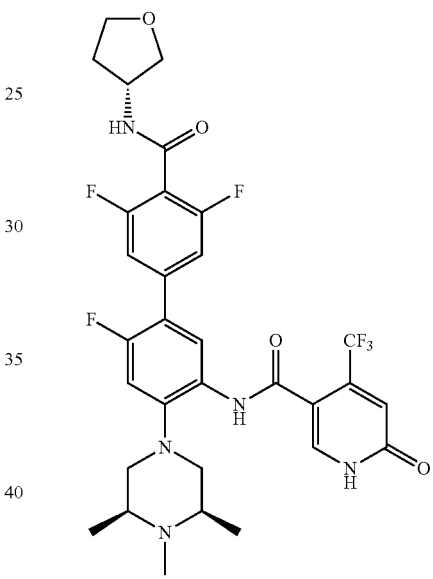

The title compound was collected as a white fluffy powder (15.7 mg, 0.023 mmol, 44.4% yield). $^1$H NMR (500 MHz, METHANOL-d4) δ=7.86 (s, 1H), 7.83 (d, J=8.2 Hz, 1H), 7.17 (d, J=8.4 Hz, 2H), 6.98 (d, J=12.3 Hz, 1H), 6.83-6.80 (m, 1H), 4.54-4.45 (m, 1H), 3.89-3.81 (m, 2H), 3.74 (dt, J=5.5, 8.4 Hz, 1H), 3.64 (dd, J=3.4, 9.3 Hz, 1H), 3.00 (br d, J=11.1 Hz, 2H), 2.57-2.42 (m, 4H), 2.29 (s, 3H), 2.21 (qd, J=7.7, 13.0 Hz, 1H), 1.90-1.82 (m, 1H), 1.07 (d, J=6.1 Hz, 6H); LCMS [M+H]$^+$ 652.

Example 763: 6-oxo-N-(3',5',6-trifluoro-4'-(methyl (oxetan-3-yl)carbamoyl)-4-((3S,5R)-3,4,5-trimethylpiperazin-1-yl)-[1,1'-biphenyl]-3-yl)-4-(trifluoromethyl)-1,6-dihydropyridine-3-carboxamide

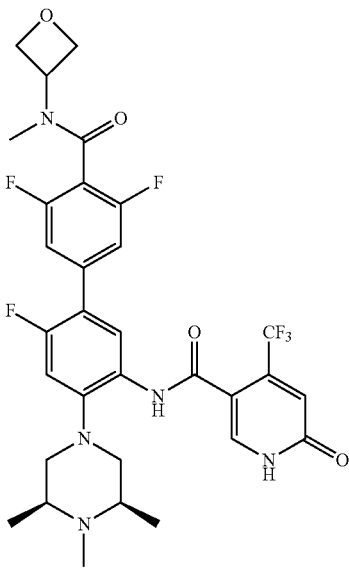 [SMILES: C[C@@H]1CN(c2cc(F)c(-c3cc(F)c(C(=O)N(C)C4COC4)c(F)c3)cc2NC(=O)c2c[nH]c(=O)cc2C(F)(F)F)C[C@H](C)N1C]

The title compound was collected as a white fluffy powder (14 mg, 0.020 mmol, 32.1% yield). $^1$H NMR (500 MHz, METHANOL-d4) δ=7.88-7.83 (m, 2H), 7.24 (t, J=7.6 Hz, 2H), 7.00 (d, J=12.2 Hz, 1H), 6.83-6.81 (m, 1H), 5.37 (quin, J=7.2 Hz, 1H), 4.96-4.86 (m, 1H), 3.32 (s, 2H), 3.03 (s, 2H), 3.01 (s, 1H), 2.59-2.43 (m, 5H), 2.30 (s, 3H), 1.08 (d, J=5.9 Hz, 6H); LCMS [M+H]$^+$ 652.

Example 764: 6-oxo-N-(3',5',6-trifluoro-4'-(methyl (2,2,2-trifluoroethyl)carbamoyl)-4-((3S,5R)-3,4,5-trimethylpiperazin-1-yl)-[1,1'-biphenyl]-3-yl)-4-(trifluoromethyl)-1,6-dihydropyridine-3-carboxamide

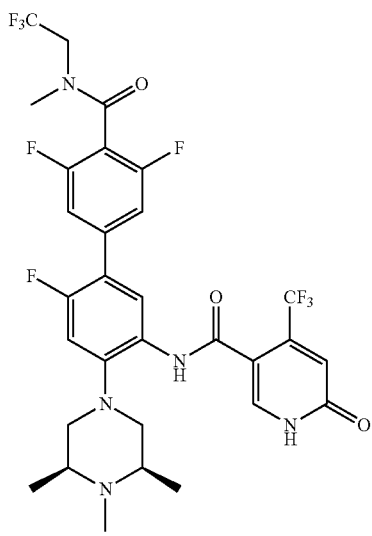 [SMILES: C[C@@H]1CN(c2cc(F)c(-c3cc(F)c(C(=O)N(C)CC(F)(F)F)c(F)c3)cc2NC(=O)c2c[nH]c(=O)cc2C(F)(F)F)C[C@H](C)N1C]

The title compound was collected as a white fluffy powder (16.9 mg, 0.024 mmol, 46.0% yield). $^1$H NMR (500 MHz, METHANOL-d4) δ=7.87 (t, J=4.0 Hz, 2H), 7.28-7.22 (m, 2H), 7.03 (d, J=12.2 Hz, 1H), 6.83 (s, 1H), 4.27 (q, J=9.1 Hz, 2H), 4.03-3.97 (m, 1H), 3.09 (br d, J=12.0 Hz, 2H), 3.03 (s, 3H), 2.76 (br d, J=2.3 Hz, 2H), 2.67-2.58 (m, 2H), 2.46 (br s, 3H), 1.15 (d, J=6.2 Hz, 6H); LCMS [M+H]$^+$ 678.

(c) Biological Assays

Compounds of the present application displayed inhibition of the binding between WDR5 and its binding partners as evidenced in the following assays:

(i) Surface Plasmon Resonance (SPR) Assay (1) Protocol

Exemplary compounds of the application were dissolved in 100% DMSO at 10 mM, assayed fresh, and then stored at −20° C. for repeat studies and other experiments. Full length WDR5 with an N-terminal His tag and C-terminal AviTag (Avidity Inc.) was expressed in *E. coli* with coexpression of BirA to biotin labelled protein in vivo. Purification of the protein was performed using Ni-NTA. The purified WDR5 protein has a molecular weight of 41976 Da.

SPR studies were performed using a Biacore™ T200 instrument (GE Health Sciences Inc.). Biotinylated WDR5 protein (approximately 3000RU) was stably captured to streptavidin coupled SA chips according to the manufacture's protocol (GE Health Sciences Inc.). The running buffer used was HBS-EP (20 mM Hepes pH 7.4, 150 mM NaCl, 3 mM EDTA, 0.05% P-20) plus 5% DMSO with a flow rate of 40 µl/min. For SPR analysis, 5 different concentrations of each exemplary compound of the application were sprayed into 96 or 384 well plates using an HP D300 digital dispenser. The concentration ranged from about 195 nM to about 12 nM in a two-fold series. Concentration ranges were adjusted higher or lower for weaker or more potent compounds respectively when necessary. For the $K_D$ determinations, single cycle kinetic analysis was performed with an on time of 60 seconds, and an off time of 300 or 600 seconds. Curve fitting and $K_D$ calculations were performed with the Biacore T200 Evaluation software (GE Health Sciences Inc).

(2) Results

Table 1 shows the binding affinity values ($K_D$) of exemplary compounds of the application for the WDR5 protein. The exemplary compounds of the application have binding affinities which range in the nanomolar concentrations.

(ii) MLL1 WRAD2 Enzyme Assay

Compound potency was assessed through incorporation of 3H-SAM into oligonucleosomes purified from HeLa cells. Specifically, recombinant human MLL1 (aa 3745-3969, GenBank Accession No. NM_005933), WDR5 (aa 22-334, GenBank Accession No. NM_017588), RbBP5 (aa 1-538, GenBank Accession No. NM_005057), Ash2L (aa 2-534, GenBank Accession No. NM_001105214), and DPY-30 (aa 1-99, GenBank Accession No. NM_0325742), all with N-terminal His tag, were expressed in *E. coli* and mixed at a molar ratio of 1:1:1:1:2. 10 nM of the assembled MLL1-WRAD2 complex was mixed with 100 nM WRAD2 to enhance complex formation before incubation with 0.05 mg/ml nucleosome substrate and exemplary compounds of the application (as 10 point duplicate dose response titrations) for 15 min in a buffer consisting of 50 mM Tris (pH 8.5), 5 mM MgCl$_2$, 50 mM NaCl, 1 mM DTT, 0.01% Brij-35, and 1% DMSO. Reaction was initiated with 1 µM 3H-SAM and incubated for 1 hour at 30° C. Reaction mixture was transferred to P81 filter-paper and washed with PBS before detection.

(1) Results

Table 2 shows the inhibitory activity of representative compounds of the invention in the in vitro methyl transferase assay (MLL1-WRAD2 assay).

(iii) Detection of In-Cell H3K4 Dimethylation

T24 cells were seeded into a 96-well plate at 400 cells/well in 150 µl medium (McCoy 5A containing 10% FBS, 100 µg/ml Normocin, and 50 µg/ml Gentamycin, Invitrogen). A HP D300 digital dispenser was used to dose cells with DMSO or test compounds across a 10-point range of concentrations (high dose of 10 µM), and cultures were grown in a humidified 5% $CO_2$ incubator at 37° C. After five days, plates were removed from incubator, media was aspirated, and the cells washed in PBS. Cell lysis, histone extraction, and detection of H3K4 dimethylation (H3K4me2) were performed using an AlphaLisa kit according to the manufacturer's instructions (Perkin Elmer). Signal was measured using an Envision plate reader.

(1) Results

Exemplary compounds of the application significantly inhibit the demethylation of H3K4 in T24 cells as shown in Table 3.

(iv) Cell Proliferation Assay

MV4-11 cells were seeded into a 96-well plate at 1,000 cells/well in 150 µl medium (Alpha-MEM containing 10% FBS, 100 µg/ml Normocin, and 50 µg/ml Gentamycin, Invitrogen). A HP D300 digital dispenser was used to dose cells with DMSO or test compounds across a 10-point range of concentrations (high dose of 10 µM), and cultures were grown in a humidified 5% $CO_2$ incubator at 37° C. After five days, plates were removed from the incubator and equilibrated to room temperature. An equal volume of ATPlite assay reagent was added to each well, and samples were processed according to manufacturer's instructions (Perkin Elmer). Luminescent signal was measured using an Envision plate reader equipped with a US-Luminescence detector.

(1) Results

Table 4 illustrates the anti-proliferative activity of exemplary compounds of the invention, (v) Residency Time Biochemical and cellular assays of drug interactions with their target macromolecules have traditionally been based on measures of drug-target binding affinity under thermodynamic equilibrium conditions. Equilibrium binding metrics such as the half-maximal inhibitory concentration ($IC_{50}$), the effector concentration for half-maximal response ($EC_{50}$), the equilibrium dissociation constant ($K_D$) and the inhibition constant ($K_i$), all pertain to in vitro assays run under closed system conditions, in which the drug molecule and target are present at invariant concentrations throughout the time course of the experiment [*Nat. Rev. Drug Discov.* 2006, 5, 730-739; *Biochemistry* 2008, 47, 5481-5492; *Expert Opin. Drug Discov.* 2010, 5, 305-310]. In living organisms, the concentration of drug available for interaction with a localized protein target is in constant flux because of various physiological processes. Such processes include gastrointestinal absorption, hepatic and renal metabolism, and tissue distribution. Hence, equilibrium measures of drug-target interactions are not entirely valid in the context of the open, non-equilibrium conditions of in vivo pharmacology. It has been suggested that the key determinant of in vivo pharmacological activity and duration is not the binding affinity of a drug for its intended target but the lifetime, or residence time, of the binary drug-target complex. Pharmacological activity typically depends on the binding of the drug to its intended target, and pharmacological activity will usually only persist while the drug remains bound. As soon as a drug dissociates from its target, that target protein is then free to resume its pathophysiological function, which is presumably the molecular progenitor of disease.

The lifetime of a drug on its target is determined by two rate constants: the association rate constant ($k_{on}$) and the dissociation rate constant ($k_{off}$). In principle, the lifetime of the binary drug-target complex is thus extended by a rapid rate of drug binding and/or a slow rate of drug-target complex dissociation. The in vivo lifetime of a drug-target complex is most critically dependent on the value of the $k_{off}$ [*Nat. Rev. Drug Discov.* 2006, 5, 730-739; *Biochemistry* 2008, 47, 5481-5492; *Expert Opin. Drug Discov.* 2010, 5, 305-310]. Drug-target residence time is defined as the reciprocal of $k_{off}$ ($=1/k_{off}$), making the residence time a parameter that is easily measured by routine in vitro assay methods. Moreover, residence time contributes to the multiple, critical parameters that influence in vivo pharmacodynamics [*Anal. Biochem.* 2014, 468, 42-49].

The potency of drug-target binding interactions (as measured by the $K_D$) and residence time are distinct parameters, they are nevertheless interdependent. This interdependency is clear from the mathematical definitions of the $K_D$ for various modalities of binding (see below). The simplest binding interaction is a 1:1 binding reaction in which one molecule of ligand (L, in this case a drug molecule) interacts with one molecule of the protein target (R, the target of pharmacological intervention), that is held in a single conformational state. The association of ligand and target occurs in a single kinetic step, defined by the $k_{on}$; similarly, binary complex dissociation occurs in a single kinetic step, defined by the $k_{off}$. For this binding mode, the $K_D$ is defined by equation shown below.

$$K_D = k_{off}/k_{on}$$

Hence, from this model, the $K_D$ would be expected to be directly related to the $k_{off}$ and inversely related to both the residence time ($1/k_{off}$) and the $k_{on}$. However, in many cases of high-potency ligand binding to protein targets, one finds that the value of $k_{on}$ is invariant over a series of chemically related ligands (for example, a pharmacophore series) binding to a protein target, or for a specific ligand binding to variants of a protein target.

The drug-target residence time model was formulated on the basis of a foundation of experimental data suggesting that slow binding and particularly slow drug-target complex dissociation might be a critical molecular antecedent of durable pharmacological activity in vivo [*Proc. Natl Acad. Sci. USA* 1994, 91, 11202-11206; *J. Am. Chem. Soc. USA* 1996, 118, 2359-2365; *Proc. Natl Acad. Sci. USA* 2006,103, 7625-7630]. The mathematical basis for analyzing slow binding and dissociating enzyme inhibition kinetics was developed in the seminal work of Morrison and Walsh [*Adv. Enzymol. Relat. Areas Mol. Biol.* 1988, 61, 201-299]. The advent of surface plasmon resonance (SPR) methods led to the ability to measure, and therefore renewed interest in, protein-ligand association and dissociation kinetics [*Future Med. Chem.* 2009, 1, 1399-1414].

Based on a number of experimental studies, the drug-target residence time model predicts that durable pharmacodynamics can be achieved by developing drug molecules with long residence times on their intended target. If the residence time of the drug on its target exceeds the pharmacokinetic half-life of the drug in systemic circulation, one could even achieve the seemingly paradoxical situation of sustained pharmacodynamics activity, even after the bulk of drug has been cleared from the body [*Nat. Rev. Drug Discov.* 2006, 5, 730-739; *Biochemistry* 2008, 47, 5481-5492; *Drug Discov. Today* 2013, 18: 697-707 (2013). Indeed, numerous examples of long-residence-time drugs that exhibit this unexpected pharmacokinetics-pharmacodynamics temporal relationship now exist [*Curr. Opin. Drug Discov.* 2009,12 488-496; *Curr. Opin. Chem. Biol.* 2010, 14, 467-474]. The ability to sustain durable pharmacodynamics after the clearance of bulk drug from the circulation can provide important advantages in terms of convenient dosing schedules for patients and avoiding off-target mediated toxicities[*Nat Rev Drug Discov.* 2016,15(2):87-95].

Over the past 10 years, the drug-target residence time model has been further refined and applied to drug discovery and development efforts. We have discovered a novel class of compounds which inhibit the WDR5 protein-protein binding. In addition, structure-activity relationship studies demonstrated that specific chemical features contribute to longer residence times. WDR5 inhibitors with longer residence times has demonstrated increased inhibition of MLL1 catalytic activity resulting in significantly improved growth inhibition observed in hematologic and solid tumors (Table 5 and 6).

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Binding affinities ($K_D$) derived from surface plasmon resonance (SPR) assays

| Example No. | Structure | IUPAC Name | WDR5 binding affinity ($K_D$, μM) |
|---|---|---|---|
| 1 | 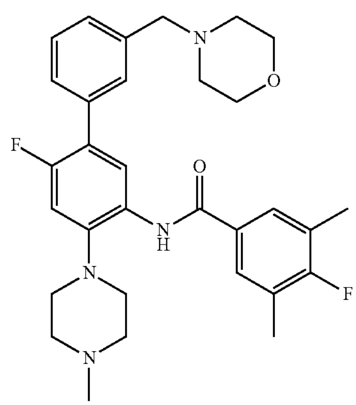 [SMILES: Cc1cc(C(=O)Nc2cc(-c3cccc(CN4CCOCC4)c3)c(F)cc2N2CCN(C)CC2)cc(C)c1F] | 4-fluoro-N-[4-fluoro-2-(4-methylpiperazin-1-yl)-5-[3-(morpholin-4-ylmethyl)phenyl]phenyl]-3,5-dimethylbenzamide | 0.084 |
| 2 | 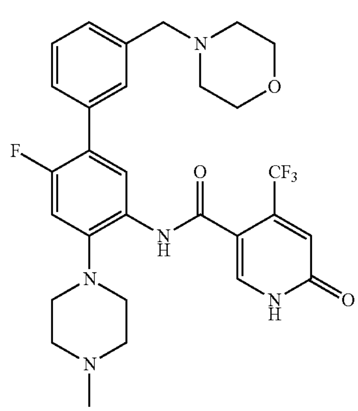 [SMILES: CN1CCN(c2cc(F)c(-c3cccc(CN4CCOCC4)c3)cc2NC(=O)c2c[nH]c(=O)cc2C(F)(F)F)CC1] | N-[4-fluoro-2-(4-methylpiperazin-1-yl)-5-[3-(morpholin-4-ylmethyl)phenyl]phenyl]-6-oxo-4-(trifluoromethyl)-1H-pyridine-3-carboxamide | 0.011 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 3 | 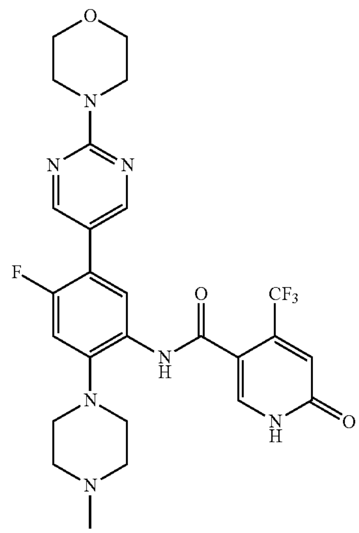 [SMILES: CN1CCN(c2cc(F)c(-c3cnc(N4CCOCC4)nc3)cc2NC(=O)c2c[nH]c(=O)cc2C(F)(F)F)CC1] | N-[4-fluoro-2-(4-methylpiperazin-1-yl)-5-(2-morpholin-4-ylpyrimidin-5-yl)phenyl]-6-oxo-4-(trifluoromethyl)-1H-pyridine-3-carboxamide | 0.002 |
| 4 | 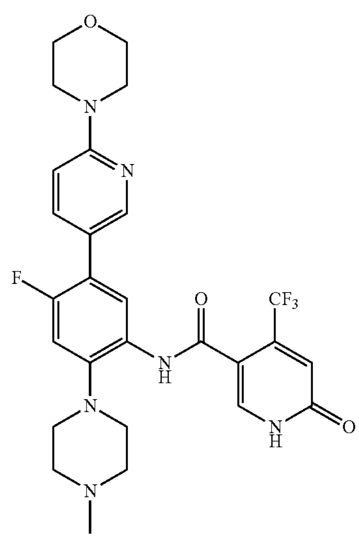 | N-[4-fluoro-2-(4-methylpiperazin-1-yl)-5-(6-morpholin-4-ylpyridin-3-yl)phenyl]-6-oxo-4-(trifluoromethyl)-1H-pyridine-3-carboxamide | 0.004 |
| 5 | 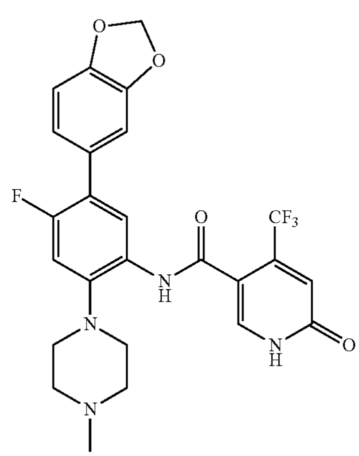 [SMILES: CN1CCN(c2cc(F)c(-c3ccc4c(c3)OCO4)cc2NC(=O)c2c[nH]c(=O)cc2C(F)(F)F)CC1] | N-[5-(1,3-benzodioxol-5-yl)-4-fluoro-2-(4-methylpiperazin-1-yl)phenyl]-6-oxo-4-(trifluoromethyl)-1H-pyridine-3-carboxamide | 0.033 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 6 | 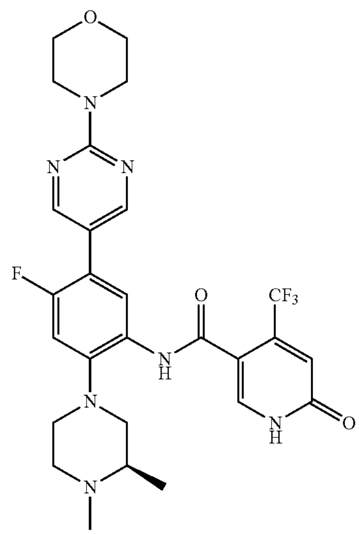 | N-[2-[(3R)-3,4-dimethylpiperazin-1-yl]-4-fluoro-5-(2-morpholin-4-ylpyrimidin-5-yl)phenyl]-6-oxo-4-(trifluoromethyl)-1H-pyridine-3-carboxamide | 0.003 |
| 7 | 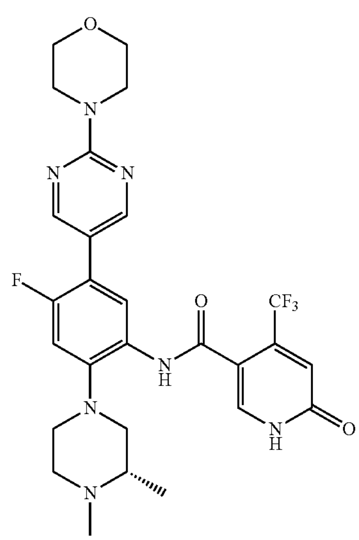 [SMILES: C[C@H]1CN(c2cc(F)c(-c3cnc(N4CCOCC4)nc3)cc2NC(=O)c2c[nH]c(=O)cc2C(F)(F)F)CCN1C] | N-[2-[(3S)-3,4-dimethylpiperazin-1-yl]-4-fluoro-5-(2-morpholin-4-ylpyrimidin-5-yl)phenyl]-6-oxo-4-(trifluoromethyl)-1H-pyridine-3-carboxamide | 0.00006 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 8 | 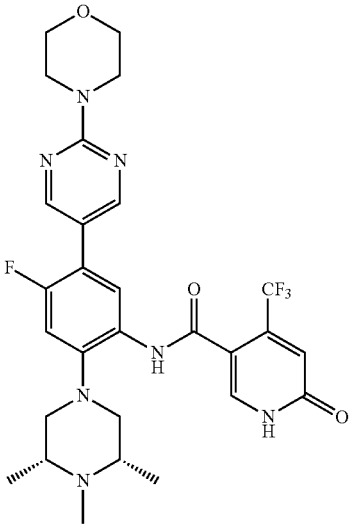 [SMILES: C[C@@H]1CN(c2cc(F)c(-c3cnc(N4CCOCC4)nc3)cc2NC(=O)c2c[nH]c(=O)cc2C(F)(F)F)C[C@H](C)N1C] | N-[4-fluoro-5-(2-morpholin-4-ylpyrimidin-5-yl)-2-[(3R,5S)-3,4,5-trimethylpiperazin-1-yl]phenyl]-6-oxo-4-(trifluoromethyl)-1H-pyridine-3-carboxamide | 0.0003 |
| 9 | 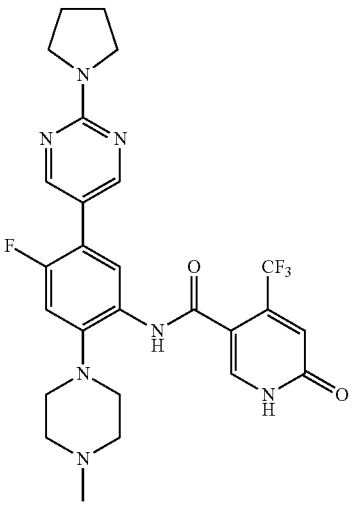 [SMILES: CN1CCN(c2cc(F)c(-c3cnc(N4CCCC4)nc3)cc2NC(=O)c2c[nH]c(=O)cc2C(F)(F)F)CC1] | N-[4-fluoro-2-(4-methylpiperazin-1-yl)-5-(2-pyrrolidin-1-ylpyrimidin-5-yl)phenyl]-6-oxo-4-(trifluoromethyl)-1H-pyridine-3-carboxamide | 0.005 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 10 | 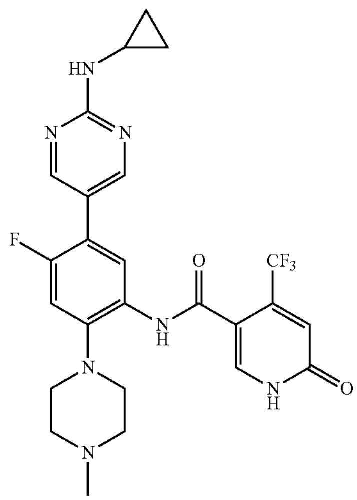 [SMILES: CN1CCN(c2cc(F)c(-c3cnc(NC4CC4)nc3)cc2NC(=O)c2c[nH]c(=O)cc2C(F)(F)F)CC1] | N-[5-[2-(cyclopropylamino)pyrimidin-5-yl]-4-fluoro-2-(4-methylpiperazin-1-yl)phenyl]-6-oxo-4-(trifluoromethyl)-1H-pyridine-3-carboxamide | 0.013 |
| 11 | 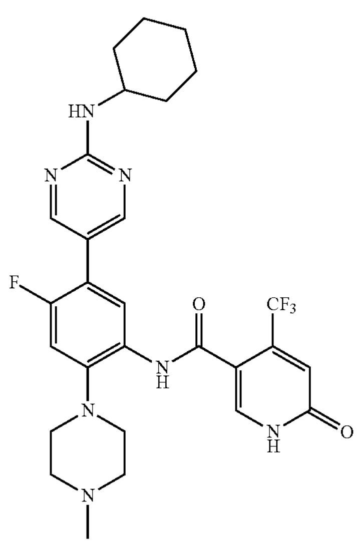 [SMILES: CN1CCN(c2cc(F)c(-c3cnc(NC4CCCCC4)nc3)cc2NC(=O)c2c[nH]c(=O)cc2C(F)(F)F)CC1] | N-[5-[2-(cyclohexylamino)pyrimidin-5-yl]-4-fluoro-2-(4-methylpiperazin-1-yl)phenyl]-6-oxo-4-(trifluoromethyl)-1H-pyridine-3-carboxamide | 0.005 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 12 | 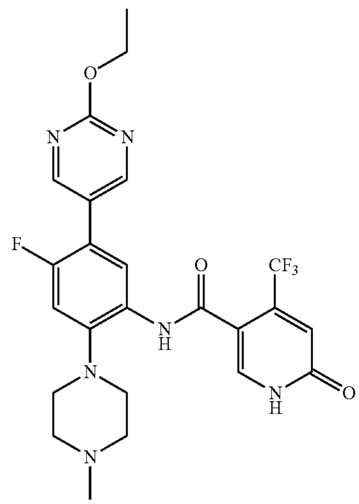 [SMILES: CCOc1ncc(-c2cc(NC(=O)c3c[nH]c(=O)cc3C(F)(F)F)c(N3CCN(C)CC3)cc2F)cn1] | N-[5-(2-ethoxypyrimidin-5-yl)-4-fluoro-2-(4-methylpiperazin-1-yl)phenyl]-6-oxo-4-(trifluoromethyl)-1H-pyridine-3-carboxamide | 0.005 |
| 13 | 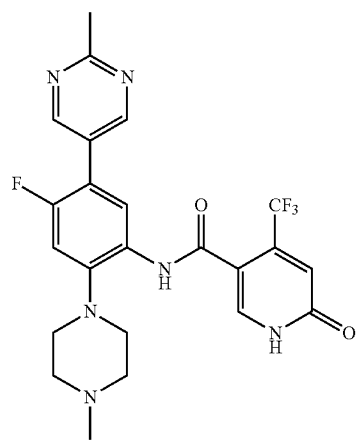 [SMILES: Cc1ncc(-c2cc(NC(=O)c3c[nH]c(=O)cc3C(F)(F)F)c(N3CCN(C)CC3)cc2F)cn1] | N-[4-fluoro-2-(4-methylpiperazin-1-yl)-5-(2-methylpyrimidin-5-yl)phenyl]-6-oxo-4-(trifluoromethyl)-1H-pyridine-3-carboxamide | 0.004 |
| 14 | 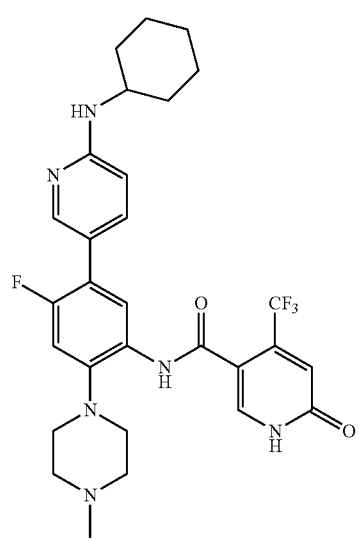 [SMILES: CN1CCN(c2cc(F)c(-c3ccc(NC4CCCCC4)nc3)cc2NC(=O)c2c[nH]c(=O)cc2C(F)(F)F)CC1] | N-[5-[6-(cyclohexylamino)pyridin-3-yl]-4-fluoro-2-(4-methylpiperazin-1-yl)phenyl]-6-oxo-4-(trifluoromethyl)-1H-pyridine-3-carboxamide | 0.005 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 15 | 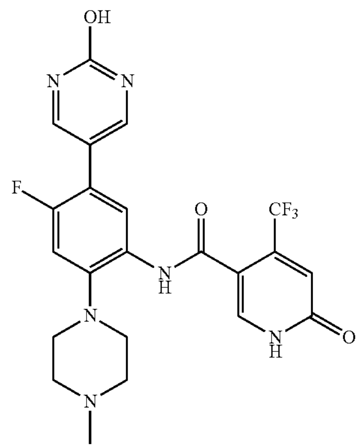 [SMILES: CN1CCN(c2cc(F)c(-c3cnc(O)nc3)cc2NC(=O)c2c[nH]c(=O)cc2C(F)(F)F)CC1] | N-[4-fluoro-5-(2-hydroxypyrimidin-5-yl)-2-(4-methylpiperazin-1-yl)phenyl]-6-oxo-4-(trifluoromethyl)-1H-pyridine-3-carboxamide | 0.026 |
| 16 | 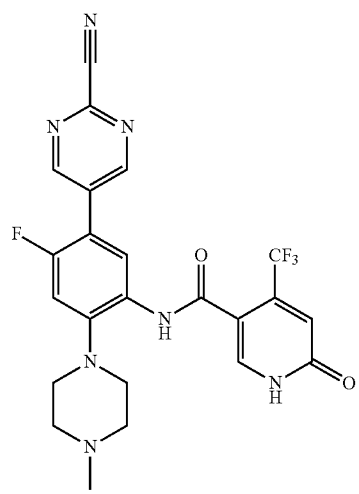 [SMILES: CN1CCN(c2cc(F)c(-c3cnc(C#N)nc3)cc2NC(=O)c2c[nH]c(=O)cc2C(F)(F)F)CC1] | N-[5-(2-cyanopyrimidin-5-yl)-4-fluoro-2-(4-methylpiperazin-1-yl)phenyl]-6-oxo-4-(trifluoromethyl)-1H-pyridine-3-carboxamide | 0.002 |
| 17 | 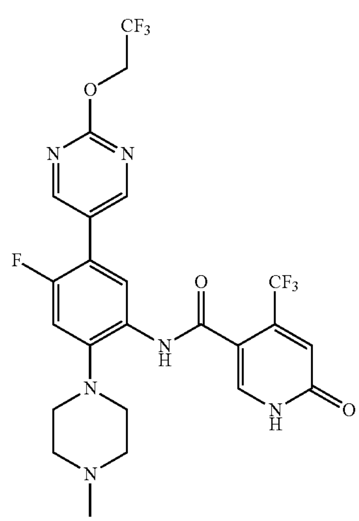 [SMILES: CN1CCN(c2cc(F)c(-c3cnc(OCC(F)(F)F)nc3)cc2NC(=O)c2c[nH]c(=O)cc2C(F)(F)F)CC1] | N-[4-fluoro-2-(4-methylpiperazin-1-yl)-5-[2-(2,2,2-trifluoroethoxy)pyrimidin-5-yl]phenyl]-6-oxo-4-(trifluoromethyl)-1H-pyridine-3-carboxamide | 0.006 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 18 | 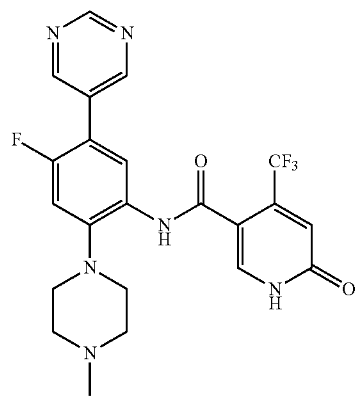 [SMILES: CN1CCN(c2cc(F)c(-c3cncnc3)cc2NC(=O)c2c[nH]c(=O)cc2C(F)(F)F)CC1] | N-[4-fluoro-2-(4-methylpiperazin-1-yl)-5-pyrimidin-5-ylphenyl]-6-oxo-4-(trifluoromethyl)-1H-pyridine-3-carboxamide | 0.009 |
| 19 | 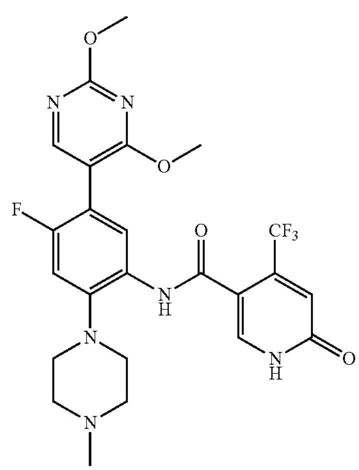 [SMILES: COc1ncc(-c2cc(NC(=O)c3c[nH]c(=O)cc3C(F)(F)F)c(N3CCN(C)CC3)cc2F)c(OC)n1] | N-[5-(2,4-dimethoxypyrimidin-5-yl)-4-fluoro-2-(4-methylpiperazin-1-yl)phenyl]-6-oxo-4-(trifluoromethyl)-1H-pyridine-3-carboxamide | 0.004 |
| 20 | 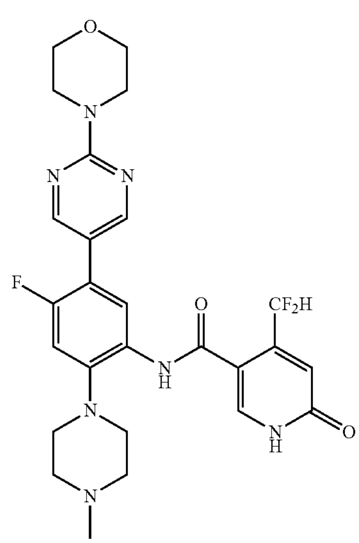 | 4-(difluoromethyl)-N-[4-fluoro-2-(4-methylpiperazin-1-yl)-5-(2-morpholin-4-ylpyrimidin-5-yl)phenyl]-6-oxo-1H-pyridine-3-carboxamide | 0.002 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 21 | 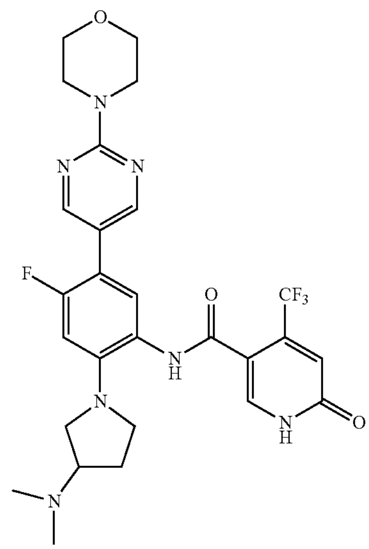 | N-[2-[3-(dimethylamino)pyrrolidin-1-yl]-4-fluoro-5-(2-morpholin-4-ylpyrimidin-5-yl)phenyl]-6-oxo-4-(trifluoromethyl)-1H-pyridine-3-carboxamide | 0.0009 |
| 22 | 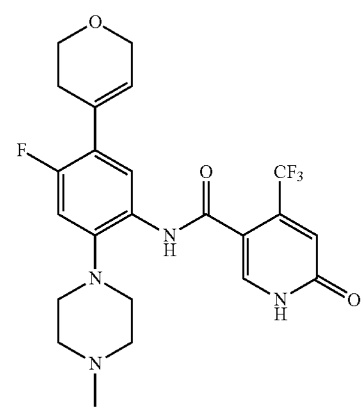 [SMILES: CN1CCN(c2cc(F)c(C3=CCOCC3)cc2NC(=O)c2c[nH]c(=O)cc2C(F)(F)F)CC1] | N-[5-(3,6-dihydro-2H-pyran-4-yl)-4-fluoro-2-(4-methylpiperazin-1-yl)phenyl]-6-oxo-4-(trifluoromethyl)-1H-pyridine-3-carboxamide | 0.0076 |
| 23 | 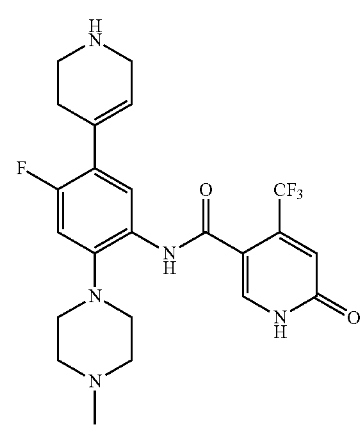 [SMILES: CN1CCN(c2cc(F)c(C3=CCNCC3)cc2NC(=O)c2c[nH]c(=O)cc2C(F)(F)F)CC1] | N-[4-fluoro-2-(4-methylpiperazin-1-yl)-5-(1,2,3,6-tetrahydropyridin-4-yl)phenyl]-6-oxo-4-(trifluoromethyl)-1H-pyridine-3-carboxamide | 0.0171 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 24 | 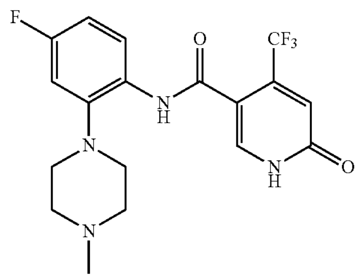 [SMILES: CN1CCN(c2cc(F)ccc2NC(=O)c2c[nH]c(=O)cc2C(F)(F)F)CC1] | N-[4-fluoro-2-(4-methylpiperazin-1-yl)phenyl]-6-oxo-4-(trifluoromethyl)-1H-pyridine-3-carboxamide | 0.0756 |
| 25 | 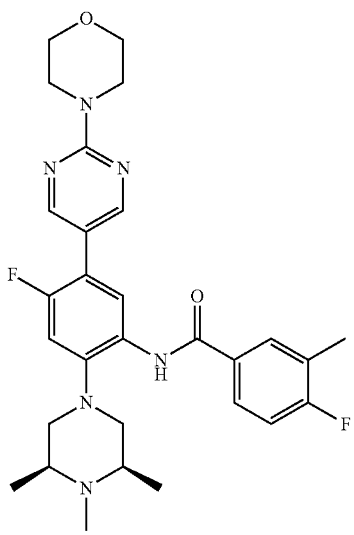 [SMILES: Cc1cc(C(=O)Nc2cc(-c3cnc(N4CCOCC4)nc3)c(F)cc2N2C[C@@H](C)N(C)[C@@H](C)C2)ccc1F] | 4-fluoro-N-[4-fluoro-5-(2-morpholin-4-ylpyrimidin-5-yl)-2-[(3R,5S)-3,4,5-trimethylpiperazin-1-yl]phenyl]-3-methylbenzamide | 0.0085 |
| 26 | 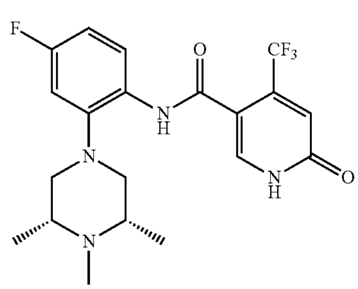 [SMILES: C[C@@H]1CN(c2cc(F)ccc2NC(=O)c2c[nH]c(=O)cc2C(F)(F)F)C[C@H](C)N1C] | N-[4-fluoro-2-[(3R,5S)-3,4,5-trimethylpiperazin-1-yl]phenyl]-6-oxo-4-(trifluoromethyl)-1H-pyridine-3-carboxamide | 0.0425 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 27 | 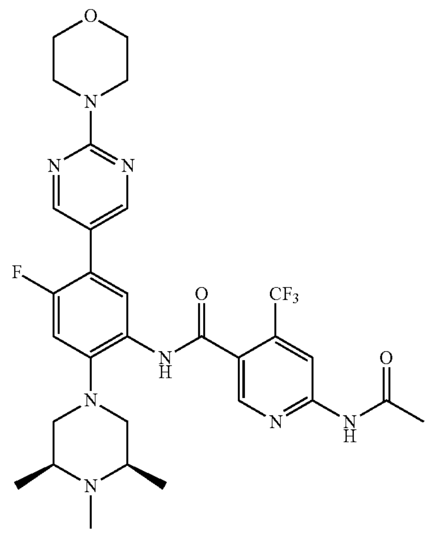 [SMILES: CC(=O)Nc1cc(C(F)(F)F)c(C(=O)Nc2cc(-c3cnc(N4CCOCC4)nc3)c(F)cc2N2C[C@@H](C)N(C)[C@@H](C)C2)cn1] | 6-acetamido-N-[4-fluoro-5-(2-morpholin-4-ylpyrimidin-5-yl)-2-[(3R,5S)-3,4,5-trimethylpiperazin-1-yl]phenyl]-4-(trifluoromethyl)pyridine-3-carboxamide | 0.2940 |
| 28 | 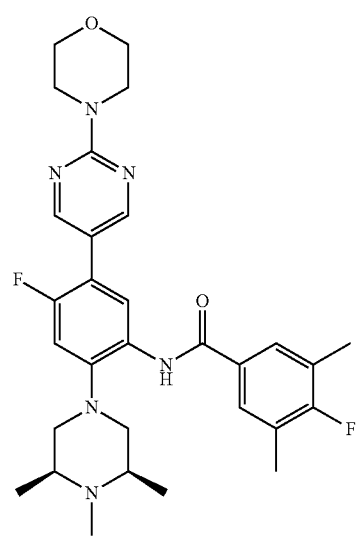 [SMILES: Cc1cc(C(=O)Nc2cc(-c3cnc(N4CCOCC4)nc3)c(F)cc2N2C[C@@H](C)N(C)[C@@H](C)C2)cc(C)c1F] | 4-fluoro-N-[4-fluoro-5-(2-morpholin-4-ylpyrimidin-5-yl)-2-[(3R,5S)-3,4,5-trimethylpiperazin-1-yl]phenyl]-3,5-dimethylbenzamide | 0.0015 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 29 | 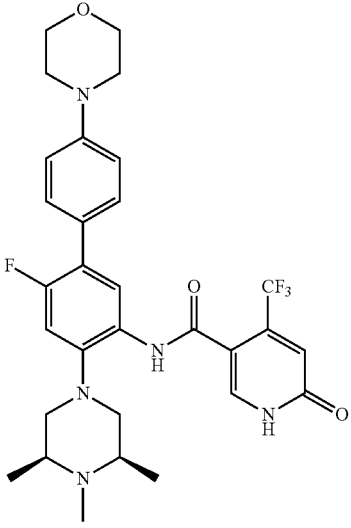 [SMILES: C[C@@H]1CN(c2cc(F)c(-c3ccc(N4CCOCC4)cc3)cc2NC(=O)c2c[nH]c(=O)cc2C(F)(F)F)C[C@H](C)N1C] | N-[4-fluoro-5-(4-morpholin-4-ylphenyl)-2-[(3R,5S)-3,4,5-trimethylpiperazin-1-yl]phenyl]-6-oxo-4-(trifluoromethyl)-1H-pyridine-3-carboxamide | 0.0009 |
| 30 | 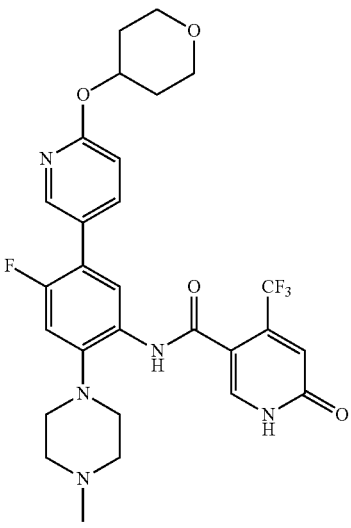 | N-[4-fluoro-2-(4-methylpiperazin-1-yl)-5-[6-(oxan-4-yloxy)pyridin-3-yl]phenyl]-6-oxo-4-(trifluoromethyl)-1H-pyridine-3-carboxamide | 0.0032 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 31 | 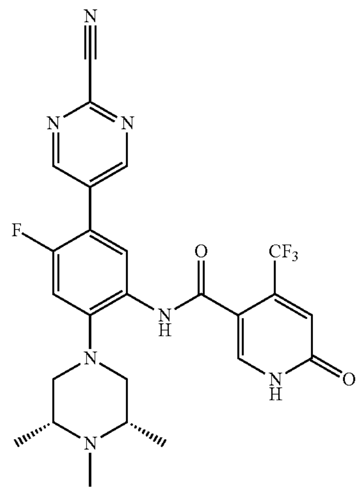 [SMILES: C[C@@H]1CN(c2cc(F)c(-c3cnc(C#N)nc3)cc2NC(=O)c2c[nH]c(=O)cc2C(F)(F)F)C[C@H](C)N1C] | N-[5-(2-cyanopyrimidin-5-yl)-4-fluoro-2-[(3S,5R)-3,4,5-trimethylpiperazin-1-yl]phenyl]-6-oxo-4-(trifluoromethyl)-1H-pyridine-3-carboxamide | 0.0014 |
| 32 | 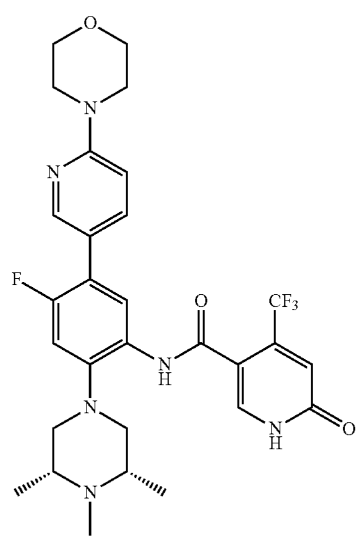 [SMILES: C[C@@H]1CN(c2cc(F)c(-c3ccc(N4CCOCC4)nc3)cc2NC(=O)c2c[nH]c(=O)cc2C(F)(F)F)C[C@H](C)N1C] | N-[4-fluoro-5-(6-morpholin-4-ylpyridin-3-yl)-2-[(3S,5R)-3,4,5-trimethylpiperazin-1-yl]phenyl]-6-oxo-4-(trifluoromethyl)-1H-pyridine-3-carboxamide | 0.0004 |
| 33 | 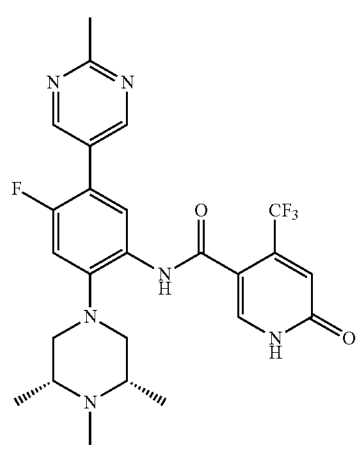 [SMILES: Cc1ncc(-c2cc(NC(=O)c3c[nH]c(=O)cc3C(F)(F)F)c(N3C[C@@H](C)N(C)[C@@H](C)C3)cc2F)cn1] | N-[4-fluoro-5-(2-methylpyrimidin-5-yl)-2-[(3S,5R)-3,4,5-trimethylpiperazin-1-yl]phenyl]-6-oxo-4-(trifluoromethyl)-1H-pyridine-3-carboxamide | 0.0005 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 34 | 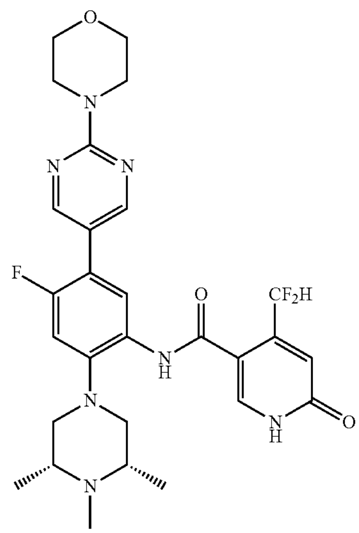 [SMILES: C[C@@H]1CN(c2cc(F)c(-c3cnc(N4CCOCC4)nc3)cc2NC(=O)c2c[nH]c(=O)cc2C(F)F)C[C@H](C)N1C] | 4-(difluoromethyl)-N-[4-fluoro-5-(2-morpholin-4-ylpyrimidin-5-yl)-2-[(3S,5R)-3,4,5-trimethylpiperazin-1-yl]phenyl]-6-oxo-1H-pyridine-3-carboxamide | 0.0001 |
| 35 | 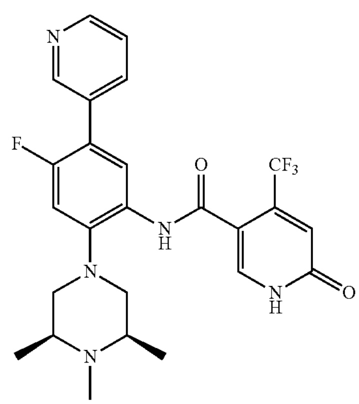 [SMILES: C[C@@H]1CN(c2cc(F)c(-c3cccnc3)cc2NC(=O)c2c[nH]c(=O)cc2C(F)(F)F)C[C@H](C)N1C] | N-[4-fluoro-5-pyridin-3-yl-2-[(3R,5S)-3,4,5-trimethylpiperazin-1-yl]phenyl]-6-oxo-4-(trifluoromethyl)-1H-pyridine-3-carboxamide | 0.0026 |
| 36 | 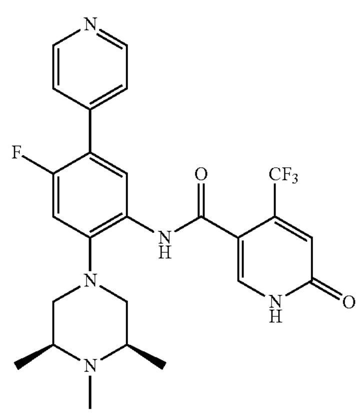 [SMILES: C[C@@H]1CN(c2cc(F)c(-c3ccncc3)cc2NC(=O)c2c[nH]c(=O)cc2C(F)(F)F)C[C@H](C)N1C] | N-[4-fluoro-5-pyridin-4-yl-2-[(3R,5S)-3,4,5-trimethylpiperazin-1-yl]phenyl]-6-oxo-4-(trifluoromethyl)-1H-pyridine-3-carboxamide | 0.0022 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 37 | 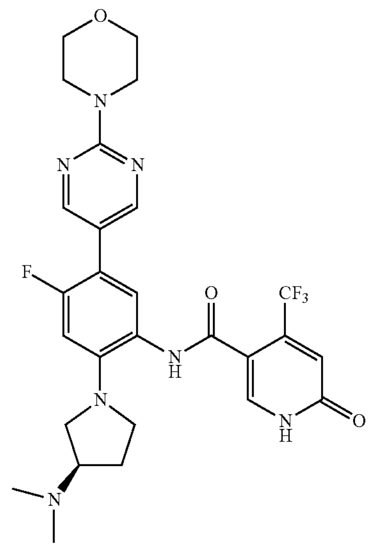 | N-[2-[(3R)-3-(dimethylamino)pyrrolidin-1-yl]-4-fluoro-5-(2-morpholin-4-ylpyrimidin-5-yl)phenyl]-6-oxo-4-(trifluoromethyl)-1H-pyridine-3-carboxamide | 0.0002 |
| 38 | 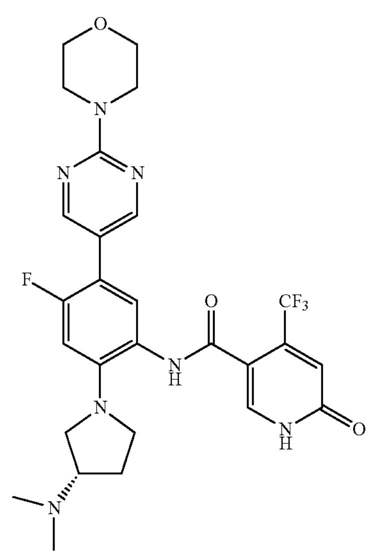 | N-[2-[(3S)-3-(dimethylamino)pyrrolidin-1-yl]-4-fluoro-5-(2-morpholin-4-ylpyrimidin-5-yl)phenyl]-6-oxo-4-(trifluoromethyl)-1H-pyridine-3-carboxamide | 0.0038 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 39 | 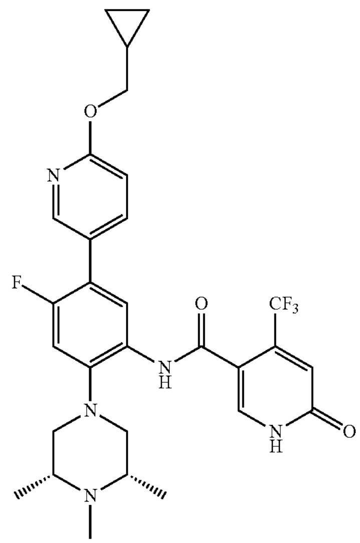 [SMILES: C[C@@H]1CN(c2cc(F)c(-c3ccc(OCC4CC4)nc3)cc2NC(=O)c2c[nH]c(=O)cc2C(F)(F)F)C[C@H](C)N1C] | N-[5-[6-(cyclopropylmethoxy)pyridin-3-yl]-4-fluoro-2-[(3S,5R)-3,4,5-trimethylpiperazin-1-yl]phenyl]-6-oxo-4-(trifluoromethyl)-1H-pyridine-3-carboxamide | 0.0003 |
| 40 | 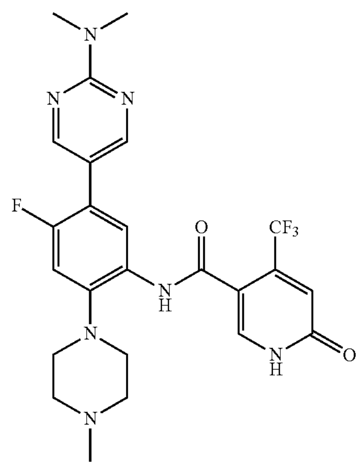 [SMILES: CN1CCN(c2cc(F)c(-c3cnc(N(C)C)nc3)cc2NC(=O)c2c[nH]c(=O)cc2C(F)(F)F)CC1] | N-[5-[2-(dimethylamino)pyrimidin-5-yl]-4-fluoro-2-(4-methylpiperazin-1-yl)phenyl]-6-oxo-4-(trifluoromethyl)-1H-pyridine-3-carboxamide | 0.0078 |
| 41 | 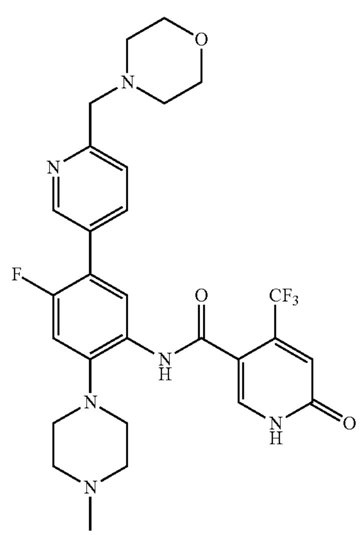 [SMILES: CN1CCN(c2cc(F)c(-c3ccc(CN4CCOCC4)nc3)cc2NC(=O)c2c[nH]c(=O)cc2C(F)(F)F)CC1] | N-[4-fluoro-2-(4-methylpiperazin-1-yl)-5-[6-(morpholin-4-ylmethyl)pyridin-3-yl]phenyl]-6-oxo-4-(trifluoromethyl)-1H-pyridine-3-carboxamide | 0.0086 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 42 | 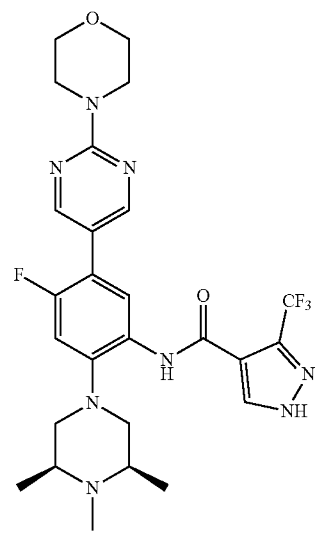 [SMILES: C[C@@H]1CN(c2cc(F)c(-c3cnc(N4CCOCC4)nc3)cc2NC(=O)c2c[nH]nc2C(F)(F)F)C[C@H](C)N1C] | N-[4-fluoro-5-(2-morpholin-4-ylpyrimidin-5-yl)-2-[(3R,5S)-3,4,5-trimethylpiperazin-1-yl]phenyl]-3-(trifluoromethyl)-1H-pyrazole-4-carboxamide | 0.009 |
| 43 | 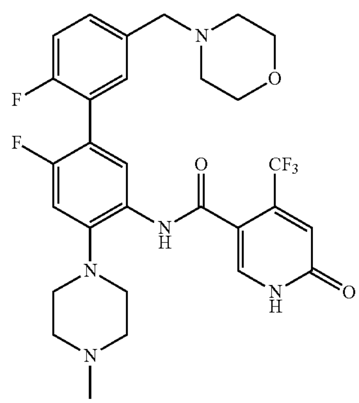 [SMILES: CN1CCN(c2cc(F)c(-c3cc(CN4CCOCC4)ccc3F)cc2NC(=O)c2c[nH]c(=O)cc2C(F)(F)F)CC1] | N-(2',6-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide | 0.020 |
| 44 | 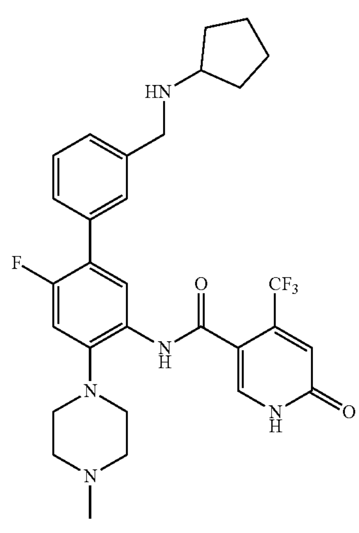 [SMILES: CN1CCN(c2cc(F)c(-c3cccc(CNC4CCCC4)c3)cc2NC(=O)c2c[nH]c(=O)cc2C(F)(F)F)CC1] | N-(3'-((cyclopentylamino)methyl)-6-fluoro-4-(4-methylpiperazin-1-yl)-[1,1'-biphenyl]-3-yl)-6-oxo-4-(trifluoromethyl)-1,6-dihydropyridine-3-carboxamide | 0.005 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 45 | 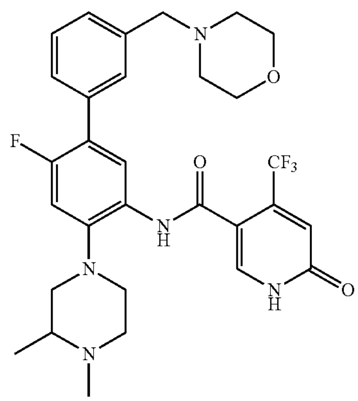 [SMILES: CC1CN(c2cc(F)c(-c3cccc(CN4CCOCC4)c3)cc2NC(=O)c2c[nH]c(=O)cc2C(F)(F)F)CCN1C] | N-(4-(3,4-dimethylpiperazin-1-yl)-6-fluoro-3'-(morpholinomethyl)-[1,1'-biphenyl]-3-yl)-6-oxo-4-(trifluoromethyl)-1,6-dihydropyridine-3-carboxamide | 0.009 |
| 46 | 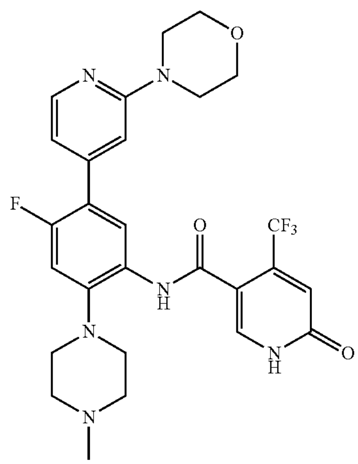 [SMILES: CN1CCN(c2cc(F)c(-c3ccnc(N4CCOCC4)c3)cc2NC(=O)c2c[nH]c(=O)cc2C(F)(F)F)CC1] | N-(4-fluoro-2-(4-methylpiperazin-1-yl)-5-(2-morpholinopyridin-4-yl)phenyl)-6-oxo-4-(trifluoromethyl)-1,6-dihydropyridine-3-carboxamide | 0.005 |
| 47 | 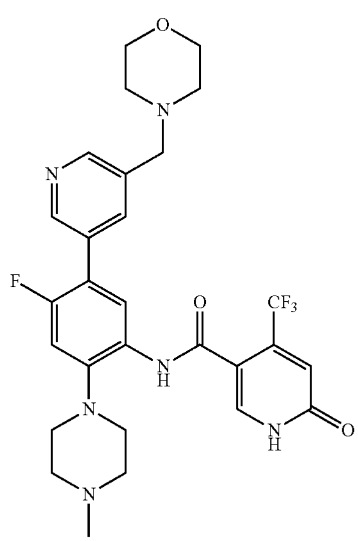 [SMILES: CN1CCN(c2cc(F)c(-c3cncc(CN4CCOCC4)c3)cc2NC(=O)c2c[nH]c(=O)cc2C(F)(F)F)CC1] | N-(4-fluoro-2-(4-methylpiperazin-1-yl)-5-(5-(morpholinomethyl)pyridin-3-yl)phenyl)-6-oxo-4-(trifluoromethyl)-1,6-dihydropyridine-3-carboxamide | 0.019 |

TABLE 1-continued

Binding affinities (K_D) derived from surface plasmon resonance (SPR) assays

| Example No. | Structure | IUPAC Name | WDR5 binding affinity (K_D, μM) |
|---|---|---|---|
| 48 | 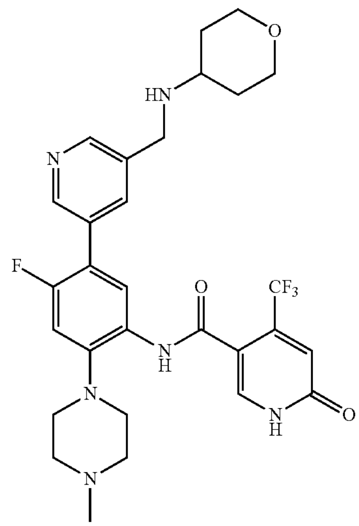 [SMILES: CN1CCN(c2cc(F)c(-c3cncc(CNC4CCOCC4)c3)cc2NC(=O)c2c[nH]c(=O)cc2C(F)(F)F)CC1] | N-(4-fluoro-2-(4-methylpiperazin-1-yl)-5-(5-(((tetrahydro-2H-pyran-4-yl)amino)methyl)pyridin-3-yl)phenyl)-6-oxo-4-(trifluoromethyl)-1,6-dihydropyridine-3-carboxamide | 0.015 |
| 49 | 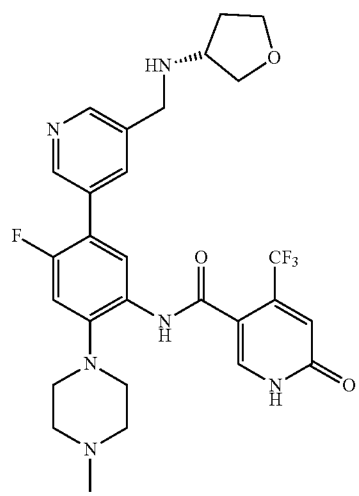 | (R)-N-(4-fluoro-2-(4-methylpiperazin-1-yl)-5-(5-(((tetrahydrofuran-3-yl)amino)methyl)pyridin-3-yl)phenyl)-6-oxo-4-(trifluoromethyl)-1,6-dihydropyridine-3-carboxamide | 0.014 |
| 50 | 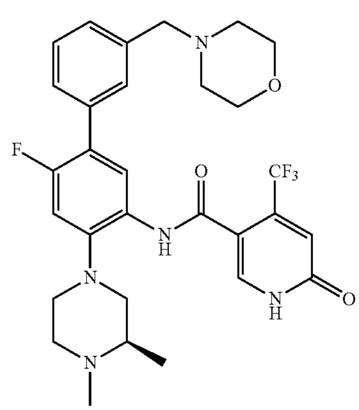 [SMILES: C[C@@H]1CN(c2cc(F)c(-c3cccc(CN4CCOCC4)c3)cc2NC(=O)c2c[nH]c(=O)cc2C(F)(F)F)CCN1C] | (R)-N-(4-(3,4-dimethylpiperazin-1-yl)-6-fluoro-3'-(morpholinomethyl)-[1,1'-biphenyl]-3-yl)-6-oxo-4-(trifluoromethyl)-1,6-dihydropyridine-3-carboxamide | 0.012 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 51 | 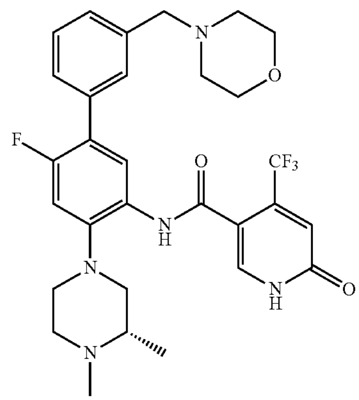 [SMILES: C[C@H]1CN(c2cc(F)c(-c3cccc(CN4CCOCC4)c3)cc2NC(=O)c2c[nH]c(=O)cc2C(F)(F)F)CCN1C] | (S)-N-(4-(3,4-dimethylpiperazin-1-yl)-6-fluoro-3'-(morpholinomethyl)-[1,1'-biphenyl]-3-yl)-6-oxo-4-(trifluoromethyl)-1,6-dihydropyridine-3-carboxamide | 0.007 |
| 52 | 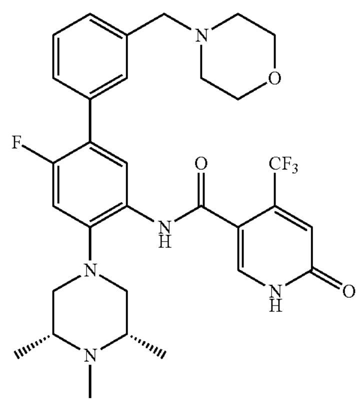 [SMILES: C[C@@H]1CN(c2cc(F)c(-c3cccc(CN4CCOCC4)c3)cc2NC(=O)c2c[nH]c(=O)cc2C(F)(F)F)C[C@H](C)N1C] | N-(6-fluoro-3'-(morpholinomethyl)-4-((3R,5S)-3,4,5-trimethylpiperazin-1-yl)-[1,1'-biphenyl]-3-yl)-6-oxo-4-(trifluoromethyl)-1,6-dihydropyridine-3-carboxamide | 0.006 |
| 53 | 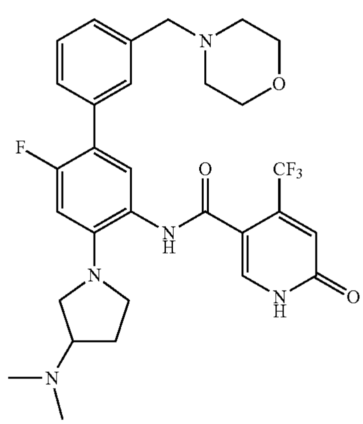 [SMILES: CN(C)C1CCN(c2cc(F)c(-c3cccc(CN4CCOCC4)c3)cc2NC(=O)c2c[nH]c(=O)cc2C(F)(F)F)C1] | N-(4-(3-(dimethylamino)pyrrolidin-1-yl)-6-fluoro-3'-(morpholinomethyl)-[1,1'-biphenyl]-3-yl)-6-oxo-4-(trifluoromethyl)-1,6-dihydropyridine-3-carboxamide | 0.0057 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 54 | 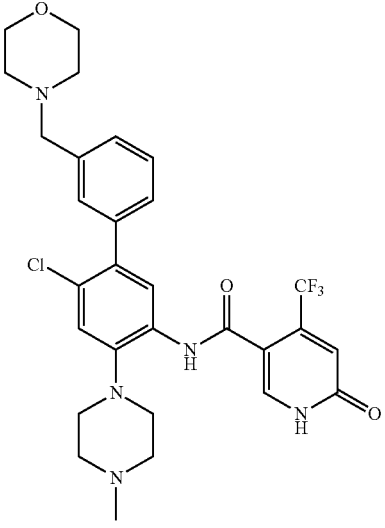 [SMILES: CN1CCN(c2cc(Cl)c(-c3cccc(CN4CCOCC4)c3)cc2NC(=O)c2c[nH]c(=O)cc2C(F)(F)F)CC1] | N-(6-chloro-4-(4-methylpiperazin-1-yl)-3'-(morpholinomethyl)-[1,1-biphenyl]-3-yl)-6-oxo-4-(trifluoromethyl)-1,6-dihydropyridine-3-carboxamide | 0.0510 |
| 55 (Comparative Ex.) | 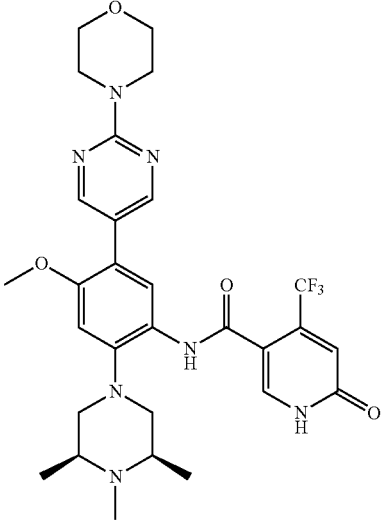 [SMILES: COc1cc(N2C[C@@H](C)N(C)[C@@H](C)C2)c(NC(=O)c2c[nH]c(=O)cc2C(F)(F)F)cc1-c1cnc(N2CCOCC2)nc1] | N-[4-methoxy-5-(2-morpholin-4-ylpyrimidin-5-yl)-2-[rac-(3R,5S)-3,4,5-trimethylpiperazin-1-yl]phenyl]-6-oxo-4-(trifluoromethyl)-1H-pyridine-3-carboxamide | >0.200 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 56 | 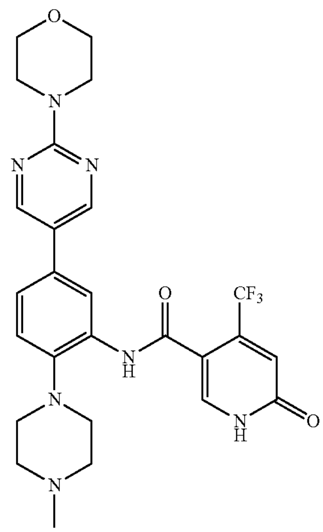 [SMILES: CN1CCN(c2ccc(-c3cnc(N4CCOCC4)nc3)cc2NC(=O)c2c[nH]c(=O)cc2C(F)(F)F)CC1] | N-(2-(4-methylpiperazin-1-yl)-5-(2-morpholinopyrimidin-5-yl)phenyl)-6-oxo-4-(trifluoromethyl)-1,6-dihydropyridine-3-carboxamide | 0.0175 |
| 57 | 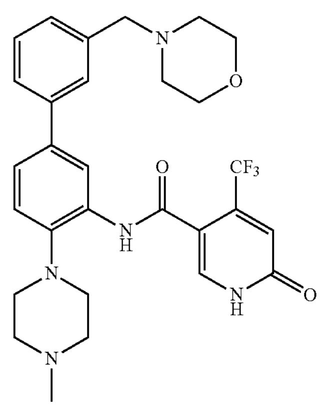 [SMILES: CN1CCN(c2ccc(-c3cccc(CN4CCOCC4)c3)cc2NC(=O)c2c[nH]c(=O)cc2C(F)(F)F)CC1] | N-[2-(4-methylpiperazin-1-yl)-5-[3-(morpholin-4-ylmethyl)phenyl]phenyl]-6-oxo-4-(trifluoromethyl)-1H-pyridine-3-carboxamide | 0.036 |
| 58 | 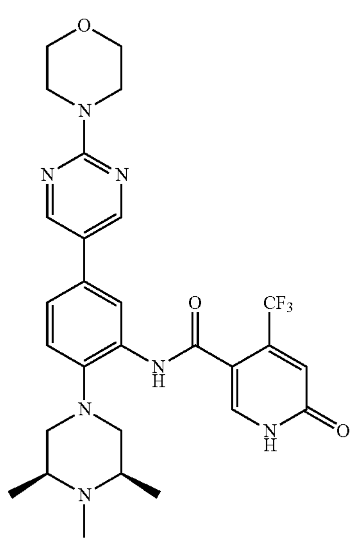 | N-(5-(2-morpholinopyrimidin-5-yl)-2-((3R,5S)-3,4,5-trimethylpiperazin-1-yl)phenyl)-6-oxo-4-(trifluoromethyl)-1,6-dihydropyridine-3-carboxamide | 0.0035 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 59 (Comparative Ex.) | 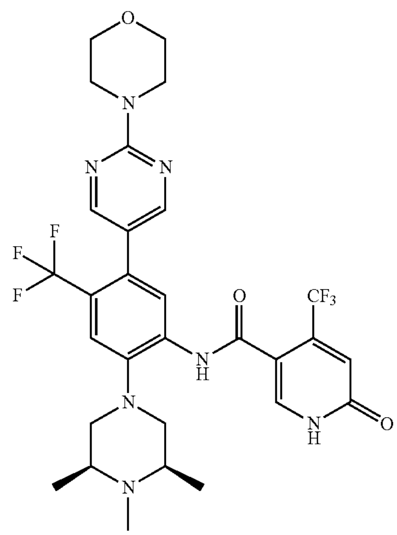 [SMILES: C[C@@H]1CN(c2cc(C(F)(F)F)c(-c3cnc(N4CCOCC4)nc3)cc2NC(=O)c2c[nH]c(=O)cc2C(F)(F)F)C[C@H](C)N1C] | N-[5-(2-morpholin-4-ylpyrimidin-5-yl)-2-[rac-(3R,5S)-3,4,5-trimethylpiperazin-1-yl]-4-(trifluoromethyl)phenyl]-6-oxo-4-(trifluoromethyl)-1H-pyridine-3-carboxamide | >0.200 |
| 60 | 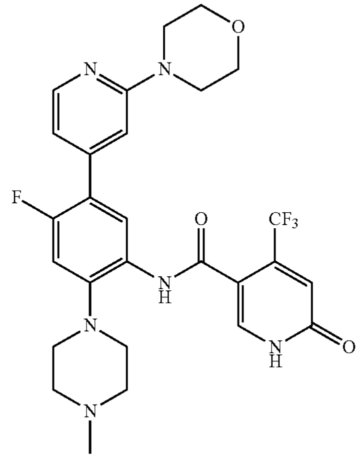 [SMILES: CN1CCN(c2cc(F)c(-c3ccnc(N4CCOCC4)c3)cc2NC(=O)c2c[nH]c(=O)cc2C(F)(F)F)CC1] | N-[4-fluoro-2-(4-methylpiperazin-1-yl)-5-(2-morpholin-4-ylpyridin-4-yl)phenyl]-6-oxo-4-(trifluoromethyl)-1H-pyridine-3-carboxamide | 0.00479 |
| 61 (Comparative Ex.) | 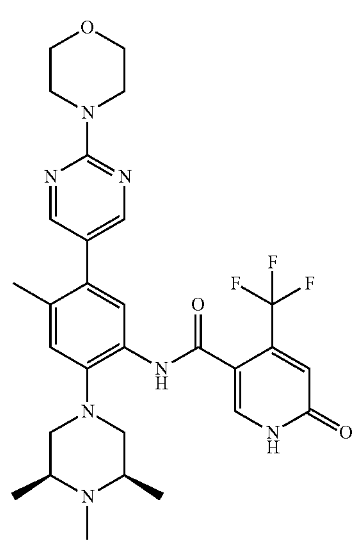 [SMILES: Cc1cc(N2C[C@@H](C)N(C)[C@@H](C)C2)c(NC(=O)c2c[nH]c(=O)cc2C(F)(F)F)cc1-c1cnc(N2CCOCC2)nc1] | N-[4-methyl-5-(2-morpholin-4-ylpyrimidin-5-yl)-2-[rac-(3R,5S)-3,4,5-trimethylpiperazin-1-yl]phenyl]-6-oxo-4-(trifluoromethyl)-1H-pyridine-3-carboxamide | 0.026 |

TABLE 1-continued

Binding affinities (K_D) derived from surface plasmon resonance (SPR) assays

| Example No. | Structure | IUPAC Name | WDR5 binding affinity (K_D, μM) |
|---|---|---|---|
| 62 | 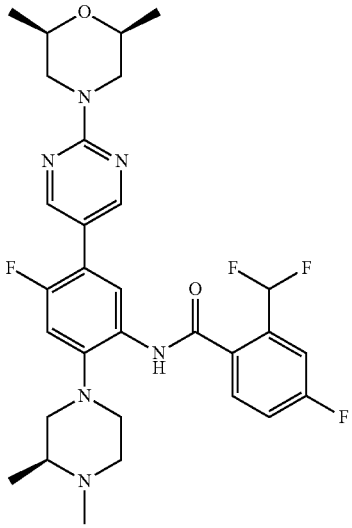 [SMILES: C[C@@H]1CN(c2ncc(-c3cc(NC(=O)c4ccc(F)cc4C(F)F)c(N4CCN(C)[C@@H](C)C4)cc3F)cn2)C[C@H](C)O1] | 2-(difluoromethyl)-N-(5-(2-((2S,6R)-2,6-dimethylmorpholino)pyrimidin-5-yl)-2-((S)-3,4-dimethylpiperazin-1-yl)-4-fluorophenyl)-4-fluorobenzamide | XXX |
| 63 | 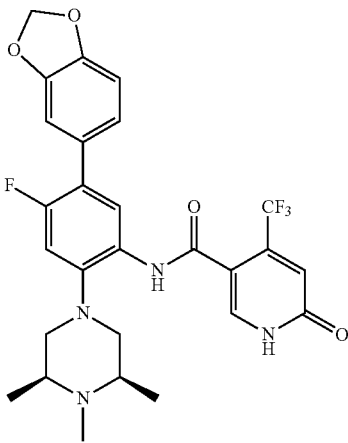 [SMILES: C[C@@H]1CN(c2cc(F)c(-c3ccc4c(c3)OCO4)cc2NC(=O)c2c[nH]c(=O)cc2C(F)(F)F)C[C@H](C)N1C] | N-[5-(1,3-benzodioxol-5-yl)4-fluoro-2-[rac-(3R,5S)-3,4,5-trimethylpiperazin-1-yl]phenyl]-6-oxo-4-(trifluoromethyl)-1H-pyridine-3-carboxamide | 0.000694 |
| 64 | 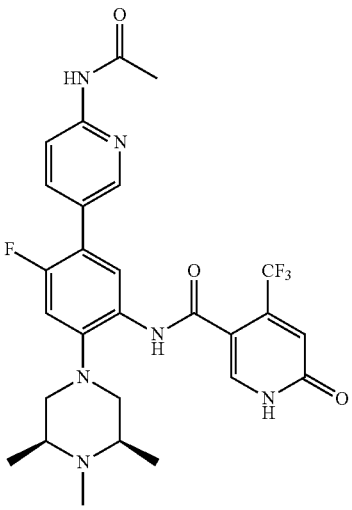 [SMILES: CC(=O)Nc1ccc(-c2cc(NC(=O)c3c[nH]c(=O)cc3C(F)(F)F)c(N3C[C@@H](C)N(C)[C@@H](C)C3)cc2F)cn1] | N-[5-(6-acetamidopyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.000199 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 65 | 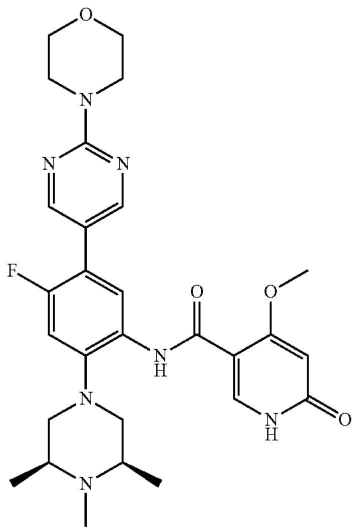 [SMILES: COc1cc(=O)[nH]cc1C(=O)Nc1cc(-c2cnc(N3CCOCC3)nc2)c(F)cc1N1C[C@@H](C)N(C)[C@@H](C)C1] | N-[4-fluoro-5-(2-morpholin-4-ylpyrimidin-5-yl)-2-[rac-(3R,5S)-3,4,5-trimethylpiperazin-1-yl]phenyl]-4-methoxy-6-oxo-1H-pyridine-3-carboxamide | 0.0572 |
| 66 | 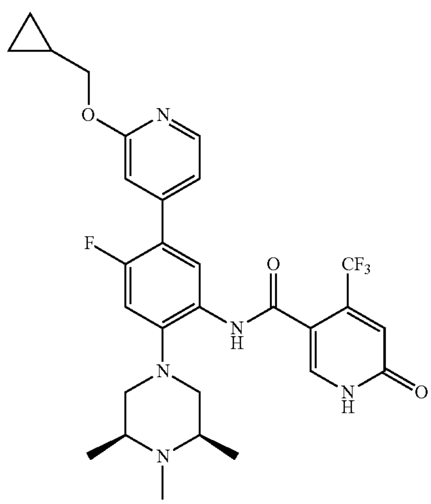 [SMILES: C[C@@H]1CN(c2cc(F)c(-c3ccnc(OCC4CC4)c3)cc2NC(=O)c2c[nH]c(=O)cc2C(F)(F)F)C[C@H](C)N1C] | N-[5-[2-(cyclopropylmethoxy)pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00116 |
| 67 | 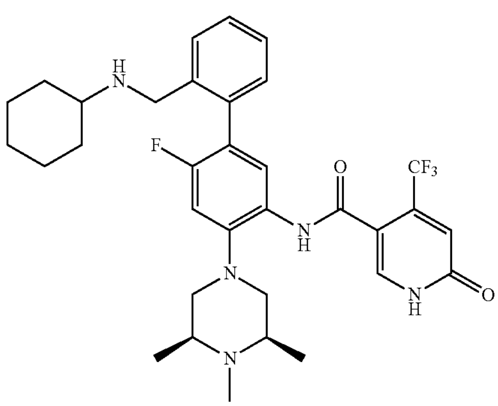 [SMILES: C[C@@H]1CN(c2cc(F)c(-c3ccccc3CNC3CCCCC3)cc2NC(=O)c2c[nH]c(=O)cc2C(F)(F)F)C[C@H](C)N1C] | N-[5-[2-(cyclohexylamino)methyl]phenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00482 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 68 | 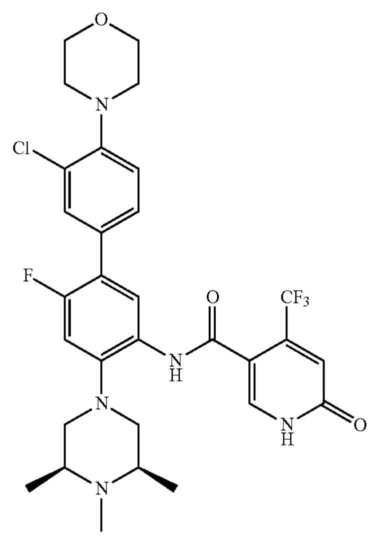 | N-[5-(3-chloro-4-morpholin-4-ylphenyl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00134 |
| 69 | 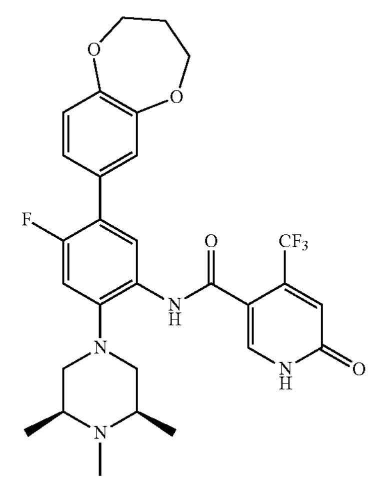 [SMILES: C[C@@H]1CN(c2cc(F)c(-c3ccc4c(c3)OCCCO4)cc2NC(=O)c2c[nH]c(=O)cc2C(F)(F)F)C[C@H](C)N1C] | N-[5-(3,4-dihydro-2H-1,5-benzodioxepin-7-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.000225 |
| 70 | 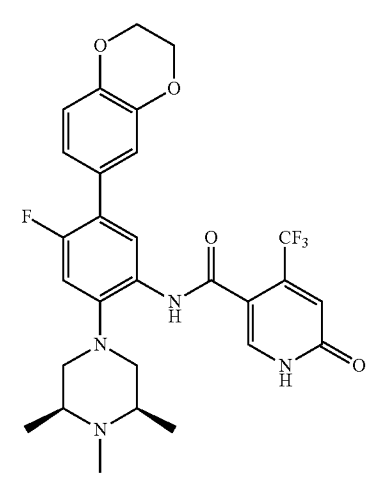 [SMILES: C[C@@H]1CN(c2cc(F)c(-c3ccc4c(c3)OCCO4)cc2NC(=O)c2c[nH]c(=O)cc2C(F)(F)F)C[C@H](C)N1C] | N-[5-(2,3-dihydro-1,4-benzodioxin-6-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.000429 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 71 | 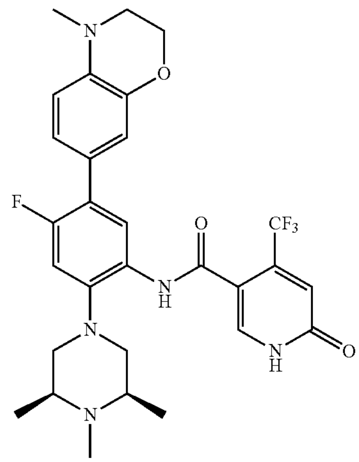 [SMILES: C[C@@H]1CN(c2cc(F)c(-c3ccc4c(c3)OCCN4C)cc2NC(=O)c2c[nH]c(=O)cc2C(F)(F)F)C[C@H](C)N1C] | N-[4-fluoro-5-(4-methyl-2,3-dihydro-1,4-benzoxazin-7-yl)-2-[rac-(3R,5S)-3,4,5-trimethylpiperazin-1-yl]phenyl]-6-oxo-4-(trifluoromethyl)-1H-pyridine-3-carboxamide | 0.000623 |
| 72 | 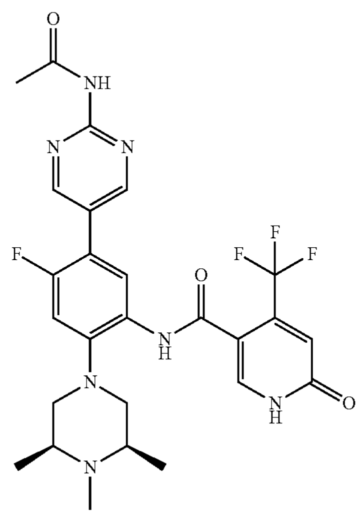 [SMILES: CC(=O)Nc1ncc(-c2cc(NC(=O)c3c[nH]c(=O)cc3C(F)(F)F)c(N3C[C@@H](C)N(C)[C@@H](C)C3)cc2F)cn1] | N-[5-(2-acetamidopyrimidin-5-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.000823 |
| 73 | 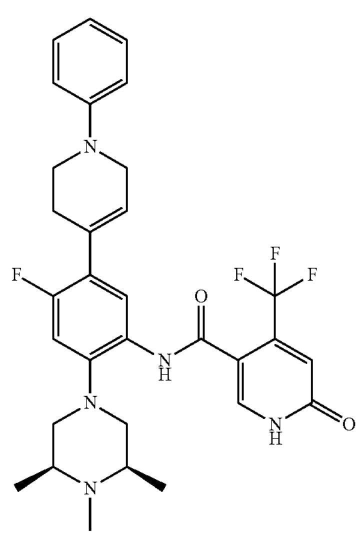 | N-[4-fluoro-5-(1-phenyl-3,6-dihydro-2H-pyridin-4-yl)-2-[rac-(3R,5S)-3,4,5-trimethylpiperazin-1-yl]phenyl]-6-oxo-4-(trifluoromethyl)-1H-pyridine-3-carboxamide | 0.00363 |

TABLE 1-continued
Binding affinities (K$_D$) derived from surface plasmon resonance (SPR) assays
| Example No. | Structure | IUPAC Name | WDR5 binding affinity (K$_D$, μM) |
|---|---|---|---|
| 74 | 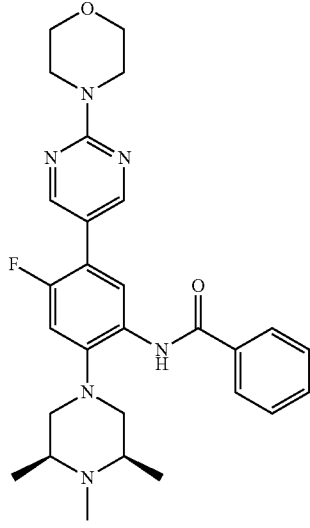 | N-[4-fluoro-5-(2-morpholin-4-ylpyrimidin-5-yl)-2-[rac-(3R,5S)-3,4,5-trimethylpiperazin-1-yl]phenyl]benzamide | 0.253 |
| 75 | 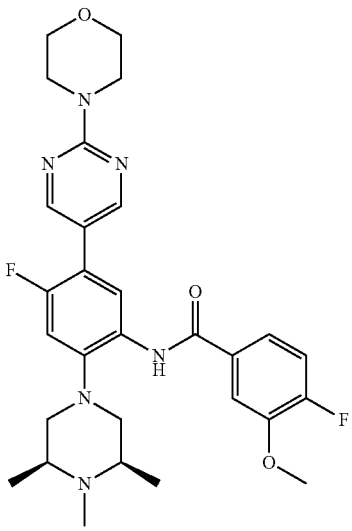 | 4-fluoro-N-[4-fluoro-5-(2-morpholin-4-ylpyrimidin-5-yl)-2-[rac-(3R,5S)-3,4,5-trimethylpiperazin-1-yl]phenyl]-3-methoxybenzamide | 0.0409 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 76 | 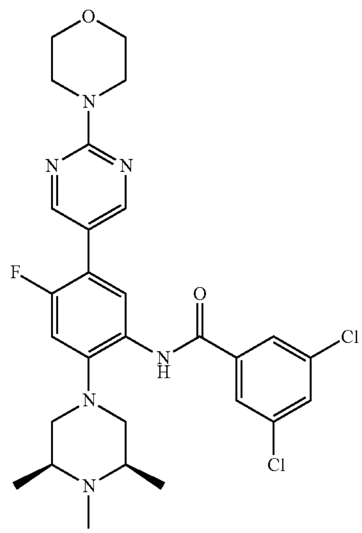 [SMILES: C[C@@H]1CN(c2cc(F)c(-c3cnc(N4CCOCC4)nc3)cc2NC(=O)c2cc(Cl)cc(Cl)c2)C[C@H](C)N1C] | 3,5-dichloro-N-[4-fluoro-5-(2-morpholin-4-ylpyrimidin-5-yl)-2-[rac-(3R,5S)-3,4,5-trimethylpiperazin-1-yl]phenyl]benzamide | 0.00207 |
| 77 | 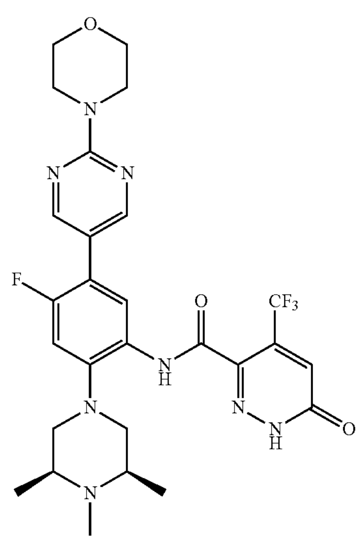 [SMILES: C[C@@H]1CN(c2cc(F)c(-c3cnc(N4CCOCC4)nc3)cc2NC(=O)c2n[nH]c(=O)cc2C(F)(F)F)C[C@H](C)N1C] | N-[4-fluoro-5-(2-morpholin-4-ylpyrimidin-5-yl)-2-[rac-(3R,5S)-3,4,5-trimethylpiperazin-1-yl]phenyl]-6-oxo-4-(trifluoromethyl)-1H-pyridazine-3-carboxamide | 0.00443 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 78 | 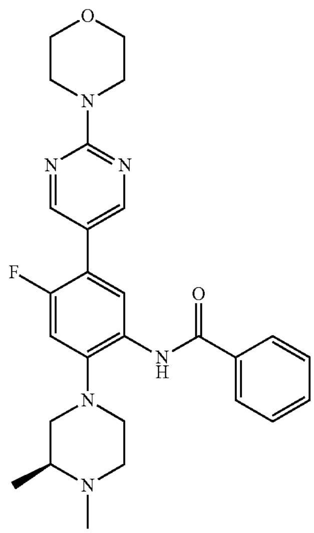 | N-[4-fluoro-5-(2-morpholin-4-ylpyrimidin-5-yl)-2-[rac-(3R)-3,4-dimethylpiperazin-1-yl]phenyl]benzamide | 0.0179 |
| 79 | 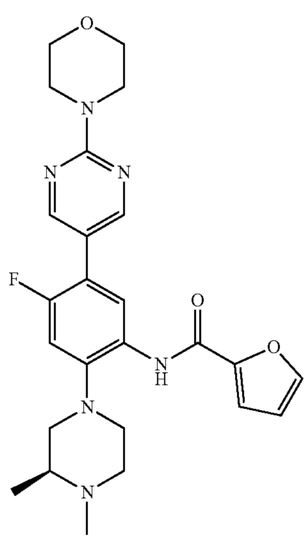 [SMILES: C[C@H]1CN(c2cc(F)c(-c3cnc(N4CCOCC4)nc3)cc2NC(=O)c2ccco2)CCN1C] | N-[4-fluoro-5-(2-morpholin-4-ylpyrimidin-5-yl)-2-[rac-(3R)-3,4-dimethylpiperazin-1-yl]phenyl]furan-2-carboxamide | >0.200 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 80 | 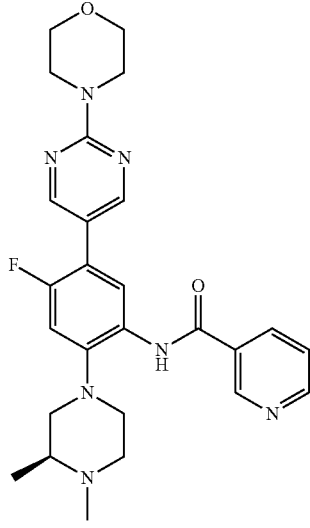 | N-[4-fluoro-5-(2-morpholin-4-ylpyrimidin-5-yl)-2-[rac-(3R)-3,4-dimethylpiperazin-1-yl]phenyl]pyridine-3-carboxamide | >0.200 |
| 81 (Comparative Ex.) | 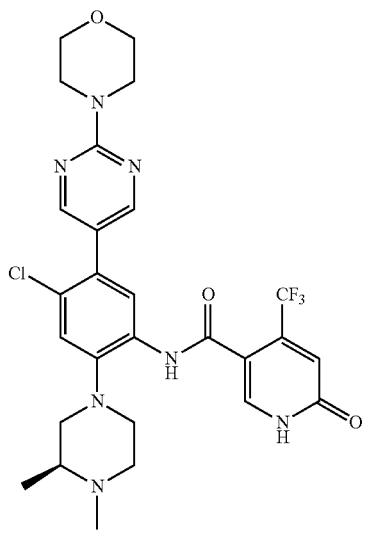 [SMILES: C[C@H]1CN(c2cc(Cl)c(-c3cnc(N4CCOCC4)nc3)cc2NC(=O)c2c[nH]c(=O)cc2C(F)(F)F)CCN1C] | N-[4-chloro-5-(2-morpholin-4-ylpyrimidin-5-yl)-2-[rac-(3R)-3,4-dimethylpiperazin-1-yl]phenyl]-6-oxo-4-(trifluoromethyl)-1H-pyridine-3-carboxamide | 0.0111 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 82 (Comparative Ex.) | 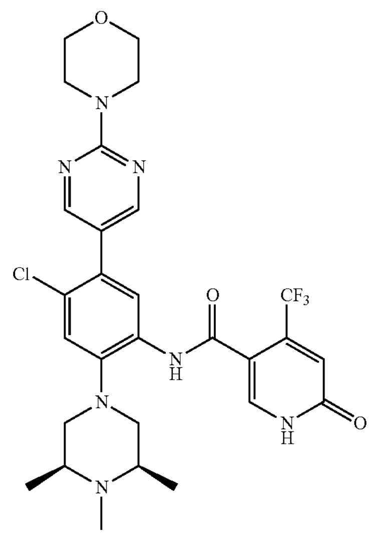 [SMILES: C[C@@H]1CN(c2cc(Cl)c(-c3cnc(N4CCOCC4)nc3)cc2NC(=O)c2c[nH]c(=O)cc2C(F)(F)F)C[C@H](C)N1C] | N-[4-chloro-5-(2-morpholin-4-ylpyrimidin-5-yl)-2-[rac-(3R,5S)-3,4,5-trimethylpiperazin-1-yl]phenyl]-6-oxo-4-(trifluoromethyl)-1H-pyridine-3-carboxamide | 0.0106 |
| 83 | 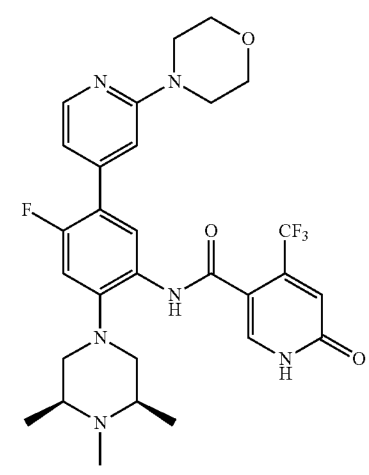 | N-[4-fluoro-5-(2-morpholin-4-ylpyridin-4-yl)-2-[rac-(3R,5S)-3,4,5-trimethylpiperazin-1-yl]phenyl]-6-oxo-4-(trifluoromethyl)-1H-pyridine-3-carboxamide | 0.000391 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 84 | 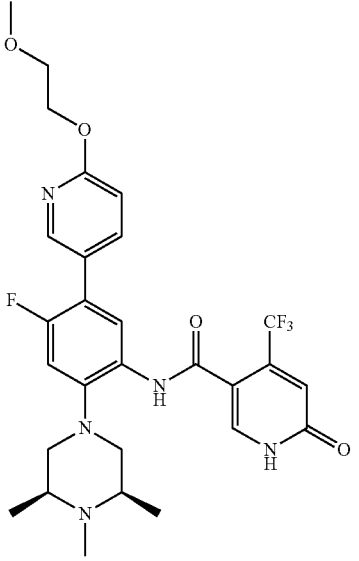 | N-[4-fluoro-5-[6-(2-methoxyethoxy)pyridin-3-yl]-2-[rac-(3R,5S)-3,4,5-trimethylpiperazin-1-yl]phenyl]-6-oxo-4-(trifluoromethyl)-1H-pyridine-3-carboxamide | 0.000338 |
| 85 | 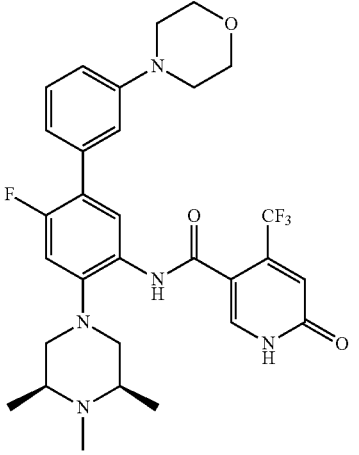 | N-[4-fluoro-5-(3-morpholin-4-ylphenyl)-2-[rac-(3R,5S)-3,4,5-trimethylpiperazin-1-yl]phenyl]-6-oxo-4-(trifluoromethyl)-1H-pyridine-3-carboxamide | 0.000703 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 86 | 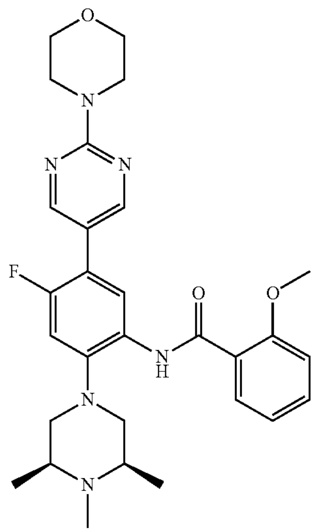 | N-[4-fluoro-5-(2-morpholin-4-ylpyrimidin-5-yl)-2-[rac-(3R,5S)-3,4,5-trimethylpiperazin-1-yl]phenyl]-2-methoxybenzamide | 0.204 |
| 87 | 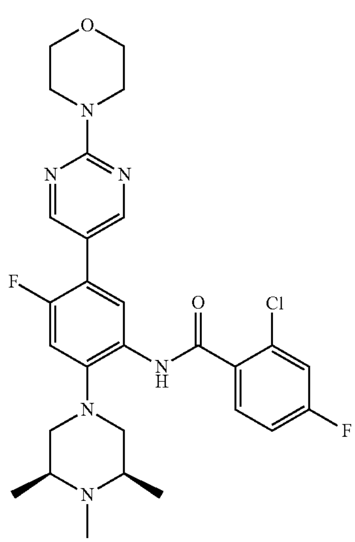 | 2-chloro-4-fluoro-N-[4-fluoro-5-(2-morpholin-4-ylpyrimidin-5-yl)-2-[rac-(3R,5S)-3,4,5-trimethylpiperazin-1-yl]phenyl]benzamide | 0.00821 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 88 | 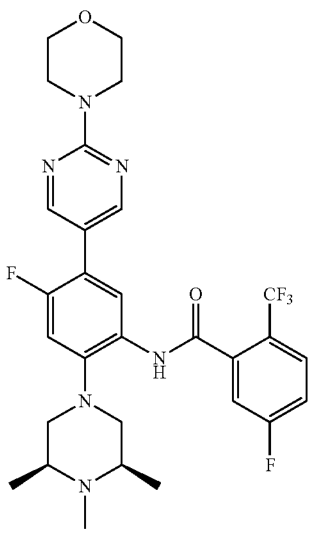 [SMILES: C[C@@H]1CN(c2cc(F)c(-c3cnc(N4CCOCC4)nc3)cc2NC(=O)c2cc(F)ccc2C(F)(F)F)C[C@H](C)N1C] | 5-fluoro-N-[4-fluoro-5-(2-morpholin-4-ylpyrimidin-5-yl)-2-[rac-(3R,5S)-3,4,5-trimethylpiperazin-1-yl]phenyl]-2-(trifluoromethyl)benzamide | 0.0241 |
| 89 | 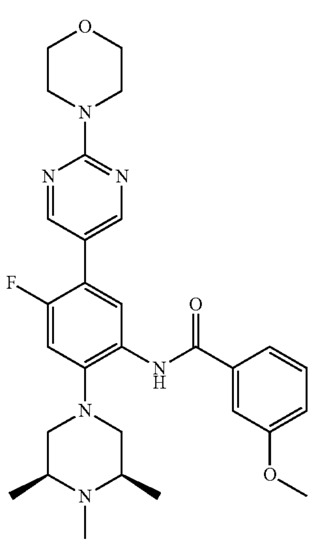 | N-[4-fluoro-5-(2-morpholin-4-ylpyrimidin-5-yl)-2-[rac-(3R,5S)-3,4,5-trimethylpiperazin-1-yl]phenyl]-3-methoxybenzamide | 0.0338 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 90 | 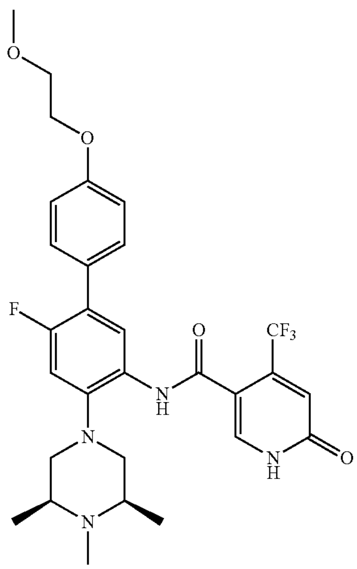 | N-[4-fluoro-5-[4-(2-methoxyethoxy)phenyl]-2-[rac-(3R,5S)-3,4,5-trimethylpiperazin-1-yl]phenyl]-6-oxo-4-(trifluoromethyl)-1H-pyridine-3-carboxamide | 0.000441 |
| 91 | 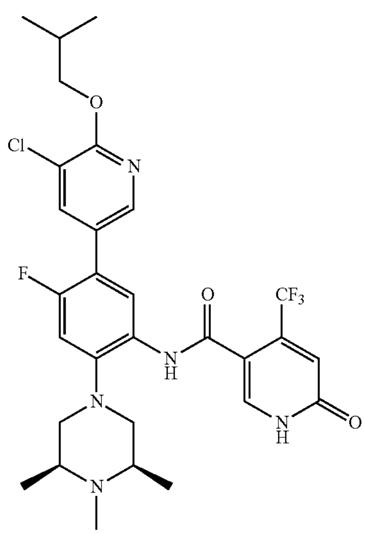 [SMILES: CC(C)COc1ncc(-c2cc(NC(=O)c3c[nH]c(=O)cc3C(F)(F)F)c(N3C[C@@H](C)N(C)[C@@H](C)C3)cc2F)cc1Cl] | N-[5-[5-chloro-6-(2-methylpropoxy)pyridin-3-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00447 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 92 | 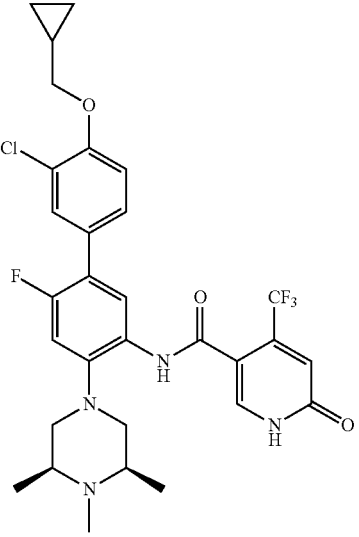 [SMILES: C[C@@H]1CN(c2cc(F)c(-c3ccc(OCC4CC4)c(Cl)c3)cc2NC(=O)c2c[nH]c(=O)cc2C(F)(F)F)C[C@H](C)N1C] | N-[5-[3-chloro-4-(cyclopropylmethoxy)phenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.0109 |
| 93 | 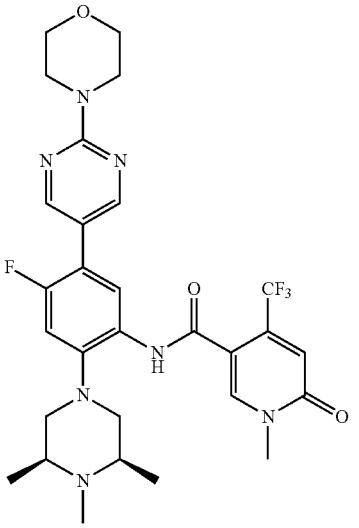 | N-[4-fluoro-5-(2-morpholin-4-ylpyrimidin-5-yl)-2-[rac-(3R,5S)-3,4,5-trimethylpiperazin-1-yl]phenyl]-1-methyl-6-oxo-4-(trifluoromethyl)pyridine-3-carboxamide | 0.00217 |
| 94 | 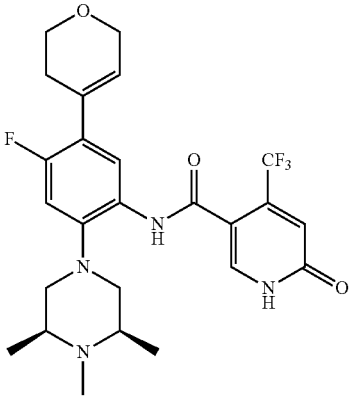 | N-[5-(3,6-dihydro-2H-pyran-4-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00406 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 95 | 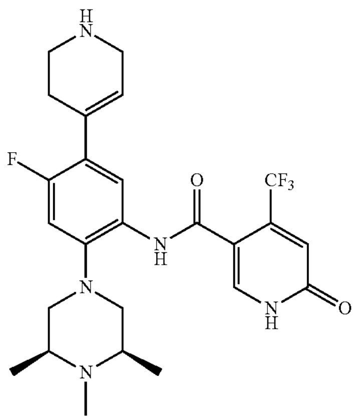 [SMILES: C[C@@H]1CN(c2cc(F)c(C3=CCNCC3)cc2NC(=O)c2c[nH]c(=O)cc2C(F)(F)F)C[C@H](C)N1C] | N-[4-fluoro-2-[rac-(3R,5S)-3,4,5-trimethylpiperazin-1-yl]-5-(1,2,3,6-tetrahydropyridin-4-yl)phenyl]-6-oxo-4-(trifluoromethyl)-1H-pyridine-3-carboxamide | 0.00718 |
| 96 | 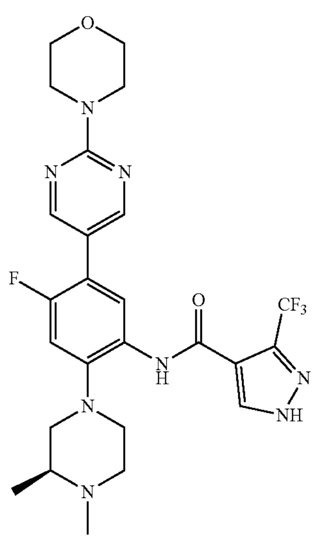 [SMILES: C[C@H]1CN(c2cc(F)c(-c3cnc(N4CCOCC4)nc3)cc2NC(=O)c2c[nH]nc2C(F)(F)F)CCN1C] | N-[4-fluoro-5-(2-morpholin-4-ylpyrimidin-5-yl)-2-[rac-(3R)-3,4-dimethylpiperazin-1-yl]phenyl]-3-(trifluoromethyl)-1H-pyrazole-4-carboxamide | 0.00771 |
| 97 | 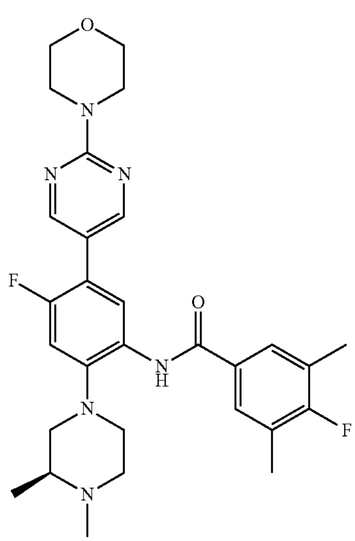 [SMILES: Cc1cc(C(=O)Nc2cc(-c3cnc(N4CCOCC4)nc3)c(F)cc2N2CCN(C)[C@@H](C)C2)cc(C)c1F] | 4-fluoro-N-[4-fluoro-5-(2-morpholin-4-ylpyrimidin-5-yl)-2-[rac-(3R)-3,4-dimethylpiperazin-1-yl]phenyl]-3,5-dimethylbenzamide | 0.00221 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 98 | 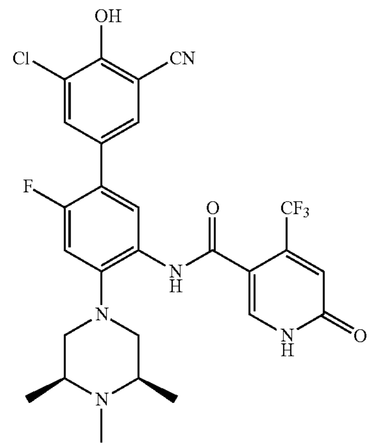 [SMILES: C[C@@H]1CN(c2cc(F)c(-c3cc(Cl)c(O)c(C#N)c3)cc2NC(=O)c2c[nH]c(=O)cc2C(F)(F)F)C[C@H](C)N1C] | N-[5-(3-chloro-5-cyano-4-hydroxyphenyl)-4-fluoro-2-[rac-(3R,5S)-3,4,5-trimethylpiperazin-1-yl]phenyl]-6-oxo-4-(trifluoromethyl)-1H-pyridine-3-carboxamide | 0.0195 |
| 99 | 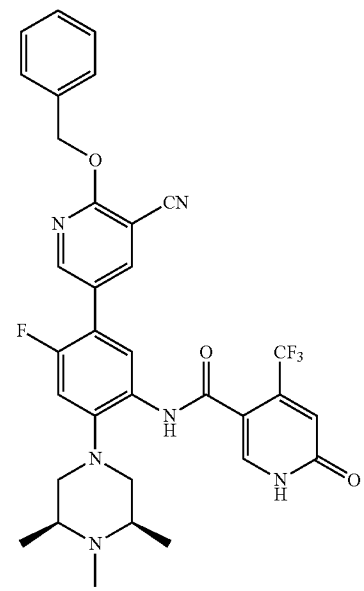 [SMILES: C[C@@H]1CN(c2cc(F)c(-c3cnc(OCc4ccccc4)c(C#N)c3)cc2NC(=O)c2c[nH]c(=O)cc2C(F)(F)F)C[C@H](C)N1C] | N-[5-(5-cyano-6-phenylmethoxypyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.0111 |
| 100 | 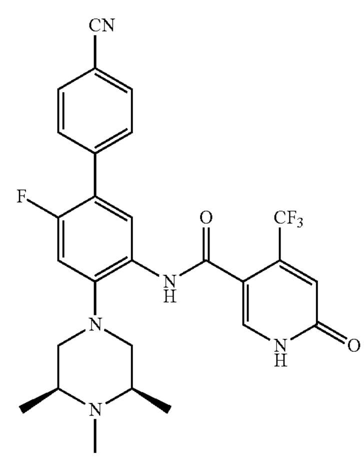 | N-[5-(4-cyanophenyl)-4-fluoro-2-[rac-(3R,5S)-3,4,5-trimethylpiperazin-1-yl]phenyl]-6-oxo-4-(trifluoromethyl)-1H-pyridine-3-carboxamide | 0.000508 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 101 | 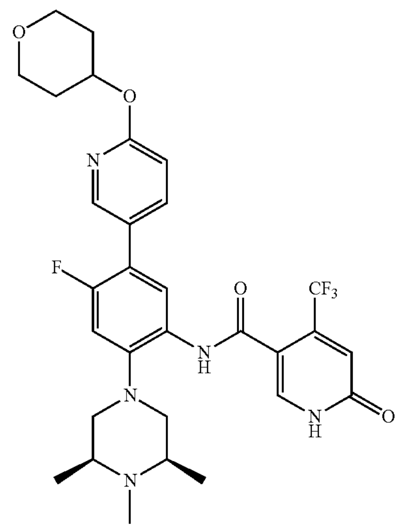 [SMILES: C[C@@H]1CN(c2cc(F)c(-c3ccc(OC4CCOCC4)nc3)cc2NC(=O)c2c[nH]c(=O)cc2C(F)(F)F)C[C@H](C)N1C] | N-[4-fluoro-5-[6-(oxan-4-yloxy)pyridin-3-yl]-2-[rac-(3R,5S)-3,4,5-trimethylpiperazin-1-yl]phenyl]-6-oxo-4-(trifluoromethyl)-1H-pyridine-3-carboxamide | 0.00032 |
| 102 | 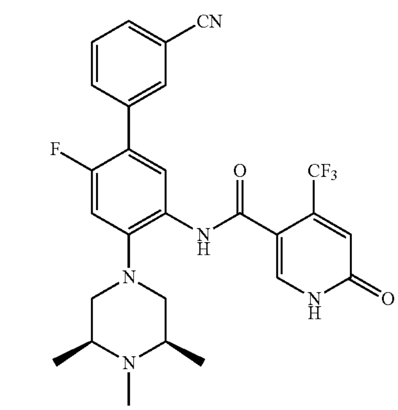 | N-[5-(3-cyanophenyl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00208 |
| 103 | 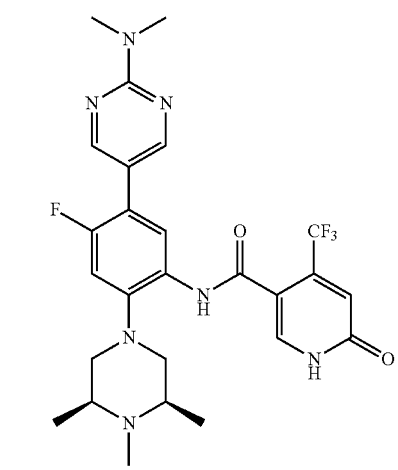 | N-[5-[2-(dimethylamino)pyrimidin-5-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.000168 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 104 | 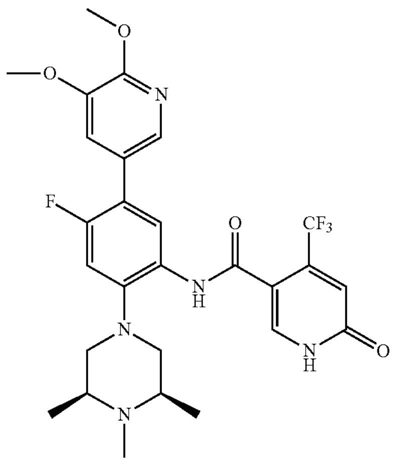 [SMILES: COc1cc(-c2cc(NC(=O)c3c[nH]c(=O)cc3C(F)(F)F)c(N3C[C@@H](C)N(C)[C@@H](C)C3)cc2F)cnc1OC] | N-[5-(5,6-dimethoxypyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00241 |
| 105 | 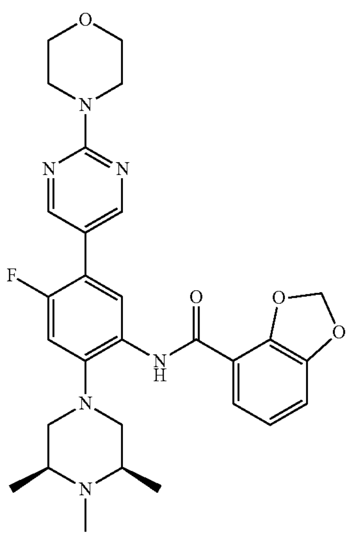 [SMILES: C[C@@H]1CN(c2cc(F)c(-c3cnc(N4CCOCC4)nc3)cc2NC(=O)c2cccc3c2OCO3)C[C@H](C)N1C] | N-[4-fluoro-5-(2-morpholin-4-ylpyrimidin-5-yl)-2-[rac-(3R,5S)-3,4,5-trimethylpiperazin-1-yl]phenyl]-1,3-benzodioxole-4-carboxamide | 0.466 |
| 106 | 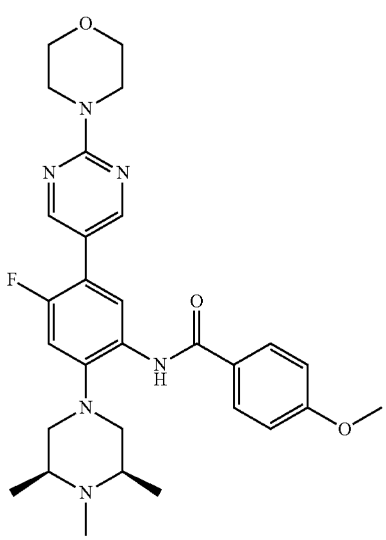 [SMILES: COc1ccc(C(=O)Nc2cc(-c3cnc(N4CCOCC4)nc3)c(F)cc2N2C[C@@H](C)N(C)[C@@H](C)C2)cc1] | N-[4-fluoro-5-(2-morpholin-4-ylpyrimidin-5-yl)-2-[rac-(3R,5S)-3,4,5-trimethylpiperazin-1-yl]phenyl]-4-methoxybenzamide | 5.4 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 107 | 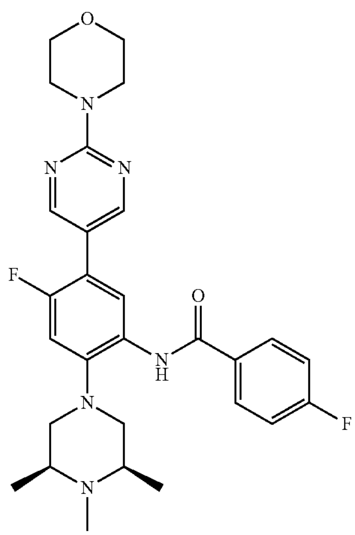 | 4-fluoro-N-[4-fluoro-5-(2-morpholin-4-ylpyrimidin-5-yl)-2-[rac-(3R,5S)-3,4,5-trimethylpiperazin-1-yl]phenyl]benzamide | 0.137 |
| 108 | 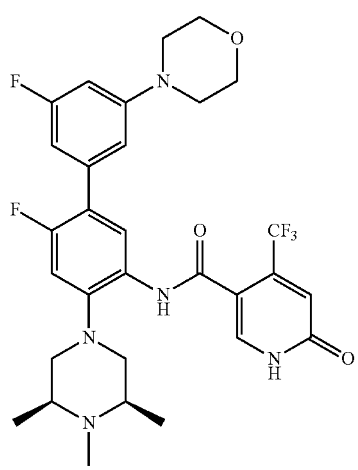 | N-[4-fluoro-5-(3-fluoro-5-morpholin-4-ylphenyl)-2-[rac-(3R,5S)-3,4,5-trimethylpiperazin-1-yl]phenyl]-6-oxo-4-(trifluoromethyl)-1H-pyridine-3-carboxamide | 0.00391 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 109 | 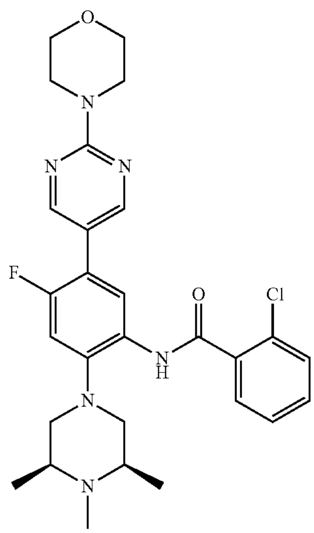 | 2-chloro-N-[4-fluoro-5-(2-morpholin-4-ylpyrimidin-5-yl)-2-[rac-(3R,5S)-3,4,5-trimethylpiperazin-1-yl]phenyl]benzamide | 0.175 |
| 110 | 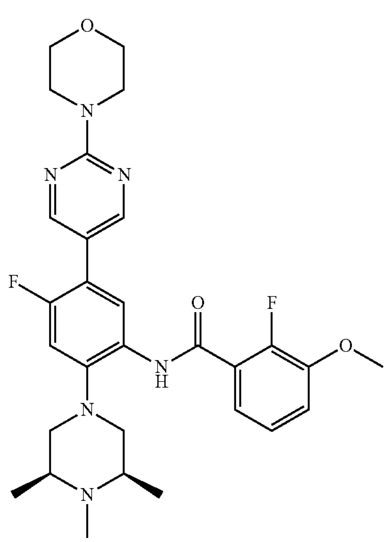 [SMILES: COc1cccc(C(=O)Nc2cc(-c3cnc(N4CCOCC4)nc3)c(F)cc2N2C[C@@H](C)N(C)[C@@H](C)C2)c1F] | 2-fluoro-N-[4-fluoro-5-(2-morpholin-4-ylpyrimidin-5-yl)-2-[rac-(3R,5S)-3,4,5-trimethylpiperazin-1-yl]phenyl]-3-methoxybenzamide | 1.73 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 111 | 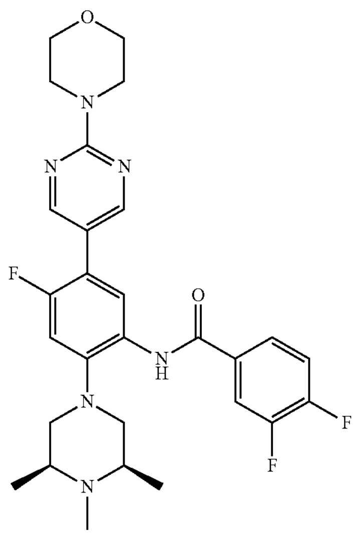 [SMILES: C[C@@H]1CN(c2cc(F)c(-c3cnc(N4CCOCC4)nc3)cc2NC(=O)c2ccc(F)c(F)c2)C[C@H](C)N1C] | 3,4-difluoro-N-[4-fluoro-5-(2-morpholin-4-ylpyrimidin-5-yl)-2-[rac-(3R,5S)-3,4,5-trimethylpiperazin-1-yl]phenyl]benzamide | 0.0706 |
| 112 | 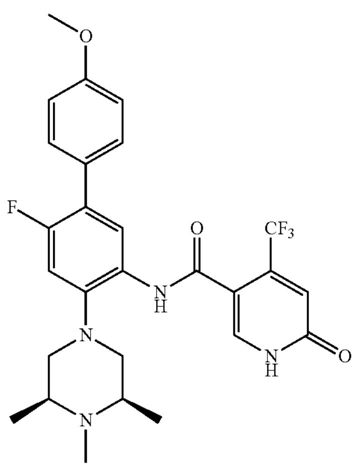 | N-[4-fluoro-5-(4-methoxyphenyl)-2-[rac-(3R,5S)-3,4,5-trimethylpiperazin-1-yl]phenyl]-6-oxo-4-(trifluoromethyl)-1H-pyridine-3-carboxamide | 0.00244 |
| 113 | 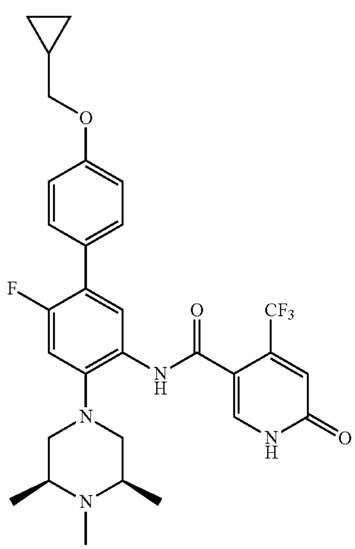 [SMILES: C[C@@H]1CN(c2cc(F)c(-c3ccc(OCC4CC4)cc3)cc2NC(=O)c2c[nH]c(=O)cc2C(F)(F)F)C[C@H](C)N1C] | N-[5-[4-(cyclopropylmethoxy)phenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.000858 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 114 | 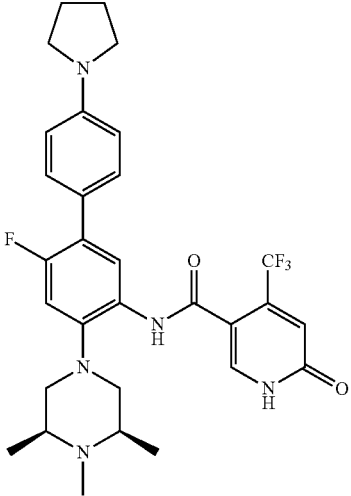 [SMILES: C[C@@H]1CN(c2cc(F)c(-c3ccc(N4CCCC4)cc3)cc2NC(=O)c2c[nH]c(=O)cc2C(F)(F)F)C[C@H](C)N1C] | N-[4-fluoro-5-(4-pyrrolidin-1-ylphenyl)-2-[rac-(3R,5S)-3,4,5-trimethylpiperazin-1-yl]phenyl]-6-oxo-4-(trifluoromethyl)-1H-pyridine-3-carboxamide | 0.00406 |
| 115 | 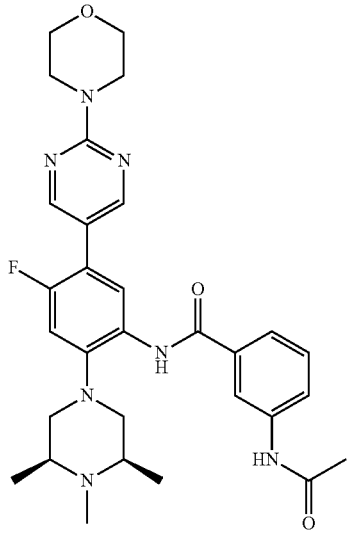 [SMILES: CC(=O)Nc1cccc(C(=O)Nc2cc(-c3cnc(N4CCOCC4)nc3)c(F)cc2N2C[C@@H](C)N(C)[C@@H](C)C2)c1] | 3-acetamido-N-[4-fluoro-5-(2-morpholin-4-ylpyrimidin-5-yl)-2-[rac-(3R,5S)-3,4,5-trimethylpiperazin-1-yl]phenyl]benzamide | >0.200 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 116 | 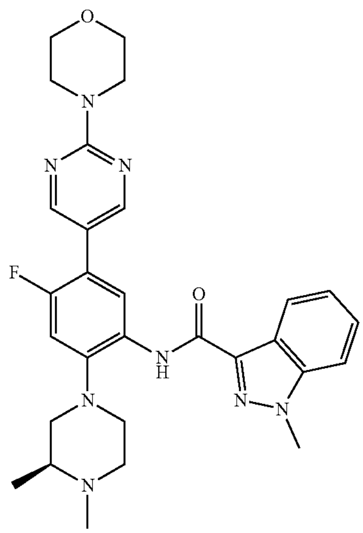 | N-[4-fluoro-5-(2-morpholin-4-ylpyrimidin-5-yl)-2-[rac-(3R)-3,4-dimethylpiperazin-1-yl]phenyl]-1-methylindazole-3-carboxamide | 0.0768 |
| 117 | 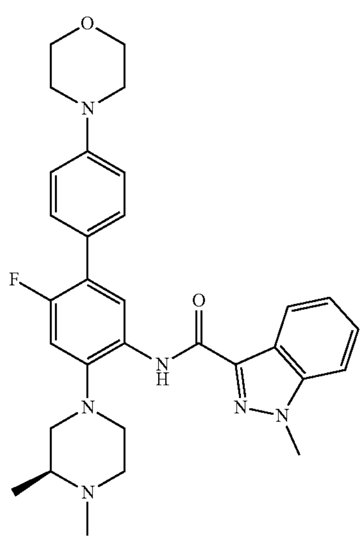 [SMILES: C[C@H]1CN(c2cc(F)c(-c3ccc(N4CCOCC4)cc3)cc2NC(=O)c2nn(C)c3ccccc23)CCN1C] | N-[4-fluoro-5-(4-morpholin-4-ylphenyl)-2-[rac-(3R)-3,4-dimethylpiperazin-1-yl]phenyl]-1-methylindazole-3-carboxamide | 0.0428 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 118 | 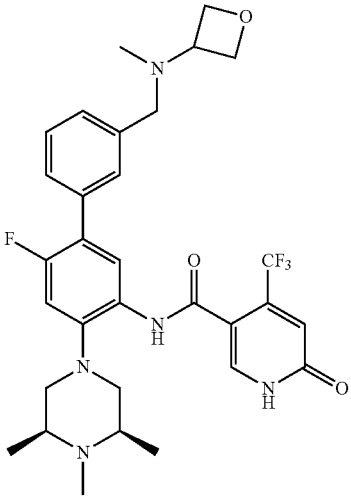 [SMILES: C[C@@H]1CN(c2cc(F)c(-c3cccc(CN(C)C4COC4)c3)cc2NC(=O)c2c[nH]c(=O)cc2C(F)(F)F)C[C@H](C)N1C] | N-[4-fluoro-5-[3-[[methyl(oxetan-3-yl)amino]methyl]phenyl]-2-[rac-(3R,5S)-3,4,5-trimethylpiperazin-1-yl]phenyl]-6-oxo-4-(trifluoromethyl)-1H-pyridine-3-carboxamide | 0.00453 |
| 119 | 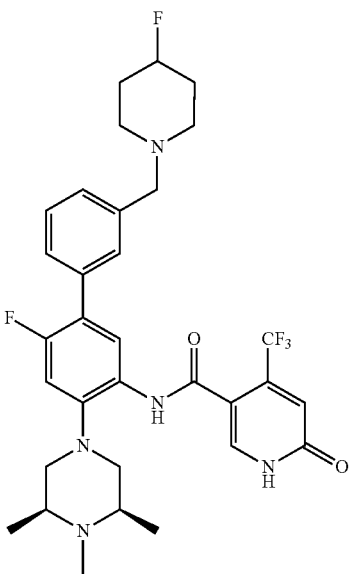 [SMILES: C[C@@H]1CN(c2cc(F)c(-c3cccc(CN4CCC(F)CC4)c3)cc2NC(=O)c2c[nH]c(=O)cc2C(F)(F)F)C[C@H](C)N1C] | N-[4-fluoro-5-[3-[(4-fluoropiperidin-1-yl)methyl]phenyl]-2-[rac-(3R,5S)-3,4,5-trimethylpiperazin-1-yl]phenyl]-6-oxo-4-(trifluoromethyl)-1H-pyridine-3-carboxamide | 0.00512 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 120 | 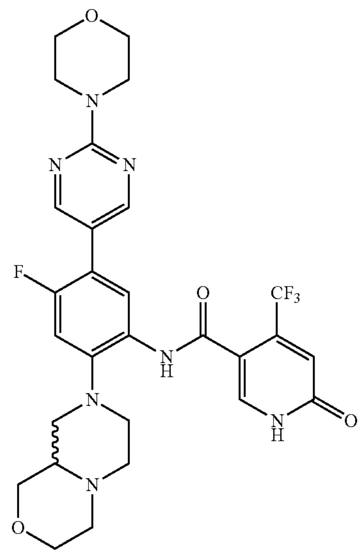 [SMILES: O=C(Nc1cc(-c2cnc(N3CCOCC3)nc2)c(F)cc1N1CCN2CCOCC2C1)c1c[nH]c(=O)cc1C(F)(F)F] | N-[2-(3,4,6,7,9,9a-hexahydro-1H-pyrazino[2,1-c][1,4]oxazin-8-yl)-4-fluoro-5-(2-morpholin-4-ylpyrimidin-5-yl)phenyl]-6-oxo-4-(trifluoromethyl)-1H-pyridine-3-carboxamide | >0.200 |
| 121 | 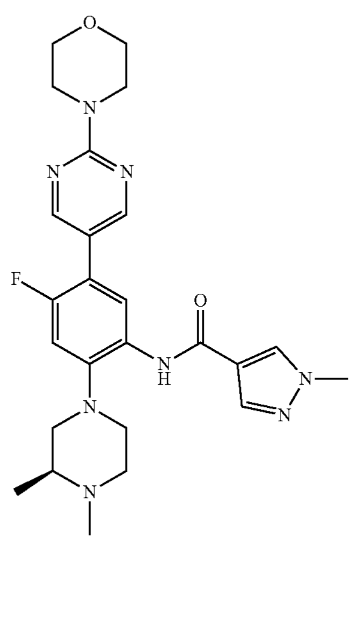 | N-[4-fluoro-5-(2-morpholin-4-ylpyrimidin-5-yl)-2-[rac-(3R)-3,4-dimethylpiperazin-1-yl]phenyl]-1-methylpyrazole-4-carboxamide | 0.0334 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 122 | 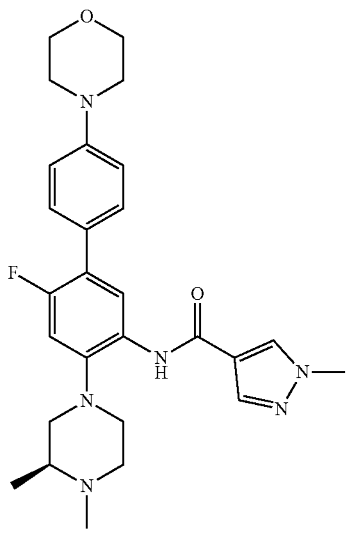 [SMILES: C[C@H]1CN(c2cc(F)c(-c3ccc(N4CCOCC4)cc3)cc2NC(=O)c2cnn(C)c2)CCN1C] | N-[4-fluoro-5-(4-morpholin-4-ylphenyl)-2-[rac-(3R)-3,4-dimethylpiperazin-1-yl]phenyl]-1-methylpyrazole-4-carboxamide | 0.0702 |
| 123 | 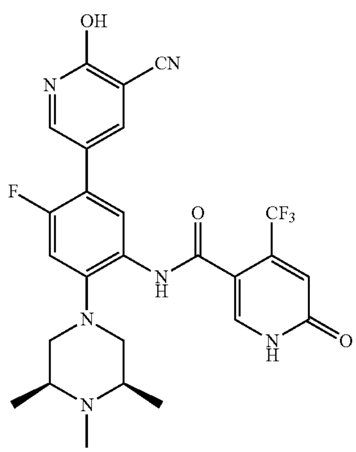 [SMILES: C[C@@H]1CN(c2cc(F)c(-c3cnc(O)c(C#N)c3)cc2NC(=O)c2c[nH]c(=O)cc2C(F)(F)F)C[C@H](C)N1C] | N-[5-(5-cyano-6-hydroxypyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00988 |
| 124 | 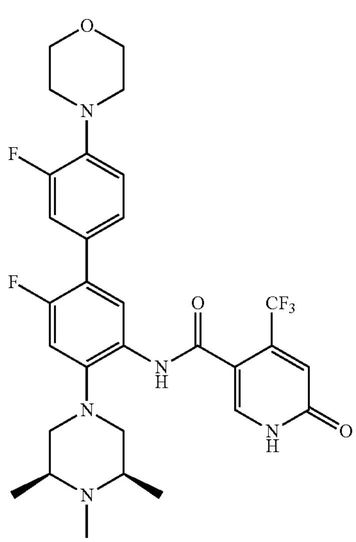 [SMILES: C[C@@H]1CN(c2cc(F)c(-c3ccc(N4CCOCC4)c(F)c3)cc2NC(=O)c2c[nH]c(=O)cc2C(F)(F)F)C[C@H](C)N1C] | N-[4-fluoro-5-(3-fluoro-4-morpholin-4-ylphenyl)-2-[rac-(3R,5S)-3,4,5-trimethylpiperazin-1-yl]phenyl]-6-oxo-4-(trifluoromethyl)-1H-pyridine-3-carboxamide | 0.000439 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 125 | 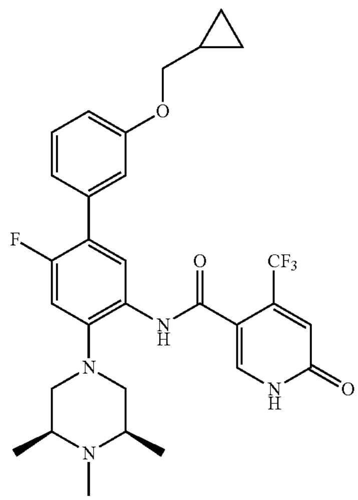 | N-[5-[3-(cyclopropylmethoxy)phenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.0109 |
| 126 | 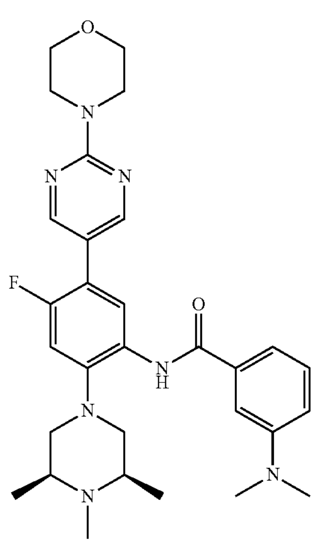 [SMILES: C[C@@H]1CN(c2cc(F)c(-c3cnc(N4CCOCC4)nc3)cc2NC(=O)c2cccc(N(C)C)c2)C[C@H](C)N1C] | 3-(dimethylamino)-N-[4-fluoro-5-(2-morpholin-4-ylpyrimidin-5-yl)-2-[rac-(3R,5S)-3,4,5-trimethylpiperazin-1-yl]phenyl]benzamide | 3.5 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 127 | 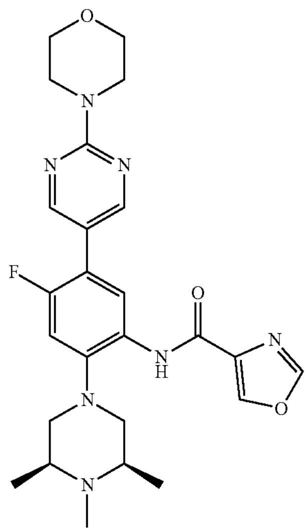 [SMILES: C[C@@H]1CN(c2cc(F)c(-c3cnc(N4CCOCC4)nc3)cc2NC(=O)c2cocn2)C[C@H](C)N1C] | N-[4-fluoro-5-(2-morpholin-4-ylpyrimidin-5-yl)-2-[rac-(3R,5S)-3,4,5-trimethylpiperazin-1-yl]phenyl]-1,3-oxazole-4-carboxamide | >0.200 |
| 128 | 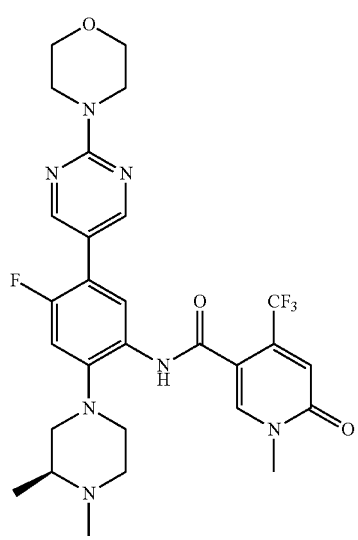 | N-[4-fluoro-5-(2-morpholin-4-ylpyrimidin-5-yl)-2-[rac-(3R)-3,4-dimethylpiperazin-1-yl]phenyl]-1-methyl-6-oxo-4-(trifluoromethyl)pyridine-3-carboxamide | 0.00636 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 129 | 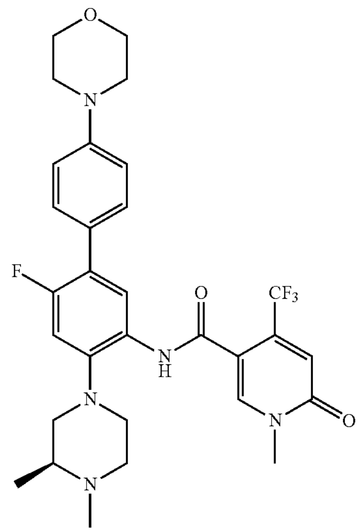 | N-[4-fluoro-5-(4-morpholin-4-ylphenyl)-2-[rac-(3R)-3,4-dimethylpiperazin-1-yl]phenyl]-1-methyl-6-oxo-4-(trifluoromethyl)pyridine-3-carboxamide | 0.0129 |
| 130 | 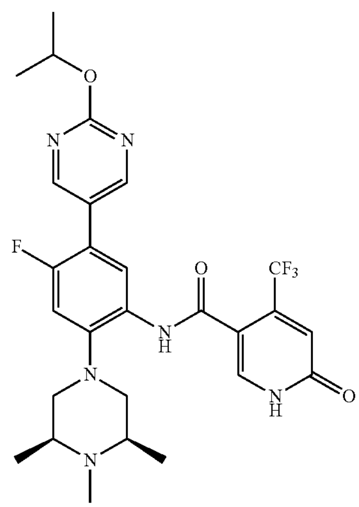 [SMILES: CC(C)Oc1ncc(-c2cc(NC(=O)c3c[nH]c(=O)cc3C(F)(F)F)c(N3C[C@@H](C)N(C)[C@@H](C)C3)cc2F)cn1] | N-[4-fluoro-5-(2-propan-2-yloxypyrimidin-5-yl)-2-[rac-(3R,5S)-3,4,5-trimethylpiperazin-1-yl]phenyl]-6-oxo-4-(trifluoromethyl)-1H-pyridine-3-carboxamide | 0.000656 |
| 131 | 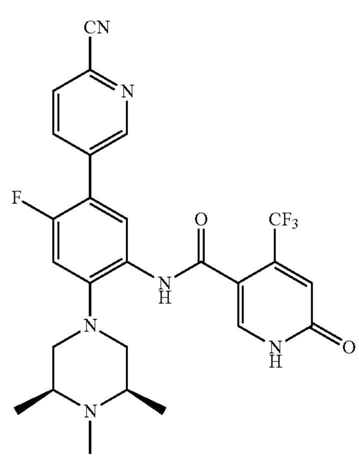 | N-[5-(6-cyanopyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00243 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 132 | 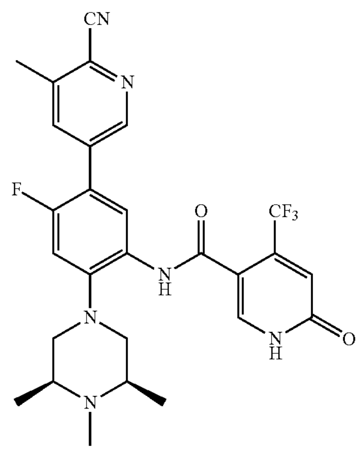 [SMILES: Cc1cc(-c2cc(NC(=O)c3c[nH]c(=O)cc3C(F)(F)F)c(N3C[C@@H](C)N(C)[C@@H](C)C3)cc2F)cnc1C#N] | N-[5-(6-cyano-5-methylpyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.0014 |
| 133 | 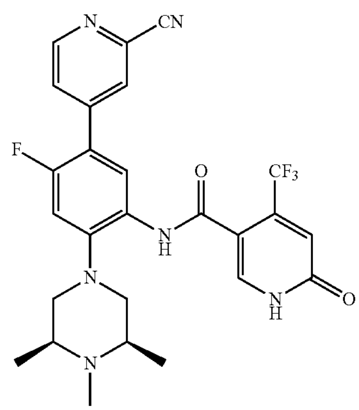 [SMILES: C[C@@H]1CN(c2cc(F)c(-c3ccnc(C#N)c3)cc2NC(=O)c2c[nH]c(=O)cc2C(F)(F)F)C[C@H](C)N1C] | N-[5-(2-cyanopyridin-4-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00133 |
| 134 | 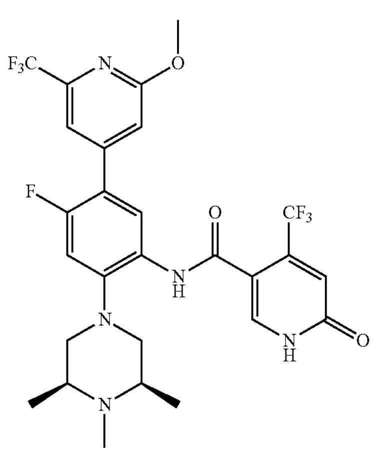 [SMILES: COc1cc(-c2cc(NC(=O)c3c[nH]c(=O)cc3C(F)(F)F)c(N3C[C@@H](C)N(C)[C@@H](C)C3)cc2F)cc(C(F)(F)F)n1] | N-[4-fluoro-5-[2-methoxy-6-(trifluoromethyl)pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00101 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 135 | 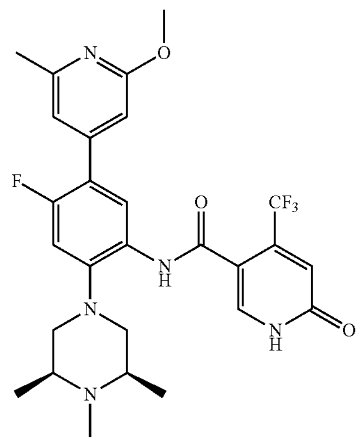 [SMILES: COc1cc(-c2cc(NC(=O)c3c[nH]c(=O)cc3C(F)(F)F)c(N3C[C@@H](C)N(C)[C@@H](C)C3)cc2F)cc(C)n1] | N-[4-fluoro-5-(2-methoxy-6-methylpyridin-4-yl)-2-[rac-(3R,5S)-3,4,5-trimethylpiperazin-1-yl]phenyl]-6-oxo-4-(trifluoromethyl)-1H-pyridine-3-carboxamide | 0.00281 |
| 136 | 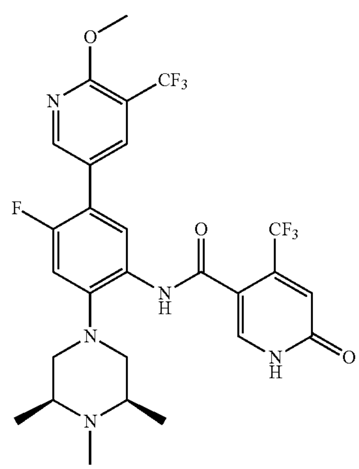 [SMILES: COc1ncc(-c2cc(NC(=O)c3c[nH]c(=O)cc3C(F)(F)F)c(N3C[C@@H](C)N(C)[C@@H](C)C3)cc2F)cc1C(F)(F)F] | N-[4-fluoro-5-[6-methoxy-5-(trifluoromethyl)pyridin-3-yl]-2-[rac-(3R,5S)-3,4,5-trimethylpiperazin-1-yl]phenyl]-6-oxo-4-(trifluoromethyl)-1H-pyridine-3-carboxamide | 0.000463 |
| 137 | 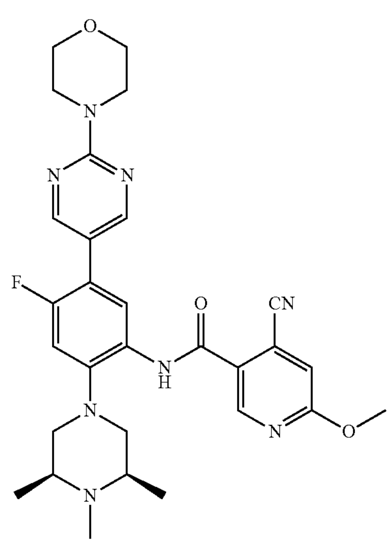 [SMILES: COc1cc(C#N)c(C(=O)Nc2cc(-c3cnc(N4CCOCC4)nc3)c(F)cc2N2C[C@@H](C)N(C)[C@@H](C)C2)cn1] | 4-cyano-N-[4-fluoro-5-(2-morpholin-4-ylpyrimidin-5-yl)-2-[rac-(3R,5S)-3,4,5-trimethylpiperazin-1-yl]phenyl]-6-methoxypyridine-3-carboxamide | 0.0197 |

TABLE 1-continued
Binding affinities (K$_D$) derived from surface plasmon resonance (SPR) assays
| Example No. | Structure | IUPAC Name | WDR5 binding affinity (K$_D$, μM) |
|---|---|---|---|
| 138 | 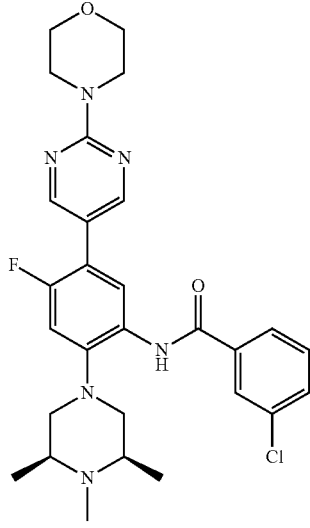 | 3-chloro-N-[4-fluoro-5-(2-morpholin-4-ylpyrimidin-5-yl)-2-[rac-(3R,5S)-3,4,5-trimethylpiperazin-1-yl]phenyl]benzamide | 0.0113 |
| 139 | 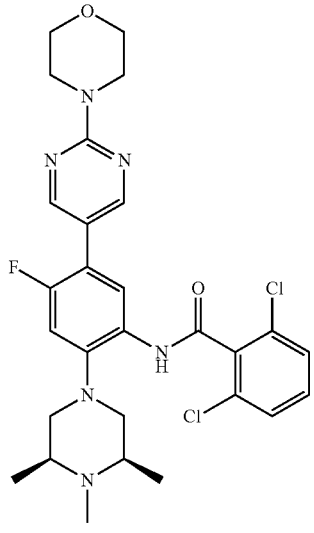 | 2,6-dichloro-N-[4-fluoro-5-(2-morpholin-4-ylpyrimidin-5-yl)-2-[rac-(3R,5S)-3,4,5-trimethylpiperazin-1-yl]phenyl]benzamide | 0.00586 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 140 | 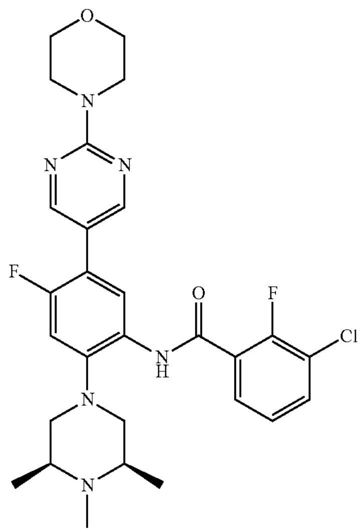 | 3-chloro-2-fluoro-N-[4-fluoro-5-(2-morpholin-4-ylpyrimidin-5-yl)-2-[rac-(3R,5S)-3,4,5-trimethylpiperazin-1-yl]phenyl]benzamide | 0.0188 |
| 141 | 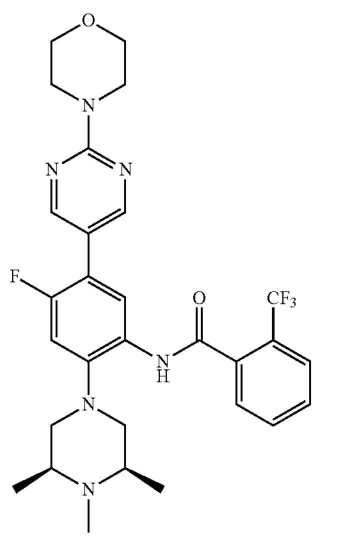 | N-[4-fluoro-5-(2-morpholin-4-ylpyrimidin-5-yl)-2-[rac-(3R,5S)-3,4,5-trimethylpiperazin-1-yl]phenyl]-2-(trifluoromethyl)benzamide | 0.0162 |
| 142 | 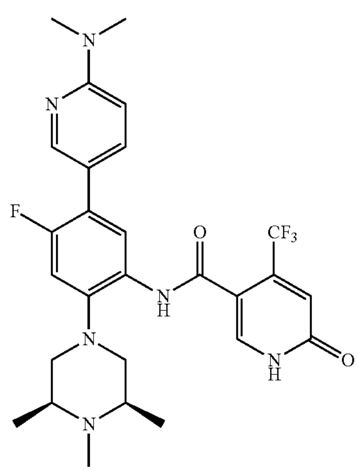 [SMILES: C[C@@H]1CN(c2cc(F)c(-c3ccc(N(C)C)nc3)cc2NC(=O)c2c[nH]c(=O)cc2C(F)(F)F)C[C@H](C)N1C] | N-[5-[6-(dimethylamino)pyridin-3-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.000985 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 143 | 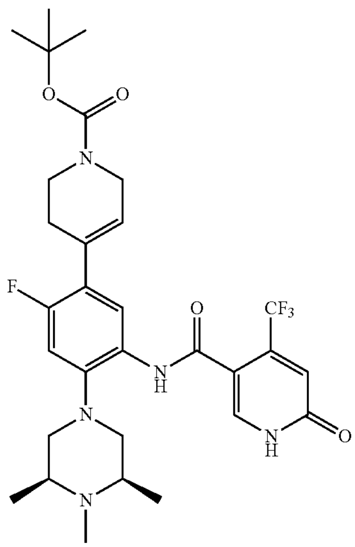 [SMILES: C[C@@H]1CN(c2cc(F)c(C3=CCN(C(=O)OC(C)(C)C)CC3)cc2NC(=O)c2c[nH]c(=O)cc2C(F)(F)F)C[C@H](C)N1C] | tert-butyl 4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.00124 |
| 144 | 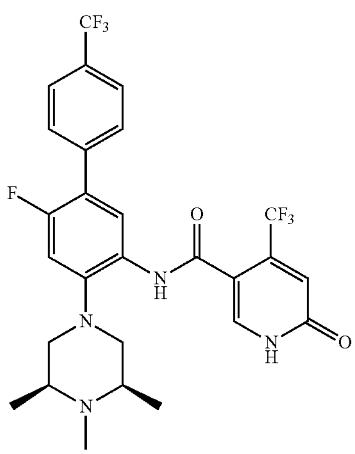 | N-[4-fluoro-2-[rac-(3R,5S)-3,4,5-trimethylpiperazin-1-yl]-5-[4-(trifluoromethyl)phenyl]phenyl]-6-oxo-4-(trifluoromethyl)-1H-pyridine-3-carboxamide | 0.00606 |
| 145 | 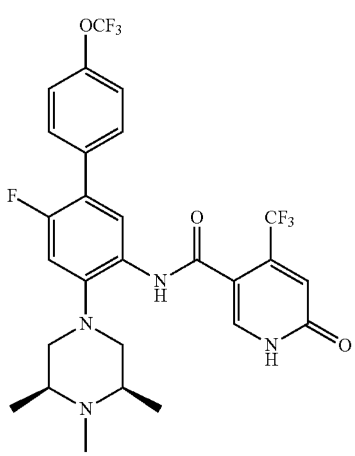 | N-[4-fluoro-2-[rac-(3R,5S)-3,4,5-trimethylpiperazin-1-yl]-5-[4-(trifluoromethoxy)phenyl]phenyl]-6-oxo-4-(trifluoromethyl)-1H-pyridine-3-carboxamide | 0.00683 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 146 | 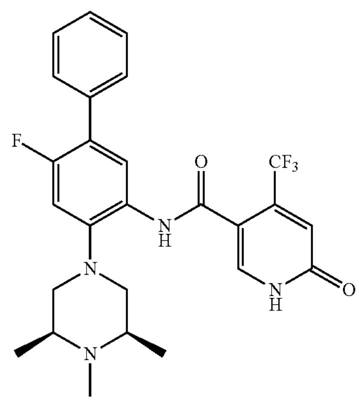 | N-[4-fluoro-5-phenyl-2-[rac-(3R,5S)-3,4,5-trimethylpiperazin-1-yl]phenyl]-6-oxo-4-(trifluoromethyl)-1H-pyridine-3-carboxamide | 0.00602 |
| 147 | 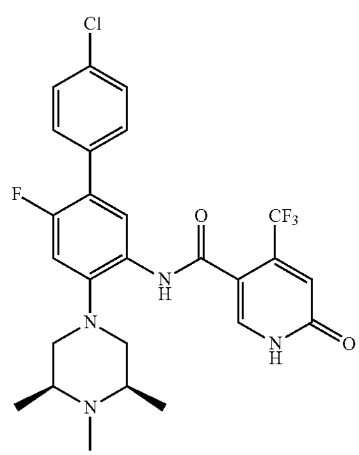 | N-[5-(4-chlorophenyl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00444 |
| 148 | 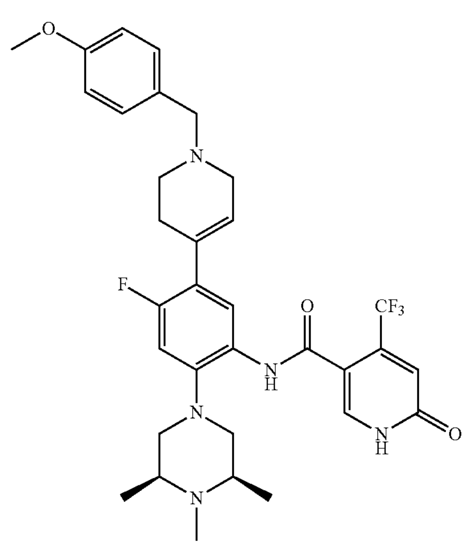 [SMILES: COc1ccc(CN2CC=C(c3cc(NC(=O)c4c[nH]c(=O)cc4C(F)(F)F)c(N4C[C@@H](C)N(C)[C@@H](C)C4)cc3F)CC2)cc1] | N-[4-fluoro-5-[1-[(4-methoxyphenyl)methyl]-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00054 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 149 | 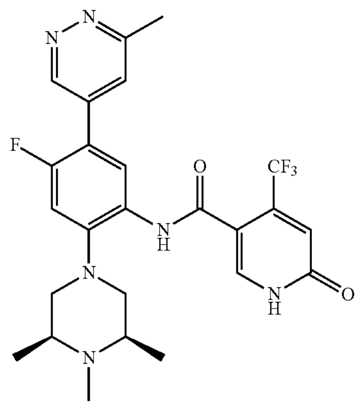 | N-[4-fluoro-5-(6-methylpyridazin-4-yl)-2-[rac-(3R,5S)-3,4,5-trimethylpiperazin-1-yl]phenyl]-6-oxo-4-(trifluoromethyl)-1H-pyridine-3-carboxamide | 0.00465 |
| 150 | 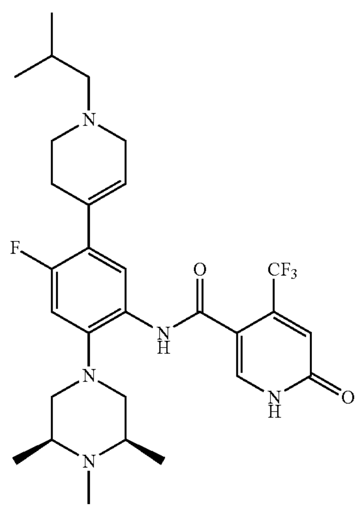 [SMILES: CC(C)CN1CC=C(c2cc(NC(=O)c3c[nH]c(=O)cc3C(F)(F)F)c(N3C[C@@H](C)N(C)[C@@H](C)C3)cc2F)CC1] | N-[4-fluoro-5-[1-(2-methylpropyl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.009 |
| 151 | 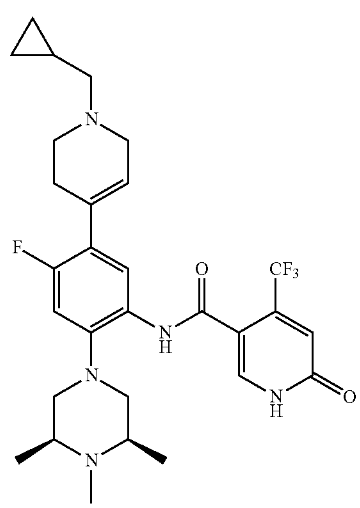 [SMILES: C[C@@H]1CN(c2cc(F)c(C3=CCN(CC4CC4)CC3)cc2NC(=O)c2c[nH]c(=O)cc2C(F)(F)F)C[C@H](C)N1C] | N-[5-[1-(cyclopropylmethyl)-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00746 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 152 | 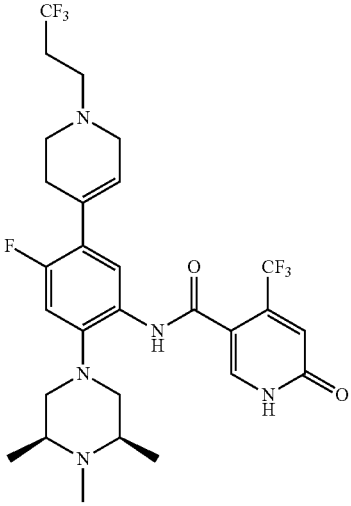 [SMILES: C[C@@H]1CN(c2cc(F)c(C3=CCN(CCC(F)(F)F)CC3)cc2NC(=O)c2c[nH]c(=O)cc2C(F)(F)F)C[C@H](C)N1C] | N-[4-fluoro-2-[rac-(3R,5S)-3,4,5-trimethylpiperazin-1-yl]-5-[1-(3,3,3-trifluoropropyl)-3,6-dihydro-2H-pyridin-4-yl]phenyl]-6-oxo-4-(trifluoromethyl)-1H-pyridine-3-carboxamide | 0.00633 |
| 153 | 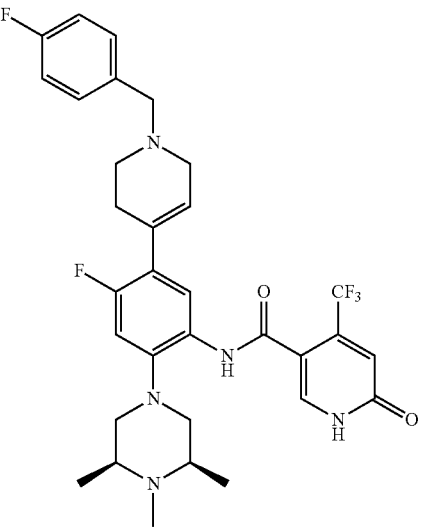 [SMILES: C[C@@H]1CN(c2cc(F)c(C3=CCN(Cc4ccc(F)cc4)CC3)cc2NC(=O)c2c[nH]c(=O)cc2C(F)(F)F)C[C@H](C)N1C] | N-[4-fluoro-5-[1-[(4-fluorophenyl)methyl]-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00108 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 154 | 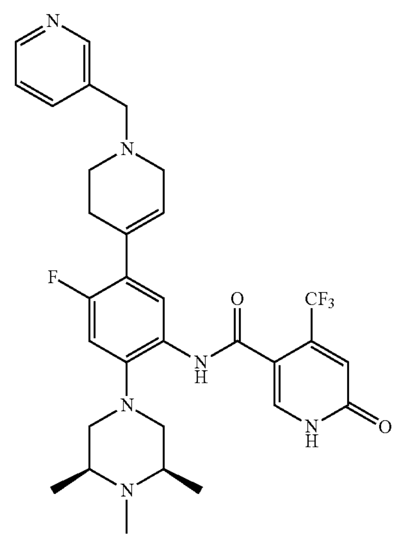 [SMILES: C[C@@H]1CN(c2cc(F)c(C3=CCN(Cc4cccnc4)CC3)cc2NC(=O)c2c[nH]c(=O)cc2C(F)(F)F)C[C@H](C)N1C] | N-[4-fluoro-5-[1-(pyridin-3-ylmethyl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00546 |
| 155 | 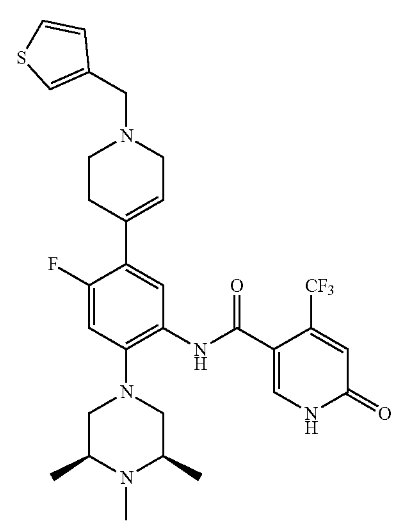 [SMILES: C[C@@H]1CN(c2cc(F)c(C3=CCN(Cc4ccsc4)CC3)cc2NC(=O)c2c[nH]c(=O)cc2C(F)(F)F)C[C@H](C)N1C] | N-[4-fluoro-2-[rac-(3R,5S)-3,4,5-trimethylpiperazin-1-yl]-5-[1-(thiophen-3-ylmethyl)-3,6-dihydro-2H-pyridin-4-yl]phenyl]-6-oxo-4-(trifluoromethyl)-1H-pyridine-3-carboxamide | 0.00476 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 156 | 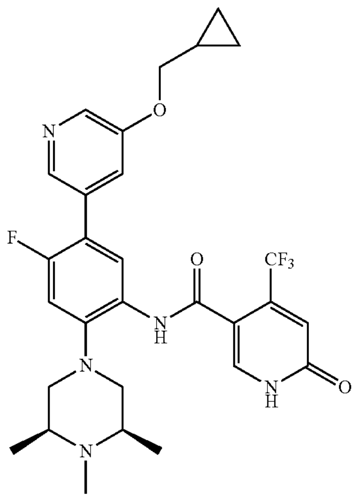 | N-[5-[5-(cyclopropylmethoxy)pyridin-3-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00861 |
| 157 | 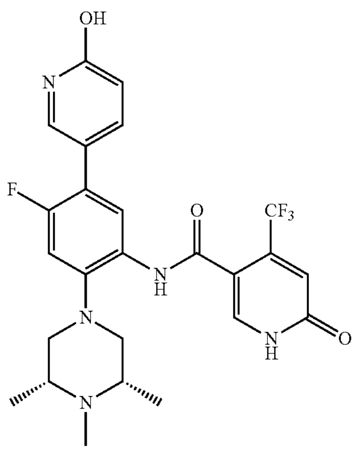 [SMILES: C[C@@H]1CN(c2cc(F)c(-c3ccc(O)nc3)cc2NC(=O)c2c[nH]c(=O)cc2C(F)(F)F)C[C@H](C)N1C] | N-[4-fluoro-5-(6-hydroxypyridin-3-yl)-2-[rac-(3R,5S)-3,4,5-trimethylpiperazin-1-yl]phenyl]-6-oxo-4-(trifluoromethyl)-1H-pyridine-3-carboxamide | 0.00216 |
| 158 | 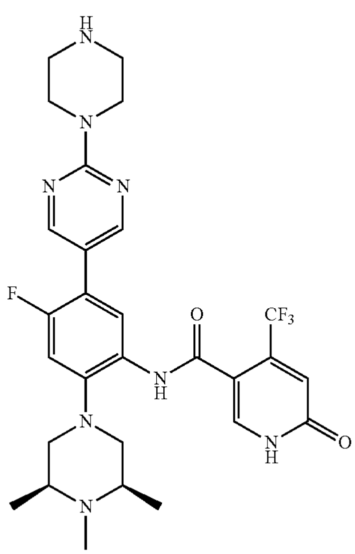 [SMILES: C[C@@H]1CN(c2cc(F)c(-c3cnc(N4CCNCC4)nc3)cc2NC(=O)c2c[nH]c(=O)cc2C(F)(F)F)C[C@H](C)N1C] | N-[4-fluoro-5-(2-piperazin-1-ylpyrimidin-5-yl)-2-[rac-(3R,5S)-3,4,5-trimethylpiperazin-1-yl]phenyl]-6-oxo-4-(trifluoromethyl)-1H-pyridine-3-carboxamide | 0.000345 |

TABLE 1-continued
Binding affinities (K$_D$) derived from surface plasmon resonance (SPR) assays
| Example No. | Structure | IUPAC Name | WDR5 binding affinity (K$_D$, µM) |
|---|---|---|---|
| 159 | 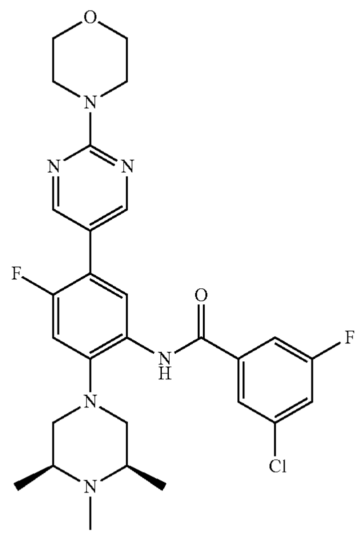 [SMILES: C[C@@H]1CN(c2cc(F)c(-c3cnc(N4CCOCC4)nc3)cc2NC(=O)c2cc(F)cc(Cl)c2)C[C@H](C)N1C] | 3-chloro-5-fluoro-N-[4-fluoro-5-(2-morpholin-4-ylpyrimidin-5-yl)-2-[rac-(3R,5S)-3,4,5-trimethylpiperazin-1-yl]phenyl]benzamide | 0.029 |
| 160 | 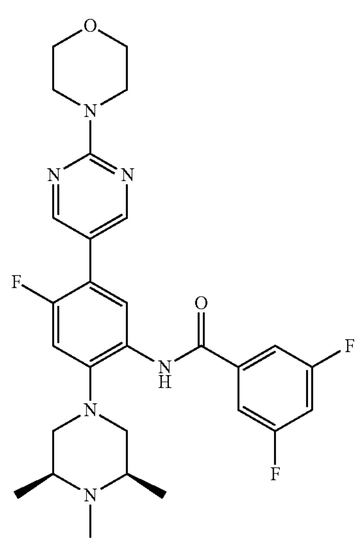 [SMILES: C[C@@H]1CN(c2cc(F)c(-c3cnc(N4CCOCC4)nc3)cc2NC(=O)c2cc(F)cc(F)c2)C[C@H](C)N1C] | 3,5-difluoro-N-[4-fluoro-5-(2-morpholin-4-ylpyrimidin-5-yl)-2-[rac-(3R,5S)-3,4,5-trimethylpiperazin-1-yl]phenyl]benzamide | 0.0268 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 161 | 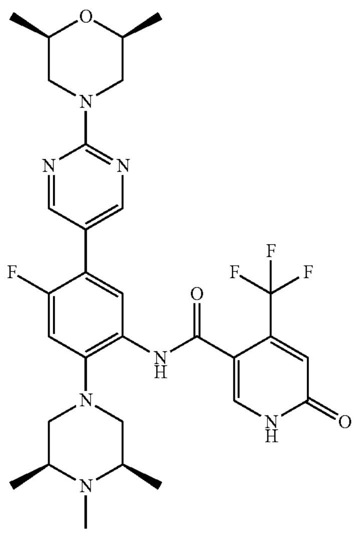 [SMILES: C[C@@H]1CN(c2ncc(-c3cc(NC(=O)c4c[nH]c(=O)cc4C(F)(F)F)c(N4C[C@@H](C)N(C)[C@@H](C)C4)cc3F)cn2)C[C@H](C)O1] | N-[4-fluoro-5-[2-[rac-(2R,6S)-2,6-dimethylmorpholin-4-yl]pyrimidin-5-yl]-2-[rac-(3S,5R)-3,4,5-trimethylpiperazin-1-yl]phenyl]-6-oxo-4-(trifluoromethyl)-1H-pyridine-3-carboxamide | 0.001 |
| 162 | 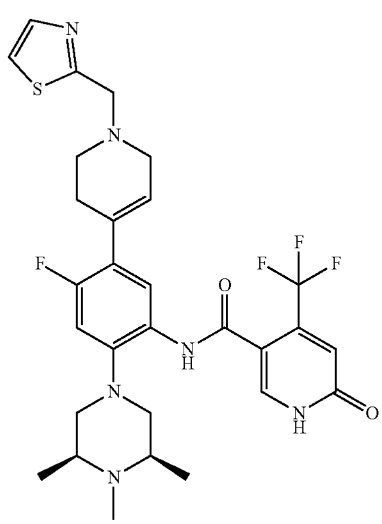 [SMILES: C[C@@H]1CN(c2cc(F)c(C3=CCN(Cc4nccs4)CC3)cc2NC(=O)c2c[nH]c(=O)cc2C(F)(F)F)C[C@H](C)N1C] | N-[4-fluoro-2-[rac-(3R,5S)-3,4,5-trimethylpiperazin-1-yl]-5-[1-(1,3-thiazol-2-ylmethyl)-3,6-dihydro-2H-pyridin-4-yl]phenyl]-6-oxo-4-(trifluoromethyl)-1H-pyridine-3-carboxamide | 0.00283 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 163 | 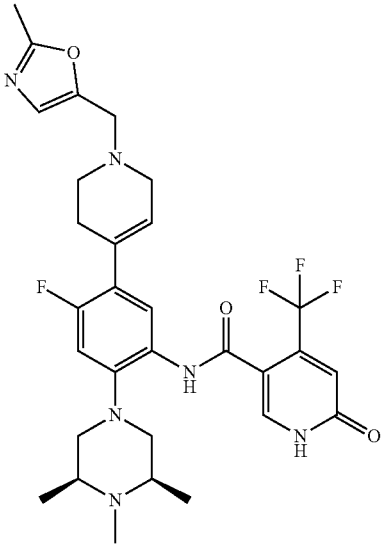 [SMILES: Cc1ncc(CN2CC=C(c3cc(NC(=O)c4c[nH]c(=O)cc4C(F)(F)F)c(N4C[C@@H](C)N(C)[C@@H](C)C4)cc3F)CC2)o1] | N-[4-fluoro-5-[1-[(2-methyl-1,3-oxazol-5-yl)methyl]-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00405 |
| 164 | 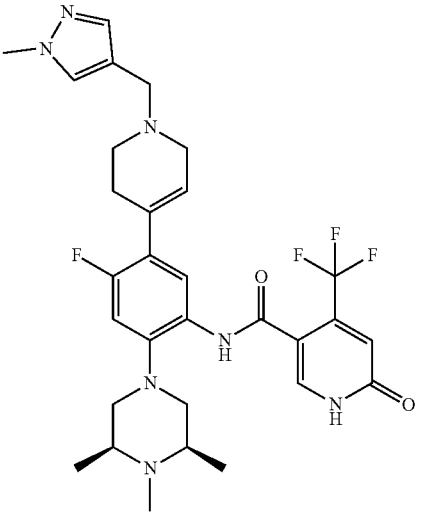 [SMILES: C[C@@H]1CN(c2cc(F)c(C3=CCN(Cc4cnn(C)c4)CC3)cc2NC(=O)c2c[nH]c(=O)cc2C(F)(F)F)C[C@H](C)N1C] | N-[4-fluoro-5-[1-[(1-methylpyrazol-4-yl)methyl]-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00143 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 165 | 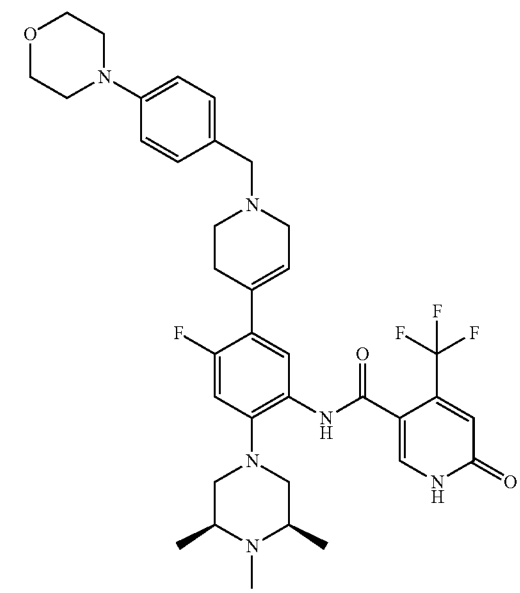 [SMILES: C[C@@H]1CN(c2cc(F)c(C3=CCN(Cc4ccc(N5CCOCC5)cc4)CC3)cc2NC(=O)c2c[nH]c(=O)cc2C(F)(F)F)C[C@H](C)N1C] | N-[4-fluoro-5-[1-[(4-morpholin-4-ylphenyl)methyl]-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00628 |
| 166 | 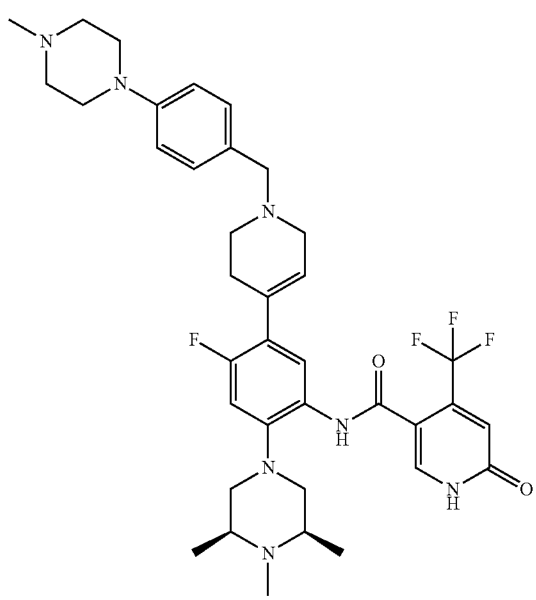 [SMILES: C[C@@H]1CN(c2cc(F)c(C3=CCN(Cc4ccc(N5CCN(C)CC5)cc4)CC3)cc2NC(=O)c2c[nH]c(=O)cc2C(F)(F)F)C[C@H](C)N1C] | N-[4-fluoro-5-[1-[[4-(4-methylpiperazin-1-yl)phenyl]methyl]-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00023 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 167 | 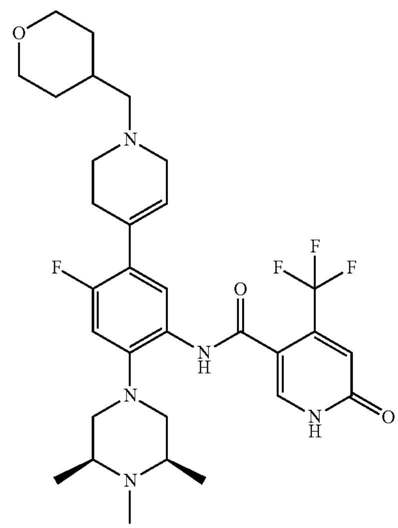 [SMILES: C[C@@H]1CN(c2cc(F)c(C3=CCN(CC4CCOCC4)CC3)cc2NC(=O)c2c[nH]c(=O)cc2C(F)(F)F)C[C@H](C)N1C] | N-[4-fluoro-5-[1-(oxan-4-ylmethyl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00576 |
| 168 | 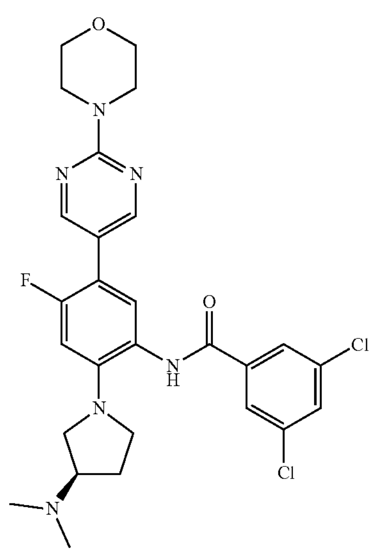 [SMILES: CN(C)[C@@H]1CCN(c2cc(F)c(-c3cnc(N4CCOCC4)nc3)cc2NC(=O)c2cc(Cl)cc(Cl)c2)C1] | 3,5-dichloro-N-[4-fluoro-5-(2-morpholin-4-ylpyrimidin-5-yl)-2-[rac-(3R)-3-(dimethylamino)pyrrolidin-1-yl]phenyl]benzamide | 0.03 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 169 | 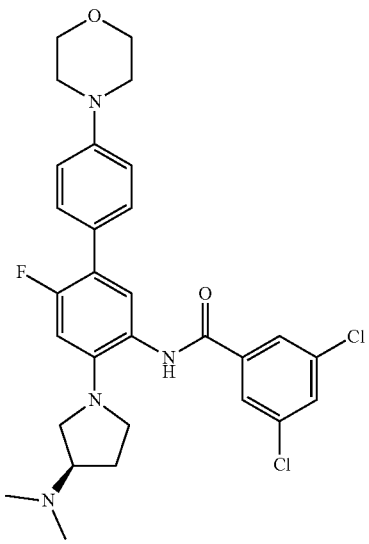 [SMILES: CN(C)[C@@H]1CCN(c2cc(F)c(-c3ccc(N4CCOCC4)cc3)cc2NC(=O)c2cc(Cl)cc(Cl)c2)C1] | 3,5-dichloro-N-[4-fluoro-5-(4-morpholin-4-ylphenyl)-2-[rac-(3R)-3-(dimethylamino)pyrrolidin-1-yl]phenyl]benzamide | 0.122 |
| 170 | 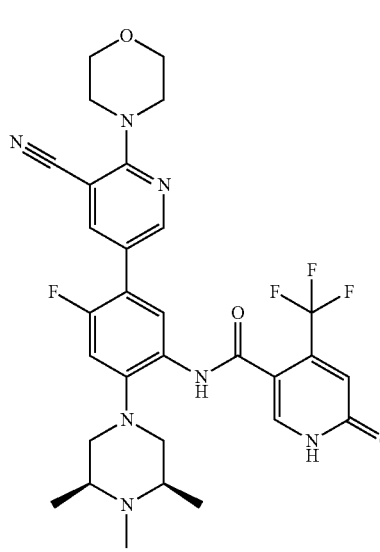 | N-[5-(5-cyano-6-morpholin-4-ylpyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00117 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 171 | 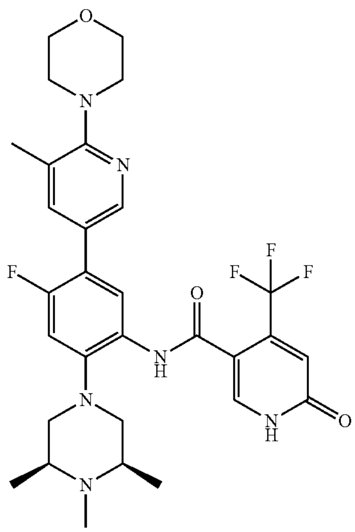 | N-[4-fluoro-5-(5-methyl-6-morpholin-4-ylpyridin-3-yl)-2-[rac-(3R,5S)-3,4,5-trimethylpiperazin-1-yl]phenyl]-6-oxo-4-(trifluoromethyl)-1H-pyridine-3-carboxamide | 0.0025 |
| 172 | 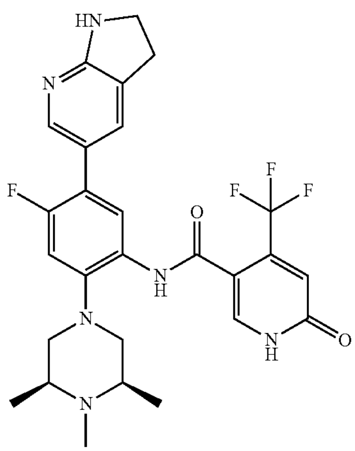 [SMILES: C[C@@H]1CN(c2cc(F)c(-c3cnc4c(c3)CCN4)cc2NC(=O)c2c[nH]c(=O)cc2C(F)(F)F)C[C@H](C)N1C] | N-[5-(2,3-dihydro-1H-pyrrolo[2,3-b]pyridin-5-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.0103 |
| 173 | 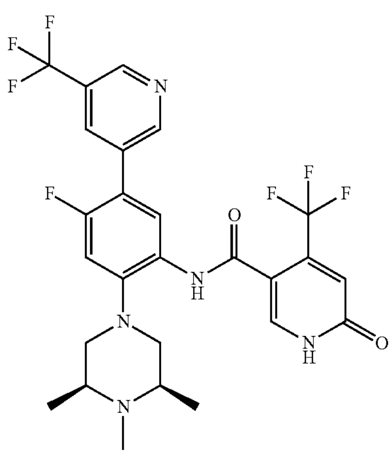 [SMILES: C[C@@H]1CN(c2cc(F)c(-c3cncc(C(F)(F)F)c3)cc2NC(=O)c2c[nH]c(=O)cc2C(F)(F)F)C[C@H](C)N1C] | N-[4-fluoro-2-[rac-(3R,5S)-3,4,5-trimethylpiperazin-1-yl]-5-[5-(trifluoromethyl)pyridin-3-yl]phenyl]-6-oxo-4-(trifluoromethyl)-1H-pyridine-3-carboxamide | 0.00278 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 174 | 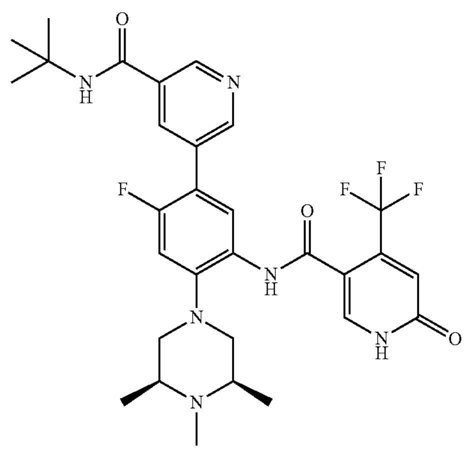 [SMILES: C[C@@H]1CN(c2cc(F)c(-c3cncc(C(=O)NC(C)(C)C)c3)cc2NC(=O)c2c[nH]c(=O)cc2C(F)(F)F)C[C@H](C)N1C] | N-[5-[5-(tert-butylcarbamoyl)pyridin-3-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00153 |
| 175 | 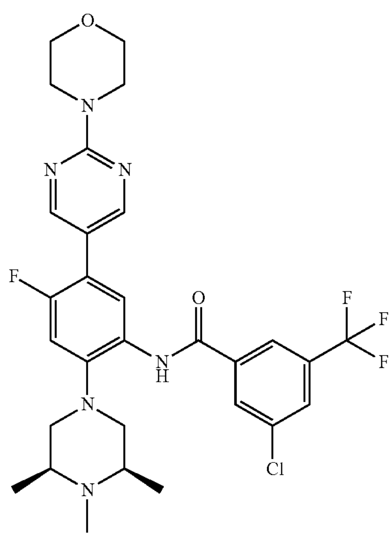 | 3-chloro-N-[4-fluoro-5-(2-morpholin-4-ylpyrimidin-5-yl)-2-[rac-(3R,5S)-3,4,5-trimethylpiperazin-1-yl]phenyl]-5-(trifluoromethyl)benzamide | 0.0206 |
| 176 | 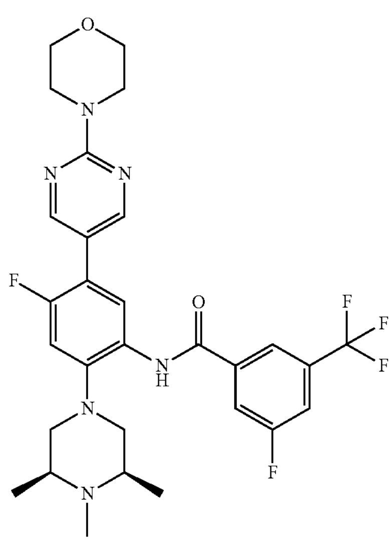 [SMILES: C[C@@H]1CN(c2cc(F)c(-c3cnc(N4CCOCC4)nc3)cc2NC(=O)c2cc(F)cc(C(F)(F)F)c2)C[C@H](C)N1C] | 3-fluoro-N-[4-fluoro-5-(2-morpholin-4-ylpyrimidin-5-yl)-2-[rac-(3R,5S)-3,4,5-trimethylpiperazin-1-yl]phenyl]-5-(trifluoromethyl)benzamide | 0.0509 |

TABLE 1-continued

Binding affinities (K_D) derived from surface plasmon resonance (SPR) assays

| Example No. | Structure | IUPAC Name | WDR5 binding affinity (K_D, μM) |
|---|---|---|---|
| 177 | 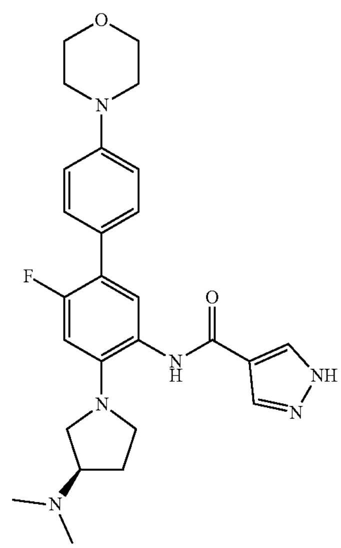 [SMILES: CN(C)[C@@H]1CCN(c2cc(F)c(-c3ccc(N4CCOCC4)cc3)cc2NC(=O)c2cn[nH]c2)C1] | N-[4-fluoro-5-(4-morpholin-4-ylphenyl)-2-[rac-(3R)-3-(dimethylamino)pyrrolidin-1-yl]phenyl]-1H-pyrazole-4-carboxamide | >0.200 |
| 178 | 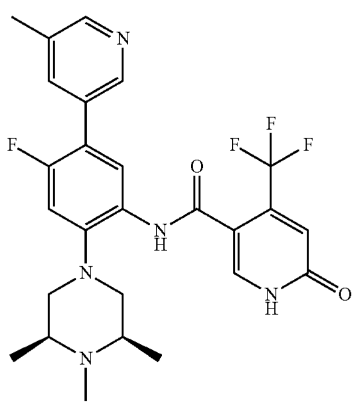 [SMILES: Cc1cncc(-c2cc(NC(=O)c3c[nH]c(=O)cc3C(F)(F)F)c(N3C[C@@H](C)N(C)[C@@H](C)C3)cc2F)c1] | N-[4-fluoro-5-(5-methylpyridin-3-yl)-2-[rac-(3R,5S)-3,4,5-trimethylpiperazin-1-yl]phenyl]-6-oxo-4-(trifluoromethyl)-1H-pyridine-3-carboxamide | 0.0065 |
| 179 | 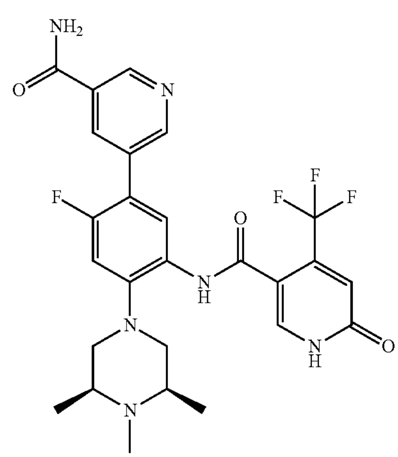 [SMILES: C[C@@H]1CN(c2cc(F)c(-c3cncc(C(N)=O)c3)cc2NC(=O)c2c[nH]c(=O)cc2C(F)(F)F)C[C@H](C)N1C] | N-[5-(5-carbamoylpyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.0115 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 180 | 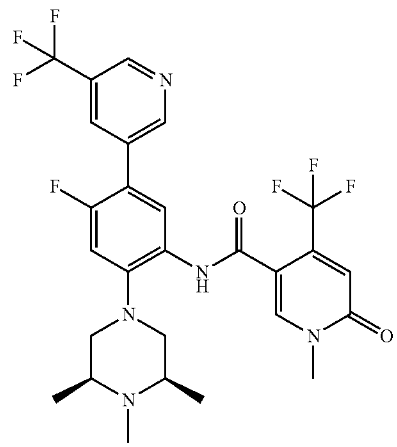 | N-[4-fluoro-2-[rac-(3R,5S)-3,4,5-trimethylpiperazin-1-yl]-5-[5-(trifluoromethyl)pyridin-3-yl]phenyl]-1-methyl-6-oxo-4-(trifluoromethyl)pyridine-3-carboxamide | 0.0354 |
| 181 | 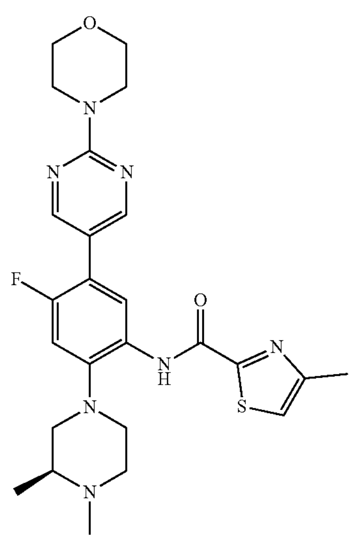 [SMILES: Cc1csc(C(=O)Nc2cc(-c3cnc(N4CCOCC4)nc3)c(F)cc2N2CCN(C)[C@@H](C)C2)n1] | N-[4-fluoro-5-(2-morpholin-4-ylpyrimidin-5-yl)-2-[rac-(3R)-3,4-dimethylpiperazin-1-yl]phenyl]-4-methyl-1,3-thiazole-2-carboxamide | >0.200 |
| 182 | 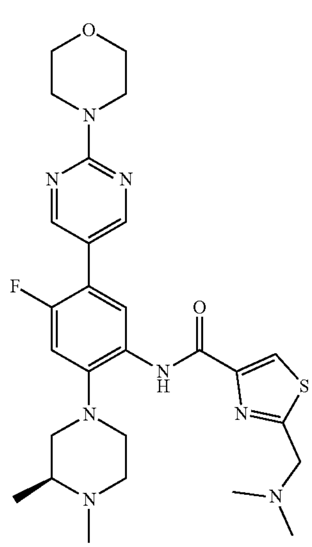 [SMILES: C[C@H]1CN(c2cc(F)c(-c3cnc(N4CCOCC4)nc3)cc2NC(=O)c2csc(CN(C)C)n2)CCN1C] | 2-[(dimethylamino)methyl]-N-[4-fluoro-5-(2-morpholin-4-ylpyrimidin-5-yl)-2-[rac-(3R)-3,4-dimethylpiperazin-1-yl]phenyl]-1,3-thiazole-4-carboxamide | >0.200 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 183 | 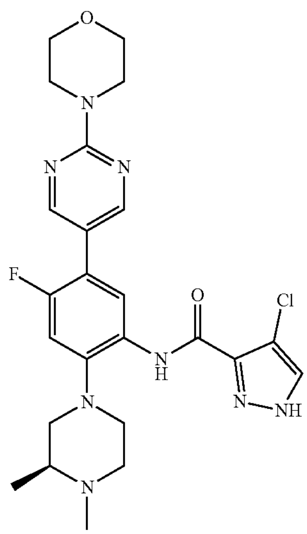 [SMILES: C[C@H]1CN(c2cc(F)c(-c3cnc(N4CCOCC4)nc3)cc2NC(=O)c2n[nH]cc2Cl)CCN1C] | 4-chloro-N-[4-fluoro-5-(2-morpholin-4-ylpyrimidin-5-yl)-2-[rac-(3R)-3,4-dimethylpiperazin-1-yl]phenyl]-1H-pyrazole-3-carboxamide | 0.113 |
| 184 | 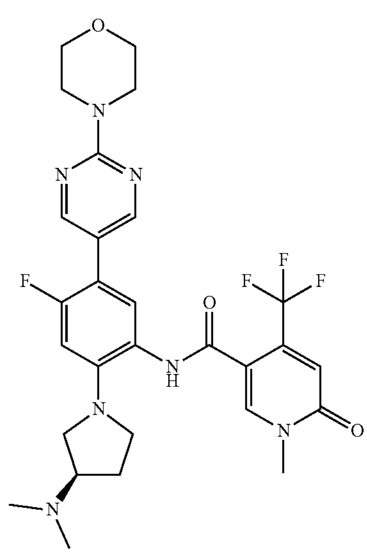 | N-[4-fluoro-5-(2-morpholin-4-ylpyrimidin-5-yl)-2-[rac-(3R)-3-(dimethylamino)pyrrolidin-1-yl]phenyl]-1-methyl-6-oxo-4-(trifluoromethyl)pyridine-3-carboxamide | 0.0098 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 185 | 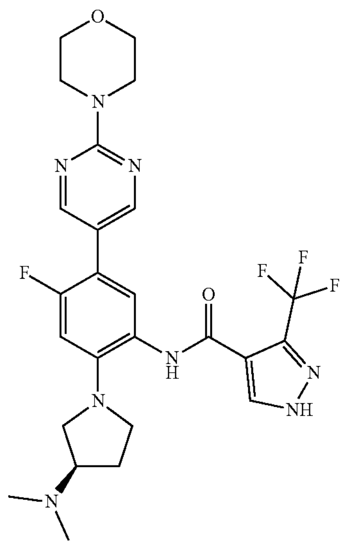 | N-[4-fluoro-5-(2-morpholin-4-ylpyrimidin-5-yl)-2-[rac-(3R)-3-(dimethylamino)pyrrolidin-1-yl]phenyl]-3-(trifluoromethyl)-1H-pyrazole-4-carboxamide | 0.0298 |
| 186 | 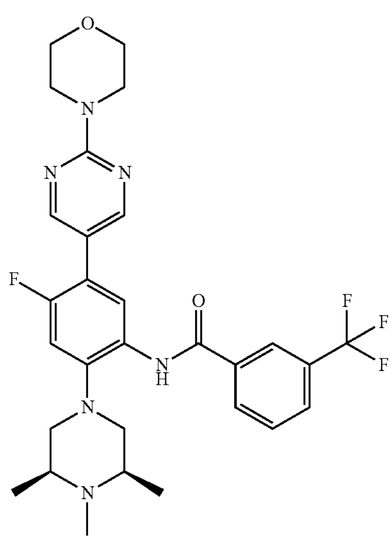 [SMILES: C[C@@H]1CN(c2cc(F)c(-c3cnc(N4CCOCC4)nc3)cc2NC(=O)c2cccc(C(F)(F)F)c2)C[C@H](C)N1C] | N-[4-fluoro-5-(2-morpholin-4-ylpyrimidin-5-yl)-2-[rac-(3R,5S)-3,4,5-trimethylpiperazin-1-yl]phenyl]-3-(trifluoromethyl)benzamide | 0.0402 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 187 | 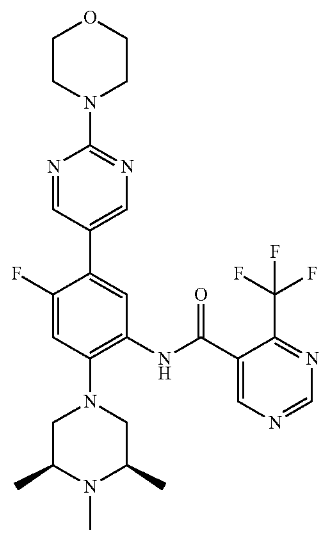 [SMILES: C[C@@H]1CN(c2cc(F)c(-c3cnc(N4CCOCC4)nc3)cc2NC(=O)c2cncnc2C(F)(F)F)C[C@H](C)N1C] | N-[4-fluoro-5-(2-morpholin-4-ylpyrimidin-5-yl)-2-[rac-(3R,5S)-3,4,5-trimethylpiperazin-1-yl]phenyl]-4-(trifluoromethyl)pyrimidine-5-carboxamide | 0.209 |
| 188 | 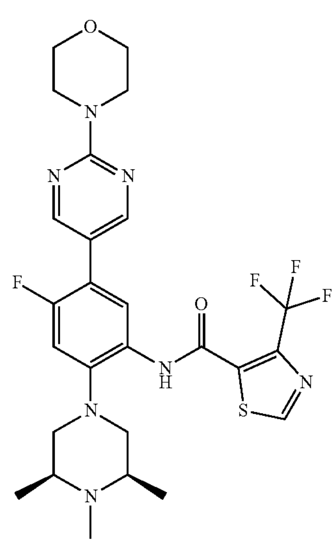 [SMILES: C[C@@H]1CN(c2cc(F)c(-c3cnc(N4CCOCC4)nc3)cc2NC(=O)c2scnc2C(F)(F)F)C[C@H](C)N1C] | N-[4-fluoro-5-(2-morpholin-4-ylpyrimidin-5-yl)-2-[rac-(3R,5S)-3,4,5-trimethylpiperazin-1-yl]phenyl]-4-(trifluoromethyl)-1,3-thiazole-5-carboxamide | 0.0932 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 189 | 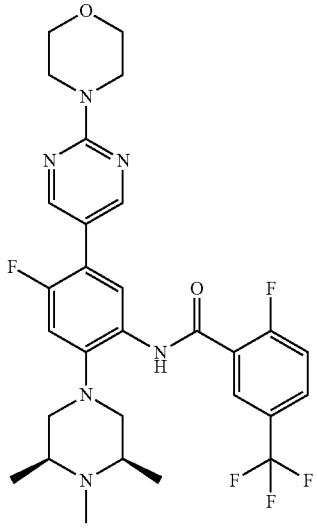 [SMILES: C[C@@H]1CN(c2cc(F)c(-c3cnc(N4CCOCC4)nc3)cc2NC(=O)c2cc(C(F)(F)F)ccc2F)C[C@H](C)N1C] | 2-fluoro-N-[4-fluoro-5-(2-morpholin-4-ylpyrimidin-5-yl)-2-[rac-(3R,5S)-3,4,5-trimethylpiperazin-1-yl]phenyl]-5-(trifluoromethyl)benzamide | 0.442 |
| 190 | 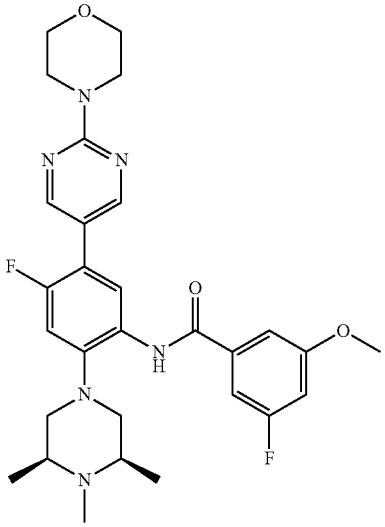 | 3-fluoro-N-[4-fluoro-5-(2-morpholin-4-ylpyrimidin-5-yl)-2-[rac-(3R,5S)-3,4,5-trimethylpiperazin-1-yl]phenyl]-5-methoxybenzamide | 0.0147 |

TABLE 1-continued
Binding affinities (K$_D$) derived from surface plasmon resonance (SPR) assays
| Example No. | Structure | IUPAC Name | WDR5 binding affinity (K$_D$, μM) |
|---|---|---|---|
| 191 | 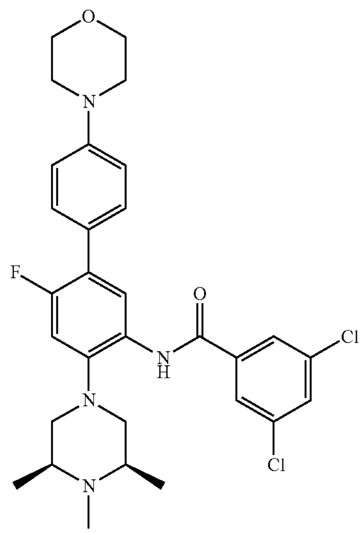 [SMILES: C[C@@H]1CN(c2cc(F)c(-c3ccc(N4CCOCC4)cc3)cc2NC(=O)c2cc(Cl)cc(Cl)c2)C[C@H](C)N1C] | 3,5-dichloro-N-[4-fluoro-5-(4-morpholin-4-ylphenyl)-2-[rac-(3R,5S)-3,4,5-trimethylpiperazin-1-yl]phenyl]benzamide | 0.0215 |
| 192 | 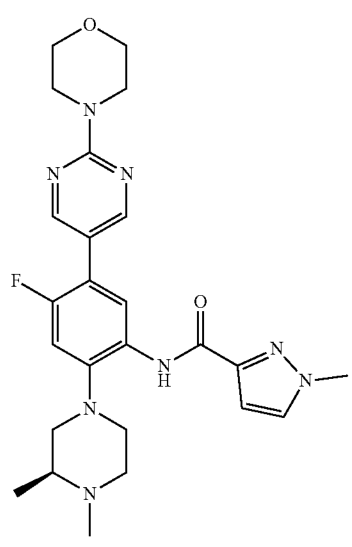 [SMILES: C[C@H]1CN(c2cc(F)c(-c3cnc(N4CCOCC4)nc3)cc2NC(=O)c2ccn(C)n2)CCN1C] | N-[4-fluoro-5-(2-morpholin-4-ylpyrimidin-5-yl)-2-[rac-(3R)-3,4-dimethylpiperazin-1-yl]phenyl]-1-methylpyrazole-3-carboxamide | 1.26 |

TABLE 1-continued
Binding affinities (K$_D$) derived from surface plasmon resonance (SPR) assays
| Example No. | Structure | IUPAC Name | WDR5 binding affinity (K$_D$, μM) |
|---|---|---|---|
| 193 | 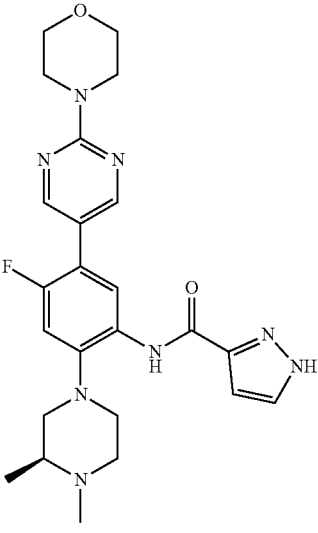 [SMILES: C[C@H]1CN(c2cc(F)c(-c3cnc(N4CCOCC4)nc3)cc2NC(=O)c2cc[nH]n2)CCN1C] | N-[4-fluoro-5-(2-morpholin-4-ylpyrimidin-5-yl)-2-[rac-(3R)-3,4-dimethylpiperazin-1-yl]phenyl]-1H-pyrazole-3-carboxamide | 0.592 |
| 194 | 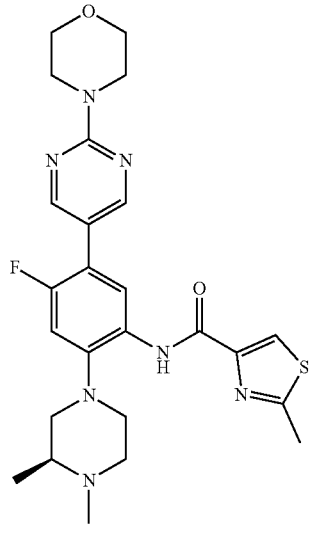 [SMILES: Cc1nc(C(=O)Nc2cc(-c3cnc(N4CCOCC4)nc3)c(F)cc2N2CCN(C)[C@@H](C)C2)cs1] | N-[4-fluoro-5-(2-morpholin-4-ylpyrimidin-5-yl)-2-[rac-(3R)-3,4-dimethylpiperazin-1-yl]phenyl]-2-methyl-1,3-thiazole-4-carboxamide | 0.113 |

TABLE 1-continued

Binding affinities (K_D) derived from surface plasmon resonance (SPR) assays

| Example No. | Structure | IUPAC Name | WDR5 binding affinity ($K_D$, µM) |
|---|---|---|---|
| 195 | 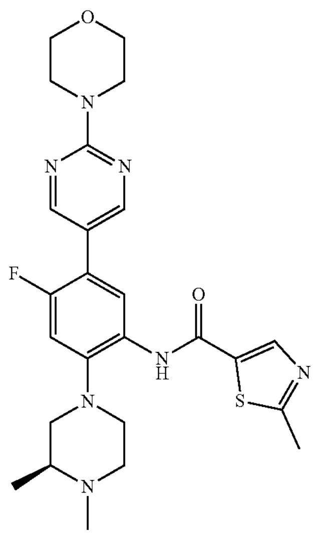 [SMILES: Cc1ncc(C(=O)Nc2cc(-c3cnc(N4CCOCC4)nc3)c(F)cc2N2CCN(C)[C@@H](C)C2)s1] | N-[4-fluoro-5-(2-morpholin-4-ylpyrimidin-5-yl)-2-[rac-(3R)-3,4-dimethylpiperazin-1-yl]phenyl]-2-methyl-1,3-thiazole-5-carboxamide | 0.106 |
| 196 | 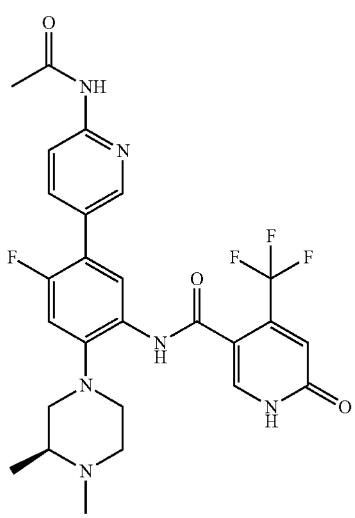 [SMILES: CC(=O)Nc1ccc(-c2cc(NC(=O)c3c[nH]c(=O)cc3C(F)(F)F)c(N3CCN(C)[C@@H](C)C3)cc2F)cn1] | N-[5-(6-acetamidopyridin-3-yl)-4-fluoro-2-[rac-(3R)-3,4-dimethylpiperazin-1-yl]phenyl]-6-oxo-4-(trifluoromethyl)-1H-pyridine-3-carboxamide | 0.00024 |
| 197 | 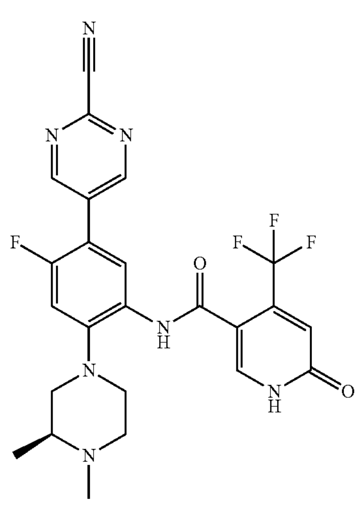 | N-[5-(2-cyanopyrimidin-5-yl)-4-fluoro-2-[rac-(3R)-3,4-dimethylpiperazin-1-yl]phenyl]-6-oxo-4-(trifluoromethyl)-1H-pyridine-3-carboxamide | 0.000681 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 198 | 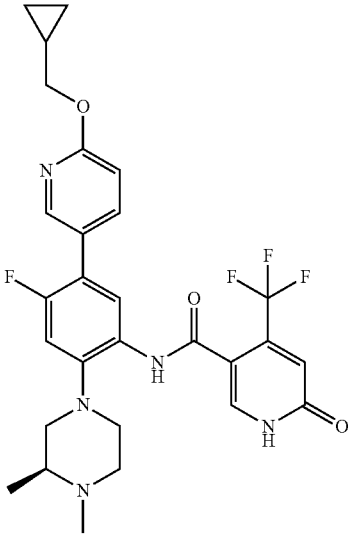 | N-[5-[6-(cyclopropylmethoxy)pyridin-3-yl]-4-fluoro-2-[rac-(3R)-3,4-dimethylpiperazin-1-yl]phenyl]-6-oxo-4-(trifluoromethyl)-1H-pyridine-3-carboxamide | 0.000666 |
| 199 | 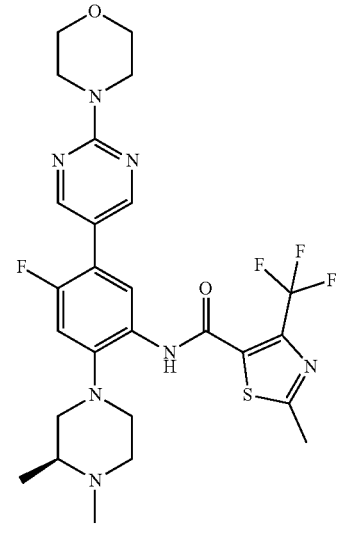 [SMILES: Cc1nc(C(F)(F)F)c(C(=O)Nc2cc(-c3cnc(N4CCOCC4)nc3)c(F)cc2N2CCN(C)[C@@H](C)C2)s1] | N-[4-fluoro-5-(2-morpholin-4-ylpyrimidin-5-yl)-2-[rac-(3R)-3,4-dimethylpiperazin-1-yl]phenyl]-2-methyl-4-(trifluoromethyl)-1,3-thiazole-5-carboxamide | 0.0234 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 200 | 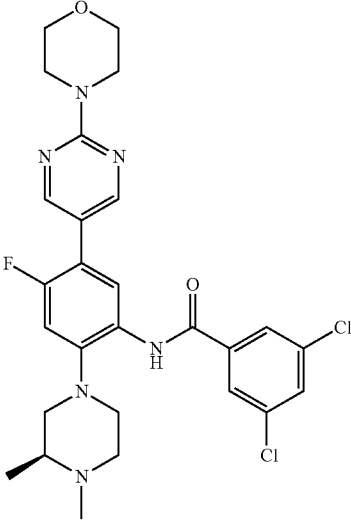 [SMILES: C[C@H]1CN(c2cc(F)c(-c3cnc(N4CCOCC4)nc3)cc2NC(=O)c2cc(Cl)cc(Cl)c2)CCN1C] | 3,5-dichloro-N-[4-fluoro-5-(2-morpholin-4-ylpyrimidin-5-yl)-2-[rac-(3R)-3,4-dimethylpiperazin-1-yl]phenyl]benzamide | 0.0097 |
| 201 | 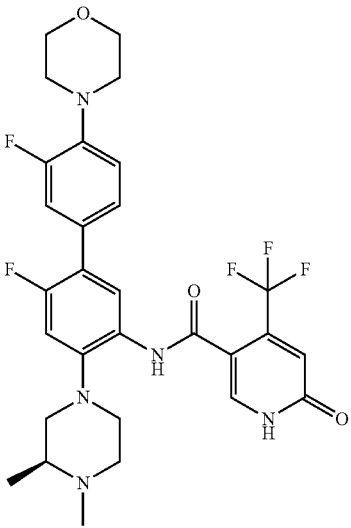 | N-[4-fluoro-5-(3-fluoro-4-morpholin-4-ylphenyl)-2-[rac-(3R)-3,4-dimethylpiperazin-1-yl]phenyl]-6-oxo-4-(trifluoromethyl)-1H-pyridine-3-carboxamide | 0.000466 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 202 | 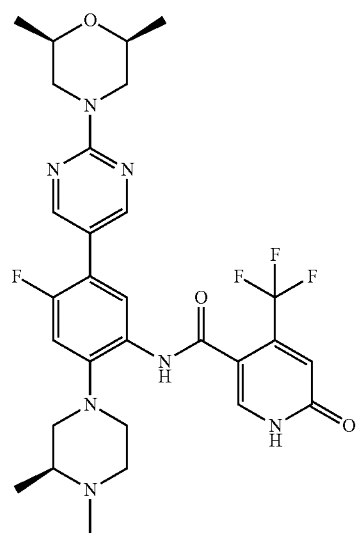 | N-[4-fluoro-5-[2-[rac-(2R,6S)-2,6-dimethylmorpholin-4-yl]pyrimidin-5-yl]-2-[rac-(3R)-3,4-dimethylpiperazin-1-yl]phenyl]-6-oxo-4-(trifluoromethyl)-1H-pyridine-3-carboxamide | 0.000434 |
| 203 | 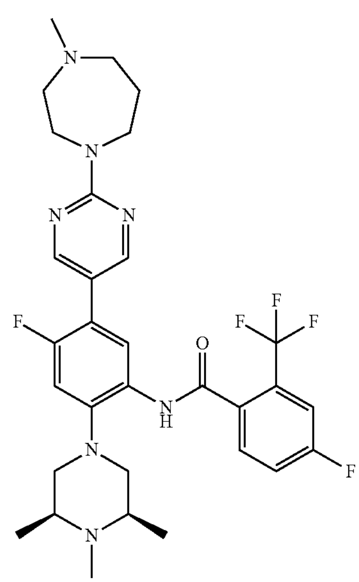 [SMILES: C[C@@H]1CN(c2cc(F)c(-c3cnc(N4CCCN(C)CC4)nc3)cc2NC(=O)c2ccc(F)cc2C(F)(F)F)C[C@H](C)N1C] | 4-fluoro-N-[4-fluoro-5-[2-(4-methyl-1,4-diazepan-1-yl)pyrimidin-5-yl]-2-[rac-(3R,5S)-3,4,5-trimethylpiperazin-1-yl]phenyl]-2-(trifluoromethyl)benzamide | 0.00166 |

TABLE 1-continued

Binding affinities (K_D) derived from surface plasmon resonance (SPR) assays

| Example No. | Structure | IUPAC Name | WDR5 binding affinity ($K_D$, µM) |
|---|---|---|---|
| 204 | 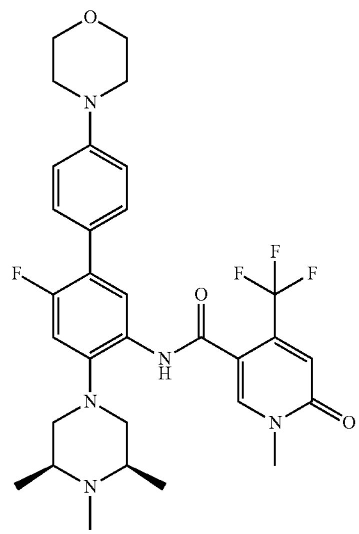 [SMILES: C[C@@H]1CN(c2cc(F)c(-c3ccc(N4CCOCC4)cc3)cc2NC(=O)c2cn(C)c(=O)cc2C(F)(F)F)C[C@H](C)N1C] | N-[4-fluoro-5-(4-morpholin-4-ylphenyl)-2-[rac-(3R,5S)-3,4,5-trimethylpiperazin-1-yl]phenyl]-1-methyl-6-oxo-4-(trifluoromethyl)pyridine-3-carboxamide | 0.0138 |
| 205 | 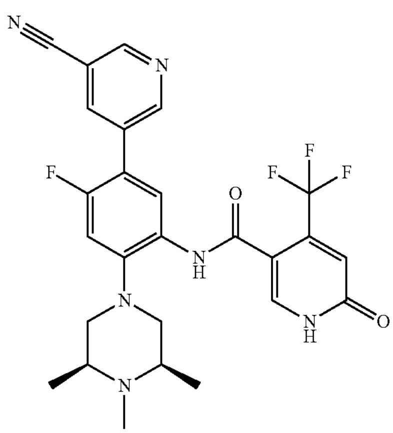 [SMILES: C[C@@H]1CN(c2cc(F)c(-c3cncc(C#N)c3)cc2NC(=O)c2c[nH]c(=O)cc2C(F)(F)F)C[C@H](C)N1C] | N-[5-(5-cyanopyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00815 |
| 206 | 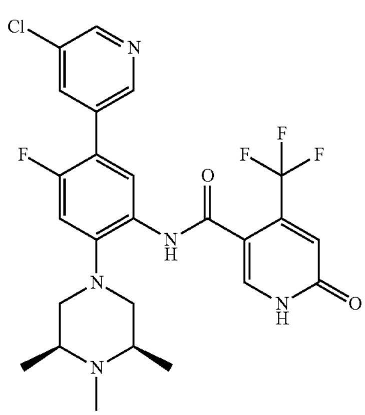 [SMILES: C[C@@H]1CN(c2cc(F)c(-c3cncc(Cl)c3)cc2NC(=O)c2c[nH]c(=O)cc2C(F)(F)F)C[C@H](C)N1C] | N-[5-(5-chloropyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00385 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 207 | 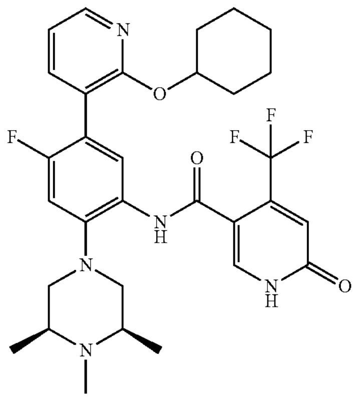 [SMILES: C[C@@H]1CN(c2cc(F)c(-c3cccnc3OC3CCCCC3)cc2NC(=O)c2c[nH]c(=O)cc2C(F)(F)F)C[C@H](C)N1C] | N-[5-(2-cyclohexyloxypyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00669 |
| 208 | 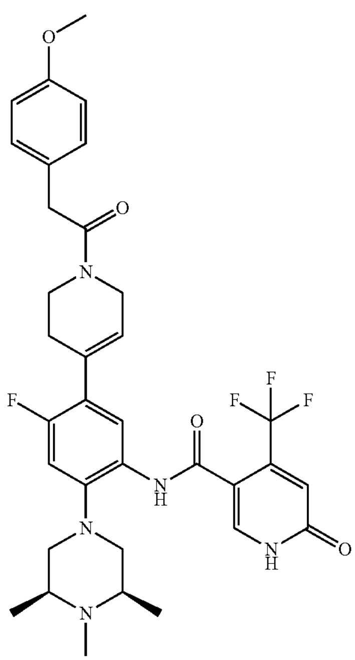 [SMILES: COc1ccc(CC(=O)N2CC=C(c3cc(NC(=O)c4c[nH]c(=O)cc4C(F)(F)F)c(N4C[C@@H](C)N(C)[C@@H](C)C4)cc3F)CC2)cc1] | N-[4-fluoro-5-[1-[2-(4-methoxyphenyl)acetyl]-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00057 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 209 | 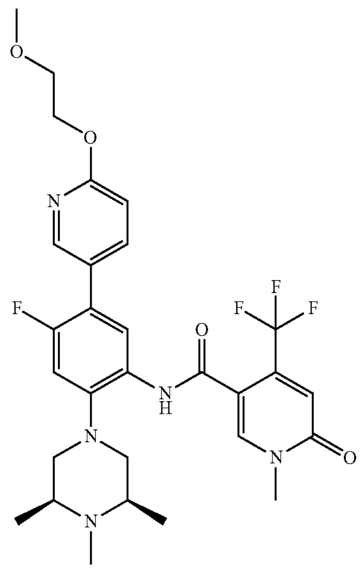 [SMILES: COCCOc1ccc(-c2cc(NC(=O)c3cn(C)c(=O)cc3C(F)(F)F)c(N3C[C@@H](C)N(C)[C@@H](C)C3)cc2F)cn1] | N-[4-fluoro-5-[6-(2-methoxyethoxy)pyridin-3-yl]-2-[rac-(3R,5S)-3,4,5-trimethylpiperazin-1-yl]phenyl]-1-methyl-6-oxo-4-(trifluoromethyl)pyridine-3-carboxamide | 0.00953 |
| 210 | 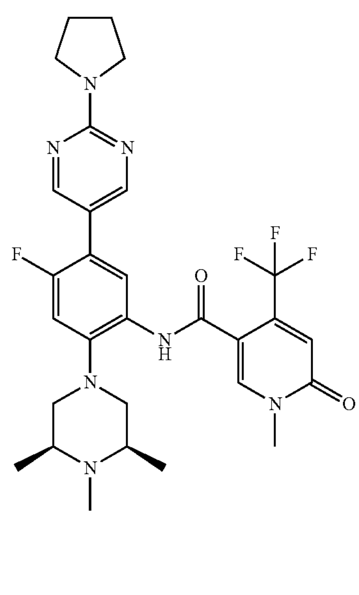 | N-[4-fluoro-5-(2-pyrrolidin-1-ylpyrimidin-5-yl)-2-[rac-(3R,5S)-3,4,5-trimethylpiperazin-1-yl]phenyl]-1-methyl-6-oxo-4-(trifluoromethyl)pyridine-3-carboxamide | 0.00386 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 211 | 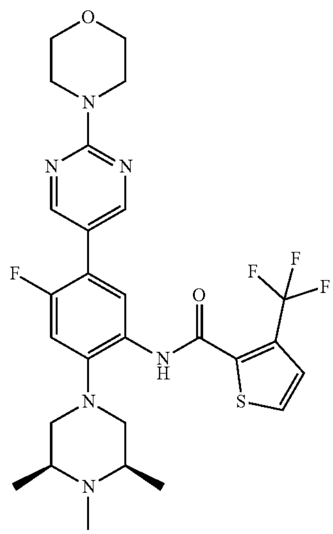 [SMILES: C[C@@H]1CN(c2cc(F)c(-c3cnc(N4CCOCC4)nc3)cc2NC(=O)c2sccc2C(F)(F)F)C[C@H](C)N1C] | N-[4-fluoro-5-(2-morpholin-4-ylpyrimidin-5-yl)-2-[rac-(3R,5S)-3,4,5-trimethylpiperazin-1-yl]phenyl]-3-(trifluoromethyl)thiophene-2-carboxamide | 0.12 |
| 212 | 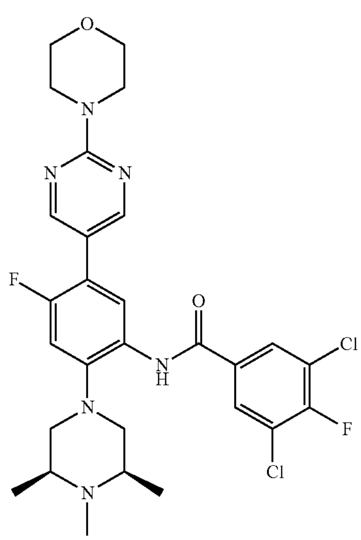 [SMILES: C[C@@H]1CN(c2cc(F)c(-c3cnc(N4CCOCC4)nc3)cc2NC(=O)c2cc(Cl)c(F)c(Cl)c2)C[C@H](C)N1C] | 3,5-dichloro-4-fluoro-N-[4-fluoro-5-(2-morpholin-4-ylpyrimidin-5-yl)-2-[rac-(3R,5S)-3,4,5-trimethylpiperazin-1-yl]phenyl]benzamide | 0.00271 |

TABLE 1-continued

Binding affinities (K_D) derived from surface plasmon resonance (SPR) assays

| Example No. | Structure | IUPAC Name | WDR5 binding affinity (K_D, μM) |
|---|---|---|---|
| 213 | 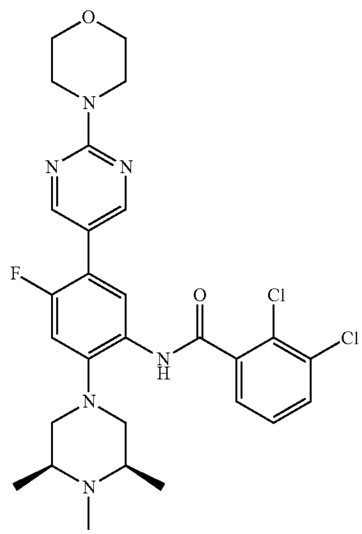 | 2,3-dichloro-N-[4-fluoro-5-(2-morpholin-4-ylpyrimidin-5-yl)-2-[rac-(3R,5S)-3,4,5-trimethylpiperazin-1-yl]phenyl]benzamide | 0.00691 |
| 214 | 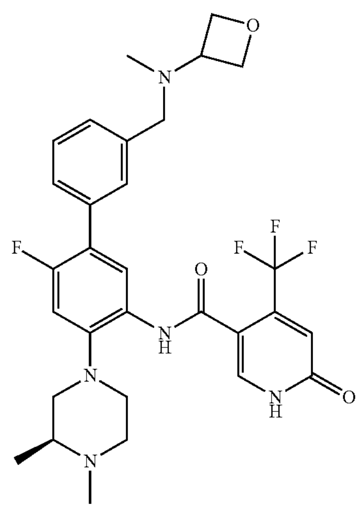 [SMILES: C[C@H]1CN(c2cc(F)c(-c3cccc(CN(C)C4COC4)c3)cc2NC(=O)c2c[nH]c(=O)cc2C(F)(F)F)CCN1C] | N-[4-fluoro-5-[3-[[methyl(oxetan-3-yl)amino]methyl]phenyl]-2-[rac-(3R)-3,4-dimethylpiperazin-1-yl]phenyl]-6-oxo-4-(trifluoromethyl)-1H-pyridine-3-carboxamide | 0.00215 |
| 215 | 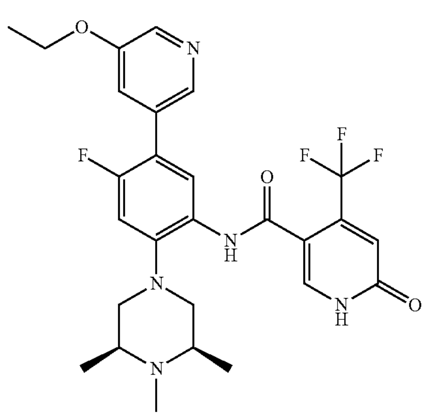 [SMILES: CCOc1cncc(-c2cc(NC(=O)c3c[nH]c(=O)cc3C(F)(F)F)c(N3C[C@@H](C)N(C)[C@@H](C)C3)cc2F)c1] | N-[5-(5-ethoxypyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00576 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 216 | 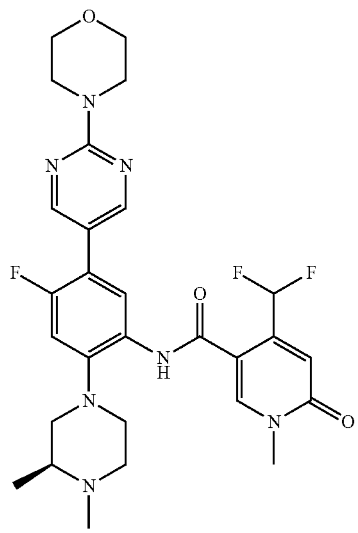 | 4-(difluoromethyl)-N-[4-fluoro-5-(2-morpholin-4-ylpyrimidin-5-yl)-2-[rac-(3R)-3,4-dimethylpiperazin-1-yl]phenyl]-1-methyl-6-oxopyridine-3-carboxamide | 0.00271 |
| 217 | 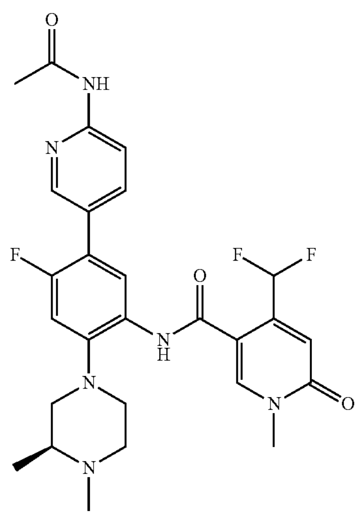 [SMILES: CC(=O)Nc1ccc(-c2cc(NC(=O)c3cn(C)c(=O)cc3C(F)F)c(N3CCN(C)[C@@H](C)C3)cc2F)cn1] | N-[5-(6-acetamidopyridin-3-yl)-4-fluoro-2-[rac-(3R)-3,4-dimethylpiperazin-1-yl]phenyl]-4-(difluoromethyl)-1-methyl-6-oxopyridine-3-carboxamide | 0.00432 |
| 218 | 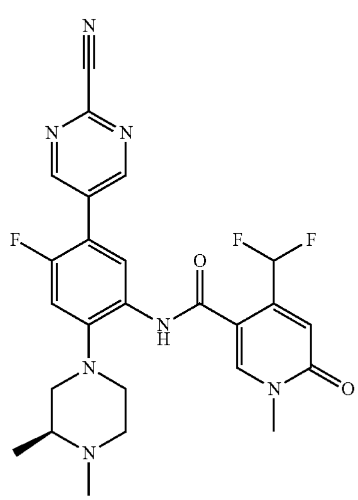 [SMILES: C[C@H]1CN(c2cc(F)c(-c3cnc(C#N)nc3)cc2NC(=O)c2cn(C)c(=O)cc2C(F)F)CCN1C] | N-[5-(2-cyanopyrimidin-5-yl)-4-fluoro-2-[rac-(3R)-3,4-dimethylpiperazin-1-yl]phenyl]-4-(difluoromethyl)-1-methyl-6-oxopyridine-3-carboxamide | 0.00318 |

TABLE 1-continued

Binding affinities (K_D) derived from surface plasmon resonance (SPR) assays

| Example No. | Structure | IUPAC Name | WDR5 binding affinity (K_D, μM) |
|---|---|---|---|
| 219 | 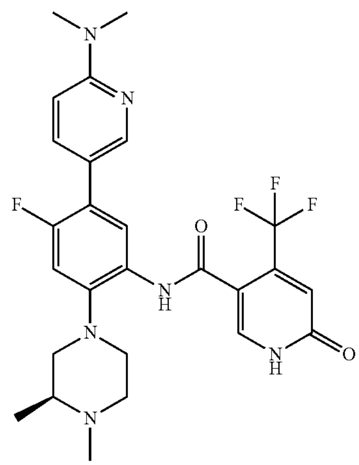 [SMILES: C[C@H]1CN(c2cc(F)c(-c3ccc(N(C)C)nc3)cc2NC(=O)c2c[nH]c(=O)cc2C(F)(F)F)CCN1C] | N-[5-[6-(dimethylamino) pyridin-3-yl]-4-fluoro-2-[rac-(3R)-3,4-dimethylpiperazin-1-yl]phenyl]-6-oxo-4-(trifluoromethyl)-1H-pyridine-3-carboxamide | 0.0014 |
| 220 | 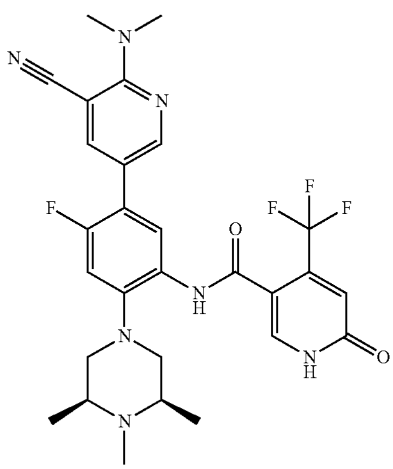 [SMILES: C[C@@H]1CN(c2cc(F)c(-c3cnc(N(C)C)c(C#N)c3)cc2NC(=O)c2c[nH]c(=O)cc2C(F)(F)F)C[C@H](C)N1C] | N-[5-[5-cyano-6-(dimethylamino)pyridin-3-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00225 |
| 221 | 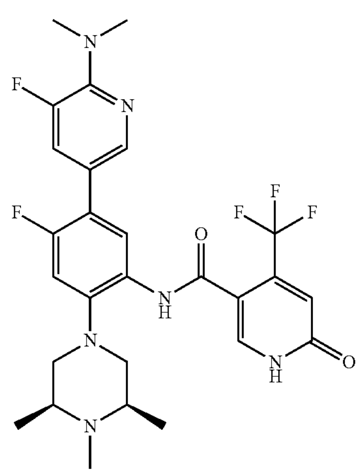 [SMILES: C[C@@H]1CN(c2cc(F)c(-c3cnc(N(C)C)c(F)c3)cc2NC(=O)c2c[nH]c(=O)cc2C(F)(F)F)C[C@H](C)N1C] | N-[5-[6-(dimethylamino)-5-fluoropyridin-3-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.000769 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 222 | 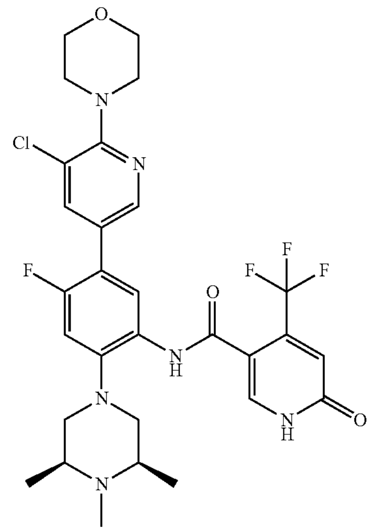 [SMILES: C[C@@H]1CN(c2cc(F)c(-c3cnc(N4CCOCC4)c(Cl)c3)cc2NC(=O)c2c[nH]c(=O)cc2C(F)(F)F)C[C@H](C)N1C] | N-[5-(5-chloro-6-morpholin-4-ylpyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00134 |
| 223 | 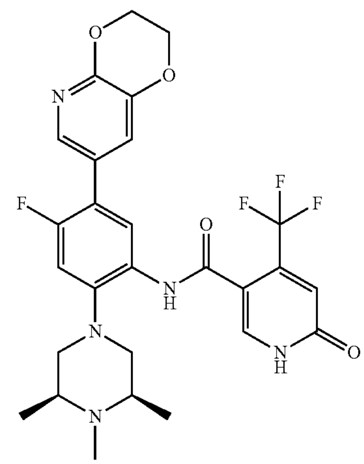 [SMILES: C[C@@H]1CN(c2cc(F)c(-c3cnc4c(c3)OCCO4)cc2NC(=O)c2c[nH]c(=O)cc2C(F)(F)F)C[C@H](C)N1C] | N-[5-(2,3-dihydro-[1,4]dioxino[2,3-b]pyridin-7-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00163 |
| 224 | 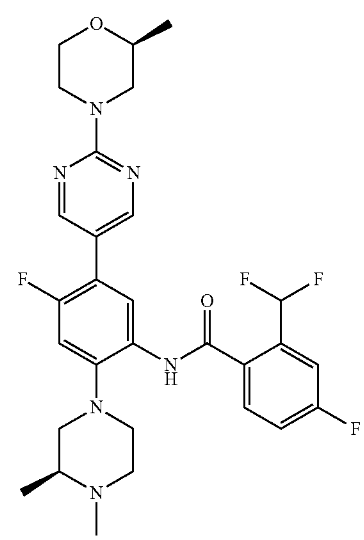 [SMILES: C[C@H]1CN(c2ncc(-c3cc(NC(=O)c4ccc(F)cc4C(F)F)c(N4CCN(C)[C@@H](C)C4)cc3F)cn2)CCO1] | 2-(difluoromethyl)-N-(2-((S)-3,4-dimethylpiperazin-1-yl)-4-fluoro-5-(2-((S)-2-methylmorpholino)pyrimidin-5-yl)phenyl)-4-fluorobenzamide | |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 225 | 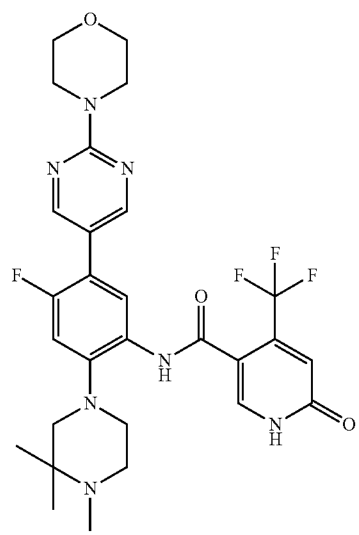 [SMILES: CN1CCN(c2cc(F)c(-c3cnc(N4CCOCC4)nc3)cc2NC(=O)c2c[nH]c(=O)cc2C(F)(F)F)CC1(C)C] | N-[4-fluoro-5-(2-morpholin-4-ylpyrimidin-5-yl)-2-(3,3,4-trimethylpiperazin-1-yl)phenyl]-6-oxo-4-(trifluoromethyl)-1H-pyridine-3-carboxamide | 3 |
| 226 | 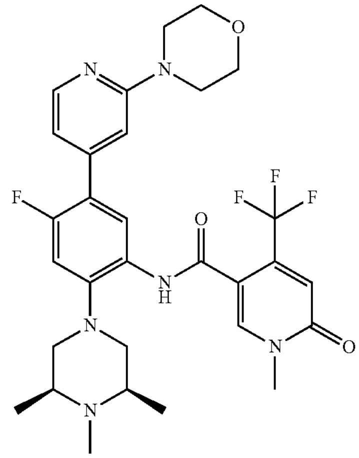 [SMILES: C[C@@H]1CN(c2cc(F)c(-c3ccnc(N4CCOCC4)c3)cc2NC(=O)c2cn(C)c(=O)cc2C(F)(F)F)C[C@H](C)N1C] | N-[4-fluoro-5-(2-morpholin-4-ylpyridin-4-yl)-2-[rac-(3R,5S)-3,4,5-trimethylpiperazin-1-yl]phenyl]-1-methyl-6-oxo-4-(trifluoromethyl)pyridine-3-carboxamide | 0.00799 |
| 227 | 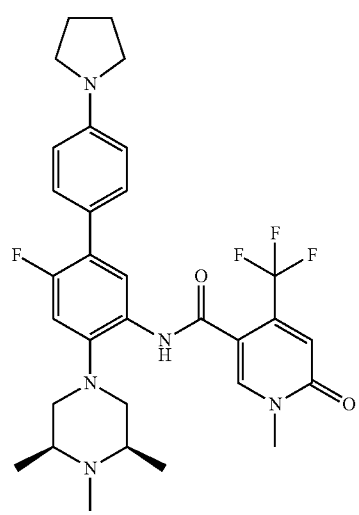 [SMILES: C[C@@H]1CN(c2cc(F)c(-c3ccc(N4CCCC4)cc3)cc2NC(=O)c2cn(C)c(=O)cc2C(F)(F)F)C[C@H](C)N1C] | N-[4-fluoro-5-(4-pyrrolidin-1-ylphenyl)-2-[rac-(3R,5S)-3,4,5-trimethylpiperazin-1-yl]phenyl]-1-methyl-6-oxo-4-(trifluoromethyl)pyridine-3-carboxamide | 0.00914 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 228 | 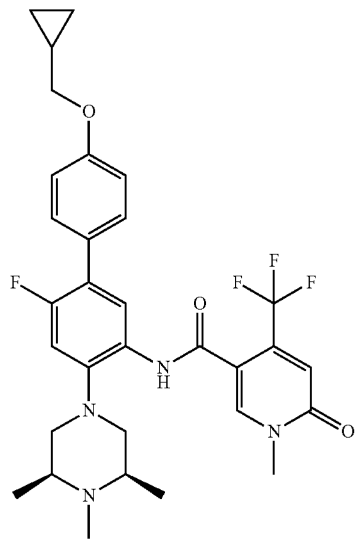 [SMILES: C[C@@H]1CN(c2cc(F)c(-c3ccc(OCC4CC4)cc3)cc2NC(=O)c2cn(C)c(=O)cc2C(F)(F)F)C[C@H](C)N1C] | N-[5-[4-(cyclopropylmethoxy)phenyl]-4-fluoro-2-[rac-(3R,5S)-3,4,5-trimethylpiperazin-1-yl]phenyl]-1-methyl-6-oxo-4-(trifluoromethyl)pyridine-3-carboxamide | 0.00726 |
| 229 | 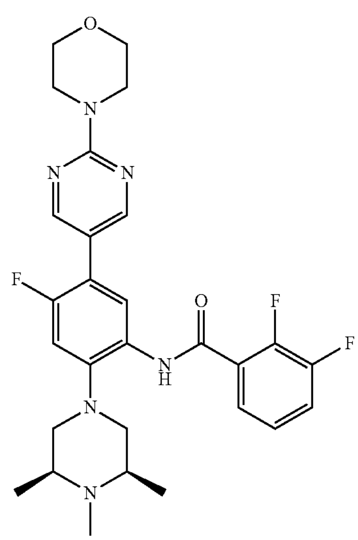 | 2,3-difluoro-N-[4-fluoro-5-(2-morpholin-4-ylpyrimidin-5-yl)-2-[rac-(3R,5S)-3,4,5-trimethylpiperazin-1-yl]phenyl]benzamide | 0.083 |

TABLE 1-continued

Binding affinities (K_D) derived from surface plasmon resonance (SPR) assays

| Example No. | Structure | IUPAC Name | WDR5 binding affinity ($K_D$, µM) |
|---|---|---|---|
| 230 | 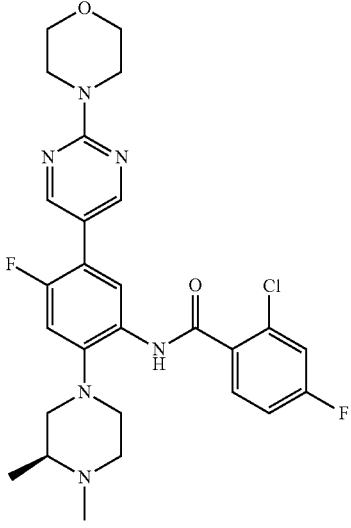 [SMILES: C[C@H]1CN(c2cc(F)c(-c3cnc(N4CCOCC4)nc3)cc2NC(=O)c2ccc(F)cc2Cl)CCN1C] | 2-chloro-4-fluoro-N-[4-fluoro-5-(2-morpholin-4-ylpyrimidin-5-yl)-2-[rac-(3R)-3,4-dimethylpiperazin-1-yl]phenyl]benzamide | 0.00895 |
| 231 | 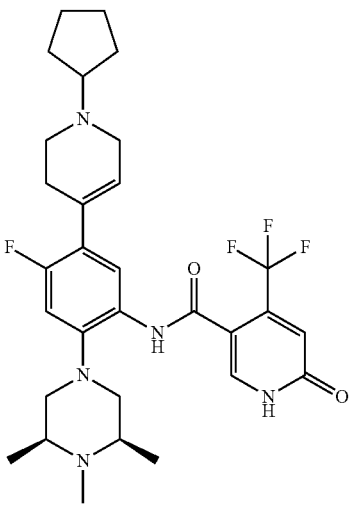 [SMILES: C[C@@H]1CN(c2cc(F)c(C3=CCN(C4CCCC4)CC3)cc2NC(=O)c2c[nH]c(=O)cc2C(F)(F)F)C[C@H](C)N1C] | N-[5-(1-cyclopentyl-3,6-dihydro-2H-pyridin-4-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00251 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 232 | 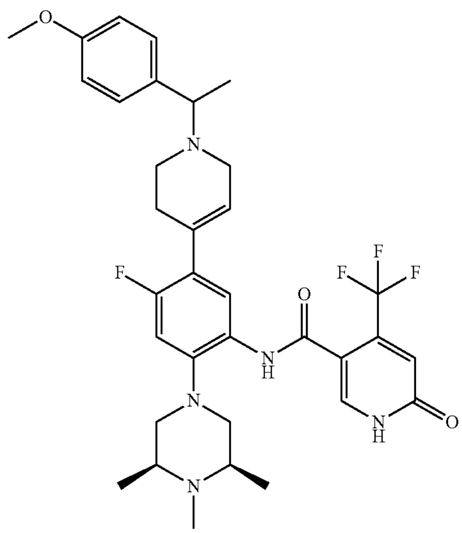 [SMILES: COc1ccc(C(C)N2CC=C(c3cc(NC(=O)c4c[nH]c(=O)cc4C(F)(F)F)c(N4C[C@@H](C)N(C)[C@@H](C)C4)cc3F)CC2)cc1] | N-[4-fluoro-5-[1-[1-(4-methoxyphenyl)ethyl]-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00272 |
| 233 | 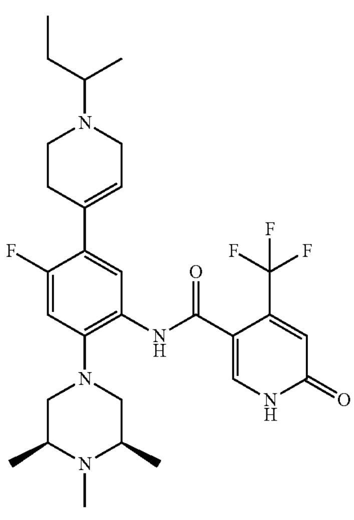 | N-[5-(1-butan-2-yl-3,6-dihydro-2H-pyridin-4-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00389 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 234 | 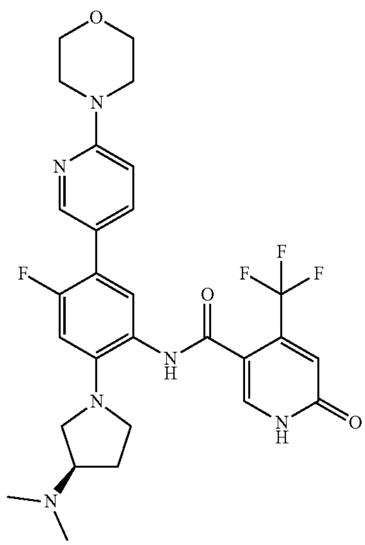 [SMILES: CN(C)[C@@H]1CCN(c2cc(F)c(-c3ccc(N4CCOCC4)nc3)cc2NC(=O)c2c[nH]c(=O)cc2C(F)(F)F)C1] | N-[4-fluoro-5-(6-morpholin-4-ylpyridin-3-yl)-2-[rac-(3R)-3-(dimethylamino)pyrrolidin-1-yl]phenyl]-6-oxo-4-(trifluoromethyl)-1H-pyridine-3-carboxamide | 0.00186 |
| 235 | 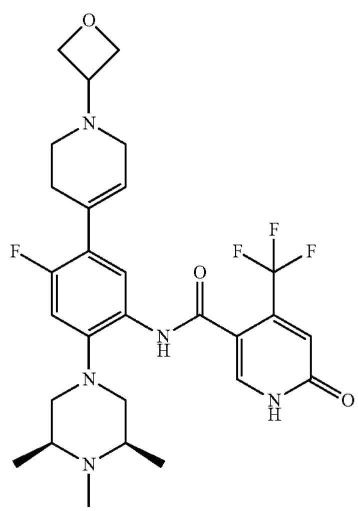 [SMILES: C[C@@H]1CN(c2cc(F)c(C3=CCN(C4COC4)CC3)cc2NC(=O)c2c[nH]c(=O)cc2C(F)(F)F)C[C@H](C)N1C] | N-[4-fluoro-5-[1-(oxetan-3-yl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.000943 |
| 236 | 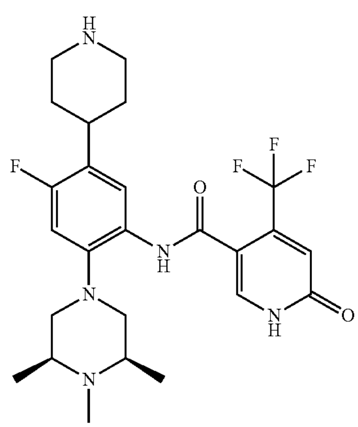 [SMILES: C[C@@H]1CN(c2cc(F)c(C3CCNCC3)cc2NC(=O)c2c[nH]c(=O)cc2C(F)(F)F)C[C@H](C)N1C] | N-[4-fluoro-5-piperidin-4-yl-2-[rac-(3R,5S)-3,4,5-trimethylpiperazin-1-yl]phenyl]-6-oxo-4-(trifluoromethyl)-1H-pyridine-3-carboxamide | 0.0311 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 237 | 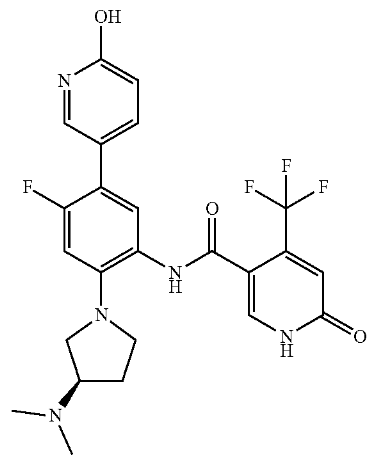 [SMILES: CN(C)[C@@H]1CCN(c2cc(F)c(-c3ccc(O)nc3)cc2NC(=O)c2c[nH]c(=O)cc2C(F)(F)F)C1] | N-[4-fluoro-5-(6-hydroxypyridin-3-yl)-2-[rac-(3R)-3-(dimethylamino)pyrrolidin-1-yl]phenyl]-6-oxo-4-(trifluoromethyl)-1H-pyridine-3-carboxamide | 0.00933 |
| 238 | 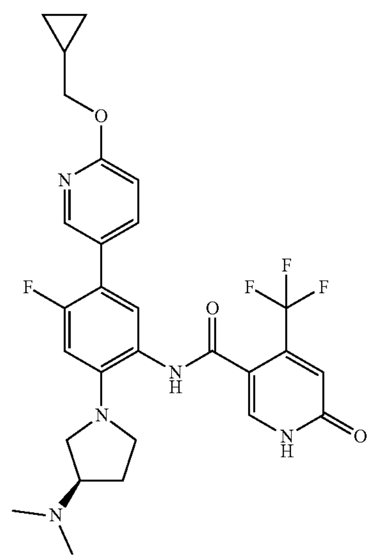 [SMILES: CN(C)[C@@H]1CCN(c2cc(F)c(-c3ccc(OCC4CC4)nc3)cc2NC(=O)c2c[nH]c(=O)cc2C(F)(F)F)C1] | N-[5-[6-(cyclopropylmethoxy)pyridin-3-yl]-4-fluoro-2-[rac-(3R)-3-(dimethylamino)pyrrolidin-1-yl]phenyl]-6-oxo-4-(trifluoromethyl)-1H-pyridine-3-carboxamide | 0.00511 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 239 | 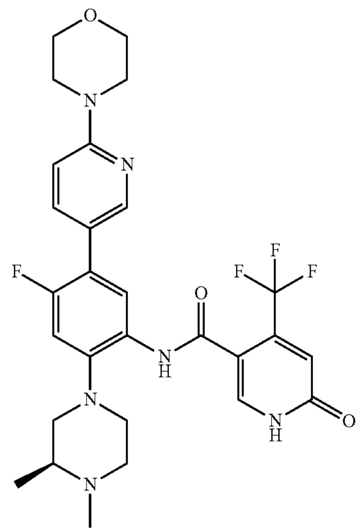 | N-[4-fluoro-5-(6-morpholin-4-ylpyridin-3-yl)-2-[rac-(3R)-3,4-dimethylpiperazin-1-yl]phenyl]-6-oxo-4-(trifluoromethyl)-1H-pyridine-3-carboxamide | 0.00107 |
| 240 | 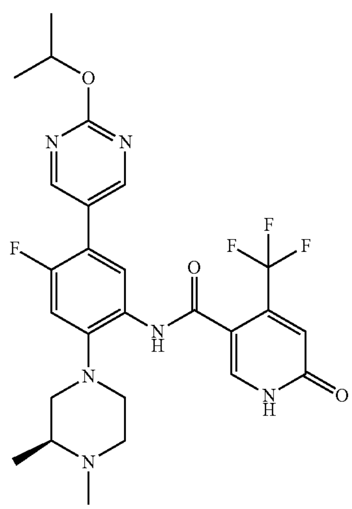 [SMILES: CC(C)Oc1ncc(-c2cc(NC(=O)c3c[nH]c(=O)cc3C(F)(F)F)c(N3CCN(C)[C@@H](C)C3)cc2F)cn1] | N-[4-fluoro-5-(2-propan-2-yloxypyrimidin-5-yl)-2-[rac-(3R)-3,4-dimethylpiperazin-1-yl]phenyl]-6-oxo-4-(trifluoromethyl)-1H-pyridine-3-carboxamide | 0.00223 |
| 241 | 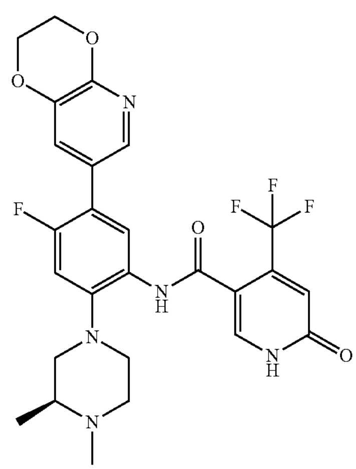 [SMILES: C[C@H]1CN(c2cc(F)c(-c3cnc4c(c3)OCCO4)cc2NC(=O)c2c[nH]c(=O)cc2C(F)(F)F)CCN1C] | N-[5-(2,3-dihydro-[1,4]dioxino[2,3-b]pyridin-7-yl)-4-fluoro-2-[rac-(3R)-3,4-dimethylpiperazin-1-yl]phenyl]-6-oxo-4-(trifluoromethyl)-1H-pyridine-3-carboxamide | 0.00282 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 242 | 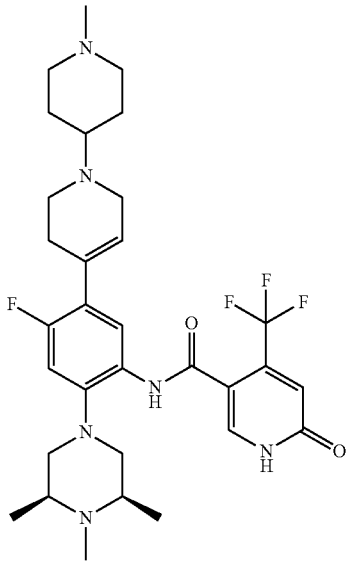 [SMILES: C[C@@H]1CN(c2cc(F)c(C3=CCN(C4CCN(C)CC4)CC3)cc2NC(=O)c2c[nH]c(=O)cc2C(F)(F)F)C[C@H](C)N1C] | N-[4-fluoro-5-[1-(1-methylpiperidin-4-yl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00349 |
| 243 | 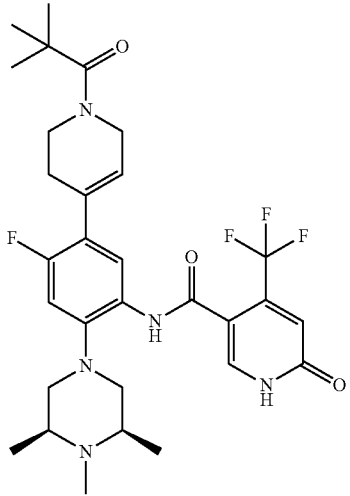 [SMILES: C[C@@H]1CN(c2cc(F)c(C3=CCN(C(=O)C(C)(C)C)CC3)cc2NC(=O)c2c[nH]c(=O)cc2C(F)(F)F)C[C@H](C)N1C] | N-[5-[1-(2,2-dimethylpropanoyl)-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00216 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 244 | 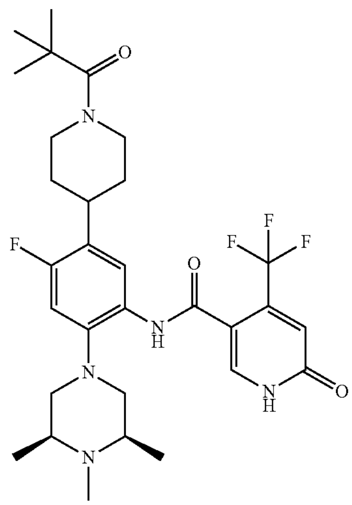 [SMILES: C[C@@H]1CN(c2cc(F)c(C3CCN(C(=O)C(C)(C)C)CC3)cc2NC(=O)c2c[nH]c(=O)cc2C(F)(F)F)C[C@H](C)N1C] | N-[5-[1-(2,2-dimethylpropanoyl)piperidin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00197 |
| 245 | 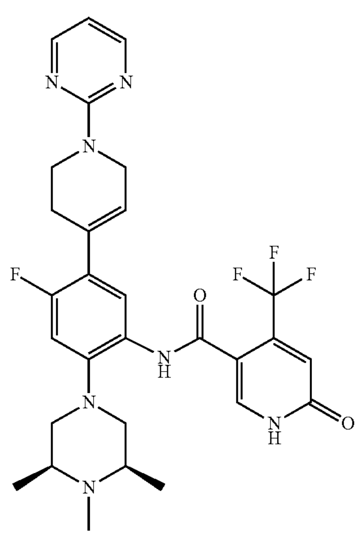 | N-[4-fluoro-5-(1-pyrimidin-2-yl-3,6-dihydro-2H-pyridin-4-yl)-2-[rac-(3R,5S)-3,4,5-trimethylpiperazin-1-yl]phenyl]-6-oxo-4-(trifluoromethyl)-1H-pyridine-3-carboxamide | 0.00139 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 246 | 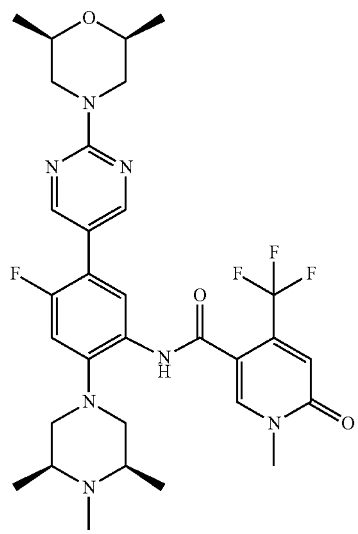 | N-[4-fluoro-5-[2-[rac-(2R,6S)-2,6-dimethylmorpholin-4-yl]pyrimidin-5-yl]-2-[rac-(3S,5R)-3,4,5-trimethylpiperazin-1-yl]phenyl]-1-methyl-6-oxo-4-(trifluoromethyl)pyridine-3-carboxamide | 0.00251 |
| 247 | 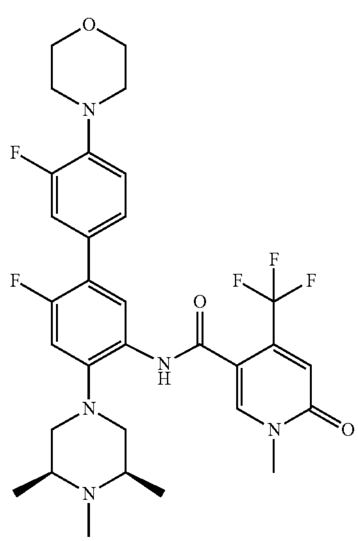 | N-[4-fluoro-5-(3-fluoro-4-morpholin-4-ylphenyl)-2-[rac-(3R,5S)-3,4,5-trimethylpiperazin-1-yl]phenyl]-1-methyl-6-oxo-4-(trifluoromethyl)pyridine-3-carboxamide | 0.00516 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 248 | 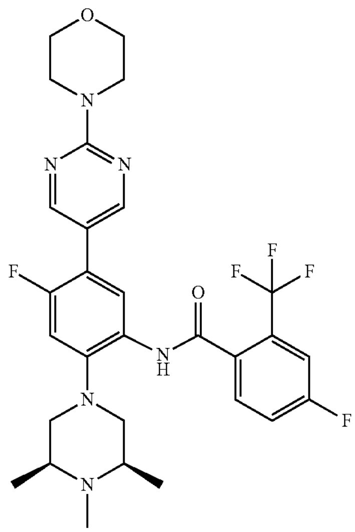 | 4-fluoro-N-[4-fluoro-5-(2-morpholin-4-ylpyrimidin-5-yl)-2-[rac-(3R,5S)-3,4,5-trimethylpiperazin-1-yl]phenyl]-2-(trifluoromethyl)benzamide | 0.00133 |
| 249 | 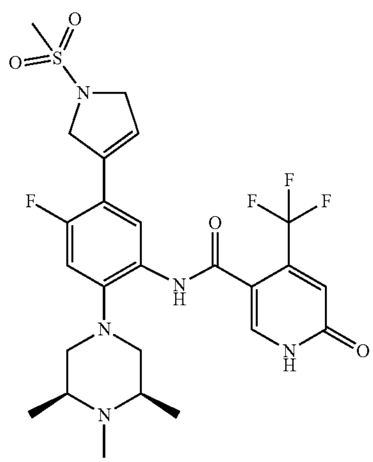 [SMILES: C[C@@H]1CN(c2cc(F)c(C3=CCN(S(C)(=O)=O)C3)cc2NC(=O)c2c[nH]c(=O)cc2C(F)(F)F)C[C@H](C)N1C] | N-[4-fluoro-5-(1-methylsulfonyl-2,5-dihydropyrrol-3-yl)-2-[rac-(3R,5S)-3,4,5-trimethylpiperazin-1-yl]phenyl]-6-oxo-4-(trifluoromethyl)-1H-pyridine-3-carboxamide | 0.000665 |
| 250 | 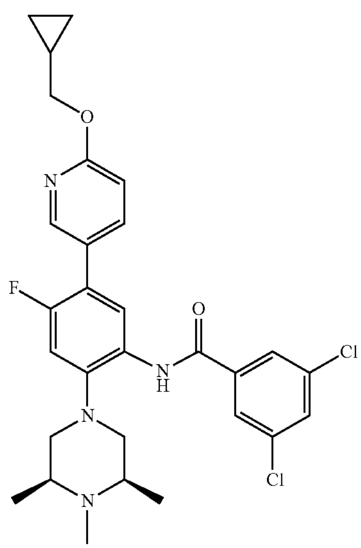 [SMILES: C[C@@H]1CN(c2cc(F)c(-c3ccc(OCC4CC4)nc3)cc2NC(=O)c2cc(Cl)cc(Cl)c2)C[C@H](C)N1C] | 3,5-dichloro-N-[5-[6-(cyclopropylmethoxy)pyridin-3-yl]-4-fluoro-2-[rac-(3R,5S)-3,4,5-trimethylpiperazin-1-yl]phenyl]benzamide | 0.0769 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 251 | 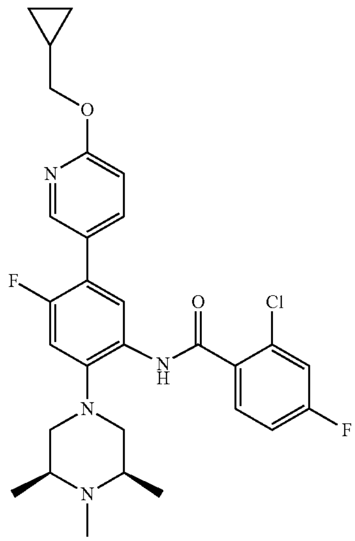 [SMILES: C[C@@H]1CN(c2cc(F)c(-c3ccc(OCC4CC4)nc3)cc2NC(=O)c2ccc(F)cc2Cl)C[C@H](C)N1C] | 2-chloro-N-[5-[6-(cyclopropylmethoxy)pyridin-3-yl]-4-fluoro-2-[rac-(3R,5S)-3,4,5-trimethylpiperazin-1-yl]phenyl]-4-fluorobenzamide | 0.0156 |
| 252 | 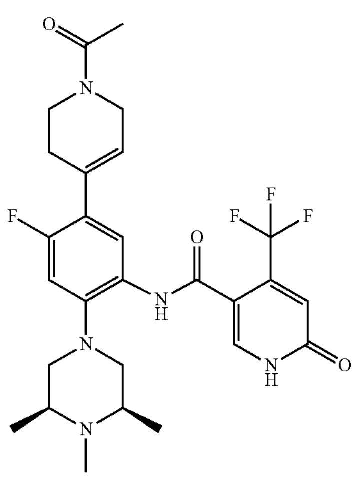 [SMILES: CC(=O)N1CC=C(c2cc(NC(=O)c3c[nH]c(=O)cc3C(F)(F)F)c(N3C[C@@H](C)N(C)[C@@H](C)C3)cc2F)CC1] | N-[5-(1-acetyl-3,6-dihydro-2H-pyridin-4-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00279 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 253 | 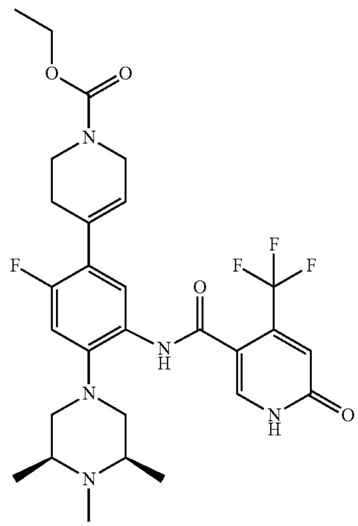 | ethyl 4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.0033 |
| 254 | 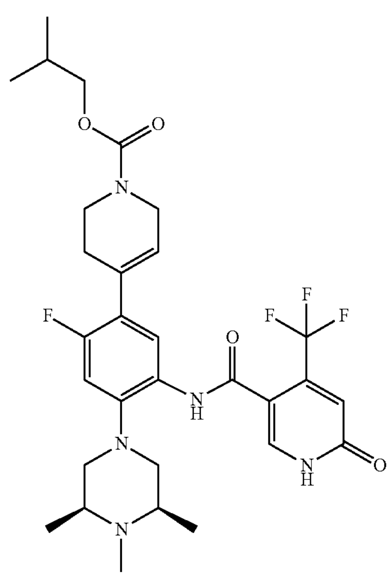 [SMILES: CC(C)COC(=O)N1CC=C(c2cc(NC(=O)c3c[nH]c(=O)cc3C(F)(F)F)c(N3C[C@@H](C)N(C)[C@@H](C)C3)cc2F)CC1] | 2-methylpropyl 4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.00334 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 255 | 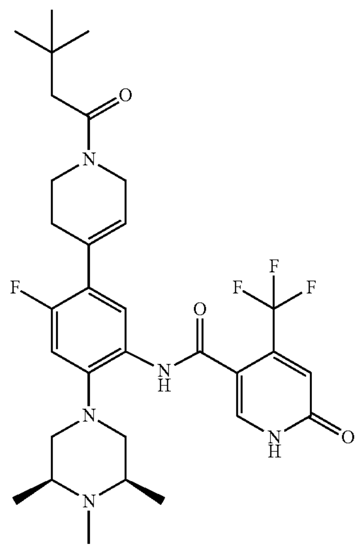 | N-[5-[1-(3,3-dimethylbutanoyl)-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00198 |
| 256 | 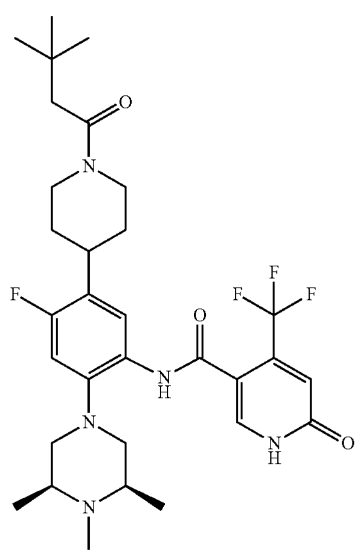 [SMILES: C[C@@H]1CN(c2cc(F)c(C3CCN(C(=O)CC(C)(C)C)CC3)cc2NC(=O)c2c[nH]c(=O)cc2C(F)(F)F)C[C@H](C)N1C] | N-[5-[1-(3,3-dimethylbutanoyl)piperidin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.0118 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 257 | 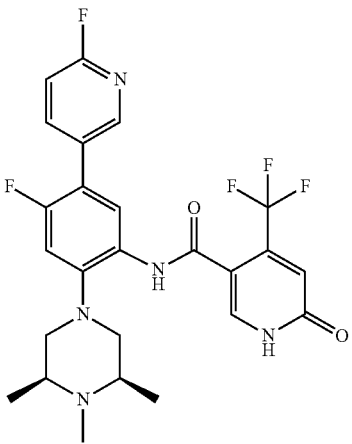 [SMILES: C[C@@H]1CN(c2cc(F)c(-c3ccc(F)nc3)cc2NC(=O)c2c[nH]c(=O)cc2C(F)(F)F)C[C@H](C)N1C] | N-[4-fluoro-5-(6-fluoropyridin-3-yl)-2-[rac-(3R,5S)-3,4,5-trimethylpiperazin-1-yl]phenyl]-6-oxo-4-(trifluoromethyl)-1H-pyridine-3-carboxamide | 0.0017 |
| 258 | 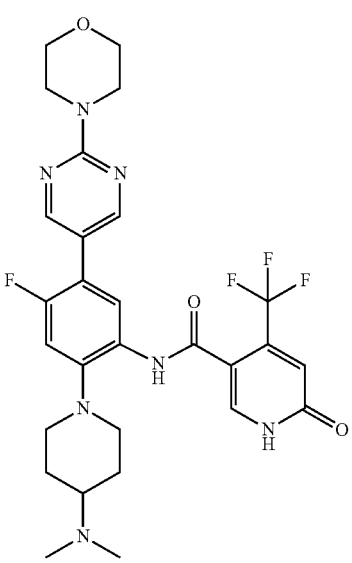 [SMILES: CN(C)C1CCN(c2cc(F)c(-c3cnc(N4CCOCC4)nc3)cc2NC(=O)c2c[nH]c(=O)cc2C(F)(F)F)CC1] | N-[2-[4-(dimethylamino)piperidin-1-yl]-4-fluoro-5-(2-morpholin-4-ylpyrimidin-5-yl)phenyl]-6-oxo-4-(trifluoromethyl)-1H-pyridine-3-carboxamide | 0.0661 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 259 | 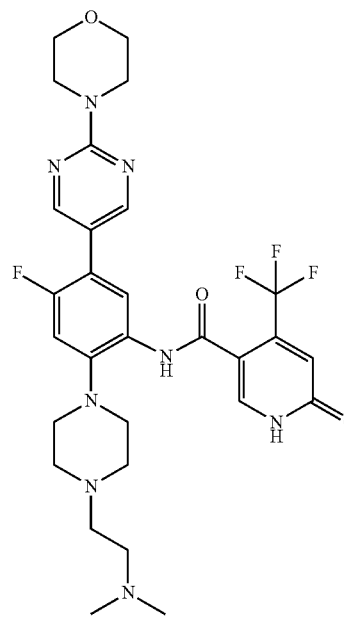 | N-[2-[4-[2-(dimethylamino)ethyl]piperazin-1-yl]-4-fluoro-5-(2-morpholin-4-ylpyrimidin-5-yl)phenyl]-6-oxo-4-(trifluoromethyl)-1H-pyridine-3-carboxamide | — |
| 260 | 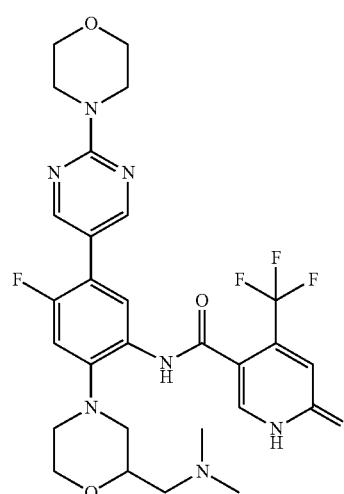 | N-[2-[2-[(dimethylamino)methyl]morpholin-4-yl]-4-fluoro-5-(2-morpholin-4-ylpyrimidin-5-yl)phenyl]-6-oxo-4-(trifluoromethyl)-1H-pyridine-3-carboxamide | — |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 261 | 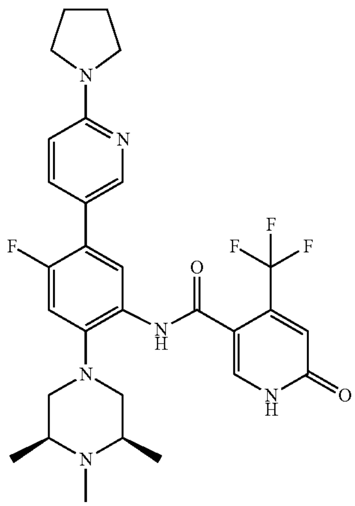 [SMILES: C[C@@H]1CN(c2cc(F)c(-c3ccc(N4CCCC4)nc3)cc2NC(=O)c2c[nH]c(=O)cc2C(F)(F)F)C[C@H](C)N1C] | N-[4-fluoro-5-(6-pyrrolidin-1-ylpyridin-3-yl)-2-[rac-(3R,5S)-3,4,5-trimethylpiperazin-1-yl]phenyl]-6-oxo-4-(trifluoromethyl)-1H-pyridine-3-carboxamide | 0.00164 |
| 262 | 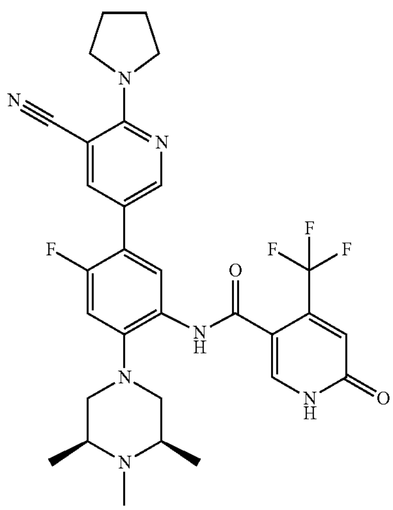 [SMILES: C[C@@H]1CN(c2cc(F)c(-c3cnc(N4CCCC4)c(C#N)c3)cc2NC(=O)c2c[nH]c(=O)cc2C(F)(F)F)C[C@H](C)N1C] | N-[5-(5-cyano-6-pyrrolidin-1-ylpyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | — |
| 263 | 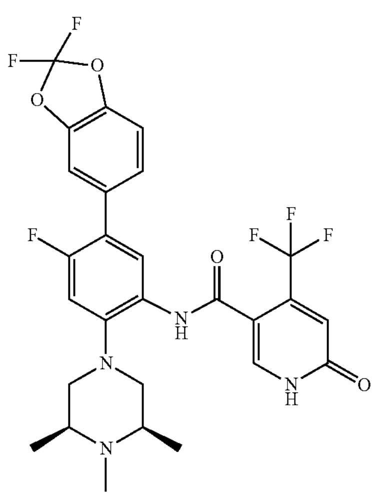 [SMILES: C[C@@H]1CN(c2cc(F)c(-c3ccc4c(c3)OC(F)(F)O4)cc2NC(=O)c2c[nH]c(=O)cc2C(F)(F)F)C[C@H](C)N1C] | N-[5-(2,2-difluoro-1,3-benzodioxol-5-yl)-4-fluoro-2-[rac-(3R,5S)-3,4,5-trimethylpiperazin-1-yl]phenyl]-6-oxo-4-(trifluoromethyl)-1H-pyridine-3-carboxamide | — |

TABLE 1-continued
Binding affinities (K$_D$) derived from surface plasmon resonance (SPR) assays
| Example No. | Structure | IUPAC Name | WDR5 binding affinity (K$_D$, μM) |
|---|---|---|---|
| 264 | 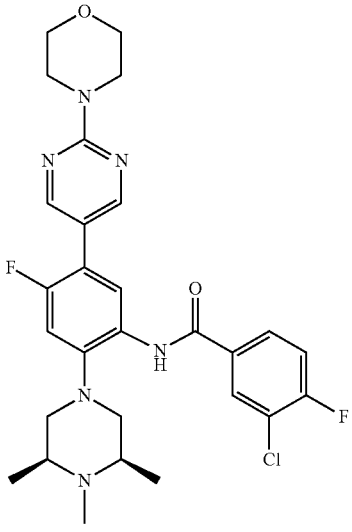 | 3-chloro-4-fluoro-N-[4-fluoro-5-(2-morpholin-4-ylpyrimidin-5-yl)-2-[rac-(3R,5S)-3,4,5-trimethylpiperazin-1-yl]phenyl]benzamide | 0.00294 |
| 265 | 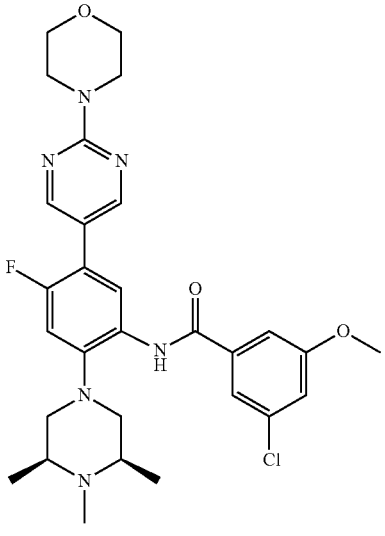 | 3-chloro-N-[4-fluoro-5-(2-morpholin-4-ylpyrimidin-5-yl)-2-[rac-(3R,5S)-3,4,5-trimethylpiperazin-1-yl]phenyl]-5-methoxybenzamide | 0.0283 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 266 | 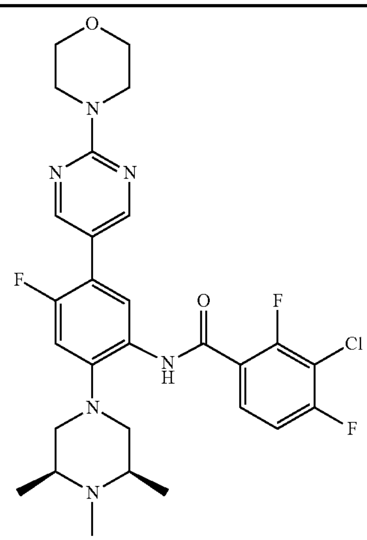 | 3-chloro-2,4-difluoro-N-[4-fluoro-5-(2-morpholin-4-ylpyrimidin-5-yl)-2-[rac-(3R,5S)-3,4,5-trimethylpiperazin-1-yl]phenyl]benzamide | 0.0137 |
| 267 | 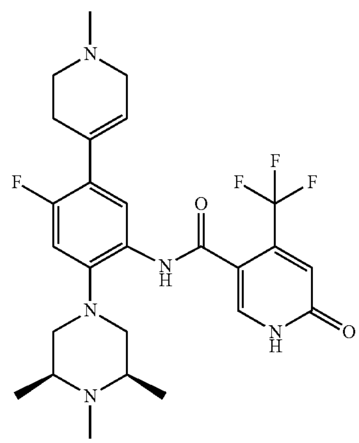 [SMILES: C[C@@H]1CN(c2cc(F)c(C3=CCN(C)CC3)cc2NC(=O)c2c[nH]c(=O)cc2C(F)(F)F)C[C@H](C)N1C] | N-[4-fluoro-5-(1-methyl-3,6-dihydro-2H-pyridin-4-yl)-2-[rac-(3R,5S)-3,4,5-trimethylpiperazin-1-yl]phenyl]-6-oxo-4-(trifluoromethyl)-1H-pyridine-3-carboxamide | 0.0107 |
| 268 | 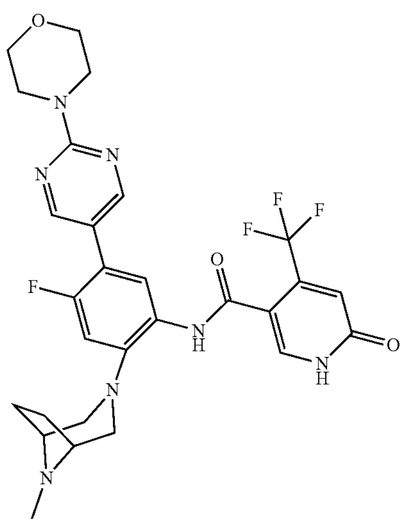 [SMILES: CN1C2CCC1CN(c1cc(F)c(-c3cnc(N4CCOCC4)nc3)cc1NC(=O)c1c[nH]c(=O)cc1C(F)(F)F)C2] | N-[4-fluoro-2-(8-methyl-3,8-diazabicyclo[3.2.1]octan-3-yl)-5-(2-morpholin-4-ylpyrimidin-5-yl)phenyl]-6-oxo-4-(trifluoromethyl)-1H-pyridine-3-carboxamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 269 | 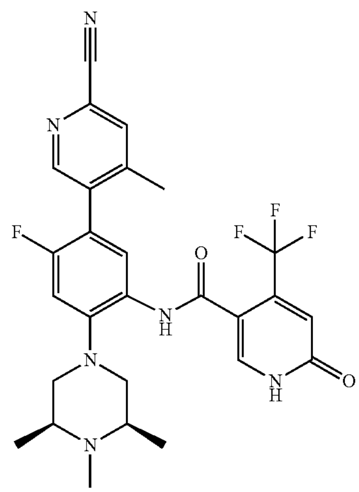 [SMILES: Cc1cc(C#N)ncc1-c1cc(NC(=O)c2c[nH]c(=O)cc2C(F)(F)F)c(N2C[C@@H](C)N(C)[C@@H](C)C2)cc1F] | N-[5-(6-cyano-4-methylpyridin-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00874 |
| 270 | 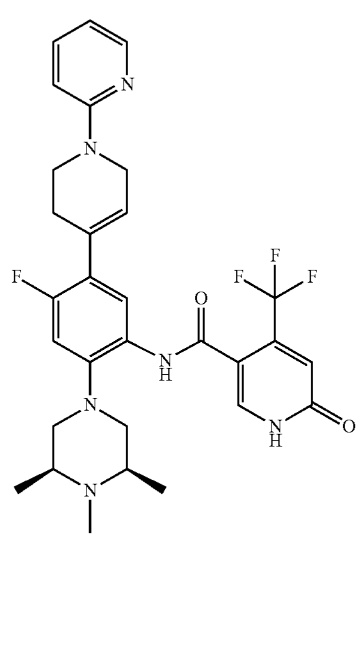 | N-[4-fluoro-5-(1-pyridin-2-yl-3,6-dihydro-2H-pyridin-4-yl)-2-[rac-(3R,5S)-3,4,5-trimethylpiperazin-1-yl]phenyl]-6-oxo-4-(trifluoromethyl)-1H-pyridine-3-carboxamide | 0.000938 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 271 | 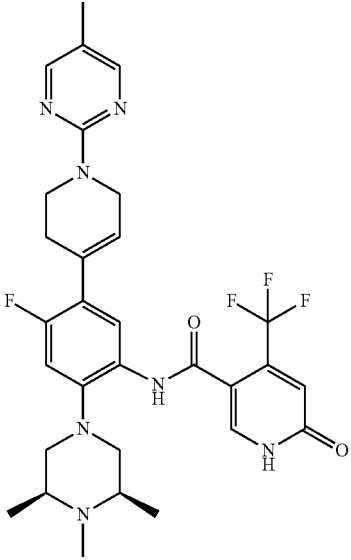 [SMILES: Cc1cnc(N2CC=C(c3cc(NC(=O)c4c[nH]c(=O)cc4C(F)(F)F)c(N4C[C@@H](C)N(C)[C@@H](C)C4)cc3F)CC2)nc1] | N-[4-fluoro-5-[1-(5-methylpyrimidin-2-yl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.000499 |
| 272 | 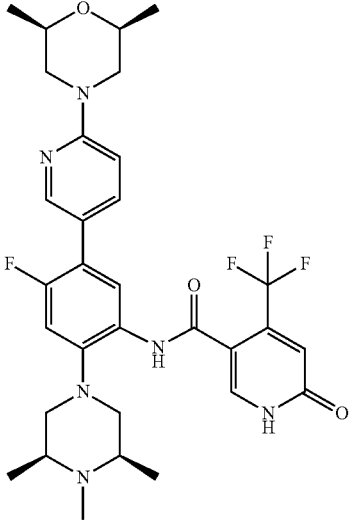 | N-[4-fluoro-5-[6-[rac-(2R,6S)-2,6-dimethylmorpholin-4-yl]pyridin-3-yl]-2-[rac-(3S,5R)-3,4,5-trimethylpiperazin-1-yl]phenyl]-6-oxo-4-(trifluoromethyl)-1H-pyridine-3-carboxamide | 0.000532 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 273 | 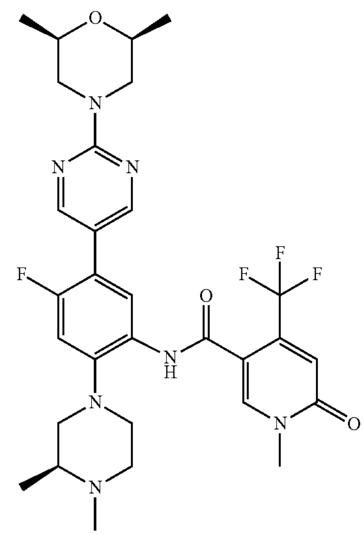 [SMILES: C[C@@H]1CN(c2ncc(-c3cc(NC(=O)c4cn(C)c(=O)cc4C(F)(F)F)c(N4CCN(C)[C@@H](C)C4)cc3F)cn2)C[C@H](C)O1] | N-[4-fluoro-5-[2-[rac-(2R,6S)-2,6-dimethylmorpholin-4-yl]pyrimidin-5-yl]-2-[rac-(3R)-3,4-dimethylpiperazin-1-yl]phenyl]-1-methyl-6-oxo-4-(trifluoromethyl)pyridine-3-carboxamide | 0.00211 |
| 274 | 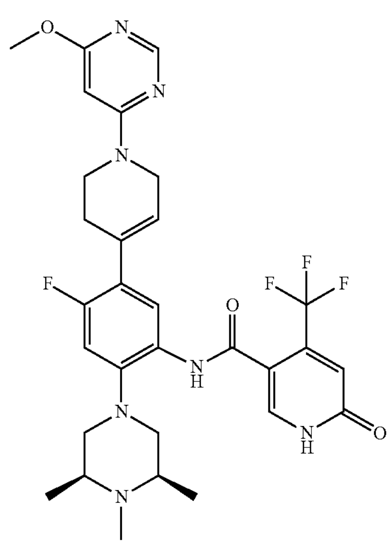 [SMILES: COc1cc(N2CC=C(c3cc(NC(=O)c4c[nH]c(=O)cc4C(F)(F)F)c(N4C[C@@H](C)N(C)[C@@H](C)C4)cc3F)CC2)ncn1] | N-[4-fluoro-5-[1-(6-methoxypyrimidin-4-yl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00129 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 275 | 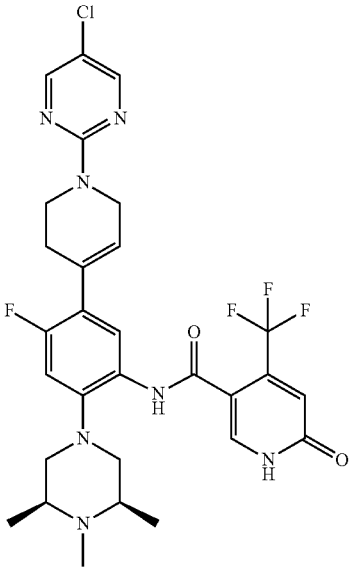 | N-[5-[1-(5-chloropyrimidin-2-yl)-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00154 |
| 276 | 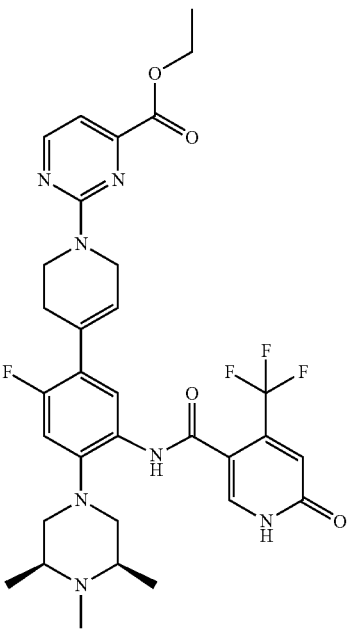 [SMILES: CCOC(=O)c1ccnc(N2CC=C(c3cc(NC(=O)c4c[nH]c(=O)cc4C(F)(F)F)c(N4C[C@@H](C)N(C)[C@@H](C)C4)cc3F)CC2)n1] | ethyl 2-[4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridin-1-yl]pyrimidine-4-carboxylate | 0.00167 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 277 | 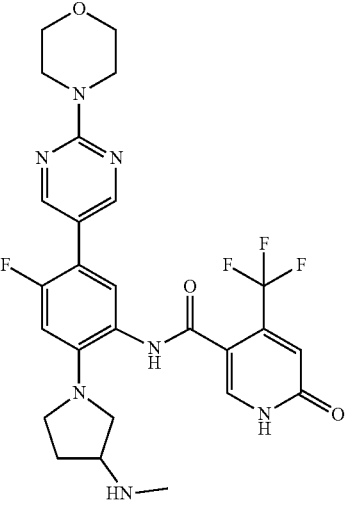 [SMILES: CNC1CCN(c2cc(F)c(-c3cnc(N4CCOCC4)nc3)cc2NC(=O)c2c[nH]c(=O)cc2C(F)(F)F)C1] | N-[4-fluoro-2-[3-(methylamino)pyrrolidin-1-yl]-5-(2-morpholin-4-ylpyrimidin-5-yl)phenyl]-6-oxo-4-(trifluoromethyl)-1H-pyridine-3-carboxamide | 0.0149 |
| 278 | 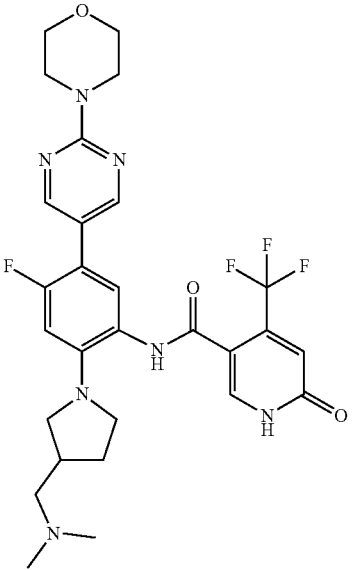 [SMILES: CN(C)CC1CCN(c2cc(F)c(-c3cnc(N4CCOCC4)nc3)cc2NC(=O)c2c[nH]c(=O)cc2C(F)(F)F)C1] | N-[2-[3-[(dimethylamino)methyl]pyrrolidin-1-yl]-4-fluoro-5-(2-morpholin-4-ylpyrimidin-5-yl)phenyl]-6-oxo-4-(trifluoromethyl)-1H-pyridine-3-carboxamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 279 | 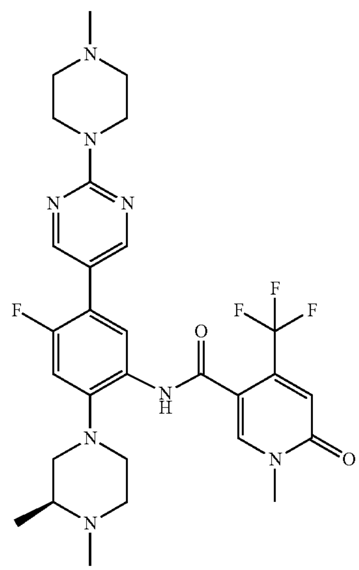 [SMILES: C[C@H]1CN(c2cc(F)c(-c3cnc(N4CCN(C)CC4)nc3)cc2NC(=O)c2cn(C)c(=O)cc2C(F)(F)F)CCN1C] | N-[4-fluoro-5-[2-(4-methylpiperazin-1-yl)pyrimidin-5-yl]-2-[rac-(3R)-3,4-dimethylpiperazin-1-yl]phenyl]-1-methyl-6-oxo-4-(trifluoromethyl)pyridine-3-carboxamide | 0.00208 |
| 280 | 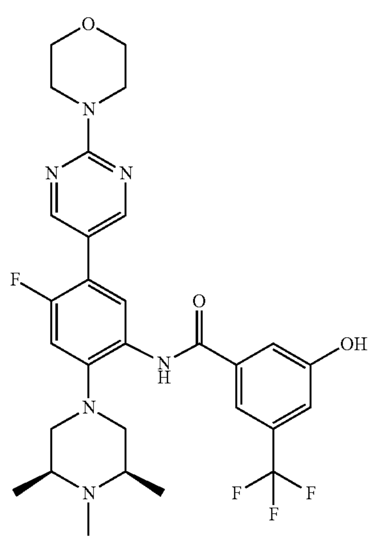 [SMILES: C[C@@H]1CN(c2cc(F)c(-c3cnc(N4CCOCC4)nc3)cc2NC(=O)c2cc(O)cc(C(F)(F)F)c2)C[C@H](C)N1C] | N-[4-fluoro-5-(2-morpholin-4-ylpyrimidin-5-yl)-2-[rac-(3R,5S)-3,4,5-trimethylpiperazin-1-yl]phenyl]-3-hydroxy-5-(trifluoromethyl)benzamide | 0.00312 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 281 | 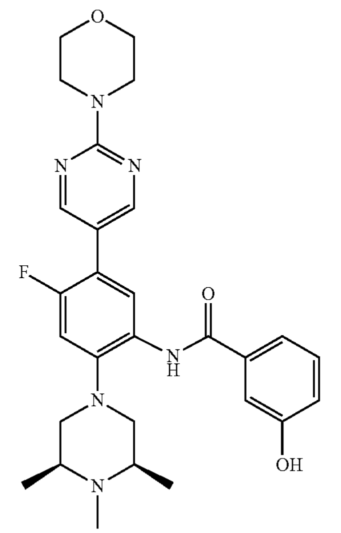 | N-[4-fluoro-5-(2-morpholin-4-ylpyrimidin-5-yl)-2-[rac-(3R,5S)-3,4,5-trimethylpiperazin-1-yl]phenyl]-3-hydroxybenzamide | 0.0291 |
| 282 | 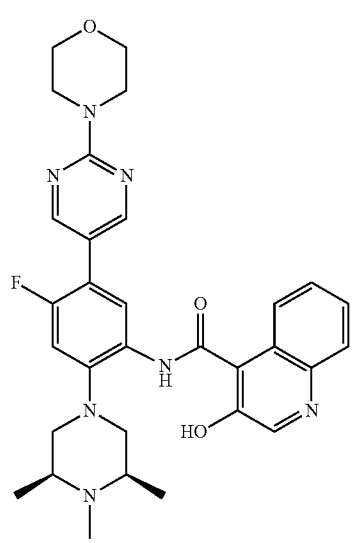 [SMILES: C[C@@H]1CN(c2cc(F)c(-c3cnc(N4CCOCC4)nc3)cc2NC(=O)c2c(O)cnc3ccccc23)C[C@H](C)N1C] | N-[4-fluoro-5-(2-morpholin-4-ylpyrimidin-5-yl)-2-[rac-(3R,5S)-3,4,5-trimethylpiperazin-1-yl]phenyl]-3-hydroxyquinoline-4-carboxamide | 0.00198 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 283 | 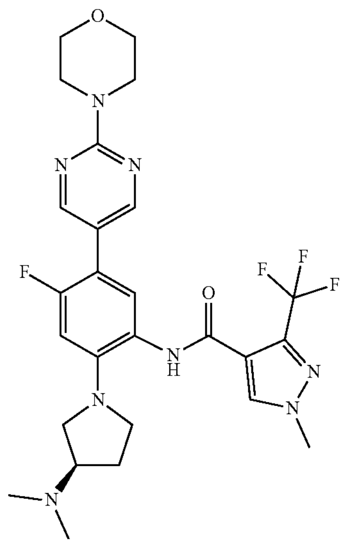 [SMILES: CN(C)[C@@H]1CCN(c2cc(F)c(-c3cnc(N4CCOCC4)nc3)cc2NC(=O)c2cn(C)nc2C(F)(F)F)C1] | N-[4-fluoro-5-(2-morpholin-4-ylpyrimidin-5-yl)-2-[rac-(3R)-3-(dimethylamino)pyrrolidin-1-yl]phenyl]-1-methyl-3-(trifluoromethyl)pyrazole-4-carboxamide | 0.0148 |
| 284 | 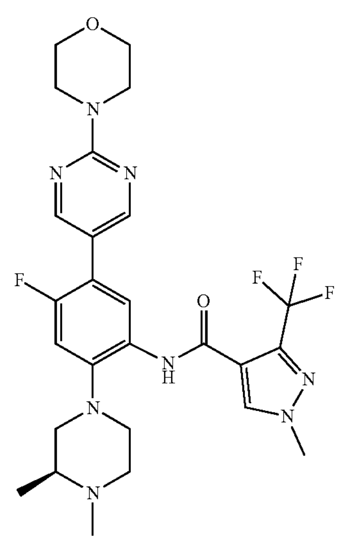 [SMILES: C[C@H]1CN(c2cc(F)c(-c3cnc(N4CCOCC4)nc3)cc2NC(=O)c2cn(C)nc2C(F)(F)F)CCN1C] | N-[4-fluoro-5-(2-morpholin-4-ylpyrimidin-5-yl)-2-[rac-(3R)-3,4-dimethylpiperazin-1-yl]phenyl]-1-methyl-3-(trifluoromethyl)pyrazole-4-carboxamide | 0.00813 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 285 | 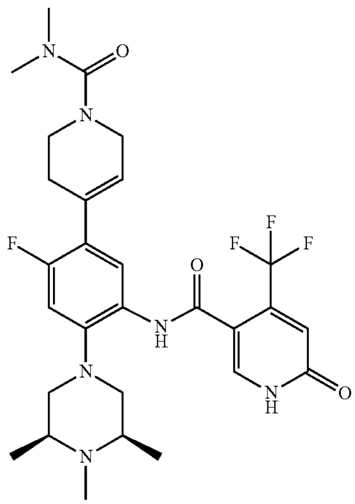 [SMILES: C[C@@H]1CN(c2cc(F)c(C3=CCN(C(=O)N(C)C)CC3)cc2NC(=O)c2c[nH]c(=O)cc2C(F)(F)F)C[C@H](C)N1C] | N-[5-[1-(dimethylcarbamoyl)-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00101 |
| 286 | 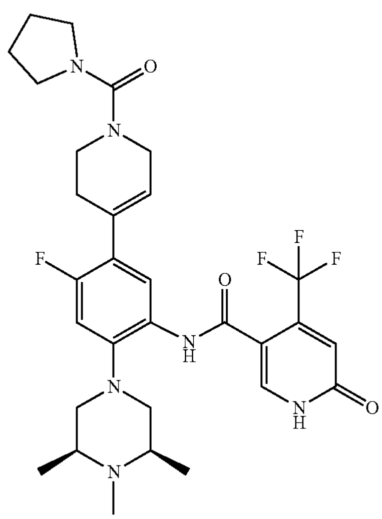 [SMILES: C[C@@H]1CN(c2cc(F)c(C3=CCN(C(=O)N4CCCC4)CC3)cc2NC(=O)c2c[nH]c(=O)cc2C(F)(F)F)C[C@H](C)N1C] | N-[4-fluoro-5-[1-(pyrrolidine-1-carbonyl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00118 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 287 | 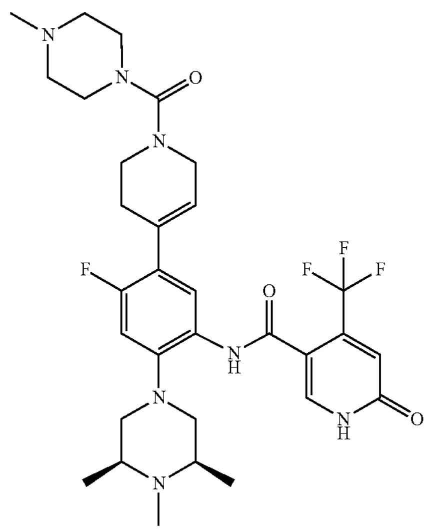 [SMILES: C[C@@H]1CN(c2cc(F)c(C3=CCN(C(=O)N4CCN(C)CC4)CC3)cc2NC(=O)c2c[nH]c(=O)cc2C(F)(F)F)C[C@H](C)N1C] | N-[4-fluoro-5-[1-(4-methylpiperazine-1-carbonyl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00139 |
| 288 | 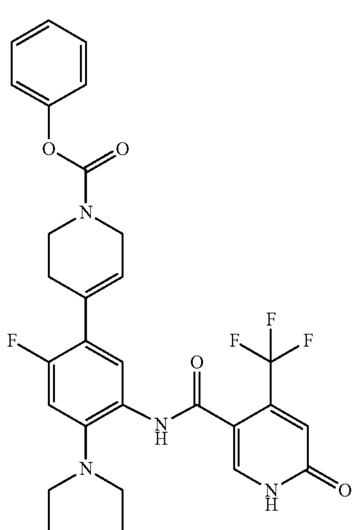 | phenyl 4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.00111 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 289 | 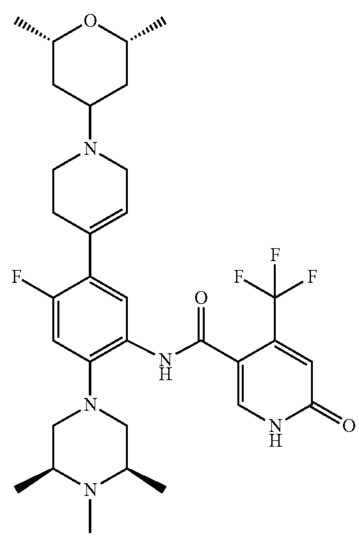 [SMILES: C[C@@H]1CC(N2CC=C(c3cc(NC(=O)c4c[nH]c(=O)cc4C(F)(F)F)c(N4C[C@@H](C)N(C)[C@@H](C)C4)cc3F)CC2)C[C@H](C)O1] | N-[4-fluoro-5-[1-[rac-(2R,6S)-2,6-dimethyloxan-4-yl]-3,6-dihydro-2H-pyridin-4-yl]-2-[rac-(3S,5R)-3,4,5-trimethylpiperazin-1-yl]phenyl]-6-oxo-4-(trifluoromethyl)-1H-pyridine-3-carboxamide | 0.00374 |
| 290 | 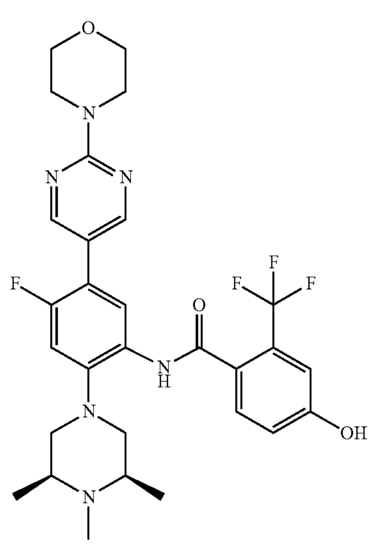 [SMILES: C[C@@H]1CN(c2cc(F)c(-c3cnc(N4CCOCC4)nc3)cc2NC(=O)c2ccc(O)cc2C(F)(F)F)C[C@H](C)N1C] | N-[4-fluoro-5-(2-morpholin-4-ylpyrimidin-5-yl)-2-[rac-(3R,5S)-3,4,5-trimethylpiperazin-1-yl]phenyl]-4-hydroxy-2-(trifluoromethyl)benzamide | 0.0089 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 291 | 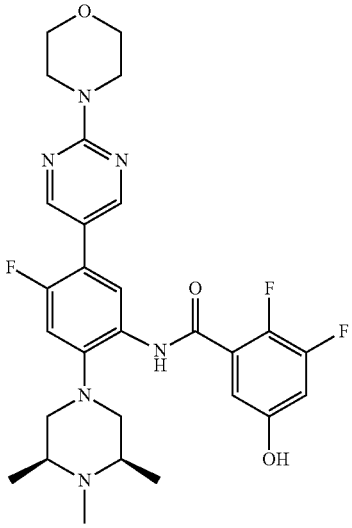 [SMILES: C[C@@H]1CN(c2cc(F)c(-c3cnc(N4CCOCC4)nc3)cc2NC(=O)c2cc(O)cc(F)c2F)C[C@H](C)N1C] | 2,3-difluoro-N-[4-fluoro-5-(2-morpholin-4-ylpyrimidin-5-yl)-2-[rac-(3R,5S)-3,4,5-trimethylpiperazin-1-yl]phenyl]-5-hydroxybenzamide | 0.00421 |
| 292 | 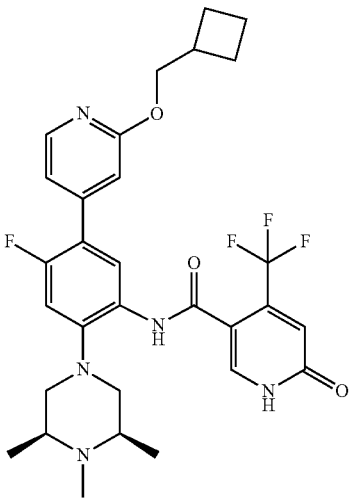 [SMILES: C[C@@H]1CN(c2cc(F)c(-c3ccnc(OCC4CCC4)c3)cc2NC(=O)c2c[nH]c(=O)cc2C(F)(F)F)C[C@H](C)N1C] | N-[5-[2-(cyclobutylmethoxy)pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00432 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 293 | 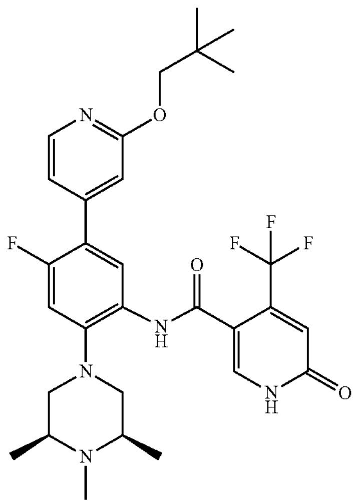 [SMILES: C[C@@H]1CN(c2cc(F)c(-c3ccnc(OCC(C)(C)C)c3)cc2NC(=O)c2c[nH]c(=O)cc2C(F)(F)F)C[C@H](C)N1C] | N-[5-[2-(2,2-dimethylpropoxy)pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.003 |
| 294 | 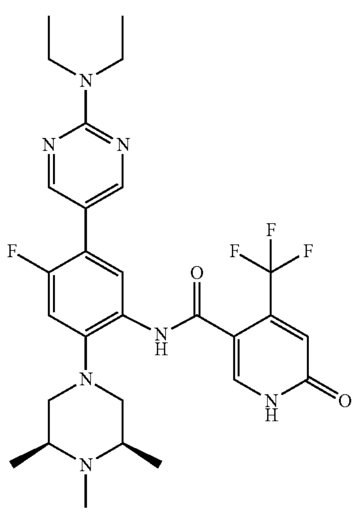 [SMILES: CCN(CC)c1ncc(-c2cc(NC(=O)c3c[nH]c(=O)cc3C(F)(F)F)c(N3C[C@@H](C)N(C)[C@@H](C)C3)cc2F)cn1] | N-[5-[2-(diethylamino)pyrimidin-5-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00224 |

TABLE 1-continued
Binding affinities (K$_D$) derived from surface plasmon resonance (SPR) assays
| Example No. | Structure | IUPAC Name | WDR5 binding affinity (K$_D$, μM) |
|---|---|---|---|
| 295 | 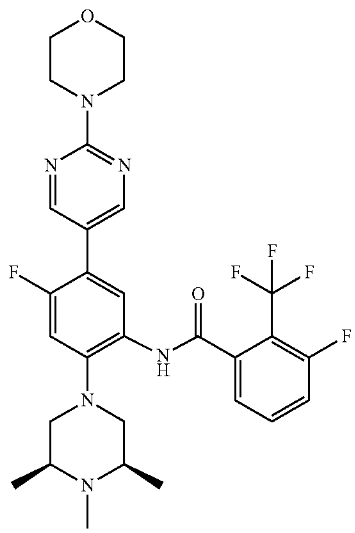 [SMILES: C[C@@H]1CN(c2cc(F)c(-c3cnc(N4CCOCC4)nc3)cc2NC(=O)c2cccc(F)c2C(F)(F)F)C[C@H](C)N1C] | 3-fluoro-N-[4-fluoro-5-(2-morpholin-4-ylpyrimidin-5-yl)-2-[rac-(3R,5S)-3,4,5-trimethylpiperazin-1-yl]phenyl]-2-(trifluoromethyl)benzamide | 0.0111 |
| 296 | 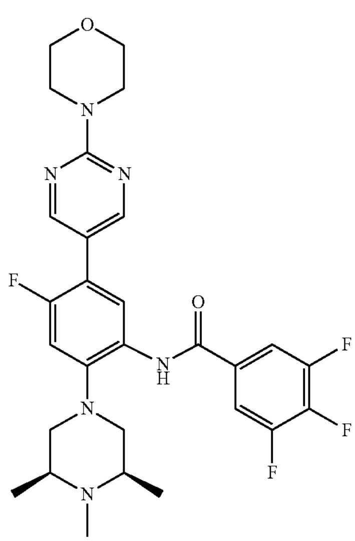 | 3,4,5-trifluoro-N-[4-fluoro-5-(2-morpholin-4-ylpyrimidin-5-yl)-2-[rac-(3R,5S)-3,4,5-trimethylpiperazin-1-yl]phenyl]benzamide | 0.0212 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 297 | 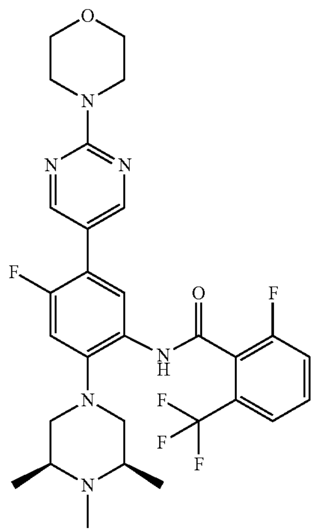 [SMILES: C[C@@H]1CN(c2cc(F)c(-c3cnc(N4CCOCC4)nc3)cc2NC(=O)c2c(F)cccc2C(F)(F)F)C[C@H](C)N1C] | 2-fluoro-N-[4-fluoro-5-(2-morpholin-4-ylpyrimidin-5-yl)-2-[rac-(3R,5S)-3,4,5-trimethylpiperazin-1-yl]phenyl]-6-(trifluoromethyl)benzamide | 0.0229 |
| 298 | 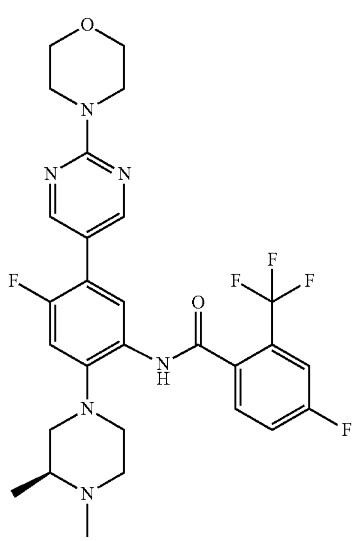 [SMILES: C[C@H]1CN(c2cc(F)c(-c3cnc(N4CCOCC4)nc3)cc2NC(=O)c2ccc(F)cc2C(F)(F)F)CCN1C] | 4-fluoro-N-[4-fluoro-5-(2-morpholin-4-ylpyrimidin-5-yl)-2-[rac-(3R)-3,4-dimethylpiperazin-1-yl]phenyl]-2-(trifluoromethyl)benzamide | 0.00422 |

TABLE 1-continued
Binding affinities ($K_D$) derived from surface plasmon resonance (SPR) assays
| Example No. | Structure | IUPAC Name | WDR5 binding affinity ($K_D$, μM) |
|---|---|---|---|
| 299 | 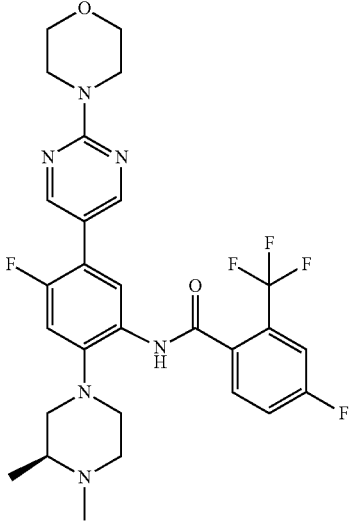 [SMILES: C[C@H]1CN(c2cc(F)c(-c3cnc(N4CCOCC4)nc3)cc2NC(=O)c2ccc(F)cc2C(F)(F)F)CCN1C] | 4-fluoro-N-[4-fluoro-5-(2-morpholin-4-ylpyrimidin-5-yl)-2-[rac-(3R)-3,4-dimethylpiperazin-1-yl]phenyl]-2-(trifluoromethyl)benzamide | 0.000569 |
| 300 | 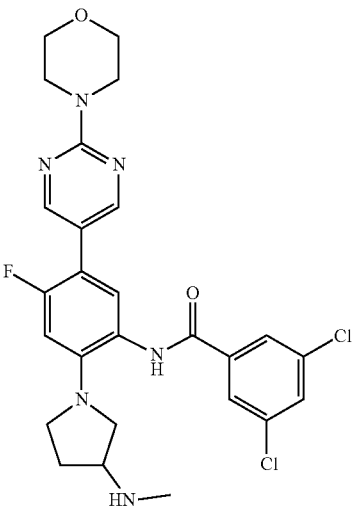 [SMILES: CNC1CCN(c2cc(F)c(-c3cnc(N4CCOCC4)nc3)cc2NC(=O)c2cc(Cl)cc(Cl)c2)C1] | 3,5-dichloro-N-[4-fluoro-2-[3-(methylamino)pyrrolidin-1-yl]-5-(2-morpholin-4-ylpyrimidin-5-yl)phenyl]benzamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 301 | 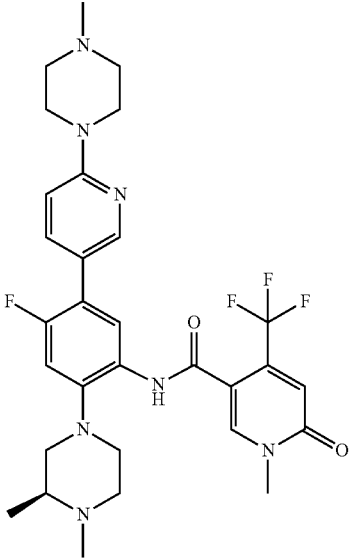 | N-[4-fluoro-5-[6-(4-methylpiperazin-1-yl)pyridin-3-yl]-2-[rac-(3R)-3,4-dimethylpiperazin-1-yl]phenyl]-1-methyl-6-oxo-(trifluoromethyl)pyridine-3-carboxamide | 0.00526 |
| 302 | 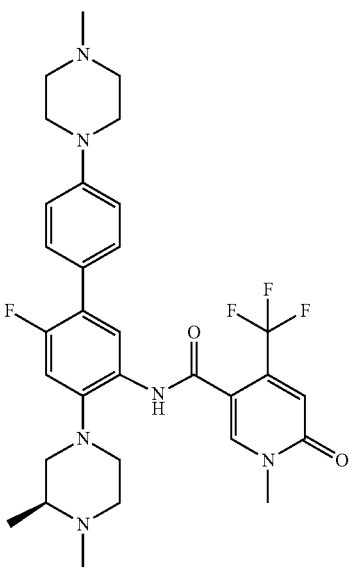 [SMILES: C[C@H]1CN(c2cc(F)c(-c3ccc(N4CCN(C)CC4)cc3)cc2NC(=O)c2cn(C)c(=O)cc2C(F)(F)F)CCN1C] | N-[4-fluoro-5-[4-(4-methylpiperazin-1-yl)phenyl]-2-[rac-(3R)-3,4-dimethylpiperazin-1-yl]phenyl]-1-methyl-6-oxo-4-(trifluoromethyl)pyridine-3-carboxamide | 0.00537 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 303 | 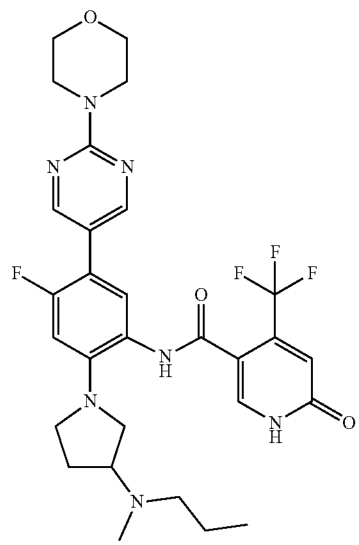 [SMILES: CCCN(C)C1CCN(c2cc(F)c(-c3cnc(N4CCOCC4)nc3)cc2NC(=O)c2c[nH]c(=O)cc2C(F)(F)F)C1] | N-[4-fluoro-2-[3-[methyl(propyl)amino]pyrrolidin-1-yl]-5-(2-morpholin-4-ylpyrimidin-5-yl)phenyl]-6-oxo-4-(trifluoromethyl)-1H-pyridine-3-carboxamide | 0.00168 |
| 304 | 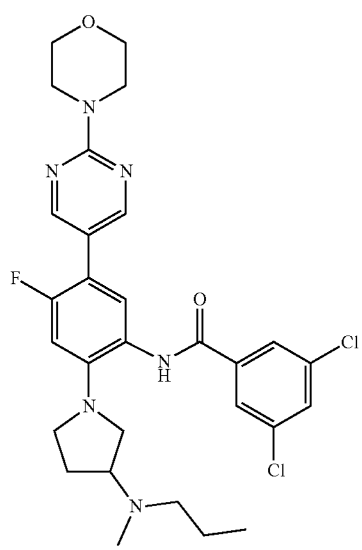 [SMILES: CCCN(C)C1CCN(c2cc(F)c(-c3cnc(N4CCOCC4)nc3)cc2NC(=O)c2cc(Cl)cc(Cl)c2)C1] | 3,5-dichloro-N-[4-fluoro-2-[3-[methyl(propyl)amino]pyrrolidin-1-yl]-5-(2-morpholin-4-ylpyrimidin-5-yl)phenyl]benzamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 305 | 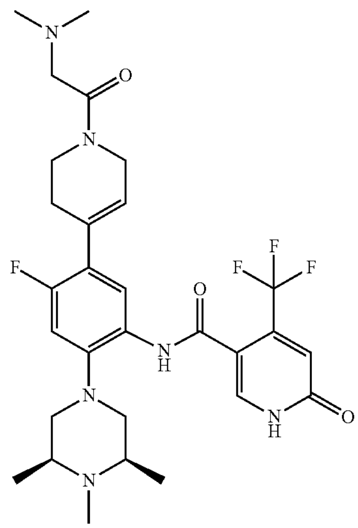 [SMILES: C[C@@H]1CN(c2cc(F)c(C3=CCN(C(=O)CN(C)C)CC3)cc2NC(=O)c2c[nH]c(=O)cc2C(F)(F)F)C[C@H](C)N1C] | N-[5-[1-[2-(dimethylamino)acetyl]-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00261 |
| 306 | 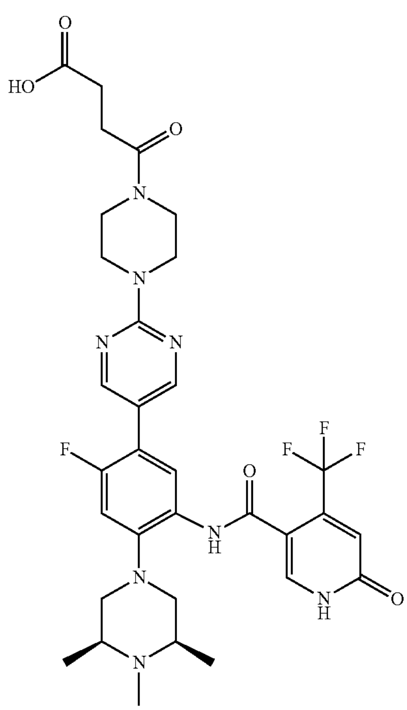 [SMILES: C[C@@H]1CN(c2cc(F)c(-c3cnc(N4CCN(C(=O)CCC(=O)O)CC4)nc3)cc2NC(=O)c2c[nH]c(=O)cc2C(F)(F)F)C[C@H](C)N1C] | 4-[4-[5-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]pyrimidin-2-yl]piperazin-1-yl]-4-oxobutanoic acid | 0.000789 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 307 | 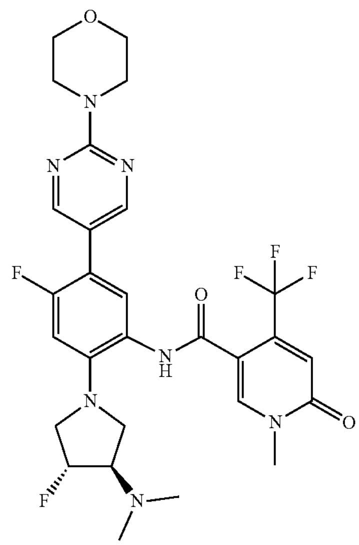 [SMILES: CN(C)[C@@H]1CN(c2cc(F)c(-c3cnc(N4CCOCC4)nc3)cc2NC(=O)c2cn(C)c(=O)cc2C(F)(F)F)C[C@H]1F] | N-[4-fluoro-5-(2-morpholin-4-ylpyrimidin-5-yl)-2-[rac-(3R,4R)-3-(dimethylamino)-4-fluoropyrrolidin-1-yl]phenyl]-1-methyl-6-oxo-4-(trifluoromethyl)pyridine-3-carboxamide | — |
| 308 | 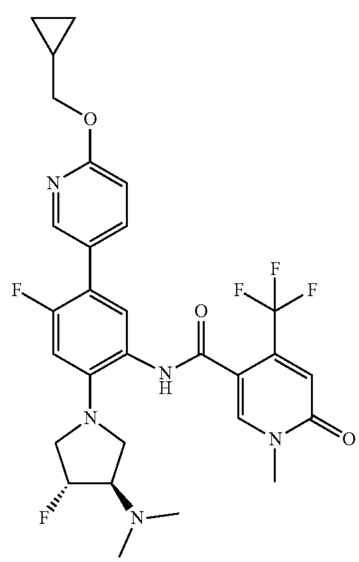 [SMILES: CN(C)[C@@H]1CN(c2cc(F)c(-c3ccc(OCC4CC4)nc3)cc2NC(=O)c2cn(C)c(=O)cc2C(F)(F)F)C[C@H]1F] | N-[5-[6-(cyclopropylmethoxy)pyridin-3-yl]-4-fluoro-2-[rac-(3R,4R)-3-(dimethylamino)-4-fluoropyrrolidin-1-yl]phenyl]-1-methyl-6-oxo-4-(trifluoromethyl)pyridine-3-carboxamide | — |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 309 | 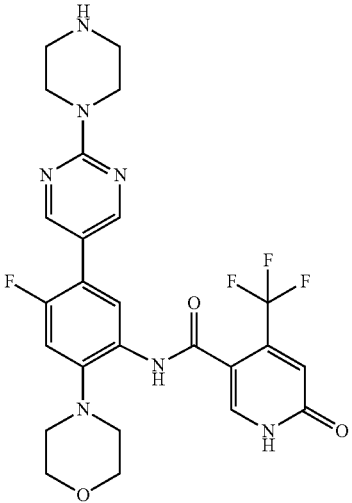 [SMILES: O=C(Nc1cc(-c2cnc(N3CCNCC3)nc2)c(F)cc1N1CCOCC1)c1c[nH]c(=O)cc1C(F)(F)F] | N-[4-fluoro-2-morpholin-4-yl-5-(2-piperazin-1-ylpyrimidin-5-yl)phenyl]-6-oxo-4-(trifluoromethyl)-1H-pyridine-3-carboxamide | — |
| 310 | 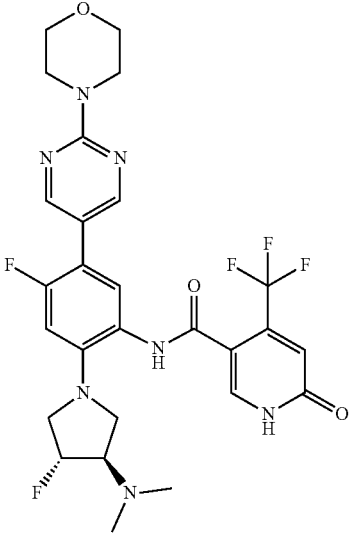 | N-[4-fluoro-5-(2-morpholin-4-ylpyrimidin-5-yl)-2-[rac-(3R,4R)-3-(dimethylamino)-4-fluoropyrrolidin-1-yl]phenyl]-6-oxo-4-(trifluoromethyl)-1H-pyridine-3-carboxamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 311 | 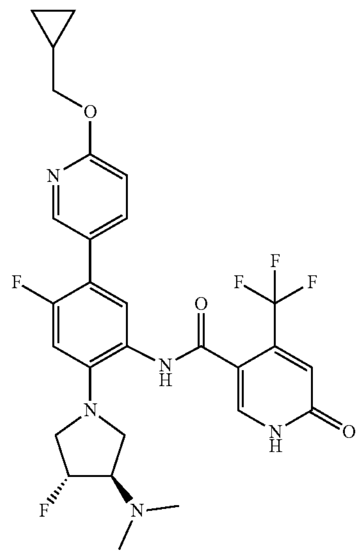 | N-[5-[6-(cyclopropylmethoxy) pyridin-3-yl]-4-fluoro-2-[rac-(3R,4R)-3-(dimethylamino)-4-fluoropyrrolidin-1-yl]phenyl]-6-oxo-4-(trifluoromethyl)-1H-pyridine-3-carboxamide | — |
| 312 | 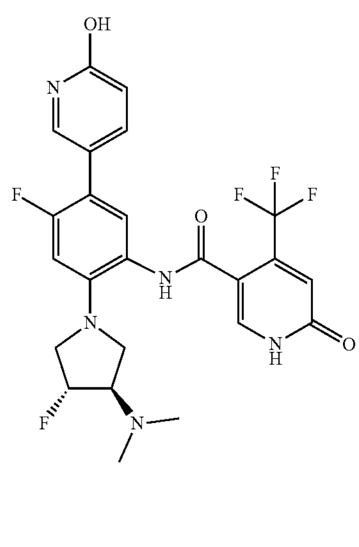 [SMILES: CN(C)[C@@H]1CN(c2cc(F)c(-c3ccc(O)nc3)cc2NC(=O)c2c[nH]c(=O)cc2C(F)(F)F)C[C@H]1F] | N-[4-fluoro-5-(6-hydroxypyridin-3-yl)-2-[rac-(3R,4R)-3-(dimethylamino)-4-fluoropyrrolidin-1-yl]phenyl]-6-oxo-4-(trifluoromethyl)-1H-pyridine-3-carboxamide | — |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 313 | 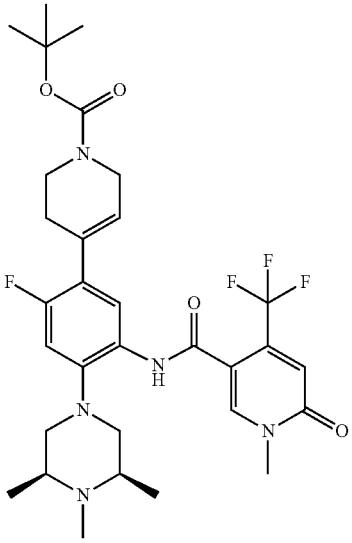 | tert-butyl 4-[2-fluoro-5-[[1-methyl-6-oxo-4-(trifluoromethyl)pyridine-3-carbonyl]amino]-4-[rac-(3R,5S)-3,4,5-trimethylpiperazin-1-yl]phenyl]-3,6-dihydro-2H-pyridine-1-carboxylate | 0.0031 |
| 314 | 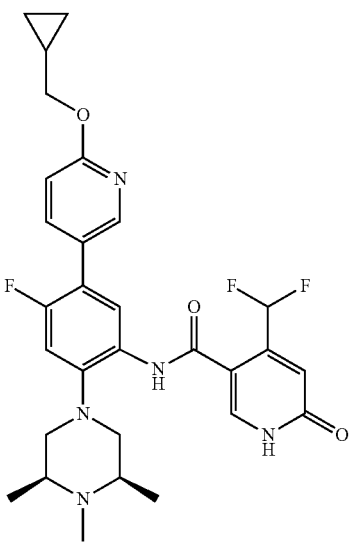 [SMILES: C[C@@H]1CN(c2cc(F)c(-c3ccc(OCC4CC4)nc3)cc2NC(=O)c2c[nH]c(=O)cc2C(F)F)C[C@H](C)N1C] | N-[5-[6-(cyclopropylmethoxy)pyridin-3-yl]-4-fluoro-2-[rac-(3R,5S)-3,4,5-trimethylpiperazin-1-yl]phenyl]-4-(difluoromethyl)-6-oxo-1H-pyridine-3-carboxamide | 0.00167 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 315 | 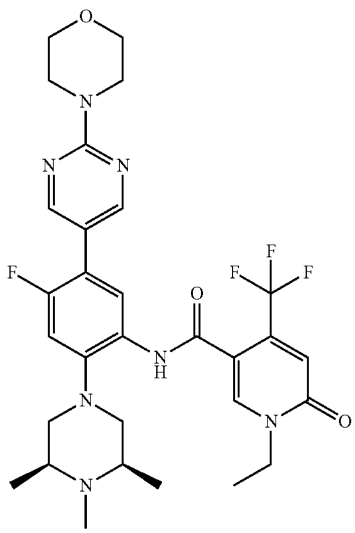 | 1-ethyl-N-[4-fluoro-5-(2-morpholin-4-ylpyrimidin-5-yl)-2-[rac-(3R,5S)-3,4,5-trimethylpiperazin-1-yl]phenyl]-6-oxo-4-(trifluoromethyl)pyridine-3-carboxamide | 0.00849 |
| 316 | 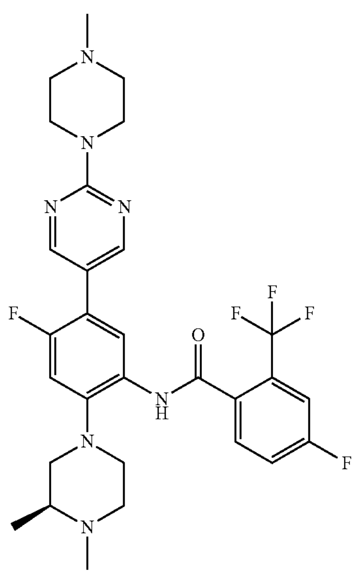 [SMILES: C[C@H]1CN(c2cc(F)c(-c3cnc(N4CCN(C)CC4)nc3)cc2NC(=O)c2ccc(F)cc2C(F)(F)F)CCN1C] | 4-fluoro-N-[4-fluoro-5-[2-(4-methylpiperazin-1-yl)pyrimidin-5-yl]-2-[rac-(3R)-3,4-dimethylpiperazin-1-yl]phenyl]-2-(trifluoromethyl)benzamide | 0.000989 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 317 | 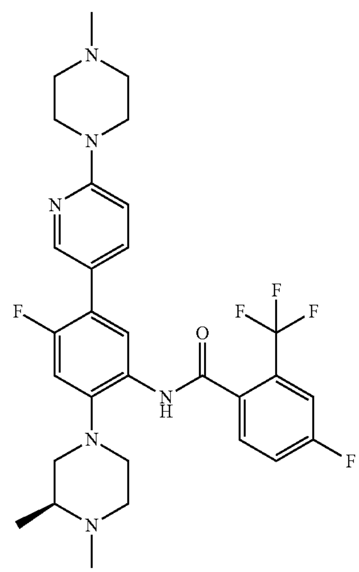 [SMILES: C[C@H]1CN(c2cc(F)c(-c3ccc(N4CCN(C)CC4)nc3)cc2NC(=O)c2ccc(F)cc2C(F)(F)F)CCN1C] | 4-fluoro-N-[4-fluoro-5-[6-(4-methylpiperazin-1-yl)pyridin-3-yl]-2-[rac-(3R)-3,4-dimethylpiperazin-1-yl]phenyl]-2-(trifluoromethyl)benzamide | 0.00554 |
| 318 | 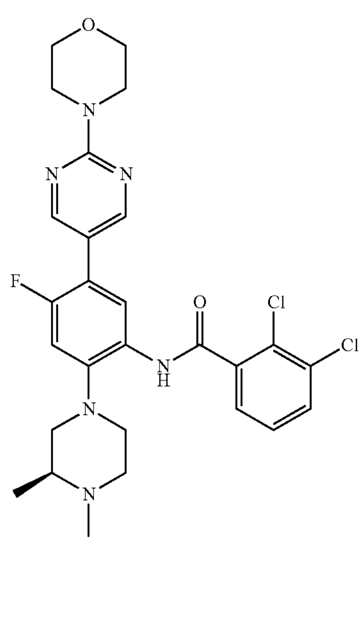 [SMILES: C[C@H]1CN(c2cc(F)c(-c3cnc(N4CCOCC4)nc3)cc2NC(=O)c2cccc(Cl)c2Cl)CCN1C] | 2,3-dichloro-N-[4-fluoro-5-(2-morpholin-4-ylpyrimidin-5-yl)-2-[rac-(3R)-3,4-dimethylpiperazin-1-yl]phenyl]benzamide | 0.00668 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 319 | 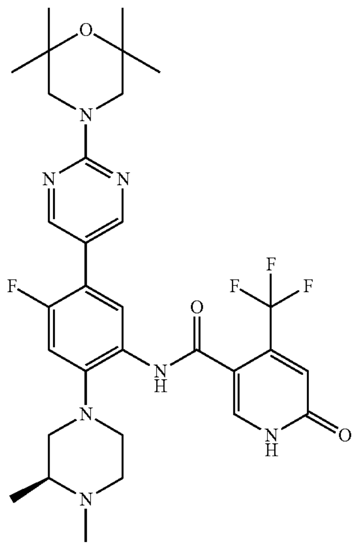 [SMILES: C[C@H]1CN(c2cc(F)c(-c3cnc(N4CC(C)(C)OC(C)(C)C4)nc3)cc2NC(=O)c2c[nH]c(=O)cc2C(F)(F)F)CCN1C] | N-[4-fluoro-2-[rac-(3R)-3,4-dimethylpiperazin-1-yl]-5-[2-(2,2,6,6-tetramethylmorpholin-4-yl)pyrimidin-5-yl]phenyl]-6-oxo-4-(trifluoromethyl)-1H-pyridine-3-carboxamide | 0.00161 |
| 320 | 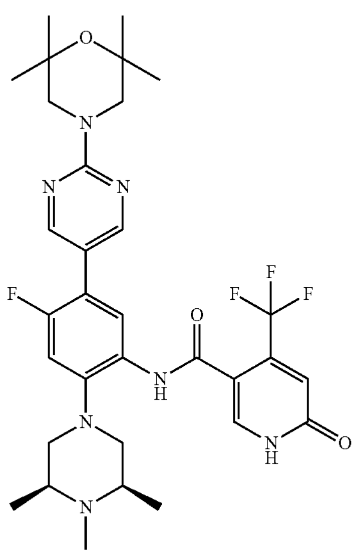 [SMILES: C[C@@H]1CN(c2cc(F)c(-c3cnc(N4CC(C)(C)OC(C)(C)C4)nc3)cc2NC(=O)c2c[nH]c(=O)cc2C(F)(F)F)C[C@H](C)N1C] | N-[4-fluoro-2-[rac-(3R,5S)-3,4,5-trimethylpiperazin-1-yl]-5-[2-(2,2,6,6-tetramethylmorpholin-4-yl)pyrimidin-5-yl]phenyl]-6-oxo-4-(trifluoromethyl)-1H-pyridine-3-carboxamide | 0.000722 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 321 | 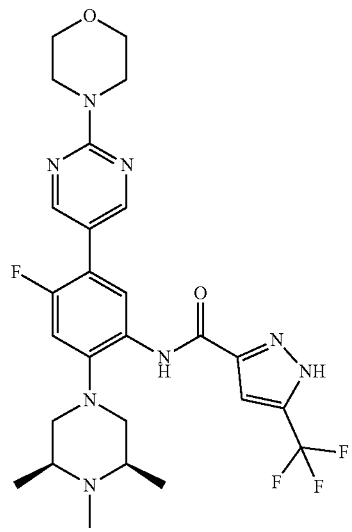 [SMILES: C[C@@H]1CN(c2cc(F)c(-c3cnc(N4CCOCC4)nc3)cc2NC(=O)c2cc(C(F)(F)F)[nH]n2)C[C@H](C)N1C] | N-[4-fluoro-5-(2-morpholin-4-ylpyrimidin-5-yl)-2-[rac-(3R,5S)-3,4,5-trimethylpiperazin-1-yl]phenyl]-5-(trifluoromethyl)-1H-pyrazole-3-carboxamide | 0.0631 |
| 322 | 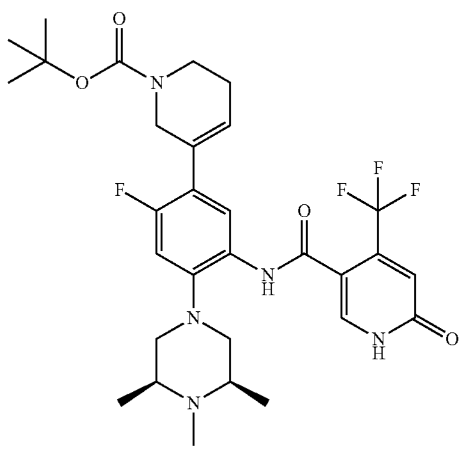 | tert-butyl 5-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.00136 |
| 323 | 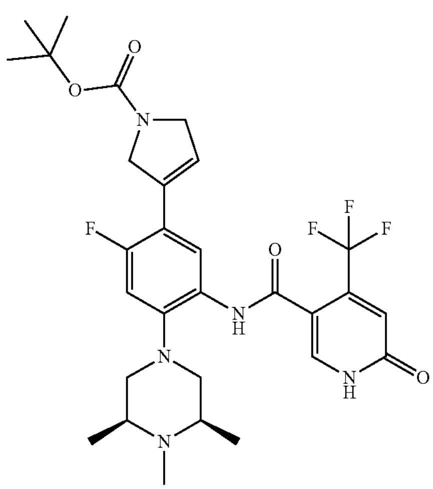 [SMILES: C[C@@H]1CN(c2cc(F)c(C3=CCN(C(=O)OC(C)(C)C)C3)cc2NC(=O)c2c[nH]c(=O)cc2C(F)(F)F)C[C@H](C)N1C] | tert-butyl 3-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-2,5-dihydropyrrole-1-carboxylate | 0.00248 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 324 | 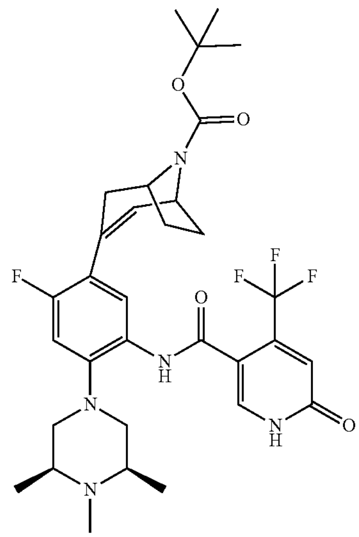 [SMILES: C[C@@H]1CN(c2cc(F)c(C3=CC4CCC(C3)N4C(=O)OC(C)(C)C)cc2NC(=O)c2c[nH]c(=O)cc2C(F)(F)F)C[C@H](C)N1C] | tert-butyl 3-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-8-azabicyclo[3.2.1]oct-2-ene-8-carboxylate | 0.0152 |
| 325 | 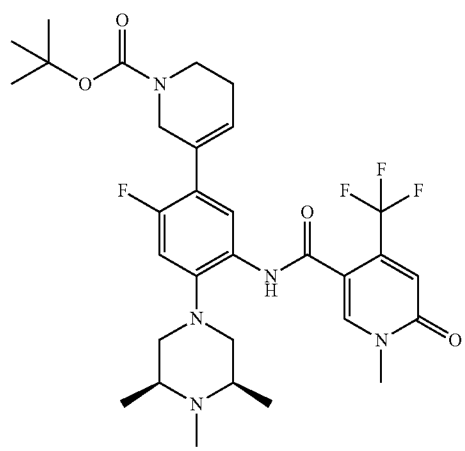 | tert-butyl 5-[2-fluoro-5-[[1-methyl-6-oxo-4-(trifluoromethyl)pyridine-3-carbonyl]amino]-4-[rac-(3R,5S)-3,4,5-trimethylpiperazin-1-yl]phenyl]-3,6-dihydro-2H-pyridine-1-carboxylate | 0.0073 |
| 326 | 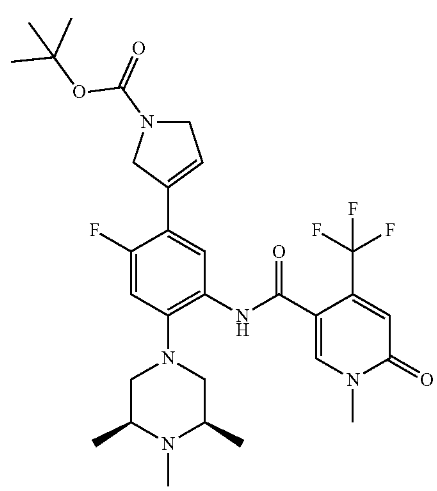 [SMILES: C[C@@H]1CN(c2cc(F)c(C3=CCN(C(=O)OC(C)(C)C)C3)cc2NC(=O)c2cn(C)c(=O)cc2C(F)(F)F)C[C@H](C)N1C] | tert-butyl 3-[2-fluoro-5-[[1-methyl-6-oxo-4-(trifluoromethyl)pyridine-3-carbonyl]amino]-4-[rac-(3R,5S)-3,4,5-trimethylpiperazin-1-yl]phenyl]-2,5-dihydropyrrole-1-carboxylate | 0.00305 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 327 | 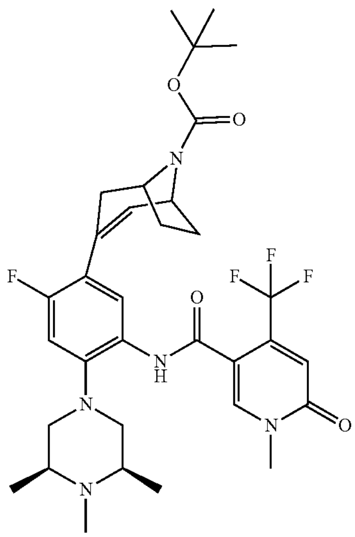 | tert-butyl 3-[2-fluoro-5-[[1-methyl-6-oxo-4-(trifluoromethyl)pyridine-3-carbonyl]amino]-4-[rac-(3R,5S)-3,4,5-trimethylpiperazin-1-yl]phenyl]-8-azabicyclo[3.2.1]oct-2-ene-8-carboxylate | 0.123 |
| 328 | 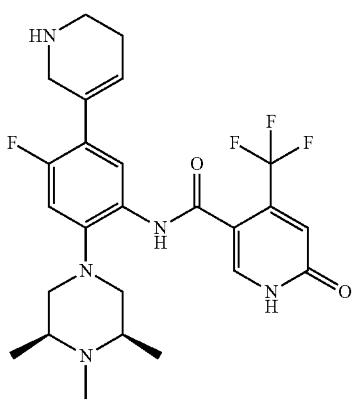 [SMILES: C[C@@H]1CN(c2cc(F)c(C3=CCCNC3)cc2NC(=O)c2c[nH]c(=O)cc2C(F)(F)F)C[C@H](C)N1C] | N-[4-fluoro-2-[rac-(3R,5S)-3,4,5-trimethylpiperazin-1-yl]-5-(1,2,3,6-tetrahydropyridin-5-yl)phenyl]-6-oxo-4-(trifluoromethyl)-1H-pyridine-3-carboxamide | 0.00189 |
| 329 | 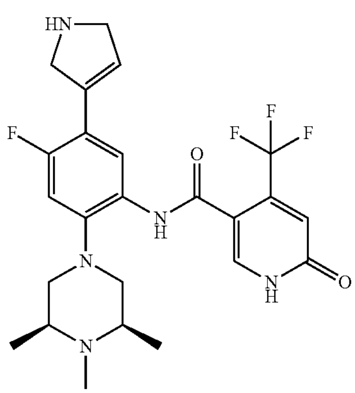 [SMILES: C[C@@H]1CN(c2cc(F)c(C3=CCNC3)cc2NC(=O)c2c[nH]c(=O)cc2C(F)(F)F)C[C@H](C)N1C] | N-[5-(2,5-dihydro-1H-pyrrol-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00405 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 330 | 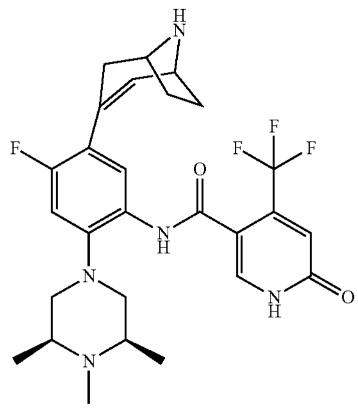 [SMILES: C[C@@H]1CN(c2cc(F)c(C3=CC4CCC(C3)N4)cc2NC(=O)c2c[nH]c(=O)cc2C(F)(F)F)C[C@H](C)N1C] | N-[5-(8-azabicyclo[3.2.1]oct-2-en-3-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00574 |
| 331 | 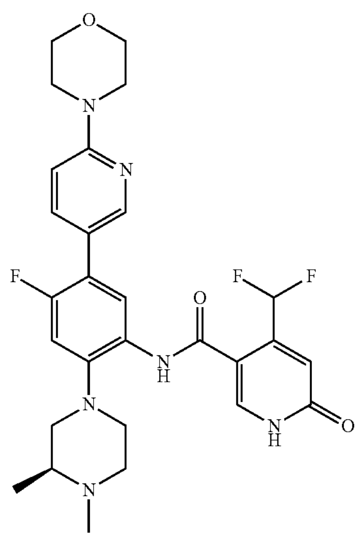 | 4-(difluoromethyl)-N-[4-fluoro-5-(6-morpholin-4-ylpyridin-3-yl)-2-[rac-(3R)-3,4-dimethylpiperazin-1-yl]phenyl]-6-oxo-1H-pyridine-3-carboxamide | 0.00201 |
| 332 | 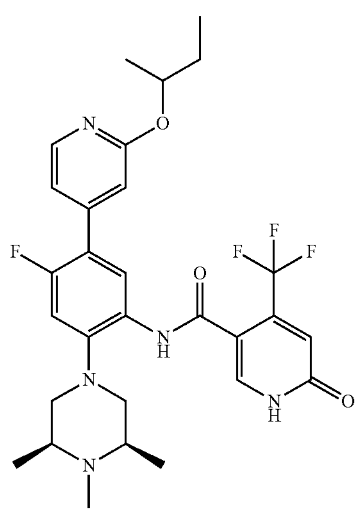 [SMILES: CCC(C)Oc1cc(-c2cc(NC(=O)c3c[nH]c(=O)cc3C(F)(F)F)c(N3C[C@@H](C)N(C)[C@@H](C)C3)cc2F)ccn1] | N-[5-(2-butan-2-yloxypyridin-4-yl)-4-fluoro-2-[rac-(3R,5S)-3,4,5-trimethylpiperazin-1-yl]phenyl]-6-oxo-4-(trifluoromethyl)-1H-pyridine-3-carboxamide | — |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 333 | 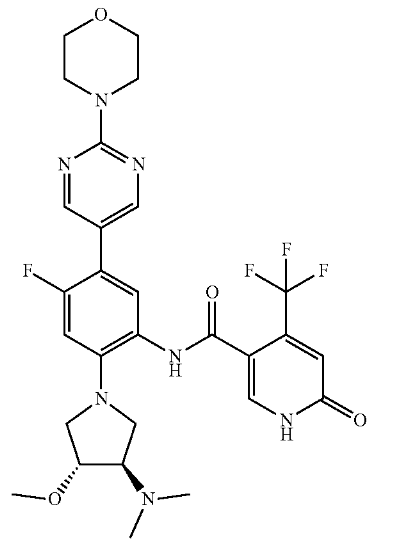 [SMILES: CO[C@@H]1CN(c2cc(F)c(-c3cnc(N4CCOCC4)nc3)cc2NC(=O)c2c[nH]c(=O)cc2C(F)(F)F)C[C@H]1N(C)C] | N-[4-fluoro-5-(2-morpholin-4-ylpyrimidin-5-yl)-2-[rac-(3R,4R)-3-(dimethylamino)-4-methoxypyrrolidin-1-yl]phenyl]-6-oxo-4-(trifluoromethyl)-1H-pyridine-3-carboxamide | — |
| 334 | 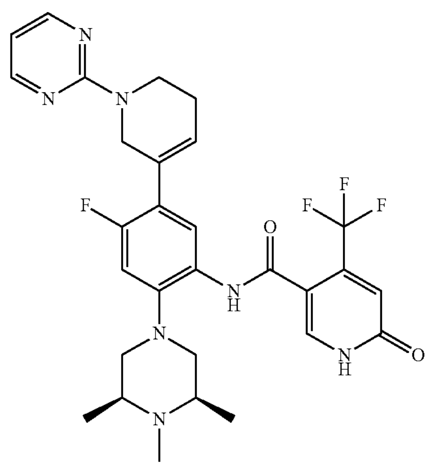 [SMILES: C[C@@H]1CN(c2cc(F)c(C3=CCCN(c4ncccn4)C3)cc2NC(=O)c2c[nH]c(=O)cc2C(F)(F)F)C[C@H](C)N1C] | N-[4-fluoro-5-(1-pyrimidin-2-yl-3,6-dihydro-2H-pyridin-5-yl)-2-[rac-(3R,5S)-3,4,5-trimethylpiperazin-1-yl]phenyl]-6-oxo-4-(trifluoromethyl)-1H-pyridine-3-carboxamide | 9.5e−05 |
| 335 | 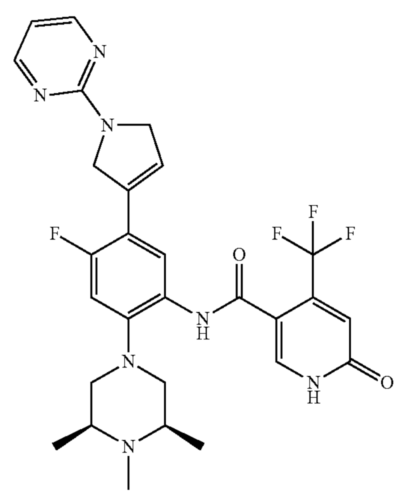 [SMILES: C[C@@H]1CN(c2cc(F)c(C3=CCN(c4ncccn4)C3)cc2NC(=O)c2c[nH]c(=O)cc2C(F)(F)F)C[C@H](C)N1C] | N-[4-fluoro-5-(1-pyrimidin-2-yl-2,5-dihydropyrrol-3-yl)-2-[rac-(3R,5S)-3,4,5-trimethylpiperazin-1-yl]phenyl]-6-oxo-4-(trifluoromethyl)-1H-pyridine-3-carboxamide | 0.00256 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 336 | 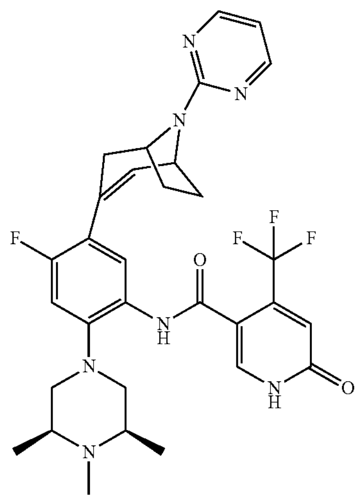 [SMILES: C[C@@H]1CN(c2cc(F)c(C3=CC4CCC(C3)N4c3ncccn3)cc2NC(=O)c2c[nH]c(=O)cc2C(F)(F)F)C[C@H](C)N1C] | N-[4-fluoro-5-(8-pyrimidin-2-yl-8-azabicyclo[3.2.1]oct-2-en-3-yl)-2-[rac-(3R,5S)-3,4,5-trimethylpiperazin-1-yl]phenyl]-6-oxo-4-(trifluoromethyl)-1H-pyridine-3-carboxamide | 0.0125 |
| 337 | 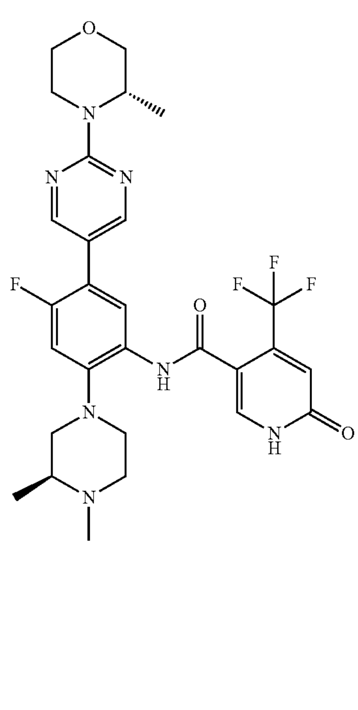 [SMILES: C[C@H]1CN(c2cc(F)c(-c3cnc(N4CCOC[C@@H]4C)nc3)cc2NC(=O)c2c[nH]c(=O)cc2C(F)(F)F)CCN1C] | N-[4-fluoro-2-[rac-(3R)-3,4-dimethylpiperazin-1-yl]-5-[2-[rac-(3R)-3-methylmorpholin-4-yl]pyrimidin-5-yl]phenyl]-6-oxo-4-(trifluoromethyl)-1H-pyridine-3-carboxamide | 0.00116 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 338 | 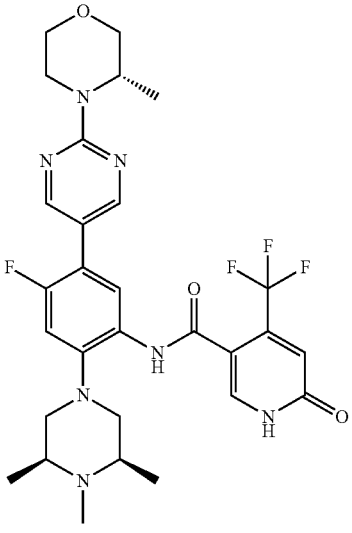 [SMILES: C[C@@H]1CN(c2cc(F)c(-c3cnc(N4CCOC[C@@H]4C)nc3)cc2NC(=O)c2c[nH]c(=O)cc2C(F)(F)F)C[C@H](C)N1C] | N-[4-fluoro-5-[2-[rac-(3R)-3-methylmorpholin-4-yl]pyrimidin-5-yl]-2-[rac-(3S,5R)-3,4,5-trimethylpiperazin-1-yl]phenyl]-6-oxo-4-(trifluoromethyl)-1H-pyridine-3-carboxamide | 0.00208 |
| 339 | 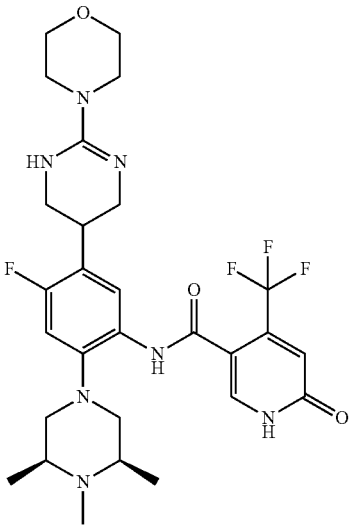 [SMILES: C[C@@H]1CN(c2cc(F)c(C3CN=C(N4CCOCC4)NC3)cc2NC(=O)c2c[nH]c(=O)cc2C(F)(F)F)C[C@H](C)N1C] | N-[4-fluoro-5-(2-morpholin-4-yl-1,4,5,6-tetrahydropyrimidin-5-yl)-2-[rac-(3R,5S)-3,4,5-trimethylpiperazin-1-yl]phenyl]-6-oxo-4-(trifluoromethyl)-1H-pyridine-3-carboxamide | 0.275 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 340 | 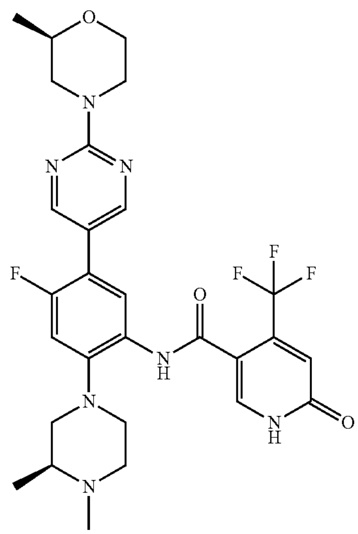 [SMILES: C[C@@H]1CN(c2ncc(-c3cc(NC(=O)c4c[nH]c(=O)cc4C(F)(F)F)c(N4CCN(C)[C@@H](C)C4)cc3F)cn2)CCO1] | N-[4-fluoro-2-[rac-(3S)-3,4-dimethylpiperazin-1-yl]-5-[2-[rac-(2R)-2-methylmorpholin-4-yl]pyrimidin-5-yl]phenyl]-6-oxo-4-(trifluoromethyl)-1H-pyridine-3-carboxamide | 0.000551 |
| 341 | 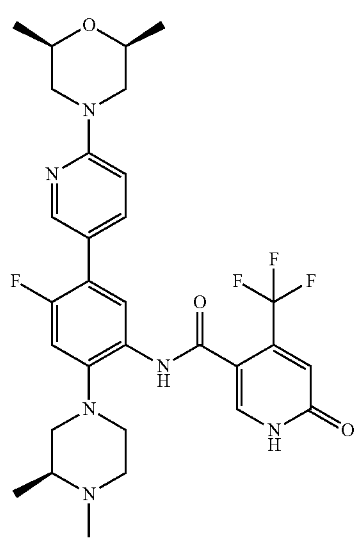 [SMILES: C[C@@H]1CN(c2ccc(-c3cc(NC(=O)c4c[nH]c(=O)cc4C(F)(F)F)c(N4CCN(C)[C@@H](C)C4)cc3F)cn2)C[C@H](C)O1] | N-[4-fluoro-5-[6-[rac-(2R,6S)-2,6-dimethylmorpholin-4-yl]pyridin-3-yl]-2-[rac-(3R)-3,4-dimethylpiperazin-1-yl]phenyl]-6-oxo-4-(trifluoromethyl)-1H-pyridine-3-carboxamide | 0.00197 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 342 | 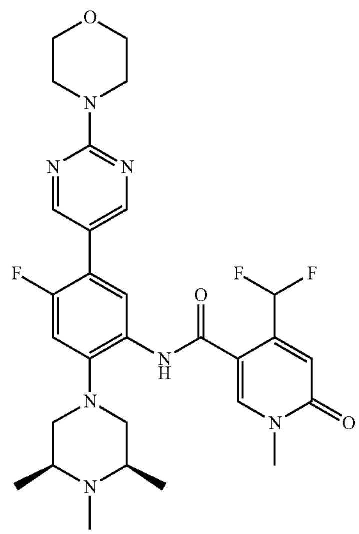 [SMILES: C[C@@H]1CN(c2cc(F)c(-c3cnc(N4CCOCC4)nc3)cc2NC(=O)c2cn(C)c(=O)cc2C(F)F)C[C@H](C)N1C] | 4-(difluoromethyl)-N-[4-fluoro-5-(2-morpholin-4-ylpyrimidin-5-yl)-2-[rac-(3R,5S)-3,4,5-trimethylpiperazin-1-yl]phenyl]-1-methyl-6-oxopyridine-3-carboxamide | 0.00687 |
| 343 | 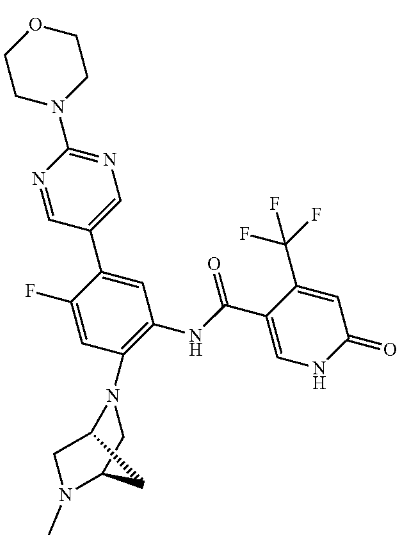 [SMILES: CN1C[C@H]2C[C@@H]1CN2c1cc(F)c(-c2cnc(N3CCOCC3)nc2)cc1NC(=O)c1c[nH]c(=O)cc1C(F)(F)F] | N-[4-fluoro-5-(2-morpholin-4-ylpyrimidin-5-yl)-2-[rac-(1R,4R)-5-methyl-2,5-diazabicyclo[2.2.1]heptan-2-yl]phenyl]-6-oxo-4-(trifluoromethyl)-1H-pyridine-3-carboxamide | — |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 344 | 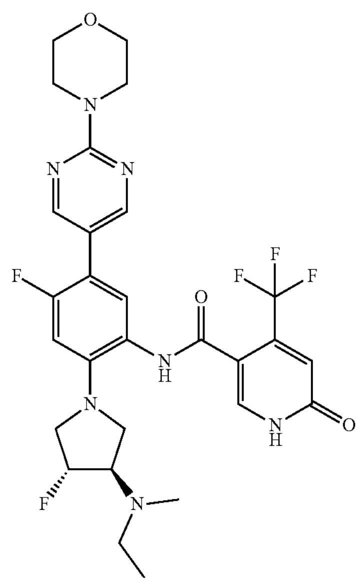 | N-[4-fluoro-5-(2-morpholin-4-ylpyrimidin-5-yl)-2-[rac-(3R,4R)-3-[ethyl(methyl)amino]-4-fluoropyrrolidin-1-yl]phenyl]-6-oxo-4-(trifluoromethyl)-1H-pyridine-3-carboxamide | 0.0124 |
| 345 | 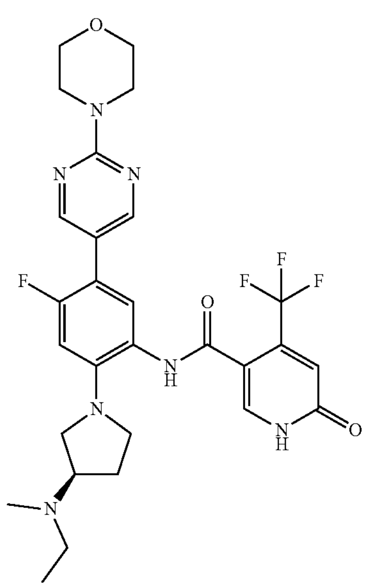 | N-[4-fluoro-5-(2-morpholin-4-ylpyrimidin-5-yl)-2-[rac-(3R)-3-[ethyl(methyl)amino]pyrrolidin-1-yl]phenyl]-6-oxo-4-(trifluoromethyl)-1H-pyridine-3-carboxamide | 0.0012 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 346 | 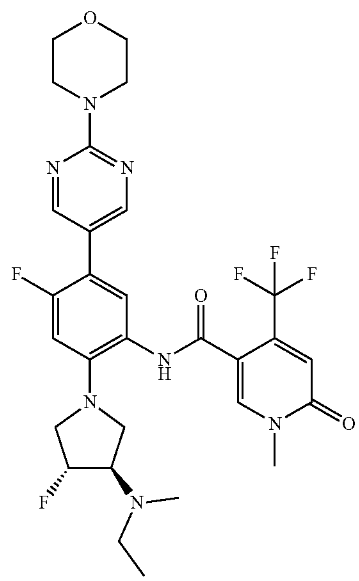 [SMILES: CCN(C)[C@@H]1CN(c2cc(F)c(-c3cnc(N4CCOCC4)nc3)cc2NC(=O)c2cn(C)c(=O)cc2C(F)(F)F)C[C@H]1F] | N-[4-fluoro-5-(2-morpholin-4-ylpyrimidin-5-yl)-2-[rac-(3R,4R)-3-[ethyl(methyl)amino]-4-fluoropyrrolidin-1-yl]phenyl]-1-methyl-6-oxo-4-(trifluoromethyl)pyridine-3-carboxamide | — |
| 347 | 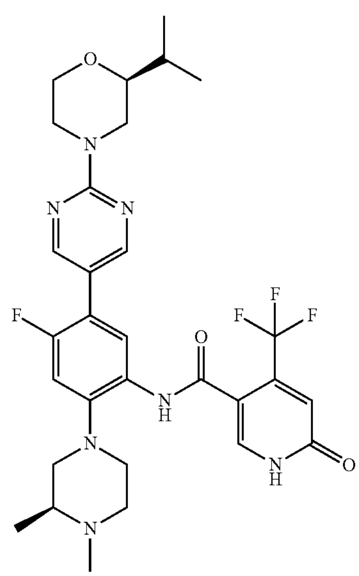 [SMILES: CC(C)[C@H]1CN(c2ncc(-c3cc(NC(=O)c4c[nH]c(=O)cc4C(F)(F)F)c(N4CCN(C)[C@@H](C)C4)cc3F)cn2)CCO1] | N-[4-fluoro-2-[rac-(3R)-3,4-dimethylpiperazin-1-yl]-5-[2-[rac-(2R)-2-propan-2-ylmorpholin-4-yl]pyrimidin-5-yl]phenyl]-6-oxo-4-(trifluoromethyl)-1H-pyridine-3-carboxamide | 0.000606 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 348 | 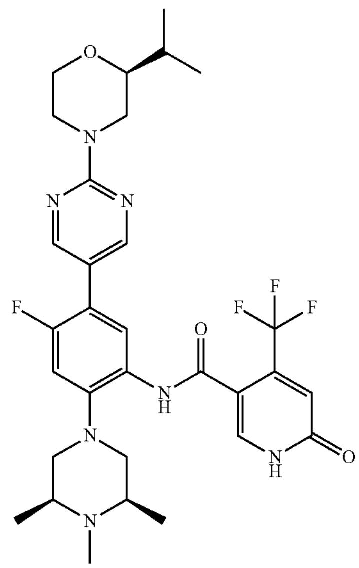 [SMILES: CC(C)[C@H]1CN(c2ncc(-c3cc(NC(=O)c4c[nH]c(=O)cc4C(F)(F)F)c(N4C[C@@H](C)N(C)[C@@H](C)C4)cc3F)cn2)CCO1] | N-[4-fluoro-5-[2-[rac-(2R)-2-propan-2-ylmorpholin-4-yl]pyrimidin-5-yl]-2-[rac-(3S,5R)-3,4,5-trimethylpiperazin-1-yl]phenyl]-6-oxo-4-(trifluoromethyl)-1H-pyridine-3-carboxamide | 0.00228 |
| 349 | 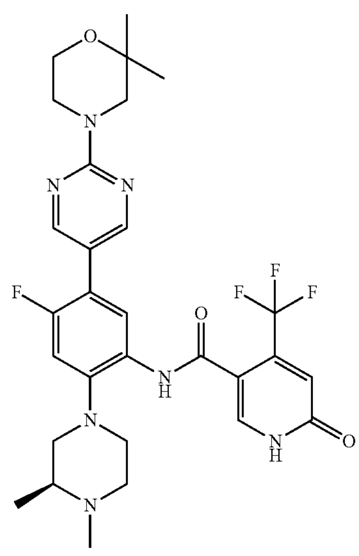 [SMILES: C[C@H]1CN(c2cc(F)c(-c3cnc(N4CCOC(C)(C)C4)nc3)cc2NC(=O)c2c[nH]c(=O)cc2C(F)(F)F)CCN1C] | N-[5-[2-(2,2-dimethylmorpholin-4-yl)pyrimidin-5-yl]-4-fluoro-2-[rac-(3R)-3,4-dimethylpiperazin-1-yl]phenyl]-6-oxo-4-(trifluoromethyl)-1H-pyridine-3-carboxamide | 0.00235 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 350 | 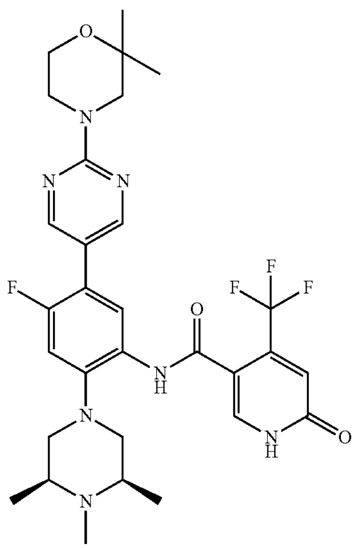 [SMILES: C[C@@H]1CN(c2cc(F)c(-c3cnc(N4CCOC(C)(C)C4)nc3)cc2NC(=O)c2c[nH]c(=O)cc2C(F)(F)F)C[C@H](C)N1C] | N-[5-[2-(2,2-dimethylmorpholin-4-yl)pyrimidin-5-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00142 |
| 351 | 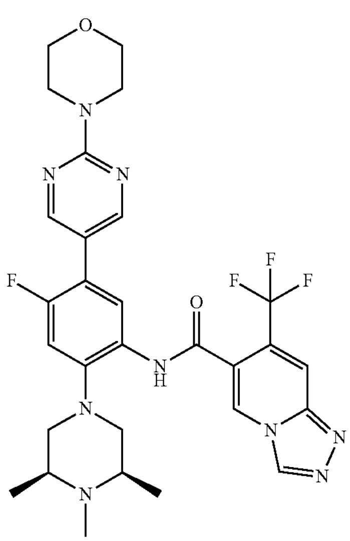 [SMILES: C[C@@H]1CN(c2cc(F)c(-c3cnc(N4CCOCC4)nc3)cc2NC(=O)c2cn3cnnc3cc2C(F)(F)F)C[C@H](C)N1C] | N-[4-fluoro-5-(2-morpholin-4-ylpyrimidin-5-yl)-2-[rac-(3R,5S)-3,4,5-trimethylpiperazin-1-yl]phenyl]-7-(trifluoromethyl)-[1,2,4]triazolo[4,3-a]pyridine-6-carboxamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 352 | 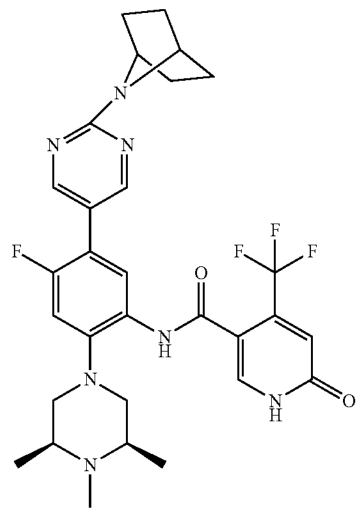 [SMILES: C[C@@H]1CN(c2cc(F)c(-c3cnc(N4C5CCC4CC5)nc3)cc2NC(=O)c2c[nH]c(=O)cc2C(F)(F)F)C[C@H](C)N1C] | N-[5-[2-(7-azabicyclo[2.2.1]heptan-7-yl)pyrimidin-5-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00273 |
| 353 | 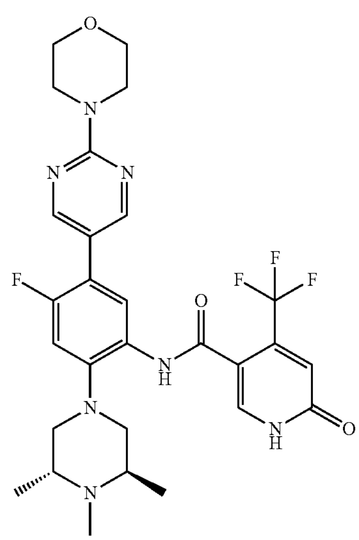 [SMILES: C[C@@H]1CN(c2cc(F)c(-c3cnc(N4CCOCC4)nc3)cc2NC(=O)c2c[nH]c(=O)cc2C(F)(F)F)C[C@@H](C)N1C] | N-[4-fluoro-5-(2-morpholin-4-ylpyrimidin-5-yl)-2-[rac-(3R,5R)-3,4,5-trimethylpiperazin-1-yl]phenyl]-6-oxo-4-(trifluoromethyl)-1H-pyridine-3-carboxamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 354 | 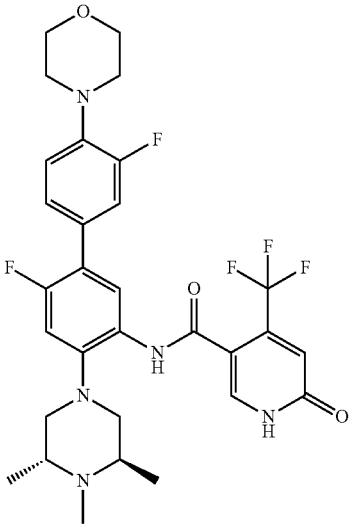 [SMILES: C[C@@H]1CN(c2cc(F)c(-c3ccc(N4CCOCC4)c(F)c3)cc2NC(=O)c2c[nH]c(=O)cc2C(F)(F)F)C[C@@H](C)N1C] | N-[4-fluoro-5-(3-fluoro-4-morpholin-4-ylphenyl)-2-[rac-(3R,5R)-3,4,5-trimethylpiperazin-1-yl]phenyl]-6-oxo-4-(trifluoromethyl)-1H-pyridine-3-carboxamide | — |
| 355 | 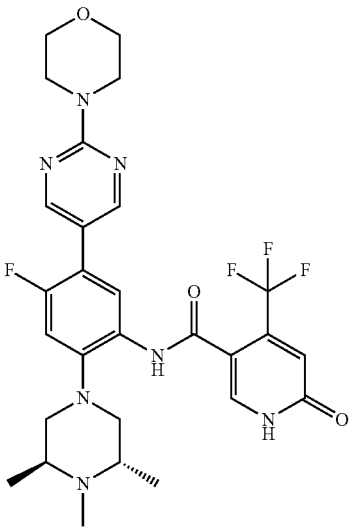 [SMILES: C[C@H]1CN(c2cc(F)c(-c3cnc(N4CCOCC4)nc3)cc2NC(=O)c2c[nH]c(=O)cc2C(F)(F)F)C[C@H](C)N1C] | N-[4-fluoro-5-(2-morpholin-4-ylpyrimidin-5-yl)-2-[rac-(3R,5R)-3,4,5-trimethylpiperazin-1-yl]phenyl]-6-oxo-4-(trifluoromethyl)-1H-pyridine-3-carboxamide | 0.0379 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 356 | 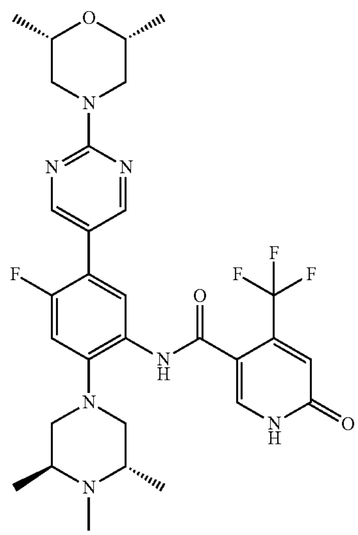 [SMILES: C[C@@H]1CN(c2ncc(-c3cc(NC(=O)c4c[nH]c(=O)cc4C(F)(F)F)c(N4C[C@H](C)N(C)[C@@H](C)C4)cc3F)cn2)C[C@H](C)O1] | N-[4-fluoro-5-[2-[rac-(2R,6S)-2,6-dimethylmorpholin-4-yl]pyrimidin-5-yl]-2-[rac-(3R,5R)-3,4,5-trimethylpiperazin-1-yl]phenyl]-6-oxo-4-(trifluoromethyl)-1H-pyridine-3-carboxamide | 0.0199 |
| 357 | 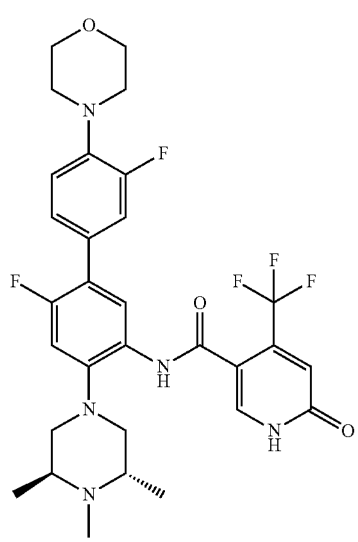 [SMILES: C[C@H]1CN(c2cc(F)c(-c3ccc(N4CCOCC4)c(F)c3)cc2NC(=O)c2c[nH]c(=O)cc2C(F)(F)F)C[C@H](C)N1C] | N-[4-fluoro-5-(3-fluoro-4-morpholin-4-ylphenyl)-2-[rac-(3R,5R)-3,4,5-trimethylpiperazin-1-yl]phenyl]-6-oxo-4-(trifluoromethyl)-1H-pyridine-3-carboxamide | 0.133 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 358 | 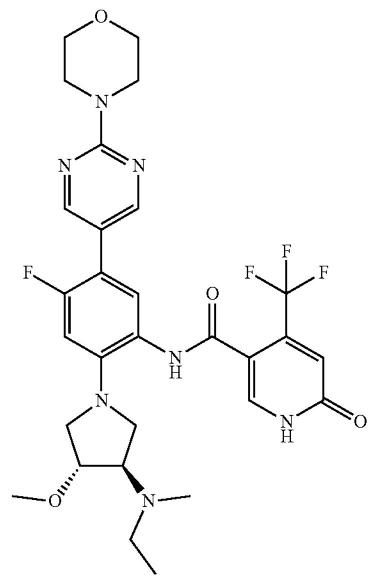 [SMILES: CCN(C)[C@@H]1CN(c2cc(F)c(-c3cnc(N4CCOCC4)nc3)cc2NC(=O)c2c[nH]c(=O)cc2C(F)(F)F)C[C@H]1OC] | N-[4-fluoro-5-(2-morpholin-4-ylpyrimidin-5-yl)-2-[rac-(3R,4R)-3-[ethyl(methyl)amino]-4-methoxypyrrolidin-1-yl]phenyl]-6-oxo-4-(trifluoromethyl)-1H-pyridine-3-carboxamide | — |
| 359 | 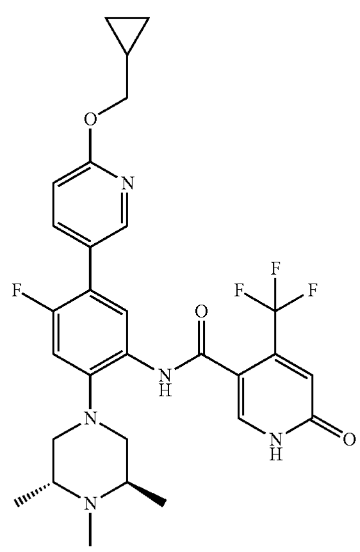 [SMILES: C[C@@H]1CN(c2cc(F)c(-c3ccc(OCC4CC4)nc3)cc2NC(=O)c2c[nH]c(=O)cc2C(F)(F)F)C[C@@H](C)N1C] | N-[5-[6-(cyclopropylmethoxy)pyridin-3-yl]-4-fluoro-2-[rac-(3R,5R)-3,4,5-trimethylpiperazin-1-yl]phenyl]-6-oxo-4-(trifluoromethyl)-1H-pyridine-3-carboxamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 360 | 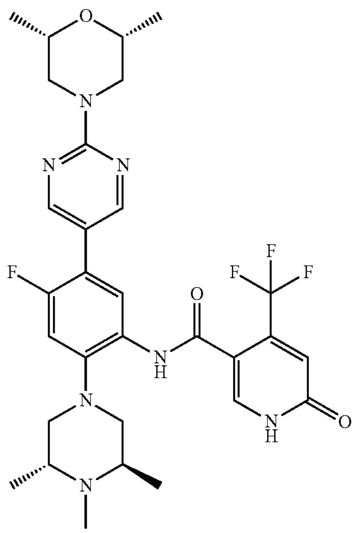 [SMILES: C[C@@H]1CN(c2ncc(-c3cc(NC(=O)c4c[nH]c(=O)cc4C(F)(F)F)c(N4C[C@@H](C)N(C)[C@H](C)C4)cc3F)cn2)C[C@H](C)O1] | N-[4-fluoro-5-[2-[rac-(2R,6S)-2,6-dimethylmorpholin-4-yl]pyrimidin-5-yl]-2-[rac-(3S,5S)-3,4,5-trimethylpiperazin-1-yl]phenyl]-6-oxo-4-(trifluoromethyl)-1H-pyridine-3-carboxamide | — |
| 361 | 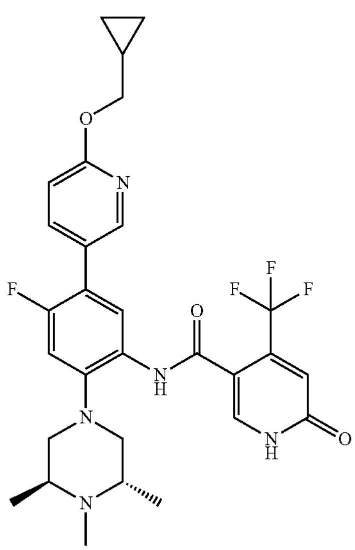 [SMILES: C[C@H]1CN(c2cc(F)c(-c3ccc(OCC4CC4)nc3)cc2NC(=O)c2c[nH]c(=O)cc2C(F)(F)F)C[C@H](C)N1C] | N-[5-[6-(cyclopropylmethoxy)pyridin-3-yl]-4-fluoro-2-[rac-(3R,5R)-3,4,5-trimethylpiperazin-1-yl]phenyl]-6-oxo-4-(trifluoromethyl)-1H-pyridine-3-carboxamide | 0.0483 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 362 | 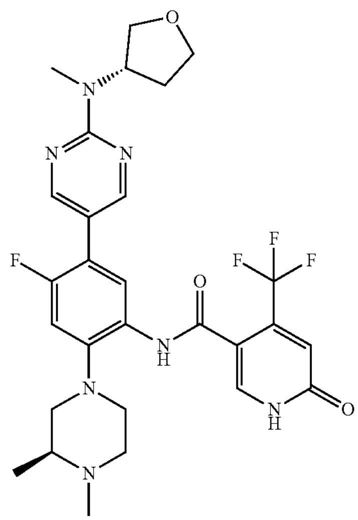 [SMILES: C[C@H]1CN(c2cc(F)c(-c3cnc(N(C)[C@H]4CCOC4)nc3)cc2NC(=O)c2c[nH]c(=O)cc2C(F)(F)F)CCN1C] | N-[4-fluoro-5-[2-[methyl-[rac-(3R)-oxolan-3-yl]amino]pyrimidin-5-yl]-2-[rac-(3R)-3,4-dimethylpiperazin-1-yl]phenyl]-6-oxo-4-(trifluoromethyl)-1H-pyridine-3-carboxamide | 0.000244 |
| 363 | 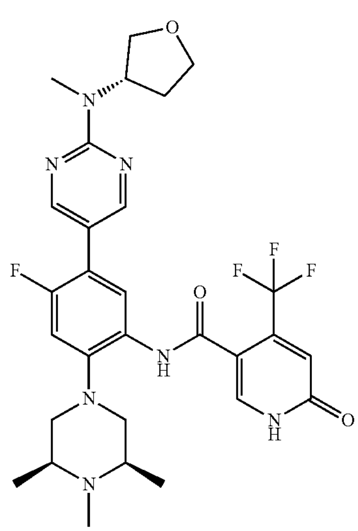 [SMILES: C[C@@H]1CN(c2cc(F)c(-c3cnc(N(C)[C@H]4CCOC4)nc3)cc2NC(=O)c2c[nH]c(=O)cc2C(F)(F)F)C[C@H](C)N1C] | N-[4-fluoro-5-[2-[methyl-[rac-(3R)-oxolan-3-yl]amino]pyrimidin-5-yl]-2-[rac-(3S,5R)-3,4,5-trimethylpiperazin-1-yl]phenyl]-6-oxo-4-(trifluoromethyl)-1H-pyridine-3-carboxamide | 0.000634 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 364 | 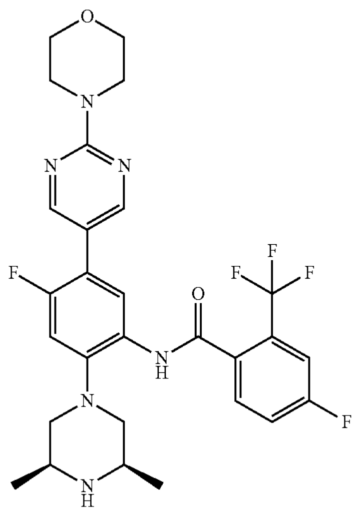 [SMILES: C[C@@H]1CN(c2cc(F)c(-c3cnc(N4CCOCC4)nc3)cc2NC(=O)c2ccc(F)cc2C(F)(F)F)C[C@H](C)N1] | 4-fluoro-N-[4-fluoro-5-(2-morpholin-4-ylpyrimidin-5-yl)-2-[rac-(3R,5S)-3,5-dimethylpiperazin-1-yl]phenyl]-2-(trifluoromethyl)benzamide | 0.00587 |
| 365 | 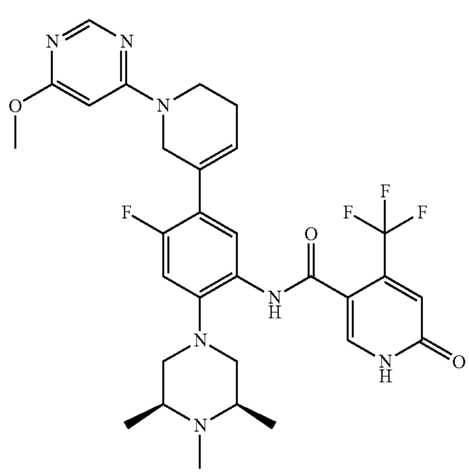 [SMILES: COc1cc(N2CCC=C(c3cc(NC(=O)c4c[nH]c(=O)cc4C(F)(F)F)c(N4C[C@@H](C)N(C)[C@@H](C)C4)cc3F)C2)ncn1] | N-[4-fluoro-5-[1-(6-methoxypyrimidin-4-yl)-3,6-dihydro-2H-pyridin-5-yl]-2-[rac-(3R,5S)-3,4,5-trimethylpiperazin-1-yl]phenyl]-6-oxo-4-(trifluoromethyl)-1H-pyridine-3-carboxamide | 0.000246 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 366 | 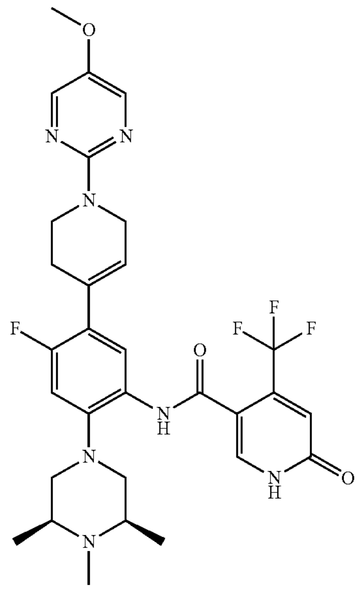 [SMILES: COc1cnc(N2CC=C(c3cc(NC(=O)c4c[nH]c(=O)cc4C(F)(F)F)c(N4C[C@@H](C)N(C)[C@@H](C)C4)cc3F)CC2)nc1] | N-[4-fluoro-5-[1-(5-methoxypyrimidin-2-yl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00176 |
| 367 | 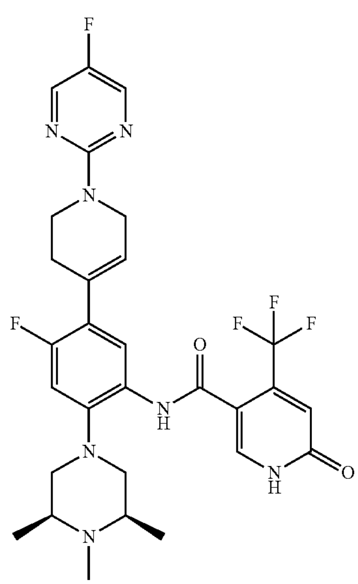 | N-[4-fluoro-5-[1-(5-fluoropyrimidin-2-yl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00104 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 368 | 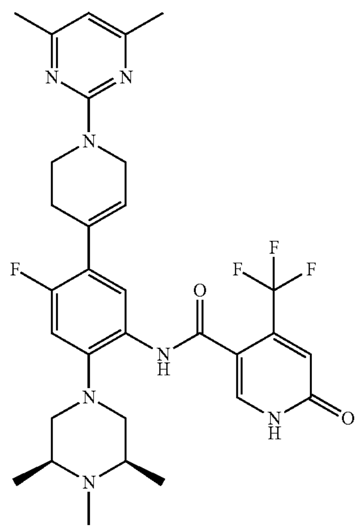 [SMILES: Cc1cc(C)nc(N2CC=C(c3cc(NC(=O)c4c[nH]c(=O)cc4C(F)(F)F)c(N4C[C@@H](C)N(C)[C@@H](C)C4)cc3F)CC2)n1] | N-[5-[1-(4,6-dimethylpyrimidin-2-yl)-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.0023 |
| 369 | 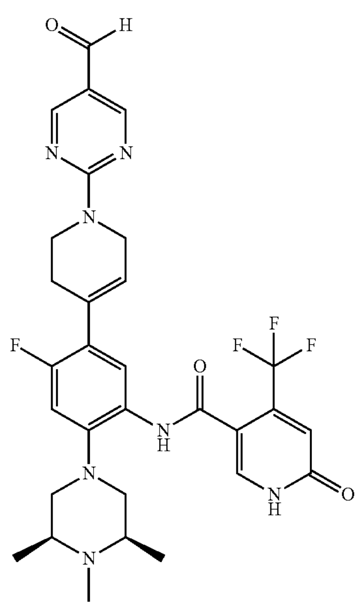 [SMILES: C[C@@H]1CN(c2cc(F)c(C3=CCN(c4ncc(C=O)cn4)CC3)cc2NC(=O)c2c[nH]c(=O)cc2C(F)(F)F)C[C@H](C)N1C] | N-[4-fluoro-5-[1-(5-formylpyrimidin-2-yl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.000685 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 370 | 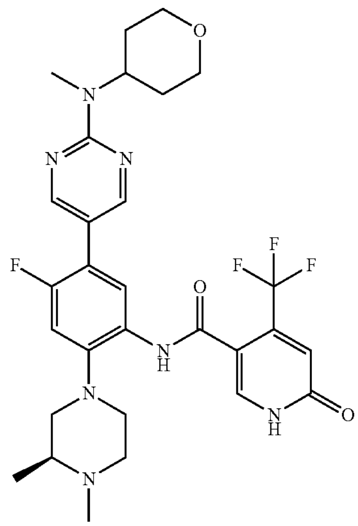 [SMILES: C[C@H]1CN(c2cc(F)c(-c3cnc(N(C)C4CCOCC4)nc3)cc2NC(=O)c2c[nH]c(=O)cc2C(F)(F)F)CCN1C] | N-[4-fluoro-5-[2-[methyl(oxan-4-yl)amino]pyrimidin-5-yl]-2-[rac-(3R)-3,4-dimethylpiperazin-1-yl]phenyl]-6-oxo-4-(trifluoromethyl)-1H-pyridine-3-carboxamide | 0.000866 |
| 371 | 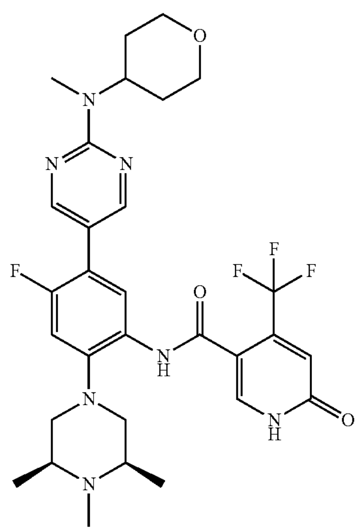 [SMILES: C[C@@H]1CN(c2cc(F)c(-c3cnc(N(C)C4CCOCC4)nc3)cc2NC(=O)c2c[nH]c(=O)cc2C(F)(F)F)C[C@H](C)N1C] | N-[4-fluoro-5-[2-[methyl(oxan-4-yl)amino]pyrimidin-5-yl]-2-[rac-(3R,5S)-3,4,5-trimethylpiperazin-1-yl]phenyl]-6-oxo-4-(trifluoromethyl)-1H-pyridine-3-carboxamide | 0.00059 |
| 372 | 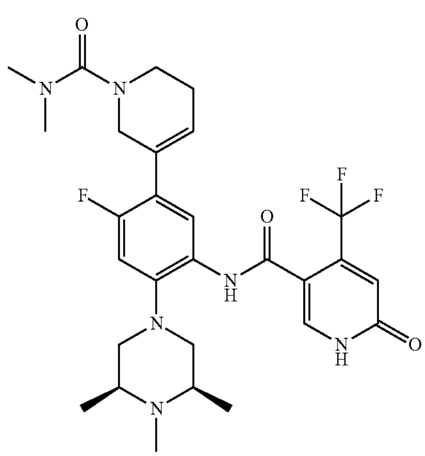 [SMILES: C[C@@H]1CN(c2cc(F)c(C3=CCCN(C(=O)N(C)C)C3)cc2NC(=O)c2c[nH]c(=O)cc2C(F)(F)F)C[C@H](C)N1C] | N-[5-[1-(dimethylcarbamoyl)-3,6-dihydro-2H-pyridin-5-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00175 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 373 | 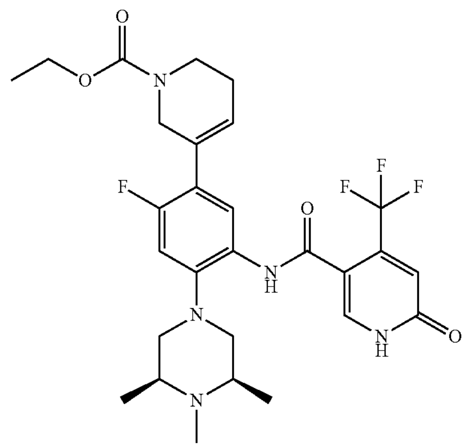 | ethyl 5-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.000808 |
| 374 | 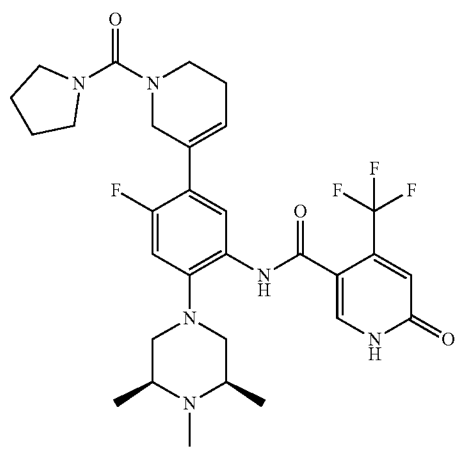 [SMILES: C[C@@H]1CN(c2cc(F)c(C3=CCCN(C(=O)N4CCCC4)C3)cc2NC(=O)c2c[nH]c(=O)cc2C(F)(F)F)C[C@H](C)N1C] | N-[4-fluoro-5-[1-pyrrolidine-1-carbonyl)-3,6-dihydro-2H-pyridin-5-yl]-2-[rac-(3R,5S)-3,4,5-trimethylpiperazin-1-yl]phenyl]-6-oxo-4-(trifluoromethyl)-1H-pyridine-3-carboxamide | 0.00115 |
| 375 | 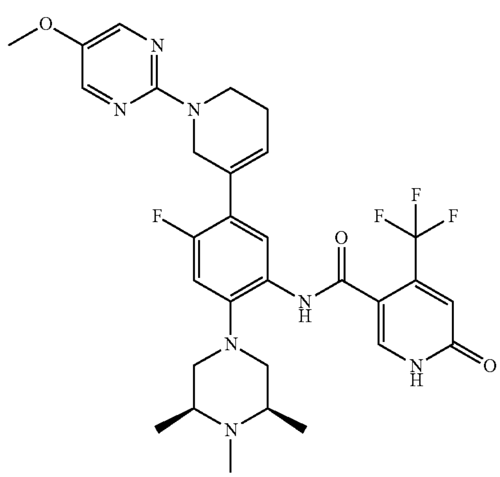 [SMILES: COc1cnc(N2CCC=C(c3cc(NC(=O)c4c[nH]c(=O)cc4C(F)(F)F)c(N4C[C@@H](C)N(C)[C@@H](C)C4)cc3F)C2)nc1] | N-[4-fluoro-5-[1-(5-methoxypyrimidin-2-yl)-3,6-dihydro-2H-pyridin-5-yl]-2-[rac-(3R,5S)-3,4,5-trimethylpiperazin-1-yl]phenyl]-6-oxo-4-(trifluoromethyl)-1H-pyridine-3-carboxamide | 0.000688 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 376 | 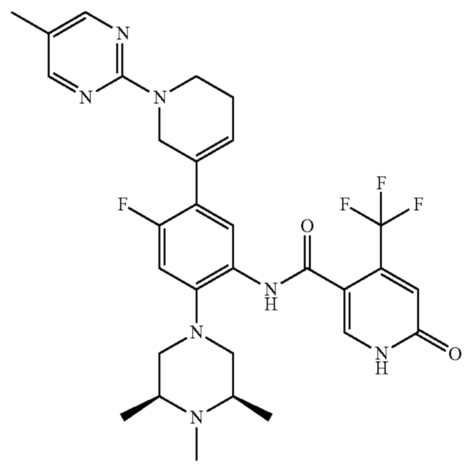 [SMILES: Cc1cnc(N2CCC=C(c3cc(NC(=O)c4c[nH]c(=O)cc4C(F)(F)F)c(N4C[C@@H](C)N(C)[C@@H](C)C4)cc3F)C2)nc1] | N-[4-fluoro-5-[1-(5-methylpyrimidin-2-yl)-3,6-dihydro-2H-pyridin-5-yl]-2-[rac-(3R,5S)-3,4,5-trimethylpiperazin-1-yl]phenyl]-6-oxo-4-(trifluoromethyl)-1H-pyridine-3-carboxamide | 0.000673 |
| 377 | 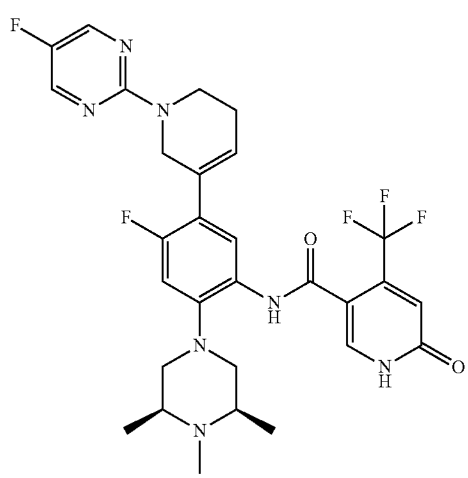 [SMILES: C[C@@H]1CN(c2cc(F)c(C3=CCCN(c4ncc(F)cn4)C3)cc2NC(=O)c2c[nH]c(=O)cc2C(F)(F)F)C[C@H](C)N1C] | N-[4-fluoro-5-[1-(5-fluoropyrimidin-2-yl)-3,6-dihydro-2H-pyridin-5-yl]-2-[rac-(3R,5S)-3,4,5-trimethylpiperazin-1-yl]phenyl]-6-oxo-4-(trifluoromethyl)-1H-pyridine-3-carboxamide | 0.0013 |
| 378 | 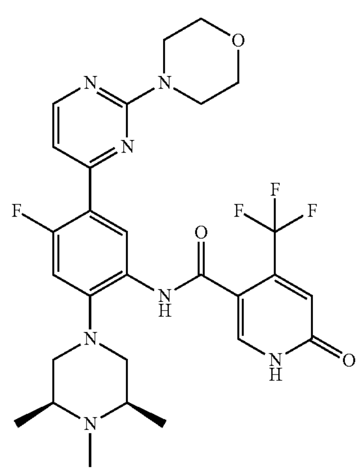 | N-[4-fluoro-5-(2-morpholin-4-ylpyrimidin-4-yl)-2-[rac-(3R,5S)-3,4,5-trimethylpiperazin-1-yl]phenyl]-6-oxo-4-(trifluoromethyl)-1H-pyridine-3-carboxamide | 0.000877 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 379 | 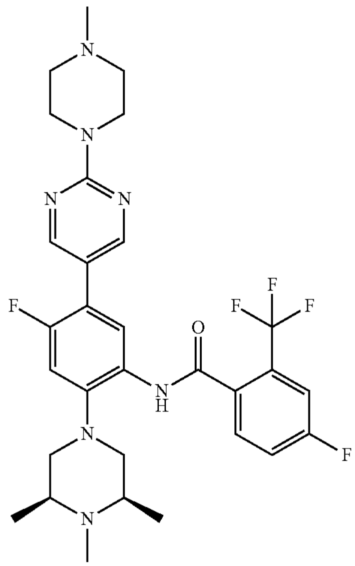 [SMILES: C[C@@H]1CN(c2cc(F)c(-c3cnc(N4CCN(C)CC4)nc3)cc2NC(=O)c2ccc(F)cc2C(F)(F)F)C[C@H](C)N1C] | 4-fluoro-N-[4-fluoro-5-[2-(4-methylpiperazin-1-yl)pyrimidin-5-yl]-2-[rac-(3R,5S)-3,4,5-trimethylpiperazin-1-yl]phenyl]-2-(trifluoromethyl)benzamide | 0.000933 |
| 380 | 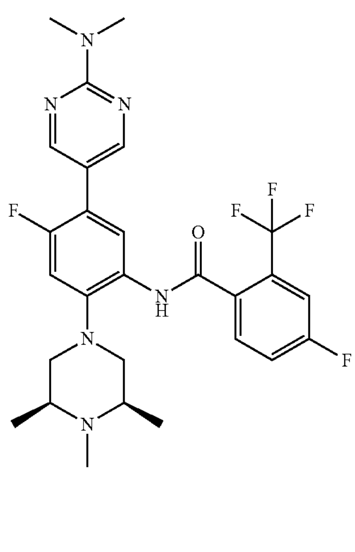 [SMILES: C[C@@H]1CN(c2cc(F)c(-c3cnc(N(C)C)nc3)cc2NC(=O)c2ccc(F)cc2C(F)(F)F)C[C@H](C)N1C] | N-[5-[2-(dimethylamino)pyrimidin-5-yl]-4-fluoro-2-[rac-(3R,5S)-3,4,5-trimethylpiperazin-1-yl]phenyl]-4-fluoro-2-(trifluoromethyl)benzamide | 0.0017 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 381 | 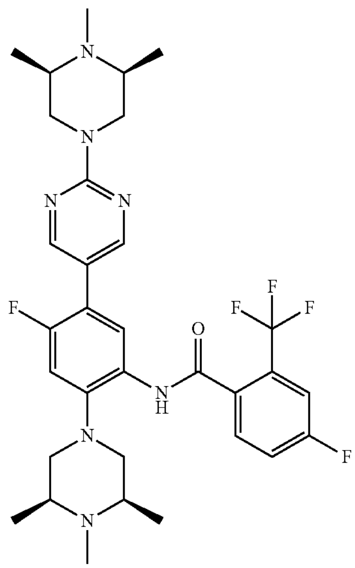 [SMILES: C[C@@H]1CN(c2ncc(-c3cc(NC(=O)c4ccc(F)cc4C(F)(F)F)c(N4C[C@@H](C)N(C)[C@@H](C)C4)cc3F)cn2)C[C@H](C)N1C] | 4-fluoro-N-[4-fluoro-2-[rac-(3R,5S)-3,4,5-trimethylpiperazin-1-yl]-5-[2-[rac-(3R,5S)-3,4,5-trimethylpiperazin-1-yl]pyrimidin-5-yl]phenyl]-2-(trifluoromethyl)benzamide | 0.00031 |
| 382 | 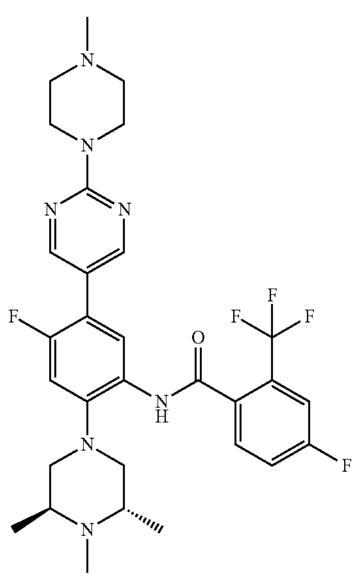 [SMILES: C[C@H]1CN(c2cc(F)c(-c3cnc(N4CCN(C)CC4)nc3)cc2NC(=O)c2ccc(F)cc2C(F)(F)F)C[C@H](C)N1C] | 4-fluoro-N-[4-fluoro-5-[2-(4-methylpiperazin-1-yl)pyrimidin-5-yl]-2-[rac-(3R,5R)-3,4,5-trimethylpiperazin-1-yl]phenyl]-2-(trifluoromethyl)benzamide | 0.117 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 383 | 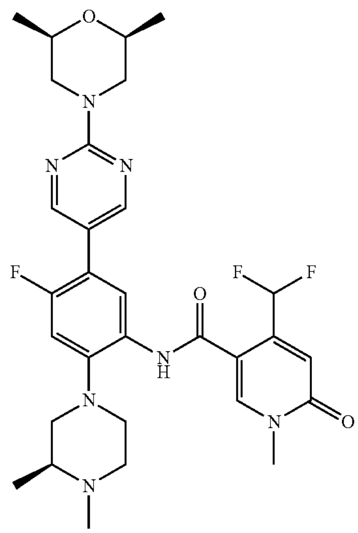 [SMILES: C[C@@H]1CN(c2ncc(-c3cc(NC(=O)c4cn(C)c(=O)cc4C(F)F)c(N4CCN(C)[C@@H](C)C4)cc3F)cn2)C[C@H](C)O1] | 4-(difluoromethyl)-N-[4-fluoro-5-[2-[rac-(2R,6S)-2,6-dimethylmorpholin-4-yl]pyrimidin-5-yl]-2-[rac-(3R)-3,4-dimethylpiperazin-1-yl]phenyl]-1-methyl-6-oxopyridine-3-carboxamide | 0.00119 |
| 384 | 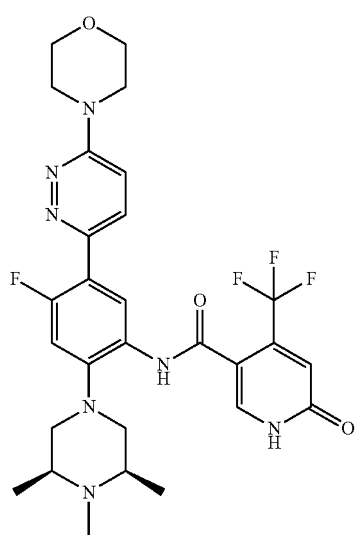 [SMILES: C[C@@H]1CN(c2cc(F)c(-c3ccc(N4CCOCC4)nn3)cc2NC(=O)c2c[nH]c(=O)cc2C(F)(F)F)C[C@H](C)N1C] | N-[4-fluoro-5-(6-morpholin-4-ylpyridazin-3-yl)-2-[rac-(3R,5S)-3,4,5-trimethylpiperazin-1-yl]phenyl]-6-oxo-4-(trifluoromethyl)-1H-pyridine-3-carboxamide | 0.00153 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 385 | 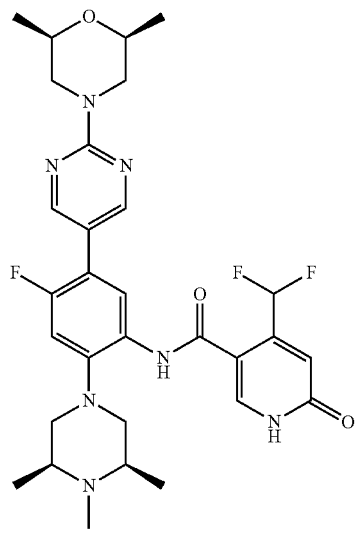 [SMILES: C[C@@H]1CN(c2ncc(-c3cc(NC(=O)c4c[nH]c(=O)cc4C(F)F)c(N4C[C@@H](C)N(C)[C@@H](C)C4)cc3F)cn2)C[C@H](C)O1] | 4-(difluoromethyl)-N-[4-fluoro-5-[2-[rac-(2R,6S)-2,6-dimethylmorpholin-4-yl]pyrimidin-5-yl]-2-[rac-(3S,5R)-3,4,5-trimethylpiperazin-1-yl]phenyl]-6-oxo-1H-pyridine-3-carboxamide | 0.00072 |
| 386 | 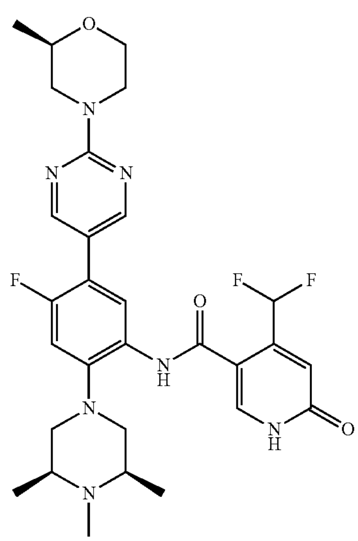 [SMILES: C[C@@H]1CN(c2ncc(-c3cc(NC(=O)c4c[nH]c(=O)cc4C(F)F)c(N4C[C@@H](C)N(C)[C@@H](C)C4)cc3F)cn2)CCO1] | 4-(difluoromethyl)-N-[4-fluoro-5-[2-[rac-(2R)-2-methylmorpholin-4-yl]pyrimidin-5-yl]-2-[rac-(3R,5S)-3,4,5-trimethylpiperazin-1-yl]phenyl]-6-oxo-1H-pyridine-3-carboxamide | 0.00149 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 387 | 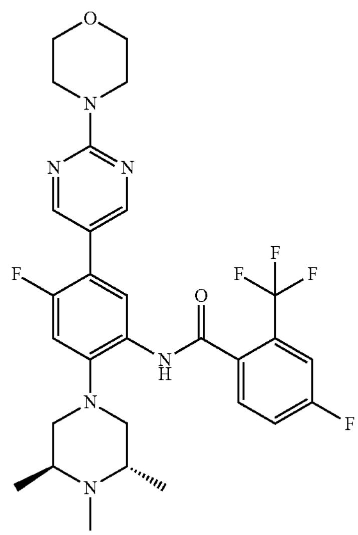 | 4-fluoro-N-[4-fluoro-5-(2-morpholin-4-ylpyrimidin-5-yl)-2-[rac-(3R,5R)-3,4,5-trimethylpiperazin-1-yl]phenyl]-2-(trifluoromethyl)benzamide | 0.0835 |
| 388 | 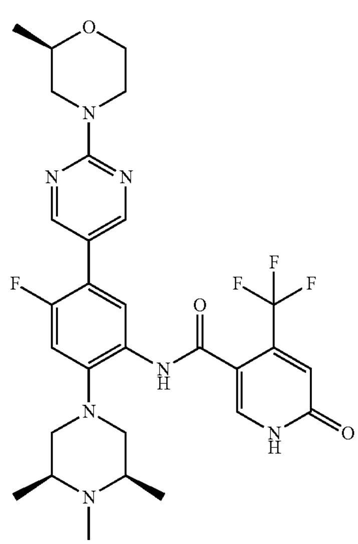 | N-[4-fluoro-5-[2-[rac-(2R)-2-methylmorpholin-4-yl]pyrimidin-5-yl]-2-[rac-(3R,5S)-3,4,5-trimethylpiperazin-1-yl]phenyl]-6-oxo-4-(trifluoromethyl)-1H-pyridine-3-carboxamide | 0.000788 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 389 | 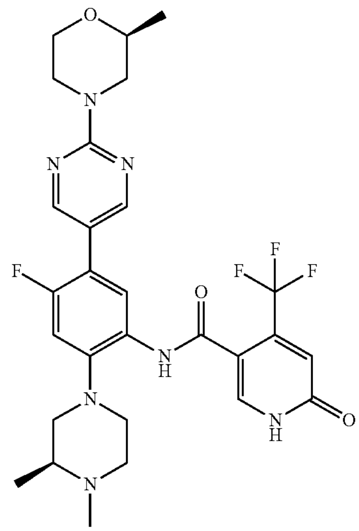 [SMILES: C[C@H]1CN(c2ncc(-c3cc(NC(=O)c4c[nH]c(=O)cc4C(F)(F)F)c(N4CCN(C)[C@@H](C)C4)cc3F)cn2)CCO1] | N-[4-fluoro-2-[rac-(3R)-3,4-dimethylpiperazin-1-yl]-5-[2-[rac-(2R)-2-methylmorpholin-4-yl]pyrimidin-5-yl]phenyl]-6-oxo-4-(trifluoromethyl)-1H-pyridine-3-carboxamide | 0.000522 |
| 390 | 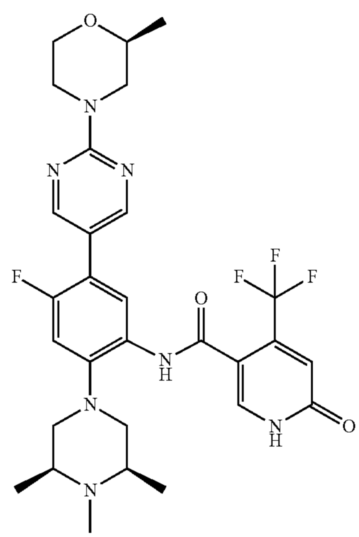 | N-[4-fluoro-5-[2-[rac-(2R)-2-methylmorpholin-4-yl]pyrimidin-5-yl]-2-[rac-(3S,5R)-3,4,5-trimethylpiperazin-1-yl]phenyl]-6-oxo-4-(trifluoromethyl)-1H-pyridine-3-carboxamide | 0.000634 |
| 391 | 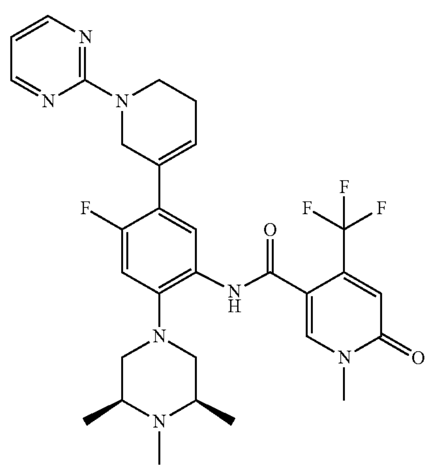 [SMILES: C[C@@H]1CN(c2cc(F)c(C3=CCCN(c4ncccn4)C3)cc2NC(=O)c2cn(C)c(=O)cc2C(F)(F)F)C[C@H](C)N1C] | N-[4-fluoro-5-(1-pyrimidin-2-yl-3,6-dihydro-2H-pyridin-5-yl)-2-[rac-(3R,5S)-3,4,5-trimethylpiperazin-1-yl]phenyl]-1-methyl-6-oxo-4-(trifluoromethyl)pyridine-3-carboxamide | 0.00427 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 392 | 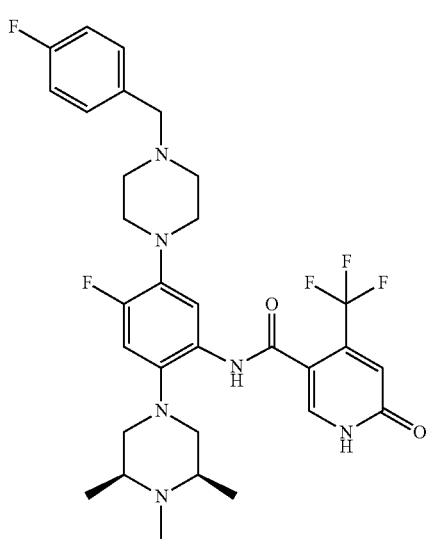 [SMILES: C[C@@H]1CN(c2cc(F)c(N3CCN(Cc4ccc(F)cc4)CC3)cc2NC(=O)c2c[nH]c(=O)cc2C(F)(F)F)C[C@H](C)N1C] | N-[4-fluoro-5-[4-[(4-fluorophenyl)methyl]piperazin-1-yl]-2-[rac-(3R,5S)-3,4,5-trimethylpiperazin-1-yl]phenyl]-6-oxo-4-(trifluoromethyl)-1H-pyridine-3-carboxamide | 0.00808 |
| 393 | 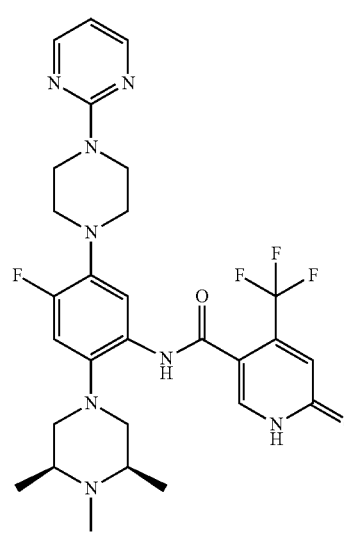 | N-[4-fluoro-5-(4-pyrimidin-2-ylpiperazin-1-yl)-2-[rac-(3R,5S)-3,4,5-trimethylpiperazin-1-yl]phenyl]-6-oxo-4-(trifluoromethyl)-1H-pyridine-3-carboxamide | 0.0133 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 394 | 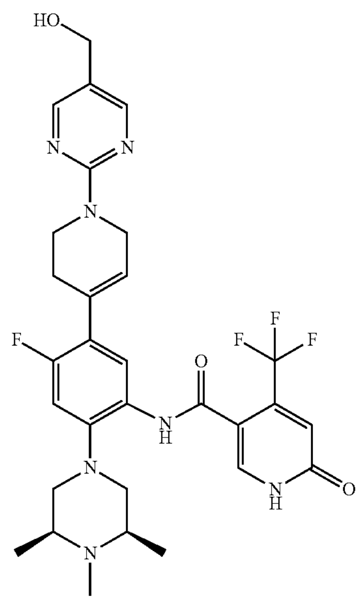 [SMILES: C[C@@H]1CN(c2cc(F)c(C3=CCN(c4ncc(CO)cn4)CC3)cc2NC(=O)c2c[nH]c(=O)cc2C(F)(F)F)C[C@H](C)N1C] | N-[4-fluoro-5-[1-[5-(hydroxymethyl)pyrimidin-2-yl]-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.000775 |
| 395 | 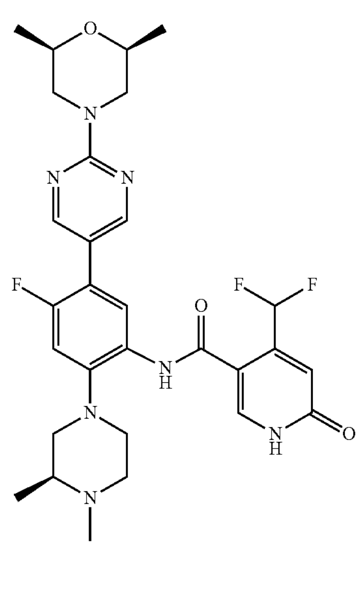 [SMILES: C[C@@H]1CN(c2ncc(-c3cc(NC(=O)c4c[nH]c(=O)cc4C(F)F)c(N4CCN(C)[C@@H](C)C4)cc3F)cn2)C[C@H](C)O1] | 4-(difluoromethyl)-N-[4-fluoro-5-[2-[rac-(2R,6S)-2,6-dimethylmorpholin-4-yl]pyrimidin-5-yl]-2-[rac-(3S)-3,4-dimethylpiperazin-1-yl]phenyl]-6-oxo-1H-pyridine-3-carboxamide | 0.000152 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 396 | 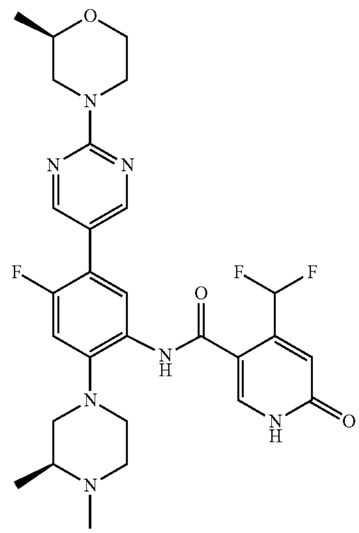 | 4-(difluoromethyl)-N-[4-fluoro-2-[rac-(3S)-3,4-dimethylpiperazin-1-yl]-5-[2-[rac-(2R)-2-methylmorpholin-4-yl]pyrimidin-5-yl]phenyl]-6-oxo-1H-pyridine-3-carboxamide | 0.000564 |
| 397 | 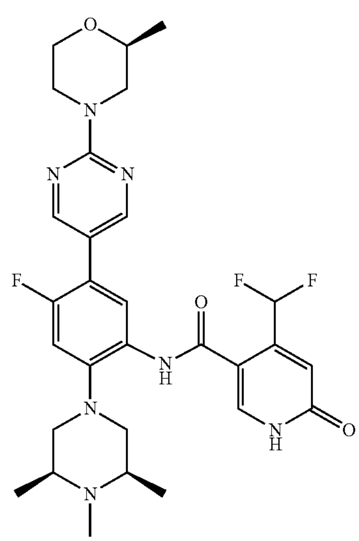 | 4-(difluoromethyl)-N-[4-fluoro-5-[2-[rac-(2R)-2-methylmorpholin-4-yl]pyrimidin-5-yl]-2-[rac-(3S,5R)-3,4,5-trimethylpiperazin-1-yl]phenyl]-6-oxo-1H-pyridine-3-carboxamide | 0.00068 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 398 | 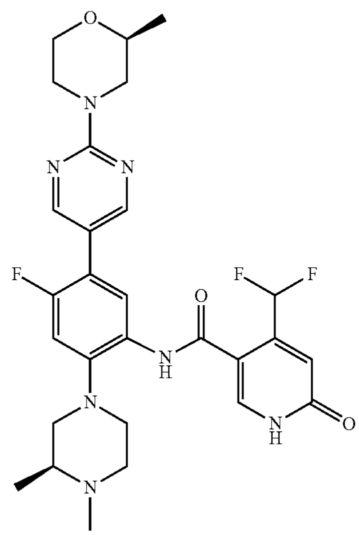 | 4-(difluoromethyl)-N-[4-fluoro-2-[rac-(3R)-3,4-dimethylpiperazin-1-yl]-5-[2-[rac-(2R)-2-methylmorpholin-4-yl]pyrimidin-5-yl]phenyl]-6-oxo-1H-pyridine-3-carboxamide | 0.000899 |
| 399 | 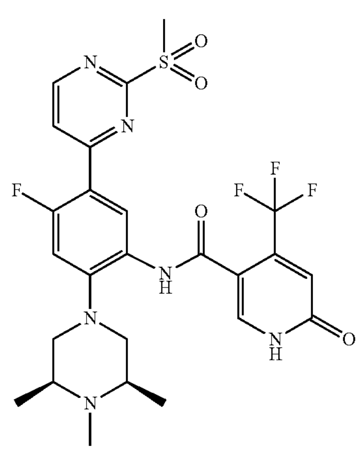 [SMILES: C[C@@H]1CN(c2cc(F)c(-c3ccnc(S(C)(=O)=O)n3)cc2NC(=O)c2c[nH]c(=O)cc2C(F)(F)F)C[C@H](C)N1C] | N-[4-fluoro-5-(2-methylsulfonylpyrimidin-4-yl)-2-[rac-(3R,5S)-3,4,5-trimethylpiperazin-1-yl]phenyl]-6-oxo-4-(trifluoromethyl)-1H-pyridine-3-carboxamide | 0.00458 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 400 | 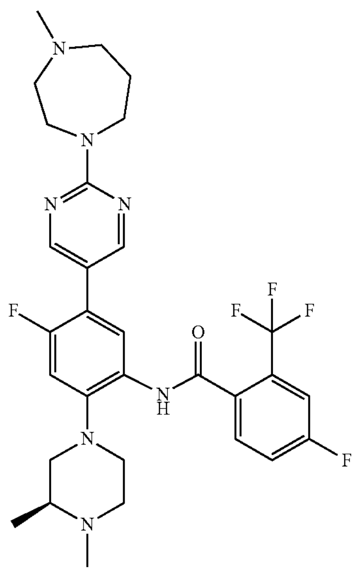 [SMILES: C[C@H]1CN(c2cc(F)c(-c3cnc(N4CCCN(C)CC4)nc3)cc2NC(=O)c2ccc(F)cc2C(F)(F)F)CCN1C] | 4-fluoro-N-[4-fluoro-5-[2-(4-methyl-1,4-diazepan-1-yl)pyrimidin-5-yl]-2-[rac-(3R)-3,4-dimethylpiperazin-1-yl]phenyl]-2-(trifluoromethyl)benzamide | 0.00147 |
| 401 | 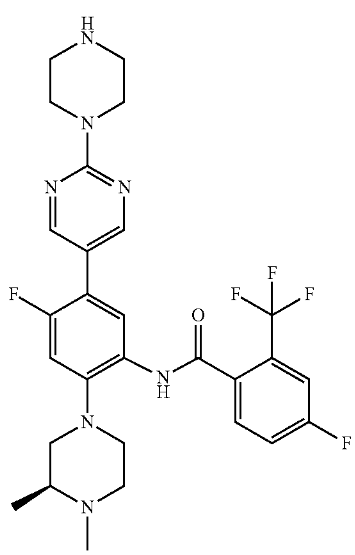 | 4-fluoro-N-[4-fluoro-5-(2-piperazin-1-ylpyrimidin-5-yl)-2-[rac-(3R)-3,4-dimethylpiperazin-1-yl]phenyl]-2-(trifluoromethyl)benzamide | 0.00111 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 402 | 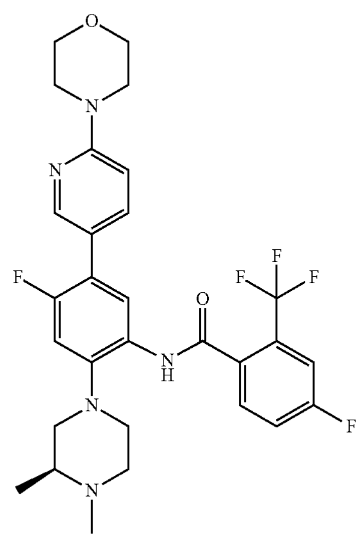 | 4-fluoro-N-[4-fluoro-5-(6-morpholin-4-ylpyridin-3-yl)-2-[rac-(3R)-3,4-dimethylpiperazin-1-yl]phenyl]-2-(trifluoromethyl)benzamide | 0.0037 |
| 403 | 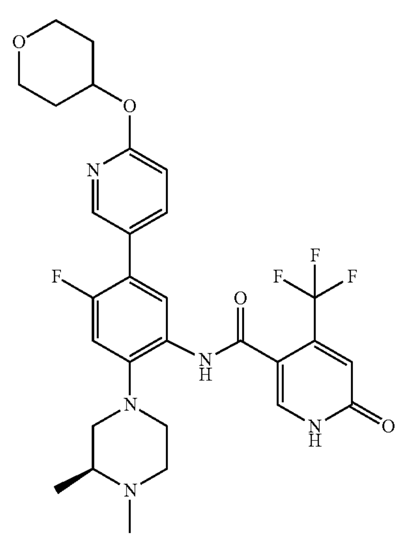 | 4-(difluoromethyl)-N-[4-fluoro-5-[6-(oxan-4-yloxy)pyridin-3-yl]-2-[rac-(3R)-3,4-dimethylpiperazin-1-yl]phenyl]-6-oxo-1H-pyridine-3-carboxamide | 0.00116 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 404 | 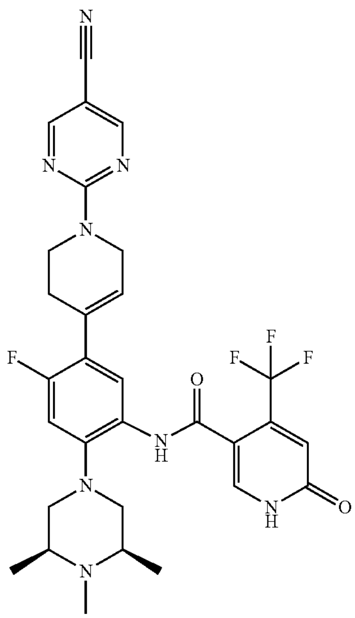 [SMILES: C[C@@H]1CN(c2cc(F)c(C3=CCN(c4ncc(C#N)cn4)CC3)cc2NC(=O)c2c[nH]c(=O)cc2C(F)(F)F)C[C@H](C)N1C] | N-[5-[1-(5-cyanopyrimidin-2-yl)-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.001 |
| 405 | 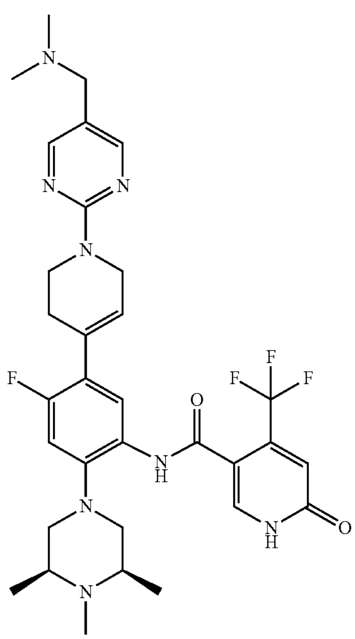 [SMILES: C[C@@H]1CN(c2cc(F)c(C3=CCN(c4ncc(CN(C)C)cn4)CC3)cc2NC(=O)c2c[nH]c(=O)cc2C(F)(F)F)C[C@H](C)N1C] | N-[5-[1-[5-[(dimethylamino)methyl]pyrimidin-2-yl]-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 9.5e−05 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 406 | 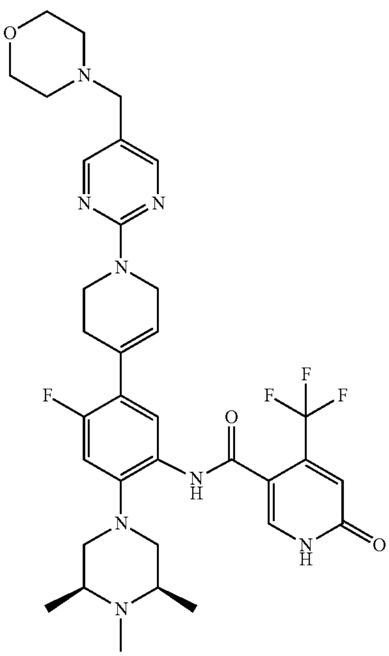 [SMILES: C[C@@H]1CN(c2cc(F)c(C3=CCN(c4ncc(CN5CCOCC5)cn4)CC3)cc2NC(=O)c2c[nH]c(=O)cc2C(F)(F)F)C[C@H](C)N1C] | N-[4-fluoro-5-[1-[5-(morpholin-4-ylmethyl)pyrimidin-2-yl]-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.000457 |
| 407 | 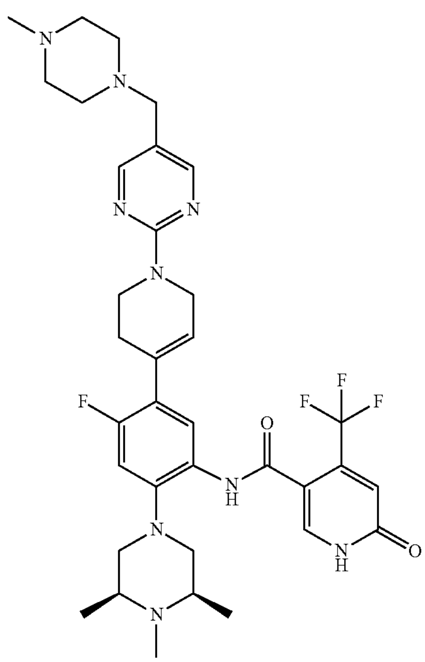 [SMILES: C[C@@H]1CN(c2cc(F)c(C3=CCN(c4ncc(CN5CCN(C)CC5)cn4)CC3)cc2NC(=O)c2c[nH]c(=O)cc2C(F)(F)F)C[C@H](C)N1C] | N-[4-fluoro-5-[1-[5-[(4-methylpiperazin-1-yl)methyl]pyrimidin-2-yl]-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.000231 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 408 | 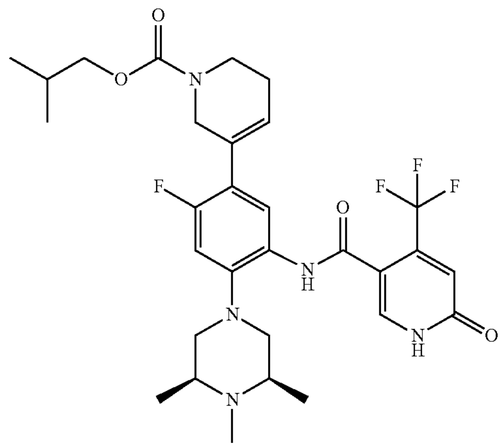 [SMILES: CC(C)COC(=O)N1CCC=C(c2cc(NC(=O)c3c[nH]c(=O)cc3C(F)(F)F)c(N3C[C@@H](C)N(C)[C@@H](C)C3)cc2F)C1] | 2-methylpropyl 5-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.00275 |
| 409 | 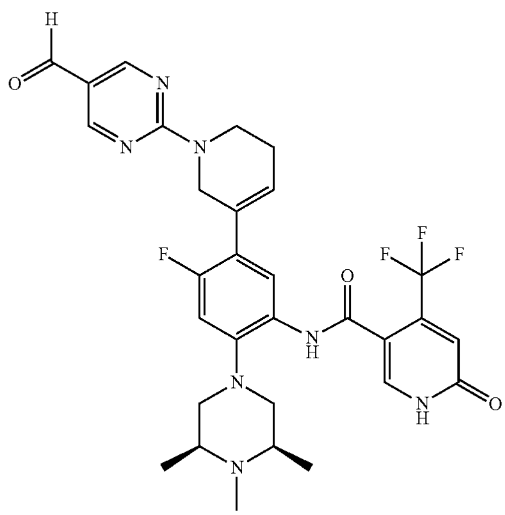 [SMILES: C[C@@H]1CN(c2cc(F)c(C3=CCCN(c4ncc(C=O)cn4)C3)cc2NC(=O)c2c[nH]c(=O)cc2C(F)(F)F)C[C@H](C)N1C] | N-[4-fluoro-5-[1-(5-formylpyrimidin-2-yl)-3,6-dihydro-2H-pyridin-5-yl]-2-[rac-(3R,5S)-3,4,5-trimethylpiperazin-1-yl]phenyl]-6-oxo-4-(trifluoromethyl)-1H-pyridine-3-carboxamide | 0.000229 |
| 410 | 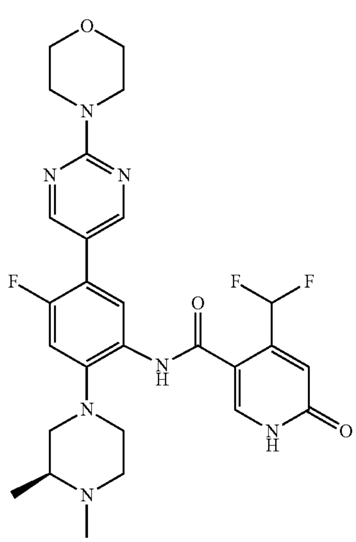 | 4-(difluoromethyl)-N-[4-fluoro-5-(2-morpholin-4-ylpyrimidin-5-yl)-2-[rac-(3R)-3,4-dimethylpiperazin-1-yl]phenyl]-6-oxo-1H-pyridine-3-carboxamide | 0.00084 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 411 | 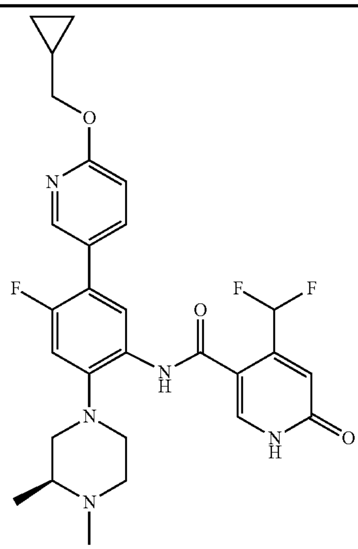 | N-[5-[6-(cyclopropylmethoxy)pyridin-3-yl]-4-fluoro-2-[rac-(3R)-3,4-dimethylpiperazin-1-yl]phenyl]-4-(difluoromethyl)-6-oxo-1H-pyridine-3-carboxamide | 0.00229 |
| 412 | 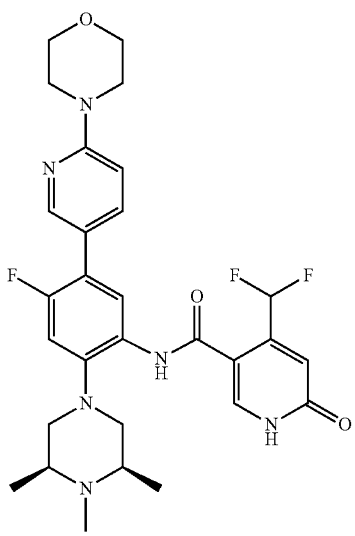 [SMILES: C[C@@H]1CN(c2cc(F)c(-c3ccc(N4CCOCC4)nc3)cc2NC(=O)c2c[nH]c(=O)cc2C(F)F)C[C@H](C)N1C] | 4-(difluoromethyl)-N-[4-fluoro-5-(6-morpholin-4-ylpyridin-3-yl)-2-[rac-(3R,5S)-3,4,5-trimethylpiperazin-1-yl]phenyl]-6-oxo-1H-pyridine-3-carboxamide | 0.000962 |
| 413 | 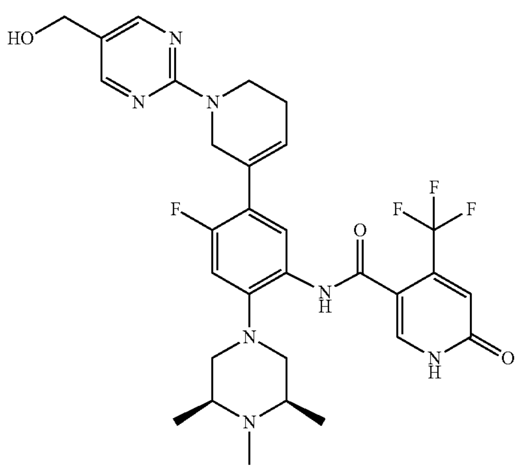 [SMILES: C[C@@H]1CN(c2cc(F)c(C3=CCCN(c4ncc(CO)cn4)C3)cc2NC(=O)c2c[nH]c(=O)cc2C(F)(F)F)C[C@H](C)N1C] | N-[4-fluoro-5-[1-[5-(hydroxymethyl)pyrimidin-2-yl]-3,6-dihydro-2H-pyridin-5-yl]-2-[rac-(3R,5S)-3,4,5-trimethylpiperazin-1-yl]phenyl]-6-oxo-4-(trifluoromethyl)-1H-pyridine-3-carboxamide | 0.000302 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 414 | 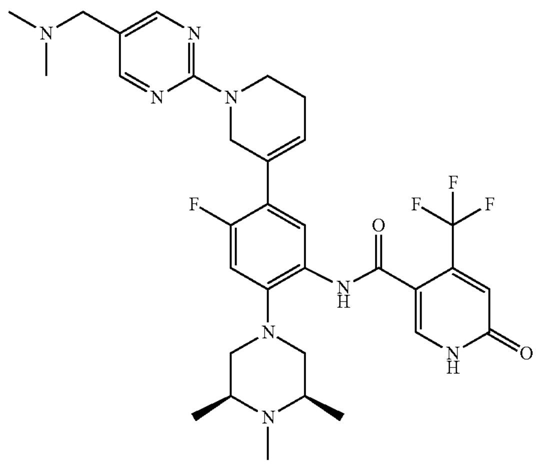 [SMILES: C[C@@H]1CN(c2cc(F)c(C3=CCCN(c4ncc(CN(C)C)cn4)C3)cc2NC(=O)c2c[nH]c(=O)cc2C(F)(F)F)C[C@H](C)N1C] | N-[5-[1-[5-[(dimethylamino)methyl]pyrimidin-2-yl]-3,6-dihydro-2H-pyridin-5-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.000658 |
| 415 | 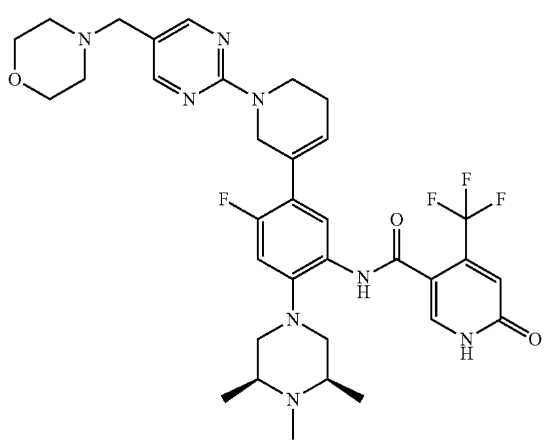 [SMILES: C[C@@H]1CN(c2cc(F)c(C3=CCCN(c4ncc(CN5CCOCC5)cn4)C3)cc2NC(=O)c2c[nH]c(=O)cc2C(F)(F)F)C[C@H](C)N1C] | N-[4-fluoro-5-[1-[5-(morpholin-4-ylmethyl)pyrimidin-2-yl]-3,6-dihydro-2H-pyridin-5-yl]-2-[rac-(3R,5S)-3,4,5-trimethylpiperazin-1-yl]phenyl]-6-oxo-4-(trifluoromethyl)-1H-pyridine-3-carboxamide | 0.0011 |
| 416 | 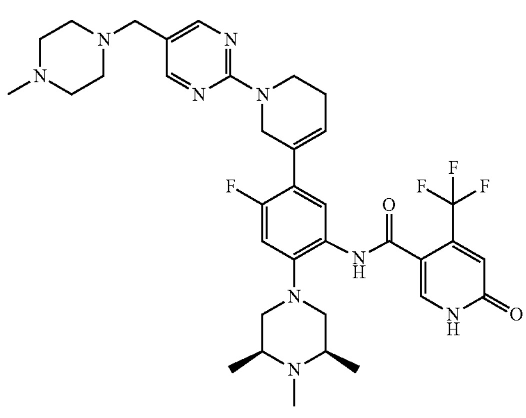 [SMILES: C[C@@H]1CN(c2cc(F)c(C3=CCCN(c4ncc(CN5CCN(C)CC5)cn4)C3)cc2NC(=O)c2c[nH]c(=O)cc2C(F)(F)F)C[C@H](C)N1C] | N-[4-fluoro-5-[1-[5-[(4-methylpiperazin-1-yl)methyl]pyrimidin-2-yl]-3,6-dihydro-2H-pyridin-5-yl]-2-[rac-(3R,5S)-3,4,5-trimethylpiperazin-1-yl]phenyl]-6-oxo-4-(trifluoromethyl)-1H-pyridine-3-carboxamide | 0.000108 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 417 | 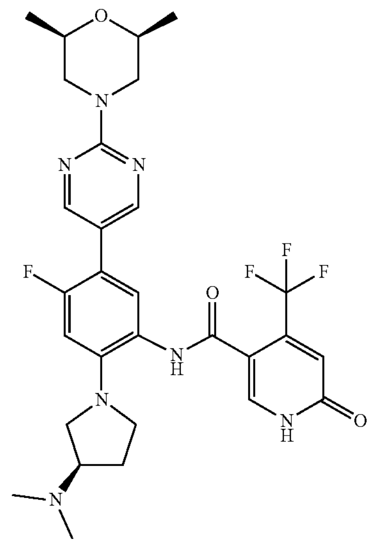 | N-[4-fluoro-2-[rac-(3S)-3-(dimethylamino)pyrrolidin-1-yl]-5-[2-[rac-(2R,6S)-2,6-dimethylmorpholin-4-yl]pyrimidin-5-yl]phenyl]-6-oxo-4-(trifluoromethyl)-1H-pyridine-3-carboxamide | 0.00141 |
| 418 | 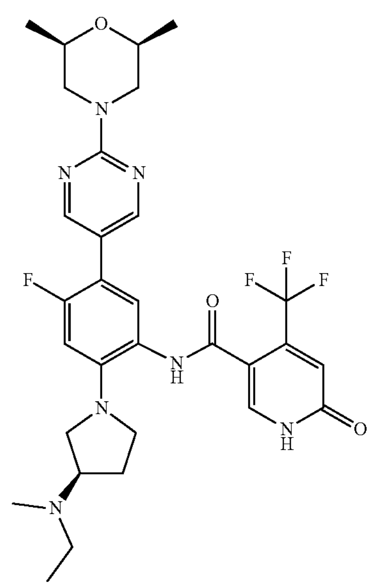 | N-[4-fluoro-5-[2-[rac-(2R,6S)-2,6-dimethylmorpholin-4-yl]pyrimidin-5-yl]-2-[rac-(3S)-3-[ethyl(methyl)amino]pyrrolidin-1-yl]phenyl]-6-oxo-4-(trifluoromethyl)-1H-pyridine-3-carboxamide | 0.00105 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 419 | 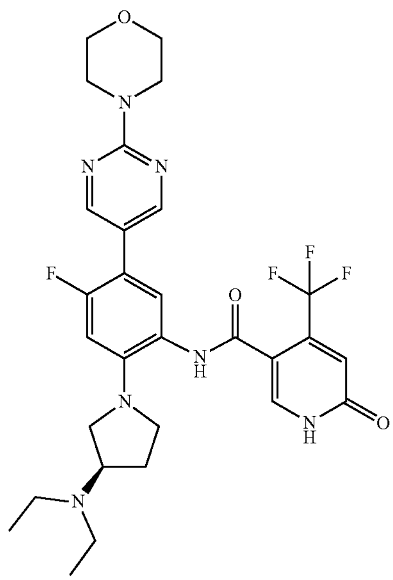 | N-[4-fluoro-5-(2-morpholin-4-ylpyrimidin-5-yl)-2-[rac-(3R)-3-(diethylamino)pyrrolidin-1-yl]phenyl]-6-oxo-4-(trifluoromethyl)-1H-pyridine-3-carboxamide | 0.00537 |
| 420 | 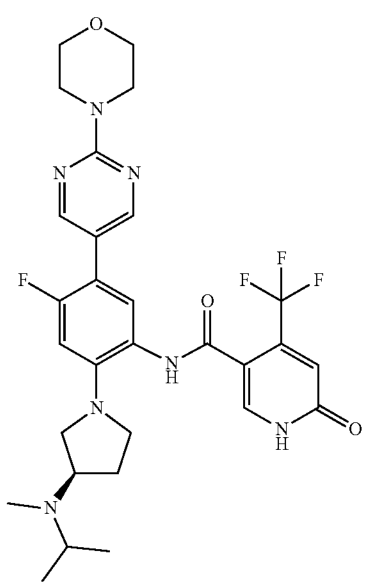 | N-[4-fluoro-5-(2-morpholin-4-ylpyrimidin-5-yl)-2-[rac-(3R)-3-[methyl(propan-2-yl)amino]pyrrolidin-1-yl]phenyl]-6-oxo-4-(trifluoromethyl)-1H-pyridine-3-carboxamide | 0.172 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 421 | 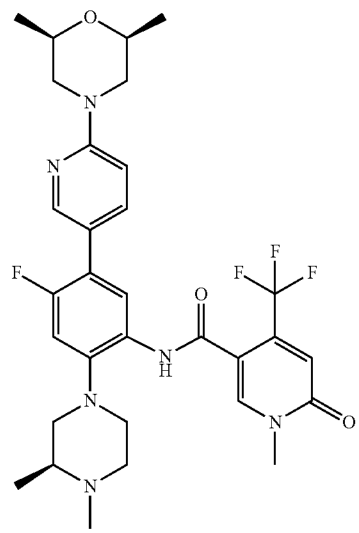 [SMILES: C[C@@H]1CN(c2ccc(-c3cc(NC(=O)c4cn(C)c(=O)cc4C(F)(F)F)c(N4CCN(C)[C@@H](C)C4)cc3F)cn2)C[C@H](C)O1] | N-[4-fluoro-5-[6-[rac-(2R,6S)-2,6-dimethylmorpholin-4-yl]pyridin-3-yl]-2-[rac-(3R)-3,4-dimethylpiperazin-1-yl]phenyl]-1-methyl-6-oxo-4-(trifluoromethyl)pyridine-3-carboxamide | 0.00196 |
| 422 | 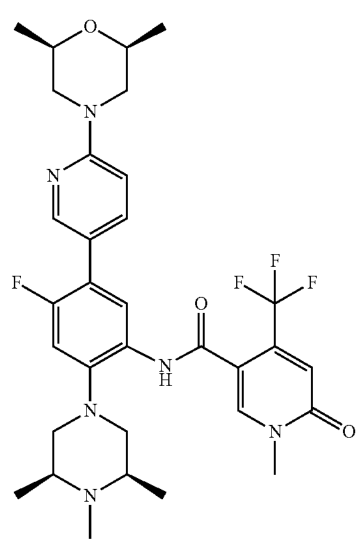 [SMILES: C[C@@H]1CN(c2ccc(-c3cc(NC(=O)c4cn(C)c(=O)cc4C(F)(F)F)c(N4C[C@@H](C)N(C)[C@@H](C)C4)cc3F)cn2)C[C@H](C)O1] | N-(4-fluoro-5-[6-[rac-(2R,6S)-2,6-dimethylmorpholin-4-yl]pyridin-3-yl]-2-[rac-(3S,5R)-3,4,5-trimethylpiperazin-1-yl]phenyl]-1-methyl-6-oxo-4-(trifluoromethyl)pyridine-3-carboxamide | 0.00243 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 423 | 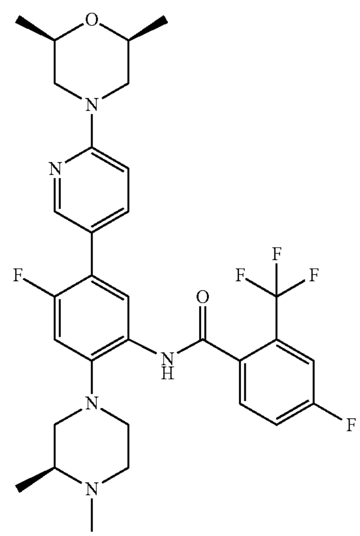 [SMILES: C[C@@H]1CN(c2ccc(-c3cc(NC(=O)c4ccc(F)cc4C(F)(F)F)c(N4CCN(C)[C@@H](C)C4)cc3F)cn2)C[C@H](C)O1] | 4-fluoro-N-[4-fluoro-5-[6-[rac-(2R,6S)-2,6-dimethylmorpholin-4-yl]pyridin-3-yl]-2-[rac-(3R)-3,4-dimethylpiperazin-1-yl]phenyl]-2-(trifluoromethyl)benzamide | 0.00193 |
| 424 | 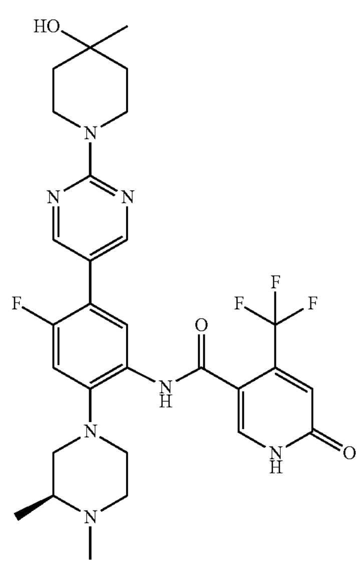 [SMILES: C[C@H]1CN(c2cc(F)c(-c3cnc(N4CCC(C)(O)CC4)nc3)cc2NC(=O)c2c[nH]c(=O)cc2C(F)(F)F)CCN1C] | N-[4-fluoro-5-[2-(4-hydroxy-4-methylpiperidin-1-yl)pyrimidin-5-yl]-2-[rac-(3R)-3,4-dimethylpiperazin-1-yl]phenyl]-6-oxo-4-(trifluoromethyl)-1H-pyridine-3-carboxamide | 0.000609 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 425 | 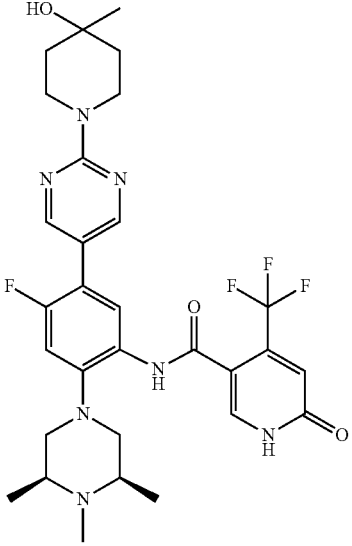 [SMILES: C[C@@H]1CN(c2cc(F)c(-c3cnc(N4CCC(C)(O)CC4)nc3)cc2NC(=O)c2c[nH]c(=O)cc2C(F)(F)F)C[C@H](C)N1C] | N-[4-fluoro-5-[2-(4-hydroxy-4-methylpiperidin-1-yl)pyrimidin-5-yl]-2-[rac-(3R,5S)-3,4,5-trimethylpiperazin-1-yl]phenyl]-6-oxo-4-(trifluoromethyl)-1H-pyridine-3-carboxamide | 0.00106 |
| 426 | 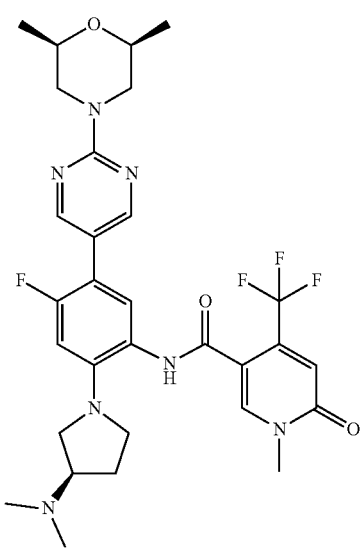 [SMILES: C[C@@H]1CN(c2ncc(-c3cc(NC(=O)c4cn(C)c(=O)cc4C(F)(F)F)c(N4CC[C@@H](N(C)C)C4)cc3F)cn2)C[C@H](C)O1] | N-[4-fluoro-2-[rac-(3S)-3-(dimethylamino)pyrrolidin-1-yl]-5-[2-[rac-(2R,6S)-2,6-dimethylmorpholin-4-yl]pyrimidin-5-yl]phenyl]-1-methyl-6-oxo-4-(trifluoromethyl)pyridine-3-carboxamide | 0.0109 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 427 | 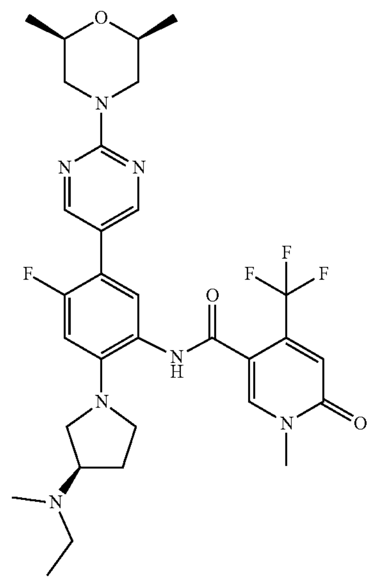 | N-[4-fluoro-5-[2-[rac-(2R,6S)-2,6-dimethylmorpholin-4-yl]pyrimidin-5-yl]-2-[rac-(3S)-3-[ethyl(methyl)amino]pyrrolidin-1-yl]phenyl]-1-methyl-6-oxo-4-(trifluoromethyl)pyridine-3-carboxamide | 0.00559 |
| 428 | 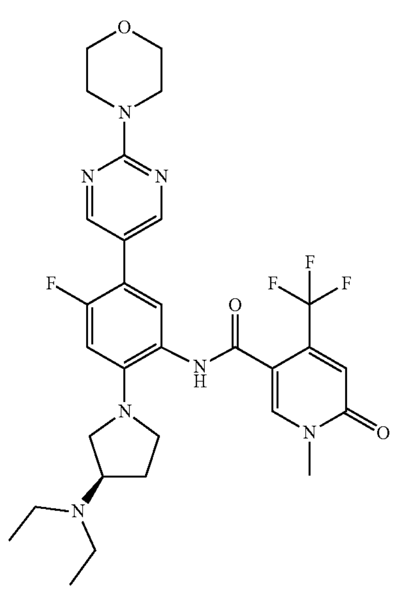 | N-[4-fluoro-5-(2-morpholin-ylpyrimidin-5-yl)-2-[rac-(3R)-3-(diethylamino)pyrrolidin-1-yl]phenyl]-1-methyl-6-oxo-4-(trifluoromethyl)pyridine-3-carboxamide | 0.145 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 429 | 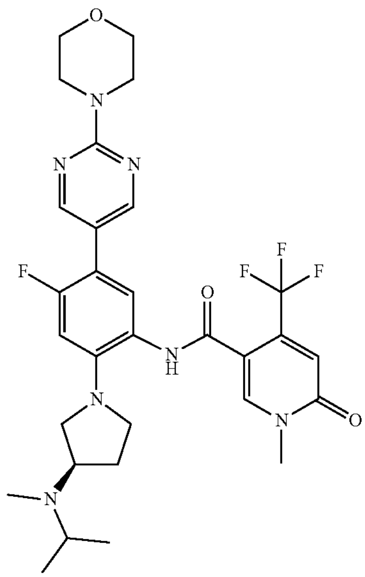 | N-[4-fluoro-5-(2-morpholin-4-ylpyrimidin-5-yl)-2-[rac-(3R)-3-[methyl(propan-2-yl)amino]pyrrolidin-1-yl]phenyl]-1-methyl-6-oxo-4-(trifluoromethyl)pyridine-3-carboxamide | — |
| 430 | 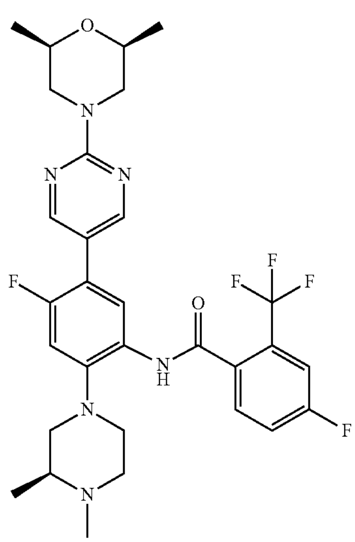 [SMILES: C[C@@H]1CN(c2ncc(-c3cc(NC(=O)c4ccc(F)cc4C(F)(F)F)c(N4CCN(C)[C@@H](C)C4)cc3F)cn2)C[C@H](C)O1] | 4-fluoro-N-[4-fluoro-5-[2-[rac-(2R,6S)-2,6-dimethylmorpholin-4-yl]pyrimidin-5-yl]-2-[rac-(3R)-3,4-dimethylpiperazin-1-yl]phenyl]-2-(trifluoromethyl)benzamide | 0.000296 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 431 | 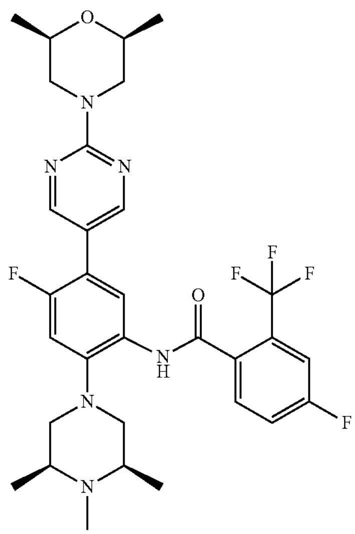 [SMILES: C[C@@H]1CN(c2ncc(-c3cc(NC(=O)c4ccc(F)cc4C(F)(F)F)c(N4C[C@@H](C)N(C)[C@@H](C)C4)cc3F)cn2)C[C@H](C)O1] | 4-fluoro-N-[4-fluoro-5-[2-[rac-(2R,6S)-2,6-dimethylmorpholin-4-yl]pyrimidin-5-yl]-2-[rac-(3S,5R)-3,4,5-trimethylpiperazin-1-yl]phenyl]-2-(trifluoromethyl)benzamide | 0.000649 |
| 432 | 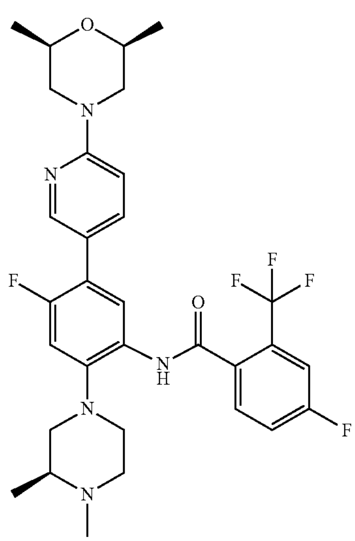 [SMILES: C[C@@H]1CN(c2ccc(-c3cc(NC(=O)c4ccc(F)cc4C(F)(F)F)c(N4CCN(C)[C@@H](C)C4)cc3F)cn2)C[C@H](C)O1] | 4-fluoro-N-[4-fluoro-5-[6-[rac-(2R,6S)-2,6-dimethylmorpholin-4-yl]pyridin-3-yl]-2-[rac-(3S,5R)-3,4,5-trimethylpiperazin-1-yl]phenyl]-2-(trifluoromethyl)benzamide | 0.00231 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 433 | 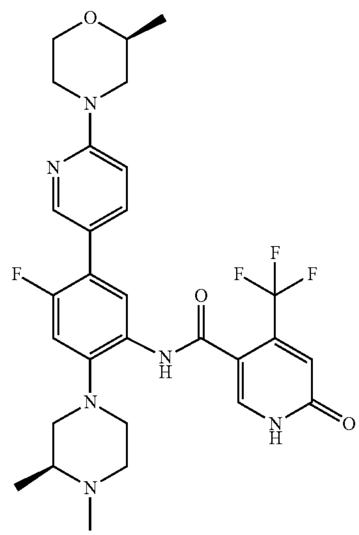 [SMILES: C[C@H]1CN(c2ccc(-c3cc(NC(=O)c4c[nH]c(=O)cc4C(F)(F)F)c(N4CCN(C)[C@@H](C)C4)cc3F)cn2)CCO1] | N-[4-fluoro-2-[rac-(3R)-3,4-dimethylpiperazin-1-yl]-5-[6-[rac-(2R)-2-methylmorpholin-4-yl]pyridin-3-yl]phenyl]-6-oxo-4-(trifluoromethyl)-1H-pyridine-3-carboxamide | 0.00284 |
| 434 | 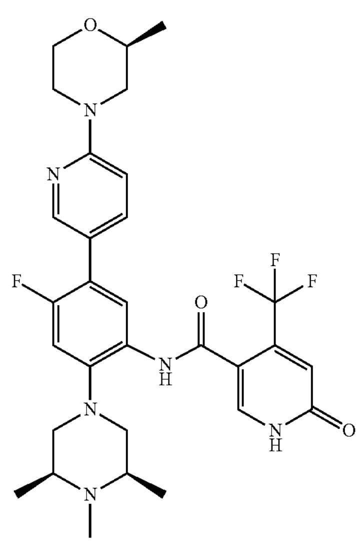 [SMILES: C[C@@H]1CN(c2cc(F)c(-c3ccc(N4CCO[C@@H](C)C4)nc3)cc2NC(=O)c2c[nH]c(=O)cc2C(F)(F)F)C[C@H](C)N1C] | N-[4-fluoro-5-[6-[rac-(2R)-2-methylmorpholin-4-yl]pyridin-3-yl]-2-[rac-(3S,5R)-3,4,5-trimethylpiperazin-1-yl]phenyl]-6-oxo-4-(trifluoromethyl)-1H-pyridine-3-carboxamide | 0.000617 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 435 | 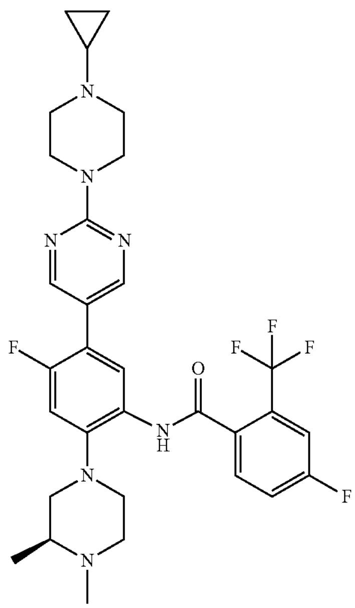 [SMILES: C[C@H]1CN(c2cc(F)c(-c3cnc(N4CCN(C5CC5)CC4)nc3)cc2NC(=O)c2ccc(F)cc2C(F)(F)F)CCN1C] | N-[5-[2-(4-cyclopropylpiperazin-1-yl)pyrimidin-5-yl]-4-fluoro-2-[rac-(3R)-3,4-dimethylpiperazin-1-yl]phenyl]-4-fluoro-2-(trifluoromethyl)benzamide | 0.00147 |
| 436 | 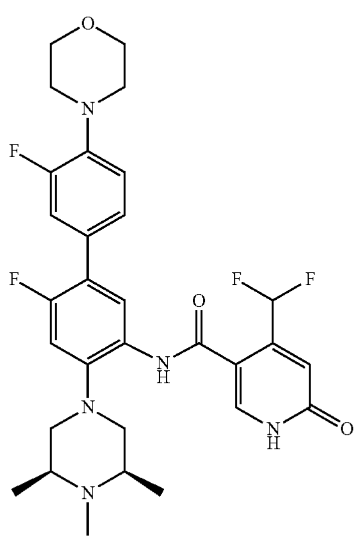 [SMILES: C[C@@H]1CN(c2cc(F)c(-c3ccc(N4CCOCC4)c(F)c3)cc2NC(=O)c2c[nH]c(=O)cc2C(F)F)C[C@H](C)N1C] | 4-(difluoromethyl)-N-[4-fluoro-5-(3-fluoro-4-morpholin-4-ylphenyl)-2-[rac-(3R,5S)-3,4,5-trimethylpiperazin-1-yl]phenyl]-6-oxo-1H-pyridine-3-carboxamide | 0.00139 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 437 | 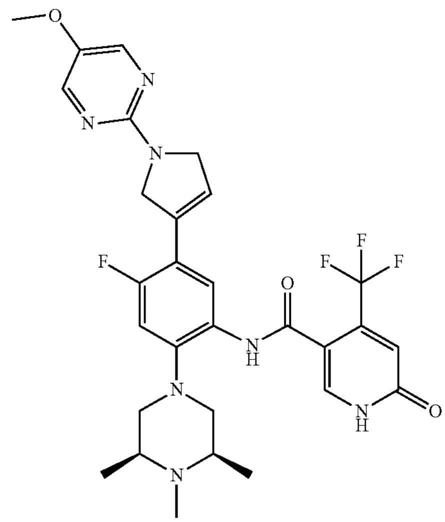 [SMILES: COc1cnc(N2CC=C(c3cc(NC(=O)c4c[nH]c(=O)cc4C(F)(F)F)c(N4C[C@@H](C)N(C)[C@@H](C)C4)cc3F)C2)nc1] | N-[4-fluoro-5-[1-(5-methoxypyrimidin-2-yl)-2,5-dihydropyrrol-3-yl]-2-[rac-(3R,5S)-3,4,5-trimethylpiperazin-1-yl]phenyl]-6-oxo-4-(trifluoromethyl)-1H-pyridine-3-carboxamide | 0.000721 |
| 438 | 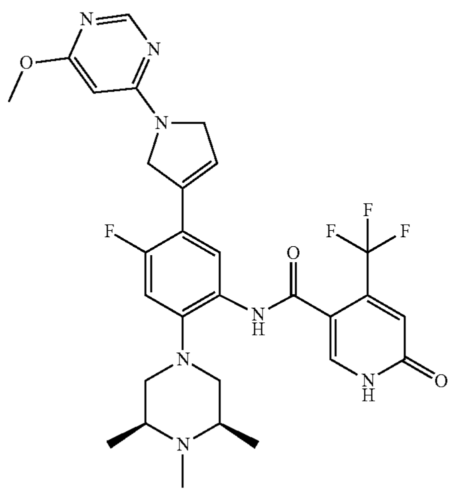 [SMILES: COc1cc(N2CC=C(c3cc(NC(=O)c4c[nH]c(=O)cc4C(F)(F)F)c(N4C[C@@H](C)N(C)[C@@H](C)C4)cc3F)C2)ncn1] | N-[4-fluoro-5-[1-(6-methoxypyrimidin-4-yl)-2,5-dihydropyrrol-3-yl]-2-[rac-(3R,5S)-3,4,5-trimethylpiperazin-1-yl]phenyl]-6-oxo-4-(trifluoromethyl)-1H-pyridine-3-carboxamide | 0.00199 |
| 439 | 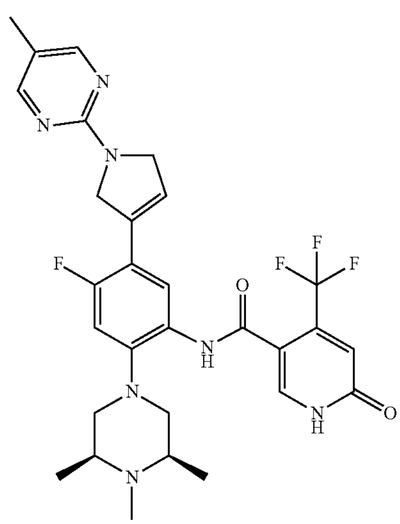 [SMILES: Cc1cnc(N2CC=C(c3cc(NC(=O)c4c[nH]c(=O)cc4C(F)(F)F)c(N4C[C@@H](C)N(C)[C@@H](C)C4)cc3F)C2)nc1] | N-[4-fluoro-5-[1-(5-methylpyrimidin-2-yl)-2,5-dihydropyrrol-3-yl]-2-[rac-(3R,5S)-3,4,5-trimethylpiperazin-1-yl]phenyl]-6-oxo-4-(trifluoromethyl)-1H-pyridine-3-carboxamide | 0.00245 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 440 | 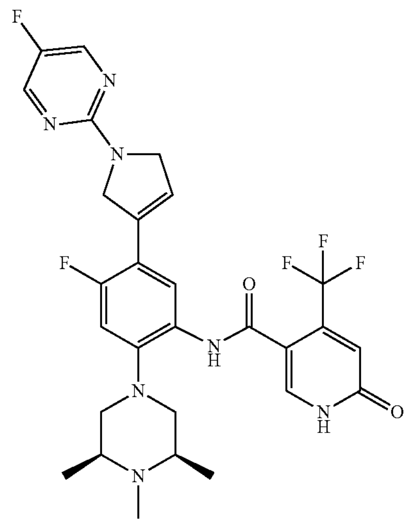 [SMILES: C[C@@H]1CN(c2cc(F)c(C3=CCN(c4ncc(F)cn4)C3)cc2NC(=O)c2c[nH]c(=O)cc2C(F)(F)F)C[C@H](C)N1C] | N-[4-fluoro-5-[1-(5-fluoropyrimidin-2-yl)-2,5-dihydropyrrol-3-yl]-2-[rac-(3R,5S)-3,4,5-trimethylpiperazin-1-yl]phenyl]-6-oxo-4-(trifluoromethyl)-1H-pyridine-3-carboxamide | 0.00288 |
| 441 | 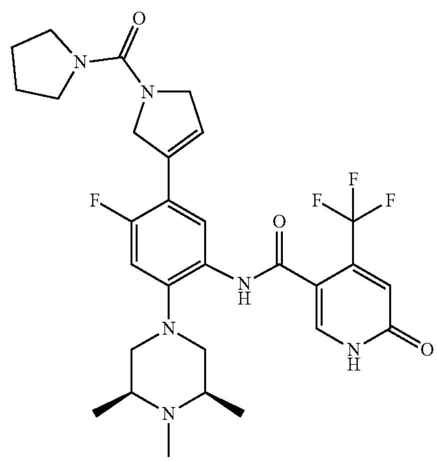 [SMILES: C[C@@H]1CN(c2cc(F)c(C3=CCN(C(=O)N4CCCC4)C3)cc2NC(=O)c2c[nH]c(=O)cc2C(F)(F)F)C[C@H](C)N1C] | N-[4-fluoro-5-[1-(pyrrolidine-1-carbonyl)-2,5-dihydropyrrol-3-yl]-2-[rac-(3R,5S)-3,4,5-trimethylpiperazin-1-yl]phenyl]-6-oxo-4-(trifluoromethyl)-1H-pyridine-3-carboxamide | 0.00191 |
| 442 | 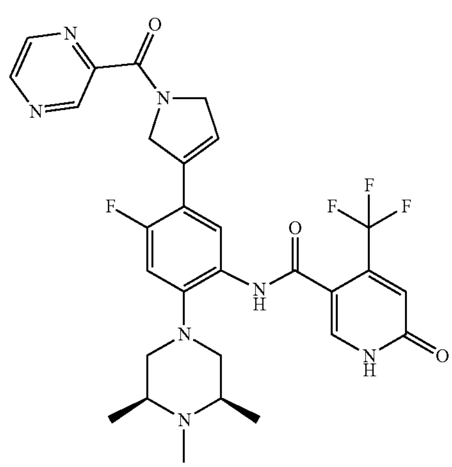 [SMILES: C[C@@H]1CN(c2cc(F)c(C3=CCN(C(=O)c4cnccn4)C3)cc2NC(=O)c2c[nH]c(=O)cc2C(F)(F)F)C[C@H](C)N1C] | N-[4-fluoro-5-[1-(pyrazine-2-carbonyl)-2,5-dihydropyrrol-3-yl]-2-[rac-(3R,5S)-3,4,5-trimethylpiperazin-1-yl]phenyl]-6-oxo-4-(trifluoromethyl)-1H-pyridine-3-carboxamide | 0.00367 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 443 | 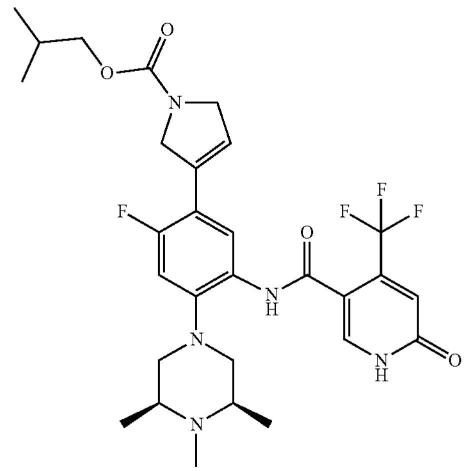 [SMILES: CC(C)COC(=O)N1CC=C(c2cc(NC(=O)c3c[nH]c(=O)cc3C(F)(F)F)c(N3C[C@@H](C)N(C)[C@@H](C)C3)cc2F)C1] | 2-methylpropyl 3-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-2,5-dihydropyrrole-1-carboxylate | 0.00237 |
| 444 | 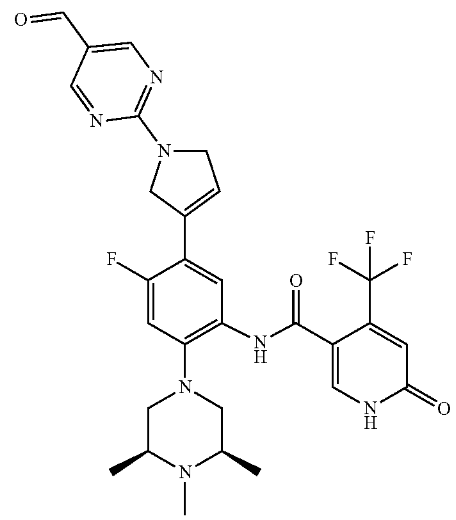 [SMILES: C[C@@H]1CN(c2cc(F)c(C3=CCN(c4ncc(C=O)cn4)C3)cc2NC(=O)c2c[nH]c(=O)cc2C(F)(F)F)C[C@H](C)N1C] | N-[4-fluoro-5-[1-(5-formylpyrimidin-2-yl)-2,5-dihydropyrrol-3-yl]-2-[rac-(3R,5S)-3,4,5-trimethylpiperazin-1-yl]phenyl]-6-oxo-4-(trifluoromethyl)-1H-pyridine-3-carboxamide | 0.00296 |
| 445 | 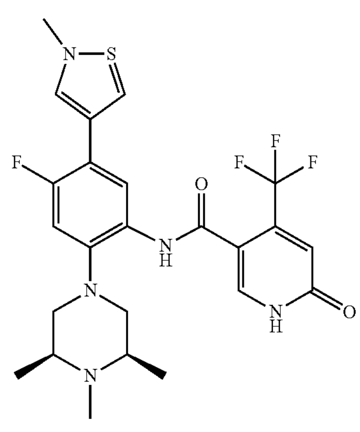 | N-[4-fluoro-5-(1-methylpyrazol-4-yl)-2-[rac-(3R,5S)-3,4,5-trimethylpiperazin-1-yl]phenyl]-6-oxo-4-(trifluoromethyl)-1H-pyridine-3-carboxamide | 0.00195 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 446 | 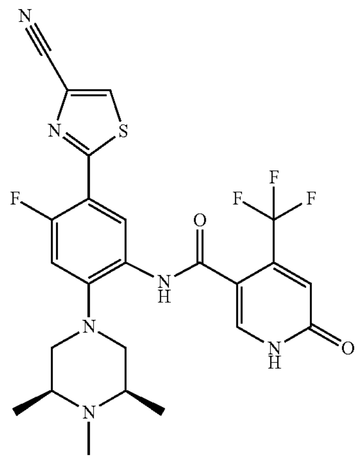 [SMILES: C[C@@H]1CN(c2cc(F)c(-c3nc(C#N)cs3)cc2NC(=O)c2c[nH]c(=O)cc2C(F)(F)F)C[C@H](C)N1C] | N-[5-(4-cyano-1,3-thiazol-2-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00294 |
| 447 | 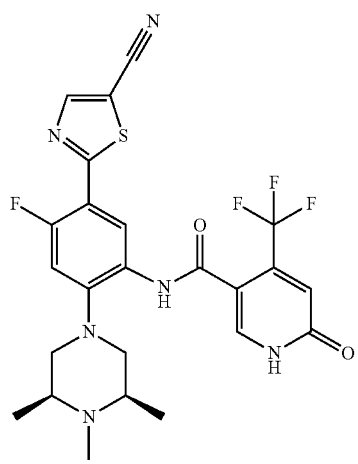 [SMILES: C[C@@H]1CN(c2cc(F)c(-c3ncc(C#N)s3)cc2NC(=O)c2c[nH]c(=O)cc2C(F)(F)F)C[C@H](C)N1C] | N-[5-(5-cyano-1,3-thiazol-2-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00288 |
| 448 | 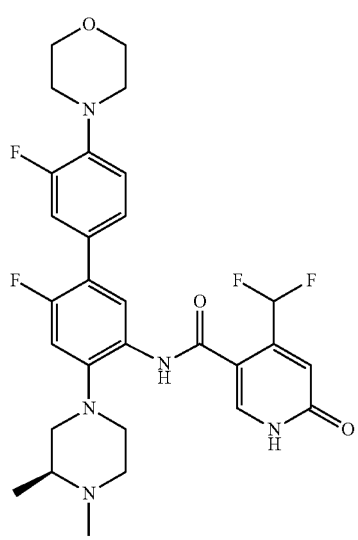 | 4-(difluoromethyl)-N-[4-fluoro-5-(3-fluoro-4-morpholin-4-ylphenyl)-2-[rac-(3R)-3,4-dimethylpiperazin-1-yl]phenyl]-6-oxo-1H-pyridine-3-carboxamide | 0.00101 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 449 | 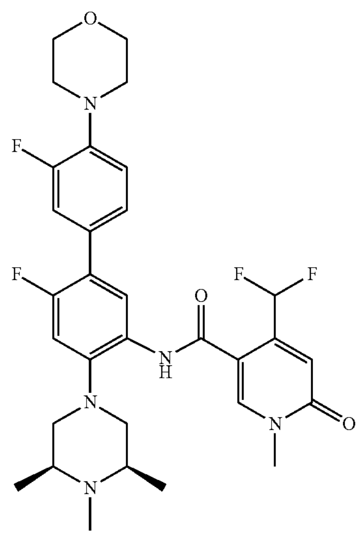 [SMILES: C[C@@H]1CN(c2cc(F)c(-c3ccc(N4CCOCC4)c(F)c3)cc2NC(=O)c2cn(C)c(=O)cc2C(F)F)C[C@H](C)N1C] | 4-(difluoromethyl)-N-[4-fluoro-5-(3-fluoro-4-morpholin-4-ylphenyl)-2-[rac-(3R,5S)-3,4,5-trimethylpiperazin-1-yl]phenyl]-1-methyl-6-oxopyridine-3-carboxamide | 0.00903 |
| 450 | 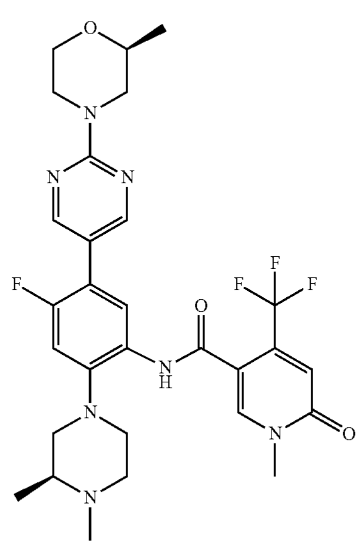 [SMILES: C[C@H]1CN(c2ncc(-c3cc(NC(=O)c4cn(C)c(=O)cc4C(F)(F)F)c(N4CCN(C)[C@@H](C)C4)cc3F)cn2)CCO1] | N-[4-fluoro-2-[rac-(3R)-3,4-dimethylpiperazin-1-yl]-5-[2-[rac-(2R)-2-methylmorpholin-4-yl]pyrimidin-5-yl]phenyl]-1-methyl-6-oxo-4-(trifluoromethyl)pyridine-3-carboxamide | 0.00102 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 451 | 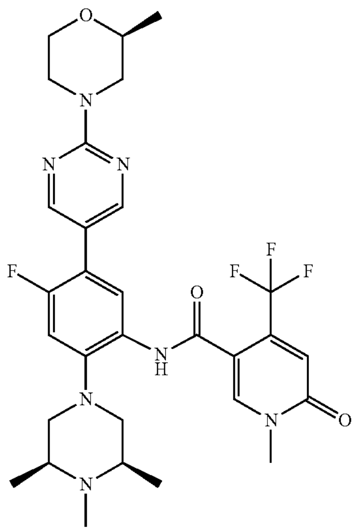 [SMILES: C[C@@H]1CN(c2cc(F)c(-c3cnc(N4CCO[C@@H](C)C4)nc3)cc2NC(=O)c2cn(C)c(=O)cc2C(F)(F)F)C[C@H](C)N1C] | N-[4-fluoro-5-[2-[rac-(2R)-2-methylmorpholin-4-yl]pyrimidin-5-yl]-2-[rac-(3S,5R)-3,4,5-trimethylpiperazin-1-yl]phenyl]-1-methyl-6-oxo-4-(trifluoromethyl)pyridine-3-carboxamide | 0.00172 |
| 452 | 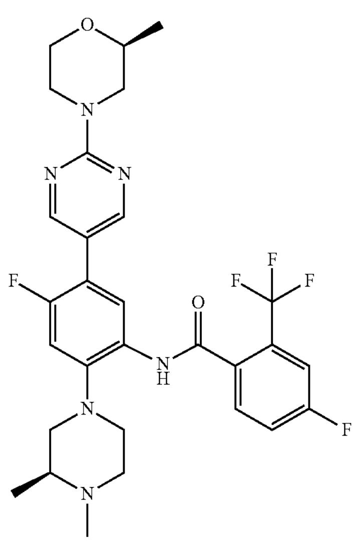 [SMILES: C[C@H]1CN(c2ncc(-c3cc(NC(=O)c4ccc(F)cc4C(F)(F)F)c(N4CCN(C)[C@@H](C)C4)cc3F)cn2)CCO1] | 4-fluoro-N-[4-fluoro-2-[rac-(3R)-3,4-dimethylpiperazin-1-yl]-5-[2-[rac-(2R)-2-methylmorpholin-4-yl]pyrimidin-5-yl]phenyl]-2-(trifluoromethyl)benzamide | 0.000493 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 453 | 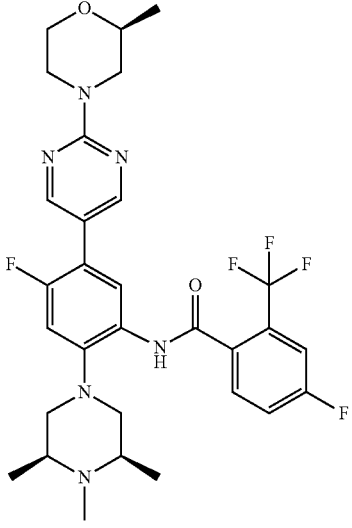 [SMILES: C[C@@H]1CN(c2cc(F)c(-c3cnc(N4CCO[C@@H](C)C4)nc3)cc2NC(=O)c2ccc(F)cc2C(F)(F)F)C[C@H](C)N1C] | 4-fluoro-N-[4-fluoro-5-[2-[rac-(2R)-2-methylmorpholin-4-yl]pyrimidin-5-yl]-2-[rac-(3S,5R)-3,4,5-trimethylpiperazin-1-yl]phenyl]-2-(trifluoromethyl)benzamide | 0.000822 |
| 454 | 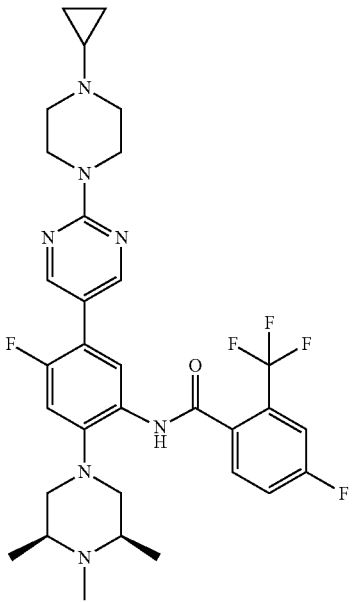 [SMILES: C[C@@H]1CN(c2cc(F)c(-c3cnc(N4CCN(C5CC5)CC4)nc3)cc2NC(=O)c2ccc(F)cc2C(F)(F)F)C[C@H](C)N1C] | N-[5-[2-(4-cyclopropylpiperazin-1-yl)pyrimidin-5-yl]-4-fluoro-2-[rac-(3R,5S)-3,4,5-trimethylpiperazin-1-yl]phenyl]-4-fluoro-2-(trifluoromethyl)benzamide | 0.00405 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 455 | 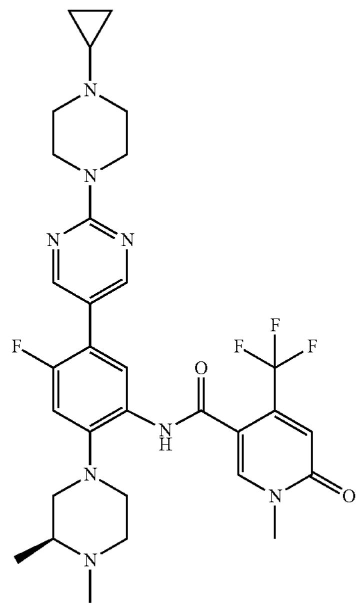 [SMILES: C[C@H]1CN(c2cc(F)c(-c3cnc(N4CCN(C5CC5)CC4)nc3)cc2NC(=O)c2cn(C)c(=O)cc2C(F)(F)F)CCN1C] | N-[5-[2-(4-cyclopropylpiperazin-1-yl)pyrimidin-5-yl]-4-fluoro-2-[rac-(3R)-3,4-dimethylpiperazin-1-yl]phenyl]-1-methyl-6-oxo-4-(trifluoromethyl)pyridine-3-carboxamide | 0.00198 |
| 456 | 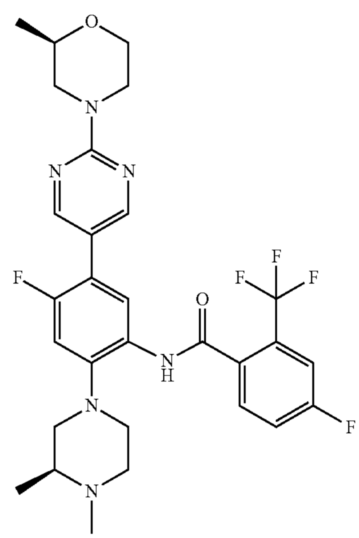 [SMILES: C[C@@H]1CN(c2ncc(-c3cc(NC(=O)c4ccc(F)cc4C(F)(F)F)c(N4CCN(C)[C@@H](C)C4)cc3F)cn2)CCO1] | 4-fluoro-N-[4-fluoro-2-[rac-(3S)-3,4-dimethylpiperazin-1-yl]-5-[2-[rac-(2R)-2-methylmorpholin-4-yl]pyrimidin-5-yl]phenyl]-2-(trifluoromethyl)benzamide | 0.00108 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 457 | 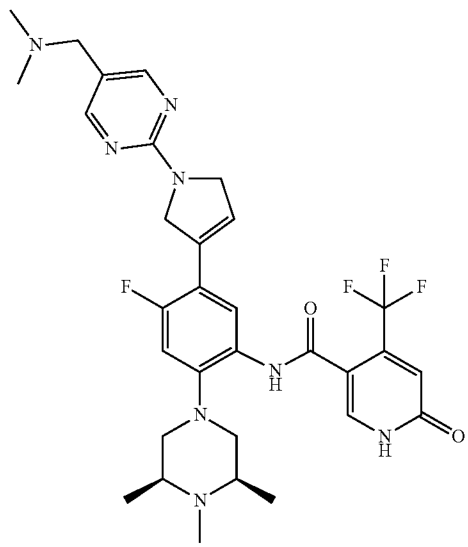 [SMILES: C[C@@H]1CN(c2cc(F)c(C3=CCN(c4ncc(CN(C)C)cn4)C3)cc2NC(=O)c2c[nH]c(=O)cc2C(F)(F)F)C[C@H](C)N1C] | N-[5-[1-[5-[(dimethylamino)methyl]pyrimidin-2-yl]-2,5-dihydropyrrol-3-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00257 |
| 458 | 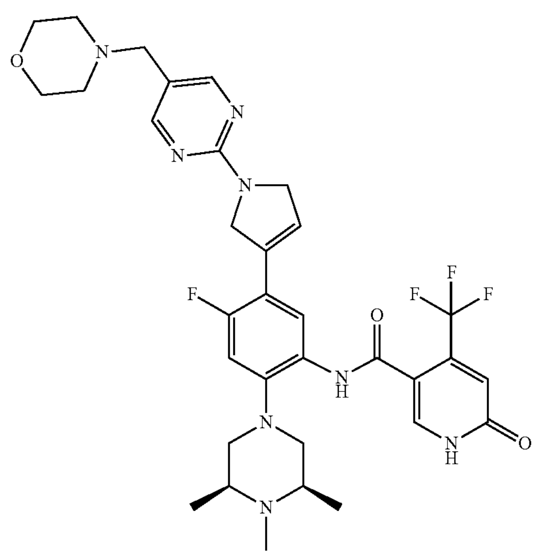 [SMILES: C[C@@H]1CN(c2cc(F)c(C3=CCN(c4ncc(CN5CCOCC5)cn4)C3)cc2NC(=O)c2c[nH]c(=O)cc2C(F)(F)F)C[C@H](C)N1C] | N-[4-fluoro-5-[1-[5-(morpholin-4-ylmethyl)pyrimidin-2-yl]-2,5-dihydropyrrol-3-yl]-2-[rac-(3R,5S)-3,4,5-trimethylpiperazin-1-yl]phenyl]-6-oxo-4-(trifluoromethyl)-1H-pyridine-3-carboxamide | 0.000474 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 459 | 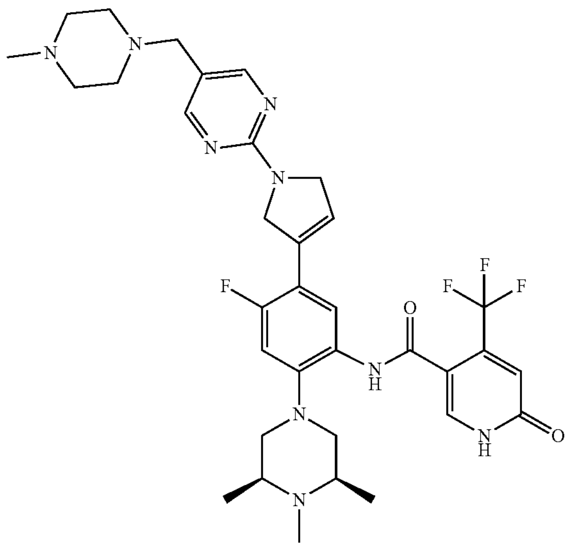 [SMILES: C[C@@H]1CN(c2cc(F)c(C3=CCN(c4ncc(CN5CCN(C)CC5)cn4)C3)cc2NC(=O)c2c[nH]c(=O)cc2C(F)(F)F)C[C@H](C)N1C] | N-[4-fluoro-5-[1-[5-[(4-methylpiperazin-1-yl)methyl]pyrimidin-2-yl]-2,5-dihydropyrrol-3-yl]-2-[rac-(3R,5S)-3,4,5-trimethylpiperazin-1-yl]phenyl]-6-oxo-4-(trifluoromethyl)-1H-pyridine-3-carboxamide | 0.000392 |
| 460 | 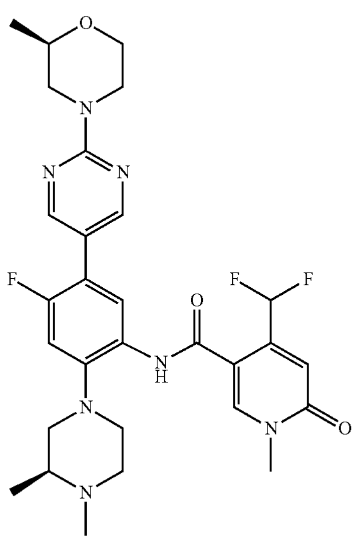 [SMILES: C[C@@H]1CN(c2ncc(-c3cc(NC(=O)c4cn(C)c(=O)cc4C(F)F)c(N4CCN(C)[C@@H](C)C4)cc3F)cn2)CCO1] | 4-(difluoromethyl)-N-[4-fluoro-2-[rac-(3S)-3,4-dimethylpiperazin-1-yl]-5-[2-[rac-(2R)-2-methylmorpholin-4-yl]pyrimidin-5-yl]phenyl]-1-methyl-6-oxopyridine-3-carboxamide | 0.00343 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 461 | 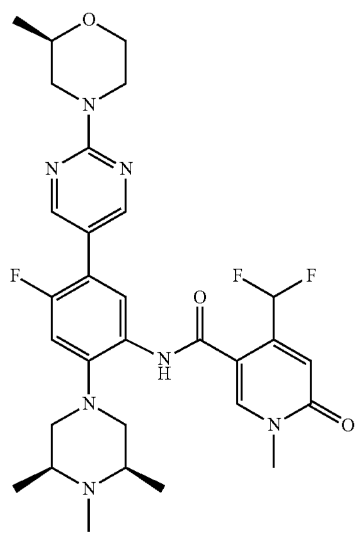 [SMILES: C[C@@H]1CN(c2ncc(-c3cc(NC(=O)c4cn(C)c(=O)cc4C(F)F)c(N4C[C@@H](C)N(C)[C@@H](C)C4)cc3F)cn2)CCO1] | 4-(difluoromethyl)-N-[4-fluoro-5-[2-[rac-(2R)-2-methylmorpholin-4-yl]pyrimidin-5-yl]-2-[rac-(3R,5S)-3,4,5-trimethylpiperazin-1-yl]phenyl]-1-methyl-6-oxopyridine-3-carboxamide | 0.00493 |
| 462 | 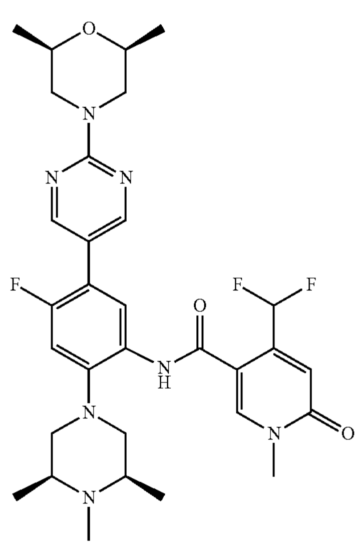 [SMILES: C[C@@H]1CN(c2ncc(-c3cc(NC(=O)c4cn(C)c(=O)cc4C(F)F)c(N4C[C@@H](C)N(C)[C@@H](C)C4)cc3F)cn2)C[C@H](C)O1] | 4-(difluoromethyl)-N-[4-fluoro-5-[2-[rac-(2R,6S)-2,6-dimethylmorpholin-4-yl]pyrimidin-5-yl]-2-[rac-(3R,5S)-3,4,5-trimethylpiperazin-1-yl]phenyl]-1-methyl-6-oxopyridine-3-carboxamide | 0.0037 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 463 | 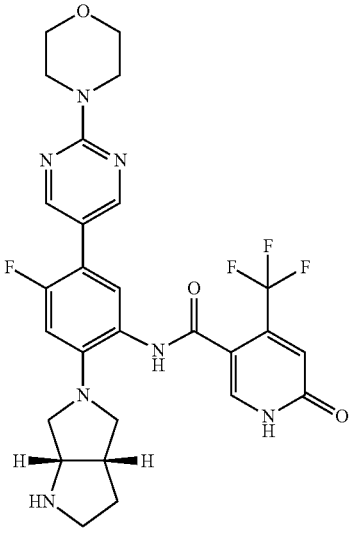 [SMILES: O=C(Nc1cc(-c2cnc(N3CCOCC3)nc2)c(F)cc1N1C[C@@H]2CCN[C@@H]2C1)c1c[nH]c(=O)cc1C(F)(F)F] | N-[4-fluoro-5-(2-morpholin-4-ylpyrimidin-5-yl)-2-[rac-(3aR,6aR)-2,3,3a,4,6,6a-hexahydro-1H-pyrrolo[2,3-c]pyrrol-5-yl]phenyl]-6-oxo-4-(trifluoromethyl)-1H-pyridine-3-carboxamide | 0.168 |
| 464 | 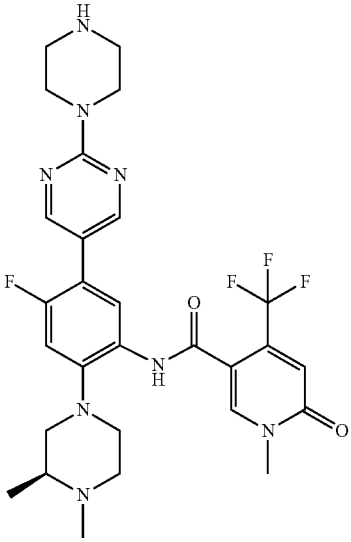 [SMILES: C[C@H]1CN(c2cc(F)c(-c3cnc(N4CCNCC4)nc3)cc2NC(=O)c2cn(C)c(=O)cc2C(F)(F)F)CCN1C] | N-[4-fluoro-5-(2-piperazin-1-ylpyrimidin-5-yl)-2-[rac-(3R)-3,4-dimethylpiperazin-1-yl]phenyl]-1-methyl-6-oxo-4-(trifluoromethyl)pyridine-3-carboxamide | 0.00221 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 465 | 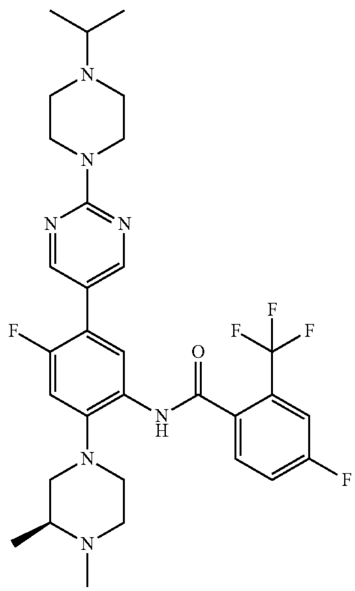 [SMILES: CC(C)N1CCN(c2ncc(-c3cc(NC(=O)c4ccc(F)cc4C(F)(F)F)c(N4CCN(C)[C@@H](C)C4)cc3F)cn2)CC1] | 4-fluoro-N-[4-fluoro-5-[2-(4-propan-2-ylpiperazin-1-yl)pyrimidin-5-yl]-2-[rac-(3R)-3,4-dimethylpiperazin-1-yl]phenyl]-2-(trifluoromethyl)benzamide | 0.00177 |
| 466 | 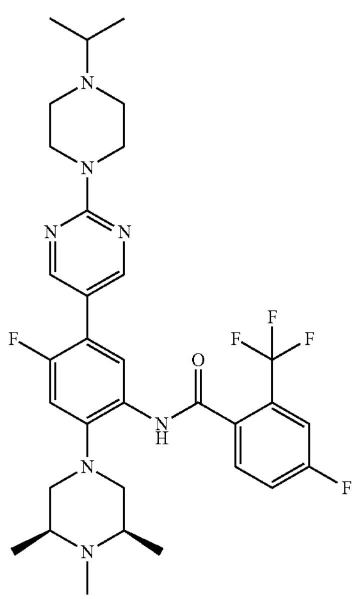 [SMILES: CC(C)N1CCN(c2ncc(-c3cc(NC(=O)c4ccc(F)cc4C(F)(F)F)c(N4C[C@@H](C)N(C)[C@@H](C)C4)cc3F)cn2)CC1] | 4-fluoro-N-[4-fluoro-5-[2-(4-propan-2-ylpiperazin-1-yl)pyrimidin-5-yl]-2-[rac-(3R,5S)-3,4,5-trimethylpiperazin-1-yl]phenyl]-2-(trifluoromethyl)benzamide | 0.00228 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 467 | 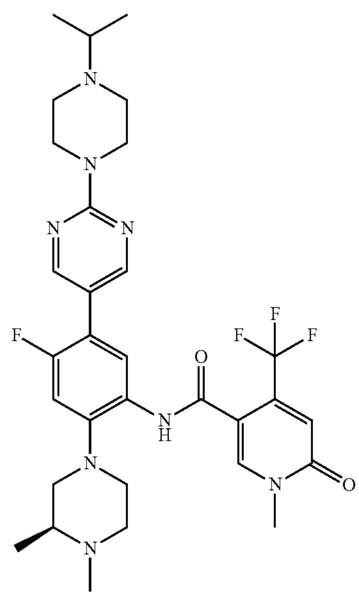 [SMILES: CC(C)N1CCN(c2ncc(-c3cc(NC(=O)c4cn(C)c(=O)cc4C(F)(F)F)c(N4CCN(C)[C@@H](C)C4)cc3F)cn2)CC1] | N-[4-fluoro-5-[2-(4-propan-2-ylpiperazin-1-yl)pyrimidin-5-yl]-2-[rac-(3R)-3,4-dimethylpiperazin-1-yl]phenyl]-1-methyl-6-oxo-4-(trifluoromethyl)pyridine-3-carboxamide | 0.00254 |
| 468 | 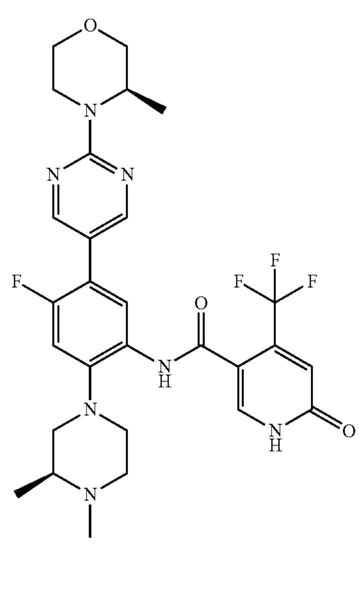 [SMILES: C[C@@H]1COCCN1c1ncc(-c2cc(NC(=O)c3c[nH]c(=O)cc3C(F)(F)F)c(N3CCN(C)[C@@H](C)C3)cc2F)cn1] | N-[4-fluoro-2-[rac-(3S)-3,4-dimethylpiperazin-1-yl]-5-[2-[rac-(3R)-3-methylmorpholin-4-yl]pyrimidin-5-yl]phenyl]-6-oxo-4-(trifluoromethyl)-1H-pyridine-3-carboxamide | 0.00228 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 469 | 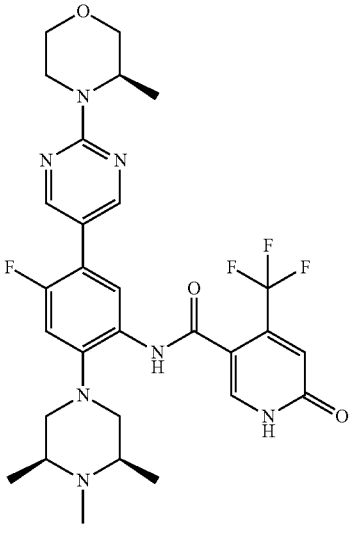 [SMILES: C[C@@H]1COCCN1c1ncc(-c2cc(NC(=O)c3c[nH]c(=O)cc3C(F)(F)F)c(N3C[C@@H](C)N(C)[C@@H](C)C3)cc2F)cn1] | N-[4-fluoro-5-[2-[rac-(3R)-3-methylmorpholin-4-yl]pyrimidin-5-yl]-2-[rac-(3R,5S)-3,4,5-trimethylpiperazin-1-yl]phenyl]-6-oxo-4-(trifluoromethyl)-1H-pyridine-3-carboxamide | 0.00564 |
| 470 | 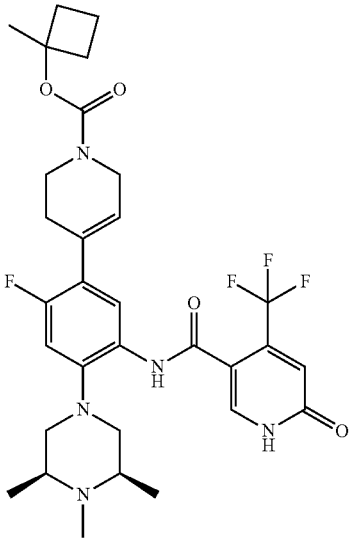 | (1-methylcyclobutyl) 4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.00427 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 471 | 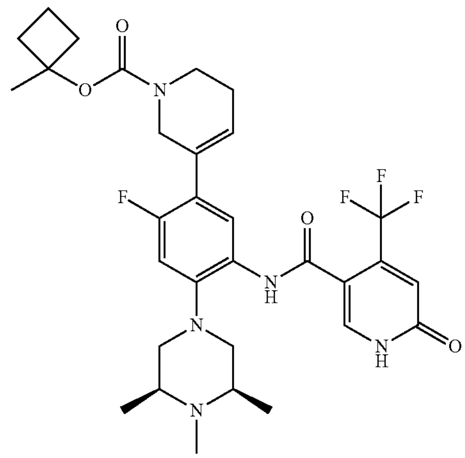 [SMILES: C[C@@H]1CN(c2cc(F)c(C3=CCCN(C(=O)OC4(C)CCC4)C3)cc2NC(=O)c2c[nH]c(=O)cc2C(F)(F)F)C[C@H](C)N1C] | (1-methylcyclobutyl) 5-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.000494 |
| 472 | 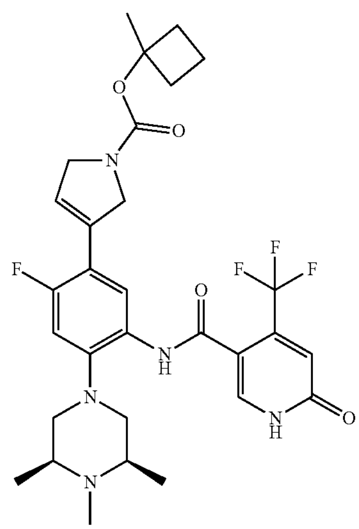 [SMILES: C[C@@H]1CN(c2cc(F)c(C3=CCN(C(=O)OC4(C)CCC4)C3)cc2NC(=O)c2c[nH]c(=O)cc2C(F)(F)F)C[C@H](C)N1C] | (1-methylcyclobutyl) 3-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-2,5-dihydropyrrole-1-carboxylate | 0.000407 |
| 473 | 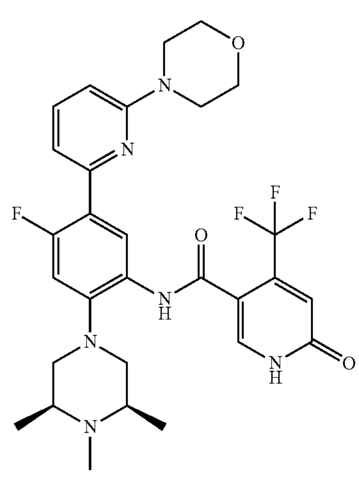 | N-[4-fluoro-5-(6-morpholin-4-ylpyridin-2-yl)-2-[rac-(3R,5S)-3,4,5-trimethylpiperazin-1-yl]phenyl]-6-oxo-4-(trifluoromethyl)-1H-pyridine-3-carboxamide | 0.000533 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 474 | 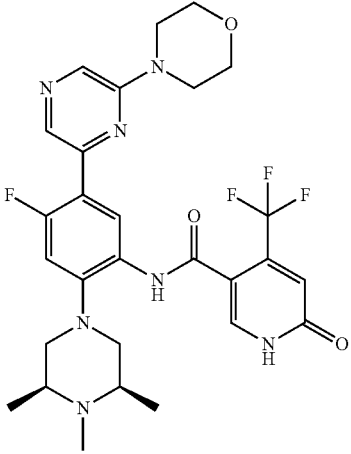 [SMILES: C[C@@H]1CN(c2cc(F)c(-c3cncc(N4CCOCC4)n3)cc2NC(=O)c2c[nH]c(=O)cc2C(F)(F)F)C[C@H](C)N1C] | N-[4-fluoro-5-(6-morpholin-4-ylpyrazin-2-yl)-2-[rac-(3R,5S)-3,4,5-trimethylpiperazin-1-yl]phenyl]-6-oxo-4-(trifluoromethyl)-1H-pyridine-3-carboxamide | 0.0012 |
| 475 | 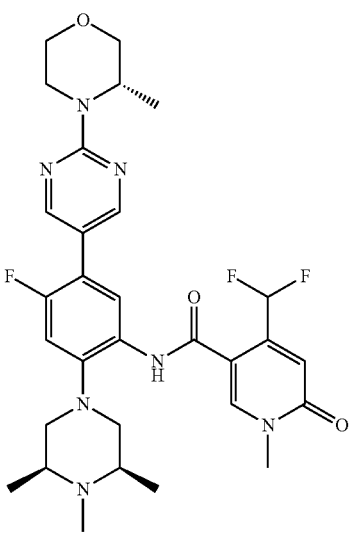 [SMILES: C[C@@H]1CN(c2cc(F)c(-c3cnc(N4CCOC[C@@H]4C)nc3)cc2NC(=O)c2cn(C)c(=O)cc2C(F)F)C[C@H](C)N1C] | 4-(difluoromethyl)-N-[4-fluoro-5-[2-[rac-(3R)-3-methylmorpholin-4-yl]pyrimidin-5-yl]-2-[rac-(3S,5R)-3,4,5-trimethylpiperazin-1-yl]phenyl]-1-methyl-6-oxopyridine-3-carboxamide | 0.00352 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 476 | 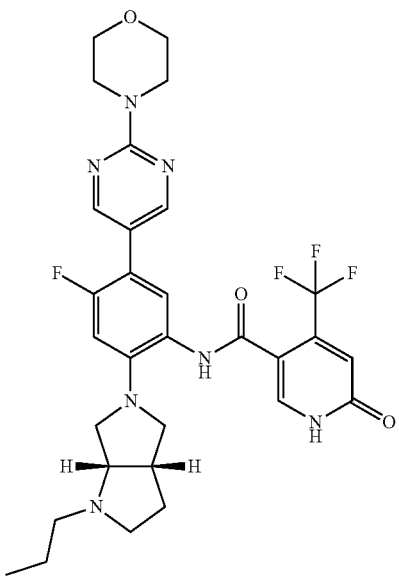 [SMILES: CCCN1CC[C@H]2CN(c3cc(F)c(-c4cnc(N5CCOCC5)nc4)cc3NC(=O)c3c[nH]c(=O)cc3C(F)(F)F)C[C@H]21] | N-[4-fluoro-5-(2-morpholin-4-ylpyrimidin-5-yl)-2-[rac-(3aR,6aR)-1-propyl-2,3,3a,4,6,6a-hexahydropyrrolo[2,3-c]pyrrol-5-yl]phenyl]-6-oxo-4-(trifluoromethyl)-1H-pyridine-3-carboxamide | 0.00971 |
| 477 | 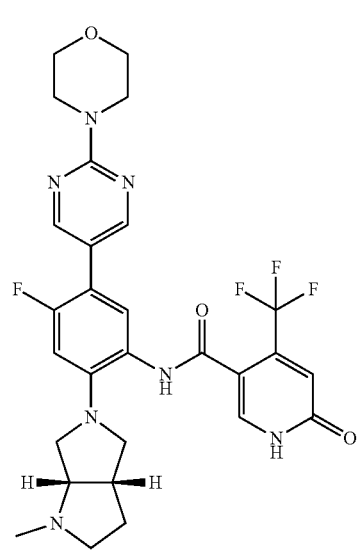 [SMILES: CN1CC[C@H]2CN(c3cc(F)c(-c4cnc(N5CCOCC5)nc4)cc3NC(=O)c3c[nH]c(=O)cc3C(F)(F)F)C[C@H]21] | N-[4-fluoro-5-(2-morpholin-4-ylpyrimidin-5-yl)-2-[rac-(3aR,6aR)-1-methyl-2,3,3a,4,6,6a-hexahydropyrrolo[2,3-c]pyrrol-5-yl]phenyl]-6-oxo-4-(trifluoromethyl)-1H-pyridine-3-carboxamide | 0.0242 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 478 | 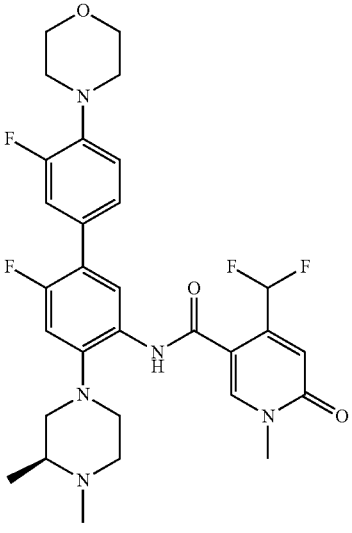 [SMILES: C[C@H]1CN(c2cc(F)c(-c3ccc(N4CCOCC4)c(F)c3)cc2NC(=O)c2cn(C)c(=O)cc2C(F)F)CCN1C] | 4-(difluoromethyl)-N-[4-fluoro-5-(3-fluoro-4-morpholin-4-ylphenyl)-2-[rac-(3R)-3,4-dimethylpiperazin-1-yl]phenyl]-1-methyl-6-oxopyridine-3-carboxamide | 0.00532 |
| 479 | 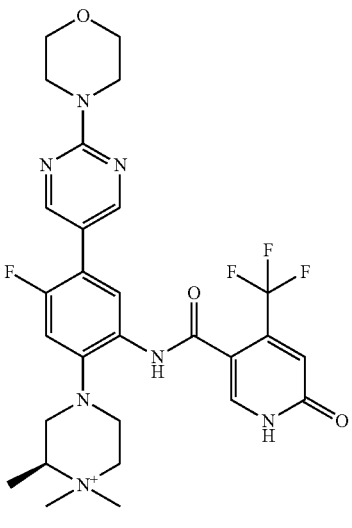 [SMILES: C[C@H]1CN(c2cc(F)c(-c3cnc(N4CCOCC4)nc3)cc2NC(=O)c2c[nH]c(=O)cc2C(F)(F)F)CC[N+]1(C)C] | N-[4-fluoro-5-(2-morpholin-4-ylpyrimidin-5-yl)-2-[rac-(3R,5S)-3,4,4,5-tetramethylpiperazin-4-ium-1-yl]phenyl]-6-oxo-4-(trifluoromethyl)-1H-pyridine-3-carboxamide | 0.00354 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 480 | 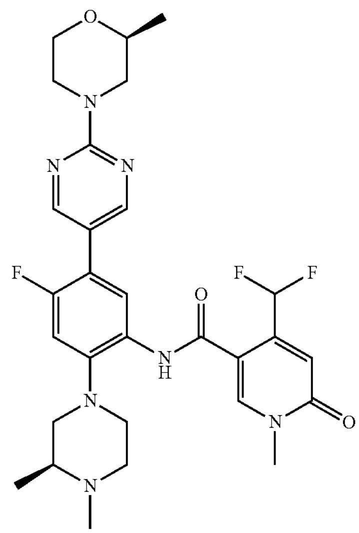 [SMILES: C[C@H]1CN(c2ncc(-c3cc(NC(=O)c4cn(C)c(=O)cc4C(F)F)c(N4CCN(C)[C@@H](C)C4)cc3F)cn2)CCO1] | 4-(difluoromethyl)-N-[4-fluoro-2-[rac-(3R)-3,4-dimethylpiperazin-1-yl]-5-[2-[rac-(2R)-2-methylmorpholin-4-yl]pyrimidin-5-yl]phenyl]-1-methyl-6-oxopyridine-3-carboxamide | 0.00215 |
| 481 | 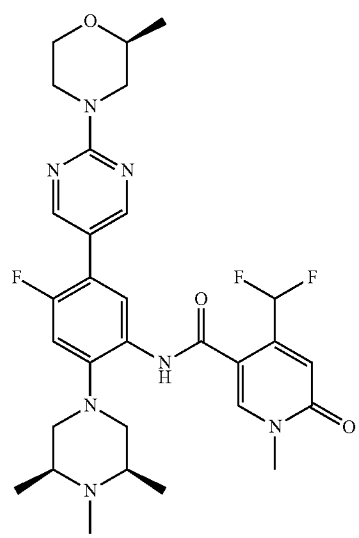 [SMILES: C[C@@H]1CN(c2cc(F)c(-c3cnc(N4CCO[C@@H](C)C4)nc3)cc2NC(=O)c2cn(C)c(=O)cc2C(F)F)C[C@H](C)N1C] | 4-(difluoromethyl)-N-[4-fluoro-5-[2-[rac-(2R)-2-methylmorpholin-4-yl]pyrimidin-5-yl]-2-[rac-(3S,5R)-3,4,5-trimethylpiperazin-1-yl]phenyl]-1-methyl-6-oxopyridine-3-carboxamide | 0.00489 |
| 482 | 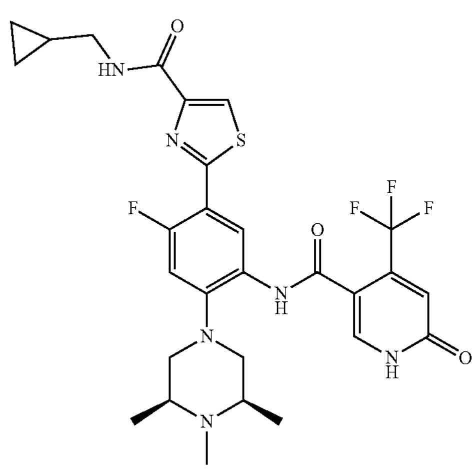 | N-(cyclopropylmethyl)-2-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-1,3-thiazole-4-carboxamide | 0.00175 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 483 | 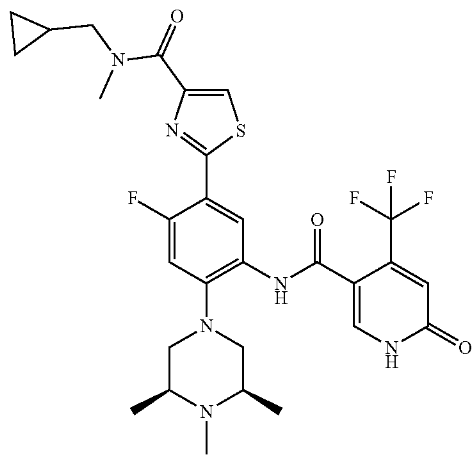 [SMILES: C[C@@H]1CN(c2cc(F)c(-c3nc(C(=O)N(C)CC4CC4)cs3)cc2NC(=O)c2c[nH]c(=O)cc2C(F)(F)F)C[C@H](C)N1C] | N-(cyclopropylmethyl)-2-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-N-methyl-1,3-thiazole-4-carboxamide | 0.00397 |
| 484 | 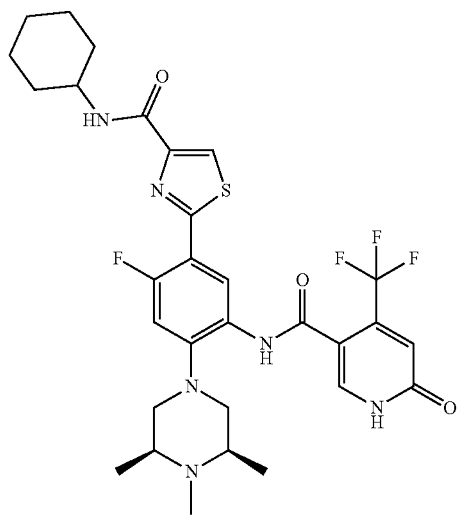 | N-cyclohexyl-2-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-1,3-thiazole-4-carboxamide | 0.00307 |
| 485 | 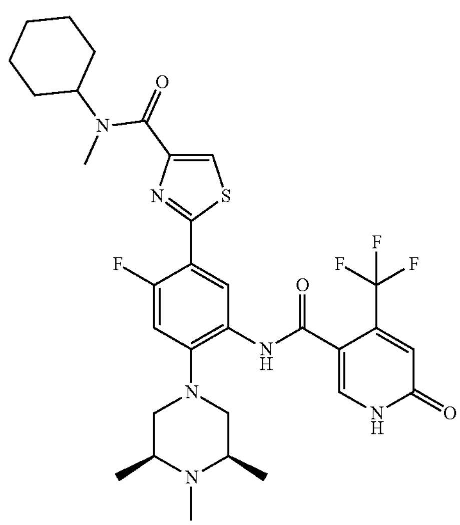 [SMILES: C[C@@H]1CN(c2cc(F)c(-c3nc(C(=O)N(C)C4CCCCC4)cs3)cc2NC(=O)c2c[nH]c(=O)cc2C(F)(F)F)C[C@H](C)N1C] | N-cyclohexyl-2-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-N-methyl-1,3-thiazole-4-carboxamide | 0.00221 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 486 | 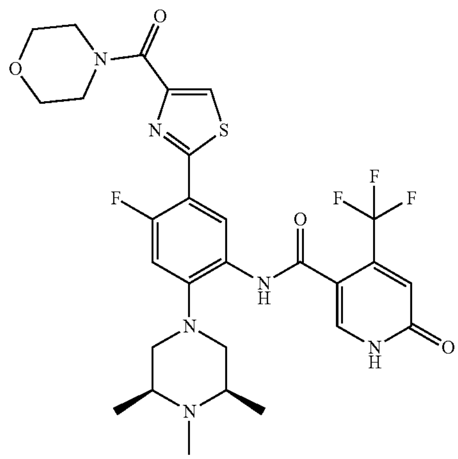 [SMILES: C[C@@H]1CN(c2cc(F)c(-c3nc(C(=O)N4CCOCC4)cs3)cc2NC(=O)c2c[nH]c(=O)cc2C(F)(F)F)C[C@H](C)N1C] | N-[4-fluoro-5-[4-(morpholine-4-carbonyl)-1,3-thiazol-2-yl]-2-[rac-(3R,5S)-3,4,5-trimethylpiperazin-1-yl]phenyl]-6-oxo-4-(trifluoromethyl)-1H-pyridine-3-carboxamide | 0.00244 |
| 487 | 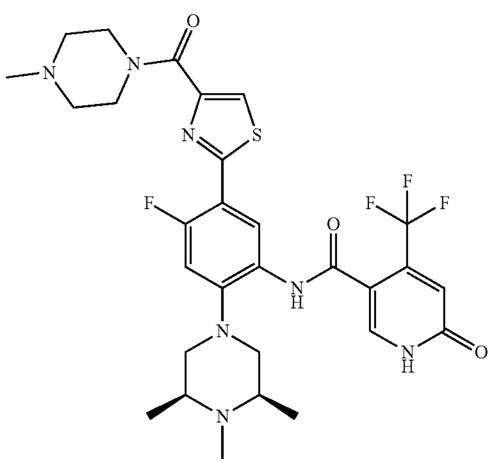 [SMILES: C[C@@H]1CN(c2cc(F)c(-c3nc(C(=O)N4CCN(C)CC4)cs3)cc2NC(=O)c2c[nH]c(=O)cc2C(F)(F)F)C[C@H](C)N1C] | N-[4-fluoro-5-[4-(4-methylpiperazine-1-carbonyl)-1,3-thiazol-2-yl]-2-[rac-(3R,5S)-3,4,5-trimethylpiperazin-1-yl]phenyl]-6-oxo-4-(trifluoromethyl)-1H-pyridine-3-carboxamide | 0.00281 |
| 488 | 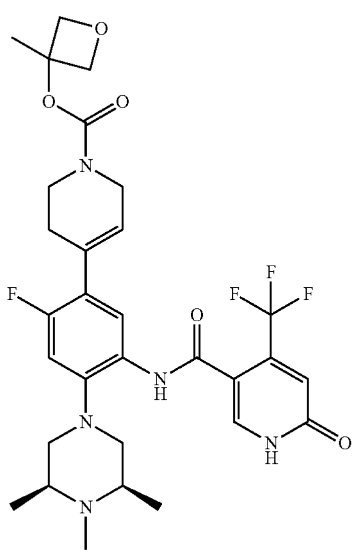 | (3-methyloxetan-3-yl) 4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.00487 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 489 | 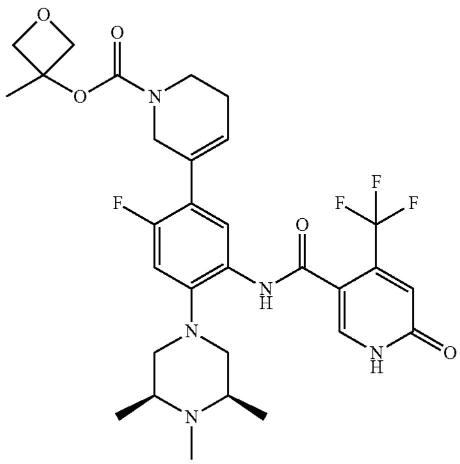 [SMILES: C[C@@H]1CN(c2cc(F)c(C3=CCCN(C(=O)OC4(C)COC4)C3)cc2NC(=O)c2c[nH]c(=O)cc2C(F)(F)F)C[C@H](C)N1C] | (3-methyloxetan-3-yl) 5-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.00274 |
| 490 | 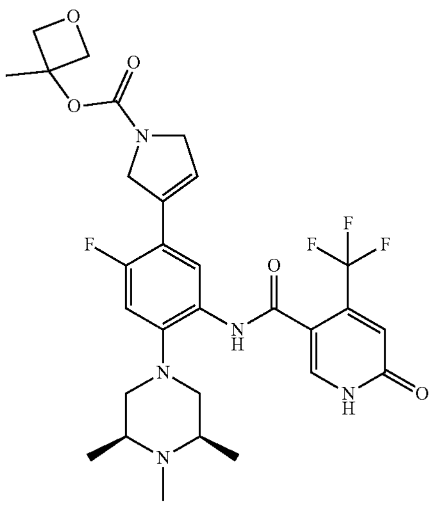 [SMILES: C[C@@H]1CN(c2cc(F)c(C3=CCN(C(=O)OC4(C)COC4)C3)cc2NC(=O)c2c[nH]c(=O)cc2C(F)(F)F)C[C@H](C)N1C] | (3-methyloxetan-3-yl) 3-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-2,5-dihydropyrrole-1-carboxylate | 0.00324 |
| 491 | 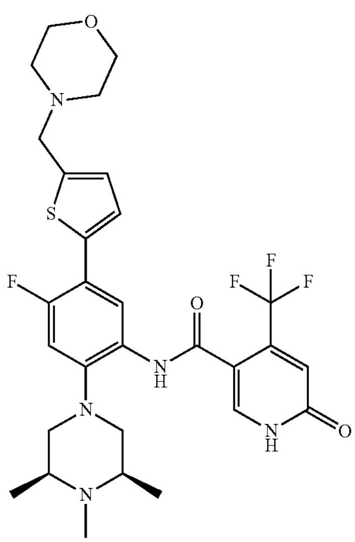 [SMILES: C[C@@H]1CN(c2cc(F)c(-c3ccc(CN4CCOCC4)s3)cc2NC(=O)c2c[nH]c(=O)cc2C(F)(F)F)C[C@H](C)N1C] | N-[4-fluoro-5-[5-(morpholin-4-ylmethyl)thiophen-2-yl]-2-[rac-(3R,5S)-3,4,5-trimethylpiperazin-1-yl]phenyl]-6-oxo-4-(trifluoromethyl)-1H-pyridine-3-carboxamide | 0.00359 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 492 | 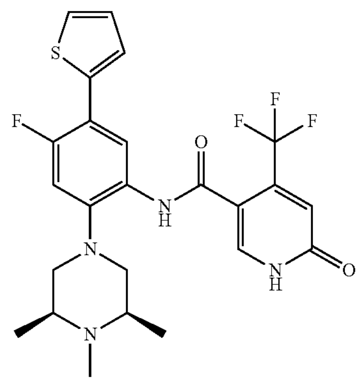 [SMILES: C[C@@H]1CN(c2cc(F)c(-c3cccs3)cc2NC(=O)c2c[nH]c(=O)cc2C(F)(F)F)C[C@H](C)N1C] | N-[4-fluoro-2-[rac-(3R,5S)-3,4,5-trimethylpiperazin-1-yl]-5-thiophen-2-ylphenyl]-6-oxo-4-(trifluoromethyl)-1H-pyridine-3-carboxamide | 0.00335 |
| 493 | 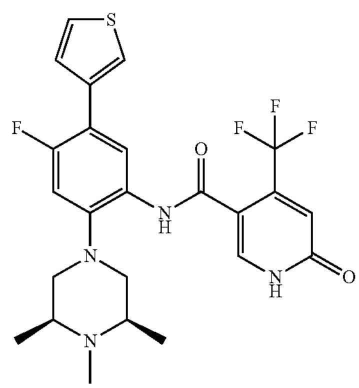 [SMILES: C[C@@H]1CN(c2cc(F)c(-c3ccsc3)cc2NC(=O)c2c[nH]c(=O)cc2C(F)(F)F)C[C@H](C)N1C] | N-[4-fluoro-2-[rac-(3R,5S)-3,4,5-trimethylpiperazin-1-yl]-5-thiophen-3-ylphenyl]-6-oxo-4-(trifluoromethyl)-1H-pyridine-3-carboxamide | 0.00286 |
| 494 | 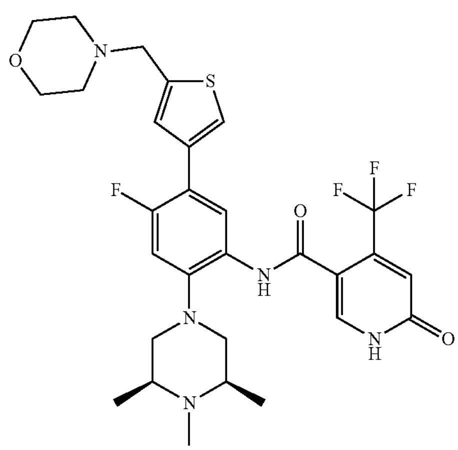 [SMILES: C[C@@H]1CN(c2cc(F)c(-c3csc(CN4CCOCC4)c3)cc2NC(=O)c2c[nH]c(=O)cc2C(F)(F)F)C[C@H](C)N1C] | N-[4-fluoro-5-[5-(morpholin-4-ylmethyl)thiophen-3-yl]-2-[rac-(3R,5S)-3,4,5-trimethylpiperazin-1-yl]phenyl]-6-oxo-4-(trifluoromethyl)-1H-pyridine-3-carboxamide | 0.00301 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 495 | 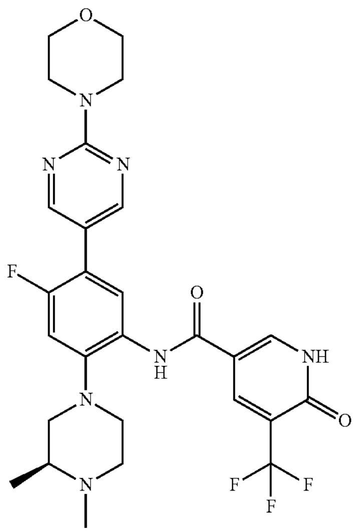 [SMILES: C[C@H]1CN(c2cc(F)c(-c3cnc(N4CCOCC4)nc3)cc2NC(=O)c2c[nH]c(=O)c(C(F)(F)F)c2)CCN1C] | N-[4-fluoro-5-(2-morpholin-4-ylpyrimidin-5-yl)-2-[rac-(3R)-3,4-dimethylpiperazin-1-yl]phenyl]-6-oxo-5-(trifluoromethyl)-1H-pyridine-3-carboxamide | 0.0249 |
| 496 | 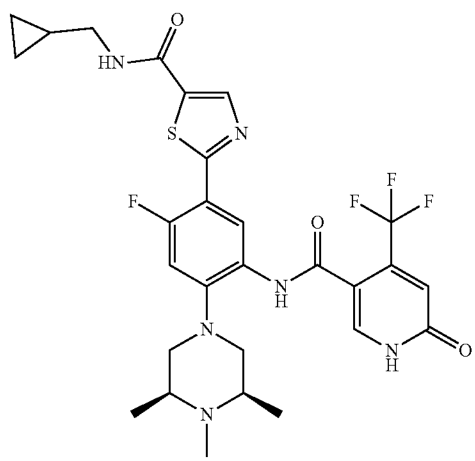 | N-(cyclopropylmethyl)-2-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-1,3-thiazole-5-carboxamide | 0.00303 |
| 497 | 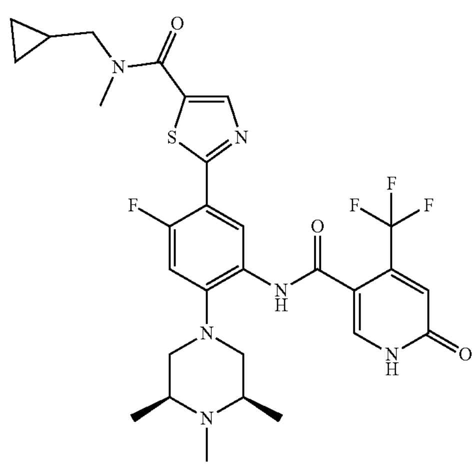 [SMILES: C[C@@H]1CN(c2cc(F)c(-c3ncc(C(=O)N(C)CC4CC4)s3)cc2NC(=O)c2c[nH]c(=O)cc2C(F)(F)F)C[C@H](C)N1C] | N-(cyclopropylmethyl)-2-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-N-methyl-1,3-thiazole-5-carboxamide | 0.00259 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 498 | 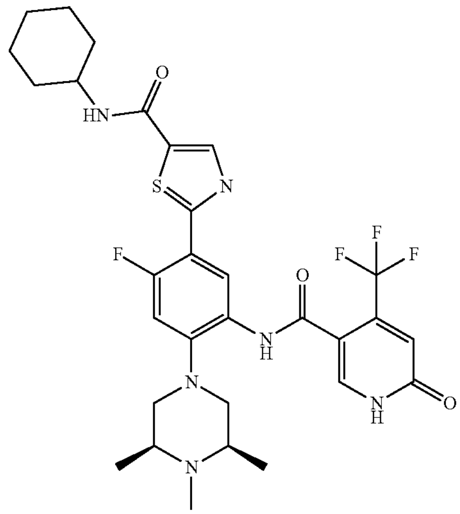 | N-cyclohexyl-2-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-1,3-thiazole-5-carboxamide | 0.00147 |
| 499 | 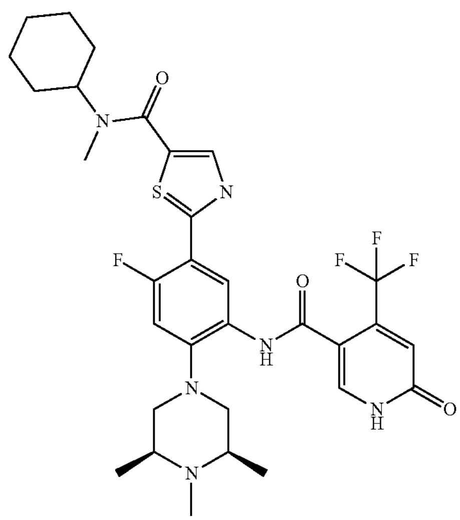 | N-cyclohexyl-2-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-N-methyl-1,3-thiazole-5-carboxamide | 0.0034 |
| 500 | 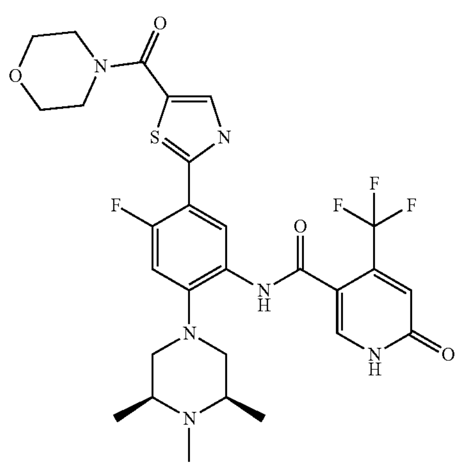 | N-[4-fluoro-5-[5-(morpholine-4-carbonyl)-1,3-thiazol-2-yl]-2-[rac-(3R,5S)-3,4,5-trimethylpiperazin-1-yl]phenyl]-6-oxo-4-(trifluoromethyl)-1H-pyridine-3-carboxamide | 0.00185 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 501 | 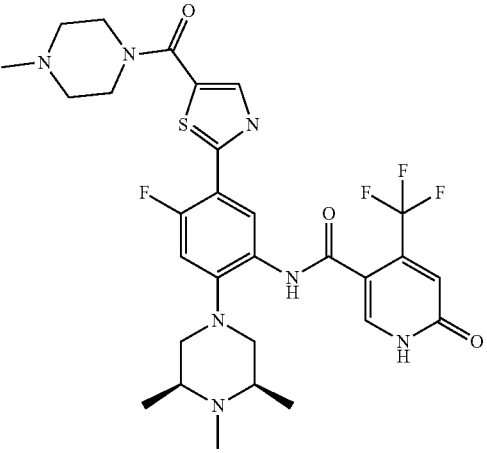 | N-[4-fluoro-5-[5-(4-methylpiperazine-1-carbonyl)-1,3-thiazol-2-yl]-2-[rac-(3R,5S)-3,4,5-trimethylpiperazin-1-yl]phenyl]-6-oxo-4-(trifluoromethyl)-1H-pyridine-3-carboxamide | 0.00344 |
| 502 | 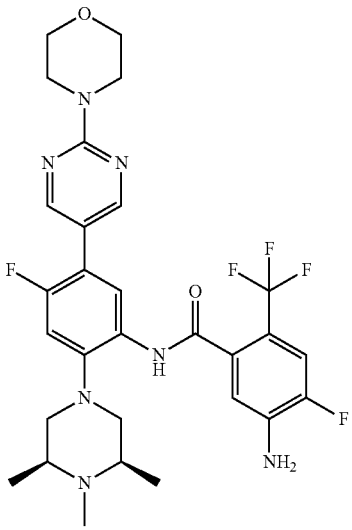 [SMILES: C[C@@H]1CN(c2cc(F)c(-c3cnc(N4CCOCC4)nc3)cc2NC(=O)c2cc(N)c(F)cc2C(F)(F)F)C[C@H](C)N1C] | 5-amino-4-fluoro-N-[4-fluoro-5-(2-morpholin-4-ylpyrimidin-5-yl)-2-[rac-(3R,5S)-3,4,5-trimethylpiperazin-1-yl]phenyl]-2-(trifluoromethyl)benzamide | 0.00115 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 503 | 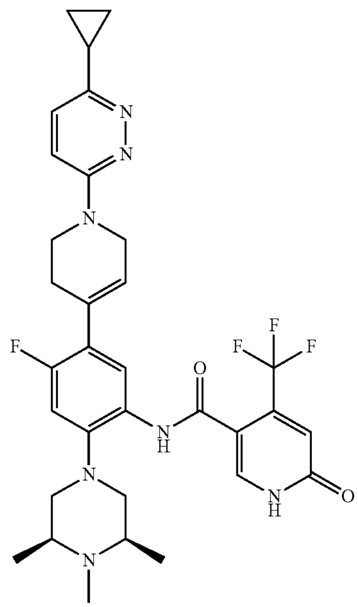 [SMILES: C[C@@H]1CN(c2cc(F)c(C3=CCN(c4ccc(C5CC5)nn4)CC3)cc2NC(=O)c2c[nH]c(=O)cc2C(F)(F)F)C[C@H](C)N1C] | N-[5-[1-(6-cyclopropylpyridazin-3-yl)-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00244 |
| 504 | 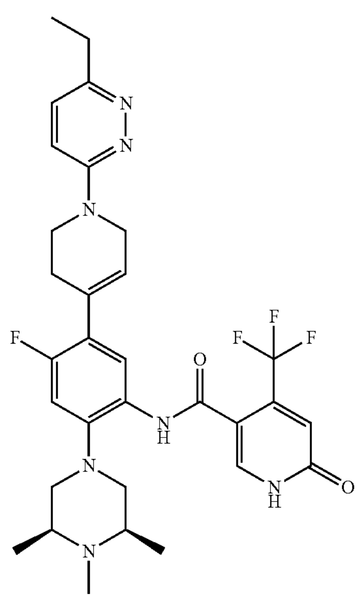 [SMILES: CCc1ccc(N2CC=C(c3cc(NC(=O)c4c[nH]c(=O)cc4C(F)(F)F)c(N4C[C@@H](C)N(C)[C@@H](C)C4)cc3F)CC2)nn1] | N-[5-[1-(6-ethylpyridazin-3-yl)-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00244 |

| Example No. | Structure | IUPAC Name | WDR5 binding affinity ($K_D$, μM) |
|---|---|---|---|
| 505 | 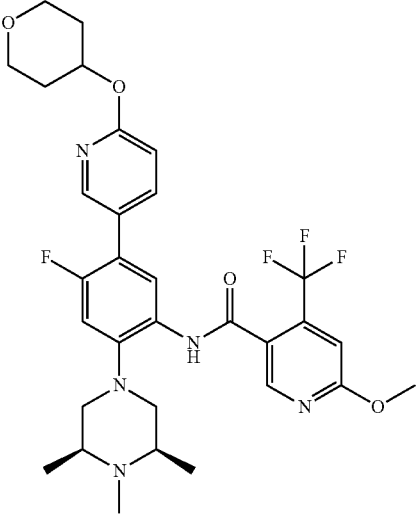 [SMILES: COc1cc(C(F)(F)F)c(C(=O)Nc2cc(-c3ccc(OC4CCOCC4)nc3)c(F)cc2N2C[C@@H](C)N(C)[C@@H](C)C2)cn1] | N-[4-fluoro-5-[6-(oxan-yloxy)pyridin-3-yl]-2-[rac-(3R,5S)-3,4,5-trimethylpiperazin-1-yl]phenyl]-6-methoxy-4-(trifluoromethyl)pyridine-3-carboxamide | — |
| 506 | 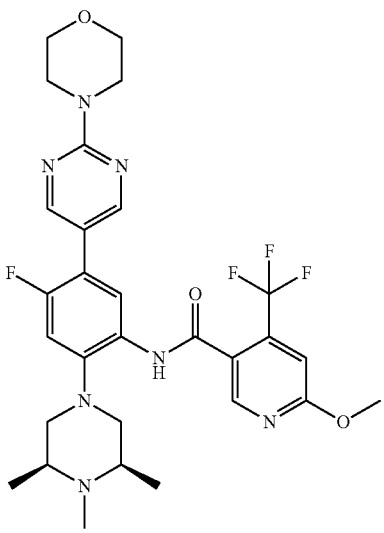 | N-[4-fluoro-5-(2-morpholin-4-ylpyrimidin-5-yl)-2-[rac-(3R,5S)-3,4,5-trimethylpiperazin-1-yl]phenyl]-6-methoxy-4-(trifluoromethyl)pyridine-3-carboxamide | 0.354 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 507 | 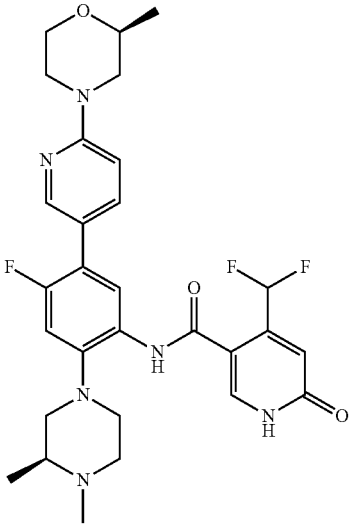 [SMILES: C[C@H]1CN(c2ccc(-c3cc(NC(=O)c4c[nH]c(=O)cc4C(F)F)c(N4CCN(C)[C@@H](C)C4)cc3F)cn2)CCO1] | 4-(difluoromethyl)-N-[4-fluoro-2-[rac-(3R)-3,4-dimethylpiperazin-1-yl]-5-[6-[rac-(2R)-2-methylmorpholin-4-yl]Pyridin-3-yl]phenyl]-6-oxo-1H-pyridine-3-carboxamide | 0.00176 |
| 508 | 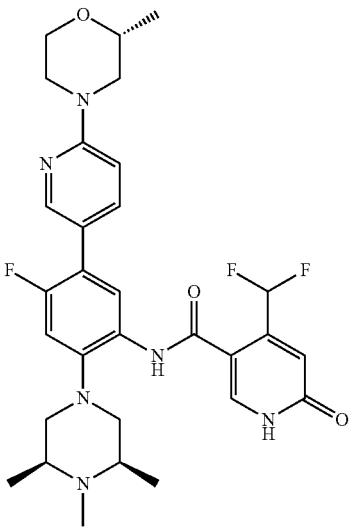 [SMILES: C[C@@H]1CN(c2ccc(-c3cc(NC(=O)c4c[nH]c(=O)cc4C(F)F)c(N4C[C@@H](C)N(C)[C@@H](C)C4)cc3F)cn2)CCO1] | 4-(difluoromethyl)-N-[4-fluoro-5-[6-[rac-(2R)-2-methylmorpholin-4-yl]pyridin-3-yl)-2-[rac-(3R,5S)-3,4,5-trimethylpiperazin-1-yl]phenyl]-6-oxo-1H-pyridine-3-carboxamide | 0.00266 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 509 | 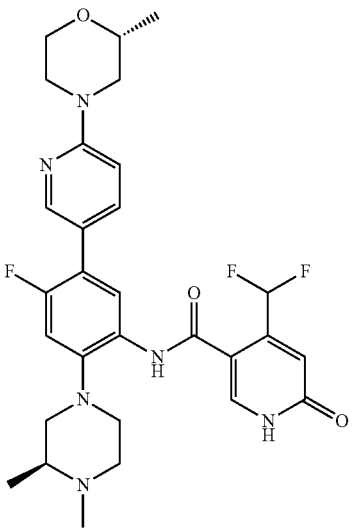 [SMILES: C[C@@H]1CN(c2ccc(-c3cc(NC(=O)c4c[nH]c(=O)cc4C(F)F)c(N4CCN(C)[C@@H](C)C4)cc3F)cn2)CCO1] | 4-(difluoromethyl)-N-[4-fluoro-2-[rac-(3S)-3,4-dimethylpiperazin-1-yl]-5-[6-[rac-(2R)-2-methylmorpholin-4-yl]pyridin-3-yl]phenyl]-6-oxo-1H-pyridine-3-carboxamide | 0.000947 |
| 510 | 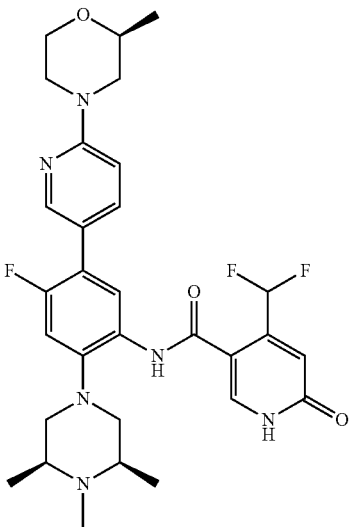 [SMILES: C[C@@H]1CN(c2cc(F)c(-c3ccc(N4CCO[C@@H](C)C4)nc3)cc2NC(=O)c2c[nH]c(=O)cc2C(F)F)C[C@H](C)N1C] | 4-(difluoromethyl)-N-[4-fluoro-5-[6-[rac-(2R)-2-methylmorpholin-4-yl]pyridin-3-yl]-2-[rac-(3S,5R)-3,4,5-trimethylpiperazin-1-yl]phenyl]-6-oxo-1H-pyridine-3-carboxamide | 0.000623 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 511 | 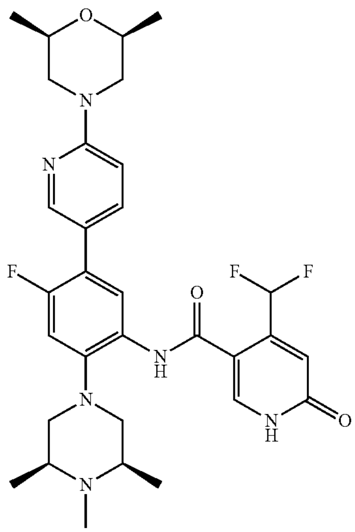 [SMILES: C[C@@H]1CN(c2ccc(-c3cc(NC(=O)c4c[nH]c(=O)cc4C(F)F)c(N4C[C@@H](C)N(C)[C@@H](C)C4)cc3F)cn2)C[C@H](C)O1] | 4-(difluoromethyl)-N-[4-fluoro-5-[6-[rac-(2R,6S)-2,6-dimethylmorpholin-4-yl]pyridin-3-yl]-2-[rac-(3R,5S)-3,4,5-trimethylpiperazin-1-yl]phenyl]-6-oxo-1H-pyridine-3-carboxamide | 0.000779 |
| 512 | 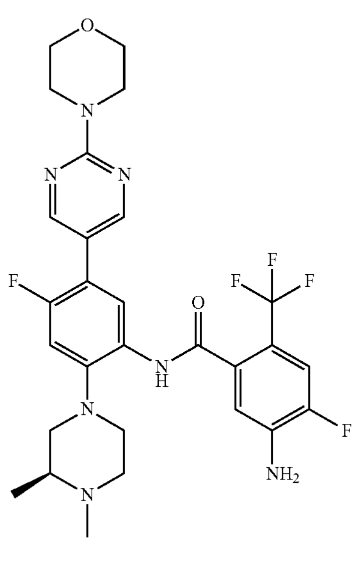 [SMILES: C[C@H]1CN(c2cc(F)c(-c3cnc(N4CCOCC4)nc3)cc2NC(=O)c2cc(N)c(F)cc2C(F)(F)F)CCN1C] | 5-amino-4-fluoro-N-[4-fluoro-5-(2-morpholin-4-ylpyrimidin-5-yl)-2-[rac-(3R)-3,4-dimethylpiperazin-1-yl]phenyl]-2-(trifluoromethyl)benzamide | 0.000711 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 513 | 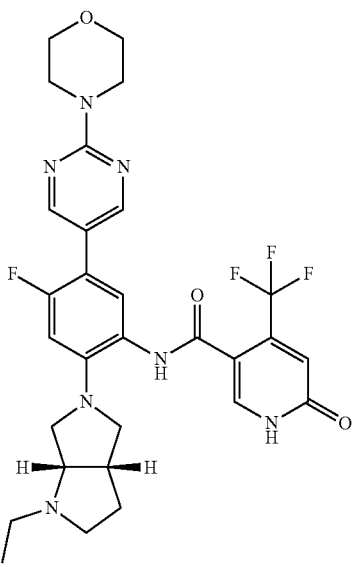 [SMILES: CCN1CC[C@H]2CN(c3cc(F)c(-c4cnc(N5CCOCC5)nc4)cc3NC(=O)c3c[nH]c(=O)cc3C(F)(F)F)C[C@H]21] | N-[4-fluoro-5-(2-morpholin-4-ylpyrimidin-5-yl)-2-[rac-(3aR,6aR)-1-ethyl-2,3,3a,4,6,6a-hexahydropyrrolo[2,3-c]pyrrol-5-yl]phenyl]-6-oxo-4-(trifluoromethyl)-1H-pyridine-3-carboxamide | 0.0099 |
| 514 | 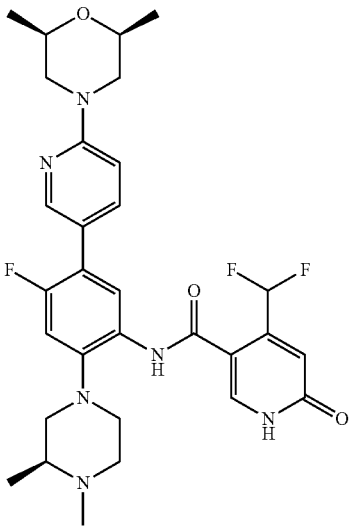 [SMILES: C[C@@H]1CN(c2ccc(-c3cc(NC(=O)c4c[nH]c(=O)cc4C(F)F)c(N4CCN(C)[C@@H](C)C4)cc3F)cn2)C[C@H](C)O1] | 4-(difluoromethyl)-N-[4-fluoro-5-[6-[rac-(2R,6S)-2,6-dimethylmorpholin-4-yl]pyridin-3-yl]-2-[rac-(3S)-3,4-dimethylpiperazin-1-yl]phenyl]-6-oxo-1H-pyridine-3-carboxamide | 0.000959 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 515 | 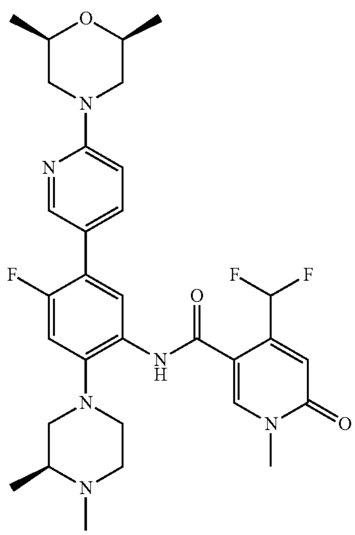 [SMILES: C[C@@H]1CN(c2ccc(-c3cc(NC(=O)c4cn(C)c(=O)cc4C(F)F)c(N4CCN(C)[C@@H](C)C4)cc3F)cn2)C[C@H](C)O1] | 4-(difluoromethyl)-N-[4-fluoro-5-[6-[rac-(2R,6S)-2,6-dimethylmorpholin-4-yl]pyridin-3-yl]-2-[rac-(3S)-3,4-dimethylpiperazin-1-yl]phenyl]-1-methyl-6-oxopyridine-3-carboxamide | 0.00409 |
| 516 | 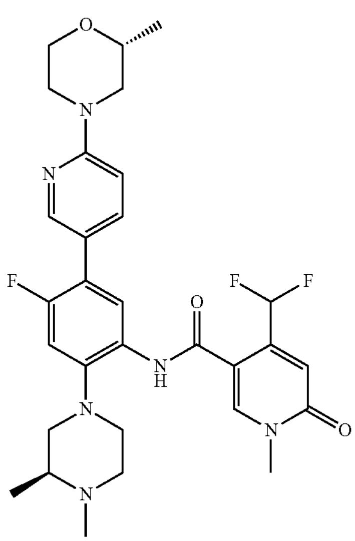 [SMILES: C[C@@H]1CN(c2ccc(-c3cc(NC(=O)c4cn(C)c(=O)cc4C(F)F)c(N4CCN(C)[C@@H](C)C4)cc3F)cn2)CCO1] | 4-(difluoromethyl)-N-[4-fluoro-2-[rac-(3S)-3,4-dimethylpiperazin-1-yl]-5-[6-[rac-(2R)-2-methylmorpholin-4-yl]pyridin-3-yl]phenyl]-1-methyl-6-oxopyridine-3-carboxamide | 0.004 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 517 | 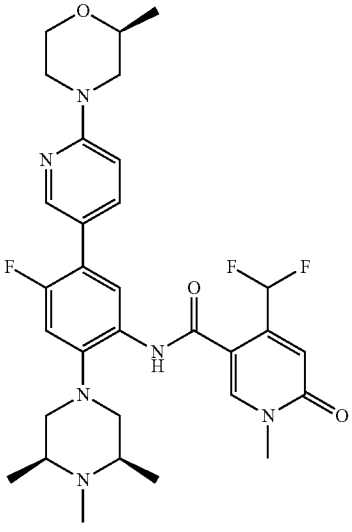 [SMILES: C[C@@H]1CN(c2cc(F)c(-c3ccc(N4CCO[C@@H](C)C4)nc3)cc2NC(=O)c2cn(C)c(=O)cc2C(F)F)C[C@H](C)N1C] | 4-(difluoromethyl)-N-[4-fluoro-5-[6-[rac-(2R)-2-methylmorpholin-4-yl]pyridin-3-yl]-2-[rac-(3S,5R)-3,4,5-trimethylpiperazin-1-yl]phenyl]-1-methyl-6-oxopyridine-3-carboxamide | 0.00597 |
| 518 | 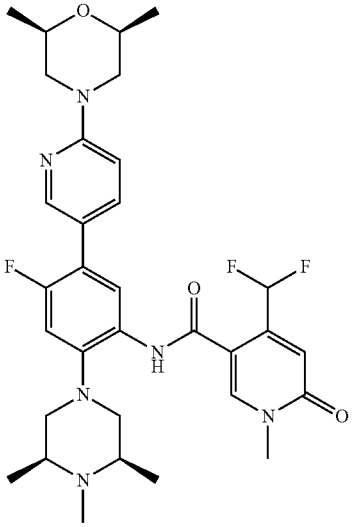 [SMILES: C[C@@H]1CN(c2ccc(-c3cc(NC(=O)c4cn(C)c(=O)cc4C(F)F)c(N4C[C@@H](C)N(C)[C@@H](C)C4)cc3F)cn2)C[C@H](C)O1] | 4-(difluoromethyl)-N-[4-fluoro-5-[6-[rac-(2R,6S)-2,6-dimethylmorpholin-4-yl]pyridin-3-yl]-2-[rac-(3R,5S)-3,4,5-trimethylpiperazin-1-yl]phenyl]-1-methyl-6-oxopyridine-3-carboxamide | 0.00341 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 519 | 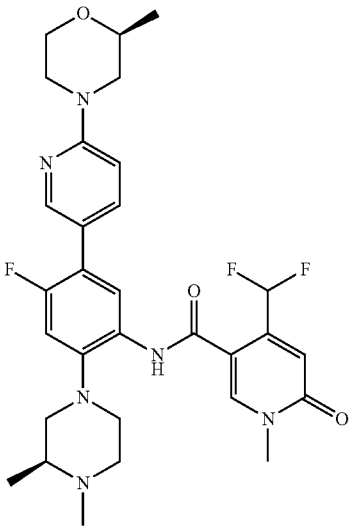 [SMILES: C[C@H]1CN(c2ccc(-c3cc(NC(=O)c4cn(C)c(=O)cc4C(F)F)c(N4CCN(C)[C@@H](C)C4)cc3F)cn2)CCO1] | 4-(difluoromethyl)-N-[4-fluoro-2-[rac-(3R)-3,4-dimethylpiperazin-1-yl]-5-[6-[rac-(2R)-2-methylmorpholin-4-yl]pyridin-3-yl]phenyl]-1-methyl-6-oxopyridine-3-carboxamide | 0.00339 |
| 520 | 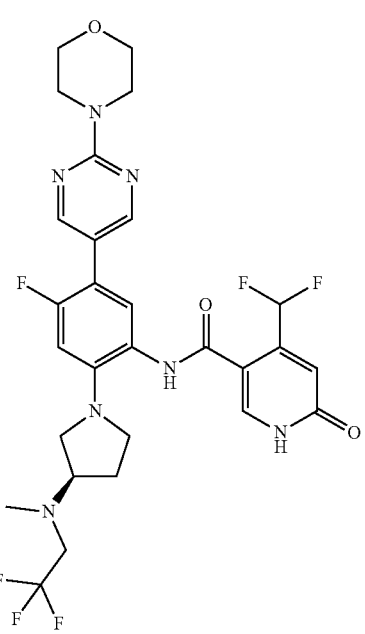 | N-[4-fluoro-5-(2-morpholin-4-ylpyrimidin-5-yl)-2-[rac-(3R)-3-[methyl(2,2,2-trifluoroethyl)amino]pyrrolidin-1-yl]phenyl]-6-oxo-4-(trifluoromethyl)-1H-pyridine-3-carboxamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 521 | 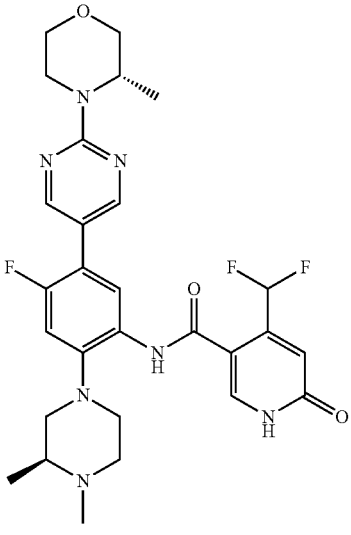 [SMILES: C[C@H]1CN(c2cc(F)c(-c3cnc(N4CCOC[C@@H]4C)nc3)cc2NC(=O)c2c[nH]c(=O)cc2C(F)F)CCN1C] | 4-(difluoromethyl)-N-[4-fluoro-5-[2-[rac-(3R)-3-methylmorpholin-4-yl]pyrimidin-5-yl]-2-[rac-(3S,5R)-3,4,5-trimethylpiperazin-1-yl]phenyl]-6-oxo-1H-pyridine-3-carboxamide | 0.000579 |
| 522 | 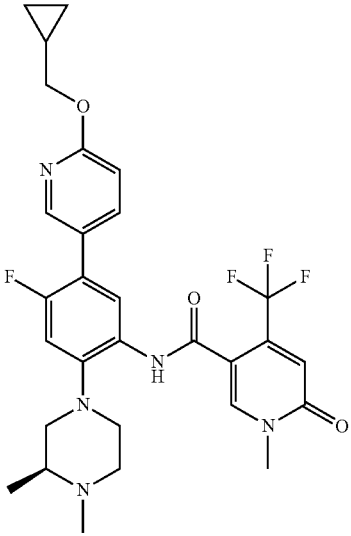 [SMILES: C[C@H]1CN(c2cc(F)c(-c3ccc(OCC4CC4)nc3)cc2NC(=O)c2cn(C)c(=O)cc2C(F)(F)F)CCN1C] | N-[5-[6-(cyclopropylmethoxy)pyridin-3-yl]-4-fluoro-2-[rac-(3R)-3,4-dimethylpiperazin-1-yl]phenyl]-1-methyl-6-oxo-4-(trifluoromethyl)pyridine-3-carboxamide | 0.00562 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 523 | 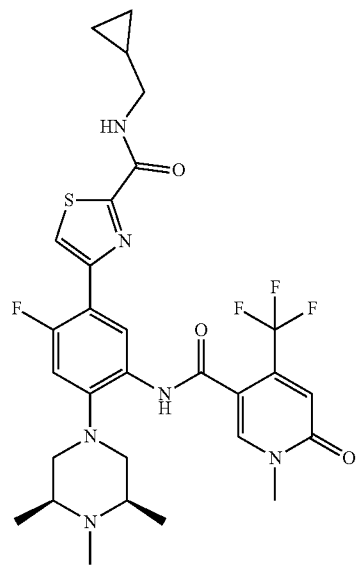 | N-(cyclopropylmethyl)-4-[2-fluoro-5-[[1-methyl-6-oxo-4-(trifluoromethyl)pyridine-3-carbonyl]amino]-4-[rac-(3R,5S)-3,4,5-trimethylpiperazin-1-yl]phenyl]-1,3-thiazole-2-carboxamide | 0.00459 |
| 524 | 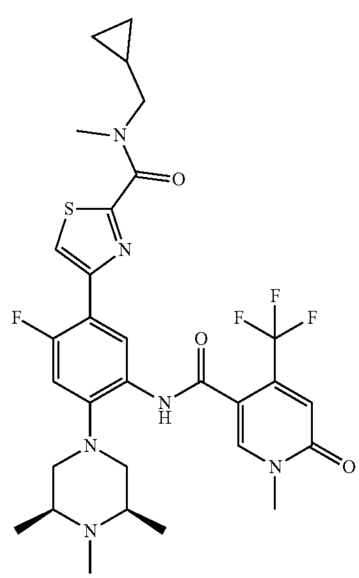 [SMILES: C[C@@H]1CN(c2cc(F)c(-c3csc(C(=O)N(C)CC4CC4)n3)cc2NC(=O)c2cn(C)c(=O)cc2C(F)(F)F)C[C@H](C)N1C] | N-(cyclopropylmethyl)-4-[2-fluoro-5-[[1-methyl-6-oxo-4-(trifluoromethyl)pyridine-3-carbonyl]amino]-4-[rac-(3R,5S)-3,4,5-trimethylpiperazin-1-yl]phenyl]-N-methyl-1,3-thiazole-2-carboxamide | 0.00503 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 525 | 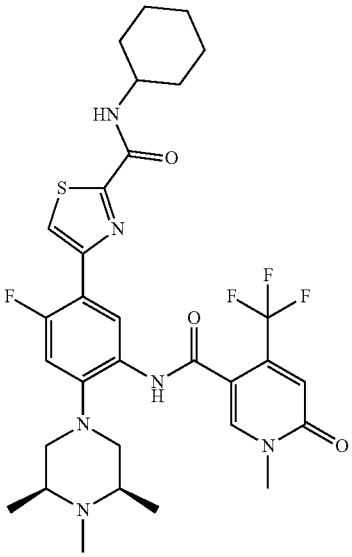 [SMILES: C[C@@H]1CN(c2cc(F)c(-c3csc(C(=O)NC4CCCCC4)n3)cc2NC(=O)c2cn(C)c(=O)cc2C(F)(F)F)C[C@H](C)N1C] | N-cyclohexyl-4-[2-fluoro-5-[[1-methyl-6-oxo-4-(trifluoromethyl)pyridine-3-carbonyl]amino]-4-[rac-(3R,5S)-3,4,5-trimethylpiperazin-1-yl]phenyl]-1,3-thiazole-2-carboxamide | 0.00542 |
| 526 | 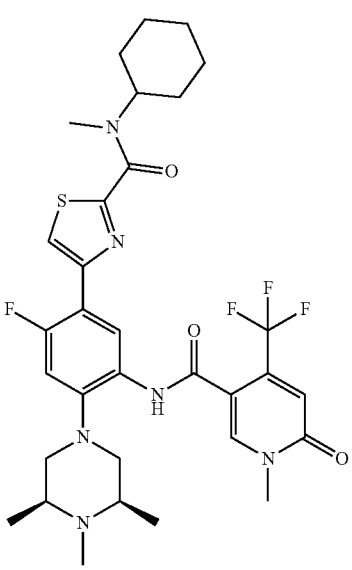 [SMILES: C[C@@H]1CN(c2cc(F)c(-c3csc(C(=O)N(C)C4CCCCC4)n3)cc2NC(=O)c2cn(C)c(=O)cc2C(F)(F)F)C[C@H](C)N1C] | N-cyclohexyl-4-[2-fluoro-5-[[1-methyl-6-oxo-4-(trifluoromethyl)pyridine-3-carbonyl]amino]-4-[rac-(3R,5S)-3,4,5-trimethylpiperazin-1-yl]phenyl]-N-methyl-1,3-thiazole-2-carboxamide | 0.00489 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 527 | 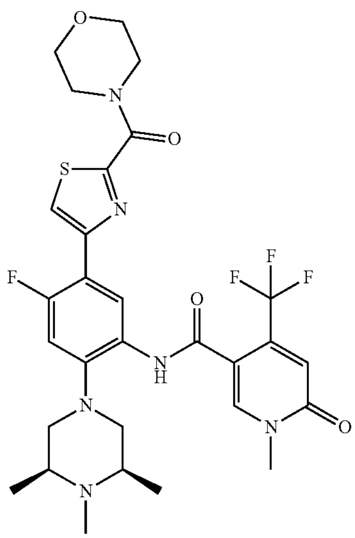 [SMILES: C[C@@H]1CN(c2cc(F)c(-c3csc(C(=O)N4CCOCC4)n3)cc2NC(=O)c2cn(C)c(=O)cc2C(F)(F)F)C[C@H](C)N1C] | N-[4-fluoro-5-[2-(morpholine-4-carbonyl)-1,3-thiazol-4-yl]-2-[rac-(3R,5S)-3,4,5-trimethylpiperazin-1-yl]phenyl]-1-methyl-6-oxo-4-(trifluoromethyl)pyridine-3-carboxamide | 0.00566 |
| 528 | 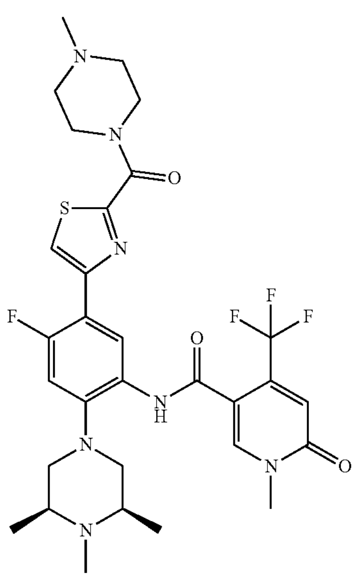 [SMILES: C[C@@H]1CN(c2cc(F)c(-c3csc(C(=O)N4CCN(C)CC4)n3)cc2NC(=O)c2cn(C)c(=O)cc2C(F)(F)F)C[C@H](C)N1C] | N-[4-fluoro-5-[2-(4-methylpiperazine-1-carbonyl)-1,3-thiazol-4-yl]-2-[rac-(3R,5S)-3,4,5-trimethylpiperazin-1-yl]phenyl]-1-methyl-6-oxo-4-(trifluoromethyl)pyridine-3-carboxamide | 0.00405 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 529 | 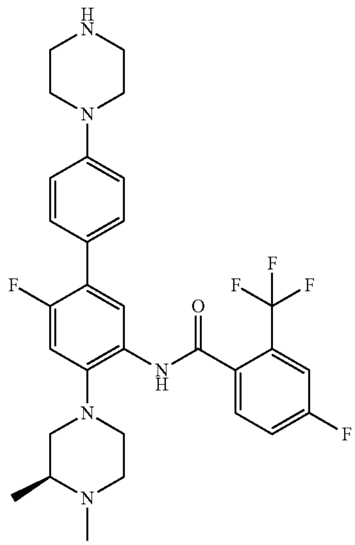 | 4-fluoro-N-[4-fluoro-5-(4-piperazin-1-ylphenyl)-2-[rac-(3R)-3,4-dimethylpiperazin-1-yl]phenyl]-2-(trifluoromethyl)benzamide | 0.00292 |
| 530 | 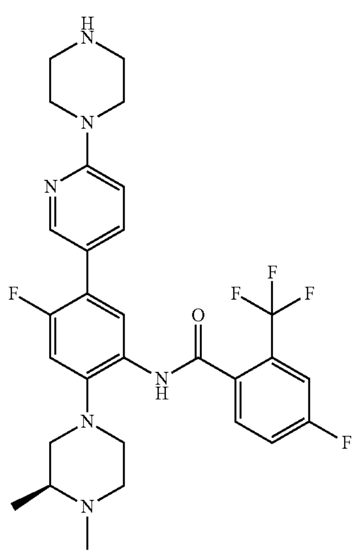 | 4-fluoro-N-[4-fluoro-5-(6-piperazin-1-ylpyridin-3-yl)-2-[rac-(3R)-3,4-dimethylpiperazin-1-yl]phenyl]-2-(trifluoromethyl)benzamide | 0.00216 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 531 | 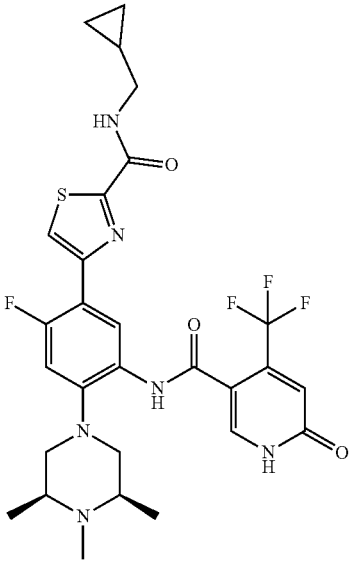 [SMILES: C[C@@H]1CN(c2cc(F)c(-c3csc(C(=O)NCC4CC4)n3)cc2NC(=O)c2c[nH]c(=O)cc2C(F)(F)F)C[C@H](C)N1C] | N-(cyclopropylmethyl)-4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-1,3-thiazole-2-carboxamide | 0.00106 |
| 532 | 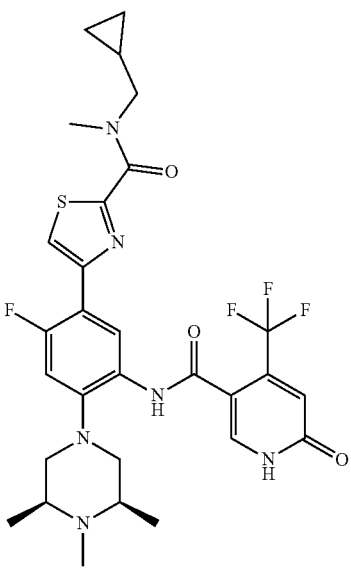 [SMILES: C[C@@H]1CN(c2cc(F)c(-c3csc(C(=O)N(C)CC4CC4)n3)cc2NC(=O)c2c[nH]c(=O)cc2C(F)(F)F)C[C@H](C)N1C] | N-(cyclopropylmethyl)-4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-N-methyl-1,3-thiazole-2-carboxamide | 0.000694 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 533 | 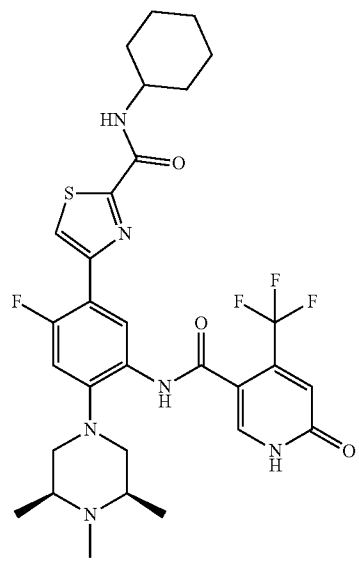 | N-cyclohexyl-4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-1,3-thiazole-2-carboxamide | 0.00198 |
| 534 | 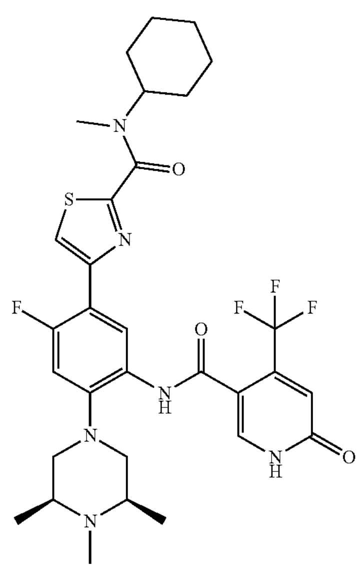 [SMILES: C[C@@H]1CN(c2cc(F)c(-c3csc(C(=O)N(C)C4CCCCC4)n3)cc2NC(=O)c2c[nH]c(=O)cc2C(F)(F)F)C[C@H](C)N1C] | N-cyclohexyl-4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-N-methyl-1,3-thiazole-2-carboxamide | 0.00131 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 535 | 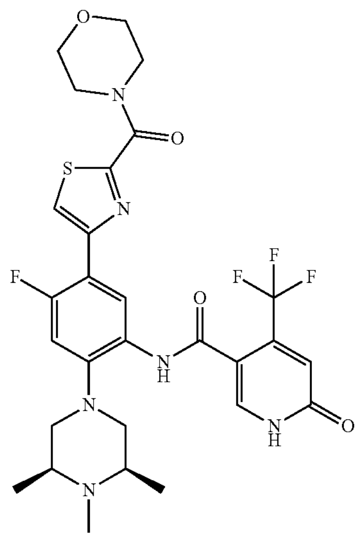 [SMILES: C[C@@H]1CN(c2cc(F)c(-c3csc(C(=O)N4CCOCC4)n3)cc2NC(=O)c2c[nH]c(=O)cc2C(F)(F)F)C[C@H](C)N1C] | N-[4-fluoro-5-[2-(morpholine-4-carbonyl)-1,3-thiazol-4-yl]-2-[rac-(3R,5S)-3,4,5-trimethylpiperazin-1-yl]phenyl]-6-oxo-4-(trifluoromethyl)-1H-pyridine-3-carboxamide | 0.0028 |
| 536 | 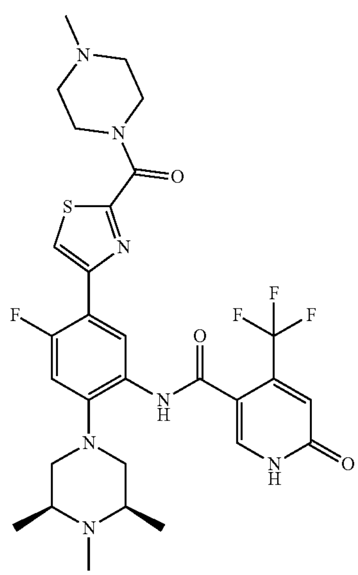 | N-[4-fluoro-5-[2-(4-methylpiperazine-1-carbonyl)-1,3-thiazol-4-yl]-2-[rac-(3R,5S)-3,4,5-trimethylpiperazin-1-yl]phenyl]-6-oxo-4-(trifluoromethyl)-1H-pyridine-3-carboxamide | 0.00103 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 537 | 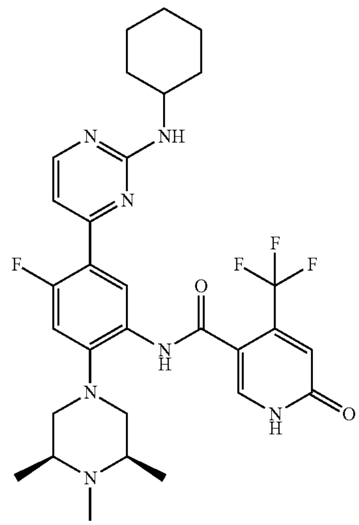 [SMILES: C[C@@H]1CN(c2cc(F)c(-c3ccnc(NC4CCCCC4)n3)cc2NC(=O)c2c[nH]c(=O)cc2C(F)(F)F)C[C@H](C)N1C] | N-[5-[2-(cyclohexylamino)pyrimidin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.000944 |
| 538 | 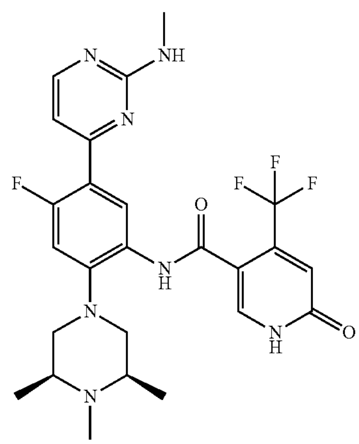 [SMILES: CNc1nccc(-c2cc(NC(=O)c3c[nH]c(=O)cc3C(F)(F)F)c(N3C[C@@H](C)N(C)[C@@H](C)C3)cc2F)n1] | N-[4-fluoro-5-[2-(methylamino)pyrimidin-4-yl]-2-[rac-(3R,5S)-3,4,5-trimethylpiperazin-1-yl]phenyl]-6-oxo-4-(trifluoromethyl)-1H-pyridine-3-carboxamide | 0.00302 |
| 539 | 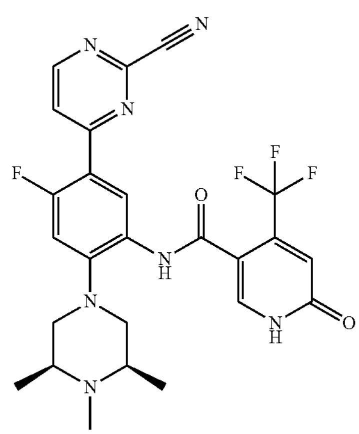 [SMILES: C[C@@H]1CN(c2cc(F)c(-c3ccnc(C#N)n3)cc2NC(=O)c2c[nH]c(=O)cc2C(F)(F)F)C[C@H](C)N1C] | N-[5-(2-cyanopyrimidin-4-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00256 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 540 | 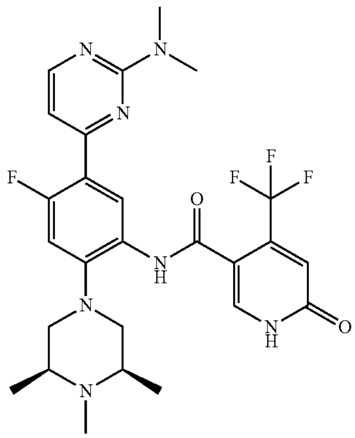 [SMILES: C[C@@H]1CN(c2cc(F)c(-c3ccnc(N(C)C)n3)cc2NC(=O)c2c[nH]c(=O)cc2C(F)(F)F)C[C@H](C)N1C] | N-[5-[2-(dimethylamino)pyrimidin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.0011 |
| 541 | 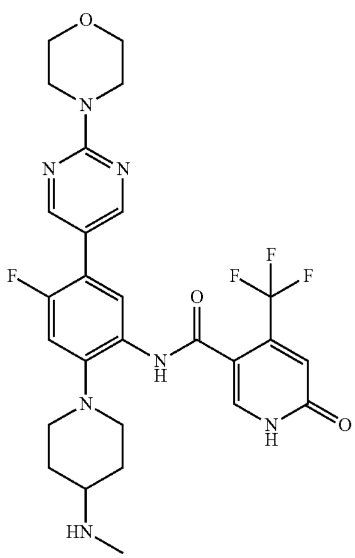 | N-[4-fluoro-2-[4-(methylamino)piperidin-1-yl]-5-(2-morpholin-4-ylpyrimidin-5-yl)phenyl]-6-oxo-4-(trifluoromethyl)-1H-pyridine-3-carboxamide | 0.00744 |
| 542 | 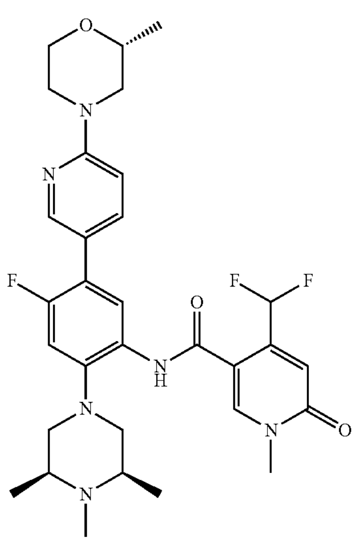 [SMILES: C[C@@H]1CN(c2ccc(-c3cc(NC(=O)c4cn(C)c(=O)cc4C(F)F)c(N4C[C@@H](C)N(C)[C@@H](C)C4)cc3F)cn2)CCO1] | 4-(difluoromethyl)-N-[4-fluoro-5-[6-[rac-(2R)-2-methylmorpholin-4-yl]pyridin-3-yl]-2-[rac-(3R,5S)-3,4,5-trimethylpiperazin-1-yl]phenyl]-1-methyl-6-oxopyridine-3-carboxamide | 0.00553 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 543 | 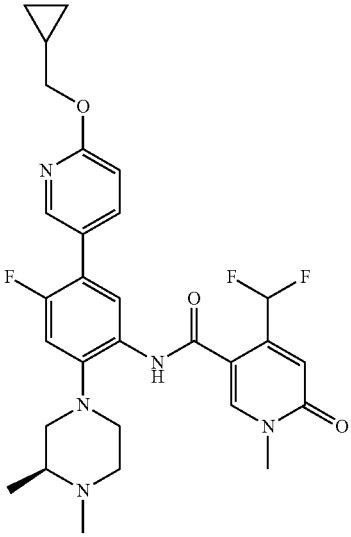 [SMILES: C[C@H]1CN(c2cc(F)c(-c3ccc(OCC4CC4)nc3)cc2NC(=O)c2cn(C)c(=O)cc2C(F)F)CCN1C] | N-[5-[6-(cyclopropylmethoxy)pyridin-3-yl]-4-fluoro-2-[rac-(3R)-3,4-dimethylpiperazin-1-yl]phenyl]-4-(difluoromethyl)-1-methyl-6-oxopyridine-3-carboxamide | 0.00821 |
| 544 | 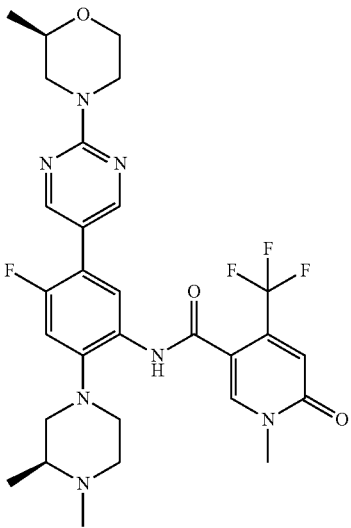 [SMILES: C[C@@H]1CN(c2ncc(-c3cc(NC(=O)c4cn(C)c(=O)cc4C(F)(F)F)c(N4CCN(C)[C@@H](C)C4)cc3F)cn2)CCO1] | N-[4-fluoro-2-[rac-(3S)-3,4-dimethylpiperazin-1-yl]-5-[2-[rac-(2R)-2-methylmorpholin-4-yl]pyrimidin-5-yl]phenyl]-1-methyl-6-oxo-4-(trifluoromethyl)pyridine-3-carboxamide | 0.0018 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 545 | 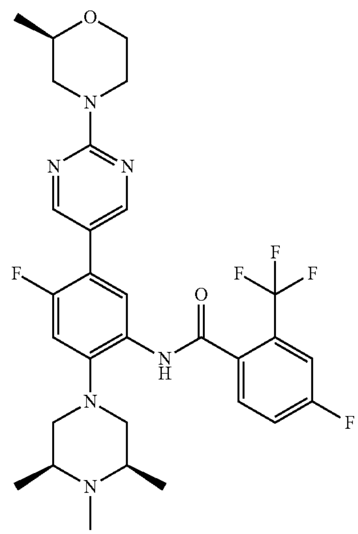 [SMILES: C[C@@H]1CN(c2ncc(-c3cc(NC(=O)c4ccc(F)cc4C(F)(F)F)c(N4C[C@@H](C)N(C)[C@@H](C)C4)cc3F)cn2)CCO1] | 4-fluoro-N-[4-fluoro-5-[2-[rac-(2R)-2-methylmorpholin-4-yl]pyrimidin-5-yl]-2-[rac-(3R,5S)-3,4,5-trimethylpiperazin-1-yl]phenyl]-2-(trifluoromethyl)benzamide | 0.0034 |
| 546 | 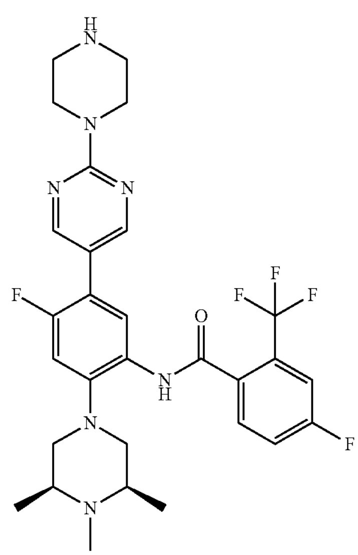 [SMILES: C[C@@H]1CN(c2cc(F)c(-c3cnc(N4CCNCC4)nc3)cc2NC(=O)c2ccc(F)cc2C(F)(F)F)C[C@H](C)N1C] | 4-fluoro-N-[4-fluoro-5-(2-piperazin-1-ylpyrimidin-5-yl)-2-[rac-(3R,5S)-3,4,5-trimethylpiperazin-1-yl]phenyl]-2-(trifluoromethyl)benzamide | 0.0021 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 547 | 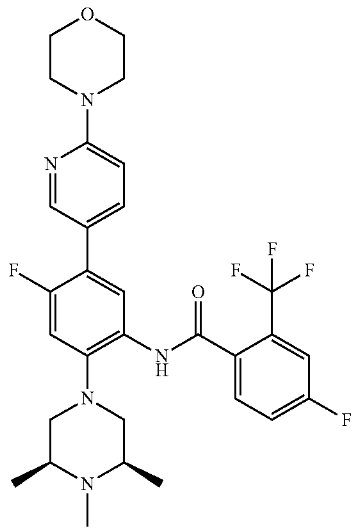 [SMILES: C[C@@H]1CN(c2cc(F)c(-c3ccc(N4CCOCC4)nc3)cc2NC(=O)c2ccc(F)cc2C(F)(F)F)C[C@H](C)N1C] | 4-fluoro-N-[4-fluoro-5-(6-morpholin-4-ylpyridin-3-yl)-2-[rac-(3R,5S)-3,4,5-trimethylpiperazin-1-yl]phenyl]-2-(trifluoromethyl)benzamide | 0.0015 |
| 548 | 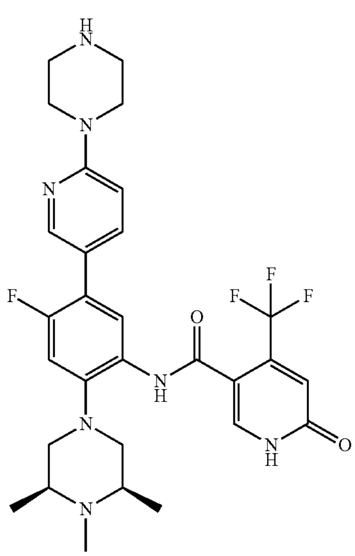 | N-[4-fluoro-5-(6-piperazin-1-ylpyridin-3-yl)-2-[rac-(3R,5S)-3,4,5-trimethylpiperazin-1-yl]phenyl]-6-oxo-4-(trifluoromethyl)-1H-pyridine-3-carboxamide | 0.0005 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 549 | 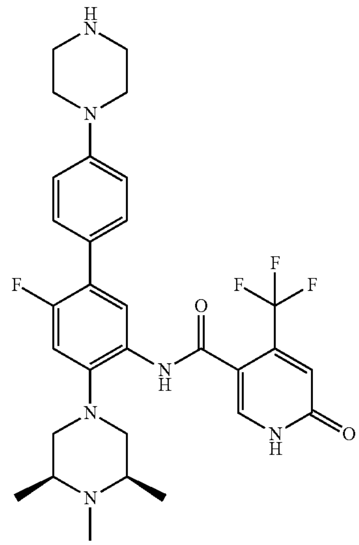 [SMILES: C[C@@H]1CN(c2cc(F)c(-c3ccc(N4CCNCC4)cc3)cc2NC(=O)c2c[nH]c(=O)cc2C(F)(F)F)C[C@H](C)N1C] | N-[4-fluoro-5-(4-piperazin-1-ylphenyl)-2-[rac-(3R,5S)-3,4,5-trimethylpiperazin-1-yl]phenyl]-6-oxo-4-(trifluoromethyl)-1H-pyridine-3-carboxamide | 0.0008 |
| 550 | 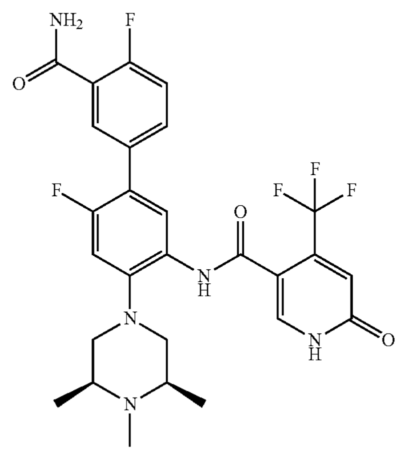 | N-[5-(3-carbamoyl-4-fluorophenyl)-4-fluoro-2-[rac-(3R,5S)-3,4,5-trimethylpiperazin-1-yl]phenyl]-6-oxo-4-(trifluoromethyl)-1H-pyridine-3-carboxamide | 0.0025 |
| 551 | 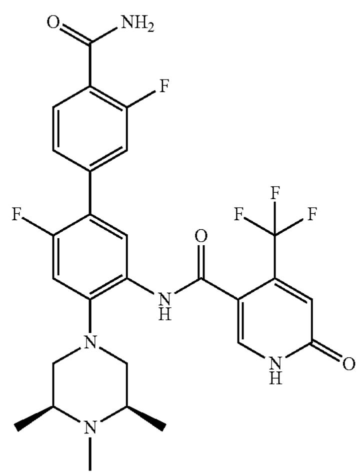 | N-[5-(4-carbamoyl-3-fluorophenyl)-4-fluoro-2-[rac-(3R,5S)-3,4,5-trimethylpiperazin-1-yl]phenyl]-6-oxo-4-(trifluoromethyl)-1H-pyridine-3-carboxamide | 0.0006 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 552 | 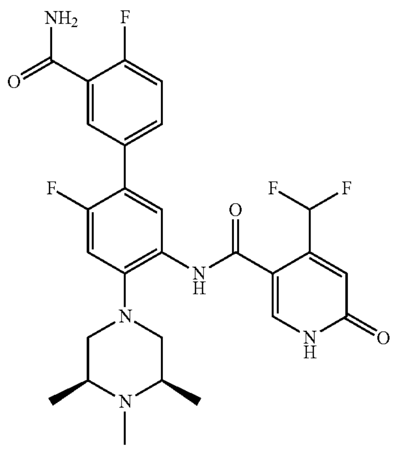 | N-[5-(3-carbamoyl-4-fluorophenyl)-4-fluoro-2-[rac-(3R,5S)-3,4,5-trimethylpiperazin-1-yl]phenyl]-4-(difluoromethyl)-6-oxo-1H-pyridine-3-carboxamide | 0.0031 |
| 553 | 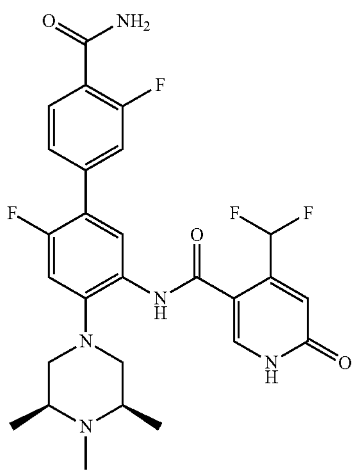 | N-[5-(4-carbamoyl-3-fluorophenyl)-4-fluoro-2-[rac-(3R,5S)-3,4,5-trimethylpiperazin-1-yl]phenyl]-4-(difluoromethyl)-6-oxo-1H-pyridine-3-carboxamide | 0.001 |
| 554 | 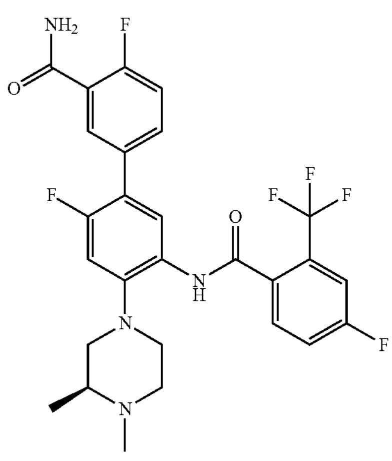 [SMILES: C[C@H]1CN(c2cc(F)c(-c3ccc(F)c(C(N)=O)c3)cc2NC(=O)c2ccc(F)cc2C(F)(F)F)CCN1C] | 2-fluoro-5-[2-fluoro-5-[[4-fluoro-2-(trifluoromethyl)benzoyl]amino]-4-[rac-(3R)-3,4-dimethylpiperazin-1-yl]phenyl]benzamide | 0.0053 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 555 | 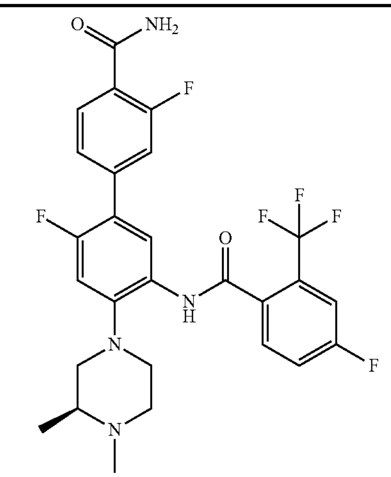 | 2-fluoro-4-[2-fluoro-5-[[4-fluoro-2-(trifluoromethyl)benzoyl]amino]-4-[rac-(3R)-3,4-dimethylpiperazin-1-yl]phenyl]benzamide | 0.00294 |
| 556 | 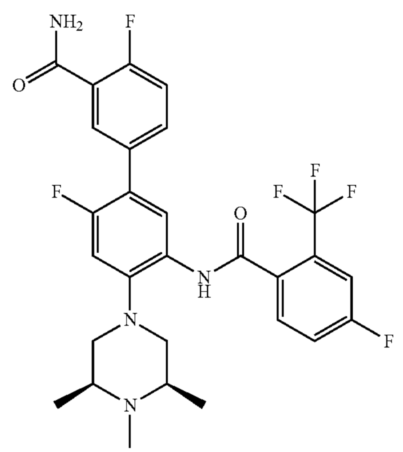 [SMILES: C[C@@H]1CN(c2cc(F)c(-c3ccc(F)c(C(N)=O)c3)cc2NC(=O)c2ccc(F)cc2C(F)(F)F)C[C@H](C)N1C] | 2-fluoro-5-[2-fluoro-5-[[4-fluoro-2-(trifluoromethyl)benzoyl]amino]-4-[rac-(3R,5S)-3,4,5-trimethylpiperazin-1-yl]phenyl]benzamide | 0.0104 |
| 557 | 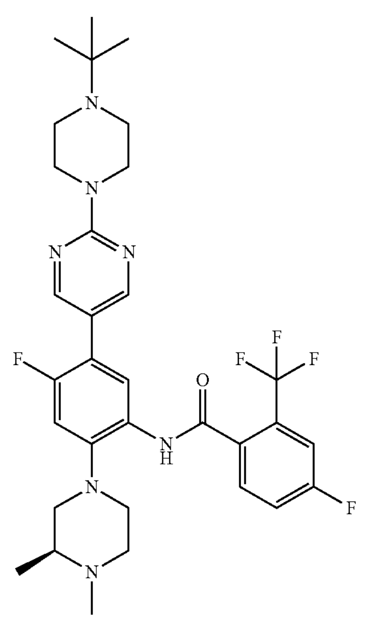 [SMILES: C[C@H]1CN(c2cc(F)c(-c3cnc(N4CCN(C(C)(C)C)CC4)nc3)cc2NC(=O)c2ccc(F)cc2C(F)(F)F)CCN1C] | N-[5-[2-(4-tert-butylpiperazin-1-yl)pyrimidin-5-yl]-4-fluoro-2-[rac-(3R)-3,4-dimethylpiperazin-1-yl]phenyl]-4-fluoro-2-(trifluoromethyl)benzamide | 0.00109 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 558 | 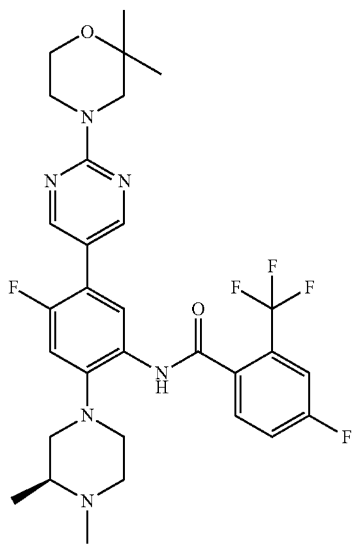 [SMILES: C[C@H]1CN(c2cc(F)c(-c3cnc(N4CCOC(C)(C)C4)nc3)cc2NC(=O)c2ccc(F)cc2C(F)(F)F)CCN1C] | N-[5-[2-(2,2-dimethylmorpholin-4-yl)pyrimidin-5-yl]-4-fluoro-2-[rac-(3R)-3,4-dimethylpiperazin-1-yl]phenyl]-4-fluoro-2-(trifluoromethyl)benzamide | 0.00378 |
| 559 | 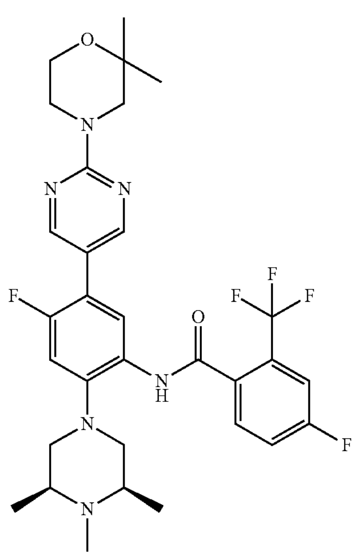 [SMILES: C[C@@H]1CN(c2cc(F)c(-c3cnc(N4CCOC(C)(C)C4)nc3)cc2NC(=O)c2ccc(F)cc2C(F)(F)F)C[C@H](C)N1C] | N-[5-[2-(2,2-dimethylmorpholin-4-yl)pyrimidin-5-yl]-4-fluoro-2-[rac-(3R,5S)-3,4,5-trimethylpiperazin-1-yl]phenyl]-4-fluoro-2-(trifluoromethyl)benzamide | 0.00292 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 560 | 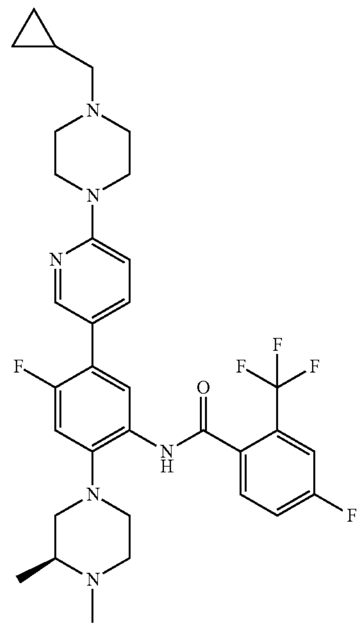 | N-[5-[2-[4-(cyclopropylmethyl)piperazin-1-yl]pyrimidin-5-yl]-4-fluoro-2-[rac-(3R)-3,4-dimethylpiperazin-1-yl]phenyl]-4-fluoro-2-(trifluoromethyl)benzamide | 0.00112 |
| 561 | 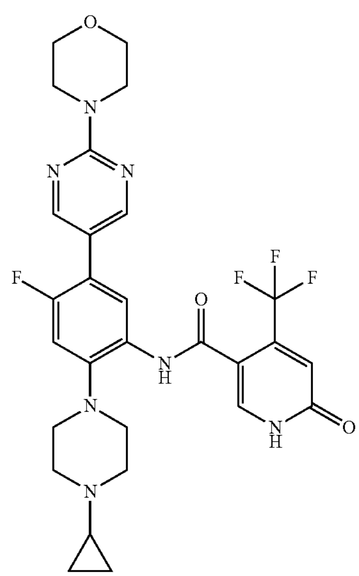 [SMILES: O=C(Nc1cc(-c2cnc(N3CCOCC3)nc2)c(F)cc1N1CCN(C2CC2)CC1)c1c[nH]c(=O)cc1C(F)(F)F] | N-[2-(4-cyclopropylpiperazin-1-yl)-4-fluoro-5-(2-morpholin-4-ylpyrimidin-5-yl)phenyl]-6-oxo-4-(trifluoromethyl)-1H-pyridine-3-carboxamide | 0.0235 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 562 | 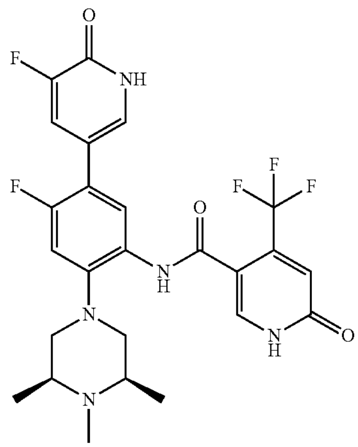 | N-[4-fluoro-5-(5-fluoro-6-oxo-1H-pyridin-3-yl)-2-[rac-(3R,5S)-3,4,5-trimethylpiperazin-1-yl]phenyl]-6-oxo-4-(trifluoromethyl)-1H-pyridine-3-carboxamide | 0.000904 |
| 563 | 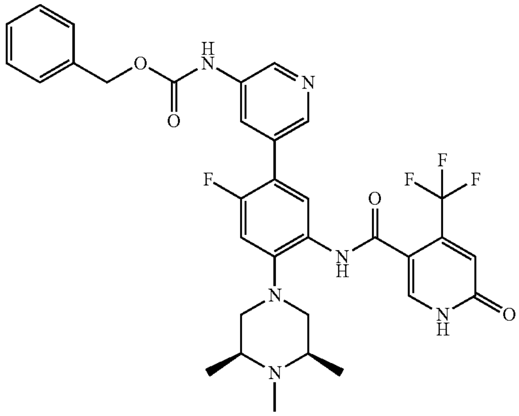 [SMILES: C[C@@H]1CN(c2cc(F)c(-c3cncc(NC(=O)OCc4ccccc4)c3)cc2NC(=O)c2c[nH]c(=O)cc2C(F)(F)F)C[C@H](C)N1C] | benzyl N-[5-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]pyridin-3-yl]carbamate | 0.00332 |
| 564 | 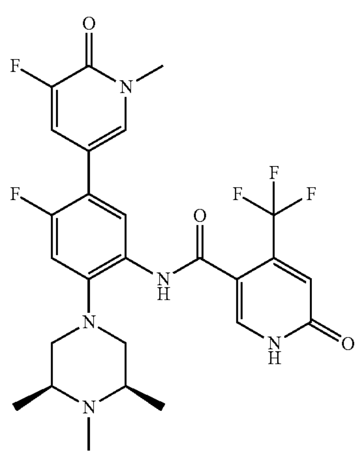 [SMILES: C[C@@H]1CN(c2cc(F)c(-c3cc(F)c(=O)n(C)c3)cc2NC(=O)c2c[nH]c(=O)cc2C(F)(F)F)C[C@H](C)N1C] | N-[4-fluoro-5-(5-fluoro-1-methyl-6-oxopyridin-3-yl)-2-[rac-(3R,5S)-3,4,5-trimethylpiperazin-1-yl]phenyl]-6-oxo-4-(trifluoromethyl)-1H-pyridine-3-carboxamide | 0.00152 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 565 | 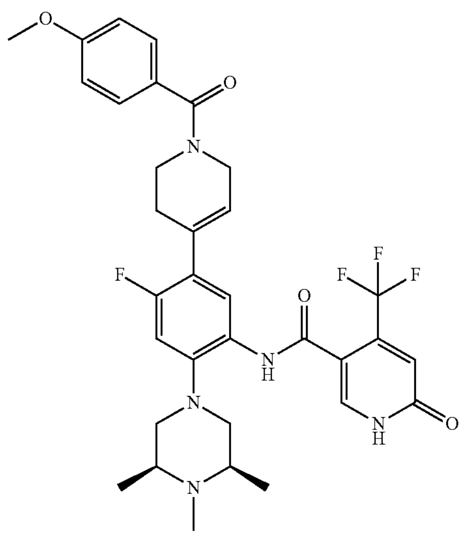 | N-[4-fluoro-5-[1-(4-methoxybenzoyl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.000943 |
| 566 | 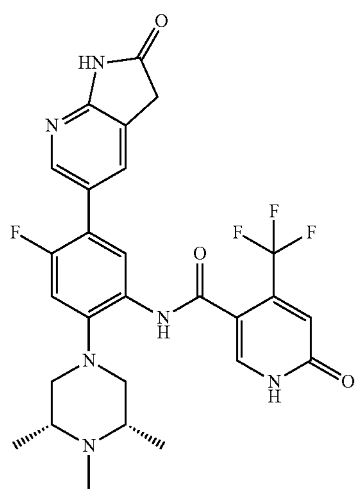 [SMILES: C[C@@H]1CN(c2cc(F)c(-c3cnc4c(c3)CC(=O)N4)cc2NC(=O)c2c[nH]c(=O)cc2C(F)(F)F)C[C@H](C)N1C] | N-[4-fluoro-5-(2-oxo-1,3-dihydropyrrolo[2,3-b]pyridin-5-yl)-2-[rac-(3R,5S)-3,4,5-trimethylpiperazin-1-yl]phenyl]-6-oxo-4-(trifluoromethyl)-1H-pyridine-3-carboxamide | 0.000896 |
| 567 | 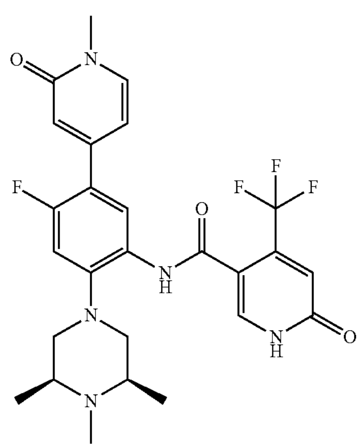 [SMILES: C[C@@H]1CN(c2cc(F)c(-c3ccn(C)c(=O)c3)cc2NC(=O)c2c[nH]c(=O)cc2C(F)(F)F)C[C@H](C)N1C] | N-[4-fluoro-5-(1-methyl-2-oxopyridin-4-yl)-2-[rac-(3R,5S)-3,4,5-trimethylpiperazin-1-yl]phenyl]-6-oxo-4-(trifluoromethyl)-1H-pyridine-3-carboxamide | 0.00118 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 568 | 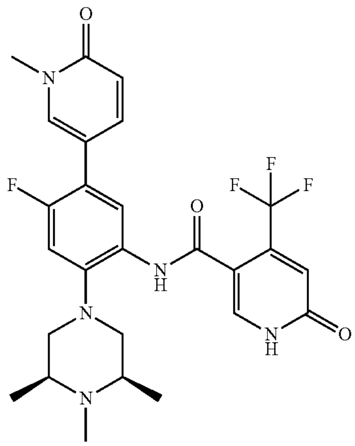 [SMILES: C[C@@H]1CN(c2cc(F)c(-c3ccc(=O)n(C)c3)cc2NC(=O)c2c[nH]c(=O)cc2C(F)(F)F)C[C@H](C)N1C] | N-[4-fluoro-5-(1-methyl-6-oxopyridin-3-yl)-2-[rac-(3R,5S)-3,4,5-trimethylpiperazin-1-yl]phenyl]-6-oxo-4-(trifluoromethyl)-1H-pyridine-3-carboxamide | 0.00458 |
| 569 | 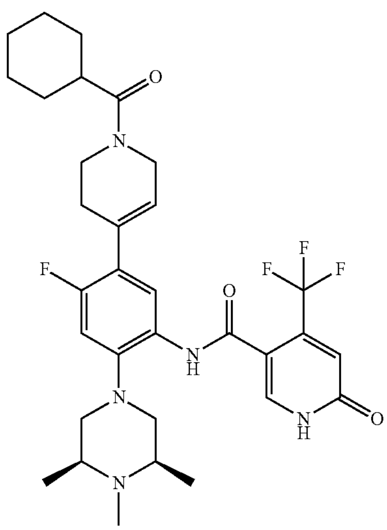 [SMILES: C[C@@H]1CN(c2cc(F)c(C3=CCN(C(=O)C4CCCCC4)CC3)cc2NC(=O)c2c[nH]c(=O)cc2C(F)(F)F)C[C@H](C)N1C] | N-[5-[1-(cyclohexanecarbonyl)-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00199 |
| 570 | 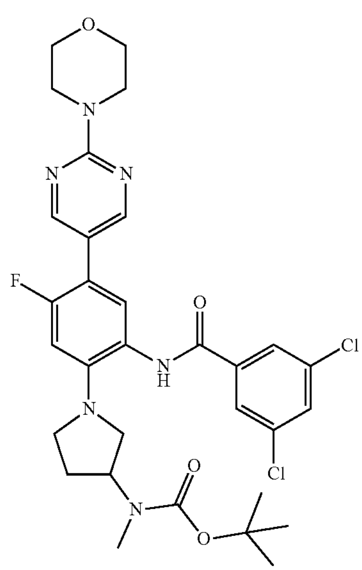 [SMILES: CN(C(=O)OC(C)(C)C)C1CCN(c2cc(F)c(-c3cnc(N4CCOCC4)nc3)cc2NC(=O)c2cc(Cl)cc(Cl)c2)C1] | tert-butyl N-[1-[2-[(3,5-dichlorobenzoyl)amino]-5-fluoro-4-(2-morpholin-4-ylpyrimidin-5-yl)phenyl]pyrrolidin-3-yl]-N-methylcarbamate | — |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 571 | 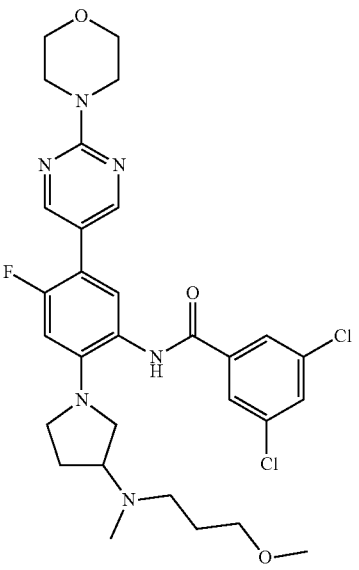 [SMILES: COCCCN(C)C1CCN(c2cc(F)c(-c3cnc(N4CCOCC4)nc3)cc2NC(=O)c2cc(Cl)cc(Cl)c2)C1] | 3,5-dichloro-N-[4-fluoro-2-[3-[3-methoxypropyl(methyl)amino]pyrrolidin-1-yl]-5-(2-morpholin-4-ylpyrimidin-5-yl)phenyl]benzamide | — |
| 572 | 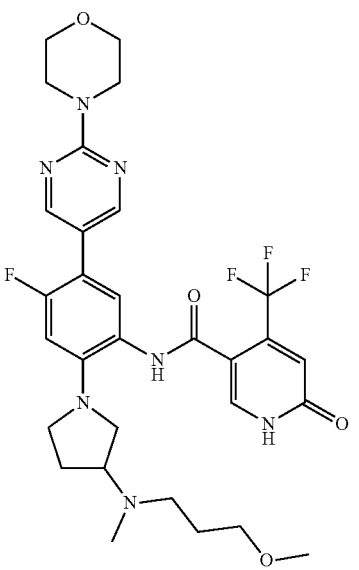 [SMILES: COCCCN(C)C1CCN(c2cc(F)c(-c3cnc(N4CCOCC4)nc3)cc2NC(=O)c2c[nH]c(=O)cc2C(F)(F)F)C1] | N-[4-fluoro-2-[3-[3-methoxypropyl(methyl)amino]pyrrolidin-1-yl]-5-(2-morpholin-4-ylpyrimidin-5-yl)phenyl]-6-oxo-4-(trifluoromethyl)-1H-pyridine-3-carboxamide | 0.113 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 573 | 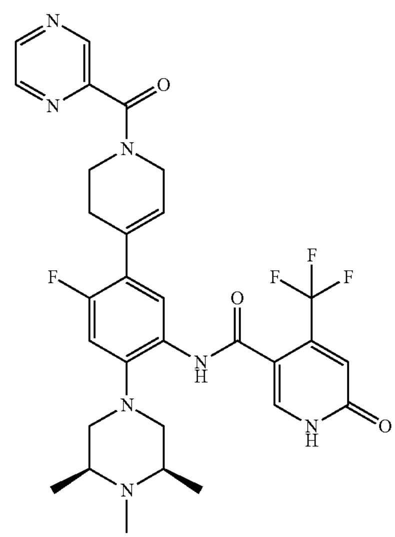 [SMILES: C[C@@H]1CN(c2cc(F)c(C3=CCN(C(=O)c4cnccn4)CC3)cc2NC(=O)c2c[nH]c(=O)cc2C(F)(F)F)C[C@H](C)N1C] | N-[4-fluoro-5-[1-(pyrazine-2-carbonyl)-3,6-dihydro-2H-pyridin-4-yl]-2-[rac-(3R,5S)-3,4,5-trimethylpiperazin-1-yl]phenyl]-6-oxo-4-(trifluoromethyl)-1H-pyridine-3-carboxamide | 0.00219 |
| 574 | 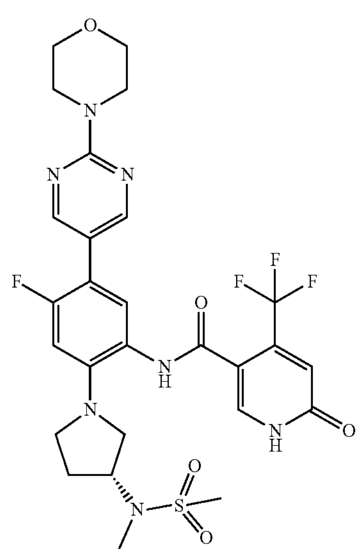 [SMILES: CN([C@@H]1CCN(c2cc(F)c(-c3cnc(N4CCOCC4)nc3)cc2NC(=O)c2c[nH]c(=O)cc2C(F)(F)F)C1)S(C)(=O)=O] | N-[4-fluoro-5-(2-morpholin-4-ylpyrimidin-5-yl)-2-[rac-(3R)-3-[methyl(methylsulfonyl)amino]pyrrolidin-1-yl]phenyl]-6-oxo-4-(trifluoromethyl)-1H-pyridine-3-carboxamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 575 | 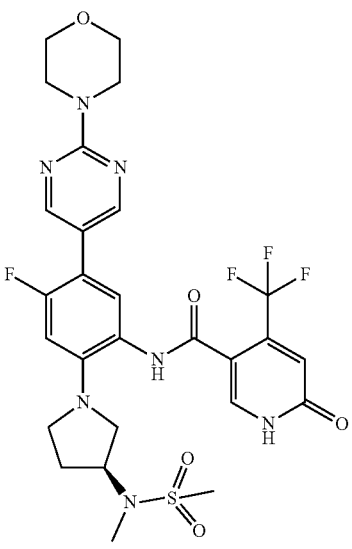 [SMILES: CN([C@H]1CCN(c2cc(F)c(-c3cnc(N4CCOCC4)nc3)cc2NC(=O)c2c[nH]c(=O)cc2C(F)(F)F)C1)S(C)(=O)=O] | N-[4-fluoro-5-(2-morpholin-4-ylpyrimidin-5-yl)-2-[rac-(3R)-3-[methyl(methylsulfonyl)amino]pyrrolidin-1-yl]phenyl]-6-oxo-4-(trifluoromethyl)-1H-pyridine-3-carboxamide | — |
| 576 | 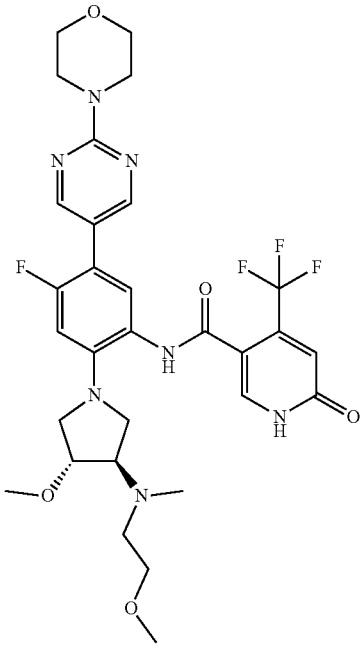 [SMILES: COCCN(C)[C@@H]1CN(c2cc(F)c(-c3cnc(N4CCOCC4)nc3)cc2NC(=O)c2c[nH]c(=O)cc2C(F)(F)F)C[C@H]1OC] | N-[4-fluoro-5-(2-morpholin-4-ylpyrimidin-5-yl)-2-[rac-(3R,4R)-3-methoxy-4-[2-methoxyethyl(methyl)amino]pyrrolidin-1-yl]phenyl]-6-oxo-4-(trifluoromethyl)-1H-pyridine-3-carboxamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 577 | 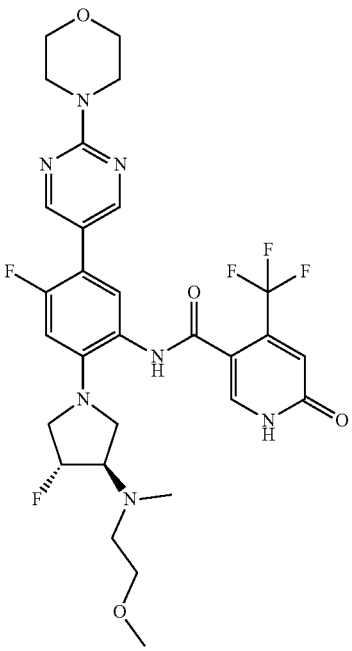 [SMILES: COCCN(C)[C@@H]1CN(c2cc(F)c(-c3cnc(N4CCOCC4)nc3)cc2NC(=O)c2c[nH]c(=O)cc2C(F)(F)F)C[C@H]1F] | N-[4-fluoro-5-(2-morpholin-4-ylpyrimidin-5-yl)-2-[rac-(3R,4R)-3-fluoro-4-[2-methoxyethyl(methyl)amino]pyrrolidin-1-yl]phenyl]-6-oxo-4-(trifluoromethyl)-1H-pyridine-3-carboxamide | — |
| 578 | 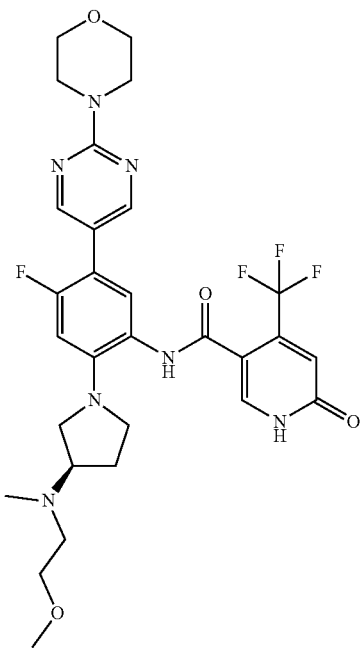 | N-[4-fluoro-5-(2-morpholin-4-ylpyrimidin-5-yl)-2-[rac-(3R)-3-[2-methoxyethyl(methyl)amino]pyrrolidin-1-yl]phenyl]-6-oxo-4-(trifluoromethyl)-1H-pyridine-3-carboxamide | 0.0169 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 579 | 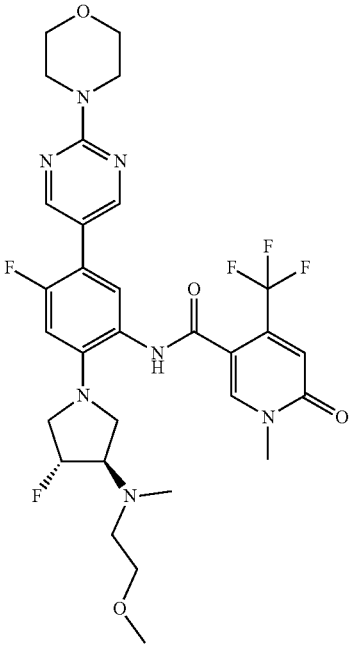 | N-[4-fluoro-5-(2-morpholin-4-ylpyrimidin-5-yl)-2-[rac-(3R,4R)-3-fluoro-4-[2-methoxyethyl(methyl)amino]pyrrolidin-1-yl]phenyl]-1-methyl-6-oxo-4-(trifluoromethyl)pyridine-3-carboxamide | — |
| 580 | 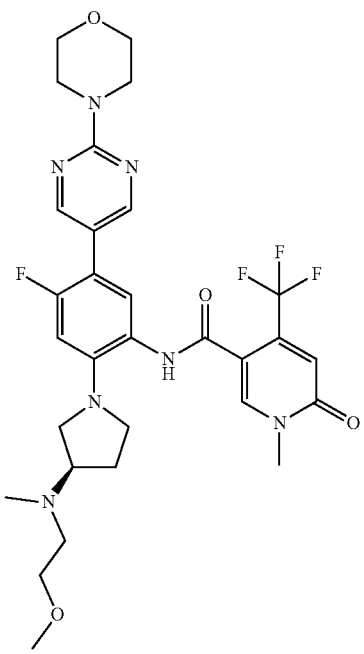 | N-[4-fluoro-5-(2-morpholin-4-ylpyrimidin-5-yl)-2-[rac-(3R)-3-[2-methoxyethyl(methyl)amino]pyrrolidin-1-yl]phenyl]-1-methyl-6-oxo-4-(trifluoromethyl)pyridine-3-carboxamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 581 | 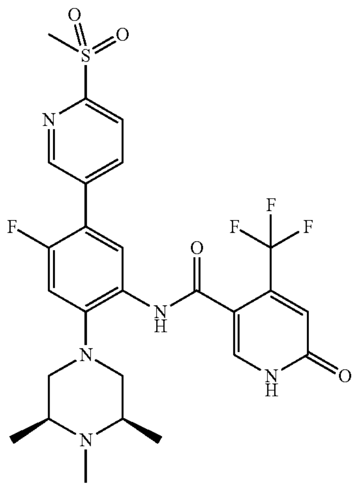 [SMILES: C[C@@H]1CN(c2cc(F)c(-c3ccc(S(C)(=O)=O)nc3)cc2NC(=O)c2c[nH]c(=O)cc2C(F)(F)F)C[C@H](C)N1C] | N-[4-fluoro-5-(6-methylsulfonylpyridin-3-yl)-2-[rac-(3R,5S)-3,4,5-trimethylpiperazin-1-yl]phenyl]-6-oxo-4-(trifluoromethyl)-1H-pyridine-3-carboxamide | 0.000768 |
| 582 | 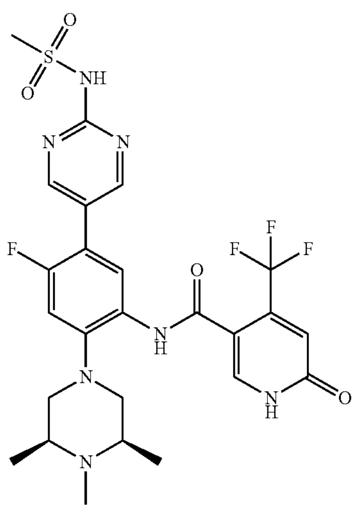 [SMILES: C[C@@H]1CN(c2cc(F)c(-c3cnc(NS(C)(=O)=O)nc3)cc2NC(=O)c2c[nH]c(=O)cc2C(F)(F)F)C[C@H](C)N1C] | N-[4-fluoro-5-[2-(methanesulfonamido)pyrimidin-5-yl]-2-[rac-(3R,5S)-3,4,5-trimethylpiperazin-1-yl]phenyl]-6-oxo-4-(trifluoromethyl)-1H-pyridine-3-carboxamide | 0.00578 |
| 583 | 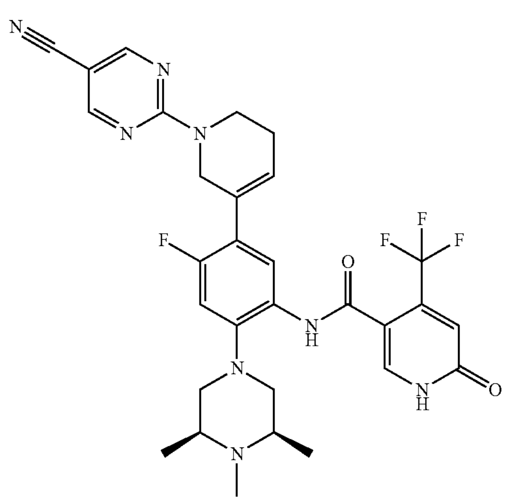 [SMILES: C[C@@H]1CN(c2cc(F)c(C3=CCCN(c4ncc(C#N)cn4)C3)cc2NC(=O)c2c[nH]c(=O)cc2C(F)(F)F)C[C@H](C)N1C] | N-[5-[1-(5-cyanopyrimdin-2-yl)-3,6-dihydro-2H-pyridin-5-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.000877 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 584 | 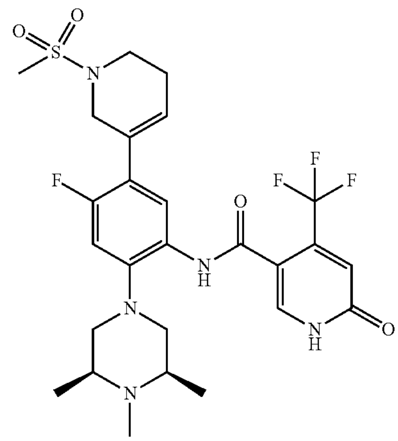 [SMILES: C[C@@H]1CN(c2cc(F)c(C3=CCCN(S(C)(=O)=O)C3)cc2NC(=O)c2c[nH]c(=O)cc2C(F)(F)F)C[C@H](C)N1C] | N-[4-fluoro-5-(1-methylsulfonyl-3,6-dihydro-2H-pyridin-5-yl)-2-[rac-(3R,5S)-3,4,5-trimethylpiperazin-1-yl]phenyl]-6-oxo-4-(trifluoromethyl)-1H-pyridine-3-carboxamide | 0.00121 |
| 585 | 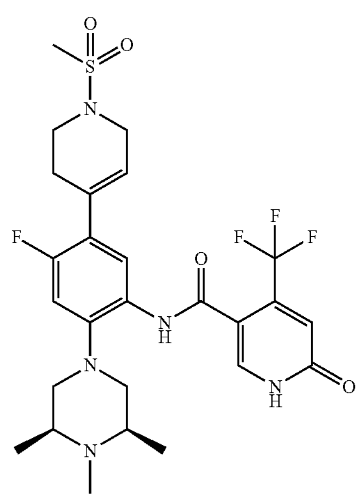 [SMILES: C[C@@H]1CN(c2cc(F)c(C3=CCN(S(C)(=O)=O)CC3)cc2NC(=O)c2c[nH]c(=O)cc2C(F)(F)F)C[C@H](C)N1C] | N-[4-fluoro-5-(1-methylsulfonyl-3,6-dihydro-2H-pyridin-4-yl)-2-[rac-(3R,5S)-3,4,5-trimethylpiperazin-1-yl]phenyl]-6-oxo-4-(trifluoromethyl)-1H-pyridine-3-carboxamide | 0.000829 |

TABLE 1-continued

Binding affinities (K$_D$) derived from surface plasmon resonance (SPR) assays

| Example No. | Structure | IUPAC Name | WDR5 binding affinity (K$_D$, μM) |
| --- | --- | --- | --- |
| 586 | 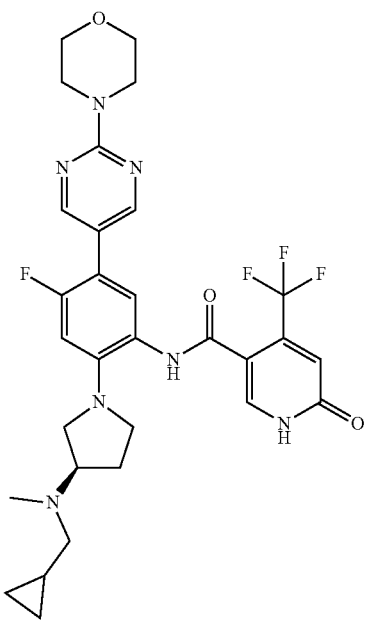 | N-[4-fluoro-5-(2-morpholin-4-ylpyrimidin-5-yl)-2-[rac-(3R)-3-[cyclopropylmethyl(methyl)amino]pyrrolidin-1-yl]phenyl]-6-oxo-4-(trifluoromethyl)-1H-pyridine-3-carboxamide | 0.0155 |
| 587 | 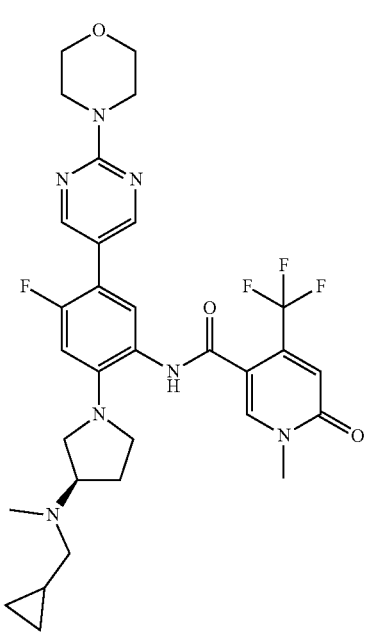 [SMILES: CN(CC1CC1)[C@@H]1CCN(c2cc(F)c(-c3cnc(N4CCOCC4)nc3)cc2NC(=O)c2cn(C)c(=O)cc2C(F)(F)F)C1] | N-[4-fluoro-5-(2-morpholin-4-ylpyrimidin-5-yl)-2-[rac-(3R)-3-[cyclopropylmethyl(methyl)amino]pyrrolidin-1-yl]phenyl]-1-methyl-6-oxo-4-(trifluoromethyl)pyridine-3-carboxamide | 0.253 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 588 | 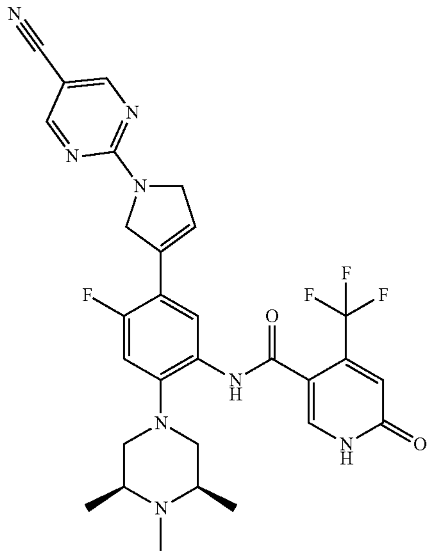 [SMILES: C[C@@H]1CN(c2cc(F)c(C3=CCN(c4ncc(C#N)cn4)C3)cc2NC(=O)c2c[nH]c(=O)cc2C(F)(F)F)C[C@H](C)N1C] | N-[5-[1-(5-cyanopyrimidin-2-yl)-2,5-dihydropyrrol-3-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00172 |
| 589 | 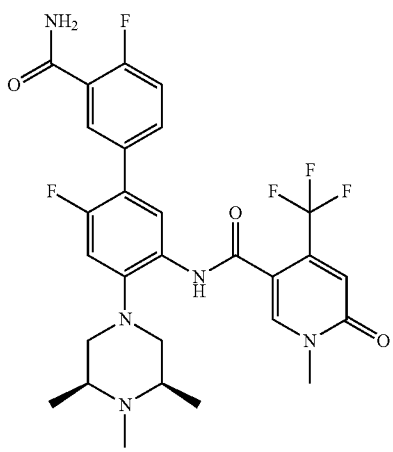 | N-[5-(3-carbamoyl-4-fluorophenyl)-4-fluoro-2-[rac-(3R,5S)-3,4,5-trimethylpiperazin-1-yl]phenyl]-1-methyl-6-oxo-4-(trifluoromethyl)pyridine-3-carboxamide | 0.00746 |
| 590 | 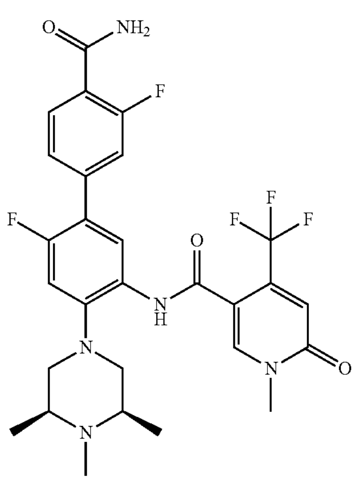 | N-[5-(4-carbamoyl-3-fluorophenyl)-4-fluoro-2-[rac-(3R,5S)-3,4,5-trimethylpiperazin-1-yl]phenyl]-1-methyl-6-oxo-4-(trifluoromethyl)pyridine-3-carboxamide | 0.00332 |

TABLE 1-continued

Binding affinities (K_D) derived from surface plasmon resonance (SPR) assays

| Example No. | Structure | IUPAC Name | WDR5 binding affinity (K$_D$, µM) |
|---|---|---|---|
| 591 | 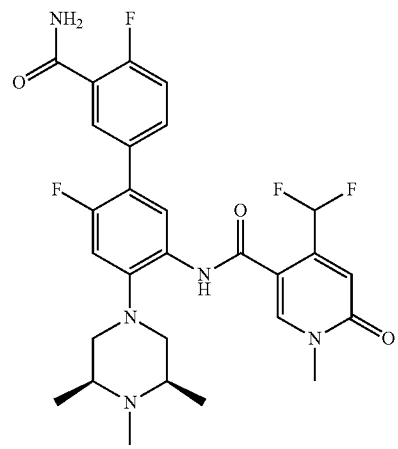 | N-[5-(3-carbamoyl-4-fluorophenyl)-4-fluoro-2-[rac-(3R,5S)-3,4,5-trimethylpiperazin-1-yl]phenyl]-4-(difluoromethyl)-1-methyl-6-oxopyridine-3-carboxamide | 0.0155 |
| 592 | 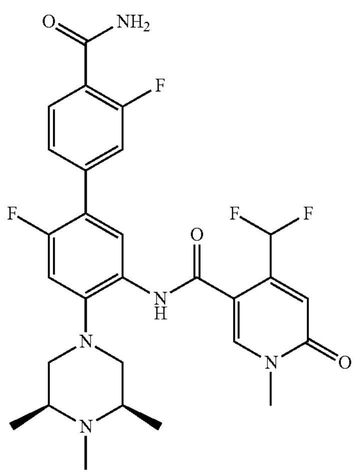 [SMILES: C[C@@H]1CN(c2cc(F)c(-c3ccc(C(N)=O)c(F)c3)cc2NC(=O)c2cn(C)c(=O)cc2C(F)F)C[C@H](C)N1C] | N-[5-(4-carbamoyl-3-fluorophenyl)-4-fluoro-2-[rac-(3R,5S)-3,4,5-trimethylpiperazin-1-yl]phenyl]-4-(difluoromethyl)-1-methyl-6-oxopyridine-3-carboxamide | 0.0068 |
| 593 | 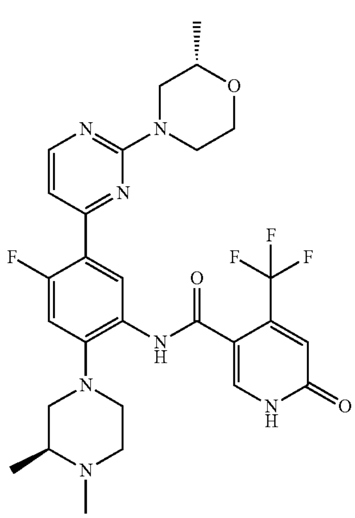 [SMILES: C[C@H]1CN(c2nccc(-c3cc(NC(=O)c4c[nH]c(=O)cc4C(F)(F)F)c(N4CCN(C)[C@@H](C)C4)cc3F)n2)CCO1] | N-[4-fluoro-2-[rac-(3R)-3,4-dimethylpiperazin-1-yl]-5-[2-[rac-(2R)-2-methylmorpholin-4-yl]pyrimidin-4-yl]phenyl]-6-oxo-4-(trifluoromethyl)-1H-pyridine-3-carboxamide | 0.000737 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 594 | 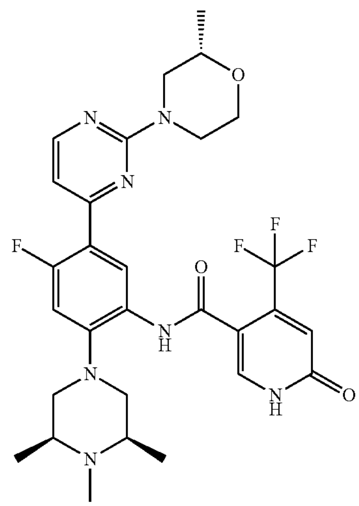 [SMILES: C[C@@H]1CN(c2cc(F)c(-c3ccnc(N4CCO[C@@H](C)C4)n3)cc2NC(=O)c2c[nH]c(=O)cc2C(F)(F)F)C[C@H](C)N1C] | N-[4-fluoro-5-[2-[rac-(2R)-2-methylmorpholin-4-yl]pyrimidin-4-yl]-2-[rac-(3S,5R)-3,4,5-trimethylpiperazin-1-yl]phenyl]-6-oxo-4-(trifluoromethyl)-1H-pyridine-3-carboxamide | 0.000712 |
| 595 | 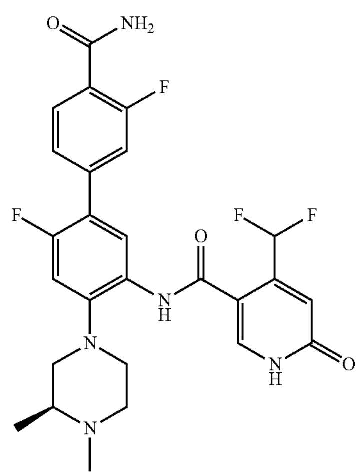 [SMILES: C[C@H]1CN(c2cc(F)c(-c3ccc(C(N)=O)c(F)c3)cc2NC(=O)c2c[nH]c(=O)cc2C(F)F)CCN1C] | N-[5-(4-carbamoyl-3-fluorophenyl)-4-fluoro-2-[rac-(3R)-3,4-dimethylpiperazin-1-yl]phenyl]-4-(difluoromethyl)-6-oxo-1H-pyridine-3-carboxamide | 0.00118 |
| 596 | 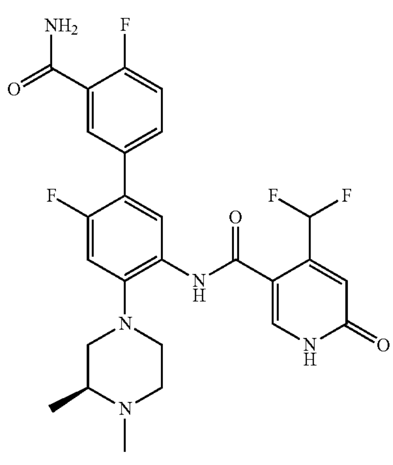 [SMILES: C[C@H]1CN(c2cc(F)c(-c3ccc(F)c(C(N)=O)c3)cc2NC(=O)c2c[nH]c(=O)cc2C(F)F)CCN1C] | N-[5-(3-carbamoyl-4-fluorophenyl)-4-fluoro-2-[rac-(3R)-3,4-dimethylpiperazin-1-yl]phenyl]-4-(difluoromethyl)-6-oxo-1H-pyridine-3-carboxamide | 0.00403 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 597 | 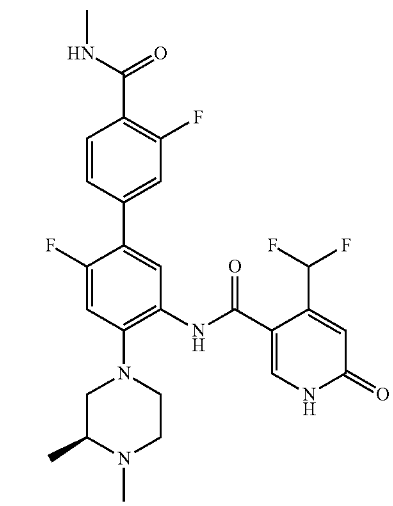 [SMILES: CNC(=O)c1ccc(-c2cc(NC(=O)c3c[nH]c(=O)cc3C(F)F)c(N3CCN(C)[C@@H](C)C3)cc2F)cc1F] | 4-(difluoromethyl)-N-[4-fluoro-5-[3-fluoro-4-(methylcarbamoyl)phenyl]-2-[rac-(3R)-3,4-dimethylpiperazin-1-yl]phenyl]-6-oxo-1H-pyridine-3-carboxamide | 0.000711 |
| 598 | 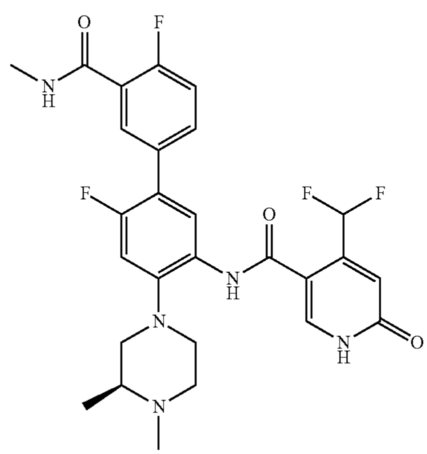 [SMILES: CNC(=O)c1cc(-c2cc(NC(=O)c3c[nH]c(=O)cc3C(F)F)c(N3CCN(C)[C@@H](C)C3)cc2F)ccc1F] | 4-(difluoromethyl)-N-[4-fluoro-5-[4-fluoro-3-(methylcarbamoyl)phenyl]-2-[rac-(3R)-3,4-dimethylpiperazin-1-yl]phenyl]-6-oxo-1H-pyridine-3-carboxamide | 0.00151 |
| 599 | 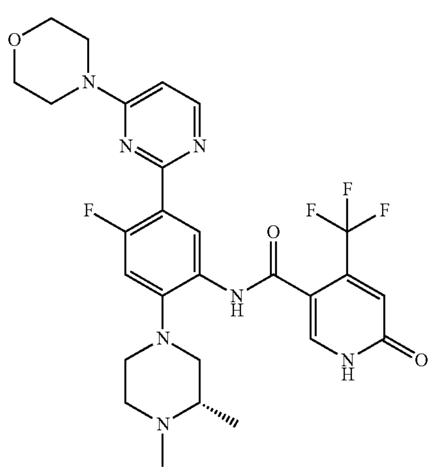 [SMILES: C[C@H]1CN(c2cc(F)c(-c3nccc(N4CCOCC4)n3)cc2NC(=O)c2c[nH]c(=O)cc2C(F)(F)F)CCN1C] | N-[4-fluoro-5-(4-morpholin-4-ylpyrimidin-2-yl)-2-[rac-(3R)-3,4-dimethylpiperazin-1-yl]phenyl]-6-oxo-4-(trifluoromethyl)-1H-pyridine-3-carboxamide | 0.00418 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 600 | 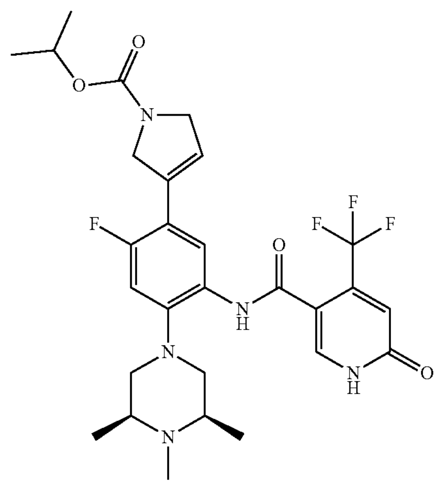 | propan-2-yl 3-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-2,5-dihydropyrrole-1-carboxylate | 0.000779 |
| 601 | 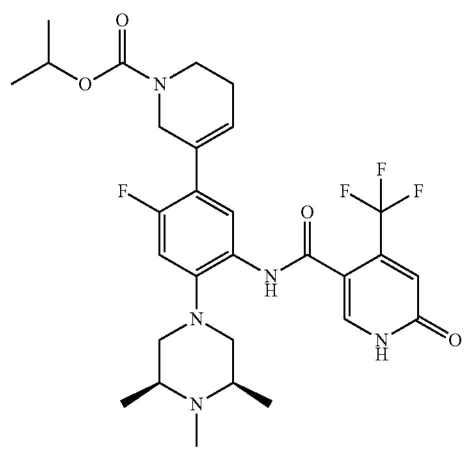 | propan-2-yl 5-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.000271 |
| 602 | 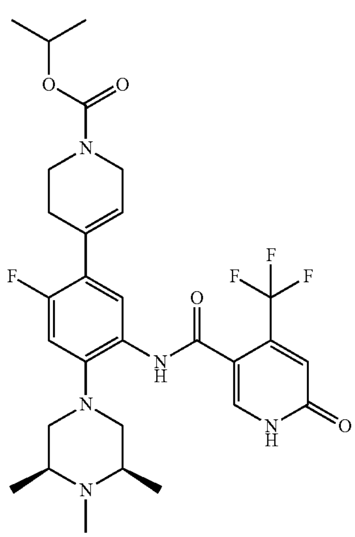 [SMILES: CC(C)OC(=O)N1CC=C(c2cc(NC(=O)c3c[nH]c(=O)cc3C(F)(F)F)c(N3C[C@@H](C)N(C)[C@@H](C)C3)cc2F)CC1] | propan-2-yl 4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-3,6-dihydro-2H-pyridine-1-carboxylate | 0.000475 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 603 | 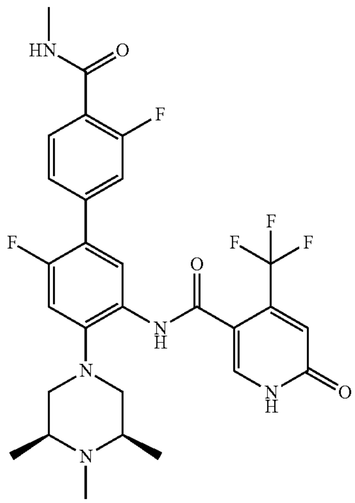 [SMILES: CNC(=O)c1ccc(-c2cc(NC(=O)c3c[nH]c(=O)cc3C(F)(F)F)c(N3C[C@@H](C)N(C)[C@@H](C)C3)cc2F)cc1F] | N-[4-fluoro-5-[3-fluoro-4-(methylcarbamoyl)phenyl]-2-[rac-(3R,5S)-3,4,5-trimethylpiperazin-1-yl]phenyl]-6-oxo-4-(trifluoromethyl)-1H-pyridine-3-carboxamide | 0.00109 |
| 604 | 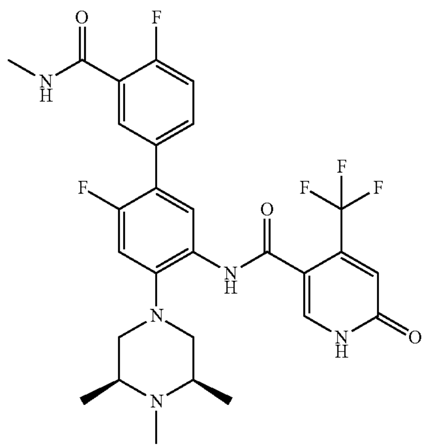 [SMILES: CNC(=O)c1cc(-c2cc(NC(=O)c3c[nH]c(=O)cc3C(F)(F)F)c(N3C[C@@H](C)N(C)[C@@H](C)C3)cc2F)ccc1F] | N-[4-fluoro-5-[4-fluoro-3-(methylcarbamoyl)phenyl]-2-[rac-(3R,5S)-3,4,5-trimethylpiperazin-1-yl]phenyl]-6-oxo-4-(trifluoromethyl)-1H-pyridine-3-carboxamide | 0.00171 |
| 605 | 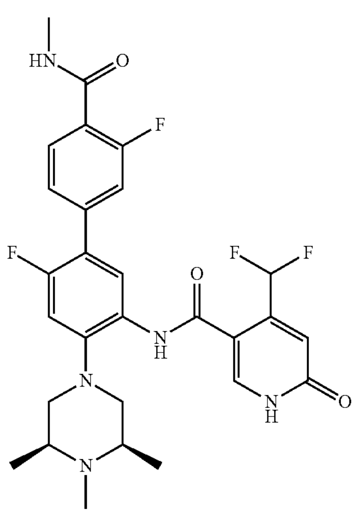 [SMILES: CNC(=O)c1ccc(-c2cc(NC(=O)c3c[nH]c(=O)cc3C(F)F)c(N3C[C@@H](C)N(C)[C@@H](C)C3)cc2F)cc1F] | 4-(difluoromethyl)-N-[4-fluoro-5-[3-fluoro-4-(methylcarbamoyl)phenyl]-2-[rac-(3R,5S)-3,4,5-trimethylpiperazin-1-yl]phenyl]-6-oxo-1H-pyridine-3-carboxamide | 0.0006 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 606 | 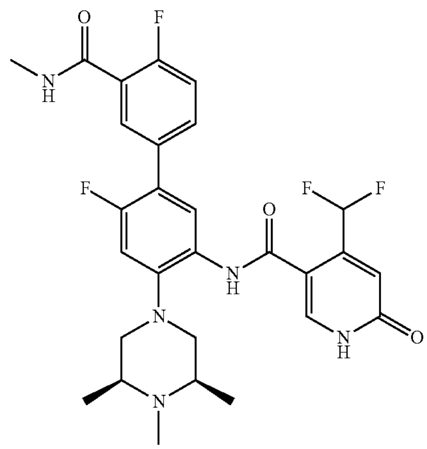 [SMILES: CNC(=O)c1cc(-c2cc(NC(=O)c3c[nH]c(=O)cc3C(F)F)c(N3C[C@@H](C)N(C)[C@@H](C)C3)cc2F)ccc1F] | 4-(difluoromethyl)-N-[4-fluoro-5-[4-fluoro-3-(methylcarbamoyl)phenyl]-2-[rac-(3R,5S)-3,4,5-trimethylpiperazin-1-yl]phenyl]-6-oxo-1H-pyridine-3-carboxamide | 0.00186 |
| 607 | 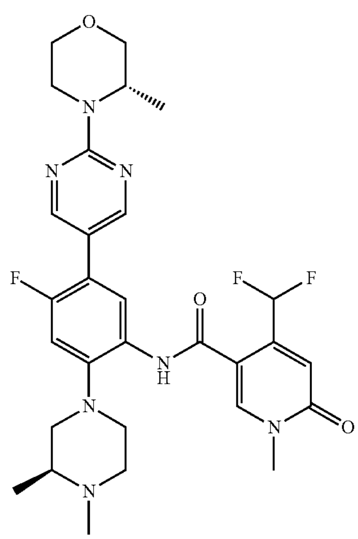 [SMILES: C[C@H]1CN(c2cc(F)c(-c3cnc(N4CCOC[C@@H]4C)nc3)cc2NC(=O)c2cn(C)c(=O)cc2C(F)F)CCN1C] | 4-(difluoromethyl)-N-[4-fluoro-2-[rac-(3R)-3,4-dimethylpiperazin-1-yl]-5-[2-[rac-(3R)-3-methylmorpholin-4-yl]pyrimidin-5-yl]phenyl]-1-methyl-6-oxopyridine-3-carboxamide | 0.00153 |
| 608 | 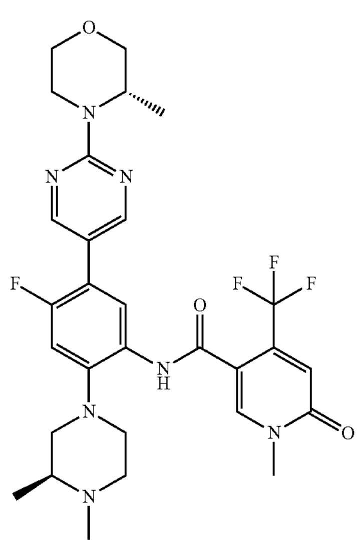 [SMILES: C[C@H]1CN(c2cc(F)c(-c3cnc(N4CCOC[C@@H]4C)nc3)cc2NC(=O)c2cn(C)c(=O)cc2C(F)(F)F)CCN1C] | N-[4-fluoro-2-[rac-(3R)-3,4-dimethylpiperazin-1-yl]-5-[2-[rac-(3R)-3-methylmorpholin-4-yl]pyrimidin-5-yl]phenyl]-1-methyl-6-oxo-4-(trifluoromethyl)pyridine-3-carboxamide | 0.000977 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 609 | 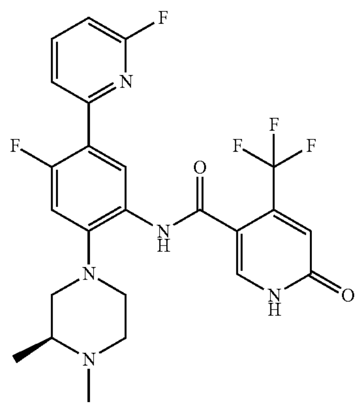 [SMILES: C[C@H]1CN(c2cc(F)c(-c3cccc(F)n3)cc2NC(=O)c2c[nH]c(=O)cc2C(F)(F)F)CCN1C] | N-[4-fluoro-5-(6-fluoropyridin-2-yl)-2-[rac-(3R)-3,4-dimethylpiperazin-1-yl]phenyl]-6-oxo-4-(trifluoromethyl)-1H-pyridine-3-carboxamide | 0.000774 |
| 610 | 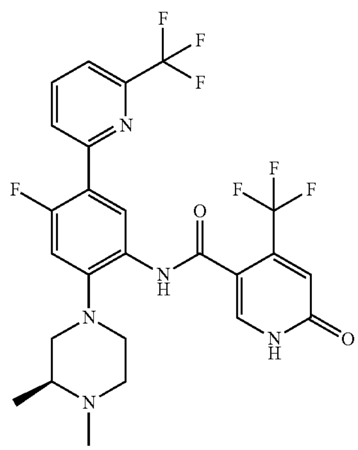 [SMILES: C[C@H]1CN(c2cc(F)c(-c3cccc(C(F)(F)F)n3)cc2NC(=O)c2c[nH]c(=O)cc2C(F)(F)F)CCN1C] | N-[-4-fluoro-2-[rac-(3R)-3,4-dimethylpiperazin-1-yl]-5-[6-(trifluoromethyl)pyridin-2-yl]phenyl]-6-oxo-4-(trifluoromethyl)-1H-pyridine-3-carboxamide | 0.000552 |
| 611 | 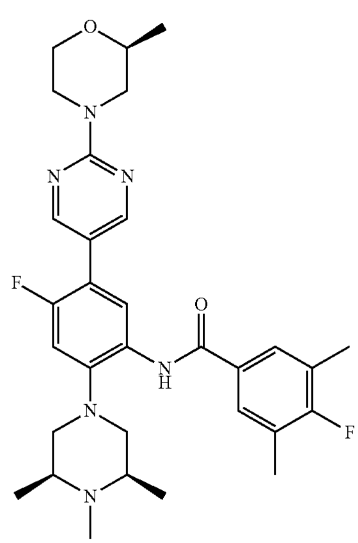 [SMILES: Cc1cc(C(=O)Nc2cc(-c3cnc(N4CCO[C@@H](C)C4)nc3)c(F)cc2N2C[C@@H](C)N(C)[C@@H](C)C2)cc(C)c1F] | 4-fluoro-N-[4-fluoro-5-[2-[rac-(2R)-2-methylmorpholin-4-yl]pyrimidin-5-yl]-2-[rac-(3S,5R)-3,4,5-trimethylpiperazin-1-yl]phenyl]-3,5-dimethylbenzamide | 0.00155 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 612 | 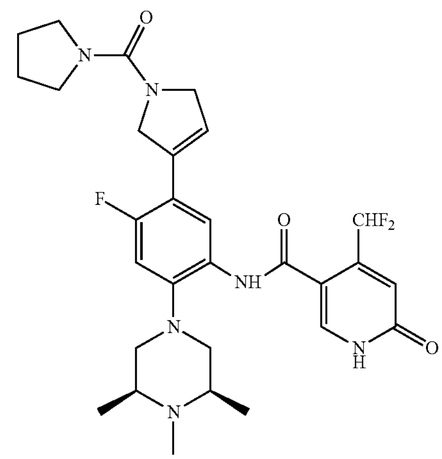 [SMILES: C[C@@H]1CN(c2cc(F)c(C3=CCN(C(=O)N4CCCC4)C3)cc2NC(=O)c2c[nH]c(=O)cc2C(F)F)C[C@H](C)N1C] | 4-(Difluoromethyl)-N-(4-fluoro-5-(1-(pyrrolidine-1-carbonyl)-2,5-dihydro-1H-pyrrol-3-yl)-2-((3S,5R)-3,4,5-trimethylpiperazin-1-yl)phenyl)-6-oxo-1,6-dihydropyridine-3-carboxamide | 0.00194 |
| 613 | 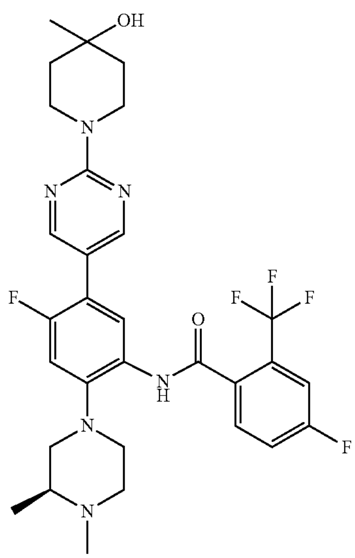 [SMILES: C[C@H]1CN(c2cc(F)c(-c3cnc(N4CCC(C)(O)CC4)nc3)cc2NC(=O)c2ccc(F)cc2C(F)(F)F)CCN1C] | 4-fluoro-N-[4-fluoro-5-[2-(4-hydroxy-4-methylpiperidin-1-yl)pyrimidin-5-yl]-2-[rac-(3R)-3,4-dimethylpiperazin-1-yl]phenyl]-2-(trifluoromethyl)benzamide | 0.000922 |
| 614 | 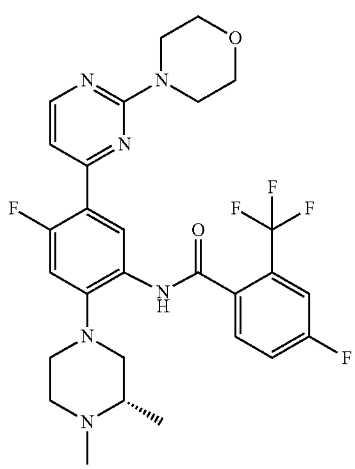 [SMILES: C[C@H]1CN(c2cc(F)c(-c3ccnc(N4CCOCC4)n3)cc2NC(=O)c2ccc(F)cc2C(F)(F)F)CCN1C] | 4-fluoro-N-[4-fluoro-5-(2-morpholin-4-ylpyrimidin-4-yl)-2-[rac-(3R)-3,4-dimethylpiperazin-1-yl]phenyl]-2-(trifluoromethyl)benzamide | 0.000733 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 615 | 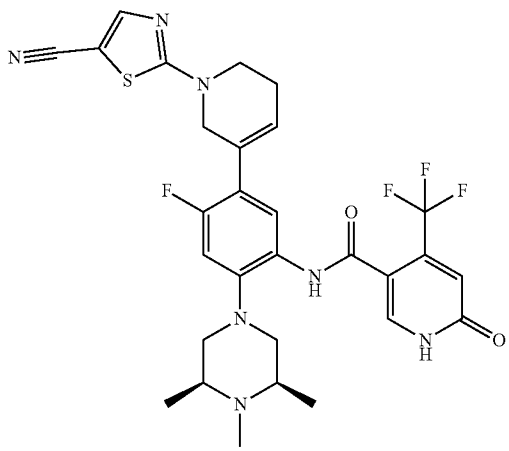 [SMILES: C[C@@H]1CN(c2cc(F)c(C3=CCCN(c4ncc(C#N)s4)C3)cc2NC(=O)c2c[nH]c(=O)cc2C(F)(F)F)C[C@H](C)N1C] | N-[5-[1-(5-cyano-1,3-thiazol-2-yl)-3,6-dihydro-2H-pyridin-5-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.000375 |
| 616 | 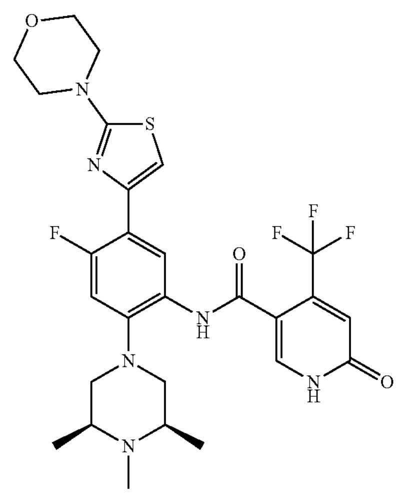 [SMILES: C[C@@H]1CN(c2cc(F)c(-c3csc(N4CCOCC4)n3)cc2NC(=O)c2c[nH]c(=O)cc2C(F)(F)F)C[C@H](C)N1C] | N-[4-fluoro-5-(2-morpholin-4-yl-1,3-thiazol-4-yl)-2-[rac-(3R,5S)-3,4,5-trimethylpiperazin-1-yl]phenyl]-6-oxo-4-(trifluoromethyl)-1H-pyridine-3-carboxamide | 0.000748 |
| 617 | 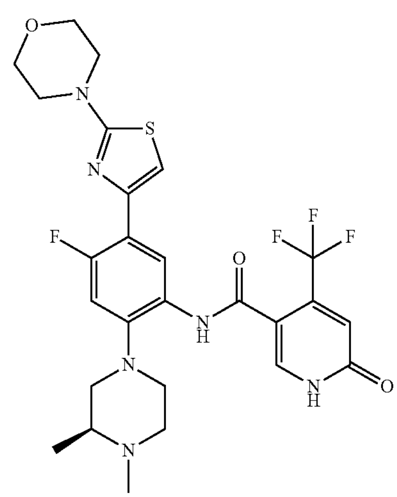 [SMILES: C[C@H]1CN(c2cc(F)c(-c3csc(N4CCOCC4)n3)cc2NC(=O)c2c[nH]c(=O)cc2C(F)(F)F)CCN1C] | N-[4-fluoro-5-(2-morpholin-4-yl-1,3-thiazol-4-yl)-2-[rac-(3R)-3,4-dimethylpiperazin-1-yl]phenyl]-6-oxo-4-(trifluoromethyl)-1H-pyridine-3-carboxamide | 000558 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 618 | 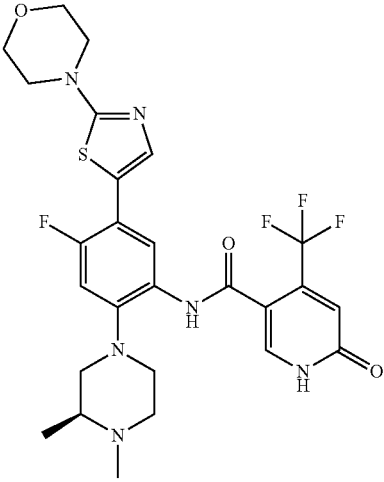 [SMILES: C[C@H]1CN(c2cc(F)c(-c3cnc(N4CCOCC4)s3)cc2NC(=O)c2c[nH]c(=O)cc2C(F)(F)F)CCN1C] | N-[4-fluoro-5-(2-morpholin-4-yl-1,3-thiazol-5-yl)-2-[rac-(3R)-3,4-dimethylpiperazin-1-yl]phenyl]-6-oxo-4-(trifluoromethyl)-1H-pyridine-3-carboxamide | 0.001130. |
| 619 | 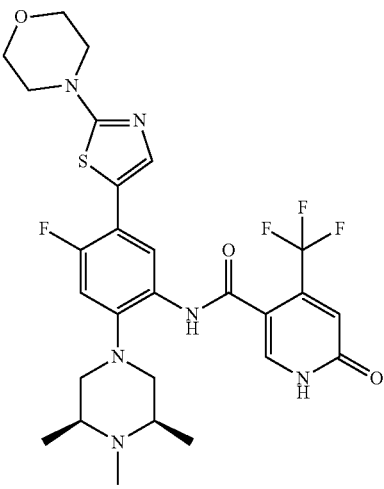 [SMILES: C[C@@H]1CN(c2cc(F)c(-c3cnc(N4CCOCC4)s3)cc2NC(=O)c2c[nH]c(=O)cc2C(F)(F)F)C[C@H](C)N1C] | N-[4-fluoro-5-(2-morpholin-4-yl-1,3-thiazol-5-yl)-2-[rac-(3R,5S)-3,4,5-trimethylpiperazin-1-yl]phenyl]-6-oxo-4-(trifluoromethyl)-1H-pyridine-3-carboxamide | 0.000948 |
| 620 | 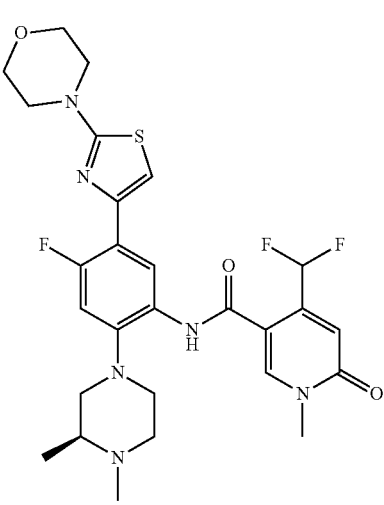 [SMILES: C[C@H]1CN(c2cc(F)c(-c3csc(N4CCOCC4)n3)cc2NC(=O)c2cn(C)c(=O)cc2C(F)F)CCN1C] | 4-(difluoromethyl)-N-[4-fluoro-5-(2-morpholin-4-yl-1,3-thiazol-4-yl)-2-[rac-(3R)-3,4-dimethylpiperazin-1-yl]phenyl]-1-methyl-6-oxopyridine-3-carboxamide | 0.00419 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 621 | 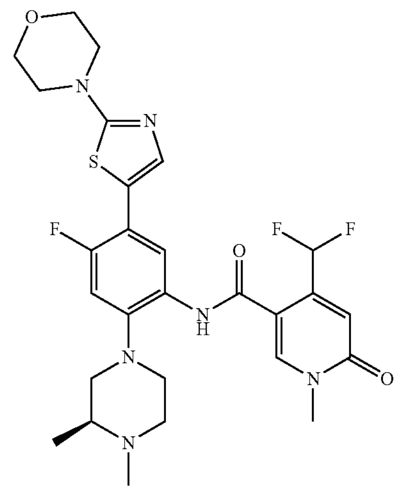 [SMILES: C[C@H]1CN(c2cc(F)c(-c3cnc(N4CCOCC4)s3)cc2NC(=O)c2cn(C)c(=O)cc2C(F)F)CCN1C] | 4-(difluoromethyl)-N-[4-fluoro-5-(2-morpholin-4-yl-1,3-thiazol-5-yl)-2-[rac-(3R)-3,4-dimethylpiperazin-1-yl]phenyl]-1-methyl-6-oxopyridine-3-carboxamide | 0.00484 |
| 622 | 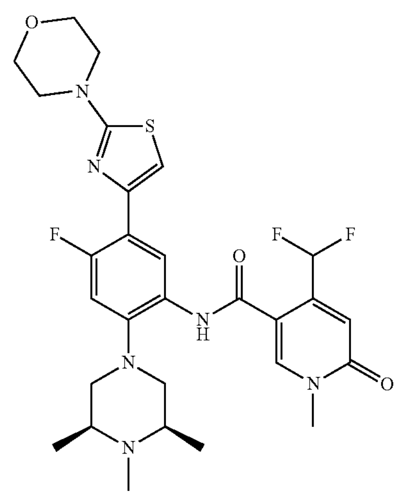 [SMILES: C[C@@H]1CN(c2cc(F)c(-c3csc(N4CCOCC4)n3)cc2NC(=O)c2cn(C)c(=O)cc2C(F)F)C[C@H](C)N1C] | 4-(difluoromethyl)-N-[4-fluoro-5-(2-morpholin-4-yl-1,3-thiazol-4-yl)-2-[rac-(3R,5S)-3,4,5-trimethylpiperazin-1-yl]phenyl]-1-methyl-6-oxopyridine-3-carboxamide | 0.00515 |
| 623 | 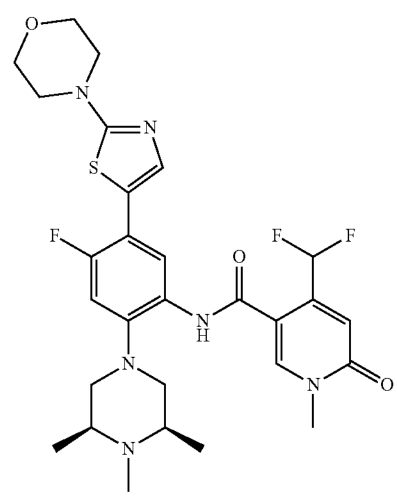 [SMILES: C[C@@H]1CN(c2cc(F)c(-c3cnc(N4CCOCC4)s3)cc2NC(=O)c2cn(C)c(=O)cc2C(F)F)C[C@H](C)N1C] | 4-(difluoromethyl)-N-[4-fluoro-5-(2-morpholin-4-yl-1,3-thiazol-5-yl)-2-[rac-(3R,5S)-3,4,5-trimethylpiperazin-1-yl]phenyl]-1-methyl-6-oxopyridine-3-carboxamide | 0.00557 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 624 | 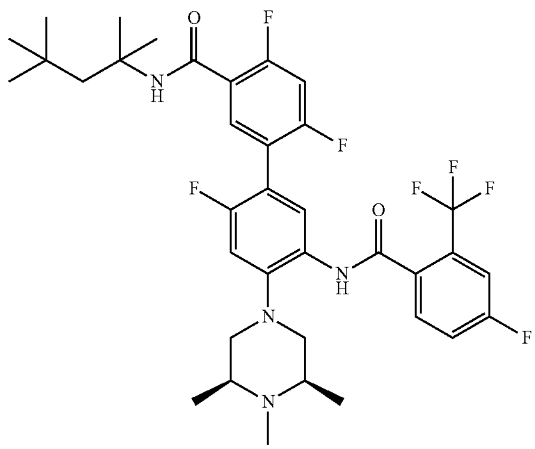 [SMILES: C[C@@H]1CN(c2cc(F)c(-c3cc(C(=O)NC(C)(C)CC(C)(C)C)c(F)cc3F)cc2NC(=O)c2ccc(F)cc2C(F)(F)F)C[C@H](C)N1C] | 2,4-difluoro-5-[2-fluoro-5-[[4-fluoro-2-(trifluoromethyl)benzoyl]amino]-4-[rac-(3R,5S)-3,4,5-trimethylpiperazin-1-yl]phenyl]-N-(2,4,4-trimethylpentan-2-yl)benzamide | — |
| 625 | 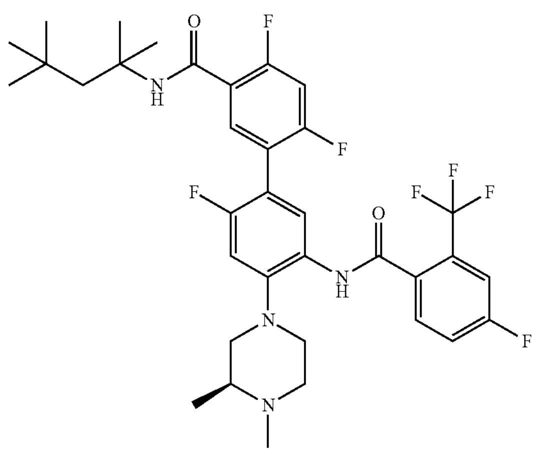 [SMILES: C[C@H]1CN(c2cc(F)c(-c3cc(C(=O)NC(C)(C)CC(C)(C)C)c(F)cc3F)cc2NC(=O)c2ccc(F)cc2C(F)(F)F)CCN1C] | 2,4-difluoro-5-[2-fluoro-5-[[4-fluoro-2-(trifluoromethyl)benzoyl]amino]-4-[rac-(3R)-3,4-dimethylpiperazin-1-yl]phenyl]-N-(2,4,4-trimethylpentan-2-yl)benzamide | 0.172 |
| 626 | 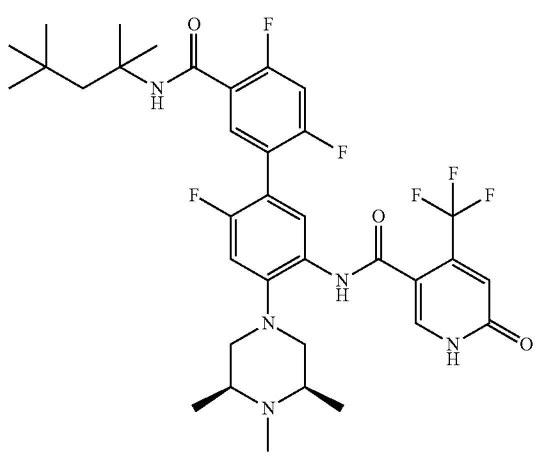 | N-[5-[2,4-difluoro-5-(2,4,4-trimethylpentan-2-ylcarbamoyl)phenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00524 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 627 | 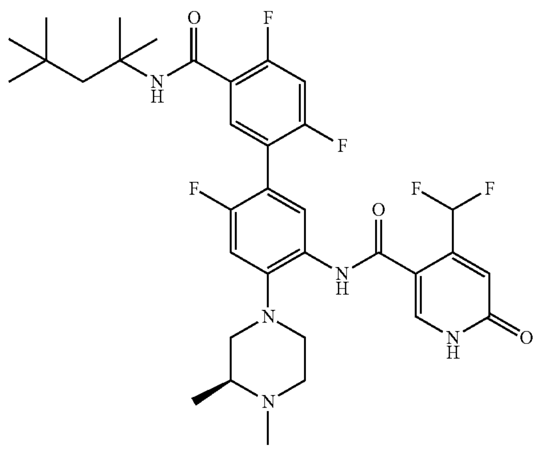 [SMILES: C[C@H]1CN(c2cc(F)c(-c3cc(C(=O)NC(C)(C)CC(C)(C)C)c(F)cc3F)cc2NC(=O)c2c[nH]c(=O)cc2C(F)F)CCN1C] | 4-(difluoromethyl)-N-[5-[2,4-difluoro-5-(2,4,4-trimethylpentan-2-ylcarbamoyl)phenyl]-4-fluoro-2-[rac-(3R,5S)-3,4,5-trimethylpiperazin-1-yl]phenyl]-6-oxo-1H-pyridine-3-carboxamide | 0.0233 |
| 628 | 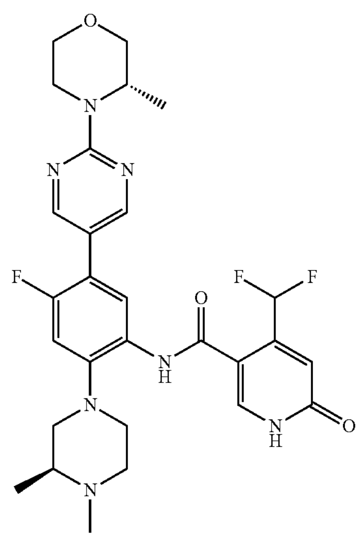 [SMILES: C[C@H]1CN(c2cc(F)c(-c3cnc(N4CCOC[C@@H]4C)nc3)cc2NC(=O)c2c[nH]c(=O)cc2C(F)F)CCN1C] | 4-(difluoromethyl)-N-[4-fluoro-2-[rac-(3R)-3,4-dimethylpiperazin-1-yl]-5-[2-[rac-(3R)-3-methylmorpholin-4-yl]pyrimidin-5-yl]phenyl]-6-oxo-1H-pyridine-3-carboxamide | 0.00125 |
| 629 | 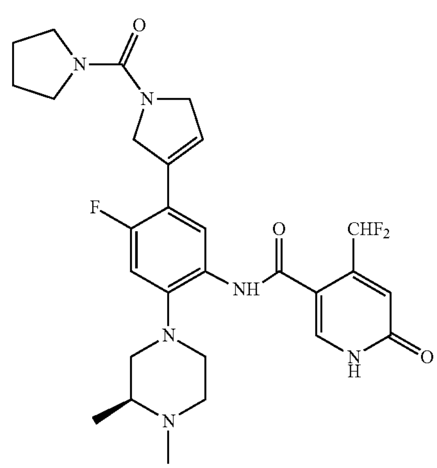 [SMILES: C[C@H]1CN(c2cc(F)c(C3=CCN(C(=O)N4CCCC4)C3)cc2NC(=O)c2c[nH]c(=O)cc2C(F)F)CCN1C] | (S)-4-(Sifluoromethyl)-N-(2-(3,4-dimethylpiperazin-1-yl)-4-fluoro-5-(1-(pyrrolidine-1-carbonyl)-2,5-dihydro-1H-pyrrol-3-yl)phenyl)-6-oxo-1,6-dihydropyridine-3-carboxamide | 0.00222 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 630 | 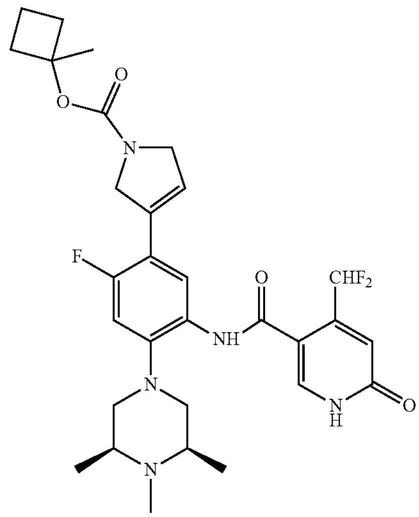 [SMILES: C[C@@H]1CN(c2cc(F)c(C3=CCN(C(=O)OC4(C)CCC4)C3)cc2NC(=O)c2c[nH]c(=O)cc2C(F)F)C[C@H](C)N1C] | 1-Methylcyclobutyl 3-(5-(4-(difluoromethyl)-6-oxo-1,6-dihydropyridine-3-carboxamido)-2-fluoro-4-((3S,5R)-3,4,5-trimethylpiperazin-1-yl)phenyl)-2,5-dihydro-1H-pyrrole-1-carboxylate | 0.00198 |
| 631 | 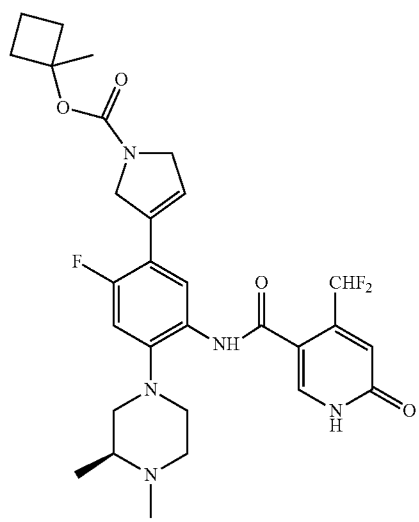 [SMILES: C[C@H]1CN(c2cc(F)c(C3=CCN(C(=O)OC4(C)CCC4)C3)cc2NC(=O)c2c[nH]c(=O)cc2C(F)F)CCN1C] | 1-Methylcyclobutyl (S)-3-(5-(4-(difluoromethyl)-6-oxo-1,6-dihydropyridine-3-carboxamido)-4-(3,4-dimethylpiperazin-1-yl)-2-fluorophenyl)-2,5-dihydro-1H-pyrrole-1-carboxylate | 0.00265 |
| 632 | 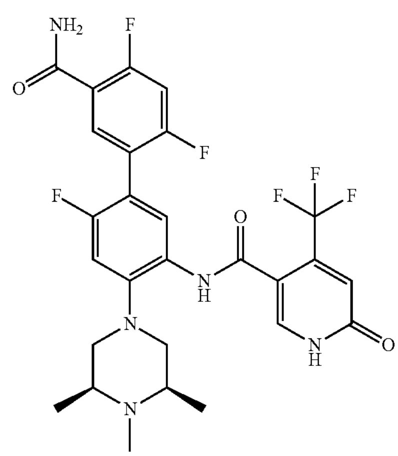 | N-[5-(5-carbamoyl-2,4-difluorophenyl)-4-fluoro-2-[rac-(3R,5S)-3,4,5-trimethylpiperazin-1-yl]phenyl]-6-oxo-4-(trifluoromethyl)-1H-pyridine-3-carboxamide | 0.0114 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 633 | 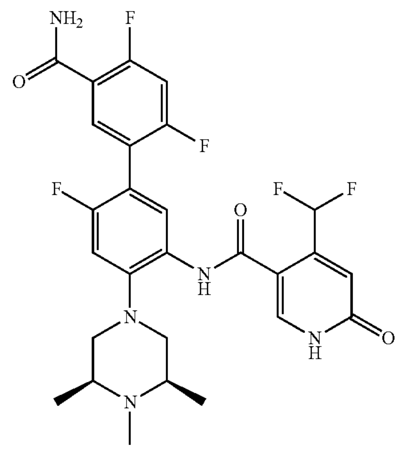 | N-[5-(5-carbamoyl-2,4-difluorophenyl)-4-fluoro-2-[rac-(3R,5S)-3,4,5-trimethylpiperazin-1-yl]phenyl]-4-(difluoromethyl)-6-oxo-1H-pyridine-3-carboxamide | 0.0119 |
| 634 | 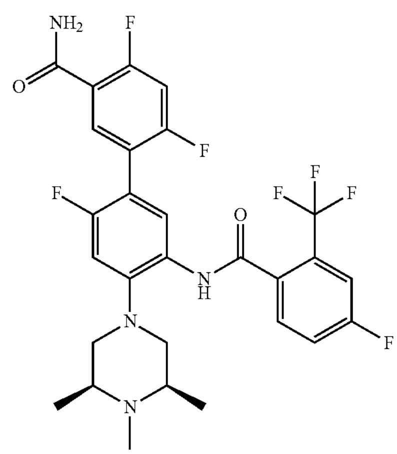 [SMILES: C[C@@H]1CN(c2cc(F)c(-c3cc(C(N)=O)c(F)cc3F)cc2NC(=O)c2ccc(F)cc2C(F)(F)F)C[C@H](C)N1C] | 2,4-difluoro-5-[2-fluoro-5-[[4-fluoro-2-(trifluoromethyl)benzoyl]amino]-4-[rac-(3R,5S)-3,4,5-trimethylpiperazin-1-yl]phenyl]benzamide | 0.0695 |
| 635 | 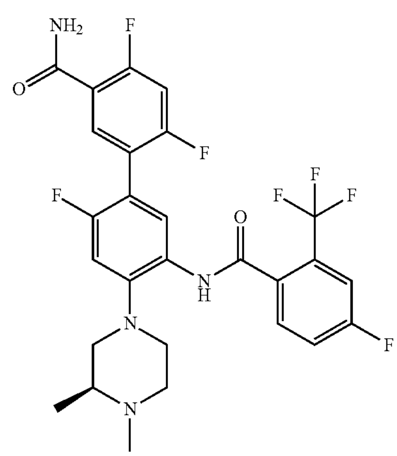 [SMILES: C[C@H]1CN(c2cc(F)c(-c3cc(C(N)=O)c(F)cc3F)cc2NC(=O)c2ccc(F)cc2C(F)(F)F)CCN1C] | 2,4-difluoro-5-[2-fluoro-5-[[4-fluoro-2-(trifluoromethyl)benzoyl]amino]-4-[rac-(3R)-3,4-dimethylpiperazin-1-yl]phenyl]benzamide | 0.0669 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 636 | 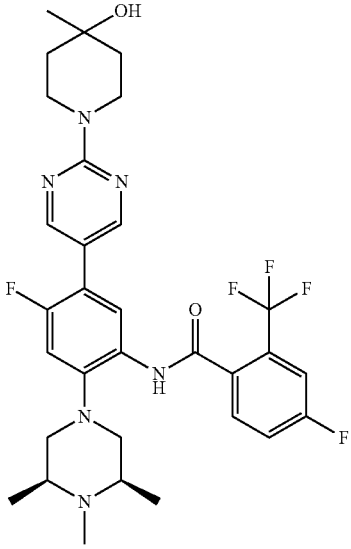 [SMILES: C[C@@H]1CN(c2cc(F)c(-c3cnc(N4CCC(C)(O)CC4)nc3)cc2NC(=O)c2ccc(F)cc2C(F)(F)F)C[C@H](C)N1C] | 4-fluoro-N-[4-fluoro-5-[2-(4-hydroxy-4-methylpiperidin-1-yl)pyrimidin-5-yl]-2-[rac-(3R,5S)-3,4,5-trimethylpiperazin-1-yl]phenyl]-2-(trifluoromethyl)benzamide | 0.00142 |
| 637 | 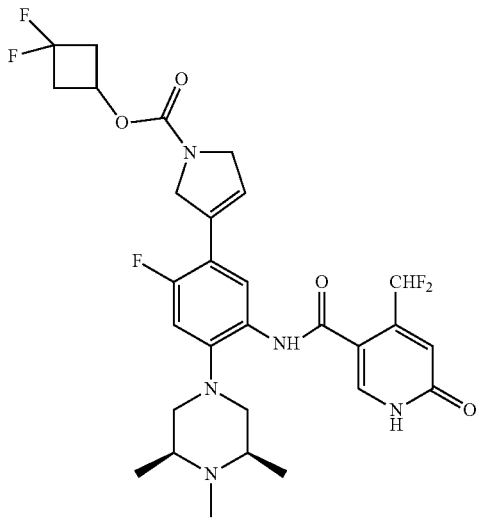 [SMILES: C[C@@H]1CN(c2cc(F)c(C3=CCN(C(=O)OC4CC(F)(F)C4)C3)cc2NC(=O)c2c[nH]c(=O)cc2C(F)F)C[C@H](C)N1C] | 3,3-Difluorocyclobutyl 3-(5-(4-(difluoromethyl)-6-oxo-1,6-dihydropyridine-3-carboxamido)-2-fluoro-4-((3S,5R)-3,4,5-trimethylpiperazin-1-yl)phenyl)-2,5-dihydro-1H-pyrrole-1-carboxylate | 0.00226 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 638 | 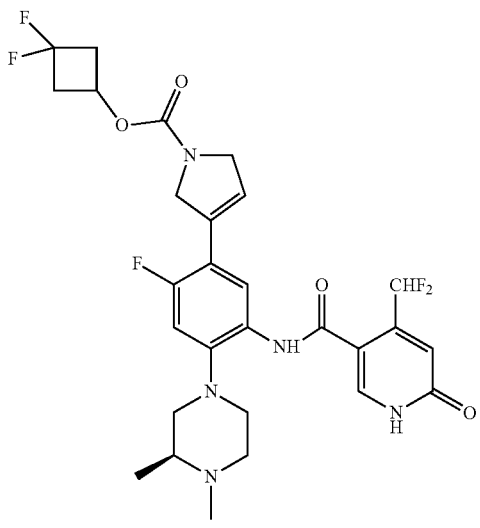 [SMILES: C[C@H]1CN(c2cc(F)c(C3=CCN(C(=O)OC4CC(F)(F)C4)C3)cc2NC(=O)c2c[nH]c(=O)cc2C(F)F)CCN1C] | 3,3-Difluorocyclobutyl (S)-3-(5-(4-(difluoromethyl)-6-oxo-1,6-dihydropyridine-3-carboxamido)-4-(3,4-dimethylpiperazin-1-yl)-2-fluorophenyl)-2,5-dihydro-1H-pyrrole-1-carboxylate | 0.00227 |
| 639 | 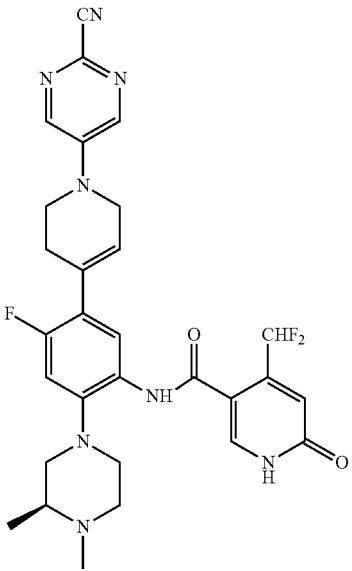 [SMILES: C[C@H]1CN(c2cc(F)c(C3=CCN(c4cnc(C#N)nc4)CC3)cc2NC(=O)c2c[nH]c(=O)cc2C(F)F)CCN1C] | (S)-N-(5-(1-(2-cyanopyrimidin-5-yl)-1,2,3,6-tetrahydropyridin-4-yl)-2-(3,4-dimethylpiperazin-1-yl)-4-fluorophenyl)-4-(difluoromethyl)-6-oxo-1,6-dihydropyridine-3-carboxamide | 0.00497 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 640 | 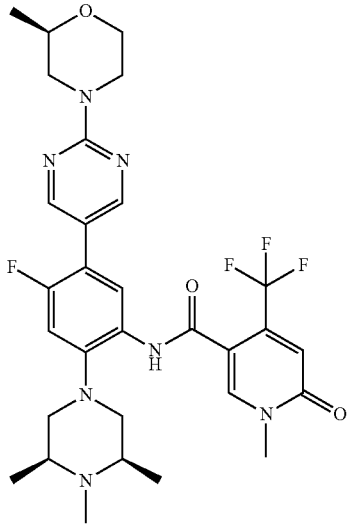 [SMILES: C[C@@H]1CN(c2ncc(-c3cc(NC(=O)c4cn(C)c(=O)cc4C(F)(F)F)c(N4C[C@@H](C)N(C)[C@@H](C)C4)cc3F)cn2)CCO1] | N-[4-fluoro-5-[2-[rac-(2R)-2-methylmorpholin-4-yl]pyrimidin-5-yl]-2-[rac-(3R,5S)-3,4,5-trimethylpiperazin-1-yl]phenyl]-1-methyl-6-oxo-4-(trifluoromethyl)pyridine-3-carboxamide | 0.00174 |
| 641 | 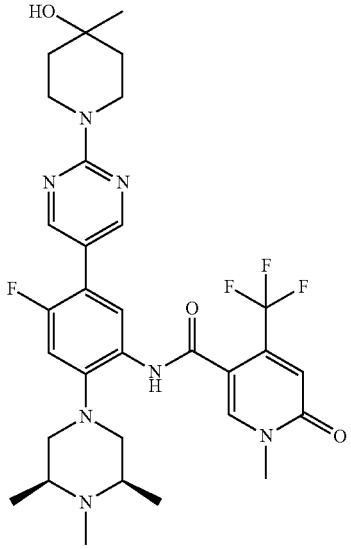 [SMILES: C[C@@H]1CN(c2cc(F)c(-c3cnc(N4CCC(C)(O)CC4)nc3)cc2NC(=O)c2cn(C)c(=O)cc2C(F)(F)F)C[C@H](C)N1C] | N-[4-fluoro-5-[2-(4-hydroxy-4-methylpiperidin-1-yl)pyrimidin-5-yl]-2-[rac-(3R,5S)-3,4,5-trimethylpiperazin-1-yl]phenyl]-1-methyl-6-oxo-4-(trifluoromethyl)pyridine-3-carboxamide | 0.00192 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 642 | 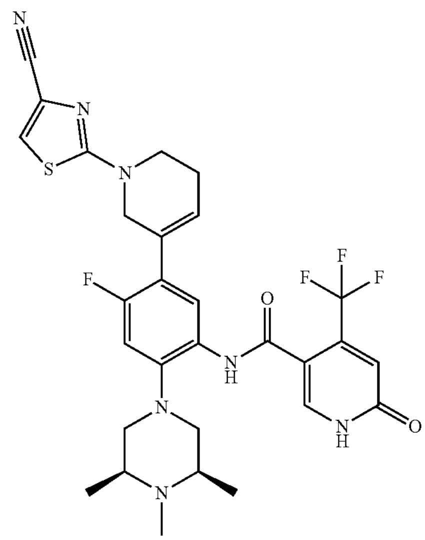 [SMILES: C[C@@H]1CN(c2cc(F)c(C3=CCCN(c4nc(C#N)cs4)C3)cc2NC(=O)c2c[nH]c(=O)cc2C(F)(F)F)C[C@H](C)N1C] | N-[5-[1-(4-cyano-1,3-thiazol-2-yl)-3,6-dihydro-2H-pyridin-5-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.0013 |
| 643 | 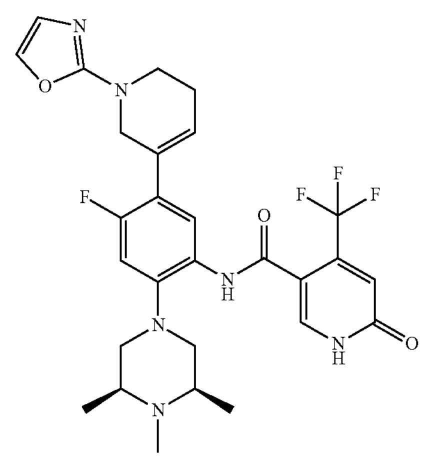 [SMILES: C[C@@H]1CN(c2cc(F)c(C3=CCCN(c4ncco4)C3)cc2NC(=O)c2c[nH]c(=O)cc2C(F)(F)F)C[C@H](C)N1C] | N-[4-fluoro-5-[1-(1,3-oxazol-2-yl)-3,6-dihydro-2H-pyridin-5-yl]-2-[rac-(3R,5S)-3,4,5-trimethylpiperazin-1-yl]phenyl]-6-oxo-4-(trifluoromethyl)-1H-pyridine-3-carboxamide | 0.00126 |
| 644 | 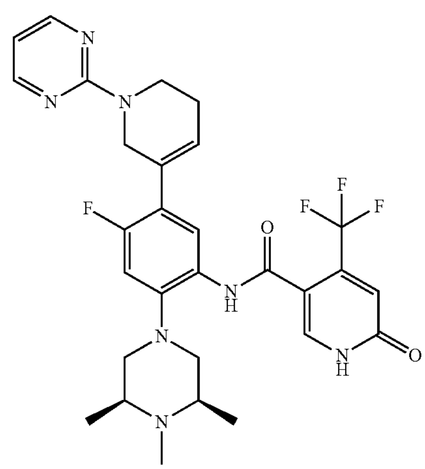 [SMILES: C[C@@H]1CN(c2cc(F)c(C3=CCCN(c4ncccn4)C3)cc2NC(=O)c2c[nH]c(=O)cc2C(F)(F)F)C[C@H](C)N1C] | 4-(difluoromethyl)-N-[4-fluoro-5-(1-pyrimidin-2-yl-3,6-dihydro-2H-pyridin-5-yl)-2-[rac-(3R,5S)-3,4,5-trimethylpiperazin-1-yl]phenyl]-6-oxo-1H-pyridine-3-carboxamide | 0.00132 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 645 | 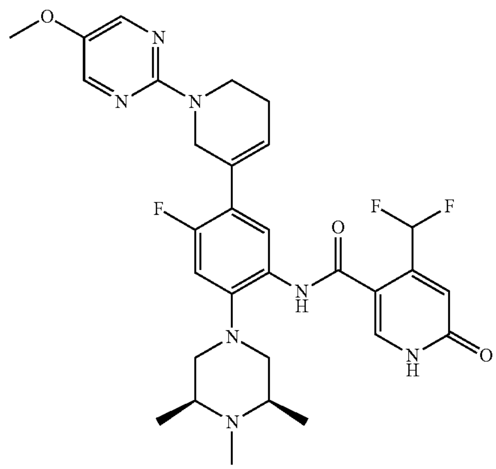 [SMILES: COc1cnc(N2CCC=C(c3cc(NC(=O)c4c[nH]c(=O)cc4C(F)F)c(N4C[C@@H](C)N(C)[C@@H](C)C4)cc3F)C2)nc1] | 4-(difluoromethyl)-N-[4-fluoro-5-[1-(5-methoxypyrimidin-2-yl)-3,6-dihydro-2H-pyridin-5-yl]-2-[rac-(3R,5S)-3,4,5-trimethylpiperazin-1-yl]phenyl]-6-oxo-1H-pyridine-3-carboxamide | 0.00141 |
| 646 | | 4-(difluoromethyl)-N-[4-fluoro-5-[1-(5-formylpyrimidin-2-yl)-3,6-dihydro-2H-pyridin-4-yl]-2-[rac-(3R,5S)-3,4,5-trimethylpiperazin-1-yl]phenyl]-6-oxo-1H-pyridine-3-carboxamide | 0.00141 | ns
TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 647 | 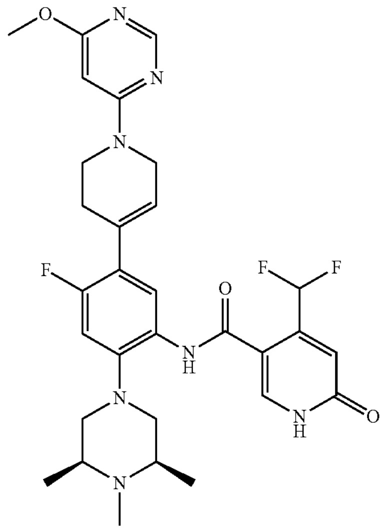 [SMILES: COc1cc(N2CC=C(c3cc(NC(=O)c4c[nH]c(=O)cc4C(F)F)c(N4C[C@@H](C)N(C)[C@@H](C)C4)cc3F)CC2)ncn1] | 4-(difluoromethyl)-N-[4-fluoro-5-[1-(6-methoxypyrimidin-4-yl)-3,6-dihydro-2H-pyridin-4-yl]-2-[rac-(3R,5S)-3,4,5-trimethylpiperazin-1-yl]phenyl]-6-oxo-1H-pyridine-3-carboxamide | 0.00159 |
| 648 | 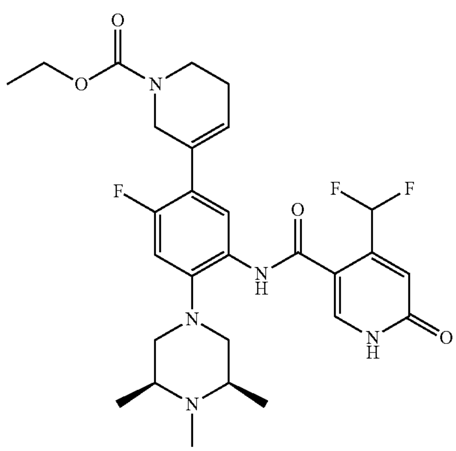 [SMILES: CCOC(=O)N1CCC=C(c2cc(NC(=O)c3c[nH]c(=O)cc3C(F)F)c(N3C[C@@H](C)N(C)[C@@H](C)C3)cc2F)C1] | ethyl 5-[5-[[4-((difluoromethyl)-6-oxo-1H-pyridine-3-carbonyl]amino]-2-fluoro-4-[rac-(3R,5S)-3,4,5-trimethylpiperazin-1-yl]phenyl]-3,6-dihydro-2H-pyridine-1-carboxylate | 0.00197 |
| 649 | 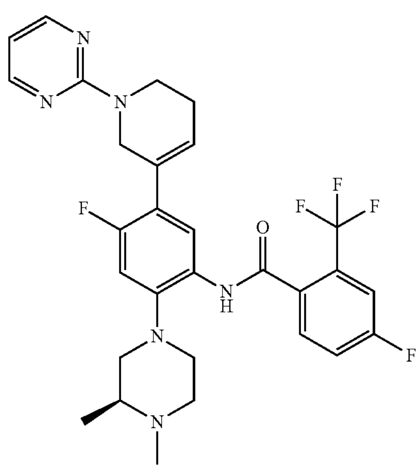 [SMILES: C[C@H]1CN(c2cc(F)c(C3=CCCN(c4ncccn4)C3)cc2NC(=O)c2ccc(F)cc2C(F)(F)F)CCN1C] | 4-fluoro-N-[4-fluoro-5-(1-pyrimidin-2-yl-3,6-dihydro-2H-pyridin-5-yl)-2-[rac-(3R)-3,4-dimethylpiperazin-1-yl]phenyl]-2-(trifluoromethyl)benzamide | 0.00187 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 650 | 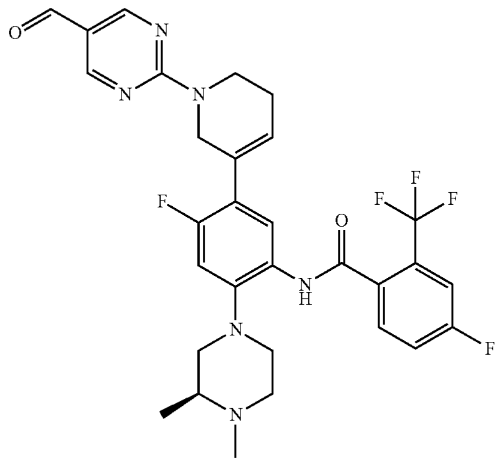 [SMILES: C[C@H]1CN(c2cc(F)c(C3=CCCN(c4ncc(C=O)cn4)C3)cc2NC(=O)c2ccc(F)cc2C(F)(F)F)CCN1C] | 4-fluoro-N-[4-fluoro-5-[1-(5-formylpyrimidin-2-yl)-3,6-dihydro-2H-pyridin-5-yl]-2-[rac-(3R)-3,4-dimethylpiperazin-1-yl]phenyl]-2-(trifluoromethyl)benzamide | 0.00518 |
| 651 | 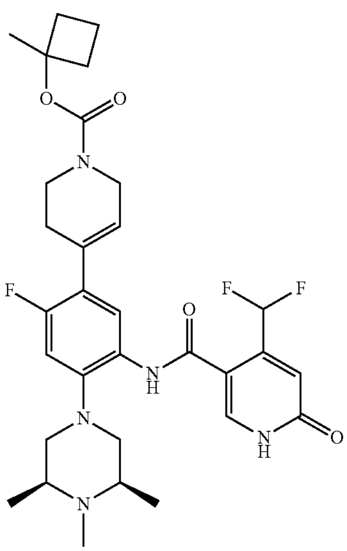 [SMILES: C[C@@H]1CN(c2cc(F)c(C3=CCN(C(=O)OC4(C)CCC4)CC3)cc2NC(=O)c2c[nH]c(=O)cc2C(F)F)C[C@H](C)N1C] | (1-methylcyclobutyl) 4-[5-[[4-(difluoromethyl)-6-oxo-1H-pyridine-3-carbonyl]amino]-2-fluoro-4-[rac-(3R,5S)-3,4,5-trimethylpiperazin-1-yl]phenyl]-3,6-dihydro-2H-pyridine-1-carboxylate | 0.000897 |
| 652 | 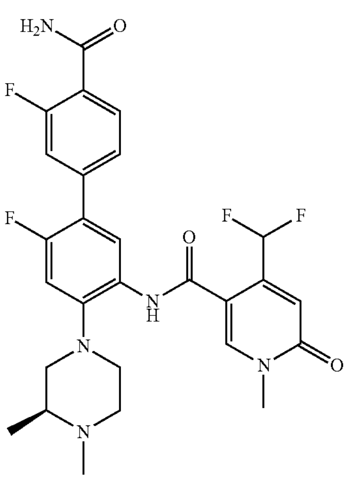 [SMILES: C[C@H]1CN(c2cc(F)c(-c3ccc(C(N)=O)c(F)c3)cc2NC(=O)c2cn(C)c(=O)cc2C(F)F)CCN1C] | N-[5-(4-carbamoyl-3-fluorophenyl)-4-fluoro-2-[rac-(3R)-3,4-dimethylpiperazin-1-yl]phenyl]-4-(difluoromethyl)-1-methyl-6-oxopyridine-3-carboxamide | 0.00529 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 653 | 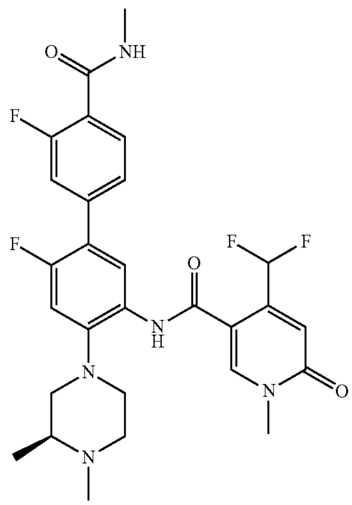 [SMILES: CNC(=O)c1ccc(-c2cc(NC(=O)c3cn(C)c(=O)cc3C(F)F)c(N3CCN(C)[C@@H](C)C3)cc2F)cc1F] | 4-(difluoromethyl)-N-[4-fluoro-5-[3-fluoro-4-(methylcarbamoyl)phenyl]-2-[rac-(3R)-3,4-dimethylpiperazin-1-yl]phenyl]-1-methyl-6-oxopyridine-3-carboxamide | 0.00343 |
| 654 | 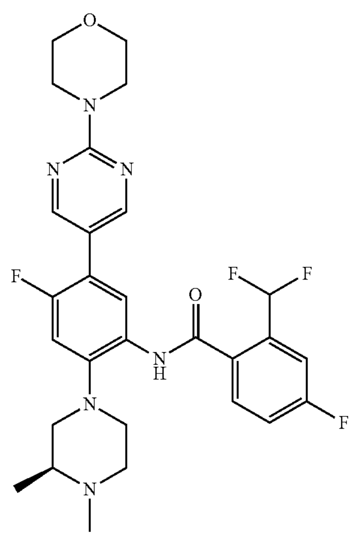 [SMILES: C[C@H]1CN(c2cc(F)c(-c3cnc(N4CCOCC4)nc3)cc2NC(=O)c2ccc(F)cc2C(F)F)CCN1C] | 2-(difluoromethyl)-4-fluoro-N-[4-fluoro-5-(2-morpholin-4-ylpyrimidin-5-yl)-2-[rac-(3R)-3,4-dimethylpiperazin-1-yl]phenyl]benzamide | — |
| 655 | 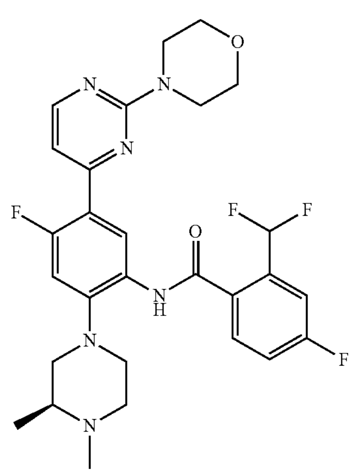 [SMILES: C[C@H]1CN(c2cc(F)c(-c3ccnc(N4CCOCC4)n3)cc2NC(=O)c2ccc(F)cc2C(F)F)CCN1C] | 2-(difluoromethyl)-4-fluoro-N-[4-fluoro-5-(2-morpholin-4-ylpyrimidin-4-yl)-2-[rac-(3R)-3,4-dimethylpiperazin-1-yl]phenyl]benzamide | 0.00106 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 656 | 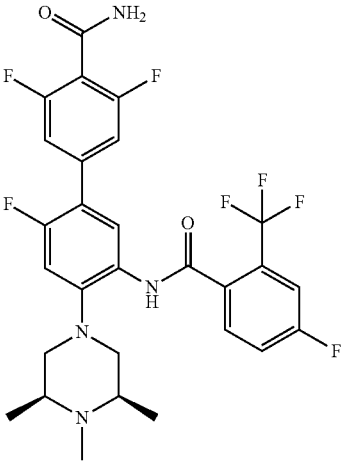 [SMILES: C[C@@H]1CN(c2cc(F)c(-c3cc(F)c(C(N)=O)c(F)c3)cc2NC(=O)c2ccc(F)cc2C(F)(F)F)C[C@H](C)N1C] | 2,6-difluoro-4-[2-fluoro-5-[[4-fluoro-2-(trifluoromethyl)benzoyl]amino]-4-[rac-(3R,5S)-3,4,5-trimethylpiperazin-1-yl]phenyl]benzamide | 0.00544 |
| 657 | 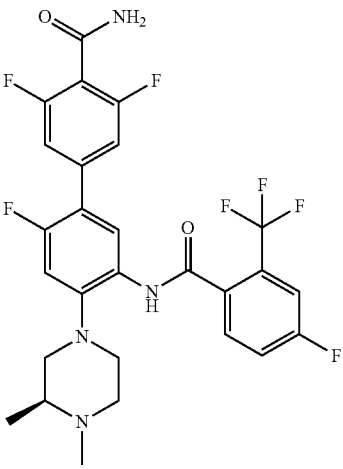 [SMILES: C[C@H]1CN(c2cc(F)c(-c3cc(F)c(C(N)=O)c(F)c3)cc2NC(=O)c2ccc(F)cc2C(F)(F)F)CCN1C] | 2,6-difluoro-4-[2-fluoro-5-[[4-fluoro-2-(trifluoromethyl)benzoyl]amino]-4-[rac-(3R)-3,4-dimethylpiperazin-1-yl]phenyl]benzamide | 0.00469 |
| 658 | 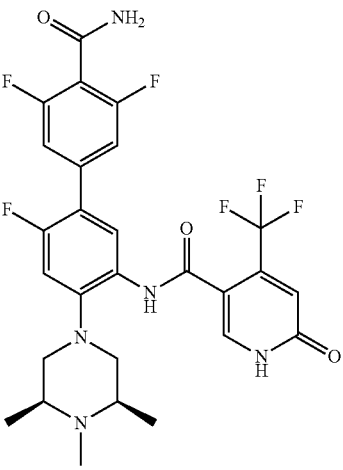 [SMILES: C[C@@H]1CN(c2cc(F)c(-c3cc(F)c(C(N)=O)c(F)c3)cc2NC(=O)c2c[nH]c(=O)cc2C(F)(F)F)C[C@H](C)N1C] | N-[5-(4-carbamoyl-3,5-difluorophenyl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00188 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 659 | 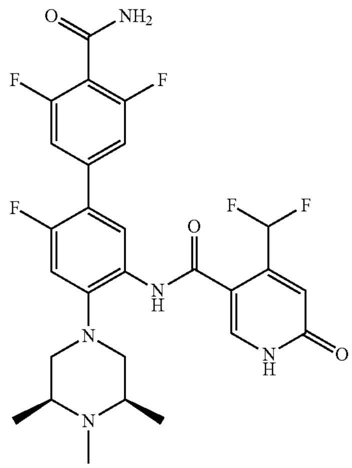 [SMILES: C[C@@H]1CN(c2cc(F)c(-c3cc(F)c(C(N)=O)c(F)c3)cc2NC(=O)c2c[nH]c(=O)cc2C(F)F)C[C@H](C)N1C] | N-[5-(4-carbamoyl-3,5-difluorophenyl)-4-fluoro-2-[rac-(3R,5S)-3,4,5-trimethylpiperazin-1-yl]phenyl]-4-(difluoromethyl)-6-oxo-1H-pyridine-3-carboxamide | 0.00193 |
| 660 | 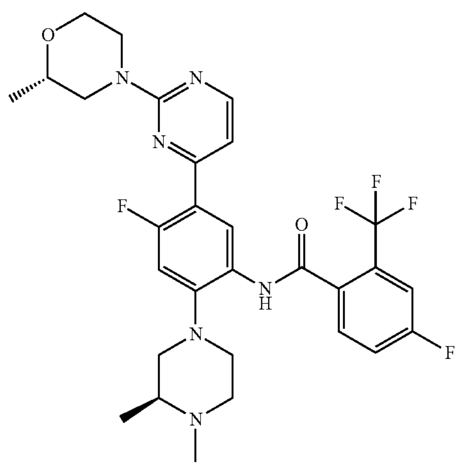 [SMILES: C[C@H]1CN(c2nccc(-c3cc(NC(=O)c4ccc(F)cc4C(F)(F)F)c(N4CCN(C)[C@@H](C)C4)cc3F)n2)CCO1] | 4-fluoro-N-[4-fluoro-2-[rac-(3R)-3,4-dimethylpiperazin-1-yl]-5-[2-[rac-(3R)-3-methylmorpholin-4-yl]pyrimidin-5-yl]phenyl]-2-(trifluoromethyl)benzamide | 0.00029 |
| 661 | 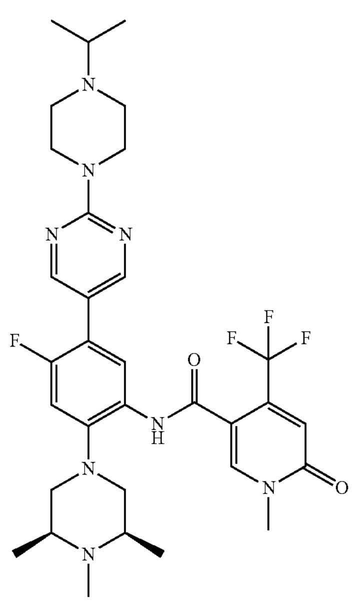 [SMILES: CC(C)N1CCN(c2ncc(-c3cc(NC(=O)c4cn(C)c(=O)cc4C(F)(F)F)c(N4C[C@@H](C)N(C)[C@@H](C)C4)cc3F)cn2)CC1] | N-[4-fluoro-5-[2-(4-propan-2-ylpiperazin-1-yl)pyrimidin-5-yl]-2-[rac-(3R,5S)-3,4,5-trimethylpiperazin-1-yl]phenyl]-1-methyl-6-oxo-4-(trifluoromethyl)pyridine-3-carboxamide | 0.00323 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 662 | 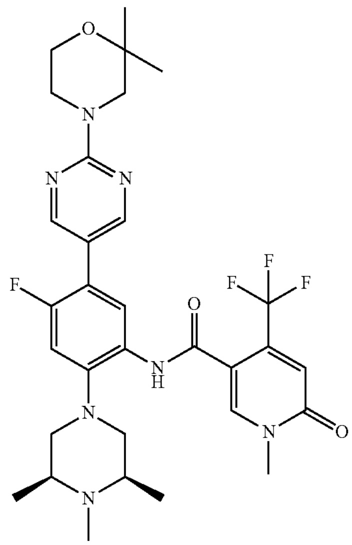 [SMILES: C[C@@H]1CN(c2cc(F)c(-c3cnc(N4CCOC(C)(C)C4)nc3)cc2NC(=O)c2cn(C)c(=O)cc2C(F)(F)F)C[C@H](C)N1C] | N-[5-[2-(2,2-dimethylmorpholin-4-yl)pyrimidin-5-yl]-4-fluoro-2-[rac-(3R,5S)-3,4,5-trimethylpiperazin-1-yl]phenyl]-1-methyl-6-oxo-4-(trifluoromethyl)pyridine-3-carboxamide | 0.00229 |
| 663 | 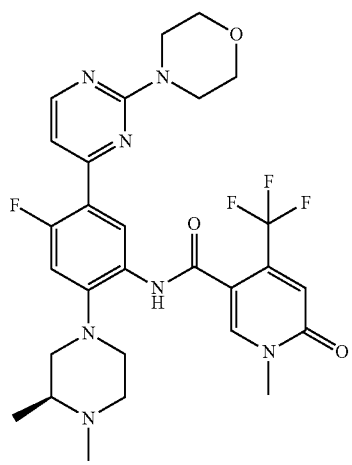 | N-[4-fluoro-5-(2-morpholin-4-ylpyrimidin-4-yl)-2-[rac-(3R)-3,4-dimethylpiperazin-1-yl]phenyl]-1-methyl-6-oxo-4-(trifluoromethyl)pyridine-3-carboxamide | 0.0025 |
| 664 | 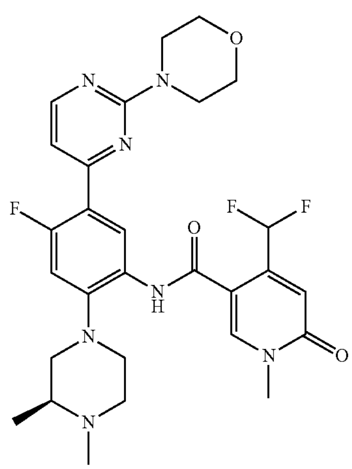 [SMILES: C[C@H]1CN(c2cc(F)c(-c3ccnc(N4CCOCC4)n3)cc2NC(=O)c2cn(C)c(=O)cc2C(F)F)CCN1C] | 4-(difluoromethyl)-N-[4-fluoro-5-(2-morpholin-4-ylpyrimidin-4-yl)-2-[rac-(3R)-3,4-dimethylpiperazin-1-yl]phenyl]-1-methyl-6-oxopyridine-3-carboxamide | 0.00268 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 665 | 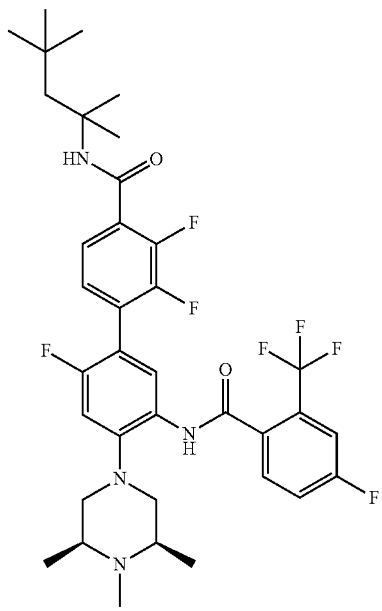 [SMILES: C[C@@H]1CN(c2cc(F)c(-c3ccc(C(=O)NC(C)(C)CC(C)(C)C)c(F)c3F)cc2NC(=O)c2ccc(F)cc2C(F)(F)F)C[C@H](C)N1C] | 2,3-difluoro-4-[2-fluoro-5-[[4-fluoro-2-(trifluoromethyl)benzoyl]amino]-4-[rac-(3R,5S)-3,4,5-trimethylpiperazin-1-yl]phenyl]-N-(2,4,4-trimethylpentan-2-yl)benzamide | 0.151 |
| 666 | 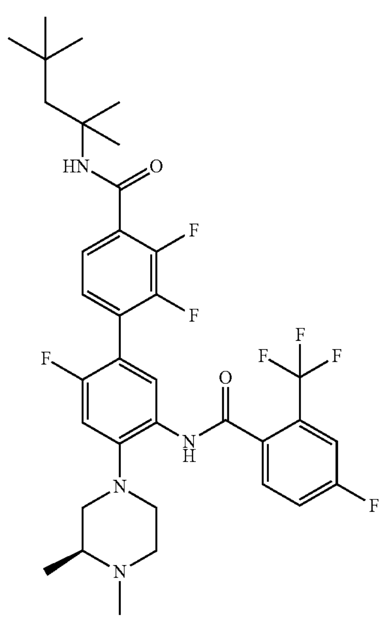 [SMILES: C[C@H]1CN(c2cc(F)c(-c3ccc(C(=O)NC(C)(C)CC(C)(C)C)c(F)c3F)cc2NC(=O)c2ccc(F)cc2C(F)(F)F)CCN1C] | 2,3-difluoro-4-[2-fluoro-5-[[4-fluoro-2-(trifluoromethyl)benzoyl]amino]-4-[rac-(3R)-3,4-dimethylpiperazin-1-yl]phenyl]-N-(2,4,4-trimethylpentan-2-yl)benzamide | 0.117 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 667 | 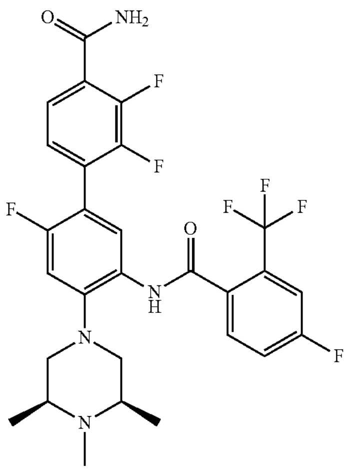 [SMILES: C[C@@H]1CN(c2cc(F)c(-c3ccc(C(N)=O)c(F)c3F)cc2NC(=O)c2ccc(F)cc2C(F)(F)F)C[C@H](C)N1C] | 2,3-difluoro-4-[2-fluoro-5-[[4-fluoro-2-(trifluoromethyl)benzoyl]amino]-4-[rac-(3R,5S)-3,4,5-trimethylpiperazin-1-yl]phenyl]benzamide | 0.00965 |
| 668 | 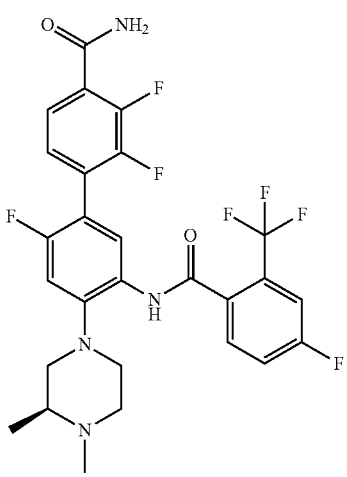 [SMILES: C[C@H]1CN(c2cc(F)c(-c3ccc(C(N)=O)c(F)c3F)cc2NC(=O)c2ccc(F)cc2C(F)(F)F)CCN1C] | 2,3-difluoro-4-[2-fluoro-5-[[4-fluoro-2-(trifluoromethyl)benzoyl]amino]-4-[rac-(3R)-3,4-dimethylpiperazin-1-yl]phenyl]benzamide | 0.0183 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 669 | 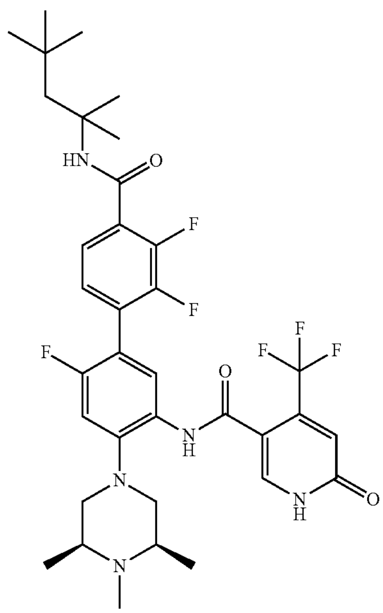 [SMILES: C[C@@H]1CN(c2cc(F)c(-c3ccc(C(=O)NC(C)(C)CC(C)(C)C)c(F)c3F)cc2NC(=O)c2c[nH]c(=O)cc2C(F)(F)F)C[C@H](C)N1C] | N-[5-[2,3-difluoro-4-(2,4,4-trimethylpentan-2-ylcarbamoyl)phenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00971 |
| 670 | 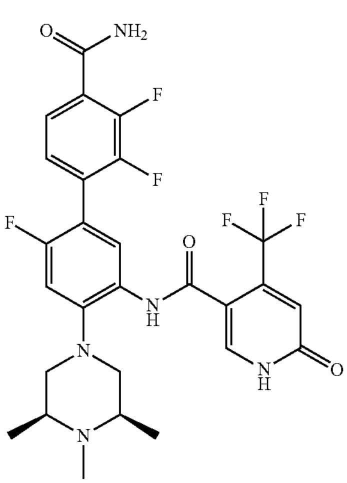 [SMILES: C[C@@H]1CN(c2cc(F)c(-c3ccc(C(N)=O)c(F)c3F)cc2NC(=O)c2c[nH]c(=O)cc2C(F)(F)F)C[C@H](C)N1C] | N-[5-(4-carbamoyl-2,3-difluorophenyl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00385 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 671 | 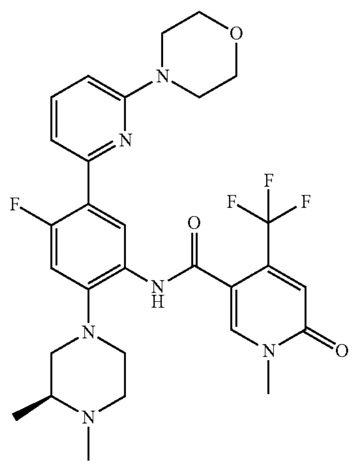 [SMILES: C[C@H]1CN(c2cc(F)c(-c3cccc(N4CCOCC4)n3)cc2NC(=O)c2cn(C)c(=O)cc2C(F)(F)F)CCN1C] | N-[4-fluoro-5-(6-morpholin-4-ylpyridin-2-yl)-2-[rac-(3R)-3,4-dimethylpiperazin-1-yl]phenyl]-1-methyl-6-oxo-4-(trifluoromethyl)pyridine-3-carboxamide | 0.00442 |
| 672 | 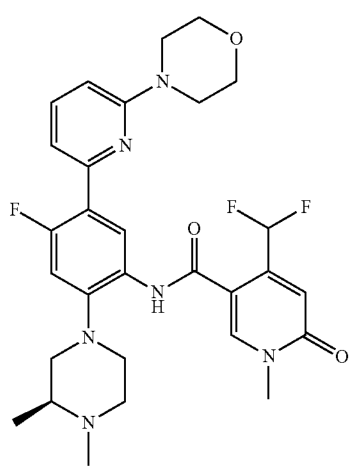 [SMILES: C[C@H]1CN(c2cc(F)c(-c3cccc(N4CCOCC4)n3)cc2NC(=O)c2cn(C)c(=O)cc2C(F)F)CCN1C] | 4-(difluoromethyl)-N-[4-fluoro-5-(6-morpholin-4-ylpyridin-2-yl)-2-[rac-(3R)-3,4-dimethylpiperazin-1-yl]phenyl]-1-methyl-6-oxopyridine-3-carboxamide | 0.00502 |
| 673 | 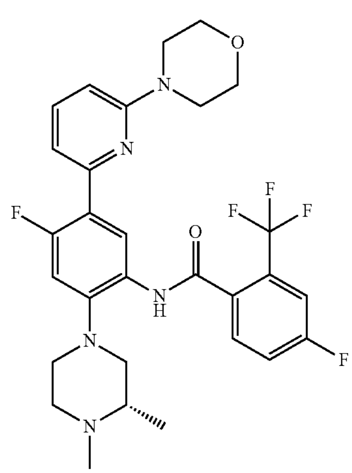 [SMILES: C[C@H]1CN(c2cc(F)c(-c3cccc(N4CCOCC4)n3)cc2NC(=O)c2ccc(F)cc2C(F)(F)F)CCN1C] | 4-fluoro-N-[4-fluoro-5-(6-morpholin-4-ylpyridin-2-yl)-2-[rac-(3R)-3,4-dimethylpiperazin-1-yl]phenyl]-2-(trifluoromethyl)benzamide | 0.00318 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 674 | 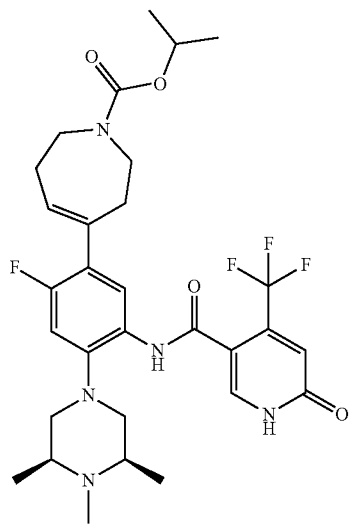 [SMILES: CC(C)OC(=O)N1CCC=C(c2cc(NC(=O)c3c[nH]c(=O)cc3C(F)(F)F)c(N3C[C@@H](C)N(C)[C@@H](C)C3)cc2F)CC1] | propan-2-yl 4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-2,3,6,7-tetrahydroazepine-1-carboxylate | 0.00494 |
| 675 | 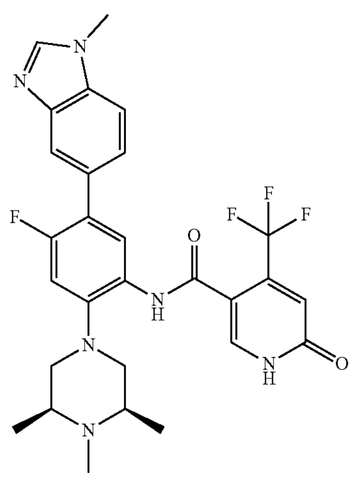 [SMILES: C[C@@H]1CN(c2cc(F)c(-c3ccc4c(c3)ncn4C)cc2NC(=O)c2c[nH]c(=O)cc2C(F)(F)F)C[C@H](C)N1C] | N-[4-fluoro-5-(1-methylbenzimidazol-5-yl)-2-[rac-(3R,5S)-3,4,5-trimethylpiperazin-1-yl]phenyl]-6-oxo-4-(trifluoromethyl)-1H-pyridine-3-carboxamide | 0.00197 |
| 676 | 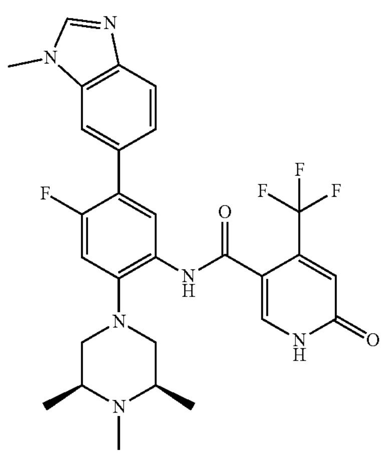 [SMILES: C[C@@H]1CN(c2cc(F)c(-c3ccc4ncn(C)c4c3)cc2NC(=O)c2c[nH]c(=O)cc2C(F)(F)F)C[C@H](C)N1C] | N-[4-fluoro-5-(3-methylbenzimidazol-5-yl)-2-[rac-(3R,5S)-3,4,5-trimethylpiperazin-1-yl]phenyl]-6-oxo-4-(trifluoromethyl)-1H-pyridine-3-carboxamide | 0.00439 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 677 | 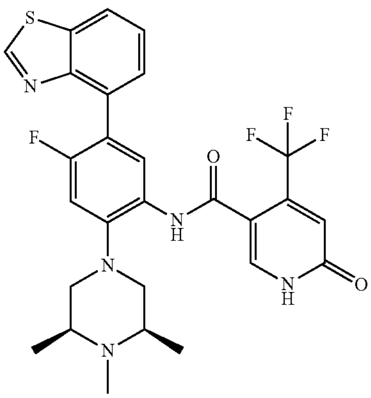 | N-[5-(1,3-benzothiazol-4-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00529 |
| 678 | 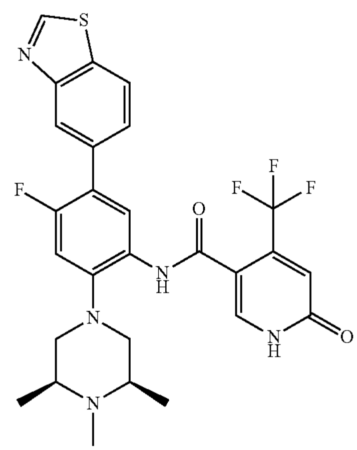 [SMILES: C[C@@H]1CN(c2cc(F)c(-c3ccc4scnc4c3)cc2NC(=O)c2c[nH]c(=O)cc2C(F)(F)F)C[C@H](C)N1C] | N-[5-(1,3-benzothiazol-5-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00326 |
| 679 | 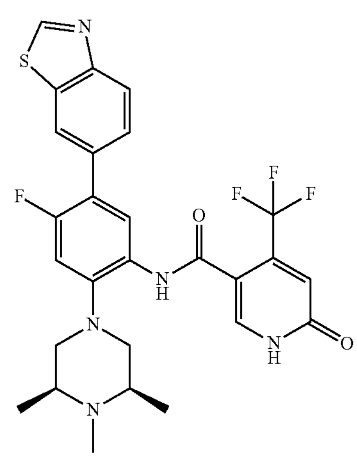 [SMILES: C[C@@H]1CN(c2cc(F)c(-c3ccc4ncsc4c3)cc2NC(=O)c2c[nH]c(=O)cc2C(F)(F)F)C[C@H](C)N1C] | N-[5-(1,3-benzothiazol-6-yl)-4-fluoro-2-[rac-(3R,5S)-3,4,5-trimethylpiperazin-1-yl]phenyl]-6-oxo-4-(trifluoromethyl)-1H-pyridine-3-carboxamide | 0.00297 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 680 | 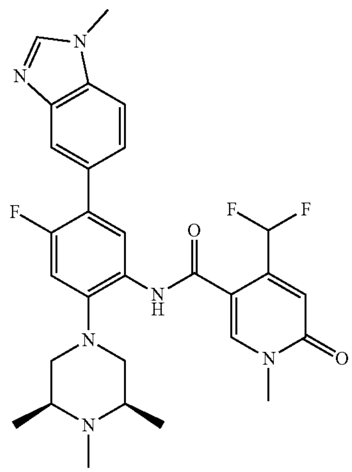 [SMILES: C[C@@H]1CN(c2cc(F)c(-c3ccc4c(c3)ncn4C)cc2NC(=O)c2cn(C)c(=O)cc2C(F)F)C[C@H](C)N1C] | 4-(difluoromethyl)-N-[4-fluoro-5-(1-methylbenzimidazol-5-yl)-2-[rac-(3R,5S)-3,4,5-trimethylpiperazin-1-yl]phenyl]-1-methyl-6-oxopyridine-3-carboxamide | 0.0582 |
| 681 | 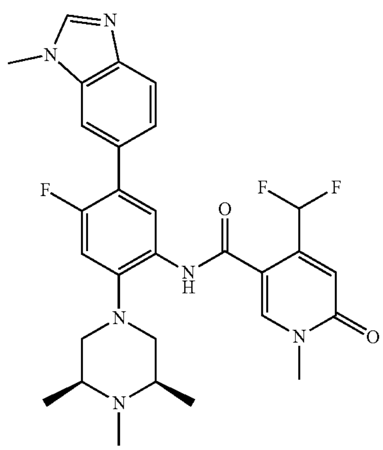 [SMILES: C[C@@H]1CN(c2cc(F)c(-c3ccc4ncn(C)c4c3)cc2NC(=O)c2cn(C)c(=O)cc2C(F)F)C[C@H](C)N1C] | 4-(difluoromethyl)-N-[4-fluoro-5-(3-methylbenzimidazol-5-yl)-2-[rac-(3R,5S)-3,4,5-trimethylpiperazin-1-yl]phenyl]-1-methyl-6-oxopyridine-3-carboxamide | 0.0393 |
| 682 | 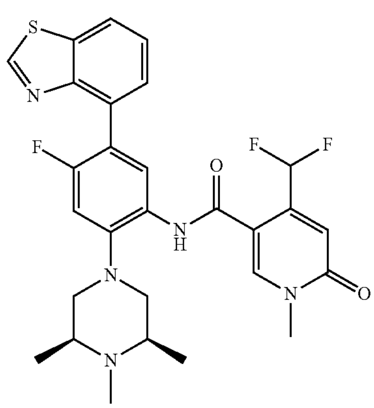 [SMILES: C[C@@H]1CN(c2cc(F)c(-c3cccc4scnc34)cc2NC(=O)c2cn(C)c(=O)cc2C(F)F)C[C@H](C)N1C] | N-[5-(1,3-benzothiazol-4-yl)-4-fluoro-2-[rac-(3R,5S)-3,4,5-trimethylpiperazin-1-yl]phenyl]-4-(difluoromethyl)-1-methyl-6-oxopyridine-3-carboxamide | 0.0204 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 683 | 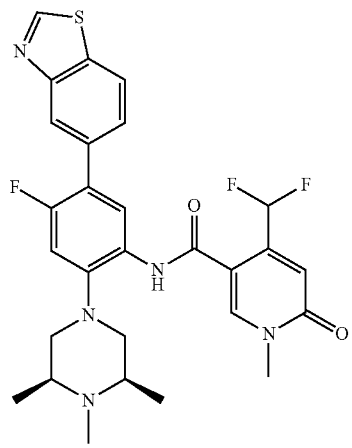 [SMILES: C[C@@H]1CN(c2cc(F)c(-c3ccc4scnc4c3)cc2NC(=O)c2cn(C)c(=O)cc2C(F)F)C[C@H](C)N1C] | N-[5-(1,3-benzothiazol-5-yl)-4-fluoro-2-[rac-(3R,5S)-3,4,5-trimethylpiperazin-1-yl]phenyl]-4-(difluoromethyl)-1-methyl-6-oxopyridine-3-carboxamide | 0.0123 |
| 684 | 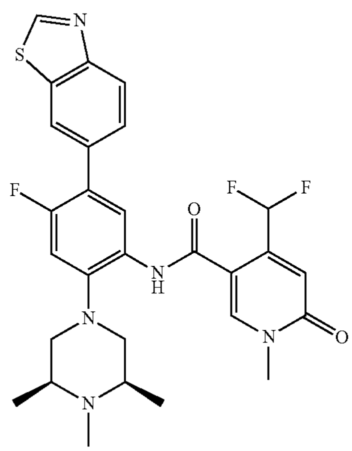 [SMILES: C[C@@H]1CN(c2cc(F)c(-c3ccc4ncsc4c3)cc2NC(=O)c2cn(C)c(=O)cc2C(F)F)C[C@H](C)N1C] | N-[5-(1,3-benzothiazol-6-yl)-4-fluoro-2-[rac-(3R,5S)-3,4,5-trimethylpiperazin-1-yl]phenyl]-4-(difluoromethyl)-1-methyl-6-oxopyridine-3-carboxamide | 0.00782 |
| 685 | 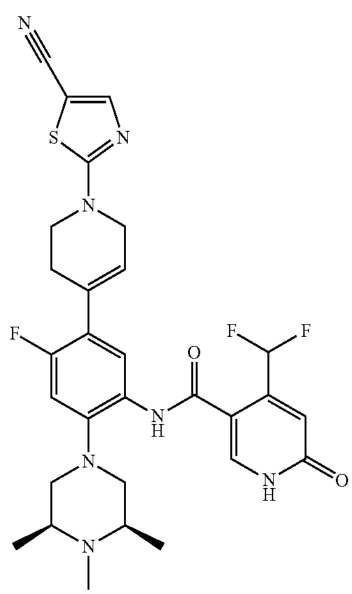 [SMILES: C[C@@H]1CN(c2cc(F)c(C3=CCN(c4ncc(C#N)s4)CC3)cc2NC(=O)c2c[nH]c(=O)cc2C(F)F)C[C@H](C)N1C] | N-[5-[1-(5-cyano-1,3-thiazol-2-yl)-3,6-dihydro-2H-pyridin-4-yl]-4-fluoro-2-[rac-(3R,5S)-3,4,5-trimethylpiperazin-1-yl]phenyl]-4-(difluoromethyl)-6-oxo-1H-pyridine-3-carboxamide | 0.00223 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 686 | 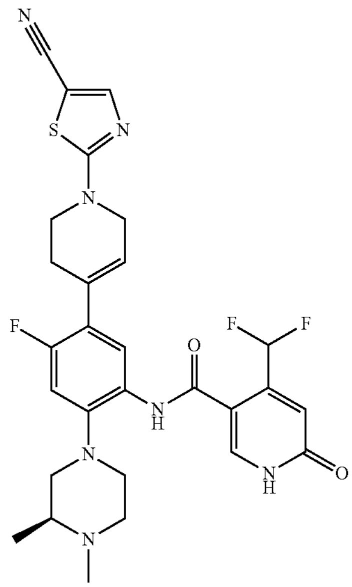 [SMILES: C[C@H]1CN(c2cc(F)c(C3=CCN(c4ncc(C#N)s4)CC3)cc2NC(=O)c2c[nH]c(=O)cc2C(F)F)CCN1C] | N-[5-[1-(5-cyano-1,3-thiazol-2-yl)-3,6-dihydro-2H-pyridin-4-yl]-4-fluoro-2-[rac-(3R)-3,4-dimethylpiperazin-1-yl]phenyl]-4-(difluoromethyl)-6-oxo-1H-pyridine-3-carboxamide | 0.00199 |
| 687 | 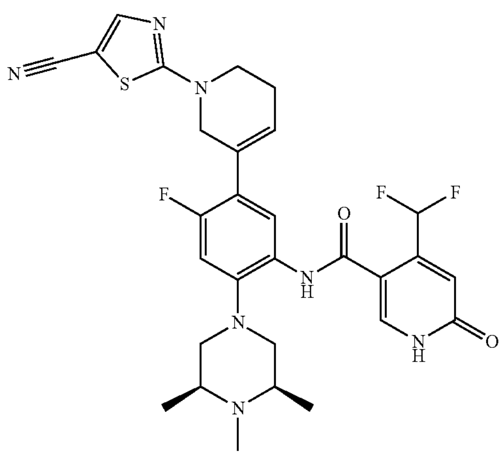 [SMILES: C[C@@H]1CN(c2cc(F)c(C3=CCCN(c4ncc(C#N)s4)C3)cc2NC(=O)c2c[nH]c(=O)cc2C(F)F)C[C@H](C)N1C] | N-[5-[1-(5-cyano-1,3-thiazol-2-yl)-3,6-dihydro-2H-pyridin-5-yl]-4-fluoro-2-[rac-(3R,5S)-3,4,5-trimethylpiperazin-1-yl]phenyl]-4-(difluoromethyl)-6-oxo-1H-pyridine-3-carboxamide | 0.00184 |
| 688 | 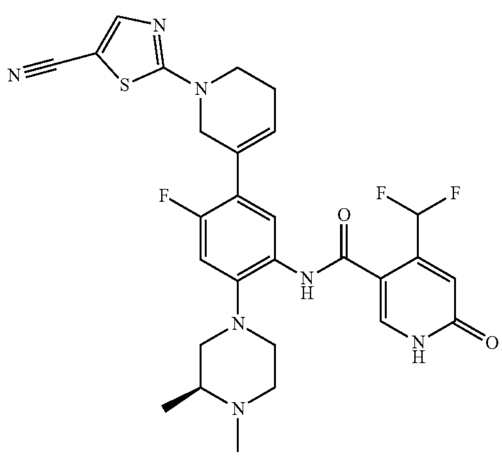 [SMILES: C[C@H]1CN(c2cc(F)c(C3=CCCN(c4ncc(C#N)s4)C3)cc2NC(=O)c2c[nH]c(=O)cc2C(F)F)CCN1C] | N-[5-[1-(5-cyano-1,3-thiazol-2-yl)-3,6-dihydro-2H-pyridin-5-yl]-4-fluoro-2-[rac-(3R)-3,4-dimethylpiperazin-1-yl]phenyl]-4-(difluoromethyl)-6-oxo-1H-pyridine-3-carboxamide | 0.00249 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 689 | 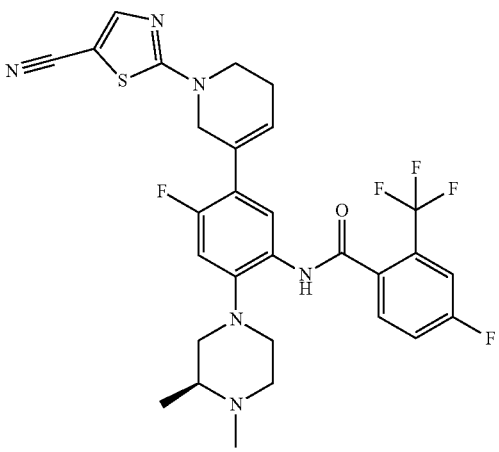 [SMILES: C[C@H]1CN(c2cc(F)c(C3=CCCN(c4ncc(C#N)s4)C3)cc2NC(=O)c2ccc(F)cc2C(F)(F)F)CCN1C] | N-[5-[1-(5-cyano-1,3-thiazol-2-yl)-3,6-dihydro-2H-pyridin-5-yl]-4-fluoro-2-[rac-(3R)-3,4-dimethylpiperazin-1-yl]phenyl]-4-fluoro-2-(trifluoromethyl)benzamide | 0.00628 |
| 690 | 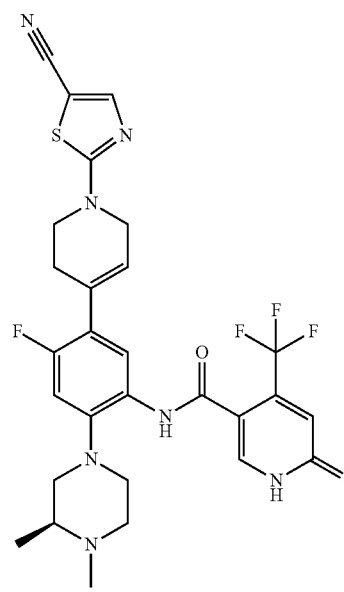 | N-[5-[1-(5-cyano-1,3-diazol-2-yl)-3,6-dihydro-2H-pyridin-4-yl]-4-fluoro-2-[rac-(3R)-3,4-dimethylpiperazin-1-yl]phenyl]-4-fluoro-2-(trifluoromethyl)benzamide | 0.00417 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 691 | 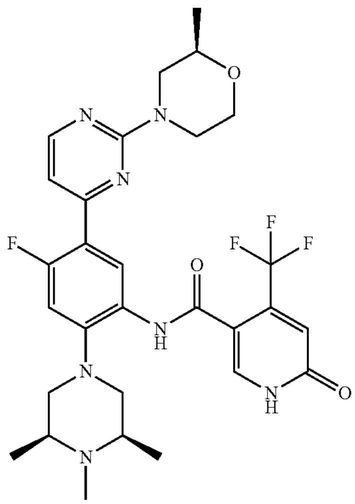 [SMILES: C[C@@H]1CN(c2nccc(-c3cc(NC(=O)c4c[nH]c(=O)cc4C(F)(F)F)c(N4C[C@@H](C)N(C)[C@@H](C)C4)cc3F)n2)CCO1] | N-[4-fluoro-5-[2-[rac-(2R)-2-methylmorpholin-4-yl]pyrimidin-4-yl]-2-[rac-(3R,5S)-3,4,5-trimethylpiperazin-1-yl]phenyl]-6-oxo-4-(trifluoromethyl)-1H-pyridine-3-carboxamide | 0.00131 |
| 692 | 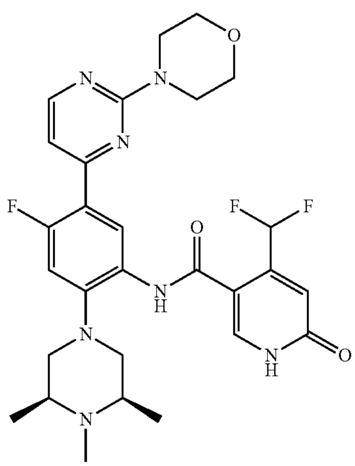 [SMILES: C[C@@H]1CN(c2cc(F)c(-c3ccnc(N4CCOCC4)n3)cc2NC(=O)c2c[nH]c(=O)cc2C(F)F)C[C@H](C)N1C] | 4-(difluoromethyl)-N-[4-fluoro-5-(2-morpholin-4-ylpyrimidin-4-yl)pyrimidin-4-yl]-2-[rac-(3R,5S)-3,4,5-trimethylpiperazin-1-yl]phenyl]-6-oxo-1H-pyridine-3-carboxamide | 0.0024 |
| 693 | 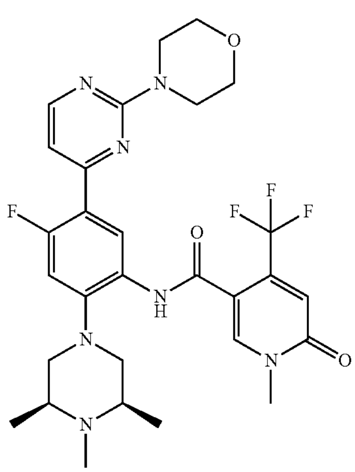 [SMILES: C[C@@H]1CN(c2cc(F)c(-c3ccnc(N4CCOCC4)n3)cc2NC(=O)c2cn(C)c(=O)cc2C(F)(F)F)C[C@H](C)N1C] | N-[4-fluoro-5-(2-morpholin-4-ylpyrimidin-4-yl)-2-[rac-(3R,5S)-3,4,5-trimethylpiperazin-1-yl]phenyl]-1-methyl-6-oxo-4-(trifluoromethyl)pyridine-3-carboxamide | 0.00479 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 694 | 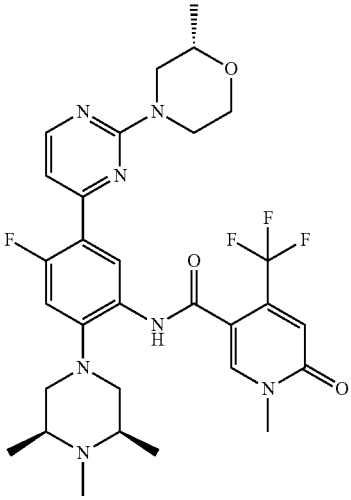 [SMILES: C[C@@H]1CN(c2cc(F)c(-c3ccnc(N4CCO[C@@H](C)C4)n3)cc2NC(=O)c2cn(C)c(=O)cc2C(F)(F)F)C[C@H](C)N1C] | N-[4-fluoro-5-[2-[rac-(2R)-2-methylmorpholin-4-yl]pyrimidin-4-yl]-2-[rac-(3S,5R)-3,4,5-trimethylpiperazin-1-yl]phenyl]-1-methyl-6-oxo-4-(trifluoromethyl)pyridine-3-carboxamide | 0.00492 |
| 695 | 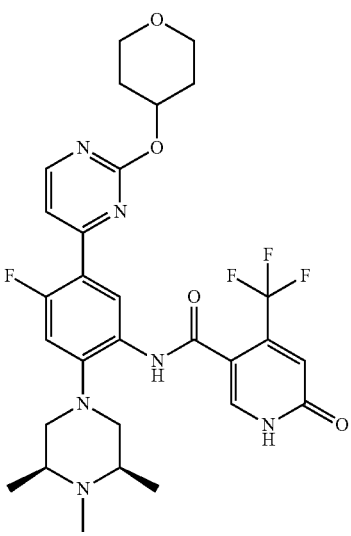 [SMILES: C[C@@H]1CN(c2cc(F)c(-c3ccnc(OC4CCOCC4)n3)cc2NC(=O)c2c[nH]c(=O)cc2C(F)(F)F)C[C@H](C)N1C] | N-[4-fluoro-5-[2-(oxan-4-yloxy)pyrimidin-4-yl]-2-[rac-(3R,5S)-3,4,5-trimethylpiperazin-1-yl]phenyl]-6-oxo-4-(trifluoromethyl)-1H-pyridine-3-carboxamide | 0.00253 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 696 | 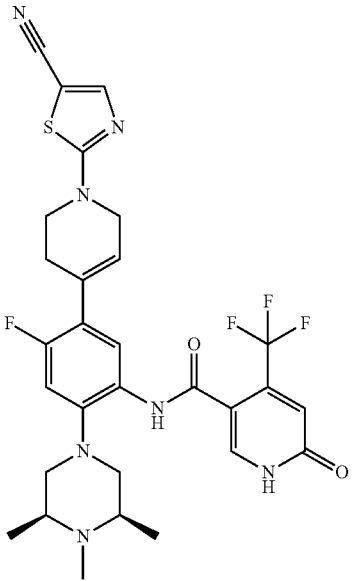 [SMILES: C[C@@H]1CN(c2cc(F)c(C3=CCN(c4ncc(C#N)s4)CC3)cc2NC(=O)c2c[nH]c(=O)cc2C(F)(F)F)C[C@H](C)N1C] | N-[5-[1-(5-cyano-1,3-thiazol-2-yl)-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00131 |
| 697 | 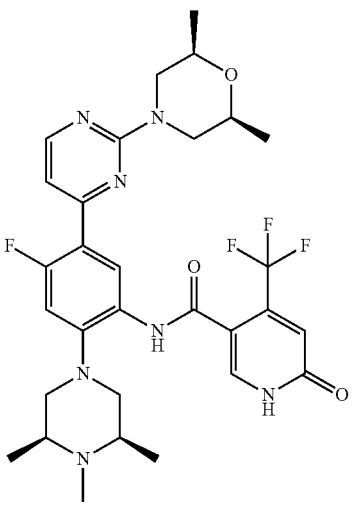 [SMILES: C[C@@H]1CN(c2nccc(-c3cc(NC(=O)c4c[nH]c(=O)cc4C(F)(F)F)c(N4C[C@@H](C)N(C)[C@@H](C)C4)cc3F)n2)C[C@H](C)O1] | N-[4-fluoro-5-[2-[rac-(2R,6S)-2,6-dimethylmorpholin-4-yl]pyrimidin-4-yl]-2-[rac-(3S,5R)-3,4,5-trimethylpiperazin-1-yl]phenyl]-6-oxo-4-(trifluoromethyl)-1H-pyridine-3-carboxamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 698 | 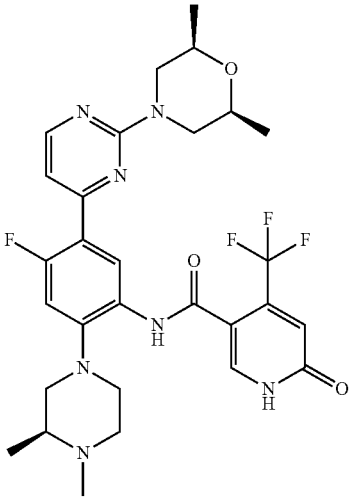 [SMILES: C[C@@H]1CN(c2nccc(-c3cc(NC(=O)c4c[nH]c(=O)cc4C(F)(F)F)c(N4CCN(C)[C@@H](C)C4)cc3F)n2)C[C@H](C)O1] | N-[4-fluoro-5-[2-[rac-(2R,6S)-2,6-dimethylmorpholin-4-yl]pyrimidin-4-yl]-2-[rac-(3R)-3,4-dimethylpiperazin-1-yl]phenyl]-6-oxo-4-(trifluoromethyl)-1H-pyridine-3-carboxamide | 0.00159 |
| 699 | 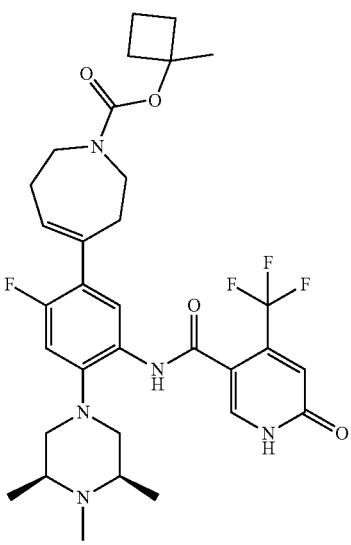 [SMILES: C[C@@H]1CN(c2cc(F)c(C3=CCCN(C(=O)OC4(C)CCC4)CC3)cc2NC(=O)c2c[nH]c(=O)cc2C(F)(F)F)C[C@H](C)N1C] | (1-methylcyclobutyl) 4-[2-fluoro-5-[[6-oxo-4-(trifluoromethyl)-1H-pyridine-3-carbonyl]amino]-4-[rac-(3R,5S)-3,4,5-trimethylpiperazin-1-yl]phenyl]-2,3,6,7-tetrahydroazepine-1-carboxylate | 0.0037 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 700 | 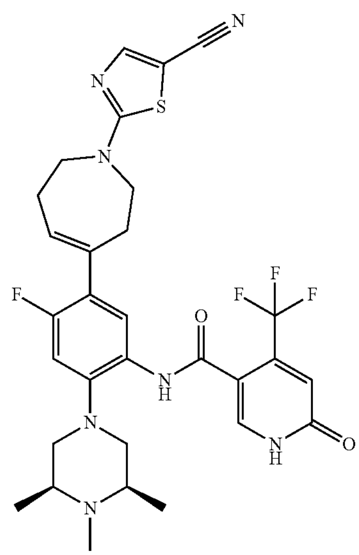 [SMILES: C[C@@H]1CN(c2cc(F)c(C3=CCCN(c4ncc(C#N)s4)CC3)cc2NC(=O)c2c[nH]c(=O)cc2C(F)(F)F)C[C@H](C)N1C] | N-[5-[1-(5-cyano-1,3-thiazol-2-yl)-2,3,6,7-tetrahydroazepin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00731 |
| 701 | 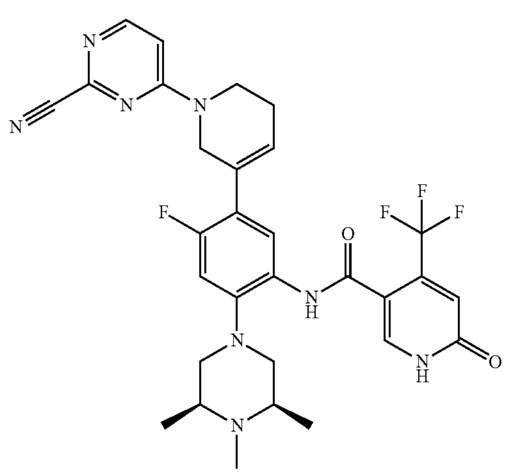 [SMILES: C[C@@H]1CN(c2cc(F)c(C3=CCCN(c4ccnc(C#N)n4)C3)cc2NC(=O)c2c[nH]c(=O)cc2C(F)(F)F)C[C@H](C)N1C] | N-[5-[1-(2-cyanopyrimidin-4-yl)-3,6-dihydro-2H-pyridin-5-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00173 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 702 | 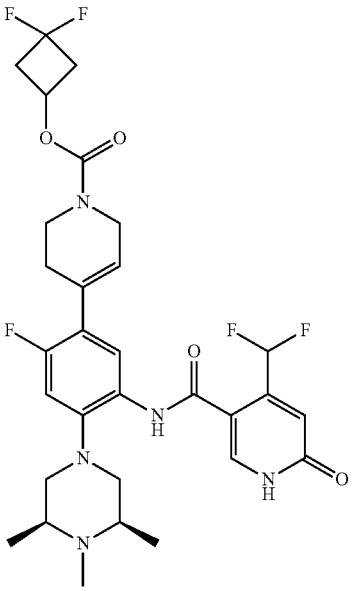 [SMILES: C[C@@H]1CN(c2cc(F)c(C3=CCN(C(=O)OC4CC(F)(F)C4)CC3)cc2NC(=O)c2c[nH]c(=O)cc2C(F)F)C[C@H](C)N1C] | (3,3-difluorocyclobutyl) 4-[5-[[4-(difluoromethyl)-6-oxo-1H-pyridine-3-carbonyl]amino]-2-fluoro-4-[rac-(3R,5S)-3,4,5-trimethylpiperazin-1-yl]phenyl]-3,6-dihydro-2H-pyridine-1-carboxylate | 0.00347 |
| 703 | 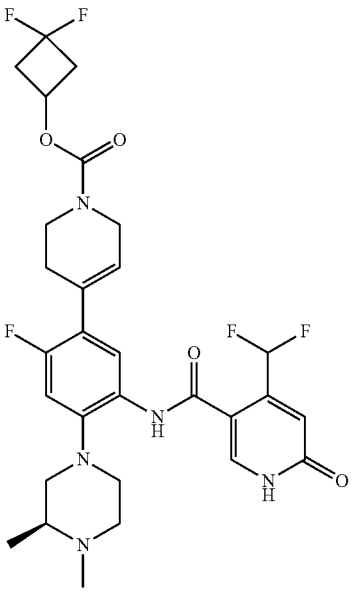 [SMILES: C[C@H]1CN(c2cc(F)c(C3=CCN(C(=O)OC4CC(F)(F)C4)CC3)cc2NC(=O)c2c[nH]c(=O)cc2C(F)F)CCN1C] | (3,3-difluorocyclobutyl) 4-[5-[[4-(difluoromethyl)-6-oxo-1H-pyridine-3-carbonyl]amino]-2-fluoro-4-[rac-(3R)-3,4-dimethylpiperazin-1-yl]phenyl]-3,6-dihydro-2H-pyridine-1-carboxylate | 0.00103 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 704 | 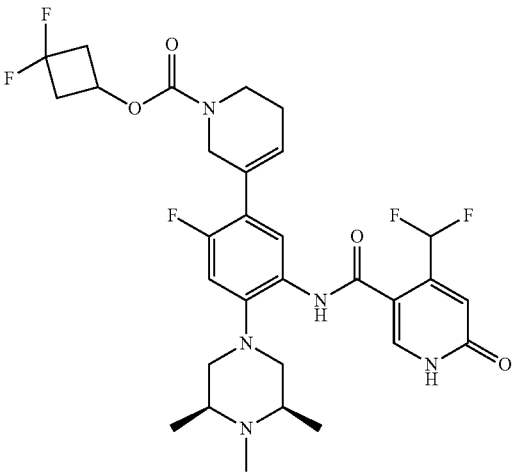 [SMILES: C[C@@H]1CN(c2cc(F)c(C3=CCCN(C(=O)OC4CC(F)(F)C4)C3)cc2NC(=O)c2c[nH]c(=O)cc2C(F)F)C[C@H](C)N1C] | (3,3-difluorocyclobutyl) 5-[5-[[4-(difluoromethyl)-6-oxo-1H-pyridine-3-carbonyl]amino]-2-fluoro-4-[rac-(3R,5S)-3,4,5-trimethylpiperazin-1-yl]phenyl]-3,6-dihydro-2H-pyridine-1-carboxylate | 0.00272 |
| 705 | 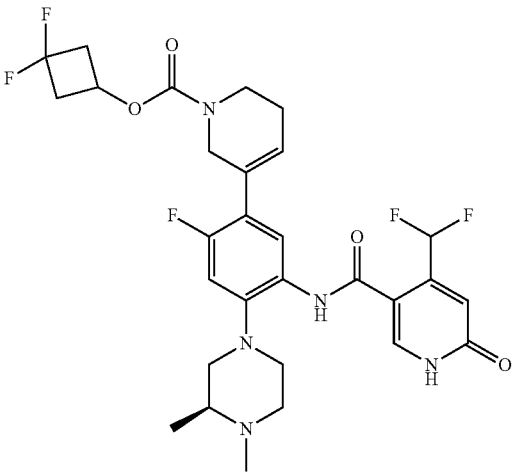 [SMILES: C[C@H]1CN(c2cc(F)c(C3=CCCN(C(=O)OC4CC(F)(F)C4)C3)cc2NC(=O)c2c[nH]c(=O)cc2C(F)F)CCN1C] | (3,3-difluorocyclobutyl) 5-[5-[[4-(difluoromethyl)-6-oxo-1H-pyridine-3-carbonyl]amino]-2-fluoro-4-[rac-(3R)-3,4-dimethylpiperazin-1-yl]phenyl]-3,6-dihydro-2H-pyridine-1-carboxylate | 0.00202 |
| 706 | 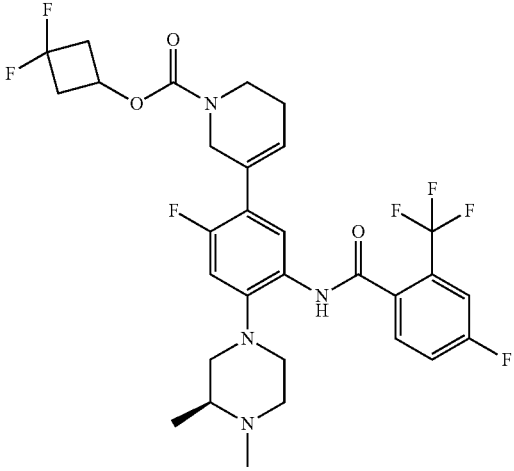 [SMILES: C[C@H]1CN(c2cc(F)c(C3=CCCN(C(=O)OC4CC(F)(F)C4)C3)cc2NC(=O)c2ccc(F)cc2C(F)(F)F)CCN1C] | (3,3-difluorocyclobutyl) 5-[2-fluoro-5-[[4-fluoro-2-(trifluoromethyl)benzoyl]amino]-4-[rac-(3R)-3,4-dimethylpiperazin-1-yl]phenyl]-3,6-dihydro-2H-pyridine-1-carboxylate | 0.00381 |

TABLE 1-continued

Binding affinities (K_D) derived from surface plasmon resonance (SPR) assays

| Example No. | Structure | IUPAC Name | WDR5 binding affinity ($K_D$, µM) |
|---|---|---|---|
| 707 | 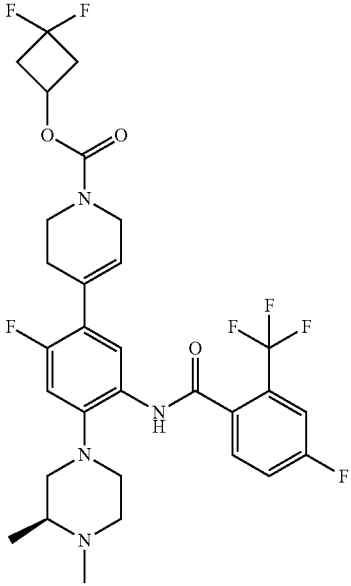 [SMILES: C[C@H]1CN(c2cc(F)c(C3=CCN(C(=O)OC4CC(F)(F)C4)CC3)cc2NC(=O)c2ccc(F)cc2C(F)(F)F)CCN1C] | (3,3-difluorocyclobutyl) 4-[2-fluoro-5-[[4-fluoro-2-(trifluoromethyl)benzoyl]amino]-4-[rac-(3R)-3,4-dimethylpiperazin-1-yl]phenyl]-3,6-dihydro-2H-pyridine-1-carboxylate | 0.00216 |
| 708 | 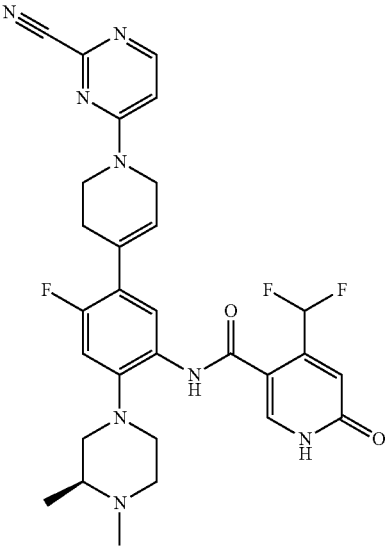 [SMILES: C[C@H]1CN(c2cc(F)c(C3=CCN(c4ccnc(C#N)n4)CC3)cc2NC(=O)c2c[nH]c(=O)cc2C(F)F)CCN1C] | N-[5-[1-(2-cyanopyrimidin-4-yl)-3,6-dihydro-2H-pyridin-4-yl]-4-fluoro-2-[rac-(3R)-3,4-dimethylpiperazin-1-yl]phenyl]-4-(difluoromethyl)-6-oxo-1H-pyridine-3-carboxamide | 0.00058 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 709 | 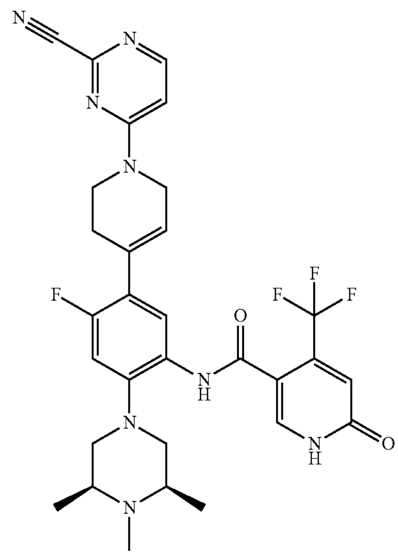 [SMILES: C[C@@H]1CN(c2cc(F)c(C3=CCN(c4ccnc(C#N)n4)CC3)cc2NC(=O)c2c[nH]c(=O)cc2C(F)(F)F)C[C@H](C)N1C] | N-[5-[1-(2-cyanopyrimidin-4-yl)-3,6-dihydro-2H-pyridin-4-yl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00072 |
| 710 | 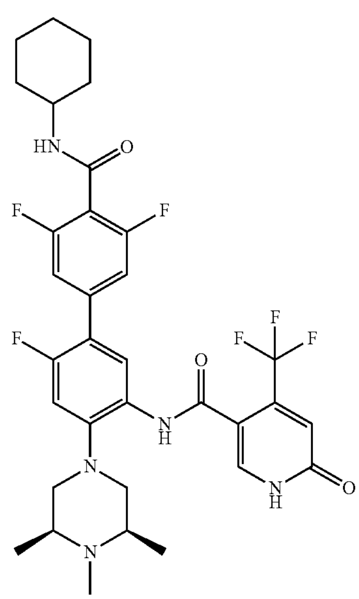 [SMILES: C[C@@H]1CN(c2cc(F)c(-c3cc(F)c(C(=O)NC4CCCCC4)c(F)c3)cc2NC(=O)c2c[nH]c(=O)cc2C(F)(F)F)C[C@H](C)N1C] | N-[5-[4-(cyclohexylcarbamoyl)-3,5-difluorophenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00203 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 711 | 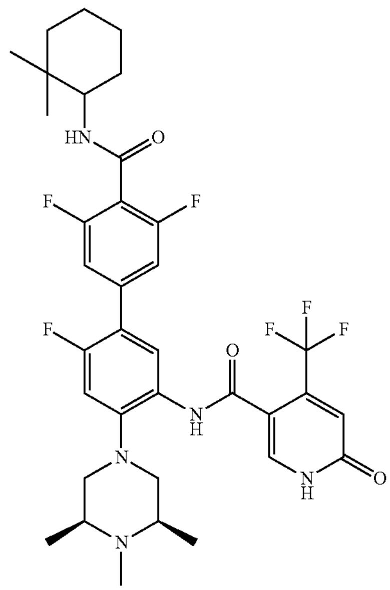 [SMILES: C[C@@H]1CN(c2cc(F)c(-c3cc(F)c(C(=O)NC4CCCCC4(C)C)c(F)c3)cc2NC(=O)c2c[nH]c(=O)cc2C(F)(F)F)C[C@H](C)N1C] | N-[5-[4-[(2,2-dimethylcyclohexyl)carbamoyl]-3,5-difluorophenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00317 |
| 712 | 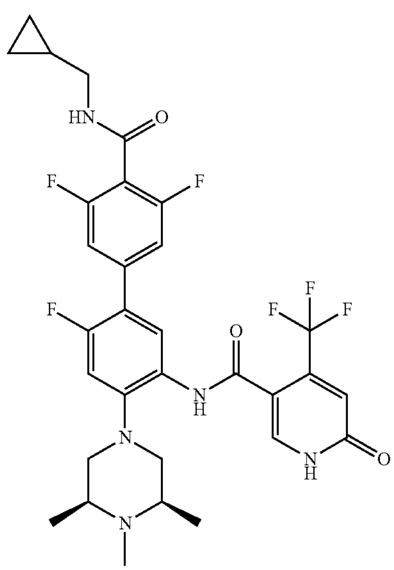 [SMILES: C[C@@H]1CN(c2cc(F)c(-c3cc(F)c(C(=O)NCC4CC4)c(F)c3)cc2NC(=O)c2c[nH]c(=O)cc2C(F)(F)F)C[C@H](C)N1C] | N-[5-[4-(cyclopropylmethylcarbamoyl)-3,5-difluorophenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00223 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 713 | 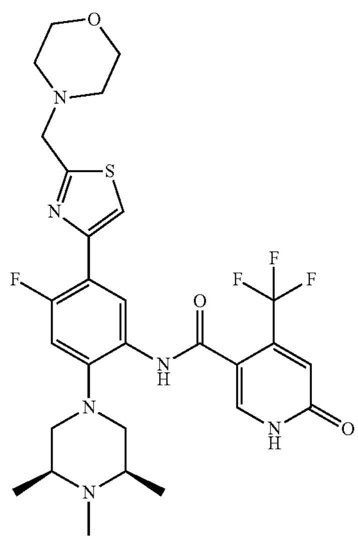 [SMILES: C[C@@H]1CN(c2cc(F)c(-c3csc(CN4CCOCC4)n3)cc2NC(=O)c2c[nH]c(=O)cc2C(F)(F)F)C[C@H](C)N1C] | N-[4-fluoro-5-[2-(morpholin-4-ylmethyl)-1,3-thiazol-4-yl]-2-[rac-(3R,5S)-3,4,5-trimethylpiperazin-1-yl]phenyl]-6-oxo-4-(trifluoromethyl)-1H-pyridine-3-carboxamide | 0.00259 |
| 714 | 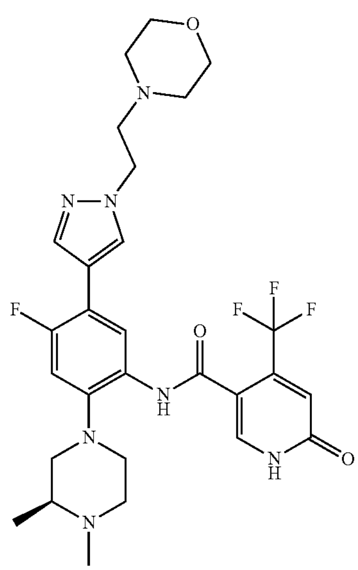 [SMILES: C[C@H]1CN(c2cc(F)c(-c3cnn(CCN4CCOCC4)c3)cc2NC(=O)c2c[nH]c(=O)cc2C(F)(F)F)CCN1C] | N-[4-fluoro-5-[1-(2-morpholin-4-ylethyl)pyrazol-4-yl]-2-[rac-(3R)-3,4-dimethylpiperazin-1-yl]phenyl]-6-oxo-4-(trifluoromethyl)-1H-pyridine-3-carboxamide | 0.00276 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 715 | 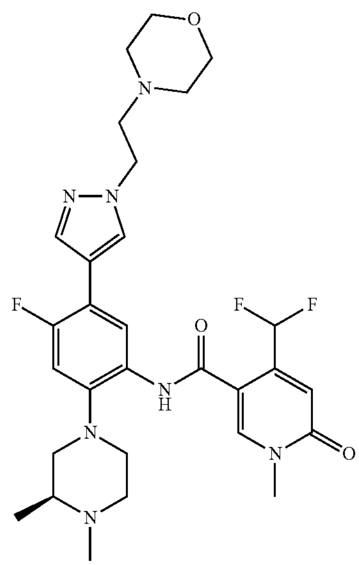 [SMILES: C[C@H]1CN(c2cc(F)c(-c3cnn(CCN4CCOCC4)c3)cc2NC(=O)c2cn(C)c(=O)cc2C(F)F)CCN1C] | 4-(difluoromethyl)-N-[4-fluoro-5-[1-(2-morpholin-4-ylethyl)pyrazol-4-yl]-2-[rac-(3R)-3,4-dimethylpiperazin-1-yl]phenyl]-1-methyl-6-oxopyridine-3-carboxamide | 0.01092 |
| 716 | 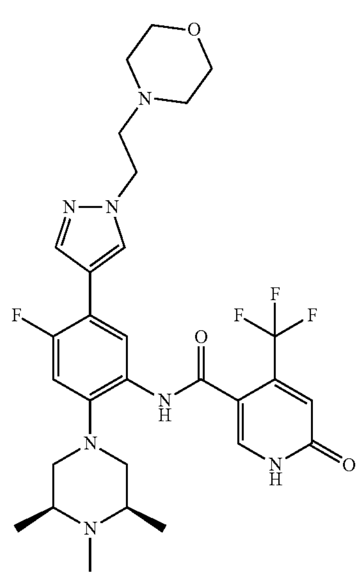 [SMILES: C[C@@H]1CN(c2cc(F)c(-c3cnn(CCN4CCOCC4)c3)cc2NC(=O)c2c[nH]c(=O)cc2C(F)(F)F)C[C@H](C)N1C] | N-[4-fluoro-5-[1-(2-morpholin-4-ylethyl)pyrazol-4-yl]-2-[rac-(3R,5S)-3,4?5-trimethylpiperazin-1-yl]phenyl]-6-oxo-4-(trifluoromethyl)-1H-pyridine-3-carboxamide | 0.00242 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 717 | 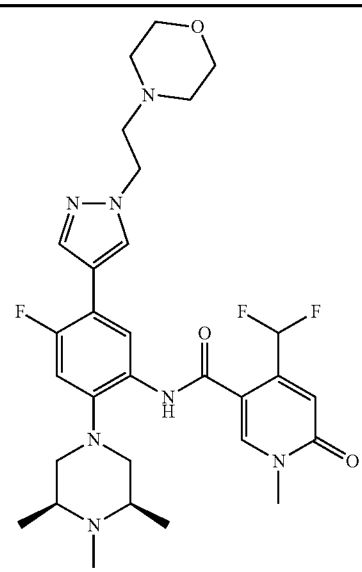 | 4-(difluoromethyl)-N-[4-fluoro-5-[1-(2-morpholin-4-ylethyl)pyrazol-4-yl]-2-[rac-(3R,5S)-3,4,5-trimethylpiperazin-1-yl]phenyl]-1-methyl-6-oxopyridine-3-carboxamide | 0.02157 |
| 718 | 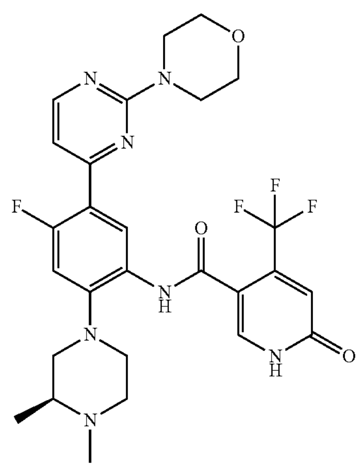 | N-[4-fluoro-5-(2-morpholin-4-ylpyrimidin-4-yl)-2-[rac-(3R)-3,4-dimethylpiperazin-1-yl]phenyl]-6-oxo-4-(trifluoromethyl)-1H-pyridine-3-carboxamide | 0.00109 |
| 719 | 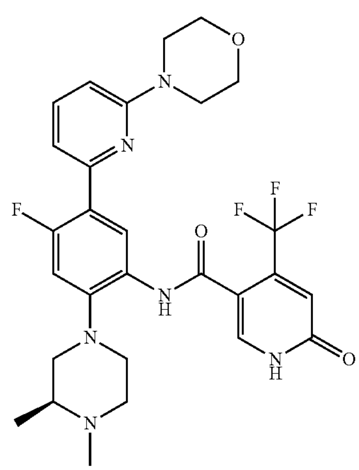 | N-[4-fluoro-5-(6-morpholin-4-ylpyridin-2-yl)-2-[rac-(3R)-3,4-dimethylpiperazin-1-yl]phenyl]-6-oxo-4-(trifluoromethyl)-1H-pyridine-3-carboxamide | 0.00118 |

TABLE 1-continued

Binding affinities ($K_D$) derived from surface plasmon resonance (SPR) assays

| Example No. | Structure | IUPAC Name | WDR5 binding affinity ($K_D$, μM) |
|---|---|---|---|
| 720 | 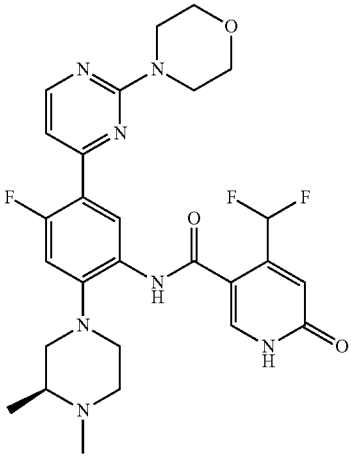 [SMILES: C[C@H]1CN(c2cc(F)c(-c3ccnc(N4CCOCC4)n3)cc2NC(=O)c2c[nH]c(=O)cc2C(F)F)CCN1C] | 4-(difluoromethyl)-N-[4-fluoro-5-(2-morpholin-4-ylpyrimidin-4-yl)-2-[rac-(3R)-3,4-dimethylpiperazin-1-yl]phenyl]-6-oxo-1H-pyridine-3-carboxamide | 0.00131 |
| 721 | 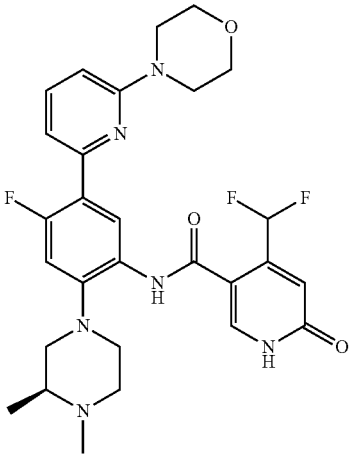 [SMILES: C[C@H]1CN(c2cc(F)c(-c3cccc(N4CCOCC4)n3)cc2NC(=O)c2c[nH]c(=O)cc2C(F)F)CCN1C] | 4-(difluoromethyl)-N-[4-fluoro-5-(6-morpholin-4-ylpyridin-2-yl)-2-[rac-(3R)-3,4-dimethylpiperazin-1-yl]phenyl]-6-oxo-1H-pyridine-3-carboxamide | 0.00162 |
| 722 | 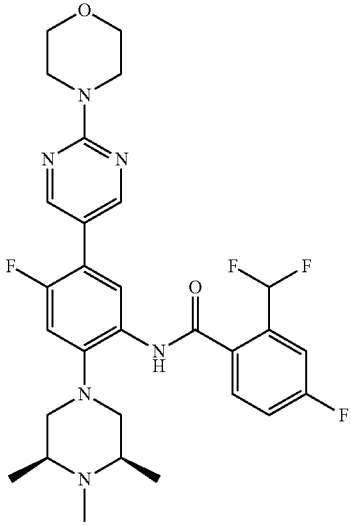 | 2-(difluoromethyl)-4-fluoro-N-[4-fluoro-5-(2-morpholin-4-ylpyrimidin-5-yl)-2-[rac-(3R,5S)-3,4,5-trimethylpiperazin-1-yl]phenyl]benzamide | 0.00136 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 723 | 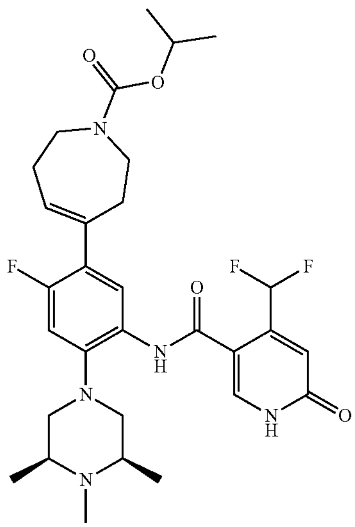 [SMILES: CC(C)OC(=O)N1CCC=C(c2cc(NC(=O)c3c[nH]c(=O)cc3C(F)F)c(N3C[C@@H](C)N(C)[C@@H](C)C3)cc2F)CC1] | propan-2-yl 4-[5-[[4-(difluoromethyl)-6-oxo-1H-pyridine-3-carbonyl]amino]-2-fluoro-4-[rac-(3R,5S)-3,4,5-trimethylpiperazin-1-yl]phenyl]-2,3,6,7-tetrahydroazepine-1-carboxylate | 0.00312 |
| 724 | 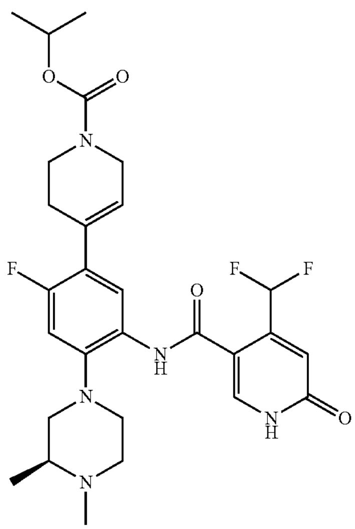 [SMILES: CC(C)OC(=O)N1CC=C(c2cc(NC(=O)c3c[nH]c(=O)cc3C(F)F)c(N3CCN(C)[C@@H](C)C3)cc2F)CC1] | propan-2-yl 4-[5-[[4-(difluoromethyl)-6-oxo-1H-pyridine-3-carbonyl]amino]-2-fluoro-4-[rac-(3R)-3,4-dimethylpiperazin-1-yl]phenyl]-3,6-dihydro-2H-pyridine-1-carboxylate | 0.00282 |
| 725 | 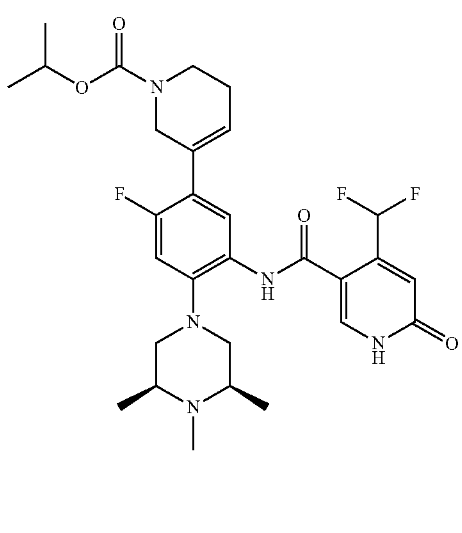 | propan-2-yl 5-[5-[[4-(difluoromethyl)-6-oxo-1H-pyridine-3-carbonyl]amino]-2-fluoro-4-[rac-(3R,5S)-3,4,5-trimethylpiperazin-1-yl]phenyl]-3,6-dihydro-2H-pyridine-1-carboxylate | 0.00159 |

TABLE 1-continued

Binding affinities (K_D) derived from surface plasmon resonance (SPR) assays

| Example No. | Structure | IUPAC Name | WDR5 binding affinity (K_D, μM) |
|---|---|---|---|
| 726 | 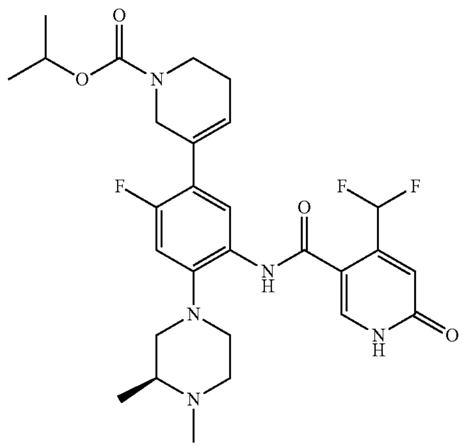 [SMILES: CC(C)OC(=O)N1CCC=C(c2cc(NC(=O)c3c[nH]c(=O)cc3C(F)F)c(N3CCN(C)[C@@H](C)C3)cc2F)C1] | propan-2-yl 5-[5-[[4-(difluoromethyl)-6-oxo-1H-pyridine-3-carbonyl]amino]-2-fluoro-4-[rac-(3R)-3,4-dimethylpiperazin-1-yl]phenyl]-3,6-dihydro-2H-pyridine-1-carboxylate | 0.0021 |
| 727 | 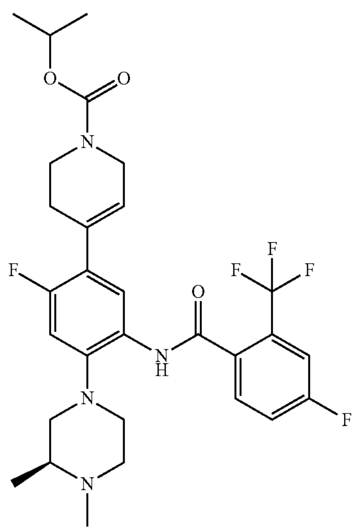 [SMILES: CC(C)OC(=O)N1CC=C(c2cc(NC(=O)c3ccc(F)cc3C(F)(F)F)c(N3CCN(C)[C@@H](C)C3)cc2F)CC1] | propan-2-yl 4-[2-fluoro-5-[[4-fluoro-2-(trifluoromethyl)benzoyl]amino]-4-[rac-(3R)-3,4-dimethylpiperazin-1-yl]phenyl]-3,6-dihydro-2H-pyridine-1-carboxylate | 0.00246 |
| 728 | 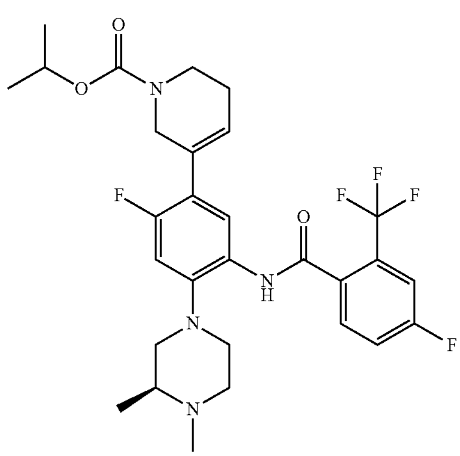 [SMILES: CC(C)OC(=O)N1CCC=C(c2cc(NC(=O)c3ccc(F)cc3C(F)(F)F)c(N3CCN(C)[C@@H](C)C3)cc2F)C1] | propan-2-yl 5-[2-fluoro-5-[[4-fluoro-2-(trifluoromethyl)benzoyl]amino]-4-[rac-(3R)-3,4-dimethylpiperazin-1-yl]phenyl]-3,6-dihydro-2H-pyridine-1-carboxylate | 0.00355 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 729 | 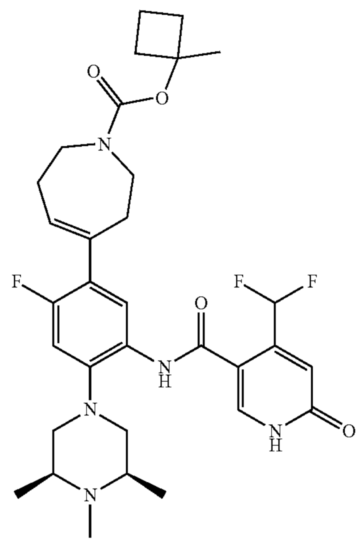 [SMILES: C[C@@H]1CN(c2cc(F)c(C3=CCCN(C(=O)OC4(C)CCC4)CC3)cc2NC(=O)c2c[nH]c(=O)cc2C(F)F)C[C@H](C)N1C] | (1-methylcyclobutyl) 4-[5-[[4-(difluoromethyl)-6-oxo-1H-pyridine-3-carbonyl]amino]-2-fluoro-4-[rac-(3R,5S)-3,4,5-trimethylpiperazin-1-yl]phenyl]-2,3,6,7-tetrahydroazepine-1-carboxylate | 0.00311 |
| 730 | 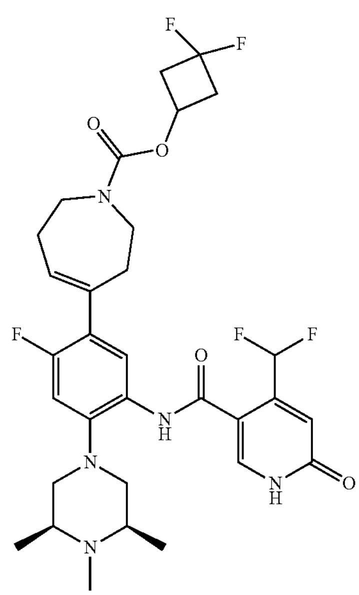 [SMILES: C[C@@H]1CN(c2cc(F)c(C3=CCCN(C(=O)OC4CC(F)(F)C4)CC3)cc2NC(=O)c2c[nH]c(=O)cc2C(F)F)C[C@H](C)N1C] | (3,3-difluorocyclobutyl) 4-[5-[[4-(difluoromethyl)-6-oxo-1H-pyridine-3-carbonyl]amino]-2-fluoro-4-[rac-(3R,5S)-3,4,5-trimethylpiperazin-1-yl]phenyl]-2,3,6,7-tetrahydroazepine-1-carboxylate | 0.00799 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 731 | 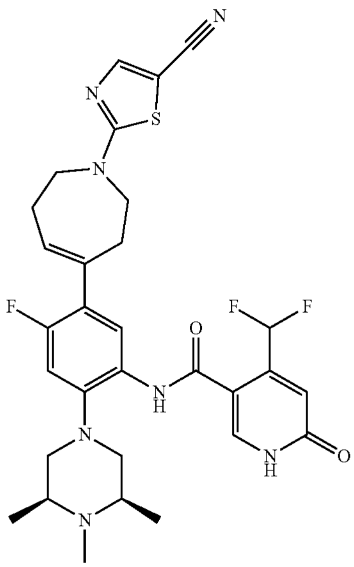 [SMILES: C[C@@H]1CN(c2cc(F)c(C3=CCCN(c4ncc(C#N)s4)CC3)cc2NC(=O)c2c[nH]c(=O)cc2C(F)F)C[C@H](C)N1C] | N-[5-[1-(5-cyano-1,3-thiazol-2-yl)-2,3,6,7-tetrahydroazepin-4-yl]-4-fluoro-2-[rac-(3R,5S)-3,4,5-trimethylpiperazin-1-yl]phenyl]-4-(difluoromethyl)-6-oxo-1H-pyridine-3-carboxamide | 0.00761 |
| 732 | 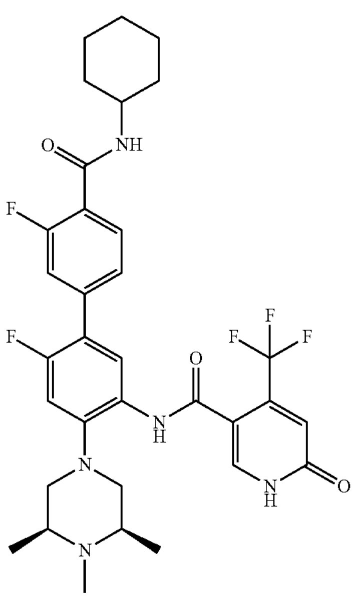 [SMILES: C[C@@H]1CN(c2cc(F)c(-c3ccc(C(=O)NC4CCCCC4)c(F)c3)cc2NC(=O)c2c[nH]c(=O)cc2C(F)(F)F)C[C@H](C)N1C] | N-[5-[4-(cyclohexylcarbamoyl)-3-fluorophenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00276 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 733 | 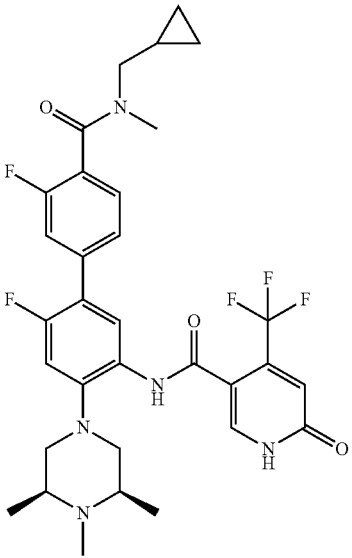 [SMILES: C[C@@H]1CN(c2cc(F)c(-c3ccc(C(=O)N(C)CC4CC4)c(F)c3)cc2NC(=O)c2c[nH]c(=O)cc2C(F)(F)F)C[C@H](C)N1C] | N-[5-[4-[cyclopropylmethyl(methyl)carbamoyl]-3-fluorophenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00129 |
| 734 | 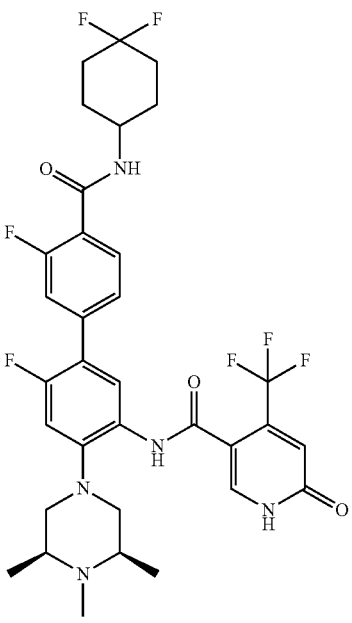 [SMILES: C[C@@H]1CN(c2cc(F)c(-c3ccc(C(=O)NC4CCC(F)(F)CC4)c(F)c3)cc2NC(=O)c2c[nH]c(=O)cc2C(F)(F)F)C[C@H](C)N1C] | N-[5-[4-[(4,4-difluorocyclohexyl)carbamoyl]-3-fluorophenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00413 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 735 | 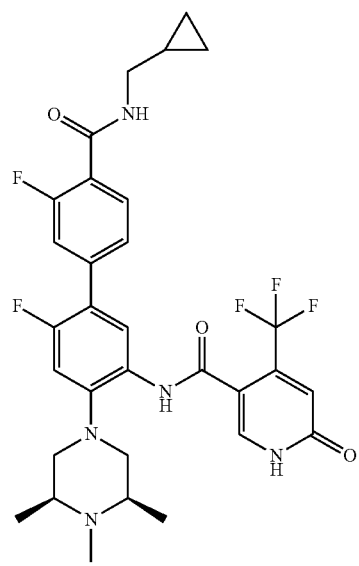 [SMILES: C[C@@H]1CN(c2cc(F)c(-c3ccc(C(=O)NCC4CC4)c(F)c3)cc2NC(=O)c2c[nH]c(=O)cc2C(F)(F)F)C[C@H](C)N1C] | N-[5-[4-(cyclopropylmethylcarbamoyl)-3-fluorophenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00423 |
| 736 | 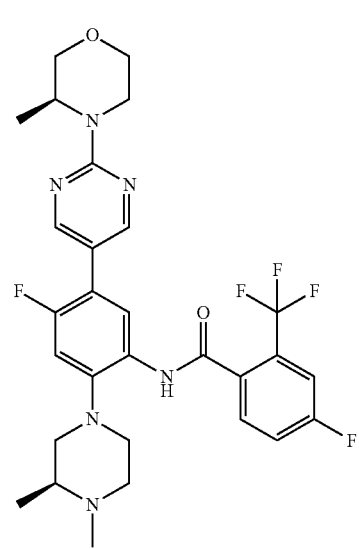 [SMILES: C[C@H]1CN(c2cc(F)c(-c3cnc(N4CCOC[C@@H]4C)nc3)cc2NC(=O)c2ccc(F)cc2C(F)(F)F)CCN1C] | 4-fluoro-N-[4-fluoro-2-[rac-(3R)-3,4-dimethylpiperazin-1-yl]-5-[2-[rac-(2R)-2-methylmorpholin-4-yl]pyrimidin-4-yl]phenyl]-2-(trifluoromethyl)benzamide | 0.00029 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 737 | 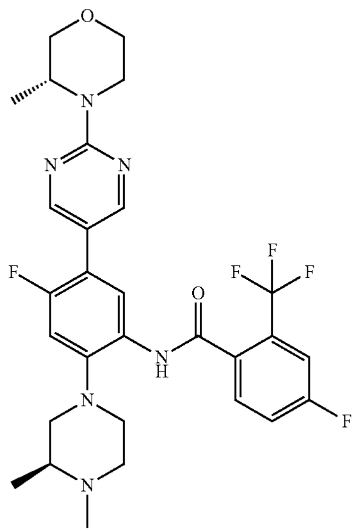 [SMILES: C[C@@H]1COCCN1c1ncc(-c2cc(NC(=O)c3ccc(F)cc3C(F)(F)F)c(N3CCN(C)[C@@H](C)C3)cc2F)cn1] | 4-fluoro-N-[4-fluoro-2-[rac-(3S)-3,4-dimethylpiperazin-1-yl]-5-[2-[rac-(3R)-3-methylmorpholin-4-yl]pyrimidin-5-yl]phenyl]-2-(trifluoromethyl)benzamide | 0.00461 |
| 738 | 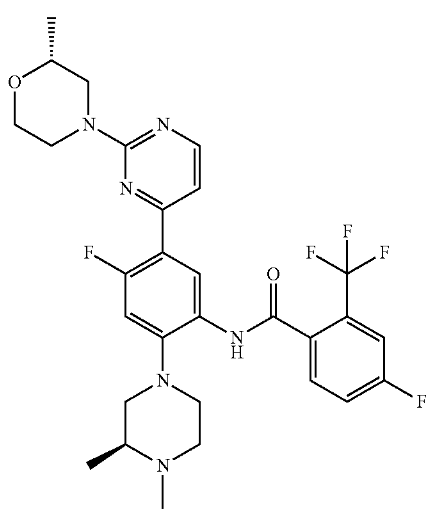 [SMILES: C[C@@H]1CN(c2nccc(-c3cc(NC(=O)c4ccc(F)cc4C(F)(F)F)c(N4CCN(C)[C@@H](C)C4)cc3F)n2)CCO1] | 4-fluoro-N-[4-fluoro-2-[rac-(3S)-3,4-dimethylpiperazin-1-yl]-5-[2-[rac-(2R)-2-methylmorpholin-4-yl]pyriimdin-4-yl]phenyl]-2-(trifluoromethyl)benzamide | 0.004 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 739 | 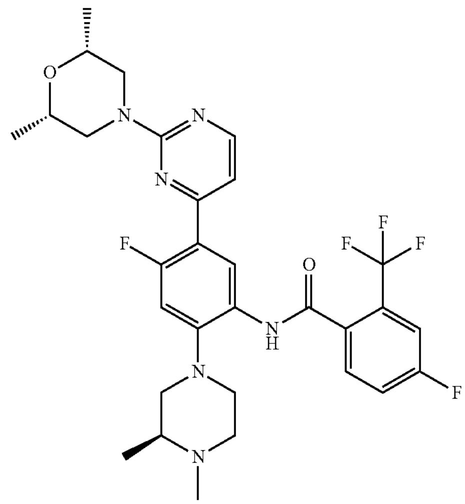 [SMILES: C[C@@H]1CN(c2nccc(-c3cc(NC(=O)c4ccc(F)cc4C(F)(F)F)c(N4CCN(C)[C@@H](C)C4)cc3F)n2)C[C@H](C)O1] | 4-fluoro-N-[4-fluoro-5-[2-[rac-(2R,6S)-2,6-dimethylmorpholin-4-yl]pyrimidin-4-yl]-2-[rac-(3R)-3,4-dimethylpiperazin-1-yl]phenyl]-2-(trifluoromethyl)benzamide | 0.003 |
| 740 | 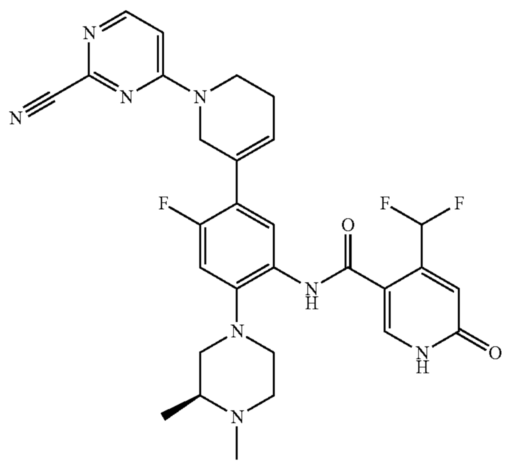 [SMILES: C[C@H]1CN(c2cc(F)c(C3=CCCN(c4ccnc(C#N)n4)C3)cc2NC(=O)c2c[nH]c(=O)cc2C(F)F)CCN1C] | N-[5-[1-(2-cyanopyrimidin-4-yl)-3,6-dihydro-2H-pyridin-5-yl]-4-fluoro-2-[rac-(3R)-3,4-dimethylpiperazin-1-yl]phenyl]-4-(difluoromethyl)-6-oxo-1H-pyridine-3-carboxamide | 0.00447 |
| 741 | 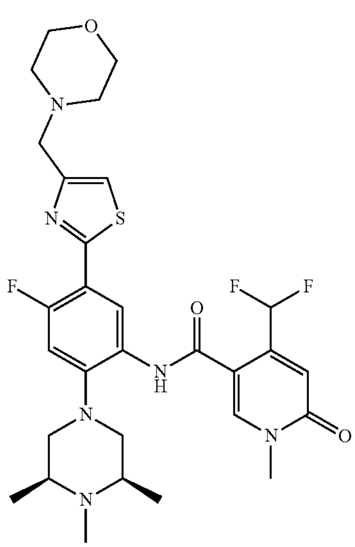 [SMILES: C[C@@H]1CN(c2cc(F)c(-c3nc(CN4CCOCC4)cs3)cc2NC(=O)c2cn(C)c(=O)cc2C(F)F)C[C@H](C)N1C] | 4-(difluoromethyl)-N-[4-fluoro-5-[4-(morpholin-4-ylmethyl)-1,3-thiazol-2-yl]-2-[rac-(3R,5S)-3,4,5-trimethylpiperazin-1-yl]phenyl]-1-methyl-6-oxopyridine-3-carboxamide | 0.00675 |

TABLE 1-continued

*Binding affinities (K_D) derived from surface plasmon resonance (SPR) assays*

| Example No. | Structure | IUPAC Name | WDR5 binding affinity ($K_D$, μM) |
|---|---|---|---|
| 742 | 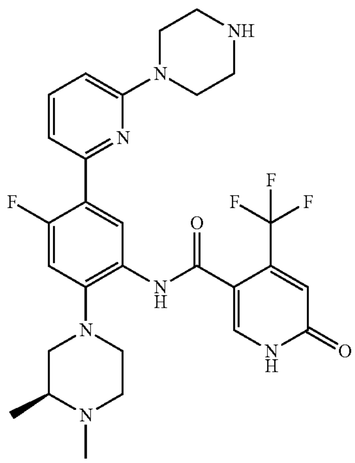 | N-[4-fluoro-5-(6-piperazin-1-ylpyridin-2-yl)-2-[rac-(3R)-3,4-dimethylpiperazin-1-yl]phenyl]-6-oxo-4-(trifluoromethyl)-1H-pyridine-3-carboxamide | 0.00287 |
| 743 | 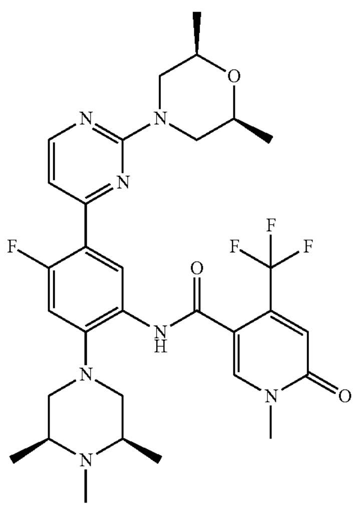 [SMILES: C[C@@H]1CN(c2nccc(-c3cc(NC(=O)c4cn(C)c(=O)cc4C(F)(F)F)c(N4C[C@@H](C)N(C)[C@@H](C)C4)cc3F)n2)C[C@H](C)O1] | N-[4-fluoro-5-[2-[rac-(2R,6S)-2,6-dimethylmorpholin-4-yl]pyrimidin-4-yl]-2-[rac-(3R,5S)-3,4,5-trimethylpiperazin-1-yl]phenyl]-1-methyl-6-oxo-4-(trifluoromethyl)pyridine-3-carboxamide | 0.00522 |
| 744 | 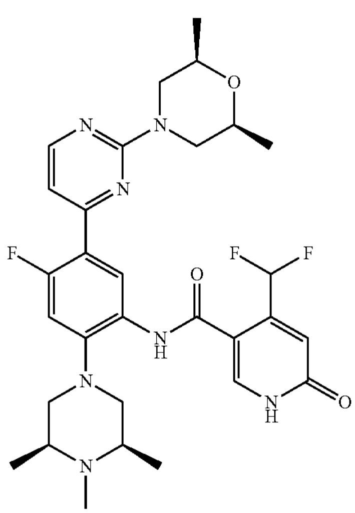 [SMILES: C[C@@H]1CN(c2nccc(-c3cc(NC(=O)c4c[nH]c(=O)cc4C(F)F)c(N4C[C@@H](C)N(C)[C@@H](C)C4)cc3F)n2)C[C@H](C)O1] | 4-(difluoromethyl)-N-[4-fluoro-5-[2-[rac-(2R,6S)-2,6-dimethylmorpholin-4-yl]pyrimidin-4-yl]-2-[rac-(3S,5R)-3,4,5-trimethylpiperazin-1-yl]phenyl]-6-oxo-1H-pyridine-3-carboxamide | 0.00276 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 745 | 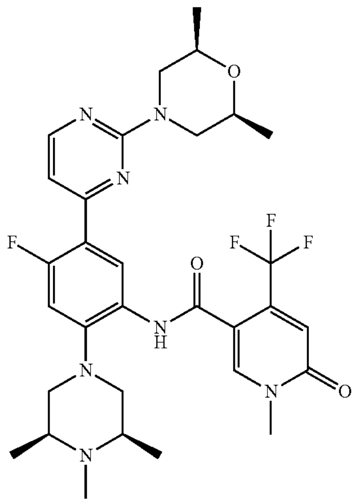 [SMILES: C[C@@H]1CN(c2nccc(-c3cc(NC(=O)c4cn(C)c(=O)cc4C(F)(F)F)c(N4C[C@@H](C)N(C)[C@@H](C)C4)cc3F)n2)C[C@H](C)O1] | 4-(difluoromethyl)-N-[4-fluoro-5-[2-[rac-(2R,6S)-2,6-dimethylmorpholin-4-yl]pyrimidin-4-yl]-2-[rac-(3R,5S)-3,4,5-trimethylpiperazin-1-yl]phenyl]-1-methyl-6-oxopyridine-3-carboxamide | 0.0056 |
| 746 | 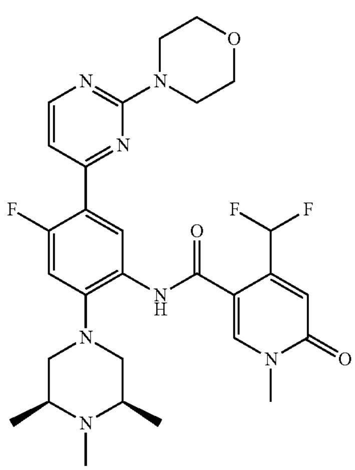 [SMILES: C[C@@H]1CN(c2cc(F)c(-c3ccnc(N4CCOCC4)n3)cc2NC(=O)c2cn(C)c(=O)cc2C(F)F)C[C@H](C)N1C] | 4-(difluoromethyl)-N-[4-fluoro-5-(2-morpholin-4-ylpyrimidin-4-yl)-2-[rac-(3R,5S)-3,4,5-trimethylpiperazin-1-yl]phenyl]-1-methyl-6-oxopyridine-3-carboxamide | 13565 |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 747 | 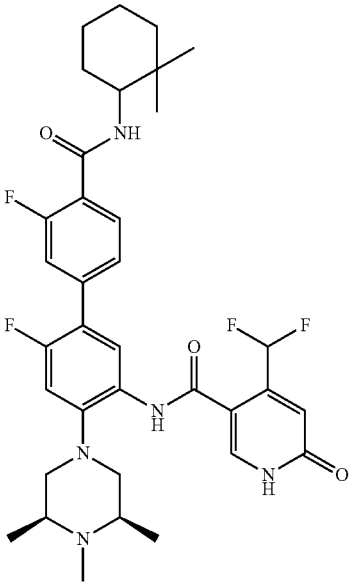 [SMILES: C[C@@H]1CN(c2cc(F)c(-c3ccc(C(=O)NC4CCCCC4(C)C)c(F)c3)cc2NC(=O)c2c[nH]c(=O)cc2C(F)F)C[C@H](C)N1C] | N-[5-[4-[(2,2-dimethylcyclohexyl)carbamoyl]-3-fluorophenyl]-4-fluoro-2-[rac-(3R,5S)-3,4,5-trimethylpiperazin-1-yl]phenyl]-6-oxo-4-(trifluoromethyl)-1H-pyridine-3-carboxamide | 0.00485 |
| 748 | 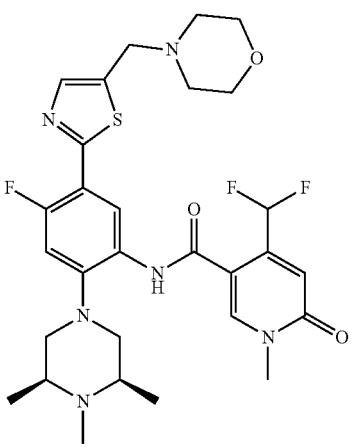 [SMILES: C[C@@H]1CN(c2cc(F)c(-c3ncc(CN4CCOCC4)s3)cc2NC(=O)c2cn(C)c(=O)cc2C(F)F)C[C@H](C)N1C] | 4-(difluoromethyl)-N-[4-fluoro-5-[5-(morpholin-4-ylmethyl)-1,3-thiazol-2-yl]-2-[rac-(3R,5S)-3,4,5-trimethylpiperazin-1-yl]phenyl]-1-methyl-6-oxopyridine-3-carboxamide | 0.05181 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 749 | 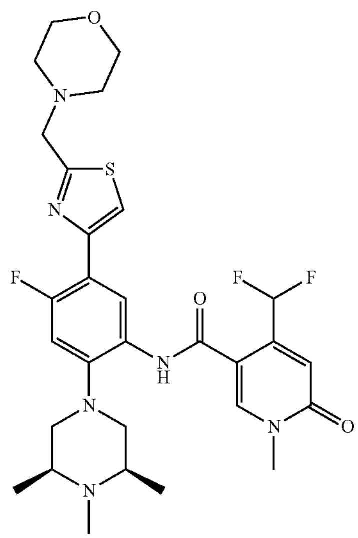 [SMILES: C[C@@H]1CN(c2cc(F)c(-c3csc(CN4CCOCC4)n3)cc2NC(=O)c2cn(C)c(=O)cc2C(F)F)C[C@H](C)N1C] | 4-(difluoromethyl)-N-[4-fluoro-5-[2-(morpholin-4-ylmethyl)-1,3-thiazol-4-yl]-2-[rac-(3R,5S)-3,4,5-trimethylpiperazin-1-yl]phenyl]-1-methyl-6-oxopyridine-3-carboxamide | 0.01061 |
| 750 | 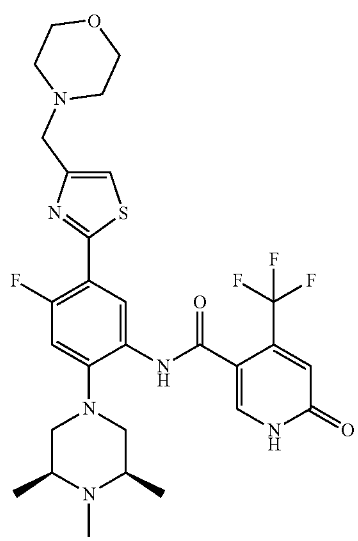 [SMILES: C[C@@H]1CN(c2cc(F)c(-c3nc(CN4CCOCC4)cs3)cc2NC(=O)c2c[nH]c(=O)cc2C(F)(F)F)C[C@H](C)N1C] | N-[4-fluoro-5-[4-(morpholin-4-ylmethyl)-1,3-thiazol-2-yl]-2-[rac-(3R,5S)-3,4,5-trimethylpiperazin-1-yl]phenyl]-6-oxo-4-(trifluoromethyl)-1H-pyridine-3-carboxamide | 0.00171 |
| 751 | 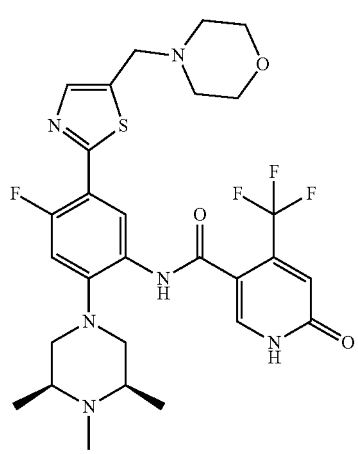 [SMILES: C[C@@H]1CN(c2cc(F)c(-c3ncc(CN4CCOCC4)s3)cc2NC(=O)c2c[nH]c(=O)cc2C(F)(F)F)C[C@H](C)N1C] | N-[4-fluoro-5-[5-(morpholin-4-ylmethyl)-1,3-thiazol-2-yl]-2-[rac-(3R,5S)-3,4,5-trimethylpiperazin-1-yl]phenyl]-6-oxo-4-(trifluoromethyl)-1H-pyridine-3-carboxamide | 0.00827 |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 752 | 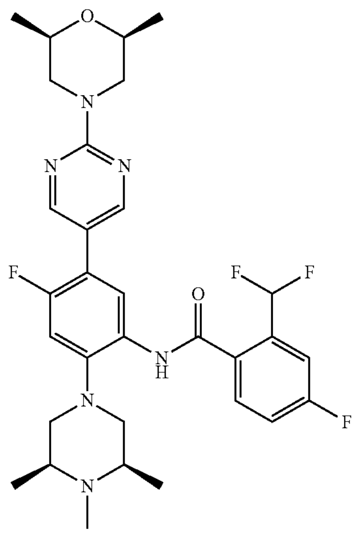 [SMILES: C[C@@H]1CN(c2ncc(-c3cc(NC(=O)c4ccc(F)cc4C(F)F)c(N4C[C@@H](C)N(C)[C@@H](C)C4)cc3F)cn2)C[C@H](C)O1] | 2-(difluoromethyl)-N-(5-(2-((2S,6R)-2,6-dimethylmorpholino)pyrimidin-5-yl)-4-fluoro-2-((3S,5R)-3,4,5-trimethylpiperazin-1-yl)phenyl)-4-fluorobenzamide | — |
| 753 | 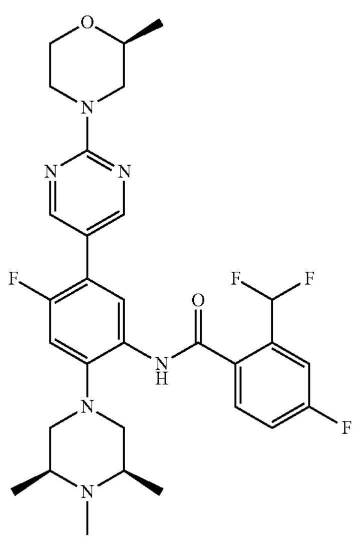 [SMILES: C[C@@H]1CN(c2cc(F)c(-c3cnc(N4CCO[C@@H](C)C4)nc3)cc2NC(=O)c2ccc(F)cc2C(F)F)C[C@H](C)N1C] | 2-(difluoromethyl)-4-fluoro-N-(4-fluoro-5-(2-((S)-2-methylmorpholino)pyrimidin-5-yl)-2-((3S,5R)-3,4,5-trimethylpiperazin-1-yl)phenyl)benzamide | — |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 754 | 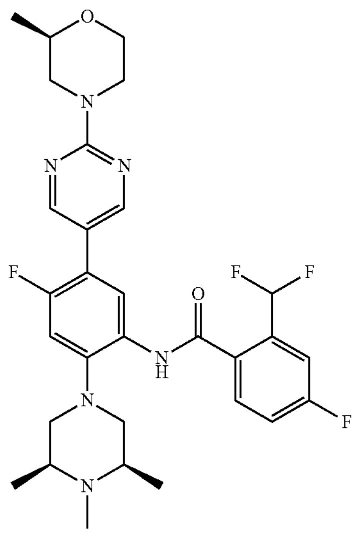 [SMILES: C[C@@H]1CN(c2ncc(-c3cc(NC(=O)c4ccc(F)cc4C(F)F)c(N4C[C@@H](C)N(C)[C@@H](C)C4)cc3F)cn2)CCO1] | 2-(difluoromethyl)-4-fluoro-N-(4-fluoro-5-(2-((R)-2-methylmorpholino)pyrimidin-5-yl)-2-((3S,5R)-3,4,5-trimethylpiperazin-1-yl)phenyl)benzamide | — |
| 755 | 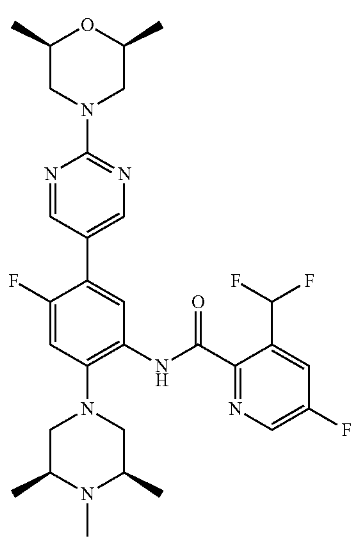 [SMILES: C[C@@H]1CN(c2ncc(-c3cc(NC(=O)c4ncc(F)cc4C(F)F)c(N4C[C@@H](C)N(C)[C@@H](C)C4)cc3F)cn2)C[C@H](C)O1] | 3-(difluoromethyl)-N-(5-(2-((2S,6R)-2,6-dimethylmorpholino)pyrimidin-5-yl)-4-fluoro-2-((3S,5R)-3,4,5-trimethylpiperazin-1-yl)phenyl)-5-fluoropicolinamide | — |

TABLE 1-continued

Binding affinities (K$_D$) derived from surface plasmon resonance (SPR) assays

| Example No. | Structure | IUPAC Name | WDR5 binding affinity (K$_D$, μM) |
|---|---|---|---|
| 756 | 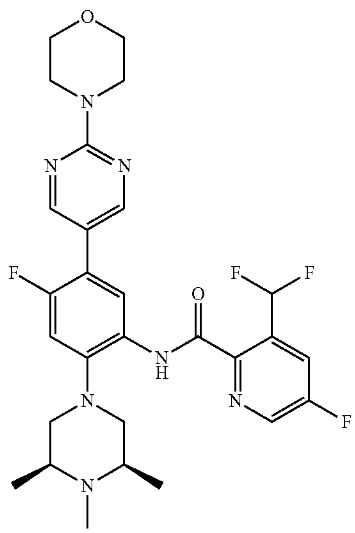 | 3-(difluoromethyl)-5-fluoro-N-(4-fluoro-5-(2-morpholinopyrimidin-5-yl)-2-((3S,5R)-3,4,5-trimethylpiperazin-1-yl)phenyl)picolinamide | — |
| 757 | 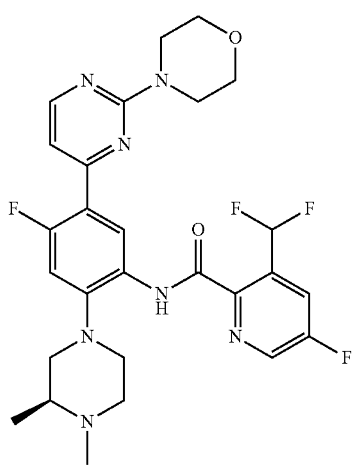 | (S)-3-(difluoromethyl)-N-(2-(3,4-dimethylpiperazin-1-yl)-4-fluoro-5-(2-morpholinopyrimidin-4-yl)phenyl)-5-fluoropicolinamide | — |
| 758 | 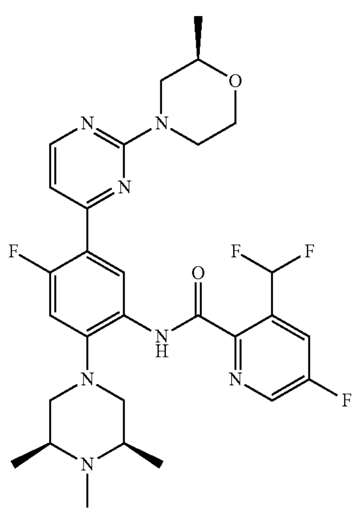 [SMILES: C[C@@H]1CN(c2nccc(-c3cc(NC(=O)c4ncc(F)cc4C(F)F)c(N4C[C@@H](C)N(C)[C@@H](C)C4)cc3F)n2)CCO1] | 3-(difluoromethyl)-5-fluoro-N-(4-fluoro-5-(2-((R)-2-methylmorpholino)pyrimidin-4-yl)-2-((3S,5R)-3,4,5-trimethylpiperazin-1-yl)phenyl)picolinamide | — |

TABLE 1-continued

Binding affinities (K$_D$) derived from surface plasmon resonance (SPR) assays

| Example No. | Structure | IUPAC Name | WDR5 binding affinity (K$_D$, µM) |
|---|---|---|---|
| 759 | 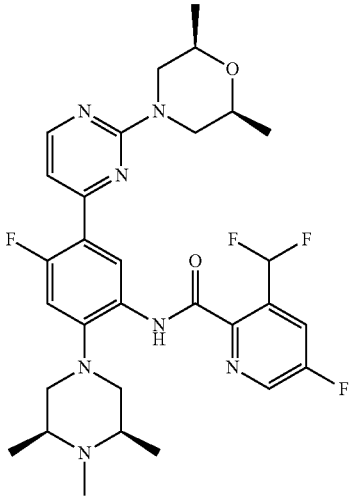 [SMILES: C[C@@H]1CN(c2nccc(-c3cc(NC(=O)c4ncc(F)cc4C(F)F)c(N4C[C@@H](C)N(C)[C@@H](C)C4)cc3F)n2)C[C@H](C)O1] | 3-(difluoromethyl)-N-(5-(2-((2S,6R)-2,6-dimethylmorpholino)pyrimidin-4-yl)-4-fluoro-2-((3S,5R)-3,4,5-trimethylpiperazin-1-yl)phenyl)-5-fluoropicolinamide | — |
| 760 | 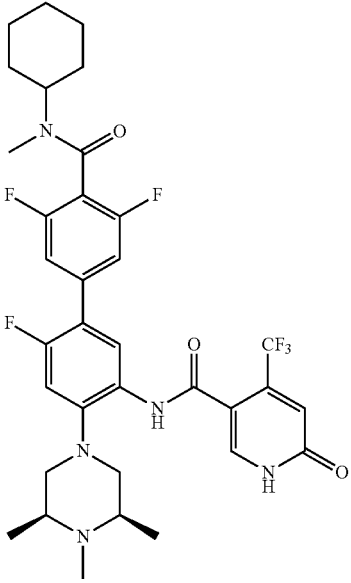 [SMILES: C[C@@H]1CN(c2cc(F)c(-c3cc(F)c(C(=O)N(C)C4CCCCC4)c(F)c3)cc2NC(=O)c2c[nH]c(=O)cc2C(F)(F)F)C[C@H](C)N1C] | N-(4'-(cyclohexyl(methyl)carbamoyl)-3',5',6-trifluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide | 0.002 |

TABLE 1-continued

Binding affinities ($K_D$) derived from surface plasmon resonance (SPR) assays

| Example No. | Structure | IUPAC Name | WDR5 binding affinity ($K_D$, µM) |
|---|---|---|---|
| 761 | 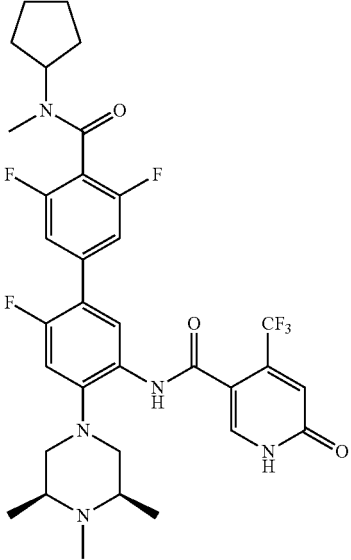 [SMILES: C[C@@H]1CN(c2cc(F)c(-c3cc(F)c(C(=O)N(C)C4CCCC4)c(F)c3)cc2NC(=O)c2c[nH]c(=O)cc2C(F)(F)F)C[C@H](C)N1C] | N-(4'-(cyclopentyl (methyl)carbamoyl)-3',5',6-trifluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide | 0.002 |
| 762 | 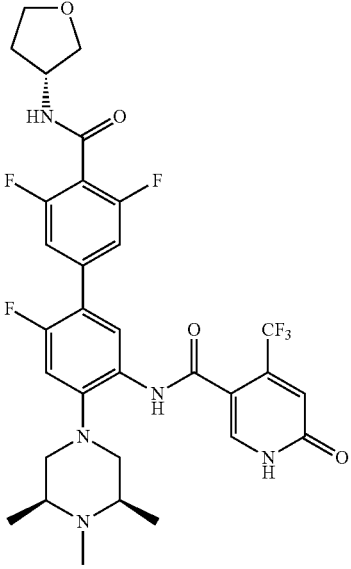 [SMILES: C[C@@H]1CN(c2cc(F)c(-c3cc(F)c(C(=O)N[C@@H]4CCOC4)c(F)c3)cc2NC(=O)c2c[nH]c(=O)cc2C(F)(F)F)C[C@H](C)N1C] | 6-oxo-N-(3',5',6-trifluoro-4'-(((R)-tetrahydrofuran-3-yl)carbamoyl)-4-((3S,5R)-3,4,5-trimethylpiperazin-1-yl)-[1,1'-biphenyl]-3-yl)-4-(trifluoromethyl)-1,6-dihydropyridine-3-carboxamide | 0.0009 |

TABLE 1-continued

Binding affinities (K_D) derived from surface plasmon resonance (SPR) assays

| Example No. | Structure | IUPAC Name | WDR5 binding affinity ($K_D$, μM) |
|---|---|---|---|
| 763 | 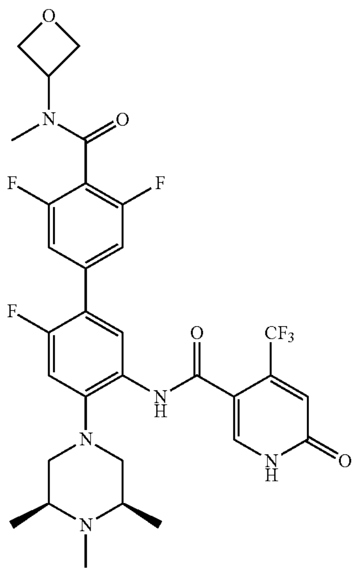 [SMILES: C[C@@H]1CN(c2cc(F)c(-c3cc(F)c(C(=O)N(C)C4COC4)c(F)c3)cc2NC(=O)c2c[nH]c(=O)cc2C(F)(F)F)C[C@H](C)N1C] | 6-oxo-N-(3',5',6-trifluoro-4'-(methyl(oxetan-3-yl)carbamoyl)-4-((3S,5R)-3,4,5-trimethylpiperazin-1-yl)-[1,1'-biphenyl]-3-yl)-4-(trifluoromethyl)-1,6-dihydropyridine-3-carboxamide | 0.0007 |
| 764 | 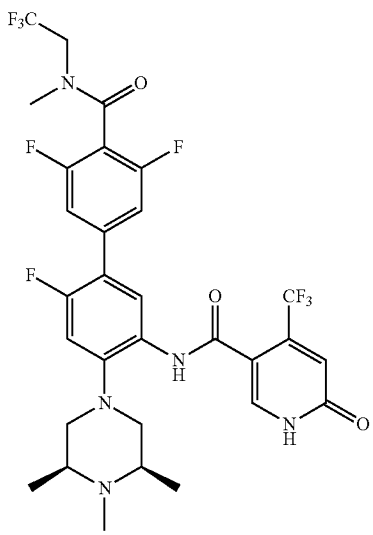 [SMILES: C[C@@H]1CN(c2cc(F)c(-c3cc(F)c(C(=O)N(C)CC(F)(F)F)c(F)c3)cc2NC(=O)c2c[nH]c(=O)cc2C(F)(F)F)C[C@H](C)N1C] | 6-oxo-N-(3',5',6-trifluoro-4'-(methyl(2,2,2-trifluoroethyl)carbamoyl)-4-((3S,5R)-3,4,5-trimethylpiperazin-1-yl)-[1,1'-biphenyl]-3-yl)-4-(trifluoromethyl)-1,6-dihydropyridine-3-carboxamide | — |

TABLE 2

Inhibitory activity of exemplary compounds of the application in the in vitro methyl transferase assay (MLL1-WRAD2 assay).

| Example No. | WDR5 binding affinity ($K_D$, μM) | In vitro MLL1 activity ($IC_{50}$, μM) | Residence Time (t, min) |
|---|---|---|---|
| 1 | 0.084 | 15 | 1.36 |
| 2 | 0.011 | 2.71 | 4.62 |
| 3 | 0.002 | 0.272 | 26.50 |
| 4 | 0.004 | 0.82 | 12.94 |
| 5 | 0.033 | 1.31 | 6.76 |
| 6 | 0.003 | 0.885 | 14.2 |
| 7 | 0.00006 | 0.054 | 299.22 |
| 8 | 0.0003 | 0.043 | 132.28 |
| 9 | 0.005 | 0.984 | 11.22 |
| 10 | 0.013 | 8.36 | 8.23 |
| 11 | 0.005 | 0.993 | 17.29 |
| 12 | 0.005 | 2.07 | 14.66 |
| 13 | 0.004 | 9.53 | 7.51 |
| 14 | 0.005 | 1.49 | 13.26 |
| 15 | 0.026 | 19 | 1.59 |
| 16 | 0.002 | 0.467 | 22.61 |

TABLE 2-continued

Inhibitory activity of exemplary compounds of the application in the in vitro methyl transferase assay (MLL1-WRAD2 assay).

| Example No. | WDR5 binding affinity ($K_D$, μM) | In vitro MLL1 activity ($IC_{50}$, μM) | Residence Time (t, min) |
|---|---|---|---|
| 17 | 0.006 | 2.07 | 16.20 |
| 18 | 0.009 | 9.83 | 4.05 |
| 19 | 0.004 | 3.67 | 9.29 |
| 20 | 0.002 | 0.213 | 14.93 |
| 21 | 0.0009 | 0.272 | 54.29 |
| 22 | 0.0076 | 6.65 | 6.49 |
| 23 | 0.017 | >30 | 1.61 |
| 24 | 0.076 | >30 | 1.68 |
| 25 | 0.009 | 3.34 | 12.98 |
| 26 | 0.043 | >30 | 1.82 |
| 27 | 0.294 | NT | ND |
| 28 | 0.002 | 2.74 | 72.78 |
| 29 | 0.0009 | 0.182 | 66.40 |
| 30 | 0.003 | 1.0 | 13.65 |
| 31 | 0.001 | 0.075 | 31.69 |
| 32 | 0.0004 | 0.111 | 56.31 |
| 33 | 0.0005 | 1.01 | 39.78 |
| 34 | 0.0001 | 0.036 | 114.16 |
| 35 | 0.003 | 0.620 | 20.20 |
| 36 | 0.002 | 0.316 | 39.78 |
| 37 | 0.0002 | 0.106 | 55.93 |
| 38 | 0.004 | 9.85 | 2.04 |
| 39 | 0.0003 | 0.174 | 69.44 |
| 40 | 0.008 | 0.774 | 5.52 |
| 41 | 0.009 | 4.91 | 5.39 |
| 42 | 0.009 | NT | 3.45 |
| 43 | 0.020 | 15.7 | 1.35 |
| 44 | 0.005 | 1.64 | 7.4 |
| 45 | 0.009 | 0.78 | 3.09 |
| 46 | 0.005 | 2.29 | 6.96 |
| 47 | 0.019 | 19.6 | 4.82 |
| 48 | 0.015 | 11.2 | 2.88 |
| 49 | 0.014 | 17.7 | 3.38 |
| 50 | 0.012 | 9.41 | 1.37 |
| 51 | 0.007 | 0.478 | 25.84 |
| 52 | 0.006 | 1.28 | 17.25 |
| 53 | 0.006 | 1.49 | 7.65 |
| 54 | 0.051 | 26.7 | 0.53 |
| 55 | 0.052 | NT | 0.63 |
| 56 | 0.019 | 0.864 | 2.32 |
| 57 | 0.030 | 9.50 | 1.26 |
| 58 | 0.004 | 1.57 | 11.52 |

TABLE 3 in-cell H3K4 dimethylation of exemplary compounds of the application.

| Compound ID | In vitro whole cell potency in T24 cells, H3K4Me2 ($IC_{50}$, μM) |
|---|---|
| 3 | 0.882 |
| 6 | 1.07 |
| 7 | 0.166 |
| 8 | 0.144 |
| 39 | 0.626 |

TABLE 4

Whole cell potency of exemplary compounds of the application in MV-411 cells.

| Example No. | In vitro whole cell potency in MV-411 cells, ($IC_{50}$, μM) |
|---|---|
| 1 | NT |
| 2 | 2.25 |
| 3 | 0.749 |
| 4 | 0.574 |
| 5 | 0.881 |
| 6 | 0.828 |
| 7 | 0.051 |
| 8 | 0.044 |
| 9 | 0.507 |
| 10 | >10 |
| 11 | 1.27 |
| 12 | 0.929 |
| 13 | >10 |
| 14 | 1.524 |
| 15 | >10 |
| 16 | 0.844 |
| 17 | NT |
| 18 | NT |
| 19 | NT |
| 20 | 0.604 |
| 21 | 0.271 |
| 22 | 5.266 |
| 23 | >10 |
| 24 | >10 |
| 25 | >10 |
| 26 | >10 |
| 27 | NT |
| 28 | 2.76 |
| 29 | 0.045 |
| 30 | 0.21 |
| 31 | 0.571 |
| 32 | 0.067 |
| 33 | 0.072 |
| 34 | 0.038 |
| 35 | 0.669 |
| 36 | 0.85 |
| 37 | 0.054 |
| 38 | 4.07 |
| 39 | 0.213 |
| 40 | >10 |
| 41 | 0.213 |
| 42 | 0.428 |
| 43 | NT |
| 44 | NT |
| 45 | 0.491 |
| 46 | 2.90 |
| 47 | NT |
| 48 | >10 |
| 49 | >10 |
| 50 | 2.895 |
| 51 | 0.389 |
| 52 | >10 |
| 53 | >10 |
| 54 | NT |
| 55 | 0.389 |
| 56 | 0.435 |
| 57 | NT |
| 58 | 1.47 |
| 63 | 0.206 |
| 64 | 0.366 |
| 90 | 0.120 |
| 91 | 0.257 |
| 92 | 0.071 |
| 93 | 0.048 |
| 161 | 0.028 |
| 197 | 0.044 |
| 201 | 0.113 |
| 202 | 0.020 |
| 216 | 0.388 |
| 221 | 0.120 |
| 245 | 0.125 |
| 247 | 0.854 |
| 248 | 0.137 |
| 274 | 0.075 |

TABLE 4-continued

Whole cell potency of exemplary compounds of the application in MV-411 cells.

| Example No. | In vitro whole cell potency in MV-411 cells, (IC$_{50}$, μM) |
|---|---|
| 279 | 0.118 |
| 334 | 0.031 |
| 341 | 0.052 |
| 348 | 0.042 |
| 378 | 0.020 |
| 383 | 0.149 |
| 395 | 0.031 |
| 398 | 0.044 |
| 401 | 0.030 |
| 410 | 0.063 |
| 413 | 0.057 |
| 414 | 0.008 |
| 415 | 0.017 |
| 418 | 0.070 |
| 430 | 0.049 |
| 451 | 0.092 |
| 452 | 0.062 |
| 456 | 0.089 |
| 464 | 0.049 |
| 465 | 0.100 |
| 470 | 0.056 |
| 471 | 0.078 |
| 472 | 0.104 |
| 473 | 0.032 |
| 483 | 0.024 |
| 508 | 0.073 |
| 521 | 0.068 |
| 532 | 0.022 |
| 540 | 0.027 |
| 593 | 0.014 |
| 594 | 0.019 |
| 600 | 0.052 |
| 617 | 0.036 |

TABLE 5

Effect of Fluoro-substitution at A on residence time (t) and MLL1 inhibition:

| Comp. No. | Structure | Assay Results | Comp. No. | Compound | Assay Results |
|---|---|---|---|---|---|
| 56 | [structure] | K$_D$ (SPR) = 0.0175 μM<br>τ = 1.8 min<br>IC$_{50}$ (HMT) = 0.86 μM | 3 | [structure] | K$_D$ (SPR) = 0.0015 μM<br>τ = 26 min<br>IC$_{50}$ (MLL1) = 0.38 μM |
| 57 | [structure] | K$_D$ (SPR) = 0.036 μM<br>τ = 0.78 min<br>IC$_{50}$ (HMT) = 9.5 μM | 2 | [structure] | K$_D$ (SPR) = 0.011 μM<br>τ = 4.6 min<br>IC$_{50}$ (MLL1) = 2.71 μM |

TABLE 5-continued

Effect of Fluoro-substitution at A on residence time (t) and MLL1 inhibition:

| Comp. No. | Structure | Assay Results | Comp. No. | Compound | Assay Results |
|---|---|---|---|---|---|
| 58 | 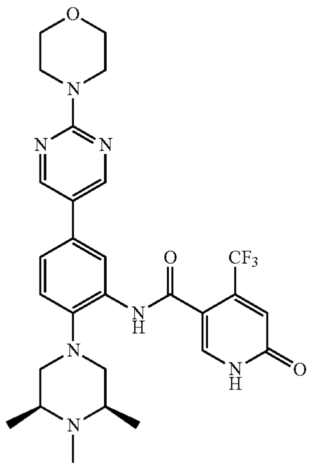 [SMILES: C[C@@H]1CN(c2ccc(-c3cnc(N4CCOCC4)nc3)cc2NC(=O)c2c[nH]c(=O)cc2C(F)(F)F)C[C@H](C)N1C] | $K_D$ (SPR) = 0.0035 μM<br>τ = 11.5 min<br>$IC_{50}$ (HMT) = 1.57 μM | 8 | | $K_D$ (SPR) = 0.000323 μM<br>τ = 132 min<br>$IC_{50}$ (MLL1) = 0.043 μM |

TABLE 6

Effect of different substituents at A on residence time (t) and MLL1 inhibition:

| Example Number | A | SPR Kd (nM) | T (min) |
|---|---|---|---|
| 8 | F | <0.5 | >100 |
| 58 | H | 3.5 | 11.5 |
| 82 | Cl | 10 | 6.7 |
| 591 | CH$_3$ | 26 | 17.4 |
| 592 | CF$_3$ | >10000 | ND |
| 593 | OCH$_3$ | >200 | ND |

The invention claimed is:

1. A compound selected from the group consisting of:

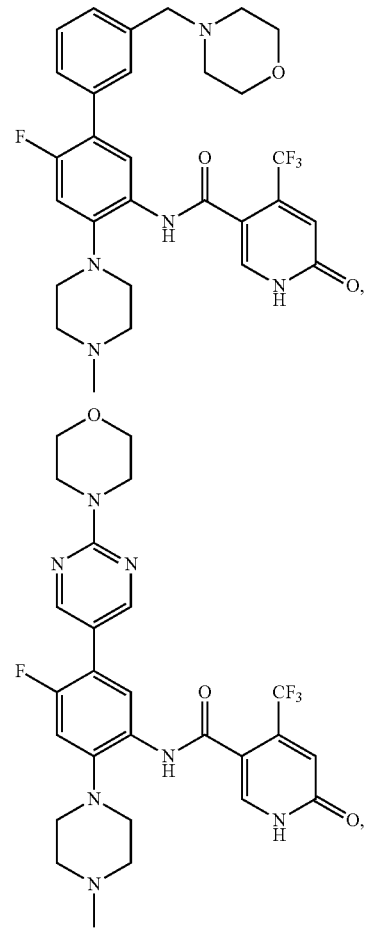

1557
-continued
1558
-continued
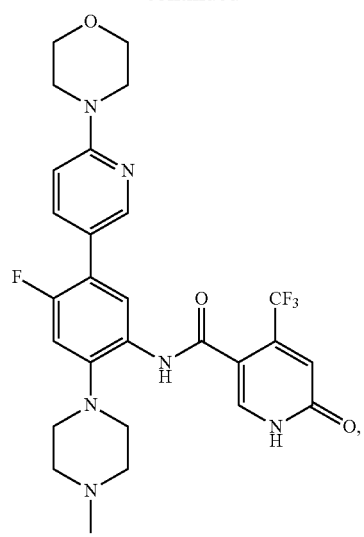
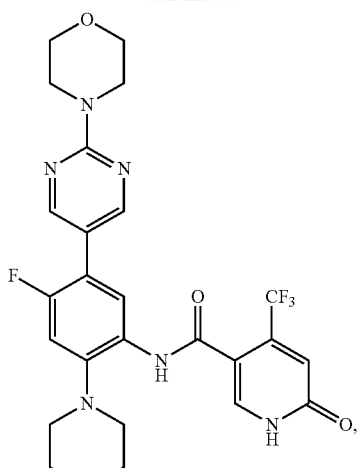

1559
-continued
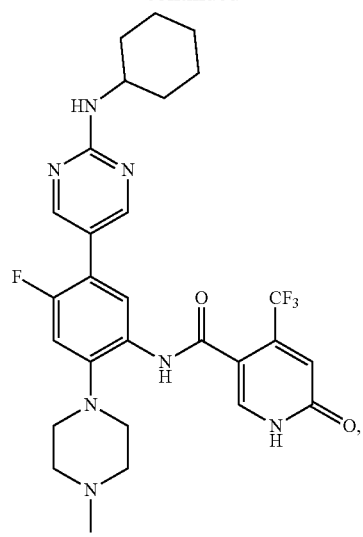
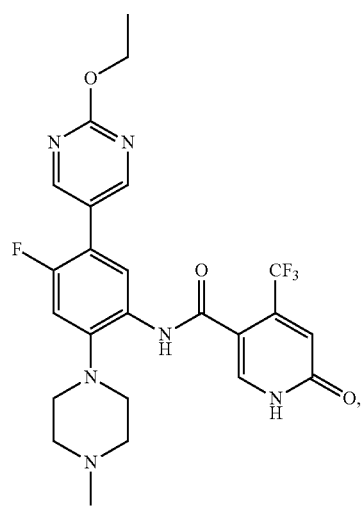
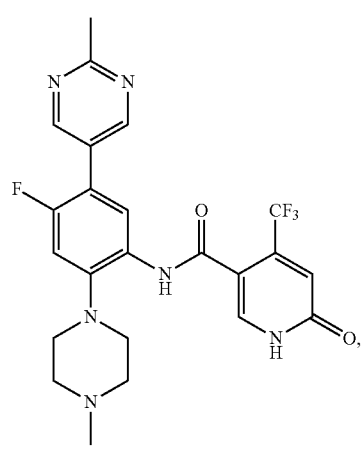
1560
-continued
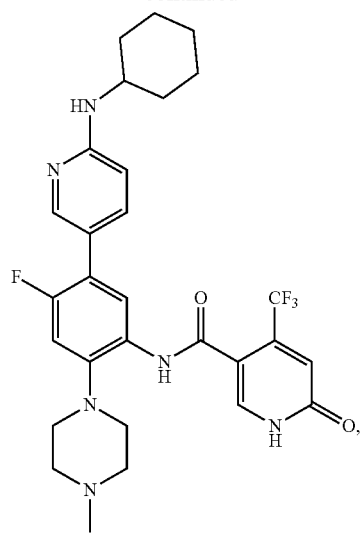
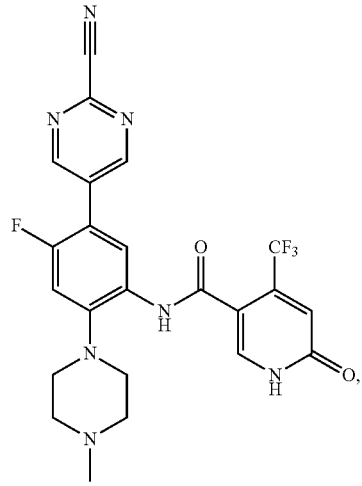

1561
-continued
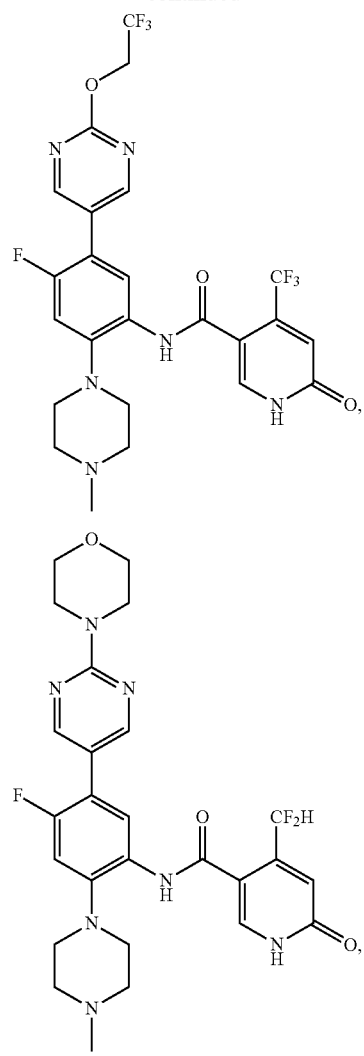
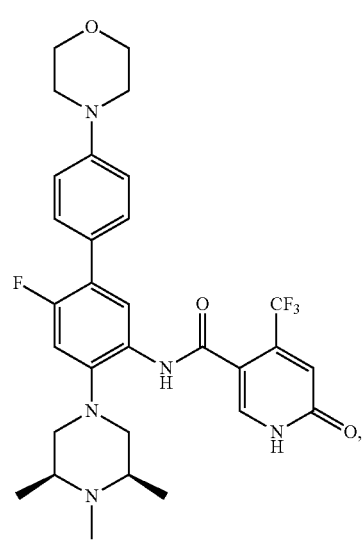
1562
-continued
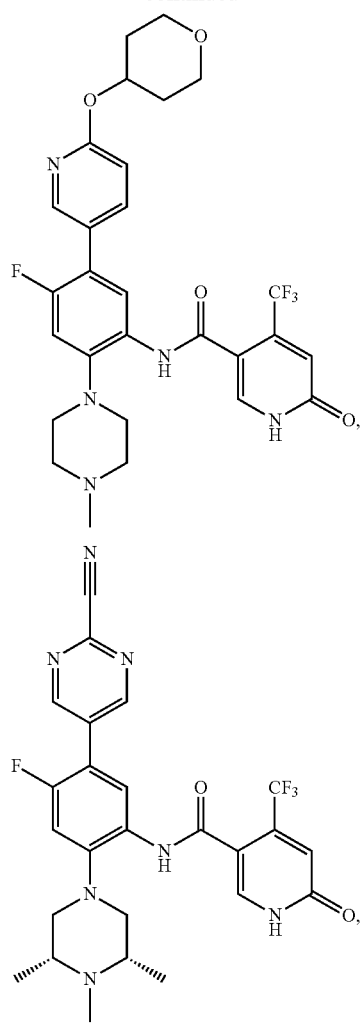
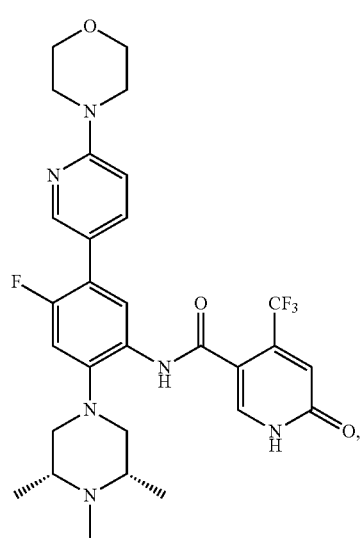

1563
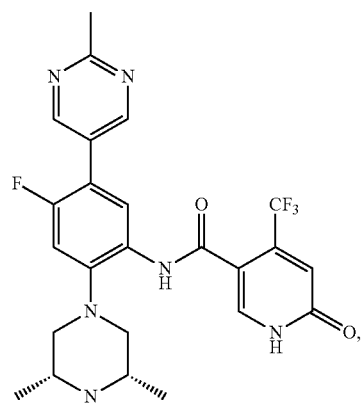
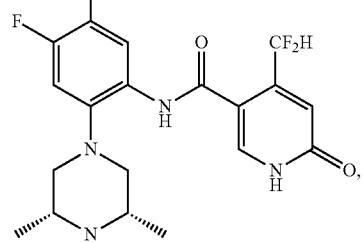
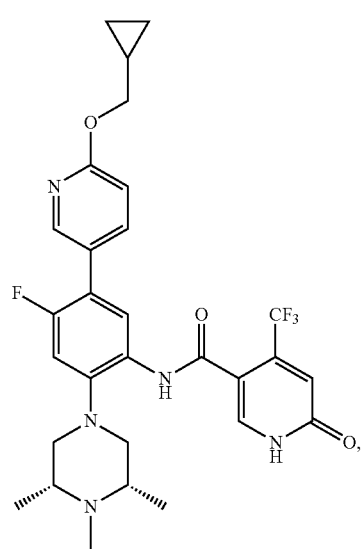
1564
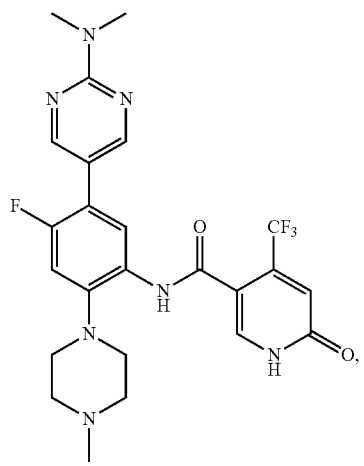
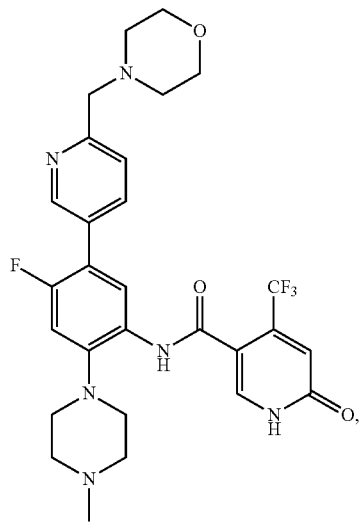
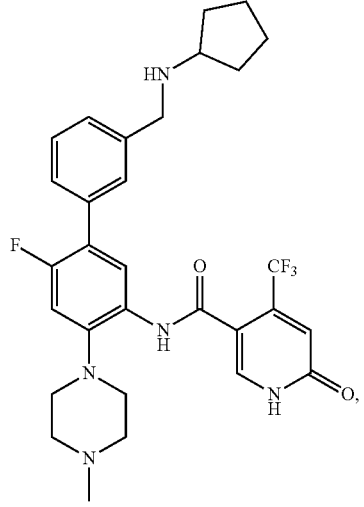

1565
-continued
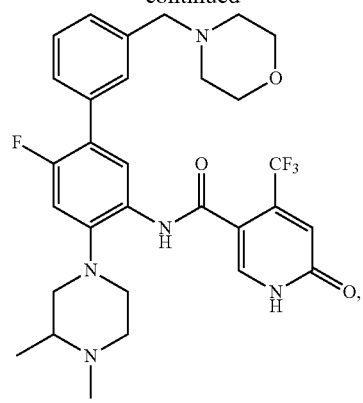
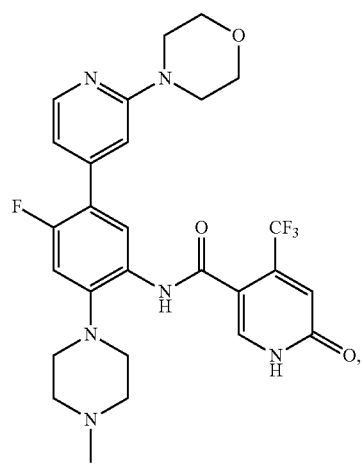
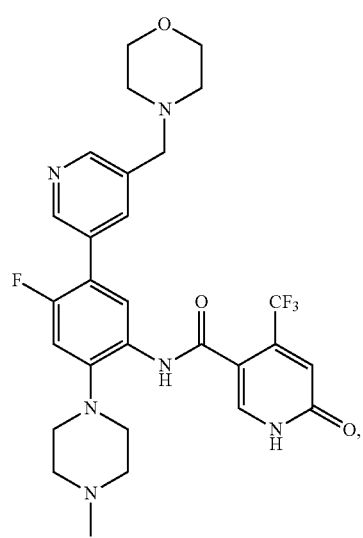
1566
-continued
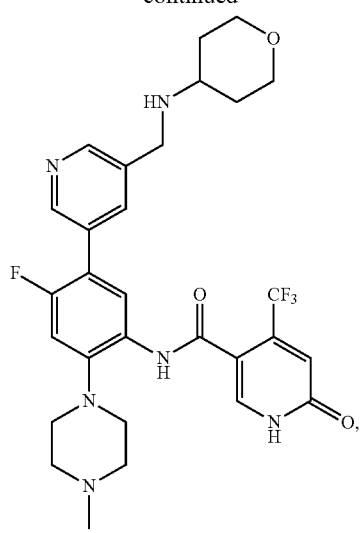
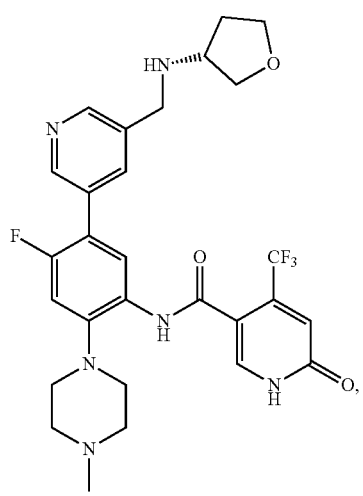
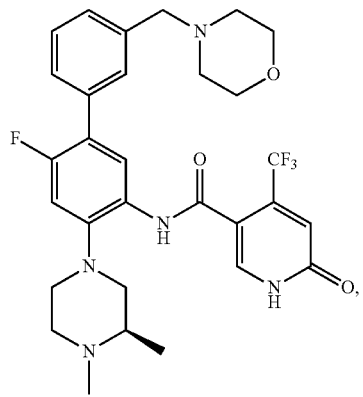

1567
-continued
1568
-continued
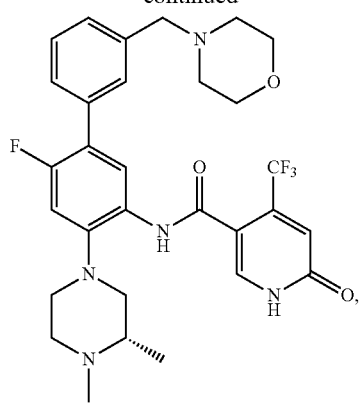
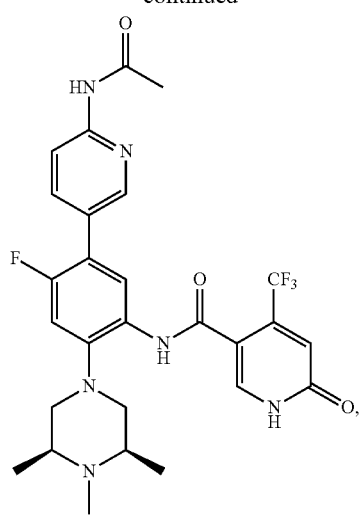
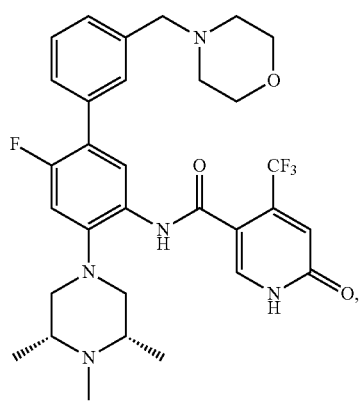
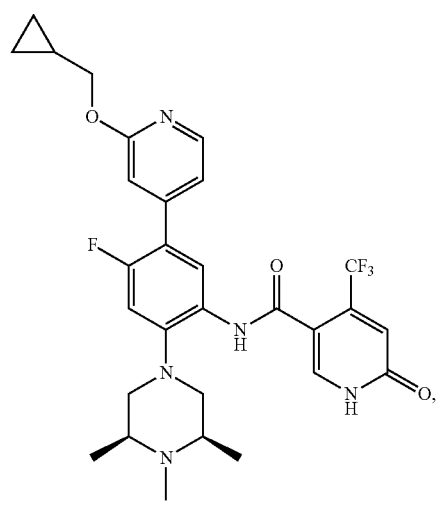
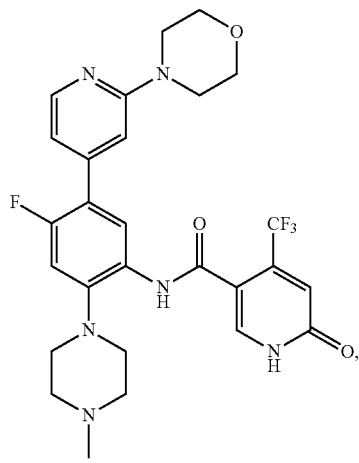
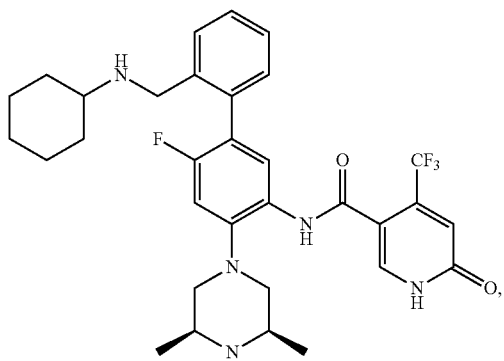

1569
-continued
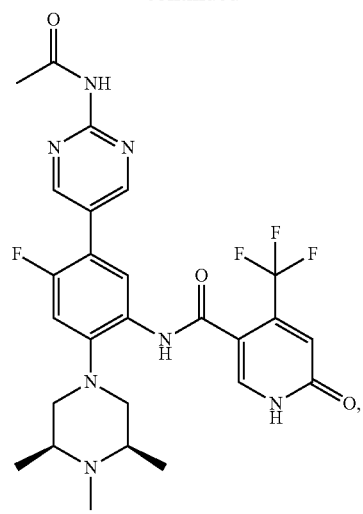
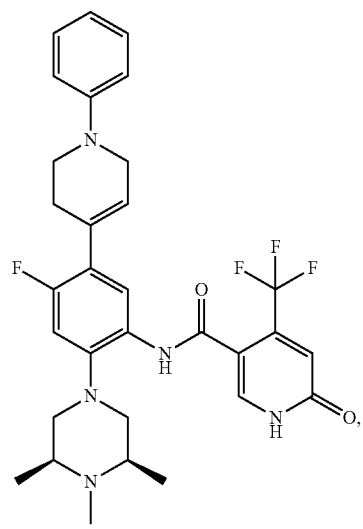

1570
-continued
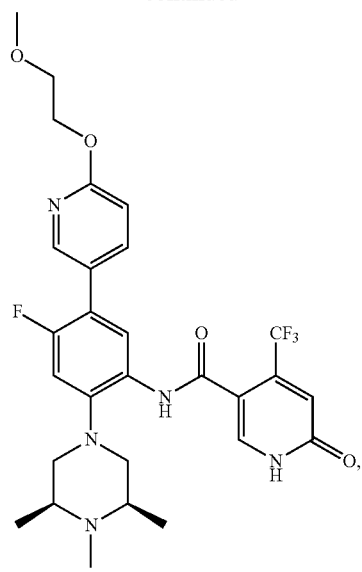
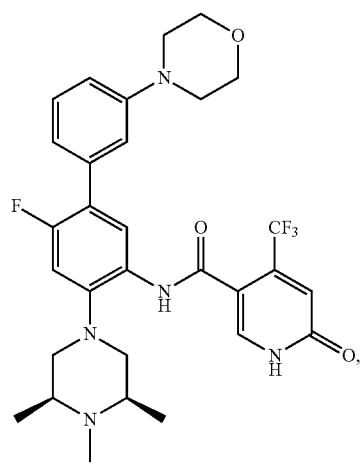
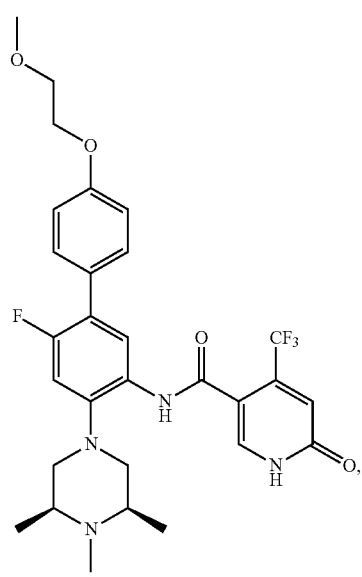

1571
-continued
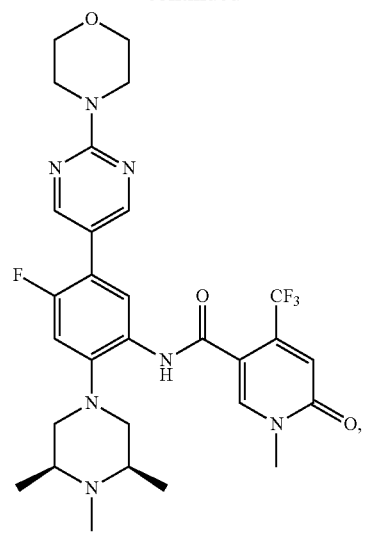
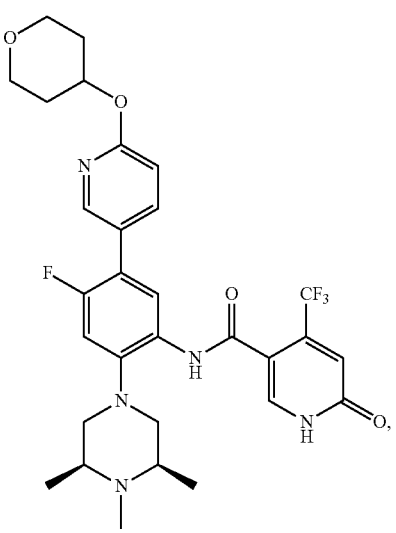
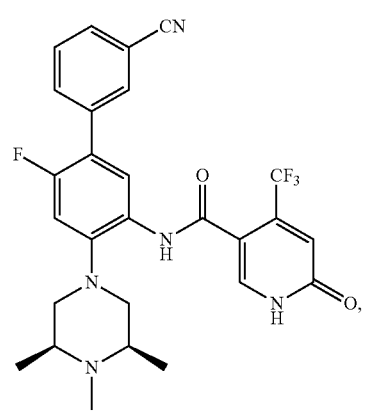
1572
-continued
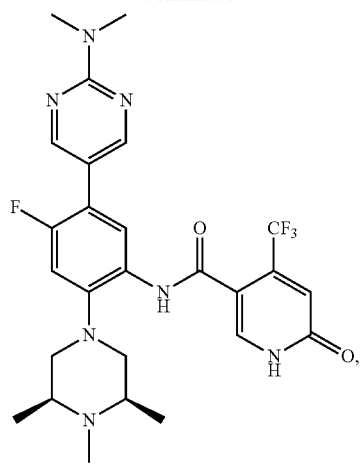
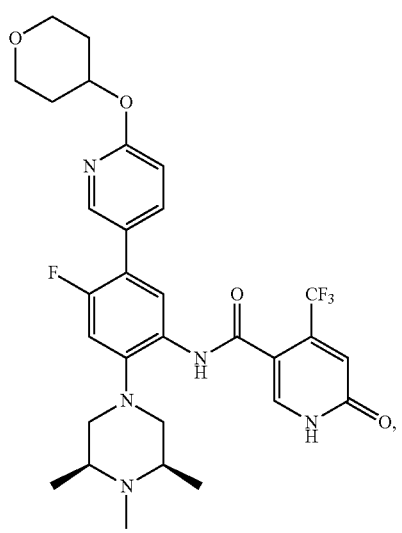
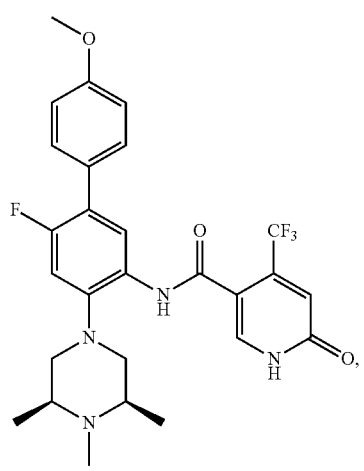

1573
-continued
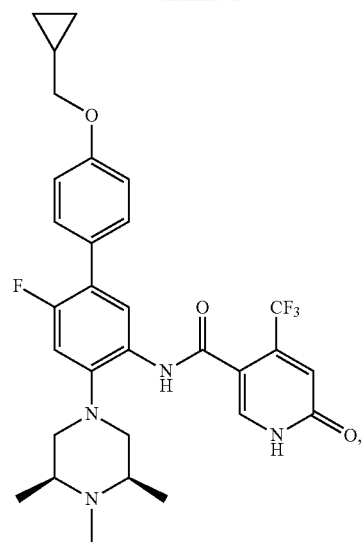
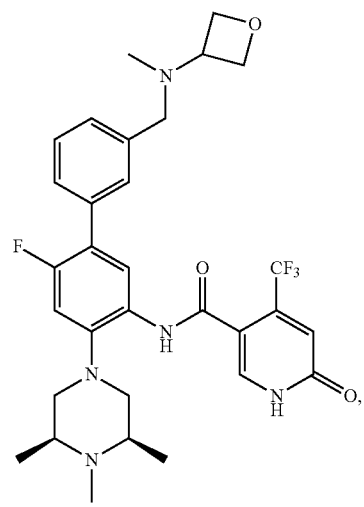
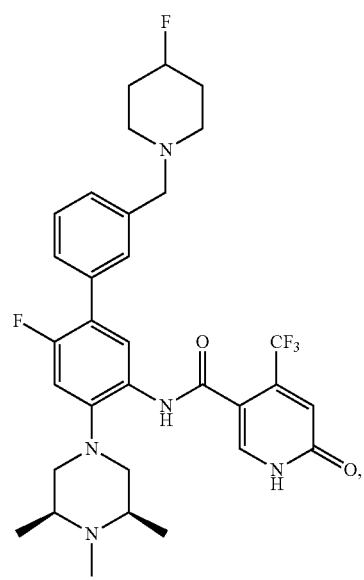
1574
-continued
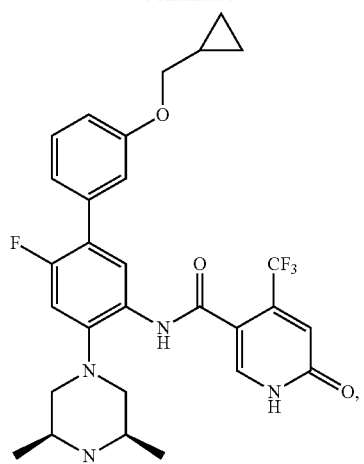
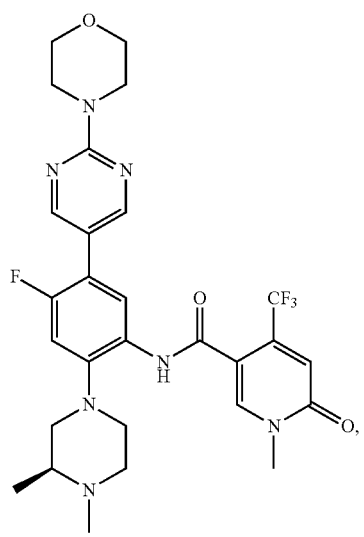
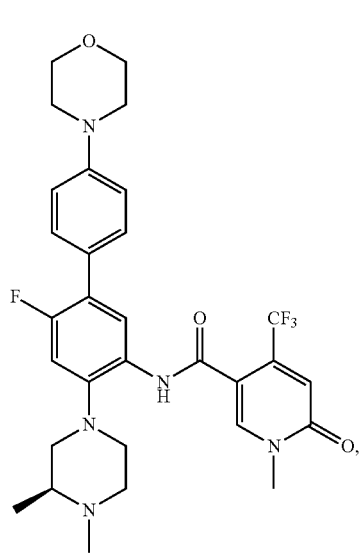

1575
-continued
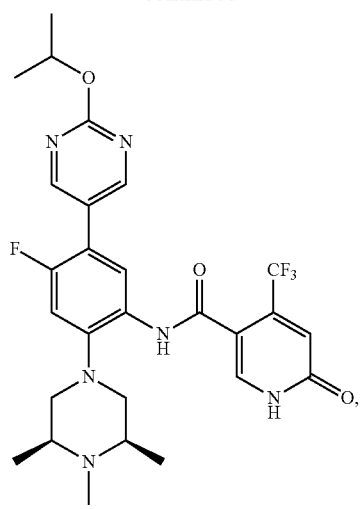
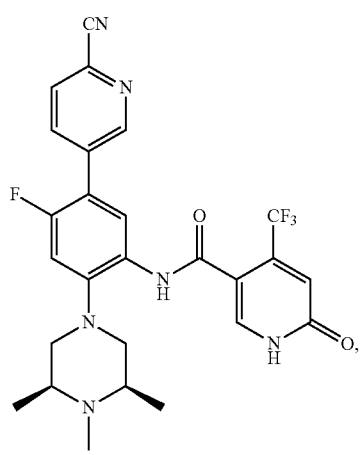
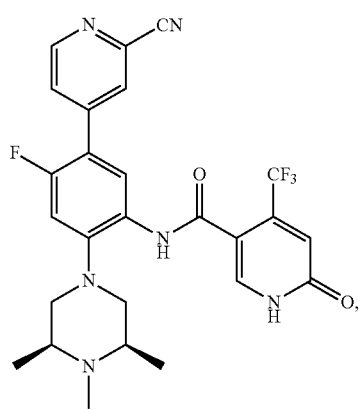
1576
-continued
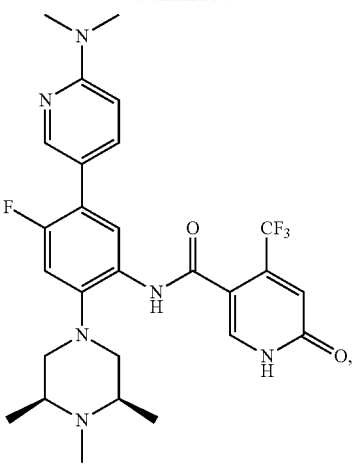
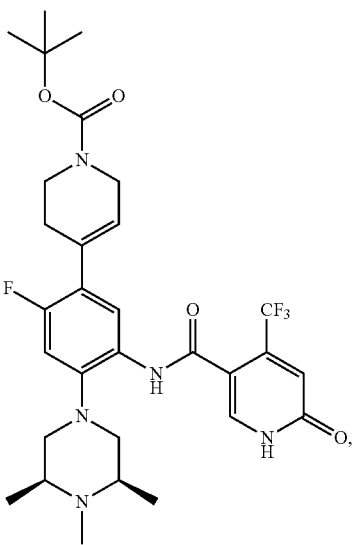
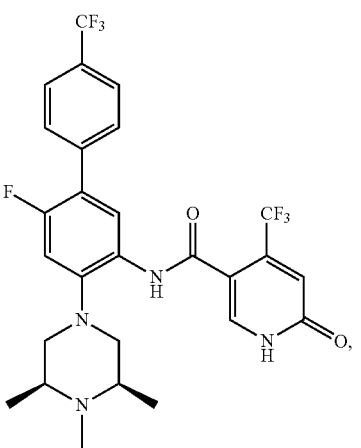

1577
-continued
1578
-continued
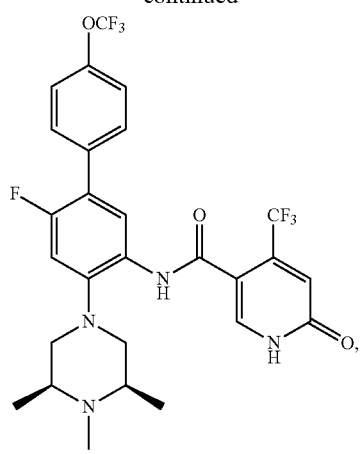
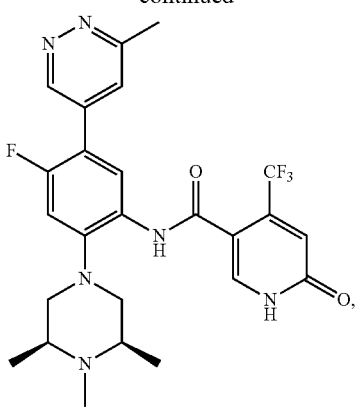
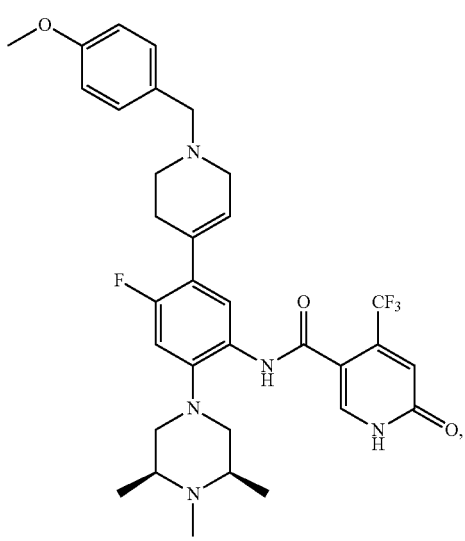

1579
-continued
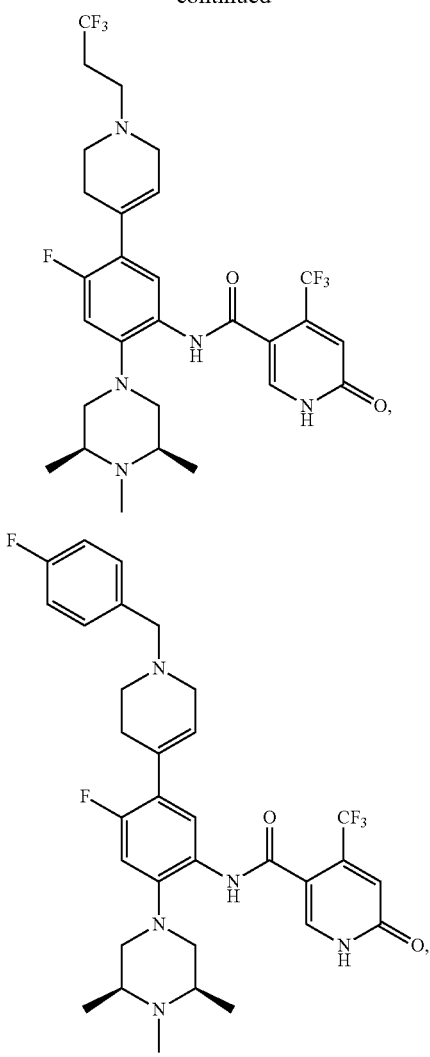
1580
-continued
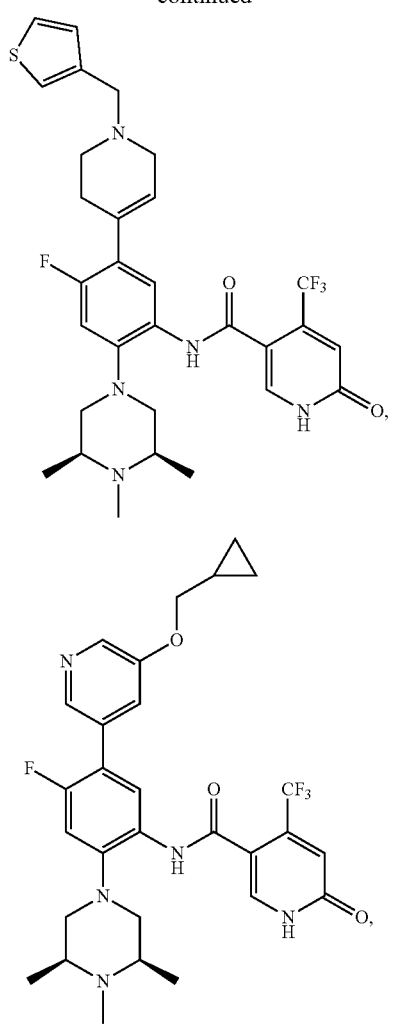

1581
-continued
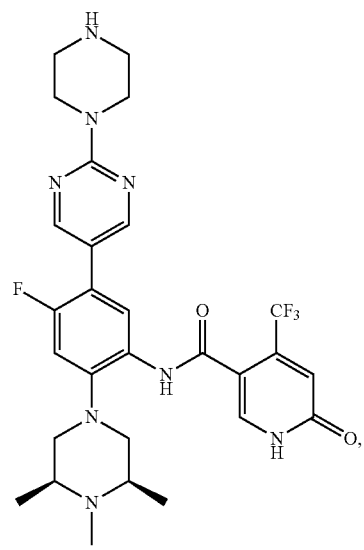
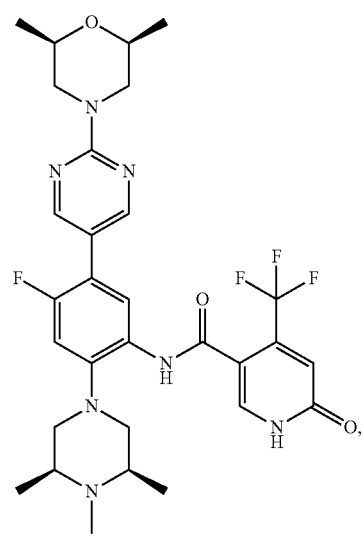
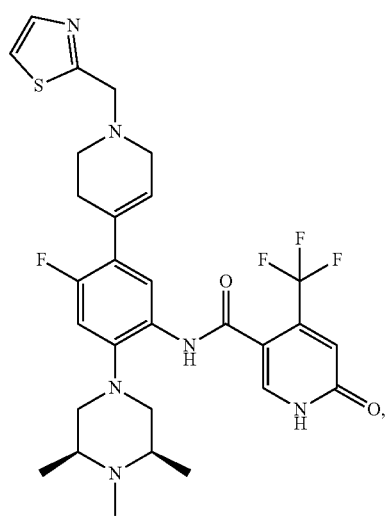
1582
-continued
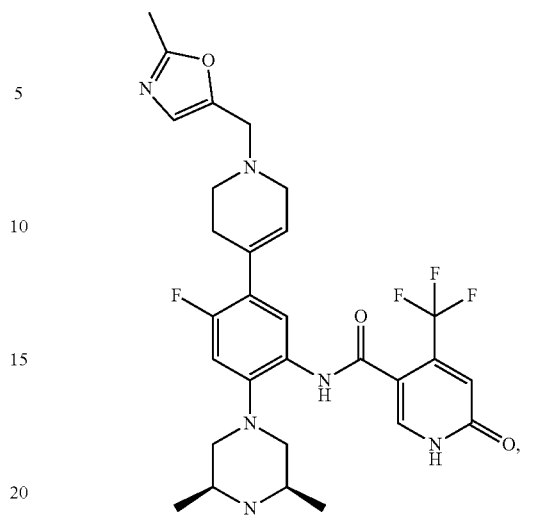
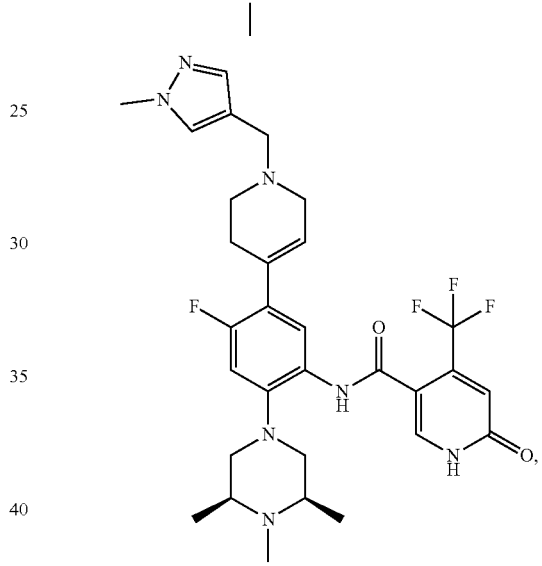
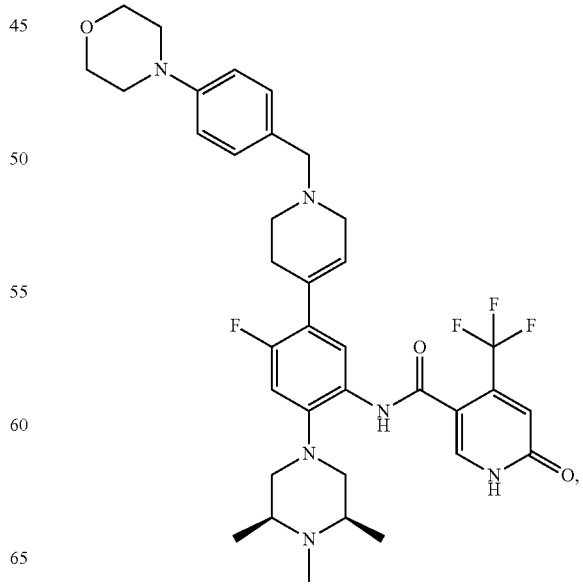

1583
-continued
1584
-continued
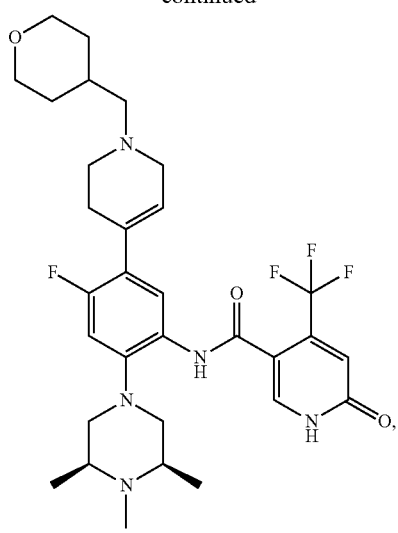
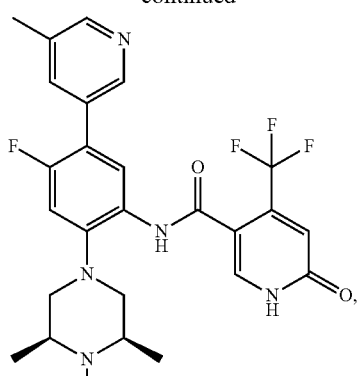
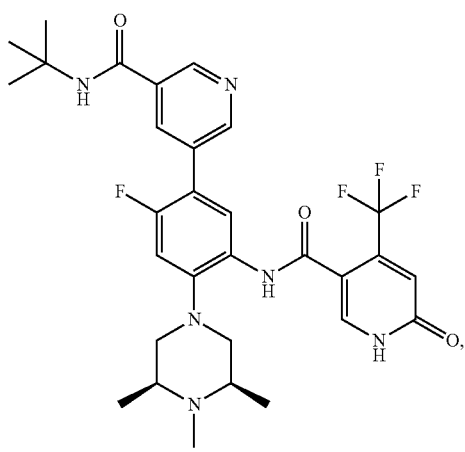
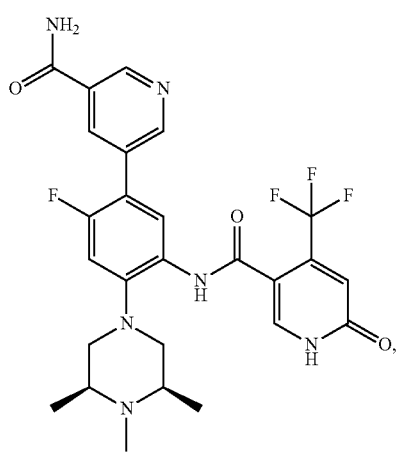

1585
-continued
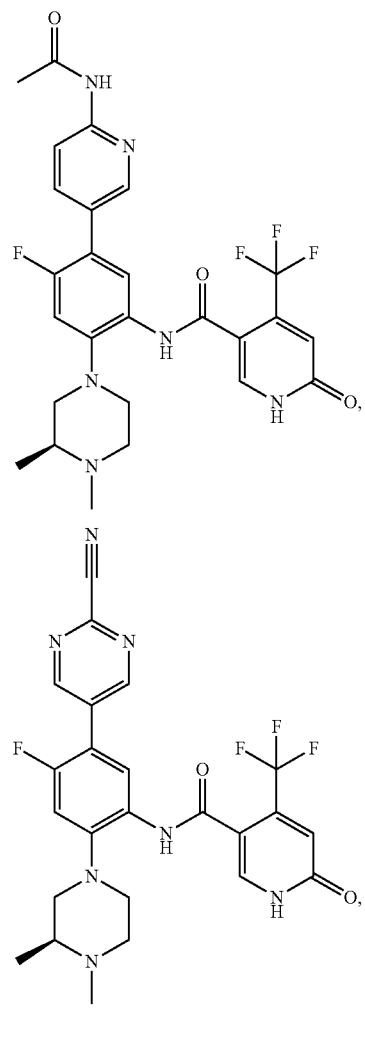
1586
-continued
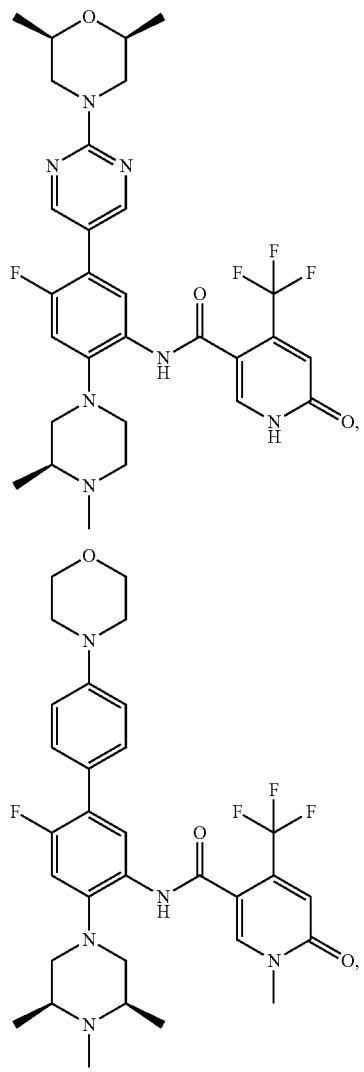
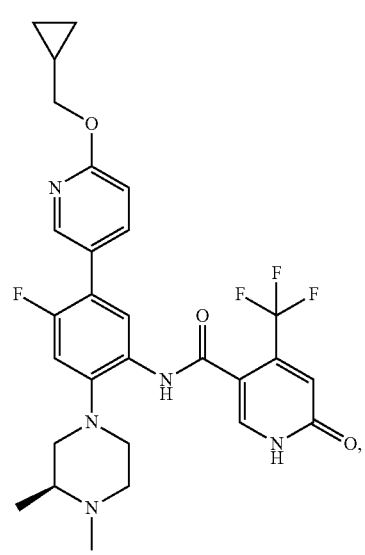
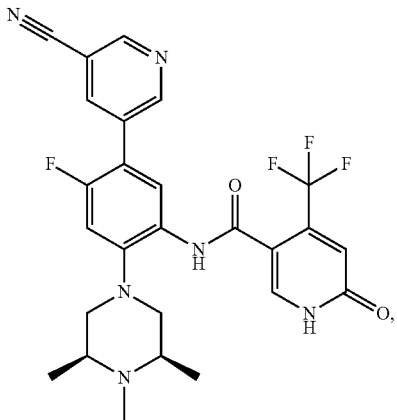

1587
-continued
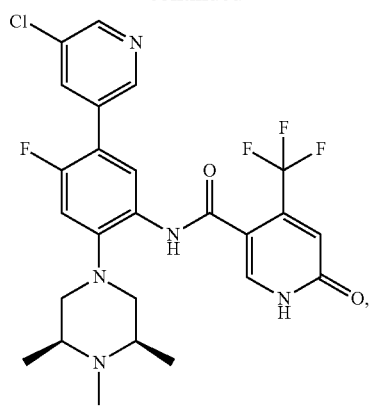
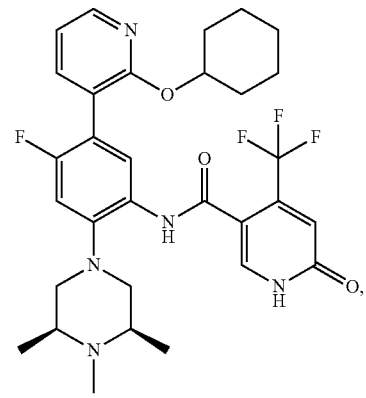
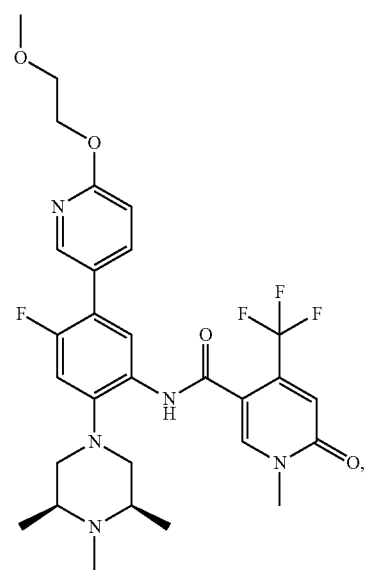
1588
-continued
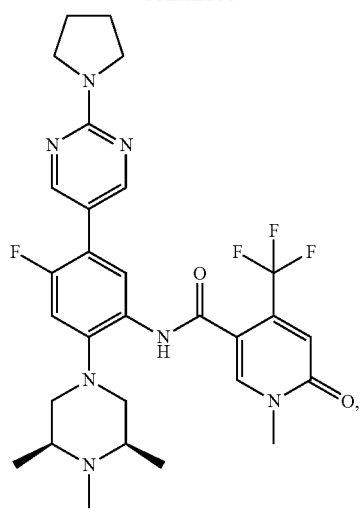
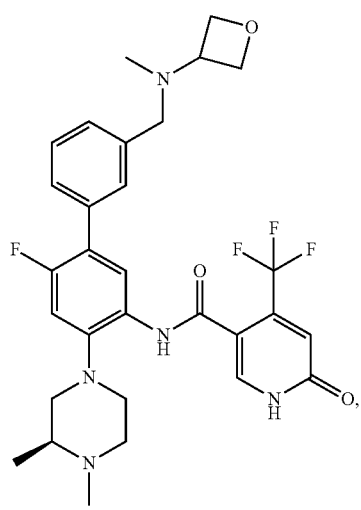
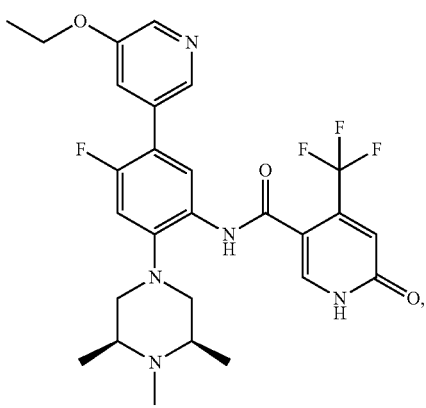

1589
-continued
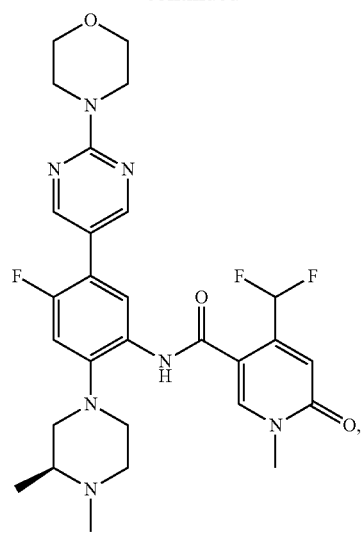
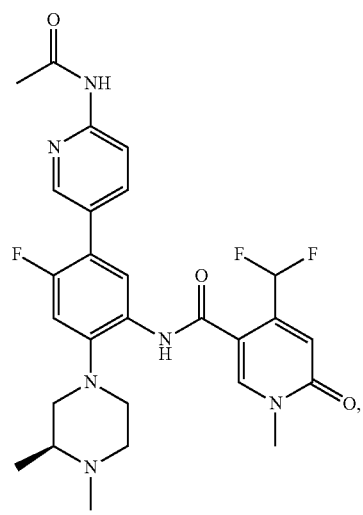
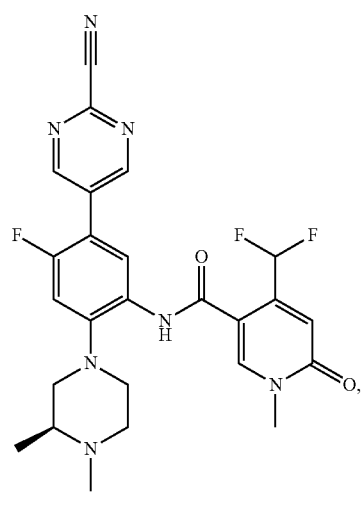
1590
-continued
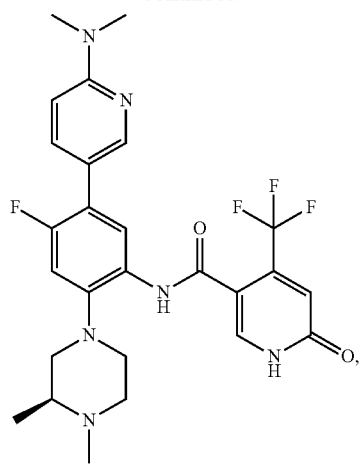
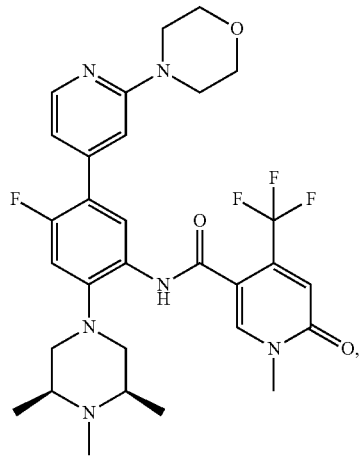
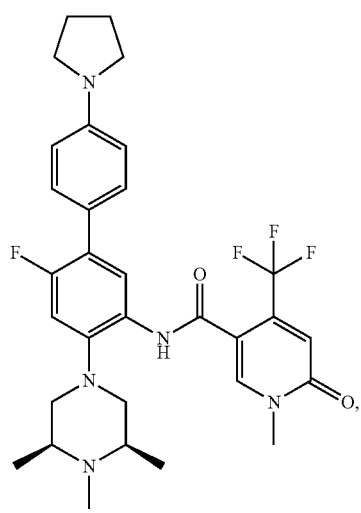

1591
-continued
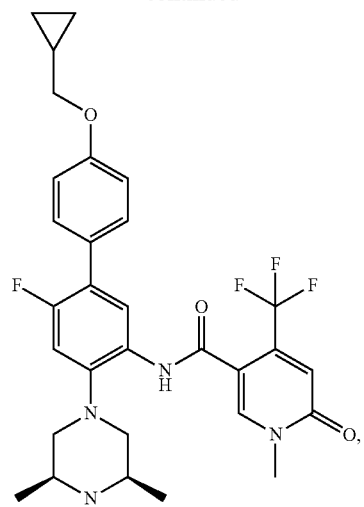
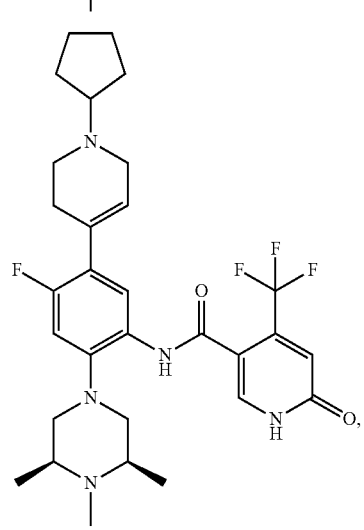
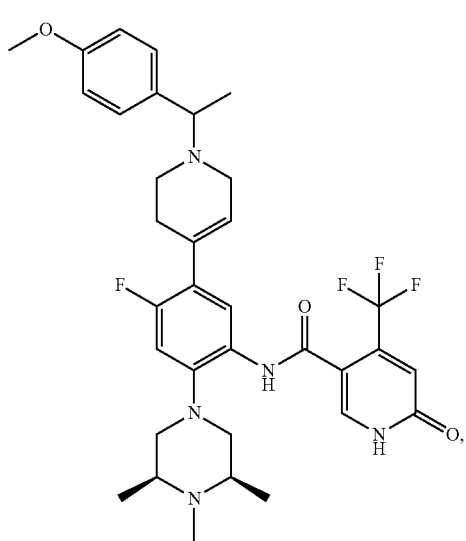
1592
-continued
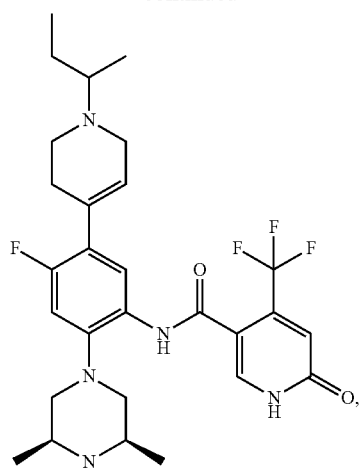
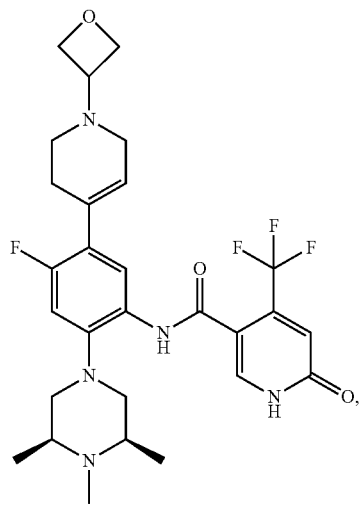
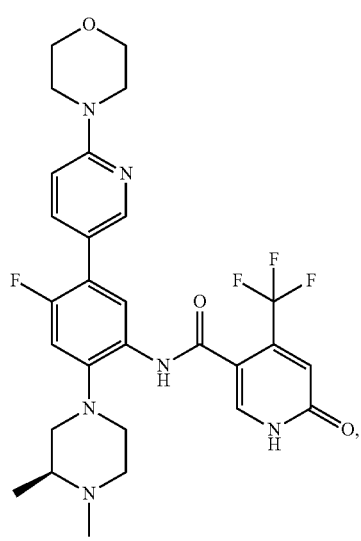

1593
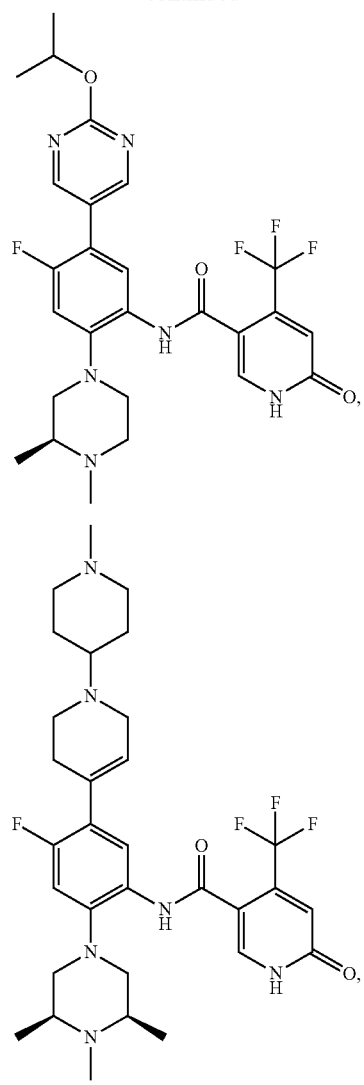
1594
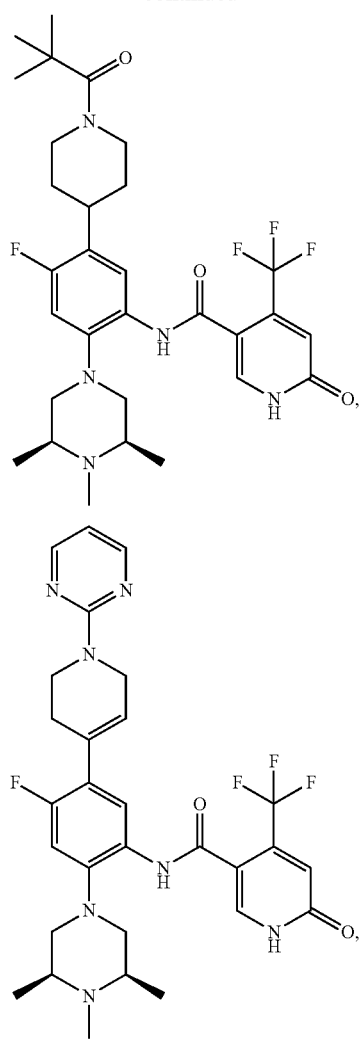
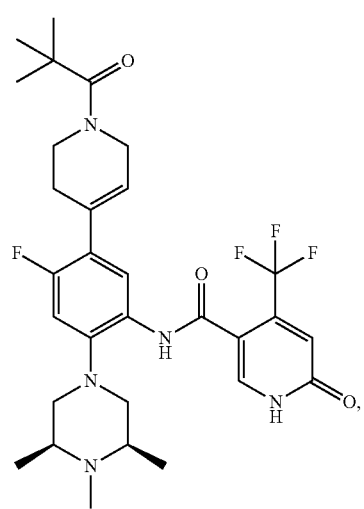
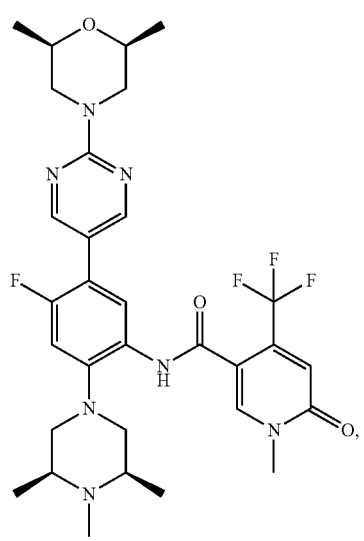

1595
-continued
1596
-continued
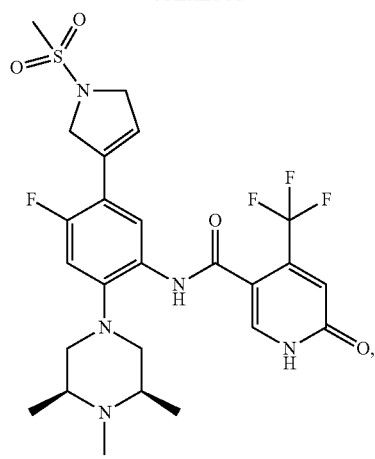
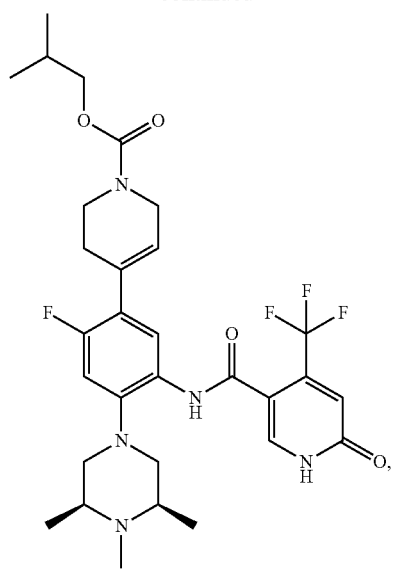
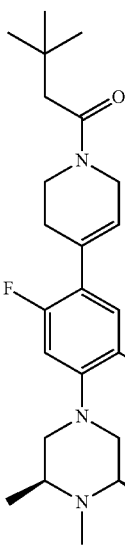
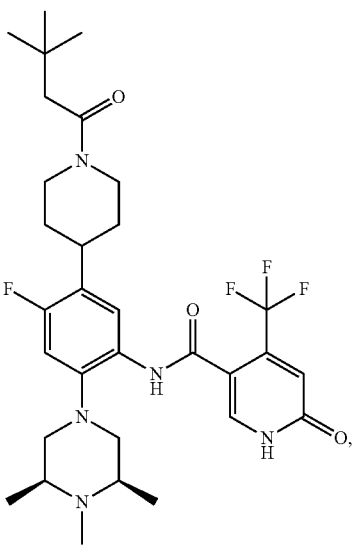

1597
-continued
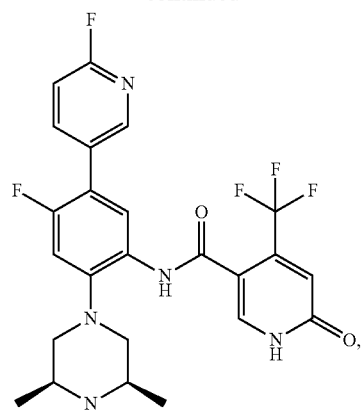
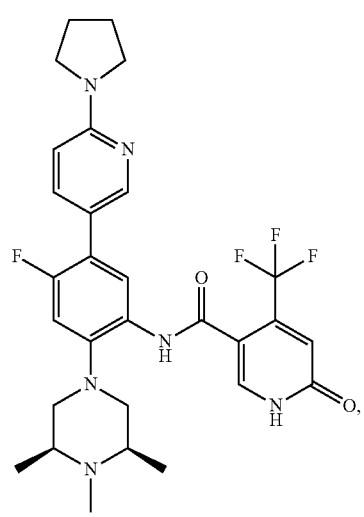
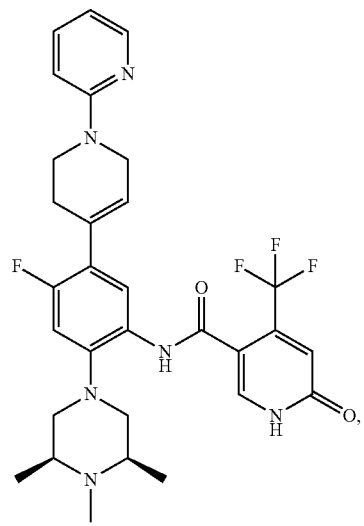
1598
-continued
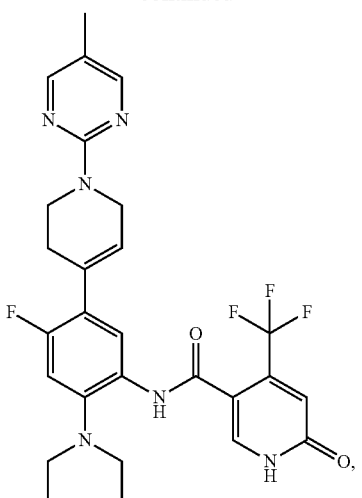
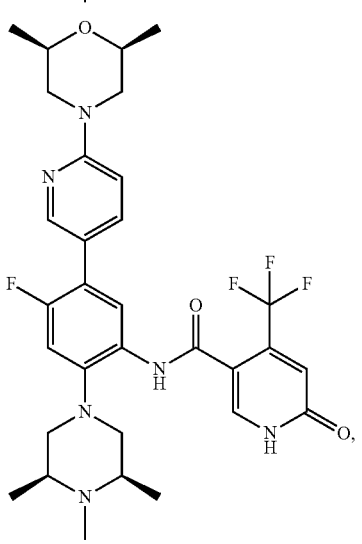
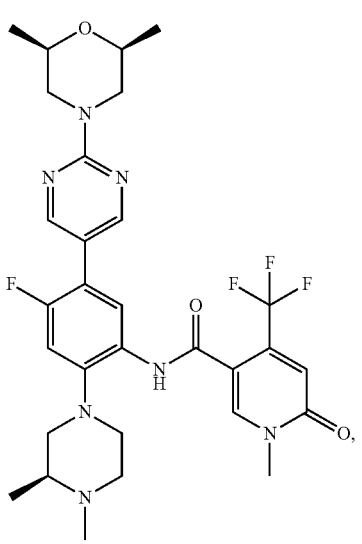

1599
-continued
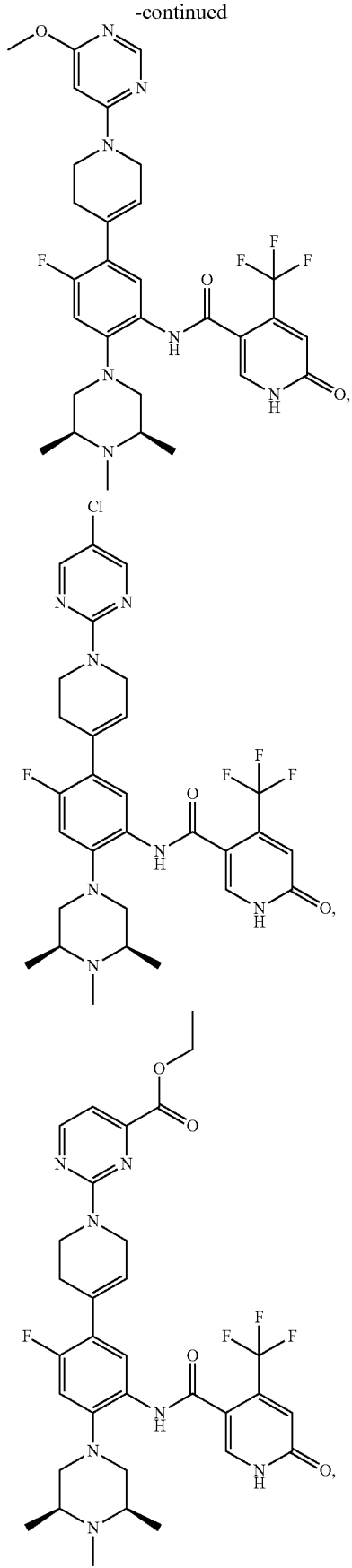
1600
-continued
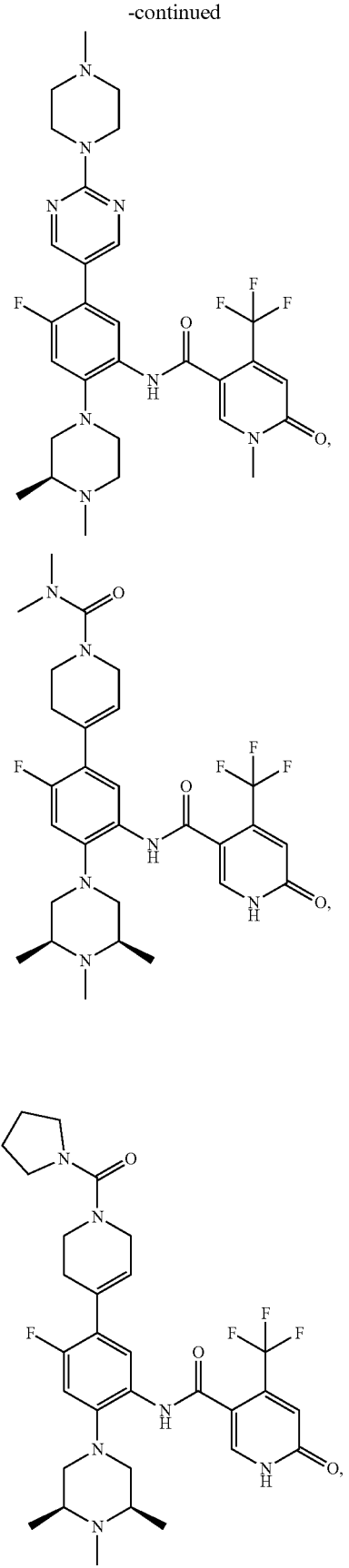

1601
-continued
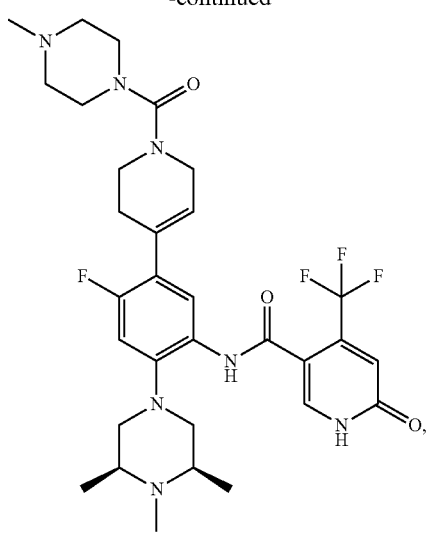
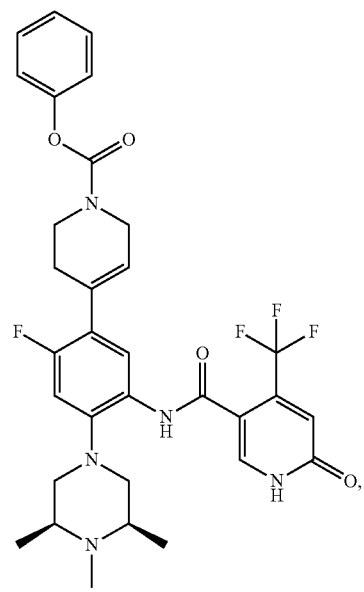
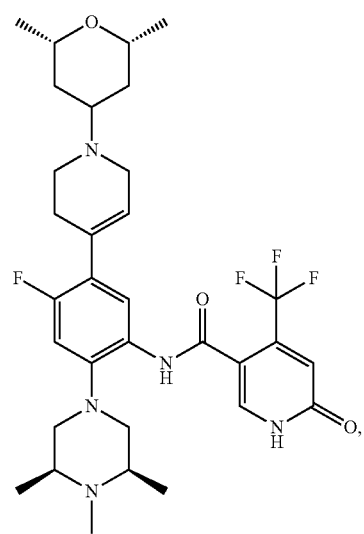
1602
-continued
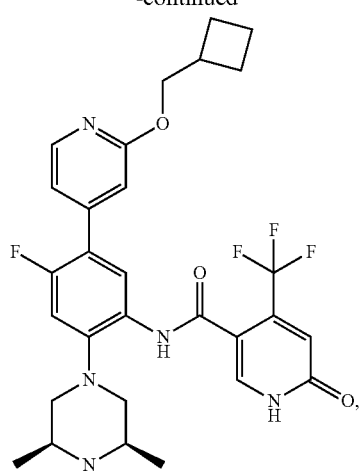
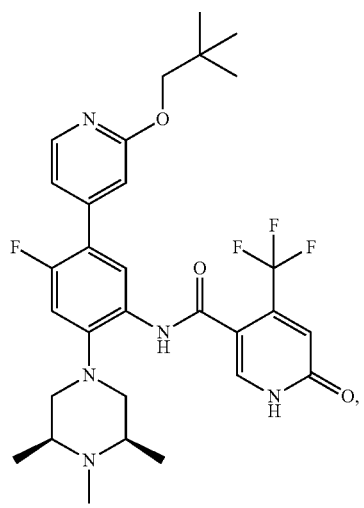
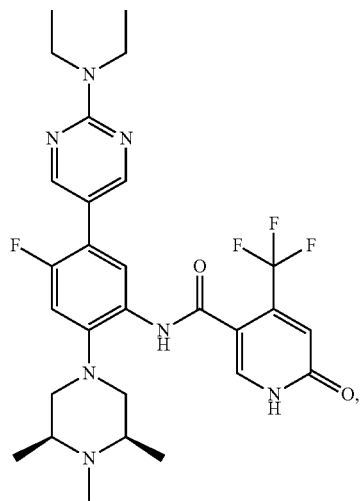

1603
-continued
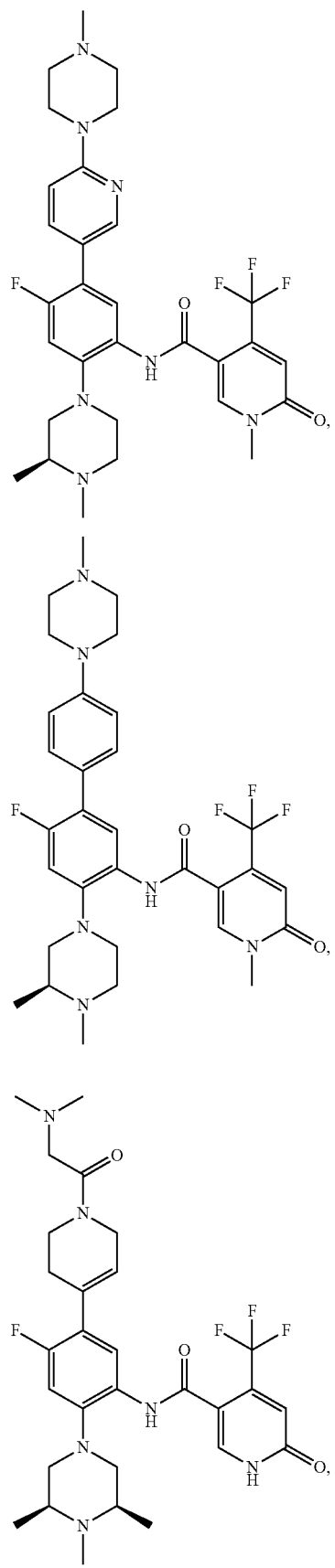
1604
-continued
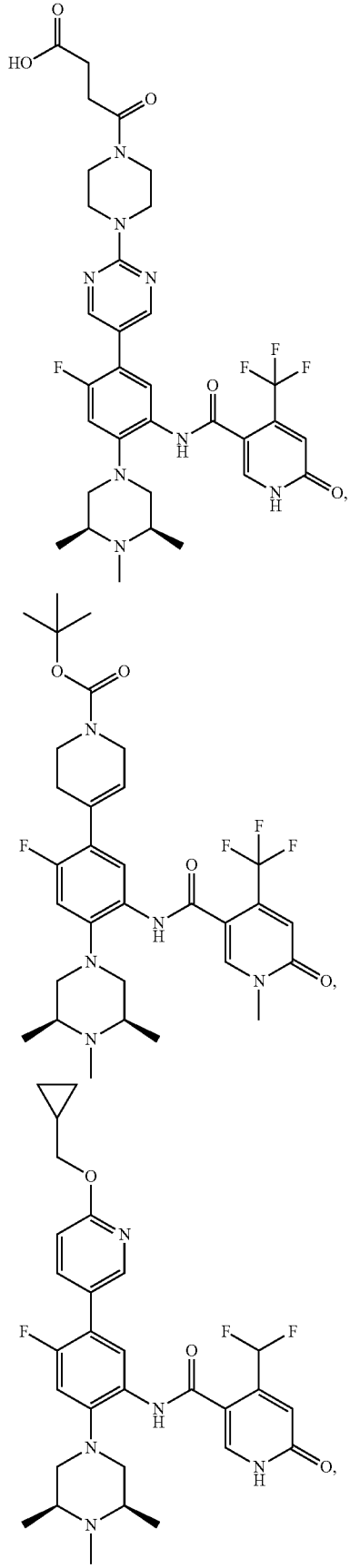

1605
-continued
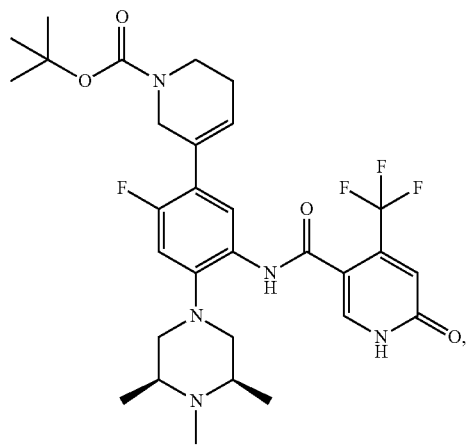
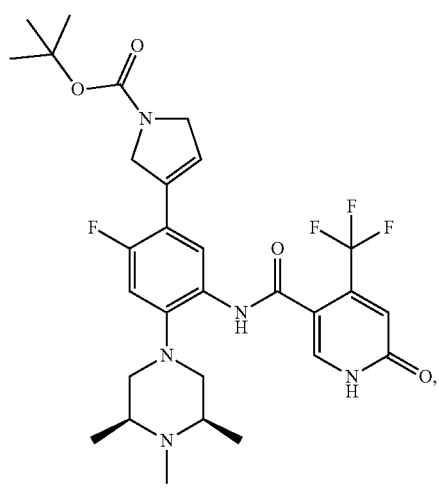
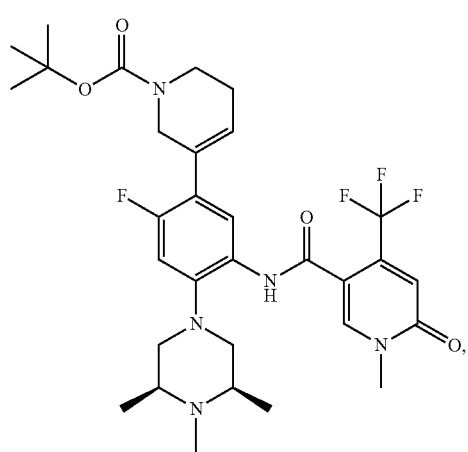
1606
-continued
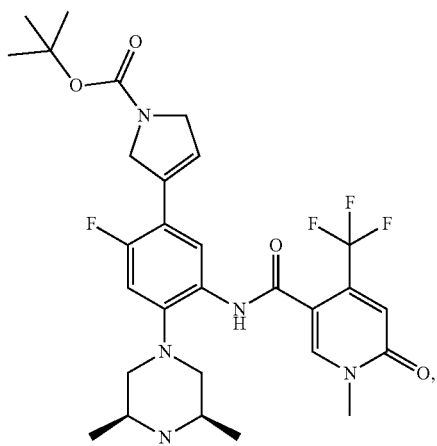
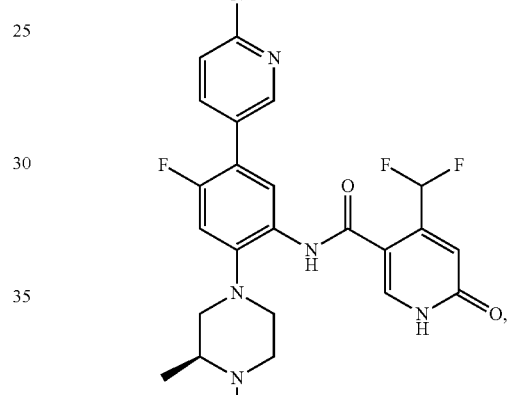
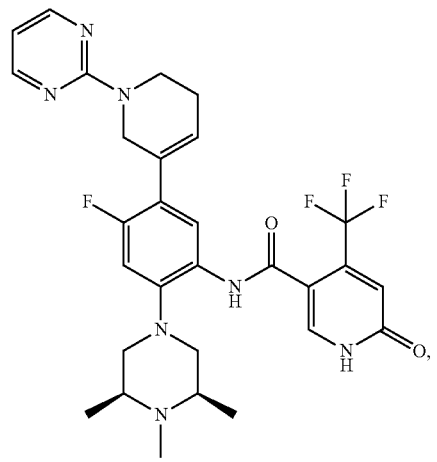

1607
-continued
1608
-continued
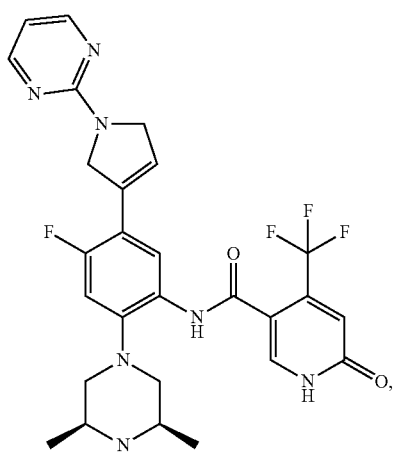
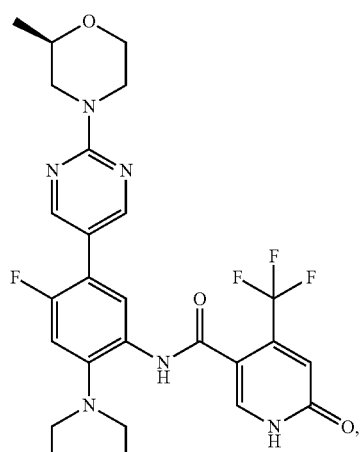
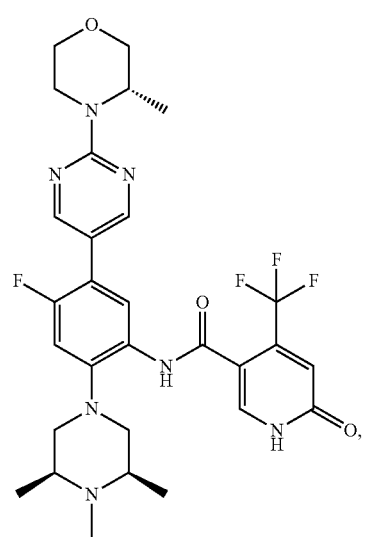

1609
-continued
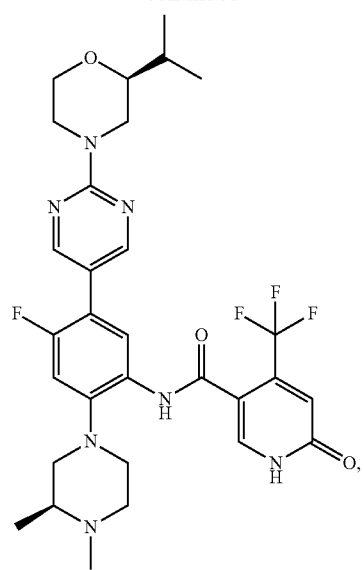
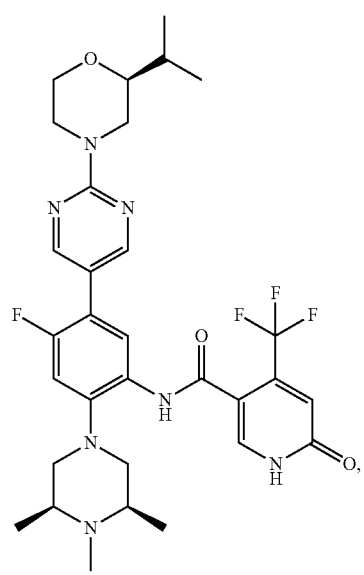
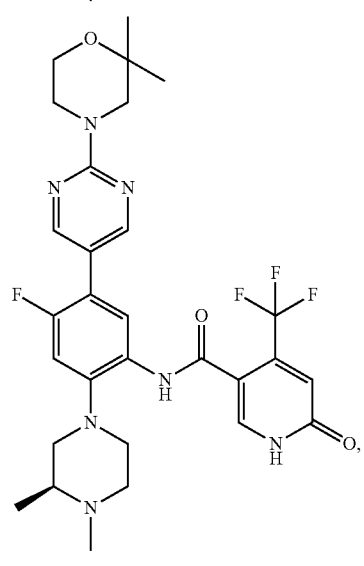
1610
-continued
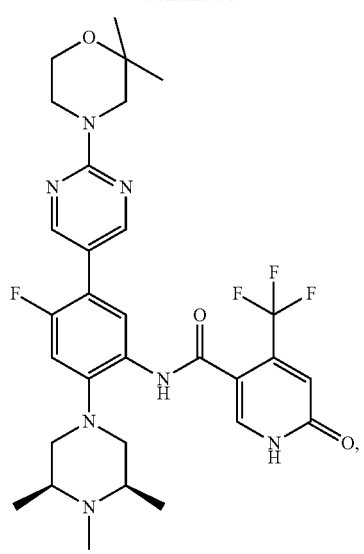
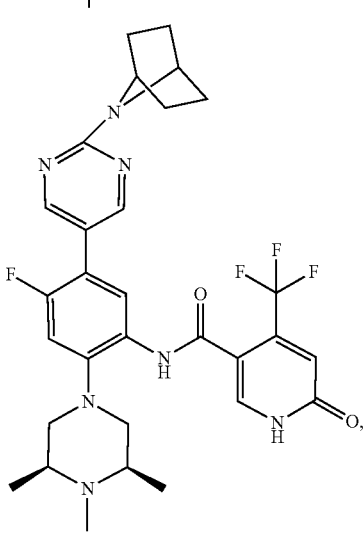
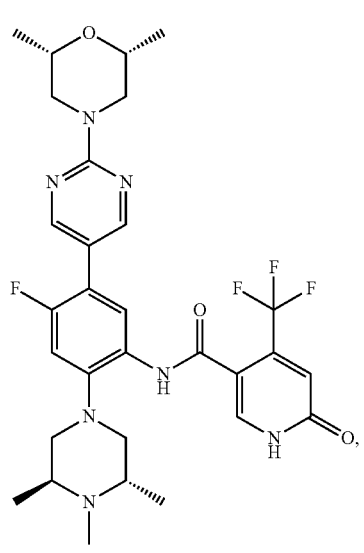

1611
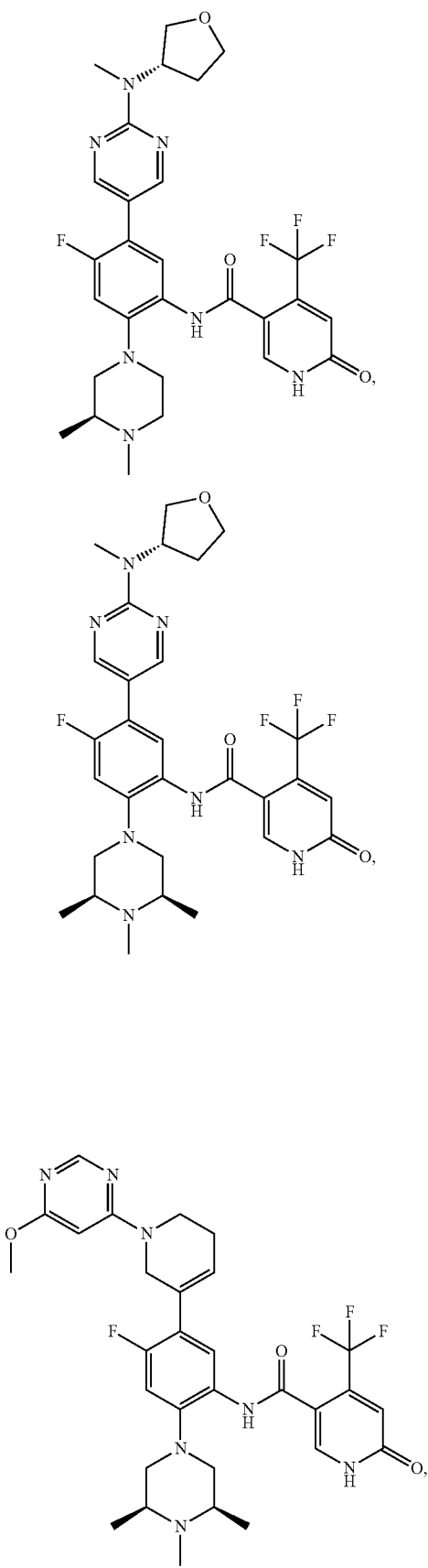
1612
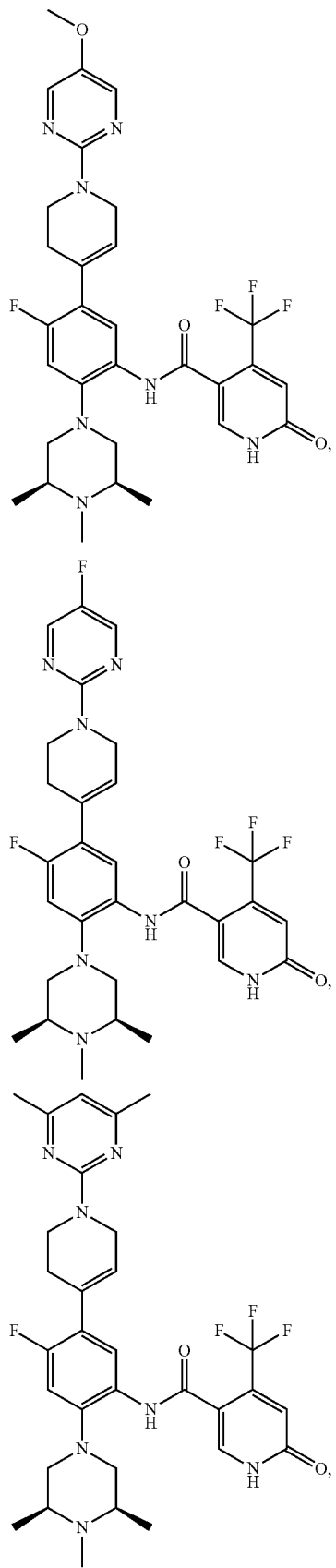

1613
-continued
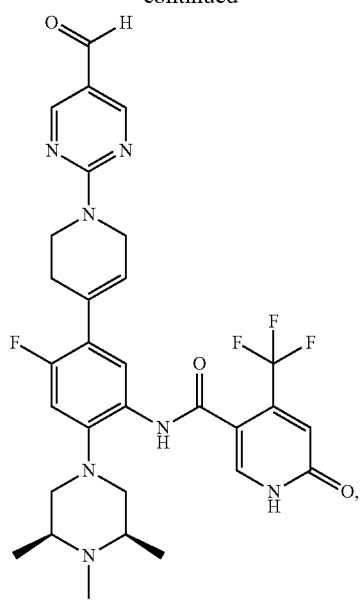
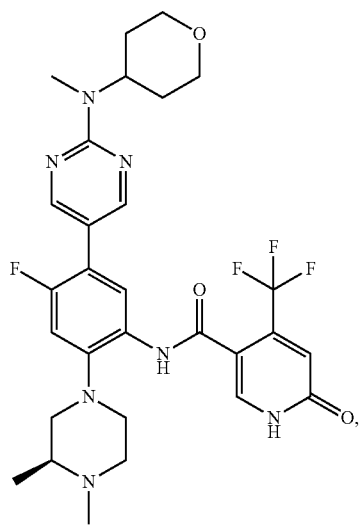
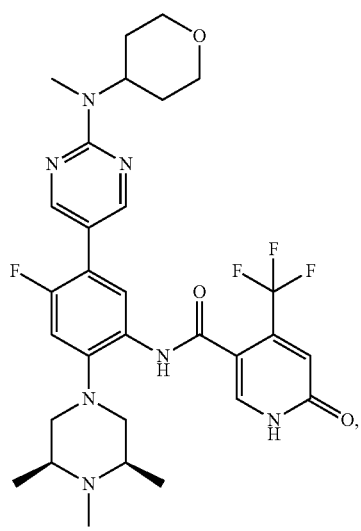
1614
-continued
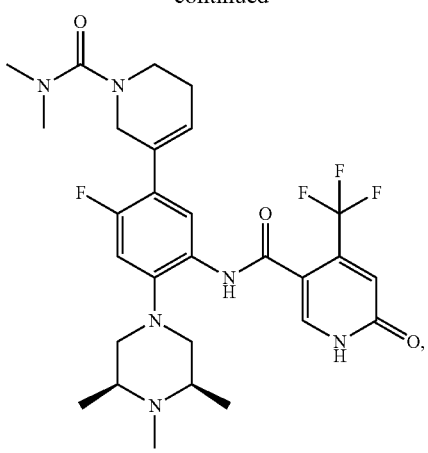
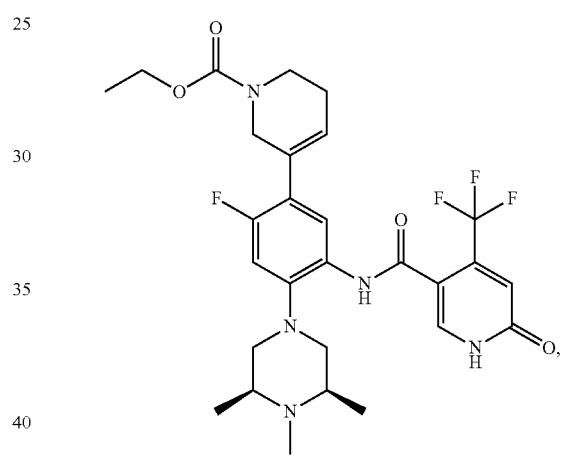
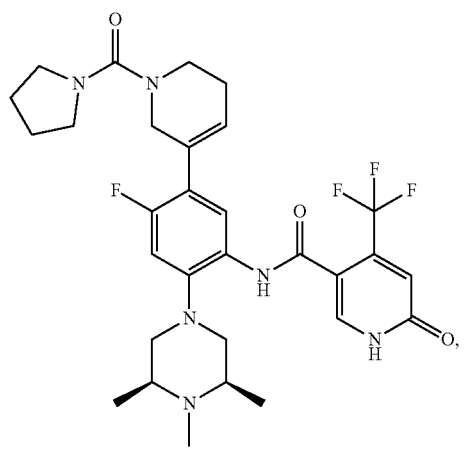

1615
-continued
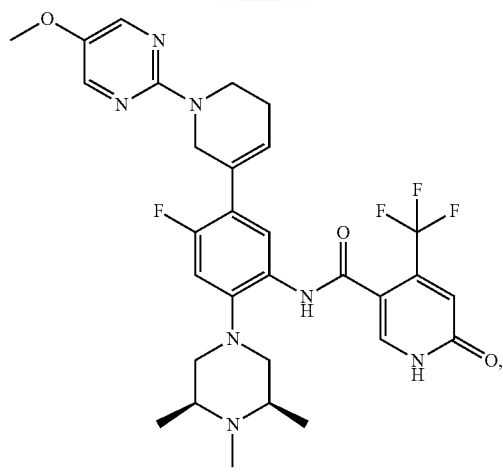
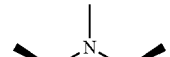
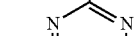
1616
-continued
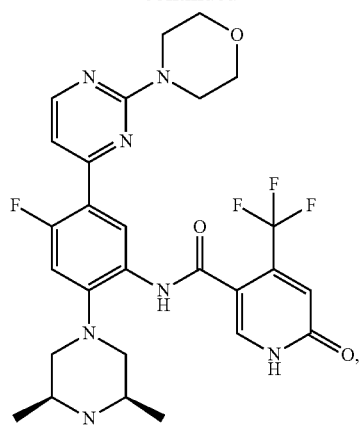
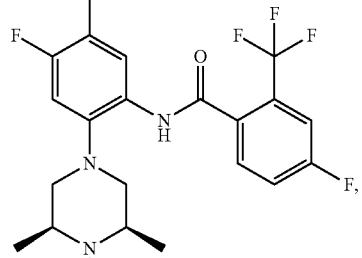
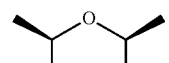
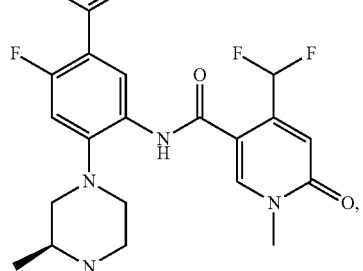

1617
-continued
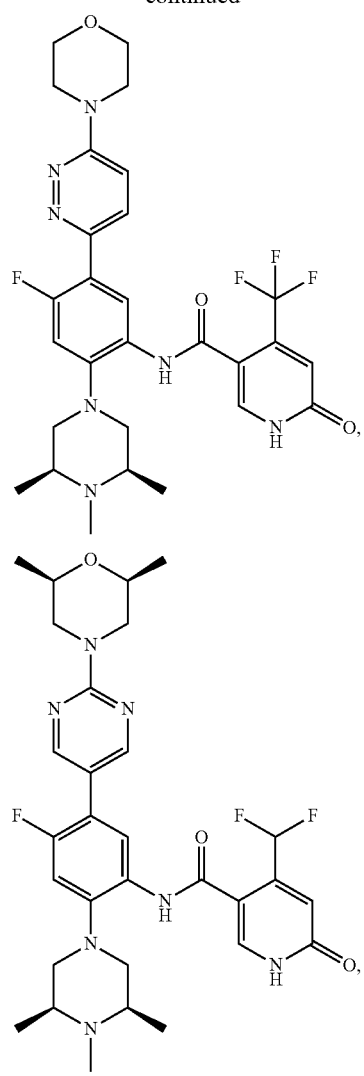
1618
-continued
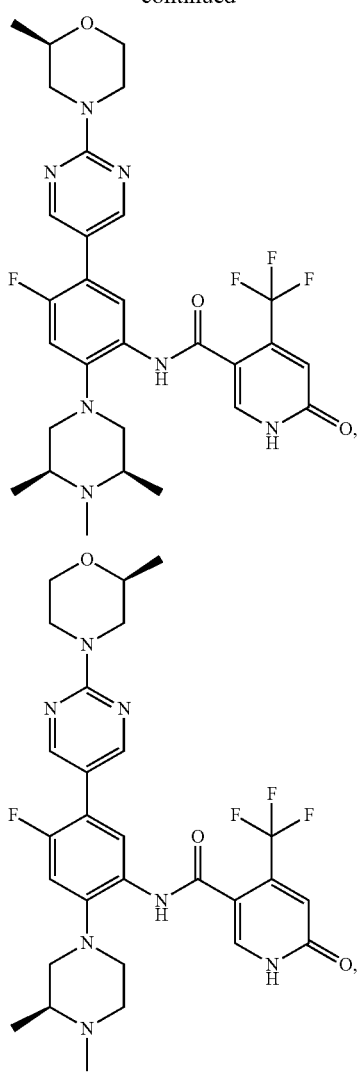
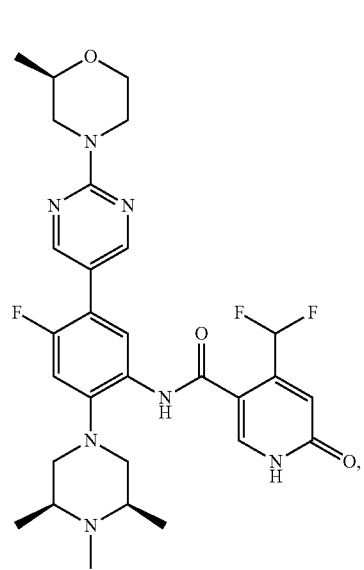

1619
-continued
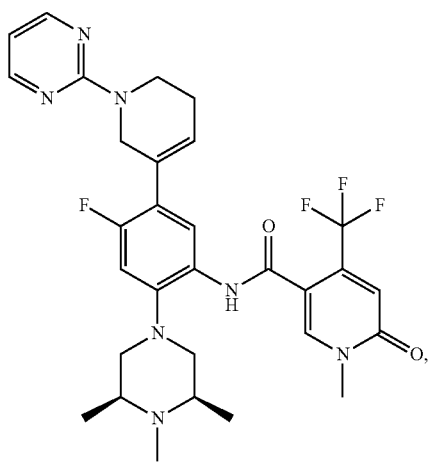
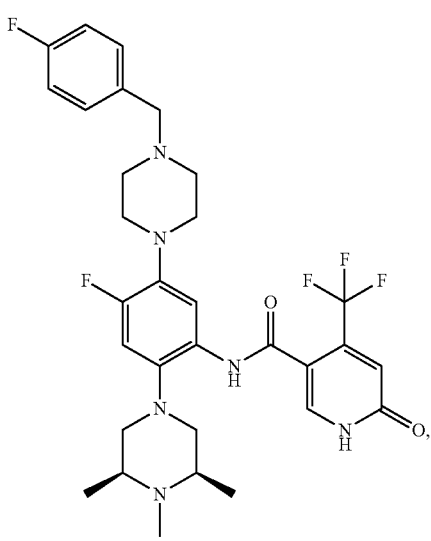
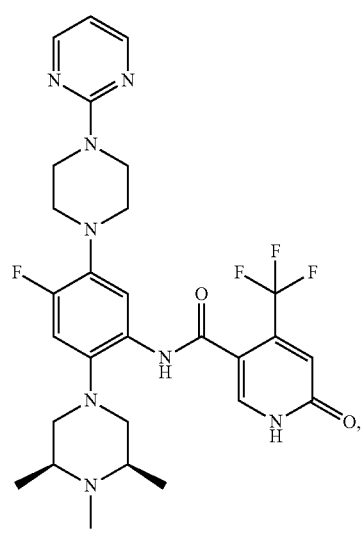
1620
-continued
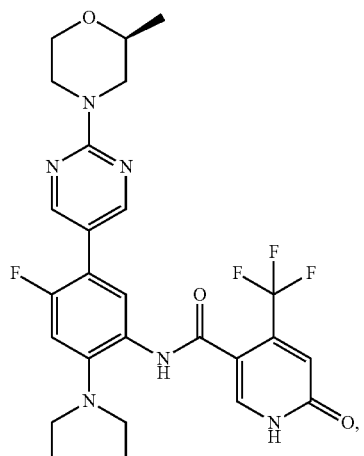
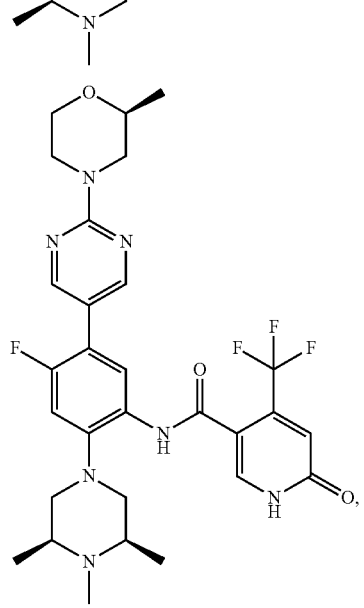
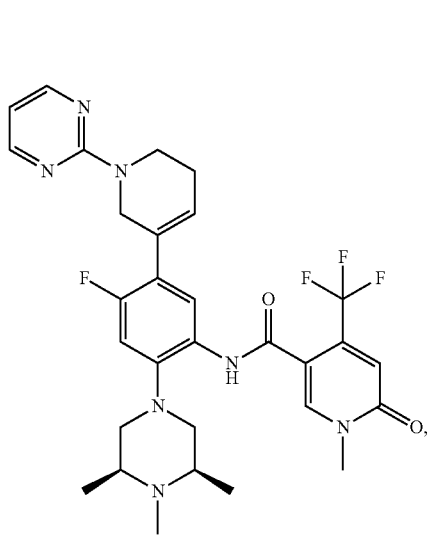

1621
-continued
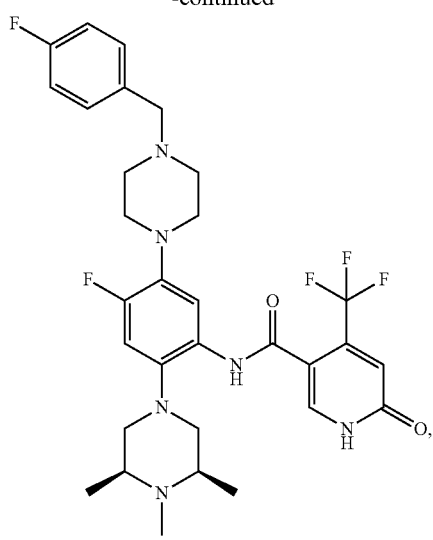
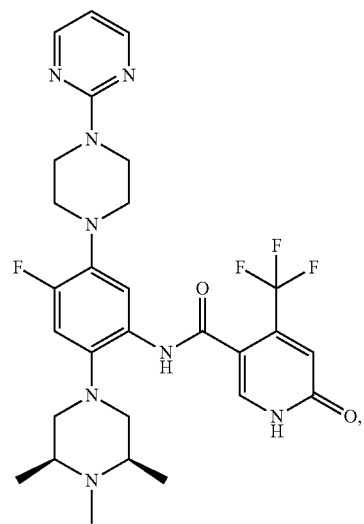
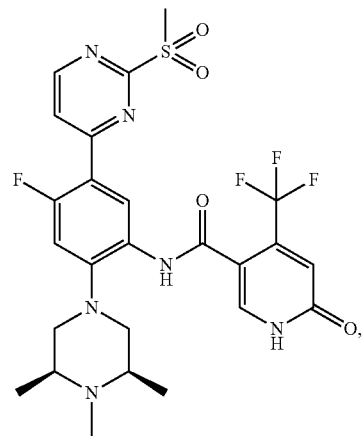
1622
-continued
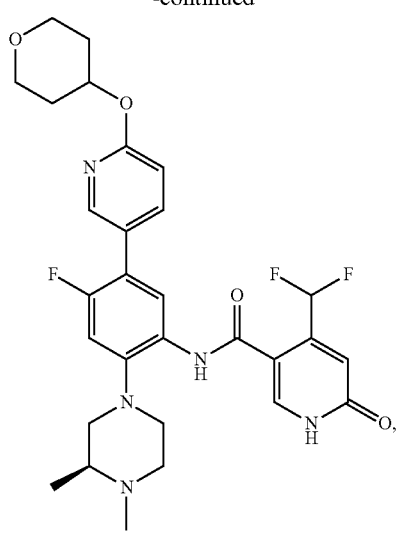
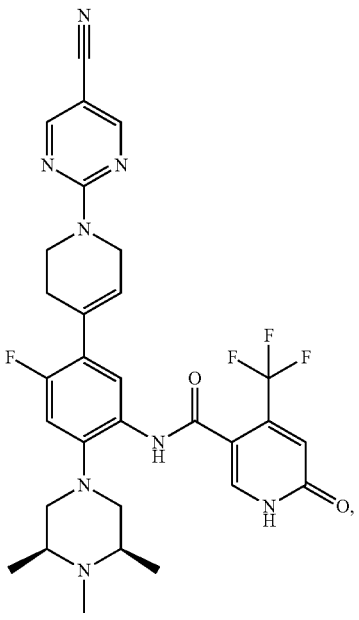

1623
-continued
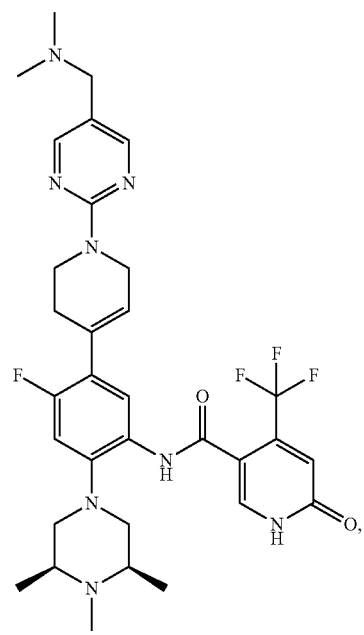
1624
-continued
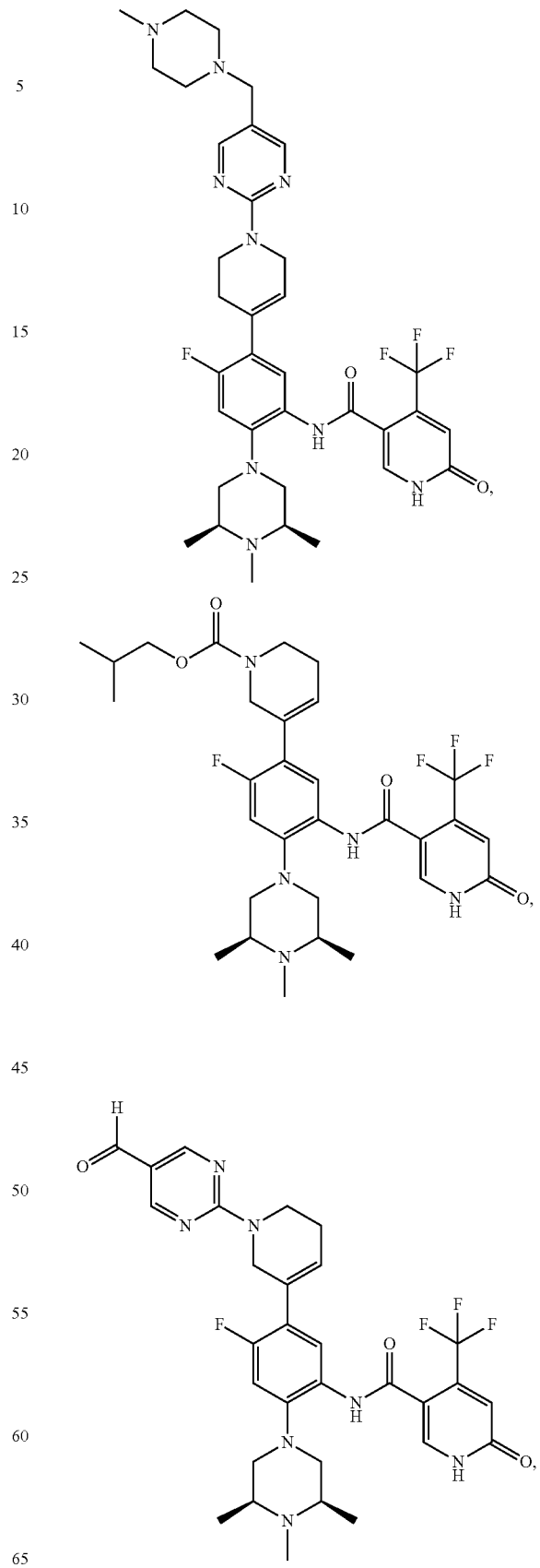

1625
-continued
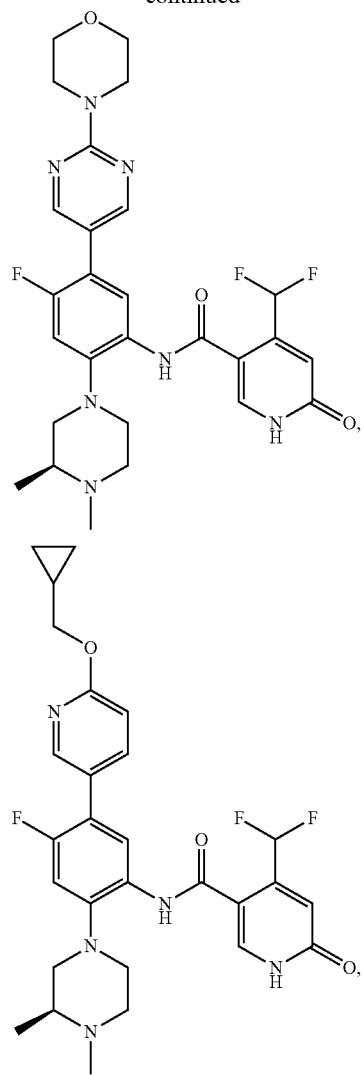
1626
-continued
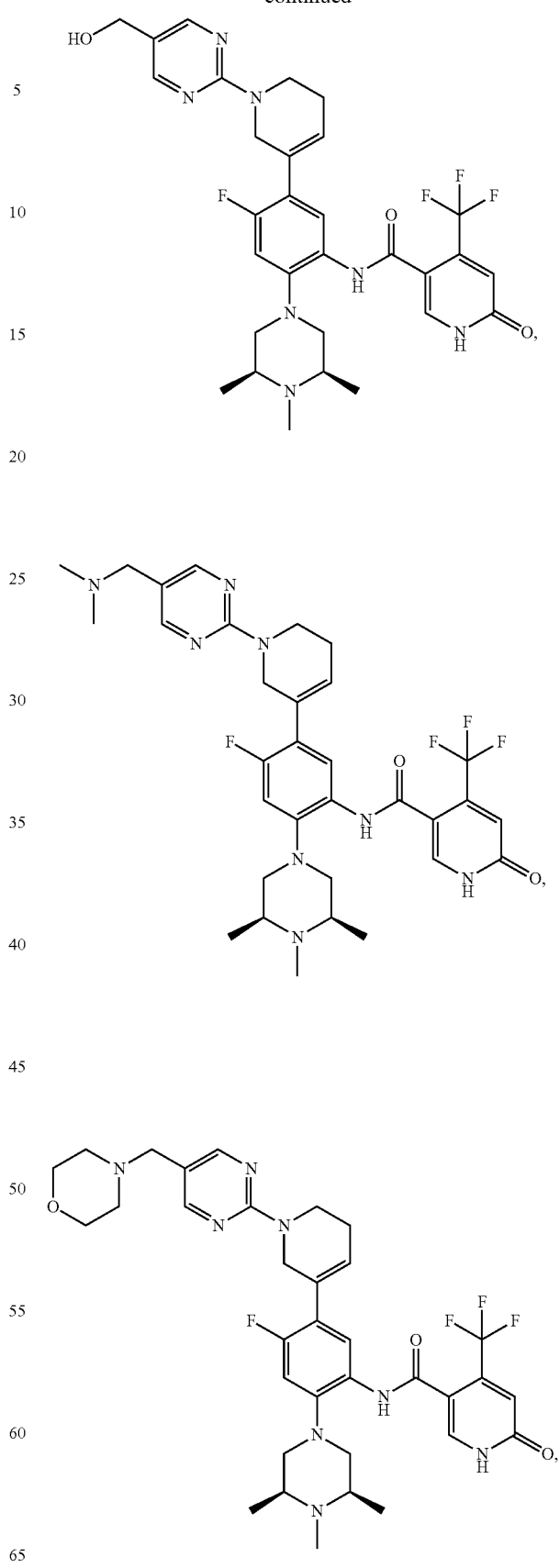

1627
-continued
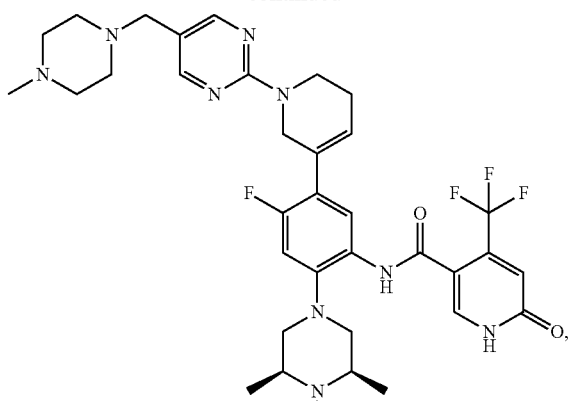
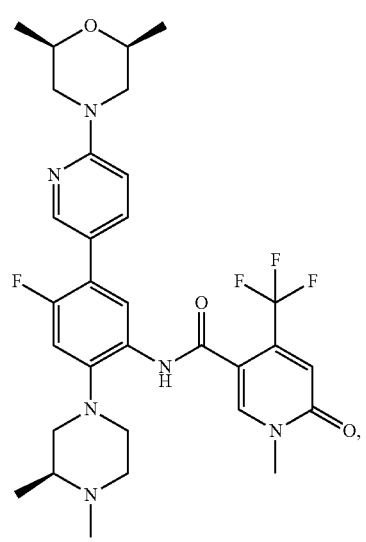
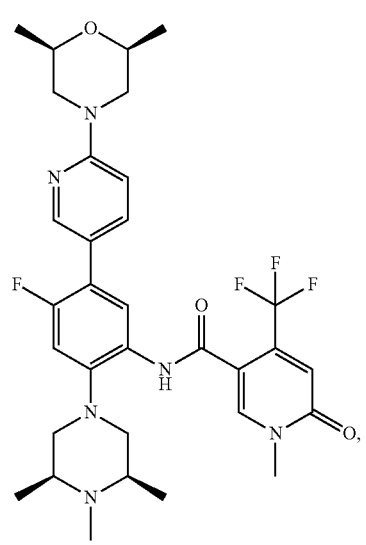
1628
-continued
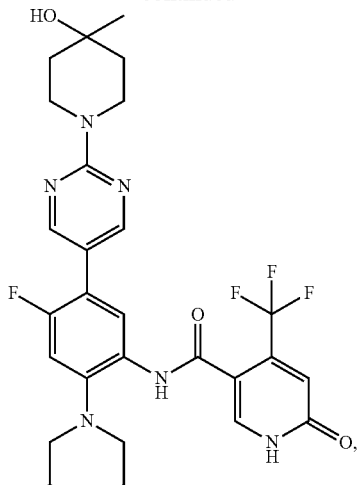
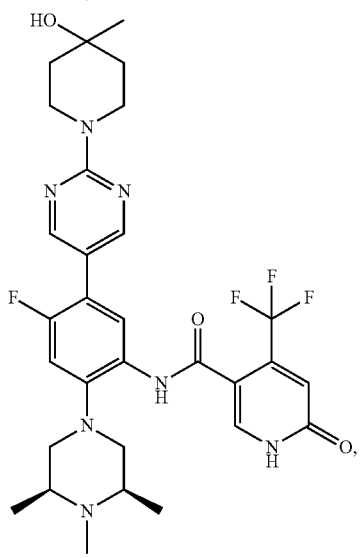
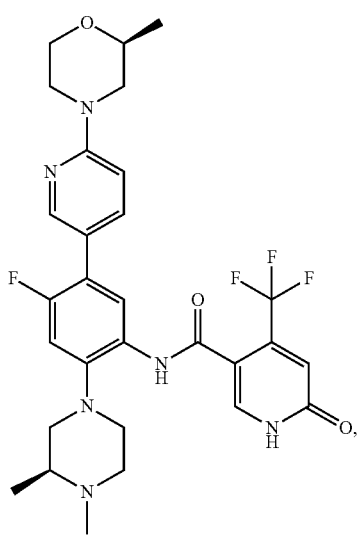

1629
-continued
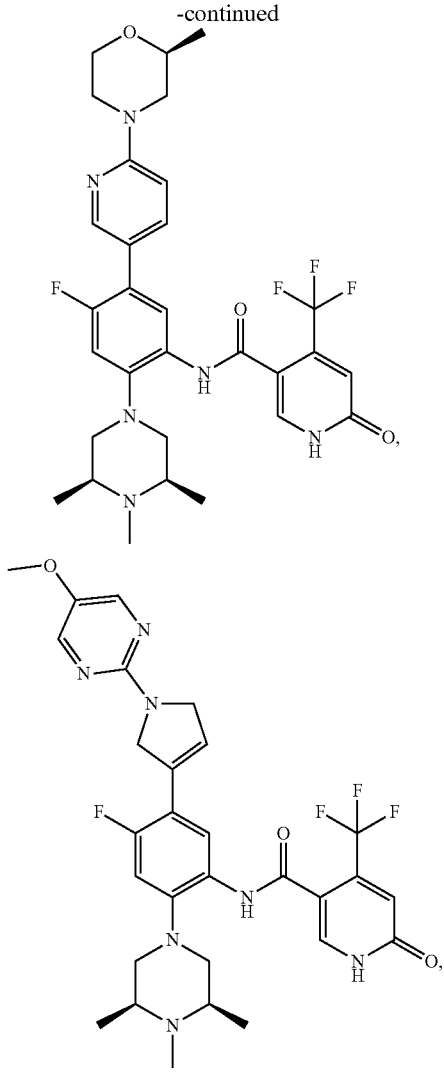
1630
-continued
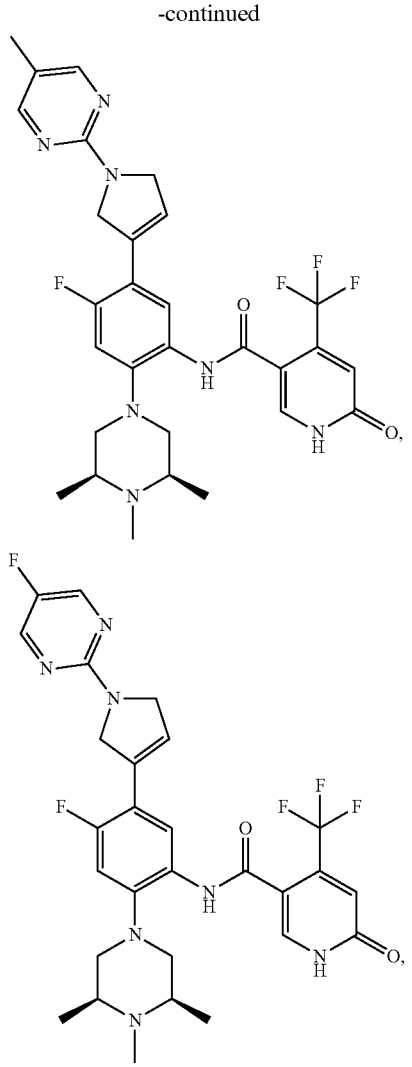
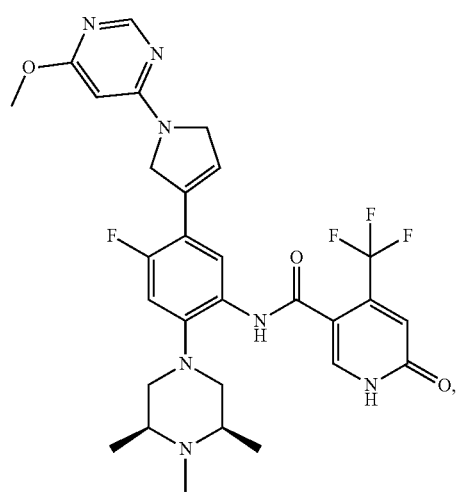
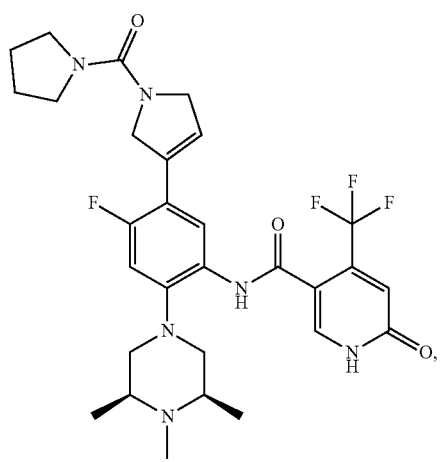

1631
-continued
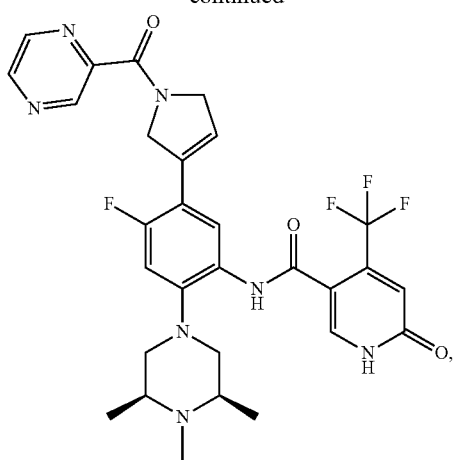
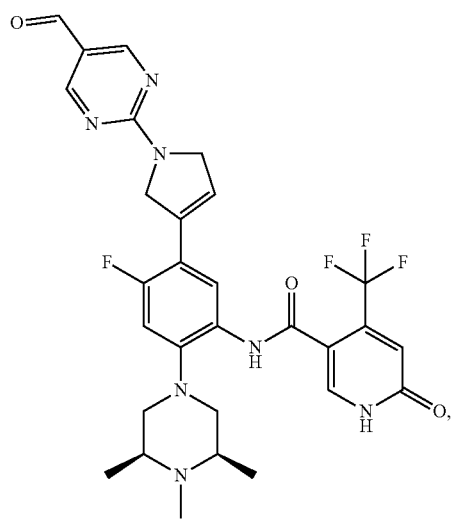
1632
-continued
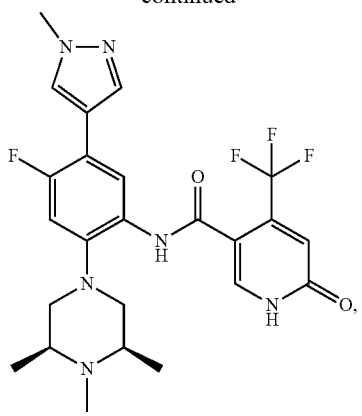
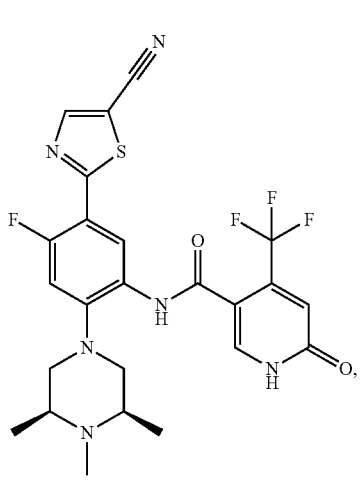

1633
-continued
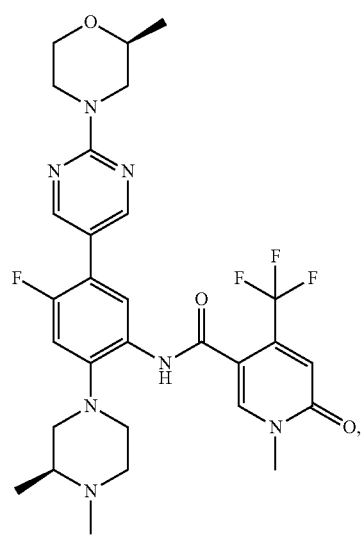
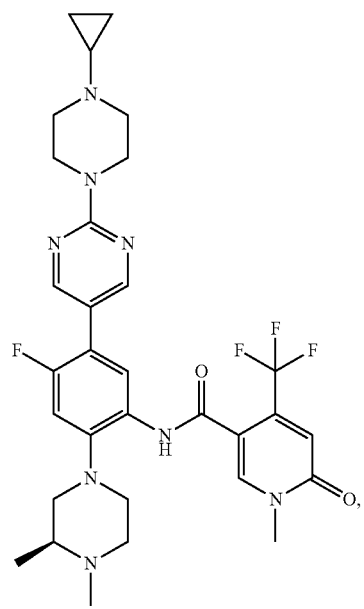
1634
-continued
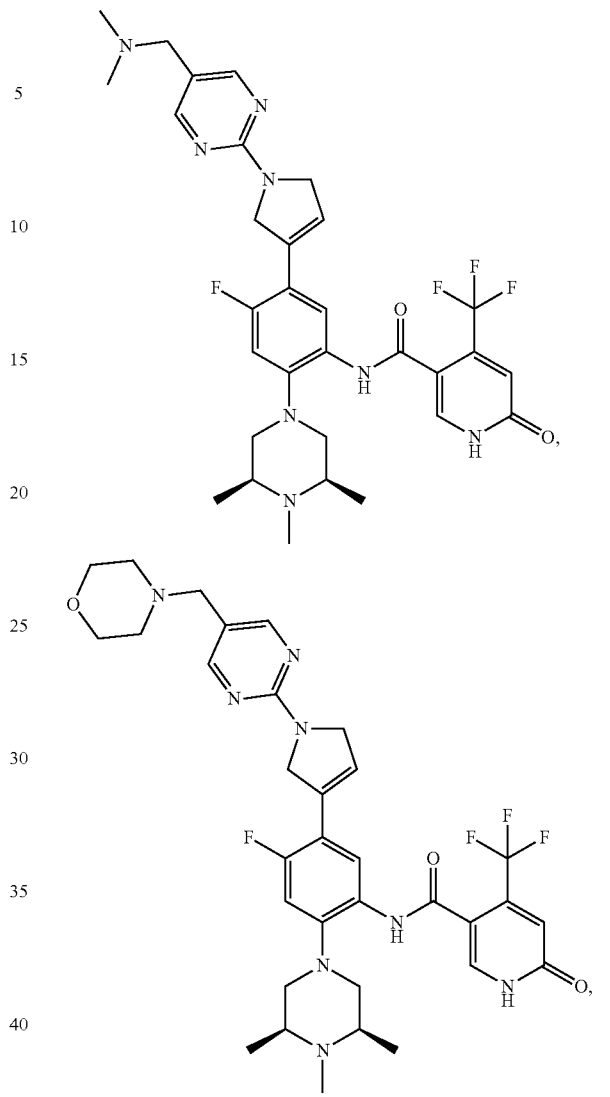

1635
-continued
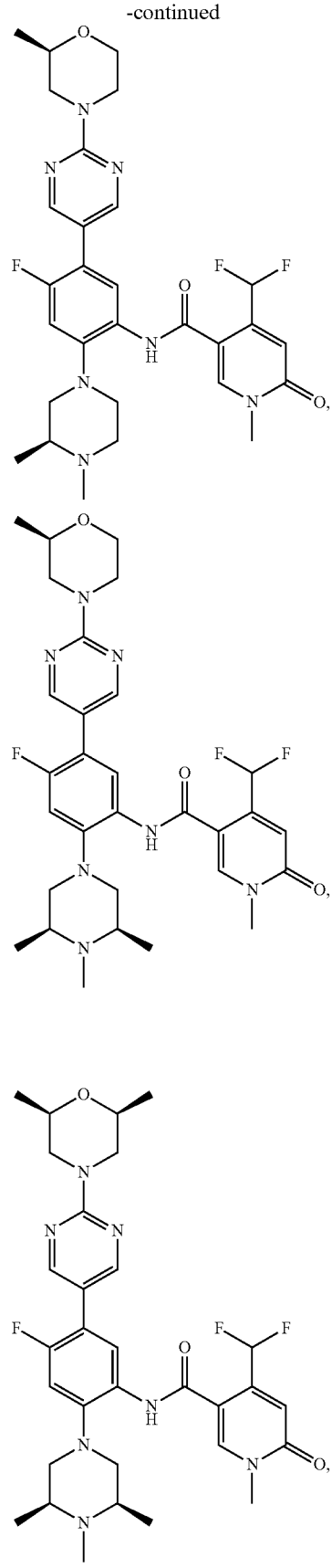
1636
-continued
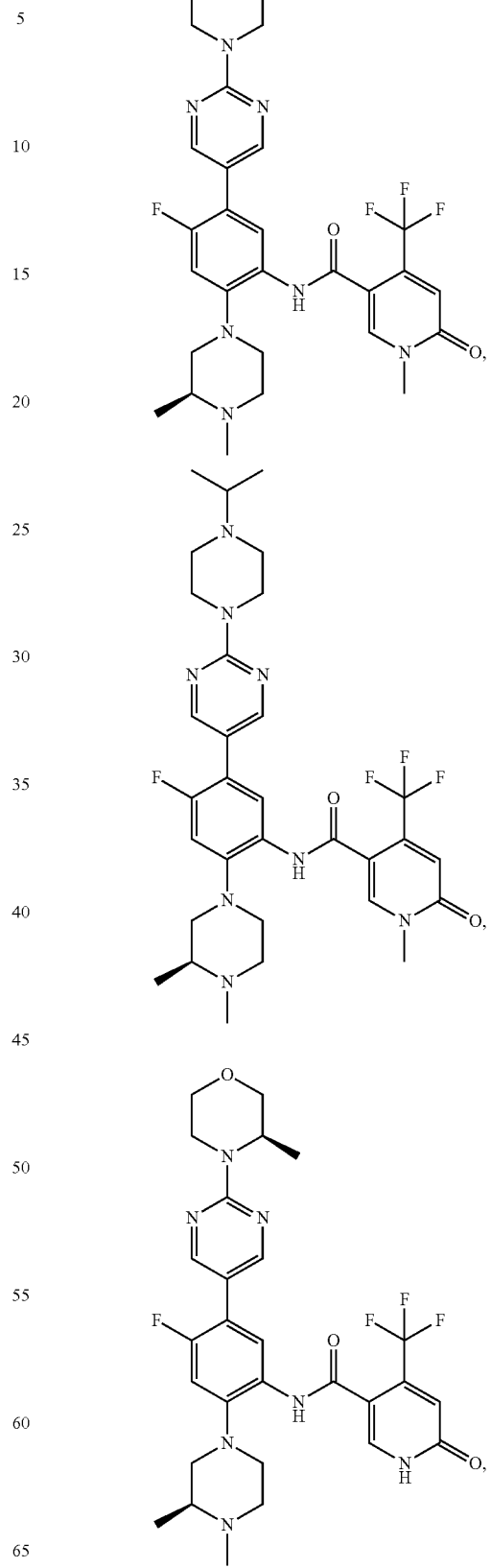

1637
-continued
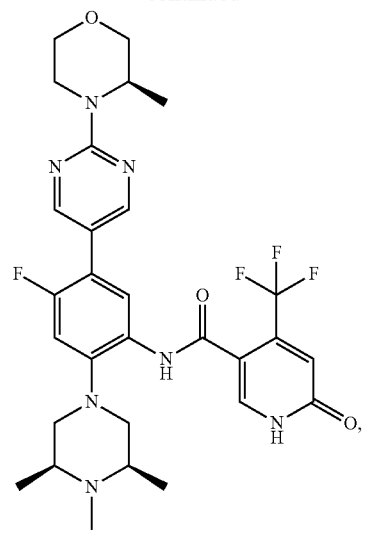
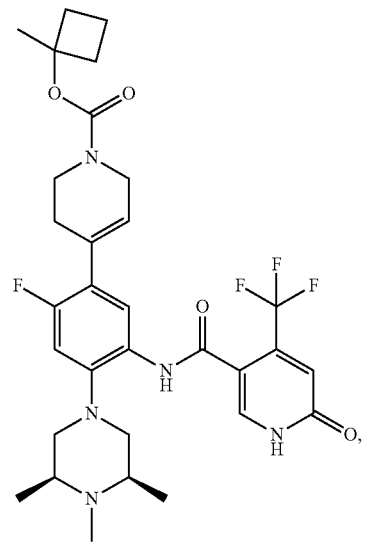
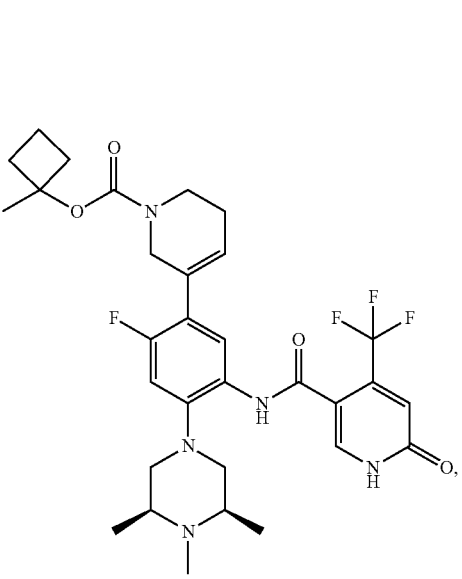
1638
-continued
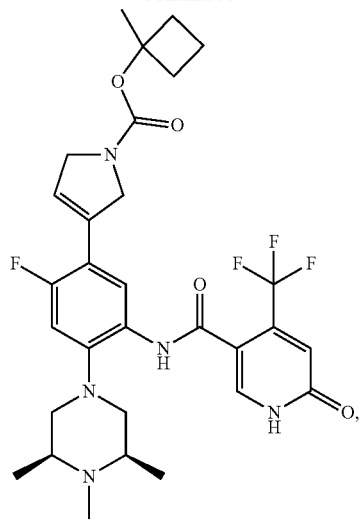
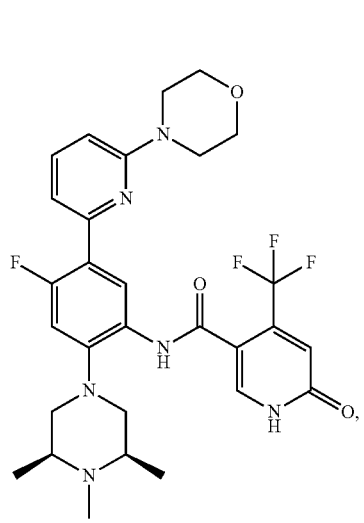
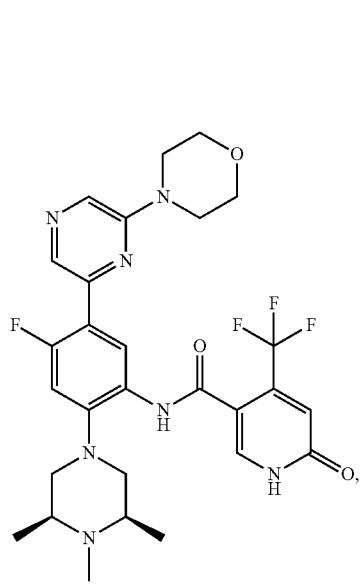

1639
-continued
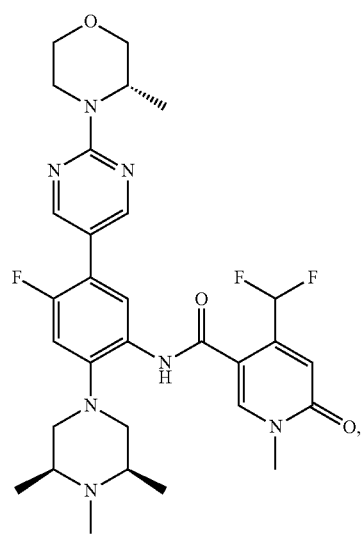
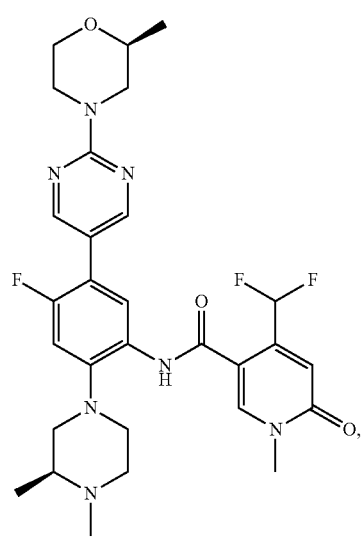
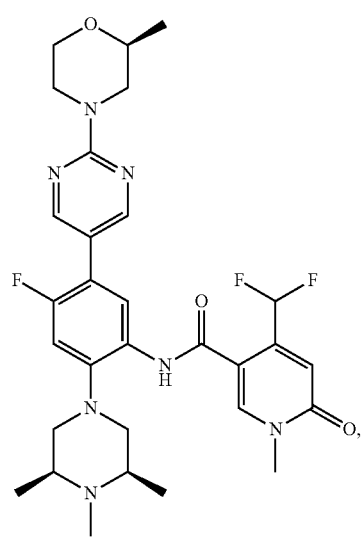
1640
-continued
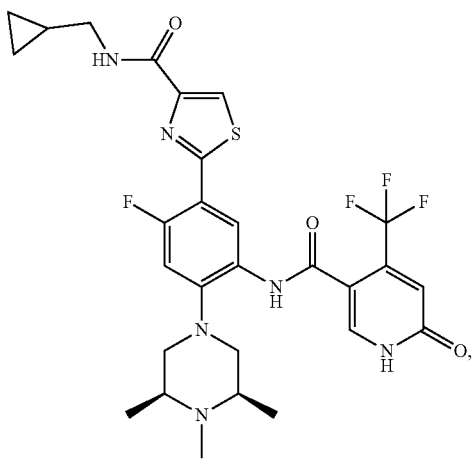
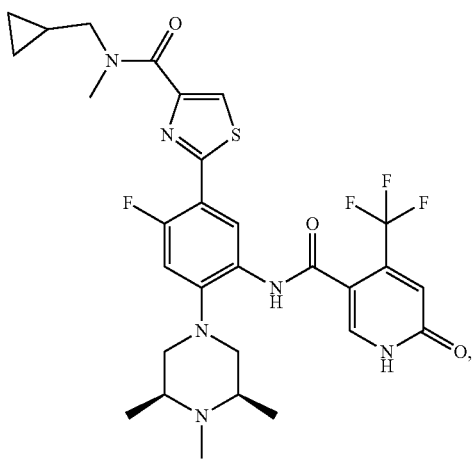
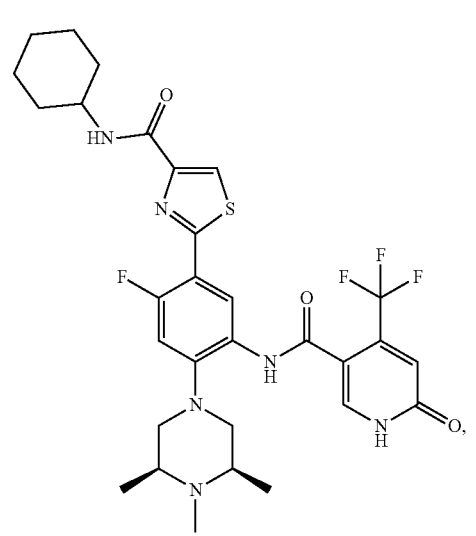

1641
-continued
1642
-continued
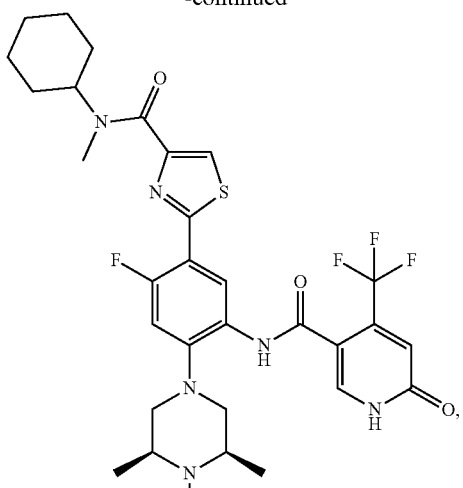
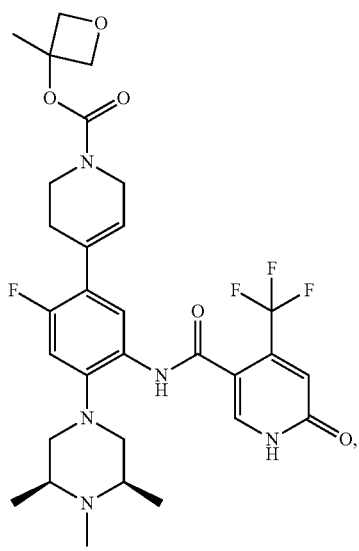
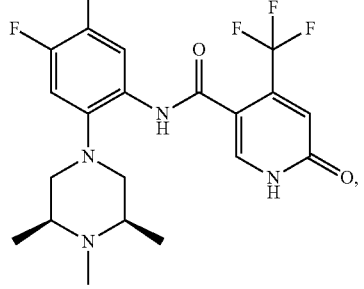
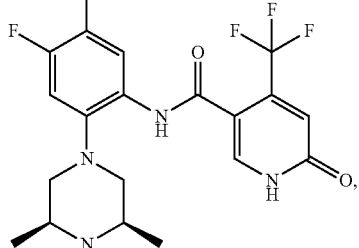

1643
-continued
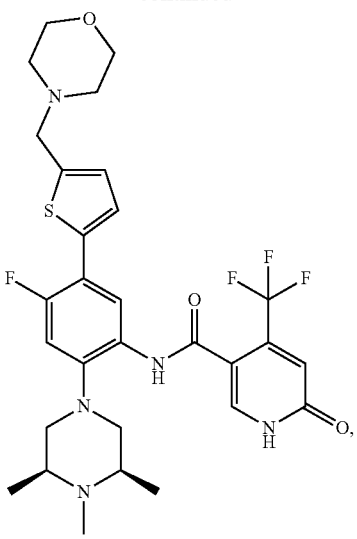
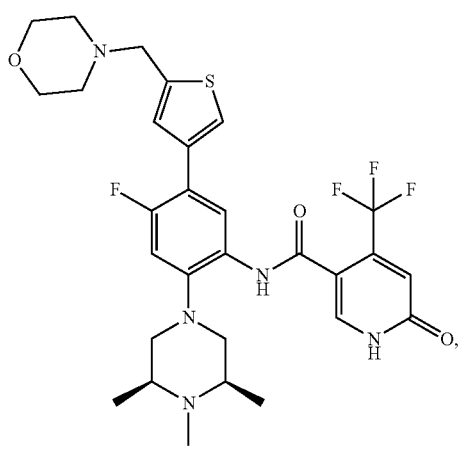
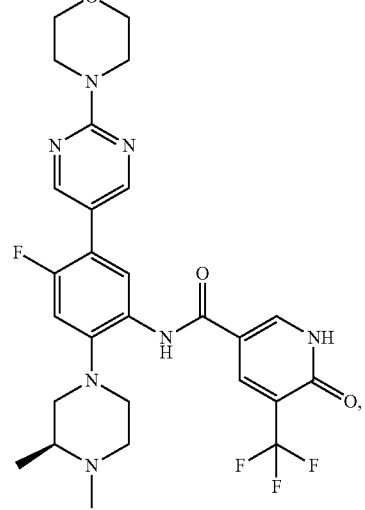
1644
-continued
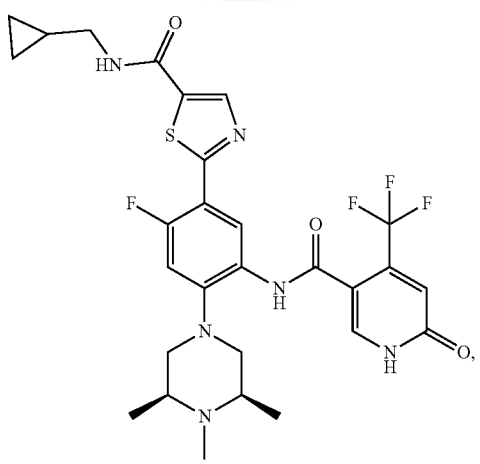
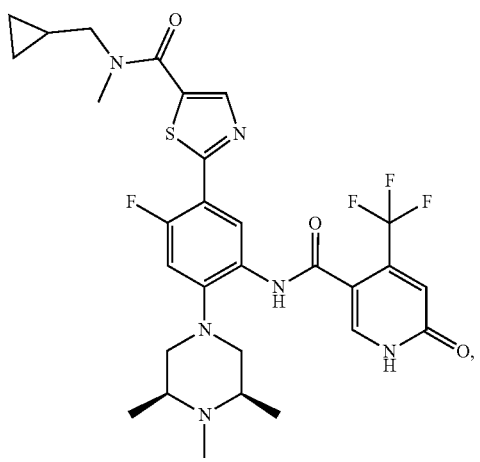
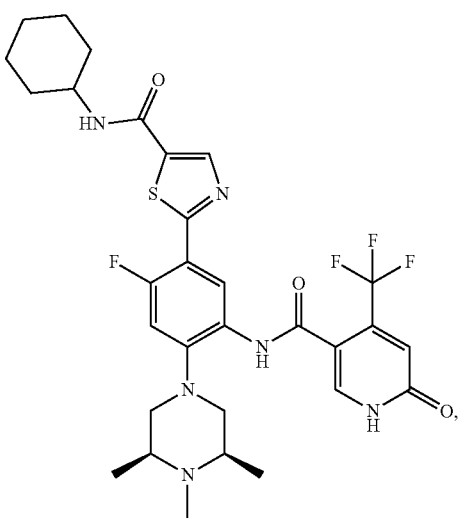

1645
-continued
1646
-continued
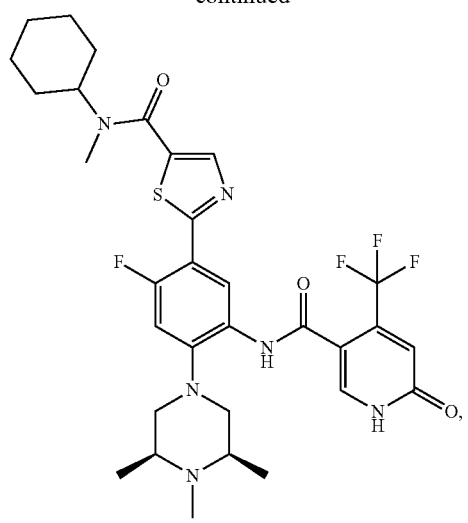
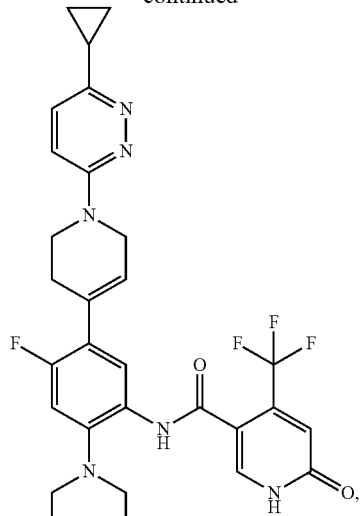
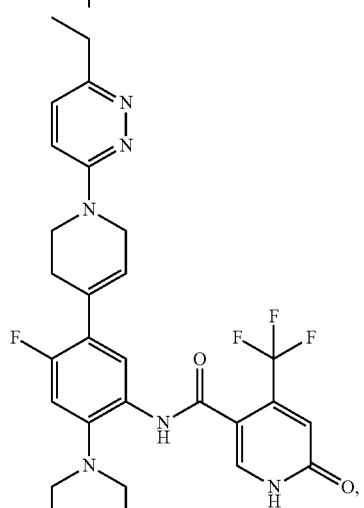
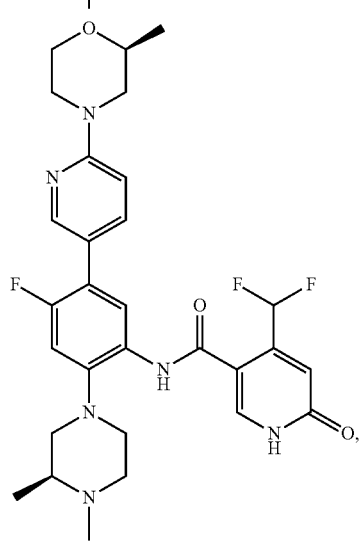

1647
-continued
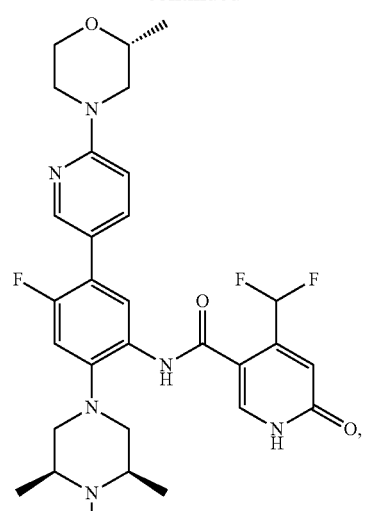
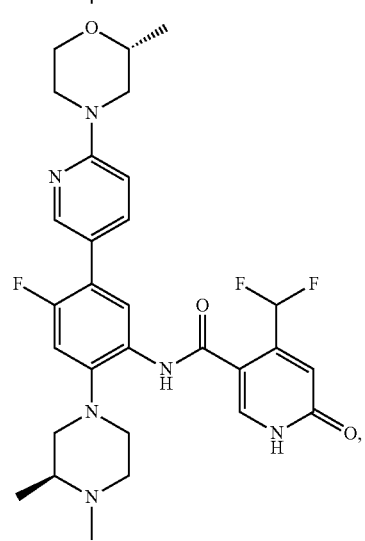
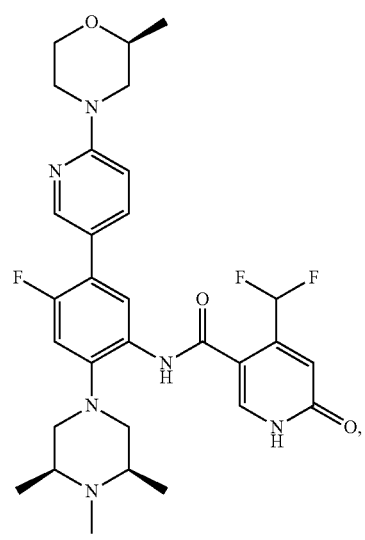
1648
-continued
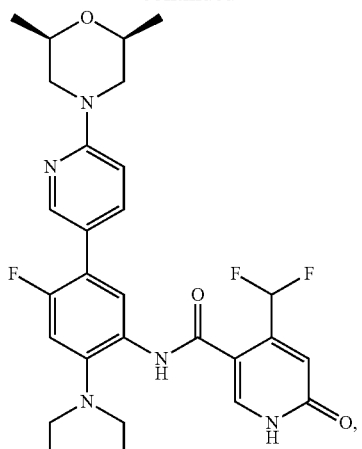
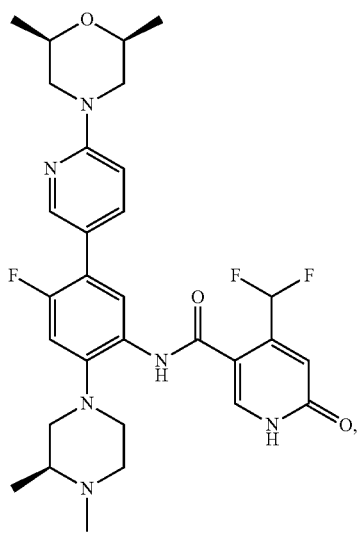

1649
-continued
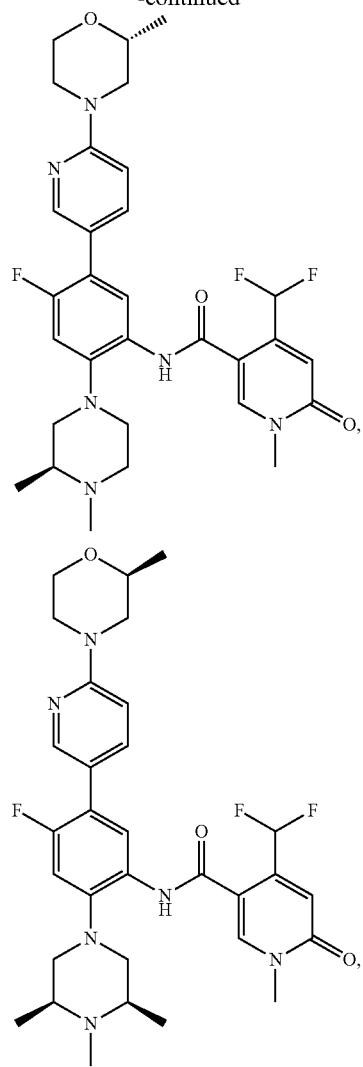
1650
-continued
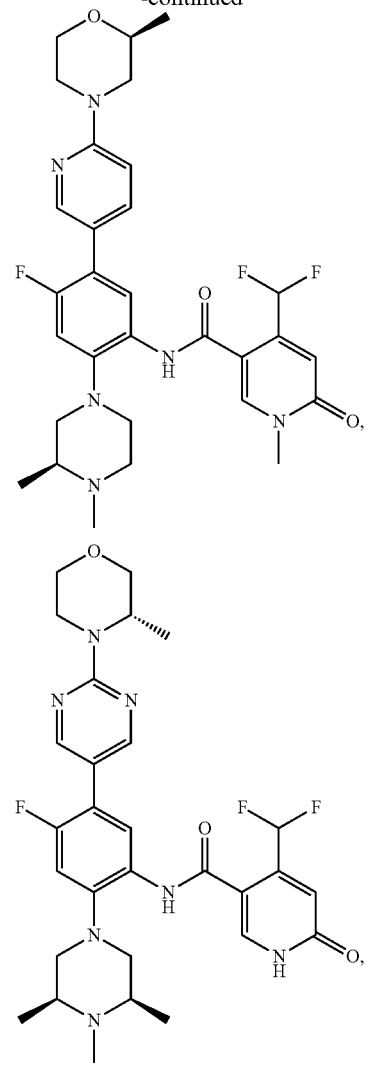
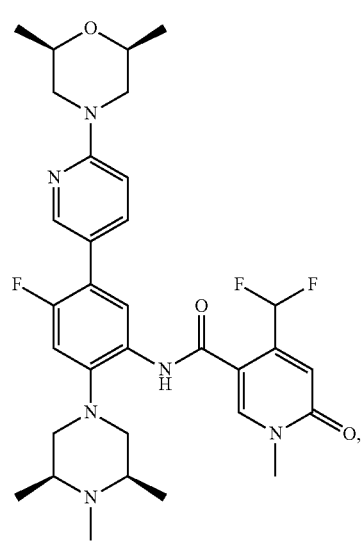
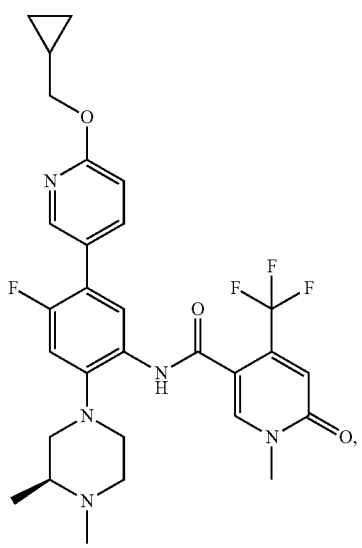

1651
-continued
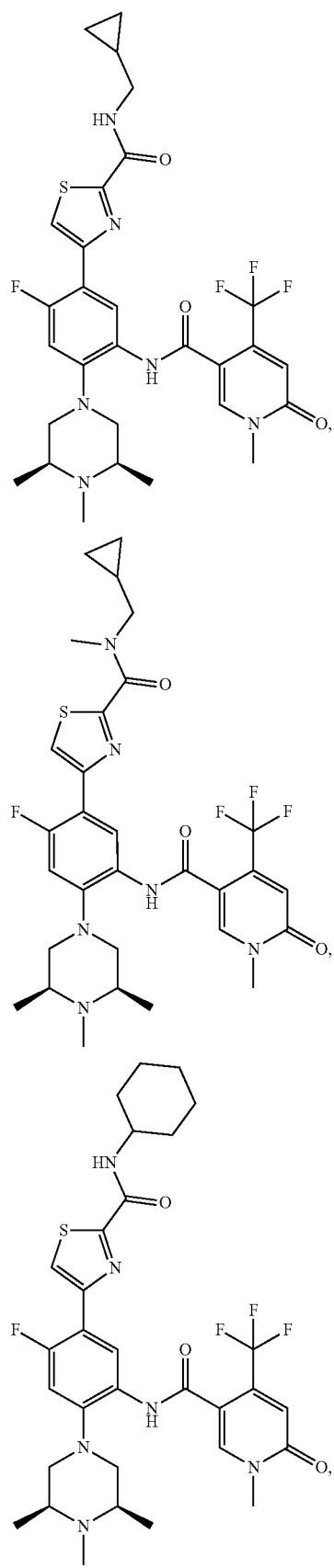
1652
-continued
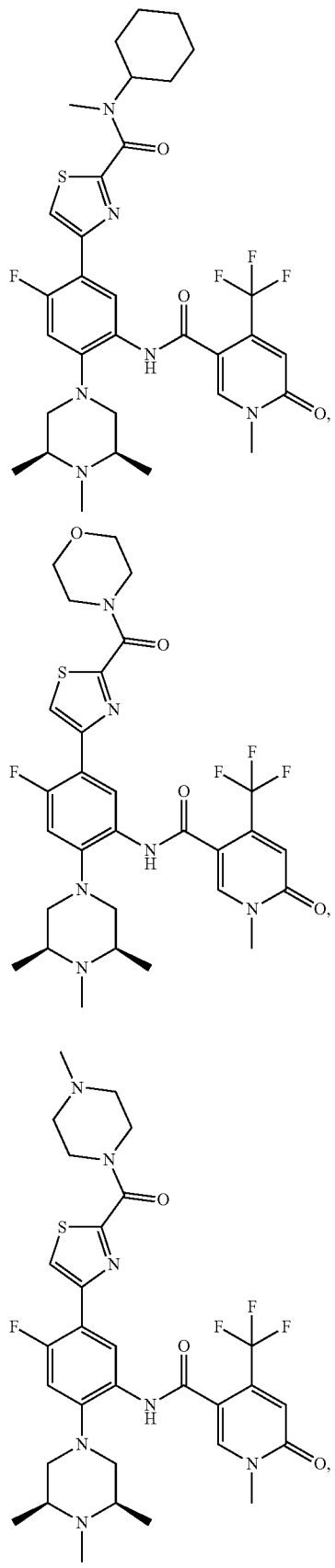

1653
-continued
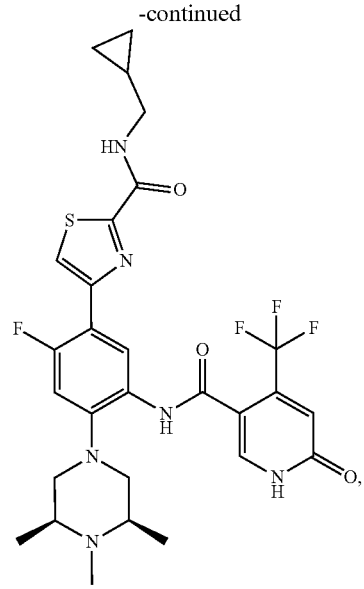
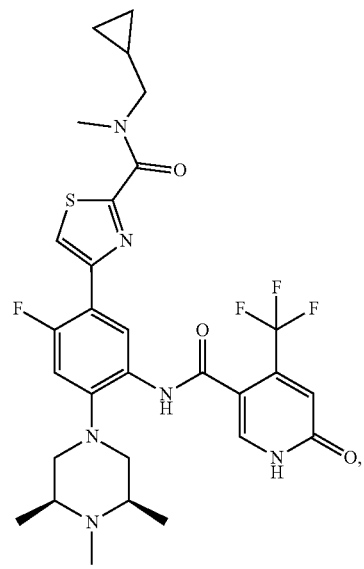
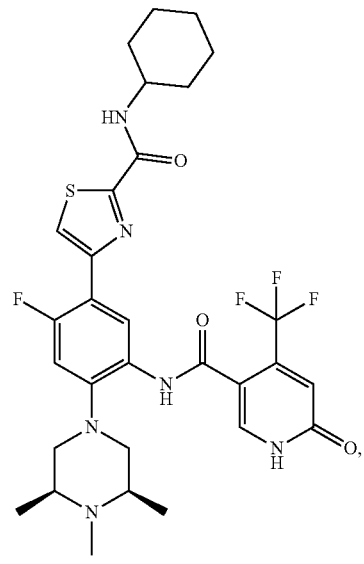
1654
-continued
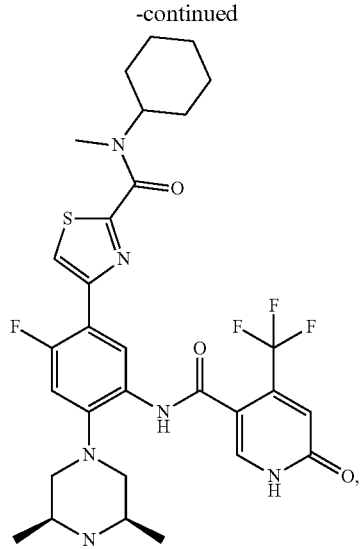
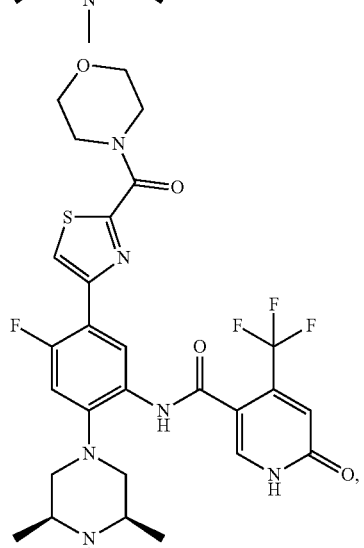
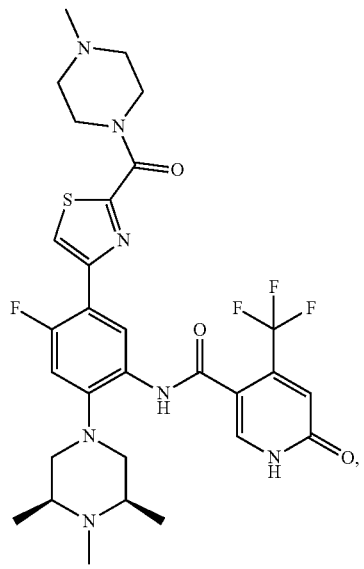

1655
-continued
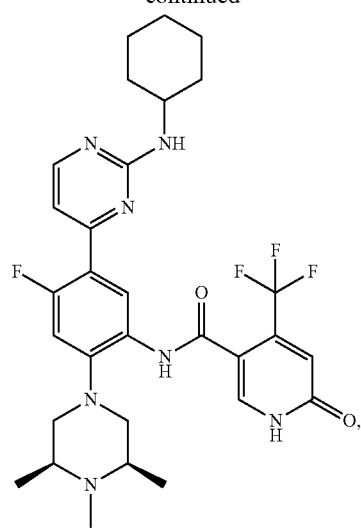
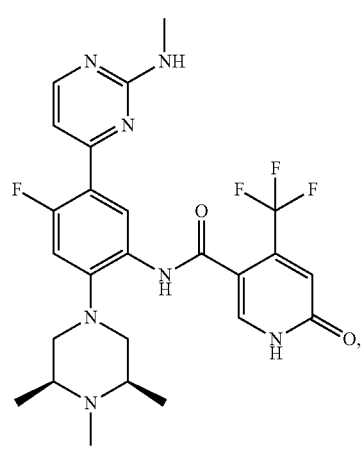
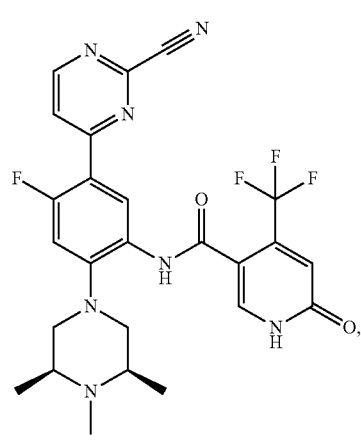
1656
-continued
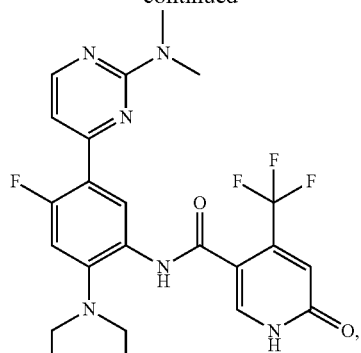
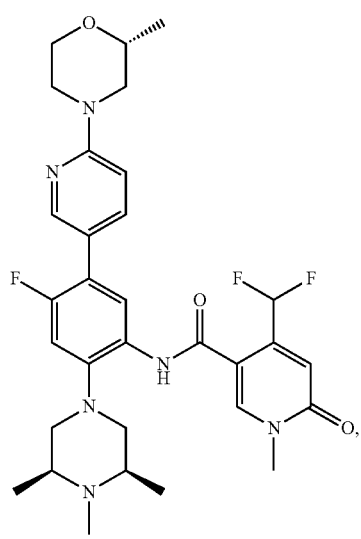
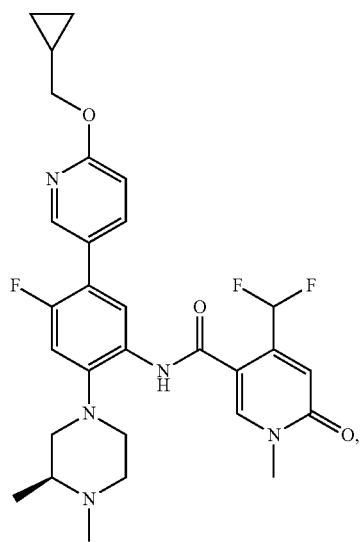

1657
-continued
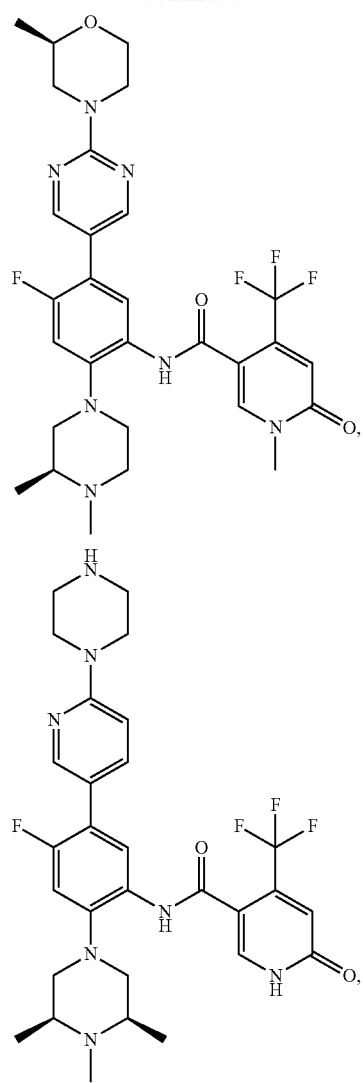
1658
-continued
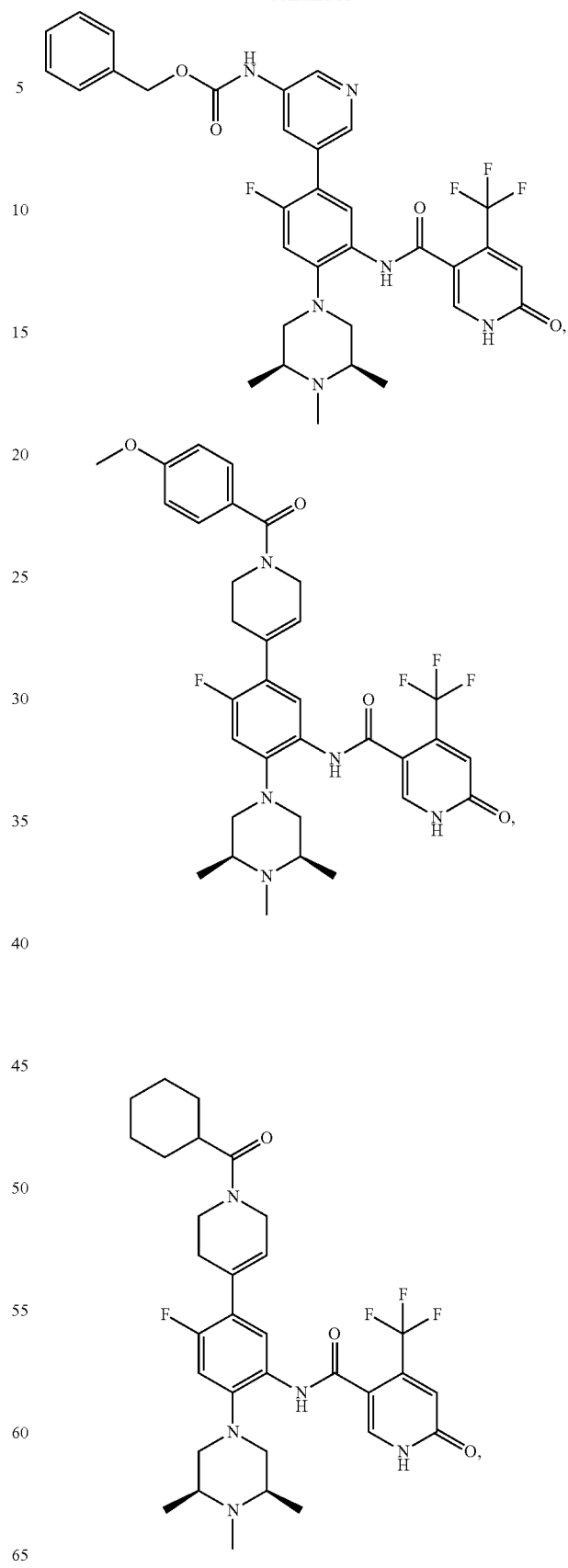

1659
-continued
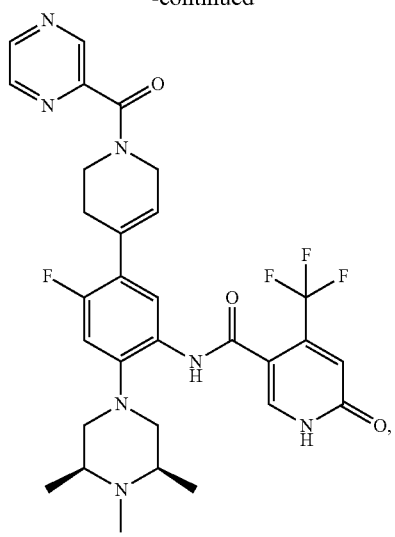
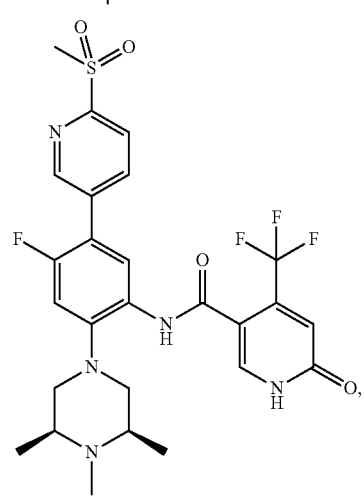
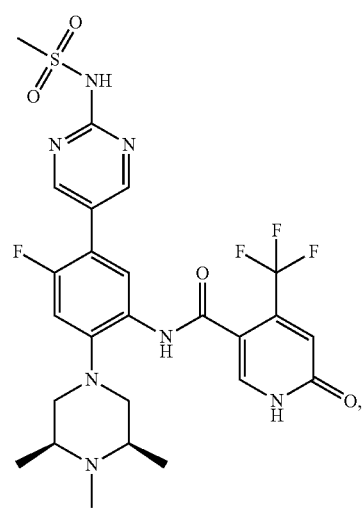
1660
-continued
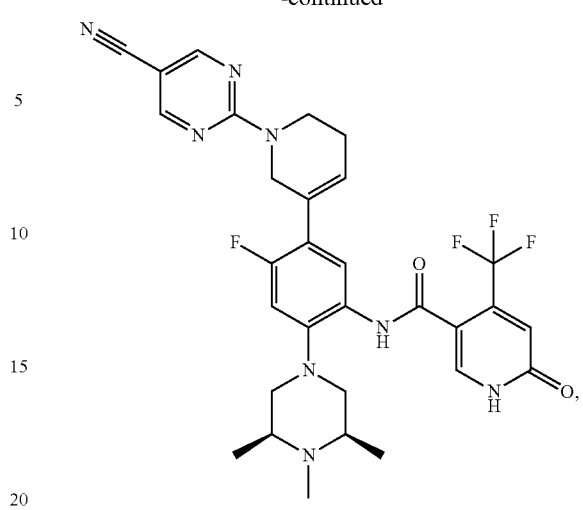
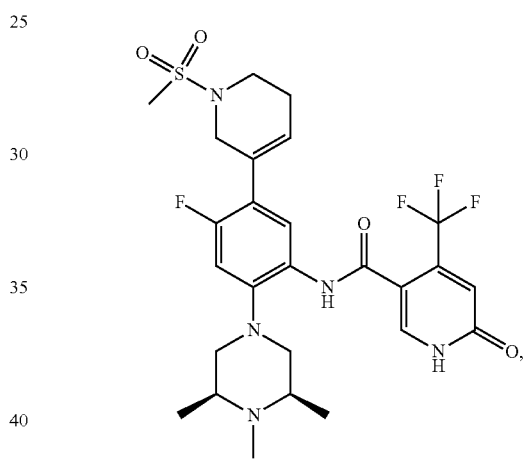
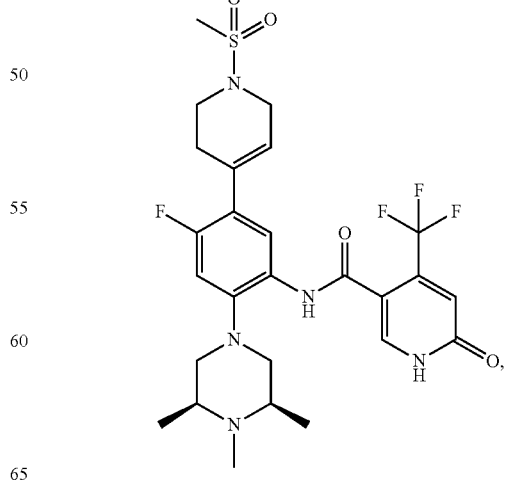

1661
-continued
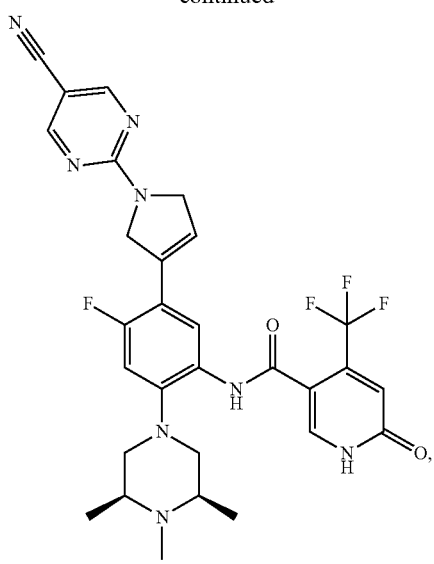
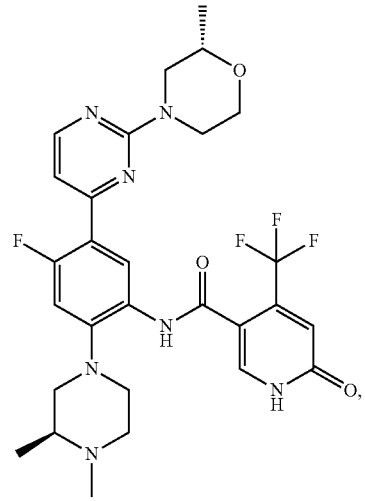
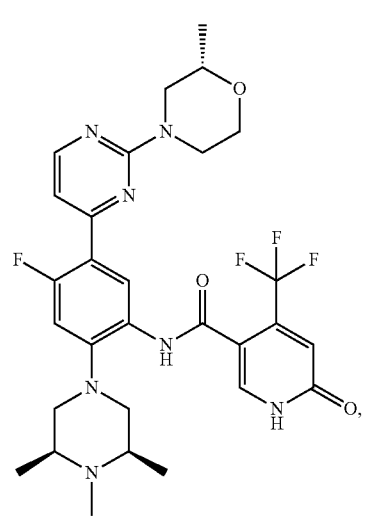
1662
-continued
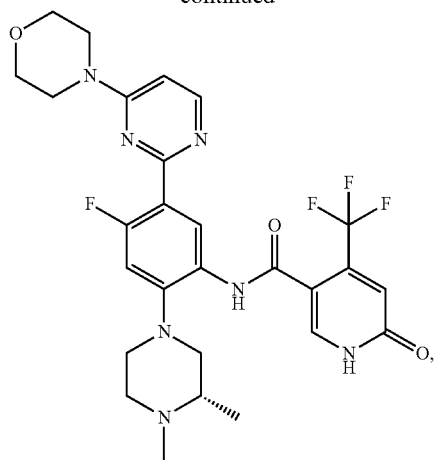
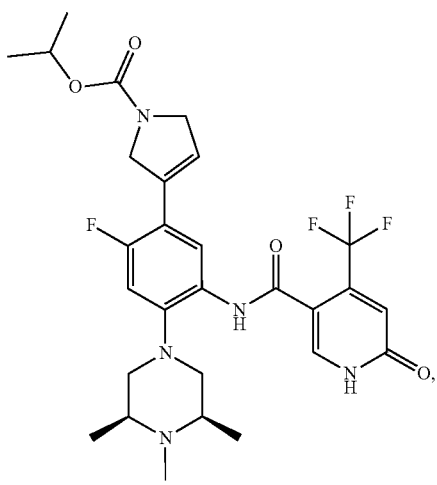
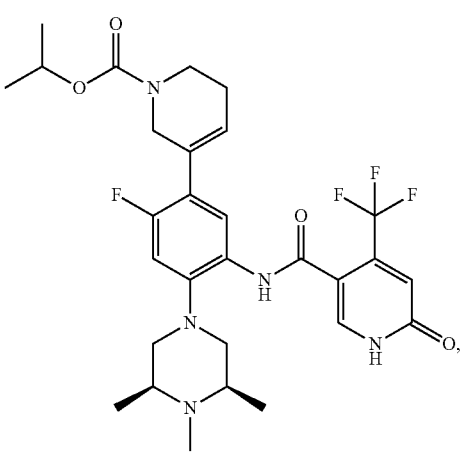

1663
-continued
1664
-continued
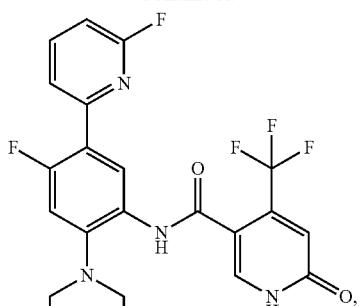
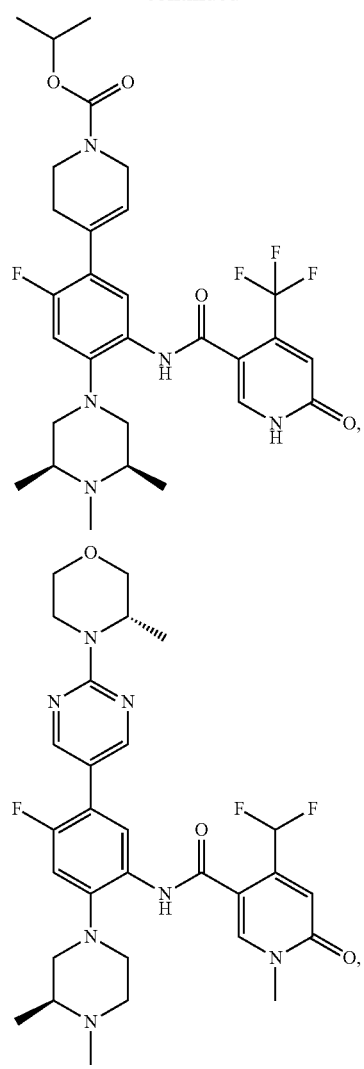
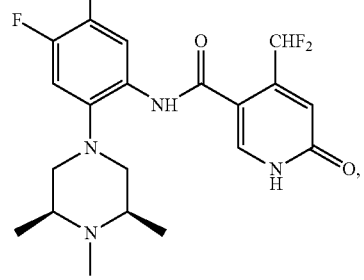

1665
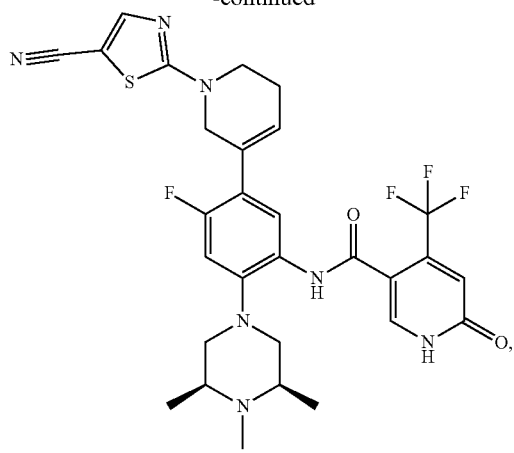
1666
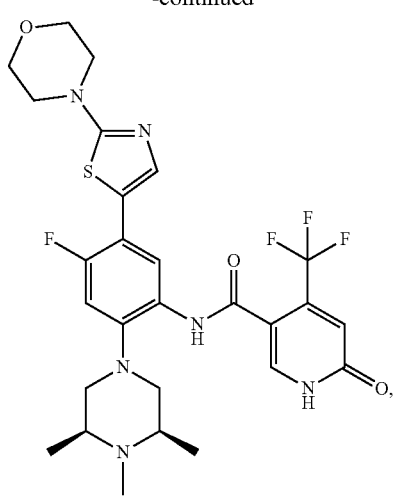
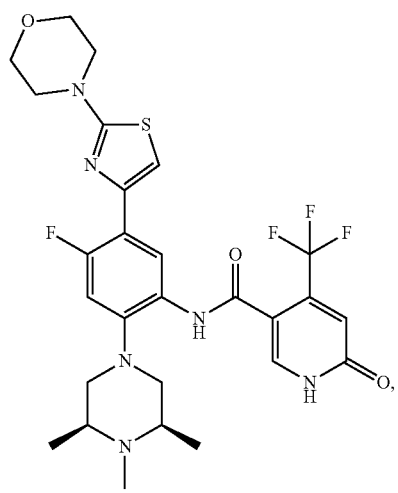
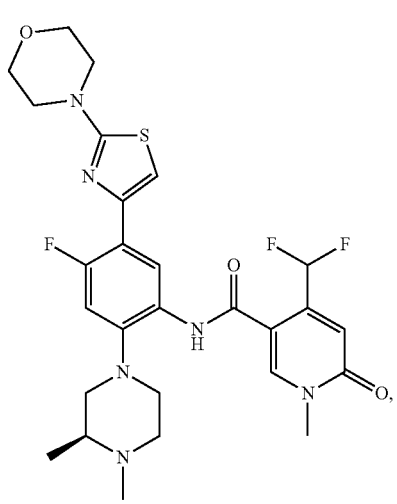
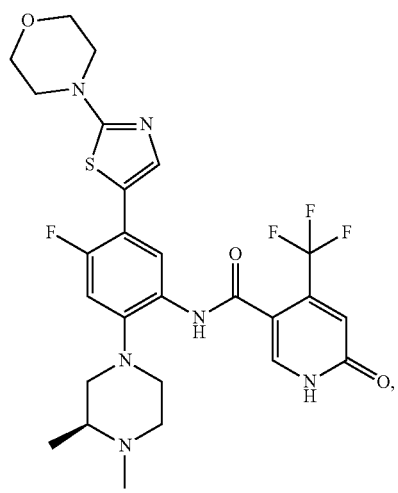
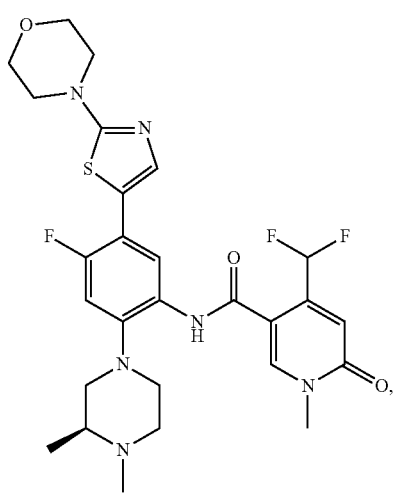

1667
-continued
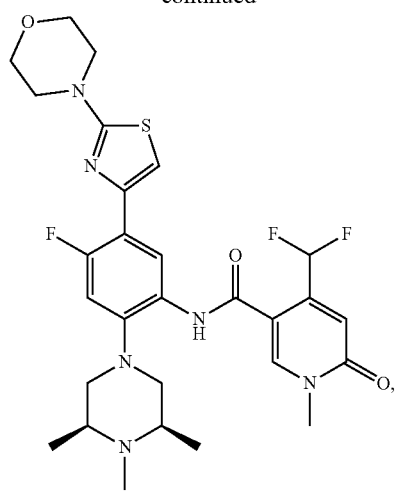
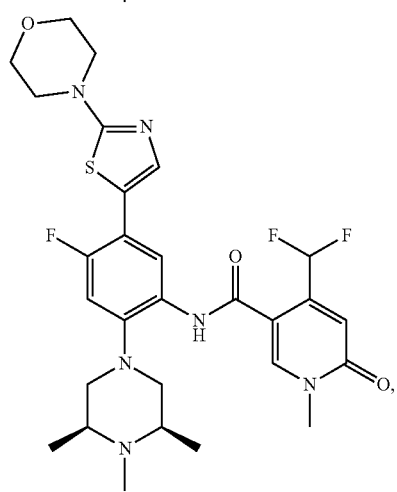
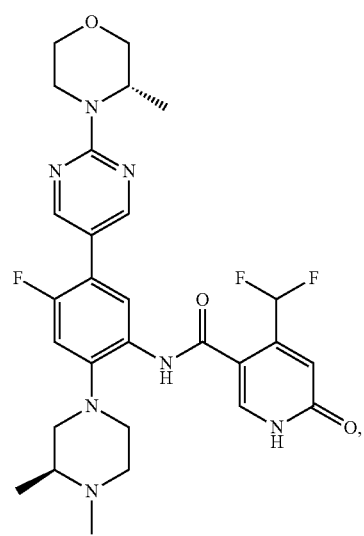
1668
-continued
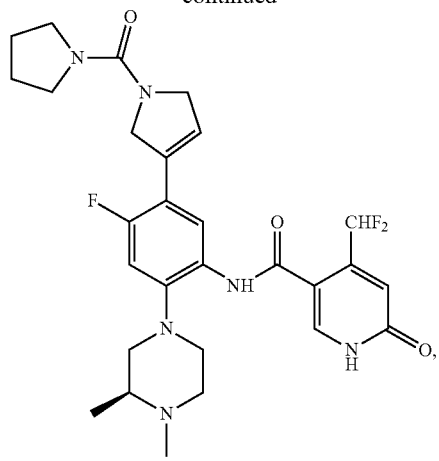
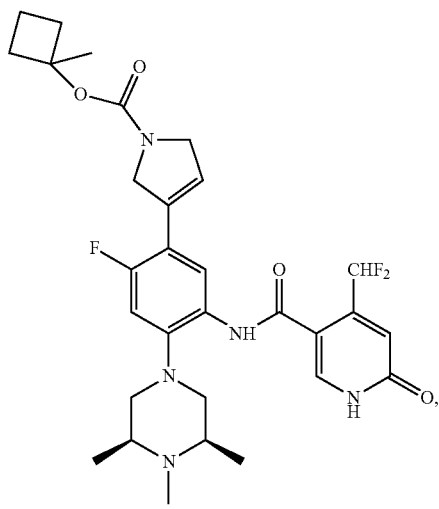
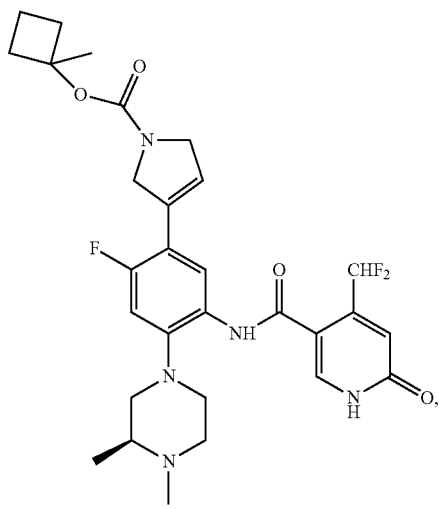

1669
-continued
1670
-continued
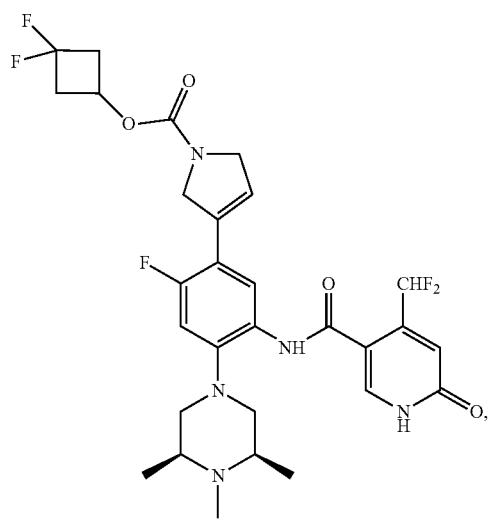
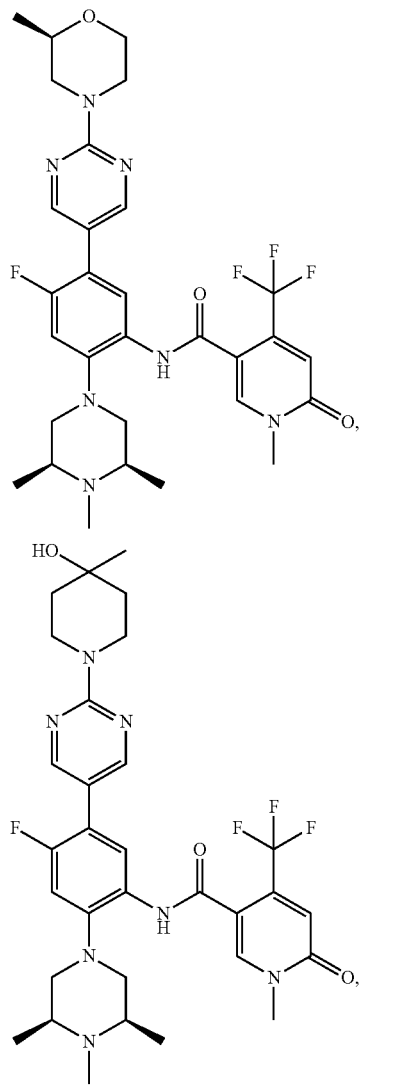
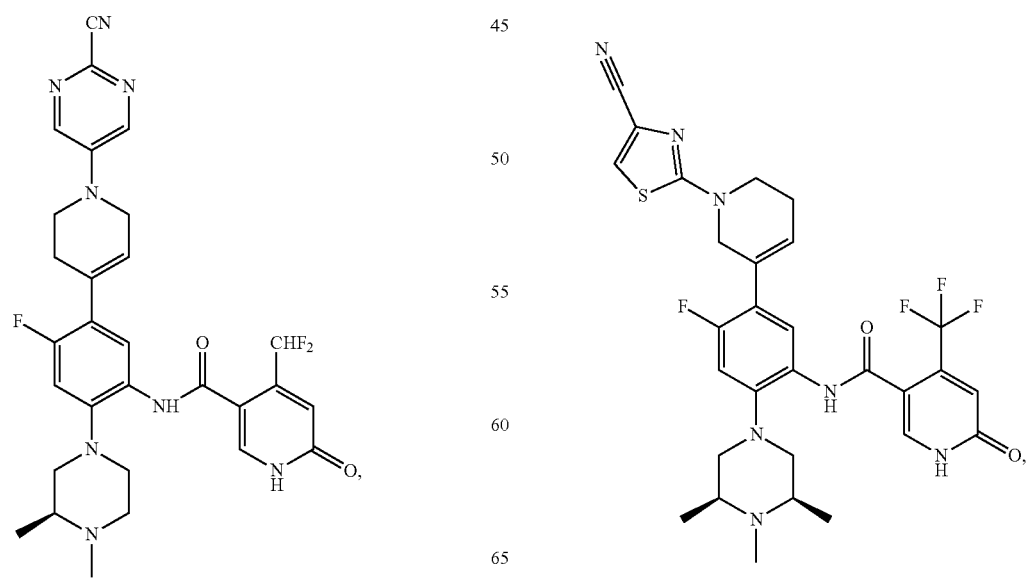

1671
-continued
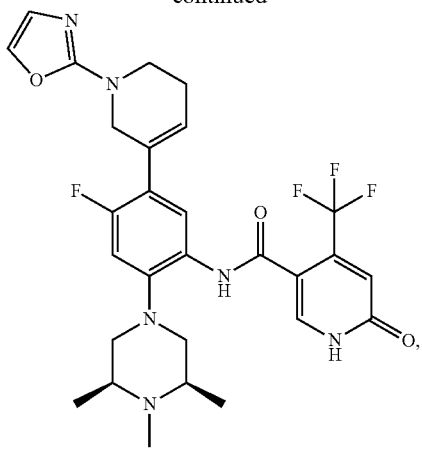
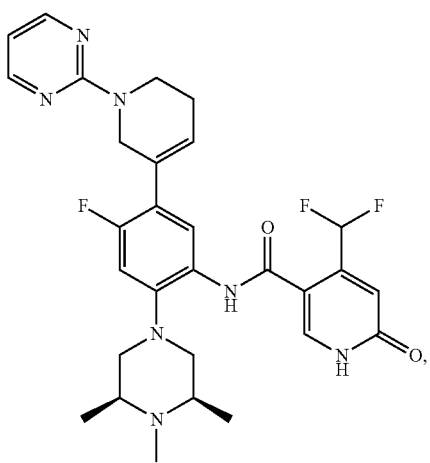
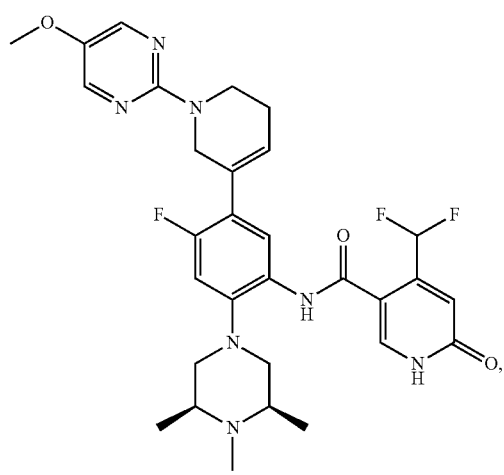
1672
-continued
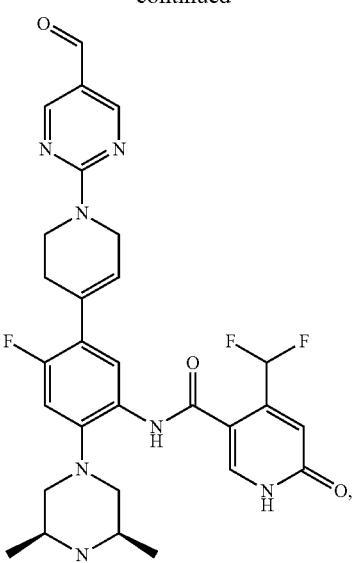
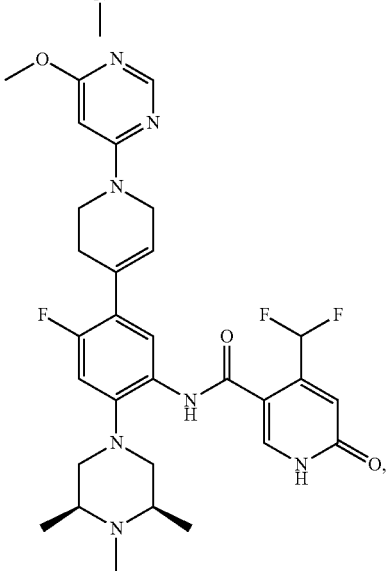
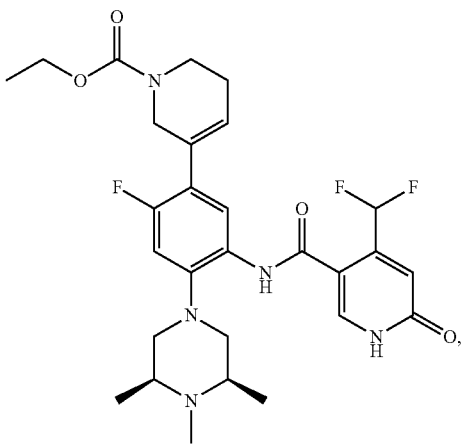

1673
-continued
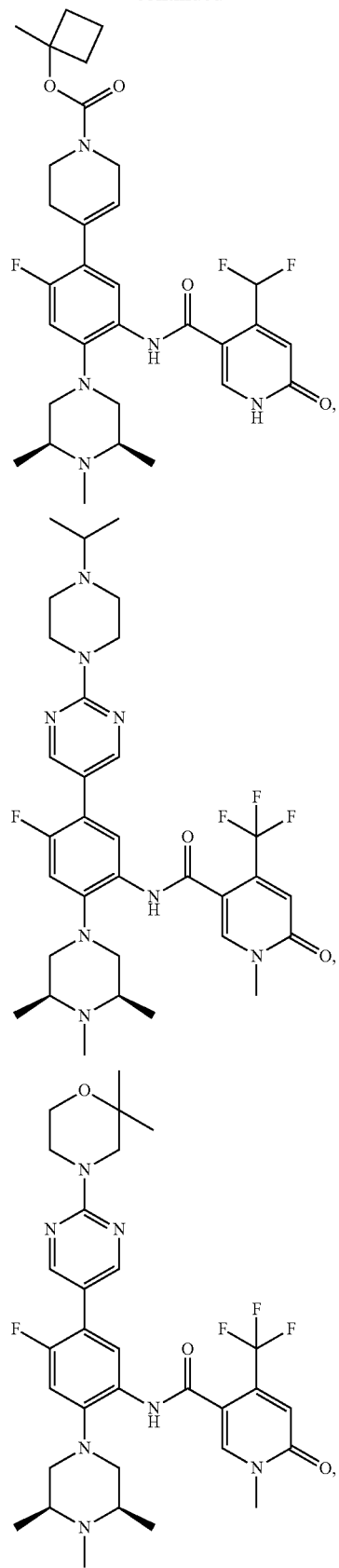
1674
-continued
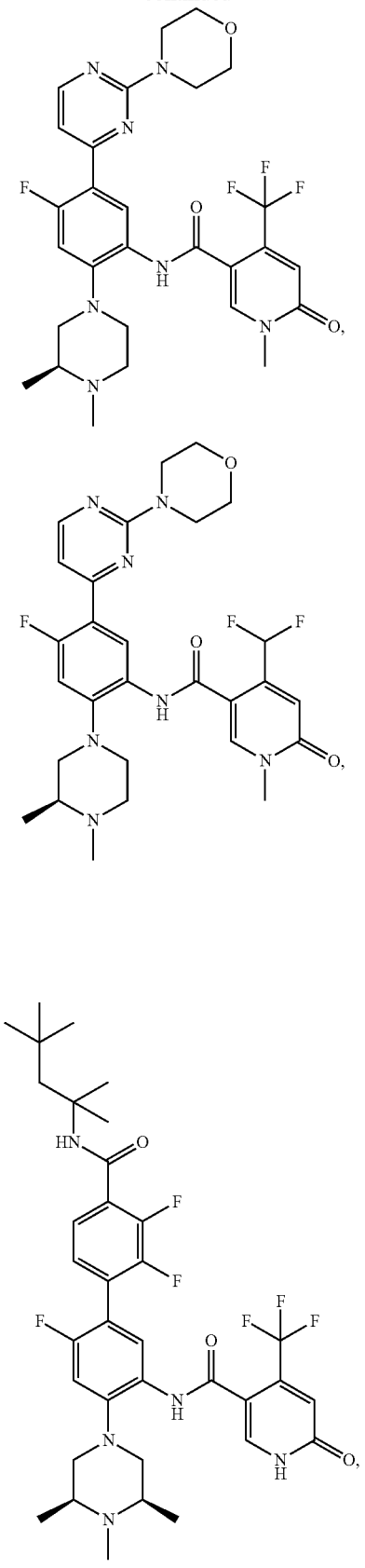

1675
-continued
1676
-continued
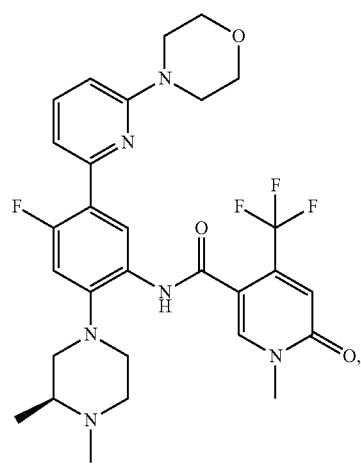
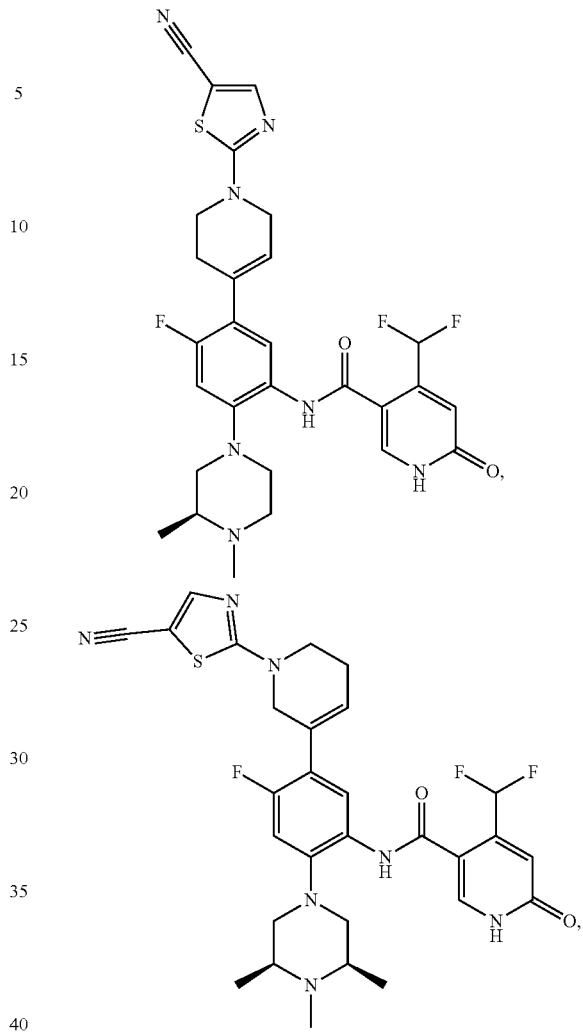
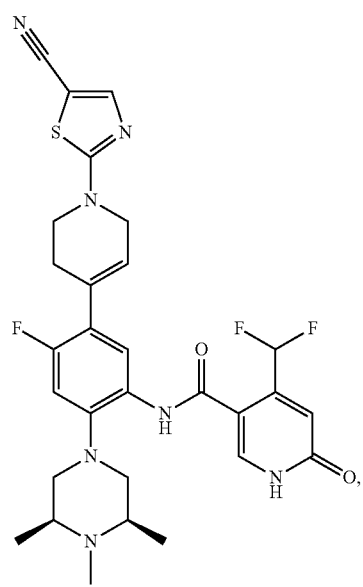
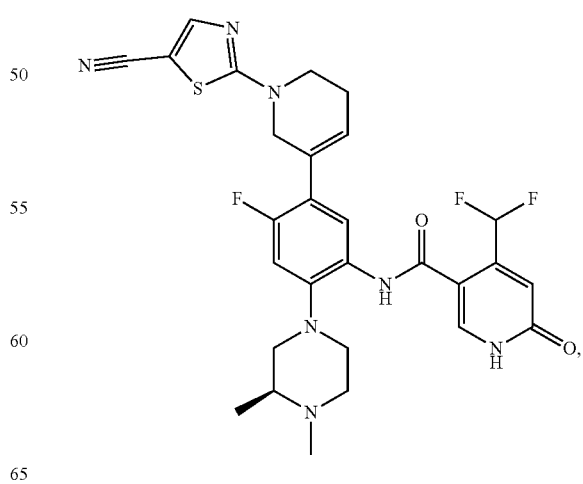

1677
-continued
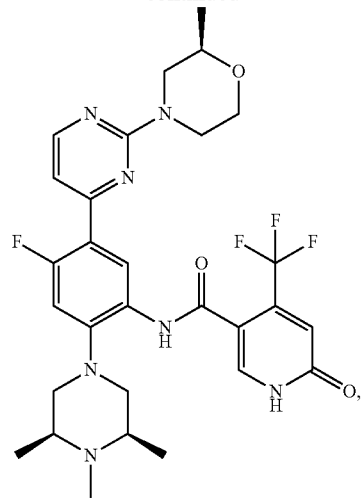
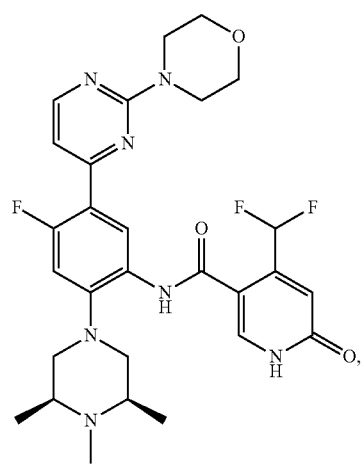
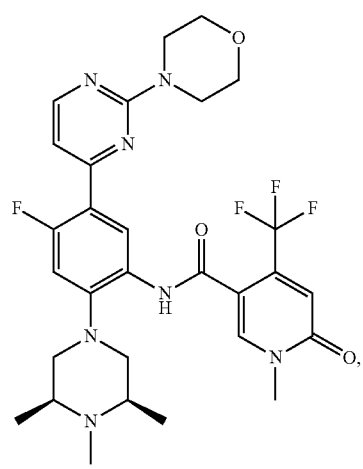
1678
-continued
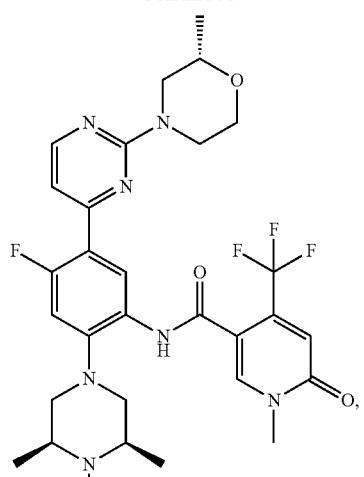
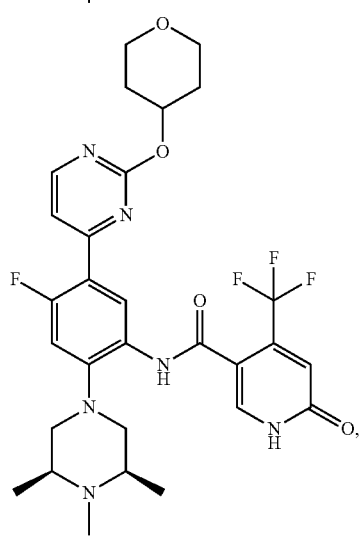
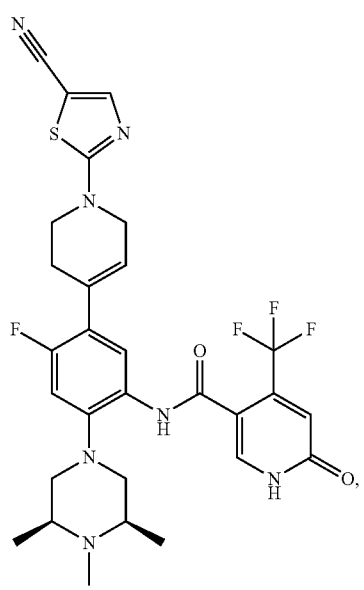

1679
-continued
1680
-continued
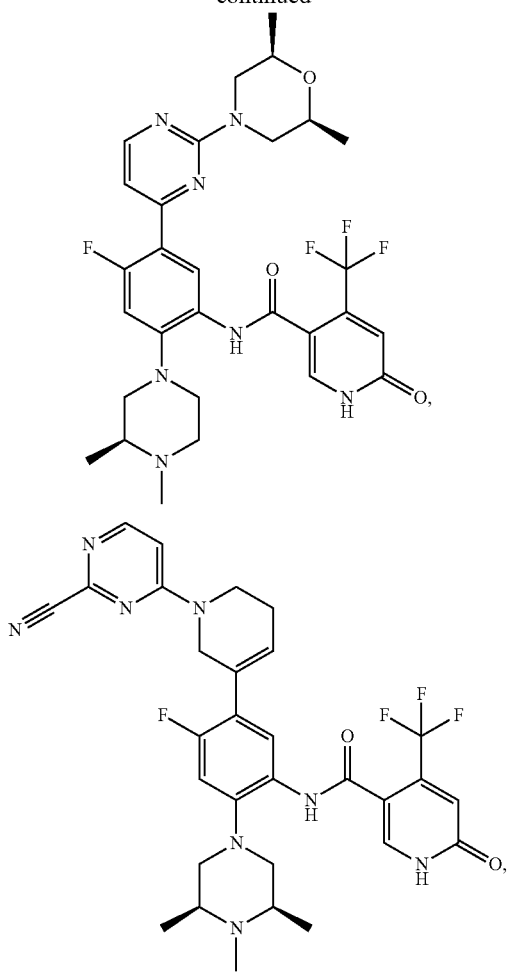
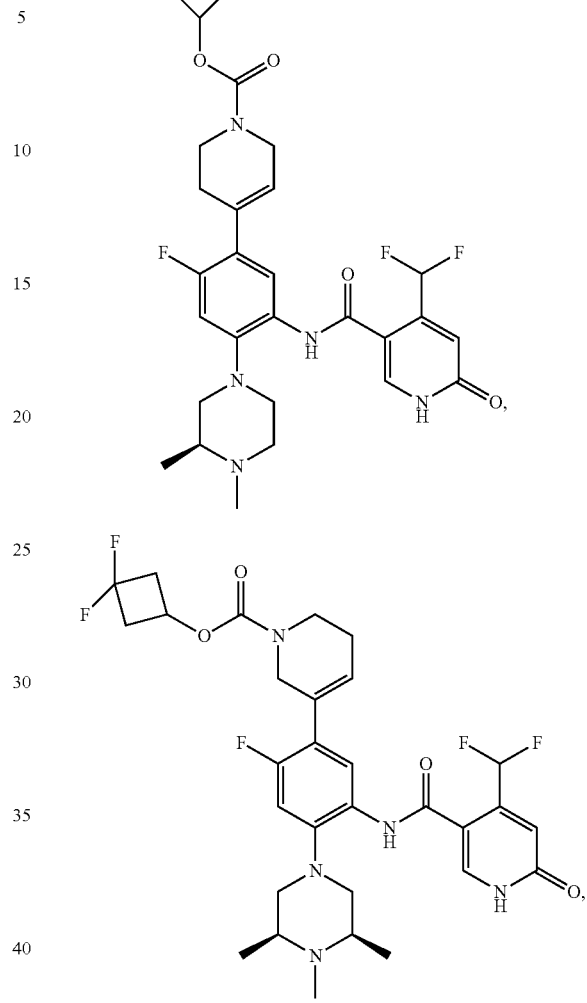
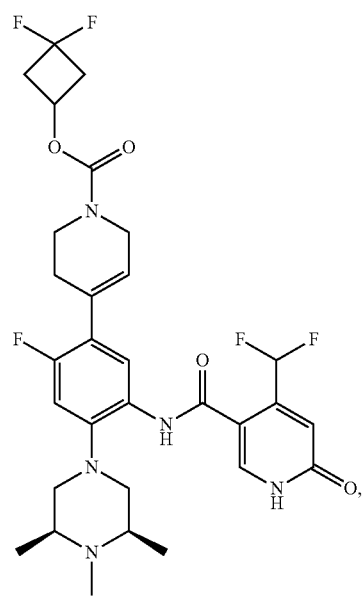

1681
-continued
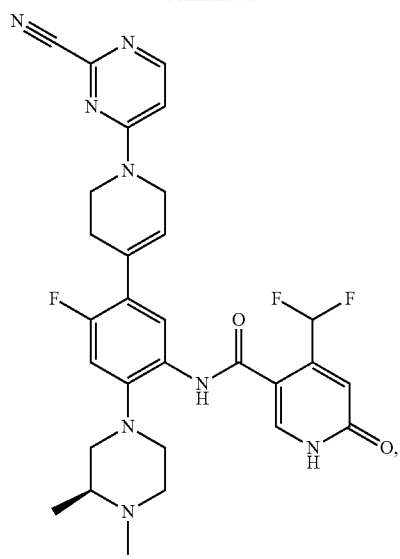
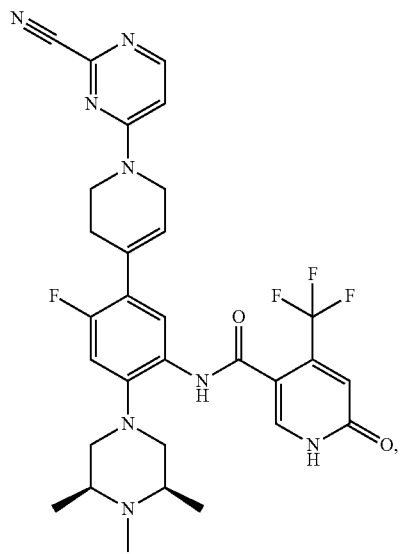
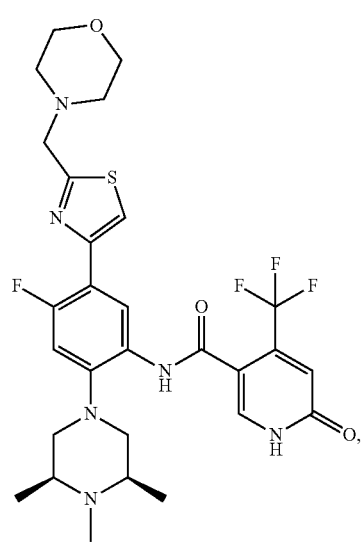
1682
-continued
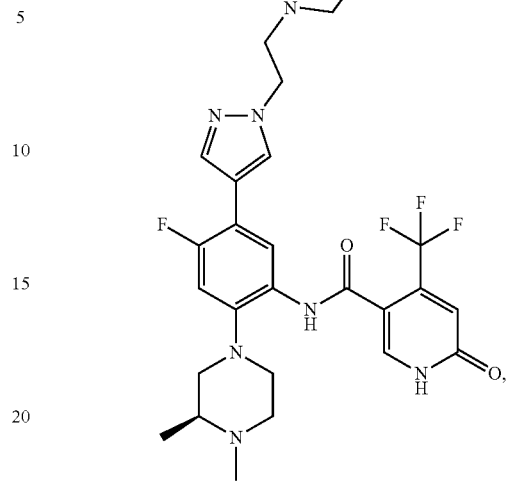
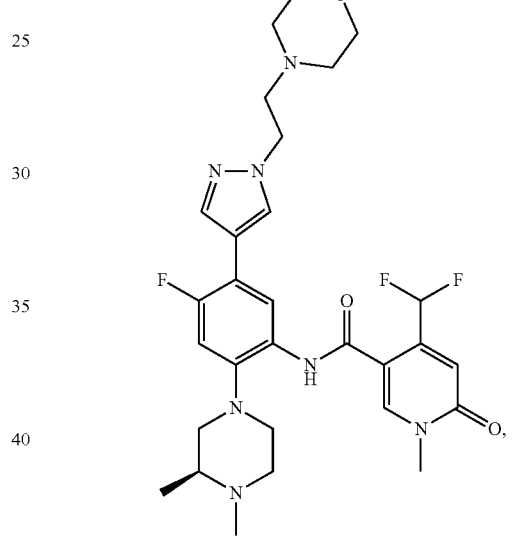
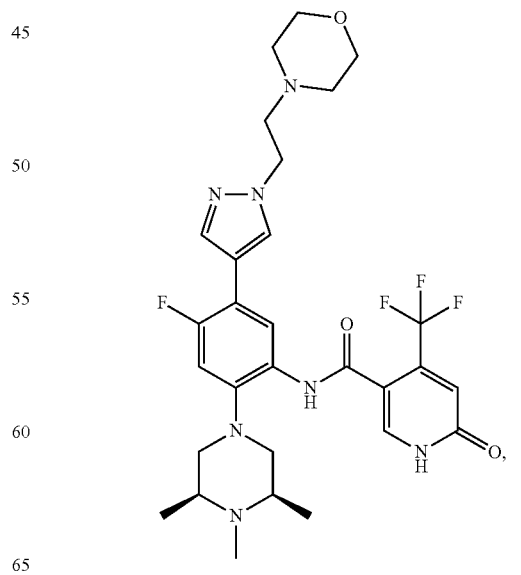

1683
-continued
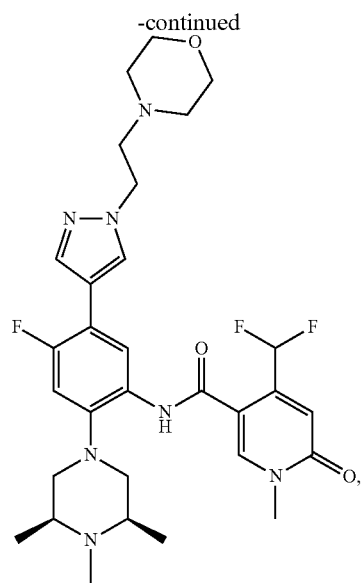
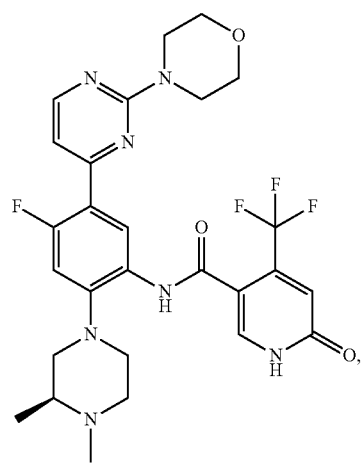
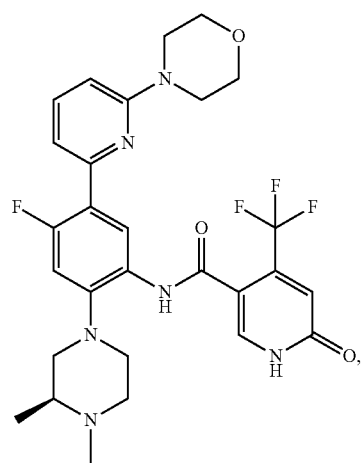
1684
-continued
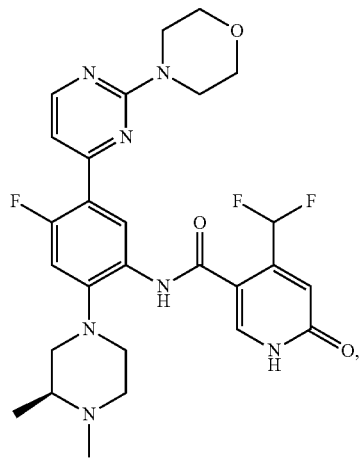
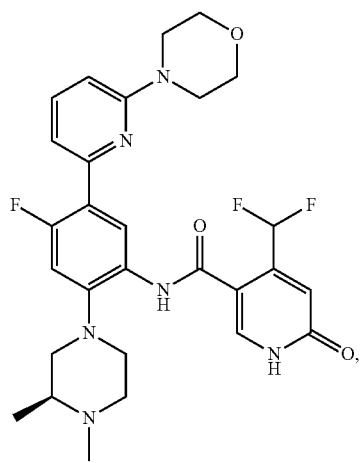
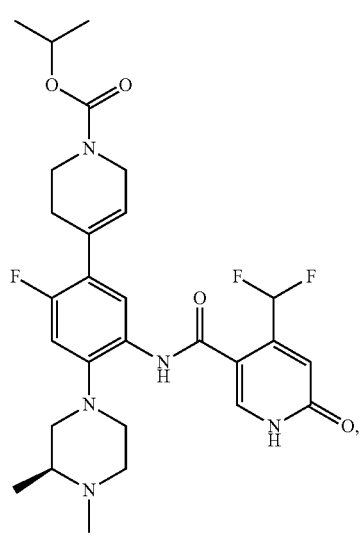

1685
-continued
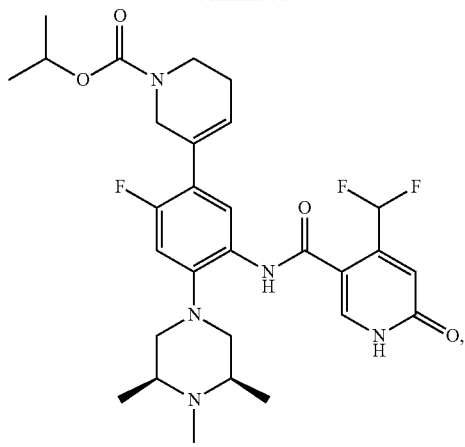
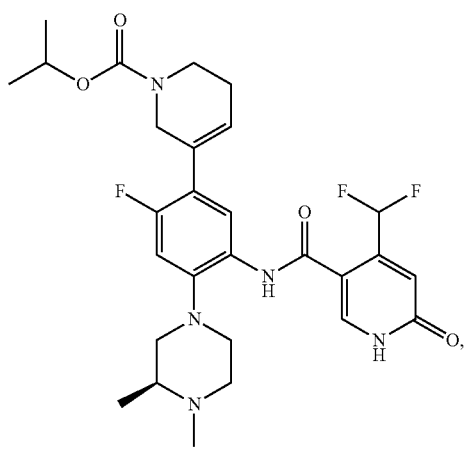
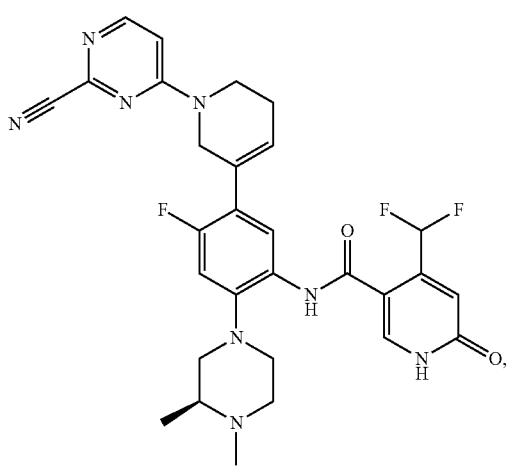
1686
-continued
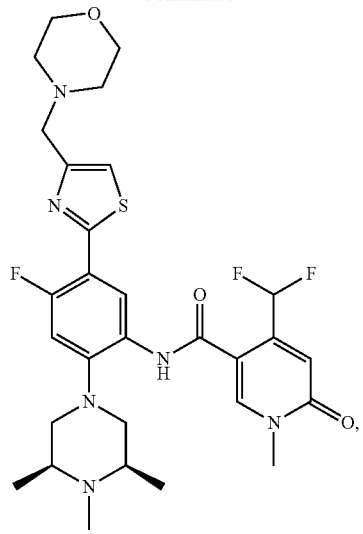
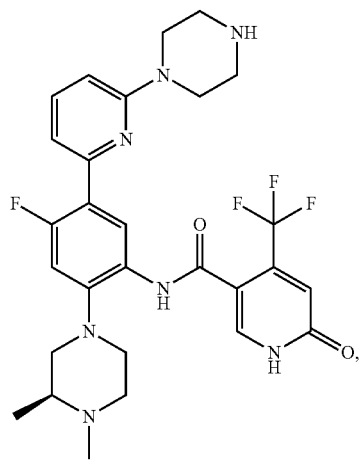
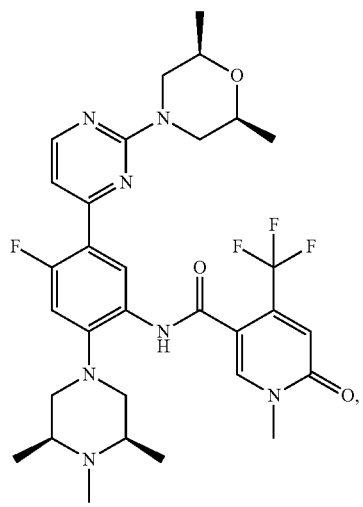

1687
-continued
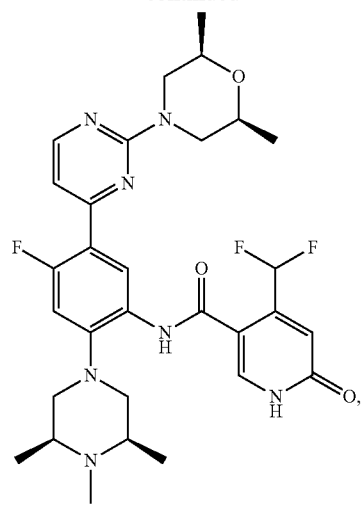
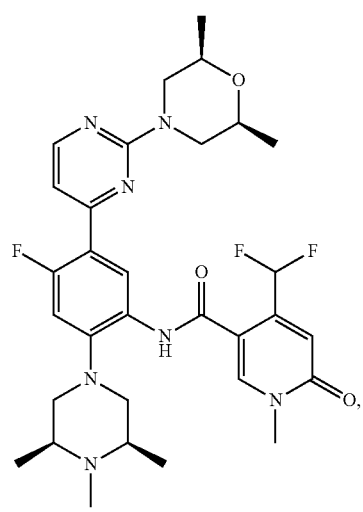
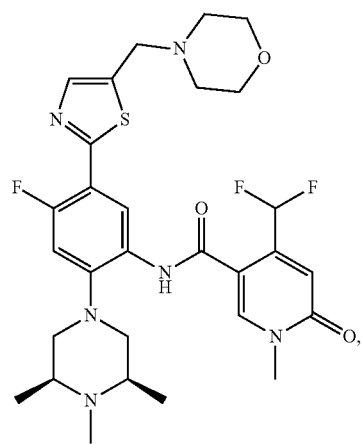
1688
-continued
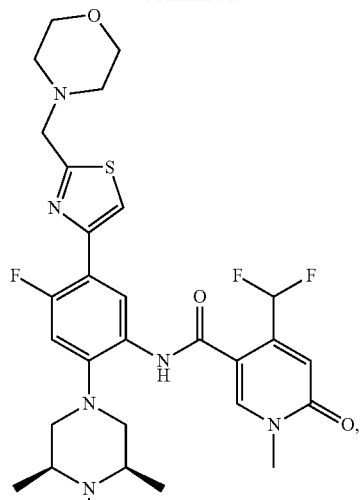
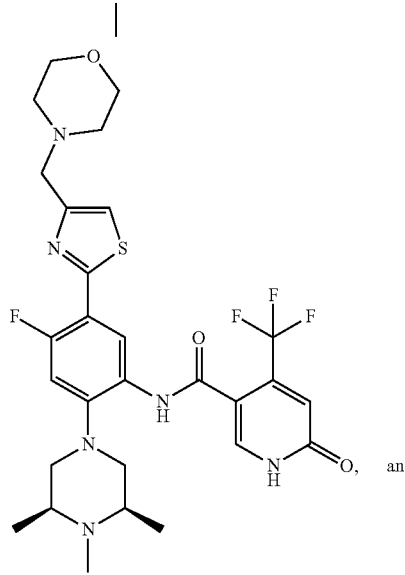
and
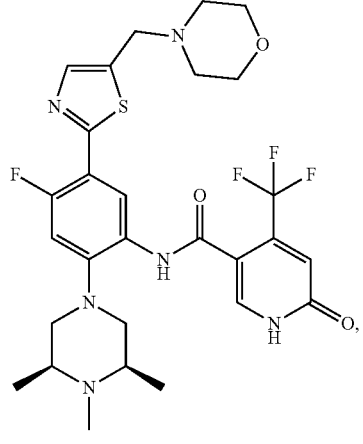
or a pharmaceutically acceptable salt thereof.

2. A compound selected from the group consisting of:
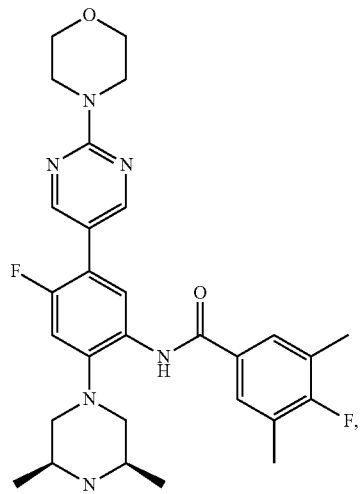
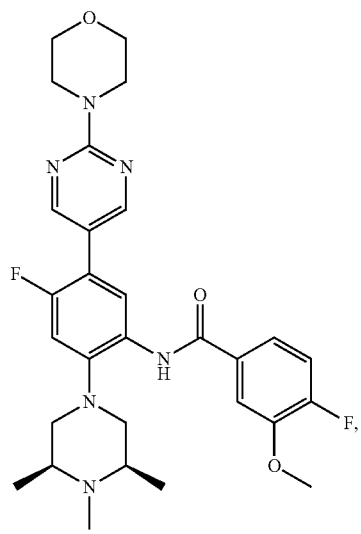
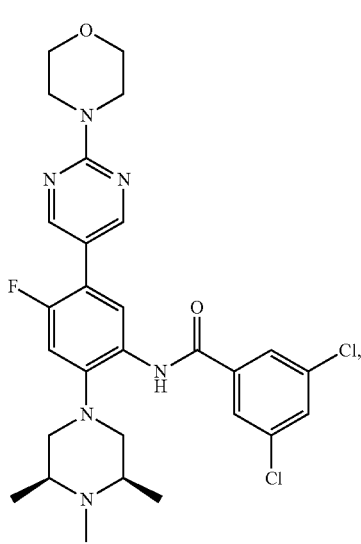
-continued
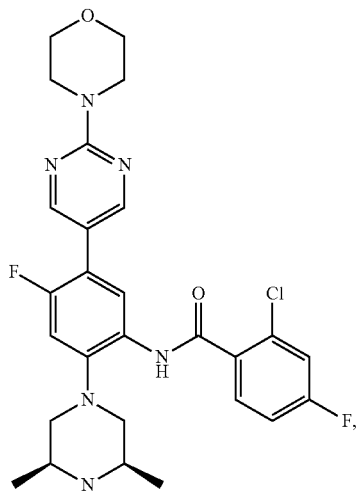
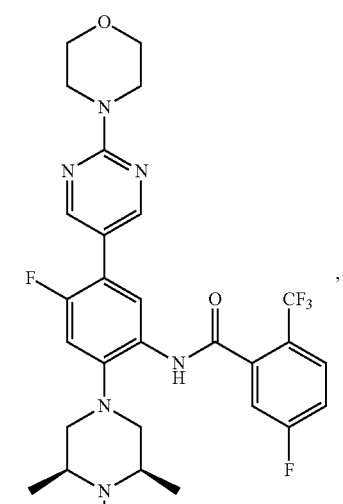
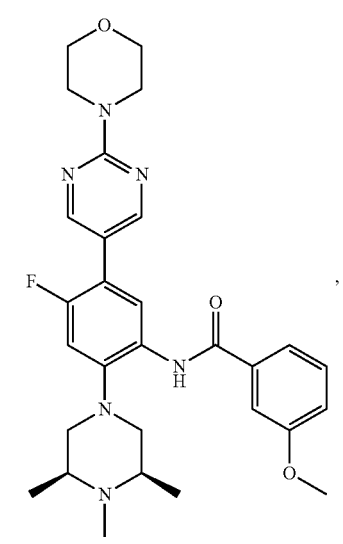

1691
-continued
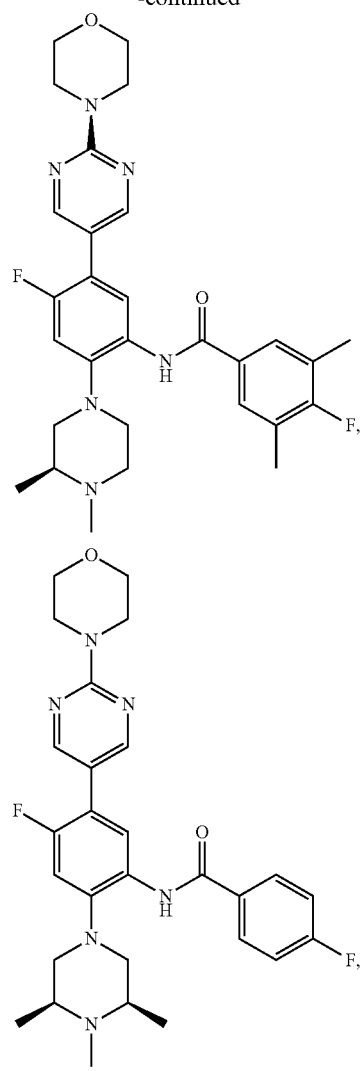
1692
-continued
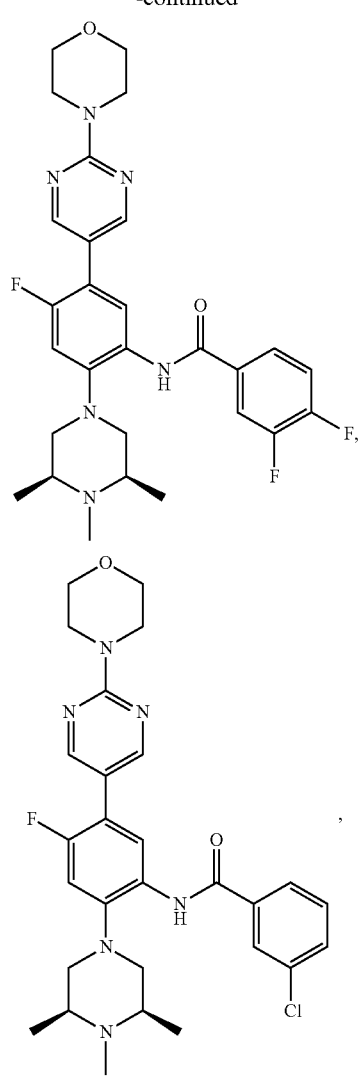
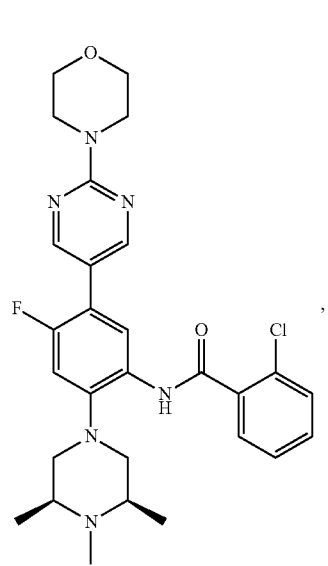
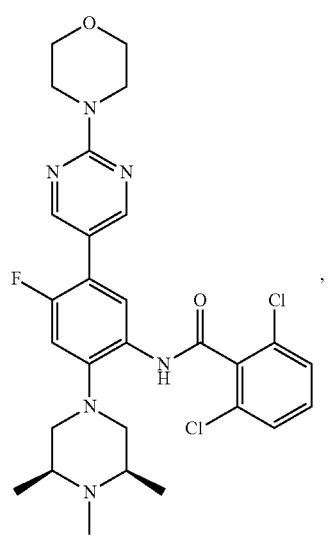

1693
-continued
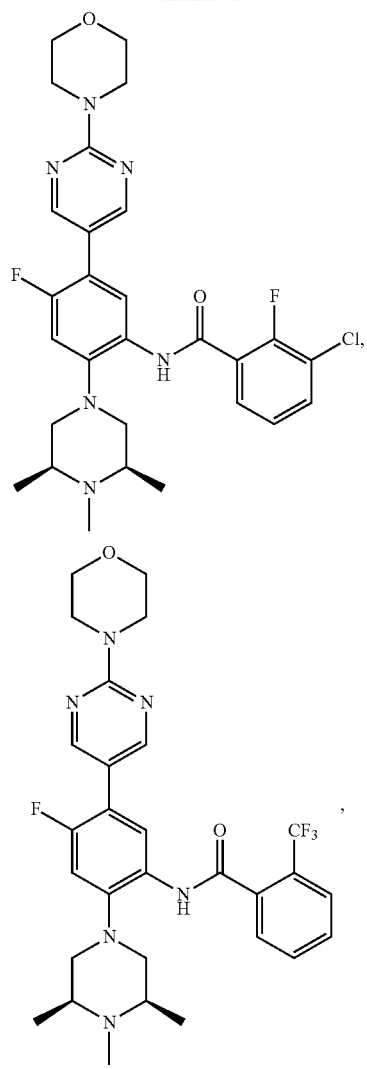
1694
-continued
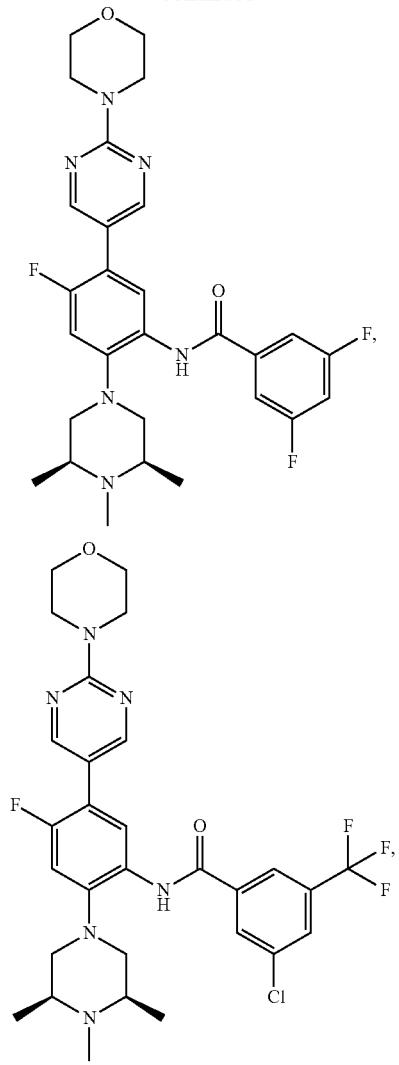
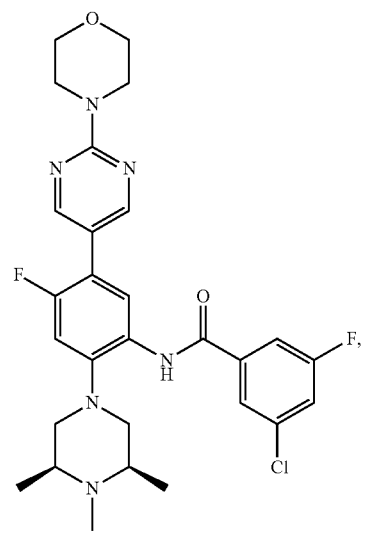
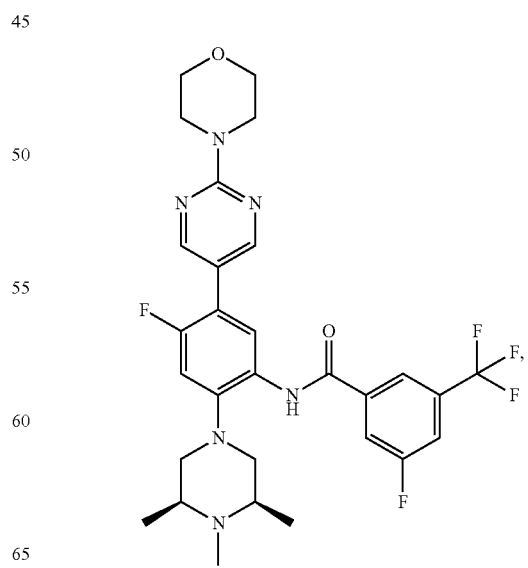

1695 1696
-continued -continued
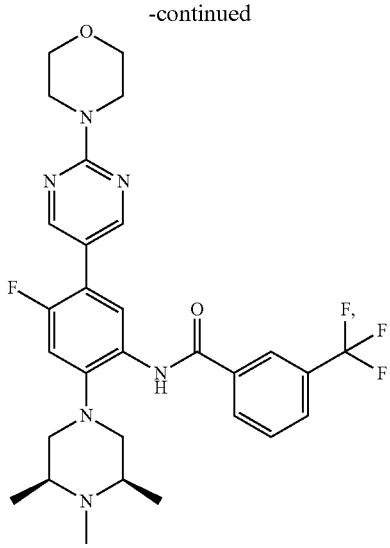
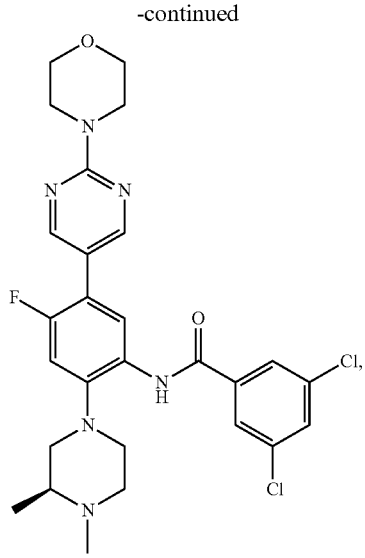

1697
-continued
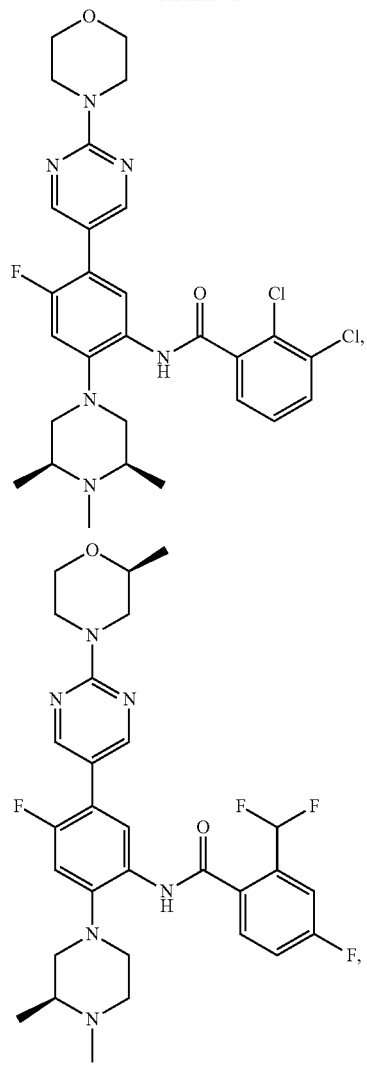
1698
-continued
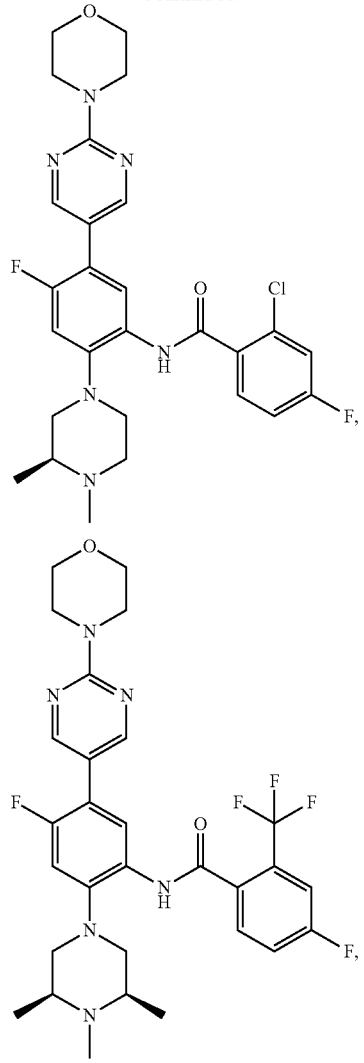
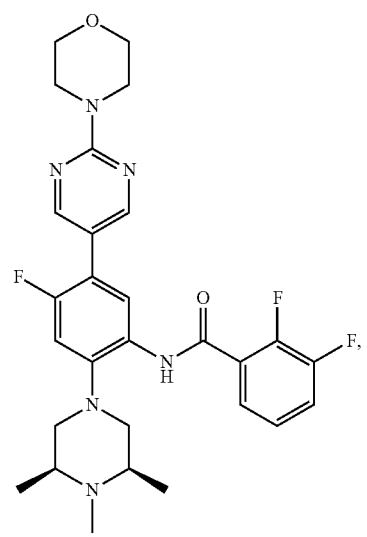

1699
-continued
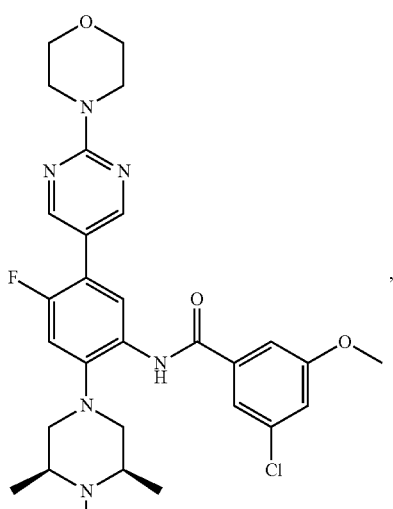
,
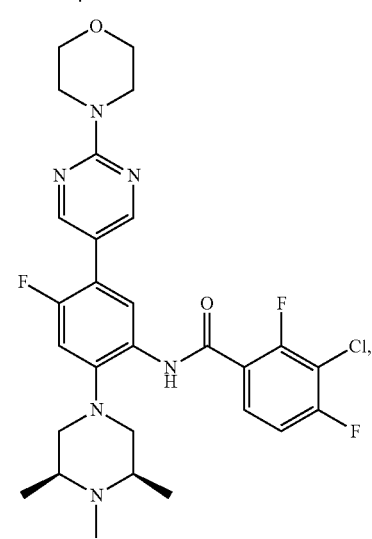
,
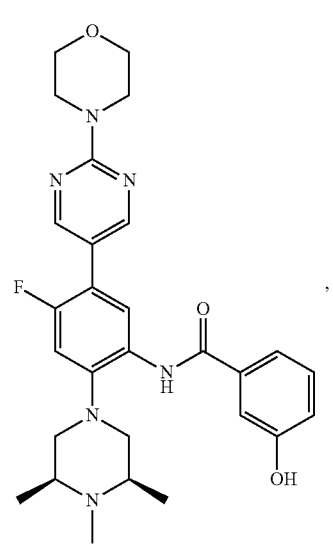
1700
-continued
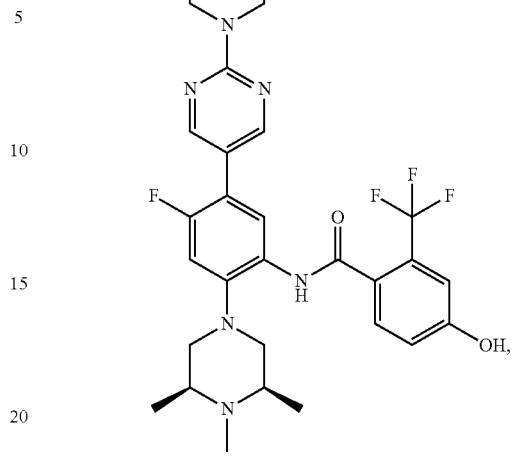
,
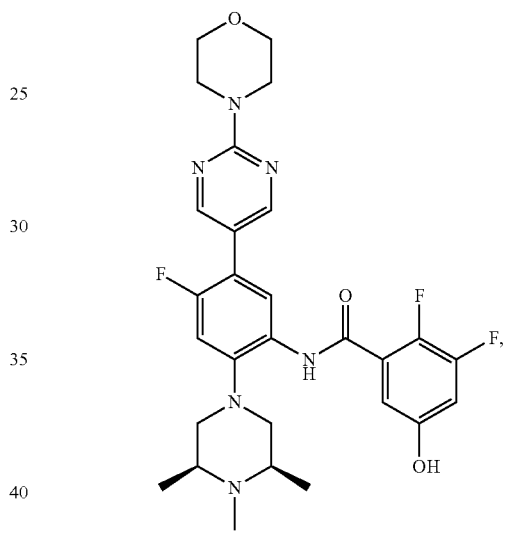
,
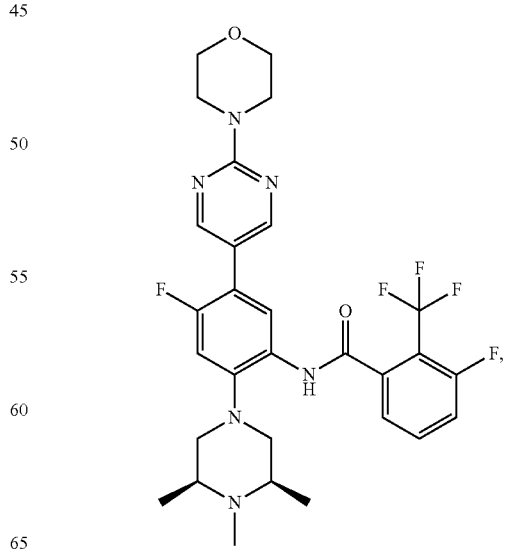

1701
-continued
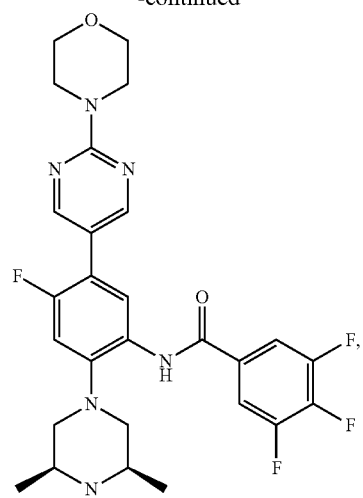
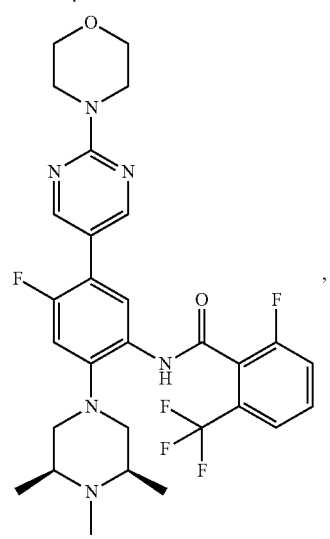
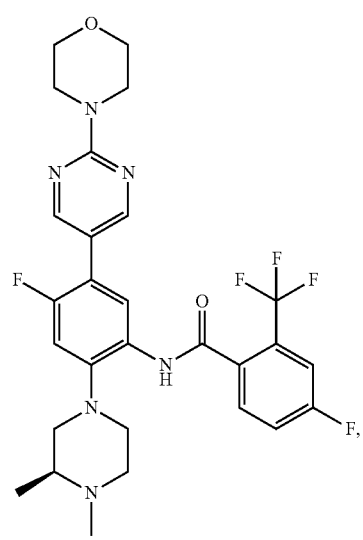
1702
-continued
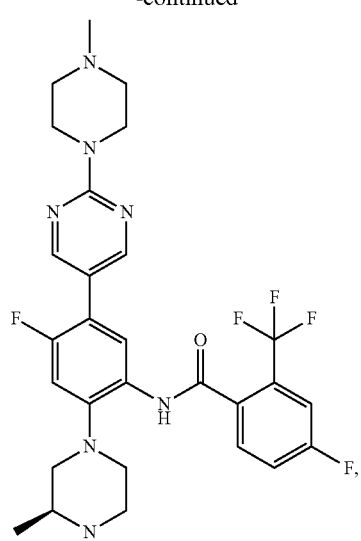
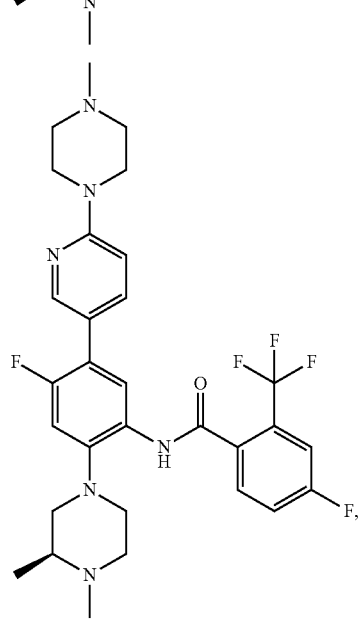
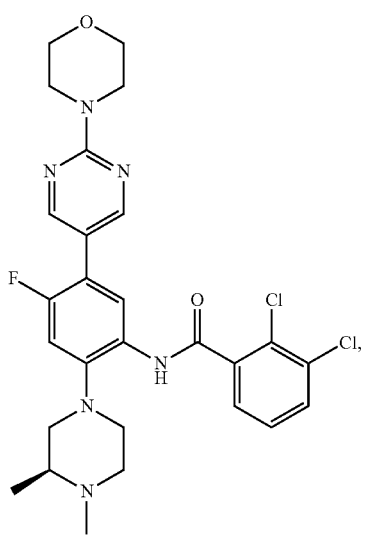

1703
-continued
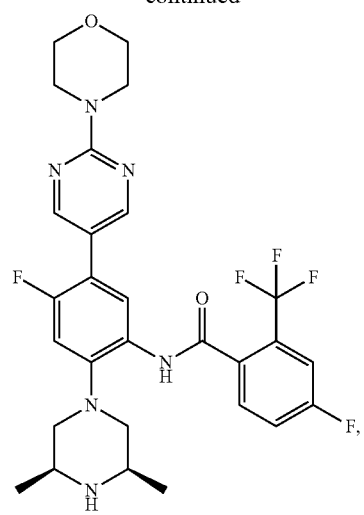
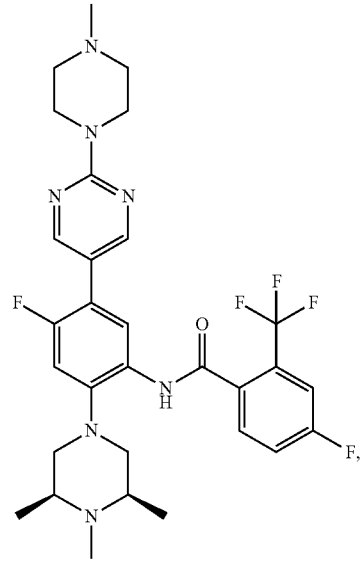
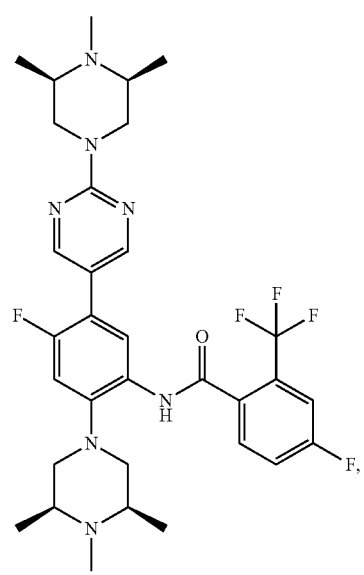
1704
-continued
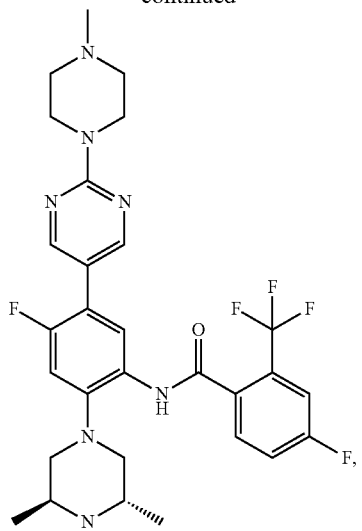
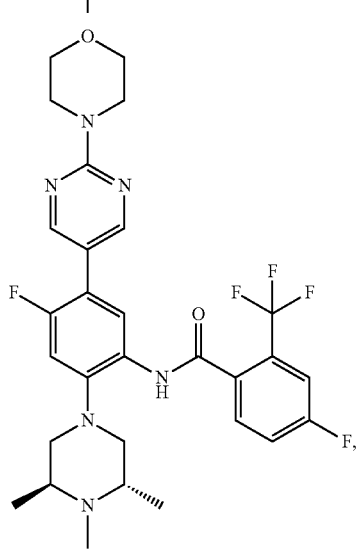
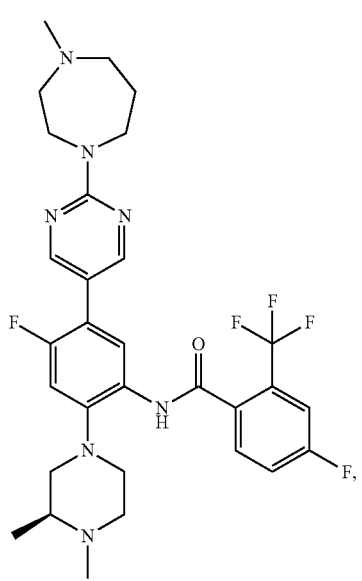

1705
-continued
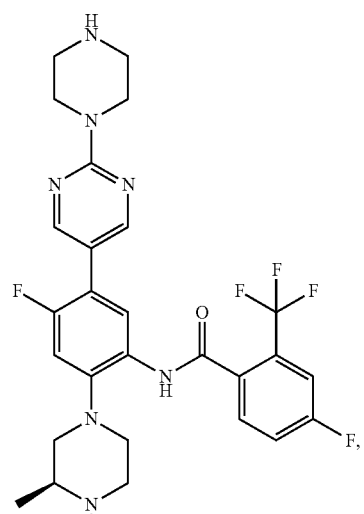
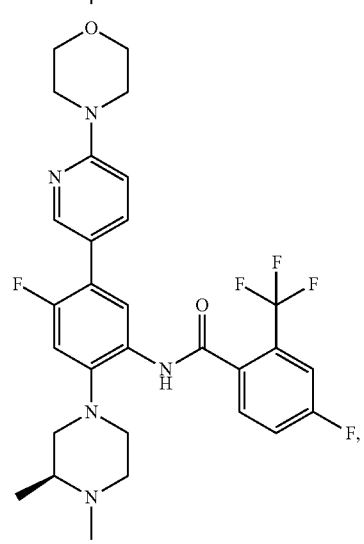
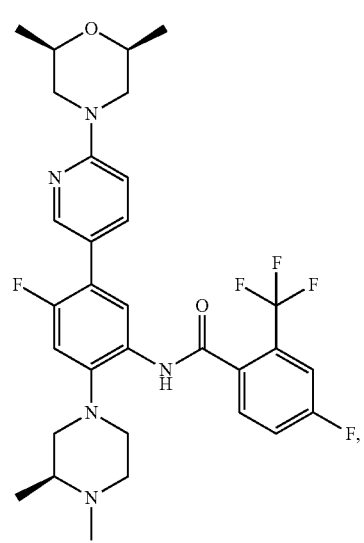
1706
-continued
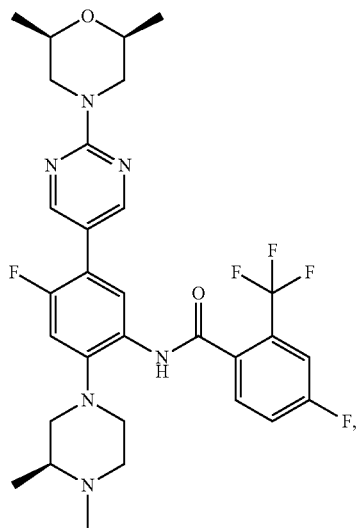
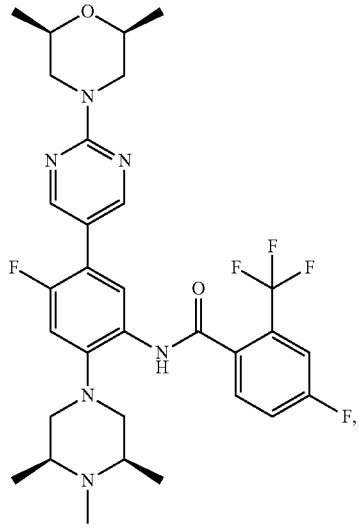
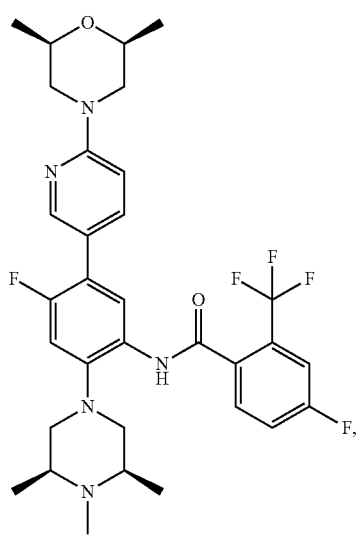

1707
-continued
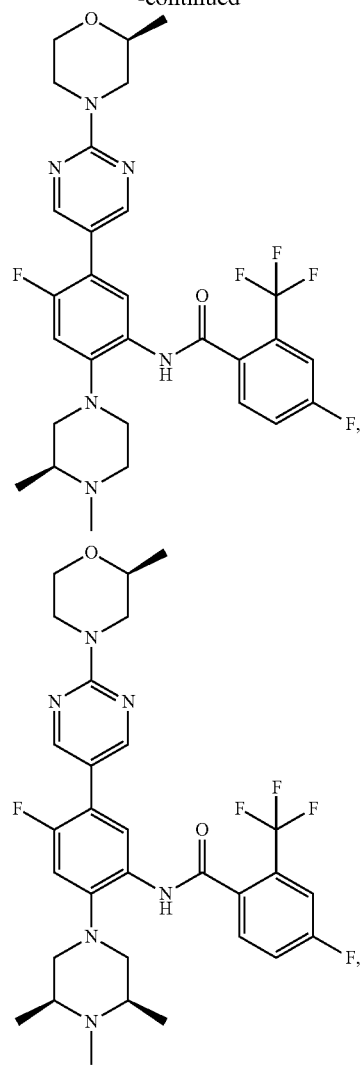
1708
-continued
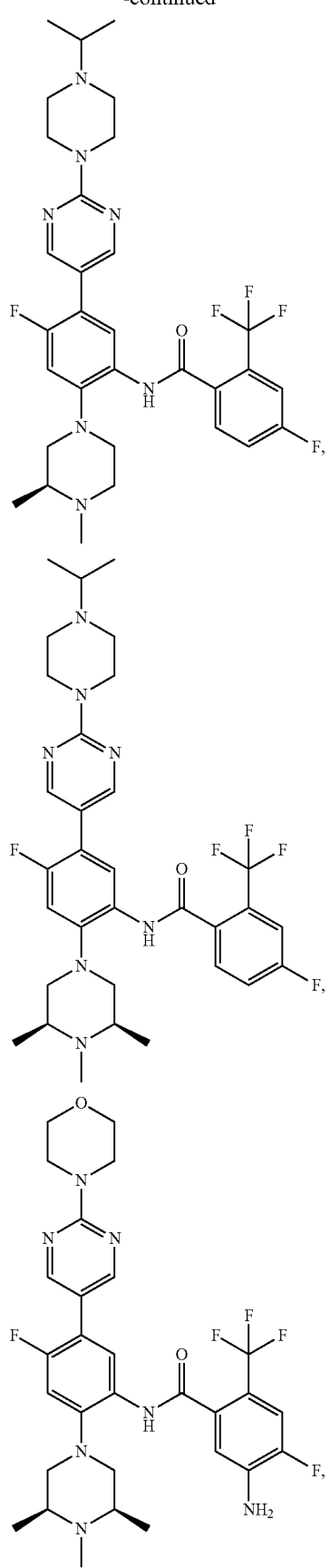

1709
-continued
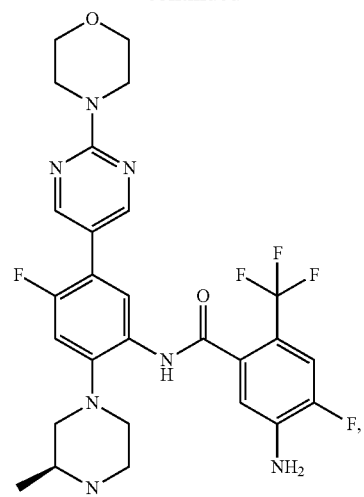
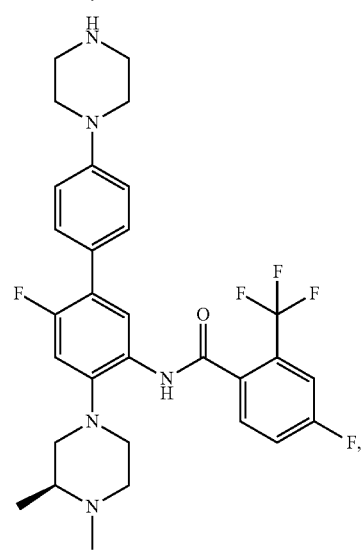
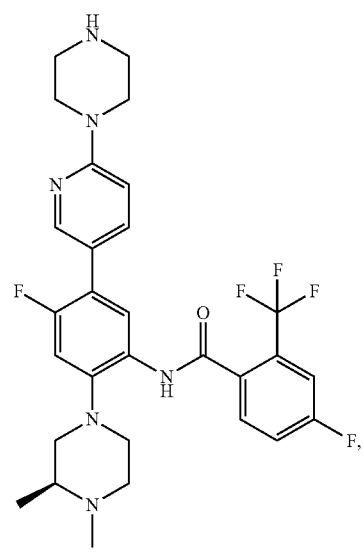
1710
-continued
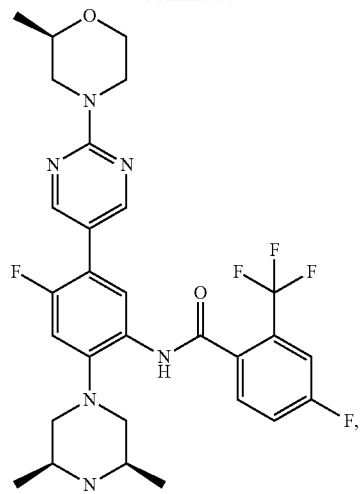
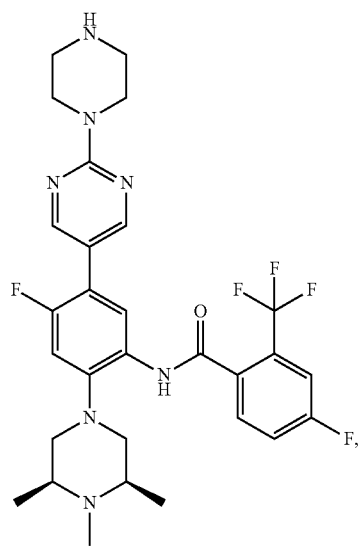
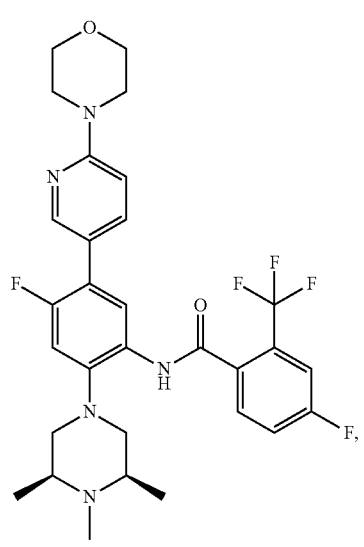

1711
-continued
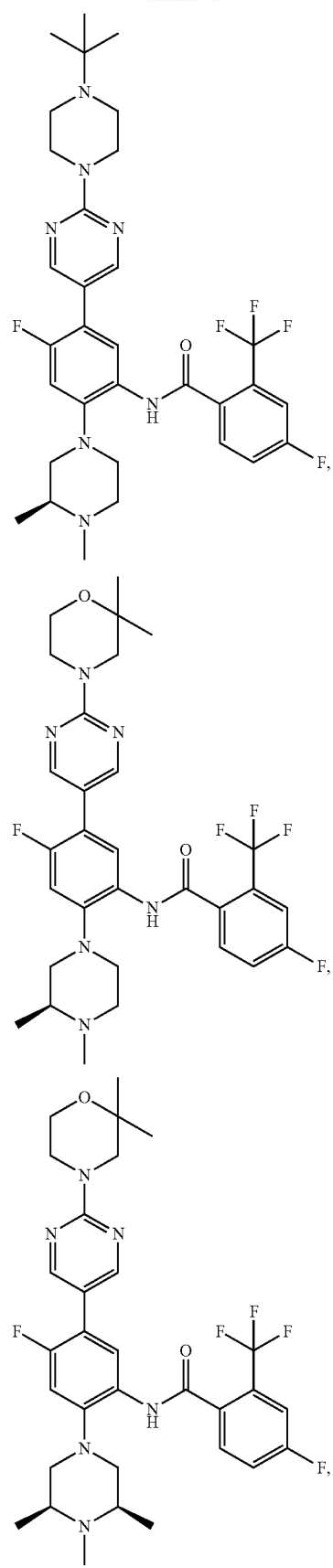
1712
-continued
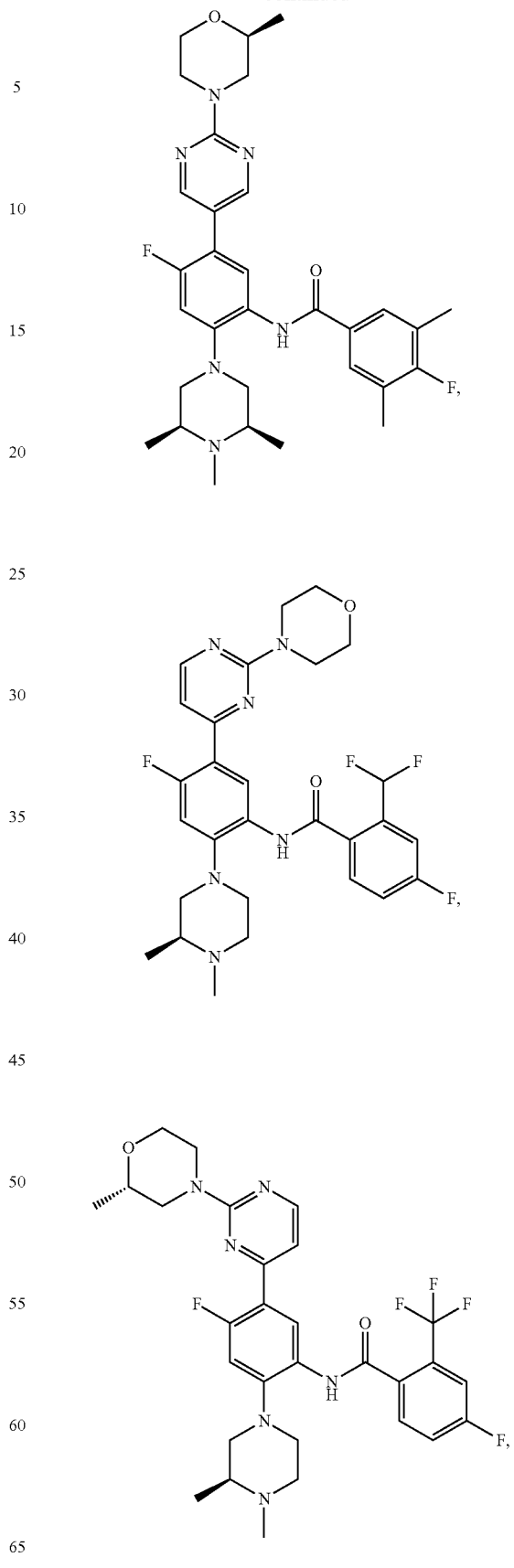

1713
-continued
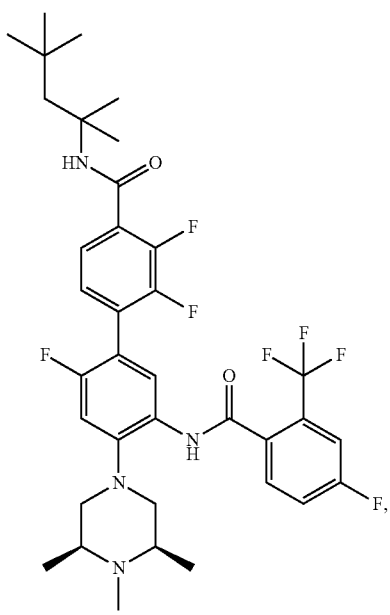
1714
-continued
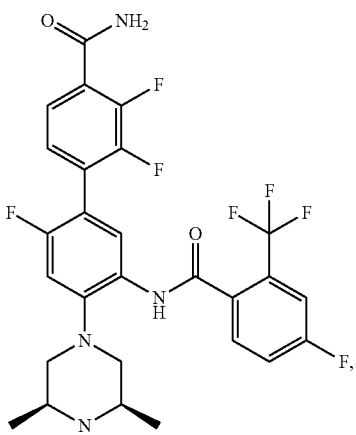
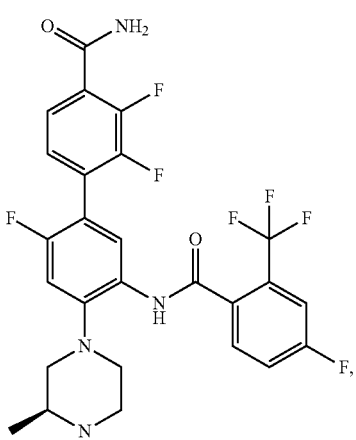
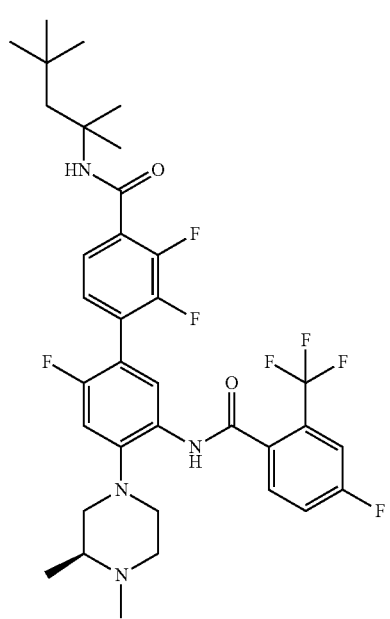
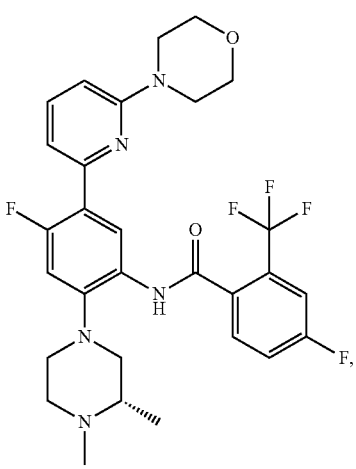

1715
-continued
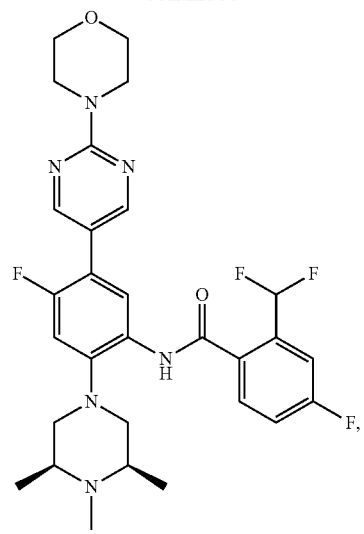
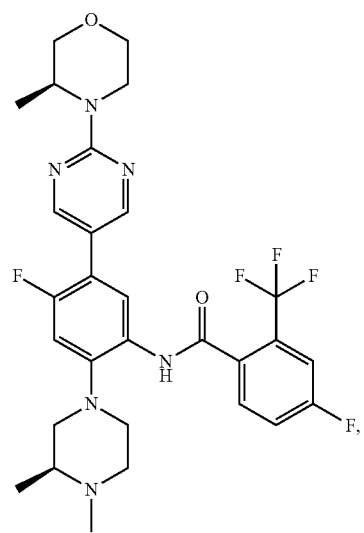
1716
-continued
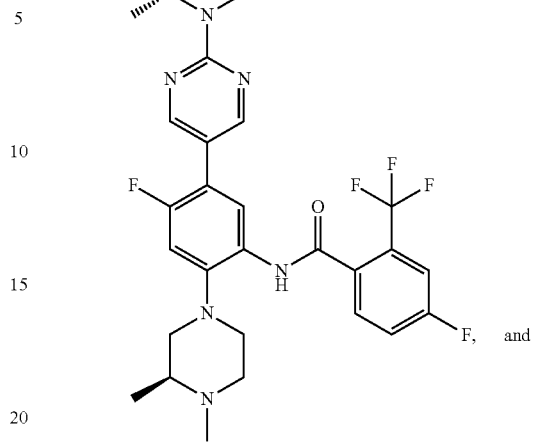
or a pharmaceutically acceptable salt thereof.
* * * * *